US007064123B1

(12) United States Patent
Graupe et al.

(10) Patent No.: US 7,064,123 B1
(45) Date of Patent: Jun. 20, 2006

(54) COMPOUNDS AND COMPOSITIONS AS CATHEPSIN INHIBITORS

(75) Inventors: Michael Graupe, Pacifica, CA (US); John W. Patterson, Mountain View, CA (US); Stephen D. Pickett, West Malling (GB); John O. Link, San Francisco, CA (US); Jiayao Li, Foster City, CA (US); David Aldous, Gillette, NJ (US); Sukanthini Thurairatnam, Bedminster, NJ (US); Andreas P. Timm, Bridgewater, NJ (US); Frank Halley, Sevres (FR); Justine Lai Yeun Quai, Epping (GB)

(73) Assignees: Aventis Pharmaceuticals Inc., Bridgewater, NJ (US); Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/035,783

(22) Filed: Dec. 24, 2001

Related U.S. Application Data

(60) Provisional application No. 60/257,603, filed on Dec. 22, 2000.

(51) Int. Cl.
*A61K 31/535* (2006.01)
*C07D 295/00* (2006.01)
*A61P 29/00* (2006.01)

(52) U.S. Cl. .............................. 514/233.5; 514/236.2; 514/253.8; 514/234.5; 514/236.5; 514/237.2; 544/114; 544/127; 544/137; 544/138; 544/140; 544/141; 544/111

(58) Field of Classification Search ................ 544/114, 544/127, 137, 138, 140, 141; 514/233.5, 514/236.2, 253.8, 234.5, 236.5, 237.2
See application file for complete search history.

(56) References Cited

U.S. PATENT DOCUMENTS

| 4,927,809 | A | 5/1990 | Stuber et al. |
| 5,424,325 | A | 6/1995 | Ando et al. |
| 5,486,623 | A | 1/1996 | Zimmerman et al. |
| 5,498,616 | A | 3/1996 | Mallano et al. |
| 5,847,135 | A | 12/1998 | Bemis et al. |
| 5,852,007 | A | 12/1998 | Chatterjee et al. |
| 5,874,424 | A | 2/1999 | Batchelor et al. |
| 5,998,390 | A | 12/1999 | Ramamurthy et al. |
| 6,004,933 | A | 12/1999 | Spruce et al. |
| 6,015,791 | A | 1/2000 | Gyorkos et al. |
| 6,022,861 | A | 2/2000 | Scarborough et al. |
| 6,114,310 | A | 9/2000 | Chamberland et al. |
| 6,124,333 | A | 9/2000 | Miller et al. |
| 6,255,453 | B1 | 7/2001 | Gyorkos |
| 6,353,017 | B1 | 3/2002 | Altmann et al. |
| 6,455,502 | B1 | 9/2002 | Bryant et al. |
| 6,476,026 | B1 | 11/2002 | Bryant et al. |
| 6,492,362 | B1 | 12/2002 | Graupe et al. |
| 6,506,733 | B1 | 1/2003 | Buysse et al. |
| 6,576,630 | B1 | 6/2003 | Link et al. |
| 6,608,057 | B1 | 8/2003 | Cywin et al. |

FOREIGN PATENT DOCUMENTS

| EP | 0272671 | 6/1988 |
| EP | 0355572 | 2/1990 |
| EP | 0376012 | 7/1990 |
| EP | 0419683 | 4/1991 |
| EP | 0536399 | 4/1993 |
| EP | 0652009 | 10/1995 |
| EP | 0754454 | 1/1997 |
| EP | 0291234 | 11/1998 |
| EP | WO 01/19816 | 3/2001 |
| JP | 42009133 | 5/1967 |
| JP | 63303868 | 12/1988 |
| JP | 06192199 | 7/1994 |
| JP | 2001-011037 | 1/2001 |
| JP | 2001-055366 | 2/2001 |
| WO | WO 95/13069 | 5/1995 |
| WO | WO 95/15309 | 6/1995 |
| WO | WO 95/24382 | 9/1995 |
| WO | WO 96/21655 | 7/1996 |
| WO | WO 96/30353 | 10/1996 |
| WO | WO 96/40647 | 12/1996 |
| WO | WO 96/40744 | 12/1996 |
| WO | WO 96/41638 | 12/1996 |
| WO | WO 97/03679 | 2/1997 |
| WO | WO 98/01133 | 1/1998 |
| WO | WO 98/01428 | 1/1998 |
| WO | WO 98/05336 | 2/1998 |
| WO | WO 98/08802 | 3/1998 |
| WO | WO 98/08867 | 3/1998 |
| WO | WO 98/21188 | 5/1998 |
| WO | WO 98/23588 | 6/1998 |
| WO | WO 98/49190 | 11/1998 |
| WO | WO 99/24460 | 5/1999 |
| WO | WO 00/48992 | 8/2000 |
| WO | WO 00/49007 | 8/2000 |
| WO | WO 00/49008 | 8/2000 |
| WO | WO 00/51998 | 9/2000 |
| WO | WO 00/59881 | 10/2000 |
| WO | WO00/59881 | 10/2000 |

(Continued)

OTHER PUBLICATIONS

U.S. Appl. No. 10/035,783, filed Dec. 24, 2001, Graupe et al.

(Continued)

*Primary Examiner*—Taofiq Solola
*Assistant Examiner*—Robert Shiao
(74) *Attorney, Agent, or Firm*—Joseph D. Rossi

(57) ABSTRACT

The present invention relates to novel selective cathepsin S inhibitors, the pharmaceutically acceptable salts and N-oxides thereof, their uses as therapeutic agents and the methods of their making.

22 Claims, No Drawings

FOREIGN PATENT DOCUMENTS

| WO | WO 00/69855 | 11/2000 |
|---|---|---|
| WO | WO 01/09110 | 2/2001 |
| WO | WO01/09169 | 2/2001 |
| WO | WO 01/19796 | 3/2001 |
| WO | WO 01/19808 | 3/2001 |
| WO | WO 01/30772 | 5/2001 |
| WO | WO 01/55125 | 8/2001 |
| WO | WO 01/58886 | 8/2001 |
| WO | WO02/20485 | 3/2002 |
| WO | WO02/096892 | 5/2002 |
| WO | WO02/057248 | 7/2002 |
| WO | WO02/057249 | 7/2002 |
| WO | WO02/057270 | 7/2002 |
| WO | WO02/100849 | 12/2002 |

OTHER PUBLICATIONS

U.S. Appl. No. 10/719,080, filed Nov. 21, 2003, Graupe et al.
U.S. Appl. No. 02/17922, filed Nov. 24, 2003, Graupe et al.
U.S. Appl. No. 10/787,367, filed Sep. 16, 2002, Graupe et al.
U.S. Appl. No. 10/418,163, filed Oct. 23, 2003, Li et al.
Adams, et al., Potent and Selective Inhibitors of the Proteasom: Dipeptidyl Boronic Acids, Biooganic & Medicinal Chemistry Letters, 8: 333-338 (1998).
Ashworth, et al, 4-Cyanothiazolidides as very potent, stable inhibitors of dipeptidyl peptidase IV, Bioorganic & Med. Chem. Letters, B,Oxford, 6(22):2745-2748 (1996).
Bergeman, et al., Studies on the reactivity of α-cyanoα-Isocyano alkanoates. Versitile synthons for the assembly of imidazolea, Helv.Chim. ACTA, 62(6):909-918 (1999).
Billson, et al., The Design and Synthesis of Inhibitors of the Cystelnyl, Bioorg. Med. Chem. Lett. vol. 8, pp. 993-998, 1998.
Bromme, et al., Potent Inactivation of Cathepsins S and L, Biol. Chem. Hoppe-Seyler. vol. 375, No. 5, pp. 343-347, 1994.
Chatterjee, et al., D-Amino Acid Containing, High-Affinity Inhibitors of Recombinant Human Calpain I, Journal of Medicinal Chemistry, vol. 41, No. 15, p.: 2663-2666 (1998).
Cohen, et al., Therapy of relapsing multiple sclerosis. Treatment approaches for nonresponders, Journal of Neuroimmunology, 98:29-36 (1999).
Dufour, et al., Engineering nitrile hydratase activity into a cysteine protease by a single mutation, Bio.chemistry, US, Am. Chem. Soc., Easton, PA, 34(50):16382-16388 (1995).
Edwards, et al., Design, Synthesis, and Kinetic Evaluation of a Unique Class of Elastase Inhibitors, the Peptidyl a-Ketobenzoxazoles, and the X-ray Crystal Structure of the Covalant Complex between Porcine Pancreatic Elastase and Ac-Ala-Pro-Val-2-Benzoxazole, Journal of American Chemical Society, vol. 114, No. 5, p. 1854-1863 (1992).
Evoli, et al., abstract only, Drugs, 1996, 52(5), 662-70.
Gour-Salin, et al., Inhibition of papain by peptide nitriles: conversion of the nitrile group into other functionalitles via the papain:nitrile thiomidate ester adduct, Can. J. of Chem, CA, National Research Council. Ottawa, 69(8):1288-1297 (1991).
Hallegua, et al., Cyclosporine for lupus membranous nephritis: experience with ten patients and review of the literature, Lupus, 9:241-251 (2000).
Hanzlik, et al., Reversible covalent binding of peptide nitriles to papain, Biochim. Biophys, Acta, vol. 1035, No. 1, 1990, pp. 62-70.
Harris, et al., Characteristics of a continuous fluorogenic assay for calpain I. Kinetic evaluation of peptide aldehydes, halomethyl ketones and )achalasia) methyl ketones as inhibitors of the enzyme, Chemical Abstracts, 110:7, Bioorg. Med. Chem. Lett, 5(4) 393-398 (1995).
Heitmiller, R.F., abstract only., Semin. Thorac. Cardiovasc. Surg., 1999, 11(1), 41-6.
Katritzky, et al., Benzotriazole-assisted synthesis of α-(acylamino) nitrites and a conceptually novel method for peptide elongation, Chem. Soo., Perkin. Trana. 1(7):1853-1857 (1990).
Khamashta, et al., Expert. Opin. Investig. Drugs, 2000, 9(7), 1581-93.
Krantz, et al., Peptidyl (Acyloxy)methyl Ketones and the Qulescent, Biochemistry. vol. 30, pp. 4878-4687, 1991.
Levy, E.G., Baillieres Clin. Endocrinol. Metab., 1997, 11(3) 585-595.
Li, et al., Aminoacylpyrrolidine-2-nitriles: Potent and stable inhibitors of dipeptidyl-peptidase IV (CD 26), Archives of Biochem. and Bioph., 323(1) 148-154 (1995).
Lipshutz, et al., Chiral Induction in orginally racemic amino adds via 5-acyl and 5-acyloxyaminooxazoles, Isr, J. Chem. 27(1):49-55 (1986), abstract.
Lipshutz, et al., Heterocycles as masked diamide/dipeptide equivalents, Formation and reactions of substituted 5-(acylamino)oxazoles as intermediates en route to the cyclopeptide alkaloids, . Am. Chem. Soc., 105(26):7703-7713 (1983).
Lipshutz et al., Oxazolophanes as masked cyclopeptide alkaloid equivalents: cyclic peptide chemistry without peptides couplings, J. Am. Chem. Soc., 112(19):7032-7041 (1990).
Marquis, et al., Potent dipeptidyketone inhibitors of the cysteine protease cathepsin, Chemical Abstracts. 7:4 581-588 (1999).
McMath, et al., Direct dialkylation of peptide nitriles, Application of the synthesis of 1-aminocyclopropane-1 carboxylic acid (Acc)-containing dipeptides, Bull. Soc. Chim. Fr. 134(1):105-110 (1997).
Moriya, et al., Synthesis and Hypolipidemic Activities of 5-Thienyl-4-oxazoleacetic Acid Derivatives.sup.1, J. Med. Chem., 29:333-341 (1986).
Moser, et al., 130 Poly (dipeptamidinium)-Salze: definition und metoden zur praparatven herstellung, poly (dipeptamidinium) salts: definition and methods of preparation, Helvitica Chimica ACTA, CH, Verlag, Basal 69:1224-1262 (1986).
Nippon, K., Patent Abstracts of Japan, Publication No. 63301868, 013(137)(1988), abstract.
North, et al., Synthetic studies towards cyclic peptides. Concise sythesis of thiazoline and thiazole containing amino acids, Tetrahedron, 48(24):8627-8290 (1990).
Ogilvie, et al., Peptidomimetric Inhibitors of the human cytomegalovirus protease, Journal of Medicinal Chemistry vol. 40 No. 25 (1997).
Picken, et al., Inhibition of bovine cathepsin B by amino acid-derived nitriles, Biochemical Socitey Transactions, vol. 18, No. 2, p:316 (1990).
Pliura, et al., Comparative behavior of colpain and cathepsin B, Biochem. J. vol. 288, pp. 759-762, 1992.
Polman, et al., Drug treatment of multiple sclerosis, BMJ, 321: 19-26 (2000).
Riese, et al., Essential Role for Cathesin S in MHC Class II-Associated Invariant Chain Processing and Peptide Loading, Immunity, 4:357-368 (Apr. 1996).
Smith, et al., New Inhibitors of Cysteine Proteinases, J. Am. Chem. Soc. vol. 110, No. 13, pp. 4429-4431, 1988.

Suave, et al., Carboxylmodified amino acids and peptides, I An efficient method for the synthesis of monofuctionalized enamines and monofuntionalized methyl ketone derivatives form thioamides via episulfides and thloiminium salts, Tetrahedron Lett, 29:19 2295-2298 (1988).

Suzue, S., Hepatic agents, I. Synthesis of aminocyl (and hydroxyacyl) aminoacetonitriles, Chem. and Pharm. Bull. (Tokyo) (1988), 16(6), 1417-32.

Suzue, et al., Studies on Heptic Agents, Chem. Pharm. Bull. vol. 16, No. 8, pp. 1417-1432, Aug. 1968.

Suzuki, et al., Synthesis of 2-Aryl-4(3-thienyl)imidazole Derivatives with Antinflammatory Properties .sup.1), Chem. Pharm. Bull, 34(8): 3111-3120 (1998).

Tao, et al., Inhibition of Calpain By Peptidyl Heterocycles, Bioorganic & Medicinal Chemnistry Letters, 6.24 3009-3112 (1996).

Thompson, et al., Carboxyl-modified amino acids and peptides as protease inhibitors, J. Med. Chem., 29(1):104-111 (1986).

Tsutsumi, et al., Synthesis and Structure-Activity Relationships of Peptidyl a-Keto Heterocycles as Novel Inhibitors of Protyl Endopeptidase, Journal of Medicinal Chemistry, vol. 37, No. 21, p. 3492-3502 (1994).

Vargha, E., Peptide derivatives. VI. N-protected di- and tripeptide nitriles, Stud. Univ. Babes-Bolyal, Ser. Chem., 19(2):31-5 (English abstract of article in Romanian) (1956).

Varghese, The structure and resonance Raman spectra-structure correlations for methloxycarbonyl-L-phenylalanyl-L-alanine ethyl dithioester, Can. J. Chem., 64(8):1668-1673 (1985).

Yamada, et al., Studies of unusual amino acids and their peptides. IX. The synthetic study of bottomycine B1 and B2, Bul. Chem. Soc. Jpn. 51(3):878-83 (1978), abstract.

Derwant Abstract of Japanese Patent Application 08-192199, (Jul. 12, 1994).

U.S. Appl. No. 09/927,188, filed Aug. 10, 2001, Cai et al.
U.S. Appl. No. 09/927,324, filed Aug. 10, 2001, Butler et al.
U.S. Appl. No. 09/928,122, filed Aug. 10, 2001, Breitenbucher et al.
U.S. Appl. No. 09/946,214, filed Sep. 5, 2001, Gu et al.
U.S. Appl. No. 10/042,565, filed Nov. 16, 2001, Quibell et al.
U.S. Appl. No. 10/148,612, filed Aug. 21, 2002, Ohmoto et al.
U.S. Appl. No. 10/148,613, filed Aug. 28, 2002, Ohmoto et al.
U.S. Appl. No. 10/181,713, filed Jul. 22, 2002, Ohmoto et al.
U.S. Appl. No. 10/181,799, filed Jul. 23, 2002, Ohmoto et al.
U.S. Appl. No. 10/231,425, filed Aug. 28, 2002, Buxton et al.
U.S. Appl. No. 10/256,512, filed Sep. 27, 2002, Bekkali et al.
U.S. Appl. No. 10/258,053, filed Oct. 17, 2002, Cummings et al.
U.S. Appl. No. 10/275,563, filed Nov. 7, 2002, Cowen et al.
U.S. Appl. No. 10/279,424, filed Oct. 24, 2002, Bekkali et al.
U.S. Appl. No. 10/466,385, filed Jan. 8, 2004, Quibell et al.

Chapman, et al., Emerging Roles for Cysteine Proteasas In Human Biology, Ann. Rev. Physiol.; 1997; 69: pp. 63-68.

Dranoff, et al., Cathepsin S Required for Normal MHC Class II Peptide Loading and Germinal Center Development, Immunity; 1999; 10; pp. 197-208.

Fenwick, et al., Diastereoselective Synthesis, Activity and Chiral Stability of Cycilo Alkoxyketone Inhibitors of Cathepsin K., Bioorg. Med. Chemm. Lett.; 2001; 11(2); pp. 199-202.

Fenwick, et al., Solid-phase Synthesis of Cyclic Alkoxyketones, Inhibitors of the Cysteine Protease Cathepsin K., Bioorg. Med. Chem. Lett.; 2001; 11(2); pp. 195-198.

Greenspan, et al., Identification of Dipeptidyl Nitriles as Potent and Selective Inhibitors of cathepsin B Through Structure-based Drug Design, J. Med. Chem.; 2001; 44; pp. 4524-4534.

Lowe, et al., Kinetto Specificity in Papain-catalyzed Hydrolyses, Biochem. J.; 1971; 124(1); pp. 107-115.

Maciewicz, et al., A comparison of Four Cathepsins (B,L,N and S) with Collagenolytic Activity From Rabbit Spleen, Biochem J.; 1998; 256; pp. 433-440.

Marquis, et al., Azeanone-based Inhibitors of Human and Rat Cathepsin K., J. Med. Chem.; 2000; 44(9); pp. 1380-1395.

Nakagawa, et al., Imparied Invariant Chain Degradation and Antigen Presentation and Diminished Collagen-induced Arthritis in Cathepsin S-null Mice, Immunity: 1999; 10; pp. 207-217.

Otto, et al., Cysteine Proteases and their Inhibitors, Chem. Rev.; 1997; 97; pp. 133-171.

Shi, et al., Molecular Cloning and Expression of Human Alveolar Macrophage Cathepsin S, an Elastinolytic Cysteine Protease, J. Biol. Chem.; 1992; 267; pp. 7258-7262.

Singh, et al., β-lactama as Enzyme Inhibitors, IDrugs; 2000; 3(6): pp. 612-617.

Villadangos, et al., Cathepsin S Activity Regulates Antigen Presentation and Immunity, J. Clin. Invest.; 1998; 101(10): pp. 2351-2363.

COMPOUNDS AND COMPOSITIONS AS CATHEPSIN INHIBITORS

This application is based on and claims priority from U.S. Provisional Application Ser. No. 60/257,603 filed on Dec. 22, 2000.

This Application relates to compounds and compositions for treating diseases associated with cysteine protease activity, particularly diseases associated with activity of cathepsin S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. An increase in cathepsin S activity contributes to the pathology and/or symptomatology of a number of diseases. Accordingly, molecules that inhibit the activity of cathepsin S protease are useful as therapeutic agents in the treatment of such diseases.

SUMMARY OF THE INVENTION

This Application relates to compounds of Formula I:

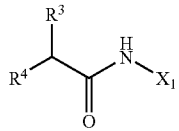

I $X^1$ is —C($R^1$)($R^2$)$X^2$ or —$X^3$;

$X^2$ is cyano, —CHO, —C($R^7$)($R^8$)$R^5$, —C($R^7$)($R^8$)$CF_3$, —C($R^7$)($R^8$)$CF_2CF_2R^9$, —CH=CHS(O)$_2R^5$, —C($R^7$)($R^8$)$CF_2$C(O)NR$^5R^6$, —C($R^7$)($R^8$)C($R^7$)($R^8$)NR$^5R^6$, —C($R^7$)($R^8$)C($R^7$)($R^8$)OR$^5$, —C($R^7$)($R^8$)CH$_2$OR$^5$, —C($R^7$)($R^8$)CH$_2$N($R^6$)SO$_2R^5$, —C($R^7$)($R^8$)C($R^7$)($R^8$)N($R^6$)(CH$_2$)$_2$OR$^6$, —C($R^7$)($R^8$)C($R^7$)($R^8$)N($R^6$)(CH$_2$)$_2$NR$^6$ or —C($R^7$)($R^8$)C($R^7$)($R^8$)R$^5$; wherein R$^5$ is (C$_{1-4}$)alkyl, (C$_{6-10}$)aryl(C$_{0-6}$)alkyl, hetero(C$_{4-10}$)aryl(C$_{0-6}$)alkyl, (C$_{4-10}$)cycloalkyl(C$_{0-6}$)alkyl or hetero(C$_{4-10}$)cycloalkyl(C$_{0-6}$)alkyl; R$^6$ is hydrogen or (C$_{1-6}$)alkyl; R$^7$ is hydrogen or (C$_{1-4}$)alkyl and R$^8$ is hydroxy or R$^7$ and R$^8$ together form oxo; R$^9$ is hydrogen, halo, (C$_{1-4}$)alkyl, (C$_{5-10}$)aryl(C$_{0-6}$)alkyl or hetero(C$_{5-10}$)aryl(C$_{0-6}$)alkyl;

$X^3$ represents a group of Formula (a):

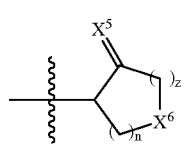

(a)

in which n is 1 or 2, z is 0 or 1, $X^5$ is selected from NR$^{10}$, S or O, wherein R$^{10}$ is hydrogen or (C$_{1-6}$)alkyl, and $X^6$ is O, S or NR$^{11}$, wherein R$^{11}$ is selected from hydrogen, (C$_{1-6}$)alkyl, —$X^4$C(O)OR$^{12}$, —$X^4$C(O)R$^{13}$, —$X^4$C(O)NR$^{12}$R$^{12}$, —$X^4$S(O)$_2$NR$^{12}$R$^{12}$, —$X^4$S(O)$_2$R$^{14}$, —R$^{15}$, —$X^4$S(O)$_2$R$^{15}$, —$X^4$C(O)R$^{15}$, —$X^4$C(O)OR$^{15}$—$X^4$C(O)NR$^{12}$R$^{15}$ and —$X^4$S(O)$_2$NR$^{12}$R$^{15}$, in which $X^4$ is a bond or (C$_{1-6}$)alkylene; R$^{12}$ at each occurrence independently is hydrogen or (C$_{1-6}$)alkyl; R$^{13}$ is hydrogen, (C$_{1-6}$)alkyl or halo-substituted (C$_{1-6}$)alkyl, R$^{14}$ is (C$_{1-6}$)alkyl or halo-substituted(C$_{1-6}$)alkyl and is (C$_{3-10}$)cycloalkyl(C$_{0-6}$)alkyl, hetero(C$_{3-10}$)cycloalkyl (C$_{0-3}$)alkyl, (C$_{6-10}$)aryl(C$_{0-6}$)alkyl, hetero(C$_{5-10}$)aryl(C$_{0-6}$) alkyl, (C$_{9-12}$)bicycloaryl(C$_{0-6}$)alkyl or hetero(C$_{8-12}$)bicycloaryl(C$_{0-6}$)alkyl;

wherein within $X^1$ any cycloalkyl, heterocycloalkyl, aryl or heteroaryl may be substituted with 1 radical R$^{20}$ selected from —R$^{15}$, —$X^4$OR$^{15}$, —$X^4$SR$^{15}$, —$X^4$S(O) R$^{15}$, —$X^4$S(O)$_2$R$^{15}$, —$X^4$C(O)R$^{15}$, —$X^4$C(O)OR$^{15}$, —$X^4$OC(O)R$^{15}$, —$X^4$NR$^{15}$R$^{12}$, —$X^4$NR$^{12}$C(O)R$^{15}$, —$X^4$NR$^{12}$C(O)OR$^{15}$, —$X^4$C(O)NR$^{15}$R$^{12}$, —$X^4$S(O)$_2$NR$^{15}$R$^{12}$, —$X^4$NR$^{12}$S(O)$_2$R$^{15}$, —$X^4$NR$^{12}$C(O) NR$^{15}$R$^{12}$ and —$X^4$NR$^{12}$C(NR$^{12}$)NR$^{15}$R$^{12}$; and wherein $X^1$ and R$^{20}$ may be substituted further with 1 to 5 radicals independently selected from (C$_{1-6}$)alkyl, cyano, halo, halo-substituted(C$_{1-4}$)alkyl, nitro, —$X^4$NR$^{12}$R$^{12}$, —$X^4$NR$^{12}$C(O)R$^{12}$, —$X^4$NR$^{12}$C(O) OR$^{12}$, —$X^4$NR$^{12}$C(O)NR$^{12}$R$^{12}$—$X^4$NR$^{12}$C(R$^{12}$) NR$^{12}$R$^{12}$—$X^4$OR$^{13}$, —$X^4$SR$^{13}$, —$X^4$C(O)OR$^{12}$, —$X^4$C(O)R$^{13}$, —$X^4$OC(O)R$^{13}$, —$X^4$C(O)NR$^{12}$R$^{12}$, —$X^4$S(O)$_2$NR$^{12}$R$^{12}$, —$X^4$NR$^{12}$S(O)$_2$R$^{13}$, —$X^4$P(O) (OR$^{12}$)OR$^{12}$, —$X^4$OP(O)(OR$^{12}$)OR$^{12}$, —$X^4$S(O)R$^{14}$ and —$X^4$S(O)$_2$R$^{14}$ wherein $X^4$, R$^{12}$, R$^{13}$, R$^{14}$ and R$^{15}$ are as defined above;

R$^1$ and R$^2$ are both fluoro; or

R$^1$ is hydrogen or (C$_{1-6}$)alkyl and R$^2$ is selected from the group consisting of hydrogen, (C$_{1-6}$)alkyl, cyano, —$X^4$NR$^{12}$R$^{12}$, —$X^4$NR$^{12}$C(O)R$^{12}$, —$X^4$NR$^{12}$C(O) OR$^{12}$, —$X^4$NR$^{12}$C(O)NR$^{12}$R$^{12}$, —$X^4$NR$^{12}$C(NR$^{12}$) NR$^{12}$R$^{12}$, —$X^4$OR$^{13}$, —$X^4$SR$^{13}$, —$X^4$C(O)OR$^{12}$, —$X^4$C(O)R$^{13}$, —$X^4$OC(O)R$^{13}$, —$X^4$C(O)NR$^{12}$R$^{12}$, —$X^4$S(O)$_2$NR$^{12}$R$^{12}$, —$X^4$NR$^{12}$S(O)$_2$R$^{13}$, —$X^4$P(O) (OR$^{12}$)OR$^{12}$, —$X^4$OP(O)(OR$^{12}$)OR$^{12}$, —$X^4$S(O)R$^{14}$, —$X^4$S(O)$_2$R$^{14}$, —R$^{15}$, —$X^4$OR$^{15}$, —$X^4$SR$^{15}$, —$X^4$S (O)R$^{15}$, —$X^4$S(O)$_2$R$^{15}$, —$X^4$C(O)R$^{15}$, —$X^4$C(O) OR$^{15}$, —$X^4$OC(O)R$^{15}$, —$X^4$NR$^{15}$R$^{12}$, —$X^4$NR$^{12}$C(O) R$^{15}$, —$X^4$NR$^{12}$C(O)OR$^{15}$, —$X^4$C(O)NR$^{15}$R$^{12}$, —$X^4$S (O)$_2$NR$^{15}$R$^{12}$, —$X^4$NR$^{12}$S(O)$_2$R$^{15}$, —$X^4$NR$^{12}$C(O) NR$^{15}$R$^{12}$ and —$X^4$NR$^{12}$C(NR$^{12}$)NR$^{15}$R$^{12}$, wherein $X^4$, R$^{12}$, R$^{13}$, R$^{14}$ and R$^{15}$ are as defined above; or R$^1$ and R$^2$ taken together with the carbon atom to which both R$^1$ and R$^2$ are attached form (C$_{3-8}$)cycloalkylene or hetero(C$_{3-8}$)cycloalkylene; wherein R$^2$, said cycloalkylene and said heterocycloalkylene may be substituted further with 1 to 3 radicals independently selected from (C$_{1-6}$)alkyl, cyano, halo, halo-substituted (C$_{1-4}$)alkyl, nitro, —$X^4$NR$^{12}$R$^{12}$, —$X^4$NR$^{12}$C(O)R$^{12}$, —$X^4$NR$^{12}$C(O)OR$^{12}$, —$X^4$NR$^{12}$C(O)NR$^{12}$R$^{12}$, —$X^4$NR$^{12}$C(NR$^{12}$)NR$^{12}$R$^{12}$, —$X^4$OR$^{13}$, —$X^4$SR$^{13}$, —$X^4$C(O)OR$^{12}$, —$X^4$C(O)R$^{13}$, —$X^4$OC(O)R$^{13}$, —$X^4$C(O)NR$^{12}$R$^{12}$, —$X^4$S(O)$_2$NR$^{12}$R$^{12}$, —$X^4$NR$^{12}$S (O)$_2$R$^{13}$, —$X^4$P(O)(OR$^{12}$)OR$^{12}$, —$X^4$OP(O)(OR$^{12}$) OR$^{12}$, —$X^4$S(O)R$^{14}$ and —$X^4$S(O)$_2$R$^{14}$, wherein $X^4$, R$^{12}$, R$^{13}$ and R$^{14}$ are as defined above;

R$^3$ and R$^4$ are independently —C(R$^{16}$)(R$^{17}$)$X^7$, wherein R$^{16}$ and R$^{17}$ are hydrogen, (C$_{1-6}$)alkyl or fluoro, or R$^{16}$ is hydrogen and R$^{17}$ is hydroxy and $X^7$ is selected from —$X^4$NR$^{12}$R$^{12}$, —$X^4$NR$^{12}$C(O)R$^{12}$, —$X^4$NR$^{12}$C(O)

$OR^{12}$, $-X^4NR^{12}C(O)NR^{12}R^{12}$, $-X^4NR^{12}C(NR^{12})NR^{12}R^{12}$, $-X^4OR^{13}$, $-X^4SR^{13}$, $-X^4C(O)R^{12}$, $-X^4C(O)R^{13}$, $-X^4OC(O)R^{13}$, $-X^4C(O)NR^{12}R^{12}$, $-X^4S(O)_2NR^{12}R^{12}$, $-X^4NR^{12}R^{12}S(O)_2R^{13}$, $-X^4P(O)(OR^{12})OR^{12}$, $-X^4OP(O)(OR^{12})OR^{12}$, $-X^4S(O)R^{14}$, $-X^4S(O)_2R^{14}$, $-R^{15}$, $-X^4OR^{15}$, $-X^4SR^{15}$, $-X^4S(O)R^{15}$, $-X^4S(O)_2R^{15}$, $-X^4C(O)R^{15}$, $-X^4C(O)OR^{15}$, $-X^4OC(O)R^{15}$, $-X^4NR^{15}R^{12}$, $-X^4NR^{12}C(O)R^{15}$ $-X^4NR^{12}C(O)OR^{15}$, $-X^4C(O)NR^{15}R^{12}$, $-X^4S(O)_2NR^{15}R^{12}$, $-X^4NR^{12}S(O)_2R^{15}$, $-X^4NR^{12}C(O)NR^{15}R^{12}$ and $-X^4NR^{12}C(NR^{12})NR^{15}R^{12}$, wherein $X^4$, $R^{12}$, $R^{13}$, $R^{14}$ and $R^{15}$ are as defined above;

wherein within one of $R^3$ or $R^4$ any cycloalkyl, heterocycloalkyl, aryl or heteroaryl may be substituted with 1 radical $R^{21}$ selected from $-R^{15}$, $-X^4OR^{15}$, $-X^4SR^{15}$, $-X^4S(O)R^{15}$, $-X^4S(O)_2R^{15}$, $-X^4C(O)R^{15}$, $-X^4C(O)OR^{15}$, $-X^4OC(O)R^{15}$, $-X^4NR^{15}R^{12}$, $-X^4NR^{12}C(O)R^{15}$, $-X^4NR^{12}C(O)OR^{15}$, $-X^4C(O)NR^{12}R^{15}$, $-X^4S(O)_2NR^{15}R^{12}$, $-X^4NR^{12}S(O)_2R^{15}$, $-X^4NR^{12}C(O)NR^{15}R^{12}$ and $-X^4NR^{12}C(NR^{12})NR^{15}R^{12}$, wherein $X^4$, $R^{12}$ and $R^{15}$ are as defined above; and wherein each of $R^3$, $R^4$ and $R^{21}$ may be substituted further with 1 to 5 radicals independently selected from $(C_{1-6})$alkyl, cyano, halo, halo-substituted $(C_{1-4})$alkyl, nitro, $-X^4NR^{12}R^{12}$, $-X^4NR^{12}C(O)R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{13}$, $-X^4SR^{13}$, $-X^4C(O)OR^{12}$, $-X^4C(O)R^{13}$, $-X^4OC(O)R^{13}$, $-X^4C(O)NR^{12}R^{12}$, $-X^4S(O)_2NR^{12}R^{12}$, $-X^4NR^{12}S(O)_2R^{13}$, $-X^4P(O)(OR^{12})OR^{12}$, $-X^4OP(O)(OR^{12})OR^{12}$, $-X^4S(O)R^{14}$ and $-X^4S(O)_2R^{14}$, wherein $X^4$, $R^{12}$, $R^{13}$ and $R^{14}$ are as defined above; provided that only one bicyclic ring structure is present within each of $R^3$ or $R^4$; and provided that when $X^2$ is cyano and $X^7$ within one of $R^3$ or $R^4$ is $-X^4C(O)R^{13}$ or $-X^4C(O)R^{15}$, wherein $X^4$ is a bond, then $X^7$ within the other of $R^3$ or $R^4$ is limited to $-X^4SR^{15}$, $-X^4S(O)R^{15}$ and $-X^4S(O)_2R^{15}$, wherein $R^{15}$ is $(C_{6-10})$aryl$(C_{1-6})$alkyl substituted with 1 to 5 radicals or hetero$(C_{5-10})$aryl $(C_{6-10})$alkyl optionally substituted with 1 to 5 radicals, wherein said radicals are independently selected from $(C_{1-6})$alkyl, cyano, halo, halo-substituted$(C_{1-4})$alkyl, nitro, $-X^4NR^{12}R^{12}$, $-X^4NR^{12}C(O)R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{13}$, $-X^4SR^{13}$, $-X^4C(O)OR^{12}$, $-X^4C(O)R^{13}$, $-X^4OC(O)R^{13}$, $-X^4C(O)NR^{12}R^{12}$, $-X^4S(O)_2NR^{12}R^{12}$, $-X^4NR^{12}S(O)_2R^{13}$, $-X^4P(O)(OR^{12})OR^{12}$, $-X^4OP(O)(OR^{12})OR^{12}$, $-X^4S(O)R^{14}$ and $-X^4S(O)_2R^{14}$, wherein $X^4$, $R^{12}$, $R^{13}$ and $R^{14}$ are as defined above, provided that the radical is not selected from only halo when $R^{15}$ is $(C_{6-10})$aryl $(C_{1-6})$alkyl; and provided that when $X^2$ is cyano then $X^7$ within $R^3$ and $R^4$ is not $-X^4C(O)NR^{12}R^{12}$, $-X^4C(O)NR^{15}R^{12}$ or $-X^4C(O)NR^{18}R^{19}$, wherein $X^4$ is a bond and $R^{18}$ and $R^{19}$ together with the nitrogen atom to which they are attached form hetero$(C_{3-10})$cycloalkyl or hetero$(C_{5-10})$aryl;

and the N-oxide derivatives, prodrug derivatives, protected derivatives, individual isomers and mixtures of isomers thereof; and the pharmaceutically acceptable salts and solvates (e.g. hydrates) of such compounds and the N-oxide derivatives, prodrug derivatives, protected derivatives, individual isomers and mixtures of isomers thereof.

A second aspect of the invention is a pharmaceutical composition which contains a compound of Formula I or a N-oxide derivative, individual isomer or mixture of isomers thereof, or a pharmaceutically acceptable salt thereof, in admixture with one or more suitable excipients.

A third aspect of the invention is a method for treating a disease in an animal in which inhibition of cathepsin S can prevent, inhibit or ameliorate the pathology and/or symptomatology of the disease, which method comprises administering to the animal a therapeutically effective amount of compound of Formula I or a N-oxide derivative, individual isomer or mixture of isomers thereof; or a pharmaceutically acceptable salt thereof.

A fourth aspect of the invention is the processes for preparing compounds of Formula I and the N-oxide derivatives, prodrug derivatives, protected derivatives, individual isomers and mixtures of isomers thereof; and the pharmaceutically acceptable salts thereof.

DETAILED DESCRIPTION OF THE INVENTION

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by a straight or branched chain arrangement of the constituent carbon atoms and may be saturated or partially unsaturated with two or more double or triple bonds.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g., $(C_{1-6})$alkylene includes methylene ($-CH_2-$), ethylene ($-CH_2CH_2-$), trimethylene ($-CH_2CH_2CH_2-$), tetramethylene ($-CH_2CH_2CH_2CH_2-$)2-butenylene ($-CH_2CH=CHCH_2-$), 2-methyltetramethylene ($-CH_2CH(CH_3)CH_2CH_2-$), pentamethylene ($-CH_2CH_2CH_2CH_2CH_2-$) and the like).

"Alkylidene" means a straight or branched saturated or unsaturated, aliphatic, divalent radical having the number of carbon atoms indicated (e.g. $(C_{1-6})$alkylidene includes methylene ($=CH_2$), ethylidene ($=CHCH_3$), isopropylidene ($=C(CH_3)_2$), propylidene ($=CHCH_2CH_3$), allylidene ($=CH-CH=CH_2$), and the like).

"Amino" means the radical $-NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to $4n+2$.

"Aryl" means a monocyclic or fused bicyclic ring assembly containing the total number of ring carbon atoms indicated, wherein each ring is comprised of 6 ring carbon atoms and is aromatic or when fused with a second ring forms an aromatic ring assembly. For example, optionally substituted $(C_{6-10})$aryl as used in this Application includes, but is not limited to, biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluorophenyl, 2-iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like.

"Bicycloaryl" means a bicyclic ring assembly containing the number of ring carbon atoms indicated, wherein the rings are linked by a single bond or fused and at least one of the rings comprising the assembly is aromatic, and any $(C_{1-6})$ alkylidene, carbocyclic ketone, thioketone or iminoketone derivative thereof (e.g., $(C_{9-12})$bicycloaryl includes biphenyl, cyclohexylphenyl, 1,2-dihydronaphthyl, 2,4-dioxo-1,2,3,4-tetrahydronaphthyl, indanyl, indenyl, 1,2,3,4-tetrahydronaphthyl, and the like).

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone derivative" means a derivative containing the moiety —C(O)—.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic, fused bicyclic or bridged polycyclic ring assembly containing the number of ring carbon atoms indicated, and any $(C_{1-6})$alkylidene, carbocyclic ketone, thioketone or iminoketone derivative thereof (e.g., $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Cycloalkylene" means a divalent saturated or partially unsaturated, monocyclic ring or bridged polycyclic ring assembly containing the number of ring carbon atoms indicated, and any carbocyclic ketone, thioketone or iminoketone derivative thereof. For example, the instance wherein "R$^1$ and R$^2$ together with the carbon atom to which both R$^1$ and R$^2$ are attached form $(C_{3-8})$cycloalkylene" includes, but is not limited to, the following:

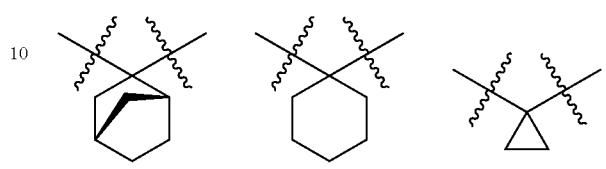

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom moiety" includes —N═, —NR—, —O—, —S— or —S(O)$_2$—, wherein R is hydrogen, $(C_{1-6})$alkyl or a protecting group.

"Heterocycloalkylene" means cycloalkylene, as defined in this Application, provided that one or more of the ring member carbon atoms indicated, is replaced by heteroatom moiety selected from —N═, —NR—, —O—, —S— or —S(O)$_2$—, wherein R is hydrogen or $(C_{1-6})$alkyl. For example, the instance wherein R$^1$ and R$^2$ together with the carbon atom to which both R$^1$ and R$^2$ are attached form hetero$(C_{3-8})$cycloalkyl" includes, but is not limited to, the following:

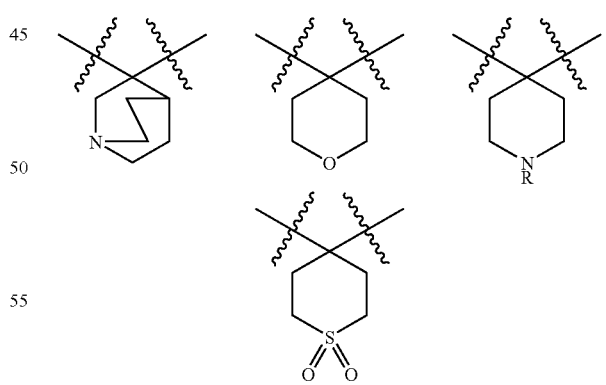

in which R is hydrogen, $(C_{1-6})$alkyl, or a protecting group.

"Heteroaryl" as a group or part of a group denotes an optionally substituted aromatic monocyclic or multicyclic organic moiety of about 5 to about 10 ring members in which one or more of the ring members is/are element(s) other than carbon, for example nitrogen, NR, oxygen or sulfur, wherein R is hydrogen, $(C_{1-6})$alkyl, a protecting group or represents the free valence which serves as the point of attachment to a ring nitrogen. For example, optionally substituted hetero($C_{5-10}$)aryl as used in this Application includes, but is not limited to, 4-amino-2-hydroxypyrimidin-5-yl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4]triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3]triazol-4-yl, 5-trifluoromethylpyrid-2-yl, and the like. Suitable protecting groups include tert-butoxycarbonyl, benzyloxycarbonyl, benzyl, 4-methoxybenzyl, 2-nitrobenzyl, and the like. Optionally substituted hetero($C_{5-10}$)aryl as used in this Application to define $R^5$ includes 1H-benzoimidazol-2-yl, pyrimidin-2-yl, benzooxazol-2-yl, benzothiazol-2-yl, pyridazin-3-yl, 3-phenyl-[1,2,4]oxadiazol-5-yl, 3-ethyl-[1,2,4]oxadiazol-5-yl, and the like.

"Heterobicycloaryl" means bicycloaryl, as defined in this Application, provided that one or more of the ring carbon atoms indicated are replaced by a heteroatom moiety selected from —N=, —NR—, —O— or —S—, wherein R is hydrogen, ($C_{1-6}$)alkyl, a protecting group or represents the free valence which serves as the point of attachment to a ring nitrogen, and any carbocyclic ketone, thioketone or iminoketone derivative thereof. For example, optionally substituted hetero($C_{8-10}$)bicycloaryl as used in this Application includes, but is not limited to, 2-amino-4-oxo-3,4-dihydropteridin-6-yl, and the like. In general, the term heterobicycloaryl as used in this Application includes, for example, benzo[1,3]dioxol-5-yl, 3,4-dihydro-2H-[1,8]naphthyridinyl, 3,4-dihydro-2H-quinolinyl, 2,4-dioxo-3,4-dihydro-2H-quinazolinyl, 1,2,3,4,5,6-hexahydro[2,2']bipyridinylyl, 3-oxo-2,3-dihydrobenzo[1,4]oxazinyl, 5,6,7,8-tetrahydroquinolinyl, and the like.

"Heterocycloalkyl" means cycloalkyl, as defined in this Application, provided that one or more of the ring carbon atoms indicated are replaced by a heteroatom moiety selected from —N=, —NR—, —O— or —S—, wherein R is hydrogen, ($C_{1-6}$)alkyl, a protecting group or represents the free valence which serves as the point of attachment to a ring nitrogen, and any carbocyclic ketone, thioketone or iminoketone derivative thereof (e.g., the term hetero($C_{5-10}$) cycloalkyl includes imidazolidinyl, morpholinyl, piperazinyl, piperidyl, pyrrolidinyl, pyrrolinyl, quinuclidinyl, and the like. A ketone derivative of piperazinyl would be 3-oxo-piperazin-1-yl). Suitable protecting groups include tert-butoxycarbonyl, benzyloxycarbonyl, benzyl, 4-methoxybenzyl, 2-nitrobenzyl, and the like. Both the unprotected and protected derivatives fall within the scope of the invention.

"Hydroxy" means the radical —OH. Unless indicated otherwise, the compounds of the invention containing hydroxy radicals include protected derivatives thereof. Suitable protecting groups for hydroxy moieties include benzyl and the like.

"Iminoketone derivative" means a derivative containing the moiety —C(NR)—, wherein R is hydrogen or ($C_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula I are meant to be encompassed all possible stereoisomers. Thus, for example, the name N-[1-(1-benzylcarbamoyl-methanoyl)-propyl]-4-morpholin-4-yl-4-oxo-2-benzylsulfonylmethyl-butyramide is meant to include N-[(S)-1-(1-benzylcarbamoyl-methanoyl)-propyl]-4-morpholin-4-yl-4-oxo-2-benzylsulfonylmethyl-butyramide and N-[(R)-1-(1-benzylcarbamoyl-methanoyl)-propyl]-4-morpholin-4-yl-4-oxo-2-benzylsulfonylmethyl-butyramide and any mixture, racemic or otherwise, thereof.

"Ketone derivative" means a derivative containing the moiety —C(O)—.

"Nitro" means the radical —$NO_2$.

"Optional" or "optionally" or "may be" means that the subsequently described event or circumstance may or may not occur, and that the description includes instances where the event or circumstance occurs and instances in which it does not. For example, the phrase "wherein $R^3$, $R^4$ and $R^{21}$ may be substituted further by 1 to 5 radicals . . . " means that $R^3$, $R^4$ and/or $R^{21}$ may or may not be substituted in order to fall within the scope of the invention.

"N-oxide derivatives" means derivatives of compounds of Formula I in which nitrogens are in an oxidized state (i.e., O—N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound which is convertible in vivo by metabolic means (e.g. by hydrolysis) to a compound of Formula I. For example an ester of a compound of Formula I containing a hydroxy group may be convertible by hydrolysis in vivo to the parent molecule. Alternatively an ester of a compound of Formula I containing a carboxy group may be convertible by hydrolysis in vivo to the parent molecule. Suitable esters of compounds of Formula I containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula I containing a carboxy group, are for example those described by F. J. Leinweber, Drug Metab. Res., 1987, 18, page 379. An especially useful class of esters of compounds of Formula I containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl) benzoates, and (4-alkylpiperazin-1-yl)benzoates, e.g. 3- or 4-(4-alkylpiperazin-1-yl)benzoates.

"Protected derivatives" means derivatives of compounds of Formula I in which a reactive site or sites are blocked with protecting groups. Protected derivatives of compounds of Formula I are useful in the preparation of compounds of Formula I or in themselves may be active cathepsin S inhibitors. A comprehensive list of suitable protecting groups can be found in T. W. Greene, *Protecting Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature:

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound of Formula I in which $R^1$ is hydrogen, $R^2$ is propyl, $R^3$ and $R^4$ are each benzylsulfonylmethyl; that is, a compound having the following structure:

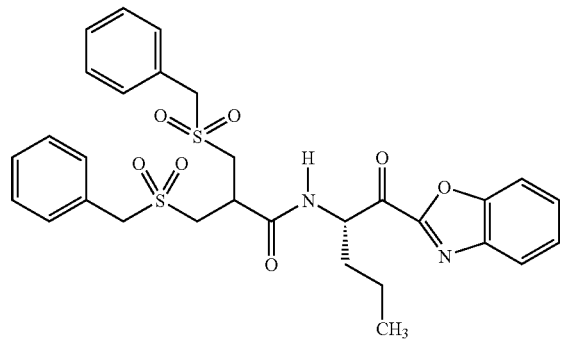

is named N-[(S)-1-(1-benzooxazol-2-yl-methanoyl)-butyl]-3-benzylsulfonyl-2-benzylsulfonylmethyl-propionamide;

With reference to formula (I) above, the following are particular and preferred groupings:

$X^1$ may particularly represent —$C(R^1)(R^2)X^2$ in which $R^1$ is hydrogen or $(C_{1-6})$alkyl and $R^2$ is hydrogen, —$X^4OR^{13}$ or —$R^{15}$, in which within $R^{15}$ any aryl, heteroaryl, cycloalkyl or heterocycloalkyl may be substituted with 1 to 3 radicals independently selected from $(C_{1-6})$alkyl, cyano, halo, halo-substituted$(C_{1-4})$alkyl, nitro, —$X^4NR^{12}R^{12}$, —$X^4NR^{12}C(O)R^{12}$, $X^4NR^{12}C(O)OR^{12}$, —$X^4NR^{12}C(O)NR^{12}R^{12}$, —$X^4NR^{12}C(NR^{12})NR^{12}R^{12}$, —$X^4OR^{13}$, —$X^4SR^{13}$, $X^4C(O)OR^{12}$, —$X^4C(O)R^{13}$, —$X^4OC(O)R^{13}$, —$X^4C(O)NR^{12}R^{12}$, —$X^4S(O)_2NR^{12}R^{12}$, —$X^4NR^{12}S(O)_2R^{13}$, —$X^4P(O)(OR^{12})OR^{12}$, —$X^4O$ $P(O)(OR^{12})OR^{12}$, —$X^4S(O)R^{14}$ and —$X^4S(O)_2R^{14}$ wherein $X^4$ is a bond or $(C_{1-6})$alkylene, $R^{12}$ at each occurrence independently is hydrogen or $(C_{1-6})$ alkyl, $R^{13}$ is hydrogen, $(C_{1-6})$alkyl or halo-substituted$(C_{1-6})$ alkyl, $R^{14}$ is $(C_{1-6})$alkyl or halo-substituted$(C_{1-6})$alkyl; and $X^5$ is cyano, —CHO, —C(O)$R^5$, —C(O)CF$_3$, —C(O) CF$_2$CF$_2$R$^9$—CH=CHS(O)$_2$R$^5$, —C(O)CF$_2$C(O)NR$^5$R$^6$, —C(O)C(O)NR$^5$R$^6$, —C(O)C(O)OR$^5$, —C(O)CH$_2$OR$^5$, —C(O)CH$_2$N(R$^6$)SO$_2$R$^5$, —C(O)C(O)N(R$^6$)(CH$_2$)$_2$OR$^6$, —C(O)C(O)N(R$^6$)(CH$_2$)$_2$NR$^6$ or —C(O)C(O)R$^5$; wherein $R^5$ is $(C_{1-4})$alkyl, $(C_{6-10})$aryl$(C_{0-6})$alkyl, hetero$(C_{4-10})$aryl$(C_{0-6})$alkyl, $(C_{4-10})$cycloalkyl$(C_{0-6})$alkyl or hetero$(C_{4-10})$cycloalkyl$(C_{0-6})$alkyl, $R^6$ is hydrogen or $(C_{1-6})$alkyl and $R^9$ is halo.

$X^1$ may also particularly represent —C(R$^1$)(R$^2$)X$^2$ in which $R^1$ and $R^2$ taken together with the carbon atom to which both $R^1$ and $R^2$ are attached form $(C_{3-8})$cycloalkylene or hetero$(C_{3-8})$cycloalkylene, in which the cycloalkylene or the heterocycloalkylene is optionally substituted with 1 to 3 radicals independently selected from $(C_{1-6})$alkyl and hydroxy and $X^2$ is cyano, —CHO, —C(O)R$^5$, —C(O)CF$_3$, —C(O)CF$_2$CF$_2$R$^9$ —CH=CHS(O)$_2$R$^5$, —C(O)CF$_2$C(O) NR$^5$R$^6$, —C(O)C(O)NR$^5$R$^6$—C(O)C(O)OR$^5$, —C(O) CH$_2$OR$^5$, —C(O)CH$_2$N(R$^6$)SO$_2$R$^5$, —C(O)C(O)N(R$^6$) (CH$_2$)$_2$OR$^6$, —C(O)C(O)N(R$^6$)(CH$_2$)$_2$NR$^6$ or —C(O)C(O) R$^5$.

$X^1$ may also particularly represent —$X^3$, wherein $X^3$ is a group of formula (b):

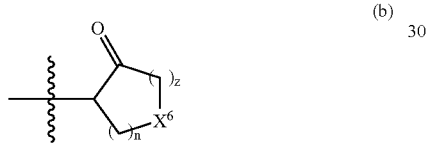

(b)

in which n is 1 or 2, z is 0 or 1, $X^6$ is O or $NR^{11}$, wherein $R^{11}$ is selected from hydrogen $(C_{1-6})$alkyl, —X$^4$C(O)OR$^{12}$, —X$^4$OC(O)R$^{12}$, —X$^4$C(O)R$^{13}$, —X$^4$S(O)$_2$R$^{12}$, X$^4$S(O)$_2$R$^{15}$, X$^4$C(O)R$^{15}$ and —X$^4$C(O)OR$^{15}$, in which $X^4$ is a bond or $(C_{1-6})$alkylene; $R^{12}$ at each occurrence independently is hydrogen or $(C_{1-6})$alkyl; $R^{13}$ is hydrogen, $(C_{1-6})$alkyl or halo-substituted$(C_{1-6})$alkyl and $R^{15}$ is $(C_{3-10})$cycloalkyl$(C_{0-6})$alkyl, hetero$(C_{3-10})$cycloalkyl$(C_{0-3})$ alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl $(C_{0-6})$alkyl; within $X^3$ any cycloalkyl or heterocycloalkyl group may be optionally substituted by substituted further by 1 to 5 radicals independently selected from $(C_{1-6})$alkyl, cyano, halo, halo-substituted$(C_{1-4})$alkyl, nitro, —X$^4$NR$^{12}$R$^{12}$, —X$^4$NR$^{12}$C(O)R$^{12}$, —X$^4$NR$^{12}$C(O)OR$^{12}$, —X$^4$NR$^{12}$C(O)NR$^{12}$R$^{12}$, —X$^4$NR$^{12}$C(NR$^{12}$)NR$^{12}$R$^{12}$, —X$^4$OR$^{13}$, —X$^4$SR$^{13}$, —X$^4$C(O)OR$^{12}$, —X$^4$C(O)R$^{13}$, —X$^4$OC(O)R$^{13}$, —X$^4$C(O)NR$^{12}$R$^{12}$, —X$^4$S(O)$_2$NR$^{12}$R$^{12}$, —X$^4$NR$^{12}$S(O)$_2$R$^{13}$, —X$^4$P(O)(OR$^{12}$)OR$^{12}$, —X$^4$OP(O) (OR$^{12}$)OR$^{12}$, —X$^4$S(O)R$^{14}$ and —X$^4$S(O)$_2$R$^{14}$ and/or 1 radical selected from —R$^{15}$, —OR$^{15}$, —SR$^{15}$, —S(O)R$^{15}$, —S(O)$_2$R$^{15}$, —C(O)R$^{15}$, —C(O)OR$^{15}$, —OC(O)R$^{15}$, —NR$^{15}$R$^{12}$, —NR$^{12}$C(O)R$^{15}$, —NR$^{12}$C(O)OR$^{15}$, —C(O) NR$^{15}$R$^{12}$, —S(O)$_2$NR$^{15}$R$^{12}$, —NR$^{12}$S(O)$_2$R$^{15}$, —NR$^{12}$C(O) NR$^{15}$R$^{12}$ and —NR$^{12}$C(NR$^{12}$)NR$^{15}$R$^{12}$ wherein $X^4$ is a bond or $(C_{1-6})$alkylene, $R^{12}$ at each occurrence independently is hydrogen or $(C_{1-6})$alkyl, $R^{13}$ is hydrogen, $(C_{1-6})$ alkyl or halo-substituted$(C_{1-6})$alkyl, $R^{14}$ is $(C_{1-6})$alkyl or halo-substituted$(C_{1-6})$alkyl and $R^{15}$ is $(C_{3-10})$cycloalkyl$(C_{0-6})$alkyl, $(C_{3-10})$cycloalkyl$(C_{0-6})$alkyl, hetero$(C_{3-10})$cycloalkyl$(C_{0-3})$alkyl, $(C_{6-10})$aryl$(C_{0-6})$alkyl, hetero$(C_{5-10})$aryl$(C_{0-6})$alkyl, $(C_{9-12})$bicycloaryl$(C_{0-6})$alkyl or hetero$(C_{8-12})$bicycloaryl$(C_{0-6})$alkyl;

$R^3$ and $R^4$ may particularly represent —C(R$^{16}$)(R$^{17}$)X$^7$, wherein $R^{16}$ and $R^{17}$ are hydrogen, $(C_{1-6})$alkyl or fluoro, or $R^{16}$ is hydrogen and $R^{17}$ is hydroxy and $X^7$ is selected from —X$^4$SR$^{13}$, —X$^4$C(O)R$^{13}$, —X$^4$C(O)NR$^{12}$R$^{12}$, —R$^{15}$, —X$^4$OR$^{15}$, —X$^4$SR$^{15}$, —X$^4$S(O)$_2$R$^{15}$—X$^4$C(O)R$^{15}$ and —X$^4$C(O)NR$^{15}$R$^{12}$, wherein $X^4$ is a bond or $(C_{1-6})$alkylene, $R^{12}$ at each occurrence independently is hydrogen or $(C_{1-6})$ alkyl, $R^{13}$ is hydrogen, $(C_{1-6})$alkyl or halo-substituted$(C_{1-6})$ alkyl, $R^{14}$ is $(C_{1-6})$alkyl or halo-substituted$(C_{1-6})$alkyl and $R^{15}$ is $(C_{3-10})$cycloalkyl$(C_{0-6})$alkyl, $(C_{3-10})$cycloalkyl$(C_{0-6})$ alkyl, hetero$(C_{3-10})$cycloalkyl$(C_{0-3})$alkyl, $(C_{6-10})$aryl$(C_{0-6})$ alkyl, hetero$(C_{5-10})$aryl$(C_{0-6})$alkyl, $(C_{9-12})$bicycloaryl$(C_{0-6})$ alkyl or hetero$(C_{8-12})$bicycloaryl$(C_{0-6})$alkyl;

within $R^3$ and $R^4$ may be substituted further by 1–5 radicals independently selected from $(C_{1-6})$alkyl, cyano, halo, halo-substituted$(C_{1-4})$alkyl, —X$^4$NR$^{12}$C (O)OR$^{12}$, —X$^4$OR$^{13}$, —X$^4$C(O)OR$^{12}$, —X$^4$C(O)R$^{13}$, —X$^4$C(O)NR$^{12}$R$^{12}$, —X$^4$NR$^{12}$S(O)$_2$R$^{13}$ and —X$^4$S (O)$_2$R$^{14}$ and one of $R^3$ or $R^4$ may be further substituted with 1 radical selected from —R$^{15}$ and —X$^4$OR$^{15}$, wherein $X^4$ is a bond or $(C_{1-6})$alkylene, $R^{12}$ at each occurrence independently is hydrogen or $(C_{1-6})$alkyl, $R^{13}$ is hydrogen, $(C_{1-6})$alkyl or halo-substituted$(C_{1-6})$ alkyl, $R^{14}$ is $(C_{1-6})$alkyl or halo-substituted$(C_{1-6})$alkyl and $R^{15}$ is $(C_{3-10})$cycloalkyl$(C_{0-6})$alkyl, $(C_{3-10})$cycloalkyl$(C_{0-6})$alkyl, hetero$(C_{3-10})$cycloalkyl$(C_{0-3})$ alkyl, $(C_{6-10})$aryl$(C_{0-6})$alkyl, hetero$(C_{5-10})$aryl$(C_{0-6})$ alkyl, $(C_{9-12})$bicycloaryl$(C_{0-6})$alkyl or hetero$(C_{8-12})$ bicycloaryl$(C_{0-6})$alkyl.

$R^3$ and $R^4$ groups include allylsulfonylmethyl, benzylcarbamoyl-methyl, benzyl, benzylsulfanylmethyl, 2-benzenesulfonyl-ethyl, benzenesulfonylmethyl, 2-benzo[1,3]dioxol-5-yl-2-oxo-ethyl, 2-benzo[b]thiophen-2-yl-2-oxo-ethyl, biphenyl-2-ylmethylsulfonylmethyl, biphenyl-4-ylmethylsulfonylmethyl, biphenyl-3-ylmethyl, biphenyl-4-ylmethyl, 2-biphenyl-4-yl-2-oxo-ethyl, 3,5-bis-trifluoromethyl-benzyl-sulfonylmethyl, 3-bromo-benzyl, 2-oxo-2-pyrrolidin-1-yl-ethyl, 2-bromo-benzyl-sulfonylmethyl, (butyl-methyl-carbamoyl)-methyl, 4-tert-butyl-benzylsulfonylmethyl, (3-carbamoyl-phenylcarbamoyl)-methyl, (4-carbamoyl-phenylcarbamoyl)-methyl, 4-carboxy-benzylsulfonylmethyl, 2-(3-chloro-benzo[b]thiophen-2-yl)-2-oxo-ethyl, 2-(4'-chloro-biphenyl-4-yl)-2-oxo-ethyl, 3-chloro-2-fluoro-benzylsulfonylmethyl, 2-chloro-benzylsulfonylmethyl, 3-chloro-benzylsulfonylmethyl, 4-chloro-benzylsulfonylmethyl, 2-(4-chloro-phenyl)-2-oxo-ethyl, 5-chloro-thiophen-2-ylmethylsulfonylmethyl, 2-(3-chloro-thiophen-2-yl)-2-oxo-ethyl, 2-chloro-5-trifluoromethylbenzylsulfonylmethyl, (cyanomethyl-methyl-carbamoyl)-methyl, cyclohexylcarbamoylmethyl, 2-cyclohexyl-ethanesulfonyl, cyclohexylmethylsulfonylmethyl, 2-cyclohexyl-ethyl, cyclohexylmethyl, 2-cyano-benzylsulfonylmethyl, cyclopropylmethylsulfonylmethyl, 3-cyano-benzylsulfonylmethyl, 4-cyano-benzylsulfonylmethyl, 2,5-dichloro-benzylsulfonylmethyl, 2,6-dichloro-benzylsulfonylmethyl, 3,4-dichloro-benzylsulfonylmethyl, 2-[2-(1,1-difluoro-methoxy)-benzenesulfonyl]-ethyl, 2-[3-(1,1-difluoro-methoxy)-benzenesulfonyl]-ethyl, 2-[4-(1,1-difluoro-methoxy)-benzenesulfonyl]-ethyl, 2-(1,1-difluoro-methoxy)-benzylsulfonylmethyl, 3-(1,1-difluoro-methoxy)-benzylsulfonylmethyl, 4-(1,1-difluoro-methoxy)-benzylsulfonylmethyl, 2,3-difluoro-benzylsulfonylmethyl, 2,4-difluoro-benzylsulfonylmethyl, 2,5-difluoro-benzylsulfonylmethyl, 2,6-difluoro-benzylsulfonylmethyl, 3,4-difluoro-benzylsulfonylmethyl, 3,4-dichloro-benzyl-sulfonylmethyl, 2-(3,4-difluoro-phenyl)-2-oxo-ethyl, 2-(3,4-dimethoxy-phenyl)-2-oxo-ethyl, 4-dimethylcarbamoylmethyl, 3,5-dimethyl-isoxazol-4-ylmethylsulfonylmethyl, 3,5-dimethyl-benzylsulfonylmethyl, 2-(3-fluoro-4-methoxy-phenyl)-2-oxo-ethyl, 2-fluoro-3-methyl-benzylsulfonylmethyl, 2-fluoro-benzylsulfonylmethyl, 3-fluoro-benzylsulfonylmethyl, 4-fluoro-benzylsulfonylmethyl, 2-(4-fluoro-phenyl)-2-oxo-ethyl, 4-fluoro-2-trifluoromethoxy-benzyl-sulfonylmethyl, 2-fluoro-3-trifluoromethylbenzylsulfonylmethyl, 2-fluoro-4-trifluoromethylphenyl-methylsulfonylmethyl, 2-fluoro-5-trifluoromethylbenzyl-sulfonylmethyl, 2-fluoro-6-trifluoromethyl-benzylsulfonylmethyl, 4-fluoro-3-trifluoromethyl-benzylsulfonylmethyl, 2-(4-hydroxyphenyl)-2-oxo-ethyl, isobutylsulfanylmethyl, isopropylcarbamoyl-methyl, 2-(4-methylsulfonylaminophenyl)-2-oxo-ethyl, 2-(4-methylsulfonyl-piperazin-1-yl)-2-oxo-ethyl, 5-methyl-2-oxo-hexyl, 2-methoxy-benzyl-sulfonylmethyl, 4-methoxy-benzylsulfonylmethyl, 2-(4-methoxy-phenyl)-2-oxo-ethyl, 3-methyl-benzylsulfonylmethyl, 2-methyl-propane-1-sulfonyl, 2-(5-methyl-thiophen-2-yl)-2-oxo-ethyl, 2-methyl-thiazol-4-yl-methylsulfonylmethyl 5-methyl-thiophene-2-sulfonylmethyl, naphthalen-2-yl, naphthalen-2-ylmethylsulfonylmethyl, 2-naphthalen-2-yl-2-oxo-ethyl, naphthalene-2-sulfonylmethyl, 2-morpholin-4-yl-2-oxo-ethyl, 2-oxo-2-piperidin-1-yl-ethyl, 2-oxo-2-(4-phenoxyphenyl)-ethyl, 2-oxo-2-phenyl-ethyl, 2-oxo-2-pyrrolidin-1-yl-ethyl, 2-oxo-2-thiophen-2-yl-ethyl, 2-oxo-2-thiophen-3-yl-ethyl, 2-oxo-2-p-tolyl-ethyl, 2-oxo-2-(4-trifluoromethoxy-phenyl)-ethyl, 1-oxy-pyridin-2-ylmethylsulfonylmethyl, phenylcarbamoylmethyl, 2-benzylsulfonyl-ethyl, benzylsulfonylmethyl, 4-benzylsulfonylmethyl, 2-phenylsulfanyl-ethyl, prop-2-ene-1-sulfonylmethyl, pyridin-3-ylcarbamoylmethyl, pyridin-4-ylcarbamoylmethyl, 2-(pyridine-2-sulfonyl)-ethyl, 2-(pyridine-4-sulfonyl)-ethyl, pyridin-2-ylmethylsulfonylmethyl, pyridin-3-ylmethylsulfonylmethyl, pyridin-4-ylmethylsulfonylmethyl, (5,6,7,8-tetrahydro-naphthalen-1-ylcarbamoyl)-methyl, tetrahydropyran-4-yloxymethyl, thiophene-2-sulfonylmethyl, o-tolylmethylsulfonylmethyl, m-tolylmethylsulfonylmethyl, p-tolylmethylsulfonylmethyl, 2-(2-trifluoromethoxy-benzenesulfonyl)-ethyl, 2-(3-trifluoromethoxy-benzenesulfonyl)-ethyl, 2-(4-trifluoromethoxy-benzenesulfonyl)-ethyl, 2-trifluoromethoxy-benzylsulfanylmethyl, 2-trifluoromethoxy-benzylsulfonylmethyl, 3-trifluoromethoxy-benzylsulfonylmethyl, 4-trifluoromethoxy-benzylsulfonylmethyl, 2-trifluoromethyl-benzylsulfanylmethyl, 2-trifluoromethyl-benzylsulfonylmethyl, 3-trifluoromethyl-benzylsulfonylmethyl, 4-trifluoromethyl-benzylsulfonylmethyl, 2,3,4-trifluoro-benzylsulfonylmethyl, 2,3,5-trifluoro-benzylsulfonylmethyl, 2,4,5-trifluoro-benzylsulfonylmethyl, 2,4,6-trifluoro-benzylsulfonylmethyl and 2,5,6-trifluoro-benzylsulfonylmethyl. Preferred $R^3$ and $R^4$ groups include allylsulfonylmethyl, benzylsulfanylmethyl, 3-cyano-benzylsulfonylmethyl, cyclohexylmethyl, 2-difluoromethoxy-benzylsulfonylmethyl, isobutylsulfanylmethyl, (2-methyl-thiazol-4-yl)-methylsulfonylmethyl, 2-morpholin-4-yl-2-oxo-ethyl, 2-oxo-2-piperidin-1-yl-ethyl, 2-oxo-2-pyrrolidin-1-yl-ethyl, benzylsulfonylmethyl, tetrahydropyran-4-yloxymethyl, and 3-trifluoromethyl-benzylsulfonylmethyl. Particularly preferred $R^3$ and $R^4$ groups include benzylsulfanylmethyl, 2-difluoromethoxy-benzylsulfonylmethyl, 2-morpholin-4-yl-2-oxo-ethyl and benzylsulfonylmethyl.

It is to be understood that this invention covers all appropriate combinations of the particular and preferred groupings referred to herein unless otherwise stated.

A particular preferred group of compounds of the invention are compounds of formula I(a):

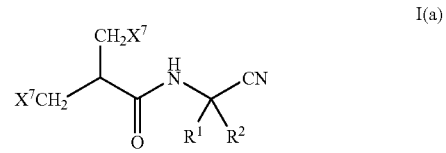

I(a)

wherein $R^1$, $R^2$ and $X^7$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(a) and their N-oxides and their prodrugs, and their protected derivatives, individual isomers and mixtures of isomers thereof.

Compounds of formula I(a) in which $R^1$ is hydrogen and $R^2$ is:
(i) hydrogen;
(ii) —$X^4OR^{13}$, e.g., —$CH_2$—O—$CH_3$ or —$CH_2$—$CH_2$—O—$CH_3$;
(iii) hetero($C_{5-10}$)aryl($C_{0-6}$)alkyl, e.g., thien-2-yl or 5-methylfuran-2-yl;
(iv) ($C_{5-10}$)aryl($C_{0-6}$)alkyl, e.g., phenethyl;
(v) ($C_{1-6}$)alkyl, e.g. ethyl, n-propyl or n-butyl] are preferred.

Compounds of formula I(a) in which $R^1$ and $R^2$ are both methyl are also preferred.

Compounds of formula I(a) in which $R^1$ and $R^2$ taken together with the carbon atom to which both $R^1$ and $R^2$ are attached form ($C_{3-8}$)cycloalkylene, e.g., cyclopropyl, or hetero($C_{3-8}$)cycloalkylene, e.g., tetrahydropyran-4-yl and N-methylpiperidin-4-yl, are also preferred.

Compounds of formula I(a) in which $X^7$ is:
(i) —$R^{15}$ or —$R^{13}$, e.g.,

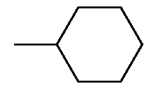

or —CH=$CH_2$, respectively;
(ii) —$X^4C(O)R^{15}$ in which $X^4$ is a direct bond and $R^{15}$ is hetero($C_{3-10}$)cycloalkyl($C_{0-6}$)alkyl, e.g.,

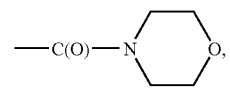

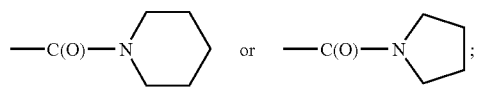

(iii) —$X^4OR^{15}$ in which $X^4$ is a direct bond and $R^{15}$ is hetero($C_{3-10}$)cycloalkyl($C_{0-6}$)alkyl, e.g.,

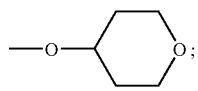

(iv) —X⁴SR¹³ or —X⁴SR¹⁵ in which X⁴ is a direct bond or (C₁₋₆)alkylene, R¹³ is (C₁₋₆)alkyl and R¹⁵ is (C₆₋₁₀)aryl(C₀₋₆)alkyl, e.g.,

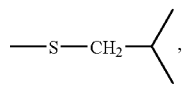

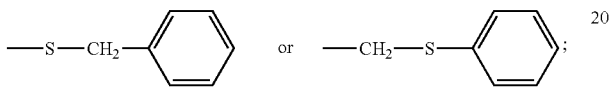

(v) —X⁴S(O)₂R¹³ or —X⁴S(O)₂R¹⁵ in which X⁴ is a direct bond, R¹³ is (C₁₋₆)alkyl and R¹⁵ is (C₆₋₁₀)aryl(C₀₋₆)alkyl, e.g., —SO₂—CH₂—

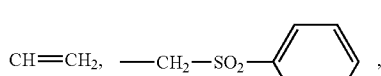

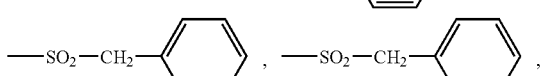

are preferred. Compounds of formula I(a) in which X⁷ represents

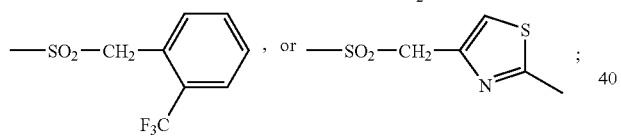

are especially preferred.

A preferred group of compounds of the invention are compounds of formula I(a) in which: R¹ is hydrogen and R²(i) hydrogen, (ii) X⁴OR¹³ e.g. —CH₂—O—CH₃ or —CH₂—CH₂O—CH₃, (iii) hetero(C₅₋₁₀)aryl(C₀₋₆)alkyl, e.g. thien-2-yl or 5-methylfuran-2-yl, (iv)(C₅₋₁₀)aryl(C₀₋₆)alkyl, e.g. phenethyl or (v) (C₁₋₆)alkyl, e.g. ethyl, n-propyl or n-butyl; X⁷ is (i) —R¹³ or —R¹⁵, e.g.

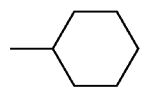

or —CH=CH₂ respectively, (ii) —X⁴C(O)R¹⁵ in which X⁴ is a direct bond and R¹⁵ is hetero(C₃₋₁₀)cycloalkyl(C₀₋₆)alkyl, e.g.

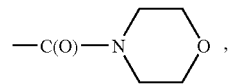

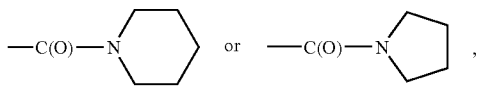

(iii) —X⁴OR¹⁵ in which X⁴ is a direct bond and R¹⁵ is hetero(C₃₋₁₀)cycloalkyl(C₀₋₆)alkyl, e.g.

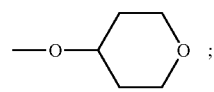

(iv) —X⁴SR¹³ or —X⁴SR¹⁵ in which X⁴ is a direct bond or (C₁₋₆)alkylene, R¹³ is (C₁₋₆)alkyl and R¹⁵ is (C₆₋₁₀)aryl(C₀₋₆)alkyl, e.g.

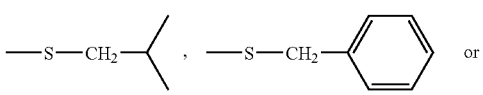

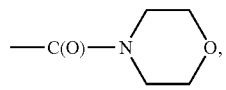

or (v) —X⁴S(O)₂R¹³ or —X⁴S(O)₂R¹⁵ in which X⁴ is a direct bond, R¹³ is (C₁₋₆)alkyl and R¹⁵ is (C₆₋₁₀)aryl(C₀₋₆)alkyl, e.g. —SO₂—CH₂—CH=CH₂,

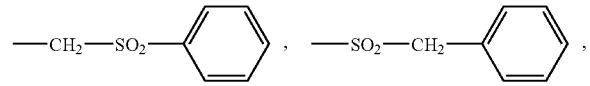

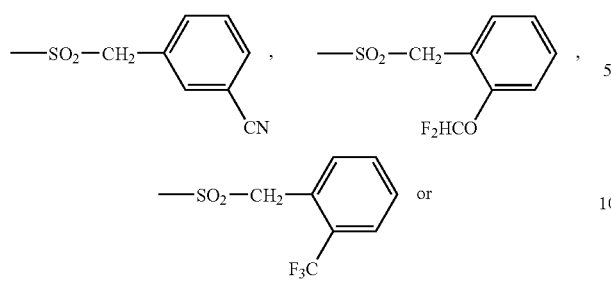

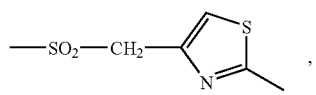

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(a) in which: $R^1$ and $R^2$ are both methyl; $X^7$ is (i) —$R^{15}$, e.g.

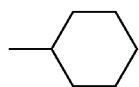

or —CH=CH$_2$, (ii) —$X^4$C(O)$R^{12a}$ in which $X^4$ is a direct bond and $R^{12a}$ is hetero($C_{3-10}$)cycloalkyl($C_{0-6}$)alkyl, e.g.

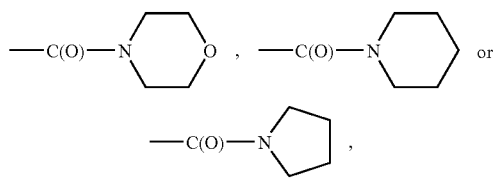

(iii) —$X^4$O$R^{15}$ in which $X^4$ is a direct bond and $R^{15}$ is hetero($C_{3-10}$)cycloalkyl($C_{0-6}$)alkyl, e.g.

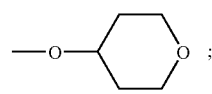

(iv) —$X^4$S$R^{13}$ or —$X^4$S$R^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

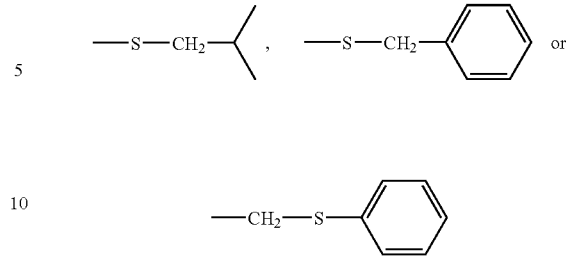

or (v) —$X^4$S(O)$_2$$R^{13}$ or —$X^4$S(O)$_2$$R^{15}$ in which $X^4$ is a direct bond, $R^{13}$ is ($C_{1-6}$)alkyl and $R^{15}$ is ($C_{6-10}$)aryl($C_{0-6}$)alkyl, e.g. —SO$_2$—CH$_2$—CH=CH$_2$,

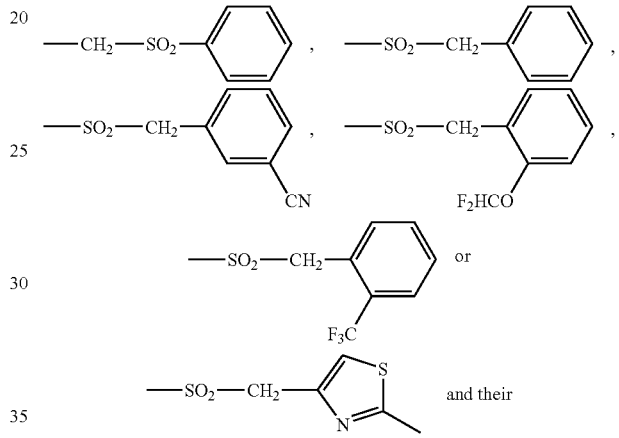

and their corresponding N-oxides, and their prodrugs, and their protected derivatives, individual isomers and mixers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(a) in which: $R^1$ and $R^2$ taken together with the carbon atom to which both $R^1$ and $R^2$ are attached form (i) ($C_{3-8}$)cycloalkylene, e.g. cyclopropyl or (ii) hetero($C_{3-8}$)cycloalkylene, e.g. tetrahydropyran-4-yl and N-methylpiperidin-4-yl; $X^7$ is (i) —$R^{15}$ or —$R^{13}$, e.g.

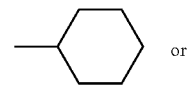

—CH=CH$_2$, respectively, (ii) —$X^4$C(O)$R^{15}$ in which $X^4$ is a direct bond and $R^{15}$ is hetero($C_{3-10}$)cycloalkyl($C_{0-6}$)alkyl, e.g.

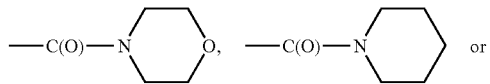

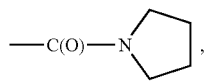

(iii) —X⁴OR¹⁵ in which X⁴ is a direct bond and R¹⁵ is hetero(C₃₋₁₀)cycloalkyl(C₀₋₆)alkyl, e.g.

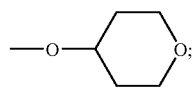

(iv) —X⁴SR¹³ or —X⁴SR¹⁵ in which X⁴ is a direct bond or (C₁₋₆)alkylene, R¹³ is (C₁₋₆)alkyl and R¹⁵ is (C₆₋₁₀)aryl(C₀₋₆)alkyl, e.g.

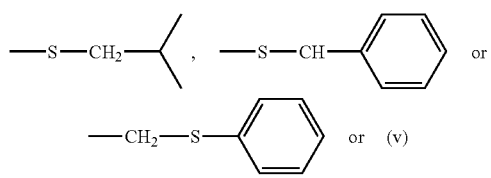

—X⁴S(O)₂R¹³ or —X⁴S(O)₂R¹⁵ in which X⁴ is a direct bond, R¹³ is (C₁₋₆)alkyl and R¹⁵ is (C₆₋₁₀)aryl(C₀₋₆)alkyl, e.g. . —SO₂—CH₂—CH=CH₂,

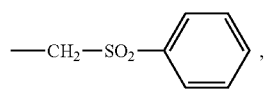

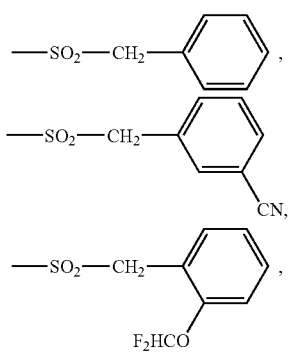

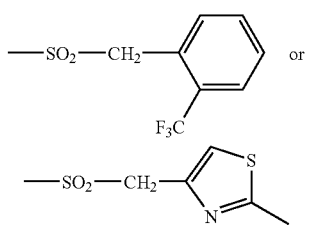

and their corresponding N-oxides, and their prodrugs, and their protected derivatives, individual isomers and mixtures of isomers thereof, and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(b):

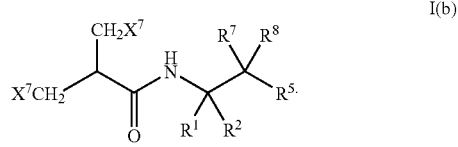

I(b)

wherein R¹, R² and X⁷ are as hereinbefore described, and their corresponding N-oxides, and their prodrugs, and their protected derivatives, individual isomers and mixtures of isomers thereof, and the pharmaceutically acceptable salts and solvates (e.g. hydrates) of such compounds of formula I(b) and their N-oxides and their prodrugs, and their protected derivatives, individual isomers and mixtures of isomers thereof.

Compounds of formula I(b) in which R¹ is hydrogen and R² is:

(vi) hydrogen;

(vii) —X⁴OR¹³, e.g. —CH₂—O—CH₃ or —CH₂—CH₂—O—CH₃;

(viii) hetero(C₅₋₁₀)aryl(C₀₋₆)alkyl, e.g. thien-2-yl or 5-methylfuran-2-yl;

(ix) (C₅₋₁₀)aryl(C₀₋₆)alkyl, e.g. phenethyl;

(x) (C₁₋₆)alkyl, e.g. ethyl, n-propyl or n-butyl are preferred.

Compounds of formula I(b) in which R¹ and R² are both methyl are also preferred.

Compounds of formula I(b) in which R¹ and R² taken together with the carbon atom to which both R¹ and R² are attached form (C₃₋₈)cycloalkylene, e.g. cyclopropyl or hetero(C₃₋₈)cycloalkylene, e.g. tetrahydropyran-4-yl and N-methylpiperidin-4-yl are also preferred.

Compounds of formula I(b) in which R⁷ and R⁸ together form oxo are preferred.

Compounds of formula I(b) in which R⁵ is 1H-benzoimidazol-2-yl, pyrimidin-2-yl, benzooxazol-2-yl, benzothiazol-2-yl, pyridazin-3-yl, 3-phenyl-[1,2,4]oxadiazol-5-yl, 3-ethyl-[1,2,4]oxadiazol-5-yl are preferred.

Compounds of formula I(a) in which X⁷ is:

(vi)-R¹⁵ or —R¹³ e.g.

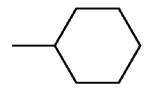

or —CH=CH₂;

(vii) —X⁴C(O)R¹⁵ in which X⁴ is a direct bond and R¹⁵ is hetero(C₃₋₁₀)cycloalkyl(C₀₋₆)alkyl, e.g.

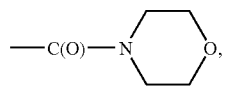

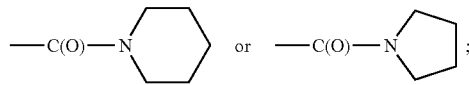

(viii) —X⁴OR¹⁵ in which X⁴ is a direct bond and R¹⁵ is hetero(C₃₋₁₀)cycloalkyl(C₀₋₆)alkyl, e.g.

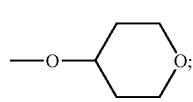

(ix) —X⁴SR¹³ or —R¹⁵ in which X⁴ is a direct bond or (C₁₋₆)alkylene, R¹³ is (C₁₋₆)alkyl and R¹⁵ is (C₆₋₁₀)aryl (C₀₋₆)alkyl, e.g.

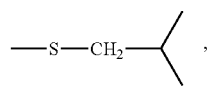

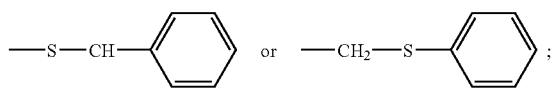

(x) —X⁴S(O)₂R¹³ or —X⁴S(O)₂R¹⁵ in which X⁴ is a direct bond, R¹³ is (C₁₋₆)alkyl and R¹⁵ is (C₆₋₁₀)aryl (C₀₋₆)alkyl, e.g. —SO₂—CH₂—

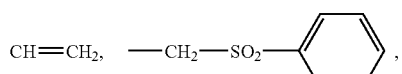

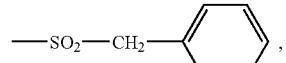

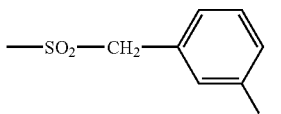

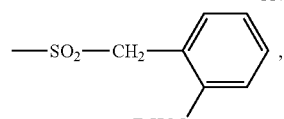

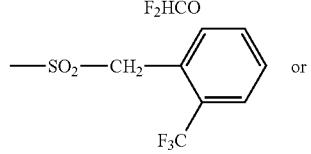

-continued

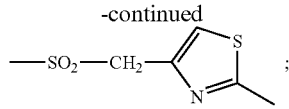

are preferred. Compounds of formula I(b) in which X⁷ represents

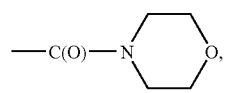

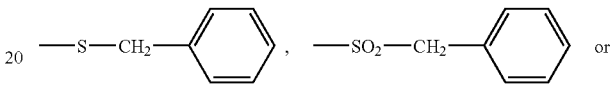

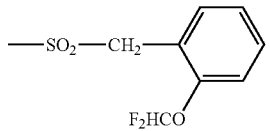

are especially preferred.

A preferred group of compounds of the invention are compounds of formula I(b) in which: R¹ is hydrogen and R² is (i) hydrogen, (ii) X⁴OR¹³, e.g. —CH₂—O—CH₃ or —CH₂—CH₂—O—CH₃, (iii) hetero(C₅₋₁₀)aryl(C₀₋₆)alkyl, e.g. thien-2-yl or 5-methylfuran-2-yl, (iv)(C₅₋₁₀)aryl(C₀₋₆) alkyl, e.g. phenethyl or (v) (C₁₋₆)alkyl, e.g. ethyl, n-propyl or n-butyl; R⁷ and R⁸ together form oxo; R⁵ is 1H-benzoimidazol-2-yl, pyrimidin-2-yl, benzooxazol-2-yl, benzothiazol-2-yl, pyridazin-3-yl, 3-phenyl-[1,2,4]oxadiazol-5-yl, 3-ethyl-[1,2,4]oxadiazol-5-yl; X7 is (i) —R¹⁵ e.g.

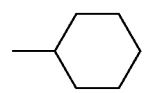

or —CH=CH₂, (ii) —X⁴C(O)R¹⁵ in which X⁴ is a direct bond and R¹⁵ is hetero(C₃₋₁₀)cycloalkyl(C₀₋₆)alkyl, e.g. 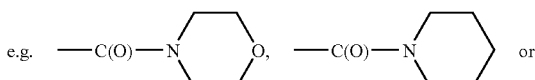

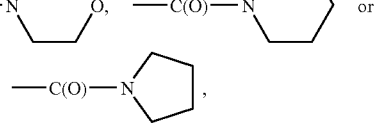

(iii) —X⁴OR¹⁵ in which X⁴ is a direct bond and R¹⁵ is hetero(C₃₋₁₀)cycloalkyl(C₀₋₆)alkyl, e.g.

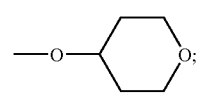

(iv) —$X^4SR^{13}$ or —$X^4SR^{15}$ in which $X^4$ is a direct bond or($C_{1-6}$)alkylene, $R^{13}$ is ($C_{1-6}$)alkyl and $R^{15}$ is ($C_{6-10}$)aryl ($C_{0-6}$)alkyl, e.g.

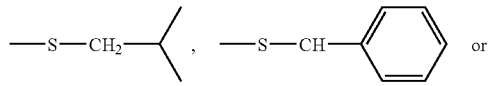

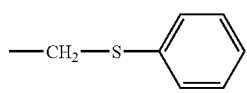

or (v) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. . —$SO_2$—$CH_2$—CH=$CH_2$,

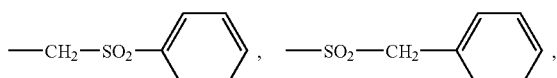

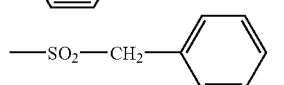

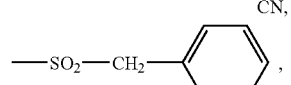

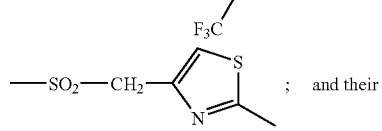

; and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(b) in which: $R^1$ and $R^2$ are both methyl; $R^7$ and $R^8$ together form oxo; $R^5$ is 1H-benzoimidazol-2-yl, pyrimidin-2-yl, benzooxazol-2-yl, benzothiazol-2-yl, pyridazin-3-yl, 3-phenyl-[1,2,4]oxadiazol-5-yl, 3-ethyl-[1,2,4]oxadiazol-5-yl; X7 is (i) —$R^{14a}$, e.g.

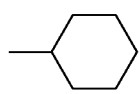

or —CH=$CH_2$, (ii) —$X^4C(O)R^{15}$ in which $X^4$ is a direct bond and $R^{15}$ is hetero($C_{3-10}$)cycloalkyl($C_{0-6}$)alkyl, e.g.

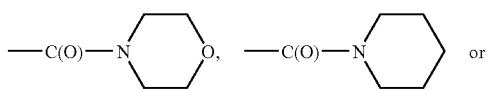

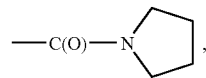

(iii) —$X^4OR^{15}$ in which $X^4$ is a direct bond and $R^{15}$ is hetero($C_{3-10}$)cycloalkyl($C_{0-6}$)alkyl, e.g.

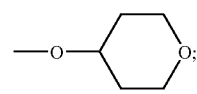

(iv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

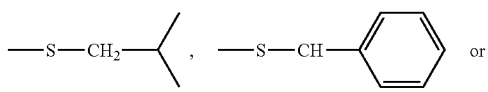

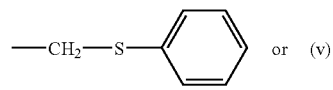  or (v)

—$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. . —$SO_2$—$CH_2$—CH=$CH_2$,

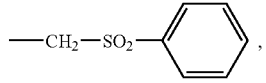

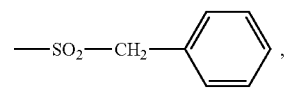

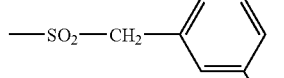

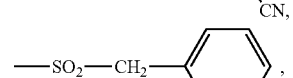

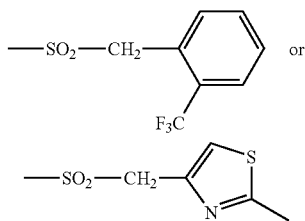

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(b) in which: $R^1$ and $R^2$ taken together with the carbon atom to which both $R^1$ and $R^2$ are attached form (i) ($C_{3-8}$)cycloalkylene, e.g. cyclopropyl or (ii) hetero($C_{3-8}$)cycloalkylene, e.g. tetrahydropyran-4-yl and N-methylpiperidin-4-yl; $R^7$ and $R^8$ together form oxo; $R^5$ is 1H-benzoimidazol-2-yl, pyrimidin-2-yl, benzooxazol-2-yl, benzothiazol-2-yl, pyridazin-3-yl, 3-phenyl-[1,2,4]oxadiazol-5-yl, 3-ethyl-[1,2,4]oxadiazol-5-yl; $X^7$ is (i)—$R^{15}$ or —$R^{13}$, e.g.

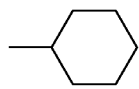

or —CH=CH$_2$, respectively, (ii) —$X^4$C(O)$R^{15}$ in which $X^4$ is a direct bond and $R^{15}$ is hetero($C_{3-10}$)cycloalkyl($C_{0-6}$)alkyl, e.g.

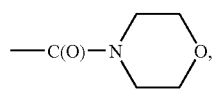

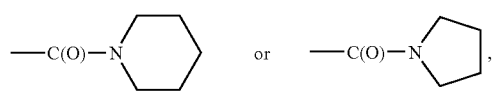

(iii) —$X^4$O$R^{15}$ in which $X^4$ is a direct bond and $R^{15}$ is hetero($C_{3-10}$)cycloalkyl($C_{0-6}$)alkyl, e.g.

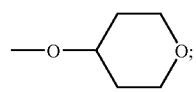

(iv) —$X^4$S$R^{13}$ or —$X^4$S$R^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

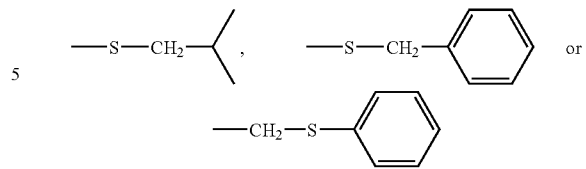

—$X^4$S(O)$_2$R$^{13}$ or —$X^4$S(O)$_2$R$^{15}$ in which $X^4$ is a direct bond, $R^{13}$ is ($C_{1-6}$)alkyl and $R^{15}$ is ($C_{6-10}$)aryl($C_{0-6}$)alkyl, e.g., —SO$_2$—CH$_2$—CH=CH$_2$,

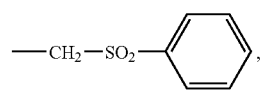

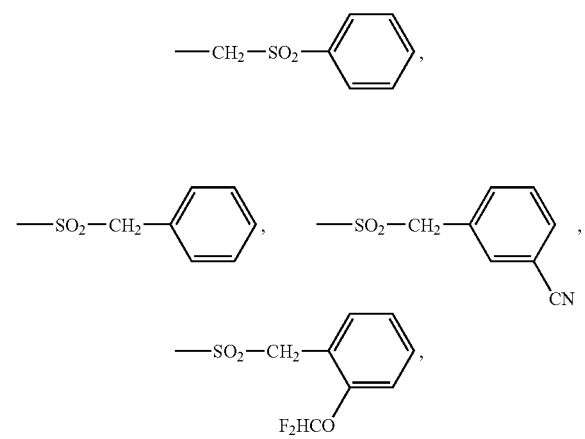

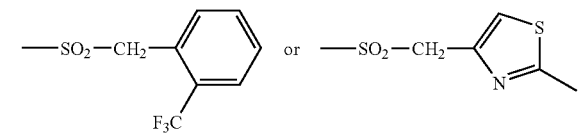

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(c):

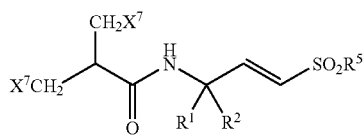

I(c)

wherein $R^1$, $R^2$ and $X^7$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(c) and their N-oxides and their prodrugs, and their protected derivatives, individual isomers and mixtures of isomers thereof.

Compounds of formula I(c) in which $R^1$ is hydrogen and $R^2$ is:

(xi) hydrogen;

(xii) —$X^4OR^{13}$, e.g. —$CH_2$—O—$CH_3$ or —$CH_2$—$CH_2$—O—$CH_3$;

(xiii) hetero($C_{5-10}$)aryl($C_{0-6}$)alkyl, e.g. thien-2-yl or 5-methylfuran-2-yl;

(xiv) ($C_{5-10}$)aryl($C_{0-6}$)alkyl, e.g. phenethyl;

(xv) ($C_{1-6}$)alkyl, e.g. ethyl, n-propyl or n-butyl are preferred.

Compounds of formula I(c) in which $R^1$ and $R^2$ are both methyl are also preferred.

Compounds of formula I(c) in which $R^1$ and $R^2$ taken together with the carbon atom to which both $R^1$ and $R^2$ are attached form ($C_{3-8}$)cycloalkylene, e.g. cyclopropyl or hetero($C_{3-8}$)cycloalkylene, e.g. tetrahydropyran-4-yl and N-methylpiperidin-4-yl are also preferred.

Compounds of formula I(c) in which $R^5$ is ($C_{6-10}$)aryl($C_{0-6}$)alkyl, e.g. phenyl are preferred.

Compounds of formula I(a) in which $X^7$ is:

(xi) -$R^{15}$ or —$R^{13}$, e.g.

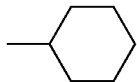

or —$CH=CH_2$, respectively;

(xii) —$X^4C(O)R^{15}$ in which $X^4$ is a direct bond and $R^{15}$ is hetero($C_{3-10}$)cycloalkyl($C_6$)alkyl, e.g.

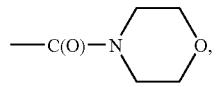

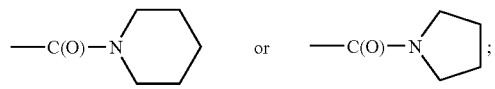

(xiii) —$X^4OR^{15}$ in which $X^4$ is a direct bond and $R^{15}$ is hetero($C_{3-10}$)cycloalkyl($C_{0-6}$)alkyl, e.g.

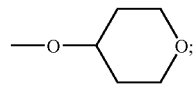

(xiv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

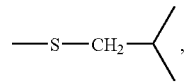

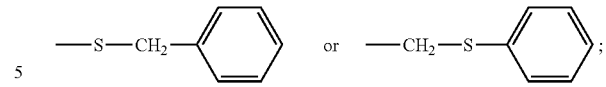

(xv) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. —$SO_2$—$CH_2$—

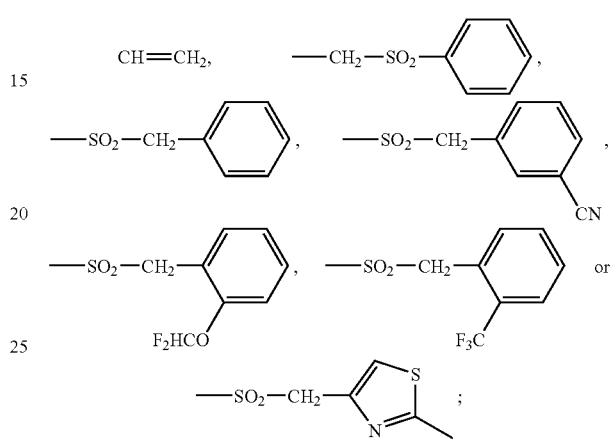

are preferred. Compounds of formula I(c) in which $X^7$ represents

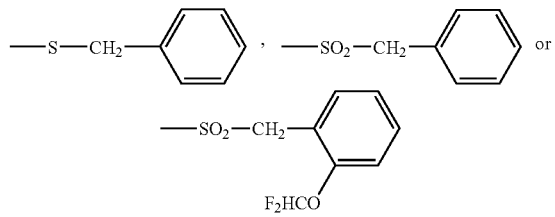

are especially preferred.

A preferred group of compounds of the invention are compounds of formula I(c) in which: $R^1$ is hydrogen and $R^2$ is (i) hydrogen, (ii) $X^4OR^{13}$ e.g. —$CH_2$—O—$CH_3$ or —$CH_2$—$CH_2$—O—$CH_3$, (iii) hetero($C_{5-10}$)aryl($C_{0-6}$)alkyl, e.g. thien-2-yl or 5-methylfuran-2-yl, (iv)($C_{5-10}$)aryl($C_{0-6}$)alkyl, e.g. phenethyl or (v) ($C_{1-6}$)alkyl, e.g. ethyl, n-propyl or n-butyl; $R^5$ is ($C_{6-10}$)aryl($C_{0-6}$)alkyl, e.g. phenyl; $X^7$ is (i) —$R^{15}$ or —$R^{13}$, e.g.

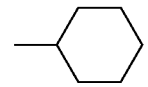

or —CH=CH$_2$, respectively, (ii) —X$^4$C(O)R$^{15}$ in which X$^4$ is a direct bond and R$^{15}$ is hetero(C$_{3-10}$)cycloalkyl(C$_{0-6}$)alkyl, e.g.

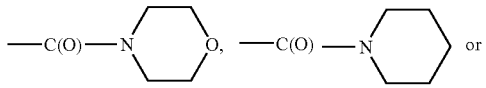

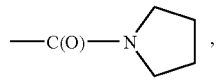

(iii) —X$^4$OR$^{15}$ in which X$^4$ is a direct bond and R$^{15}$ is hetero(C$_{3-10}$)cycloalkyl(C$_{0-6}$)alkyl, e.g.

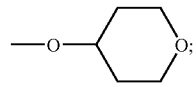

(iv) —X$^4$SR$^{13}$ or —X$^4$SR$^{15}$ in which X$^4$ is a direct bond or (C$_{1-6}$)alkylene, R$^{13}$ is (C$_{1-6}$)alkyl and R$^{15}$ is (C$_{6-10}$)aryl(C$_{0-6}$)alkyl, e.g.

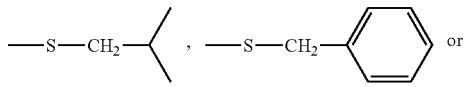

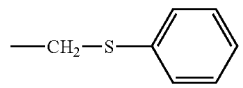

or (v) —X$^4$S(O)$_2$R$^{13}$ or —X$^4$S(O)$_2$R$^{15}$ in which X$^4$ is a direct bond, R$^{13}$ is (C$_{1-6}$)alkyl and R$^{15}$ is (C$_{6-10}$)aryl(C$_{0-6}$)alkyl, e.g. . —SO$_2$—CH$_2$—CH=CH$_2$,

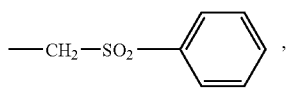

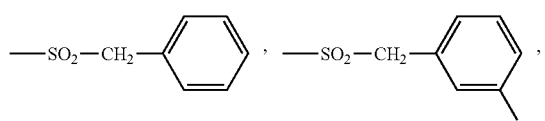

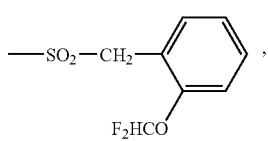

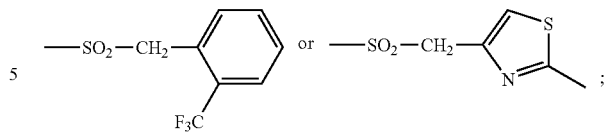

and their corresponding N-oxides, and their prodrugs, and their protected derivatives, individual isomers and mixtures of isomers thereof, and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(c) in which: R$^1$ and R$^2$ are both methyl; R$^5$ is (C$_{6-10}$)aryl(C$_{0-6}$)alkyl, e.g. phenyl; X$^7$ is (i) —R$^{19}$ or —R$^{13}$, e.g.

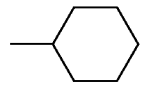

or —CH=CH$_2$, (ii) —X$^4$C(O)R$^{15}$ in which X$^4$ is a direct bond, R$^{15}$ is hetero(C$_{3-10}$)cycloalkyl(C$_{0-6}$)alkyl, e.g.

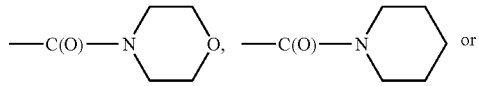

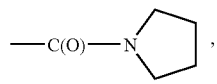

(iii) —X$^4$OR$^{15}$ in which X$^4$ is a direct bond and R$^{15}$ is hetero(C$_{3-10}$)cycloalkyl(C$_{0-6}$)alkyl, e.g.

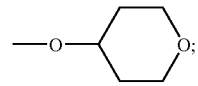

(iv) —X$^4$SR$^{13}$ or —X$^4$SR$^{15}$ in which X$^4$ is a direct bond or (C$_{1-6}$)alkylene, R$^{13}$ is (C$_{1-6}$)alkyl and R$^{15}$ is (C$_{6-10}$)aryl(C$_{0-6}$)alkyl, e.g.

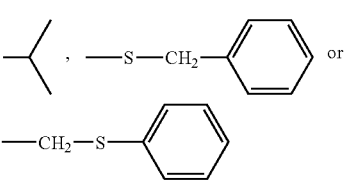

or (v) —X$^4$S(O)$_2$R$^{13}$ or —X$^4$S(O)$_2$R$^{13}$ in which X$^4$ is a direct bond, R$^{13}$ is (C$_{1-6}$)alkyl and R$^{15}$ is (C$_{6-10}$)aryl(C$_{0-6}$)alkyl, e.g. . —SO$_2$—CH$_2$—CH=CH$_2$,

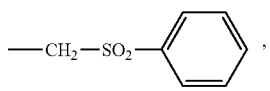

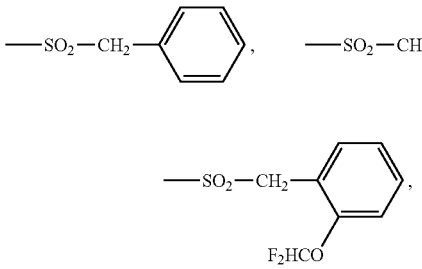

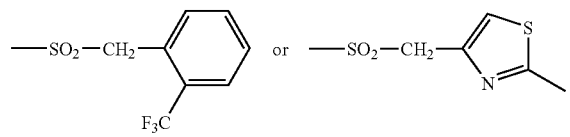

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(c) in which: $R^1$ and $R^2$ taken together with the carbon atom to which both $R^1$ and $R^2$ are attached form (i) $(C_{3-8})$cycloalkylene, e.g. cyclopropyl or (ii) hetero$(C_{3-8})$cycloalkylene, e.g. tetrahydropyran-4-yl and N-methylpiperidin-4-yl; $R^5$ is $(C_{6-10})$aryl$(C_{0-6})$alkyl, e.g. phenyl; $X^7$ is (i) —$R^{15}$ or —$R^{13}$, e.g.

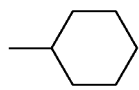

or —CH=CH$_2$, respectively, (ii) —$X^4$C(O)$R^{15}$ in which $X^4$ is a direct bond and $R^{15}$ is hetero$(C_{3-10})$cycloalkyl$(C_{0-6})$alkyl, e.g.

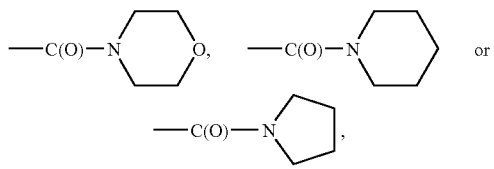

(iii) —$X^4OR^{15}$ in which $X^4$ is a direct bond and $R^{15}$ is hetero$(C_{3-10})$cycloalkyl$(C_{0-6})$alkyl, e.g.

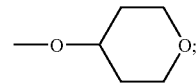

(iv) —$X^4SR^{13}$ or —$X^4SR^{15}$ in which $X^4$ is a direct bond or $(C_{1-6})$alkylene, $R^{13}$ is $(C_{1-6})$alkyl and $R^{15}$ is $(C_{6-10})$aryl$(C_{0-6})$alkyl, e.g. or

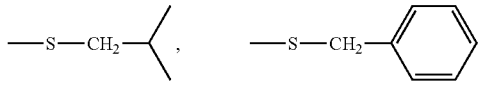

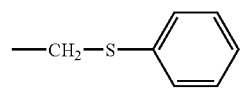

or (v) —$X^4S(O)_2R^{13}$ or —$X^4S(O)_2R^{15}$ in which $X^4$ is a direct bond, $R^{13}$ is $(C_{1-6})$alkyl and $R^{15}$ is $(C_{6-10})$aryl$(C_{0-6})$alkyl, e.g. . —SO$_2$—CH$_2$—CH=CH$_2$,

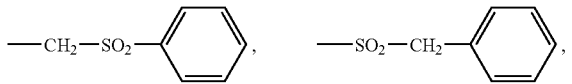

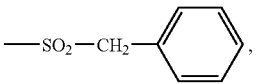

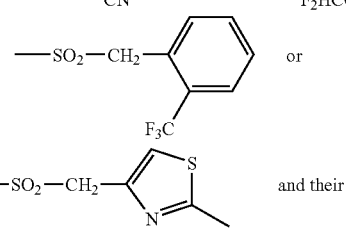

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(d):

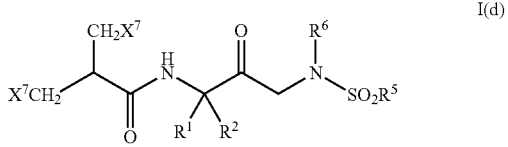

I(d)

wherein $R^1$, $R^2$ and $X^7$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(d) and their N-oxides and their prodrugs, and their protected derivatives, individual isomers and mixtures of isomers thereof.

Compounds of formula I(d) in which $R^1$ is hydrogen and $R^2$ is:

(xvi) hydrogen;
(xvii) —$X^4OR^{13}$, e.g. —$CH_2$—O—$CH_3$ or —$CH_2$—$CH_2$—O—$CH_3$;
(xviii) hetero($C_{5-10}$)aryl($C_{0-6}$)alkyl, e.g. thien-2-yl or 5-methylfuran-2-yl;
(xix) ($C_{5-10}$)aryl($C_{0-6}$)alkyl, e.g. phenethyl;
(xx) ($C_{1-6}$)alkyl, e.g. ethyl, n-propyl or n-butyl are preferred.

Compounds of formula I(d) in which $R^1$ and $R^2$ are both methyl are also preferred.

Compounds of formula I(d) in which $R^1$ and $R^2$ taken together with the carbon atom to which both $R^1$ and $R^2$ are attached form ($C_{3-8}$)cycloalkylene, e.g. cyclopropyl or hetero($C_{3-8}$)cycloalkylene, e.g. tetrahydropyran-4-yl and N-methylpiperidin-4-yl are also preferred.

Compounds of formula I(d) in which $R^5$ is ($C_{6-10}$)aryl($C_{0-6}$)alkyl, e.g. phenyl are preferred.

Compounds of formula I(d) in which $R^6$ is hydrogen are preferred.

Compounds of formula I(a) in which $X^7$ is:
(xvi) —$R^{15}$ or —$R^{13}$ e.g.

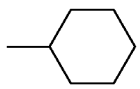

or —CH=$CH_2$;

(xvii) —$X^4C(O)R^{15}$ in which $X^4$ is a direct bond and $R^{15}$ is hetero($C_{3-10}$)cycloalkyl($C_{0-6}$)alkyl, e.g.

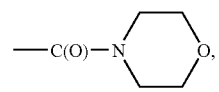

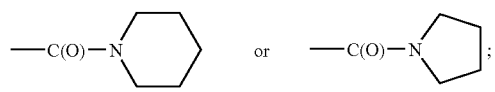

(xviii) —$X^4OR^{15}$ in which $X^4$ is a direct bond and $R^{15}$ is hetero($C_{3-10}$)cycloalkyl($C_{0-6}$)alkyl, e.g.

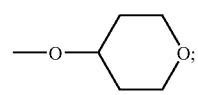

(xix) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

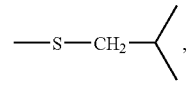

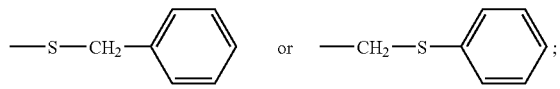

(xx) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. —$SO_2$—$CH_2$—

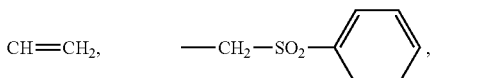

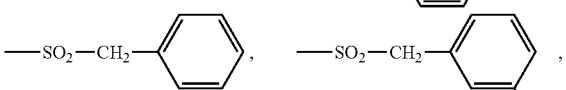

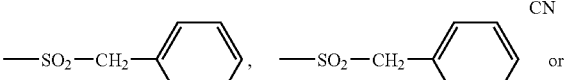

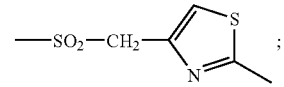

are preferred. Compounds of formula I(c) in which $X^7$ represents

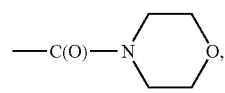

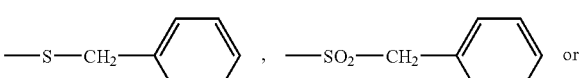

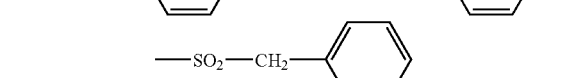

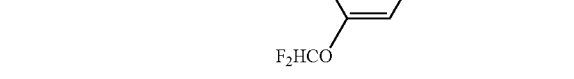

are especially preferred.

A preferred group of compounds of the invention are compounds of formula I(d) in which: $R^1$ is hydrogen and $R^2$ is (i) hydrogen, (ii) $X^4OR^{13}$ e.g. —$CH_2$—O—$CH_3$ or —$CH_2$—$CH_2$—O—$CH_3$, (iii) hetero($C_{5-10}$)aryl($C_{0-6}$)alkyl, e.g. thien-2-yl or 5-methylfuran-2-yl, (iv)($C_{5-10}$)aryl($C_{0-6}$) alkyl, e.g. phenethyl or (v) ($C_{1-6}$)alkyl, e.g. ethyl, n-propyl or n-butyl; $R^5$ is ($C_{6-10}$)aryl($C_{0-6}$)alkyl, e.g. phenyl; $R^6$ is hydrogen; X7 is (i) —$R^{15}$ or —$R^{13}$ e.g.

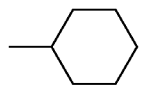

or —CH=CH$_2$, respectively, (ii) —X$^4$C(O)R$^{15}$ in which X$^4$ is a direct bond and R$^{15}$ is hetero(C$_{3-10}$)cycloalkyl(C$_{0-6}$)alkyl, e.g.

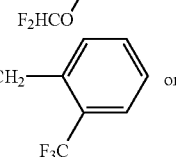

(iii) —X$^4$OR$^{15}$ in which X$^4$ is a direct bond and R$^{15}$ is hetero(C$_{3-10}$)cycloalkyl(C$_{0-6}$)alkyl, e.g.

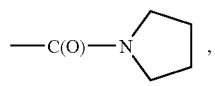

(iv) —X$^4$SR$^{13}$ or —X$^4$SR$^{15}$ in which X$^4$ is a direct bond or (C$_{1-6}$)alkyl, R$^{13}$ is (C$_{1-6}$)alkyl and R$^{15}$ is (C$_{6-10}$)aryl(C$_{0-6}$)alkyl, e.g.

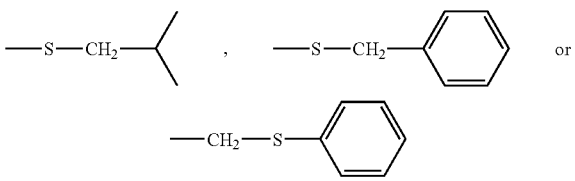

or (v) —X$^4$S(O)$_2$R$^{13}$ or —X$^4$S(O)$_2$R$^{15}$ in which X$^4$ is a direct bond, R$^{13}$ is (C$_{1-6}$)alkyl and R$^{15}$ is (C$_{6-10}$)aryl(C$_{0-6}$)alkyl, e.g. —SO$_2$—CH$_2$—CH=CH$_2$,

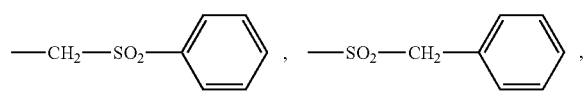

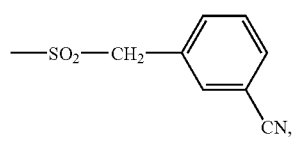

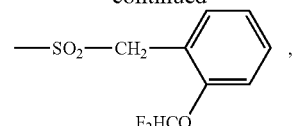

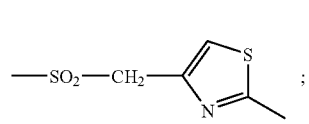

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(d) in which: R$^1$ and R$^2$ are both methyl; R$^5$ is (C$_{6-10}$)aryl(C$_{0-6}$)alkyl, e.g. phenyl; R$^6$ is hydrogen; X$^7$ is (i) —R$^{15}$ or —R$^{13}$, e.g.

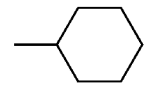

or —CH=CH$_2$, (ii) —X$^4$C(O)R$^{15}$ in which X$^4$ is a direct bond and R$^{15}$ is hetero(C$_{3-10}$)cycloalkyl(C$_{0-6}$)alkyl, e.g.

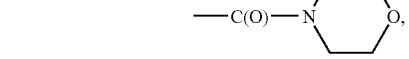

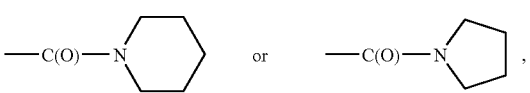

(iii) —X$^4$OR$^{15}$ in which X$^4$ is a direct bond and R$^{15}$ is hetero(C$_{3-10}$)cycloalkyl(C$_{0-6}$)alkyl, e.g.

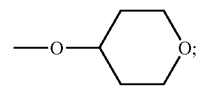

(iv) —X$^4$SR$^{13}$ or —X$^4$SR$^{15}$ in which X$^4$ is a direct bond or (C$_{1-6}$)alkylene, R$^{13}$ is (C$_{1-6}$)alkyl and R$^{15}$ is (C$_{6-10}$)aryl(C$_{0-6}$)alkyl, e.g.

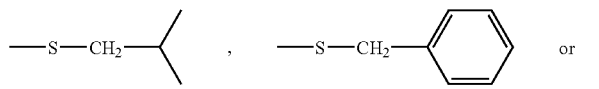 or 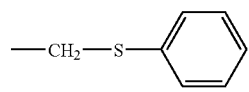

or (v) —$X^4S(O)_2R^{13}$ or —$X^4S(O)_2R^{15}$ in which $X^4$ is a direct bond, $R^{13}$ is $(C_{1-6})$alkyl and $R^{15}$ is $(C_{6-10})$aryl$(C_{0-6})$alkyl, e.g. . —$SO_2$—$CH_2$—$CH$=$CH_2$,

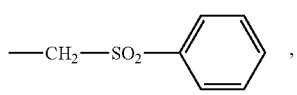,

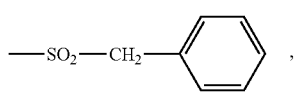,

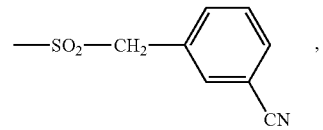,

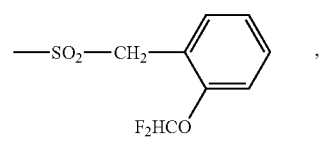 or

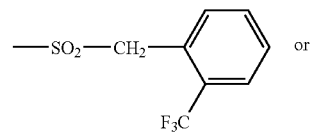

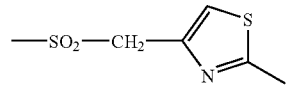

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(d) in which: $R^1$ and $R^2$ taken together with the carbon atom to which both $R^1$ and $R^2$ are attached form (i) $(C_{3-8})$cycloalkylene, e.g. cyclopropyl or (ii) hetero$(C_{3-8})$cycloalkylene, e.g. tetrahydropyran-4-yl and N-methylpiperidin-4-yl; $R^5$ is $(C_{6-10})$aryl$(C_{0-6})$alkyl, e.g. phenyl; $R^6$ is hydrogen; $X^7$ is (i) —$R^{15}$ or —$R^{13}$, e.g.

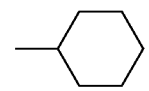

or —CH=CH$_2$, (ii) —$X^4C(O)R^{15}$ in which $X^4$ is a direct bond and $R^{15}$ is hetero$(C_{3-10})$cycloalkyl$(C_{0-6})$alkyl, e.g.

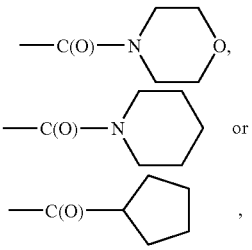

(iii) —$X^4OR^{15}$ in which $X^4$ is a direct bond and $R^{15}$ is hetero$(C_{3-10})$cycloalkyl$(C_{0-6})$alkyl, e.g.

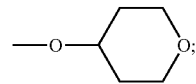;

(iv) —$X^4SR^{13}$ or —$X^4SR^{15}$ in which $X^4$ is a direct bond or $(C_{1-6})$alkylene, $R^{13}$ is $(C_{1-6})$alkyl and $R^{15}$ is $(C_{6-10})$aryl$(C_{0-6})$alkyl, e.g.

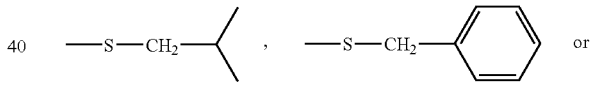

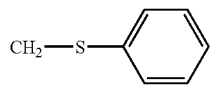

or (v) —$X^4S(O)_2R^{13}$ or —$X^4S(O)_2R^{15}$ in which $X^4$ is a direct bond, $R^{13}$ is $(C_{1-6})$alkyl and $R^{15}$ is $(C_{6-10})$aryl$(C_{0-6})$alkyl, e.g. . —$SO_2$—$CH_2$—$CH$=$CH_2$,

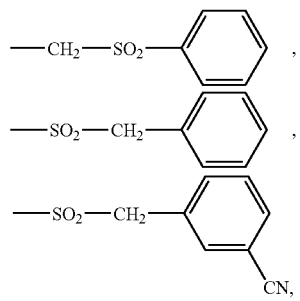

-continued

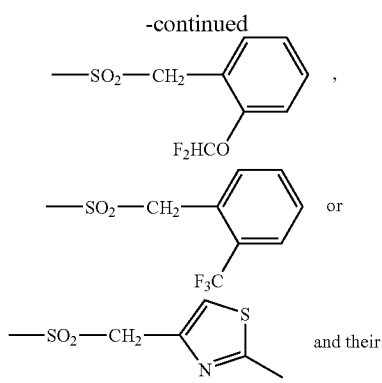

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(e):

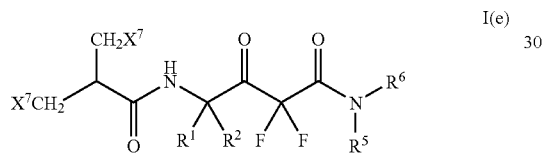

wherein $R^1$, $R^2$ and $X^7$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(e) and their N-oxides and their prodrugs, and their protected derivatives, individual isomers and mixtures of isomers thereof.

Compounds of formula I(e) in which $R^1$ is hydrogen and $R^2$ is:

(xxi) hydrogen;
(xxii) —$X^4OR^{13}$ e.g. —$CH_2$—O—$CH_3$ or —$CH_2$—$CH_2$—O—$CH_3$;
(xxiii) hetero($C_{5-10}$)aryl($C_{0-6}$)alkyl, e.g. thien-2-yl or 5-methylfuran-2-yl;
(xxiv) ($C_{5-10}$)aryl($C_{0-6}$)alkyl, e.g. phenethyl;
(xxv) ($C_{1-6}$)alkyl, e.g. ethyl, n-propyl or n-butyl are preferred.

Compounds of formula I(e) in which $R^1$ and $R^2$ are both methyl are also preferred.

Compounds of formula I(e) in which $R^1$ and $R^2$ taken together with the carbon atom to which both $R^1$ and $R^2$ are attached form ($C_{3-8}$)cycloalkylene, e.g. cyclopropyl or hetero($C_{3-8}$)cycloalkylene, e.g. tetrahydropyran-4-yl and N-methylpiperidin-4-yl are also preferred.

Compounds of formula I(e) in which $R^5$ and $R^6$ are ($C_{1-4}$)alkyl, e.g. methyl are preferred.

Compounds of formula I(a) in which $X^7$ is:
(xxi) —$R^{15}$ or —$R^{13}$ e.g.

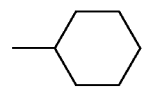

or —CH=$CH_2$, respectively;
(xxii) —$X^4C(O)R^{15}$ in which $X^4$ is a direct bond and $R^{15}$ is hetero($C_{3-10}$)cycloalkyl($C_{0-6}$)alkyl, e.g.

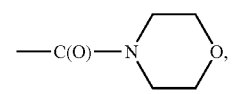

(xxiii) —$X^4OR^{15}$ in which $X^4$ is a direct bond and $R^{15}$ is hetero($C_{3-10}$)cycloalkyl($C_{0-6}$)alkyl, e.g.

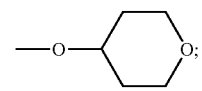

(xxiv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

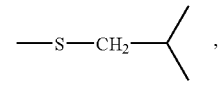

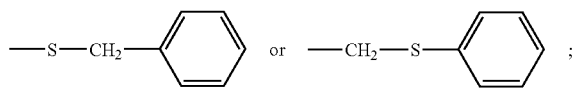

(xxv) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. —$SO_2$—$CH_2$—

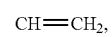

CH=$CH_2$,

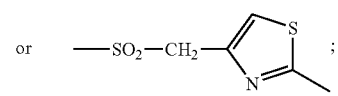

are preferred. Compounds of formula I(e) in which $X^7$ represents

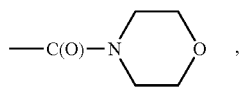

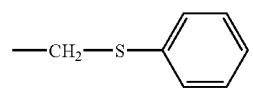

are especially preferred.

A preferred group of compounds of the invention are compounds of formula I(e) in which: $R^1$ is hydrogen and $R^2$ is (i) hydrogen, (ii) $X^4OR^{13}$, e.g. —CH$_2$—O—CH$_3$ or —CH$_2$—CH$_2$—O—CH$_3$, (iii) hetero(C$_{5-10}$)aryl(C$_{0-6}$)alkyl, e.g. thien-2-yl or 5-methylfuran-2-yl, (iv)(C$_{5-10}$)aryl(C$_{0-6}$)alkyl, e.g. phenethyl or (v) (C$_{1-6}$)alkyl, e.g. ethyl, n-propyl or n-butyl; $R^5$ is (C$_{1-4}$)alkyl, e.g. methyl; $X^7$ is (i) —R$^{15}$ or —R$^{13}$ e.g.

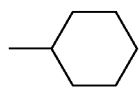

or —CH=CH$_2$, (ii) —X$^4$C(O)R$^{15}$ in which $X^4$ is a direct bond and $R^{15}$ is hetero(C$_{3-10}$)cycloalkyl(C$_{0-6}$)alkyl,

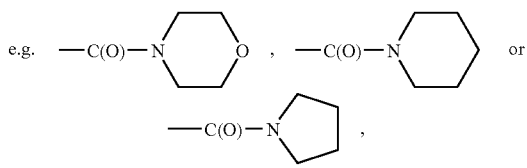

(iii) —X$^4$OR$^{15}$ in which $X^4$ is a direct bond and $R^{15}$ is hetero(C$_{3-10}$)cycloalkyl(C$_{0-6}$)alkyl, e.g.

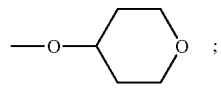

(iv) —X$^4$SR$^{13}$ or —X$^4$SR$^{15}$ in which $X^4$ is a direct bond or (C$_{1-6}$)alkylene, $R^{13}$ is (C$_{1-6}$)alkyl and $R^{15}$ is (C$_{6-10}$)aryl(C$_{0-6}$)alkyl, e.g.

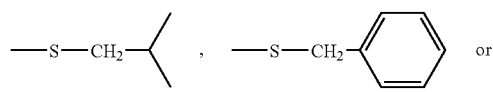

or (v) —X$^4$S(O)$_2$R$^{13}$ or —X$^4$S(O)$_2$R$^{15}$ in which $X^4$ is a direct bond, $R^{13}$ is (C$_{1-6}$)alkyl and $R^{15}$ is (C$_{6-10}$)aryl(C$_{0-6}$)alkyl, e.g. —SO$_2$—CH$_2$—CH=CH$_2$,

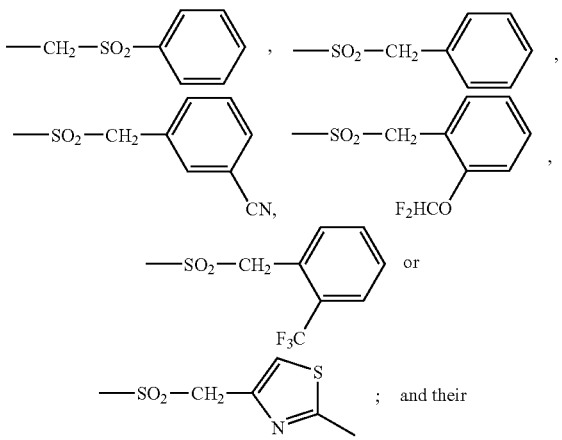

corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(e) in which: $R^1$ and $R^2$ are both methyl; $R^5$ is (C$_{1-4}$)alkyl, e.g. methyl; $X^7$ is (i) —R$^{15}$ or —R$^{13}$ e.g.

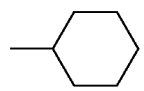

or —CH=CH$_2$, (ii) —X$^4$C(O)R$^{15}$ in which $X^4$ is a direct bond and $R^{15}$ is hetero(C$_{3-10}$)cycloalkyl(C$_{0-6}$)alkyl, e.g.

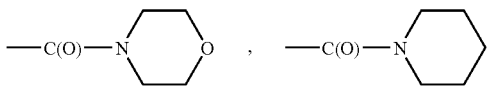

or

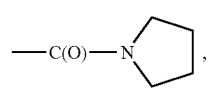

(iii) —X$^4$OR$^{15}$ in which $X^4$ is a direct bond and $R^{15}$ is hetero(C$_{3-10}$)cycloalkyl(C$_{0-6}$)alkyl, e.g.

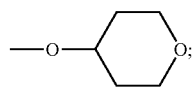

(iv) —X⁴SR¹³ or —X⁴SR¹⁵ in which X⁴ is a direct bond or ($C_{1-6}$)alkylene, R¹³ is ($C_{1-6}$)alkyl and R¹⁵ is ($C_{6-10}$)aryl($C_{0-6}$)alkyl, e.g.

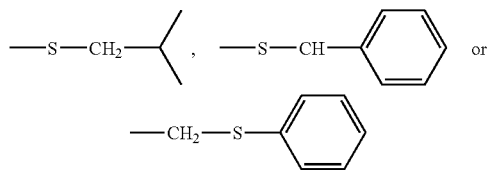

or (v) —X⁴S(O)₂R¹³ or —X⁴S(O)₂R¹⁵ in which X⁴ is a direct bond and R¹³ is ($C_{1-6}$)alkyl and R¹⁵ is ($C_{6-10}$)aryl($C_{0-6}$)alkyl, e.g. —SO₂—CH₂—CH=CH₂,

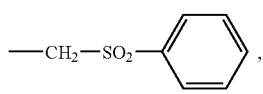

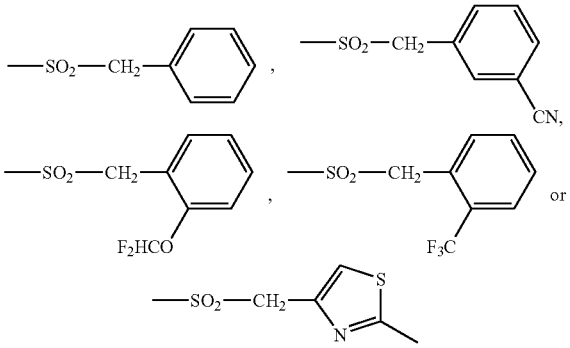

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(e) in which: R¹ and R² taken together with the carbon atom to which both R¹ and R² are attached form (i) ($C_{3-8}$)cycloalkylene, e.g. cyclopropyl or (ii) hetero($C_{3-8}$)cycloalkylene, e.g. tetrahydropyran-4-yl and N-methylpiperidin-4-yl; R⁵ is ($C_{1-4}$)alkyl, e.g. methyl; X⁷ is (i) —R¹⁵ or —R¹³ e.g.

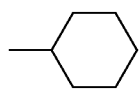

or —CH=CH₂, (ii) —X⁴C(O)R¹⁵ in which X⁴ is a direct bond and R¹⁵ is hetero($C_{3-10}$)cycloalkyl($C_{0-6}$)alkyl, e.g.

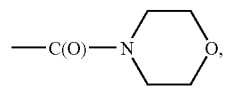

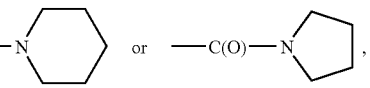

(iii) —X⁴OR¹⁵ in which X⁴ is a direct bond and R¹⁵ is hetero($C_{3-10}$)cycloalkyl($C_{0-6}$)alkyl, e.g.

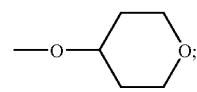

(iv) —X⁴SR¹³ or —X⁴SR¹⁵ in which X⁴ is a direct bond or ($C_{1-6}$)alkylene, R¹³ is ($C_{1-6}$)alkyl and R¹⁵ is ($C_{6-10}$)aryl($C_{0-6}$)alkyl, e.g.

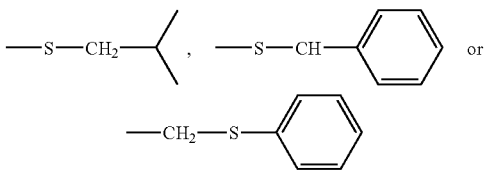

or (v) —X⁴S(O)₂R¹³ or —X⁴S(O)₂R¹⁵ in which X⁴ is a direct bond, R¹³ is ($C_{1-6}$)alkyl and R¹⁵ is ($C_{6-10}$)aryl($C_{0-6}$)alkyl, e.g. —SO₂—CH₂—CH=CH₂,

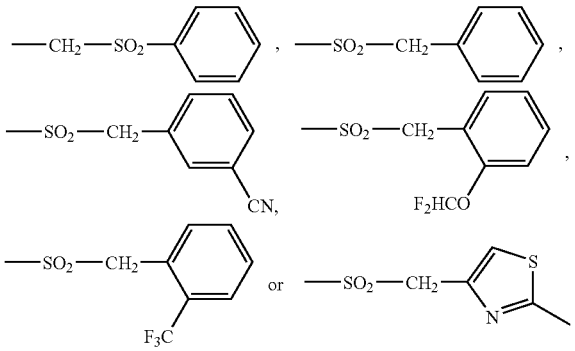

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(f):

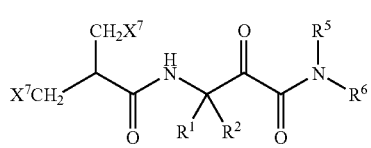

wherein $R^1$, $R^2$ and $X^7$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(f) and their N-oxides and their prodrugs, and their protected derivatives, individual isomers and mixtures of isomers thereof.

Compounds of formula I(f) in which $R^1$ is hydrogen and $R^2$ is:
- (xxvi) hydrogen;
- (xxvii) —$X^4OR^{13}$ e.g. —$CH_2$—O—$CH_3$ or —$CH_2$—$CH_2$—O—$CH_3$;
- (xxviii) hetero($C_{5-10}$)aryl($C_{0-6}$)alkyl, e.g. thien-2-yl or 5-methylfuran-2-yl;
- (xxix) ($C_{5-10}$)aryl($C_{0-6}$)alkyl, e.g. phenethyl;
- (xxx) ($C_{1-6}$)alkyl, e.g. ethyl, n-propyl or n-butyl are preferred.

Compounds of formula I(f) in which $R^1$ and $R^2$ are both methyl are also preferred.

Compounds of formula I(f) in which $R^1$ and $R^2$ taken together with the carbon atom to which both $R^1$ and $R^2$ are attached form ($C_{3-8}$)cycloalkylene, e.g. cyclopropyl or hetero($C_{3-8}$)cycloalkylene, e.g. tetrahydropyran-4-yl and N-methylpiperidin-4-yl are also preferred.

Compounds of formula I(f) in which $R^5$ is ($C_{6-10}$)aryl($C_{0-6}$)alkyl, e.g. benzyl are preferred.

Compounds of formula I(f) in which $R^6$ is hydrogen are preferred.

Compounds of formula I(f) in which $X^7$ is:
- (xxvi) —$R^{15}$ or —$R^{13}$ e.g.

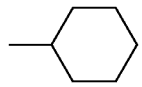

or —CH=$CH_2$;
- (xxvii) —$X^4C(O)R^{15}$ in which $X^4$ is a direct bond, $R^{15}$ is hetero($C_{3-10}$)cycloalkyl($C_{0-6}$)alkyl, e.g.

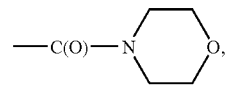

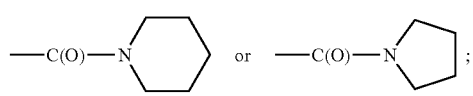

- (xxviii) —$X^4OR^{15}$ in which $X^4$ is a direct bond and $R^{15}$ is hetero($C_{3-10}$)cycloalkyl($C_{0-6}$)alkyl, e.g.

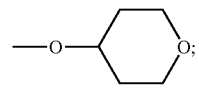

- (xxix) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

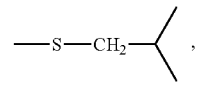

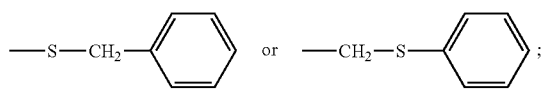

- (xxx) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$)alkyl, e.g. —$SO_2$—$CH_2$

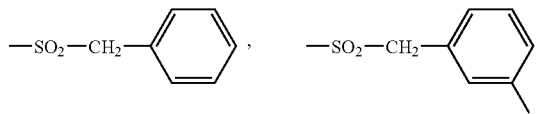

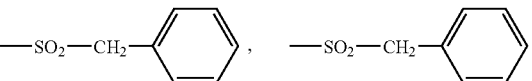

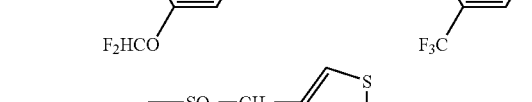

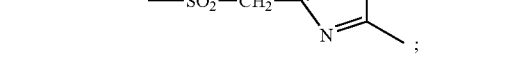

are preferred. Compounds of formula I(f) in which $X^7$ represents

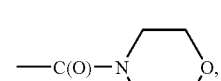

-continued

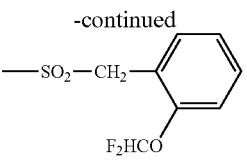

are especially preferred.

A preferred group of compounds of the invention are compounds of formula I(f) in which: $R^1$ is hydrogen and $R^2$ is (i) hydrogen, (ii) $X^4 OR^{13}$, e.g. —$CH_2$—O—$CH_3$ or —$CH_2$—$CH_2$—O—$CH_3$, (iii) hetero($C_{5-10}$)aryl($C_{0-6}$)alkyl, e.g. thien-2-yl or 5-methylfuran-2-yl, (iv)($C_{5-10}$)aryl($C_{0-6}$) alkyl, e.g. phenethyl or (v) ($C_{1-6}$)alkyl, e.g. ethyl, n-propyl or n-butyl; $R^5$ is ($C_{6-10}$)aryl($C_{0-6}$)alkyl, e.g. benzyl; $R^6$ is hydrogen; X7 is (i) —$R^{15}$ or —$R^{13}$, e.g.

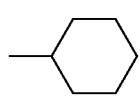

or —CH=$CH_2$, (ii) —$X^4C(O)R^{15}$ in which $X^4$ is a direct bond and $R^{15}$ is hetero($C_{3-10}$)cycloalkyl($C_{0-6}$)alkyl, e.g.

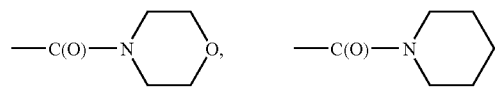

(iii) —$X^4OR^{15}$ in which $X^4$ is a direct bond and $R^{15}$ is hetero($C_{3-10}$)cycloalkyl($C_{0-6}$)alkyl, e.g.

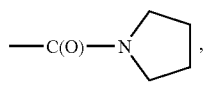

(iv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl ($C_{0-6}$)alkyl, e.g.

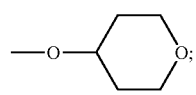

or (v) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$) alkyl, e.g. —$SO_2$—$CH_2$—CH=$CH_2$,

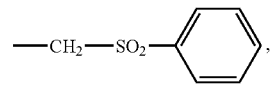

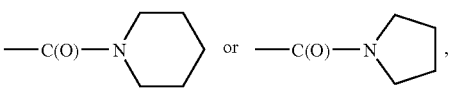

; and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(f) in which: $R^1$ and $R^2$ are both methyl; $R^5$ is ($C_{6-10}$)aryl($C_{0-6}$)alkyl, e.g. benzyl; $R^6$ is hydrogen; X7 is (i) —$R^{15}$ or —$R^{13}$, e.g.

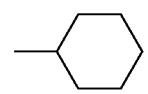

or —CH=$CH_2$, (ii) —$X^4C(O)R^{15}$ in which $X^4$ is a direct bond and $R^{15}$ is hetero($C_{3-10}$)cycloalkyl($C_{0-6}$)alkyl, e.g.

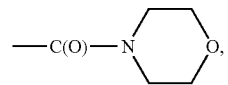

(iii) —$X^4OR^{15}$ in which $X^4$ is a direct bond and $R^{15}$ is hetero($C_{3-10}$)cycloalkyl($C_{0-6}$)alkyl, e.g.

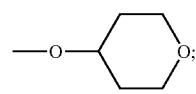

(iv) —X⁴SR¹³ or —X⁴SR¹⁵ in which X⁴ is a direct bond or (C$_{1-6}$)alkylene, R¹³ is (C$_{1-6}$)alkyl and R¹⁵ is (C$_{6-10}$)aryl(C$_{0-6}$)alkyl, e.g.

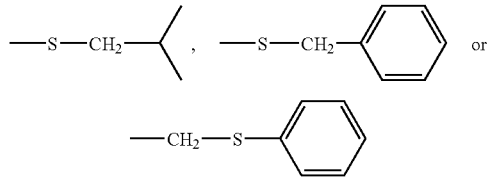

or (v) —X⁴S(O)$_2$R¹³ or —X⁴S(O)$_2$R¹⁵ in which X⁴ is a direct bond, R¹³ is (C$_{1-6}$)alkyl and R¹⁵ is (C$_{6-10}$)aryl(C$_{0-6}$)alkyl, e.g. . —SO$_2$—CH$_2$—CH=CH$_2$,

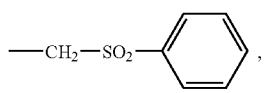

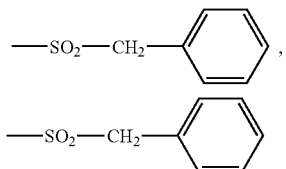

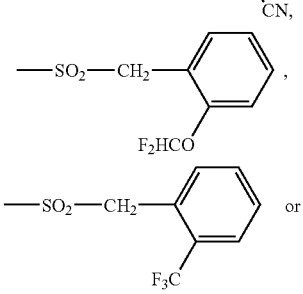

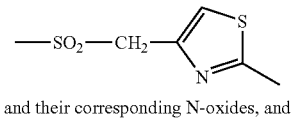

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(f) in which: R¹ and R² taken together with the carbon atom to which both R¹ and R² are attached form (i) (C$_{3-8}$)cycloalkylene, e.g. cyclopropyl or (ii) hetero(C$_{3-8}$)cycloalkylene, e.g. tetrahydropyran-4-yl and N-methylpiperidin-4-yl; R⁵ is (C$_{6-10}$)aryl(C$_{0-6}$)alkyl, e.g. benzyl; R⁶ is hydrogen; X7 is (i) —R¹⁵ or —R¹³, e.g.

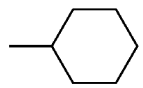

or —CH=CH$_2$, (ii) —X⁴C(O)R¹⁵ in which X⁴ is a direct bond and R¹⁵ is hetero(C$_{3-10}$)cycloalkyl(C$_{0-6}$)alkyl, e.g.

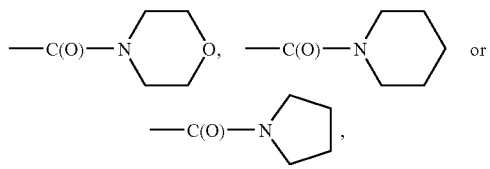

(iii) —X⁴OR¹⁵ in which X⁴ is a direct bond and R¹⁵ is hetero(C$_{3-10}$)cycloalkyl(C$_{0-6}$)alkyl, e.g.

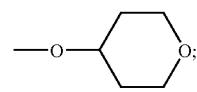

(iv) —X⁴SR¹³ or —X⁴SR¹⁵ in which X⁴ is a direct bond or (C$_{1-6}$)alkyl, R¹³ is (C$_{1-6}$)alkyl and R¹⁵ is (C$_{6-10}$)aryl(C$_{0-6}$)alkyl, e.g.

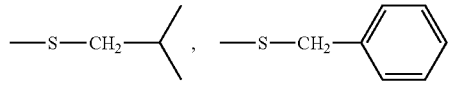

or

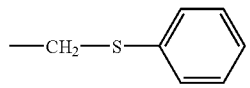

or (v) —X⁴S(O)$_2$R¹³ or —X⁴S(O)$_2$R¹³ in which X⁴ is a direct bond, R¹³ is (C$_{1-6}$)alkyl and R¹⁵ is (C$_{6-10}$)aryl(C$_{0-6}$)alkyl, e.g. . —SO$_2$—CH$_2$—CH=CH$_2$,

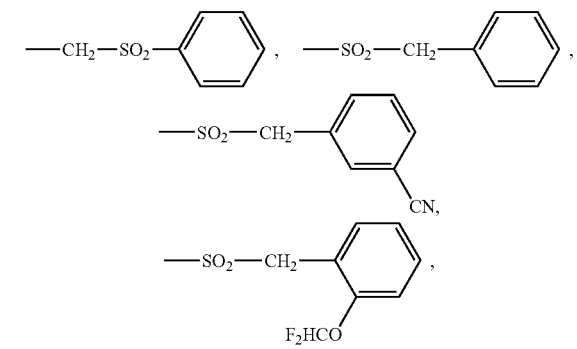

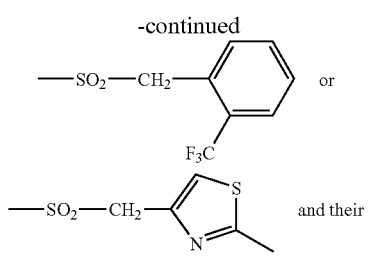

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Another particular group of compounds of the invention are compounds of formula I(g):

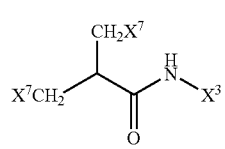

I(g)

wherein $R^1$, $R^2$ and X7 are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of formula I(g) and their N-oxides and their prodrugs, and their protected derivatives, individual isomers and mixtures of isomers thereof.

Compounds of formula I(g) in which $R^1$ is hydrogen and $R^2$ is:

(xxxi) hydrogen;
(xxxii) —$X^4OR^{13}$ e.g. —$CH_2$—O—$CH_3$ or —$CH_2$—$CH_2$—O—$CH_3$;
(xxxiii) hetero($C_{5-10}$)aryl($C_{0-6}$)alkyl, e.g. thien-2-yl or 5-methylfuran-2-yl;
(xxxiv)($C_{5-10}$)aryl($C_{0-6}$)alkyl, e.g. phenethyl;
(xxxv) ($C_{1-6}$)alkyl, e.g. ethyl, n-propyl or n-butyl are preferred.

Compounds of formula I(g) in which $R^1$ and $R^2$ are both methyl are also preferred.

Compounds of formula I(g) in which $R^1$ and $R^2$ taken together with the carbon atom to which both $R^1$ and $R^2$ are attached form ($C_{3-8}$)cycloalkylene, e.g. cyclopropyl or hetero($C_{3-8}$)cycloalkylene, e.g. tetrahydropyran-4-yl and N-methylpiperidin-4-yl are also preferred.

Compounds of formula I(g) in which $X^3$ is 2-methyl-4-oxo-tetrahydro-furan-3-yl, 2-ethyl-4-oxo-tetrahydro-furan-3-yl, 4-oxo-1-(1-phenyl-methanoyl)-pyrrolidin-3-yl or (S)-2-Acetoxy-4-oxo-azetidin-3-yl are preferred.

Compounds of formula I(g) in which X7 is:

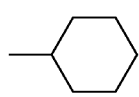

(xxxi)-$R^{15}$ or —$R^{13}$, e.g. or —CH=$CH_2$;
(xxxii) —$X^4C(O)R^{15}$ in which $X^4$ is a direct bond and $R^{15}$ is hetero($C_{3-10}$)cycloalkyl($C_{0-6}$)alkyl, e.g.

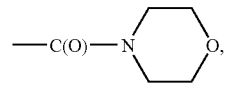

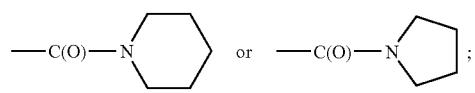

(xxxiii) —$X^4OR^{15}$ in which $X^4$ is a direct bond and $R^{15}$ is hetero($C_{3-10}$)cycloalkyl($C_{0-6}$)alkyl, e.g.

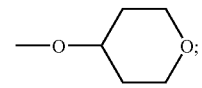

(xxxiv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl ($C_{0-6}$)alkyl, e.g.

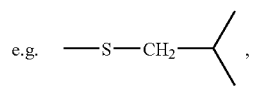

(xxxv) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$) alkyl, e.g. —$SO_2$—$CH_2$—

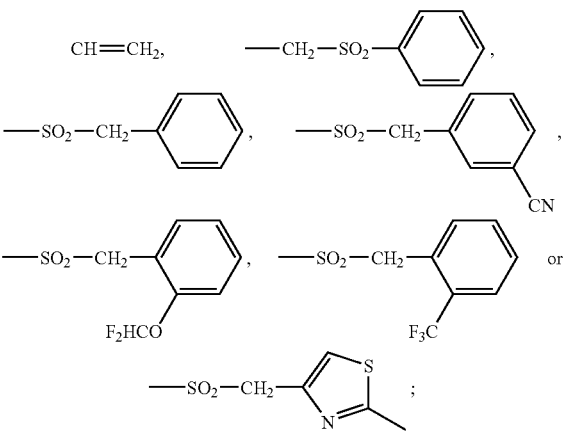

are preferred. Compounds of formula I(g) in which X7 represents

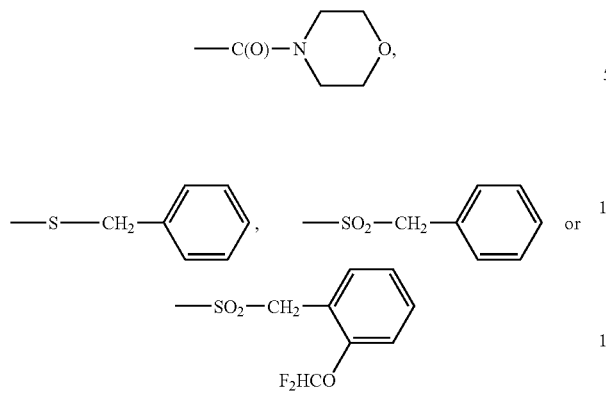

are especially preferred.

A preferred group of compounds of the invention are compounds of formula I(g) in which: $R^1$ is hydrogen and $R^2$ is (i) hydrogen, (ii) $X^4OR^{13}$ e.g. —$CH_2$—O—$CH_3$ or —$CH_2$—$CH_2$—O—$CH_3$, (iii) hetero($C_{5-10}$)aryl($C_{0-6}$)alkyl, e.g. thien-2-yl or 5-methylfuran-2-yl, (iv)($C_{5-10}$)aryl($C_{0-6}$)alkyl, e.g. phenethyl or (v) ($C_{1-6}$)alkyl, e.g. ethyl, n-propyl or n-butyl; $X^3$ is 2-methyl-4-oxo-tetrahydro-furan-3-yl, 2-ethyl-4-oxo-tetrahydro-furan-3-yl, 4-oxo-1-(1-phenyl-methanoyl)-pyrrolidin-3-yl or (S)-2-acetoxy-4-oxo-azetidin-3-yl; X7 is (i)—$R^{15}$ or —$R^{13}$ e.g.

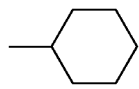

or —$CH$=$CH_2$, (ii) —$X^4C(O)R^{15}$ in which $X^4$ is a direct bond and $R^{15}$ is hetero($C_{3-10}$)cycloalkyl($C_{0-6}$)alkyl, e.g.

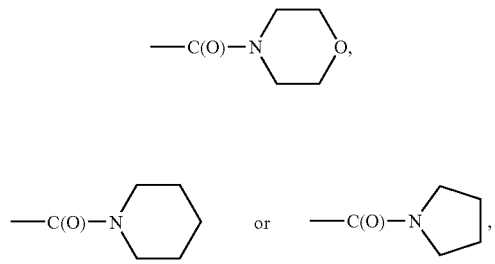

(iii) —$X^4OR^{15}$ in which $X^4$ is a direct bond and $R^{15}$ is hetero($C_{3-10}$)cycloalkyl($C_{0-6}$)alkyl, e.g.

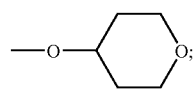

(iv) —$X^4SR^{13}$ or —$X^4SR^{15}$ in which $X^4$ is a direct bond or ($C_{1-6}$)alkylene, $R^{13}$ is ($C_{1-6}$)alkyl and $R^{15}$ is ($C_{6-10}$)aryl($C_{0-6}$)alkyl, e.g.

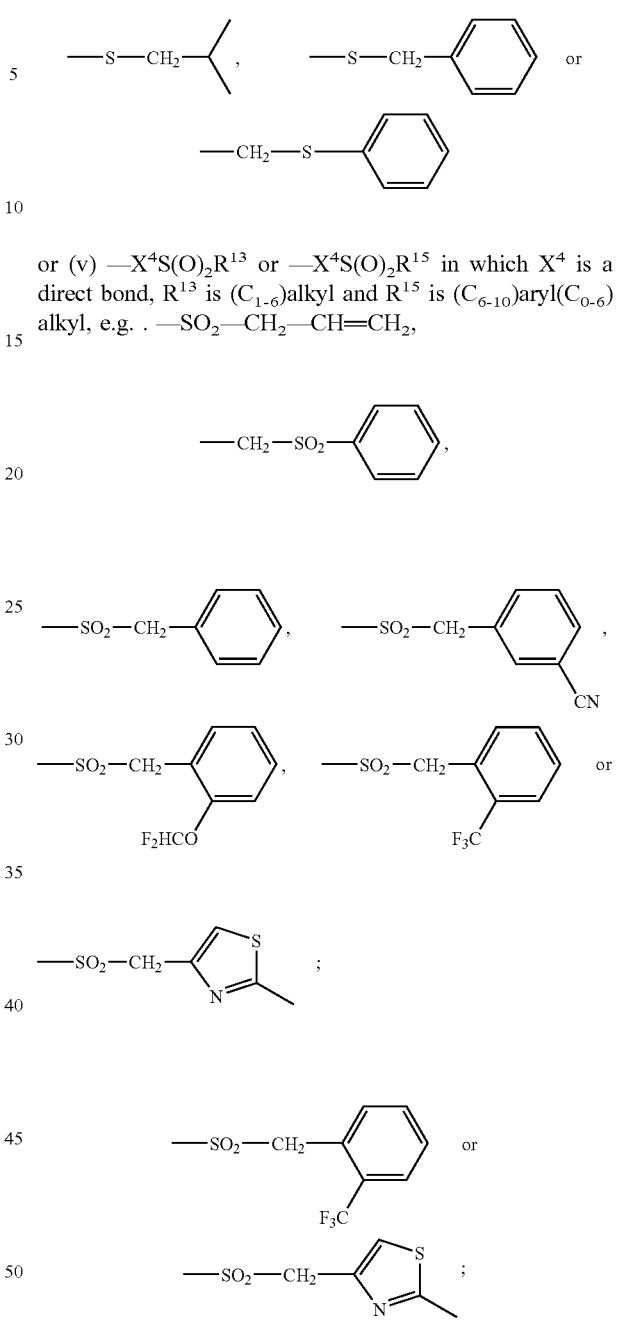

or (v) —$X^4S(O)_2R^{13}$ or —$X^4S(O)_2R^{15}$ in which $X^4$ is a direct bond, $R^{13}$ is ($C_{1-6}$)alkyl and $R^{15}$ is ($C_{6-10}$)aryl($C_{0-6}$) alkyl, e.g. . —$SO_2$—$CH_2$—$CH$=$CH_2$, and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(g) in which: $R^1$ and $R^2$ are both methyl; $X^3$ is 2-methyl-4-oxo-tetrahydro-furan-3-yl, 2-ethyl-4-oxo-tetrahydro-furan-3-yl, 4-oxo-1-(1-phenyl-methanoyl)-pyrrolidin-3-yl or (S)-2-acetoxy-4-oxo-azetidin-3-yl; X7 is (i) —$R^{15}$ or —$R^{13}$ e.g.

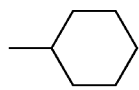

or —CH=CH$_2$, (ii) —X$^4$C(O)R$^{15}$ in which X$^4$ is a direct bond and R$^{15}$ is hetero(C$_{3-10}$)cycloalkyl(C$_{0-6}$)alkyl, e.g.

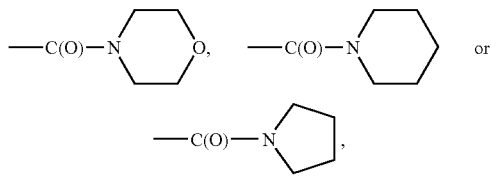

(iii) —X$^4$OR$^{15}$ in which X$^4$ is a direct bond and R$^{15}$ is hetero(C$_{3-10}$)cycloalkyl(C$_{0-6}$)alkyl, e.g.

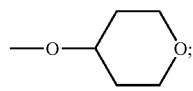

(iv) —X$^4$SR$^{13}$ or —X$^4$SR$^{15}$ in which X$^4$ is a direct bond or (C$_{1-6}$)alkylene, R$^{13}$ is (C$_{1-6}$)alkyl and R$^{15}$ is (C$_{6-10}$)aryl(C$_{0-6}$)alkyl, e.g.

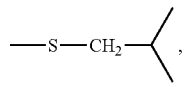

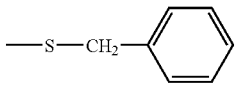 or 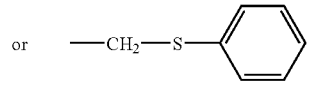

or (v) —X$^4$S(O)$_2$R$^{13}$ or —X$^4$S(O)$_2$R$^{15}$ in which X$^4$ is a direct bond, R$^{13}$ is (C$_{1-6}$)alkyl and R$^{15}$ is (C$_{6-10}$)aryl(C$_{0-6}$)alkyl, e.g. —SO$_2$—

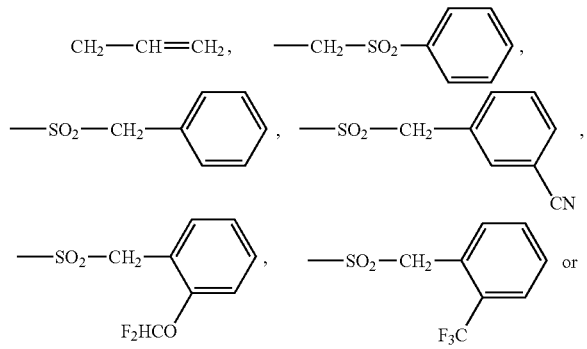

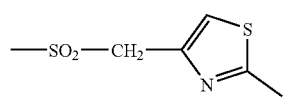 and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

A further preferred group of compounds of the invention are compounds of formula I(g) in which: R$^1$ and R$^2$ taken together with the carbon atom to which both R$^1$ and R$^2$ are attached form (i) (C$_{3-8}$)cycloalkylene, e.g. cyclopropyl or (ii) hetero(C$_{3-8}$)cycloalkylene, e.g. tetrahydropyran-4-yl and N-methylpiperidin-4-yl; X$^3$ is 2-methyl-4-oxo-tetrahydro-furan-3-yl, 2-ethyl-4-oxo-tetrahydro-furan-3-yl, 4-oxo-1-(1-phenyl-methanoyl)-pyrrolidin-3-yl or (S)-2-Acetoxy-4-oxo-azetidin-3-yl; X$^7$ is (i) —R$^{15}$ or —R$^{13}$ e.g.

or —CH=CH$_2$, (ii) —X$^4$C(O)R$^{15}$ in which X$^4$ is a direct bond and R$^{15}$ is hetero(C$_{3-10}$)cycloalkyl(C$_{0-6}$)alkyl, e.g.

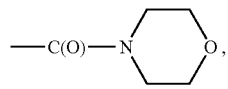

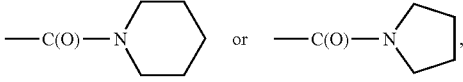

(iii) —X$^4$OR$^{15}$ in which X$^4$ is a direct bond and R$^{15}$ is hetero(C$_{3-10}$)cycloalkyl(C$_{0-6}$)alkyl, e.g.

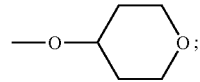

(iv) —X$^4$SR$^{13}$ or —X$^4$SR$^{15}$ in which X$^4$ is a direct bond or (C$_{1-6}$)alkylene, R$^{13}$ is (C$_{1-6}$)alkyl and R$^{15}$ is (C$_{6-10}$)aryl(C$_{0-6}$)alkyl, e.g.

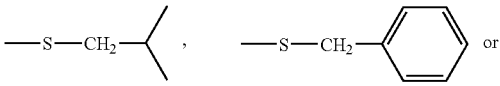 or

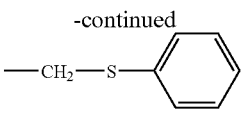

or (v) —X⁴S(O)₂R¹³ or —X⁴S(O)₂R¹⁵ in which X⁴ is a direct bond, R¹³ is (C₁₋₆)alkyl and R¹⁵ is (C₆₋₁₀)aryl(C₀₋₆)alkyl, e.g.

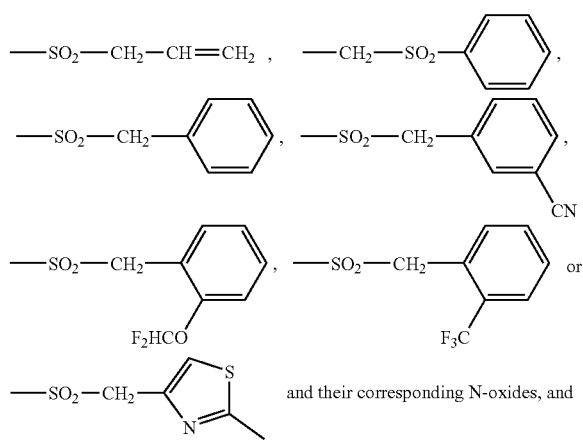

and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Reference to the preferred embodiments set forth above is meant to include all combinations of particular and preferred groups unless stated otherwise.

Reference to the preferred embodiments set forth above is meant to include all combinations of particular and preferred groups.

Particular compounds of the invention are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments (C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the carbon atom (C*) of a cyano group, the acyl carbon atom (C*) of one of the fragments (D2–D6 or D8–D56) depicted in Table 4, the vinyl carbon atom (C*) of the fragment (D7) depicted in Table 4 or the acyl carbon atom (C*) of one of the fragments (E1–E14) depicted in Table 5.

Particular compounds of formula I(a) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments (C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the carbon atom (C*) of a cyano group depicted in Table 4.

Particular compounds of formula (1b) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C₁₁ or C13) or the tertiary carbon atom (C*) of one of the fragments (C2–C5 or C12) depicted in Table 3 to the acyl carbon atom (C*) of one of the fragments (D2, D4–D6, D9–D11, D18–D24, D45–D46 or D48–D56) depicted in Table 4.

Particular compounds of formula I(c) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the vinyl carbon atom (C*) of the fragment (D7) depicted in Table 4.

Particular compounds of formula I(d) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the acyl carbon atom (C*) of the fragment (D17) depicted in Table 4.

Particular compounds of formula I(e) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the acyl carbon atom (C*) of the fragment (D15) depicted in Table 4.

Particular compounds of formula I(f) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the acyl carbon atom (C*) of one of the fragments (D8, D25–D44) depicted in Table 4.

Particular compounds of formula I(g) are selected from the compounds formed by: joining the methylene carbon atom (CH₂*) of one of the fragments (A1 to A116) shown in Table 1 to the carbon atom (*CH*) of one of the fragments (B1 to B115) shown in Table 2; joining the carbon atom (*CH*) of one of the fragments (B1 to B115) shown in Table 2 to the acyl carbon atom (C*) of one of the fragments(C1 to C13) depicted in Table 3; and joining the methylene carbon atom (CH₂*) of fragment D1, the carbon atom (*CH*) of one of the fragments (C2, C6–C11 or C13) or the tertiary carbon atom (C*) of one of the fragments (C2–C5 or C12) depicted in Table 3 to the acyl carbon atom (C*) of one of the fragments (E1–E14) depicted in Table 5.

TABLE 1

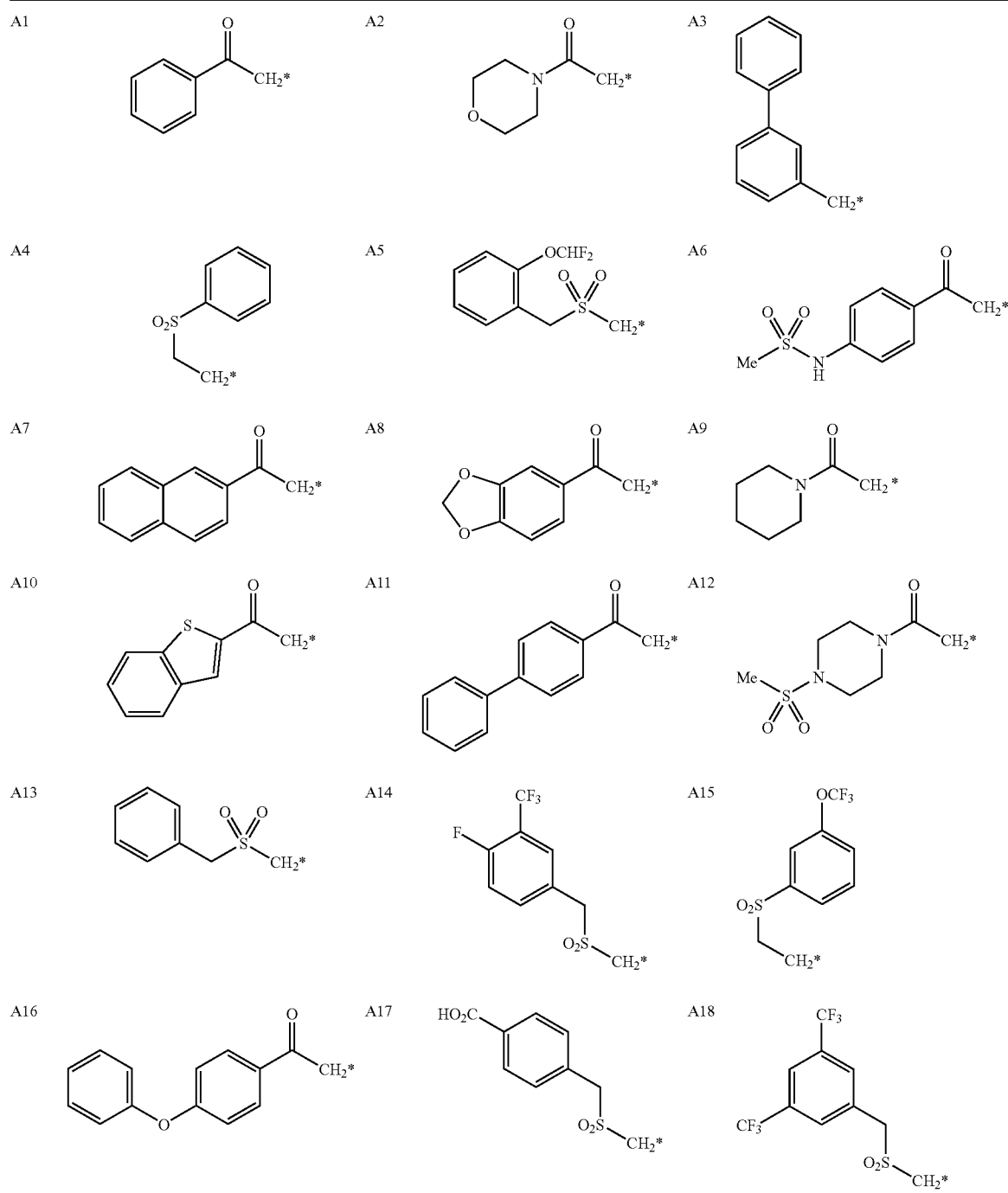

TABLE 1-continued
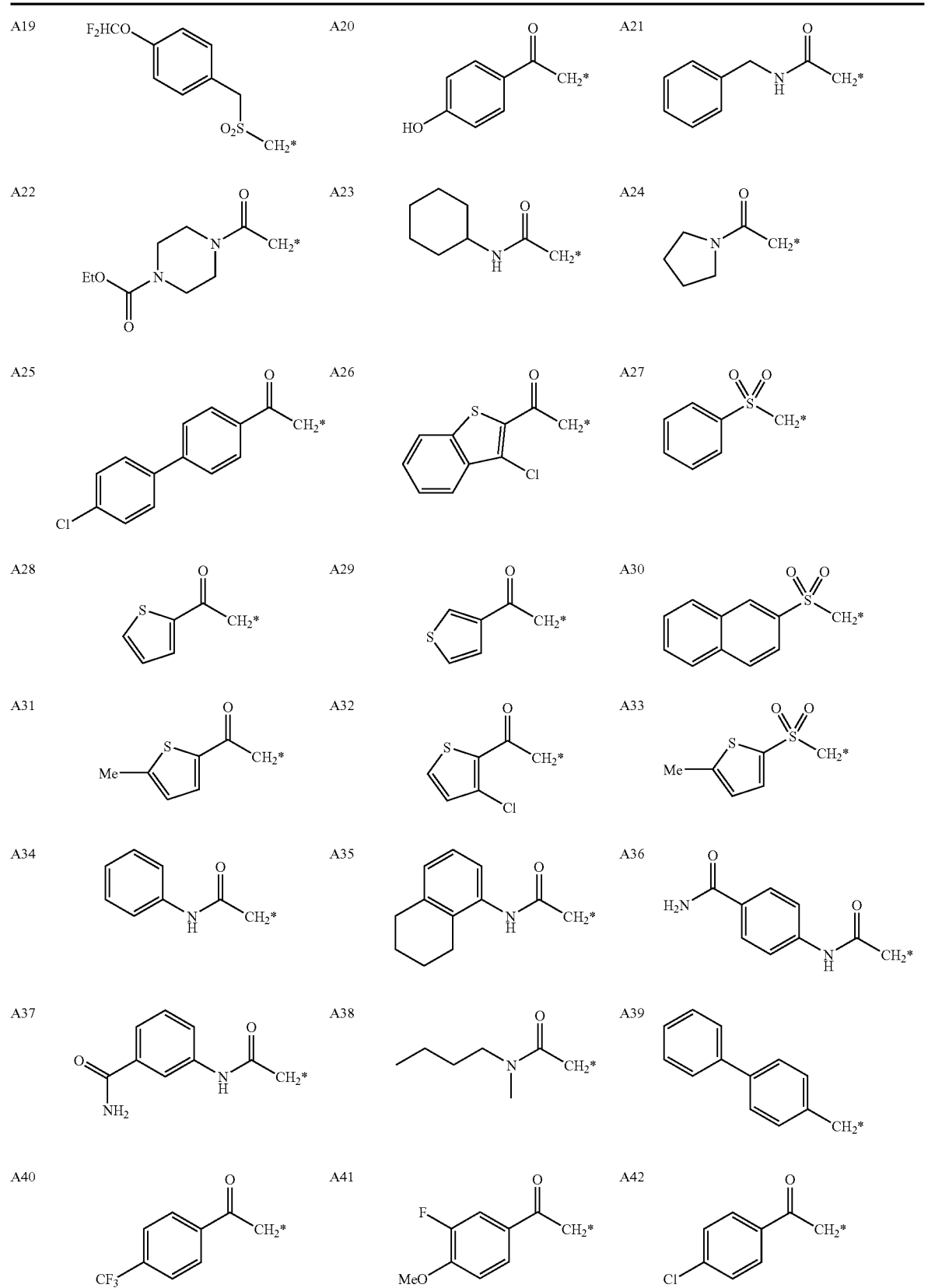

TABLE 1-continued

TABLE 1-continued
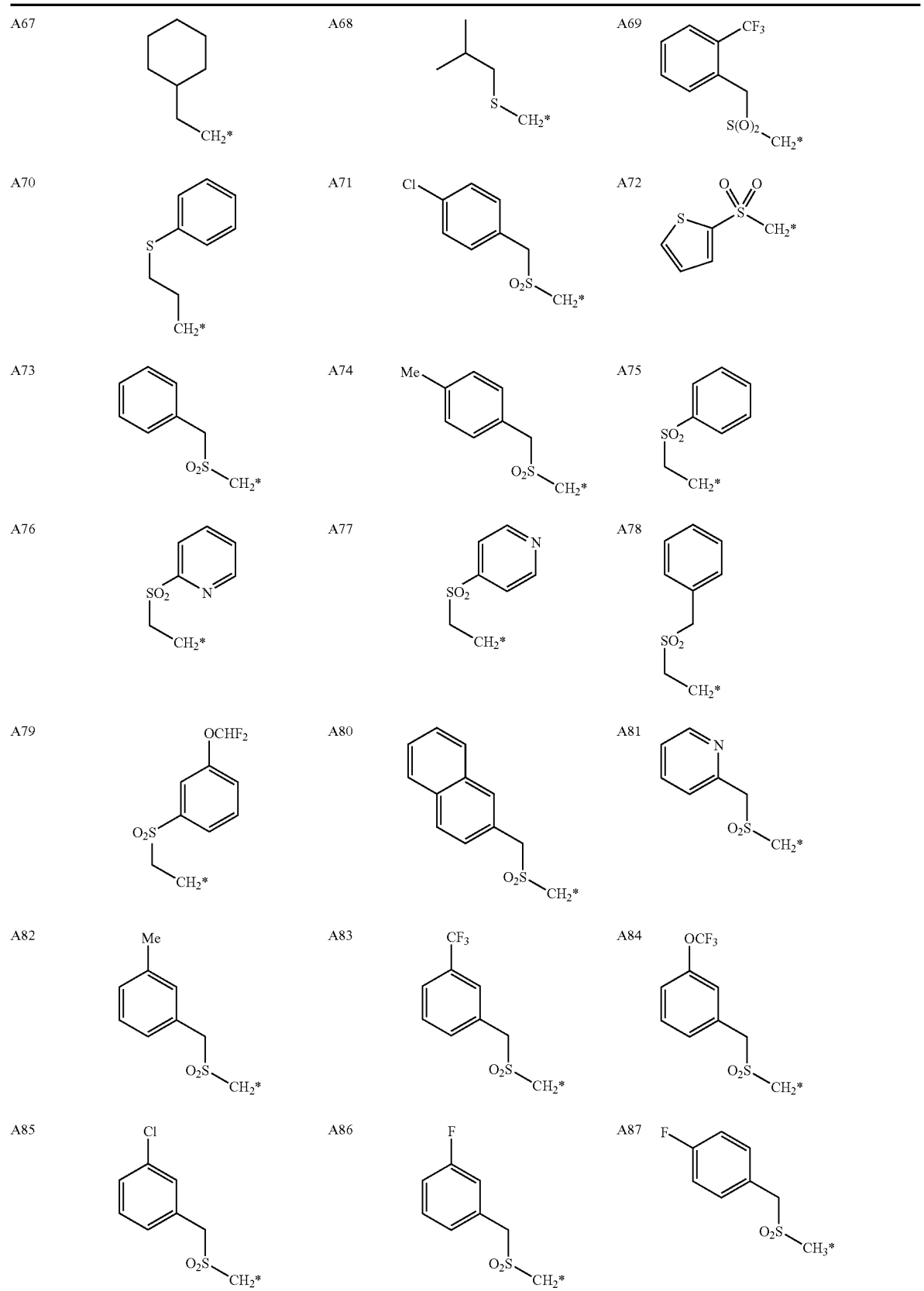

TABLE 1-continued
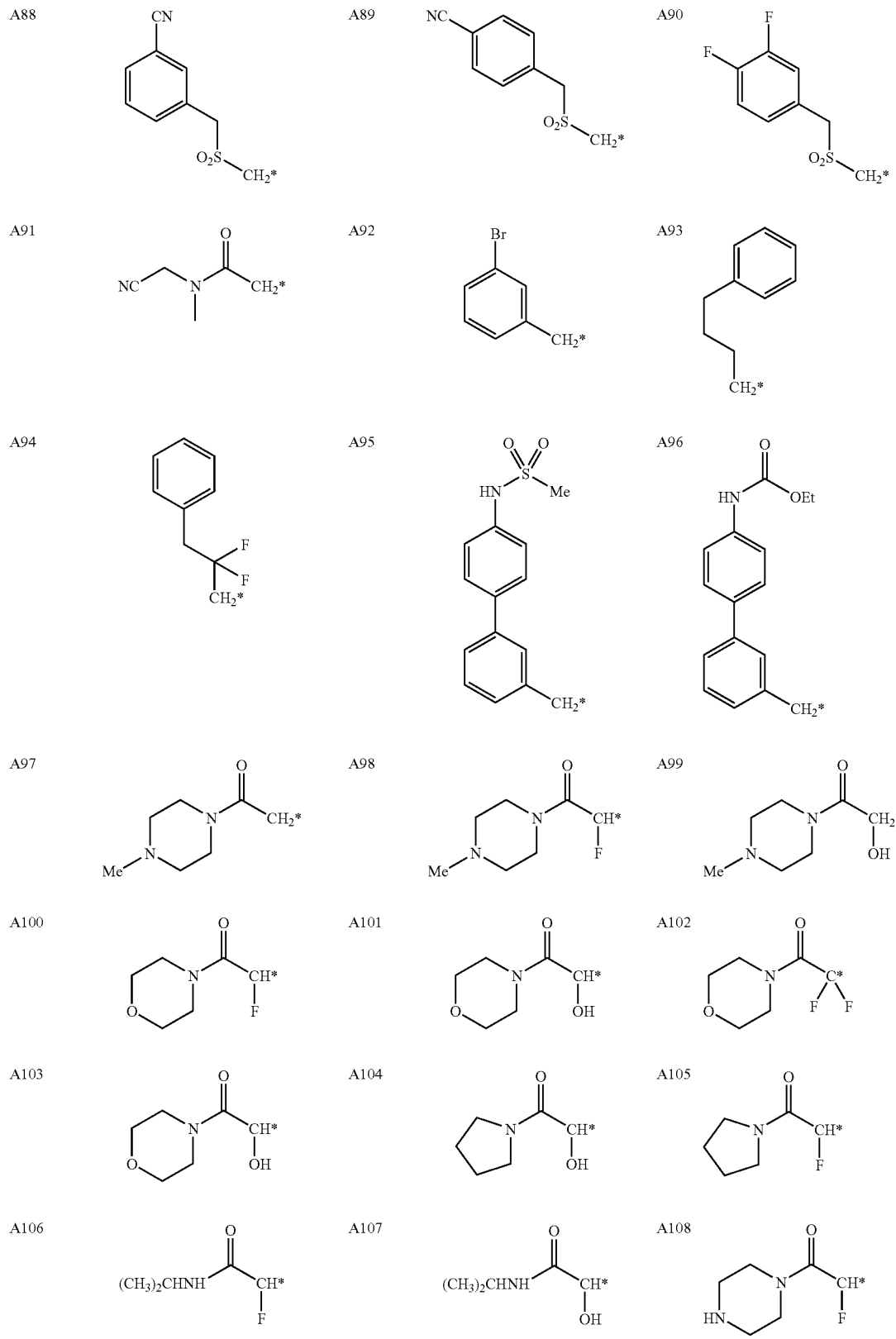

TABLE 1-continued
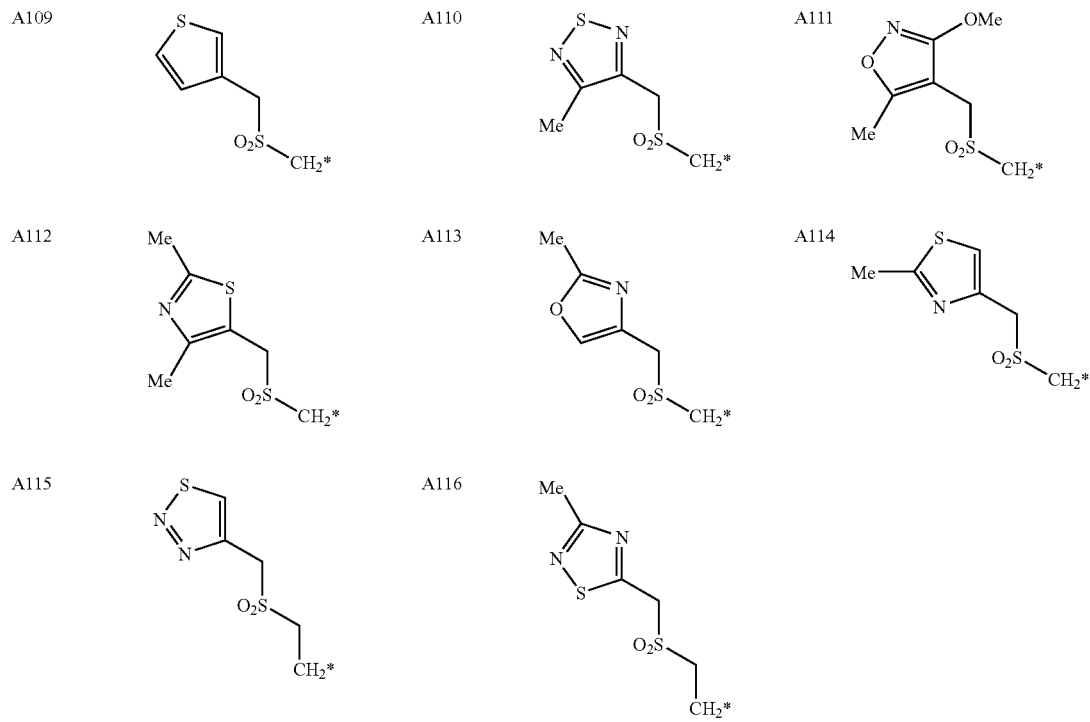
TABLE 2
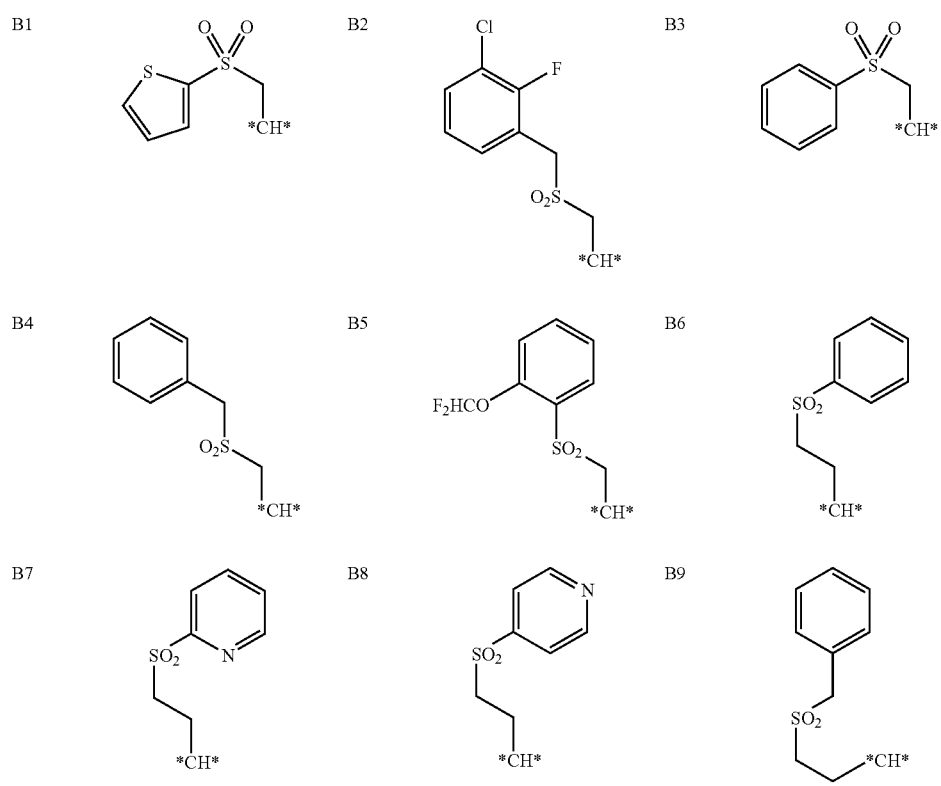

TABLE 2-continued
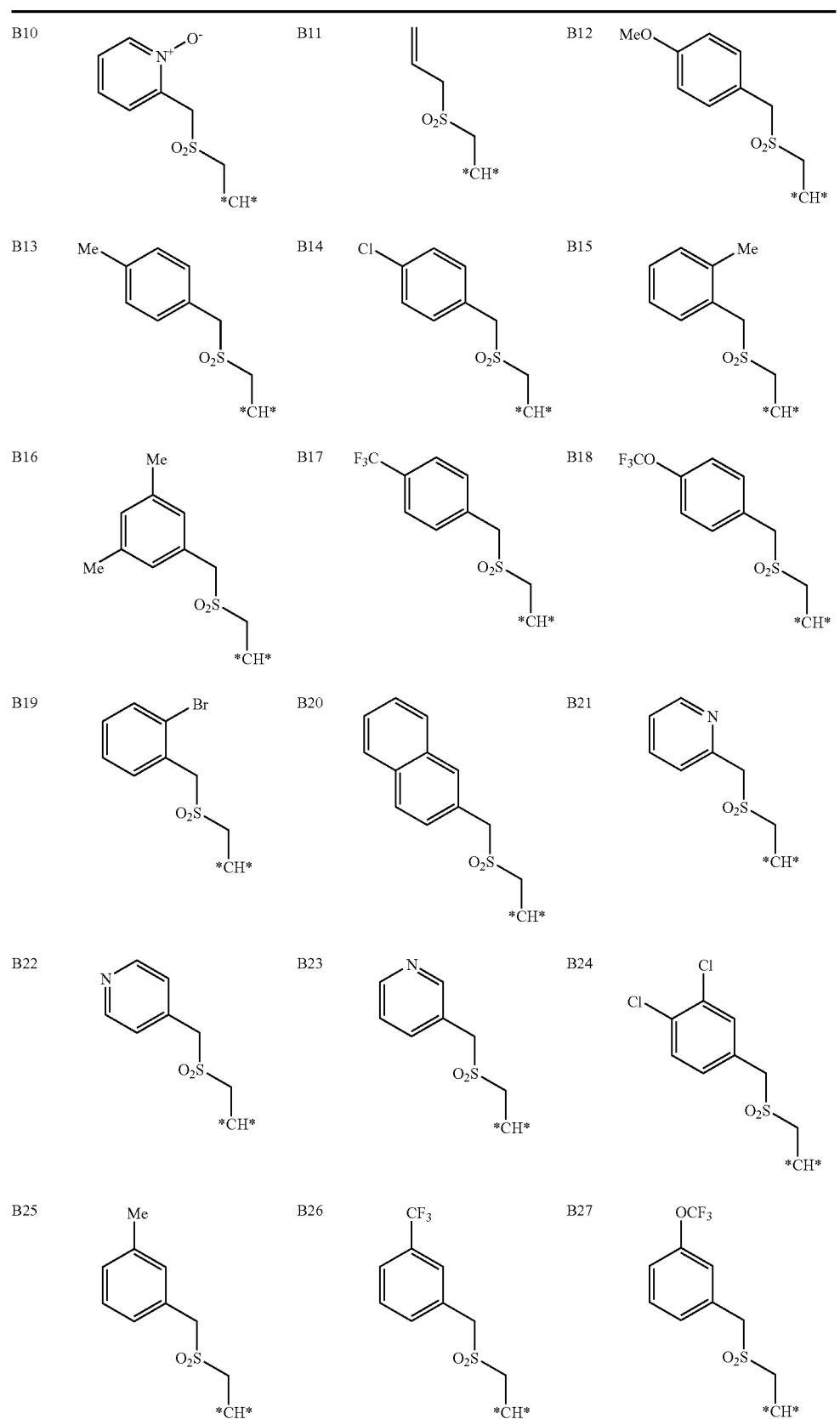

TABLE 2-continued
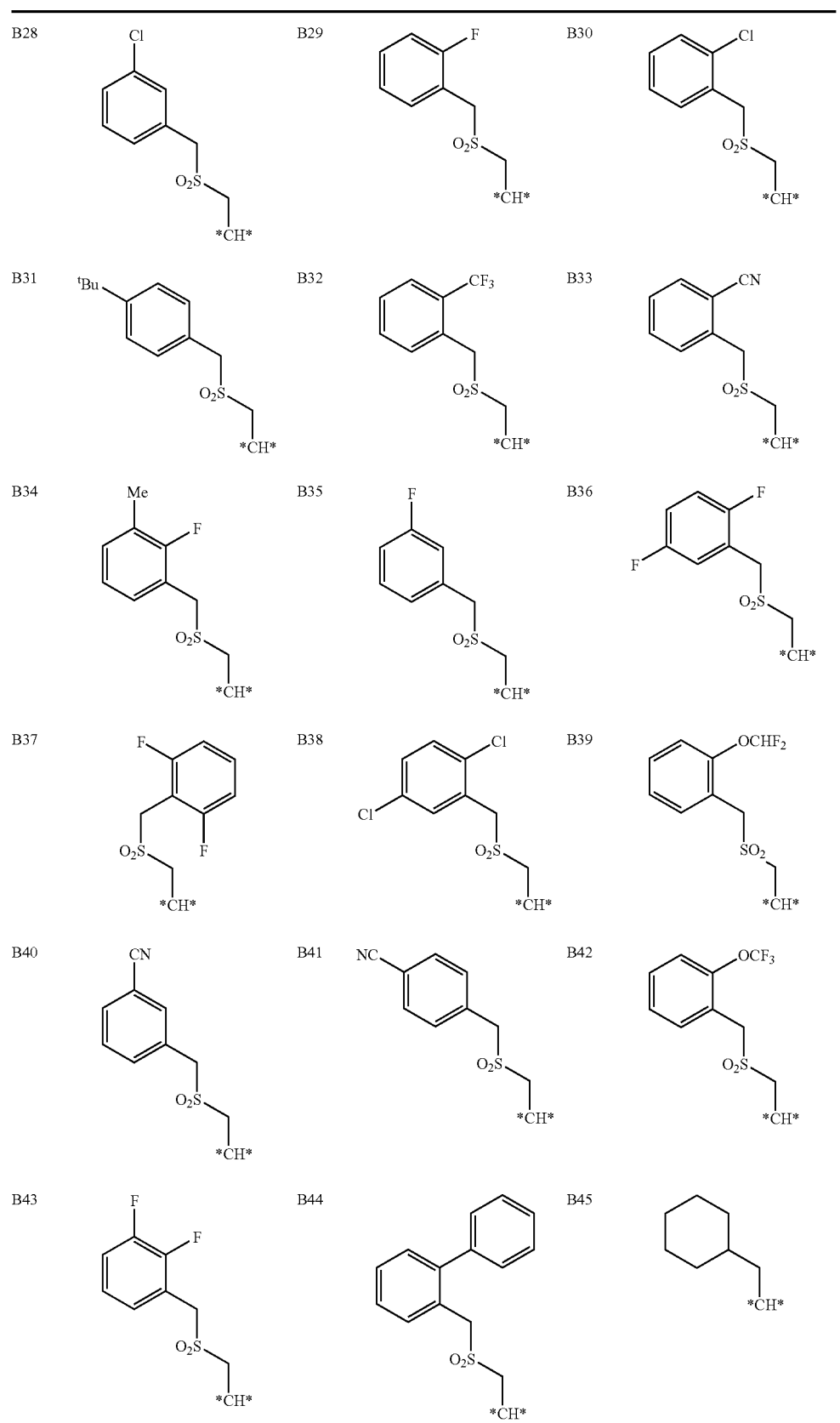

TABLE 2-continued
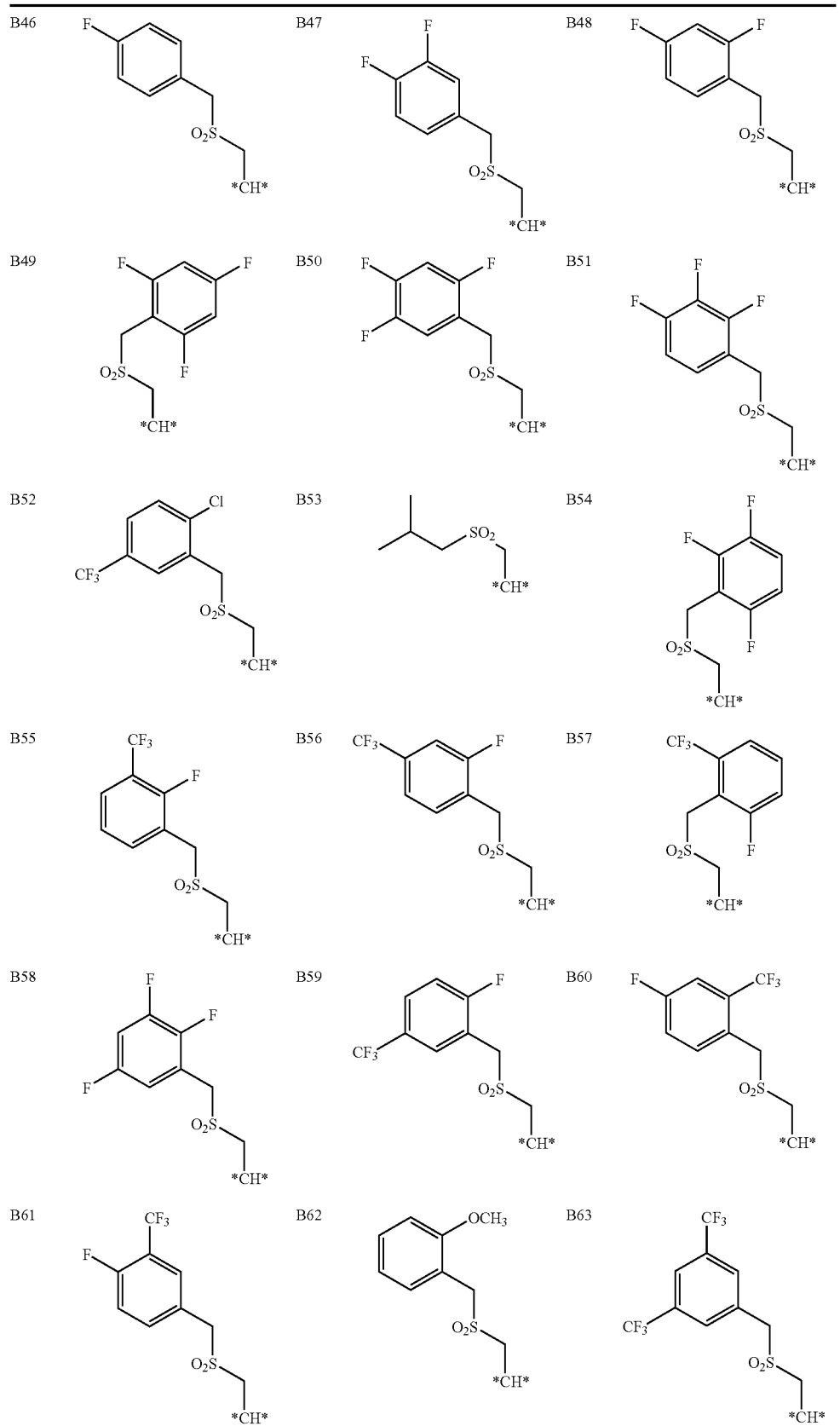

TABLE 2-continued
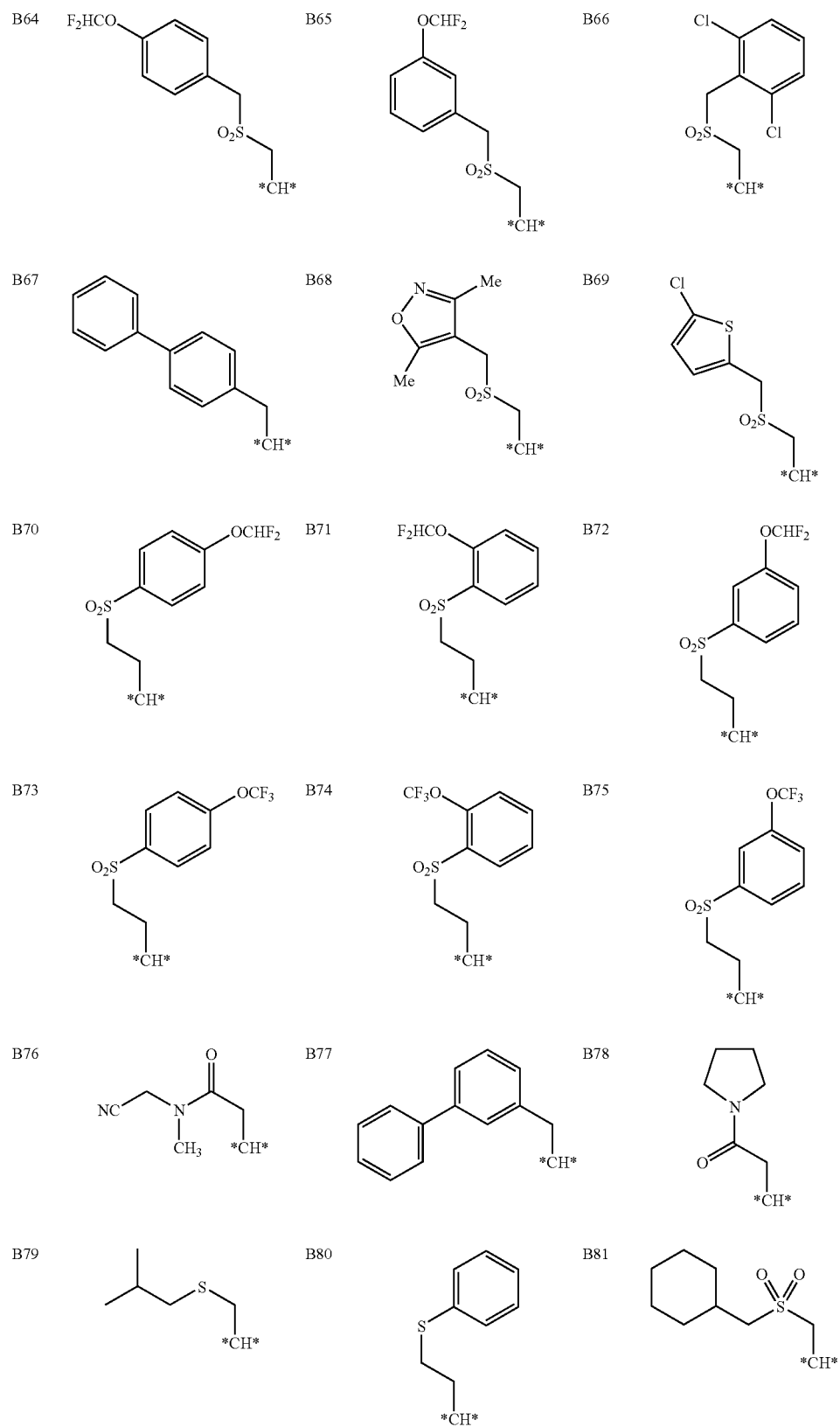

TABLE 2-continued
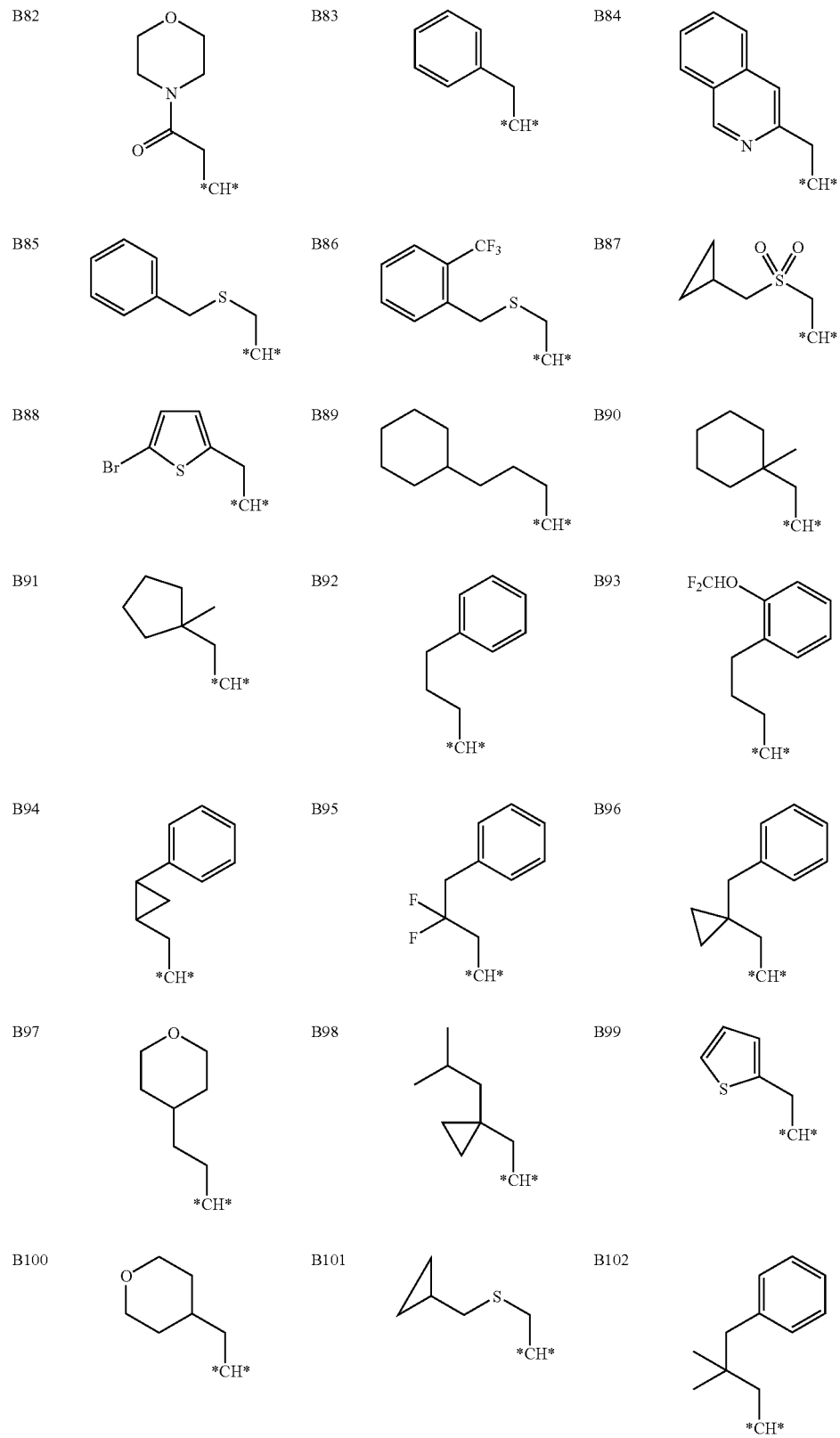

TABLE 2-continued
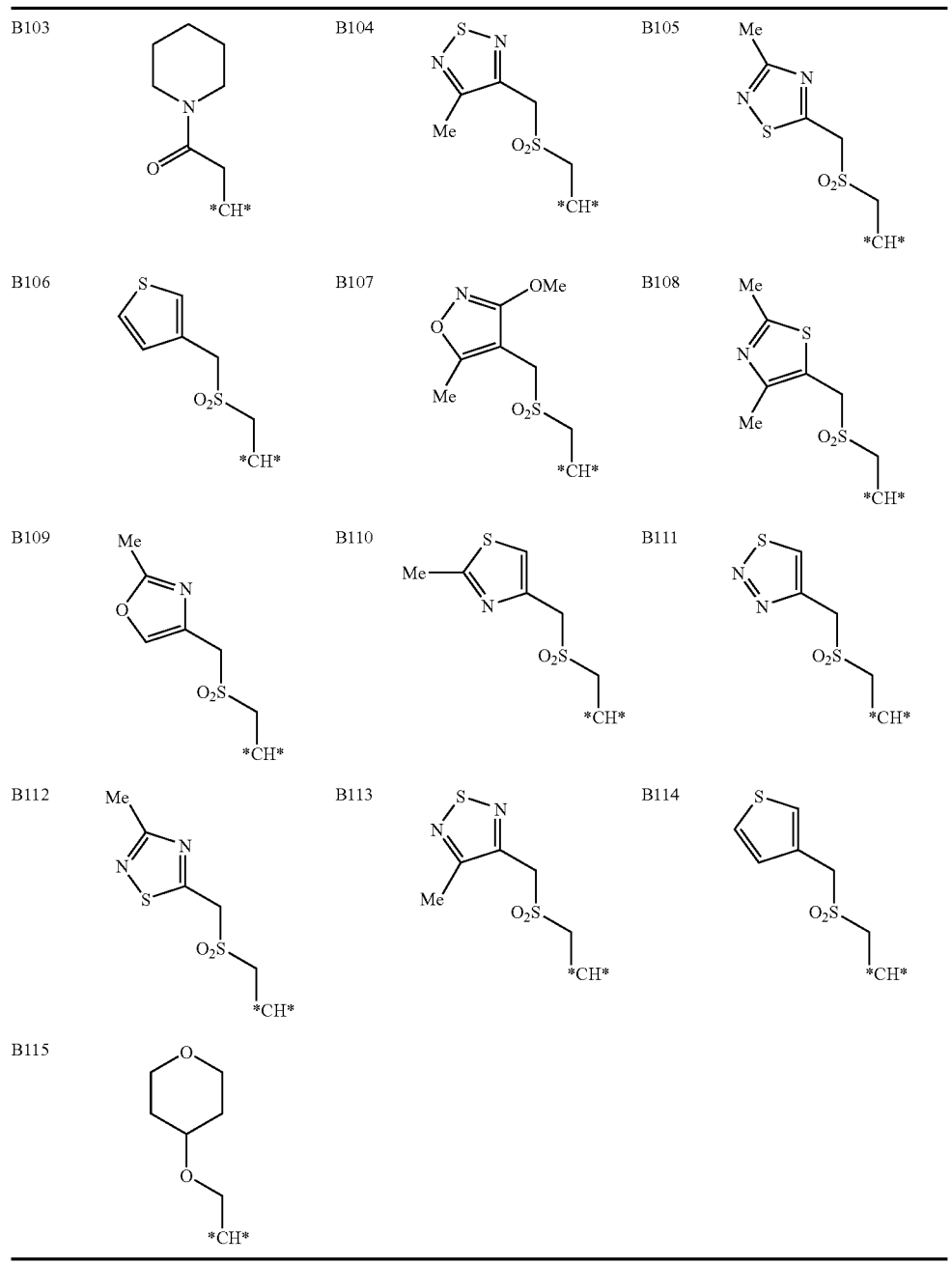
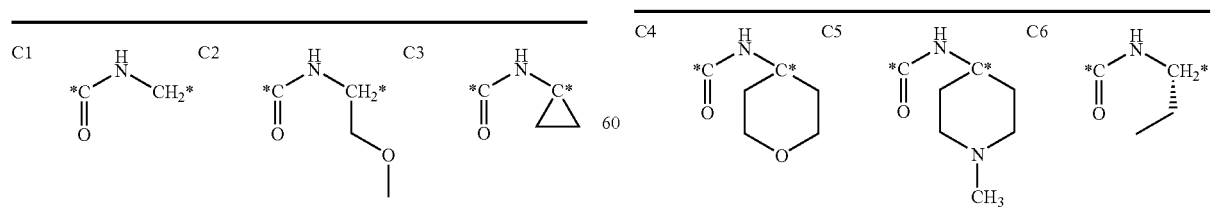

TABLE 3-continued
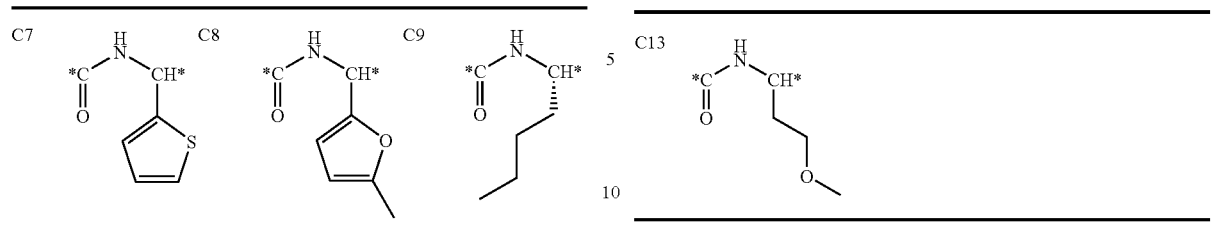
TABLE 4
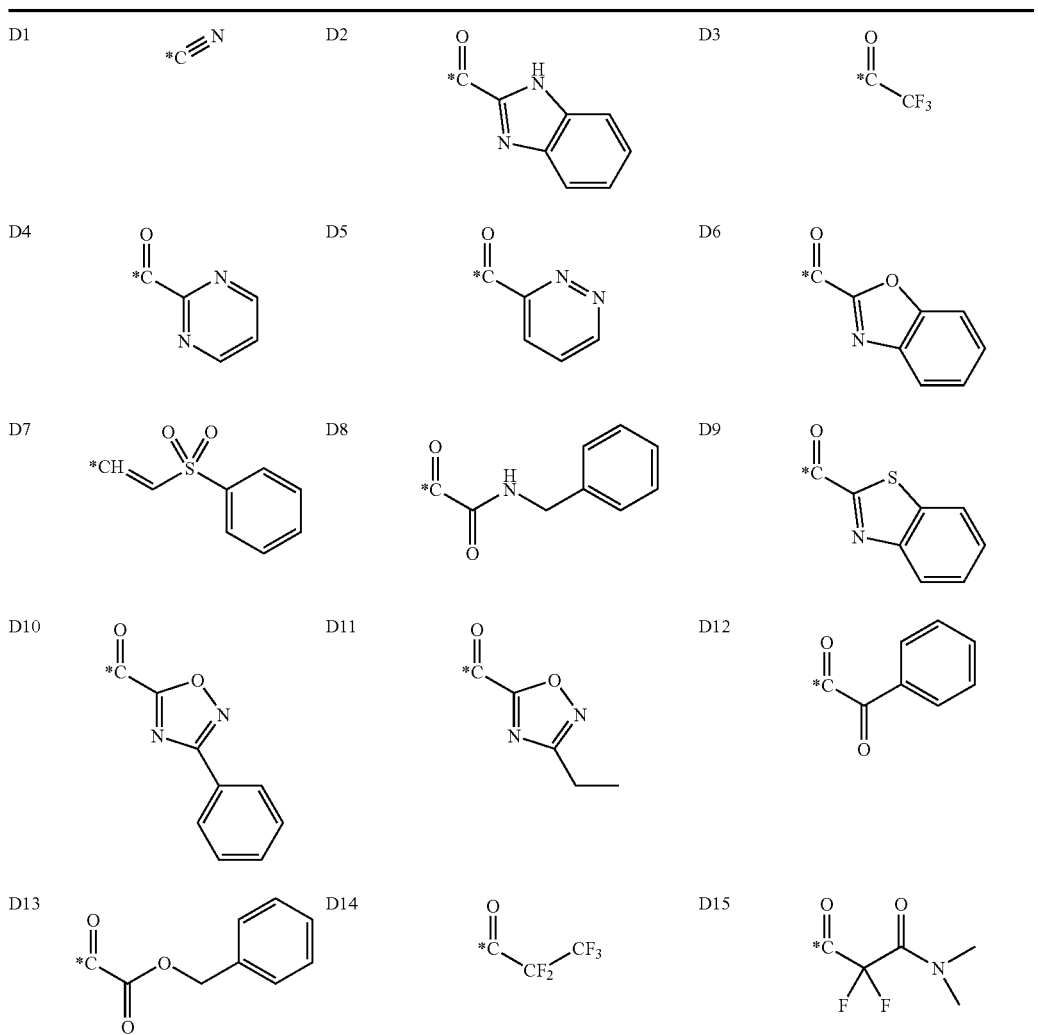

TABLE 4-continued
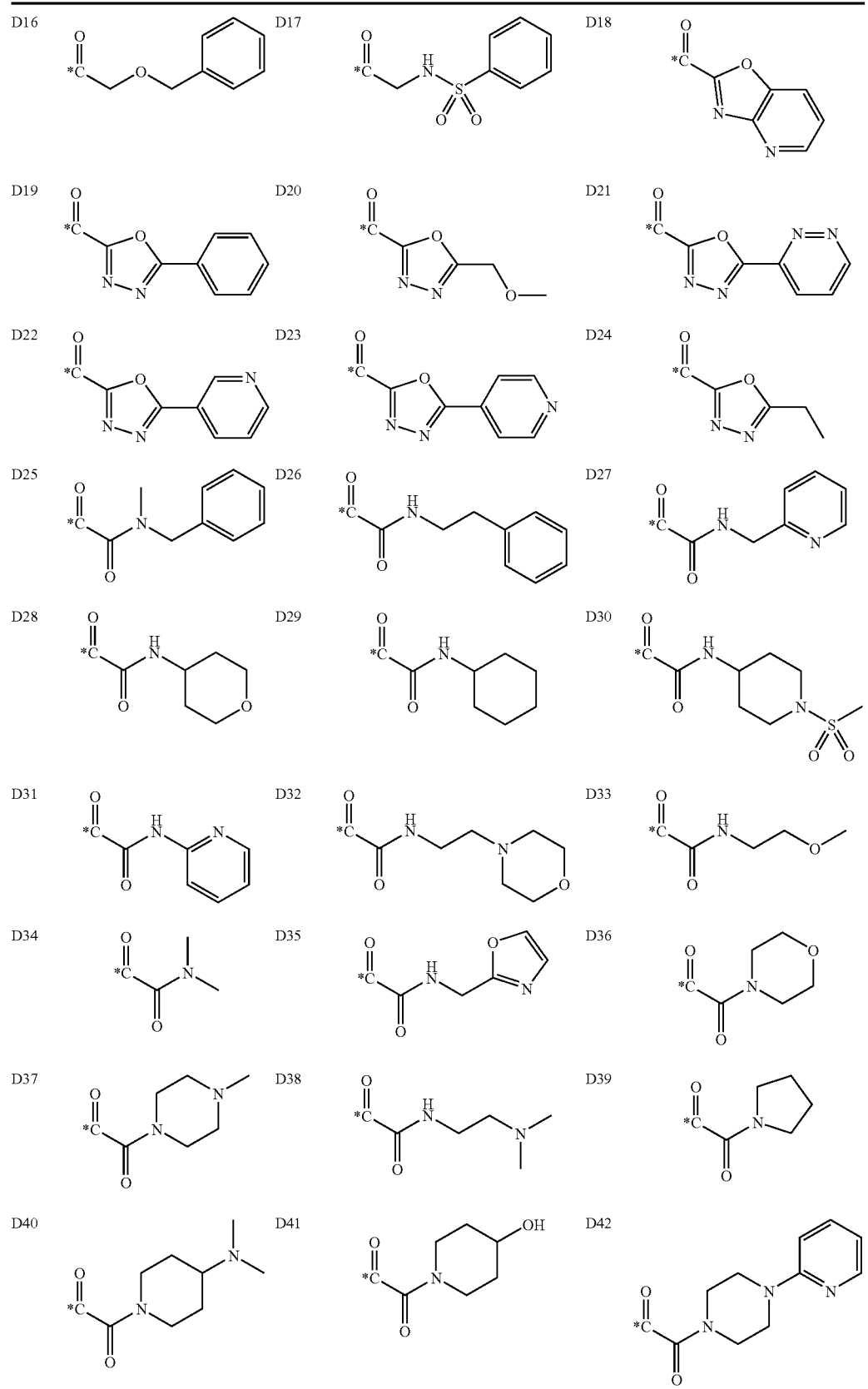

TABLE 4-continued
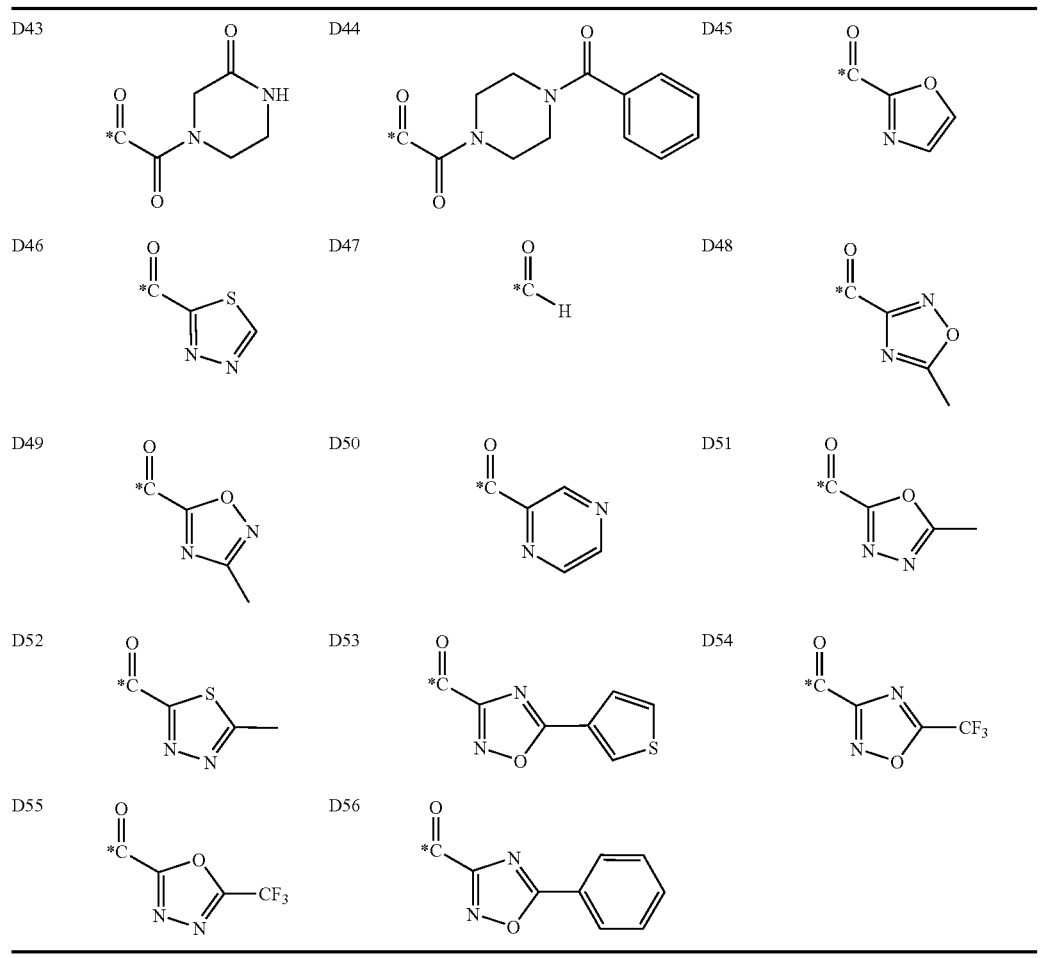
TABLE 5
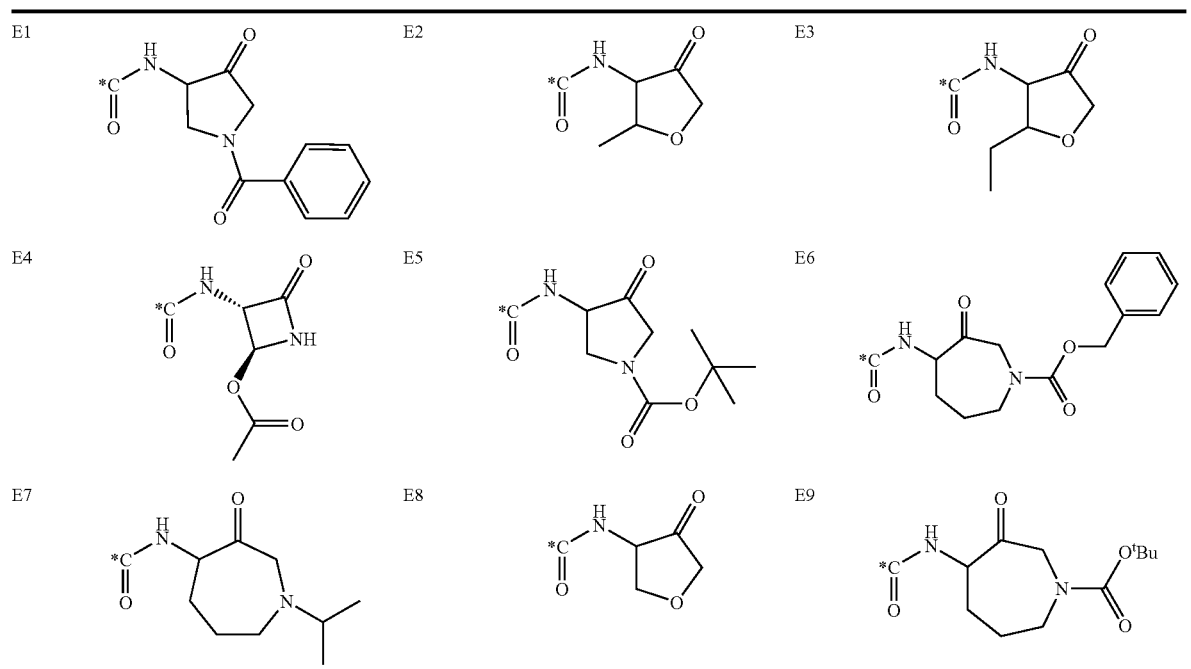

TABLE 5-continued

E10, E11, E12, E13, E14, E15, E16, E17

Particularly preferred compounds of "A", "B", "C" and "D" or "A", "B" and "E" combinations are illustrated in table 6:

TABLE 6

A2-B4-C1-D2
A3-B4-C1-D2
A9-B4-C1-D2
A13-B4-C1-D2
A24-B4-C1-D2
A69-B4-C1-D2
A67-B4-C1-D2
A39-B4-C1-D2
A65-B4-C1-D2
A66-B4-C1-D2
A2-B5-C1-D2
A3-B5-C1-D2
A9-B5-C1-D2
A13-B5-C1-D2
A24-B5-C1-D2
A69-B5-C1-D2
A67-B5-C1-D2
A39-B5-C1-D2
A65-B5-C1-D2
A66-B5-C1-D2
A2-B6-C1-D2
A3-B6-C1-D2
A9-B6-C1-D2
A13-B6-C1-D2
A24-B6-C1-D2
A69-B6-C1-D2
A67-B6-C1-D2
A39-B6-C1-D2
A65-B6-C1-D2
A66-B6-C1-D2
A2-B32-C1-D2
A3-B32-C1-D2
A9-B32-C1-D2
A13-B32-C1-D2
A24-B32-C1-D2
A69-B32-C1-D2
A67-B32-C1-D2
A39-B32-C1-D2

TABLE 6-continued

A65-B32-C1-D2
A66-B32-C1-D2
A2-B39-C1-D2
A3-B39-C1-D2
A9-B39-C1-D2
A13-B39-C1-D2
A24-B39-C1-D2
A69-B39-C1-D2
A67-B39-C1-D2
A39-B39-C1-D2
A65-B39-C1-D2
A66-B39-C1-D2
A2-B45-C1-D2
A3-B45-C1-D2
A9-B45-C1-D2
A13-B45-C1-D2
A24-B45-C1-D2
A69-B45-C1-D2
A67-B45-C1-D2
A39-B45-C1-D2
A65-B45-C1-D2
A66-B45-C1-D2
A2-B53-C1-D2
A3-B53-C1-D2
A9-B53-C1-D2
A13-B53-C1-D2
A24-B53-C1-D2
A69-B53-C1-D2
A67-B53-C1-D2
A39-B53-C1-D2
A65-B53-C1-D2
A66-B53-C1-D2
A2-B79-C1-D2
A3-B79-C1-D2
A9-B79-C1-D2
A13-B79-C1-D2
A24-B79-C1-D2
A69-B79-C1-D2
A67-B79-C1-D2
A39-B79-C1-D2
A65-B79-C1-D2
A66-B79-C1-D2

TABLE 6-continued

A2-B80-C1-D2
A3-B80-C1-D2
A9-B80-C1-D2
A13-B80-C1-D2
A24-B80-C1-D2
A69-B80-C1-D2
A67-B80-C1-D2
A39-B80-C1-D2
A65-B80-C1-D2
A66-B80-C1-D2
A2-B85-C1-D2
A3-B85-C1-D2
A9-B85-C1-D2
A13-B85-C1-D2
A24-B85-C1-D2
A69-B85-C1-D2
A67-B85-C1-D2
A39-B85-C1-D2
A65-B85-C1-D2
A66-B85-C1-D2
A2-B86-C1-D2
A3-B86-C1-D2
A9-B86-C1-D2
A13-B86-C1-D2
A24-B86-C1-D2
A69-B86-C1-D2
A67-B86-C1-D2
A39-B86-C1-D2
A65-B86-C1-D2
A66-B86-C1-D2
A2-B87-C1-D2
A3-B87-C1-D2
A9-B87-C1-D2
A13-B87-C1-D2
A24-B87-C1-D2
A69-B87-C1-D2
A67-B87-C1-D2
A39-B87-C1-D2
A65-B87-C1-D2
A66-B87-C1-D2
A2-B89-C1-D2
A3-B89-C1-D2
A9-B89-C1-D2
A13-B89-C1-D2
A24-B89-C1-D2
A69-B89-C1-D2
A67-B89-C1-D2
A39-B89-C1-D2
A65-B89-C1-D2
A66-B89-C1-D2
A2-B92-C1-D2
A3-B92-C1-D2
A9-B92-C1-D2
A13-B92-C1-D2
A24-B92-C1-D2
A69-B92-C1-D2
A67-B92-C1-D2
A39-B92-C1-D2
A65-B92-C1-D2
A66-B92-C1-D2
A2-B4-C2-D2
A3-B4-C2-D2
A9-B4-C2-D2
A13-B4-C2-D2
A24-B4-C2-D2
A69-B4-C2-D2
A67-B4-C2-D2
A39-B4-C2-D2
A65-B4-C2-D2
A66-B4-C2-D2
A2-B5-C2-D2
A3-B5-C2-D2
A9-B5-C2-D2
A13-B5-C2-D2
A24-B5-C2-D2
A69-B5-C2-D2
A67-B5-C2-D2
A39-B5-C2-D2
A65-B5-C2-D2

TABLE 6-continued

A66-B5-C2-D2
A2-B6-C2-D2
A3-B6-C2-D2
A9-B6-C2-D2
A13-B6-C2-D2
A24-B6-C2-D2
A69-B6-C2-D2
A67-B6-C2-D2
A39-B6-C2-D2
A65-B6-C2-D2
A66-B6-C2-D2
A2-B32-C2-D2
A3-B32-C2-D2
A9-B32-C2-D2
A13-B32-C2-D2
A24-B32-C2-D2
A69-B32-C2-D2
A67-B32-C2-D2
A39-B32-C2-D2
A65-B32-C2-D2
A66-B32-C2-D2
A2-B39-C2-D2
A3-B39-C2-D2
A9-B39-C2-D2
A13-B39-C2-D2
A24-B39-C2-D2
A69-B39-C2-D2
A67-B39-C2-D2
A39-B39-C2-D2
A65-B39-C2-D2
A66-B39-C2-D2
A2-B45-C2-D2
A3-B45-C2-D2
A9-B45-C2-D2
A13-B45-C2-D2
A24-B45-C2-D2
A69-B45-C2-D2
A67-B45-C2-D2
A39-B45-C2-D2
A65-B45-C2-D2
A66-B45-C2-D2
A2-B53-C2-D2
A3-B53-C2-D2
A9-B53-C2-D2
A13-B53-C2-D2
A24-B53-C2-D2
A69-B53-C2-D2
A67-B53-C2-D2
A39-B53-C2-D2
A65-B53-C2-D2
A66-B53-C2-D2
A2-B79-C2-D2
A3-B79-C2-D2
A9-B79-C2-D2
A13-B79-C2-D2
A24-B79-C2-D2
A69-B79-C2-D2
A67-B79-C2-D2
A39-B79-C2-D2
A65-B79-C2-D2
A66-B79-C2-D2
A2-B80-C2-D2
A3-B80-C2-D2
A9-B80-C2-D2
A13-B80-C2-D2
A24-B80-C2-D2
A69-B80-C2-D2
A67-B80-C2-D2
A39-B80-C2-D2
A65-B80-C2-D2
A66-B80-C2-D2
A2-B85-C2-D2
A3-B85-C2-D2
A9-B85-C2-D2
A13-B85-C2-D2
A24-B85-C2-D2
A69-B85-C2-D2
A67-B85-C2-D2
A39-B85-C2-D2

TABLE 6-continued

| | |
|---|---|
| A65-B85-C2-D2 | A39-B32-C3-D2 |
| A66-B85-C2-D2 | A65-B32-C3-D2 |
| A2-B86-C2-D2 | A66-B32-C3-D2 |
| A3-B86-C2-D2 | A2-B39-C3-D2 |
| A9-B86-C2-D2 | A3-B39-C3-D2 |
| A13-B86-C2-D2 | A9-B39-C3-D2 |
| A24-B86-C2-D2 | A13-B39-C3-D2 |
| A69-B86-C2-D2 | A24-B39-C3-D2 |
| A67-B86-C2-D2 | A69-B39-C3-D2 |
| A39-B86-C2-D2 | A67-B39-C3-D2 |
| A65-B86-C2-D2 | A39-B39-C3-D2 |
| A66-B86-C2-D2 | A65-B39-C3-D2 |
| A2-B87-C2-D2 | A66-B39-C3-D2 |
| A3-B87-C2-D2 | A2-B45-C3-D2 |
| A9-B87-C2-D2 | A3-B45-C3-D2 |
| A13-B87-C2-D2 | A9-B45-C3-D2 |
| A24-B87-C2-D2 | A13-B45-C3-D2 |
| A69-B87-C2-D2 | A24-B45-C3-D2 |
| A67-B87-C2-D2 | A69-B45-C3-D2 |
| A39-B87-C2-D2 | A67-B45-C3-D2 |
| A65-B87-C2-D2 | A39-B45-C3-D2 |
| A66-B87-C2-D2 | A65-B45-C3-D2 |
| A2-B89-C2-D2 | A66-B45-C3-D2 |
| A3-B89-C2-D2 | A2-B53-C3-D2 |
| A9-B89-C2-D2 | A3-B53-C3-D2 |
| A13-B89-C2-D2 | A9-B53-C3-D2 |
| A24-B89-C2-D2 | A13-B53-C3-D2 |
| A69-B89-C2-D2 | A24-B53-C3-D2 |
| A67-B89-C2-D2 | A69-B53-C3-D2 |
| A39-B89-C2-D2 | A67-B53-C3-D2 |
| A65-B89-C2-D2 | A39-B53-C3-D2 |
| A66-B89-C2-D2 | A65-B53-C3-D2 |
| A2-B92-C2-D2 | A66-B53-C3-D2 |
| A3-B92-C2-D2 | A2-B79-C3-D2 |
| A9-B92-C2-D2 | A3-B79-C3-D2 |
| A13-B92-C2-D2 | A9-B79-C3-D2 |
| A24-B92-C2-D2 | A13-B79-C3-D2 |
| A69-B92-C2-D2 | A24-B79-C3-D2 |
| A67-B92-C2-D2 | A69-B79-C3-D2 |
| A39-B92-C2-D2 | A67-B79-C3-D2 |
| A65-B92-C2-D2 | A39-B79-C3-D2 |
| A66-B92-C2-D2 | A65-B79-C3-D2 |
| A2-B4-C3-D2 | A66-B79-C3-D2 |
| A3-B4-C3-D2 | A2-B80-C3-D2 |
| A9-B4-C3-D2 | A3-B80-C3-D2 |
| A13-B4-C3-D2 | A9-B80-C3-D2 |
| A24-B4-C3-D2 | A13-B80-C3-D2 |
| A69-B4-C3-D2 | A24-B80-C3-D2 |
| A67-B4-C3-D2 | A69-B80-C3-D2 |
| A39-B4-C3-D2 | A67-B80-C3-D2 |
| A65-B4-C3-D2 | A39-B80-C3-D2 |
| A66-B4-C3-D2 | A65-B80-C3-D2 |
| A2-B5-C3-D2 | A66-B80-C3-D2 |
| A3-B5-C3-D2 | A2-B85-C3-D2 |
| A9-B5-C3-D2 | A3-B85-C3-D2 |
| A13-B5-C3-D2 | A9-B85-C3-D2 |
| A24-B5-C3-D2 | A13-B85-C3-D2 |
| A69-B5-C3-D2 | A24-B85-C3-D2 |
| A67-B5-C3-D2 | A69-B85-C3-D2 |
| A39-B5-C3-D2 | A67-B85-C3-D2 |
| A65-B5-C3-D2 | A39-B85-C3-D2 |
| A66-B5-C3-D2 | A65-B85-C3-D2 |
| A2-B6-C3-D2 | A66-B85-C3-D2 |
| A3-B6-C3-D2 | A2-B86-C3-D2 |
| A9-B6-C3-D2 | A3-B86-C3-D2 |
| A13-B6-C3-D2 | A9-B86-C3-D2 |
| A24-B6-C3-D2 | A13-B86-C3-D2 |
| A69-B6-C3-D2 | A24-B86-C3-D2 |
| A67-B6-C3-D2 | A69-B86-C3-D2 |
| A39-B6-C3-D2 | A67-B86-C3-D2 |
| A65-B6-C3-D2 | A39-B86-C3-D2 |
| A66-B6-C3-D2 | A65-B86-C3-D2 |
| A2-B32-C3-D2 | A66-B86-C3-D2 |
| A3-B32-C3-D2 | A2-B87-C3-D2 |
| A9-B32-C3-D2 | A3-B87-C3-D2 |
| A13-B32-C3-D2 | A9-B87-C3-D2 |
| A24-B32-C3-D2 | A13-B87-C3-D2 |
| A69-B32-C3-D2 | A24-B87-C3-D2 |
| A67-B32-C3-D2 | A69-B87-C3-D2 |

TABLE 6-continued

| | |
|---|---|
| A67-B87-C3-D2 | A69-B45-C4-D2 |
| A39-B87-C3-D2 | A67-B45-C4-D2 |
| A65-B87-C3-D2 | A39-B45-C4-D2 |
| A66-B87-C3-D2 | A65-B45-C4-D2 |
| A2-B89-C3-D2 | A66-B45-C4-D2 |
| A3-B89-C3-D2 | A2-B53-C4-D2 |
| A9-B89-C3-D2 | A3-B53-C4-D2 |
| A13-B89-C3-D2 | A9-B53-C4-D2 |
| A24-B89-C3-D2 | A13-B53-C4-D2 |
| A69-B89-C3-D2 | A24-B53-C4-D2 |
| A67-B89-C3-D2 | A69-B53-C4-D2 |
| A39-B89-C3-D2 | A67-B53-C4-D2 |
| A65-B89-C3-D2 | A39-B53-C4-D2 |
| A66-B89-C3-D2 | A65-B53-C4-D2 |
| A2-B92-C3-D2 | A66-B53-C4-D2 |
| A3-B92-C3-D2 | A2-B79-C4-D2 |
| A9-B92-C3-D2 | A3-B79-C4-D2 |
| A13-B92-C3-D2 | A9-B79-C4-D2 |
| A24-B92-C3-D2 | A13-B79-C4-D2 |
| A69-B92-C3-D2 | A24-B79-C4-D2 |
| A67-B92-C3-D2 | A69-B79-C4-D2 |
| A39-B92-C3-D2 | A67-B79-C4-D2 |
| A65-B92-C3-D2 | A39-B79-C4-D2 |
| A66-B92-C3-D2 | A65-B79-C4-D2 |
| A2-B4-C4-D2 | A66-B79-C4-D2 |
| A3-B4-C4-D2 | A2-B80-C4-D2 |
| A9-B4-C4-D2 | A3-B80-C4-D2 |
| A13-B4-C4-D2 | A9-B80-C4-D2 |
| A24-B4-C4-D2 | A13-B80-C4-D2 |
| A69-B4-C4-D2 | A24-B80-C4-D2 |
| A67-B4-C4-D2 | A69-B80-C4-D2 |
| A39-B4-C4-D2 | A67-B80-C4-D2 |
| A65-B4-C4-D2 | A39-B80-C4-D2 |
| A66-B4-C4-D2 | A65-B80-C4-D2 |
| A2-B5-C4-D2 | A66-B80-C4-D2 |
| A3-B5-C4-D2 | A2-B85-C4-D2 |
| A9-B5-C4-D2 | A3-B85-C4-D2 |
| A13-B5-C4-D2 | A9-B85-C4-D2 |
| A24-B5-C4-D2 | A13-B85-C4-D2 |
| A69-B5-C4-D2 | A24-B85-C4-D2 |
| A67-B5-C4-D2 | A69-B85-C4-D2 |
| A39-B5-C4-D2 | A67-B85-C4-D2 |
| A65-B5-C4-D2 | A39-B85-C4-D2 |
| A66-B5-C4-D2 | A65-B85-C4-D2 |
| A2-B6-C4-D2 | A66-B85-C4-D2 |
| A3-B6-C4-D2 | A2-B86-C4-D2 |
| A9-B6-C4-D2 | A3-B86-C4-D2 |
| A13-B6-C4-D2 | A9-B86-C4-D2 |
| A24-B6-C4-D2 | A13-B86-C4-D2 |
| A69-B6-C4-D2 | A24-B86-C4-D2 |
| A67-B6-C4-D2 | A69-B86-C4-D2 |
| A39-B6-C4-D2 | A67-B86-C4-D2 |
| A65-B6-C4-D2 | A39-B86-C4-D2 |
| A66-B6-C4-D2 | A65-B86-C4-D2 |
| A2-B32-C4-D2 | A66-B86-C4-D2 |
| A3-B32-C4-D2 | A2-B87-C4-D2 |
| A9-B32-C4-D2 | A3-B87-C4-D2 |
| A13-B32-C4-D2 | A9-B87-C4-D2 |
| A24-B32-C4-D2 | A13-B87-C4-D2 |
| A69-B32-C4-D2 | A24-B87-C4-D2 |
| A67-B32-C4-D2 | A69-B87-C4-D2 |
| A39-B32-C4-D2 | A67-B87-C4-D2 |
| A65-B32-C4-D2 | A39-B87-C4-D2 |
| A66-B32-C4-D2 | A65-B87-C4-D2 |
| A2-B39-C4-D2 | A66-B87-C4-D2 |
| A3-B39-C4-D2 | A2-B89-C4-D2 |
| A9-B39-C4-D2 | A3-B89-C4-D2 |
| A13-B39-C4-D2 | A9-B89-C4-D2 |
| A24-B39-C4-D2 | A13-B89-C4-D2 |
| A69-B39-C4-D2 | A24-B89-C4-D2 |
| A67-B39-C4-D2 | A69-B89-C4-D2 |
| A39-B39-C4-D2 | A67-B89-C4-D2 |
| A65-B39-C4-D2 | A39-B89-C4-D2 |
| A66-B39-C4-D2 | A65-B89-C4-D2 |
| A2-B45-C4-D2 | A66-B89-C4-D2 |
| A3-B45-C4-D2 | A2-B92-C4-D2 |
| A9-B45-C4-D2 | A3-B92-C4-D2 |
| A13-B45-C4-D2 | A9-B92-C4-D2 |
| A24-B45-C4-D2 | A13-B92-C4-D2 |

TABLE 6-continued

| | |
|---|---|
| A24-B92-C4-D2 | A13-B79-C5-D2 |
| A69-B92-C4-D2 | A24-B79-C5-D2 |
| A67-B92-C4-D2 | A69-B79-C5-D2 |
| A39-B92-C4-D2 | A67-B79-C5-D2 |
| A65-B92-C4-D2 | A39-B79-C5-D2 |
| A66-B92-C4-D2 | A65-B79-C5-D2 |
| A2-B4-C5-D2 | A66-B79-C5-D2 |
| A3-B4-C5-D2 | A2-B80-C5-D2 |
| A9-B4-C5-D2 | A3-B80-C5-D2 |
| A13-B4-C5-D2 | A9-B80-C5-D2 |
| A24-B4-C5-D2 | A13-B80-C5-D2 |
| A69-B4-C5-D2 | A24-B80-C5-D2 |
| A67-B4-C5-D2 | A69-B80-C5-D2 |
| A39-B4-C5-D2 | A67-B80-C5-D2 |
| A65-B4-C5-D2 | A39-B80-C5-D2 |
| A66-B4-C5-D2 | A65-B80-C5-D2 |
| A2-B5-C5-D2 | A66-B80-C5-D2 |
| A3-B5-C5-D2 | A2-B85-C5-D2 |
| A9-B5-C5-D2 | A3-B85-C5-D2 |
| A13-B5-C5-D2 | A9-B85-C5-D2 |
| A24-B5-C5-D2 | A13-B85-C5-D2 |
| A69-B5-C5-D2 | A24-B85-C5-D2 |
| A67-B5-C5-D2 | A69-B85-C5-D2 |
| A39-B5-C5-D2 | A67-B85-C5-D2 |
| A65-B5-C5-D2 | A39-B85-C5-D2 |
| A66-B5-C5-D2 | A65-B85-C5-D2 |
| A2-B6-C5-D2 | A66-B85-C5-D2 |
| A3-B6-C5-D2 | A2-B86-C5-D2 |
| A9-B6-C5-D2 | A3-B86-C5-D2 |
| A13-B6-C5-D2 | A9-B86-C5-D2 |
| A24-B6-C5-D2 | A13-B86-C5-D2 |
| A69-B6-C5-D2 | A24-B86-C5-D2 |
| A67-B6-C5-D2 | A69-B86-C5-D2 |
| A39-B6-C5-D2 | A67-B86-C5-D2 |
| A65-B6-C5-D2 | A39-B86-C5-D2 |
| A66-B6-C5-D2 | A65-B86-C5-D2 |
| A2-B32-C5-D2 | A66-B86-C5-D2 |
| A3-B32-C5-D2 | A2-B87-C5-D2 |
| A9-B32-C5-D2 | A3-B87-C5-D2 |
| A13-B32-C5-D2 | A9-B87-C5-D2 |
| A24-B32-C5-D2 | A13-B87-C5-D2 |
| A69-B32-C5-D2 | A24-B87-C5-D2 |
| A67-B32-C5-D2 | A69-B87-C5-D2 |
| A39-B32-C5-D2 | A67-B87-C5-D2 |
| A65-B32-C5-D2 | A39-B87-C5-D2 |
| A66-B32-C5-D2 | A65-B87-C5-D2 |
| A2-B39-C5-D2 | A66-B87-C5-D2 |
| A3-B39-C5-D2 | A2-B89-C5-D2 |
| A9-B39-C5-D2 | A3-B89-C5-D2 |
| A13-B39-C5-D2 | A9-B89-C5-D2 |
| A24-B39-C5-D2 | A13-B89-C5-D2 |
| A69-B39-C5-D2 | A24-B89-C5-D2 |
| A67-B39-C5-D2 | A69-B89-C5-D2 |
| A39-B39-C5-D2 | A67-B89-C5-D2 |
| A65-B39-C5-D2 | A39-B89-C5-D2 |
| A66-B39-C5-D2 | A65-B89-C5-D2 |
| A2-B45-C5-D2 | A66-B89-C5-D2 |
| A3-B45-C5-D2 | A2-B92-C5-D2 |
| A9-B45-C5-D2 | A3-B92-C5-D2 |
| A13-B45-C5-D2 | A9-B92-C5-D2 |
| A24-B45-C5-D2 | A13-B92-C5-D2 |
| A69-B45-C5-D2 | A24-B92-C5-D2 |
| A67-B45-C5-D2 | A69-B92-C5-D2 |
| A39-B45-C5-D2 | A67-B92-C5-D2 |
| A65-B45-C5-D2 | A39-B92-C5-D2 |
| A66-B45-C5-D2 | A65-B92-C5-D2 |
| A2-B53-C5-D2 | A66-B92-C5-D2 |
| A3-B53-C5-D2 | A2-B4-C6-D2 |
| A9-B53-C5-D2 | A3-B4-C6-D2 |
| A13-B53-C5-D2 | A9-B4-C6-D2 |
| A24-B53-C5-D2 | A13-B4-C6-D2 |
| A69-B53-C5-D2 | A24-B4-C6-D2 |
| A67-B53-C5-D2 | A69-B4-C6-D2 |
| A39-B53-C5-D2 | A67-B4-C6-D2 |
| A65-B53-C5-D2 | A39-B4-C6-D2 |
| A66-B53-C5-D2 | A65-B4-C6-D2 |
| A2-B79-C5-D2 | A66-B4-C6-D2 |
| A3-B79-C5-D2 | A2-B5-C6-D2 |
| A9-B79-C5-D2 | A3-B5-C6-D2 |

TABLE 6-continued

| | |
|---|---|
| A9-B5-C6-D2 | A3-B85-C6-D2 |
| A13-B5-C6-D2 | A9-B85-C6-D2 |
| A24-B5-C6-D2 | A13-B85-C6-D2 |
| A69-B5-C6-D2 | A24-B85-C6-D2 |
| A67-B5-C6-D2 | A69-B85-C6-D2 |
| A39-B5-C6-D2 | A67-B85-C6-D2 |
| A65-B5-C6-D2 | A39-B85-C6-D2 |
| A66-B5-C6-D2 | A65-B85-C6-D2 |
| A2-B6-C6-D2 | A66-B85-C6-D2 |
| A3-B6-C6-D2 | A2-B86-C6-D2 |
| A9-B6-C6-D2 | A3-B86-C6-D2 |
| A13-B6-C6-D2 | A9-B86-C6-D2 |
| A24-B6-C6-D2 | A13-B86-C6-D2 |
| A69-B6-C6-D2 | A24-B86-C6-D2 |
| A67-B6-C6-D2 | A69-B86-C6-D2 |
| A39-B6-C6-D2 | A67-B86-C6-D2 |
| A65-B6-C6-D2 | A39-B86-C6-D2 |
| A66-B6-C6-D2 | A65-B86-C6-D2 |
| A2-B32-C6-D2 | A66-B86-C6-D2 |
| A3-B32-C6-D2 | A2-B87-C6-D2 |
| A9-B32-C6-D2 | A3-B87-C6-D2 |
| A13-B32-C6-D2 | A9-B87-C6-D2 |
| A24-B32-C6-D2 | A13-B87-C6-D2 |
| A69-B32-C6-D2 | A24-B87-C6-D2 |
| A67-B32-C6-D2 | A69-B87-C6-D2 |
| A39-B32-C6-D2 | A67-B87-C6-D2 |
| A65-B32-C6-D2 | A39-B87-C6-D2 |
| A66-B32-C6-D2 | A65-B87-C6-D2 |
| A2-B39-C6-D2 | A66-B87-C6-D2 |
| A3-B39-C6-D2 | A2-B89-C6-D2 |
| A9-B39-C6-D2 | A3-B89-C6-D2 |
| A13-B39-C6-D2 | A9-B89-C6-D2 |
| A24-B39-C6-D2 | A13-B89-C6-D2 |
| A69-B39-C6-D2 | A24-B89-C6-D2 |
| A67-B39-C6-D2 | A69-B89-C6-D2 |
| A39-B39-C6-D2 | A67-B89-C6-D2 |
| A65-B39-C6-D2 | A39-B89-C6-D2 |
| A66-B39-C6-D2 | A65-B89-C6-D2 |
| A2-B45-C6-D2 | A66-B89-C6-D2 |
| A3-B45-C6-D2 | A2-B92-C6-D2 |
| A9-B45-C6-D2 | A3-B92-C6-D2 |
| A13-B45-C6-D2 | A9-B92-C6-D2 |
| A24-B45-C6-D2 | A13-B92-C6-D2 |
| A69-B45-C6-D2 | A24-B92-C6-D2 |
| A67-B45-C6-D2 | A69-B92-C6-D2 |
| A39-B45-C6-D2 | A67-B92-C6-D2 |
| A65-B45-C6-D2 | A39-B92-C6-D2 |
| A66-B45-C6-D2 | A65-B92-C6-D2 |
| A2-B53-C6-D2 | A66-B92-C6-D2 |
| A3-B53-C6-D2 | A2-B4-C7-D2 |
| A9-B53-C6-D2 | A3-B4-C7-D2 |
| A13-B53-C6-D2 | A9-B4-C7-D2 |
| A24-B53-C6-D2 | A13-B4-C7-D2 |
| A69-B53-C6-D2 | A24-B4-C7-D2 |
| A67-B53-C6-D2 | A69-B4-C7-D2 |
| A39-B53-C6-D2 | A67-B4-C7-D2 |
| A65-B53-C6-D2 | A39-B4-C7-D2 |
| A66-B53-C6-D2 | A65-B4-C7-D2 |
| A2-B79-C6-D2 | A66-B4-C7-D2 |
| A3-B79-C6-D2 | A2-B5-C7-D2 |
| A9-B79-C6-D2 | A3-B5-C7-D2 |
| A13-B79-C6-D2 | A9-B5-C7-D2 |
| A24-B79-C6-D2 | A13-B5-C7-D2 |
| A69-B79-C6-D2 | A24-B5-C7-D2 |
| A67-B79-C6-D2 | A69-B5-C7-D2 |
| A39-B79-C6-D2 | A67-B5-C7-D2 |
| A65-B79-C6-D2 | A39-B5-C7-D2 |
| A66-B79-C6-D2 | A65-B5-C7-D2 |
| A2-B80-C6-D2 | A66-B5-C7-D2 |
| A3-B80-C6-D2 | A2-B6-C7-D2 |
| A9-B80-C6-D2 | A3-B6-C7-D2 |
| A13-B80-C6-D2 | A9-B6-C7-D2 |
| A24-B80-C6-D2 | A13-B6-C7-D2 |
| A69-B80-C6-D2 | A24-B6-C7-D2 |
| A67-B80-C6-D2 | A69-B6-C7-D2 |
| A39-B80-C6-D2 | A67-B6-C7-D2 |
| A65-B80-C6-D2 | A39-B6-C7-D2 |
| A66-B80-C6-D2 | A65-B6-C7-D2 |
| A2-B85-C6-D2 | A66-B6-C7-D2 |

TABLE 6-continued

| |
|---|
| A2-B32-C7-D2 |
| A3-B32-C7-D2 |
| A9-B32-C7-D2 |
| A13-B32-C7-D2 |
| A24-B32-C7-D2 |
| A69-B32-C7-D2 |
| A67-B32-C7-D2 |
| A39-B32-C7-D2 |
| A65-B32-C7-D2 |
| A66-B32-C7-D2 |
| A2-B39-C7-D2 |
| A3-B39-C7-D2 |
| A9-B39-C7-D2 |
| A13-B39-C7-D2 |
| A24-B39-C7-D2 |
| A69-B39-C7-D2 |
| A67-B39-C7-D2 |
| A39-B39-C7-D2 |
| A65-B39-C7-D2 |
| A66-B39-C7-D2 |
| A2-B45-C7-D2 |
| A3-B45-C7-D2 |
| A9-B45-C7-D2 |
| A13-B45-C7-D2 |
| A24-B45-C7-D2 |
| A69-B45-C7-D2 |
| A67-B45-C7-D2 |
| A39-B45-C7-D2 |
| A65-B45-C7-D2 |
| A66-B45-C7-D2 |
| A2-B53-C7-D2 |
| A3-B53-C7-D2 |
| A9-B53-C7-D2 |
| A13-B53-C7-D2 |
| A24-B53-C7-D2 |
| A69-B53-C7-D2 |
| A67-B53-C7-D2 |
| A39-B53-C7-D2 |
| A65-B53-C7-D2 |
| A66-B53-C7-D2 |
| A2-B79-C7-D2 |
| A3-B79-C7-D2 |
| A9-B79-C7-D2 |
| A13-B79-C7-D2 |
| A24-B79-C7-D2 |
| A69-B79-C7-D2 |
| A67-B79-C7-D2 |
| A39-B79-C7-D2 |
| A65-B79-C7-D2 |
| A66-B79-C7-D2 |
| A2-B80-C7-D2 |
| A3-B80-C7-D2 |
| A9-B80-C7-D2 |
| A13-B80-C7-D2 |
| A24-B80-C7-D2 |
| A69-B80-C7-D2 |
| A67-B80-C7-D2 |
| A39-B80-C7-D2 |
| A65-B80-C7-D2 |
| A66-B80-C7-D2 |
| A2-B85-C7-D2 |
| A3-B85-C7-D2 |
| A9-B85-C7-D2 |
| A13-B85-C7-D2 |
| A24-B85-C7-D2 |
| A69-B85-C7-D2 |
| A67-B85-C7-D2 |
| A39-B85-C7-D2 |
| A65-B85-C7-D2 |
| A66-B85-C7-D2 |
| A2-B86-C7-D2 |
| A3-B86-C7-D2 |
| A9-B86-C7-D2 |
| A13-B86-C7-D2 |
| A24-B86-C7-D2 |
| A69-B86-C7-D2 |
| A67-B86-C7-D2 |
| A39-B86-C7-D2 |
| A65-B86-C7-D2 |

TABLE 6-continued

| |
|---|
| A66-B86-C7-D2 |
| A2-B87-C7-D2 |
| A3-B87-C7-D2 |
| A9-B87-C7-D2 |
| A13-B87-C7-D2 |
| A24-B87-C7-D2 |
| A69-B87-C7-D2 |
| A67-B87-C7-D2 |
| A39-B87-C7-D2 |
| A65-B87-C7-D2 |
| A66-B87-C7-D2 |
| A2-B89-C7-D2 |
| A3-B89-C7-D2 |
| A9-B89-C7-D2 |
| A13-B89-C7-D2 |
| A24-B89-C7-D2 |
| A69-B89-C7-D2 |
| A67-B89-C7-D2 |
| A39-B89-C7-D2 |
| A65-B89-C7-D2 |
| A66-B89-C7-D2 |
| A2-B92-C7-D2 |
| A3-B92-C7-D2 |
| A9-B92-C7-D2 |
| A13-B92-C7-D2 |
| A24-B92-C7-D2 |
| A69-B92-C7-D2 |
| A67-B92-C7-D2 |
| A39-B92-C7-D2 |
| A65-B92-C7-D2 |
| A66-B92-C7-D2 |
| A2-B4-C8-D2 |
| A3-B4-C8-D2 |
| A9-B4-C8-D2 |
| A13-B4-C8-D2 |
| A24-B4-C8-D2 |
| A69-B4-C8-D2 |
| A67-B4-C8-D2 |
| A39-B4-C8-D2 |
| A65-B4-C8-D2 |
| A66-B4-C8-D2 |
| A2-B5-C8-D2 |
| A3-B5-C8-D2 |
| A9-B5-C8-D2 |
| A13-B5-C8-D2 |
| A24-B5-C8-D2 |
| A69-B5-C8-D2 |
| A67-B5-C8-D2 |
| A39-B5-C8-D2 |
| A65-B5-C8-D2 |
| A66-B5-C8-D2 |
| A2-B6-C8-D2 |
| A3-B6-C8-D2 |
| A9-B6-C8-D2 |
| A13-B6-C8-D2 |
| A24-B6-C8-D2 |
| A69-B6-C8-D2 |
| A67-B6-C8-D2 |
| A39-B6-C8-D2 |
| A65-B6-C8-D2 |
| A66-B6-C8-D2 |
| A2-B32-C8-D2 |
| A3-B32-C8-D2 |
| A9-B32-C8-D2 |
| A13-B32-C8-D2 |
| A24-B32-C8-D2 |
| A69-B32-C8-D2 |
| A67-B32-C8-D2 |
| A39-B32-C8-D2 |
| A65-B32-C8-D2 |
| A66-B32-C8-D2 |
| A2-B39-C8-D2 |
| A3-B39-C8-D2 |
| A9-B39-C8-D2 |
| A13-B39-C8-D2 |
| A24-B39-C8-D2 |
| A69-B39-C8-D2 |
| A67-B39-C8-D2 |
| A39-B39-C8-D2 |

TABLE 6-continued

A65-B39-C8-D2
A66-B39-C8-D2
A2-B45-C8-D2
A3-B45-C8-D2
A9-B45-C8-D2
A13-B45-C8-D2
A24-B45-C8-D2
A69-B45-C8-D2
A67-B45-C8-D2
A39-B45-C8-D2
A65-B45-C8-D2
A66-B45-C8-D2
A2-B53-C8-D2
A3-B53-C8-D2
A9-B53-C8-D2
A13-B53-C8-D2
A24-B53-C8-D2
A69-B53-C8-D2
A67-B53-C8-D2
A39-B53-C8-D2
A65-B53-C8-D2
A66-B53-C8-D2
A2-B79-C8-D2
A3-B79-C8-D2
A9-B79-C8-D2
A13-B79-C8-D2
A24-B79-C8-D2
A69-B79-C8-D2
A67-B79-C8-D2
A39-B79-C8-D2
A65-B79-C8-D2
A66-B79-C8-D2
A2-B80-C8-D2
A3-B80-C8-D2
A9-B80-C8-D2
A13-B80-C8-D2
A24-B80-C8-D2
A69-B80-C8-D2
A67-B80-C8-D2
A39-B80-C8-D2
A65-B80-C8-D2
A66-B80-C8-D2
A2-B85-C8-D2
A3-B85-C8-D2
A9-B85-C8-D2
A13-B85-C8-D2
A24-B85-C8-D2
A69-B85-C8-D2
A67-B85-C8-D2
A39-B85-C8-D2
A65-B85-C8-D2
A66-B85-C8-D2
A2-B86-C8-D2
A3-B86-C8-D2
A9-B86-C8-D2
A13-B86-C8-D2
A24-B86-C8-D2
A69-B86-C8-D2
A67-B86-C8-D2
A39-B86-C8-D2
A65-B86-C8-D2
A66-B86-C8-D2
A2-B87-C8-D2
A3-B87-C8-D2
A9-B87-C8-D2
A13-B87-C8-D2
A24-B87-C8-D2
A69-B87-C8-D2
A67-B87-C8-D2
A39-B87-C8-D2
A65-B87-C8-D2
A66-B87-C8-D2
A2-B89-C8-D2
A3-B89-C8-D2
A9-B89-C8-D2
A13-B89-C8-D2
A24-B89-C8-D2
A69-B89-C8-D2
A67-B89-C8-D2
A39-B89-C8-D2
A65-B89-C8-D2
A66-B89-C8-D2
A2-B92-C8-D2
A3-B92-C8-D2
A9-B92-C8-D2
A13-B92-C8-D2
A24-B92-C8-D2
A69-B92-C8-D2
A67-B92-C8-D2
A39-B92-C8-D2
A65-B92-C8-D2
A66-B92-C8-D2
A2-B4-C9-D2
A3-B4-C9-D2
A9-B4-C9-D2
A13-B4-C9-D2
A24-B4-C9-D2
A69-B4-C9-D2
A67-B4-C9-D2
A39-B4-C9-D2
A65-B4-C9-D2
A66-B4-C9-D2
A2-B5-C9-D2
A3-B5-C9-D2
A9-B5-C9-D2
A13-B5-C9-D2
A24-B5-C9-D2
A69-B5-C9-D2
A67-B5-C9-D2
A39-B5-C9-D2
A65-B5-C9-D2
A66-B5-C9-D2
A2-B6-C9-D2
A3-B6-C9-D2
A9-B6-C9-D2
A13-B6-C9-D2
A24-B6-C9-D2
A69-B6-C9-D2
A67-B6-C9-D2
A39-B6-C9-D2
A65-B6-C9-D2
A66-B6-C9-D2
A2-B32-C9-D2
A3-B32-C9-D2
A9-B32-C9-D2
A13-B32-C9-D2
A24-B32-C9-D2
A69-B32-C9-D2
A67-B32-C9-D2
A39-B32-C9-D2
A65-B32-C9-D2
A66-B32-C9-D2
A2-B39-C9-D2
A3-B39-C9-D2
A9-B39-C9-D2
A13-B39-C9-D2
A24-B39-C9-D2
A69-B39-C9-D2
A67-B39-C9-D2
A39-B39-C9-D2
A65-B39-C9-D2
A66-B39-C9-D2
A2-B45-C9-D2
A3-B45-C9-D2
A9-B45-C9-D2
A13-B45-C9-D2
A24-B45-C9-D2
A69-B45-C9-D2
A67-B45-C9-D2
A39-B45-C9-D2
A65-B45-C9-D2
A66-B45-C9-D2
A2-B53-C9-D2
A3-B53-C9-D2
A9-B53-C9-D2
A13-B53-C9-D2
A24-B53-C9-D2
A69-B53-C9-D2

TABLE 6-continued

A67-B53-C9-D2
A39-B53-C9-D2
A65-B53-C9-D2
A66-B53-C9-D2
A2-B79-C9-D2
A3-B79-C9-D2
A9-B79-C9-D2
A13-B79-C9-D2
A24-B79-C9-D2
A69-B79-C9-D2
A67-B79-C9-D2
A39-B79-C9-D2
A65-B79-C9-D2
A66-B79-C9-D2
A2-B80-C9-D2
A3-B80-C9-D2
A9-B80-C9-D2
A13-B80-C9-D2
A24-B80-C9-D2
A69-B80-C9-D2
A67-B80-C9-D2
A39-B80-C9-D2
A65-B80-C9-D2
A66-B80-C9-D2
A2-B85-C9-D2
A3-B85-C9-D2
A9-B85-C9-D2
A13-B85-C9-D2
A24-B85-C9-D2
A69-B85-C9-D2
A67-B85-C9-D2
A39-B85-C9-D2
A65-B85-C9-D2
A66-B85-C9-D2
A2-B86-C9-D2
A3-B86-C9-D2
A9-B86-C9-D2
A13-B86-C9-D2
A24-B86-C9-D2
A69-B86-C9-D2
A67-B86-C9-D2
A39-B86-C9-D2
A65-B86-C9-D2
A66-B86-C9-D2
A2-B87-C9-D2
A3-B87-C9-D2
A9-B87-C9-D2
A13-B87-C9-D2
A24-B87-C9-D2
A69-B87-C9-D2
A67-B87-C9-D2
A39-B87-C9-D2
A65-B87-C9-D2
A66-B87-C9-D2
A2-B89-C9-D2
A3-B89-C9-D2
A9-B89-C9-D2
A13-B89-C9-D2
A24-B89-C9-D2
A69-B89-C9-D2
A67-B89-C9-D2
A39-B89-C9-D2
A65-B89-C9-D2
A66-B89-C9-D2
A2-B92-C9-D2
A3-B92-C9-D2
A9-B92-C9-D2
A13-B92-C9-D2
A24-B92-C9-D2
A69-B92-C9-D2
A67-B92-C9-D2
A39-B92-C9-D2
A65-B92-C9-D2
A66-B92-C9-D2
A2-B4-C10-D2
A3-B4-C10-D2
A9-B4-C10-D2
A13-B4-C10-D2
A24-B4-C10-D2

TABLE 6-continued

A69-B4-C10-D2
A67-B4-C10-D2
A39-B4-C10-D2
A65-B4-C10-D2
A66-B4-C10-D2
A2-B5-C10-D2
A3-B5-C10-D2
A9-B5-C10-D2
A13-B5-C10-D2
A24-B5-C10-D2
A69-B5-C10-D2
A67-B5-C10-D2
A39-B5-C10-D2
A65-B5-C10-D2
A66-B5-C10-D2
A2-B6-C10-D2
A3-B6-C10-D2
A9-B6-C10-D2
A13-B6-C10-D2
A24-B6-C10-D2
A69-B6-C10-D2
A67-B6-C10-D2
A39-B6-C10-D2
A65-B6-C10-D2
A66-B6-C10-D2
A2-B32-C10-D2
A3-B32-C10-D2
A9-B32-C10-D2
A13-B32-C10-D2
A24-B32-C10-D2
A69-B32-C10-D2
A67-B32-C10-D2
A39-B32-C10-D2
A65-B32-C10-D2
A66-B32-C10-D2
A2-B39-C10-D2
A3-B39-C10-D2
A9-B39-C10-D2
A13-B39-C10-D2
A24-B39-C10-D2
A69-B39-C10-D2
A67-B39-C10-D2
A39-B39-C10-D2
A65-B39-C10-D2
A66-B39-C10-D2
A2-B45-C10-D2
A3-B45-C10-D2
A9-B45-C10-D2
A13-B45-C10-D2
A24-B45-C10-D2
A69-B45-C10-D2
A67-B45-C10-D2
A39-B45-C10-D2
A65-B45-C10-D2
A66-B45-C10-D2
A2-B53-C10-D2
A3-B53-C10-D2
A9-B53-C10-D2
A13-B53-C10-D2
A24-B53-C10-D2
A69-B53-C10-D2
A67-B53-C10-D2
A39-B53-C10-D2
A65-B53-C10-D2
A66-B53-C10-D2
A2-B79-C10-D2
A3-B79-C10-D2
A9-B79-C10-D2
A13-B79-C10-D2
A24-B79-C10-D2
A69-B79-C10-D2
A67-B79-C10-D2
A39-B79-C10-D2
A65-B79-C10-D2
A66-B79-C10-D2
A2-B80-C10-D2
A3-B80-C10-D2
A9-B80-C10-D2
A13-B80-C10-D2

TABLE 6-continued

A24-B80-C10-D2
A69-B80-C10-D2
A67-B80-C10-D2
A39-B80-C10-D2
A65-B80-C10-D2
A66-B80-C10-D2
A2-B85-C10-D2
A3-B85-C10-D2
A9-B85-C10-D2
A13-B85-C10-D2
A24-B85-C10-D2
A69-B85-C10-D2
A67-B85-C10-D2
A39-B85-C10-D2
A65-B85-C10-D2
A66-B85-C10-D2
A2-B86-C10-D2
A3-B86-C10-D2
A9-B86-C10-D2
A13-B86-C10-D2
A24-B86-C10-D2
A69-B86-C10-D2
A67-B86-C10-D2
A39-B86-C10-D2
A65-B86-C10-D2
A66-B86-C10-D2
A2-B87-C10-D2
A3-B87-C10-D2
A9-B87-C10-D2
A13-B87-C10-D2
A24-B87-C10-D2
A69-B87-C10-D2
A67-B87-C10-D2
A39-B87-C10-D2
A65-B87-C10-D2
A66-B87-C10-D2
A2-B89-C10-D2
A3-B89-C10-D2
A9-B89-C10-D2
A13-B89-C10-D2
A24-B89-C10-D2
A69-B89-C10-D2
A67-B89-C10-D2
A39-B89-C10-D2
A65-B89-C10-D2
A66-B89-C10-D2
A2-B92-C10-D2
A3-B92-C10-D2
A9-B92-C10-D2
A13-B92-C10-D2
A24-B92-C10-D2
A69-B92-C10-D2
A67-B92-C10-D2
A39-B92-C10-D2
A65-B92-C10-D2
A66-B92-C10-D2
A2-B4-C11-D2
A3-B4-C11-D2
A9-B4-C11-D2
A13-B4-C11-D2
A24-B4-C11-D2
A69-B4-C11-D2
A67-B4-C11-D2
A39-B4-C11-D2
A65-B4-C11-D2
A66-B4-C11-D2
A2-B5-C11-D2
A3-B5-C11-D2
A9-B5-C11-D2
A13-B5-C11-D2
A24-B5-C11-D2
A69-B5-C11-D2
A67-B5-C11-D2
A39-B5-C11-D2
A65-B5-C11-D2
A66-B5-C11-D2
A2-B6-C11-D2
A3-B6-C11-D2
A9-B6-C11-D2

TABLE 6-continued

A13-B6-C11-D2
A24-B6-C11-D2
A69-B6-C11-D2
A67-B6-C11-D2
A39-B6-C11-D2
A65-B6-C11-D2
A66-B6-C11-D2
A2-B32-C11-D2
A3-B32-C11-D2
A9-B32-C11-D2
A13-B32-C11-D2
A24-B32-C11-D2
A69-B32-C11-D2
A67-B32-C11-D2
A39-B32-C11-D2
A65-B32-C11-D2
A66-B32-C11-D2
A2-B39-C11-D2
A3-B39-C11-D2
A9-B39-C11-D2
A13-B39-C11-D2
A24-B39-C11-D2
A69-B39-C11-D2
A67-B39-C11-D2
A39-B39-C11-D2
A65-B39-C11-D2
A66-B39-C11-D2
A2-B45-C11-D2
A3-B45-C11-D2
A9-B45-C11-D2
A13-B45-C11-D2
A24-B45-C11-D2
A69-B45-C11-D2
A67-B45-C11-D2
A39-B45-C11-D2
A65-B45-C11-D2
A66-B45-C11-D2
A2-B53-C11-D2
A3-B53-C11-D2
A9-B53-C11-D2
A13-B53-C11-D2
A24-B53-C11-D2
A69-B53-C11-D2
A67-B53-C11-D2
A39-B53-C11-D2
A65-B53-C11-D2
A66-B53-C11-D2
A2-B79-C11-D2
A3-B79-C11-D2
A9-B79-C11-D2
A13-B79-C11-D2
A24-B79-C11-D2
A69-B79-C11-D2
A67-B79-C11-D2
A39-B79-C11-D2
A65-B79-C11-D2
A66-B79-C11-D2
A2-B80-C11-D2
A3-B80-C11-D2
A9-B80-C11-D2
A13-B80-C11-D2
A24-B80-C11-D2
A69-B80-C11-D2
A67-B80-C11-D2
A39-B80-C11-D2
A65-B80-C11-D2
A66-B80-C11-D2
A2-B85-C11-D2
A3-B85-C11-D2
A9-B85-C11-D2
A13-B85-C11-D2
A24-B85-C11-D2
A69-B85-C11-D2
A67-B85-C11-D2
A39-B85-C11-D2
A65-B85-C11-D2
A66-B85-C11-D2
A2-B86-C11-D2
A3-B86-C11-D2

TABLE 6-continued

| | |
|---|---|
| A9-B86-C11-D2 | A3-B39-C12-D2 |
| A13-B86-C11-D2 | A9-B39-C12-D2 |
| A24-B86-C11-D2 | A13-B39-C12-D2 |
| A69-B86-C11-D2 | A24-B39-C12-D2 |
| A67-B86-C11-D2 | A69-B39-C12-D2 |
| A39-B86-C11-D2 | A67-B39-C12-D2 |
| A65-B86-C11-D2 | A39-B39-C12-D2 |
| A66-B86-C11-D2 | A65-B39-C12-D2 |
| A2-B87-C11-D2 | A66-B39-C12-D2 |
| A3-B87-C11-D2 | A2-B45-C12-D2 |
| A9-B87-C11-D2 | A3-B45-C12-D2 |
| A13-B87-C11-D2 | A9-B45-C12-D2 |
| A24-B87-C11-D2 | A13-B45-C12-D2 |
| A69-B87-C11-D2 | A24-B45-C12-D2 |
| A67-B87-C11-D2 | A69-B45-C12-D2 |
| A39-B87-C11-D2 | A67-B45-C12-D2 |
| A65-B87-C11-D2 | A39-B45-C12-D2 |
| A66-B87-C11-D2 | A65-B45-C12-D2 |
| A2-B89-C11-D2 | A66-B45-C12-D2 |
| A3-B89-C11-D2 | A2-B53-C12-D2 |
| A9-B89-C11-D2 | A3-B53-C12-D2 |
| A13-B89-C11-D2 | A9-B53-C12-D2 |
| A24-B89-C11-D2 | A13-B53-C12-D2 |
| A69-B89-C11-D2 | A24-B53-C12-D2 |
| A67-B89-C11-D2 | A69-B53-C12-D2 |
| A39-B89-C11-D2 | A67-B53-C12-D2 |
| A65-B89-C11-D2 | A39-B53-C12-D2 |
| A66-B89-C11-D2 | A65-B53-C12-D2 |
| A2-B92-C11-D2 | A66-B53-C12-D2 |
| A3-B92-C11-D2 | A2-B79-C12-D2 |
| A9-B92-C11-D2 | A3-B79-C12-D2 |
| A13-B92-C11-D2 | A9-B79-C12-D2 |
| A24-B92-C11-D2 | A13-B79-C12-D2 |
| A69-B92-C11-D2 | A24-B79-C12-D2 |
| A67-B92-C11-D2 | A69-B79-C12-D2 |
| A39-B92-C11-D2 | A67-B79-C12-D2 |
| A65-B92-C11-D2 | A39-B79-C12-D2 |
| A66-B92-C11-D2 | A65-B79-C12-D2 |
| A2-B4-C12-D2 | A66-B79-C12-D2 |
| A3-B4-C12-D2 | A2-B80-C12-D2 |
| A9-B4-C12-D2 | A3-B80-C12-D2 |
| A13-B4-C12-D2 | A9-B80-C12-D2 |
| A24-B4-C12-D2 | A13-B80-C12-D2 |
| A69-B4-C12-D2 | A24-B80-C12-D2 |
| A67-B4-C12-D2 | A69-B80-C12-D2 |
| A39-B4-C12-D2 | A67-B80-C12-D2 |
| A65-B4-C12-D2 | A39-B80-C12-D2 |
| A66-B4-C12-D2 | A65-B80-C12-D2 |
| A2-B5-C12-D2 | A66-B80-C12-D2 |
| A3-B5-C12-D2 | A2-B85-C12-D2 |
| A9-B5-C12-D2 | A3-B85-C12-D2 |
| A13-B5-C12-D2 | A9-B85-C12-D2 |
| A24-B5-C12-D2 | A13-B85-C12-D2 |
| A69-B5-C12-D2 | A24-B85-C12-D2 |
| A67-B5-C12-D2 | A69-B85-C12-D2 |
| A39-B5-C12-D2 | A67-B85-C12-D2 |
| A65-B5-C12-D2 | A39-B85-C12-D2 |
| A66-B5-C12-D2 | A65-B85-C12-D2 |
| A2-B6-C12-D2 | A66-B85-C12-D2 |
| A3-B6-C12-D2 | A2-B86-C12-D2 |
| A9-B6-C12-D2 | A3-B86-C12-D2 |
| A13-B6-C12-D2 | A9-B86-C12-D2 |
| A24-B6-C12-D2 | A13-B86-C12-D2 |
| A69-B6-C12-D2 | A24-B86-C12-D2 |
| A67-B6-C12-D2 | A69-B86-C12-D2 |
| A39-B6-C12-D2 | A67-B86-C12-D2 |
| A65-B6-C12-D2 | A39-B86-C12-D2 |
| A66-B6-C12-D2 | A65-B86-C12-D2 |
| A2-B32-C12-D2 | A66-B86-C12-D2 |
| A3-B32-C12-D2 | A2-B87-C12-D2 |
| A9-B32-C12-D2 | A3-B87-C12-D2 |
| A13-B32-C12-D2 | A9-B87-C12-D2 |
| A24-B32-C12-D2 | A13-B87-C12-D2 |
| A69-B32-C12-D2 | A24-B87-C12-D2 |
| A67-B32-C12-D2 | A69-B87-C12-D2 |
| A39-B32-C12-D2 | A67-B87-C12-D2 |
| A65-B32-C12-D2 | A39-B87-C12-D2 |
| A66-B32-C12-D2 | A65-B87-C12-D2 |
| A2-B39-C12-D2 | A66-B87-C12-D2 |

TABLE 6-continued

A2-B89-C12-D2
A3-B89-C12-D2
A9-B89-C12-D2
A13-B89-C12-D2
A24-B89-C12-D2
A69-B89-C12-D2
A67-B89-C12-D2
A39-B89-C12-D2
A65-B89-C12-D2
A66-B89-C12-D2
A2-B92-C12-D2
A3-B92-C12-D2
A9-B92-C12-D2
A13-B92-C12-D2
A24-B92-C12-D2
A69-B92-C12-D2
A67-B92-C12-D2
A39-B92-C12-D2
A65-B92-C12-D2
A66-B92-C12-D2
A2-B4-C13-D2
A3-B4-C13-D2
A9-B4-C13-D2
A13-B4-C13-D2
A24-B4-C13-D2
A69-B4-C13-D2
A67-B4-C13-D2
A39-B4-C13-D2
A65-B4-C13-D2
A66-B4-C13-D2
A2-B5-C13-D2
A3-B5-C13-D2
A9-B5-C13-D2
A13-B5-C13-D2
A24-B5-C13-D2
A69-B5-C13-D2
A67-B5-C13-D2
A39-B5-C13-D2
A65-B5-C13-D2
A66-B5-C13-D2
A2-B6-C13-D2
A3-B6-C13-D2
A9-B6-C13-D2
A13-B6-C13-D2
A24-B6-C13-D2
A69-B6-C13-D2
A67-B6-C13-D2
A39-B6-C13-D2
A65-B6-C13-D2
A66-B6-C13-D2
A2-B32-C13-D2
A3-B32-C13-D2
A9-B32-C13-D2
A13-B32-C13-D2
A24-B32-C13-D2
A69-B32-C13-D2
A67-B32-C13-D2
A39-B32-C13-D2
A65-B32-C13-D2
A66-B32-C13-D2
A2-B39-C13-D2
A3-B39-C13-D2
A9-B39-C13-D2
A13-B39-C13-D2
A24-B39-C13-D2
A69-B39-C13-D2
A67-B39-C13-D2
A39-B39-C13-D2
A65-B39-C13-D2
A66-B39-C13-D2
A2-B45-C13-D2
A3-B45-C13-D2
A9-B45-C13-D2
A13-B45-C13-D2
A24-B45-C13-D2
A69-B45-C13-D2
A67-B45-C13-D2
A39-B45-C13-D2
A65-B45-C13-D2

TABLE 6-continued

A66-B45-C13-D2
A2-B53-C13-D2
A3-B53-C13-D2
A9-B53-C13-D2
A13-B53-C13-D2
A24-B53-C13-D2
A69-B53-C13-D2
A67-B53-C13-D2
A39-B53-C13-D2
A65-B53-C13-D2
A66-B53-C13-D2
A2-B79-C13-D2
A3-B79-C13-D2
A9-B79-C13-D2
A13-B79-C13-D2
A24-B79-C13-D2
A69-B79-C13-D2
A67-B79-C13-D2
A39-B79-C13-D2
A65-B79-C13-D2
A66-B79-C13-D2
A2-B80-C13-D2
A3-B80-C13-D2
A9-B80-C13-D2
A13-B80-C13-D2
A24-B80-C13-D2
A69-B80-C13-D2
A67-B80-C13-D2
A39-B80-C13-D2
A65-B80-C13-D2
A66-B80-C13-D2
A2-B85-C13-D2
A3-B85-C13-D2
A9-B85-C13-D2
A13-B85-C13-D2
A24-B85-C13-D2
A69-B85-C13-D2
A67-B85-C13-D2
A39-B85-C13-D2
A65-B85-C13-D2
A66-B85-C13-D2
A2-B86-C13-D2
A3-B86-C13-D2
A9-B86-C13-D2
A13-B86-C13-D2
A24-B86-C13-D2
A69-B86-C13-D2
A67-B86-C13-D2
A39-B86-C13-D2
A65-B86-C13-D2
A66-B86-C13-D2
A2-B87-C13-D2
A3-B87-C13-D2
A9-B87-C13-D2
A13-B87-C13-D2
A24-B87-C13-D2
A69-B87-C13-D2
A67-B87-C13-D2
A39-B87-C13-D2
A65-B87-C13-D2
A66-B87-C13-D2
A2-B89-C13-D2
A3-B89-C13-D2
A9-B89-C13-D2
A13-B89-C13-D2
A24-B89-C13-D2
A69-B89-C13-D2
A67-B89-C13-D2
A39-B89-C13-D2
A65-B89-C13-D2
A66-B89-C13-D2
A2-B92-C13-D2
A3-B92-C13-D2
A9-B92-C13-D2
A13-B92-C13-D2
A24-B92-C13-D2
A69-B92-C13-D2
A67-B92-C13-D2
A39-B92-C13-D2

TABLE 6-continued

A65-B92-C13-D2
A66-B92-C13-D2
A2-B4-C1-D3
A3-B4-C1-D3
A9-B4-C1-D3
A13-B4-C1-D3
A24-B4-C1-D3
A69-B4-C1-D3
A67-B4-C1-D3
A39-B4-C1-D3
A65-B4-C1-D3
A66-B4-C1-D3
A2-B5-C1-D3
A3-B5-C1-D3
A9-B5-C1-D3
A13-B5-C1-D3
A24-B5-C1-D3
A69-B5-C1-D3
A67-B5-C1-D3
A39-B5-C1-D3
A65-B5-C1-D3
A66-B5-C1-D3
A2-B6-C1-D3
A3-B6-C1-D3
A9-B6-C1-D3
A13-B6-C1-D3
A24-B6-C1-D3
A69-B6-C1-D3
A67-B6-C1-D3
A39-B6-C1-D3
A65-B6-C1-D3
A66-B6-C1-D3
A2-B32-C1-D3
A3-B32-C1-D3
A9-B32-C1-D3
A13-B32-C1-D3
A24-B32-C1-D3
A69-B32-C1-D3
A67-B32-C1-D3
A39-B32-C1-D3
A65-B32-C1-D3
A66-B32-C1-D3
A2-B39-C1-D3
A3-B39-C1-D3
A9-B39-C1-D3
A13-B39-C1-D3
A24-B39-C1-D3
A69-B39-C1-D3
A67-B39-C1-D3
A39-B39-C1-D3
A65-B39-C1-D3
A66-B39-C1-D3
A2-B45-C1-D3
A3-B45-C1-D3
A9-B45-C1-D3
A13-B45-C1-D3
A24-B45-C1-D3
A69-B45-C1-D3
A67-B45-C1-D3
A39-B45-C1-D3
A65-B45-C1-D3
A66-B45-C1-D3
A2-B53-C1-D3
A3-B53-C1-D3
A9-B53-C1-D3
A13-B53-C1-D3
A24-B53-C1-D3
A69-B53-C1-D3
A67-B53-C1-D3
A39-B53-C1-D3
A65-B53-C1-D3
A66-B53-C1-D3
A2-B79-C1-D3
A3-B79-C1-D3
A9-B79-C1-D3
A13-B79-C1-D3
A24-B79-C1-D3
A69-B79-C1-D3
A67-B79-C1-D3

TABLE 6-continued

A39-B79-C1-D3
A65-B79-C1-D3
A66-B79-C1-D3
A2-B80-C1-D3
A3-B80-C1-D3
A9-B80-C1-D3
A13-B80-C1-D3
A24-B80-C1-D3
A69-B80-C1-D3
A67-B80-C1-D3
A39-B80-C1-D3
A65-B80-C1-D3
A66-B80-C1-D3
A2-B85-C1-D3
A3-B85-C1-D3
A9-B85-C1-D3
A13-B85-C1-D3
A24-B85-C1-D3
A69-B85-C1-D3
A67-B85-C1-D3
A39-B85-C1-D3
A65-B85-C1-D3
A66-B85-C1-D3
A2-B86-C1-D3
A3-B86-C1-D3
A9-B86-C1-D3
A13-B86-C1-D3
A24-B86-C1-D3
A69-B86-C1-D3
A67-B86-C1-D3
A39-B86-C1-D3
A65-B86-C1-D3
A66-B86-C1-D3
A2-B87-C1-D3
A3-B87-C1-D3
A9-B87-C1-D3
A13-B87-C1-D3
A24-B87-C1-D3
A69-B87-C1-D3
A67-B87-C1-D3
A39-B87-C1-D3
A65-B87-C1-D3
A66-B87-C1-D3
A2-B89-C1-D3
A3-B89-C1-D3
A9-B89-C1-D3
A13-B89-C1-D3
A24-B89-C1-D3
A69-B89-C1-D3
A67-B89-C1-D3
A39-B89-C1-D3
A65-B89-C1-D3
A66-B89-C1-D3
A2-B92-C1-D3
A3-B92-C1-D3
A9-B92-C1-D3
A13-B92-C1-D3
A24-B92-C1-D3
A69-B92-C1-D3
A67-B92-C1-D3
A39-B92-C1-D3
A65-B92-C1-D3
A66-B92-C1-D3
A2-B4-C2-D3
A3-B4-C2-D3
A9-B4-C2-D3
A13-B4-C2-D3
A24-B4-C2-D3
A69-B4-C2-D3
A67-B4-C2-D3
A39-B4-C2-D3
A65-B4-C2-D3
A66-B4-C2-D3
A2-B5-C2-D3
A3-B5-C2-D3
A9-B5-C2-D3
A13-B5-C2-D3
A24-B5-C2-D3
A69-B5-C2-D3

TABLE 6-continued

A67-B5-C2-D3
A39-B5-C2-D3
A65-B5-C2-D3
A66-B5-C2-D3
A2-B6-C2-D3
A3-B6-C2-D3
A9-B6-C2-D3
A13-B6-C2-D3
A24-B6-C2-D3
A69-B6-C2-D3
A67-B6-C2-D3
A39-B6-C2-D3
A65-B6-C2-D3
A66-B6-C2-D3
A2-B32-C2-D3
A3-B32-C2-D3
A9-B32-C2-D3
A13-B32-C2-D3
A24-B32-C2-D3
A69-B32-C2-D3
A67-B32-C2-D3
A39-B32-C2-D3
A65-B32-C2-D3
A66-B32-C2-D3
A2-B39-C2-D3
A3-B39-C2-D3
A9-B39-C2-D3
A13-B39-C2-D3
A24-B39-C2-D3
A69-B39-C2-D3
A67-B39-C2-D3
A39-B39-C2-D3
A65-B39-C2-D3
A66-B39-C2-D3
A2-B45-C2-D3
A3-B45-C2-D3
A9-B45-C2-D3
A13-B45-C2-D3
A24-B45-C2-D3
A69-B45-C2-D3
A67-B45-C2-D3
A39-B45-C2-D3
A65-B45-C2-D3
A66-B45-C2-D3
A2-B53-C2-D3
A3-B53-C2-D3
A9-B53-C2-D3
A13-B53-C2-D3
A24-B53-C2-D3
A69-B53-C2-D3
A67-B53-C2-D3
A39-B53-C2-D3
A65-B53-C2-D3
A66-B53-C2-D3
A2-B79-C2-D3
A3-B79-C2-D3
A9-B79-C2-D3
A13-B79-C2-D3
A24-B79-C2-D3
A69-B79-C2-D3
A67-B79-C2-D3
A39-B79-C2-D3
A65-B79-C2-D3
A66-B79-C2-D3
A2-B80-C2-D3
A3-B80-C2-D3
A9-B80-C2-D3
A13-B80-C2-D3
A24-B80-C2-D3
A69-B80-C2-D3
A67-B80-C2-D3
A39-B80-C2-D3
A65-B80-C2-D3
A66-B80-C2-D3
A2-B85-C2-D3
A3-B85-C2-D3
A9-B85-C2-D3
A13-B85-C2-D3
A24-B85-C2-D3

TABLE 6-continued

A69-B85-C2-D3
A67-B85-C2-D3
A39-B85-C2-D3
A65-B85-C2-D3
A66-B85-C2-D3
A2-B86-C2-D3
A3-B86-C2-D3
A9-B86-C2-D3
A13-B86-C2-D3
A24-B86-C2-D3
A69-B86-C2-D3
A67-B86-C2-D3
A39-B86-C2-D3
A65-B86-C2-D3
A66-B86-C2-D3
A2-B87-C2-D3
A3-B87-C2-D3
A9-B87-C2-D3
A13-B87-C2-D3
A24-B87-C2-D3
A69-B87-C2-D3
A67-B87-C2-D3
A39-B87-C2-D3
A65-B87-C2-D3
A66-B87-C2-D3
A2-B89-C2-D3
A3-B89-C2-D3
A9-B89-C2-D3
A13-B89-C2-D3
A24-B89-C2-D3
A69-B89-C2-D3
A67-B89-C2-D3
A39-B89-C2-D3
A65-B89-C2-D3
A66-B89-C2-D3
A2-B92-C2-D3
A3-B92-C2-D3
A9-B92-C2-D3
A13-B92-C2-D3
A24-B92-C2-D3
A69-B92-C2-D3
A67-B92-C2-D3
A39-B92-C2-D3
A65-B92-C2-D3
A66-B92-C2-D3
A2-B4-C3-D3
A3-B4-C3-D3
A9-B4-C3-D3
A13-B4-C3-D3
A24-B4-C3-D3
A69-B4-C3-D3
A67-B4-C3-D3
A39-B4-C3-D3
A65-B4-C3-D3
A66-B4-C3-D3
A2-B5-C3-D3
A3-B5-C3-D3
A9-B5-C3-D3
A13-B5-C3-D3
A24-B5-C3-D3
A69-B5-C3-D3
A67-B5-C3-D3
A39-B5-C3-D3
A65-B5-C3-D3
A66-B5-C3-D3
A2-B6-C3-D3
A3-B6-C3-D3
A9-B6-C3-D3
A13-B6-C3-D3
A24-B6-C3-D3
A69-B6-C3-D3
A67-B6-C3-D3
A39-B6-C3-D3
A65-B6-C3-D3
A66-B6-C3-D3
A2-B32-C3-D3
A3-B32-C3-D3
A9-B32-C3-D3
A13-B32-C3-D3

TABLE 6-continued

A24-B32-C3-D3
A69-B32-C3-D3
A67-B32-C3-D3
A39-B32-C3-D3
A65-B32-C3-D3
A66-B32-C3-D3
A2-B39-C3-D3
A3-B39-C3-D3
A9-B39-C3-D3
A13-B39-C3-D3
A24-B39-C3-D3
A69-B39-C3-D3
A67-B39-C3-D3
A39-B39-C3-D3
A65-B39-C3-D3
A66-B39-C3-D3
A2-B45-C3-D3
A3-B45-C3-D3
A9-B45-C3-D3
A13-B45-C3-D3
A24-B45-C3-D3
A69-B45-C3-D3
A67-B45-C3-D3
A39-B45-C3-D3
A65-B45-C3-D3
A66-B45-C3-D3
A2-B53-C3-D3
A3-B53-C3-D3
A9-B53-C3-D3
A13-B53-C3-D3
A24-B53-C3-D3
A69-B53-C3-D3
A67-B53-C3-D3
A39-B53-C3-D3
A65-B53-C3-D3
A66-B53-C3-D3
A2-B79-C3-D3
A3-B79-C3-D3
A9-B79-C3-D3
A13-B79-C3-D3
A24-B79-C3-D3
A69-B79-C3-D3
A67-B79-C3-D3
A39-B79-C3-D3
A65-B79-C3-D3
A66-B79-C3-D3
A2-B80-C3-D3
A3-B80-C3-D3
A9-B80-C3-D3
A13-B80-C3-D3
A24-B80-C3-D3
A69-B80-C3-D3
A67-B80-C3-D3
A39-B80-C3-D3
A65-B80-C3-D3
A66-B80-C3-D3
A2-B85-C3-D3
A3-B85-C3-D3
A9-B85-C3-D3
A13-B85-C3-D3
A24-B85-C3-D3
A69-B85-C3-D3
A67-B85-C3-D3
A39-B85-C3-D3
A65-B85-C3-D3
A66-B85-C3-D3
A2-B86-C3-D3
A3-B86-C3-D3
A9-B86-C3-D3
A13-B86-C3-D3
A24-B86-C3-D3
A69-B86-C3-D3
A67-B86-C3-D3
A39-B86-C3-D3
A65-B86-C3-D3
A66-B86-C3-D3
A2-B87-C3-D3
A3-B87-C3-D3
A9-B87-C3-D3

TABLE 6-continued

A13-B87-C3-D3
A24-B87-C3-D3
A69-B87-C3-D3
A67-B87-C3-D3
A39-B87-C3-D3
A65-B87-C3-D3
A66-B87-C3-D3
A2-B89-C3-D3
A3-B89-C3-D3
A9-B89-C3-D3
A13-B89-C3-D3
A24-B89-C3-D3
A69-B89-C3-D3
A67-B89-C3-D3
A39-B89-C3-D3
A65-B89-C3-D3
A66-B89-C3-D3
A2-B92-C3-D3
A3-B92-C3-D3
A9-B92-C3-D3
A13-B92-C3-D3
A24-B92-C3-D3
A69-B92-C3-D3
A67-B92-C3-D3
A39-B92-C3-D3
A65-B92-C3-D3
A66-B92-C3-D3
A2-B4-C4-D3
A3-B4-C4-D3
A9-B4-C4-D3
A13-B4-C4-D3
A24-B4-C4-D3
A69-B4-C4-D3
A67-B4-C4-D3
A39-B4-C4-D3
A65-B4-C4-D3
A66-B4-C4-D3
A2-B5-C4-D3
A3-B5-C4-D3
A9-B5-C4-D3
A13-B5-C4-D3
A24-B5-C4-D3
A69-B5-C4-D3
A67-B5-C4-D3
A39-B5-C4-D3
A65-B5-C4-D3
A66-B5-C4-D3
A2-B6-C4-D3
A3-B6-C4-D3
A9-B6-C4-D3
A13-B6-C4-D3
A24-B6-C4-D3
A69-B6-C4-D3
A67-B6-C4-D3
A39-B6-C4-D3
A65-B6-C4-D3
A66-B6-C4-D3
A2-B32-C4-D3
A3-B32-C4-D3
A9-B32-C4-D3
A13-B32-C4-D3
A24-B32-C4-D3
A69-B32-C4-D3
A67-B32-C4-D3
A39-B32-C4-D3
A65-B32-C4-D3
A66-B32-C4-D3
A2-B39-C4-D3
A3-B39-C4-D3
A9-B39-C4-D3
A13-B39-C4-D3
A24-B39-C4-D3
A69-B39-C4-D3
A67-B39-C4-D3
A39-B39-C4-D3
A65-B39-C4-D3
A66-B39-C4-D3
A2-B45-C4-D3
A3-B45-C4-D3

TABLE 6-continued

| | |
|---|---|
| A9-B45-C4-D3 | A3-B92-C4-D3 |
| A13-B45-C4-D3 | A9-B92-C4-D3 |
| A24-B45-C4-D3 | A13-B92-C4-D3 |
| A69-B45-C4-D3 | A24-B92-C4-D3 |
| A67-B45-C4-D3 | A69-B92-C4-D3 |
| A39-B45-C4-D3 | A67-B92-C4-D3 |
| A65-B45-C4-D3 | A39-B92-C4-D3 |
| A66-B45-C4-D3 | A65-B92-C4-D3 |
| A2-B53-C4-D3 | A66-B92-C4-D3 |
| A3-B53-C4-D3 | A2-B4-C5-D3 |
| A9-B53-C4-D3 | A3-B4-C5-D3 |
| A13-B53-C4-D3 | A9-B4-C5-D3 |
| A24-B53-C4-D3 | A13-B4-C5-D3 |
| A69-B53-C4-D3 | A24-B4-C5-D3 |
| A67-B53-C4-D3 | A69-B4-C5-D3 |
| A39-B53-C4-D3 | A67-B4-C5-D3 |
| A65-B53-C4-D3 | A39-B4-C5-D3 |
| A66-B53-C4-D3 | A65-B4-C5-D3 |
| A2-B79-C4-D3 | A66-B4-C5-D3 |
| A3-B79-C4-D3 | A2-B5-C5-D3 |
| A9-B79-C4-D3 | A3-B5-C5-D3 |
| A13-B79-C4-D3 | A9-B5-C5-D3 |
| A24-B79-C4-D3 | A13-B5-C5-D3 |
| A69-B79-C4-D3 | A24-B5-C5-D3 |
| A67-B79-C4-D3 | A69-B5-C5-D3 |
| A39-B79-C4-D3 | A67-B5-C5-D3 |
| A65-B79-C4-D3 | A39-B5-C5-D3 |
| A66-B79-C4-D3 | A65-B5-C5-D3 |
| A2-B80-C4-D3 | A66-B5-C5-D3 |
| A3-B80-C4-D3 | A2-B6-C5-D3 |
| A9-B80-C4-D3 | A3-B6-C5-D3 |
| A13-B80-C4-D3 | A9-B6-C5-D3 |
| A24-B80-C4-D3 | A13-B6-C5-D3 |
| A69-B80-C4-D3 | A24-B6-C5-D3 |
| A67-B80-C4-D3 | A69-B6-C5-D3 |
| A39-B80-C4-D3 | A67-B6-C5-D3 |
| A65-B80-C4-D3 | A39-B6-C5-D3 |
| A66-B80-C4-D3 | A65-B6-C5-D3 |
| A2-B85-C4-D3 | A66-B6-C5-D3 |
| A3-B85-C4-D3 | A2-B32-C5-D3 |
| A9-B85-C4-D3 | A3-B32-C5-D3 |
| A13-B85-C4-D3 | A9-B32-C5-D3 |
| A24-B85-C4-D3 | A13-B32-C5-D3 |
| A69-B85-C4-D3 | A24-B32-C5-D3 |
| A67-B85-C4-D3 | A69-B32-C5-D3 |
| A39-B85-C4-D3 | A67-B32-C5-D3 |
| A65-B85-C4-D3 | A39-B32-C5-D3 |
| A66-B85-C4-D3 | A65-B32-C5-D3 |
| A2-B86-C4-D3 | A66-B32-C5-D3 |
| A3-B86-C4-D3 | A2-B39-C5-D3 |
| A9-B86-C4-D3 | A3-B39-C5-D3 |
| A13-B86-C4-D3 | A9-B39-C5-D3 |
| A24-B86-C4-D3 | A13-B39-C5-D3 |
| A69-B86-C4-D3 | A24-B39-C5-D3 |
| A67-B86-C4-D3 | A69-B39-C5-D3 |
| A39-B86-C4-D3 | A67-B39-C5-D3 |
| A65-B86-C4-D3 | A39-B39-C5-D3 |
| A66-B86-C4-D3 | A65-B39-C5-D3 |
| A2-B87-C4-D3 | A66-B39-C5-D3 |
| A3-B87-C4-D3 | A2-B45-C5-D3 |
| A9-B87-C4-D3 | A3-B45-C5-D3 |
| A13-B87-C4-D3 | A9-B45-C5-D3 |
| A24-B87-C4-D3 | A13-B45-C5-D3 |
| A69-B87-C4-D3 | A24-B45-C5-D3 |
| A67-B87-C4-D3 | A69-B45-C5-D3 |
| A39-B87-C4-D3 | A67-B45-C5-D3 |
| A65-B87-C4-D3 | A39-B45-C5-D3 |
| A66-B87-C4-D3 | A65-B45-C5-D3 |
| A2-B89-C4-D3 | A66-B45-C5-D3 |
| A3-B89-C4-D3 | A2-B53-C5-D3 |
| A9-B89-C4-D3 | A3-B53-C5-D3 |
| A13-B89-C4-D3 | A9-B53-C5-D3 |
| A24-B89-C4-D3 | A13-B53-C5-D3 |
| A69-B89-C4-D3 | A24-B53-C5-D3 |
| A67-B89-C4-D3 | A69-B53-C5-D3 |
| A39-B89-C4-D3 | A67-B53-C5-D3 |
| A65-B89-C4-D3 | A39-B53-C5-D3 |
| A66-B89-C4-D3 | A65-B53-C5-D3 |
| A2-B92-C4-D3 | A66-B53-C5-D3 |

TABLE 6-continued

| | |
|---|---|
| A2-B79-C5-D3 | A66-B4-C6-D3 |
| A3-B79-C5-D3 | A2-B5-C6-D3 |
| A9-B79-C5-D3 | A3-B5-C6-D3 |
| A13-B79-C5-D3 | A9-B5-C6-D3 |
| A24-B79-C5-D3 | A13-B5-C6-D3 |
| A69-B79-C5-D3 | A24-B5-C6-D3 |
| A67-B79-C5-D3 | A69-B5-C6-D3 |
| A39-B79-C5-D3 | A67-B5-C6-D3 |
| A65-B79-C5-D3 | A39-B5-C6-D3 |
| A66-B79-C5-D3 | A65-B5-C6-D3 |
| A2-B80-C5-D3 | A66-B5-C6-D3 |
| A3-B80-C5-D3 | A2-B6-C6-D3 |
| A9-B80-C5-D3 | A3-B6-C6-D3 |
| A13-B80-C5-D3 | A9-B6-C6-D3 |
| A24-B80-C5-D3 | A13-B6-C6-D3 |
| A69-B80-C5-D3 | A24-B6-C6-D3 |
| A67-B80-C5-D3 | A69-B6-C6-D3 |
| A39-B80-C5-D3 | A67-B6-C6-D3 |
| A65-B80-C5-D3 | A39-B6-C6-D3 |
| A66-B80-C5-D3 | A65-B6-C6-D3 |
| A2-B85-C5-D3 | A66-B6-C6-D3 |
| A3-B85-C5-D3 | A2-B32-C6-D3 |
| A9-B85-C5-D3 | A3-B32-C6-D3 |
| A13-B85-C5-D3 | A9-B32-C6-D3 |
| A24-B85-C5-D3 | A13-B32-C6-D3 |
| A69-B85-C5-D3 | A24-B32-C6-D3 |
| A67-B85-C5-D3 | A69-B32-C6-D3 |
| A39-B85-C5-D3 | A67-B32-C6-D3 |
| A65-B85-C5-D3 | A39-B32-C6-D3 |
| A66-B85-C5-D3 | A65-B32-C6-D3 |
| A2-B86-C5-D3 | A66-B32-C6-D3 |
| A3-B86-C5-D3 | A2-B39-C6-D3 |
| A9-B86-C5-D3 | A3-B39-C6-D3 |
| A13-B86-C5-D3 | A9-B39-C6-D3 |
| A24-B86-C5-D3 | A13-B39-C6-D3 |
| A69-B86-C5-D3 | A24-B39-C6-D3 |
| A67-B86-C5-D3 | A69-B39-C6-D3 |
| A39-B86-C5-D3 | A67-B39-C6-D3 |
| A65-B86-C5-D3 | A39-B39-C6-D3 |
| A66-B86-C5-D3 | A65-B39-C6-D3 |
| A2-B87-C5-D3 | A66-B39-C6-D3 |
| A3-B87-C5-D3 | A2-B45-C6-D3 |
| A9-B87-C5-D3 | A3-B45-C6-D3 |
| A13-B87-C5-D3 | A9-B45-C6-D3 |
| A24-B87-C5-D3 | A13-B45-C6-D3 |
| A69-B87-C5-D3 | A24-B45-C6-D3 |
| A67-B87-C5-D3 | A69-B45-C6-D3 |
| A39-B87-C5-D3 | A67-B45-C6-D3 |
| A65-B87-C5-D3 | A39-B45-C6-D3 |
| A66-B87-C5-D3 | A65-B45-C6-D3 |
| A2-B89-C5-D3 | A66-B45-C6-D3 |
| A3-B89-C5-D3 | A2-B53-C6-D3 |
| A9-B89-C5-D3 | A3-B53-C6-D3 |
| A13-B89-C5-D3 | A9-B53-C6-D3 |
| A24-B89-C5-D3 | A13-B53-C6-D3 |
| A69-B89-C5-D3 | A24-B53-C6-D3 |
| A67-B89-C5-D3 | A69-B53-C6-D3 |
| A39-B89-C5-D3 | A67-B53-C6-D3 |
| A65-B89-C5-D3 | A39-B53-C6-D3 |
| A66-B89-C5-D3 | A65-B53-C6-D3 |
| A2-B92-C5-D3 | A66-B53-C6-D3 |
| A3-B92-C5-D3 | A2-B79-C6-D3 |
| A9-B92-C5-D3 | A3-B79-C6-D3 |
| A13-B92-C5-D3 | A9-B79-C6-D3 |
| A24-B92-C5-D3 | A13-B79-C6-D3 |
| A69-B92-C5-D3 | A24-B79-C6-D3 |
| A67-B92-C5-D3 | A69-B79-C6-D3 |
| A39-B92-C5-D3 | A67-B79-C6-D3 |
| A65-B92-C5-D3 | A39-B79-C6-D3 |
| A66-B92-C5-D3 | A65-B79-C6-D3 |
| A2-B4-C6-D3 | A66-B79-C6-D3 |
| A3-B4-C6-D3 | A2-B80-C6-D3 |
| A9-B4-C6-D3 | A3-B80-C6-D3 |
| A13-B4-C6-D3 | A9-B80-C6-D3 |
| A24-B4-C6-D3 | A13-B80-C6-D3 |
| A69-B4-C6-D3 | A24-B80-C6-D3 |
| A67-B4-C6-D3 | A69-B80-C6-D3 |
| A39-B4-C6-D3 | A67-B80-C6-D3 |
| A65-B4-C6-D3 | A39-B80-C6-D3 |

TABLE 6-continued

A65-B80-C6-D3
A66-B80-C6-D3
A2-B85-C6-D3
A3-B85-C6-D3
A9-B85-C6-D3
A13-B85-C6-D3
A24-B85-C6-D3
A69-B85-C6-D3
A67-B85-C6-D3
A39-B85-C6-D3
A65-B85-C6-D3
A66-B85-C6-D3
A2-B86-C6-D3
A3-B86-C6-D3
A9-B86-C6-D3
A13-B86-C6-D3
A24-B86-C6-D3
A69-B86-C6-D3
A67-B86-C6-D3
A39-B86-C6-D3
A65-B86-C6-D3
A66-B86-C6-D3
A2-B87-C6-D3
A3-B87-C6-D3
A9-B87-C6-D3
A13-B87-C6-D3
A24-B87-C6-D3
A69-B87-C6-D3
A67-B87-C6-D3
A39-B87-C6-D3
A65-B87-C6-D3
A66-B87-C6-D3
A2-B89-C6-D3
A3-B89-C6-D3
A9-B89-C6-D3
A13-B89-C6-D3
A24-B89-C6-D3
A69-B89-C6-D3
A67-B89-C6-D3
A39-B89-C6-D3
A65-B89-C6-D3
A66-B89-C6-D3
A2-B92-C6-D3
A3-B92-C6-D3
A9-B92-C6-D3
A13-B92-C6-D3
A24-B92-C6-D3
A69-B92-C6-D3
A67-B92-C6-D3
A39-B92-C6-D3
A65-B92-C6-D3
A66-B92-C6-D3
A2-B4-C7-D3
A3-B4-C7-D3
A9-B4-C7-D3
A13-B4-C7-D3
A24-B4-C7-D3
A69-B4-C7-D3
A67-B4-C7-D3
A39-B4-C7-D3
A65-B4-C7-D3
A66-B4-C7-D3
A2-B5-C7-D3
A3-B5-C7-D3
A9-B5-C7-D3
A13-B5-C7-D3
A24-B5-C7-D3
A69-B5-C7-D3
A67-B5-C7-D3
A39-B5-C7-D3
A65-B5-C7-D3
A66-B5-C7-D3
A2-B6-C7-D3
A3-B6-C7-D3
A9-B6-C7-D3
A13-B6-C7-D3
A24-B6-C7-D3
A69-B6-C7-D3
A67-B6-C7-D3

TABLE 6-continued

A39-B6-C7-D3
A65-B6-C7-D3
A66-B6-C7-D3
A2-B32-C7-D3
A3-B32-C7-D3
A9-B32-C7-D3
A13-B32-C7-D3
A24-B32-C7-D3
A69-B32-C7-D3
A67-B32-C7-D3
A39-B32-C7-D3
A65-B32-C7-D3
A66-B32-C7-D3
A2-B39-C7-D3
A3-B39-C7-D3
A9-B39-C7-D3
A13-B39-C7-D3
A24-B39-C7-D3
A69-B39-C7-D3
A67-B39-C7-D3
A39-B39-C7-D3
A65-B39-C7-D3
A66-B39-C7-D3
A2-B45-C7-D3
A3-B45-C7-D3
A9-B45-C7-D3
A13-B45-C7-D3
A24-B45-C7-D3
A69-B45-C7-D3
A67-B45-C7-D3
A39-B45-C7-D3
A65-B45-C7-D3
A66-B45-C7-D3
A2-B53-C7-D3
A3-B53-C7-D3
A9-B53-C7-D3
A13-B53-C7-D3
A24-B53-C7-D3
A69-B53-C7-D3
A67-B53-C7-D3
A39-B53-C7-D3
A65-B53-C7-D3
A66-B53-C7-D3
A2-B79-C7-D3
A3-B79-C7-D3
A9-B79-C7-D3
A13-B79-C7-D3
A24-B79-C7-D3
A69-B79-C7-D3
A67-B79-C7-D3
A39-B79-C7-D3
A65-B79-C7-D3
A66-B79-C7-D3
A2-B80-C7-D3
A3-B80-C7-D3
A9-B80-C7-D3
A13-B80-C7-D3
A24-B80-C7-D3
A69-B80-C7-D3
A67-B80-C7-D3
A39-B80-C7-D3
A65-B80-C7-D3
A66-B80-C7-D3
A2-B85-C7-D3
A3-B85-C7-D3
A9-B85-C7-D3
A13-B85-C7-D3
A24-B85-C7-D3
A69-B85-C7-D3
A67-B85-C7-D3
A39-B85-C7-D3
A65-B85-C7-D3
A66-B85-C7-D3
A2-B86-C7-D3
A3-B86-C7-D3
A9-B86-C7-D3
A13-B86-C7-D3
A24-B86-C7-D3
A69-B86-C7-D3

TABLE 6-continued

A67-B86-C7-D3
A39-B86-C7-D3
A65-B86-C7-D3
A66-B86-C7-D3
A2-B87-C7-D3
A3-B87-C7-D3
A9-B87-C7-D3
A13-B87-C7-D3
A24-B87-C7-D3
A69-B87-C7-D3
A67-B87-C7-D3
A39-B87-C7-D3
A65-B87-C7-D3
A66-B87-C7-D3
A2-B89-C7-D3
A3-B89-C7-D3
A9-B89-C7-D3
A13-B89-C7-D3
A24-B89-C7-D3
A69-B89-C7-D3
A67-B89-C7-D3
A39-B89-C7-D3
A65-B89-C7-D3
A66-B89-C7-D3
A2-B92-C7-D3
A3-B92-C7-D3
A9-B92-C7-D3
A13-B92-C7-D3
A24-B92-C7-D3
A69-B92-C7-D3
A67-B92-C7-D3
A39-B92-C7-D3
A65-B92-C7-D3
A66-B92-C7-D3
A2-B4-C8-D3
A3-B4-C8-D3
A9-B4-C8-D3
A13-B4-C8-D3
A24-B4-C8-D3
A69-B4-C8-D3
A67-B4-C8-D3
A39-B4-C8-D3
A65-B4-C8-D3
A66-B4-C8-D3
A2-B5-C8-D3
A3-B5-C8-D3
A9-B5-C8-D3
A13-B5-C8-D3
A24-B5-C8-D3
A69-B5-C8-D3
A67-B5-C8-D3
A39-B5-C8-D3
A65-B5-C8-D3
A66-B5-C8-D3
A2-B6-C8-D3
A3-B6-C8-D3
A9-B6-C8-D3
A13-B6-C8-D3
A24-B6-C8-D3
A69-B6-C8-D3
A67-B6-C8-D3
A39-B6-C8-D3
A65-B6-C8-D3
A66-B6-C8-D3
A2-B32-C8-D3
A3-B32-C8-D3
A9-B32-C8-D3
A13-B32-C8-D3
A24-B32-C8-D3
A69-B32-C8-D3
A67-B32-C8-D3
A39-B32-C8-D3
A65-B32-C8-D3
A66-B32-C8-D3
A2-B39-C8-D3
A3-B39-C8-D3
A9-B39-C8-D3
A13-B39-C8-D3
A24-B39-C8-D3

TABLE 6-continued

A69-B39-C8-D3
A67-B39-C8-D3
A39-B39-C8-D3
A65-B39-C8-D3
A66-B39-C8-D3
A2-B45-C8-D3
A3-B45-C8-D3
A9-B45-C8-D3
A13-B45-C8-D3
A24-B45-C8-D3
A69-B45-C8-D3
A67-B45-C8-D3
A39-B45-C8-D3
A65-B45-C8-D3
A66-B45-C8-D3
A2-B53-C8-D3
A3-B53-C8-D3
A9-B53-C8-D3
A13-B53-C8-D3
A24-B53-C8-D3
A69-B53-C8-D3
A67-B53-C8-D3
A39-B53-C8-D3
A65-B53-C8-D3
A66-B53-C8-D3
A2-B79-C8-D3
A3-B79-C8-D3
A9-B79-C8-D3
A13-B79-C8-D3
A24-B79-C8-D3
A69-B79-C8-D3
A67-B79-C8-D3
A39-B79-C8-D3
A65-B79-C8-D3
A66-B79-C8-D3
A2-B80-C8-D3
A3-B80-C8-D3
A9-B80-C8-D3
A13-B80-C8-D3
A24-B80-C8-D3
A69-B80-C8-D3
A67-B80-C8-D3
A39-B80-C8-D3
A65-B80-C8-D3
A66-B80-C8-D3
A2-B85-C8-D3
A3-B85-C8-D3
A9-B85-C8-D3
A13-B85-C8-D3
A24-B85-C8-D3
A69-B85-C8-D3
A67-B85-C8-D3
A39-B85-C8-D3
A65-B85-C8-D3
A66-B85-C8-D3
A2-B86-C8-D3
A3-B86-C8-D3
A9-B86-C8-D3
A13-B86-C8-D3
A24-B86-C8-D3
A69-B86-C8-D3
A67-B86-C8-D3
A39-B86-C8-D3
A65-B86-C8-D3
A66-B86-C8-D3
A2-B87-C8-D3
A3-B87-C8-D3
A9-B87-C8-D3
A13-B87-C8-D3
A24-B87-C8-D3
A69-B87-C8-D3
A67-B87-C8-D3
A39-B87-C8-D3
A65-B87-C8-D3
A66-B87-C8-D3
A2-B89-C8-D3
A3-B89-C8-D3
A9-B89-C8-D3
A13-B89-C8-D3

TABLE 6-continued

A24-B89-C8-D3
A69-B89-C8-D3
A67-B89-C8-D3
A39-B89-C8-D3
A65-B89-C8-D3
A66-B89-C8-D3
A2-B92-C8-D3
A3-B92-C8-D3
A9-B92-C8-D3
A13-B92-C8-D3
A24-B92-C8-D3
A69-B92-C8-D3
A67-B92-C8-D3
A39-B92-C8-D3
A65-B92-C8-D3
A66-B92-C8-D3
A2-B4-C9-D3
A3-B4-C9-D3
A9-B4-C9-D3
A13-B4-C9-D3
A24-B4-C9-D3
A69-B4-C9-D3
A67-B4-C9-D3
A39-B4-C9-D3
A65-B4-C9-D3
A66-B4-C9-D3
A2-B5-C9-D3
A3-B5-C9-D3
A9-B5-C9-D3
A13-B5-C9-D3
A24-B5-C9-D3
A69-B5-C9-D3
A67-B5-C9-D3
A39-B5-C9-D3
A65-B5-C9-D3
A66-B5-C9-D3
A2-B6-C9-D3
A3-B6-C9-D3
A9-B6-C9-D3
A13-B6-C9-D3
A24-B6-C9-D3
A69-B6-C9-D3
A67-B6-C9-D3
A39-B6-C9-D3
A65-B6-C9-D3
A66-B6-C9-D3
A2-B32-C9-D3
A3-B32-C9-D3
A9-B32-C9-D3
A13-B32-C9-D3
A24-B32-C9-D3
A69-B32-C9-D3
A67-B32-C9-D3
A39-B32-C9-D3
A65-B32-C9-D3
A66-B32-C9-D3
A2-B39-C9-D3
A3-B39-C9-D3
A9-B39-C9-D3
A13-B39-C9-D3
A24-B39-C9-D3
A69-B39-C9-D3
A67-B39-C9-D3
A39-B39-C9-D3
A65-B39-C9-D3
A66-B39-C9-D3
A2-B45-C9-D3
A3-B45-C9-D3
A9-B45-C9-D3
A13-B45-C9-D3
A24-B45-C9-D3
A69-B45-C9-D3
A67-B45-C9-D3
A39-B45-C9-D3
A65-B45-C9-D3
A66-B45-C9-D3
A2-B53-C9-D3
A3-B53-C9-D3
A9-B53-C9-D3

TABLE 6-continued

A13-B53-C9-D3
A24-B53-C9-D3
A69-B53-C9-D3
A67-B53-C9-D3
A39-B53-C9-D3
A65-B53-C9-D3
A66-B53-C9-D3
A2-B79-C9-D3
A3-B79-C9-D3
A9-B79-C9-D3
A13-B79-C9-D3
A24-B79-C9-D3
A69-B79-C9-D3
A67-B79-C9-D3
A39-B79-C9-D3
A65-B79-C9-D3
A66-B79-C9-D3
A2-B80-C9-D3
A3-B80-C9-D3
A9-B80-C9-D3
A13-B80-C9-D3
A24-B80-C9-D3
A69-B80-C9-D3
A67-B80-C9-D3
A39-B80-C9-D3
A65-B80-C9-D3
A66-B80-C9-D3
A2-B85-C9-D3
A3-B85-C9-D3
A9-B85-C9-D3
A13-B85-C9-D3
A24-B85-C9-D3
A69-B85-C9-D3
A67-B85-C9-D3
A39-B85-C9-D3
A65-B85-C9-D3
A66-B85-C9-D3
A2-B86-C9-D3
A3-B86-C9-D3
A9-B86-C9-D3
A13-B86-C9-D3
A24-B86-C9-D3
A69-B86-C9-D3
A67-B86-C9-D3
A39-B86-C9-D3
A65-B86-C9-D3
A66-B86-C9-D3
A2-B87-C9-D3
A3-B87-C9-D3
A9-B87-C9-D3
A13-B87-C9-D3
A24-B87-C9-D3
A69-B87-C9-D3
A67-B87-C9-D3
A39-B87-C9-D3
A65-B87-C9-D3
A66-B87-C9-D3
A2-B89-C9-D3
A3-B89-C9-D3
A9-B89-C9-D3
A13-B89-C9-D3
A24-B89-C9-D3
A69-B89-C9-D3
A67-B89-C9-D3
A39-B89-C9-D3
A65-B89-C9-D3
A66-B89-C9-D3
A2-B92-C9-D3
A3-B92-C9-D3
A9-B92-C9-D3
A13-B92-C9-D3
A24-B92-C9-D3
A69-B92-C9-D3
A67-B92-C9-D3
A39-B92-C9-D3
A65-B92-C9-D3
A66-B92-C9-D3
A2-B4-C10-D3
A3-B4-C10-D3

TABLE 6-continued

A9-B4-C10-D3
A13-B4-C10-D3
A24-B4-C10-D3
A69-B4-C10-D3
A67-B4-C10-D3
A39-B4-C10-D3
A65-B4-C10-D3
A66-B4-C10-D3
A2-B5-C10-D3
A3-B5-C10-D3
A9-B5-C10-D3
A13-B5-C10-D3
A24-B5-C10-D3
A69-B5-C10-D3
A67-B5-C10-D3
A39-B5-C10-D3
A65-B5-C10-D3
A66-B5-C10-D3
A2-B6-C10-D3
A3-B6-C10-D3
A9-B6-C10-D3
A13-B6-C10-D3
A24-B6-C10-D3
A69-B6-C10-D3
A67-B6-C10-D3
A39-B6-C10-D3
A65-B6-C10-D3
A66-B6-C10-D3
A2-B32-C10-D3
A3-B32-C10-D3
A9-B32-C10-D3
A13-B32-C10-D3
A24-B32-C10-D3
A69-B32-C10-D3
A67-B32-C10-D3
A39-B32-C10-D3
A65-B32-C10-D3
A66-B32-C10-D3
A2-B39-C10-D3
A3-B39-C10-D3
A9-B39-C10-D3
A13-B39-C10-D3
A24-B39-C10-D3
A69-B39-C10-D3
A67-B39-C10-D3
A39-B39-C10-D3
A65-B39-C10-D3
A66-B39-C10-D3
A2-B45-C10-D3
A3-B45-C10-D3
A9-B45-C10-D3
A13-B45-C10-D3
A24-B45-C10-D3
A69-B45-C10-D3
A67-B45-C10-D3
A39-B45-C10-D3
A65-B45-C10-D3
A66-B45-C10-D3
A1-B53-C10-D3
A3-B53-C10-D3
A9-B53-C10-D3
A13-B53-C10-D3
A24-B53-C10-D3
A69-B53-C10-D3
A67-B53-C10-D3
A39-B53-C10-D3
A65-B53-C10-D3
A66-B53-C10-D3
A2-B79-C10-D3
A3-B79-C10-D3
A9-B79-C10-D3
A13-B79-C10-D3
A24-B79-C10-D3
A69-B79-C10-D3
A67-B79-C10-D3
A39-B79-C10-D3
A65-B79-C10-D3
A66-B79-C10-D3
A2-B80-C10-D3

TABLE 6-continued

A3-B80-C10-D3
A9-B80-C10-D3
A13-B80-C10-D3
A24-B80-C10-D3
A69-B80-C10-D3
A67-B80-C10-D3
A39-B80-C10-D3
A65-B80-C10-D3
A66-B80-C10-D3
A2-B85-C10-D3
A3-B85-C10-D3
A9-B85-C10-D3
A13-B85-C10-D3
A24-B85-C10-D3
A69-B85-C10-D3
A67-B85-C10-D3
A39-B85-C10-D3
A65-B85-C10-D3
A66-B85-C10-D3
A2-B86-C10-D3
A3-B86-C10-D3
A9-B86-C10-D3
A13-B86-C10-D3
A24-B86-C10-D3
A69-B86-C10-D3
A67-B86-C10-D3
A39-B86-C10-D3
A65-B86-C10-D3
A66-B86-C10-D3
A2-B87-C10-D3
A3-B87-C10-D3
A9-B87-C10-D3
A13-B87-C10-D3
A24-B87-C10-D3
A69-B87-C10-D3
A67-B87-C10-D3
A39-B87-C10-D3
A65-B87-C10-D3
A66-B87-C10-D3
A2-B89-C10-D3
A3-B89-C10-D3
A9-B89-C10-D3
A13-B89-C10-D3
A24-B89-C10-D3
A69-B89-C10-D3
A67-B89-C10-D3
A39-B89-C10-D3
A65-B89-C10-D3
A66-B89-C10-D3
A2-B92-C10-D3
A3-B92-C10-D3
A9-B92-C10-D3
A13-B92-C10-D3
A24-B92-C10-D3
A69-B92-C10-D3
A67-B92-C10-D3
A39-B92-C10-D3
A65-B92-C10-D3
A66-B92-C10-D3
A2-B4-C11-D3
A3-B4-C11-D3
A9-B4-C11-D3
A13-B4-C11-D3
A24-B4-C11-D3
A69-B4-C11-D3
A67-B4-C11-D3
A39-B4-C11-D3
A65-B4-C11-D3
A66-B4-C11-D3
A2-B5-C11-D3
A3-B5-C11-D3
A9-B5-C11-D3
A13-B5-C11-D3
A24-B5-C11-D3
A69-B5-C11-D3
A67-B5-C11-D3
A39-B5-C11-D3
A65-B5-C11-D3
A66-B5-C11-D3

TABLE 6-continued

| | |
|---|---|
| A2-B6-C11-D3 | A66-B85-C11-D3 |
| A3-B6-C11-D3 | A2-B86-C11-D3 |
| A9-B6-C11-D3 | A3-B86-C11-D3 |
| A13-B6-C11-D3 | A9-B86-C11-D3 |
| A24-B6-C11-D3 | A13-B86-C11-D3 |
| A69-B6-C11-D3 | A24-B86-C11-D3 |
| A67-B6-C11-D3 | A69-B86-C11-D3 |
| A39-B6-C11-D3 | A67-B86-C11-D3 |
| A65-B6-C11-D3 | A39-B86-C11-D3 |
| A66-B6-C11-D3 | A65-B86-C11-D3 |
| A2-B32-C11-D3 | A66-B86-C11-D3 |
| A3-B32-C11-D3 | A2-B87-C11-D3 |
| A9-B32-C11-D3 | A3-B87-C11-D3 |
| A13-B32-C11-D3 | A9-B87-C11-D3 |
| A24-B32-C11-D3 | A13-B87-C11-D3 |
| A69-B32-C11-D3 | A24-B87-C11-D3 |
| A67-B32-C11-D3 | A69-B87-C11-D3 |
| A39-B32-C11-D3 | A67-B87-C11-D3 |
| A65-B32-C11-D3 | A39-B87-C11-D3 |
| A66-B32-C11-D3 | A65-B87-C11-D3 |
| A2-B39-C11-D3 | A66-B87-C11-D3 |
| A3-B39-C11-D3 | A2-B89-C11-D3 |
| A9-B39-C11-D3 | A3-B89-C11-D3 |
| A13-B39-C11-D3 | A9-B89-C11-D3 |
| A24-B39-C11-D3 | A13-B89-C11-D3 |
| A69-B39-C11-D3 | A24-B89-C11-D3 |
| A67-B39-C11-D3 | A69-B89-C11-D3 |
| A39-B39-C11-D3 | A67-B89-C11-D3 |
| A65-B39-C11-D3 | A39-B89-C11-D3 |
| A66-B39-C11-D3 | A65-B89-C11-D3 |
| A2-B45-C11-D3 | A66-B89-C11-D3 |
| A3-B45-C11-D3 | A2-B92-C11-D3 |
| A9-B45-C11-D3 | A3-B92-C11-D3 |
| A13-B45-C11-D3 | A9-B92-C11-D3 |
| A24-B45-C11-D3 | A13-B92-C11-D3 |
| A69-B45-C11-D3 | A24-B92-C11-D3 |
| A67-B45-C11-D3 | A69-B92-C11-D3 |
| A39-B45-C11-D3 | A67-B92-C11-D3 |
| A65-B45-C11-D3 | A39-B92-C11-D3 |
| A66-B45-C11-D3 | A65-B92-C11-D3 |
| A2-B53-C11-D3 | A66-B92-C11-D3 |
| A3-B53-C11-D3 | A2-B4-C12-D3 |
| A9-B53-C11-D3 | A3-B4-C12-D3 |
| A13-B53-C11-D3 | A9-B4-C12-D3 |
| A24-B53-C11-D3 | A13-B4-C12-D3 |
| A69-B53-C11-D3 | A24-B4-C12-D3 |
| A67-B53-C11-D3 | A69-B4-C12-D3 |
| A39-B53-C11-D3 | A67-B4-C12-D3 |
| A65-B53-C11-D3 | A39-B4-C12-D3 |
| A66-B53-C11-D3 | A65-B4-C12-D3 |
| A2-B79-C11-D3 | A66-B4-C12-D3 |
| A3-B79-C11-D3 | A2-B5-C12-D3 |
| A9-B79-C11-D3 | A3-B5-C12-D3 |
| A13-B79-C11-D3 | A9-B5-C12-D3 |
| A24-B79-C11-D3 | A13-B5-C12-D3 |
| A69-B79-C11-D3 | A24-B5-C12-D3 |
| A67-B79-C11-D3 | A69-B5-C12-D3 |
| A39-B79-C11-D3 | A67-B5-C12-D3 |
| A65-B79-C11-D3 | A39-B5-C12-D3 |
| A66-B79-C11-D3 | A65-B5-C12-D3 |
| A2-B80-C11-D3 | A66-B5-C12-D3 |
| A3-B80-C11-D3 | A2-B6-C12-D3 |
| A9-B80-C11-D3 | A3-B6-C12-D3 |
| A13-B80-C11-D3 | A9-B6-C12-D3 |
| A24-B80-C11-D3 | A13-B6-C12-D3 |
| A69-B80-C11-D3 | A24-B6-C12-D3 |
| A67-B80-C11-D3 | A69-B6-C12-D3 |
| A39-B80-C11-D3 | A67-B6-C12-D3 |
| A65-B80-C11-D3 | A39-B6-C12-D3 |
| A66-B80-C11-D3 | A65-B6-C12-D3 |
| A2-B85-C11-D3 | A66-B6-C12-D3 |
| A3-B85-C11-D3 | A2-B32-C12-D3 |
| A9-B85-C11-D3 | A3-B32-C12-D3 |
| A13-B85-C11-D3 | A9-B32-C12-D3 |
| A24-B85-C11-D3 | A13-B32-C12-D3 |
| A69-B85-C11-D3 | A24-B32-C12-D3 |
| A67-B85-C11-D3 | A69-B32-C12-D3 |
| A39-B85-C11-D3 | A67-B32-C12-D3 |
| A65-B85-C11-D3 | A39-B32-C12-D3 |

TABLE 6-continued

| | |
|---|---|
| A65-B32-C12-D3 | A39-B87-C12-D3 |
| A66-B32-C12-D3 | A65-B87-C12-D3 |
| A2-B39-C12-D3 | A66-B87-C12-D3 |
| A3-B39-C12-D3 | A2-B89-C12-D3 |
| A9-B39-C12-D3 | A3-B89-C12-D3 |
| A13-B39-C12-D3 | A9-B89-C12-D3 |
| A24-B39-C12-D3 | A13-B89-C12-D3 |
| A69-B39-C12-D3 | A24-B89-C12-D3 |
| A67-B39-C12-D3 | A69-B89-C12-D3 |
| A39-B39-C12-D3 | A67-B89-C12-D3 |
| A65-B39-C12-D3 | A39-B89-C12-D3 |
| A66-B39-C12-D3 | A65-B89-C12-D3 |
| A2-B45-C12-D3 | A66-B89-C12-D3 |
| A3-B45-C12-D3 | A2-B92-C12-D3 |
| A9-B45-C12-D3 | A3-B92-C12-D3 |
| A13-B45-C12-D3 | A9-B92-C12-D3 |
| A24-B45-C12-D3 | A13-B92-C12-D3 |
| A69-B45-C12-D3 | A24-B92-C12-D3 |
| A67-B45-C12-D3 | A69-B92-C12-D3 |
| A39-B45-C12-D3 | A67-B92-C12-D3 |
| A65-B45-C12-D3 | A39-B92-C12-D3 |
| A66-B45-C12-D3 | A65-B92-C12-D3 |
| A2-B53-C12-D3 | A66-B92-C12-D3 |
| A3-B53-C12-D3 | A2-B4-C13-D3 |
| A9-B53-C12-D3 | A3-B4-C13-D3 |
| A13-B53-C12-D3 | A9-B4-C13-D3 |
| A24-B53-C12-D3 | A13-B4-C13-D3 |
| A69-B53-C12-D3 | A24-B4-C13-D3 |
| A67-B53-C12-D3 | A69-B4-C13-D3 |
| A39-B53-C12-D3 | A67-B4-C13-D3 |
| A65-B53-C12-D3 | A39-B4-C13-D3 |
| A66-B53-C12-D3 | A65-B4-C13-D3 |
| A2-B79-C12-D3 | A66-B4-C13-D3 |
| A3-B79-C12-D3 | A2-B5-C13-D3 |
| A9-B79-C12-D3 | A3-B5-C13-D3 |
| A13-B79-C12-D3 | A9-B5-C13-D3 |
| A24-B79-C12-D3 | A13-B5-C13-D3 |
| A69-B79-C12-D3 | A24-B5-C13-D3 |
| A67-B79-C12-D3 | A69-B5-C13-D3 |
| A39-B79-C12-D3 | A67-B5-C13-D3 |
| A65-B79-C12-D3 | A39-B5-C13-D3 |
| A66-B79-C12-D3 | A65-B5-C13-D3 |
| A2-B80-C12-D3 | A66-B5-C13-D3 |
| A3-B80-C12-D3 | A2-B6-C13-D3 |
| A9-B80-C12-D3 | A3-B6-C13-D3 |
| A13-B80-C12-D3 | A9-B6-C13-D3 |
| A24-B80-C12-D3 | A13-B6-C13-D3 |
| A69-B80-C12-D3 | A24-B6-C13-D3 |
| A67-B80-C12-D3 | A69-B6-C13-D3 |
| A39-B80-C12-D3 | A67-B6-C13-D3 |
| A65-B80-C12-D3 | A39-B6-C13-D3 |
| A66-B80-C12-D3 | A65-B6-C13-D3 |
| A2-B85-C12-D3 | A66-B6-C13-D3 |
| A3-B85-C12-D3 | A2-B32-C13-D3 |
| A9-B85-C12-D3 | A3-B32-C13-D3 |
| A13-B85-C12-D3 | A9-B32-C13-D3 |
| A24-B85-C12-D3 | A13-B32-C13-D3 |
| A69-B85-C12-D3 | A24-B32-C13-D3 |
| A67-B85-C12-D3 | A69-B32-C13-D3 |
| A39-B85-C12-D3 | A67-B32-C13-D3 |
| A65-B85-C12-D3 | A39-B32-C13-D3 |
| A66-B85-C12-D3 | A65-B32-C13-D3 |
| A2-B86-C12-D3 | A66-B32-C13-D3 |
| A3-B86-C12-D3 | A2-B39-C13-D3 |
| A9-B86-C12-D3 | A3-B39-C13-D3 |
| A13-B86-C12-D3 | A9-B39-C13-D3 |
| A24-B86-C12-D3 | A13-B39-C13-D3 |
| A69-B86-C12-D3 | A24-B39-C13-D3 |
| A67-B86-C12-D3 | A69-B39-C13-D3 |
| A39-B86-C12-D3 | A67-B39-C13-D3 |
| A65-B86-C12-D3 | A39-B39-C13-D3 |
| A66-B86-C12-D3 | A65-B39-C13-D3 |
| A2-B87-C12-D3 | A66-B39-C13-D3 |
| A3-B87-C12-D3 | A2-B45-C13-D3 |
| A9-B87-C12-D3 | A3-B45-C13-D3 |
| A13-B87-C12-D3 | A9-B45-C13-D3 |
| A24-B87-C12-D3 | A13-B45-C13-D3 |
| A69-B87-C12-D3 | A24-B45-C13-D3 |
| A67-B87-C12-D3 | A69-B45-C13-D3 |

TABLE 6-continued

A67-B45-C13-D3
A39-B45-C13-D3
A65-B45-C13-D3
A66-B45-C13-D3
A2-B53-C13-D3
A3-B53-C13-D3
A9-B53-C13-D3
A13-B53-C13-D3
A24-B53-C13-D3
A69-B53-C13-D3
A67-B53-C13-D3
A39-B53-C13-D3
A65-B53-C13-D3
A66-B53-C13-D3
A2-B79-C13-D3
A3-B79-C13-D3
A9-B79-C13-D3
A13-B79-C13-D3
A24-B79-C13-D3
A69-B79-C13-D3
A67-B79-C13-D3
A39-B79-C13-D3
A65-B79-C13-D3
A66-B79-C13-D3
A2-B80-C13-D3
A3-B80-C13-D3
A9-B80-C13-D3
A13-B80-C13-D3
A24-B80-C13-D3
A69-B80-C13-D3
A67-B80-C13-D3
A39-B80-C13-D3
A65-B80-C13-D3
A66-B80-C13-D3
A2-B85-C13-D3
A3-B85-C13-D3
A9-B85-C13-D3
A13-B85-C13-D3
A24-B85-C13-D3
A69-B85-C13-D3
A67-B85-C13-D3
A39-B85-C13-D3
A65-B85-C13-D3
A66-B85-C13-D3
A2-B86-C13-D3
A3-B86-C13-D3
A9-B86-C13-D3
A13-B86-C13-D3
A24-B86-C13-D3
A69-B86-C13-D3
A67-B86-C13-D3
A39-B86-C13-D3
A65-B86-C13-D3
A66-B86-C13-D3
A2-B87-C13-D3
A3-B87-C13-D3
A9-B87-C13-D3
A13-B87-C13-D3
A24-B87-C13-D3
A69-B87-C13-D3
A67-B87-C13-D3
A39-B87-C13-D3
A65-B87-C13-D3
A66-B87-C13-D3
A2-B89-C13-D3
A3-B89-C13-D3
A9-B89-C13-D3
A13-B89-C13-D3
A24-B89-C13-D3
A69-B89-C13-D3
A67-B89-C13-D3
A39-B89-C13-D3
A65-B89-C13-D3
A66-B89-C13-D3
A2-B92-C13-D3
A3-B92-C13-D3
A9-B92-C13-D3
A13-B92-C13-D3
A24-B92-C13-D3

TABLE 6-continued

A69-B92-C13-D3
A67-B92-C13-D3
A39-B92-C13-D3
A65-B92-C13-D3
A66-B92-C13-D3
A2-B4-C1-D4
A3-B4-C1-D4
A9-B4-C1-D4
A13-B4-C1-D4
A24-B4-C1-D4
A69-B4-C1-D4
A67-B4-C1-D4
A39-B4-C1-D4
A65-B4-C1-D4
A66-B4-C1-D4
A2-B5-C1-D4
A3-B5-C1-D4
A9-B5-C1-D4
A13-B5-C1-D4
A24-B5-C1-D4
A69-B5-C1-D4
A67-B5-C1-D4
A39-B5-C1-D4
A65-B5-C1-D4
A66-B5-C1-D4
A2-B6-C1-D4
A3-B6-C1-D4
A9-B6-C1-D4
A13-B6-C1-D4
A24-B6-C1-D4
A69-B6-C1-D4
A67-B6-C1-D4
A39-B6-C1-D4
A65-B6-C1-D4
A66-B6-C1-D4
A2-B32-C1-D4
A3-B32-C1-D4
A9-B32-C1-D4
A13-B32-C1-D4
A24-B32-C1-D4
A69-B32-C1-D4
A67-B32-C1-D4
A39-B32-C1-D4
A65-B32-C1-D4
A66-B32-C1-D4
A2-B39-C1-D4
A3-B39-C1-D4
A9-B39-C1-D4
A13-B39-C1-D4
A24-B39-C1-D4
A69-B39-C1-D4
A67-B39-C1-D4
A39-B39-C1-D4
A65-B39-C1-D4
A66-B39-C1-D4
A2-B45-C1-D4
A3-B45-C1-D4
A9-B45-C1-D4
A13-B45-C1-D4
A24-B45-C1-D4
A69-B45-C1-D4
A67-B45-C1-D4
A39-B45-C1-D4
A65-B45-C1-D4
A66-B45-C1-D4
A2-B53-C1-D4
A3-B53-C1-D4
A9-B53-C1-D4
A13-B53-C1-D4
A24-B53-C1-D4
A69-B53-C1-D4
A67-B53-C1-D4
A39-B53-C1-D4
A65-B53-C1-D4
A66-B53-C1-D4
A2-B79-C1-D4
A3-B79-C1-D4
A9-B79-C1-D4
A13-B79-C1-D4

TABLE 6-continued

A24-B79-C1-D4
A69-B79-C1-D4
A67-B79-C1-D4
A39-B79-C1-D4
A65-B79-C1-D4
A66-B79-C1-D4
A2-B80-C1-D4
A3-B80-C1-D4
A9-B80-C1-D4
A13-B80-C1-D4
A24-B80-C1-D4
A69-B80-C1-D4
A67-B80-C1-D4
A39-B80-C1-D4
A65-B80-C1-D4
A66-B80-C1-D4
A2-B85-C1-D4
A3-B85-C1-D4
A9-B85-C1-D4
A13-B85-C1-D4
A24-B85-C1-D4
A69-B85-C1-D4
A67-B85-C1-D4
A39-B85-C1-D4
A65-B85-C1-D4
A66-B85-C1-D4
A2-B86-C1-D4
A3-B86-C1-D4
A9-B86-C1-D4
A13-B86-C1-D4
A24-B86-C1-D4
A69-B86-C1-D4
A67-B86-C1-D4
A39-B86-C1-D4
A65-B86-C1-D4
A66-B86-C1-D4
A2-B87-C1-D4
A3-B87-C1-D4
A9-B87-C1-D4
A13-B87-C1-D4
A24-B87-C1-D4
A69-B87-C1-D4
A67-B87-C1-D4
A39-B87-C1-D4
A65-B87-C1-D4
A66-B87-C1-D4
A2-B89-C1-D4
A3-B89-C1-D4
A9-B89-C1-D4
A13-B89-C1-D4
A24-B89-C1-D4
A69-B89-C1-D4
A67-B89-C1-D4
A39-B89-C1-D4
A65-B89-C1-D4
A66-B89-C1-D4
A2-B92-C1-D4
A3-B92-C1-D4
A9-B92-C1-D4
A13-B92-C1-D4
A24-B92-C1-D4
A69-B92-C1-D4
A67-B92-C1-D4
A39-B92-C1-D4
A65-B92-C1-D4
A66-B92-C1-D4
A2-B4-C2-D4
A3-B4-C2-D4
A9-B4-C2-D4
A13-B4-C2-D4
A24-B4-C2-D4
A69-B4-C2-D4
A67-B4-C2-D4
A39-B4-C2-D4
A65-B4-C2-D4
A66-B4-C2-D4
A2-B5-C2-D4
A3-B5-C2-D4
A9-B5-C2-D4

TABLE 6-continued

A13-B5-C2-D4
A24-B5-C2-D4
A69-B5-C2-D4
A67-B5-C2-D4
A39-B5-C2-D4
A65-B5-C2-D4
A66-B5-C2-D4
A2-B6-C2-D4
A3-B6-C2-D4
A9-B6-C2-D4
A13-B6-C2-D4
A24-B6-C2-D4
A69-B6-C2-D4
A67-B6-C2-D4
A39-B6-C2-D4
A65-B6-C2-D4
A66-B6-C2-D4
A2-B32-C2-D4
A3-B32-C2-D4
A9-B32-C2-D4
A13-B32-C2-D4
A24-B32-C2-D4
A69-B32-C2-D4
A67-B32-C2-D4
A39-B32-C2-D4
A65-B32-C2-D4
A66-B32-C2-D4
A2-B39-C2-D4
A3-B39-C2-D4
A9-B39-C2-D4
A13-B39-C2-D4
A24-B39-C2-D4
A69-B39-C2-D4
A67-B39-C2-D4
A39-B39-C2-D4
A65-B39-C2-D4
A66-B39-C2-D4
A2-B45-C2-D4
A3-B45-C2-D4
A9-B45-C2-D4
A13-B45-C2-D4
A24-B45-C2-D4
A69-B45-C2-D4
A67-B45-C2-D4
A39-B45-C2-D4
A65-B45-C2-D4
A66-B45-C2-D4
A2-B53-C2-D4
A3-B53-C2-D4
A9-B53-C2-D4
A13-B53-C2-D4
A24-B53-C2-D4
A69-B53-C2-D4
A67-B53-C2-D4
A39-B53-C2-D4
A65-B53-C2-D4
A66-B53-C2-D4
A2-B79-C2-D4
A3-B79-C2-D4
A9-B79-C2-D4
A13-B79-C2-D4
A24-B79-C2-D4
A69-B79-C2-D4
A67-B79-C2-D4
A39-B79-C2-D4
A65-B79-C2-D4
A66-B79-C2-D4
A2-B80-C2-D4
A3-B80-C2-D4
A9-B80-C2-D4
A13-B80-C2-D4
A24-B80-C2-D4
A69-B80-C2-D4
A67-B80-C2-D4
A39-B80-C2-D4
A65-B80-C2-D4
A66-B80-C2-D4
A2-B85-C2-D4
A3-B85-C2-D4

TABLE 6-continued

A9-B85-C2-D4
A13-B85-C2-D4
A24-B85-C2-D4
A69-B85-C2-D4
A67-B85-C2-D4
A39-B85-C2-D4
A65-B85-C2-D4
A66-B85-C2-D4
A2-B86-C2-D4
A3-B86-C2-D4
A9-B86-C2-D4
A13-B86-C2-D4
A24-B86-C2-D4
A69-B86-C2-D4
A67-B86-C2-D4
A39-B86-C2-D4
A65-B86-C2-D4
A66-B86-C2-D4
A2-B87-C2-D4
A3-B87-C2-D4
A9-B87-C2-D4
A13-B87-C2-D4
A24-B87-C2-D4
A69-B87-C2-D4
A67-B87-C2-D4
A39-B87-C2-D4
A65-B87-C2-D4
A66-B87-C2-D4
A2-B89-C2-D4
A3-B89-C2-D4
A9-B89-C2-D4
A13-B89-C2-D4
A24-B89-C2-D4
A69-B89-C2-D4
A67-B89-C2-D4
A39-B89-C2-D4
A65-B89-C2-D4
A66-B89-C2-D4
A2-B92-C2-D4
A3-B92-C2-D4
A9-B92-C2-D4
A13-B92-C2-D4
A24-B92-C2-D4
A69-B92-C2-D4
A67-B92-C2-D4
A39-B92-C2-D4
A65-B92-C2-D4
A66-B92-C2-D4
A2-B4-C3-D4
A3-B4-C3-D4
A9-B4-C3-D4
A13-B4-C3-D4
A24-B4-C3-D4
A69-B4-C3-D4
A67-B4-C3-D4
A39-B4-C3-D4
A65-B4-C3-D4
A66-B4-C3-D4
A2-B5-C3-D4
A3-B5-C3-D4
A9-B5-C3-D4
A13-B5-C3-D4
A24-B5-C3-D4
A69-B5-C3-D4
A67-B5-C3-D4
A39-B5-C3-D4
A65-B5-C3-D4
A66-B5-C3-D4
A2-B6-C3-D4
A3-B6-C3-D4
A9-B6-C3-D4
A13-B6-C3-D4
A24-B6-C3-D4
A69-B6-C3-D4
A67-B6-C3-D4
A39-B6-C3-D4
A65-B6-C3-D4
A66-B6-C3-D4
A2-B32-C3-D4
A3-B32-C3-D4
A9-B32-C3-D4
A13-B32-C3-D4
A24-B32-C3-D4
A69-B32-C3-D4
A67-B32-C3-D4
A39-B32-C3-D4
A65-B32-C3-D4
A66-B32-C3-D4
A2-B39-C3-D4
A3-B39-C3-D4
A9-B39-C3-D4
A13-B39-C3-D4
A24-B39-C3-D4
A69-B39-C3-D4
A67-B39-C3-D4
A39-B39-C3-D4
A65-B39-C3-D4
A66-B39-C3-D4
A2-B45-C3-D4
A3-B45-C3-D4
A9-B45-C3-D4
A13-B45-C3-D4
A24-B45-C3-D4
A69-B45-C3-D4
A67-B45-C3-D4
A39-B45-C3-D4
A65-B45-C3-D4
A66-B45-C3-D4
A2-B53-C3-D4
A3-B53-C3-D4
A9-B53-C3-D4
A13-B53-C3-D4
A24-B53-C3-D4
A69-B53-C3-D4
A67-B53-C3-D4
A39-B53-C3-D4
A65-B53-C3-D4
A66-B53-C3-D4
A2-B79-C3-D4
A3-B79-C3-D4
A9-B79-C3-D4
A13-B79-C3-D4
A24-B79-C3-D4
A69-B79-C3-D4
A67-B79-C3-D4
A39-B79-C3-D4
A65-B79-C3-D4
A66-B79-C3-D4
A2-B80-C3-D4
A3-B80-C3-D4
A9-B80-C3-D4
A13-B80-C3-D4
A24-B80-C3-D4
A69-B80-C3-D4
A67-B80-C3-D4
A39-B80-C3-D4
A65-B80-C3-D4
A66-B80-C3-D4
A2-B85-C3-D4
A3-B85-C3-D4
A9-B85-C3-D4
A13-B85-C3-D4
A24-B85-C3-D4
A69-B85-C3-D4
A67-B85-C3-D4
A39-B85-C3-D4
A65-B85-C3-D4
A66-B85-C3-D4
A2-B86-C3-D4
A3-B86-C3-D4
A9-B86-C3-D4
A13-B86-C3-D4
A24-B86-C3-D4
A69-B86-C3-D4
A67-B86-C3-D4
A39-B86-C3-D4
A65-B86-C3-D4
A66-B86-C3-D4

TABLE 6-continued

A2-B87-C3-D4
A3-B87-C3-D4
A9-B87-C3-D4
A13-B87-C3-D4
A24-B87-C3-D4
A69-B87-C3-D4
A67-B87-C3-D4
A39-B87-C3-D4
A65-B87-C3-D4
A66-B87-C3-D4
A2-B89-C3-D4
A3-B89-C3-D4
A9-B89-C3-D4
A13-B89-C3-D4
A24-B89-C3-D4
A69-B89-C3-D4
A67-B89-C3-D4
A39-B89-C3-D4
A65-B89-C3-D4
A66-B89-C3-D4
A2-B92-C3-D4
A3-B92-C3-D4
A9-B92-C3-D4
A13-B92-C3-D4
A24-B92-C3-D4
A69-B92-C3-D4
A67-B92-C3-D4
A39-B92-C3-D4
A65-B92-C3-D4
A66-B92-C3-D4
A2-B4-C4-D4
A3-B4-C4-D4
A9-B4-C4-D4
A13-B4-C4-D4
A24-B4-C4-D4
A69-B4-C4-D4
A67-B4-C4-D4
A39-B4-C4-D4
A65-B4-C4-D4
A66-B4-C4-D4
A2-B5-C4-D4
A3-B5-C4-D4
A9-B5-C4-D4
A13-B5-C4-D4
A24-B5-C4-D4
A69-B5-C4-D4
A67-B5-C4-D4
A39-B5-C4-D4
A65-B5-C4-D4
A66-B5-C4-D4
A2-B6-C4-D4
A3-B6-C4-D4
A9-B6-C4-D4
A13-B6-C4-D4
A24-B6-C4-D4
A69-B6-C4-D4
A67-B6-C4-D4
A39-B6-C4-D4
A65-B6-C4-D4
A66-B6-C4-D4
A2-B32-C4-D4
A3-B32-C4-D4
A9-B32-C4-D4
A13-B32-C4-D4
A24-B32-C4-D4
A69-B32-C4-D4
A67-B32-C4-D4
A39-B32-C4-D4
A65-B32-C4-D4
A66-B32-C4-D4
A2-B39-C4-D4
A3-B39-C4-D4
A9-B39-C4-D4
A13-B39-C4-D4
A24-B39-C4-D4
A69-B39-C4-D4
A67-B39-C4-D4
A39-B39-C4-D4
A65-B39-C4-D4

TABLE 6-continued

A66-B39-C4-D4
A2-B45-C4-D4
A3-B45-C4-D4
A9-B45-C4-D4
A13-B45-C4-D4
A24-B45-C4-D4
A69-B45-C4-D4
A67-B45-C4-D4
A39-B45-C4-D4
A65-B45-C4-D4
A66-B45-C4-D4
A2-B53-C4-D4
A3-B53-C4-D4
A9-B53-C4-D4
A13-B53-C4-D4
A24-B53-C4-D4
A69-B53-C4-D4
A67-B53-C4-D4
A39-B53-C4-D4
A65-B53-C4-D4
A66-B53-C4-D4
A2-B79-C4-D4
A3-B79-C4-D4
A9-B79-C4-D4
A13-B79-C4-D4
A24-B79-C4-D4
A69-B79-C4-D4
A67-B79-C4-D4
A39-B79-C4-D4
A65-B79-C4-D4
A66-B79-C4-D4
A2-B80-C4-D4
A3-B80-C4-D4
A9-B80-C4-D4
A13-B80-C4-D4
A24-B80-C4-D4
A69-B80-C4-D4
A67-B80-C4-D4
A39-B80-C4-D4
A65-B80-C4-D4
A66-B80-C4-D4
A2-B85-C4-D4
A3-B85-C4-D4
A9-B85-C4-D4
A13-B85-C4-D4
A24-B85-C4-D4
A69-B85-C4-D4
A67-B85-C4-D4
A39-B85-C4-D4
A65-B85-C4-D4
A66-B85-C4-D4
A2-B86-C4-D4
A3-B86-C4-D4
A9-B86-C4-D4
A13-B86-C4-D4
A24-B86-C4-D4
A69-B86-C4-D4
A67-B86-C4-D4
A39-B86-C4-D4
A65-B86-C4-D4
A66-B86-C4-D4
A2-B87-C4-D4
A3-B87-C4-D4
A9-B87-C4-D4
A13-B87-C4-D4
A24-B87-C4-D4
A69-B87-C4-D4
A67-B87-C4-D4
A39-B87-C4-D4
A65-B87-C4-D4
A66-B87-C4-D4
A2-B89-C4-D4
A3-B89-C4-D4
A9-B89-C4-D4
A13-B89-C4-D4
A24-B89-C4-D4
A69-B89-C4-D4
A67-B89-C4-D4
A39-B89-C4-D4

TABLE 6-continued

A65-B89-C4-D4
A66-B89-C4-D4
A2-B92-C4-D4
A3-B92-C4-D4
A9-B92-C4-D4
A13-B92-C4-D4
A24-B92-C4-D4
A69-B92-C4-D4
A67-B92-C4-D4
A39-B92-C4-D4
A65-B92-C4-D4
A66-B92-C4-D4
A2-B4-C5-D4
A3-B4-C5-D4
A9-B4-C5-D4
A13-B4-C5-D4
A24-B4-C5-D4
A69-B4-C5-D4
A67-B4-C5-D4
A39-B4-C5-D4
A65-B4-C5-D4
A66-B4-C5-D4
A2-B5-C5-D4
A3-B5-C5-D4
A9-B5-C5-D4
A13-B5-C5-D4
A24-B5-C5-D4
A69-B5-C5-D4
A67-B5-C5-D4
A39-B5-C5-D4
A65-B5-C5-D4
A66-B5-C5-D4
A2-B6-C5-D4
A3-B6-C5-D4
A9-B6-C5-D4
A13-B6-C5-D4
A24-B6-C5-D4
A69-B6-C5-D4
A67-B6-C5-D4
A39-B6-C5-D4
A65-B6-C5-D4
A66-B6-C5-D4
A2-B32-C5-D4
A3-B32-C5-D4
A9-B32-C5-D4
A13-B32-C5-D4
A24-B32-C5-D4
A69-B32-C5-D4
A67-B32-C5-D4
A39-B32-C5-D4
A65-B32-C5-D4
A66-B32-C5-D4
A2-B39-C5-D4
A3-B39-C5-D4
A9-B39-C5-D4
A13-B39-C5-D4
A24-B39-C5-D4
A69-B39-C5-D4
A67-B39-C5-D4
A39-B39-C5-D4
A65-B39-C5-D4
A66-B39-C5-D4
A2-B45-C5-D4
A3-B45-C5-D4
A9-B45-C5-D4
A13-B45-C5-D4
A24-B45-C5-D4
A69-B45-C5-D4
A67-B45-C5-D4
A39-B45-C5-D4
A65-B45-C5-D4
A66-B45-C5-D4
A2-B53-C5-D4
A3-B53-C5-D4
A9-B53-C5-D4
A13-B53-C5-D4
A24-B53-C5-D4
A69-B53-C5-D4
A67-B53-C5-D4
A39-B53-C5-D4
A65-B53-C5-D4
A66-B53-C5-D4
A2-B79-C5-D4
A3-B79-C5-D4
A9-B79-C5-D4
A13-B79-C5-D4
A24-B79-C5-D4
A69-B79-C5-D4
A67-B79-C5-D4
A39-B79-C5-D4
A65-B79-C5-D4
A66-B79-C5-D4
A2-B80-C5-D4
A3-B80-C5-D4
A9-B80-C5-D4
A13-B80-C5-D4
A24-B80-C5-D4
A69-B80-C5-D4
A67-B80-C5-D4
A39-B80-C5-D4
A65-B80-C5-D4
A66-B80-C5-D4
A2-B85-C5-D4
A3-B85-C5-D4
A9-B85-C5-D4
A13-B85-C5-D4
A24-B85-C5-D4
A69-B85-C5-D4
A67-B85-C5-D4
A39-B85-C5-D4
A65-B85-C5-D4
A66-B85-C5-D4
A2-B86-C5-D4
A3-B86-C5-D4
A9-B86-C5-D4
A13-B86-C5-D4
A24-B86-C5-D4
A69-B86-C5-D4
A67-B86-C5-D4
A39-B86-C5-D4
A65-B86-C5-D4
A66-B86-C5-D4
A2-B87-C5-D4
A3-B87-C5-D4
A9-B87-C5-D4
A13-B87-C5-D4
A24-B87-C5-D4
A69-B87-C5-D4
A67-B87-C5-D4
A39-B87-C5-D4
A65-B87-C5-D4
A66-B87-C5-D4
A2-B89-C5-D4
A3-B89-C5-D4
A9-B89-C5-D4
A13-B89-C5-D4
A24-B89-C5-D4
A69-B89-C5-D4
A67-B89-C5-D4
A39-B89-C5-D4
A65-B89-C5-D4
A66-B89-C5-D4
A2-B92-C5-D4
A3-B92-C5-D4
A9-B92-C5-D4
A13-B92-C5-D4
A24-B92-C5-D4
A69-B92-C5-D4
A67-B92-C5-D4
A39-B92-C5-D4
A65-B92-C5-D4
A66-B92-C5-D4
A2-B4-C6-D4
A3-B4-C6-D4
A9-B4-C6-D4
A13-B4-C6-D4
A24-B4-C6-D4
A69-B4-C6-D4

TABLE 6-continued

A67-B4-C6-D4
A39-B4-C6-D4
A65-B4-C6-D4
A66-B4-C6-D4
A2-B5-C6-D4
A3-B5-C6-D4
A9-B5-C6-D4
A13-B5-C6-D4
A24-B5-C6-D4
A69-B5-C6-D4
A67-B5-C6-D4
A39-B5-C6-D4
A65-B5-C6-D4
A66-B5-C6-D4
A2-B6-C6-D4
A3-B6-C6-D4
A9-B6-C6-D4
A13-B6-C6-D4
A24-B6-C6-D4
A69-B6-C6-D4
A67-B6-C6-D4
A39-B6-C6-D4
A65-B6-C6-D4
A66-B6-C6-D4
A2-B32-C6-D4
A3-B32-C6-D4
A9-B32-C6-D4
A13-B32-C6-D4
A24-B32-C6-D4
A69-B32-C6-D4
A67-B32-C6-D4
A39-B32-C6-D4
A65-B32-C6-D4
A66-B32-C6-D4
A2-B39-C6-D4
A3-B39-C6-D4
A9-B39-C6-D4
A13-B39-C6-D4
A24-B39-C6-D4
A69-B39-C6-D4
A67-B39-C6-D4
A39-B39-C6-D4
A65-B39-C6-D4
A66-B39-C6-D4
A2-B45-C6-D4
A3-B45-C6-D4
A9-B45-C6-D4
A13-B45-C6-D4
A24-B45-C6-D4
A69-B45-C6-D4
A67-B45-C6-D4
A39-B45-C6-D4
A65-B45-C6-D4
A66-B45-C6-D4
A2-B53-C6-D4
A3-B53-C6-D4
A9-B53-C6-D4
A13-B53-C6-D4
A24-B53-C6-D4
A69-B53-C6-D4
A67-B53-C6-D4
A39-B53-C6-D4
A65-B53-C6-D4
A66-B53-C6-D4
A2-B79-C6-D4
A3-B79-C6-D4
A9-B79-C6-D4
A13-B79-C6-D4
A24-B79-C6-D4
A69-B79-C6-D4
A67-B79-C6-D4
A39-B79-C6-D4
A65-B79-C6-D4
A66-B79-C6-D4
A2-B80-C6-D4
A3-B80-C6-D4
A9-B80-C6-D4
A13-B80-C6-D4
A24-B80-C6-D4

TABLE 6-continued

A69-B80-C6-D4
A67-B80-C6-D4
A39-B80-C6-D4
A65-B80-C6-D4
A66-B80-C6-D4
A2-B85-C6-D4
A3-B85-C6-D4
A9-B85-C6-D4
A13-B85-C6-D4
A24-B85-C6-D4
A69-B85-C6-D4
A67-B85-C6-D4
A39-B85-C6-D4
A65-B85-C6-D4
A66-B85-C6-D4
A2-B86-C6-D4
A3-B86-C6-D4
A9-B86-C6-D4
A13-B86-C6-D4
A24-B86-C6-D4
A69-B86-C6-D4
A67-B86-C6-D4
A39-B86-C6-D4
A65-B86-C6-D4
A66-B86-C6-D4
A2-B87-C6-D4
A3-B87-C6-D4
A9-B87-C6-D4
A13-B87-C6-D4
A24-B87-C6-D4
A69-B87-C6-D4
A67-B87-C6-D4
A39-B87-C6-D4
A65-B87-C6-D4
A66-B87-C6-D4
A2-B89-C6-D4
A3-B89-C6-D4
A9-B89-C6-D4
A13-B89-C6-D4
A24-B89-C6-D4
A69-B89-C6-D4
A67-B89-C6-D4
A39-B89-C6-D4
A65-B89-C6-D4
A66-B89-C6-D4
A2-B92-C6-D4
A3-B92-C6-D4
A9-B92-C6-D4
A13-B92-C6-D4
A24-B92-C6-D4
A69-B92-C6-D4
A67-B92-C6-D4
A39-B92-C6-D4
A65-B92-C6-D4
A66-B92-C6-D4
A2-B4-C7-D4
A3-B4-C7-D4
A9-B4-C7-D4
A13-B4-C7-D4
A24-B4-C7-D4
A69-B4-C7-D4
A67-B4-C7-D4
A39-B4-C7-D4
A65-B4-C7-D4
A66-B4-C7-D4
A2-B5-C7-D4
A3-B5-C7-D4
A9-B5-C7-D4
A13-B5-C7-D4
A24-B5-C7-D4
A69-B5-C7-D4
A67-B5-C7-D4
A39-B5-C7-D4
A65-B5-C7-D4
A66-B5-C7-D4
A2-B6-C7-D4
A3-B6-C7-D4
A9-B6-C7-D4
A13-B6-C7-D4

TABLE 6-continued

A24-B6-C7-D4
A69-B6-C7-D4
A67-B6-C7-D4
A39-B6-C7-D4
A65-B6-C7-D4
A66-B6-C7-D4
A2-B32-C7-D4
A3-B32-C7-D4
A9-B32-C7-D4
A13-B32-C7-D4
A24-B32-C7-D4
A69-B32-C7-D4
A67-B32-C7-D4
A39-B32-C7-D4
A65-B32-C7-D4
A66-B32-C7-D4
A2-B39-C7-D4
A3-B39-C7-D4
A9-B39-C7-D4
A13-B39-C7-D4
A24-B39-C7-D4
A69-B39-C7-D4
A67-B39-C7-D4
A39-B39-C7-D4
A65-B39-C7-D4
A66-B39-C7-D4
A2-B45-C7-D4
A3-B45-C7-D4
A9-B45-C7-D4
A13-B45-C7-D4
A24-B45-C7-D4
A69-B45-C7-D4
A67-B45-C7-D4
A39-B45-C7-D4
A65-B45-C7-D4
A66-B45-C7-D4
A2-B53-C7-D4
A3-B53-C7-D4
A9-B53-C7-D4
A13-B53-C7-D4
A24-B53-C7-D4
A69-B53-C7-D4
A67-B53-C7-D4
A39-B53-C7-D4
A65-B53-C7-D4
A66-B53-C7-D4
A2-B79-C7-D4
A3-B79-C7-D4
A9-B79-C7-D4
A13-B79-C7-D4
A24-B79-C7-D4
A69-B79-C7-D4
A67-B79-C7-D4
A39-B79-C7-D4
A65-B79-C7-D4
A66-B79-C7-D4
A2-B80-C7-D4
A3-B80-C7-D4
A9-B80-C7-D4
A13-B80-C7-D4
A24-B80-C7-D4
A69-B80-C7-D4
A67-B80-C7-D4
A39-B80-C7-D4
A65-B80-C7-D4
A66-B80-C7-D4
A2-B85-C7-D4
A3-B85-C7-D4
A9-B85-C7-D4
A13-B85-C7-D4
A24-B85-C7-D4
A69-B85-C7-D4
A67-B85-C7-D4
A39-B85-C7-D4
A65-B85-C7-D4
A66-B85-C7-D4
A2-B86-C7-D4
A3-B86-C7-D4
A9-B86-C7-D4

TABLE 6-continued

A13-B86-C7-D4
A24-B86-C7-D4
A69-B86-C7-D4
A67-B86-C7-D4
A39-B86-C7-D4
A65-B86-C7-D4
A66-B86-C7-D4
A2-B87-C7-D4
A3-B87-C7-D4
A9-B87-C7-D4
A13-B87-C7-D4
A24-B87-C7-D4
A69-B87-C7-D4
A67-B87-C7-D4
A39-B87-C7-D4
A65-B87-C7-D4
A66-B87-C7-D4
A2-B89-C7-D4
A3-B89-C7-D4
A9-B89-C7-D4
A13-B89-C7-D4
A24-B89-C7-D4
A69-B89-C7-D4
A67-B89-C7-D4
A39-B89-C7-D4
A65-B89-C7-D4
A66-B89-C7-D4
A2-B92-C7-D4
A3-B92-C7-D4
A9-B92-C7-D4
A13-B92-C7-D4
A24-B92-C7-D4
A69-B92-C7-D4
A67-B92-C7-D4
A39-B92-C7-D4
A65-B92-C7-D4
A66-B92-C7-D4
A2-B4-C8-D4
A3-B4-C8-D4
A9-B4-C8-D4
A13-B4-C8-D4
A24-B4-C8-D4
A69-B4-C8-D4
A67-B4-C8-D4
A39-B4-C8-D4
A65-B4-C8-D4
A66-B4-C8-D4
A2-B5-C8-D4
A3-B5-C8-D4
A9-B5-C8-D4
A13-B5-C8-D4
A24-B5-C8-D4
A69-B5-C8-D4
A67-B5-C8-D4
A39-B5-C8-D4
A65-B5-C8-D4
A66-B5-C8-D4
A2-B6-C8-D4
A3-B6-C8-D4
A9-B6-C8-D4
A13-B6-C8-D4
A24-B6-C8-D4
A69-B6-C8-D4
A67-B6-C8-D4
A39-B6-C8-D4
A65-B6-C8-D4
A66-B6-C8-D4
A2-B32-C8-D4
A3-B32-C8-D4
A9-B32-C8-D4
A13-B32-C8-D4
A24-B32-C8-D4
A69-B32-C8-D4
A67-B32-C8-D4
A39-B32-C8-D4
A65-B32-C8-D4
A66-B32-C8-D4
A2-B39-C8-D4
A3-B39-C8-D4

TABLE 6-continued

A9-B39-C8-D4
A13-B39-C8-D4
A24-B39-C8-D4
A69-B39-C8-D4
A67-B39-C8-D4
A39-B39-C8-D4
A65-B39-C8-D4
A66-B39-C8-D4
A2-B45-C8-D4
A3-B45-C8-D4
A9-B45-C8-D4
A13-B45-C8-D4
A24-B45-C8-D4
A69-B45-C8-D4
A67-B45-C8-D4
A39-B45-C8-D4
A65-B45-C8-D4
A66-B45-C8-D4
A2-B53-C8-D4
A3-B53-C8-D4
A9-B53-C8-D4
A13-B53-C8-D4
A24-B53-C8-D4
A69-B53-C8-D4
A67-B53-C8-D4
A39-B53-C8-D4
A65-B53-C8-D4
A66-B53-C8-D4
A2-B79-C8-D4
A3-B79-C8-D4
A9-B79-C8-D4
A13-B79-C8-D4
A24-B79-C8-D4
A69-B79-C8-D4
A67-B79-C8-D4
A39-B79-C8-D4
A65-B79-C8-D4
A66-B79-C8-D4
A2-B80-C8-D4
A3-B80-C8-D4
A9-B80-C8-D4
A13-B80-C8-D4
A24-B80-C8-D4
A69-B80-C8-D4
A67-B80-C8-D4
A39-B80-C8-D4
A65-B80-C8-D4
A66-B80-C8-D4
A2-B85-C8-D4
A3-B85-C8-D4
A9-B85-C8-D4
A13-B85-C8-D4
A24-B85-C8-D4
A69-B85-C8-D4
A67-B85-C8-D4
A39-B85-C8-D4
A65-B85-C8-D4
A66-B85-C8-D4
A2-B86-C8-D4
A3-B86-C8-D4
A9-B86-C8-D4
A13-B86-C8-D4
A24-B86-C8-D4
A69-B86-C8-D4
A67-B86-C8-D4
A39-B86-C8-D4
A65-B86-C8-D4
A66-B86-C8-D4
A2-B87-C8-D4
A3-B87-C8-D4
A9-B87-C8-D4
A13-B87-C8-D4
A24-B87-C8-D4
A69-B87-C8-D4
A67-B87-C8-D4
A39-B87-C8-D4
A65-B87-C8-D4
A66-B87-C8-D4
A2-B89-C8-D4

TABLE 6-continued

A3-B89-C8-D4
A9-B89-C8-D4
A13-B89-C8-D4
A24-B89-C8-D4
A69-B89-C8-D4
A67-B89-C8-D4
A39-B89-C8-D4
A65-B89-C8-D4
A66-B89-C8-D4
A2-B92-C8-D4
A3-B92-C8-D4
A9-B92-C8-D4
A13-B92-C8-D4
A24-B92-C8-D4
A69-B92-C8-D4
A67-B92-C8-D4
A39-B92-C8-D4
A65-B92-C8-D4
A66-B92-C8-D4
A2-B4-C9-D4
A3-B4-C9-D4
A9-B4-C9-D4
A13-B4-C9-D4
A24-B4-C9-D4
A69-B4-C9-D4
A67-B4-C9-D4
A39-B4-C9-D4
A65-B4-C9-D4
A66-B4-C9-D4
A2-B5-C9-D4
A3-B5-C9-D4
A9-B5-C9-D4
A13-B5-C9-D4
A24-B5-C9-D4
A69-B5-C9-D4
A67-B5-C9-D4
A39-B5-C9-D4
A65-B5-C9-D4
A66-B5-C9-D4
A2-B6-C9-D4
A3-B6-C9-D4
A9-B6-C9-D4
A13-B6-C9-D4
A24-B6-C9-D4
A69-B6-C9-D4
A67-B6-C9-D4
A39-B6-C9-D4
A65-B6-C9-D4
A66-B6-C9-D4
A2-B32-C9-D4
A3-B32-C9-D4
A9-B32-C9-D4
A13-B32-C9-D4
A24-B32-C9-D4
A69-B32-C9-D4
A67-B32-C9-D4
A39-B32-C9-D4
A65-B32-C9-D4
A66-B32-C9-D4
A2-B39-C9-D4
A3-B39-C9-D4
A9-B39-C9-D4
A13-B39-C9-D4
A24-B39-C9-D4
A69-B39-C9-D4
A67-B39-C9-D4
A39-B39-C9-D4
A65-B39-C9-D4
A66-B39-C9-D4
A2-B45-C9-D4
A3-B45-C9-D4
A9-B45-C9-D4
A13-B45-C9-D4
A24-B45-C9-D4
A69-B45-C9-D4
A67-B45-C9-D4
A39-B45-C9-D4
A65-B45-C9-D4
A66-B45-C9-D4

TABLE 6-continued

A2-B53-C9-D4
A3-B53-C9-D4
A9-B53-C9-D4
A13-B53-C9-D4
A24-B53-C9-D4
A69-B53-C9-D4
A67-B53-C9-D4
A39-B53-C9-D4
A65-B53-C9-D4
A66-B53-C9-D4
A2-B79-C9-D4
A3-B79-C9-D4
A9-B79-C9-D4
A13-B79-C9-D4
A24-B79-C9-D4
A69-B79-C9-D4
A67-B79-C9-D4
A39-B79-C9-D4
A65-B79-C9-D4
A66-B79-C9-D4
A2-B80-C9-D4
A3-B80-C9-D4
A9-B80-C9-D4
A13-B80-C9-D4
A24-B80-C9-D4
A69-B80-C9-D4
A67-B80-C9-D4
A39-B80-C9-D4
A65-B80-C9-D4
A66-B80-C9-D4
A2-B85-C9-D4
A3-B85-C9-D4
A9-B85-C9-D4
A13-B85-C9-D4
A24-B85-C9-D4
A69-B85-C9-D4
A67-B85-C9-D4
A39-B85-C9-D4
A65-B85-C9-D4
A66-B85-C9-D4
A2-B86-C9-D4
A3-B86-C9-D4
A9-B86-C9-D4
A13-B86-C9-D4
A24-B86-C9-D4
A69-B86-C9-D4
A67-B86-C9-D4
A39-B86-C9-D4
A65-B86-C9-D4
A66-B86-C9-D4
A2-B87-C9-D4
A3-B87-C9-D4
A9-B87-C9-D4
A13-B87-C9-D4
A24-B87-C9-D4
A69-B87-C9-D4
A67-B87-C9-D4
A39-B87-C9-D4
A65-B87-C9-D4
A66-B87-C9-D4
A2-B89-C9-D4
A3-B89-C9-D4
A9-B89-C9-D4
A13-B89-C9-D4
A24-B89-C9-D4
A69-B89-C9-D4
A67-B89-C9-D4
A39-B89-C9-D4
A65-B89-C9-D4
A66-B89-C9-D4
A2-B92-C9-D4
A3-B92-C9-D4
A9-B92-C9-D4
A13-B92-C9-D4
A24-B92-C9-D4
A69-B92-C9-D4
A67-B92-C9-D4
A39-B92-C9-D4
A65-B92-C9-D4

TABLE 6-continued

A66-B92-C9-D4
A2-B4-C10-D4
A3-B4-C10-D4
A9-B4-C10-D4
A13-B4-C10-D4
A24-B4-C10-D4
A69-B4-C10-D4
A67-B4-C10-D4
A39-B4-C10-D4
A65-B4-C10-D4
A66-B4-C10-D4
A2-B5-C10-D4
A3-B5-C10-D4
A9-B5-C10-D4
A13-B5-C10-D4
A24-B5-C10-D4
A69-B5-C10-D4
A67-B5-C10-D4
A39-B5-C10-D4
A65-B5-C10-D4
A66-B5-C10-D4
A2-B6-C10-D4
A3-B6-C10-D4
A9-B6-C10-D4
A13-B6-C10-D4
A24-B6-C10-D4
A69-B6-C10-D4
A67-B6-C10-D4
A39-B6-C10-D4
A65-B6-C10-D4
A66-B6-C10-D4
A2-B32-C10-D4
A3-B32-C10-D4
A9-B32-C10-D4
A13-B32-C10-D4
A24-B32-C10-D4
A69-B32-C10-D4
A67-B32-C10-D4
A39-B32-C10-D4
A65-B32-C10-D4
A66-B32-C10-D4
A2-B39-C10-D4
A3-B39-C10-D4
A9-B39-C10-D4
A13-B39-C10-D4
A24-B39-C10-D4
A69-B39-C10-D4
A67-B39-C10-D4
A39-B39-C10-D4
A65-B39-C10-D4
A66-B39-C10-D4
A2-B45-C10-D4
A3-B45-C10-D4
A9-B45-C10-D4
A13-B45-C10-D4
A24-B45-C10-D4
A69-B45-C10-D4
A67-B45-C10-D4
A39-B45-C10-D4
A65-B45-C10-D4
A66-B45-C10-D4
A2-B53-C10-D4
A3-B53-C10-D4
A9-B53-C10-D4
A13-B53-C10-D4
A24-B53-C10-D4
A69-B53-C10-D4
A67-B53-C10-D4
A39-B53-C10-D4
A65-B53-C10-D4
A66-B53-C10-D4
A2-B79-C10-D4
A3-B79-C10-D4
A9-B79-C10-D4
A13-B79-C10-D4
A24-B79-C10-D4
A69-B79-C10-D4
A67-B79-C10-D4
A39-B79-C10-D4

TABLE 6-continued

A65-B79-C10-D4
A66-B79-C10-D4
A2-B80-C10-D4
A3-B80-C10-D4
A9-B80-C10-D4
A13-B80-C10-D4
A24-B80-C10-D4
A69-B80-C10-D4
A67-B80-C10-D4
A39-B80-C10-D4
A65-B80-C10-D4
A66-B80-C10-D4
A2-B85-C10-D4
A3-B85-C10-D4
A9-B85-C10-D4
A13-B85-C10-D4
A24-B85-C10-D4
A69-B85-C10-D4
A67-B85-C10-D4
A39-B85-C10-D4
A65-B85-C10-D4
A66-B85-C10-D4
A2-B86-C10-D4
A3-B86-C10-D4
A9-B86-C10-D4
A13-B86-C10-D4
A24-B86-C10-D4
A69-B86-C10-D4
A67-B86-C10-D4
A39-B86-C10-D4
A65-B86-C10-D4
A66-B86-C10-D4
A2-B87-C10-D4
A3-B87-C10-D4
A9-B87-C10-D4
A13-B87-C10-D4
A24-B87-C10-D4
A69-B87-C10-D4
A67-B87-C10-D4
A39-B87-C10-D4
A65-B87-C10-D4
A66-B87-C10-D4
A2-B89-C10-D4
A3-B89-C10-D4
A9-B89-C10-D4
A13-B89-C10-D4
A24-B89-C10-D4
A69-B89-C10-D4
A67-B89-C10-D4
A39-B89-C10-D4
A65-B89-C10-D4
A66-B89-C10-D4
A2-B92-C10-D4
A3-B92-C10-D4
A9-B92-C10-D4
A13-B92-C10-D4
A24-B92-C10-D4
A69-B92-C10-D4
A67-B92-C10-D4
A39-B92-C10-D4
A65-B92-C10-D4
A66-B92-C10-D4
A2-B4-C11-D4
A3-B4-C11-D4
A9-B4-C11-D4
A13-B4-C11-D4
A24-B4-C11-D4
A69-B4-C11-D4
A67-B4-C11-D4
A39-B4-C11-D4
A65-B4-C11-D4
A66-B4-C11-D4
A2-B5-C11-D4
A3-B5-C11-D4
A9-B5-C11-D4
A13-B5-C11-D4
A24-B5-C11-D4
A69-B5-C11-D4
A67-B5-C11-D4

TABLE 6-continued

A39-B5-C11-D4
A65-B5-C11-D4
A66-B5-C11-D4
A2-B6-C11-D4
A3-B6-C11-D4
A9-B6-C11-D4
A13-B6-C11-D4
A24-B6-C11-D4
A69-B6-C11-D4
A67-B6-C11-D4
A39-B6-C11-D4
A65-B6-C11-D4
A66-B6-C11-D4
A2-B32-C11-D4
A3-B32-C11-D4
A9-B32-C11-D4
A13-B32-C11-D4
A24-B32-C11-D4
A69-B32-C11-D4
A67-B32-C11-D4
A39-B32-C11-D4
A65-B32-C11-D4
A66-B32-C11-D4
A2-B39-C11-D4
A3-B39-C11-D4
A9-B39-C11-D4
A13-B39-C11-D4
A24-B39-C11-D4
A69-B39-C11-D4
A67-B39-C11-D4
A39-B39-C11-D4
A65-B39-C11-D4
A66-B39-C11-D4
A2-B45-C11-D4
A3-B45-C11-D4
A9-B45-C11-D4
A13-B45-C11-D4
A24-B45-C11-D4
A69-B45-C11-D4
A67-B45-C11-D4
A39-B45-C11-D4
A65-B45-C11-D4
A66-B45-C11-D4
A2-B53-C11-D4
A3-B53-C11-D4
A9-B53-C11-D4
A13-B53-C11-D4
A24-B53-C11-D4
A69-B53-C11-D4
A67-B53-C11-D4
A39-B53-C11-D4
A65-B53-C11-D4
A66-B53-C11-D4
A2-B79-C11-D4
A3-B79-C11-D4
A9-B79-C11-D4
A13-B79-C11-D4
A24-B79-C11-D4
A69-B79-C11-D4
A67-B79-C11-D4
A39-B79-C11-D4
A65-B79-C11-D4
A66-B79-C11-D4
A2-B80-C11-D4
A3-B80-C11-D4
A9-B80-C11-D4
A13-B80-C11-D4
A24-B80-C11-D4
A69-B80-C11-D4
A67-B80-C11-D4
A39-B80-C11-D4
A65-B80-C11-D4
A66-B80-C11-D4
A2-B85-C11-D4
A3-B85-C11-D4
A9-B85-C11-D4
A13-B85-C11-D4
A24-B85-C11-D4
A69-B85-C11-D4

TABLE 6-continued

A67-B85-C11-D4
A39-B85-C11-D4
A65-B85-C11-D4
A66-B85-C11-D4
A2-B86-C11-D4
A3-B86-C11-D4
A9-B86-C11-D4
A13-B86-C11-D4
A24-B86-C11-D4
A69-B86-C11-D4
A67-B86-C11-D4
A39-B86-C11-D4
A65-B86-C11-D4
A66-B86-C11-D4
A2-B87-C11-D4
A3-B87-C11-D4
A9-B87-C11-D4
A13-B87-C11-D4
A24-B87-C11-D4
A69-B87-C11-D4
A67-B87-C11-D4
A39-B87-C11-D4
A65-B87-C11-D4
A66-B87-C11-D4
A2-B89-C11-D4
A3-B89-C11-D4
A9-B89-C11-D4
A13-B89-C11-D4
A24-B89-C11-D4
A69-B89-C11-D4
A67-B89-C11-D4
A39-B89-C11-D4
A65-B89-C11-D4
A66-B89-C11-D4
A2-B92-C11-D4
A3-B92-C11-D4
A9-B92-C11-D4
A13-B92-C11-D4
A24-B92-C11-D4
A69-B92-C11-D4
A67-B92-C11-D4
A39-B92-C11-D4
A65-B92-C11-D4
A66-B92-C11-D4
A2-B4-C12-D4
A3-B4-C12-D4
A9-B4-C12-D4
A13-B4-C12-D4
A24-B4-C12-D4
A69-B4-C12-D4
A67-B4-C12-D4
A39-B4-C12-D4
A65-B4-C12-D4
A66-B4-C12-D4
A2-B5-C12-D4
A3-B5-C12-D4
A9-B5-C12-D4
A13-B5-C12-D4
A24-B5-C12-D4
A69-B5-C12-D4
A67-B5-C12-D4
A39-B5-C12-D4
A65-B5-C12-D4
A66-B5-C12-D4
A2-B6-C12-D4
A3-B6-C12-D4
A9-B6-C12-D4
A13-B6-C12-D4
A24-B6-C12-D4
A69-B6-C12-D4
A67-B6-C12-D4
A39-B6-C12-D4
A65-B6-C12-D4
A66-B6-C12-D4
A2-B32-C12-D4
A3-B32-C12-D4
A9-B32-C12-D4
A13-B32-C12-D4
A24-B32-C12-D4

TABLE 6-continued

A69-B32-C12-D4
A67-B32-C12-D4
A39-B32-C12-D4
A65-B32-C12-D4
A66-B32-C12-D4
A2-B39-C12-D4
A3-B39-C12-D4
A9-B39-C12-D4
A13-B39-C12-D4
A24-B39-C12-D4
A69-B39-C12-D4
A67-B39-C12-D4
A39-B39-C12-D4
A65-B39-C12-D4
A66-B39-C12-D4
A2-B45-C12-D4
A3-B45-C12-D4
A9-B45-C12-D4
A13-B45-C12-D4
A24-B45-C12-D4
A69-B45-C12-D4
A67-B45-C12-D4
A39-B45-C12-D4
A65-B45-C12-D4
A66-B45-C12-D4
A2-B53-C12-D4
A3-B53-C12-D4
A9-B53-C12-D4
A13-B53-C12-D4
A24-B53-C12-D4
A69-B53-C12-D4
A67-B53-C12-D4
A39-B53-C12-D4
A65-B53-C12-D4
A66-B53-C12-D4
A2-B79-C12-D4
A3-B79-C12-D4
A9-B79-C12-D4
A13-B79-C12-D4
A24-B79-C12-D4
A69-B79-C12-D4
A67-B79-C12-D4
A39-B79-C12-D4
A65-B79-C12-D4
A66-B79-C12-D4
A2-B80-C12-D4
A3-B80-C12-D4
A9-B80-C12-D4
A13-B80-C12-D4
A24-B80-C12-D4
A69-B80-C12-D4
A67-B80-C12-D4
A39-B80-C12-D4
A65-B80-C12-D4
A66-B80-C12-D4
A2-B85-C12-D4
A37-B85-C12-D4
A9-B85-C12-D4
A13-B85-C12-D4
A24-B85-C12-D4
A69-B85-C12-D4
A67-B85-C12-D4
A39-B85-C12-D4
A65-B85-C12-D4
A66-B85-C12-D4
A2-B86-C12-D4
A3-B86-C12-D4
A9-B86-C12-D4
A13-B86-C12-D4
A24-B86-C12-D4
A69-B86-C12-D4
A67-B86-C12-D4
A39-B86-C12-D4
A65-B86-C12-D4
A66-B86-C12-D4
A2-B87-C12-D4
A3-B87-C12-D4
A9-B87-C12-D4
A13-B87-C12-D4

TABLE 6-continued

A24-B87-C12-D4
A69-B87-C12-D4
A67-B87-C12-D4
A39-B87-C12-D4
A65-B87-C12-D4
A66-B87-C12-D4
A2-B89-C12-D4
A3-B89-C12-D4
A9-B89-C12-D4
A13-B89-C12-D4
A24-B89-C12-D4
A69-B89-C12-D4
A67-B89-C12-D4
A39-B89-C12-D4
A65-B89-C12-D4
A66-B89-C12-D4
A2-B92-C12-D4
A3-B92-C12-D4
A9-B92-C12-D4
A13-B92-C12-D4
A24-B92-C12-D4
A69-B92-C12-D4
A67-B92-C12-D4
A39-B92-C12-D4
A65-B92-C12-D4
A66-B92-C12-D4
A2-B4-C13-D4
A3-B4-C13-D4
A9-B4-C13-D4
A13-B4-C13-D4
A24-B4-C13-D4
A69-B4-C13-D4
A67-B4-C13-D4
A39-B4-C13-D4
A65-B4-C13-D4
A66-B4-C13-D4
A2-B5-C13-D4
A3-B5-C13-D4
A9-B5-C13-D4
A13-B5-C13-D4
A24-B5-C13-D4
A69-B5-C13-D4
A67-B5-C13-D4
A39-B5-C13-D4
A65-B5-C13-D4
A66-B5-C13-D4
A2-B6-C13-D4
A3-B6-C13-D4
A9-B6-C13-D4
A13-B6-C13-D4
A24-B6-C13-D4
A69-B6-C13-D4
A67-B6-C13-D4
A39-B6-C13-D4
A65-B6-C13-D4
A66-B6-C13-D4
A2-B32-C13-D4
A3-B32-C13-D4
A9-B32-C13-D4
A13-B32-C13-D4
A24-B32-C13-D4
A69-B32-C13-D4
A67-B32-C13-D4
A39-B32-C13-D4
A65-B32-C13-D4
A66-B32-C13-D4
A2-B39-C13-D4
A3-B39-C13-D4
A9-B39-C13-D4
A13-B39-C13-D4
A24-B39-C13-D4
A69-B39-C13-D4
A67-B39-C13-D4
A39-B39-C13-D4
A65-B39-C13-D4
A66-B39-C13-D4
A2-B45-C13-D4
A3-B45-C13-D4
A9-B45-C13-D4
A13-B45-C13-D4
A24-B45-C13-D4
A69-B45-C13-D4
A67-B45-C13-D4
A39-B45-C13-D4
A65-B45-C13-D4
A66-B45-C13-D4
A2-B53-C13-D4
A3-B53-C13-D4
A9-B53-C13-D4
A13-B53-C13-D4
A24-B53-C13-D4
A69-B53-C13-D4
A67-B53-C13-D4
A39-B53-C13-D4
A65-B53-C13-D4
A66-B53-C13-D4
A2-B79-C13-D4
A3-B79-C13-D4
A9-B79-C13-D4
A13-B79-C13-D4
A24-B79-C13-D4
A69-B79-C13-D4
A67-B79-C13-D4
A39-B79-C13-D4
A65-B79-C13-D4
A66-B79-C13-D4
A2-B80-C13-D4
A3-B80-C13-D4
A9-B80-C13-D4
A13-B80-C13-D4
A24-B80-C13-D4
A69-B80-C13-D4
A67-B80-C13-D4
A39-B80-C13-D4
A65-B80-C13-D4
A66-B80-C13-D4
A2-B85-C13-D4
A3-B85-C13-D4
A9-B85-C13-D4
A13-B85-C13-D4
A24-B85-C13-D4
A69-B85-C13-D4
A67-B85-C13-D4
A39-B85-C13-D4
A65-B85-C13-D4
A66-B85-C13-D4
A2-B86-C13-D4
A3-B86-C13-D4
A9-B86-C13-D4
A13-B86-C13-D4
A24-B86-C13-D4
A69-B86-C13-D4
A67-B86-C13-D4
A39-B86-C13-D4
A65-B86-C13-D4
A66-B86-C13-D4
A2-B87-C13-D4
A3-B87-C13-D4
A9-B87-C13-D4
A13-B87-C13-D4
A24-B87-C13-D4
A69-B87-C13-D4
A67-B87-C13-D4
A39-B87-C13-D4
A65-B87-C13-D4
A66-B87-C13-D4
A2-B89-C13-D4
A3-B89-C13-D4
A9-B89-C13-D4
A13-B89-C13-D4
A24-B89-C13-D4
A69-B89-C13-D4
A67-B89-C13-D4
A39-B89-C13-D4
A65-B89-C13-D4
A66-B89-C13-D4
A2-B92-C13-D4
A3-B92-C13-D4

TABLE 6-continued

A9-B92-C13-D4
A13-B92-C13-D4
A24-B92-C13-D4
A69-B92-C13-D4
A67-B92-C13-D4
A39-B92-C13-D4
A65-B92-C13-D4
A66-B92-C13-D4
A2-B4-C1-D5
A3-B4-C1-D5
A9-B4-C1-D5
A13-B4-C1-D5
A24-B4-C1-D5
A69-B4-C1-D5
A67-B4-C1-D5
A39-B4-C1-D5
A65-B4-C1-D5
A66-B4-C1-D5
A2-B5-C1-D5
A3-B5-C1-D5
A9-B5-C1-D5
A13-B5-C1-D5
A24-B5-C1-D5
A69-B5-C1-D5
A67-B5-C1-D5
A39-B5-C1-D5
A65-B5-C1-D5
A66-B5-C1-D5
A2-B6-C1-D5
A3-B6-C1-D5
A9-B6-C1-D5
A13-B6-C1-D5
A24-B6-C1-D5
A69-B6-C1-D5
A67-B6-C1-D5
A39-B6-C1-D5
A65-B6-C1-D5
A66-B6-C1-D5
A2-B32-C1-D5
A3-B32-C1-D5
A9-B32-C1-D5
A13-B32-C1-D5
A24-B32-C1-D5
A69-B32-C1-D5
A67-B32-C1-D5
A39-B32-C1-D5
A65-B32-C1-D5
A66-B32-C1-D5
A2-B39-C1-D5
A3-B39-C1-D5
A9-B39-C1-D5
A13-B39-C1-D5
A24-B39-C1-D5
A69-B39-C1-D5
A67-B39-C1-D5
A39-B39-C1-D5
A65-B39-C1-D5
A66-B39-C1-D5
A2-B45-C1-D5
A3-B45-C1-D5
A9-B45-C1-D5
A13-B45-C1-D5
A24-B45-C1-D5
A69-B45-C1-D5
A67-B45-C1-D5
A39-B45-C1-D5
A65-B45-C1-D5
A66-B45-C1-D5
A2-B53-C1-D5
A3-B53-C1-D5
A9-B53-C1-D5
A13-B53-C1-D5
A24-B53-C1-D5
A69-B53-C1-D5
A67-B53-C1-D5
A39-B53-C1-D5
A65-B53-C1-D5
A66-B53-C1-D5
A2-B79-C1-D5

TABLE 6-continued

A3-B79-C1-D5
A9-B79-C1-D5
A13-B79-C1-D5
A24-B79-C1-D5
A69-B79-C1-D5
A67-B79-C1-D5
A39-B79-C1-D5
A65-B79-C1-D5
A66-B79-C1-D5
A2-B80-C1-D5
A3-B80-C1-D5
A9-B80-C1-D5
A13-B80-C1-D5
A24-B80-C1-D5
A69-B80-C1-D5
A67-B80-C1-D5
A39-B80-C1-D5
A65-B80-C1-D5
A66-B80-C1-D5
A2-B85-C1-D5
A3-B85-C1-D5
A9-B85-C1-D5
A13-B85-C1-D5
A24-B85-C1-D5
A69-B85-C1-D5
A67-B85-C1-D5
A39-B85-C1-D5
A65-B85-C1-D5
A66-B85-C1-D5
A2-B86-C1-D5
A3-B86-C1-D5
A9-B86-C1-D5
A13-B86-C1-D5
A24-B86-C1-D5
A69-B86-C1-D5
A67-B86-C1-D5
A39-B86-C1-D5
A65-B86-C1-D5
A66-B86-C1-D5
A2-B87-C1-D5
A3-B87-C1-D5
A9-B87-C1-D5
A13-B87-C1-D5
A24-B87-C1-D5
A69-B87-C1-D5
A67-B87-C1-D5
A39-B87-C1-D5
A65-B87-C1-D5
A66-B87-C1-D5
A2-B89-C1-D5
A3-B89-C1-D5
A9-B89-C1-D5
A13-B89-C1-D5
A24-B89-C1-D5
A69-B89-C1-D5
A67-B89-C1-D5
A39-B89-C1-D5
A65-B89-C1-D5
A66-B89-C1-D5
A2-B92-C1-D5
A3-B92-C1-D5
A9-B92-C1-D5
A13-B92-C1-D5
A24-B92-C1-D5
A69-B92-C1-D5
A67-B92-C1-D5
A39-B92-C1-D5
A65-B92-C1-D5
A66-B92-C1-D5
A2-B4-C2-D5
A3-B4-C2-D5
A9-B4-C2-D5
A13-B4-C2-D5
A24-B4-C2-D5
A69-B4-C2-D5
A67-B4-C2-D5
A39-B4-C2-D5
A65-B4-C2-D5
A66-B4-C2-D5

TABLE 6-continued

A2-B5-C2-D5
A3-B5-C2-D5
A9-B5-C2-D5
A13-B5-C2-D5
A24-B5-C2-D5
A69-B5-C2-D5
A67-B5-C2-D5
A39-B5-C2-D5
A65-B5-C2-D5
A66-B5-C2-D5
A2-B6-C2-D5
A3-B6-C2-D5
A9-B6-C2-D5
A13-B6-C2-D5
A24-B6-C2-D5
A69-B6-C2-D5
A67-B6-C2-D5
A39-B6-C2-D5
A65-B6-C2-D5
A66-B6-C2-D5
A2-B32-C2-D5
A3-B32-C2-D5
A9-B32-C2-D5
A13-B32-C2-D5
A24-B32-C2-D5
A69-B32-C2-D5
A67-B32-C2-D5
A39-B32-C2-D5
A65-B32-C2-D5
A66-B32-C2-D5
A2-B39-C2-D5
A3-B39-C2-D5
A9-B39-C2-D5
A13-B39-C2-D5
A24-B39-C2-D5
A69-B39-C2-D5
A67-B39-C2-D5
A39-B39-C2-D5
A65-B39-C2-D5
A66-B39-C2-D5
A2-B45-C2-D5
A3-B45-C2-D5
A9-B45-C2-D5
A13-B45-C2-D5
A24-B45-C2-D5
A69-B45-C2-D5
A67-B45-C2-D5
A39-B45-C2-D5
A65-B45-C2-D5
A66-B45-C2-D5
A2-B53-C2-D5
A3-B53-C2-D5
A9-B53-C2-D5
A13-B53-C2-D5
A24-B53-C2-D5
A69-B53-C2-D5
A67-B53-C2-D5
A39-B53-C2-D5
A65-B53-C2-D5
A66-B53-C2-D5
A2-B79-C2-D5
A3-B79-C2-D5
A9-B79-C2-D5
A13-B79-C2-D5
A24-B79-C2-D5
A69-B79-C2-D5
A67-B79-C2-D5
A39-B79-C2-D5
A65-B79-C2-D5
A66-B79-C2-D5
A2-B80-C2-D5
A3-B80-C2-D5
A9-B80-C2-D5
A13-B80-C2-D5
A24-B80-C2-D5
A69-B80-C2-D5
A67-B80-C2-D5
A39-B80-C2-D5
A65-B80-C2-D5

TABLE 6-continued

A66-B80-C2-D5
A2-B85-C2-D5
A3-B85-C2-D5
A9-B85-C2-D5
A13-B85-C2-D5
A24-B85-C2-D5
A69-B85-C2-D5
A67-B85-C2-D5
A39-B85-C2-D5
A65-B85-C2-D5
A66-B85-C2-D5
A2-B86-C2-D5
A3-B86-C2-D5
A9-B86-C2-D5
A13-B86-C2-D5
A24-B86-C2-D5
A69-B86-C2-D5
A67-B86-C2-D5
A39-B86-C2-D5
A65-B86-C2-D5
A66-B86-C2-D5
A2-B87-C2-D5
A3-B87-C2-D5
A9-B87-C2-D5
A13-B87-C2-D5
A24-B87-C2-D5
A69-B87-C2-D5
A67-B87-C2-D5
A39-B87-C2-D5
A65-B87-C2-D5
A66-B87-C2-D5
A2-B89-C2-D5
A3-B89-C2-D5
A9-B89-C2-D5
A13-B89-C2-D5
A24-B89-C2-D5
A69-B89-C2-D5
A67-B89-C2-D5
A39-B89-C2-D5
A65-B89-C2-D5
A66-B89-C2-D5
A2-B92-C2-D5
A3-B92-C2-D5
A9-B92-C2-D5
A13-B92-C2-D5
A24-B92-C2-D5
A69-B92-C2-D5
A67-B92-C2-D5
A39-B92-C2-D5
A65-B92-C2-D5
A66-B92-C2-D5
A2-B4-C3-D5
A3-B4-C3-D5
A9-B4-C3-D5
A13-B4-C3-D5
A24-B4-C3-D5
A69-B4-C3-D5
A67-B4-C3-D5
A39-B4-C3-D5
A65-B4-C3-D5
A66-B4-C3-D5
A2-B5-C3-D5
A3-B5-C3-D5
A9-B5-C3-D5
A13-B5-C3-D5
A24-B5-C3-D5
A69-B5-C3-D5
A67-B5-C3-D5
A39-B5-C3-D5
A65-B5-C3-D5
A66-B5-C3-D5
A2-B6-C3-D5
A3-B6-C3-D5
A9-B6-C3-D5
A13-B6-C3-D5
A24-B6-C3-D5
A69-B6-C3-D5
A67-B6-C3-D5
A39-B6-C3-D5

TABLE 6-continued

A65-B6-C3-D5
A66-B6-C3-D5
A2-B32-C3-D5
A3-B32-C3-D5
A9-B32-C3-D5
A13-B32-C3-D5
A24-B32-C3-D5
A69-B32-C3-D5
A67-B32-C3-D5
A39-B32-C3-D5
A65-B32-C3-D5
A66-B32-C3-D5
A2-B39-C3-D5
A3-B39-C3-D5
A9-B39-C3-D5
A13-B39-C3-D5
A24-B39-C3-D5
A69-B39-C3-D5
A67-B39-C3-D5
A39-B39-C3-D5
A65-B39-C3-D5
A66-B39-C3-D5
A2-B45-C3-D5
A3-B45-C3-D5
A9-B45-C3-D5
A13-B45-C3-D5
A24-B45-C3-D5
A69-B45-C3-D5
A67-B45-C3-D5
A39-B45-C3-D5
A65-B45-C3-D5
A66-B45-C3-D5
A2-B53-C3-D5
A3-B53-C3-D5
A9-B53-C3-D5
A13-B53-C3-D5
A24-B53-C3-D5
A69-B53-C3-D5
A67-B53-C3-D5
A39-B53-C3-D5
A65-B53-C3-D5
A66-B53-C3-D5
A2-B79-C3-D5
A3-B79-C3-D5
A9-B79-C3-D5
A13-B79-C3-D5
A24-B79-C3-D5
A69-B79-C3-D5
A67-B79-C3-D5
A39-B79-C3-D5
A65-B79-C3-D5
A66-B79-C3-D5
A2-B80-C3-D5
A3-B80-C3-D5
A9-B80-C3-D5
A13-B80-C3-D5
A24-B80-C3-D5
A69-B80-C3-D5
A67-B80-C3-D5
A39-B80-C3-D5
A65-B80-C3-D5
A66-B80-C3-D5
A2-B85-C3-D5
A3-B85-C3-D5
A9-B85-C3-D5
A13-B85-C3-D5
A24-B85-C3-D5
A69-B85-C3-D5
A67-B85-C3-D5
A39-B85-C3-D5
A65-B85-C3-D5
A66-B85-C3-D5
A2-B86-C3-D5
A3-B86-C3-D5
A9-B86-C3-D5
A13-B86-C3-D5
A24-B86-C3-D5
A69-B86-C3-D5
A67-B86-C3-D5
A39-B86-C3-D5
A65-B86-C3-D5
A66-B86-C3-D5
A2-B87-C3-D5
A3-B87-C3-D5
A9-B87-C3-D5
A13-B87-C3-D5
A24-B87-C3-D5
A69-B87-C3-D5
A67-B87-C3-D5
A39-B87-C3-D5
A65-B87-C3-D5
A66-B87-C3-D5
A2-B89-C3-D5
A3-B89-C3-D5
A9-B89-C3-D5
A13-B89-C3-D5
A24-B89-C3-D5
A69-B89-C3-D5
A67-B89-C3-D5
A39-B89-C3-D5
A65-B89-C3-D5
A66-B89-C3-D5
A2-B92-C3-D5
A3-B92-C3-D5
A9-B92-C3-D5
A13-B92-C3-D5
A24-B92-C3-D5
A69-B92-C3-D5
A67-B92-C3-D5
A39-B92-C3-D5
A65-B92-C3-D5
A66-B92-C3-D5
A2-B4-C4-D5
A3-B4-C4-D5
A9-B4-C4-D5
A13-B4-C4-D5
A24-B4-C4-D5
A69-B4-C4-D5
A67-B4-C4-D5
A39-B4-C4-D5
A65-B4-C4-D5
A66-B4-C4-D5
A2-B5-C4-D5
A3-B5-C4-D5
A9-B5-C4-D5
A13-B5-C4-D5
A24-B5-C4-D5
A69-B5-C4-D5
A67-B5-C4-D5
A39-B5-C4-D5
A65-B5-C4-D5
A66-B5-C4-D5
A2-B6-C4-D5
A3-B6-C4-D5
A9-B6-C4-D5
A13-B6-C4-D5
A24-B6-C4-D5
A69-B6-C4-D5
A67-B6-C4-D5
A39-B6-C4-D5
A65-B6-C4-D5
A66-B6-C4-D5
A2-B32-C4-D5
A3-B32-C4-D5
A9-B32-C4-D5
A13-B32-C4-D5
A24-B32-C4-D5
A69-B32-C4-D5
A67-B32-C4-D5
A39-B32-C4-D5
A65-B32-C4-D5
A66-B32-C4-D5
A2-B39-C4-D5
A3-B39-C4-D5
A9-B39-C4-D5
A13-B39-C4-D5
A24-B39-C4-D5
A69-B39-C4-D5

TABLE 6-continued

A67-B39-C4-D5
A39-B39-C4-D5
A65-B39-C4-D5
A66-B39-C4-D5
A2-B45-C4-D5
A3-B45-C4-D5
A9-B45-C4-D5
A13-B45-C4-D5
A24-B45-C4-D5
A69-B45-C4-D5
A67-B45-C4-D5
A39-B45-C4-D5
A65-B45-C4-D5
A66-B45-C4-D5
A2-B53-C4-D5
A3-B53-C4-D5
A9-B53-C4-D5
A13-B53-C4-D5
A24-B53-C4-D5
A69-B53-C4-D5
A67-B53-C4-D5
A39-B53-C4-D5
A65-B53-C4-D5
A66-B53-C4-D5
A2-B79-C4-D5
A3-B79-C4-D5
A9-B79-C4-D5
A13-B79-C4-D5
A24-B79-C4-D5
A69-B79-C4-D5
A67-B79-C4-D5
A39-B79-C4-D5
A65-B79-C4-D5
A66-B79-C4-D5
A2-B80-C4-D5
A3-B80-C4-D5
A9-B80-C4-D5
A13-B80-C4-D5
A24-B80-C4-D5
A69-B80-C4-D5
A67-B80-C4-D5
A39-B80-C4-D5
A65-B80-C4-D5
A66-B80-C4-D5
A2-B85-C4-D5
A3-B85-C4-D5
A9-B85-C4-D5
A13-B85-C4-D5
A24-B85-C4-D5
A69-B85-C4-D5
A67-B85-C4-D5
A39-B85-C4-D5
A65-B85-C4-D5
A66-B85-C4-D5
A2-B86-C4-D5
A3-B86-C4-D5
A9-B86-C4-D5
A13-B86-C4-D5
A24-B86-C4-D5
A69-B86-C4-D5
A67-B86-C4-D5
A39-B86-C4-D5
A65-B86-C4-D5
A66-B86-C4-D5
A2-B87-C4-D5
A3-B87-C4-D5
A9-B87-C4-D5
A13-B87-C4-D5
A24-B87-C4-D5
A69-B87-C4-D5
A67-B87-C4-D5
A39-B87-C4-D5
A65-B87-C4-D5
A66-B87-C4-D5
A2-B89-C4-D5
A3-B89-C4-D5
A9-B89-C4-D5
A13-B89-C4-D5
A24-B89-C4-D5

TABLE 6-continued

A69-B89-C4-D5
A67-B89-C4-D5
A39-B89-C4-D5
A65-B89-C4-D5
A66-B89-C4-D5
A2-B92-C4-D5
A3-B92-C4-D5
A9-B92-C4-D5
A13-B92-C4-D5
A24-B92-C4-D5
A69-B92-C4-D5
A67-B92-C4-D5
A39-B92-C4-D5
A65-B92-C4-D5
A66-B92-C4-D5
A2-B4-C5-D5
A3-B4-C5-D5
A9-B4-C5-D5
A13-B4-C5-D5
A24-B4-C5-D5
A69-B4-C5-D5
A67-B4-C5-D5
A39-B4-C5-D5
A65-B4-C5-D5
A66-B4-C5-D5
A2-B5-C5-D5
A3-B5-C5-D5
A9-B5-C5-D5
A13-B5-C5-D5
A24-B5-C5-D5
A69-B5-C5-D5
A67-B5-C5-D5
A39-B5-C5-D5
A65-B5-C5-D5
A66-B5-C5-D5
A2-B6-C5-D5
A3-B6-C5-D5
A9-B6-C5-D5
A13-B6-C5-D5
A24-B6-C5-D5
A69-B6-C5-D5
A67-B6-C5-D5
A39-B6-C5-D5
A65-B6-C5-D5
A66-B6-C5-D5
A2-B32-C5-D5
A3-B32-C5-D5
A9-B32-C5-D5
A13-B32-C5-D5
A24-B32-C5-D5
A69-B32-C5-D5
A67-B32-C5-D5
A39-B32-C5-D5
A65-B32-C5-D5
A66-B32-C5-D5
A2-B39-C5-D5
A3-B39-C5-D5
A9-B39-C5-D5
A13-B39-C5-D5
A24-B39-C5-D5
A69-B39-C5-D5
A67-B39-C5-D5
A39-B39-C5-D5
A65-B39-C5-D5
A66-B39-C5-D5
A2-B45-C5-D5
A3-B45-C5-D5
A9-B45-C5-D5
A13-B45-C5-D5
A24-B45-C5-D5
A69-B45-C5-D5
A67-B45-C5-D5
A39-B45-C5-D5
A65-B45-C5-D5
A66-B45-C5-D5
A2-B53-C5-D5
A3-B53-C5-D5
A9-B53-C5-D5
A13-B53-C5-D5

TABLE 6-continued

A24-B53-C5-D5
A69-B53-C5-D5
A67-B53-C5-D5
A39-B53-C5-D5
A65-B53-C5-D5
A66-B53-C5-D5
A2-B79-C5-D5
A3-B79-C5-D5
A9-B79-C5-D5
A13-B79-C5-D5
A24-B79-C5-D5
A69-B79-C5-D5
A67-B79-C5-D5
A39-B79-C5-D5
A65-B79-C5-D5
A66-B79-C5-D5
A2-B80-C5-D5
A3-B80-C5-D5
A9-B80-C5-D5
A13-B80-C5-D5
A24-B80-C5-D5
A69-B80-C5-D5
A67-B80-C5-D5
A39-B80-C5-D5
A65-B80-C5-D5
A66-B80-C5-D5
A2-B85-C5-D5
A3-B85-C5-D5
A9-B85-C5-D5
A13-B85-C5-D5
A24-B85-C5-D5
A69-B85-C5-D5
A67-B85-C5-D5
A39-B85-C5-D5
A65-B85-C5-D5
A66-B85-C5-D5
A2-B86-C5-D5
A3-B86-C5-D5
A9-B86-C5-D5
A13-B86-C5-D5
A24-B86-C5-D5
A69-B86-C5-D5
A67-B86-C5-D5
A39-B86-C5-D5
A65-B86-C5-D5
A66-B86-C5-D5
A2-B87-C5-D5
A3-B87-C5-D5
A9-B87-C5-D5
A13-B87-C5-D5
A24-B87-C5-D5
A69-B87-C5-D5
A67-B87-C5-D5
A39-B87-C5-D5
A65-B87-C5-D5
A66-B87-C5-D5
A2-B89-C5-D5
A3-B89-C5-D5
A9-B89-C5-D5
A13-B89-C5-D5
A24-B89-C5-D5
A69-B89-C5-D5
A67-B89-C5-D5
A39-B89-C5-D5
A65-B89-C5-D5
A66-B89-C5-D5
A2-B92-C5-D5
A3-B92-C5-D5
A9-B92-C5-D5
A13-B92-C5-D5
A24-B92-C5-D5
A69-B92-C5-D5
A67-B92-C5-D5
A39-B92-C5-D5
A65-B92-C5-D5
A66-B92-C5-D5
A2-B4-C6-D5
A3-B4-C6-D5
A9-B4-C6-D5

A13-B4-C6-D5
A24-B4-C6-D5
A69-B4-C6-D5
A67-B4-C6-D5
A39-B4-C6-D5
A65-B4-C6-D5
A66-B4-C6-D5
A2-B5-C6-D5
A3-B5-C6-D5
A9-B5-C6-D5
A13-B5-C6-D5
A24-B5-C6-D5
A69-B5-C6-D5
A67-B5-C6-D5
A39-B5-C6-D5
A65-B5-C6-D5
A66-B5-C6-D5
A2-B6-C6-D5
A3-B6-C6-D5
A9-B6-C6-D5
A13-B6-C6-D5
A24-B6-C6-D5
A69-B6-C6-D5
A67-B6-C6-D5
A39-B6-C6-D5
A65-B6-C6-D5
A66-B6-C6-D5
A2-B32-C6-D5
A3-B32-C6-D5
A9-B32-C6-D5
A13-B32-C6-D5
A24-B32-C6-D5
A69-B32-C6-D5
A67-B32-C6-D5
A39-B32-C6-D5
A65-B32-C6-D5
A66-B32-C6-D5
A2-B39-C6-D5
A3-B39-C6-D5
A9-B39-C6-D5
A13-B39-C6-D5
A24-B39-C6-D5
A69-B39-C6-D5
A67-B39-C6-D5
A39-B39-C6-D5
A65-B39-C6-D5
A66-B39-C6-D5
A2-B45-C6-D5
A3-B45-C6-D5
A9-B45-C6-D5
A13-B45-C6-D5
A24-B45-C6-D5
A69-B45-C6-D5
A67-B45-C6-D5
A39-B45-C6-D5
A65-B45-C6-D5
A66-B45-C6-D5
A2-B53-C6-D5
A3-B53-C6-D5
A9-B53-C6-D5
A13-B53-C6-D5
A24-B53-C6-D5
A69-B53-C6-D5
A67-B53-C6-D5
A39-B53-C6-D5
A65-B53-C6-D5
A66-B53-C6-D5
A2-B79-C6-D5
A3-B79-C6-D5
A9-B79-C6-D5
A13-B79-C6-D5
A24-B79-C6-D5
A69-B79-C6-D5
A67-B79-C6-D5
A39-B79-C6-D5
A65-B79-C6-D5
A66-B79-C6-D5
A2-B80-C6-D5
A3-B80-C6-D5

TABLE 6-continued

A9-B80-C6-D5
A13-B80-C6-D5
A24-B80-C6-D5
A69-B80-C6-D5
A67-B80-C6-D5
A39-B80-C6-D5
A65-B80-C6-D5
A66-B80-C6-D5
A2-B85-C6-D5
A3-B85-C6-D5
A9-B85-C6-D5
A13-B85-C6-D5
A24-B85-C6-D5
A69-B85-C6-D5
A67-B85-C6-D5
A39-B85-C6-D5
A65-B85-C6-D5
A66-B85-C6-D5
A2-B86-C6-D5
A3-B86-C6-D5
A9-B86-C6-D5
A13-B86-C6-D5
A24-B86-C6-D5
A69-B86-C6-D5
A67-B86-C6-D5
A39-B86-C6-D5
A65-B86-C6-D5
A66-B86-C6-D5
A2-B87-C6-D5
A3-B87-C6-D5
A9-B87-C6-D5
A13-B87-C6-D5
A24-B87-C6-D5
A69-B87-C6-D5
A67-B87-C6-D5
A39-B87-C6-D5
A65-B87-C6-D5
A66-B87-C6-D5
A2-B89-C6-D5
A3-B89-C6-D5
A9-B89-C6-D5
A13-B89-C6-D5
A24-B89-C6-D5
A69-B89-C6-D5
A67-B89-C6-D5
A39-B89-C6-D5
A65-B89-C6-D5
A66-B89-C6-D5
A2-B92-C6-D5
A3-B92-C6-D5
A9-B92-C6-D5
A13-B92-C6-D5
A24-B92-C6-D5
A69-B92-C6-D5
A67-B92-C6-D5
A39-B92-C6-D5
A65-B92-C6-D5
A66-B92-C6-D5
A2-B4-C7-D5
A3-B4-C7-D5
A9-B4-C7-D5
A13-B4-C7-D5
A24-B4-C7-D5
A69-B4-C7-D5
A67-B4-C7-D5
A39-B4-C7-D5
A65-B4-C7-D5
A66-B4-C7-D5
A2-B5-C7-D5
A3-B5-C7-D5
A9-B5-C7-D5
A13-B5-C7-D5
A24-B5-C7-D5
A69-B5-C7-D5
A67-B5-C7-D5
A39-B5-C7-D5
A65-B5-C7-D5
A66-B5-C7-D5
A2-B6-C7-D5

TABLE 6-continued

A3-B6-C7-D5
A9-B6-C7-D5
A13-B6-C7-D5
A24-B6-C7-D5
A69-B6-C7-D5
A67-B6-C7-D5
A39-B6-C7-D5
A65-B6-C7-D5
A66-B6-C7-D5
A2-B32-C7-D5
A3-B32-C7-D5
A9-B32-C7-D5
A13-B32-C7-D5
A24-B32-C7-D5
A69-B32-C7-D5
A67-B32-C7-D5
A39-B32-C7-D5
A65-B32-C7-D5
A66-B32-C7-D5
A2-B39-C7-D5
A3-B39-C7-D5
A9-B39-C7-D5
A13-B39-C7-D5
A24-B39-C7-D5
A69-B39-C7-D5
A67-B39-C7-D5
A39-B39-C7-D5
A65-B39-C7-D5
A66-B39-C7-D5
A2-B45-C7-D5
A3-B45-C7-D5
A9-B45-C7-D5
A13-B45-C7-D5
A24-B45-C7-D5
A69-B45-C7-D5
A67-B45-C7-D5
A39-B45-C7-D5
A65-B45-C7-D5
A66-B45-C7-D5
A2-B53-C7-D5
A3-B53-C7-D5
A9-B53-C7-D5
A13-B53-C7-D5
A24-B53-C7-D5
A69-B53-C7-D5
A67-B53-C7-D5
A39-B53-C7-D5
A65-B53-C7-D5
A66-B53-C7-D5
A2-B79-C7-D5
A3-B79-C7-D5
A13-B79-C7-D5
A24-B79-C7-D5
A69-B79-C7-D5
A67-B79-C7-D5
A39-B79-C7-D5
A65-B79-C7-D5
A66-B79-C7-D5
A2-B80-C7-D5
A3-B80-C7-D5
A9-B80-C7-D5
A13-B80-C7-D5
A24-B80-C7-D5
A69-B80-C7-D5
A67-B80-C7-D5
A39-B80-C7-D5
A65-B80-C7-D5
A66-B80-C7-D5
A2-B85-C7-D5
A3-B85-C7-D5
A9-B85-C7-D5
A13-B85-C7-D5
A24-B85-C7-D5
A69-B85-C7-D5
A67-B85-C7-D5
A39-B85-C7-D5
A65-B85-C7-D5
A66-B85-C7-D5
A2-B86-C7-D5

TABLE 6-continued

A3-B86-C7-D5
A9-B86-C7-D5
A13-B86-C7-D5
A24-B86-C7-D5
A69-B86-C7-D5
A67-B86-C7-D5
A39-B86-C7-D5
A65-B86-C7-D5
A66-B86-C7-D5
A2-B87-C7-D5
A3-B87-C7-D5
A9-B87-C7-D5
A13-B87-C7-D5
A24-B87-C7-D5
A69-B87-C7-D5
A67-B87-C7-D5
A39-B87-C7-D5
A65-B87-C7-D5
A66-B87-C7-D5
A2-B89-C7-D5
A3-B89-C7-D5
A9-B89-C7-D5
A13-B89-C7-D5
A24-B89-C7-D5
A69-B89-C7-D5
A67-B89-C7-D5
A65-B89-C7-D5
A66-B89-C7-D5
A2-B92-C7-D5
A3-B92-C7-D5
A9-B92-C7-D5
A13-B92-C7-D5
A24-B92-C7-D5
A69-B92-C7-D5
A67-B92-C7-D5
A39-B92-C7-D5
A65-B92-C7-D5
A66-B92-C7-D5
A2-B4-C8-D5
A3-B4-C8-D5
A9-B4-C8-D5
A13-B4-C8-D5
A24-B4-C8-D5
A69-B4-C8-D5
A67-B4-C8-D5
A39-B4-C8-D5
A65-B4-C8-D5
A66-B4-C8-D5
A2-B5-C8-D5
A3-B5-C8-D5
A9-B5-C8-D5
A13-B5-C8-D5
A24-B5-C8-D5
A69-B5-C8-D5
A67-B5-C8-D5
A39-B5-C8-D5
A65-B5-C8-D5
A66-B5-C8-D5
A2-B6-C8-D5
A3-B6-C8-D5
A9-B6-C8-D5
A13-B6-C8-D5
A24-B6-C8-D5
A69-B6-C8-D5
A67-B6-C8-D5
A39-B6-C8-D5
A65-B6-C8-D5
A66-B6-C8-D5
A2-B32-C8-D5
A3-B32-C8-D5
A9-B32-C8-D5
A13-B32-C8-D5
A24-B32-C8-D5
A69-B32-C8-D5
A67-B32-C8-D5
A39-B32-C8-D5
A65-B32-C8-D5
A66-B32-C8-D5
A2-B39-C8-D5

TABLE 6-continued

A3-B39-C8-D5
A13-B39-C8-D5
A24-B39-C8-D5
A69-B39-C8-D5
A67-B39-C8-D5
A39-B39-C8-D5
A65-B39-C8-D5
A66-B39-C8-D5
A2-B45-C8-D5
A3-B45-C8-D5
A9-B45-C8-D5
A13-B45-C8-D5
A24-B45-C8-D5
A69-B45-C8-D5
A67-B45-C8-D5
A39-B45-C8-D5
A65-B45-C8-D5
A66-B45-C8-D5
A2-B53-C8-D5
A3-B53-C8-D5
A9-B53-C8-D5
A13-B53-C8-D5
A24-B53-C8-D5
A69-B53-C8-D5
A67-B53-C8-D5
A39-B53-C8-D5
A65-B53-C8-D5
A66-B53-C8-D5
A2-B79-C8-D5
A3-B79-C8-D5
A9-B79-C8-D5
A13-B79-C8-D5
A24-B79-C8-D5
A69-B79-C8-D5
A67-B79-C8-D5
A39-B79-C8-D5
A65-B79-C8-D5
A66-B79-C8-D5
A2-B80-C8-D5
A3-B80-C8-D5
A9-B80-C8-D5
A13-B80-C8-D5
A24-B80-C8-D5
A69-B80-C8-D5
A67-B80-C8-D5
A39-B80-C8-D5
A65-B80-C8-D5
A66-B80-C8-D5
A2-B85-C8-D5
A3-B85-C8-D5
A9-B85-C8-D5
A13-B85-C8-D5
A24-B85-C8-D5
A69-B85-C8-D5
A67-B85-C8-D5
A65-B85-C8-D5
A66-B85-C8-D5
A2-B86-C8-D5
A3-B86-C8-D5
A9-B86-C8-D5
A13-B86-C8-D5
A24-B86-C8-D5
A69-B86-C8-D5
A67-B86-C8-D5
A39-B86-C8-D5
A65-B86-C8-D5
A66-B86-C8-D5
A2-B87-C8-D5
A3-B87-C8-D5
A9-B87-C8-D5
A13-B87-C8-D5
A24-B87-C8-D5
A69-B87-C8-D5
A67-B87-C8-D5
A39-B87-C8-D5
A65-B87-C8-D5
A66-B87-C8-D5
A2-B89-C8-D5
A3-B89-C8-D5

TABLE 6-continued

A9-B89-C8-D5
A13-B89-C8-D5
A24-B89-C8-D5
A69-B89-C8-D5
A67-B89-C8-D5
A39-B89-C8-D5
A65-B89-C8-D5
A66-B89-C8-D5
A2-B92-C8-D5
A3-B92-C8-D5
A9-B92-C8-D5
A13-B92-C8-D5
A24-B92-C8-D5
A69-B92-C8-D5
A67-B92-C8-D5
A39-B92-C8-D5
A65-B92-C8-D5
A66-B92-C8-D5
A2-B4-C9-D5
A3-B4-C9-D5
A9-B4-C9-D5
A13-B4-C9-D5
A24-B4-C9-D5
A69-B4-C9-D5
A67-B4-C9-D5
A39-B4-C9-D5
A65-B4-C9-D5
A66-B4-C9-D5
A2-B5-C9-D5
A3-B5-C9-D5
A9-B5-C9-D5
A13-B5-C9-D5
A24-B5-C9-D5
A69-B5-C9-D5
A67-B5-C9-D5
A39-B5-C9-D5
A65-B5-C9-D5
A66-B5-C9-D5
A2-B6-C9-D5
A3-B6-C9-D5
A9-B6-C9-D5
A13-B6-C9-D5
A24-B6-C9-D5
A69-B6-C9-D5
A67-B6-C9-D5
A39-B6-C9-D5
A65-B6-C9-D5
A66-B6-C9-D5
A2-B32-C9-D5
A3-B32-C9-D5
A9-B32-C9-D5
A13-B32-C9-D5
A24-B32-C9-D5
A69-B32-C9-D5
A67-B32-C9-D5
A39-B32-C9-D5
A65-B32-C9-D5
A66-B32-C9-D5
A2-B39-C9-D5
A3-B39-C9-D5
A9-B39-C9-D5
A13-B39-C9-D5
A24-B39-C9-D5
A69-B39-C9-D5
A67-B39-C9-D5
A39-B39-C9-D5
A65-B39-C9-D5
A66-B39-C9-D5
A2-B45-C9-D5
A3-B45-C9-D5
A9-B45-C9-D5
A13-B45-C9-D5
A24-B45-C9-D5
A69-B45-C9-D5
A67-B45-C9-D5
A39-B45-C9-D5
A65-B45-C9-D5
A66-B45-C9-D5
A2-B53-C9-D5

TABLE 6-continued

A3-B53-C9-D5
A9-B53-C9-D5
A13-B53-C9-D5
A24-B53-C9-D5
A69-B53-C9-D5
A67-B53-C9-D5
A39-B53-C9-D5
A65-B53-C9-D5
A66-B53-C9-D5
A2-B79-C9-D5
A3-B79-C9-D5
A9-B79-C9-D5
A13-B79-C9-D5
A24-B79-C9-D5
A69-B79-C9-D5
A67-B79-C9-D5
A39-B79-C9-D5
A65-B79-C9-D5
A66-B79-C9-D5
A2-B80-C9-D5
A3-B80-C9-D5
A9-B80-C9-D5
A13-B80-C9-D5
A24-B80-C9-D5
A69-B80-C9-D5
A67-B80-C9-D5
A39-B80-C9-D5
A65-B80-C9-D5
A66-B80-C9-D5
A2-B85-C9-D5
A3-B85-C9-D5
A9-B85-C9-D5
A13-B85-C9-D5
A24-B85-C9-D5
A69-B85-C9-D5
A67-B85-C9-D5
A39-B85-C9-D5
A65-B85-C9-D5
A66-B85-C9-D5
A2-B86-C9-D5
A3-B86-C9-D5
A9-B86-C9-D5
A13-B86-C9-D5
A24-B86-C9-D5
A69-B86-C9-D5
A67-B86-C9-D5
A39-B86-C9-D5
A65-B86-C9-D5
A66-B86-C9-D5
A2-B87-C9-D5
A3-B87-C9-D5
A9-B87-C9-D5
A13-B87-C9-D5
A24-B87-C9-D5
A69-B87-C9-D5
A67-B87-C9-D5
A39-B87-C9-D5
A65-B87-C9-D5
A66-B87-C9-D5
A2-B89-C9-D5
A3-B89-C9-D5
A9-B89-C9-D5
A13-B89-C9-D5
A24-B89-C9-D5
A69-B89-C9-D5
A67-B89-C9-D5
A39-B89-C9-D5
A65-B89-C9-D5
A66-B89-C9-D5
A2-B92-C9-D5
A3-B92-C9-D5
A9-B92-C9-D5
A13-B92-C9-D5
A24-B92-C9-D5
A69-B92-C9-D5
A67-B92-C9-D5
A39-B92-C9-D5
A65-B92-C9-D5
A66-B92-C9-D5

TABLE 6-continued

A2-B4-C10-D5
A3-B4-C10-D5
A9-B4-C10-D5
A13-B4-C10-D5
A24-B4-C10-D5
A69-B4-C10-D5
A67-B4-C10-D5
A39-B4-C10-D5
A65-B4-C10-D5
A66-B4-C10-D5
A2-B5-C10-D5
A3-B5-C10-D5
A9-B5-C10-D5
A13-B5-C10-D5
A24-B5-C10-D5
A69-B5-C10-D5
A67-B5-C10-D5
A39-B5-C10-D5
A65-B5-C10-D5
A66-B5-C10-D5
A2-B6-C10-D5
A3-B6-C10-D5
A9-B6-C10-D5
A13-B6-C10-D5
A24-B6-C10-D5
A69-B6-C10-D5
A67-B6-C10-D5
A39-B6-C10-D5
A65-B6-C10-D5
A66-B6-C10-D5
A2-B32-C10-D5
A3-B32-C10-D5
A9-B32-C10-D5
A13-B32-C10-D5
A24-B32-C10-D5
A69-B32-C10-D5
A67-B32-C10-D5
A39-B32-C10-D5
A65-B32-C10-D5
A66-B32-C10-D5
A2-B39-C10-D5
A3-B39-C10-D5
A9-B39-C10-D5
A13-B39-C10-D5
A24-B39-C10-D5
A69-B39-C10-D5
A67-B39-C10-D5
A39-B39-C10-D5
A65-B39-C10-D5
A66-B39-C10-D5
A2-B45-C10-D5
A3-B45-C10-D5
A9-B45-C10-D5
A13-B45-C10-D5
A24-B45-C10-D5
A69-B45-C10-D5
A67-B45-C10-D5
A39-B45-C10-D5
A65-B45-C10-D5
A66-B45-C10-D5
A2-B53-C10-D5
A3-B53-C10-D5
A9-B53-C10-D5
A13-B53-C10-D5
A24-B53-C10-D5
A69-B53-C10-D5
A67-B53-C10-D5
A39-B53-C10-D5
A65-B53-C10-D5
A66-B53-C10-D5
A2-B79-C10-D5
A3-B79-C10-D5
A9-B79-C10-D5
A13-B79-C10-D5
A24-B79-C10-D5
A69-B79-C10-D5
A67-B79-C10-D5
A39-B79-C10-D5
A65-B79-C10-D5

TABLE 6-continued

A66-B79-C10-D5
A2-B80-C10-D5
A3-B80-C10-D5
A9-B80-C10-D5
A13-B80-C10-D5
A24-B80-C10-D5
A69-B80-C10-D5
A67-B80-C10-D5
A39-B80-C10-D5
A65-B80-C10-D5
A66-B80-C10-D5
A2-B85-C10-D5
A3-B85-C10-D5
A9-B85-C10-D5
A13-B85-C10-D5
A24-B85-C10-D5
A69-B85-C10-D5
A67-B85-C10-D5
A39-B85-C10-D5
A65-B85-C10-D5
A66-B85-C10-D5
A2-B86-C10-D5
A3-B86-C10-D5
A9-B86-C10-D5
A13-B86-C10-D5
A24-B86-C10-D5
A69-B86-C10-D5
A67-B86-C10-D5
A39-B86-C10-D5
A65-B86-C10-D5
A66-B86-C10-D5
A2-B87-C10-D5
A3-B87-C10-D5
A9-B87-C10-D5
A13-B87-C10-D5
A24-B87-C10-D5
A69-B87-C10-D5
A67-B87-C10-D5
A39-B87-C10-D5
A65-B87-C10-D5
A66-B87-C10-D5
A2-B89-C10-D5
A3-B89-C10-D5
A9-B89-C10-D5
A13-B89-C10-D5
A24-B89-C10-D5
A69-B89-C10-D5
A67-B89-C10-D5
A39-B89-C10-D5
A65-B89-C10-D5
A66-B89-C10-D5
A2-B92-C10-D5
A3-B92-C10-D5
A9-B92-C10-D5
A13-B92-C10-D5
A24-B92-C10-D5
A69-B92-C10-D5
A67-B92-C10-D5
A39-B92-C10-D5
A65-B92-C10-D5
A66-B92-C10-D5
A2-B4-C11-D5
A3-B4-C11-D5
A9-B4-C11-D5
A13-B4-C11-D5
A24-B4-C11-D5
A69-B4-C11-D5
A67-B4-C11-D5
A39-B4-C11-D5
A65-B4-C11-D5
A66-B4-C11-D5
A2-B5-C11-D5
A3-B5-C11-D5
A9-B5-C11-D5
A13-B5-C11-D5
A24-B5-C11-D5
A69-B5-C11-D5
A67-B5-C11-D5
A39-B5-C11-D5

TABLE 6-continued

A65-B5-C11-D5
A66-B5-C11-D5
A2-B6-C11-D5
A3-B6-C11-D5
A9-B6-C11-D5
A13-B6-C11-D5
A24-B6-C11-D5
A69-B6-C11-D5
A67-B6-C11-D5
A39-B6-C11-D5
A65-B6-C11-D5
A66-B6-C11-D5
A2-B32-C11-D5
A3-B32-C11-D5
A9-B32-C11-D5
A13-B32-C11-D5
A24-B32-C11-D5
A69-B32-C11-D5
A67-B32-C11-D5
A39-B32-C11-D5
A65-B32-C11-D5
A66-B32-C11-D5
A2-B39-C11-D5
A3-B39-C11-D5
A9-B39-C11-D5
A13-B39-C11-D5
A24-B39-C11-D5
A69-B39-C11-D5
A67-B39-C11-D5
A39-B39-C11-D5
A65-B39-C11-D5
A66-B39-C11-D5
A2-B45-C11-D5
A3-B45-C11-D5
A9-B45-C11-D5
A13-B45-C11-D5
A24-B45-C11-D5
A69-B45-C11-D5
A67-B45-C11-D5
A39-B45-C11-D5
A65-B45-C11-D5
A66-B45-C11-D5
A2-B53-C11-D5
A3-B53-C11-D5
A9-B53-C11-D5
A13-B53-C11-D5
A24-B53-C11-D5
A69-B53-C11-D5
A67-B53-C11-D5
A39-B53-C11-D5
A65-B53-C11-D5
A66-B53-C11-D5
A2-B79-C11-D5
A3-B79-C11-D5
A9-B79-C11-D5
A13-B79-C11-D5
A24-B79-C11-D5
A69-B79-C11-D5
A67-B79-C11-D5
A39-B79-C11-D5
A65-B79-C11-D5
A66-B79-C11-D5
A2-B80-C11-D5
A3-B80-C11-D5
A9-B80-C11-D5
A13-B80-C11-D5
A24-B80-C11-D5
A69-B80-C11-D5
A67-B80-C11-D5
A39-B80-C11-D5
A65-B80-C11-D5
A66-B80-C11-D5
A2-B85-C11-D5
A3-B85-C11-D5
A9-B85-C11-D5
A13-B85-C11-D5
A24-B85-C11-D5
A69-B85-C11-D5
A67-B85-C11-D5
A39-B85-C11-D5
A65-B85-C11-D5
A66-B85-C11-D5
A2-B86-C11-D5
A3-B86-C11-D5
A9-B86-C11-D5
A13-B86-C11-D5
A24-B86-C11-D5
A69-B86-C11-D5
A67-B86-C11-D5
A39-B86-C11-D5
A65-B86-C11-D5
A66-B86-C11-D5
A2-B87-C11-D5
A3-B87-C11-D5
A9-B87-C11-D5
A13-B87-C11-D5
A24-B87-C11-D5
A69-B87-C11-D5
A67-B87-C11-D5
A39-B87-C11-D5
A65-B87-C11-D5
A66-B87-C11-D5
A2-B89-C11-D5
A3-B89-C11-D5
A9-B89-C11-D5
A13-B89-C11-D5
A24-B89-C11-D5
A69-B89-C11-D5
A67-B89-C11-D5
A39-B89-C11-D5
A65-B89-C11-D5
A66-B89-C11-D5
A2-B92-C11-D5
A3-B92-C11-D5
A9-B92-C11-D5
A13-B92-C11-D5
A24-B92-C11-D5
A69-B92-C11-D5
A67-B92-C11-D5
A39-B92-C11-D5
A65-B92-C11-D5
A66-B92-C11-D5
A2-B4-C12-D5
A3-B4-C12-D5
A9-B4-C12-D5
A13-B4-C12-D5
A24-B4-C12-D5
A69-B4-C12-D5
A67-B4-C12-D5
A39-B4-C12-D5
A65-B4-C12-D5
A66-B4-C12-D5
A2-B5-C12-D5
A3-B5-C12-D5
A9-B5-C12-D5
A13-B5-C12-D5
A24-B5-C12-D5
A69-B5-C12-D5
A67-B5-C12-D5
A39-B5-C12-D5
A65-B5-C12-D5
A66-B5-C12-D5
A2-B6-C12-D5
A3-B6-C12-D5
A9-B6-C12-D5
A13-B6-C12-D5
A24-B6-C12-D5
A69-B6-C12-D5
A67-B6-C12-D5
A39-B6-C12-D5
A65-B6-C12-D5
A66-B6-C12-D5
A2-B32-C12-D5
A3-B32-C12-D5
A9-B32-C12-D5
A13-B32-C12-D5
A24-B32-C12-D5
A69-B32-C12-D5

TABLE 6-continued

A67-B32-C12-D5
A39-B32-C12-D5
A65-B32-C12-D5
A66-B32-C12-D5
A2-B39-C12-D5
A3-B39-C12-D5
A9-B39-C12-D5
A13-B39-C12-D5
A24-B39-C12-D5
A69-B39-C12-D5
A67-B39-C12-D5
A39-B39-C12-D5
A65-B39-C12-D5
A66-B39-C12-D5
A2-B45-C12-D5
A3-B45-C12-D5
A9-B45-C12-D5
A13-B45-C12-D5
A24-B45-C12-D5
A69-B45-C12-D5
A67-B45-C12-D5
A39-B45-C12-D5
A65-B45-C12-D5
A66-B45-C12-D5
A2-B53-C12-D5
A3-B53-C12-D5
A9-B53-C12-D5
A13-B53-C12-D5
A24-B53-C12-D5
A69-B53-C12-D5
A67-B53-C12-D5
A39-B53-C12-D5
A65-B53-C12-D5
A66-B53-C12-D5
A2-B79-C12-D5
A3-B79-C12-D5
A9-B79-C12-D5
A13-B79-C12-D5
A24-B79-C12-D5
A69-B79-C12-D5
A67-B79-C12-D5
A39-B79-C12-D5
A65-B79-C12-D5
A66-B79-C12-D5
A2-B80-C12-D5
A3-B80-C12-D5
A9-B80-C12-D5
A13-B80-C12-D5
A24-B80-C12-D5
A69-B80-C12-D5
A67-B80-C12-D5
A39-B80-C12-D5
A65-B80-C12-D5
A66-B80-C12-D5
A2-B85-C12-D5
A3-B85-C12-D5
A9-B85-C12-D5
A13-B85-C12-D5
A24-B85-C12-D5
A69-B85-C12-D5
A67-B85-C12-D5
A39-B85-C12-D5
A65-B85-C12-D5
A66-B85-C12-D5
A2-B86-C12-D5
A3-B86-C12-D5
A9-B86-C12-D5
A13-B86-C12-D5
A24-B86-C12-D5
A69-B86-C12-D5
A67-B86-C12-D5
A39-B86-C12-D5
A65-B86-C12-D5
A66-B86-C12-D5
A2-B87-C12-D5
A3-B87-C12-D5
A9-B87-C12-D5
A13-B87-C12-D5
A24-B87-C12-D5

TABLE 6-continued

A69-B87-C12-D5
A67-B87-C12-D5
A39-B87-C12-D5
A65-B87-C12-D5
A66-B87-C12-D5
A2-B89-C12-D5
A3-B89-C12-D5
A9-B89-C12-D5
A13-B89-C12-D5
A24-B89-C12-D5
A69-B89-C12-D5
A67-B89-C12-D5
A39-B89-C12-D5
A65-B89-C12-D5
A66-B89-C12-D5
A2-B92-C12-D5
A3-B92-C12-D5
A9-B92-C12-D5
A13-B92-C12-D5
A24-B92-C12-D5
A69-B92-C12-D5
A67-B92-C12-D5
A39-B92-C12-D5
A65-B92-C12-D5
A66-B92-C12-D5
A2-B4-C13-D5
A3-B4-C13-D5
A9-B4-C13-D5
A13-B4-C13-D5
A24-B4-C13-D5
A69-B4-C13-D5
A67-B4-C13-D5
A39-B4-C13-D5
A65-B4-C13-D5
A66-B4-C13-D5
A2-B5-C13-D5
A3-B5-C13-D5
A9-B5-C13-D5
A13-B5-C13-D5
A24-B5-C13-D5
A69-B5-C13-D5
A67-B5-C13-D5
A39-B5-C13-D5
A65-B5-C13-D5
A66-B5-C13-D5
A2-B6-C13-D5
A3-B6-C13-D5
A9-B6-C13-D5
A13-B6-C13-D5
A24-B6-C13-D5
A69-B6-C13-D5
A67-B6-C13-D5
A39-B6-C13-D5
A65-B6-C13-D5
A66-B6-C13-D5
A2-B32-C13-D5
A3-B32-C13-D5
A9-B32-C13-D5
A13-B32-C13-D5
A24-B32-C13-D5
A69-B32-C13-D5
A67-B32-C13-D5
A39-B32-C13-D5
A65-B32-C13-D5
A66-B32-C13-D5
A2-B39-C13-D5
A3-B39-C13-D5
A9-B39-C13-D5
A13-B39-C13-D5
A24-B39-C13-D5
A69-B39-C13-D5
A67-B39-C13-D5
A39-B39-C13-D5
A65-B39-C13-D5
A66-B39-C13-D5
A2-B45-C13-D5
A3-B45-C13-D5
A9-B45-C13-D5
A13-B45-C13-D5

TABLE 6-continued

A24-B45-C13-D5
A69-B45-C13-D5
A67-B45-C13-D5
A39-B45-C13-D5
A65-B45-C13-D5
A66-B45-C13-D5
A2-B53-C13-D5
A3-B53-C13-D5
A9-B53-C13-D5
A13-B53-C13-D5
A24-B53-C13-D5
A69-B53-C13-D5
A67-B53-C13-D5
A39-B53-C13-D5
A65-B53-C13-D5
A66-B53-C13-D5
A2-B79-C13-D5
A3-B79-C13-D5
A9-B79-C13-D5
A13-B79-C13-D5
A24-B79-C13-D5
A69-B79-C13-D5
A67-B79-C13-D5
A39-B79-C13-D5
A65-B79-C13-D5
A66-B79-C13-D5
A2-B80-C13-D5
A3-B80-C13-D5
A9-B80-C13-D5
A13-B80-C13-D5
A24-B80-C13-D5
A69-B80-C13-D5
A67-B80-C13-D5
A39-B80-C13-D5
A65-B80-C13-D5
A66-B80-C13-D5
A2-B85-C13-D5
A3-B85-C13-D5
A9-B85-C13-D5
A13-B85-C13-D5
A24-B85-C13-D5
A69-B85-C13-D5
A67-B85-C13-D5
A39-B85-C13-D5
A65-B85-C13-D5
A66-B85-C13-D5
A2-B86-C13-D5
A3-B86-C13-D5
A9-B86-C13-D5
A13-B86-C13-D5
A24-B86-C13-D5
A69-B86-C13-D5
A67-B86-C13-D5
A39-B86-C13-D5
A65-B86-C13-D5
A66-B86-C13-D5
A2-B87-C13-D5
A3-B87-C13-D5
A9-B87-C13-D5
A13-B87-C13-D5
A24-B87-C13-D5
A69-B87-C13-D5
A67-B87-C13-D5
A39-B87-C13-D5
A65-B87-C13-D5
A66-B87-C13-D5
A2-B89-C13-D5
A3-B89-C13-D5
A9-B89-C13-D5
A13-B89-C13-D5
A24-B89-C13-D5
A69-B89-C13-D5
A67-B89-C13-D5
A39-B89-C13-D5
A65-B89-C13-D5
A66-B89-C13-D5
A2-B92-C13-D5
A3-B92-C13-D5
A9-B92-C13-D5

TABLE 6-continued

A13-B92-C13-D5
A24-B92-C13-D5
A69-B92-C13-D5
A67-B92-C13-D5
A39-B92-C13-D5
A65-B92-C13-D5
A66-B92-C13-D5
A2-B4-C1-D6
A3-B4-C1-D6
A9-B4-C1-D6
A13-B4-C1-D6
A24-B4-C1-D6
A69-B4-C1-D6
A67-B4-C1-D6
A39-B4-C1-D6
A65-B4-C1-D6
A66-B4-C1-D6
A2-B5-C1-D6
A3-B5-C1-D6
A9-B5-C1-D6
A13-B5-C1-D6
A24-B5-C1-D6
A69-B5-C1-D6
A67-B5-C1-D6
A39-B5-C1-D6
A65-B5-C1-D6
A66-B5-C1-D6
A2-B6-C1-D6
A3-B6-C1-D6
A9-B6-C1-D6
A13-B6-C1-D6
A24-B6-C1-D6
A69-B6-C1-D6
A67-B6-C1-D6
A39-B6-C1-D6
A65-B6-C1-D6
A66-B6-C1-D6
A2-B32-C1-D6
A3-B32-C1-D6
A9-B32-C1-D6
A13-B32-C1-D6
A24-B32-C1-D6
A69-B32-C1-D6
A67-B32-C1-D6
A39-B32-C1-D6
A65-B32-C1-D6
A66-B32-C1-D6
A2-B39-C1-D6
A3-B39-C1-D6
A9-B39-C1-D6
A13-B39-C1-D6
A24-B39-C1-D6
A69-B39-C1-D6
A67-B39-C1-D6
A39-B39-C1-D6
A65-B39-C1-D6
A66-B39-C1-D6
A2-B45-C1-D6
A3-B45-C1-D6
A9-B45-C1-D6
A13-B45-C1-D6
A24-B45-C1-D6
A69-B45-C1-D6
A67-B45-C1-D6
A39-B45-C1-D6
A65-B45-C1-D6
A66-B45-C1-D6
A2-B53-C1-D6
A3-B53-C1-D6
A9-B53-C1-D6
A13-B53-C1-D6
A24-B53-C1-D6
A69-B53-C1-D6
A67-B53-C1-D6
A39-B53-C1-D6
A65-B53-C1-D6
A66-B53-C1-D6
A2-B79-C1-D6
A3-B79-C1-D6

TABLE 6-continued

| | |
|---|---|
| A9-B79-C1-D6 | A3-B5-C2-D6 |
| A13-B79-C1-D6 | A9-B5-C2-D6 |
| A24-B79-C1-D6 | A13-B5-C2-D6 |
| A69-B79-C1-D6 | A24-B5-C2-D6 |
| A67-B79-C1-D6 | A69-B5-C2-D6 |
| A39-B79-C1-D6 | A67-B5-C2-D6 |
| A65-B79-C1-D6 | A39-B5-C2-D6 |
| A66-B79-C1-D6 | A65-B5-C2-D6 |
| A2-B80-C1-D6 | A66-B5-C2-D6 |
| A3-B80-C1-D6 | A2-B6-C2-D6 |
| A9-B80-C1-D6 | A3-B6-C2-D6 |
| A13-B80-C1-D6 | A9-B6-C2-D6 |
| A24-B80-C1-D6 | A13-B6-C2-D6 |
| A69-B80-C1-D6 | A24-B6-C2-D6 |
| A67-B80-C1-D6 | A69-B6-C2-D6 |
| A39-B80-C1-D6 | A67-B6-C2-D6 |
| A65-B80-C1-D6 | A39-B6-C2-D6 |
| A66-B80-C1-D6 | A65-B6-C2-D6 |
| A2-B85-C1-D6 | A66-B6-C2-D6 |
| A3-B85-C1-D6 | A2-B32-C2-D6 |
| A9-B85-C1-D6 | A3-B32-C2-D6 |
| A13-B85-C1-D6 | A9-B32-C2-D6 |
| A24-B85-C1-D6 | A13-B32-C2-D6 |
| A69-B85-C1-D6 | A24-B32-C2-D6 |
| A67-B85-C1-D6 | A69-B32-C2-D6 |
| A39-B85-C1-D6 | A67-B32-C2-D6 |
| A65-B85-C1-D6 | A39-B32-C2-D6 |
| A66-B85-C1-D6 | A65-B32-C2-D6 |
| A2-B86-C1-D6 | A66-B32-C2-D6 |
| A3-B86-C1-D6 | A2-B39-C2-D6 |
| A9-B86-C1-D6 | A3-B39-C2-D6 |
| A13-B86-C1-D6 | A9-B39-C2-D6 |
| A24-B86-C1-D6 | A13-B39-C2-D6 |
| A69-B86-C1-D6 | A24-B39-C2-D6 |
| A67-B86-C1-D6 | A69-B39-C2-D6 |
| A39-B86-C1-D6 | A67-B39-C2-D6 |
| A65-B86-C1-D6 | A39-B39-C2-D6 |
| A66-B86-C1-D6 | A65-B39-C2-D6 |
| A2-B87-C1-D6 | A66-B39-C2-D6 |
| A3-B87-C1-D6 | A2-B45-C2-D6 |
| A9-B87-C1-D6 | A3-B45-C2-D6 |
| A13-B87-C1-D6 | A9-B45-C2-D6 |
| A24-B87-C1-D6 | A13-B45-C2-D6 |
| A69-B87-C1-D6 | A24-B45-C2-D6 |
| A67-B87-C1-D6 | A69-B45-C2-D6 |
| A39-B87-C1-D6 | A67-B45-C2-D6 |
| A65-B87-C1-D6 | A39-B45-C2-D6 |
| A66-B87-C1-D6 | A65-B45-C2-D6 |
| A2-B89-C1-D6 | A66-B45-C2-D6 |
| A3-B89-C1-D6 | A2-B53-C2-D6 |
| A9-B89-C1-D6 | A3-B53-C2-D6 |
| A13-B89-C1-D6 | A9-B53-C2-D6 |
| A24-B89-C1-D6 | A13-B53-C2-D6 |
| A69-B89-C1-D6 | A24-B53-C2-D6 |
| A67-B89-C1-D6 | A69-B53-C2-D6 |
| A39-B89-C1-D6 | A67-B53-C2-D6 |
| A65-B89-C1-D6 | A39-B53-C2-D6 |
| A66-B89-C1-D6 | A65-B53-C2-D6 |
| A2-B92-C1-D6 | A66-B53-C2-D6 |
| A3-B92-C1-D6 | A2-B79-C2-D6 |
| A9-B92-C1-D6 | A3-B79-C2-D6 |
| A13-B92-C1-D6 | A9-B79-C2-D6 |
| A24-B92-C1-D6 | A13-B79-C2-D6 |
| A69-B92-C1-D6 | A24-B79-C2-D6 |
| A67-B92-C1-D6 | A69-B79-C2-D6 |
| A39-B92-C1-D6 | A67-B79-C2-D6 |
| A65-B92-C1-D6 | A39-B79-C2-D6 |
| A66-B92-C1-D6 | A65-B79-C2-D6 |
| A2-B4-C2-D6 | A66-B79-C2-D6 |
| A3-B4-C2-D6 | A2-B80-C2-D6 |
| A9-B4-C2-D6 | A3-B80-C2-D6 |
| A13-B4-C2-D6 | A9-B80-C2-D6 |
| A24-B4-C2-D6 | A13-B80-C2-D6 |
| A69-B4-C2-D6 | A24-B80-C2-D6 |
| A67-B4-C2-D6 | A69-B80-C2-D6 |
| A39-B4-C2-D6 | A67-B80-C2-D6 |
| A65-B4-C2-D6 | A39-B80-C2-D6 |
| A66-B4-C2-D6 | A65-B80-C2-D6 |
| A2-B5-C2-D6 | A66-B80-C2-D6 |

TABLE 6-continued

A2-B85-C2-D6
A3-B85-C2-D6
A9-B85-C2-D6
A13-B85-C2-D6
A24-B85-C2-D6
A69-B85-C2-D6
A67-B85-C2-D6
A39-B85-C2-D6
A65-B85-C2-D6
A66-B85-C2-D6
A2-B86-C2-D6
A3-B86-C2-D6
A9-B86-C2-D6
A13-B86-C2-D6
A24-B86-C2-D6
A69-B86-C2-D6
A67-B86-C2-D6
A39-B86-C2-D6
A65-B86-C2-D6
A66-B86-C2-D6
A2-B87-C2-D6
A3-B87-C2-D6
A9-B87-C2-D6
A13-B87-C2-D6
A24-B87-C2-D6
A69-B87-C2-D6
A67-B87-C2-D6
A39-B87-C2-D6
A65-B87-C2-D6
A66-B87-C2-D6
A2-B89-C2-D6
A3-B89-C2-D6
A9-B89-C2-D6
A13-B89-C2-D6
A24-B89-C2-D6
A69-B89-C2-D6
A67-B89-C2-D6
A39-B89-C2-D6
A65-B89-C2-D6
A66-B89-C2-D6
A2-B92-C2-D6
A3-B92-C2-D6
A9-B92-C2-D6
A13-B92-C2-D6
A24-B92-C2-D6
A69-B92-C2-D6
A67-B92-C2-D6
A39-B92-C2-D6
A65-B92-C2-D6
A66-B92-C2-D6
A2-B4-C3-D6
A3-B4-C3-D6
A9-B4-C3-D6
A13-B4-C3-D6
A24-B4-C3-D6
A69-B4-C3-D6
A67-B4-C3-D6
A39-B4-C3-D6
A65-B4-C3-D6
A66-B4-C3-D6
A2-B5-C3-D6
A3-B5-C3-D6
A9-B5-C3-D6
A13-B5-C3-D6
A24-B5-C3-D6
A69-B5-C3-D6
A67-B5-C3-D6
A39-B5-C3-D6
A65-B5-C3-D6
A66-B5-C3-D6
A2-B6-C3-D6
A3-B6-C3-D6
A9-B6-C3-D6
A13-B6-C3-D6
A24-B6-C3-D6
A69-B6-C3-D6
A67-B6-C3-D6
A39-B6-C3-D6
A65-B6-C3-D6

TABLE 6-continued

A66-B6-C3-D6
A2-B32-C3-D6
A3-B32-C3-D6
A9-B32-C3-D6
A13-B32-C3-D6
A24-B32-C3-D6
A69-B32-C3-D6
A67-B32-C3-D6
A39-B32-C3-D6
A65-B32-C3-D6
A66-B32-C3-D6
A2-B39-C3-D6
A3-B39-C3-D6
A9-B39-C3-D6
A13-B39-C3-D6
A24-B39-C3-D6
A69-B39-C3-D6
A67-B39-C3-D6
A39-B39-C3-D6
A65-B39-C3-D6
A66-B39-C3-D6
A2-B45-C3-D6
A3-B45-C3-D6
A9-B45-C3-D6
A13-B45-C3-D6
A24-B45-C3-D6
A69-B45-C3-D6
A67-B45-C3-D6
A39-B45-C3-D6
A65-B45-C3-D6
A66-B45-C3-D6
A2-B53-C3-D6
A3-B53-C3-D6
A9-B53-C3-D6
A13-B53-C3-D6
A24-B53-C3-D6
A69-B53-C3-D6
A67-B53-C3-D6
A39-B53-C3-D6
A65-B53-C3-D6
A66-B53-C3-D6
A2-B79-C3-D6
A3-B79-C3-D6
A9-B79-C3-D6
A13-B79-C3-D6
A24-B79-C3-D6
A69-B79-C3-D6
A67-B79-C3-D6
A39-B79-C3-D6
A65-B79-C3-D6
A66-B79-C3-D6
A2-B80-C3-D6
A3-B80-C3-D6
A9-B80-C3-D6
A13-B80-C3-D6
A24-B80-C3-D6
A69-B80-C3-D6
A67-B80-C3-D6
A39-B80-C3-D6
A65-B80-C3-D6
A66-B80-C3-D6
A2-B85-C3-D6
A3-B85-C3-D6
A9-B85-C3-D6
A13-B85-C3-D6
A24-B85-C3-D6
A69-B85-C3-D6
A67-B85-C3-D6
A39-B85-C3-D6
A65-B85-C3-D6
A66-B85-C3-D6
A2-B86-C3-D6
A3-B86-C3-D6
A9-B86-C3-D6
A13-B86-C3-D6
A24-B86-C3-D6
A69-B86-C3-D6
A67-B86-C3-D6
A39-B86-C3-D6

TABLE 6-continued

A65-B86-C3-D6
A66-B86-C3-D6
A2-B87-C3-D6
A3-B87-C3-D6
A9-B87-C3-D6
A13-B87-C3-D6
A24-B87-C3-D6
A69-B87-C3-D6
A67-B87-C3-D6
A39-B87-C3-D6
A65-B87-C3-D6
A66-B87-C3-D6
A2-B89-C3-D6
A3-B89-C3-D6
A9-B89-C3-D6
A13-B89-C3-D6
A24-B89-C3-D6
A69-B89-C3-D6
A67-B89-C3-D6
A39-B89-C3-D6
A65-B89-C3-D6
A66-B89-C3-D6
A2-B92-C3-D6
A3-B92-C3-D6
A9-B92-C3-D6
A13-B92-C3-D6
A24-B92-C3-D6
A69-B92-C3-D6
A67-B92-C3-D6
A39-B92-C3-D6
A65-B92-C3-D6
A66-B92-C3-D6
A2-B4-C4-D6
A3-B4-C4-D6
A9-B4-C4-D6
A13-B4-C4-D6
A24-B4-C4-D6
A69-B4-C4-D6
A67-B4-C4-D6
A39-B4-C4-D6
A65-B4-C4-D6
A66-B4-C4-D6
A2-B5-C4-D6
A3-B5-C4-D6
A9-B5-C4-D6
A13-B5-C4-D6
A24-B5-C4-D6
A69-B5-C4-D6
A67-B5-C4-D6
A39-B5-C4-D6
A65-B5-C4-D6
A66-B5-C4-D6
A2-B6-C4-D6
A3-B6-C4-D6
A9-B6-C4-D6
A13-B6-C4-D6
A24-B6-C4-D6
A69-B6-C4-D6
A67-B6-C4-D6
A39-B6-C4-D6
A65-B6-C4-D6
A66-B6-C4-D6
A2-B32-C4-D6
A3-B32-C4-D6
A9-B32-C4-D6
A13-B32-C4-D6
A24-B32-C4-D6
A69-B32-C4-D6
A67-B32-C4-D6
A39-B32-C4-D6
A65-B32-C4-D6
A66-B32-C4-D6
A2-B39-C4-D6
A3-B39-C4-D6
A9-B39-C4-D6
A13-B39-C4-D6
A24-B39-C4-D6
A69-B39-C4-D6
A67-B39-C4-D6

TABLE 6-continued

A39-B39-C4-D6
A65-B39-C4-D6
A66-B39-C4-D6
A2-B45-C4-D6
A3-B45-C4-D6
A9-B45-C4-D6
A13-B45-C4-D6
A24-B45-C4-D6
A69-B45-C4-D6
A67-B45-C4-D6
A39-B45-C4-D6
A65-B45-C4-D6
A66-B45-C4-D6
A2-B53-C4-D6
A3-B53-C4-D6
A9-B53-C4-D6
A13-B53-C4-D6
A24-B53-C4-D6
A69-B53-C4-D6
A67-B53-C4-D6
A39-B53-C4-D6
A65-B53-C4-D6
A66-B53-C4-D6
A2-B79-C4-D6
A3-B79-C4-D6
A9-B79-C4-D6
A13-B79-C4-D6
A24-B79-C4-D6
A69-B79-C4-D6
A67-B79-C4-D6
A39-B79-C4-D6
A65-B79-C4-D6
A66-B79-C4-D6
A2-B80-C4-D6
A3-B80-C4-D6
A9-B80-C4-D6
A13-B80-C4-D6
A24-B80-C4-D6
A69-B80-C4-D6
A67-B80-C4-D6
A39-B80-C4-D6
A65-B80-C4-D6
A66-B80-C4-D6
A2-B85-C4-D6
A3-B85-C4-D6
A9-B85-C4-D6
A13-B85-C4-D6
A24-B85-C4-D6
A69-B85-C4-D6
A67-B85-C4-D6
A39-B85-C4-D6
A65-B85-C4-D6
A66-B85-C4-D6
A2-B86-C4-D6
A3-B86-C4-D6
A9-B86-C4-D6
A13-B86-C4-D6
A24-B86-C4-D6
A69-B86-C4-D6
A67-B86-C4-D6
A39-B86-C4-D6
A65-B86-C4-D6
A66-B86-C4-D6
A2-B87-C4-D6
A3-B87-C4-D6
A9-B87-C4-D6
A13-B87-C4-D6
A24-B87-C4-D6
A69-B87-C4-D6
A67-B87-C4-D6
A39-B87-C4-D6
A65-B87-C4-D6
A66-B87-C4-D6
A2-B89-C4-D6
A3-B89-C4-D6
A9-B89-C4-D6
A13-B89-C4-D6
A24-B89-C4-D6
A69-B89-C4-D6

TABLE 6-continued

A67-B89-C4-D6
A39-B89-C4-D6
A65-B89-C4-D6
A66-B89-C4-D6
A2-B92-C4-D6
A3-B92-C4-D6
A9-B92-C4-D6
A13-B92-C4-D6
A24-B92-C4-D6
A69-B92-C4-D6
A67-B92-C4-D6
A39-B92-C4-D6
A65-B92-C4-D6
A66-B92-C4-D6
A2-B4-C5-D6
A3-B4-C5-D6
A9-B4-C5-D6
A13-B4-C5-D6
A24-B4-C5-D6
A69-B4-C5-D6
A67-B4-C5-D6
A39-B4-C5-D6
A65-B4-C5-D6
A66-B4-C5-D6
A2-B5-C5-D6
A3-B5-C5-D6
A9-B5-C5-D6
A13-B5-C5-D6
A24-B5-C5-D6
A69-B5-C5-D6
A67-B5-C5-D6
A39-B5-C5-D6
A65-B5-C5-D6
A66-B5-C5-D6
A2-B6-C8-D6
A3-B6-C5-D6
A9-B6-C5-D6
A13-B6-C5-D6
A24-B6-C5-D6
A69-B6-C5-D6
A67-B6-C5-D6
A39-B6-C5-D6
A65-B6-C5-D6
A66-B6-C5-D6
A2-B32-C5-D6
A3-B32-C5-D6
A9-B32-C5-D6
A13-B32-C5-D6
A24-B32-C5-D6
A69-B32-C5-D6
A67-B32-C5-D6
A39-B32-C5-D6
A65-B32-C5-D6
A66-B32-C5-D6
A2-B39-C5-D6
A3-B39-C5-D6
A9-B39-C5-D6
A13-B39-C5-D6
A24-B39-C5-D6
A69-B39-C5-D6
A67-B39-C5-D6
A39-B39-C5-D6
A65-B39-C5-D6
A66-B39-C5-D6
A2-B45-C5-D6
A3-B45-C5-D6
A9-B45-C5-D6
A13-B45-C5-D6
A24-B45-C5-D6
A69-B45-C5-D6
A67-B45-C5-D6
A39-B45-C5-D6
A65-B45-C5-D6
A66-B45-C5-D6
A2-B53-C5-D6
A3-B53-C5-D6
A9-B53-C5-D6
A13-B53-C5-D6
A24-B53-C5-D6

TABLE 6-continued

A69-B53-C5-D6
A67-B53-C5-D6
A39-B53-C5-D6
A65-B53-C5-D6
A66-B53-C5-D6
A2-B79-C5-D6
A3-B79-C5-D6
A9-B79-C5-D6
A13-B79-C5-D6
A24-B79-C5-D6
A69-B79-C5-D6
A67-B79-C5-D6
A39-B79-C5-D6
A65-B79-C5-D6
A66-B79-C5-D6
A2-B80-C5-D6
A3-B80-C5-D6
A9-B80-C5-D6
A13-B80-C5-D6
A24-B80-C5-D6
A69-B80-C5-D6
A67-B80-C5-D6
A39-B80-C5-D6
A65-B80-C5-D6
A66-B80-C5-D6
A2-B85-C5-D6
A3-B85-C5-D6
A9-B85-C5-D6
A13-B85-C5-D6
A24-B85-C5-D6
A69-B85-C5-D6
A67-B85-C5-D6
A39-B85-C5-D6
A65-B85-C5-D6
A66-B85-C5-D6
A2-B86-C5-D6
A3-B86-C5-D6
A9-B86-C5-D6
A13-B86-C5-D6
A24-B86-C5-D6
A69-B86-C5-D6
A67-B86-C5-D6
A39-B86-C5-D6
A65-B86-C5-D6
A66-B86-C5-D6
A2-B87-C5-D6
A3-B87-C5-D6
A9-B87-C5-D6
A13-B87-C5-D6
A24-B87-C5-D6
A69-B87-C5-D6
A67-B87-C5-D6
A39-B87-C5-D6
A65-B87-C5-D6
A66-B87-C5-D6
A2-B89-C5-D6
A3-B89-C5-D6
A9-B89-C5-D6
A13-B89-C5-D6
A24-B89-C5-D6
A69-B89-C5-D6
A67-B89-C5-D6
A39-B89-C5-D6
A65-B89-C5-D6
A66-B89-C5-D6
A2-B92-C5-D6
A3-B92-C5-D6
A9-B92-C5-D6
A13-B92-C5-D6
A24-B92-C5-D6
A69-B92-C5-D6
A67-B92-C5-D6
A39-B92-C5-D6
A65-B92-C5-D6
A66-B92-C5-D6
A2-B4-C6-D6
A3-B4-C6-D6
A9-B4-C6-D6
A13-B4-C6-D6

TABLE 6-continued

A24-B4-C6-D6
A69-B4-C6-D6
A67-B4-C6-D6
A39-B4-C6-D6
A65-B4-C6-D6
A66-B4-C6-D6
A2-B5-C6-D6
A3-B5-C6-D6
A9-B5-C6-D6
A13-B5-C6-D6
A24-B5-C6-D6
A69-B5-C6-D6
A67-B5-C6-D6
A39-B5-C6-D6
A65-B5-C6-D6
A66-B5-C6-D6
A2-B6-C6-D6
A3-B6-C6-D6
A9-B6-C6-D6
A13-B6-C6-D6
A24-B6-C6-D6
A69-B6-C6-D6
A67-B6-C6-D6
A39-B6-C6-D6
A65-B6-C6-D6
A66-B6-C6-D6
A2-B32-C6-D6
A3-B32-C6-D6
A9-B32-C6-D6
A13-B32-C6-D6
A24-B32-C6-D6
A69-B32-C6-D6
A67-B32-C6-D6
A39-B32-C6-D6
A65-B32-C6-D6
A66-B32-C6-D6
A2-B39-C6-D6
A3-B39-C6-D6
A9-B39-C6-D6
A13-B39-C6-D6
A24-B39-C6-D6
A69-B39-C6-D6
A67-B39-C6-D6
A39-B39-C6-D6
A65-B39-C6-D6
A66-B39-C6-D6
A2-B45-C6-D6
A3-B45-C6-D6
A9-B45-C6-D6
A13-B45-C6-D6
A24-B45-C6-D6
A69-B45-C6-D6
A67-B45-C6-D6
A39-B45-C6-D6
A65-B45-C6-D6
A66-B45-C6-D6
A2-B53-C6-D6
A3-B53-C6-D6
A9-B53-C6-D6
A13-B53-C6-D6
A24-B53-C6-D6
A69-B53-C6-D6
A67-B53-C6-D6
A39-B53-C6-D6
A65-B53-C6-D6
A66-B53-C6-D6
A2-B79-C6-D6
A3-B79-C6-D6
A9-B79-C6-D6
A13-B79-C6-D6
A24-B79-C6-D6
A69-B79-C6-D6
A67-B79-C6-D6
A39-B79-C6-D6
A65-B79-C6-D6
A66-B79-C6-D6
A2-B80-C6-D6
A3-B80-C6-D6
A9-B80-C6-D6

TABLE 6-continued

A13-B80-C6-D6
A24-B80-C6-D6
A69-B80-C6-D6
A67-B80-C6-D6
A39-B80-C6-D6
A65-B80-C6-D6
A66-B80-C6-D6
A2-B85-C6-D6
A3-B85-C6-D6
A9-B85-C6-D6
A13-B85-C6-D6
A24-B85-C6-D6
A69-B85-C6-D6
A67-B85-C6-D6
A39-B85-C6-D6
A65-B85-C6-D6
A66-B85-C6-D6
A2-B86-C6-D6
A3-B86-C6-D6
A9-B86-C6-D6
A13-B86-C6-D6
A24-B86-C6-D6
A69-B86-C6-D6
A67-B86-C6-D6
A39-B86-C6-D6
A65-B86-C6-D6
A66-B86-C6-D6
A2-B87-C6-D6
A3-B87-C6-D6
A9-B87-C6-D6
A13-B87-C6-D6
A24-B87-C6-D6
A69-B87-C6-D6
A67-B87-C6-D6
A39-B87-C6-D6
A65-B87-C6-D6
A66-B87-C6-D6
A2-B89-C6-D6
A3-B89-C6-D6
A9-B89-C6-D6
A13-B89-C6-D6
A24-B89-C6-D6
A69-B89-C6-D6
A67-B89-C6-D6
A39-B89-C6-D6
A65-B89-C6-D6
A66-B89-C6-D6
A2-B92-C6-D6
A3-B92-C6-D6
A9-B92-C6-D6
A13-B92-C6-D6
A24-B92-C6-D6
A69-B92-C6-D6
A67-B92-C6-D6
A39-B92-C6-D6
A65-B92-C6-D6
A66-B92-C6-D6
A2-B4-C7-D6
A3-B4-C7-D6
A9-B4-C7-D6
A13-B4-C7-D6
A24-B4-C7-D6
A69-B4-C7-D6
A67-B4-C7-D6
A39-B4-C7-D6
A65-B4-C7-D6
A66-B4-C7-D6
A2-B5-C7-D6
A3-B5-C7-D6
A9-B5-C7-D6
A13-B5-C7-D6
A24-B5-C7-D6
A69-B5-C7-D6
A67-B5-C7-D6
A39-B5-C7-D6
A65-B5-C7-D6
A66-B5-C7-D6
A2-B6-C7-D6
A3-B6-C7-D6

TABLE 6-continued

A9-B6-C7-D6
A13-B6-C7-D6
A24-B6-C7-D6
A69-B6-C7-D6
A67-B6-C7-D6
A39-B6-C7-D6
A65-B6-C7-D6
A66-B6-C7-D6
A2-B32-C7-D6
A3-B32-C7-D6
A9-B32-C7-D6
A13-B32-C7-D6
A24-B32-C7-D6
A69-B32-C7-D6
A67-B32-C7-D6
A39-B32-C7-D6
A65-B32-C7-D6
A66-B32-C7-D6
A2-B39-C7-D6
A3-B39-C7-D6
A9-B39-C7-D6
A13-B39-C7-D6
A24-B39-C7-D6
A69-B39-C7-D6
A67-B39-C7-D6
A39-B39-C7-D6
A65-B39-C7-D6
A66-B39-C7-D6
A2-B45-C7-D6
A3-B45-C7-D6
A9-B45-C7-D6
A13-B45-C7-D6
A24-B45-C7-D6
A69-B45-C7-D6
A67-B45-C7-D6
A39-B45-C7-D6
A65-B45-C7-D6
A66-B45-C7-D6
A2-B53-C7-D6
A3-B53-C7-D6
A9-B53-C7-D6
A13-B53-C7-D6
A24-B53-C7-D6
A69-B53-C7-D6
A67-B53-C7-D6
A39-B53-C7-D6
A65-B53-C7-D6
A66-B53-C7-D6
A2-B79-C7-D6
A3-B79-C7-D6
A9-B79-C7-D6
A13-B79-C7-D6
A24-B79-C7-D6
A69-B79-C7-D6
A67-B79-C7-D6
A39-B79-C7-D6
A65-B79-C7-D6
A66-B79-C7-D6
A2-B80-C7-D6
A3-B80-C7-D6
A9-B80-C7-D6
A13-B80-C7-D6
A24-B80-C7-D6
A69-B80-C7-D6
A67-B80-C7-D6
A39-B80-C7-D6
A65-B80-C7-D6
A66-B80-C7-D6
A2-B85-C7-D6
A3-B85-C7-D6
A9-B85-C7-D6
A13-B85-C7-D6
A24-B85-C7-D6
A69-B85-C7-D6
A39-B85-C7-D6
A65-B85-C7-D6
A66-B85-C7-D6
A2-B86-C7-D6

TABLE 6-continued

A3-B86-C7-D6
A9-B86-C7-D6
A13-B86-C7-D6
A24-B86-C7-D6
A69-B86-C7-D6
A67-B86-C7-D6
A39-B86-C7-D6
A65-B86-C7-D6
A66-B86-C7-D6
A2-B87-C7-D6
A3-B87-C7-D6
A9-B87-C7-D6
A13-B87-C7-D6
A24-B87-C7-D6
A69-B87-C7-D6
A67-B87-C7-D6
A39-B87-C7-D6
A65-B87-C7-D6
A66-B87-C7-D6
A2-B89-C7-D6
A3-B89-C7-D6
A9-B89-C7-D6
A13-B89-C7-D6
A24-B89-C7-D6
A69-B89-C7-D6
A67-B89-C7-D6
A39-B89-C7-D6
A65-B89-C7-D6
A66-B89-C7-D6
A2-B92-C7-D6
A3-B92-C7-D6
A9-B92-C7-D6
A13-B92-C7-D6
A24-B92-C7-D6
A69-B92-C7-D6
A67-B92-C7-D6
A39-B92-C7-D6
A65-B92-C7-D6
A66-B92-C7-D6
A2-B4-C8-D6
A3-B4-C8-D6
A9-B4-C8-D6
A13-B4-C8-D6
A24-B4-C8-D6
A69-B4-C8-D6
A67-B4-C8-D6
A39-B4-C8-D6
A65-B4-C8-D6
A66-B4-C8-D6
A2-B5-C8-D6
A3-B5-C8-D6
A9-B5-C8-D6
A13-B5-C8-D6
A24-B5-C8-D6
A69-B5-C8-D6
A67-B5-C8-D6
A39-B5-C8-D6
A65-B5-C8-D6
A66-B5-C8-D6
A2-B6-C8-D6
A3-B6-C8-D6
A9-B6-C8-D6
A13-B6-C8-D6
A24-B6-C8-D6
A69-B6-C8-D6
A67-B6-C8-D6
A39-B6-C8-D6
A65-B6-C8-D6
A66-B6-C8-D6
A2-B32-C8-D6
A3-B32-C8-D6
A9-B32-C8-D6
A13-B32-C8-D6
A24-B32-C8-D6
A69-B32-C8-D6
A67-B32-C8-D6
A39-B32-C8-D6
A65-B32-C8-D6
A66-B32-C8-D6

TABLE 6-continued

A2-B39-C8-D6
A3-B39-C8-D6
A9-B39-C8-D6
A13-B39-C8-D6
A24-B39-C8-D6
A69-B39-C8-D6
A67-B39-C8-D6
A39-B39-C8-D6
A65-B39-C8-D6
A66-B39-C8-D6
A2-B45-C8-D6
A3-B45-C8-D6
A9-B45-C8-D6
A13-B45-C8-D6
A24-B45-C8-D6
A69-B45-C8-D6
A67-B45-C8-D6
A39-B45-C8-D6
A65-B45-C8-D6
A66-B45-C8-D6
A2-B53-C8-D6
A3-B53-C8-D6
A9-B53-C8-D6
A13-B53-C8-D6
A24-B53-C8-D6
A69-B53-C8-D6
A67-B53-C8-D6
A39-B53-C8-D6
A65-B53-C8-D6
A66-B53-C8-D6
A2-B79-C8-D6
A3-B79-C8-D6
A9-B79-C8-D6
A13-B79-C8-D6
A24-B79-C8-D6
A69-B79-C8-D6
A67-B79-C8-D6
A39-B79-C8-D6
A65-B79-C8-D6
A66-B79-C8-D6
A2-B80-C8-D6
A3-B80-C8-D6
A9-B80-C8-D6
A13-B80-C8-D6
A24-B80-C8-D6
A69-B80-C8-D6
A67-B80-C8-D6
A39-B80-C8-D6
A65-B80-C8-D6
A66-B80-C8-D6
A2-B85-C8-D6
A3-B85-C8-D6
A9-B85-C8-D6
A13-B85-C8-D6
A24-B85-C8-D6
A69-B85-C8-D6
A67-B85-C8-D6
A39-B85-C8-D6
A65-B85-C8-D6
A66-B85-C8-D6
A2-B86-C8-D6
A3-B86-C8-D6
A9-B86-C8-D6
A13-B86-C8-D6
A24-B86-C8-D6
A69-B86-C8-D6
A67-B86-C8-D6
A39-B86-C8-D6
A65-B86-C8-D6
A66-B86-C8-D6
A2-B87-C8-D6
A3-B87-C8-D6
A9-B87-C8-D6
A13-B87-C8-D6
A24-B87-C8-D6
A69-B87-C8-D6
A67-B87-C8-D6
A39-B87-C8-D6
A65-B87-C8-D6

TABLE 6-continued

A66-B87-C8-D6
A2-B89-C8-D6
A3-B89-C8-D6
A9-B89-C8-D6
A13-B89-C8-D6
A24-B89-C8-D6
A69-B89-C8-D6
A67-B89-C8-D6
A39-B89-C8-D6
A65-B89-C8-D6
A66-B89-C8-D6
A2-B92-C8-D6
A3-B92-C8-D6
A9-B92-C8-D6
A13-B92-C8-D6
A24-B92-C8-D6
A69-B92-C8-D6
A67-B92-C8-D6
A39-B92-C8-D6
A65-B92-C8-D6
A66-B92-C8-D6
A2-B4-C9-D6
A3-B4-C9-D6
A9-B4-C9-D6
A13-B4-C9-D6
A24-B4-C9-D6
A69-B4-C9-D6
A67-B4-C9-D6
A39-B4-C9-D6
A65-B4-C9-D6
A66-B4-C9-D6
A2-B5-C9-D6
A3-B5-C9-D6
A9-B5-C9-D6
A13-B5-C9-D6
A24-B5-C9-D6
A69-B5-C9-D6
A67-B5-C9-D6
A39-B5-C9-D6
A65-B5-C9-D6
A66-B5-C9-D6
A2-B6-C9-D6
A3-B6-C9-D6
A9-B6-C9-D6
A13-B6-C9-D6
A24-B6-C9-D6
A69-B6-C9-D6
A67-B6-C9-D6
A39-B6-C9-D6
A65-B6-C9-D6
A66-B6-C9-D6
A2-B32-C9-D6
A3-B32-C9-D6
A9-B32-C9-D6
A13-B32-C9-D6
A24-B32-C9-D6
A69-B32-C9-D6
A67-B32-C9-D6
A39-B32-C9-D6
A65-B32-C9-D6
A66-B32-C9-D6
A2-B39-C9-D6
A3-B39-C9-D6
A9-B39-C9-D6
A13-B39-C9-D6
A24-B39-C9-D6
A69-B39-C9-D6
A67-B39-C9-D6
A39-B39-C9-D6
A65-B39-C9-D6
A66-B39-C9-D6
A2-B45-C9-D6
A3-B45-C9-D6
A9-B45-C9-D6
A13-B45-C9-D6
A24-B45-C9-D6
A69-B45-C9-D6
A67-B45-C9-D6
A39-B45-C9-D6

TABLE 6-continued

| | |
|---|---|
| A65-B45-C9-D6 | A39-B92-C9-D6 |
| A66-B45-C9-D6 | A65-B92-C9-D6 |
| A2-B53-C9-D6 | A66-B92-C9-D6 |
| A3-B53-C9-D6 | A2-B4-C10-D6 |
| A9-B53-C9-D6 | A3-B4-C10-D6 |
| A13-B53-C9-D6 | A9-B4-C10-D6 |
| A24-B53-C9-D6 | A13-B4-C10-D6 |
| A69-B53-C9-D6 | A24-B4-C10-D6 |
| A67-B53-C9-D6 | A69-B4-C10-D6 |
| A39-B53-C9-D6 | A67-B4-C10-D6 |
| A65-B53-C9-D6 | A39-B4-C10-D6 |
| A66-B53-C9-D6 | A65-B4-C10-D6 |
| A2-B79-C9-D6 | A66-B4-C10-D6 |
| A3-B79-C9-D6 | A2-B5-C10-D6 |
| A9-B79-C9-D6 | A3-B5-C10-D6 |
| A13-B79-C9-D6 | A9-B5-C10-D6 |
| A24-B79-C9-D6 | A13-B5-C10-D6 |
| A69-B79-C9-D6 | A24-B5-C10-D6 |
| A67-B79-C9-D6 | A69-B5-C10-D6 |
| A39-B79-C9-D6 | A67-B5-C10-D6 |
| A65-B79-C9-D6 | A39-B5-C10-D6 |
| A66-B79-C9-D6 | A65-B5-C10-D6 |
| A2-B80-C9-D6 | A66-B5-C10-D6 |
| A3-B80-C9-D6 | A2-B6-C10-D6 |
| A9-B80-C9-D6 | A3-B6-C10-D6 |
| A13-B80-C9-D6 | A9-B6-C10-D6 |
| A24-B80-C9-D6 | A13-B6-C10-D6 |
| A69-B80-C9-D6 | A24-B6-C10-D6 |
| A67-B80-C9-D6 | A69-B6-C10-D6 |
| A39-B80-C9-D6 | A67-B6-C10-D6 |
| A65-B80-C9-D6 | A39-B6-C10-D6 |
| A66-B80-C9-D6 | A65-B6-C10-D6 |
| A2-B85-C9-D6 | A66-B6-C10-D6 |
| A3-B85-C9-D6 | A2-B32-C10-D6 |
| A9-B85-C9-D6 | A3-B32-C10-D6 |
| A13-B85-C9-D6 | A9-B32-C10-D6 |
| A24-B85-C9-D6 | A13-B32-C10-D6 |
| A69-B85-C9-D6 | A24-B32-C10-D6 |
| A67-B85-C9-D6 | A69-B32-C10-D6 |
| A39-B85-C9-D6 | A67-B32-C10-D6 |
| A65-B85-C9-D6 | A39-B32-C10-D6 |
| A66-B85-C9-D6 | A65-B32-C10-D6 |
| A2-B86-C9-D6 | A66-B32-C10-D6 |
| A3-B86-C9-D6 | A2-B39-C10O-D6 |
| A9-B86-C9-D6 | A3-B39-C10-D6 |
| A13-B86-C9-D6 | A9-B39-C10-D6 |
| A24-B86-C9-D6 | A13-B39-C10-D6 |
| A69-B86-C9-D6 | A24-B39-C10-D6 |
| A67-B86-C9-D6 | A69-B39-C10-D6 |
| A39-B86-C9-D6 | A67-B39-C10-D6 |
| A65-B86-C9-D6 | A39-B39-C10-D6 |
| A66-B86-C9-D6 | A65-B39-C10-D6 |
| A2-B87-C9-D6 | A66-B39-C10-D6 |
| A3-B87-C9-D6 | A2-B45-C10-D6 |
| A9-B87-C9-D6 | A3-B45-C10-D6 |
| A13-B87-C9-D6 | A9-B45-C10-D6 |
| A24-B87-C9-D6 | A13-B45-C10-D6 |
| A69-B87-C9-D6 | A24-B45-C10-D6 |
| A67-B87-C9-D6 | A69-B45-C10-D6 |
| A39-B87-C9-D6 | A67-B45-C10-D6 |
| A65-B87-C9-D6 | A39-B45-C10-D6 |
| A66-B87-C9-D6 | A65-B45-C10-D6 |
| A2-B89-C9-D6 | A66-B45-C10-D6 |
| A3-B89-C9-D6 | A2-B53-C10-D6 |
| A9-B89-C9-D6 | A3-B53-C10-D6 |
| A13-B89-C9-D6 | A9-B53-C10-D6 |
| A24-B89-C9-D6 | A13-B53-C10-D6 |
| A69-B89-C9-D6 | A24-B53-C10-D6 |
| A67-B89-C9-D6 | A69-B53-C10-D6 |
| A39-B89-C9-D6 | A67-B53-C10-D6 |
| A65-B89-C9-D6 | A39-B53-C10-D6 |
| A66-B89-C9-D6 | A65-B53-C10-D6 |
| A2-B92-C9-D6 | A66-B53-C10-D6 |
| A3-B92-C9-D6 | A2-B79-C10-D6 |
| A9-B92-C9-D6 | A3-B79-C10-D6 |
| A13-B92-C9-D6 | A9-B79-C10-D6 |
| A24-B92-C9-D6 | A13-B79-C10-D6 |
| A69-B92-C9-D6 | A24-B79-C10-D6 |
| A67-B92-C9-D6 | A69-B79-C10-D6 |

TABLE 6-continued

A67-B79-C10-D6
A39-B79-C10-D6
A65-B79-C10-D6
A66-B79-C10-D6
A2-B80-C10-D6
A3-B80-C10-D6
A9-B80-C10-D6
A13-B80-C10-D6
A24-B80-C10-D6
A69-B80-C10-D6
A67-B80-C10-D6
A39-B80-C10-D6
A65-B80-C10-D6
A66-B80-C10-D6
A2-B85-C10-D6
A3-B85-C10-D6
A9-B85-C10-D6
A13-B85-C10-D6
A24-B85-C10-D6
A69-B85-C10-D6
A67-B85-C10-D6
A39-B85-C10-D6
A65-B85-C10-D6
A66-B85-C10-D6
A2-B86-C10-D6
A3-B86-C10-D6
A9-B86-C10-D6
A13-B86-C10-D6
A24-B86-C10-D6
A69-B86-C10-D6
A67-B86-C10-D6
A39-B86-C10-D6
A65-B86-C10-D6
A66-B86-C10-D6
A2-B87-C10-D6
A3-B87-C10-D6
A9-B87-C10-D6
A13-B87-C10-D6
A24-B87-C10-D6
A69-B87-C10-D6
A67-B87-C10-D6
A39-B87-C10-D6
A65-B87-C10-D6
A66-B87-C10-D6
A2-B89-C10-D6
A3-B89-C10-D6
A9-B89-C10-D6
A13-B89-C10-D6
A24-B89-C10-D6
A69-B89-C10-D6
A67-B89-C10-D6
A39-B89-C10-D6
A65-B89-C10-D6
A66-B89-C10-D6
A2-B92-C10-D6
A3-B92-C10-D6
A9-B92-C10-D6
A13-B92-C10-D6
A24-B92-C10-D6
A69-B92-C10-D6
A67-B92-C10-D6
A39-B92-C10-D6
A65-B92-C10-D6
A66-B92-C10-D6
A2-B4-C11-D6
A3-B4-C11-D6
A9-B4-C11-D6
A13-B4-C11-D6
A24-B4-C11-D6
A69-B4-C11-D6
A67-B4-C11-D6
A39-B4-C11-D6
A65-B4-C11-D6
A66-B4-C11-D6
A2-B5-C11-D6
A3-B5-C11-D6
A9-B5-C11-D6
A13-B5-C11-D6
A24-B5-C11-D6

TABLE 6-continued

A69-B5-C11-D6
A67-B5-C11-D6
A39-B5-C11-D6
A65-B5-C11-D6
A66-B5-C11-D6
A2-B6-C11-D6
A3-B6-C11-D6
A9-B6-C11-D6
A13-B6-C11-D6
A24-B6-C11-D6
A69-B6-C11-D6
A67-B6-C11-D6
A39-B6-C11-D6
A65-B6-C11-D6
A66-B6-C11-D6
A2-B32-C11-D6
A3-B32-C11-D6
A9-B32-C11-D6
A13-B32-C11-D6
A24-B32-C11-D6
A69-B32-C11-D6
A67-B32-C11-D6
A39-B32-C11-D6
A65-B32-C11-D6
A66-B32-C11-D6
A2-B39-C11-D6
A3-B39-C11-D6
A9-B39-C11-D6
A13-B39-C11-D6
A24-B39-C11-D6
A69-B39-C11-D6
A67-B39-C11-D6
A39-B39-C11-D6
A65-B39-C11-D6
A66-B39-C11-D6
A2-B45-C11-D6
A3-B45-C11-D6
A9-B45-C11-D6
A13-B45-C11-D6
A24-B45-C11-D6
A69-B45-C11-D6
A67-B45-C11-D6
A39-B45-C11-D6
A65-B45-C11-D6
A66-B45-C11-D6
A2-B53-C11-D6
A3-B53-C11-D6
A9-B53-C11-D6
A13-B53-C11-D6
A24-B53-C11-D6
A69-B53-C11-D6
A67-B53-C11-D6
A39-B53-C11-D6
A65-B53-C11-D6
A66-B53-C11-D6
A2-B79-C11-D6
A3-B79-C11-D6
A9-B79-C11-D6
A13-B79-C11-D6
A24-B79-C11-D6
A69-B79-C11-D6
A67-B79-C11-D6
A39-B79-C11-D6
A65-B79-C11-D6
A66-B79-C11-D6
A2-B80-C11-D6
A3-B80-C11-D6
A9-B80-C11-D6
A13-B80-C11-D6
A24-B80-C11-D6
A69-B80-C11-D6
A67-B80-C11-D6
A39-B80-C11-D6
A65-B80-C11-D6
A66-B80-C11-D6
A2-B85-C11-D6
A3-B85-C11-D6
A9-B85-C11-D6
A13-B85-C11-D6

TABLE 6-continued

A24-B85-C11-D6
A69-B85-C11-D6
A67-B85-C11-D6
A39-B85-C11-D6
A65-B85-C11-D6
A66-B85-C11-D6
A2-B86-C11-D6
A3-B86-C11-D6
A9-B86-C11-D6
A13-B86-C11-D6
A24-B86-C11-D6
A69-B86-C11-D6
A67-B86-C11-D6
A39-B86-C11-D6
A65-B86-C11-D6
A66-B86-C11-D6
A2-B87-C11-D6
A3-B87-C11-D6
A9-B87-C11-D6
A13-B87-C11-D6
A24-B87-C11-D6
A69-B87-C11-D6
A67-B87-C11-D6
A39-B87-C11-D6
A65-B87-C11-D6
A66-B87-C11-D6
A2-B89-C11-D6
A3-B89-C11-D6
A9-B89-C11-D6
A13-B89-C11-D6
A24-B89-C11-D6
A69-B89-C11-D6
A67-B89-C11-D6
A39-B89-C11-D6
A65-B89-C11-D6
A66-B89-C11-D6
A2-B92-C11-D6
A3-B92-C11-D6
A9-B92-C11-D6
A13-B92-C11-D6
A24-B92-C11-D6
A69-B92-C11-D6
A67-B92-C11-D6
A39-B92-C11-D6
A65-B92-C11-D6
A66-B92-C11-D6
A2-B4-C12-D6
A3-B4-C12-D6
A9-B4-C12-D6
A13-B4-C12-D6
A24-B4-C12-D6
A69-B4-C12-D6
A67-B4-C12-D6
A39-B4-C12-D6
A65-B4-C12-D6
A66-B4-C12-D6
A2-B5-C12-D6
A3-B5-C12-D6
A9-B5-C12-D6
A13-B5-C12-D6
A24-B5-C12-D6
A69-B5-C12-D6
A67-B5-C12-D6
A39-B5-C12-D6
A65-B5-C12-D6
A66-B5-C12-D6
A2-B6-C12-D6
A3-B6-C12-D6
A9-B6-C12-D6
A13-B6-C12-D6
A24-B6-C12-D6
A69-B6-C12-D6
A67-B6-C12-D6
A39-B6-C12-D6
A65-B6-C12-D6
A66-B6-C12-D6
A2-B32-C12-D6
A3-B32-C12-D6
A9-B32-C12-D6

TABLE 6-continued

A13-B32-C12-D6
A24-B32-C12-D6
A69-B32-C12-D6
A67-B32-C12-D6
A39-B32-C12-D6
A65-B32-C12-D6
A66-B32-C12-D6
A2-B39-C12-D6
A3-B39-C12-D6
A9-B39-C12-D6
A13-B39-C12-D6
A24-B39-C12-D6
A69-B39-C12-D6
A67-B39-C12-D6
A39-B39-C12-D6
A65-B39-C12-D6
A66-B39-C12-D6
A2-B45-C12-D6
A3-B45-C12-D6
A9-B45-C12-D6
A13-B45-C12-D6
A24-B45-C12-D6
A69-B45-C12-D6
A67-B45-C12-D6
A39-B45-C12-D6
A65-B45-C12-D6
A66-B45-C12-D6
A2-B53-C12-D6
A3-B53-C12-D6
A9-B53-C12-D6
A13-B53-C12-D6
A24-B53-C12-D6
A69-B53-C12-D6
A67-B53-C12-D6
A39-B53-C12-D6
A65-B53-C12-D6
A66-B53-C12-D6
A2-B79-C12-D6
A3-B79-C12-D6
A9-B79-C12-D6
A13-B79-C12-D6
A24-B79-C12-D6
A69-B79-C12-D6
A67-B79-C12-D6
A39-B79-C12-D6
A65-B79-C12-D6
A66-B79-C12-D6
A2-B80-C12-D6
A3-B80-C12-D6
A9-B80-C12-D6
A13-B80-C12-D6
A24-B80-C12-D6
A69-B80-C12-D6
A67-B80-C12-D6
A39-B80-C12-D6
A65-B80-C12-D6
A66-B80-C12-D6
A2-B85-C12-D6
A3-B85-C12-D6
A9-B85-C12-D6
A13-B85-C12-D6
A24-B85-C12-D6
A69-B85-C12-D6
A67-B85-C12-D6
A39-B85-C12-D6
A65-B85-C12-D6
A66-B85-C12-D6
A2-B86-C12-D6
A3-B86-C12-D6
A9-B86-C12-D6
A13-B86-C12-D6
A24-B86-C12-D6
A69-B86-C12-D6
A67-B86-C12-D6
A39-B86-C12-D6
A65-B86-C12-D6
A66-B86-C12-D6
A2-B87-C12-D6
A3-B87-C12-D6

TABLE 6-continued

A9-B87-C12-D6
A13-B87-C12-D6
A24-B87-C12-D6
A69-B87-C12-D6
A67-B87-C12-D6
A39-B87-C12-D6
A65-B87-C12-D6
A66-B87-C12-D6
A2-B89-C12-D6
A3-B89-C12-D6
A9-B89-C12-D6
A13-B89-C12-D6
A24-B89-C12-D6
A69-B89-C12-D6
A67-B89-C12-D6
A39-B89-C12-D6
A65-B89-C12-D6
A66-B89-C12-D6
A2-B92-C12-D6
A3-B92-C12-D6
A9-B92-C12-D6
A13-B92-C12-D6
A24-B92-C12-D6
A69-B92-C12-D6
A67-B92-C12-D6
A39-B92-C12-D6
A65-B92-C12-D6
A66-B92-C12-D6
A2-B4-C13-D6
A3-B4-C13-D6
A9-B4-C13-D6
A13-B4-C13-D6
A24-B4-C13-D6
A69-B4-C13-D6
A67-B4-C13-D6
A39-B4-C13-D6
A65-B4-C13-D6
A66-B4-C13-D6
A2-B5-C13-D6
A3-B5-C13-D6
A9-B5-C13-D6
A13-B5-C13-D6
A24-B5-C13-D6
A69-B5-C13-D6
A67-B5-C13-D6
A39-B5-C13-D6
A65-B5-C13-D6
A66-B5-C13-D6
A2-B6-C13-D6
A3-B6-C13-D6
A9-B6-C13-D6
A13-B6-C13-D6
A24-B6-C13-D6
A69-B6-C13-D6
A67-B6-C13-D6
A39-B6-C13-D6
A65-B6-C13-D6
A66-B6-C13-D6
A2-B32-C13-D6
A3-B32-C13-D6
A9-B32-C13-D6
A13-B32-C13-D6
A24-B32-C13-D6
A69-B32-C13-D6
A67-B32-C13-D6
A39-B32-C13-D6
A65-B32-C13-D6
A66-B32-C13-D6
A2-B39-C13-D6
A3-B39-C13-D6
A9-B39-C13-D6
A13-B39-C13-D6
A24-B39-C13-D6
A69-B39-C13-D6
A67-B39-C13-D6
A39-B39-C13-D6
A65-B39-C13-D6
A66-B39-C13-D6
A2-B45-C13-D6

TABLE 6-continued

A3-B45-C13-D6
A9-B45-C13-D6
A13-B45-C13-D6
A24-B45-C13-D6
A69-B45-C13-D6
A67-B45-C13-D6
A39-B45-C13-D6
A65-B45-C13-D6
A66-B45-C13-D6
A2-B53-C13-D6
A3-B53-C13-D6
A9-B53-C13-D6
A13-B53-C13-D6
A24-B53-C13-D6
A69-B53-C13-D6
A67-B53-C13-D6
A39-B53-C13-D6
A65-B53-C13-D6
A66-B53-C13-D6
A2-B79-C13-D6
A3-B79-C13-D6
A9-B79-C13-D6
A13-B79-C13-D6
A24-B79-C13-D6
A69-B79-C13-D6
A67-B79-C13-D6
A39-B79-C13-D6
A65-B79-C13-D6
A66-B79-C13-D6
A2-B80-C13-D6
A3-B80-C13-D6
A9-B80-C13-D6
A13-B80-C13-D6
A24-B80-C13-D6
A69-B80-C13-D6
A67-B80-C13-D6
A39-B80-C13-D6
A65-B80-C13-D6
A66-B80-C13-D6
A2-B85-C13-D6
A3-B85-C13-D6
A9-B85-C13-D6
A13-B85-C13-D6
A24-B85-C13-D6
A69-B85-C13-D6
A67-B85-C13-D6
A39-B85-C13-D6
A65-B85-C13-D6
A66-B85-C13-D6
A2-B86-C13-D6
A3-B86-C13-D6
A9-B86-C13-D6
A13-B86-C13-D6
A24-B86-C13-D6
A69-B86-C13-D6
A67-B86-C13-D6
A39-B86-C13-D6
A65-B86-C13-D6
A66-B86-C13-D6
A2-B87-C13-D6
A3-B87-C13-D6
A9-B87-C13-D6
A13-B87-C13-D6
A24-B87-C13-D6
A69-B87-C13-D6
A67-B87-C13-D6
A39-B87-C13-D6
A65-B87-C13-D6
A66-B87-C13-D6
A2-B89-C13-D6
A3-B89-C13-D6
A9-B89-C13-D6
A13-B89-C13-D6
A24-B89-C13-D6
A69-B89-C13-D6
A67-B89-C13-D6
A39-B89-C13-D6
A65-B89-C13-D6
A66-B89-C13-D6

TABLE 6-continued

| | |
|---|---|
| A2-B92-C13-D6 | A66-B53-C1-D7 |
| A3-B92-C13-D6 | A2-B79-C1-D7 |
| A9-B92-C13-D6 | A3-B79-C1-D7 |
| A13-B92-C13-D6 | A9-B79-C1-D7 |
| A24-B92-C13-D6 | A13-B79-C1-D7 |
| A69-B92-C13-D6 | A24-B79-C1-D7 |
| A67-B92-C13-D6 | A69-B79-C1-D7 |
| A39-B92-C13-D6 | A67-B79-C1-D7 |
| A65-B92-C13-D6 | A39-B79-C1-D7 |
| A66-B92-C13-D6 | A65-B79-C1-D7 |
| A2-B4-C1-D7 | A66-B79-C1-D7 |
| A3-B4-C1-D7 | A2-B80-C1-D7 |
| A9-B4-C1-D7 | A3-B80-C1-D7 |
| A13-B4-C1-D7 | A9-B80-C1-D7 |
| A24-B4-C1-D7 | A13-B80-C1-D7 |
| A69-B4-C1-D7 | A24-B80-C1-D7 |
| A67-B4-C1-D7 | A69-B80-C1-D7 |
| A39-B4-C1-D7 | A67-B80-C1-D7 |
| A65-B4-C1-D7 | A39-B80-C1-D7 |
| A66-B4-C1-D7 | A65-B80-C1-D7 |
| A2-B5-C1-D7 | A66-B80-C1-D7 |
| A3-B5-C1-D7 | A2-B85-C1-D7 |
| A9-B5-C1-D7 | A3-B85-C1-D7 |
| A13-B5-C1-D7 | A9-B85-C1-D7 |
| A24-B5-C1-D7 | A13-B85-C1-D7 |
| A69-B5-C1-D7 | A24-B85-C1-D7 |
| A67-B5-C1-D7 | A69-B85-C1-D7 |
| A39-B5-C1-D7 | A67-B85-C1-D7 |
| A65-B5-C1-D7 | A39-B85-C1-D7 |
| A66-B5-C1-D7 | A65-B85-C1-D7 |
| A2-B6-C1-D7 | A66-B85-C1-D7 |
| A3-B6-C1-D7 | A2-B86-C1-D7 |
| A9-B6-C1-D7 | A3-B86-C1-D7 |
| A13-B6-C1-D7 | A9-B86-C1-D7 |
| A24-B6-C1-D7 | A13-B86-C1-D7 |
| A69-B6-C1-D7 | A24-B86-C1-D7 |
| A67-B6-C1-D7 | A69-B86-C1-D7 |
| A39-B6-C1-D7 | A67-B86-C1-D7 |
| A65-B6-C1-D7 | A39-B86-C1-D7 |
| A66-B6-C1-D7 | A65-B86-C1-D7 |
| A2-B32-C1-D7 | A66-B86-C1-D7 |
| A3-B32-C1-D7 | A2-B87-C1-D7 |
| A9-B32-C1-D7 | A3-B87-C1-D7 |
| A13-B32-C1-D7 | A9-B87-C1-D7 |
| A24-B32-C1-D7 | A13-B87-C1-D7 |
| A69-B32-C1-D7 | A24-B87-C1-D7 |
| A67-B32-C1-D7 | A69-B87-C1-D7 |
| A39-B32-C1-D7 | A67-B87-C1-D7 |
| A65-B32-C1-D7 | A39-B87-C1-D7 |
| A66-B32-C1-D7 | A65-B87-C1-D7 |
| A2-B39-C1-D7 | A66-B87-C1-D7 |
| A3-B39-C1-D7 | A2-B89-C1-D7 |
| A9-B39-C1-D7 | A3-B89-C1-D7 |
| A13-B39-C1-D7 | A9-B89-C1-D7 |
| A24-B39-C1-D7 | A13-B89-C1-D7 |
| A69-B39-C1-D7 | A24-B89-C1-D7 |
| A67-B39-C1-D7 | A69-B89-C1-D7 |
| A39-B39-C1-D7 | A67-B89-C1-D7 |
| A65-B39-C1-D7 | A39-B89-C1-D7 |
| A66-B39-C1-D7 | A65-B89-C1-D7 |
| A2-B45-C1-D7 | A66-B89-C1-D7 |
| A3-B45-C1-D7 | A2-B92-C1-D7 |
| A9-B45-C1-D7 | A3-B92-C1-D7 |
| A13-B45-C1-D7 | A9-B92-C1-D7 |
| A24-B45-C1-D7 | A13-B92-C1-D7 |
| A69-B45-C1-D7 | A24-B92-C1-D7 |
| A67-B45-C1-D7 | A69-B92-C1-D7 |
| A39-B45-C1-D7 | A67-B92-C1-D7 |
| A65-B45-C1-D7 | A39-B92-C1-D7 |
| A66-B45-C1-D7 | A65-B92-C1-D7 |
| A2-B53-C1-D7 | A66-B92-C1-D7 |
| A3-B53-C1-D7 | A2-B4-C2-D7 |
| A9-B53-C1-D7 | A3-B4-C2-D7 |
| A13-B53-C1-D7 | A9-B4-C2-D7 |
| A24-B53-C1-D7 | A13-B4-C2-D7 |
| A69-B53-C1-D7 | A24-B4-C2-D7 |
| A67-B53-C1-D7 | A69-B4-C2-D7 |
| A39-B53-C1-D7 | A67-B4-C2-D7 |
| A65-B53-C1-D7 | A39-B4-C2-D7 |

TABLE 6-continued

A65-B4-C2-D7
A66-B4-C2-D7
A2-B5-C2-D7
A3-B5-C2-D7
A9-B5-C2-D7
A13-B5-C2-D7
A24-B5-C2-D7
A69-B5-C2-D7
A67-B5-C2-D7
A39-B5-C2-D7
A65-B5-C2-D7
A66-B5-C2-D7
A2-B6-C2-D7
A3-B6-C2-D7
A9-B6-C2-D7
A13-B6-C2-D7
A24-B6-C2-D7
A69-B6-C2-D7
A67-B6-C2-D7
A39-B6-C2-D7
A65-B6-C2-D7
A66-B6-C2-D7
A2-B32-C2-D7
A3-B32-C2-D7
A9-B32-C2-D7
A13-B32-C2-D7
A24-B32-C2-D7
A69-B32-C2-D7
A67-B32-C2-D7
A39-B32-C2-D7
A65-B32-C2-D7
A66-B32-C2-D7
A2-B39-C2-D7
A3-B39-C2-D7
A9-B39-C2-D7
A13-B39-C2-D7
A24-B39-C2-D7
A69-B39-C2-D7
A67-B39-C2-D7
A39-B39-C2-D7
A65-B39-C2-D7
A66-B39-C2-D7
A2-B45-C2-D7
A3-B45-C2-D7
A9-B45-C2-D7
A13-B45-C2-D7
A24-B45-C2-D7
A69-B45-C2-D7
A67-B45-C2-D7
A39-B45-C2-D7
A65-B45-C2-D7
A66-B45-C2-D7
A2-B53-C2-D7
A3-B53-C2-D7
A9-B53-C2-D7
A13-B53-C2-D7
A24-B53-C2-D7
A69-B53-C2-D7
A67-B53-C2-D7
A39-B53-C2-D7
A65-B53-C2-D7
A66-B53-C2-D7
A2-B79-C2-D7
A3-B79-C2-D7
A9-B79-C2-D7
A13-B79-C2-D7
A24-B79-C2-D7
A69-B79-C2-D7
A67-B79-C2-D7
A39-B79-C2-D7
A65-B79-C2-D7
A66-B79-C2-D7
A2-B80-C2-D7
A3-B80-C2-D7
A9-B80-C2-D7
A13-B80-C2-D7
A24-B80-C2-D7
A69-B80-C2-D7
A67-B80-C2-D7
A39-B80-C2-D7
A65-B80-C2-D7
A66-B80-C2-D7
A2-B85-C2-D7
A3-B85-C2-D7
A9-B85-C2-D7
A13-B85-C2-D7
A24-B85-C2-D7
A69-B85-C2-D7
A67-B85-C2-D7
A39-B85-C2-D7
A65-B85-C2-D7
A66-B85-C2-D7
A2-B86-C2-D7
A3-B86-C2-D7
A9-B86-C2-D7
A13-B86-C2-D7
A24-B86-C2-D7
A69-B86-C2-D7
A67-B86-C2-D7
A39-B86-C2-D7
A65-B86-C2-D7
A66-B86-C2-D7
A2-B87-C2-D7
A3-B87-C2-D7
A9-B87-C2-D7
A13-B87-C2-D7
A24-B87-C2-D7
A69-B87-C2-D7
A67-B87-C2-D7
A39-B87-C2-D7
A65-B87-C2-D7
A66-B87-C2-D7
A2-B89-C2-D7
A3-B89-C2-D7
A9-B89-C2-D7
A13-B89-C2-D7
A24-B89-C2-D7
A69-B89-C2-D7
A67-B89-C2-D7
A39-B89-C2-D7
A65-B89-C2-D7
A66-B89-C2-D7
A2-B92-C2-D7
A3-B92-C2-D7
A9-B92-C2-D7
A13-B92-C2-D7
A24-B92-C2-D7
A69-B92-C2-D7
A67-B92-C2-D7
A39-B92-C2-D7
A65-B92-C2-D7
A66-B92-C2-D7
A2-B4-C3-D7
A3-B4-C3-D7
A9-B4-C3-D7
A13-B4-C3-D7
A24-B4-C3-D7
A69-B4-C3-D7
A67-B4-C3-D7
A39-B4-C3-D7
A65-B4-C3-D7
A66-B4-C3-D7
A2-B5-C3-D7
A3-B5-C3-D7
A9-B5-C3-D7
A13-B5-C3-D7
A24-B5-C3-D7
A69-B5-C3-D7
A67-B5-C3-D7
A39-B5-C3-D7
A65-B5-C3-D7
A66-B5-C3-D7
A2-B6-C3-D7
A3-B6-C3-D7
A9-B6-C3-D7
A13-B6-C3-D7
A24-B6-C3-D7
A69-B6-C3-D7

TABLE 6-continued

A67-B6-C3-D7
A39-B6-C3-D7
A65-B6-C3-D7
A66-B6-C3-D7
A2-B32-C3-D7
A3-B32-C3-D7
A9-B32-C3-D7
A13-B32-C3-D7
A24-B32-C3-D7
A69-B32-C3-D7
A67-B32-C3-D7
A39-B32-C3-D7
A65-B32-C3-D7
A66-B32-C3-D7
A2-B39-C3-D7
A3-B39-C3-D7
A9-B39-C3-D7
A13-B39-C3-D7
A24-B39-C3-D7
A69-B39-C3-D7
A67-B39-C3-D7
A39-B39-C3-D7
A65-B39-C3-D7
A66-B39-C3-D7
A2-B45-C3-D7
A3-B45-C3-D7
A9-B45-C3-D7
A13-B45-C3-D7
A24-B45-C3-D7
A69-B45-C3-D7
A67-B45-C3-D7
A39-B45-C3-D7
A65-B45-C3-D7
A66-B45-C3-D7
A2-B53-C3-D7
A3-B53-C3-D7
A9-B53-C3-D7
A13-B53-C3-D7
A24-B53-C3-D7
A69-B53-C3-D7
A67-B53-C3-D7
A39-B53-C3-D7
A65-B53-C3-D7
A66-B53-C3-D7
A2-B79-C3-D7
A3-B79-C3-D7
A9-B79-C3-D7
A13-B79-C3-D7
A24-B79-C3-D7
A69-B79-C3-D7
A67-B79-C3-D7
A39-B79-C3-D7
A65-B79-C3-D7
A66-B79-C3-D7
A2-B80-C3-D7
A3-B80-C3-D7
A9-B80-C3-D7
A13-B80-C3-D7
A24-B80-C3-D7
A69-B80-C3-D7
A67-B80-C3-D7
A39-B80-C3-D7
A65-B80-C3-D7
A66-B80-C3-D7
A2-B85-C3-D7
A3-B85-C3-D7
A9-B85-C3-D7
A13-B85-C3-D7
A24-B85-C3-D7
A69-B85-C3-D7
A67-B85-C3-D7
A39-B85-C3-D7
A65-B85-C3-D7
A66-B85-C3-D7
A2-B86-C3-D7
A3-B86-C3-D7
A9-B86-C3-D7
A13-B86-C3-D7
A24-B86-C3-D7
A69-B86-C3-D7
A67-B86-C3-D7
A39-B86-C3-D7
A65-B86-C3-D7
A66-B86-C3-D7
A2-B87-C3-D7
A3-B87-C3-D7
A9-B87-C3-D7
A13-B87-C3-D7
A24-B87-C3-D7
A69-B87-C3-D7
A67-B87-C3-D7
A39-B87-C3-D7
A65-B87-C3-D7
A66-B87-C3-D7
A2-B89-C3-D7
A3-B89-C3-D7
A9-B89-C3-D7
A13-B89-C3-D7
A24-B89-C3-D7
A69-B89-C3-D7
A67-B89-C3-D7
A39-B89-C3-D7
A65-B89-C3-D7
A66-B89-C3-D7
A2-B92-C3-D7
A3-B92-C3-D7
A9-B92-C3-D7
A13-B92-C3-D7
A24-B92-C3-D7
A69-B92-C3-D7
A67-B92-C3-D7
A39-B92-C3-D7
A65-B92-C3-D7
A66-B92-C3-D7
A2-B4-C4-D7
A3-B4-C4-D7
A9-B4-C4-D7
A13-B4-C4-D7
A24-B4-C4-D7
A69-B4-C4-D7
A67-B4-C4-D7
A39-B4-C4-D7
A65-B4-C4-D7
A66-B4-C4-D7
A2-B5-C4-D7
A3-B5-C4-D7
A9-B5-C4-D7
A13-B5-C4-D7
A24-B5-C4-D7
A69-B5-C4-D7
A67-B5-C4-D7
A39-B5-C4-D7
A65-B5-C4-D7
A66-B5-C4-D7
A2-B6-C4-D7
A3-B6-C4-D7
A9-B6-C4-D7
A13-B6-C4-D7
A24-B6-C4-D7
A69-B6-C4-D7
A67-B6-C4-D7
A39-B6-C4-D7
A65-B6-C4-D7
A66-B6-C4-D7
A2-B32-C4-D7
A3-B32-C4-D7
A9-B32-C4-D7
A13-B32-C4-D7
A24-B32-C4-D7
A69-B32-C4-D7
A67-B32-C4-D7
A39-B32-C4-D7
A65-B32-C4-D7
A66-B32-C4-D7
A2-B39-C4-D7
A3-B39-C4-D7
A9-B39-C4-D7
A13-B39-C4-D7

TABLE 6-continued

A24-B39-C4-D7
A69-B39-C4-D7
A67-B39-C4-D7
A39-B39-C4-D7
A65-B39-C4-D7
A66-B39-C4-D7
A2-B45-C4-D7
A3-B45-C4-D7
A9-B45-C4-D7
A13-B45-C4-D7
A24-B45-C4-D7
A69-B45-C4-D7
A67-B45-C4-D7
A39-B45-C4-D7
A65-B45-C4-D7
A66-B45-C4-D7
A2-B53-C4-D7
A3-B53-C4-D7
A9-B53-C4-D7
A13-B53-C4-D7
A24-B53-C4-D7
A69-B53-C4-D7
A67-B53-C4-D7
A39-B53-C4-D7
A65-B53-C4-D7
A66-B53-C4-D7
A2-B79-C4-D7
A3-B79-C4-D7
A9-B79-C4-D7
A13-B79-C4-D7
A24-B79-C4-D7
A69-B79-C4-D7
A67-B79-C4-D7
A39-B79-C4-D7
A65-B79-C4-D7
A66-B79-C4-D7
A2-B80-C4-D7
A3-B80-C4-D7
A9-B80-C4-D7
A13-B80-C4-D7
A24-B80-C4-D7
A69-B80-C4-D7
A67-B80-C4-D7
A39-B80-C4-D7
A65-B80-C4-D7
A66-B80-C4-D7
A2-B85-C4-D7
A3-B85-C4-D7
A9-B85-C4-D7
A13-B85-C4-D7
A24-B85-C4-D7
A69-B85-C4-D7
A67-B85-C4-D7
A39-B85-C4-D7
A65-B85-C4-D7
A66-B85-C4-D7
A2-B86-C4-D7
A3-B86-C4-D7
A9-B86-C4-D7
A13-B86-C4-D7
A24-B86-C4-D7
A69-B86-C4-D7
A67-B86-C4-D7
A39-B86-C4-D7
A65-B86-C4-D7
A66-B86-C4-D7
A2-B87-C4-D7
A3-B87-C4-D7
A9-B87-C4-D7
A13-B87-C4-D7
A24-B87-C4-D7
A69-B87-C4-D7
A67-B87-C4-D7
A39-B87-C4-D7
A65-B87-C4-D7
A66-B87-C4-D7
A2-B89-C4-D7
A3-B89-C4-D7
A9-B89-C4-D7

TABLE 6-continued

A13-B89-C4-D7
A24-B89-C4-D7
A69-B89-C4-D7
A67-B89-C4-D7
A39-B89-C4-D7
A65-B89-C4-D7
A66-B89-C4-D7
A2-B92-C4-D7
A3-B92-C4-D7
A9-B92-C4-D7
A13-B92-C4-D7
A24-B92-C4-D7
A69-B92-C4-D7
A67-B92-C4-D7
A39-B92-C4-D7
A65-B92-C4-D7
A66-B92-C4-D7
A2-B4-C5-D7
A3-B4-C5-D7
A9-B4-C5-D7
A13-B4-C5-D7
A24-B4-C5-D7
A69-B4-C5-D7
A67-B4-C5-D7
A39-B4-C5-D7
A65-B4-C5-D7
A66-B4-C5-D7
A2-B5-C5-D7
A3-B5-C5-D7
A9-B5-C5-D7
A13-B5-C5-D7
A24-B5-C5-D7
A69-B5-C5-D7
A67-B5-C5-D7
A39-B5-C5-D7
A65-B5-C5-D7
A66-B5-C5-D7
A2-B6-C5-D7
A3-B6-C5-D7
A9-B6-C5-D7
A13-B6-C5-D7
A24-B6-C5-D7
A69-B6-C5-D7
A67-B6-C5-D7
A39-B6-C5-D7
A65-B6-C5-D7
A66-B6-C5-D7
A2-B32-C5-D7
A3-B32-C5-D7
A9-B32-C5-D7
A13-B32-C5-D7
A24-B32-C5-D7
A69-B32-C5-D7
A67-B32-C5-D7
A39-B32-C5-D7
A65-B32-C5-D7
A66-B32-C5-D7
A2-B39-C5-D7
A3-B39-C5-D7
A9-B39-C5-D7
A13-B39-C5-D7
A24-B39-C5-D7
A69-B39-C5-D7
A67-B39-C5-D7
A39-B39-C5-D7
A65-B39-C5-D7
A66-B39-C5-D7
A2-B45-C5-D7
A3-B45-C5-D7
A9-B45-C5-D7
A13-B45-C5-D7
A24-B45-C5-D7
A69-B45-C5-D7
A67-B45-C5-D7
A39-B45-C5-D7
A65-B45-C5-D7
A66-B45-C5-D7
A2-B53-C5-D7
A3-B53-C5-D7

TABLE 6-continued

A9-B53-C5-D7
A13-B53-C5-D7
A24-B53-C5-D7
A69-B53-C5-D7
A67-B53-C5-D7
A39-B53-C5-D7
A65-B53-C5-D7
A66-B53-C5-D7
A2-B79-C5-D7
A3-B79-C5-D7
A9-B79-C5-D7
A13-B79-C5-D7
A24-B79-C5-D7
A69-B79-C5-D7
A67-B79-C5-D7
A39-B79-C5-D7
A65-B79-C5-D7
A66-B79-C5-D7
A2-B80-C5-D7
A3-B80-C5-D7
A9-B80-C5-D7
A13-B80-C5-D7
A24-B80-C5-D7
A69-B80-C5-D7
A67-B80-C5-D7
A39-B80-C5-D7
A65-B80-C5-D7
A66-B80-C5-D7
A2-B85-C5-D7
A3-B85-C5-D7
A9-B85-C5-D7
A13-B85-C5-D7
A24-B85-C5-D7
A69-B85-C5-D7
A67-B85-C5-D7
A39-B85-C5-D7
A65-B85-C5-D7
A66-B85-C5-D7
A2-B86-C5-D7
A3-B86-C5-D7
A9-B86-C5-D7
A13-B86-C5-D7
A24-B86-C5-D7
A69-B86-C5-D7
A67-B86-C5-D7
A39-B86-C5-D7
A65-B86-C5-D7
A66-B86-C5-D7
A2-B87-C5-D7
A3-B87-C5-D7
A9-B87-C5-D7
A13-B87-C5-D7
A24-B87-C5-D7
A69-B87-C5-D7
A67-B87-C5-D7
A39-B87-C5-D7
A65-B87-C5-D7
A66-B87-C5-D7
A2-B89-C5-D7
A3-B89-C5-D7
A9-B89-C5-D7
A13-B89-C5-D7
A24-B89-C5-D7
A69-B89-C5-D7
A67-B89-C5-D7
A39-B89-C5-D7
A65-B89-C5-D7
A66-B89-C5-D7
A2-B92-C5-D7
A3-B92-C5-D7
A9-B92-C5-D7
A13-B92-C5-D7
A24-B92-C5-D7
A69-B92-C5-D7
A67-B92-C5-D7
A39-B92-C5-D7
A65-B92-C5-D7
A66-B92-C5-D7
A2-B4-C6-D7

TABLE 6-continued

A3-B4-C6-D7
A9-B4-C6-D7
A13-B4-C6-D7
A24-B4-C6-D7
A69-B4-C6-D7
A67-B4-C6-D7
A39-B4-C6-D7
A65-B4-C6-D7
A66-B4-C6-D7
A2-B5-C6-D7
A3-B5-C6-D7
A9-B5-C6-D7
A13-B5-C6-D7
A24-B5-C6-D7
A69-B5-C6-D7
A67-B5-C6-D7
A39-B5-C6-D7
A65-B5-C6-D7
A66-B5-C6-D7
A2-B6-C6-D7
A3-B6-C6-D7
A9-B6-C6-D7
A13-B6-C6-D7
A24-B6-C6-D7
A69-B6-C6-D7
A67-B6-C6-D7
A39-B6-C6-D7
A65-B6-C6-D7
A66-B6-C6-D7
A2-B32-C6-D7
A3-B32-C6-D7
A9-B32-C6-D7
A13-B32-C6-D7
A24-B32-C6-D7
A69-B32-C6-D7
A67-B32-C6-D7
A39-B32-C6-D7
A65-B32-C6-D7
A66-B32-C6-D7
A2-B39-C6-D7
A3-B39-C6-D7
A9-B39-C6-D7
A13-B39-C6-D7
A24-B39-C6-D7
A69-B39-C6-D7
A67-B39-C6-D7
A39-B39-C6-D7
A65-B39-C6-D7
A66-B39-C6-D7
A2-B45-C6-D7
A3-B45-C6-D7
A9-B45-C6-D7
A13-B45-C6-D7
A24-B45-C6-D7
A69-B45-C6-D7
A67-B45-C6-D7
A39-B45-C6-D7
A65-B45-C6-D7
A66-B45-C6-D7
A2-B53-C6-D7
A3-B53-C6-D7
A9-B53-C6-D7
A13-B53-C6-D7
A24-B53-C6-D7
A69-B53-C6-D7
A67-B53-C6-D7
A39-B53-C6-D7
A65-B53-C6-D7
A66-B53-C6-D7
A2-B79-C6-D7
A3-B79-C6-D7
A9-B79-C6-D7
A13-B79-C6-D7
A24-B79-C6-D7
A69-B79-C6-D7
A67-B79-C6-D7
A39-B79-C6-D7
A65-B79-C6-D7
A66-B79-C6-D7

TABLE 6-continued

A2-B80-C6-D7
A3-B80-C6-D7
A9-B80-C6-D7
A13-B80-C6-D7
A24-B80-C6-D7
A69-B80-C6-D7
A67-B80-C6-D7
A39-B80-C6-D7
A65-B80-C6-D7
A66-B80-C6-D7
A2-B85-C6-D7
A3-B85-C6-D7
A9-B85-C6-D7
A13-B85-C6-D7
A24-B85-C6-D7
A69-B85-C6-D7
A67-B85-C6-D7
A39-B85-C6-D7
A65-B85-C6-D7
A66-B85-C6-D7
A2-B86-C6-D7
A3-B86-C6-D7
A9-B86-C6-D7
A13-B86-C6-D7
A24-B86-C6-D7
A69-B86-C6-D7
A67-B86-C6-D7
A39-B86-C6-D7
A65-B86-C6-D7
A66-B86-C6-D7
A2-B87-C6-D7
A3-B87-C6-D7
A9-B87-C6-D7
A13-B87-C6-D7
A24-B87-C6-D7
A69-B87-C6-D7
A67-B87-C6-D7
A39-B87-C6-D7
A65-B87-C6-D7
A66-B87-C6-D7
A2-B89-C6-D7
A3-B89-C6-D7
A9-B89-C6-D7
A13-B89-C6-D7
A24-B89-C6-D7
A69-B89-C6-D7
A67-B89-C6-D7
A39-B89-C6-D7
A65-B89-C6-D7
A66-B89-C6-D7
A2-B92-C6-D7
A3-B92-C6-D7
A9-B92-C6-D7
A13-B92-C6-D7
A24-B92-C6-D7
A69-B92-C6-D7
A67-B92-C6-D7
A39-B92-C6-D7
A65-B92-C6-D7
A66-B92-C6-D7
A2-B4-C7-D7
A3-B4-C7-D7
A9-B4-C7-D7
A13-B4-C7-D7
A24-B4-C7-D7
A69-B4-C7-D7
A67-B4-C7-D7
A39-B4-C7-D7
A65-B4-C7-D7
A66-B4-C7-D7
A2-B5-C7-D7
A3-B5-C7-D7
A9-B5-C7-D7
A13-B5-C7-D7
A24-B5-C7-D7
A69-B5-C7-D7
A67-B5-C7-D7
A39-B5-C7-D7
A65-B5-C7-D7

TABLE 6-continued

A66-B5-C7-D7
A2-B6-C7-D7
A3-B6-C7-D7
A9-B6-C7-D7
A13-B6-C7-D7
A24-B6-C7-D7
A69-B6-C7-D7
A67-B6-C7-D7
A39-B6-C7-D7
A65-B6-C7-D7
A66-B6-C7-D7
A2-B32-C7-D7
A3-B32-C7-D7
A9-B32-C7-D7
A13-B32-C7-D7
A24-B32-C7-D7
A69-B32-C7-D7
A67-B32-C7-D7
A39-B32-C7-D7
A65-B32-C7-D7
A66-B32-C7-D7
A2-B39-C7-D7
A3-B39-C7-D7
A9-B39-C7-D7
A13-B39-C7-D7
A24-B39-C7-D7
A69-B39-C7-D7
A67-B39-C7-D7
A39-B39-C7-D7
A65-B39-C7-D7
A66-B39-C7-D7
A2-B45-C7-D7
A3-B45-C7-D7
A9-B45-C7-D7
A13-B45-C7-D7
A24-B45-C7-D7
A69-B45-C7-D7
A67-B45-C7-D7
A39-B45-C7-D7
A65-B45-C7-D7
A66-B45-C7-D7
A2-B53-C7-D7
A3-B53-C7-D7
A9-B53-C7-D7
A13-B53-C7-D7
A24-B53-C7-D7
A69-B53-C7-D7
A67-B53-C7-D7
A39-B53-C7-D7
A65-B53-C7-D7
A66-B53-C7-D7
A2-B79-C7-D7
A3-B79-C7-D7
A9-B79-C7-D7
A13-B79-C7-D7
A24-B79-C7-D7
A69-B79-C7-D7
A67-B79-C7-D7
A39-B79-C7-D7
A65-B79-C7-D7
A66-B79-C7-D7
A2-B80-C7-D7
A3-B80-C7-D7
A9-B80-C7-D7
A13-B80-C7-D7
A24-B80-C7-D7
A69-B80-C7-D7
A67-B80-C7-D7
A39-B80-C7-D7
A65-B80-C7-D7
A66-B80-C7-D7
A2-B85-C7-D7
A3-B85-C7-D7
A9-B85-C7-D7
A13-B85-C7-D7
A24-B85-C7-D7
A69-B85-C7-D7
A67-B85-C7-D7
A39-B85-C7-D7

TABLE 6-continued

A65-B85-C7-D7
A66-B85-C7-D7
A2-B86-C7-D7
A3-B86-C7-D7
A9-B86-C7-D7
A13-B86-C7-D7
A24-B86-C7-D7
A69-B86-C7-D7
A67-B86-C7-D7
A39-B86-C7-D7
A65-B86-C7-D7
A66-B86-C7-D7
A2-B87-C7-D7
A3-B87-C7-D7
A9-B87-C7-D7
A13-B87-C7-D7
A24-B87-C7-D7
A69-B87-C7-D7
A67-B87-C7-D7
A39-B87-C7-D7
A65-B87-C7-D7
A66-B87-C7-D7
A2-B89-C7-D7
A3-B89-C7-D7
A9-B89-C7-D7
A13-B89-C7-D7
A24-B89-C7-D7
A69-B89-C7-D7
A67-B89-C7-D7
A39-B89-C7-D7
A65-B89-C7-D7
A66-B89-C7-D7
A2-B92-C7-D7
A3-B92-C7-D7
A9-B92-C7-D7
A13-B92-C7-D7
A24-B92-C7-D7
A69-B92-C7-D7
A67-B92-C7-D7
A39-B92-C7-D7
A65-B92-C7-D7
A66-B92-C7-D7
A2-B4-C8-D7
A3-B4-C8-D7
A9-B4-C8-D7
A13-B4-C8-D7
A24-B4-C8-D7
A69-B4-C8-D7
A67-B4-C8-D7
A39-B4-C8-D7
A65-B4-C8-D7
A66-B4-C8-D7
A2-B5-C8-D7
A3-B5-C8-D7
A9-B5-C8-D7
A13-B5-C8-D7
A24-B5-C8-D7
A69-B5-C8-D7
A67-B5-C8-D7
A39-B5-C8-D7
A65-B5-C8-D7
A66-B5-C8-D7
A2-B6-C8-D7
A3-B6-C8-D7
A9-B6-C8-D7
A13-B6-C8-D7
A24-B6-C8-D7
A69-B6-C8-D7
A67-B6-C8-D7
A39-B6-C8-D7
A65-B6-C8-D7
A66-B6-C8-D7
A2-B32-C8-D7
A3-B32-C8-D7
A9-B32-C8-D7
A13-B32-C8-D7
A24-B32-C8-D7
A69-B32-C8-D7
A67-B32-C8-D7

TABLE 6-continued

A39-B32-C8-D7
A65-B32-C8-D7
A66-B32-C8-D7
A2-B39-C8-D7
A3-B39-C8-D7
A9-B39-C8-D7
A13-B39-C8-D7
A24-B39-C8-D7
A69-B39-C8-D7
A67-B39-C8-D7
A39-B39-C8-D7
A65-B39-C8-D7
A66-B39-C8-D7
A2-B45-C8-D7
A3-B45-C8-D7
A9-B45-C8-D7
A13-B45-C8-D7
A24-B45-C8-D7
A69-B45-C8-D7
A67-B45-C8-D7
A39-B45-C8-D7
A65-B45-C8-D7
A66-B45-C8-D7
A2-B53-C8-D7
A3-B53-C8-D7
A9-B53-C8-D7
A13-B53-C8-D7
A24-B53-C8-D7
A69-B53-C8-D7
A67-B53-C8-D7
A39-B53-C8-D7
A65-B53-C8-D7
A66-B53-C8-D7
A2-B79-C8-D7
A3-B79-C8-D7
A9-B79-C8-D7
A13-B79-C8-D7
A24-B79-C8-D7
A69-B79-C8-D7
A67-B79-C8-D7
A39-B79-C8-D7
A65-B79-C8-D7
A66-B79-C8-D7
A2-B80-C8-D7
A3-B80-C8-D7
A9-B80-C8-D7
A13-B80-C8-D7
A24-B80-C8-D7
A69-B80-C8-D7
A67-B80-C8-D7
A39-B80-C8-D7
A65-B80-C8-D7
A66-B80-C8-D7
A2-B85-C8-D7
A3-B85-C8-D7
A9-B85-C8-D7
A13-B85-C8-D7
A24-B85-C8-D7
A69-B85-C8-D7
A67-B85-C8-D7
A39-B85-C8-D7
A65-B85-C8-D7
A66-B85-C8-D7
A2-B86-C8-D7
A3-B86-C8-D7
A9-B86-C8-D7
A13-B86-C8-D7
A24-B86-C8-D7
A69-B86-C8-D7
A67-B86-C8-D7
A39-B86-C8-D7
A65-B86-C8-D7
A66-B86-C8-D7
A2-B87-C8-D7
A3-B87-C8-D7
A9-B87-C8-D7
A13-B87-C8-D7
A24-B87-C8-D7
A69-B87-C8-D7

TABLE 6-continued

A67-B87-C8-D7
A39-B87-C8-D7
A65-B87-C8-D7
A66-B87-C8-D7
A2-B89-C8-D7
A3-B89-C8-D7
A9-B89-C8-D7
A13-B89-C8-D7
A24-B89-C8-D7
A69-B89-C8-D7
A67-B89-C8-D7
A39-B89-C8-D7
A65-B89-C8-D7
A66-B89-C8-D7
A2-B92-C8-D7
A3-B92-C8-D7
A9-B92-C8-D7
A13-B92-C8-D7
A24-B92-C8-D7
A69-B92-C8-D7
A67-B92-C8-D7
A39-B92-C8-D7
A65-B92-C8-D7
A66-B92-C8-D7
A2-B4-C9-D7
A3-B4-C9-D7
A9-B4-C9-D7
A13-B4-C9-D7
A24-B4-C9-D7
A69-B4-C9-D7
A67-B4-C9-D7
A39-B4-C9-D7
A65-B4-C9-D7
A66-B4-C9-D7
A2-B5-C9-D7
A3-B5-C9-D7
A9-B5-C9-D7
A13-B5-C9-D7
A24-B5-C9-D7
A69-B5-C9-D7
A67-B5-C9-D7
A39-B5-C9-D7
A65-B5-C9-D7
A66-B5-C9-D7
A2-B6-C9-D7
A3-B6-C9-D7
A9-B6-C9-D7
A13-B6-C9-D7
A24-B6-C9-D7
A69-B6-C9-D7
A67-B6-C9-D7
A39-B6-C9-D7
A65-B6-C9-D7
A66-B6-C9-D7
A2-B32-C9-D7
A3-B32-C9-D7
A9-B32-C9-D7
A13-B32-C9-D7
A24-B32-C9-D7
A69-B32-C9-D7
A67-B32-C9-D7
A39-B32-C9-D7
A65-B32-C9-D7
A66-B32-C9-D7
A2-B39-C9-D7
A3-B39-C9-D7
A9-B39-C9-D7
A13-B39-C9-D7
A24-B39-C9-D7
A69-B39-C9-D7
A67-B39-C9-D7
A39-B39-C9-D7
A65-B39-C9-D7
A66-B39-C9-D7
A2-B45-C9-D7
A3-B45-C9-D7
A9-B45-C9-D7
A13-B45-C9-D7
A24-B45-C9-D7

TABLE 6-continued

A69-B45-C9-D7
A67-B45-C9-D7
A39-B45-C9-D7
A65-B45-C9-D7
A66-B45-C9-D7
A2-B53-C9-D7
A3-B53-C9-D7
A9-B53-C9-D7
A13-B53-C9-D7
A24-B53-C9-D7
A69-B53-C9-D7
A67-B53-C9-D7
A39-B53-C9-D7
A65-B53-C9-D7
A66-B53-C9-D7
A2-B79-C9-D7
A3-B79-C9-D7
A9-B79-C9-D7
A13-B79-C9-D7
A24-B79-C9-D7
A69-B79-C9-D7
A67-B79-C9-D7
A39-B79-C9-D7
A65-B79-C9-D7
A66-B79-C9-D7
A2-B80-C9-D7
A3-B80-C9-D7
A9-B80-C9-D7
A13-B80-C9-D7
A24-B80-C9-D7
A69-B80-C9-D7
A67-B80-C9-D7
A39-B80-C9-D7
A65-B80-C9-D7
A66-B80-C9-D7
A2-B85-C9-D7
A3-B85-C9-D7
A9-B85-C9-D7
A13-B85-C9-D7
A24-B85-C9-D7
A69-B85-C9-D7
A67-B85-C9-D7
A39-B85-C9-D7
A65-B85-C9-D7
A66-B85-C9-D7
A2-B86-C9-D7
A3-B86-C9-D7
A9-B86-C9-D7
A13-B86-C9-D7
A24-B86-C9-D7
A69-B86-C9-D7
A67-B86-C9-D7
A39-B86-C9-D7
A65-B86-C9-D7
A66-B86-C9-D7
A2-B87-C9-D7
A3-B87-C9-D7
A9-B87-C9-D7
A13-B87-C9-D7
A24-B87-C9-D7
A69-B87-C9-D7
A67-B87-C9-D7
A39-B87-C9-D7
A65-B87-C9-D7
A66-B87-C9-D7
A2-B89-C9-D7
A3-B89-C9-D7
A9-B89-C9-D7
A13-B89-C9-D7
A24-B89-C9-D7
A69-B89-C9-D7
A67-B89-C9-D7
A39-B89-C9-D7
A65-B89-C9-D7
A66-B89-C9-D7
A2-B92-C9-D7
A3-B92-C9-D7
A9-B92-C9-D7
A13-B92-C9-D7

TABLE 6-continued

A24-B92-C9-D7
A69-B92-C9-D7
A67-B92-C9-D7
A39-B92-C9-D7
A65-B92-C9-D7
A66-B92-C9-D7
A2-B4-C10-D7
A3-B4-C10-D7
A9-B4-C10-D7
A13-B4-C10-D7
A24-B4-C10-D7
A69-B4-C10-D7
A67-B4-C10-D7
A39-B4-C10-D7
A65-B4-C10-D7
A66-B4-C10-D7
A2-B5-C10-D7
A3-B5-C10-D7
A9-B5-C10-D7
A13-B5-C10-D7
A24-B5-C10-D7
A69-B5-C10-D7
A67-B5-C10-D7
A39-B5-C10-D7
A65-B5-C10-D7
A66-B5-C10-D7
A2-B6-C10-D7
A3-B6-C10-D7
A9-B6-C10-D7
A13-B6-C10-D7
A24-B6-C10-D7
A69-B6-C10-D7
A67-B6-C10-D7
A39-B6-C10-D7
A65-B6-C10-D7
A66-B6-C10-D7
A2-B32-C10-D7
A3-B32-C10-D7
A9-B32-C10-D7
A13-B32-C10-D7
A24-B32-C10-D7
A69-B32-C10-D7
A67-B32-C10-D7
A39-B32-C10-D7
A65-B32-C10-D7
A66-B32-C10-D7
A2-B39-C10-D7
A3-B39-C10-D7
A9-B39-C10-D7
A13-B39-C10-D7
A24-B39-C10-D7
A69-B39-C10-D7
A67-B39-C10-D7
A39-B39-C10-D7
A65-B39-C10-D7
A66-B39-C10-D7
A2-B45-C10-D7
A3-B45-C10-D7
A9-B45-C10-D7
A13-B45-C10-D7
A24-B45-C10-D7
A69-B45-C10-D7
A67-B45-C10-D7
A39-B45-C10-D7
A65-B45-C10-D7
A66-B45-C10-D7
A2-B53-C10-D7
A3-B53-C10-D7
A9-B53-C10-D7
A13-B53-C10-D7
A24-B53-C10-D7
A69-B53-C10-D7
A67-B53-C10-D7
A39-B53-C10-D7
A65-B53-C10-D7
A66-B53-C10-D7
A2-B79-C10-D7
A3-B79-C10-D7
A9-B79-C10-D7

TABLE 6-continued

A13-B79-C10-D7
A24-B79-C10-D7
A69-B79-C10-D7
A67-B79-C10-D7
A39-B79-C10-D7
A65-B79-C10-D7
A66-B79-C10-D7
A2-B80-C10-D7
A3-B80-C10-D7
A9-B80-C10-D7
A13-B80-C10-D7
A24-B80-C10-D7
A69-B80-C10-D7
A67-B80-C10-D7
A39-B80-C10-D7
A65-B80-C10-D7
A66-B80-C10-D7
A2-B85-C10-D7
A3-B85-C10-D7
A9-B85-C10-D7
A13-B85-C10-D7
A24-B85-C10-D7
A69-B85-C10-D7
A67-B85-C10-D7
A39-B85-C10-D7
A65-B85-C10-D7
A66-B85-C10-D7
A2-B86-C10-D7
A3-B86-C10-D7
A9-B86-C10-D7
A13-B86-C10-D7
A24-B86-C10-D7
A69-B86-C10-D7
A67-B86-C10-D7
A39-B86-C10-D7
A65-B86-C10-D7
A66-B86-C10-D7
A2-B87-C10-D7
A3-B87-C10-D7
A9-B87-C10-D7
A13-B87-C10-D7
A24-B87-C10-D7
A69-B87-C10-D7
A67-B87-C10-D7
A39-B87-C10-D7
A65-B87-C10-D7
A66-B87-C10-D7
A2-B89-C10-D7
A3-B89-C10-D7
A9-B89-C10-D7
A13-B89-C10-D7
A24-B89-C10-D7
A69-B89-C10-D7
A67-B89-C10-D7
A39-B89-C10-D7
A65-B89-C10-D7
A66-B89-C10-D7
A2-B92-C10-D7
A3-B92-C10-D7
A9-B92-C10-D7
A13-B92-C10-D7
A24-B92-C10-D7
A69-B92-C10-D7
A67-B92-C10-D7
A39-B92-C10-D7
A65-B92-C10-D7
A66-B92-C10-D7
A2-B4-C11-D7
A3-B4-C11-D7
A9-B4-C11-D7
A13-B4-C11-D7
A24-B4-C11-D7
A69-B4-C11-D7
A67-B4-C11-D7
A39-B4-C11-D7
A65-B4-C11-D7
A66-B4-C11-D7
A2-B5-C11-D7
A3-B5-C11-D7

TABLE 6-continued

| | |
|---|---|
| A9-B5-C11-D7 | A3-B85-C11-D7 |
| A13-B5-C11-D7 | A9-B85-C11-D7 |
| A24-B5-C11-D7 | A13-B85-C11-D7 |
| A69-B5-C11-D7 | A24-B85-C11-D7 |
| A67-B5-C11-D7 | A69-B85-C11-D7 |
| A39-B5-C11-D7 | A67-B85-C11-D7 |
| A65-B5-C11-D7 | A39-B85-C11-D7 |
| A66-B5-C11-D7 | A65-B85-C11-D7 |
| A2-B6-C11-D7 | A66-B85-C11-D7 |
| A3-B6-C11-D7 | A2-B86-C11-D7 |
| A9-B6-C11-D7 | A3-B86-C11-D7 |
| A13-B6-C11-D7 | A9-B86-C11-D7 |
| A24-B6-C11-D7 | A13-B86-C11-D7 |
| A69-B6-C11-D7 | A24-B86-C11-D7 |
| A67-B6-C11-D7 | A69-B86-C11-D7 |
| A39-B6-C11-D7 | A67-B86-C11-D7 |
| A65-B6-C11-D7 | A39-B86-C11-D7 |
| A66-B6-C11-D7 | A65-B86-C11-D7 |
| A2-B32-C11-D7 | A66-B86-C11-D7 |
| A3-B32-C11-D7 | A2-B87-C11-D7 |
| A9-B32-C11-D7 | A3-B87-C11-D7 |
| A13-B32-C11-D7 | A9-B87-C11-D7 |
| A24-B32-C11-D7 | A13-B87-C11-D7 |
| A69-B32-C11-D7 | A24-B87-C11-D7 |
| A67-B32-C11-D7 | A69-B87-C11-D7 |
| A39-B32-C11-D7 | A67-B87-C11-D7 |
| A65-B32-C11-D7 | A39-B87-C11-D7 |
| A66-B32-C11-D7 | A65-B87-C11-D7 |
| A2-B39-C11-D7 | A66-B87-C11-D7 |
| A3-B39-C11-D7 | A2-B89-C11-D7 |
| A9-B39-C11-D7 | A3-B89-C11-D7 |
| A13-B39-C11-D7 | A9-B89-C11-D7 |
| A24-B39-C11-D7 | A13-B89-C11-D7 |
| A69-B39-C11-D7 | A24-B89-C11-D7 |
| A67-B39-C11-D7 | A69-B89-C11-D7 |
| A39-B39-C11-D7 | A67-B89-C11-D7 |
| A65-B39-C11-D7 | A39-B89-C11-D7 |
| A66-B39-C11-D7 | A65-B89-C11-D7 |
| A2-B45-C11-D7 | A66-B89-C11-D7 |
| A3-B45-C11-D7 | A2-B92-C11-D7 |
| A9-B45-C11-D7 | A3-B92-C11-D7 |
| A13-B45-C11-D7 | A9-B92-C11-D7 |
| A24-B45-C11-D7 | A13-B92-C11-D7 |
| A69-B45-C11-D7 | A24-B92-C11-D7 |
| A67-B45-C11-D7 | A69-B92-C11-D7 |
| A39-B45-C11-D7 | A67-B92-C11-D7 |
| A65-B45-C11-D7 | A39-B92-C11-D7 |
| A66-B45-C11-D7 | A65-B92-C11-D7 |
| A2-B53-C11-D7 | A66-B92-C11-D7 |
| A3-B53-C11-D7 | A2-B4-C12-D7 |
| A9-B53-C11-D7 | A3-B4-C12-D7 |
| A13-B53-C11-D7 | A9-B4-C12-D7 |
| A24-B53-C11-D7 | A13-B4-C12-D7 |
| A69-B53-C11-D7 | A24-B4-C12-D7 |
| A67-B53-C11-D7 | A69-B4-C12-D7 |
| A39-B53-C11-D7 | A67-B4-C12-D7 |
| A65-B53-C11-D7 | A39-B4-C12-D7 |
| A66-B53-C11-D7 | A65-B4-C12-D7 |
| A2-B79-C11-D7 | A66-B4-C12-D7 |
| A3-B79-C11-D7 | A2-B5-C12-D7 |
| A9-B79-C11-D7 | A3-B5-C12-D7 |
| A13-B79-C11-D7 | A9-B5-C12-D7 |
| A24-B79-C11-D7 | A13-B5-C12-D7 |
| A69-B79-C11-D7 | A24-B5-C12-D7 |
| A67-B79-C11-D7 | A69-B5-C12-D7 |
| A39-B79-C11-D7 | A67-B5-C12-D7 |
| A65-B79-C11-D7 | A39-B5-C12-D7 |
| A66-B79-C11-D7 | A65-B5-C12-D7 |
| A2-B80-C11-D7 | A66-B5-C12-D7 |
| A3-B80-C11-D7 | A2-B6-C12-D7 |
| A9-B80-C11-D7 | A3-B6-C12-D7 |
| A13-B80-C11-D7 | A9-B6-C12-D7 |
| A24-B80-C11-D7 | A13-B6-C12-D7 |
| A69-B80-C11-D7 | A24-B6-C12-D7 |
| A67-B80-C11-D7 | A69-B6-C12-D7 |
| A39-B80-C11-D7 | A67-B6-C12-D7 |
| A65-B80-C11-D7 | A39-B6-C12-D7 |
| A66-B80-C11-D7 | A65-B6-C12-D7 |
| A2-B85-C11-D7 | A66-B6-C12-D7 |

TABLE 6-continued

A2-B32-C12-D7
A3-B32-C12-D7
A9-B32-C12-D7
A13-B32-C12-D7
A24-B32-C12-D7
A69-B32-C12-D7
A67-B32-C12-D7
A39-B32-C12-D7
A65-B32-C12-D7
A66-B32-C12-D7
A2-B39-C12-D7
A3-B39-C12-D7
A9-B39-C12-D7
A13-B39-C12-D7
A24-B39-C12-D7
A69-B39-C12-D7
A67-B39-C12-D7
A39-B39-C12-D7
A65-B39-C12-D7
A66-B39-C12-D7
A2-B45-C12-D7
A3-B45-C12-D7
A9-B45-C12-D7
A13-B45-C12-D7
A24-B45-C12-D7
A69-B45-C12-D7
A67-B45-C12-D7
A39-B45-C12-D7
A65-B45-C12-D7
A66-B45-C12-D7
A2-B53-C12-D7
A3-B53-C12-D7
A9-B53-C12-D7
A13-B53-C12-D7
A24-B53-C12-D7
A69-B53-C12-D7
A67-B53-C12-D7
A39-B53-C12-D7
A65-B53-C12-D7
A66-B53-C12-D7
A2-B79-C12-D7
A3-B79-C12-D7
A9-B79-C12-D7
A13-B79-C12-D7
A24-B79-C12-D7
A69-B79-C12-D7
A67-B79-C12-D7
A39-B79-C12-D7
A65-B79-C12-D7
A66-B79-C12-D7
A2-B80-C12-D7
A3-B80-C12-D7
A9-B80-C12-D7
A13-B80-C12-D7
A24-B80-C12-D7
A69-B80-C12-D7
A67-B80-C12-D7
A39-B80-C12-D7
A65-B80-C12-D7
A66-B80-C12-D7
A2-B85-C12-D7
A3-B85-C12-D7
A9-B85-C12-D7
A13-B85-C12-D7
A24-B85-C12-D7
A69-B85-C12-D7
A67-B85-C12-D7
A39-B85-C12-D7
A65-B85-C12-D7
A66-B85-C12-D7
A2-B86-C12-D7
A3-B86-C12-D7
A9-B86-C12-D7
A13-B86-C12-D7
A24-B86-C12-D7
A69-B86-C12-D7
A67-B86-C12-D7
A39-B86-C12-D7
A65-B86-C12-D7

TABLE 6-continued

A66-B86-C12-D7
A2-B87-C12-D7
A3-B87-C12-D7
A9-B87-C12-D7
A13-B87-C12-D7
A24-B87-C12-D7
A69-B87-C12-D7
A67-B87-C12-D7
A39-B87-C12-D7
A65-B87-C12-D7
A66-B87-C12-D7
A2-B89-C12-D7
A3-B89-C12-D7
A9-B89-C12-D7
A13-B89-C12-D7
A24-B89-C12-D7
A69-B89-C12-D7
A67-B89-C12-D7
A39-B89-C12-D7
A65-B89-C12-D7
A66-B89-C12-D7
A2-B92-C12-D7
A3-B92-C12-D7
A9-B92-C12-D7
A13-B92-C12-D7
A24-B92-C12-D7
A69-B92-C12-D7
A67-B92-C12-D7
A39-B92-C12-D7
A65-B92-C12-D7
A66-B92-C12-D7
A2-B4-C13-D7
A3-B4-C13-D7
A9-B4-C13-D7
A13-B4-C13-D7
A24-B4-C13-D7
A69-B4-C13-D7
A67-B4-C13-D7
A39-B4-C13-D7
A65-B4-C13-D7
A66-B4-C13-D7
A2-B5-C13-D7
A3-B5-C13-D7
A9-B5-C13-D7
A13-B5-C13-D7
A24-B5-C13-D7
A69-B5-C13-D7
A67-B5-C13-D7
A39-B5-C13-D7
A65-B5-C13-D7
A66-B5-C13-D7
A2-B6-C13-D7
A3-B6-C13-D7
A9-B6-C13-D7
A13-B6-C13-D7
A24-B6-C13-D7
A69-B6-C13-D7
A67-B6-C13-D7
A39-B6-C13-D7
A65-B6-C13-D7
A66-B6-C13-D7
A2-B32-C13-D7
A3-B32-C13-D7
A9-B32-C13-D7
A13-B32-C13-D7
A24-B32-C13-D7
A69-B32-C13-D7
A67-B32-C13-D7
A39-B32-C13-D7
A65-B32-C13-D7
A66-B32-C13-D7
A2-B39-C13-D7
A3-B39-C13-D7
A9-B39-C13-D7
A13-B39-C13-D7
A24-B39-C13-D7
A69-B39-C13-D7
A67-B39-C13-D7
A39-B39-C13-D7

TABLE 6-continued

A65-B39-C13-D7
A66-B39-C13-D7
A2-B45-C13-D7
A3-B45-C13-D7
A9-B45-C13-D7
A13-B45-C13-D7
A24-B45-C13-D7
A69-B45-C13-D7
A67-B45-C13-D7
A39-B45-C13-D7
A65-B45-C13-D7
A66-B45-C13-D7
A2-B53-C13-D7
A3-B53-C13-D7
A9-B53-C13-D7
A13-B53-C13-D7
A24-B53-C13-D7
A69-B53-C13-D7
A67-B53-C13-D7
A39-B53-C13-D7
A65-B53-C13-D7
A66-B53-C13-D7
A2-B79-C13-D7
A3-B79-C13-D7
A9-B79-C13-D7
A13-B79-C13-D7
A24-B79-C13-D7
A69-B79-C13-D7
A67-B79-C13-D7
A39-B79-C13-D7
A65-B79-C13-D7
A66-B79-C13-D7
A2-B80-C13-D7
A3-B80-C13-D7
A9-B80-C13-D7
A13-B80-C13-D7
A24-B80-C13-D7
A69-B80-C13-D7
A67-B80-C13-D7
A39-B80-C13-D7
A65-B80-C13-D7
A66-B80-C13-D7
A2-B85-C13-D7
A3-B85-C13-D7
A9-B85-C13-D7
A13-B85-C13-D7
A24-B85-C13-D7
A69-B85-C13-D7
A67-B85-C13-D7
A39-B85-C13-D7
A65-B85-C13-D7
A66-B85-C13-D7
A2-B86-C13-D7
A3-B86-C13-D7
A9-B86-C13-D7
A13-B86-C13-D7
A24-B86-C13-D7
A69-B86-C13-D7
A67-B86-C13-D7
A39-B86-C13-D7
A65-B86-C13-D7
A66-B86-C13-D7
A2-B87-C13-D7
A3-B87-C13-D7
A9-B87-C13-D7
A13-B87-C13-D7
A24-B87-C13-D7
A69-B87-C13-D7
A67-B87-C13-D7
A39-B87-C13-D7
A65-B87-C13-D7
A66-B87-C13-D7
A2-B89-C13-D7
A3-B89-C13-D7
A9-B89-C13-D7
A13-B89-C13-D7
A24-B89-C13-D7
A69-B89-C13-D7
A67-B89-C13-D7

TABLE 6-continued

A39-B89-C13-D7
A65-B89-C13-D7
A66-B89-C13-D7
A2-B92-C13-D7
A3-B92-C13-D7
A9-B92-C13-D7
A13-B92-C13-D7
A24-B92-C13-D7
A69-B92-C13-D7
A67-B92-C13-D7
A39-B92-C13-D7
A65-B92-C13-D7
A66-B92-C13-D7
A2-B4-C1-D8
A3-B4-C1-D8
A9-B4-C1-D8
A13-B4-C1-D8
A24-B4-C1-D8
A69-B4-C1-D8
A67-B4-C1-D8
A39-B4-C1-D8
A65-B4-C1-D8
A66-B4-C1-D8
A2-B5-C1-D8
A3-B5-C1-D8
A9-B5-C1-D8
A13-B5-C1-D8
A24-B5-C1-D8
A69-B5-C1-D8
A67-B5-C1-D8
A39-B5-C1-D8
A65-B5-C1-D8
A66-B5-C1-D8
A2-B6-C1-D8
A3-B6-C1-D8
A9-B6-C1-D8
A13-B6-C1-D8
A24-B6-C1-D8
A69-B6-C1-D8
A67-B6-C1-D8
A39-B6-C1-D8
A65-B6-C1-D8
A66-B6-C1-D8
A2-B32-C1-D8
A3-B32-C1-D8
A9-B32-C1-D8
A13-B32-C1-D8
A24-B32-C1-D8
A69-B32-C1-D8
A67-B32-C1-D8
A39-B32-C1-D8
A65-B32-C1-D8
A66-B32-C1-D8
A2-B39-C1-D8
A3-B39-C1-D8
A9-B39-C1-D8
A13-B39-C1-D8
A24-B39-C1-D8
A69-B39-C1-D8
A67-B39-C1-D8
A39-B39-C1-D8
A65-B39-C1-D8
A66-B39-C1-D8
A2-B45-C1-D8
A3-B45-C1-D8
A9-B45-C1-D8
A13-B45-C1-D8
A24-B45-C1-D8
A69-B45-C1-D8
A67-B45-C1-D8
A39-B45-C1-D8
A65-B45-C1-D8
A66-B45-C1-D8
A2-B53-C1-D8
A3-B53-C1-D8
A9-B53-C1-D8
A13-B53-C1-D8
A24-B53-C1-D8
A69-B53-C1-D8

TABLE 6-continued

A67-B53-C1-D8
A39-B53-C1-D8
A65-B53-C1-D8
A66-B53-C1-D8
A2-B79-C1-D8
A3-B79-C1-D8
A9-B79-C1-D8
A13-B79-C1-D8
A24-B79-C1-D8
A69-B79-C1-D8
A67-B79-C1-D8
A39-B79-C1-D8
A65-B79-C1-D8
A66-B79-C1-D8
A2-B80-C1-D8
A3-B80-C1-D8
A9-B80-C1-D8
A13-B80-C1-D8
A24-B80-C1-D8
A69-B80-C1-D8
A67-B80-C1-D8
A39-B80-C1-D8
A65-B80-C1-D8
A66-B80-C1-D8
A2-B85-C1-D8
A3-B85-C1-D8
A9-B85-C1-D8
A13-B85-C1-D8
A24-B85-C1-D8
A69-B85-C1-D8
A67-B85-C1-D8
A39-B85-C1-D8
A65-B85-C1-D8
A66-B85-C1-D8
A2-B86-C1-D8
A3-B86-C1-D8
A9-B86-C1-D8
A13-B86-C1-D8
A24-B86-C1-D8
A69-B86-C1-D8
A67-B86-C1-D8
A39-B86-C1-D8
A65-B86-C1-D8
A66-B86-C1-D8
A2-B87-C1-D8
A3-B87-C1-D8
A9-B87-C1-D8
A13-B87-C1-D8
A24-B87-C1-D8
A69-B87-C1-D8
A67-B87-C1-D8
A39-B87-C1-D8
A65-B87-C1-D8
A66-B87-C1-D8
A2-B89-C1-D8
A3-B89-C1-D8
A9-B89-C1-D8
A13-B89-C1-D8
A24-B89-C1-D8
A69-B89-C1-D8
A67-B89-C1-D8
A39-B89-C1-D8
A65-B89-C1-D8
A66-B89-C1-D8
A2-B92-C1-D8
A3-B92-C1-D8
A9-B92-C1-D8
A13-B92-C1-D8
A24-B92-C1-D8
A69-B92-C1-D8
A67-B92-C1-D8
A39-B92-C1-D8
A65-B92-C1-D8
A66-B92-C1-D8
A2-B4-C2-D8
A3-B4-C2-D8
A9-B4-C2-D8
A13-B4-C2-D8
A24-B4-C2-D8
A69-B4-C2-D8
A67-B4-C2-D8
A39-B4-C2-D8
A65-B4-C2-D8
A66-B4-C2-D8
A2-B5-C2-D8
A3-B5-C2-D8
A9-B5-C2-D8
A13-B5-C2-D8
A24-B5-C2-D8
A69-B5-C2-D8
A67-B5-C2-D8
A39-B5-C2-D8
A65-B5-C2-D8
A66-B5-C2-D8
A2-B6-C2-D8
A3-B6-C2-D8
A9-B6-C2-D8
A13-B6-C2-D8
A24-B6-C2-D8
A69-B6-C2-D8
A67-B6-C2-D8
A39-B6-C2-D8
A65-B6-C2-D8
A66-B6-C2-D8
A2-B32-C2-D8
A3-B32-C2-D8
A9-B32-C2-D8
A13-B32-C2-D8
A24-B32-C2-D8
A69-B32-C2-D8
A67-B32-C2-D8
A39-B32-C2-D8
A65-B32-C2-D8
A66-B32-C2-D8
A2-B39-C2-D8
A3-B39-C2-D8
A9-B39-C2-D8
A13-B39-C2-D8
A24-B39-C2-D8
A69-B39-C2-D8
A67-B39-C2-D8
A39-B39-C2-D8
A65-B39-C2-D8
A66-B39-C2-D8
A2-B45-C2-D8
A3-B45-C2-D8
A9-B45-C2-D8
A13-B45-C2-D8
A24-B45-C2-D8
A69-B45-C2-D8
A67-B45-C2-D8
A39-B45-C2-D8
A65-B45-C2-D8
A66-B45-C2-D8
A2-B53-C2-D8
A3-B53-C2-D8
A9-B53-C2-D8
A13-B53-C2-D8
A24-B53-C2-D8
A69-B53-C2-D8
A67-B53-C2-D8
A39-B53-C2-D8
A65-B53-C2-D8
A66-B53-C2-D8
A2-B79-C2-D8
A3-B79-C2-D8
A9-B79-C2-D8
A13-B79-C2-D8
A24-B79-C2-D8
A69-B79-C2-D8
A67-B79-C2-D8
A39-B79-C2-D8
A65-B79-C2-D8
A66-B79-C2-D8
A2-B80-C2-D8
A3-B80-C2-D8
A9-B80-C2-D8
A13-B80-C2-D8

TABLE 6-continued

A24-B80-C2-D8
A69-B80-C2-D8
A67-B80-C2-D8
A39-B80-C2-D8
A65-B80-C2-D8
A66-B80-C2-D8
A2-B85-C2-D8
A3-B85-C2-D8
A9-B85-C2-D8
A13-B85-C2-D8
A24-B85-C2-D8
A69-B85-C2-D8
A67-B85-C2-D8
A39-B85-C2-D8
A65-B85-C2-D8
A66-B85-C2-D8
A2-B86-C2-D8
A3-B86-C2-D8
A9-B86-C2-D8
A13-B86-C2-D8
A24-B86-C2-D8
A69-B86-C2-D8
A67-B86-C2-D8
A39-B86-C2-D8
A65-B86-C2-D8
A66-B86-C2-D8
A2-B87-C2-D8
A3-B87-C2-D8
A9-B87-C2-D8
A13-B87-C2-D8
A24-B87-C2-D8
A69-B87-C2-D8
A67-B87-C2-D8
A39-B87-C2-D8
A65-B87-C2-D8
A66-B87-C2-D8
A2-B89-C2-D8
A3-B89-C2-D8
A9-B89-C2-D8
A13-B89-C2-D8
A24-B89-C2-D8
A69-B89-C2-D8
A67-B89-C2-D8
A39-B89-C2-D8
A65-B89-C2-D8
A66-B89-C2-D8
A2-B92-C2-D8
A3-B92-C2-D8
A9-B92-C2-D8
A13-B92-C2-D8
A24-B92-C2-D8
A69-B92-C2-D8
A67-B92-C2-D8
A39-B92-C2-D8
A65-B92-C2-D8
A66-B92-C2-D8
A2-B4-C3-D8
A3-B4-C3-D8
A9-B4-C3-D8
A13-B4-C3-D8
A24-B4-C3-D8
A69-B4-C3-D8
A67-B4-C3-D8
A39-B4-C3-D8
A65-B4-C3-D8
A66-B4-C3-D8
A2-B5-C3-D8
A3-B5-C3-D8
A9-B5-C3-D8
A13-B5-C3-D8
A24-B5-C3-D8
A69-B5-C3-D8
A67-B5-C3-D8
A39-B5-C3-D8
A65-B5-C3-D8
A66-B5-C3-D8
A2-B6-C3-D8
A3-B6-C3-D8
A9-B6-C3-D8

TABLE 6-continued

A13-B6-C3-D8
A24-B6-C3-D8
A69-B6-C3-D8
A67-B6-C3-D8
A39-B6-C3-D8
A65-B6-C3-D8
A66-B6-C3-D8
A2-B32-C3-D8
A3-B32-C3-D8
A9-B32-C3-D8
A13-B32-C3-D8
A24-B32-C3-D8
A69-B32-C3-D8
A67-B32-C3-D8
A39-B32-C3-D8
A65-B32-C3-D8
A66-B32-C3-D8
A2-B39-C3-D8
A3-B39-C3-D8
A9-B39-C3-D8
A13-B39-C3-D8
A24-B39-C3-D8
A69-B39-C3-D8
A67-B39-C3-D8
A39-B39-C3-D8
A65-B39-C3-D8
A66-B39-C3-D8
A2-B45-C3-D8
A3-B45-C3-D8
A9-B45-C3-D8
A13-B45-C3-D8
A24-B45-C3-D8
A69-B45-C3-D8
A67-B45-C3-D8
A39-B45-C3-D8
A65-B45-C3-D8
A66-B45-C3-D8
A2-B53-C3-D8
A3-B53-C3-D8
A9-B53-C3-D8
A13-B53-C3-D8
A24-B53-C3-D8
A69-B53-C3-D8
A67-B53-C3-D8
A39-B53-C3-D8
A65-B53-C3-D8
A66-B53-C3-D8
A2-B79-C3-D8
A3-B79-C3-D8
A9-B79-C3-D8
A13-B79-C3-D8
A24-B79-C3-D8
A69-B79-C3-D8
A67-B79-C3-D8
A39-B79-C3-D8
A65-B79-C3-D8
A66-B79-C3-D8
A2-B80-C3-D8
A3-B80-C3-D8
A9-B80-C3-D8
A13-B80-C3-D8
A24-B80-C3-D8
A69-B80-C3-D8
A67-B80-C3-D8
A39-B80-C3-D8
A65-B80-C3-D8
A66-B80-C3-D8
A2-B85-C3-D8
A3-B85-C3-D8
A9-B85-C3-D8
A13-B85-C3-D8
A24-B85-C3-D8
A69-B85-C3-D8
A67-B85-C3-D8
A39-B85-C3-D8
A65-B85-C3-D8
A66-B85-C3-D8
A2-B86-C3-D8
A3-B86-C3-D8

TABLE 6-continued

A9-B86-C3-D8
A13-B86-C3-D8
A24-B86-C3-D8
A69-B86-C3-D8
A67-B86-C3-D8
A39-B86-C3-D8
A65-B86-C3-D8
A66-B86-C3-D8
A2-B87-C3-D8
A3-B87-C3-D8
A9-B87-C3-D8
A13-B87-C3-D8
A24-B87-C3-D8
A69-B87-C3-D8
A67-B87-C3-D8
A39-B87-C3-D8
A65-B87-C3-D8
A66-B87-C3-D8
A2-B89-C3-D8
A3-B89-C3-D8
A9-B89-C3-D8
A13-B89-C3-D8
A24-B89-C3-D8
A69-B89-C3-D8
A67-B89-C3-D8
A39-B89-C3-D8
A65-B89-C3-D8
A66-B89-C3-D8
A2-B92-C3-D8
A3-B92-C3-D8
A9-B92-C3-D8
A13-B92-C3-D8
A24-B92-C3-D8
A69-B92-C3-D8
A67-B92-C3-D8
A39-B92-C3-D8
A65-B92-C3-D8
A66-B92-C3-D8
A2-B4-C4-D8
A3-B4-C4-D8
A9-B4-C4-D8
A13-B4-C4-D8
A24-B4-C4-D8
A69-B4-C4-D8
A67-B4-C4-D8
A39-B4-C4-D8
A65-B4-C4-D8
A66-B4-C4-D8
A2-B5-C4-D8
A3-B5-C4-D8
A9-B5-C4-D8
A13-B5-C4-D8
A24-B5-C4-D8
A69-B5-C4-D8
A67-B5-C4-D8
A39-B5-C4-D8
A65-B5-C4-D8
A66-B5-C4-D8
A2-B6-C4-D8
A3-B6-C4-D8
A9-B6-C4-D8
A13-B6-C4-D8
A24-B6-C4-D8
A69-B6-C4-D8
A67-B6-C4-D8
A39-B6-C4-D8
A65-B6-C4-D8
A66-B6-C4-D8
A2-B32-C4-D8
A3-B32-C4-D8
A9-B32-C4-D8
A13-B32-C4-D8
A24-B32-C4-D8
A69-B32-C4-D8
A67-B32-C4-D8
A39-B32-C4-D8
A65-B32-C4-D8
A66-B32-C4-D8
A2-B39-C4-D8

TABLE 6-continued

A3-B39-C4-D8
A9-B39-C4-D8
A13-B39-C4-D8
A24-B39-C4-D8
A69-B39-C4-D8
A67-B39-C4-D8
A39-B39-C4-D8
A65-B39-C4-D8
A66-B39-C4-D8
A2-B45-C4-D8
A3-B45-C4-D8
A9-B45-C4-D8
A13-B45-C4-D8
A24-B45-C4-D8
A69-B45-C4-D8
A67-B45-C4-D8
A39-B45-C4-D8
A65-B45-C4-D8
A66-B45-C4-D8
A2-B53-C4-D8
A3-B53-C4-D8
A9-B53-C4-D8
A13-B53-C4-D8
A24-B53-C4-D8
A69-B53-C4-D8
A67-B53-C4-D8
A39-B53-C4-D8
A65-B53-C4-D8
A66-B53-C4-D8
A2-B79-C4-D8
A3-B79-C4-D8
A9-B79-C4-D8
A13-B79-C4-D8
A24-B79-C4-D8
A69-B79-C4-D8
A67-B79-C4-D8
A39-B79-C4-D8
A65-B79-C4-D8
A66-B79-C4-D8
A2-B80-C4-D8
A3-B80-C4-D8
A9-B80-C4-D8
A13-B80-C4-D8
A24-B80-C4-D8
A69-B80-C4-D8
A67-B80-C4-D8
A39-B80-C4-D8
A65-B80-C4-D8
A66-B80-C4-D8
A2-B85-C4-D8
A3-B85-C4-D8
A9-B85-C4-D8
A13-B85-C4-D8
A24-B85-C4-D8
A69-B85-C4-D8
A67-B85-C4-D8
A39-B85-C4-D8
A65-B85-C4-D8
A66-B85-C4-D8
A2-B86-C4-D8
A3-B86-C4-D8
A9-B86-C4-D8
A13-B86-C4-D8
A24-B86-C4-D8
A69-B86-C4-D8
A67-B86-C4-D8
A39-B86-C4-D8
A65-B86-C4-D8
A66-B86-C4-D8
A2-B87-C4-D8
A3-B87-C4-D8
A9-B87-C4-D8
A13-B87-C4-D8
A24-B87-C4-D8
A69-B87-C4-D8
A67-B87-C4-D8
A39-B87-C4-D8
A65-B87-C4-D8
A66-B87-C4-D8

TABLE 6-continued

A2-B89-C4-D8
A3-B89-C4-D8
A9-B89-C4-D8
A13-B89-C4-D8
A24-B89-C4-D8
A69-B89-C4-D8
A67-B89-C4-D8
A39-B89-C4-D8
A65-B89-C4-D8
A66-B89-C4-D8
A2-B92-C4-D8
A3-B92-C4-D8
A9-B92-C4-D8
A13-B92-C4-D8
A24-B92-C4-D8
A69-B92-C4-D8
A67-B92-C4-D8
A39-B92-C4-D8
A65-B92-C4-D8
A66-B92-C4-D8
A2-B4-C5-D8
A3-B4-C5-D8
A9-B4-C5-D8
A13-B4-C5-D8
A24-B4-C5-D8
A69-B4-C5-D8
A67-B4-C5-D8
A39-B4-C5-D8
A65-B4-C5-D8
A66-B4-C5-D8
A2-B5-C5-D8
A3-B5-C5-D8
A9-B5-C5-D8
A13-B5-C5-D8
A24-B5-C5-D8
A69-B5-C5-D8
A67-B5-C5-D8
A39-B5-C5-D8
A65-B5-C5-D8
A66-B5-C5-D8
A2-B6-C5-D8
A3-B6-C5-D8
A9-B6-C5-D8
A13-B6-C5-D8
A24-B6-C5-D8
A69-B6-C5-D8
A67-B6-C5-D8
A39-B6-C5-D8
A65-B6-C5-D8
A66-B6-C5-D8
A2-B32-C5-D8
A3-B32-C5-D8
A9-B32-C5-D8
A13-B32-C5-D8
A24-B32-C5-D8
A69-B32-C5-D8
A67-B32-C5-D8
A39-B32-C5-D8
A65-B32-C5-D8
A66-B32-C5-D8
A2-B39-C5-D8
A3-B39-C5-D8
A9-B39-C5-D8
A13-B39-C5-D8
A24-B39-C5-D8
A69-B39-C5-D8
A67-B39-C5-D8
A39-B39-C5-D8
A65-B39-C5-D8
A66-B39-C5-D8
A2-B45-C5-D8
A3-B45-C5-D8
A9-B45-C5-D8
A13-B45-C5-D8
A24-B45-C5-D8
A69-B45-C5-D8
A67-B45-C5-D8
A39-B45-C5-D8
A65-B45-C5-D8

TABLE 6-continued

A66-B45-C5-D8
A2-B53-C5-D8
A3-B53-C5-D8
A9-B53-C5-D8
A13-B53-C5-D8
A24-B53-C5-D8
A69-B53-C5-D8
A67-B53-C5-D8
A39-B53-C5-D8
A65-B53-C5-D8
A66-B53-C5-D8
A2-B79-C5-D8
A3-B79-C5-D8
A9-B79-C5-D8
A13-B79-C5-D8
A24-B79-C5-D8
A69-B79-C5-D8
A67-B79-C5-D8
A39-B79-C5-D8
A65-B79-C5-D8
A66-B79-C5-D8
A2-B80-C5-D8
A3-B80-C5-D8
A9-B80-C5-D8
A13-B80-C5-D8
A24-B80-C5-D8
A69-B80-C5-D8
A67-B80-C5-D8
A39-B80-C5-D8
A65-B80-C5-D8
A66-B80-C5-D8
A2-B85-C5-D8
A3-B85-C5-D8
A9-B85-C5-D8
A13-B85-C5-D8
A24-B85-C5-D8
A69-B85-C5-D8
A67-B85-C5-D8
A39-B85-C5-D8
A65-B85-C5-D8
A66-B85-C5-D8
A2-B86-C5-D8
A3-B86-C5-D8
A9-B86-C5-D8
A13-B86-C5-D8
A24-B86-C5-D8
A69-B86-C5-D8
A67-B86-C5-D8
A39-B86-C5-D8
A65-B86-C5-D8
A66-B86-C5-D8
A2-B87-C5-D8
A3-B87-C5-D8
A9-B87-C5-D8
A13-B87-C5-D8
A24-B87-C5-D8
A69-B87-C5-D8
A67-B87-C5-D8
A39-B87-C5-D8
A65-B87-C5-D8
A66-B87-C5-D8
A2-B89-C5-D8
A3-B89-C5-D8
A9-B89-C5-D8
A13-B89-C5-D8
A24-B89-C5-D8
A69-B89-C5-D8
A67-B89-C5-D8
A39-B89-C5-D8
A65-B89-C5-D8
A66-B89-C5-D8
A2-B92-C5-D8
A3-B92-C5-D8
A9-B92-C5-D8
A13-B92-C5-D8
A24-B92-C5-D8
A69-B92-C5-D8
A67-B92-C5-D8
A39-B92-C5-D8

TABLE 6-continued

A65-B92-C5-D8
A66-B92-C5-D8
A2-B4-C6-D8
A3-B4-C6-D8
A9-B4-C6-D8
A13-B4-C6-D8
A24-B4-C6-D8
A69-B4-C6-D8
A67-B4-C6-D8
A39-B4-C6-D8
A65-B4-C6-D8
A66-B4-C6-D8
A2-B5-C6-D8
A3-B5-C6-D8
A9-B5-C6-D8
A13-B5-C6-D8
A24-B5-C6-D8
A69-B5-C6-D8
A67-B5-C6-D8
A39-B5-C6-D8
A65-B5-C6-D8
A66-B5-C6-D8
A2-B6-C6-D8
A3-B6-C6-D8
A9-B6-C6-D8
A13-B6-C6-D8
A24-B6-C6-D8
A69-B6-C6-D8
A67-B6-C6-D8
A39-B6-C6-D8
A65-B6-C6-D8
A66-B6-C6-D8
A2-B32-C6-D8
A3-B32-C6-D8
A9-B32-C6-D8
A13-B32-C6-D8
A24-B32-C6-D8
A69-B32-C6-D8
A67-B32-C6-D8
A39-B32-C6-D8
A65-B32-C6-D8
A66-B32-C6-D8
A2-B39-C6-D8
A3-B39-C6-D8
A9-B39-C6-D8
A13-B39-C6-D8
A24-B39-C6-D8
A69-B39-C6-D8
A67-B39-C6-D8
A39-B39-C6-D8
A65-B39-C6-D8
A66-B39-C6-D8
A2-B45-C6-D8
A3-B45-C6-D8
A9-B45-C6-D8
A13-B45-C6-D8
A24-B45-C6-D8
A69-B45-C6-D8
A67-B45-C6-D8
A39-B45-C6-D8
A65-B45-C6-D8
A66-B45-C6-D8
A2-B53-C6-D8
A3-B53-C6-D8
A9-B53-C6-D8
A13-B53-C6-D8
A24-B53-C6-D8
A69-B53-C6-D8
A67-B53-C6-D8
A39-B53-C6-D8
A65-B53-C6-D8
A66-B53-C6-D8
A2-B79-C6-D8
A3-B79-C6-D8
A9-B79-C6-D8
A13-B79-C6-D8
A24-B79-C6-D8
A69-B79-C6-D8
A67-B79-C6-D8

TABLE 6-continued

A39-B79-C6-D8
A65-B79-C6-D8
A66-B79-C6-D8
A2-B80-C6-D8
A3-B80-C6-D8
A9-B80-C6-D8
A13-B80-C6-D8
A24-B80-C6-D8
A69-B80-C6-D8
A67-B80-C6-D8
A39-B80-C6-D8
A65-B80-C6-D8
A66-B80-C6-D8
A2-B85-C6-D8
A3-B85-C6-D8
A9-B85-C6-D8
A13-B85-C6-D8
A24-B85-C6-D8
A69-B85-C6-D8
A67-B85-C6-D8
A39-B85-C6-D8
A65-B85-C6-D8
A66-B85-C6-D8
A2-B86-C6-D8
A3-B86-C6-D8
A9-B86-C6-D8
A13-B86-C6-D8
A24-B86-C6-D8
A69-B86-C6-D8
A67-B86-C6-D8
A39-B86-C6-D8
A65-B86-C6-D8
A66-B86-C6-D8
A2-B87-C6-D8
A3-B87-C6-D8
A9-B87-C6-D8
A13-B87-C6-D8
A24-B87-C6-D8
A69-B87-C6-D8
A67-B87-C6-D8
A39-B87-C6-D8
A65-B87-C6-D8
A66-B87-C6-D8
A2-B89-C6-D8
A3-B89-C6-D8
A9-B89-C6-D8
A13-B89-C6-D8
A24-B89-C6-D8
A69-B89-C6-D8
A67-B89-C6-D8
A39-B89-C6-D8
A65-B89-C6-D8
A66-B89-C6-D8
A2-B92-C6-D8
A3-B92-C6-D8
A9-B92-C6-D8
A13-B92-C6-D8
A24-B92-C6-D8
A69-B92-C6-D8
A67-B92-C6-D8
A39-B92-C6-D8
A65-B92-C6-D8
A66-B92-C6-D8
A2-B4-C7-D8
A3-B4-C7-D8
A9-B4-C7-D8
A13-B4-C7-D8
A24-B4-C7-D8
A69-B4-C7-D8
A67-B4-C7-D8
A39-B4-C7-D8
A65-B4-C7-D8
A66-B4-C7-D8
A2-B5-C7-D8
A3-B5-C7-D8
A9-B5-C7-D8
A13-B5-C7-D8
A24-B5-C7-D8
A69-B5-C7-D8

TABLE 6-continued

A67-B5-C7-D8
A39-B5-C7-D8
A65-B5-C7-D8
A66-B5-C7-D8
A2-B6-C7-D8
A3-B6-C7-D8
A9-B6-C7-D8
A13-B6-C7-D8
A24-B6-C7-D8
A69-B6-C7-D8
A67-B6-C7-D8
A39-B6-C7-D8
A65-B6-C7-D8
A66-B6-C7-D8
A2-B32-C7-D8
A3-B32-C7-D8
A9-B32-C7-D8
A13-B32-C7-D8
A24-B32-C7-D8
A69-B32-C7-D8
A67-B32-C7-D8
A39-B32-C7-D8
A65-B32-C7-D8
A66-B32-C7-D8
A2-B39-C7-D8
A3-B39-C7-D8
A9-B39-C7-D8
A13-B39-C7-D8
A24-B39-C7-D8
A69-B39-C7-D8
A67-B39-C7-D8
A39-B39-C7-D8
A65-B39-C7-D8
A66-B39-C7-D8
A2-B45-C7-D8
A3-B45-C7-D8
A9-B45-C7-D8
A13-B45-C7-D8
A24-B45-C7-D8
A69-B45-C7-D8
A67-B45-C7-D8
A39-B45-C7-D8
A65-B45-C7-D8
A66-B45-C7-D8
A2-B53-C7-D8
A3-B53-C7-D8
A9-B53-C7-D8
A13-B53-C7-D8
A24-B53-C7-D8
A69-B53-C7-D8
A67-B53-C7-D8
A39-B53-C7-D8
A65-B53-C7-D8
A66-B53-C7-D8
A2-B79-C7-D8
A3-B79-C7-D8
A9-B79-C7-D8
A13-B79-C7-D8
A24-B79-C7-D8
A69-B79-C7-D8
A67-B79-C7-D8
A39-B79-C7-D8
A65-B79-C7-D8
A66-B79-C7-D8
A2-B80-C7-D8
A3-B80-C7-D8
A9-B80-C7-D8
A13-B80-C7-D8
A24-B80-C7-D8
A69-B80-C7-D8
A67-B80-C7-D8
A39-B80-C7-D8
A65-B80-C7-D8
A66-B80-C7-D8
A2-B85-C7-D8
A3-B85-C7-D8
A9-B85-C7-D8
A13-B85-C7-D8
A24-B85-C7-D8

TABLE 6-continued

A69-B85-C7-D8
A67-B85-C7-D8
A39-B85-C7-D8
A65-B85-C7-D8
A66-B85-C7-D8
A2-B86-C7-D8
A3-B86-C7-D8
A9-B86-C7-D8
A13-B86-C7-D8
A24-B86-C7-D8
A69-B86-C7-D8
A67-B86-C7-D8
A39-B86-C7-D8
A65-B86-C7-D8
A66-B86-C7-D8
A2-B87-C7-D8
A3-B87-C7-D8
A9-B87-C7-D8
A13-B87-C7-D8
A24-B87-C7-D8
A69-B87-C7-D8
A67-B87-C7-D8
A39-B87-C7-D8
A65-B87-C7-D8
A66-B87-C7-D8
A2-B89-C7-D8
A3-B89-C7-D8
A9-B89-C7-D8
A13-B89-C7-D8
A24-B89-C7-D8
A69-B89-C7-D8
A67-B89-C7-D8
A39-B89-C7-D8
A65-B89-C7-D8
A66-B89-C7-D8
A2-B92-C7-D8
A3-B92-C7-D8
A9-B92-C7-D8
A13-B92-C7-D8
A24-B92-C7-D8
A69-B92-C7-D8
A67-B92-C7-D8
A39-B92-C7-D8
A65-B92-C7-D8
A66-B92-C7-D8
A2-B4-C8-D8
A3-B4-C8-D8
A9-B4-C8-D8
A13-B4-C8-D8
A24-B4-C8-D8
A69-B4-C8-D8
A67-B4-C8-D8
A39-B4-C8-D8
A65-B4-C8-D8
A66-B4-C8-D8
A2-B5-C8-D8
A3-B5-C8-D8
A9-B5-C8-D8
A13-B5-C8-D8
A24-B5-C8-D8
A69-B5-C8-D8
A67-B5-C8-D8
A39-B5-C8-D8
A65-B5-C8-D8
A66-B5-C8-D8
A2-B6-C8-D8
A3-B6-C8-D8
A9-B6-C8-D8
A13-B6-C8-D8
A24-B6-C8-D8
A69-B6-C8-D8
A67-B6-C8-D8
A39-B6-C8-D8
A65-B6-C8-D8
A66-B6-C8-D8
A2-B32-C8-D8
A3-B32-C8-D8
A9-B32-C8-D8
A13-B32-C8-D8

TABLE 6-continued

A24-B32-C8-D8
A69-B32-C8-D8
A67-B32-C8-D8
A39-B32-C8-D8
A65-B32-C8-D8
A66-B32-C8-D8
A2-B39-C8-D8
A3-B39-C8-D8
A9-B39-C8-D8
A13-B39-C8-D8
A24-B39-C8-D8
A69-B39-C8-D8
A67-B39-C8-D8
A39-B39-C8-D8
A65-B39-C8-D8
A66-B39-C8-D8
A2-B45-C8-D8
A3-B45-C8-D8
A9-B45-C8-D8
A13-B45-C8-D8
A24-B45-C8-D8
A69-B45-C8-D8
A67-B45-C8-D8
A39-B45-C8-D8
A65-B45-C8-D8
A66-B45-C8-D8
A2-B53-C8-D8
A3-B53-C8-D8
A9-B53-C8-D8
A13-B53-C8-D8
A24-B53-C8-D8
A69-B53-C8-D8
A67-B53-C8-D8
A39-B53-C8-D8
A65-B53-C8-D8
A66-B53-C8-D8
A2-B79-C8-D8
A3-B79-C8-D8
A9-B79-C8-D8
A13-B79-C8-D8
A24-B79-C8-D8
A69-B79-C8-D8
A67-B79-C8-D8
A39-B79-C8-D8
A65-B79-C8-D8
A66-B79-C8-D8
A2-B80-C8-D8
A3-B80-C8-D8
A9-B80-C8-D8
A13-B80-C8-D8
A24-B80-C8-D8
A69-B80-C8-D8
A67-B80-C8-D8
A39-B80-C8-D8
A65-B80-C8-D8
A66-B80-C8-D8
A2-B85-C8-D8
A3-B85-C8-D8
A9-B85-C8-D8
A13-B85-C8-D8
A24-B85-C8-D8
A69-B85-C8-D8
A67-B85-C8-D8
A39-B85-C8-D8
A65-B85-C8-D8
A66-B85-C8-D8
A2-B86-C8-D8
A3-B86-C8-D8
A9-B86-C8-D8
A13-B86-C8-D8
A24-B86-C8-D8
A69-B86-C8-D8
A67-B86-C8-D8
A39-B86-C8-D8
A65-B86-C8-D8
A66-B86-C8-D8
A2-B87-C8-D8
A3-B87-C8-D8
A9-B87-C8-D8

TABLE 6-continued

A13-B87-C8-D8
A24-B87-C8-D8
A69-B87-C8-D8
A67-B87-C8-D8
A39-B87-C8-D8
A65-B87-C8-D8
A66-B87-C8-D8
A2-B89-C8-D8
A3-B89-C8-D8
A9-B89-C8-D8
A13-B89-C8-D8
A24-B89-C8-D8
A69-B89-C8-D8
A67-B89-C8-D8
A39-B89-C8-D8
A65-B89-C8-D8
A66-B89-C8-D8
A2-B92-C8-D8
A3-B92-C8-D8
A9-B92-C8-D8
A13-B92-C8-D8
A24-B92-C8-D8
A69-B92-C8-D8
A67-B92-C8-D8
A39-B92-C8-D8
A65-B92-C8-D8
A66-B92-C8-D8
A2-B4-C9-D8
A3-B4-C9-D8
A9-B4-C9-D8
A13-B4-C9-D8
A24-B4-C9-D8
A69-B4-C9-D8
A67-B4-C9-D8
A39-B4-C9-D8
A65-B4-C9-D8
A66-B4-C9-D8
A2-B5-C9-D8
A3-B5-C9-D8
A9-B5-C9-D8
A13-B5-C9-D8
A24-B5-C9-D8
A69-B5-C9-D8
A67-B5-C9-D8
A39-B5-C9-D8
A65-B5-C9-D8
A66-B5-C9-D8
A2-B6-C9-D8
A3-B6-C9-D8
A9-B6-C9-D8
A13-B6-C9-D8
A24-B6-C9-D8
A69-B6-C9-D8
A67-B6-C9-D8
A39-B6-C9-D8
A65-B6-C9-D8
A66-B6-C9-D8
A2-B32-C9-D8
A3-B32-C9-D8
A9-B32-C9-D8
A13-B32-C9-D8
A24-B32-C9-D8
A69-B32-C9-D8
A67-B32-C9-D8
A39-B32-C9-D8
A65-B32-C9-D8
A66-B32-C9-D8
A2-B39-C9-D8
A3-B39-C9-D8
A9-B39-C9-D8
A13-B39-C9-D8
A24-B39-C9-D8
A69-B39-C9-D8
A67-B39-C9-D8
A39-B39-C9-D8
A65-B39-C9-D8
A66-B39-C9-D8
A2-B45-C9-D8
A3-B45-C9-D8

TABLE 6-continued

A9-B45-C9-D8
A3-B45-C9-D8
A24-B45-C9-D8
A69-B45-C9-D8
A67-B45-C9-D8
A39-B45-C9-D8
A65-B45-C9-D8
A66-B45-C9-D8
A2-B53-C9-D8
A3-B53-C9-D8
A9-B53-C9-D8
A13-B53-C9-D8
A24-B53-C9-D8
A69-B53-C9-D8
A67-B53-C9-D8
A39-B53-C9-D8
A65-B53-C9-D8
A66-B53-C9-D8
A2-B79-C9-D8
A3-B79-C9-D8
A9-B79-C9-D8
A13-B79-C9-D8
A24-B79-C9-D8
A69-B79-C9-D8
A67-B79-C9-D8
A39-B79-C9-D8
A65-B79-C9-D8
A66-B79-C9-D8
A2-B80-C9-D8
A3-B80-C9-D8
A9-B80-C9-D8
A13-B80-C9-D8
A24-B80-C9-D8
A69-B80-C9-D8
A67-B80-C9-D8
A39-B80-C9-D8
A65-B80-C9-D8
A66-B80-C9-D8
A2-B85-C9-D8
A3-B85-C9-D8
A9-B85-C9-D8
A13-B85-C9-D8
A24-B85-C9-D8
A69-B85-C9-D8
A67-B85-C9-D8
A39-B85-C9-D8
A65-B85-C9-D8
A66-B85-C9-D8
A2-B86-C9-D8
A3-B86-C9-D8
A9-B86-C9-D8
A13-B86-C9-D8
A24-B86-C9-D8
A69-B86-C9-D8
A67-B86-C9-D8
A39-B86-C9-D8
A65-B86-C9-D8
A66-B86-C9-D8
A2-B87-C9-D8
A3-B87-C9-D8
A9-B87-C9-D8
A13-B87-C9-D8
A24-B87-C9-D8
A69-B87-C9-D8
A67-B87-C9-D8
A39-B87-C9-D8
A65-B87-C9-D8
A66-B87-C9-D8
A2-B89-C9-D8
A3-B89-C9-D8
A9-B89-C9-D8
A13-B89-C9-D8
A24-B89-C9-D8
A69-B89-C9-D8
A67-B89-C9-D8
A39-B89-C9-D8
A65-B89-C9-D8
A66-B89-C9-D8
A2-B92-C9-D8
A3-B92-C9-D8
A9-B92-C9-D8
A13-B92-C9-D8
A24-B92-C9-D8
A69-B92-C9-D8
A67-B92-C9-D8
A39-B92-C9-D8
A65-B92-C9-D8
A66-B92-C9-D8
A2-B4-C10-D8
A3-B4-C10-D8
A9-B4-C10-D8
A13-B4-C10-D8
A24-B4-C10-D8
A69-B4-C10-D8
A67-B4-C10-D8
A39-B4-C10-D8
A65-B4-C10-D8
A66-B4-C10-D8
A2-B5-C10-D8
A3-B5-C10-D8
A9-B5-C10-D8
A13-B5-C10-D8
A24-B5-C10-D8
A69-B5-C10-D8
A67-B5-C10-D8
A39-B5-C10-D8
A65-B5-C10-D8
A66-B5-C10-D8
A2-B6-C10-D8
A3-B6-C10-D8
A9-B6-C10-D8
A13-B6-C10-D8
A24-B6-C10-D8
A69-B6-C10-D8
A67-B6-C10-D8
A39-B6-C10-D8
A65-B6-C10-D8
A66-B6-C10-D8
A2-B32-C10-D8
A3-B32-C10-D8
A9-B32-C10-D8
A13-B32-C10-D8
A24-B32-C10-D8
A69-B32-C10-D8
A67-B32-C10-D8
A39-B32-C10-D8
A65-B32-C10-D8
A66-B32-C10-D8
A2-B39-C10-D8
A3-B39-C10-D8
A9-B39-C10-D8
A13-B39-C10-D8
A24-B39-C10-D8
A69-B39-C10-D8
A67-B39-C10-D8
A39-B39-C10-D8
A65-B39-C10-D8
A66-B39-C10-D8
A2-B45-C10-D8
A3-B45-C10-D8
A9-B45-C10-D8
A13-B45-C10-D8
A24-B45-C10-D8
A69-B45-C10-D8
A67-B45-C10-D8
A39-B45-C10-D8
A65-B45-C10-D8
A66-B45-C10-D8
A2-B53-C10-D8
A3-B53-C10-D8
A9-B53-C10-D8
A13-B53-C10-D8
A24-B53-C10-D8
A69-B53-C10-D8
A67-B53-C10-D8
A39-B53-C10-D8
A65-B53-C10-D8
A66-B53-C10-D8

TABLE 6-continued

A2-B79-C10-D8
A3-B79-C10-D8
A9-B79-C10-D8
A13-B79-C10-D8
A24-B79-C10-D8
A69-B79-C10-D8
A67-B79-C10-D8
A39-B79-C10-D8
A65-B79-C10-D8
A66-B79-C10-D8
A2-B80-C10-D8
A3-B80-C10-D8
A9-B80-C10-D8
A13-B80-C10-D8
A24-B80-C10-D8
A69-B80-C10-D8
A67-B80-C10-D8
A39-B80-C10-D8
A65-B80-C10-D8
A66-B80-C10-D8
A2-B85-C10-D8
A3-B85-C10-D8
A9-B85-C10-D8
A13-B85-C10-D8
A24-B85-C10-D8
A69-B85-C10-D8
A67-B85-C10-D8
A39-B85-C10-D8
A65-B85-C10-D8
A66-B85-C10-D8
A2-B86-C10-D8
A3-B86-C10-D8
A9-B86-C10-D8
A13-B86-C10-D8
A24-B86-C10-D8
A69-B86-C10-D8
A67-B86-C10-D8
A39-B86-C10-D8
A65-B86-C10-D8
A66-B86-C10-D8
A2-B87-C10-D8
A3-B87-C10-D8
A9-B87-C10-D8
A13-B87-C10-D8
A24-B87-C10-D8
A69-B87-C10-D8
A67-B87-C10-D8
A39-B87-C10-D8
A65-B87-C10-D8
A66-B87-C10-D8
A2-B89-C10-D8
A3-B89-C10-D8
A9-B89-C10-D8
A13-B89-C10-D8
A24-B89-C10-D8
A69-B89-C10-D8
A67-B89-C10-D8
A39-B89-C10-D8
A65-B89-C10-D8
A66-B89-C10-D8
A2-B92-C10-D8
A3-B92-C10-D8
A9-B92-C10-D8
A13-B92-C10-D8
A24-B92-C10-D8
A69-B92-C10-D8
A67-B92-C10-D8
A39-B92-C10-D8
A65-B92-C10-D8
A66-B92-C10-D8
A2-B4-C11-D8
A3-B4-C11-D8
A9-B4-C11-D8
A13-B4-C11-D8
A24-B4-C11-D8
A69-B4-C11-D8
A67-B4-C11-D8
A39-B4-C11-D8
A65-B4-C11-D8

TABLE 6-continued

A66-B4-C11-D8
A2-B5-C11-D8
A3-B5-C11-D8
A9-B5-C11-D8
A13-B5-C11-D8
A24-B5-C11-D8
A69-B5-C11-D8
A67-B5-C11-D8
A39-B5-C11-D8
A65-B5-C11-D8
A66-B5-C11-D8
A2-B6-C11-D8
A3-B6-C11-D8
A9-B6-C11-D8
A13-B6-C11-D8
A24-B6-C11-D8
A69-B6-C11-D8
A67-B6-C11-D8
A39-B6-C11-D8
A65-B6-C11-D8
A66-B6-C11-D8
A2-B32-C11-D8
A3-B32-C11-D8
A9-B32-C11-D8
A13-B32-C11-D8
A24-B32-C11-D8
A69-B32-C11-D8
A67-B32-C11-D8
A39-B32-C11-D8
A65-B32-C11-D8
A66-B32-C11-D8
A2-B39-C11-D8
A3-B39-C11-D8
A9-B39-C11-D8
A13-B39-C11-D8
A24-B39-C11-D8
A69-B39-C11-D8
A67-B39-C11-D8
A39-B39-C11-D8
A65-B39-C11-D8
A66-B39-C11-D8
A2-B45-C11-D8
A3-B45-C11-D8
A9-B45-C11-D8
A13-B45-C11-D8
A24-B45-C11-D8
A69-B45-C11-D8
A67-B45-C11-D8
A39-B45-C11-D8
A65-B45-C11-D8
A66-B45-C11-D8
A2-B53-C11-D8
A3-B53-C11-D8
A9-B53-C11-D8
A13-B53-C11-D8
A24-B53-C11-D8
A69-B53-C11-D8
A67-B53-C11-D8
A39-B53-C11-D8
A65-B53-C11-D8
A66-B53-C11-D8
A2-B79-C11-D8
A3-B79-C11-D8
A9-B79-C11-D8
A13-B79-C11-D8
A24-B79-C11-D8
A69-B79-C11-D8
A67-B79-C11-D8
A39-B79-C11-D8
A65-B79-C11-D8
A66-B79-C11-D8
A2-B80-C11-D8
A3-B80-C11-D8
A9-B80-C11-D8
A13-B80-C11-D8
A24-B80-C11-D8
A69-B80-C11-D8
A67-B80-C11-D8
A39-B80-C11-D8

TABLE 6-continued

A65-B80-C11-D8
A66-B80-C11-D8
A2-B85-C11-D8
A3-B85-C11-D8
A9-B85-C11-D8
A13-B85-C11-D8
A24-B85-C11-D8
A69-B85-C11-D8
A67-B85-C11-D8
A39-B85-C11-D8
A65-B85-C11-D8
A66-B85-C11-D8
A2-B86-C11-D8
A3-B86-C11-D8
A9-B86-C11-D8
A13-B86-C11-D8
A24-B86-C11-D8
A69-B86-C11-D8
A67-B86-C11-D8
A39-B86-C11-D8
A65-B86-C11-D8
A66-B86-C11-D8
A2-B87-C11-D8
A3-B87-C11-D8
A9-B87-C11-D8
A13-B87-C11-D8
A24-B87-C11-D8
A69-B87-C11-D8
A67-B87-C11-D8
A39-B87-C11-D8
A65-B87-C11-D8
A66-B87-C11-D8
A2-B89-C11-D8
A3-B89-C11-D8
A9-B89-C11-D8
A13-B89-C11-D8
A24-B89-C11-D8
A69-B89-C11-D8
A67-B89-C11-D8
A39-B89-C11-D8
A65-B89-C11-D8
A66-B89-C11-D8
A2-B92-C11-D8
A3-B92-C11-D8
A9-B92-C11-D8
A13-B92-C11-D8
A24-B92-C11-D8
A69-B92-C11-D8
A67-B92-C11-D8
A39-B92-C11-D8
A65-B92-C11-D8
A66-B92-C11-D8
A2-B4-C12-D8
A3-B4-C12-D8
A9-B4-C12-D8
A13-B4-C12-D8
A24-B4-C12-D8
A69-B4-C12-D8
A67-B4-C12-D8
A39-B4-C12-D8
A65-B4-C12-D8
A66-B4-C12-D8
A2-B5-C12-D8
A3-B5-C12-D8
A9-B5-C12-D8
A13-B5-C12-D8
A24-B5-C12-D8
A69-B5-C12-D8
A67-B5-C12-D8
A39-B5-C12-D8
A65-B5-C12-D8
A66-B5-C12-D8
A2-B6-C12-D8
A3-B6-C12-D8
A9-B6-C12-D8
A13-B6-C12-D8
A24-B6-C12-D8
A69-B6-C12-D8
A67-B6-C12-D8
A39-B6-C12-D8
A65-B6-C12-D8
A66-B6-C12-D8
A2-B32-C12-D8
A3-B32-C12-D8
A9-B32-C12-D8
A13-B32-C12-D8
A24-B32-C12-D8
A69-B32-C12-D8
A67-B32-C12-D8
A39-B32-C12-D8
A65-B32-C12-D8
A66-B32-C12-D8
A2-B39-C12-D8
A3-B39-C12-D8
A9-B39-C12-D8
A13-B39-C12-D8
A24-B39-C12-D8
A69-B39-C12-D8
A67-B39-C12-D8
A39-B39-C12-D8
A65-B39-C12-D8
A66-B39-C12-D8
A2-B45-C12-D8
A3-B45-C12-D8
A9-B45-C12-D8
A13-B45-C12-D8
A24-B45-C12-D8
A69-B45-C12-D8
A67-B45-C12-D8
A39-B45-C12-D8
A65-B45-C12-D8
A66-B45-C12-D8
A2-B53-C12-D8
A3-B53-C12-D8
A9-B53-C12-D8
A13-B53-C12-D8
A24-B53-C12-D8
A69-B53-C12-D8
A67-B53-C12-D8
A39-B53-C12-D8
A65-B53-C12-D8
A66-B53-C12-D8
A2-B79-C12-D8
A3-B79-C12-D8
A9-B79-C12-D8
A13-B79-C12-D8
A24-B79-C12-D8
A69-B79-C12-D8
A67-B79-C12-D8
A39-B79-C12-D8
A65-B79-C12-D8
A66-B79-C12-D8
A2-B80-C12-D8
A3-B80-C12-D8
A9-B80-C12-D8
A13-B80-C12-D8
A24-B80-C12-D8
A69-B80-C12-D8
A67-B80-C12-D8
A39-B80-C12-D8
A65-B80-C12-D8
A66-B80-C12-D8
A2-B85-C12-D8
A3-B85-C12-D8
A9-B85-C12-D8
A13-B85-C12-D8
A24-B85-C12-D8
A69-B85-C12-D8
A67-B85-C12-D8
A39-B85-C12-D8
A65-B85-C12-D8
A66-B85-C12-D8
A2-B86-C12-D8
A3-B86-C12-D8
A9-B86-C12-D8
A13-B86-C12-D8
A24-B86-C12-D8
A69-B86-C12-D8

TABLE 6-continued

A67-B86-C12-D8
A39-B86-C12-D8
A65-B86-C12-D8
A66-B86-C12-D8
A2-B87-C12-D8
A3-B87-C12-D8
A9-B87-C12-D8
A13-B87-C12-D8
A24-B87-C12-D8
A69-B87-C12-D8
A67-B87-C12-D8
A39-B87-C12-D8
A65-B87-C12-D8
A66-B87-C12-D8
A2-B89-C12-D8
A3-B89-C12-D8
A9-B89-C12-D8
A13-B89-C12-D8
A24-B89-C12-D8
A69-B89-C12-D8
A67-B89-C12-D8
A39-B89-C12-D8
A65-B89-C12-D8
A66-B89-C12-D8
A2-B92-C12-D8
A3-B92-C12-D8
A9-B92-C12-D8
A13-B92-C12-D8
A24-B92-C12-D8
A69-B92-C12-D8
A67-B92-C12-D8
A39-B92-C12-D8
A65-B92-C12-D8
A66-B92-C12-D8
A2-B4-C13-D8
A3-B4-C13-D8
A9-B4-C13-D8
A13-B4-C13-D8
A24-B4-C13-D8
A69-B4-C13-D8
A67-B4-C13-D8
A39-B4-C13-D8
A65-B4-C13-D8
A66-B4-C13-D8
A2-B5-C13-D8
A3-B5-C13-D8
A9-B5-C13-D8
A13-B5-C13-D8
A24-B5-C13-D8
A69-B5-C13-D8
A67-B5-C13-D8
A39-B5-C13-D8
A65-B5-C13-D8
A66-B5-C13-D8
A2-B6-C13-D8
A3-B6-C13-D8
A9-B6-C13-D8
A13-B6-C13-D8
A24-B6-C13-D8
A69-B6-C13-D8
A67-B6-C13-D8
A39-B6-C13-D8
A65-B6-C13-D8
A66-B6-C13-D8
A2-B32-C13-D8
A3-B32-C13-D8
A9-B32-C13-D8
A13-B32-C13-D8
A24-B32-C13-D8
A69-B32-C13-D8
A67-B32-C13-D8
A39-B32-C13-D8
A65-B32-C13-D8
A66-B32-C13-D8
A2-B39-C13-D8
A3-B39-C13-D8
A9-B39-C13-D8
A13-B39-C13-D8
A24-B39-C13-D8

TABLE 6-continued

A69-B39-C13-D8
A67-B39-C13-D8
A39-B39-C13-D8
A65-B39-C13-D8
A66-B39-C13-D8
A2-B45-C13-D8
A3-B45-C13-D8
A9-B45-C13-D8
A13-B45-C13-D8
A24-B45-C13-D8
A69-B45-C13-D8
A67-B45-C13-D8
A39-B45-C13-D8
A65-B45-C13-D8
A66-B45-C13-D8
A2-B53-C13-D8
A3-B53-C13-D8
A9-B53-C13-D8
A13-B53-C13-D8
A24-B53-C13-D8
A69-B53-C13-D8
A67-B53-C13-D8
A39-B53-C13-D8
A65-B53-C13-D8
A66-B53-C13-D8
A2-B79-C13-D8
A3-B79-C13-D8
A9-B79-C13-D8
A13-B79-C13-D8
A24-B79-C13-D8
A69-B79-C13-D8
A67-B79-C13-D8
A39-B79-C13-D8
A65-B79-C13-D8
A66-B79-C13-D8
A2-B80-C13-D8
A3-B80-C13-D8
A9-B80-C13-D8
A13-B80-C13-D8
A24-B80-C13-D8
A69-B80-C13-D8
A67-B80-C13-D8
A39-B80-C13-D8
A65-B80-C13-D8
A66-B80-C13-D8
A2-B85-C13-D8
A3-B85-C13-D8
A9-B85-C13-D8
A13-B85-C13-D8
A24-B85-C13-D8
A69-B85-C13-D8
A67-B85-C13-D8
A39-B85-C13-D8
A65-B85-C13-D8
A66-B85-C13-D8
A2-B86-C13-D8
A3-B86-C13-D8
A9-B86-C13-D8
A13-B86-C13-D8
A24-B86-C13-D8
A69-B86-C13-D8
A67-B86-C13-D8
A39-B86-C13-D8
A65-B86-C13-D8
A66-B86-C13-D8
A2-B87-C13-D8
A3-B87-C13-D8
A9-B87-C13-D8
A13-B87-C13-D8
A24-B87-C13-D8
A69-B87-C13-D8
A67-B87-C13-D8
A39-B87-C13-D8
A65-B87-C13-D8
A66-B87-C13-D8
A2-B89-C13-D8
A3-B89-C13-D8
A9-B89-C13-D8
A13-B89-C13-D8

TABLE 6-continued

A24-B89-C13-D8
A69-B89-C13-D8
A67-B89-C13-D8
A39-B89-C13-D8
A65-B89-C13-D8
A66-B89-C13-D8
A2-B92-C13-D8
A3-B92-C13-D8
A9-B92-C13-D8
A13-B92-C13-D8
A24-B92-C13-D8
A69-B92-C13-D8
A67-B92-C13-D8
A39-B92-C13-D8
A65-B92-C13-D8
A66-B92-C13-D8
A2-B4-C1-D9
A3-B4-C1-D9
A9-B4-C1-D9
A13-B4-C1-D9
A24-B4-C1-D9
A69-B4-C1-D9
A67-B4-C1-D9
A39-B4-C1-D9
A65-B4-C1-D9
A66-B4-C1-D9
A2-B5-C1-D9
A3-B5-C1-D9
A9-B5-C1-D9
A13-B5-C1-D9
A24-B5-C1-D9
A69-B5-C1-D9
A67-B5-C1-D9
A39-B5-C1-D9
A65-B5-C1-D9
A66-B5-C1-D9
A2-B6-C1-D9
A3-B6-C1-D9
A9-B6-C1-D9
A13-B6-C1-D9
A24-B6-C1-D9
A69-B6-C1-D9
A67-B6-C1-D9
A39-B6-C1-D9
A65-B6-C1-D9
A66-B6-C1-D9
A2-B32-C1-D9
A3-B32-C1-D9
A9-B32-C1-D9
A13-B32-C1-D9
A24-B32-C1-D9
A69-B32-C1-D9
A67-B32-C1-D9
A39-B32-C1-D9
A65-B32-C1-D9
A66-B32-C1-D9
A2-B39-C1-D9
A3-B39-C1-D9
A9-B39-C1-D9
A13-B39-C1-D9
A24-B39-C1-D9
A69-B39-C1-D9
A67-B39-C1-D9
A39-B39-C1-D9
A65-B39-C1-D9
A66-B39-C1-D9
A2-B45-C1-D9
A3-B45-C1-D9
A9-B45-C1-D9
A13-B45-C1-D9
A24-B45-C1-D9
A69-B45-C1-D9
A67-B45-C1-D9
A39-B45-C1-D9
A65-B45-C1-D9
A66-B45-C1-D9
A2-B53-C1-D9
A3-B53-C1-D9
A9-B53-C1-D9
A13-B53-C1-D9
A24-B53-C1-D9
A69-B53-C1-D9
A67-B53-C1-D9
A39-B53-C1-D9
A65-B53-C1-D9
A66-B53-C1-D9
A2-B79-C1-D9
A3-B79-C1-D9
A9-B79-C1-D9
A13-B79-C1-D9
A24-B79-C1-D9
A69-B79-C1-D9
A67-B79-C1-D9
A39-B79-C1-D9
A65-B79-C1-D9
A66-B79-C1-D9
A2-B80-C1-D9
A3-B80-C1-D9
A9-B80-C1-D9
A13-B80-C1-D9
A24-B80-C1-D9
A69-B80-C1-D9
A67-B80-C1-D9
A39-B80-C1-D9
A65-B80-C1-D9
A66-B80-C1-D9
A2-B85-C1-D9
A3-B85-C1-D9
A9-B85-C1-D9
A13-B85-C1-D9
A24-B85-C1-D9
A69-B85-C1-D9
A67-B85-C1-D9
A39-B85-C1-D9
A65-B85-C1-D9
A66-B85-C1-D9
A2-B86-C1-D9
A3-B86-C1-D9
A9-B86-C1-D9
A13-B86-C1-D9
A24-B86-C1-D9
A69-B86-C1-D9
A67-B86-C1-D9
A39-B86-C1-D9
A65-B86-C1-D9
A66-B86-C1-D9
A2-B87-C1-D9
A3-B87-C1-D9
A9-B87-C1-D9
A13-B87-C1-D9
A24-B87-C1-D9
A69-B87-C1-D9
A67-B87-C1-D9
A39-B87-C1-D9
A65-B87-C1-D9
A66-B87-C1-D9
A2-B89-C1-D9
A3-B89-C1-D9
A9-B89-C1-D9
A13-B89-C1-D9
A24-B89-C1-D9
A69-B89-C1-D9
A67-B89-C1-D9
A39-B89-C1-D9
A65-B89-C1-D9
A66-B89-C1-D9
A2-B92-C1-D9
A3-B92-C1-D9
A9-B92-C1-D9
A13-B92-C1-D9
A24-B92-C1-D9
A69-B92-C1-D9
A67-B92-C1-D9
A39-B92-C1-D9
A65-B92-C1-D9
A66-B92-C1-D9
A2-B4-C2-D9
A3-B4-C2-D9

TABLE 6-continued

A9-B4-C2-D9
A13-B4-C2-D9
A24-B4-C2-D9
A69-B4-C2-D9
A67-B4-C2-D9
A39-B4-C2-D9
A65-B4-C2-D9
A66-B4-C2-D9
A2-B5-C2-D9
A3-B5-C2-D9
A9-B5-C2-D9
A13-B5-C2-D9
A24-B5-C2-D9
A69-B5-C2-D9
A67-B5-C2-D9
A39-B5-C2-D9
A65-B5-C2-D9
A66-B5-C2-D9
A2-B6-C2-D9
A3-B6-C2-D9
A9-B6-C2-D9
A13-B6-C2-D9
A24-B6-C2-D9
A69-B6-C2-D9
A67-B6-C2-D9
A39-B6-C2-D9
A65-B6-C2-D9
A66-B6-C2-D9
A2-B32-C2-D9
A3-B32-C2-D9
A9-B32-C2-D9
A13-B32-C2-D9
A24-B32-C2-D9
A69-B32-C2-D9
A67-B32-C2-D9
A39-B32-C2-D9
A65-B32-C2-D9
A66-B32-C2-D9
A2-B39-C2-D9
A3-B39-C2-D9
A9-B39-C2-D9
A13-B39-C2-D9
A24-B39-C2-D9
A69-B39-C2-D9
A67-B39-C2-D9
A39-B39-C2-D9
A65-B39-C2-D9
A66-B39-C2-D9
A2-B45-C2-D9
A3-B45-C2-D9
A9-B45-C2-D9
A13-B45-C2-D9
A24-B45-C2-D9
A69-B45-C2-D9
A67-B45-C2-D9
A39-B45-C2-D9
A65-B45-C2-D9
A66-B45-C2-D9
A2-B53-C2-D9
A3-B53-C2-D9
A9-B53-C2-D9
A13-B53-C2-D9
A24-B53-C2-D9
A69-B53-C2-D9
A67-B53-C2-D9
A39-B53-C2-D9
A65-B53-C2-D9
A66-B53-C2-D9
A2-B79-C2-D9
A3-B79-C2-D9
A9-B79-C2-D9
A13-B79-C2-D9
A24-B79-C2-D9
A69-B79-C2-D9
A67-B79-C2-D9
A39-B79-C2-D9
A65-B79-C2-D9
A66-B79-C2-D9
A2-B80-C2-D9

TABLE 6-continued

A3-B80-C2-D9
A9-B80-C2-D9
A13-B80-C2-D9
A24-B80-C2-D9
A69-B80-C2-D9
A67-B80-C2-D9
A39-B80-C2-D9
A65-B80-C2-D9
A66-B80-C2-D9
A2-B85-C2-D9
A3-B85-C2-D9
A9-B85-C2-D9
A13-B85-C2-D9
A24-B85-C2-D9
A69-B85-C2-D9
A67-B85-C2-D9
A39-B85-C2-D9
A65-B85-C2-D9
A66-B85-C2-D9
A2-B86-C2-D9
A3-B86-C2-D9
A9-B86-C2-D9
A13-B86-C2-D9
A24-B86-C2-D9
A69-B86-C2-D9
A67-B86-C2-D9
A39-B86-C2-D9
A65-B86-C2-D9
A66-B86-C2-D9
A2-B87-C2-D9
A3-B87-C2-D9
A9-B87-C2-D9
A13-B87-C2-D9
A24-B87-C2-D9
A69-B87-C2-D9
A67-B87-C2-D9
A39-B87-C2-D9
A65-B87-C2-D9
A66-B87-C2-D9
A2-B89-C2-D9
A3-B89-C2-D9
A9-B89-C2-D9
A13-B89-C2-D9
A24-B89-C2-D9
A69-B89-C2-D9
A67-B89-C2-D9
A39-B89-C2-D9
A65-B89-C2-D9
A66-B89-C2-D9
A2-B92-C2-D9
A3-B92-C2-D9
A9-B92-C2-D9
A13-B92-C2-D9
A24-B92-C2-D9
A69-B92-C2-D9
A67-B92-C2-D9
A39-B92-C2-D9
A65-B92-C2-D9
A66-B92-C2-D9
A2-B4-C3-D9
A3-B4-C3-D9
A9-B4-C3-D9
A13-B4-C3-D9
A24-B4-C3-D9
A69-B4-C3-D9
A67-B4-C3-D9
A39-B4-C3-D9
A65-B4-C3-D9
A66-B4-C3-D9
A2-B5-C3-D9
A3-B5-C3-D9
A9-B5-C3-D9
A13-B5-C3-D9
A24-B5-C3-D9
A69-B5-C3-D9
A67-B5-C3-D9
A39-B5-C3-D9
A65-B5-C3-D9
A66-B5-C3-D9

TABLE 6-continued

A2-B6-C3-D9
A3-B6-C3-D9
A9-B6-C3-D9
A13-B6-C3-D9
A24-B6-C3-D9
A69-B6-C3-D9
A67-B6-C3-D9
A39-B6-C3-D9
A65-B6-C3-D9
A66-B6-C3-D9
A2-B32-C3-D9
A3-B32-C3-D9
A9-B32-C3-D9
A13-B32-C3-D9
A24-B32-C3-D9
A69-B32-C3-D9
A67-B32-C3-D9
A39-B32-C3-D9
A65-B32-C3-D9
A66-B32-C3-D9
A2-B39-C3-D9
A3-B39-C3-D9
A9-B39-C3-D9
A13-B39-C3-D9
A24-B39-C3-D9
A69-B39-C3-D9
A67-B39-C3-D9
A39-B39-C3-D9
A65-B39-C3-D9
A66-B39-C3-D9
A2-B45-C3-D9
A3-B45-C3-D9
A9-B45-C3-D9
A13-B45-C3-D9
A24-B45-C3-D9
A69-B45-C3-D9
A67-B45-C3-D9
A39-B45-C3-D9
A65-B45-C3-D9
A66-B45-C3-D9
A2-B53-C3-D9
A3-B53-C3-D9
A9-B53-C3-D9
A13-B53-C3-D9
A24-B53-C3-D9
A69-B53-C3-D9
A67-B53-C3-D9
A39-B53-C3-D9
A65-B53-C3-D9
A66-B53-C3-D9
A2-B79-C3-D9
A3-B79-C3-D9
A9-B79-C3-D9
A13-B79-C3-D9
A24-B79-C3-D9
A69-B79-C3-D9
A67-B79-C3-D9
A39-B79-C3-D9
A65-B79-C3-D9
A66-B79-C3-D9
A2-B80-C3-D9
A3-B80-C3-D9
A9-B80-C3-D9
A13-B80-C3-D9
A24-B80-C3-D9
A69-B80-C3-D9
A67-B80-C3-D9
A39-B80-C3-D9
A65-B80-C3-D9
A66-B80-C3-D9
A2-B85-C3-D9
A3-B85-C3-D9
A9-B85-C3-D9
A13-B85-C3-D9
A24-B85-C3-D9
A69-B85-C3-D9
A67-B85-C3-D9
A39-B85-C3-D9
A65-B85-C3-D9
A66-B85-C3-D9
A2-B86-C3-D9
A3-B86-C3-D9
A9-B86-C3-D9
A13-B86-C3-D9
A24-B86-C3-D9
A69-B86-C3-D9
A67-B86-C3-D9
A39-B86-C3-D9
A65-B86-C3-D9
A66-B86-C3-D9
A2-B87-C3-D9
A3-B87-C3-D9
A9-B87-C3-D9
A13-B87-C3-D9
A24-B87-C3-D9
A69-B87-C3-D9
A67-B87-C3-D9
A39-B87-C3-D9
A65-B87-C3-D9
A66-B87-C3-D9
A2-B89-C3-D9
A3-B89-C3-D9
A9-B89-C3-D9
A13-B89-C3-D9
A24-B89-C3-D9
A69-B89-C3-D9
A67-B89-C3-D9
A39-B89-C3-D9
A65-B89-C3-D9
A66-B89-C3-D9
A2-B92-C3-D9
A3-B92-C3-D9
A9-B92-C3-D9
A13-B92-C3-D9
A24-B92-C3-D9
A69-B92-C3-D9
A67-B92-C3-D9
A39-B92-C3-D9
A65-B92-C3-D9
A66-B92-C3-D9
A2-B4-C4-D9
A3-B4-C4-D9
A9-B4-C4-D9
A13-B4-C4-D9
A24-B4-C4-D9
A69-B4-C4-D9
A67-B4-C4-D9
A39-B4-C4-D9
A65-B4-C4-D9
A66-B4-C4-D9
A2-B5-C4-D9
A3-B5-C4-D9
A9-B5-C4-D9
A13-B5-C4-D9
A24-B5-C4-D9
A69-B5-C4-D9
A67-B5-C4-D9
A39-B5-C4-D9
A65-B5-C4-D9
A66-B5-C4-D9
A2-B6-C4-D9
A3-B6-C4-D9
A9-B6-C4-D9
A13-B6-C4-D9
A24-B6-C4-D9
A69-B6-C4-D9
A67-B6-C4-D9
A39-B6-C4-D9
A65-B6-C4-D9
A66-B6-C4-D9
A2-B32-C4-D9
A3-B32-C4-D9
A9-B32-C4-D9
A13-B32-C4-D9
A24-B32-C4-D9
A69-B32-C4-D9
A67-B32-C4-D9
A39-B32-C4-D9

TABLE 6-continued

A65-B32-C4-D9
A66-B32-C4-D9
A2-B39-C4-D9
A3-B39-C4-D9
A9-B39-C4-D9
A13-B39-C4-D9
A24-B39-C4-D9
A69-B39-C4-D9
A67-B39-C4-D9
A39-B39-C4-D9
A65-B39-C4-D9
A66-B39-C4-D9
A2-B45-C4-D9
A3-B45-C4-D9
A9-B45-C4-D9
A13-B45-C4-D9
A24-B45-C4-D9
A69-B45-C4-D9
A67-B45-C4-D9
A39-B45-C4-D9
A65-B45-C4-D9
A66-B45-C4-D9
A2-B53-C4-D9
A3-B53-C4-D9
A9-B53-C4-D9
A13-B53-C4-D9
A24-B53-C4-D9
A69-B53-C4-D9
A67-B53-C4-D9
A39-B53-C4-D9
A65-B53-C4-D9
A66-B53-C4-D9
A2-B79-C4-D9
A3-B79-C4-D9
A9-B79-C4-D9
A13-B79-C4-D9
A24-B79-C4-D9
A69-B79-C4-D9
A67-B79-C4-D9
A39-B79-C4-D9
A65-B79-C4-D9
A66-B79-C4-D9
A2-B80-C4-D9
A3-B80-C4-D9
A9-B80-C4-D9
A13-B80-C4-D9
A24-B80-C4-D9
A69-B80-C4-D9
A67-B80-C4-D9
A39-B80-C4-D9
A65-B80-C4-D9
A66-B80-C4-D9
A2-B85-C4-D9
A3-B85-C4-D9
A9-B85-C4-D9
A13-B85-C4-D9
A24-B85-C4-D9
A69-B85-C4-D9
A67-B85-C4-D9
A39-B85-C4-D9
A65-B85-C4-D9
A66-B85-C4-D9
A2-B86-C4-D9
A3-B86-C4-D9
A9-B86-C4-D9
A13-B86-C4-D9
A24-B86-C4-D9
A69-B86-C4-D9
A67-B86-C4-D9
A39-B86-C4-D9
A65-B86-C4-D9
A66-B86-C4-D9
A2-B87-C4-D9
A3-B87-C4-D9
A9-B87-C4-D9
A13-B87-C4-D9
A24-B87-C4-D9
A69-B87-C4-D9
A67-B87-C4-D9
A39-B87-C4-D9
A65-B87-C4-D9
A66-B87-C4-D9
A2-B89-C4-D9
A3-B89-C4-D9
A9-B89-C4-D9
A13-B89-C4-D9
A24-B89-C4-D9
A69-B89-C4-D9
A67-B89-C4-D9
A39-B89-C4-D9
A65-B89-C4-D9
A66-B89-C4-D9
A2-B92-C4-D9
A3-B92-C4-D9
A9-B92-C4-D9
A13-B92-C4-D9
A24-B92-C4-D9
A69-B92-C4-D9
A67-B92-C4-D9
A39-B92-C4-D9
A65-B92-C4-D9
A66-B92-C4-D9
A2-B4-C5-D9
A3-B4-C5-D9
A9-B4-C5-D9
A13-B4-C5-D9
A24-B4-C5-D9
A69-B4-C5-D9
A67-B4-C5-D9
A39-B4-C5-D9
A65-B4-C5-D9
A66-B4-C5-D9
A2-B5-C5-D9
A3-B5-C5-D9
A9-B5-C5-D9
A13-B5-C5-D9
A24-B5-C5-D9
A69-B5-C5-D9
A67-B5-C5-D9
A39-B5-C5-D9
A65-B5-C5-D9
A66-B5-C5-D9
A2-B6-C5-D9
A3-B6-C5-D9
A9-B6-C5-D9
A13-B6-C5-D9
A24-B6-C5-D9
A69-B6-C5-D9
A67-B6-C5-D9
A39-B6-C5-D9
A65-B6-C5-D9
A66-B6-C5-D9
A2-B32-C5-D9
A3-B32-C5-D9
A9-B32-C5-D9
A13-B32-C5-D9
A24-B32-C5-D9
A69-B32-C5-D9
A67-B32-C5-D9
A39-B32-C5-D9
A65-B32-C5-D9
A66-B32-C5-D9
A2-B39-C5-D9
A3-B39-C5-D9
A9-B39-C5-D9
A13-B39-C5-D9
A24-B39-C5-D9
A69-B39-C5-D9
A67-B39-C5-D9
A39-B39-C5-D9
A65-B39-C5-D9
A66-B39-C5-D9
A2-B45-C5-D9
A3-B45-C5-D9
A9-B45-C5-D9
A13-B45-C5-D9
A24-B45-C5-D9
A69-B45-C5-D9

TABLE 6-continued

A67-B45-C5-D9
A39-B45-C5-D9
A65-B45-C5-D9
A66-B45-C5-D9
A2-B53-C5-D9
A3-B53-C5-D9
A9-B53-C5-D9
A13-B53-C5-D9
A24-B53-C5-D9
A69-B53-C5-D9
A67-B53-C5-D9
A39-B53-C5-D9
A65-B53-C5-D9
A66-B53-C5-D9
A2-B79-C5-D9
A3-B79-C5-D9
A9-B79-C5-D9
A13-B79-C5-D9
A24-B79-C5-D9
A69-B79-C5-D9
A67-B79-C5-D9
A39-B79-C5-D9
A65-B79-C5-D9
A66-B79-C5-D9
A2-B80-C5-D9
A3-B80-C5-D9
A9-B80-C5-D9
A13-B80-C5-D9
A24-B80-C5-D9
A69-B80-C5-D9
A67-B80-C5-D9
A39-B80-C5-D9
A65-B80-C5-D9
A66-B80-C5-D9
A2-B85-C5-D9
A3-B85-C5-D9
A9-B85-C5-D9
A13-B85-C5-D9
A24-B85-C5-D9
A69-B85-C5-D9
A67-B85-C5-D9
A39-B85-C5-D9
A65-B85-C5-D9
A66-B85-C5-D9
A2-B86-C5-D9
A3-B86-C5-D9
A9-B86-C5-D9
A13-B86-C5-D9
A24-B86-C5-D9
A69-B86-C5-D9
A67-B86-C5-D9
A39-B86-C5-D9
A65-B86-C5-D9
A66-B86-C5-D9
A2-B87-C5-D9
A3-B87-C5-D9
A9-B87-C5-D9
A13-B87-C5-D9
A24-B87-C5-D9
A69-B87-C5-D9
A67-B87-C5-D9
A39-B87-C5-D9
A65-B87-C5-D9
A66-B87-C5-D9
A2-B89-C5-D9
A3-B89-C5-D9
A9-B89-C5-D9
A13-B89-C5-D9
A24-B89-C5-D9
A69-B89-C5-D9
A67-B89-C5-D9
A39-B89-C5-D9
A65-B89-C5-D9
A66-B89-C5-D9
A2-B92-C5-D9
A3-B92-C5-D9
A9-B92-C5-D9
A13-B92-C5-D9
A24-B92-C5-D9

TABLE 6-continued

A69-B92-C5-D9
A67-B92-C5-D9
A39-B92-C5-D9
A65-B92-C5-D9
A66-B92-C5-D9
A2-B4-C6-D9
A3-B4-C6-D9
A9-B4-C6-D9
A13-B4-C6-D9
A24-B4-C6-D9
A69-B4-C6-D9
A67-B4-C6-D9
A39-B4-C6-D9
A65-B4-C6-D9
A66-B4-C6-D9
A2-B5-C6-D9
A3-B5-C6-D9
A9-B5-C6-D9
A13-B5-C6-D9
A24-B5-C6-D9
A69-B5-C6-D9
A67-B5-C6-D9
A39-B5-C6-D9
A65-B5-C6-D9
A66-B5-C6-D9
A2-B6-C6-D9
A3-B6-C6-D9
A9-B6-C6-D9
A13-B6-C6-D9
A24-B6-C6-D9
A69-B6-C6-D9
A67-B6-C6-D9
A39-B6-C6-D9
A65-B6-C6-D9
A66-B6-C6-D9
A2-B32-C6-D9
A3-B32-C6-D9
A9-B32-C6-D9
A13-B32-C6-D9
A24-B32-C6-D9
A69-B32-C6-D9
A67-B32-C6-D9
A39-B32-C6-D9
A65-B32-C6-D9
A66-B32-C6-D9
A2-B39-C6-D9
A3-B39-C6-D9
A9-B39-C6-D9
A13-B39-C6-D9
A24-B39-C6-D9
A69-B39-C6-D9
A67-B39-C6-D9
A39-B39-C6-D9
A65-B39-C6-D9
A66-B39-C6-D9
A2-B45-C6-D9
A3-B45-C6-D9
A9-B45-C6-D9
A13-B45-C6-D9
A24-B45-C6-D9
A69-B45-C6-D9
A67-B45-C6-D9
A39-B45-C6-D9
A65-B45-C6-D9
A66-B45-C6-D9
A2-B53-C6-D9
A3-B53-C6-D9
A9-B53-C6-D9
A13-B53-C6-D9
A24-B53-C6-D9
A69-B53-C6-D9
A67-B53-C6-D9
A39-B53-C6-D9
A65-B53-C6-D9
A66-B53-C6-D9
A2-B79-C6-D9
A3-B79-C6-D9
A9-B79-C6-D9
A13-B79-C6-D9

TABLE 6-continued

A24-B79-C6-D9
A69-B79-C6-D9
A67-B79-C6-D9
A39-B79-C6-D9
A65-B79-C6-D9
A66-B79-C6-D9
A2-B80-C6-D9
A3-B80-C6-D9
A9-B80-C6-D9
A13-B80-C6-D9
A24-B80-C6-D9
A69-B80-C6-D9
A67-B80-C6-D9
A39-B80-C6-D9
A65-B80-C6-D9
A66-B80-C6-D9
A2-B85-C6-D9
A3-B85-C6-D9
A9-B85-C6-D9
A13-B85-C6-D9
A24-B85-C6-D9
A69-B85-C6-D9
A67-B85-C6-D9
A39-B85-C6-D9
A65-B85-C6-D9
A66-B85-C6-D9
A2-B86-C6-D9
A3-B86-C6-D9
A9-B86-C6-D9
A13-B86-C6-D9
A24-B86-C6-D9
A69-B86-C6-D9
A67-B86-C6-D9
A39-B86-C6-D9
A65-B86-C6-D9
A66-B86-C6-D9
A2-B87-C6-D9
A3-B87-C6-D9
A9-B87-C6-D9
A13-B87-C6-D9
A24-B87-C6-D9
A69-B87-C6-D9
A67-B87-C6-D9
A39-B87-C6-D9
A65-B87-C6-D9
A66-B87-C6-D9
A2-B89-C6-D9
A3-B89-C6-D9
A9-B89-C6-D9
A13-B89-C6-D9
A24-B89-C6-D9
A69-B89-C6-D9
A67-B89-C6-D9
A39-B89-C6-D9
A65-B89-C6-D9
A66-B89-C6-D9
A2-B92-C6-D9
A3-B92-C6-D9
A9-B92-C6-D9
A13-B92-C6-D9
A24-B92-C6-D9
A69-B92-C6-D9
A67-B92-C6-D9
A39-B92-C6-D9
A65-B92-C6-D9
A66-B92-C6-D9
A2-B4-C7-D9
A3-B4-C7-D9
A9-B4-C7-D9
A13-B4-C7-D9
A24-B4-C7-D9
A69-B4-C7-D9
A67-B4-C7-D9
A39-B4-C7-D9
A65-B4-C7-D9
A66-B4-C7-D9
A2-B5-C7-D9
A3-B5-C7-D9
A9-B5-C7-D9

TABLE 6-continued

A13-B5-C7-D9
A24-B5-C7-D9
A69-B5-C7-D9
A67-B5-C7-D9
A39-B5-C7-D9
A65-B5-C7-D9
A66-B5-C7-D9
A2-B6-C7-D9
A3-B6-C7-D9
A9-B6-C7-D9
A13-B6-C7-D9
A24-B6-C7-D9
A69-B6-C7-D9
A67-B6-C7-D9
A39-B6-C7-D9
A65-B6-C7-D9
A66-B6-C7-D9
A2-B32-C7-D9
A3-B32-C7-D9
A9-B32-C7-D9
A13-B32-C7-D9
A24-B32-C7-D9
A69-B32-C7-D9
A67-B32-C7-D9
A39-B32-C7-D9
A65-B32-C7-D9
A66-B32-C7-D9
A2-B39-C7-D9
A3-B39-C7-D9
A9-B39-C7-D9
A13-B39-C7-D9
A24-B39-C7-D9
A69-B39-C7-D9
A67-B39-C7-D9
A39-B39-C7-D9
A65-B39-C7-D9
A66-B39-C7-D9
A2-B45-C7-D9
A3-B45-C7-D9
A9-B45-C7-D9
A13-B45-C7-D9
A24-B45-C7-D9
A69-B45-C7-D9
A67-B45-C7-D9
A39-B45-C7-D9
A65-B45-C7-D9
A66-B45-C7-D9
A2-B53-C7-D9
A3-B53-C7-D9
A9-B53-C7-D9
A13-B53-C7-D9
A24-B53-C7-D9
A69-B53-C7-D9
A67-B53-C7-D9
A39-B53-C7-D9
A65-B53-C7-D9
A66-B53-C7-D9
A2-B79-C7-D9
A3-B79-C7-D9
A9-B79-C7-D9
A13-B79-C7-D9
A24-B79-C7-D9
A69-B79-C7-D9
A67-B79-C7-D9
A39-B79-C7-D9
A65-B79-C7-D9
A66-B79-C7-D9
A2-B80-C7-D9
A3-B80-C7-D9
A9-B80-C7-D9
A13-B80-C7-D9
A24-B80-C7-D9
A69-B80-C7-D9
A67-B80-C7-D9
A39-B80-C7-D9
A65-B80-C7-D9
A66-B80-C7-D9
A2-B85-C7-D9
A3-B85-C7-D9

TABLE 6-continued

A9-B85-C7-D9
A13-B85-C7-D9
A24-B85-C7-D9
A69-B85-C7-D9
A67-B85-C7-D9
A39-B85-C7-D9
A65-B85-C7-D9
A66-B85-C7-D9
A2-B86-C7-D9
A3-B86-C7-D9
A9-B86-C7-D9
A13-B86-C7-D9
A24-B86-C7-D9
A69-B86-C7-D9
A67-B86-C7-D9
A39-B86-C7-D9
A65-B86-C7-D9
A66-B86-C7-D9
A2-B87-C7-D9
A3-B87-C7-D9
A9-B87-C7-D9
A13-B87-C7-D9
A24-B87-C7-D9
A69-B87-C7-D9
A67-B87-C7-D9
A39-B87-C7-D9
A65-B87-C7-D9
A66-B87-C7-D9
A2-B89-C7-D9
A3-B89-C7-D9
A9-B89-C7-D9
A13-B89-C7-D9
A24-B89-C7-D9
A69-B89-C7-D9
A67-B89-C7-D9
A39-B89-C7-D9
A65-B89-C7-D9
A66-B89-C7-D9
A2-B92-C7-D9
A3-B92-C7-D9
A9-B92-C7-D9
A13-B92-C7-D9
A24-B92-C7-D9
A69-B92-C7-D9
A67-B92-C7-D9
A39-B92-C7-D9
A65-B92-C7-D9
A66-B92-C7-D9
A2-B4-C8-D9
A3-B4-C8-D9
A9-B4-C8-D9
A13-B4-C8-D9
A24-B4-C8-D9
A69-B4-C8-D9
A67-B4-C8-D9
A39-B4-C8-D9
A65-B4-C8-D9
A66-B4-C8-D9
A2-B5-C8-D9
A3-B5-C8-D9
A9-B5-C8-D9
A13-B5-C8-D9
A24-B5-C8-D9
A69-B5-C8-D9
A67-B5-C8-D9
A39-B5-C8-D9
A65-B5-C8-D9
A66-B5-C8-D9
A2-B6-C8-D9
A3-B6-C8-D9
A9-B6-C8-D9
A13-B6-C8-D9
A24-B6-C8-D9
A69-B6-C8-D9
A67-B6-C8-D9
A39-B6-C8-D9
A65-B6-C8-D9
A66-B6-C8-D9
A2-B32-C8-D9

TABLE 6-continued

A3-B32-C8-D9
A9-B32-C8-D9
A13-B32-C8-D9
A24-B32-C8-D9
A69-B32-C8-D9
A67-B32-C8-D9
A39-B32-C8-D9
A65-B32-C8-D9
A66-B32-C8-D9
A2-B39-C8-D9
A3-B39-C8-D9
A9-B39-C8-D9
A13-B39-C8-D9
A24-B39-C8-D9
A69-B39-C8-D9
A67-B39-C8-D9
A39-B39-C8-D9
A65-B39-C8-D9
A66-B39-C8-D9
A2-B45-C8-D9
A3-B45-C8-D9
A9-B45-C8-D9
A13-B45-C8-D9
A24-B45-C8-D9
A69-B45-C8-D9
A67-B45-C8-D9
A39-B45-C8-D9
A65-B45-C8-D9
A66-B45-C8-D9
A2-B53-C8-D9
A3-B53-C8-D9
A9-B53-C8-D9
A13-B53-C8-D9
A24-B53-C8-D9
A69-B53-C8-D9
A67-B53-C8-D9
A39-B53-C8-D9
A65-B53-C8-D9
A66-B53-C8-D9
A2-B79-C8-D9
A3-B79-C8-D9
A9-B79-C8-D9
A13-B79-C8-D9
A24-B79-C8-D9
A69-B79-C8-D9
A67-B79-C8-D9
A39-B79-C8-D9
A65-B79-C8-D9
A66-B79-C8-D9
A2-B80-C8-D9
A3-B80-C8-D9
A9-B80-C8-D9
A13-B80-C8-D9
A24-B80-C8-D9
A69-B80-C8-D9
A67-B80-C8-D9
A39-B80-C8-D9
A65-B80-C8-D9
A66-B80-C8-D9
A2-B85-C8-D9
A3-B85-C8-D9
A9-B85-C8-D9
A13-B85-C8-D9
A24-B85-C8-D9
A69-B85-C8-D9
A67-B85-C8-D9
A39-B85-C8-D9
A65-B85-C8-D9
A66-B85-C8-D9
A2-B86-C8-D9
A3-B86-C8-D9
A9-B86-C8-D9
A13-B86-C8-D9
A24-B86-C8-D9
A69-B86-C8-D9
A67-B86-C8-D9
A39-B86-C8-D9
A65-B86-C8-D9
A66-B86-C8-D9

TABLE 6-continued

A2-B87-C8-D9
A3-B87-C8-D9
A9-B87-C8-D9
A13-B87-C8-D9
A24-B87-C8-D9
A69-B87-C8-D9
A67-B87-C8-D9
A39-B87-C8-D9
A65-B87-C8-D9
A66-B87-C8-D9
A2-B89-C8-D9
A3-B89-C8-D9
A9-B89-C8-D9
A13-B89-C8-D9
A24-B89-C8-D9
A69-B89-C8-D9
A67-B89-C8-D9
A39-B89-C8-D9
A65-B89-C8-D9
A66-B89-C8-D9
A2-B92-C8-D9
A3-B92-C8-D9
A9-B92-C8-D9
A13-B92-C8-D9
A24-B92-C8-D9
A69-B92-C8-D9
A67-B92-C8-D9
A39-B92-C8-D9
A65-B92-C8-D9
A66-B92-C8-D9
A2-B4-C9-D9
A3-B4-C9-D9
A9-B4-C9-D9
A13-B4-C9-D9
A24-B4-C9-D9
A69-B4-C9-D9
A67-B4-C9-D9
A39-B4-C9-D9
A65-B4-C9-D9
A66-B4-C9-D9
A2-B5-C9-D9
A3-B5-C9-D9
A9-B5-C9-D9
A13-B5-C9-D9
A24-B5-C9-D9
A69-B5-C9-D9
A67-B5-C9-D9
A39-B5-C9-D9
A65-B5-C9-D9
A66-B5-C9-D9
A2-B6-C9-D9
A3-B6-C9-D9
A9-B6-C9-D9
A13-B6-C9-D9
A24-B6-C9-D9
A69-B6-C9-D9
A67-B6-C9-D9
A39-B6-C9-D9
A65-B6-C9-D9
A66-B6-C9-D9
A2-B32-C9-D9
A3-B32-C9-D9
A9-B32-C9-D9
A13-B32-C9-D9
A24-B32-C9-D9
A69-B32-C9-D9
A67-B32-C9-D9
A39-B32-C9-D9
A65-B32-C9-D9
A66-B32-C9-D9
A2-B39-C9-D9
A3-B39-C9-D9
A9-B39-C9-D9
A13-B39-C9-D9
A24-B39-C9-D9
A69-B39-C9-D9
A67-B39-C9-D9
A39-B39-C9-D9
A65-B39-C9-D9

TABLE 6-continued

A66-B39-C9-D9
A2-B45-C9-D9
A3-B45-C9-D9
A9-B45-C9-D9
A13-B45-C9-D9
A24-B45-C9-D9
A69-B45-C9-D9
A67-B45-C9-D9
A39-B45-C9-D9
A65-B45-C9-D9
A66-B45-C9-D9
A2-B53-C9-D9
A3-B53-C9-D9
A9-B53-C9-D9
A13-B53-C9-D9
A24-B53-C9-D9
A69-B53-C9-D9
A67-B53-C9-D9
A39-B53-C9-D9
A65-B53-C9-D9
A66-B53-C9-D9
A2-B79-C9-D9
A3-B79-C9-D9
A9-B79-C9-D9
A13-B79-C9-D9
A24-B79-C9-D9
A69-B79-C9-D9
A67-B79-C9-D9
A39-B79-C9-D9
A65-B79-C9-D9
A66-B79-C9-D9
A2-B80-C9-D9
A3-B80-C9-D9
A9-B80-C9-D9
A13-B80-C9-D9
A24-B80-C9-D9
A69-B80-C9-D9
A67-B80-C9-D9
A39-B80-C9-D9
A65-B80-C9-D9
A66-B80-C9-D9
A2-B85-C9-D9
A3-B85-C9-D9
A9-B85-C9-D9
A13-B85-C9-D9
A24-B85-C9-D9
A69-B85-C9-D9
A67-B85-C9-D9
A39-B85-C9-D9
A65-B85-C9-D9
A66-B85-C9-D9
A2-B86-C9-D9
A3-B86-C9-D9
A9-B86-C9-D9
A13-B86-C9-D9
A24-B86-C9-D9
A69-B86-C9-D9
A67-B86-C9-D9
A39-B86-C9-D9
A65-B86-C9-D9
A66-B86-C9-D9
A2-B87-C9-D9
A3-B87-C9-D9
A9-B87-C9-D9
A13-B87-C9-D9
A24-B87-C9-D9
A69-B87-C9-D9
A67-B87-C9-D9
A39-B87-C9-D9
A65-B87-C9-D9
A66-B87-C9-D9
A2-B89-C9-D9
A3-B89-C9-D9
A9-B89-C9-D9
A13-B89-C9-D9
A24-B89-C9-D9
A69-B89-C9-D9
A67-B89-C9-D9
A39-B89-C9-D9

TABLE 6-continued

A65-B89-C9-D9
A66-B89-C9-D9
A2-B92-C9-D9
A3-B92-C9-D9
A9-B92-C9-D9
A13-B92-C9-D9
A24-B92-C9-D9
A69-B92-C9-D9
A67-B92-C9-D9
A39-B92-C9-D9
A65-B92-C9-D9
A66-B92-C9-D9
A2-B4-C10-D9
A3-B4-C10-D9
A9-B4-C10-D9
A13-B4-C10-D9
A24-B4-C10-D9
A69-B4-C10-D9
A67-B4-C10-D9
A39-B4-C10-D9
A65-B4-C10-D9
A66-B4-C10-D9
A2-B5-C10-D9
A3-B5-C10-D9
A9-B5-C10-D9
A13-B5-C10-D9
A24-B5-C10-D9
A69-B5-C10-D9
A67-B5-C10-D9
A39-B5-C10-D9
A65-B5-C10-D9
A66-B5-C10-D9
A2-B6-C10-D9
A3-B6-C10-D9
A9-B6-C10-D9
A13-B6-C10-D9
A24-B6-C10-D9
A69-B6-C10-D9
A67-B6-C10-D9
A39-B6-C10-D9
A65-B6-C10-D9
A66-B6-C10-D9
A2-B32-C10-D9
A3-B32-C10-D9
A9-B32-C10-D9
A13-B32-C10-D9
A24-B32-C10-D9
A69-B32-C10-D9
A67-B32-C10-D9
A39-B32-C10-D9
A65-B32-C10-D9
A66-B32-C10-D9
A2-B39-C10-D9
A3-B39-C10-D9
A9-B39-C10-D9
A13-B39-C10-D9
A24-B39-C10-D9
A69-B39-C10-D9
A67-B39-C10-D9
A39-B39-C10-D9
A65-B39-C10-D9
A66-B39-C10-D9
A2-B45-C10-D9
A3-B45-C10-D9
A9-B45-C10-D9
A13-B45-C10-D9
A24-B45-C10-D9
A69-B45-C10-D9
A67-B45-C10-D9
A39-B45-C10-D9
A65-B45-C10-D9
A66-B45-C10-D9
A2-B53-C10-D9
A3-B53-C10-D9
A9-B53-C10-D9
A13-B53-C10-D9
A24-B53-C10-D9
A69-B53-C10-D9
A67-B53-C10-D9

TABLE 6-continued

A39-B53-C10-D9
A65-B53-C10-D9
A66-B53-C10-D9
A2-B79-C10-D9
A3-B79-C10-D9
A9-B79-C10-D9
A13-B79-C10-D9
A24-B79-C10-D9
A69-B79-C10-D9
A67-B79-C10-D9
A39-B79-C10-D9
A65-B79-C10-D9
A66-B79-C10-D9
A2-B80-C10-D9
A3-B80-C10-D9
A9-B80-C10-D9
A13-B80-C10-D9
A24-B80-C10-D9
A69-B80-C10-D9
A67-B80-C10-D9
A39-B80-C10-D9
A65-B80-C10-D9
A66-B80-C10-D9
A2-B85-C10-D9
A3-B85-C10-D9
A9-B85-C10-D9
A13-B85-C10-D9
A24-B85-C10-D9
A69-B85-C10-D9
A67-B85-C10-D9
A39-B85-C10-D9
A65-B85-C10-D9
A66-B85-C10-D9
A2-B86-C10-D9
A3-B86-C10-D9
A9-B86-C10-D9
A13-B86-C10-D9
A24-B86-C10-D9
A69-B86-C10-D9
A67-B86-C10-D9
A39-B86-C10-D9
A65-B86-C10-D9
A66-B86-C10-D9
A2-B87-C10-D9
A3-B87-C10-D9
A9-B87-C10-D9
A13-B87-C10-D9
A24-B87-C10-D9
A69-B87-C10-D9
A67-B87-C10-D9
A39-B87-C10-D9
A65-B87-C10-D9
A66-B87-C10-D9
A2-B89-C10-D9
A3-B89-C10-D9
A9-B89-C10-D9
A13-B89-C10-D9
A24-B89-C10-D9
A69-B89-C10-D9
A67-B89-C10-D9
A39-B89-C10-D9
A65-B89-C10-D9
A66-B89-C10-D9
A2-B92-C10-D9
A3-B92-C10-D9
A9-B92-C10-D9
A13-B92-C10-D9
A24-B92-C10-D9
A69-B92-C10-D9
A67-B92-C10-D9
A39-B92-C10-D9
A65-B92-C10-D9
A66-B92-C10-D9
A2-B4-C11-D9
A3-B4-C11-D9
A9-B4-C11-D9
A13-B4-C11-D9
A24-B4-C11-D9
A69-B4-C11-D9

TABLE 6-continued

A67-B4-C11-D9
A39-B4-C11-D9
A65-B4-C11-D9
A66-B4-C11-D9
A2-B5-C11-D9
A3-B5-C11-D9
A9-B5-C11-D9
A13-B5-C11-D9
A24-B5-C11-D9
A69-B5-C11-D9
A67-B5-C11-D9
A39-B5-C11-D9
A65-B5-C11-D9
A66-B5-C11-D9
A2-B6-C11-D9
A3-B6-C11-D9
A9-B6-C11-D9
A13-B6-C11-D9
A24-B6-C11-D9
A69-B6-C11-D9
A67-B6-C11-D9
A39-B6-C11-D9
A65-B6-C11-D9
A66-B6-C11-D9
A2-B32-C11-D9
A3-B32-C11-D9
A9-B32-C11-D9
A13-B32-C11-D9
A24-B32-C11-D9
A69-B32-C11-D9
A67-B32-C11-D9
A39-B32-C11-D9
A65-B32-C11-D9
A66-B32-C11-D9
A2-B39-C11-D9
A3-B39-C11-D9
A9-B39-C11-D9
A13-B39-C11-D9
A24-B39-C11-D9
A69-B39-C11-D9
A67-B39-C11-D9
A39-B39-C11-D9
A65-B39-C11-D9
A66-B39-C11-D9
A2-B45-C11-D9
A3-B45-C11-D9
A9-B45-C11-D9
A13-B45-C11-D9
A24-B45-C11-D9
A69-B45-C11-D9
A67-B45-C11-D9
A39-B45-C11-D9
A65-B45-C11-D9
A66-B45-C11-D9
A2-B53-C11-D9
A3-B53-C11-D9
A9-B53-C11-D9
A13-B53-C11-D9
A24-B53-C11-D9
A69-B53-C11-D9
A67-B53-C11-D9
A39-B53-C11-D9
A65-B53-C11-D9
A66-B53-C11-D9
A2-B79-C11-D9
A3-B79-C11-D9
A9-B79-C11-D9
A13-B79-C11-D9
A24-B79-C11-D9
A69-B79-C11-D9
A67-B79-C11-D9
A39-B79-C11-D9
A65-B79-C11-D9
A66-B79-C11-D9
A2-B80-C11-D9
A3-B80-C11-D9
A9-B80-C11-D9
A13-B80-C11-D9
A24-B80-C11-D9
A69-B80-C11-D9
A67-B80-C11-D9
A39-B80-C11-D9
A65-B80-C11-D9
A66-B80-C11-D9
A2-B85-C11-D9
A3-B85-C11-D9
A9-B85-C11-D9
A13-B85-C11-D9
A24-B85-C11-D9
A69-B85-C11-D9
A67-B85-C11-D9
A39-B85-C11-D9
A65-B85-C11-D9
A66-B85-C11-D9
A2-B86-C11-D9
A3-B86-C11-D9
A9-B86-C11-D9
A13-B86-C11-D9
A24-B86-C11-D9
A69-B86-C11-D9
A67-B86-C11-D9
A39-B86-C11-D9
A65-B86-C11-D9
A66-B86-C11-D9
A2-B87-C11-D9
A3-B87-C11-D9
A9-B87-C11-D9
A13-B87-C11-D9
A24-B87-C11-D9
A69-B87-C11-D9
A67-B87-C11-D9
A39-B87-C11-D9
A65-B87-C11-D9
A66-B87-C11-D9
A2-B89-C11-D9
A3-B89-C11-D9
A9-B89-C11-D9
A13-B89-C11-D9
A24-B89-C11-D9
A69-B89-C11-D9
A67-B89-C11-D9
A39-B89-C11-D9
A65-B89-C11-D9
A66-B89-C11-D9
A2-B92-C11-D9
A3-B92-C11-D9
A9-B92-C11-D9
A13-B92-C11-D9
A24-B92-C11-D9
A69-B92-C11-D9
A67-B92-C11-D9
A39-B92-C11-D9
A65-B92-C11-D9
A66-B92-C11-D9
A2-B4-C12-D9
A3-B4-C12-D9
A9-B4-C12-D9
A13-B4-C12-D9
A24-B4-C12-D9
A69-B4-C12-D9
A67-B4-C12-D9
A39-B4-C12-D9
A65-B4-C12-D9
A66-B4-C12-D9
A2-B5-C12-D9
A3-B5-C12-D9
A9-B5-C12-D9
A13-B5-C12-D9
A24-B5-C12-D9
A69-B5-C12-D9
A67-B5-C12-D9
A39-B5-C12-D9
A65-B5-C12-D9
A66-B5-C12-D9
A2-B6-C12-D9
A3-B6-C12-D9
A9-B6-C12-D9
A13-B6-C12-D9

TABLE 6-continued

A24-B6-C12-D9
A69-B6-C12-D9
A67-B6-C12-D9
A39-B6-C12-D9
A65-B6-C12-D9
A66-B6-C12-D9
A2-B32-C12-D9
A3-B32-C12-D9
A9-B32-C12-D9
A13-B32-C12-D9
A24-B32-C12-D9
A69-B32-C12-D9
A67-B32-C12-D9
A39-B32-C12-D9
A65-B32-C12-D9
A66-B32-C12-D9
A2-B39-C12-D9
A3-B39-C12-D9
A9-B39-C12-D9
A13-B39-C12-D9
A24-B39-C12-D9
A69-B39-C12-D9
A67-B39-C12-D9
A39-B39-C12-D9
A65-B39-C12-D9
A66-B39-C12-D9
A2-B45-C12-D9
A3-B45-C12-D9
A9-B45-C12-D9
A13-B45-C12-D9
A24-B45-C12-D9
A69-B45-C12-D9
A67-B45-C12-D9
A39-B45-C12-D9
A65-B45-C12-D9
A66-B45-C12-D9
A2-B53-C12-D9
A3-B53-C12-D9
A9-B53-C12-D9
A13-B53-C12-D9
A24-B53-C12-D9
A69-B53-C12-D9
A67-B53-C12-D9
A39-B53-C12-D9
A65-B53-C12-D9
A66-B53-C12-D9
A2-B79-C12-D9
A3-B79-C12-D9
A9-B79-C12-D9
A13-B79-C12-D9
A24-B79-C12-D9
A69-B79-C12-D9
A67-B79-C12-D9
A39-B79-C12-D9
A65-B79-C12-D9
A66-B79-C12-D9
A2-B80-C12-D9
A3-B80-C12-D9
A9-B80-C12-D9
A13-B80-C12-D9
A24-B80-C12-D9
A69-B80-C12-D9
A67-B80-C12-D9
A39-B80-C12-D9
A65-B80-C12-D9
A66-B80-C12-D9
A2-B85-C12-D9
A3-B85-C12-D9
A9-B85-C12-D9
A13-B85-C12-D9
A24-B85-C12-D9
A69-B85-C12-D9
A67-B85-C12-D9
A39-B85-C12-D9
A65-B85-C12-D9
A66-B85-C12-D9
A2-B86-C12-D9
A3-B86-C12-D9
A9-B86-C12-D9

TABLE 6-continued

A13-B86-C12-D9
A24-B86-C12-D9
A69-B86-C12-D9
A67-B86-C12-D9
A39-B86-C12-D9
A65-B86-C12-D9
A66-B86-C12-D9
A2-B87-C12-D9
A3-B87-C12-D9
A9-B87-C12-D9
A13-B87-C12-D9
A24-B87-C12-D9
A69-B87-C12-D9
A67-B87-C12-D9
A39-B87-C12-D9
A65-B87-C12-D9
A66-B87-C12-D9
A2-B89-C12-D9
A3-B89-C12-D9
A9-B89-C12-D9
A13-B89-C12-D9
A24-B89-C12-D9
A69-B89-C12-D9
A67-B89-C12-D9
A39-B89-C12-D9
A65-B89-C12-D9
A66-B89-C12-D9
A2-B92-C12-D9
A3-B92-C12-D9
A9-B92-C12-D9
A13-B92-C12-D9
A24-B92-C12-D9
A69-B92-C12-D9
A67-B92-C12-D9
A39-B92-C12-D9
A65-B92-C12-D9
A66-B92-C12-D9
A2-B4-C13-D9
A3-B4-C13-D9
A9-B4-C13-D9
A13-B4-C13-D9
A24-B4-C13-D9
A69-B4-C13-D9
A67-B4-C13-D9
A39-B4-C13-D9
A65-B4-C13-D9
A66-B4-C13-D9
A2-B5-C13-D9
A3-B5-C13-D9
A9-B5-C13-D9
A13-B5-C13-D9
A24-B5-C13-D9
A69-B5-C13-D9
A67-B5-C13-D9
A39-B5-C13-D9
A65-B5-C13-D9
A66-B5-C13-D9
A2-B6-C13-D9
A3-B6-C13-D9
A9-B6-C13-D9
A13-B6-C13-D9
A24-B6-C13-D9
A69-B6-C13-D9
A67-B6-C13-D9
A39-B6-C13-D9
A65-B6-C13-D9
A66-B6-C13-D9
A2-B32-C13-D9
A3-B32-C13-D9
A9-B32-C13-D9
A13-B32-C13-D9
A24-B32-C13-D9
A69-B32-C13-D9
A67-B32-C13-D9
A39-B32-C13-D9
A65-B32-C13-D9
A66-B32-C13-D9
A2-B39-C13-D9
A3-B39-C13-D9

TABLE 6-continued

| | |
|---|---|
| A9-B39-C13-D9 | A3-B89-C13-D9 |
| A13-B39-C13-D9 | A9-B89-C13-D9 |
| A24-B39-C13-D9 | A13-B89-C13-D9 |
| A69-B39-C13-D9 | A24-B89-C13-D9 |
| A67-B39-C13-D9 | A69-B89-C13-D9 |
| A39-B39-C13-D9 | A67-B89-C13-D9 |
| A65-B39-C13-D9 | A39-B89-C13-D9 |
| A66-B39-C13-D9 | A65-B89-C13-D9 |
| A2-B45-C13-D9 | A66-B89-C13-D9 |
| A3-B45-C13-D9 | A2-B92-C13-D9 |
| A9-B45-C13-D9 | A3-B92-C13-D9 |
| A13-B45-C13-D9 | A9-B92-C13-D9 |
| A24-B45-C13-D9 | A13-B92-C13-D9 |
| A69-B45-C13-D9 | A24-B92-C13-D9 |
| A67-B45-C13-D9 | A69-B92-C13-D9 |
| A39-B45-C13-D9 | A67-B92-C13-D9 |
| A65-B45-C13-D9 | A39-B92-C13-D9 |
| A66-B45-C13-D9 | A65-B92-C13-D9 |
| A2-B53-C13-D9 | A66-B92-C13-D9 |
| A3-B53-C13-D9 | A2-B4-C1-D10 |
| A9-B53-C13-D9 | A3-B4-C1-D10 |
| A13-B53-C13-D9 | A9-B4-C1-D10 |
| A24-B53-C13-D9 | A13-B4-C1-D10 |
| A69-B53-C13-D9 | A24-B4-C1-D10 |
| A67-B53-C13-D9 | A69-B4-C1-D10 |
| A39-B53-C13-D9 | A67-B4-C1-D10 |
| A65-B53-C13-D9 | A39-B4-C1-D10 |
| A66-B53-C13-D9 | A65-B4-C1-D10 |
| A2-B79-C13-D9 | A66-B4-C1-D10 |
| A3-B79-C13-D9 | A2-B5-C1-D10 |
| A9-B79-C13-D9 | A3-B5-C1-D10 |
| A13-B79-C13-D9 | A9-B5-C1-D10 |
| A24-B79-C13-D9 | A13-B5-C1-D10 |
| A69-B79-C13-D9 | A24-B5-C1-D10 |
| A67-B79-C13-D9 | A69-B5-C1-D10 |
| A39-B79-C13-D9 | A67-B5-C1-D10 |
| A65-B79-C13-D9 | A39-B5-C1-D10 |
| A66-B79-C13-D9 | A65-B5-C1-D10 |
| A2-B80-C13-D9 | A66-B5-C1-D10 |
| A3-B80-C13-D9 | A2-B6-C1-D10 |
| A9-B80-C13-D9 | A3-B6-C1-D10 |
| A13-B80-C13-D9 | A9-B6-C1-D10 |
| A24-B80-C13-D9 | A13-B6-C1-D10 |
| A69-B80-C13-D9 | A24-B6-C1-D10 |
| A67-B80-C13-D9 | A69-B6-C1-D10 |
| A39-B80-C13-D9 | A67-B6-C1-D10 |
| A65-B80-C13-D9 | A39-B6-C1-D10 |
| A66-B80-C13-D9 | A65-B6-C1-D10 |
| A2-B85-C13-D9 | A66-B6-C1-D10 |
| A3-B85-C13-D9 | A2-B32-C1-D10 |
| A9-B85-C13-D9 | A3-B32-C1-D10 |
| A13-B85-C13-D9 | A9-B32-C1-D10 |
| A24-B85-C13-D9 | A13-B32-C1-D10 |
| A69-B85-C13-D9 | A24-B32-C1-D10 |
| A67-B85-C13-D9 | A69-B32-C1-D10 |
| A39-B85-C13-D9 | A67-B32-C1-D10 |
| A65-B85-C13-D9 | A39-B32-C1-D10 |
| A66-B85-C13-D9 | A65-B32-C1-D10 |
| A2-B86-C13-D9 | A66-B32-C1-D10 |
| A3-B86-C13-D9 | A2-B39-C1-D10 |
| A9-B86-C13-D9 | A3-B39-C1-D10 |
| A13-B86-C13-D9 | A9-B39-C1-D10 |
| A24-B86-C13-D9 | A13-B39-C1-D10 |
| A69-B86-C13-D9 | A24-B39-C1-D10 |
| A67-B86-C13-D9 | A69-B39-C1-D10 |
| A39-B86-C13-D9 | A67-B39-C1-D10 |
| A65-B86-C13-D9 | A39-B39-C1-D10 |
| A66-B86-C13-D9 | A65-B39-C1-D10 |
| A2-B87-C13-D9 | A66-B39-C1-D10 |
| A3-B87-C13-D9 | A2-B45-C1-D10 |
| A9-B87-C13-D9 | A3-B45-C1-D10 |
| A13-B87-C13-D9 | A9-B45-C1-D10 |
| A24-B87-C13-D9 | A13-B45-C1-D10 |
| A69-B87-C13-D9 | A24-B45-C1-D10 |
| A67-B87-C13-D9 | A69-B45-C1-D10 |
| A39-B87-C13-D9 | A67-B45-C1-D10 |
| A65-B87-C13-D9 | A39-B45-C1-D10 |
| A66-B87-C13-D9 | A65-B45-C1-D10 |
| A2-B89-C13-D9 | A66-B45-C1-D10 |

TABLE 6-continued

A2-B53-C1-D10
A3-B53-C1-D10
A9-B53-C1-D10
A13-B53-C1-D10
A24-B53-C1-D10
A69-B53-C1-D10
A67-B53-C1-D10
A39-B53-C1-D10
A65-B53-C1-D10
A66-B53-C1-D10
A2-B79-C1-D10
A3-B79-C1-D10
A9-B79-C1-D10
A13-B79-C1-D10
A24-B79-C1-D10
A69-B79-C1-D10
A67-B79-C1-D10
A39-B79-C1-D10
A65-B79-C1-D10
A66-B79-C1-D10
A2-B80-C1-D10
A3-B80-C1-D10
A9-B80-C1-D10
A13-B80-C1-D10
A24-B80-C1-D10
A69-B80-C1-D10
A67-B80-C1-D10
A39-B80-C1-D10
A65-B80-C1-D10
A66-B80-C1-D10
A2-B85-C1-D10
A3-B85-C1-D10
A9-B85-C1-D10
A13-B85-C1-D10
A24-B85-C1-D10
A69-B85-C1-D10
A67-B85-C1-D10
A39-B85-C1-D10
A65-B85-C1-D10
A66-B85-C1-D10
A2-B86-C1-D10
A3-B86-C1-D10
A9-B86-C1-D10
A13-B86-C1-D10
A24-B86-C1-D10
A69-B86-C1-D10
A67-B86-C1-D10
A39-B86-C1-D10
A65-B86-C1-D10
A66-B86-C1-D10
A2-B87-C1-D10
A3-B87-C1-D10
A9-B87-C1-D10
A13-B87-C1-D10
A24-B87-C1-D10
A69-B87-C1-D10
A67-B87-C1-D10
A39-B87-C1-D10
A65-B87-C1-D10
A66-B87-C1-D10
A2-B89-C1-D10
A3-B89-C1-D10
A9-B89-C1-D10
A13-B89-C1-D10
A24-B89-C1-D10
A69-B89-C1-D10
A67-B89-C1-D10
A39-B89-C1-D10
A65-B89-C1-D10
A66-B89-C1-D10
A2-B92-C1-D10
A3-B92-C1-D10
A9-B92-C1-D10
A13-B92-C1-D10
A24-B92-C1-D10
A69-B92-C1-D10
A67-B92-C1-D10
A39-B92-C1-D10
A65-B92-C1-D10

TABLE 6-continued

A66-B92-C1-D10
A2-B4-C2-D10
A3-B4-C2-D10
A9-B4-C2-D10
A13-B4-C2-D10
A24-B4-C2-D10
A69-B4-C2-D10
A67-B4-C2-D10
A39-B4-C2-D10
A65-B4-C2-D10
A66-B4-C2-D10
A2-B5-C2-D10
A3-B5-C2-D10
A9-B5-C2-D10
A13-B5-C2-D10
A24-B5-C2-D10
A69-B5-C2-D10
A67-B5-C2-D10
A39-B5-C2-D10
A65-B5-C2-D10
A66-B5-C2-D10
A2-B6-C2-D10
A3-B6-C2-D10
A9-B6-C2-D10
A13-B6-C2-D10
A24-B6-C2-D10
A69-B6-C2-D10
A67-B6-C2-D10
A39-B6-C2-D10
A65-B6-C2-D10
A66-B6-C2-D10
A2-B32-C2-D10
A3-B32-C2-D10
A9-B32-C2-D10
A13-B32-C2-D10
A24-B32-C2-D10
A69-B32-C2-D10
A67-B32-C2-D10
A39-B32-C2-D10
A65-B32-C2-D10
A66-B32-C2-D10
A2-B39-C2-D10
A3-B39-C2-D10
A9-B39-C2-D10
A13-B39-C2-D10
A24-B39-C2-D10
A69-B39-C2-D10
A67-B39-C2-D10
A39-B39-C2-D10
A65-B39-C2-D10
A66-B39-C2-D10
A2-B45-C2-D10
A3-B45-C2-D10
A9-B45-C2-D10
A13-B45-C2-D10
A24-B45-C2-D10
A69-B45-C2-D10
A67-B45-C2-D10
A39-B45-C2-D10
A65-B45-C2-D10
A66-B45-C2-D10
A2-B53-C2-D10
A3-B53-C2-D10
A9-B53-C2-D10
A13-B53-C2-D10
A24-B53-C2-D10
A69-B53-C2-D10
A67-B53-C2-D10
A39-B53-C2-D10
A65-B53-C2-D10
A66-B53-C2-D10
A2-B79-C2-D10
A3-B79-C2-D10
A9-B79-C2-D10
A13-B79-C2-D10
A24-B79-C2-D10
A69-B79-C2-D10
A67-B79-C2-D10
A39-B79-C2-D10

TABLE 6-continued

| |
|---|
| A65-B79-C2-D10 |
| A66-B79-C2-D10 |
| A2-B80-C2-D10 |
| A3-B80-C2-D10 |
| A9-B80-C2-D10 |
| A13-B80-C2-D10 |
| A24-B80-C2-D10 |
| A69-B80-C2-D10 |
| A67-B80-C2-D10 |
| A39-B80-C2-D10 |
| A65-B80-C2-D10 |
| A66-B80-C2-D10 |
| A2-B85-C2-D10 |
| A3-B85-C2-D10 |
| A9-B85-C2-D10 |
| A13-B85-C2-D10 |
| A24-B85-C2-D10 |
| A69-B85-C2-D10 |
| A67-B85-C2-D10 |
| A39-B85-C2-D10 |
| A65-B85-C2-D10 |
| A66-B85-C2-D10 |
| A2-B86-C2-D10 |
| A3-B86-C2-D10 |
| A9-B86-C2-D10 |
| A13-B86-C2-D10 |
| A24-B86-C2-D10 |
| A69-B86-C2-D10 |
| A67-B86-C2-D10 |
| A39-B86-C2-D10 |
| A65-B86-C2-D10 |
| A66-B86-C2-D10 |
| A2-B87-C2-D10 |
| A3-B87-C2-D10 |
| A9-B87-C2-D10 |
| A13-B87-C2-D10 |
| A24-B87-C2-D10 |
| A69-B87-C2-D10 |
| A67-B87-C2-D10 |
| A39-B87-C2-D10 |
| A65-B87-C2-D10 |
| A66-B87-C2-D10 |
| A2-B89-C2-D10 |
| A3-B89-C2-D10 |
| A9-B89-C2-D10 |
| A13-B89-C2-D10 |
| A24-B89-C2-D10 |
| A69-B89-C2-D10 |
| A67-B89-C2-D10 |
| A39-B89-C2-D10 |
| A65-B89-C2-D10 |
| A66-B89-C2-D10 |
| A2-B92-C2-D10 |
| A3-B92-C2-D10 |
| A9-B92-C2-D10 |
| A13-B92-C2-D10 |
| A24-B92-C2-D10 |
| A69-B92-C2-D10 |
| A67-B92-C2-D10 |
| A39-B92-C2-D10 |
| A65-B92-C2-D10 |
| A66-B92-C2-D10 |
| A2-B4-C3-D10 |
| A3-B4-C3-D10 |
| A9-B4-C3-D10 |
| A13-B4-C3-D10 |
| A24-B4-C3-D10 |
| A69-B4-C3-D10 |
| A67-B4-C3-D10 |
| A39-B4-C3-D10 |
| A65-B4-C3-D10 |
| A66-B4-C3-D10 |
| A2-B5-C3-D10 |
| A3-B5-C3-D10 |
| A9-B5-C3-D10 |
| A13-B5-C3-D10 |
| A24-B5-C3-D10 |
| A69-B5-C3-D10 |
| A67-B5-C3-D10 |
| A39-B5-C3-D10 |
| A65-B5-C3-D10 |
| A66-B5-C3-D10 |
| A2-B6-C3-D10 |
| A3-B6-C3-D10 |
| A9-B6-C3-D10 |
| A13-B6-C3-D10 |
| A24-B6-C3-D10 |
| A69-B6-C3-D10 |
| A67-B6-C3-D10 |
| A39-B6-C3-D10 |
| A65-B6-C3-D10 |
| A66-B6-C3-D10 |
| A2-B32-C3-D10 |
| A3-B32-C3-D10 |
| A9-B32-C3-D10 |
| A13-B32-C3-D10 |
| A24-B32-C3-D10 |
| A69-B32-C3-D10 |
| A67-B32-C3-D10 |
| A39-B32-C3-D10 |
| A65-B32-C3-D10 |
| A66-B32-C3-D10 |
| A2-B39-C3-D10 |
| A3-B39-C3-D10 |
| A9-B39-C3-D10 |
| A13-B39-C3-D10 |
| A24-B39-C3-D10 |
| A69-B39-C3-D10 |
| A67-B39-C3-D10 |
| A39-B39-C3-D10 |
| A65-B39-C3-D10 |
| A66-B39-C3-D10 |
| A2-B45-C3-D10 |
| A3-B45-C3-D10 |
| A9-B45-C3-D10 |
| A13-B45-C3-D10 |
| A24-B45-C3-D10 |
| A69-B45-C3-D10 |
| A67-B45-C3-D10 |
| A39-B45-C3-D10 |
| A65-B45-C3-D10 |
| A66-B45-C3-D10 |
| A2-B53-C3-D10 |
| A3-B53-C3-D10 |
| A9-B53-C3-D10 |
| A13-B53-C3-D10 |
| A24-B53-C3-D10 |
| A69-B53-C3-D10 |
| A67-B53-C3-D10 |
| A39-B53-C3-D10 |
| A65-B53-C3-D10 |
| A66-B53-C3-D10 |
| A2-B79-C3-D10 |
| A3-B79-C3-D10 |
| A9-B79-C3-D10 |
| A13-B79-C3-D10 |
| A24-B79-C3-D10 |
| A69-B79-C3-D10 |
| A67-B79-C3-D10 |
| A39-B79-C3-D10 |
| A65-B79-C3-D10 |
| A66-B79-C3-D10 |
| A2-B80-C3-D10 |
| A3-B80-C3-D10 |
| A9-B80-C3-D10 |
| A13-B80-C3-D10 |
| A24-B80-C3-D10 |
| A69-B80-C3-D10 |
| A67-B80-C3-D10 |
| A39-B80-C3-D10 |
| A65-B80-C3-D10 |
| A66-B80-C3-D10 |
| A2-B85-C3-D10 |
| A3-B85-C3-D10 |
| A9-B85-C3-D10 |
| A13-B85-C3-D10 |
| A24-B85-C3-D10 |
| A69-B85-C3-D10 |

TABLE 6-continued

A67-B85-C3-D10
A39-B85-C3-D10
A65-B85-C3-D10
A66-B85-C3-D10
A2-B86-C3-D10
A3-B86-C3-D10
A9-B86-C3-D10
A13-B86-C3-D10
A24-B86-C3-D10
A69-B86-C3-D10
A67-B86-C3-D10
A39-B86-C3-D10
A65-B86-C3-D10
A66-B86-C3-D10
A2-B87-C3-D10
A3-B87-C3-D10
A9-B87-C3-D10
A13-B87-C3-D10
A24-B87-C3-D10
A69-B87-C3-D10
A67-B87-C3-D10
A39-B87-C3-D10
A65-B87-C3-D10
A66-B87-C3-D10
A2-B89-C3-D10
A3-B89-C3-D10
A9-B89-C3-D10
A13-B89-C3-D10
A24-B89-C3-D10
A69-B89-C3-D10
A67-B89-C3-D10
A39-B89-C3-D10
A65-B89-C3-D10
A66-B89-C3-D10
A2-B92-C3-D10
A3-B92-C3-D10
A9-B92-C3-D10
A13-B92-C3-D10
A24-B92-C3-D10
A69-B92-C3-D10
A67-B92-C3-D10
A39-B92-C3-D10
A65-B92-C3-D10
A66-B92-C3-D10
A2-B4-C4-D10
A3-B4-C4-D10
A9-B4-C4-D10
A13-B4-C4-D10
A24-B4-C4-D10
A69-B4-C4-D10
A67-B4-C4-D10
A39-B4-C4-D10
A65-B4-C4-D10
A66-B4-C4-D10
A2-B5-C4-D10
A3-B5-C4-D10
A9-B5-C4-D10
A13-B5-C4-D10
A24-B5-C4-D10
A69-B5-C4-D10
A67-B5-C4-D10
A39-B5-C4-D10
A65-B5-C4-D10
A66-B5-C4-D10
A2-B6-C4-D10
A3-B6-C4-D10
A9-B6-C4-D10
A13-B6-C4-D10
A24-B6-C4-D10
A69-B6-C4-D10
A67-B6-C4-D10
A39-B6-C4-D10
A65-B6-C4-D10
A66-B6-C4-D10
A2-B32-C4-D10
A3-B32-C4-D10
A9-B32-C4-D10
A13-B32-C4-D10
A24-B32-C4-D10
A69-B32-C4-D10
A67-B32-C4-D10
A39-B32-C4-D10
A65-B32-C4-D10
A66-B32-C4-D10
A2-B39-C4-D10
A3-B39-C4-D10
A9-B39-C4-D10
A13-B39-C4-D10
A24-B39-C4-D10
A69-B39-C4-D10
A67-B39-C4-D10
A39-B39-C4-D10
A65-B39-C4-D10
A66-B39-C4-D10
A2-B45-C4-D10
A3-B45-C4-D10
A9-B45-C4-D10
A13-B45-C4-D10
A24-B45-C4-D10
A69-B45-C4-D10
A67-B45-C4-D10
A39-B45-C4-D10
A65-B45-C4-D10
A66-B45-C4-D10
A2-B53-C4-D10
A3-B53-C4-D10
A9-B53-C4-D10
A13-B53-C4-D10
A24-B53-C4-D10
A69-B53-C4-D10
A67-B53-C4-D10
A39-B53-C4-D10
A65-B53-C4-D10
A66-B53-C4-D10
A2-B79-C4-D10
A3-B79-C4-D10
A9-B79-C4-D10
A13-B79-C4-D10
A24-B79-C4-D10
A69-B79-C4-D10
A67-B79-C4-D10
A39-B79-C4-D10
A65-B79-C4-D10
A66-B79-C4-D10
A2-B80-C4-D10
A3-B80-C4-D10
A9-B80-C4-D10
A13-B80-C4-D10
A24-B80-C4-D10
A69-B80-C4-D10
A67-B80-C4-D10
A39-B80-C4-D10
A65-B80-C4-D10
A66-B80-C4-D10
A2-B85-C4-D10
A3-B85-C4-D10
A9-B85-C4-D10
A13-B85-C4-D10
A24-B85-C4-D10
A69-B85-C4-D10
A67-B85-C4-D10
A39-B85-C4-D10
A65-B85-C4-D10
A66-B85-C4-D10
A2-B86-C4-D10
A3-B86-C4-D10
A9-B86-C4-D10
A13-B86-C4-D10
A24-B86-C4-D10
A69-B86-C4-D10
A67-B86-C4-D10
A39-B86-C4-D10
A65-B86-C4-D10
A66-B86-C4-D10
A2-B87-C4-D10
A3-B87-C4-D10
A9-B87-C4-D10
A13-B87-C4-D10

TABLE 6-continued

A24-B87-C4-D10
A69-B87-C4-D10
A67-B87-C4-D10
A39-B87-C4-D10
A65-B87-C4-D10
A66-B87-C4-D10
A2-B89-C4-D10
A3-B89-C4-D10
A9-B89-C4-D10
A13-B89-C4-D10
A24-B89-C4-D10
A69-B89-C4-D10
A67-B89-C4-D10
A39-B89-C4-D10
A65-B89-C4-D10
A66-B89-C4-D10
A2-B92-C4-D10
A3-B92-C4-D10
A9-B92-C4-D10
A13-B92-C4-D10
A24-B92-C4-D10
A69-B92-C4-D10
A67-B92-C4-D10
A39-B92-C4-D10
A65-B92-C4-D10
A66-B92-C4-D10
A2-B4-C5-D10
A3-B4-C5-D10
A9-B4-C5-D10
A13-B4-C5-D10
A24-B4-C5-D10
A69-B4-C5-D10
A67-B4-C5-D10
A39-B4-C5-D10
A65-B4-C5-D10
A66-B4-C5-D10
A2-B5-C5-D10
A3-B5-C5-D10
A9-B5-C5-D10
A13-B5-C5-D10
A24-B5-C5-D10
A69-B5-C5-D10
A67-B5-C5-D10
A39-B5-C5-D10
A65-B5-C5-D10
A66-B5-C5-D10
A2-B6-C5-D10
A3-B6-C5-D10
A9-B6-C5-D10
A13-B6-C5-D10
A24-B6-C5-D10
A69-B6-C5-D10
A67-B6-C5-D10
A39-B6-C5-D10
A65-B6-C5-D10
A66-B6-C5-D10
A2-B32-C5-D10
A3-B32-C5-D10
A9-B32-C5-D10
A13-B32-C5-D10
A24-B32-C5-D10
A69-B32-C5-D10
A67-B32-C5-D10
A39-B32-C5-D10
A65-B32-C5-D10
A66-B32-C5-D10
A2-B39-C5-D10
A3-B39-C5-D10
A9-B39-C5-D10
A13-B39-C5-D10
A24-B39-C5-D10
A69-B39-C5-D10
A67-B39-C5-D10
A39-B39-C5-D10
A65-B39-C5-D10
A66-B39-C5-D10
A2-B45-C5-D10
A3-B45-C5-D10
A9-B45-C5-D10
A13-B45-C5-D10
A24-B45-C5-D10
A69-B45-C5-D10
A67-B45-C5-D10
A39-B45-C5-D10
A65-B45-C5-D10
A66-B45-C5-D10
A2-B53-C5-D10
A3-B53-C5-D10
A9-B53-C5-D10
A13-B53-C5-D10
A24-B53-C5-D10
A69-B53-C5-D10
A67-B53-C5-D10
A39-B53-C5-D10
A65-B53-C5-D10
A66-B53-C5-D10
A2-B79-C5-D10
A3-B79-C5-D10
A9-B79-C5-D10
A13-B79-C5-D10
A24-B79-C5-D10
A69-B79-C5-D10
A67-B79-C5-D10
A39-B79-C5-D10
A65-B79-C5-D10
A66-B79-C5-D10
A2-B80-C5-D10
A3-B80-C5-D10
A9-B80-C5-D10
A13-B80-C5-D10
A24-B80-C5-D10
A69-B80-C5-D10
A67-B80-C5-D10
A39-B80-C5-D10
A65-B80-C5-D10
A66-B80-C5-D10
A2-B85-C5-D10
A3-B85-C5-D10
A9-B85-C5-D10
A13-B85-C5-D10
A24-B85-C5-D10
A69-B85-C5-D10
A67-B85-C5-D10
A39-B85-C5-D10
A65-B85-C5-D10
A66-B85-C5-D10
A2-B86-C5-D10
A3-B86-C5-D10
A9-B86-C5-D10
A13-B86-C5-D10
A24-B86-C5-D10
A69-B86-C5-D10
A67-B86-C5-D10
A39-B86-C5-D10
A65-B86-C5-D10
A66-B86-C5-D10
A2-B87-C5-D10
A3-B87-C5-D10
A9-B87-C5-D10
A13-B87-C5-D10
A24-B87-C5-D10
A69-B87-C5-D10
A67-B87-C5-D10
A39-B87-C5-D10
A65-B87-C5-D10
A66-B87-C5-D10
A2-B89-C5-D10
A3-B89-C5-D10
A9-B89-C5-D10
A13-B89-C5-D10
A24-B89-C5-D10
A69-B89-C5-D10
A67-B89-C5-D10
A39-B89-C5-D10
A65-B89-C5-D10
A66-B89-C5-D10
A2-B92-C5-D10
A3-B92-C5-D10

TABLE 6-continued

A9-B92-C5-D10
A13-B92-C5-D10
A24-B92-C5-D10
A69-B92-C5-D10
A39-B92-C5-D10
A65-B92-C5-D10
A66-B92-C5-D10
A2-B4-C6-D10
A3-B4-C6-D10
A9-B4-C6-D10
A13-B4-C6-D10
A24-B4-C6-D10
A69-B4-C6-D10
A67-B4-C6-D10
A39-B4-C6-D10
A65-B4-C6-D10
A66-B4-C6-D10
A2-B5-C6-D10
A3-B5-C6-D10
A9-B5-C6-D10
A13-B5-C6-D10
A24-B5-C6-D10
A69-B5-C6-D10
A67-B5-C6-D10
A39-B5-C6-D10
A65-B5-C6-D10
A66-B5-C6-D10
A2-B6-C6-D10
A3-B6-C6-D10
A9-B6-C6-D10
A13-B6-C6-D10
A24-B6-C6-D10
A69-B6-C6-D10
A67-B6-C6-D10
A39-B6-C6-D10
A65-B6-C6-D10
A66-B6-C6-D10
A2-B32-C6-D10
A3-B32-C6-D10
A9-B32-C6-D10
A13-B32-C6-D10
A24-B32-C6-D10
A69-B32-C6-D10
A67-B32-C6-D10
A39-B32-C6-D10
A65-B32-C6-D10
A66-B32-C6-D10
A2-B39-C6-D10
A3-B39-C6-D10
A9-B39-C6-D10
A13-B39-C6-D10
A24-B39-C6-D10
A69-B39-C6-D10
A67-B39-C6-D10
A39-B39-C6-D10
A65-B39-C6-D10
A66-B39-C6-D10
A2-B45-C6-D10
A3-B45-C6-D10
A9-B45-C6-D10
A13-B45-C6-D10
A24-B45-C6-D10
A69-B45-C6-D10
A67-B45-C6-D10
A39-B45-C6-D10
A65-B45-C6-D10
A66-B45-C6-D10
A2-B53-C6-D10
A3-B53-C6-D10
A9-B53-C6-D10
A13-B53-C6-D10
A24-B53-C6-D10
A69-B53-C6-D10
A67-B53-C6-D10
A39-B53-C6-D10
A65-B53-C6-D10
A66-B53-C6-D10
A2-B79-C6-D10

TABLE 6-continued

A3-B79-C6-D10
A9-B79-C6-D10
A13-B79-C6-D10
A24-B79-C6-D10
A69-B79-C6-D10
A67-B79-C6-D10
A39-B79-C6-D10
A65-B79-C6-D10
A66-B79-C6-D10
A2-B80-C6-D10
A3-B80-C6-D10
A9-B80-C6-D10
A13-B80-C6-D10
A24-B80-C6-D10
A69-B80-C6-D10
A67-B80-C6-D10
A39-B80-C6-D10
A65-B80-C6-D10
A66-B80-C6-D10
A2-B85-C6-D10
A3-B85-C6-D10
A9-B85-C6-D10
A13-B85-C6-D10
A24-B85-C6-D10
A69-B85-C6-D10
A67-B85-C6-D10
A39-B85-C6-D10
A65-B85-C6-D10
A66-B85-C6-D10
A2-B86-C6-D10
A3-B86-C6-D10
A9-B86-C6-D10
A13-B86-C6-D10
A24-B86-C6-D10
A69-B86-C6-D10
A67-B86-C6-D10
A39-B86-C6-D10
A65-B86-C6-D10
A66-B86-C6-D10
A2-B87-C6-D10
A3-B87-C6-D10
A9-B87-C6-D10
A13-B87-C6-D10
A24-B87-C6-D10
A69-B87-C6-D10
A67-B87-C6-D10
A39-B87-C6-D10
A65-B87-C6-D10
A66-B87-C6-D10
A2-B89-C6-D10
A3-B89-C6-D10
A9-B89-C6-D10
A13-B89-C6-D10
A24-B89-C6-D10
A69-B89-C6-D10
A67-B89-C6-D10
A39-B89-C6-D10
A65-B89-C6-D10
A66-B89-C6-D10
A2-B92-C6-D10
A3-B92-C6-D10
A9-B92-C6-D10
A13-B92-C6-D10
A24-B92-C6-D10
A69-B92-C6-D10
A67-B92-C6-D10
A39-B92-C6-D10
A65-B92-C6-D10
A66-B92-C6-D10
A2-B4-C7-D10
A3-B4-C7-D10
A9-B4-C7-D10
A13-B4-C7-D10
A24-B4-C7-D10
A69-B4-C7-D10
A67-B4-C7-D10
A39-B4-C7-D10
A65-B4-C7-D10
A66-B4-C7-D10

TABLE 6-continued

| | |
|---|---|
| A2-B5-C7-D10 | A66-B80-C7-D10 |
| A3-B5-C7-D10 | A2-B85-C7-D10 |
| A9-B5-C7-D10 | A3-B85-C7-D10 |
| A13-B5-C7-D10 | A9-B85-C7-D10 |
| A24-B5-C7-D10 | A13-B85-C7-D10 |
| A69-B5-C7-D10 | A24-B85-C7-D10 |
| A67-B5-C7-D10 | A69-B85-C7-D10 |
| A39-B5-C7-D10 | A67-B85-C7-D10 |
| A65-B5-C7-D10 | A39-B85-C7-D10 |
| A66-B5-C7-D10 | A65-B85-C7-D10 |
| A2-B6-C7-D10 | A66-B85-C7-D10 |
| A3-B6-C7-D10 | A2-B86-C7-D10 |
| A9-B6-C7-D10 | A3-B86-C7-D10 |
| A13-B6-C7-D10 | A9-B86-C7-D10 |
| A24-B6-C7-D10 | A13-B86-C7-D10 |
| A69-B6-C7-D10 | A24-B86-C7-D10 |
| A67-B6-C7-D10 | A69-B86-C7-D10 |
| A39-B6-C7-D10 | A67-B86-C7-D10 |
| A65-B6-C7-D10 | A39-B86-C7-D10 |
| A66-B6-C7-D10 | A65-B86-C7-D10 |
| A2-B32-C7-D10 | A66-B86-C7-D10 |
| A3-B32-C7-D10 | A2-B87-C7-D10 |
| A9-B32-C7-D10 | A3-B87-C7-D10 |
| A13-B32-C7-D10 | A9-B87-C7-D10 |
| A24-B32-C7-D10 | A13-B87-C7-D10 |
| A69-B32-C7-D10 | A24-B87-C7-D10 |
| A67-B32-C7-D10 | A69-B87-C7-D10 |
| A39-B32-C7-D10 | A67-B87-C7-D10 |
| A65-B32-C7-D10 | A39-B87-C7-D10 |
| A66-B32-C7-D10 | A65-B87-C7-D10 |
| A2-B39-C7-D10 | A66-B87-C7-D10 |
| A3-B39-C7-D10 | A2-B89-C7-D10 |
| A9-B39-C7-D10 | A3-B89-C7-D10 |
| A13-B39-C7-D10 | A9-B89-C7-D10 |
| A24-B39-C7-D10 | A13-B89-C7-D10 |
| A69-B39-C7-D10 | A24-B89-C7-D10 |
| A67-B39-C7-D10 | A69-B89-C7-D10 |
| A39-B39-C7-D10 | A67-B89-C7-D10 |
| A65-B39-C7-D10 | A39-B89-C7-D10 |
| A66-B39-C7-D10 | A65-B89-C7-D10 |
| A2-B45-C7-D10 | A66-B89-C7-D10 |
| A3-B45-C7-D10 | A2-B92-C7-D10 |
| A9-B45-C7-D10 | A3-B92-C7-D10 |
| A13-B45-C7-D10 | A9-B92-C7-D10 |
| A24-B45-C7-D10 | A13-B92-C7-D10 |
| A69-B45-C7-D10 | A24-B92-C7-D10 |
| A67-B45-C7-D10 | A69-B92-C7-D10 |
| A39-B45-C7-D10 | A67-B92-C7-D10 |
| A65-B45-C7-D10 | A39-B92-C7-D10 |
| A66-B45-C7-D10 | A65-B92-C7-D10 |
| A2-B53-C7-D10 | A66-B92-C7-D10 |
| A3-B53-C7-D10 | A2-B4-C8-D10 |
| A9-B53-C7-D10 | A3-B4-C8-D10 |
| A13-B53-C7-D10 | A9-B4-C8-D10 |
| A24-B53-C7-D10 | A13-B4-C8-D10 |
| A69-B53-C7-D10 | A24-B4-C8-D10 |
| A67-B53-C7-D10 | A69-B4-C8-D10 |
| A39-B53-C7-D10 | A67-B4-C8-D10 |
| A65-B53-C7-D10 | A39-B4-C8-D10 |
| A66-B53-C7-D10 | A65-B4-C8-D10 |
| A2-B79-C7-D10 | A66-B4-C8-D10 |
| A3-B79-C7-D10 | A2-B5-C8-D10 |
| A9-B79-C7-D10 | A3-B5-C8-D10 |
| A13-B79-C7-D10 | A9-B5-C8-D10 |
| A24-B79-C7-D10 | A13-B5-C8-D10 |
| A69-B79-C7-D10 | A24-B5-C8-D10 |
| A67-B79-C7-D10 | A69-B5-C8-D10 |
| A39-B79-C7-D10 | A67-B5-C8-D10 |
| A65-B79-C7-D10 | A39-B5-C8-D10 |
| A66-B79-C7-D10 | A65-B5-C8-D10 |
| A2-B80-C7-D10 | A66-B5-C8-D10 |
| A3-B80-C7-D10 | A2-B6-C8-D10 |
| A9-B80-C7-D10 | A3-B6-C8-D10 |
| A13-B80-C7-D10 | A9-B6-C8-D10 |
| A24-B80-C7-D10 | A13-B6-C8-D10 |
| A69-B80-C7-D10 | A24-B6-C8-D10 |
| A67-B80-C7-D10 | A69-B6-C8-D10 |
| A39-B80-C7-D10 | A67-B6-C8-D10 |
| A65-B80-C7-D10 | A39-B6-C8-D10 |

TABLE 6-continued

A65-B6-C8-D10
A66-B6-C8-D10
A2-B32-C8-D10
A3-B32-C8-D10
A9-B32-C8-D10
A13-B32-C8-D10
A24-B32-C8-D10
A69-B32-C8-D10
A67-B32-C8-D10
A39-B32-C8-D10
A65-B32-C8-D10
A66-B32-C8-D10
A2-B39-C8-D10
A3-B39-C8-D10
A9-B39-C8-D10
A13-B39-C8-D10
A24-B39-C8-D10
A69-B39-C8-D10
A67-B39-C8-D10
A39-B39-C8-D10
A65-B39-C8-D10
A66-B39-C8-D10
A2-B45-C8-D10
A3-B45-C8-D10
A9-B45-C8-D10
A13-B45-C8-D10
A24-B45-C8-D10
A69-B45-C8-D10
A67-B45-C8-D10
A39-B45-C8-D10
A65-B45-C8-D10
A66-B45-C8-D10
A2-B53-C8-D10
A3-B53-C8-D10
A9-B53-C8-D10
A13-B53-C8-D10
A24-B53-C8-D10
A69-B53-C8-D10
A67-B53-C8-D10
A39-B53-C8-D10
A65-B53-C8-D10
A66-B53-C8-D10
A2-B79-C8-D10
A3-B79-C8-D10
A9-B79-C8-D10
A13-B79-C8-D10
A24-B79-C8-D10
A69-B79-C8-D10
A67-B79-C8-D10
A39-B79-C8-D10
A65-B79-C8-D10
A66-B79-C8-D10
A2-B80-C8-D10
A3-B80-C8-D10
A9-B80-C8-D10
A13-B80-C8-D10
A24-B80-C8-D10
A69-B80-C8-D10
A67-B80-C8-D10
A39-B80-C8-D10
A65-B80-C8-D10
A66-B80-C8-D10
A2-B85-C8-D10
A3-B85-C8-D10
A9-B85-C8-D10
A13-B85-C8-D10
A24-B85-C8-D10
A69-B85-C8-D10
A67-B85-C8-D10
A39-B85-C8-D10
A65-B85-C8-D10
A66-B85-C8-D10
A2-B86-C8-D10
A3-B86-C8-D10
A9-B86-C8-D10
A13-B86-C8-D10
A24-B86-C8-D10
A69-B86-C8-D10
A67-B86-C8-D10

TABLE 6-continued

A39-B86-C8-D10
A65-B86-C8-D10
A66-B86-C8-D10
A2-B87-C8-D10
A3-B87-C8-D10
A9-B87-C8-D10
A13-B87-C8-D10
A24-B87-C8-D10
A69-B87-C8-D10
A67-B87-C8-D10
A39-B87-C8-D10
A65-B87-C8-D10
A66-B87-C8-D10
A2-B89-C8-D10
A3-B89-C8-D10
A9-B89-C8-D10
A13-B89-C8-D10
A24-B89-C8-D10
A69-B89-C8-D10
A67-B89-C8-D10
A39-B89-C8-D10
A65-B89-C8-D10
A66-B89-C8-D10
A2-B92-C8-D10
A3-B92-C8-D10
A9-B92-C8-D10
A13-B92-C8-D10
A24-B92-C8-D10
A69-B92-C8-D10
A67-B92-C8-D10
A39-B92-C8-D10
A65-B92-C8-D10
A66-B92-C8-D10
A2-B4-C9-D10
A3-B4-C9-D10
A9-B4-C9-D10
A13-B4-C9-D10
A24-B4-C9-D10
A69-B4-C9-D10
A67-B4-C9-D10
A39-B4-C9-D10
A65-B4-C9-D10
A66-B4-C9-D10
A2-B5-C9-D10
A3-B5-C9-D10
A9-B5-C9-D10
A13-B5-C9-D10
A24-B5-C9-D10
A69-B5-C9-D10
A67-B5-C9-D10
A39-B5-C9-D10
A65-B5-C9-D10
A66-B5-C9-D10
A2-B6-C9-D10
A3-B6-C9-D10
A9-B6-C9-D10
A13-B6-C9-D10
A24-B6-C9-D10
A69-B6-C9-D10
A67-B6-C9-D10
A39-B6-C9-D10
A65-B6-C9-D10
A66-B6-C9-D10
A2-B32-C9-D10
A3-B32-C9-D10
A9-B32-C9-D10
A13-B32-C9-D10
A24-B32-C9-D10
A69-B32-C9-D10
A67-B32-C9-D10
A39-B32-C9-D10
A65-B32-C9-D10
A66-B32-C9-D10
A2-B39-C9-D10
A3-B39-C9-D10
A9-B39-C9-D10
A13-B39-C9-D10
A24-B39-C9-D10
A69-B39-C9-D10

TABLE 6-continued

A67-B39-C9-D10
A39-B39-C9-D10
A65-B39-C9-D10
A66-B39-C9-D10
A2-B45-C9-D10
A3-B45-C9-D10
A9-B45-C9-D10
A13-B45-C9-D10
A24-B45-C9-D10
A69-B45-C9-D10
A67-B45-C9-D10
A39-B45-C9-D10
A65-B45-C9-D10
A66-B45-C9-D10
A2-B53-C9-D10
A3-B53-C9-D10
A9-B53-C9-D10
A13-B53-C9-D10
A24-B53-C9-D10
A69-B53-C9-D10
A67-B53-C9-D10
A39-B53-C9-D10
A65-B53-C9-D10
A66-B53-C9-D10
A2-B79-C9-D10
A3-B79-C9-D10
A9-B79-C9-D10
A13-B79-C9-D10
A24-B79-C9-D10
A69-B79-C9-D10
A67-B79-C9-D10
A39-B79-C9-D10
A65-B79-C9-D10
A66-B79-C9-D10
A2-B80-C9-D10
A3-B80-C9-D10
A9-B80-C9-D10
A13-B80-C9-D10
A24-B80-C9-D10
A69-B80-C9-D10
A67-B80-C9-D10
A39-B80-C9-D10
A65-B80-C9-D10
A66-B80-C9-D10
A2-B85-C9-D10
A3-B85-C9-D10
A9-B85-C9-D10
A13-B85-C9-D10
A24-B85-C9-D10
A69-B85-C9-D10
A67-B85-C9-D10
A39-B85-C9-D10
A65-B85-C9-D10
A66-B85-C9-D10
A2-B86-C9-D10
A3-B86-C9-D10
A9-B86-C9-D10
A13-B86-C9-D10
A24-B86-C9-D10
A69-B86-C9-D10
A67-B86-C9-D10
A39-B86-C9-D10
A65-B86-C9-D10
A66-B86-C9-D10
A2-B87-C9-D10
A3-B87-C9-D10
A9-B87-C9-D10
A13-B87-C9-D10
A24-B87-C9-D10
A69-B87-C9-D10
A67-B87-C9-D10
A39-B87-C9-D10
A65-B87-C9-D10
A66-B87-C9-D10
A2-B89-C9-D10
A3-B89-C9-D10
A9-B89-C9-D10
A13-B89-C9-D10
A24-B89-C9-D10

TABLE 6-continued

A69-B89-C9-D10
A67-B89-C9-D10
A39-B89-C9-D10
A65-B89-C9-D10
A66-B89-C9-D10
A2-B92-C9-D10
A3-B92-C9-D10
A9-B92-C9-D10
A13-B92-C9-D10
A24-B92-C9-D10
A69-B92-C9-D10
A67-B92-C9-D10
A39-B92-C9-D10
A65-B92-C9-D10
A66-B92-C9-D10
A2-B4-C10-D10
A3-B4-C10-D10
A9-B4-C10-D10
A13-B4-C10-D10
A24-B4-C10-D10
A69-B4-C10-D10
A67-B4-C10-D10
A39-B4-C10-D10
A65-B4-C10-D10
A66-B4-C10-D10
A2-B5-C10-D10
A3-B5-C10-D10
A9-B5-C10-D10
A13-B5-C10-D10
A24-B5-C10-D10
A69-B5-C10-D10
A67-B5-C10-D10
A39-B5-C10-D10
A65-B5-C10-D10
A66-B5-C10-D10
A2-B6-C10-D10
A3-B6-C10-D10
A9-B6-C10-D10
A13-B6-C10-D10
A24-B6-C10-D10
A69-B6-C10-D10
A67-B6-C10-D10
A39-B6-C10-D10
A65-B6-C10-D10
A66-B6-C10-D10
A2-B32-C10-D10
A3-B32-C10-D10
A9-B32-C10-D10
A13-B32-C10-D10
A24-B32-C10-D10
A69-B32-C10-D10
A67-B32-C10-D10
A39-B32-C10-D10
A65-B32-C10-D10
A66-B32-C10-D10
A2-B39-C10-D10
A3-B39-C10-D10
A9-B39-C10-D10
A13-B39-C10-D10
A24-B39-C10-D10
A69-B39-C10-D10
A67-B39-C10-D10
A39-B39-C10-D10
A65-B39-C10-D10
A66-B39-C10-D10
A2-B45-C10-D10
A3-B45-C10-D10
A9-B45-C10-D10
A13-B45-C10-D10
A24-B45-C10-D10
A69-B45-C10-D10
A67-B45-C10-D10
A39-B45-C10-D10
A65-B45-C10-D10
A66-B45-C10-D10
A2-B53-C10-D10
A3-B53-C10-D10
A9-B53-C10-D10
A13-B53-C10-D10

TABLE 6-continued

A24-B53-C10-D10
A69-B53-C10-D10
A67-B53-C10-D10
A39-B53-C10-D10
A65-B53-C10-D10
A66-B53-C10-D10
A2-B79-C10-D10
A3-B79-C10-D10
A9-B79-C10-D10
A13-B79-C10-D10
A24-B79-C10-D10
A69-B79-C10-D10
A67-B79-C10-D10
A39-B79-C10-D10
A65-B79-C10-D10
A66-B79-C10-D10
A2-B80-C10-D10
A3-B80-C10-D10
A9-B80-C10-D10
A13-B80-C10-D10
A24-B80-C10-D10
A69-B80-C10-D10
A67-B80-C10-D10
A39-B80-C10-D10
A65-B80-C10-D10
A66-B80-C10-D10
A2-B85-C10-D10
A3-B85-C10-D10
A9-B85-C10-D10
A13-B85-C10-D10
A24-B85-C10-D10
A69-B85-C10-D10
A67-B85-C10-D10
A39-B85-C10-D10
A65-B85-C10-D10
A66-B85-C10-D10
A2-B86-C10-D10
A3-B86-C10-D10
A9-B86-C10-D10
A13-B86-C10-D10
A24-B86-C10-D10
A69-B86-C10-D10
A67-B86-C10-D10
A39-B86-C10-D10
A65-B86-C10-D10
A66-B86-C10-D10
A2-B87-C10-D10
A3-B87-C10-D10
A9-B87-C10-D10
A13-B87-C10-D10
A24-B87-C10-D10
A69-B87-C10-D10
A67-B87-C10-D10
A39-B87-C10-D10
A65-B87-C10-D10
A66-B87-C10-D10
A2-B89-C10-D10
A3-B89-C10-D10
A9-B89-C10-D10
A13-B89-C10-D10
A24-B89-C10-D10
A69-B89-C10-D10
A67-B89-C10-D10
A39-B89-C10-D10
A65-B89-C10-D10
A66-B89-C10-D10
A2-B92-C10-D10
A3-B92-C10-D10
A9-B92-C10-D10
A13-B92-C10-D10
A24-B92-C10-D10
A69-B92-C10-D10
A67-B92-C10-D10
A39-B92-C10-D10
A65-B92-C10-D10
A66-B92-C10-D10
A2-B4-C11-D10
A3-B4-C11-D10
A9-B4-C11-D10

TABLE 6-continued

A13-B4-C11-D10
A24-B4-C11-D10
A69-B4-C11-D10
A67-B4-C11-D10
A39-B4-C11-D10
A65-B4-C11-D10
A66-B4-C11-D10
A2-B5-C11-D10
A3-B5-C11-D10
A9-B5-C11-D10
A13-B5-C11-D10
A24-B5-C11-D10
A69-B5-C11-D10
A67-B5-C11-D10
A39-B5-C11-D10
A65-B5-C11-D10
A66-B5-C11-D10
A2-B6-C11-D10
A3-B6-C11-D10
A9-B6-C11-D10
A13-B6-C11-D10
A24-B6-C11-D10
A69-B6-C11-D10
A67-B6-C11-D10
A39-B6-C11-D10
A65-B6-C11-D10
A66-B6-C11-D10
A2-B32-C11-D10
A3-B32-C11-D10
A9-B32-C11-D10
A13-B32-C11-D10
A24-B32-C11-D10
A69-B32-C11-D10
A67-B32-C11-D10
A39-B32-C11-D10
A65-B32-C11-D10
A66-B32-C11-D10
A2-B39-C11-D10
A3-B39-C11-D10
A9-B39-C11-D10
A13-B39-C11-D10
A24-B39-C11-D10
A69-B39-C11-D10
A67-B39-C11-D10
A39-B39-C11-D10
A65-B39-C11-D10
A66-B39-C11-D10
A2-B45-C11-D10
A3-B45-C11-D10
A9-B45-C11-D10
A13-B45-C11-D10
A24-B45-C11-D10
A69-B45-C11-D10
A67-B45-C11-D10
A39-B45-C11-D10
A65-B45-C11-D10
A66-B45-C11-D10
A2-B53-C11-D10
A3-B53-C11-D10
A9-B53-C11-D10
A13-B53-C11-D10
A24-B53-C11-D10
A69-B53-C11-D10
A67-B53-C11-D10
A39-B53-C11-D10
A65-B53-C11-D10
A66-B53-C11-D10
A2-B79-C11-D10
A3-B79-C11-D10
A9-B79-C11-D10
A13-B79-C11-D10
A24-B79-C11-D10
A69-B79-C11-D10
A67-B79-C11-D10
A39-B79-C11-D10
A65-B79-C11-D10
A66-B79-C11-D10
A2-B80-C11-D10
A3-B80-C11-D10

TABLE 6-continued

A9-B80-C11-D10
A13-B80-C11-D10
A24-B80-C11-D10
A69-B80-C11-D10
A67-B80-C11-D10
A39-B80-C11-D10
A65-B80-C11-D10
A66-B80-C11-D10
A2-B85-C11-D10
A3-B85-C11-D10
A9-B85-C11-D10
A13-B85-C11-D10
A24-B85-C11-D10
A69-B85-C11-D10
A67-B85-C11-D10
A39-B85-C11-D10
A65-B85-C11-D10
A66-B85-C11-D10
A2-B86-C11-D10
A3-B86-C11-D10
A9-B86-C11-D10
A13-B86-C11-D10
A24-B86-C11-D10
A69-B86-C11-D10
A67-B86-C11-D10
A39-B86-C11-D10
A65-B86-C11-D10
A66-B86-C11-D10
A2-B87-C11-D10
A3-B87-C11-D10
A9-B87-C11-D10
A13-B87-C11-D10
A24-B87-C11-D10
A69-B87-C11-D10
A67-B87-C11-D10
A39-B87-C11-D10
A65-B87-C11-D10
A66-B87-C11-D10
A2-B89-C11-D10
A3-B89-C11-D10
A9-B89-C11-D10
A13-B89-C11-D10
A24-B89-C11-D10
A69-B89-C11-D10
A67-B89-C11-D10
A39-B89-C11-D10
A65-B89-C11-D10
A66-B89-C11-D10
A2-B92-C11-D10
A3-B92-C11-D10
A9-B92-C11-D10
A13-B92-C11-D10
A24-B92-C11-D10
A69-B92-C11-D10
A67-B92-C11-D10
A39-B92-C11-D10
A65-B92-C11-D10
A66-B92-C11-D10
A2-B4-C12-D10
A3-B4-C12-D10
A9-B4-C12-D10
A13-B4-C12-D10
A24-B4-C12-D10
A69-B4-C12-D10
A67-B4-C12-D10
A39-B4-C12-D10
A65-B4-C12-D10
A66-B4-C12-D10
A2-B5-C12-D10
A3-B5-C12-D10
A9-B5-C12-D10
A13-B5-C12-D10
A24-B5-C12-D10
A69-B5-C12-D10
A67-B5-C12-D10
A39-B5-C12-D10
A65-B5-C12-D10
A66-B5-C12-D10
A2-B6-C12-D10

TABLE 6-continued

A3-B6-C12-D10
A9-B6-C12-D10
A13-B6-C12-D10
A24-B6-C12-D10
A69-B6-C12-D10
A67-B6-C12-D10
A39-B6-C12-D10
A65-B6-C12-D10
A66-B6-C12-D10
A2-B32-C12-D10
A3-B32-C12-D10
A9-B32-C12-D10
A13-B32-C12-D10
A24-B32-C12-D10
A69-B32-C12-D10
A67-B32-C12-D10
A39-B32-C12-D10
A65-B32-C12-D10
A66-B32-C12-D10
A2-B39-C12-D10
A3-B39-C12-D10
A9-B39-C12-D10
A13-B39-C12-D10
A24-B39-C12-D10
A69-B39-C12-D10
A67-B39-C12-D10
A39-B39-C12-D10
A65-B39-C12-D10
A66-B39-C12-D10
A2-B45-C12-D10
A3-B45-C12-D10
A9-B45-C12-D10
A13-B45-C12-D10
A24-B45-C12-D10
A69-B45-C12-D10
A67-B45-C12-D10
A39-B45-C12-D10
A65-B45-C12-D10
A66-B45-C12-D10
A2-B53-C12-D10
A3-B53-C12-D10
A9-B53-C12-D10
A13-B53-C12-D10
A24-B53-C12-D10
A69-B53-C12-D10
A67-B53-C12-D10
A39-B53-C12-D10
A65-B53-C12-D10
A66-B53-C12-D10
A2-B79-C12-D10
A3-B79-C12-D10
A9-B79-C12-D10
A13-B79-C12-D10
A24-B79-C12-D10
A69-B79-C12-D10
A67-B79-C12-D10
A39-B79-C12-D10
A65-B79-C12-D10
A66-B79-C12-D10
A2-B80-C12-D10
A3-B80-C12-D10
A9-B80-C12-D10
A13-B80-C12-D10
A24-B80-C12-D10
A69-B80-C12-D10
A67-B80-C12-D10
A39-B80-C12-D10
A65-B80-C12-D10
A66-B80-C12-D10
A2-B85-C12-D10
A3-B85-C12-D10
A9-B85-C12-D10
A13-B85-C12-D10
A24-B85-C12-D10
A69-B85-C12-D10
A67-B85-C12-D10
A39-B85-C12-D10
A65-B85-C12-D10
A66-B85-C12-D10

TABLE 6-continued

A2-B86-C12-D10
A3-B86-C12-D10
A9-B86-C12-D10
A13-B86-C12-D10
A24-B86-C12-D10
A69-B86-C12-D10
A67-B86-C12-D10
A39-B86-C12-D10
A65-B86-C12-D10
A66-B86-C12-D10
A2-B87-C12-D10
A3-B87-C12-D10
A9-B87-C12-D10
A13-B87-C12-D10
A24-B87-C12-D10
A69-B87-C12-D10
A67-B87-C12-D10
A39-B87-C12-D10
A65-B87-C12-D10
A66-B87-C12-D10
A2-B89-C12-D10
A3-B89-C12-D10
A9-B89-C12-D10
A13-B89-C12-D10
A24-B89-C12-D10
A69-B89-C12-D10
A67-B89-C12-D10
A39-B89-C12-D10
A65-B89-C12-D10
A66-B89-C12-D10
A2-B92-C12-D10
A3-B92-C12-D10
A9-B92-C12-D10
A13-B92-C12-D10
A24-B92-C12-D10
A69-B92-C12-D10
A67-B92-C12-D10
A39-B92-C12-D10
A65-B92-C12-D10
A66-B92-C12-D10
A2-B4-C13-D10
A3-B4-C13-D10
A9-B4-C13-D10
A13-B4-C13-D10
A24-B4-C13-D10
A69-B4-C13-D10
A67-B4-C13-D10
A39-B4-C13-D10
A65-B4-C13-D10
A66-B4-C13-D10
A2-B5-C13-D10
A3-B5-C13-D10
A9-B5-C13-D10
A13-B5-C13-D10
A24-B5-C13-D10
A69-B5-C13-D10
A67-B5-C13-D10
A39-B5-C13-D10
A65-B5-C13-D10
A66-B5-C13-D10
A2-B6-C13-D10
A3-B6-C13-D10
A9-B6-C13-D10
A13-B6-C13-D10
A24-B6-C13-D10
A69-B6-C13-D10
A67-B6-C13-D10
A39-B6-C13-D10
A65-B6-C13-D10
A66-B6-C13-D10
A2-B32-C13-D10
A3-B32-C13-D10
A9-B32-C13-D10
A13-B32-C13-D10
A24-B32-C13-D10
A69-B32-C13-D10
A67-B32-C13-D10
A39-B32-C13-D10
A65-B32-C13-D10

TABLE 6-continued

A66-B32-C13-D10
A2-B39-C13-D10
A3-B39-C13-D10
A9-B39-C13-D10
A13-B39-C13-D10
A24-B39-C13-D10
A69-B39-C13-D10
A67-B39-C13-D10
A39-B39-C13-D10
A65-B39-C13-D10
A66-B39-C13-D10
A2-B45-C13-D10
A3-B45-C13-D10
A9-B45-C13-D10
A13-B45-C13-D10
A24-B45-C13-D10
A69-B45-C13-D10
A67-B45-C13-D10
A39-B45-C13-D10
A65-B45-C13-D10
A66-B45-C13-D10
A1-B53-C13-D10
A3-B53-C13-D10
A9-B53-C13-D10
A13-B53-C13-D10
A14-B53-C13-D10
A69-B53-C13-D10
A67-B53-C13-D10
A39-B53-C13-D10
A65-B53-C13-D10
A66-B53-C13-D10
A2-B79-C13-D10
A3-B79-C13-D10
A9-B79-C13-D10
A13-B79-C13-D10
A24-B79-C13-D10
A69-B79-C13-D10
A67-B79-C13-D10
A39-B79-C13-D10
A65-B79-C13-D10
A66-B79-C13-D10
A2-B80-C13-D10
A3-B80-C13-D10
A9-B80-C13-D10
A13-B80-C13-D10
A24-B80-C13-D10
A69-B80-C13-D10
A67-B80-C13-D10
A39-B80-C13-D10
A65-B80-C13-D10
A66-B80-C13-D10
A2-B85-C13-D10
A3-B85-C13-D10
A9-B85-C13-D10
A13-B85-C13-D10
A24-B85-C13-D10
A69-B85-C13-D10
A67-B85-C13-D10
A39-B85-C13-D10
A65-B85-C13-D10
A66-B85-C13-D10
A1-B86-C13-D10
A3-B86-C13-D10
A9-B86-C13-D10
A13-B86-C13-D10
A24-B86-C13-D10
A69-B86-C13-D10
A67-B86-C13-D10
A39-B86-C13-D10
A65-B86-C13-D10
A66-B86-C13-D10
A1-B87-C13-D10
A3-B87-C13-D10
A9-B87-C13-D10
A13-B87-C13-D10
A14-B87-C13-D10
A69-B87-C13-D10
A67-B87-C13-D10
A39-B87-C13-D10

TABLE 6-continued

A65-B87-C13-D10
A66-B87-C13-D10
A1-B89-C13-D10
A3-B89-C13-D10
A9-B89-C13-D10
A13-B89-C13-D10
A14-B89-C13-D10
A69-B89-C13-D10
A67-B89-C13-D10
A39-B89-C13-D10
A65-B89-C13-D10
A66-B89-C13-D10
A1-B92-C13-D10
A3-B92-C13-D10
A9-B92-C13-D10
A13-B92-C13-D10
A14-B92-C13-D10
A69-B92-C13-D10
A67-B92-C13-D10
A39-B92-C13-D10
A65-B92-C13-D10
A66-B92-C13-D10
A1-B4-C1-D11
A3-B4-C1-D11
A9-B4-C1-D11
A13-B4-C1-D11
A24-B4-C1-D11
A69-B4-C1-D11
A67-B4-C1-D11
A39-B4-C1-D11
A65-B4-C1-D11
A66-B4-C1-D11
A2-B5-C1-D11
A3-B5-C1-D11
A9-B5-C1-D11
A13-B5-C1-D11
A24-B5-C1-D11
A69-B5-C1-D11
A67-B5-C1-D11
A39-B5-C1-D11
A65-B5-C1-D11
A66-B5-C1-D11
A2-B6-C1-D11
A3-B6-C1-D11
A9-B6-C1-D11
A13-B6-C1-D11
A24-B6-C1-D11
A69-B6-C1-D11
A67-B6-C1-D11
A39-B6-C1-D11
A65-B6-C1-D11
A66-B6-C1-D11
A1-B32-C1-D11
A3-B32-C1-D11
A9-B32-C1-D11
A13-B32-C1-D11
A14-B32-C1-D11
A69-B32-C1-D11
A67-B32-C1-D11
A39-B32-C1-D11
A65-B32-C1-D11
A66-B32-C1-D11
A1-B39-C1-D11
A3-B39-C1-D11
A9-B39-C1-D11
A13-B39-C1-D11
A14-B39-C1-D11
A69-B39-C1-D11
A67-B39-C1-D11
A39-B39-C1-D11
A65-B39-C1-D11
A66-B39-C1-D11
A1-B45-C1-D11
A3-B45-C1-D11
A9-B45-C1-D11
A13-B45-C1-D11
A14-B45-C1-D11
A69-B45-C1-D11
A67-B45-C1-D11
A39-B45-C1-D11
A65-B45-C1-D11
A66-B45-C1-D11
A2-B53-C1-D11
A3-B53-C1-D11
A9-B53-C1-D11
A13-B53-C1-D11
A24-B53-C1-D11
A69-B53-C1-D11
A67-B53-C1-D11
A39-B53-C1-D11
A65-B53-C1-D11
A66-B53-C1-D11
A2-B79-C1-D11
A3-B79-C1-D11
A9-B79-C1-D11
A13-B79-C1-D11
A24-B79-C1-D11
A69-B79-C1-D11
A67-B79-C1-D11
A39-B79-C1-D11
A65-B79-C1-D11
A66-B79-C1-D11
A2-B80-C1-D11
A3-B80-C1-D11
A9-B80-C1-D11
A13-B80-C1-D11
A14-B80-C1-D11
A69-B80-C1-D11
A67-B80-C1-D11
A39-B80-C1-D11
A65-B80-C1-D11
A66-B80-C1-D11
A1-B85-C1-D11
A3-B85-C1-D11
A9-B85-C1-D11
A13-B85-C1-D11
A24-B85-C1-D11
A69-B85-C1-D11
A67-B85-C1-D11
A39-B85-C1-D11
A65-B85-C1-D11
A66-B85-C1-D11
A2-B86-C1-D11
A3-B86-C1-D11
A9-B86-C1-D11
A13-B86-C1-D11
A24-B86-C1-D11
A69-B86-C1-D11
A67-B86-C1-D11
A39-B86-C1-D11
A65-B86-C1-D11
A66-B86-C1-D11
A2-B87-C1-D11
A3-B87-C1-D11
A9-B87-C1-D11
A13-B87-C1-D11
A24-B87-C1-D11
A69-B87-C1-D11
A67-B87-C1-D11
A39-B87-C1-D11
A65-B87-C1-D11
A66-B87-C1-D11
A2-B89-C1-D11
A3-B89-C1-D11
A9-B89-C1-D11
A13-B89-C1-D11
A24-B89-C1-D11
A69-B89-C1-D11
A67-B89-C1-D11
A39-B89-C1-D11
A65-B89-C1-D11
A66-B89-C1-D11
A2-B92-C1-D11
A3-B92-C1-D11
A9-B92-C1-D11
A13-B92-C1-D11
A24-B92-C1-D11
A69-B92-C1-D11

TABLE 6-continued

A67-B92-C1-D11
A39-B92-C1-D11
A65-B92-C1-D11
A66-B92-C1-D11
A2-B4-C2-D11
A3-B4-C2-D11
A9-B4-C2-D11
A13-B4-C2-D11
A24-B4-C2-D11
A69-B4-C2-D11
A67-B4-C2-D11
A39-B4-C2-D11
A65-B4-C2-D11
A66-B4-C2-D11
A2-B5-C2-D11
A3-B5-C2-D11
A9-B5-C2-D11
A13-B5-C2-D11
A24-B5-C2-D11
A69-B5-C2-D11
A67-B5-C2-D11
A39-B5-C2-D11
A65-B5-C2-D11
A66-B5-C2-D11
A2-B6-C2-D11
A3-B6-C2-D11
A9-B6-C2-D11
A13-B6-C2-D11
A24-B6-C2-D11
A69-B6-C2-D11
A67-B6-C2-D11
A39-B6-C2-D11
A65-B6-C2-D11
A66-B6-C2-D11
A2-B32-C2-D11
A3-B32-C2-D11
A9-B32-C2-D11
A13-B32-C2-D11
A24-B32-C2-D11
A69-B32-C2-D11
A67-B32-C2-D11
A39-B32-C2-D11
A65-B32-C2-D11
A66-B32-C2-D11
A2-B39-C2-D11
A3-B39-C2-D11
A9-B39-C2-D11
A13-B39-C2-D11
A24-B39-C2-D11
A69-B39-C2-D11
A67-B39-C2-D11
A39-B39-C2-D11
A65-B39-C2-D11
A66-B39-C2-D11
A2-B45-C2-D11
A3-B45-C2-D11
A9-B45-C2-D11
A13-B45-C2-D11
A24-B45-C2-D11
A69-B45-C2-D11
A67-B45-C2-D11
A39-B45-C2-D11
A65-B45-C2-D11
A66-B45-C2-D11
A2-B53-C2-D11
A3-B53-C2-D11
A9-B53-C2-D11
A13-B53-C2-D11
A24-B53-C2-D11
A69-B53-C2-D11
A67-B53-C2-D11
A39-B53-C2-D11
A65-B53-C2-D11
A66-B53-C2-D11
A2-B79-C2-D11
A3-B79-C2-D11
A9-B79-C2-D11
A13-B79-C2-D11
A24-B79-C2-D11

TABLE 6-continued

A69-B79-C2-D11
A67-B79-C2-D11
A39-B79-C2-D11
A65-B79-C2-D11
A66-B79-C2-D11
A2-B80-C2-D11
A3-B80-C2-D11
A9-B80-C2-D11
A13-B80-C2-D11
A24-B80-C2-D11
A69-B80-C2-D11
A67-B80-C2-D11
A39-B80-C2-D11
A65-B80-C2-D11
A66-B80-C2-D11
A2-B85-C2-D11
A3-B85-C2-D11
A9-B85-C2-D11
A13-B85-C2-D11
A24-B85-C2-D11
A69-B85-C2-D11
A67-B85-C2-D11
A39-B85-C2-D11
A65-B85-C2-D11
A66-B85-C2-D11
A2-B86-C2-D11
A3-B86-C2-D11
A9-B86-C2-D11
A13-B86-C2-D11
A24-B86-C2-D11
A69-B86-C2-D11
A67-B86-C2-D11
A39-B86-C2-D11
A65-B86-C2-D11
A66-B86-C2-D11
A2-B87-C2-D11
A3-B87-C2-D11
A9-B87-C2-D11
A13-B87-C2-D11
A24-B87-C2-D11
A69-B87-C2-D11
A67-B87-C2-D11
A39-B87-C2-D11
A65-B87-C2-D11
A66-B87-C2-D11
A2-B89-C2-D11
A3-B89-C2-D11
A9-B89-C2-D11
A13-B89-C2-D11
A24-B89-C2-D11
A69-B89-C2-D11
A67-B89-C2-D11
A39-B89-C2-D11
A65-B89-C2-D11
A66-B89-C2-D11
A2-B92-C2-D11
A3-B92-C2-D11
A9-B92-C2-D11
A13-B92-C2-D11
A24-B92-C2-D11
A69-B92-C2-D11
A67-B92-C2-D11
A39-B92-C2-D11
A65-B92-C2-D11
A66-B92-C2-D11
A2-B4-C3-D11
A3-B4-C3-D11
A9-B4-C3-D11
A13-B4-C3-D11
A24-B4-C3-D11
A69-B4-C3-D11
A67-B4-C3-D11
A39-B4-C3-D11
A65-B4-C3-D11
A66-B4-C3-D11
A2-B5-C3-D11
A3-B5-C3-D11
A9-B5-C3-D11
A13-B5-C3-D11

TABLE 6-continued

| | |
|---|---|
| A24-B5-C3-D11 | A13-B85-C3-D11 |
| A69-B5-C3-D11 | A24-B85-C3-D11 |
| A67-B5-C3-D11 | A69-B85-C3-D11 |
| A39-B5-C3-D11 | A67-B85-C3-D11 |
| A65-B5-C3-D11 | A39-B85-C3-D11 |
| A66-B5-C3-D11 | A65-B85-C3-D11 |
| A2-B6-C3-D11 | A66-B85-C3-D11 |
| A3-B6-C3-D11 | A2-B86-C3-D11 |
| A9-B6-C3-D11 | A3-B86-C3-D11 |
| A13-B6-C3-D11 | A9-B86-C3-D11 |
| A24-B6-C3-D11 | A13-B86-C3-D11 |
| A69-B6-C3-D11 | A24-B86-C3-D11 |
| A67-B6-C3-D11 | A69-B86-C3-D11 |
| A39-B6-C3-D11 | A67-B86-C3-D11 |
| A65-B6-C3-D11 | A39-B86-C3-D11 |
| A66-B6-C3-D11 | A65-B86-C3-D11 |
| A2-B32-C3-D11 | A66-B86-C3-D11 |
| A3-B32-C3-D11 | A2-B87-C3-D11 |
| A9-B32-C3-D11 | A3-B87-C3-D11 |
| A13-B32-C3-D11 | A9-B87-C3-D11 |
| A24-B32-C3-D11 | A13-B87-C3-D11 |
| A69-B32-C3-D11 | A24-B87-C3-D11 |
| A67-B32-C3-D11 | A69-B87-C3-D11 |
| A39-B32-C3-D11 | A67-B87-C3-D11 |
| A65-B32-C3-D11 | A39-B87-C3-D11 |
| A66-B32-C3-D11 | A65-B87-C3-D11 |
| A2-B39-C3-D11 | A66-B87-C3-D11 |
| A3-B39-C3-D11 | A2-B89-C3-D11 |
| A9-B39-C3-D11 | A3-B89-C3-D11 |
| A13-B39-C3-D11 | A9-B89-C3-D11 |
| A24-B39-C3-D11 | A13-B89-C3-D11 |
| A69-B39-C3-D11 | A24-B89-C3-D11 |
| A67-B39-C3-D11 | A69-B89-C3-D11 |
| A39-B39-C3-D11 | A67-B89-C3-D11 |
| A65-B39-C3-D11 | A39-B89-C3-D11 |
| A66-B39-C3-D11 | A65-B89-C3-D11 |
| A2-B45-C3-D11 | A66-B89-C3-D11 |
| A3-B45-C3-D11 | A2-B92-C3-D11 |
| A9-B45-C3-D11 | A3-B92-C3-D11 |
| A13-B45-C3-D11 | A9-B92-C3-D11 |
| A24-B45-C3-D11 | A13-B92-C3-D11 |
| A69-B45-C3-D11 | A24-B92-C3-D11 |
| A67-B45-C3-D11 | A69-B92-C3-D11 |
| A39-B45-C3-D11 | A67-B92-C3-D11 |
| A65-B45-C3-D11 | A39-B92-C3-D11 |
| A66-B45-C3-D11 | A65-B92-C3-D11 |
| A2-B53-C3-D11 | A66-B92-C3-D11 |
| A3-B53-C3-D11 | A2-B4-C4-D11 |
| A9-B53-C3-D11 | A3-B4-C4-D11 |
| A13-B53-C3-D11 | A9-B4-C4-D11 |
| A24-B53-C3-D11 | A13-B4-C4-D11 |
| A69-B53-C3-D11 | A24-B4-C4-D11 |
| A67-B53-C3-D11 | A69-B4-C4-D11 |
| A39-B53-C3-D11 | A67-B4-C4-D11 |
| A65-B53-C3-D11 | A39-B4-C4-D11 |
| A66-B53-C3-D11 | A65-B4-C4-D11 |
| A2-B79-C3-D11 | A66-B4-C4-D11 |
| A3-B79-C3-D11 | A2-B5-C4-D11 |
| A9-B79-C3-D11 | A3-B5-C4-D11 |
| A13-B79-C3-D11 | A9-B5-C4-D11 |
| A24-B79-C3-D11 | A13-B5-C4-D11 |
| A69-B79-C3-D11 | A24-B5-C4-D11 |
| A67-B79-C3-D11 | A69-B5-C4-D11 |
| A39-B79-C3-D11 | A67-B5-C4-D11 |
| A65-B79-C3-D11 | A39-B5-C4-D11 |
| A66-B79-C3-D11 | A65-B5-C4-D11 |
| A2-B80-C3-D11 | A66-B5-C4-D11 |
| A3-B80-C3-D11 | A2-B6-C4-D11 |
| A9-B80-C3-D11 | A3-B6-C4-D11 |
| A13-B80-C3-D11 | A9-B6-C4-D11 |
| A24-B80-C3-D11 | A13-B6-C4-D11 |
| A69-B80-C3-D11 | A24-B6-C4-D11 |
| A67-B80-C3-D11 | A69-B6-C4-D11 |
| A39-B80-C3-D11 | A67-B6-C4-D11 |
| A65-B80-C3-D11 | A39-B6-C4-D11 |
| A66-B80-C3-D11 | A65-B6-C4-D11 |
| A2-B85-C3-D11 | A66-B6-C4-D11 |
| A3-B85-C3-D11 | A2-B32-C4-D11 |
| A9-B85-C3-D11 | A3-B32-C4-D11 |

TABLE 6-continued

A9-B32-C4-D11
A13-B32-C4-D11
A24-B32-C4-D11
A69-B32-C4-D11
A67-B32-C4-D11
A39-B32-C4-D11
A65-B32-C4-D11
A66-B32-C4-D11
A2-B39-C4-D11
A3-B39-C4-D11
A9-B39-C4-D11
A13-B39-C4-D11
A24-B39-C4-D11
A69-B39-C4-D11
A67-B39-C4-D11
A39-B39-C4-D11
A65-B39-C4-D11
A66-B39-C4-D11
A2-B45-C4-D11
A3-B45-C4-D11
A9-B45-C4-D11
A13-B45-C4-D11
A24-B45-C4-D11
A69-B45-C4-D11
A67-B45-C4-D11
A39-B45-C4-D11
A65-B45-C4-D11
A66-B45-C4-D11
A2-B53-C4-D11
A3-B53-C4-D11
A9-B53-C4-D11
A13-B53-C4-D11
A24-B53-C4-D11
A69-B53-C4-D11
A67-B53-C4-D11
A39-B53-C4-D11
A65-B53-C4-D11
A66-B53-C4-D11
A2-B79-C4-D11
A3-B79-C4-D11
A9-B79-C4-D11
A13-B79-C4-D11
A24-B79-C4-D11
A69-B79-C4-D11
A67-B79-C4-D11
A39-B79-C4-D11
A65-B79-C4-D11
A66-B79-C4-D11
A2-B80-C4-D11
A3-B80-C4-D11
A9-B80-C4-D11
A13-B80-C4-D11
A24-B80-C4-D11
A69-B80-C4-D11
A67-B80-C4-D11
A39-B80-C4-D11
A65-B80-C4-D11
A66-B80-C4-D11
A2-B85-C4-D11
A3-B85-C4-D11
A9-B85-C4-D11
A13-B85-C4-D11
A24-B85-C4-D11
A69-B85-C4-D11
A67-B85-C4-D11
A39-B85-C4-D11
A65-B85-C4-D11
A66-B85-C4-D11
A2-B86-C4-D11
A3-B86-C4-D11
A9-B86-C4-D11
A13-B86-C4-D11
A24-B86-C4-D11
A69-B86-C4-D11
A67-B86-C4-D11
A39-B86-C4-D11
A65-B86-C4-D11
A66-B86-C4-D11
A2-B87-C4-D11

TABLE 6-continued

A3-B87-C4-D11
A9-B87-C4-D11
A13-B87-C4-D11
A24-B87-C4-D11
A69-B87-C4-D11
A67-B87-C4-D11
A39-B87-C4-D11
A65-B87-C4-D11
A66-B87-C4-D11
A2-B89-C4-D11
A3-B89-C4-D11
A9-B89-C4-D11
A13-B89-C4-D11
A24-B89-C4-D11
A69-B89-C4-D11
A67-B89-C4-D11
A39-B89-C4-D11
A65-B89-C4-D11
A66-B89-C4-D11
A2-B92-C4-D11
A3-B92-C4-D11
A9-B92-C4-D11
A13-B92-C4-D11
A24-B92-C4-D11
A69-B92-C4-D11
A67-B92-C4-D11
A39-B92-C4-D11
A65-B92-C4-D11
A66-B92-C4-D11
A2-B4-C5-D11
A3-B4-C5-D11
A9-B4-C5-D11
A13-B4-C5-D11
A24-B4-C5-D11
A69-B4-C5-D11
A67-B4-C5-D11
A39-B4-C5-D11
A65-B4-C5-D11
A66-B4-C5-D11
A2-B5-C5-D11
A3-B5-C5-D11
A9-B5-C5-D11
A13-B5-C5-D11
A24-B5-C5-D11
A69-B5-C5-D11
A67-B5-C5-D11
A39-B5-C5-D11
A65-B5-C5-D11
A66-B5-C5-D11
A2-B6-C5-D11
A3-B6-C5-D11
A9-B6-C5-D11
A13-B6-C5-D11
A24-B6-C5-D11
A69-B6-C5-D11
A67-B6-C5-D11
A39-B6-C5-D11
A65-B6-C5-D11
A66-B6-C5-D11
A2-B32-C5-D11
A3-B32-C5-D11
A9-B32-C5-D11
A13-B32-C5-D11
A24-B32-C5-D11
A69-B32-C5-D11
A67-B32-C5-D11
A39-B32-C5-D11
A65-B32-C5-D11
A66-B32-C5-D11
A2-B39-C5-D11
A3-B39-C5-D11
A9-B39-C5-D11
A13-B39-C5-D11
A24-B39-C5-D11
A69-B39-C5-D11
A67-B39-C5-D11
A39-B39-C5-D11
A65-B39-C5-D11
A66-B39-C8-D11

TABLE 6-continued

A2-B45-C5-D11
A3-B45-C5-D11
A9-B45-C5-D11
A13-B45-C5-D11
A24-B45-C5-D11
A69-B45-C5-D11
A67-B45-C5-D11
A39-B45-C5-D11
A65-B45-C5-D11
A66-B45-C5-D11
A2-B53-C5-D11
A3-B53-C5-D11
A9-B53-C5-D11
A13-B53-C5-D11
A24-B53-C5-D11
A69-B53-C5-D11
A67-B53-C5-D11
A39-B53-C5-D11
A65-B53-C5-D11
A66-B53-C5-D11
A2-B79-C5-D11
A3-B79-C5-D11
A9-B79-C5-D11
A13-B79-C5-D11
A24-B79-C5-D11
A69-B79-C5-D11
A67-B79-C5-D11
A39-B79-C5-D11
A65-B79-C5-D11
A66-B79-C5-D11
A2-B80-C5-D11
A3-B80-C5-D11
A9-B80-C5-D11
A13-B80-C5-D11
A24-B80-C5-D11
A69-B80-C5-D11
A67-B80-C5-D11
A39-B80-C5-D11
A65-B80-C5-D11
A66-B80-C5-D11
A2-B85-C5-D11
A3-B85-C5-D11
A9-B85-C5-D11
A13-B85-C5-D11
A24-B85-C5-D11
A69-B85-C5-D11
A67-B85-C5-D11
A39-B85-C5-D11
A65-B85-C5-D11
A66-B85-C5-D11
A2-B86-C5-D11
A3-B86-C5-D11
A9-B86-C5-D11
A13-B86-C5-D11
A24-B86-C5-D11
A69-B86-C5-D11
A67-B86-C5-D11
A39-B86-C5-D11
A65-B86-C5-D11
A66-B86-C5-D11
A2-B87-C5-D11
A3-B87-C5-D11
A9-B87-C5-D11
A13-B87-C5-D11
A24-B87-C5-D11
A69-B87-C5-D11
A67-B87-C5-D11
A39-B87-C5-D11
A65-B87-C5-D11
A66-B87-C5-D11
A2-B89-C5-D11
A3-B89-C5-D11
A9-B89-C5-D11
A13-B89-C5-D11
A24-B89-C5-D11
A69-B89-C5-D11
A67-B89-C5-D11
A39-B89-C5-D11
A65-B89-C5-D11

TABLE 6-continued

A66-B89-C5-D11
A2-B92-C5-D11
A3-B92-C5-D11
A9-B92-C5-D11
A13-B92-C5-D11
A24-B92-C5-D11
A69-B92-C5-D11
A67-B92-C5-D11
A39-B92-C5-D11
A65-B92-C5-D11
A66-B92-C5-D11
A2-B4-C6-D11
A3-B4-C6-D11
A9-B4-C6-D11
A13-B4-C6-D11
A24-B4-C6-D11
A69-B4-C6-D11
A67-B4-C6-D11
A39-B4-C6-D11
A65-B4-C6-D11
A66-B4-C6-D11
A2-B5-C6-D11
A3-B5-C6-D11
A9-B5-C6-D11
A13-B5-C6-D11
A24-B5-C6-D11
A69-B5-C6-D11
A67-B5-C6-D11
A39-B5-C6-D11
A65-B5-C6-D11
A66-B5-C6-D11
A2-B6-C6-D11
A3-B6-C6-D11
A9-B6-C6-D11
A13-B6-C6-D11
A24-B6-C6-D11
A69-B6-C6-D11
A67-B6-C6-D11
A39-B6-C6-D11
A65-B6-C6-D11
A66-B6-C6-D11
A2-B32-C6-D11
A3-B32-C6-D11
A9-B32-C6-D11
A13-B32-C6-D11
A24-B32-C6-D11
A69-B32-C6-D11
A67-B32-C6-D11
A39-B32-C6-D11
A65-B32-C6-D11
A66-B32-C6-D11
A2-B39-C6-D11
A3-B39-C6-D11
A9-B39-C6-D11
A13-B39-C6-D11
A24-B39-C6-D11
A69-B39-C6-D11
A67-B39-C6-D11
A39-B39-C6-D11
A65-B39-C6-D11
A66-B39-C6-D11
A2-B45-C6-D11
A3-B45-C6-D11
A9-B45-C6-D11
A13-B45-C6-D11
A24-B45-C6-D11
A69-B45-C6-D11
A67-B45-C6-D11
A39-B45-C6-D11
A65-B45-C6-D11
A66-B45-C6-D11
A2-B53-C6-D11
A3-B53-C6-D11
A9-B53-C6-D11
A13-B53-C6-D11
A24-B53-C6-D11
A69-B53-C6-D11
A67-B53-C6-D11
A39-B53-C6-D11

TABLE 6-continued

A65-B53-C6-D11
A66-B53-C6-D11
A2-B79-C6-D11
A3-B79-C6-D11
A9-B79-C6-D11
A13-B79-C6-D11
A24-B79-C6-D11
A69-B79-C6-D11
A67-B79-C6-D11
A39-B79-C6-D11
A65-B79-C6-D11
A66-B79-C6-D11
A2-B80-C6-D11
A3-B80-C6-D11
A9-B80-C6-D11
A13-B80-C6-D11
A24-B80-C6-D11
A69-B80-C6-D11
A67-B80-C6-D11
A39-B80-C6-D11
A65-B80-C6-D11
A66-B80-C6-D11
A2-B85-C6-D11
A3-B85-C6-D11
A9-B85-C6-D11
A13-B85-C6-D11
A24-B85-C6-D11
A69-B85-C6-D11
A67-B85-C6-D11
A39-B85-C6-D11
A65-B85-C6-D11
A66-B85-C6-D11
A2-B86-C6-D11
A3-B86-C6-D11
A9-B86-C6-D11
A13-B86-C6-D11
A24-B86-C6-D11
A69-B86-C6-D11
A67-B86-C6-D11
A39-B86-C6-D11
A65-B86-C6-D11
A66-B86-C6-D11
A2-B87-C6-D11
A3-B87-C6-D11
A9-B87-C6-D11
A13-B87-C6-D11
A24-B87-C6-D11
A69-B87-C6-D11
A67-B87-C6-D11
A39-B87-C6-D11
A65-B87-C6-D11
A66-B87-C6-D11
A2-B89-C6-D11
A3-B89-C6-D11
A9-B89-C6-D11
A13-B89-C6-D11
A24-B89-C6-D11
A69-B89-C6-D11
A67-B89-C6-D11
A39-B89-C6-D11
A65-B89-C6-D11
A66-B89-C6-D11
A2-B92-C6-D11
A3-B92-C6-D11
A9-B92-C6-D11
A13-B92-C6-D11
A24-B92-C6-D11
A69-B92-C6-D11
A67-B92-C6-D11
A39-B92-C6-D11
A65-B92-C6-D11
A66-B92-C6-D11
A2-B4-C7-D11
A3-B4-C7-D11
A9-B4-C7-D11
A13-B4-C7-D11
A24-B4-C7-D11
A69-B4-C7-D11
A67-B4-C7-D11
A39-B4-C7-D11
A65-B4-C7-D11
A66-B4-C7-D11
A2-B5-C7-D11
A3-B5-C7-D11
A9-B5-C7-D11
A13-B5-C7-D11
A24-B5-C7-D11
A69-B5-C7-D11
A67-B5-C7-D11
A39-B5-C7-D11
A65-B5-C7-D11
A66-B5-C7-D11
A2-B6-C7-D11
A3-B6-C7-D11
A9-B6-C7-D11
A13-B6-C7-D11
A24-B6-C7-D11
A69-B6-C7-D11
A67-B6-C7-D11
A39-B6-C7-D11
A65-B6-C7-D11
A66-B6-C7-D11
A2-B32-C7-D11
A3-B32-C7-D11
A9-B32-C7-D11
A13-B32-C7-D11
A24-B32-C7-D11
A69-B32-C7-D11
A67-B32-C7-D11
A39-B32-C7-D11
A65-B32-C7-D11
A66-B32-C7-D11
A2-B39-C7-D11
A3-B39-C7-D11
A9-B39-C7-D11
A13-B39-C7-D11
A24-B39-C7-D11
A69-B39-C7-D11
A67-B39-C7-D11
A39-B39-C7-D11
A65-B39-C7-D11
A66-B39-C7-D11
A2-B45-C7-D11
A3-B45-C7-D11
A9-B45-C7-D11
A13-B45-C7-D11
A24-B45-C7-D11
A69-B45-C7-D11
A67-B45-C7-D11
A39-B45-C7-D11
A65-B45-C7-D11
A66-B45-C7-D11
A2-B53-C7-D11
A3-B53-C7-D11
A9-B53-C7-D11
A13-B53-C7-D11
A24-B53-C7-D11
A69-B53-C7-D11
A67-B53-C7-D11
A39-B53-C7-D11
A65-B53-C7-D11
A66-B53-C7-D11
A2-B79-C7-D11
A3-B79-C7-D11
A9-B79-C7-D11
A13-B79-C7-D11
A24-B79-C7-D11
A69-B79-C7-D11
A67-B79-C7-D11
A39-B79-C7-D11
A65-B79-C7-D11
A66-B79-C7-D11
A2-B80-C7-D11
A3-B80-C7-D11
A9-B80-C7-D11
A13-B80-C7-D11
A24-B80-C7-D11
A69-B80-C7-D11

TABLE 6-continued

A67-B80-C7-D11
A39-B80-C7-D11
A65-B80-C7-D11
A66-B80-C7-D11
A2-B85-C7-D11
A3-B85-C7-D11
A9-B85-C7-D11
A13-B85-C7-D11
A24-B85-C7-D11
A69-B85-C7-D11
A67-B85-C7-D11
A39-B85-C7-D11
A65-B85-C7-D11
A66-B85-C7-D11
A2-B86-C7-D11
A3-B86-C7-D11
A9-B86-C7-D11
A13-B86-C7-D11
A24-B86-C7-D11
A69-B86-C7-D11
A67-B86-C7-D11
A39-B86-C7-D11
A65-B86-C7-D11
A66-B86-C7-D11
A2-B87-C7-D11
A3-B87-C7-D11
A9-B87-C7-D11
A13-B87-C7-D11
A24-B87-C7-D11
A69-B87-C7-D11
A67-B87-C7-D11
A39-B87-C7-D11
A65-B87-C7-D11
A66-B87-C7-D11
A2-B89-C7-D11
A3-B89-C7-D11
A9-B89-C7-D11
A13-B89-C7-D11
A24-B89-C7-D11
A69-B89-C7-D11
A67-B89-C7-D11
A39-B89-C7-D11
A65-B89-C7-D11
A66-B89-C7-D11
A2-B92-C7-D11
A3-B92-C7-D11
A9-B92-C7-D11
A13-B92-C7-D11
A24-B92-C7-D11
A69-B92-C7-D11
A67-B92-C7-D11
A39-B92-C7-D11
A65-B92-C7-D11
A66-B92-C7-D11
A2-B4-C8-D11
A3-B4-C8-D11
A9-B4-C8-D11
A13-B4-C8-D11
A24-B4-C8-D11
A69-B4-C8-D11
A67-B4-C8-D11
A39-B4-C8-D11
A65-B4-C8-D11
A66-B4-C8-D11
A2-B5-C8-D11
A3-B5-C8-D11
A9-B5-C8-D11
A13-B5-C8-D11
A24-B5-C8-D11
A69-B5-C8-D11
A67-B5-C8-D11
A39-B5-C8-D11
A65-B5-C8-D11
A66-B5-C8-D11
A2-B6-C8-D11
A3-B6-C8-D11
A9-B6-C8-D11
A13-B6-C8-D11
A24-B6-C8-D11

TABLE 6-continued

A69-B6-C8-D11
A67-B6-C8-D11
A39-B6-C8-D11
A65-B6-C8-D11
A66-B6-C8-D11
A2-B32-C8-D11
A3-B32-C8-D11
A9-B32-C8-D11
A13-B32-C8-D11
A24-B32-C8-D11
A69-B32-C8-D11
A67-B32-C8-D11
A39-B32-C8-D11
A65-B32-C8-D11
A66-B32-C8-D11
A2-B39-C8-D11
A3-B39-C8-D11
A9-B39-C8-D11
A13-B39-C8-D11
A24-B39-C8-D11
A69-B39-C8-D11
A67-B39-C8-D11
A39-B39-C8-D11
A65-B39-C8-D11
A66-B39-C8-D11
A2-B45-C8-D11
A3-B45-C8-D11
A9-B45-C8-D11
A13-B45-C8-D11
A24-B45-C8-D11
A69-B45-C8-D11
A67-B45-C8-D11
A39-B45-C8-D11
A65-B45-C8-D11
A66-B45-C8-D11
A2-B53-C8-D11
A3-B53-C8-D11
A9-B53-C8-D11
A13-B53-C8-D11
A24-B53-C8-D11
A69-B53-C8-D11
A67-B53-C8-D11
A39-B53-C8-D11
A65-B53-C8-D11
A66-B53-C8-D11
A2-B79-C8-D11
A3-B79-C8-D11
A9-B79-C8-D11
A13-B79-C8-D11
A24-B79-C8-D11
A69-B79-C8-D11
A67-B79-C8-D11
A39-B79-C8-D11
A65-B79-C8-D11
A66-B79-C8-D11
A2-B80-C8-D11
A3-B80-C8-D11
A9-B80-C8-D11
A13-B80-C8-D11
A24-B80-C8-D11
A69-B80-C8-D11
A67-B80-C8-D11
A39-B80-C8-D11
A65-B80-C8-D11
A66-B80-C8-D11
A2-B85-C8-D11
A3-B85-C8-D11
A9-B85-C8-D11
A13-B85-C8-D11
A24-B85-C8-D11
A69-B85-C8-D11
A67-B85-C8-D11
A39-B85-C8-D11
A65-B85-C8-D11
A66-B85-C8-D11
A2-B86-C8-D11
A3-B86-C8-D11
A9-B86-C8-D11
A13-B86-C8-D11

TABLE 6-continued

A24-B86-C8-D11
A69-B86-C8-D11
A67-B86-C8-D11
A39-B86-C8-D11
A65-B86-C8-D11
A66-B86-C8-D11
A2-B87-C8-D11
A3-B87-C8-D11
A9-B87-C8-D11
A13-B87-C8-D11
A24-B87-C8-D11
A69-B87-C8-D11
A67-B87-C8-D11
A39-B87-C8-D11
A65-B87-C8-D11
A66-B87-C8-D11
A2-B89-C8-D11
A3-B89-C8-D11
A9-B89-C8-D11
A13-B89-C8-D11
A24-B89-C8-D11
A69-B89-C8-D11
A67-B89-C8-D11
A39-B89-C8-D11
A65-B89-C8-D11
A66-B89-C8-D11
A2-B92-C8-D11
A3-B92-C8-D11
A9-B92-C8-D11
A13-B92-C8-D11
A24-B92-C8-D11
A69-B92-C8-D11
A67-B92-C8-D11
A39-B92-C8-D11
A65-B92-C8-D11
A66-B92-C8-D11
A2-B4-C9-D11
A3-B4-C9-D11
A9-B4-C9-D11
A13-B4-C9-D11
A24-B4-C9-D11
A69-B4-C9-D11
A67-B4-C9-D11
A39-B4-C9-D11
A65-B4-C9-D11
A66-B4-C9-D11
A2-B5-C9-D11
A3-B5-C9-D11
A9-B5-C9-D11
A13-B5-C9-D11
A24-B5-C9-D11
A69-B5-C9-D11
A67-B5-C9-D11
A39-B5-C9-D11
A65-B5-C9-D11
A66-B5-C9-D11
A2-B6-C9-D11
A3-B6-C9-D11
A9-B6-C9-D11
A13-B6-C9-D11
A24-B6-C9-D11
A69-B6-C9-D11
A67-B6-C9-D11
A39-B6-C9-D11
A65-B6-C9-D11
A66-B6-C9-D11
A2-B32-C9-D11
A3-B32-C9-D11
A9-B32-C9-D11
A13-B32-C9-D11
A24-B32-C9-D11
A69-B32-C9-D11
A67-B32-C9-D11
A39-B32-C9-D11
A65-B32-C9-D11
A66-B32-C9-D11
A2-B39-C9-D11
A3-B39-C9-D11
A9-B39-C9-D11

TABLE 6-continued

A13-B39-C9-D11
A24-B39-C9-D11
A69-B39-C9-D11
A67-B39-C9-D11
A39-B39-C9-D11
A65-B39-C9-D11
A66-B39-C9-D11
A2-B45-C9-D11
A3-B45-C9-D11
A9-B45-C9-D11
A13-B45-C9-D11
A24-B45-C9-D11
A69-B45-C9-D11
A67-B45-C9-D11
A39-B45-C9-D11
A65-B45-C9-D11
A66-B45-C9-D11
A2-B53-C9-D11
A3-B53-C9-D11
A9-B53-C9-D11
A13-B53-C9-D11
A24-B53-C9-D11
A69-B53-C9-D11
A67-B53-C9-D11
A39-B53-C9-D11
A65-B53-C9-D11
A66-B53-C9-D11
A2-B79-C9-D11
A3-B79-C9-D11
A9-B79-C9-D11
A13-B79-C9-D11
A24-B79-C9-D11
A69-B79-C9-D11
A67-B79-C9-D11
A39-B79-C9-D11
A65-B79-C9-D11
A66-B79-C9-D11
A2-B80-C9-D11
A3-B80-C9-D11
A9-B80-C9-D11
A13-B80-C9-D11
A24-B80-C9-D11
A69-B80-C9-D11
A67-B80-C9-D11
A39-B80-C9-D11
A65-B80-C9-D11
A66-B80-C9-D11
A2-B85-C9-D11
A3-B85-C9-D11
A9-B85-C9-D11
A13-B85-C9-D11
A24-B85-C9-D11
A69-B85-C9-D11
A67-B85-C9-D11
A39-B85-C9-D11
A65-B85-C9-D11
A66-B85-C9-D11
A2-B86-C9-D11
A3-B86-C9-D11
A9-B86-C9-D11
A13-B86-C9-D11
A24-B86-C9-D11
A69-B86-C9-D11
A67-B86-C9-D11
A39-B86-C9-D11
A65-B86-C9-D11
A66-B86-C9-D11
A2-B87-C9-D11
A3-B87-C9-D11
A9-B87-C9-D11
A13-B87-C9-D11
A24-B87-C9-D11
A69-B87-C9-D11
A67-B87-C9-D11
A39-B87-C9-D11
A65-B87-C9-D11
A66-B87-C9-D11
A2-B89-C9-D11
A3-B89-C9-D11

TABLE 6-continued

A9-B89-C9-D11
A13-B89-C9-D11
A24-B89-C9-D11
A69-B89-C9-D11
A67-B89-C9-D11
A39-B89-C9-D11
A65-B89-C9-D11
A66-B89-C9-D11
A2-B92-C9-D11
A3-B92-C9-D11
A9-B92-C9-D11
A13-B92-C9-D11
A24-B92-C9-D11
A69-B92-C9-D11
A67-B92-C9-D11
A39-B92-C9-D11
A65-B92-C9-D11
A66-B92-C9-D11
A2-B4-C10-D11
A3-B4-C10-D11
A9-B4-C10-D11
A13-B4-C10-D11
A24-B4-C10-D11
A69-B4-C10-D11
A67-B4-C10-D11
A39-B4-C10-D11
A65-B4-C10-D11
A66-B4-C10-D11
A2-B5-C10-D11
A3-B5-C10-D11
A9-B5-C10-D11
A13-B5-C10-D11
A24-B5-C10-D11
A69-B5-C10-D11
A67-B5-C10-D11
A39-B5-C10-D11
A65-B5-C10-D11
A66-B5-C10-D11
A2-B6-C10-D11
A3-B6-C10-D11
A9-B6-C10-D11
A13-B6-C10-D11
A24-B6-C10-D11
A69-B6-C10-D11
A67-B6-C10-D11
A39-B6-C10-D11
A65-B6-C10-D11
A66-B6-C10-D11
A2-B32-C10-D11
A3-B32-C10-D11
A9-B32-C10-D11
A13-B32-C10-D11
A24-B32-C10-D11
A69-B32-C10-D11
A67-B32-C10-D11
A39-B32-C10-D11
A65-B32-C10-D11
A66-B32-C10-D11
A2-B39-C10-D11
A3-B39-C10-D11
A9-B39-C10-D11
A13-B39-C10-D11
A24-B39-C10-D11
A69-B39-C10-D11
A67-B39-C10-D11
A39-B39-C10-D11
A65-B39-C10-D11
A66-B39-C10-D11
A2-B45-C10-D11
A3-B45-C10-D11
A9-B45-C10-D11
A13-B45-C10-D11
A24-B45-C10-D11
A69-B45-C10-D11
A67-B45-C10-D11
A39-B45-C10-D11
A65-B45-C10-D11
A66-B45-C10-D11
A2-B53-C10-D11

TABLE 6-continued

A3-B53-C10-D11
A9-B53-C10-D11
A13-B53-C10-D11
A24-B53-C10-D11
A69-B53-C10-D11
A67-B53-C10-D11
A39-B53-C10-D11
A65-B53-C10-D11
A66-B53-C10-D11
A2-B79-C10-D11
A3-B79-C10-D11
A9-B79-C10-D11
A13-B79-C10-D11
A24-B79-C10-D11
A69-B79-C10-D11
A67-B79-C10-D11
A39-B79-C10-D11
A65-B79-C10-D11
A66-B79-C10-D11
A2-B80-C10-D11
A3-B80-C10-D11
A9-B80-C10-D11
A13-B80-C10-D11
A24-B80-C10-D11
A69-B80-C10-D11
A67-B80-C10-D11
A39-B80-C10-D11
A65-B80-C10-D11
A66-B80-C10-D11
A2-B85-C10-D11
A3-B85-C10-D11
A9-B85-C10-D11
A13-B85-C10-D11
A24-B85-C10-D11
A69-B85-C10-D11
A67-B85-C10-D11
A39-B85-C10-D11
A65-B85-C10-D11
A66-B85-C10-D11
A2-B86-C10-D11
A3-B86-C10-D11
A9-B86-C10-D11
A13-B86-C10-D11
A24-B86-C10-D11
A69-B86-C10-D11
A67-B86-C10-D11
A39-B86-C10-D11
A65-B86-C10-D11
A66-B86-C10-D11
A2-B87-C10-D11
A3-B87-C10-D11
A9-B87-C10-D11
A13-B87-C10-D11
A24-B87-C10-D11
A69-B87-C10-D11
A67-B87-C10-D11
A39-B87-C10-D11
A65-B87-C10-D11
A66-B87-C10-D11
A2-B89-C10-D11
A3-B89-C10-D11
A9-B89-C10-D11
A13-B89-C10-D11
A24-B89-C10-D11
A69-B89-C10-D11
A67-B89-C10-D11
A39-B89-C10-D11
A65-B89-C10-D11
A66-B89-C10-D11
A2-B92-C10-D11
A3-B92-C10-D11
A9-B92-C10-D11
A13-B92-C10-D11
A24-B92-C10-D11
A69-B92-C10-D11
A67-B92-C10-D11
A39-B92-C10-D11
A65-B92-C10-D11
A66-B92-C10-D11

TABLE 6-continued

A2-B4-C11-D11
A3-B4-C11-D11
A9-B4-C11-D11
A13-B4-C11-D11
A24-B4-C11-D11
A69-B4-C11-D11
A67-B4-C11-D11
A39-B4-C11-D11
A65-B4-C11-D11
A66-B4-C11-D11
A2-B5-C11-D11
A3-B5-C11-D11
A9-B5-C11-D11
A13-B5-C11-D11
A24-B5-C11-D11
A69-B5-C11-D11
A67-B5-C11-D11
A39-B5-C11-D11
A65-B5-C11-D11
A66-B5-C11-D11
A2-B6-C11-D11
A3-B6-C11-D11
A9-B6-C11-D11
A13-B6-C11-D11
A24-B6-C11-D11
A69-B6-C11-D11
A67-B6-C11-D11
A39-B6-C11-D11
A65-B6-C11-D11
A66-B6-C11-D11
A2-B32-C11-D11
A3-B32-C11-D11
A9-B32-C11-D11
A13-B32-C11-D11
A24-B32-C11-D11
A69-B32-C11-D11
A67-B32-C11-D11
A39-B32-C11-D11
A65-B32-C11-D11
A66-B32-C11-D11
A2-B39-C11-D11
A3-B39-C11-D11
A9-B39-C11-D11
A13-B39-C11-D11
A24-B39-C11-D11
A69-B39-C11-D11
A67-B39-C11-D11
A39-B39-C11-D11
A65-B39-C11-D11
A66-B39-C11-D11
A2-B45-C11-D11
A3-B45-C11-D11
A9-B45-C11-D11
A13-B45-C11-D11
A24-B45-C11-D11
A69-B45-C11-D11
A67-B45-C11-D11
A39-B45-C11-D11
A65-B45-C11-D11
A66-B45-C11-D11
A2-B53-C11-D11
A3-B53-C11-D11
A9-B53-C11-D11
A13-B53-C11-D11
A24-B53-C11-D11
A69-B53-C11-D11
A67-B53-C11-D11
A39-B53-C11-D11
A65-B53-C11-D11
A66-B53-C11-D11
A2-B79-C11-D11
A3-B79-C11-D11
A9-B79-C11-D11
A13-B79-C11-D11
A24-B79-C11-D11

-continued

A69-B79-C11-D11
A67-B79-C11-D11
A39-B79-C11-D11
A65-B79-C11-D11
A66-B79-C11-D11
A2-B80-C11-D11
A3-B80-C11-D11
A9-B80-C11-D11
A13-B80-C11-D11
A24-B80-C11-D11
A69-B80-C11-D11
A67-B80-C11-D11
A39-B80-C11-D11
A65-B80-C11-D11
A66-B80-C11-D11
A2-B85-C11-D11
A3-B85-C11-D11
A9-B85-C11-D11
A13-B85-C11-D11
A24-B85-C11-D11
A69-B85-C11-D11
A67-B85-C11-D11
A39-B85-C11-D11
A65-B85-C11-D11
A66-B85-C11-D11
A2-B86-C11-D11
A3-B86-C11-D11
A9-B86-C11-D11
A13-B86-C11-D11
A24-B86-C11-D11
A69-B86-C11-D11
A67-B86-C11-D11
A39-B86-C11-D11
A65-B86-C11-D11
A66-B86-C11-D11
A2-B87-C11-D11
A3-B87-C11-D11
A9-B87-C11-D11
A13-B87-C11-D11
A24-B87-C11-D11
A69-B87-C11-D11
A67-B87-C11-D11
A39-B87-C11-D11
A65-B87-C11-D11
A66-B87-C11-D11
A2-B89-C11-D11
A3-B89-C11-D11
A9-B89-C11-D11
A13-B89-C11-D11
A24-B89-C11-D11
A69-B89-C11-D11
A67-B89-C11-D11
A39-B89-C11-D11
A65-B89-C11-D11
A66-B89-C11-D11
A2-B92-C11-D11
A3-B92-C11-D11
A9-B92-C11-D11
A13-B92-C11-D11
A24-B92-C11-D11
A69-B92-C11-D11
A67-B92-C11-D11
A39-B92-C11-D11
A65-B92-C11-D11
A66-B92-C11-D11
A2-B4-C12-D11
A3-B4-C12-D11
A9-B4-C12-D11
A13-B4-C12-D11
A24-B4-C12-D11
A69-B4-C12-D11
A67-B4-C12-D11
A39-B4-C12-D11
A65-B4-C12-D11
A66-B4-C12-D11
A2-B5-C12-D11
A3-B5-C12-D11
A9-B5-C12-D11
A13-B5-C12-D11
A24-B5-C12-D11

-continued
A69-B5-C12-D11
A67-B5-C12-D11
A39-B5-C12-D11
A65-B5-C12-D11
A66-B5-C12-D11
A2-B6-C12-D11
A3-B6-C12-D11
A9-B6-C12-D11
A13-B6-C12-D11
A24-B6-C12-D11
A69-B6-C12-D11
A67-B6-C12-D11
A39-B6-C12-D11
A65-B6-C12-D11
A66-B6-C12-D11
A2-B32-C12-D11
A3-B32-C12-D11
A9-B32-C12-D11
A13-B32-C12-D11
A24-B32-C12-D11
A69-B32-C12-D11
A67-B32-C12-D11
A39-B32-C12-D11
A65-B32-C12-D11
A66-B32-C12-D11
A2-B39-C12-D11
A3-B39-C12-D11
A9-B39-C12-D11
A13-B39-C12-D11
A24-B39-C12-D11
A69-B39-C12-D11
A67-B39-C12-D11
A39-B39-C12-D11
A65-B39-C12-D11
A66-B39-C12-D11
A2-B45-C12-D11
A3-B45-C12-D11
A9-B45-C12-D11
A13-B45-C12-D11
A24-B45-C12-D11
A69-B45-C12-D11
A67-B45-C12-D11
A39-B45-C12-D11
A65-B45-C12-D11
A66-B45-C12-D11
A2-B53-C12-D11
A3-B53-C12-D11
A9-B53-C12-D11
A13-B53-C12-D11
A24-B53-C12-D11
A69-B53-C12-D11
A67-B53-C12-D11
A39-B53-C12-D11
A65-B53-C12-D11
A66-B53-C12-D11
A2-B79-C12-D11
A3-B79-C12-D11
A9-B79-C12-D11
A13-B79-C12-D11
A24-B79-C12-D11
A69-B79-C12-D11
A67-B79-C12-D11
A39-B79-C12-D11
A65-B79-C12-D11
A66-B79-C12-D11
A2-B80-C12-D11
A3-B80-C12-D11
A9-B80-C12-D11
A13-B80-C12-D11
A24-B80-C12-D11
A69-B80-C12-D11
A67-B80-C12-D11
A39-B80-C12-D11
A65-B80-C12-D11
A66-B80-C12-D11
A2-B85-C12-D11
A3-B85-C12-D11
A9-B85-C12-D11
A13-B85-C12-D11
A24-B85-C12-D11

-continued
A69-B85-C12-D11
A67-B85-C12-D11
A39-B85-C12-D11
A65-B85-C12-D11
A66-B85-C12-D11
A2-B86-C12-D11
A3-B86-C12-D11
A9-B86-C12-D11
A13-B86-C12-D11
A24-B86-C12-D11
A69-B86-C12-D11
A67-B86-C12-D11
A39-B86-C12-D11
A65-B86-C12-D11
A66-B86-C12-D11
A2-B87-C12-D11
A3-B87-C12-D11
A9-B87-C12-D11
A13-B87-C12-D11
A24-B87-C12-D11
A69-B87-C12-D11
A67-B87-C12-D11
A39-B87-C12-D11
A65-B87-C12-D11
A66-B87-C12-D11
A2-B89-C12-D11
A3-B89-C12-D11
A9-B89-C12-D11
A13-B89-C12-D11
A24-B89-C12-D11
A69-B89-C12-D11
A67-B89-C12-D11
A39-B89-C12-D11
A65-B89-C12-D11
A66-B89-C12-D11
A2-B92-C12-D11
A3-B92-C12-D11
A9-B92-C12-D11
A13-B92-C12-D11
A24-B92-C12-D11
A69-B92-C12-D11
A67-B92-C12-D11
A39-B92-C12-D11
A65-B92-C12-D11
A66-B92-C12-D11
A2-B4-C13-D11
A3-B4-C13-D11
A9-B4-C13-D11
A13-B4-C13-D11
A24-B4-C13-D11
A69-B4-C13-D11
A67-B4-C13-D11
A39-B4-C13-D11
A65-B4-C13-D11
A66-B4-C13-D11
A2-B5-C13-D11
A3-B5-C13-D11
A9-B5-C13-D11
A13-B5-C13-D11
A24-B5-C13-D11
A69-B5-C13-D11
A67-B5-C13-D11
A39-B5-C13-D11
A65-B5-C13-D11
A66-B5-C13-D11
A2-B6-C13-D11
A3-B6-C13-D11
A9-B6-C13-D11
A13-B6-C13-D11
A24-B6-C13-D11
A69-B6-C13-D11
A67-B6-C13-D11
A39-B6-C13-D11
A65-B6-C13-D11
A66-B6-C13-D11
A2-B32-C13-D11
A3-B32-C13-D11
A9-B32-C13-D11
A13-B32-C13-D11
A24-B32-C13-D11

-continued
A69-B32-C13-D11
A67-B32-C13-D11
A39-B32-C13-D11
A65-B32-C13-D11
A66-B32-C13-D11
A2-B39-C13-D11
A3-B39-C13-D11
A9-B39-C13-D11
A13-B39-C13-D11
A24-B39-C13-D11
A69-B39-C13-D11
A67-B39-C13-D11
A39-B39-C13-D11
A65-B39-C13-D11
A66-B39-C13-D11
A2-B45-C13-D11
A3-B45-C13-D11
A9-B45-C13-D11
A13-B45-C13-D11
A24-B45-C13-D11
A69-B45-C13-D11
A67-B45-C13-D11
A39-B45-C13-D11
A65-B45-C13-D11
A66-B45-C13-D11
A2-B53-C13-D11
A3-B53-C13-D11
A9-B53-C13-D11
A13-B53-C13-D11
A24-B53-C13-D11
A69-B53-C13-D11
A67-B53-C13-D11
A39-B53-C13-D11
A65-B53-C13-D11
A66-B53-C13-D11
A2-B79-C13-D11
A3-B79-C13-D11
A9-B79-C13-D11
A13-B79-C13-D11
A24-B79-C13-D11
A69-B79-C13-D11
A67-B79-C13-D11
A39-B79-C13-D11
A65-B79-C13-D11
A66-B79-C13-D11
A2-B80-C13-D11
A3-B80-C13-D11
A9-B80-C13-D11
A13-B80-C13-D11
A24-B80-C13-D11
A69-B80-C13-D11
A67-B80-C13-D11
A39-B80-C13-D11
A65-B80-C13-D11
A66-B80-C13-D11
A2-B85-C13-D11
A3-B85-C13-D11
A9-B85-C13-D11
A13-B85-C13-D11
A24-B85-C13-D11
A69-B85-C13-D11
A67-B85-C13-D11
A39-B85-C13-D11
A65-B85-C13-D11
A66-B85-C13-D11
A2-B86-C13-D11
A3-B86-C13-D11
A9-B86-C13-D11
A13-B86-C13-D11
A24-B86-C13-D11
A69-B86-C13-D11
A67-B86-C13-D11
A39-B86-C13-D11
A65-B86-C13-D11
A66-B86-C13-D11
A2-B87-C13-D11
A3-B87-C13-D11
A9-B87-C13-D11
A13-B87-C13-D11
A24-B87-C13-D11

-continued
A69-B87-C13-D11
A67-B87-C13-D11
A39-B87-C13-D11
A65-B87-C13-D11
A66-B87-C13-D11
A2-B89-C13-D11
A3-B89-C13-D11
A9-B89-C13-D11
A13-B89-C13-D11
A24-B89-C13-D11
A69-B89-C13-D11
A67-B89-C13-D11
A39-B89-C13-D11
A65-B89-C13-D11
A66-B89-C13-D11
A2-B92-C13-D11
A3-B92-C13-D11
A9-B92-C13-D11
A13-B92-C13-D11
A24-B92-C13-D11
A69-B92-C13-D11
A67-B92-C13-D11
A39-B92-C13-D11
A65-B92-C13-D11
A66-B92-C13-D11
A2-B4-C1-D12
A3-B4-C1-D12
A9-B4-C1-D12
A13-B4-C1-D12
A24-B4-C1-D12
A69-B4-C1-D12
A67-B4-C1-D12
A39-B4-C1-D12
A65-B4-C1-D12
A66-B4-C1-D12
A2-B5-C1-D12
A3-B5-C1-D12
A9-B5-C1-D12
A13-B5-C1-D12
A24-B5-C1-D12
A69-B5-C1-D12
A67-B5-C1-D12
A39-B5-C1-D12
A65-B5-C1-D12
A66-B5-C1-D12
A2-B6-C1-D12
A3-B6-C1-D12
A9-B6-C1-D12
A13-B6-C1-D12
A24-B6-C1-D12
A69-B6-C1-D12
A67-B6-C1-D12
A39-B6-C1-D12
A65-B6-C1-D12
A66-B6-C1-D12
A2-B32-C1-D12
A3-B32-C1-D12
A9-B32-C1-D12
A13-B32-C1-D12
A24-B32-C1-D12
A69-B32-C1-D12
A67-B32-C1-D12
A39-B32-C1-D12
A65-B32-C1-D12
A66-B32-C1-D12
A2-B39-C1-D12
A3-B39-C1-D12
A9-B39-C1-D12
A13-B39-C1-D12
A24-B39-C1-D12
A69-B39-C1-D12
A67-B39-C1-D12
A39-B39-C1-D12
A65-B39-C1-D12
A66-B39-C1-D12
A2-B45-C1-D12
A3-B45-C1-D12
A9-B45-C1-D12
A13-B45-C1-D12
A24-B45-C1-D12

-continued
A69-B45-C1-D12
A67-B45-C1-D12
A39-B45-C1-D12
A65-B45-C1-D12
A66-B45-C1-D12
A2-B53-C1-D12
A3-B53-C1-D12
A9-B53-C1-D12
A13-B53-C1-D12
A24-B53-C1-D12
A69-B53-C1-D12
A67-B53-C1-D12
A39-B53-C1-D12
A65-B53-C1-D12
A66-B53-C1-D12
A2-B79-C1-D12
A3-B79-C1-D12
A9-B79-C1-D12
A13-B79-C1-D12
A24-B79-C1-D12
A69-B79-C1-D12
A67-B79-C1-D12
A39-B79-C1-D12
A65-B79-C1-D12
A66-B79-C1-D12
A2-B80-C1-D12
A3-B80-C1-D12
A9-B80-C1-D12
A13-B80-C1-D12
A24-B80-C1-D12
A69-B80-C1-D12
A67-B80-C1-D12
A39-B80-C1-D12
A65-B80-C1-D12
A66-B80-C1-D12
A2-B85-C1-D12
A3-B85-C1-D12
A9-B85-C1-D12
A13-B85-C1-D12
A24-B85-C1-D12
A69-B85-C1-D12
A67-B85-C1-D12
A39-B85-C1-D12
A65-B85-C1-D12
A66-B85-C1-D12
A2-B86-C1-D12
A3-B86-C1-D12
A9-B86-C1-D12
A13-B86-C1-D12
A24-B86-C1-D12
A69-B86-C1-D12
A67-B86-C1-D12
A39-B86-C1-D12
A65-B86-C1-D12
A66-B86-C1-D12
A2-B87-C1-D12
A3-B87-C1-D12
A9-B87-C1-D12
A13-B87-C1-D12
A24-B87-C1-D12
A69-B87-C1-D12
A67-B87-C1-D12
A39-B87-C1-D12
A65-B87-C1-D12
A66-B87-C1-D12
A2-B89-C1-D12
A3-B89-C1-D12
A9-B89-C1-D12
A13-B89-C1-D12
A24-B89-C1-D12
A69-B89-C1-D12
A67-B89-C1-D12
A39-B89-C1-D12
A65-B89-C1-D12
A66-B89-C1-D12
A2-B92-C1-D12
A3-B92-C1-D12
A9-B92-C1-D12
A13-B92-C1-D12
A24-B92-C1-D12

-continued
A69-B92-C1-D12
A67-B92-C1-D12
A39-B92-C1-D12
A65-B92-C1-D12
A66-B92-C1-D12
A2-B4-C2-D12
A3-B4-C2-D12
A9-B4-C2-D12
A13-B4-C2-D12
A24-B4-C2-D12
A69-B4-C2-D12
A67-B4-C2-D12
A39-B4-C2-D12
A65-B4-C2-D12
A66-B4-C2-D12
A2-B5-C2-D12
A3-B5-C2-D12
A9-B5-C2-D12
A13-B5-C2-D12
A24-B5-C2-D12
A69-B5-C2-D12
A67-B5-C2-D12
A39-B5-C2-D12
A65-B5-C2-D12
A66-B5-C2-D12
A2-B6-C2-D12
A3-B6-C2-D12
A9-B6-C2-D12
A13-B6-C2-D12
A24-B6-C2-D12
A69-B6-C2-D12
A67-B6-C2-D12
A39-B6-C2-D12
A65-B6-C2-D12
A66-B6-C2-D12
A2-B32-C2-D12
A3-B32-C2-D12
A9-B32-C2-D12
A13-B32-C2-D12
A24-B32-C2-D12
A69-B32-C2-D12
A67-B32-C2-D12
A39-B32-C2-D12
A65-B32-C2-D12
A66-B32-C2-D12
A2-B39-C2-D12
A3-B39-C2-D12
A9-B39-C2-D12
A13-B39-C2-D12
A24-B39-C2-D12
A69-B39-C2-D12
A67-B39-C2-D12
A39-B39-C2-D12
A65-B39-C2-D12
A66-B39-C2-D12
A2-B45-C2-D12
A3-B45-C2-D12
A9-B45-C2-D12
A13-B45-C2-D12
A24-B45-C2-D12
A69-B45-C2-D12
A67-B45-C2-D12
A39-B45-C2-D12
A65-B45-C2-D12
A66-B45-C2-D12
A2-B53-C2-D12
A3-B53-C2-D12
A9-B53-C2-D12
A13-B53-C2-D12
A24-B53-C2-D12
A69-B53-C2-D12
A67-B53-C2-D12
A39-B53-C2-D12
A65-B53-C2-D12
A66-B53-C2-D12
A2-B79-C2-D12
A3-B79-C2-D12
A9-B79-C2-D12
A13-B79-C2-D12
A24-B79-C2-D12

-continued

A69-B79-C2-D12
A67-B79-C2-D12
A39-B79-C2-D12
A65-B79-C2-D12
A66-B79-C2-D12
A2-B80-C2-D12
A3-B80-C2-D12
A9-B80-C2-D12
A13-B80-C2-D12
A24-B80-C2-D12
A69-B80-C2-D12
A67-B80-C2-D12
A39-B80-C2-D12
A65-B80-C2-D12
A66-B80-C2-D12
A2-B85-C2-D12
A3-B85-C2-D12
A9-B85-C2-D12
A13-B85-C2-D12
A24-B85-C2-D12
A69-B85-C2-D12
A67-B85-C2-D12
A39-B85-C2-D12
A65-B85-C2-D12
A66-B85-C2-D12
A2-B86-C2-D12
A3-B86-C2-D12
A9-B86-C2-D12
A13-B86-C2-D12
A24-B86-C2-D12
A69-B86-C2-D12
A67-B86-C2-D12
A39-B86-C2-D12
A65-B86-C2-D12
A66-B86-C2-D12
A2-B87-C2-D12
A3-B87-C2-D12
A9-B87-C2-D12
A13-B87-C2-D12
A24-B87-C2-D12
A69-B87-C2-D12
A67-B87-C2-D12
A39-B87-C2-D12
A65-B87-C2-D12
A66-B87-C2-D12
A2-B89-C2-D12
A3-B89-C2-D12
A9-B89-C2-D12
A13-B89-C2-D12
A24-B89-C2-D12
A69-B89-C2-D12
A67-B89-C2-D12
A39-B89-C2-D12
A65-B89-C2-D12
A66-B89-C2-D12
A2-B92-C2-D12
A3-B92-C2-D12
A9-B92-C2-D12
A13-B92-C2-D12
A24-B92-C2-D12
A69-B92-C2-D12
A67-B92-C2-D12
A39-B92-C2-D12
A65-B92-C2-D12
A66-B92-C2-D12
A2-B4-C3-D12
A3-B4-C3-D12
A9-B4-C3-D12
A13-B4-C3-D12
A24-B4-C3-D12
A69-B4-C3-D12
A67-B4-C3-D12
A39-B4-C3-D12
A65-B4-C3-D12
A66-B4-C3-D12
A2-B5-C3-D12
A3-B5-C3-D12
A9-B5-C3-D12
A13-B5-C3-D12
A24-B5-C3-D12

-continued

A69-B5-C3-D12
A67-B5-C3-D12
A39-B5-C3-D12
A65-B5-C3-D12
A66-B5-C3-D12
A2-B6-C3-D12
A3-B6-C3-D12
A9-B6-C3-D12
A13-B6-C3-D12
A24-B6-C3-D12
A69-B6-C3-D12
A67-B6-C3-D12
A39-B6-C3-D12
A65-B6-C3-D12
A66-B6-C3-D12
A2-B32-C3-D12
A3-B32-C3-D12
A9-B32-C3-D12
A13-B32-C3-D12
A24-B32-C3-D12
A69-B32-C3-D12
A67-B32-C3-D12
A39-B32-C3-D12
A65-B32-C3-D12
A66-B32-C3-D12
A2-B39-C3-D12
A3-B39-C3-D12
A9-B39-C3-D12
A13-B39-C3-D12
A24-B39-C3-D12
A69-B39-C3-D12
A67-B39-C3-D12
A39-B39-C3-D12
A65-B39-C3-D12
A66-B39-C3-D12
A2-B45-C3-D12
A3-B45-C3-D12
A9-B45-C3-D12
A13-B45-C3-D12
A24-B45-C3-D12
A69-B45-C3-D12
A67-B45-C3-D12
A39-B45-C3-D12
A65-B45-C3-D12
A66-B45-C3-D12
A2-B53-C3-D12
A3-B53-C3-D12
A9-B53-C3-D12
A13-B53-C3-D12
A24-B53-C3-D12
A69-B53-C3-D12
A67-B53-C3-D12
A39-B53-C3-D12
A65-B53-C3-D12
A66-B53-C3-D12
A2-B79-C3-D12
A3-B79-C3-D12
A9-B79-C3-D12
A13-B79-C3-D12
A24-B79-C3-D12
A69-B79-C3-D12
A67-B79-C3-D12
A39-B79-C3-D12
A65-B79-C3-D12
A66-B79-C3-D12
A2-B80-C3-D12
A3-B80-C3-D12
A9-B80-C3-D12
A13-B80-C3-D12
A24-B80-C3-D12
A69-B80-C3-D12
A67-B80-C3-D12
A39-B80-C3-D12
A65-B80-C3-D12
A66-B80-C3-D12
A2-B85-C3-D12
A3-B85-C3-D12
A9-B85-C3-D12
A13-B85-C3-D12
A24-B85-C3-D12

-continued
A69-B85-C3-D12
A67-B85-C3-D12
A39-B85-C3-D12
A65-B85-C3-D12
A66-B85-C3-D12
A2-B86-C3-D12
A3-B86-C3-D12
A9-B86-C3-D12
A13-B86-C3-D12
A24-B86-C3-D12
A69-B86-C3-D12
A67-B86-C3-D12
A39-B86-C3-D12
A65-B86-C3-D12
A66-B86-C3-D12
A2-B87-C3-D12
A3-B87-C3-D12
A9-B87-C3-D12
A13-B87-C3-D12
A24-B87-C3-D12
A69-B87-C3-D12
A67-B87-C3-D12
A39-B87-C3-D12
A65-B87-C3-D12
A66-B87-C3-D12
A2-B89-C3-D12
A3-B89-C3-D12
A9-B89-C3-D12
A13-B89-C3-D12
A24-B89-C3-D12
A69-B89-C3-D12
A67-B89-C3-D12
A39-B89-C3-D12
A65-B89-C3-D12
A66-B89-C3-D12
A2-B92-C3-D12
A3-B92-C3-D12
A9-B92-C3-D12
A13-B92-C3-D12
A24-B92-C3-D12
A69-B92-C3-D12
A67-B92-C3-D12
A39-B92-C3-D12
A65-B92-C3-D12
A66-B92-C3-D12
A2-B4-C4-D12
A3-B4-C4-D12
A9-B4-C4-D12
A13-B4-C4-D12
A24-B4-C4-D12
A69-B4-C4-D12
A67-B4-C4-D12
A39-B4-C4-D12
A65-B4-C4-D12
A66-B4-C4-D12
A2-B5-C4-D12
A3-B5-C4-D12
A9-B5-C4-D12
A13-B5-C4-D12
A24-B5-C4-D12
A69-B5-C4-D12
A67-B5-C4-D12
A39-B5-C4-D12
A65-B5-C4-D12
A66-B5-C4-D12
A2-B6-C4-D12
A3-B6-C4-D12
A9-B6-C4-D12
A13-B6-C4-D12
A24-B6-C4-D12
A69-B6-C4-D12
A67-B6-C4-D12
A39-B6-C4-D12
A65-B6-C4-D12
A66-B6-C4-D12
A2-B32-C4-D12
A3-B32-C4-D12
A9-B32-C4-D12
A13-B32-C4-D12
A24-B32-C4-D12

-continued
A69-B32-C4-D12
A67-B32-C4-D12
A39-B32-C4-D12
A65-B32-C4-D12
A66-B32-C4-D12
A2-B39-C4-D12
A3-B39-C4-D12
A9-B39-C4-D12
A13-B39-C4-D12
A24-B39-C4-D12
A69-B39-C4-D12
A67-B39-C4-D12
A39-B39-C4-D12
A65-B39-C4-D12
A66-B39-C4-D12
A2-B45-C4-D12
A3-B45-C4-D12
A9-B45-C4-D12
A13-B45-C4-D12
A24-B45-C4-D12
A69-B45-C4-D12
A67-B45-C4-D12
A39-B45-C4-D12
A65-B45-C4-D12
A66-B45-C4-D12
A2-B53-C4-D12
A3-B53-C4-D12
A9-B53-C4-D12
A13-B53-C4-D12
A24-B53-C4-D12
A69-B53-C4-D12
A67-B53-C4-D12
A39-B53-C4-D12
A65-B53-C4-D12
A66-B53-C4-D12
A2-B79-C4-D12
A3-B79-C4-D12
A9-B79-C4-D12
A13-B79-C4-D12
A24-B79-C4-D12
A69-B79-C4-D12
A67-B79-C4-D12
A39-B79-C4-D12
A65-B79-C4-D12
A66-B79-C4-D12
A2-B80-C4-D12
A3-B80-C4-D12
A9-B80-C4-D12
A13-B80-C4-D12
A24-B80-C4-D12
A69-B80-C4-D12
A67-B80-C4-D12
A39-B80-C4-D12
A65-B80-C4-D12
A66-B80-C4-D12
A2-B85-C4-D12
A3-B85-C4-D12
A9-B85-C4-D12
A13-B85-C4-D12
A24-B85-C4-D12
A69-B85-C4-D12
A67-B85-C4-D12
A39-B85-C4-D12
A65-B85-C4-D12
A66-B85-C4-D12
A2-B86-C4-D12
A3-B86-C4-D12
A9-B86-C4-D12
A13-B86-C4-D12
A24-B86-C4-D12
A69-B86-C4-D12
A67-B86-C4-D12
A39-B86-C4-D12
A65-B86-C4-D12
A66-B86-C4-D12
A2-B87-C4-D12
A3-B87-C4-D12
A9-B87-C4-D12
A13-B87-C4-D12
A24-B87-C4-D12

-continued

A69-B87-C4-D12
A67-B87-C4-D12
A39-B87-C4-D12
A65-B87-C4-D12
A66-B87-C4-D12
A2-B89-C4-D12
A3-B89-C4-D12
A9-B89-C4-D12
A13-B89-C4-D12
A24-B89-C4-D12
A69-B89-C4-D12
A67-B89-C4-D12
A39-B89-C4-D12
A65-B89-C4-D12
A66-B89-C4-D12
A2-B92-C4-D12
A3-B92-C4-D12
A9-B92-C4-D12
A13-B92-C4-D12
A24-B92-C4-D12
A69-B92-C4-D12
A67-B92-C4-D12
A39-B92-C4-D12
A65-B92-C4-D12
A66-B92-C4-D12
A2-B4-C5-D12
A3-B4-C5-D12
A9-B4-C5-D12
A13-B4-C5-D12
A24-B4-C5-D12
A69-B4-C5-D12
A67-B4-C5-D12
A39-B4-C5-D12
A65-B4-C5-D12
A66-B4-C5-D12
A2-B5-C5-D12
A3-B5-C5-D12
A9-B5-C5-D12
A13-B5-C5-D12
A24-B5-C5-D12
A69-B5-C5-D12
A67-B5-C5-D12
A39-B5-C5-D12
A65-B5-C5-D12
A66-B5-C5-D12
A2-B6-C5-D12
A3-B6-C5-D12
A9-B6-C5-D12
A13-B6-C5-D12
A24-B6-C5-D12
A69-B6-C5-D12
A67-B6-C5-D12
A39-B6-C5-D12
A65-B6-C5-D12
A66-B6-C5-D12
A2-B32-C5-D12
A3-B32-C5-D12
A9-B32-C5-D12
A13-B32-C5-D12
A24-B32-C5-D12
A69-B32-C5-D12
A67-B32-C5-D12
A39-B32-C5-D12
A65-B32-C5-D12
A66-B32-C5-D12
A2-B39-C5-D12
A3-B39-C5-D12
A9-B39-C5-D12
A13-B39-C5-D12
A24-B39-C5-D12
A69-B39-C5-D12
A67-B39-C5-D12
A39-B39-C5-D12
A65-B39-C5-D12
A66-B39-C5-D12
A2-B45-C5-D12
A3-B45-C5-D12
A9-B45-C5-D12
A13-B45-C5-D12
A24-B45-C5-D12

-continued

A69-B45-C5-D12
A67-B45-C5-D12
A39-B45-C5-D12
A65-B45-C5-D12
A66-B45-C5-D12
A2-B53-C5-D12
A3-B53-C5-D12
A9-B53-CS-D12
A13-B53-C5-D12
A24-B53-C5-D12
A69-B53-C5-D12
A67-B53-C5-D12
A39-B53-C5-D12
A65-B53-C5-D12
A66-B53-C5-D12
A2-B79-C5-D12
A3-B79-C5-D12
A9-B79-C5-D12
A13-B79-C5-D12
A24-B79-C5-D12
A69-B79-C5-D12
A67-B79-C5-D12
A39-B79-C5-D12
A65-B79-C5-D12
A66-B79-C5-D12
A2-B80-C5-D12
A3-B80-C5-D12
A9-B80-C5-D12
A13-B80-C5-D12
A24-B80-C5-D12
A69-B80-C5-D12
A67-B80-C5-D12
A39-B80-C5-D12
A65-B80-C5-D12
A66-B80-C5-D12
A2-B85-C5-D12
A3-B85-C5-D12
A9-B85-C5-D12
A13-B85-C5-D12
A24-B85-C5-D12
A69-B85-C5-D12
A67-B85-C5-D12
A39-B85-C5-D12
A65-B85-C5-D12
A66-B85-C5-D12
A2-B86-C5-D12
A3-B86-C5-D12
A9-B86-C5-D12
A13-B86-C5-D12
A24-B86-C5-D12
A69-B86-C5-D12
A67-B86-C5-D12
A39-B86-C5-D12
A65-B86-C5-D12
A66-B86-C5-D12
A2-B87-C5-D12
A3-B87-C5-D12
A9-B87-C5-D12
A13-B87-C5-D12
A24-B87-C5-D12
A69-B87-C5-D12
A67-B87-C5-D12
A39-B87-C5-D12
A65-B87-C5-D12
A66-B87-C5-D12
A2-B89-C5-D12
A3-B89-C5-D12
A9-B89-C5-D12
A13-B89-C5-D12
A24-B89-C5-D12
A69-B89-C5-D12
A67-B89-C5-D12
A39-B89-C5-D12
A65-B89-C5-D12
A66-B89-C5-D12
A2-B92-C5-D12
A3-B92-C5-D12
A9-B92-C5-D12
A13-B92-C5-D12
A24-B92-C5-D12

-continued
A69-B92-C5-D12
A67-B92-C5-D12
A39-B92-C5-D12
A65-B92-C5-D12
A66-B92-C5-D12
A2-B4-C6-D12
A3-B4-C6-D12
A9-B4-C6-D12
A13-B4-C6-D12
A24-B4-C6-D12
A69-B4-C6-D12
A67-B4-C6-D12
A39-B4-C6-D12
A65-B4-C6-D12
A66-B4-C6-D12
A2-B5-C6-D12
A3-B5-C6-D12
A9-B5-C6-D12
A13-B5-C6-D12
A24-B5-C6-D12
A69-B5-C6-D12
A67-B5-C6-D12
A39-B5-C6-D12
A65-B5-C6-D12
A66-B5-C6-D12
A2-B6-C6-D12
A3-B6-C6-D12
A9-B6-C6-D12
A13-B6-C6-D12
A24-B6-C6-D12
A69-B6-C6-D12
A67-B6-C6-D12
A39-B6-C6-D12
A65-B6-C6-D12
A66-B6-C6-D12
A2-B32-C6-D12
A3-B32-C6-D12
A9-B32-C6-D12
A13-B32-C6-D12
A24-B32-C6-D12
A69-B32-C6-D12
A67-B32-C6-D12
A39-B32-C6-D12
A65-B32-C6-D12
A66-B32-C6-D12
A2-B39-C6-D12
A3-B39-C6-D12
A9-B39-C6-D12
A13-B39-C6-D12
A24-B39-C6-D12
A69-B39-C6-D12
A67-B39-C6-D12
A39-B39-C6-D12
A65-B39-C6-D12
A66-B39-C6-D12
A2-B45-C6-D12
A3-B45-C6-D12
A9-B45-C6-D12
A13-B45-C6-D12
A24-B45-C6-D12
A69-B45-C6-D12
A67-B45-C6-D12
A39-B45-C6-D12
A65-B45-C6-D12
A66-B45-C6-D12
A2-B53-C6-D12
A3-B53-C6-D12
A9-B53-C6-D12
A13-B53-C6-D12
A24-B53-C6-D12
A69-B53-C6-D12
A67-B53-C6-D12
A39-B53-C6-D12
A65-B53-C6-D12
A66-B53-C6-D12
A2-B79-C6-D12
A3-B79-C6-D12
A9-B79-C6-D12
A13-B79-C6-D12
A24-B79-C6-D12

-continued
A69-B79-C6-D12
A67-B79-C6-D12
A39-B79-C6-D12
A65-B79-C6-D12
A66-B79-C6-D12
A2-B80-C6-D12
A3-B80-C6-D12
A9-B80-C6-D12
A13-B80-C6-D12
A24-B80-C6-D12
A69-B80-C6-D12
A67-B80-C6-D12
A39-B80-C6-D12
A65-B80-C6-D12
A66-B80-C6-D12
A2-B85-C6-D12
A3-B85-C6-D12
A9-B85-C6-D12
A13-B85-C6-D12
A24-B85-C6-D12
A69-B85-C6-D12
A67-B85-C6-D12
A39-B85-C6-D12
A65-B85-C6-D12
A66-B85-C6-D12
A2-B86-C6-D12
A3-B86-C6-D12
A9-B86-C6-D12
A13-B86-C6-D12
A24-B86-C6-D12
A69-B86-C6-D12
A67-B86-C6-D12
A39-B86-C6-D12
A65-B86-C6-D12
A66-B86-C6-D12
A2-B87-C6-D12
A3-B87-C6-D12
A9-B87-C6-D12
A13-B87-C6-D12
A24-B87-C6-D12
A69-B87-C6-D12
A67-B87-C6-D12
A39-B87-C6-D12
A65-B87-C6-D12
A66-B87-C6-D12
A2-B89-C6-D12
A3-B89-C6-D12
A9-B89-C6-D12
A13-B89-C6-D12
A24-B89-C6-D12
A69-B89-C6-D12
A67-B89-C6-D12
A39-B89-C6-D12
A65-B89-C6-D12
A66-B89-C6-D12
A2-B92-C6-D12
A3-B92-C6-D12
A9-B92-C6-D12
A13-B92-C6-D12
A24-B92-C6-D12
A69-B92-C6-D12
A67-B92-C6-D12
A39-B92-C6-D12
A65-B92-C6-D12
A66-B92-C6-D12
A2-B4-C7-D12
A3-B4-C7-D12
A9-B4-C7-D12
A13-B4-C7-D12
A24-B4-C7-D12
A69-B4-C7-D12
A67-B4-C7-D12
A39-B4-C7-D12
A65-B4-C7-D12
A66-B4-C7-D12
A2-B5-C7-D12
A3-B5-C7-D12
A9-B5-C7-D12
A13-B5-C7-D12
A24-B5-C7-D12

-continued

A69-B5-C7-D12
A67-B5-C7-D12
A39-B5-C7-D12
A65-B5-C7-D12
A66-B5-C7-D12
A2-B6-C7-D12
A3-B6-C7-D12
A9-B6-C7-D12
A13-B6-C7-D12
A24-B6-C7-D12
A69-B6-C7-D12
A67-B6-C7-D12
A39-B6-C7-D12
A65-B6-C7-D12
A66-B6-C7-D12
A2-B32-C7-D12
A3-B32-C7-D12
A9-B32-C7-D12
A13-B32-C7-D12
A24-B32-C7-D12
A69-B32-C7-D12
A67-B32-C7-D12
A39-B32-C7-D12
A65-B32-C7-D12
A66-B32-C7-D12
A2-B39-C7-D12
A3-B39-C7-D12
A9-B39-C7-D12
A13-B39-C7-D12
A24-B39-C7-D12
A69-B39-C7-D12
A67-B39-C7-D12
A39-B39-C7-D12
A65-B39-C7-D12
A66-B39-C7-D12
A2-B45-C7-D12
A3-B45-C7-D12
A9-B45-C7-D12
A13-B45-C7-D12
A24-B45-C7-D12
A69-B45-C7-D12
A67-B45-C7-D12
A39-B45-C7-D12
A65-B45-C7-D12
A66-B45-C7-D12
A2-B53-C7-D12
A3-B53-C7-D12
A9-B53-C7-D12
A13-B53-C7-D12
A24-B53-C7-D12
A69-B53-C7-D12
A67-B53-C7-D12
A39-B53-C7-D12
A65-B53-C7-D12
A66-B53-C7-D12
A2-B79-C7-D12
A3-B79-C7-D12
A9-B79-C7-D12
A13-B79-C7-D12
A24-B79-C7-D12
A69-B79-C7-D12
A67-B79-C7-D12
A39-B79-C7-D12
A65-B79-C7-D12
A66-B79-C7-D12
A2-B80-C7-D12
A3-B80-C7-D12
A9-B80-C7-D12
A13-B80-C7-D12
A24-B80-C7-D12
A69-B80-C7-D12
A67-B80-C7-D12
A39-B80-C7-D12
A65-B80-C7-D12
A66-B80-C7-D12
A2-B85-C7-D12
A3-B85-C7-D12
A9-B85-C7-D12
A13-B85-C7-D12
A24-B85-C7-D12

-continued

A69-B85-C7-D12
A67-B85-C7-D12
A39-B85-C7-D12
A65-B85-C7-D12
A66-B85-C7-D12
A2-B86-C7-D12
A3-B86-C7-D12
A9-B86-C7-D12
A13-B86-C7-D12
A24-B86-C7-D12
A69-B86-C7-D12
A67-B86-C7-D12
A39-B86-C7-D12
A65-B86-C7-D12
A66-B86-C7-D12
A2-B87-C7-D12
A3-B87-C7-D12
A9-B87-C7-D12
A13-B87-C7-D12
A24-B87-C7-D12
A69-B87-C7-D12
A67-B87-C7-D12
A39-B87-C7-D12
A65-B87-C7-D12
A66-B87-C7-D12
A2-B89-C7-D12
A3-B89-C7-D12
A9-B89-C7-D12
A13-B89-C7-D12
A24-B89-C7-D12
A69-B89-C7-D12
A67-B89-C7-D12
A39-B89-C7-D12
A65-B89-C7-D12
A66-B89-C7-D12
A2-B92-C7-D12
A3-B92-C7-D12
A9-B92-C7-D12
A13-B92-C7-D12
A24-B92-C7-D12
A69-B92-C7-D12
A67-B92-C7-D12
A39-B92-C7-D12
A65-B92-C7-D12
A66-B92-C7-D12
A2-B4-C8-D12
A3-B4-C8-D12
A9-B4-C8-D12
A13-B4-C8-D12
A24-B4-C8-D12
A69-B4-CS-D12
A67-B4-C8-D12
A39-B4-C8-D12
A65-B4-C8-D12
A66-B4-C8-D12
A2-B5-C8-D12
A3-B5-C8-D12
A9-B5-C8-D12
A13-B5-C8-D12
A24-B5-C8-D12
A69-B5-C8-D12
A67-B5-C8-D12
A39-B5-C8-D12
A65-B5-C8-D12
A66-B5-C8-D12
A2-B6-C8-D12
A3-B6-C8-D12
A9-B6-C8-D12
A13-B6-C8-D12
A24-B6-C8-D12
A69-B6-C8-D12
A67-B6-C8-D12
A39-B6-C8-D12
A65-B6-C8-D12
A66-B6-C8-D12
A2-B32-C8-D12
A3-B32-C8-D12
A9-B32-C8-D12
A13-B32-C8-D12
A24-B32-C8-D12

-continued
A69-B32-C8-D12
A67-B32-C8-D12
A39-B32-C8-D12
A65-B32-C8-D12
A66-B32-C8-D12
A2-B39-C8-D12
A3-B39-C8-D12
A9-B39-C8-D12
A13-B39-C8-D12
A24-B39-C8-D12
A69-B39-C8-D12
A67-B39-C8-D12
A39-B39-C8-D12
A65-B39-C8-D12
A66-B39-C8-D12
A2-B45-C8-D12
A3-B45-C8-D12
A9-B45-C8-D12
A13-B45-C8-D12
A24-B45-C8-D12
A69-B45-C8-D12
A67-B45-C8-D12
A39-B45-C8-D12
A65-B45-C8-D12
A66-B45-C8-D12
A2-B53-C8-D12
A3-B53-C8-D12
A9-B53-C8-D12
A13-B53-C8-D12
A24-B53-C8-D12
A69-B53-C8-D12
A67-B53-C8-D12
A39-B53-C8-D12
A65-B53-C8-D12
A66-B53-C8-D12
A2-B79-C8-D12
A3-B79-C8-D12
A9-B79-C8-D12
A13-B79-C8-D12
A24-B79-C8-D12
A69-B79-C8-D12
A67-B79-C8-D12
A39-B79-C8-D12
A65-B79-C8-D12
A66-B79-C8-D12
A2-B80-C8-D12
A3-B80-C8-D12
A9-B80-C8-D12
A13-B80-C8-D12
A24-B80-C8-D12
A69-B80-C8-D12
A67-B80-C8-D12
A39-B80-C8-D12
A65-B80-C8-D12
A66-B80-C8-D12
A2-B85-C8-D12
A3-B85-C8-D12
A9-B85-C8-D12
A13-B85-C8-D12
A24-B85-C8-D12
A69-B85-C8-D12
A67-B85-C8-D12
A39-B85-C8-D12
A65-B85-C8-D12
A66-B85-C8-D12
A2-B86-C8-D12
A3-B86-C8-D12
A9-B86-C8-D12
A13-B86-C8-D12
A24-B86-C8-D12
A69-B86-C8-D12
A67-B86-C8-D12
A39-B86-C8-D12
A65-B86-C8-D12
A66-B86-C8-D12
A2-B87-C8-D12
A3-B87-C8-D12
A9-B87-C8-D12
A13-B87-C8-D12
A24-B87-C8-D12

-continued
A69-B87-C8-D12
A67-B87-C8-D12
A39-B87-C8-D12
A65-B87-C8-D12
A66-B87-C8-D12
A2-B89-C8-D12
A3-B89-C8-D12
A9-B89-C8-D12
A13-B89-C8-D12
A24-B89-C8-D12
A69-B89-C8-D12
A67-B89-C8-D12
A39-B89-C8-D12
A65-B89-C8-D12
A66-B89-C8-D12
A2-B92-C8-D12
A3-B92-C8-D12
A9-B92-C8-D12
A13-B92-C8-D12
A24-B92-C8-D12
A69-B92-C8-D12
A67-B92-C8-D12
A39-B92-C8-D12
A65-B92-C8-D12
A66-B92-C8-D12
A2-B4-C9-D12
A3-B4-C9-D12
A9-B4-C9-D12
A13-B4-C9-D12
A24-B4-C9-D12
A69-B4-C9-D12
A67-B4-C9-D12
A39-B4-C9-D12
A65-B4-C9-D12
A66-B4-C9-D12
A2-B5-C9-D12
A3-B5-C9-D12
A9-B5-C9-D12
A13-B5-C9-D12
A24-B5-C9-D12
A69-B5-C9-D12
A67-B5-C9-D12
A39-B5-C9-D12
A65-B5-C9-D12
A66-B5-C9-D12
A2-B6-C9-D12
A3-B6-C9-D12
A9-B6-C9-D12
A13-B6-C9-D12
A24-B6-C9-D12
A69-B6-C9-D12
A67-B6-C9-D12
A39-B6-C9-D12
A65-B6-C9-D12
A66-B6-C9-D12
A2-B32-C9-D12
A3-B32-C9-D12
A9-B32-C9-D12
A13-B32-C9-D12
A24-B32-C9-D12
A69-B32-C9-D12
A67-B32-C9-D12
A39-B32-C9-D12
A65-B32-C9-D12
A66-B32-C9-D12
A2-B39-C9-D12
A3-B39-C9-D12
A9-B39-C9-D12
A13-B39-C9-D12
A24-B39-C9-D12
A69-B39-C9-D12
A67-B39-C9-D12
A39-B39-C9-D12
A65-B39-C9-D12
A66-B39-C9-D12
A2-B45-C9-D12
A3-B45-C9-D12
A9-B45-C9-D12
A13-B45-C9-D12
A24-B45-C9-D12

-continued

A69-B45-C9-D12
A67-B45-C9-D12
A39-B45-C9-D12
A65-B45-C9-D12
A66-B45-C9-D12
A2-B53-C9-D12
A3-B53-C9-D12
A9-B53-C9-D12
A13-B53-C9-D12
A24-B53-C9-D12
A69-B53-C9-D12
A67-B53-C9-D12
A39-B53-C9-D12
A65-B53-C9-D12
A66-B53-C9-D12
A2-B79-C9-D12
A3-B79-C9-D12
A9-B79-C9-D12
A13-B79-C9-D12
A24-B79-C9-D12
A69-B79-C9-D12
A67-B79-C9-D12
A39-B79-C9-D12
A65-B79-C9-D12
A66-B79-C9-D12
A2-B80-C9-D12
A3-B80-C9-D12
A9-B80-C9-D12
A13-B80-C9-D12
A24-B80-C9-D12
A69-B80-C9-D12
A67-B80-C9-D12
A39-B80-C9-D12
A65-B80-C9-D12
A66-B80-C9-D12
A2-B85-C9-D12
A3-B85-C9-D12
A9-B85-C9-D12
A13-B85-C9-D12
A24-B85-C9-D12
A69-B85-C9-D12
A67-B85-C9-D12
A39-B85-C9-D12
A65-B85-C9-D12
A66-B85-C9-D12
A2-B86-C9-D12
A3-B86-C9-D12
A9-B86-C9-D12
A13-B86-C9-D12
A24-B86-C9-D12
A69-B86-C9-D12
A67-B86-C9-D12
A39-B86-C9-D12
A65-B86-C9-D12
A66-B86-C9-D12
A2-B87-C9-D12
A3-B87-C9-D12
A9-B87-C9-D12
A13-B87-C9-D12
A24-B87-C9-D12
A69-B87-C9-D12
A67-B87-C9-D12
A39-B87-C9-D12
A65-B87-C9-D12
A66-B87-C9-D12
A2-B89-C9-D12
A3-B89-C9-D12
A9-B89-C9-D12
A13-B89-C9-D12
A24-B89-C9-D12
A69-B89-C9-D12
A67-B89-C9-D12
A39-B89-C9-D12
A65-B89-C9-D12
A66-B89-C9-D12
A2-B92-C9-D12
A3-B92-C9-D12
A9-B92-C9-D12
A13-B92-C9-D12
A24-B92-C9-D12

-continued

A69-B92-C9-D12
A67-B92-C9-D12
A39-B92-C9-D12
A65-B92-C9-D12
A66-B92-C9-D12
A2-B4-C10-D12
A3-B4-C10-D12
A9-B4-C10-D12
A13-B4-C10-D12
A24-B4-C10-D12
A69-B4-C10-D12
A67-B4-C10-D12
A39-B4-C10-D12
A65-B4-C10-D12
A66-B4-C10-D12
A2-B5-C10-D12
A3-B5-C10-D12
A9-B5-C10-D12
A13-B5-C10-D12
A24-B5-C10-D12
A69-B5-C10-D12
A67-B5-C10-D12
A39-B5-C10-D12
A65-B5-C10-D12
A66-B5-C10-D12
A2-B6-C10-D12
A3-B6-C10-D12
A9-B6-C10-D12
A13-B6-C10-D12
A24-B6-C10-D12
A69-B6-C10-D12
A67-B6-C10-D12
A39-B6-C10-D12
A65-B6-C10-D12
A66-B6-C10-D12
A2-B32-C10-D12
A3-B32-C10-D12
A9-B32-C10-D12
A13-B32-C10-D12
A24-B32-C10-D12
A69-B32-C10-D12
A67-B32-C10-D12
A39-B32-C10-D12
A65-B32-C10-D12
A66-B32-C10-D12
A2-B39-C10-D12
A3-B39-C10-D12
A9-B39-C10-D12
A13-B39-C10-D12
A24-B39-C10-D12
A69-B39-C10-D12
A67-B39-C10-D12
A39-B39-C10-D12
A65-B39-C10-D12
A66-B39-C10-D12
A2-B45-C10-D12
A3-B45-C10-D12
A9-B45-C10-D12
A13-B45-C10-D12
A24-B45-C10-D12
A69-B45-C10-D12
A67-B45-C10-D12
A39-B45-C10-D12
A65-B45-C10-D12
A66-B45-C10-D12
A2-B53-C10-D12
A3-B53-C10-D12
A9-B53-C10-D12
A13-B53-C10-D12
A24-B53-C10-D12
A69-B53-C10-D12
A67-B53-C10-D12
A39-B53-C10-D12
A65-B53-C10-D12
A66-B53-C10-D12
A2-B79-C10-D12
A3-B79-C10-D12
A9-B79-C10-D12
A13-B79-C10-D12
A24-B79-C10-D12

-continued

A69-B79-C10-D12
A67-B79-C10-D12
A39-B79-C10-D12
A65-B79-C10-D12
A66-B79-C10-D12
A2-B80-C10-D12
A3-B80-C10-D12
A9-B80-C10-D12
A13-B80-C10-D12
A24-B80-C10-D12
A69-B80-C10-D12
A67-B80-C10-D12
A39-B80-C10-D12
A65-B80-C10-D12
A66-B80-C10-D12
A2-B85-C10-D12
A3-B85-C10-D12
A9-B85-C10-D12
A13-B85-C10-D12
A24-B85-C10-D12
A69-B85-C10-D12
A67-B85-C10-D12
A39-B85-C10-D12
A65-B85-C10-D12
A66-B85-C10-D12
A2-B86-C10-D12
A3-B86-C10-D12
A9-B86-C10-D12
A13-B86-C10-D12
A24-B86-C10-D12
A69-B86-C10-D12
A67-B86-C10-D12
A39-B86-C10-D12
A65-B86-C10-D12
A66-B86-C10-D12
A2-B87-C10-D12
A3-B87-C10-D12
A9-B87-C10-D12
A13-B87-C10-D12
A24-B87-C10-D12
A69-B87-C10-D12
A67-B87-C10-D12
A39-B87-C10-D12
A65-B87-C10-D12
A66-B87-C10-D12
A2-B89-C10-D12
A3-B89-C10-D12
A9-B89-C10-D12
A13-B89-C10-D12
A24-B89-C10-D12
A69-B89-C10-D12
A67-B89-C10-D12
A39-B89-C10-D12
A65-B89-C10-D12
A66-B89-C10-D12
A2-B92-C10-D12
A3-B92-C10-D12
A9-B92-C10-D12
A13-B92-C10-D12
A24-B92-C10-D12
A69-B92-C10-D12
A67-B92-C10-D12
A39-B92-C10-D12
A65-B92-C10-D12
A66-B92-C10-D12
A2-B4-C11-D12
A3-B4-C11-D12
A9-B4-C11-D12
A13-B4-C11-D12
A24-B4-C11-D12
A69-B4-C11-D12
A67-B4-C11-D12
A39-B4-C11-D12
A65-B4-C11-D12
A66-B4-C11-D12
A2-B5-C11-D12
A3-B5-C11-D12
A9-B5-C11-D12
A13-B5-C11-D12
A24-B5-C11-D12

-continued

A69-B5-C11-D12
A67-B5-C11-D12
A39-B5-C11-D12
A65-B5-C11-D12
A66-B5-C11-D12
A2-B6-C11-D12
A3-B6-C11-D12
A9-B6-C11-D12
A13-B6-C11-D12
A24-B6-C11-D12
A69-B6-C11-D12
A67-B6-C11-D12
A39-B6-C11-D12
A65-B6-C11-D12
A66-B6-C11-D12
A2-B32-C11-D12
A3-B32-C11-D12
A9-B32-C11-D12
A13-B32-C11-D12
A24-B32-C11-D12
A69-B32-C11-D12
A67-B32-C11-D12
A39-B32-C11-D12
A65-B32-C11-D12
A66-B32-C11-D12
A2-B39-C11-D12
A3-B39-C11-D12
A9-B39-C11-D12
A13-B39-C11-D12
A24-B39-C11-D12
A69-B39-C11-D12
A67-B39-C11-D12
A39-B39-C11-D12
A65-B39-C11-D12
A66-B39-C11-D12
A2-B45-C11-D12
A3-B45-C11-D12
A9-B45-C11-D12
A13-B45-C11-D12
A24-B45-C11-D12
A69-B45-C11-D12
A67-B45-C11-D12
A39-B45-C11-D12
A65-B45-C11-D12
A66-B45-C11-D12
A2-B53-C11-D12
A3-B53-C11-D12
A9-B53-C11-D12
A13-B53-C11-D12
A24-B53-C11-D12
A69-B53-C11-D12
A67-B53-C11-D12
A39-B53-C11-D12
A65-B53-C11-D12
A66-B53-C11-D12
A2-B79-C11-D12
A3-B79-C11-D12
A9-B79-C11-D12
A13-B79-C11-D12
A24-B79-C11-D12
A69-B79-C11-D12
A67-B79-C11-D12
A39-B79-C11-D12
A65-B79-C11-D12
A66-B79-C11-D12
A2-B80-C11-D12
A3-B80-C11-D12
A9-B80-C11-D12
A13-B80-C11-D12
A24-B80-C11-D12
A69-B80-C11-D12
A67-B80-C11-D12
A39-B80-C11-D12
A65-B80-C11-D12
A66-B80-C11-D12
A2-B85-C11-D12
A3-B85-C11-D12
A9-B85-C11-D12
A13-B85-C11-D12
A24-B85-C11-D12

-continued

A69-B85-C11-D12
A67-B85-C11-D12
A39-B85-C11-D12
A65-B85-C11-D12
A66-B85-C11-D12
A2-B86-C11-D12
A3-B86-C11-D12
A9-B86-C11-D12
A13-B86-C11-D12
A24-B86-C11-D12
A69-B86-C11-D12
A67-B86-C11-D12
A39-B86-C11-D12
A65-B86-C11-D12
A66-B86-C11-D12
A2-B87-C11-D12
A3-B87-C11-D12
A9-B87-C11-D12
A13-B87-C11-D12
A24-B87-C11-D12
A69-B87-C11-D12
A67-B87-C11-D12
A39-B87-C11-D12
A65-B87-C11-D12
A66-B87-C11-D12
A2-B89-C11-D12
A3-B89-C11-D12
A9-B89-C11-D12
A13-B89-C11-D12
A24-B89-C11-D12
A69-B89-C11-D12
A67-B89-C11-D12
A39-B89-C11-D12
A65-B89-C11-D12
A66-B89-C11-D12
A2-B92-C11-D12
A3-B92-C11-D12
A9-B92-C11-D12
A13-B92-C11-D12
A24-B92-C11-D12
A69-B92-C11-D12
A67-B92-C11-D12
A39-B92-C11-D12
A65-B92-C11-D12
A66-B92-C11-D12
A2-B4-C12-D12
A3-B4-C12-D12
A9-B4-C12-D12
A13-B4-C12-D12
A24-B4-C12-D12
A69-B4-C12-D12
A67-B4-C12-D12
A39-B4-C12-D12
A65-B4-C12-D12
A66-B4-C12-D12
A2-B5-C12-D12
A3-B5-C12-D12
A9-B5-C12-D12
A13-B5-C12-D12
A24-B5-C12-D12
A69-B5-C12-D12
A67-B5-C12-D12
A39-B5-C12-D12
A65-B5-C12-D12
A66-B5-C12-D12
A2-B6-C12-D12
A3-B6-C12-D12
A9-B6-C12-D12
A13-B6-C12-D12
A24-B6-C12-D12
A69-B6-C12-D12
A67-B6-C12-D12
A39-B6-C12-D12
A65-B6-C12-D12
A66-B6-C12-D12
A2-B32-C12-D12
A3-B32-C12-D12
A9-B32-C12-D12
A13-B32-C12-D12
A24-B32-C12-D12

-continued

A69-B32-C12-D12
A67-B32-C12-D12
A39-B32-C12-D12
A65-B32-C12-D12
A66-B32-C12-D12
A2-B39-C12-D12
A3-B39-C12-D12
A9-B39-C12-D12
A13-B39-C12-D12
A24-B39-C12-D12
A69-B39-C12-D12
A67-B39-C12-D12
A39-B39-C12-D12
A65-B39-C12-D12
A66-B39-C12-D12
A2-B45-C12-D12
A3-B45-C12-D12
A9-B45-C12-D12
A13-B45-C12-D12
A24-B45-C12-D12
A69-B45-C12-D12
A67-B45-C12-D12
A39-B45-C12-D12
A65-B45-C12-D12
A66-B45-C12-D12
A2-B53-C12-D12
A3-B53-C12-D12
A9-B53-C12-D12
A13-B53-C12-D12
A24-B53-C12-D12
A69-B53-C12-D12
A67-B53-C12-D12
A39-B53-C12-D12
A65-B53-C12-D12
A66-B53-C12-D12
A2-B79-C12-D12
A3-B79-C12-D12
A9-B79-C12-D12
A13-B79-C12-D12
A24-B79-C12-D12
A69-B79-C12-D12
A67-B79-C12-D12
A39-B79-C12-D12
A65-B79-C12-D12
A66-B79-C12-D12
A2-B80-C12-D12
A3-B80-C12-D12
A9-B80-C12-D12
A13-B80-C12-D12
A24-B80-C12-D12
A69-B80-C12-D12
A67-B80-C12-D12
A39-B80-C12-D12
A65-B80-C12-D12
A66-B80-C12-D12
A2-B85-C12-D12
A3-B85-C12-D12
A9-B85-C12-D12
A13-B85-C12-D12
A24-B85-C12-D12
A69-B85-C12-D12
A67-B85-C12-D12
A39-B85-C12-D12
A65-B85-C12-D12
A66-B85-C12-D12
A2-B86-C12-D12
A3-B86-C12-D12
A9-B86-C12-D12
A13-B86-C12-D12
A24-B86-C12-D12
A69-B86-C12-D12
A67-B86-C12-D12
A39-B86-C12-D12
A65-B86-C12-D12
A66-B86-C12-D12
A2-B87-C12-D12
A3-B87-C12-D12
A9-B87-C12-D12
A13-B87-C12-D12
A24-B87-C12-D12

-continued
A69-B87-C12-D12
A67-B87-C12-D12
A39-B87-C12-D12
A65-B87-C12-D12
A66-B87-C12-D12
A2-B89-C12-D12
A3-B89-C12-D12
A9-B89-C12-D12
A13-B89-C12-D12
A24-B89-C12-D12
A69-B89-C12-D12
A67-B89-C12-D12
A39-B89-C12-D12
A65-B89-C12-D12
A66-B89-C12-D12
A2-B92-C12-D12
A3-B92-C12-D12
A9-B92-C12-D12
A13-B92-C12-D12
A24-B92-C12-D12
A69-B92-C12-D12
A67-B92-C12-D12
A39-B92-C12-D12
A65-B92-C12-D12
A66-B92-C12-D12
A2-B4-C13-D12
A3-B4-C13-D12
A9-B4-C13-D12
A13-B4-C13-D12
A24-B4-C13-D12
A69-B4-C13-D12
A67-B4-C13-D12
A39-B4-C13-D12
A65-B4-C13-D12
A66-B4-C13-D12
A2-B5-C13-D12
A3-B5-C13-D12
A9-B5-C13-D12
A13-B5-C13-D12
A24-B5-C13-D12
A69-B5-C13-D12
A67-B5-C13-D12
A39-B5-C13-D12
A65-B5-C13-D12
A66-B5-C13-D12
A2-B6-C13-D12
A3-B6-C13-D12
A9-B6-C13-D12
A13-B6-C13-D12
A24-B6-C13-D12
A69-B6-C13-D12
A67-B6-C13-D12
A39-B6-C13-D12
A65-B6-C13-D12
A66-B6-C13-D12
A2-B32-C13-D12
A3-B32-C13-D12
A9-B32-C13-D12
A13-B32-C13-D12
A24-B32-C13-D12
A69-B32-C13-D12
A67-B32-C13-D12
A39-B32-C13-D12
A65-B32-C13-D12
A66-B32-C13-D12
A2-B39-C13-D12
A3-B39-C13-D12
A9-B39-C13-D12
A13-B39-C13-D12
A24-B39-C13-D12
A69-B39-C13-D12
A67-B39-C13-D12
A39-B39-C13-D12
A65-B39-C13-D12
A66-B39-C13-D12
A2-B45-C13-D12
A3-B45-C13-D12
A9-B45-C13-D12
A13-B45-C13-D12
A24-B45-C13-D12

-continued
A69-B45-C13-D12
A67-B45-C13-D12
A39-B45-C13-D12
A65-B45-C13-D12
A66-B45-C13-D12
A2-B53-C13-D12
A3-B53-C13-D12
A9-B53-C13-D12
A13-B53-C13-D12
A24-B53-C13-D12
A69-B53-C13-D12
A67-B53-C13-D12
A39-B53-C13-D12
A65-B53-C13-D12
A66-B53-C13-D12
A2-B79-C13-D12
A3-B79-C13-D12
A9-B79-C13-D12
A13-B79-C13-D12
A24-B79-C13-D12
A69-B79-C13-D12
A67-B79-C13-D12
A39-B79-C13-D12
A65-B79-C13-D12
A66-B79-C13-D12
A2-B80-C13-D12
A3-B80-C13-D12
A9-B80-C13-D12
A13-B80-C13-D12
A24-B80-C13-D12
A69-B80-C13-D12
A67-B80-C13-D12
A39-B80-C13-D12
A65-B80-C13-D12
A66-B80-C13-D12
A2-B85-C13-D12
A3-B85-C13-D12
A9-B85-C13-D12
A13-B85-C13-D12
A24-B85-C13-D12
A69-B85-C13-D12
A67-B85-C13-D12
A39-B85-C13-D12
A65-B85-C13-D12
A66-B85-C13-D12
A2-B86-C13-D12
A3-B86-C13-D12
A9-B86-C13-D12
A13-B86-C13-D12
A24-B86-C13-D12
A69-B86-C13-D12
A67-B86-C13-D12
A39-B86-C13-D12
A65-B86-C13-D12
A66-B86-C13-D12
A2-B87-C13-D12
A3-B87-C13-D12
A9-B87-C13-D12
A13-B87-C13-D12
A24-B87-C13-D12
A69-B87-C13-D12
A67-B87-C13-D12
A39-B87-C13-D12
A65-B87-C13-D12
A66-B87-C13-D12
A2-B89-C13-D12
A3-B89-C13-D12
A9-B89-C13-D12
A13-B89-C13-D12
A24-B89-C13-D12
A69-B89-C13-D12
A67-B89-C13-D12
A39-B89-C13-D12
A65-B89-C13-D12
A66-B89-C13-D12
A2-B92-C13-D12
A3-B92-C13-D12
A9-B92-C13-D12
A13-B92-C13-D12
A24-B92-C13-D12

-continued

A69-B92-C13-D12
A67-B92-C13-D12
A39-B92-C13-D12
A65-B92-C13-D12
A66-B92-C13-D12
A2-B4-C1-D13
A3-B4-C1-D13
A9-B4-C1-D13
A13-B4-C1-D13
A24-B4-C1-D13
A69-B4-C1-D13
A67-B4-C1-D13
A39-B4-C1-D13
A65-B4-C1-D13
A66-B4-C1-D13
A2-B5-C1-D13
A3-B5-C1-D13
A9-B5-C1-D13
A13-B5-C1-D13
A24-B5-C1-D13
A69-B5-C1-D13
A67-B5-C1-D13
A39-B5-C1-D13
A65-B5-C1-D13
A66-B5-C1-D13
A2-B6-C1-D13
A3-B6-C1-D13
A9-B6-C1-D13
A13-B6-C1-D13
A24-B6-C1-D13
A69-B6-C1-D13
A67-B6-C1-D13
A39-B6-C1-D13
A65-B6-C1-D13
A66-B6-C1-D13
A2-B32-C1-D13
A3-B32-C1-D13
A9-B32-C1-D13
A13-B32-C1-D13
A24-B32-C1-D13
A69-B32-C1-D13
A67-B32-C1-D13
A39-B32-C1-D13
A65-B32-C1-D13
A66-B32-C1-D13
A2-B39-C1-D13
A3-B39-C1-D13
A9-B39-C1-D13
A13-B39-C1-D13
A24-B39-C1-D13
A69-B39-C1-D13
A67-B39-C1-D13
A39-B39-C1-D13
A65-B39-C1-D13
A66-B39-C1-D13
A2-B45-C1-D13
A3-B45-C1-D13
A9-B45-C1-D13
A13-B45-C1-D13
A24-B45-C1-D13
A69-B45-C1-D13
A67-B45-C1-D13
A39-B45-C1-D13
A65-B45-C1-D13
A66-B45-C1-D13
A2-B53-C1-D13
A3-B53-C1-D13
A9-B53-C1-D13
A13-B53-C1-D13
A24-B53-C1-D13
A69-B53-C1-D13
A67-B53-C1-D13
A39-B53-C1-D13
A65-B53-C1-D13
A66-B53-C1-D13
A2-B79-C1-D13
A3-B79-C1-D13
A9-B79-C1-D13
A13-B79-C1-D13
A24-B79-C1-D13

-continued

A69-B79-C1-D13
A67-B79-C1-D13
A39-B79-C1-D13
A65-B79-C1-D13
A66-B79-C1-D13
A2-B80-C1-D13
A3-B80-C1-D13
A9-B80-C1-D13
A13-B80-C1-D13
A24-B80-C1-D13
A69-B80-C1-D13
A67-B80-C1-D13
A39-B80-C1-D13
A65-B80-C1-D13
A66-B80-C1-D13
A2-B85-C1-D13
A3-B85-C1-D13
A9-B85-C1-D13
A13-B85-C1-D13
A24-B85-C1-D13
A69-B85-C1-D13
A67-B85-C1-D13
A39-B85-C1-D13
A65-B85-C1-D13
A66-B85-C1-D13
A2-B86-C1-D13
A3-B86-C1-D13
A9-B86-C1-D13
A13-B86-C1-D13
A24-B86-C1-D13
A69-B86-C1-D13
A67-B86-C1-D13
A39-B86-C1-D13
A65-B86-C1-D13
A66-B86-C1-D13
A2-B87-C1-D13
A3-B87-C1-D13
A9-B87-C1-D13
A13-B87-C1-D13
A24-B87-C1-D13
A69-B87-C1-D13
A67-B87-C1-D13
A39-B87-C1-D13
A65-B87-C1-D13
A66-B87-C1-D13
A2-B89-C1-D13
A3-B89-C1-D13
A9-B89-C1-D13
A13-B89-C1-D13
A24-B89-C1-D13
A69-B89-CL-D13
A67-B89-C1-D13
A39-B89-C1-D13
A65-B89-C1-D13
A66-B89-C1-D13
A2-B92-C1-D13
A3-B92-C1-D13
A9-B92-C1-D13
A13-B92-C1-D13
A24-B92-C1-D13
A69-B92-C1-D13
A67-B92-C1-D13
A39-B92-C1-D13
A65-B92-C1-D13
A66-B92-C1-D13
A2-B4-C2-D13
A3-B4-C2-D13
A9-B4-C2-D13
A13-B4-C2-D13
A24-B4-C2-D13
A69-B4-C2-D13
A67-B4-C2-D13
A39-B4-C2-D13
A65-B4-C2-D13
A66-B4-C2-D13
A2-B5-C2-D13
A3-B5-C2-D13
A9-B5-C2-D13
A13-B5-C2-D13
A24-B5-C2-D13

-continued
A69-B5-C2-D13
A67-B5-C2-D13
A39-B5-C2-D13
A65-B5-C2-D13
A66-B5-C2-D13
A2-B6-C2-D13
A3-B6-C2-D13
A9-B6-C2-D13
A13-B6-C2-D13
A24-B6-C2-D13
A69-B6-C2-D13
A67-B6-C2-D13
A39-B6-C2-D13
A65-B6-C2-D13
A66-B6-C2-D13
A2-B32-C2-D13
A3-B32-C2-D13
A9-B32-C2-D13
A13-B32-C2-D13
A24-B32-C2-D13
A69-B32-C2-D13
A67-B32-C2-D13
A39-B32-C2-D13
A65-B32-C2-D13
A66-B32-C2-D13
A2-B39-C2-D13
A3-B39-C2-D13
A9-B39-C2-D13
A13-B39-C2-D13
A24-B39-C2-D13
A69-B39-C2-D13
A67-B39-C2-D13
A39-B39-C2-D13
A65-B39-C2-D13
A66-B39-C2-D13
A2-B45-C2-D13
A3-B45-C2-D13
A9-B45-C2-D13
A13-B45-C2-D13
A24-B45-C2-D13
A69-B45-C2-D13
A67-B45-C2-D13
A39-B45-C2-D13
A65-B45-C2-D13
A66-B45-C2-D13
A2-B53-C2-D13
A3-B53-C2-D13
A9-B53-C2-D13
A13-B53-C2-D13
A24-B53-C2-D13
A69-B53-C2-D13
A67-B53-C2-D13
A39-B53-C2-D13
A65-B53-C2-D13
A66-B53-C2-D13
A2-B79-C2-D13
A3-B79-C2-D13
A9-B79-C2-D13
A13-B79-C2-D13
A24-B79-C2-D13
A69-B79-C2-D13
A67-B79-C2-D13
A39-B79-C2-D13
A65-B79-C2-D13
A66-B79-C2-D13
A2-B80-C2-D13
A3-B80-C2-D13
A9-B80-C2-D13
A13-B80-C2-D13
A24-B80-C2-D13
A69-B80-C2-D13
A67-B80-C2-D13
A39-B80-C2-D13
A65-B80-C2-D13
A66-B80-C2-D13
A2-B85-C2-D13
A3-B85-C2-D13
A9-B85-C2-D13
A13-B85-C2-D13
A24-B85-C2-D13

-continued
A69-B85-C2-D13
A67-B85-C2-D13
A39-B85-C2-D13
A65-B85-C2-D13
A66-B85-C2-D13
A2-B86-C2-D13
A3-B86-C2-D13
A9-B86-C2-D13
A13-B86-C2-D13
A24-B86-C2-D13
A69-B86-C2-D13
A67-B86-C2-D13
A39-B86-C2-D13
A65-B86-C2-D13
A66-B86-C2-D13
A2-B87-C2-D13
A3-B87-C2-D13
A9-B87-C2-D13
A13-B87-C2-D13
A24-B87-C2-D13
A69-B87-C2-D13
A67-B87-C2-D13
A39-B87-C2-D13
A65-B87-C2-D13
A66-B87-C2-D13
A2-B89-C2-D13
A3-B89-C2-D13
A9-B89-C2-D13
A13-B89-C2-D13
A24-B89-C2-D13
A69-B89-C2-D13
A67-B89-C2-D13
A39-B89-C2-D13
A65-B89-C2-D13
A66-B89-C2-D13
A2-B92-C2-D13
A3-B92-C2-D13
A9-B92-C2-D13
A13-B92-C2-D13
A24-B92-C2-D13
A69-B92-C2-D13
A67-B92-C2-D13
A39-B92-C2-D13
A65-B92-C2-D13
A66-B92-C2-D13
A2-B4-C3-D13
A3-B4-C3-D13
A9-B4-C3-D13
A13-B4-C3-D13
A24-B4-C3-D13
A69-B4-C3-D13
A67-B4-C3-D13
A39-B4-C3-D13
A65-B4-C3-D13
A66-B4-C3-D13
A2-B5-C3-D13
A3-B5-C3-D13
A9-B5-C3-D13
A13-B5-C3-D13
A24-B5-C3-D13
A69-B5-C3-D13
A67-B5-C3-D13
A39-B5-C3-D13
A65-B5-C3-D13
A66-B5-C3-D13
A2-B6-C3-D13
A3-B6-C3-D13
A9-B6-C3-D13
A13-B6-C3-D13
A24-B6-C3-D13
A69-B6-C3-D13
A67-B6-C3-D13
A39-B6-C3-D13
A65-B6-C3-D13
A66-B6-C3-D13
A2-B32-C3-D13
A3-B32-C3-D13
A9-B32-C3-D13
A13-B32-C3-D13
A24-B32-C3-D13

-continued
A69-B32-C3-D13
A67-B32-C3-D13
A39-B32-C3-D13
A65-B32-C3-D13
A66-B32-C3-D13
A2-B39-C3-D13
A3-B39-C3-D13
A9-B39-C3-D13
A13-B39-C3-D13
A24-B39-C3-D13
A69-B39-C3-D13
A67-B39-C3-D13
A39-B39-C3-D13
A65-B39-C3-D13
A66-B39-C3-D13
A2-B45-C3-D13
A3-B45-C3-D13
A9-B45-C3-D13
A13-B45-C3-D13
A24-B45-C3-D13
A69-B45-C3-D13
A67-B45-C3-D13
A39-B45-C3-D13
A65-B45-C3-D13
A66-B45-C3-D13
A2-B53-C3-D13
A3-B53-C3-D13
A9-B53-C3-D13
A13-B53-C3-D13
A24-B53-C3-D13
A69-B53-C3-D13
A67-B53-C3-D13
A39-B53-C3-D13
A65-B53-C3-D13
A66-B53-C3-D13
A2-B79-C3-D13
A3-B79-C3-D13
A9-B79-C3-D13
A13-B79-C3-D13
A24-B79-C3-D13
A69-B79-C3-D13
A67-B79-C3-D13
A39-B79-C3-D13
A65-B79-C3-D13
A66-B79-C3-D13
A2-B80-C3-D13
A3-B80-C3-D13
A9-B80-C3-D13
A13-B80-C3-D13
A24-B80-C3-D13
A69-B80-C3-D13
A67-B80-C3-D13
A39-B80-C3-D13
A65-B80-C3-D13
A66-B80-C3-D13
A2-B85-C3-D13
A3-B85-C3-D13
A9-B85-C3-D13
A13-B85-C3-D13
A24-B85-C3-D13
A69-B85-C3-D13
A67-B85-C3-D13
A39-B85-C3-D13
A65-B85-C3-D13
A66-B85-C3-D13
A2-B86-C3-D13
A3-B86-C3-D13
A9-B86-C3-D13
A13-B86-C3-D13
A24-B86-C3-D13
A69-B86-C3-D13
A67-B86-C3-D13
A39-B86-C3-D13
A65-B86-C3-D13
A66-B86-C3-D13
A2-B87-C3-D13
A3-B87-C3-D13
A9-B87-C3-D13
A13-B87-C3-D13
A24-B87-C3-D13

-continued
A69-B87-C3-D13
A67-B87-C3-D13
A39-B87-C3-D13
A65-B87-C3-D13
A66-B87-C3-D13
A2-B89-C3-D13
A3-B89-C3-D13
A9-B89-C3-D13
A13-B89-C3-D13
A24-B89-C3-D13
A69-B89-C3-D13
A67-B89-C3-D13
A39-B89-C3-D13
A65-B89-C3-D13
A66-B89-C3-D13
A2-B92-C3-D13
A3-B92-C3-D13
A9-B92-C3-D13
A13-B92-C3-D13
A24-B92-C3-D13
A69-B92-C3-D13
A67-B92-C3-D13
A39-B92-C3-D13
A65-B92-C3-D13
A66-B92-C3-D13
A2-B4-C4-D13
A3-B4-C4-D13
A9-B4-C4-D13
A13-B4-C4-D13
A24-B4-C4-D13
A69-B4-C4-D13
A67-B4-C4-D13
A39-B4-C4-D13
A65-B4-C4-D13
A66-B4-C4-D13
A2-B5-C4-D13
A3-B5-C4-D13
A9-B5-C4-D13
A13-B5-C4-D13
A24-B5-C4-D13
A69-B5-C4-D13
A67-B5-C4-D13
A39-B5-C4-D13
A65-B5-C4-D13
A66-B5-C4-D13
A2-B6-C4-D13
A3-B6-C4-D13
A9-B6-C4-D13
A13-B6-C4-D13
A24-B6-C4-D13
A69-B6-C4-D13
A67-B6-C4-D13
A39-B6-C4-D13
A65-B6-C4-D13
A66-B6-C4-D13
A2-B32-C4-D13
A3-B32-C4-D13
A9-B32-C4-D13
A13-B32-C4-D13
A24-B32-C4-D13
A69-B32-C4-D13
A67-B32-C4-D13
A39-B32-C4-D13
A65-B32-C4-D13
A66-B32-C4-D13
A2-B39-C4-D13
A3-B39-C4-D13
A9-B39-C4-D13
A13-B39-C4-D13
A24-B39-C4-D13
A69-B39-C4-D13
A67-B39-C4-D13
A39-B39-C4-D13
A65-B39-C4-D13
A66-B39-C4-D13
A2-B45-C4-D13
A3-B45-C4-D13
A9-B45-C4-D13
A13-B45-C4-D13
A24-B45-C4-D13

-continued
A69-B45-C4-D13
A67-B45-C4-D13
A39-B45-C4-D13
A65-B45-C4-D13
A66-B45-C4-D13
A2-B53-C4-D13
A3-B53-C4-D13
A9-B53-C4-D13
A13-B53-C4-D13
A24-B53-C4-D13
A69-B53-C4-D13
A67-B53-C4-D13
A39-B53-C4-D13
A65-B53-C4-D13
A66-B53-C4-D13
A2-B79-C4-D13
A3-B79-C4-D13
A9-B79-C4-D13
A13-B79-C4-D13
A24-B79-C4-D13
A69-B79-C4-D13
A67-B79-C4-D13
A39-B79-C4-D13
A65-B79-C4-D13
A66-B79-C4-D13
A2-B80-C4-D13
A3-B80-C4-D13
A9-B80-C4-D13
A13-B80-C4-D13
A24-B80-C4-D13
A69-B80-C4-D13
A67-B80-C4-D13
A39-B80-C4-D13
A65-B80-C4-D13
A66-B80-C4-D13
A2-B85-C4-D13
A3-B85-C4-D13
A9-B85-C4-D13
A13-B85-C4-D13
A24-B85-C4-D13
A69-B85-C4-D13
A67-B85-C4-D13
A39-B85-C4-D13
A65-B85-C4-D13
A66-B85-C4-D13
A2-B86-C4-D13
A3-B86-C4-D13
A9-B86-C4-D13
A13-B86-C4-D13
A24-B86-C4-D13
A69-B86-C4-D13
A67-B86-C4-D13
A39-B86-C4-D13
A65-B86-C4-D13
A66-B86-C4-D13
A2-B87-C4-D13
A3-B87-C4-D13
A9-B87-C4-D13
A13-B87-C4-D13
A24-B87-C4-D13
A69-B87-C4-D13
A67-B87-C4-D13
A39-B87-C4-D13
A65-B87-C4-D13
A66-B87-C4-D13
A2-B89-C4-D13
A3-B89-C4-D13
A9-B89-C4-D13
A13-B89-C4-D13
A24-B89-C4-D13
A69-B89-C4-D13
A67-B89-C4-D13
A39-B89-C4-D13
A65-B89-C4-D13
A66-B89-C4-D13
A2-B92-C4-D13
A3-B92-C4-D13
A9-B92-C4-D13
A13-B92-C4-D13
A24-B92-C4-D13

-continued
A69-B92-C4-D13
A67-B92-C4-D13
A39-B92-C4-D13
A65-B92-C4-D13
A66-B92-C4-D13
A2-B4-C5-D13
A3-B4-C5-D13
A9-B4-C5-D13
A13-B4-C5-D13
A24-B4-C5-D13
A69-B4-C5-D13
A67-B4-C5-D13
A39-B4-C5-D13
A65-B4-C5-D13
A66-B4-C5-D13
A2-B5-C5-D13
A3-B5-C5-D13
A9-B5-C5-D13
A13-B5-C5-D13
A24-B5-C5-D13
A69-B5-C5-D13
A67-B5-C5-D13
A39-B5-C5-D13
A65-B5-C5-D13
A66-B5-C5-D13
A2-B6-C5-D13
A3-B6-C5-D13
A9-B6-C5-D13
A13-B6-C5-D13
A24-B6-C5-D13
A69-B6-C5-D13
A67-B6-C5-D13
A39-B6-C5-D13
A65-B6-C5-D13
A66-B6-C5-D13
A2-B32-C5-D13
A3-B32-C5-D13
A9-B32-C5-D13
A13-B32-C5-D13
A24-B32-C5-D13
A69-B32-C5-D13
A67-B32-C5-D13
A39-B32-C5-D13
A65-B32-C5-D13
A66-B32-C5-D13
A2-B39-C5-D13
A3-B39-C5-D13
A9-B39-C5-D13
A13-B39-C5-D13
A24-B39-C5-D13
A69-B39-C5-D13
A67-B39-C5-D13
A39-B39-C5-D13
A65-B39-C5-D13
A66-B39-C5-D13
A2-B45-C5-D13
A3-B45-C5-D13
A9-B45-C5-D13
A13-B45-C5-D13
A24-B45-C5-D13
A69-B45-C5-D13
A67-B45-C5-D13
A39-B45-C5-D13
A65-B45-C5-D13
A66-B45-C5-D13
A2-B53-C5-D13
A3-B53-C5-D13
A9-B53-C5-D13
A13-B53-C5-D13
A24-B53-C5-D13
A69-B53-C5-D13
A67-B53-C5-D13
A39-B53-C5-D13
A65-B53-C5-D13
A66-B53-C5-D13
A2-B79-C5-D13
A3-B79-C5-D13
A9-B79-C5-D13
A13-B79-C5-D13
A24-B79-C5-D13

-continued
A69-B79-C5-D13
A67-B79-C5-D13
A39-B79-C5-D13
A65-B79-C5-D13
A66-B79-C5-D13
A2-B80-C5-D13
A3-B80-C5-D13
A9-B80-C5-D13
A13-B80-C5-D13
A24-B80-C5-D13
A69-B80-C5-D13
A67-B80-C5-D13
A39-B80-C5-D13
A65-B80-C5-D13
A66-B80-C5-D13
A2-B85-C5-D13
A3-B85-C5-D13
A9-B85-C5-D13
A13-B85-C5-D13
A24-B85-C5-D13
A69-B85-C5-D13
A67-B85-C5-D13
A39-B85-C5-D13
A65-B85-C5-D13
A66-B85-C5-D13
A2-B86-C5-D13
A3-B86-C5-D13
A9-B86-C5-D13
A13-B86-C5-D13
A24-B86-C5-D13
A69-B86-C5-D13
A67-B86-C5-D13
A39-B86-C5-D13
A65-B86-C5-D13
A66-B86-C5-D13
A2-B87-C5-D13
A3-B87-C5-D13
A9-B87-C5-D13
A13-B87-C5-D13
A24-B87-C5-D13
A69-B87-C5-D13
A67-B87-C5-D13
A39-B87-C5-D13
A65-B87-C5-D13
A66-B87-C5-D13
A2-B89-C5-D13
A3-B89-C5-D13
A9-B89-C5-D13
A13-B89-C5-D13
A24-B89-C5-D13
A69-B89-C5-D13
A67-B89-C5-D13
A39-B89-C5-D13
A65-B89-C5-D13
A66-B89-C5-D13
A2-B92-C5-D13
A3-B92-C5-D13
A9-B92-C5-D13
A13-B92-C5-D13
A24-B92-C5-D13
A69-B92-C5-D13
A67-B92-C5-D13
A39-B92-C5-D13
A65-B92-C5-D13
A66-B92-C5-D13
A2-B4-C6-D13
A3-B4-C6-D13
A9-B4-C6-D13
A13-B4-C6-D13
A24-B4-C6-D13
A69-B4-C6-D13
A67-B4-C6-D13
A39-B4-C6-D13
A65-B4-C6-D13
A66-B4-C6-D13
A2-B5-C6-D13
A3-B5-C6-D13
A9-B5-C6-D13
A13-B5-C6-D13
A24-B5-C6-D13

-continued
A69-B5-C6-D13
A67-B5-C6-D13
A39-B5-C6-D13
A65-B5-C6-D13
A66-B5-C6-D13
A2-B6-C6-D13
A3-B6-C6-D13
A9-B6-C6-D13
A13-B6-C6-D13
A24-B6-C6-D13
A69-B6-C6-D13
A67-B6-C6-D13
A39-B6-C6-D13
A65-B6-C6-D13
A66-B6-C6-D13
A2-B32-C6-D13
A3-B32-C6-D13
A9-B32-C6-D13
A13-B32-C6-D13
A24-B32-C6-D13
A69-B32-C6-D13
A67-B32-C6-D13
A39-B32-C6-D13
A65-B32-C6-D13
A66-B32-C6-D13
A2-B39-C6-D13
A3-B39-C6-D13
A9-B39-C6-D13
A13-B39-C6-D13
A24-B39-C6-D13
A69-B39-C6-D13
A67-B39-C6-D13
A39-B39-C6-D13
A65-B39-C6-D13
A66-B39-C6-D13
A2-B45-C6-D13
A3-B45-C6-D13
A9-B45-C6-D13
A13-B45-C6-D13
A24-B45-C6-D13
A69-B45-C6-D13
A67-B45-C6-D13
A39-B45-C6-D13
A65-B45-C6-D13
A66-B45-C6-D13
A2-B53-C6-D13
A3-B53-C6-D13
A9-B53-C6-D13
A13-B53-C6-D13
A24-B53-C6-D13
A69-B53-C6-D13
A67-B53-C6-D13
A39-B53-C6-D13
A65-B53-C6-D13
A66-B53-C6-D13
A2-B79-C6-D13
A3-B79-C6-D13
A9-B79-C6-D13
A13-B79-C6-D13
A24-B79-C6-D13
A69-B79-C6-D13
A67-B79-C6-D13
A39-B79-C6-D13
A65-B79-C6-D13
A66-B79-C6-D13
A2-B80-C6-D13
A3-B80-C6-D13
A9-B80-C6-D13
A13-B80-C6-D13
A24-B80-C6-D13
A69-B80-C6-D13
A67-B80-C6-D13
A39-B80-C6-D13
A65-B80-C6-D13
A66-B80-C6-D13
A2-B85-C6-D13
A3-B85-C6-D13
A9-B85-C6-D13
A13-B85-C6-D13
A24-B85-C6-D13

-continued
A69-B85-C6-D13
A67-B85-C6-D13
A39-B85-C6-D13
A65-B85-C6-D13
A66-B85-C6-D13
A2-B86-C6-D13
A3-B86-C6-D13
A9-B86-C6-D13
A13-B86-C6-D13
A24-B86-C6-D13
A69-B86-C6-D13
A67-B86-C6-D13
A39-B86-C6-D13
A65-B86-C6-D13
A66-B86-C6-D13
A2-B87-C6-D13
A3-B87-C6-D13
A9-B87-C6-D13
A13-B87-C6-D13
A24-B87-C6-D13
A69-B87-C6-D13
A67-B87-C6-D13
A39-B87-C6-D13
A65-B87-C6-D13
A66-B87-C6-D13
A2-B89-C6-D13
A3-B89-C6-D13
A9-B89-C6-D13
A13-B89-C6-D13
A24-B89-C6-D13
A69-B89-C6-D13
A67-B89-C6-D13
A39-B89-C6-D13
A65-B89-C6-D13
A66-B89-C6-D13
A2-B92-C6-D13
A3-B92-C6-D13
A9-B92-C6-D13
A13-B92-C6-D13
A24-B92-C6-D13
A69-B92-C6-D13
A67-B92-C6-D13
A39-B92-C6-D13
A65-B92-C6-D13
A66-B92-C6-D13
A2-B4-C7-D13
A3-B4-C7-D13
A9-B4-C7-D13
A13-B4-C7-D13
A24-B4-C7-D13
A69-B4-C7-D13
A67-B4-C7-D13
A39-B4-C7-D13
A65-B4-C7-D13
A66-B4-C7-D13
A2-B5-C7-D13
A3-B5-C7-D13
A9-B5-C7-D13
A13-B5-C7-D13
A24-B5-C7-D13
A69-B5-C7-D13
A67-B5-C7-D13
A39-B5-C7-D13
A65-B5-C7-D13
A66-B5-C7-D13
A2-B6-C7-D13
A3-B6-C7-D13
A9-B6-C7-D13
A13-B6-C7-D13
A24-B6-C7-D13
A69-B6-C7-D13
A67-B6-C7-D13
A39-B6-C7-D13
A65-B6-C7-D13
A66-B6-C7-D13
A2-B32-C7-D13
A3-B32-C7-D13
A9-B32-C7-D13
A13-B32-C7-D13
A24-B32-C7-D13

-continued
A69-B32-C7-D13
A67-B32-C7-D13
A39-B32-C7-D13
A65-B32-C7-D13
A66-B32-C7-D13
A2-B39-C7-D13
A3-B39-C7-D13
A9-B39-C7-D13
A13-B39-C7-D13
A24-B39-C7-D13
A69-B39-C7-D13
A67-B39-C7-D13
A39-B39-C7-D13
A65-B39-C7-D13
A66-B39-C7-D13
A2-B45-C7-D13
A3-B45-C7-D13
A9-B45-C7-D13
A13-B45-C7-D13
A24-B45-C7-D13
A69-B45-C7-D13
A67-B45-C7-D13
A39-B45-C7-D13
A65-B45-C7-D13
A66-B45-C7-D13
A2-B53-C7-D13
A3-B53-C7-D13
A9-B53-C7-D13
A13-B53-C7-D13
A24-B53-C7-D13
A69-B53-C7-D13
A67-B53-C7-D13
A39-B53-C7-D13
A65-B53-C7-D13
A66-B53-C7-D13
A2-B79-C7-D13
A3-B79-C7-D13
A9-B79-C7-D13
A13-B79-C7-D13
A24-B79-C7-D13
A69-B79-C7-D13
A67-B79-C7-D13
A39-B79-C7-D13
A65-B79-C7-D13
A66-B79-C7-D13
A2-B80-C7-D13
A3-B80-C7-D13
A9-B80-C7-D13
A13-B80-C7-D13
A24-B80-C7-D13
A69-B80-C7-D13
A67-B80-C7-D13
A39-B80-C7-D13
A65-B80-C7-D13
A66-B80-C7-D13
A2-B85-C7-D13
A3-B85-C7-D13
A9-B85-C7-D13
A13-B85-C7-D13
A24-B85-C7-D13
A69-B85-C7-D13
A67-B85-C7-D13
A39-B85-C7-D13
A65-B85-C7-D13
A66-B85-C7-D13
A2-B86-C7-D13
A3-B86-C7-D13
A9-B86-C7-D13
A13-B86-C7-D13
A24-B86-C7-D13
A69-B86-C7-D13
A67-B86-C7-D13
A39-B86-C7-D13
A65-B86-C7-D13
A66-B86-C7-D13
A2-B87-C7-D13
A3-B87-C7-D13
A9-B87-C7-D13
A13-B87-C7-D13
A24-B87-C7-D13

-continued
A69-B87-C7-D13
A67-B87-C7-D13
A39-B87-C7-D13
A65-B87-C7-D13
A66-B87-C7-D13
A2-B89-C7-D13
A3-B89-C7-D13
A9-B89-C7-D13
A13-B89-C7-D13
A24-B89-C7-D13
A69-B89-C7-D13
A67-B89-C7-D13
A39-B89-C7-D13
A65-B89-C7-D13
A66-B89-C7-D13
A2-B92-C7-D13
A3-B92-C7-D13
A9-B92-C7-D13
A13-B92-C7-D13
A24-B92-C7-D13
A69-B92-C7-D13
A67-B92-C7-D13
A39-B92-C7-D13
A65-B92-C7-D13
A66-B92-C7-D13
A2-B4-C8-D13
A3-B4-C8-D13
A9-B4-C8-D13
A13-B4-C8-D13
A24-B4-C8-D13
A69-B4-C8-D13
A67-B4-C8-D13
A39-B4-C8-D13
A65-B4-C8-D13
A66-B4-C8-D13
A2-B5-C8-D13
A3-B5-C8-D13
A9-B5-C8-D13
A13-B5-C8-D13
A24-B5-C8-D13
A69-B5-C8-D13
A67-B5-C8-D13
A39-B5-C8-D13
A65-B5-C8-D13
A66-B5-C8-D13
A2-B6-C8-D13
A3-B6-C8-D13
A9-B6-C8-D13
A13-B6-C8-D13
A24-B6-C8-D13
A69-B6-C8-D13
A67-B6-C8-D13
A39-B6-C8-D13
A65-B6-C8-D13
A66-B6-C8-D13
A2-B32-C8-D13
A3-B32-C8-D13
A9-B32-C8-D13
A13-B32-C8-D13
A24-B32-C8-D13
A69-B32-C8-D13
A67-B32-C8-D13
A39-B32-C8-D13
A65-B32-C8-D13
A66-B32-C8-D13
A2-B39-C8-D13
A3-B39-C8-D13
A9-B39-C8-D13
A13-B39-C8-D13
A24-B39-C8-D13
A69-B39-C8-D13
A67-B39-C8-D13
A39-B39-C8-D13
A65-B39-C8-D13
A66-B39-C8-D13
A2-B45-C8-D13
A3-B45-C8-D13
A9-B45-C8-D13
A13-B45-C8-D13
A24-B45-C8-D13

-continued
A69-B45-C8-D13
A67-B45-C8-D13
A39-B45-C8-D13
A65-B45-C8-D13
A66-B45-C8-D13
A2-B53-C8-D13
A3-B53-C8-D13
A9-B53-C8-D13
A13-B53-C8-D13
A24-B53-C8-D13
A69-B53-C8-D13
A67-B53-C8-D13
A39-B53-C8-D13
A65-B53-C8-D13
A66-B53-C8-D13
A2-B79-C8-D13
A3-B79-C8-D13
A9-B79-C8-D13
A13-B79-C8-D13
A24-B79-C8-D13
A69-B79-C8-D13
A67-B79-C8-D13
A39-B79-C8-D13
A65-B79-C8-D13
A66-B79-C8-D13
A2-B80-C8-D13
A3-B80-C8-D13
A9-B80-C8-D13
A13-B80-C8-D13
A24-B80-C8-D13
A69-B80-C8-D13
A67-B80-C8-D13
A39-B80-C8-D13
A65-B80-C8-D13
A66-B80-C8-D13
A2-B85-C8-D13
A3-B85-C8-D13
A9-B85-C8-D13
A13-B85-C8-D13
A24-B85-C8-D13
A69-B85-C8-D13
A67-B85-C8-D13
A39-B85-C8-D13
A65-B85-C8-D13
A66-B85-C8-D13
A2-B86-C8-D13
A3-B86-C8-D13
A9-B86-C8-D13
A13-B86-C8-D13
A24-B86-C8-D13
A69-B86-C8-D13
A67-B86-C8-D13
A39-B86-C8-D13
A65-B86-C8-D13
A66-B86-C8-D13
A2-B87-C8-D13
A3-B87-C8-D13
A9-B87-C8-D13
A13-B87-C8-D13
A24-B87-C8-D13
A69-B87-C8-D13
A67-B87-C8-D13
A39-B87-C8-D13
A65-B87-C8-D13
A66-B87-C8-D13
A2-B89-C8-D13
A3-B89-C8-D13
A9-B89-C8-D13
A13-B89-C8-D13
A24-B89-C8-D13
A69-B89-C8-D13
A67-B89-C8-D13
A39-B89-C8-D13
A65-B89-C8-D13
A66-B89-C8-D13
A2-B92-C8-D13
A3-B92-C8-D13
A9-B92-C8-D13
A13-B92-C8-D13
A24-B92-C8-D13

-continued
A69-B92-C8-D13
A67-B92-C8-D13
A39-B92-C8-D13
A65-B92-C8-D13
A66-B92-C8-D13
A2-B4-C9-D13
A3-B4-C9-D13
A9-B4-C9-D13
A13-B4-C9-D13
A24-B4-C9-D13
A69-B4-C9-D13
A67-B4-C9-D13
A39-B4-C9-D13
A65-B4-C9-D13
A66-B4-C9-D13
A2-B5-C9-D13
A3-B5-C9-D13
A9-B5-C9-D13
A13-B5-C9-D13
A24-B5-C9-D13
A69-B5-C9-D13
A67-B5-C9-D13
A39-B5-C9-D13
A65-B5-C9-D13
A66-B5-C9-D13
A2-B6-C9-D13
A3-B6-C9-D13
A9-B6-C9-D13
A13-B6-C9-D13
A24-B6-C9-D13
A69-B6-C9-D13
A67-B6-C9-D13
A39-B6-C9-D13
A65-B6-C9-D13
A66-B6-C9-D13
A2-B32-C9-D13
A3-B32-C9-D13
A9-B32-C9-D13
A13-B32-C9-D13
A24-B32-C9-D13
A69-B32-C9-D13
A67-B32-C9-D13
A39-B32-C9-D13
A65-B32-C9-D13
A66-B32-C9-D13
A2-B39-C9-D13
A3-B39-C9-D13
A9-B39-C9-D13
A13-B39-C9-D13
A24-B39-C9-D13
A69-B39-C9-D13
A67-B39-C9-D13
A39-B39-C9-D13
A65-B39-C9-D13
A66-B39-C9-D13
A2-B45-C9-D13
A3-B45-C9-D13
A9-B45-C9-D13
A13-B45-C9-D13
A24-B45-C9-D13
A69-B45-C9-D13
A67-B45-C9-D13
A39-B45-C9-D13
A65-B45-C9-D13
A66-B45-C9-D13
A2-B53-C9-D13
A3-B53-C9-D13
A9-B53-C9-D13
A13-B53-C9-D13
A24-B53-C9-D13
A69-B53-C9-D13
A67-B53-C9-D13
A39-B53-C9-D13
A65-B53-C9-D13
A66-B53-C9-D13
A2-B79-C9-D13
A3-B79-C9-D13
A9-B79-C9-D13
A13-B79-C9-D13
A24-B79-C9-D13

-continued
A69-B79-C9-D13
A67-B79-C9-D13
A39-B79-C9-D13
A65-B79-C9-D13
A66-B79-C9-D13
A2-B80-C9-D13
A3-B80-C9-D13
A9-B80-C9-D13
A13-B80-C9-D13
A24-B80-C9-D13
A69-B80-C9-D13
A67-B80-C9-D13
A39-B80-C9-D13
A65-B80-C9-D13
A66-B80-C9-D13
A2-B85-C9-D13
A3-B85-C9-D13
A9-B85-C9-D13
A13-B85-C9-D13
A24-B85-C9-D13
A69-B85-C9-D13
A67-B85-C9-D13
A39-B85-C9-D13
A65-B85-C9-D13
A66-B85-C9-D13
A2-B86-C9-D13
A3-B86-C9-D13
A9-B86-C9-D13
A13-B86-C9-D13
A24-B86-C9-D13
A69-B86-C9-D13
A67-B86-C9-D13
A39-B86-C9-D13
A65-B86-C9-D13
A66-B86-C9-D13
A2-B87-C9-D13
A3-B87-C9-D13
A9-B87-C9-D13
A13-B87-C9-D13
A24-B87-C9-D13
A69-B87-C9-D13
A67-B87-C9-D13
A39-B87-C9-D13
A65-B87-C9-D13
A66-B87-C9-D13
A2-B89-C9-D13
A3-B89-C9-D13
A9-B89-C9-D13
A13-B89-C9-D13
A24-B89-C9-D13
A69-B89-C9-D13
A67-B89-C9-D13
A39-B89-C9-D13
A65-B89-C9-D13
A66-B89-C9-D13
A2-B92-C9-D13
A3-B92-C9-D13
A9-B92-C9-D13
A13-B92-C9-D13
A24-B92-C9-D13
A69-B92-C9-D13
A67-B92-C9-D13
A39-B92-C9-D13
A65-B92-C9-D13
A66-B92-C9-D13
A2-B4-C10-D13
A3-B4-C10-D13
A9-B4-C10-D13
A13-B4-C10-D13
A24-B4-C10-D13
A69-B4-C10-D13
A67-B4-C10-D13
A39-B4-C10-D13
A65-B4-C10-D13
A66-B4-C10-D13
A2-B5-C10-D13
A3-B5-C10-D13
A9-B5-C10-D13
A13-B5-C10-D13
A24-B5-C10-D13

-continued
A69-B5-C10-D13
A67-B5-C10-D13
A39-B5-C10-D13
A65-B5-C10-D13
A66-B5-C10-D13
A2-B6-C10-D13
A3-B6-C10-D13
A9-B6-C10-D13
A13-B6-C10-D13
A24-B6-C10-D13
A69-B6-C10-D13
A67-B6-C10-D13
A39-B6-C10-D13
A65-B6-C10-D13
A66-B6-C10-D13
A2-B32-C10-D13
A3-B32-C10-D13
A9-B32-C10-D13
A13-B32-C10-D13
A24-B32-C10-D13
A69-B32-C10-D13
A67-B32-C10-D13
A39-B32-C10-D13
A65-B32-C10-D13
A66-B32-C10-D13
A2-B39-C10-D13
A3-B39-C10-D13
A9-B39-C10-D13
A13-B39-C10-D13
A24-B39-C10-D13
A69-B39-C10-D13
A67-B39-C10-D13
A39-B39-C10-D13
A65-B39-C10-D13
A66-B39-C10-D13
A2-B45-C10-D13
A3-B45-C10-D13
A9-B45-C10-D13
A13-B45-C10-D13
A24-B45-C10-D13
A69-B45-C10-D13
A67-B45-C10-D13
A39-B45-C10-D13
A65-B45-C10-D13
A66-B45-C10-D13
A2-B53-C10-D13
A3-B53-C10-D13
A9-B53-C10-D13
A13-B53-C10-D13
A24-B53-C10-D13
A69-B53-C10-D13
A67-B53-C10-D13
A39-B53-C10-D13
A65-B53-C10-D13
A66-B53-C10-D13
A2-B79-C10-D13
A3-B79-C10-D13
A9-B79-C10-D13
A13-B79-C10-D13
A24-B79-C10-D13
A69-B79-C10-D13
A67-B79-C10-D13
A39-B79-C10-D13
A65-B79-C10-D13
A66-B79-C10-D13
A2-B80-C10-D13
A3-B80-C10-D13
A9-B80-C10-D13
A13-B80-C10-D13
A24-B80-C10-D13
A69-B80-C10-D13
A67-B80-C10-D13
A39-B80-C10-D13
A65-B80-C10-D13
A66-B80-C10-D13
A2-B85-C10-D13
A3-B85-C10-D13
A9-B85-C10-D13
A13-B85-C10-D13
A24-B85-C10-D13

-continued
A69-B85-C10-D13
A67-B85-C10-D13
A39-B85-C10-D13
A65-B85-C10-D13
A66-B85-C10-D13
A2-B86-C10-D13
A3-B86-C10-D13
A9-B86-C10-D13
A13-B86-C10-D13
A24-B86-C10-D13
A69-B86-C10-D13
A67-B86-C10-D13
A39-B86-C10-D13
A65-B86-C10-D13
A66-B86-C10-D13
A2-B87-C10-D13
A3-B87-C10-D13
A9-B87-C10-D13
A13-B87-C10-D13
A24-B87-C10-D13
A69-B87-C10-D13
A67-B87-C10-D13
A39-B87-C10-D13
A65-B87-C10-D13
A66-B87-C10-D13
A2-B89-C10-D13
A3-B89-C10-D13
A9-B89-C10-D13
A13-B89-C10-D13
A24-B89-C10-D13
A69-B89-C10-D13
A67-B89-C10-D13
A39-B89-C10-D13
A65-B89-C10-D13
A66-B89-C10-D13
A2-B92-C10-D13
A3-B92-C10-D13
A9-B92-C10-D13
A13-B92-C10-D13
A24-B92-C10-D13
A69-B92-C10-D13
A67-B92-C10-D13
A39-B92-C10-D13
A65-B92-C10-D13
A66-B92-C10-D13
A2-B4-C11-D13
A3-B4-C11-D13
A9-B4-C11-D13
A13-B4-C11-D13
A24-B4-C11-D13
A69-B4-C11-D13
A67-B4-C11-D13
A39-B4-C11-D13
A65-B4-C11-D13
A66-B4-C11-D13
A2-B5-C11-D13
A3-B5-C11-D13
A9-B5-C11-D13
A13-B5-C11-D13
A24-B5-C11-D13
A69-B5-C11-D13
A67-B5-C11-D13
A39-B5-C11-D13
A65-B5-C11-D13
A66-B5-C11-D13
A2-B6-C11-D13
A3-B6-C11-D13
A9-B6-C11-D13
A13-B6-C11-D13
A24-B6-C11-D13
A69-B6-C11-D13
A67-B6-C11-D13
A39-B6-C11-D13
A65-B6-C11-D13
A66-B6-C11-D13
A2-B32-C11-D13
A3-B32-C11-D13
A9-B32-C11-D13
A13-B32-C11-D13
A24-B32-C11-D13

-continued

A69-B32-C11-D13
A67-B32-C11-D13
A39-B32-C11-D13
A65-B32-C11-D13
A66-B32-C11-D13
A2-B39-C11-D13
A3-B39-C11-D13
A9-B39-C11-D13
A13-B39-C11-D13
A24-B39-C11-D13
A69-B39-C11-D13
A67-B39-C11-D13
A39-B39-C11-D13
A65-B39-C11-D13
A66-B39-C11-D13
A2-B45-C11-D13
A3-B45-C11-D13
A9-B45-C11-D13
A13-B45-C11-D13
A24-B45-C11-D13
A69-B45-C11-D13
A67-B45-C11-D13
A39-B45-C11-D13
A65-B45-C11-D13
A66-B45-C11-D13
A2-B53-C11-D13
A3-B53-C11-D13
A9-B53-C11-D13
A13-B53-C11-D13
A24-B53-C11-D13
A69-B53-C11-D13
A67-B53-C11-D13
A39-B53-C11-D13
A65-B53-C11-D13
A66-B53-C11-D13
A2-B79-C11-D13
A3-B79-C11-D13
A9-B79-C11-D13
A13-B79-C11-D13
A24-B79-C11-D13
A69-B79-C11-D13
A67-B79-C11-D13
A39-B79-C11-D13
A65-B79-C11-D13
A66-B79-C11-D13
A2-B80-C11-D13
A3-B80-C11-D13
A9-B80-C11-D13
A13-B80-C11-D13
A24-B80-C11-D13
A69-B80-C11-D13
A67-B80-C11-D13
A39-B80-C11-D13
A65-B80-C11-D13
A66-B80-C11-D13
A2-B85-C11-D13
A3-B85-C11-D13
A9-B85-C11-D13
A13-B85-C11-D13
A24-B85-C11-D13
A69-B85-C11-D13
A67-B85-C11-D13
A39-B85-C11-D13
A65-B85-C11-D13
A66-B85-C11-D13
A2-B86-C11-D13
A3-B86-C11-D13
A9-B86-C11-D13
A13-B86-C11-D13
A24-B86-C11-D13
A69-B86-C11-D13
A67-B86-C11-D13
A39-B86-C11-D13
A65-B86-C11-D13
A66-B86-C11-D13
A2-B87-C11-D13
A3-B87-C11-D13
A9-B87-C11-D13
A13-B87-C11-D13
A24-B87-C11-D13

-continued

A69-B87-C11-D13
A67-B87-C11-D13
A39-B87-C11-D13
A65-B87-C11-D13
A66-B87-C11-D13
A2-B89-C11-D13
A3-B89-C11-D13
A9-B89-C11-D13
A13-B89-C11-D13
A24-B89-C11-D13
A69-B89-C11-D13
A67-B89-C11-D13
A39-B89-C11-D13
A65-B89-C11-D13
A66-B89-C11-D13
A2-B92-C11-D13
A3-B92-C11-D13
A9-B92-C11-D13
A13-B92-C11-D13
A24-B92-C11-D13
A69-B92-C11-D13
A67-B92-C11-D13
A39-B92-C11-D13
A65-B92-C11-D13
A66-B92-C11-D13
A2-B4-C12-D13
A3-B4-C12-D13
A9-B4-C12-D13
A13-B4-C12-D13
A24-B4-C12-D13
A69-B4-C12-D13
A67-B4-C12-D13
A39-B4-C12-D13
A65-B4-C12-D13
A66-B4-C12-D13
A2-B5-C12-D13
A3-B5-C12-D13
A9-B5-C12-D13
A13-B5-C12-D13
A24-B5-C12-D13
A69-B5-C12-D13
A67-B5-C12-D13
A39-B5-C12-D13
A65-B5-C12-D13
A66-B5-C12-D13
A2-B6-C12-D13
A3-B6-C12-D13
A9-B6-C12-D13
A13-B6-C12-D13
A24-B6-C12-D13
A69-B6-C12-D13
A67-B6-C12-D13
A39-B6-C12-D13
A65-B6-C12-D13
A66-B6-C12-D13
A2-B32-C12-D13
A3-B32-C12-D13
A9-B32-C12-D13
A13-B32-C12-D13
A24-B32-C12-D13
A69-B32-C12-D13
A67-B32-C12-D13
A39-B32-C12-D13
A65-B32-C12-D13
A66-B32-C12-D13
A2-B39-C12-D13
A3-B39-C12-D13
A9-B39-C12-D13
A13-B39-C12-D13
A24-B39-C12-D13
A69-B39-C12-D13
A67-B39-C12-D13
A39-B39-C12-D13
A65-B39-C12-D13
A66-B39-C12-D13
A2-B45-C12-D13
A3-B45-C12-D13
A9-B45-C12-D13
A13-B45-C12-D13
A24-B45-C12-D13

-continued

A69-B45-C12-D13
A67-B45-C12-D13
A39-B45-C12-D13
A65-B45-C12-D13
A66-B45-C12-D13
A2-B53-C12-D13
A3-B53-C12-D13
A9-B53-C12-D13
A13-B53-C12-D13
A24-B53-C12-D13
A69-B53-C12-D13
A67-B53-C12-D13
A39-B53-C12-D13
A65-B53-C12-D13
A66-B53-C12-D13
A2-B79-C12-D13
A3-B79-C12-D13
A9-B79-C12-D13
A13-B79-C12-D13
A24-B79-C12-D13
A69-B79-C12-D13
A67-B79-C12-D13
A39-B79-C12-D13
A65-B79-C12-D13
A66-B79-C12-D13
A2-B80-C12-D13
A3-B80-C12-D13
A9-B80-C12-D13
A13-B80-C12-D13
A24-B80-C12-D13
A69-B80-C12-D13
A67-B80-C12-D13
A39-B80-C12-D13
A65-B80-C12-D13
A66-B80-C12-D13
A2-B85-C12-D13
A3-B85-C12-D13
A9-B85-C12-D13
A13-B85-C12-D13
A24-B85-C12-D13
A69-B85-C12-D13
A67-B85-C12-D13
A39-B85-C12-D13
A65-B85-C12-D13
A66-B85-C12-D13
A2-B86-C12-D13
A3-B86-C12-D13
A9-B86-C12-D13
A13-B86-C12-D13
A24-B86-C12-D13
A69-B86-C12-D13
A67-B86-C12-D13
A39-B86-C12-D13
A65-B86-C12-D13
A66-B86-C12-D13
A2-B87-C12-D13
A3-B87-C12-D13
A9-B87-C12-D13
A13-B87-C12-D13
A24-B87-C12-D13
A69-B87-C12-D13
A67-B87-C12-D13
A39-B87-C12-D13
A65-B87-C12-D13
A66-B87-C12-D13
A2-B89-C12-D13
A3-B89-C12-D13
A9-B89-C12-D13
A13-B89-C12-D13
A24-B89-C12-D13
A69-B89-C12-D13
A67-B89-C12-D13
A39-B89-C12-D13
A65-B89-C12-D13
A66-B89-C12-D13
A2-B92-C12-D13
A3-B92-C12-D13
A9-B92-C12-D13
A13-B92-C12-D13
A24-B92-C12-D13

-continued

A69-B92-C12-D13
A67-B92-C12-D13
A39-B92-C12-D13
A65-B92-C12-D13
A66-B92-C12-D13
A2-B4-C13-D13
A3-B4-C13-D13
A9-B4-C13-D13
A13-B4-C13-D13
A24-B4-C13-D13
A69-B4-C13-D13
A67-B4-C13-D13
A39-B4-C13-D13
A65-B4-C13-D13
A66-B4-C13-D13
A2-B5-C13-D13
A3-B5-C13-D13
A9-B5-C13-D13
A13-B5-C13-D13
A24-B5-C13-D13
A69-B5-C13-D13
A67-B5-C13-D13
A39-B5-C13-D13
A65-B5-C13-D13
A66-B5-C13-D13
A2-B6-C13-D13
A3-B6-C13-D13
A9-B6-C13-D13
A13-B6-C13-D13
A24-B6-C13-D13
A69-B6-C13-D13
A67-B6-C13-D13
A39-B6-C13-D13
A65-B6-C13-D13
A66-B6-C13-D13
A2-B32-C13-D13
A3-B32-C13-D13
A9-B32-C13-D13
A13-B32-C13-D13
A24-B32-C13-D13
A69-B32-C13-D13
A67-B32-C13-D13
A39-B32-C13-D13
A65-B32-C13-D13
A66-B32-C13-D13
A2-B39-C13-D13
A3-B39-C13-D13
A9-B39-C13-D13
A13-B39-C13-D13
A24-B39-C13-D13
A69-B39-C13-D13
A67-B39-C13-D13
A39-B39-C13-D13
A65-B39-C13-D13
A66-B39-C13-D13
A2-B45-C13-D13
A3-B45-C13-D13
A9-B45-C13-D13
A13-B45-C13-D13
A24-B45-C13-D13
A69-B45-C13-D13
A67-B45-C13-D13
A39-B45-C13-D13
A65-B45-C13-D13
A66-B45-C13-D13
A2-B53-C13-D13
A3-B53-C13-D13
A9-B53-C13-D13
A13-B53-C13-D13
A24-B53-C13-D13
A69-B53-C13-D13
A67-B53-C13-D13
A39-B53-C13-D13
A65-B53-C13-D13
A66-B53-C13-D13
A2-B79-C13-D13
A3-B79-C13-D13
A9-B79-C13-D13
A13-B79-C13-D13
A24-B79-C13-D13

-continued

A69-B79-C13-D13
A67-B79-C13-D13
A39-B79-C13-D13
A65-B79-C13-D13
A66-B79-C13-D13
A2-B80-C13-D13
A3-B80-C13-D13
A9-B80-C13-D13
A13-B80-C13-D13
A24-B80-C13-D13
A69-B80-C13-D13
A67-B80-C13-D13
A39-B80-C13-D13
A65-B80-C13-D13
A66-B80-C13-D13
A2-B85-C13-D13
A3-B85-C13-D13
A9-B85-C13-D13
A13-B85-C13-D13
A24-B85-C13-D13
A69-B85-C13-D13
A67-B85-C13-D13
A39-B85-C13-D13
A65-B85-C13-D13
A66-B85-C13-D13
A2-B86-C13-D13
A3-B86-C13-D13
A9-B86-C13-D13
A13-B86-C13-D13
A24-B86-C13-D13
A69-B86-C13-D13
A67-B86-C13-D13
A39-B86-C13-D13
A65-B86-C13-D13
A66-B86-C13-D13
A2-B87-C13-D13
A3-B87-C13-D13
A9-B87-C13-D13
A13-B87-C13-D13
A24-B87-C13-D13
A69-B87-C13-D13
A67-B87-C13-D13
A39-B87-C13-D13
A65-B87-C13-D13
A66-B87-C13-D13
A2-B89-C13-D13
A3-B89-C13-D13
A9-B89-C13-D13
A13-B89-C13-D13
A24-B89-C13-D13
A69-B89-C13-D13
A67-B89-C13-D13
A39-B89-C13-D13
A65-B89-C13-D13
A66-B89-C13-D13
A2-B92-C13-D13
A3-B92-C13-D13
A9-B92-C13-D13
A13-B92-C13-D13
A24-B92-C13-D13
A69-B92-C13-D13
A67-B92-C13-D13
A39-B92-C13-D13
A65-B92-C13-D13
A66-B92-C13-D13
A2-B4-C1-D14
A3-B4-C1-D14
A9-B4-C1-D14
A13-B4-C1-D14
A24-B4-C1-D14
A69-B4-C1-D14
A67-B4-C1-D14
A39-B4-C1-D14
A65-B4-C1-D14
A66-B4-C1-D14
A2-B5-C1-D14
A3-B5-C1-D14
A9-B5-C1-D14
A13-B5-C1-D14
A24-B5-C1-D14

-continued

A69-B5-C1-D14
A67-B5-C1-D14
A39-B5-C1-D14
A65-B5-C1-D14
A66-B5-C1-D14
A2-B6-C1-D14
A3-B6-C1-D14
A9-B6-C1-D14
A13-B6-C1-D14
A24-B6-C1-D14
A69-B6-C1-D14
A67-B6-C1-D14
A39-B6-C1-D14
A65-B6-C1-D14
A66-B6-C1-D14
A2-B32-C1-D14
A3-B32-C1-D14
A9-B32-C1-D14
A13-B32-C1-D14
A24-B32-C1-D14
A69-B32-C1-D14
A67-B32-C1-D14
A39-B32-C1-D14
A65-B32-C1-D14
A66-B32-C1-D14
A2-B39-C1-D14
A3-B39-C1-D14
A9-B39-C1-D14
A13-B39-C1-D14
A24-B39-C1-D14
A69-B39-C1-D14
A67-B39-C1-D14
A39-B39-C1-D14
A65-B39-C1-D14
A66-B39-C1-D14
A2-B45-C1-D14
A3-B45-C1-D14
A9-B45-C1-D14
A13-B45-C1-D14
A24-B45-C1-D14
A69-B45-C1-D14
A67-B45-C1-D14
A39-B45-C1-D14
A65-B45-C1-D14
A66-B45-C1-D14
A2-B53-C1-D14
A3-B53-C1-D14
A9-B53-C1-D14
A13-B53-C1-D14
A24-B53-C1-D14
A69-B53-C1-D14
A67-B53-C1-D14
A39-B53-C1-D14
A65-B53-C1-D14
A66-B53-C1-D14
A2-B79-C1-D14
A3-B79-C1-D14
A9-B79-C1-D14
A13-B79-C1-D14
A24-B79-C1-D14
A69-B79-C1-D14
A67-B79-C1-D14
A39-B79-C1-D14
A65-B79-C1-D14
A66-B79-C1-D14
A2-B80-C1-D14
A3-B80-C1-D14
A9-B80-C1-D14
A13-B80-C1-D14
A24-B80-C1-D14
A69-B80-C1-D14
A67-B80-C1-D14
A39-B80-C1-D14
A65-B80-C1-D14
A66-B80-C1-D14
A2-B85-C1-D14
A3-B85-C1-D14
A9-B85-C1-D14
A13-B85-C1-D14
A24-B85-C1-D14

-continued
A69-B85-C1-D14
A67-B85-C1-D14
A39-B85-C1-D14
A65-B85-C1-D14
A66-B85-C1-D14
A2-B86-C1-D14
A3-B86-C1-D14
A9-B86-C1-D14
A13-B86-C1-D14
A24-B86-C1-D14
A69-B86-C1-D14
A67-B86-C1-D14
A39-B86-C1-D14
A65-B86-C1-D14
A66-B86-C1-D14
A2-B87-C1-D14
A3-B87-C1-D14
A9-B87-C1-D14
A13-B87-C1-D14
A24-B87-C1-D14
A69-B87-C1-D14
A67-B87-C1-D14
A39-B87-C1-D14
A65-B87-C1-D14
A66-B87-C1-D14
A2-B89-C1-D14
A3-B89-C1-D14
A9-B89-C1-D14
A13-B89-C1-D14
A24-B89-C1-D14
A69-B89-C1-D14
A67-B89-C1-D14
A39-B89-C1-D14
A65-B89-C1-D14
A66-B89-C1-D14
A2-B92-C1-D14
A3-B92-C1-D14
A9-B92-C1-D14
A13-B92-C1-D14
A24-B92-C1-D14
A69-B92-C1-D14
A67-B92-C1-D14
A39-B92-C1-D14
A65-B92-C1-D14
A66-B92-C1-D14
A2-B4-C2-D14
A3-B4-C2-D14
A9-B4-C2-D14
A13-B4-C2-D14
A24-B4-C2-D14
A69-B4-C2-D14
A67-B4-C2-D14
A39-B4-C2-D14
A65-B4-C2-D14
A66-B4-C2-D14
A2-B5-C2-D14
A3-B5-C2-D14
A9-B5-C2-D14
A13-B5-C2-D14
A24-B5-C2-D14
A69-B5-C2-D14
A67-B5-C2-D14
A39-B5-C2-D14
A65-B5-C2-D14
A66-B5-C2-D14
A2-B6-C2-D14
A3-B6-C2-D14
A9-B6-C2-D14
A13-B6-C2-D14
A24-B6-C2-D14
A69-B6-C2-D14
A67-B6-C2-D14
A39-B6-C2-D14
A65-B6-C2-D14
A66-B6-C2-D14
A2-B32-C2-D14
A3-B32-C2-D14
A9-B32-C2-D14
A13-B32-C2-D14
A24-B32-C2-D14

-continued
A69-B32-C2-D14
A67-B32-C2-D14
A39-B32-C2-D14
A65-B32-C2-D14
A66-B32-C2-D14
A2-B39-C2-D14
A3-B39-C2-D14
A9-B39-C2-D14
A13-B39-C2-D14
A24-B39-C2-D14
A69-B39-C2-D14
A67-B39-C2-D14
A39-B39-C2-D14
A65-B39-C2-D14
A66-B39-C2-D14
A2-B45-C2-D14
A3-B45-C2-D14
A9-B45-C2-D14
A13-B45-C2-D14
A24-B45-C2-D14
A69-B45-C2-D14
A67-B45-C2-D14
A39-B45-C2-D14
A65-B45-C2-D14
A66-B45-C2-D14
A2-B53-C2-D14
A3-B53-C2-D14
A9-B53-C2-D14
A13-B53-C2-D14
A24-B53-C2-D14
A69-B53-C2-D14
A67-B53-C2-D14
A39-B53-C2-D14
A65-B53-C2-D14
A66-B53-C2-D14
A2-B79-C2-D14
A3-B79-C2-D14
A9-B79-C2-D14
A13-B79-C2-D14
A24-B79-C2-D14
A69-B79-C2-D14
A67-B79-C2-D14
A39-B79-C2-D14
A65-B79-C2-D14
A66-B79-C2-D14
A2-B80-C2-D14
A3-B80-C2-D14
A9-B80-C2-D14
A13-B80-C2-D14
A24-B80-C2-D14
A69-B80-C2-D14
A67-B80-C2-D14
A39-B80-C2-D14
A65-B80-C2-D14
A66-B80-C2-D14
A2-B85-C2-D14
A3-B85-C2-D14
A9-B85-C2-D14
A13-B85-C2-D14
A24-B85-C2-D14
A69-B85-C2-D14
A67-B85-C2-D14
A39-B85-C2-D14
A65-B85-C2-D14
A66-B85-C2-D14
A2-B86-C2-D14
A3-B86-C2-D14
A9-B86-C2-D14
A13-B86-C2-D14
A24-B86-C2-D14
A69-B86-C2-D14
A67-B86-C2-D14
A39-B86-C2-D14
A65-B86-C2-D14
A66-B86-C2-D14
A2-B87-C2-D14
A3-B87-C2-D14
A9-B87-C2-D14
A13-B87-C2-D14
A24-B87-C2-D14

-continued

A69-B87-C2-D14
A67-B87-C2-D14
A39-B87-C2-D14
A65-B87-C2-D14
A66-B87-C2-D14
A2-B89-C2-D14
A3-B89-C2-D14
A9-B89-C2-D14
A13-B89-C2-D14
A24-B89-C2-D14
A69-B89-C2-D14
A67-B89-C2-D14
A39-B89-C2-D14
A65-B89-C2-D14
A66-B89-C2-D14
A2-B92-C2-D14
A3-B92-C2-D14
A9-B92-C2-D14
A13-B92-C2-D14
A24-B92-C2-D14
A69-B92-C2-D14
A67-B92-C2-D14
A39-B92-C2-D14
A65-B92-C2-D14
A66-B92-C2-D14
A2-B4-C3-D14
A3-B4-C3-D14
A9-B4-C3-D14
A13-B4-C3-D14
A24-B4-C3-D14
A69-B4-C3-D14
A67-B4-C3-D14
A39-B4-C3-D14
A65-B4-C3-D14
A66-B4-C3-D14
A2-B5-C3-D14
A3-B5-C3-D14
A9-B5-C3-D14
A13-B5-C3-D14
A24-B5-C3-D14
A69-B5-C3-D14
A67-B5-C3-D14
A39-B5-C3-D14
A65-B5-C3-D14
A66-B5-C3-D14
A2-B6-C3-D14
A3-B6-C3-D14
A9-B6-C3-D14
A13-B6-C3-D14
A24-B6-C3-D14
A69-B6-C3-D14
A67-B6-C3-D14
A39-B6-C3-D14
A65-B6-C3-D14
A66-B6-C3-D14
A2-B32-C3-D14
A3-B32-C3-D14
A9-B32-C3-D14
A13-B32-C3-D14
A24-B32-C3-D14
A69-B32-C3-D14
A67-B32-C3-D14
A39-B32-C3-D14
A65-B32-C3-D14
A66-B32-C3-D14
A2-B39-C3-D14
A3-B39-C3-D14
A9-B39-C3-D14
A13-B39-C3-D14
A24-B39-C3-D14
A69-B39-C3-D14
A67-B39-C3-D14
A39-B39-C3-D14
A65-B39-C3-D14
A66-B39-C3-D14
A2-B45-C3-D14
A3-B45-C3-D14
A9-B45-C3-D14
A13-B45-C3-D14
A24-B45-C3-D14

-continued

A69-B45-C3-D14
A67-B45-C3-D14
A39-B45-C3-D14
A65-B45-C3-D14
A66-B45-C3-D14
A2-B53-C3-D14
A3-B53-C3-D14
A9-B53-C3-D14
A13-B53-C3-D14
A24-B53-C3-D14
A69-B53-C3-D14
A67-B53-C3-D14
A39-B53-C3-D14
A65-B53-C3-D14
A66-B53-C3-D14
A2-B79-C3-D14
A3-B79-C3-D14
A9-B79-C3-D14
A13-B79-C3-D14
A24-B79-C3-D14
A69-B79-C3-D14
A67-B79-C3-D14
A39-B79-C3-D14
A65-B79-C3-D14
A66-B79-C3-D14
A2-B80-C3-D14
A3-B80-C3-D14
A9-B80-C3-D14
A13-B80-C3-D14
A24-B80-C3-D14
A69-B80-C3-D14
A67-B80-C3-D14
A39-B80-C3-D14
A65-B80-C3-D14
A66-B80-C3-D14
A2-B85-C3-D14
A3-B85-C3-D14
A9-B85-C3-D14
A13-B85-C3-D14
A24-B85-C3-D14
A69-B85-C3-D14
A67-B85-C3-D14
A39-B85-C3-D14
A65-B85-C3-D14
A66-B85-C3-D14
A2-B86-C3-D14
A3-B86-C3-D14
A9-B86-C3-D14
A13-B86-C3-D14
A24-B86-C3-D14
A69-B86-C3-D14
A67-B86-C3-D14
A39-B86-C3-D14
A65-B86-C3-D14
A66-B86-C3-D14
A2-B87-C3-D14
A3-B87-C3-D14
A9-B87-C3-D14
A13-B87-C3-D14
A24-B87-C3-D14
A69-B87-C3-D14
A67-B87-C3-D14
A39-B87-C3-D14
A65-B87-C3-D14
A66-B87-C3-D14
A2-B89-C3-D14
A3-B89-C3-D14
A9-B89-C3-D14
A13-B89-C3-D14
A24-B89-C3-D14
A69-B89-C3-D14
A67-B89-C3-D14
A39-B89-C3-D14
A65-B89-C3-D14
A66-B89-C3-D14
A2-B92-C3-D14
A3-B92-C3-D14
A9-B92-C3-D14
A13-B92-C3-D14
A24-B92-C3-D14

-continued
A69-B92-C3-D14
A67-B92-C3-D14
A39-B92-C3-D14
A65-B92-C3-D14
A66-B92-C3-D14
A2-B4-C4-D14
A3-B4-C4-D14
A9-B4-C4-D14
A13-B4-C4-D14
A24-B4-C4-D14
A69-B4-C4-D14
A67-B4-C4-D14
A39-B4-C4-D14
A65-B4-C4-D14
A66-B4-C4-D14
A2-B5-C4-D14
A3-B5-C4-D14
A9-B5-C4-D14
A13-B5-C4-D14
A24-B5-C4-D14
A69-B5-C4-D14
A67-B5-C4-D14
A39-B5-C4-D14
A65-B5-C4-D14
A66-B5-C4-D14
A2-B6-C4-D14
A3-B6-C4-D14
A9-B6-C4-D14
A13-B6-C4-D14
A24-B6-C4-D14
A69-B6-C4-D14
A67-B6-C4-D14
A39-B6-C4-D14
A65-B6-C4-D14
A66-B6-C4-D14
A2-B32-C4-D14
A3-B32-C4-D14
A9-B32-C4-D14
A13-B32-C4-D14
A24-B32-C4-D14
A69-B32-C4-D14
A67-B32-C4-D14
A39-B32-C4-D14
A65-B32-C4-D14
A66-B32-C4-D14
A2-B39-C4-D14
A3-B39-C4-D14
A9-B39-C4-D14
A13-B39-C4-D14
A24-B39-C4-D14
A69-B39-C4-D14
A67-B39-C4-D14
A39-B39-C4-D14
A65-B39-C4-D14
A66-B39-C4-D14
A2-B45-C4-D14
A3-B45-C4-D14
A9-B45-C4-D14
A13-B45-C4-D14
A24-B45-C4-D14
A69-B45-C4-D14
A67-B45-C4-D14
A39-B45-C4-D14
A65-B45-C4-D14
A66-B45-C4-D14
A2-B53-C4-D14
A3-B53-C4-D14
A9-B53-C4-D14
A13-B53-C4-D14
A24-B53-C4-D14
A69-B53-C4-D14
A67-B53-C4-D14
A39-B53-C4-D14
A65-B53-C4-D14
A66-B53-C4-D14
A2-B79-C4-D14
A3-B79-C4-D14
A9-B79-C4-D14
A13-B79-C4-D14
A24-B79-C4-D14

-continued
A69-B79-C4-D14
A67-B79-C4-D14
A39-B79-C4-D14
A65-B79-C4-D14
A66-B79-C4-D14
A2-B80-C4-D14
A3-B80-C4-D14
A9-B80-C4-D14
A13-B80-C4-D14
A24-B80-C4-D14
A69-B80-C4-D14
A67-B80-C4-D14
A39-B80-C4-D14
A65-B80-C4-D14
A66-B80-C4-D14
A2-B85-C4-D14
A3-B85-C4-D14
A9-B85-C4-D14
A13-B85-C4-D14
A24-B85-C4-D14
A69-B85-C4-D14
A67-B85-C4-D14
A39-B85-C4-D14
A65-B85-C4-D14
A66-B85-C4-D14
A2-B86-C4-D14
A3-B86-C4-D14
A9-B86-C4-D14
A13-B86-C4-D14
A24-B86-C4-D14
A69-B86-C4-D14
A67-B86-C4-D14
A39-B86-C4-D14
A65-B86-C4-D14
A66-B86-C4-D14
A2-B87-C4-D14
A3-B87-C4-D14
A9-B87-C4-D14
A13-B87-C4-D14
A24-B87-C4-D14
A69-B87-C4-D14
A67-B87-C4-D14
A39-B87-C4-D14
A65-B87-C4-D14
A66-B87-C4-D14
A2-B89-C4-D14
A3-B89-C4-D14
A9-B89-C4-D14
A13-B89-C4-D14
A24-B89-C4-D14
A69-B89-C4-D14
A67-B89-C4-D14
A39-B89-C4-D14
A65-B89-C4-D14
A66-B89-C4-D14
A2-B92-C4-D14
A3-B92-C4-D14
A9-B92-C4-D14
A13-B92-C4-D14
A24-B92-C4-D14
A69-B92-C4-D14
A67-B92-C4-D14
A39-B92-C4-D14
A65-B92-C4-D14
A66-B92-C4-D14
A2-B4-C5-D14
A3-B4-C5-D14
A9-B4-C5-D14
A13-B4-C5-D14
A24-B4-C5-D14
A69-B4-C5-D14
A67-B4-C5-D14
A39-B4-C5-D14
A65-B4-C5-D14
A66-B4-C5-D14
A2-B5-C5-D14
A3-B5-C5-D14
A9-B5-C5-D14
A13-B5-C5-D14
A24-B5-C5-D14

-continued

A69-B5-C5-D14
A67-B5-C5-D14
A39-B5-C5-D14
A65-B5-C5-D14
A66-B5-C5-D14
A2-B6-C5-D14
A3-B6-C5-D14
A9-B6-C5-D14
A13-B6-C5-D14
A24-B6-C5-D14
A69-B6-C5-D14
A67-B6-C5-D14
A39-B6-C5-D14
A65-B6-C5-D14
A66-B6-C5-D14
A2-B32-C5-D14
A3-B32-C5-D14
A9-B32-C5-D14
A13-B32-C5-D14
A24-B32-C5-D14
A69-B32-C5-D14
A67-B32-C5-D14
A39-B32-C5-D14
A65-B32-C5-D14
A66-B32-C5-D14
A2-B39-C5-D14
A3-B39-C5-D14
A9-B39-C5-D14
A13-B39-C5-D14
A24-B39-C5-D14
A69-B39-C5-D14
A67-B39-C5-D14
A39-B39-C5-D14
A65-B39-C5-D14
A66-B39-C5-D14
A2-B45-C5-D14
A3-B45-C5-D14
A9-B45-C5-D14
A13-B45-C5-D14
A24-B45-C5-D14
A69-B45-C5-D14
A67-B45-C5-D14
A39-B45-C5-D14
A65-B45-C5-D14
A66-B45-C5-D14
A2-B53-C5-D14
A3-B53-C5-D14
A9-B53-C5-D14
A13-B53-C5-D14
A24-B53-C5-D14
A69-B53-C5-D14
A67-B53-C5-D14
A39-B53-C5-D14
A65-B53-C5-D14
A66-B53-C5-D14
A2-B79-C5-D14
A3-B79-C5-D14
A9-B79-C5-D14
A13-B79-C5-D14
A24-B79-C5-D14
A69-B79-C5-D14
A67-B79-C5-D14
A39-B79-C5-D14
A65-B79-C5-D14
A66-B79-C5-D14
A2-B80-C5-D14
A3-B80-C5-D14
A9-B80-C5-D14
A13-B80-C5-D14
A24-B80-C5-D14
A69-B80-C5-D14
A67-B80-C5-D14
A39-B80-C5-D14
A65-B80-C5-D14
A66-B80-C5-D14
A2-B85-C5-D14
A3-B85-C5-D14
A9-B85-C5-D14
A13-B85-C5-D14
A24-B85-C5-D14

-continued

A69-B85-C5-D14
A67-B85-C5-D14
A39-B85-C5-D14
A65-B85-C5-D14
A66-B85-C5-D14
A2-B86-C5-D14
A3-B86-C5-D14
A9-B86-C5-D14
A13-B86-C5-D14
A24-B86-C5-D14
A69-B86-C5-D14
A67-B86-C5-D14
A39-B86-C5-D14
A65-B86-C5-D14
A66-B86-C5-D14
A2-B87-C5-D14
A3-B87-C5-D14
A9-B87-C5-D14
A13-B87-C5-D14
A24-B87-C5-D14
A69-B87-C5-D14
A67-B87-C5-D14
A39-B87-C5-D14
A65-B87-C5-D14
A66-B87-C5-D14
A2-B89-C5-D14
A3-B89-C5-D14
A9-B89-C5-D14
A13-B89-C5-D14
A24-B89-C5-D14
A69-B89-C5-D14
A67-B89-C5-D14
A39-B89-C5-D14
A65-B89-C5-D14
A66-B89-C5-D14
A2-B92-C5-D14
A3-B92-C5-D14
A9-B92-C5-D14
A13-B92-C5-D14
A24-B92-C5-D14
A69-B92-C5-D14
A67-B92-C5-D14
A39-B92-C5-D14
A65-B92-C5-D14
A66-B92-C5-D14
A2-B4-C6-D14
A3-B4-C6-D14
A9-B4-C6-D14
A13-B4-C6-D14
A24-B4-C6-D14
A69-B4-C6-D14
A67-B4-C6-D14
A39-B4-C6-D14
A65-B4-C6-D14
A66-B4-C6-D14
A2-B5-C6-D14
A3-B5-C6-D14
A9-B5-C6-D14
A13-B5-C6-D14
A24-B5-C6-D14
A69-B5-C6-D14
A67-B5-C6-D14
A39-B5-C6-D14
A65-B5-C6-D14
A66-B5-C6-D14
A2-B6-C6-D14
A3-B6-C6-D14
A9-B6-C6-D14
A13-B6-C6-D14
A24-B6-C6-D14
A69-B6-C6-D14
A67-B6-C6-D14
A39-B6-C6-D14
A65-B6-C6-D14
A66-B6-C6-D14
A2-B32-C6-D14
A3-B32-C6-D14
A9-B32-C6-D14
A13-B32-C6-D14
A24-B32-C6-D14

-continued

A69-B32-C6-D14
A67-B32-C6-D14
A39-B32-C6-D14
A65-B32-C6-D14
A66-B32-C6-D14
A2-B39-C6-D14
A3-B39-C6-D14
A9-B39-C6-D14
A13-B39-C6-D14
A24-B39-C6-D14
A69-B39-C6-D14
A67-B39-C6-D14
A39-B39-C6-D14
A65-B39-C6-D14
A66-B39-C6-D14
A2-B45-C6-D14
A3-B45-C6-D14
A9-B45-C6-D14
A13-B45-C6-D14
A24-B45-C6-D14
A69-B45-C6-D14
A67-B45-C6-D14
A39-B45-C6-D14
A65-B45-C6-D14
A66-B45-C6-D14
A2-B53-C6-D14
A3-B53-C6-D14
A9-B53-C6-D14
A13-B53-C6-D14
A24-B53-C6-D14
A69-B53-C6-D14
A67-B53-C6-D14
A39-B53-C6-D14
A65-B53-C6-D14
A66-B53-C6-D14
A2-B79-C6-D14
A3-B79-C6-D14
A9-B79-C6-D14
A13-B79-C6-D14
A24-B79-C6-D14
A69-B79-C6-D14
A67-B79-C6-D14
A39-B79-C6-D14
A65-B79-C6-D14
A66-B79-C6-D14
A2-B80-C6-D14
A3-B80-C6-D14
A9-B80-C6-D14
A13-B80-C6-D14
A24-B80-C6-D14
A69-B80-C6-D14
A67-B80-C6-D14
A39-B80-C6-D14
A65-B80-C6-D14
A66-B80-C6-D14
A2-B85-C6-D14
A3-B85-C6-D14
A9-B85-C6-D14
A13-B85-C6-D14
A24-B85-C6-D14
A69-B85-C6-D14
A67-B85-C6-D14
A39-B85-C6-D14
A65-B85-C6-D14
A66-B85-C6-D14
A2-B86-C6-D14
A3-B86-C6-D14
A9-B86-C6-D14
A13-B86-C6-D14
A24-B86-C6-D14
A69-B86-C6-D14
A67-B86-C6-D14
A39-B86-C6-D14
A65-B86-C6-D14
A66-B86-C6-D14
A2-B87-C6-D14
A3-B87-C6-D14
A9-B87-C6-D14
A13-B87-C6-D14
A24-B87-C6-D14

-continued

A69-B87-C6-D14
A67-B87-C6-D14
A39-B87-C6-D14
A65-B87-C6-D14
A66-B87-C6-D14
A2-B89-C6-D14
A3-B89-C6-D14
A9-B89-C6-D14
A13-B89-C6-D14
A24-B89-C6-D14
A69-B89-C6-D14
A67-B89-C6-D14
A39-B89-C6-D14
A65-B89-C6-D14
A66-B89-C6-D14
A2-B92-C6-D14
A3-B92-C6-D14
A9-B92-C6-D14
A13-B92-C6-D14
A24-B92-C6-D14
A69-B92-C6-D14
A67-B92-C6-D14
A39-B92-C6-D14
A65-B92-C6-D14
A66-B92-C6-D14
A2-B4-C7-D14
A3-B4-C7-D14
A9-B4-C7-D14
A13-B4-C7-D14
A24-B4-C7-D14
A69-B4-C7-D14
A67-B4-C7-D14
A39-B4-C7-D14
A65-B4-C7-D14
A66-B4-C7-D14
A2-B5-C7-D14
A3-B5-C7-D14
A9-B5-C7-D14
A13-B5-C7-D14
A24-B5-C7-D14
A69-B5-C7-D14
A67-B5-C7-D14
A39-B5-C7-D14
A65-B5-C7-D14
A66-B5-C7-D14
A2-B6-C7-D14
A3-B6-C7-D14
A9-B6-C7-D14
A13-B6-C7-D14
A24-B6-C7-D14
A69-B6-C7-D14
A67-B6-C7-D14
A39-B6-C7-D14
A65-B6-C7-D14
A66-B6-C7-D14
A2-B32-C7-D14
A3-B32-C7-D14
A9-B32-C7-D14
A13-B32-C7-D14
A24-B32-C7-D14
A69-B32-C7-D14
A67-B32-C7-D14
A39-B32-C7-D14
A65-B32-C7-D14
A66-B32-C7-D14
A2-B39-C7-D14
A3-B39-C7-D14
A9-B39-C7-D14
A13-B39-C7-D14
A24-B39-C7-D14
A69-B39-C7-D14
A67-B39-C7-D14
A39-B39-C7-D14
A65-B39-C7-D14
A66-B39-C7-D14
A2-B45-C7-D14
A3-B45-C7-D14
A9-B45-C7-D14
A13-B45-C7-D14
A24-B45-C7-D14

-continued
A69-B45-C7-D14
A67-B45-C7-D14
A39-B45-C7-D14
A65-B45-C7-D14
A66-B45-C7-D14
A2-B53-C7-D14
A3-B53-C7-D14
A9-B53-C7-D14
A13-B53-C7-D14
A24-B53-C7-D14
A69-B53-C7-D14
A67-B53-C7-D14
A39-B53-C7-D14
A65-B53-C7-D14
A66-B53-C7-D14
A2-B79-C7-D14
A3-B79-C7-D14
A9-B79-C7-D14
A13-B79-C7-D14
A24-B79-C7-D14
A69-B79-C7-D14
A67-B79-C7-D14
A39-B79-C7-D14
A65-B79-C7-D14
A66-B79-C7-D14
A2-B80-C7-D14
A3-B80-C7-D14
A9-B80-C7-D14
A13-B80-C7-D14
A24-B80-C7-D14
A69-B80-C7-D14
A67-B80-C7-D14
A39-B80-C7-D14
A65-B80-C7-D14
A66-B80-C7-D14
A2-B85-C7-D14
A3-B85-C7-D14
A9-B85-C7-D14
A13-B85-C7-D14
A24-B85-C7-D14
A69-B85-C7-D14
A67-B85-C7-D14
A39-B85-C7-D14
A65-B85-C7-D14
A66-B85-C7-D14
A2-B86-C7-D14
A3-B86-C7-D14
A9-B86-C7-D14
A13-B86-C7-D14
A24-B86-C7-D14
A69-B86-C7-D14
A67-B86-C7-D14
A39-B86-C7-D14
A65-B86-C7-D14
A66-B86-C7-D14
A2-B87-C7-D14
A3-B87-C7-D14
A9-B87-C7-D14
A13-B87-C7-D14
A24-B87-C7-D14
A69-B87-C7-D14
A67-B87-C7-D14
A39-B87-C7-D14
A65-B87-C7-D14
A66-B87-C7-D14
A2-B89-C7-D14
A3-B89-C7-D14
A9-B89-C7-D14
A13-B89-C7-D14
A24-B89-C7-D14
A69-B89-C7-D14
A67-B89-C7-D14
A39-B89-C7-D14
A65-B89-C7-D14
A66-B89-C7-D14
A2-B92-C7-D14
A3-B92-C7-D14
A9-B92-C7-D14
A13-B92-C7-D14
A24-B92-C7-D14

-continued
A69-B92-C7-D14
A67-B92-C7-D14
A39-B92-C7-D14
A65-B92-C7-D14
A66-B92-C7-D14
A2-B4-C8-D14
A3-B4-C8-D14
A9-B4-C8-D14
A13-B4-C8-D14
A24-B4-C8-D14
A69-B4-C8-D14
A67-B4-C8-D14
A39-B4-C8-D14
A65-B4-C8-D14
A66-B4-C8-D14
A2-B5-C8-D14
A3-B5-C8-D14
A9-B5-C8-D14
A13-B5-C8-D14
A24-B5-C8-D14
A69-B5-C8-D14
A67-B5-C8-D14
A39-B5-C8-D14
A65-B5-C8-D14
A66-B5-C8-D14
A2-B6-C8-D14
A3-B6-C8-D14
A9-B6-C8-D14
A13-B6-C8-D14
A24-B6-C8-D14
A69-B6-C8-D14
A67-B6-C8-D14
A39-B6-C8-D14
A65-B6-C8-D14
A66-B6-C8-D14
A2-B32-C8-D14
A3-B32-C8-D14
A9-B32-C8-D14
A13-B32-C8-D14
A24-B32-C8-D14
A69-B32-C8-D14
A67-B32-C8-D14
A39-B32-C8-D14
A65-B32-C8-D14
A66-B32-C8-D14
A2-B39-C8-D14
A3-B39-C8-D14
A9-B39-C8-D14
A13-B39-C8-D14
A24-B39-C8-D14
A69-B39-C8-D14
A67-B39-C8-D14
A39-B39-C8-D14
A65-B39-C8-D14
A66-B39-C8-D14
A2-B45-C8-D14
A3-B45-C8-D14
A9-B45-C8-D14
A13-B45-C8-D14
A24-B45-C8-D14
A69-B45-C8-D14
A67-B45-C8-D14
A39-B45-C8-D14
A65-B45-C8-D14
A66-B45-C8-D14
A2-B53-C8-D14
A3-B53-C8-D14
A9-B53-C8-D14
A13-B53-C8-D14
A24-B53-C8-D14
A69-B53-C8-D14
A67-B53-C8-D14
A39-B53-C8-D14
A65-B53-C8-D14
A66-B53-C8-D14
A2-B79-C8-D14
A3-B79-C8-D14
A9-B79-C8-D14
A13-B79-C8-D14
A24-B79-C8-D14

-continued
A69-B79-C8-D14
A67-B79-C8-D14
A39-B79-C8-D14
A65-B79-C8-D14
A66-B79-C8-D14
A2-B80-C8-D14
A3-B80-C8-D14
A9-B80-C8-D14
A13-B80-C8-D14
A24-B80-C8-D14
A69-B80-C8-D14
A67-B80-C8-D14
A39-B80-C8-D14
A65-B80-C8-D14
A66-B80-C8-D14
A2-B85-C8-D14
A3-B85-C8-D14
A9-B85-C8-D14
A13-B85-C8-D14
A24-B85-C8-D14
A69-B85-C8-D14
A67-B85-C8-D14
A39-B85-C8-D14
A65-B85-C8-D14
A66-B85-C8-D14
A2-B86-C8-D14
A3-B86-C8-D14
A9-B86-C8-D14
A13-B86-C8-D14
A24-B86-C8-D14
A69-B86-C8-D14
A67-B86-C8-D14
A39-B86-C8-D14
A65-B86-C8-D14
A66-B86-C8-D14
A2-B87-C8-D14
A3-B87-C8-D14
A9-B87-C8-D14
A13-B87-C8-D14
A24-B87-C8-D14
A69-B87-C8-D14
A67-B87-C8-D14
A39-B87-C8-D14
A65-B87-C8-D14
A66-B87-C8-D14
A2-B89-C8-D14
A3-B89-C8-D14
A9-B89-C8-D14
A13-B89-C8-D14
A24-B89-C8-D14
A69-B89-C8-D14
A67-B89-C8-D14
A39-B89-C8-D14
A65-B89-C8-D14
A66-B89-C8-D14
A2-B92-C8-D14
A3-B92-C8-D14
A9-B92-C8-D14
A13-B92-C8-D14
A24-B92-C8-D14
A69-B92-C8-D14
A67-B92-C8-D14
A39-B92-C8-D14
A65-B92-C8-D14
A66-B92-C8-D14
A2-B4-C9-D14
A3-B4-C9-D14
A9-B4-C9-D14
A13-B4-C9-D14
A24-B4-C9-D14
A69-B4-C9-D14
A67-B4-C9-D14
A39-B4-C9-D14
A65-B4-C9-D14
A66-B4-C9-D14
A2-B5-C9-D14
A3-B5-C9-D14
A9-B5-C9-D14
A13-B5-C9-D14
A24-B5-C9-D14

-continued
A69-B5-C9-D14
A67-B5-C9-D14
A39-B5-C9-D14
A65-B5-C9-D14
A66-B5-C9-D14
A2-B6-C9-D14
A3-B6-C9-D14
A9-B6-C9-D14
A13-B6-C9-D14
A24-B6-C9-D14
A69-B6-C9-D14
A67-B6-C9-D14
A39-B6-C9-D14
A65-B6-C9-D14
A66-B6-C9-D14
A2-B32-C9-D14
A3-B32-C9-D14
A9-B32-C9-D14
A13-B32-C9-D14
A24-B32-C9-D14
A69-B32-C9-D14
A67-B32-C9-D14
A39-B32-C9-D14
A65-B32-C9-D14
A66-B32-C9-D14
A2-B39-C9-D14
A3-B39-C9-D14
A9-B39-C9-D14
A13-B39-C9-D14
A24-B39-C9-D14
A69-B39-C9-D14
A67-B39-C9-D14
A39-B39-C9-D14
A65-B39-C9-D14
A66-B39-C9-D14
A2-B45-C9-D14
A3-B45-C9-D14
A9-B45-C9-D14
A13-B45-C9-D14
A24-B45-C9-D14
A69-B45-C9-D14
A67-B45-C9-D14
A39-B45-C9-D14
A65-B45-C9-D14
A66-B45-C9-D14
A2-B53-C9-D14
A3-B53-C9-D14
A9-B53-C9-D14
A13-B53-C9-D14
A24-B53-C9-D14
A69-B53-C9-D14
A67-B53-C9-D14
A39-B53-C9-D14
A65-B53-C9-D14
A66-B53-C9-D14
A2-B79-C9-D14
A3-B79-C9-D14
A9-B79-C9-D14
A13-B79-C9-D14
A24-B79-C9-D14
A69-B79-C9-D14
A67-B79-C9-D14
A39-B79-C9-D14
A65-B79-C9-D14
A66-B79-C9-D14
A2-B80-C9-D14
A3-B80-C9-D14
A9-B80-C9-D14
A13-B80-C9-D14
A24-B80-C9-D14
A69-B80-C9-D14
A67-B80-C9-D14
A39-B80-C9-D14
A65-B80-C9-D14
A66-B80-C9-D14
A2-B85-C9-D14
A3-B85-C9-D14
A9-B85-C9-D14
A13-B85-C9-D14
A24-B85-C9-D14

-continued
A69-B85-C9-D14
A67-B85-C9-D14
A39-B85-C9-D14
A65-B85-C9-D14
A66-B85-C9-D14
A2-B86-C9-D14
A3-B86-C9-D14
A9-B86-C9-D14
A13-B86-C9-D14
A24-B86-C9-D14
A69-B86-C9-D14
A67-B86-C9-D14
A39-B86-C9-D14
A65-B86-C9-D14
A66-B86-C9-D14
A2-B87-C9-D14
A3-B87-C9-D14
A9-B87-C9-D14
A13-B87-C9-D14
A24-B87-C9-D14
A69-B87-C9-D14
A67-B87-C9-D14
A39-B87-C9-D14
A65-B87-C9-D14
A66-B87-C9-D14
A2-B89-C9-D14
A3-B89-C9-D14
A9-B89-C9-D14
A13-B89-C9-D14
A24-B89-C9-D14
A69-B89-C9-D14
A67-B89-C9-D14
A39-B89-C9-D14
A65-B89-C9-D14
A66-B89-C9-D14
A2-B92-C9-D14
A3-B92-C9-D14
A9-B92-C9-D14
A13-B92-C9-D14
A24-B92-C9-D14
A69-B92-C9-D14
A67-B92-C9-D14
A39-B92-C9-D14
A65-B92-C9-D14
A66-B92-C9-D14
A2-B4-C10-D14
A3-B4-C10-D14
A9-B4-C10-D14
A13-B4-C10-D14
A24-B4-C10-D14
A69-B4-C10-D14
A67-B4-C10-D14
A39-B4-C10-D14
A65-B4-C10-D14
A66-B4-C10-D14
A2-B5-C10-D14
A3-B5-C10-D14
A9-B5-C10-D14
A13-B5-C10-D14
A24-B5-C10-D14
A69-B5-C10-D14
A67-B5-C10-D14
A39-B5-C10-D14
A65-B5-C10-D14
A66-B5-C10-D14
A2-B6-C10-D14
A3-B6-C10-D14
A9-B6-C10-D14
A13-B6-C10-D14
A24-B6-C10-D14
A69-B6-C10-D14
A67-B6-C10-D14
A39-B6-C10-D14
A65-B6-C10-D14
A66-B6-C10-D14
A2-B32-C10-D14
A3-B32-C10-D14
A9-B32-C10-D14
A13-B32-C10-D14
A24-B32-C10-D14

-continued
A69-B32-C10-D14
A67-B32-C10-D14
A39-B32-C10-D14
A65-B32-C10-D14
A66-B32-C10-D14
A2-B39-C10-D14
A3-B39-C10-D14
A9-B39-C10-D14
A13-B39-C10-D14
A24-B39-C10-D14
A69-B39-C10-D14
A67-B39-C10-D14
A39-B39-C10-D14
A65-B39-C10-D14
A66-B39-C10-D14
A2-B45-C10-D14
A3-B45-C10-D14
A9-B45-C10-D14
A13-B45-C10-D14
A24-B45-C10-D14
A69-B45-C10-D14
A67-B45-C10-D14
A39-B45-C10-D14
A65-B45-C10-D14
A66-B45-C10-D14
A2-B53-C10-D14
A3-B53-C10-D14
A9-B53-C10-D14
A13-B53-C10-D14
A24-B53-C10-D14
A69-B53-C10-D14
A67-B53-C10-D14
A39-B53-C10-D14
A65-B53-C10-D14
A66-B53-C10-D14
A2-B79-C10-D14
A3-B79-C10-D14
A9-B79-C10-D14
A13-B79-C10-D14
A24-B79-C10-D14
A69-B79-C10-D14
A67-B79-C10-D14
A39-B79-C10-D14
A65-B79-C10-D14
A66-B79-C10-D14
A2-B80-C10-D14
A3-B80-C10-D14
A9-B80-C10-D14
A13-B80-C10-D14
A24-B80-C10-D14
A69-B80-C10-D14
A67-B80-C10-D14
A39-B80-C10-D14
A65-B80-C10-D14
A66-B80-C10-D14
A2-B85-C10-D14
A3-B85-C10-D14
A9-B85-C10-D14
A13-B85-C10-D14
A24-B85-C10-D14
A69-B85-C10-D14
A67-B85-C10-D14
A39-B85-C10-D14
A65-B85-C10-D14
A66-B85-C10-D14
A2-B86-C10-D14
A3-B86-C10-D14
A9-B86-C10-D14
A13-B86-C10-D14
A24-B86-C10-D14
A69-B86-C10-D14
A67-B86-C10-D14
A39-B86-C10-D14
A65-B86-C10-D14
A66-B86-C10-D14
A2-B87-C10-D14
A3-B87-C10-D14
A9-B87-C10-D14
A13-B87-C10-D14
A24-B87-C10-D14

-continued

A69-B87-C10-D14
A67-B87-C10-D14
A39-B87-C10-D14
A65-B87-C10-D14
A66-B87-C10-D14
A2-B89-C10-D14
A3-B89-C10-D14
A9-B89-C10-D14
A13-B89-C10-D14
A24-B89-C10-D14
A69-B89-C10-D14
A67-B89-C10-D14
A39-B89-C10-D14
A65-B89-C10-D14
A66-B89-C10-D14
A2-B92-C10-D14
A3-B92-C10-D14
A9-B92-C10-D14
A13-B92-C10-D14
A24-B92-C10-D14
A69-B92-C10-D14
A67-B92-C10-D14
A39-B92-C10-D14
A65-B92-C10-D14
A66-B92-C10-D14
A2-B4-C11-D14
A3-B4-C11-D14
A9-B4-C11-D14
A13-B4-C11-D14
A24-B4-C11-D14
A69-B4-C11-D14
A67-B4-C11-D14
A39-B4-C11-D14
A65-B4-C11-D14
A66-B4-C11-D14
A2-B5-C11-D14
A3-B5-C11-D14
A9-B5-C11-D14
A13-B5-C11-D14
A24-B5-C11-D14
A69-B5-C11-D14
A67-B5-C11-D14
A39-B5-C11-D14
A65-B5-C11-D14
A66-B5-C11-D14
A2-B6-C11-D14
A3-B6-C11-D14
A9-B6-C11-D14
A13-B6-C11-D14
A24-B6-C11-D14
A69-B6-C11-D14
A67-B6-C11-D14
A39-B6-C11-D14
A65-B6-C11-D14
A66-B6-C11-D14
A2-B32-C11-D14
A3-B32-C11-D14
A9-B32-C11-D14
A13-B32-C11-D14
A24-B32-C11-D14
A69-B32-C11-D14
A67-B32-C11-D14
A39-B32-C11-D14
A65-B32-C11-D14
A66-B32-C11-D14
A2-B39-C11-D14
A3-B39-C11-D14
A9-B39-C11-D14
A13-B39-C11-D14
A24-B39-C11-D14
A69-B39-C11-D14
A67-B39-C11-D14
A39-B39-C11-D14
A65-B39-C11-D14
A66-B39-C11-D14
A2-B45-C11-D14
A3-B45-C11-D14
A9-B45-C11-D14
A13-B45-C11-D14
A24-B45-C11-D14

-continued

A69-B45-C11-D14
A67-B45-C11-D14
A39-B45-C11-D14
A65-B45-C11-D14
A66-B45-C11-D14
A2-B53-C11-D14
A3-B53-C11-D14
A9-B53-C11-D14
A13-B53-C11-D14
A24-B53-C11-D14
A69-B53-C11-D14
A67-B53-C11-D14
A39-B53-C11-D14
A65-B53-C11-D14
A66-B53-C11-D14
A2-B79-C11-D14
A3-B79-C11-D14
A9-B79-C11-D14
A13-B79-C11-D14
A24-B79-C11-D14
A69-B79-C11-D14
A67-B79-C11-D14
A39-B79-C11-D14
A65-B79-C11-D14
A66-B79-C11-D14
A2-B80-C11-D14
A3-B80-C11-D14
A9-B80-C11-D14
A13-B80-C11-D14
A24-B80-C11-D14
A69-B80-C11-D14
A67-B80-C11-D14
A39-B80-C11-D14
A65-B80-C11-D14
A66-B80-C11-D14
A2-B85-C11-D14
A3-B85-C11-D14
A9-B85-C11-D14
A13-B85-C11-D14
A24-B85-C11-D14
A69-B85-C11-D14
A67-B85-C11-D14
A39-B85-C11-D14
A65-B85-C11-D14
A66-B85-C11-D14
A2-B86-C11-D14
A3-B86-C11-D14
A9-B86-C11-D14
A13-B86-C11-D14
A24-B86-C11-D14
A69-B86-C11-D14
A67-B86-C11-D14
A39-B86-C11-D14
A65-B86-C11-D14
A66-B86-C11-D14
A2-B87-C11-D14
A3-B87-C11-D14
A9-B87-C11-D14
A13-B87-C11-D14
A24-B87-C11-D14
A69-B87-C11-D14
A67-B87-C11-D14
A39-B87-C11-D14
A65-B87-C11-D14
A66-B87-C11-D14
A2-B89-C11-D14
A3-B89-C11-D14
A9-B89-C11-D14
A13-B89-C11-D14
A24-B89-C11-D14
A69-B89-C11-D14
A67-B89-C11-D14
A39-B89-C11-D14
A65-B89-C11-D14
A66-B89-C11-D14
A2-B92-C11-D14
A3-B92-C11-D14
A9-B92-C11-D14
A13-B92-C11-D14
A24-B92-C11-D14

-continued

A69-B92-C11-D14
A67-B92-C11-D14
A39-B92-C11-D14
A65-B92-C11-D14
A66-B92-C11-D14
A2-B4-C12-D14
A3-B4-C12-D14
A9-B4-C12-D14
A13-B4-C12-D14
A24-B4-C12-D14
A69-B4-C12-D14
A67-B4-C12-D14
A39-B4-C12-D14
A65-B4-C12-D14
A66-B4-C12-D14
A2-B5-C12-D14
A3-B5-C12-D14
A9-B5-C12-D14
A13-B5-C12-D14
A24-B5-C12-D14
A69-B5-C12-D14
A67-B5-C12-D14
A39-B5-C12-D14
A65-B5-C12-D14
A66-B5-C12-D14
A2-B6-C12-D14
A3-B6-C12-D14
A9-B6-C12-D14
A13-B6-C12-D14
A24-B6-C12-D14
A69-B6-C12-D14
A67-B6-C12-D14
A39-B6-C12-D14
A65-B6-C12-D14
A66-B6-C12-D14
A2-B32-C12-D14
A3-B32-C12-D14
A9-B32-C12-D14
A13-B32-C12-D14
A24-B32-C12-D14
A69-B32-C12-D14
A67-B32-C12-D14
A39-B32-C12-D14
A65-B32-C12-D14
A66-B32-C12-D14
A2-B39-C12-D14
A3-B39-C12-D14
A9-B39-C12-D14
A13-B39-C12-D14
A24-B39-C12-D14
A69-B39-C12-D14
A67-B39-C12-D14
A39-B39-C12-D14
A65-B39-C12-D14
A66-B39-C12-D14
A2-B45-C12-D14
A3-B45-C12-D14
A9-B45-C12-D14
A13-B45-C12-D14
A24-B45-C12-D14
A69-B45-C12-D14
A67-B45-C12-D14
A39-B45-C12-D14
A65-B45-C12-D14
A66-B45-C12-D14
A2-B53-C12-D14
A3-B53-C12-D14
A9-B53-C12-D14
A13-B53-C12-D14
A24-B53-C12-D14
A69-B53-C12-D14
A67-B53-C12-D14
A39-B53-C12-D14
A65-B53-C12-D14
A66-B53-C12-D14
A2-B79-C12-D14
A3-B79-C12-D14
A9-B79-C12-D14
A13-B79-C12-D14
A24-B79-C12-D14

-continued

A69-B79-C12-D14
A67-B79-C12-D14
A39-B79-C12-D14
A65-B79-C12-D14
A66-B79-C12-D14
A2-B80-C12-D14
A3-B80-C12-D14
A9-B80-C12-D14
A13-B80-C12-D14
A24-B80-C12-D14
A69-B80-C12-D14
A67-B80-C12-D14
A39-B80-C12-D14
A65-B80-C12-D14
A66-B80-C12-D14
A2-B85-C12-D14
A3-B85-C12-D14
A9-B85-C12-D14
A13-B85-C12-D14
A24-B85-C12-D14
A69-B85-C12-D14
A67-B85-C12-D14
A39-B85-C12-D14
A65-B85-C12-D14
A66-B85-C12-D14
A2-B86-C12-D14
A3-B86-C12-D14
A9-B86-C12-D14
A13-B86-C12-D14
A24-B86-C12-D14
A69-B86-C12-D14
A67-B86-C12-D14
A39-B86-C12-D14
A65-B86-C12-D14
A66-B86-C12-D14
A2-B87-C12-D14
A3-B87-C12-D14
A9-B87-C12-D14
A13-B87-C12-D14
A24-B87-C12-D14
A69-B87-C12-D14
A67-B87-C12-D14
A39-B87-C12-D14
A65-B87-C12-D14
A66-B87-C12-D14
A2-B89-C12-D14
A3-B89-C12-D14
A9-B89-C12-D14
A13-B89-C12-D14
A24-B89-C12-D14
A69-B89-C12-D14
A67-B89-C12-D14
A39-B89-C12-D14
A65-B89-C12-D14
A66-B89-C12-D14
A2-B92-C12-D14
A3-B92-C12-D14
A9-B92-C12-D14
A13-B92-C12-D14
A24-B92-C12-D14
A69-B92-C12-D14
A67-B92-C12-D14
A39-B92-C12-D14
A65-B92-C12-D14
A66-B92-C12-D14
A2-B4-C13-D14
A3-B4-C13-D14
A9-B4-C13-D14
A13-B4-C13-D14
A24-B4-C13-D14
A69-B4-C13-D14
A67-B4-C13-D14
A39-B4-C13-D14
A65-B4-C13-D14
A66-B4-C13-D14
A2-B5-C13-D14
A3-B5-C13-D14
A9-B5-C13-D14
A13-B5-C13-D14
A24-B5-C13-D14

-continued

A69-B5-C13-D14
A67-B5-C13-D14
A39-B5-C13-D14
A65-B5-C13-D14
A66-B5-C13-D14
A2-B6-C13-D14
A3-B6-C13-D14
A9-B6-C13-D14
A13-B6-C13-D14
A24-B6-C13-D14
A69-B6-C13-D14
A67-B6-C13-D14
A39-B6-C13-D14
A65-B6-C13-D14
A66-B6-C13-D14
A2-B32-C13-D14
A3-B32-C13-D14
A9-B32-C13-D14
A13-B32-C13-D14
A24-B32-C13-D14
A69-B32-C13-D14
A67-B32-C13-D14
A39-B32-C13-D14
A65-B32-C13-D14
A66-B32-C13-D14
A2-B39-C13-D14
A3-B39-C13-D14
A9-B39-C13-D14
A13-B39-C13-D14
A24-B39-C13-D14
A69-B39-C13-D14
A67-B39-C13-D14
A39-B39-C13-D14
A65-B39-C13-D14
A66-B39-C13-D14
A2-B45-C13-D14
A3-B45-C13-D14
A9-B45-C13-D14
A13-B45-C13-D14
A24-B45-C13-D14
A69-B45-C13-D14
A67-B45-C13-D14
A39-B45-C13-D14
A65-B45-C13-D14
A66-B45-C13-D14
A2-B53-C13-D14
A3-B53-C13-D14
A9-B53-C13-D14
A13-B53-C13-D14
A24-B53-C13-D14
A69-B53-C13-D14
A67-B53-C13-D14
A39-B53-C13-D14
A65-B53-C13-D14
A66-B53-C13-D14
A2-B79-C13-D14
A3-B79-C13-D14
A9-B79-C13-D14
A13-B79-C13-D14
A24-B79-C13-D14
A69-B79-C13-D14
A67-B79-C13-D14
A39-B79-C13-D14
A65-B79-C13-D14
A66-B79-C13-D14
A2-B80-C13-D14
A3-B80-C13-D14
A9-B80-C13-D14
A13-B80-C13-D14
A24-B80-C13-D14
A69-B80-C13-D14
A67-B80-C13-D14
A39-B80-C13-D14
A65-B80-C13-D14
A66-B80-C13-D14
A2-B85-C13-D14
A3-B85-C13-D14
A9-B85-C13-D14
A13-B85-C13-D14
A24-B85-C13-D14

-continued

A69-B85-C13-D14
A67-B85-C13-D14
A39-B85-C13-D14
A65-B85-C13-D14
A66-B85-C13-D14
A2-B86-C13-D14
A3-B86-C13-D14
A9-B86-C13-D14
A13-B86-C13-D14
A24-B86-C13-D14
A69-B86-C13-D14
A67-B86-C13-D14
A39-B86-C13-D14
A65-B86-C13-D14
A66-B86-C13-D14
A2-B87-C13-D14
A3-B87-C13-D14
A9-B87-C13-D14
A13-B87-C13-D14
A24-B87-C13-D14
A69-B87-C13-D14
A67-B87-C13-D14
A39-B87-C13-D14
A65-B87-C13-D14
A66-B87-C13-D14
A2-B89-C13-D14
A3-B89-C13-D14
A9-B89-C13-D14
A13-B89-C13-D14
A24-B89-C13-D14
A69-B89-C13-D14
A67-B89-C13-D14
A39-B89-C13-D14
A65-B89-C13-D14
A66-B89-C13-D14
A2-B92-C13-D14
A3-B92-C13-D14
A9-B92-C13-D14
A13-B92-C13-D14
A24-B92-C13-D14
A69-B92-C13-D14
A67-B92-C13-D14
A39-B92-C13-D14
A65-B92-C13-D14
A66-B92-C13-D14
A2-B4-C1-D15
A3-B4-C1-D15
A9-B4-C1-D15
A13-B4-C1-D15
A24-B4-C1-D15
A69-B4-C1-D15
A67-B4-C1-D15
A39-B4-C1-D15
A65-B4-C1-D15
A66-B4-C1-D15
A2-B5-C1-D15
A3-B5-C1-D15
A9-B5-C1-D15
A13-B5-C1-D15
A24-B5-C1-D15
A69-B5-C1-D15
A67-B5-C1-D15
A39-B5-C1-D15
A65-B5-C1-D15
A66-B5-C1-D15
A2-B6-C1-D15
A3-B6-C1-D15
A9-B6-C1-D15
A13-B6-C1-D15
A24-B6-C1-D15
A69-B6-C1-D15
A67-B6-C1-D15
A39-B6-C1-D15
A65-B6-C1-D15
A66-B6-C1-D15
A2-B32-C1-D15
A3-B32-C1-D15
A9-B32-C1-D15
A13-B32-C1-D15
A24-B32-C1-D15

-continued
A69-B32-C1-D15
A67-B32-C1-D15
A39-B32-C1-D15
A65-B32-C1-D15
A66-B32-C1-D15
A2-B39-C1-D15
A3-B39-C1-D15
A9-B39-C1-D15
A13-B39-C1-D15
A24-B39-C1-D15
A69-B39-C1-D15
A67-B39-C1-D15
A39-B39-C1-D15
A65-B39-C1-D15
A66-B39-C1-D15
A2-B45-C1-D15
A3-B45-C1-D15
A9-B45-C1-D15
A13-B45-C1-D15
A24-B45-C1-D15
A69-B45-C1-D15
A67-B45-C1-D15
A39-B45-C1-D15
A65-B45-C1-D15
A66-B45-C1-D15
A2-B53-C1-D15
A3-B53-C1-D15
A9-B53-C1-D15
A13-B53-C1-D15
A24-B53-C1-D15
A69-B53-C1-D15
A67-B53-C1-D15
A39-B53-C1-D15
A65-B53-C1-D15
A66-B53-C1-D15
A2-B79-C1-D15
A3-B79-C1-D15
A9-B79-C1-D15
A13-B79-C1-D15
A24-B79-C1-D15
A69-B79-C1-D15
A67-B79-C1-D15
A39-B79-C1-D15
A65-B79-C1-D15
A66-B79-C1-D15
A2-B80-C1-D15
A3-B80-C1-D15
A9-B80-C1-D15
A13-B80-C1-D15
A24-B80-C1-D15
A69-B80-C1-D15
A67-B80-C1-D15
A39-B80-C1-D15
A65-B80-C1-D15
A66-B80-C1-D15
A2-B85-C1-D15
A3-B85-C1-D15
A9-B85-C1-D15
A13-B85-C1-D15
A24-B85-C1-D15
A69-B85-C1-D15
A67-B85-C1-D15
A39-B85-C1-D15
A65-B85-C1-D15
A66-B85-C1-D15
A2-B86-C1-D15
A3-B86-C1-D15
A9-B86-C1-D15
A13-B86-C1-D15
A24-B86-C1-D15
A69-B86-C1-D15
A67-B86-C1-D15
A39-B86-C1-D15
A65-B86-C1-D15
A66-B86-C1-D15
A2-B87-C1-D15
A3-B87-C1-D15
A9-B87-C1-D15
A13-B87-C1-D15
A24-B87-C1-D15

-continued
A69-B87-C1-DLS
A67-B87-C1-D15
A39-B87-C1-D15
A65-B87-C1-D15
A66-B87-C1-D15
A2-B89-C1-D15
A3-B89-C1-D15
A9-B89-C1-D15
A13-B89-C1-D15
A24-B89-C1-D15
A69-B89-C1-D15
A67-B89-C1-D15
A39-B89-C1-D15
A65-B89-C1-D15
A66-B89-C1-D15
A2-B92-C1-D15
A3-B92-C1-D15
A9-B92-C1-D15
A13-B92-C1-D15
A24-B92-C1-D15
A69-B92-C1-D15
A67-B92-C1-D15
A39-B92-C1-D15
A65-B92-C1-D15
A66-B92-C1-D15
A2-B4-C2-D15
A3-B4-C2-D15
A9-B4-C2-D15
A13-B4-C2-D15
A24-B4-C2-D15
A69-B4-C2-D15
A67-B4-C2-D15
A39-B4-C2-D15
A65-B4-C2-D15
A66-B4-C2-D15
A2-B5-C2-D15
A3-B5-C2-D15
A9-B5-C2-D15
A13-B5-C2-D15
A24-B5-C2-D15
A69-B5-C2-D15
A67-B5-C2-D15
A39-B5-C2-D15
A65-B5-C2-D15
A66-B5-C2-D15
A2-B6-C2-D15
A3-B6-C2-D15
A9-B6-C2-D15
A13-B6-C2-D15
A24-B6-C2-D15
A69-B6-C2-D15
A67-B6-C2-D15
A39-B6-C2-D15
A65-B6-C2-D15
A66-B6-C2-D15
A2-B32-C2-D15
A3-B32-C2-D15
A9-B32-C2-D15
A13-B32-C2-D15
A24-B32-C2-D15
A69-B32-C2-D15
A67-B32-C2-D15
A39-B32-C2-D15
A65-B32-C2-D15
A66-B32-C2-D15
A2-B39-C2-D15
A3-B39-C2-D15
A9-B39-C2-D15
A13-B39-C2-D15
A24-B39-C2-D15
A69-B39-C2-D15
A67-B39-C2-D15
A39-B39-C2-D15
A65-B39-C2-D15
A66-B39-C2-D15
A2-B45-C2-D15
A3-B45-C2-D15
A9-B45-C2-D15
A13-B45-C2-D15
A24-B45-C2-D15

-continued

A69-B45-C2-D15
A67-B45-C2-D15
A39-B45-C2-D15
A65-B45-C2-D15
A66-B45-C2-D15
A2-B53-C2-D15
A3-B53-C2-D15
A9-B53-C2-D15
A13-B53-C2-D15
A24-B53-C2-D15
A69-B53-C2-D15
A67-B53-C2-D15
A39-B53-C2-D15
A65-B53-C2-D15
A66-B53-C2-D15
A2-B79-C2-D15
A3-B79-C2-D15
A9-B79-C2-D15
A13-B79-C2-D15
A24-B79-C2-D15
A69-B79-C2-D15
A67-B79-C2-D15
A39-B79-C2-D15
A65-B79-C2-D15
A66-B79-C2-D15
A2-B80-C2-D15
A3-B80-C2-D15
A9-B80-C2-D15
A13-B80-C2-D15
A24-B80-C2-D15
A69-B80-C2-D15
A67-B80-C2-D15
A39-B80-C2-D15
A65-B80-C2-D15
A66-B80-C2-D15
A2-B85-C2-D15
A3-B85-C2-D15
A9-B85-C2-D15
A13-B85-C2-D15
A24-B85-C2-D15
A69-B85-C2-D15
A67-B85-C2-D15
A39-B85-C2-D15
A65-B85-C2-D15
A66-B85-C2-D15
A2-B86-C2-D15
A3-B86-C2-D15
A9-B86-C2-D15
A13-B86-C2-D15
A24-B86-C2-D15
A69-B86-C2-D15
A67-B86-C2-D15
A39-B86-C2-D15
A65-B86-C2-D15
A66-B86-C2-D15
A2-B87-C2-D15
A3-B87-C2-D15
A9-B87-C2-D15
A13-B87-C2-D15
A24-B87-C2-D15
A69-B87-C2-D15
A67-B87-C2-D15
A39-B87-C2-D15
A65-B87-C2-D15
A66-B87-C2-D15
A2-B89-C2-D15
A3-B89-C2-D15
A9-B89-C2-D15
A13-B89-C2-D15
A24-B89-C2-D15
A69-B89-C2-D15
A67-B89-C2-D15
A39-B89-C2-D15
A65-B89-C2-D15
A66-B89-C2-D15
A2-B92-C2-D15
A3-B92-C2-D15
A9-B92-C2-D15
A13-B92-C2-D15
A24-B92-C2-D15

-continued

A69-B92-C2-D15
A67-B92-C2-D15
A39-B92-C2-D15
A65-B92-C2-D15
A66-B92-C2-D15
A2-B4-C3-D15
A3-B4-C3-D15
A9-B4-C3-D15
A13-B4-C3-D15
A24-B4-C3-D15
A69-B4-C3-D15
A67-B4-C3-D15
A39-B4-C3-D15
A65-B4-C3-D15
A66-B4-C3-D15
A2-B5-C3-D15
A3-B5-C3-D15
A9-B5-C3-D15
A13-B5-C3-D15
A24-B5-C3-D15
A69-B5-C3-D15
A67-B5-C3-D15
A39-B5-C3-D15
A65-B5-C3-D15
A66-B5-C3-D15
A2-B6-C3-D15
A3-B6-C3-D15
A9-B6-C3-D15
A13-B6-C3-D15
A24-B6-C3-D15
A69-B6-C3-D15
A67-B6-C3-D15
A39-B6-C3-D15
A65-B6-C3-D15
A66-B6-C3-D15
A2-B32-C3-D15
A3-B32-C3-D15
A9-B32-C3-D15
A13-B32-C3-D15
A24-B32-C3-D15
A69-B32-C3-D15
A67-B32-C3-D15
A39-B32-C3-D15
A65-B32-C3-D15
A66-B32-C3-D15
A2-B39-C3-D15
A3-B39-C3-D15
A9-B39-C3-D15
A13-B39-C3-D15
A24-B39-C3-D15
A69-B39-C3-D15
A67-B39-C3-D15
A39-B39-C3-D15
A65-B39-C3-D15
A66-B39-C3-D15
A2-B45-C3-D15
A3-B45-C3-D15
A9-B45-C3-D15
A13-B45-C3-D15
A24-B45-C3-D15
A69-B45-C3-D15
A67-B45-C3-D15
A39-B45-C3-D15
A65-B45-C3-D15
A66-B45-C3-D15
A2-B53-C3-D15
A3-B53-C3-D15
A9-B53-C3-D15
A13-B53-C3-D15
A24-B53-C3-D15
A69-B53-C3-D15
A67-B53-C3-D15
A39-B53-C3-D15
A65-B53-C3-D15
A66-B53-C3-D15
A2-B79-C3-D15
A3-B79-C3-D15
A9-B79-C3-D15
A13-B79-C3-D15
A24-B79-C3-D15

-continued

A69-B79-C3-D15
A67-B79-C3-D15
A39-B79-C3-D15
A65-B79-C3-D15
A66-B79-C3-D15
A2-B80-C3-D15
A3-B80-C3-D15
A9-B80-C3-D15
A13-B80-C3-D15
A24-B80-C3-D15
A69-B80-C3-D15
A67-B80-C3-D15
A39-B80-C3-D15
A65-B80-C3-D15
A66-B80-C3-D15
A2-B85-C3-D15
A3-B85-C3-D15
A9-B85-C3-D15
A13-B85-C3-D15
A24-B85-C3-D15
A69-B85-C3-D15
A67-B85-C3-D15
A39-B85-C3-D15
A65-B85-C3-D15
A66-B85-C3-D15
A2-B86-C3-D15
A3-B86-C3-D15
A9-B86-C3-D15
A13-B86-C3-D15
A24-B86-C3-D15
A69-B86-C3-D15
A67-B86-C3-D15
A39-B86-C3-D15
A65-B86-C3-D15
A66-B86-C3-D15
A2-B87-C3-D15
A3-B87-C3-D15
A9-B87-C3-D15
A13-B87-C3-D15
A24-B87-C3-D15
A69-B87-C3-D15
A67-B87-C3-D15
A39-B87-C3-D15
A65-B87-C3-D15
A66-B87-C3-D15
A2-B89-C3-D15
A3-B89-C3-D15
A9-B89-C3-D15
A13-B89-C3-D15
A24-B89-C3-D15
A69-B89-C3-D15
A67-B89-C3-D15
A39-B89-C3-D15
A65-B89-C3-D15
A66-B89-C3-D15
A2-B92-C3-D15
A3-B92-C3-D15
A9-B92-C3-D15
A13-B92-C3-D15
A24-B92-C3-D15
A69-B92-C3-D15
A67-B92-C3-D15
A39-B92-C3-D15
A65-B92-C3-D15
A66-B92-C3-D15
A2-B4-C4-D15
A3-B4-C4-D15
A9-B4-C4-D15
A13-B4-C4-D15
A24-B4-C4-D15
A69-B4-C4-D15
A67-B4-C4-D15
A39-B4-C4-D15
A65-B4-C4-D15
A66-B4-C4-D15
A2-B5-C4-D15
A3-B5-C4-D15
A9-B5-C4-D15
A13-B5-C4-D15
A24-B5-C4-D15

-continued

A69-B5-C4-D15
A67-B5-C4-D15
A39-B5-C4-D15
A65-B5-C4-D15
A66-B5-C4-D15
A2-B6-C4-D15
A3-B6-C4-D15
A9-B6-C4-D15
A13-B6-C4-D15
A24-B6-C4-D15
A69-B6-C4-D15
A67-B6-C4-D15
A39-B6-C4-D15
A65-B6-C4-D15
A66-B6-C4-D15
A2-B32-C4-D15
A3-B32-C4-D15
A9-B32-C4-D15
A13-B32-C4-D15
A24-B32-C4-D15
A69-B32-C4-D15
A67-B32-C4-D15
A39-B32-C4-D15
A65-B32-C4-D15
A66-B32-C4-D15
A2-B39-C4-D15
A3-B39-C4-D15
A9-B39-C4-D15
A13-B39-C4-D15
A24-B39-C4-D15
A69-B39-C4-D15
A67-B39-C4-D15
A39-B39-C4-D15
A65-B39-C4-D15
A66-B39-C4-D15
A2-B45-C4-D15
A3-B45-C4-D15
A9-B45-C4-D15
A13-B45-C4-D15
A24-B45-C4-D15
A69-B45-C4-D15
A67-B45-C4-D15
A39-B45-C4-D15
A65-B45-C4-D15
A66-B45-C4-D15
A2-B53-C4-D15
A3-B53-C4-D15
A9-B53-C4-D15
A13-B53-C4-D15
A24-B53-C4-D15
A69-B53-C4-D15
A67-B53-C4-D15
A39-B53-C4-D15
A65-B53-C4-D15
A66-B53-C4-D15
A2-B79-C4-D15
A3-B79-C4-D15
A9-B79-C4-D15
A13-B79-C4-D15
A24-B79-C4-D15
A69-B79-C4-D15
A67-B79-C4-D15
A39-B79-C4-D15
A65-B79-C4-D15
A66-B79-C4-D15
A2-B80-C4-D15
A3-B80-C4-D15
A9-B80-C4-D15
A13-B80-C4-D15
A24-B80-C4-D15
A69-B80-C4-D15
A67-B80-C4-D15
A39-B80-C4-D15
A65-B80-C4-D15
A66-B80-C4-D15
A2-B85-C4-D15
A3-B85-C4-D15
A9-B85-C4-D15
A13-B85-C4-D15
A24-B85-C4-D15

-continued

A69-B85-C4-D15
A67-B85-C4-D15
A39-B85-C4-D15
A65-B85-C4-D15
A66-B85-C4-D15
A2-B86-C4-D15
A3-B86-C4-D15
A9-B86-C4-D15
A13-B86-C4-D15
A24-B86-C4-D15
A69-B86-C4-D15
A67-B86-C4-D15
A39-B86-C4-D15
A65-B86-C4-D15
A66-B86-C4-D15
A2-B87-C4-D15
A3-B87-C4-D15
A9-B87-C4-D15
A13-B87-C4-D15
A24-B87-C4-D15
A69-B87-C4-D15
A67-B87-C4-D15
A39-B87-C4-D15
A65-B87-C4-D15
A66-B87-C4-D15
A2-B89-C4-D15
A3-B89-C4-D15
A9-B89-C4-D15
A13-B89-C4-D15
A24-B89-C4-D15
A69-B89-C4-D15
A67-B89-C4-D15
A39-B89-C4-D15
A65-B89-C4-D15
A66-B89-C4-D15
A2-B92-C4-D15
A3-B92-C4-D15
A9-B92-C4-D15
A13-B92-C4-D15
A24-B92-C4-D15
A69-B92-C4-D15
A67-B92-C4-D15
A39-B92-C4-D15
A65-B92-C4-D15
A66-B92-C4-D15
A2-B4-C5-D15
A3-B4-C5-D15
A9-B4-C5-D15
A13-B4-C5-D15
A24-B4-C5-D15
A69-B4-C5-D15
A67-B4-C5-D15
A39-B4-C5-D15
A65-B4-C5-D15
A66-B4-C5-D15
A2-B5-C5-D15
A3-B5-C5-D15
A9-B5-C5-D15
A13-B5-C5-D15
A24-B5-C5-D15
A69-B5-C5-D15
A67-B5-C5-D15
A39-B5-C5-D15
A65-B5-C5-D15
A66-B5-C5-D15
A2-B6-C5-D15
A3-B6-C5-D15
A9-B6-C5-D15
A13-B6-C5-D15
A24-B6-C5-D15
A69-B6-C5-D15
A67-B6-C5-D15
A39-B6-C5-D15
A65-B6-C5-D15
A66-B6-C5-D15
A2-B32-C5-D15
A3-B32-C5-D15
A9-B32-C5-D15
A13-B32-C5-D15
A24-B32-C5-D15

-continued

A69-B32-C5-D15
A67-B32-C5-D15
A39-B32-C5-D15
A65-B32-C5-D15
A66-B32-C5-D15
A2-B39-C5-D15
A3-B39-C5-D15
A9-B39-C5-D15
A13-B39-C5-D15
A24-B39-C5-D15
A69-B39-C5-D15
A67-B39-C5-D15
A39-B39-C5-D15
A65-B39-C5-D15
A66-B39-C5-D15
A2-B45-C5-D15
A3-B45-C5-D15
A9-B45-C5-D15
A13-B45-C5-D15
A24-B45-C5-D15
A69-B45-C5-D15
A67-B45-C5-D15
A39-B45-C5-D15
A65-B45-C5-D15
A66-B45-C5-D15
A2-B53-C5-D15
A3-B53-C5-D15
A9-B53-C5-D15
A13-B53-C5-D15
A24-B53-C5-D15
A69-B53-C5-D15
A67-B53-C5-D15
A39-B53-C5-D15
A65-B53-C5-D15
A66-B53-C5-D15
A2-B79-C5-D15
A3-B79-C5-D15
A9-B79-C5-D15
A13-B79-C5-D15
A24-B79-C5-D15
A69-B79-C5-D15
A67-B79-C5-D15
A39-B79-C5-D15
A65-B79-C5-D15
A66-B79-C5-D15
A2-B80-C5-D15
A3-B80-C5-D15
A9-B80-C5-D15
A13-B80-C5-D15
A24-B80-C5-D15
A69-B80-C5-D15
A67-B80-C5-D15
A39-B80-C5-D15
A65-B80-C5-D15
A66-B80-C5-D15
A2-B85-C5-D15
A3-B85-C5-D15
A9-B85-C5-D15
A13-B85-C5-D15
A24-B85-C5-D15
A69-B85-C5-D15
A67-B85-C5-D15
A39-B85-C5-D15
A65-B85-C5-D15
A66-B85-C5-D15
A2-B86-C5-D15
A3-B86-C5-D15
A9-B86-C5-D15
A13-B86-C5-D15
A24-B86-C5-D15
A69-B86-C5-D15
A67-B86-C5-D15
A39-B86-C5-D15
A65-B86-C5-D15
A66-B86-C5-D15
A2-B87-C5-D15
A3-B87-C5-D15
A9-B87-C5-D15
A13-B87-C5-D15
A24-B87-C5-D15

-continued

A69-B87-C5-D15
A67-B87-C5-D15
A39-B87-C5-D15
A65-B87-C5-D15
A66-B87-C5-D15
A2-B89-C5-D15
A3-B89-C5-D15
A9-B89-C5-D15
A13-B89-C5-D15
A24-B89-C5-D15
A69-B89-C5-D15
A67-B89-C5-D15
A39-B89-C5-D15
A65-B89-C5-D15
A66-B89-C5-D15
A2-B92-C5-D15
A3-B92-C5-D15
A9-B92-C5-D15
A13-B92-C5-D15
A24-B92-C5-D15
A69-B92-C5-D15
A67-B92-C5-D15
A39-B92-C5-D15
A65-B92-C5-D15
A66-B92-C5-D15
A2-B4-C6-D15
A3-B4-C6-D15
A9-B4-C6-D15
A13-B4-C6-D15
A24-B4-C6-D15
A69-B4-C6-D15
A67-B4-C6-D15
A39-B4-C6-D15
A65-B4-C6-D15
A66-B4-C6-D15
A2-B5-C6-D15
A3-B5-C6-D15
A9-B5-C6-D15
A13-B5-C6-D15
A24-B5-C6-D15
A69-B5-C6-D15
A67-B5-C6-D15
A39-B5-C6-D15
A65-B5-C6-D15
A66-B5-C6-D15
A2-B6-C6-D15
A3-B6-C6-D15
A9-B6-C6-D15
A13-B6-C6-D15
A24-B6-C6-D15
A69-B6-C6-D15
A67-B6-C6-D15
A39-B6-C6-D15
A65-B6-C6-D15
A66-B6-C6-D15
A2-B32-C6-D15
A3-B32-C6-D15
A9-B32-C6-D15
A13-B32-C6-D15
A24-B32-C6-D15
A69-B32-C6-D15
A67-B32-C6-D15
A39-B32-C6-D15
A65-B32-C6-D15
A66-B32-C6-D15
A2-B39-C6-D15
A3-B39-C6-D15
A9-B39-C6-D15
A13-B39-C6-D15
A24-B39-C6-D15
A69-B39-C6-D15
A67-B39-C6-D15
A39-B39-C6-D15
A65-B39-C6-D15
A66-B39-C6-D15
A2-B45-C6-D15
A3-B45-C6-D15
A9-B45-C6-D15
A13-B45-C6-D15
A24-B45-C6-D15

-continued

A69-B45-C6-D15
A67-B45-C6-D15
A39-B45-C6-D15
A65-B45-C6-D15
A66-B45-C6-D15
A2-B53-C6-D15
A3-B53-C6-D15
A9-B53-C6-D15
A13-B53-C6-D15
A24-B53-C6-D15
A69-B53-C6-D15
A67-B53-C6-D15
A39-B53-C6-D15
A65-B53-C6-D15
A66-B53-C6-D15
A2-B79-C6-D15
A3-B79-C6-D15
A9-B79-C6-D15
A13-B79-C6-D15
A24-B79-C6-D15
A69-B79-C6-D15
A67-B79-C6-D15
A39-B79-C6-D15
A65-B79-C6-D15
A66-B79-C6-D15
A2-B80-C6-D15
A3-B80-C6-D15
A9-B80-C6-D15
A13-B80-C6-D15
A24-B80-C6-D15
A69-B80-C6-D15
A67-B80-C6-D15
A39-B80-C6-D15
A65-B80-C6-D15
A66-B80-C6-D15
A2-B85-C6-D15
A3-B85-C6-D15
A9-B85-C6-D15
A13-B85-C6-D15
A24-B85-C6-D15
A69-B85-C6-D15
A67-B85-C6-D15
A39-B85-C6-D15
A65-B85-C6-D15
A66-B85-C6-D15
A2-B86-C6-D15
A3-B86-C6-D15
A9-B86-C6-D15
A13-B86-C6-D15
A24-B86-C6-D15
A69-B86-C6-D15
A67-B86-C6-D15
A39-B86-C6-D15
A65-B86-C6-D15
A66-B86-C6-D15
A2-B87-C6-D15
A3-B87-C6-D15
A9-B87-C6-D15
A13-B87-C6-D15
A24-B87-C6-D15
A69-B87-C6-D15
A67-B87-C6-D15
A39-B87-C6-D15
A65-B87-C6-D15
A66-B87-C6-D15
A2-B89-C6-D15
A3-B89-C6-D15
A9-B89-C6-D15
A13-B89-C6-D15
A24-B89-C6-D15
A69-B89-C6-D15
A67-B89-C6-D15
A39-B89-C6-D15
A65-B89-C6-D15
A66-B89-C6-D15
A2-B92-C6-D15
A3-B92-C6-D15
A9-B92-C6-D15
A13-B92-C6-D15
A24-B92-C6-D15

-continued

```
A69-B92-C6-D15
A67-B92-C6-D15
A39-B92-C6-D15
A65-B92-C6-D15
A66-B92-C6-D15
A2-B4-C7-D15
A3-B4-C7-D15
A9-B4-C7-D15
A13-B4-C7-D15
A24-B4-C7-D15
A69-B4-C7-D15
A67-B4-C7-D15
A39-B4-C7-D15
A65-B4-C7-D15
A66-B4-C7-D15
A2-B5-C7-D15
A3-B5-C7-D15
A9-B5-C7-D15
A13-B5-C7-D15
A24-B5-C7-D15
A69-B5-C7-D15
A67-B5-C7-D15
A39-B5-C7-D15
A65-B5-C7-D15
A66-B5-C7-D15
A2-B6-C7-D15
A3-B6-C7-D15
A9-B6-C7-D15
A13-B6-C7-D15
A24-B6-C7-D15
A69-B6-C7-D15
A67-B6-C7-D15
A39-B6-C7-D15
A65-B6-C7-D15
A66-B6-C7-D15
A2-B32-C7-D15
A3-B32-C7-D15
A9-B32-C7-D15
A13-B32-C7-D15
A24-B32-C7-D15
A69-B32-C7-D15
A67-B32-C7-D15
A39-B32-C7-D15
A65-B32-C7-D15
A66-B32-C7-D15
A2-B39-C7-D15
A3-B39-C7-D15
A9-B39-C7-D15
A13-B39-C7-D15
A24-B39-C7-D15
A69-B39-C7-D15
A67-B39-C7-D15
A39-B39-C7-D15
A65-B39-C7-D15
A66-B39-C7-D15
A2-B45-C7-D15
A3-B45-C7-D15
A9-B45-C7-D15
A13-B45-C7-D15
A24-B45-C7-D15
A69-B45-C7-D15
A67-B45-C7-D15
A39-B45-C7-D15
A65-B45-C7-D15
A66-B45-C7-D15
A2-B53-C7-D15
A3-B53-C7-D15
A9-B53-C7-D15
A13-B53-C7-D15
A24-B53-C7-D15
A69-B53-C7-D15
A67-B53-C7-D15
A39-B53-C7-D15
A65-B53-C7-D15
A66-B53-C7-D15
A2-B79-C7-D15
A3-B79-C7-D15
A9-B79-C7-D15
A13-B79-C7-D15
A24-B79-C7-D15
```

-continued

```
A69-B79-C7-D15
A67-B79-C7-D15
A39-B79-C7-D15
A65-B79-C7-D15
A66-B79-C7-D15
A2-B80-C7-D15
A3-B80-C7-D15
A9-B80-C7-D15
A13-B80-C7-D15
A24-B80-C7-D15
A69-B80-C7-D15
A67-B80-C7-D15
A39-B80-C7-D15
A65-B80-C7-D15
A66-B80-C7-D15
A2-B85-C7-D15
A3-B85-C7-D15
A9-B85-C7-D15
A13-B85-C7-D15
A24-B85-C7-D15
A69-B85-C7-D15
A67-B85-C7-D15
A39-B85-C7-D15
A65-B85-C7-D15
A66-B85-C7-D15
A2-B86-C7-D15
A3-B86-C7-D15
A9-B86-C7-D15
A13-B86-C7-D15
A24-B86-C7-D15
A69-B86-C7-D15
A67-B86-C7-D15
A39-B86-C7-D15
A65-B86-C7-D15
A66-B86-C7-D15
A2-B87-C7-D15
A3-B87-C7-D15
A9-B87-C7-D15
A13-B87-C7-D15
A24-B87-C7-D15
A69-B87-C7-D15
A67-B87-C7-D15
A39-B87-C7-D15
A65-B87-C7-D15
A66-B87-C7-D15
A2-B89-C7-D15
A3-B89-C7-D15
A9-B89-C7-D15
A13-B89-C7-D15
A24-B89-C7-D15
A69-B89-C7-D15
A67-B89-C7-D15
A39-B89-C7-D15
A65-B89-C7-D15
A66-B89-C7-D15
A2-B92-C7-D15
A3-B92-C7-D15
A9-B92-C7-D15
A13-B92-C7-D15
A24-B92-C7-D15
A69-B92-C7-D15
A67-B92-C7-D15
A39-B92-C7-D15
A65-B92-C7-D15
A66-B92-C7-D15
A2-B4-C8-D15
A3-B4-C8-D15
A9-B4-C8-D15
A13-B4-C8-D15
A24-B4-C8-D15
A69-B4-C8-D15
A67-B4-C8-D15
A39-B4-C8-D15
A65-B4-C8-D15
A66-B4-C8-D15
A2-B5-C8-D15
A3-B5-C8-D15
A9-B5-C8-D15
A13-B5-C8-D15
A24-B5-C8-D15
```

-continued
A69-B5-C8-D15
A67-B5-C8-D15
A39-B5-C8-D15
A65-B5-C8-D15
A66-B5-C8-D15
A2-B6-C8-D15
A3-B6-C8-D15
A9-B6-C8-D15
A13-B6-C8-D15
A24-B6-C8-D15
A69-B6-C8-D15
A67-B6-C8-D15
A39-B6-C8-D15
A65-B6-C8-D15
A66-B6-C8-D15
A2-B32-C8-D15
A3-B32-C8-D15
A9-B32-C8-D15
A13-B32-C8-D15
A24-B32-C8-D15
A69-B32-C8-D15
A67-B32-C8-D15
A39-B32-C8-D15
A65-B32-C8-D15
A66-B32-C8-D15
A2-B39-C8-D15
A3-B39-C8-D15
A9-B39-C8-D15
A13-B39-C8-D15
A24-B39-C8-D15
A69-B39-C8-D15
A67-B39-C8-D15
A39-B39-C8-D15
A65-B39-C8-D15
A66-B39-C8-D15
A2-B45-C8-D15
A3-B45-C8-D15
A9-B45-C8-D15
A13-B45-C8-D15
A24-B45-C8-D15
A69-B45-C8-D15
A67-B45-C8-D15
A39-B45-C8-D15
A65-B45-C8-D15
A66-B45-C8-D15
A2-B53-C8-D15
A3-B53-C8-D15
A9-B53-C8-D15
A13-B53-C8-D15
A24-B53-C8-D15
A69-B53-C8-D15
A67-B53-C8-D15
A39-B53-C8-D15
A65-B53-C8-D15
A66-B53-C8-D15
A2-B79-C8-D15
A3-B79-C8-D15
A9-B79-C8-D15
A13-B79-C8-D15
A24-B79-C8-D15
A69-B79-C8-D15
A67-B79-C8-D15
A39-B79-C8-D15
A65-B79-C8-D15
A66-B79-C8-D15
A2-B80-C8-D15
A3-B80-C8-D15
A9-B80-C8-D15
A13-B80-C8-D15
A24-B80-C8-D15
A69-B80-C8-D15
A67-B80-C8-D15
A39-B80-C8-D15
A65-B80-C8-D15
A66-B80-C8-D15
A2-B85-C8-D15
A3-B85-C8-D15
A9-B85-C8-D15
A13-B85-C8-D15
A24-B85-C8-D15

-continued
A69-B85-C8-D15
A67-B85-C8-D15
A39-B85-C8-D15
A65-B85-C8-D15
A66-B85-C8-D15
A2-B86-C8-D15
A3-B86-C8-D15
A9-B86-C8-D15
A13-B86-C8-D15
A24-B86-C8-D15
A69-B86-C8-D15
A67-B86-C8-D15
A39-B86-C8-D15
A65-B86-C8-D15
A66-B86-C8-D15
A2-B87-C8-D15
A3-B87-C8-D15
A9-B87-C8-D15
A13-B87-C8-D15
A24-B87-C8-D15
A69-B87-C8-D15
A67-B87-C8-D15
A39-B87-C8-D15
A65-B87-C8-D15
A66-B87-C8-D15
A2-B89-C8-D15
A3-B89-C8-D15
A9-B89-C8-D15
A13-B89-C8-D15
A24-B89-C8-D15
A69-B89-C8-D15
A67-B89-C8-D15
A39-B89-C8-D15
A65-B89-C8-D15
A66-B89-C8-D15
A2-B92-C8-D15
A3-B92-C8-D15
A9-B92-C8-D15
A13-B92-C8-D15
A24-B92-C8-D15
A69-B92-C8-D15
A67-B92-C8-D15
A39-B92-C8-D15
A65-B92-C8-D15
A66-B92-C8-D15
A2-B4-C9-D15
A3-B4-C9-D15
A9-B4-C9-D15
A13-B4-C9-D15
A24-B4-C9-D15
A69-B4-C9-D15
A67-B4-C9-D15
A39-B4-C9-D15
A65-B4-C9-D15
A66-B4-C9-D15
A2-B5-C9-D15
A3-B5-C9-D15
A9-B5-C9-D15
A13-B5-C9-D15
A24-B5-C9-D15
A69-B5-C9-D15
A67-B5-C9-D15
A39-B5-C9-D15
A65-B5-C9-D15
A66-B5-C9-D15
A2-B6-C9-D15
A3-B6-C9-D15
A9-B6-C9-D15
A13-B6-C9-D15
A24-B6-C9-D15
A69-B6-C9-D15
A67-B6-C9-D15
A39-B6-C9-D15
A65-B6-C9-D15
A66-B6-C9-D15
A2-B32-C9-D15
A3-B32-C9-D15
A9-B32-C9-D15
A13-B32-C9-D15
A24-B32-C9-D15

-continued
A69-B32-C9-D15
A67-B32-C9-D15
A39-B32-C9-D15
A65-B32-C9-D15
A66-B32-C9-D15
A2-B39-C9-D15
A3-B39-C9-D15
A9-B39-C9-D15
A13-B39-C9-D15
A24-B39-C9-D15
A69-B39-C9-D15
A67-B39-C9-D15
A39-B39-C9-D15
A65-B39-C9-D15
A66-B39-C9-D15
A2-B45-C9-D15
A3-B45-C9-D15
A9-B45-C9-D15
A13-B45-C9-D15
A24-B45-C9-D15
A69-B45-C9-D15
A67-B45-C9-D15
A39-B45-C9-D15
A65-B45-C9-D15
A66-B45-C9-D15
A2-B53-C9-D15
A3-B53-C9-D15
A9-B53-C9-D15
A13-B53-C9-D15
A24-B53-C9-D15
A69-B53-C9-D15
A67-B53-C9-D15
A39-B53-C9-D15
A65-B53-C9-D15
A66-B53-C9-D15
A2-B79-C9-D15
A3-B79-C9-D15
A9-B79-C9-D15
A13-B79-C9-D15
A24-B79-C9-D15
A69-B79-C9-D15
A67-B79-C9-D15
A39-B79-C9-D15
A65-B79-C9-D15
A66-B79-C9-D15
A2-B80-C9-D15
A3-B80-C9-D15
A9-B80-C9-D15
A13-B80-C9-D15
A24-B80-C9-D15
A69-B80-C9-D15
A67-B80-C9-D15
A39-B80-C9-D15
A65-B80-C9-D15
A66-B80-C9-D15
A2-B85-C9-D15
A3-B85-C9-D15
A9-B85-C9-D15
A13-B85-C9-D15
A24-B85-C9-D15
A69-B85-C9-D15
A67-B85-C9-D15
A39-B85-C9-D15
A65-B85-C9-D15
A66-B85-C9-D15
A2-B86-C9-D15
A3-B86-C9-D15
A9-B86-C9-D15
A13-B86-C9-D15
A24-B86-C9-D15
A69-B86-C9-D15
A67-B86-C9-D15
A39-B86-C9-D15
A65-B86-C9-D15
A66-B86-C9-D15
A2-B87-C9-D15
A3-B87-C9-D15
A9-B87-C9-D15
A13-B87-C9-D15
A24-B87-C9-D15

-continued
A69-B87-C9-D15
A67-B87-C9-D15
A39-B87-C9-D15
A65-B87-C9-D15
A66-B87-C9-D15
A2-B89-C9-D15
A3-B89-C9-D15
A9-B89-C9-D15
A13-B89-C9-D15
A24-B89-C9-D15
A69-B89-C9-D15
A67-B89-C9-D15
A39-B89-C9-D15
A65-B89-C9-D15
A66-B89-C9-D15
A2-B92-C9-D15
A3-B92-C9-D15
A9-B92-C9-D15
A13-B92-C9-D15
A24-B92-C9-D15
A69-B92-C9-D15
A67-B92-C9-D15
A39-B92-C9-D15
A65-B92-C9-D15
A66-B92-C9-D15
A2-B4-C10-D15
A3-B4-C10-D15
A9-B4-C10-D15
A13-B4-C10-D15
A24-B4-C10-D15
A69-B4-C10-D15
A67-B4-C10-D15
A39-B4-C10-D15
A65-B4-C10-D15
A66-B4-C10-D15
A2-B5-C10-D15
A3-B5-C10-D15
A9-B5-C10-D15
A13-B5-C10-D15
A24-B5-C10-D15
A69-B5-C10-D15
A67-B5-C10-D15
A39-B5-C10-D15
A65-B5-C10-D15
A66-B5-C10-D15
A2-B6-C10-D15
A3-B6-C10-D15
A9-B6-C10-D15
A13-B6-C10-D15
A24-B6-C10-D15
A69-B6-C10-D15
A67-B6-C10-D15
A39-B6-C10-D15
A65-B6-C10-D15
A66-B6-C10-D15
A2-B32-C10-D15
A3-B32-C10-D15
A9-B32-C10-D15
A13-B32-C10-D15
A24-B32-C10-D15
A69-B32-C10-D15
A67-B32-C10-D15
A39-B32-C10-D15
A65-B32-C10-D15
A66-B32-C10-D15
A2-B39-C10-D15
A3-B39-C10-D15
A9-B39-C10-D15
A13-B39-C10-D15
A24-B39-C10-D15
A69-B39-C10-D15
A67-B39-C10-D15
A39-B39-C10-D15
A65-B39-C10-D15
A66-B39-C10-D15
A2-B45-C10-D15
A3-B45-C10-D15
A9-B45-C10-D15
A13-B45-C10-D15
A24-B45-C10-D15

-continued

A69-B45-C10-D15
A67-B45-C10-D15
A39-B45-C10-D15
A65-B45-C10-D15
A66-B45-C10-D15
A2-B53-C10-D15
A3-B53-C10-D15
A9-B53-C10-D15
A13-B53-C10-D15
A24-B53-C10-D15
A69-B53-C10-D15
A67-B53-C10-D15
A39-B53-C10-D15
A65-B53-C10-D15
A66-B53-C10-D15
A2-B79-C10-D15
A3-B79-C10-D15
A9-B79-C10-D15
A13-B79-C10-D15
A24-B79-C10-D15
A69-B79-C10-D15
A67-B79-C10-D15
A39-B79-C10-D15
A65-B79-C10-D15
A66-B79-C10-D15
A2-B80-C10-D15
A3-B80-C10-D15
A9-B80-C10-D15
A13-B80-C10-D15
A24-B80-C10-D15
A69-B80-C10-D15
A67-B80-C10-D15
A39-B80-C10-D15
A65-B80-C10-D15
A66-B80-C10-D15
A2-B85-C10-D15
A3-B85-C10-D15
A9-B85-C10-D15
A13-B85-C10-D15
A24-B85-C10-D15
A69-B85-C10-D15
A67-B85-C10-D15
A39-B85-C10-D15
A65-B85-C10-D15
A66-B85-C10-D15
A2-B86-C10-D15
A3-B86-C10-D15
A9-B86-C10-D15
A13-B86-C10-D15
A24-B86-C10-D15
A69-B86-C10-D15
A67-B86-C10-D15
A39-B86-C10-D15
A65-B86-C10-D15
A66-B86-C10-D15
A2-B87-C10-D15
A3-B87-C10-D15
A9-B87-C10-D15
A13-B87-C10-D15
A24-B87-C10-D15
A69-B87-C10-D15
A67-B87-C10-D15
A39-B87-C10-D15
A65-B87-C10-D15
A66-B87-C10-D15
A2-B89-C10-D15
A3-B89-C10-D15
A9-B89-C10-D15
A13-B89-C10-D15
A24-B89-C10-D15
A69-B89-C10-D15
A67-B89-C10-D15
A39-B89-C10-D15
A65-B89-C10-D15
A66-B89-C10-D15
A2-B92-C10-D15
A3-B92-C10-D15
A9-B92-C10-D15
A13-B92-C10-D15
A24-B92-C10-D15

-continued

A69-B92-C10-D15
A67-B92-C10-D15
A39-B92-C10-D15
A65-B92-C10-D15
A66-B92-C10-D15
A2-B4-C11-D15
A3-B4-C11-D15
A9-B4-C11-D15
A13-B4-C11-D15
A24-B4-C11-D15
A69-B4-C11-D15
A67-B4-C11-D15
A39-B4-C11-D15
A65-B4-C11-D15
A66-B4-C11-D15
A2-B5-C11-D15
A3-B5-C11-D15
A9-B5-C11-D15
A13-B5-C11-D15
A24-B5-C11-D15
A69-B5-C11-D15
A67-B5-C11-D15
A39-B5-C11-D15
A65-B5-C11-D15
A66-B5-C11-D15
A2-B6-C11-D15
A3-B6-C11-D15
A9-B6-C11-D15
A13-B6-C11-D15
A24-B6-C11-D15
A69-B6-C11-D15
A67-B6-C11-D15
A39-B6-C11-D15
A65-B6-C11-D15
A66-B6-C11-D15
A2-B32-C11-D15
A3-B32-C11-D15
A9-B32-C11-D15
A13-B32-C11-D15
A24-B32-C11-D15
A69-B32-C11-D15
A67-B32-C11-D15
A39-B32-C11-D15
A65-B32-C11-D15
A66-B32-C11-D15
A2-B39-C11-D15
A3-B39-C11-D15
A9-B39-C11-D15
A13-B39-C11-D15
A24-B39-C11-D15
A69-B39-C11-D15
A67-B39-C11-D15
A39-B39-C11-D15
A65-B39-C11-D15
A66-B39-C11-D15
A2-B45-C11-D15
A3-B45-C11-D15
A9-B45-C11-D15
A13-B45-C11-D15
A24-B45-C11-D15
A69-B45-C11-D15
A67-B45-C11-D15
A39-B45-C11-D15
A65-B45-C11-D15
A66-B45-C11-D15
A2-B53-C11-D15
A3-B53-C11-D15
A9-B53-C11-D15
A13-B53-C11-D15
A24-B53-C11-D15
A69-B53-C11-D15
A67-B53-C11-D15
A39-B53-C11-D15
A65-B53-C11-D15
A66-B53-C11-D15
A2-B79-C11-D15
A3-B79-C11-D15
A9-B79-C11-D15
A13-B79-C11-D15
A24-B79-C11-D15

-continued

A69-B79-C11-D15
A67-B79-C11-D15
A39-B79-C11-D15
A65-B79-C11-D15
A66-B79-C11-D15
A2-B80-C11-D15
A3-B80-C11-D15
A9-B80-C11-D15
A13-B80-C11-D15
A24-B80-C11-D15
A69-B80-C11-D15
A67-B80-C11-D15
A39-B80-C11-D15
A65-B80-C11-D15
A66-B80-C11-D15
A2-B85-C11-D15
A3-B85-C11-D15
A9-B85-C11-D15
A13-B85-C11-D15
A24-B85-C11-D15
A69-B85-C11-D15
A67-B85-C11-D15
A39-B85-C11-D15
A65-B85-C11-D15
A66-B85-C11-D15
A2-B86-C11-D15
A3-B86-C11-D15
A9-B86-C11-D15
A13-B86-C11-D15
A24-B86-C11-D15
A69-B86-C11-D15
A67-B86-C11-D15
A39-B86-C11-D15
A65-B86-C11-D15
A66-B86-C11-D15
A2-B87-C11-D15
A3-B87-C11-D15
A9-B87-C11-D15
A13-B87-C11-D15
A24-B87-C11-D15
A69-B87-C11-D15
A67-B87-C11-D15
A39-B87-C11-D15
A65-B87-C11-D15
A66-B87-C11-D15
A2-B89-C11-D15
A3-B89-C11-D15
A9-B89-C11-D15
A13-B89-C11-D15
A24-B89-C11-D15
A69-B89-C11-D15
A67-B89-C11-D15
A39-B89-C11-D15
A65-B89-C11-D15
A66-B89-C11-D15
A2-B92-C11-D15
A3-B92-C11-D15
A9-B92-C11-D15
A13-B92-C11-D15
A24-B92-C11-D15
A69-B92-C11-D15
A67-B92-C11-D15
A39-B92-C11-D15
A65-B92-C11-D15
A66-B92-C11-D15
A2-B4-C12-D15
A3-B4-C12-D15
A9-B4-C12-D15
A13-B4-C12-D15
A24-B4-C12-D15
A69-B4-C12-D15
A67-B4-C12-D15
A39-B4-C12-D15
A65-B4-C12-D15
A66-B4-C12-D15
A2-B5-C12-D15
A3-B5-C12-D15
A9-B5-C12-D15
A13-B5-C12-D15
A24-B5-C12-D15

-continued

A69-B5-C12-D15
A67-B5-C12-D15
A39-B5-C12-D15
A65-B5-C12-D15
A66-B5-C12-D15
A2-B6-C12-D15
A3-B6-C12-D15
A9-B6-C12-D15
A13-B6-C12-D15
A24-B6-C12-D15
A69-B6-C12-D15
A67-B6-C12-D15
A39-B6-C12-D15
A65-B6-C12-D15
A66-B6-C12-D15
A2-B32-C12-D15
A3-B32-C12-D15
A9-B32-C12-D15
A13-B32-C12-D15
A24-B32-C12-D15
A69-B32-C12-D15
A67-B32-C12-D15
A39-B32-C12-D15
A65-B32-C12-D15
A66-B32-C12-D15
A2-B39-C12-D15
A3-B39-C12-D15
A9-B39-C12-D15
A13-B39-C12-D15
A24-B39-C12-D15
A69-B39-C12-D15
A67-B39-C12-D15
A39-B39-C12-D15
A65-B39-C12-D15
A66-B39-C12-D15
A2-B45-C12-D15
A3-B45-C12-D15
A9-B45-C12-D15
A13-B45-C12-D15
A24-B45-C12-D15
A69-B45-C12-D15
A67-B45-C12-D15
A39-B45-C12-D15
A65-B45-C12-D15
A66-B45-C12-D15
A2-B53-C12-D15
A3-B53-C12-D15
A9-B53-C12-D15
A13-B53-C12-D15
A24-B53-C12-D15
A69-B53-C12-D15
A67-B53-C12-D15
A39-B53-C12-D15
A65-B53-C12-D15
A66-B53-C12-D15
A2-B79-C12-D15
A3-B79-C12-D15
A9-B79-C12-D15
A13-B79-C12-D15
A24-B79-C12-D15
A69-B79-C12-D15
A67-B79-C12-D15
A39-B79-C12-D15
A65-B79-C12-D15
A66-B79-C12-D15
A2-B80-C12-D15
A3-B80-C12-D15
A9-B80-C12-D15
A13-B80-C12-D15
A24-B80-C12-D15
A69-B80-C12-D15
A67-B80-C12-D15
A39-B80-C12-D15
A65-B80-C12-D15
A66-B80-C12-D15
A2-B85-C12-D15
A3-B85-C12-D15
A9-B85-C12-D15
A13-B85-C12-D15
A24-B85-C12-D15

-continued
A69-B85-C12-D15
A67-B85-C12-D15
A39-B85-C12-D15
A65-B85-C12-D15
A66-B85-C12-D15
A2-B86-C12-D15
A3-B86-C12-D15
A9-B86-C12-D15
A13-B86-C12-D15
A24-B86-C12-D15
A69-B86-C12-D15
A67-B86-C12-D15
A39-B86-C12-D15
A65-B86-C12-D15
A66-B86-C12-D15
A2-B87-C12-D15
A3-B87-C12-D15
A9-B87-C12-D15
A13-B87-C12-D15
A24-B87-C12-D15
A69-B87-C12-D15
A67-B87-C12-D15
A39-B87-C12-D15
A65-B87-C12-D15
A66-B87-C12-D15
A2-B89-C12-D15
A3-B89-C12-D15
A9-B89-C12-D15
A13-B89-C12-D15
A24-B89-C12-D15
A69-B89-C12-D15
A67-B89-C12-D15
A39-B89-C12-D15
A65-B89-C12-D15
A66-B89-C12-D15
A2-B92-C12-D15
A3-B92-C12-D15
A9-B92-C12-D15
A13-B92-C12-D15
A24-B92-C12-D15
A69-B92-C12-D15
A67-B92-C12-D15
A39-B92-C12-D15
A65-B92-C12-D15
A66-B92-C12-D15
A2-B4-C13-D15
A3-B4-C13-D15
A9-B4-C13-D15
A13-B4-C13-D15
A24-B4-C13-D15
A69-B4-C13-D15
A67-B4-C13-D15
A39-B4-C13-D15
A65-B4-C13-D15
A66-B4-C13-D15
A2-B5-C13-D15
A3-B5-C13-D15
A9-B5-C13-D15
A13-B5-C13-D15
A24-B5-C13-D15
A69-B5-C13-D15
A67-B5-C13-D15
A39-B5-C13-D15
A65-B5-C13-D15
A66-B5-C13-D15
A2-B6-C13-D15
A3-B6-C13-D15
A9-B6-C13-D15
A13-B6-C13-D15
A24-B6-C13-D15
A69-B6-C13-D15
A67-B6-C13-D15
A39-B6-C13-D15
A65-B6-C13-D15
A66-B6-C13-D15
A2-B32-C13-D15
A3-B32-C13-D15
A9-B32-C13-D15
A13-B32-C13-D15
A24-B32-C13-D15

-continued
A69-B32-C13-D15
A67-B32-C13-D15
A39-B32-C13-D15
A65-B32-C13-D15
A66-B32-C13-D15
A2-B39-C13-D15
A3-B39-C13-D15
A9-B39-C13-D15
A13-B39-C13-D15
A24-B39-C13-D15
A69-B39-C13-D15
A67-B39-C13-D15
A39-B39-C13-D15
A65-B39-C13-D15
A66-B39-C13-D15
A2-B45-C13-D15
A3-B45-C13-D15
A9-B45-C13-D15
A13-B45-C13-D15
A24-B45-C13-D15
A69-B45-C13-D15
A67-B45-C13-D15
A39-B45-C13-D15
A65-B45-C13-D15
A66-B45-C13-D15
A2-B53-C13-D15
A3-B53-C13-D15
A9-B53-C13-D15
A13-B53-C13-D15
A24-B53-C13-D15
A69-B53-C13-D15
A67-B53-C13-D15
A39-B53-C13-D15
A65-B53-C13-D15
A66-B53-C13-D15
A2-B79-C13-D15
A3-B79-C13-D15
A9-B79-C13-D15
A13-B79-C13-D15
A24-B79-C13-D15
A69-B79-C13-D15
A67-B79-C13-D15
A39-B79-C13-D15
A65-B79-C13-D15
A66-B79-C13-D15
A2-B80-C13-D15
A3-B80-C13-D15
A9-B80-C13-D15
A13-B80-C13-D15
A24-B80-C13-D15
A69-B80-C13-D15
A67-B80-C13-D15
A39-B80-C13-D15
A65-B80-C13-D15
A66-B80-C13-D15
A2-B85-C13-D15
A3-B85-C13-D15
A9-B85-C13-D15
A13-B85-C13-D15
A24-B85-C13-D15
A69-B85-C13-D15
A67-B85-C13-D15
A39-B85-C13-D15
A65-B85-C13-D15
A66-B85-C13-D15
A2-B86-C13-D15
A3-B86-C13-D15
A9-B86-C13-D15
A13-B86-C13-D15
A24-B86-C13-D15
A69-B86-C13-D15
A67-B86-C13-D15
A39-B86-C13-D15
A65-B86-C13-D15
A66-B86-C13-D15
A2-B87-C13-D15
A3-B87-C13-D15
A9-B87-C13-D15
A13-B87-C13-D15
A24-B87-C13-D15

-continued
A69-B87-C13-D15
A67-B87-C13-D15
A39-B87-C13-D15
A65-B87-C13-D15
A66-B87-C13-D15
A2-B89-C13-D15
A3-B89-C13-D15
A9-B89-C13-D15
A13-B89-C13-D15
A24-B89-C13-D15
A69-B89-C13-D15
A67-B89-C13-D15
A39-B89-C13-D15
A65-B89-C13-D15
A66-B89-C13-D15
A2-B92-C13-D15
A3-B92-C13-D15
A9-B92-C13-D15
A13-B92-C13-D15
A24-B92-C13-D15
A69-B92-C13-D15
A67-B92-C13-D15
A39-B92-C13-D15
A65-B92-C13-D15
A66-B92-C13-D15
A2-B4-C1-D16
A3-B4-C1-D16
A9-B4-C1-D16
A13-B4-C1-D16
A24-B4-C1-D16
A69-B4-C1-D16
A67-B4-C1-D16
A39-B4-C1-D16
A65-B4-C1-D16
A66-B4-C1-D16
A2-B5-C1-D16
A3-B5-C1-D16
A9-B5-C1-D16
A13-B5-C1-D16
A24-B5-C1-D16
A69-B5-C1-D16
A67-B5-C1-D16
A39-B5-C1-D16
A65-B5-C1-D16
A66-B5-C1-D16
A2-B6-C1-D16
A3-B6-C1-D16
A9-B6-C1-D16
A13-B6-C1-D16
A24-B6-C1-D16
A69-B6-C1-D16
A67-B6-C1-D16
A39-B6-C1-D16
A65-B6-C1-D16
A66-B6-C1-D16
A2-B32-C1-D16
A3-B32-C1-D16
A9-B32-C1-D16
A13-B32-C1-D16
A24-B32-C1-D16
A69-B32-C1-D16
A67-B32-C1-D16
A39-B32-C1-D16
A65-B32-C1-D16
A66-B32-C1-D16
A2-B39-C1-D16
A3-B39-C1-D16
A9-B39-C1-D16
A13-B39-C1-D16
A24-B39-C1-D16
A69-B39-C1-D16
A67-B39-C1-D16
A39-B39-C1-D16
A65-B39-C1-D16
A66-B39-C1-D16
A2-B45-C1-D16
A3-B45-C1-D16
A9-B45-C1-D16
A13-B45-C1-D16
A24-B45-C1-D16

-continued
A69-B45-C1-D16
A67-B45-C1-D16
A39-B45-C1-D16
A65-B45-C1-D16
A66-B45-C1-D16
A2-B53-C1-D16
A3-B53-C1-D16
A9-B53-C1-D16
A13-B53-C1-D16
A24-B53-C1-D16
A69-B53-C1-D16
A67-B53-C1-D16
A39-B53-C1-D16
A65-B53-C1-D16
A66-B53-C1-D16
A2-B79-C1-D16
A3-B79-C1-D16
A9-B79-C1-D16
A13-B79-C1-D16
A24-B79-C1-D16
A69-B79-C1-D16
A67-B79-C1-D16
A39-B79-C1-D16
A65-B79-C1-D16
A66-B79-C1-D16
A2-B80-C1-D16
A3-B80-C1-D16
A9-B80-C1-D16
A13-B80-C1-D16
A24-B80-C1-D16
A69-B80-C1-D16
A67-B80-C1-D16
A39-B80-C1-D16
A65-B80-C1-D16
A66-B80-C1-D16
A2-B85-C1-D16
A3-B85-C1-D16
A9-B85-C1-D16
A13-B85-C1-D16
A24-B85-C1-D16
A69-B85-C1-D16
A67-B85-C1-D16
A39-B85-C1-D16
A65-B85-C1-D16
A66-B85-C1-D16
A2-B86-C1-D16
A3-B86-C1-D16
A9-B86-C1-D16
A13-B86-C1-D16
A24-B86-C1-D16
A69-B86-C1-D16
A67-B86-C1-D16
A39-B86-C1-D16
A65-B86-C1-D16
A66-B86-C1-D16
A2-B87-C1-D16
A3-B87-C1-D16
A9-B87-C1-D16
A13-B87-C1-D16
A24-B87-C1-D16
A69-B87-C1-D16
A67-B87-C1-D16
A39-B87-C1-D16
A65-B87-C1-D16
A66-B87-C1-D16
A2-B89-C1-D16
A3-B89-C1-D16
A9-B89-C1-D16
A13-B89-C1-D16
A24-B89-C1-D16
A69-B89-C1-D16
A67-B89-C1-D16
A39-B89-C1-D16
A65-B89-C1-D16
A66-B89-C1-D16
A2-B92-C1-D16
A3-B92-C1-D16
A9-B92-C1-D16
A13-B92-C1-D16
A24-B92-C1-D16

-continued
A69-B92-C1-D16
A67-B92-C1-D16
A39-B92-C1-D16
A65-B92-C1-D16
A66-B92-C1-D16
A2-B4-C2-D16
A3-B4-C2-D16
A9-B4-C2-D16
A13-B4-C2-D16
A24-B4-C2-D16
A69-B4-C2-D16
A67-B4-C2-D16
A39-B4-C2-D16
A65-B4-C2-D16
A66-B4-C2-D16
A2-B5-C2-D16
A3-B5-C2-D16
A9-B5-C2-D16
A13-B5-C2-D16
A24-B5-C2-D16
A69-B5-C2-D16
A67-B5-C2-D16
A39-B5-C2-D16
A65-B5-C2-D16
A66-B5-C2-D16
A2-B6-C2-D16
A3-B6-C2-D16
A9-B6-C2-D16
A13-B6-C2-D16
A24-B6-C2-D16
A69-B6-C2-D16
A67-B6-C2-D16
A39-B6-C2-D16
A65-B6-C2-D16
A66-B6-C2-D16
A2-B32-C2-D16
A3-B32-C2-D16
A9-B32-C2-D16
A13-B32-C2-D16
A24-B32-C2-D16
A69-B32-C2-D16
A67-B32-C2-D16
A39-B32-C2-D16
A65-B32-C2-D16
A66-B32-C2-D16
A2-B39-C2-D16
A3-B39-C2-D16
A9-B39-C2-D16
A13-B39-C2-D16
A24-B39-C2-D16
A69-B39-C2-D16
A67-B39-C2-D16
A39-B39-C2-D16
A65-B39-C2-D16
A66-B39-C2-D16
A2-B45-C2-D16
A3-B45-C2-D16
A9-B45-C2-D16
A13-B45-C2-D16
A24-B45-C2-D16
A69-B45-C2-D16
A67-B45-C2-D16
A39-B45-C2-D16
A65-B45-C2-D16
A66-B45-C2-D16
A2-B53-C2-D16
A3-B53-C2-D16
A9-B53-C2-D16
A13-B53-C2-D16
A24-B53-C2-D16
A69-B53-C2-D16
A67-B53-C2-D16
A39-B53-C2-D16
A65-B53-C2-D16
A66-B53-C2-D16
A2-B79-C2-D16
A3-B79-C2-D16
A9-B79-C2-D16
A13-B79-C2-D16
A24-B79-C2-D16

-continued
A69-B79-C2-D16
A67-B79-C2-D16
A39-B79-C2-D16
A65-B79-C2-D16
A66-B79-C2-D16
A2-B80-C2-D16
A3-B80-C2-D16
A9-B80-C2-D16
A13-B80-C2-D16
A24-B80-C2-D16
A69-B80-C2-D16
A67-B80-C2-D16
A39-B80-C2-D16
A65-B80-C2-D16
A66-B80-C2-D16
A2-B85-C2-D16
A3-B85-C2-D16
A9-B85-C2-D16
A13-B85-C2-D16
A24-B85-C2-D16
A69-B85-C2-D16
A67-B85-C2-D16
A39-B85-C2-D16
A65-B85-C2-D16
A66-B85-C2-D16
A2-B86-C2-D16
A3-B86-C2-D16
A9-B86-C2-D16
A13-B86-C2-D16
A24-B86-C2-D16
A69-B86-C2-D16
A67-B86-C2-D16
A39-B86-C2-D16
A65-B86-C2-D16
A66-B86-C2-D16
A2-B87-C2-D16
A3-B87-C2-D16
A9-B87-C2-D16
A13-B87-C2-D16
A24-B87-C2-D16
A69-B87-C2-D16
A67-B87-C2-D16
A39-B87-C2-D16
A65-B87-C2-D16
A66-B87-C2-D16
A2-B89-C2-D16
A3-B89-C2-D16
A9-B89-C2-D16
A13-B89-C2-D16
A24-B89-C2-D16
A69-B89-C2-D16
A67-B89-C2-D16
A39-B89-C2-D16
A65-B89-C2-D16
A66-B89-C2-D16
A2-B92-C2-D16
A3-B92-C2-D16
A9-B92-C2-D16
A13-B92-C2-D16
A24-B92-C2-D16
A69-B92-C2-D16
A67-B92-C2-D16
A39-B92-C2-D16
A65-B92-C2-D16
A66-B92-C2-D16
A2-B4-C3-D16
A3-B4-C3-D16
A9-B4-C3-D16
A13-B4-C3-D16
A24-B4-C3-D16
A69-B4-C3-D16
A67-B4-C3-D16
A39-B4-C3-D16
A65-B4-C3-D16
A66-B4-C3-D16
A2-B5-C3-D16
A3-B5-C3-D16
A9-B5-C3-D16
A13-B5-C3-D16
A24-B5-C3-D16

-continued
A69-B5-C3-D16
A67-B5-C3-D16
A39-B5-C3-D16
A65-B5-C3-D16
A66-B5-C3-D16
A2-B6-C3-D16
A3-B6-C3-D16
A9-B6-C3-D16
A13-B6-C3-D16
A24-B6-C3-D16
A69-B6-C3-D16
A67-B6-C3-D16
A39-B6-C3-D16
A65-B6-C3-D16
A66-B6-C3-D16
A2-B32-C3-D16
A3-B32-C3-D16
A9-B32-C3-D16
A13-B32-C3-D16
A24-B32-C3-D16
A69-B32-C3-D16
A67-B32-C3-D16
A39-B32-C3-D16
A65-B32-C3-D16
A66-B32-C3-D16
A2-B39-C3-D16
A3-B39-C3-D16
A9-B39-C3-D16
A13-B39-C3-D16
A24-B39-C3-D16
A69-B39-C3-D16
A67-B39-C3-D16
A39-B39-C3-D16
A65-B39-C3-D16
A66-B39-C3-D16
A2-B45-C3-D16
A3-B45-C3-D16
A9-B45-C3-D16
A13-B45-C3-D16
A24-B45-C3-D16
A69-B45-C3-D16
A67-B45-C3-D16
A39-B45-C3-D16
A65-B45-C3-D16
A66-B45-C3-D16
A2-B53-C3-D16
A3-B53-C3-D16
A9-B53-C3-D16
A13-B53-C3-D16
A24-B53-C3-D16
A69-B53-C3-D16
A67-B53-C3-D16
A39-B53-C3-D16
A65-B53-C3-D16
A66-B53-C3-D16
A2-B79-C3-D16
A3-B79-C3-D16
A9-B79-C3-D16
A13-B79-C3-D16
A24-B79-C3-D16
A69-B79-C3-D16
A67-B79-C3-D16
A39-B79-C3-D16
A65-B79-C3-D16
A66-B79-C3-D16
A2-B80-C3-D16
A3-B80-C3-D16
A9-B80-C3-D16
A13-B80-C3-D16
A24-B80-C3-D16
A69-B80-C3-D16
A67-B80-C3-D16
A39-B80-C3-D16
A65-B80-C3-D16
A66-B80-C3-D16
A2-B85-C3-D16
A3-B85-C3-D16
A9-B85-C3-D16
A13-B85-C3-D16
A24-B85-C3-D16

-continued
A69-B85-C3-D16
A67-B85-C3-D16
A39-B85-C3-D16
A65-B85-C3-D16
A66-B85-C3-D16
A2-B86-C3-D16
A3-B86-C3-D16
A9-B86-C3-D16
A13-B86-C3-D16
A24-B86-C3-D16
A69-B86-C3-D16
A67-B86-C3-D16
A39-B86-C3-D16
A65-B86-C3-D16
A66-B86-C3-D16
A2-B87-C3-D16
A3-B87-C3-D16
A9-B87-C3-D16
A13-B87-C3-D16
A24-B87-C3-D16
A69-B87-C3-D16
A67-B87-C3-D16
A39-B87-C3-D16
A65-B87-C3-D16
A66-B87-C3-D16
A2-B89-C3-D16
A3-B89-C3-D16
A9-B89-C3-D16
A13-B89-C3-D16
A24-B89-C3-D16
A69-B89-C3-D16
A67-B89-C3-D16
A39-B89-C3-D16
A65-B89-C3-D16
A66-B89-C3-D16
A2-B92-C3-D16
A3-B92-C3-D16
A9-B92-C3-D16
A13-B92-C3-D16
A24-B92-C3-D16
A69-B92-C3-D16
A67-B92-C3-D16
A39-B92-C3-D16
A65-B92-C3-D16
A66-B92-C3-D16
A2-B4-C4-D16
A3-B4-C4-D16
A9-B4-C4-D16
A13-B4-C4-D16
A24-B4-C4-D16
A69-B4-C4-D16
A67-B4-C4-D16
A39-B4-C4-D16
A65-B4-C4-D16
A66-B4-C4-D16
A2-B5-C4-D16
A3-B5-C4-D16
A9-B5-C4-D16
A13-B5-C4-D16
A24-B5-C4-D16
A69-B5-C4-D16
A67-B5-C4-D16
A39-B5-C4-D16
A65-B5-C4-D16
A66-B5-C4-D16
A2-B6-C4-D16
A3-B6-C4-D16
A9-B6-C4-D16
A13-B6-C4-D16
A24-B6-C4-D16
A69-B6-C4-D16
A67-B6-C4-D16
A39-B6-C4-D16
A65-B6-C4-D16
A66-B6-C4-D16
A2-B32-C4-D16
A3-B32-C4-D16
A9-B32-C4-D16
A13-B32-C4-D16
A24-B32-C4-D16

-continued
A69-B32-C4-D16
A67-B32-C4-D16
A39-B32-C4-D16
A65-B32-C4-D16
A66-B32-C4-D16
A2-B39-C4-D16
A3-B39-C4-D16
A9-B39-C4-D16
A13-B39-C4-D16
A24-B39-C4-D16
A69-B39-C4-D16
A67-B39-C4-D16
A39-B39-C4-D16
A65-B39-C4-D16
A66-B39-C4-D16
A2-B45-C4-D16
A3-B45-C4-D16
A9-B45-C4-D16
A13-B45-C4-D16
A24-B45-C4-D16
A69-B45-C4-D16
A67-B45-C4-D16
A39-B45-C4-D16
A65-B45-C4-D16
A66-B45-C4-D16
A2-B53-C4-D16
A3-B53-C4-D16
A9-B53-C4-D16
A13-B53-C4-D16
A24-B53-C4-D16
A69-B53-C4-D16
A67-B53-C4-D16
A39-B53-C4-D16
A65-B53-C4-D16
A66-B53-C4-D16
A2-B79-C4-D16
A3-B79-C4-D16
A9-B79-C4-D16
A13-B79-C4-D16
A24-B79-C4-D16
A69-B79-C4-D16
A67-B79-C4-D16
A39-B79-C4-D16
A65-B79-C4-D16
A66-B79-C4-D16
A2-B80-C4-D16
A3-B80-C4-D16
A9-B80-C4-D16
A13-B80-C4-D16
A24-B80-C4-D16
A69-B80-C4-D16
A67-B80-C4-D16
A39-B80-C4-D16
A65-B80-C4-D16
A66-B80-C4-D16
A2-B85-C4-D16
A3-B85-C4-D16
A9-B85-C4-D16
A13-B85-C4-D16
A24-B85-C4-D16
A69-B85-C4-D16
A67-B85-C4-D16
A39-B85-C4-D16
A65-B85-C4-D16
A66-B85-C4-D16
A2-B86-C4-D16
A3-B86-C4-D16
A9-B86-C4-D16
A13-B86-C4-D16
A24-B86-C4-D16
A69-B86-C4-D16
A67-B86-C4-D16
A39-B86-C4-D16
A65-B86-C4-D16
A66-B86-C4-D16
A2-B87-C4-D16
A3-B87-C4-D16
A9-B87-C4-D16
A13-B87-C4-D16
A24-B87-C4-D16

-continued
A69-B87-C4-D16
A67-B87-C4-D16
A39-B87-C4-D16
A65-B87-C4-D16
A66-B87-C4-D16
A2-B89-C4-D16
A3-B89-C4-D16
A9-B89-C4-D16
A13-B89-C4-D16
A24-B89-C4-D16
A69-B89-C4-D16
A67-B89-C4-D16
A39-B89-C4-D16
A65-B89-C4-D16
A66-B89-C4-D16
A2-B92-C4-D16
A3-B92-C4-D16
A9-B92-C4-D16
A13-B92-C4-D16
A24-B92-C4-D16
A69-B92-C4-D16
A67-B92-C4-D16
A39-B92-C4-D16
A65-B92-C4-D16
A66-B92-C4-D16
A2-B4-C5-D16
A3-B4-C5-D16
A9-B4-C5-D16
A13-B4-C5-D16
A24-B4-C5-D16
A69-B4-C5-D16
A67-B4-C5-D16
A39-B4-C5-D16
A65-B4-C5-D16
A66-B4-C5-D16
A2-B5-C5-D16
A3-B5-C5-D16
A9-B5-C5-D16
A13-B5-C5-D16
A24-B5-C5-D16
A69-B5-C5-D16
A67-B5-C5-D16
A39-B5-C5-D16
A65-B5-C5-D16
A66-B5-C5-D16
A2-B6-C5-D16
A3-B6-C5-D16
A9-B6-C5-D16
A13-B6-C5-D16
A24-B6-C5-D16
A69-B6-C5-D16
A67-B6-C5-D16
A39-B6-C5-D16
A65-B6-C5-D16
A66-B6-C5-D16
A2-B32-C5-D16
A3-B32-C5-D16
A9-B32-C5-D16
A13-B32-C5-D16
A24-B32-C5-D16
A69-B32-C5-D16
A67-B32-C5-D16
A39-B32-C5-D16
A65-B32-C5-D16
A66-B32-C5-D16
A2-B39-C5-D16
A3-B39-C5-D16
A9-B39-C5-D16
A13-B39-C5-D16
A24-B39-C5-D16
A69-B39-C5-D16
A67-B39-C5-D16
A39-B39-C5-D16
A65-B39-C5-D16
A66-B39-C5-D16
A2-B45-C5-D16
A3-B45-C5-D16
A9-B45-C5-D16
A13-B45-C5-D16
A24-B45-C5-D16

-continued
A69-B45-C5-D16
A67-B45-C5-D16
A39-B45-C5-D16
A65-B45-C5-D16
A66-B45-C5-D16
A2-B53-C5-D16
A3-B53-C5-D16
A9-B53-C5-D16
A13-B53-C5-D16
A24-B53-C5-D16
A69-B53-C5-D16
A67-B53-C5-D16
A39-B53-C5-D16
A65-B53-C5-D16
A66-B53-C5-D16
A2-B79-C5-D16
A3-B79-C5-D16
A9-B79-C5-D16
A13-B79-C5-D16
A24-B79-C5-D16
A69-B79-C5-D16
A67-B79-C5-D16
A39-B79-C5-D16
A65-B79-C5-D16
A66-B79-C5-D16
A2-B80-C5-D16
A3-B80-C5-D16
A9-B80-C5-D16
A13-B80-C5-D16
A24-B80-C5-D16
A69-B80-C5-D16
A67-B80-C5-D16
A39-B80-C5-D16
A65-B80-C5-D16
A66-B80-C5-D16
A2-B85-C5-D16
A3-B85-C5-D16
A9-B85-C5-D16
A13-B85-C5-D16
A24-B85-C5-D16
A69-B85-C5-D16
A67-B85-C5-D16
A39-B85-C5-D16
A65-B85-C5-D16
A66-B85-C5-D16
A2-B86-C5-D16
A3-B86-C5-D16
A9-B86-C5-D16
A13-B86-C5-D16
A24-B86-C5-D16
A69-B86-C5-D16
A67-B86-C5-D16
A39-B86-C5-D16
A65-B86-C5-D16
A66-B86-C5-D16
A2-B87-C5-D16
A3-B87-C5-D16
A9-B87-C5-D16
A13-B87-C5-D16
A24-B87-C5-D16
A69-B87-C5-D16
A67-B87-C5-D16
A39-B87-C5-D16
A65-B87-C5-D16
A66-B87-C5-D16
A2-B89-C5-D16
A3-B89-C5-D16
A9-B89-C5-D16
A13-B89-C5-D16
A24-B89-C5-D16
A69-B89-C5-D16
A67-B89-C5-D16
A39-B89-C5-D16
A65-B89-C5-D16
A66-B89-C5-D16
A2-B92-C5-D16
A3-B92-C5-D16
A9-B92-C5-D16
A13-B92-C5-D16
A24-B92-C5-D16

-continued
A69-B92-C5-D16
A67-B92-C5-D16
A39-B92-C5-D16
A65-B92-C5-D16
A66-B92-C5-D16
A2-B4-C6-D16
A3-B4-C6-D16
A9-B4-C6-D16
A13-B4-C6-D16
A24-B4-C6-D16
A69-B4-C6-D16
A67-B4-C6-D16
A39-B4-C6-D16
A65-B4-C6-D16
A66-B4-C6-D16
A2-B5-C6-D16
A3-B5-C6-D16
A9-B5-C6-D16
A13-B5-C6-D16
A24-B5-C6-D16
A69-B5-C6-D16
A67-B5-C6-D16
A39-B5-C6-D16
A65-B5-C6-D16
A66-B5-C6-D16
A2-B6-C6-D16
A3-B6-C6-D16
A9-B6-C6-D16
A13-B6-C6-D16
A24-B6-C6-D16
A69-B6-C6-D16
A67-B6-C6-D16
A39-B6-C6-D16
A65-B6-C6-D16
A66-B6-C6-D16
A2-B32-C6-D16
A3-B32-C6-D16
A9-B32-C6-D16
A13-B32-C6-D16
A24-B32-C6-D16
A69-B32-C6-D16
A67-B32-C6-D16
A39-B32-C6-D16
A65-B32-C6-D16
A66-B32-C6-D16
A2-B39-C6-D16
A3-B39-C6-D16
A9-B39-C6-D16
A13-B39-C6-D16
A24-B39-C6-D16
A69-B39-C6-D16
A67-B39-C6-D16
A39-B39-C6-D16
A65-B39-C6-D16
A66-B39-C6-D16
A2-B45-C6-D16
A3-B45-C6-D16
A9-B45-C6-D16
A13-B45-C6-D16
A24-B45-C6-D16
A69-B45-C6-D16
A67-B45-C6-D16
A39-B45-C6-D16
A65-B45-C6-D16
A66-B45-C6-D16
A2-B53-C6-D16
A3-B53-C6-D16
A9-B53-C6-D16
A13-B53-C6-D16
A24-B53-C6-D16
A69-B53-C6-D16
A67-B53-C6-D16
A39-B53-C6-D16
A65-B53-C6-D16
A66-B53-C6-D16
A2-B79-C6-D16
A3-B79-C6-D16
A9-B79-C6-D16
A13-B79-C6-D16
A24-B79-C6-D16

-continued
A69-B79-C6-D16
A67-B79-C6-D16
A39-B79-C6-D16
A65-B79-C6-D16
A66-B79-C6-D16
A2-B80-C6-D16
A3-B80-C6-D16
A9-B80-C6-D16
A13-B80-C6-D16
A24-B80-C6-D16
A69-B80-C6-D16
A67-B80-C6-D16
A39-B80-C6-D16
A65-B80-C6-D16
A66-B80-C6-D16
A2-B85-C6-D16
A3-B85-C6-D16
A9-B85-C6-D16
A13-B85-C6-D16
A24-B85-C6-D16
A69-B85-C6-D16
A67-B85-C6-D16
A39-B85-C6-D16
A65-B85-C6-D16
A66-B85-C6-D16
A2-B86-C6-D16
A3-B86-C6-D16
A9-B86-C6-D16
A13-B86-C6-D16
A24-B86-C6-D16
A69-B86-C6-D16
A67-B86-C6-D16
A39-B86-C6-D16
A65-B86-C6-D16
A66-B86-C6-D16
A2-B87-C6-D16
A3-B87-C6-D16
A9-B87-C6-D16
A13-B87-C6-D16
A24-B87-C6-D16
A69-B87-C6-D16
A67-B87-C6-D16
A39-B87-C6-D16
A65-B87-C6-D16
A66-B87-C6-D16
A2-B89-C6-D16
A3-B89-C6-D16
A9-B89-C6-D16
A13-B89-C6-D16
A24-B89-C6-D16
A69-B89-C6-D16
A67-B89-C6-D16
A39-B89-C6-D16
A65-B89-C6-D16
A66-B89-C6-D16
A2-B92-C6-D16
A3-B92-C6-D16
A9-B92-C6-D16
A13-B92-C6-D16
A24-B92-C6-D16
A69-B92-C6-D16
A67-B92-C6-D16
A39-B92-C6-D16
A65-B92-C6-D16
A66-B92-C6-D16
A2-B4-C7-D16
A3-B4-C7-D16
A9-B4-C7-D16
A13-B4-C7-D16
A24-B4-C7-D16
A69-B4-C7-D16
A67-B4-C7-D16
A39-B4-C7-D16
A65-B4-C7-D16
A66-B4-C7-D16
A2-B5-C7-D16
A3-B5-C7-D16
A9-B5-C7-D16
A13-B5-C7-D16
A24-B5-C7-D16

-continued
A69-B5-C7-D16
A67-B5-C7-D16
A39-B5-C7-D16
A65-B5-C7-D16
A66-B5-C7-D16
A2-B6-C7-D16
A3-B6-C7-D16
A9-B6-C7-D16
A13-B6-C7-D16
A24-B6-C7-D16
A69-B6-C7-D16
A67-B6-C7-D16
A39-B6-C7-D16
A65-B6-C7-D16
A66-B6-C7-D16
A2-B32-C7-D16
A3-B32-C7-D16
A9-B32-C7-D16
A13-B32-C7-D16
A24-B32-C7-D16
A69-B32-C7-D16
A67-B32-C7-D16
A39-B32-C7-D16
A65-B32-C7-D16
A66-B32-C7-D16
A2-B39-C7-D16
A3-B39-C7-D16
A9-B39-C7-D16
A13-B39-C7-D16
A24-B39-C7-D16
A69-B39-C7-D16
A67-B39-C7-D16
A39-B39-C7-D16
A65-B39-C7-D16
A66-B39-C7-D16
A2-B45-C7-D16
A3-B45-C7-D16
A9-B45-C7-D16
A13-B45-C7-D16
A24-B45-C7-D16
A69-B45-C7-D16
A67-B45-C7-D16
A39-B45-C7-D16
A65-B45-C7-D16
A66-B45-C7-D16
A2-B53-C7-D16
A3-B53-C7-D16
A9-B53-C7-D16
A13-B53-C7-D16
A24-B53-C7-D16
A69-B53-C7-D16
A67-B53-C7-D16
A39-B53-C7-D16
A65-B53-C7-D16
A66-B53-C7-D16
A2-B79-C7-D16
A3-B79-C7-D16
A9-B79-C7-D16
A13-B79-C7-D16
A24-B79-C7-D16
A69-B79-C7-D16
A67-B79-C7-D16
A39-B79-C7-D16
A65-B79-C7-D16
A66-B79-C7-D16
A2-B80-C7-D16
A3-B80-C7-D16
A9-B80-C7-D16
A13-B80-C7-D16
A24-B80-C7-D16
A69-B80-C7-D16
A67-B80-C7-D16
A39-B80-C7-D16
A65-B80-C7-D16
A66-B80-C7-D16
A2-B85-C7-D16
A3-B85-C7-D16
A9-B85-C7-D16
A13-B85-C7-D16
A24-B85-C7-D16

-continued
A69-B85-C7-D16
A67-B85-C7-D16
A39-B85-C7-D16
A65-B85-C7-D16
A66-B85-C7-D16
A2-B86-C7-D16
A3-B86-C7-D16
A9-B86-C7-D16
A13-B86-C7-D16
A24-B86-C7-D16
A69-B86-C7-D16
A67-B86-C7-D16
A39-B86-C7-D16
A65-B86-C7-D16
A66-B86-C7-D16
A2-B87-C7-D16
A3-B87-C7-D16
A9-B87-C7-D16
A13-B87-C7-D16
A24-B87-C7-D16
A69-B87-C7-D16
A67-B87-C7-D16
A39-B87-C7-D16
A65-B87-C7-D16
A66-B87-C7-D16
A2-B89-C7-D16
A3-B89-C7-D16
A9-B89-C7-D16
A13-B89-C7-D16
A24-B89-C7-D16
A69-B89-C7-D16
A67-B89-C7-D16
A39-B89-C7-D16
A65-B89-C7-D16
A66-B89-C7-D16
A2-B92-C7-D16
A3-B92-C7-D16
A9-B92-C7-D16
A13-B92-C7-D16
A24-B92-C7-D16
A69-B92-C7-D16
A67-B92-C7-D16
A39-B92-C7-D16
A65-B92-C7-D16
A66-B92-C7-D16
A2-B4-C8-D16
A3-B4-C8-D16
A9-B4-C8-D16
A13-B4-C8-D16
A24-B4-C8-D16
A69-B4-C8-D16
A67-B4-C8-D16
A39-B4-C8-D16
A65-B4-C8-D16
A66-B4-C8-D16
A2-B5-C8-D16
A3-B5-C8-D16
A9-B5-C8-D16
A13-B5-C8-D16
A24-B5-C8-D16
A69-B5-C8-D16
A67-B5-C8-D16
A39-B5-C8-D16
A65-B5-C8-D16
A66-B5-C8-D16
A2-B6-C8-D16
A3-B6-C8-D16
A9-B6-C8-D16
A13-B6-C8-D16
A24-B6-C8-D16
A69-B6-C8-D16
A67-B6-C8-D16
A39-B6-C8-D16
A65-B6-C8-D16
A66-B6-C8-D16
A2-B32-C8-D16
A3-B32-C8-D16
A9-B32-C8-D16
A13-B32-C8-D16
A24-B32-C8-D16

-continued
A69-B32-C8-D16
A67-B32-C8-D16
A39-B32-C8-D16
A65-B32-C8-D16
A66-B32-C8-D16
A2-B39-C8-D16
A3-B39-C8-D16
A9-B39-C8-D16
A13-B39-C8-D16
A24-B39-C8-D16
A69-B39-C8-D16
A67-B39-C8-D16
A39-B39-C8-D16
A65-B39-C8-D16
A66-B39-C8-D16
A2-B45-C8-D16
A3-B45-C8-D16
A9-B45-C8-D16
A13-B45-C8-D16
A24-B45-C8-D16
A69-B45-C8-D16
A67-B45-C8-D16
A39-B45-C8-D16
A65-B45-C8-D16
A66-B45-C8-D16
A2-B53-C8-D16
A3-B53-C8-D16
A9-B53-C8-D16
A13-B53-C8-D16
A24-B53-C8-D16
A69-B53-C8-D16
A67-B53-C8-D16
A39-B53-C8-D16
A65-B53-C8-D16
A66-B53-C8-D16
A2-B79-C8-D16
A3-B79-C8-D16
A9-B79-C8-D16
A13-B79-C8-D16
A24-B79-C8-D16
A69-B79-C8-D16
A67-B79-C8-D16
A39-B79-C8-D16
A65-B79-C8-D16
A66-B79-C8-D16
A2-B80-C8-D16
A3-B80-C8-D16
A9-B80-C8-D16
A13-B80-C8-D16
A24-B80-C8-D16
A69-B80-C8-D16
A67-B80-C8-D16
A39-B80-C8-D16
A65-B80-C8-D16
A66-B80-C8-D16
A2-B85-C8-D16
A3-B85-C8-D16
A9-B85-C8-D16
A13-B85-C8-D16
A24-B85-C8-D16
A69-B85-C8-D16
A67-B85-C8-D16
A39-B85-C8-D16
A65-B85-C8-D16
A66-B85-C8-D16
A2-B86-C8-D16
A3-B86-C8-D16
A9-B86-C8-D16
A13-B86-C8-D16
A24-B86-C8-D16
A69-B86-C8-D16
A67-B86-C8-D16
A39-B86-C8-D16
A65-B86-C8-D16
A66-B86-C8-D16
A2-B87-C8-D16
A3-B87-C8-D16
A9-B87-C8-D16
A13-B87-C8-D16
A24-B87-C8-D16

-continued
A69-B87-C8-D16
A67-B87-C8-D16
A39-B87-C8-D16
A65-B87-C8-D16
A66-B87-C8-D16
A2-B89-C8-D16
A3-B89-C8-D16
A9-B89-C8-D16
A13-B89-C8-D16
A24-B89-C8-D16
A69-B89-C8-D16
A67-B89-C8-D16
A39-B89-C8-D16
A65-B89-C8-D16
A66-B89-C8-D16
A2-B92-C8-D16
A3-B92-C8-D16
A9-B92-C8-D16
A13-B92-C8-D16
A24-B92-C8-D16
A69-B92-C8-D16
A67-B92-C8-D16
A39-B92-C8-D16
A65-B92-C8-D16
A66-B92-C8-D16
A2-B4-C9-D16
A3-B4-C9-D16
A9-B4-C9-D16
A13-B4-C9-D16
A24-B4-C9-D16
A69-B4-C9-D16
A67-B4-C9-D16
A39-B4-C9-D16
A65-B4-C9-D16
A66-B4-C9-D16
A2-B5-C9-D16
A3-B5-C9-D16
A9-B5-C9-D16
A13-B5-C9-D16
A24-B5-C9-D16
A69-B5-C9-D16
A67-B5-C9-D16
A39-B5-C9-D16
A65-B5-C9-D16
A66-B5-C9-D16
A2-B6-C9-D16
A3-B6-C9-D16
A9-B6-C9-D16
A13-B6-C9-D16
A24-B6-C9-D16
A69-B6-C9-D16
A67-B6-C9-D16
A39-B6-C9-D16
A65-B6-C9-D16
A66-B6-C9-D16
A2-B32-C9-D16
A3-B32-C9-D16
A9-B32-C9-D16
A13-B32-C9-D16
A24-B32-C9-D16
A69-B32-C9-D16
A67-B32-C9-D16
A39-B32-C9-D16
A65-B32-C9-D16
A66-B32-C9-D16
A2-B39-C9-D16
A3-B39-C9-D16
A9-B39-C9-D16
A13-B39-C9-D16
A24-B39-C9-D16
A69-B39-C9-D16
A67-B39-C9-D16
A39-B39-C9-D16
A65-B39-C9-D16
A66-B39-C9-D16
A2-B45-C9-D16
A3-B45-C9-D16
A9-B45-C9-D16
A13-B45-C9-D16
A24-B45-C9-D16

-continued
A69-B45-C9-D16
A67-B45-C9-D16
A39-B45-C9-D16
A65-B45-C9-D16
A66-B45-C9-D16
A2-B53-C9-D16
A3-B53-C9-D16
A9-B53-C9-D16
A13-B53-C9-D16
A24-B53-C9-D16
A69-B53-C9-D16
A67-B53-C9-D16
A39-B53-C9-D16
A65-B53-C9-D16
A66-B53-C9-D16
A2-B79-C9-D16
A3-B79-C9-D16
A9-B79-C9-D16
A13-B79-C9-D16
A24-B79-C9-D16
A69-B79-C9-D16
A67-B79-C9-D16
A39-B79-C9-D16
A65-B79-C9-D16
A66-B79-C9-D16
A2-B80-C9-D16
A3-B80-C9-D16
A9-B80-C9-D16
A13-B80-C9-D16
A24-B80-C9-D16
A69-B80-C9-D16
A67-B80-C9-D16
A39-B80-C9-D16
A65-B80-C9-D16
A66-B80-C9-D16
A2-B85-C9-D16
A3-B85-C9-D16
A9-B85-C9-D16
A13-B85-C9-D16
A24-B85-C9-D16
A69-B85-C9-D16
A67-B85-C9-D16
A39-B85-C9-D16
A65-B85-C9-D16
A66-B85-C9-D16
A2-B86-C9-D16
A3-B86-C9-D16
A9-B86-C9-D16
A13-B86-C9-D16
A24-B86-C9-D16
A69-B86-C9-D16
A67-B86-C9-D16
A39-B86-C9-D16
A65-B86-C9-D16
A66-B86-C9-D16
A2-B87-C9-D16
A3-B87-C9-D16
A9-B87-C9-D16
A13-B87-C9-D16
A24-B87-C9-D16
A69-B87-C9-D16
A67-B87-C9-D16
A39-B87-C9-D16
A65-B87-C9-D16
A66-B87-C9-D16
A2-B89-C9-D16
A3-B89-C9-D16
A9-B89-C9-D16
A13-B89-C9-D16
A24-B89-C9-D16
A69-B89-C9-D16
A67-B89-C9-D16
A39-B89-C9-D16
A65-B89-C9-D16
A66-B89-C9-D16
A2-B92-C9-D16
A3-B92-C9-D16
A9-B92-C9-D16
A13-B92-C9-D16
A24-B92-C9-D16

-continued
A69-B92-C9-D16
A67-B92-C9-D16
A39-B92-C9-D16
A65-B92-C9-D16
A66-B92-C9-D16
A2-B4-C10-D16
A3-B4-C10-D16
A9-B4-C10-D16
A13-B4-C10-D16
A24-B4-C10-D16
A69-B4-C10-D16
A67-B4-C10-D16
A39-B4-C10-D16
A65-B4-C10-D16
A66-B4-C10-D16
A2-B5-C10-D16
A3-B5-C10-D16
A9-B5-C10-D16
A13-B5-C10-D16
A24-B5-C10-D16
A69-B5-C10-D16
A67-B5-C10-D16
A39-B5-C10-D16
A65-B5-C10-D16
A66-B5-C10-D16
A2-B6-C10-D16
A3-B6-C10-D16
A9-B6-C10-D16
A13-B6-C10-D16
A24-B6-C10-D16
A69-B6-C10-D16
A67-B6-C10-D16
A39-B6-C10-D16
A65-B6-C10-D16
A66-B6-C10-D16
A2-B32-C10-D16
A3-B32-C10-D16
A9-B32-C10-D16
A13-B32-C10-D16
A24-B32-C10-D16
A69-B32-C10-D16
A67-B32-C10-D16
A39-B32-C10-D16
A65-B32-C10-D16
A66-B32-C10-D16
A2-B39-C10-D16
A3-B39-C10-D16
A9-B39-C10-D16
A13-B39-C10-D16
A24-B39-C10-D16
A69-B39-C10-D16
A67-B39-C10-D16
A39-B39-C10-D16
A65-B39-C10-D16
A66-B39-C10-D16
A2-B45-C10-D16
A3-B45-C10-D16
A9-B45-C10-D16
A13-B45-C10-D16
A24-B45-C10-D16
A69-B45-C10-D16
A67-B45-C10-D16
A39-B45-C10-D16
A65-B45-C10-D16
A66-B45-C10-D16
A2-B53-C10-D16
A3-B53-C10-D16
A9-B53-C10-D16
A13-B53-C10-D16
A24-B53-C10-D16
A69-B53-C10-D16
A67-B53-C10-D16
A39-B53-C10-D16
A65-B53-C10-D16
A66-B53-C10-D16
A2-B79-C10-D16
A3-B79-C10-D16
A9-B79-C10-D16
A13-B79-C10-D16
A24-B79-C10-D16

-continued
A69-B79-C10-D16
A67-B79-C10-D16
A39-B79-C10-D16
A65-B79-C10-D16
A66-B79-C10-D16
A2-B80-C10-D16
A3-B80-C10-D16
A9-B80-C10-D16
A13-B80-C10-D16
A24-B80-C10-D16
A69-B80-C10-D16
A67-B80-C10-D16
A39-B80-C10-D16
A65-B80-C10-D16
A66-B80-C10-D16
A2-B85-C10-D16
A3-B85-C10-D16
A9-B85-C10-D16
A13-B85-C10-D16
A24-B85-C10-D16
A69-B85-C10-D16
A67-B85-C10-D16
A39-B85-C10-D16
A65-B85-C10-D16
A66-B85-C10-D16
A2-B86-C10-D16
A3-B86-C10-D16
A9-B86-C10-D16
A13-B86-C10-D16
A24-B86-C10-D16
A69-B86-C10-D16
A67-B86-C10-D16
A39-B86-C10-D16
A65-B86-C10-D16
A66-B86-C10-D16
A2-B87-C10-D16
A3-B87-C10-D16
A9-B87-C10-D16
A13-B87-C10-D16
A24-B87-C10-D16
A69-B87-C10-D16
A67-B87-C10-D16
A39-B87-C10-D16
A65-B87-C10-D16
A66-B87-C10-D16
A2-B89-C10-D16
A3-B89-C10-D16
A9-B89-C10-D16
A13-B89-C10-D16
A24-B89-C10-D16
A69-B89-C10-D16
A67-B89-C10-D16
A39-B89-C10-D16
A65-B89-C10-D16
A66-B89-C10-D16
A2-B92-C10-D16
A3-B92-C10-D16
A9-B92-C10-D16
A13-B92-C10-D16
A24-B92-C10-D16
A69-B92-C10-D16
A67-B92-C10-D16
A39-B92-C10-D16
A65-B92-C10-D16
A66-B92-C10-D16
A2-B4-C11-D16
A3-B4-C11-D16
A9-B4-C11-D16
A13-B4-C11-D16
A24-B4-C11-D16
A69-B4-C11-D16
A67-B4-C11-D16
A39-B4-C11-D16
A65-B4-C11-D16
A66-B4-C11-D16
A2-B5-C11-D16
A3-B5-C11-D16
A9-B5-C11-D16
A13-B5-C11-D16
A24-B5-C11-D16

-continued
A69-B5-C11-D16
A67-B5-C11-D16
A39-B5-C11-D16
A65-B5-C11-D16
A66-B5-C11-D16
A2-B6-C11-D16
A3-B6-C11-D16
A9-B6-C11-D16
A13-B6-C11-D16
A24-B6-C11-D16
A69-B6-C11-D16
A67-B6-C11-D16
A39-B6-C11-D16
A65-B6-C11-D16
A66-B6-C11-D16
A2-B32-C11-D16
A3-B32-C11-D16
A9-B32-C11-D16
A13-B32-C11-D16
A24-B32-C11-D16
A69-B32-C11-D16
A67-B32-C11-D16
A39-B32-C11-D16
A65-B32-C11-D16
A66-B32-C11-D16
A2-B39-C11-D16
A3-B39-C11-D16
A9-B39-C11-D16
A13-B39-C11-D16
A24-B39-C11-D16
A69-B39-C11-D16
A67-B39-C11-D16
A39-B39-C11-D16
A65-B39-C11-D16
A66-B39-C11-D16
A2-B45-C11-D16
A3-B45-C11-D16
A9-B45-C11-D16
A13-B45-C11-D16
A24-B45-C11-D16
A69-B45-C11-D16
A67-B45-C11-D16
A39-B45-C11-D16
A65-B45-C11-D16
A66-B45-C11-D16
A2-B53-C11-D16
A3-B53-C11-D16
A9-B53-C11-D16
A13-B53-C11-D16
A24-B53-C11-D16
A69-B53-C11-D16
A67-B53-C11-D16
A39-B53-C11-D16
A65-B53-C11-D16
A66-B53-C11-D16
A2-B79-C11-D16
A3-B79-C11-D16
A9-B79-C11-D16
A13-B79-C11-D16
A24-B79-C11-D16
A69-B79-C11-D16
A67-B79-C11-D16
A39-B79-C11-D16
A65-B79-C11-D16
A66-B79-C11-D16
A2-B80-C11-D16
A3-B80-C11-D16
A9-B80-C11-D16
A13-B80-C11-D16
A24-B80-C11-D16
A69-B80-C11-D16
A67-B80-C11-D16
A39-B80-C11-D16
A65-B80-C11-D16
A66-B80-C11-D16
A2-B85-C11-D16
A3-B85-C11-D16
A9-B85-C11-D16
A13-B85-C11-D16
A24-B85-C11-D16

-continued
A69-B85-C11-D16
A67-B85-C11-D16
A39-B85-C11-D16
A65-B85-C11-D16
A66-B85-C11-D16
A2-B86-C11-D16
A3-B86-C11-D16
A9-B86-C11-D16
A13-B86-C11-D16
A24-B86-C11-D16
A69-B86-C11-D16
A67-B86-C11-D16
A39-B86-C11-D16
A65-B86-C11-D16
A66-B86-C11-D16
A2-B87-C11-D16
A3-B87-C11-D16
A9-B87-C11-D16
A13-B87-C11-D16
A24-B87-C11-D16
A69-B87-C11-D16
A67-B87-C11-D16
A39-B87-C11-D16
A65-B87-C11-D16
A66-B87-C11-D16
A2-B89-C11-D16
A3-B89-C11-D16
A9-B89-C11-D16
A13-B89-C11-D16
A24-B89-C11-D16
A69-B89-C11-D16
A67-B89-C11-D16
A39-B89-C11-D16
A65-B89-C11-D16
A66-B89-C11-D16
A2-B92-C11-D16
A3-B92-C11-D16
A9-B92-C11-D16
A13-B92-C11-D16
A24-B92-C11-D16
A69-B92-C11-D16
A67-B92-C11-D16
A39-B92-C11-D16
A65-B92-C11-D16
A66-B92-C11-D16
A2-B4-C12-D16
A3-B4-C12-D16
A9-B4-C12-D16
A13-B4-C12-D16
A24-B4-C12-D16
A69-B4-C12-D16
A67-B4-C12-D16
A39-B4-C12-D16
A65-B4-C12-D16
A66-B4-C12-D16
A2-B5-C12-D16
A3-B5-C12-D16
A9-B5-C12-D16
A13-B5-C12-D16
A24-B5-C12-D16
A69-B5-C12-D16
A67-B5-C12-D16
A39-B5-C12-D16
A65-B5-C12-D16
A66-B5-C12-D16
A2-B6-C12-D16
A3-B6-C12-D16
A9-B6-C12-D16
A13-B6-C12-D16
A24-B6-C12-D16
A69-B6-C12-D16
A67-B6-C12-D16
A39-B6-C12-D16
A65-B6-C12-D16
A66-B6-C12-D16
A2-B32-C12-D16
A3-B32-C12-D16
A9-B32-C12-D16
A13-B32-C12-D16
A24-B32-C12-D16

-continued

A69-B32-C12-D16
A67-B32-C12-D16
A39-B32-C12-D16
A65-B32-C12-D16
A66-B32-C12-D16
A2-B39-C12-D16
A3-B39-C12-D16
A9-B39-C12-D16
A13-B39-C12-D16
A24-B39-C12-D16
A69-B39-C12-D16
A67-B39-C12-D16
A39-B39-C12-D16
A65-B39-C12-D16
A66-B39-C12-D16
A2-B45-C12-D16
A3-B45-C12-D16
A9-B45-C12-D16
A13-B45-C12-D16
A24-B45-C12-D16
A69-B45-C12-D16
A67-B45-C12-D16
A39-B45-C12-D16
A65-B45-C12-D16
A66-B45-C12-D16
A2-B53-C12-D16
A3-B53-C12-D16
A9-B53-C12-D16
A13-B53-C12-D16
A24-B53-C12-D16
A69-B53-C12-D16
A67-B53-C12-D16
A39-B53-C12-D16
A65-B53-C12-D16
A66-B53-C12-D16
A2-B79-C12-D16
A3-B79-C12-D16
A9-B79-C12-D16
A13-B79-C12-D16
A24-B79-C12-D16
A69-B79-C12-D16
A67-B79-C12-D16
A39-B79-C12-D16
A65-B79-C12-D16
A66-B79-C12-D16
A2-B80-C12-D16
A3-B80-C12-D16
A9-B80-C12-D16
A13-B80-C12-D16
A24-B80-C12-D16
A69-B80-C12-D16
A67-B80-C12-D16
A39-B80-C12-D16
A65-B80-C12-D16
A66-B80-C12-D16
A2-B85-C12-D16
A3-B85-C12-D16
A9-B85-C12-D16
A13-B85-C12-D16
A24-B85-C12-D16
A69-B85-C12-D16
A67-B85-C12-D16
A39-B85-C12-D16
A65-B85-C12-D16
A66-B85-C12-D16
A2-B86-C12-D16
A3-B86-C12-D16
A9-B86-C12-D16
A13-B86-C12-D16
A24-B86-C12-D16
A69-B86-C12-D16
A67-B86-C12-D16
A39-B86-C12-D16
A65-B86-C12-D16
A66-B86-C12-D16
A2-B87-C12-D16
A3-B87-C12-D16
A9-B87-C12-D16
A13-B87-C12-D16
A24-B87-C12-D16

-continued

A69-B87-C12-D16
A67-B87-C12-D16
A39-B87-C12-D16
A65-B87-C12-D16
A66-B87-C12-D16
A2-B89-C12-D16
A3-B89-C12-D16
A9-B89-C12-D16
A13-B89-C12-D16
A24-B89-C12-D16
A69-B89-C12-D16
A67-B89-C12-D16
A39-B89-C12-D16
A65-B89-C12-D16
A66-B89-C12-D16
A2-B92-C12-D16
A3-B92-C12-D16
A9-B92-C12-D16
A13-B92-C12-D16
A24-B92-C12-D16
A69-B92-C12-D16
A67-B92-C12-D16
A39-B92-C12-D16
A65-B92-C12-D16
A66-B92-C12-D16
A2-B4-C13-D16
A3-B4-C13-D16
A9-B4-C13-D16
A13-B4-C13-D16
A24-B4-C13-D16
A69-B4-C13-D16
A67-B4-C13-D16
A39-B4-C13-D16
A65-B4-C13-D16
A66-B4-C13-D16
A2-B5-C13-D16
A3-B5-C13-D16
A9-B5-C13-D16
A13-B5-C13-D16
A24-B5-C13-D16
A69-B5-C13-D16
A67-B5-C13-D16
A39-B5-C13-D16
A65-B5-C13-D16
A66-B5-C13-D16
A2-B6-C13-D16
A3-B6-C13-D16
A9-B6-C13-D16
A13-B6-C13-D16
A24-B6-C13-D16
A69-B6-C13-D16
A67-B6-C13-D16
A39-B6-C13-D16
A65-B6-C13-D16
A66-B6-C13-D16
A2-B32-C13-D16
A3-B32-C13-D16
A9-B32-C13-D16
A13-B32-C13-D16
A24-B32-C13-D16
A69-B32-C13-D16
A67-B32-C13-D16
A39-B32-C13-D16
A65-B32-C13-D16
A66-B32-C13-D16
A2-B39-C13-D16
A3-B39-C13-D16
A9-B39-C13-D16
A13-B39-C13-D16
A24-B39-C13-D16
A69-B39-C13-D16
A67-B39-C13-D16
A39-B39-C13-D16
A65-B39-C13-D16
A66-B39-C13-D16
A2-B45-C13-D16
A3-B45-C13-D16
A9-B45-C13-D16
A13-B45-C13-D16
A24-B45-C13-D16

-continued

A69-B45-C13-D16
A67-B45-C13-D16
A39-B45-C13-D16
A65-B45-C13-D16
A66-B45-C13-D16
A2-B53-C13-D16
A3-B53-C13-D16
A9-B53-C13-D16
A13-B53-C13-D16
A24-B53-C13-D16
A69-B53-C13-D16
A67-B53-C13-D16
A39-B53-C13-D16
A65-B53-C13-D16
A66-B53-C13-D16
A2-B79-C13-D16
A3-B79-C13-D16
A9-B79-C13-D16
A13-B79-C13-D16
A24-B79-C13-D16
A69-B79-C13-D16
A67-B79-C13-D16
A39-B79-C13-D16
A65-B79-C13-D16
A66-B79-C13-D16
A2-B80-C13-D16
A3-B80-C13-D16
A9-B80-C13-D16
A13-B80-C13-D16
A24-B80-C13-D16
A69-B80-C13-D16
A67-B80-C13-D16
A39-B80-C13-D16
A65-B80-C13-D16
A66-B80-C13-D16
A2-B85-C13-D16
A3-B85-C13-D16
A9-B85-C13-D16
A13-B85-C13-D16
A24-B85-C13-D16
A69-B85-C13-D16
A67-B85-C13-D16
A39-B85-C13-D16
A65-B85-C13-D16
A66-B85-C13-D16
A2-B86-C13-D16
A3-B86-C13-D16
A9-B86-C13-D16
A13-B86-C13-D16
A24-B86-C13-D16
A69-B86-C13-D16
A67-B86-C13-D16
A39-B86-C13-D16
A65-B86-C13-D16
A66-B86-C13-D16
A2-B87-C13-D16
A3-B87-C13-D16
A9-B87-C13-D16
A13-B87-C13-D16
A24-B87-C13-D16
A69-B87-C13-D16
A67-B87-C13-D16
A39-B87-C13-D16
A65-B87-C13-D16
A66-B87-C13-D16
A2-B89-C13-D16
A3-B89-C13-D16
A9-B89-C13-D16
A13-B89-C13-D16
A24-B89-C13-D16
A69-B89-C13-D16
A67-B89-C13-D16
A39-B89-C13-D16
A65-B89-C13-D16
A66-B89-C13-D16
A2-B92-C13-D16
A3-B92-C13-D16
A9-B92-C13-D16
A13-B92-C13-D16
A24-B92-C13-D16

-continued

A69-B92-C13-D16
A67-B92-C13-D16
A39-B92-C13-D16
A65-B92-C13-D16
A66-B92-C13-D16
A2-B4-C1-D17
A3-B4-C1-D17
A9-B4-C1-D17
A13-B4-C1-D17
A24-B4-C1-D17
A69-B4-C1-D17
A67-B4-C1-D17
A39-B4-C1-D17
A65-B4-C1-D17
A66-B4-C1-D17
A2-B5-C1-D17
A3-B5-C1-D17
A9-B5-C1-D17
A13-B5-C1-D17
A24-B5-C1-D17
A69-B5-C1-D17
A67-B5-C1-D17
A39-B5-C1-D17
A65-B5-C1-D17
A66-B5-C1-D17
A2-B6-C1-D17
A3-B6-C1-D17
A9-B6-C1-D17
A13-B6-C1-D17
A24-B6-C1-D17
A69-B6-C1-D17
A67-B6-C1-D17
A39-B6-C1-D17
A65-B6-C1-D17
A66-B6-C1-D17
A2-B32-C1-D17
A3-B32-C1-D17
A9-B32-C1-D17
A13-B32-C1-D17
A24-B32-C1-D17
A69-B32-C1-D17
A67-B32-C1-D17
A39-B32-C1-D17
A65-B32-C1-D17
A66-B32-C1-D17
A2-B39-C1-D17
A3-B39-C1-D17
A9-B39-C1-D17
A13-B39-C1-D17
A24-B39-C1-D17
A69-B39-C1-D17
A67-B39-C1-D17
A39-B39-C1-D17
A65-B39-C1-D17
A66-B39-C1-D17
A2-B45-C1-D17
A3-B45-C1-D17
A9-B45-C1-D17
A13-B45-C1-D17
A24-B45-C1-D17
A69-B45-C1-D17
A67-B45-C1-D17
A39-B45-C1-D17
A65-B45-C1-D17
A66-B45-C1-D17
A2-B53-C1-D17
A3-B53-C1-D17
A9-B53-C1-D17
A13-B53-C1-D17
A24-B53-C1-D17
A69-B53-C1-D17
A67-B53-C1-D17
A39-B53-C1-D17
A65-B53-C1-D17
A66-B53-C1-D17
A2-B79-C1-D17
A3-B79-C1-D17
A9-B79-C1-D17
A13-B79-C1-D17
A24-B79-C1-D17

-continued
A69-B79-C1-D17
A67-B79-C1-D17
A39-B79-C1-D17
A65-B79-C1-D17
A66-B79-C1-D17
A2-B80-C1-D17
A3-B80-C1-D17
A9-B80-C1-D17
A13-B80-C1-D17
A24-B80-C1-D17
A69-B80-C1-D17
A67-B80-C1-D17
A39-B80-C1-D17
A65-B80-C1-D17
A66-B80-C1-D17
A2-B85-C1-D17
A3-B85-C1-D17
A9-B85-C1-D17
A13-B85-C1-D17
A24-B85-C1-D17
A69-B85-C1-D17
A67-B85-C1-D17
A39-B85-C1-D17
A65-B85-C1-D17
A66-B85-C1-D17
A2-B86-C1-D17
A3-B86-C1-D17
A9-B86-C1-D17
A13-B86-C1-D17
A24-B86-C1-D17
A69-B86-C1-D17
A67-B86-C1-D17
A39-B86-C1-D17
A65-B86-C1-D17
A66-B86-C1-D17
A2-B87-C1-D17
A3-B87-C1-D17
A9-B87-C1-D17
A13-B87-C1-D17
A24-B87-C1-D17
A69-B87-C1-D17
A67-B87-C1-D17
A39-B87-C1-D17
A65-B87-C1-D17
A66-B87-C1-D17
A2-B89-C1-D17
A3-B89-C1-D17
A9-B89-C1-D17
A13-B89-C1-D17
A24-B89-C1-D17
A69-B89-C1-D17
A67-B89-C1-D17
A39-B89-C1-D17
A65-B89-C1-D17
A66-B89-C1-D17
A2-B92-C1-D17
A3-B92-C1-D17
A9-B92-C1-D17
A13-B92-C1-D17
A24-B92-C1-D17
A69-B92-C1-D17
A67-B92-C1-D17
A39-B92-C1-D17
A65-B92-C1-D17
A66-B92-C1-D17
A2-B4-C2-D17
A3-B4-C2-D17
A9-B4-C2-D17
A13-B4-C2-D17
A24-B4-C2-D17
A69-B4-C2-D17
A67-B4-C2-D17
A39-B4-C2-D17
A65-B4-C2-D17
A66-B4-C2-D17
A2-B5-C2-D17
A3-B5-C2-D17
A9-B5-C2-D17
A13-B5-C2-D17
A24-B5-C2-D17

-continued
A69-B5-C2-D17
A67-B5-C2-D17
A39-B5-C2-D17
A65-B5-C2-D17
A66-B5-C2-D17
A2-B6-C2-D17
A3-B6-C2-D17
A9-B6-C2-D17
A13-B6-C2-D17
A24-B6-C2-D17
A69-B6-C2-D17
A67-B6-C2-D17
A39-B6-C2-D17
A65-B6-C2-D17
A66-B6-C2-D17
A2-B32-C2-D17
A3-B32-C2-D17
A9-B32-C2-D17
A13-B32-C2-D17
A24-B32-C2-D17
A69-B32-C2-D17
A67-B32-C2-D17
A39-B32-C2-D17
A65-B32-C2-D17
A66-B32-C2-D17
A2-B39-C2-D17
A3-B39-C2-D17
A9-B39-C2-D17
A13-B39-C2-D17
A24-B39-C2-D17
A69-B39-C2-D17
A67-B39-C2-D17
A39-B39-C2-D17
A65-B39-C2-D17
A66-B39-C2-D17
A2-45-C2-D17
A3-45-C2-D17
A9-B45-C2-D17
A13-B45-C2-D17
A24-B45-C2-D17
A69-B45-C2-D17
A67-B45-C2-D17
A39-B45-C2-D17
A65-B45-C2-D17
A66-B45-C2-D17
A2-B53-C2-D17
A3-B53-C2-D17
A9-B53-C2-D17
A13-B53-C2-D17
A24-B53-C2-D17
A69-B53-C2-D17
A67-B53-C2-D17
A39-B53-C2-D17
A65-B53-C2-D17
A66-B53-C2-D17
A2-B79-C2-D17
A3-B79-C2-D17
A9-B79-C2-D17
A13-B79-C2-D17
A24-B79-C2-D17
A69-B79-C2-D17
A67-B79-C2-D17
A39-B79-C2-D17
A65-B79-C2-D17
A66-B79-C2-D17
A2-B80-C2-D17
A3-B80-C2-D17
A9-B80-C2-D17
A13-B80-C2-D17
A24-B80-C2-D17
A69-B80-C2-D17
A67-B80-C2-D17
A39-B80-C2-D17
A65-B80-C2-D17
A66-B80-C2-D17
A2-B85-C2-D17
A3-B85-C2-D17
A9-B85-C2-D17
A13-B85-C2-D17
A24-B85-C2-D17

-continued
A69-B85-C2-D17
A67-B85-C2-D17
A39-B85-C2-D17
A65-B85-C2-D17
A66-B85-C2-D17
A2-B86-C2-D17
A3-B86-C2-D17
A9-B86-C2-D17
A13-B86-C2-D17
A24-B86-C2-D17
A69-B86-C2-D17
A67-B86-C2-D17
A39-B86-C2-D17
A65-B86-C2-D17
A66-B86-C2-D17
A2-B87-C2-D17
A3-B87-C2-D17
A9-B87-C2-D17
A13-B87-C2-D17
A24-B87-C2-D17
A69-B87-C2-D17
A67-B87-C2-D17
A39-B87-C2-D17
A65-B87-C2-D17
A66-B87-C2-D17
A2-B89-C2-D17
A3-B89-C2-D17
A9-B89-C2-D17
A13-B89-C2-D17
A24-B89-C2-D17
A69-B89-C2-D17
A67-B89-C2-D17
A39-B89-C2-D17
A65-B89-C2-D17
A66-B89-C2-D17
A2-B92-C2-D17
A3-B92-C2-D17
A9-B92-C2-D17
A13-B92-C2-D17
A24-B92-C2-D17
A69-B92-C2-D17
A67-B92-C2-D17
A39-B92-C2-D17
A65-B92-C2-D17
A66-B92-C2-D17
A2-B4-C3-D17
A3-B4-C3-D17
A9-B4-C3-D17
A13-B4-C3-D17
A24-B4-C3-D17
A69-B4-C3-D17
A67-B4-C3-D17
A39-B4-C3-D17
A65-B4-C3-D17
A66-B4-C3-D17
A2-B5-C3-D17
A3-B5-C3-D17
A9-B5-C3-D17
A13-B5-C3-D17
A24-B5-C3-D17
A69-B5-C3-D17
A67-B5-C3-D17
A39-B5-C3-D17
A65-B5-C3-D17
A66-B5-C3-D17
A2-B6-C3-D17
A3-B6-C3-D17
A9-B6-C3-D17
A13-B6-C3-D17
A24-B6-C3-D17
A69-B6-C3-D17
A67-B6-C3-D17
A39-B6-C3-D17
A65-B6-C3-D17
A66-B6-C3-D17
A2-B32-C3-D17
A3-B32-C3-D17
A9-B32-C3-D17
A13-B32-C3-D17
A24-B32-C3-D17

-continued
A69-B32-C3-D17
A67-B32-C3-D17
A39-B32-C3-D17
A65-B32-C3-D17
A66-B32-C3-D17
A2-B39-C3-D17
A3-B39-C3-D17
A9-B39-C3-D17
A13-B39-C3-D17
A24-B39-C3-D17
A69-B39-C3-D17
A67-B39-C3-D17
A39-B39-C3-D17
A65-B39-C3-D17
A66-B39-C3-D17
A2-B45-C3-D17
A3-B45-C3-D17
A9-B45-C3-D17
A13-B45-C3-D17
A24-B45-C3-D17
A69-B45-C3-D17
A67-B45-C3-D17
A39-B45-C3-D17
A65-B45-C3-D17
A66-B45-C3-D17
A2-B53-C3-D17
A3-B53-C3-D17
A9-B53-C3-D17
A13-B53-C3-D17
A24-B53-C3-D17
A69-B53-C3-D17
A67-B53-C3-D17
A39-B53-C3-D17
A65-B53-C3-D17
A66-B53-C3-D17
A2-B79-C3-D17
A3-B79-C3-D17
A9-B79-C3-D17
A13-B79-C3-D17
A24-B79-C3-D17
A69-B79-C3-D17
A67-B79-C3-D17
A39-B79-C3-D17
A65-B79-C3-D17
A66-B79-C3-D17
A2-B80-C3-D17
A3-B80-C3-D17
A9-B80-C3-D17
A13-B80-C3-D17
A24-B80-C3-D17
A69-B80-C3-D17
A67-B80-C3-D17
A39-B80-C3-D17
A65-B80-C3-D17
A66-B80-C3-D17
A2-B85-C3-D17
A3-B85-C3-D17
A9-B85-C3-D17
A13-B85-C3-D17
A24-B85-C3-D17
A69-B85-C3-D17
A67-B85-C3-D17
A39-B85-C3-D17
A65-B85-C3-D17
A66-B85-C3-D17
A2-B86-C3-D17
A3-B86-C3-D17
A9-B86-C3-D17
A13-B86-C3-D17
A24-B86-C3-D17
A69-B86-C3-D17
A67-B86-C3-D17
A39-B86-C3-D17
A65-B86-C3-D17
A66-B86-C3-D17
A2-B87-C3-D17
A3-B87-C3-D17
A9-B87-C3-D17
A13-B87-C3-D17
A24-B87-C3-D17

-continued

A69-B87-C3-D17
A67-B87-C3-D17
A39-B87-C3-D17
A65-B87-C3-D17
A66-B87-C3-D17
A2-B89-C3-D17
A3-B89-C3-D17
A9-B89-C3-D17
A13-B89-C3-D17
A24-B89-C3-D17
A69-B89-C3-D17
A67-B89-C3-D17
A39-B89-C3-D17
A65-B89-C3-D17
A66-B89-C3-D17
A2-B92-C3-D17
A3-B92-C3-D17
A9-B92-C3-D17
A13-B92-C3-D17
A24-B92-C3-D17
A69-B92-C3-D17
A67-B92-C3-D17
A39-B92-C3-D17
A65-B92-C3-D17
A66-B92-C3-D17
A2-B4-C4-D17
A3-B4-C4-D17
A9-B4-C4-D17
A13-B4-C4-D17
A24-B4-C4-D17
A69-B4-C4-D17
A67-B4-C4-D17
A39-B4-C4-D17
A65-B4-C4-D17
A66-B4-C4-D17
A2-B5-C4-D17
A3-B5-C4-D17
A9-B5-C4-D17
A13-B5-C4-D17
A24-B5-C4-D17
A69-B5-C4-D17
A67-B5-C4-D17
A39-B5-C4-D17
A65-B5-C4-D17
A66-B5-C4-D17
A2-B6-C4-D17
A3-B6-C4-D17
A9-B6-C4-D17
A13-B6-C4-D17
A24-B6-C4-D17
A69-B6-C4-D17
A67-B6-C4-D17
A39-B6-C4-D17
A65-B6-C4-D17
A66-B6-C4-D17
A2-B32-C4-D17
A3-B32-C4-D17
A9-B32-C4-D17
A13-B32-C4-D17
A24-B32-C4-D17
A69-B32-C4-D17
A67-B32-C4-D17
A39-B32-C4-D17
A65-B32-C4-D17
A66-B32-C4-D17
A2-B39-C4-D17
A3-B39-C4-D17
A9-B39-C4-D17
A13-B39-C4-D17
A24-B39-C4-D17
A69-B39-C4-D17
A67-B39-C4-D17
A39-B39-C4-D17
A65-B39-C4-D17
A66-B39-C4-D17
A2-B45-C4-D17
A3-B45-C4-D17
A9-B45-C4-D17
A13-B45-C4-D17
A24-B45-C4-D17

-continued

A69-B45-C4-D17
A67-B45-C4-D17
A39-B45-C4-D17
A65-B45-C4-D17
A66-B45-C4-D17
A2-B53-C4-D17
A3-B53-C4-D17
A9-B53-C4-D17
A13-B53-C4-D17
A24-B53-C4-D17
A69-B53-C4-D17
A67-B53-C4-D17
A39-B53-C4-D17
A65-B53-C4-D17
A66-B53-C4-D17
A2-B79-C4-D17
A3-B79-C4-D17
A9-B79-C4-D17
A13-B79-C4-D17
A24-B79-C4-D17
A69-B79-C4-D17
A67-B79-C4-D17
A39-B79-C4-D17
A65-B79-C4-D17
A66-B79-C4-D17
A2-B80-C4-D17
A3-B80-C4-D17
A9-B80-C4-D17
A13-B80-C4-D17
A24-B80-C4-D17
A69-B80-C4-D17
A67-B80-C4-D17
A39-B80-C4-D17
A65-B80-C4-D17
A66-B80-C4-D17
A2-B85-C4-D17
A3-B85-C4-D17
A9-B85-C4-D17
A13-B85-C4-D17
A24-B85-C4-D17
A69-B85-C4-D17
A67-B85-C4-D17
A39-B85-C4-D17
A65-B85-C4-D17
A66-B85-C4-D17
A2-B86-C4-D17
A3-B86-C4-D17
A9-B86-C4-D17
A13-B86-C4-D17
A24-B86-C4-D17
A69-B86-C4-D17
A67-B86-C4-D17
A39-B86-C4-D17
A65-B86-C4-D17
A66-B86-C4-D17
A2-B87-C4-D17
A3-B87-C4-D17
A9-B87-C4-D17
A13-B87-C4-D17
A24-B87-C4-D17
A69-B87-C4-D17
A67-B87-C4-D17
A39-B87-C4-D17
A65-B87-C4-D17
A66-B87-C4-D17
A2-B89-C4-D17
A3-B89-C4-D17
A9-B89-C4-D17
A13-B89-C4-D17
A24-B89-C4-D17
A69-B89-C4-D17
A67-B89-C4-D17
A39-B89-C4-D17
A65-B89-C4-D17
A66-B89-C4-D17
A2-B92-C4-D17
A3-B92-C4-D17
A9-B92-C4-D17
A13-B92-C4-D17
A24-B92-C4-D17

-continued

A69-B92-C4-D17
A67-B92-C4-D17
A39-B92-C4-D17
A65-B92-C4-D17
A66-B92-C4-D17
A2-B4-C5-D17
A3-B4-C5-D17
A9-B4-C5-D17
A13-B4-C5-D17
A24-B4-C5-D17
A69-B4-C5-D17
A67-B4-C5-D17
A39-B4-C5-D17
A65-B4-C5-D17
A66-B4-C5-D17
A2-B5-C5-D17
A3-B5-C5-D17
A9-B5-C5-D17
A13-B5-C5-D17
A24-B5-C5-D17
A69-B5-C5-D17
A67-B5-C5-D17
A39-B5-C5-D17
A65-B5-C5-D17
A66-B5-C5-D17
A2-B6-C5-D17
A3-B6-C5-D17
A9-B6-C5-D17
A13-B6-C5-D17
A24-B6-C5-D17
A69-B6-C5-D17
A67-B6-C5-D17
A39-B6-C5-D17
A65-B6-C5-D17
A66-B6-C5-D17
A2-B32-C5-D17
A3-B32-C5-D17
A9-B32-C5-D17
A13-B32-C5-D17
A24-B32-C5-D17
A69-B32-C5-D17
A67-B32-C5-D17
A39-B32-C5-D17
A65-B32-C5-D17
A66-B32-C5-D17
A2-B39-C5-D17
A3-B39-C5-D17
A9-B39-C5-D17
A13-B39-C5-D17
A24-B39-C5-D17
A69-B39-C5-D17
A67-B39-C5-D17
A39-B39-C5-D17
A65-B39-C5-D17
A66-B39-C5-D17
A2-B45-C5-D17
A3-B45-C5-D17
A9-B45-C5-D17
A13-B45-C5-D17
A24-B45-C5-D17
A69-B45-C5-D17
A67-B45-C5-D17
A39-B45-C5-D17
A65-B45-C5-D17
A66-B45-C5-D17
A2-B53-C5-D17
A3-B53-C5-D17
A9-B53-C5-D17
A13-B53-C5-D17
A24-B53-C5-D17
A69-B53-C5-D17
A67-B53-C5-D17
A39-B53-C5-D17
A65-B53-C5-D17
A66-B53-C5-D17
A2-B79-C5-D17
A3-B79-C5-D17
A9-B79-C5-D17
A13-B79-C5-D17
A24-B79-C5-D17

-continued

A69-B79-C5-D17
A67-B79-C5-D17
A39-B79-C5-D17
A65-B79-C5-D17
A66-B79-C5-D17
A2-B80-C5-D17
A3-B80-C5-D17
A9-B80-C5-D17
A13-B80-C5-D17
A24-B80-C5-D17
A69-B80-C5-D17
A67-B80-C5-D17
A39-B80-C5-D17
A65-B80-C5-D17
A66-B80-C5-D17
A2-B85-C5-D17
A3-B85-C5-D17
A9-B85-C5-D17
A13-B85-C5-D17
A24-B85-C5-D17
A69-B85-C5-D17
A67-B85-C5-D17
A39-B85-C5-D17
A65-B85-C5-D17
A66-B85-C5-D17
A2-B86-C5-D17
A3-B86-C5-D17
A9-B86-C5-D17
A13-B86-C5-D17
A24-B86-C5-D17
A69-B86-C5-D17
A67-B86-C5-D17
A39-B86-C5-D17
A65-B86-C5-D17
A66-B86-C5-D17
A2-B87-C5-D17
A3-B87-C5-D17
A9-B87-C5-D17
A13-B87-C5-D17
A24-B87-C5-D17
A69-B87-C5-D17
A67-B87-C5-D17
A39-B87-C5-D17
A65-B87-C5-D17
A66-B87-C5-D17
A2-B89-C5-D17
A3-B89-C5-D17
A9-B89-C5-D17
A13-B89-C5-D17
A24-B89-C5-D17
A69-B89-C5-D17
A67-B89-C5-D17
A39-B89-C5-D17
A65-B89-C5-D17
A66-B89-C5-D17
A2-B92-C5-D17
A3-B92-C5-D17
A9-B92-C5-D17
A13-B92-C5-D17
A24-B92-C5-D17
A69-B92-C5-D17
A67-B92-C5-D17
A39-B92-C5-D17
A65-B92-C5-D17
A66-B92-C5-D17
A2-B4-C6-D17
A3-B4-C6-D17
A9-B4-C6-D17
A13-B4-C6-D17
A24-B4-C6-D17
A69-B4-C6-D17
A67-B4-C6-D17
A39-B4-C6-D17
A65-B4-C6-D17
A66-B4-C6-D17
A2-B5-C6-D17
A3-B5-C6-D17
A9-B5-C6-D17
A13-B5-C6-D17
A24-B5-C6-D17

-continued
A69-B5-C6-D17
A67-B5-C6-D17
A39-B5-C6-D17
A65-B5-C6-D17
A66-B5-C6-D17
A2-B6-C6-D17
A3-B6-C6-D17
A9-B6-C6-D17
A13-B6-C6-D17
A24-B6-C6-D17
A69-B6-C6-D17
A67-B6-C6-D17
A39-B6-C6-D17
A65-B6-C6-D17
A66-B6-C6-D17
A2-B32-C6-D17
A3-B32-C6-D17
A9-B32-C6-D17
A13-B32-C6-D17
A24-B32-C6-D17
A69-B32-C6-D17
A67-B32-C6-D17
A39-B32-C6-D17
A65-B32-C6-D17
A66-B32-C6-D17
A2-B39-C6-D17
A3-B39-C6-D17
A9-B39-C6-D17
A13-B39-C6-D17
A24-B39-C6-D17
A69-B39-C6-D17
A67-B39-C6-D17
A39-B39-C6-D17
A65-B39-C6-D17
A66-B39-C6-D17
A2-B45-C6-D17
A3-B45-C6-D17
A9-B45-C6-D17
A13-B45-C6-D17
A24-B45-C6-D17
A69-B45-C6-D17
A67-B45-C6-D17
A39-B45-C6-D17
A65-B45-C6-D17
A66-B45-C6-D17
A2-B53-C6-D17
A3-B53-C6-D17
A9-B53-C6-D17
A13-B53-C6-D17
A24-B53-C6-D17
A69-B53-C6-D17
A67-B53-C6-D17
A39-B53-C6-D17
A65-B53-C6-D17
A66-B53-C6-D17
A2-B79-C6-D17
A3-B79-C6-D17
A9-B79-C6-D17
A13-B79-C6-D17
A24-B79-C6-D17
A69-B79-C6-D17
A67-B79-C6-D17
A39-B79-C6-D17
A65-B79-C6-D17
A66-B79-C6-D17
A2-B80-C6-D17
A3-B80-C6-D17
A9-B80-C6-D17
A13-B80-C6-D17
A24-B80-C6-D17
A69-B80-C6-D17
A67-B80-C6-D17
A39-B80-C6-D17
A65-B80-C6-D17
A66-B80-C6-D17
A2-B85-C6-D17
A3-B85-C6-D17
A9-B85-C6-D17
A13-B85-C6-D17
A24-B85-C6-D17

-continued
A69-B85-C6-D17
A67-B85-C6-D17
A39-B85-C6-D17
A65-B85-C6-D17
A66-B85-C6-D17
A2-B86-C6-D17
A3-B86-C6-D17
A9-B86-C6-D17
A13-B86-C6-D17
A24-B86-C6-D17
A69-B86-C6-D17
A67-B86-C6-D17
A39-B86-C6-D17
A65-B86-C6-D17
A66-B86-C6-D17
A2-B87-C6-D17
A3-B87-C6-D17
A9-B87-C6-D17
A13-B87-C6-D17
A24-B87-C6-D17
A69-B87-C6-D17
A67-B87-C6-D17
A39-B87-C6-D17
A65-B87-C6-D17
A66-B87-C6-D17
A2-B89-C6-D17
A3-B89-C6-D17
A9-B89-C6-D17
A13-B89-C6-D17
A24-B89-C6-D17
A69-B89-C6-D17
A67-B89-C6-D17
A39-B89-C6-D17
A65-B89-C6-D17
A66-B89-C6-D17
A2-B92-C6-D17
A3-B92-C6-D17
A9-B92-C6-D17
A13-B92-C6-D17
A24-B92-C6-D17
A69-B92-C6-D17
A67-B92-C6-D17
A39-B92-C6-D17
A65-B92-C6-D17
A66-B92-C6-D17
A2-B4-C7-D17
A3-B4-C7-D17
A9-B4-C7-D17
A13-B4-C7-D17
A24-B4-C7-D17
A69-B4-C7-D17
A67-B4-C7-D17
A39-B4-C7-D17
A65-B4-C7-D17
A66-B4-C7-D17
A2-B5-C7-D17
A3-B5-C7-D17
A9-B5-C7-D17
A13-B5-C7-D17
A24-B5-C7-D17
A69-B5-C7-D17
A67-B5-C7-D17
A39-B5-C7-D17
A65-B5-C7-D17
A66-B5-C7-D17
A2-B6-C7-D17
A3-B6-C7-D17
A9-B6-C7-D17
A13-B6-C7-D17
A24-B6-C7-D17
A69-B6-C7-D17
A67-B6-C7-D17
A39-B6-C7-D17
A65-B6-C7-D17
A66-B6-C7-D17
A2-B32-C7-D17
A3-B32-C7-D17
A9-B32-C7-D17
A13-B32-C7-D17
A24-B32-C7-D17

-continued

A69-B32-C7-D17
A67-B32-C7-D17
A39-B32-C7-D17
A65-B32-C7-D17
A66-B32-C7-D17
A2-B39-C7-D17
A3-B39-C7-D17
A9-B39-C7-D17
A13-B39-C7-D17
A24-B39-C7-D17
A69-B39-C7-D17
A67-B39-C7-D17
A39-B39-C7-D17
A65-B39-C7-D17
A66-B39-C7-D17
A2-B45-C7-D17
A3-B45-C7-D17
A9-B45-C7-D17
A13-B45-C7-D17
A24-B45-C7-D17
A69-B45-C7-D17
A67-B45-C7-D17
A39-B45-C7-D17
A65-B45-C7-D17
A66-B45-C7-D17
A2-B53-C7-D17
A3-B53-C7-D17
A9-B53-C7-D17
A13-B53-C7-D17
A24-B53-C7-D17
A69-B53-C7-D17
A67-B53-C7-D17
A39-B53-C7-D17
A65-B53-C7-D17
A66-B53-C7-D17
A2-B79-C7-D17
A3-B79-C7-D17
A9-B79-C7-D17
A13-B79-C7-D17
A24-B79-C7-D17
A69-B79-C7-D17
A67-B79-C7-D17
A39-B79-C7-D17
A65-B79-C7-D17
A66-B79-C7-D17
A2-B80-C7-D17
A3-B80-C7-D17
A9-B80-C7-D17
A13-B80-C7-D17
A24-B80-C7-D17
A69-B80-C7-D17
A67-B80-C7-D17
A39-B80-C7-D17
A65-B80-C7-D17
A66-B80-C7-D17
A2-B85-C7-D17
A3-B85-C7-D17
A9-B85-C7-D17
A13-B85-C7-D17
A24-B85-C7-D17
A69-B85-C7-D17
A67-B85-C7-D17
A39-B85-C7-D17
A65-B85-C7-D17
A66-B85-C7-D17
A2-B86-C7-D17
A3-B86-C7-D17
A9-B86-C7-D17
A13-B86-C7-D17
A24-B86-C7-D17
A69-B86-C7-D17
A67-B86-C7-D17
A39-B86-C7-D17
A65-B86-C7-D17
A66-B86-C7-D17
A2-B87-C7-D17
A3-B87-C7-D17
A9-B87-C7-D17
A13-B87-C7-D17
A24-B87-C7-D17

-continued

A69-B87-C7-D17
A67-B87-C7-D17
A39-B87-C7-D17
A65-B87-C7-D17
A66-B87-C7-D17
A2-B89-C7-D17
A3-B89-C7-D17
A9-B89-C7-D17
A13-B89-C7-D17
A24-B89-C7-D17
A69-B89-C7-D17
A67-B89-C7-D17
A39-B89-C7-D17
A65-B89-C7-D17
A66-B89-C7-D17
A2-B92-C7-D17
A3-B92-C7-D17
A9-B92-C7-D17
A13-B92-C7-D17
A24-B92-C7-D17
A69-B92-C7-D17
A67-B92-C7-D17
A39-B92-C7-D17
A65-B92-C7-D17
A66-B92-C7-D17
A2-B4-C8-D17
A3-B4-C8-D17
A9-B4-C8-D17
A13-B4-C8-D17
A24-B4-C8-D17
A69-B4-C8-D17
A67-B4-C8-D17
A39-B4-C8-D17
A65-B4-C8-D17
A66-B4-C8-D17
A2-B5-C8-D17
A3-B5-C8-D17
A9-B5-C8-D17
A13-B5-C8-D17
A24-B5-C8-D17
A69-B5-C8-D17
A67-B5-C8-D17
A39-B5-C8-D17
A65-B5-C8-D17
A66-B5-C8-D17
A2-B6-C8-D17
A3-B6-C8-D17
A9-B6-C8-D17
A13-B6-C8-D17
A24-B6-C8-D17
A69-B6-C8-D17
A67-B6-C8-D17
A39-B6-C8-D17
A65-B6-C8-D17
A66-B6-C8-D17
A2-B32-C8-D17
A3-B32-C8-D17
A9-B32-C8-D17
A13-B32-C8-D17
A24-B32-C8-D17
A69-B32-C8-D17
A67-B32-C8-D17
A39-B32-C8-D17
A65-B32-C8-D17
A66-B32-C8-D17
A2-B39-C8-D17
A3-B39-C8-D17
A9-B39-C8-D17
A13-B39-C8-D17
A24-B39-C8-D17
A69-B39-C8-D17
A67-B39-C8-D17
A39-B39-C8-D17
A65-B39-C8-D17
A66-B39-C8-D17
A2-B45-C8-D17
A3-B45-C8-D17
A9-B45-C8-D17
A13-B45-C8-D17
A24-B45-C8-D17

-continued
A69-B45-C8-D17
A67-B45-C8-D17
A39-B45-C8-D17
A65-B45-C8-D17
A66-B45-C8-D17
A2-B53-C8-D17
A3-B53-C8-D17
A9-B53-C8-D17
A13-B53-C8-D17
A24-B53-C8-D17
A69-B53-C8-D17
A67-B53-C8-D17
A39-B53-C8-D17
A65-B53-C8-D17
A66-B53-C8-D17
A2-B79-C8-D17
A3-B79-C8-D17
A9-B79-C8-D17
A13-B79-C8-D17
A24-B79-C8-D17
A69-B79-C8-D17
A67-B79-C8-D17
A39-B79-C8-D17
A65-B79-C8-D17
A66-B79-C8-D17
A2-B80-C8-D17
A3-B80-C8-D17
A9-B80-C8-D17
A13-B80-C8-D17
A24-B80-C8-D17
A69-B80-C8-D17
A67-B80-C8-D17
A39-B80-C8-D17
A65-B80-C8-D17
A66-B80-C8-D17
A2-B85-C8-D17
A3-B85-C8-D17
A9-B85-C8-D17
A13-B85-C8-D17
A24-B85-C8-D17
A69-B85-C8-D17
A67-B85-C8-D17
A39-B85-C8-D17
A65-B85-C8-D17
A66-B85-C8-D17
A2-B86-C8-D17
A3-B86-C8-D17
A9-B86-C8-D17
A13-B86-C8-D17
A24-B86-C8-D17
A69-B86-C8-D17
A67-B86-C8-D17
A39-B86-C8-D17
A65-B86-C8-D17
A66-B86-C8-D17
A2-B87-C8-D17
A3-B87-C8-D17
A9-B87-C8-D17
A13-B87-C8-D17
A24-B87-C8-D17
A69-B87-C8-D17
A67-B87-C8-D17
A39-B87-C8-D17
A65-B87-C8-D17
A66-B87-C8-D17
A2-B89-C8-D17
A3-B89-C8-D17
A9-B89-C8-D17
A13-B89-C8-D17
A24-B89-C8-D17
A69-B89-C8-D17
A67-B89-C8-D17
A39-B89-C8-D17
A65-B89-C8-D17
A66-B89-C8-D17
A2-B92-C8-D17
A3-B92-C8-D17
A9-B92-C8-D17
A13-B92-C8-D17
A24-B92-C8-D17

-continued
A69-B92-C8-D17
A67-B92-C8-D17
A39-B92-C8-D17
A65-B92-C8-D17
A66-B92-C8-D17
A2-B4-C9-D17
A3-B4-C9-D17
A9-B4-C9-D17
A13-B4-C9-D17
A24-B4-C9-D17
A69-B4-C9-D17
A67-B4-C9-D17
A39-B4-C9-D17
A65-B4-C9-D17
A66-B4-C9-D17
A2-B5-C9-D17
A3-B5-C9-D17
A9-B5-C9-D17
A13-B5-C9-D17
A24-B5-C9-D17
A69-B5-C9-D17
A67-B5-C9-D17
A39-B5-C9-D17
A65-B5-C9-D17
A66-B5-C9-D17
A2-B6-C9-D17
A3-B6-C9-D17
A9-B6-C9-D17
A13-B6-C9-D17
A24-B6-C9-D17
A69-B6-C9-D17
A67-B6-C9-D17
A39-B6-C9-D17
A65-B6-C9-D17
A66-B6-C9-D17
A2-B32-C9-D17
A3-B32-C9-D17
A9-B32-C9-D17
A13-B32-C9-D17
A24-B32-C9-D17
A69-B32-C9-D17
A67-B32-C9-D17
A39-B32-C9-D17
A65-B32-C9-D17
A66-B32-C9-D17
A2-B39-C9-D17
A3-B39-C9-D17
A9-B39-C9-D17
A13-B39-C9-D17
A24-B39-C9-D17
A69-B39-C9-D17
A67-B39-C9-D17
A39-B39-C9-D17
A65-B39-C9-D17
A66-B39-C9-D17
A2-B45-C9-D17
A3-B45-C9-D17
A9-B45-C9-D17
A13-B45-C9-D17
A24-B45-C9-D17
A69-B45-C9-D17
A67-B45-C9-D17
A39-B45-C9-D17
A65-B45-C9-D17
A66-B45-C9-D17
A2-B53-C9-D17
A3-B53-C9-D17
A9-B53-C9-D17
A13-B53-C9-D17
A24-B53-C9-D17
A69-B53-C9-D17
A67-B53-C9-D17
A39-B53-C9-D17
A65-B53-C9-D17
A66-B53-C9-D17
A2-B79-C9-D17
A3-B79-C9-D17
A9-B79-C9-D17
A13-B79-C9-D17
A24-B79-C9-D17

-continued

A69-B79-C9-D17
A67-B79-C9-D17
A39-B79-C9-D17
A65-B79-C9-D17
A66-B79-C9-D17
A2-B80-C9-D17
A3-B80-C9-D17
A9-B80-C9-D17
A13-B80-C9-D17
A24-B80-C9-D17
A69-B80-C9-D17
A67-B80-C9-D17
A39-B80-C9-D17
A65-B80-C9-D17
A66-B80-C9-D17
A2-B85-C9-D17
A3-B85-C9-D17
A9-B85-C9-D17
A13-B85-C9-D17
A24-B85-C9-D17
A69-B85-C9-D17
A67-B85-C9-D17
A39-B85-C9-D17
A65-B85-C9-D17
A66-B85-C9-D17
A2-B86-C9-D17
A3-B86-C9-D17
A9-B86-C9-D17
A13-B86-C9-D17
A24-B86-C9-D17
A69-B86-C9-D17
A67-B86-C9-D17
A39-B86-C9-D17
A65-B86-C9-D17
A66-B86-C9-D17
A2-B87-C9-D17
A3-B87-C9-D17
A9-B87-C9-D17
A13-B87-C9-D17
A24-B87-C9-D17
A69-B87-C9-D17
A67-B87-C9-D17
A39-B87-C9-D17
A65-B87-C9-D17
A66-B87-C9-D17
A2-B89-C9-D17
A3-B89-C9-D17
A9-B89-C9-D17
A13-B89-C9-D17
A24-B89-C9-D17
A69-B89-C9-D17
A67-B89-C9-D17
A39-B89-C9-D17
A65-B89-C9-D17
A66-B89-C9-D17
A2-B92-C9-D17
A3-B92-C9-D17
A9-B92-C9-D17
A13-B92-C9-D17
A24-B92-C9-D17
A69-B92-C9-D17
A67-B92-C9-D17
A39-B92-C9-D17
A65-B92-C9-D17
A66-B92-C9-D17
A2-B4-C10-D17
A3-B4-C10-D17
A9-B4-C10-D17
A13-B4-C10-D17
A24-B4-C10-D17
A69-B4-C10-D17
A67-B4-C10-D17
A39-B4-C10-D17
A65-B4-C10-D17
A66-B4-C10-D17
A2-B5-C10-D17
A3-B5-C10-D17
A9-B5-C10-D17
A13-B5-C10-D17
A24-B5-C10-D17

-continued

A69-B5-C10-D17
A67-B5-C10-D17
A39-B5-C10-D17
A65-B5-C10-D17
A66-B5-C10-D17
A2-B6-C10-D17
A3-B6-C10-D17
A9-B6-C10-D17
A13-B6-C10-D17
A24-B6-C10-D17
A69-B6-C10-D17
A67-B6-C10-D17
A39-B6-C10-D17
A65-B6-C10-D17
A66-B6-C10-D17
A2-B32-C10-D17
A3-B32-C10-D17
A9-B32-C10-D17
A13-B32-C10-D17
A24-B32-C10-D17
A69-B32-C10-D17
A67-B32-C10-D17
A39-B32-C10-D17
A65-B32-C10-D17
A66-B32-C10-D17
A2-B39-C10-D17
A3-B39-C10-D17
A9-B39-C10-D17
A13-B39-C10-D17
A24-B39-C10-D17
A69-B39-C10-D17
A67-B39-C10-D17
A39-B39-C10-D17
A65-B39-C10-D17
A66-B39-C10-D17
A2-B45-C10-D17
A3-B45-C10-D17
A9-B45-C10-D17
A13-B45-C10-D17
A24-B45-C10-D17
A69-B45-C10-D17
A67-B45-C10-D17
A39-B45-C10-D17
A65-B45-C10-D17
A66-B45-C10-D17
A2-B53-C10-D17
A3-B53-C10-D17
A9-B53-C10-D17
A13-B53-C10-D17
A24-B53-C10-D17
A69-B53-C10-D17
A67-B53-C10-D17
A39-B53-C10-D17
A65-B53-C10-D17
A66-B53-C10-D17
A2-B79-C10-D17
A3-B79-C10-D17
A9-B79-C10-D17
A13-B79-C10-D17
A24-B79-C10-D17
A69-B79-C10-D17
A67-B79-C10-D17
A39-B79-C10-D17
A65-B79-C10-D17
A66-B79-C10-D17
A2-B80-C10-D17
A3-B80-C10-D17
A9-B80-C10-D17
A13-B80-C10-D17
A24-B80-C10-D17
A69-B80-C10-D17
A67-B80-C10-D17
A39-B80-C10-D17
A65-B80-C10-D17
A66-B80-C10-D17
A2-B85-C10-D17
A3-B85-C10-D17
A9-B85-C10-D17
A13-B85-C10-D17
A24-B85-C10-D17

-continued
A69-B85-C10-D17
A67-B85-C10-D17
A39-B85-C10-D17
A65-B85-C10-D17
A66-B85-C10-D17
A2-B86-C10-D17
A3-B86-C10-D17
A9-B86-C10-D17
A13-B86-C10-D17
A24-B86-C10-D17
A69-B86-C10-D17
A67-B86-C10-D17
A39-B86-C10-D17
A65-B86-C10-D17
A66-B86-C10-D17
A2-B87-C10-D17
A3-B87-C10-D17
A9-B87-C10-D17
A13-B87-C10-D17
A24-B87-C10-D17
A69-B87-C10-D17
A67-B87-C10-D17
A39-B87-C10-D17
A65-B87-C10-D17
A66-B87-C10-D17
A2-B89-C10-D17
A3-B89-C10-D17
A9-B89-C10-D17
A13-B89-C10-D17
A24-B89-C10-D17
A69-B89-C10-D17
A67-B89-C10-D17
A39-B89-C10-D17
A65-B89-C10-D17
A66-B89-C10-D17
A2-B92-C10-D17
A3-B92-C10-D17
A9-B92-C10-D17
A13-B92-C10-D17
A24-B92-C10-D17
A69-B92-C10-D17
A67-B92-C10-D17
A39-B92-C10-D17
A65-B92-C10-D17
A66-B92-C10-D17
A2-B4-C11-D17
A3-B4-C11-D17
A9-B4-C11-D17
A13-B4-C11-D17
A24-B4-C11-D17
A69-B4-C11-D17
A67-B4-C11-D17
A39-B4-C11-D17
A65-B4-C11-D17
A66-B4-C11-D17
A2-B5-C11-D17
A3-B5-C11-D17
A9-B5-C11-D17
A13-B5-C11-D17
A24-B5-C11-D17
A69-B5-C11-D17
A67-B5-C11-D17
A39-B5-C11-D17
A65-B5-C11-D17
A66-B5-C11-D17
A2-B6-C11-D17
A3-B6-C11-D17
A9-B6-C11-D17
A13-B6-C11-D17
A24-B6-C11-D17
A69-B6-C11-D17
A67-B6-C11-D17
A39-B6-C11-D17
A65-B6-C11-D17
A66-B6-C11-D17
A2-B32-C11-D17
A3-B32-C11-D17
A9-B32-C11-D17
A13-B32-C11-D17
A24-B32-C11-D17

-continued
A69-B32-C11-D17
A67-B32-C11-D17
A39-B32-C11-D17
A65-B32-C11-D17
A66-B32-C11-D17
A2-B39-C11-D17
A3-B39-C11-D17
A9-B39-C11-D17
A13-B39-C11-D17
A24-B39-C11-D17
A69-B39-C11-D17
A67-B39-C11-D17
A39-B39-C11-D17
A65-B39-C11-D17
A66-B39-C11-D17
A2-B45-C11-D17
A3-B45-C11-D17
A9-B45-C11-D17
A13-B45-C11-D17
A24-B45-C11-D17
A69-B45-C11-D17
A67-B45-C11-D17
A39-B45-C11-D17
A65-B45-C11-D17
A66-B45-C11-D17
A2-B53-C11-D17
A3-B53-C11-D17
A9-B53-C11-D17
A13-B53-C11-D17
A24-B53-C11-D17
A69-B53-C11-D17
A67-B53-C11-D17
A39-B53-C11-D17
A65-B53-C11-D17
A66-B53-C11-D17
A2-B79-C11-D17
A3-B79-C11-D17
A9-B79-C11-D17
A13-B79-C11-D17
A24-B79-C11-D17
A69-B79-C11-D17
A67-B79-C11-D17
A39-B79-C11-D17
A65-B79-C11-D17
A66-B79-C11-D17
A2-B80-C11-D17
A3-B80-C11-D17
A9-B80-C11-D17
A13-B80-C11-D17
A24-B80-C11-D17
A69-B80-C11-D17
A67-B80-C11-D17
A39-B80-C11-D17
A65-B80-C11-D17
A66-B80-C11-D17
A2-B85-C11-D17
A3-B85-C11-D17
A9-B85-C11-D17
A13-B85-C11-D17
A24-B85-C11-D17
A69-B85-C11-D17
A67-B85-C11-D17
A39-B85-C11-D17
A65-B85-C11-D17
A66-B85-C11-D17
A2-B86-C11-D17
A3-B86-C11-D17
A9-B86-C11-D17
A13-B86-C11-D17
A24-B86-C11-D17
A69-B86-C11-D17
A67-B86-C11-D17
A39-B86-C11-D17
A65-B86-C11-D17
A66-B86-C11-D17
A2-B87-C11-D17
A3-B87-C11-D17
A9-B87-C11-D17
A13-B87-C11-D17
A24-B87-C11-D17

-continued

A69-B87-C11-D17
A67-B87-C11-D17
A39-B87-C11-D17
A65-B87-C11-D17
A66-B87-C11-D17
A2-B89-C11-D17
A3-B89-C11-D17
A9-B89-C11-D17
A13-B89-C11-D17
A24-B89-C11-D17
A69-B89-C11-D17
A67-B89-C11-D17
A39-B89-C11-D17
A65-B89-C11-D17
A66-B89-C11-D17
A2-B92-C11-D17
A3-B92-C11-D17
A9-B92-C11-D17
A13-B92-C11-D17
A24-B92-C11-D17
A69-B92-C11-D17
A67-B92-C11-D17
A39-B92-C11-D17
A65-B92-C11-D17
A66-B92-C11-D17
A2-B4-C12-D17
A3-B4-C12-D17
A9-B4-C12-D17
A13-B4-C12-D17
A24-B4-C12-D17
A69-B4-C12-D17
A67-B4-C12-D17
A39-B4-C12-D17
A65-B4-C12-D17
A66-B4-C12-D17
A2-B5-C12-D17
A3-B5-C12-D17
A9-B5-C12-D17
A13-B5-C12-D17
A24-B5-C12-D17
A69-B5-C12-D17
A67-B5-C12-D17
A39-B5-C12-D17
A65-B5-C12-D17
A66-B5-C12-D17
A2-B6-C12-D17
A3-B6-C12-D17
A9-B6-C12-D17
A13-B6-C12-D17
A24-B6-C12-D17
A69-B6-C12-D17
A67-B6-C12-D17
A39-B6-C12-D17
A65-B6-C12-D17
A66-B6-C12-D17
A2-B32-C12-D17
A3-B32-C12-D17
A9-B32-C12-D17
A13-B32-C12-D17
A24-B32-C12-D17
A69-B32-C12-D17
A67-B32-C12-D17
A39-B32-C12-D17
A65-B32-C12-D17
A66-B32-C12-D17
A2-B39-C12-D17
A3-B39-C12-D17
A9-B39-C12-D17
A13-B39-C12-D17
A24-B39-C12-D17
A69-B39-C12-D17
A67-B39-C12-D17
A39-B39-C12-D17
A65-B39-C12-D17
A66-B39-C12-D17
A2-B45-C12-D17
A3-B45-C12-D17
A9-B45-C12-D17
A13-B45-C12-D17
A24-B45-C12-D17

-continued

A69-B45-C12-D17
A67-B45-C12-D17
A39-B45-C12-D17
A65-B45-C12-D17
A66-B45-C12-D17
A2-B53-C12-D17
A3-B53-C12-D17
A9-B53-C12-D17
A13-B53-C12-D17
A24-B53-C12-D17
A69-B53-C12-D17
A67-B53-C12-D17
A39-B53-C12-D17
A65-B53-C12-D17
A66-B53-C12-D17
A2-B79-C12-D17
A3-B79-C12-D17
A9-B79-C12-D17
A13-B79-C12-D17
A24-B79-C12-D17
A69-B79-C12-D17
A67-B79-C12-D17
A39-B79-C12-D17
A65-B79-C12-D17
A66-B79-C12-D17
A2-B80-C12-D17
A3-B80-C12-D17
A9-B80-C12-D17
A13-B80-C12-D17
A24-B80-C12-D17
A69-B80-C12-D17
A67-B80-C12-D17
A39-B80-C12-D17
A65-B80-C12-D17
A66-B80-C12-D17
A2-B85-C12-D17
A3-B85-C12-D17
A9-B85-C12-D17
A13-B85-C12-D17
A24-B85-C12-D17
A69-B85-C12-D17
A67-B85-C12-D17
A39-B85-C12-D17
A65-B85-C12-D17
A66-B85-C12-D17
A2-B86-C12-D17
A3-B86-C12-D17
A9-B86-C12-D17
A13-B86-C12-D17
A24-B86-C12-D17
A69-B86-C12-D17
A67-B86-C12-D17
A39-B86-C12-D17
A65-B86-C12-D17
A66-B86-C12-D17
A2-B87-C12-D17
A3-B87-C12-D17
A9-B87-C12-D17
A13-B87-C12-D17
A24-B87-C12-D17
A69-B87-C12-D17
A67-B87-C12-D17
A39-B87-C12-D17
A65-B87-C12-D17
A66-B87-C12-D17
A2-B89-C12-D17
A3-B89-C12-D17
A9-B89-C12-D17
A13-B89-C12-D17
A24-B89-C12-D17
A69-B89-C12-D17
A67-B89-C12-D17
A39-B89-C12-D17
A65-B89-C12-D17
A66-B89-C12-D17
A2-B92-C12-D17
A3-B92-C12-D17
A9-B92-C12-D17
A13-B92-C12-D17
A24-B92-C12-D17

-continued
A69-B92-C12-D17
A67-B92-C12-D17
A39-B92-C12-D17
A65-B92-C12-D17
A66-B92-C12-D17
A2-B4-C13-D17
A3-B4-C13-D17
A9-B4-C13-D17
A13-B4-C13-D17
A24-B4-C13-D17
A69-B4-C13-D17
A67-B4-C13-D17
A39-B4-C13-D17
A65-B4-C13-D17
A66-B4-C13-D17
A2-B5-C13-D17
A3-B5-C13-D17
A9-B5-C13-D17
A13-B5-C13-D17
A24-B5-C13-D17
A69-B5-C13-D17
A67-B5-C13-D17
A39-B5-C13-D17
A65-B5-C13-D17
A66-B5-C13-D17
A2-B6-C13-D17
A3-B6-C13-D17
A9-B6-C13-D17
A13-B6-C13-D17
A24-B6-C13-D17
A69-B6-C13-D17
A67-B6-C13-D17
A39-B6-C13-D17
A65-B6-C13-D17
A66-B6-C13-D17
A2-B32-C13-D17
A3-B32-C13-D17
A9-B32-C13-D17
A13-B32-C13-D17
A24-B32-C13-D17
A69-B32-C13-D17
A67-B32-C13-D17
A39-B32-C13-D17
A65-B32-C13-D17
A66-B32-C13-D17
A2-B39-C13-D17
A3-B39-C13-D17
A9-B39-C13-D17
A13-B39-C13-D17
A24-B39-C13-D17
A69-B39-C13-D17
A67-B39-C13-D17
A39-B39-C13-D17
A65-B39-C13-D17
A66-B39-C13-D17
A2-B45-C13-D17
A3-B45-C13-D17
A9-B45-C13-D17
A13-B45-C13-D17
A24-B45-C13-D17
A69-B45-C13-D17
A67-B45-C13-D17
A39-B45-C13-D17
A65-B45-C13-D17
A66-B45-C13-D17
A2-B53-C13-D17
A3-B53-C13-D17
A9-B53-C13-D17
A13-B53-C13-D17
A24-B53-C13-D17
A69-B53-C13-D17
A67-B53-C13-D17
A39-B53-C13-D17
A65-B53-C13-D17
A66-B53-C13-D17
A2-B79-C13-D17
A3-B79-C13-D17
A9-B79-C13-D17
A13-B79-C13-D17
A24-B79-C13-D17

-continued
A69-B79-C13-D17
A67-B79-C13-D17
A39-B79-C13-D17
A65-B79-C13-D17
A66-B79-C13-D17
A2-B80-C13-D17
A3-B80-C13-D17
A9-B80-C13-D17
A13-B80-C13-D17
A24-B80-C13-D17
A69-B80-C13-D17
A67-B80-C13-D17
A39-B80-C13-D17
A65-B80-C13-D17
A66-B80-C13-D17
A2-B85-C13-D17
A3-B85-C13-D17
A9-B85-C13-D17
A13-B85-C13-D17
A24-B85-C13-D17
A69-B85-C13-D17
A67-B85-C13-D17
A39-B85-C13-D17
A65-B85-C13-D17
A66-B85-C13-D17
A2-B86-C13-D17
A3-B86-C13-D17
A9-B86-C13-D17
A13-B86-C13-D17
A24-B86-C13-D17
A69-B86-C13-D17
A67-B86-C13-D17
A39-B86-C13-D17
A65-B86-C13-D17
A66-B86-C13-D17
A2-B87-C13-D17
A3-B87-C13-D17
A9-B87-C13-D17
A13-B87-C13-D17
A24-B87-C13-D17
A69-B87-C13-D17
A67-B87-C13-D17
A39-B87-C13-D17
A65-B87-C13-D17
A66-B87-C13-D17
A2-B89-C13-D17
A3-B89-C13-D17
A9-B89-C13-D17
A13-B89-C13-D17
A24-B89-C13-D17
A69-B89-C13-D17
A67-B89-C13-D17
A39-B89-C13-D17
A65-B89-C13-D17
A66-B89-C13-D17
A2-B92-C13-D17
A3-B92-C13-D17
A9-B92-C13-D17
A13-B92-C13-D17
A24-B92-C13-D17
A69-B92-C13-D17
A67-B92-C13-D17
A39-B92-C13-D17
A65-B92-C13-D17
A66-B92-C13-D17
A2-B4-C1-D18
A3-B4-C1-D18
A9-B4-C1-D18
A13-B4-C1-D18
A24-B4-C1-D18
A69-B4-C1-D18
A67-B4-C1-D18
A39-B4-C1-D18
A65-B4-C1-D18
A66-B4-C1-D18
A2-B5-C1-D18
A3-B5-C1-D18
A9-B5-C1-D18
A13-B5-C1-D18
A24-B5-C1-D18

-continued

A69-B5-C1-D18
A67-B5-C1-D18
A39-B5-C1-D18
A65-B5-C1-D18
A66-B5-C1-D18
A2-B6-C1-D18
A3-B6-C1-D18
A9-B6-C1-D18
A13-B6-C1-D18
A24-B6-C1-D18
A69-B6-C1-D18
A67-B6-C1-D18
A39-B6-C1-D18
A65-B6-C1-D18
A66-B6-C1-D18
A2-B32-C1-D18
A3-B32-C1-D18
A9-B32-C1-D18
A13-B32-C1-D18
A24-B32-C1-D18
A69-B32-C1-D18
A67-B32-C1-D18
A39-B32-C1-D18
A65-B32-C1-D18
A66-B32-C1-D18
A2-B39-C1-D18
A3-B39-C1-D18
A9-B39-C1-D18
A13-B39-C1-D18
A24-B39-C1-D18
A69-B39-C1-D18
A67-B39-C1-D18
A39-B39-C1-D18
A65-B39-C1-D18
A66-B39-C1-D18
A2-B45-C1-D18
A3-B45-C1-D18
A9-B45-C1-D18
A13-B45-C1-D18
A24-B45-C1-D18
A69-B45-C1-D18
A67-B45-C1-D18
A39-B45-C1-D18
A65-B45-C1-D18
A66-B45-C1-D18
A2-B53-C1-D18
A3-B53-C1-D18
A9-B53-C1-D18
A13-B53-C1-D18
A24-B53-C1-D18
A69-B53-C1-D18
A67-B53-C1-D18
A39-B53-C1-D18
A65-B53-C1-D18
A66-B53-C1-D18
A2-B79-C1-D18
A3-B79-C1-D18
A9-B79-C1-D18
A13-B79-C1-D18
A24-B79-C1-D18
A69-B79-C1-D18
A67-B79-C1-D18
A39-B79-C1-D18
A65-B79-C1-D18
A66-B79-C1-D18
A2-B80-C1-D18
A3-B80-C1-D18
A9-B80-C1-D18
A13-B80-C1-D18
A24-B80-C1-D18
A69-B80-C1-D18
A67-B80-C1-D18
A39-B80-C1-D18
A65-B80-C1-D18
A66-B80-C1-D18
A2-B85-C1-D18
A3-B85-C1-D18
A9-B85-C1-D18
A13-B85-C1-D18
A24-B85-C1-D18

-continued

A69-B85-C1-D18
A67-B85-C1-D18
A39-B85-C1-D18
A65-B85-C1-D18
A66-B85-C1-D18
A2-B86-C1-D18
A3-B86-C1-D18
A9-B86-C1-D18
A13-B86-C1-D18
A24-B86-C1-D18
A69-B86-C1-D18
A67-B86-C1-D18
A39-B86-C1-D18
A65-B86-C1-D18
A66-B86-C1-D18
A2-B87-C1-D18
A3-B87-C1-D18
A9-B87-C1-D18
A13-B87-C1-D18
A24-B87-C1-D18
A69-B87-C1-D18
A67-B87-C1-D18
A39-B87-C1-D18
A65-B87-C1-D18
A66-B87-C1-D18
A2-B89-C1-D18
A3-B89-C1-D18
A9-B89-C1-D18
A13-B89-C1-D18
A24-B89-C1-D18
A69-B89-C1-D18
A67-B89-C1-D18
A39-B89-C1-D18
A65-B89-C1-D18
A66-B89-C1-D18
A2-B92-C1-D18
A3-B92-C1-D18
A9-B92-C1-D18
A13-B92-C1-D18
A24-B92-C1-D18
A69-B92-C1-D18
A67-B92-C1-D18
A39-B92-C1-D18
A65-B92-C1-D18
A66-B92-C1-D18
A2-B4-C2-D18
A3-B4-C2-D18
A9-B4-C2-D18
A13-B4-C2-D18
A24-B4-C2-D18
A69-B4-C2-D18
A67-B4-C2-D18
A39-B4-C2-D18
A65-B4-C2-D18
A66-B4-C2-D18
A2-B5-C2-D18
A3-B5-C2-D18
A9-B5-C2-D18
A13-B5-C2-D18
A24-B5-C2-D18
A69-B5-C2-D18
A67-B5-C2-D18
A39-B5-C2-D18
A65-B5-C2-D18
A66-B5-C2-D18
A2-B6-C2-D18
A3-B6-C2-D18
A9-B6-C2-D18
A13-B6-C2-D18
A24-B6-C2-D18
A69-B6-C2-D18
A67-B6-C2-D18
A39-B6-C2-D18
A65-B6-C2-D18
A66-B6-C2-D18
A2-B32-C2-D18
A3-B32-C2-D18
A9-B32-C2-D18
A13-B32-C2-D18
A24-B32-C2-D18

-continued

A69-B32-C2-D18
A67-B32-C2-D18
A39-B32-C2-D18
A65-B32-C2-D18
A66-B32-C2-D18
A2-B39-C2-D18
A3-B39-C2-D18
A9-B39-C2-D18
A13-B39-C2-D18
A24-B39-C2-D18
A69-B39-C2-D18
A67-B39-C2-D18
A39-B39-C2-D18
A65-B39-C2-D18
A66-B39-C2-D18
A2-B45-C2-D18
A3-B45-C2-D18
A9-B45-C2-D18
A13-B45-C2-D18
A24-B45-C2-D18
A69-B45-C2-D18
A67-B45-C2-D18
A39-B45-C2-D18
A65-B45-C2-D18
A66-B45-C2-D18
A2-B53-C2-D18
A3-B53-C2-D18
A9-B53-C2-D18
A13-B53-C2-D18
A24-B53-C2-D18
A69-B53-C2-D18
A67-B53-C2-D18
A39-B53-C2-D18
A65-B53-C2-D18
A66-B53-C2-D18
A2-B79-C2-D18
A3-B79-C2-D18
A9-B79-C2-D18
A13-B79-C2-D18
A24-B79-C2-D18
A69-B79-C2-D18
A67-B79-C2-D18
A39-B79-C2-D18
A65-B79-C2-D18
A66-B79-C2-D18
A2-B80-C2-D18
A3-B80-C2-D18
A9-B80-C2-D18
A13-B80-C2-D18
A24-B80-C2-D18
A69-B80-C2-D18
A67-B80-C2-D18
A39-B80-C2-D18
A65-B80-C2-D18
A66-B80-C2-D18
A2-B85-C2-D18
A3-B85-C2-D18
A9-B85-C2-D18
A13-B85-C2-D18
A24-B85-C2-D18
A69-B85-C2-D18
A67-B85-C2-D18
A39-B85-C2-D18
A65-B85-C2-D18
A66-B85-C2-D18
A2-B86-C2-D18
A3-B86-C2-D18
A9-B86-C2-D18
A13-B86-C2-D18
A24-B86-C2-D18
A69-B86-C2-D18
A67-B86-C2-D18
A39-B86-C2-D18
A65-B86-C2-D18
A66-B86-C2-D18
A2-B87-C2-D18
A3-B87-C2-D18
A9-B87-C2-D18
A13-B87-C2-D18
A24-B87-C2-D18

-continued

A69-B87-C2-D18
A67-B87-C2-D18
A39-B87-C2-D18
A65-B87-C2-D18
A66-B87-C2-D18
A2-B89-C2-D18
A3-B89-C2-D18
A9-B89-C2-D18
A13-B89-C2-D18
A24-B89-C2-D18
A69-B89-C2-D18
A67-B89-C2-D18
A39-B89-C2-D18
A65-B89-C2-D18
A66-B89-C2-D18
A2-B92-C2-D18
A3-B92-C2-D18
A9-B92-C2-D18
A13-B92-C2-D18
A24-B92-C2-D18
A69-B92-C2-D18
A67-B92-C2-D18
A39-B92-C2-D18
A65-B92-C2-D18
A66-B92-C2-D18
A2-B4-C3-D18
A3-B4-C3-D18
A9-B4-C3-D18
A13-B4-C3-D18
A24-B4-C3-D18
A69-B4-C3-D18
A67-B4-C3-D18
A39-B4-C3-D18
A65-B4-C3-D18
A66-B4-C3-D18
A2-B5-C3-D18
A3-B5-C3-D18
A9-B5-C3-D18
A13-B5-C3-D18
A24-B5-C3-D18
A69-B5-C3-D18
A67-B5-C3-D18
A39-B5-C3-D18
A65-B5-C3-D18
A66-B5-C3-D18
A2-B6-C3-D18
A3-B6-C3-D18
A9-B6-C3-D18
A13-B6-C3-D18
A24-B6-C3-D18
A69-B6-C3-D18
A67-B6-C3-D18
A39-B6-C3-D18
A65-B6-C3-D18
A66-B6-C3-D18
A2-B32-C3-D18
A3-B32-C3-D18
A9-B32-C3-D18
A13-B32-C3-D18
A24-B32-C3-D18
A69-B32-C3-D18
A67-B32-C3-D18
A39-B32-C3-D18
A65-B32-C3-D18
A66-B32-C3-D18
A2-B39-C3-D18
A3-B39-C3-D18
A9-B39-C3-D18
A13-B39-C3-D18
A24-B39-C3-D18
A69-B39-C3-D18
A67-B39-C3-D18
A39-B39-C3-D18
A65-B39-C3-D18
A66-B39-C3-D18
A2-B45-C3-D18
A3-B45-C3-D18
A9-B45-C3-D18
A13-B45-C3-D18
A24-B45-C3-D18

-continued
A69-B45-C3-D18
A67-B45-C3-D18
A39-B45-C3-D18
A65-B45-C3-D18
A66-B45-C3-D18
A2-B53-C3-D18
A3-B53-C3-D18
A9-B53-C3-D18
A13-B53-C3-D18
A24-B53-C3-D18
A69-B53-C3-D18
A67-B53-C3-D18
A39-B53-C3-D18
A65-B53-C3-D18
A66-B53-C3-D18
A2-B79-C3-D18
A3-B79-C3-D18
A9-B79-C3-D18
A13-B79-C3-D18
A24-B79-C3-D18
A69-B79-C3-D18
A67-B79-C3-D18
A39-B79-C3-D18
A65-B79-C3-D18
A66-B79-C3-D18
A2-B80-C3-D18
A3-B80-C3-D18
A9-B80-C3-D18
A13-B80-C3-D18
A24-B80-C3-D18
A69-B80-C3-D18
A67-B80-C3-D18
A39-B80-C3-D18
A65-B80-C3-D18
A66-B80-C3-D18
A2-B85-C3-D18
A3-B85-C3-D18
A9-B85-C3-D18
A13-B85-C3-D18
A24-B85-C3-D18
A69-B85-C3-D18
A67-B85-C3-D18
A39-B85-C3-D18
A65-B85-C3-D18
A66-B85-C3-D18
A2-B86-C3-D18
A3-B86-C3-D18
A9-B86-C3-D18
A13-B86-C3-D18
A24-B86-C3-D18
A69-B86-C3-D18
A67-B86-C3-D18
A39-B86-C3-D18
A65-B86-C3-D18
A66-B86-C3-D18
A2-B87-C3-D18
A3-B87-C3-D18
A9-B87-C3-D18
A13-B87-C3-D18
A24-B87-C3-D18
A69-B87-C3-D18
A67-B87-C3-D18
A39-B87-C3-D18
A65-B87-C3-D18
A66-B87-C3-D18
A2-B89-C3-D18
A3-B89-C3-D18
A9-B89-C3-D18
A13-B89-C3-D18
A24-B89-C3-D18
A69-B89-C3-D18
A67-B89-C3-D18
A39-B89-C3-D18
A65-B89-C3-D18
A66-B89-C3-D18
A2-B92-C3-D18
A3-B92-C3-D18
A9-B92-C3-D18
A13-B92-C3-D18
A24-B92-C3-D18

-continued
A69-B92-C3-D18
A67-B92-C3-D18
A39-B92-C3-D18
A65-B92-C3-D18
A66-B92-C3-D18
A2-B4-C4-D18
A3-B4-C4-D18
A9-B4-C4-D18
A13-B4-C4-D18
A24-B4-C4-D18
A69-B4-C4-D18
A67-B4-C4-D18
A39-B4-C4-D18
A65-B4-C4-D18
A66-B4-C4-D18
A2-B5-C4-D18
A3-B5-C4-D18
A9-B5-C4-D18
A13-B5-C4-D18
A24-B5-C4-D18
A69-B5-C4-D18
A67-B5-C4-D18
A39-B5-C4-D18
A65-B5-C4-D18
A66-B5-C4-D18
A2-B6-C4-D18
A3-B6-C4-D18
A9-B6-C4-D18
A13-B6-C4-D18
A24-B6-C4-D18
A69-B6-C4-D18
A67-B6-C4-D18
A39-B6-C4-D18
A65-B6-C4-D18
A66-B6-C4-D18
A2-B32-C4-D18
A3-B32-C4-D18
A9-B32-C4-D18
A13-B32-C4-D18
A24-B32-C4-D18
A69-B32-C4-D18
A67-B32-C4-D18
A39-B32-C4-D18
A65-B32-C4-D18
A66-B32-C4-D18
A2-B39-C4-D18
A3-B39-C4-D18
A9-B39-C4-D18
A13-B39-C4-D18
A24-B39-C4-D18
A69-B39-C4-D18
A67-B39-C4-D18
A39-B39-C4-D18
A65-B39-C4-D18
A66-B39-C4-D18
A2-B45-C4-D18
A3-B45-C4-D18
A9-B45-C4-D18
A13-B45-C4-D18
A24-B45-C4-D18
A69-B45-C4-D18
A67-B45-C4-D18
A39-B45-C4-D18
A65-B45-C4-D18
A66-B45-C4-D18
A2-B53-C4-D18
A3-B53-C4-D18
A9-B53-C4-D18
A13-B53-C4-D18
A24-B53-C4-D18
A69-B53-C4-D18
A67-B53-C4-D18
A39-B53-C4-D18
A65-B53-C4-D18
A66-B53-C4-D18
A2-B79-C4-D18
A3-B79-C4-D18
A9-B79-C4-D18
A13-B79-C4-D18
A24-B79-C4-D18

-continued
A69-B79-C4-D18
A67-B79-C4-D18
A39-B79-C4-D18
A65-B79-C4-D18
A66-B79-C4-D18
A2-B80-C4-D18
A3-B80-C4-D18
A9-B80-C4-D18
A13-B80-C4-D18
A24-B80-C4-D18
A69-B80-C4-D18
A67-B80-C4-D18
A39-B80-C4-D18
A65-B80-C4-D18
A66-B80-C4-D18
A2-B85-C4-D18
A3-B85-C4-D18
A9-B85-C4-D18
A13-B85-C4-D18
A24-B85-C4-D18
A69-B85-C4-D18
A67-B85-C4-D18
A39-B85-C4-D18
A65-B85-C4-D18
A66-B85-C4-D18
A2-B86-C4-D18
A3-B86-C4-D18
A9-B86-C4-D18
A13-B86-C4-D18
A24-B86-C4-D18
A69-B86-C4-D18
A67-B86-C4-D18
A39-B86-C4-D18
A65-B86-C4-D18
A66-B86-C4-D18
A2-B87-C4-D18
A3-B87-C4-D18
A9-B87-C4-D18
A13-B87-C4-D18
A24-B87-C4-D18
A69-B87-C4-D18
A67-B87-C4-D18
A39-B87-C4-D18
A65-B87-C4-D18
A66-B87-C4-D18
A2-B89-C4-D18
A3-B89-C4-D18
A9-B89-C4-D18
A13-B89-C4-D18
A24-B89-C4-D18
A69-B89-C4-D18
A67-B89-C4-D18
A39-B89-C4-D18
A65-B89-C4-D18
A66-B89-C4-D18
A2-B92-C4-D18
A3-B92-C4-D18
A9-B92-C4-D18
A13-B92-C4-D18
A24-B92-C4-D18
A69-B92-C4-D18
A67-B92-C4-D18
A39-B92-C4-D18
A65-B92-C4-D18
A66-B92-C4-D18
A2-B4-C5-D18
A3-B4-C5-D18
A9-B4-C5-D18
A13-B4-C5-D18
A24-B4-C5-D18
A69-B4-C5-D18
A67-B4-C5-D18
A39-B4-C5-D18
A65-B4-C5-D18
A66-B4-C5-D18
A2-B5-C5-D18
A3-B5-C5-D18
A9-B5-C5-D18
A13-B5-C5-D18
A24-B5-C5-D18

-continued
A69-B5-C5-D18
A67-B5-C5-D18
A39-B5-C5-D18
A65-B5-C5-D18
A66-B5-C5-D18
A2-B6-C5-D18
A3-B6-C5-D18
A9-B6-C5-D18
A13-B6-C5-D18
A24-B6-C5-D18
A69-B6-C5-D18
A67-B6-C5-D18
A39-B6-C5-D18
A65-B6-C5-D18
A66-B6-C5-D18
A2-B32-C5-D18
A3-B32-C5-D18
A9-B32-C5-D18
A13-B32-C5-D18
A24-B32-C5-D18
A69-B32-C5-D18
A67-B32-C5-D18
A39-B32-C5-D18
A65-B32-C5-D18
A66-B32-C5-D18
A2-B39-C5-D18
A3-B39-C5-D18
A9-B39-C5-D18
A13-B39-C5-D18
A24-B39-C5-D18
A69-B39-C5-D18
A67-B39-C5-D18
A39-B39-C5-D18
A65-B39-C5-D18
A66-B39-C5-D18
A2-B45-C5-D18
A3-B45-C5-D18
A9-B45-C5-D18
A13-B45-C5-D18
A24-B45-C5-D18
A69-B45-C5-D18
A67-B45-C5-D18
A39-B45-C5-D18
A65-B45-C5-D18
A66-B45-C5-D18
A2-B53-C5-D18
A3-B53-C5-D18
A9-B53-C5-D18
A13-B53-C5-D18
A24-B53-C5-D18
A69-B53-C5-D18
A67-B53-C5-D18
A39-B53-C5-D18
A65-B53-C5-D18
A66-B53-C5-D18
A2-B79-C5-D18
A3-B79-C5-D18
A9-B79-C5-D18
A13-B79-C5-D18
A24-B79-C5-D18
A69-B79-C5-D18
A67-B79-C5-D18
A39-B79-C5-D18
A65-B79-C5-D18
A66-B79-C5-D18
A2-B80-C5-D18
A3-B80-C5-D18
A9-B80-C5-D18
A13-B80-C5-D18
A24-B80-C5-D18
A69-B80-C5-D18
A67-B80-C5-D18
A39-B80-C5-D18
A65-B80-C5-D18
A66-B80-C5-D18
A2-B85-C5-D18
A3-B85-C5-D18
A9-B85-C5-D18
A13-B85-C5-D18
A24-B85-C5-D18

-continued
A69-B85-C5-D18
A67-B85-C5-D18
A39-B85-C5-D18
A65-B85-C5-D18
A66-B85-C5-D18
A2-B86-C5-D18
A3-B86-C5-D18
A9-B86-C5-D18
A13-B86-C5-D18
A24-B86-C5-D18
A69-B86-C5-D18
A67-B86-C5-D18
A39-B86-C5-D18
A65-B86-C5-D18
A66-B86-C5-D18
A2-B87-C5-D18
A3-B87-C5-D18
A9-B87-C5-D18
A13-B87-C5-D18
A24-B87-C5-D18
A69-B87-C5-D18
A67-B87-C5-D18
A39-B87-C5-D18
A65-B87-C5-D18
A66-B87-C5-D18
A2-B89-C5-D18
A3-B89-C5-D18
A9-B89-C5-D18
A13-B89-C5-D18
A24-B89-C5-D18
A69-B89-C5-D18
A67-B89-C5-D18
A39-B89-C5-D18
A65-B89-C5-D18
A66-B89-C5-D18
A2-B92-C5-D18
A3-B92-C5-D18
A9-B92-C5-D18
A13-B92-C5-D18
A24-B92-C5-D18
A69-B92-C5-D18
A67-B92-C5-D18
A39-B92-C5-D18
A65-B92-C5-D18
A66-B92-C5-D18
A2-B4-C6-D18
A3-B4-C6-D18
A9-B4-C6-D18
A13-B4-C6-D18
A24-B4-C6-D18
A69-B4-C6-D18
A67-B4-C6-D18
A39-B4-C6-D18
A65-B4-C6-D18
A66-B4-C6-D18
A2-B5-C6-D18
A3-B5-C6-D18
A9-B5-C6-D18
A13-B5-C6-D18
A24-B5-C6-D18
A69-B5-C6-D18
A67-B5-C6-D18
A39-B5-C6-D18
A65-B5-C6-D18
A66-B5-C6-D18
A2-B6-C6-D18
A3-B6-C6-D18
A9-B6-C6-D18
A13-B6-C6-D18
A24-B6-C6-D18
A69-B6-C6-D18
A67-B6-C6-D18
A39-B6-C6-D18
A65-B6-C6-D18
A66-B6-C6-D18
A2-B32-C6-D18
A3-B32-C6-D18
A9-B32-C6-D18
A13-B32-C6-D18
A24-B32-C6-D18

-continued
A69-B32-C6-D18
A67-B32-C6-D18
A39-B32-C6-D18
A65-B32-C6-D18
A66-B32-C6-D18
A2-B39-C6-D18
A3-B39-C6-D18
A9-B39-C6-D18
A13-B39-C6-D18
A24-B39-C6-D18
A69-B39-C6-D18
A67-B39-C6-D18
A39-B39-C6-D18
A65-B39-C6-D18
A66-B39-C6-D18
A2-B45-C6-D18
A3-B45-C6-D18
A9-B45-C6-D18
A13-B45-C6-D18
A24-B45-C6-D18
A69-B45-C6-D18
A67-B45-C6-D18
A39-B45-C6-D18
A65-B45-C6-D18
A66-B45-C6-D18
A2-B53-C6-D18
A3-B53-C6-D18
A9-B53-C6-D18
A13-B53-C6-D18
A24-B53-C6-D18
A69-B53-C6-D18
A67-B53-C6-D18
A39-B53-C6-D18
A65-B53-C6-D18
A66-B53-C6-D18
A2-B79-C6-D18
A3-B79-C6-D18
A9-B79-C6-D18
A13-B79-C6-D18
A24-B79-C6-D18
A69-B79-C6-D18
A67-B79-C6-D18
A39-B79-C6-D18
A65-B79-C6-D18
A66-B79-C6-D18
A2-B80-C6-D18
A3-B80-C6-D18
A9-B80-C6-D18
A13-B80-C6-D18
A24-B80-C6-D18
A69-B80-C6-D18
A67-B80-C6-D18
A39-B80-C6-D18
A65-B80-C6-D18
A66-B80-C6-D18
A2-B85-C6-D18
A3-B85-C6-D18
A9-B85-C6-D18
A13-B85-C6-D18
A24-B85-C6-D18
A69-B85-C6-D18
A67-B85-C6-D18
A39-B85-C6-D18
A65-B85-C6-D18
A66-B85-C6-D18
A2-B86-C6-D18
A3-B86-C6-D18
A9-B86-C6-D18
A13-B86-C6-D18
A24-B86-C6-D18
A69-B86-C6-D18
A67-B86-C6-D18
A39-B86-C6-D18
A65-B86-C6-D18
A66-B86-C6-D18
A2-B87-C6-D18
A3-B87-C6-D18
A9-B87-C6-D18
A13-B87-C6-D18
A24-B87-C6-D18

-continued
A69-B87-C6-D18
A67-B87-C6-D18
A39-B87-C6-D18
A65-B87-C6-D18
A66-B87-C6-D18
A2-B89-C6-D18
A3-B89-C6-D18
A9-B89-C6-D18
A13-B89-C6-D18
A24-B89-C6-D18
A69-B89-C6-D18
A67-B89-C6-D18
A39-B89-C6-D18
A65-B89-C6-D18
A66-B89-C6-D18
A2-B92-C6-D18
A3-B92-C6-D18
A9-B92-C6-D18
A13-B92-C6-D18
A24-B92-C6-D18
A69-B92-C6-D18
A67-B92-C6-D18
A39-B92-C6-D18
A65-B92-C6-D18
A66-B92-C6-D18
A2-B4-C7-D18
A3-B4-C7-D18
A9-B4-C7-D18
A13-B4-C7-D18
A24-B4-C7-D18
A69-B4-C7-D18
A67-B4-C7-D18
A39-B4-C7-D18
A65-B4-C7-D18
A66-B4-C7-D18
A2-B5-C7-D18
A3-B5-C7-D18
A9-B5-C7-D18
A13-B5-C7-D18
A24-B5-C7-D18
A69-B5-C7-D18
A67-B5-C7-D18
A39-B5-C7-D18
A65-B5-C7-D18
A66-B5-C7-D18
A2-B6-C7-D18
A3-B6-C7-D18
A9-B6-C7-D18
A13-B6-C7-D18
A24-B6-C7-D18
A69-B6-C7-D18
A67-B6-C7-D18
A39-B6-C7-D18
A65-B6-C7-D18
A66-B6-C7-D18
A2-B32-C7-D18
A3-B32-C7-D18
A9-B32-C7-D18
A13-B32-C7-D18
A24-B32-C7-D18
A69-B32-C7-D18
A67-B32-C7-D18
A39-B32-C7-D18
A65-B32-C7-D18
A66-B32-C7-D18
A2-B39-C7-D18
A3-B39-C7-D18
A9-B39-C7-D18
A13-B39-C7-D18
A24-B39-C7-D18
A69-B39-C7-D18
A67-B39-C7-D18
A39-B39-C7-D18
A65-B39-C7-D18
A66-B39-C7-D18
A2-B45-C7-D18
A3-B45-C7-D18
A9-B45-C7-D18
A13-B45-C7-D18
A24-B45-C7-D18

-continued
A69-B45-C7-D18
A67-B45-C7-D18
A39-B45-C7-D18
A65-B45-C7-D18
A66-B45-C7-D18
A2-B53-C7-D18
A3-B53-C7-D18
A9-B53-C7-D18
A13-B53-C7-D18
A24-B53-C7-D18
A69-B53-C7-D18
A67-B53-C7-D18
A39-B53-C7-D18
A65-B53-C7-D18
A66-B53-C7-D18
A2-B79-C7-D18
A3-B79-C7-D18
A9-B79-C7-D18
A13-B79-C7-D18
A24-B79-C7-D18
A69-B79-C7-D18
A67-B79-C7-D18
A39-B79-C7-D18
A65-B79-C7-D18
A66-B79-C7-D18
A2-B80-C7-D18
A3-B80-C7-D18
A9-B80-C7-D18
A13-B80-C7-D18
A24-B80-C7-D18
A69-B80-C7-D18
A67-B80-C7-D18
A39-B80-C7-D18
A65-B80-C7-D18
A66-B80-C7-D18
A2-B85-C7-D18
A3-B85-C7-D18
A9-B85-C7-D18
A13-B85-C7-D18
A24-B85-C7-D18
A69-B85-C7-D18
A67-B85-C7-D18
A39-B85-C7-D18
A65-B85-C7-D18
A66-B85-C7-D18
A2-B86-C7-D18
A3-B86-C7-D18
A9-B86-C7-D18
A13-B86-C7-D18
A24-B86-C7-D18
A69-B86-C7-D18
A67-B86-C7-D18
A39-B86-C7-D18
A65-B86-C7-D18
A66-B86-C7-D18
A2-B87-C7-D18
A3-B87-C7-D18
A9-B87-C7-D18
A13-B87-C7-D18
A24-B87-C7-D18
A69-B87-C7-D18
A67-B87-C7-D18
A39-B87-C7-D18
A65-B87-C7-D18
A66-B87-C7-D18
A2-B89-C7-D18
A3-B89-C7-D18
A9-B89-C7-D18
A13-B89-C7-D18
A24-B89-C7-D18
A69-B89-C7-D18
A67-B89-C7-D18
A39-B89-C7-D18
A65-B89-C7-D18
A66-B89-C7-D18
A2-B92-C7-D18
A3-B92-C7-D18
A9-B92-C7-D18
A13-B92-C7-D18
A24-B92-C7-D18

-continued
A69-B92-C7-D18
A67-B92-C7-D18
A39-B92-C7-D18
A65-B92-C7-D18
A66-B92-C7-D18
A2-B4-C8-D18
A3-B4-C8-D18
A9-B4-C8-D18
A13-B4-C8-D18
A24-B4-C8-D18
A69-B4-C8-D18
A67-B4-C8-D18
A39-B4-C8-D18
A65-B4-C8-D18
A66-B4-C8-D18
A2-B5-C8-D18
A3-B5-C8-D18
A9-B5-C8-D18
A13-B5-C8-D18
A24-B5-C8-D18
A69-B5-C8-D18
A67-B5-C8-D18
A39-B5-C8-D18
A65-B5-C8-D18
A66-B5-C8-D18
A2-B6-C8-D18
A3-B6-C8-D18
A9-B6-C8-D18
A13-B6-C8-D18
A24-B6-C8-D18
A69-B6-C8-D18
A67-B6-C8-D18
A39-B6-C8-D18
A65-B6-C8-D18
A66-B6-C8-D18
A2-B32-C8-D18
A3-B32-C8-D18
A9-B32-C8-D18
A13-B32-C8-D18
A24-B32-C8-D18
A69-B32-C8-D18
A67-B32-C8-D18
A39-B32-C8-D18
A65-B32-C8-D18
A66-B32-C8-D18
A2-B39-C8-D18
A3-B39-C8-D18
A9-B39-C8-D18
A13-B39-C8-D18
A24-B39-C8-D18
A69-B39-C8-D18
A67-B39-C8-D18
A39-B39-C8-D18
A65-B39-C8-D18
A66-B39-C8-D18
A2-B45-C8-D18
A3-B45-C8-D18
A9-B45-C8-D18
A13-B45-C8-D18
A24-B45-C8-D18
A69-B45-C8-D18
A67-B45-C8-D18
A39-B45-C8-D18
A65-B45-C8-D18
A66-B45-C8-D18
A2-B53-C8-D18
A3-B53-C8-D18
A9-B53-C8-D18
A13-B53-C8-D18
A24-B53-C8-D18
A69-B53-C8-D18
A67-B53-C8-D18
A39-B53-C8-D18
A65-B53-C8-D18
A66-B53-C8-D18
A2-B79-C8-D18
A3-B79-C8-D18
A9-B79-C8-D18
A13-B79-C8-D18
A24-B79-C8-D18

-continued
A69-B79-C8-D18
A67-B79-C8-D18
A39-B79-C8-D18
A65-B79-C8-D18
A66-B79-C8-D18
A2-B80-C8-D18
A3-B80-C8-D18
A9-B80-C8-D18
A13-B80-C8-D18
A24-B80-C8-D18
A69-B80-C8-D18
A67-B80-C8-D18
A39-B80-C8-D18
A65-B80-C8-D18
A66-B80-C8-D18
A2-B85-C8-D18
A3-B85-C8-D18
A9-B85-C8-D18
A13-B85-C8-D18
A24-B85-C8-D18
A69-B85-C8-D18
A67-B85-C8-D18
A39-B85-C8-D18
A65-B85-C8-D18
A66-B85-C8-D18
A2-B86-C8-D18
A3-B86-C8-D18
A9-B86-C8-D18
A13-B86-C8-D18
A24-B86-C8-D18
A69-B86-C8-D18
A67-B86-C8-D18
A39-B86-C8-D18
A65-B86-C8-D18
A66-B86-C8-D18
A2-B87-C8-D18
A3-B87-C8-D18
A9-B87-C8-D18
A13-B87-C8-D18
A24-B87-C8-D18
A69-B87-C8-D18
A67-B87-C8-D18
A39-B87-C8-D18
A65-B87-C8-D18
A66-B87-C8-D18
A2-B89-C8-D18
A3-B89-C8-D18
A9-B89-C8-D18
A13-B89-C8-D18
A24-B89-C8-D18
A69-B89-C8-D18
A67-B89-C8-D18
A39-B89-C8-D18
A65-B89-C8-D18
A66-B89-C8-D18
A2-B92-C8-D18
A3-B92-C8-D18
A9-B92-C8-D18
A13-B92-C8-D18
A24-B92-C8-D18
A69-B92-C8-D18
A67-B92-C8-D18
A39-B92-C8-D18
A65-B92-C8-D18
A66-B92-C8-D18
A2-B4-C9-D18
A3-B4-C9-D18
A9-B4-C9-D18
A13-B4-C9-D18
A24-B4-C9-D18
A69-B4-C9-D18
A67-B4-C9-D18
A39-B4-C9-D18
A65-B4-C9-D18
A66-B4-C9-D18
A2-B5-C9-D18
A3-B5-C9-D18
A9-B5-C9-D18
A13-B5-C9-D18
A24-B5-C9-D18

-continued
A69-B5-C9-D18
A67-B5-C9-D18
A39-B5-C9-D18
A65-B5-C9-D18
A66-B5-C9-D18
A2-B6-C9-D18
A3-B6-C9-D18
A9-B6-C9-D18
A13-B6-C9-D18
A24-B6-C9-D18
A69-B6-C9-D18
A67-B6-C9-D18
A39-B6-C9-D18
A65-B6-C9-D18
A66-B6-C9-D18
A2-B32-C9-D18
A3-B32-C9-D18
A9-B32-C9-D18
A13-B32-C9-D18
A24-B32-C9-D18
A69-B32-C9-D18
A67-B32-C9-D18
A39-B32-C9-D18
A65-B32-C9-D18
A66-B32-C9-D18
A2-B39-C9-D18
A3-B39-C9-D18
A9-B39-C9-D18
A13-B39-C9-D18
A24-B39-C9-D18
A69-B39-C9-D18
A67-B39-C9-D18
A39-B39-C9-D18
A65-B39-C9-D18
A66-B39-C9-D18
A2-B45-C9-D18
A3-B45-C9-D18
A9-B45-C9-D18
A13-B45-C9-D18
A24-B45-C9-D18
A69-B45-C9-D18
A67-B45-C9-D18
A39-B45-C9-D18
A65-B45-C9-D18
A66-B45-C9-D18
A2-B53-C9-D18
A3-B53-C9-D18
A9-B53-C9-D18
A13-B53-C9-D18
A24-B53-C9-D18
A69-B53-C9-D18
A67-B53-C9-D18
A39-B53-C9-D18
A65-B53-C9-D18
A66-B53-C9-D18
A2-B79-C9-D18
A3-B79-C9-D18
A9-B79-C9-D18
A13-B79-C9-D18
A24-B79-C9-D18
A69-B79-C9-D18
A67-B79-C9-D18
A39-B79-C9-D18
A65-B79-C9-D18
A66-B79-C9-D18
A2-B80-C9-D18
A3-B80-C9-D18
A9-B80-C9-D18
A13-B80-C9-D18
A24-B80-C9-D18
A69-B80-C9-D18
A67-B80-C9-D18
A39-B80-C9-D18
A65-B80-C9-D18
A66-B80-C9-D18
A2-B85-C9-D18
A3-B85-C9-D18
A9-B85-C9-D18
A13-B85-C9-D18
A24-B85-C9-D18

-continued
A69-B85-C9-D18
A67-B85-C9-D18
A39-B85-C9-D18
A65-B85-C9-D18
A66-B85-C9-D18
A2-B86-C9-D18
A3-B86-C9-D18
A9-B86-C9-D18
A13-B86-C9-D18
A24-B86-C9-D18
A69-B86-C9-D18
A67-B86-C9-D18
A39-B86-C9-D18
A65-B86-C9-D18
A66-B86-C9-D18
A2-B87-C9-D18
A3-B87-C9-D18
A9-B87-C9-D18
A13-B87-C9-D18
A24-B87-C9-D18
A69-B87-C9-D18
A67-B87-C9-D18
A39-B87-C9-D18
A65-B87-C9-D18
A66-B87-C9-D18
A2-B89-C9-D18
A3-B89-C9-D18
A9-B89-C9-D18
A13-B89-C9-D18
A24-B89-C9-D18
A69-B89-C9-D18
A67-B89-C9-D18
A39-B89-C9-D18
A65-B89-C9-D18
A66-B89-C9-D18
A2-B92-C9-D18
A3-B92-C9-D18
A9-B92-C9-D18
A13-B92-C9-D18
A24-B92-C9-D18
A69-B92-C9-D18
A67-B92-C9-D18
A39-B92-C9-D18
A65-B92-C9-D18
A66-B92-C9-D18
A2-B4-C10-D18
A3-B4-C10-D18
A9-B4-C10-D18
A13-B4-C10-D18
A24-B4-C10-D18
A69-B4-C10-D18
A67-B4-C10-D18
A39-B4-C10-D18
A65-B4-C10-D18
A66-B4-C10-D18
A2-B5-C10-D18
A3-B5-C10-D18
A9-B5-C10-D18
A13-B5-C10-D18
A24-B5-C10-D18
A69-B5-C10-D18
A67-B5-C10-D18
A39-B5-C10-D18
A65-B5-C10-D18
A66-B5-C10-D18
A2-B6-C10-D18
A3-B6-C10-D18
A9-B6-C10-D18
A13-B6-C10-D18
A24-B6-C10-D18
A69-B6-C10-D18
A67-B6-C10-D18
A39-B6-C10-D18
A65-B6-C10-D18
A66-B6-C10-D18
A2-B32-C10-D18
A3-B32-C10-D18
A9-B32-C10-D18
A13-B32-C10-D18
A24-B32-C10-D18

-continued
A69-B32-C10-D18
A67-B32-C10-D18
A39-B32-C10-D18
A65-B32-C10-D18
A66-B32-C10-D18
A2-B39-C10-D18
A3-B39-C10-D18
A9-B39-C10-D18
A13-B39-C10-D18
A24-B39-C10-D18
A69-B39-C10-D18
A67-B39-C10-D18
A39-B39-C10-D18
A65-B39-C10-D18
A66-B39-C10-D18
A2-B45-C10-D18
A3-B45-C10-D18
A9-B45-C10-D18
A13-B45-C10-D18
A24-B45-C10-D18
A69-B45-C10-D18
A67-B45-C10-D18
A39-B45-C10-D18
A65-B45-C10-D18
A66-B45-C10-D18
A2-B53-C10-D18
A3-B53-C10-D18
A9-B53-C10-D18
A13-B53-C10-D18
A24-B53-C10-D18
A69-B53-C10-D18
A67-B53-C10-D18
A39-B53-C10-D18
A65-B53-C10-D18
A66-B53-C10-D18
A2-B79-C10-D18
A3-B79-C10-D18
A9-B79-C10-D18
A13-B79-C10-D18
A24-B79-C10-D18
A69-B79-C10-D18
A67-B79-C10-D18
A39-B79-C10-D18
A65-B79-C10-D18
A66-B79-C10-D18
A2-B80-C10-D18
A3-B80-C10-D18
A9-B80-C10-D18
A13-B80-C10-D18
A24-B80-C10-D18
A69-B80-C10-D18
A67-B80-C10-D18
A39-B80-C10-D18
A65-B80-C10-D18
A66-B80-C10-D18
A2-B85-C10-D18
A3-B85-C10-D18
A9-B85-C10-D18
A13-B85-C10-D18
A24-B85-C10-D18
A69-B85-C10-D18
A67-B85-C10-D18
A39-B85-C10-D18
A65-B85-C10-D18
A66-B85-C10-D18
A2-B86-C10-D18
A3-B86-C10-D18
A9-B86-C10-D18
A13-B86-C10-D18
A24-B86-C10-D18
A69-B86-C10-D18
A67-B86-C10-D18
A39-B86-CiO-D18
A65-B86-C10-D18
A66-B86-C10-D18
A2-B87-C10-D18
A3-B87-C10-D18
A9-B87-C10-D18
A13-B87-C10-D18
A24-B87-C10-D18

-continued
A69-B87-C10-D18
A67-B87-C10-D18
A39-B87-C10-D18
A65-B87-C10-D18
A66-B87-C10-D18
A2-B89-C10-D18
A3-B89-C10-D18
A9-B89-C10-D18
A13-B89-C10-D18
A24-B89-C10-D18
A69-B89-C10-D18
A67-B89-C10-D18
A39-B89-C10-D18
A65-B89-C10-D18
A66-B89-C10-D18
A2-B92-C10-D18
A3-B92-C10-D18
A9-B92-C10-D18
A13-B92-C10-D18
A24-B92-C10-D18
A69-B92-C10-D18
A67-B92-C10-D18
A39-B92-C10-D18
A65-B92-C10-D18
A66-B92-C10-D18
A2-B4-C11-D18
A3-B4-C11-D18
A9-B4-C11-D18
A13-B4-C11-D18
A24-B4-C11-D18
A69-B4-C11-D18
A67-B4-C11-D18
A39-B4-C11-D18
A65-B4-C11-D18
A66-B4-C11-D18
A2-B5-C11-D18
A3-B5-C11-D18
A9-B5-C11-D18
A13-B5-C11-D18
A24-B5-C11-D18
A69-B5-C11-D18
A67-B5-C11-D18
A39-B5-C11-D18
A65-B5-C11-D18
A66-B5-C11-D18
A2-B6-C11-D18
A3-B6-C11-D18
A9-B6-C11-D18
A13-B6-C11-D18
A24-B6-C11-D18
A69-B6-C11-D18
A67-B6-C11-D18
A39-B6-C11-D18
A65-B6-C11-D18
A66-B6-C11-D18
A2-B32-C11-D18
A3-B32-C11-D18
A9-B32-C11-D18
A13-B32-C11-D18
A24-B32-C11-D18
A69-B32-C11-D18
A67-B32-C11-D18
A39-B32-C11-D18
A65-B32-C11-D18
A66-B32-C11-D18
A2-B39-C11-D18
A3-B39-C11-D18
A9-B39-C11-D18
A13-B39-C11-D18
A24-B39-C11-D18
A69-B39-C11-D18
A67-B39-C11-D18
A39-B39-C11-D18
A65-B39-C11-D18
A66-B39-C11-D18
A2-B45-C11-D18
A3-B45-C11-D18
A9-B45-C11-D18
A13-B45-C11-D18
A24-B45-C11-D18

-continued

A69-B45-C11-D18
A67-B45-C11-D18
A39-B45-C11-D18
A65-B45-C11-D15
A66-B45-C11-D18
A2-B53-C11-D18
A3-B53-C11-D18
A9-B53-C11-D18
A13-B53-C11-D18
A24-B53-C11-D18
A69-B53-C11-D18
A67-B53-C11-D18
A39-B53-C11-D18
A65-B53-C11-D18
A66-B53-C11-D18
A2-B79-C11-D18
A3-B79-C11-D18
A9-B79-C11-D18
A13-B79-C11-D18
A24-B79-C11-D18
A69-B79-C11-D18
A67-B79-C11-D18
A39-B79-C11-D18
A65-B79-C11-D18
A66-B79-C11-D18
A2-B80-C11-D18
A3-B80-C11-D18
A9-B80-C11-D18
A13-B80-C11-D18
A24-B80-C11-D18
A69-B80-C11-D18
A67-B80-C11-D18
A39-B80-C11-D18
A65-B80-C11-D18
A66-B80-C11-D18
A2-B85-C11-D18
A3-B85-C11-D18
A9-B85-C11-D18
A13-B85-C11-D18
A24-B85-C11-D18
A69-B85-C11-D18
A67-B85-C11-D18
A39-B85-C11-D18
A65-B85-C11-D18
A66-B85-C11-D18
A2-B86-C11-D18
A3-B86-C11-D18
A9-B86-C11-D18
A13-B86-C11-D18
A24-B86-C11-D18
A69-B86-C11-D18
A67-B86-C11-D18
A39-B86-C11-D18
A65-B86-C11-D18
A66-B86-C11-D18
A2-B87-C11-D18
A3-B87-C11-D18
A9-B87-C11-D18
A13-B87-C11-D18
A24-B87-C11-D18
A69-B87-C11-D18
A67-B87-C11-D18
A39-B87-C11-D18
A65-B87-C11-D18
A66-B87-C11-D18
A2-B89-C11-D18
A3-B89-C11-D18
A9-B89-C11-D18
A13-B89-C11-D18
A24-B89-C11-D18
A69-B89-C11-D18
A67-B89-C11-D18
A39-B89-C11-D18
A65-B89-C11-D18
A66-B89-C11-D18
A2-B92-C11-D18
A3-B92-C11-D18
A9-B92-C11-D18
A13-B92-C11-D18
A24-B92-C11-D18

-continued

A69-B92-C11-D18
A67-B92-C11-D18
A39-B92-C11-D18
A65-B92-C11-D18
A66-B92-C11-D18
A2-B4-C12-D18
A3-B4-C12-D18
A9-B4-C12-D18
A13-B4-C12-D18
A24-B4-C12-D18
A69-B4-C12-D18
A67-B4-C12-D18
A39-B4-C12-D18
A65-B4-C12-D18
A66-B4-C12-D18
A2-B5-C12-D18
A3-B5-C12-D18
A9-B5-C12-D18
A13-B5-C12-D18
A24-B5-C12-D18
A69-B5-C12-D18
A67-B5-C12-D18
A39-B5-C12-D18
A65-B5-C12-D18
A66-B5-C12-D18
A2-B6-C12-D18
A3-B6-C12-D18
A9-B6-C12-D18
A13-B6-C12-D18
A24-B6-C12-D18
A69-B6-C12-D18
A67-B6-C12-D18
A39-B6-C12-D18
A65-B6-C12-D18
A66-B6-C12-D18
A2-B32-C12-D18
A3-B32-C12-D18
A9-B32-C12-D18
A13-B32-C12-D18
A24-B32-C12-D18
A69-B32-C12-D18
A67-B32-C12-D18
A39-B32-C12-D18
A65-B32-C12-D18
A66-B32-C12-D18
A2-B39-C12-D18
A3-B39-C12-D18
A9-B39-C12-D18
A13-B39-C12-D18
A24-B39-C12-D18
A69-B39-C12-D18
A67-B39-C12-D18
A39-B39-C12-D18
A65-B39-C12-D18
A66-B39-C12-D18
A2-B45-C12-D18
A3-B45-C12-D18
A9-B45-C12-D18
A13-B45-C12-D18
A24-B45-C12-D18
A69-B45-C12-D18
A67-B45-C12-D18
A39-B45-C12-D18
A65-B45-C12-D18
A66-B45-C12-D18
A2-B53-C12-D18
A3-B53-C12-D18
A9-B53-C12-D18
A13-B53-C12-D18
A24-B53-C12-D18
A69-B53-C12-D18
A67-B53-C12-D18
A39-B53-C12-D18
A65-B53-C12-D18
A66-B53-C12-D18
A2-B79-C12-D18
A3-B79-C12-D18
A9-B79-C12-D18
A13-B79-C12-D18
A24-B79-C12-D18

-continued

A69-B79-C12-D18
A67-B79-C12-D18
A39-B79-C12-D18
A65-B79-C12-D18
A66-B79-C12-D18
A2-B80-C12-D18
A3-B80-C12-D18
A9-B80-C12-D18
A13-B80-C12-D18
A24-B80-C12-D18
A69-B80-C12-D18
A67-B80-C12-D18
A39-B80-C12-D18
A65-B80-C12-D18
A66-B80-C12-D18
A2-B85-C12-D18
A3-B85-C12-D18
A9-B85-C12-D18
A13-B85-C12-D18
A24-B85-C12-D18
A69-B85-C12-D18
A67-B85-C12-D18
A39-B85-C12-D18
A65-B85-C12-D18
A66-B85-C12-D18
A2-B86-C12-D18
A3-B86-C12-D18
A9-B86-C12-D18
A13-B86-C12-D18
A24-B86-C12-D18
A69-B86-C12-D18
A67-B86-C12-D18
A39-B86-C12-D18
A65-B86-C12-D18
A66-B86-C12-D18
A2-B87-C12-D18
A3-B87-C12-D18
A9-B87-C12-D18
A13-B87-C12-D18
A24-B87-C12-D18
A69-B87-C12-D18
A67-B87-C12-D18
A39-B87-C12-D18
A65-B87-C12-D18
A66-B87-C12-D18
A2-B89-C12-D18
A3-B89-C12-D18
A9-B89-C12-D18
A13-B89-C12-D18
A24-B89-C12-D18
A69-B89-C12-D18
A67-B89-C12-D18
A39-B89-C12-D18
A65-B89-C12-D18
A66-B89-C12-D18
A2-B92-C12-D18
A3-B92-C12-D18
A9-B92-C12-D18
A13-B92-C12-D18
A24-B92-C12-D18
A69-B92-C12-D18
A67-B92-C12-D18
A39-B92-C12-D18
A65-B92-C12-D18
A66-B92-C12-D18
A2-B4-C13-D18
A3-B4-C13-D18
A9-B4-C13-D18
A13-B4-C13-D18
A24-B4-C13-D18
A69-B4-C13-D18
A67-B4-C13-D18
A39-B4-C13-D18
A65-B4-C13-D18
A66-B4-C13-D18
A2-B5-C13-D18
A3-B5-C13-D18
A9-B5-C13-D18
A13-B5-C13-D18
A24-B5-C13-D18

-continued

A69-B5-C13-D18
A67-B5-C13-D18
A39-B5-C13-D18
A65-B5-C13-D18
A66-B5-C13-D18
A2-B6-C13-D18
A3-B6-C13-D18
A9-B6-C13-D18
A13-B6-C13-D18
A24-B6-C13-D18
A69-B6-C13-D18
A67-B6-C13-D18
A39-B6-C13-D18
A65-B6-C13-D18
A66-B6-C13-D18
A2-B32-C13-D18
A3-B32-C13-D18
A9-B32-C13-D18
A13-B32-C13-D18
A24-B32-C13-D18
A69-B32-C13-D18
A67-B32-C13-D18
A39-B32-C13-D18
A65-B32-C13-D18
A66-B32-C13-D18
A2-B39-C13-D18
A3-B39-C13-D18
A9-B39-C13-D18
A13-B39-C13-D18
A24-B39-C13-D18
A69-B39-C13-D18
A67-B39-C13-D18
A39-B39-C13-D18
A65-B39-C13-D18
A66-B39-C13-D18
A2-B45-C13-D18
A3-B45-C13-D18
A9-B45-C13-D18
A13-B45-C13-D18
A24-B45-C13-D18
A69-B45-C13-D18
A67-B45-C13-D18
A39-B45-C13-D18
A65-B45-C13-D18
A66-B45-C13-D18
A2-B53-C13-D18
A3-B53-C13-D18
A9-B53-C13-D18
A13-B53-C13-D18
A24-B53-C13-D18
A69-B53-C13-D18
A67-B53-C13-D18
A39-B53-C13-D18
A65-B53-C13-D18
A66-B53-C13-D18
A2-B79-C13-D18
A3-B79-C13-D18
A9-B79-C13-D18
A13-B79-C13-D18
A24-B79-C13-D18
A69-B79-C13-D18
A67-B79-C13-D18
A39-B79-C13-D18
A65-B79-C13-D18
A66-B79-C13-D18
A2-B80-C13-D18
A3-B80-C13-D18
A9-B80-C13-D18
A13-B80-C13-D18
A24-B80-C13-D18
A69-B80-C13-D18
A67-B80-C13-D18
A39-B80-C13-D18
A65-B80-C13-D18
A66-B80-C13-D18
A2-B85-C13-D18
A3-B85-C13-D18
A9-B85-C13-D18
A13-B85-C13-D18
A24-B85-C13-D18

-continued

A69-B85-C13-D18
A67-B85-C13-D18
A39-B85-C13-D18
A65-B85-C13-D18
A66-B85-C13-D18
A2-B86-C13-D18
A3-B86-C13-D18
A9-B86-C13-D18
A13-B86-C13-D18
A24-B86-C13-D18
A69-B86-C13-D18
A67-B86-C13-D18
A39-B86-C13-D18
A65-B86-C13-D18
A66-B86-C13-D18
A2-B87-C13-D18
A3-B87-C13-D18
A9-B87-C13-D18
A13-B87-C13-D18
A24-B87-C13-D18
A69-B87-C13-D18
A67-B87-C13-D18
A39-B87-C13-D18
A65-B87-C13-D18
A66-B87-C13-D18
A2-B89-C13-D18
A3-B89-C13-D18
A9-B89-C13-D18
A13-B89-C13-D18
A24-B89-C13-D18
A69-B89-C13-D18
A67-B89-C13-D18
A39-B89-C13-D18
A65-B89-C13-D18
A66-B89-C13-D18
A2-B92-C13-D18
A3-B92-C13-D18
A9-B92-C13-D18
A13-B92-C13-D18
A24-B92-C13-D18
A69-B92-C13-D18
A67-B92-C13-D15
A39-B92-C13-D18
A65-B92-C13-D18
A66-B92-C13-D18
A2-B4-C1-D19
A3-B4-C1-D19
A9-B4-C1-D19
A13-B4-C1-D19
A24-B4-C1-D19
A69-B4-C1-D19
A67-B4-C1-D19
A39-B4-C1-D19
A65-B4-C1-D19
A66-B4-C1-D19
A2-B5-C1-D19
A3-B5-C1-D19
A9-B5-C1-D19
A13-B5-C1-D19
A24-B5-C1-D19
A69-B5-C1-D19
A67-B5-C1-D19
A39-B5-C1-D19
A65-B5-C1-D19
A66-B5-C1-D19
A2-B6-C1-D19
A3-B6-C1-D19
A9-B6-C1-D19
A13-B6-C1-D19
A24-B6-C1-D19
A69-B6-C1-D19
A67-B6-C1-D19
A39-B6-C1-D19
A65-B6-C1-D19
A66-B6-C1-D19
A2-B32-C1-D19
A3-B32-C1-D19
A9-B32-C1-D19
A13-B32-C1-D19
A24-B32-C1-D19

-continued

A69-B32-C1-D19
A67-B32-C1-D19
A39-B32-C1-D19
A65-B32-C1-D19
A66-B32-C1-D19
A2-B39-C1-D19
A3-B39-C1-D19
A9-B39-C1-D19
A13-B39-C1-D19
A24-B39-C1-D19
A69-B39-C1-D19
A67-B39-C1-D19
A39-B39-C1-D19
A65-B39-C1-D19
A66-B39-C1-D19
A2-B45-C1-D19
A3-B45-C1-D19
A9-B45-C1-D19
A13-B45-C1-D19
A24-B45-C1-D19
A69-B45-C1-D19
A67-B45-C1-D19
A39-B45-C1-D19
A65-B45-C1-D19
A66-B45-C1-D19
A2-B53-C1-D19
A3-B53-C1-D19
A9-B53-C1-D19
A13-B53-C1-D19
A24-B53-C1-D19
A69-B53-C1-D19
A67-B53-C1-D19
A39-B53-C1-D19
A65-B53-C1-D19
A66-B53-C1-D19
A2-B79-C1-D19
A3-B79-C1-D19
A9-B79-C1-D19
A13-B79-C1-D19
A24-B79-C1-D19
A69-B79-C1-D19
A67-B79-C1-D19
A39-B79-C1-D19
A65-B79-C1-D19
A66-B79-C1-D19
A2-B80-C1-D19
A3-B80-C1-D19
A9-B80-C1-D19
A13-B80-C1-D19
A24-B80-C1-D19
A69-B80-C1-D19
A67-B80-C1-D19
A39-B80-C1-D19
A65-B80-C1-D19
A66-B80-C1-D19
A2-B85-C1-D19
A3-B85-C1-D19
A9-B85-C1-D19
A13-B85-C1-D19
A24-B85-C1-D19
A69-B85-C1-D19
A67-B85-C1-D19
A39-B85-C1-D19
A65-B85-C1-D19
A66-B85-C1-D19
A2-B86-C1-D19
A3-B86-C1-D19
A9-B86-C1-D19
A13-B86-C1-D19
A24-B86-C1-D19
A69-B86-C1-D19
A67-B86-C1-D19
A39-B86-C1-D19
A65-B86-C1-D19
A66-B86-C1-D19
A2-B87-C1-D19
A3-B87-C1-D19
A9-B87-C1-D19
A13-B87-C1-D19
A24-B87-C1-D19

-continued
A69-B87-C1-D19
A67-B87-C1-D19
A39-B87-C1-D19
A65-B87-C1-D19
A66-B87-C1-D19
A2-B89-C1-D19
A3-B89-C1-D19
A9-B89-C1-D19
A13-B89-C1-D19
A24-B89-C1-D19
A69-B89-C1-D19
A67-B89-C1-D19
A39-B89-C1-D19
A65-B89-C1-D19
A66-B89-C1-D19
A2-B92-C1-D19
A3-B92-C1-D19
A9-B92-C1-D19
A13-B92-C1-D19
A24-B92-C1-D19
A69-B92-C1-D19
A67-B92-C1-D19
A39-B92-C1-D19
A65-B92-C1-D19
A66-B92-C1-D19
A2-B4-C2-D19
A3-B4-C2-D19
A9-B4-C2-D19
A13-B4-C2-D19
A24-B4-C2-D19
A69-B4-C2-D19
A67-B4-C2-D19
A39-B4-C2-D19
A65-B4-C2-D19
A66-B4-C2-D19
A2-B5-C2-D19
A3-B5-C2-D19
A9-B5-C2-D19
A13-B5-C2-D19
A24-B5-C2-D19
A69-B5-C2-D19
A67-B5-C2-D19
A39-B5-C2-D19
A65-B5-C2-D19
A66-B5-C2-D19
A2-B6-C2-D19
A3-B6-C2-D19
A9-B6-C2-D19
A13-B6-C2-D19
A24-B6-C2-D19
A69-B6-C2-D19
A67-B6-C2-D19
A39-B6-C2-D19
A65-B6-C2-D19
A66-B6-C2-D19
A2-B32-C2-D19
A3-B32-C2-D19
A9-B32-C2-D19
A13-B32-C2-D19
A24-B32-C2-D19
A69-B32-C2-D19
A67-B32-C2-D19
A39-B32-C2-D19
A65-B32-C2-D19
A66-B32-C2-D19
A2-B39-C2-D19
A3-B39-C2-D19
A9-B39-C2-D19
A13-B39-C2-D19
A24-B39-C2-D19
A69-B39-C2-D19
A67-B39-C2-D19
A39-B39-C2-D19
A65-B39-C2-D19
A66-B39-C2-D19
A2-B45-C2-D19
A3-B45-C2-D19
A9-B45-C2-D19
A13-B45-C2-D19
A24-B45-C2-D19

-continued
A69-B45-C2-D19
A67-B45-C2-D19
A39-B45-C2-D19
A65-B45-C2-D19
A66-B45-C2-D19
A2-B53-C2-D19
A3-B53-C2-D19
A9-B53-C2-D19
A13-B53-C2-D19
A24-B53-C2-D19
A69-B53-C2-D19
A67-B53-C2-D19
A39-B53-C2-D19
A65-B53-C2-D19
A66-B53-C2-D19
A2-B79-C2-D19
A3-B79-C2-D19
A9-B79-C2-D19
A13-B79-C2-D19
A24-B79-C2-D19
A69-B79-C2-D19
A67-B79-C2-D19
A39-B79-C2-D19
A65-B79-C2-D19
A66-B79-C2-D19
A2-B80-C2-D19
A3-B80-C2-D19
A9-B80-C2-D19
A13-B80-C2-D19
A24-B80-C2-D19
A69-B80-C2-D19
A67-B80-C2-D19
A39-B80-C2-D19
A65-B80-C2-D19
A66-B80-C2-D19
A2-B85-C2-D19
A3-B85-C2-D19
A9-B85-C2-D19
A13-B85-C2-D19
A24-B85-C2-D19
A69-B85-C2-D19
A67-B85-C2-D19
A39-B85-C2-D19
A65-B85-C2-D19
A66-B85-C2-D19
A2-B86-C2-D19
A3-B86-C2-D19
A9-B86-C2-D19
A13-B86-C2-D19
A24-B86-C2-D19
A69-B86-C2-D19
A67-B86-C2-D19
A39-B86-C2-D19
A65-B86-C2-D19
A66-B86-C2-D19
A2-B87-C2-D19
A3-B87-C2-D19
A9-B87-C2-D19
A13-B87-C2-D19
A24-B87-C2-D19
A69-B87-C2-D19
A67-B87-C2-D19
A39-B87-C2-D19
A65-B87-C2-D19
A66-B87-C2-D19
A2-B89-C2-D19
A3-B89-C2-D19
A9-B89-C2-D19
A13-B89-C2-D19
A24-B89-C2-D19
A69-B89-C2-D19
A67-B89-C2-D19
A39-B89-C2-D19
A65-B89-C2-D19
A66-B89-C2-D19
A2-B92-C2-D19
A3-B92-C2-D19
A9-B92-C2-D19
A13-B92-C2-D19
A24-B92-C2-D19

-continued
A69-B92-C2-D19
A67-B92-C2-D19
A39-B92-C2-D19
A65-B92-C2-D19
A66-B92-C2-D19
A2-B4-C3-D19
A3-B4-C3-D19
A9-B4-C3-D19
A13-B4-C3-D19
A24-B4-C3-D19
A69-B4-C3-D19
A67-B4-C3-D19
A39-B4-C3-D19
A65-B4-C3-D19
A66-B4-C3-D19
A2-B5-C3-D19
A3-B5-C3-D19
A9-B5-C3-D19
A13-B5-C3-D19
A24-B5-C3-D19
A69-B5-C3-D19
A67-B5-C3-D19
A39-B5-C3-D19
A65-B5-C3-D19
A66-B5-C3-D19
A2-B6-C3-D19
A3-B6-C3-D19
A9-B6-C3-D19
A13-B6-C3-D19
A24-B6-C3-D19
A69-B6-C3-D19
A67-B6-C3-D19
A39-B6-C3-D19
A65-B6-C3-D19
A66-B6-C3-D19
A2-B32-C3-D19
A3-B32-C3-D19
A9-B32-C3-D19
A13-B32-C3-D19
A24-B32-C3-D19
A69-B32-C3-D19
A67-B32-C3-D19
A39-B32-C3-D19
A65-B32-C3-D19
A66-B32-C3-D19
A2-B39-C3-D19
A3-B39-C3-D19
A9-B39-C3-D19
A13-B39-C3-D19
A24-B39-C3-D19
A69-B39-C3-D19
A67-B39-C3-D19
A39-B39-C3-D19
A65-B39-C3-D19
A66-B39-C3-D19
A2-B45-C3-D19
A3-B45-C3-D19
A9-B45-C3-D19
A13-B45-C3-D19
A24-B45-C3-D19
A69-B45-C3-D19
A67-B45-C3-D19
A39-B45-C3-D19
A65-B45-C3-D19
A66-B45-C3-D19
A2-B53-C3-D19
A3-B53-C3-D19
A9-B53-C3-D19
A13-B53-C3-D19
A24-B53-C3-D19
A69-B53-C3-D19
A67-B53-C3-D19
A39-B53-C3-D19
A65-B53-C3-D19
A66-B53-C3-D19
A2-B79-C3-D19
A3-B79-C3-D19
A9-B79-C3-D19
A13-B79-C3-D19
A24-B79-C3-D19

-continued
A69-B79-C3-D19
A67-B79-C3-D19
A39-B79-C3-D19
A65-B79-C3-D19
A66-B79-C3-D19
A2-B80-C3-D19
A3-B80-C3-D19
A9-B80-C3-D19
A13-B80-C3-D19
A24-B80-C3-D19
A69-B80-C3-D19
A67-B80-C3-D19
A39-B80-C3-D19
A65-B80-C3-D19
A66-B80-C3-D19
A2-B85-C3-D19
A3-B85-C3-D19
A9-B85-C3-D19
A13-B85-C3-D19
A24-B85-C3-D19
A69-B85-C3-D19
A67-B85-C3-D19
A39-B85-C3-D19
A65-B85-C3-D19
A66-B85-C3-D19
A2-B86-C3-D19
A3-B86-C3-D19
A9-B86-C3-D19
A13-B86-C3-D19
A24-B86-C3-D19
A69-B86-C3-D19
A67-B86-C3-D19
A39-B86-C3-D19
A65-B86-C3-D19
A66-B86-C3-D19
A2-B87-C3-D19
A3-B87-C3-D19
A9-B87-C3-D19
A13-B87-C3-D19
A24-B87-C3-D19
A69-B87-C3-D19
A67-B87-C3-D19
A39-B87-C3-D19
A65-B87-C3-D19
A66-B87-C3-D19
A2-B89-C3-D19
A3-B89-C3-D19
A9-B89-C3-D19
A13-B89-C3-D19
A24-B89-C3-D19
A69-B89-C3-D19
A67-B89-C3-D19
A39-B89-C3-D19
A65-B89-C3-D19
A66-B89-C3-D19
A2-B92-C3-D19
A3-B92-C3-D19
A9-B92-C3-D19
A13-B92-C3-D19
A24-B92-C3-D19
A69-B92-C3-D19
A67-B92-C3-D19
A39-B92-C3-D19
A65-B92-C3-D19
A66-B92-C3-D19
A2-B4-C4-D19
A3-B4-C4-D19
A9-B4-C4-D19
A13-B4-C4-D19
A24-B4-C4-D19
A69-B4-C4-D19
A67-B4-C4-D19
A39-B4-C4-D19
A65-B4-C4-D19
A66-B4-C4-D19
A2-B5-C4-D19
A3-B5-C4-D191
A9-B5-C4-D19
A13-B5-C4-D19
A24-B5-C4-D19

-continued
A69-B5-C4-D19
A67-B5-C4-D19
A39-B5-C4-D19
A65-B5-C4-D19
A66-B5-C4-D19
A2-B6-C4-D19
A3-B6-C4-D19
A9-B6-C4-D19
A13-B6-C4-D19
A24-B6-C4-D19
A69-B6-C4-D19
A67-B6-C4-D19
A39-B6-C4-D19
A65-B6-C4-D19
A66-B6-C4-D19
A2-B32-C4-D19
A3-B32-C4-D19
A9-B32-C4-D19
A13-B32-C4-D19
A24-B32-C4-D19
A69-B32-C4-D19
A67-B32-C4-D19
A39-B32-C4-D19
A65-B32-C4-D19
A66-B32-C4-D19
A2-B39-C4-D19
A3-B39-C4-D19
A9-B39-C4-D19
A13-B39-C4-D19
A24-B39-C4-D19
A69-B39-C4-D19
A67-B39-C4-D19
A39-B39-C4-D19
A65-B39-C4-D19
A66-B39-C4-D19
A2-B45-C4-D19
A3-B45-C4-D19
A9-B45-C4-D19
A13-B45-C4-D19
A24-B45-C4-D19
A69-B45-C4-D19
A67-B45-C4-D19
A39-B45-C4-D19
A65-B45-C4-D19
A66-B45-C4-D19
A2-B53-C4-D19
A3-B53-C4-D19
A9-B53-C4-D19
A13-B53-C4-D19
A24-B53-C4-D19
A69-B53-C4-D19
A67-B53-C4-D19
A39-B53-C4-D19
A65-B53-C4-D19
A66-B53-C4-D19
A2-B79-C4-D19
A3-B79-C4-D19
A9-B79-C4-D19
A13-B79-C4-D19
A24-B79-C4-D19
A69-B79-C4-D19
A67-B79-C4-D19
A39-B79-C4-D19
A65-B79-C4-D19
A66-B79-C4-D19
A2-B80-C4-D19
A3-B80-C4-D19
A9-B80-C4-D19
A13-B80-C4-D19
A24-B80-C4-D19
A69-B80-C4-D19
A67-B80-C4-D19
A39-B80-C4-D19
A65-B80-C4-D19
A66-B80-C4-D19
A2-B85-C4-D19
A3-B85-C4-D19
A9-B85-C4-D19
A13-B85-C4-D19
A24-B85-C4-D19

-continued
A69-B85-C4-D19
A67-B85-C4-D19
A39-B85-C4-D19
A65-B85-C4-D19
A66-B85-C4-D19
A2-B86-C4-D19
A3-B86-C4-D19
A9-B86-C4-D19
A13-B86-C4-D19
A24-B86-C4-D19
A69-B86-C4-D19
A67-B86-C4-D19
A39-B86-C4-D19
A65-B86-C4-D19
A66-B86-C4-D19
A2-B87-C4-D19
A3-B87-C4-D19
A9-B87-C4-D19
A13-B87-C4-D19
A24-B87-C4-D19
A69-B87-C4-D19
A67-B87-C4-D19
A39-B87-C4-D19
A65-B87-C4-D19
A66-B87-C4-D19
A2-B89-C4-D19
A3-B89-C4-D19
A9-B89-C4-D19
A13-B89-C4-D19
A24-B89-C4-D19
A69-B89-C4-D19
A67-B89-C4-D19
A39-B89-C4-D19
A65-B89-C4-D19
A66-B89-C4-D19
A2-B92-C4-D19
A3-B92-C4-D19
A9-B92-C4-D19
A13-B92-C4-D19
A24-B92-C4-D19
A69-B92-C4-D19
A67-B92-C4-D19
A39-B92-C4-D19
A65-B92-C4-D19
A66-B92-C4-D19
A2-B4-C5-D19
A3-B4-C5-D19
A9-B4-C5-D19
A13-B4-C5-D19
A24-B4-C5-D19
A69-B4-C5-D19
A67-B4-C5-D19
A39-B4-C5-D19
A65-B4-C5-D19
A66-B4-C5-D19
A2-B5-C5-D19
A3-B5-C5-D19
A9-B5-C5-D19
A13-B5-C5-D19
A24-B5-C5-D19
A69-B5-C5-D19
A67-B5-C5-D19
A39-B5-C5-D19
A65-B5-C5-D19
A66-B5-C5-D19
A2-B6-C5-D19
A3-B6-C5-D19
A9-B6-C5-D19
A13-B6-C5-D19
A24-B6-C5-D19
A69-B6-C5-D19
A67-B6-C5-D19
A39-B6-C5-D19
A65-B6-C5-D19
A66-B6-C5-D19
A2-B32-C5-D19
A3-B32-C5-D19
A9-B32-C5-D19
A13-B32-C5-D19
A24-B32-C5-D19

-continued
A69-B32-C5-D19
A67-B32-C5-D19
A39-B32-C5-D19
A65-B32-C5-D19
A66-B32-C5-D19
A2-B39-C5-D19
A3-B39-C5-D19
A9-B39-C5-D19
A13-B39-C5-D19
A24-B39-C5-D19
A69-B39-C5-D19
A67-B39-C5-D19
A39-B39-C5-D19
A65-B39-C5-D19
A66-B39-C5-D19
A2-B45-C5-D19
A3-B45-C5-D19
A9-B45-C5-D19
A13-B45-C5-D19
A24-B45-C5-D19
A69-B45-C5-D19
A67-B45-C5-D19
A39-B45-C5-D19
A65-B45-C5-D19
A66-B45-C5-D19
A2-B53-C5-D19
A3-B53-C5-D19
A9-B53-C5-D19
A13-B53-C5-D19
A24-B53-C5-D19
A69-B53-C5-D19
A67-B53-C5-D19
A39-B53-C5-D19
A65-B53-C5-D19
A66-B53-C5-D19
A2-B79-C5-D19
A3-B79-C5-D19
A9-B79-C5-D19
A13-B79-C5-D19
A24-B79-C5-D19
A69-B79-C5-D19
A67-B79-C5-D19
A39-B79-C5-D19
A65-B79-C5-D19
A66-B79-C5-D19
A2-B80-C5-D19
A3-B80-C5-D19
A9-B80-C5-D19
A13-B80-C5-D19
A24-B80-C5-D19
A69-B80-C5-D19
A67-B80-C5-D19
A39-B80-C5-D19
A65-B80-C5-D19
A66-B80-C5-D19
A2-B85-C5-D19
A3-B85-C5-D19
A9-B85-C5-D19
A13-B85-C5-D19
A24-B85-C5-D19
A69-B85-C5-D19
A67-B85-C5-D19
A39-B85-C5-D19
A65-B85-C5-D19
A66-B85-C5-D19
A2-B86-C5-D19
A3-B86-C5-D19
A9-B86-C5-D19
A13-B86-C5-D19
A24-B86-C5-D19
A69-B86-C5-D19
A67-B86-C5-D19
A39-B86-C5-D19
A65-B86-C5-D19
A66-B86-C5-D19
A2-B87-C5-D19
A3-B87-C5-D19
A9-B87-C5-D19
A13-B87-C5-D19
A24-B87-C5-D19

-continued
A69-B87-C5-D19
A67-B87-C5-D19
A39-B87-C5-D19
A65-B87-C5-D19
A66-B87-C5-D19
A2-B89-C5-D19
A3-B89-C5-D19
A9-B89-C5-D19
A13-B89-C5-D19
A24-B89-C5-D19
A69-B89-C5-D19
A67-B89-C5-D19
A39-B89-C5-D19
A65-B89-C5-D19
A66-B89-C5-D19
A2-B92-C5-D19
A3-B92-C5-D19
A9-B92-C5-D19
A13-B92-C5-D19
A24-B92-C5-D19
A69-B92-C5-D19
A67-B92-C5-D19
A39-B92-C5-D19
A65-B92-C5-D19
A66-B92-C5-D19
A2-B4-C6-D19
A3-B4-C6-D19
A9-B4-C6-D19
A13-B4-C6-D19
A24-B4-C6-D19
A69-B4-C6-D19
A67-B4-C6-D19
A39-B4-C6-D19
A65-B4-C6-D19
A66-B4-C6-D19
A2-B5-C6-D19
A3-B5-C6-D19
A9-B5-C6-D19
A13-B5-C6-D19
A24-B5-C6-D19
A69-B5-C6-D19
A67-B5-C6-D19
A39-B5-C6-D19
A65-B5-C6-D19
A66-B5-C6-D19
A2-B6-C6-D19
A3-B6-C6-D19
A9-B6-C6-D19
A13-B6-C6-D19
A24-B6-C6-D19
A69-B6-C6-D19
A67-B6-C6-D19
A39-B6-C6-D19
A65-B6-C6-D19
A66-B6-C6-D19
A2-B32-C6-D19
A3-B32-C6-D19
A9-B32-C6-D19
A13-B32-C6-D19
A24-B32-C6-D19
A69-B32-C6-D19
A67-B32-C6-D19
A39-B32-C6-D19
A65-B32-C6-D19
A66-B32-C6-D19
A2-B39-C6-D19
A3-B39-C6-D19
A9-B39-C6-D19
A13-B39-C6-D19
A24-B39-C6-D19
A69-B39-C6-D19
A67-B39-C6-D19
A39-B39-C6-D19
A65-B39-C6-D19
A66-B39-C6-D19
A2-B45-C6-D19
A3-B45-C6-D19
A9-B45-C6-D19
A13-B45-C6-D19
A24-B45-C6-D19

-continued
A69-B45-C6-D19
A67-B45-C6-D19
A39-B45-C6-D19
A65-B45-C6-D19
A66-B45-C6-D19
A2-B53-C6-D19
A3-B53-C6-D19
A9-B53-C6-D19
A13-B53-C6-D19
A24-B53-C6-D19
A69-B53-C6-D19
A67-B53-C6-D19
A39-B53-C6-D19
A65-B53-C6-D19
A66-B53-C6-D19
A2-B79-C6-D19
A3-B79-C6-D19
A9-B79-C6-D19
A13-B79-C6-D19
A24-B79-C6-D19
A69-B79-C6-D19
A67-B79-C6-D19
A39-B79-C6-D19
A65-B79-C6-D19
A66-B79-C6-D19
A2-B80-C6-D19
A3-B80-C6-D19
A9-B80-C6-D19
A13-B80-C6-D19
A24-B80-C6-D19
A69-B80-C6-D19
A67-B80-C6-D19
A39-B80-C6-D19
A65-B80-C6-D19
A66-B80-C6-D19
A2-B85-C6-D19
A3-B85-C6-D19
A9-B85-C6-D19
A13-B85-C6-D19
A24-B85-C6-D19
A69-B85-C6-D19
A67-B85-C6-D19
A39-B85-C6-D19
A65-B85-C6-D19
A66-B85-C6-D19
A2-B86-C6-D19
A3-B86-C6-D19
A9-B86-C6-D19
A13-B86-C6-D19
A24-B86-C6-D19
A69-B86-C6-D19
A67-B86-C6-D19
A39-B86-C6-D19
A65-B86-C6-D19
A66-B86-C6-D19
A2-B87-C6-D19
A3-B87-C6-D19
A9-B87-C6-D19
A13-B87-C6-D19
A24-B87-C6-D19
A69-B87-C6-D19
A67-B87-C6-D19
A39-B87-C6-D19
A65-B87-C6-D19
A66-B87-C6-D19
A2-B89-C6-D19
A3-B89-C6-D19
A9-B89-C6-D19
A13-B89-C6-D19
A24-B89-C6-D19
A69-B89-C6-D19
A67-B89-C6-D19
A39-B89-C6-D19
A65-B89-C6-D19
A66-B89-C6-D19
A2-B92-C6-D19
A3-B92-C6-D19
A9-B92-C6-D19
A13-B92-C6-D19
A24-B92-C6-D19

-continued
A69-B92-C6-D19
A67-B92-C6-D19
A39-B92-C6-D19
A65-B92-C6-D19
A66-B92-C6-D19
A2-B4-C7-D19
A3-B4-C7-D19
A9-B4-C7-D19
A13-B4-C7-D19
A24-B4-C7-D19
A69-B4-C7-D19
A67-B4-C7-D19
A39-B4-C7-D19
A65-B4-C7-D19
A66-B4-C7-D19
A2-B5-C7-D19
A3-B5-C7-D19
A9-B5-C7-D19
A13-B5-C7-D19
A24-B5-C7-D19
A69-B5-C7-D19
A67-B5-C7-D19
A39-B5-C7-D19
A65-B5-C7-D19
A66-B5-C7-D19
A2-B6-C7-D19
A3-B6-C7-D19
A9-B6-C7-D19
A13-B6-C7-D19
A24-B6-C7-D19
A69-B6-C7-D19
A67-B6-C7-D19
A39-B6-C7-D19
A65-B6-C7-D19
A66-B6-C7-D19
A2-B32-C7-D19
A3-B32-C7-D19
A9-B32-C7-D19
A13-B32-C7-D19
A24-B32-C7-D19
A69-B32-C7-D19
A67-B32-C7-D19
A39-B32-C7-D19
A65-B32-C7-D19
A66-B32-C7-D19
A2-B39-C7-D19
A3-B39-C7-D19
A9-B39-C7-D19
A13-B39-C7-D19
A24-B39-C7-D19
A69-B39-C7-D19
A67-B39-C7-D19
A39-B39-C7-D19
A65-B39-C7-D19
A66-B39-C7-D19
A2-B45-C7-D19
A3-B45-C7-D19
A9-B45-C7-D19
A13-B45-C7-D19
A24-B45-C7-D19
A69-B45-C7-D19
A67-B45-C7-D19
A39-B45-C7-D19
A65-B45-C7-D19
A66-B45-C7-D19
A2-B53-C7-D19
A3-B53-C7-D19
A9-B53-C7-D19
A13-B53-C7-D19
A24-B53-C7-D19
A69-B53-C7-D19
A67-B53-C7-D19
A39-B53-C7-D19
A65-B53-C7-D19
A66-B53-C7-D19
A2-B79-C7-D19
A3-B79-C7-D19
A9-B79-C7-D19
A13-B79-C7-D19
A24-B79-C7-D19

-continued
A69-B79-C7-D19
A67-B79-C7-D19
A39-B79-C7-D19
A65-B79-C7-D19
A66-B79-C7-D19
A2-B80-C7-D19
A3-B80-C7-D19
A9-B80-C7-D19
A13-B80-C7-D19
A24-B80-C7-D19
A69-B80-C7-D19
A67-B80-C7-D19
A39-B80-C7-D19
A65-B80-C7-D19
A66-B80-C7-D19
A2-B85-C7-D19
A3-B85-C7-D19
A9-B85-C7-D19
A13-B85-C7-D19
A24-B85-C7-D19
A69-B85-C7-D19
A67-B85-C7-D19
A39-B85-C7-D19
A65-B85-C7-D19
A66-B85-C7-D19
A2-B86-C7-D19
A3-B86-C7-D19
A9-B86-C7-D19
A13-B86-C7-D19
A24-B86-C7-D19
A69-B86-C7-D19
A67-B86-C7-D19
A39-B86-C7-D19
A65-B86-C7-D19
A66-B86-C7-D19
A2-B87-C7-D19
A3-B87-C7-D19
A9-B87-C7-D19
A13-B87-C7-D19
A24-B87-C7-D19
A69-B87-C7-D19
A67-B87-C7-D19
A39-B87-C7-D19
A65-B87-C7-D19
A66-B87-C7-D19
A2-B89-C7-D19
A3-B89-C7-D19
A9-B89-C7-D19
A13-B89-C7-D19
A24-B89-C7-D19
A69-B89-C7-D19
A67-B89-C7-D19
A39-B89-C7-D19
A65-B89-C7-D19
A66-B89-C7-D19
A2-B92-C7-D19
A3-B92-C7-D19
A9-B92-C7-D19
A13-B92-C7-D19
A24-B92-C7-D19
A69-B92-C7-D19
A67-B92-C7-D19
A39-B92-C7-D19
A65-B92-C7-D19
A66-B92-C7-D19
A2-B4-C8-D19
A3-B4-C8-D19
A9-B4-C8-D19
A13-B4-C8-D19
A24-B4-C8-D19
A69-B4-C8-D19
A67-B4-C8-D19
A39-B4-C8-D19
A65-B4-C8-D19
A66-B4-C8-D19
A2-B5-C8-D19
A3-B5-C8-D19
A9-B5-C8-D19
A13-B5-C8-D19
A24-B5-C8-D19

-continued
A69-B5-C8-D19
A67-B5-C8-D19
A39-B5-C8-D19
A65-B5-C8-D19
A66-B5-C8-D19
A2-B6-C8-D19
A3-B6-C8-D19
A9-B6-C8-D19
A13-B6-C8-D19
A24-B6-C8-D19
A69-B6-C8-D19
A67-B6-C8-D19
A39-B6-C8-D19
A65-B6-C8-D19
A66-B6-C8-D19
A2-B32-C8-D19
A3-B32-C8-D19
A9-B32-C8-D19
A13-B32-C8-D19
A24-B32-C8-D19
A69-B32-C8-D19
A67-B32-C8-D19
A39-B32-C8-D19
A65-B32-C8-D19
A66-B32-C8-D19
A2-B39-C8-D19
A3-B39-C8-D19
A9-B39-C8-D19
A13-B39-C8-D19
A24-B39-C8-D19
A69-B39-C8-D19
A67-B39-C8-D19
A39-B39-C8-D19
A65-B39-C8-D19
A66-B39-C8-D19
A2-B45-C8-D19
A3-B45-C8-D19
A9-B45-C8-D19
A13-B45-C8-D19
A24-B45-C8-D19
A69-B45-C8-D19
A67-B45-C8-D19
A39-B45-C8-D19
A65-B45-C8-D19
A66-B45-C8-D19
A2-B53-C8-D19
A3-B53-C8-D19
A9-B53-C8-D19
A13-B53-C8-D19
A24-B53-C8-D19
A69-B53-C8-D19
A67-B53-C8-D19
A39-B53-C8-D19
A65-B53-C8-D19
A66-B53-C8-D19
A2-B79-C8-D19
A3-B79-C8-D19
A9-B79-C8-D19
A13-B79-C8-D19
A24-B79-C8-D19
A69-B79-C8-D19
A67-B79-C8-D19
A39-B79-C8-D19
A65-B79-C8-D19
A66-B79-C8-D19
A2-B80-C8-D19
A3-B80-C8-D19
A9-B80-C8-D19
A13-B80-C8-D19
A24-B80-C8-D19
A69-B80-C8-D19
A67-B80-C8-D19
A39-B80-C8-D19
A65-B80-C8-D19
A66-B80-C8-D19
A2-B85-C8-D19
A3-B85-C8-D19
A9-B85-C8-D19
A13-B85-C8-D19
A24-B85-C8-D19

-continued
A69-B85-C8-D19
A67-B85-C8-D19
A39-B85-C8-D19
A65-B85-C8-D19
A66-B85-C8-D19
A2-B86-C8-D19
A3-B86-C8-D19
A9-B86-C8-D19
A13-B86-C8-D19
A24-B86-C8-D19
A69-B86-C8-D19
A67-B86-C8-D19
A39-B86-C8-D19
A65-B86-C8-D19
A66-B86-C8-D19
A2-B87-C8-D19
A3-B87-C8-D19
A9-B87-C8-D19
A13-B87-C8-D19
A24-B87-C8-D19
A69-B87-C8-D19
A67-B87-C8-D19
A39-B87-C8-D19
A65-B87-C8-D19
A66-B87-C8-D19
A2-B89-C8-D19
A3-B89-C8-D19
A9-B89-C8-D19
A13-B89-C8-D19
A24-B89-C8-D19
A69-B89-C8-D19
A67-B89-C8-D19
A39-B89-C8-D19
A65-B89-C8-D19
A66-B89-C8-D19
A2-B92-C8-D19
A3-B92-C8-D19
A9-B92-C8-D19
A13-B92-C8-D19
A24-B92-C8-D19
A69-B92-C8-D19
A67-B92-C8-D19
A39-B92-C8-D19
A65-B92-C8-D19
A66-B92-C8-D19
A2-B4-C9-D19
A3-B4-C9-D19
A9-B4-C9-D19
A13-B4-C9-D19
A24-B4-C9-D19
A69-B4-C9-D19
A67-B4-C9-D19
A39-B4-C9-D19
A65-B4-C9-D19
A66-B4-C9-D19
A2-B5-C9-D19
A3-B5-C9-D19
A9-B5-C9-D19
A13-B5-C9-D19
A24-B5-C9-D19
A69-B5-C9-D19
A67-B5-C9-D19
A39-B5-C9-D19
A65-B5-C9-D19
A66-B5-C9-D19
A2-B6-C9-D19
A3-B6-C9-D19
A9-B6-C9-D19
A13-B6-C9-D19
A24-B6-C9-D19
A69-B6-C9-D19
A67-B6-C9-D19
A39-B6-C9-D19
A65-B6-C9-D19
A66-B6-C9-D19
A2-B32-C9-D19
A3-B32-C9-D19
A9-B32-C9-D19
A13-B32-C9-D19
A24-B32-C9-D19

-continued
A69-B32-C9-D19
A67-B32-C9-D19
A39-B32-C9-D19
A65-B32-C9-D19
A66-B32-C9-D19
A2-B39-C9-D19
A3-B39-C9-D19
A9-B39-C9-D19
A13-B39-C9-D19
A24-B39-C9-D19
A69-B39-C9-D19
A67-B39-C9-D19
A39-B39-C9-D19
A65-B39-C9-D19
A66-B39-C9-D19
A2-B45-C9-D19
A3-B45-C9-D19
A9-B45-C9-D19
A13-B45-C9-D19
A24-B45-C9-D19
A69-B45-C9-D19
A67-B45-C9-D19
A39-B45-C9-D19
A65-B45-C9-D19
A66-B45-C9-D19
A2-B53-C9-D19
A3-B53-C9-D19
A9-B53-C9-D19
A13-B53-C9-D19
A24-B53-C9-D19
A69-B53-C9-D19
A67-B53-C9-D19
A39-B53-C9-D19
A65-B53-C9-D19
A66-B53-C9-D19
A2-B79-C9-D19
A3-B79-C9-D19
A9-B79-C9-D19
A13-B79-C9-D19
A24-B79-C9-D19
A69-B79-C9-D19
A67-B79-C9-D19
A39-B79-C9-D19
A65-B79-C9-D19
A66-B79-C9-D19
A2-B80-C9-D19
A3-B80-C9-D19
A9-B80-C9-D19
A13-B80-C9-D19
A24-B80-C9-D19
A69-B80-C9-D19
A67-B80-C9-D19
A39-B80-C9-D19
A65-B80-C9-D19
A66-B80-C9-D19
A2-B85-C9-D19
A3-B85-C9-D19
A9-B85-C9-D19
A13-B85-C9-D19
A24-B85-C9-D19
A69-B85-C9-D19
A67-B85-C9-D19
A39-B85-C9-D19
A65-B85-C9-D19
A66-B85-C9-D19
A2-B86-C9-D19
A3-B86-C9-D19
A9-B86-C9-D19
A13-B86-C9-D19
A24-B86-C9-D19
A69-B86-C9-D19
A67-B86-C9-D19
A39-B86-C9-D19
A65-B86-C9-D19
A66-B86-C9-D19
A2-B87-C9-D19
A3-B87-C9-D19
A9-B87-C9-D19
A13-B87-C9-D19
A24-B87-C9-D19

-continued
A69-B87-C9-D19
A67-B87-C9-D19
A39-B87-C9-D19
A65-B87-C9-D19
A66-B87-C9-D19
A2-B89-C9-D19
A3-B89-C9-D19
A9-B89-C9-D19
A13-B89-C9-D19
A24-B89-C9-D19
A69-B89-C9-D19
A67-B89-C9-D19
A39-B89-C9-D19
A65-B89-C9-D19
A66-B89-C9-D19
A2-B92-C9-D19
A3-B92-C9-D19
A9-B92-C9-D19
A13-B92-C9-D19
A24-B92-C9-D19
A69-B92-C9-D19
A67-B92-C9-D19
A39-B92-C9-D19
A65-B92-C9-D19
A66-B92-C9-D19
A2-B4-C10-D19
A3-B4-C10-D19
A9-B4-C10-D19
A13-B4-C10-D19
A24-B4-C10-D19
A69-B4-C10-D19
A67-B4-C10-D19
A39-B4-C10-D19
A65-B4-C10-D19
A66-B4-C10-D19
A2-B5-C10-D19
A3-B5-C10-D19
A9-B5-C10-D19
A13-B5-C10-D19
A24-B5-C10-D19
A69-B5-C10-D19
A67-B5-C10-D19
A39-B5-C10-D19
A65-B5-C10-D19
A66-B5-C10-D19
A2-B6-C10-D19
A3-B6-C10-D19
A9-B6-C10-D19
A13-B6-C10-D19
A24-B6-C10-D19
A69-B6-C10-D19
A67-B6-C10-D19
A39-B6-C10-D19
A65-B6-C10-D19
A66-B6-C10-D19
A2-B32-C10-D19
A3-B32-C10-D19
A9-B32-C10-D19
A13-B32-C10-D19
A24-B32-C10-D19
A69-B32-C10-D19
A67-B32-C10-D19
A39-B32-C10-D19
A65-B32-C10-D19
A66-B32-C10-D19
A2-B39-C10-D19
A3-B39-C10-D19
A9-B39-C10-D19
A13-B39-C10-D19
A24-B39-C10-D19
A69-B39-C10-D19
A67-B39-C10-D19
A39-B39-C10-D19
A65-B39-C10-D19
A66-B39-C10-D19
A2-B45-C10-D19
A3-B45-C10-D19
A9-B45-C10-D19
A13-B45-C10-D19
A24-B45-C10-D19

-continued
A69-B45-C10-D19
A67-B45-C10-D19
A39-B45-C10-D19
A65-B45-C10-D19
A66-B45-C10-D19
A2-B53-C10-D19
A3-B53-C10-D19
A9-B53-C10-D19
A13-B53-C10-D19
A24-B53-C10-D19
A69-B53-C10-D19
A67-B53-C10-D19
A39-B53-C10-D19
A65-B53-C10-D19
A66-B53-C10-D19
A2-B79-C10-D19
A3-B79-C10-D19
A9-B79-C10-D19
A13-B79-C10-D19
A24-B79-C10-D19
A69-B79-C10-D19
A67-B79-C10-D19
A39-B79-C10-D19
A65-B79-C10-D19
A66-B79-C10-D19
A2-B80-C10-D19
A3-B80-C10-D19
A9-B80-C10-D19
A13-B80-C10-D19
A24-B80-C10-D19
A69-B80-C10-D19
A67-B80-C10-D19
A39-B80-C10-D19
A65-B80-C10-D19
A66-B80-C10-D19
A2-B85-C10-D19
A3-B85-C10-D19
A9-B85-C10-D19
A13-B85-C10-D19
A24-B85-C10-D19
A69-B85-C10-D19
A67-B85-C10-D19
A39-B85-C10-D19
A65-B85-C10-D19
A66-B85-C10-D19
A2-B86-C10-D19
A3-B86-C10-D19
A9-B86-C10-D19
A13-B86-C10-D19
A24-B86-C10-D19
A69-B86-C10-D19
A67-B86-C10-D19
A39-B86-C10-D19
A65-B86-C10-D19
A66-B86-C10-D19
A2-B87-C10-D19
A3-B87-C10-D19
A9-B87-C10-D19
A13-B87-C10-D19
A24-B87-C10-D19
A69-B87-C10-D19
A67-B87-C10-D19
A39-B87-C10-D19
A65-B87-C10-D19
A66-B87-C10-D19
A2-B89-C10-D19
A3-B89-C10-D19
A9-B89-C10-D19
A13-B89-C10-D19
A24-B89-C10-D19
A69-B89-C10-D19
A67-B89-C10-D19
A39-B89-C10-D19
A65-B89-C10-D19
A66-B89-C10-D19
A2-B92-C10-D19
A3-B92-C10-D19
A9-B92-C10-D19
A13-B92-C10-D19
A24-B92-C10-D19

-continued
A69-B92-C10-D19
A67-B92-C10-D19
A39-B92-C10-D19
A65-B92-C10-D19
A66-B92-C10-D19
A2-B4-C11-D19
A3-B4-C11-D19
A9-B4-C11-D19
A13-B4-C11-D19
A24-B4-C11-D19
A69-B4-C11-D19
A67-B4-C11-D19
A39-B4-C11-D19
A65-B4-C11-D19
A66-B4-C11-D19
A2-B5-C11-D19
A3-B5-C11-D19
A9-B5-C11-D19
A13-B5-C11-D19
A24-B5-C11-D19
A69-B5-C11-D19
A67-B5-C11-D19
A39-B5-C11-D19
A65-B5-C11-D19
A66-B5-C11-D19
A2-B6-C11-D19
A3-B6-C11-D19
A9-B6-C11-D19
A13-B6-C11-D19
A24-B6-C11-D19
A69-B6-C11-D19
A67-B6-C11-D19
A39-B6-C11-D19
A65-B6-C11-D19
A66-B6-C11-D19
A2-B32-C11-D19
A3-B32-C11-D19
A9-B32-C11-D19
A13-B32-C11-D19
A24-B32-C11-D19
A69-B32-C11-D19
A67-B32-C11-D19
A39-B32-C11-D19
A65-B32-C11-D19
A66-B32-C11-D19
A2-B39-C11-D19
A3-B39-C11-D19
A9-B39-C11-D19
A13-B39-C11-D19
A24-B39-C11-D19
A69-B39-C11-D19
A67-B39-C11-D19
A39-B39-C11-D19
A65-B39-C11-D19
A66-B39-C11-D19
A2-B45-C11-D19
A3-B45-C11-D19
A9-B45-C11-D19
A13-B45-C11-D19
A24-B45-C11-D19
A69-B45-C11-D19
A67-B45-C11-D19
A39-B45-C11-D19
A65-B45-C11-D19
A66-B45-C11-D19
A2-B53-C11-D19
A3-B53-C11-D19
A9-B53-C11-D19
A13-B53-C11-D19
A24-B53-C11-D19
A69-B53-C11-D19
A67-B53-C11-D19
A39-B53-C11-D19
A65-B53-C11-D19
A66-B53-C11-D19
A2-B79-C11-D19
A3-B79-C11-D19
A9-B79-C11-D19
A13-B79-C11-D19
A24-B79-C11-D19

-continued
A69-B79-C11-D19
A67-B79-C11-D19
A39-B79-C11-D19
A65-B79-C11-D19
A66-B79-C11-D19
A2-B80-C11-D19
A3-B80-C11-D19
A9-B80-C11-D19
A13-B80-C11-D19
A24-B80-C11-D19
A69-B80-C11-D19
A67-B80-C11-D19
A39-B80-C11-D19
A65-B80-C11-D19
A66-B80-C11-D19
A2-B85-C11-D19
A3-B85-C11-D19
A9-B85-C11-D19
A13-B85-C11-D19
A24-B85-C11-D19
A69-B85-C11-D19
A67-B85-C11-D19
A39-B85-C11-D19
A65-B85-C11-D19
A66-B85-C11-D19
A2-B86-C11-D19
A3-B86-C11-D19
A9-B86-C11-D19
A13-B86-C11-D19
A24-B86-C11-D19
A69-B86-C11-D19
A67-B86-C11-D19
A39-B86-C11-D19
A65-B86-C11-D19
A66-B86-C11-D19
A2-B87-C11-D19
A3-B87-C11-D19
A9-B87-C11-D19
A13-B87-C11-D19
A24-B87-C11-D19
A69-B87-C11-D19
A67-B87-C11-D19
A39-B87-C11-D19
A65-B87-C11-D19
A66-B87-C11-D19
A2-B89-C11-D19
A3-B89-C11-D19
A9-B89-C11-D19
A13-B89-C11-D19
A24-B89-C11-D19
A69-B89-C11-D19
A67-B89-C11-D19
A39-B89-C11-D19
A65-B89-C11-D19
A66-B89-C11-D19
A2-B92-C11-D19
A3-B92-C11-D19
A9-B92-C11-D19
A13-B92-C11-D19
A24-B92-C11-D19
A69-B92-C11-D19
A67-B92-C11-D19
A39-B92-C11-D19
A65-B92-C11-D19
A66-B92-C11-D19
A2-B4-C12-D19
A3-B4-C12-D19
A9-B4-C12-D19
A13-B4-C12-D19
A24-B4-C12-D19
A69-B4-C12-D19
A67-B4-C12-D19
A39-B4-C12-D19
A65-B4-C12-D19
A66-B4-C12-D19
A2-B5-C12-D19
A3-B5-C12-D19
A9-B5-C12-D19
A13-B5-C12-D19
A24-B5-C12-D19

-continued
A69-B5-C12-D19
A67-B5-C12-D19
A39-B5-C12-D19
A65-B5-C12-D19
A66-B5-C12-D19
A2-B6-C12-D19
A3-B6-C12-D19
A9-B6-C12-D19
A13-B6-C12-D19
A24-B6-C12-D19
A69-B6-C12-D19
A67-B6-C12-D19
A39-B6-C12-D19
A65-B6-C12-D19
A66-B6-C12-D19
A2-B32-C12-D19
A3-B32-C12-D19
A9-B32-C12-D19
A13-B32-C12-D19
A24-B32-C12-D19
A69-B32-C12-D19
A67-B32-C12-D19
A39-B32-C12-D19
A65-B32-C12-D19
A66-B32-C12-D19
A2-B39-C12-D19
A3-B39-C12-D19
A9-B39-C12-D19
A13-B39-C12-D19
A24-B39-C12-D19
A69-B39-C12-D19
A67-B39-C12-D19
A39-B39-C12-D19
A65-B39-C12-D19
A66-B39-C12-D19
A2-B45-C12-D19
A3-B45-C12-D19
A9-B45-C12-D19
A13-B45-C12-D19
A24-B45-C12-D19
A69-B45-C12-D19
A67-B45-C12-D19
A39-B45-C12-D19
A65-B45-C12-D19
A66-B45-C12-D19
A2-B53-C12-D19
A3-B53-C12-D19
A9-B53-C12-D19
A13-B53-C12-D19
A24-B53-C12-D19
A69-B53-C12-D19
A67-B53-C12-D19
A39-B53-C12-D19
A65-B53-C12-D19
A66-B53-C12-D19
A2-B79-C12-D19
A3-B79-C12-D19
A9-B79-C12-D19
A13-B79-C12-D19
A24-B79-C12-D19
A69-B79-C12-D19
A67-B79-C12-D19
A39-B79-C12-D19
A65-B79-C12-D19
A66-B79-C12-D19
A2-B80-C12-D19
A3-B80-C12-D19
A9-B80-C12-D19
A13-B80-C12-D19
A24-B80-C12-D19
A69-B80-C12-D19
A67-B80-C12-D19
A39-B80-C12-D19
A65-B80-C12-D19
A66-B80-C12-D19
A2-B85-C12-D19
A3-B85-C12-D19
A9-B85-C12-D19
A13-B85-C12-D19
A24-B85-C12-D19

-continued
A69-B85-C12-D19
A67-B85-C12-D19
A39-B85-C12-D19
A65-B85-C12-D19
A66-B85-C12-D19
A2-B86-C12-D19
A3-B86-C12-D19
A9-B86-C12-D19
A13-B86-C12-D19
A24-B86-C12-D19
A69-B86-C12-D19
A67-B86-C12-D19
A39-B86-C12-D19
A65-B86-C12-D19
A66-B86-C12-D19
A2-B87-C12-D19
A3-B87-C12-D19
A9-B87-C12-D19
A13-B87-C12-D19
A24-B87-C12-D19
A69-B87-C12-D19
A67-B87-C12-D19
A39-B87-C12-D19
A65-B87-C12-D19
A66-B87-C12-D19
A2-B89-C12-D19
A3-B89-C12-D19
A9-B89-C12-D19
A13-B89-C12-D19
A24-B89-C12-D19
A69-B89-C12-D19
A67-B89-C12-D19
A39-B89-C12-D19
A65-B89-C12-D19
A66-B89-C12-D19
A2-B92-C12-D19
A3-B92-C12-D19
A9-B92-C12-D19
A13-B92-C12-D19
A24-B92-C12-D19
A69-B92-C12-D19
A67-B92-C12-D19
A39-B92-C12-D19
A65-B92-C12-D19
A66-B92-C12-D19
A2-B4-C13-D19
A3-B4-C13-D19
A9-B4-C13-D19
A13-B4-C13-D19
A24-B4-C13-D19
A69-B4-C13-D19
A67-B4-C13-D19
A39-B4-C13-D19
A65-B4-C13-D19
A66-B4-C13-D19
A2-B5-C13-D19
A3-B5-C13-D19
A9-B5-C13-D19
A13-B5-C13-D19
A24-B5-C13-D19
A69-B5-C13-D19
A67-B5-C13-D19
A39-B5-C13-D19
A65-B5-C13-D19
A66-B5-C13-D19
A2-B6-C13-D19
A3-B6-C13-D19
A9-B6-C13-D19
A13-B6-C13-D19
A24-B6-C13-D19
A69-B6-C13-D19
A67-B6-C13-D19
A39-B6-C13-D19
A65-B6-C13-D19
A66-B6-C13-D19
A2-B32-C13-D19
A3-B32-C13-D19
A9-B32-C13-D19
A13-B32-C13-D19
A24-B32-C13-D19

-continued

A69-B32-C13-D19
A67-B32-C13-D19
A39-B32-C13-D19
A65-B32-C13-D19
A66-B32-C13-D19
A2-B39-C13-D19
A3-B39-C13-D19
A9-B39-C13-D19
A13-B39-C13-D19
A24-B39-C13-D19
A69-B39-C13-D19
A67-B39-C13-D19
A39-B39-C13-D19
A65-B39-C13-D19
A66-B39-C13-D19
A2-B45-C13-D19
A3-B45-C13-D19
A9-B45-C13-D19
A13-B45-C13-D19
A24-B45-C13-D19
A69-B45-C13-D19
A67-B45-C13-D19
A39-B45-C13-D19
A65-B45-C13-D19
A66-B45-C13-D19
A2-B53-C13-D19
A3-B53-C13-D19
A9-B53-C13-D19
A13-B53-C13-D19
A24-B53-C13-D19
A69-B53-C13-D19
A67-B53-C13-D19
A39-B53-C13-D19
A65-B53-C13-D19
A66-B53-C13-D19
A2-B79-C13-D19
A3-B79-C13-D19
A9-B79-C13-D19
A13-B79-C13-D19
A24-B79-C13-D19
A69-B79-C13-D19
A67-B79-C13-D19
A39-B79-C13-D19
A65-B79-C13-D19
A66-B79-C13-D19
A2-B80-C13-D19
A3-B80-C13-D19
A9-B80-C13-D19
A13-B80-C13-D19
A24-B80-C13-D19
A69-B80-C13-D19
A67-B80-C13-D19
A39-B80-C13-D19
A65-B80-C13-D19
A66-B80-C13-D19
A2-B85-C13-D19
A3-B85-C13-D19
A9-B85-C13-D19
A13-B85-C13-D19
A24-B85-C13-D19
A69-B85-C13-D19
A67-B85-C13-D19
A39-B85-C13-D19
A65-B85-C13-D19
A66-B85-C13-D19
A2-B86-C13-D19
A3-B86-C13-D19
A9-B86-C13-D19
A13-B86-C13-D19
A24-B86-C13-D19
A69-B86-C13-D19
A67-B86-C13-D19
A39-B86-C13-D19
A65-B86-C13-D19
A66-B86-C13-D19
A2-B87-C13-D19
A3-B87-C13-D19
A9-B87-C13-D19
A13-B87-C13-D19
A24-B87-C13-D19

-continued

A69-B87-C13-D19
A67-B87-C13-D19
A39-B87-C13-D19
A65-B87-C13-D19
A66-B87-C13-D19
A2-B89-C13-D19
A3-B89-C13-D19
A9-B89-C13-D19
A13-B89-C13-D19
A24-B89-C13-D19
A69-B89-C13-D19
A67-B89-C13-D19
A39-B89-C13-D19
A65-B89-C13-D19
A66-B89-C13-D19
A2-B92-C13-D19
A3-B92-C13-D19
A9-B92-C13-D19
A13-B92-C13-D19
A24-B92-C13-D19
A69-B92-C13-D19
A67-B92-C13-D19
A39-B92-C13-D19
A65-B92-C13-D19
A66-B92-C13-D19
A2-B4-C1-D20
A3-B4-C1-D20
A9-B4-C1-D20
A13-B4-C1-D20
A24-B4-C1-D20
A69-B4-C1-D20
A67-B4-C1-D20
A39-B4-C1-D20
A65-B4-C1-D20
A66-B4-C1-D20
A2-B5-C1-D20
A3-B5-C1-D20
A9-B5-C1-D20
A13-B5-C1-D20
A24-B5-C1-D20
A69-B5-C1-D20
A67-B5-C1-D20
A39-B5-C1-D20
A65-B5-C1-D20
A66-B5-C1-D20
A2-B6-C1-D20
A3-B6-C1-D20
A9-B6-C1-D20
A13-B6-C1-D20
A24-B6-C1-D20
A69-B6-C1-D20
A67-B6-C1-D20
A39-B6-C1-D20
A65-B6-C1-D20
A66-B6-C1-D20
A2-B32-C1-D20
A3-B32-C1-D20
A9-B32-C1-D20
A13-B32-C1-D20
A24-B32-C1-D20
A69-B32-C1-D20
A67-B32-C1-D20
A39-B32-C1-D20
A65-B32-C1-D20
A66-B32-C1-D20
A2-B39-C1-D20
A3-B39-C1-D20
A9-B39-C1-D20
A13-B39-C1-D20
A24-B39-C1-D20
A69-B39-C1-D20
A67-B39-C1-D20
A39-B39-C1-D20
A65-B39-C1-D20
A66-B39-C1-D20
A2-B45-C1-D20
A3-B45-C1-D20
A9-B45-C1-D20
A13-B45-C1-D20
A24-B45-C1-D20

-continued
A69-B45-C1-D20
A67-B45-C1-D20
A39-B45-C1-D20
A65-B45-C1-D20
A66-B45-C1-D20
A2-B53-C1-D20
A3-B53-C1-D20
A9-B53-C1-D20
A13-B53-C1-D20
A24-B53-C1-D20
A69-B53-C1-D20
A67-B53-C1-D20
A39-B53-C1-D20
A65-B53-C1-D20
A66-B53-C1-D20
A2-B79-C1-D20
A3-B79-C1-D20
A9-B79-C1-D20
A13-B79-C1-D20
A24-B79-C1-D20
A69-B79-C1-D20
A67-B79-C1-D20
A39-B79-C1-D20
A65-B79-C1-D20
A66-B79-C1-D20
A2-B80-C1-D20
A3-B80-C1-D20
A9-B80-C1-D20
A13-B80-C1-D20
A24-B80-C1-D20
A69-B80-C1-D20
A67-B80-C1-D20
A39-B80-C1-D20
A65-B80-C1-D20
A66-B80-C1-D20
A2-B85-C1-D20
A3-B85-C1-D20
A9-B85-C1-D20
A13-B85-C1-D20
A24-B85-C1-D20
A69-B85-C1-D20
A67-B85-C1-D20
A39-B85-C1-D20
A65-B85-C1-D20
A66-B85-C1-D20
A2-B86-C1-D20
A3-B86-C1-D20
A9-B86-C1-D20
A13-B86-C1-D20
A24-B86-C1-D20
A69-B86-C1-D20
A67-B86-C1-D20
A39-B86-C1-D20
A65-B86-C1-D20
A66-B86-C1-D20
A2-B87-C1-D20
A3-B87-C1-D20
A9-B87-C1-D20
A13-B87-C1-D20
A24-B87-C1-D20
A69-B87-C1-D20
A67-B87-C1-D20
A39-B87-C1-D20
A65-B87-C1-D20
A66-B87-C1-D20
A2-B89-C1-D20
A3-B89-C1-D20
A9-B89-C1-D20
A13-B89-C1-D20
A24-B89-C1-D20
A69-B89-C1-D20
A67-B89-C1-D20
A39-B89-C1-D20
A65-B89-C1-D20
A66-B89-C1-D20
A2-B92-C1-D20
A3-B92-C1-D20
A9-B92-C1-D20
A13-B92-C1-D20
A24-B92-C1-D20

-continued
A69-B92-C1-D20
A67-B92-C1-D20
A39-B92-C1-D20
A65-B92-C1-D20
A66-B92-C1-D20
A2-B4-C2-D20
A3-B4-C2-D20
A9-B4-C2-D20
A13-B4-C2-D20
A24-B4-C2-D20
A69-B4-C2-D20
A67-B4-C2-D20
A39-B4-C2-D20
A65-B4-C2-D20
A66-B4-C2-D20
A2-B5-C2-D20
A3-B5-C2-D20
A9-B5-C2-D20
A13-B5-C2-D20
A24-B5-C2-D20
A69-B5-C2-D20
A67-B5-C2-D20
A39-B5-C2-D20
A65-B5-C2-D20
A66-B5-C2-D20
A2-B6-C2-D20
A3-B6-C2-D20
A9-B6-C2-D20
A13-B6-C2-D20
A24-B6-C2-D20
A69-B6-C2-D20
A67-B6-C2-D20
A39-B6-C2-D20
A65-B6-C2-D20
A66-B6-C2-D20
A2-B32-C2-D20
A3-B32-C2-D20
A9-B32-C2-D20
A13-B32-C2-D20
A24-B32-C2-D20
A69-B32-C2-D20
A67-B32-C2-D20
A39-B32-C2-D20
A65-B32-C2-D20
A66-B32-C2-D20
A2-B39-C2-D20
A3-B39-C2-D20
A9-B39-C2-D20
A13-B39-C2-D20
A24-B39-C2-D20
A69-B39-C2-D20
A67-B39-C2-D20
A39-B39-C2-D20
A65-B39-C2-D20
A66-B39-C2-D20
A2-B45-C2-D20
A3-B45-C2-D20
A9-B45-C2-D20
A13-B45-C2-D20
A24-B45-C2-D20
A69-B45-C2-D20
A67-B45-C2-D20
A39-B45-C2-D20
A65-B45-C2-D20
A66-B45-C2-D20
A2-B53-C2-D20
A3-B53-C2-D20
A9-B53-C2-D20
A13-B53-C2-D20
A24-B53-C2-D20
A69-B53-C2-D20
A67-B53-C2-D20
A39-B53-C2-D20
A65-B53-C2-D20
A66-B53-C2-D20
A2-B79-C2-D20
A3-B79-C2-D20
A9-B79-C2-D20
A13-B79-C2-D20
A24-B79-C2-D20

-continued

| | |
|---|---|
| A69-B79-C2-D20 | A69-B5-C3-D20 |
| A67-B79-C2-D20 | A67-B5-C3-D20 |
| A39-B79-C2-D20 | A39-B5-C3-D20 |
| A65-B79-C2-D20 | A65-B5-C3-D20 |
| A66-B79-C2-D20 | A66-B5-C3-D20 |
| A2-B80-C2-D20 | A2-B6-C3-D20 |
| A3-B80-C2-D20 | A3-B6-C3-D20 |
| A9-B80-C2-D20 | A9-B6-C3-D20 |
| A13-B80-C2-D20 | A13-B6-C3-D20 |
| A24-B80-C2-D20 | A24-B6-C3-D20 |
| A69-B80-C2-D20 | A69-B6-C3-D20 |
| A67-B80-C2-D20 | A67-B6-C3-D20 |
| A39-B80-C2-D20 | A39-B6-C3-D20 |
| A65-B80-C2-D20 | A65-B6-C3-D20 |
| A66-B80-C2-D20 | A66-B6-C3-D20 |
| A2-B85-C2-D20 | A2-B32-C3-D20 |
| A3-B85-C2-D20 | A3-B32-C3-D20 |
| A9-B85-C2-D20 | A9-B32-C3-D20 |
| A13-B85-C2-D20 | A13-B32-C3-D20 |
| A24-B85-C2-D20 | A24-B32-C3-D20 |
| A69-B85-C2-D20 | A69-B32-C3-D20 |
| A67-B85-C2-D20 | A67-B32-C3-D20 |
| A39-B85-C2-D20 | A39-B32-C3-D20 |
| A65-B85-C2-D20 | A65-B32-C3-D20 |
| A66-B85-C2-D20 | A66-B32-C3-D20 |
| A2-B86-C2-D20 | A2-B39-C3-D20 |
| A3-B86-C2-D20 | A3-B39-C3-D20 |
| A9-B86-C2-D20 | A9-B39-C3-D20 |
| A13-B86-C2-D20 | A13-B39-C3-D20 |
| A24-B86-C2-D20 | A24-B39-C3-D20 |
| A69-B86-C2-D20 | A69-B39-C3-D20 |
| A67-B86-C2-D20 | A67-B39-C3-D20 |
| A39-B86-C2-D20 | A39-B39-C3-D20 |
| A65-B86-C2-D20 | A65-B39-C3-D20 |
| A66-B86-C2-D20 | A66-B39-C3-D20 |
| A2-B87-C2-D20 | A2-B45-C3-D20 |
| A3-B87-C2-D20 | A3-B45-C3-D20 |
| A9-B87-C2-D20 | A9-B45-C3-D20 |
| A13-B87-C2-D20 | A13-B45-C3-D20 |
| A24-B87-C2-D20 | A24-B45-C3-D20 |
| A69-B87-C2-D20 | A69-B45-C3-D20 |
| A67-B87-C2-D20 | A67-B45-C3-D20 |
| A39-B87-C2-D20 | A39-B45-C3-D20 |
| A65-B87-C2-D20 | A65-B45-C3-D20 |
| A66-B87-C2-D20 | A66-B45-C3-D20 |
| A2-B89-C2-D20 | A2-B53-C3-D20 |
| A3-B89-C2-D20 | A3-B53-C3-D20 |
| A9-B89-C2-D20 | A9-B53-C3-D20 |
| A13-B89-C2-D20 | A13-B53-C3-D20 |
| A24-B89-C2-D20 | A24-B53-C3-D20 |
| A69-B89-C2-D20 | A69-B53-C3-D20 |
| A67-B89-C2-D20 | A67-B53-C3-D20 |
| A39-B89-C2-D20 | A39-B53-C3-D20 |
| A65-B89-C2-D20 | A65-B53-C3-D20 |
| A66-B89-C2-D20 | A66-B53-C3-D20 |
| A2-B92-C2-D20 | A2-B79-C3-D20 |
| A3-B92-C2-D20 | A3-B79-C3-D20 |
| A9-B92-C2-D20 | A9-B79-C3-D20 |
| A13-B92-C2-D20 | A13-B79-C3-D20 |
| A24-B92-C2-D20 | A24-B79-C3-D20 |
| A69-B92-C2-D20 | A69-B79-C3-D20 |
| A67-B92-C2-D20 | A67-B79-C3-D20 |
| A39-B92-C2-D20 | A39-B79-C3-D20 |
| A65-B92-C2-D20 | A65-B79-C3-D20 |
| A66-B92-C2-D20 | A66-B79-C3-D20 |
| A2-B4-C3-D20 | A2-B80-C3-D20 |
| A3-B4-C3-D20 | A3-B80-C3-D20 |
| A9-B4-C3-D20 | A9-B80-C3-D20 |
| A13-B4-C3-D20 | A13-B80-C3-D20 |
| A24-B4-C3-D20 | A24-B80-C3-D20 |
| A69-B4-C3-D20 | A69-B80-C3-D20 |
| A67-B4-C3-D20 | A67-B80-C3-D20 |
| A39-B4-C3-D20 | A39-B80-C3-D20 |
| A65-B4-C3-D20 | A65-B80-C3-D20 |
| A66-B4-C3-D20 | A66-B80-C3-D20 |
| A2-B5-C3-D20 | A2-B85-C3-D20 |
| A3-B5-C3-D20 | A3-B85-C3-D20 |
| A9-B5-C3-D20 | A9-B85-C3-D20 |
| A13-B5-C3-D20 | A13-B85-C3-D20 |
| A24-B5-C3-D20 | A24-B85-C3-D20 |

-continued
A69-B85-C3-D20
A67-B85-C3-D20
A39-B85-C3-D20
A65-B85-C3-D20
A66-B85-C3-D20
A2-B86-C3-D20
A3-B86-C3-D20
A9-B86-C3-D20
A13-B86-C3-D20
A24-B86-C3-D20
A69-B86-C3-D20
A67-B86-C3-D20
A39-B86-C3-D20
A65-B86-C3-D20
A66-B86-C3-D20
A2-B87-C3-D20
A3-B87-C3-D20
A9-B87-C3-D20
A13-B87-C3-D20
A24-B87-C3-D20
A69-B87-C3-D20
A67-B87-C3-D20
A39-B87-C3-D20
A65-B87-C3-D20
A66-B87-C3-D20
A2-B89-C3-D20
A3-B89-C3-D20
A9-B89-C3-D20
A13-B89-C3-D20
A24-B89-C3-D20
A69-B89-C3-D20
A67-B89-C3-D20
A39-B89-C3-D20
A65-B89-C3-D20
A66-B89-C3-D20
A2-B92-C3-D20
A3-B92-C3-D20
A9-B92-C3-D20
A13-B92-C3-D20
A24-B92-C3-D20
A69-B92-C3-D20
A67-B92-C3-D20
A39-B92-C3-D20
A65-B92-C3-D20
A66-B92-C3-D20
A2-B4-C4-D20
A3-B4-C4-D20
A9-B4-C4-D20
A13-B4-C4-D20
A24-B4-C4-D20
A69-B4-C4-D20
A67-B4-C4-D20
A39-B4-C4-D20
A65-B4-C4-D20
A66-B4-C4-D20
A2-B5-C4-D20
A3-B5-C4-D20
A9-B5-C4-D20
A13-B5-C4-D20
A24-B5-C4-D20
A69-B5-C4-D20
A67-B5-C4-D20
A39-B5-C4-D20
A65-B5-C4-D20
A66-B5-C4-D20
A2-B6-C4-D20
A3-B6-C4-D20
A9-B6-C4-D20
A13-B6-C4-D20
A24-B6-C4-D20
A69-B6-C4-D20
A67-B6-C4-D20
A39-B6-C4-D20
A65-B6-C4-D20
A66-B6-C4-D20
A2-B32-C4-D20
A3-B32-C4-D20
A9-B32-C4-D20
A13-B32-C4-D20
A24-B32-C4-D20

-continued
A69-B32-C4-D20
A67-B32-C4-D20
A39-B32-C4-D20
A65-B32-C4-D20
A66-B32-C4-D20
A2-B39-C4-D20
A3-B39-C4-D20
A9-B39-C4-D20
A13-B39-C4-D20
A24-B39-C4-D20
A69-B39-C4-D20
A67-B39-C4-D20
A39-B39-C4-D20
A65-B39-C4-D20
A66-B39-C4-D20
A2-B45-C4-D20
A3-B45-C4-D20
A9-B45-C4-D20
A13-B45-C4-D20
A24-B45-C4-D20
A69-B45-C4-D20
A67-B45-C4-D20
A39-B45-C4-D20
A65-B45-C4-D20
A66-B45-C4-D20
A2-B53-C4-D20
A3-B53-C4-D20
A9-B53-C4-D20
A13-B53-C4-D20
A24-B53-C4-D20
A69-B53-C4-D20
A67-B53-C4-D20
A39-B53-C4-D20
A65-B53-C4-D20
A66-B53-C4-D20
A2-B79-C4-D20
A3-B79-C4-D20
A9-B79-C4-D20
A13-B79-C4-D20
A24-B79-C4-D20
A69-B79-C4-D20
A67-B79-C4-D20
A39-B79-C4-D20
A65-B79-C4-D20
A66-B79-C4-D20
A2-B80-C4-D20
A3-B80-C4-D20
A9-B80-C4-D20
A13-B80-C4-D20
A24-B80-C4-D20
A69-B80-C4-D20
A67-B80-C4-D20
A39-B80-C4-D20
A65-B80-C4-D20
A66-B80-C4-D20
A2-B85-C4-D20
A3-B85-C4-D20
A9-B85-C4-D20
A13-B85-C4-D20
A24-B85-C4-D20
A69-B85-C4-D20
A67-B85-C4-D20
A39-B85-C4-D20
A65-B85-C4-D20
A66-B85-C4-D20
A2-B86-C4-D20
A3-B86-C4-D20
A9-B86-C4-D20
A13-B86-C4-D20
A24-B86-C4-D20
A69-B86-C4-D20
A67-B86-C4-D20
A39-B86-C4-D20
A65-B86-C4-D20
A66-B86-C4-D20
A2-B87-C4-D20
A3-B87-C4-D20
A9-B87-C4-D20
A13-B87-C4-D20
A24-B87-C4-D20

-continued

A69-B87-C4-D20
A67-B87-C4-D20
A39-B87-C4-D20
A65-B87-C4-D20
A66-B87-C4-D20
A2-B89-C4-D20
A3-B89-C4-D20
A9-B89-C4-D20
A13-B89-C4-D20
A24-B89-C4-D20
A69-B89-C4-D20
A67-B89-C4-D20
A39-B89-C4-D20
A65-B89-C4-D20
A66-B89-C4-D20
A2-B92-C4-D20
A3-B92-C4-D20
A9-B92-C4-D20
A13-B92-C4-D20
A24-B92-C4-D20
A69-B92-C4-D20
A67-B92-C4-D20
A39-B92-C4-D20
A65-B92-C4-D20
A66-B92-C4-D20
A2-B4-C5-D20
A3-B4-C5-D20
A9-B4-C5-D20
A13-B4-C5-D20
A24-B4-C5-D20
A69-B4-C5-D20
A67-B4-C5-D20
A39-B4-C5-D20
A65-B4-C5-D20
A66-B4-C5-D20
A2-B5-C5-D20
A3-B5-C5-D20
A9-B5-C5-D20
A13-B5-C5-D20
A24-B5-C5-D20
A69-B5-C5-D20
A67-B5-C5-D20
A39-B5-C5-D20
A65-B5-C5-D20
A66-B5-C5-D20
A2-B6-C5-D20
A3-B6-C5-D20
A9-B6-C5-D20
A13-B6-C5-D20
A24-B6-C5-D20
A69-B6-C5-D20
A67-B6-C5-D20
A39-B6-C5-D20
A65-B6-C5-D20
A66-B6-C5-D20
A2-B32-C5-D20
A3-B32-C5-D20
A9-B32-C5-D20
A13-B32-C5-D20
A24-B32-C5-D20
A69-B32-C5-D20
A67-B32-C5-D20
A39-B32-C5-D20
A65-B32-C5-D20
A66-B32-C5-D20
A2-B39-C5-D20
A3-B39-C5-D20
A9-B39-C5-D20
A13-B39-C5-D20
A24-B39-C5-D20
A69-B39-C5-D20
A67-B39-C5-D20
A39-B39-C5-D20
A65-B39-C5-D20
A66-B39-C5-D20
A2-B45-C5-D20
A3-B45-C5-D20
A9-B45-C5-D20
A13-B45-C5-D20
A24-B45-C5-D20

-continued

A69-B45-C5-D20
A67-B45-C5-D20
A39-B45-C5-D20
A65-B45-C5-D20
A66-B45-C5-D20
A2-B53-C5-D20
A3-B53-C5-D20
A9-B53-C5-D20
A13-B53-C5-D20
A24-B53-C5-D20
A69-B53-C5-D20
A67-B53-C5-D20
A39-B53-C5-D20
A65-B53-C5-D20
A66-B53-C5-D20
A2-B79-C5-D20
A3-B79-C5-D20
A9-B79-C5-D20
A13-B79-C5-D20
A24-B79-C5-D20
A69-B79-C5-D20
A67-B79-C5-D20
A39-B79-C5-D20
A65-B79-C5-D20
A66-B79-C5-D20
A2-B80-C5-D20
A3-B80-C5-D20
A9-B80-C5-D20
A13-B80-C5-D20
A24-B80-C5-D20
A69-B80-C5-D20
A67-B80-C5-D20
A39-B80-C5-D20
A65-B80-C5-D20
A66-B80-C5-D20
A2-B85-C5-D20
A3-B85-C5-D20
A9-B85-C5-D20
A13-B85-C5-D20
A24-B85-C5-D20
A69-B85-C5-D20
A67-B85-C5-D20
A39-B85-C5-D20
A65-B85-C5-D20
A66-B85-C5-D20
A2-B86-C5-D20
A3-B86-C5-D20
A9-B86-C5-D20
A13-B86-C5-D20
A24-B86-C5-D20
A69-B86-C5-D20
A67-B86-C5-D20
A39-B86-C5-D20
A65-B86-C5-D20
A66-B86-C5-D20
A2-B87-C5-D20
A3-B87-C5-D20
A9-B87-C5-D20
A13-B87-C5-D20
A24-B87-C5-D20
A69-B87-C5-D20
A67-B87-C5-D20
A39-B87-C5-D20
A65-B87-C5-D20
A66-B87-C5-D20
A2-B89-C5-D20
A3-B89-C5-D20
A9-B89-C5-D20
A13-B89-C5-D20
A24-B89-C5-D20
A69-B89-C5-D20
A67-B89-C5-D20
A39-B89-C5-D20
A65-B89-C5-D20
A66-B89-C5-D20
A2-B92-C5-D20
A3-B92-C5-D20
A9-B92-C5-D20
A13-B92-C5-D20
A24-B92-C5-D20

-continued
A69-B92-C5-D20
A67-B92-C5-D20
A39-B92-C5-D20
A65-B92-C5-D20
A66-B92-C8-D20
A2-B4-C6-D20
A3-B4-C6-D20
A9-B4-C6-D20
A13-B4-C6-D20
A24-B4-C6-D20
A69-B4-C6-D20
A67-B4-C6-D20
A39-B4-C6-D20
A65-B4-C6-D20
A66-B4-C6-D20
A2-B5-C6-D20
A3-B5-C6-D20
A9-B5-C6-D20
A13-B5-C6-D20
A24-B5-C6-D20
A69-B5-C6-D20
A67-B5-C6-D20
A39-B5-C6-D20
A65-B5-C6-D20
A66-B5-C6-D20
A2-B6-C6-D20
A3-B6-C6-D20
A9-B6-C6-D20
A13-B6-C6-D20
A24-B6-C6-D20
A69-B6-C6-D20
A67-B6-C6-D20
A39-B6-C6-D20
A65-B6-C6-D20
A66-B6-C6-D20
A2-B32-C6-D20
A3-B32-C6-D20
A9-B32-C6-D20
A13-B32-C6-D20
A24-B32-C6-D20
A69-B32-C6-D20
A67-B32-C6-D20
A39-B32-C6-D20
A65-B32-C6-D20
A66-B32-C6-D20
A2-B39-C6-D20
A3-B39-C6-D20
A9-B39-C6-D20
A13-B39-C6-D20
A24-B39-C6-D20
A69-B39-C6-D20
A67-B39-C6-D20
A39-B39-C6-D20
A65-B39-C6-D20
A66-B39-C6-D20
A2-B45-C6-D20
A3-B45-C6-D20
A9-B45-C6-D20
A13-B45-C6-D20
A24-B45-C6-D20
A69-B45-C6-D20
A67-B45-C6-D20
A39-B45-C6-D20
A65-B45-C6-D20
A66-B45-C6-D20
A2-B53-C6-D20
A3-B53-C6-D20
A9-B53-C6-D20
A13-B53-C6-D20
A24-B53-C6-D20
A69-B53-C6-D20
A67-B53-C6-D20
A39-B53-C6-D20
A65-B53-C6-D20
A66-B53-C6-D20
A2-B79-C6-D20
A3-B79-C6-D20
A9-B79-C6-D20
A13-B79-C6-D20
A24-B79-C6-D20

-continued
A69-B79-C6-D20
A67-B79-C6-D20
A39-B79-C6-D20
A65-B79-C6-D20
A66-B79-C6-D20
A2-B80-C6-D20
A3-B80-C6-D20
A9-B80-C6-D20
A13-B80-C6-D20
A24-B80-C6-D20
A69-B80-C6-D20
A67-B80-C6-D20
A39-B80-C6-D20
A65-B80-C6-D20
A66-B80-C6-D20
A2-B85-C6-D20
A3-B85-C6-D20
A9-B85-C6-D20
A13-B85-C6-D20
A24-B85-C6-D20
A69-B85-C6-D20
A67-B85-C6-D20
A39-B85-C6-D20
A65-B85-C6-D20
A66-B85-C6-D20
A2-B86-C6-D20
A3-B86-C6-D20
A9-B86-C6-D20
A13-B86-C6-D20
A24-B86-C6-D20
A69-B86-C6-D20
A67-B86-C6-D20
A39-B86-C6-D20
A65-B86-C6-D20
A66-B86-C6-D20
A2-B87-C6-D20
A3-B87-C6-D20
A9-B87-C6-D20
A13-B87-C6-D20
A24-B87-C6-D20
A69-B87-C6-D20
A67-B87-C6-D20
A39-B87-C6-D20
A65-B87-C6-D20
A66-B87-C6-D20
A2-B89-C6-D20
A3-B89-C6-D20
A9-B89-C6-D20
A13-B89-C6-D20
A24-B89-C6-D20
A69-B89-C6-D20
A67-B89-C6-D20
A39-B89-C6-D20
A65-B89-C6-D20
A66-B89-C6-D20
A2-B92-C6-D20
A3-B92-C6-D20
A9-B92-C6-D20
A13-B92-C6-D20
A24-B92-C6-D20
A69-B92-C6-D20
A67-B92-C6-D20
A39-B92-C6-D20
A65-B92-C6-D20
A66-B92-C6-D20
A2-B4-C7-D20
A3-B4-C7-D20
A9-B4-C7-D20
A13-B4-C7-D20
A24-B4-C7-D20
A69-B4-C7-D20
A67-B4-C7-D20
A39-B4-C7-D20
A65-B4-C7-D20
A66-B4-C7-D20
A2-B5-C7-D20
A3-B5-C7-D20
A9-B5-C7-D20
A13-B5-C7-D20
A24-B5-C7-D20

-continued

A69-B5-C7-D20
A67-B5-C7-D20
A39-B5-C7-D20
A65-B5-C7-D20
A66-B5-C7-D20
A2-B6-C7-D20
A3-B6-C7-D20
A9-B6-C7-D20
A13-B6-C7-D20
A24-B6-C7-D20
A69-B6-C7-D20
A67-B6-C7-D20
A39-B6-C7-D20
A65-B6-C7-D20
A66-B6-C7-D20
A2-B32-C7-D20
A3-B32-C7-D20
A9-B32-C7-D20
A13-B32-C7-D20
A24-B32-C7-D20
A69-B32-C7-D20
A67-B32-C7-D20
A39-B32-C7-D20
A65-B32-C7-D20
A66-B32-C7-D20
A2-B39-C7-D20
A3-B39-C7-D20
A9-B39-C7-D20
A13-B39-C7-D20
A24-B39-C7-D20
A69-B39-C7-D20
A67-B39-C7-D20
A39-B39-C7-D20
A65-B39-C7-D20
A66-B39-C7-D20
A2-B45-C7-D20
A3-B45-C7-D20
A9-B45-C7-D20
A13-B45-C7-D20
A24-B45-C7-D20
A69-B45-C7-D20
A67-B45-C7-D20
A39-B45-C7-D20
A65-B45-C7-D20
A66-B45-C7-D20
A2-B53-C7-D20
A3-B53-C7-D20
A9-B53-C7-D20
A13-B53-C7-D20
A24-B53-C7-D20
A69-B53-C7-D20
A67-B53-C7-D20
A39-B53-C7-D20
A65-B53-C7-D20
A66-B53-C7-D20
A2-B79-C7-D20
A3-B79-C7-D20
A9-B79-C7-D20
A13-B79-C7-D20
A24-B79-C7-D20
A69-B79-C7-D20
A67-B79-C7-D20
A39-B79-C7-D20
A65-B79-C7-D20
A66-B79-C7-D20
A2-B80-C7-D20
A3-B80-C7-D20
A9-B80-C7-D20
A13-B80-C7-D20
A24-B80-C7-D20
A69-B80-C7-D20
A67-B80-C7-D20
A39-B80-C7-D20
A65-B80-C7-D20
A66-B80-C7-D20
A2-B85-C7-D20
A3-B85-C7-D20
A9-B85-C7-D20
A13-B85-C7-D20
A24-B85-C7-D20

-continued

A69-B85-C7-D20
A67-B85-C7-D20
A39-B85-C7-D20
A65-B85-C7-D20
A66-B85-C7-D20
A2-B86-C7-D20
A3-B86-C7-D20
A9-B86-C7-D20
A13-B86-C7-D20
A24-B86-C7-D20
A69-B86-C7-D20
A67-B86-C7-D20
A39-B86-C7-D20
A65-B86-C7-D20
A66-B86-C7-D20
A2-B87-C7-D20
A3-B87-C7-D20
A9-B87-C7-D20
A13-B87-C7-D20
A24-B87-C7-D20
A69-B87-C7-D20
A67-B87-C7-D20
A39-B87-C7-D20
A65-B87-C7-D20
A66-B87-C7-D20
A2-B89-C7-D20
A3-B89-C7-D20
A9-B89-C7-D20
A13-B89-C7-D20
A24-B89-C7-D20
A69-B89-C7-D20
A67-B89-C7-D20
A39-B89-C7-D20
A65-B89-C7-D20
A66-B89-C7-D20
A2-B92-C7-D20
A3-B92-C7-D20
A9-B92-C7-D20
A13-B92-C7-D20
A24-B92-C7-D20
A69-B92-C7-D20
A67-B92-C7-D20
A39-B92-C7-D20
A65-B92-C7-D20
A66-B92-C7-D20
A2-B4-C8-D20
A3-B4-C8-D20
A9-B4-C8-D20
A13-B4-C8-D20
A24-B4-C8-D20
A69-B4-C8-D20
A67-B4-C8-D20
A39-B4-C8-D20
A65-B4-C8-D20
A66-B4-C8-D20
A2-B5-C8-D20
A3-B5-C8-D20
A9-B5-C8-D20
A13-B5-C8-D20
A24-B5-C8-D20
A69-B5-C8-D20
A67-B5-C8-D20
A39-B5-C8-D20
A65-B5-C8-D20
A66-B5-C8-D20
A2-B6-C8-D20
A3-B6-C8-D20
A9-B6-C8-D20
A13-B6-C8-D20
A24-B6-C8-D20
A69-B6-C8-D20
A67-B6-C8-D20
A39-B6-C8-D20
A65-B6-C8-D20
A66-B6-C8-D20
A2-B32-C8-D20
A3-B32-C8-D20
A9-B32-C8-D20
A13-B32-C8-D20
A24-B32-C8-D20

-continued
A69-B32-C8-D20
A67-B32-C8-D20
A39-B32-C8-D20
A65-B32-C8-D20
A66-B32-C8-D20
A2-B39-C8-D20
A3-B39-C8-D20
A9-B39-C8-D20
A13-B39-C8-D20
A24-B39-C8-D20
A69-B39-C8-D20
A67-B39-C8-D20
A39-B39-C8-D20
A65-B39-C8-D20
A66-B39-C8-D20
A2-B45-C8-D20
A3-B45-C8-D20
A9-B45-C8-D20
A13-B45-C8-D20
A24-B45-C8-D20
A69-B45-C8-D20
A67-B45-C8-D20
A39-B45-C8-D20
A65-B45-C8-D20
A66-B45-C8-D20
A2-B53-C8-D20
A3-B53-C8-D20
A9-B53-C8-D20
A13-B53-C8-D20
A24-B53-C8-D20
A69-B53-C8-D20
A67-B53-C8-D20
A39-B53-C8-D20
A65-B53-C8-D20
A66-B53-C8-D20
A2-B79-C8-D20
A3-B79-C8-D20
A9-B79-C8-D20
A13-B79-C8-D20
A24-B79-C8-D20
A69-B79-C8-D20
A67-B79-C8-D20
A39-B79-C8-D20
A65-B79-C8-D20
A66-B79-C8-D20
A2-B80-C8-D20
A3-B80-C8-D20
A9-B80-C8-D20
A13-B80-C8-D20
A24-B80-C8-D20
A69-B80-C8-D20
A67-B80-C8-D20
A39-B80-C8-D20
A65-B80-C8-D20
A66-B80-C8-D20
A2-B85-C8-D20
A3-B85-C8-D20
A9-B85-C8-D20
A13-B85-C8-D20
A24-B85-C8-D20
A69-B85-C8-D20
A67-B85-C8-D20
A39-B85-C8-D20
A65-B85-C8-D20
A66-B85-C8-D20
A2-B86-C8-D20
A3-B86-C8-D20
A9-B86-C8-D20
A13-B86-C8-D20
A24-B86-C8-D20
A69-B86-C8-D20
A67-B86-C8-D20
A39-B86-C8-D20
A65-B86-C8-D20
A66-B86-C8-D20
A2-B87-C8-D20
A3-B87-C8-D20
A9-B87-C8-D20
A13-B87-C8-D20
A24-B87-C8-D20

-continued
A69-B87-C8-D20
A67-B87-C8-D20
A39-B87-C8-D20
A65-B87-C8-D20
A66-B87-C8-D20
A2-B89-C8-D20
A3-B89-C8-D20
A9-B89-C8-D20
A13-B89-C8-D20
A24-B89-C8-D20
A69-B89-C8-D20
A67-B89-C8-D20
A39-B89-C8-D20
A65-B89-C8-D20
A66-B89-C8-D20
A2-B92-C8-D20
A3-B92-C8-D20
A9-B92-C8-D20
A13-B92-C8-D20
A24-B92-C8-D20
A69-B92-C8-D20
A67-B92-C8-D20
A39-B92-C8-D20
A65-B92-C8-D20
A66-B92-C8-D20
A2-B4-C9-D20
A3-B4-C9-D20
A9-B4-C9-D20
A13-B4-C9-D20
A24-B4-C9-D20
A69-B4-C9-D20
A67-B4-C9-D20
A39-B4-C9-D20
A65-B4-C9-D20
A66-B4-C9-D20
A2-B5-C9-D20
A3-B5-C9-D20
A9-B5-C9-D20
A13-B5-C9-D20
A24-B5-C9-D20
A69-B5-C9-D20
A67-B5-C9-D20
A39-B5-C9-D20
A65-B5-C9-D20
A66-B5-C9-D20
A2-B6-C9-D20
A3-B6-C9-D20
A9-B6-C9-D20
A13-B6-C9-D20
A24-B6-C9-D20
A69-B6-C9-D20
A67-B6-C9-D20
A39-B6-C9-D20
A65-B6-C9-D20
A66-B6-C9-D20
A2-B32-C9-D20
A3-B32-C9-D20
A9-B32-C9-D20
A13-B32-C9-D20
A24-B32-C9-D20
A69-B32-C9-D20
A67-B32-C9-D20
A39-B32-C9-D20
A65-B32-C9-D20
A66-B32-C9-D20
A2-B39-C9-D20
A3-B39-C9-D20
A9-B39-C9-D20
A13-B39-C9-D20
A24-B39-C9-D20
A69-B39-C9-D20
A67-B39-C9-D20
A39-B39-C9-D20
A65-B39-C9-D20
A66-B39-C9-D20
A2-B45-C9-D20
A3-B45-C9-D20
A9-B45-C9-D20
A13-B45-C9-D20
A24-B45-C9-D20

-continued
A69-B45-C9-D20
A67-B45-C9-D20
A39-B45-C9-D20
A65-B45-C9-D20
A66-B45-C9-D20
A2-B53-C9-D20
A3-B53-C9-D20
A9-B53-C9-D20
A13-B53-C9-D20
A24-B53-C9-D20
A69-B53-C9-D20
A67-B53-C9-D20
A39-B53-C9-D20
A65-B53-C9-D20
A66-B53-C9-D20
A2-B79-C9-D20
A3-B79-C9-D20
A9-B79-C9-D20
A13-B79-C9-D20
A24-B79-C9-D20
A69-B79-C9-D20
A67-B79-C9-D20
A39-B79-C9-D20
A65-B79-C9-D20
A66-B79-C9-D20
A2-B80-C9-D20
A3-B80-C9-D20
A9-B80-C9-D20
A13-B80-C9-D20
A24-B80-C9-D20
A69-B80-C9-D20
A67-B80-C9-D20
A39-B80-C9-D20
A65-B80-C9-D20
A66-B80-C9-D20
A2-B85-C9-D20
A3-B85-C9-D20
A9-B85-C9-D20
A13-B85-C9-D20
A24-B85-C9-D20
A69-B85-C9-D20
A67-B85-C9-D20
A39-B85-C9-D20
A65-B85-C9-D20
A66-B85-C9-D20
A2-B86-C9-D20
A3-B86-C9-D20
A9-B86-C9-D20
A13-B86-C9-D20
A24-B86-C9-D20
A69-B86-C9-D20
A67-B86-C9-D20
A39-B86-C9-D20
A65-B86-C9-D20
A66-B86-C9-D20
A2-B87-C9-D20
A3-B87-C9-D20
A9-B87-C9-D20
A13-B87-C9-D20
A24-B87-C9-D20
A69-B87-C9-D20
A67-B87-C9-D20
A39-B87-C9-D20
A65-B87-C9-D20
A66-B87-C9-D20
A2-B89-C9-D20
A3-B89-C9-D20
A9-B89-C9-D20
A13-B89-C9-D20
A24-B89-C9-D20
A69-B89-C9-D20
A67-B89-C9-D20
A39-B89-C9-D20
A65-B89-C9-D20
A66-B89-C9-D20
A2-B92-C9-D20
A3-B92-C9-D20
A9-B92-C9-D20
A13-B92-C9-D20
A24-B92-C9-D20

-continued
A69-B92-C9-D20
A67-B92-C9-D20
A39-B92-C9-D20
A65-B92-C9-D20
A66-B92-C9-D20
A2-B4-C10-D20
A3-B4-C10-D20
A9-B4-C10-D20
A13-B4-C10-D20
A24-B4-C10-D20
A69-B4-C10-D20
A67-B4-C10-D20
A39-B4-C10-D20
A65-B4-C10-D20
A66-B4-C10-D20
A2-B5-C10-D20
A3-B5-C10-D20
A9-B5-C10-D20
A13-B5-C10-D20
A24-B5-C10-D20
A69-B5-C10-D20
A67-B5-C10-D20
A39-B5-C10-D20
A65-B5-C10-D20
A66-B5-C10-D20
A2-B6-C10-D20
A3-B6-C10-D20
A9-B6-C10-D20
A13-B6-C10-D20
A24-B6-C10-D20
A69-B6-C10-D20
A67-B6-C10-D20
A39-B6-C10-D20
A65-B6-C10-D20
A66-B6-C10-D20
A2-B32-C10-D20
A3-B32-C10-D20
A9-B32-C10-D20
A13-B32-C10-D20
A24-B32-C10-D20
A69-B32-C10-D20
A67-B32-C10-D20
A39-B32-C10-D20
A65-B32-C10-D20
A66-B32-C10-D20
A2-B39-C10-D20
A3-B39-C10-D20
A9-B39-C10-D20
A13-B39-C10-D20
A24-B39-C10-D20
A69-B39-C10-D20
A67-B39-C10-D20
A39-B39-C10-D20
A65-B39-C10-D20
A66-B39-C10-D20
A2-B45-C10-D20
A3-B45-C10-D20
A9-B45-C10-D20
A13-B45-C10-D20
A24-B45-C10-D20
A69-B45-C10-D20
A67-B45-C10-D20
A39-B45-C10-D20
A65-B45-C10-D20
A66-B45-C10-D20
A2-B53-C10-D20
A3-B53-C10-D20
A9-B53-C10-D20
A13-B53-C10-D20
A24-B53-C10-D20
A69-B53-C10-D20
A67-B53-C10-D20
A39-B53-C10-D20
A65-B53-C10-D20
A66-B53-C10-D20
A2-B79-C10-D20
A3-B79-C10-D20
A9-B79-C10-D20
A13-B79-C10-D20
A24-B79-C10-D20

-continued
A69-B79-C10-D20
A67-B79-C10-D20
A39-B79-C10-D20
A65-B79-C10-D20
A66-B79-C10-D20
A2-B80-C10-D20
A3-B80-C10-D20
A9-B80-C10-D20
A13-B80-C10-D20
A24-B80-C10-D20
A69-B80-C10-D20
A67-B80-C10-D20
A39-B80-C10-D20
A65-B80-C10-D20
A66-B80-C10-D20
A2-B85-C10-D20
A3-B85-C10-D20
A9-B85-C10-D20
A13-B85-C10-D20
A24-B85-C10-D20
A69-B85-C10-D20
A67-B85-C10-D20
A39-B85-C10-D20
A65-B85-C10-D20
A66-B85-C10-D20
A2-B86-C10-D20
A3-B86-C10-D20
A9-B86-C10-D20
A13-B86-C10-D20
A24-B86-C10-D20
A69-B86-C10-D20
A67-B86-C10-D20
A39-B86-C10-D20
A65-B86-C10-D20
A66-B86-C10-D20
A2-B87-C10-D20
A3-B87-C10-D20
A9-B87-C10-D20
A13-B87-C10-D20
A24-B87-C10-D20
A69-B87-C10-D20
A67-B87-C10-D20
A39-B87-C10-D20
A65-B87-C10-D20
A66-B87-C10-D20
A2-B89-C10-D20
A3-B89-C10-D20
A9-B89-C10-D20
A13-B89-C10-D20
A24-B89-C10-D20
A69-B89-C10-D20
A67-B89-C10-D20
A39-B89-C10-D20
A65-B89-C10-D20
A66-B89-C10-D20
A2-B92-C10-D20
A3-B92-C10-D20
A9-B92-C10-D20
A13-B92-C10-D20
A24-B92-C10-D20
A69-B92-C10-D20
A67-B92-C10-D20
A39-B92-C10-D20
A65-B92-C10-D20
A66-B92-C10-D20
A2-B4-C11-D20
A3-B4-C11-D20
A9-B4-C11-D20
A13-B4-C11-D20
A24-B4-C11-D20
A69-B4-C11-D20
A67-B4-C11-D20
A39-B4-C11-D20
A65-B4-C11-D20
A66-B4-C11-D20
A2-B5-C11-D20
A3-B5-C11-D20
A9-B5-C11-D20
A13-B5-C11-D20
A24-B5-C11-D20

-continued
A69-B5-C11-D20
A67-B5-C11-D20
A39-B5-C11-D20
A65-B5-C11-D20
A66-B5-C11-D20
A2-B6-C11-D20
A3-B6-C11-D20
A9-B6-C11-D20
A13-B6-C11-D20
A24-B6-C11-D20
A69-B6-C11-D20
A67-B6-C11-D20
A39-B6-C11-D20
A65-B6-C11-D20
A66-B6-C11-D20
A2-B32-C11-D20
A3-B32-C11-D20
A9-B32-C11-D20
A13-B32-C11-D20
A24-B32-C11-D20
A69-B32-C11-D20
A67-B32-C11-D20
A39-B32-C11-D20
A65-B32-C11-D20
A66-B32-C11-D20
A2-B39-C11-D20
A3-B39-C11-D20
A9-B39-C11-D20
A13-B39-C11-D20
A24-B39-C11-D20
A69-B39-C11-D20
A67-B39-C11-D20
A39-B39-C11-D20
A65-B39-C11-D20
A66-B39-C11-D20
A2-B45-C11-D20
A3-B45-C11-D20
A9-B45-C11-D20
A13-B45-C11-D20
A24-B45-C11-D20
A69-B45-C11-D20
A67-B45-C11-D20
A39-B45-C11-D20
A65-B45-C11-D20
A66-B45-C11-D20
A2-B53-C11-D20
A3-B53-C11-D20
A9-B53-C11-D20
A13-B53-C11-D20
A24-B53-C11-D20
A69-B53-C11-D20
A67-B53-C11-D20
A39-B53-C11-D20
A65-B53-C11-D20
A66-B53-C11-D20
A2-B79-C11-D20
A3-B79-C11-D20
A9-B79-C11-D20
A13-B79-C11-D20
A24-B79-C11-D20
A69-B79-C11-D20
A67-B79-C11-D20
A39-B79-C11-D20
A65-B79-C11-D20
A66-B79-C11-D20
A2-B80-C11-D20
A3-B80-C11-D20
A9-B80-C11-D20
A13-B80-C11-D20
A24-B80-C11-D20
A69-B80-C11-D20
A67-B80-C11-D20
A39-B80-C11-D20
A65-B80-C11-D20
A66-B80-C11-D20
A2-B85-C11-D20
A3-B85-C11-D20
A9-B85-C11-D20
A13-B85-C11-D20
A24-B85-C11-D20

-continued
A69-B85-C11-D20
A67-B85-C11-D20
A39-B85-C11-D20
A65-B85-C11-D20
A66-B85-C11-D20
A2-B86-C11-D20
A3-B86-C11-D20
A9-B86-C11-D20
A13-B86-C11-D20
A24-B86-C11-D20
A69-B86-C11-D20
A67-B86-C11-D20
A39-B86-C11-D20
A65-B86-C11-D20
A66-B86-C11-D20
A2-B87-C11-D20
A3-B87-C11-D20
A9-B87-C11-D20
A13-B87-C11-D20
A24-B87-C11-D20
A69-B87-C11-D20
A67-B87-C11-D20
A39-B87-C11-D20
A65-B87-C11-D20
A66-B87-C11-D20
A2-B89-C11-D20
A3-B89-C11-D20
A9-B89-C11-D20
A13-B89-C11-D20
A24-B89-C11-D20
A69-B89-C11-D20
A67-B89-C11-D20
A39-B89-C11-D20
A65-B89-C11-D20
A66-B89-C11-D20
A2-B92-C11-D20
A3-B92-C11-D20
A9-B92-C11-D20
A13-B92-C11-D20
A24-B92-C11-D20
A69-B92-C11-D20
A67-B92-C11-D20
A39-B92-C11-D20
A65-B92-C11-D20
A66-B92-C11-D20
A2-B4-C12-D20
A3-B4-C12-D20
A9-B4-C12-D20
A13-B4-C12-D20
A24-B4-C12-D20
A69-B4-C12-D20
A67-B4-C12-D20
A39-B4-C12-D20
A65-B4-C12-D20
A66-B4-C12-D20
A2-B5-C12-D20
A3-B5-C12-D20
A9-B5-C12-D20
A13-B5-C12-D20
A24-B5-C12-D20
A69-B5-C12-D20
A67-B5-C12-D20
A39-B5-C12-D20
A65-B5-C12-D20
A66-B5-C12-D20
A2-B6-C12-D20
A3-B6-C12-D20
A9-B6-C12-D20
A13-B6-C12-D20
A24-B6-C12-D20
A69-B6-C12-D20
A67-B6-C12-D20
A39-B6-C12-D20
A65-B6-C12-D20
A66-B6-C12-D20
A2-B32-C12-D20
A3-B32-C12-D20
A9-B32-C12-D20
A13-B32-C12-D20
A24-B32-C12-D20

-continued
A69-B32-C12-D20
A67-B32-C12-D20
A39-B32-C12-D20
A65-B32-C12-D20
A66-B32-C12-D20
A2-B39-C12-D20
A3-B39-C12-D20
A9-B39-C12-D20
A13-B39-C12-D20
A24-B39-C12-D20
A69-B39-C12-D20
A67-B39-C12-D20
A39-B39-C12-D20
A65-B39-C12-D20
A66-B39-C12-D20
A2-B45-C12-D20
A3-B45-C12-D20
A9-B45-C12-D20
A13-B45-C12-D20
A24-B45-C12-D20
A69-B45-C12-D20
A67-B45-C12-D20
A39-B45-C12-D20
A65-B45-C12-D20
A66-B45-C12-D20
A2-B53-C12-D20
A3-B53-C12-D20
A9-B53-C12-D20
A13-B53-C12-D20
A24-B53-C12-D20
A69-B53-C12-D20
A67-B53-C12-D20
A39-B53-C12-D20
A65-B53-C12-D20
A66-B53-C12-D20
A2-B79-C12-D20
A3-B79-C12-D20
A9-B79-C12-D20
A13-B79-C12-D20
A24-B79-C12-D20
A69-B79-C12-D20
A67-B79-C12-D20
A39-B79-C12-D20
A65-B79-C12-D20
A66-B79-C12-D20
A2-B80-C12-D20
A3-B80-C12-D20
A9-B80-C12-D20
A13-B80-C12-D20
A24-B80-C12-D20
A69-B80-C12-D20
A67-B80-C12-D20
A39-B80-C12-D20
A65-B80-C12-D20
A66-B80-C12-D20
A2-B85-C12-D20
A3-B85-C12-D20
A9-B85-C12-D20
A13-B85-C12-D20
A24-B85-C12-D20
A69-B85-C12-D20
A67-B85-C12-D20
A39-B85-C12-D20
A65-B85-C12-D20
A66-B85-C12-D20
A2-B86-C12-D20
A3-B86-C12-D20
A9-B86-C12-D20
A13-B86-C12-D20
A24-B86-C12-D20
A69-B86-C12-D20
A67-B86-C12-D20
A39-B86-C12-D20
A65-B86-C12-D20
A66-B86-C12-D20
A2-B87-C12-D20
A3-B87-C12-D20
A9-B87-C12-D20
A13-B87-C12-D20
A24-B87-C12-D20

-continued
A69-B87-C12-D20
A67-B87-C12-D20
A39-B87-C12-D20
A65-B87-C12-D20
A66-B87-C12-D20
A2-B89-C12-D20
A3-B89-C12-D20
A9-B89-C12-D20
A13-B89-C12-D20
A24-B89-C12-D20
A69-B89-C12-D20
A67-B89-C12-D20
A39-B89-C12-D20
A65-B89-C12-D20
A66-B89-C12-D20
A2-B92-C12-D20
A3-B92-C12-D20
A9-B92-C12-D20
A13-B92-C12-D20
A24-B92-C12-D20
A69-B92-C12-D20
A67-B92-C12-D20
A39-B92-C12-D20
A65-B92-C12-D20
A66-B92-C12-D20
A2-B4-C13-D20
A3-B4-C13-D20
A9-B4-C13-D20
A13-B4-C13-D20
A24-B4-C13-D20
A69-B4-C13-D20
A67-B4-C13-D20
A39-B4-C13-D20
A65-B4-C13-D20
A66-B4-C13-D20
A2-B5-C13-D20
A3-B5-C13-D20
A9-B5-C13-D20
A13-B5-C13-D20
A24-B5-C13-D20
A69-B5-C13-D20
A67-B5-C13-D20
A39-B5-C13-D20
A65-B5-C13-D20
A66-B5-C13-D20
A2-B6-C13-D20
A3-B6-C13-D20
A9-B6-C13-D20
A13-B6-C13-D20
A24-B6-C13-D20
A69-B6-C13-D20
A67-B6-C13-D20
A39-B6-C13-D20
A65-B6-C13-D20
A66-B6-C13-D20
A2-B32-C13-D20
A3-B32-C13-D20
A9-B32-C13-D20
A13-B32-C13-D20
A24-B32-C13-D20
A69-B32-C13-D20
A67-B32-C13-D20
A39-B32-C13-D20
A65-B32-C13-D20
A66-B32-C13-D20
A2-B39-C13-D20
A3-B39-C13-D20
A9-B39-C13-D20
A13-B39-C13-D20
A24-B39-C13-D20
A69-B39-C13-D20
A67-B39-C13-D20
A39-B39-C13-D20
A65-B39-C13-D20
A66-B39-C13-D20
A2-B45-C13-D20
A3-B45-C13-D20
A9-B45-C13-D20
A13-B45-C13-D20
A24-B45-C13-D20

-continued
A69-B45-C13-D20
A67-B45-C13-D20
A39-B45-C13-D20
A65-B45-C13-D20
A66-B45-C13-D20
A2-B53-C13-D20
A3-B53-C13-D20
A9-B53-C13-D20
A13-B53-C13-D20
A24-B53-C13-D20
A69-B53-C13-D20
A67-B53-C13-D20
A39-B53-C13-D20
A65-B53-C13-D20
A66-B53-C13-D20
A2-B79-C13-D20
A3-B79-C13-D20
A9-B79-C13-D20
A13-B79-C13-D20
A24-B79-C13-D20
A69-B79-C13-D20
A67-B79-C13-D20
A39-B79-C13-D20
A65-B79-C13-D20
A66-B79-C13-D20
A2-B80-C13-D20
A3-B80-C13-D20
A9-B80-C13-D20
A13-B80-C13-D20
A24-B80-C13-D20
A69-B80-C13-D20
A67-B80-C13-D20
A39-B80-C13-D20
A65-B80-C13-D20
A66-B80-C13-D20
A2-B85-C13-D20
A3-B85-C13-D20
A9-B85-C13-D20
A13-B85-C13-D20
A24-B85-C13-D20
A69-B85-C13-D20
A67-B85-C13-D20
A39-B85-C13-D20
A65-B85-C13-D20
A66-B85-C13-D20
A2-B86-C13-D20
A3-B86-C13-D20
A9-B86-C13-D20
A13-B86-C13-D20
A24-B86-C13-D20
A69-B86-C13-D20
A67-B86-C13-D20
A39-B86-C13-D20
A65-B86-C13-D20
A66-B86-C13-D20
A2-B87-C13-D20
A3-B87-C13-D20
A9-B87-C13-D20
A13-B87-C13-D20
A24-B87-C13-D20
A69-B87-C13-D20
A67-B87-C13-D20
A39-B87-C13-D20
A65-B87-C13-D20
A66-B87-C13-D20
A2-B89-C13-D20
A3-B89-C13-D20
A9-B89-C13-D20
A13-B89-C13-D20
A24-B89-C13-D20
A69-B89-C13-D20
A67-B89-C13-D20
A39-B89-C13-D20
A65-B89-C13-D20
A66-B89-C13-D20
A2-B92-C13-D20
A3-B92-C13-D20
A9-B92-C13-D20
A13-B92-C13-D20
A24-B92-C13-D20

-continued
A69-B92-C13-D20
A67-B92-C13-D20
A39-B92-C13-D20
A65-B92-C13-D20
A66-B92-C13-D20
A2-B4-C1-D21
A3-B4-C1-D21
A9-B4-C1-D21
A13-B4-C1-D21
A24-B4-C1-D21
A69-B4-C1-D21
A67-B4-C1-D21
A39-B4-C1-D21
A65-B4-C1-D21
A66-B4-C1-D21
A2-B5-C1-D21
A3-B5-C1-D21
A9-B5-C1-D21
A13-B5-C1-D21
A24-B5-C1-D21
A69-B5-C1-D21
A67-B5-C1-D21
A39-B5-C1-D21
A65-B5-C1-D21
A66-B5-C1-D21
A2-B6-C1-D21
A3-B6-C1-D21
A9-B6-C1-D21
A13-B6-C1-D21
A24-B6-C1-D21
A69-B6-C1-D21
A67-B6-C1-D21
A39-B6-C1-D21
A65-B6-C1-D21
A66-B6-C1-D21
A2-B32-C1-D21
A3-B32-C1-D21
A9-B32-C1-D21
A13-B32-C1-D21
A24-B32-C1-D21
A69-B32-C1-D21
A67-B32-C1-D21
A39-B32-C1-D21
A65-B32-C1-D21
A66-B32-C1-D21
A2-B39-C1-D21
A3-B39-C1-D21
A9-B39-C1-D21
A13-B39-C1-D21
A24-B39-C1-D21
A69-B39-C1-D21
A67-B39-C1-D21
A39-B39-C1-D21
A65-B39-C1-D21
A66-B39-C1-D21
A2-B45-C1-D21
A3-B45-C1-D21
A9-B45-C1-D21
A13-B45-C1-D21
A24-B45-C1-D21
A69-B45-C1-D21
A67-B45-C1-D21
A39-B45-C1-D21
A65-B45-C1-D21
A66-B45-C1-D21
A2-B53-C1-D21
A3-B53-C1-D21
A9-B53-C1-D21
A13-B53-C1-D21
A24-B53-C1-D21
A69-B53-C1-D21
A67-B53-C1-D21
A39-B53-C1-D21
A65-B53-C1-D21
A66-B53-C1-D21
A2-B79-C1-D21
A3-B79-C1-D21
A9-B79-C1-D21
A13-B79-C1-D21
A24-B79-C1-D21

-continued
A69-B79-C1-D21
A67-B79-C1-D21
A39-B79-C1-D21
A65-B79-C1-D21
A66-B79-C1-D21
A2-B80-C1-D21
A3-B80-C1-D21
A9-B80-C1-D21
A13-B80-C1-D21
A24-B80-C1-D21
A69-B80-C1-D21
A67-B80-C1-D21
A39-B80-C1-D21
A65-B80-C1-D21
A66-B80-C1-D21
A2-B85-C1-D21
A3-B85-C1-D21
A9-B85-C1-D21
A13-B85-C1-D21
A24-B85-C1-D21
A69-B85-C1-D21
A67-B85-C1-D21
A39-B85-C1-D21
A65-B85-C1-D21
A66-B85-C1-D21
A2-B86-C1-D21
A3-B86-C1-D21
A9-B86-C1-D21
A13-B86-C1-D21
A24-B86-C1-D21
A69-B86-C1-D21
A67-B86-C1-D21
A39-B86-C1-D21
A65-B86-C1-D21
A66-B86-C1-D21
A2-B87-C1-D21
A3-B87-C1-D21
A9-B87-C1-D21
A13-B87-C1-D21
A24-B87-C1-D21
A69-B87-C1-D21
A67-B87-C1-D21
A39-B87-C1-D21
A65-B87-C1-D21
A66-B87-C1-D21
A2-B89-C1-D21
A3-B89-C1-D21
A9-B89-C1-D21
A13-B89-C1-D21
A24-B89-C1-D21
A69-B89-C1-D21
A67-B89-C1-D21
A39-B89-C1-D21
A65-B89-C1-D21
A66-B89-C1-D21
A2-B92-C1-D21
A3-B92-C1-D21
A9-B92-C1-D21
A13-B92-C1-D21
A24-B92-C1-D21
A69-B92-C1-D21
A67-B92-C1-D21
A39-B92-C1-D21
A65-B92-C1-D21
A66-B92-C1-D21
A2-B4-C2-D21
A3-B4-C2-D21
A9-B4-C2-D21
A13-B4-C2-D21
A24-B4-C2-D21
A69-B4-C2-D21
A67-B4-C2-D21
A39-B4-C2-D21
A65-B4-C2-D21
A66-B4-C2-D21
A2-B5-C2-D21
A3-B5-C2-D21
A9-B5-C2-D21
A13-B5-C2-D21
A24-B5-C2-D21

-continued
A69-B5-C2-D21
A67-B5-C2-D21
A39-B5-C2-D21
A65-B5-C2-D21
A66-B5-C2-D21
A2-B6-C2-D21
A3-B6-C2-D21
A9-B6-C2-D21
A13-B6-C2-D21
A24-B6-C2-D21
A69-B6-C2-D21
A67-B6-C2-D21
A39-B6-C2-D21
A65-B6-C2-D21
A66-B6-C2-D21
A2-B32-C2-D21
A3-B32-C2-D21
A9-B32-C2-D21
A13-B32-C2-D21
A24-B32-C2-D21
A69-B32-C2-D21
A67-B32-C2-D21
A39-B32-C2-D21
A65-B32-C2-D21
A66-B32-C2-D21
A2-B39-C2-D21
A3-B39-C2-D21
A9-B39-C2-D21
A13-B39-C2-D21
A24-B39-C2-D21
A69-B39-C2-D21
A67-B39-C2-D21
A39-B39-C2-D21
A65-B39-C2-D21
A66-B39-C2-D21
A2-B45-C2-D21
A3-B45-C2-D21
A9-B45-C2-D21
A13-B45-C2-D21
A24-B45-C2-D21
A69-B45-C2-D21
A67-B45-C2-D21
A39-B45-C2-D21
A65-B45-C2-D21
A66-B45-C2-D21
A2-B53-C2-D21
A3-B53-C2-D21
A9-B53-C2-D21
A13-B53-C2-D21
A24-B53-C2-D21
A69-B53-C2-D21
A67-B53-C2-D21
A39-B53-C2-D21
A65-B53-C2-D21
A66-B53-C2-D21
A2-B79-C2-D21
A3-B79-C2-D21
A9-B79-C2-D21
A13-B79-C2-D21
A24-B79-C2-D21
A69-B79-C2-D21
A67-B79-C2-D21
A39-B79-C2-D21
A65-B79-C2-D21
A66-B79-C2-D21
A2-B80-C2-D21
A3-B80-C2-D21
A9-B80-C2-D21
A13-B80-C2-D21
A24-B80-C2-D21
A69-B80-C2-D21
A67-B80-C2-D21
A39-B80-C2-D21
A65-B80-C2-D21
A66-B80-C2-D21
A2-B85-C2-D21
A3-B85-C2-D21
A9-B85-C2-D21
A13-B85-C2-D21
A24-B85-C2-D21

-continued
A69-B85-C2-D21
A67-B85-C2-D21
A39-B85-C2-D21
A65-B85-C2-D21
A66-B85-C2-D21
A2-B86-C2-D21
A3-B86-C2-D21
A9-B86-C2-D21
A13-B86-C2-D21
A24-B86-C2-D21
A69-B86-C2-D21
A67-B86-C2-D21
A39-B86-C2-D21
A65-B86-C2-D21
A66-B86-C2-D21
A2-B87-C2-D21
A3-B87-C2-D21
A9-B87-C2-D21
A13-B87-C2-D21
A24-B87-C2-D21
A69-B87-C2-D21
A67-B87-C2-D21
A39-B87-C2-D21
A65-B87-C2-D21
A66-B87-C2-D21
A2-B89-C2-D21
A3-B89-C2-D21
A9-B89-C2-D21
A13-B89-C2-D21
A24-B89-C2-D21
A69-B89-C2-D21
A67-B89-C2-D21
A39-B89-C2-D21
A65-B89-C2-D21
A66-B89-C2-D21
A2-B92-C2-D21
A3-B92-C2-D21
A9-B92-C2-D21
A13-B92-C2-D21
A24-B92-C2-D21
A69-B92-C2-D21
A67-B92-C2-D21
A39-B92-C2-D21
A65-B92-C2-D21
A66-B92-C2-D21
A2-B4-C3-D21
A3-B4-C3-D21
A9-B4-C3-D21
A13-B4-C3-D21
A24-B4-C3-D21
A69-B4-C3-D21
A67-B4-C3-D21
A39-B4-C3-D21
A65-B4-C3-D21
A66-B4-C3-D21
A2-B5-C3-D21
A3-B5-C3-D21
A9-B5-C3-D21
A13-B5-C3-D21
A24-B5-C3-D21
A69-B5-C3-D21
A67-B5-C3-D21
A39-B5-C3-D21
A65-B5-C3-D21
A66-B5-C3-D21
A2-B6-C3-D21
A3-B6-C3-D21
A9-B6-C3-D21
A13-B6-C3-D21
A24-B6-C3-D21
A69-B6-C3-D21
A67-B6-C3-D21
A39-B6-C3-D21
A65-B6-C3-D21
A66-B6-C3-D21
A2-B32-C3-D21
A3-B32-C3-D21
A9-B32-C3-D21
A13-B32-C3-D21
A24-B32-C3-D21

-continued

A69-B32-C3-D21
A67-B32-C3-D21
A39-B32-C3-D21
A65-B32-C3-D21
A66-B32-C3-D21
A2-B39-C3-D21
A3-B39-C3-D21
A9-B39-C3-D21
A13-B39-C3-D21
A24-B39-C3-D21
A69-B39-C3-D21
A67-B39-C3-D21
A39-B39-C3-D21
A65-B39-C3-D21
A66-B39-C3-D21
A2-B45-C3-D21
A3-B45-C3-D21
A9-B45-C3-D21
A13-B45-C3-D21
A24-B45-C3-D21
A69-B45-C3-D21
A67-B45-C3-D21
A39-B45-C3-D21
A65-B45-C3-D21
A66-B45-C3-D21
A2-B53-C3-D21
A3-B53-C3-D21
A9-B53-C3-D21
A13-B53-C3-D21
A24-B53-C3-D21
A69-B53-C3-D21
A67-B53-C3-D21
A39-B53-C3-D21
A65-B53-C3-D21
A66-B53-C3-D21
A2-B79-C3-D21
A3-B79-C3-D21
A9-B79-C3-D21
A13-B79-C3-D21
A24-B79-C3-D21
A69-B79-C3-D21
A67-B79-C3-D21
A39-B79-C3-D21
A65-B79-C3-D21
A66-B79-C3-D21
A2-B80-C3-D21
A3-B80-C3-D21
A9-B80-C3-D21
A13-B80-C3-D21
A24-B80-C3-D21
A69-B80-C3-D21
A67-B80-C3-D21
A39-B80-C3-D21
A65-B80-C3-D21
A66-B80-C3-D21
A2-B85-C3-D21
A3-B85-C3-D21
A9-B85-C3-D21
A13-B85-C3-D21
A24-B85-C3-D21
A69-B85-C3-D21
A67-B85-C3-D21
A39-B85-C3-D21
A65-B85-C3-D21
A66-B85-C3-D21
A2-B86-C3-D21
A3-B86-C3-D21
A9-B86-C3-D21
A13-B86-C3-D21
A24-B86-C3-D21
A69-B86-C3-D21
A67-B86-C3-D21
A39-B86-C3-D21
A65-B86-C3-D21
A66-B86-C3-D21
A2-B87-C3-D21
A3-B87-C3-D21
A9-B87-C3-D21
A13-B87-C3-D21
A24-B87-C3-D21

-continued

A69-B87-C3-D21
A67-B87-C3-D21
A39-B87-C3-D21
A65-B87-C3-D21
A66-B87-C3-D21
A2-B89-C3-D21
A3-B89-C3-D21
A9-B89-C3-D21
A13-B89-C3-D21
A24-B89-C3-D21
A69-B89-C3-D21
A67-B89-C3-D21
A39-B89-C3-D21
A65-B89-C3-D21
A66-B89-C3-D21
A2-B92-C3-D21
A3-B92-C3-D21
A9-B92-C3-D21
A13-B92-C3-D21
A24-B92-C3-D21
A69-B92-C3-D21
A67-B92-C3-D21
A39-B92-C3-D21
A65-B92-C3-D21
A66-B92-C3-D21
A2-B4-C4-D21
A3-B4-C4-D21
A9-B4-C4-D21
A13-B4-C4-D21
A24-B4-C4-D21
A69-B4-C4-D21
A67-B4-C4-D21
A39-B4-C4-D21
A65-B4-C4-D21
A66-B4-C4-D21
A2-B5-C4-D21
A3-B5-C4-D21
A9-B5-C4-D21
A13-B5-C4-D21
A24-B5-C4-D21
A69-B5-C4-D21
A67-B5-C4-D21
A39-B5-C4-D21
A65-B5-C4-D21
A66-B5-C4-D21
A2-B6-C4-D21
A3-B6-C4-D21
A9-B6-C4-D21
A13-B6-C4-D21
A24-B6-C4-D21
A69-B6-C4-D21
A67-B6-C4-D21
A39-B6-C4-D21
A65-B6-C4-D21
A66-B6-C4-D21
A2-B32-C4-D21
A3-B32-C4-D21
A9-B32-C4-D21
A13-B32-C4-D21
A24-B32-C4-D21
A69-B32-C4-D21
A67-B32-C4-D21
A39-B32-C4-D21
A65-B32-C4-D21
A66-B32-C4-D21
A2-B39-C4-D21
A3-B39-C4-D21
A9-B39-C4-D21
A13-B39-C4-D21
A24-B39-C4-D21
A69-B39-C4-D21
A67-B39-C4-D21
A39-B39-C4-D21
A65-B39-C4-D21
A66-B39-C4-D21
A2-B45-C4-D21
A3-B45-C4-D21
A9-B45-C4-D21
A13-B45-C4-D21
A24-B45-C4-D21

-continued
A69-B45-C4-D21
A67-B45-C4-D21
A39-B45-C4-D21
A65-B45-C4-D21
A66-B45-C4-D21
A2-B53-C4-D21
A3-B53-C4-D21
A9-B53-C4-D21
A13-B53-C4-D21
A24-B53-C4-D21
A69-B53-C4-D21
A67-B53-C4-D21
A39-B53-C4-D21
A65-B53-C4-D21
A66-B53-C4-D21
A2-B79-C4-D21
A3-B79-C4-D21
A9-B79-C4-D21
A13-B79-C4-D21
A24-B79-C4-D21
A69-B79-C4-D21
A67-B79-C4-D21
A39-B79-C4-D21
A65-B79-C4-D21
A66-B79-C4-D21
A2-B80-C4-D21
A3-B80-C4-D21
A9-B80-C4-D21
A13-B80-C4-D21
A24-B80-C4-D21
A69-B80-C4-D21
A67-B80-C4-D21
A39-B80-C4-D21
A65-B80-C4-D21
A66-B80-C4-D21
A2-B85-C4-D21
A3-B85-C4-D21
A9-B85-C4-D21
A13-B85-C4-D21
A24-B85-C4-D21
A69-B85-C4-D21
A67-B85-C4-D21
A39-B85-C4-D21
A65-B85-C4-D21
A66-B85-C4-D21
A2-B86-C4-D21
A3-B86-C4-D21
A9-B86-C4-D21
A13-B86-C4-D21
A24-B86-C4-D21
A69-B86-C4-D21
A67-B86-C4-D21
A39-B86-C4-D21
A65-B86-C4-D21
A66-B86-C4-D21
A2-B87-C4-D21
A3-B87-C4-D21
A9-B87-C4-D21
A13-B87-C4-D21
A24-B87-C4-D21
A69-B87-C4-D21
A67-B87-C4-D21
A39-B87-C4-D21
A65-B87-C4-D21
A66-B87-C4-D21
A2-B89-C4-D21
A3-B89-C4-D21
A9-B89-C4-D21
A13-B89-C4-D21
A24-B89-C4-D21
A69-B89-C4-D21
A67-B89-C4-D21
A39-B89-C4-D21
A65-B89-C4-D21
A66-B89-C4-D21
A2-B92-C4-D21
A3-B92-C4-D21
A9-B92-C4-D21
A13-B92-C4-D21
A24-B92-C4-D21

-continued
A69-B92-C4-D21
A67-B92-C4-D21
A39-B92-C4-D21
A65-B92-C4-D21
A66-B92-C4-D21
A2-B4-C5-D21
A3-B4-C5-D21
A9-B4-C5-D21
A13-B4-C5-D21
A24-B4-C5-D21
A69-B4-C5-D21
A67-B4-C5-D21
A39-B4-C5-D21
A65-B4-C5-D21
A66-B4-C5-D21
A2-B5-C5-D21
A3-B5-C5-D21
A9-B5-C5-D21
A13-B5-C5-D21
A24-B5-C5-D21
A69-B5-C5-D21
A67-B5-C5-D21
A39-B5-C5-D21
A65-B5-C5-D21
A66-B5-C5-D21
A2-B6-C5-D21
A3-B6-C5-D21
A9-B6-C5-D21
A13-B6-C5-D21
A24-B6-C5-D21
A69-B6-C5-D21
A67-B6-C5-D21
A39-B6-C5-D21
A65-B6-C5-D21
A66-B6-C5-D21
A2-B32-C5-D21
A3-B32-C5-D21
A9-B32-C5-D21
A13-B32-C5-D21
A24-B32-C5-D21
A69-B32-C5-D21
A67-B32-C5-D21
A39-B32-C5-D21
A65-B32-C5-D21
A66-B32-C5-D21
A2-B39-C5-D21
A3-B39-C5-D21
A9-B39-C5-D21
A13-B39-C5-D21
A24-B39-C5-D21
A69-B39-C5-D21
A67-B39-C5-D21
A39-B39-C5-D21
A65-B39-C5-D21
A66-B39-C5-D21
A2-B45-C5-D21
A3-B45-C5-D21
A9-B45-C5-D21
A13-B45-C5-D21
A24-B45-C5-D21
A69-B45-C5-D21
A67-B45-C5-D21
A39-B45-C5-D21
A65-B45-C5-D21
A66-B45-C5-D21
A2-B53-C5-D21
A3-B53-C5-D21
A9-B53-C5-D21
A13-B53-C5-D21
A24-B53-C5-D21
A69-B53-C5-D21
A67-B53-C5-D21
A39-B53-C5-D21
A65-B53-C5-D21
A66-B53-C5-D21
A2-B79-C5-D21
A3-B79-C5-D21
A9-B79-C5-D21
A13-B79-C5-D21
A24-B79-C5-D21

-continued
A69-B79-C5-D21
A67-B79-C5-D21
A39-B79-C5-D21
A65-B79-C5-D21
A66-B79-C5-D21
A2-B80-C5-D21
A3-B80-C5-D21
A9-B80-C5-D21
A13-B80-C5-D21
A24-B80-C5-D21
A69-B80-C5-D21
A67-B80-C5-D21
A39-B80-C5-D21
A65-B80-C5-D21
A66-B80-C5-D21
A2-B85-C5-D21
A3-B85-C5-D21
A9-B85-C5-D21
A13-B85-C5-D21
A24-B85-C5-D21
A69-B85-C5-D21
A67-B85-C5-D21
A39-B85-C5-D21
A65-B85-C5-D21
A66-B85-C5-D21
A2-B86-C5-D21
A3-B86-C5-D21
A9-B86-C5-D21
A13-B86-C5-D21
A24-B86-C5-D21
A69-B86-C5-D21
A67-B86-C5-D21
A39-B86-C5-D21
A65-B86-C5-D21
A66-B86-C5-D21
A2-B87-C5-D21
A3-B87-C5-D21
A9-B87-C5-D21
A13-B87-C5-D21
A24-B87-C5-D21
A69-B87-C5-D21
A67-B87-C5-D21
A39-B87-C5-D21
A65-B87-C5-D21
A66-B87-C5-D21
A2-B89-C5-D21
A3-B89-C5-D21
A9-B89-C5-D21
A13-B89-C5-D21
A24-B89-C5-D21
A69-B89-C5-D21
A67-B89-C5-D21
A39-B89-C5-D21
A65-B89-C5-D21
A66-B89-C5-D21
A2-B92-C5-D21
A3-B92-C5-D21
A9-B92-C5-D21
A13-B92-C5-D21
A24-B92-C5-D21
A69-B92-C5-D21
A67-B92-C5-D21
A39-B92-C5-D21
A65-B92-C5-D21
A66-B92-C5-D21
A2-B4-C6-D21
A3-B4-C6-D21
A9-B4-C6-D21
A13-B4-C6-D21
A24-B4-C6-D21
A69-B4-C6-D21
A67-B4-C6-D21
A39-B4-C6-D21
A65-B4-C6-D21
A66-B4-C6-D21
A2-B5-C6-D21
A3-B5-C6-D21
A9-B5-C6-D21
A13-B5-C6-D21
A24-B5-C6-D21

-continued
A69-B5-C6-D21
A67-B5-C6-D21
A39-B5-C6-D21
A65-B5-C6-D21
A66-B5-C6-D21
A2-B6-C6-D21
A3-B6-C6-D21
A9-B6-C6-D21
A13-B6-C6-D21
A24-B6-C6-D21
A69-B6-C6-D21
A67-B6-C6-D21
A39-B6-C6-D21
A65-B6-C6-D21
A66-B6-C6-D21
A2-B32-C6-D21
A3-B32-C6-D21
A9-B32-C6-D21
A13-B32-C6-D21
A24-B32-C6-D21
A69-B32-C6-D21
A67-B32-C6-D21
A39-B32-C6-D21
A65-B32-C6-D21
A66-B32-C6-D21
A2-B39-C6-D21
A3-B39-C6-D21
A9-B39-C6-D21
A13-B39-C6-D21
A24-B39-C6-D21
A69-B39-C6-D21
A67-B39-C6-D21
A39-B39-C6-D21
A65-B39-C6-D21
A66-B39-C6-D21
A2-B45-C6-D21
A3-B45-C6-D21
A9-B45-C6-D21
A13-B45-C6-D21
A24-B45-C6-D21
A69-B45-C6-D21
A67-B45-C6-D21
A39-B45-C6-D21
A65-B45-C6-D21
A66-B45-C6-D21
A2-B53-C6-D21
A3-B53-C6-D21
A9-B53-C6-D21
A13-B53-C6-D21
A24-B53-C6-D21
A69-B53-C6-D21
A67-B53-C6-D21
A39-B53-C6-D21
A65-B53-C6-D21
A66-B53-C6-D21
A2-B79-C6-D21
A3-B79-C6-D21
A9-B79-C6-D21
A13-B79-C6-D21
A24-B79-C6-D21
A69-B79-C6-D21
A67-B79-C6-D21
A39-B79-C6-D21
A65-B79-C6-D21
A66-B79-C6-D21
A2-B80-C6-D21
A3-B80-C6-D21
A9-B80-C6-D21
A13-B80-C6-D21
A24-B80-C6-D21
A69-B80-C6-D21
A67-B80-C6-D21
A39-B80-C6-D21
A65-B80-C6-D21
A66-B80-C6-D21
A2-B85-C6-D21
A3-B85-C6-D21
A9-B85-C6-D21
A13-B85-C6-D21
A24-B85-C6-D21

-continued

A69-B85-C6-D21
A67-B85-C6-D21
A39-B85-C6-D21
A65-B85-C6-D21
A66-B85-C6-D21
A2-B86-C6-D21
A3-B86-C6-D21
A9-B86-C6-D21
A13-B86-C6-D21
A24-B86-C6-D21
A69-B86-C6-D21
A67-B86-C6-D21
A39-B86-C6-D21
A65-B86-C6-D21
A66-B86-C6-D21
A2-B87-C6-D21
A3-B87-C6-D21
A9-B87-C6-D21
A13-B87-C6-D21
A24-B87-C6-D21
A69-B87-C6-D21
A67-B87-C6-D21
A39-B87-C6-D21
A65-B87-C6-D21
A66-B87-C6-D21
A2-B89-C6-D21
A3-B89-C6-D21
A9-B89-C6-D21
A13-B89-C6-D21
A24-B89-C6-D21
A69-B89-C6-D21
A67-B89-C6-D21
A39-B89-C6-D21
A65-B89-C6-D21
A66-B89-C6-D21
A2-B92-C6-D21
A3-B92-C6-D21
A9-B92-C6-D21
A13-B92-C6-D21
A24-B92-C6-D21
A69-B92-C6-D21
A67-B92-C6-D21
A39-B92-C6-D21
A65-B92-C6-D21
A66-B92-C6-D21
A2-B4-C7-D21
A3-B4-C7-D21
A9-B4-C7-D21
A13-B4-C7-D21
A24-B4-C7-D21
A69-B4-C7-D21
A67-B4-C7-D21
A39-B4-C7-D21
A65-B4-C7-D21
A66-B4-C7-D21
A2-B5-C7-D21
A3-B5-C7-D21
A9-B5-C7-D21
A13-B5-C7-D21
A24-B5-C7-D21
A69-B5-C7-D21
A67-B5-C7-D21
A39-B5-C7-D21
A65-B5-C7-D21
A66-B5-C7-D21
A2-B6-C7-D21
A3-B6-C7-D21
A9-B6-C7-D21
A13-B6-C7-D21
A24-B6-C7-D21
A69-B6-C7-D21
A67-B6-C7-D21
A39-B6-C7-D21
A65-B6-C7-D21
A66-B6-C7-D21
A2-B32-C7-D21

-continued

A3-B32-C7-D21
A9-B32-C7-D21
A13-B32-C7-D21
A24-B32-C7-D21
A69-B32-C7-D21
A67-B32-C7-D21
A39-B32-C7-D21
A65-B32-C7-D21
A66-B32-C7-D21
A2-B39-C7-D21
A3-B39-C7-D21
A9-B39-C7-D21
A13-B39-C7-D21
A24-B39-C7-D21
A69-B39-C7-D21
A67-B39-C7-D21
A39-B39-C7-D21
A65-B39-C7-D21
A66-B39-C7-D21
A2-B45-C7-D21
A3-B45-C7-D21
A9-B45-C7-D21
A13-B45-C7-D21
A24-B45-C7-D21
A69-B45-C7-D21
A67-B45-C7-D21
A39-B45-C7-D21
A65-B45-C7-D21
A66-B45-C7-D21
A2-B53-C7-D21
A3-B53-C7-D21
A9-B53-C7-D21
A13-B53-C7-D21
A24-B53-C7-D21
A69-B53-C7-D21
A67-B53-C7-D21
A39-B53-C7-D21
A65-B53-C7-D21
A66-B53-C7-D21
A2-B79-C7-D21
A3-B79-C7-D21
A9-B79-C7-D21
A13-B79-C7-D21
A24-B79-C7-D21
A69-B79-C7-D21
A67-B79-C7-D21
A39-B79-C7-D21
A65-B79-C7-D21
A66-B79-C7-D21
A2-B80-C7-D21
A3-B80-C7-D21
A9-B80-C7-D21
A13-B80-C7-D21
A24-B80-C7-D21
A69-B80-C7-D21
A67-B80-C7-D21
A39-B80-C7-D21
A65-B80-C7-D21
A66-B80-C7-D21
A2-B85-C7-D21
A3-B85-C7-D21
A9-B85-C7-D21
A13-B85-C7-D21
A24-B85-C7-D21
A69-B85-C7-D21
A67-B85-C7-D21
A39-B85-C7-D21
A65-B85-C7-D21
A66-B85-C7-D21
A2-B86-C7-D21
A3-B86-C7-D21
A9-B86-C7-D21
A13-B86-C7-D21
A24-B86-C7-D21
A69-B86-C7-D21
A67-B86-C7-D21
A39-B86-C7-D21
A65-B86-C7-D21
A66-B86-C7-D21
A2-B87-C7-D21

-continued
A3-B87-C7-D21
A9-B87-C7-D21
A13-B87-C7-D21
A24-B87-C7-D21
A69-B87-C7-D21
A67-B87-C7-D21
A39-B87-C7-D21
A65-B87-C7-D21
A66-B87-C7-D21
A2-B89-C7-D21
A3-B89-C7-D21
A9-B89-C7-D21
A13-B89-C7-D21
A24-B89-C7-D21
A69-B89-C7-D21
A67-B89-C7-D21
A39-B89-C7-D21
A65-B89-C7-D21
A66-B89-C7-D21
A2-B92-C7-D21
A3-B92-C7-D21
A9-B92-C7-D21
A13-B92-C7-D21
A24-B92-C7-D21
A69-B92-C7-D21
A67-B92-C7-D21
A39-B92-C7-D21
A65-B92-C7-D21
A66-B92-C7-D21
A2-B4-C8-D21
A3-B4-C8-D21
A9-B4-C8-D21
A13-B4-C8-D21
A24-B4-C8-D21
A69-B4-C8-D21
A67-B4-C8-D21
A39-B4-C8-D21
A65-B4-C8-D21
A66-B4-C8-D21
A2-B5-C8-D21
A3-B5-C8-D21
A9-B5-C8-D21
A13-B5-C8-D21
A24-B5-C8-D21
A69-B5-C8-D21
A67-B5-C8-D21
A39-B5-C8-D21
A65-B5-C8-D21
A66-B5-C8-D21
A2-B6-C8-D21
A3-B6-C8-D21
A9-B6-C8-D21
A13-B6-C8-D21
A24-B6-C8-D21
A69-B6-C8-D21
A67-B6-C8-D21
A39-B6-C8-D21
A65-B6-C8-D21
A66-B6-C8-D21
A2-B32-C8-D21
A3-B32-C8-D21
A9-B32-C8-D21
A13-B32-C8-D21
A24-B32-C8-D21
A69-B32-C8-D21
A67-B32-C8-D21
A39-B32-C8-D21
A65-B32-C8-D21
A66-B32-C8-D21
A2-B39-C8-D21
A3-B39-C8-D21
A9-B39-C8-D21
A13-B39-C8-D21
A24-B39-C8-D21
A69-B39-C8-D21
A67-B39-C8-D21
A39-B39-C8-D21
A65-B39-C8-D21
A66-B39-C8-D21
A2-B45-C8-D21

-continued
A3-B45-C8-D21
A9-B45-C8-D21
A13-B45-C8-D21
A24-B45-C8-D21
A69-B45-C8-D21
A67-B45-C8-D21
A39-B45-C8-D21
A65-B45-C8-D21
A66-B45-C8-D21
A2-B53-C8-D21
A3-B53-C8-D21
A9-B53-C8-D21
A13-B53-C8-D21
A24-B53-C8-D21
A69-B53-C8-D21
A67-B53-C8-D21
A39-B53-C8-D21
A65-B53-C8-D21
A66-B53-C8-D21
A2-B79-C8-D21
A3-B79-C8-D21
A9-B79-C8-D21
A13-B79-C8-D21
A24-B79-C8-D21
A69-B79-C8-D21
A67-B79-C8-D21
A39-B79-C8-D21
A65-B79-C8-D21
A66-B79-C8-D21
A2-B80-C8-D21
A3-B80-C8-D21
A9-B80-C8-D21
A13-B80-C8-D21
A24-B80-C8-D21
A69-B80-C8-D21
A67-B80-C8-D21
A39-B80-C8-D21
A65-B80-C8-D21
A66-B80-C8-D21
A2-B85-C8-D21
A3-B85-C8-D21
A9-B85-C8-D21
A13-B85-C8-D21
A24-B85-C8-D21
A69-B85-C8-D21
A67-B85-C8-D21
A39-B85-C8-D21
A65-B85-C8-D21
A66-B85-C8-D21
A2-B86-C8-D21
A3-B86-C8-D21
A9-B86-C8-D21
A13-B86-C8-D21
A24-B86-C8-D21
A69-B86-C8-D21
A67-B86-C8-D21
A39-B86-C8-D21
A65-B86-C8-D21
A66-B86-C8-D21
A2-B87-C8-D21
A3-B87-C8-D21
A9-B87-C8-D21
A13-B87-C8-D21
A24-B87-C8-D21
A69-B87-C8-D21
A67-B87-C8-D21
A39-B87-C8-D21
A65-B87-C8-D21
A66-B87-C8-D21
A2-B89-C8-D21
A3-B89-C8-D21
A9-B89-C8-D21
A13-B89-C8-D21
A24-B89-C8-D21
A69-B89-C8-D21
A67-B89-C8-D21
A39-B89-C8-D21
A65-B89-C8-D21
A66-B89-C8-D21
A2-B92-C8-D21

-continued
A3-B92-C8-D21
A9-B92-C8-D21
A13-B92-C8-D21
A24-B92-C8-D21
A69-B92-C8-D21
A67-B92-C8-D21
A39-B92-C8-D21
A65-B92-C8-D21
A66-B92-C8-D21
A2-B4-C9-D21
A3-B4-C9-D21
A9-B4-C9-D21
A13-B4-C9-D21
A24-B4-C9-D21
A69-B4-C9-D21
A67-B4-C9-D21
A39-B4-C9-D21
A65-B4-C9-D21
A66-B4-C9-D21
A2-B5-C9-D21
A3-B5-C9-D21
A9-B5-C9-D21
A13-B5-C9-D21
A24-B5-C9-D21
A69-B5-C9-D21
A67-B5-C9-D21
A39-B5-C9-D21
A65-B5-C9-D21
A66-B5-C9-D21
A2-B6-C9-D21
A3-B6-C9-D21
A9-B6-C9-D21
A13-B6-C9-D21
A24-B6-C9-D21
A69-B6-C9-D21
A67-B6-C9-D21
A39-B6-C9-D21
A65-B6-C9-D21
A66-B6-C9-D21
A2-B32-C9-D21
A3-B32-C9-D21
A9-B32-C9-D21
A13-B32-C9-D21
A24-B32-C9-D21
A69-B32-C9-D21
A67-B32-C9-D21
A39-B32-C9-D21
A65-B32-C9-D21
A66-B32-C9-D21
A2-B39-C9-D21
A3-B39-C9-D21
A9-B39-C9-D21
A13-B39-C9-D21
A24-B39-C9-D21
A69-B39-C9-D21
A67-B39-C9-D21
A39-B39-C9-D21
A65-B39-C9-D21
A66-B39-C9-D21
A2-B45-C9-D21
A3-B45-C9-D21
A9-B45-C9-D21
A13-B45-C9-D21
A24-B45-C9-D21
A69-B45-C9-D21
A67-B45-C9-D21
A39-B45-C9-D21
A65-B45-C9-D21
A66-B45-C9-D21
A2-B53-C9-D21
A3-B53-C9-D21
A9-B53-C9-D21
A13-B53-C9-D21
A24-B53-C9-D21
A69-B53-C9-D21
A67-B53-C9-D21
A39-B53-C9-D21
A65-B53-C9-D21
A66-B53-C9-D21
A2-B79-C9-D21

-continued
A3-B79-C9-D21
A9-B79-C9-D21
A13-B79-C9-D21
A24-B79-C9-D21
A69-B79-C9-D21
A67-B79-C9-D21
A39-B79-C9-D21
A65-B79-C9-D21
A66-B79-C9-D21
A2-B80-C9-D21
A3-B80-C9-D21
A9-B80-C9-D21
A13-B80-C9-D21
A24-B80-C9-D21
A69-B80-C9-D21
A67-B80-C9-D21
A39-B80-C9-D21
A65-B80-C9-D21
A66-B80-C9-D21
A2-B85-C9-D21
A3-B85-C9-D21
A9-B85-C9-D21
A13-B85-C9-D21
A24-B85-C9-D21
A69-B85-C9-D21
A67-B85-C9-D21
A39-B85-C9-D21
A65-B85-C9-D21
A66-B85-C9-D21
A2-B86-C9-D21
A3-B86-C9-D21
A9-B86-C9-D21
A13-B86-C9-D21
A24-B86-C9-D21
A69-B86-C9-D21
A67-B86-C9-D21
A39-B86-C9-D21
A65-B86-C9-D21
A66-B86-C9-D21
A2-B87-C9-D21
A3-B87-C9-D21
A9-B87-C9-D21
A13-B87-C9-D21
A24-B87-C9-D21
A69-B87-C9-D21
A67-B87-C9-D21
A39-B87-C9-D21
A65-B87-C9-D21
A66-B87-C9-D21
A2-B89-C9-D21
A3-B89-C9-D21
A9-B89-C9-D21
A13-B89-C9-D21
A24-B89-C9-D21
A69-B89-C9-D21
A67-B89-C9-D21
A39-B89-C9-D21
A65-B89-C9-D21
A66-B89-C9-D21
A2-B92-C9-D21
A3-B92-C9-D21
A9-B92-C9-D21
A13-B92-C9-D21
A24-B92-C9-D21
A69-B92-C9-D21
A67-B92-C9-D21
A39-B92-C9-D21
A65-B92-C9-D21
A66-B92-C9-D21
A2-B4-C10-D21
A3-B4-C10-D21
A9-B4-C10-D21
A13-B4-C10-D21
A24-B4-C10-D21
A69-B4-C10-D21
A67-B4-C10-D21
A39-B4-C10-D21
A65-B4-C10-D21
A66-B4-C10-D21
A2-B5-C10-D21

-continued
A3-B5-C10-D21
A9-B5-C10-D21
A13-B5-C10-D21
A24-B5-C10-D21
A69-B5-C10-D21
A67-B5-C10-D21
A39-B5-C10-D21
A65-B5-C10-D21
A66-B5-C10-D21
A2-B6-C10-D21
A3-B6-C10-D21
A9-B6-C10-D21
A13-B6-C10-D21
A24-B6-C10-D21
A69-B6-C10-D21
A67-B6-C10-D21
A39-B6-C10-D21
A65-B6-C10-D21
A66-B6-C10-D21
A2-B32-C10-D21
A3-B32-C10-D21
A9-B32-C10-D21
A13-B32-C10-D21
A24-B32-C10-D21
A69-B32-C10-D21
A67-B32-C10-D21
A39-B32-C10-D21
A65-B32-C10-D21
A66-B32-C10-D21
A2-B39-C10-D21
A3-B39-C10-D21
A9-B39-C10-D21
A13-B39-C10-D21
A24-B39-C10-D21
A69-B39-C10-D21
A67-B39-C10-D21
A39-B39-C10-D21
A65-B39-C10-D21
A66-B39-C10-D21
A2-B45-C10-D21
A3-B45-C10-D21
A9-B45-C10-D21
A13-B45-C10-D21
A24-B45-C10-D21
A69-B45-C10-D21
A67-B45-C10-D21
A39-B45-C10-D21
A65-B45-C10-D21
A66-B45-C10-D21
A2-B53-C10-D21
A3-B53-C10-D21
A9-B53-C10-D21
A13-B53-C10-D21
A24-B53-C10-D21
A69-B53-C10-D21
A67-B53-C10-D21
A39-B53-C10-D21
A65-B53-C10-D21
A66-B53-C10-D21
A2-B79-C10-D21
A3-B79-C10-D21
A9-B79-C10-D21
A13-B79-C10-D21
A24-B79-C10-D21
A69-B79-C10-D21
A67-B79-C10-D21
A39-B79-C10-D21
A65-B79-C10-D21
A66-B79-C10-D21
A2-B80-C10-D21
A3-B80-C10-D21
A9-B80-C10-D21
A13-B80-C10-D21
A24-B80-C10-D21
A69-B80-C10-D21
A67-B80-C10-D21
A39-B80-C10-D21
A65-B80-C10-D21
A66-B80-C10-D21
A2-B85-C10-D21

-continued
A3-B85-C10-D21
A9-B85-C10-D21
A13-B85-C10-D21
A24-B85-C10-D21
A69-B85-C10-D21
A67-B85-C10-D21
A39-B85-C10-D21
A65-B85-C10-D21
A66-B85-C10-D21
A2-B86-C10-D21
A3-B86-C10-D21
A9-B86-C10-D21
A13-B86-C10-D21
A24-B86-C10-D21
A69-B86-C10-D21
A67-B86-C10-D21
A39-B86-C10-D21
A65-B86-C10-D21
A66-B86-C10-D21
A2-B87-C10-D21
A3-B87-C10-D21
A9-B87-C10-D21
A13-B87-C10-D21
A24-B87-C10-D21
A69-B87-C10-D21
A67-B87-C10-D21
A39-B87-C10-D21
A65-B87-C10-D21
A66-B87-C10-D21
A2-B89-C10-D21
A3-B89-C10-D21
A9-B89-C10-D21
A13-B89-C10-D21
A24-B89-C10-D21
A69-B89-C10-D21
A67-B89-C10-D21
A39-B89-C10-D21
A65-B89-C10-D21
A66-B89-C10-D21
A2-B92-C10-D21
A3-B92-C10-D21
A9-B92-C10-D21
A13-B92-C10-D21
A24-B92-C10-D21
A69-B92-C10-D21
A67-B92-C10-D21
A39-B92-C10-D21
A65-B92-C10-D21
A66-B92-C10-D21
A2-B4-C11-D21
A3-B4-C11-D21
A9-B4-C11-D21
A13-B4-C11-D21
A24-B4-C11-D21
A69-B4-C11-D21
A67-B4-C11-D21
A39-B4-C11-D21
A65-B4-C11-D21
A66-B4-C11-D21
A2-B5-C11-D21
A3-B5-C11-D21
A9-B5-C11-D21
A13-B5-C11-D21
A24-B5-C11-D21
A69-B5-C11-D21
A67-B5-C11-D21
A39-B5-C11-D21
A65-B5-C11-D21
A66-B5-C11-D21
A2-B6-C11-D21
A3-B6-C11-D21
A9-B6-C11-D21
A13-B6-C11-D21
A24-B6-C11-D21
A69-B6-C11-D21
A67-B6-C11-D21
A39-B6-C11-D21
A65-B6-C11-D21
A66-B6-C11-D21
A2-B32-C11-D21

-continued
A3-B32-C11-D21
A9-B32-C11-D21
A13-B32-C11-D21
A24-B32-C11-D21
A69-B32-C11-D21
A67-B32-C11-D21
A39-B32-C11-D21
A65-B32-C11-D21
A66-B32-C11-D21
A2-B39-C11-D21
A3-B39-C11-D21
A9-B39-C11-D21
A13-B39-C11-D21
A24-B39-C11-D21
A69-B39-C11-D21
A67-B39-C11-D21
A39-B39-C11-D21
A65-B39-C11-D21
A66-B39-C11-D21
A2-B45-C11-D21
A3-B45-C11-D21
A9-B45-C11-D21
A13-B45-C11-D21
A24-B45-C11-D21
A69-B45-C11-D21
A67-B45-C11-D21
A39-B45-C11-D21
A65-B45-C11-D21
A66-B45-C11-D21
A2-B53-C11-D21
A3-B53-C11-D21
A9-B53-C11-D21
A13-B53-C11-D21
A24-B53-C11-D21
A69-B53-C11-D21
A67-B53-C11-D21
A39-B53-C11-D21
A65-B53-C11-D21
A66-B53-C11-D21
A2-B79-C11-D21
A3-B79-C11-D21
A9-B79-C11-D21
A13-B79-C11-D21
A24-B79-C11-D21
A69-B79-C11-D21
A67-B79-C11-D21
A39-B79-C11-D21
A65-B79-C11-D21
A66-B79-C11-D21
A2-B80-C11-D21
A3-B80-C11-D21
A9-B80-C11-D21
A13-B80-C11-D21
A24-B80-C11-D21
A69-B80-C11-D21
A67-B80-C11-D21
A39-B80-C11-D21
A65-B80-C11-D21
A66-B80-C11-D21
A2-B85-C11-D21
A3-B85-C11-D21
A9-B85-C11-D21
A13-B85-C11-D21
A24-B85-C11-D21
A69-B85-C11-D21
A67-B85-C11-D21
A39-B85-C11-D21
A65-B85-C11-D21
A66-B85-C11-D21
A2-B86-C11-D21
A3-B86-C11-D21
A9-B86-C11-D21
A13-B86-C11-D21
A24-B86-C11-D21
A69-B86-C11-D21
A67-B86-C11-D21
A39-B86-C11-D21
A65-B86-C11-D21
A66-B86-C11-D21
A2-B87-C11-D21

-continued
A3-B87-C11-D21
A9-B87-C11-D21
A13-B87-C11-D21
A24-B87-C11-D21
A69-B87-C11-D21
A67-B87-C11-D21
A39-B87-C11-D21
A65-B87-C11-D21
A66-B87-C11-D21
A2-B89-C11-D21
A3-B89-C11-D21
A9-B89-C11-D21
A13-B89-C11-D21
A24-B89-C11-D21
A69-B89-C11-D21
A67-B89-C11-D21
A39-B89-C11-D21
A65-B89-C11-D21
A66-B89-C11-D21
A2-B92-C11-D21
A3-B92-C11-D21
A9-B92-C11-D21
A13-B92-C11-D21
A24-B92-C11-D21
A69-B92-C11-D21
A67-B92-C11-D21
A39-B92-C11-D21
A65-B92-C11-D21
A66-B92-C11-D21
A2-B4-C12-D21
A3-B4-C12-D21
A9-B4-C12-D21
A13-B4-C12-D21
A24-B4-C12-D21
A69-B4-C12-D21
A67-B4-C12-D21
A39-B4-C12-D21
A65-B4-C12-D21
A66-B4-C12-D21
A2-B5-C12-D21
A3-B5-C12-D21
A9-B5-C12-D21
A13-B5-C12-D21
A24-B5-C12-D21
A69-B5-C12-D21
A67-B5-C12-D21
A39-B5-C12-D21
A65-B5-C12-D21
A66-B5-C12-D21
A2-B6-C12-D21
A3-B6-C12-D21
A9-B6-C12-D21
A13-B6-C12-D21
A24-B6-C12-D21
A69-B6-C12-D21
A67-B6-C12-D21
A39-B6-C12-D21
A65-B6-C12-D21
A66-B6-C12-D21
A2-B32-C12-D21
A3-B32-C12-D21
A9-B32-C12-D21
A13-B32-C12-D21
A24-B32-C12-D21
A69-B32-C12-D21
A67-B32-C12-D21
A39-B32-C12-D21
A65-B32-C12-D21
A66-B32-C12-D21
A2-B39-C12-D21
A3-B39-C12-D21
A9-B39-C12-D21
A13-B39-C12-D21
A24-B39-C12-D21
A69-B39-C12-D21
A67-B39-C12-D21
A39-B39-C12-D21
A65-B39-C12-D21
A66-B39-C12-D21
A2-B45-C12-D21

-continued

A3-B45-C12-D21
A9-B45-C12-D21
A13-B45-C12-D21
A24-B45-C12-D21
A69-B45-C12-D21
A67-B45-C12-D21
A39-B45-C12-D21
A65-B45-C12-D21
A66-B45-C12-D21
A2-B53-C12-D21
A3-B53-C12-D21
A9-B53-C12-D21
A13-B53-C12-D21
A24-B53-C12-D21
A69-B53-C12-D21
A67-B53-C12-D21
A39-B53-C12-D21
A65-B53-C12-D21
A66-B53-C12-D21
A2-B79-C12-D21
A3-B79-C12-D21
A9-B79-C12-D21
A13-B79-C12-D21
A24-B79-C12-D21
A69-B79-C12-D21
A67-B79-C12-D21
A39-B79-C12-D21
A65-B79-C12-D21
A66-B79-C12-D21
A2-B80-C12-D21
A3-B80-C12-D21
A9-B80-C12-D21
A13-B80-C12-D21
A24-B80-C12-D21
A69-B80-C12-D21
A67-B80-C12-D21
A39-B80-C12-D21
A65-B80-C12-D21
A66-B80-C12-D21
A2-B85-C12-D21
A3-B85-C12-D21
A9-B85-C12-D21
A13-B85-C12-D21
A24-B85-C12-D21
A69-B85-C12-D21
A67-B85-C12-D21
A39-B85-C12-D21
A65-B85-C12-D21
A66-B85-C12-D21
A2-B86-C12-D21
A3-B86-C12-D21
A9-B86-C12-D21
A13-B86-C12-D21
A24-B86-C12-D21
A69-B86-C12-D21
A67-B86-C12-D21
A39-B86-C12-D21
A65-B86-C12-D21
A66-B86-C12-D21
A2-B87-C12-D21
A3-B87-C12-D21
A9-B87-C12-D21
A13-B87-C12-D21
A24-B87-C12-D21
A69-B87-C12-D21
A67-B87-C12-D21
A39-B87-C12-D21
A65-B87-C12-D21
A66-B87-C12-D21
A2-B89-C12-D21
A3-B89-C12-D21
A9-B89-C12-D21
A13-B89-C12-D21
A24-B89-C12-D21
A69-B89-C12-D21
A67-B89-C12-D21
A39-B89-C12-D21
A65-B89-C12-D21
A66-B89-C12-D21
A2-B92-C12-D21

-continued

A3-B92-C12-D21
A9-B92-C12-D21
A13-B92-C12-D21
A24-B92-C12-D21
A69-B92-C12-D21
A67-B92-C12-D21
A39-B92-C12-D21
A65-B92-C12-D21
A66-B92-C12-D21
A2-B4-C13-D21
A3-B4-C13-D21
A9-B4-C13-D21
A13-B4-C13-D21
A24-B4-C13-D21
A69-B4-C13-D21
A67-B4-C13-D21
A39-B4-C13-D21
A65-B4-C13-D21
A66-B4-C13-D21
A2-B5-C13-D21
A3-B5-C13-D21
A9-B5-C13-D21
A13-B5-C13-D21
A24-B5-C13-D21
A69-B5-C13-D21
A67-B5-C13-D21
A39-B5-C13-D21
A65-B5-C13-D21
A66-B5-C13-D21
A2-B6-C13-D21
A3-B6-C13-D21
A9-B6-C13-D21
A13-B6-C13-D21
A24-B6-C13-D21
A69-B6-C13-D21
A67-B6-C13-D21
A39-B6-C13-D21
A65-B6-C13-D21
A66-B6-C13-D21
A2-B32-C13-D21
A3-B32-C13-D21
A9-B32-C13-D21
A13-B32-C13-D21
A24-B32-C13-D21
A69-B32-C13-D21
A67-B32-C13-D21
A39-B32-C13-D21
A65-B32-C13-D21
A66-B32-C13-D21
A2-B39-C13-D21
A3-B39-C13-D21
A9-B39-C13-D21
A13-B39-C13-D21
A24-B39-C13-D21
A69-B39-C13-D21
A67-B39-C13-D21
A39-B39-C13-D21
A65-B39-C13-D21
A66-B39-C13-D21
A2-B45-C13-D21
A3-B45-C13-D21
A9-B45-C13-D21
A13-B45-C13-D21
A24-B45-C13-D21
A69-B45-C13-D21
A67-B45-C13-D21
A39-B45-C13-D21
A65-B45-C13-D21
A66-B45-C13-D21
A2-B53-C13-D21
A3-B53-C13-D21
A9-B53-C13-D21
A13-B53-C13-D21
A24-B53-C13-D21
A69-B53-C13-D21
A67-B53-C13-D21
A39-B53-C13-D21
A65-B53-C13-D21
A66-B53-C13-D21
A2-B79-C13-D21

-continued
A3-B79-C13-D21
A9-B79-C13-D21
A13-B79-C13-D21
A24-B79-C13-D21
A69-B79-C13-D21
A67-B79-C13-D21
A39-B79-C13-D21
A65-B79-C13-D21
A66-B79-C13-D21
A2-B80-C13-D21
A3-B80-C13-D21
A9-B80-C13-D21
A13-B80-C13-D21
A24-B80-C13-D21
A69-B80-C13-D21
A67-B80-C13-D21
A39-B80-C13-D21
A65-B80-C13-D21
A66-B80-C13-D21
A2-B85-C13-D21
A3-B85-C13-D21
A9-B85-C13-D21
A13-B85-C13-D21
A24-B85-C13-D21
A69-B85-C13-D21
A67-B85-C13-D21
A39-B85-C13-D21
A65-B85-C13-D21
A66-B85-C13-D21
A2-B86-C13-D21
A3-B86-C13-D21
A9-B86-C13-D21
A13-B86-C13-D21
A24-B86-C13-D21
A69-B86-C13-D21
A67-B86-C13-D21
A39-B86-C13-D21
A65-B86-C13-D21
A66-B86-C13-D21
A2-B87-C13-D21
A3-B87-C13-D21
A9-B87-C13-D21
A13-B87-C13-D21
A24-B87-C13-D21
A69-B87-C13-D21
A67-B87-C13-D21
A39-B87-C13-D21
A65-B87-C13-D21
A66-B87-C13-D21
A2-B89-C13-D21
A3-B89-C13-D21
A9-B89-C13-D21
A13-B89-C13-D21
A24-B89-C13-D21
A69-B89-C13-D21
A67-B89-C13-D21
A39-B89-C13-D21
A65-B89-C13-D21
A66-B89-C13-D21
A2-B92-C13-D21
A3-B92-C13-D21
A9-B92-C13-D21
A13-B92-C13-D21
A24-B92-C13-D21
A69-B92-C13-D21
A67-B92-C13-D21
A39-B92-C13-D21
A65-B92-C13-D21
A66-B92-C13-D21
A2-B4-C1-D22
A3-B4-C1-D22
A9-B4-C1-D22
A13-B4-C1-D22
A24-B4-C1-D22
A69-B4-C1-D22
A67-B4-C1-D22
A39-B4-C1-D22
A65-B4-C1-D22
A66-B4-C1-D22
A2-B5-C1-D22

-continued
A3-B5-C1-D22
A9-B5-C1-D22
A13-B5-C1-D22
A24-B5-C1-D22
A69-B5-C1-D22
A67-B5-C1-D22
A39-B5-C1-D22
A65-B5-C1-D22
A66-B5-C1-D22
A2-B6-C1-D22
A3-B6-C1-D22
A9-B6-C1-D22
A13-B6-C1-D22
A24-B6-C1-D22
A69-B6-C1-D22
A67-B6-C1-D22
A39-B6-C1-D22
A65-B6-C1-D22
A66-B6-C1-D22
A2-B32-C1-D22
A3-B32-C1-D22
A9-B32-C1-D22
A13-B32-C1-D22
A24-B32-C1-D22
A69-B32-C1-D22
A67-B32-C1-D22
A39-B32-C1-D22
A65-B32-C1-D22
A66-B32-C1-D22
A2-B39-C1-D22
A3-B39-C1-D22
A9-B39-C1-D22
A13-B39-C1-D22
A24-B39-C1-D22
A69-B39-C1-D22
A67-B39-C1-D22
A39-B39-C1-D22
A65-B39-C1-D22
A66-B39-C1-D22
A2-B45-C1-D22
A3-B45-C1-D22
A9-B45-C1-D22
A13-B45-C1-D22
A24-B45-C1-D22
A69-B45-C1-D22
A67-B45-C1-D22
A39-B45-C1-D22
A65-B45-C1-D22
A66-B45-C1-D22
A2-B53-C1-D22
A3-B53-C1-D22
A9-B53-C1-D22
A13-B53-C1-D22
A24-B53-C1-D22
A69-B53-C1-D22
A67-B53-C1-D22
A39-B53-C1-D22
A65-B53-C1-D22
A66-B53-C1-D22
A2-B79-C1-D22
A3-B79-C1-D22
A9-B79-C1-D22
A13-B79-C1-D22
A24-B79-C1-D22
A69-B79-C1-D22
A67-B79-C1-D22
A39-B79-C1-D22
A65-B79-C1-D22
A66-B79-C1-D22
A2-B80-C1-D22
A3-B80-C1-D22
A9-B80-C1-D22
A13-B80-C1-D22
A24-B80-C1-D22
A69-B80-C1-D22
A67-B80-C1-D22
A39-B80-C1-D22
A65-B80-C1-D22
A66-B80-C1-D22
A2-B85-C1-D22

-continued
A3-B85-C1-D22
A9-B85-C1-D22
A13-B85-C1-D22
A24-B85-C1-D22
A69-B85-C1-D22
A67-B85-C1-D22
A39-B85-C1-D22
A65-B85-C1-D22
A66-B85-C1-D22
A2-B86-C1-D22
A3-B86-C1-D22
A9-B86-C1-D22
A13-B86-C1-D22
A24-B86-C1-D22
A69-B86-C1-D22
A67-B86-C1-D22
A39-B86-C1-D22
A65-B86-C1-D22
A66-B86-C1-D22
A2-B87-C1-D22
A3-B87-C1-D22
A9-B87-C1-D22
A13-B87-C1-D22
A24-B87-C1-D22
A69-B87-C1-D22
A67-B87-C1-D22
A39-B87-C1-D22
A65-B87-C1-D22
A66-B87-C1-D22
A2-B89-C1-D22
A3-B89-C1-D22
A9-B89-C1-D22
A13-B89-C1-D22
A24-B89-C1-D22
A69-B89-C1-D22
A67-B89-C1-D22
A39-B89-C1-D22
A65-B89-C1-D22
A66-B89-C1-D22
A2-B92-C1-D22
A3-B92-C1-D22
A9-B92-C1-D22
A13-B92-C1-D22
A24-B92-C1-D22
A69-B92-C1-D22
A67-B92-C1-D22
A39-B92-C1-D22
A65-B92-C1-D22
A66-B92-C1-D22
A2-B4-C2-D22
A3-B4-C2-D22
A9-B4-C2-D22
A13-B4-C2-D22
A24-B4-C2-D22
A69-B4-C2-D22
A67-B4-C2-D22
A39-B4-C2-D22
A65-B4-C2-D22
A66-B4-C2-D22
A2-B5-C2-D22
A3-B5-C2-D22
A9-B5-C2-D22
A13-B5-C2-D22
A24-B5-C2-D22
A69-B5-C2-D22
A67-B5-C2-D22
A39-B5-C2-D22
A65-B5-C2-D22
A66-B5-C2-D22
A2-B6-C2-D22
A3-B6-C2-D22
A9-B6-C2-D22
A13-B6-C2-D22
A24-B6-C2-D22
A69-B6-C2-D22
A67-B6-C2-D22
A39-B6-C2-D22
A65-B6-C2-D22
A66-B6-C2-D22
A2-B32-C2-D22

-continued
A3-B32-C2-D22
A9-B32-C2-D22
A13-B32-C2-D22
A24-B32-C2-D22
A69-B32-C2-D22
A67-B32-C2-D22
A39-B32-C2-D22
A65-B32-C2-D22
A66-B32-C2-D22
A2-B39-C2-D22
A3-B39-C2-D22
A9-B39-C2-D22
A13-B39-C2-D22
A24-B39-C2-D22
A69-B39-C2-D22
A67-B39-C2-D22
A39-B39-C2-D22
A65-B39-C2-D22
A66-B39-C2-D22
A2-B45-C2-D22
A3-B45-C2-D22
A9-B45-C2-D22
A13-B45-C2-D22
A24-B45-C2-D22
A69-B45-C2-D22
A67-B45-C2-D22
A39-B45-C2-D22
A65-B45-C2-D22
A66-B45-C2-D22
A2-B53-C2-D22
A3-B53-C2-D22
A9-B53-C2-D22
A13-B53-C2-D22
A24-B53-C2-D22
A69-B53-C2-D22
A67-B53-C2-D22
A39-B53-C2-D22
A65-B53-C2-D22
A66-B53-C2-D22
A2-B79-C2-D22
A3-B79-C2-D22
A9-B79-C2-D22
A13-B79-C2-D22
A24-B79-C2-D22
A69-B79-C2-D22
A67-B79-C2-D22
A39-B79-C2-D22
A65-B79-C2-D22
A66-B79-C2-D22
A2-B80-C2-D22
A3-B80-C2-D22
A9-B80-C2-D22
A13-B80-C2-D22
A24-B80-C2-D22
A69-B80-C2-D22
A67-B80-C2-D22
A39-B80-C2-D22
A65-B80-C2-D22
A66-B80-C2-D22
A2-B85-C2-D22
A3-B85-C2-D22
A9-B85-C2-D22
A13-B85-C2-D22
A24-B85-C2-D22
A69-B85-C2-D22
A67-B85-C2-D22
A39-B85-C2-D22
A65-B85-C2-D22
A66-B85-C2-D22
A2-B86-C2-D22
A3-B86-C2-D22
A9-B86-C2-D22
A13-B86-C2-D22
A24-B86-C2-D22
A69-B86-C2-D22
A67-B86-C2-D22
A39-B86-C2-D22
A65-B86-C2-D22
A66-B86-C2-D22
A2-B87-C2-D22

-continued

A3-B87-C2-D22
A9-B87-C2-D22
A13-B87-C2-D22
A24-B87-C2-D22
A69-B87-C2-D22
A67-B87-C2-D22
A39-B87-C2-D22
A65-B87-C2-D22
A66-B87-C2-D22
A2-B89-C2-D22
A3-B89-C2-D22
A9-B89-C2-D22
A13-B89-C2-D22
A24-B89-C2-D22
A69-B89-C2-D22
A67-B89-C2-D22
A39-B89-C2-D22
A65-B89-C2-D22
A66-B89-C2-D22
A2-B92-C2-D22
A3-B92-C2-D22
A9-B92-C2-D22
A13-B92-C2-D22
A24-B92-C2-D22
A69-B92-C2-D22
A67-B92-C2-D22
A39-B92-C2-D22
A65-B92-C2-D22
A66-B92-C2-D22
A2-B4-C3-D22
A3-B4-C3-D22
A9-B4-C3-D22
A13-B4-C3-D22
A24-B4-C3-D22
A69-B4-C3-D22
A67-B4-C3-D22
A39-B4-C3-D22
A65-B4-C3-D22
A66-B4-C3-D22
A2-B5-C3-D22
A3-B5-C3-D22
A9-B5-C3-D22
A13-B5-C3-D22
A24-B5-C3-D22
A69-B5-C3-D22
A67-B5-C3-D22
A39-B5-C3-D22
A65-B5-C3-D22
A66-B5-C3-D22
A2-B6-C3-D22
A3-B6-C3-D22
A9-B6-C3-D22
A13-B6-C3-D22
A24-B6-C3-D22
A69-B6-C3-D22
A67-B6-C3-D22
A39-B6-C3-D22
A65-B6-C3-D22
A66-B6-C3-D22
A2-B32-C3-D22
A3-B32-C3-D22
A9-B32-C3-D22
A13-B32-C3-D22
A24-B32-C3-D22
A69-B32-C3-D22
A67-B32-C3-D22
A39-B32-C3-D22
A65-B32-C3-D22
A66-B32-C3-D22
A2-B39-C3-D22
A3-B39-C3-D22
A9-B39-C3-D22
A13-B39-C3-D22
A24-B39-C3-D22
A69-B39-C3-D22
A67-B39-C3-D22
A39-B39-C3-D22
A65-B39-C3-D22
A66-B39-C3-D22
A2-B45-C3-D22

-continued

A3-B45-C3-D22
A9-B45-C3-D22
A13-B45-C3-D22
A24-B45-C3-D22
A69-B45-C3-D22
A67-B45-C3-D22
A39-B45-C3-D22
A65-B45-C3-D22
A66-B45-C3-D22
A2-B53-C3-D22
A3-B53-C3-D22
A9-B53-C3-D22
A13-B53-C3-D22
A24-B53-C3-D22
A69-B53-C3-D22
A67-B53-C3-D22
A39-B53-C3-D22
A65-B53-C3-D22
A66-B53-C3-D22
A2-B79-C3-D22
A3-B79-C3-D22
A9-B79-C3-D22
A13-B79-C3-D22
A24-B79-C3-D22
A69-B79-C3-D22
A67-B79-C3-D22
A39-B79-C3-D22
A65-B79-C3-D22
A66-B79-C3-D22
A2-B80-C3-D22
A3-B80-C3-D22
A9-B80-C3-D22
A13-B80-C3-D22
A24-B80-C3-D22
A69-B80-C3-D22
A67-B80-C3-D22
A39-B80-C3-D22
A65-B80-C3-D22
A66-B80-C3-D22
A2-B85-C3-D22
A3-B85-C3-D22
A9-B85-C3-D22
A13-B85-C3-D22
A24-B85-C3-D22
A69-B85-C3-D22
A67-B85-C3-D22
A39-B85-C3-D22
A65-B85-C3-D22
A66-B85-C3-D22
A2-B86-C3-D22
A3-B86-C3-D22
A9-B86-C3-D22
A13-B86-C3-D22
A24-B86-C3-D22
A69-B86-C3-D22
A67-B86-C3-D22
A39-B86-C3-D22
A65-B86-C3-D22
A66-B86-C3-D22
A2-B87-C3-D22
A3-B87-C3-D22
A9-B87-C3-D22
A13-B87-C3-D22
A24-B87-C3-D22
A69-B87-C3-D22
A67-B87-C3-D22
A39-B87-C3-D22
A65-B87-C3-D22
A66-B87-C3-D22
A2-B89-C3-D22
A3-B89-C3-D22
A9-B89-C3-D22
A13-B89-C3-D22
A24-B89-C3-D22
A69-B89-C3-D22
A67-B89-C3-D22
A39-B89-C3-D22
A65-B89-C3-D22
A66-B89-C3-D22
A2-B92-C3-D22

-continued
A3-B92-C3-D22
A9-B92-C3-D22
A13-B92-C3-D22
A24-B92-C3-D22
A69-B92-C3-D22
A67-B92-C3-D22
A39-B92-C3-D22
A65-B92-C3-D22
A66-B92-C3-D22
A2-B4-C4-D22
A3-B4-C4-D22
A9-B4-C4-D22
A13-B4-C4-D22
A24-B4-C4-D22
A69-B4-C4-D22
A67-B4-C4-D22
A39-B4-C4-D22
A65-B4-C4-D22
A66-B4-C4-D22
A2-B5-C4-D22
A3-B5-C4-D22
A9-B5-C4-D22
A13-B5-C4-D22
A24-B5-C4-D22
A69-B5-C4-D22
A67-B5-C4-D22
A39-B5-C4-D22
A65-B5-C4-D22
A66-B5-C4-D22
A2-B6-C4-D22
A3-B6-C4-D22
A9-B6-C4-D22
A13-B6-C4-D22
A24-B6-C4-D22
A69-B6-C4-D22
A67-B6-C4-D22
A39-B6-C4-D22
A65-B6-C4-D22
A66-B6-C4-D22
A2-B32-C4-D22
A3-B32-C4-D22
A9-B32-C4-D22
A13-B32-C4-D22
A24-B32-C4-D22
A69-B32-C4-D22
A67-B32-C4-D22
A39-B32-C4-D22
A65-B32-C4-D22
A66-B32-C4-D22
A2-B39-C4-D22
A3-B39-C4-D22
A9-B39-C4-D22
A13-B39-C4-D22
A24-B39-C4-D22
A69-B39-C4-D22
A67-B39-C4-D22
A39-B39-C4-D22
A65-B39-C4-D22
A66-B39-C4-D22
A2-B45-C4-D22
A3-B45-C4-D22
A9-B45-C4-D22
A13-B45-C4-D22
A24-B45-C4-D22
A69-B45-C4-D22
A67-B45-C4-D22
A39-B45-C4-D22
A65-B45-C4-D22
A66-B45-C4-D22
A2-B53-C4-D22
A3-B53-C4-D22
A9-B53-C4-D22
A13-B53-C4-D22
A24-B53-C4-D22
A69-B53-C4-D22
A67-B53-C4-D22
A39-B53-C4-D22
A65-B53-C4-D22
A66-B53-C4-D22
A2-B79-C4-D22

-continued
A3-B79-C4-D22
A9-B79-C4-D22
A13-B79-C4-D22
A24-B79-C4-D22
A69-B79-C4-D22
A67-B79-C4-D22
A39-B79-C4-D22
A65-B79-C4-D22
A66-B79-C4-D22
A2-B80-C4-D22
A3-B80-C4-D22
A9-B80-C4-D22
A13-B80-C4-D22
A24-B80-C4-D22
A69-B80-C4-D22
A67-B80-C4-D22
A39-B80-C4-D22
A65-B80-C4-D22
A66-B80-C4-D22
A2-B85-C4-D22
A3-B85-C4-D22
A9-B85-C4-D22
A13-B85-C4-D22
A24-B85-C4-D22
A69-B85-C4-D22
A67-B85-C4-D22
A39-B85-C4-D22
A65-B85-C4-D22
A66-B85-C4-D22
A2-B86-C4-D22
A3-B86-C4-D22
A9-B86-C4-D22
A13-B86-C4-D22
A24-B86-C4-D22
A69-B86-C4-D22
A67-B86-C4-D22
A39-B86-C4-D22
A65-B86-C4-D22
A66-B86-C4-D22
A2-B87-C4-D22
A3-B87-C4-D22
A9-B87-C4-D22
A13-B87-C4-D22
A24-B87-C4-D22
A69-B87-C4-D22
A67-B87-C4-D22
A39-B87-C4-D22
A65-B87-C4-D22
A66-B87-C4-D22
A2-B89-C4-D22
A3-B89-C4-D22
A9-B89-C4-D22
A13-B89-C4-D22
A24-B89-C4-D22
A69-B89-C4-D22
A67-B89-C4-D22
A39-B89-C4-D22
A65-B89-C4-D22
A66-B89-C4-D22
A2-B92-C4-D22
A3-B92-C4-D22
A9-B92-C4-D22
A13-B92-C4-D22
A24-B92-C4-D22
A69-B92-C4-D22
A67-B92-C4-D22
A39-B92-C4-D22
A65-B92-C4-D22
A66-B92-C4-D22
A2-B4-C5-D22
A3-B4-C5-D22
A9-B4-C5-D22
A13-B4-C5-D22
A24-B4-C5-D22
A69-B4-C5-D22
A67-B4-C5-D22
A39-B4-C5-D22
A65-B4-C5-D22
A66-B4-C5-D22
A2-B5-C5-D22

-continued

A3-B5-C5-D22
A9-B5-C5-D22
A13-B5-C5-D22
A24-B5-C5-D22
A69-B5-C5-D22
A67-B5-C5-D22
A39-B5-C5-D22
A65-B5-C5-D22
A66-B5-C5-D22
A2-B6-C5-D22
A3-B6-C5-D22
A9-B6-C5-D22
A13-B6-C5-D22
A24-B6-C5-D22
A69-B6-C5-D22
A67-B6-C5-D22
A39-B6-C5-D22
A65-B6-C5-D22
A66-B6-C5-D22
A2-B32-C5-D22
A3-B32-C5-D22
A9-B32-C5-D22
A13-B32-C5-D22
A24-B32-C5-D22
A69-B32-C5-D22
A67-B32-C5-D22
A39-B32-C5-D22
A65-B32-C5-D22
A66-B32-C5-D22
A2-B39-C5-D22
A3-B39-C5-D22
A9-B39-C5-D22
A13-B39-C5-D22
A24-B39-C5-D22
A69-B39-C5-D22
A67-B39-C5-D22
A39-B39-C5-D22
A65-B39-C5-D22
A66-B39-C5-D22
A2-B45-C5-D22
A3-B45-C5-D22
A9-B45-C5-D22
A13-B45-C5-D22
A24-B45-C5-D22
A69-B45-C5-D22
A67-B45-C5-D22
A39-B45-C5-D22
A65-B45-C5-D22
A66-B45-C5-D22
A2-B53-C5-D22
A3-B53-C5-D22
A9-B53-C5-D22
A13-B53-C5-D22
A24-B53-C5-D22
A69-B53-C5-D22
A67-B53-C5-D22
A39-B53-C5-D22
A65-B53-C5-D22
A66-B53-C5-D22
A2-B79-C5-D22
A3-B79-C5-D22
A9-B79-C5-D22
A13-B79-C5-D22
A24-B79-C5-D22
A69-B79-C5-D22
A67-B79-C5-D22
A39-B79-C5-D22
A65-B79-C5-D22
A66-B79-C5-D22
A2-B80-C5-D22
A3-B80-C5-D22
A9-B80-C5-D22
A13-B80-C5-D22
A24-B80-C5-D22
A69-B80-C5-D22
A67-B80-C5-D22
A39-B80-C5-D22
A65-B80-C5-D22
A66-B80-C5-D22
A2-B85-C5-D22

-continued

A3-B85-C5-D22
A9-B85-C5-D22
A13-B85-C5-D22
A24-B85-C5-D22
A69-B85-C5-D22
A67-B85-C5-D22
A39-B85-C5-D22
A65-B85-C5-D22
A66-B85-C5-D22
A2-B86-C5-D22
A3-B86-C5-D22
A9-B86-C5-D22
A13-B86-C5-D22
A24-B86-C5-D22
A69-B86-C5-D22
A67-B86-C5-D22
A39-B86-C5-D22
A65-B86-C5-D22
A66-B86-C5-D22
A2-B87-C5-D22
A3-B87-C5-D22
A9-B87-C5-D22
A13-B87-C5-D22
A24-B87-C5-D22
A69-B87-C5-D22
A67-B87-C5-D22
A39-B87-C5-D22
A65-B87-C5-D22
A66-B87-C5-D22
A2-B89-C5-D22
A3-B89-C5-D22
A9-B89-C5-D22
A13-B89-C5-D22
A24-B89-C5-D22
A69-B89-C5-D22
A67-B89-C5-D22
A39-B89-C5-D22
A65-B89-C5-D22
A66-B89-C5-D22
A2-B92-C5-D22
A3-B92-C5-D22
A9-B92-C5-D22
A13-B92-C5-D22
A24-B92-C5-D22
A69-B92-C5-D22
A67-B92-C5-D22
A39-B92-C5-D22
A65-B92-C5-D22
A66-B92-C5-D22
A2-B4-C6-D22
A3-B4-C6-D22
A9-B4-C6-D22
A13-B4-C6-D22
A24-B4-C6-D22
A69-B4-C6-D22
A67-B4-C6-D22
A39-B4-C6-D22
A65-B4-C6-D22
A66-B4-C6-D22
A2-B5-C6-D22
A3-B5-C6-D22
A9-B5-C6-D22
A13-B5-C6-D22
A24-B5-C6-D22
A69-B5-C6-D22
A67-B5-C6-D22
A39-B5-C6-D22
A65-B5-C6-D22
A66-B5-C6-D22
A2-B6-C6-D22
A3-B6-C6-D22
A9-B6-C6-D22
A13-B6-C6-D22
A24-B6-C6-D22
A69-B6-C6-D22
A67-B6-C6-D22
A39-B6-C6-D22
A65-B6-C6-D22
A66-B6-C6-D22
A2-B32-C6-D22

-continued

A3-B32-C6-D22
A9-B32-C6-D22
A13-B32-C6-D22
A24-B32-C6-D22
A69-B32-C6-D22
A67-B32-C6-D22
A39-B32-C6-D22
A65-B32-C6-D22
A66-B32-C6-D22
A2-B39-C6-D22
A3-B39-C6-D22
A9-B39-C6-D22
A13-B39-C6-D22
A24-B39-C6-D22
A69-B39-C6-D22
A67-B39-C6-D22
A39-B39-C6-D22
A65-B39-C6-D22
A66-B39-C6-D22
A2-B45-C6-D22
A3-B45-C6-D22
A9-B45-C6-D22
A13-B45-C6-D22
A24-B45-C6-D22
A69-B45-C6-D22
A67-B45-C6-D22
A39-B45-C6-D22
A65-B45-C6-D22
A66-B45-C6-D22
A2-B53-C6-D22
A3-B53-C6-D22
A9-B53-C6-D22
A13-B53-C6-D22
A24-B53-C6-D22
A69-B53-C6-D22
A67-B53-C6-D22
A39-B53-C6-D22
A65-B53-C6-D22
A66-B53-C6-D22
A2-B79-C6-D22
A3-B79-C6-D22
A9-B79-C6-D22
A13-B79-C6-D22
A24-B79-C6-D22
A69-B79-C6-D22
A67-B79-C6-D22
A39-B79-C6-D22
A65-B79-C6-D22
A66-B79-C6-D22
A2-B80-C6-D22
A3-B80-C6-D22
A9-B80-C6-D22
A13-B80-C6-D22
A24-B80-C6-D22
A69-B80-C6-D22
A67-B80-C6-D22
A39-B80-C6-D22
A65-B80-C6-D22
A66-B80-C6-D22
A2-B85-C6-D22
A3-B85-C6-D22
A9-B85-C6-D22
A13-B85-C6-D22
A24-B85-C6-D22
A69-B85-C6-D22
A67-B85-C6-D22
A39-B85-C6-D22
A65-B85-C6-D22
A66-B85-C6-D22
A2-B86-C6-D22
A3-B86-C6-D22
A9-B86-C6-D22
A13-B86-C6-D22
A24-B86-C6-D22
A69-B86-C6-D22
A67-B86-C6-D22
A39-B86-C6-D22
A65-B86-C6-D22
A66-B86-C6-D22
A2-B87-C6-D22

-continued

A3-B87-C6-D22
A9-B87-C6-D22
A13-B87-C6-D22
A24-B87-C6-D22
A69-B87-C6-D22
A67-B87-C6-D22
A39-B87-C6-D22
A65-B87-C6-D22
A66-B87-C6-D22
A2-B89-C6-D22
A3-B89-C6-D22
A9-B89-C6-D22
A13-B89-C6-D22
A24-B89-C6-D22
A69-B89-C6-D22
A67-B89-C6-D22
A39-B89-C6-D22
A65-B89-C6-D22
A66-B89-C6-D22
A2-B92-C6-D22
A3-B92-C6-D22
A9-B92-C6-D22
A13-B92-C6-D22
A24-B92-C6-D22
A69-B92-C6-D22
A67-B92-C6-D22
A39-B92-C6-D22
A65-B92-C6-D22
A66-B92-C6-D22
A2-B4-C7-D22
A3-B4-C7-D22
A9-B4-C7-D22
A13-B4-C7-D22
A24-B4-C7-D22
A69-B4-C7-D22
A67-B4-C7-D22
A39-B4-C7-D22
A65-B4-C7-D22
A66-B4-C7-D22
A2-B5-C7-D22
A3-B5-C7-D22
A9-B5-C7-D22
A13-B5-C7-D22
A24-B5-C7-D22
A69-B5-C7-D22
A67-B5-C7-D22
A39-B5-C7-D22
A65-B5-C7-D22
A66-B5-C7-D22
A2-B6-C7-D22
A3-B6-C7-D22
A9-B6-C7-D22
A13-B6-C7-D22
A24-B6-C7-D22
A69-B6-C7-D22
A67-B6-C7-D22
A39-B6-C7-D22
A65-B6-C7-D22
A66-B6-C7-D22
A2-B32-C7-D22
A3-B32-C7-D22
A9-B32-C7-D22
A13-B32-C7-D22
A24-B32-C7-D22
A69-B32-C7-D22
A67-B32-C7-D22
A39-B32-C7-D22
A65-B32-C7-D22
A66-B32-C7-D22
A2-B39-C7-D22
A3-B39-C7-D22
A9-B39-C7-D22
A13-B39-C7-D22
A24-B39-C7-D22
A69-B39-C7-D22
A67-B39-C7-D22
A39-B39-C7-D22
A65-B39-C7-D22
A66-B39-C7-D22
A2-B45-C7-D22

-continued
A3-B45-C7-D22
A9-B45-C7-D22
A13-B45-C7-D22
A24-B45-C7-D22
A69-B45-C7-D22
A67-B45-C7-D22
A39-B45-C7-D22
A65-B45-C7-D22
A66-B45-C7-D22
A2-B53-C7-D22
A3-B53-C7-D22
A9-B53-C7-D22
A13-B53-C7-D22
A24-B53-C7-D22
A69-B53-C7-D22
A67-B53-C7-D22
A39-B53-C7-D22
A65-B53-C7-D22
A66-B53-C7-D22
A2-B79-C7-D22
A3-B79-C7-D22
A9-B79-C7-D22
A13-B79-C7-D22
A24-B79-C7-D22
A69-B79-C7-D22
A67-B79-C7-D22
A39-B79-C7-D22
A65-B79-C7-D22
A66-B79-C7-D22
A2-B80-C7-D22
A3-B80-C7-D22
A9-B80-C7-D22
A13-B80-C7-D22
A24-B80-C7-D22
A69-B80-C7-D22
A67-B80-C7-D22
A39-B80-C7-D22
A65-B80-C7-D22
A66-B80-C7-D22
A2-B85-C7-D22
A3-B85-C7-D22
A9-B85-C7-D22
A13-B85-C7-D22
A24-B85-C7-D22
A69-B85-C7-D22
A67-B85-C7-D22
A39-B85-C7-D22
A65-B85-C7-D22
A66-B85-C7-D22
A2-B86-C7-D22
A3-B86-C7-D22
A9-B86-C7-D22
A13-B86-C7-D22
A24-B86-C7-D22
A69-B86-C7-D22
A67-B86-C7-D22
A39-B86-C7-D22
A65-B86-C7-D22
A66-B86-C7-D22
A2-B87-C7-D22
A3-B87-C7-D22
A9-B87-C7-D22
A13-B87-C7-D22
A24-B87-C7-D22
A69-B87-C7-D22
A67-B87-C7-D22
A39-B87-C7-D22
A65-B87-C7-D22
A66-B87-C7-D22
A2-B89-C7-D22
A3-B89-C7-D22
A9-B89-C7-D22
A13-B89-C7-D22
A24-B89-C7-D22
A69-B89-C7-D22
A67-B89-C7-D22
A39-B89-C7-D22
A65-B89-C7-D22
A66-B89-C7-D22
A2-B92-C7-D22

-continued
A3-B92-C7-D22
A9-B92-C7-D22
A13-B92-C7-D22
A24-B92-C7-D22
A69-B92-C7-D22
A67-B92-C7-D22
A39-B92-C7-D22
A65-B92-C7-D22
A66-B92-C7-D22
A2-B4-C8-D22
A3-B4-C8-D22
A9-B4-C8-D22
A13-B4-C8-D22
A24-B4-C8-D22
A69-B4-C8-D22
A67-B4-C8-D22
A39-B4-C8-D22
A65-B4-C8-D22
A66-B4-C8-D22
A2-B5-C8-D22
A3-B5-C8-D22
A9-B5-C8-D22
A13-B5-C8-D22
A24-B5-C8-D22
A69-B5-C8-D22
A67-B5-C8-D22
A39-B5-C8-D22
A65-B5-C8-D22
A66-B5-C8-D22
A2-B6-C8-D22
A3-B6-C8-D22
A9-B6-C8-D22
A13-B6-C8-D22
A24-B6-C8-D22
A69-B6-C8-D22
A67-B6-C8-D22
A39-B6-C8-D22
A65-B6-C8-D22
A66-B6-C8-D22
A2-B32-C8-D22
A3-B32-C8-D22
A9-B32-C8-D22
A13-B32-C8-D22
A24-B32-C8-D22
A69-B32-C8-D22
A67-B32-C8-D22
A39-B32-C8-D22
A65-B32-C8-D22
A66-B32-C8-D22
A2-B39-C8-D22
A3-B39-C8-D22
A9-B39-C8-D22
A13-B39-C8-D22
A24-B39-C8-D22
A69-B39-C8-D22
A67-B39-C8-D22
A39-B39-C8-D22
A65-B39-C8-D22
A66-B39-C8-D22
A2-B45-C8-D22
A3-B45-C8-D22
A9-B45-C8-D22
A13-B45-C8-D22
A24-B45-C8-D22
A69-B45-C8-D22
A67-B45-C8-D22
A39-B45-C8-D22
A65-B45-C8-D22
A66-B45-C8-D22
A2-B53-C8-D22
A3-B53-C8-D22
A9-B53-C8-D22
A13-B53-C8-D22
A24-B53-C8-D22
A69-B53-C8-D22
A67-B53-C8-D22
A39-B53-C8-D22
A65-B53-C8-D22
A66-B53-C8-D22
A2-B79-C8-D22

-continued

A3-B79-C8-D22
A9-B79-C8-D22
A13-B79-C8-D22
A24-B79-C8-D22
A69-B79-C8-D22
A67-B79-C8-D22
A39-B79-C8-D22
A65-B79-C8-D22
A66-B79-C8-D22
A2-B80-C8-D22
A3-B80-C8-D22
A9-B80-C8-D22
A13-B80-C8-D22
A24-B80-C8-D22
A69-B80-C8-D22
A67-B80-C8-D22
A39-B80-C8-D22
A65-B80-C8-D22
A66-B80-C8-D22
A2-B85-C8-D22
A3-B85-C8-D22
A9-B85-C8-D22
A13-B85-C8-D22
A24-B85-C8-D22
A69-B85-C8-D22
A67-B85-C8-D22
A39-B85-C8-D22
A65-B85-C8-D22
A66-B85-C8-D22
A2-B86-C8-D22
A3-B86-C8-D22
A9-B86-C8-D22
A13-B86-C8-D22
A24-B86-C8-D22
A69-B86-C8-D22
A67-B86-C8-D22
A39-B86-C8-D22
A65-B86-C8-D22
A66-B86-C8-D22
A2-B87-C8-D22
A3-B87-C8-D22
A9-B87-C8-D22
A13-B87-C8-D22
A24-B87-C8-D22
A69-B87-C8-D22
A67-B87-C8-D22
A39-B87-C8-D22
A65-B87-C8-D22
A66-B87-C8-D22
A2-B89-C8-D22
A3-B89-C8-D22
A9-B89-C8-D22
A13-B89-C8-D22
A24-B89-C8-D22
A69-B89-C8-D22
A67-B89-C8-D22
A39-B89-C8-D22
A65-B89-C8-D22
A66-B89-C8-D22
A2-B92-C8-D22
A3-B92-C8-D22
A9-B92-C8-D22
A13-B92-C8-D22
A24-B92-C8-D22
A69-B92-C8-D22
A67-B92-C8-D22
A39-B92-C8-D22
A65-B92-C8-D22
A66-B92-C8-D22
A2-B4-C9-D22
A3-B4-C9-D22
A9-B4-C9-D22
A13-B4-C9-D22
A24-B4-C9-D22
A69-B4-C9-D22
A67-B4-C9-D22
A39-B4-C9-D22
A65-B4-C9-D22
A66-B4-C9-D22
A2-B5-C9-D22

-continued

A3-B5-C9-D22
A9-B5-C9-D22
A13-B5-C9-D22
A24-B5-C9-D22
A69-B5-C9-D22
A67-B5-C9-D22
A39-B5-C9-D22
A65-B5-C9-D22
A66-B5-C9-D22
A2-B6-C9-D22
A3-B6-C9-D22
A9-B6-C9-D22
A13-B6-C9-D22
A24-B6-C9-D22
A69-B6-C9-D22
A67-B6-C9-D22
A39-B6-C9-D22
A65-B6-C9-D22
A66-B6-C9-D22
A2-B32-C9-D22
A3-B32-C9-D22
A9-B32-C9-D22
A13-B32-C9-D22
A24-B32-C9-D22
A69-B32-C9-D22
A67-B32-C9-D22
A39-B32-C9-D22
A65-B32-C9-D22
A66-B32-C9-D22
A2-B39-C9-D22
A3-B39-C9-D22
A9-B39-C9-D22
A13-B39-C9-D22
A24-B39-C9-D22
A69-B39-C9-D22
A67-B39-C9-D22
A39-B39-C9-D22
A65-B39-C9-D22
A66-B39-C9-D22
A2-B45-C9-D22
A3-B45-C9-D22
A9-B45-C9-D22
A13-B45-C9-D22
A24-B45-C9-D22
A69-B45-C9-D22
A67-B45-C9-D22
A39-B45-C9-D22
A65-B45-C9-D22
A66-B45-C9-D22
A2-B53-C9-D22
A3-B53-C9-D22
A9-B53-C9-D22
A13-B53-C9-D22
A24-B53-C9-D22
A69-B53-C9-D22
A67-B53-C9-D22
A39-B53-C9-D22
A65-B53-C9-D22
A66-B53-C9-D22
A2-B79-C9-D22
A3-B79-C9-D22
A9-B79-C9-D22
A13-B79-C9-D22
A24-B79-C9-D22
A69-B79-C9-D22
A67-B79-C9-D22
A39-B79-C9-D22
A65-B79-C9-D22
A66-B79-C9-D22
A2-B80-C9-D22
A3-B80-C9-D22
A9-B80-C9-D22
A13-B80-C9-D22
A24-B80-C9-D22
A69-B80-C9-D22
A67-B80-C9-D22
A39-B80-C9-D22
A65-B80-C9-D22
A66-B80-C9-D22
A2-B85-C9-D22

-continued

A3-B85-C9-D22
A9-B85-C9-D22
A13-B85-C9-D22
A24-B85-C9-D22
A69-B85-C9-D22
A67-B85-C9-D22
A39-B85-C9-D22
A65-B85-C9-D22
A66-B85-C9-D22
A2-B86-C9-D22
A3-B86-C9-D22
A9-B86-C9-D22
A13-B86-C9-D22
A24-B86-C9-D22
A69-B86-C9-D22
A67-B86-C9-D22
A39-B86-C9-D22
A65-B86-C9-D22
A66-B86-C9-D22
A2-B87-C9-D22
A3-B87-C9-D22
A9-B87-C9-D22
A13-B87-C9-D22
A24-B87-C9-D22
A69-B87-C9-D22
A67-B87-C9-D22
A39-B87-C9-D22
A65-B87-C9-D22
A66-B87-C9-D22
A2-B89-C9-D22
A3-B89-C9-D22
A9-B89-C9-D22
A13-B89-C9-D22
A24-B89-C9-D22
A69-B89-C9-D22
A67-B89-C9-D22
A39-B89-C9-D22
A65-B89-C9-D22
A66-B89-C9-D22
A2-B92-C9-D22
A3-B92-C9-D22
A9-B92-C9-D22
A13-B92-C9-D22
A24-B92-C9-D22
A69-B92-C9-D22
A67-B92-C9-D22
A39-B92-C9-D22
A65-B92-C9-D22
A66-B92-C9-D22
A2-B4-C10-D22
A3-B4-C10-D22
A9-B4-C10-D22
A13-B4-C10-D22
A24-B4-C10-D22
A69-B4-C10-D22
A67-B4-C10-D22
A39-B4-C10-D22
A65-B4-C10-D22
A66-B4-C10-D22
A2-B5-C10-D22
A3-B5-C10-D22
A9-B5-C10-D22
A13-B5-C10-D22
A24-B5-C10-D22
A69-B5-C10-D22
A67-B5-C10-D22
A39-B5-C10-D22
A65-B5-C10-D22
A66-B5-C10-D22
A2-B6-C10-D22
A3-B6-C10-D22
A9-B6-C10-D22
A13-B6-C10-D22
A24-B6-C10-D22
A69-B6-C10-D22
A67-B6-C10-D22
A39-B6-C10-D22
A65-B6-C10-D22
A66-B6-C10-D22
A2-B32-C10-D22

-continued

A3-B32-C10-D22
A9-B32-C10-D22
A13-B32-C10-D22
A24-B32-C10-D22
A69-B32-C10-D22
A67-B32-C10-D22
A39-B32-C10-D22
A65-B32-C10-D22
A66-B32-C10-D22
A2-B39-C10-D22
A3-B39-C10-D22
A9-B39-C10-D22
A13-B39-C10-D22
A24-B39-C10-D22
A69-B39-C10-D22
A67-B39-C10-D22
A39-B39-C10-D22
A65-B39-C10-D22
A66-B39-C10-D22
A2-B45-C10-D22
A3-B45-C10-D22
A9-B45-C10-D22
A13-B45-C10-D22
A24-B45-C10-D22
A69-B45-C10-D22
A67-B45-C10-D22
A39-B45-C10-D22
A65-B45-C10-D22
A66-B45-C10-D22
A2-B53-C10-D22
A3-B53-C10-D22
A9-B53-C10-D22
A13-B53-C10-D22
A24-B53-C10-D22
A69-B53-C10-D22
A67-B53-C10-D22
A39-B53-C10-D22
A65-B53-C10-D22
A66-B53-C10-D22
A2-B79-C10-D22
A3-B79-C10-D22
A9-B79-C10-D22
A13-B79-C10-D22
A24-B79-C10-D22
A69-B79-C10-D22
A67-B79-C10-D22
A39-B79-C10-D22
A65-B79-C10-D22
A66-B79-C10-D22
A2-B80-C10-D22
A3-B80-C10-D22
A9-B80-C10-D22
A13-B80-C10-D22
A24-B80-C10-D22
A69-B80-C10-D22
A67-B80-C10-D22
A39-B80-C10-D22
A65-B80-C10-D22
A66-B80-C10-D22
A2-B85-C10-D22
A3-B85-C10-D22
A9-B85-C10-D22
A13-B85-C10-D22
A24-B85-C10-D22
A69-B85-C10-D22
A67-B85-C10-D22
A39-B85-C10-D22
A65-B85-C10-D22
A66-B85-C10-D22
A2-B86-C10-D22
A3-B86-C10-D22
A9-B86-C10-D22
A13-B86-C10-D22
A24-B86-C10-D22
A69-B86-C10-D22
A67-B86-C10-D22
A39-B86-C10-D22
A65-B86-C10-D22
A66-B86-C10-D22
A2-B87-C10-D22

-continued

A3-B87-C10-D22
A9-B87-C10-D22
A13-B87-C10-D22
A24-B87-C10-D22
A69-B87-C10-D22
A67-B87-C10-D22
A39-B87-C10-D22
A65-B87-C10-D22
A66-B87-C10-D22
A2-B89-C10-D22
A3-B89-C10-D22
A9-B89-C10-D22
A13-B89-C10-D22
A24-B89-C10-D22
A69-B89-C10-D22
A67-B89-C10-D22
A39-B89-C10-D22
A65-B89-C10-D22
A66-B89-C10-D22
A2-B92-C10-D22
A3-B92-C10-D22
A9-B92-C10-D22
A13-B92-C10-D22
A24-B92-C10-D22
A69-B92-C10-D22
A67-B92-C10-D22
A39-B92-C10-D22
A65-B92-C10-D22
A66-B92-C10-D22
A2-B4-C11-D22
A3-B4-C11-D22
A9-B4-C11-D22
A13-B4-C11-D22
A24-B4-C11-D22
A69-B4-C11-D22
A67-B4-C11-D22
A39-B4-C11-D22
A65-B4-C11-D22
A66-B4-C11-D22
A2-B5-C11-D22
A3-B5-C11-D22
A9-B5-C11-D22
A13-B5-C11-D22
A24-B5-C11-D22
A69-B5-C11-D22
A67-B5-C11-D22
A39-B5-C11-D22
A65-B5-C11-D22
A66-B5-C11-D22
A2-B6-C11-D22
A3-B6-C11-D22
A9-B6-C11-D22
A13-B6-C11-D22
A24-B6-C11-D22
A69-B6-C11-D22
A67-B6-C11-D22
A39-B6-C11-D22
A65-B6-C11-D22
A66-B6-C11-D22
A2-B32-C11-D22
A3-B32-C11-D22
A9-B32-C11-D22
A13-B32-C11-D22
A24-B32-C11-D22
A69-B32-C11-D22
A67-B32-C11-D22
A39-B32-C11-D22
A65-B32-C11-D22
A66-B32-C11-D22
A2-B39-C11-D22
A3-B39-C11-D22
A9-B39-C11-D22
A13-B39-C11-D22
A24-B39-C11-D22
A69-B39-C11-D22
A67-B39-C11-D22
A39-B39-C11-D22
A65-B39-C11-D22
A66-B39-C11-D22
A2-B45-C11-D22

-continued

A3-B45-C11-D22
A9-B45-C11-D22
A13-B45-C11-D22
A24-B45-C11-D22
A69-B45-C11-D22
A67-B45-C11-D22
A39-B45-C11-D22
A65-B45-C11-D22
A66-B45-C11-D22
A2-B53-C11-D22
A3-B53-C11-D22
A9-B53-C11-D22
A13-B53-C11-D22
A24-B53-C11-D22
A69-B53-C11-D22
A67-B53-C11-D22
A39-B53-C11-D22
A65-B53-C11-D22
A66-B53-C11-D22
A2-B79-C11-D22
A3-B79-C11-D22
A9-B79-C11-D22
A13-B79-C11-D22
A24-B79-C11-D22
A69-B79-C11-D22
A67-B79-C11-D22
A39-B79-C11-D22
A65-B79-C11-D22
A66-B79-C11-D22
A2-B80-C11-D22
A3-B80-C11-D22
A9-B80-C11-D22
A13-B80-C11-D22
A24-B80-C11-D22
A69-B80-C11-D22
A67-B80-C11-D22
A39-B80-C11-D22
A65-B80-C11-D22
A66-B80-C11-D22
A2-B85-C11-D22
A3-B85-C11-D22
A9-B85-C11-D22
A13-B85-C11-D22
A24-B85-C11-D22
A69-B85-C11-D22
A67-B85-C11-D22
A39-B85-C11-D22
A65-B85-C11-D22
A66-B85-C11-D22
A2-B86-C11-D22
A3-B86-C11-D22
A9-B86-C11-D22
A13-B86-C11-D22
A24-B86-C11-D22
A69-B86-C11-D22
A67-B86-C11-D22
A39-B86-C11-D22
A65-B86-C11-D22
A66-B86-C11-D22
A2-B87-C11-D22
A3-B87-C11-D22
A9-B87-C11-D22
A13-B87-C11-D22
A24-B87-C11-D22
A69-B87-C11-D22
A67-B87-C11-D22
A39-B87-C11-D22
A65-B87-C11-D22
A66-B87-C11-D22
A2-B89-C11-D22
A3-B89-C11-D22
A9-B89-C11-D22
A13-B89-C11-D22
A24-B89-C11-D22
A69-B89-C11-D22
A67-B89-C11-D22
A39-B89-C11-D22
A65-B89-C11-D22
A66-B89-C11-D22
A2-B92-C11-D22

-continued

A3-B92-C11-D22
A9-B92-C11-D22
A13-B92-C11-D22
A24-B92-C11-D22
A69-B92-C11-D22
A67-B92-C11-D22
A39-B92-C11-D22
A65-B92-C11-D22
A66-B92-C11-D22
A2-B4-C12-D22
A3-B4-C12-D22
A9-B4-C12-D22
A13-B4-C12-D22
A24-B4-C12-D22
A69-B4-C12-D22
A67-B4-C12-D22
A39-B4-C12-D22
A65-B4-C12-D22
A66-B4-C12-D22
A2-B5-C12-D22
A3-B5-C12-D22
A9-B5-C12-D22
A13-B5-C12-D22
A24-B5-C12-D22
A69-B5-C12-D22
A67-B5-C12-D22
A39-B5-C12-D22
A65-B5-C12-D22
A66-B5-C12-D22
A2-B6-C12-D22
A3-B6-C12-D22
A9-B6-C12-D22
A13-B6-C12-D22
A24-B6-C12-D22
A69-B6-C12-D22
A67-B6-C12-D22
A39-B6-C12-D22
A65-B6-C12-D22
A66-B6-C12-D22
A2-B32-C12-D22
A3-B32-C12-D22
A9-B32-C12-D22
A13-B32-C12-D22
A24-B32-C12-D22
A69-B32-C12-D22
A67-B32-C12-D22
A39-B32-C12-D22
A65-B32-C12-D22
A66-B32-C12-D22
A2-B39-C12-D22
A3-B39-C12-D22
A9-B39-C12-D22
A13-B39-C12-D22
A24-B39-C12-D22
A69-B39-C12-D22
A67-B39-C12-D22
A39-B39-C12-D22
A65-B39-C12-D22
A66-B39-C12-D22
A2-B45-C12-D22
A3-B45-C12-D22
A9-B45-C12-D22
A13-B45-C12-D22
A24-B45-C12-D22
A69-B45-C12-D22
A67-B45-C12-D22
A39-B45-C12-D22
A65-B45-C12-D22
A66-B45-C12-D22
A2-B53-C12-D22
A3-B53-C12-D22
A9-B53-C12-D22
A13-B53-C12-D22
A24-B53-C12-D22
A69-B53-C12-D22
A67-B53-C12-D22
A39-B53-C12-D22
A65-B53-C12-D22
A66-B53-C12-D22
A2-B79-C12-D22

-continued

A3-B79-C12-D22
A9-B79-C12-D22
A13-B79-C12-D22
A24-B79-C12-D22
A69-B79-C12-D22
A67-B79-C12-D22
A39-B79-C12-D22
A65-B79-C12-D22
A66-B79-C12-D22
A2-B80-C12-D22
A3-B80-C12-D22
A9-B80-C12-D22
A13-B80-C12-D22
A24-B80-C12-D22
A69-B80-C12-D22
A67-B80-C12-D22
A39-B80-C12-D22
A65-B80-C12-D22
A66-B80-C12-D22
A2-B85-C12-D22
A3-B85-C12-D22
A9-B85-C12-D22
A13-B85-C12-D22
A24-B85-C12-D22
A69-B85-C12-D22
A67-B85-C12-D22
A39-B85-C12-D22
A65-B85-C12-D22
A66-B85-C12-D22
A2-B86-C12-D22
A3-B86-C12-D22
A9-B86-C12-D22
A13-B86-C12-D22
A24-B86-C12-D22
A69-B86-C12-D22
A67-B86-C12-D22
A39-B86-C12-D22
A65-B86-C12-D22
A66-B86-C12-D22
A2-B87-C12-D22
A3-B87-C12-D22
A9-B87-C12-D22
A13-B87-C12-D22
A24-B87-C12-D22
A69-B87-C12-D22
A67-B87-C12-D22
A39-B87-C12-D22
A65-B87-C12-D22
A66-B87-C12-D22
A2-B89-C12-D22
A3-B89-C12-D22
A9-B89-C12-D22
A13-B89-C12-D22
A24-B89-C12-D22
A69-B89-C12-D22
A67-B89-C12-D22
A39-B89-C12-D22
A65-B89-C12-D22
A66-B89-C12-D22
A2-B92-C12-D22
A3-B92-C12-D22
A9-B92-C12-D22
A13-B92-C12-D22
A24-B92-C12-D22
A69-B92-C12-D22
A67-B92-C12-D22
A39-B92-C12-D22
A65-B92-C12-D22
A66-B92-C12-D22
A2-B4-C13-D22
A3-B4-C13-D22
A9-B4-C13-D22
A13-B4-C13-D22
A24-B4-C13-D22
A69-B4-C13-D22
A67-B4-C13-D22
A39-B4-C13-D22
A65-B4-C13-D22
A66-B4-C13-D22
A2-B5-C13-D22

-continued

A3-B5-C13-D22
A9-B5-C13-D22
A13-B5-C13-D22
A24-B5-C13-D22
A69-B5-C13-D22
A67-B5-C13-D22
A39-B5-C13-D22
A65-B5-C13-D22
A66-B5-C13-D22
A2-B6-C13-D22
A3-B6-C13-D22
A9-B6-C13-D22
A13-B6-C13-D22
A24-B6-C13-D22
A69-B6-C13-D22
A67-B6-C13-D22
A39-B6-C13-D22
A65-B6-C13-D22
A66-B6-C13-D22
A2-B32-C13-D22
A3-B32-C13-D22
A9-B32-C13-D22
A13-B32-C13-D22
A24-B32-C13-D22
A69-B32-C13-D22
A67-B32-C13-D22
A39-B32-C13-D22
A65-B32-C13-D22
A66-B32-C13-D22
A2-B39-C13-D22
A3-B39-C13-D22
A9-B39-C13-D22
A13-B39-C13-D22
A24-B39-C13-D22
A69-B39-C13-D22
A67-B39-C13-D22
A39-B39-C13-D22
A65-B39-C13-D22
A66-B39-C13-D22
A2-B45-C13-D22
A3-B45-C13-D22
A9-B45-C13-D22
A13-B45-C13-D22
A24-B45-C13-D22
A69-B45-C13-D22
A67-B45-C13-D22
A39-B45-C13-D22
A65-B45-C13-D22
A66-B45-C13-D22
A2-B53-C13-D22
A3-B53-C13-D22
A9-B53-C13-D22
A13-B53-C13-D22
A24-B53-C13-D22
A69-B53-C13-D22
A67-B53-C13-D22
A39-B53-C13-D22
A65-B53-C13-D22
A66-B53-C13-D22
A2-B79-C13-D22
A3-B79-C13-D22
A9-B79-C13-D22
A13-B79-C13-D22
A24-B79-C13-D22
A69-B79-C13-D22
A67-B79-C13-D22
A39-B79-C13-D22
A65-B79-C13-D22
A66-B79-C13-D22
A2-B80-C13-D22
A3-B80-C13-D22
A9-B80-C13-D22
A13-B80-C13-D22
A24-B80-C13-D22
A69-B80-C13-D22
A67-B80-C13-D22
A39-B80-C13-D22
A65-B80-C13-D22
A66-B80-C13-D22
A2-B85-C13-D22

-continued

A3-B85-C13-D22
A9-B85-C13-D22
A13-B85-C13-D22
A24-B85-C13-D22
A69-B85-C13-D22
A67-B85-C13-D22
A39-B85-C13-D22
A65-B85-C13-D22
A66-B85-C13-D22
A2-B86-C13-D22
A3-B86-C13-D22
A9-B86-C13-D22
A13-B86-C13-D22
A24-B86-C13-D22
A69-B86-C13-D22
A67-B86-C13-D22
A39-B86-C13-D22
A65-B86-C13-D22
A66-B86-C13-D22
A2-B87-C13-D22
A3-B87-C13-D22
A9-B87-C13-D22
A13-B87-C13-D22
A24-B87-C13-D22
A69-B87-C13-D22
A67-B87-C13-D22
A39-B87-C13-D22
A65-B87-C13-D22
A66-B87-C13-D22
A2-B89-C13-D22
A3-B89-C13-D22
A9-B89-C13-D22
A13-B89-C13-D22
A24-B89-C13-D22
A69-B89-C13-D22
A67-B89-C13-D22
A39-B89-C13-D22
A65-B89-C13-D22
A66-B89-C13-D22
A2-B92-C13-D22
A3-B92-C13-D22
A9-B92-C13-D22
A13-B92-C13-D22
A24-B92-C13-D22
A69-B92-C13-D22
A67-B92-C13-D22
A39-B92-C13-D22
A65-B92-C13-D22
A66-B92-C13-D22
A2-B4-C1-D23
A3-B4-C1-D23
A9-B4-C1-D23
A13-B4-C1-D23
A24-B4-C1-D23
A69-B4-C1-D23
A67-B4-C1-D23
A39-B4-C1-D23
A65-B4-C1-D23
A66-B4-C1-D23
A2-B5-C1-D23
A3-B5-C1-D23
A9-B5-C1-D23
A13-B5-C1-D23
A24-B5-C1-D23
A69-B5-C1-D23
A67-B5-C1-D23
A39-B5-C1-D23
A65-B5-C1-D23
A66-B5-C1-D23
A2-B6-C1-D23
A3-B6-C1-D23
A9-B6-C1-D23
A13-B6-C1-D23
A24-B6-C1-D23
A69-B6-C1-D23
A67-B6-C1-D23
A39-B6-C1-D23
A65-B6-C1-D23
A66-B6-C1-D23
A2-B32-C1-D23

-continued
A3-B32-C1-D23
A9-B32-C1-D23
A13-B32-C1-D23
A24-B32-C1-D23
A69-B32-C1-D23
A67-B32-C1-D23
A39-B32-C1-D23
A65-B32-C1-D23
A66-B32-C1-D23
A2-B39-C1-D23
A3-B39-C1-D23
A9-B39-C1-D23
A13-B39-C1-D23
A24-B39-C1-D23
A69-B39-C1-D23
A67-B39-C1-D23
A39-B39-C1-D23
A65-B39-C1-D23
A66-B39-C1-D23
A2-B45-C1-D23
A3-B45-C1-D23
A9-B45-C1-D23
A13-B45-C1-D23
A24-B45-C1-D23
A69-B45-C1-D23
A67-B45-C1-D23
A39-B45-C1-D23
A65-B45-C1-D23
A66-B45-C1-D23
A2-B53-C1-D23
A3-B53-C1-D23
A9-B53-C1-D23
A13-B53-C1-D23
A24-B53-C1-D23
A69-B53-C1-D23
A67-B53-C1-D23
A39-B53-C1-D23
A65-B53-C1-D23
A66-B53-C1-D23
A2-B79-C1-D23
A3-B79-C1-D23
A9-B79-C1-D23
A13-B79-C1-D23
A24-B79-C1-D23
A69-B79-C1-D23
A67-B79-C1-D23
A39-B79-C1-D23
A65-B79-C1-D23
A66-B79-C1-D23
A2-B80-C1-D23
A3-B80-C1-D23
A9-B80-C1-D23
A13-B80-C1-D23
A24-B80-C1-D23
A69-B80-C1-D23
A67-B80-C1-D23
A39-B80-C1-D23
A65-B80-C1-D23
A66-B80-C1-D23
A2-B85-C1-D23
A3-B85-C1-D23
A9-B85-C1-D23
A13-B85-C1-D23
A24-B85-C1-D23
A69-B85-C1-D23
A67-B85-C1-D23
A39-B85-C1-D23
A65-B85-C1-D23
A66-B85-C1-D23
A2-B86-C1-D23
A3-B86-C1-D23
A9-B86-C1-D23
A13-B86-C1-D23
A24-B86-C1-D23
A69-B86-C1-D23
A67-B86-C1-D23
A39-B86-C1-D23
A65-B86-C1-D23
A66-B86-C1-D23
A2-B87-C1-D23

-continued
A3-B87-C1-D23
A9-B87-C1-D23
A13-B87-C1-D23
A24-B87-C1-D23
A69-B87-C1-D23
A67-B87-C1-D23
A39-B87-C1-D23
A65-B87-C1-D23
A66-B87-C1-D23
A2-B89-C1-D23
A3-B89-C1-D23
A9-B89-C1-D23
A13-B89-C1-D23
A24-B89-C1-D23
A69-B89-C1-D23
A67-B89-C1-D23
A39-B89-C1-D23
A65-B89-C1-D23
A66-B89-C1-D23
A2-B92-C1-D23
A3-B92-C1-D23
A9-B92-C1-D23
A13-B92-C1-D23
A24-B92-C1-D23
A69-B92-C1-D23
A67-B92-C1-D23
A39-B92-C1-D23
A65-B92-C1-D23
A66-B92-C1-D23
A2-B4-C2-D23
A3-B4-C2-D23
A9-B4-C2-D23
A13-B4-C2-D23
A24-B4-C2-D23
A69-B4-C2-D23
A67-B4-C2-D23
A39-B4-C2-D23
A65-B4-C2-D23
A66-B4-C2-D23
A2-B5-C2-D23
A3-B5-C2-D23
A9-B5-C2-D23
A13-B5-C2-D23
A24-B5-C2-D23
A69-B5-C2-D23
A67-B5-C2-D23
A39-B5-C2-D23
A65-B5-C2-D23
A66-B5-C2-D23
A2-B6-C2-D23
A3-B6-C2-D23
A9-B6-C2-D23
A13-B6-C2-D23
A24-B6-C2-D23
A69-B6-C2-D23
A67-B6-C2-D23
A39-B6-C2-D23
A65-B6-C2-D23
A66-B6-C2-D23
A2-B32-C2-D23
A3-B32-C2-D23
A9-B32-C2-D23
A13-B32-C2-D23
A24-B32-C2-D23
A69-B32-C2-D23
A67-B32-C2-D23
A39-B32-C2-D23
A65-B32-C2-D23
A66-B32-C2-D23
A2-B39-C2-D23
A3-B39-C2-D23
A9-B39-C2-D23
A13-B39-C2-D23
A24-B39-C2-D23
A69-B39-C2-D23
A67-B39-C2-D23
A39-B39-C2-D23
A65-B39-C2-D23
A66-B39-C2-D23
A2-B45-C2-D23

-continued
A3-B45-C2-D23
A9-B45-C2-D23
A13-B45-C2-D23
A24-B45-C2-D23
A69-B45-C2-D23
A67-B45-C2-D23
A39-B45-C2-D23
A65-B45-C2-D23
A66-B45-C2-D23
A2-B53-C2-D23
A3-B53-C2-D23
A9-B53-C2-D23
A13-B53-C2-D23
A24-B53-C2-D23
A69-B53-C2-D23
A67-B53-C2-D23
A39-B53-C2-D23
A65-B53-C2-D23
A66-B53-C2-D23
A2-B79-C2-D23
A3-B79-C2-D23
A9-B79-C2-D23
A13-B79-C2-D23
A24-B79-C2-D23
A69-B79-C2-D23
A67-B79-C2-D23
A39-B79-C2-D23
A65-B79-C2-D23
A66-B79-C2-D23
A2-B80-C2-D23
A3-B80-C2-D23
A9-B80-C2-D23
A13-B80-C2-D23
A24-B80-C2-D23
A69-B80-C2-D23
A67-B80-C2-D23
A39-B80-C2-D23
A65-B80-C2-D23
A66-B80-C2-D23
A2-B85-C2-D23
A3-B85-C2-D23
A9-B85-C2-D23
A13-B85-C2-D23
A24-B85-C2-D23
A69-B85-C2-D23
A67-B85-C2-D23
A39-B85-C2-D23
A65-B85-C2-D23
A66-B85-C2-D23
A2-B86-C2-D23
A3-B86-C2-D23
A9-B86-C2-D23
A13-B86-C2-D23
A24-B86-C2-D23
A69-B86-C2-D23
A67-B86-C2-D23
A39-B86-C2-D23
A65-B86-C2-D23
A66-B86-C2-D23
A2-B87-C2-D23
A3-B87-C2-D23
A9-B87-C2-D23
A13-B87-C2-D23
A24-B87-C2-D23
A69-B87-C2-D23
A67-B87-C2-D23
A39-B87-C2-D23
A65-B87-C2-D23
A66-B87-C2-D23
A2-B89-C2-D23
A3-B89-C2-D23
A9-B89-C2-D23
A13-B89-C2-D23
A24-B89-C2-D23
A69-B89-C2-D23
A67-B89-C2-D23
A39-B89-C2-D23
A65-B89-C2-D23
A66-B89-C2-D23
A2-B92-C2-D23

-continued
A3-B92-C2-D23
A9-B92-C2-D23
A13-B92-C2-D23
A24-B92-C2-D23
A69-B92-C2-D23
A67-B92-C2-D23
A39-B92-C2-D23
A65-B92-C2-D23
A66-B92-C2-D23
A2-B4-C3-D23
A3-B4-C3-D23
A9-B4-C3-D23
A13-B4-C3-D23
A24-B4-C3-D23
A69-B4-C3-D23
A67-B4-C3-D23
A39-B4-C3-D23
A65-B4-C3-D23
A66-B4-C3-D23
A2-B5-C3-D23
A3-B5-C3-D23
A9-B5-C3-D23
A13-B5-C3-D23
A24-B5-C3-D23
A69-B5-C3-D23
A67-B5-C3-D23
A39-B5-C3-D23
A65-B5-C3-D23
A66-B5-C3-D23
A2-B6-C3-D23
A3-B6-C3-D23
A9-B6-C3-D23
A13-B6-C3-D23
A24-B6-C3-D23
A69-B6-C3-D23
A67-B6-C3-D23
A39-B6-C3-D23
A65-B6-C3-D23
A66-B6-C3-D23
A2-B32-C3-D23
A3-B32-C3-D23
A9-B32-C3-D23
A13-B32-C3-D23
A24-B32-C3-D23
A69-B32-C3-D23
A67-B32-C3-D23
A39-B32-C3-D23
A65-B32-C3-D23
A66-B32-C3-D23
A2-B39-C3-D23
A3-B39-C3-D23
A9-B39-C3-D23
A13-B39-C3-D23
A24-B39-C3-D23
A69-B39-C3-D23
A67-B39-C3-D23
A39-B39-C3-D23
A65-B39-C3-D23
A66-B39-C3-D23
A2-B45-C3-D23
A3-B45-C3-D23
A9-B45-C3-D23
A13-B45-C3-D23
A24-B45-C3-D23
A69-B45-C3-D23
A67-B45-C3-D23
A39-B45-C3-D23
A65-B45-C3-D23
A66-B45-C3-D23
A2-B53-C3-D23
A3-B53-C3-D23
A9-B53-C3-D23
A13-B53-C3-D23
A24-B53-C3-D23
A69-B53-C3-D23
A67-B53-C3-D23
A39-B53-C3-D23
A65-B53-C3-D23
A66-B53-C3-D23
A2-B79-C3-D23

-continued
A3-B79-C3-D23
A9-B79-C3-D23
A13-B79-C3-D23
A24-B79-C3-D23
A69-B79-C3-D23
A67-B79-C3-D23
A39-B79-C3-D23
A65-B79-C3-D23
A66-B79-C3-D23
A2-B80-C3-D23
A3-B80-C3-D23
A9-B80-C3-D23
A13-B80-C3-D23
A24-B80-C3-D23
A69-B80-C3-D23
A67-B80-C3-D23
A39-B80-C3-D23
A65-B80-C3-D23
A66-B80-C3-D23
A2-B85-C3-D23
A3-B85-C3-D23
A9-B85-C3-D23
A13-B85-C3-D23
A24-B85-C3-D23
A69-B85-C3-D23
A67-B85-C3-D23
A39-B85-C3-D23
A65-B85-C3-D23
A66-B85-C3-D23
A2-B86-C3-D23
A3-B86-C3-D23
A9-B86-C3-D23
A13-B86-C3-D23
A24-B86-C3-D23
A69-B86-C3-D23
A67-B86-C3-D23
A39-B86-C3-D23
A65-B86-C3-D23
A66-B86-C3-D23
A2-B87-C3-D23
A3-B87-C3-D23
A9-B87-C3-D23
A13-B87-C3-D23
A24-B87-C3-D23
A69-B87-C3-D23
A67-B87-C3-D23
A39-B87-C3-D23
A65-B87-C3-D23
A66-B87-C3-D23
A2-B89-C3-D23
A3-B89-C3-D23
A9-B89-C3-D23
A13-B89-C3-D23
A24-B89-C3-D23
A69-B89-C3-D23
A67-B89-C3-D23
A39-B89-C3-D23
A65-B89-C3-D23
A66-B89-C3-D23
A2-B92-C3-D23
A3-B92-C3-D23
A9-B92-C3-D23
A13-B92-C3-D23
A24-B92-C3-D23
A69-B92-C3-D23
A67-B92-C3-D23
A39-B92-C3-D23
A65-B92-C3-D23
A66-B92-C3-D23
A2-B4-C4-D23
A3-B4-C4-D23
A9-B4-C4-D23
A13-B4-C4-D23
A24-B4-C4-D23
A69-B4-C4-D23
A67-B4-C4-D23
A39-B4-C4-D23
A65-B4-C4-D23
A66-B4-C4-D23
A2-B5-C4-D23

-continued
A3-B5-C4-D23
A9-B5-C4-D23
A13-B5-C4-D23
A24-B5-C4-D23
A69-B5-C4-D23
A67-B5-C4-D23
A39-B5-C4-D23
A65-B5-C4-D23
A66-B5-C4-D23
A2-B6-C4-D23
A3-B6-C4-D23
A9-B6-C4-D23
A13-B6-C4-D23
A24-B6-C4-D23
A69-B6-C4-D23
A67-B6-C4-D23
A39-B6-C4-D23
A65-B6-C4-D23
A66-B6-C4-D23
A2-B32-C4-D23
A3-B32-C4-D23
A9-B32-C4-D23
A13-B32-C4-D23
A24-B32-C4-D23
A69-B32-C4-D23
A67-B32-C4-D23
A39-B32-C4-D23
A65-B32-C4-D23
A66-B32-C4-D23
A2-B39-C4-D23
A3-B39-C4-D23
A9-B39-C4-D23
A13-B39-C4-D23
A24-B39-C4-D23
A69-B39-C4-D23
A67-B39-C4-D23
A39-B39-C4-D23
A65-B39-C4-D23
A66-B39-C4-D23
A2-B45-C4-D23
A3-B45-C4-D23
A9-B45-C4-D23
A13-B45-C4-D23
A24-B45-C4-D23
A69-B45-C4-D23
A67-B45-C4-D23
A39-B45-C4-D23
A65-B45-C4-D23
A66-B45-C4-D23
A2-B53-C4-D23
A3-B53-C4-D23
A9-B53-C4-D23
A13-B53-C4-D23
A24-B53-C4-D23
A69-B53-C4-D23
A67-B53-C4-D23
A39-B53-C4-D23
A65-B53-C4-D23
A66-B53-C4-D23
A2-B79-C4-D23
A3-B79-C4-D23
A9-B79-C4-D23
A13-B79-C4-D23
A24-B79-C4-D23
A69-B79-C4-D23
A67-B79-C4-D23
A39-B79-C4-D23
A65-B79-C4-D23
A66-B79-C4-D23
A2-B80-C4-D23
A3-B80-C4-D23
A9-B80-C4-D23
A13-B80-C4-D23
A24-B80-C4-D23
A69-B80-C4-D23
A67-B80-C4-D23
A39-B80-C4-D23
A65-B80-C4-D23
A66-B80-C4-D23
A2-B85-C4-D23

-continued

A3-B85-C4-D23
A9-B85-C4-D23
A13-B85-C4-D23
A24-B85-C4-D23
A69-B85-C4-D23
A67-B85-C4-D23
A39-B85-C4-D23
A65-B85-C4-D23
A66-B85-C4-D23
A2-B86-C4-D23
A3-B86-C4-D23
A9-B86-C4-D23
A13-B86-C4-D23
A24-B86-C4-D23
A69-B86-C4-D23
A67-B86-C4-D23
A39-B86-C4-D23
A65-B86-C4-D23
A66-B86-C4-D23
A2-B87-C4-D23
A3-B87-C4-D23
A9-B87-C4-D23
A13-B87-C4-D23
A24-B87-C4-D23
A69-B87-C4-D23
A67-B87-C4-D23
A39-B87-C4-D23
A65-B87-C4-D23
A66-B87-C4-D23
A2-B89-C4-D23
A3-B89-C4-D23
A9-B89-C4-D23
A13-B89-C4-D23
A24-B89-C4-D23
A69-B89-C4-D23
A67-B89-C4-D23
A39-B89-C4-D23
A65-B89-C4-D23
A66-B89-C4-D23
A2-B92-C4-D23
A3-B92-C4-D23
A9-B92-C4-D23
A13-B92-C4-D23
A24-B92-C4-D23
A69-B92-C4-D23
A67-B92-C4-D23
A39-B92-C4-D23
A65-B92-C4-D23
A66-B92-C4-D23
A2-B4-C5-D23
A3-B4-C5-D23
A9-B4-C5-D23
A13-B4-C5-D23
A24-B4-C5-D23
A69-B4-C5-D23
A67-B4-C5-D23
A39-B4-C5-D23
A65-B4-C5-D23
A66-B4-C5-D23
A2-B5-C5-D23
A3-B5-C5-D23
A9-B5-C5-D23
A13-B5-C5-D23
A24-B5-C5-D23
A69-B5-C5-D23
A67-B5-C5-D23
A39-B5-C5-D23
A65-B5-C5-D23
A66-B5-C5-D23
A2-B6-C5-D23
A3-B6-C5-D23
A9-B6-C5-D23
A13-B6-C5-D23
A24-B6-C5-D23
A69-B6-C5-D23
A67-B6-C5-D23
A39-B6-C5-D23
A65-B6-C5-D23
A66-B6-C5-D23
A2-B32-C5-D23

-continued

A3-B32-C5-D23
A9-B32-C5-D23
A13-B32-C5-D23
A24-B32-C5-D23
A69-B32-C5-D23
A67-B32-C5-D23
A39-B32-C5-D23
A65-B32-C5-D23
A66-B32-C5-D23
A2-B39-C5-D23
A3-B39-C5-D23
A9-B39-C5-D23
A13-B39-C5-D23
A24-B39-C5-D23
A69-B39-C5-D23
A67-B39-C5-D23
A39-B39-C5-D23
A65-B39-C5-D23
A66-B39-C5-D23
A2-B45-C5-D23
A3-B45-C5-D23
A9-B45-C5-D23
A13-B45-C5-D23
A24-B45-C5-D23
A69-B45-C5-D23
A67-B45-C5-D23
A39-B45-C5-D23
A65-B45-C5-D23
A66-B45-C5-D23
A2-B53-C5-D23
A3-B53-C5-D23
A9-B53-C5-D23
A13-B53-C5-D23
A24-B53-C5-D23
A69-B53-C5-D23
A67-B53-C5-D23
A39-B53-C5-D23
A65-B53-C5-D23
A66-B53-C5-D23
A2-B79-C5-D23
A3-B79-C5-D23
A9-B79-C5-D23
A13-B79-C5-D23
A24-B79-C5-D23
A69-B79-C5-D23
A67-B79-C5-D23
A39-B79-C5-D23
A65-B79-C5-D23
A66-B79-C5-D23
A2-B80-C5-D23
A3-B80-C5-D23
A9-B80-C5-D23
A13-B80-C5-D23
A24-B80-C5-D23
A69-B80-C5-D23
A67-B80-C5-D23
A39-B80-C5-D23
A65-B80-C5-D23
A66-B80-C5-D23
A2-B85-C5-D23
A3-B85-C5-D23
A9-B85-C5-D23
A13-B85-C5-D23
A24-B85-C5-D23
A69-B85-C5-D23
A67-B85-C5-D23
A39-B85-C5-D23
A65-B85-C5-D23
A66-B85-C5-D23
A2-B86-C5-D23
A3-B86-C5-D23
A9-B86-C5-D23
A13-B86-C5-D23
A24-B86-C5-D23
A69-B86-C5-D23
A67-B86-C5-D23
A39-B86-C5-D23
A65-B86-C5-D23
A66-B86-C5-D23
A2-B87-C5-D23

-continued
A3-B87-C5-D23
A9-B87-C5-D23
A13-B87-C5-D23
A24-B87-C5-D23
A69-B87-C5-D23
A67-B87-C5-D23
A39-B87-C5-D23
A65-B87-C5-D23
A66-B87-C5-D23
A2-B89-C5-D23
A3-B89-C5-D23
A9-B89-C5-D23
A13-B89-C5-D23
A24-B89-C5-D23
A69-B89-C5-D23
A67-B89-C5-D23
A39-B89-C5-D23
A65-B89-C5-D23
A66-B89-C5-D23
A2-B92-C5-D23
A3-B92-C5-D23
A9-B92-C5-D23
A13-B92-C5-D23
A24-B92-C5-D23
A69-B92-C5-D23
A67-B92-C5-D23
A39-B92-C5-D23
A65-B92-C5-D23
A66-B92-C5-D23
A2-B4-C6-D23
A3-B4-C6-D23
A9-B4-C6-D23
A13-B4-C6-D23
A24-B4-C6-D23
A69-B4-C6-D23
A67-B4-C6-D23
A39-B4-C6-D23
A65-B4-C6-D23
A66-B4-C6-D23
A2-B5-C6-D23
A3-B5-C6-D23
A9-B5-C6-D23
A13-B5-C6-D23
A24-B5-C6-D23
A69-B5-C6-D23
A67-B5-C6-D23
A39-B5-C6-D23
A65-B5-C6-D23
A66-B5-C6-D23
A2-B6-C6-D23
A3-B6-C6-D23
A9-B6-C6-D23
A13-B6-C6-D23
A24-B6-C6-D23
A69-B6-C6-D23
A67-B6-C6-D23
A39-B6-C6-D23
A65-B6-C6-D23
A66-B6-C6-D23
A2-B32-C6-D23
A3-B32-C6-D23
A9-B32-C6-D23
A13-B32-C6-D23
A24-B32-C6-D23
A69-B32-C6-D23
A67-B32-C6-D23
A39-B32-C6-D23
A65-B32-C6-D23
A66-B32-C6-D23
A2-B39-C6-D23
A3-B39-C6-D23
A9-B39-C6-D23
A13-B39-C6-D23
A24-B39-C6-D23
A69-B39-C6-D23
A67-B39-C6-D23
A39-B39-C6-D23
A65-B39-C6-D23
A66-B39-C6-D23
A2-B45-C6-D23

-continued
A3-B45-C6-D23
A9-B45-C6-D23
A13-B45-C6-D23
A24-B45-C6-D23
A69-B45-C6-D23
A67-B45-C6-D23
A39-B45-C6-D23
A65-B45-C6-D23
A66-B45-C6-D23
A2-B53-C6-D23
A3-B53-C6-D23
A9-B53-C6-D23
A13-B53-C6-D23
A24-B53-C6-D23
A69-B53-C6-D23
A67-B53-C6-D23
A39-B53-C6-D23
A65-B53-C6-D23
A66-B53-C6-D23
A2-B79-C6-D23
A3-B79-C6-D23
A9-B79-C6-D23
A13-B79-C6-D23
A24-B79-C6-D23
A69-B79-C6-D23
A67-B79-C6-D23
A39-B79-C6-D23
A65-B79-C6-D23
A66-B79-C6-D23
A2-B80-C6-D23
A3-B80-C6-D23
A9-B80-C6-D23
A13-B80-C6-D23
A24-B80-C6-D23
A69-B80-C6-D23
A67-B80-C6-D23
A39-B80-C6-D23
A65-B80-C6-D23
A66-B80-C6-D23
A2-B85-C6-D23
A3-B85-C6-D23
A9-B85-C6-D23
A13-B85-C6-D23
A24-B85-C6-D23
A69-B85-C6-D23
A67-B85-C6-D23
A39-B85-C6-D23
A65-B85-C6-D23
A66-B85-C6-D23
A2-B86-C6-D23
A3-B86-C6-D23
A9-B86-C6-D23
A13-B86-C6-D23
A24-B86-C6-D23
A69-B86-C6-D23
A67-B86-C6-D23
A39-B86-C6-D23
A65-B86-C6-D23
A66-B86-C6-D23
A2-B87-C6-D23
A3-B87-C6-D23
A9-B87-C6-D23
A13-B87-C6-D23
A24-B87-C6-D23
A69-B87-C6-D23
A67-B87-C6-D23
A39-B87-C6-D23
A65-B87-C6-D23
A66-B87-C6-D23
A2-B89-C6-D23
A3-B89-C6-D23
A9-B89-C6-D23
A13-B89-C6-D23
A24-B89-C6-D23
A69-B89-C6-D23
A67-B89-C6-D23
A39-B89-C6-D23
A65-B89-C6-D23
A66-B89-C6-D23
A2-B92-C6-D23

-continued
A3-B92-C6-D23
A9-B92-C6-D23
A13-B92-C6-D23
A24-B92-C6-D23
A69-B92-C6-D23
A67-B92-C6-D23
A39-B92-C6-D23
A65-B92-C6-D23
A66-B92-C6-D23
A2-B4-C7-D23
A3-B4-C7-D23
A9-B4-C7-D23
A13-B4-C7-D23
A24-B4-C7-D23
A69-B4-C7-D23
A67-B4-C7-D23
A39-B4-C7-D23
A65-B4-C7-D23
A66-B4-C7-D23
A2-B5-C7-D23
A3-B5-C7-D23
A9-B5-C7-D23
A13-B5-C7-D23
A24-B5-C7-D23
A69-B5-C7-D23
A67-B5-C7-D23
A39-B5-C7-D23
A65-B5-C7-D23
A66-B5-C7-D23
A2-B6-C7-D23
A3-B6-C7-D23
A9-B6-C7-D23
A13-B6-C7-D23
A24-B6-C7-D23
A69-B6-C7-D23
A67-B6-C7-D23
A39-B6-C7-D23
A65-B6-C7-D23
A66-B6-C7-D23
A2-B32-C7-D23
A3-B32-C7-D23
A9-B32-C7-D23
A13-B32-C7-D23
A24-B32-C7-D23
A69-B32-C7-D23
A67-B32-C7-D23
A39-B32-C7-D23
A65-B32-C7-D23
A66-B32-C7-D23
A2-B39-C7-D23
A3-B39-C7-D23
A9-B39-C7-D23
A13-B39-C7-D23
A24-B39-C7-D23
A69-B39-C7-D23
A67-B39-C7-D23
A39-B39-C7-D23
A65-B39-C7-D23
A66-B39-C7-D23
A2-B45-C7-D23
A3-B45-C7-D23
A9-B45-C7-D23
A13-B45-C7-D23
A24-B45-C7-D23
A69-B45-C7-D23
A67-B45-C7-D23
A39-B45-C7-D23
A65-B45-C7-D23
A66-B45-C7-D23
A2-B53-C7-D23
A3-B53-C7-D23
A9-B53-C7-D23
A13-B53-C7-D23
A24-B53-C7-D23
A69-B53-C7-D23
A67-B53-C7-D23
A39-B53-C7-D23
A65-B53-C7-D23
A66-B53-C7-D23
A2-B79-C7-D23

-continued
A3-B79-C7-D23
A9-B79-C7-D23
A13-B79-C7-D23
A24-B79-C7-D23
A69-B79-C7-D23
A67-B79-C7-D23
A39-B79-C7-D23
A65-B79-C7-D23
A66-B79-C7-D23
A2-B80-C7-D23
A3-B80-C7-D23
A9-B80-C7-D23
A13-B80-C7-D23
A24-B80-C7-D23
A69-B80-C7-D23
A67-B80-C7-D23
A39-B80-C7-D23
A65-B80-C7-D23
A66-B80-C7-D23
A2-B85-C7-D23
A3-B85-C7-D23
A9-B85-C7-D23
A13-B85-C7-D23
A24-B85-C7-D23
A69-B85-C7-D23
A67-B85-C7-D23
A39-B85-C7-D23
A65-B85-C7-D23
A66-B85-C7-D23
A2-B86-C7-D23
A3-B86-C7-D23
A9-B86-C7-D23
A13-B86-C7-D23
A24-B86-C7-D23
A69-B86-C7-D23
A67-B86-C7-D23
A39-B86-C7-D23
A65-B86-C7-D23
A66-B86-C7-D23
A2-B87-C7-D23
A3-B87-C7-D23
A9-B87-C7-D23
A13-B87-C7-D23
A24-B87-C7-D23
A69-B87-C7-D23
A67-B87-C7-D23
A39-B87-C7-D23
A65-B87-C7-D23
A66-B87-C7-D23
A2-B89-C7-D23
A3-B89-C7-D23
A9-B89-C7-D23
A13-B89-C7-D23
A24-B89-C7-D23
A69-B89-C7-D23
A67-B89-C7-D23
A39-B89-C7-D23
A65-B89-C7-D23
A66-B89-C7-D23
A2-B92-C7-D23
A3-B92-C7-D23
A9-B92-C7-D23
A13-B92-C7-D23
A24-B92-C7-D23
A69-B92-C7-D23
A67-B92-C7-D23
A39-B92-C7-D23
A65-B92-C7-D23
A66-B92-C7-D23
A2-B4-C8-D23
A3-B4-C8-D23
A9-B4-C8-D23
A13-B4-C8-D23
A24-B4-C8-D23
A69-B4-C8-D23
A67-B4-C8-D23
A39-B4-C8-D23
A65-B4-C8-D23
A66-B4-C8-D23
A2-B5-C8-D23

-continued
A3-B5-C8-D23
A9-B5-C8-D23
A13-B5-C8-D23
A24-B5-C8-D23
A69-B5-C8-D23
A67-B5-C8-D23
A39-B5-C8-D23
A65-B5-C8-D23
A66-B5-C8-D23
A2-B6-C8-D23
A3-B6-C8-D23
A9-B6-C8-D23
A13-B6-C8-D23
A24-B6-C8-D23
A69-B6-C8-D23
A67-B6-C8-D23
A39-B6-C8-D23
A65-B6-C8-D23
A66-B6-C8-D23
A2-B32-C8-D23
A3-B32-C8-D23
A9-B32-C8-D23
A13-B32-C8-D23
A24-B32-C8-D23
A69-B32-C8-D23
A67-B32-C8-D23
A39-B32-C8-D23
A65-B32-C8-D23
A66-B32-C8-D23
A2-B39-C8-D23
A3-B39-C8-D23
A9-B39-C8-D23
A13-B39-C8-D23
A24-B39-C8-D23
A69-B39-C8-D23
A67-B39-C8-D23
A39-B39-C8-D23
A65-B39-C8-D23
A66-B39-C8-D23
A2-B45-C8-D23
A3-B45-C8-D23
A9-B45-C8-D23
A13-B45-C8-D23
A24-B45-C8-D23
A69-B45-C8-D23
A67-B45-C8-D23
A39-B45-C8-D23
A65-B45-C8-D23
A66-B45-C8-D23
A2-B53-C8-D23
A3-B53-C8-D23
A9-B53-C8-D23
A13-B53-C8-D23
A24-B53-C8-D23
A69-B53-C8-D23
A67-B53-C8-D23
A39-B53-C8-D23
A65-B53-C8-D23
A66-B53-C8-D23
A2-B79-C8-D23
A3-B79-C8-D23
A9-B79-C8-D23
A13-B79-C8-D23
A24-B79-C8-D23
A69-B79-C8-D23
A67-B79-C8-D23
A39-B79-C8-D23
A65-B79-C8-D23
A66-B79-C8-D23
A2-B80-C8-D23
A3-B80-C8-D23
A9-B80-C8-D23
A13-B80-C8-D23
A24-B80-C8-D23
A69-B80-C8-D23
A67-B80-C8-D23
A39-B80-C8-D23
A65-B80-C8-D23
A66-B80-C8-D23
A2-B85-C8-D23

-continued
A3-B85-C8-D23
A9-B85-C8-D23
A13-B85-C8-D23
A24-B85-C8-D23
A69-B85-C8-D23
A67-B85-C8-D23
A39-B85-C8-D23
A65-B85-C8-D23
A66-B85-C8-D23
A2-B86-C8-D23
A3-B86-C8-D23
A9-B86-C8-D23
A13-B86-C8-D23
A24-B86-C8-D23
A69-B86-C8-D23
A67-B86-C8-D23
A39-B86-C8-D23
A65-B86-C8-D23
A66-B86-C8-D23
A2-B87-C8-D23
A3-B87-C8-D23
A9-B87-C8-D23
A13-B87-C8-D23
A24-B87-C8-D23
A69-B87-C8-D23
A67-B87-C8-D23
A39-B87-C8-D23
A65-B87-C8-D23
A66-B87-C8-D23
A2-B89-C8-D23
A3-B89-C8-D23
A9-B89-C8-D23
A13-B89-C8-D23
A24-B89-C8-D23
A69-B89-C8-D23
A67-B89-C8-D23
A39-B89-C8-D23
A65-B89-C8-D23
A66-B89-C8-D23
A2-B92-C8-D23
A3-B92-C8-D23
A9-B92-C8-D23
A13-B92-C8-D23
A24-B92-C8-D23
A69-B92-C8-D23
A67-B92-C8-D23
A39-B92-C8-D23
A65-B92-C8-D23
A66-B92-C8-D23
A2-B4-C9-D23
A3-B4-C9-D23
A9-B4-C9-D23
A13-B4-C9-D23
A24-B4-C9-D23
A69-B4-C9-D23
A67-B4-C9-D23
A39-B4-C9-D23
A65-B4-C9-D23
A66-B4-C9-D23
A2-B5-C9-D23
A3-B5-C9-D23
A9-B5-C9-D23
A13-B5-C9-D23
A24-B5-C9-D23
A69-B5-C9-D23
A67-B5-C9-D23
A39-B5-C9-D23
A65-B5-C9-D23
A66-B5-C9-D23
A2-B6-C9-D23
A3-B6-C9-D23
A9-B6-C9-D23
A13-B6-C9-D23
A24-B6-C9-D23
A69-B6-C9-D23
A67-B6-C9-D23
A39-B6-C9-D23
A65-B6-C9-D23
A66-B6-C9-D23
A2-B32-C9-D23

-continued
A3-B32-C9-D23
A9-B32-C9-D23
A13-B32-C9-D23
A24-B32-C9-D23
A69-B32-C9-D23
A67-B32-C9-D23
A39-B32-C9-D23
A65-B32-C9-D23
A66-B32-C9-D23
A2-B39-C9-D23
A3-B39-C9-D23
A9-B39-C9-D23
A13-B39-C9-D23
A24-B39-C9-D23
A69-B39-C9-D23
A67-B39-C9-D23
A39-B39-C9-D23
A65-B39-C9-D23
A66-B39-C9-D23
A2-B45-C9-D23
A3-B45-C9-D23
A9-B45-C9-D23
A13-B45-C9-D23
A24-B45-C9-D23
A69-B45-C9-D23
A67-B45-C9-D23
A39-B45-C9-D23
A65-B45-C9-D23
A66-B45-C9-D23
A2-B53-C9-D23
A3-B53-C9-D23
A9-B53-C9-D23
A13-B53-C9-D23
A24-B53-C9-D23
A69-B53-C9-D23
A67-B53-C9-D23
A39-B53-C9-D23
A65-B53-C9-D23
A66-B53-C9-D23
A2-B79-C9-D23
A3-B79-C9-D23
A9-B79-C9-D23
A13-B79-C9-D23
A24-B79-C9-D23
A69-B79-C9-D23
A67-B79-C9-D23
A39-B79-C9-D23
A65-B79-C9-D23
A66-B79-C9-D23
A2-B80-C9-D23
A3-B80-C9-D23
A9-B80-C9-D23
A13-B80-C9-D23
A24-B80-C9-D23
A69-B80-C9-D23
A67-B80-C9-D23
A39-B80-C9-D23
A65-B80-C9-D23
A66-B80-C9-D23
A2-B85-C9-D23
A3-B85-C9-D23
A9-B85-C9-D23
A13-B85-C9-D23
A24-B85-C9-D23
A69-B85-C9-D23
A67-B85-C9-D23
A39-B85-C9-D23
A65-B85-C9-D23
A66-B85-C9-D23
A2-B86-C9-D23
A3-B86-C9-D23
A9-B86-C9-D23
A13-B86-C9-D23
A24-B86-C9-D23
A69-B86-C9-D23
A67-B86-C9-D23
A39-B86-C9-D23
A65-B86-C9-D23
A66-B86-C9-D23
A2-B87-C9-D23

-continued
A3-B87-C9-D23
A9-B87-C9-D23
A13-B87-C9-D23
A24-B87-C9-D23
A69-B87-C9-D23
A67-B87-C9-D23
A39-B87-C9-D23
A65-B87-C9-D23
A66-B87-C9-D23
A2-B89-C9-D23
A3-B89-C9-D23
A9-B89-C9-D23
A13-B89-C9-D23
A24-B89-C9-D23
A69-B89-C9-D23
A67-B89-C9-D23
A39-B89-C9-D23
A65-B89-C9-D23
A66-B89-C9-D23
A2-B92-C9-D23
A3-B92-C9-D23
A9-B92-C9-D23
A13-B92-C9-D23
A24-B92-C9-D23
A69-B92-C9-D23
A67-B92-C9-D23
A39-B92-C9-D23
A65-B92-C9-D23
A66-B92-C9-D23
A2-B4-C10-D23
A3-B4-C10-D23
A9-B4-C10-D23
A13-B4-C10-D23
A24-B4-C10-D23
A69-B4-C10-D23
A67-B4-C10-D23
A39-B4-C10-D23
A65-B4-C10-D23
A66-B4-C10-D23
A2-B5-C10-D23
A3-B5-C10-D23
A9-B5-C10-D23
A13-B5-C10-D23
A24-B5-C10-D23
A69-B5-C10-D23
A67-B5-C10-D23
A39-B5-C10-D23
A65-B5-C10-D23
A66-B5-C10-D23
A2-B6-C10-D23
A3-B6-C10-D23
A9-B6-C10-D23
A13-B6-C10-D23
A24-B6-C10-D23
A69-B6-C10-D23
A67-B6-C10-D23
A39-B6-C10-D23
A65-B6-C10-D23
A66-B6-C10-D23
A2-B32-C10-D23
A3-B32-C10-D23
A9-B32-C10-D23
A13-B32-C10-D23
A24-B32-C10-D23
A69-B32-C10-D23
A67-B32-C10-D23
A39-B32-C10-D23
A65-B32-C10-D23
A66-B32-C10-D23
A2-B39-C10-D23
A3-B39-C10-D23
A9-B39-C10-D23
A13-B39-C10-D23
A24-B39-C10-D23
A69-B39-C10-D23
A67-B39-C10-D23
A39-B39-C10-D23
A65-B39-C10-D23
A66-B39-C10-D23
A2-B45-C10-D23

-continued
A3-B45-C10-D23
A9-B45-C10-D23
A13-B45-C10-D23
A24-B45-C10-D23
A69-B45-C10-D23
A67-B45-C10-D23
A39-B45-C10-D23
A65-B45-C10-D23
A66-B45-C10-D23
A2-B53-C10-D23
A3-B53-C10-D23
A9-B53-C10-D23
A13-B53-C10-D23
A24-B53-C10-D23
A69-B53-C10-D23
A67-B53-C10-D23
A39-B53-C10-D23
A65-B53-C10-D23
A66-B53-C10-D23
A2-B79-C10-D23
A3-B79-C10-D23
A9-B79-C10-D23
A13-B79-C10-D23
A24-B79-C10-D23
A69-B79-C10-D23
A67-B79-C10-D23
A39-B79-C10-D23
A65-B79-C10-D23
A66-B79-C10-D23
A2-B80-C10-D23
A3-B80-C10-D23
A9-B80-C10-D23
A13-B80-C10-D23
A24-B80-C10-D23
A69-B80-C10-D23
A67-B80-C10-D23
A39-B80-C10-D23
A65-B80-C10-D23
A66-B80-C10-D23
A2-B85-C10-D23
A3-B85-C10-D23
A9-B85-C10-D23
A13-B85-C10-D23
A24-B85-C10-D23
A69-B85-C10-D23
A67-B85-C10-D23
A39-B85-C10-D23
A65-B85-C10-D23
A66-B85-C10-D23
A2-B86-C10-D23
A3-B86-C10-D23
A9-B86-C10-D23
A13-B86-C10-D23
A24-B86-C10-D23
A69-B86-C10-D23
A67-B86-C10-D23
A39-B86-C10-D23
A65-B86-C10-D23
A66-B86-C10-D23
A2-B87-C10-D23
A3-B87-C10-D23
A9-B87-C10-D23
A13-B87-C10-D23
A24-B87-C10-D23
A69-B87-C10-D23
A67-B87-C10-D23
A39-B87-C10-D23
A65-B87-C10-D23
A66-B87-C10-D23
A2-B89-C10-D23
A3-B89-C10-D23
A9-B89-C10-D23
A13-B89-C10-D23
A24-B89-C10-D23
A69-B89-C10-D23
A67-B89-C10-D23
A39-B89-C10-D23
A65-B89-C10-D23
A66-B89-C10-D23
A2-B92-C10-D23

-continued
A3-B92-C10-D23
A9-B92-C10-D23
A13-B92-C10-D23
A24-B92-C10-D23
A69-B92-C10-D23
A67-B92-C10-D23
A39-B92-C10-D23
A65-B92-C10-D23
A66-B92-C10-D23
A2-B4-C11-D23
A3-B4-C11-D23
A9-B4-C11-D23
A13-B4-C11-D23
A24-B4-C11-D23
A69-B4-C11-D23
A67-B4-C11-D23
A39-B4-C11-D23
A65-B4-C11-D23
A66-B4-C11-D23
A2-B5-C11-D23
A3-B5-C11-D23
A9-B5-C11-D23
A13-B5-C11-D23
A24-B5-C11-D23
A69-B5-C11-D23
A67-B5-C11-D23
A39-B5-C11-D23
A65-B5-C11-D23
A66-B5-C11-D23
A2-B6-C11-D23
A3-B6-C11-D23
A9-B6-C11-D23
A13-B6-C11-D23
A24-B6-C11-D23
A69-B6-C11-D23
A67-B6-C11-D23
A39-B6-C11-D23
A65-B6-C11-D23
A66-B6-C11-D23
A2-B32-C11-D23
A3-B32-C11-D23
A9-B32-C11-D23
A13-B32-C11-D23
A24-B32-C11-D23
A69-B32-C11-D23
A67-B32-C11-D23
A39-B32-C11-D23
A65-B32-C11-D23
A66-B32-C11-D23
A2-B39-C11-D23
A3-B39-C11-D23
A9-B39-C11-D23
A13-B39-C11-D23
A24-B39-C11-D23
A69-B39-C11-D23
A67-B39-C11-D23
A39-B39-C11-D23
A65-B39-C11-D23
A66-B39-C11-D23
A2-B45-C11-D23
A3-B45-C11-D23
A9-B45-C11-D23
A13-B45-C11-D23
A24-B45-C11-D23
A69-B45-C11-D23
A67-B45-C11-D23
A39-B45-C11-D23
A65-B45-C11-D23
A66-B45-C11-D23
A2-B53-C11-D23
A3-B53-C11-D23
A9-B53-C11-D23
A13-B53-C11-D23
A24-B53-C11-D23
A69-B53-C11-D23
A67-B53-C11-D23
A39-B53-C11-D23
A65-B53-C11-D23
A66-B53-C11-D23
A2-B79-C11-D23

-continued
A3-B79-C11-D23
A9-B79-C11-D23
A13-B79-C11-D23
A24-B79-C11-D23
A69-B79-C11-D23
A67-B79-C11-D23
A39-B79-C11-D23
A65-B79-C11-D23
A66-B79-C11-D23
A2-B80-C11-D23
A3-B80-C11-D23
A9-B80-C11-D23
A13-B80-C11-D23
A24-B80-C11-D23
A69-B80-C11-D23
A67-B80-C11-D23
A39-B80-C11-D23
A65-B80-C11-D23
A66-B80-C11-D23
A2-B85-C11-D23
A3-B85-C11-D23
A9-B85-C11-D23
A13-B85-C11-D23
A24-B85-C11-D23
A69-B85-C11-D23
A67-B85-C11-D23
A39-B85-C11-D23
A65-B85-C11-D23
A66-B85-C11-D23
A2-B86-C11-D23
A3-B86-C11-D23
A9-B86-C11-D23
A13-B86-C11-D23
A24-B86-C11-D23
A69-B86-C11-D23
A67-B86-C11-D23
A39-B86-C11-D23
A65-B86-C11-D23
A66-B86-C11-D23
A2-B87-C11-D23
A3-B87-C11-D23
A9-B87-C11-D23
A13-B87-C11-D23
A24-B87-C11-D23
A69-B87-C11-D23
A67-B87-C11-D23
A39-B87-C11-D23
A65-B87-C11-D23
A66-B87-C11-D23
A2-B89-C11-D23
A3-B89-C11-D23
A9-B89-C11-D23
A13-B89-C11-D23
A24-B89-C11-D23
A69-B89-C11-D23
A67-B89-C11-D23
A39-B89-C11-D23
A65-B89-C11-D23
A66-B89-C11-D23
A2-B92-C11-D23
A3-B92-C11-D23
A9-B92-C11-D23
A13-B92-C11-D23
A24-B92-C11-D23
A69-B92-C11-D23
A67-B92-C11-D23
A39-B92-C11-D23
A65-B92-C11-D23
A66-B92-C11-D23
A2-B4-C12-D23
A3-B4-C12-D23
A9-B4-C12-D23
A13-B4-C12-D23
A24-B4-C12-D23
A69-B4-C12-D23
A67-B4-C12-D23
A39-B4-C12-D23
A65-B4-C12-D23
A66-B4-C12-D23
A2-B5-C12-D23

-continued
A3-B5-C12-D23
A9-B5-C12-D23
A13-B5-C12-D23
A24-B5-C12-D23
A69-B5-C12-D23
A67-B5-C12-D23
A39-B5-C12-D23
A65-B5-C12-D23
A66-B5-C12-D23
A2-B6-C12-D23
A3-B6-C12-D23
A9-B6-C12-D23
A13-B6-C12-D23
A24-B6-C12-D23
A69-B6-C12-D23
A67-B6-C12-D23
A39-B6-C12-D23
A65-B6-C12-D23
A66-B6-C12-D23
A2-B32-C12-D23
A3-B32-C12-D23
A9-B32-C12-D23
A13-B32-C12-D23
A24-B32-C12-D23
A69-B32-C12-D23
A67-B32-C12-D23
A39-B32-C12-D23
A65-B32-C12-D23
A66-B32-C12-D23
A2-B39-C12-D23
A3-B39-C12-D23
A9-B39-C12-D23
A13-B39-C12-D23
A24-B39-C12-D23
A69-B39-C12-D23
A67-B39-C12-D23
A39-B39-C12-D23
A65-B39-C12-D23
A66-B39-C12-D23
A2-B45-C12-D23
A3-B45-C12-D23
A9-B45-C12-D23
A13-B45-C12-D23
A24-B45-C12-D23
A69-B45-C12-D23
A67-B45-C12-D23
A39-B45-C12-D23
A65-B45-C12-D23
A66-B45-C12-D23
A2-B53-C12-D23
A3-B53-C12-D23
A9-B53-C12-D23
A13-B53-C12-D23
A24-B53-C12-D23
A69-B53-C12-D23
A67-B53-C12-D23
A39-B53-C12-D23
A65-B53-C12-D23
A66-B53-C12-D23
A2-B79-C12-D23
A3-B79-C12-D23
A9-B79-C12-D23
A13-B79-C12-D23
A24-B79-C12-D23
A69-B79-C12-D23
A67-B79-C12-D23
A39-B79-C12-D23
A65-B79-C12-D23
A66-B79-C12-D23
A2-B80-C12-D23
A3-B80-C12-D23
A9-B80-C12-D23
A13-B80-C12-D23
A24-B80-C12-D23
A69-B80-C12-D23
A67-B80-C12-D23
A39-B80-C12-D23
A65-B80-C12-D23
A66-B80-C12-D23
A2-B85-C12-D23

-continued
A3-B85-C12-D23
A9-B85-C12-D23
A13-B85-C12-D23
A24-B85-C12-D23
A69-B85-C12-D23
A67-B85-C12-D23
A39-B85-C12-D23
A65-B85-C12-D23
A66-B85-C12-D23
A2-B86-C12-D23
A3-B86-C12-D23
A9-B86-C12-D23
A13-B86-C12-D23
A24-B86-C12-D23
A69-B86-C12-D23
A67-B86-C12-D23
A39-B86-C12-D23
A65-B86-C12-D23
A66-B86-C12-D23
A2-B87-C12-D23
A3-B87-C12-D23
A9-B87-C12-D23
A13-B87-C12-D23
A24-B87-C12-D23
A69-B87-C12-D23
A67-B87-C12-D23
A39-B87-C12-D23
A65-B87-C12-D23
A66-B87-C12-D23
A2-B89-C12-D23
A3-B89-C12-D23
A9-B89-C12-D23
A13-B89-C12-D23
A24-B89-C12-D23
A69-B89-C12-D23
A67-B89-C12-D23
A39-B89-C12-D23
A65-B89-C12-D23
A66-B89-C12-D23
A2-B92-C12-D23
A3-B92-C12-D23
A9-B92-C12-D23
A13-B92-C12-D23
A24-B92-C12-D23
A69-B92-C12-D23
A67-B92-C12-D23
A39-B92-C12-D23
A65-B92-C12-D23
A66-B92-C12-D23
A2-B4-C13-D23
A3-B4-C13-D23
A9-B4-C13-D23
A13-B4-C13-D23
A24-B4-C13-D23
A69-B4-C13-D23
A67-B4-C13-D23
A39-B4-C13-D23
A65-B4-C13-D23
A66-B4-C13-D23
A2-B5-C13-D23
A3-B5-C13-D23
A9-B5-C13-D23
A13-B5-C13-D23
A24-B5-C13-D23
A69-B5-C13-D23
A67-B5-C13-D23
A39-B5-C13-D23
A65-B5-C13-D23
A66-B5-C13-D23
A2-B6-C13-D23
A3-B6-C13-D23
A9-B6-C13-D23
A13-B6-C13-D23
A24-B6-C13-D23
A69-B6-C13-D23
A67-B6-C13-D23
A39-B6-C13-D23
A65-B6-C13-D23
A66-B6-C13-D23
A2-B32-C13-D23

-continued
A3-B32-C13-D23
A9-B32-C13-D23
A13-B32-C13-D23
A24-B32-C13-D23
A69-B32-C13-D23
A67-B32-C13-D23
A39-B32-C13-D23
A65-B32-C13-D23
A66-B32-C13-D23
A2-B39-C13-D23
A3-B39-C13-D23
A9-B39-C13-D23
A13-B39-C13-D23
A24-B39-C13-D23
A69-B39-C13-D23
A67-B39-C13-D23
A39-B39-C13-D23
A65-B39-C13-D23
A66-B39-C13-D23
A2-B45-C13-D23
A3-B45-C13-D23
A9-B45-C13-D23
A13-B45-C13-D23
A24-B45-C13-D23
A69-B45-C13-D23
A67-B45-C13-D23
A39-B45-C13-D23
A65-B45-C13-D23
A66-B45-C13-D23
A2-B53-C13-D23
A3-B53-C13-D23
A9-B53-C13-D23
A13-B53-C13-D23
A24-B53-C13-D23
A69-B53-C13-D23
A67-B53-C13-D23
A39-B53-C13-D23
A65-B53-C13-D23
A66-B53-C13-D23
A2-B79-C13-D23
A3-B79-C13-D23
A9-B79-C13-D23
A13-B79-C13-D23
A24-B79-C13-D23
A69-B79-C13-D23
A67-B79-C13-D23
A39-B79-C13-D23
A65-B79-C13-D23
A66-B79-C13-D23
A2-B80-C13-D23
A3-B80-C13-D23
A9-B80-C13-D23
A13-B80-C13-D23
A24-B80-C13-D23
A69-B80-C13-D23
A67-B80-C13-D23
A39-B80-C13-D23
A65-B80-C13-D23
A66-B80-C13-D23
A2-B85-C13-D23
A3-B85-C13-D23
A9-B85-C13-D23
A13-B85-C13-D23
A24-B85-C13-D23
A69-B85-C13-D23
A67-B85-C13-D23
A39-B85-C13-D23
A65-B85-C13-D23
A66-B85-C13-D23
A2-B86-C13-D23
A3-B86-C13-D23
A9-B86-C13-D23
A13-B86-C13-D23
A24-B86-C13-D23
A69-B86-C13-D23
A67-B86-C13-D23
A39-B86-C13-D23
A65-B86-C13-D23
A66-B86-C13-D23
A2-B87-C13-D23

-continued
A3-B87-C13-D23
A9-B87-C13-D23
A13-B87-C13-D23
A24-B87-C13-D23
A69-B87-C13-D23
A67-B87-C13-D23
A39-B87-C13-D23
A65-B87-C13-D23
A66-B87-C13-D23
A2-B89-C13-D23
A3-B89-C13-D23
A9-B89-C13-D23
A13-B89-C13-D23
A24-B89-C13-D23
A69-B89-C13-D23
A67-B89-C13-D23
A39-B89-C13-D23
A65-B89-C13-D23
A66-B89-C13-D23
A2-B92-C13-D23
A3-B92-C13-D23
A9-B92-C13-D23
A13-B92-C13-D23
A24-B92-C13-D23
A69-B92-C13-D23
A67-B92-C13-D23
A39-B92-C13-D23
A65-B92-C13-D23
A66-B92-C13-D23
A2-B4-C1-D24
A3-B4-C1-D24
A9-B4-C1-D24
A13-B4-C1-D24
A24-B4-C1-D24
A69-B4-C1-D24
A67-B4-C1-D24
A39-B4-C1-D24
A65-B4-C1-D24
A66-B4-C1-D24
A2-B5-C1-D24
A3-B5-C1-D24
A9-B5-C1-D24
A13-B5-C1-D24
A24-B5-C1-D24
A69-B5-C1-D24
A67-B5-C1-D24
A39-B5-C1-D24
A65-B5-C1-D24
A66-B5-C1-D24
A2-B6-C1-D24
A3-B6-C1-D24
A9-B6-C1-D24
A13-B6-C1-D24
A24-B6-C1-D24
A69-B6-C1-D24
A67-B6-C1-D24
A39-B6-C1-D24
A65-B6-C1-D24
A66-B6-C1-D24
A2-B32-C1-D24
A3-B32-C1-D24
A9-B32-C1-D24
A13-B32-C1-D24
A24-B32-C1-D24
A69-B32-C1-D24
A67-B32-C1-D24
A39-B32-C1-D24
A65-B32-C1-D24
A66-B32-C1-D24
A2-B39-C1-D24
A3-B39-C1-D24
A9-B39-C1-D24
A13-B39-C1-D24
A24-B39-C1-D24
A69-B39-C1-D24
A67-B39-C1-D24
A39-B39-C1-D24
A65-B39-C1-D24
A66-B39-C1-D24
A2-B45-C1-D24

-continued
A3-B45-C1-D24
A9-B45-C1-D24
A13-B45-C1-D24
A24-B45-C1-D24
A69-B45-C1-D24
A67-B45-C1-D24
A39-B45-C1-D24
A65-B45-C1-D24
A66-B45-C1-D24
A2-B53-C1-D24
A3-B53-C1-D24
A9-B53-C1-D24
A13-B53-C1-D24
A24-B53-C1-D24
A69-B53-C1-D24
A67-B53-C1-D24
A39-B53-C1-D24
A65-B53-C1-D24
A66-B53-C1-D24
A2-B79-C1-D24
A3-B79-C1-D24
A9-B79-C1-D24
A13-B79-C1-D24
A24-B79-C1-D24
A69-B79-C1-D24
A67-B79-C1-D24
A39-B79-C1-D24
A65-B79-C1-D24
A66-B79-C1-D24
A2-B80-C1-D24
A3-B80-C1-D24
A9-B80-C1-D24
A13-B80-C1-D24
A24-B80-C1-D24
A69-B80-C1-D24
A67-B80-C1-D24
A39-B80-C1-D24
A65-B80-C1-D24
A66-B80-C1-D24
A2-B85-C1-D24
A3-B85-C1-D24
A9-B85-C1-D24
A13-B85-C1-D24
A24-B85-C1-D24
A69-B85-C1-D24
A67-B85-C1-D24
A39-B85-C1-D24
A65-B85-C1-D24
A66-B85-C1-D24
A2-B86-C1-D24
A3-B86-C1-D24
A9-B86-C1-D24
A13-B86-C1-D24
A24-B86-C1-D24
A69-B86-C1-D24
A67-B86-C1-D24
A39-B86-C1-D24
A65-B86-C1-D24
A66-B86-C1-D24
A2-B87-C1-D24
A3-B87-C1-D24
A9-B87-C1-D24
A13-B87-C1-D24
A24-B87-C1-D24
A69-B87-C1-D24
A67-B87-C1-D24
A39-B87-C1-D24
A65-B87-C1-D24
A66-B87-C1-D24
A2-B89-C1-D24
A3-B89-C1-D24
A9-B89-C1-D24
A13-B89-C1-D24
A24-B89-C1-D24
A69-B89-C1-D24
A67-B89-C1-D24
A39-B89-C1-D24
A65-B89-C1-D24
A66-B89-C1-D24
A2-B92-C1-D24

-continued
A3-B92-C1-D24
A9-B92-C1-D24
A13-B92-C1-D24
A24-B92-C1-D24
A69-B92-C1-D24
A67-B92-C1-D24
A39-B92-C1-D24
A65-B92-C1-D24
A66-B92-C1-D24
A2-B4-C2-D24
A3-B4-C2-D24
A9-B4-C2-D24
A13-B4-C2-D24
A24-B4-C2-D24
A69-B4-C2-D24
A67-B4-C2-D24
A39-B4-C2-D24
A65-B4-C2-D24
A66-B4-C2-D24
A2-B5-C2-D24
A3-B5-C2-D24
A9-B5-C2-D24
A13-B5-C2-D24
A24-B5-C2-D24
A69-B5-C2-D24
A67-B5-C2-D24
A39-B5-C2-D24
A65-B5-C2-D24
A66-B5-C2-D24
A2-B6-C2-D24
A3-B6-C2-D24
A9-B6-C2-D24
A13-B6-C2-D24
A24-B6-C2-D24
A69-B6-C2-D24
A67-B6-C2-D24
A39-B6-C2-D24
A65-B6-C2-D24
A66-B6-C2-D24
A2-B32-C2-D24
A3-B32-C2-D24
A9-B32-C2-D24
A13-B32-C2-D24
A24-B32-C2-D24
A69-B32-C2-D24
A67-B32-C2-D24
A39-B32-C2-D24
A65-B32-C2-D24
A66-B32-C2-D24
A2-B39-C2-D24
A3-B39-C2-D24
A9-B39-C2-D24
A13-B39-C2-D24
A24-B39-C2-D24
A69-B39-C2-D24
A67-B39-C2-D24
A39-B39-C2-D24
A65-B39-C2-D24
A66-B39-C2-D24
A2-B45-C2-D24
A3-B45-C2-D24
A9-B45-C2-D24
A13-B45-C2-D24
A24-B45-C2-D24
A69-B45-C2-D24
A67-B45-C2-D24
A39-B45-C2-D24
A65-B45-C2-D24
A66-B45-C2-D24
A2-B53-C2-D24
A3-B53-C2-D24
A9-B53-C2-D24
A13-B53-C2-D24
A24-B53-C2-D24
A69-B53-C2-D24
A67-B53-C2-D24
A39-B53-C2-D24
A65-B53-C2-D24
A66-B53-C2-D24
A2-B79-C2-D24

-continued
A3-B79-C2-D24
A9-B79-C2-D24
A13-B79-C2-D24
A24-B79-C2-D24
A69-B79-C2-D24
A67-B79-C2-D24
A39-B79-C2-D24
A65-B79-C2-D24
A66-B79-C2-D24
A2-B80-C2-D24
A3-B80-C2-D24
A9-B80-C2-D24
A13-B80-C2-D24
A24-B80-C2-D24
A69-B80-C2-D24
A67-B80-C2-D24
A39-B80-C2-D24
A65-B80-C2-D24
A66-B80-C2-D24
A2-B85-C2-D24
A3-B85-C2-D24
A9-B85-C2-D24
A13-B85-C2-D24
A24-B85-C2-D24
A69-B85-C2-D24
A67-B85-C2-D24
A39-B85-C2-D24
A65-B85-C2-D24
A66-B85-C2-D24
A2-B86-C2-D24
A3-B86-C2-D24
A9-B86-C2-D24
A13-B86-C2-D24
A24-B86-C2-D24
A69-B86-C2-D24
A67-B86-C2-D24
A39-B86-C2-D24
A65-B86-C2-D24
A66-B86-C2-D24
A2-B87-C2-D24
A3-B87-C2-D24
A9-B87-C2-D24
A13-B87-C2-D24
A24-B87-C2-D24
A69-B87-C2-D24
A67-B87-C2-D24
A39-B87-C2-D24
A65-B87-C2-D24
A66-B87-C2-D24
A2-B89-C2-D24
A3-B89-C2-D24
A9-B89-C2-D24
A13-B89-C2-D24
A24-B89-C2-D24
A69-B89-C2-D24
A67-B89-C2-D24
A39-B89-C2-D24
A65-B89-C2-D24
A66-B89-C2-D24
A2-B92-C2-D24
A3-B92-C2-D24
A9-B92-C2-D24
A13-B92-C2-D24
A24-B92-C2-D24
A69-B92-C2-D24
A67-B92-C2-D24
A39-B92-C2-D24
A65-B92-C2-D24
A66-B92-C2-D24
A2-B4-C3-D24
A3-B4-C3-D24
A9-B4-C3-D24
A13-B4-C3-D24
A24-B4-C3-D24
A69-B4-C3-D24
A67-B4-C3-D24
A39-B4-C3-D24
A65-B4-C3-D24
A66-B4-C3-D24
A2-B5-C3-D24

-continued
A3-B5-C3-D24
A9-B5-C3-D24
A13-B5-C3-D24
A24-B5-C3-D24
A69-B5-C3-D24
A67-B5-C3-D24
A39-B5-C3-D24
A65-B5-C3-D24
A66-B5-C3-D24
A2-B6-C3-D24
A3-B6-C3-D24
A9-B6-C3-D24
A13-B6-C3-D24
A24-B6-C3-D24
A69-B6-C3-D24
A67-B6-C3-D24
A39-B6-C3-D24
A65-B6-C3-D24
A66-B6-C3-D24
A2-B32-C3-D24
A3-B32-C3-D24
A9-B32-C3-D24
A13-B32-C3-D24
A24-B32-C3-D24
A69-B32-C3-D24
A67-B32-C3-D24
A39-B32-C3-D24
A65-B32-C3-D24
A66-B32-C3-D24
A2-B39-C3-D24
A3-B39-C3-D24
A9-B39-C3-D24
A13-B39-C3-D24
A24-B39-C3-D24
A69-B39-C3-D24
A67-B39-C3-D24
A39-B39-C3-D24
A65-B39-C3-D24
A66-B39-C3-D24
A2-B45-C3-D24
A3-B45-C3-D24
A9-B45-C3-D24
A13-B45-C3-D24
A24-B45-C3-D24
A69-B45-C3-D24
A67-B45-C3-D24
A39-B45-C3-D24
A65-B45-C3-D24
A66-B45-C3-D24
A2-B53-C3-D24
A3-B53-C3-D24
A9-B53-C3-D24
A13-B53-C3-D24
A24-B53-C3-D24
A69-B53-C3-D24
A67-B53-C3-D24
A39-B53-C3-D24
A65-B53-C3-D24
A66-B53-C3-D24
A2-B79-C3-D24
A3-B79-C3-D24
A9-B79-C3-D24
A13-B79-C3-D24
A24-B79-C3-D24
A69-B79-C3-D24
A67-B79-C3-D24
A39-B79-C3-D24
A65-B79-C3-D24
A66-B79-C3-D24
A2-B80-C3-D24
A3-B80-C3-D24
A9-B80-C3-D24
A13-B80-C3-D24
A24-B80-C3-D24
A69-B80-C3-D24
A67-B80-C3-D24
A39-B80-C3-D24
A65-B80-C3-D24
A66-B80-C3-D24
A2-B85-C3-D24

-continued
A3-B85-C3-D24
A9-B85-C3-D24
A13-B85-C3-D24
A24-B85-C3-D24
A69-B85-C3-D24
A67-B85-C3-D24
A39-B85-C3-D24
A65-B85-C3-D24
A66-B85-C3-D24
A2-B86-C3-D24
A3-B86-C3-D24
A9-B86-C3-D24
A13-B86-C3-D24
A24-B86-C3-D24
A69-B86-C3-D24
A67-B86-C3-D24
A39-B86-C3-D24
A65-B86-C3-D24
A66-B86-C3-D24
A2-B87-C3-D24
A3-B87-C3-D24
A9-B87-C3-D24
A13-B87-C3-D24
A24-B87-C3-D24
A69-B87-C3-D24
A67-B87-C3-D24
A39-B87-C3-D24
A65-B87-C3-D24
A66-B87-C3-D24
A2-B89-C3-D24
A3-B89-C3-D24
A9-B89-C3-D24
A13-B89-C3-D24
A24-B89-C3-D24
A69-B89-C3-D24
A67-B89-C3-D24
A39-B89-C3-D24
A65-B89-C3-D24
A66-B89-C3-D24
A2-B92-C3-D24
A3-B92-C3-D24
A9-B92-C3-D24
A13-B92-C3-D24
A24-B92-C3-D24
A69-B92-C3-D24
A67-B92-C3-D24
A39-B92-C3-D24
A65-B92-C3-D24
A66-B92-C3-D24
A2-B4-C4-D24
A3-B4-C4-D24
A9-B4-C4-D24
A13-B4-C4-D24
A24-B4-C4-D24
A69-B4-C4-D24
A67-B4-C4-D24
A39-B4-C4-D24
A65-B4-C4-D24
A66-B4-C4-D24
A2-B5-C4-D24
A3-B5-C4-D24
A9-B5-C4-D24
A13-B5-C4-D24
A24-B5-C4-D24
A69-B5-C4-D24
A67-B5-C4-D24
A39-B5-C4-D24
A65-B5-C4-D24
A66-B5-C4-D24
A2-B6-C4-D24
A3-B6-C4-D24
A9-B6-C4-D24
A13-B6-C4-D24
A24-B6-C4-D24
A69-B6-C4-D24
A67-B6-C4-D24
A39-B6-C4-D24
A65-B6-C4-D24
A66-B6-C4-D24
A2-B32-C4-D24

-continued
A3-B32-C4-D24
A9-B32-C4-D24
A13-B32-C4-D24
A24-B32-C4-D24
A69-B32-C4-D24
A67-B32-C4-D24
A39-B32-C4-D24
A65-B32-C4-D24
A66-B32-C4-D24
A2-B39-C4-D24
A3-B39-C4-D24
A9-B39-C4-D24
A13-B39-C4-D24
A24-B39-C4-D24
A69-B39-C4-D24
A67-B39-C4-D24
A39-B39-C4-D24
A65-B39-C4-D24
A66-B39-C4-D24
A2-B45-C4-D24
A3-B45-C4-D24
A9-B45-C4-D24
A13-B45-C4-D24
A24-B45-C4-D24
A69-B45-C4-D24
A67-B45-C4-D24
A39-B45-C4-D24
A65-B45-C4-D24
A66-B45-C4-D24
A2-B53-C4-D24
A3-B53-C4-D24
A9-B53-C4-D24
A13-B53-C4-D24
A24-B53-C4-D24
A69-B53-C4-D24
A67-B53-C4-D24
A39-B53-C4-D24
A65-B53-C4-D24
A66-B53-C4-D24
A2-B79-C4-D24
A3-B79-C4-D24
A9-B79-C4-D24
A13-B79-C4-D24
A24-B79-C4-D24
A69-B79-C4-D24
A67-B79-C4-D24
A39-B79-C4-D24
A65-B79-C4-D24
A66-B79-C4-D24
A2-B80-C4-D24
A3-B80-C4-D24
A9-B80-C4-D24
A13-B80-C4-D24
A24-B80-C4-D24
A69-B80-C4-D24
A67-B80-C4-D24
A39-B80-C4-D24
A65-B80-C4-D24
A66-B80-C4-D24
A2-B85-C4-D24
A3-B85-C4-D24
A9-B85-C4-D24
A13-B85-C4-D24
A24-B85-C4-D24
A69-B85-C4-D24
A67-B85-C4-D24
A39-B85-C4-D24
A65-B85-C4-D24
A66-B85-C4-D24
A2-B86-C4-D24
A3-B86-C4-D24
A9-B86-C4-D24
A13-B86-C4-D24
A24-B86-C4-D24
A69-B86-C4-D24
A67-B86-C4-D24
A39-B86-C4-D24
A65-B86-C4-D24
A66-B86-C4-D24
A2-B87-C4-D24

-continued
A3-B87-C4-D24
A9-B87-C4-D24
A13-B87-C4-D24
A24-B87-C4-D24
A69-B87-C4-D24
A67-B87-C4-D24
A39-B87-C4-D24
A65-B87-C4-D24
A66-B87-C4-D24
A2-B89-C4-D24
A3-B89-C4-D24
A9-B89-C4-D24
A13-B89-C4-D24
A24-B89-C4-D24
A69-B89-C4-D24
A67-B89-C4-D24
A39-B89-C4-D24
A65-B89-C4-D24
A66-B89-C4-D24
A2-B92-C4-D24
A3-B92-C4-D24
A9-B92-C4-D24
A13-B92-C4-D24
A24-B92-C4-D24
A69-B92-C4-D24
A67-B92-C4-D24
A39-B92-C4-D24
A65-B92-C4-D24
A66-B92-C4-D24
A2-B4-C5-D24
A3-B4-C5-D24
A9-B4-C5-D24
A13-B4-C5-D24
A24-B4-C5-D24
A69-B4-C5-D24
A67-B4-C5-D24
A39-B4-C5-D24
A65-B4-C5-D24
A66-B4-C5-D24
A2-B5-C5-D24
A3-B5-C5-D24
A9-B5-C5-D24
A13-B5-C5-D24
A24-B5-C5-D24
A69-B5-C5-D24
A67-B5-C5-D24
A39-B5-C5-D24
A65-B5-C5-D24
A66-B5-C5-D24
A2-B6-C5-D24
A3-B6-C5-D24
A9-B6-C5-D24
A13-B6-C5-D24
A24-B6-C5-D24
A69-B6-C5-D24
A67-B6-C5-D24
A39-B6-C5-D24
A65-B6-C5-D24
A66-B6-C5-D24
A2-B32-C5-D24
A3-B32-C5-D24
A9-B32-C5-D24
A13-B32-C5-D24
A24-B32-C5-D24
A69-B32-C5-D24
A67-B32-C5-D24
A39-B32-C5-D24
A65-B32-C5-D24
A66-B32-C5-D24
A2-B39-C5-D24
A3-B39-C5-D24
A9-B39-C5-D24
A13-B39-C5-D24
A24-B39-C5-D24
A69-B39-C5-D24
A67-B39-C5-D24
A39-B39-C5-D24
A65-B39-C5-D24
A66-B39-C5-D24
A2-B45-C5-D24

-continued

A3-B45-C5-D24
A9-B45-C5-D24
A13-B45-C5-D24
A24-B45-C5-D24
A69-B45-C5-D24
A67-B45-C5-D24
A39-B45-C5-D24
A65-B45-C5-D24
A66-B45-C5-D24
A2-B53-C5-D24
A3-B53-C5-D24
A9-B53-C5-D24
A13-B53-C5-D24
A24-B53-C5-D24
A69-B53-C5-D24
A67-B53-C5-D24
A39-B53-C5-D24
A65-B53-C5-D24
A66-B53-C5-D24
A2-B79-C5-D24
A3-B79-C5-D24
A9-B79-C5-D24
A13-B79-C5-D24
A24-B79-C5-D24
A69-B79-C5-D24
A67-B79-C5-D24
A39-B79-C5-D24
A65-B79-C5-D24
A66-B79-C5-D24
A2-B80-C5-D24
A3-B80-C5-D24
A9-B80-C5-D24
A13-B80-C5-D24
A24-B80-C5-D24
A69-B80-C5-D24
A67-B80-C5-D24
A39-B80-C5-D24
A65-B80-C5-D24
A66-B80-C5-D24
A2-B85-C5-D24
A3-B85-C5-D24
A9-B85-C5-D24
A13-B85-C5-D24
A24-B85-C5-D24
A69-B85-C5-D24
A67-B85-C5-D24
A39-B85-C5-D24
A65-B85-C5-D24
A66-B85-C5-D24
A2-B86-C5-D24
A3-B86-C5-D24
A9-B86-C5-D24
A13-B86-C5-D24
A24-B86-C5-D24
A69-B86-C5-D24
A67-B86-C5-D24
A39-B86-C5-D24
A65-B86-C5-D24
A66-B86-C5-D24
A2-B87-C5-D24
A3-B87-C5-D24
A9-B87-C5-D24
A13-B87-C5-D24
A24-B87-C5-D24
A69-B87-C5-D24
A67-B87-C5-D24
A39-B87-C5-D24
A65-B87-C5-D24
A66-B87-C5-D24
A2-B89-C5-D24
A3-B89-C5-D24
A9-B89-C5-D24
A13-B89-C5-D24
A24-B89-C5-D24
A69-B89-C5-D24
A67-B89-C5-D24
A39-B89-C5-D24
A65-B89-C5-D24
A66-B89-C5-D24
A2-B92-C5-D24

-continued

A3-B92-C5-D24
A9-B92-C5-D24
A13-B92-C5-D24
A24-B92-C5-D24
A69-B92-C5-D24
A67-B92-C5-D24
A39-B92-C5-D24
A65-B92-C5-D24
A66-B92-C5-D24
A2-B4-C6-D24
A3-B4-C6-D24
A9-B4-C6-D24
A13-B4-C6-D24
A24-B4-C6-D24
A69-B4-C6-D24
A67-B4-C6-D24
A39-B4-C6-D24
A65-B4-C6-D24
A66-B4-C6-D24
A2-B5-C6-D24
A3-B5-C6-D24
A9-B5-C6-D24
A13-B5-C6-D24
A24-B5-C6-D24
A69-B5-C6-D24
A67-B5-C6-D24
A39-B5-C6-D24
A65-B5-C6-D24
A66-B5-C6-D24
A2-B6-C6-D24
A3-B6-C6-D24
A9-B6-C6-D24
A13-B6-C6-D24
A24-B6-C6-D24
A69-B6-C6-D24
A67-B6-C6-D24
A39-B6-C6-D24
A65-B6-C6-D24
A66-B6-C6-D24
A2-B32-C6-D24
A3-B32-C6-D24
A9-B32-C6-D24
A13-B32-C6-D24
A24-B32-C6-D24
A69-B32-C6-D24
A67-B32-C6-D24
A39-B32-C6-D24
A65-B32-C6-D24
A66-B32-C6-D24
A2-B39-C6-D24
A3-B39-C6-D24
A9-B39-C6-D24
A13-B39-C6-D24
A24-B39-C6-D24
A69-B39-C6-D24
A67-B39-C6-D24
A39-B39-C6-D24
A65-B39-C6-D24
A66-B39-C6-D24
A2-B45-C6-D24
A3-B45-C6-D24
A9-B45-C6-D24
A13-B45-C6-D24
A24-B45-C6-D24
A69-B45-C6-D24
A67-B45-C6-D24
A39-B45-C6-D24
A65-B45-C6-D24
A66-B45-C6-D24
A2-B53-C6-D24
A3-B53-C6-D24
A9-B53-C6-D24
A13-B53-C6-D24
A24-B53-C6-D24
A69-B53-C6-D24
A67-B53-C6-D24
A39-B53-C6-D24
A65-B53-C6-D24
A66-B53-C6-D24
A2-B79-C6-D24

-continued
A3-B79-C6-D24
A9-B79-C6-D24
A13-B79-C6-D24
A24-B79-C6-D24
A69-B79-C6-D24
A67-B79-C6-D24
A39-B79-C6-D24
A65-B79-C6-D24
A66-B79-C6-D24
A2-B80-C6-D24
A3-B80-C6-D24
A9-B80-C6-D24
A13-B80-C6-D24
A24-B80-C6-D24
A69-B80-C6-D24
A67-B80-C6-D24
A39-B80-C6-D24
A65-B80-C6-D24
A66-B80-C6-D24
A2-B85-C6-D24
A3-B85-C6-D24
A9-B85-C6-D24
A13-B85-C6-D24
A24-B85-C6-D24
A69-B85-C6-D24
A67-B85-C6-D24
A39-B85-C6-D24
A65-B85-C6-D24
A66-B85-C6-D24
A2-B86-C6-D24
A3-B86-C6-D24
A9-B86-C6-D24
A13-B86-C6-D24
A24-B86-C6-D24
A69-B86-C6-D24
A67-B86-C6-D24
A39-B86-C6-D24
A65-B86-C6-D24
A66-B86-C6-D24
A2-B87-C6-D24
A3-B87-C6-D24
A9-B87-C6-D24
A13-B87-C6-D24
A24-B87-C6-D24
A69-B87-C6-D24
A67-B87-C6-D24
A39-B87-C6-D24
A65-B87-C6-D24
A66-B87-C6-D24
A2-B89-C6-D24
A3-B89-C6-D24
A9-B89-C6-D24
A13-B89-C6-D24
A24-B89-C6-D24
A69-B89-C6-D24
A67-B89-C6-D24
A39-B89-C6-D24
A65-B89-C6-D24
A66-B89-C6-D24
A2-B92-C6-D24
A3-B92-C6-D24
A9-B92-C6-D24
A13-B92-C6-D24
A24-B92-C6-D24
A69-B92-C6-D24
A67-B92-C6-D24
A39-B92-C6-D24
A65-B92-C6-D24
A66-B92-C6-D24
A2-B4-C7-D24
A3-B4-C7-D24
A9-B4-C7-D24
A13-B4-C7-D24
A24-B4-C7-D24
A69-B4-C7-D24
A67-B4-C7-D24
A39-B4-C7-D24
A65-B4-C7-D24
A66-B4-C7-D24
A2-B5-C7-D24

-continued
A3-B5-C7-D24
A9-B5-C7-D24
A13-B5-C7-D24
A24-B5-C7-D24
A69-B5-C7-D24
A67-B5-C7-D24
A39-B5-C7-D24
A65-B5-C7-D24
A66-B5-C7-D24
A2-B6-C7-D24
A3-B6-C7-D24
A9-B6-C7-D24
A13-B6-C7-D24
A24-B6-C7-D24
A69-B6-C7-D24
A67-B6-C7-D24
A39-B6-C7-D24
A65-B6-C7-D24
A66-B6-C7-D24
A2-B32-C7-D24
A3-B32-C7-D24
A9-B32-C7-D24
A13-B32-C7-D24
A24-B32-C7-D24
A69-B32-C7-D24
A67-B32-C7-D24
A39-B32-C7-D24
A65-B32-C7-D24
A66-B32-C7-D24
A2-B39-C7-D24
A3-B39-C7-D24
A9-B39-C7-D24
A13-B39-C7-D24
A24-B39-C7-D24
A69-B39-C7-D24
A67-B39-C7-D24
A39-B39-C7-D24
A65-B39-C7-D24
A66-B39-C7-D24
A2-B45-C7-D24
A3-B45-C7-D24
A9-B45-C7-D24
A13-B45-C7-D24
A24-B45-C7-D24
A69-B45-C7-D24
A67-B45-C7-D24
A39-B45-C7-D24
A65-B45-C7-D24
A66-B45-C7-D24
A2-B53-C7-D24
A3-B53-C7-D24
A9-B53-C7-D24
A13-B53-C7-D24
A24-B53-C7-D24
A69-B53-C7-D24
A67-B53-C7-D24
A39-B53-C7-D24
A65-B53-C7-D24
A66-B53-C7-D24
A2-B79-C7-D24
A3-B79-C7-D24
A9-B79-C7-D24
A13-B79-C7-D24
A24-B79-C7-D24
A69-B79-C7-D24
A67-B79-C7-D24
A39-B79-C7-D24
A65-B79-C7-D24
A66-B79-C7-D24
A2-B80-C7-D24
A3-B80-C7-D24
A9-B80-C7-D24
A13-B80-C7-D24
A24-B80-C7-D24
A69-B80-C7-D24
A67-B80-C7-D24
A39-B80-C7-D24
A65-B80-C7-D24
A66-B80-C7-D24
A2-B85-C7-D24

-continued
A3-B85-C7-D24
A9-B85-C7-D24
A13-B85-C7-D24
A24-B85-C7-D24
A69-B85-C7-D24
A67-B85-C7-D24
A39-B85-C7-D24
A65-B85-C7-D24
A66-B85-C7-D24
A2-B86-C7-D24
A3-B86-C7-D24
A9-B86-C7-D24
A13-B86-C7-D24
A24-B86-C7-D24
A69-B86-C7-D24
A67-B86-C7-D24
A39-B86-C7-D24
A65-B86-C7-D24
A66-B86-C7-D24
A2-B87-C7-D24
A3-B87-C7-D24
A9-B87-C7-D24
A13-B87-C7-D24
A24-B87-C7-D24
A69-B87-C7-D24
A67-B87-C7-D24
A39-B87-C7-D24
A65-B87-C7-D24
A66-B87-C7-D24
A2-B89-C7-D24
A3-B89-C7-D24
A9-B89-C7-D24
A13-B89-C7-D24
A24-B89-C7-D24
A69-B89-C7-D24
A67-B89-C7-D24
A39-B89-C7-D24
A65-B89-C7-D24
A66-B89-C7-D24
A2-B92-C7-D24
A3-B92-C7-D24
A9-B92-C7-D24
A13-B92-C7-D24
A24-B92-C7-D24
A69-B92-C7-D24
A67-B92-C7-D24
A39-B92-C7-D24
A65-B92-C7-D24
A66-B92-C7-D24
A2-B4-C8-D24
A3-B4-C8-D24
A9-B4-C8-D24
A13-B4-C8-D24
A24-B4-C8-D24
A69-B4-C8-D24
A67-B4-C8-D24
A39-B4-C8-D24
A65-B4-C8-D24
A66-B4-C8-D24
A2-B5-C8-D24
A3-B5-C8-D24
A9-B5-C8-D24
A13-B5-C8-D24
A24-B5-C8-D24
A69-B5-C8-D24
A67-B5-C8-D24
A39-B5-C8-D24
A65-B5-C8-D24
A66-B5-C8-D24
A2-B6-C8-D24
A3-B6-C8-D24
A9-B6-C8-D24
A13-B6-C8-D24
A24-B6-C8-D24
A69-B6-C8-D24
A67-B6-C8-D24
A39-B6-C8-D24
A65-B6-C8-D24
A66-B6-C8-D24
A2-B32-C8-D24

-continued
A3-B32-C8-D24
A9-B32-C8-D24
A13-B32-C8-D24
A24-B32-C8-D24
A69-B32-C8-D24
A67-B32-C8-D24
A39-B32-C8-D24
A65-B32-C8-D24
A66-B32-C8-D24
A2-B39-C8-D24
A3-B39-C8-D24
A9-B39-C8-D24
A13-B39-C8-D24
A24-B39-C8-D24
A69-B39-C8-D24
A67-B39-C8-D24
A39-B39-C8-D24
A65-B39-C8-D24
A66-B39-C8-D24
A2-B45-C8-D24
A3-B45-C8-D24
A9-B45-C8-D24
A13-B45-C8-D24
A24-B45-C8-D24
A69-B45-C8-D24
A67-B45-C8-D24
A39-B45-C8-D24
A65-B45-C8-D24
A66-B45-C8-D24
A2-B53-C8-D24
A3-B53-C8-D24
A9-B53-C8-D24
A13-B53-C8-D24
A24-B53-C8-D24
A69-B53-C8-D24
A67-B53-C8-D24
A39-B53-C8-D24
A65-B53-C8-D24
A66-B53-C8-D24
A2-B79-C8-D24
A3-B79-C8-D24
A9-B79-C8-D24
A13-B79-C8-D24
A24-B79-C8-D24
A69-B79-C8-D24
A67-B79-C8-D24
A39-B79-C8-D24
A65-B79-C8-D24
A66-B79-C8-D24
A2-B80-C8-D24
A3-B80-C8-D24
A9-B80-C8-D24
A13-B80-C8-D24
A24-B80-C8-D24
A69-B80-C8-D24
A67-B80-C8-D24
A39-B80-C8-D24
A65-B80-C8-D24
A66-B80-C8-D24
A2-B85-C8-D24
A3-B85-C8-D24
A9-B85-C8-D24
A13-B85-C8-D24
A24-B85-C8-D24
A69-B85-C8-D24
A67-B85-C8-D24
A39-B85-C8-D24
A65-B85-C8-D24
A66-B85-C8-D24
A2-B86-C8-D24
A3-B86-C8-D24
A9-B86-C8-D24
A13-B86-C8-D24
A24-B86-C8-D24
A69-B86-C8-D24
A67-B86-C8-D24
A39-B86-C8-D24
A65-B86-C8-D24
A66-B86-C8-D24
A2-B87-C8-D24

-continued

A3-B87-C8-D24
A9-B87-C8-D24
A13-B87-C8-D24
A24-B87-C8-D24
A69-B87-C8-D24
A67-B87-C8-D24
A39-B87-C8-D24
A65-B87-C8-D24
A66-B87-C8-D24
A2-B89-C8-D24
A3-B89-C8-D24
A9-B89-C8-D24
A13-B89-C8-D24
A24-B89-C8-D24
A69-B89-C8-D24
A67-B89-C8-D24
A39-B89-C8-D24
A65-B89-C8-D24
A66-B89-C8-D24
A2-B92-C8-D24
A3-B92-C8-D24
A9-B92-C8-D24
A13-B92-C8-D24
A24-B92-C8-D24
A69-B92-C8-D24
A67-B92-C8-D24
A39-B92-C8-D24
A65-B92-C8-D24
A66-B92-C8-D24
A2-B4-C9-D24
A3-B4-C9-D24
A9-B4-C9-D24
A13-B4-C9-D24
A24-B4-C9-D24
A69-B4-C9-D24
A67-B4-C9-D24
A39-B4-C9-D24
A65-B4-C9-D24
A66-B4-C9-D24
A2-B5-C9-D24
A3-B5-C9-D24
A9-B5-C9-D24
A13-B5-C9-D24
A24-B5-C9-D24
A69-B5-C9-D24
A67-B5-C9-D24
A39-B5-C9-D24
A65-B5-C9-D24
A66-B5-C9-D24
A2-B6-C9-D24
A3-B6-C9-D24
A9-B6-C9-D24
A13-B6-C9-D24
A24-B6-C9-D24
A69-B6-C9-D24
A67-B6-C9-D24
A39-B6-C9-D24
A65-B6-C9-D24
A66-B6-C9-D24
A2-B32-C9-D24
A3-B32-C9-D24
A9-B32-C9-D24
A13-B32-C9-D24
A24-B32-C9-D24
A69-B32-C9-D24
A67-B32-C9-D24
A39-B32-C9-D24
A65-B32-C9-D24
A66-B32-C9-D24
A2-B39-C9-D24
A3-B39-C9-D24
A9-B39-C9-D24
A13-B39-C9-D24
A24-B39-C9-D24
A69-B39-C9-D24
A67-B39-C9-D24
A39-B39-C9-D24
A65-B39-C9-D24
A66-B39-C9-D24
A2-B45-C9-D24

-continued

A3-B45-C9-D24
A9-B45-C9-D24
A13-B45-C9-D24
A24-B45-C9-D24
A69-B45-C9-D24
A67-B45-C9-D24
A39-B45-C9-D24
A65-B45-C9-D24
A66-B45-C9-D24
A2-B53-C9-D24
A3-B53-C9-D24
A9-B53-C9-D24
A13-B53-C9-D24
A24-B53-C9-D24
A69-B53-C9-D24
A67-B53-C9-D24
A39-B53-C9-D24
A65-B53-C9-D24
A66-B53-C9-D24
A2-B79-C9-D24
A3-B79-C9-D24
A9-B79-C9-D24
A13-B79-C9-D24
A24-B79-C9-D24
A69-B79-C9-D24
A67-B79-C9-D24
A39-B79-C9-D24
A65-B79-C9-D24
A66-B79-C9-D24
A2-B80-C9-D24
A3-B80-C9-D24
A9-B80-C9-D24
A13-B80-C9-D24
A24-B80-C9-D24
A69-B80-C9-D24
A67-B80-C9-D24
A39-B80-C9-D24
A65-B80-C9-D24
A66-B80-C9-D24
A2-B85-C9-D24
A3-B85-C9-D24
A9-B85-C9-D24
A13-B85-C9-D24
A24-B85-C9-D24
A69-B85-C9-D24
A67-B85-C9-D24
A39-B85-C9-D24
A65-B85-C9-D24
A66-B85-C9-D24
A2-B86-C9-D24
A3-B86-C9-D24
A9-B86-C9-D24
A13-B86-C9-D24
A24-B86-C9-D24
A69-B86-C9-D24
A67-B86-C9-D24
A39-B86-C9-D24
A65-B86-C9-D24
A66-B86-C9-D24
A2-B87-C9-D24
A3-B87-C9-D24
A9-B87-C9-D24
A13-B87-C9-D24
A24-B87-C9-D24
A69-B87-C9-D24
A67-B87-C9-D24
A39-B87-C9-D24
A65-B87-C9-D24
A66-B87-C9-D24
A2-B89-C9-D24
A3-B89-C9-D24
A9-B89-C9-D24
A13-B89-C9-D24
A24-B89-C9-D24
A69-B89-C9-D24
A67-B89-C9-D24
A39-B89-C9-D24
A65-B89-C9-D24
A66-B89-C9-D24
A2-B92-C9-D24

-continued

A3-B92-C9-D24
A9-B92-C9-D24
A13-B92-C9-D24
A24-B92-C9-D24
A69-B92-C9-D24
A67-B92-C9-D24
A39-B92-C9-D24
A65-B92-C9-D24
A66-B92-C9-D24
A2-B4-C10-D24
A3-B4-C10-D24
A9-B4-C10-D24
A13-B4-C10-D24
A24-B4-C10-D24
A69-B4-C10-D24
A67-B4-C10-D24
A39-B4-C10-D24
A65-B4-C10-D24
A66-B4-C10-D24
A2-B5-C10-D24
A3-B5-C10-D24
A9-B5-C10-D24
A13-B5-C10-D24
A24-B5-C10-D24
A69-B5-C10-D24
A67-B5-C10-D24
A39-B5-C10-D24
A65-B5-C10-D24
A66-B5-C10-D24
A2-B6-C10-D24
A3-B6-C10-D24
A9-B6-C10-D24
A13-B6-C10-D24
A24-B6-C10-D24
A69-B6-C10-D24
A67-B6-C10-D24
A39-B6-C10-D24
A65-B6-C10-D24
A66-B6-C10-D24
A2-B32-C10-D24
A3-B32-C10-D24
A9-B32-C10-D24
A13-B32-C10-D24
A24-B32-C10-D24
A69-B32-C10-D24
A67-B32-C10-D24
A39-B32-C10-D24
A65-B32-C10-D24
A66-B32-C10-D24
A2-B39-C10-D24
A3-B39-C10-D24
A9-B39-C10-D24
A13-B39-C10-D24
A24-B39-C10-D24
A69-B39-C10-D24
A67-B39-C10-D24
A39-B39-C10-D24
A65-B39-C10-D24
A66-B39-C10-D24
A2-B45-C10-D24
A3-B45-C10-D24
A9-B45-C10-D24
A13-B45-C10-D24
A24-B45-C10-D24
A69-B45-C10-D24
A67-B45-C10-D24
A39-B45-C10-D24
A65-B45-C10-D24
A66-B45-C10-D24
A2-B53-C10-D24
A3-B53-C10-D24
A9-B53-C10-D24
A13-B53-C10-D24
A24-B53-C10-D24
A69-B53-C10-D24
A67-B53-C10-D24
A39-B53-C10-D24
A65-B53-C10-D24
A66-B53-C10-D24
A2-B79-C10-D24

-continued

A3-B79-C10-D24
A9-B79-C10-D24
A13-B79-C10-D24
A14-B79-C10-D24
A69-B79-C10-D24
A67-B79-C10-D24
A39-B79-C10-D24
A65-B79-C10-D24
A66-B79-C10-D24
A2-B80-C10-D24
A3-B80-C10-D24
A9-B80-C10-D24
A13-B80-C10-D24
A24-B80-C10-D24
A69-B80-C10-D24
A67-B80-C10-D24
A39-B80-C10-D24
A65-B80-C10-D24
A66-B80-C10-D24
A2-B85-C10-D24
A3-B85-C10-D24
A9-B85-C10-D24
A13-B85-C10-D24
A24-B85-C10-D24
A69-B85-C10-D24
A67-B85-C10-D24
A39-B85-C10-D24
A65-B85-C10-D24
A66-B85-C10-D24
A2-B86-C10-D24
A3-B86-C10-D24
A9-B86-C10-D24
A13-B86-C10-D24
A24-B86-C10-D24
A69-B86-C10-D24
A67-B86-C10-D24
A39-B86-C10-D24
A65-B86-C10-D24
A66-B86-C10-D24
A2-B87-C10-D24
A3-B87-C10-D24
A9-B87-C10-D24
A13-B87-C10-D24
A24-B87-C10-D24
A69-B87-C10-D24
A67-B87-C10-D24
A39-B87-C10-D24
A65-B87-C10-D24
A66-B87-C10-D24
A2-B89-C10-D24
A3-B89-C10-D24
A9-B89-C10-D24
A13-B89-C10-D24
A24-B89-C10-D24
A69-B89-C10-D24
A67-B89-C10-D24
A39-B89-C10-D24
A65-B89-C10-D24
A66-B89-C10-D24
A2-B92-C10-D24
A3-B92-C10-D24
A9-B92-C10-D24
A13-B92-C10-D24
A24-B92-C10-D24
A69-B92-C10-D24
A67-B92-C10-D24
A39-B92-C10-D24
A65-B92-C10-D24
A66-B92-C10-D24
A2-B4-C11-D24
A3-B4-C11-D24
A9-B4-C11-D24
A13-B4-C11-D24
A24-B4-C11-D24
A69-B4-C11-D24
A67-B4-C11-D24
A39-B4-C11-D24
A65-B4-C11-D24
A66-B4-C11-D24
A2-B5-C11-D24

-continued
A3-B5-C11-D24
A9-B5-C11-D24
A13-B5-C11-D24
A24-B5-C11-D24
A69-B5-C11-D24
A67-B5-C11-D24
A39-B5-C11-D24
A65-B5-C11-D24
A66-B5-C11-D24
A2-B6-C11-D24
A3-B6-C11-D24
A9-B6-C11-D24
A13-B6-C11-D24
A24-B6-C11-D24
A69-B6-C11-D24
A67-B6-C11-D24
A39-B6-C11-D24
A65-B6-C11-D24
A66-B6-C11-D24
A2-B32-C11-D24
A3-B32-C11-D24
A9-B32-C11-D24
A13-B32-C11-D24
A24-B32-C11-D24
A69-B32-C11-D24
A67-B32-C11-D24
A39-B32-C11-D24
A65-B32-C11-D24
A66-B32-C11-D24
A2-B39-C11-D24
A3-B39-C11-D24
A9-B39-C11-D24
A13-B39-C11-D24
A24-B39-C11-D24
A69-B39-C11-D24
A67-B39-C11-D24
A39-B39-C11-D24
A65-B39-C11-D24
A66-B39-C11-D24
A2-B45-C11-D24
A3-B45-C11-D24
A9-B45-C11-D24
A13-B45-C11-D24
A24-B45-C11-D24
A69-B45-C11-D24
A67-B45-C11-D24
A39-B45-C11-D24
A65-B45-C11-D24
A66-B45-C11-D24
A2-B53-C11-D24
A3-B53-C11-D24
A9-B53-C11-D24
A13-B53-C11-D24
A24-B53-C11-D24
A69-B53-C11-D24
A67-B53-C11-D24
A39-B53-C11-D24
A65-B53-C11-D24
A66-B53-C11-D24
A2-B79-C11-D24
A3-B79-C11-D24
A9-B79-C11-D24
A13-B79-C11-D24
A24-B79-C11-D24
A69-B79-C11-D24
A67-B79-C11-D24
A39-B79-C11-D24
A65-B79-C11-D24
A66-B79-C11-D24
A2-B80-C11-D24
A3-B80-C11-D24
A9-B80-C11-D24
A13-B80-C11-D24
A24-B80-C11-D24
A69-B80-C11-D24
A67-B80-C11-D24
A39-B80-C11-D24
A65-B80-C11-D24
A66-B80-C11-D24
A2-B85-C11-D24

-continued
A3-B85-C11-D24
A9-B85-C11-D24
A13-B85-C11-D24
A24-B85-C11-D24
A69-B85-C11-D24
A67-B85-C11-D24
A39-B85-C11-D24
A65-B85-C11-D24
A66-B85-C11-D24
A2-B86-C11-D24
A3-B86-C11-D24
A9-B86-C11-D24
A13-B86-C11-D24
A24-B86-C11-D24
A69-B86-C11-D24
A67-B86-C11-D24
A39-B86-C11-D24
A65-B86-C11-D24
A66-B86-C11-D24
A2-B87-C11-D24
A3-B87-C11-D24
A9-B87-C11-D24
A13-B87-C11-D24
A24-B87-C11-D24
A69-B87-C11-D24
A67-B87-C11-D24
A39-B87-C11-D24
A65-B87-C11-D24
A66-B87-C11-D24
A2-B89-C11-D24
A3-B89-C11-D24
A9-B89-C11-D24
A13-B89-C11-D24
A24-B89-C11-D24
A69-B89-C11-D24
A67-B89-C11-D24
A39-B89-C11-D24
A65-B89-C11-D24
A66-B89-C11-D24
A2-B92-C11-D24
A3-B92-C11-D24
A9-B92-C11-D24
A13-B92-C11-D24
A24-B92-C11-D24
A69-B92-C11-D24
A67-B92-C11-D24
A39-B92-C11-D24
A65-B92-C11-D24
A66-B92-C11-D24
A2-B4-C12-D24
A3-B4-C12-D24
A9-B4-C12-D24
A13-B4-C12-D24
A24-B4-C12-D24
A69-B4-C12-D24
A67-B4-C12-D24
A39-B4-C12-D24
A65-B4-C12-D24
A66-B4-C12-D24
A2-B5-C12-D24
A3-B5-C12-D24
A9-B5-C12-D24
A13-B5-C12-D24
A24-B5-C12-D24
A69-B5-C12-D24
A67-B5-C12-D24
A39-B5-C12-D24
A65-B5-C12-D24
A66-B5-C12-D24
A2-B6-C12-D24
A3-B6-C12-D24
A9-B6-C12-D24
A13-B6-C12-D24
A24-B6-C12-D24
A69-B6-C12-D24
A67-B6-C12-D24
A39-B6-C12-D24
A65-B6-C12-D24
A66-B6-C12-D24
A2-B32-C12-D24

-continued

A3-B32-C12-D24
A9-B32-C12-D24
A13-B32-C12-D24
A24-B32-C12-D24
A69-B32-C12-D24
A67-B32-C12-D24
A39-B32-C12-D24
A65-B32-C12-D24
A66-B32-C12-D24
A2-B39-C12-D24
A3-B39-C12-D24
A9-B39-C12-D24
A13-B39-C12-D24
A24-B39-C12-D24
A69-B39-C12-D24
A67-B39-C12-D24
A39-B39-C12-D24
A65-B39-C12-D24
A66-B39-C12-D24
A2-B45-C12-D24
A3-B45-C12-D24
A9-B45-C12-D24
A13-B45-C12-D24
A24-B45-C12-D24
A69-B45-C12-D24
A67-B45-C12-D24
A39-B45-C12-D24
A65-B45-C12-D24
A66-B45-C12-D24
A2-B53-C12-D24
A3-B53-C12-D24
A9-B53-C12-D24
A13-B53-C12-D24
A24-B53-C12-D24
A69-B53-C12-D24
A67-B53-C12-D24
A39-B53-C12-D24
A65-B53-C12-D24
A66-B53-C12-D24
A2-B79-C12-D24
A3-B79-C12-D24
A9-B79-C12-D24
A13-B79-C12-D24
A24-B79-C12-D24
A69-B79-C12-D24
A67-B79-C12-D24
A39-B79-C12-D24
A65-B79-C12-D24
A66-B79-C12-D24
A2-B80-C12-D24
A3-B80-C12-D24
A9-B80-C12-D24
A13-B80-C12-D24
A24-B80-C12-D24
A69-B80-C12-D24
A67-B80-C12-D24
A39-B80-C12-D24
A65-B80-C12-D24
A66-B80-C12-D24
A2-B85-C12-D24
A3-B85-C12-D24
A9-B85-C12-D24
A13-B85-C12-D24
A24-B85-C12-D24
A69-B85-C12-D24
A67-B85-C12-D24
A39-B85-C12-D24
A65-B85-C12-D24
A66-B85-C12-D24
A2-B86-C12-D24
A3-B86-C12-D24
A9-B86-C12-D24
A13-B86-C12-D24
A24-B86-C12-D24
A69-B86-C12-D24
A67-B86-C12-D24
A39-B86-C12-D24
A65-B86-C12-D24
A66-B86-C12-D24
A2-B87-C12-D24

-continued

A3-B87-C12-D24
A9-B87-C12-D24
A13-B87-C12-D24
A24-B87-C12-D24
A69-B87-C12-D24
A67-B87-C12-D24
A39-B87-C12-D24
A65-B87-C12-D24
A66-B87-C12-D24
A2-B89-C12-D24
A3-B89-C12-D24
A9-B89-C12-D24
A13-B89-C12-D24
A24-B89-C12-D24
A69-B89-C12-D24
A67-B89-C12-D24
A39-B89-C12-D24
A65-B89-C12-D24
A66-B89-C12-D24
A2-B92-C12-D24
A3-B92-C12-D24
A9-B92-C12-D24
A13-B92-C12-D24
A24-B92-C12-D24
A69-B92-C12-D24
A67-B92-C12-D24
A39-B92-C12-D24
A65-B92-C12-D24
A66-B92-C12-D24
A2-B4-C13-D24
A3-B4-C13-D24
A9-B4-C13-D24
A13-B4-C13-D24
A24-B4-C13-D24
A69-B4-C13-D24
A67-B4-C13-D24
A39-B4-C13-D24
A65-B4-C13-D24
A66-B4-C13-D24
A2-B5-C13-D24
A3-B5-C13-D24
A9-B5-C13-D24
A13-B5-C13-D24
A24-B5-C13-D24
A69-B5-C13-D24
A67-B5-C13-D24
A39-B5-C13-D24
A65-B5-C13-D24
A66-B5-C13-D24
A2-B6-C13-D24
A3-B6-C13-D24
A9-B6-C13-D24
A13-B6-C13-D24
A24-B6-C13-D24
A69-B6-C13-D24
A67-B6-C13-D24
A39-B6-C13-D24
A65-B6-C13-D24
A66-B6-C13-D24
A2-B32-C13-D24
A3-B32-C13-D24
A9-B32-C13-D24
A13-B32-C13-D24
A24-B32-C13-D24
A69-B32-C13-D24
A67-B32-C13-D24
A39-B32-C13-D24
A65-B32-C13-D24
A66-B32-C13-D24
A2-B39-C13-D24
A3-B39-C13-D24
A9-B39-C13-D24
A13-B39-C13-D24
A24-B39-C13-D24
A69-B39-C13-D24
A67-B39-C13-D24
A39-B39-C13-D24
A65-B39-C13-D24
A66-B39-C13-D24
A2-B45-C13-D24

-continued

A3-B45-C13-D24
A9-B45-C13-D24
A13-B45-C13-D24
A24-B45-C13-D24
A69-B45-C13-D24
A67-B45-C13-D24
A39-B45-C13-D24
A65-B45-C13-D24
A66-B45-C13-D24
A2-B53-C13-D24
A3-B53-C13-D24
A9-B53-C13-D24
A13-B53-C13-D24
A24-B53-C13-D24
A69-B53-C13-D24
A67-B53-C13-D24
A39-B53-C13-D24
A65-B53-C13-D24
A66-B53-C13-D24
A2-B79-C13-D24
A3-B79-C13-D24
A9-B79-C13-D24
A13-B79-C13-D24
A24-B79-C13-D24
A69-B79-C13-D24
A67-B79-C13-D24
A39-B79-C13-D24
A65-B79-C13-D24
A66-B79-C13-D24
A2-B80-C13-D24
A3-B80-C13-D24
A9-B80-C13-D24
A13-B80-C13-D24
A24-B80-C13-D24
A69-B80-C13-D24
A67-B80-C13-D24
A39-B80-C13-D24
A65-B80-C13-D24
A66-B80-C13-D24
A2-B85-C13-D24
A3-B85-C13-D24
A9-B85-C13-D24
A13-B85-C13-D24
A24-B85-C13-D24
A69-B85-C13-D24
A67-B85-C13-D24
A39-B85-C13-D24
A65-B85-C13-D24
A66-B85-C13-D24
A2-B86-C13-D24
A3-B86-C13-D24
A9-B86-C13-D24
A13-B86-C13-D24
A24-B86-C13-D24
A69-B86-C13-D24
A67-B86-C13-D24
A39-B86-C13-D24
A65-B86-C13-D24
A66-B86-C13-D24
A2-B87-C13-D24
A3-B87-C13-D24
A9-B87-C13-D24
A13-B87-C13-D24
A24-B87-C13-D24
A69-B87-C13-D24
A67-B87-C13-D24
A39-B87-C13-D24
A65-B87-C13-D24
A66-B87-C13-D24
A2-B89-C13-D24
A3-B89-C13-D24
A9-B89-C13-D24
A13-B89-C13-D24
A24-B89-C13-D24
A69-B89-C13-D24
A67-B89-C13-D24
A39-B89-C13-D24
A65-B89-C13-D24
A66-B89-C13-D24
A2-B92-C13-D24

-continued

A3-B92-C13-D24
A9-B92-C13-D24
A13-B92-C13-D24
A24-B92-C13-D24
A69-B92-C13-D24
A67-B92-C13-D24
A39-B92-C13-D24
A65-B92-C13-D24
A66-B92-C13-D24
A2-B4-C1-D25
A3-B4-C1-D25
A9-B4-C1-D25
A13-B4-C1-D25
A24-B4-C1-D25
A69-B4-C1-D25
A67-B4-C1-D25
A39-B4-C1-D25
A65-B4-C1-D25
A66-B4-C1-D25
A2-B5-C1-D25
A3-B5-C1-D25
A9-B5-C1-D25
A13-B5-C1-D25
A24-B5-C1-D25
A69-B5-C1-D25
A67-B5-C1-D25
A39-B5-C1-D25
A65-B5-C1-D25
A66-B5-C1-D25
A2-B6-C1-D25
A3-B6-C1-D25
A9-B6-C1-D25
A13-B6-C1-D25
A24-B6-C1-D25
A69-B6-C1-D25
A67-B6-C1-D25
A39-B6-C1-D25
A65-B6-C1-D25
A66-B6-C1-D25
A2-B32-C1-D25
A3-B32-C1-D25
A9-B32-C1-D25
A13-B32-C1-D25
A24-B32-C1-D25
A69-B32-C1-D25
A67-B32-C1-D25
A39-B32-C1-D25
A65-B32-C1-D25
A66-B32-C1-D25
A2-B39-C1-D25
A3-B39-C1-D25
A9-B39-C1-D25
A13-B39-C1-D25
A24-B39-C1-D25
A69-B39-C1-D25
A67-B39-C1-D25
A39-B39-C1-D25
A65-B39-C1-D25
A66-B39-C1-D25
A2-B45-C1-D25
A3-B45-C1-D25
A9-B45-C1-D25
A13-B45-C1-D25
A24-B45-C1-D25
A69-B45-C1-D25
A67-B45-C1-D25
A39-B45-C1-D25
A65-B45-C1-D25
A66-B45-C1-D25
A2-B53-C1-D25
A3-B53-C1-D25
A9-B53-C1-D25
A13-B53-C1-D25
A24-B53-C1-D25
A69-B53-C1-D25
A67-B53-C1-D25
A39-B53-C1-D25
A65-B53-C1-D25
A66-B53-C1-D25
A2-B79-C1-D25

-continued
A3-B79-C1-D25
A9-B79-C1-D25
A13-B79-C1-D25
A24-B79-C1-D25
A69-B79-C1-D25
A67-B79-C1-D25
A39-B79-C1-D25
A65-B79-C1-D25
A66-B79-C1-D25
A2-B80-C1-D25
A3-B80-C1-D25
A9-B80-C1-D25
A13-B80-C1-D25
A24-B80-C1-D25
A69-B80-C1-D25
A67-B80-C1-D25
A39-B80-C1-D25
A65-B80-C1-D25
A66-B80-C1-D25
A2-B85-C1-D25
A3-B85-C1-D25
A9-B85-C1-D25
A13-B85-C1-D25
A24-B85-C1-D25
A69-B85-C1-D25
A67-B85-C1-D25
A39-B85-C1-D25
A65-B85-C1-D25
A66-B85-C1-D25
A2-B86-C1-D25
A3-B86-C1-D25
A9-B86-C1-D25
A13-B86-C1-D25
A24-B86-C1-D25
A69-B86-C1-D25
A67-B86-C1-D25
A39-B86-C1-D25
A65-B86-C1-D25
A66-B86-C1-D25
A2-B87-C1-D25
A3-B87-C1-D25
A9-B87-C1-D25
A13-B87-C1-D25
A24-B87-C1-D25
A69-B87-C1-D25
A67-B87-C1-D25
A39-B87-C1-D25
A65-B87-C1-D25
A66-B87-C1-D25
A2-B89-C1-D25
A3-B89-C1-D25
A9-B89-C1-D25
A13-B89-C1-D25
A24-B89-C1-D25
A69-B89-C1-D25
A67-B89-C1-D25
A39-B89-C1-D25
A65-B89-C1-D25
A66-B89-C1-D25
A2-B92-C1-D25
A3-B92-C1-D25
A9-B92-C1-D25
A13-B92-C1-D25
A24-B92-C1-D25
A69-B92-C1-D25
A67-B92-C1-D25
A39-B92-C1-D25
A65-B92-C1-D25
A66-B92-C1-D25
A2-B4-C2-D25
A3-B4-C2-D25
A9-B4-C2-D25
A13-B4-C2-D25
A24-B4-C2-D25
A69-B4-C2-D25
A67-B4-C2-D25
A39-B4-C2-D25
A65-B4-C2-D25
A66-B4-C2-D25
A2-B5-C2-D25

-continued
A3-B5-C2-D25
A9-B5-C2-D25
A13-B5-C2-D25
A24-B5-C2-D25
A69-B5-C2-D25
A67-B5-C2-D25
A39-B5-C2-D25
A65-B5-C2-D25
A66-B5-C2-D25
A2-B6-C2-D25
A3-B6-C2-D25
A9-B6-C2-D25
A13-B6-C2-D25
A24-B6-C2-D25
A69-B6-C2-D25
A67-B6-C2-D25
A39-B6-C2-D25
A65-B6-C2-D25
A66-B6-C2-D25
A2-B32-C2-D25
A3-B32-C2-D25
A9-B32-C2-D25
A13-B32-C2-D25
A24-B32-C2-D25
A69-B32-C2-D25
A67-B32-C2-D25
A39-B32-C2-D25
A65-B32-C2-D25
A66-B32-C2-D25
A2-B39-C2-D25
A3-B39-C2-D25
A9-B39-C2-D25
A13-B39-C2-D25
A24-B39-C2-D25
A69-B39-C2-D25
A67-B39-C2-D25
A39-B39-C2-D25
A65-B39-C2-D25
A66-B39-C2-D25
A2-B45-C2-D25
A3-B45-C2-D25
A9-B45-C2-D25
A13-B45-C2-D25
A24-B45-C2-D25
A69-B45-C2-D25
A67-B45-C2-D25
A39-B45-C2-D25
A65-B45-C2-D25
A66-B45-C2-D25
A2-B53-C2-D25
A3-B53-C2-D25
A9-B53-C2-D25
A13-B53-C2-D25
A24-B53-C2-D25
A69-B53-C2-D25
A67-B53-C2-D25
A39-B53-C2-D25
A65-B53-C2-D25
A66-B53-C2-D25
A2-B79-C2-D25
A3-B79-C2-D25
A9-B79-C2-D25
A13-B79-C2-D25
A24-B79-C2-D25
A69-B79-C2-D25
A67-B79-C2-D25
A39-B79-C2-D25
A65-B79-C2-D25
A66-B79-C2-D25
A2-B80-C2-D25
A3-B80-C2-D25
A9-B80-C2-D25
A13-B80-C2-D25
A24-B80-C2-D25
A69-B80-C2-D25
A67-B80-C2-D25
A39-B80-C2-D25
A65-B80-C2-D25
A66-B80-C2-D25
A2-B85-C2-D25

-continued

A3-B85-C2-D25
A9-B85-C2-D25
A13-B85-C2-D25
A24-B85-C2-D25
A69-B85-C2-D25
A67-B85-C2-D25
A39-B85-C2-D25
A65-B85-C2-D25
A66-B85-C2-D25
A2-B86-C2-D25
A3-B86-C2-D25
A9-B86-C2-D25
A13-B86-C2-D25
A24-B86-C2-D25
A69-B86-C2-D25
A67-B86-C2-D25
A39-B86-C2-D25
A65-B86-C2-D25
A66-B86-C2-D25
A2-B87-C2-D25
A3-B87-C2-D25
A9-B87-C2-D25
A13-B87-C2-D25
A24-B87-C2-D25
A69-B87-C2-D25
A67-B87-C2-D25
A39-B87-C2-D25
A65-B87-C2-D25
A66-B87-C2-D25
A2-B89-C2-D25
A3-B89-C2-D25
A9-B89-C2-D25
A13-B89-C2-D25
A24-B89-C2-D25
A69-B89-C2-D25
A67-B89-C2-D25
A39-B89-C2-D25
A65-B89-C2-D25
A66-B89-C2-D25
A2-B92-C2-D25
A3-B92-C2-D25
A9-B92-C2-D25
A13-B92-C2-D25
A24-B92-C2-D25
A69-B92-C2-D25
A67-B92-C2-D25
A39-B92-C2-D25
A65-B92-C2-D25
A66-B92-C2-D25
A2-B4-C3-D25
A3-B4-C3-D25
A9-B4-C3-D25
A13-B4-C3-D25
A24-B4-C3-D25
A69-B4-C3-D25
A67-B4-C3-D25
A39-B4-C3-D25
A65-B4-C3-D25
A66-B4-C3-D25
A2-B5-C3-D25
A3-B5-C3-D25
A9-B5-C3-D25
A13-B5-C3-D25
A24-B5-C3-D25
A69-B5-C3-D25
A67-B5-C3-D25
A39-B5-C3-D25
A65-B5-C3-D25
A66-B5-C3-D25
A2-B6-C3-D25
A3-B6-C3-D25
A9-B6-C3-D25
A13-B6-C3-D25
A24-B6-C3-D25
A69-B6-C3-D25
A67-B6-C3-D25
A39-B6-C3-D25
A65-B6-C3-D25
A66-B6-C3-D25
A2-B32-C3-D25

-continued

A3-B32-C3-D25
A9-B32-C3-D25
A13-B32-C3-D25
A24-B32-C3-D25
A69-B32-C3-D25
A67-B32-C3-D25
A39-B32-C3-D25
A65-B32-C3-D25
A66-B32-C3-D25
A2-B39-C3-D25
A3-B39-C3-D25
A9-B39-C3-D25
A13-B39-C3-D25
A24-B39-C3-D25
A69-B39-C3-D25
A67-B39-C3-D25
A39-B39-C3-D25
A65-B39-C3-D25
A66-B39-C3-D25
A2-B45-C3-D25
A3-B45-C3-D25
A9-B45-C3-D25
A13-B45-C3-D25
A24-B45-C3-D25
A69-B45-C3-D25
A67-B45-C3-D25
A39-B45-C3-D25
A65-B45-C3-D25
A66-B45-C3-D25
A2-B53-C3-D25
A3-B53-C3-D25
A9-B53-C3-D25
A13-B53-C3-D25
A24-B53-C3-D25
A69-B53-C3-D25
A67-B53-C3-D25
A39-B53-C3-D25
A65-B53-C3-D25
A66-B53-C3-D25
A2-B79-C3-D25
A3-B79-C3-D25
A9-B79-C3-D25
A13-B79-C3-D25
A24-B79-C3-D25
A69-B79-C3-D25
A67-B79-C3-D25
A39-B79-C3-D25
A65-B79-C3-D25
A66-B79-C3-D25
A2-B80-C3-D25
A3-B80-C3-D25
A9-B80-C3-D25
A13-B80-C3-D25
A24-B80-C3-D25
A69-B80-C3-D25
A67-B80-C3-D25
A39-B80-C3-D25
A65-B80-C3-D25
A66-B80-C3-D25
A2-B85-C3-D25
A3-B85-C3-D25
A9-B85-C3-D25
A13-B85-C3-D25
A24-B85-C3-D25
A69-B85-C3-D25
A67-B85-C3-D25
A39-B85-C3-D25
A65-B85-C3-D25
A66-B85-C3-D25
A2-B86-C3-D25
A3-B86-C3-D25
A9-B86-C3-D25
A13-B86-C3-D25
A24-B86-C3-D25
A69-B86-C3-D25
A67-B86-C3-D25
A39-B86-C3-D25
A65-B86-C3-D25
A66-B86-C3-D25
A2-B87-C3-D25

-continued

A3-B87-C3-D25
A9-B87-C3-D25
A13-B87-C3-D25
A24-B87-C3-D25
A69-B87-C3-D25
A67-B87-C3-D25
A39-B87-C3-D25
A65-B87-C3-D25
A66-B87-C3-D25
A2-B89-C3-D25
A3-B89-C3-D25
A9-B89-C3-D25
A13-B89-C3-D25
A24-B89-C3-D25
A69-B89-C3-D25
A67-B89-C3-D25
A39-B89-C3-D25
A65-B89-C3-D25
A66-B89-C3-D25
A2-B92-C3-D25
A3-B92-C3-D25
A9-B92-C3-D25
A13-B92-C3-D25
A24-B92-C3-D25
A69-B92-C3-D25
A67-B92-C3-D25
A39-B92-C3-D25
A65-B92-C3-D25
A66-B92-C3-D25
A2-B4-C4-D25
A3-B4-C4-D25
A9-B4-C4-D25
A13-B4-C4-D25
A24-B4-C4-D25
A69-B4-C4-D25
A67-B4-C4-D25
A39-B4-C4-D25
A65-B4-C4-D25
A66-B4-C4-D25
A2-B5-C4-D25
A3-B5-C4-D25
A9-B5-C4-D25
A13-B5-C4-D25
A24-B5-C4-D25
A69-B5-C4-D25
A67-B5-C4-D25
A39-B5-C4-D25
A65-B5-C4-D25
A66-B5-C4-D25
A2-B6-C4-D25
A3-B6-C4-D25
A9-B6-C4-D25
A13-B6-C4-D25
A24-B6-C4-D25
A69-B6-C4-D25
A67-B6-C4-D25
A39-B6-C4-D25
A65-B6-C4-D25
A66-B6-C4-D25
A2-B32-C4-D25
A3-B32-C4-D25
A9-B32-C4-D25
A13-B32-C4-D25
A24-B32-C4-D25
A69-B32-C4-D25
A67-B32-C4-D25
A39-B32-C4-D25
A65-B32-C4-D25
A66-B32-C4-D25
A2-B39-C4-D25
A3-B39-C4-D25
A9-B39-C4-D25
A13-B39-C4-D25
A24-B39-C4-D25
A69-B39-C4-D25
A67-B39-C4-D25
A39-B39-C4-D25
A65-B39-C4-D25
A66-B39-C4-D25
A2-B45-C4-D25

-continued

A3-B45-C4-D25
A9-B45-C4-D25
A13-B45-C4-D25
A24-B45-C4-D25
A69-B45-C4-D25
A67-B45-C4-D25
A39-B45-C4-D25
A65-B45-C4-D25
A66-B45-C4-D25
A2-B53-C4-D25
A3-B53-C4-D25
A9-B53-C4-D25
A13-B53-C4-D25
A24-B53-C4-D25
A69-B53-C4-D25
A67-B53-C4-D25
A39-B53-C4-D25
A65-B53-C4-D25
A66-B53-C4-D25
A2-B79-C4-D25
A3-B79-C4-D25
A9-B79-C4-D25
A13-B79-C4-D25
A24-B79-C4-D25
A69-B79-C4-D25
A67-B79-C4-D25
A39-B79-C4-D25
A65-B79-C4-D25
A66-B79-C4-D25
A2-B80-C4-D25
A3-B80-C4-D25
A9-B80-C4-D25
A13-B80-C4-D25
A24-B80-C4-D25
A69-B80-C4-D25
A67-B80-C4-D25
A39-B80-C4-D25
A65-B80-C4-D25
A66-B80-C4-D25
A2-B85-C4-D25
A3-B85-C4-D25
A9-B85-C4-D25
A13-B85-C4-D25
A24-B85-C4-D25
A69-B85-C4-D25
A67-B85-C4-D25
A39-B85-C4-D25
A65-B85-C4-D25
A66-B85-C4-D25
A2-B86-C4-D25
A3-B86-C4-D25
A9-B86-C4-D25
A13-B86-C4-D25
A24-B86-C4-D25
A69-B86-C4-D25
A67-B86-C4-D25
A39-B86-C4-D25
A65-B86-C4-D25
A66-B86-C4-D25
A2-B87-C4-D25
A3-B87-C4-D25
A9-B87-C4-D25
A13-B87-C4-D25
A24-B87-C4-D25
A69-B87-C4-D25
A67-B87-C4-D25
A39-B87-C4-D25
A65-B87-C4-D25
A66-B87-C4-D25
A2-B89-C4-D25
A3-B89-C4-D25
A9-B89-C4-D25
A13-B89-C4-D25
A24-B89-C4-D25
A69-B89-C4-D25
A67-B89-C4-D25
A39-B89-C4-D25
A65-B89-C4-D25
A66-B89-C4-D25
A2-B92-C4-D25

-continued
A3-B92-C4-D25
A9-B92-C4-D25
A13-B92-C4-D25
A24-B92-C4-D25
A69-B92-C4-D25
A67-B92-C4-D25
A39-B92-C4-D25
A65-B92-C4-D25
A66-B92-C4-D25
A2-B4-C5-D25
A3-B4-C5-D25
A9-B4-C5-D25
A13-B4-C5-D25
A24-B4-C5-D25
A69-B4-C5-D25
A67-B4-C5-D25
A39-B4-C5-D25
A65-B4-C5-D25
A66-B4-C5-D25
A2-B5-C5-D25
A3-B5-C5-D25
A9-B5-C5-D25
A13-B5-C5-D25
A24-B5-C5-D25
A69-B5-C5-D25
A67-B5-C5-D25
A39-B5-C5-D25
A65-B5-C5-D25
A66-B5-C5-D25
A2-B6-C5-D25
A3-B6-C5-D25
A9-B6-C5-D25
A13-B6-C5-D25
A24-B6-C5-D25
A69-B6-C5-D25
A67-B6-C5-D25
A39-B6-C5-D25
A65-B6-C5-D25
A66-B6-C5-D25
A2-B32-C5-D25
A3-B32-C5-D25
A9-B32-C5-D25
A13-B32-C5-D25
A24-B32-C5-D25
A69-B32-C5-D25
A67-B32-C5-D25
A39-B32-C5-D25
A65-B32-C5-D25
A66-B32-C5-D25
A2-B39-C5-D25
A3-B39-C5-D25
A9-B39-C5-D25
A13-B39-C5-D25
A24-B39-C5-D25
A69-B39-C5-D25
A67-B39-C5-D25
A39-B39-C5-D25
A65-B39-C5-D25
A66-B39-C5-D25
A2-B45-C5-D25
A3-B45-C5-D25
A9-B45-C5-D25
A13-B45-C5-D25
A24-B45-C5-D25
A69-B45-C5-D25
A67-B45-C5-D25
A39-B45-C5-D25
A65-B45-C5-D25
A66-B45-C5-D25
A2-B53-C5-D25
A3-B53-C5-D25
A9-B53-C5-D25
A13-B53-C5-D25
A24-B53-C5-D25
A69-B53-C5-D25
A67-B53-C5-D25
A39-B53-C5-D25
A65-B53-C5-D25
A66-B53-C5-D25
A2-B79-C5-D25

-continued
A3-B79-C5-D25
A9-B79-C5-D25
A13-B79-C5-D25
A24-B79-C5-D25
A69-B79-C5-D25
A67-B79-C5-D25
A39-B79-C5-D25
A65-B79-C5-D25
A66-B79-C5-D25
A2-B80-C5-D25
A3-B80-C5-D25
A9-B80-C5-D25
A13-B80-C5-D25
A24-B80-C5-D25
A69-B80-C5-D25
A67-B80-C5-D25
A39-B80-C5-D25
A65-B80-C5-D25
A66-B80-C5-D25
A2-B85-C5-D25
A3-B85-C5-D25
A9-B85-C5-D25
A13-B85-C5-D25
A24-B85-C5-D25
A69-B85-C5-D25
A67-B85-C5-D25
A39-B85-C5-D25
A65-B85-C5-D25
A66-B85-C5-D25
A2-B86-C5-D25
A3-B86-C5-D25
A9-B86-C5-D25
A13-B86-C5-D25
A24-B86-C5-D25
A69-B86-C5-D25
A67-B86-C5-D25
A39-B86-C5-D25
A65-B86-C5-D25
A66-B86-C5-D25
A2-B87-C5-D25
A3-B87-C5-D25
A9-B87-C5-D25
A13-B87-C5-D25
A24-B87-C5-D25
A69-B87-C5-D25
A67-B87-C5-D25
A39-B87-C5-D25
A65-B87-C5-D25
A66-B87-C5-D25
A2-B89-C5-D25
A3-B89-C5-D25
A9-B89-C5-D25
A13-B89-C5-D25
A24-B89-C5-D25
A69-B89-C5-D25
A67-B89-C5-D25
A39-B89-C5-D25
A65-B89-C5-D25
A66-B89-C5-D25
A2-B92-C5-D25
A3-B92-C5-D25
A9-B92-C5-D25
A13-B92-C5-D25
A24-B92-C5-D25
A69-B92-C5-D25
A67-B92-C5-D25
A39-B92-C5-D25
A65-B92-C5-D25
A66-B92-C5-D25
A2-B4-C6-D25
A3-B4-C6-D25
A9-B4-C6-D25
A13-B4-C6-D25
A24-B4-C6-D25
A69-B4-C6-D25
A67-B4-C6-D25
A39-B4-C6-D25
A65-B4-C6-D25
A66-B4-C6-D25
A2-B5-C6-D25

-continued
A3-B5-C6-D25
A9-B5-C6-D25
A13-B5-C6-D25
A24-B5-C6-D25
A69-B5-C6-D25
A67-B5-C6-D25
A39-B5-C6-D25
A65-B5-C6-D25
A66-B5-C6-D25
A2-B6-C6-D25
A3-B6-C6-D25
A9-B6-C6-D25
A13-B6-C6-D25
A24-B6-C6-D25
A69-B6-C6-D25
A67-B6-C6-D25
A39-B6-C6-D25
A65-B6-C6-D25
A66-B6-C6-D25
A2-B32-C6-D25
A3-B32-C6-D25
A9-B32-C6-D25
A13-B32-C6-D25
A24-B32-C6-D25
A69-B32-C6-D25
A67-B32-C6-D25
A39-B32-C6-D25
A65-B32-C6-D25
A66-B32-C6-D25
A2-B39-C6-D25
A3-B39-C6-D25
A9-B39-C6-D25
A13-B39-C6-D25
A24-B39-C6-D25
A69-B39-C6-D25
A67-B39-C6-D25
A39-B39-C6-D25
A65-B39-C6-D25
A66-B39-C6-D25
A2-B45-C6-D25
A3-B45-C6-D25
A9-B45-C6-D25
A13-B45-C6-D25
A24-B45-C6-D25
A69-B45-C6-D25
A67-B45-C6-D25
A39-B45-C6-D25
A65-B45-C6-D25
A66-B45-C6-D25
A2-B53-C6-D25
A3-B53-C6-D25
A9-B53-C6-D25
A13-B53-C6-D25
A24-B53-C6-D25
A69-B53-C6-D25
A67-B53-C6-D25
A39-B53-C6-D25
A65-B53-C6-D25
A66-B53-C6-D25
A2-B79-C6-D25
A3-B79-C6-D25
A9-B79-C6-D25
A13-B79-C6-D25
A24-B79-C6-D25
A69-B79-C6-D25
A67-B79-C6-D25
A39-B79-C6-D25
A65-B79-C6-D25
A66-B79-C6-D25
A2-B80-C6-D25
A3-B80-C6-D25
A9-B80-C6-D25
A13-B80-C6-D25
A24-B80-C6-D25
A69-B80-C6-D25
A67-B80-C6-D25
A39-B80-C6-D25
A65-B80-C6-D25
A66-B80-C6-D25
A2-B85-C6-D25

-continued
A3-B85-C6-D25
A9-B85-C6-D25
A13-B85-C6-D25
A24-B85-C6-D25
A69-B85-C6-D25
A67-B85-C6-D25
A39-B85-C6-D25
A65-B85-C6-D25
A66-B85-C6-D25
A2-B86-C6-D25
A3-B86-C6-D25
A9-B86-C6-D25
A13-B86-C6-D25
A24-B86-C6-D25
A69-B86-C6-D25
A67-B86-C6-D25
A39-B86-C6-D25
A65-B86-C6-D25
A66-B86-C6-D25
A2-B87-C6-D25
A3-B87-C6-D25
A9-B87-C6-D25
A13-B87-C6-D25
A24-B87-C6-D25
A69-B87-C6-D25
A67-B87-C6-D25
A39-B87-C6-D25
A65-B87-C6-D25
A66-B87-C6-D25
A2-B89-C6-D25
A3-B89-C6-D25
A9-B89-C6-D25
A13-B89-C6-D25
A24-B89-C6-D25
A69-B89-C6-D25
A67-B89-C6-D25
A39-B89-C6-D25
A65-B89-C6-D25
A66-B89-C6-D25
A2-B92-C6-D25
A3-B92-C6-D25
A9-B92-C6-D25
A13-B92-C6-D25
A24-B92-C6-D25
A69-B92-C6-D25
A67-B92-C6-D25
A39-B92-C6-D25
A65-B92-C6-D25
A66-B92-C6-D25
A2-B4-C7-D25
A3-B4-C7-D25
A9-B4-C7-D25
A13-B4-C7-D25
A24-B4-C7-D25
A69-B4-C7-D25
A67-B4-C7-D25
A39-B4-C7-D25
A65-B4-C7-D25
A66-B4-C7-D25
A2-B5-C7-D25
A3-B5-C7-D25
A9-B5-C7-D25
A13-B5-C7-D25
A24-B5-C7-D25
A69-B5-C7-D25
A67-B5-C7-D25
A39-B5-C7-D25
A65-B5-C7-D25
A66-B5-C7-D25
A2-B6-C7-D25
A3-B6-C7-D25
A9-B6-C7-D25
A13-B6-C7-D25
A24-B6-C7-D25
A69-B6-C7-D25
A67-B6-C7-D25
A39-B6-C7-D25
A65-B6-C7-D25
A66-B6-C7-D25
A2-B32-C7-D25

-continued
A3-B32-C7-D25
A9-B32-C7-D25
A13-B32-C7-D25
A24-B32-C7-D25
A69-B32-C7-D25
A67-B32-C7-D25
A39-B32-C7-D25
A65-B32-C7-D25
A66-B32-C7-D25
A2-B39-C7-D25
A3-B39-C7-D25
A9-B39-C7-D25
A13-B39-C7-D25
A24-B39-C7-D25
A69-B39-C7-D25
A67-B39-C7-D25
A39-B39-C7-D25
A65-B39-C7-D25
A66-B39-C7-D25
A2-B45-C7-D25
A3-B45-C7-D25
A9-B45-C7-D25
A13-B45-C7-D25
A24-B45-C7-D25
A69-B45-C7-D25
A67-B45-C7-D25
A39-B45-C7-D25
A65-B45-C7-D25
A66-B45-C7-D25
A2-B53-C7-D25
A3-B53-C7-D25
A9-B53-C7-D25
A13-B53-C7-D25
A24-B53-C7-D25
A69-B53-C7-D25
A67-B53-C7-D25
A39-B53-C7-D25
A65-B53-C7-D25
A66-B53-C7-D25
A2-B79-C7-D25
A3-B79-C7-D25
A9-B79-C7-D25
A13-B79-C7-D25
A24-B79-C7-D25
A69-B79-C7-D25
A67-B79-C7-D25
A39-B79-C7-D25
A65-B79-C7-D25
A66-B79-C7-D25
A2-B80-C7-D25
A3-B80-C7-D25
A9-B80-C7-D25
A13-B80-C7-D25
A24-B80-C7-D25
A69-B80-C7-D25
A67-B80-C7-D25
A39-B80-C7-D25
A65-B80-C7-D25
A66-B80-C7-D25
A2-B85-C7-D25
A3-B85-C7-D25
A9-B85-C7-D25
A13-B85-C7-D25
A24-B85-C7-D25
A69-B85-C7-D25
A67-B85-C7-D25
A39-B85-C7-D25
A65-B85-C7-D25
A66-B85-C7-D25
A2-B86-C7-D25
A3-B86-C7-D25
A9-B86-C7-D25
A13-B86-C7-D25
A24-B86-C7-D25
A69-B86-C7-D25
A67-B86-C7-D25
A39-B86-C7-D25
A65-B86-C7-D25
A66-B86-C7-D25
A2-B87-C7-D25

-continued
A3-B87-C7-D25
A9-B87-C7-D25
A13-B87-C7-D25
A24-B87-C7-D25
A69-B87-C7-D25
A67-B87-C7-D25
A39-B87-C7-D25
A65-B87-C7-D25
A66-B87-C7-D25
A2-B89-C7-D25
A3-B89-C7-D25
A9-B89-C7-D25
A13-B89-C7-D25
A24-B89-C7-D25
A69-B89-C7-D25
A67-B89-C7-D25
A39-B89-C7-D25
A65-B89-C7-D25
A66-B89-C7-D25
A2-B92-C7-D25
A3-B92-C7-D25
A9-B92-C7-D25
A13-B92-C7-D25
A24-B92-C7-D25
A69-B92-C7-D25
A67-B92-C7-D25
A39-B92-C7-D25
A65-B92-C7-D25
A66-B92-C7-D25
A2-B4-C8-D25
A3-B4-C8-D25
A9-B4-C8-D25
A13-B4-C8-D25
A24-B4-C8-D25
A69-B4-C8-D25
A67-B4-C8-D25
A39-B4-C8-D25
A65-B4-C8-D25
A66-B4-C8-D25
A2-B5-C8-D25
A3-B5-C8-D25
A9-B5-C8-D25
A13-B5-C8-D25
A24-B5-C8-D25
A69-B5-C8-D25
A67-B5-C8-D25
A39-B5-C8-D25
A65-B5-C8-D25
A66-B5-C8-D25
A2-B6-C8-D25
A3-B6-C8-D25
A9-B6-C8-D25
A13-B6-C8-D25
A24-B6-C8-D25
A69-B6-C8-D25
A67-B6-C8-D25
A39-B6-C8-D25
A65-B6-C8-D25
A66-B6-C8-D25
A2-B32-C8-D25
A3-B32-C8-D25
A9-B32-C8-D25
A13-B32-C8-D25
A24-B32-C8-D25
A69-B32-C8-D25
A67-B32-C8-D25
A39-B32-C8-D25
A65-B32-C8-D25
A66-B32-C8-D25
A2-B39-C8-D25
A3-B39-C8-D25
A9-B39-C8-D25
A13-B39-C8-D25
A24-B39-C8-D25
A69-B39-C8-D25
A67-B39-C8-D25
A39-B39-C8-D25
A65-B39-C8-D25
A66-B39-C8-D25
A2-B45-C8-D25

-continued

A3-B45-C8-D25
A9-B45-C8-D25
A13-B45-C8-D25
A24-B45-C8-D25
A69-B45-C8-D25
A67-B45-C8-D25
A39-B45-C8-D25
A65-B45-C8-D25
A66-B45-C8-D25
A2-B53-C8-D25
A3-B53-C8-D25
A9-B53-C8-D25
A13-B53-C8-D25
A24-B53-C8-D25
A69-B53-C8-D25
A67-B53-C8-D25
A39-B53-C8-D25
A65-B53-C8-D25
A66-B53-C8-D25
A2-B79-C8-D25
A3-B79-C8-D25
A9-B79-C8-D25
A13-B79-C8-D25
A24-B79-C8-D25
A69-B79-C8-D25
A67-B79-C8-D25
A39-B79-C8-D25
A65-B79-C8-D25
A66-B79-C8-D25
A2-B80-C8-D25
A3-B80-C8-D25
A9-B80-C8-D25
A13-B80-C8-D25
A24-B80-C8-D25
A69-B80-C8-D25
A67-B80-C8-D25
A39-B80-C8-D25
A65-B80-C8-D25
A66-B80-C8-D25
A2-B85-C8-D25
A3-B85-C8-D25
A9-B85-C8-D25
A13-B85-C8-D25
A24-B85-C8-D25
A69-B85-C8-D25
A67-B85-C8-D25
A39-B85-C8-D25
A65-B85-C8-D25
A66-B85-C8-D25
A2-B86-C8-D25
A3-B86-C8-D25
A9-B86-C8-D25
A13-B86-C8-D25
A24-B86-C8-D25
A69-B86-C8-D25
A67-B86-C8-D25
A39-B86-C8-D25
A65-B86-C8-D25
A66-B86-C8-D25
A2-B87-C8-D25
A3-B87-C8-D25
A9-B87-C8-D25
A13-B87-C8-D25
A24-B87-C8-D25
A69-B87-C8-D25
A67-B87-C8-D25
A39-B87-C8-D25
A65-B87-C8-D25
A66-B87-C8-D25
A2-B89-C8-D25
A3-B89-C8-D25
A9-B89-C8-D25
A13-B89-C8-D25
A24-B89-C8-D25
A69-B89-C8-D25
A67-B89-C8-D25
A39-B89-C8-D25
A65-B89-C8-D25
A66-B89-C8-D25
A2-B92-C8-D25

-continued

A3-B92-C8-D25
A9-B92-C8-D25
A13-B92-C8-D25
A24-B92-C8-D25
A69-B92-C8-D25
A67-B92-C8-D25
A39-B92-C8-D25
A65-B92-C8-D25
A66-B92-C8-D25
A2-B4-C9-D25
A3-B4-C9-D25
A9-B4-C9-D25
A13-B4-C9-D25
A24-B4-C9-D25
A69-B4-C9-D25
A67-B4-C9-D25
A39-B4-C9-D25
A65-B4-C9-D25
A66-B4-C9-D25
A2-B5-C9-D25
A3-B5-C9-D25
A9-B5-C9-D25
A13-B5-C9-D25
A24-B5-C9-D25
A69-B5-C9-D25
A67-B5-C9-D25
A39-B5-C9-D25
A65-B5-C9-D25
A66-B5-C9-D25
A2-B6-C9-D25
A3-B6-C9-D25
A9-B6-C9-D25
A13-B6-C9-D25
A24-B6-C9-D25
A69-B6-C9-D25
A67-B6-C9-D25
A39-B6-C9-D25
A65-B6-C9-D25
A66-B6-C9-D25
A2-B32-C9-D25
A3-B32-C9-D25
A9-B32-C9-D25
A13-B32-C9-D25
A24-B32-C9-D25
A69-B32-C9-D25
A67-B32-C9-D25
A39-B32-C9-D25
A65-B32-C9-D25
A66-B32-C9-D25
A2-B39-C9-D25
A3-B39-C9-D25
A9-B39-C9-D25
A13-B39-C9-D25
A24-B39-C9-D25
A69-B39-C9-D25
A67-B39-C9-D25
A39-B39-C9-D25
A65-B39-C9-D25
A66-B39-C9-D25
A2-B45-C9-D25
A3-B45-C9-D25
A9-B45-C9-D25
A13-B45-C9-D25
A24-B45-C9-D25
A69-B45-C9-D25
A67-B45-C9-D25
A39-B45-C9-D25
A65-B45-C9-D25
A66-B45-C9-D25
A2-B53-C9-D25
A3-B53-C9-D25
A9-B53-C9-D25
A13-B53-C9-D25
A24-B53-C9-D25
A69-B53-C9-D25
A67-B53-C9-D25
A39-B53-C9-D25
A65-B53-C9-D25
A66-B53-C9-D25
A2-B79-C9-D25

-continued

A3-B79-C9-D25
A9-B79-C9-D25
A13-B79-C9-D25
A24-B79-C9-D25
A69-B79-C9-D25
A67-B79-C9-D25
A39-B79-C9-D25
A65-B79-C9-D25
A66-B79-C9-D25
A2-B80-C9-D25
A3-B80-C9-D25
A9-B80-C9-D25
A13-B80-C9-D25
A24-B80-C9-D25
A69-B80-C9-D25
A67-B80-C9-D25
A39-B80-C9-D25
A65-B80-C9-D25
A66-B80-C9-D25
A2-B85-C9-D25
A3-B85-C9-D25
A9-B85-C9-D25
A13-B85-C9-D25
A24-B85-C9-D25
A69-B85-C9-D25
A67-B85-C9-D25
A39-B85-C9-D25
A65-B85-C9-D25
A66-B85-C9-D25
A2-B86-C9-D25
A3-B86-C9-D25
A9-B86-C9-D25
A13-B86-C9-D25
A24-B86-C9-D25
A69-B86-C9-D25
A67-B86-C9-D25
A39-B86-C9-D25
A65-B86-C9-D25
A66-B86-C9-D25
A2-B87-C9-D25
A3-B87-C9-D25
A9-B87-C9-D25
A13-B87-C9-D25
A24-B87-C9-D25
A69-B87-C9-D25
A67-B87-C9-D25
A39-B87-C9-D25
A65-B87-C9-D25
A66-B87-C9-D25
A2-B89-C9-D25
A3-B89-C9-D25
A9-B89-C9-D25
A13-B89-C9-D25
A24-B89-C9-D25
A69-B89-C9-D25
A67-B89-C9-D25
A39-B89-C9-D25
A65-B89-C9-D25
A66-B89-C9-D25
A2-B92-C9-D25
A3-B92-C9-D25
A9-B92-C9-D25
A13-B92-C9-D25
A24-B92-C9-D25
A69-B92-C9-D25
A67-B92-C9-D25
A39-B92-C9-D25
A65-B92-C9-D25
A66-B92-C9-D25
A2-B4-C10-D25
A3-B4-C10-D25
A9-B4-C10-D25
A13-B4-C10-D25
A24-B4-C10-D25
A69-B4-C10-D25
A67-B4-C10-D25
A39-B4-C10-D25
A65-B4-C10-D25
A66-B4-C10-D25
A2-B5-C10-D25

-continued

A3-B5-C10-D25
A9-B5-C10-D25
A13-B5-C10-D25
A24-B5-C10-D25
A69-B5-C10-D25
A67-B5-C10-D25
A39-B5-C10-D25
A65-B5-C10-D25
A66-B5-C10-D25
A2-B6-C10-D25
A3-B6-C10-D25
A9-B6-C10-D25
A13-B6-C10-D25
A24-B6-C10-D25
A69-B6-C10-D25
A67-B6-C10-D25
A39-B6-C10-D25
A65-B6-C10-D25
A66-B6-C10-D25
A2-B32-C10-D25
A3-B32-C10-D25
A9-B32-C10-D25
A13-B32-C10-D25
A24-B32-C10-D25
A69-B32-C10-D25
A67-B32-C10-D25
A39-B32-C10-D25
A65-B32-C10-D25
A66-B32-C10-D25
A2-B39-C10-D25
A3-B39-C10-D25
A9-B39-C10-D25
A13-B39-C10-D25
A24-B39-C10-D25
A69-B39-C10-D25
A67-B39-C10-D25
A39-B39-C10-D25
A65-B39-C10-D25
A66-B39-C10-D25
A2-B45-C10-D25
A3-B45-C10-D25
A9-B45-C10-D25
A13-B45-C10-D25
A24-B45-C10-D25
A69-B45-C10-D25
A67-B45-C10-D25
A39-B45-C10-D25
A65-B45-C10-D25
A66-B45-C10-D25
A2-B53-C10-D25
A3-B53-C10-D25
A9-B53-C10-D25
A13-B53-C10-D25
A24-B53-C10-D25
A69-B53-C10-D25
A67-B53-C10-D25
A39-B53-C10-D25
A65-B53-C10-D25
A66-B53-C10-D25
A2-B79-C10-D25
A3-B79-C10-D25
A9-B79-C10-D25
A13-B79-C10-D25
A24-B79-C10-D25
A69-B79-C10-D25
A67-B79-C10-D25
A39-B79-C10-D25
A65-B79-C10-D25
A66-B79-C10-D25
A2-B80-C10-D25
A3-B80-C10-D25
A9-B80-C10-D25
A13-B80-C10-D25
A24-B80-C10-D25
A69-B80-C10-D25
A67-B80-C10-D25
A39-B80-C10-D25
A65-B80-C10-D25
A66-B80-C10-D25
A2-B85-C10-D25

-continued

A3-B85-C10-D25
A9-B85-C10-D25
A13-B85-C10-D25
A24-B85-C10-D25
A69-B85-C10-D25
A67-B85-C10-D25
A39-B85-C10-D25
A65-B85-C10-D25
A66-B85-C10-D25
A2-B86-C10-D25
A3-B86-C10-D25
A9-B86-C10-D25
A13-B86-C10-D25
A24-B86-C10-D25
A69-B86-C10-D25
A67-B86-C10-D25
A39-B86-C10-D25
A65-B86-C10-D25
A66-B86-C10-D25
A2-B87-C10-D25
A3-B87-C10-D25
A9-B87-C10-D25
A13-B87-C10-D25
A24-B87-C10-D25
A69-B87-C10-D25
A67-B87-C10-D25
A39-B87-C10-D25
A65-B87-C10-D25
A66-B87-C10-D25
A2-B89-C10-D25
A3-B89-C10-D25
A9-B89-C10-D25
A13-B89-C10-D25
A24-B89-C10-D25
A69-B89-C10-D25
A67-B89-C10-D25
A39-B89-C10-D25
A65-B89-C10-D25
A66-B89-C10-D25
A2-B92-C10-D25
A3-B92-C10-D25
A9-B92-C10-D25
A13-B92-C10-D25
A24-B92-C10-D25
A69-B92-C10-D25
A67-B92-C10-D25
A39-B92-C10-D25
A65-B92-C10-D25
A66-B92-C10-D25
A2-B4-C11-D25
A3-B4-C11-D25
A9-B4-C11-D25
A13-B4-C11-D25
A24-B4-C11-D25
A69-B4-C11-D25
A67-B4-C11-D25
A39-B4-C11-D25
A65-B4-C11-D25
A66-B4-C11-D25
A2-B5-C11-D25
A3-B5-C11-D25
A9-B5-C11-D25
A13-B5-C11-D25
A24-B5-C11-D25
A69-B5-C11-D25
A67-B5-C11-D25
A39-B5-C11-D25
A65-B5-C11-D25
A66-B5-C11-D25
A2-B6-C11-D25
A3-B6-C11-D25
A9-B6-C11-D25
A13-B6-C11-D25
A24-B6-C11-D25
A69-B6-C11-D25
A67-B6-C11-D25
A39-B6-C11-D25
A65-B6-C11-D25
A66-B6-C11-D25
A2-B32-C11-D25

-continued

A3-B32-C11-D25
A9-B32-C11-D25
A13-B32-C11-D25
A24-B32-C11-D25
A69-B32-C11-D25
A67-B32-C11-D25
A39-B32-C11-D25
A65-B32-C11-D25
A66-B32-C11-D25
A2-B39-C11-D25
A3-B39-C11-D25
A9-B39-C11-D25
A13-B39-C11-D25
A24-B39-C11-D25
A69-B39-C11-D25
A67-B39-C11-D25
A39-B39-C11-D25
A65-B39-C11-D25
A66-B39-C11-D25
A2-B45-C11-D25
A3-B45-C11-D25
A9-B45-C11-D25
A13-B45-C11-D25
A24-B45-C11-D25
A69-B45-C11-D25
A67-B45-C11-D25
A39-B45-C11-D25
A65-B45-C11-D25
A66-B45-C11-D25
A2-B53-C11-D25
A3-B53-C11-D25
A9-B53-C11-D25
A13-B53-C11-D25
A24-B53-C11-D25
A69-B53-C11-D25
A67-B53-C11-D25
A39-B53-C11-D25
A65-B53-C11-D25
A66-B53-C11-D25
A2-B79-C11-D25
A3-B79-C11-D25
A9-B79-C11-D25
A13-B79-C11-D25
A24-B79-C11-D25
A69-B79-C11-D25
A67-B79-C11-D25
A39-B79-C11-D25
A65-B79-C11-D25
A66-B79-C11-D25
A2-B80-C11-D25
A3-B80-C11-D25
A9-B80-C11-D25
A13-B80-C11-D25
A24-B80-C11-D25
A69-B80-C11-D25
A67-B80-C11-D25
A39-B80-C11-D25
A65-B80-C11-D25
A66-B80-C11-D25
A2-B85-C11-D25
A3-B85-C11-D25
A9-B85-C11-D25
A13-B85-C11-D25
A24-B85-C11-D25
A69-B85-C11-D25
A67-B85-C11-D25
A39-B85-C11-D25
A65-B85-C11-D25
A66-B85-C11-D25
A2-B86-C11-D25
A3-B86-C11-D25
A9-B86-C11-D25
A13-B86-C11-D25
A24-B86-C11-D25
A69-B86-C11-D25
A67-B86-C11-D25
A39-B86-C11-D25
A65-B86-C11-D25
A66-B86-C11-D25
A2-B87-C11-D25

-continued

A3-B87-C11-D25
A9-B87-C11-D25
A13-B87-C11-D25
A24-B87-C11-D25
A69-B87-C11-D25
A67-B87-C11-D25
A39-B87-C11-D25
A65-B87-C11-D25
A66-B87-C11-D25
A2-B89-C11-D25
A3-B89-C11-D25
A9-B89-C11-D25
A13-B89-C11-D25
A24-B89-C11-D25
A69-B89-C11-D25
A67-B89-C11-D25
A39-B89-C11-D25
A65-B89-C11-D25
A66-B89-C11-D25
A2-B92-C11-D25
A3-B92-C11-D25
A9-B92-C11-D25
A13-B92-C11-D25
A24-B92-C11-D25
A69-B92-C11-D25
A67-B92-C11-D25
A39-B92-C11-D25
A65-B92-C11-D25
A66-B92-C11-D25
A2-B4-C12-D25
A3-B4-C12-D25
A9-B4-C12-D25
A13-B4-C12-D25
A24-B4-C12-D25
A69-B4-C12-D25
A67-B4-C12-D25
A39-B4-C12-D25
A65-B4-C12-D25
A66-B4-C12-D25
A2-B5-C12-D25
A3-B5-C12-D25
A9-B5-C12-D25
A13-B5-C12-D25
A24-B5-C12-D25
A69-B5-C12-D25
A67-B5-C12-D25
A39-B5-C12-D25
A65-B5-C12-D25
A66-B5-C12-D25
A2-B6-C12-D25
A3-B6-C12-D25
A9-B6-C12-D25
A13-B6-C12-D25
A24-B6-C12-D25
A69-B6-C12-D25
A67-B6-C12-D25
A39-B6-C12-D25
A65-B6-C12-D25
A66-B6-C12-D25
A2-B32-C12-D25
A3-B32-C12-D25
A9-B32-C12-D25
A13-B32-C12-D25
A24-B32-C12-D25
A69-B32-C12-D25
A67-B32-C12-D25
A39-B32-C12-D25
A65-B32-C12-D25
A66-B32-C12-D25
A2-B39-C12-D25
A3-B39-C12-D25
A9-B39-C12-D25
A13-B39-C12-D25
A24-B39-C12-D25
A69-B39-C12-D25
A67-B39-C12-D25
A39-B39-C12-D25
A65-B39-C12-D25
A66-B39-C12-D25
A2-B45-C12-D25

-continued

A3-B45-C12-D25
A9-B45-C12-D25
A13-B45-C12-D25
A24-B45-C12-D25
A69-B45-C12-D25
A67-B45-C12-D25
A39-B45-C12-D25
A65-B45-C12-D25
A66-B45-C12-D25
A2-B53-C12-D25
A3-B53-C12-D25
A9-B53-C12-D25
A13-B53-C12-D25
A24-B53-C12-D25
A69-B53-C12-D25
A67-B53-C12-D25
A39-B53-C12-D25
A65-B53-C12-D25
A66-B53-C12-D25
A2-B79-C12-D25
A3-B79-C12-D25
A9-B79-C12-D25
A13-B79-C12-D25
A24-B79-C12-D25
A69-B79-C12-D25
A67-B79-C12-D25
A39-B79-C12-D25
A65-B79-C12-D25
A66-B79-C12-D25
A2-B80-C12-D25
A3-B80-C12-D25
A9-B80-C12-D25
A13-B80-C12-D25
A24-B80-C12-D25
A69-B80-C12-D25
A67-B80-C12-D25
A39-B80-C12-D25
A65-B80-C12-D25
A66-B80-C12-D25
A2-B85-C12-D25
A3-B85-C12-D25
A9-B85-C12-D25
A13-B85-C12-D25
A24-B85-C12-D25
A69-B85-C12-D25
A67-B85-C12-D25
A39-B85-C12-D25
A65-B85-C12-D25
A66-B85-C12-D25
A2-B86-C12-D25
A3-B86-C12-D25
A9-B86-C12-D25
A13-B86-C12-D25
A24-B86-C12-D25
A69-B86-C12-D25
A67-B86-C12-D25
A39-B86-C12-D25
A65-B86-C12-D25
A66-B86-C12-D25
A2-B87-C12-D25
A3-B87-C12-D25
A9-B87-C12-D25
A13-B87-C12-D25
A24-B87-C12-D25
A69-B87-C12-D25
A67-B87-C12-D25
A39-B87-C12-D25
A65-B87-C12-D25
A66-B87-C12-D25
A2-B89-C12-D25
A3-B89-C12-D25
A9-B89-C12-D25
A13-B89-C12-D25
A24-B89-C12-D25
A69-B89-C12-D25
A67-B89-C12-D25
A39-B89-C12-D25
A65-B89-C12-D25
A66-B89-C12-D25
A2-B92-C12-D25

-continued
A3-B92-C12-D25
A9-B92-C12-D25
A13-B92-C12-D25
A24-B92-C12-D25
A69-B92-C12-D25
A67-B92-C12-D25
A39-B92-C12-D25
A65-B92-C12-D25
A66-B92-C12-D25
A2-B4-C13-D25
A3-B4-C13-D25
A9-B4-C13-D25
A13-B4-C13-D25
A24-B4-C13-D25
A69-B4-C13-D25
A67-B4-C13-D25
A39-B4-C13-D25
A65-B4-C13-D25
A66-B4-C13-D25
A2-B5-C13-D25
A3-B5-C13-D25
A9-B5-C13-D25
A13-B5-C13-D25
A24-B5-C13-D25
A69-B5-C13-D25
A67-B5-C13-D25
A39-B5-C13-D25
A65-B5-C13-D25
A66-B5-C13-D25
A2-B6-C13-D25
A3-B6-C13-D25
A9-B6-C13-D25
A13-B6-C13-D25
A24-B6-C13-D25
A69-B6-C13-D25
A67-B6-C13-D25
A39-B6-C13-D25
A65-B6-C13-D25
A66-B6-C13-D25
A2-B32-C13-D25
A3-B32-C13-D25
A9-B32-C13-D25
A13-B32-C13-D25
A24-B32-C13-D25
A69-B32-C13-D25
A67-B32-C13-D25
A39-B32-C13-D25
A65-B32-C13-D25
A66-B32-C13-D25
A2-B39-C13-D25
A3-B39-C13-D25
A9-B39-C13-D25
A13-B39-C13-D25
A24-B39-C13-D25
A69-B39-C13-D25
A67-B39-C13-D25
A39-B39-C13-D25
A65-B39-C13-D25
A66-B39-C13-D25
A2-B45-C13-D25
A3-B45-C13-D25
A9-B45-C13-D25
A13-B45-C13-D25
A24-B45-C13-D25
A69-B45-C13-D25
A67-B45-C13-D25
A39-B45-C13-D25
A65-B45-C13-D25
A66-B45-C13-D25
A2-B53-C13-D25
A3-B53-C13-D25
A9-B53-C13-D25
A13-B53-C13-D25
A24-B53-C13-D25
A69-B53-C13-D25
A67-B53-C13-D25
A39-B53-C13-D25
A65-B53-C13-D25
A66-B53-C13-D25
A2-B79-C13-D25

-continued
A3-B79-C13-D25
A9-B79-C13-D25
A13-B79-C13-D25
A24-B79-C13-D25
A69-B79-C13-D25
A67-B79-C13-D25
A39-B79-C13-D25
A65-B79-C13-D25
A66-B79-C13-D25
A2-B80-C13-D25
A3-B80-C13-D25
A9-B80-C13-D25
A13-B80-C13-D25
A24-B80-C13-D25
A69-B80-C13-D25
A67-B80-C13-D25
A39-B80-C13-D25
A65-B80-C13-D25
A66-B80-C13-D25
A2-B85-C13-D25
A3-B85-C13-D25
A9-B85-C13-D25
A13-B85-C13-D25
A24-B85-C13-D25
A69-B85-C13-D25
A67-B85-C13-D25
A39-B85-C13-D25
A65-B85-C13-D25
A66-B85-C13-D25
A2-B86-C13-D25
A3-B86-C13-D25
A9-B86-C13-D25
A13-B86-C13-D25
A24-B86-C13-D25
A69-B86-C13-D25
A67-B86-C13-D25
A39-B86-C13-D25
A65-B86-C13-D25
A66-B86-C13-D25
A2-B87-C13-D25
A3-B87-C13-D25
A9-B87-C13-D25
A13-B87-C13-D25
A24-B87-C13-D25
A69-B87-C13-D25
A67-B87-C13-D25
A39-B87-C13-D25
A65-B87-C13-D25
A66-B87-C13-D25
A2-B89-C13-D25
A3-B89-C13-D25
A9-B89-C13-D25
A13-B89-C13-D25
A24-B89-C13-D25
A69-B89-C13-D25
A67-B89-C13-D25
A39-B89-C13-D25
A65-B89-C13-D25
A66-B89-C13-D25
A2-B92-C13-D25
A3-B92-C13-D25
A9-B92-C13-D25
A13-B92-C13-D25
A24-B92-C13-D25
A69-B92-C13-D25
A67-B92-C13-D25
A39-B92-C13-D25
A65-B92-C13-D25
A66-B92-C13-D25
A2-B4-C1-D26
A3-B4-C1-D26
A9-B4-C1-D26
A13-B4-C1-D26
A24-B4-C1-D26
A69-B4-C1-D26
A67-B4-C1-D26
A39-B4-C1-D26
A65-B4-C1-D26
A66-B4-C1-D26
A2-B5-C1-D26

-continued
A3-B5-C1-D26
A9-B5-C1-D26
A13-B5-C1-D26
A24-B5-C1-D26
A69-B5-C1-D26
A67-B5-C1-D26
A39-B5-C1-D26
A65-B5-C1-D26
A66-B5-C1-D26
A2-B6-C1-D26
A3-B6-C1-D26
A9-B6-C1-D26
A13-B6-C1-D26
A24-B6-C1-D26
A69-B6-C1-D26
A67-B6-C1-D26
A39-B6-C1-D26
A65-B6-C1-D26
A66-B6-C1-D26
A2-B32-C1-D26
A3-B32-C1-D26
A9-B32-C1-D26
A13-B32-C1-D26
A24-B32-C1-D26
A69-B32-C1-D26
A67-B32-C1-D26
A39-B32-C1-D26
A65-B32-C1-D26
A66-B32-C1-D26
A2-B39-C1-D26
A3-B39-C1-D26
A9-B39-C1-D26
A13-B39-C1-D26
A24-B39-C1-D26
A69-B39-C1-D26
A67-B39-C1-D26
A39-B39-C1-D26
A65-B39-C1-D26
A66-B39-C1-D26
A2-B45-C1-D26
A3-B45-C1-D26
A9-B45-C1-D26
A13-B45-C1-D26
A24-B45-C1-D26
A69-B45-C1-D26
A67-B45-C1-D26
A39-B45-C1-D26
A65-B45-C1-D26
A66-B45-C1-D26
A2-B53-C1-D26
A3-B53-C1-D26
A9-B53-C1-D26
A13-B53-C1-D26
A24-B53-C1-D26
A69-B53-C1-D26
A67-B53-C1-D26
A39-B53-C1-D26
A65-B53-C1-D26
A66-B53-C1-D26
A2-B79-C1-D26
A3-B79-C1-D26
A9-B79-C1-D26
A13-B79-C1-D26
A24-B79-C1-D26
A69-B79-C1-D26
A67-B79-C1-D26
A39-B79-C1-D26
A65-B79-C1-D26
A66-B79-C1-D26
A2-B80-C1-D26
A3-B80-C1-D26
A9-B80-C1-D26
A13-B80-C1-D26
A24-B80-C1-D26
A69-B80-C1-D26
A67-B80-C1-D26
A39-B80-C1-D26
A65-B80-C1-D26
A66-B80-C1-D26
A2-B85-C1-D26

-continued
A3-B85-C1-D26
A9-B85-C1-D26
A13-B85-C1-D26
A24-B85-C1-D26
A69-B85-C1-D26
A67-B85-C1-D26
A39-B85-C1-D26
A65-B85-C1-D26
A66-B85-C1-D26
A2-B86-C1-D26
A3-B86-C1-D26
A9-B86-C1-D26
A13-B86-C1-D26
A24-B86-C1-D26
A69-B86-C1-D26
A67-B86-C1-D26
A39-B86-C1-D26
A65-B86-C1-D26
A66-B86-C1-D26
A2-B87-C1-D26
A3-B87-C1-D26
A9-B87-C1-D26
A13-B87-C1-D26
A24-B87-C1-D26
A69-B87-C1-D26
A67-B87-C1-D26
A39-B87-C1-D26
A65-B87-C1-D26
A66-B87-C1-D26
A2-B89-C1-D26
A3-B89-C1-D26
A9-B89-C1-D26
A13-B89-C1-D26
A24-B89-C1-D26
A69-B89-C1-D26
A67-B89-C1-D26
A39-B89-C1-D26
A65-B89-C1-D26
A66-B89-C1-D26
A2-B92-C1-D26
A3-B92-C1-D26
A9-B92-C1-D26
A13-B92-C1-D26
A24-B92-C1-D26
A69-B92-C1-D26
A67-B92-C1-D26
A39-B92-C1-D26
A65-B92-C1-D26
A66-B92-C1-D26
A2-B4-C2-D26
A3-B4-C2-D26
A9-B4-C2-D26
A13-B4-C2-D26
A24-B4-C2-D26
A69-B4-C2-D26
A67-B4-C2-D26
A39-B4-C2-D26
A65-B4-C2-D26
A66-B4-C2-D26
A2-B5-C2-D26
A3-B5-C2-D26
A9-B5-C2-D26
A13-B5-C2-D26
A24-B5-C2-D26
A69-B5-C2-D26
A67-B5-C2-D26
A39-B5-C2-D26
A65-B5-C2-D26
A66-B5-C2-D26
A2-B6-C2-D26
A3-B6-C2-D26
A9-B6-C2-D26
A13-B6-C2-D26
A24-B6-C2-D26
A69-B6-C2-D26
A67-B6-C2-D26
A39-B6-C2-D26
A65-B6-C2-D26
A66-B6-C2-D26
A2-B32-C2-D26

-continued

A3-B32-C2-D26
A9-B32-C2-D26
A13-B32-C2-D26
A24-B32-C2-D26
A69-B32-C2-D26
A67-B32-C2-D26
A39-B32-C2-D26
A65-B32-C2-D26
A66-B32-C2-D26
A2-B39-C2-D26
A3-B39-C2-D26
A9-B39-C2-D26
A13-B39-C2-D26
A24-B39-C2-D26
A69-B39-C2-D26
A67-B39-C2-D26
A39-B39-C2-D26
A65-B39-C2-D26
A66-B39-C2-D26
A2-B45-C2-D26
A3-B45-C2-D26
A9-B45-C2-D26
A13-B45-C2-D26
A24-B45-C2-D26
A69-B45-C2-D26
A67-B45-C2-D26
A39-B45-C2-D26
A65-B45-C2-D26
A66-B45-C2-D26
A2-B53-C2-D26
A3-B53-C2-D26
A9-B53-C2-D26
A13-B53-C2-D26
A24-B53-C2-D26
A69-B53-C2-D26
A67-B53-C2-D26
A39-B53-C2-D26
A65-B53-C2-D26
A66-B53-C2-D26
A2-B79-C2-D26
A3-B79-C2-D26
A9-B79-C2-D26
A13-B79-C2-D26
A24-B79-C2-D26
A69-B79-C2-D26
A67-B79-C2-D26
A39-B79-C2-D26
A65-B79-C2-D26
A66-B79-C2-D26
A2-B80-C2-D26
A3-B80-C2-D26
A9-B80-C2-D26
A13-B80-C2-D26
A24-B80-C2-D26
A69-B80-C2-D26
A67-B80-C2-D26
A39-B80-C2-D26
A65-B80-C2-D26
A66-B80-C2-D26
A2-B85-C2-D26
A3-B85-C2-D26
A9-B85-C2-D26
A13-B85-C2-D26
A24-B85-C2-D26
A69-B85-C2-D26
A67-B85-C2-D26
A39-B85-C2-D26
A65-B85-C2-D26
A66-B85-C2-D26
A2-B86-C2-D26
A3-B86-C2-D26
A9-B86-C2-D26
A13-B86-C2-D26
A24-B86-C2-D26
A69-B86-C2-D26
A67-B86-C2-D26
A39-B86-C2-D26
A65-B86-C2-D26
A66-B86-C2-D26
A2-B87-C2-D26

-continued

A3-B87-C2-D26
A9-B87-C2-D26
A13-B87-C2-D26
A24-B87-C2-D26
A69-B87-C2-D26
A67-B87-C2-D26
A39-B87-C2-D26
A65-B87-C2-D26
A66-B87-C2-D26
A2-B89-C2-D26
A3-B89-C2-D26
A9-B89-C2-D26
A13-B89-C2-D26
A24-B89-C2-D26
A69-B89-C2-D26
A67-B89-C2-D26
A39-B89-C2-D26
A65-B89-C2-D26
A66-B89-C2-D26
A2-B92-C2-D26
A3-B92-C2-D26
A9-B92-C2-D26
A13-B92-C2-D26
A24-B92-C2-D26
A69-B92-C2-D26
A67-B92-C2-D26
A39-B92-C2-D26
A65-B92-C2-D26
A66-B92-C2-D26
A2-B4-C3-D26
A3-B4-C3-D26
A9-B4-C3-D26
A13-B4-C3-D26
A24-B4-C3-D26
A69-B4-C3-D26
A67-B4-C3-D26
A39-B4-C3-D26
A65-B4-C3-D26
A66-B4-C3-D26
A2-B5-C3-D26
A3-B5-C3-D26
A9-B5-C3-D26
A13-B5-C3-D26
A24-B5-C3-D26
A69-B5-C3-D26
A67-B5-C3-D26
A39-B5-C3-D26
A65-B5-C3-D26
A66-B5-C3-D26
A2-B6-C3-D26
A3-B6-C3-D26
A9-B6-C3-D26
A13-B6-C3-D26
A24-B6-C3-D26
A69-B6-C3-D26
A67-B6-C3-D26
A39-B6-C3-D26
A65-B6-C3-D26
A66-B6-C3-D26
A2-B32-C3-D26
A3-B32-C3-D26
A9-B32-C3-D26
A13-B32-C3-D26
A24-B32-C3-D26
A69-B32-C3-D26
A67-B32-C3-D26
A39-B32-C3-D26
A65-B32-C3-D26
A66-B32-C3-D26
A2-B39-C3-D26
A3-B39-C3-D26
A9-B39-C3-D26
A13-B39-C3-D26
A24-B39-C3-D26
A69-B39-C3-D26
A67-B39-C3-D26
A39-B39-C3-D26
A65-B39-C3-D26
A66-B39-C3-D26
A2-B45-C3-D26

-continued

A3-B45-C3-D26
A9-B45-C3-D26
A13-B45-C3-D26
A24-B45-C3-D26
A69-B45-C3-D26
A67-B45-C3-D26
A39-B45-C3-D26
A65-B45-C3-D26
A66-B45-C3-D26
A2-B53-C3-D26
A3-B53-C3-D26
A9-B53-C3-D26
A13-B53-C3-D26
A24-B53-C3-D26
A69-B53-C3-D26
A67-B53-C3-D26
A39-B53-C3-D26
A65-B53-C3-D26
A66-B53-C3-D26
A2-B79-C3-D26
A3-B79-C3-D26
A9-B79-C3-D26
A13-B79-C3-D26
A24-B79-C3-D26
A69-B79-C3-D26
A67-B79-C3-D26
A39-B79-C3-D26
A65-B79-C3-D26
A66-B79-C3-D26
A2-B80-C3-D26
A3-B80-C3-D26
A9-B80-C3-D26
A13-B80-C3-D26
A24-B80-C3-D26
A69-B80-C3-D26
A67-B80-C3-D26
A39-B80-C3-D26
A65-B80-C3-D26
A66-B80-C3-D26
A2-B85-C3-D26
A3-B85-C3-D26
A9-B85-C3-D26
A13-B85-C3-D26
A24-B85-C3-D26
A69-B85-C3-D26
A67-B85-C3-D26
A39-B85-C3-D26
A65-B85-C3-D26
A66-B85-C3-D26
A2-B86-C3-D26
A3-B86-C3-D26
A9-B86-C3-D26
A13-B86-C3-D26
A24-B86-C3-D26
A69-B86-C3-D26
A67-B86-C3-D26
A39-B86-C3-D26
A65-B86-C3-D26
A66-B86-C3-D26
A2-B87-C3-D26
A3-B87-C3-D26
A9-B87-C3-D26
A13-B87-C3-D26
A24-B87-C3-D26
A69-B87-C3-D26
A67-B87-C3-D26
A39-B87-C3-D26
A65-B87-C3-D26
A66-B87-C3-D26
A2-B89-C3-D26
A3-B89-C3-D26
A9-B89-C3-D26
A13-B89-C3-D26
A24-B89-C3-D26
A69-B89-C3-D26
A67-B89-C3-D26
A39-B89-C3-D26
A65-B89-C3-D26
A66-B89-C3-D26
A2-B92-C3-D26

-continued

A3-B92-C3-D26
A9-B92-C3-D26
A13-B92-C3-D26
A24-B92-C3-D26
A69-B92-C3-D26
A67-B92-C3-D26
A39-B92-C3-D26
A65-B92-C3-D26
A66-B92-C3-D26
A2-B4-C4-D26
A3-B4-C4-D26
A9-B4-C4-D26
A13-B4-C4-D26
A24-B4-C4-D26
A69-B4-C4-D26
A67-B4-C4-D26
A39-B4-C4-D26
A65-B4-C4-D26
A66-B4-C4-D26
A2-B5-C4-D26
A3-B5-C4-D26
A9-B5-C4-D26
A13-B5-C4-D26
A24-B5-C4-D26
A69-B5-C4-D26
A67-B5-C4-D26
A39-B5-C4-D26
A65-B5-C4-D26
A66-B5-C4-D26
A2-B6-C4-D26
A3-B6-C4-D26
A9-B6-C4-D26
A13-B6-C4-D26
A24-B6-C4-D26
A69-B6-C4-D26
A67-B6-C4-D26
A39-B6-C4-D26
A65-B6-C4-D26
A66-B6-C4-D26
A2-B32-C4-D26
A3-B32-C4-D26
A9-B32-C4-D26
A13-B32-C4-D26
A24-B32-C4-D26
A69-B32-C4-D26
A67-B32-C4-D26
A39-B32-C4-D26
A65-B32-C4-D26
A66-B32-C4-D26
A2-B39-C4-D26
A3-B39-C4-D26
A9-B39-C4-D26
A13-B39-C4-D26
A24-B39-C4-D26
A69-B39-C4-D26
A67-B39-C4-D26
A39-B39-C4-D26
A65-B39-C4-D26
A66-B39-C4-D26
A2-B45-C4-D26
A3-B45-C4-D26
A9-B45-C4-D26
A13-B45-C4-D26
A24-B45-C4-D26
A69-B45-C4-D26
A67-B45-C4-D26
A39-B45-C4-D26
A65-B45-C4-D26
A66-B45-C4-D26
A2-B53-C4-D26
A3-B53-C4-D26
A9-B53-C4-D26
A13-B53-C4-D26
A24-B53-C4-D26
A69-B53-C4-D26
A67-B53-C4-D26
A39-B53-C4-D26
A65-B53-C4-D26
A66-B53-C4-D26
A2-B79-C4-D26

-continued

A3-B79-C4-D26
A9-B79-C4-D26
A13-B79-C4-D26
A24-B79-C4-D26
A69-B79-C4-D26
A67-B79-C4-D26
A39-B79-C4-D26
A65-B79-C4-D26
A66-B79-C4-D26
A2-B80-C4-D26
A3-B80-C4-D26
A9-B80-C4-D26
A13-B80-C4-D26
A24-B80-C4-D26
A69-B80-C4-D26
A67-B80-C4-D26
A39-B80-C4-D26
A65-B80-C4-D26
A66-B80-C4-D26
A2-B85-C4-D26
A3-B85-C4-D26
A9-B85-C4-D26
A13-B85-C4-D26
A24-B85-C4-D26
A69-B85-C4-D26
A67-B85-C4-D26
A39-B85-C4-D26
A65-B85-C4-D26
A66-B85-C4-D26
A2-B86-C4-D26
A3-B86-C4-D26
A9-B86-C4-D26
A13-B86-C4-D26
A24-B86-C4-D26
A69-B86-C4-D26
A67-B86-C4-D26
A39-B86-C4-D26
A65-B86-C4-D26
A66-B86-C4-D26
A2-B87-C4-D26
A3-B87-C4-D26
A9-B87-C4-D26
A13-B87-C4-D26
A24-B87-C4-D26
A69-B87-C4-D26
A67-B87-C4-D26
A39-B87-C4-D26
A65-B87-C4-D26
A66-B87-C4-D26
A2-B89-C4-D26
A3-B89-C4-D26
A9-B89-C4-D26
A13-B89-C4-D26
A24-B89-C4-D26
A69-B89-C4-D26
A67-B89-C4-D26
A39-B89-C4-D26
A65-B89-C4-D26
A66-B89-C4-D26
A2-B92-C4-D26
A3-B92-C4-D26
A9-B92-C4-D26
A13-B92-C4-D26
A24-B92-C4-D26
A69-B92-C4-D26
A67-B92-C4-D26
A39-B92-C4-D26
A65-B92-C4-D26
A66-B92-C4-D26
A2-B4-C5-D26
A3-B4-C5-D26
A9-B4-C5-D26
A13-B4-C5-D26
A24-B4-C5-D26
A69-B4-C5-D26
A67-B4-C5-D26
A39-B4-C5-D26
A65-B4-C5-D26
A66-B4-C5-D26
A2-B5-C5-D26

-continued

A3-B5-C5-D26
A9-B5-C5-D26
A13-B5-C5-D26
A24-B5-C5-D26
A69-B5-C5-D26
A67-B5-C5-D26
A39-B5-C5-D26
A65-B5-C5-D26
A66-B5-C5-D26
A2-B6-C5-D26
A3-B6-C5-D26
A9-B6-C5-D26
A13-B6-C5-D26
A24-B6-C5-D26
A69-B6-C5-D26
A67-B6-C5-D26
A39-B6-C5-D26
A65-B6-C5-D26
A66-B6-C5-D26
A2-B32-C5-D26
A3-B32-C5-D26
A9-B32-C5-D26
A13-B32-C5-D26
A24-B32-C5-D26
A69-B32-C5-D26
A67-B32-C5-D26
A39-B32-C5-D26
A65-B32-C5-D26
A66-B32-C5-D26
A2-B39-C5-D26
A3-B39-C5-D26
A9-B39-C5-D26
A13-B39-C5-D26
A24-B39-C5-D26
A69-B39-C5-D26
A67-B39-C5-D26
A39-B39-C5-D26
A65-B39-C5-D26
A66-B39-C5-D26
A2-B45-C5-D26
A3-B45-C5-D26
A9-B45-C5-D26
A13-B45-C5-D26
A24-B45-C5-D26
A69-B45-C5-D26
A67-B45-C5-D26
A39-B45-C5-D26
A65-B45-C5-D26
A66-B45-C5-D26
A2-B53-C5-D26
A3-B53-C5-D26
A9-B53-C5-D26
A13-B53-C5-D26
A24-B53-C5-D26
A69-B53-C5-D26
A67-B53-C5-D26
A39-B53-C5-D26
A65-B53-C5-D26
A66-B53-C5-D26
A2-B79-C5-D26
A3-B79-C5-D26
A9-B79-C5-D26
A13-B79-C5-D26
A24-B79-C5-D26
A69-B79-C5-D26
A67-B79-C5-D26
A39-B79-C5-D26
A65-B79-C5-D26
A66-B79-C5-D26
A2-B80-C5-D26
A3-B80-C5-D26
A9-B80-C5-D26
A13-B80-C5-D26
A24-B80-C5-D26
A69-B80-C5-D26
A67-B80-C5-D26
A39-B80-C5-D26
A65-B80-C5-D26
A66-B80-C5-D26
A2-B85-C5-D26

-continued
A3-B85-C5-D26
A9-B85-C5-D26
A13-B85-C5-D26
A24-B85-C5-D26
A69-B85-C5-D26
A67-B85-C5-D26
A39-B85-C5-D26
A65-B85-C5-D26
A66-B85-C5-D26
A2-B86-C5-D26
A3-B86-C5-D26
A9-B86-C5-D26
A13-B86-C5-D26
A24-B86-C5-D26
A69-B86-C5-D26
A67-B86-C5-D26
A39-B86-C5-D26
A65-B86-C5-D26
A66-B86-C5-D26
A2-B87-C5-D26
A3-B87-C5-D26
A9-B87-C5-D26
A13-B87-C5-D26
A24-B87-C5-D26
A69-B87-C5-D26
A67-B87-C5-D26
A39-B87-C5-D26
A65-B87-C5-D26
A66-B87-C5-D26
A2-B89-C5-D26
A3-B89-C5-D26
A9-B89-C5-D26
A13-B89-C5-D26
A24-B89-C5-D26
A69-B89-C5-D26
A67-B89-C5-D26
A39-B89-C5-D26
A65-B89-C5-D26
A66-B89-C5-D26
A2-B92-C5-D26
A3-B92-C5-D26
A9-B92-C5-D26
A13-B92-C5-D26
A24-B92-C5-D26
A69-B92-C5-D26
A67-B92-C5-D26
A39-B92-C5-D26
A65-B92-C5-D26
A66-B92-C5-D26
A2-B4-C6-D26
A3-B4-C6-D26
A9-B4-C6-D26
A13-B4-C6-D26
A24-B4-C6-D26
A69-B4-C6-D26
A67-B4-C6-D26
A39-B4-C6-D26
A65-B4-C6-D26
A66-B4-C6-D26
A2-B5-C6-D26
A3-B5-C6-D26
A9-B5-C6-D26
A13-B5-C6-D26
A24-B5-C6-D26
A69-B5-C6-D26
A67-B5-C6-D26
A39-B5-C6-D26
A65-B5-C6-D26
A66-B5-C6-D26
A2-B6-C6-D26
A3-B6-C6-D26
A9-B6-C6-D26
A13-B6-C6-D26
A24-B6-C6-D26
A69-B6-C6-D26
A67-B6-C6-D26
A39-B6-C6-D26
A65-B6-C6-D26
A66-B6-C6-D26
A2-B32-C6-D26

-continued
A3-B32-C6-D26
A9-B32-C6-D26
A13-B32-C6-D26
A24-B32-C6-D26
A69-B32-C6-D26
A67-B32-C6-D26
A39-B32-C6-D26
A65-B32-C6-D26
A66-B32-C6-D26
A2-B39-C6-D26
A3-B39-C6-D26
A9-B39-C6-D26
A13-B39-C6-D26
A24-B39-C6-D26
A69-B39-C6-D26
A67-B39-C6-D26
A39-B39-C6-D26
A65-B39-C6-D26
A66-B39-C6-D26
A2-B45-C6-D26
A3-B45-C6-D26
A9-B45-C6-D26
A13-B45-C6-D26
A24-B45-C6-D26
A69-B45-C6-D26
A67-B45-C6-D26
A39-B45-C6-D26
A65-B45-C6-D26
A66-B45-C6-D26
A2-B53-C6-D26
A3-B53-C6-D26
A9-B53-C6-D26
A13-B53-C6-D26
A24-B53-C6-D26
A69-B53-C6-D26
A67-B53-C6-D26
A39-B53-C6-D26
A65-B53-C6-D26
A66-B53-C6-D26
A2-B79-C6-D26
A3-B79-C6-D26
A9-B79-C6-D26
A13-B79-C6-D26
A24-B79-C6-D26
A69-B79-C6-D26
A67-B79-C6-D26
A39-B79-C6-D26
A65-B79-C6-D26
A66-B79-C6-D26
A2-B80-C6-D26
A3-B80-C6-D26
A9-B80-C6-D26
A13-B80-C6-D26
A24-B80-C6-D26
A69-B80-C6-D26
A67-B80-C6-D26
A39-B80-C6-D26
A65-B80-C6-D26
A66-B80-C6-D26
A2-B85-C6-D26
A3-B85-C6-D26
A9-B85-C6-D26
A13-B85-C6-D26
A24-B85-C6-D26
A69-B85-C6-D26
A67-B85-C6-D26
A39-B85-C6-D26
A65-B85-C6-D26
A66-B85-C6-D26
A2-B86-C6-D26
A3-B86-C6-D26
A9-B86-C6-D26
A13-B86-C6-D26
A24-B86-C6-D26
A69-B86-C6-D26
A67-B86-C6-D26
A39-B86-C6-D26
A65-B86-C6-D26
A66-B86-C6-D26
A2-B87-C6-D26

-continued

A3-B87-C6-D26
A9-B87-C6-D26
A13-B87-C6-D26
A24-B87-C6-D26
A69-B87-C6-D26
A67-B87-C6-D26
A39-B87-C6-D26
A65-B87-C6-D26
A66-B87-C6-D26
A2-B89-C6-D26
A3-B89-C6-D26
A9-B89-C6-D26
A13-B89-C6-D26
A24-B89-C6-D26
A69-B89-C6-D26
A67-B89-C6-D26
A39-B89-C6-D26
A65-B89-C6-D26
A66-B89-C6-D26
A2-B92-C6-D26
A3-B92-C6-D26
A9-B92-C6-D26
A13-B92-C6-D26
A24-B92-C6-D26
A69-B92-C6-D26
A67-B92-C6-D26
A39-B92-C6-D26
A65-B92-C6-D26
A66-B92-C6-D26
A2-B4-C7-D26
A3-B4-C7-D26
A9-B4-C7-D26
A13-B4-C7-D26
A24-B4-C7-D26
A69-B4-C7-D26
A67-B4-C7-D26
A39-B4-C7-D26
A65-B4-C7-D26
A66-B4-C7-D26
A2-B5-C7-D26
A3-B5-C7-D26
A9-B5-C7-D26
A13-B5-C7-D26
A24-B5-C7-D26
A69-B5-C7-D26
A67-B5-C7-D26
A39-B5-C7-D26
A65-B5-C7-D26
A66-B5-C7-D26
A2-B6-C7-D26
A3-B6-C7-D26
A9-B6-C7-D26
A13-B6-C7-D26
A24-B6-C7-D26
A69-B6-C7-D26
A67-B6-C7-D26
A39-B6-C7-D26
A65-B6-C7-D26
A66-B6-C7-D26
A2-B32-C7-D26
A3-B32-C7-D26
A9-B32-C7-D26
A13-B32-C7-D26
A24-B32-C7-D26
A69-B32-C7-D26
A67-B32-C7-D26
A39-B32-C7-D26
A65-B32-C7-D26
A66-B32-C7-D26
A2-B39-C7-D26
A3-B39-C7-D26
A9-B39-C7-D26
A13-B39-C7-D26
A24-B39-C7-D26
A69-B39-C7-D26
A67-B39-C7-D26
A39-B39-C7-D26
A65-B39-C7-D26
A66-B39-C7-D26
A2-B45-C7-D26

-continued

A3-B45-C7-D26
A9-B45-C7-D26
A13-B45-C7-D26
A24-B45-C7-D26
A69-B45-C7-D26
A67-B45-C7-D26
A39-B45-C7-D26
A65-B45-C7-D26
A66-B45-C7-D26
A2-B53-C7-D26
A3-B53-C7-D26
A9-B53-C7-D26
A13-B53-C7-D26
A24-B53-C7-D26
A69-B53-C7-D26
A67-B53-C7-D26
A39-B53-C7-D26
A65-B53-C7-D26
A66-B53-C7-D26
A2-B79-C7-D26
A3-B79-C7-D26
A9-B79-C7-D26
A13-B79-C7-D26
A24-B79-C7-D26
A69-B79-C7-D26
A67-B79-C7-D26
A39-B79-C7-D26
A65-B79-C7-D26
A66-B79-C7-D26
A2-B80-C7-D26
A3-B80-C7-D26
A9-B80-C7-D26
A13-B80-C7-D26
A24-B80-C7-D26
A69-B80-C7-D26
A67-B80-C7-D26
A39-B80-C7-D26
A65-B80-C7-D26
A66-B80-C7-D26
A2-B85-C7-D26
A3-B85-C7-D26
A9-B85-C7-D26
A13-B85-C7-D26
A24-B85-C7-D26
A69-B85-C7-D26
A67-B85-C7-D26
A39-B85-C7-D26
A65-B85-C7-D26
A66-B85-C7-D26
A2-B86-C7-D26
A3-B86-C7-D26
A9-B86-C7-D26
A13-B86-C7-D26
A24-B86-C7-D26
A69-B86-C7-D26
A67-B86-C7-D26
A39-B86-C7-D26
A65-B86-C7-D26
A66-B86-C7-D26
A2-B87-C7-D26
A3-B87-C7-D26
A9-B87-C7-D26
A13-B87-C7-D26
A24-B87-C7-D26
A69-B87-C7-D26
A67-B87-C7-D26
A39-B87-C7-D26
A65-B87-C7-D26
A66-B87-C7-D26
A2-B89-C7-D26
A3-B89-C7-D26
A9-B89-C7-D26
A13-B89-C7-D26
A24-B89-C7-D26
A69-B89-C7-D26
A67-B89-C7-D26
A39-B89-C7-D26
A65-B89-C7-D26
A66-B89-C7-D26
A2-B92-C7-D26

-continued

A3-B92-C7-D26
A9-B92-C7-D26
A13-B92-C7-D26
A24-B92-C7-D26
A69-B92-C7-D26
A67-B92-C7-D26
A39-B92-C7-D26
A65-B92-C7-D26
A66-B92-C7-D26
A2-B4-C8-D26
A3-B4-C8-D26
A9-B4-C8-D26
A13-B4-C8-D26
A24-B4-C8-D26
A69-B4-C8-D26
A67-B4-C8-D26
A39-B4-C8-D26
A65-B4-C8-D26
A66-B4-C8-D26
A2-B5-C8-D26
A3-B5-C8-D26
A9-B5-C8-D26
A13-B5-C8-D26
A24-B5-C8-D26
A69-B5-C8-D26
A67-B5-C8-D26
A39-B5-C8-D26
A65-B5-C8-D26
A66-B5-C8-D26
A2-B6-C8-D26
A3-B6-C8-D26
A9-B6-C8-D26
A13-B6-C8-D26
A24-B6-C8-D26
A69-B6-C8-D26
A67-B6-C8-D26
A39-B6-C8-D26
A65-B6-C8-D26
A66-B6-C8-D26
A2-B32-C8-D26
A3-B32-C8-D26
A9-B32-C8-D26
A13-B32-C8-D26
A24-B32-C8-D26
A69-B32-C8-D26
A67-B32-C8-D26
A39-B32-C8-D26
A65-B32-C8-D26
A66-B32-C8-D26
A2-B39-C8-D26
A3-B39-C8-D26
A9-B39-C8-D26
A13-B39-C8-D26
A24-B39-C8-D26
A69-B39-C8-D26
A67-B39-C8-D26
A39-B39-C8-D26
A65-B39-C8-D26
A66-B39-C8-D26
A2-B45-C8-D26
A3-B45-C8-D26
A9-B45-C8-D26
A13-B45-C8-D26
A24-B45-C8-D26
A69-B45-C8-D26
A67-B45-C8-D26
A39-B45-C8-D26
A65-B45-C8-D26
A66-B45-C8-D26
A2-B53-C8-D26
A3-B53-C8-D26
A9-B53-C8-D26
A13-B53-C8-D26
A24-B53-C8-D26
A69-B53-C8-D26
A67-B53-C8-D26
A39-B53-C8-D26
A65-B53-C8-D26
A66-B53-C8-D26
A2-B79-C8-D26

-continued

A3-B79-C8-D26
A9-B79-C8-D26
A13-B79-C8-D26
A24-B79-C8-D26
A69-B79-C8-D26
A67-B79-C8-D26
A39-B79-C8-D26
A65-B79-C8-D26
A66-B79-C8-D26
A2-B80-C8-D26
A3-B80-C8-D26
A9-B80-C8-D26
A13-B80-C8-D26
A24-B80-C8-D26
A69-B80-C8-D26
A67-B80-C8-D26
A39-B80-C8-D26
A65-B80-C8-D26
A66-B80-C8-D26
A2-B85-C8-D26
A3-B85-C8-D26
A9-B85-C8-D26
A13-B85-C8-D26
A24-B85-C8-D26
A69-B85-C8-D26
A67-B85-C8-D26
A39-B85-C8-D26
A65-B85-C8-D26
A66-B85-C8-D26
A2-B86-C8-D26
A3-B86-C8-D26
A9-B86-C8-D26
A13-B86-C8-D26
A24-B86-C8-D26
A69-B86-C8-D26
A67-B86-C8-D26
A39-B86-C8-D26
A65-B86-C8-D26
A66-B86-C8-D26
A2-B87-C8-D26
A3-B87-C8-D26
A9-B87-C8-D26
A13-B87-C8-D26
A24-B87-C8-D26
A69-B87-C8-D26
A67-B87-C8-D26
A39-B87-C8-D26
A65-B87-C8-D26
A66-B87-C8-D26
A2-B89-C8-D26
A3-B89-C8-D26
A9-B89-C8-D26
A13-B89-C8-D26
A24-B89-C8-D26
A69-B89-C8-D26
A67-B89-C8-D26
A39-B89-C8-D26
A65-B89-C8-D26
A66-B89-C8-D26
A2-B92-C8-D26
A3-B92-C8-D26
A9-B92-C8-D26
A13-B92-C8-D26
A24-B92-C8-D26
A69-B92-C8-D26
A67-B92-C8-D26
A39-B92-C8-D26
A65-B92-C8-D26
A66-B92-C8-D26
A2-B4-C9-D26
A3-B4-C9-D26
A9-B4-C9-D26
A13-B4-C9-D26
A24-B4-C9-D26
A69-B4-C9-D26
A67-B4-C9-D26
A39-B4-C9-D26
A65-B4-C9-D26
A66-B4-C9-D26
A2-B5-C9-D26

-continued
A3-B5-C9-D26
A9-B5-C9-D26
A13-B5-C9-D26
A24-B5-C9-D26
A69-B5-C9-D26
A67-B5-C9-D26
A39-B5-C9-D26
A65-B5-C9-D26
A66-B5-C9-D26
A2-B6-C9-D26
A3-B6-C9-D26
A9-B6-C9-D26
A13-B6-C9-D26
A24-B6-C9-D26
A69-B6-C9-D26
A67-B6-C9-D26
A39-B6-C9-D26
A65-B6-C9-D26
A66-B6-C9-D26
A2-B32-C9-D26
A3-B32-C9-D26
A9-B32-C9-D26
A13-B32-C9-D26
A24-B32-C9-D26
A69-B32-C9-D26
A67-B32-C9-D26
A39-B32-C9-D26
A65-B32-C9-D26
A66-B32-C9-D26
A2-B39-C9-D26
A3-B39-C9-D26
A9-B39-C9-D26
A13-B39-C9-D26
A24-B39-C9-D26
A69-B39-C9-D26
A67-B39-C9-D26
A39-B39-C9-D26
A65-B39-C9-D26
A66-B39-C9-D26
A2-B45-C9-D26
A3-B45-C9-D26
A9-B45-C9-D26
A13-B45-C9-D26
A24-B45-C9-D26
A69-B45-C9-D26
A67-B45-C9-D26
A39-B45-C9-D26
A65-B45-C9-D26
A66-B45-C9-D26
A2-B53-C9-D26
A3-B53-C9-D26
A9-B53-C9-D26
A13-B53-C9-D26
A24-B53-C9-D26
A69-B53-C9-D26
A67-B53-C9-D26
A39-B53-C9-D26
A65-B53-C9-D26
A66-B53-C9-D26
A2-B79-C9-D26
A3-B79-C9-D26
A9-B79-C9-D26
A13-B79-C9-D26
A24-B79-C9-D26
A69-B79-C9-D26
A67-B79-C9-D26
A39-B79-C9-D26
A65-B79-C9-D26
A66-B79-C9-D26
A2-B80-C9-D26
A3-B80-C9-D26
A9-B80-C9-D26
A13-B80-C9-D26
A24-B80-C9-D26
A69-B80-C9-D26
A67-B80-C9-D26
A39-B80-C9-D26
A65-B80-C9-D26
A66-B80-C9-D26
A2-B85-C9-D26

-continued
A3-B85-C9-D26
A9-B85-C9-D26
A13-B85-C9-D26
A24-B85-C9-D26
A69-B85-C9-D26
A67-B85-C9-D26
A39-B85-C9-D26
A65-B85-C9-D26
A66-B85-C9-D26
A2-B86-C9-D26
A3-B86-C9-D26
A9-B86-C9-D26
A13-B86-C9-D26
A24-B86-C9-D26
A69-B86-C9-D26
A67-B86-C9-D26
A39-B86-C9-D26
A65-B86-C9-D26
A66-B86-C9-D26
A2-B87-C9-D26
A3-B87-C9-D26
A9-B87-C9-D26
A13-B87-C9-D26
A24-B87-C9-D26
A69-B87-C9-D26
A67-B87-C9-D26
A39-B87-C9-D26
A65-B87-C9-D26
A66-B87-C9-D26
A2-B89-C9-D26
A3-B89-C9-D26
A9-B89-C9-D26
A13-B89-C9-D26
A24-B89-C9-D26
A69-B89-C9-D26
A67-B89-C9-D26
A39-B89-C9-D26
A65-B89-C9-D26
A66-B89-C9-D26
A2-B92-C9-D26
A3-B92-C9-D26
A9-B92-C9-D26
A13-B92-C9-D26
A24-B92-C9-D26
A69-B92-C9-D26
A67-B92-C9-D26
A39-B92-C9-D26
A65-B92-C9-D26
A66-B92-C9-D26
A2-B4-C10-D26
A3-B4-C10-D26
A9-B4-C10-D26
A13-B4-C10-D26
A24-B4-C10-D26
A69-B4-C10-D26
A67-B4-C10-D26
A39-B4-C10-D26
A65-B4-C10-D26
A66-B4-C10-D26
A2-B5-C10-D26
A3-B5-C10-D26
A9-B5-C10-D26
A13-B5-C10-D26
A24-B5-C10-D26
A69-B5-C10-D26
A67-B5-C10-D26
A39-B5-C10-D26
A65-B5-C10-D26
A66-B5-C10-D26
A2-B6-C10-D26
A3-B6-C10-D26
A9-B6-C10-D26
A13-B6-C10-D26
A24-B6-C10-D26
A69-B6-C10-D26
A67-B6-C10-D26
A39-B6-C10-D26
A65-B6-C10-D26
A66-B6-C10-D26
A2-B32-C10-D26

-continued

A3-B32-C10-D26
A9-B32-C10-D26
A13-B32-C10-D26
A24-B32-C10-D26
A69-B32-C10-D26
A67-B32-C10-D26
A39-B32-C10-D26
A65-B32-C10-D26
A66-B32-C10-D26
A2-B39-C10-D26
A3-B39-C10-D26
A9-B39-C10-D26
A13-B39-C10-D26
A24-B39-C10-D26
A69-B39-C10-D26
A67-B39-C10-D26
A39-B39-C10-D26
A65-B39-C10-D26
A66-B39-C10-D26
A2-B45-C10-D26
A3-B45-C10-D26
A9-B45-C10-D26
A13-B45-C10-D26
A24-B45-C10-D26
A69-B45-C10-D26
A67-B45-C10-D26
A39-B45-C10-D26
A65-B45-C10-D26
A66-B45-C10-D26
A2-B53-C10-D26
A3-B53-C10-D26
A9-B53-C10-D26
A13-B53-C10-D26
A24-B53-C10-D26
A69-B53-C10-D26
A67-B53-C10-D26
A39-B53-C10-D26
A65-B53-C10-D26
A66-B53-C10-D26
A2-B79-C10-D26
A3-B79-C10-D26
A9-B79-C10-D26
A13-B79-C10-D26
A24-B79-C10-D26
A69-B79-C10-D26
A67-B79-C10-D26
A39-B79-C10-D26
A65-B79-C10-D26
A66-B79-C10-D26
A2-B80-C10-D26
A3-B80-C10-D26
A9-B80-C10-D26
A13-B80-C10-D26
A24-B80-C10-D26
A69-B80-C10-D26
A67-B80-C10-D26
A39-B80-C10-D26
A65-B80-C10-D26
A66-B80-C10-D26
A2-B85-C10-D26
A3-B85-C10-D26
A9-B85-C10-D26
A13-B85-C10-D26
A24-B85-C10-D26
A69-B85-C10-D26
A67-B85-C10-D26
A39-B85-C10-D26
A65-B85-C10-D26
A66-B85-C10-D26
A2-B86-C10-D26
A3-B86-C10-D26
A9-B86-C10-D26
A13-B86-C10-D26
A24-B86-C10-D26
A69-B86-C10-D26
A67-B86-C10-D26
A39-B86-C10-D26
A65-B86-C10-D26
A66-B86-C10-D26
A2-B87-C10-D26

-continued

A3-B87-C10-D26
A9-B87-C10-D26
A13-B87-C10-D26
A24-B87-C10-D26
A69-B87-C10-D26
A67-B87-C10-D26
A39-B87-C10-D26
A65-B87-C10-D26
A66-B87-C10-D26
A2-B89-C10-D26
A3-B89-C10-D26
A9-B89-C10-D26
A13-B89-C10-D26
A24-B89-C10-D26
A69-B89-C10-D26
A67-B89-C10-D26
A39-B89-C10-D26
A65-B89-C10-D26
A66-B89-C10-D26
A2-B92-C10-D26
A3-B92-C10-D26
A9-B92-C10-D26
A13-B92-C10-D26
A24-B92-C10-D26
A69-B92-C10-D26
A67-B92-C10-D26
A39-B92-C10-D26
A65-B92-C10-D26
A66-B92-C10-D26
A2-B4-C11-D26
A3-B4-C11-D26
A9-B4-C11-D26
A13-B4-C11-D26
A24-B4-C11-D26
A69-B4-C11-D26
A67-B4-C11-D26
A39-B4-C11-D26
A65-B4-C11-D26
A66-B4-C11-D26
A2-B5-C11-D26
A3-B5-C11-D26
A9-B5-C11-D26
A13-B5-C11-D26
A24-B5-C11-D26
A69-B5-C11-D26
A67-B5-C11-D26
A39-B5-C11-D26
A65-B5-C11-D26
A66-B5-C11-D26
A2-B6-C11-D26
A3-B6-C11-D26
A9-B6-C11-D26
A13-B6-C11-D26
A24-B6-C11-D26
A69-B6-C11-D26
A67-B6-C11-D26
A39-B6-C11-D26
A65-B6-C11-D26
A66-B6-C11-D26
A2-B32-C11-D26
A3-B32-C11-D26
A9-B32-C11-D26
A13-B32-C11-D26
A24-B32-C11-D26
A69-B32-C11-D26
A67-B32-C11-D26
A39-B32-C11-D26
A65-B32-C11-D26
A66-B32-C11-D26
A2-B39-C11-D26
A3-B39-C11-D26
A9-B39-C11-D26
A13-B39-C11-D26
A24-B39-C11-D26
A69-B39-C11-D26
A67-B39-C11-D26
A39-B39-C11-D26
A65-B39-C11-D26
A66-B39-C11-D26
A2-B45-C11-D26

-continued

A3-B45-C11-D26
A9-B45-C11-D26
A13-B45-C11-D26
A24-B45-C11-D26
A69-B45-C11-D26
A67-B45-C11-D26
A39-B45-C11-D26
A65-B45-C11-D26
A66-B45-C11-D26
A2-B53-C11-D26
A3-B53-C11-D26
A9-B53-C11-D26
A13-B53-C11-D26
A24-B53-C11-D26
A69-B53-C11-D26
A67-B53-C11-D26
A39-B53-C11-D26
A65-B53-C11-D26
A66-B53-C11-D26
A2-B79-C11-D26
A3-B79-C11-D26
A9-B79-C11-D26
A13-B79-C11-D26
A24-B79-C11-D26
A69-B79-C11-D26
A67-B79-C11-D26
A39-B79-C11-D26
A65-B79-C11-D26
A66-B79-C11-D26
A2-B80-C11-D26
A3-B80-C11-D26
A9-B80-C11-D26
A13-B80-C11-D26
A24-B80-C11-D26
A69-B80-C11-D26
A67-B80-C11-D26
A39-B80-C11-D26
A65-B80-C11-D26
A66-B80-C11-D26
A2-B85-C11-D26
A3-B85-C11-D26
A9-B85-C11-D26
A13-B85-C11-D26
A24-B85-C11-D26
A69-B85-C11-D26
A67-B85-C11-D26
A39-B85-C11-D26
A65-B85-C11-D26
A66-B85-C11-D26
A2-B86-C11-D26
A3-B86-C11-D26
A9-B86-C11-D26
A13-B86-C11-D26
A24-B86-C11-D26
A69-B86-C11-D26
A67-B86-C11-D26
A39-B86-C11-D26
A65-B86-C11-D26
A66-B86-C11-D26
A2-B87-C11-D26
A3-B87-C11-D26
A9-B87-C11-D26
A13-B87-C11-D26
A24-B87-C11-D26
A69-B87-C11-D26
A67-B87-C11-D26
A39-B87-C11-D26
A65-B87-C11-D26
A66-B87-C11-D26
A2-B89-C11-D26
A3-B89-C11-D26
A9-B89-C11-D26
A13-B89-C11-D26
A24-B89-C11-D26
A69-B89-C11-D26
A67-B89-C11-D26
A39-B89-C11-D26
A65-B89-C11-D26
A66-B89-C11-D26
A2-B92-C11-D26

-continued

A3-B92-C11-D26
A9-B92-C11-D26
A13-B92-C11-D26
A24-B92-C11-D26
A69-B92-C11-D26
A67-B92-C11-D26
A39-B92-C11-D26
A65-B92-C11-D26
A66-B92-C11-D26
A2-B4-C12-D26
A3-B4-C12-D26
A9-B4-C12-D26
A13-B4-C12-D26
A24-B4-C12-D26
A69-B4-C12-D26
A67-B4-C12-D26
A39-B4-C12-D26
A65-B4-C12-D26
A66-B4-C12-D26
A2-B5-C12-D26
A3-B5-C12-D26
A9-B5-C12-D26
A13-B5-C12-D26
A24-B5-C12-D26
A69-B5-C12-D26
A67-B5-C12-D26
A39-B5-C12-D26
A65-B5-C12-D26
A66-B5-C12-D26
A2-B6-C12-D26
A3-B6-C12-D26
A9-B6-C12-D26
A13-B6-C12-D26
A24-B6-C12-D26
A69-B6-C12-D26
A67-B6-C12-D26
A39-B6-C12-D26
A65-B6-C12-D26
A66-B6-C12-D26
A2-B32-C12-D26
A3-B32-C12-D26
A9-B32-C12-D26
A13-B32-C12-D26
A24-B32-C12-D26
A69-B32-C12-D26
A67-B32-C12-D26
A39-B32-C12-D26
A65-B32-C12-D26
A66-B32-C12-D26
A2-B39-C12-D26
A3-B39-C12-D26
A9-B39-C12-D26
A13-B39-C12-D26
A24-B39-C12-D26
A69-B39-C12-D26
A67-B39-C12-D26
A39-B39-C12-D26
A65-B39-C12-D26
A66-B39-C12-D26
A2-B45-C12-D26
A3-B45-C12-D26
A9-B45-C12-D26
A13-B45-C12-D26
A24-B45-C12-D26
A69-B45-C12-D26
A67-B45-C12-D26
A39-B45-C12-D26
A65-B45-C12-D26
A66-B45-C12-D26
A2-B53-C12-D26
A3-B53-C12-D26
A9-B53-C12-D26
A13-B53-C12-D26
A24-B53-C12-D26
A69-B53-C12-D26
A67-B53-C12-D26
A39-B53-C12-D26
A65-B53-C12-D26
A66-B53-C12-D26
A2-B79-C12-D26

-continued

A3-B79-C12-D26
A9-B79-C12-D26
A13-B79-C12-D26
A24-B79-C12-D26
A69-B79-C12-D26
A67-B79-C12-D26
A39-B79-C12-D26
A65-B79-C12-D26
A66-B79-C12-D26
A2-B80-C12-D26
A3-B80-C12-D26
A9-B80-C12-D26
A13-B80-C12-D26
A24-B80-C12-D26
A69-B80-C12-D26
A67-B80-C12-D26
A39-B80-C12-D26
A65-B80-C12-D26
A66-B80-C12-D26
A2-B85-C12-D26
A3-B85-C12-D26
A9-B85-C12-D26
A13-B85-C12-D26
A24-B85-C12-D26
A69-B85-C12-D26
A67-B85-C12-D26
A39-B85-C12-D26
A65-B85-C12-D26
A66-B85-C12-D26
A2-B86-C12-D26
A3-B86-C12-D26
A9-B86-C12-D26
A13-B86-C12-D26
A24-B86-C12-D26
A69-B86-C12-D26
A67-B86-C12-D26
A39-B86-C12-D26
A65-B86-C12-D26
A66-B86-C12-D26
A2-B87-C12-D26
A3-B87-C12-D26
A9-B87-C12-D26
A13-B87-C12-D26
A24-B87-C12-D26
A69-B87-C12-D26
A67-B87-C12-D26
A39-B87-C12-D26
A65-B87-C12-D26
A66-B87-C12-D26
A2-B89-C12-D26
A3-B89-C12-D26
A9-B89-C12-D26
A13-B89-C12-D26
A24-B89-C12-D26
A69-B89-C12-D26
A67-B89-C12-D26
A39-B89-C12-D26
A65-B89-C12-D26
A66-B89-C12-D26
A2-B92-C12-D26
A3-B92-C12-D26
A9-B92-C12-D26
A13-B92-C12-D26
A24-B92-C12-D26
A69-B92-C12-D26
A67-B92-C12-D26
A39-B92-C12-D26
A65-B92-C12-D26
A66-B92-C12-D26
A2-B4-C13-D26
A3-B4-C13-D26
A9-B4-C13-D26
A13-B4-C13-D26
A24-B4-C13-D26
A69-B4-C13-D26
A67-B4-C13-D26
A39-B4-C13-D26
A65-B4-C13-D26
A66-B4-C13-D26
A2-B5-C13-D26

-continued

A3-B5-C13-D26
A9-B5-C13-D26
A13-B5-C13-D26
A24-B5-C13-D26
A69-B5-C13-D26
A67-B5-C13-D26
A39-B5-C13-D26
A65-B5-C13-D26
A66-B5-C13-D26
A2-B6-C13-D26
A3-B6-C13-D26
A9-B6-C13-D26
A13-B6-C13-D26
A24-B6-C13-D26
A69-B6-C13-D26
A67-B6-C13-D26
A39-B6-C13-D26
A65-B6-C13-D26
A66-B6-C13-D26
A2-B32-C13-D26
A3-B32-C13-D26
A9-B32-C13-D26
A13-B32-C13-D26
A24-B32-C13-D26
A69-B32-C13-D26
A67-B32-C13-D26
A39-B32-C13-D26
A65-B32-C13-D26
A66-B32-C13-D26
A2-B39-C13-D26
A3-B39-C13-D26
A9-B39-C13-D26
A13-B39-C13-D26
A24-B39-C13-D26
A69-B39-C13-D26
A67-B39-C13-D26
A39-B39-C13-D26
A65-B39-C13-D26
A66-B39-C13-D26
A2-B45-C13-D26
A3-B45-C13-D26
A9-B45-C13-D26
A13-B45-C13-D26
A24-B45-C13-D26
A69-B45-C13-D26
A67-B45-C13-D26
A39-B45-C13-D26
A65-B45-C13-D26
A66-B45-C13-D26
A2-B53-C13-D26
A3-B53-C13-D26
A9-B53-C13-D26
A13-B53-C13-D26
A24-B53-C13-D26
A69-B53-C13-D26
A67-B53-C13-D26
A39-B53-C13-D26
A65-B53-C13-D26
A66-B53-C13-D26
A2-B79-C13-D26
A3-B79-C13-D26
A9-B79-C13-D26
A13-B79-C13-D26
A24-B79-C13-D26
A69-B79-C13-D26
A67-B79-C13-D26
A39-B79-C13-D26
A65-B79-C13-D26
A66-B79-C13-D26
A2-B80-C13-D26
A3-B80-C13-D26
A9-B80-C13-D26
A13-B80-C13-D26
A24-B80-C13-D26
A69-B80-C13-D26
A67-B80-C13-D26
A39-B80-C13-D26
A65-B80-C13-D26
A66-B80-C13-D26
A2-B85-C13-D26

-continued

A3-B85-C13-D26
A9-B85-C13-D26
A13-B85-C13-D26
A24-B85-C13-D26
A69-B85-C13-D26
A67-B85-C13-D26
A39-B85-C13-D26
A65-B85-C13-D26
A66-B85-C13-D26
A2-B86-C13-D26
A3-B86-C13-D26
A9-B86-C13-D26
A13-B86-C13-D26
A24-B86-C13-D26
A69-B86-C13-D26
A67-B86-C13-D26
A39-B86-C13-D26
A65-B86-C13-D26
A66-B86-C13-D26
A2-B87-C13-D26
A3-B87-C13-D26
A9-B87-C13-D26
A13-B87-C13-D26
A24-B87-C13-D26
A69-B87-C13-D26
A67-B87-C13-D26
A39-B87-C13-D26
A65-B87-C13-D26
A66-B87-C13-D26
A2-B89-C13-D26
A3-B89-C13-D26
A9-B89-C13-D26
A13-B89-C13-D26
A24-B89-C13-D26
A69-B89-C13-D26
A67-B89-C13-D26
A39-B89-C13-D26
A65-B89-C13-D26
A66-B89-C13-D26
A2-B92-C13-D26
A3-B92-C13-D26
A9-B92-C13-D26
A13-B92-C13-D26
A24-B92-C13-D26
A69-B92-C13-D26
A67-B92-C13-D26
A39-B92-C13-D26
A65-B92-C13-D26
A66-B92-C13-D26
A2-B4-C1-D27
A3-B4-C1-D27
A9-B4-C1-D27
A13-B4-C1-D27
A24-B4-C1-D27
A69-B4-C1-D27
A67-B4-C1-D27
A39-B4-C1-D27
A65-B4-C1-D27
A66-B4-C1-D27
A2-B5-C1-D27
A3-B5-C1-D27
A9-B5-C1-D27
A13-B5-C1-D27
A24-B5-C1-D27
A69-B5-C1-D27
A67-B5-C1-D27
A39-B5-C1-D27
A65-B5-C1-D27
A66-B5-C1-D27
A2-B6-C1-D27
A3-B6-C1-D27
A9-B6-C1-D27
A13-B6-C1-D27
A24-B6-C1-D27
A69-B6-C1-D27
A67-B6-C1-D27
A39-B6-C1-D27
A65-B6-C1-D27
A66-B6-C1-D27
A2-B32-C1-D27

-continued

A3-B32-C1-D27
A9-B32-C1-D27
A13-B32-C1-D27
A24-B32-C1-D27
A69-B32-C1-D27
A67-B32-C1-D27
A39-B32-C1-D27
A65-B32-C1-D27
A66-B32-C1-D27
A2-B39-C1-D27
A3-B39-C1-D27
A9-B39-C1-D27
A13-B39-C1-D27
A24-B39-C1-D27
A69-B39-C1-D27
A67-B39-C1-D27
A39-B39-C1-D27
A65-B39-C1-D27
A66-B39-C1-D27
A2-B45-C1-D27
A3-B45-C1-D27
A9-B45-C1-D27
A13-B45-C1-D27
A24-B45-C1-D27
A69-B45-C1-D27
A67-B45-C1-D27
A39-B45-C1-D27
A65-B45-C1-D27
A66-B45-C1-D27
A2-B53-C1-D27
A3-B53-C1-D27
A9-B53-C1-D27
A13-B53-C1-D27
A24-B53-C1-D27
A69-B53-C1-D27
A67-B53-C1-D27
A39-B53-C1-D27
A65-B53-C1-D27
A66-B53-C1-D27
A2-B79-C1-D27
A3-B79-C1-D27
A9-B79-C1-D27
A13-B79-C1-D27
A24-B79-C1-D27
A69-B79-C1-D27
A67-B79-C1-D27
A39-B79-C1-D27
A65-B79-C1-D27
A66-B79-C1-D27
A2-B80-C1-D27
A3-B80-C1-D27
A9-B80-C1-D27
A13-B80-C1-D27
A24-B80-C1-D27
A69-B80-C1-D27
A67-B80-C1-D27
A39-B80-C1-D27
A65-B80-C1-D27
A66-B80-C1-D27
A2-B85-C1-D27
A3-B85-C1-D27
A9-B85-C1-D27
A13-B85-C1-D27
A24-B85-C1-D27
A69-B85-C1-D27
A67-B85-C1-D27
A39-B85-C1-D27
A65-B85-C1-D27
A66-B85-C1-D27
A2-B86-C1-D27
A3-B86-C1-D27
A9-B86-C1-D27
A13-B86-C1-D27
A24-B86-C1-D27
A69-B86-C1-D27
A67-B86-C1-D27
A39-B86-C1-D27
A65-B86-C1-D27
A66-B86-C1-D27
A2-B87-C1-D27

-continued

A3-B87-C1-D27
A9-B87-C1-D27
A13-B87-C1-D27
A24-B87-C1-D27
A69-B87-C1-D27
A67-B87-C1-D27
A39-B87-C1-D27
A65-B87-C1-D27
A66-B87-C1-D27
A2-B89-C1-D27
A3-B89-C1-D27
A9-B89-C1-D27
A13-B89-C1-D27
A24-B89-C1-D27
A69-B89-C1-D27
A67-B89-C1-D27
A39-B89-C1-D27
A65-B89-C1-D27
A66-B89-C1-D27
A2-B92-C1-D27
A3-B92-C1-D27
A9-B92-C1-D27
A13-B92-C1-D27
A24-B92-C1-D27
A69-B92-C1-D27
A67-B92-C1-D27
A39-B92-C1-D27
A65-B92-C1-D27
A66-B92-C1-D27
A2-B4-C2-D27
A3-B4-C2-D27
A9-B4-C2-D27
A13-B4-C2-D27
A24-B4-C2-D27
A69-B4-C2-D27
A67-B4-C2-D27
A39-B4-C2-D27
A65-B4-C2-D27
A66-B4-C2-D27
A2-B5-C2-D27
A3-B5-C2-D27
A9-B5-C2-D27
A13-B5-C2-D27
A24-B5-C2-D27
A69-B5-C2-D27
A67-B5-C2-D27
A39-B5-C2-D27
A65-B5-C2-D27
A66-B5-C2-D27
A2-B6-C2-D27
A3-B6-C2-D27
A9-B6-C2-D27
A13-B6-C2-D27
A24-B6-C2-D27
A69-B6-C2-D27
A67-B6-C2-D27
A39-B6-C2-D27
A65-B6-C2-D27
A66-B6-C2-D27
A2-B32-C2-D27
A3-B32-C2-D27
A9-B32-C2-D27
A13-B32-C2-D27
A24-B32-C2-D27
A69-B32-C2-D27
A67-B32-C2-D27
A39-B32-C2-D27
A65-B32-C2-D27
A66-B32-C2-D27
A2-B39-C2-D27
A3-B39-C2-D27
A9-B39-C2-D27
A13-B39-C2-D27
A24-B39-C2-D27
A69-B39-C2-D27
A67-B39-C2-D27
A39-B39-C2-D27
A65-B39-C2-D27
A66-B39-C2-D27
A2-B45-C2-D27

-continued

A3-B45-C2-D27
A9-B45-C2-D27
A13-B45-C2-D27
A24-B45-C2-D27
A69-B45-C2-D27
A67-B45-C2-D27
A39-B45-C2-D27
A65-B45-C2-D27
A66-B45-C2-D27
A2-B53-C2-D27
A3-B53-C2-D27
A9-B53-C2-D27
A13-B53-C2-D27
A24-B53-C2-D27
A69-B53-C2-D27
A67-B53-C2-D27
A39-B53-C2-D27
A65-B53-C2-D27
A66-B53-C2-D27
A2-B79-C2-D27
A3-B79-C2-D27
A9-B79-C2-D27
A13-B79-C2-D27
A24-B79-C2-D27
A69-B79-C2-D27
A67-B79-C2-D27
A39-B79-C2-D27
A65-B79-C2-D27
A66-B79-C2-D27
A2-B80-C2-D27
A3-B80-C2-D27
A9-B80-C2-D27
A13-B80-C2-D27
A24-B80-C2-D27
A69-B80-C2-D27
A67-B80-C2-D27
A39-B80-C2-D27
A65-B80-C2-D27
A66-B80-C2-D27
A2-B85-C2-D27
A3-B85-C2-D27
A9-B85-C2-D27
A13-B85-C2-D27
A24-B85-C2-D27
A69-B85-C2-D27
A67-B85-C2-D27
A39-B85-C2-D27
A65-B85-C2-D27
A66-B85-C2-D27
A2-B86-C2-D27
A3-B86-C2-D27
A9-B86-C2-D27
A13-B86-C2-D27
A24-B86-C2-D27
A69-B86-C2-D27
A67-B86-C2-D27
A39-B86-C2-D27
A65-B86-C2-D27
A66-B86-C2-D27
A2-B87-C2-D27
A3-B87-C2-D27
A9-B87-C2-D27
A13-B87-C2-D27
A24-B87-C2-D27
A69-B87-C2-D27
A67-B87-C2-D27
A39-B87-C2-D27
A65-B87-C2-D27
A66-B87-C2-D27
A2-B89-C2-D27
A3-B89-C2-D27
A9-B89-C2-D27
A13-B89-C2-D27
A24-B89-C2-D27
A69-B89-C2-D27
A67-B89-C2-D27
A39-B89-C2-D27
A65-B89-C2-D27
A66-B89-C2-D27
A2-B92-C2-D27

-continued
A3-B92-C2-D27
A9-B92-C2-D27
A13-B92-C2-D27
A24-B92-C2-D27
A69-B92-C2-D27
A67-B92-C2-D27
A39-B92-C2-D27
A65-B92-C2-D27
A66-B92-C2-D27
A2-B4-C3-D27
A3-B4-C3-D27
A9-B4-C3-D27
A13-B4-C3-D27
A24-B4-C3-D27
A69-B4-C3-D27
A67-B4-C3-D27
A39-B4-C3-D27
A65-B4-C3-D27
A66-B4-C3-D27
A2-B5-C3-D27
A3-B5-C3-D27
A9-B5-C3-D27
A13-B5-C3-D27
A24-B5-C3-D27
A69-B5-C3-D27
A67-B5-C3-D27
A39-B5-C3-D27
A65-B5-C3-D27
A66-B5-C3-D27
A2-B6-C3-D27
A3-B6-C3-D27
A9-B6-C3-D27
A13-B6-C3-D27
A24-B6-C3-D27
A69-B6-C3-D27
A67-B6-C3-D27
A39-B6-C3-D27
A65-B6-C3-D27
A66-B6-C3-D27
A2-B32-C3-D27
A3-B32-C3-D27
A9-B32-C3-D27
A13-B32-C3-D27
A24-B32-C3-D27
A69-B32-C3-D27
A67-B32-C3-D27
A39-B32-C3-D27
A65-B32-C3-D27
A66-B32-C3-D27
A2-B39-C3-D27
A3-B39-C3-D27
A9-B39-C3-D27
A13-B39-C3-D27
A24-B39-C3-D27
A69-B39-C3-D27
A67-B39-C3-D27
A39-B39-C3-D27
A65-B39-C3-D27
A66-B39-C3-D27
A2-B45-C3-D27
A3-B45-C3-D27
A9-B45-C3-D27
A13-B45-C3-D27
A24-B45-C3-D27
A69-B45-C3-D27
A67-B45-C3-D27
A39-B45-C3-D27
A65-B45-C3-D27
A66-B45-C3-D27
A2-B53-C3-D27
A3-B53-C3-D27
A9-B53-C3-D27
A13-B53-C3-D27
A24-B53-C3-D27
A69-B53-C3-D27
A67-B53-C3-D27
A39-B53-C3-D27
A65-B53-C3-D27
A66-B53-C3-D27
A2-B79-C3-D27

-continued
A3-B79-C3-D27
A9-B79-C3-D27
A13-B79-C3-D27
A24-B79-C3-D27
A69-B79-C3-D27
A67-B79-C3-D27
A39-B79-C3-D27
A65-B79-C3-D27
A66-B79-C3-D27
A2-B80-C3-D27
A3-B80-C3-D27
A9-B80-C3-D27
A13-B80-C3-D27
A24-B80-C3-D27
A69-B80-C3-D27
A67-B80-C3-D27
A39-B80-C3-D27
A65-B80-C3-D27
A66-B80-C3-D27
A2-B85-C3-D27
A3-B85-C3-D27
A9-B85-C3-D27
A13-B85-C3-D27
A24-B85-C3-D27
A69-B85-C3-D27
A67-B85-C3-D27
A39-B85-C3-D27
A65-B85-C3-D27
A66-B85-C3-D27
A2-B86-C3-D27
A3-B86-C3-D27
A9-B86-C3-D27
A13-B86-C3-D27
A24-B86-C3-D27
A69-B86-C3-D27
A67-B86-C3-D27
A39-B86-C3-D27
A65-B86-C3-D27
A66-B86-C3-D27
A2-B87-C3-D27
A3-B87-C3-D27
A9-B87-C3-D27
A13-B87-C3-D27
A24-B87-C3-D27
A69-B87-C3-D27
A67-B87-C3-D27
A39-B87-C3-D27
A65-B87-C3-D27
A66-B87-C3-D27
A2-B89-C3-D27
A3-B89-C3-D27
A9-B89-C3-D27
A13-B89-C3-D27
A24-B89-C3-D27
A69-B89-C3-D27
A67-B89-C3-D27
A39-B89-C3-D27
A65-B89-C3-D27
A66-B89-C3-D27
A2-B92-C3-D27
A3-B92-C3-D27
A9-B92-C3-D27
A13-B92-C3-D27
A24-B92-C3-D27
A69-B92-C3-D27
A67-B92-C3-D27
A39-B92-C3-D27
A65-B92-C3-D27
A66-B92-C3-D27
A2-B4-C4-D27
A3-B4-C4-D27
A9-B4-C4-D27
A13-B4-C4-D27
A24-B4-C4-D27
A69-B4-C4-D27
A67-B4-C4-D27
A39-B4-C4-D27
A65-B4-C4-D27
A66-B4-C4-D27
A2-B5-C4-D27

-continued

A3-B5-C4-D27
A9-B5-C4-D27
A13-B5-C4-D27
A24-B5-C4-D27
A69-B5-C4-D27
A67-B5-C4-D27
A39-B5-C4-D27
A65-B5-C4-D27
A66-B5-C4-D27
A2-B6-C4-D27
A3-B6-C4-D27
A9-B6-C4-D27
A13-B6-C4-D27
A24-B6-C4-D27
A69-B6-C4-D27
A67-B6-C4-D27
A39-B6-C4-D27
A65-B6-C4-D27
A66-B6-C4-D27
A2-B32-C4-D27
A3-B32-C4-D27
A9-B32-C4-D27
A13-B32-C4-D27
A24-B32-C4-D27
A69-B32-C4-D27
A67-B32-C4-D27
A39-B32-C4-D27
A65-B32-C4-D27
A66-B32-C4-D27
A2-B39-C4-D27
A3-B39-C4-D27
A9-B39-C4-D27
A13-B39-C4-D27
A24-B39-C4-D27
A69-B39-C4-D27
A67-B39-C4-D27
A39-B39-C4-D27
A65-B39-C4-D27
A66-B39-C4-D27
A2-B45-C4-D27
A3-B45-C4-D27
A9-B45-C4-D27
A13-B45-C4-D27
A24-B45-C4-D27
A69-B45-C4-D27
A67-B45-C4-D27
A39-B45-C4-D27
A65-B45-C4-D27
A66-B45-C4-D27
A2-B53-C4-D27
A3-B53-C4-D27
A9-B53-C4-D27
A13-B53-C4-D27
A24-B53-C4-D27
A69-B53-C4-D27
A67-B53-C4-D27
A39-B53-C4-D27
A65-B53-C4-D27
A66-B53-C4-D27
A2-B79-C4-D27
A3-B79-C4-D27
A9-B79-C4-D27
A13-B79-C4-D27
A24-B79-C4-D27
A69-B79-C4-D27
A67-B79-C4-D27
A39-B79-C4-D27
A65-B79-C4-D27
A66-B79-C4-D27
A2-B80-C4-D27
A3-B80-C4-D27
A9-B80-C4-D27
A13-B80-C4-D27
A24-B80-C4-D27
A69-B80-C4-D27
A67-B80-C4-D27
A39-B80-C4-D27
A65-B80-C4-D27
A66-B80-C4-D27
A2-B85-C4-D27

-continued

A3-B85-C4-D27
A9-B85-C4-D27
A13-B85-C4-D27
A24-B85-C4-D27
A69-B85-C4-D27
A67-B85-C4-D27
A39-B85-C4-D27
A65-B85-C4-D27
A66-B85-C4-D27
A2-B86-C4-D27
A3-B86-C4-D27
A9-B86-C4-D27
A13-B86-C4-D27
A24-B86-C4-D27
A69-B86-C4-D27
A67-B86-C4-D27
A39-B86-C4-D27
A65-B86-C4-D27
A66-B86-C4-D27
A2-B87-C4-D27
A3-B87-C4-D27
A9-B87-C4-D27
A13-B87-C4-D27
A24-B87-C4-D27
A69-B87-C4-D27
A67-B87-C4-D27
A39-B87-C4-D27
A65-B87-C4-D27
A66-B87-C4-D27
A2-B89-C4-D27
A3-B89-C4-D27
A9-B89-C4-D27
A13-B89-C4-D27
A24-B89-C4-D27
A69-B89-C4-D27
A67-B89-C4-D27
A39-B89-C4-D27
A65-B89-C4-D27
A66-B89-C4-D27
A2-B92-C4-D27
A3-B92-C4-D27
A9-B92-C4-D27
A13-B92-C4-D27
A24-B92-C4-D27
A69-B92-C4-D27
A67-B92-C4-D27
A39-B92-C4-D27
A65-B92-C4-D27
A66-B92-C4-D27
A2-B4-C5-D27
A3-B4-C5-D27
A9-B4-C5-D27
A13-B4-C5-D27
A24-B4-C5-D27
A69-B4-C5-D27
A67-B4-C5-D27
A39-B4-C5-D27
A65-B4-C5-D27
A66-B4-C5-D27
A2-B5-C5-D27
A3-B5-C5-D27
A9-B5-C5-D27
A13-B5-C5-D27
A24-B5-C5-D27
A69-B5-C5-D27
A67-B5-C5-D27
A39-B5-C5-D27
A65-B5-C5-D27
A66-B5-C5-D27
A2-B6-C5-D27
A3-B6-C5-D27
A9-B6-C5-D27
A13-B6-C5-D27
A24-B6-C5-D27
A69-B6-C5-D27
A67-B6-C5-D27
A39-B6-C5-D27
A65-B6-C5-D27
A66-B6-C5-D27
A2-B32-C5-D27

-continued
A3-B32-C5-D27
A9-B32-C5-D27
A13-B32-C5-D27
A24-B32-C5-D27
A69-B32-C5-D27
A67-B32-C5-D27
A39-B32-C5-D27
A65-B32-C5-D27
A66-B32-C5-D27
A2-B39-C5-D27
A3-B39-C5-D27
A9-B39-C5-D27
A13-B39-C5-D27
A24-B39-C5-D27
A69-B39-C5-D27
A67-B39-C5-D27
A39-B39-C5-D27
A65-B39-C5-D27
A66-B39-C5-D27
A2-B45-C5-D27
A3-B45-C5-D27
A9-B45-C5-D27
A13-B45-C5-D27
A24-B45-C5-D27
A69-B45-C5-D27
A67-B45-C5-D27
A39-B45-C5-D27
A65-B45-C5-D27
A66-B45-C5-D27
A2-B53-C5-D27
A3-B53-C5-D27
A9-B53-C5-D27
A13-B53-C5-D27
A24-B53-C5-D27
A69-B53-C5-D27
A67-B53-C5-D27
A39-B53-C5-D27
A65-B53-C5-D27
A66-B53-C5-D27
A2-B79-C5-D27
A3-B79-C5-D27
A9-B79-C5-D27
A13-B79-C5-D27
A24-B79-C5-D27
A69-B79-C5-D27
A67-B79-C5-D27
A39-B79-C5-D27
A65-B79-C5-D27
A66-B79-C5-D27
A2-B80-C5-D27
A3-B80-C5-D27
A9-B80-C5-D27
A13-B80-C5-D27
A24-B80-C5-D27
A69-B80-C5-D27
A67-B80-C5-D27
A39-B80-C5-D27
A65-B80-C5-D27
A66-B80-C5-D27
A2-B85-C5-D27
A3-B85-C5-D27
A9-B85-C5-D27
A13-B85-C5-D27
A24-B85-C5-D27
A69-B85-C5-D27
A67-B85-C5-D27
A39-B85-C5-D27
A65-B85-C5-D27
A66-B85-C5-D27
A2-B86-C5-D27
A3-B86-C5-D27
A9-B86-C5-D27
A13-B86-C5-D27
A24-B86-C5-D27
A69-B86-C5-D27
A67-B86-C5-D27
A39-B86-C5-D27
A65-B86-C5-D27
A66-B86-C5-D27
A2-B87-C5-D27

-continued
A3-B87-C5-D27
A9-B87-C5-D27
A13-B87-C5-D27
A24-B87-C5-D27
A69-B87-C5-D27
A67-B87-C5-D27
A39-B87-C5-D27
A65-B87-C5-D27
A66-B87-C5-D27
A2-B89-C5-D27
A3-B89-C5-D27
A9-B89-C5-D27
A13-B89-C5-D27
A24-B89-C5-D27
A69-B89-C5-D27
A67-B89-C5-D27
A39-B89-C5-D27
A65-B89-C5-D27
A66-B89-C5-D27
A2-B92-C5-D27
A3-B92-C5-D27
A9-B92-C5-D27
A13-B92-C5-D27
A24-B92-C5-D27
A69-B92-C5-D27
A67-B92-C5-D27
A39-B92-C5-D27
A65-B92-C5-D27
A66-B92-C5-D27
A2-B4-C6-D27
A3-B4-C6-D27
A9-B4-C6-D27
A13-B4-C6-D27
A24-B4-C6-D27
A69-B4-C6-D27
A67-B4-C6-D27
A39-B4-C6-D27
A65-B4-C6-D27
A66-B4-C6-D27
A2-B5-C6-D27
A3-B5-C6-D27
A9-B5-C6-D27
A13-B5-C6-D27
A24-B5-C6-D27
A69-B5-C6-D27
A67-B5-C6-D27
A39-B5-C6-D27
A65-B5-C6-D27
A66-B5-C6-D27
A2-B6-C6-D27
A3-B6-C6-D27
A9-B6-C6-D27
A13-B6-C6-D27
A24-B6-C6-D27
A69-B6-C6-D27
A67-B6-C6-D27
A39-B6-C6-D27
A65-B6-C6-D27
A66-B6-C6-D27
A2-B32-C6-D27
A3-B32-C6-D27
A9-B32-C6-D27
A13-B32-C6-D27
A24-B32-C6-D27
A69-B32-C6-D27
A67-B32-C6-D27
A39-B32-C6-D27
A65-B32-C6-D27
A66-B32-C6-D27
A2-B39-C6-D27
A3-B39-C6-D27
A9-B39-C6-D27
A13-B39-C6-D27
A24-B39-C6-D27
A69-B39-C6-D27
A67-B39-C6-D27
A39-B39-C6-D27
A65-B39-C6-D27
A66-B39-C6-D27
A2-B45-C6-D27

-continued

A3-B45-C6-D27
A9-B45-C6-D27
A13-B45-C6-D27
A24-B45-C6-D27
A69-B45-C6-D27
A67-B45-C6-D27
A39-B45-C6-D27
A65-B45-C6-D27
A66-B45-C6-D27
A2-B53-C6-D27
A3-B53-C6-D27
A9-B53-C6-D27
A13-B53-C6-D27
A24-B53-C6-D27
A69-B53-C6-D27
A67-B53-C6-D27
A39-B53-C6-D27
A65-B53-C6-D27
A66-B53-C6-D27
A2-B79-C6-D27
A3-B79-C6-D27
A9-B79-C6-D27
A13-B79-C6-D27
A24-B79-C6-D27
A69-B79-C6-D27
A67-B79-C6-D27
A39-B79-C6-D27
A65-B79-C6-D27
A66-B79-C6-D27
A2-B80-C6-D27
A3-B80-C6-D27
A9-B80-C6-D27
A13-B80-C6-D27
A24-B80-C6-D27
A69-B80-C6-D27
A67-B80-C6-D27
A39-B80-C6-D27
A65-B80-C6-D27
A66-B80-C6-D27
A2-B85-C6-D27
A3-B85-C6-D27
A9-B85-C6-D27
A13-B85-C6-D27
A24-B85-C6-D27
A69-B85-C6-D27
A67-B85-C6-D27
A39-B85-C6-D27
A65-B85-C6-D27
A66-B85-C6-D27
A2-B86-C6-D27
A3-B86-C6-D27
A9-B86-C6-D27
A13-B86-C6-D27
A24-B86-C6-D27
A69-B86-C6-D27
A67-B86-C6-D27
A39-B86-C6-D27
A65-B86-C6-D27
A66-B86-C6-D27
A2-B87-C6-D27
A3-B87-C6-D27
A9-B87-C6-D27
A13-B87-C6-D27
A24-B87-C6-D27
A69-B87-C6-D27
A67-B87-C6-D27
A39-B87-C6-D27
A65-B87-C6-D27
A66-B87-C6-D27
A2-B89-C6-D27
A3-B89-C6-D27
A9-B89-C6-D27
A13-B89-C6-D27
A24-B89-C6-D27
A69-B89-C6-D27
A67-B89-C6-D27
A39-B89-C6-D27
A65-B89-C6-D27
A66-B89-C6-D27
A2-B92-C6-D27

-continued

A3-B92-C6-D27
A9-B92-C6-D27
A13-B92-C6-D27
A24-B92-C6-D27
A69-B92-C6-D27
A67-B92-C6-D27
A39-B92-C6-D27
A65-B92-C6-D27
A66-B92-C6-D27
A2-B4-C7-D27
A3-B4-C7-D27
A9-B4-C7-D27
A13-B4-C7-D27
A24-B4-C7-D27
A69-B4-C7-D27
A67-B4-C7-D27
A39-B4-C7-D27
A65-B4-C7-D27
A66-B4-C7-D27
A2-B5-C7-D27
A3-B5-C7-D27
A9-B5-C7-D27
A13-B5-C7-D27
A24-B5-C7-D27
A69-B5-C7-D27
A67-B5-C7-D27
A39-B5-C7-D27
A65-B5-C7-D27
A66-B5-C7-D27
A2-B6-C7-D27
A3-B6-C7-D27
A9-B6-C7-D27
A13-B6-C7-D27
A24-B6-C7-D27
A69-B6-C7-D27
A67-B6-C7-D27
A39-B6-C7-D27
A65-B6-C7-D27
A66-B6-C7-D27
A2-B32-C7-D27
A3-B32-C7-D27
A9-B32-C7-D27
A13-B32-C7-D27
A24-B32-C7-D27
A69-B32-C7-D27
A67-B32-C7-D27
A39-B32-C7-D27
A65-B32-C7-D27
A66-B32-C7-D27
A2-B39-C7-D27
A3-B39-C7-D27
A9-B39-C7-D27
A13-B39-C7-D27
A24-B39-C7-D27
A69-B39-C7-D27
A67-B39-C7-D27
A39-B39-C7-D27
A65-B39-C7-D27
A66-B39-C7-D27
A2-B45-C7-D27
A3-B45-C7-D27
A9-B45-C7-D27
A13-B45-C7-D27
A24-B45-C7-D27
A69-B45-C7-D27
A67-B45-C7-D27
A39-B45-C7-D27
A65-B45-C7-D27
A66-B45-C7-D27
A2-B53-C7-D27
A3-B53-C7-D27
A9-B53-C7-D27
A13-B53-C7-D27
A24-B53-C7-D27
A69-B53-C7-D27
A67-B53-C7-D27
A39-B53-C7-D27
A65-B53-C7-D27
A66-B53-C7-D27
A2-B79-C7-D27

-continued
A3-B79-C7-D27
A9-B79-C7-D27
A13-B79-C7-D27
A24-B79-C7-D27
A69-B79-C7-D27
A67-B79-C7-D27
A39-B79-C7-D27
A65-B79-C7-D27
A66-B79-C7-D27
A2-B80-C7-D27
A3-B80-C7-D27
A9-B80-C7-D27
A13-B80-C7-D27
A24-B80-C7-D27
A69-B80-C7-D27
A67-B80-C7-D27
A39-B80-C7-D27
A65-B80-C7-D27
A66-B80-C7-D27
A2-B85-C7-D27
A3-B85-C7-D27
A9-B85-C7-D27
A13-B85-C7-D27
A24-B85-C7-D27
A69-B85-C7-D27
A67-B85-C7-D27
A39-B85-C7-D27
A65-B85-C7-D27
A66-B85-C7-D27
A2-B86-C7-D27
A3-B86-C7-D27
A9-B86-C7-D27
A13-B86-C7-D27
A24-B86-C7-D27
A69-B86-C7-D27
A67-B86-C7-D27
A39-B86-C7-D27
A65-B86-C7-D27
A66-B86-C7-D27
A2-B87-C7-D27
A3-B87-C7-D27
A9-B87-C7-D27
A13-B87-C7-D27
A24-B87-C7-D27
A69-B87-C7-D27
A67-B87-C7-D27
A39-B87-C7-D27
A65-B87-C7-D27
A66-B87-C7-D27
A2-B89-C7-D27
A3-B89-C7-D27
A9-B89-C7-D27
A13-B89-C7-D27
A24-B89-C7-D27
A69-B89-C7-D27
A67-B89-C7-D27
A39-B89-C7-D27
A65-B89-C7-D27
A66-B89-C7-D27
A2-B92-C7-D27
A3-B92-C7-D27
A9-B92-C7-D27
A13-B92-C7-D27
A24-B92-C7-D27
A69-B92-C7-D27
A67-B92-C7-D27
A39-B92-C7-D27
A65-B92-C7-D27
A66-B92-C7-D27
A2-B4-C8-D27
A3-B4-C8-D27
A9-B4-C8-D27
A13-B4-C8-D27
A24-B4-C8-D27
A69-B4-C8-D27
A67-B4-C8-D27
A39-B4-C8-D27
A65-B4-C8-D27
A66-B4-C8-D27
A2-B5-C8-D27

-continued
A3-B5-C8-D27
A9-B5-C8-D27
A13-B5-C8-D27
A24-B5-C8-D27
A69-B5-C8-D27
A67-B5-C8-D27
A39-B5-C8-D27
A65-B5-C8-D27
A66-B5-C8-D27
A2-B6-C8-D27
A3-B6-C8-D27
A9-B6-C8-D27
A13-B6-C8-D27
A24-B6-C8-D27
A69-B6-C8-D27
A67-B6-C8-D27
A39-B6-C8-D27
A65-B6-C8-D27
A66-B6-C8-D27
A2-B32-C8-D27
A3-B32-C8-D27
A9-B32-C8-D27
A13-B32-C8-D27
A24-B32-C8-D27
A69-B32-C8-D27
A67-B32-C8-D27
A39-B32-C8-D27
A65-B32-C8-D27
A66-B32-C8-D27
A2-B39-C8-D27
A3-B39-C8-D27
A9-B39-C8-D27
A13-B39-C8-D27
A24-B39-C8-D27
A69-B39-C8-D27
A67-B39-C8-D27
A39-B39-C8-D27
A65-B39-C8-D27
A66-B39-C8-D27
A2-B45-C8-D27
A3-B45-C8-D27
A9-B45-C8-D27
A13-B45-C8-D27
A24-B45-C8-D27
A69-B45-C8-D27
A67-B45-C8-D27
A39-B45-C8-D27
A65-B45-C8-D27
A66-B45-C8-D27
A2-B53-C8-D27
A3-B53-C8-D27
A9-B53-C8-D27
A13-B53-C8-D27
A24-B53-C8-D27
A69-B53-C8-D27
A67-B53-C8-D27
A39-B53-C8-D27
A65-B53-C8-D27
A66-B53-C8-D27
A2-B79-C8-D27
A3-B79-C8-D27
A9-B79-C8-D27
A13-B79-C8-D27
A24-B79-C8-D27
A69-B79-C8-D27
A67-B79-C8-D27
A39-B79-C8-D27
A65-B79-C8-D27
A66-B79-C8-D27
A2-B80-C8-D27
A3-B80-C8-D27
A9-B80-C8-D27
A13-B80-C8-D27
A24-B80-C8-D27
A69-B80-C8-D27
A67-B80-C8-D27
A39-B80-C8-D27
A65-B80-C8-D27
A66-B80-C8-D27
A2-B85-C8-D27

-continued

A3-B85-C8-D27
A9-B85-C8-D27
A13-B85-C8-D27
A24-B85-C8-D27
A69-B85-C8-D27
A67-B85-C8-D27
A39-B85-C8-D27
A65-B85-C8-D27
A66-B85-C8-D27
A2-B86-C8-D27
A3-B86-C8-D27
A9-B86-C8-D27
A13-B86-C8-D27
A24-B86-C8-D27
A69-B86-C8-D27
A67-B86-C8-D27
A39-B86-C8-D27
A65-B86-C8-D27
A66-B86-C8-D27
A2-B87-C8-D27
A3-B87-C8-D27
A9-B87-C8-D27
A13-B87-C8-D27
A24-B87-C8-D27
A69-B87-C8-D27
A67-B87-C8-D27
A39-B87-C8-D27
A65-B87-C8-D27
A66-B87-C8-D27
A2-B89-C8-D27
A3-B89-C8-D27
A9-B89-C8-D27
A13-B89-C8-D27
A24-B89-C8-D27
A69-B89-C8-D27
A67-B89-C8-D27
A39-B89-C8-D27
A65-B89-C8-D27
A66-B89-C8-D27
A2-B92-C8-D27
A3-B92-C8-D27
A9-B92-C8-D27
A13-B92-C8-D27
A24-B92-C8-D27
A69-B92-C8-D27
A67-B92-C8-D27
A39-B92-C8-D27
A65-B92-C8-D27
A66-B92-C8-D27
A2-B4-C9-D27
A3-B4-C9-D27
A9-B4-C9-D27
A13-B4-C9-D27
A24-B4-C9-D27
A69-B4-C9-D27
A67-B4-C9-D27
A39-B4-C9-D27
A65-B4-C9-D27
A66-B4-C9-D27
A2-B5-C9-D27
A3-B5-C9-D27
A9-B5-C9-D27
A13-B5-C9-D27
A24-B5-C9-D27
A69-B5-C9-D27
A67-B5-C9-D27
A39-B5-C9-D27
A65-B5-C9-D27
A66-B5-C9-D27
A2-B6-C9-D27
A3-B6-C9-D27
A9-B6-C9-D27
A13-B6-C9-D27
A24-B6-C9-D27
A69-B6-C9-D27
A67-B6-C9-D27
A39-B6-C9-D27
A65-B6-C9-D27
A66-B6-C9-D27
A2-B32-C9-D27

-continued

A3-B32-C9-D27
A9-B32-C9-D27
A13-B32-C9-D27
A24-B32-C9-D27
A69-B32-C9-D27
A67-B32-C9-D27
A39-B32-C9-D27
A65-B32-C9-D27
A66-B32-C9-D27
A2-B39-C9-D27
A3-B39-C9-D27
A9-B39-C9-D27
A13-B39-C9-D27
A24-B39-C9-D27
A69-B39-C9-D27
A67-B39-C9-D27
A39-B39-C9-D27
A65-B39-C9-D27
A66-B39-C9-D27
A2-B45-C9-D27
A3-B45-C9-D27
A9-B45-C9-D27
A13-B45-C9-D27
A24-B45-C9-D27
A69-B45-C9-D27
A67-B45-C9-D27
A39-B45-C9-D27
A65-B45-C9-D27
A66-B45-C9-D27
A2-B53-C9-D27
A3-B53-C9-D27
A9-B53-C9-D27
A13-B53-C9-D27
A24-B53-C9-D27
A69-B53-C9-D27
A67-B53-C9-D27
A39-B53-C9-D27
A65-B53-C9-D27
A66-B53-C9-D27
A2-B79-C9-D27
A3-B79-C9-D27
A9-B79-C9-D27
A13-B79-C9-D27
A24-B79-C9-D27
A69-B79-C9-D27
A67-B79-C9-D27
A39-B79-C9-D27
A65-B79-C9-D27
A66-B79-C9-D27
A2-B80-C9-D27
A3-B80-C9-D27
A9-B80-C9-D27
A13-B80-C9-D27
A24-B80-C9-D27
A69-B80-C9-D27
A67-B80-C9-D27
A39-B80-C9-D27
A65-B80-C9-D27
A66-B80-C9-D27
A2-B85-C9-D27
A3-B85-C9-D27
A9-B85-C9-D27
A13-B85-C9-D27
A24-B85-C9-D27
A69-B85-C9-D27
A67-B85-C9-D27
A39-B85-C9-D27
A65-B85-C9-D27
A66-B85-C9-D27
A2-B86-C9-D27
A3-B86-C9-D27
A9-B86-C9-D27
A13-B86-C9-D27
A24-B86-C9-D27
A69-B86-C9-D27
A67-B86-C9-D27
A39-B86-C9-D27
A65-B86-C9-D27
A66-B86-C9-D27
A2-B87-C9-D27

-continued

A3-B87-C9-D27
A9-B87-C9-D27
A13-B87-C9-D27
A24-B87-C9-D27
A69-B87-C9-D27
A67-B87-C9-D27
A39-B87-C9-D27
A65-B87-C9-D27
A66-B87-C9-D27
A2-B89-C9-D27
A3-B89-C9-D27
A9-B89-C9-D27
A13-B89-C9-D27
A24-B89-C9-D27
A69-B89-C9-D27
A67-B89-C9-D27
A39-B89-C9-D27
A65-B89-C9-D27
A66-B89-C9-D27
A2-B92-C9-D27
A3-B92-C9-D27
A9-B92-C9-D27
A13-B92-C9-D27
A24-B92-C9-D27
A69-B92-C9-D27
A67-B92-C9-D27
A39-B92-C9-D27
A65-B92-C9-D27
A66-B92-C9-D27
A2-B4-C10-D27
A3-B4-C10-D27
A9-B4-C10-D27
A13-B4-C10-D27
A24-B4-C10-D27
A69-B4-C10-D27
A67-B4-C10-D27
A39-B4-C10-D27
A65-B4-C10-D27
A66-B4-C10-D27
A2-B5-C10-D27
A3-B5-C10-D27
A9-B5-C10-D27
A13-B5-C10-D27
A24-B5-C10-D27
A69-B5-C10-D27
A67-B5-C10-D27
A39-B5-C10-D27
A65-B5-C10-D27
A66-B5-C10-D27
A2-B6-C10-D27
A3-B6-C10-D27
A9-B6-C10-D27
A13-B6-C10-D27
A24-B6-C10-D27
A69-B6-C10-D27
A67-B6-C10-D27
A39-B6-C10-D27
A65-B6-C10-D27
A66-B6-C10-D27
A2-B32-C10-D27
A3-B32-C10-D27
A9-B32-C10-D27
A13-B32-C10-D27
A24-B32-C10-D27
A69-B32-C10-D27
A67-B32-C10-D27
A39-B32-C10-D27
A65-B32-C10-D27
A66-B32-C10-D27
A2-B39-C10-D27
A3-B39-C10-D27
A9-B39-C10-D27
A13-B39-C10-D27
A24-B39-C10-D27
A69-B39-C10-D27
A67-B39-C10-D27
A39-B39-C10-D27
A65-B39-C10-D27
A66-B39-C10-D27
A2-B45-C10-D27

-continued

A3-B45-C10-D27
A9-B45-C10-D27
A13-B45-C10-D27
A24-B45-C10-D27
A69-B45-C10-D27
A67-B45-C10-D27
A39-B45-C10-D27
A65-B45-C10-D27
A66-B45-C10-D27
A2-B53-C10-D27
A3-B53-C10-D27
A9-B53-C10-D27
A13-B53-C10-D27
A24-B53-C10-D27
A69-B53-C10-D27
A67-B53-C10-D27
A39-B53-C10-D27
A65-B53-C10-D27
A66-B53-C10-D27
A2-B79-C10-D27
A3-B79-C10-D27
A9-B79-C10-D27
A13-B79-C10-D27
A24-B79-C10-D27
A69-B79-C10-D27
A67-B79-C10-D27
A39-B79-C10-D27
A65-B79-C10-D27
A66-B79-C10-D27
A2-B80-C10-D27
A3-B80-C10-D27
A9-B80-C10-D27
A13-B80-C10-D27
A24-B80-C10-D27
A69-B80-C10-D27
A67-B80-C10-D27
A39-B80-C10-D27
A65-B80-C10-D27
A66-B80-C10-D27
A2-B85-C10-D27
A3-B85-C10-D27
A9-B85-C10-D27
A13-B85-C10-D27
A24-B85-C10-D27
A69-B85-C10-D27
A67-B85-C10-D27
A39-B85-C10-D27
A65-B85-C10-D27
A66-B85-C10-D27
A2-B86-C10-D27
A3-B86-C10-D27
A9-B86-C10-D27
A13-B86-C10-D27
A24-B86-C10-D27
A69-B86-C10-D27
A67-B86-C10-D27
A39-B86-C10-D27
A65-B86-C10-D27
A66-B86-C10-D27
A2-B87-C10-D27
A3-B87-C10-D27
A9-B87-C10-D27
A13-B87-C10-D27
A24-B87-C10-D27
A69-B87-C10-D27
A67-B87-C10-D27
A39-B87-C10-D27
A65-B87-C10-D27
A66-B87-C10-D27
A2-B89-C10-D27
A3-B89-C10-D27
A9-B89-C10-D27
A13-B89-C10-D27
A24-B89-C10-D27
A69-B89-C10-D27
A67-B89-C10-D27
A39-B89-C10-D27
A65-B89-C10-D27
A66-B89-C10-D27
A2-B92-C10-D27

-continued
A3-B92-C10-D27
A9-B92-C10-D27
A13-B92-C10-D27
A24-B92-C10-D27
A69-B92-C10-D27
A67-B92-C10-D27
A39-B92-C10-D27
A65-B92-C10-D27
A66-B92-C10-D27
A2-B4-C11-D27
A3-B4-C11-D27
A9-B4-C11-D27
A13-B4-C11-D27
A24-B4-C11-D27
A69-B4-C11-D27
A67-B4-C11-D27
A39-B4-C11-D27
A65-B4-C11-D27
A66-B4-C11-D27
A2-B5-C11-D27
A3-B5-C11-D27
A9-B5-C11-D27
A13-B5-C11-D27
A24-B5-C11-D27
A69-B5-C11-D27
A67-B5-C11-D27
A39-B5-C11-D27
A65-B5-C11-D27
A66-B5-C11-D27
A2-B6-C11-D27
A3-B6-C11-D27
A9-B6-C11-D27
A13-B6-C11-D27
A24-B6-C11-D27
A69-B6-C11-D27
A67-B6-C11-D27
A39-B6-C11-D27
A65-B6-C11-D27
A66-B6-C11-D27
A2-B32-C11-D27
A3-B32-C11-D27
A9-B32-C11-D27
A13-B32-C11-D27
A24-B32-C11-D27
A69-B32-C11-D27
A67-B32-C11-D27
A39-B32-C11-D27
A65-B32-C11-D27
A66-B32-C11-D27
A2-B39-C11-D27
A3-B39-C11-D27
A9-B39-C11-D27
A13-B39-C11-D27
A24-B39-C11-D27
A69-B39-C11-D27
A67-B39-C11-D27
A39-B39-C11-D27
A65-B39-C11-D27
A66-B39-C11-D27
A2-B45-C11-D27
A3-B45-C11-D27
A9-B45-C11-D27
A13-B45-C11-D27
A24-B45-C11-D27
A69-B45-C11-D27
A67-B45-C11-D27
A39-B45-C11-D27
A65-B45-C11-D27
A66-B45-C11-D27
A2-B53-C11-D27
A3-B53-C11-D27
A9-B53-C11-D27
A13-B53-C11-D27
A24-B53-C11-D27
A69-B53-C11-D27
A67-B53-C11-D27
A39-B53-C11-D27
A65-B53-C11-D27
A66-B53-C11-D27
A2-B79-C11-D27

-continued
A3-B79-C11-D27
A9-B79-C11-D27
A13-B79-C11-D27
A24-B79-C11-D27
A69-B79-C11-D27
A67-B79-C11-D27
A39-B79-C11-D27
A65-B79-C11-D27
A66-B79-C11-D27
A2-B80-C11-D27
A3-B80-C11-D27
A9-B80-C11-D27
A13-B80-C11-D27
A24-B80-C11-D27
A69-B80-C11-D27
A67-B80-C11-D27
A39-B80-C11-D27
A65-B80-C11-D27
A66-B80-C11-D27
A2-B85-C11-D27
A3-B85-C11-D27
A9-B85-C11-D27
A13-B85-C11-D27
A24-B85-C11-D27
A69-B85-C11-D27
A67-B85-C11-D27
A39-B85-C11-D27
A65-B85-C11-D27
A66-B85-C11-D27
A2-B86-C11-D27
A3-B86-C11-D27
A9-B86-C11-D27
A13-B86-C11-D27
A24-B86-C11-D27
A69-B86-C11-D27
A67-B86-C11-D27
A39-B86-C11-D27
A65-B86-C11-D27
A66-B86-C11-D27
A2-B87-C11-D27
A3-B87-C11-D27
A9-B87-C11-D27
A13-B87-C11-D27
A24-B87-C11-D27
A69-B87-C11-D27
A67-B87-C11-D27
A39-B87-C11-D27
A65-B87-C11-D27
A66-B87-C11-D27
A2-B89-C11-D27
A3-B89-C11-D27
A9-B89-C11-D27
A13-B89-C11-D27
A24-B89-C11-D27
A69-B89-C11-D27
A67-B89-C11-D27
A39-B89-C11-D27
A65-B89-C11-D27
A66-B89-C11-D27
A2-B92-C11-D27
A3-B92-C11-D27
A9-B92-C11-D27
A13-B92-C11-D27
A24-B92-C11-D27
A69-B92-C11-D27
A67-B92-C11-D27
A39-B92-C11-D27
A65-B92-C11-D27
A66-B92-C11-D27
A2-B4-C12-D27
A3-B4-C12-D27
A9-B4-C12-D27
A13-B4-C12-D27
A24-B4-C12-D27
A69-B4-C12-D27
A67-B4-C12-D27
A39-B4-C12-D27
A65-B4-C12-D27
A66-B4-C12-D27
A2-B5-C12-D27

-continued
A3-B5-C12-D27
A9-B5-C12-D27
A13-B5-C12-D27
A24-B5-C12-D27
A69-B5-C12-D27
A67-B5-C12-D27
A39-B5-C12-D27
A65-B5-C12-D27
A66-B5-C12-D27
A2-B6-C12-D27
A3-B6-C12-D27
A9-B6-C12-D27
A13-B6-C12-D27
A24-B6-C12-D27
A69-B6-C12-D27
A67-B6-C12-D27
A39-B6-C12-D27
A65-B6-C12-D27
A66-B6-C12-D27
A2-B32-C12-D27
A3-B32-C12-D27
A9-B32-C12-D27
A13-B32-C12-D27
A24-B32-C12-D27
A69-B32-C12-D27
A67-B32-C12-D27
A39-B32-C12-D27
A65-B32-C12-D27
A66-B32-C12-D27
A2-B39-C12-D27
A3-B39-C12-D27
A9-B39-C12-D27
A13-B39-C12-D27
A24-B39-C12-D27
A69-B39-C12-D27
A67-B39-C12-D27
A39-B39-C12-D27
A65-B39-C12-D27
A66-B39-C12-D27
A2-B45-C12-D27
A3-B45-C12-D27
A9-B45-C12-D27
A13-B45-C12-D27
A24-B45-C12-D27
A69-B45-C12-D27
A67-B45-C12-D27
A39-B45-C12-D27
A65-B45-C12-D27
A66-B45-C12-D27
A2-B53-C12-D27
A3-B53-C12-D27
A9-B53-C12-D27
A13-B53-C12-D27
A24-B53-C12-D27
A69-B53-C12-D27
A67-B53-C12-D27
A39-B53-C12-D27
A65-B53-C12-D27
A66-B53-C12-D27
A2-B79-C12-D27
A3-B79-C12-D27
A9-B79-C12-D27
A13-B79-C12-D27
A24-B79-C12-D27
A69-B79-C12-D27
A67-B79-C12-D27
A39-B79-C12-D27
A65-B79-C12-D27
A66-B79-C12-D27
A2-B80-C12-D27
A3-B80-C12-D27
A9-B80-C12-D27
A13-B80-C12-D27
A24-B80-C12-D27
A69-B80-C12-D27
A67-B80-C12-D27
A39-B80-C12-D27
A65-B80-C12-D27
A66-B80-C12-D27
A2-B85-C12-D27

-continued
A3-B85-C12-D27
A9-B85-C12-D27
A13-B85-C12-D27
A24-B85-C12-D27
A69-B85-C12-D27
A67-B85-C12-D27
A39-B85-C12-D27
A65-B85-C12-D27
A66-B85-C12-D27
A2-B86-C12-D27
A3-B86-C12-D27
A9-B86-C12-D27
A13-B86-C12-D27
A24-B86-C12-D27
A69-B86-C12-D27
A67-B86-C12-D27
A39-B86-C12-D27
A65-B86-C12-D27
A66-B86-C12-D27
A2-B87-C12-D27
A3-B87-C12-D27
A9-B87-C12-D27
A13-B87-C12-D27
A24-B87-C12-D27
A69-B87-C12-D27
A67-B87-C12-D27
A39-B87-C12-D27
A65-B87-C12-D27
A66-B87-C12-D27
A2-B89-C12-D27
A3-B89-C12-D27
A9-B89-C12-D27
A13-B89-C12-D27
A24-B89-C12-D27
A69-B89-C12-D27
A67-B89-C12-D27
A39-B89-C12-D27
A65-B89-C12-D27
A66-B89-C12-D27
A2-B92-C12-D27
A3-B92-C12-D27
A9-B92-C12-D27
A13-B92-C12-D27
A24-B92-C12-D27
A69-B92-C12-D27
A67-B92-C12-D27
A39-B92-C12-D27
A65-B92-C12-D27
A66-B92-C12-D27
A2-B4-C13-D27
A3-B4-C13-D27
A9-B4-C13-D27
A13-B4-C13-D27
A24-B4-C13-D27
A69-B4-C13-D27
A67-B4-C13-D27
A39-B4-C13-D27
A65-B4-C13-D27
A66-B4-C13-D27
A2-B5-C13-D27
A3-B5-C13-D27
A9-B5-C13-D27
A13-B5-C13-D27
A24-B5-C13-D27
A69-B5-C13-D27
A67-B5-C13-D27
A39-B5-C13-D27
A65-B5-C13-D27
A66-B5-C13-D27
A2-B6-C13-D27
A3-B6-C13-D27
A9-B6-C13-D27
A13-B6-C13-D27
A24-B6-C13-D27
A69-B6-C13-D27
A67-B6-C13-D27
A39-B6-C13-D27
A65-B6-C13-D27
A66-B6-C13-D27
A2-B32-C13-D27

-continued

A3-B32-C13-D27
A9-B32-C13-D27
A13-B32-C13-D27
A24-B32-C13-D27
A69-B32-C13-D27
A67-B32-C13-D27
A39-B32-C13-D27
A65-B32-C13-D27
A66-B32-C13-D27
A2-B39-C13-D27
A3-B39-C13-D27
A9-B39-C13-D27
A13-B39-C13-D27
A24-B39-C13-D27
A69-B39-C13-D27
A67-B39-C13-D27
A39-B39-C13-D27
A65-B39-C13-D27
A66-B39-C13-D27
A2-B45-C13-D27
A3-B45-C13-D27
A9-B45-C13-D27
A13-B45-C13-D27
A24-B45-C13-D27
A69-B45-C13-D27
A67-B45-C13-D27
A39-B45-C13-D27
A65-B45-C13-D27
A66-B45-C13-D27
A2-B53-C13-D27
A3-B53-C13-D27
A9-B53-C13-D27
A13-B53-C13-D27
A24-B53-C13-D27
A69-B53-C13-D27
A67-B53-C13-D27
A39-B53-C13-D27
A65-B53-C13-D27
A66-B53-C13-D27
A2-B79-C13-D27
A3-B79-C13-D27
A9-B79-C13-D27
A13-B79-C13-D27
A24-B79-C13-D27
A69-B79-C13-D27
A67-B79-C13-D27
A39-B79-C13-D27
A65-B79-C13-D27
A66-B79-C13-D27
A2-B80-C13-D27
A3-B80-C13-D27
A9-B80-C13-D27
A13-B80-C13-D27
A24-B80-C13-D27
A69-B80-C13-D27
A67-B80-C13-D27
A39-B80-C13-D27
A65-B80-C13-D27
A66-B80-C13-D27
A2-B85-C13-D27
A3-B85-C13-D27
A9-B85-C13-D27
A13-B85-C13-D27
A24-B85-C13-D27
A69-B85-C13-D27
A67-B85-C13-D27
A39-B85-C13-D27
A65-B85-C13-D27
A66-B85-C13-D27
A2-B86-C13-D27
A3-B86-C13-D27
A9-B86-C13-D27
A13-B86-C13-D27
A24-B86-C13-D27
A69-B86-C13-D27
A67-B86-C13-D27
A39-B86-C13-D27
A65-B86-C13-D27
A66-B86-C13-D27
A2-B87-C13-D27

-continued

A3-B87-C13-D27
A9-B87-C13-D27
A13-B87-C13-D27
A24-B87-C13-D27
A69-B87-C13-D27
A67-B87-C13-D27
A39-B87-C13-D27
A65-B87-C13-D27
A66-B87-C13-D27
A2-B89-C13-D27
A3-B89-C13-D27
A9-B89-C13-D27
A13-B89-C13-D27
A24-B89-C13-D27
A69-B89-C13-D27
A67-B89-C13-D27
A39-B89-C13-D27
A65-B89-C13-D27
A66-B89-C13-D27
A2-B92-C13-D27
A3-B92-C13-D27
A9-B92-C13-D27
A13-B92-C13-D27
A24-B92-C13-D27
A69-B92-C13-D27
A67-B92-C13-D27
A39-B92-C13-D27
A65-B92-C13-D27
A66-B92-C13-D27
A2-B4-C1-D28
A3-B4-C1-D28
A9-B4-C1-D28
A13-B4-C1-D28
A24-B4-C1-D28
A69-B4-C1-D28
A67-B4-C1-D28
A39-B4-C1-D28
A65-B4-C1-D28
A66-B4-C1-D28
A2-B5-C1-D28
A3-B5-C1-D28
A9-B5-C1-D28
A13-B5-C1-D28
A24-B5-C1-D28
A69-B5-C1-D28
A67-B5-C1-D28
A39-B5-C1-D28
A65-B5-C1-D28
A66-B5-C1-D28
A2-B6-C1-D28
A3-B6-C1-D28
A9-B6-C1-D28
A13-B6-C1-D28
A24-B6-C1-D28
A69-B6-C1-D28
A67-B6-C1-D28
A39-B6-C1-D28
A65-B6-C1-D28
A66-B6-C1-D28
A2-B32-C1-D28
A3-B32-C1-D28
A9-B32-C1-D28
A13-B32-C1-D28
A24-B32-C1-D28
A69-B32-C1-D28
A67-B32-C1-D28
A39-B32-C1-D28
A65-B32-C1-D28
A66-B32-C1-D28
A2-B39-C1-D28
A3-B39-C1-D28
A9-B39-C1-D28
A13-B39-C1-D28
A24-B39-C1-D28
A69-B39-C1-D28
A67-B39-C1-D28
A39-B39-C1-D28
A65-B39-C1-D28
A66-B39-C1-D28
A2-B45-C1-D28

-continued
A3-B45-C1-D28
A9-B45-C1-D28
A13-B45-C1-D28
A24-B45-C1-D28
A69-B45-C1-D28
A67-B45-C1-D28
A39-B45-C1-D28
A65-B45-C1-D28
A66-B45-C1-D28
A2-B53-C1-D28
A3-B53-C1-D28
A9-B53-C1-D28
A13-B53-C1-D28
A24-B53-C1-D28
A69-B53-C1-D28
A67-B53-C1-D28
A39-B53-C1-D28
A65-B53-C1-D28
A66-B53-C1-D28
A2-B79-C1-D28
A3-B79-C1-D28
A9-B79-C1-D28
A13-B79-C1-D28
A24-B79-C1-D28
A69-B79-C1-D28
A67-B79-C1-D28
A39-B79-C1-D28
A65-B79-C1-D28
A66-B79-C1-D28
A2-B80-C1-D28
A3-B80-C1-D28
A9-B80-C1-D28
A13-B80-C1-D28
A24-B80-C1-D28
A69-B80-C1-D28
A67-B80-C1-D28
A39-B80-C1-D28
A65-B80-C1-D28
A66-B80-C1-D28
A2-B85-C1-D28
A3-B85-C1-D28
A9-B85-C1-D28
A13-B85-C1-D28
A24-B85-C1-D28
A69-B85-C1-D28
A67-B85-C1-D28
A39-B85-C1-D28
A65-B85-C1-D28
A66-B85-C1-D28
A2-B86-C1-D28
A3-B86-C1-D28
A9-B86-C1-D28
A13-B86-C1-D28
A24-B86-C1-D28
A69-B86-C1-D28
A67-B86-C1-D28
A39-B86-C1-D28
A65-B86-C1-D28
A66-B86-C1-D28
A2-B87-C1-D28
A3-B87-C1-D28
A9-B87-C1-D28
A13-B87-C1-D28
A24-B87-C1-D28
A69-B87-C1-D28
A67-B87-C1-D28
A39-B87-C1-D28
A65-B87-C1-D28
A66-B87-C1-D28
A2-B89-C1-D28
A3-B89-C1-D28
A9-B89-C1-D28
A13-B89-C1-D28
A24-B89-C1-D28
A69-B89-C1-D28
A67-B89-C1-D28
A39-B89-C1-D28
A65-B89-C1-D28
A66-B89-C1-D28
A2-B92-C1-D28

-continued
A3-B92-C1-D28
A9-B92-C1-D28
A13-B92-C1-D28
A24-B92-C1-D28
A69-B92-C1-D28
A67-B92-C1-D28
A39-B92-C1-D28
A65-B92-C1-D28
A66-B92-C1-D28
A2-B4-C2-D28
A3-B4-C2-D28
A9-B4-C2-D28
A13-B4-C2-D28
A24-B4-C2-D28
A69-B4-C2-D28
A67-B4-C2-D28
A39-B4-C2-D28
A65-B4-C2-D28
A66-B4-C2-D28
A2-B5-C2-D28
A3-B5-C2-D28
A9-B5-C2-D28
A13-B5-C2-D28
A24-B5-C2-D28
A69-B5-C2-D28
A67-B5-C2-D28
A39-B5-C2-D28
A65-B5-C2-D28
A66-B5-C2-D28
A2-B6-C2-D28
A3-B6-C2-D28
A9-B6-C2-D28
A13-B6-C2-D28
A24-B6-C2-D28
A69-B6-C2-D28
A67-B6-C2-D28
A39-B6-C2-D28
A65-B6-C2-D28
A66-B6-C2-D28
A2-B32-C2-D28
A3-B32-C2-D28
A9-B32-C2-D28
A13-B32-C2-D28
A24-B32-C2-D28
A69-B32-C2-D28
A67-B32-C2-D28
A39-B32-C2-D28
A65-B32-C2-D28
A66-B32-C2-D28
A2-B39-C2-D28
A3-B39-C2-D28
A9-B39-C2-D28
A13-B39-C2-D28
A24-B39-C2-D28
A69-B39-C2-D28
A67-B39-C2-D28
A39-B39-C2-D28
A65-B39-C2-D28
A66-B39-C2-D28
A2-B45-C2-D28
A3-B45-C2-D28
A9-B45-C2-D28
A13-B45-C2-D28
A24-B45-C2-D28
A69-B45-C2-D28
A67-B45-C2-D28
A39-B45-C2-D28
A65-B45-C2-D28
A66-B45-C2-D28
A2-B53-C2-D28
A3-B53-C2-D28
A9-B53-C2-D28
A13-B53-C2-D28
A24-B53-C2-D28
A69-B53-C2-D28
A67-B53-C2-D28
A39-B53-C2-D28
A65-B53-C2-D28
A66-B53-C2-D28
A2-B79-C2-D28

-continued

A3-B79-C2-D28
A9-B79-C2-D28
A13-B79-C2-D28
A24-B79-C2-D28
A69-B79-C2-D28
A67-B79-C2-D28
A39-B79-C2-D28
A65-B79-C2-D28
A66-B79-C2-D28
A2-B80-C2-D28
A3-B80-C2-D28
A9-B80-C2-D28
A13-B80-C2-D28
A24-B80-C2-D28
A69-B80-C2-D28
A67-B80-C2-D28
A39-B80-C2-D28
A65-B80-C2-D28
A66-B80-C2-D28
A2-B85-C2-D28
A3-B85-C2-D28
A9-B85-C2-D28
A13-B85-C2-D28
A24-B85-C2-D28
A69-B85-C2-D28
A67-B85-C2-D28
A39-B85-C2-D28
A65-B85-C2-D28
A66-B85-C2-D28
A2-B86-C2-D28
A3-B86-C2-D28
A9-B86-C2-D28
A13-B86-C2-D28
A24-B86-C2-D28
A69-B86-C2-D28
A67-B86-C2-D28
A39-B86-C2-D28
A65-B86-C2-D28
A66-B86-C2-D28
A2-B87-C2-D28
A3-B87-C2-D28
A9-B87-C2-D28
A13-B87-C2-D28
A24-B87-C2-D28
A69-B87-C2-D28
A67-B87-C2-D28
A39-B87-C2-D28
A65-B87-C2-D28
A66-B87-C2-D28
A2-B89-C2-D28
A3-B89-C2-D28
A9-B89-C2-D28
A13-B89-C2-D28
A24-B89-C2-D28
A69-B89-C2-D28
A67-B89-C2-D28
A39-B89-C2-D28
A65-B89-C2-D28
A66-B89-C2-D28
A2-B92-C2-D28
A3-B92-C2-D28
A9-B92-C2-D28
A13-B92-C2-D28
A24-B92-C2-D28
A69-B92-C2-D28
A67-B92-C2-D28
A39-B92-C2-D28
A65-B92-C2-D28
A66-B92-C2-D28
A2-B4-C3-D28
A3-B4-C3-D28
A9-B4-C3-D28
A13-B4-C3-D28
A24-B4-C3-D28
A69-B4-C3-D28
A67-B4-C3-D28
A39-B4-C3-D28
A65-B4-C3-D28
A66-B4-C3-D28
A2-B5-C3-D28

-continued

A3-B5-C3-D28
A9-B5-C3-D28
A13-B5-C3-D28
A24-B5-C3-D28
A69-B5-C3-D28
A67-B5-C3-D28
A39-B5-C3-D28
A65-B5-C3-D28
A66-B5-C3-D28
A2-B6-C3-D28
A3-B6-C3-D28
A9-B6-C3-D28
A13-B6-C3-D28
A24-B6-C3-D28
A69-B6-C3-D28
A67-B6-C3-D28
A39-B6-C3-D28
A65-B6-C3-D28
A66-B6-C3-D28
A2-B32-C3-D28
A3-B32-C3-D28
A9-B32-C3-D28
A13-B32-C3-D28
A24-B32-C3-D28
A69-B32-C3-D28
A67-B32-C3-D28
A39-B32-C3-D28
A65-B32-C3-D28
A66-B32-C3-D28
A2-B39-C3-D28
A3-B39-C3-D28
A9-B39-C3-D28
A13-B39-C3-D28
A24-B39-C3-D28
A69-B39-C3-D28
A67-B39-C3-D28
A39-B39-C3-D28
A65-B39-C3-D28
A66-B39-C3-D28
A2-B45-C3-D28
A3-B45-C3-D28
A9-B45-C3-D28
A13-B45-C3-D28
A24-B45-C3-D28
A69-B45-C3-D28
A67-B45-C3-D28
A39-B45-C3-D28
A65-B45-C3-D28
A66-B45-C3-D28
A2-B53-C3-D28
A3-B53-C3-D28
A9-B53-C3-D28
A13-B53-C3-D28
A24-B53-C3-D28
A69-B53-C3-D28
A67-B53-C3-D28
A39-B53-C3-D28
A65-B53-C3-D28
A66-B53-C3-D28
A2-B79-C3-D28
A3-B79-C3-D28
A9-B79-C3-D28
A13-B79-C3-D28
A24-B79-C3-D28
A69-B79-C3-D28
A67-B79-C3-D28
A39-B79-C3-D28
A65-B79-C3-D28
A66-B79-C3-D28
A2-B80-C3-D28
A3-B80-C3-D28
A9-B80-C3-D28
A13-B80-C3-D28
A24-B80-C3-D28
A69-B80-C3-D28
A67-B80-C3-D28
A39-B80-C3-D28
A65-B80-C3-D28
A66-B80-C3-D28
A2-B85-C3-D28

-continued
A3-B85-C3-D28
A9-B85-C3-D28
A13-B85-C3-D28
A24-B85-C3-D28
A69-B85-C3-D28
A67-B85-C3-D28
A39-B85-C3-D28
A65-B85-C3-D28
A66-B85-C3-D28
A2-B86-C3-D28
A3-B86-C3-D28
A9-B86-C3-D28
A13-B86-C3-D28
A24-B86-C3-D28
A69-B86-C3-D28
A67-B86-C3-D28
A39-B86-C3-D28
A65-B86-C3-D28
A66-B86-C3-D28
A2-B87-C3-D28
A3-B87-C3-D28
A9-B87-C3-D28
A13-B87-C3-D28
A24-B87-C3-D28
A69-B87-C3-D28
A67-B87-C3-D28
A39-B87-C3-D28
A65-B87-C3-D28
A66-B87-C3-D28
A2-B89-C3-D28
A3-B89-C3-D28
A9-B89-C3-D28
A13-B89-C3-D28
A24-B89-C3-D28
A69-B89-C3-D28
A67-B89-C3-D28
A39-B89-C3-D28
A65-B89-C3-D28
A66-B89-C3-D28
A2-B92-C3-D28
A3-B92-C3-D28
A9-B92-C3-D28
A13-B92-C3-D28
A24-B92-C3-D28
A69-B92-C3-D28
A67-B92-C3-D28
A39-B92-C3-D28
A65-B92-C3-D28
A66-B92-C3-D28
A2-B4-C4-D28
A3-B4-C4-D28
A9-B4-C4-D28
A13-B4-C4-D28
A24-B4-C4-D28
A69-B4-C4-D28
A67-B4-C4-D28
A39-B4-C4-D28
A65-B4-C4-D28
A66-B4-C4-D28
A2-B5-C4-D28
A3-B5-C4-D28
A9-B5-C4-D28
A13-B5-C4-D28
A24-B5-C4-D28
A69-B5-C4-D28
A67-B5-C4-D28
A39-B5-C4-D28
A65-B5-C4-D28
A66-B5-C4-D28
A2-B6-C4-D28
A3-B6-C4-D28
A9-B6-C4-D28
A13-B6-C4-D28
A24-B6-C4-D28
A69-B6-C4-D28
A67-B6-C4-D28
A39-B6-C4-D28
A65-B6-C4-D28
A66-B6-C4-D28
A2-B32-C4-D28

-continued
A3-B32-C4-D28
A9-B32-C4-D28
A13-B32-C4-D28
A24-B32-C4-D28
A69-B32-C4-D28
A67-B32-C4-D28
A39-B32-C4-D28
A65-B32-C4-D28
A66-B32-C4-D28
A2-B39-C4-D28
A3-B39-C4-D28
A9-B39-C4-D28
A13-B39-C4-D28
A24-B39-C4-D28
A69-B39-C4-D28
A67-B39-C4-D28
A39-B39-C4-D28
A65-B39-C4-D28
A66-B39-C4-D28
A2-B45-C4-D28
A3-B45-C4-D28
A9-B45-C4-D28
A13-B45-C4-D28
A24-B45-C4-D28
A69-B45-C4-D28
A67-B45-C4-D28
A39-B45-C4-D28
A65-B45-C4-D28
A66-B45-C4-D28
A2-B53-C4-D28
A3-B53-C4-D28
A9-B53-C4-D28
A13-B53-C4-D28
A24-B53-C4-D28
A69-B53-C4-D28
A67-B53-C4-D28
A39-B53-C4-D28
A65-B53-C4-D28
A66-B53-C4-D28
A2-B79-C4-D28
A3-B79-C4-D28
A9-B79-C4-D28
A13-B79-C4-D28
A24-B79-C4-D28
A69-B79-C4-D28
A67-B79-C4-D28
A39-B79-C4-D28
A65-B79-C4-D28
A66-B79-C4-D28
A2-B80-C4-D28
A3-B80-C4-D28
A9-B80-C4-D28
A13-B80-C4-D28
A24-B80-C4-D28
A69-B80-C4-D28
A67-B80-C4-D28
A39-B80-C4-D28
A65-B80-C4-D28
A66-B80-C4-D28
A2-B85-C4-D28
A3-B85-C4-D28
A9-B85-C4-D28
A13-B85-C4-D28
A24-B85-C4-D28
A69-B85-C4-D28
A67-B85-C4-D28
A39-B85-C4-D28
A65-B85-C4-D28
A66-B85-C4-D28
A2-B86-C4-D28
A3-B86-C4-D28
A9-B86-C4-D28
A13-B86-C4-D28
A24-B86-C4-D28
A69-B86-C4-D28
A67-B86-C4-D28
A39-B86-C4-D28
A65-B86-C4-D28
A66-B86-C4-D28
A2-B87-C4-D28

-continued

A3-B87-C4-D28
A9-B87-C4-D28
A13-B87-C4-D28
A24-B87-C4-D28
A69-B87-C4-D28
A67-B87-C4-D28
A39-B87-C4-D28
A65-B87-C4-D28
A66-B87-C4-D28
A2-B89-C4-D28
A3-B89-C4-D28
A9-B89-C4-D28
A13-B89-C4-D28
A24-B89-C4-D28
A69-B89-C4-D28
A67-B89-C4-D28
A39-B89-C4-D28
A65-B89-C4-D28
A66-B89-C4-D28
A2-B92-C4-D28
A3-B92-C4-D28
A9-B92-C4-D28
A13-B92-C4-D28
A24-B92-C4-D28
A69-B92-C4-D28
A67-B92-C4-D28
A39-B92-C4-D28
A65-B92-C4-D28
A66-B92-C4-D28
A2-B4-C5-D28
A3-B4-C5-D28
A9-B4-C5-D28
A13-B4-C5-D28
A24-B4-C5-D28
A69-B4-C5-D28
A67-B4-C5-D28
A39-B4-C5-D28
A65-B4-C5-D28
A66-B4-C5-D28
A2-B5-C5-D28
A3-B5-C5-D28
A9-B5-C5-D28
A13-B5-C5-D28
A24-B5-C5-D28
A69-B5-C5-D28
A67-B5-C5-D28
A39-B5-C5-D28
A65-B5-C5-D28
A66-B5-C5-D28
A2-B6-C5-D28
A3-B6-C5-D28
A9-B6-C5-D28
A13-B6-C5-D28
A24-B6-C5-D28
A69-B6-C5-D28
A67-B6-C5-D28
A39-B6-C5-D28
A65-B6-C5-D28
A66-B6-C5-D28
A2-B32-C5-D28
A3-B32-C5-D28
A9-B32-C5-D28
A13-B32-C5-D28
A24-B32-C5-D28
A69-B32-C5-D28
A67-B32-C5-D28
A39-B32-C5-D28
A65-B32-C5-D28
A66-B32-C5-D28
A2-B39-C5-D28
A3-B39-C5-D28
A9-B39-C5-D28
A13-B39-C5-D28
A24-B39-C5-D28
A69-B39-C5-D28
A67-B39-C5-D28
A39-B39-C5-D28
A65-B39-C5-D28
A66-B39-C5-D28
A2-B45-C5-D28

-continued

A3-B45-C5-D28
A9-B45-C5-D28
A13-B45-C5-D28
A24-B45-C5-D28
A69-B45-C5-D28
A67-B45-C5-D28
A39-B45-C5-D28
A65-B45-C5-D28
A66-B45-C5-D28
A2-B53-C5-D28
A3-B53-C5-D28
A9-B53-C5-D28
A13-B53-C5-D28
A24-B53-C5-D28
A69-B53-C5-D28
A67-B53-C5-D28
A39-B53-C5-D28
A65-B53-C5-D28
A66-B53-C5-D28
A2-B79-C5-D28
A3-B79-C5-D28
A9-B79-C5-D28
A13-B79-C5-D28
A24-B79-C5-D28
A69-B79-C5-D28
A67-B79-C5-D28
A39-B79-C5-D28
A65-B79-C5-D28
A66-B79-C5-D28
A2-B80-C5-D28
A3-B80-C5-D28
A9-B80-C5-D28
A13-B80-C5-D28
A24-B80-C5-D28
A69-B80-C5-D28
A67-B80-C5-D28
A39-B80-C5-D28
A65-B80-C5-D28
A66-B80-C5-D28
A2-B85-C5-D28
A3-B85-C5-D28
A9-B85-C5-D28
A13-B85-C5-D28
A24-B85-C5-D28
A69-B85-C5-D28
A67-B85-C5-D28
A39-B85-C5-D28
A65-B85-C5-D28
A66-B85-C5-D28
A2-B86-C5-D28
A3-B86-C5-D28
A9-B86-C5-D28
A13-B86-C5-D28
A24-B86-C5-D28
A69-B86-C5-D28
A67-B86-C5-D28
A39-B86-C5-D28
A65-B86-C5-D28
A66-B86-C5-D28
A2-B87-C5-D28
A3-B87-C5-D28
A9-B87-C5-D28
A13-B87-C5-D28
A24-B87-C5-D28
A69-B87-C5-D28
A67-B87-C5-D28
A39-B87-C5-D28
A65-B87-C5-D28
A66-B87-C5-D28
A2-B89-C5-D28
A3-B89-C5-D28
A9-B89-C5-D28
A13-B89-C5-D28
A24-B89-C5-D28
A69-B89-C5-D28
A67-B89-C5-D28
A39-B89-C5-D28
A65-B89-C5-D28
A66-B89-C5-D28
A2-B92-C5-D28

-continued

A3-B92-C5-D28
A9-B92-C5-D28
A13-B92-C5-D28
A24-B92-C5-D28
A69-B92-C5-D28
A67-B92-C5-D28
A39-B92-C5-D28
A65-B92-C5-D28
A66-B92-C5-D28
A2-B4-C6-D28
A3-B4-C6-D28
A9-B4-C6-D28
A13-B4-C6-D28
A24-B4-C6-D28
A69-B4-C6-D28
A67-B4-C6-D28
A39-B4-C6-D28
A65-B4-C6-D28
A66-B4-C6-D28
A2-B5-C6-D28
A3-B5-C6-D28
A9-B5-C6-D28
A13-B5-C6-D28
A24-B5-C6-D28
A69-B5-C6-D28
A67-B5-C6-D28
A39-B5-C6-D28
A65-B5-C6-D28
A66-B5-C6-D28
A2-B6-C6-D28
A3-B6-C6-D28
A9-B6-C6-D28
A13-B6-C6-D28
A24-B6-C6-D28
A69-B6-C6-D28
A67-B6-C6-D28
A39-B6-C6-D28
A65-B6-C6-D28
A66-B6-C6-D28
A2-B32-C6-D28
A3-B32-C6-D28
A9-B32-C6-D28
A13-B32-C6-D28
A24-B32-C6-D28
A69-B32-C6-D28
A67-B32-C6-D28
A39-B32-C6-D28
A65-B32-C6-D28
A66-B32-C6-D28
A2-B39-C6-D28
A3-B39-C6-D28
A9-B39-C6-D28
A13-B39-C6-D28
A24-B39-C6-D28
A69-B39-C6-D28
A67-B39-C6-D28
A39-B39-C6-D28
A65-B39-C6-D28
A66-B39-C6-D28
A2-B45-C6-D28
A3-B45-C6-D28
A9-B45-C6-D28
A13-B45-C6-D28
A24-B45-C6-D28
A69-B45-C6-D28
A67-B45-C6-D28
A39-B45-C6-D28
A65-B45-C6-D28
A66-B45-C6-D28
A2-B53-C6-D28
A3-B53-C6-D28
A9-B53-C6-D28
A13-B53-C6-D28
A24-B53-C6-D28
A69-B53-C6-D28
A67-B53-C6-D28
A39-B53-C6-D28
A65-B53-C6-D28
A66-B53-C6-D28
A2-B79-C6-D28

-continued

A3-B79-C6-D28
A9-B79-C6-D28
A13-B79-C6-D28
A24-B79-C6-D28
A69-B79-C6-D28
A67-B79-C6-D28
A39-B79-C6-D28
A65-B79-C6-D28
A66-B79-C6-D28
A2-B80-C6-D28
A3-B80-C6-D28
A9-B80-C6-D28
A13-B80-C6-D28
A24-B80-C6-D28
A69-B80-C6-D28
A67-B80-C6-D28
A39-B80-C6-D28
A65-B80-C6-D28
A66-B80-C6-D28
A2-B85-C6-D28
A3-B85-C6-D28
A9-B85-C6-D28
A13-B85-C6-D28
A24-B85-C6-D28
A69-B85-C6-D28
A67-B85-C6-D28
A39-B85-C6-D28
A65-B85-C6-D28
A66-B85-C6-D28
A2-B86-C6-D28
A3-B86-C6-D28
A9-B86-C6-D28
A13-B86-C6-D28
A24-B86-C6-D28
A69-B86-C6-D28
A67-B86-C6-D28
A39-B86-C6-D28
A65-B86-C6-D28
A66-B86-C6-D28
A2-B87-C6-D28
A3-B87-C6-D28
A9-B87-C6-D28
A13-B87-C6-D28
A24-B87-C6-D28
A69-B87-C6-D28
A67-B87-C6-D28
A39-B87-C6-D28
A65-B87-C6-D28
A66-B87-C6-D28
A2-B89-C6-D28
A3-B89-C6-D28
A9-B89-C6-D28
A13-B89-C6-D28
A24-B89-C6-D28
A69-B89-C6-D28
A67-B89-C6-D28
A39-B89-C6-D28
A65-B89-C6-D28
A66-B89-C6-D28
A2-B92-C6-D28
A3-B92-C6-D28
A9-B92-C6-D28
A13-B92-C6-D28
A24-B92-C6-D28
A69-B92-C6-D28
A67-B92-C6-D28
A39-B92-C6-D28
A65-B92-C6-D28
A66-B92-C6-D28
A2-B4-C7-D28
A3-B4-C7-D28
A9-B4-C7-D28
A13-B4-C7-D28
A24-B4-C7-D28
A69-B4-C7-D28
A67-B4-C7-D28
A39-B4-C7-D28
A65-B4-C7-D28
A66-B4-C7-D28
A2-B5-C7-D28

-continued
A3-B5-C7-D28
A9-B5-C7-D28
A13-B5-C7-D28
A24-B5-C7-D28
A69-B5-C7-D28
A67-B5-C7-D28
A39-B5-C7-D28
A65-B5-C7-D28
A66-B5-C7-D28
A2-B6-C7-D28
A3-B6-C7-D28
A9-B6-C7-D28
A13-B6-C7-D28
A24-B6-C7-D28
A69-B6-C7-D28
A67-B6-C7-D28
A39-B6-C7-D28
A65-B6-C7-D28
A66-B6-C7-D28
A2-B32-C7-D28
A3-B32-C7-D28
A9-B32-C7-D28
A13-B32-C7-D28
A24-B32-C7-D28
A69-B32-C7-D28
A67-B32-C7-D28
A39-B32-C7-D28
A65-B32-C7-D28
A66-B32-C7-D28
A2-B39-C7-D28
A3-B39-C7-D28
A9-B39-C7-D28
A13-B39-C7-D28
A24-B39-C7-D28
A69-B39-C7-D28
A67-B39-C7-D28
A39-B39-C7-D28
A65-B39-C7-D28
A66-B39-C7-D28
A2-B45-C7-D28
A3-B45-C7-D28
A9-B45-C7-D28
A13-B45-C7-D28
A24-B45-C7-D28
A69-B45-C7-D28
A67-B45-C7-D28
A39-B45-C7-D28
A65-B45-C7-D28
A66-B45-C7-D28
A2-B53-C7-D28
A3-B53-C7-D28
A9-B53-C7-D28
A13-B53-C7-D28
A24-B53-C7-D28
A69-B53-C7-D28
A67-B53-C7-D28
A39-B53-C7-D28
A65-B53-C7-D28
A66-B53-C7-D28
A2-B79-C7-D28
A3-B79-C7-D28
A9-B79-C7-D28
A13-B79-C7-D28
A24-B79-C7-D28
A69-B79-C7-D28
A67-B79-C7-D28
A39-B79-C7-D28
A65-B79-C7-D28
A66-B79-C7-D28
A2-B80-C7-D28
A3-B80-C7-D28
A9-B80-C7-D28
A13-B80-C7-D28
A24-B80-C7-D28
A69-B80-C7-D28
A67-B80-C7-D28
A39-B80-C7-D28
A65-B80-C7-D28
A66-B80-C7-D28
A2-B85-C7-D28

-continued
A3-B85-C7-D28
A9-B85-C7-D28
A13-B85-C7-D28
A24-B85-C7-D28
A69-B85-C7-D28
A67-B85-C7-D28
A39-B85-C7-D28
A65-B85-C7-D28
A66-B85-C7-D28
A2-B86-C7-D28
A3-B86-C7-D28
A9-B86-C7-D28
A13-B86-C7-D28
A24-B86-C7-D28
A69-B86-C7-D28
A67-B86-C7-D28
A39-B86-C7-D28
A65-B86-C7-D28
A66-B86-C7-D28
A2-B87-C7-D28
A3-B87-C7-D28
A9-B87-C7-D28
A13-B87-C7-D28
A24-B87-C7-D28
A69-B87-C7-D28
A67-B87-C7-D28
A39-B87-C7-D28
A65-B87-C7-D28
A66-B87-C7-D28
A2-B89-C7-D28
A3-B89-C7-D28
A9-B89-C7-D28
A13-B89-C7-D28
A24-B89-C7-D28
A69-B89-C7-D28
A67-B89-C7-D28
A39-B89-C7-D28
A65-B89-C7-D28
A66-B89-C7-D28
A2-B92-C7-D28
A3-B92-C7-D28
A9-B92-C7-D28
A13-B92-C7-D28
A24-B92-C7-D28
A69-B92-C7-D28
A67-B92-C7-D28
A39-B92-C7-D28
A65-B92-C7-D28
A66-B92-C7-D28
A2-B4-C8-D28
A3-B4-C8-D28
A9-B4-C8-D28
A13-B4-C8-D28
A24-B4-C8-D28
A69-B4-C8-D28
A67-B4-C8-D28
A39-B4-C8-D28
A65-B4-C8-D28
A66-B4-C8-D28
A2-B5-C8-D28
A3-B5-C8-D28
A9-B5-C8-D28
A13-B5-C8-D28
A24-B5-C8-D28
A69-B5-C8-D28
A67-B5-C8-D28
A39-B5-C8-D28
A65-B5-C8-D28
A66-B5-C8-D28
A2-B6-C8-D28
A3-B6-C8-D28
A9-B6-C8-D28
A13-B6-C8-D28
A24-B6-C8-D28
A69-B6-C8-D28
A67-B6-C8-D28
A39-B6-C8-D28
A65-B6-C8-D28
A66-B6-C8-D28
A2-B32-C8-D28

-continued
A3-B32-C8-D28
A9-B32-C8-D28
A13-B32-C8-D28
A24-B32-C8-D28
A69-B32-C8-D28
A67-B32-C8-D28
A39-B32-C8-D28
A65-B32-C8-D28
A66-B32-C8-D28
A2-B39-C8-D28
A3-B39-C8-D28
A9-B39-C8-D28
A13-B39-C8-D28
A24-B39-C8-D28
A69-B39-C8-D28
A67-B39-C8-D28
A39-B39-C8-D28
A65-B39-C8-D28
A66-B39-C8-D28
A2-B45-C8-D28
A3-B45-C8-D28
A9-B45-C8-D28
A13-B45-C8-D28
A24-B45-C8-D28
A69-B45-C8-D28
A67-B45-C8-D28
A39-B45-C8-D28
A65-B45-C8-D28
A66-B45-C8-D28
A2-B53-C8-D28
A3-B53-C8-D28
A9-B53-C8-D28
A13-B53-C8-D28
A24-B53-C8-D28
A69-B53-C8-D28
A67-B53-C8-D28
A39-B53-C8-D28
A65-B53-C8-D28
A66-B53-C8-D28
A2-B79-C8-D28
A3-B79-C8-D28
A9-B79-C8-D28
A13-B79-C8-D28
A24-B79-C8-D28
A69-B79-C8-D28
A67-B79-C8-D28
A39-B79-C8-D28
A65-B79-C8-D28
A66-B79-C8-D28
A2-B80-C8-D28
A3-B80-C8-D28
A9-B80-C8-D28
A13-B80-C8-D28
A24-B80-C8-D28
A69-B80-C8-D28
A67-B80-C8-D28
A39-B80-C8-D28
A65-B80-C8-D28
A66-B80-C8-D28
A2-B85-C8-D28
A3-B85-C8-D28
A9-B85-C8-D28
A13-B85-C8-D28
A24-B85-C8-D28
A69-B85-C8-D28
A67-B85-C8-D28
A39-B85-C8-D28
A65-B85-C8-D28
A66-B85-C8-D28
A2-B86-C8-D28
A3-B86-C8-D28
A9-B86-C8-D28
A13-B86-C8-D28
A24-B86-C8-D28
A69-B86-C8-D28
A67-B86-C8-D28
A39-B86-C8-D28
A65-B86-C8-D28
A66-B86-C8-D28
A2-B87-C8-D28

-continued
A3-B87-C8-D28
A9-B87-C8-D28
A13-B87-C8-D28
A24-B87-C8-D28
A69-B87-C8-D28
A67-B87-C8-D28
A39-B87-C8-D28
A65-B87-C8-D28
A66-B87-C8-D28
A2-B89-C8-D28
A3-B89-C8-D28
A9-B89-C8-D28
A13-B89-C8-D28
A24-B89-C8-D28
A69-B89-C8-D28
A67-B89-C8-D28
A39-B89-C8-D28
A65-B89-C8-D28
A66-B89-C8-D28
A2-B92-C8-D28
A3-B92-C8-D28
A9-B92-C8-D28
A13-B92-C8-D28
A24-B92-C8-D28
A69-B92-C8-D28
A67-B92-C8-D28
A39-B92-C8-D28
A65-B92-C8-D28
A66-B92-C8-D28
A2-B4-C9-D28
A3-B4-C9-D28
A9-B4-C9-D28
A13-B4-C9-D28
A24-B4-C9-D28
A69-B4-C9-D28
A67-B4-C9-D28
A39-B4-C9-D28
A65-B4-C9-D28
A66-B4-C9-D28
A2-B5-C9-D28
A3-B5-C9-D28
A9-B5-C9-D28
A13-B5-C9-D28
A24-B5-C9-D28
A69-B5-C9-D28
A67-B5-C9-D28
A39-B5-C9-D28
A65-B5-C9-D28
A66-B5-C9-D28
A2-B6-C9-D28
A3-B6-C9-D28
A9-B6-C9-D28
A13-B6-C9-D28
A24-B6-C9-D28
A69-B6-C9-D28
A67-B6-C9-D28
A39-B6-C9-D28
A65-B6-C9-D28
A66-B6-C9-D28
A2-B32-C9-D28
A3-B32-C9-D28
A9-B32-C9-D28
A13-B32-C9-D28
A24-B32-C9-D28
A69-B32-C9-D28
A67-B32-C9-D28
A39-B32-C9-D28
A65-B32-C9-D28
A66-B32-C9-D28
A2-B39-C9-D28
A3-B39-C9-D28
A9-B39-C9-D28
A13-B39-C9-D28
A24-B39-C9-D28
A69-B39-C9-D28
A67-B39-C9-D28
A39-B39-C9-D28
A65-B39-C9-D28
A66-B39-C9-D28
A2-B45-C9-D28

-continued
A3-B45-C9-D28
A9-B45-C9-D28
A13-B45-C9-D28
A24-B45-C9-D28
A69-B45-C9-D28
A67-B45-C9-D28
A39-B45-C9-D28
A65-B45-C9-D28
A66-B45-C9-D28
A2-B53-C9-D28
A3-B53-C9-D28
A9-B53-C9-D28
A13-B53-C9-D28
A24-B53-C9-D28
A69-B53-C9-D28
A67-B53-C9-D28
A39-B53-C9-D28
A65-B53-C9-D28
A66-B53-C9-D28
A2-B79-C9-D28
A3-B79-C9-D28
A9-B79-C9-D28
A13-B79-C9-D28
A24-B79-C9-D28
A69-B79-C9-D28
A67-B79-C9-D28
A39-B79-C9-D28
A65-B79-C9-D28
A66-B79-C9-D28
A2-B80-C9-D28
A3-B80-C9-D28
A9-B80-C9-D28
A13-B80-C9-D28
A24-B80-C9-D28
A69-B80-C9-D28
A67-B80-C9-D28
A39-B80-C9-D28
A65-B80-C9-D28
A66-B80-C9-D28
A2-B85-C9-D28
A3-B85-C9-D28
A9-B85-C9-D28
A13-B85-C9-D28
A24-B85-C9-D28
A69-B85-C9-D28
A67-B85-C9-D28
A39-B85-C9-D28
A65-B85-C9-D28
A66-B85-C9-D28
A2-B86-C9-D28
A3-B86-C9-D28
A9-B86-C9-D28
A13-B86-C9-D28
A24-B86-C9-D28
A69-B86-C9-D28
A67-B86-C9-D28
A39-B86-C9-D28
A65-B86-C9-D28
A66-B86-C9-D28
A2-B87-C9-D28
A3-B87-C9-D28
A9-B87-C9-D28
A13-B87-C9-D28
A24-B87-C9-D28
A69-B87-C9-D28
A67-B87-C9-D28
A39-B87-C9-D28
A65-B87-C9-D28
A66-B87-C9-D28
A2-B89-C9-D28
A3-B89-C9-D28
A9-B89-C9-D28
A13-B89-C9-D28
A24-B89-C9-D28
A69-B89-C9-D28
A67-B89-C9-D28
A39-B89-C9-D28
A65-B89-C9-D28
A66-B89-C9-D28
A2-B92-C9-D28

-continued
A3-B92-C9-D28
A9-B92-C9-D28
A13-B92-C9-D28
A24-B92-C9-D28
A69-B92-C9-D28
A67-B92-C9-D28
A39-B92-C9-D28
A65-B92-C9-D28
A66-B92-C9-D28
A2-B4-C10-D28
A3-B4-C10-D28
A9-B4-C10-D28
A13-B4-C10-D28
A24-B4-C10-D28
A69-B4-C10-D28
A67-B4-C10-D28
A39-B4-C10-D28
A65-B4-C10-D28
A66-B4-C10-D28
A2-B5-C10-D28
A3-B5-C10-D28
A9-B5-C10-D28
A13-B5-C10-D28
A24-B5-C10-D28
A69-B5-C10-D28
A67-B5-C10-D28
A39-B5-C10-D28
A65-B5-C10-D28
A66-B5-C10-D28
A2-B6-C10-D28
A3-B6-C10-D28
A9-B6-C10-D28
A13-B6-C10-D28
A24-B6-C10-D28
A69-B6-C10-D28
A67-B6-C10-D28
A39-B6-C10-D28
A65-B6-C10-D28
A66-B6-C10-D28
A2-B32-C10-D28
A3-B32-C10-D28
A9-B32-C10-D28
A13-B32-C10-D28
A24-B32-C10-D28
A69-B32-C10-D28
A67-B32-C10-D28
A39-B32-C10-D28
A65-B32-C10-D28
A66-B32-C10-D28
A2-B39-C10-D28
A3-B39-C10-D28
A9-B39-C10-D28
A13-B39-C10-D28
A24-B39-C10-D28
A69-B39-C10-D28
A67-B39-C10-D28
A39-B39-C10-D28
A65-B39-C10-D28
A66-B39-C10-D28
A2-B45-C10-D28
A3-B45-C10-D28
A9-B45-C10-D28
A13-B45-C10-D28
A24-B45-C10-D28
A69-B45-C10-D28
A67-B45-C10-D28
A39-B45-C10-D28
A65-B45-C10-D28
A66-B45-C10-D28
A2-B53-C10-D28
A3-B53-C10-D28
A9-B53-C10-D28
A13-B53-C10-D28
A24-B53-C10-D28
A69-B53-C10-D28
A67-B53-C10-D28
A39-B53-C10-D28
A65-B53-C10-D28
A66-B53-C10-D28
A2-B79-C10-D28

-continued

A3-B79-C10-D28
A9-B79-C10-D28
A13-B79-C10-D28
A24-B79-C10-D28
A69-B79-C10-D28
A67-B79-C10-D28
A39-B79-C10-D28
A65-B79-C10-D28
A66-B79-C10-D28
A2-B80-C10-D28
A3-B80-C10-D28
A9-B80-C10-D28
A13-B80-C10-D28
A24-B80-C10-D28
A69-B80-C10-D28
A67-B80-C10-D28
A39-B80-C10-D28
A65-B80-C10-D28
A66-B80-C10-D28
A2-B85-C10-D28
A3-B85-C10-D28
A9-B85-C10-D28
A13-B85-C10-D28
A24-B85-C10-D28
A69-B85-C10-D28
A67-B85-C10-D28
A39-B85-C10-D28
A65-B85-C10-D28
A66-B85-C10-D28
A2-B86-C10-D28
A3-B86-C10-D28
A9-B86-C10-D28
A13-B86-C10-D28
A24-B86-C10-D28
A69-B86-C10-D28
A67-B86-C10-D28
A39-B86-C10-D28
A65-B86-C10-D28
A66-B86-C10-D28
A2-B87-C10-D28
A3-B87-C10-D28
A9-B87-C10-D28
A13-B87-C10-D28
A24-B87-C10-D28
A69-B87-C10-D28
A67-B87-C10-D28
A39-B87-C10-D28
A65-B87-C10-D28
A66-B87-C10-D28
A2-B89-C10-D28
A3-B89-C10-D28
A9-B89-C10-D28
A13-B89-C10-D28
A24-B89-C10-D28
A69-B89-C10-D28
A67-B89-C10-D28
A39-B89-C10-D28
A65-B89-C10-D28
A66-B89-C10-D28
A2-B92-C10-D28
A3-B92-C10-D28
A9-B92-C10-D28
A13-B92-C10-D28
A24-B92-C10-D28
A69-B92-C10-D28
A67-B92-C10-D28
A39-B92-C10-D28
A65-B92-C10-D28
A66-B92-C10-D28
A2-B4-C11-D28
A3-B4-C11-D28
A9-B4-C11-D28
A13-B4-C11-D28
A24-B4-C11-D28
A69-B4-C11-D28
A67-B4-C11-D28
A39-B4-C11-D28
A65-B4-C11-D28
A66-B4-C11-D28
A2-B5-C11-D28

-continued

A3-B5-C11-D28
A9-B5-C11-D28
A13-B5-C11-D28
A24-B5-C11-D28
A69-B5-C11-D28
A67-B5-C11-D28
A39-B5-C11-D28
A65-B5-C11-D28
A66-B5-C11-D28
A2-B6-C11-D28
A3-B6-C11-D28
A9-B6-C11-D28
A13-B6-C11-D28
A24-B6-C11-D28
A69-B6-C11-D28
A67-B6-C11-D28
A39-B6-C11-D28
A65-B6-C11-D28
A66-B6-C11-D28
A2-B32-C11-D28
A3-B32-C11-D28
A9-B32-C11-D28
A13-B32-C11-D28
A24-B32-C11-D28
A69-B32-C11-D28
A67-B32-C11-D28
A39-B32-C11-D28
A65-B32-C11-D28
A66-B32-C11-D28
A2-B39-C11-D28
A3-B39-C11-D28
A9-B39-C11-D28
A13-B39-C11-D28
A24-B39-C11-D28
A69-B39-C11-D28
A67-B39-C11-D28
A39-B39-C11-D28
A65-B39-C11-D28
A66-B39-C11-D28
A2-B45-C11-D28
A3-B45-C11-D28
A9-B45-C11-D28
A13-B45-C11-D28
A24-B45-C11-D28
A69-B45-C11-D28
A67-B45-C11-D28
A39-B45-C11-D28
A65-B45-C11-D28
A66-B45-C11-D28
A2-B53-C11-D28
A3-B53-C11-D28
A9-B53-C11-D28
A13-B53-C11-D28
A24-B53-C11-D28
A69-B53-C11-D28
A67-B53-C11-D28
A39-B53-C11-D28
A65-B53-C11-D28
A66-B53-C11-D28
A2-B79-C11-D28
A3-B79-C11-D28
A9-B79-C11-D28
A13-B79-C11-D28
A24-B79-C11-D28
A69-B79-C11-D28
A67-B79-C11-D28
A39-B79-C11-D28
A65-B79-C11-D28
A66-B79-C11-D28
A2-B80-C11-D28
A3-B80-C11-D28
A9-B80-C11-D28
A13-B80-C11-D28
A24-B80-C11-D28
A69-B80-C11-D28
A67-B80-C11-D28
A39-B80-C11-D28
A65-B80-C11-D28
A66-B80-C11-D28
A2-B85-C11-D28

-continued

A3-B85-C11-D28
A9-B85-C11-D28
A13-B85-C11-D28
A24-B85-C11-D28
A69-B85-C11-D28
A67-B85-C11-D28
A39-B85-C11-D28
A65-B85-C11-D28
A66-B85-C11-D28
A2-B86-C11-D28
A3-B86-C11-D28
A9-B86-C11-D28
A13-B86-C11-D28
A24-B86-C11-D28
A69-B86-C11-D28
A67-B86-C11-D28
A39-B86-C11-D28
A65-B86-C11-D28
A66-B86-C11-D28
A2-B87-C11-D28
A3-B87-C11-D28
A9-B87-C11-D28
A13-B87-C11-D28
A24-B87-C11-D28
A69-B87-C11-D28
A67-B87-C11-D28
A39-B87-C11-D28
A65-B87-C11-D28
A66-B87-C11-D28
A2-B89-C11-D28
A3-B89-C11-D28
A9-B89-C11-D28
A13-B89-C11-D28
A24-B89-C11-D28
A69-B89-C11-D28
A67-B89-C11-D28
A39-B89-C11-D28
A65-B89-C11-D28
A66-B89-C11-D28
A2-B92-C11-D28
A3-B92-C11-D28
A9-B92-C11-D28
A13-B92-C11-D28
A24-B92-C11-D28
A69-B92-C11-D28
A67-B92-C11-D28
A39-B92-C11-D28
A65-B92-C11-D28
A66-B92-C11-D28
A2-B4-C12-D28
A3-B4-C12-D28
A9-B4-C12-D28
A13-B4-C12-D28
A24-B4-C12-D28
A69-B4-C12-D28
A67-B4-C12-D28
A39-B4-C12-D28
A65-B4-C12-D28
A66-B4-C12-D28
A2-B5-C12-D28
A3-B5-C12-D28
A9-B5-C12-D28
A13-B5-C12-D28
A24-B5-C12-D28
A69-B5-C12-D28
A67-B5-C12-D28
A39-B5-C12-D28
A65-B5-C12-D28
A66-B5-C12-D28
A2-B6-C12-D28
A3-B6-C12-D28
A9-B6-C12-D28
A13-B6-C12-D28
A24-B6-C12-D28
A69-B6-C12-D28
A67-B6-C12-D28
A39-B6-C12-D28
A65-B6-C12-D28
A66-B6-C12-D28
A2-B32-C12-D28

-continued

A3-B32-C12-D28
A9-B32-C12-D28
A13-B32-C12-D28
A24-B32-C12-D28
A69-B32-C12-D28
A67-B32-C12-D28
A39-B32-C12-D28
A65-B32-C12-D28
A66-B32-C12-D28
A2-B39-C12-D28
A3-B39-C12-D28
A9-B39-C12-D28
A13-B39-C12-D28
A24-B39-C12-D28
A69-B39-C12-D28
A67-B39-C12-D28
A39-B39-C12-D28
A65-B39-C12-D28
A66-B39-C12-D28
A2-B45-C12-D28
A3-B45-C12-D28
A9-B45-C12-D28
A13-B45-C12-D28
A24-B45-C12-D28
A69-B45-C12-D28
A67-B45-C12-D28
A39-B45-C12-D28
A65-B45-C12-D28
A66-B45-C12-D28
A2-B53-C12-D28
A3-B53-C12-D28
A9-B53-C12-D28
A13-B53-C12-D28
A24-B53-C12-D28
A69-B53-C12-D28
A67-B53-C12-D28
A39-B53-C12-D28
A65-B53-C12-D28
A66-B53-C12-D28
A2-B79-C12-D28
A3-B79-C12-D28
A9-B79-C12-D28
A13-B79-C12-D28
A24-B79-C12-D28
A69-B79-C12-D28
A67-B79-C12-D28
A39-B79-C12-D28
A65-B79-C12-D28
A66-B79-C12-D28
A2-B80-C12-D28
A3-B80-C12-D28
A9-B80-C12-D28
A13-B80-C12-D28
A24-B80-C12-D28
A69-B80-C12-D28
A67-B80-C12-D28
A39-B80-C12-D28
A65-B80-C12-D28
A66-B80-C12-D28
A2-B85-C12-D28
A3-B85-C12-D28
A9-B85-C12-D28
A13-B85-C12-D28
A24-B85-C12-D28
A69-B85-C12-D28
A67-B85-C12-D28
A39-B85-C12-D28
A65-B85-C12-D28
A66-B85-C12-D28
A2-B86-C12-D28
A3-B86-C12-D28
A9-B86-C12-D28
A13-B86-C12-D28
A24-B86-C12-D28
A69-B86-C12-D28
A67-B86-C12-D28
A39-B86-C12-D28
A65-B86-C12-D28
A66-B86-C12-D28
A2-B87-C12-D28

-continued

A3-B87-C12-D28
A9-B87-C12-D28
A13-B87-C12-D28
A24-B87-C12-D28
A69-B87-C12-D28
A67-B87-C12-D28
A39-B87-C12-D28
A65-B87-C12-D28
A66-B87-C12-D28
A2-B89-C12-D28
A3-B89-C12-D28
A9-B89-C12-D28
A13-B89-C12-D28
A24-B89-C12-D28
A69-B89-C12-D28
A67-B89-C12-D28
A39-B89-C12-D28
A65-B89-C12-D28
A66-B89-C12-D28
A2-B92-C12-D28
A3-B92-C12-D28
A9-B92-C12-D28
A13-B92-C12-D28
A24-B92-C12-D28
A69-B92-C12-D28
A67-B92-C12-D28
A39-B92-C12-D28
A65-B92-C12-D28
A66-B92-C12-D28
A2-B4-C13-D28
A3-B4-C13-D28
A9-B4-C13-D28
A13-B4-C13-D28
A24-B4-C13-D28
A69-B4-C13-D28
A67-B4-C13-D28
A39-B4-C13-D28
A65-B4-C13-D28
A66-B4-C13-D28
A2-B5-C13-D28
A3-B5-C13-D28
A9-B5-C13-D28
A13-B5-C13-D28
A24-B5-C13-D28
A69-B5-C13-D28
A67-B5-C13-D28
A39-B5-C13-D28
A65-B5-C13-D28
A66-B5-C13-D28
A2-B6-C13-D28
A3-B6-C13-D28
A9-B6-C13-D28
A13-B6-C13-D28
A24-B6-C13-D28
A69-B6-C13-D28
A67-B6-C13-D28
A39-B6-C13-D28
A65-B6-C13-D28
A66-B6-C13-D28
A2-B32-C13-D28
A3-B32-C13-D28
A9-B32-C13-D28
A13-B32-C13-D28
A24-B32-C13-D28
A69-B32-C13-D28
A67-B32-C13-D28
A39-B32-C13-D28
A65-B32-C13-D28
A66-B32-C13-D28
A2-B39-C13-D28
A3-B39-C13-D28
A9-B39-C13-D28
A13-B39-C13-D28
A24-B39-C13-D28
A69-B39-C13-D28
A67-B39-C13-D28
A39-B39-C13-D28
A65-B39-C13-D28
A66-B39-C13-D28
A2-B45-C13-D28

-continued

A3-B45-C13-D28
A9-B45-C13-D28
A13-B45-C13-D28
A24-B45-C13-D28
A69-B45-C13-D28
A67-B45-C13-D28
A39-B45-C13-D28
A65-B45-C13-D28
A66-B45-C13-D28
A2-B53-C13-D28
A3-B53-C13-D28
A9-B53-C13-D28
A13-B53-C13-D28
A24-B53-C13-D28
A69-B53-C13-D28
A67-B53-C13-D28
A39-B53-C13-D28
A65-B53-C13-D28
A66-B53-C13-D28
A2-B79-C13-D28
A3-B79-C13-D28
A9-B79-C13-D28
A13-B79-C13-D28
A24-B79-C13-D28
A69-B79-C13-D28
A67-B79-C13-D28
A39-B79-C13-D28
A65-B79-C13-D28
A66-B79-C13-D28
A2-B80-C13-D28
A3-B80-C13-D28
A9-B80-C13-D28
A13-B80-C13-D28
A24-B80-C13-D28
A69-B80-C13-D28
A67-B80-C13-D28
A39-B80-C13-D28
A65-B80-C13-D28
A66-B80-C13-D28
A2-B85-C13-D28
A3-B85-C13-D28
A9-B85-C13-D28
A13-B85-C13-D28
A24-B85-C13-D28
A69-B85-C13-D28
A67-B85-C13-D28
A39-B85-C13-D28
A65-B85-C13-D28
A66-B85-C13-D28
A2-B86-C13-D28
A3-B86-C13-D28
A9-B86-C13-D28
A13-B86-C13-D28
A24-B86-C13-D28
A69-B86-C13-D28
A67-B86-C13-D28
A39-B86-C13-D28
A65-B86-C13-D28
A66-B86-C13-D28
A2-B87-C13-D28
A3-B87-C13-D28
A9-B87-C13-D28
A13-B87-C13-D28
A24-B87-C13-D28
A69-B87-C13-D28
A67-B87-C13-D28
A39-B87-C13-D28
A65-B87-C13-D28
A66-B87-C13-D28
A2-B89-C13-D28
A3-B89-C13-D28
A9-B89-C13-D28
A13-B89-C13-D28
A24-B89-C13-D28
A69-B89-C13-D28
A67-B89-C13-D28
A39-B89-C13-D28
A65-B89-C13-D28
A66-B89-C13-D28
A2-B92-C13-D28

-continued

A3-B92-C13-D28
A9-B92-C13-D28
A13-B92-C13-D28
A24-B92-C13-D28
A69-B92-C13-D28
A67-B92-C13-D28
A39-B92-C13-D28
A65-B92-C13-D28
A66-B92-C13-D28
A2-B4-C1-D29
A3-B4-C1-D29
A9-B4-C1-D29
A13-B4-C1-D29
A24-B4-C1-D29
A69-B4-C1-D29
A67-B4-C1-D29
A39-B4-C1-D29
A65-B4-C1-D29
A66-B4-C1-D29
A2-B5-C1-D29
A3-B5-C1-D29
A9-B5-C1-D29
A13-B5-C1-D29
A24-B5-C1-D29
A69-B5-C1-D29
A67-B5-C1-D29
A39-B5-C1-D29
A65-B5-C1-D29
A66-B5-C1-D29
A2-B6-C1-D29
A3-B6-C1-D29
A9-B6-C1-D29
A13-B6-C1-D29
A24-B6-C1-D29
A69-B6-C1-D29
A67-B6-C1-D29
A39-B6-C1-D29
A65-B6-C1-D29
A66-B6-C1-D29
A2-B32-C1-D29
A3-B32-C1-D29
A9-B32-C1-D29
A13-B32-C1-D29
A24-B32-C1-D29
A69-B32-C1-D29
A67-B32-C1-D29
A39-B32-C1-D29
A65-B32-C1-D29
A66-B32-C1-D29
A2-B39-C1-D29
A3-B39-C1-D29
A9-B39-C1-D29
A13-B39-C1-D29
A24-B39-C1-D29
A69-B39-C1-D29
A67-B39-C1-D29
A39-B39-C1-D29
A65-B39-C1-D29
A66-B39-C1-D29
A2-B45-C1-D29
A3-B45-C1-D29
A9-B45-C1-D29
A13-B45-C1-D29
A24-B45-C1-D29
A69-B45-C1-D29
A67-B45-C1-D29
A39-B45-C1-D29
A65-B45-C1-D29
A66-B45-C1-D29
A2-B53-C1-D29
A3-B53-C1-D29
A9-B53-C1-D29
A13-B53-C1-D29
A24-B53-C1-D29
A69-B53-C1-D29
A67-B53-C1-D29
A39-B53-C1-D29
A65-B53-C1-D29
A66-B53-C1-D29
A2-B79-C1-D29

-continued

A3-B79-C1-D29
A9-B79-C1-D29
A13-B79-C1-D29
A24-B79-C1-D29
A69-B79-C1-D29
A67-B79-C1-D29
A39-B79-C1-D29
A65-B79-C1-D29
A66-B79-C1-D29
A2-B80-C1-D29
A3-B80-C1-D29
A9-B80-C1-D29
A13-B80-C1-D29
A24-B80-C1-D29
A69-B80-C1-D29
A67-B80-C1-D29
A39-B80-C1-D29
A65-B80-C1-D29
A66-B80-C1-D29
A2-B85-C1-D29
A3-B85-C1-D29
A9-B85-C1-D29
A13-B85-C1-D29
A24-B85-C1-D29
A69-B85-C1-D29
A67-B85-C1-D29
A39-B85-C1-D29
A65-B85-C1-D29
A66-B85-C1-D29
A2-B86-C1-D29
A3-B86-C1-D29
A9-B86-C1-D29
A13-B86-C1-D29
A24-B86-C1-D29
A69-B86-C1-D29
A67-B86-C1-D29
A39-B86-C1-D29
A65-B86-C1-D29
A66-B86-C1-D29
A2-B87-C1-D29
A3-B87-C1-D29
A9-B87-C1-D29
A13-B87-C1-D29
A24-B87-C1-D29
A69-B87-C1-D29
A67-B87-C1-D29
A39-B87-C1-D29
A65-B87-C1-D29
A66-B87-C1-D29
A2-B89-C1-D29
A3-B89-C1-D29
A9-B89-C1-D29
A13-B89-C1-D29
A24-B89-C1-D29
A69-B89-C1-D29
A67-B89-C1-D29
A39-B89-C1-D29
A65-B89-C1-D29
A66-B89-C1-D29
A2-B92-C1-D29
A3-B92-C1-D29
A9-B92-C1-D29
A13-B92-C1-D29
A24-B92-C1-D29
A69-B92-C1-D29
A67-B92-C1-D29
A39-B92-C1-D29
A65-B92-C1-D29
A66-B92-C1-D29
A2-B4-C2-D29
A3-B4-C2-D29
A9-B4-C2-D29
A13-B4-C2-D29
A24-B4-C2-D29
A69-B4-C2-D29
A67-B4-C2-D29
A39-B4-C2-D29
A65-B4-C2-D29
A66-B4-C2-D29
A2-B5-C2-D29

-continued
A3-B5-C2-D29
A9-B5-C2-D29
A13-B5-C2-D29
A24-B5-C2-D29
A69-B5-C2-D29
A67-B5-C2-D29
A39-B5-C2-D29
A65-B5-C2-D29
A66-B5-C2-D29
A2-B6-C2-D29
A3-B6-C2-D29
A9-B6-C2-D29
A13-B6-C2-D29
A24-B6-C2-D29
A69-B6-C2-D29
A67-B6-C2-D29
A39-B6-C2-D29
A65-B6-C2-D29
A66-B6-C2-D29
A2-B32-C2-D29
A3-B32-C2-D29
A9-B32-C2-D29
A13-B32-C2-D29
A24-B32-C2-D29
A69-B32-C2-D29
A67-B32-C2-D29
A39-B32-C2-D29
A65-B32-C2-D29
A66-B32-C2-D29
A2-B39-C2-D29
A3-B39-C2-D29
A9-B39-C2-D29
A13-B39-C2-D29
A24-B39-C2-D29
A69-B39-C2-D29
A67-B39-C2-D29
A39-B39-C2-D29
A65-B39-C2-D29
A66-B39-C2-D29
A2-B45-C2-D29
A3-B45-C2-D29
A9-B45-C2-D29
A13-B45-C2-D29
A24-B45-C2-D29
A69-B45-C2-D29
A67-B45-C2-D29
A39-B45-C2-D29
A65-B45-C2-D29
A66-B45-C2-D29
A2-B53-C2-D29
A3-B53-C2-D29
A9-B53-C2-D29
A13-B53-C2-D29
A24-B53-C2-D29
A69-B53-C2-D29
A67-B53-C2-D29
A39-B53-C2-D29
A65-B53-C2-D29
A66-B53-C2-D29
A2-B79-C2-D29
A3-B79-C2-D29
A9-B79-C2-D29
A13-B79-C2-D29
A24-B79-C2-D29
A69-B79-C2-D29
A67-B79-C2-D29
A39-B79-C2-D29
A65-B79-C2-D29
A66-B79-C2-D29
A2-B80-C2-D29
A3-B80-C2-D29
A9-B80-C2-D29
A13-B80-C2-D29
A24-B80-C2-D29
A69-B80-C2-D29
A67-B80-C2-D29
A39-B80-C2-D29
A65-B80-C2-D29
A66-B80-C2-D29
A2-B85-C2-D29

-continued
A3-B85-C2-D29
A9-B85-C2-D29
A13-B85-C2-D29
A24-B85-C2-D29
A69-B85-C2-D29
A67-B85-C2-D29
A39-B85-C2-D29
A65-B85-C2-D29
A66-B85-C2-D29
A2-B86-C2-D29
A3-B86-C2-D29
A9-B86-C2-D29
A13-B86-C2-D29
A24-B86-C2-D29
A69-B86-C2-D29
A67-B86-C2-D29
A39-B86-C2-D29
A65-B86-C2-D29
A66-B86-C2-D29
A2-B87-C2-D29
A3-B87-C2-D29
A9-B87-C2-D29
A13-B87-C2-D29
A24-B87-C2-D29
A69-B87-C2-D29
A67-B87-C2-D29
A39-B87-C2-D29
A65-B87-C2-D29
A66-B87-C2-D29
A2-B89-C2-D29
A3-B89-C2-D29
A9-B89-C2-D29
A13-B89-C2-D29
A24-B89-C2-D29
A69-B89-C2-D29
A67-B89-C2-D29
A39-B89-C2-D29
A65-B89-C2-D29
A66-B89-C2-D29
A2-B92-C2-D29
A3-B92-C2-D29
A9-B92-C2-D29
A13-B92-C2-D29
A24-B92-C2-D29
A69-B92-C2-D29
A67-B92-C2-D29
A39-B92-C2-D29
A65-B92-C2-D29
A66-B92-C2-D29
A2-B4-C3-D29
A3-B4-C3-D29
A9-B4-C3-D29
A13-B4-C3-D29
A24-B4-C3-D29
A69-B4-C3-D29
A67-B4-C3-D29
A39-B4-C3-D29
A65-B4-C3-D29
A66-B4-C3-D29
A2-B5-C3-D29
A3-B5-C3-D29
A9-B5-C3-D29
A13-B5-C3-D29
A24-B5-C3-D29
A69-B5-C3-D29
A67-B5-C3-D29
A39-B5-C3-D29
A65-B5-C3-D29
A66-B5-C3-D29
A2-B6-C3-D29
A3-B6-C3-D29
A9-B6-C3-D29
A13-B6-C3-D29
A24-B6-C3-D29
A69-B6-C3-D29
A67-B6-C3-D29
A39-B6-C3-D29
A65-B6-C3-D29
A66-B6-C3-D29
A2-B32-C3-D29

-continued

A3-B32-C3-D29
A9-B32-C3-D29
A13-B32-C3-D29
A24-B32-C3-D29
A69-B32-C3-D29
A67-B32-C3-D29
A39-B32-C3-D29
A65-B32-C3-D29
A66-B32-C3-D29
A2-B39-C3-D29
A3-B39-C3-D29
A9-B39-C3-D29
A13-B39-C3-D29
A24-B39-C3-D29
A69-B39-C3-D29
A67-B39-C3-D29
A39-B39-C3-D29
A65-B39-C3-D29
A66-B39-C3-D29
A2-B45-C3-D29
A3-B45-C3-D29
A9-B45-C3-D29
A13-B45-C3-D29
A24-B45-C3-D29
A69-B45-C3-D29
A67-B45-C3-D29
A39-B45-C3-D29
A65-B45-C3-D29
A66-B45-C3-D29
A2-B53-C3-D29
A3-B53-C3-D29
A9-B53-C3-D29
A13-B53-C3-D29
A24-B53-C3-D29
A69-B53-C3-D29
A67-B53-C3-D29
A39-B53-C3-D29
A65-B53-C3-D29
A66-B53-C3-D29
A2-B79-C3-D29
A3-B79-C3-D29
A9-B79-C3-D29
A13-B79-C3-D29
A24-B79-C3-D29
A69-B79-C3-D29
A67-B79-C3-D29
A39-B79-C3-D29
A65-B79-C3-D29
A66-B79-C3-D29
A2-B80-C3-D29
A3-B80-C3-D29
A9-B80-C3-D29
A13-B80-C3-D29
A24-B80-C3-D29
A69-B80-C3-D29
A67-B80-C3-D29
A39-B80-C3-D29
A65-B80-C3-D29
A66-B80-C3-D29
A2-B85-C3-D29
A3-B85-C3-D29
A9-B85-C3-D29
A13-B85-C3-D29
A24-B85-C3-D29
A69-B85-C3-D29
A67-B85-C3-D29
A39-B85-C3-D29
A65-B85-C3-D29
A66-B85-C3-D29
A2-B86-C3-D29
A3-B86-C3-D29
A9-B86-C3-D29
A13-B86-C3-D29
A24-B86-C3-D29
A69-B86-C3-D29
A67-B86-C3-D29
A39-B86-C3-D29
A65-B86-C3-D29
A66-B86-C3-D29
A2-B87-C3-D29

-continued

A3-B87-C3-D29
A9-B87-C3-D29
A13-B87-C3-D29
A24-B87-C3-D29
A69-B87-C3-D29
A67-B87-C3-D29
A39-B87-C3-D29
A65-B87-C3-D29
A66-B87-C3-D29
A2-B89-C3-D29
A3-B89-C3-D29
A9-B89-C3-D29
A13-B89-C3-D29
A24-B89-C3-D29
A69-B89-C3-D29
A67-B89-C3-D29
A39-B89-C3-D29
A65-B89-C3-D29
A66-B89-C3-D29
A2-B92-C3-D29
A3-B92-C3-D29
A9-B92-C3-D29
A13-B92-C3-D29
A24-B92-C3-D29
A69-B92-C3-D29
A67-B92-C3-D29
A39-B92-C3-D29
A65-B92-C3-D29
A66-B92-C3-D29
A2-B4-C4-D29
A3-B4-C4-D29
A9-B4-C4-D29
A13-B4-C4-D29
A24-B4-C4-D29
A69-B4-C4-D29
A67-B4-C4-D29
A39-B4-C4-D29
A65-B4-C4-D29
A66-B4-C4-D29
A2-B5-C4-D29
A3-B5-C4-D29
A9-B5-C4-D29
A13-B5-C4-D29
A24-B5-C4-D29
A69-B5-C4-D29
A67-B5-C4-D29
A39-B5-C4-D29
A65-B5-C4-D29
A66-B5-C4-D29
A2-B6-C4-D29
A3-B6-C4-D29
A9-B6-C4-D29
A13-B6-C4-D29
A24-B6-C4-D29
A69-B6-C4-D29
A67-B6-C4-D29
A39-B6-C4-D29
A65-B6-C4-D29
A66-B6-C4-D29
A2-B32-C4-D29
A3-B32-C4-D29
A9-B32-C4-D29
A13-B32-C4-D29
A24-B32-C4-D29
A69-B32-C4-D29
A67-B32-C4-D29
A39-B32-C4-D29
A65-B32-C4-D29
A66-B32-C4-D29
A2-B39-C4-D29
A3-B39-C4-D29
A9-B39-C4-D29
A13-B39-C4-D29
A24-B39-C4-D29
A69-B39-C4-D29
A67-B39-C4-D29
A39-B39-C4-D29
A65-B39-C4-D29
A66-B39-C4-D29
A2-B45-C4-D29

-continued

A3-B45-C4-D29
A9-B45-C4-D29
A13-B45-C4-D29
A24-B45-C4-D29
A69-B45-C4-D29
A67-B45-C4-D29
A39-B45-C4-D29
A65-B45-C4-D29
A66-B45-C4-D29
A2-B53-C4-D29
A3-B53-C4-D29
A9-B53-C4-D29
A13-B53-C4-D29
A24-B53-C4-D29
A69-B53-C4-D29
A67-B53-C4-D29
A39-B53-C4-D29
A65-B53-C4-D29
A66-B53-C4-D29
A2-B79-C4-D29
A3-B79-C4-D29
A9-B79-C4-D29
A13-B79-C4-D29
A24-B79-C4-D29
A69-B79-C4-D29
A67-B79-C4-D29
A39-B79-C4-D29
A65-B79-C4-D29
A66-B79-C4-D29
A2-B80-C4-D29
A3-B80-C4-D29
A9-B80-C4-D29
A13-B80-C4-D29
A24-B80-C4-D29
A69-B80-C4-D29
A67-B80-C4-D29
A39-B80-C4-D29
A65-B80-C4-D29
A66-B80-C4-D29
A2-B85-C4-D29
A3-B85-C4-D29
A9-B85-C4-D29
A13-B85-C4-D29
A24-B85-C4-D29
A69-B85-C4-D29
A67-B85-C4-D29
A39-B85-C4-D29
A65-B85-C4-D29
A66-B85-C4-D29
A2-B86-C4-D29
A3-B86-C4-D29
A9-B86-C4-D29
A13-B86-C4-D29
A24-B86-C4-D29
A69-B86-C4-D29
A67-B86-C4-D29
A39-B86-C4-D29
A65-B86-C4-D29
A66-B86-C4-D29
A2-B87-C4-D29
A3-B87-C4-D29
A9-B87-C4-D29
A13-B87-C4-D29
A24-B87-C4-D29
A69-B87-C4-D29
A67-B87-C4-D29
A39-B87-C4-D29
A65-B87-C4-D29
A66-B87-C4-D29
A2-B89-C4-D29
A3-B89-C4-D29
A9-B89-C4-D29
A13-B89-C4-D29
A24-B89-C4-D29
A69-B89-C4-D29
A67-B89-C4-D29
A39-B89-C4-D29
A65-B89-C4-D29
A66-B89-C4-D29
A2-B92-C4-D29

-continued

A3-B92-C4-D29
A9-B92-C4-D29
A13-B92-C4-D29
A24-B92-C4-D29
A69-B92-C4-D29
A67-B92-C4-D29
A39-B92-C4-D29
A65-B92-C4-D29
A66-B92-C4-D29
A2-B4-C5-D29
A3-B4-C5-D29
A9-B4-C5-D29
A13-B4-C5-D29
A24-B4-C5-D29
A69-B4-C5-D29
A67-B4-C5-D29
A39-B4-C5-D29
A65-B4-C5-D29
A66-B4-C5-D29
A2-B5-C5-D29
A3-B5-C5-D29
A9-B5-C5-D29
A13-B5-C5-D29
A24-B5-C5-D29
A69-B5-C5-D29
A67-B5-C5-D29
A39-B5-C5-D29
A65-B5-C5-D29
A66-B5-C5-D29
A2-B6-C5-D29
A3-B6-C5-D29
A9-B6-C5-D29
A13-B6-C5-D29
A24-B6-C5-D29
A69-B6-C5-D29
A67-B6-C5-D29
A39-B6-C5-D29
A65-B6-C5-D29
A66-B6-C5-D29
A2-B32-C5-D29
A3-B32-C5-D29
A9-B32-C5-D29
A13-B32-C5-D29
A24-B32-C5-D29
A69-B32-C5-D29
A67-B32-C5-D29
A39-B32-C5-D29
A65-B32-C5-D29
A66-B32-C5-D29
A2-B39-C5-D29
A3-B39-C5-D29
A9-B39-C5-D29
A13-B39-C5-D29
A24-B39-C5-D29
A69-B39-C5-D29
A67-B39-C5-D29
A39-B39-C5-D29
A65-B39-C5-D29
A66-B39-C5-D29
A2-B45-C5-D29
A3-B45-C5-D29
A9-B45-C5-D29
A13-B45-C5-D29
A24-B45-C5-D29
A69-B45-C5-D29
A67-B45-C5-D29
A39-B45-C5-D29
A65-B45-C5-D29
A66-B45-C5-D29
A2-B53-C5-D29
A3-B53-C5-D29
A9-B53-C5-D29
A13-B53-C5-D29
A24-B53-C5-D29
A69-B53-C5-D29
A67-B53-C5-D29
A39-B53-C5-D29
A65-B53-C5-D29
A66-B53-C5-D29
A2-B79-C5-D29

-continued
A3-B79-C5-D29
A9-B79-C5-D29
A13-B79-C5-D29
A24-B79-C5-D29
A69-B79-C5-D29
A67-B79-C5-D29
A39-B79-C5-D29
A65-B79-C5-D29
A66-B79-C5-D29
A2-B80-C5-D29
A3-B80-C5-D29
A9-B80-C5-D29
A13-B80-C5-D29
A24-B80-C5-D29
A69-B80-C5-D29
A67-B80-C5-D29
A39-B80-C5-D29
A65-B80-C5-D29
A66-B80-C5-D29
A2-B85-C5-D29
A3-B85-C5-D29
A9-B85-C5-D29
A13-B85-C5-D29
A24-B85-C5-D29
A69-B85-C5-D29
A67-B85-C5-D29
A39-B85-C5-D29
A65-B85-C5-D29
A66-B85-C5-D29
A2-B86-C5-D29
A3-B86-C5-D29
A9-B86-C5-D29
A13-B86-C5-D29
A24-B86-C5-D29
A69-B86-C5-D29
A67-B86-C5-D29
A39-B86-C5-D29
A65-B86-C5-D29
A66-B86-C5-D29
A2-B87-C5-D29
A3-B87-C5-D29
A9-B87-C5-D29
A13-B87-C5-D29
A24-B87-C5-D29
A69-B87-C5-D29
A67-B87-C5-D29
A39-B87-C5-D29
A65-B87-C5-D29
A66-B87-C5-D29
A2-B89-C5-D29
A3-B89-C5-D29
A9-B89-C5-D29
A13-B89-C5-D29
A24-B89-C5-D29
A69-B89-C5-D29
A67-B89-C5-D29
A39-B89-C5-D29
A65-B89-C5-D29
A66-B89-C5-D29
A2-B92-C5-D29
A3-B92-C5-D29
A9-B92-C5-D29
A13-B92-C5-D29
A24-B92-C5-D29
A69-B92-C5-D29
A67-B92-C5-D29
A39-B92-C5-D29
A65-B92-C5-D29
A66-B92-C5-D29
A2-B4-C6-D29
A3-B4-C6-D29
A9-B4-C6-D29
A13-B4-C6-D29
A24-B4-C6-D29
A69-B4-C6-D29
A67-B4-C6-D29
A39-B4-C6-D29
A65-B4-C6-D29
A66-B4-C6-D29
A2-B5-C6-D29

-continued
A3-B5-C6-D29
A9-B5-C6-D29
A13-B5-C6-D29
A24-B5-C6-D29
A69-B5-C6-D29
A67-B5-C6-D29
A39-B5-C6-D29
A65-B5-C6-D29
A66-B5-C6-D29
A2-B6-C6-D29
A3-B6-C6-D29
A9-B6-C6-D29
A13-B6-C6-D29
A24-B6-C6-D29
A69-B6-C6-D29
A67-B6-C6-D29
A39-B6-C6-D29
A65-B6-C6-D29
A66-B6-C6-D29
A2-B32-C6-D29
A3-B32-C6-D29
A9-B32-C6-D29
A13-B32-C6-D29
A24-B32-C6-D29
A69-B32-C6-D29
A67-B32-C6-D29
A39-B32-C6-D29
A65-B32-C6-D29
A66-B32-C6-D29
A2-B39-C6-D29
A3-B39-C6-D29
A9-B39-C6-D29
A13-B39-C6-D29
A24-B39-C6-D29
A69-B39-C6-D29
A67-B39-C6-D29
A39-B39-C6-D29
A65-B39-C6-D29
A66-B39-C6-D29
A2-B45-C6-D29
A3-B45-C6-D29
A9-B45-C6-D29
A13-B45-C6-D29
A24-B45-C6-D29
A69-B45-C6-D29
A67-B45-C6-D29
A39-B45-C6-D29
A65-B45-C6-D29
A66-B45-C6-D29
A2-B53-C6-D29
A3-B53-C6-D29
A9-B53-C6-D29
A13-B53-C6-D29
A24-B53-C6-D29
A69-B53-C6-D29
A67-B53-C6-D29
A39-B53-C6-D29
A65-B53-C6-D29
A66-B53-C6-D29
A2-B79-C6-D29
A3-B79-C6-D29
A9-B79-C6-D29
A13-B79-C6-D29
A24-B79-C6-D29
A69-B79-C6-D29
A67-B79-C6-D29
A39-B79-C6-D29
A65-B79-C6-D29
A66-B79-C6-D29
A2-B80-C6-D29
A3-B80-C6-D29
A9-B80-C6-D29
A13-B80-C6-D29
A24-B80-C6-D29
A69-B80-C6-D29
A67-B80-C6-D29
A39-B80-C6-D29
A65-B80-C6-D29
A66-B80-C6-D29
A2-B85-C6-D29

-continued
A3-B85-C6-D29
A9-B85-C6-D29
A13-B85-C6-D29
A24-B85-C6-D29
A69-B85-C6-D29
A67-B85-C6-D29
A39-B85-C6-D29
A65-B85-C6-D29
A66-B85-C6-D29
A2-B86-C6-D29
A3-B86-C6-D29
A9-B86-C6-D29
A13-B86-C6-D29
A24-B86-C6-D29
A69-B86-C6-D29
A67-B86-C6-D29
A39-B86-C6-D29
A65-B86-C6-D29
A66-B86-C6-D29
A2-B87-C6-D29
A3-B87-C6-D29
A9-B87-C6-D29
A13-B87-C6-D29
A24-B87-C6-D29
A69-B87-C6-D29
A67-B87-C6-D29
A39-B87-C6-D29
A65-B87-C6-D29
A66-B87-C6-D29
A2-B89-C6-D29
A3-B89-C6-D29
A9-B89-C6-D29
A13-B89-C6-D29
A24-B89-C6-D29
A69-B89-C6-D29
A67-B89-C6-D29
A39-B89-C6-D29
A65-B89-C6-D29
A66-B89-C6-D29
A2-B92-C6-D29
A3-B92-C6-D29
A9-B92-C6-D29
A13-B92-C6-D29
A24-B92-C6-D29
A69-B92-C6-D29
A67-B92-C6-D29
A39-B92-C6-D29
A65-B92-C6-D29
A66-B92-C6-D29
A2-B4-C7-D29
A3-B4-C7-D29
A9-B4-C7-D29
A13-B4-C7-D29
A24-B4-C7-D29
A69-B4-C7-D29
A67-B4-C7-D29
A39-B4-C7-D29
A65-B4-C7-D29
A66-B4-C7-D29
A2-B5-C7-D29
A3-B5-C7-D29
A9-B5-C7-D29
A13-B5-C7-D29
A24-B5-C7-D29
A69-B5-C7-D29
A67-B5-C7-D29
A39-B5-C7-D29
A65-B5-C7-D29
A66-B5-C7-D29
A2-B6-C7-D29
A3-B6-C7-D29
A9-B6-C7-D29
A13-B6-C7-D29
A24-B6-C7-D29
A69-B6-C7-D29
A67-B6-C7-D29
A39-B6-C7-D29
A65-B6-C7-D29
A66-B6-C7-D29
A2-B32-C7-D29

-continued
A3-B32-C7-D29
A9-B32-C7-D29
A13-B32-C7-D29
A24-B32-C7-D29
A69-B32-C7-D29
A67-B32-C7-D29
A39-B32-C7-D29
A65-B32-C7-D29
A66-B32-C7-D29
A2-B39-C7-D29
A3-B39-C7-D29
A9-B39-C7-D29
A13-B39-C7-D29
A24-B39-C7-D29
A69-B39-C7-D29
A67-B39-C7-D29
A39-B39-C7-D29
A65-B39-C7-D29
A66-B39-C7-D29
A2-B45-C7-D29
A3-B45-C7-D29
A9-B45-C7-D29
A13-B45-C7-D29
A24-B45-C7-D29
A69-B45-C7-D29
A67-B45-C7-D29
A39-B45-C7-D29
A65-B45-C7-D29
A66-B45-C7-D29
A2-B53-C7-D29
A3-B53-C7-D29
A9-B53-C7-D29
A13-B53-C7-D29
A24-B53-C7-D29
A69-B53-C7-D29
A67-B53-C7-D29
A39-B53-C7-D29
A65-B53-C7-D29
A66-B53-C7-D29
A2-B79-C7-D29
A3-B79-C7-D29
A9-B79-C7-D29
A13-B79-C7-D29
A24-B79-C7-D29
A69-B79-C7-D29
A67-B79-C7-D29
A39-B79-C7-D29
A65-B79-C7-D29
A66-B79-C7-D29
A2-B80-C7-D29
A3-B80-C7-D29
A9-B80-C7-D29
A13-B80-C7-D29
A24-B80-C7-D29
A69-B80-C7-D29
A67-B80-C7-D29
A39-B80-C7-D29
A65-B80-C7-D29
A66-B80-C7-D29
A2-B85-C7-D29
A3-B85-C7-D29
A9-B85-C7-D29
A13-B85-C7-D29
A24-B85-C7-D29
A69-B85-C7-D29
A67-B85-C7-D29
A39-B85-C7-D29
A65-B85-C7-D29
A66-B85-C7-D29
A2-B86-C7-D29
A3-B86-C7-D29
A9-B86-C7-D29
A13-B86-C7-D29
A24-B86-C7-D29
A69-B86-C7-D29
A67-B86-C7-D29
A39-B86-C7-D29
A65-B86-C7-D29
A66-B86-C7-D29
A2-B87-C7-D29

-continued
A3-B87-C7-D29
A9-B87-C7-D29
A13-B87-C7-D29
A24-B87-C7-D29
A69-B87-C7-D29
A67-B87-C7-D29
A39-B87-C7-D29
A65-B87-C7-D29
A66-B87-C7-D29
A2-B89-C7-D29
A3-B89-C7-D29
A9-B89-C7-D29
A13-B89-C7-D29
A24-B89-C7-D29
A69-B89-C7-D29
A67-B89-C7-D29
A39-B89-C7-D29
A65-B89-C7-D29
A66-B89-C7-D29
A2-B92-C7-D29
A3-B92-C7-D29
A9-B92-C7-D29
A13-B92-C7-D29
A24-B92-C7-D29
A69-B92-C7-D29
A67-B92-C7-D29
A39-B92-C7-D29
A65-B92-C7-D29
A66-B92-C7-D29
A2-B4-C8-D29
A3-B4-C8-D29
A9-B4-C8-D29
A13-B4-C8-D29
A24-B4-C8-D29
A69-B4-C8-D29
A67-B4-C8-D29
A39-B4-C8-D29
A65-B4-C8-D29
A66-B4-C8-D29
A2-B5-C8-D29
A3-B5-C8-D29
A9-B5-C8-D29
A13-B5-C8-D29
A24-B5-C8-D29
A69-B5-C8-D29
A67-B5-C8-D29
A39-B5-C8-D29
A65-B5-C8-D29
A66-B5-C8-D29
A2-B6-C8-D29
A3-B6-C8-D29
A9-B6-C8-D29
A13-B6-C8-D29
A24-B6-C8-D29
A69-B6-C8-D29
A67-B6-C8-D29
A39-B6-C8-D29
A65-B6-C8-D29
A66-B6-C8-D29
A2-B32-C8-D29
A3-B32-C8-D29
A9-B32-C8-D29
A13-B32-C8-D29
A24-B32-C8-D29
A69-B32-C8-D29
A67-B32-C8-D29
A39-B32-C8-D29
A65-B32-C8-D29
A66-B32-C8-D29
A2-B39-C8-D29
A3-B39-C8-D29
A9-B39-C8-D29
A13-B39-C8-D29
A24-B39-C8-D29
A69-B39-C8-D29
A67-B39-C8-D29
A39-B39-C8-D29
A65-B39-C8-D29
A66-B39-C8-D29
A2-B45-C8-D29

-continued
A3-B45-C8-D29
A9-B45-C8-D29
A13-B45-C8-D29
A24-B45-C8-D29
A69-B45-C8-D29
A67-B45-C8-D29
A39-B45-C8-D29
A65-B45-C8-D29
A66-B45-C8-D29
A2-B53-C8-D29
A3-B53-C8-D29
A9-B53-C8-D29
A13-B53-C8-D29
A24-B53-C8-D29
A69-B53-C8-D29
A67-B53-C8-D29
A39-B53-C8-D29
A65-B53-C8-D29
A66-B53-C8-D29
A2-B79-C8-D29
A3-B79-C8-D29
A9-B79-C8-D29
A13-B79-C8-D29
A24-B79-C8-D29
A69-B79-C8-D29
A67-B79-C8-D29
A39-B79-C8-D29
A65-B79-C8-D29
A66-B79-C8-D29
A2-B80-C8-D29
A3-B80-C8-D29
A9-B80-C8-D29
A13-B80-C8-D29
A24-B80-C8-D29
A69-B80-C8-D29
A67-B80-C8-D29
A39-B80-C8-D29
A65-B80-C8-D29
A66-B80-C8-D29
A2-B85-C8-D29
A3-B85-C8-D29
A9-B85-C8-D29
A13-B85-C8-D29
A24-B85-C8-D29
A69-B85-C8-D29
A67-B85-C8-D29
A39-B85-C8-D29
A65-B85-C8-D29
A66-B85-C8-D29
A2-B86-C8-D29
A3-B86-C8-D29
A9-B86-C8-D29
A13-B86-C8-D29
A24-B86-C8-D29
A69-B86-C8-D29
A67-B86-C8-D29
A39-B86-C8-D29
A65-B86-C8-D29
A66-B86-C8-D29
A2-B87-C8-D29
A3-B87-C8-D29
A9-B87-C8-D29
A13-B87-C8-D29
A24-B87-C8-D29
A69-B87-C8-D29
A67-B87-C8-D29
A39-B87-C8-D29
A65-B87-C8-D29
A66-B87-C8-D29
A2-B89-C8-D29
A3-B89-C8-D29
A9-B89-C8-D29
A13-B89-C8-D29
A24-B89-C8-D29
A69-B89-C8-D29
A67-B89-C8-D29
A39-B89-C8-D29
A65-B89-C8-D29
A66-B89-C8-D29
A2-B92-C8-D29

-continued
A3-B92-C8-D29
A9-B92-C8-D29
A13-B92-C8-D29
A24-B92-C8-D29
A69-B92-C8-D29
A67-B92-C8-D29
A39-B92-C8-D29
A65-B92-C8-D29
A66-B92-C8-D29
A2-B4-C9-D29
A3-B4-C9-D29
A9-B4-C9-D29
A13-B4-C9-D29
A24-B4-C9-D29
A69-B4-C9-D29
A67-B4-C9-D29
A39-B4-C9-D29
A65-B4-C9-D29
A66-B4-C9-D29
A2-B5-C9-D29
A3-B5-C9-D29
A9-B5-C9-D29
A13-B5-C9-D29
A24-B5-C9-D29
A69-B5-C9-D29
A67-B5-C9-D29
A39-B5-C9-D29
A65-B5-C9-D29
A66-B5-C9-D29
A2-B6-C9-D29
A3-B6-C9-D29
A9-B6-C9-D29
A13-B6-C9-D29
A24-B6-C9-D29
A69-B6-C9-D29
A67-B6-C9-D29
A39-B6-C9-D29
A65-B6-C9-D29
A66-B6-C9-D29
A2-B32-C9-D29
A3-B32-C9-D29
A9-B32-C9-D29
A13-B32-C9-D29
A24-B32-C9-D29
A69-B32-C9-D29
A67-B32-C9-D29
A39-B32-C9-D29
A65-B32-C9-D29
A66-B32-C9-D29
A2-B39-C9-D29
A3-B39-C9-D29
A9-B39-C9-D29
A13-B39-C9-D29
A24-B39-C9-D29
A69-B39-C9-D29
A67-B39-C9-D29
A39-B39-C9-D29
A65-B39-C9-D29
A66-B39-C9-D29
A2-B45-C9-D29
A3-B45-C9-D29
A9-B45-C9-D29
A13-B45-C9-D29
A24-B45-C9-D29
A69-B45-C9-D29
A67-B45-C9-D29
A39-B45-C9-D29
A65-B45-C9-D29
A66-B45-C9-D29
A2-B53-C9-D29
A3-B53-C9-D29
A9-B53-C9-D29
A13-B53-C9-D29
A24-B53-C9-D29
A69-B53-C9-D29
A67-B53-C9-D29
A39-B53-C9-D29
A65-B53-C9-D29
A66-B53-C9-D29
A2-B79-C9-D29

-continued
A3-B79-C9-D29
A9-B79-C9-D29
A13-B79-C9-D29
A24-B79-C9-D29
A69-B79-C9-D29
A67-B79-C9-D29
A39-B79-C9-D29
A65-B79-C9-D29
A66-B79-C9-D29
A2-B80-C9-D29
A3-B80-C9-D29
A9-B80-C9-D29
A13-B80-C9-D29
A24-B80-C9-D29
A69-B80-C9-D29
A67-B80-C9-D29
A39-B80-C9-D29
A65-B80-C9-D29
A66-B80-C9-D29
A2-B85-C9-D29
A3-B85-C9-D29
A9-B85-C9-D29
A13-B85-C9-D29
A24-B85-C9-D29
A69-B85-C9-D29
A67-B85-C9-D29
A39-B85-C9-D29
A65-B85-C9-D29
A66-B85-C9-D29
A2-B86-C9-D29
A3-B86-C9-D29
A9-B86-C9-D29
A13-B86-C9-D29
A24-B86-C9-D29
A69-B86-C9-D29
A67-B86-C9-D29
A39-B86-C9-D29
A65-B86-C9-D29
A66-B86-C9-D29
A2-B87-C9-D29
A3-B87-C9-D29
A9-B87-C9-D29
A13-B87-C9-D29
A24-B87-C9-D29
A69-B87-C9-D29
A67-B87-C9-D29
A39-B87-C9-D29
A65-B87-C9-D29
A66-B87-C9-D29
A2-B89-C9-D29
A3-B89-C9-D29
A9-B89-C9-D29
A13-B89-C9-D29
A24-B89-C9-D29
A69-B89-C9-D29
A67-B89-C9-D29
A39-B89-C9-D29
A65-B89-C9-D29
A66-B89-C9-D29
A2-B92-C9-D29
A3-B92-C9-D29
A9-B92-C9-D29
A13-B92-C9-D29
A24-B92-C9-D29
A69-B92-C9-D29
A67-B92-C9-D29
A39-B92-C9-D29
A65-B92-C9-D29
A66-B92-C9-D29
A2-B4-C10-D29
A3-B4-C10-D29
A9-B4-C10-D29
A13-B4-C10-D29
A24-B4-C10-D29
A69-B4-C10-D29
A67-B4-C10-D29
A39-B4-C10-D29
A65-B4-C10-D29
A66-B4-C10-D29
A2-B5-C10-D29

-continued

A3-B5-C10-D29
A9-B5-C10-D29
A13-B5-C10-D29
A24-B5-C10-D29
A69-B5-C10-D29
A67-B5-C10-D29
A39-B5-C10-D29
A65-B5-C10-D29
A66-B5-C10-D29
A2-B6-C10-D29
A3-B6-C10-D29
A9-B6-C10-D29
A13-B6-C10-D29
A24-B6-C10-D29
A69-B6-C10-D29
A67-B6-C10-D29
A39-B6-C10-D29
A65-B6-C10-D29
A66-B6-C10-D29
A2-B32-C10-D29
A3-B32-C10-D29
A9-B32-C10-D29
A13-B32-C10-D29
A24-B32-C10-D29
A69-B32-C10-D29
A67-B32-C10-D29
A39-B32-C10-D29
A65-B32-C10-D29
A66-B32-C10-D29
A2-B39-C10-D29
A3-B39-C10-D29
A9-B39-C10-D29
A13-B39-C10-D29
A24-B39-C10-D29
A69-B39-C10-D29
A67-B39-C10-D29
A39-B39-C10-D29
A65-B39-C10-D29
A66-B39-C10-D29
A2-B45-C10-D29
A3-B45-C10-D29
A9-B45-C10-D29
A13-B45-C10-D29
A24-B45-C10-D29
A69-B45-C10-D29
A67-B45-C10-D29
A39-B45-C10-D29
A65-B45-C10-D29
A66-B45-C10-D29
A2-B53-C10-D29
A3-B53-C10-D29
A9-B53-C10-D29
A13-B53-C10-D29
A24-B53-C10-D29
A69-B53-C10-D29
A67-B53-C10-D29
A39-B53-C10-D29
A65-B53-C10-D29
A66-B53-C10-D29
A2-B79-C10-D29
A3-B79-C10-D29
A9-B79-C10-D29
A13-B79-C10-D29
A24-B79-C10-D29
A69-B79-C10-D29
A67-B79-C10-D29
A39-B79-C10-D29
A65-B79-C10-D29
A66-B79-C10-D29
A2-B80-C10-D29
A3-B80-C10-D29
A9-B80-C10-D29
A13-B80-C10-D29
A24-B80-C10-D29
A69-B80-C10-D29
A67-B80-C10-D29
A39-B80-C10-D29
A65-B80-C10-D29
A66-B80-C10-D29
A2-B85-C10-D29

-continued

A3-B85-C10-D29
A9-B85-C10-D29
A13-B85-C10-D29
A24-B85-C10-D29
A69-B85-C10-D29
A67-B85-C10-D29
A39-B85-C10-D29
A65-B85-C10-D29
A66-B85-C10-D29
A2-B86-C10-D29
A3-B86-C10-D29
A9-B86-C10-D29
A13-B86-C10-D29
A24-B86-C10-D29
A69-B86-C10-D29
A67-B86-C10-D29
A39-B86-C10-D29
A65-B86-C10-D29
A66-B86-C10-D29
A2-B87-C10-D29
A3-B87-C10-D29
A9-B87-C10-D29
A13-B87-C10-D29
A24-B87-C10-D29
A69-B87-C10-D29
A67-B87-C10-D29
A39-B87-C10-D29
A65-B87-C10-D29
A66-B87-C10-D29
A2-B89-C10-D29
A3-B89-C10-D29
A9-B89-C10-D29
A13-B89-C10-D29
A24-B89-C10-D29
A69-B89-C10-D29
A67-B89-C10-D29
A39-B89-C10-D29
A65-B89-C10-D29
A66-B89-C10-D29
A2-B92-C10-D29
A3-B92-C10-D29
A9-B92-C10-D29
A13-B92-C10-D29
A24-B92-C10-D29
A69-B92-C10-D29
A67-B92-C10-D29
A39-B92-C10-D29
A65-B92-C10-D29
A66-B92-C10-D29
A2-B4-C11-D29
A3-B4-C11-D29
A9-B4-C11-D29
A13-B4-C11-D29
A24-B4-C11-D29
A69-B4-C11-D29
A67-B4-C11-D29
A39-B4-C11-D29
A65-B4-C11-D29
A66-B4-C11-D29
A2-B5-C11-D29
A3-B5-C11-D29
A9-B5-C11-D29
A13-B5-C11-D29
A24-B5-C11-D29
A69-B5-C11-D29
A67-B5-C11-D29
A39-B5-C11-D29
A65-B5-C11-D29
A66-B5-C11-D29
A2-B6-C11-D29
A3-B6-C11-D29
A9-B6-C11-D29
A13-B6-C11-D29
A24-B6-C11-D29
A69-B6-C11-D29
A67-B6-C11-D29
A39-B6-C11-D29
A65-B6-C11-D29
A66-B6-C11-D29
A2-B32-C11-D29

-continued

A3-B32-C11-D29
A9-B32-C11-D29
A13-B32-C11-D29
A24-B32-C11-D29
A69-B32-C11-D29
A67-B32-C11-D29
A39-B32-C11-D29
A65-B32-C11-D29
A66-B32-C11-D29
A2-B39-C11-D29
A3-B39-C11-D29
A9-B39-C11-D29
A13-B39-C11-D29
A24-B39-C11-D29
A69-B39-C11-D29
A67-B39-C11-D29
A39-B39-C11-D29
A65-B39-C11-D29
A66-B39-C11-D29
A2-B45-C11-D29
A3-B45-C11-D29
A9-B45-C11-D29
A13-B45-C11-D29
A24-B45-C11-D29
A69-B45-C11-D29
A67-B45-C11-D29
A39-B45-C11-D29
A65-B45-C11-D29
A66-B45-C11-D29
A2-B53-C11-D29
A3-B53-C11-D29
A9-B53-C11-D29
A13-B53-C11-D29
A24-B53-C11-D29
A69-B53-C11-D29
A67-B53-C11-D29
A39-B53-C11-D29
A65-B53-C11-D29
A66-B53-C11-D29
A2-B79-C11-D29
A3-B79-C11-D29
A9-B79-C11-D29
A13-B79-C11-D29
A24-B79-C11-D29
A69-B79-C11-D29
A67-B79-C11-D29
A39-B79-C11-D29
A65-B79-C11-D29
A66-B79-C11-D29
A2-B80-C11-D29
A3-B80-C11-D29
A9-B80-C11-D29
A13-B80-C11-D29
A24-B80-C11-D29
A69-B80-C11-D29
A67-B80-C11-D29
A39-B80-C11-D29
A65-B80-C11-D29
A66-B80-C11-D29
A2-B85-C11-D29
A3-B85-C11-D29
A9-B85-C11-D29
A13-B85-C11-D29
A24-B85-C11-D29
A69-B85-C11-D29
A67-B85-C11-D29
A39-B85-C11-D29
A65-B85-C11-D29
A66-B85-C11-D29
A2-B86-C11-D29
A3-B86-C11-D29
A9-B86-C11-D29
A13-B86-C11-D29
A24-B86-C11-D29
A69-B86-C11-D29
A67-B86-C11-D29
A39-B86-C11-D29
A65-B86-C11-D29
A66-B86-C11-D29
A2-B87-C11-D29

-continued

A3-B87-C11-D29
A9-B87-C11-D29
A13-B87-C11-D29
A24-B87-C11-D29
A69-B87-C11-D29
A67-B87-C11-D29
A39-B87-C11-D29
A65-B87-C11-D29
A66-B87-C11-D29
A2-B89-C11-D29
A3-B89-C11-D29
A9-B89-C11-D29
A13-B89-C11-D29
A24-B89-C11-D29
A69-B89-C11-D29
A67-B89-C11-D29
A39-B89-C11-D29
A65-B89-C11-D29
A66-B89-C11-D29
A2-B92-C11-D29
A3-B92-C11-D29
A9-B92-C11-D29
A13-B92-C11-D29
A24-B92-C11-D29
A69-B92-C11-D29
A67-B92-C11-D29
A39-B92-C11-D29
A65-B92-C11-D29
A66-B92-C11-D29
A2-B4-C12-D29
A3-B4-C12-D29
A9-B4-C12-D29
A13-B4-C12-D29
A24-B4-C12-D29
A69-B4-C12-D29
A67-B4-C12-D29
A39-B4-C12-D29
A65-B4-C12-D29
A66-B4-C12-D29
A2-B5-C12-D29
A3-B5-C12-D29
A9-B5-C12-D29
A13-B5-C12-D29
A24-B5-C12-D29
A69-B5-C12-D29
A67-B5-C12-D29
A39-B5-C12-D29
A65-B5-C12-D29
A66-B5-C12-D29
A2-B6-C12-D29
A3-B6-C12-D29
A9-B6-C12-D29
A13-B6-C12-D29
A24-B6-C12-D29
A69-B6-C12-D29
A67-B6-C12-D29
A39-B6-C12-D29
A65-B6-C12-D29
A66-B6-C12-D29
A2-B32-C12-D29
A3-B32-C12-D29
A9-B32-C12-D29
A13-B32-C12-D29
A24-B32-C12-D29
A69-B32-C12-D29
A67-B32-C12-D29
A39-B32-C12-D29
A65-B32-C12-D29
A66-B32-C12-D29
A2-B39-C12-D29
A3-B39-C12-D29
A9-B39-C12-D29
A13-B39-C12-D29
A24-B39-C12-D29
A69-B39-C12-D29
A67-B39-C12-D29
A39-B39-C12-D29
A65-B39-C12-D29
A66-B39-C12-D29
A2-B45-C12-D29

-continued
A3-B45-C12-D29
A9-B45-C12-D29
A13-B45-C12-D29
A24-B45-C12-D29
A69-B45-C12-D29
A67-B45-C12-D29
A39-B45-C12-D29
A65-B45-C12-D29
A66-B45-C12-D29
A2-B53-C12-D29
A3-B53-C12-D29
A9-B53-C12-D29
A13-B53-C12-D29
A24-B53-C12-D29
A69-B53-C12-D29
A67-B53-C12-D29
A39-B53-C12-D29
A65-B53-C12-D29
A66-B53-C12-D29
A2-B79-C12-D29
A3-B79-C12-D29
A9-B79-C12-D29
A13-B79-C12-D29
A24-B79-C12-D29
A69-B79-C12-D29
A67-B79-C12-D29
A39-B79-C12-D29
A65-B79-C12-D29
A66-B79-C12-D29
A2-B80-C12-D29
A3-B80-C12-D29
A9-B80-C12-D29
A13-B80-C12-D29
A24-B80-C12-D29
A69-B80-C12-D29
A67-B80-C12-D29
A39-B80-C12-D29
A65-B80-C12-D29
A66-B80-C12-D29
A2-B85-C12-D29
A3-B85-C12-D29
A9-B85-C12-D29
A13-B85-C12-D29
A24-B85-C12-D29
A69-B85-C12-D29
A67-B85-C12-D29
A39-B85-C12-D29
A65-B85-C12-D29
A66-B85-C12-D29
A2-B86-C12-D29
A3-B86-C12-D29
A9-B86-C12-D29
A13-B86-C12-D29
A24-B86-C12-D29
A69-B86-C12-D29
A67-B86-C12-D29
A39-B86-C12-D29
A65-B86-C12-D29
A66-B86-C12-D29
A2-B87-C12-D29
A3-B87-C12-D29
A9-B87-C12-D29
A13-B87-C12-D29
A24-B87-C12-D29
A69-B87-C12-D29
A67-B87-C12-D29
A39-B87-C12-D29
A65-B87-C12-D29
A66-B87-C12-D29
A2-B89-C12-D29
A3-B89-C12-D29
A9-B89-C12-D29
A13-B89-C12-D29
A24-B89-C12-D29
A69-B89-C12-D29
A67-B89-C12-D29
A39-B89-C12-D29
A65-B89-C12-D29
A66-B89-C12-D29
A2-B92-C12-D29

-continued
A3-B92-C12-D29
A9-B92-C12-D29
A13-B92-C12-D29
A24-B92-C12-D29
A69-B92-C12-D29
A67-B92-C12-D29
A39-B92-C12-D29
A65-B92-C12-D29
A66-B92-C12-D29
A2-B4-C13-D29
A3-B4-C13-D29
A9-B4-C13-D29
A13-B4-C13-D29
A24-B4-C13-D29
A69-B4-C13-D29
A67-B4-C13-D29
A39-B4-C13-D29
A65-B4-C13-D29
A66-B4-C13-D29
A2-B5-C13-D29
A3-B5-C13-D29
A9-B5-C13-D29
A13-B5-C13-D29
A24-B5-C13-D29
A69-B5-C13-D29
A67-B5-C13-D29
A39-B5-C13-D29
A65-B5-C13-D29
A66-B5-C13-D29
A2-B6-C13-D29
A3-B6-C13-D29
A9-B6-C13-D29
A13-B6-C13-D29
A24-B6-C13-D29
A69-B6-C13-D29
A67-B6-C13-D29
A39-B6-C13-D29
A65-B6-C13-D29
A66-B6-C13-D29
A2-B32-C13-D29
A3-B32-C13-D29
A9-B32-C13-D29
A13-B32-C13-D29
A24-B32-C13-D29
A69-B32-C13-D29
A67-B32-C13-D29
A39-B32-C13-D29
A65-B32-C13-D29
A66-B32-C13-D29
A2-B39-C13-D29
A3-B39-C13-D29
A9-B39-C13-D29
A13-B39-C13-D29
A24-B39-C13-D29
A69-B39-C13-D29
A67-B39-C13-D29
A39-B39-C13-D29
A65-B39-C13-D29
A66-B39-C13-D29
A2-B45-C13-D29
A3-B45-C13-D29
A9-B45-C13-D29
A13-B45-C13-D29
A24-B45-C13-D29
A69-B45-C13-D29
A67-B45-C13-D29
A39-B45-C13-D29
A65-B45-C13-D29
A66-B45-C13-D29
A2-B53-C13-D29
A3-B53-C13-D29
A9-B53-C13-D29
A13-B53-C13-D29
A24-B53-C13-D29
A69-B53-C13-D29
A67-B53-C13-D29
A39-B53-C13-D29
A65-B53-C13-D29
A66-B53-C13-D29
A2-B79-C13-D29

-continued

A3-B79-C13-D29
A9-B79-C13-D29
A13-B79-C13-D29
A24-B79-C13-D29
A69-B79-C13-D29
A67-B79-C13-D29
A39-B79-C13-D29
A65-B79-C13-D29
A66-B79-C13-D29
A2-B80-C13-D29
A3-B80-C13-D29
A9-B80-C13-D29
A13-B80-C13-D29
A24-B80-C13-D29
A69-B80-C13-D29
A67-B80-C13-D29
A39-B80-C13-D29
A65-B80-C13-D29
A66-B80-C13-D29
A2-B85-C13-D29
A3-B85-C13-D29
A9-B85-C13-D29
A13-B85-C13-D29
A24-B85-C13-D29
A69-B85-C13-D29
A67-B85-C13-D29
A39-B85-C13-D29
A65-B85-C13-D29
A66-B85-C13-D29
A2-B86-C13-D29
A3-B86-C13-D29
A9-B86-C13-D29
A13-B86-C13-D29
A24-B86-C13-D29
A69-B86-C13-D29
A67-B86-C13-D29
A39-B86-C13-D29
A65-B86-C13-D29
A66-B86-C13-D29
A2-B87-C13-D29
A3-B87-C13-D29
A9-B87-C13-D29
A13-B87-C13-D29
A24-B87-C13-D29
A69-B87-C13-D29
A67-B87-C13-D29
A39-B87-C13-D29
A65-B87-C13-D29
A66-B87-C13-D29
A2-B89-C13-D29
A3-B89-C13-D29
A9-B89-C13-D29
A13-B89-C13-D29
A24-B89-C13-D29
A69-B89-C13-D29
A67-B89-C13-D29
A39-B89-C13-D29
A65-B89-C13-D29
A66-B89-C13-D29
A2-B92-C13-D29
A3-B92-C13-D29
A9-B92-C13-D29
A13-B92-C13-D29
A24-B92-C13-D29
A69-B92-C13-D29
A67-B92-C13-D29
A39-B92-C13-D29
A65-B92-C13-D29
A66-B92-C13-D29
A2-B4-C1-D30
A3-B4-C1-D30
A9-B4-C1-D30
A13-B4-C1-D30
A24-B4-C1-D31
A69-B4-C1-D31
A67-B4-C1-D31
A39-B4-C1-D31
A65-B4-C1-D31
A66-B4-C1-D31
A2-B5-C1-D30

-continued

A3-B5-C1-D30
A9-B5-C1-D30
A13-B5-C1-D30
A24-B5-C1-D31
A69-B5-C1-D31
A67-B5-C1-D31
A39-B5-C1-D30
A65-B5-C1-D30
A66-B5-C1-D30
A2-B6-C1-D30
A3-B6-C1-D30
A9-B6-C1-D30
A13-B6-C1-D30
A24-B6-C1-D30
A69-B6-C1-D30
A67-B6-C1-D30
A39-B6-C1-D30
A65-B6-C1-D30
A66-B6-C1-D30
A2-B32-C1-D30
A3-B32-C1-D30
A9-B32-C1-D30
A13-B32-C1-D30
A24-B32-C1-D30
A69-B32-C1-D30
A67-B32-C1-D30
A39-B32-C1-D30
A65-B32-C1-D30
A66-B32-C1-D30
A2-B39-C1-D30
A3-B39-C1-D30
A9-B39-C1-D30
A13-B39-C1-D30
A24-B39-C1-D30
A69-B39-C1-D30
A67-B39-C1-D30
A39-B39-C1-D30
A65-B39-C1-D30
A66-B39-C1-D30
A2-B45-C1-D30
A3-B45-C1-D30
A9-B45-C1-D30
A13-B45-C1-D30
A24-B45-C1-D30
A69-B45-C1-D30
A67-B45-C1-D30
A39-B45-C1-D30
A65-B45-C1-D30
A66-B45-C1-D30
A2-B53-C1-D30
A3-B53-C1-D30
A9-B53-C1-D30
A13-B53-C1-D30
A24-B53-C1-D30
A69-B53-C1-D30
A67-B53-C1-D30
A39-B53-C1-D30
A65-B53-C1-D30
A66-B53-C1-D30
A2-B79-C1-D30
A3-B79-C1-D30
A9-B79-C1-D30
A13-B79-C1-D30
A24-B79-C1-D30
A69-B79-C1-D30
A67-B79-C1-D30
A39-B79-C1-D30
A65-B79-C1-D30
A66-B79-C1-D30
A2-B80-C1-D30
A3-B80-C1-D30
A9-B80-C1-D30
A13-B80-C1-D30
A24-B80-C1-D30
A69-B80-C1-D30
A67-B80-C1-D30
A39-B80-C1-D30
A65-B80-C1-D30
A66-B80-C1-D30
A2-B85-C1-D30

-continued

A3-B85-C1-D30
A9-B85-C1-D30
A13-B85-C1-D30
A24-B85-C1-D30
A69-B85-C1-D30
A67-B85-C1-D30
A39-B85-C1-D30
A65-B85-C1-D30
A66-B85-C1-D30
A2-B86-C1-D30
A3-B86-C1-D30
A9-B86-C1-D30
A13-B86-C1-D30
A24-B86-C1-D30
A69-B86-C1-D30
A67-B86-C1-D30
A39-B86-C1-D30
A65-B86-C1-D30
A66-B86-C1-D30
A2-B87-C1-D30
A3-B87-C1-D30
A9-B87-C1-D30
A13-B87-C1-D30
A24-B87-C1-D30
A69-B87-C1-D30
A67-B87-C1-D30
A39-B87-C1-D30
A65-B87-C1-D30
A66-B87-C1-D30
A2-B89-C1-D30
A3-B89-C1-D30
A9-B89-C1-D30
A13-B89-C1-D30
A24-B89-C1-D30
A69-B89-C1-D30
A67-B89-C1-D30
A39-B89-C1-D30
A65-B89-C1-D30
A66-B89-C1-D30
A2-B92-C1-D30
A3-B92-C1-D30
A9-B92-C1-D30
A13-B92-C1-D30
A24-B92-C1-D30
A69-B92-C1-D30
A67-B92-C1-D30
A39-B92-C1-D30
A65-B92-C1-D30
A66-B92-C1-D30
A2-B4-C2-D30
A3-B4-C2-D30
A9-B4-C2-D30
A13-B4-C2-D30
A24-B4-C2-D30
A69-B4-C2-D30
A67-B4-C2-D30
A39-B4-C2-D30
A65-B4-C2-D30
A66-B4-C2-D30
A2-B5-C2-D30
A3-B5-C2-D30
A9-B5-C2-D30
A13-B5-C2-D30
A24-B5-C2-D30
A69-B5-C2-D30
A67-B5-C2-D30
A39-B5-C2-D30
A65-B5-C2-D30
A66-B5-C2-D30
A2-B6-C2-D30
A3-B6-C2-D30
A9-B6-C2-D30
A13-B6-C2-D30
A24-B6-C2-D30
A69-B6-C2-D30
A67-B6-C2-D30
A39-B6-C2-D30
A65-B6-C2-D30
A66-B6-C2-D30
A2-B32-C2-D30

-continued

A3-B32-C2-D30
A9-B32-C2-D30
A13-B32-C2-D30
A24-B32-C2-D30
A69-B32-C2-D30
A67-B32-C2-D30
A39-B32-C2-D30
A65-B32-C2-D30
A66-B32-C2-D30
A2-B39-C2-D30
A3-B39-C2-D30
A9-B39-C2-D30
A13-B39-C2-D30
A24-B39-C2-D30
A69-B39-C2-D30
A67-B39-C2-D30
A39-B39-C2-D30
A65-B39-C2-D30
A66-B39-C2-D30
A2-B45-C2-D30
A3-B45-C2-D30
A9-B45-C2-D30
A13-B45-C2-D30
A24-B45-C2-D30
A69-B45-C2-D30
A67-B45-C2-D30
A39-B45-C2-D30
A65-B45-C2-D30
A66-B45-C2-D30
A2-B53-C2-D30
A3-B53-C2-D30
A9-B53-C2-D30
A13-B53-C2-D30
A24-B53-C2-D30
A69-B53-C2-D30
A67-B53-C2-D30
A39-B53-C2-D30
A65-B53-C2-D30
A66-B53-C2-D30
A2-B79-C2-D30
A3-B79-C2-D30
A9-B79-C2-D30
A13-B79-C2-D30
A24-B79-C2-D30
A69-B79-C2-D30
A67-B79-C2-D30
A39-B79-C2-D30
A65-B79-C2-D30
A66-B79-C2-D30
A2-B80-C2-D30
A3-B80-C2-D30
A9-B80-C2-D30
A13-B80-C2-D30
A24-B80-C2-D30
A69-B80-C2-D30
A67-B80-C2-D30
A39-B80-C2-D30
A65-B80-C2-D30
A66-B80-C2-D30
A2-B85-C2-D30
A3-B85-C2-D30
A9-B85-C2-D30
A13-B85-C2-D30
A24-B85-C2-D30
A69-B85-C2-D30
A67-B85-C2-D30
A39-B85-C2-D30
A65-B85-C2-D30
A66-B85-C2-D30
A2-B86-C2-D30
A3-B86-C2-D30
A9-B86-C2-D30
A13-B86-C2-D30
A24-B86-C2-D30
A69-B86-C2-D30
A67-B86-C2-D30
A39-B86-C2-D30
A65-B86-C2-D30
A66-B86-C2-D30
A2-B87-C2-D30

-continued
A3-B87-C2-D30
A9-B87-C2-D30
A13-B87-C2-D30
A24-B87-C2-D30
A69-B87-C2-D30
A67-B87-C2-D30
A39-B87-C2-D30
A65-B87-C2-D30
A66-B87-C2-D30
A2-B89-C2-D30
A3-B89-C2-D30
A9-B89-C2-D30
A13-B89-C2-D30
A24-B89-C2-D30
A69-B89-C2-D30
A67-B89-C2-D30
A39-B89-C2-D30
A65-B89-C2-D30
A66-B89-C2-D30
A2-B92-C2-D30
A3-B92-C2-D30
A9-B92-C2-D30
A13-B92-C2-D30
A24-B92-C2-D30
A69-B92-C2-D30
A67-B92-C2-D30
A39-B92-C2-D30
A65-B92-C2-D30
A66-B92-C2-D30
A2-B4-C3-D30
A3-B4-C3-D30
A9-B4-C3-D30
A13-B4-C3-D30
A24-B4-C3-D30
A69-B4-C3-D30
A67-B4-C3-D30
A39-B4-C3-D30
A65-B4-C3-D30
A66-B4-C3-D30
A2-B5-C3-D30
A3-B5-C3-D30
A9-B5-C3-D30
A13-B5-C3-D30
A24-B5-C3-D30
A69-B5-C3-D30
A67-B5-C3-D30
A39-B5-C3-D30
A65-B5-C3-D30
A66-B5-C3-D30
A2-B6-C3-D30
A3-B6-C3-D30
A9-B6-C3-D30
A13-B6-C3-D30
A24-B6-C3-D30
A69-B6-C3-D30
A67-B6-C3-D30
A39-B6-C3-D30
A65-B6-C3-D30
A66-B6-C3-D30
A2-B32-C3-D30
A3-B32-C3-D30
A9-B32-C3-D30
A13-B32-C3-D30
A24-B32-C3-D30
A69-B32-C3-D30
A67-B32-C3-D30
A39-B32-C3-D30
A65-B32-C3-D30
A66-B32-C3-D30
A2-B39-C3-D30
A3-B39-C3-D30
A9-B39-C3-D30
A13-B39-C3-D30
A24-B39-C3-D30
A69-B39-C3-D30
A67-B39-C3-D30
A39-B39-C3-D30
A65-B39-C3-D30
A66-B39-C3-D30
A2-B45-C3-D30

-continued
A3-B45-C3-D30
A9-B45-C3-D30
A13-B45-C3-D30
A24-B45-C3-D30
A69-B45-C3-D30
A67-B45-C3-D30
A39-B45-C3-D30
A65-B45-C3-D30
A66-B45-C3-D30
A2-B53-C3-D30
A3-B53-C3-D30
A9-B53-C3-D30
A13-B53-C3-D30
A24-B53-C3-D30
A69-B53-C3-D30
A67-B53-C3-D30
A39-B53-C3-D30
A65-B53-C3-D30
A66-B53-C3-D30
A2-B79-C3-D30
A3-B79-C3-D30
A9-B79-C3-D30
A13-B79-C3-D30
A24-B79-C3-D30
A69-B79-C3-D30
A67-B79-C3-D30
A39-B79-C3-D30
A65-B79-C3-D30
A66-B79-C3-D30
A2-B80-C3-D30
A3-B80-C3-D30
A9-B80-C3-D30
A13-B80-C3-D30
A24-B80-C3-D30
A69-B80-C3-D30
A67-B80-C3-D30
A39-B80-C3-D30
A65-B80-C3-D30
A66-B80-C3-D30
A2-B85-C3-D30
A3-B85-C3-D30
A9-B85-C3-D30
A13-B85-C3-D30
A24-B85-C3-D30
A69-B85-C3-D30
A67-B85-C3-D30
A39-B85-C3-D30
A65-B85-C3-D30
A66-B85-C3-D30
A2-B86-C3-D30
A3-B86-C3-D30
A9-B86-C3-D30
A13-B86-C3-D30
A24-B86-C3-D30
A69-B86-C3-D30
A67-B86-C3-D30
A39-B86-C3-D30
A65-B86-C3-D30
A66-B86-C3-D30
A2-B87-C3-D30
A3-B87-C3-D30
A9-B87-C3-D30
A13-B87-C3-D30
A24-B87-C3-D30
A69-B87-C3-D30
A67-B87-C3-D30
A39-B87-C3-D30
A65-B87-C3-D30
A66-B87-C3-D30
A2-B89-C3-D30
A3-B89-C3-D30
A9-B89-C3-D30
A13-B89-C3-D30
A24-B89-C3-D30
A69-B89-C3-D30
A67-B89-C3-D30
A39-B89-C3-D30
A65-B89-C3-D30
A66-B89-C3-D30
A2-B92-C3-D30

-continued
A3-B92-C3-D30
A9-B92-C3-D30
A13-B92-C3-D30
A24-B92-C3-D30
A69-B92-C3-D30
A67-B92-C3-D30
A39-B92-C3-D30
A65-B92-C3-D30
A66-B92-C3-D30
A2-B4-C4-D30
A3-B4-C4-D30
A9-B4-C4-D30
A13-B4-C4-D30
A24-B4-C4-D30
A69-B4-C4-D30
A67-B4-C4-D30
A39-B4-C4-D30
A65-B4-C4-D30
A66-B4-C4-D30
A2-B5-C4-D30
A3-B5-C4-D30
A9-B5-C4-D30
A13-B5-C4-D30
A24-B5-C4-D30
A69-B5-C4-D30
A67-B5-C4-D30
A39-B5-C4-D30
A65-B5-C4-D30
A66-B5-C4-D30
A2-B6-C4-D30
A3-B6-C4-D30
A9-B6-C4-D30
A13-B6-C4-D30
A24-B6-C4-D30
A69-B6-C4-D30
A67-B6-C4-D30
A39-B6-C4-D30
A65-B6-C4-D30
A66-B6-C4-D30
A2-B32-C4-D30
A3-B32-C4-D30
A9-B32-C4-D30
A13-B32-C4-D30
A24-B32-C4-D30
A69-B32-C4-D30
A67-B32-C4-D30
A39-B32-C4-D30
A65-B32-C4-D30
A66-B32-C4-D30
A2-B39-C4-D30
A3-B39-C4-D30
A9-B39-C4-D30
A13-B39-C4-D30
A24-B39-C4-D30
A69-B39-C4-D30
A67-B39-C4-D30
A39-B39-C4-D30
A65-B39-C4-D30
A66-B39-C4-D30
A2-B45-C4-D30
A3-B45-C4-D30
A9-B45-C4-D30
A13-B45-C4-D30
A24-B45-C4-D30
A69-B45-C4-D30
A67-B45-C4-D30
A39-B45-C4-D30
A65-B45-C4-D30
A66-B45-C4-D30
A2-B53-C4-D30
A3-B53-C4-D30
A9-B53-C4-D30
A13-B53-C4-D30
A24-B53-C4-D30
A69-B53-C4-D30
A67-B53-C4-D30
A39-B53-C4-D30
A65-B53-C4-D30
A66-B53-C4-D30
A2-B79-C4-D30

-continued
A3-B79-C4-D30
A9-B79-C4-D30
A13-B79-C4-D30
A24-B79-C4-D30
A69-B79-C4-D30
A67-B79-C4-D30
A39-B79-C4-D30
A65-B79-C4-D30
A66-B79-C4-D30
A2-B80-C4-D30
A3-B80-C4-D30
A9-B80-C4-D30
A13-B80-C4-D30
A24-B80-C4-D30
A69-B80-C4-D30
A67-B80-C4-D30
A39-B80-C4-D30
A65-B80-C4-D30
A66-B80-C4-D30
A2-B85-C4-D30
A3-B85-C4-D30
A9-B85-C4-D30
A13-B85-C4-D30
A24-B85-C4-D30
A69-B85-C4-D30
A67-B85-C4-D30
A39-B85-C4-D30
A65-B85-C4-D30
A66-B85-C4-D30
A2-B86-C4-D30
A3-B86-C4-D30
A9-B86-C4-D30
A13-B86-C4-D30
A24-B86-C4-D30
A69-B86-C4-D30
A67-B86-C4-D30
A39-B86-C4-D30
A65-B86-C4-D30
A66-B86-C4-D30
A2-B87-C4-D30
A3-B87-C4-D30
A9-B87-C4-D30
A13-B87-C4-D30
A24-B87-C4-D30
A69-B87-C4-D30
A67-B87-C4-D30
A39-B87-C4-D30
A65-B87-C4-D30
A66-B87-C4-D30
A2-B89-C4-D30
A3-B89-C4-D30
A9-B89-C4-D30
A13-B89-C4-D30
A24-B89-C4-D30
A69-B89-C4-D30
A67-B89-C4-D30
A39-B89-C4-D30
A65-B89-C4-D30
A66-B89-C4-D30
A2-B92-C4-D30
A3-B92-C4-D30
A9-B92-C4-D30
A13-B92-C4-D30
A24-B92-C4-D30
A69-B92-C4-D30
A67-B92-C4-D30
A39-B92-C4-D30
A65-B92-C4-D30
A66-B92-C4-D30
A2-B4-C5-D30
A3-B4-C5-D30
A9-B4-C5-D30
A13-B4-C5-D30
A24-B4-C5-D30
A69-B4-C5-D30
A67-B4-C5-D30
A39-B4-C5-D30
A65-B4-C5-D30
A66-B4-C5-D30
A2-B5-C5-D30

-continued

A3-B5-C5-D30
A9-B5-C5-D30
A13-B5-C5-D30
A24-B5-C5-D30
A69-B5-C5-D30
A67-B5-C5-D30
A39-B5-C5-D30
A65-B5-C5-D30
A66-B5-C5-D30
A2-B6-C5-D30
A3-B6-C5-D30
A9-B6-C5-D30
A13-B6-C5-D30
A24-B6-C5-D30
A69-B6-C5-D30
A67-B6-C5-D30
A39-B6-C5-D30
A65-B6-C5-D30
A66-B6-C5-D30
A2-B32-C5-D30
A3-B32-C5-D30
A9-B32-C5-D30
A13-B32-C5-D30
A24-B32-C5-D30
A69-B32-C5-D30
A67-B32-C5-D30
A39-B32-C5-D30
A65-B32-C5-D30
A66-B32-C5-D30
A2-B39-C5-D30
A3-B39-C5-D30
A9-B39-C5-D30
A13-B39-C5-D30
A24-B39-C5-D30
A69-B39-C5-D30
A67-B39-C5-D30
A39-B39-C5-D30
A65-B39-C5-D30
A66-B39-C5-D30
A2-B45-C5-D30
A3-B45-C5-D30
A9-B45-C5-D30
A13-B45-C5-D30
A24-B45-C5-D30
A69-B45-C5-D30
A67-B45-C5-D30
A39-B45-C5-D30
A65-B45-C5-D30
A66-B45-C5-D30
A2-B53-C5-D30
A3-B53-C5-D30
A9-B53-C5-D30
A13-B53-C5-D30
A24-B53-C5-D30
A69-B53-C5-D30
A67-B53-C5-D30
A39-B53-C5-D30
A65-B53-C5-D30
A66-B53-C5-D30
A2-B79-C5-D30
A3-B79-C5-D30
A9-B79-C5-D30
A13-B79-C5-D30
A24-B79-C5-D30
A69-B79-C5-D30
A67-B79-C5-D30
A39-B79-C5-D30
A65-B79-C5-D30
A66-B79-C5-D30
A2-B80-C5-D30
A3-B80-C5-D30
A9-B80-C5-D30
A13-B80-C5-D30
A24-B80-C5-D30
A69-B80-C5-D30
A67-B80-C5-D30
A39-B80-C5-D30
A65-B80-C5-D30
A66-B80-C5-D30
A2-B85-C5-D30

-continued

A3-B85-C5-D30
A9-B85-C5-D30
A13-B85-C5-D30
A24-B85-C5-D30
A69-B85-C5-D30
A67-B85-C5-D30
A39-B85-C5-D30
A65-B85-C5-D30
A66-B85-C5-D30
A2-B86-C5-D30
A3-B86-C5-D30
A9-B86-C5-D30
A13-B86-C5-D30
A24-B86-C5-D30
A69-B86-C5-D30
A67-B86-C5-D30
A39-B86-C5-D30
A65-B86-C5-D30
A66-B86-C5-D30
A2-B87-C5-D30
A3-B87-C5-D30
A9-B87-C5-D30
A13-B87-C5-D30
A24-B87-C5-D30
A69-B87-C5-D30
A67-B87-C5-D30
A39-B87-C5-D30
A65-B87-C5-D30
A66-B87-C5-D30
A2-B89-C5-D30
A3-B89-C5-D30
A9-B89-C5-D30
A13-B89-C5-D30
A24-B89-C5-D30
A69-B89-C5-D30
A67-B89-C5-D30
A39-B89-C5-D30
A65-B89-C5-D30
A66-B89-C5-D30
A2-B92-C5-D30
A3-B92-C5-D30
A9-B92-C5-D30
A13-B92-C5-D30
A24-B92-C5-D30
A69-B92-C5-D30
A67-B92-C5-D30
A39-B92-C5-D30
A65-B92-C5-D30
A66-B92-C5-D30
A2-B4-C6-D30
A3-B4-C6-D30
A9-B4-C6-D30
A13-B4-C6-D30
A24-B4-C6-D30
A69-B4-C6-D30
A67-B4-C6-D30
A39-B4-C6-D30
A65-B4-C6-D30
A66-B4-C6-D30
A2-B5-C6-D30
A3-B5-C6-D30
A9-B5-C6-D30
A13-B5-C6-D30
A24-B5-C6-D30
A69-B5-C6-D30
A67-B5-C6-D30
A39-B5-C6-D30
A65-B5-C6-D30
A66-B5-C6-D30
A2-B6-C6-D30
A3-B6-C6-D30
A9-B6-C6-D30
A13-B6-C6-D30
A24-B6-C6-D30
A69-B6-C6-D30
A67-B6-C6-D30
A39-B6-C6-D30
A65-B6-C6-D30
A66-B6-C6-D30
A2-B32-C6-D30

-continued
A3-B32-C6-D30
A9-B32-C6-D30
A13-B32-C6-D30
A24-B32-C6-D30
A69-B32-C6-D30
A67-B32-C6-D30
A39-B32-C6-D30
A65-B32-C6-D30
A66-B32-C6-D30
A2-B39-C6-D30
A3-B39-C6-D30
A9-B39-C6-D30
A13-B39-C6-D30
A24-B39-C6-D30
A69-B39-C6-D30
A67-B39-C6-D30
A39-B39-C6-D30
A65-B39-C6-D30
A66-B39-C6-D30
A2-B45-C6-D30
A3-B45-C6-D30
A9-B45-C6-D30
A13-B45-C6-D30
A24-B45-C6-D30
A69-B45-C6-D30
A67-B45-C6-D30
A39-B45-C6-D30
A65-B45-C6-D30
A66-B45-C6-D30
A2-B53-C6-D30
A3-B53-C6-D30
A9-B53-C6-D30
A13-B53-C6-D30
A24-B53-C6-D30
A69-B53-C6-D30
A67-B53-C6-D30
A39-B53-C6-D30
A65-B53-C6-D30
A66-B53-C6-D30
A2-B79-C6-D30
A3-B79-C6-D30
A9-B79-C6-D30
A13-B79-C6-D30
A24-B79-C6-D30
A69-B79-C6-D30
A67-B79-C6-D30
A39-B79-C6-D30
A65-B79-C6-D30
A66-B79-C6-D30
A2-B80-C6-D30
A3-B80-C6-D30
A9-B80-C6-D30
A13-B80-C6-D30
A24-B80-C6-D30
A69-B80-C6-D30
A67-B80-C6-D30
A39-B80-C6-D30
A65-B80-C6-D30
A66-B80-C6-D30
A2-B85-C6-D30
A3-B85-C6-D30
A9-B85-C6-D30
A13-B85-C6-D30
A24-B85-C6-D30
A69-B85-C6-D30
A67-B85-C6-D30
A39-B85-C6-D30
A65-B85-C6-D30
A66-B85-C6-D30
A2-B86-C6-D30
A3-B86-C6-D30
A9-B86-C6-D30
A13-B86-C6-D30
A24-B86-C6-D30
A69-B86-C6-D30
A67-B86-C6-D30
A39-B86-C6-D30
A65-B86-C6-D30
A66-B86-C6-D30
A2-B87-C6-D30

-continued
A3-B87-C6-D30
A9-B87-C6-D30
A13-B87-C6-D30
A24-B87-C6-D30
A69-B87-C6-D30
A67-B87-C6-D30
A39-B87-C6-D30
A65-B87-C6-D30
A66-B87-C6-D30
A2-B89-C6-D30
A3-B89-C6-D30
A9-B89-C6-D30
A13-B89-C6-D30
A24-B89-C6-D30
A69-B89-C6-D30
A67-B89-C6-D30
A39-B89-C6-D30
A65-B89-C6-D30
A66-B89-C6-D30
A2-B92-C6-D30
A3-B92-C6-D30
A9-B92-C6-D30
A13-B92-C6-D30
A24-B92-C6-D30
A69-B92-C6-D30
A67-B92-C6-D30
A39-B92-C6-D30
A65-B92-C6-D30
A66-B92-C6-D30
A2-B4-C7-D30
A3-B4-C7-D30
A9-B4-C7-D30
A13-B4-C7-D30
A24-B4-C7-D30
A69-B4-C7-D30
A67-B4-C7-D30
A39-B4-C7-D30
A65-B4-C7-D30
A66-B4-C7-D30
A2-B5-C7-D30
A3-B5-C7-D30
A9-B5-C7-D30
A13-B5-C7-D30
A24-B5-C7-D30
A69-B5-C7-D30
A67-B5-C7-D30
A39-B5-C7-D30
A65-B5-C7-D30
A66-B5-C7-D30
A2-B6-C7-D30
A3-B6-C7-D30
A9-B6-C7-D30
A13-B6-C7-D30
A24-B6-C7-D30
A69-B6-C7-D30
A67-B6-C7-D30
A39-B6-C7-D30
A65-B6-C7-D30
A66-B6-C7-D30
A2-B32-C7-D30
A3-B32-C7-D30
A9-B32-C7-D30
A13-B32-C7-D30
A24-B32-C7-D30
A69-B32-C7-D30
A67-B32-C7-D30
A39-B32-C7-D30
A65-B32-C7-D30
A66-B32-C7-D30
A2-B39-C7-D30
A3-B39-C7-D30
A9-B39-C7-D30
A13-B39-C7-D30
A24-B39-C7-D30
A69-B39-C7-D30
A67-B39-C7-D30
A39-B39-C7-D30
A65-B39-C7-D30
A66-B39-C7-D30
A2-B45-C7-D30

-continued
A3-B45-C7-D30
A9-B45-C7-D30
A13-B45-C7-D30
A24-B45-C7-D30
A69-B45-C7-D30
A67-B45-C7-D30
A39-B45-C7-D30
A65-B45-C7-D30
A66-B45-C7-D30
A2-B53-C7-D30
A3-B53-C7-D30
A9-B53-C7-D30
A13-B53-C7-D30
A24-B53-C7-D30
A69-B53-C7-D30
A67-B53-C7-D30
A39-B53-C7-D30
A65-B53-C7-D30
A66-B53-C7-D30
A2-B79-C7-D30
A3-B79-C7-D30
A9-B79-C7-D30
A13-B79-C7-D30
A24-B79-C7-D30
A69-B79-C7-D30
A67-B79-C7-D30
A39-B79-C7-D30
A65-B79-C7-D30
A66-B79-C7-D30
A2-B80-C7-D30
A3-B80-C7-D30
A9-B80-C7-D30
A13-B80-C7-D30
A24-B80-C7-D30
A69-B80-C7-D30
A67-B80-C7-D30
A39-B80-C7-D30
A65-B80-C7-D30
A66-B80-C7-D30
A2-B85-C7-D30
A3-B85-C7-D30
A9-B85-C7-D30
A13-B85-C7-D30
A24-B85-C7-D30
A69-B85-C7-D30
A67-B85-C7-D30
A39-B85-C7-D30
A65-B85-C7-D30
A66-B85-C7-D30
A2-B86-C7-D30
A3-B86-C7-D30
A9-B86-C7-D30
A13-B86-C7-D30
A24-B86-C7-D30
A69-B86-C7-D30
A67-B86-C7-D30
A39-B86-C7-D30
A65-B86-C7-D30
A66-B86-C7-D30
A2-B87-C7-D30
A3-B87-C7-D30
A9-B87-C7-D30
A13-B87-C7-D30
A24-B87-C7-D30
A69-B87-C7-D30
A67-B87-C7-D30
A39-B87-C7-D30
A65-B87-C7-D30
A66-B87-C7-D30
A2-B89-C7-D30
A3-B89-C7-D30
A9-B89-C7-D30
A13-B89-C7-D30
A24-B89-C7-D30
A69-B89-C7-D30
A67-B89-C7-D30
A39-B89-C7-D30
A65-B89-C7-D30
A66-B89-C7-D30
A2-B92-C7-D30

-continued
A3-B92-C7-D30
A9-B92-C7-D30
A13-B92-C7-D30
A24-B92-C7-D30
A69-B92-C7-D30
A67-B92-C7-D30
A39-B92-C7-D30
A65-B92-C7-D30
A66-B92-C7-D30
A2-B4-C8-D30
A3-B4-C8-D30
A9-B4-C8-D30
A13-B4-C8-D30
A24-B4-C8-D30
A69-B4-C8-D30
A67-B4-C8-D30
A39-B4-C8-D30
A65-B4-C8-D30
A66-B4-C8-D30
A2-B5-C8-D30
A3-B5-C8-D30
A9-B5-C8-D30
A13-B5-C8-D30
A24-B5-C8-D30
A69-B5-C8-D30
A67-B5-C8-D30
A39-B5-C8-D30
A65-B5-C8-D30
A66-B5-C8-D30
A2-B6-C8-D30
A3-B6-C8-D30
A9-B6-C8-D30
A13-B6-C8-D30
A24-B6-C8-D30
A69-B6-C8-D30
A67-B6-C8-D30
A39-B6-C8-D30
A65-B6-C8-D30
A66-B6-C8-D30
A2-B32-C8-D30
A3-B32-C8-D30
A9-B32-C8-D30
A13-B32-C8-D30
A24-B32-C8-D30
A69-B32-C8-D30
A67-B32-C8-D30
A39-B32-C8-D30
A65-B32-C8-D30
A66-B32-C8-D30
A2-B39-C8-D30
A3-B39-C8-D30
A9-B39-C8-D30
A13-B39-C8-D30
A24-B39-C8-D30
A69-B39-C8-D30
A67-B39-C8-D30
A39-B39-C8-D30
A65-B39-C8-D30
A66-B39-C8-D30
A2-B45-C8-D30
A3-B45-C8-D30
A9-B45-C8-D30
A13-B45-C8-D30
A24-B45-C8-D30
A69-B45-C8-D30
A67-B45-C8-D30
A39-B45-C8-D30
A65-B45-C8-D30
A66-B45-C8-D30
A2-B53-C8-D30
A3-B53-C8-D30
A9-B53-C8-D30
A13-B53-C8-D30
A24-B53-C8-D30
A69-B53-C8-D30
A67-B53-C8-D30
A39-B53-C8-D30
A65-B53-C8-D30
A66-B53-C8-D30
A2-B79-C8-D30

-continued

A3-B79-C8-D30
A9-B79-C8-D30
A13-B79-C8-D30
A24-B79-C8-D30
A69-B79-C8-D30
A67-B79-C8-D30
A39-B79-C8-D30
A65-B79-C8-D30
A66-B79-C8-D30
A2-B80-C8-D30
A3-B80-C8-D30
A9-B80-C8-D30
A13-B80-C8-D30
A24-B80-C8-D30
A69-B80-C8-D30
A67-B80-C8-D30
A39-B80-C8-D30
A65-B80-C8-D30
A66-B80-C8-D30
A2-B85-C8-D30
A3-B85-C8-D30
A9-B85-C8-D30
A13-B85-C8-D30
A24-B85-C8-D30
A69-B85-C8-D30
A67-B85-C8-D30
A39-B85-C8-D30
A65-B85-C8-D30
A66-B85-C8-D30
A2-B86-C8-D30
A3-B86-C8-D30
A9-B86-C8-D30
A13-B86-C8-D30
A24-B86-C8-D30
A69-B86-C8-D30
A67-B86-C8-D30
A39-B86-C8-D30
A65-B86-C8-D30
A66-B86-C8-D30
A2-B87-C8-D30
A3-B87-C8-D30
A9-B87-C8-D30
A13-B87-C8-D30
A24-B87-C8-D30
A69-B87-C8-D30
A67-B87-C8-D30
A39-B87-C8-D30
A65-B87-C8-D30
A66-B87-C8-D30
A2-B89-C8-D30
A3-B89-C8-D30
A9-B89-C8-D30
A13-B89-C8-D30
A24-B89-C8-D30
A69-B89-C8-D30
A67-B89-C8-D30
A39-B89-C8-D30
A65-B89-C8-D30
A66-B89-C8-D30
A2-B92-C8-D30
A3-B92-C8-D30
A9-B92-C8-D30
A13-B92-C8-D30
A24-B92-C8-D30
A69-B92-C8-D30
A67-B92-C8-D30
A39-B92-C8-D30
A65-B92-C8-D30
A66-B92-C8-D30
A2-B4-C9-D30
A3-B4-C9-D30
A9-B4-C9-D30
A13-B4-C9-D30
A24-B4-C9-D30
A69-B4-C9-D30
A67-B4-C9-D30
A39-B4-C9-D30
A65-B4-C9-D30
A66-B4-C9-D30
A2-B5-C9-D30

-continued

A3-B5-C9-D30
A9-B5-C9-D30
A13-B5-C9-D30
A24-B5-C9-D30
A69-B5-C9-D30
A67-B5-C9-D30
A39-B5-C9-D30
A65-B5-C9-D30
A66-B5-C9-D30
A2-B6-C9-D30
A3-B6-C9-D30
A9-B6-C9-D30
A13-B6-C9-D30
A24-B6-C9-D30
A69-B6-C9-D30
A67-B6-C9-D30
A39-B6-C9-D30
A65-B6-C9-D30
A66-B6-C9-D30
A2-B32-C9-D30
A3-B32-C9-D30
A9-B32-C9-D30
A13-B32-C9-D30
A24-B32-C9-D30
A69-B32-C9-D30
A67-B32-C9-D30
A39-B32-C9-D30
A65-B32-C9-D30
A66-B32-C9-D30
A2-B39-C9-D30
A3-B39-C9-D30
A9-B39-C9-D30
A13-B39-C9-D30
A24-B39-C9-D30
A69-B39-C9-D30
A67-B39-C9-D30
A39-B39-C9-D30
A65-B39-C9-D30
A66-B39-C9-D30
A2-B45-C9-D30
A3-B45-C9-D30
A9-B45-C9-D30
A13-B45-C9-D30
A24-B45-C9-D30
A69-B45-C9-D30
A67-B45-C9-D30
A39-B45-C9-D30
A65-B45-C9-D30
A66-B45-C9-D30
A2-B53-C9-D30
A3-B53-C9-D30
A9-B53-C9-D30
A13-B53-C9-D30
A24-B53-C9-D30
A69-B53-C9-D30
A67-B53-C9-D30
A39-B53-C9-D30
A65-B53-C9-D30
A66-B53-C9-D30
A2-B79-C9-D30
A3-B79-C9-D30
A9-B79-C9-D30
A13-B79-C9-D30
A24-B79-C9-D30
A69-B79-C9-D30
A67-B79-C9-D30
A39-B79-C9-D30
A65-B79-C9-D30
A66-B79-C9-D30
A2-B80-C9-D30
A3-B80-C9-D30
A9-B80-C9-D30
A13-B80-C9-D30
A24-B80-C9-D30
A69-B80-C9-D30
A67-B80-C9-D30
A39-B80-C9-D30
A65-B80-C9-D30
A66-B80-C9-D30
A2-B85-C9-D30

-continued
A3-B85-C9-D30
A9-B85-C9-D30
A13-B85-C9-D30
A24-B85-C9-D30
A69-B85-C9-D30
A67-B85-C9-D30
A39-B85-C9-D30
A65-B85-C9-D30
A66-B85-C9-D30
A2-B86-C9-D30
A3-B86-C9-D30
A9-B86-C9-D30
A13-B86-C9-D30
A24-B86-C9-D30
A69-B86-C9-D30
A67-B86-C9-D30
A39-B86-C9-D30
A65-B86-C9-D30
A66-B86-C9-D30
A2-B87-C9-D30
A3-B87-C9-D30
A9-B87-C9-D30
A13-B87-C9-D30
A24-B87-C9-D30
A69-B87-C9-D30
A67-B87-C9-D30
A39-B87-C9-D30
A65-B87-C9-D30
A66-B87-C9-D30
A2-B89-C9-D30
A3-B89-C9-D30
A9-B89-C9-D30
A13-B89-C9-D30
A24-B89-C9-D30
A69-B89-C9-D30
A67-B89-C9-D30
A39-B89-C9-D30
A65-B89-C9-D30
A66-B89-C9-D30
A2-B92-C9-D30
A3-B92-C9-D30
A9-B92-C9-D30
A13-B92-C9-D30
A24-B92-C9-D30
A69-B92-C9-D30
A67-B92-C9-D30
A39-B92-C9-D30
A65-B92-C9-D30
A66-B92-C9-D30
A2-B4-C10-D30
A3-B4-C10-D30
A9-B4-C10-D30
A13-B4-C10-D30
A24-B4-C10-D30
A69-B4-C10-D30
A67-B4-C10-D30
A39-B4-C10-D30
A65-B4-C10-D30
A66-B4-C10-D30
A2-B5-C10-D30
A3-B5-C10-D30
A9-B5-C10-D30
A13-B5-C10-D30
A24-B5-C10-D30
A69-B5-C10-D30
A67-B5-C10-D30
A39-B5-C10-D30
A65-B5-C10-D30
A66-B5-C10-D30
A2-B6-C10-D30
A3-B6-C10-D30
A9-B6-C10-D30
A13-B6-C10-D30
A24-B6-C10-D30
A69-B6-C10-D30
A67-B6-C10-D30
A39-B6-C10-D30
A65-B6-C10-D30
A66-B6-C10-D30
A2-B32-C10-D30

-continued
A3-B32-C10-D30
A9-B32-C10-D30
A13-B32-C10-D30
A24-B32-C10-D30
A69-B32-C10-D30
A67-B32-C10-D30
A39-B32-C10-D30
A65-B32-C10-D30
A66-B32-C10-D30
A2-B39-C10-D30
A3-B39-C10-D30
A9-B39-C10-D30
A13-B39-C10-D30
A24-B39-C10-D30
A69-B39-C10-D30
A67-B39-C10-D30
A39-B39-C10-D30
A65-B39-C10-D30
A66-B39-C10-D30
A2-B45-C10-D30
A3-B45-C10-D30
A9-B45-C10-D30
A13-B45-C10-D30
A24-B45-C10-D30
A69-B45-C10-D30
A67-B45-C10-D30
A39-B45-C10-D30
A65-B45-C10-D30
A66-B45-C10-D30
A2-B53-C10-D30
A3-B53-C10-D30
A9-B53-C10-D30
A13-B53-C10-D30
A24-B53-C10-D30
A69-B53-C10-D30
A67-B53-C10-D30
A39-B53-C10-D30
A65-B53-C10-D30
A66-B53-C10-D30
A2-B79-C10-D30
A3-B79-C10-D30
A9-B79-C10-D30
A13-B79-C10-D30
A24-B79-C10-D30
A69-B79-C10-D30
A67-B79-C10-D30
A39-B79-C10-D30
A65-B79-C10-D30
A66-B79-C10-D30
A2-B80-C10-D30
A3-B80-C10-D30
A9-B80-C10-D30
A13-B80-C10-D30
A24-B80-C10-D30
A69-B80-C10-D30
A67-B80-C10-D30
A39-B80-C10-D30
A65-B80-C10-D30
A66-B80-C10-D30
A2-B85-C10-D30
A3-B85-C10-D30
A9-B85-C10-D30
A13-B85-C10-D30
A24-B85-C10-D30
A69-B85-C10-D30
A67-B85-C10-D30
A39-B85-C10-D30
A65-B85-C10-D30
A66-B85-C10-D30
A2-B86-C10-D30
A3-B86-C10-D30
A9-B86-C10-D30
A13-B86-C10-D30
A24-B86-C10-D30
A69-B86-C10-D30
A67-B86-C10-D30
A39-B86-C10-D30
A65-B86-C10-D30
A66-B86-C10-D30
A2-B87-C10-D30

-continued

A3-B87-C10-D30
A9-B87-C10-D30
A13-B87-C10-D30
A24-B87-C10-D30
A69-B87-C10-D30
A67-B87-C10-D30
A39-B87-C10-D30
A65-B87-C10-D30
A66-B87-C10-D30
A2-B89-C10-D30
A3-B89-C10-D30
A9-B89-C10-D30
A13-B89-C10-D30
A24-B89-C10-D30
A69-B89-C10-D30
A67-B89-C10-D30
A39-B89-C10-D30
A65-B89-C10-D30
A66-B89-C10-D30
A2-B92-C10-D30
A3-B92-C10-D30
A9-B92-C10-D30
A13-B92-C10-D30
A24-B92-C10-D30
A69-B92-C10-D30
A67-B92-C10-D30
A39-B92-C10-D30
A65-B92-C10-D30
A66-B92-C10-D30
A2-B4-C11-D30
A3-B4-C11-D30
A9-B4-C11-D30
A13-B4-C11-D30
A24-B4-C11-D30
A69-B4-C11-D30
A67-B4-C11-D30
A39-B4-C11-D30
A65-B4-C11-D30
A66-B4-C11-D30
A2-B5-C11-D30
A3-B5-C11-D30
A9-B5-C11-D30
A13-B5-C11-D30
A24-B5-C11-D30
A69-B5-C11-D30
A67-B5-C11-D30
A39-B5-C11-D30
A65-B5-C11-D30
A66-B5-C11-D30
A2-B6-C11-D30
A3-B6-C11-D30
A9-B6-C11-D30
A13-B6-C11-D30
A24-B6-C11-D30
A69-B6-C11-D30
A67-B6-C11-D30
A39-B6-C11-D30
A65-B6-C11-D30
A66-B6-C11-D30
A2-B32-C11-D30
A3-B32-C11-D30
A9-B32-C11-D30
A13-B32-C11-D30
A24-B32-C11-D30
A69-B32-C11-D30
A67-B32-C11-D30
A39-B32-C11-D30
A65-B32-C11-D30
A66-B32-C11-D30
A2-B39-C11-D30
A3-B39-C11-D30
A9-B39-C11-D30
A13-B39-C11-D30
A24-B39-C11-D30
A69-B39-C11-D30
A67-B39-C11-D30
A39-B39-C11-D30
A65-B39-C11-D30
A66-B39-C11-D30
A2-B45-C11-D30

-continued

A3-B45-C11-D30
A9-B45-C11-D30
A13-B45-C11-D30
A24-B45-C11-D30
A69-B45-C11-D30
A67-B45-C11-D30
A39-B45-C11-D30
A65-B45-C11-D30
A66-B45-C11-D30
A2-B53-C11-D30
A3-B53-C11-D30
A9-B53-C11-D30
A13-B53-C11-D30
A24-B53-C11-D30
A69-B53-C11-D30
A67-B53-C11-D30
A39-B53-C11-D30
A65-B53-C11-D30
A66-B53-C11-D30
A2-B79-C11-D30
A3-B79-C11-D30
A9-B79-C11-D30
A13-B79-C11-D30
A24-B79-C11-D30
A69-B79-C11-D30
A67-B79-C11-D30
A39-B79-C11-D30
A65-B79-C11-D30
A66-B79-C11-D30
A2-B80-C11-D30
A3-B80-C11-D30
A9-B80-C11-D30
A13-B80-C11-D30
A24-B80-C11-D30
A69-B80-C11-D30
A67-B80-C11-D30
A39-B80-C11-D30
A65-B80-C11-D30
A66-B80-C11-D30
A2-B85-C11-D30
A3-B85-C11-D30
A9-B85-C11-D30
A13-B85-C11-D30
A24-B85-C11-D30
A69-B85-C11-D30
A67-B85-C11-D30
A39-B85-C11-D30
A65-B85-C11-D30
A66-B85-C11-D30
A2-B86-C11-D30
A3-B86-C11-D30
A9-B86-C11-D30
A13-B86-C11-D30
A24-B86-C11-D30
A69-B86-C11-D30
A67-B86-C11-D30
A39-B86-C11-D30
A65-B86-C11-D30
A66-B86-C11-D30
A2-B87-C11-D30
A3-B87-C11-D30
A9-B87-C11-D30
A13-B87-C11-D30
A24-B87-C11-D30
A69-B87-C11-D30
A67-B87-C11-D30
A39-B87-C11-D30
A65-B87-C11-D30
A66-B87-C11-D30
A2-B89-C11-D30
A3-B89-C11-D30
A9-B89-C11-D30
A13-B89-C11-D30
A24-B89-C11-D30
A69-B89-C11-D30
A67-B89-C11-D30
A39-B89-C11-D30
A65-B89-C11-D30
A66-B89-C11-D30
A2-B92-C11-D30

-continued

A3-B92-C11-D30
A9-B92-C11-D30
A13-B92-C11-D30
A24-B92-C11-D30
A69-B92-C11-D30
A67-B92-C11-D30
A39-B92-C11-D30
A65-B92-C11-D30
A66-B92-C11-D30
A2-B4-C12-D30
A3-B4-C12-D30
A9-B4-C12-D30
A13-B4-C12-D30
A24-B4-C12-D30
A69-B4-C12-D30
A67-B4-C12-D30
A39-B4-C12-D30
A65-B4-C12-D30
A66-B4-C12-D30
A2-B5-C12-D30
A3-B5-C12-D30
A9-B5-C12-D30
A13-B5-C12-D30
A24-B5-C12-D30
A69-B5-C12-D30
A67-B5-C12-D30
A39-B5-C12-D30
A65-B5-C12-D30
A66-B5-C12-D30
A2-B6-C12-D30
A3-B6-C12-D30
A9-B6-C12-D30
A13-B6-C12-D30
A24-B6-C12-D30
A69-B6-C12-D30
A67-B6-C12-D30
A39-B6-C12-D30
A65-B6-C12-D30
A66-B6-C12-D30
A2-B32-C12-D30
A3-B32-C12-D30
A9-B32-C12-D30
A13-B32-C12-D30
A24-B32-C12-D30
A69-B32-C12-D30
A67-B32-C12-D30
A39-B32-C12-D30
A65-B32-C12-D30
A66-B32-C12-D30
A2-B39-C12-D30
A3-B39-C12-D30
A9-B39-C12-D30
A13-B39-C12-D30
A24-B39-C12-D30
A69-B39-C12-D30
A67-B39-C12-D30
A39-B39-C12-D30
A65-B39-C12-D30
A66-B39-C12-D30
A2-B45-C12-D30
A3-B45-C12-D30
A9-B45-C12-D30
A13-B45-C12-D30
A24-B45-C12-D30
A69-B45-C12-D30
A67-B45-C12-D30
A39-B45-C12-D30
A65-B45-C12-D30
A66-B45-C12-D30
A2-B53-C12-D30
A3-B53-C12-D30
A9-B53-C12-D30
A13-B53-C12-D30
A24-B53-C12-D30
A69-B53-C12-D30
A67-B53-C12-D30
A39-B53-C12-D30
A65-B53-C12-D30
A66-B53-C12-D30
A2-B79-C12-D30

-continued

A3-B79-C12-D30
A9-B79-C12-D30
A13-B79-C12-D30
A24-B79-C12-D30
A69-B79-C12-D30
A67-B79-C12-D30
A39-B79-C12-D30
A65-B79-C12-D30
A66-B79-C12-D30
A2-B80-C12-D30
A3-B80-C12-D30
A9-B80-C12-D30
A13-B80-C12-D30
A24-B80-C12-D30
A69-B80-C12-D30
A67-B80-C12-D30
A39-B80-C12-D30
A65-B80-C12-D30
A66-B80-C12-D30
A2-B85-C12-D30
A3-B85-C12-D30
A9-B85-C12-D30
A13-B85-C12-D30
A24-B85-C12-D30
A69-B85-C12-D30
A67-B85-C12-D30
A39-B85-C12-D30
A65-B85-C12-D30
A66-B85-C12-D30
A2-B86-C12-D30
A3-B86-C12-D30
A9-B86-C12-D30
A13-B86-C12-D30
A24-B86-C12-D30
A69-B86-C12-D30
A67-B86-C12-D30
A39-B86-C12-D30
A65-B86-C12-D30
A66-B86-C12-D30
A2-B87-C12-D30
A3-B87-C12-D30
A9-B87-C12-D30
A13-B87-C12-D30
A24-B87-C12-D30
A69-B87-C12-D30
A67-B87-C12-D30
A39-B87-C12-D30
A65-B87-C12-D30
A66-B87-C12-D30
A2-B89-C12-D30
A3-B89-C12-D30
A9-B89-C12-D30
A13-B89-C12-D30
A24-B89-C12-D30
A69-B89-C12-D30
A67-B89-C12-D30
A39-B89-C12-D30
A65-B89-C12-D30
A66-B89-C12-D30
A2-B92-C12-D30
A3-B92-C12-D30
A9-B92-C12-D30
A13-B92-C12-D30
A24-B92-C12-D30
A69-B92-C12-D30
A67-B92-C12-D30
A39-B92-C12-D30
A65-B92-C12-D30
A66-B92-C12-D30
A2-B4-C13-D30
A3-B4-C13-D30
A9-B4-C13-D30
A13-B4-C13-D30
A24-B4-C13-D30
A69-B4-C13-D30
A67-B4-C13-D30
A39-B4-C13-D30
A65-B4-C13-D30
A66-B4-C13-D30
A2-B5-C13-D30

-continued

A3-B5-C13-D30
A9-B5-C13-D30
A13-B5-C13-D30
A24-B5-C13-D30
A69-B5-C13-D30
A67-B5-C13-D30
A39-B5-C13-D30
A65-B5-C13-D30
A66-B5-C13-D30
A2-B6-C13-D30
A3-B6-C13-D30
A9-B6-C13-D30
A13-B6-C13-D30
A24-B6-C13-D30
A69-B6-C13-D30
A67-B6-C13-D30
A39-B6-C13-D30
A65-B6-C13-D30
A66-B6-C13-D30
A2-B32-C13-D30
A3-B32-C13-D30
A9-B32-C13-D30
A13-B32-C13-D30
A24-B32-C13-D30
A69-B32-C13-D30
A67-B32-C13-D30
A39-B32-C13-D30
A65-B32-C13-D30
A66-B32-C13-D30
A2-B39-C13-D30
A3-B39-C13-D30
A9-B39-C13-D30
A13-B39-C13-D30
A24-B39-C13-D30
A69-B39-C13-D30
A67-B39-C13-D30
A39-B39-C13-D30
A65-B39-C13-D30
A66-B39-C13-D30
A2-B45-C13-D30
A3-B45-C13-D30
A9-B45-C13-D30
A13-B45-C13-D30
A24-B45-C13-D30
A69-B45-C13-D30
A67-B45-C13-D30
A39-B45-C13-D30
A65-B45-C13-D30
A66-B45-C13-D30
A2-B53-C13-D30
A3-B53-C13-D30
A9-B53-C13-D30
A13-B53-C13-D30
A24-B53-C13-D30
A69-B53-C13-D30
A67-B53-C13-D30
A39-B53-C13-D30
A65-B53-C13-D30
A66-B53-C13-D30
A2-B79-C13-D30
A3-B79-C13-D30
A9-B79-C13-D30
A13-B79-C13-D30
A24-B79-C13-D30
A69-B79-C13-D30
A67-B79-C13-D30
A39-B79-C13-D30
A65-B79-C13-D30
A66-B79-C13-D30
A2-B80-C13-D30
A3-B80-C13-D30
A9-B80-C13-D30
A13-B80-C13-D30
A24-B80-C13-D30
A69-B80-C13-D30
A67-B80-C13-D30
A39-B80-C13-D30
A65-B80-C13-D30
A66-B80-C13-D30
A2-B85-C13-D30

-continued

A3-B85-C13-D30
A9-B85-C13-D30
A13-B85-C13-D30
A24-B85-C13-D30
A69-B85-C13-D30
A67-B85-C13-D30
A39-B85-C13-D30
A65-B85-C13-D30
A66-B85-C13-D30
A2-B86-C13-D30
A3-B86-C13-D30
A9-B86-C13-D30
A13-B86-C13-D30
A24-B86-C13-D30
A69-B86-C13-D30
A67-B86-C13-D30
A39-B86-C13-D30
A65-B86-C13-D30
A66-B86-C13-D30
A2-B87-C13-D30
A3-B87-C13-D30
A9-B87-C13-D30
A13-B87-C13-D30
A24-B87-C13-D30
A69-B87-C13-D30
A67-B87-C13-D30
A39-B87-C13-D30
A65-B87-C13-D30
A66-B87-C13-D30
A2-B89-C13-D30
A3-B89-C13-D30
A9-B89-C13-D30
A13-B89-C13-D30
A24-B89-C13-D30
A69-B89-C13-D30
A67-B89-C13-D30
A39-B89-C13-D30
A65-B89-C13-D30
A66-B89-C13-D30
A2-B92-C13-D30
A3-B92-C13-D30
A9-B92-C13-D30
A13-B92-C13-D30
A24-B92-C13-D30
A69-B92-C13-D30
A67-B92-C13-D30
A39-B92-C13-D30
A65-B92-C13-D30
A66-B92-C13-D30
A2-B4-C1-D31
A3-B4-C1-D31
A9-B4-C1-D31
A13-B4-C1-D31
A24-B4-C1-D31
A69-B4-C1-D31
A67-B4-C1-D31
A39-B4-C1-D31
A65-B4-C1-D31
A66-B4-C1-D31
A2-B5-C1-D31
A3-B5-C1-D31
A9-B5-C1-D31
A13-B5-C1-D31
A24-B5-C1-D31
A69-B5-C1-D31
A67-B5-C1-D31
A39-B5-C1-D31
A65-B5-C1-D31
A66-B5-C1-D31
A2-B6-C1-D31
A3-B6-C1-D31
A9-B6-C1-D31
A13-B6-C1-D31
A24-B6-C1-D31
A69-B6-C1-D31
A67-B6-C1-D31
A39-B6-C1-D31
A65-B6-C1-D31
A66-B6-C1-D31
A2-B32-C1-D31

-continued

A3-B32-C1-D31
A9-B32-C1-D31
A13-B32-C1-D31
A24-B32-C1-D31
A69-B32-C1-D31
A67-B32-C1-D31
A39-B32-C1-D31
A65-B32-C1-D31
A66-B32-C1-D31
A2-B39-C1-D31
A3-B39-C1-D31
A9-B39-C1-D31
A13-B39-C1-D31
A24-B39-C1-D31
A69-B39-C1-D31
A67-B39-C1-D31
A39-B39-C1-D31
A65-B39-C1-D31
A66-B39-C1-D31
A2-B45-C1-D31
A3-B45-C1-D31
A9-B45-C1-D31
A13-B45-C1-D31
A24-B45-C1-D31
A69-B45-C1-D31
A67-B45-C1-D31
A39-B45-C1-D31
A65-B45-C1-D31
A66-B45-C1-D31
A2-B53-C1-D31
A3-B53-C1-D31
A9-B53-C1-D31
A13-B53-C1-D31
A24-B53-C1-D31
A69-B53-C1-D31
A67-B53-C1-D31
A39-B53-C1-D31
A65-B53-C1-D31
A66-B53-C1-D31
A2-B79-C1-D31
A3-B79-C1-D31
A9-B79-C1-D31
A13-B79-C1-D31
A24-B79-C1-D31
A69-B79-C1-D31
A67-B79-C1-D31
A39-B79-C1-D31
A65-B79-C1-D31
A66-B79-C1-D31
A2-B80-C1-D31
A3-B80-C1-D31
A9-B80-C1-D31
A13-B80-C1-D31
A24-B80-C1-D31
A69-B80-C1-D31
A67-B80-C1-D31
A39-B80-C1-D31
A65-B80-C1-D31
A66-B80-C1-D31
A2-B85-C1-D31
A3-B85-C1-D31
A9-B85-C1-D31
A13-B85-C1-D31
A24-B85-C1-D31
A69-B85-C1-D31
A67-B85-C1-D31
A39-B85-C1-D31
A65-B85-C1-D31
A66-B85-C1-D31
A2-B86-C1-D31
A3-B86-C1-D31
A9-B86-C1-D31
A13-B86-C1-D31
A24-B86-C1-D31
A69-B86-C1-D31
A67-B86-C1-D31
A39-B86-C1-D31
A65-B86-C1-D31
A66-B86-C1-D31
A2-B87-C1-D31

-continued

A3-B87-C1-D31
A9-B87-C1-D31
A13-B87-C1-D31
A24-B87-C1-D31
A69-B87-C1-D31
A67-B87-C1-D31
A39-B87-C1-D31
A65-B87-C1-D31
A66-B87-C1-D31
A2-B89-C1-D31
A3-B89-C1-D31
A9-B89-C1-D31
A13-B89-C1-D31
A24-B89-C1-D31
A69-B89-C1-D31
A67-B89-C1-D31
A39-B89-C1-D31
A65-B89-C1-D31
A66-B89-C1-D31
A2-B92-C1-D31
A3-B92-C1-D31
A9-B92-C1-D31
A13-B92-C1-D31
A24-B92-C1-D31
A69-B92-C1-D31
A67-B92-C1-D31
A39-B92-C1-D31
A65-B92-C1-D31
A66-B92-C1-D31
A2-B4-C2-D31
A3-B4-C2-D31
A9-B4-C2-D31
A13-B4-C2-D31
A24-B4-C2-D31
A69-B4-C2-D31
A67-B4-C2-D31
A39-B4-C2-D31
A65-B4-C2-D31
A66-B4-C2-D31
A2-B5-C2-D31
A3-B5-C2-D31
A9-B5-C2-D31
A13-B5-C2-D31
A24-B5-C2-D31
A69-B5-C2-D31
A67-B5-C2-D31
A39-B5-C2-D31
A65-B5-C2-D31
A66-B5-C2-D31
A2-B6-C2-D31
A3-B6-C2-D31
A9-B6-C2-D31
A13-B6-C2-D31
A24-B6-C2-D31
A69-B6-C2-D31
A67-B6-C2-D31
A39-B6-C2-D31
A65-B6-C2-D31
A66-B6-C2-D31
A2-B32-C2-D31
A3-B32-C2-D31
A9-B32-C2-D31
A13-B32-C2-D31
A24-B32-C2-D31
A69-B32-C2-D31
A67-B32-C2-D31
A39-B32-C2-D31
A65-B32-C2-D31
A66-B32-C2-D31
A2-B39-C2-D31
A3-B39-C2-D31
A9-B39-C2-D31
A13-B39-C2-D31
A24-B39-C2-D31
A69-B39-C2-D31
A67-B39-C2-D31
A39-B39-C2-D31
A65-B39-C2-D31
A66-B39-C2-D31
A2-B45-C2-D31

-continued

A3-B45-C2-D31
A9-B45-C2-D31
A13-B45-C2-D31
A24-B45-C2-D31
A69-B45-C2-D31
A67-B45-C2-D31
A39-B45-C2-D31
A65-B45-C2-D31
A66-B45-C2-D31
A2-B53-C2-D31
A3-B53-C2-D31
A9-B53-C2-D31
A13-B53-C2-D31
A24-B53-C2-D31
A69-B53-C2-D31
A67-B53-C2-D31
A39-B53-C2-D31
A65-B53-C2-D31
A66-B53-C2-D31
A2-B79-C2-D31
A3-B79-C2-D31
A9-B79-C2-D31
A13-B79-C2-D31
A24-B79-C2-D31
A69-B79-C2-D31
A67-B79-C2-D31
A39-B79-C2-D31
A65-B79-C2-D31
A66-B79-C2-D31
A2-B80-C2-D31
A3-B80-C2-D31
A9-B80-C2-D31
A13-B80-C2-D31
A24-B80-C2-D31
A69-B80-C2-D31
A67-B80-C2-D31
A39-B80-C2-D31
A65-B80-C2-D31
A66-B80-C2-D31
A2-B85-C2-D31
A3-B85-C2-D31
A9-B85-C2-D31
A13-B85-C2-D31
A24-B85-C2-D31
A69-B85-C2-D31
A67-B85-C2-D31
A39-B85-C2-D31
A65-B85-C2-D31
A66-B85-C2-D31
A2-B86-C2-D31
A3-B86-C2-D31
A9-B86-C2-D31
A13-B86-C2-D31
A24-B86-C2-D31
A69-B86-C2-D31
A67-B86-C2-D31
A39-B86-C2-D31
A65-B86-C2-D31
A66-B86-C2-D31
A2-B87-C2-D31
A3-B87-C2-D31
A9-B87-C2-D31
A13-B87-C2-D31
A24-B87-C2-D31
A69-B87-C2-D31
A67-B87-C2-D31
A39-B87-C2-D31
A65-B87-C2-D31
A66-B87-C2-D31
A2-B89-C2-D31
A3-B89-C2-D31
A9-B89-C2-D31
A13-B89-C2-D31
A24-B89-C2-D31
A69-B89-C2-D31
A67-B89-C2-D31
A39-B89-C2-D31
A65-B89-C2-D31
A66-B89-C2-D31
A2-B92-C2-D31

-continued

A3-B92-C2-D31
A9-B92-C2-D31
A13-B92-C2-D31
A24-B92-C2-D31
A69-B92-C2-D31
A67-B92-C2-D31
A39-B92-C2-D31
A65-B92-C2-D31
A66-B92-C2-D31
A2-B4-C3-D31
A3-B4-C3-D31
A9-B4-C3-D31
A13-B4-C3-D31
A24-B4-C3-D31
A69-B4-C3-D31
A67-B4-C3-D31
A39-B4-C3-D31
A65-B4-C3-D31
A66-B4-C3-D31
A2-B5-C3-D31
A3-B5-C3-D31
A9-B5-C3-D31
A13-B5-C3-D31
A24-B5-C3-D31
A69-B5-C3-D31
A67-B5-C3-D31
A39-B5-C3-D31
A65-B5-C3-D31
A66-B5-C3-D31
A2-B6-C3-D31
A3-B6-C3-D31
A9-B6-C3-D31
A13-B6-C3-D31
A24-B6-C3-D31
A69-B6-C3-D31
A67-B6-C3-D31
A39-B6-C3-D31
A65-B6-C3-D31
A66-B6-C3-D31
A2-B32-C3-D31
A3-B32-C3-D31
A9-B32-C3-D31
A13-B32-C3-D31
A24-B32-C3-D31
A69-B32-C3-D31
A67-B32-C3-D31
A39-B32-C3-D31
A65-B32-C3-D31
A66-B32-C3-D31
A2-B39-C3-D31
A3-B39-C3-D31
A9-B39-C3-D31
A13-B39-C3-D31
A24-B39-C3-D31
A69-B39-C3-D31
A67-B39-C3-D31
A39-B39-C3-D31
A65-B39-C3-D31
A66-B39-C3-D31
A2-B45-C3-D31
A3-B45-C3-D31
A9-B45-C3-D31
A13-B45-C3-D31
A24-B45-C3-D31
A69-B45-C3-D31
A67-B45-C3-D31
A39-B45-C3-D31
A65-B45-C3-D31
A66-B45-C3-D31
A2-B53-C3-D31
A3-B53-C3-D31
A9-B53-C3-D31
A13-B53-C3-D31
A24-B53-C3-D31
A69-B53-C3-D31
A67-B53-C3-D31
A39-B53-C3-D31
A65-B53-C3-D31
A66-B53-C3-D31
A2-B79-C3-D31

-continued

A3-B79-C3-D31
A9-B79-C3-D31
A13-B79-C3-D31
A24-B79-C3-D31
A69-B79-C3-D31
A67-B79-C3-D31
A39-B79-C3-D31
A65-B79-C3-D31
A66-B79-C3-D31
A2-B80-C3-D31
A3-B80-C3-D31
A9-B80-C3-D31
A13-B80-C3-D31
A24-B80-C3-D31
A69-B80-C3-D31
A67-B80-C3-D31
A39-B80-C3-D31
A65-B80-C3-D31
A66-B80-C3-D31
A2-B85-C3-D31
A3-B85-C3-D31
A9-B85-C3-D31
A13-B85-C3-D31
A24-B85-C3-D31
A69-B85-C3-D31
A67-B85-C3-D31
A39-B85-C3-D31
A65-B85-C3-D31
A66-B85-C3-D31
A2-B86-C3-D31
A3-B86-C3-D31
A9-B86-C3-D31
A13-B86-C3-D31
A24-B86-C3-D31
A69-B86-C3-D31
A67-B86-C3-D31
A39-B86-C3-D31
A65-B86-C3-D31
A66-B86-C3-D31
A2-B87-C3-D31
A3-B87-C3-D31
A9-B87-C3-D31
A13-B87-C3-D31
A24-B87-C3-D31
A69-B87-C3-D31
A67-B87-C3-D31
A39-B87-C3-D31
A65-B87-C3-D31
A66-B87-C3-D31
A2-B89-C3-D31
A3-B89-C3-D31
A9-B89-C3-D31
A13-B89-C3-D31
A24-B89-C3-D31
A69-B89-C3-D31
A67-B89-C3-D31
A39-B89-C3-D31
A65-B89-C3-D31
A66-B89-C3-D31
A2-B92-C3-D31
A3-B92-C3-D31
A9-B92-C3-D31
A13-B92-C3-D31
A24-B92-C3-D31
A69-B92-C3-D31
A67-B92-C3-D31
A39-B92-C3-D31
A65-B92-C3-D31
A66-B92-C3-D31
A2-B4-C4-D31
A3-B4-C4-D31
A9-B4-C4-D31
A13-B4-C4-D31
A24-B4-C4-D31
A69-B4-C4-D31
A67-B4-C4-D31
A39-B4-C4-D31
A65-B4-C4-D31
A66-B4-C4-D31
A2-B5-C4-D31

-continued

A3-B5-C4-D31
A9-B5-C4-D31
A13-B5-C4-D31
A24-B5-C4-D31
A69-B5-C4-D31
A67-B5-C4-D31
A39-B5-C4-D31
A65-B5-C4-D31
A66-B5-C4-D31
A2-B6-C4-D31
A3-B6-C4-D31
A9-B6-C4-D31
A13-B6-C4-D31
A24-B6-C4-D31
A69-B6-C4-D31
A67-B6-C4-D31
A39-B6-C4-D31
A65-B6-C4-D31
A66-B6-C4-D31
A2-B32-C4-D31
A3-B32-C4-D31
A9-B32-C4-D31
A13-B32-C4-D31
A24-B32-C4-D31
A69-B32-C4-D31
A67-B32-C4-D31
A39-B32-C4-D31
A65-B32-C4-D31
A66-B32-C4-D31
A2-B39-C4-D31
A3-B39-C4-D31
A9-B39-C4-D31
A13-B39-C4-D31
A24-B39-C4-D31
A69-B39-C4-D31
A67-B39-C4-D31
A39-B39-C4-D31
A65-B39-C4-D31
A66-B39-C4-D31
A2-B45-C4-D31
A3-B45-C4-D31
A9-B45-C4-D31
A13-B45-C4-D31
A24-B45-C4-D31
A69-B45-C4-D31
A67-B45-C4-D31
A39-B45-C4-D31
A65-B45-C4-D31
A66-B45-C4-D31
A2-B53-C4-D31
A3-B53-C4-D31
A9-B53-C4-D31
A13-B53-C4-D31
A24-B53-C4-D31
A69-B53-C4-D31
A67-B53-C4-D31
A39-B53-C4-D31
A65-B53-C4-D31
A66-B53-C4-D31
A2-B79-C4-D31
A3-B79-C4-D31
A9-B79-C4-D31
A13-B79-C4-D31
A24-B79-C4-D31
A69-B79-C4-D31
A67-B79-C4-D31
A39-B79-C4-D31
A65-B79-C4-D31
A66-B79-C4-D31
A2-B80-C4-D31
A3-B80-C4-D31
A9-B80-C4-D31
A13-B80-C4-D31
A24-B80-C4-D31
A69-B80-C4-D31
A67-B80-C4-D31

-continued
A39-B80-C4-D31
A65-B80-C4-D31
A66-B80-C4-D31
A2-B85-C4-D31
A3-B85-C4-D31
A9-B85-C4-D31
A13-B85-C4-D31
A24-B85-C4-D31
A69-B85-C4-D31
A67-B85-C4-D31
A39-B85-C4-D31
A65-B85-C4-D31
A66-B85-C4-D31
A2-B86-C4-D31
A3-B86-C4-D31
A9-B86-C4-D31
A13-B86-C4-D31
A24-B86-C4-D31
A69-B86-C4-D31
A67-B86-C4-D31
A39-B86-C4-D31
A65-B86-C4-D31
A66-B86-C4-D31
A2-B87-C4-D31
A3-B87-C4-D31
A9-B87-C4-D31
A13-B87-C4-D31
A24-B87-C4-D31
A69-B87-C4-D31
A67-B87-C4-D31
A39-B87-C4-D31
A65-B87-C4-D31
A66-B87-C4-D31
A2-B89-C4-D31
A3-B89-C4-D31
A9-B89-C4-D31
A13-B89-C4-D31
A24-B89-C4-D31
A69-B89-C4-D31
A67-B89-C4-D31
A39-B89-C4-D31
A65-B89-C4-D31
A66-B89-C4-D31
A2-B92-C4-D31
A3-B92-C4-D31
A9-B92-C4-D31
A13-B92-C4-D31
A24-B92-C4-D31
A69-B92-C4-D31
A67-B92-C4-D31
A39-B92-C4-D31
A65-B92-C4-D31
A66-B92-C4-D31
A2-B4-C5-D31
A3-B4-C5-D31
A9-B4-C5-D31
A13-B4-C5-D31
A24-B4-C5-D31
A69-B4-C5-D31
A67-B4-C5-D31
A39-B4-C5-D31
A65-B4-C5-D31
A66-B4-C5-D31
A2-B5-C5-D31
A3-B5-C5-D31
A9-B5-C5-D31
A13-B5-C5-D31
A24-B5-C5-D31
A69-B5-C5-D31
A67-B5-C5-D31
A39-B5-C5-D31
A65-B5-C5-D31
A66-B5-C5-D31
A2-B6-C5-D31
A3-B6-C5-D31
A9-B6-C5-D31
A13-B6-C5-D31
A24-B6-C5-D31
A69-B6-C5-D31
A67-B6-C5-D31

-continued
A39-B6-C5-D31
A65-B6-C5-D31
A66-B6-C5-D31
A2-B32-C5-D31
A3-B32-C5-D31
A9-B32-C5-D31
A13-B32-C5-D31
A24-B32-C5-D31
A69-B32-C5-D31
A67-B32-C5-D31
A39-B32-C5-D31
A65-B32-C5-D31
A66-B32-C5-D31
A2-B39-C5-D31
A3-B39-C5-D31
A9-B39-C5-D31
A13-B39-C5-D31
A24-B39-C5-D31
A69-B39-C5-D31
A67-B39-C5-D31
A39-B39-C5-D31
A65-B39-C5-D31
A66-B39-C5-D31
A2-B45-C5-D31
A3-B45-C5-D31
A9-B45-C5-D31
A13-B45-C5-D31
A24-B45-C5-D31
A69-B45-C5-D31
A67-B45-C5-D31
A39-B45-C5-D31
A65-B45-C5-D31
A66-B45-C5-D31
A2-B53-C5-D31
A3-B53-C5-D31
A9-B53-C5-D31
A13-B53-C5-D31
A24-B53-C5-D31
A69-B53-C5-D31
A67-B53-C5-D31
A39-B53-C5-D31
A65-B53-C5-D31
A66-B53-C5-D31
A2-B79-C5-D31
A3-B79-C5-D31
A9-B79-C5-D31
A13-B79-C5-D31
A24-B79-C5-D31
A69-B79-C5-D31
A67-B79-C5-D31
A39-B79-C5-D31
A65-B79-C5-D31
A66-B79-C5-D31
A2-B80-C5-D31
A3-B80-C5-D31
A9-B80-C5-D31
A13-B80-C5-D31
A24-B80-C5-D31
A69-B80-C5-D31
A67-B80-C5-D31
A39-B80-C5-D31
A65-B80-C5-D31
A66-B80-C5-D31
A2-B85-C5-D31
A3-B85-C5-D31
A9-B85-C5-D31
A13-B85-C5-D31
A24-B85-C5-D31
A69-B85-C5-D31
A67-B85-C5-D31
A39-B85-C5-D31
A65-B85-C5-D31
A66-B85-C5-D31
A2-B86-C5-D31
A3-B86-C5-D31
A9-B86-C5-D31
A13-B86-C5-D31
A24-B86-C5-D31
A69-B86-C5-D31
A67-B86-C5-D31

-continued
A39-B86-C5-D31
A65-B86-C5-D31
A66-B86-C5-D31
A2-B87-C5-D31
A3-B87-C5-D31
A9-B87-C5-D31
A13-B87-C5-D31
A24-B87-C5-D31
A69-B87-C5-D31
A67-B87-C5-D31
A39-B87-C5-D31
A65-B87-C5-D31
A66-B87-C5-D31
A2-B89-C5-D31
A3-B89-C5-D31
A9-B89-C5-D31
A13-B89-C5-D31
A24-B89-C5-D31
A69-B89-C5-D31
A67-B89-C5-D31
A39-B89-C5-D31
A65-B89-C5-D31
A66-B89-C5-D31
A2-B92-C5-D31
A3-B92-C5-D31
A9-B92-C5-D31
A13-B92-C5-D31
A24-B92-C5-D31
A69-B92-C5-D31
A67-B92-C5-D31
A39-B92-C5-D31
A65-B92-C5-D31
A66-B92-C5-D31
A2-B4-C6-D31
A3-B4-C6-D31
A9-B4-C6-D31
A13-B4-C6-D31
A24-B4-C6-D31
A69-B4-C6-D31
A67-B4-C6-D31
A39-B4-C6-D31
A65-B4-C6-D31
A66-B4-C6-D31
A2-B5-C6-D31
A3-B5-C6-D31
A9-B5-C6-D31
A13-B5-C6-D31
A24-B5-C6-D31
A69-B5-C6-D31
A67-B5-C6-D31
A39-B5-C6-D31
A65-B5-C6-D31
A66-B5-C6-D31
A2-B6-C6-D31
A3-B6-C6-D31
A9-B6-C6-D31
A13-B6-C6-D31
A24-B6-C6-D31
A69-B6-C6-D31
A67-B6-C6-D31
A39-B6-C6-D31
A65-B6-C6-D31
A66-B6-C6-D31
A2-B32-C6-D31
A3-B32-C6-D31
A9-B32-C6-D31
A13-B32-C6-D31
A24-B32-C6-D31
A69-B32-C6-D31
A67-B32-C6-D31
A39-B32-C6-D31
A65-B32-C6-D31
A66-B32-C6-D31
A2-B39-C6-D31
A3-B39-C6-D31
A9-B39-C6-D31
A13-B39-C6-D31
A24-B39-C6-D31
A69-B39-C6-D31
A67-B39-C6-D31

-continued
A39-B39-C6-D31
A65-B39-C6-D31
A66-B39-C6-D31
A2-B45-C6-D31
A3-B45-C6-D31
A9-B45-C6-D31
A13-B45-C6-D31
A24-B45-C6-D31
A69-B45-C6-D31
A67-B45-C6-D31
A39-B45-C6-D31
A65-B45-C6-D31
A66-B45-C6-D31
A2-B53-C6-D31
A3-B53-C6-D31
A9-B53-C6-D31
A13-B53-C6-D31
A24-B53-C6-D31
A69-B53-C6-D31
A67-B53-C6-D31
A39-B53-C6-D31
A65-B53-C6-D31
A66-B53-C6-D31
A2-B79-C6-D31
A3-B79-C6-D31
A9-B79-C6-D31
A13-B79-C6-D31
A24-B79-C6-D31
A69-B79-C6-D31
A67-B79-C6-D31
A39-B79-C6-D31
A65-B79-C6-D31
A66-B79-C6-D31
A2-B80-C6-D31
A3-B80-C6-D31
A9-B80-C6-D31
A13-B80-C6-D31
A24-B80-C6-D31
A69-B80-C6-D31
A67-B80-C6-D31
A39-B80-C6-D31
A65-B80-C6-D31
A66-B80-C6-D31
A2-B85-C6-D31
A3-B85-C6-D31
A9-B85-C6-D31
A13-B85-C6-D31
A24-B85-C6-D31
A69-B85-C6-D31
A67-B85-C6-D31
A39-B85-C6-D31
A65-B85-C6-D31
A66-B85-C6-D31
A2-B86-C6-D31
A3-B86-C6-D31
A9-B86-C6-D31
A13-B86-C6-D31
A24-B86-C6-D31
A69-B86-C6-D31
A67-B86-C6-D31
A39-B86-C6-D31
A65-B86-C6-D31
A66-B86-C6-D31
A2-B87-C6-D31
A3-B87-C6-D31
A9-B87-C6-D31
A13-B87-C6-D31
A24-B87-C6-D31
A69-B87-C6-D31
A67-B87-C6-D31
A39-B87-C6-D31
A65-B87-C6-D31
A66-B87-C6-D31
A2-B89-C6-D31
A3-B89-C6-D31
A9-B89-C6-D31
A13-B89-C6-D31
A24-B89-C6-D31
A69-B89-C6-D31
A67-B89-C6-D31

-continued
A39-B89-C6-D31
A65-B89-C6-D31
A66-B89-C6-D31
A2-B92-C6-D31
A3-B92-C6-D31
A9-B92-C6-D31
A13-B92-C6-D31
A24-B92-C6-D31
A69-B92-C6-D31
A67-B92-C6-D31
A39-B92-C6-D31
A65-B92-C6-D31
A66-B92-C6-D31
A2-B4-C7-D31
A3-B4-C7-D31
A9-B4-C7-D31
A13-B4-C7-D31
A24-B4-C7-D31
A69-B4-C7-D31
A67-B4-C7-D31
A39-B4-C7-D31
A65-B4-C7-D31
A66-B4-C7-D31
A2-B5-C7-D31
A3-B5-C7-D31
A9-B5-C7-D31
A13-B5-C7-D31
A24-B5-C7-D31
A69-B5-C7-D31
A67-B5-C7-D31
A39-B5-C7-D31
A65-B5-C7-D31
A66-B5-C7-D31
A2-B6-C7-D31
A3-B6-C7-D31
A9-B6-C7-D31
A13-B6-C7-D31
A24-B6-C7-D31
A69-B6-C7-D31
A67-B6-C7-D31
A39-B6-C7-D31
A65-B6-C7-D31
A66-B6-C7-D31
A2-B32-C7-D31
A3-B32-C7-D31
A9-B32-C7-D31
A13-B32-C7-D31
A24-B32-C7-D31
A69-B32-C7-D31
A67-B32-C7-D31
A39-B32-C7-D31
A65-B32-C7-D31
A66-B32-C7-D31
A2-B39-C7-D31
A3-B39-C7-D31
A9-B39-C7-D31
A13-B39-C7-D31
A24-B39-C7-D31
A69-B39-C7-D31
A67-B39-C7-D31
A39-B39-C7-D31
A65-B39-C7-D31
A66-B39-C7-D31
A2-B45-C7-D31
A3-B45-C7-D31
A9-B45-C7-D31
A13-B45-C7-D31
A24-B45-C7-D31
A69-B45-C7-D31
A67-B45-C7-D31
A39-B45-C7-D31
A65-B45-C7-D31
A66-B45-C7-D31
A2-B53-C7-D31
A3-B53-C7-D31
A9-B53-C7-D31
A13-B53-C7-D31
A24-B53-C7-D31
A69-B53-C7-D31
A67-B53-C7-D31

-continued
A39-B53-C7-D31
A65-B53-C7-D31
A66-B53-C7-D31
A2-B79-C7-D31
A3-B79-C7-D31
A9-B79-C7-D31
A13-B79-C7-D31
A24-B79-C7-D31
A69-B79-C7-D31
A67-B79-C7-D31
A39-B79-C7-D31
A65-B79-C7-D31
A66-B79-C7-D31
A2-B80-C7-D31
A3-B80-C7-D31
A9-B80-C7-D31
A13-B80-C7-D31
A24-B80-C7-D31
A69-B80-C7-D31
A67-B80-C7-D31
A39-B80-C7-D31
A65-B80-C7-D31
A66-B80-C7-D31
A2-B85-C7-D31
A3-B85-C7-D31
A9-B85-C7-D31
A13-B85-C7-D31
A24-B85-C7-D31
A69-B85-C7-D31
A67-B85-C7-D31
A39-B85-C7-D31
A65-B85-C7-D31
A66-B85-C7-D31
A2-B86-C7-D31
A3-B86-C7-D31
A9-B86-C7-D31
A13-B86-C7-D31
A24-B86-C7-D31
A69-B86-C7-D31
A67-B86-C7-D31
A39-B86-C7-D31
A65-B86-C7-D31
A66-B86-C7-D31
A2-B87-C7-D31
A3-B87-C7-D31
A9-B87-C7-D31
A13-B87-C7-D31
A24-B87-C7-D31
A69-B87-C7-D31
A67-B87-C7-D31
A39-B87-C7-D31
A65-B87-C7-D31
A66-B87-C7-D31
A2-B89-C7-D31
A3-B89-C7-D31
A9-B89-C7-D31
A13-B89-C7-D31
A24-B89-C7-D31
A69-B89-C7-D31
A67-B89-C7-D31
A39-B89-C7-D31
A65-B89-C7-D31
A66-B89-C7-D31
A2-B92-C7-D31
A3-B92-C7-D31
A9-B92-C7-D31
A13-B92-C7-D31
A24-B92-C7-D31
A69-B92-C7-D31
A67-B92-C7-D31
A39-B92-C7-D31
A65-B92-C7-D31
A66-B92-C7-D31
A2-B4-C8-D31
A3-B4-C8-D31
A9-B4-C8-D31
A13-B4-C8-D31
A24-B4-C8-D31
A69-B4-C8-D31
A67-B4-C8-D31

-continued

A39-B4-C8-D31
A65-B4-C8-D31
A66-B4-C8-D31
A2-B5-C8-D31
A3-B5-C8-D31
A9-B5-C8-D31
A13-B5-C8-D31
A24-B5-C8-D31
A69-B5-C8-D31
A67-B5-C8-D31
A39-B5-C8-D31
A65-B5-C8-D31
A66-B5-C8-D31
A2-B6-C8-D31
A3-B6-C8-D31
A9-B6-C8-D31
A13-B6-C8-D31
A24-B6-C8-D31
A69-B6-C8-D31
A67-B6-C8-D31
A39-B6-C8-D31
A65-B6-C8-D31
A66-B6-C8-D31
A2-B32-C8-D31
A3-B32-C8-D31
A9-B32-C8-D31
A13-B32-C8-D31
A24-B32-C8-D31
A69-B32-C8-D31
A67-B32-C8-D31
A39-B32-C8-D31
A65-B32-C8-D31
A66-B32-C8-D31
A2-B39-C8-D31
A3-B39-C8-D31
A9-B39-C8-D31
A13-B39-C8-D31
A24-B39-C8-D31
A69-B39-C8-D31
A67-B39-C8-D31
A39-B39-C8-D31
A65-B39-C8-D31
A66-B39-C8-D31
A2-B45-C8-D31
A3-B45-C8-D31
A9-B45-C8-D31
A13-B45-C8-D31
A24-B45-C8-D31
A69-B45-C8-D31
A67-B45-C8-D31
A39-B45-C8-D31
A65-B45-C8-D31
A66-B45-C8-D31
A2-B53-C8-D31
A3-B53-C8-D31
A9-B53-C8-D31
A13-B53-C8-D31
A24-B53-C8-D31
A69-B53-C8-D31
A67-B53-C8-D31
A39-B53-C8-D31
A65-B53-C8-D31
A66-B53-C8-D31
A2-B79-C8-D31
A3-B79-C8-D31
A9-B79-C8-D31
A13-B79-C8-D31
A24-B79-C8-D31
A69-B79-C8-D31
A67-B79-C8-D31
A39-B79-C8-D31
A65-B79-C8-D31
A66-B79-C8-D31
A2-B80-C8-D31
A3-B80-C8-D31
A9-B80-C8-D31
A13-B80-C8-D31
A24-B80-C8-D31
A69-B80-C8-D31
A67-B80-C8-D31

-continued

A39-B80-C8-D31
A65-B80-C8-D31
A66-B80-C8-D31
A2-B85-C8-D31
A3-B85-C8-D31
A9-B85-C8-D31
A13-B85-C8-D31
A24-B85-C8-D31
A69-B85-C8-D31
A67-B85-C8-D31
A39-B85-C8-D31
A65-B85-C8-D31
A66-B85-C8-D31
A2-B86-C8-D31
A3-B86-C8-D31
A9-B86-C8-D31
A13-B86-C8-D31
A24-B86-C8-D31
A69-B86-C8-D31
A67-B86-C8-D31
A39-B86-C8-D31
A65-B86-C8-D31
A66-B86-C8-D31
A2-B87-C8-D31
A3-B87-C8-D31
A9-B87-C8-D31
A13-B87-C8-D31
A24-B87-C8-D31
A69-B87-C8-D31
A67-B87-C8-D31
A39-B87-C8-D31
A65-B87-C8-D31
A66-B87-C8-D31
A2-B89-C8-D31
A3-B89-C8-D31
A9-B89-C8-D31
A13-B89-C8-D31
A24-B89-C8-D31
A69-B89-C8-D31
A67-B89-C8-D31
A39-B89-C8-D31
A65-B89-C8-D31
A66-B89-C8-D31
A2-B92-C8-D31
A3-B92-C8-D31
A9-B92-C8-D31
A13-B92-C8-D31
A24-B92-C8-D31
A69-B92-C8-D31
A67-B92-C8-D31
A39-B92-C8-D31
A65-B92-C8-D31
A66-B92-C8-D31
A2-B4-C9-D31
A3-B4-C9-D31
A9-B4-C9-D31
A13-B4-C9-D31
A24-B4-C9-D31
A69-B4-C9-D31
A67-B4-C9-D31
A39-B4-C9-D31
A65-B4-C9-D31
A66-B4-C9-D31
A2-B5-C9-D31
A3-B5-C9-D31
A9-B5-C9-D31
A13-B5-C9-D31
A24-B5-C9-D31
A69-B5-C9-D31
A67-B5-C9-D31
A39-B5-C9-D31
A65-B5-C9-D31
A66-B5-C9-D31
A2-B6-C9-D31
A3-B6-C9-D31
A9-B6-C9-D31
A13-B6-C9-D31
A24-B6-C9-D31
A69-B6-C9-D31
A67-B6-C9-D31

-continued
A39-B6-C9-D31
A65-B6-C9-D31
A66-B6-C9-D31
A2-B32-C9-D31
A3-B32-C9-D31
A9-B32-C9-D31
A13-B32-C9-D31
A24-B32-C9-D31
A69-B32-C9-D31
A67-B32-C9-D31
A39-B32-C9-D31
A65-B32-C9-D31
A66-B32-C9-D31
A2-B39-C9-D31
A3-B39-C9-D31
A9-B39-C9-D31
A13-B39-C9-D31
A24-B39-C9-D31
A69-B39-C9-D31
A67-B39-C9-D31
A39-B39-C9-D31
A65-B39-C9-D31
A66-B39-C9-D31
A2-B45-C9-D31
A3-B45-C9-D31
A9-B45-C9-D31
A13-B45-C9-D31
A24-B45-C9-D31
A69-B45-C9-D31
A67-B45-C9-D31
A39-B45-C9-D31
A65-B45-C9-D31
A66-B45-C9-D31
A2-B53-C9-D31
A3-B53-C9-D31
A9-B53-C9-D31
A13-B53-C9-D31
A24-B53-C9-D31
A69-B53-C9-D31
A67-B53-C9-D31
A39-B53-C9-D31
A65-B53-C9-D31
A66-B53-C9-D31
A2-B79-C9-D31
A3-B79-C9-D31
A9-B79-C9-D31
A13-B79-C9-D31
A24-B79-C9-D31
A69-B79-C9-D31
A67-B79-C9-D31
A39-B79-C9-D31
A65-B79-C9-D31
A66-B79-C9-D31
A2-B80-C9-D31
A3-B80-C9-D31
A9-B80-C9-D31
A13-B80-C9-D31
A24-B80-C9-D31
A69-B80-C9-D31
A67-B80-C9-D31
A39-B80-C9-D31
A65-B80-C9-D31
A66-B80-C9-D31
A2-B85-C9-D31
A3-B85-C9-D31
A9-B85-C9-D31
A13-B85-C9-D31
A24-B85-C9-D31
A69-B85-C9-D31
A67-B85-C9-D31
A39-B85-C9-D31
A65-B85-C9-D31
A66-B85-C9-D31
A2-B86-C9-D31
A3-B86-C9-D31
A9-B86-C9-D31
A13-B86-C9-D31
A24-B86-C9-D31
A69-B86-C9-D31
A67-B86-C9-D31

-continued
A39-B86-C9-D31
A65-B86-C9-D31
A66-B86-C9-D31
A2-B87-C9-D31
A3-B87-C9-D31
A9-B87-C9-D31
A13-B87-C9-D31
A24-B87-C9-D31
A69-B87-C9-D31
A67-B87-C9-D31
A39-B87-C9-D31
A65-B87-C9-D31
A66-B87-C9-D31
A2-B89-C9-D31
A3-B89-C9-D31
A9-B89-C9-D31
A13-B89-C9-D31
A24-B89-C9-D31
A69-B89-C9-D31
A67-B89-C9-D31
A39-B89-C9-D31
A65-B89-C9-D31
A66-B89-C9-D31
A2-B92-C9-D31
A3-B92-C9-D31
A9-B92-C9-D31
A13-B92-C9-D31
A24-B92-C9-D31
A69-B92-C9-D31
A67-B92-C9-D31
A39-B92-C9-D31
A65-B92-C9-D31
A66-B92-C9-D31
A2-B4-C10-D31
A3-B4-C10-D31
A9-B4-C10-D31
A13-B4-C10-D31
A24-B4-C10-D31
A69-B4-C10-D31
A67-B4-C10-D31
A39-B4-C10-D31
A65-B4-C10-D31
A66-B4-C10-D31
A2-B5-C10-D31
A3-B5-C10-D31
A9-B5-C10-D31
A13-B5-C10-D31
A24-B5-C10-D31
A69-B5-C10-D31
A67-B5-C10-D31
A39-B5-C10-D31
A65-B5-C10-D31
A66-B5-C10-D31
A2-B6-C10-D31
A3-B6-C10-D31
A9-B6-C10-D31
A13-B6-C10-D31
A24-B6-C10-D31
A69-B6-C10-D31
A67-B6-C10-D31
A39-B6-C10-D31
A65-B6-C10-D31
A66-B6-C10-D31
A2-B32-C10-D31
A3-B32-C10-D31
A9-B32-C10-D31
A13-B32-C10-D31
A24-B32-C10-D31
A69-B32-C10-D31
A67-B32-C10-D31
A39-B32-C10-D31
A65-B32-C10-D31
A66-B32-C10-D31
A2-B39-C10-D31
A3-B39-C10-D31
A9-B39-C10-D31
A13-B39-C10-D31
A24-B39-C10-D31
A69-B39-C10-D31
A67-B39-C10-D31

-continued
A39-B39-C10-D31
A65-B39-C10-D31
A66-B39-C10-D31
A2-B45-C10-D31
A3-B45-C10-D31
A9-B45-C10-D31
A13-B45-C10-D31
A24-B45-C10-D31
A69-B45-C10-D31
A67-B45-C10-D31
A39-B45-C10-D31
A65-B45-C10-D31
A66-B45-C10-D31
A2-B53-C10-D31
A3-B53-C10-D31
A9-B53-C10-D31
A13-B53-C10-D31
A24-B53-C10-D31
A69-B53-C10-D31
A67-B53-C10-D31
A39-B53-C10-D31
A65-B53-C10-D31
A66-B53-C10-D31
A2-B79-C10-D31
A3-B79-C10-D31
A9-B79-C10-D31
A13-B79-C10-D31
A24-B79-C10-D31
A69-B79-C10-D31
A67-B79-C10-D31
A39-B79-C10-D31
A65-B79-C10-D31
A66-B79-C10-D31
A2-B80-C10-D31
A3-B80-C10-D31
A9-B80-C10-D31
A13-B80-C10-D31
A24-B80-C10-D31
A69-B80-C10-D31
A67-B80-C10-D31
A39-B80-C10-D31
A65-B80-C10-D31
A66-B80-C10-D31
A2-B85-C10-D31
A3-B85-C10-D31
A9-B85-C10-D31
A13-B85-C10-D31
A24-B85-C10-D31
A69-B85-C10-D31
A67-B85-C10-D31
A39-B85-C10-D31
A65-B85-C10-D31
A66-B85-C10-D31
A2-B86-C10-D31
A3-B86-C10-D31
A9-B86-C10-D31
A13-B86-C10-D31
A24-B86-C10-D31
A69-B86-C10-D31
A67-B86-C10-D31
A39-B86-C10-D31
A65-B86-C10-D31
A66-B86-C10-D31
A2-B87-C10-D31
A3-B87-C10-D31
A9-B87-C10-D31
A13-B87-C10-D31
A24-B87-C10-D31
A69-B87-C10-D31
A67-B87-C10-D31
A39-B87-C10-D31
A65-B87-C10-D31
A66-B87-C10-D31
A2-B89-C10-D31
A3-B89-C10-D31
A9-B89-C10-D31
A13-B89-C10-D31
A24-B89-C10-D31
A69-B89-C10-D31
A67-B89-C10-D31

-continued
A39-B89-C10-D31
A65-B89-C10-D31
A66-B89-C10-D31
A2-B92-C10-D31
A3-B92-C10-D31
A9-B92-C10-D31
A13-B92-C10-D31
A24-B92-C10-D31
A69-B92-C10-D31
A67-B92-C10-D31
A39-B92-C10-D31
A65-B92-C10-D31
A66-B92-C10-D31
A2-B4-C11-D31
A3-B4-C11-D31
A9-B4-C11-D31
A13-B4-C11-D31
A24-B4-C11-D31
A69-B4-C11-D31
A67-B4-C11-D31
A39-B4-C11-D31
A65-B4-C11-D31
A66-B4-C11-D31
A2-B5-C11-D31
A3-B5-C11-D31
A9-B5-C11-D31
A13-B5-C11-D31
A24-B5-C11-D31
A69-B5-C11-D31
A67-B5-C11-D31
A39-B5-C11-D31
A65-B5-C11-D31
A66-B5-C11-D31
A2-B6-C11-D31
A3-B6-C11-D31
A9-B6-C11-D31
A13-B6-C11-D31
A24-B6-C11-D31
A69-B6-C11-D31
A67-B6-C11-D31
A39-B6-C11-D31
A65-B6-C11-D31
A66-B6-C11-D31
A2-B32-C11-D31
A3-B32-C11-D31
A9-B32-C11-D31
A13-B32-C11-D31
A24-B32-C11-D31
A69-B32-C11-D31
A67-B32-C11-D31
A39-B32-C11-D31
A65-B32-C11-D31
A66-B32-C11-D31
A2-B39-C11-D31
A3-B39-C11-D31
A9-B39-C11-D31
A13-B39-C11-D31
A24-B39-C11-D31
A69-B39-C11-D31
A67-B39-C11-D31
A39-B39-C11-D31
A65-B39-C11-D31
A66-B39-C11-D31
A2-B45-C11-D31
A3-B45-C11-D31
A9-B45-C11-D31
A13-B45-C11-D31
A24-B45-C11-D31
A69-B45-C11-D31
A67-B45-C11-D31
A39-B45-C11-D31
A65-B45-C11-D31
A66-B45-C11-D31
A2-B53-C11-D31
A3-B53-C11-D31
A9-B53-C11-D31
A13-B53-C11-D31
A24-B53-C11-D31
A69-B53-C11-D31
A67-B53-C11-D31

-continued
A39-B53-C11-D31
A65-B53-C11-D31
A66-B53-C11-D31
A2-B79-C11-D31
A3-B79-C11-D31
A9-B79-C11-D31
A13-B79-C11-D31
A24-B79-C11-D31
A69-B79-C11-D31
A67-B79-C11-D31
A39-B79-C11-D31
A65-B79-C11-D31
A66-B79-C11-D31
A2-B80-C11-D31
A3-B80-C11-D31
A9-B80-C11-D31
A13-B80-C11-D31
A24-B80-C11-D31
A69-B80-C11-D31
A67-B80-C11-D31
A39-B80-C11-D31
A65-B80-C11-D31
A66-B80-C11-D31
A2-B85-C11-D31
A3-B85-C11-D31
A9-B85-C11-D31
A13-B85-C11-D31
A24-B85-C11-D31
A69-B85-C11-D31
A67-B85-C11-D31
A39-B85-C11-D31
A65-B85-C11-D31
A66-B85-C11-D31
A2-B86-C11-D31
A3-B86-C11-D31
A9-B86-C11-D31
A13-B86-C11-D31
A24-B86-C11-D31
A69-B86-C11-D31
A67-B86-C11-D31
A39-B86-C11-D31
A65-B86-C11-D31
A66-B86-C11-D31
A2-B87-C11-D31
A3-B87-C11-D31
A9-B87-C11-D31
A13-B87-C11-D31
A24-B87-C11-D31
A69-B87-C11-D31
A67-B87-C11-D31
A39-B87-C11-D31
A65-B87-C11-D31
A66-B87-C11-D31
A2-B89-C11-D31
A3-B89-C11-D31
A9-B89-C11-D31
A13-B89-C11-D31
A24-B89-C11-D31
A69-B89-C11-D31
A67-B89-C11-D31
A39-B89-C11-D31
A65-B89-C11-D31
A66-B89-C11-D31
A2-B92-C11-D31
A3-B92-C11-D31
A9-B92-C11-D31
A13-B92-C11-D31
A24-B92-C11-D31
A69-B92-C11-D31
A67-B92-C11-D31
A39-B92-C11-D31
A65-B92-C11-D31
A66-B92-C11-D31
A2-B4-C12-D31
A3-B4-C12-D31
A9-B4-C12-D31
A13-B4-C12-D31
A24-B4-C12-D31
A69-B4-C12-D31
A67-B4-C12-D31

-continued
A39-B4-C12-D31
A65-B4-C12-D31
A66-B4-C12-D31
A2-B5-C12-D31
A3-B5-C12-D31
A9-B5-C12-D31
A13-B5-C12-D31
A24-B5-C12-D31
A69-B5-C12-D31
A67-B5-C12-D31
A39-B5-C12-D31
A65-B5-C12-D31
A66-B5-C12-D31
A2-B6-C12-D31
A3-B6-C12-D31
A9-B6-C12-D31
A13-B6-C12-D31
A24-B6-C12-D31
A69-B6-C12-D31
A67-B6-C12-D31
A39-B6-C12-D31
A65-B6-C12-D31
A66-B6-C12-D31
A2-B32-C12-D31
A3-B32-C12-D31
A9-B32-C12-D31
A13-B32-C12-D31
A24-B32-C12-D31
A69-B32-C12-D31
A67-B32-C12-D31
A39-B32-C12-D31
A65-B32-C12-D31
A66-B32-C12-D31
A2-B39-C12-D31
A3-B39-C12-D31
A9-B39-C12-D31
A13-B39-C12-D31
A24-B39-C12-D31
A69-B39-C12-D31
A67-B39-C12-D31
A39-B39-C12-D31
A65-B39-C12-D31
A66-B39-C12-D31
A2-B45-C12-D31
A3-B45-C12-D31
A9-B45-C12-D31
A13-B45-C12-D31
A24-B45-C12-D31
A69-B45-C12-D31
A67-B45-C12-D31
A39-B45-C12-D31
A65-B45-C12-D31
A66-B45-C12-D31
A2-B53-C12-D31
A3-B53-C12-D31
A9-B53-C12-D31
A13-B53-C12-D31
A24-B53-C12-D31
A69-B53-C12-D31
A67-B53-C12-D31
A39-B53-C12-D31
A65-B53-C12-D31
A66-B53-C12-D31
A2-B79-C12-D31
A3-B79-C12-D31
A9-B79-C12-D31
A13-B79-C12-D31
A24-B79-C12-D31
A69-B79-C12-D31
A67-B79-C12-D31
A39-B79-C12-D31
A65-B79-C12-D31
A66-B79-C12-D31
A2-B80-C12-D31
A3-B80-C12-D31
A9-B80-C12-D31
A13-B80-C12-D31
A24-B80-C12-D31
A69-B80-C12-D31
A67-B80-C12-D31

-continued

A39-B80-C12-D31
A65-B80-C12-D31
A66-B80-C12-D31
A2-B85-C12-D31
A3-B85-C12-D31
A9-B85-C12-D31
A13-B85-C12-D31
A24-B85-C12-D31
A69-B85-C12-D31
A67-B85-C12-D31
A39-B85-C12-D31
A65-B85-C12-D31
A66-B85-C12-D31
A2-B86-C12-D31
A3-B86-C12-D31
A9-B86-C12-D31
A13-B86-C12-D31
A24-B86-C12-D31
A69-B86-C12-D31
A67-B86-C12-D31
A39-B86-C12-D31
A65-B86-C12-D31
A66-B86-C12-D31
A2-B87-C12-D31
A3-B87-C12-D31
A9-B87-C12-D31
A13-B87-C12-D31
A24-B87-C12-D31
A69-B87-C12-D31
A67-B87-C12-D31
A39-B87-C12-D31
A65-B87-C12-D31
A66-B87-C12-D31
A2-B89-C12-D31
A3-B89-C12-D31
A9-B89-C12-D31
A13-B89-C12-D31
A24-B89-C12-D31
A69-B89-C12-D31
A67-B89-C12-D31
A39-B89-C12-D31
A65-B89-C12-D31
A66-B89-C12-D31
A2-B92-C12-D31
A3-B92-C12-D31
A9-B92-C12-D31
A13-B92-C12-D31
A24-B92-C12-D31
A69-B92-C12-D31
A67-B92-C12-D31
A39-B92-C12-D31
A65-B92-C12-D31
A66-B92-C12-D31
A2-B4-C13-D31
A3-B4-C13-D31
A9-B4-C13-D31
A13-B4-C13-D31
A24-B4-C13-D31
A69-B4-C13-D31
A67-B4-C13-D31
A39-B4-C13-D31
A65-B4-C13-D31
A66-B4-C13-D31
A2-B5-C13-D31
A3-B5-C13-D31
A9-B5-C13-D31
A13-B5-C13-D31
A24-B5-C13-D31
A69-B5-C13-D31
A67-B5-C13-D31
A39-B5-C13-D31
A65-B5-C13-D31
A66-B5-C13-D31
A2-B6-C13-D31
A3-B6-C13-D31
A9-B6-C13-D31
A13-B6-C13-D31
A24-B6-C13-D31
A69-B6-C13-D31
A67-B6-C13-D31

-continued

A39-B6-C13-D31
A65-B6-C13-D31
A66-B6-C13-D31
A2-B32-C13-D31
A3-B32-C13-D31
A9-B32-C13-D31
A13-B32-C13-D31
A24-B32-C13-D31
A69-B32-C13-D31
A67-B32-C13-D31
A39-B32-C13-D31
A65-B32-C13-D31
A66-B32-C13-D31
A2-B39-C13-D31
A3-B39-C13-D31
A9-B39-C13-D31
A13-B39-C13-D31
A24-B39-C13-D31
A69-B39-C13-D31
A67-B39-C13-D31
A39-B39-C13-D31
A65-B39-C13-D31
A66-B39-C13-D31
A2-B45-C13-D31
A3-B45-C13-D31
A9-B45-C13-D31
A13-B45-C13-D31
A24-B45-C13-D31
A69-B45-C13-D31
A67-B45-C13-D31
A39-B45-C13-D31
A65-B45-C13-D31
A66-B45-C13-D31
A2-B53-C13-D31
A3-B53-C13-D31
A9-B53-C13-D31
A13-B53-C13-D31
A24-B53-C13-D31
A69-B53-C13-D31
A67-B53-C13-D31
A39-B53-C13-D31
A65-B53-C13-D31
A66-B53-C13-D31
A2-B79-C13-D31
A3-B79-C13-D31
A9-B79-C13-D31
A13-B79-C13-D31
A24-B79-C13-D31
A69-B79-C13-D31
A67-B79-C13-D31
A39-B79-C13-D31
A65-B79-C13-D31
A66-B79-C13-D31
A2-B80-C13-D31
A3-B80-C13-D31
A9-B80-C13-D31
A13-B80-C13-D31
A24-B80-C13-D31
A69-B80-C13-D31
A67-B80-C13-D31
A39-B80-C13-D31
A65-B80-C13-D31
A66-B80-C13-D31
A2-B85-C13-D31
A3-B85-C13-D31
A9-B85-C13-D31
A13-B85-C13-D31
A24-B85-C13-D31
A69-B85-C13-D31
A67-B85-C13-D31
A39-B85-C13-D31
A65-B85-C13-D31
A66-B85-C13-D31
A2-B86-C13-D31
A3-B86-C13-D31
A9-B86-C13-D31
A13-B86-C13-D31
A24-B86-C13-D31
A69-B86-C13-D31
A67-B86-C13-D31

-continued
A39-B86-C13-D31
A65-B86-C13-D31
A66-B86-C13-D31
A2-B87-C13-D31
A3-B87-C13-D31
A9-B87-C13-D31
A13-B87-C13-D31
A24-B87-C13-D31
A69-B87-C13-D31
A67-B87-C13-D31
A39-B87-C13-D31
A65-B87-C13-D31
A66-B87-C13-D31
A2-B89-C13-D31
A3-B89-C13-D31
A9-B89-C13-D31
A13-B89-C13-D31
A24-B89-C13-D31
A69-B89-C13-D31
A67-B89-C13-D31
A39-B89-C13-D31
A65-B89-C13-D31
A66-B89-C13-D31
A2-B92-C13-D31
A3-B92-C13-D31
A9-B92-C13-D31
A13-B92-C13-D31
A24-B92-C13-D31
A69-B92-C13-D31
A67-B92-C13-D31
A39-B92-C13-D31
A65-B92-C13-D31
A66-B92-C13-D31
A2-B4-C1-D32
A3-B4-C1-D32
A9-B4-C1-D32
A13-B4-C1-D32
A24-B4-C1-D32
A69-B4-C1-D32
A67-B4-C1-D32
A39-B4-C1-D32
A65-B4-C1-D32
A66-B4-C1-D32
A2-B5-C1-D32
A3-B5-C1-D32
A9-B5-C1-D32
A13-B5-C1-D32
A24-B5-C1-D32
A69-B5-C1-D32
A67-B5-C1-D32
A39-B5-C1-D32
A65-B5-C1-D32
A66-B5-C1-D32
A2-B6-C1-D32
A3-B6-C1-D32
A9-B6-C1-D32
A13-B6-C1-D32
A24-B6-C1-D32
A69-B6-C1-D32
A67-B6-C1-D32
A39-B6-C1-D32
A65-B6-C1-D32
A66-B6-C1-D32
A2-B32-C1-D32
A3-B32-C1-D32
A9-B32-C1-D32
A13-B32-C1-D32
A24-B32-C1-D32
A69-B32-C1-D32
A67-B32-C1-D32
A39-B32-C1-D32
A65-B32-C1-D32
A66-B32-C1-D32
A2-B39-C1-D32
A3-B39-C1-D32
A9-B39-C1-D32
A13-B39-C1-D32
A24-B39-C1-D32
A69-B39-C1-D32
A67-B39-C1-D32

-continued
A39-B39-C1-D32
A65-B39-C1-D32
A66-B39-C1-D32
A2-B45-C1-D32
A3-B45-C1-D32
A9-B45-C1-D32
A13-B45-C1-D32
A24-B45-C1-D32
A69-B45-C1-D32
A67-B45-C1-D32
A39-B45-C1-D32
A65-B45-C1-D32
A66-B45-C1-D32
A2-B53-C1-D32
A3-B53-C1-D32
A9-B53-C1-D32
A13-B53-C1-D32
A24-B53-C1-D32
A69-B53-C1-D32
A67-B53-C1-D32
A39-B53-C1-D32
A65-B53-C1-D32
A66-B53-C1-D32
A2-B79-C1-D32
A3-B79-C1-D32
A9-B79-C1-D32
A13-B79-C1-D32
A24-B79-C1-D32
A69-B79-C1-D32
A67-B79-C1-D32
A39-B79-C1-D32
A65-B79-C1-D32
A66-B79-C1-D32
A2-B80-C1-D32
A3-B80-C1-D32
A9-B80-C1-D32
A13-B80-C1-D32
A24-B80-C1-D32
A69-B80-C1-D32
A67-B80-C1-D32
A39-B80-C1-D32
A65-B80-C1-D32
A66-B80-C1-D32
A2-B85-C1-D32
A3-B85-C1-D32
A9-B85-C1-D32
A13-B85-C1-D32
A24-B85-C1-D32
A69-B85-C1-D32
A67-B85-C1-D32
A39-B85-C1-D32
A65-B85-C1-D32
A66-B85-C1-D32
A2-B86-C1-D32
A3-B86-C1-D32
A9-B86-C1-D32
A13-B86-C1-D32
A24-B86-C1-D32
A69-B86-C1-D32
A67-B86-C1-D32
A39-B86-C1-D32
A65-B86-C1-D32
A66-B86-C1-D32
A2-B87-C1-D32
A3-B87-C1-D32
A9-B87-C1-D32
A13-B87-C1-D32
A24-B87-C1-D32
A69-B87-C1-D32
A67-B87-C1-D32
A39-B87-C1-D32
A65-B87-C1-D32
A66-B87-C1-D32
A2-B89-C1-D32
A3-B89-C1-D32
A9-B89-C1-D32
A13-B89-C1-D32
A24-B89-C1-D32
A69-B89-C1-D32
A67-B89-C1-D32

-continued

A39-B89-C1-D32
A65-B89-C1-D32
A66-B89-C1-D32
A2-B92-C1-D32
A3-B92-C1-D32
A9-B92-C1-D32
A13-B92-C1-D32
A24-B92-C1-D32
A69-B92-C1-D32
A67-B92-C1-D32
A39-B92-C1-D32
A65-B92-C1-D32
A66-B92-C1-D32
A2-B4-C2-D32
A3-B4-C2-D32
A9-B4-C2-D32
A13-B4-C2-D32
A24-B4-C2-D32
A69-B4-C2-D32
A67-B4-C2-D32
A39-B4-C2-D32
A65-B4-C2-D32
A66-B4-C2-D32
A2-B5-C2-D32
A3-B5-C2-D32
A9-B5-C2-D32
A13-B5-C2-D32
A24-B5-C2-D32
A69-B5-C2-D32
A67-B5-C2-D32
A39-B5-C2-D32
A65-B5-C2-D32
A66-B5-C2-D32
A2-B6-C2-D32
A3-B6-C2-D32
A9-B6-C2-D32
A13-B6-C2-D32
A24-B6-C2-D32
A69-B6-C2-D32
A67-B6-C2-D32
A39-B6-C2-D32
A65-B6-C2-D32
A66-B6-C2-D32
A2-B32-C2-D32
A3-B32-C2-D32
A9-B32-C2-D32
A13-B32-C2-D32
A24-B32-C2-D32
A69-B32-C2-D32
A67-B32-C2-D32
A39-B32-C2-D32
A65-B32-C2-D32
A66-B32-C2-D32
A2-B39-C2-D32
A3-B39-C2-D32
A9-B39-C2-D32
A13-B39-C2-D32
A24-B39-C2-D32
A69-B39-C2-D32
A67-B39-C2-D32
A39-B39-C2-D32
A65-B39-C2-D32
A66-B39-C2-D32
A2-B45-C2-D32
A3-B45-C2-D32
A9-B45-C2-D32
A13-B45-C2-D32
A24-B45-C2-D32
A69-B45-C2-D32
A67-B45-C2-D32
A39-B45-C2-D32
A65-B45-C2-D32
A66-B45-C2-D32
A2-B53-C2-D32
A3-B53-C2-D32
A9-B53-C2-D32
A13-B53-C2-D32
A24-B53-C2-D32
A69-B53-C2-D32
A67-B53-C2-D32

-continued

A39-B53-C2-D32
A65-B53-C2-D32
A66-B53-C2-D32
A2-B79-C2-D32
A3-B79-C2-D32
A9-B79-C2-D32
A13-B79-C2-D32
A24-B79-C2-D32
A69-B79-C2-D32
A67-B79-C2-D32
A39-B79-C2-D32
A65-B79-C2-D32
A66-B79-C2-D32
A2-B80-C2-D32
A3-B80-C2-D32
A9-B80-C2-D32
A13-B80-C2-D32
A24-B80-C2-D32
A69-B80-C2-D32
A67-B80-C2-D32
A39-B80-C2-D32
A65-B80-C2-D32
A66-B80-C2-D32
A2-B85-C2-D32
A3-B85-C2-D32
A9-B85-C2-D32
A13-B85-C2-D32
A24-B85-C2-D32
A69-B85-C2-D32
A67-B85-C2-D32
A39-B85-C2-D32
A65-B85-C2-D32
A66-B85-C2-D32
A2-B86-C2-D32
A3-B86-C2-D32
A9-B86-C2-D32
A13-B86-C2-D32
A24-B86-C2-D32
A69-B86-C2-D32
A67-B86-C2-D32
A39-B86-C2-D32
A65-B86-C2-D32
A66-B86-C2-D32
A2-B87-C2-D32
A3-B87-C2-D32
A9-B87-C2-D32
A13-B87-C2-D32
A24-B87-C2-D32
A69-B87-C2-D32
A67-B87-C2-D32
A39-B87-C2-D32
A65-B87-C2-D32
A66-B87-C2-D32
A2-B89-C2-D32
A3-B89-C2-D32
A9-B89-C2-D32
A13-B89-C2-D32
A24-B89-C2-D32
A69-B89-C2-D32
A67-B89-C2-D32
A39-B89-C2-D32
A65-B89-C2-D32
A66-B89-C2-D32
A2-B92-C2-D32
A3-B92-C2-D32
A9-B92-C2-D32
A13-B92-C2-D32
A24-B92-C2-D32
A69-B92-C2-D32
A67-B92-C2-D32
A39-B92-C2-D32
A65-B92-C2-D32
A66-B92-C2-D32
A2-B4-C3-D32
A3-B4-C3-D32
A9-B4-C3-D32
A13-B4-C3-D32
A24-B4-C3-D32
A69-B4-C3-D32
A67-B4-C3-D32

-continued
A39-B4-C3-D32
A65-B4-C3-D32
A66-B4-C3-D32
A2-B5-C3-D32
A3-B5-C3-D32
A9-B5-C3-D32
A13-B5-C3-D32
A24-B5-C3-D32
A69-B5-C3-D32
A67-B5-C3-D32
A39-B5-C3-D32
A65-B5-C3-D32
A66-B5-C3-D32
A2-B6-C3-D32
A3-B6-C3-D32
A9-B6-C3-D32
A13-B6-C3-D32
A24-B6-C3-D32
A69-B6-C3-D32
A67-B6-C3-D32
A39-B6-C3-D32
A65-B6-C3-D32
A66-B6-C3-D32
A2-B32-C3-D32
A3-B32-C3-D32
A9-B32-C3-D32
A13-B32-C3-D32
A24-B32-C3-D32
A69-B32-C3-D32
A67-B32-C3-D32
A39-B32-C3-D32
A65-B32-C3-D32
A66-B32-C3-D32
A2-B39-C3-D32
A3-B39-C3-D32
A9-B39-C3-D32
A13-B39-C3-D32
A24-B39-C3-D32
A69-B39-C3-D32
A67-B39-C3-D32
A39-B39-C3-D32
A65-B39-C3-D32
A66-B39-C3-D32
A2-B45-C3-D32
A3-B45-C3-D32
A9-B45-C3-D32
A13-B45-C3-D32
A24-B45-C3-D32
A69-B45-C3-D32
A67-B45-C3-D32
A39-B45-C3-D32
A65-B45-C3-D32
A66-B45-C3-D32
A2-B53-C3-D32
A3-B53-C3-D32
A9-B53-C3-D32
A13-B53-C3-D32
A24-B53-C3-D32
A69-B53-C3-D32
A67-B53-C3-D32
A39-B53-C3-D32
A65-B53-C3-D32
A66-B53-C3-D32
A2-B79-C3-D32
A3-B79-C3-D32
A9-B79-C3-D32
A13-B79-C3-D32
A24-B79-C3-D32
A69-B79-C3-D32
A67-B79-C3-D32
A39-B79-C3-D32
A65-B79-C3-D32
A66-B79-C3-D32
A2-B80-C3-D32
A3-B80-C3-D32
A9-B80-C3-D32
A13-B80-C3-D32
A24-B80-C3-D32
A69-B80-C3-D32
A67-B80-C3-D32

-continued
A39-B80-C3-D32
A65-B80-C3-D32
A66-B80-C3-D32
A2-B85-C3-D32
A3-B85-C3-D32
A9-B85-C3-D32
A13-B85-C3-D32
A24-B85-C3-D32
A69-B85-C3-D32
A67-B85-C3-D32
A39-B85-C3-D32
A65-B85-C3-D32
A66-B85-C3-D32
A2-B86-C3-D32
A3-B86-C3-D32
A9-B86-C3-D32
A13-B86-C3-D32
A24-B86-C3-D32
A69-B86-C3-D32
A67-B86-C3-D32
A39-B86-C3-D32
A65-B86-C3-D32
A66-B86-C3-D32
A2-B87-C3-D32
A3-B87-C3-D32
A9-B87-C3-D32
A13-B87-C3-D32
A24-B87-C3-D32
A69-B87-C3-D32
A67-B87-C3-D32
A39-B87-C3-D32
A65-B87-C3-D32
A66-B87-C3-D32
A2-B89-C3-D32
A3-B89-C3-D32
A9-B89-C3-D32
A13-B89-C3-D32
A24-B89-C3-D32
A69-B89-C3-D32
A67-B89-C3-D32
A39-B89-C3-D32
A65-B89-C3-D32
A66-B89-C3-D32
A2-B92-C3-D32
A3-B92-C3-D32
A9-B92-C3-D32
A13-B92-C3-D32
A24-B92-C3-D32
A69-B92-C3-D32
A67-B92-C3-D32
A39-B92-C3-D32
A65-B92-C3-D32
A66-B92-C3-D32
A2-B4-C4-D32
A3-B4-C4-D32
A9-B4-C4-D32
A13-B4-C4-D32
A24-B4-C4-D32
A69-B4-C4-D32
A67-B4-C4-D32
A39-B4-C4-D32
A65-B4-C4-D32
A66-B4-C4-D32
A2-B5-C4-D32
A3-B5-C4-D32
A9-B5-C4-D32
A13-B5-C4-D32
A24-B5-C4-D32
A69-B5-C4-D32
A67-B5-C4-D32
A39-B5-C4-D32
A65-B5-C4-D32
A66-B5-C4-D32
A2-B6-C4-D32
A3-B6-C4-D32
A9-B6-C4-D32
A13-B6-C4-D32
A24-B6-C4-D32
A69-B6-C4-D32
A67-B6-C4-D32

-continued

A39-B6-C4-D32
A65-B6-C4-D32
A66-B6-C4-D32
A2-B32-C4-D32
A3-B32-C4-D32
A9-B32-C4-D32
A13-B32-C4-D32
A24-B32-C4-D32
A69-B32-C4-D32
A67-B32-C4-D32
A39-B32-C4-D32
A65-B32-C4-D32
A66-B32-C4-D32
A2-B39-C4-D32
A3-B39-C4-D32
A9-B39-C4-D32
A13-B39-C4-D32
A24-B39-C4-D32
A69-B39-C4-D32
A67-B39-C4-D32
A39-B39-C4-D32
A65-B39-C4-D32
A66-B39-C4-D32
A2-B45-C4-D32
A3-B45-C4-D32
A9-B45-C4-D32
A13-B45-C4-D32
A24-B45-C4-D32
A69-B45-C4-D32
A67-B45-C4-D32
A39-B45-C4-D32
A65-B45-C4-D32
A66-B45-C4-D32
A2-B53-C4-D32
A3-B53-C4-D32
A9-B53-C4-D32
A13-B53-C4-D32
A24-B53-C4-D32
A69-B53-C4-D32
A67-B53-C4-D32
A39-B53-C4-D32
A65-B53-C4-D32
A66-B53-C4-D32
A2-B79-C4-D32
A3-B79-C4-D32
A9-B79-C4-D32
A13-B79-C4-D32
A24-B79-C4-D32
A69-B79-C4-D32
A67-B79-C4-D32
A39-B79-C4-D32
A65-B79-C4-D32
A66-B79-C4-D32
A2-B80-C4-D32
A3-B80-C4-D32
A9-B80-C4-D32
A13-B80-C4-D32
A24-B80-C4-D32
A69-B80-C4-D32
A67-B80-C4-D32
A39-B80-C4-D32
A65-B80-C4-D32
A66-B80-C4-D32
A2-B85-C4-D32
A3-B85-C4-D32
A9-B85-C4-D32
A13-B85-C4-D32
A24-B85-C4-D32
A69-B85-C4-D32
A67-B85-C4-D32
A39-B85-C4-D32
A65-B85-C4-D32
A66-B85-C4-D32
A2-B86-C4-D32
A3-B86-C4-D32
A9-B86-C4-D32
A13-B86-C4-D32
A24-B86-C4-D32
A69-B86-C4-D32
A67-B86-C4-D32

-continued

A39-B86-C4-D32
A65-B86-C4-D32
A66-B86-C4-D32
A2-B87-C4-D32
A3-B87-C4-D32
A9-B87-C4-D32
A13-B87-C4-D32
A24-B87-C4-D32
A69-B87-C4-D32
A67-B87-C4-D32
A39-B87-C4-D32
A65-B87-C4-D32
A66-B87-C4-D32
A2-B89-C4-D32
A3-B89-C4-D32
A9-B89-C4-D32
A13-B89-C4-D32
A24-B89-C4-D32
A69-B89-C4-D32
A67-B89-C4-D32
A39-B89-C4-D32
A65-B89-C4-D32
A66-B89-C4-D32
A2-B92-C4-D32
A3-B92-C4-D32
A9-B92-C4-D32
A13-B92-C4-D32
A24-B92-C4-D32
A69-B92-C4-D32
A67-B92-C4-D32
A39-B92-C4-D32
A65-B92-C4-D32
A66-B92-C4-D32
A2-B4-C5-D32
A3-B4-C5-D32
A9-B4-C5-D32
A13-B4-C5-D32
A24-B4-C5-D32
A69-B4-C5-D32
A67-B4-C5-D32
A39-B4-C5-D32
A65-B4-C5-D32
A66-B4-C5-D32
A2-B5-C5-D32
A3-B5-C5-D32
A9-B5-C5-D32
A13-B5-C5-D32
A24-B5-C5-D32
A69-B5-C5-D32
A67-B5-C5-D32
A39-B5-C5-D32
A65-B5-C5-D32
A66-B5-C5-D32
A2-B6-C5-D32
A3-B6-C5-D32
A9-B6-C5-D32
A13-B6-C5-D32
A24-B6-C5-D32
A69-B6-C5-D32
A67-B6-C5-D32
A39-B6-C5-D32
A65-B6-C5-D32
A66-B6-C5-D32
A2-B32-C5-D32
A3-B32-C5-D32
A9-B32-C5-D32
A13-B32-C5-D32
A24-B32-C5-D32
A69-B32-C5-D32
A67-B32-C5-D32
A39-B32-C5-D32
A65-B32-C5-D32
A66-B32-C5-D32
A2-B39-C5-D32
A3-B39-C5-D32
A9-B39-C5-D32
A13-B39-C5-D32
A24-B39-C5-D32
A69-B39-C5-D32
A67-B39-C5-D32

-continued

A39-B39-C5-D32
A65-B39-C5-D32
A66-B39-C5-D32
A2-B45-C5-D32
A3-B45-C5-D32
A9-B45-C5-D32
A13-B45-C5-D32
A24-B45-C5-D32
A69-B45-C5-D32
A67-B45-C5-D32
A39-B45-C5-D32
A65-B45-C5-D32
A66-B45-C5-D32
A2-B53-C5-D32
A3-B53-C5-D32
A9-B53-C5-D32
A13-B53-C5-D32
A24-B53-C5-D32
A69-B53-C5-D32
A67-B53-C5-D32
A39-B53-C5-D32
A65-B53-C5-D32
A66-B53-C5-D32
A2-B79-C5-D32
A3-B79-C5-D32
A9-B79-C5-D32
A13-B79-C5-D32
A24-B79-C5-D32
A69-B79-C5-D32
A67-B79-C5-D32
A39-B79-C5-D32
A65-B79-C5-D32
A66-B79-C5-D32
A2-B80-C5-D32
A3-B80-C5-D32
A9-B80-C5-D32
A13-B80-C5-D32
A24-B80-C5-D32
A69-B80-C5-D32
A67-B80-C5-D32
A39-B80-C5-D32
A65-B80-C5-D32
A66-B80-C5-D32
A2-B85-C5-D32
A3-B85-C5-D32
A9-B85-C5-D32
A13-B85-C5-D32
A24-B85-C5-D32
A69-B85-C5-D32
A67-B85-C5-D32
A39-B85-C5-D32
A65-B85-C5-D32
A66-B85-C5-D32
A2-B86-C5-D32
A3-B86-C5-D32
A9-B86-C5-D32
A13-B86-C5-D32
A24-B86-C5-D32
A69-B86-C5-D32
A67-B86-C5-D32
A39-B86-C5-D32
A65-B86-C5-D32
A66-B86-C5-D32
A2-B87-C5-D32
A3-B87-C5-D32
A9-B87-C5-D32
A13-B87-C5-D32
A24-B87-C5-D32
A69-B87-C5-D32
A67-B87-C5-D32
A39-B87-C5-D32
A65-B87-C5-D32
A66-B87-C5-D32
A2-B89-C5-D32
A3-B89-C5-D32
A9-B89-C5-D32
A13-B89-C5-D32
A24-B89-C5-D32
A69-B89-C5-D32
A67-B89-C5-D32

-continued

A39-B89-C5-D32
A65-B89-C5-D32
A66-B89-C5-D32
A2-B92-C5-D32
A3-B92-C5-D32
A9-B92-C5-D32
A13-B92-C5-D32
A24-B92-C5-D32
A69-B92-C5-D32
A67-B92-C5-D32
A39-B92-C5-D32
A65-B92-C5-D32
A66-B92-C5-D32
A2-B4-C6-D32
A3-B4-C6-D32
A9-B4-C6-D32
A13-B4-C6-D32
A24-B4-C6-D32
A69-B4-C6-D32
A67-B4-C6-D32
A39-B4-C6-D32
A65-B4-C6-D32
A66-B4-C6-D32
A2-B5-C6-D32
A3-B5-C6-D32
A9-B5-C6-D32
A13-B5-C6-D32
A24-B5-C6-D32
A69-B5-C6-D32
A67-B5-C6-D32
A39-B5-C6-D32
A65-B5-C6-D32
A66-B5-C6-D32
A2-B6-C6-D32
A3-B6-C6-D32
A9-B6-C6-D32
A13-B6-C6-D32
A24-B6-C6-D32
A69-B6-C6-D32
A67-B6-C6-D32
A39-B6-C6-D32
A65-B6-C6-D32
A66-B6-C6-D32
A2-B32-C6-D32
A3-B32-C6-D32
A9-B32-C6-D32
A13-B32-C6-D32
A24-B32-C6-D32
A69-B32-C6-D32
A67-B32-C6-D32
A39-B32-C6-D32
A65-B32-C6-D32
A66-B32-C6-D32
A2-B39-C6-D32
A3-B39-C6-D32
A9-B39-C6-D32
A13-B39-C6-D32
A24-B39-C6-D32
A69-B39-C6-D32
A67-B39-C6-D32
A39-B39-C6-D32
A65-B39-C6-D32
A66-B39-C6-D32
A2-B45-C6-D32
A3-B45-C6-D32
A9-B45-C6-D32
A13-B45-C6-D32
A24-B45-C6-D32
A69-B45-C6-D32
A67-B45-C6-D32
A39-B45-C6-D32
A65-B45-C6-D32
A66-B45-C6-D32
A2-B53-C6-D32
A3-B53-C6-D32
A9-B53-C6-D32
A13-B53-C6-D32
A24-B53-C6-D32
A69-B53-C6-D32
A67-B53-C6-D32

-continued

A39-B53-C6-D32
A65-B53-C6-D32
A66-B53-C6-D32
A2-B79-C6-D32
A3-B79-C6-D32
A9-B79-C6-D32
A13-B79-C6-D32
A24-B79-C6-D32
A69-B79-C6-D32
A67-B79-C6-D32
A39-B79-C6-D32
A65-B79-C6-D32
A66-B79-C6-D32
A2-B80-C6-D32
A3-B80-C6-D32
A9-B80-C6-D32
A13-B80-C6-D32
A24-B80-C6-D32
A69-B80-C6-D32
A67-B80-C6-D32
A39-B80-C6-D32
A65-B80-C6-D32
A66-B80-C6-D32
A2-B85-C6-D32
A3-B85-C6-D32
A9-B85-C6-D32
A13-B85-C6-D32
A24-B85-C6-D32
A69-B85-C6-D32
A67-B85-C6-D32
A39-B85-C6-D32
A65-B85-C6-D32
A66-B85-C6-D32
A2-B86-C6-D32
A3-B86-C6-D32
A9-B86-C6-D32
A13-B86-C6-D32
A24-B86-C6-D32
A69-B86-C6-D32
A67-B86-C6-D32
A39-B86-C6-D32
A65-B86-C6-D32
A66-B86-C6-D32
A2-B87-C6-D32
A3-B87-C6-D32
A9-B87-C6-D32
A13-B87-C6-D32
A24-B87-C6-D32
A69-B87-C6-D32
A67-B87-C6-D32
A39-B87-C6-D32
A65-B87-C6-D32
A66-B87-C6-D32
A2-B89-C6-D32
A3-B89-C6-D32
A9-B89-C6-D32
A13-B89-C6-D32
A24-B89-C6-D32
A69-B89-C6-D32
A67-B89-C6-D32
A39-B89-C6-D32
A65-B89-C6-D32
A66-B89-C6-D32
A2-B92-C6-D32
A3-B92-C6-D32
A9-B92-C6-D32
A13-B92-C6-D32
A24-B92-C6-D32
A69-B92-C6-D32
A67-B92-C6-D32
A39-B92-C6-D32
A65-B92-C6-D32
A66-B92-C6-D32
A2-B4-C7-D32
A3-B4-C7-D32
A9-B4-C7-D32
A13-B4-C7-D32
A24-B4-C7-D32
A69-B4-C7-D32
A67-B4-C7-D32

-continued

A39-B4-C7-D32
A65-B4-C7-D32
A66-B4-C7-D32
A2-B5-C7-D32
A3-B5-C7-D32
A9-B5-C7-D32
A13-B5-C7-D32
A24-B5-C7-D32
A69-B5-C7-D32
A67-B5-C7-D32
A39-B5-C7-D32
A65-B5-C7-D32
A66-B5-C7-D32
A2-B6-C7-D32
A3-B6-C7-D32
A9-B6-C7-D32
A13-B6-C7-D32
A24-B6-C7-D32
A69-B6-C7-D32
A67-B6-C7-D32
A39-B6-C7-D32
A65-B6-C7-D32
A66-B6-C7-D32
A2-B32-C7-D32
A3-B32-C7-D32
A9-B32-C7-D32
A13-B32-C7-D32
A24-B32-C7-D32
A69-B32-C7-D32
A67-B32-C7-D32
A39-B32-C7-D32
A65-B32-C7-D32
A66-B32-C7-D32
A2-B39-C7-D32
A3-B39-C7-D32
A9-B39-C7-D32
A13-B39-C7-D32
A24-B39-C7-D32
A69-B39-C7-D32
A67-B39-C7-D32
A39-B39-C7-D32
A65-B39-C7-D32
A66-B39-C7-D32
A2-B45-C7-D32
A3-B45-C7-D32
A9-B45-C7-D32
A13-B45-C7-D32
A24-B45-C7-D32
A69-B45-C7-D32
A67-B45-C7-D32
A39-B45-C7-D32
A65-B45-C7-D32
A66-B45-C7-D32
A2-B53-C7-D32
A3-B53-C7-D32
A9-B53-C7-D32
A13-B53-C7-D32
A24-B53-C7-D32
A69-B53-C7-D32
A67-B53-C7-D32
A39-B53-C7-D32
A65-B53-C7-D32
A66-B53-C7-D32
A2-B79-C7-D32
A3-B79-C7-D32
A9-B79-C7-D32
A13-B79-C7-D32
A24-B79-C7-D32
A69-B79-C7-D32
A67-B79-C7-D32
A39-B79-C7-D32
A65-B79-C7-D32
A66-B79-C7-D32
A2-B80-C7-D32
A3-B80-C7-D32
A9-B80-C7-D32
A13-B80-C7-D32
A24-B80-C7-D32
A69-B80-C7-D32
A67-B80-C7-D32

-continued
A39-B80-C7-D32
A65-B80-C7-D32
A66-B80-C7-D32
A2-B85-C7-D32
A3-B85-C7-D32
A9-B85-C7-D32
A13-B85-C7-D32
A24-B85-C7-D32
A69-B85-C7-D32
A67-B85-C7-D32
A39-B85-C7-D32
A65-B85-C7-D32
A66-B85-C7-D32
A2-B86-C7-D32
A3-B86-C7-D32
A9-B86-C7-D32
A13-B86-C7-D32
A24-B86-C7-D32
A69-B86-C7-D32
A67-B86-C7-D32
A39-B86-C7-D32
A65-B86-C7-D32
A66-B86-C7-D32
A2-B87-C7-D32
A3-B87-C7-D32
A9-B87-C7-D32
A13-B87-C7-D32
A24-B87-C7-D32
A69-B87-C7-D32
A67-B87-C7-D32
A39-B87-C7-D32
A65-B87-C7-D32
A66-B87-C7-D32
A2-B89-C7-D32
A3-B89-C7-D32
A9-B89-C7-D32
A13-B89-C7-D32
A24-B89-C7-D32
A69-B89-C7-D32
A67-B89-C7-D32
A39-B89-C7-D32
A65-B89-C7-D32
A66-B89-C7-D32
A2-B92-C7-D32
A3-B92-C7-D32
A9-B92-C7-D32
A13-B92-C7-D32
A24-B92-C7-D32
A69-B92-C7-D32
A67-B92-C7-D32
A39-B92-C7-D32
A65-B92-C7-D32
A66-B92-C7-D32
A2-B4-C8-D32
A3-B4-C8-D32
A9-B4-C8-D32
A13-B4-C8-D32
A24-B4-C8-D32
A69-B4-C8-D32
A67-B4-C8-D32
A39-B4-C8-D32
A65-B4-C8-D32
A66-B4-C8-D32
A2-B5-C8-D32
A3-B5-C8-D32
A9-B5-C8-D32
A13-B5-C8-D32
A24-B5-C8-D32
A69-B5-C8-D32
A67-B5-C8-D32
A39-B5-C8-D32
A65-B5-C8-D32
A66-B5-C8-D32
A2-B6-C8-D32
A3-B6-C8-D32
A9-B6-C8-D32
A13-B6-C8-D32
A24-B6-C8-D32
A69-B6-C8-D32
A67-B6-C8-D32

-continued
A39-B6-C8-D32
A65-B6-C8-D32
A66-B6-C8-D32
A2-B32-C8-D32
A3-B32-C8-D32
A9-B32-C8-D32
A13-B32-C8-D32
A24-B32-C8-D32
A69-B32-C8-D32
A67-B32-C8-D32
A39-B32-C8-D32
A65-B32-C8-D32
A66-B32-C8-D32
A2-B39-C8-D32
A3-B39-C8-D32
A9-B39-C8-D32
A13-B39-C8-D32
A24-B39-C8-D32
A69-B39-C8-D32
A67-B39-C8-D32
A39-B39-C8-D32
A65-B39-C8-D32
A66-B39-C8-D32
A2-B45-C8-D32
A3-B45-C8-D32
A9-B45-C8-D32
A13-B45-C8-D32
A24-B45-C8-D32
A69-B45-C8-D32
A67-B45-C8-D32
A39-B45-C8-D32
A65-B45-C8-D32
A66-B45-C8-D32
A2-B53-C8-D32
A3-B53-C8-D32
A9-B53-C8-D32
A13-B53-C8-D32
A24-B53-C8-D32
A69-B53-C8-D32
A67-B53-C8-D32
A39-B53-C8-D32
A65-B53-C8-D32
A66-B53-C8-D32
A2-B79-C8-D32
A3-B79-C8-D32
A9-B79-C8-D32
A13-B79-C8-D32
A24-B79-C8-D32
A69-B79-C8-D32
A67-B79-C8-D32
A39-B79-C8-D32
A65-B79-C8-D32
A66-B79-C8-D32
A2-B80-C8-D32
A3-B80-C8-D32
A9-B80-C8-D32
A13-B80-C8-D32
A24-B80-C8-D32
A69-B80-C8-D32
A67-B80-C8-D32
A39-B80-C8-D32
A65-B80-C8-D32
A66-B80-C8-D32
A2-B85-C8-D32
A3-B85-C8-D32
A9-B85-C8-D32
A13-B85-C8-D32
A24-B85-C8-D32
A69-B85-C8-D32
A67-B85-C8-D32
A39-B85-C8-D32
A65-B85-C8-D32
A66-B85-C8-D32
A2-B86-C8-D32
A3-B86-C8-D32
A9-B86-C8-D32
A13-B86-C8-D32
A24-B86-C8-D32
A69-B86-C8-D32
A67-B86-C8-D32

-continued
A39-B86-C8-D32
A65-B86-C8-D32
A66-B86-C8-D32
A2-B87-C8-D32
A3-B87-C8-D32
A9-B87-C8-D32
A13-B87-C8-D32
A24-B87-C8-D32
A69-B87-C8-D32
A67-B87-C8-D32
A39-B87-C8-D32
A65-B87-C8-D32
A66-B87-C8-D32
A2-B89-C8-D32
A3-B89-C8-D32
A9-B89-C8-D32
A13-B89-C8-D32
A24-B89-C8-D32
A69-B89-C8-D32
A67-B89-C8-D32
A39-B89-C8-D32
A65-B89-C8-D32
A66-B89-C8-D32
A2-B92-C8-D32
A3-B92-C8-D32
A9-B92-C8-D32
A13-B92-C8-D32
A24-B92-C8-D32
A69-B92-C8-D32
A67-B92-C8-D32
A39-B92-C8-D32
A65-B92-C8-D32
A66-B92-C8-D32
A2-B4-C9-D32
A3-B4-C9-D32
A9-B4-C9-D32
A13-B4-C9-D32
A24-B4-C9-D32
A69-B4-C9-D32
A67-B4-C9-D32
A39-B4-C9-D32
A65-B4-C9-D32
A66-B4-C9-D32
A2-B5-C9-D32
A3-B5-C9-D32
A9-B5-C9-D32
A13-B5-C9-D32
A24-B5-C9-D32
A69-B5-C9-D32
A67-B5-C9-D32
A39-B5-C9-D32
A65-B5-C9-D32
A66-B5-C9-D32
A2-B6-C9-D32
A3-B6-C9-D32
A9-B6-C9-D32
A13-B6-C9-D32
A24-B6-C9-D32
A69-B6-C9-D32
A67-B6-C9-D32
A39-B6-C9-D32
A65-B6-C9-D32
A66-B6-C9-D32
A2-B32-C9-D32
A3-B32-C9-D32
A9-B32-C9-D32
A13-B32-C9-D32
A24-B32-C9-D32
A69-B32-C9-D32
A67-B32-C9-D32
A39-B32-C9-D32
A65-B32-C9-D32
A66-B32-C9-D32
A2-B39-C9-D32
A3-B39-C9-D32
A9-B39-C9-D32
A13-B39-C9-D32
A24-B39-C9-D32
A69-B39-C9-D32
A67-B39-C9-D32

-continued
A39-B39-C9-D32
A65-B39-C9-D32
A66-B39-C9-D32
A2-B45-C9-D32
A3-B45-C9-D32
A9-B45-C9-D32
A13-B45-C9-D32
A24-B45-C9-D32
A69-B45-C9-D32
A67-B45-C9-D32
A39-B45-C9-D32
A65-B45-C9-D32
A66-B45-C9-D32
A2-B53-C9-D32
A3-B53-C9-D32
A9-B53-C9-D32
A13-B53-C9-D32
A24-B53-C9-D32
A69-B53-C9-D32
A67-B53-C9-D32
A39-B53-C9-D32
A65-B53-C9-D32
A66-B53-C9-D32
A2-B79-C9-D32
A3-B79-C9-D32
A9-B79-C9-D32
A13-B79-C9-D32
A24-B79-C9-D32
A69-B79-C9-D32
A67-B79-C9-D32
A39-B79-C9-D32
A65-B79-C9-D32
A66-B79-C9-D32
A2-B80-C9-D32
A3-B80-C9-D32
A9-B80-C9-D32
A13-B80-C9-D32
A24-B80-C9-D32
A69-B80-C9-D32
A67-B80-C9-D32
A39-B80-C9-D32
A65-B80-C9-D32
A66-B80-C9-D32
A2-B85-C9-D32
A3-B85-C9-D32
A9-B85-C9-D32
A13-B85-C9-D32
A24-B85-C9-D32
A69-B85-C9-D32
A67-B85-C9-D32
A39-B85-C9-D32
A65-B85-C9-D32
A66-B85-C9-D32
A2-B86-C9-D32
A3-B86-C9-D32
A9-B86-C9-D32
A13-B86-C9-D32
A24-B86-C9-D32
A69-B86-C9-D32
A67-B86-C9-D32
A39-B86-C9-D32
A65-B86-C9-D32
A66-B86-C9-D32
A2-B87-C9-D32
A3-B87-C9-D32
A9-B87-C9-D32
A13-B87-C9-D32
A24-B87-C9-D32
A69-B87-C9-D32
A67-B87-C9-D32
A39-B87-C9-D32
A65-B87-C9-D32
A66-B87-C9-D32
A2-B89-C9-D32
A3-B89-C9-D32
A9-B89-C9-D32
A13-B89-C9-D32
A24-B89-C9-D32
A69-B89-C9-D32
A67-B89-C9-D32

-continued
A39-B89-C9-D32
A65-B89-C9-D32
A66-B89-C9-D32
A2-B92-C9-D32
A3-B92-C9-D32
A9-B92-C9-D32
A13-B92-C9-D32
A24-B92-C9-D32
A69-B92-C9-D32
A67-B92-C9-D32
A39-B92-C9-D32
A65-B92-C9-D32
A66-B92-C9-D32
A2-B4-C10-D32
A3-B4-C10-D32
A9-B4-C10-D32
A13-B4-C10-D32
A24-B4-C10-D32
A69-B4-C10-D32
A67-B4-C10-D32
A39-B4-C10-D32
A65-B4-C10-D32
A66-B4-C10-D32
A2-B5-C10-D32
A3-B5-C10-D32
A9-B5-C10-D32
A13-B5-C10-D32
A24-B5-C10-D32
A69-B5-C10-D32
A67-B5-C10-D32
A39-B5-C10-D32
A65-B5-C10-D32
A66-B5-C10-D32
A2-B6-C10-D32
A3-B6-C10-D32
A9-B6-C10-D32
A13-B6-C10-D32
A24-B6-C10-D32
A69-B6-C10-D32
A67-B6-C10-D32
A39-B6-C10-D32
A65-B6-C10-D32
A66-B6-C10-D32
A2-B32-C10-D32
A3-B32-C10-D32
A9-B32-C10-D32
A13-B32-C10-D32
A24-B32-C10-D32
A69-B32-C10-D32
A67-B32-C10-D32
A39-B32-C10-D32
A65-B32-C10-D32
A66-B32-C10-D32
A2-B39-C10-D32
A3-B39-C10-D32
A9-B39-C10-D32
A13-B39-C10-D32
A24-B39-C10-D32
A69-B39-C10-D32
A67-B39-C10-D32
A39-B39-C10-D32
A65-B39-C10-D32
A66-B39-C10-D32
A2-B45-C10-D32
A3-B45-C10-D32
A9-B45-C10-D32
A13-B45-C10-D32
A24-B45-C10-D32
A69-B45-C10-D32
A67-B45-C10-D32
A39-B45-C10-D32
A65-B45-C10-D32
A66-B45-C10-D32
A2-B53-C10-D32
A3-B53-C10-D32
A9-B53-C10-D32
A13-B53-C10-D32
A24-B53-C10-D32
A69-B53-C10-D32
A67-B53-C10-D32

-continued
A39-B53-C10-D32
A65-B53-C10-D32
A66-B53-C10-D32
A2-B79-C10-D32
A3-B79-C10-D32
A9-B79-C10-D32
A13-B79-C10-D32
A24-B79-C10-D32
A69-B79-C10-D32
A67-B79-C10-D32
A39-B79-C10-D32
A65-B79-C10-D32
A66-B79-C10-D32
A2-B80-C10-D32
A3-B80-C10-D32
A9-B80-C10-D32
A13-B80-C10-D32
A24-B80-C10-D32
A69-B80-C10-D32
A67-B80-C10-D32
A39-B80-C10-D32
A65-B80-C10-D32
A66-B80-C10-D32
A2-B85-C10-D32
A3-B85-C10-D32
A9-B85-C10-D32
A13-B85-C10-D32
A24-B85-C10-D32
A69-B85-C10-D32
A67-B85-C10-D32
A39-B85-C10-D32
A65-B85-C10-D32
A66-B85-C10-D32
A2-B86-C10-D32
A3-B86-C10-D32
A9-B86-C10-D32
A13-B86-C10-D32
A24-B86-C10-D32
A69-B86-C10-D32
A67-B86-C10-D32
A39-B86-C10-D32
A65-B86-C10-D32
A66-B86-C10-D32
A2-B87-C10-D32
A3-B87-C10-D32
A9-B87-C10-D32
A13-B87-C10-D32
A24-B87-C10-D32
A69-B87-C10-D32
A67-B87-C10-D32
A39-B87-C10-D32
A65-B87-C10-D32
A66-B87-C10-D32
A2-B89-C10-D32
A3-B89-C10-D32
A9-B89-C10-D32
A13-B89-C10-D32
A24-B89-C10-D32
A69-B89-C10-D32
A67-B89-C10-D32
A39-B89-C10-D32
A65-B89-C10-D32
A66-B89-C10-D32
A2-B92-C10-D32
A3-B92-C10-D32
A9-B92-C10-D32
A13-B92-C10-D32
A24-B92-C10-D32
A69-B92-C10-D32
A67-B92-C10-D32
A39-B92-C10-D32
A65-B92-C10-D32
A66-B92-C10-D32
A2-B4-C11-D32
A3-B4-C11-D32
A9-B4-C11-D32
A13-B4-C11-D32
A24-B4-C11-D32
A69-B4-C11-D32
A67-B4-C11-D32

-continued
A39-B4-C11-D32
A65-B4-C11-D32
A66-B4-C11-D32
A2-B5-C11-D32
A3-B5-C11-D32
A9-B5-C11-D32
A13-B5-C11-D32
A24-B5-C11-D32
A69-B5-C11-D32
A67-B5-C11-D32
A39-B5-C11-D32
A65-B5-C11-D32
A66-B5-C11-D32
A2-B6-C11-D32
A3-B6-C11-D32
A9-B6-C11-D32
A13-B6-C11-D32
A24-B6-C11-D32
A69-B6-C11-D32
A67-B6-C11-D32
A39-B6-C11-D32
A65-B6-C11-D32
A66-B6-C11-D32
A2-B32-C11-D32
A3-B32-C11-D32
A9-B32-C11-D32
A13-B32-C11-D32
A24-B32-C11-D32
A69-B32-C11-D32
A67-B32-C11-D32
A39-B32-C11-D32
A65-B32-C11-D32
A66-B32-C11-D32
A2-B39-C11-D32
A3-B39-C11-D32
A9-B39-C11-D32
A13-B39-C11-D32
A24-B39-C11-D32
A69-B39-C11-D32
A67-B39-C11-D32
A39-B39-C11-D32
A65-B39-C11-D32
A66-B39-C11-D32
A2-B45-C11-D32
A3-B45-C11-D32
A9-B45-C11-D32
A13-B45-C11-D32
A24-B45-C11-D32
A69-B45-C11-D32
A67-B45-C11-D32
A39-B45-C11-D32
A65-B45-C11-D32
A66-B45-C11-D32
A2-B53-C11-D32
A3-B53-C11-D32
A9-B53-C11-D32
A13-B53-C11-D32
A24-B53-C11-D32
A69-B53-C11-D32
A67-B53-C11-D32
A39-B53-C11-D32
A65-B53-C11-D32
A66-B53-C11-D32
A2-B79-C11-D32
A3-B79-C11-D32
A9-B79-C11-D32
A13-B79-C11-D32
A24-B79-C11-D32
A69-B79-C11-D32
A67-B79-C11-D32
A39-B79-C11-D32
A65-B79-C11-D32
A66-B79-C11-D32
A2-B80-C11-D32
A3-B80-C11-D32
A9-B80-C11-D32
A13-B80-C11-D32
A24-B80-C11-D32
A69-B80-C11-D32
A67-B80-C11-D32

-continued
A39-B80-C11-D32
A65-B80-C11-D32
A66-B80-C11-D32
A2-B85-C11-D32
A3-B85-C11-D32
A9-B85-C11-D32
A13-B85-C11-D32
A24-B85-C11-D32
A69-B85-C11-D32
A67-B85-C11-D32
A39-B85-C11-D32
A65-B85-C11-D32
A66-B85-C11-D32
A2-B86-C11-D32
A3-B86-C11-D32
A9-B86-C11-D32
A13-B86-C11-D32
A24-B86-C11-D32
A69-B86-C11-D32
A67-B86-C11-D32
A39-B86-C11-D32
A65-B86-C11-D32
A66-B86-C11-D32
A2-B87-C11-D32
A3-B87-C11-D32
A9-B87-C11-D32
A13-B87-C11-D32
A24-B87-C11-D32
A69-B87-C11-D32
A67-B87-C11-D32
A39-B87-C11-D32
A65-B87-C11-D32
A66-B87-C11-D32
A2-B89-C11-D32
A3-B89-C11-D32
A9-B89-C11-D32
A13-B89-C11-D32
A24-B89-C11-D32
A69-B89-C11-D32
A67-B89-C11-D32
A39-B89-C11-D32
A65-B89-C11-D32
A66-B89-C11-D32
A2-B92-C11-D32
A3-B92-C11-D32
A9-B92-C11-D32
A13-B92-C11-D32
A24-B92-C11-D32
A69-B92-C11-D32
A67-B92-C11-D32
A39-B92-C11-D32
A65-B92-C11-D32
A66-B92-C11-D32
A2-B4-C12-D32
A3-B4-C12-D32
A9-B4-C12-D32
A13-B4-C12-D32
A24-B4-C12-D32
A69-B4-C12-D32
A67-B4-C12-D32
A39-B4-C12-D32
A65-B4-C12-D32
A66-B4-C12-D32
A2-B5-C12-D32
A3-B5-C12-D32
A9-B5-C12-D32
A13-B5-C12-D32
A24-B5-C12-D32
A69-B5-C12-D32
A67-B5-C12-D32
A39-B5-C12-D32
A65-B5-C12-D32
A66-B5-C12-D32
A2-B6-C12-D32
A3-B6-C12-D32
A9-B6-C12-D32
A13-B6-C12-D32
A24-B6-C12-D32
A69-B6-C12-D32
A67-B6-C12-D32

-continued
A39-B6-C12-D32
A65-B6-C12-D32
A66-B6-C12-D32
A2-B32-C12-D32
A3-B32-C12-D32
A9-B32-C12-D32
A13-B32-C12-D32
A24-B32-C12-D32
A69-B32-C12-D32
A67-B32-C12-D32
A39-B32-C12-D32
A65-B32-C12-D32
A66-B32-C12-D32
A2-B39-C12-D32
A3-B39-C12-D32
A9-B39-C12-D32
A13-B39-C12-D32
A24-B39-C12-D32
A69-B39-C12-D32
A67-B39-C12-D32
A39-B39-C12-D32
A65-B39-C12-D32
A66-B39-C12-D32
A2-B45-C12-D32
A3-B45-C12-D32
A9-B45-C12-D32
A13-B45-C12-D32
A24-B45-C12-D32
A69-B45-C12-D32
A67-B45-C12-D32
A39-B45-C12-D32
A65-B45-C12-D32
A66-B45-C12-D32
A2-B53-C12-D32
A3-B53-C12-D32
A9-B53-C12-D32
A13-B53-C12-D32
A24-B53-C12-D32
A69-B53-C12-D32
A67-B53-C12-D32
A39-B53-C12-D32
A65-B53-C12-D32
A66-B53-C12-D32
A2-B79-C12-D32
A3-B79-C12-D32
A9-B79-C12-D32
A13-B79-C12-D32
A24-B79-C12-D32
A69-B79-C12-D32
A67-B79-C12-D32
A39-B79-C12-D32
A65-B79-C12-D32
A66-B79-C12-D32
A2-B80-C12-D32
A3-B80-C12-D32
A9-B80-C12-D32
A13-B80-C12-D32
A24-B80-C12-D32
A69-B80-C12-D32
A67-B80-C12-D32
A39-B80-C12-D32
A65-B80-C12-D32
A66-B80-C12-D32
A2-B85-C12-D32
A3-B85-C12-D32
A9-B85-C12-D32
A13-B85-C12-D32
A24-B85-C12-D32
A69-B85-C12-D32
A67-B85-C12-D32
A39-B85-C12-D32
A65-B85-C12-D32
A66-B85-C12-D32
A2-B86-C12-D32
A3-B86-C12-D32
A9-B86-C12-D32
A13-B86-C12-D32
A24-B86-C12-D32
A69-B86-C12-D32
A67-B86-C12-D32

-continued
A39-B86-C12-D32
A65-B86-C12-D32
A66-B86-C12-D32
A2-B87-C12-D32
A3-B87-C12-D32
A9-B87-C12-D32
A13-B87-C12-D32
A24-B87-C12-D32
A69-B87-C12-D32
A67-B87-C12-D32
A39-B87-C12-D32
A65-B87-C12-D32
A66-B87-C12-D32
A2-B89-C12-D32
A3-B89-C12-D32
A9-B89-C12-D32
A13-B89-C12-D32
A24-B89-C12-D32
A69-B89-C12-D32
A67-B89-C12-D32
A39-B89-C12-D32
A65-B89-C12-D32
A66-B89-C12-D32
A2-B92-C12-D32
A3-B92-C12-D32
A9-B92-C12-D32
A13-B92-C12-D32
A24-B92-C12-D32
A69-B92-C12-D32
A67-B92-C12-D32
A39-B92-C12-D32
A65-B92-C12-D32
A66-B92-C12-D32
A2-B4-C13-D32
A3-B4-C13-D32
A9-B4-C13-D32
A13-B4-C13-D32
A24-B4-C13-D32
A69-B4-C13-D32
A67-B4-C13-D32
A39-B4-C13-D32
A65-B4-C13-D32
A66-B4-C13-D32
A2-B5-C13-D32
A3-B5-C13-D32
A9-B5-C13-D32
A13-B5-C13-D32
A24-B5-C13-D32
A69-B5-C13-D32
A67-B5-C13-D32
A39-B5-C13-D32
A65-B5-C13-D32
A66-B5-C13-D32
A2-B6-C13-D32
A3-B6-C13-D32
A9-B6-C13-D32
A13-B6-C13-D32
A24-B6-C13-D32
A69-B6-C13-D32
A67-B6-C13-D32
A39-B6-C13-D32
A65-B6-C13-D32
A66-B6-C13-D32
A2-B32-C13-D32
A3-B32-C13-D32
A9-B32-C13-D32
A13-B32-C13-D32
A24-B32-C13-D32
A69-B32-C13-D32
A67-B32-C13-D32
A39-B32-C13-D32
A65-B32-C13-D32
A66-B32-C13-D32
A2-B39-C13-D32
A3-B39-C13-D32
A9-B39-C13-D32
A13-B39-C13-D32
A24-B39-C13-D32
A69-B39-C13-D32
A67-B39-C13-D32

-continued

A39-B39-C13-D32
A65-B39-C13-D32
A66-B39-C13-D32
A2-B45-C13-D32
A3-B45-C13-D32
A9-B45-C13-D32
A13-B45-C13-D32
A24-B45-C13-D32
A69-B45-C13-D32
A67-B45-C13-D32
A39-B45-C13-D32
A65-B45-C13-D32
A66-B45-C13-D32
A2-B53-C13-D32
A3-B53-C13-D32
A9-B53-C13-D32
A13-B53-C13-D32
A24-B53-C13-D32
A69-B53-C13-D32
A67-B53-C13-D32
A39-B53-C13-D32
A65-B53-C13-D32
A66-B53-C13-D32
A2-B79-C13-D32
A3-B79-C13-D32
A9-B79-C13-D32
A13-B79-C13-D32
A24-B79-C13-D32
A69-B79-C13-D32
A67-B79-C13-D32
A39-B79-C13-D32
A65-B79-C13-D32
A66-B79-C13-D32
A2-B80-C13-D32
A3-B80-C13-D32
A9-B80-C13-D32
A13-B80-C13-D32
A24-B80-C13-D32
A69-B80-C13-D32
A67-B80-C13-D32
A39-B80-C13-D32
A65-B80-C13-D32
A66-B80-C13-D32
A2-B85-C13-D32
A3-B85-C13-D32
A9-B85-C13-D32
A13-B85-C13-D32
A24-B85-C13-D32
A69-B85-C13-D32
A67-B85-C13-D32
A39-B85-C13-D32
A65-B85-C13-D32
A66-B85-C13-D32
A2-B86-C13-D32
A3-B86-C13-D32
A9-B86-C13-D32
A13-B86-C13-D32
A24-B86-C13-D32
A69-B86-C13-D32
A67-B86-C13-D32
A39-B86-C13-D32
A65-B86-C13-D32
A66-B86-C13-D32
A2-B87-C13-D32
A3-B87-C13-D32
A9-B87-C13-D32
A13-B87-C13-D32
A24-B87-C13-D32
A69-B87-C13-D32
A67-B87-C13-D32
A39-B87-C13-D32
A65-B87-C13-D32
A66-B87-C13-D32
A2-B89-C13-D32
A3-B89-C13-D32
A9-B89-C13-D32
A13-B89-C13-D32
A24-B89-C13-D32
A69-B89-C13-D32
A67-B89-C13-D32

-continued

A39-B89-C13-D32
A65-B89-C13-D32
A66-B89-C13-D32
A2-B92-C13-D32
A3-B92-C13-D32
A9-B92-C13-D32
A13-B92-C13-D32
A24-B92-C13-D32
A69-B92-C13-D32
A67-B92-C13-D32
A39-B92-C13-D32
A65-B92-C13-D32
A66-B92-C13-D32
A2-B4-C1-D33
A3-B4-C1-D33
A9-B4-C1-D33
A13-B4-C1-D33
A24-B4-C1-D33
A69-B4-C1-D33
A67-B4-C1-D33
A39-B4-C1-D33
A65-B4-C1-D33
A66-B4-C1-D33
A2-B5-C1-D33
A3-B5-C1-D33
A9-B5-C1-D33
A13-B5-C1-D33
A24-B5-C1-D33
A69-B5-C1-D33
A67-B5-C1-D33
A39-B5-C1-D33
A65-B5-C1-D33
A66-B5-C1-D33
A2-B6-C1-D33
A3-B6-C1-D33
A9-B6-C1-D33
A13-B6-C1-D33
A24-B6-C1-D33
A69-B6-C1-D33
A67-B6-C1-D33
A39-B6-C1-D33
A65-B6-C1-D33
A66-B6-C1-D33
A2-B32-C1-D33
A3-B32-C1-D33
A9-B32-C1-D33
A13-B32-C1-D33
A24-B32-C1-D33
A69-B32-C1-D33
A67-B32-C1-D33
A39-B32-C1-D33
A65-B32-C1-D33
A66-B32-C1-D33
A2-B39-C1-D33
A3-B39-C1-D33
A9-B39-C1-D33
A13-B39-C1-D33
A24-B39-C1-D33
A69-B39-C1-D33
A67-B39-C1-D33
A39-B39-C1-D33
A65-B39-C1-D33
A66-B39-C1-D33
A2-B45-C1-D33
A3-B45-C1-D33
A9-B45-C1-D33
A13-B45-C1-D33
A24-B45-C1-D33
A69-B45-C1-D33
A67-B45-C1-D33
A39-B45-C1-D33
A65-B45-C1-D33
A66-B45-C1-D33
A2-B53-C1-D33
A3-B53-C1-D33
A9-B53-C1-D33
A13-B53-C1-D33
A24-B53-C1-D33
A69-B53-C1-D33
A67-B53-C1-D33

-continued

A39-B53-C1-D33
A65-B53-C1-D33
A66-B53-C1-D33
A2-B79-C1-D33
A3-B79-C1-D33
A9-B79-C1-D33
A13-B79-C1-D33
A24-B79-C1-D33
A69-B79-C1-D33
A67-B79-C1-D33
A39-B79-C1-D33
A65-B79-C1-D33
A66-B79-C1-D33
A2-B80-C1-D33
A3-B80-C1-D33
A9-B80-C1-D33
A13-B80-C1-D33
A24-B80-C1-D33
A69-B80-C1-D33
A67-B80-C1-D33
A39-B80-C1-D33
A65-B80-C1-D33
A66-B80-C1-D33
A2-B85-C1-D33
A3-B85-C1-D33
A9-B85-C1-D33
A13-B85-C1-D33
A24-B85-C1-D33
A69-B85-C1-D33
A67-B85-C1-D33
A39-B85-C1-D33
A65-B85-C1-D33
A66-B85-C1-D33
A2-B86-C1-D33
A3-B86-C1-D33
A9-B86-C1-D33
A13-B86-C1-D33
A24-B86-C1-D33
A69-B86-C1-D33
A67-B86-C1-D33
A39-B86-C1-D33
A65-B86-C1-D33
A66-B86-C1-D33
A2-B87-C1-D33
A3-B87-C1-D33
A9-B87-C1-D33
A13-B87-C1-D33
A24-B87-C1-D33
A69-B87-C1-D33
A67-B87-C1-D33
A39-B87-C1-D33
A65-B87-C1-D33
A66-B87-C1-D33
A2-B89-C1-D33
A3-B89-C1-D33
A9-B89-C1-D33
A13-B89-C1-D33
A24-B89-C1-D33
A69-B89-C1-D33
A67-B89-C1-D33
A39-B89-C1-D33
A65-B89-C1-D33
A66-B89-C1-D33
A2-B92-C1-D33
A3-B92-C1-D33
A9-B92-C1-D33
A13-B92-C1-D33
A24-B92-C1-D33
A69-B92-C1-D33
A67-B92-C1-D33
A39-B92-C1-D33
A65-B92-C1-D33
A66-B92-C1-D33
A2-B4-C2-D33
A3-B4-C2-D33
A9-B4-C2-D33
A13-B4-C2-D33
A24-B4-C2-D33
A69-B4-C2-D33
A67-B4-C2-D33

-continued

A39-B4-C2-D33
A65-B4-C2-D33
A66-B4-C2-D33
A2-B5-C2-D33
A3-B5-C2-D33
A9-B5-C2-D33
A13-B5-C2-D33
A24-B5-C2-D33
A69-B5-C2-D33
A67-B5-C2-D33
A39-B5-C2-D33
A65-B5-C2-D33
A66-B5-C2-D33
A2-B6-C2-D33
A3-B6-C2-D33
A9-B6-C2-D33
A13-B6-C2-D33
A24-B6-C2-D33
A69-B6-C2-D33
A67-B6-C2-D33
A39-B6-C2-D33
A65-B6-C2-D33
A66-B6-C2-D33
A2-B32-C2-D33
A3-B32-C2-D33
A9-B32-C2-D33
A13-B32-C2-D33
A24-B32-C2-D33
A69-B32-C2-D33
A67-B32-C2-D33
A39-B32-C2-D33
A65-B32-C2-D33
A66-B32-C2-D33
A2-B39-C2-D33
A3-B39-C2-D33
A9-B39-C2-D33
A13-B39-C2-D33
A24-B39-C2-D33
A69-B39-C2-D33
A67-B39-C2-D33
A39-B39-C2-D33
A65-B39-C2-D33
A66-B39-C2-D33
A2-B45-C2-D33
A3-B45-C2-D33
A9-B45-C2-D33
A13-B45-C2-D33
A24-B45-C2-D33
A69-B45-C2-D33
A67-B45-C2-D33
A39-B45-C2-D33
A65-B45-C2-D33
A66-B45-C2-D33
A2-B53-C2-D33
A3-B53-C2-D33
A9-B53-C2-D33
A13-B53-C2-D33
A24-B53-C2-D33
A69-B53-C2-D33
A67-B53-C2-D33
A39-B53-C2-D33
A65-B53-C2-D33
A66-B53-C2-D33
A2-B79-C2-D33
A3-B79-C2-D33
A9-B79-C2-D33
A13-B79-C2-D33
A24-B79-C2-D33
A69-B79-C2-D33
A67-B79-C2-D33
A39-B79-C2-D33
A65-B79-C2-D33
A66-B79-C2-D33
A2-B80-C2-D33
A3-B80-C2-D33
A9-B80-C2-D33
A13-B80-C2-D33
A24-B80-C2-D33
A69-B80-C2-D33
A67-B80-C2-D33

-continued

| | |
|---|---|
| A39-B80-C2-D33 | A39-B6-C3-D33 |
| A65-B80-C2-D33 | A65-B6-C3-D33 |
| A66-B80-C2-D33 | A66-B6-C3-D33 |
| A2-B85-C2-D33 | A2-B32-C3-D33 |
| A3-B85-C2-D33 | A3-B32-C3-D33 |
| A9-B85-C2-D33 | A9-B32-C3-D33 |
| A13-B85-C2-D33 | A13-B32-C3-D33 |
| A24-B85-C2-D33 | A24-B32-C3-D33 |
| A69-B85-C2-D33 | A69-B32-C3-D33 |
| A67-B85-C2-D33 | A67-B32-C3-D33 |
| A39-B85-C2-D33 | A39-B32-C3-D33 |
| A65-B85-C2-D33 | A65-B32-C3-D33 |
| A66-B85-C2-D33 | A66-B32-C3-D33 |
| A2-B86-C2-D33 | A2-B39-C3-D33 |
| A3-B86-C2-D33 | A3-B39-C3-D33 |
| A9-B86-C2-D33 | A9-B39-C3-D33 |
| A13-B86-C2-D33 | A13-B39-C3-D33 |
| A24-B86-C2-D33 | A24-B39-C3-D33 |
| A69-B86-C2-D33 | A69-B39-C3-D33 |
| A67-B86-C2-D33 | A67-B39-C3-D33 |
| A39-B86-C2-D33 | A39-B39-C3-D33 |
| A65-B86-C2-D33 | A65-B39-C3-D33 |
| A66-B86-C2-D33 | A66-B39-C3-D33 |
| A2-B87-C2-D33 | A2-B45-C3-D33 |
| A3-B87-C2-D33 | A3-B45-C3-D33 |
| A9-B87-C2-D33 | A9-B45-C3-D33 |
| A13-B87-C2-D33 | A13-B45-C3-D33 |
| A24-B87-C2-D33 | A24-B45-C3-D33 |
| A69-B87-C2-D33 | A69-B45-C3-D33 |
| A67-B87-C2-D33 | A67-B45-C3-D33 |
| A39-B87-C2-D33 | A39-B45-C3-D33 |
| A65-B87-C2-D33 | A65-B45-C3-D33 |
| A66-B87-C2-D33 | A66-B45-C3-D33 |
| A2-B89-C2-D33 | A2-B53-C3-D33 |
| A3-B89-C2-D33 | A3-B53-C3-D33 |
| A9-B89-C2-D33 | A9-B53-C3-D33 |
| A13-B89-C2-D33 | A13-B53-C3-D33 |
| A24-B89-C2-D33 | A24-B53-C3-D33 |
| A69-B89-C2-D33 | A69-B53-C3-D33 |
| A67-B89-C2-D33 | A67-B53-C3-D33 |
| A39-B89-C2-D33 | A39-B53-C3-D33 |
| A65-B89-C2-D33 | A65-B53-C3-D33 |
| A66-B89-C2-D33 | A66-B53-C3-D33 |
| A2-B92-C2-D33 | A2-B79-C3-D33 |
| A3-B92-C2-D33 | A3-B79-C3-D33 |
| A9-B92-C2-D33 | A9-B79-C3-D33 |
| A13-B92-C2-D33 | A13-B79-C3-D33 |
| A24-B92-C2-D33 | A24-B79-C3-D33 |
| A69-B92-C2-D33 | A69-B79-C3-D33 |
| A67-B92-C2-D33 | A67-B79-C3-D33 |
| A39-B92-C2-D33 | A39-B79-C3-D33 |
| A65-B92-C2-D33 | A65-B79-C3-D33 |
| A66-B92-C2-D33 | A66-B79-C3-D33 |
| A2-B4-C3-D33 | A2-B80-C3-D33 |
| A3-B4-C3-D33 | A3-B80-C3-D33 |
| A9-B4-C3-D33 | A9-B80-C3-D33 |
| A13-B4-C3-D33 | A13-B80-C3-D33 |
| A24-B4-C3-D33 | A24-B80-C3-D33 |
| A69-B4-C3-D33 | A69-B80-C3-D33 |
| A67-B4-C3-D33 | A67-B80-C3-D33 |
| A39-B4-C3-D33 | A39-B80-C3-D33 |
| A65-B4-C3-D33 | A65-B80-C3-D33 |
| A66-B4-C3-D33 | A66-B80-C3-D33 |
| A2-B5-C3-D33 | A2-B85-C3-D33 |
| A3-B5-C3-D33 | A3-B85-C3-D33 |
| A9-B5-C3-D33 | A9-B85-C3-D33 |
| A13-B5-C3-D33 | A13-B85-C3-D33 |
| A24-B5-C3-D33 | A24-B85-C3-D33 |
| A69-B5-C3-D33 | A69-B85-C3-D33 |
| A67-B5-C3-D33 | A67-B85-C3-D33 |
| A39-B5-C3-D33 | A39-B85-C3-D33 |
| A65-B5-C3-D33 | A65-B85-C3-D33 |
| A66-B5-C3-D33 | A66-B85-C3-D33 |
| A2-B6-C3-D33 | A2-B86-C3-D33 |
| A3-B6-C3-D33 | A3-B86-C3-D33 |
| A9-B6-C3-D33 | A9-B86-C3-D33 |
| A13-B6-C3-D33 | A13-B86-C3-D33 |
| A24-B6-C3-D33 | A24-B86-C3-D33 |
| A69-B6-C3-D33 | A69-B86-C3-D33 |
| A67-B6-C3-D33 | A67-B86-C3-D33 |

-continued

A39-B86-C3-D33
A65-B86-C3-D33
A66-B86-C3-D33
A2-B87-C3-D33
A3-B87-C3-D33
A9-B87-C3-D33
A13-B87-C3-D33
A24-B87-C3-D33
A69-B87-C3-D33
A67-B87-C3-D33
A39-B87-C3-D33
A65-B87-C3-D33
A66-B87-C3-D33
A2-B89-C3-D33
A3-B89-C3-D33
A9-B89-C3-D33
A13-B89-C3-D33
A24-B89-C3-D33
A69-B89-C3-D33
A67-B89-C3-D33
A39-B89-C3-D33
A65-B89-C3-D33
A66-B89-C3-D33
A2-B92-C3-D33
A3-B92-C3-D33
A9-B92-C3-D33
A13-B92-C3-D33
A24-B92-C3-D33
A69-B92-C3-D33
A67-B92-C3-D33
A39-B92-C3-D33
A65-B92-C3-D33
A66-B92-C3-D33
A2-B4-C4-D33
A3-B4-C4-D33
A9-B4-C4-D33
A13-B4-C4-D33
A24-B4-C4-D33
A69-B4-C4-D33
A67-B4-C4-D33
A39-B4-C4-D33
A65-B4-C4-D33
A66-B4-C4-D33
A2-B5-C4-D33
A3-B5-C4-D33
A9-B5-C4-D33
A13-B5-C4-D33
A24-B5-C4-D33
A69-B5-C4-D33
A67-B5-C4-D33
A39-B5-C4-D33
A65-B5-C4-D33
A66-B5-C4-D33
A2-B6-C4-D33
A3-B6-C4-D33
A9-B6-C4-D33
A13-B6-C4-D33
A24-B6-C4-D33
A69-B6-C4-D33
A67-B6-C4-D33
A39-B6-C4-D33
A65-B6-C4-D33
A66-B6-C4-D33
A2-B32-C4-D33
A3-B32-C4-D33
A9-B32-C4-D33
A13-B32-C4-D33
A24-B32-C4-D33
A69-B32-C4-D33
A67-B32-C4-D33
A39-B32-C4-D33
A65-B32-C4-D33
A66-B32-C4-D33
A2-B39-C4-D33
A3-B39-C4-D33
A9-B39-C4-D33
A13-B39-C4-D33
A24-B39-C4-D33
A69-B39-C4-D33
A67-B39-C4-D33

-continued

A39-B39-C4-D33
A65-B39-C4-D33
A66-B39-C4-D33
A2-B45-C4-D33
A3-B45-C4-D33
A9-B45-C4-D33
A13-B45-C4-D33
A24-B45-C4-D33
A69-B45-C4-D33
A67-B45-C4-D33
A39-B45-C4-D33
A65-B45-C4-D33
A66-B45-C4-D33
A2-B53-C4-D33
A3-B53-C4-D33
A9-B53-C4-D33
A13-B53-C4-D33
A24-B53-C4-D33
A69-B53-C4-D33
A67-B53-C4-D33
A39-B53-C4-D33
A65-B53-C4-D33
A66-B53-C4-D33
A2-B79-C4-D33
A3-B79-C4-D33
A9-B79-C4-D33
A13-B79-C4-D33
A24-B79-C4-D33
A69-B79-C4-D33
A67-B79-C4-D33
A39-B79-C4-D33
A65-B79-C4-D33
A66-B79-C4-D33
A2-B80-C4-D33
A3-B80-C4-D33
A9-B80-C4-D33
A13-B80-C4-D33
A24-B80-C4-D33
A69-B80-C4-D33
A67-B80-C4-D33
A39-B80-C4-D33
A65-B80-C4-D33
A66-B80-C4-D33
A2-B85-C4-D33
A3-B85-C4-D33
A9-B85-C4-D33
A13-B85-C4-D33
A24-B85-C4-D33
A69-B85-C4-D33
A67-B85-C4-D33
A39-B85-C4-D33
A65-B85-C4-D33
A66-B85-C4-D33
A2-B86-C4-D33
A3-B86-C4-D33
A9-B86-C4-D33
A13-B86-C4-D33
A24-B86-C4-D33
A69-B86-C4-D33
A67-B86-C4-D33
A39-B86-C4-D33
A65-B86-C4-D33
A66-B86-C4-D33
A2-B87-C4-D33
A3-B87-C4-D33
A9-B87-C4-D33
A13-B87-C4-D33
A24-B87-C4-D33
A69-B87-C4-D33
A67-B87-C4-D33
A39-B87-C4-D33
A65-B87-C4-D33
A66-B87-C4-D33
A2-B89-C4-D33
A3-B89-C4-D33
A9-B89-C4-D33
A13-B89-C4-D33
A24-B89-C4-D33
A69-B89-C4-D33
A67-B89-C4-D33

-continued
A39-B89-C4-D33
A65-B89-C4-D33
A66-B89-C4-D33
A2-B92-C4-D33
A3-B92-C4-D33
A9-B92-C4-D33
A13-B92-C4-D33
A24-B92-C4-D33
A69-B92-C4-D33
A67-B92-C4-D33
A39-B92-C4-D33
A65-B92-C4-D33
A66-B92-C4-D33
A2-B4-C5-D33
A3-B4-C5-D33
A9-B4-C5-D33
A13-B4-C5-D33
A24-B4-C5-D33
A69-B4-C5-D33
A67-B4-C5-D33
A39-B4-C5-D33
A65-B4-C5-D33
A66-B4-C5-D33
A2-B5-C5-D33
A3-B5-C5-D33
A9-B5-C5-D33
A13-B5-C5-D33
A24-B5-C5-D33
A69-B5-C5-D33
A67-B5-C5-D33
A39-B5-C5-D33
A65-B5-C5-D33
A66-B5-C5-D33
A2-B6-C5-D33
A3-B6-C5-D33
A9-B6-C5-D33
A13-B6-C5-D33
A24-B6-C5-D33
A69-B6-C5-D33
A67-B6-C5-D33
A39-B6-C5-D33
A65-B6-C5-D33
A66-B6-C5-D33
A2-B32-C5-D33
A3-B32-C5-D33
A9-B32-C5-D33
A13-B32-C5-D33
A24-B32-C5-D33
A69-B32-C5-D33
A67-B32-C5-D33
A39-B32-C5-D33
A65-B32-C5-D33
A66-B32-C5-D33
A2-B39-C5-D33
A3-B39-C5-D33
A9-B39-C5-D33
A13-B39-C5-D33
A24-B39-C5-D33
A69-B39-C5-D33
A67-B39-C5-D33
A39-B39-C5-D33
A65-B39-C5-D33
A66-B39-C5-D33
A2-B45-C5-D33
A3-B45-C5-D33
A9-B45-C5-D33
A13-B45-C5-D33
A24-B45-C5-D33
A69-B45-C5-D33
A67-B45-C5-D33
A39-B45-C5-D33
A65-B45-C5-D33
A66-B45-C5-D33
A2-B53-C5-D33
A3-B53-C5-D33
A9-B53-C5-D33
A13-B53-C5-D33
A24-B53-C5-D33
A69-B53-C5-D33
A67-B53-C5-D33

-continued
A39-B53-C5-D33
A65-B53-C5-D33
A66-B53-C5-D33
A2-B79-C5-D33
A3-B79-C5-D33
A9-B79-C5-D33
A13-B79-C5-D33
A24-B79-C5-D33
A69-B79-C5-D33
A67-B79-C5-D33
A39-B79-C5-D33
A65-B79-C5-D33
A66-B79-C5-D33
A2-B80-C5-D33
A3-B80-C5-D33
A9-B80-C5-D33
A13-B80-C5-D33
A24-B80-C5-D33
A69-B80-C5-D33
A67-B80-C5-D33
A39-B80-C5-D33
A65-B80-C5-D33
A66-B80-C5-D33
A2-B85-C5-D33
A3-B85-C5-D33
A9-B85-C5-D33
A13-B85-C5-D33
A24-B85-C5-D33
A69-B85-C5-D33
A67-B85-C5-D33
A39-B85-C5-D33
A65-B85-C5-D33
A66-B85-C5-D33
A2-B86-C5-D33
A3-B86-C5-D33
A9-B86-C5-D33
A13-B86-C5-D33
A24-B86-C5-D33
A69-B86-C5-D33
A67-B86-C5-D33
A39-B86-C5-D33
A65-B86-C5-D33
A66-B86-C5-D33
A2-B87-C5-D33
A3-B87-C5-D33
A9-B87-C5-D33
A13-B87-C5-D33
A24-B87-C5-D33
A69-B87-C5-D33
A67-B87-C5-D33
A39-B87-C5-D33
A65-B87-C5-D33
A66-B87-C5-D33
A2-B89-C5-D33
A3-B89-C5-D33
A9-B89-C5-D33
A13-B89-C5-D33
A24-B89-C5-D33
A69-B89-C5-D33
A67-B89-C5-D33
A39-B89-C5-D33
A65-B89-C5-D33
A66-B89-C5-D33
A2-B92-C5-D33
A3-B92-C5-D33
A9-B92-C5-D33
A13-B92-C5-D33
A24-B92-C5-D33
A69-B92-C5-D33
A67-B92-C5-D33
A39-B92-C5-D33
A65-B92-C5-D33
A66-B92-C5-D33
A2-B4-C6-D33
A3-B4-C6-D33
A9-B4-C6-D33
A13-B4-C6-D33
A24-B4-C6-D33
A69-B4-C6-D33
A67-B4-C6-D33

-continued

A39-B4-C6-D33
A65-B4-C6-D33
A66-B4-C6-D33
A2-B5-C6-D33
A3-B5-C6-D33
A9-B5-C6-D33
A13-B5-C6-D33
A24-B5-C6-D33
A69-B5-C6-D33
A67-B5-C6-D33
A39-B5-C6-D33
A65-B5-C6-D33
A66-B5-C6-D33
A2-B6-C6-D33
A3-B6-C6-D33
A9-B6-C6-D33
A13-B6-C6-D33
A24-B6-C6-D33
A69-B6-C6-D33
A67-B6-C6-D33
A39-B6-C6-D33
A65-B6-C6-D33
A66-B6-C6-D33
A2-B32-C6-D33
A3-B32-C6-D33
A9-B32-C6-D33
A13-B32-C6-D33
A24-B32-C6-D33
A69-B32-C6-D33
A67-B32-C6-D33
A39-B32-C6-D33
A65-B32-C6-D33
A66-B32-C6-D33
A2-B39-C6-D33
A3-B39-C6-D33
A9-B39-C6-D33
A13-B39-C6-D33
A24-B39-C6-D33
A69-B39-C6-D33
A67-B39-C6-D33
A39-B39-C6-D33
A65-B39-C6-D33
A66-B39-C6-D33
A2-B45-C6-D33
A3-B45-C6-D33
A9-B45-C6-D33
A13-B45-C6-D33
A24-B45-C6-D33
A69-B45-C6-D33
A67-B45-C6-D33
A39-B45-C6-D33
A65-B45-C6-D33
A66-B45-C6-D33
A2-B53-C6-D33
A3-B53-C6-D33
A9-B53-C6-D33
A13-B53-C6-D33
A24-B53-C6-D33
A69-B53-C6-D33
A67-B53-C6-D33
A39-B53-C6-D33
A65-B53-C6-D33
A66-B53-C6-D33
A2-B79-C6-D33
A3-B79-C6-D33
A9-B79-C6-D33
A13-B79-C6-D33
A24-B79-C6-D33
A69-B79-C6-D33
A67-B79-C6-D33
A39-B79-C6-D33
A65-B79-C6-D33
A66-B79-C6-D33
A2-B80-C6-D33
A3-B80-C6-D33
A9-B80-C6-D33
A13-B80-C6-D33
A24-B80-C6-D33
A69-B80-C6-D33
A67-B80-C6-D33

-continued

A39-B80-C6-D33
A65-B80-C6-D33
A66-B80-C6-D33
A2-B85-C6-D33
A3-B85-C6-D33
A9-B85-C6-D33
A13-B85-C6-D33
A24-B85-C6-D33
A69-B85-C6-D33
A67-B85-C6-D33
A39-B85-C6-D33
A65-B85-C6-D33
A66-B85-C6-D33
A2-B86-C6-D33
A3-B86-C6-D33
A9-B86-C6-D33
A13-B86-C6-D33
A24-B86-C6-D33
A69-B86-C6-D33
A67-B86-C6-D33
A39-B86-C6-D33
A65-B86-C6-D33
A66-B86-C6-D33
A2-B87-C6-D33
A3-B87-C6-D33
A9-B87-C6-D33
A13-B87-C6-D33
A24-B87-C6-D33
A69-B87-C6-D33
A67-B87-C6-D33
A39-B87-C6-D33
A65-B87-C6-D33
A66-B87-C6-D33
A2-B89-C6-D33
A3-B89-C6-D33
A9-B89-C6-D33
A13-B89-C6-D33
A24-B89-C6-D33
A69-B89-C6-D33
A67-B89-C6-D33
A39-B89-C6-D33
A65-B89-C6-D33
A66-B89-C6-D33
A2-B92-C6-D33
A3-B92-C6-D33
A9-B92-C6-D33
A13-B92-C6-D33
A24-B92-C6-D33
A69-B92-C6-D33
A67-B92-C6-D33
A39-B92-C6-D33
A65-B92-C6-D33
A66-B92-C6-D33
A2-B4-C7-D33
A3-B4-C7-D33
A9-B4-C7-D33
A13-B4-C7-D33
A24-B4-C7-D33
A69-B4-C7-D33
A67-B4-C7-D33
A39-B4-C7-D33
A65-B4-C7-D33
A66-B4-C7-D33
A2-B5-C7-D33
A3-B5-C7-D33
A9-B5-C7-D33
A13-B5-C7-D33
A24-B5-C7-D33
A69-B5-C7-D33
A67-B5-C7-D33
A39-B5-C7-D33
A65-B5-C7-D33
A66-B5-C7-D33
A2-B6-C7-D33
A3-B6-C7-D33
A9-B6-C7-D33
A13-B6-C7-D33
A24-B6-C7-D33
A69-B6-C7-D33
A67-B6-C7-D33

-continued

A39-B6-C7-D33
A65-B6-C7-D33
A66-B6-C7-D33
A2-B32-C7-D33
A3-B32-C7-D33
A9-B32-C7-D33
A13-B32-C7-D33
A24-B32-C7-D33
A69-B32-C7-D33
A67-B32-C7-D33
A39-B32-C7-D33
A65-B32-C7-D33
A66-B32-C7-D33
A2-B39-C7-D33
A3-B39-C7-D33
A9-B39-C7-D33
A13-B39-C7-D33
A24-B39-C7-D33
A69-B39-C7-D33
A67-B39-C7-D33
A39-B39-C7-D33
A65-B39-C7-D33
A66-B39-C7-D33
A2-B45-C7-D33
A3-B45-C7-D33
A9-B45-C7-D33
A13-B45-C7-D33
A24-B45-C7-D33
A69-B45-C7-D33
A67-B45-C7-D33
A39-B45-C7-D33
A65-B45-C7-D33
A66-B45-C7-D33
A2-B53-C7-D33
A3-B53-C7-D33
A9-B53-C7-D33
A13-B53-C7-D33
A24-B53-C7-D33
A69-B53-C7-D33
A67-B53-C7-D33
A39-B53-C7-D33
A65-B53-C7-D33
A66-B53-C7-D33
A2-B79-C7-D33
A3-B79-C7-D33
A9-B79-C7-D33
A13-B79-C7-D33
A24-B79-C7-D33
A69-B79-C7-D33
A67-B79-C7-D33
A39-B79-C7-D33
A65-B79-C7-D33
A66-B79-C7-D33
A2-B80-C7-D33
A3-B80-C7-D33
A9-B80-C7-D33
A13-B80-C7-D33
A24-B80-C7-D33
A69-B80-C7-D33
A67-B80-C7-D33
A39-B80-C7-D33
A65-B80-C7-D33
A66-B80-C7-D33
A2-B85-C7-D33
A3-B85-C7-D33
A9-B85-C7-D33
A13-B85-C7-D33
A24-B85-C7-D33
A69-B85-C7-D33
A67-B85-C7-D33
A39-B85-C7-D33
A65-B85-C7-D33
A66-B85-C7-D33
A2-B86-C7-D33
A3-B86-C7-D33
A9-B86-C7-D33
A13-B86-C7-D33
A24-B86-C7-D33
A69-B86-C7-D33
A67-B86-C7-D33

-continued

A39-B86-C7-D33
A65-B86-C7-D33
A66-B86-C7-D33
A2-B87-C7-D33
A3-B87-C7-D33
A9-B87-C7-D33
A13-B87-C7-D33
A24-B87-C7-D33
A69-B87-C7-D33
A67-B87-C7-D33
A39-B87-C7-D33
A65-B87-C7-D33
A66-B87-C7-D33
A2-B89-C7-D33
A3-B89-C7-D33
A9-B89-C7-D33
A13-B89-C7-D33
A24-B89-C7-D33
A69-B89-C7-D33
A67-B89-C7-D33
A39-B89-C7-D33
A65-B89-C7-D33
A66-B89-C7-D33
A2-B92-C7-D33
A3-B92-C7-D33
A9-B92-C7-D33
A13-B92-C7-D33
A24-B92-C7-D33
A69-B92-C7-D33
A67-B92-C7-D33
A39-B92-C7-D33
A65-B92-C7-D33
A66-B92-C7-D33
A2-B4-C8-D33
A3-B4-C8-D33
A9-B4-C8-D33
A13-B4-C8-D33
A24-B4-C8-D33
A69-B4-C8-D33
A67-B4-C8-D33
A39-B4-C8-D33
A65-B4-C8-D33
A66-B4-C8-D33
A2-B5-C8-D33
A3-B5-C8-D33
A9-B5-C8-D33
A13-B5-C8-D33
A24-B5-C8-D33
A69-B5-C8-D33
A67-B5-C8-D33
A39-B5-C8-D33
A65-B5-C8-D33
A66-B5-C8-D33
A2-B6-C8-D33
A3-B6-C8-D33
A9-B6-C8-D33
A13-B6-C8-D33
A24-B6-C8-D33
A69-B6-C8-D33
A67-B6-C8-D33
A39-B6-C8-D33
A65-B6-C8-D33
A66-B6-C8-D33
A2-B32-C8-D33
A3-B32-C8-D33
A9-B32-C8-D33
A13-B32-C8-D33
A24-B32-C8-D33
A69-B32-C8-D33
A67-B32-C8-D33
A39-B32-C8-D33
A65-B32-C8-D33
A66-B32-C8-D33
A2-B39-C8-D33
A3-B39-C8-D33
A9-B39-C8-D33
A13-B39-C8-D33
A24-B39-C8-D33
A69-B39-C8-D33
A67-B39-C8-D33

-continued

A39-B39-C8-D33
A65-B39-C8-D33
A66-B39-C8-D33
A2-B45-C8-D33
A3-B45-C8-D33
A9-B45-C8-D33
A13-B45-C8-D33
A24-B45-C8-D33
A69-B45-C8-D33
A67-B45-C8-D33
A39-B45-C8-D33
A65-B45-C8-D33
A66-B45-C8-D33
A2-B53-C8-D33
A3-B53-C8-D33
A9-B53-C8-D33
A13-B53-C8-D33
A24-B53-C8-D33
A69-B53-C8-D33
A67-B53-C8-D33
A39-B53-C8-D33
A65-B53-C8-D33
A66-B53-C8-D33
A2-B79-C8-D33
A3-B79-C8-D33
A9-B79-C8-D33
A13-B79-C8-D33
A24-B79-C8-D33
A69-B79-C8-D33
A67-B79-C8-D33
A39-B79-C8-D33
A65-B79-C8-D33
A66-B79-C8-D33
A2-B80-C8-D33
A3-B80-C8-D33
A9-B80-C8-D33
A13-B80-C8-D33
A24-B80-C8-D33
A69-B80-C8-D33
A67-B80-C8-D33
A39-B80-C8-D33
A65-B80-C8-D33
A66-B80-C8-D33
A2-B85-C8-D33
A3-B85-C8-D33
A9-B85-C8-D33
A13-B85-C8-D33
A24-B85-C8-D33
A69-B85-C8-D33
A67-B85-C8-D33
A39-B85-C8-D33
A65-B85-C8-D33
A66-B85-C8-D33
A2-B86-C8-D33
A3-B86-C8-D33
A9-B86-C8-D33
A13-B86-C8-D33
A24-B86-C8-D33
A69-B86-C8-D33
A67-B86-C8-D33
A39-B86-C8-D33
A65-B86-C8-D33
A66-B86-C8-D33
A2-B87-C8-D33
A3-B87-C8-D33
A9-B87-C8-D33
A13-B87-C8-D33
A24-B87-C8-D33
A69-B87-C8-D33
A67-B87-C8-D33
A39-B87-C8-D33
A65-B87-C8-D33
A66-B87-C8-D33
A2-B89-C8-D33
A3-B89-C8-D33
A9-B89-C8-D33
A13-B89-C8-D33
A24-B89-C8-D33
A69-B89-C8-D33
A67-B89-C8-D33

-continued

A39-B89-C8-D33
A65-B89-C8-D33
A66-B89-C8-D33
A2-B92-C8-D33
A3-B92-C8-D33
A9-B92-C8-D33
A13-B92-C8-D33
A24-B92-C8-D33
A69-B92-C8-D33
A67-B92-C8-D33
A39-B92-C8-D33
A65-B92-C8-D33
A66-B92-C8-D33
A2-B4-C9-D33
A3-B4-C9-D33
A9-B4-C9-D33
A13-B4-C9-D33
A24-B4-C9-D33
A69-B4-C9-D33
A67-B4-C9-D33
A39-B4-C9-D33
A65-B4-C9-D33
A66-B4-C9-D33
A2-B5-C9-D33
A3-B5-C9-D33
A9-B5-C9-D33
A13-B5-C9-D33
A24-B5-C9-D33
A69-B5-C9-D33
A67-B5-C9-D33
A39-B5-C9-D33
A65-B5-C9-D33
A66-B5-C9-D33
A2-B6-C9-D33
A3-B6-C9-D33
A9-B6-C9-D33
A13-B6-C9-D33
A24-B6-C9-D33
A69-B6-C9-D33
A67-B6-C9-D33
A39-B6-C9-D33
A65-B6-C9-D33
A66-B6-C9-D33
A2-B32-C9-D33
A3-B32-C9-D33
A9-B32-C9-D33
A13-B32-C9-D33
A24-B32-C9-D33
A69-B32-C9-D33
A67-B32-C9-D33
A39-B32-C9-D33
A65-B32-C9-D33
A66-B32-C9-D33
A2-B39-C9-D33
A3-B39-C9-D33
A9-B39-C9-D33
A13-B39-C9-D33
A24-B39-C9-D33
A69-B39-C9-D33
A67-B39-C9-D33
A39-B39-C9-D33
A65-B39-C9-D33
A66-B39-C9-D33
A2-B45-C9-D33
A3-B45-C9-D33
A9-B45-C9-D33
A13-B45-C9-D33
A24-B45-C9-D33
A69-B45-C9-D33
A67-B45-C9-D33
A39-B45-C9-D33
A65-B45-C9-D33
A66-B45-C9-D33
A2-B53-C9-D33
A3-B53-C9-D33
A9-B53-C9-D33
A13-B53-C9-D33
A24-B53-C9-D33
A69-B53-C9-D33
A67-B53-C9-D33

-continued
A39-B53-C9-D33
A65-B53-C9-D33
A66-B53-C9-D33
A2-B79-C9-D33
A3-B79-C9-D33
A9-B79-C9-D33
A13-B79-C9-D33
A24-B79-C9-D33
A69-B79-C9-D33
A67-B79-C9-D33
A39-B79-C9-D33
A65-B79-C9-D33
A66-B79-C9-D33
A2-B80-C9-D33
A3-B80-C9-D33
A9-B80-C9-D33
A13-B80-C9-D33
A24-B80-C9-D33
A69-B80-C9-D33
A67-B80-C9-D33
A39-B80-C9-D33
A65-B80-C9-D33
A66-B80-C9-D33
A2-B85-C9-D33
A3-B85-C9-D33
A9-B85-C9-D33
A13-B85-C9-D33
A24-B85-C9-D33
A69-B85-C9-D33
A67-B85-C9-D33
A39-B85-C9-D33
A65-B85-C9-D33
A66-B85-C9-D33
A2-B86-C9-D33
A3-B86-C9-D33
A9-B86-C9-D33
A13-B86-C9-D33
A24-B86-C9-D33
A69-B86-C9-D33
A67-B86-C9-D33
A39-B86-C9-D33
A65-B86-C9-D33
A66-B86-C9-D33
A2-B87-C9-D33
A3-B87-C9-D33
A9-B87-C9-D33
A13-B87-C9-D33
A24-B87-C9-D33
A69-B87-C9-D33
A67-B87-C9-D33
A39-B87-C9-D33
A65-B87-C9-D33
A66-B87-C9-D33
A2-B89-C9-D33
A3-B89-C9-D33
A9-B89-C9-D33
A13-B89-C9-D33
A24-B89-C9-D33
A69-B89-C9-D33
A67-B89-C9-D33
A39-B89-C9-D33
A65-B89-C9-D33
A66-B89-C9-D33
A2-B92-C9-D33
A3-B92-C9-D33
A9-B92-C9-D33
A13-B92-C9-D33
A24-B92-C9-D33
A69-B92-C9-D33
A67-B92-C9-D33
A39-B92-C9-D33
A65-B92-C9-D33
A66-B92-C9-D33
A2-B4-C10-D33
A3-B4-C10-D33
A9-B4-C10-D33
A13-B4-C10-D33
A24-B4-C10-D33
A69-B4-C10-D33
A67-B4-C10-D33

-continued
A39-B4-C10-D33
A65-B4-C10-D33
A66-B4-C10-D33
A2-B5-C10-D33
A3-B5-C10-D33
A9-B5-C10-D33
A13-B5-C10-D33
A24-B5-C10-D33
A69-B5-C10-D33
A67-B5-C10-D33
A39-B5-C10-D33
A65-B5-C10-D33
A66-B5-C10-D33
A2-B6-C10-D33
A3-B6-C10-D33
A9-B6-C10-D33
A13-B6-C10-D33
A24-B6-C10-D33
A69-B6-C10-D33
A67-B6-C10-D33
A39-B6-C10-D33
A65-B6-C10-D33
A66-B6-C10-D33
A2-B32-C10-D33
A3-B32-C10-D33
A9-B32-C10-D33
A13-B32-C10-D33
A24-B32-C10-D33
A69-B32-C10-D33
A67-B32-C10-D33
A39-B32-C10-D33
A65-B32-C10-D33
A66-B32-C10-D33
A2-B39-C10-D33
A3-B39-C10-D33
A9-B39-C10-D33
A13-B39-C10-D33
A24-B39-C10-D33
A69-B39-C10-D33
A67-B39-C10-D33
A39-B39-C10-D33
A65-B39-C10-D33
A66-B39-C10-D33
A2-B45-C10-D33
A3-B45-C10-D33
A9-B45-C10-D33
A13-B45-C10-D33
A24-B45-C10-D33
A69-B45-C10-D33
A67-B45-C10-D33
A39-B45-C10-D33
A65-B45-C10-D33
A66-B45-C10-D33
A2-B53-C10-D33
A3-B53-C10-D33
A9-B53-C10-D33
A13-B53-C10-D33
A24-B53-C10-D33
A69-B53-C10-D33
A67-B53-C10-D33
A39-B53-C10-D33
A65-B53-C10-D33
A66-B53-C10-D33
A2-B79-C10-D33
A3-B79-C10-D33
A9-B79-C10-D33
A13-B79-C10-D33
A24-B79-C10-D33
A69-B79-C10-D33
A67-B79-C10-D33
A39-B79-C10-D33
A65-B79-C10-D33
A66-B79-C10-D33
A2-B80-C10-D33
A3-B80-C10-D33
A9-B80-C10-D33
A13-B80-C10-D33
A24-B80-C10-D33
A69-B80-C10-D33
A67-B80-C10-D33

-continued

A39-B80-C10-D33
A65-B80-C10-D33
A66-B80-C10-D33
A2-B85-C10-D33
A3-B85-C10-D33
A9-B85-C10-D33
A13-B85-C10-D33
A24-B85-C10-D33
A69-B85-C10-D33
A67-B85-C10-D33
A39-B85-C10-D33
A65-B85-C10-D33
A66-B85-C10-D33
A2-B86-C10-D33
A3-B86-C10-D33
A9-B86-C10-D33
A13-B86-C10-D33
A24-B86-C10-D33
A69-B86-C10-D33
A67-B86-C10-D33
A39-B86-C10-D33
A65-B86-C10-D33
A66-B86-C10-D33
A2-B87-C10-D33
A3-B87-C10-D33
A9-B87-C10-D33
A13-B87-C10-D33
A24-B87-C10-D33
A69-B87-C10-D33
A67-B87-C10-D33
A39-B87-C10-D33
A65-B87-C10-D33
A66-B87-C10-D33
A2-B89-C10-D33
A3-B89-C10-D33
A9-B89-C10-D33
A13-B89-C10-D33
A24-B89-C10-D33
A69-B89-C10-D33
A67-B89-C10-D33
A39-B89-C10-D33
A65-B89-C10-D33
A66-B89-C10-D33
A2-B92-C10-D33
A3-B92-C10-D33
A9-B92-C10-D33
A13-B92-C10-D33
A24-B92-C10-D33
A69-B92-C10-D33
A67-B92-C10-D33
A39-B92-C10-D33
A65-B92-C10-D33
A66-B92-C10-D33
A2-B4-C11-D33
A3-B4-C11-D33
A9-B4-C11-D33
A13-B4-C11-D33
A24-B4-C11-D33
A69-B4-C11-D33
A67-B4-C11-D33
A39-B4-C11-D33
A65-B4-C11-D33
A66-B4-C11-D33
A2-B5-C11-D33
A3-B5-C11-D33
A9-B5-C11-D33
A13-B5-C11-D33
A24-B5-C11-D33
A69-B5-C11-D33
A67-B5-C11-D33
A39-B5-C11-D33
A65-B5-C11-D33
A66-B5-C11-D33
A2-B6-C11-D33
A3-B6-C11-D33
A9-B6-C11-D33
A13-B6-C11-D33
A24-B6-C11-D33
A69-B6-C11-D33
A67-B6-C11-D33

-continued

A39-B6-C11-D33
A65-B6-C11-D33
A66-B6-C11-D33
A2-B32-C11-D33
A3-B32-C11-D33
A9-B32-C11-D33
A13-B32-C11-D33
A24-B32-C11-D33
A69-B32-C11-D33
A67-B32-C11-D33
A39-B32-C11-D33
A65-B32-C11-D33
A66-B32-C11-D33
A2-B39-C11-D33
A3-B39-C11-D33
A9-B39-C11-D33
A13-B39-C11-D33
A24-B39-C11-D33
A69-B39-C11-D33
A67-B39-C11-D33
A39-B39-C11-D33
A65-B39-C11-D33
A66-B39-C11-D33
A2-B45-C11-D33
A3-B45-C11-D33
A9-B45-C11-D33
A13-B45-C11-D33
A24-B45-C11-D33
A69-B45-C11-D33
A67-B45-C11-D33
A39-B45-C11-D33
A65-B45-C11-D33
A66-B45-C11-D33
A2-B53-C11-D33
A3-B53-C11-D33
A9-B53-C11-D33
A13-B53-C11-D33
A24-B53-C11-D33
A69-B53-C11-D33
A67-B53-C11-D33
A39-B53-C11-D33
A65-B53-C11-D33
A66-B53-C11-D33
A2-B79-C11-D33
A3-B79-C11-D33
A9-B79-C11-D33
A13-B79-C11-D33
A24-B79-C11-D33
A69-B79-C11-D33
A67-B79-C11-D33
A39-B79-C11-D33
A65-B79-C11-D33
A66-B79-C11-D33
A2-B80-C11-D33
A3-B80-C11-D33
A9-B80-C11-D33
A13-B80-C11-D33
A24-B80-C11-D33
A69-B80-C11-D33
A67-B80-C11-D33
A39-B80-C11-D33
A65-B80-C11-D33
A66-B80-C11-D33
A2-B85-C11-D33
A3-B85-C11-D33
A9-B85-C11-D33
A13-B85-C11-D33
A24-B85-C11-D33
A69-B85-C11-D33
A67-B85-C11-D33
A39-B85-C11-D33
A65-B85-C11-D33
A66-B85-C11-D33
A2-B86-C11-D33
A3-B86-C11-D33
A9-B86-C11-D33
A13-B86-C11-D33
A24-B86-C11-D33
A69-B86-C11-D33
A67-B86-C11-D33

-continued

A39-B86-C11-D33
A65-B86-C11-D33
A66-B86-C11-D33
A2-B87-C11-D33
A3-B87-C11-D33
A9-B87-C11-D33
A13-B87-C11-D33
A24-B87-C11-D33
A69-B87-C11-D33
A67-B87-C11-D33
A39-B87-C11-D33
A65-B87-C11-D33
A66-B87-C11-D33
A2-B89-C11-D33
A3-B89-C11-D33
A9-B89-C11-D33
A13-B89-C11-D33
A24-B89-C11-D33
A69-B89-C11-D33
A67-B89-C11-D33
A39-B89-C11-D33
A65-B89-C11-D33
A66-B89-C11-D33
A2-B92-C11-D33
A3-B92-C11-D33
A9-B92-C11-D33
A13-B92-C11-D33
A24-B92-C11-D33
A69-B92-C11-D33
A67-B92-C11-D33
A39-B92-C11-D33
A65-B92-C11-D33
A66-B92-C11-D33
A2-B4-C12-D33
A3-B4-C12-D33
A9-B4-C12-D33
A13-B4-C12-D33
A24-B4-C12-D33
A69-B4-C12-D33
A67-B4-C12-D33
A39-B4-C12-D33
A65-B4-C12-D33
A66-B4-C12-D33
A2-B5-C12-D33
A3-B5-C12-D33
A9-B5-C12-D33
A13-B5-C12-D33
A24-B5-C12-D33
A69-B5-C12-D33
A67-B5-C12-D33
A39-B5-C12-D33
A65-B5-C12-D33
A66-B5-C12-D33
A2-B6-C12-D33
A3-B6-C12-D33
A9-B6-C12-D33
A13-B6-C12-D33
A24-B6-C12-D33
A69-B6-C12-D33
A67-B6-C12-D33
A39-B6-C12-D33
A65-B6-C12-D33
A66-B6-C12-D33
A2-B32-C12-D33
A3-B32-C12-D33
A9-B32-C12-D33
A13-B32-C12-D33
A24-B32-C12-D33
A69-B32-C12-D33
A67-B32-C12-D33
A39-B32-C12-D33
A65-B32-C12-D33
A66-B32-C12-D33
A2-B39-C12-D33
A3-B39-C12-D33
A9-B39-C12-D33
A13-B39-C12-D33
A24-B39-C12-D33
A69-B39-C12-D33
A67-B39-C12-D33

-continued

A39-B39-C12-D33
A65-B39-C12-D33
A66-B39-C12-D33
A2-B45-C12-D33
A3-B45-C12-D33
A9-B45-C12-D33
A13-B45-C12-D33
A24-B45-C12-D33
A69-B45-C12-D33
A67-B45-C12-D33
A39-B45-C12-D33
A65-B45-C12-D33
A66-B45-C12-D33
A2-B53-C12-D33
A3-B53-C12-D33
A9-B53-C12-D33
A13-B53-C12-D33
A24-B53-C12-D33
A69-B53-C12-D33
A67-B53-C12-D33
A39-B53-C12-D33
A65-B53-C12-D33
A66-B53-C12-D33
A2-B79-C12-D33
A3-B79-C12-D33
A9-B79-C12-D33
A13-B79-C12-D33
A24-B79-C12-D33
A69-B79-C12-D33
A67-B79-C12-D33
A39-B79-C12-D33
A65-B79-C12-D33
A66-B79-C12-D33
A2-B80-C12-D33
A3-B80-C12-D33
A9-B80-C12-D33
A13-B80-C12-D33
A24-B80-C12-D33
A69-B80-C12-D33
A67-B80-C12-D33
A39-B80-C12-D33
A65-B80-C12-D33
A66-B80-C12-D33
A2-B85-C12-D33
A3-B85-C12-D33
A9-B85-C12-D33
A13-B85-C12-D33
A24-B85-C12-D33
A69-B85-C12-D33
A67-B85-C12-D33
A39-B85-C12-D33
A65-B85-C12-D33
A66-B85-C12-D33
A2-B86-C12-D33
A3-B86-C12-D33
A9-B86-C12-D33
A13-B86-C12-D33
A24-B86-C12-D33
A69-B86-C12-D33
A67-B86-C12-D33
A39-B86-C12-D33
A65-B86-C12-D33
A66-B86-C12-D33
A2-B87-C12-D33
A3-B87-C12-D33
A9-B87-C12-D33
A13-B87-C12-D33
A24-B87-C12-D33
A69-B87-C12-D33
A67-B87-C12-D33
A39-B87-C12-D33
A65-B87-C12-D33
A66-B87-C12-D33
A2-B89-C12-D33
A3-B89-C12-D33
A9-B89-C12-D33
A13-B89-C12-D33
A24-B89-C12-D33
A69-B89-C12-D33
A67-B89-C12-D33

-continued

A39-B89-C12-D33
A65-B89-C12-D33
A66-B89-C12-D33
A2-B92-C12-D33
A3-B92-C12-D33
A9-B92-C12-D33
A13-B92-C12-D33
A24-B92-C12-D33
A69-B92-C12-D33
A67-B92-C12-D33
A39-B92-C12-D33
A65-B92-C12-D33
A66-B92-C12-D33
A2-B4-C13-D33
A3-B4-C13-D33
A9-B4-C13-D33
A13-B4-C13-D33
A24-B4-C13-D33
A69-B4-C13-D33
A67-B4-C13-D33
A39-B4-C13-D33
A65-B4-C13-D33
A66-B4-C13-D33
A2-B5-C13-D33
A3-B5-C13-D33
A9-B5-C13-D33
A13-B5-C13-D33
A24-B5-C13-D33
A69-B5-C13-D33
A67-B5-C13-D33
A39-B5-C13-D33
A65-B5-C13-D33
A66-B5-C13-D33
A2-B6-C13-D33
A3-B6-C13-D33
A9-B6-C13-D33
A13-B6-C13-D33
A24-B6-C13-D33
A69-B6-C13-D33
A67-B6-C13-D33
A39-B6-C13-D33
A65-B6-C13-D33
A66-B6-C13-D33
A2-B32-C13-D33
A3-B32-C13-D33
A9-B32-C13-D33
A13-B32-C13-D33
A24-B32-C13-D33
A69-B32-C13-D33
A67-B32-C13-D33
A39-B32-C13-D33
A65-B32-C13-D33
A66-B32-C13-D33
A2-B39-C13-D33
A3-B39-C13-D33
A9-B39-C13-D33
A13-B39-C13-D33
A24-B39-C13-D33
A69-B39-C13-D33
A67-B39-C13-D33
A39-B39-C13-D33
A65-B39-C13-D33
A66-B39-C13-D33
A2-B45-C13-D33
A3-B45-C13-D33
A9-B45-C13-D33
A13-B45-C13-D33
A24-B45-C13-D33
A69-B45-C13-D33
A67-B45-C13-D33
A39-B45-C13-D33
A65-B45-C13-D33
A66-B45-C13-D33
A2-B53-C13-D33
A3-B53-C13-D33
A9-B53-C13-D33
A13-B53-C13-D33
A24-B53-C13-D33
A69-B53-C13-D33
A67-B53-C13-D33

-continued

A39-B53-C13-D33
A65-B53-C13-D33
A66-B53-C13-D33
A2-B79-C13-D33
A3-B79-C13-D33
A9-B79-C13-D33
A13-B79-C13-D33
A24-B79-C13-D33
A69-B79-C13-D33
A67-B79-C13-D33
A39-B79-C13-D33
A65-B79-C13-D33
A66-B79-C13-D33
A2-B80-C13-D33
A3-B80-C13-D33
A9-B80-C13-D33
A13-B80-C13-D33
A24-B80-C13-D33
A69-B80-C13-D33
A67-B80-C13-D33
A39-B80-C13-D33
A65-B80-C13-D33
A66-B80-C13-D33
A2-B85-C13-D33
A3-B85-C13-D33
A9-B85-C13-D33
A13-B85-C13-D33
A24-B85-C13-D33
A69-B85-C13-D33
A67-B85-C13-D33
A39-B85-C13-D33
A65-B85-C13-D33
A66-B85-C13-D33
A2-B86-C13-D33
A3-B86-C13-D33
A9-B86-C13-D33
A13-B86-C13-D33
A24-B86-C13-D33
A69-B86-C13-D33
A67-B86-C13-D33
A39-B86-C13-D33
A65-B86-C13-D33
A66-B86-C13-D33
A2-B87-C13-D33
A3-B87-C13-D33
A9-B87-C13-D33
A13-B87-C13-D33
A24-B87-C13-D33
A69-B87-C13-D33
A67-B87-C13-D33
A39-B87-C13-D33
A65-B87-C13-D33
A66-B87-C13-D33
A2-B89-C13-D33
A3-B89-C13-D33
A9-B89-C13-D33
A13-B89-C13-D33
A24-B89-C13-D33
A69-B89-C13-D33
A67-B89-C13-D33
A39-B89-C13-D33
A65-B89-C13-D33
A66-B89-C13-D33
A2-B92-C13-D33
A3-B92-C13-D33
A9-B92-C13-D33
A13-B92-C13-D33
A24-B92-C13-D33
A69-B92-C13-D33
A67-B92-C13-D33
A39-B92-C13-D33
A65-B92-C13-D33
A66-B92-C13-D33
A2-B4-C1-D34
A3-B4-C1-D34
A9-B4-C1-D34
A13-B4-C1-D34
A24-B4-C1-D34
A69-B4-C1-D34
A67-B4-C1-D34

-continued

A39-B4-C1-D34
A65-B4-C1-D34
A66-B4-C1-D34
A2-B5-C1-D34
A3-B5-C1-D34
A9-B5-C1-D34
A13-B5-C1-D34
A24-B5-C1-D34
A69-B5-C1-D34
A67-B5-C1-D34
A39-B5-C1-D34
A65-B5-C1-D34
A66-B5-C1-D34
A2-B6-C1-D34
A3-B6-C1-D34
A9-B6-C1-D34
A13-B6-C1-D34
A24-B6-C1-D34
A69-B6-C1-D34
A67-B6-C1-D34
A39-B6-C1-D34
A65-B6-C1-D34
A66-B6-C1-D34
A2-B32-C1-D34
A3-B32-C1-D34
A9-B32-C1-D34
A13-B32-C1-D34
A24-B32-C1-D34
A69-B32-C1-D34
A67-B32-C1-D34
A39-B32-C1-D34
A65-B32-C1-D34
A66-B32-C1-D34
A2-B39-C1-D34
A3-B39-C1-D34
A9-B39-C1-D34
A13-B39-C1-D34
A24-B39-C1-D34
A69-B39-C1-D34
A67-B39-C1-D34
A39-B39-C1-D34
A65-B39-C1-D34
A66-B39-C1-D34
A2-B45-C1-D34
A3-B45-C1-D34
A9-B45-C1-D34
A13-B45-C1-D34
A24-B45-C1-D34
A69-B45-C1-D34
A67-B45-C1-D34
A39-B45-C1-D34
A65-B45-C1-D34
A66-B45-C1-D34
A2-B53-C1-D34
A3-B53-C1-D34
A9-B53-C1-D34
A13-B53-C1-D34
A24-B53-C1-D34
A69-B53-C1-D34
A67-B53-C1-D34
A39-B53-C1-D34
A65-B53-C1-D34
A66-B53-C1-D34
A2-B79-C1-D34
A3-B79-C1-D34
A9-B79-C1-D34
A13-B79-C1-D34
A24-B79-C1-D34
A69-B79-C1-D34
A67-B79-C1-D34
A39-B79-C1-D34
A65-B79-C1-D34
A66-B79-C1-D34
A2-B80-C1-D34
A3-B80-C1-D34
A9-B80-C1-D34
A13-B80-C1-D34
A24-B80-C1-D34
A69-B80-C1-D34
A67-B80-C1-D34

-continued

A39-B80-C1-D34
A65-B80-C1-D34
A66-B80-C1-D34
A2-B85-C1-D34
A3-B85-C1-D34
A9-B85-C1-D34
A13-B85-C1-D34
A24-B85-C1-D34
A69-B85-C1-D34
A67-B85-C1-D34
A39-B85-C1-D34
A65-B85-C1-D34
A66-B85-C1-D34
A2-B86-C1-D34
A3-B86-C1-D34
A9-B86-C1-D34
A13-B86-C1-D34
A24-B86-C1-D34
A69-B86-C1-D34
A67-B86-C1-D34
A39-B86-C1-D34
A65-B86-C1-D34
A66-B86-C1-D34
A2-B87-C1-D34
A3-B87-C1-D34
A9-B87-C1-D34
A13-B87-C1-D34
A24-B87-C1-D34
A69-B87-C1-D34
A67-B87-C1-D34
A39-B87-C1-D34
A65-B87-C1-D34
A66-B87-C1-D34
A2-B89-C1-D34
A3-B89-C1-D34
A9-B89-C1-D34
A13-B89-C1-D34
A24-B89-C1-D34
A69-B89-C1-D34
A67-B89-C1-D34
A39-B89-C1-D34
A65-B89-C1-D34
A66-B89-C1-D34
A2-B92-C1-D34
A3-B92-C1-D34
A9-B92-C1-D34
A13-B92-C1-D34
A24-B92-C1-D34
A69-B92-C1-D34
A67-B92-C1-D34
A39-B92-C1-D34
A65-B92-C1-D34
A66-B92-C1-D34
A2-B4-C2-D34
A3-B4-C2-D34
A9-B4-C2-D34
A13-B4-C2-D34
A24-B4-C2-D34
A69-B4-C2-D34
A67-B4-C2-D34
A39-B4-C2-D34
A65-B4-C2-D34
A66-B4-C2-D34
A2-B5-C2-D34
A3-B5-C2-D34
A9-B5-C2-D34
A13-B5-C2-D34
A24-B5-C2-D34
A69-B5-C2-D34
A67-B5-C2-D34
A39-B5-C2-D34
A65-B5-C2-D34
A66-B5-C2-D34
A2-B6-C2-D34
A3-B6-C2-D34
A9-B6-C2-D34
A13-B6-C2-D34
A24-B6-C2-D34
A69-B6-C2-D34
A67-B6-C2-D34

-continued

A39-B6-C2-D34
A65-B6-C2-D34
A66-B6-C2-D34
A2-B32-C2-D34
A3-B32-C2-D34
A9-B32-C2-D34
A13-B32-C2-D34
A24-B32-C2-D34
A69-B32-C2-D34
A67-B32-C2-D34
A39-B32-C2-D34
A65-B32-C2-D34
A66-B32-C2-D34
A2-B39-C2-D34
A3-B39-C2-D34
A9-B39-C2-D34
A13-B39-C2-D34
A24-B39-C2-D34
A69-B39-C2-D34
A67-B39-C2-D34
A39-B39-C2-D34
A65-B39-C2-D34
A66-B39-C2-D34
A2-B45-C2-D34
A3-B45-C2-D34
A9-B45-C2-D34
A13-B45-C2-D34
A24-B45-C2-D34
A69-B45-C2-D34
A67-B45-C2-D34
A39-B45-C2-D34
A65-B45-C2-D34
A66-B45-C2-D34
A2-B53-C2-D34
A3-B53-C2-D34
A9-B53-C2-D34
A13-B53-C2-D34
A24-B53-C2-D34
A69-B53-C2-D34
A67-B53-C2-D34
A39-B53-C2-D34
A65-B53-C2-D34
A66-B53-C2-D34
A2-B79-C2-D34
A3-B79-C2-D34
A9-B79-C2-D34
A13-B79-C2-D34
A24-B79-C2-D34
A69-B79-C2-D34
A67-B79-C2-D34
A39-B79-C2-D34
A65-B79-C2-D34
A66-B79-C2-D34
A2-B80-C2-D34
A3-B80-C2-D34
A9-B80-C2-D34
A13-B80-C2-D34
A24-B80-C2-D34
A69-B80-C2-D34
A67-B80-C2-D34
A39-B80-C2-D34
A65-B80-C2-D34
A66-B80-C2-D34
A2-B85-C2-D34
A3-B85-C2-D34
A9-B85-C2-D34
A13-B85-C2-D34
A24-B85-C2-D34
A69-B85-C2-D34
A67-B85-C2-D34
A39-B85-C2-D34
A65-B85-C2-D34
A66-B85-C2-D34
A2-B86-C2-D34
A3-B86-C2-D34
A9-B86-C2-D34
A13-B86-C2-D34
A24-B86-C2-D34
A69-B86-C2-D34
A67-B86-C2-D34

-continued

A39-B86-C2-D34
A65-B86-C2-D34
A66-B86-C2-D34
A2-B87-C2-D34
A3-B87-C2-D34
A9-B87-C2-D34
A13-B87-C2-D34
A24-B87-C2-D34
A69-B87-C2-D34
A67-B87-C2-D34
A39-B87-C2-D34
A65-B87-C2-D34
A66-B87-C2-D34
A2-B89-C2-D34
A3-B89-C2-D34
A9-B89-C2-D34
A13-B89-C2-D34
A24-B89-C2-D34
A69-B89-C2-D34
A67-B89-C2-D34
A39-B89-C2-D34
A65-B89-C2-D34
A66-B89-C2-D34
A2-B92-C2-D34
A3-B92-C2-D34
A9-B92-C2-D34
A13-B92-C2-D34
A24-B92-C2-D34
A69-B92-C2-D34
A67-B92-C2-D34
A39-B92-C2-D34
A65-B92-C2-D34
A66-B92-C2-D34
A2-B4-C3-D34
A3-B4-C3-D34
A9-B4-C3-D34
A13-B4-C3-D34
A24-B4-C3-D34
A69-B4-C3-D34
A67-B4-C3-D34
A39-B4-C3-D34
A65-B4-C3-D34
A66-B4-C3-D34
A2-B5-C3-D34
A3-B5-C3-D34
A9-B5-C3-D34
A13-B5-C3-D34
A24-B5-C3-D34
A69-B5-C3-D34
A67-B5-C3-D34
A39-B5-C3-D34
A65-B5-C3-D34
A66-B5-C3-D34
A2-B6-C3-D34
A3-B6-C3-D34
A9-B6-C3-D34
A13-B6-C3-D34
A24-B6-C3-D34
A69-B6-C3-D34
A67-B6-C3-D34
A39-B6-C3-D34
A65-B6-C3-D34
A66-B6-C3-D34
A2-B32-C3-D34
A3-B32-C3-D34
A9-B32-C3-D34
A13-B32-C3-D34
A24-B32-C3-D34
A69-B32-C3-D34
A67-B32-C3-D34
A39-B32-C3-D34
A65-B32-C3-D34
A66-B32-C3-D34
A2-B39-C3-D34
A3-B39-C3-D34
A9-B39-C3-D34
A13-B39-C3-D34
A24-B39-C3-D34
A69-B39-C3-D34
A67-B39-C3-D34

-continued

A39-B39-C3-D34
A65-B39-C3-D34
A66-B39-C3-D34
A2-B45-C3-D34
A3-B45-C3-D34
A9-B45-C3-D34
A13-B45-C3-D34
A24-B45-C3-D34
A69-B45-C3-D34
A67-B45-C3-D34
A39-B45-C3-D34
A65-B45-C3-D34
A66-B45-C3-D34
A2-B53-C3-D34
A3-B53-C3-D34
A9-B53-C3-D34
A13-B53-C3-D34
A24-B53-C3-D34
A69-B53-C3-D34
A67-B53-G3-D34
A39-B53-C3-D34
A65-B53-C3-D34
A66-B53-C3-D34
A2-B79-C3-D34
A3-B79-C3-D34
A9-B79-C3-D34
A13-B79-C3-D34
A24-B79-C3-D34
A69-B79-C3-D34
A67-B79-C3-D34
A39-B79-C3-D34
A65-B79-C3-D34
A66-B79-C3-D34
A2-B80-C3-D34
A3-B80-C3-D34
A9-B80-C3-D34
A13-B80-C3-D34
A24-B80-C3-D34
A69-B80-C3-D34
A67-B80-C3-D34
A39-B80-C3-D34
A65-B80-C3-D34
A66-B80-C3-D34
A2-B85-C3-D34
A3-B85-C3-D34
A9-B85-C3-D34
A13-B85-C3-D34
A24-B85-C3-D34
A69-B85-C3-D34
A67-B85-C3-D34
A39-B85-C3-D34
A65-B85-C3-D34
A66-B85-C3-D34
A2-B86-C3-D34
A3-B86-C3-D34
A9-B86-C3-D34
A13-B86-C3-D34
A24-B86-C3-D34
A69-B86-C3-D34
A67-B86-C3-D34
A39-B86-C3-D34
A65-B86-C3-D34
A66-B86-C3-D34
A2-B87-C3-D34
A3-B87-C3-D34
A9-B87-C3-D34
A13-B87-C3-D34
A24-B87-C3-D34
A69-B87-C3-D34
A67-B87-C3-D34
A39-B87-C3-D34
A65-B87-C3-D34
A66-B87-C3-D34
A2-B89-C3-D34
A3-B89-C3-D34
A9-B89-C3-D34
A13-B89-C3-D34
A24-B89-C3-D34
A69-B89-C3-D34
A67-B89-C3-D34

-continued

A39-B89-C3-D34
A65-B89-C3-D34
A66-B89-C3-D34
A2-B92-C3-D34
A3-B92-C3-D34
A9-B92-C3-D34
A13-B92-C3-D34
A24-B92-C3-D34
A69-B92-C3-D34
A67-B92-C3-D34
A39-B92-C3-D34
A65-B92-C3-D34
A66-B92-C3-D34
A2-B4-C4-D34
A3-B4-C4-D34
A9-B4-C4-D34
A13-B4-C4-D34
A24-B4-C4-D34
A69-B4-C4-D34
A67-B4-C4-D34
A39-B4-C4-D34
A65-B4-C4-D34
A66-B4-C4-D34
A2-B5-C4-D34
A3-B5-C4-D34
A9-B5-C4-D34
A13-B5-C4-D34
A24-B5-C4-D34
A69-B5-C4-D34
A67-B5-C4-D34
A39-B5-C4-D34
A65-B5-C4-D34
A66-B5-C4-D34
A2-B6-C4-D34
A3-B6-C4-D34
A9-B6-C4-D34
A13-B6-C4-D34
A24-B6-C4-D34
A69-B6-C4-D34
A67-B6-C4-D34
A39-B6-C4-D34
A65-B6-C4-D34
A66-B6-C4-D34
A2-B32-C4-D34
A3-B32-C4-D34
A9-B32-C4-D34
A13-B32-C4-D34
A24-B32-C4-D34
A69-B32-C4-D34
A67-B32-C4-D34
A39-B32-C4-D34
A65-B32-C4-D34
A66-B32-C4-D34
A2-B39-C4-D34
A3-B39-C4-D34
A9-B39-C4-D34
A13-B39-C4-D34
A24-B39-C4-D34
A69-B39-C4-D34
A67-B39-C4-D34
A39-B39-C4-D34
A65-B39-C4-D34
A66-B39-C4-D34
A2-B45-C4-D34
A3-B45-C4-D34
A9-B45-C4-D34
A13-B45-C4-D34
A24-B45-C4-D34
A69-B45-C4-D34
A67-B45-C4-D34
A39-B45-C4-D34
A65-B45-C4-D34
A66-B45-C4-D34
A2-B53-C4-D34
A3-B53-C4-D34
A9-B53-C4-D34
A13-B53-C4-D34
A24-B53-C4-D34
A69-B53-C4-D34
A67-B53-C4-D34

-continued

A39-B53-C4-D34
A65-B53-C4-D34
A66-B53-C4-D34
A2-B79-C4-D34
A3-B79-C4-D34
A9-B79-C4-D34
A13-B79-C4-D34
A24-B79-C4-D34
A69-B79-C4-D34
A67-B79-C4-D34
A39-B79-C4-D34
A65-B79-C4-D34
A66-B79-C4-D34
A2-B80-C4-D34
A3-B80-C4-D34
A9-B80-C4-D34
A13-B80-C4-D34
A24-B80-C4-D34
A69-B80-C4-D34
A67-B80-C4-D34
A39-B80-C4-D34
A65-B80-C4-D34
A66-B80-C4-D34
A2-B85-C4-D34
A3-B85-C4-D34
A9-B85-C4-D34
A13-B85-C4-D34
A24-B85-C4-D34
A69-B85-C4-D34
A67-B85-C4-D34
A39-B85-C4-D34
A65-B85-C4-D34
A66-B85-C4-D34
A2-B86-C4-D34
A3-B86-C4-D34
A9-B86-C4-D34
A13-B86-C4-D34
A24-B86-C4-D34
A69-B86-C4-D34
A67-B86-C4-D34
A39-B86-C4-D34
A65-B86-C4-D34
A66-B86-C4-D34
A2-B87-C4-D34
A3-B87-C4-D34
A9-B87-C4-D34
A13-B87-C4-D34
A24-B87-C4-D34
A69-B87-C4-D34
A67-B87-C4-D34
A39-B87-C4-D34
A65-B87-C4-D34
A66-B87-C4-D34
A2-B89-C4-D34
A3-B89-C4-D34
A9-B89-C4-D34
A13-B89-C4-D34
A24-B89-C4-D34
A69-B89-C4-D34
A67-B89-C4-D34
A39-B89-C4-D34
A65-B89-C4-D34
A66-B89-C4-D34
A2-B92-C4-D34
A3-B92-C4-D34
A9-B92-C4-D34
A13-B92-C4-D34
A24-B92-C4-D34
A69-B92-C4-D34
A67-B92-C4-D34
A39-B92-C4-D34
A65-B92-C4-D34
A66-B92-C4-D34
A2-B4-C5-D34
A3-B4-C5-D34
A9-B4-C5-D34
A13-B4-C5-D34
A24-B4-C5-D34
A69-B4-C5-D34
A67-B4-C5-D34

-continued

A39-B4-C5-D34
A65-B4-C5-D34
A66-B4-C5-D34
A2-B5-C5-D34
A3-B5-C5-D34
A9-B5-C5-D34
A13-B5-C5-D34
A24-B5-C5-D34
A69-B5-C5-D34
A67-B5-C5-D34
A39-B5-C5-D34
A65-B5-C5-D34
A66-B5-C5-D34
A2-B6-C5-D34
A3-B6-C5-D34
A9-B6-C5-D34
A13-B6-C5-D34
A24-B6-C5-D34
A69-B6-C5-D34
A67-B6-C5-D34
A39-B6-C5-D34
A65-B6-C5-D34
A66-B6-C5-D34
A2-B32-C5-D34
A3-B32-C5-D34
A9-B32-C5-D34
A13-B32-C5-D34
A24-B32-C5-D34
A69-B32-C5-D34
A67-B32-C5-D34
A39-B32-C5-D34
A65-B32-C5-D34
A66-B32-C5-D34
A2-B39-C5-D34
A3-B39-C5-D34
A9-B39-C5-D34
A13-B39-C5-D34
A24-B39-C5-D34
A69-B39-C5-D34
A67-B39-C5-D34
A39-B39-C5-D34
A65-B39-C5-D34
A66-B39-C5-D34
A2-B45-C5-D34
A3-B45-C5-D34
A9-B45-C5-D34
A13-B45-C5-D34
A24-B45-C5-D34
A69-B45-C5-D34
A67-B45-C5-D34
A39-B45-C5-D34
A65-B45-C5-D34
A66-B45-C5-D34
A2-B53-C5-D34
A3-B53-C5-D34
A9-B53-C5-D34
A13-B53-C5-D34
A24-B53-C5-D34
A69-B53-C5-D34
A67-B53-C5-D34
A39-B53-C5-D34
A65-B53-C5-D34
A66-B53-C5-D34
A2-B79-C5-D34
A3-B79-C5-D34
A9-B79-C5-D34
A13-B79-C5-D34
A24-B79-C5-D34
A69-B79-C5-D34
A67-B79-C5-D34
A39-B79-C5-D34
A65-B79-C5-D34
A66-B79-C5-D34
A2-B80-C5-D34
A3-B80-C5-D34
A9-B80-C5-D34
A13-B80-C5-D34
A24-B80-C5-D34
A69-B80-C5-D34
A67-B80-C5-D34

-continued
A39-B80-C5-D34
A65-B80-C5-D34
A66-B80-C5-D34
A2-B85-C5-D34
A3-B85-C5-D34
A9-B85-C5-D34
A13-B85-C5-D34
A24-B85-C5-D34
A69-B85-C5-D34
A67-B85-C5-D34
A39-B85-C5-D34
A65-B85-C5-D34
A66-B85-C5-D34
A2-B86-C5-D34
A3-B86-C5-D34
A9-B86-C5-D34
A13-B86-C5-D34
A24-B86-C5-D34
A69-B86-C5-D34
A67-B86-C5-D34
A39-B86-C5-D34
A65-B86-C5-D34
A66-B86-C5-D34
A2-B87-C5-D34
A3-B87-C5-D34
A9-B87-C5-D34
A13-B87-C5-D34
A24-B87-C5-D34
A69-B87-C5-D34
A67-B87-C5-D34
A39-B87-C5-D34
A65-B87-C5-D34
A66-B87-C5-D34
A2-B89-C5-D34
A3-B89-C5-D34
A9-B89-C5-D34
A13-B89-C5-D34
A24-B89-C5-D34
A69-B89-C5-D34
A67-B89-C5-D34
A39-B89-C5-D34
A65-B89-C5-D34
A66-B89-C5-D34
A2-B92-C5-D34
A3-B92-C5-D34
A9-B92-C5-D34
A13-B92-C5-D34
A24-B92-C5-D34
A69-B92-C5-D34
A67-B92-C5-D34
A39-B92-C5-D34
A65-B92-C5-D34
A66-B92-C5-D34
A2-B4-C6-D34
A3-B4-C6-D34
A9-B4-C6-D34
A13-B4-C6-D34
A24-B4-C6-D34
A69-B4-C6-D34
A67-B4-C6-D34
A39-B4-C6-D34
A65-B4-C6-D34
A66-B4-C6-D34
A2-B5-C6-D34
A3-B5-C6-D34
A9-B5-C6-D34
A13-B5-C6-D34
A24-B5-C6-D34
A69-B5-C6-D34
A67-B5-C6-D34
A39-B5-C6-D34
A65-B5-C6-D34
A66-B5-C6-D34
A2-B6-C6-D34
A3-B6-C6-D34
A9-B6-C6-D34
A13-B6-C6-D34
A24-B6-C6-D34
A69-B6-C6-D34
A67-B6-C6-D34

-continued
A39-B6-C6-D34
A65-B6-C6-D34
A66-B6-C6-D34
A2-B32-C6-D34
A3-B32-C6-D34
A9-B32-C6-D34
A13-B32-C6-D34
A24-B32-C6-D34
A69-B32-C6-D34
A67-B32-C6-D34
A39-B32-C6-D34
A65-B32-C6-D34
A66-B32-C6-D34
A2-B39-C6-D34
A3-B39-C6-D34
A9-B39-C6-D34
A13-B39-C6-D34
A24-B39-C6-D34
A69-B39-C6-D34
A67-B39-C6-D34
A39-B39-C6-D34
A65-B39-C6-D34
A66-B39-C6-D34
A2-B45-C6-D34
A3-B45-C6-D34
A9-B45-C6-D34
A13-B45-C6-D34
A24-B45-C6-D34
A69-B45-C6-D34
A67-B45-C6-D34
A39-B45-C6-D34
A65-B45-C6-D34
A66-B45-C6-D34
A2-B53-C6-D34
A3-B53-C6-D34
A9-B53-C6-D34
A13-B53-C6-D34
A24-B53-C6-D34
A69-B53-C6-D34
A67-B53-C6-D34
A39-B53-C6-D34
A65-B53-C6-D34
A66-B53-C6-D34
A2-B79-C6-D34
A3-B79-C6-D34
A9-B79-C6-D34
A13-B79-C6-D34
A24-B79-C6-D34
A69-B79-C6-D34
A67-B79-C6-D34
A39-B79-C6-D34
A65-B79-C6-D34
A66-B79-C6-D34
A2-B80-C6-D34
A3-B80-C6-D34
A9-B80-C6-D34
A13-B80-C6-D34
A24-B80-C6-D34
A69-B80-C6-D34
A67-B80-C6-D34
A39-B80-C6-D34
A65-B80-C6-D34
A66-B80-C6-D34
A2-B85-C6-D34
A3-B85-C6-D34
A9-B85-C6-D34
A13-B85-C6-D34
A24-B85-C6-D34
A69-B85-C6-D34
A67-B85-C6-D34
A39-B85-C6-D34
A65-B85-C6-D34
A66-B85-C6-D34
A2-B86-C6-D34
A3-B86-C6-D34
A9-B86-C6-D34
A13-B86-C6-D34
A24-B86-C6-D34
A69-B86-C6-D34
A67-B86-C6-D34

-continued

A39-B86-C6-D34
A65-B86-C6-D34
A66-B86-C6-D34
A2-B87-C6-D34
A3-B87-C6-D34
A9-B87-C6-D34
A13-B87-C6-D34
A24-B87-C6-D34
A69-B87-C6-D34
A67-B87-C6-D34
A39-B87-C6-D34
A65-B87-C6-D34
A66-B87-C6-D34
A2-B89-C6-D34
A3-B89-C6-D34
A9-B89-C6-D34
A13-B89-C6-D34
A24-B89-C6-D34
A69-B89-C6-D34
A67-B89-C6-D34
A39-B89-C6-D34
A65-B89-C6-D34
A66-B89-C6-D34
A2-B92-C6-D34
A3-B92-C6-D34
A9-B92-C6-D34
A13-B92-C6-D34
A24-B92-C6-D34
A69-B92-C6-D34
A67-B92-C6-D34
A39-B92-C6-D34
A65-B92-C6-D34
A66-B92-C6-D34
A2-B4-C7-D34
A3-B4-C7-D34
A9-B4-C7-D34
A13-B4-C7-D34
A24-B4-C7-D34
A69-B4-C7-D34
A67-B4-C7-D34
A39-B4-C7-D34
A65-B4-C7-D34
A66-B4-C7-D34
A2-B5-C7-D34
A3-B5-C7-D34
A9-B5-C7-D34
A13-B5-C7-D34
A24-B5-C7-D34
A69-B5-C7-D34
A67-B5-C7-D34
A39-B5-C7-D34
A65-B5-C7-D34
A66-B5-C7-D34
A2-B6-C7-D34
A3-B6-C7-D34
A9-B6-C7-D34
A13-B6-C7-D34
A24-B6-C7-D34
A69-B6-C7-D34
A67-B6-C7-D34
A39-B6-C7-D34
A65-B6-C7-D34
A66-B6-C7-D34
A2-B32-C7-D34
A3-B32-C7-D34
A9-B32-C7-D34
A13-B32-C7-D34
A24-B32-C7-D34
A69-B32-C7-D34
A67-B32-C7-D34
A39-B32-C7-D34
A65-B32-C7-D34
A66-B32-C7-D34
A2-B39-C7-D34
A3-B39-C7-D34
A9-B39-C7-D34
A13-B39-C7-D34
A24-B39-C7-D34
A69-B39-C7-D34
A67-B39-C7-D34

-continued

A39-B39-C7-D34
A65-B39-C7-D34
A66-B39-C7-D34
A2-B45-C7-D34
A3-B45-C7-D34
A9-B45-C7-D34
A13-B45-C7-D34
A24-B45-C7-D34
A69-B45-C7-D34
A67-B45-C7-D34
A39-B45-C7-D34
A65-B45-C7-D34
A66-B45-C7-D34
A2-B53-C7-D34
A3-B53-C7-D34
A9-B53-C7-D34
A13-B53-C7-D34
A24-B53-C7-D34
A69-B53-C7-D34
A67-B53-C7-D34
A39-B53-C7-D34
A65-B53-C7-D34
A66-B53-C7-D34
A2-B79-C7-D34
A3-B79-C7-D34
A9-B79-C7-D34
A13-B79-C7-D34
A24-B79-C7-D34
A69-B79-C7-D34
A67-B79-C7-D34
A39-B79-C7-D34
A65-B79-C7-D34
A66-B79-C7-D34
A2-B80-C7-D34
A3-B80-C7-D34
A9-B80-C7-D34
A13-B80-C7-D34
A24-B80-C7-D34
A69-B80-C7-D34
A67-B80-C7-D34
A39-B80-C7-D34
A65-B80-C7-D34
A66-B80-C7-D34
A2-B85-C7-D34
A3-B85-C7-D34
A9-B85-C7-D34
A13-B85-C7-D34
A24-B85-C7-D34
A69-B85-C7-D34
A67-B85-C7-D34
A39-B85-C7-D34
A65-B85-C7-D34
A66-B85-C7-D34
A2-B86-C7-D34
A3-B86-C7-D34
A9-B86-C7-D34
A13-B86-C7-D34
A24-B86-C7-D34
A69-B86-C7-D34
A67-B86-C7-D34
A39-B86-C7-D34
A65-B86-C7-D34
A66-B86-C7-D34
A2-B87-C7-D34
A3-B87-C7-D34
A9-B87-C7-D34
A13-B87-C7-D34
A24-B87-C7-D34
A69-B87-C7-D34
A67-B87-C7-D34
A39-B87-C7-D34
A65-B87-C7-D34
A66-B87-C7-D34
A2-B89-C7-D34
A3-B89-C7-D34
A9-B89-C7-D34
A13-B89-C7-D34
A24-B89-C7-D34
A69-B89-C7-D34
A67-B89-C7-D34

-continued

A39-B89-C7-D34
A65-B89-C7-D34
A66-B89-C7-D34
A2-B92-C7-D34
A3-B92-C7-D34
A9-B92-C7-D34
A13-B92-C7-D34
A24-B92-C7-D34
A69-B92-C7-D34
A67-B92-C7-D34
A39-B92-C7-D34
A65-B92-C7-D34
A66-B92-C7-D34
A2-B4-C8-D34
A3-B4-C8-D34
A9-B4-C8-D34
A13-B4-C8-D34
A24-B4-C8-D34
A69-B4-C8-D34
A67-B4-C8-D34
A39-B4-C8-D34
A65-B4-C8-D34
A66-B4-C8-D34
A2-B5-C8-D34
A3-B5-C8-D34
A9-B5-C8-D34
A13-B5-C8-D34
A24-B5-C8-D34
A69-B5-C8-D34
A67-B5-C8-D34
A39-B5-C8-D34
A65-B5-C8-D34
A66-B5-C8-D34
A2-B6-C8-D34
A3-B6-C8-D34
A9-B6-C8-D34
A13-B6-C8-D34
A24-B6-C8-D34
A69-B6-C8-D34
A67-B6-C8-D34
A39-B6-C8-D34
A65-B6-C8-D34
A66-B6-C8-D34
A2-B32-C8-D34
A3-B32-C8-D34
A9-B32-C8-D34
A13-B32-C8-D34
A24-B32-C8-D34
A69-B32-C8-D34
A67-B32-C8-D34
A39-B32-C8-D34
A65-B32-C8-D34
A66-B32-C8-D34
A2-B39-C8-D34
A3-B39-C8-D34
A9-B39-C8-D34
A13-B39-C8-D34
A24-B39-C8-D34
A69-B39-C8-D34
A67-B39-C8-D34
A39-B39-C8-D34
A65-B39-C8-D34
A66-B39-C8-D34
A2-B45-C8-D34
A3-B45-C8-D34
A9-B45-C8-D34
A13-B45-C8-D34
A24-B45-C8-D34
A69-B45-C8-D34
A67-B45-C8-D34
A39-B45-C8-D34
A65-B45-C8-D34
A66-B45-C8-D34
A2-B53-C8-D34
A3-B53-C8-D34
A9-B53-C8-D34
A13-B53-C8-D34
A24-B53-C8-D34
A69-B53-C8-D34
A67-B53-C8-D34

-continued

A39-B53-C8-D34
A65-B53-C8-D34
A66-B53-C8-D34
A2-B79-C8-D34
A3-B79-C8-D34
A9-B79-C8-D34
A13-B79-C8-D34
A24-B79-C8-D34
A69-B79-C8-D34
A67-B79-C8-D34
A39-B79-C8-D34
A65-B79-C8-D34
A66-B79-C8-D34
A2-B80-C8-D34
A3-B80-C8-D34
A9-B80-C8-D34
A13-B80-C8-D34
A24-B80-C8-D34
A69-B80-C8-D34
A67-B80-C8-D34
A39-B80-C8-D34
A65-B80-C8-D34
A66-B80-C8-D34
A2-B85-C8-D34
A3-B85-C8-D34
A9-B85-C8-D34
A13-B85-C8-D34
A24-B85-C8-D34
A69-B85-C8-D34
A67-B85-C8-D34
A39-B85-C8-D34
A65-B85-C8-D34
A66-B85-C8-D34
A2-B86-C8-D34
A3-B86-C8-D34
A9-B86-C8-D34
A13-B86-C8-D34
A24-B86-C8-D34
A69-B86-C8-D34
A67-B86-C8-D34
A39-B86-C8-D34
A65-B86-C8-D34
A66-B86-C8-D34
A2-B87-C8-D34
A3-B87-C8-D342
A9-B87-C8-D34
A13-B87-C8-D34
A24-B87-C8-D34
A69-B87-C8-D34
A67-B87-C8-D34
A39-B87-C8-D34
A65-B87-C8-D34
A66-B87-C8-D34
A2-B89-C8-D34
A3-B89-C8-D34
A9-B89-C8-D34
A13-B89-C8-D34
A24-B89-C8-D34
A69-B89-C8-D34
A67-B89-C8-D34
A39-B89-C8-D34
A65-B89-C8-D34
A66-B89-C8-D34
A2-B92-C8-D34
A3-B92-C8-D34
A9-B92-C8-D34
A13-B92-C8-D34
A24-B92-C8-D34
A69-B92-C8-D34
A67-B92-C8-D34
A39-B92-C8-D34
A65-B92-C8-D34
A66-B92-C8-D34
A2-B4-C9-D34
A3-B4-C9-D34
A9-B4-C9-D34
A13-B4-C9-D34
A24-B4-C9-D34
A69-B4-C9-D34
A67-B4-C9-D34

-continued
A39-B4-C9-D34
A65-B4-C9-D34
A66-B4-C9-D34
A2-B5-C9-D34
A3-B5-C9-D34
A9-B5-C9-D34
A13-B5-C9-D34
A24-B5-C9-D34
A69-B5-C9-D34
A67-B5-C9-D34
A39-B5-C9-D34
A65-B5-C9-D34
A66-B5-C9-D34
A2-B6-C9-D34
A3-B6-C9-D34
A9-B6-C9-D34
A13-B6-C9-D34
A24-B6-C9-D34
A69-B6-C9-D34
A67-B6-C9-D34
A39-B6-C9-D34
A65-B6-C9-D34
A66-B6-C9-D34
A2-B32-C9-D34
A3-B32-C9-D34
A9-B32-C9-D34
A13-B32-C9-D34
A24-B32-C9-D34
A69-B32-C9-D34
A67-B32-C9-D34
A39-B32-C9-D34
A65-B32-C9-D34
A66-B32-C9-D34
A2-B39-C9-D34
A3-B39-C9-D34
A9-B39-C9-D34
A13-B39-C9-D34
A24-B39-C9-D34
A69-B39-C9-D34
A67-B39-C9-D34
A39-B39-C9-D34
A65-B39-C9-D34
A66-B39-C9-D34
A2-B45-C9-D34
A3-B45-C9-D34
A9-B45-C9-D34
A13-B45-C9-D34
A24-B45-C9-D34
A69-B45-C9-D34
A67-B45-C9-D34
A39-B45-C9-D34
A65-B45-C9-D34
A66-B45-C9-D34
A2-B53-C9-D34
A3-B53-C9-D34
A9-B53-C9-D34
A13-B53-C9-D34
A24-B53-C9-D34
A69-B53-C9-D34
A67-B53-C9-D34
A39-B53-C9-D34
A65-B53-C9-D34
A66-B53-C9-D34
A2-B79-C9-D34
A3-B79-C9-D34
A9-B79-C9-D34
A13-B79-C9-D34
A24-B79-C9-D34
A69-B79-C9-D34
A67-B79-C9-D34
A39-B79-C9-D34
A65-B79-C9-D34
A66-B79-C9-D34
A2-B80-C9-D34
A3-B80-C9-D34
A9-B80-C9-D34
A13-B80-C9-D34
A24-B80-C9-D34
A69-B80-C9-D34
A67-B80-C9-D34

-continued
A39-B80-C9-D34
A65-B80-C9-D34
A66-B80-C9-D34
A2-B85-C9-D34
A3-B85-C9-D34
A9-B85-C9-D34
A13-B85-C9-D34
A24-B85-C9-D34
A69-B85-C9-D34
A67-B85-C9-D34
A39-B85-C9-D34
A65-B85-C9-D34
A66-B85-C9-D34
A2-B86-C9-D34
A3-B86-C9-D34
A9-B86-C9-D34
A13-B86-C9-D34
A24-B86-C9-D34
A69-B86-C9-D34
A67-B86-C9-D34
A39-B86-C9-D34
A65-B86-C9-D34
A66-B86-C9-D34
A2-B87-C9-D34
A3-B87-C9-D34
A9-B87-C9-D34
A13-B87-C9-D34
A24-B87-C9-D34
A69-B87-C9-D34
A67-B87-C9-D34
A39-B87-C9-D34
A65-B87-C9-D34
A66-B87-C9-D34
A2-B89-C9-D34
A3-B89-C9-D34
A9-B89-C9-D34
A13-B89-C9-D34
A24-B89-C9-D34
A69-B89-C9-D34
A67-B89-C9-D34
A39-B89-C9-D34
A65-B89-C9-D34
A66-B89-C9-D34
A2-B92-C9-D34
A3-B92-C9-D34
A9-B92-C9-D34
A13-B92-C9-D34
A24-B92-C9-D34
A69-B92-C9-D34
A67-B92-C9-D34
A39-B92-C9-D34
A65-B92-C9-D34
A66-B92-C9-D34
A2-B4-C10-D34
A3-B4-C10-D34
A9-B4-C10-D34
A13-B4-C10-D34
A24-B4-C10-D34
A69-B4-C10-D34
A67-B4-C10-D34
A39-B4-C10-D34
A65-B4-C10-D34
A66-B4-C10-D34
A2-B5-C10-D34
A3-B5-C10-D34
A9-B5-C10-D34
A13-B5-C10-D34
A24-B5-C10-D34
A69-B5-C10-D34
A67-B5-C10-D34
A39-B5-C10-D34
A65-B5-C10-D34
A66-B5-C10-D34
A2-B6-C10-D34
A3-B6-C10-D34
A9-B6-C10-D34
A13-B6-C10-D34
A24-B6-C10-D34
A69-B6-C10-D34
A67-B6-C10-D34

-continued
A39-B6-C10-D34
A65-B6-C10-D34
A66-B6-C10-D34
A2-B32-C10-D34
A3-B32-C10-D34
A9-B32-C10-D34
A13-B32-C10-D34
A24-B32-C10-D34
A69-B32-C10-D34
A67-B32-C10-D34
A39-B32-C10-D34
A65-B32-C10-D34
A66-B32-C10-D34
A2-B39-C10-D34
A3-B39-C10-D34
A9-B39-C10-D34
A13-B39-C10-D34
A24-B39-C10-D34
A69-B39-C10-D34
A67-B39-C10-D34
A39-B39-C10-D34
A65-B39-C10-D34
A66-B39-C10-D34
A2-B45-C10-D34
A3-B45-C10-D34
A9-B45-C10-D34
A13-B45-C10-D34
A24-B45-C10-D34
A69-B45-C10-D34
A67-B45-C10-D34
A39-B45-C10-D34
A65-B45-C10-D34
A66-B45-C10-D34
A2-B53-C10-D34
A3-B53-C10-D34
A9-B53-C10-D34
A13-B53-C10-D34
A24-B53-C10-D34
A69-B53-C10-D34
A67-B53-C10-D34
A39-B53-C10-D34
A65-B53-C10-D34
A66-B53-C10-D34
A2-B79-C10-D34
A3-B79-C10-D34
A9-B79-C10-D34
A13-B79-C10-D34
A24-B79-C10-D34
A69-B79-C10-D34
A67-B79-C10-D34
A39-B79-C10-D34
A65-B79-C10-D34
A66-B79-C10-D34
A2-B80-C10-D34
A3-B80-C10-D34
A9-B80-C10-D34
A13-B80-C10-D34
A24-B80-C10-D34
A69-B80-C10-D34
A67-B80-C10-D34
A39-B80-C10-D34
A65-B80-C10-D34
A66-B80-C10-D34
A2-B85-C10-D34
A3-B85-C10-D34
A9-B85-C10-D34
A13-B85-C10-D34
A24-B85-C10-D34
A69-B85-C10-D34
A67-B85-C10-D34
A39-B85-C10-D34
A65-B85-C10-D34
A66-B85-C10-D34
A2-B86-C10-D34
A3-B86-C10-D34
A9-B86-C10-D34
A13-B86-C10-D34
A24-B86-C10-D34
A69-B86-C10-D34
A67-B86-C10-D34

-continued
A39-B86-C10-D34
A65-B86-C10-D34
A66-B86-C10-D34
A2-B87-C10-D34
A3-B87-C10-D34
A9-B87-C10-D34
A13-B87-C10-D34
A24-B87-C10-D34
A69-B87-C10-D34
A67-B87-C10-D34
A39-B87-C10-D34
A65-B87-C10-D34
A66-B87-C10-D34
A2-B89-C10-D34
A3-B89-C10-D34
A9-B89-C10-D34
A13-B89-C10-D34
A24-B89-C10-D34
A69-B89-C10-D34
A67-B89-C10-D34
A39-B89-C10-D34
A65-B89-C10-D34
A66-B89-C10-D34
A2-B92-C10-D34
A3-B92-C10-D34
A9-B92-C10-D34
A13-B92-C10-D34
A24-B92-C10-D34
A69-B92-C10-D34
A67-B92-C10-D34
A39-B92-C10-D34
A65-B92-C10-D34
A66-B92-C10-D34
A2-B4-C11-D34
A3-B4-C11-D34
A9-B4-C11-D34
A13-B4-C11-D34
A24-B4-C11-D34
A69-B4-C11-D34
A67-B4-C11-D34
A39-B4-C11-D34
A65-B4-C11-D34
A66-B4-C11-D34
A2-B5-C11-D34
A3-B5-C11-D34
A9-B5-C11-D34
A13-B5-C11-D34
A24-B5-C11-D34
A69-B5-C11-D34
A67-B5-C11-D34
A39-B5-C11-D34
A65-B5-C11-D34
A66-B5-C11-D34
A2-B6-C11-D34
A3-B6-C11-D34
A9-B6-C11-D34
A13-B6-C11-D34
A24-B6-C11-D34
A69-B6-C11-D34
A67-B6-C11-D34
A39-B6-C11-D34
A65-B6-C11-D34
A66-B6-C11-D34
A2-B32-C11-D34
A3-B32-C11-D34
A9-B32-C11-D34
A13-B32-C11-D34
A24-B32-C11-D34
A69-B32-C11-D34
A67-B32-C11-D34
A39-B32-C11-D34
A65-B32-C11-D34
A66-B32-C11-D34
A2-B39-C11-D34
A3-B39-C11-D34
A9-B39-C11-D34
A13-B39-C11-D34
A24-B39-C11-D34
A69-B39-C11-D34
A67-B39-C11-D34

-continued
A39-B39-C11-D34
A65-B39-C11-D34
A66-B39-C11-D34
A2-B45-C11-D34
A3-B45-C11-D34
A9-B45-C11-D34
A13-B45-C11-D34
A24-B45-C11-D34
A69-B45-C11-D34
A67-B45-C11-D34
A39-B45-C11-D34
A65-B45-C11-D34
A66-B45-C11-D34
A2-B53-C11-D34
A3-B53-C11-D34
A9-B53-C11-D34
A13-B53-C11-D34
A24-B53-C11-D34
A69-B53-C11-D34
A67-B53-C11-D34
A39-B53-C11-D34
A65-B53-C11-D34
A66-B53-C11-D34
A2-B79-C11-D34
A3-B79-C11-D34
A9-B79-C11-D34
A13-B79-C11-D34
A24-B79-C11-D34
A69-B79-C11-D34
A67-B79-C11-D34
A39-B79-C11-D34
A65-B79-C11-D34
A66-B79-C11-D34
A2-B80-C11-D34
A3-B80-C11-D34
A9-B80-C11-D34
A13-B80-C11-D34
A24-B80-C11-D34
A69-B80-C11-D34
A67-B80-C11-D34
A39-B80-C11-D34
A65-B80-C11-D34
A66-B80-C11-D34
A2-B85-C11-D34
A3-B85-C11-D34
A9-B85-C11-D34
A13-B85-C11-D34
A24-B85-C11-D34
A69-B85-C11-D34
A67-B85-C11-D34
A39-B85-C11-D34
A65-B85-C11-D34
A66-B85-C11-D34
A2-B86-C11-D34
A3-B86-C11-D34
A9-B86-C11-D34
A13-B86-C11-D34
A24-B86-C11-D34
A69-B86-C11-D34
A67-B86-C11-D34
A39-B86-C11-D34
A65-B86-C11-D34
A66-B86-C11-D34
A2-B87-C11-D34
A3-B87-C11-D34
A9-B87-C11-D34
A13-B87-C11-D34
A24-B87-C11-D34
A69-B87-C11-D34
A67-B87-C11-D34
A39-B87-C11-D34
A65-B87-C11-D34
A66-B87-C11-D34
A2-B89-C11-D34
A3-B89-C11-D34
A9-B89-C11-D34
A13-B89-C11-D34
A24-B89-C11-D34
A69-B89-C11-D34
A67-B89-C11-D34

-continued
A39-B89-C11-D34
A65-B89-C11-D34
A66-B89-C11-D34
A2-B92-C11-D34
A3-B92-C11-D34
A9-B92-C11-D34
A13-B92-C11-D34
A24-B92-C11-D34
A69-B92-C11-D34
A67-B92-C11-D34
A39-B92-C11-D34
A65-B92-C11-D34
A66-B92-C11-D34
A2-B4-C12-D34
A3-B4-C12-D34
A9-B4-C12-D34
A13-B4-C12-D34
A24-B4-C12-D34
A69-B4-C12-D34
A67-B4-C12-D34
A39-B4-C12-D34
A65-B4-C12-D34
A66-B4-C12-D34
A2-B5-C12-D34
A3-B5-C12-D34
A9-B5-C12-D34
A13-B5-C12-D34
A24-B5-C12-D34
A69-B5-C12-D34
A67-B5-C12-D34
A39-B5-C12-D34
A65-B5-C12-D34
A66-B5-C12-D34
A2-B6-C12-D34
A3-B6-C12-D34
A9-B6-C12-D34
A13-B6-C12-D34
A24-B6-C12-D34
A69-B6-C12-D34
A67-B6-C12-D34
A39-B6-C12-D34
A65-B6-C12-D34
A66-B6-C12-D34
A2-B32-C12-D34
A3-B32-C12-D34
A9-B32-C12-D34
A13-B32-C12-D34
A24-B32-C12-D34
A69-B32-C12-D34
A67-B32-C12-D34
A39-B32-C12-D34
A65-B32-C12-D34
A66-B32-C12-D34
A2-B39-C12-D34
A3-B39-C12-D34
A9-B39-C12-D34
A13-B39-C12-D34
A24-B39-C12-D34
A69-B39-C12-D34
A67-B39-C12-D34
A39-B39-C12-D34
A65-B39-C12-D34
A66-B39-C12-D34
A2-B45-C12-D34
A3-B45-C12-D34
A9-B45-C12-D34
A13-B45-C12-D34
A24-B45-C12-D34
A69-B45-C12-D34
A67-B45-C12-D34
A39-B45-C12-D34
A65-B45-C12-D34
A66-B45-C12-D34
A2-B53-C12-D34
A3-B53-C12-D34
A9-B53-C12-D34
A13-B53-C12-D34
A24-B53-C12-D34
A69-B53-C12-D34
A67-B53-C12-D34

-continued
A39-B53-C12-D34
A65-B53-C12-D34
A66-B53-C12-D34
A2-B79-C12-D34
A3-B79-C12-D34
A9-B79-C12-D34
A13-B79-C12-D34
A24-B79-C12-D34
A69-B79-C12-D34
A67-B79-C12-D34
A39-B79-C12-D34
A65-B79-C12-D34
A66-B79-C12-D34
A2-B80-C12-D34
A3-B80-C12-D34
A9-B80-C12-D34
A13-B80-C12-D34
A24-B80-C12-D34
A69-B80-C12-D34
A67-B80-C12-D34
A39-B80-C12-D34
A65-B80-C12-D34
A66-B80-C12-D34
A2-B85-C12-D34
A3-B85-C12-D34
A9-B85-C12-D34
A13-B85-C12-D34
A24-B85-C12-D34
A69-B85-C12-D34
A67-B85-C12-D34
A39-B85-C12-D34
A65-B85-C12-D34
A66-B85-C12-D34
A2-B86-C12-D34
A3-B86-C12-D34
A9-B86-C12-D34
A13-B86-C12-D34
A24-B86-C12-D34
A69-B86-C12-D34
A67-B86-C12-D34
A39-B86-C12-D34
A65-B86-C12-D34
A66-B86-C12-D34
A2-B87-C12-D34
A3-B87-C12-D34
A9-B87-C12-D34
A13-B87-C12-D34
A24-B87-C12-D34
A69-B87-C12-D34
A67-B87-C12-D34
A39-B87-C12-D34
A65-B87-C12-D34
A66-B87-C12-D34
A2-B89-C12-D34
A3-B89-C12-D34
A9-B89-C12-D34
A13-B89-C12-D34
A24-B89-C12-D34
A69-B89-C12-D34
A67-B89-C12-D34
A39-B89-C12-D34
A65-B89-C12-D34
A66-B89-C12-D34
A2-B92-C12-D34
A3-B92-C12-D34
A9-B92-C12-D34
A13-B92-C12-D34
A24-B92-C12-D34
A69-B92-C12-D34
A67-B92-C12-D34
A39-B92-C12-D34
A65-B92-C12-D34
A66-B92-C12-D34
A2-B4-C13-D34
A3-B4-C13-D34
A9-B4-C13-D34
A13-B4-C13-D34
A24-B4-C13-D34
A69-B4-C13-D34
A67-B4-C13-D34

-continued
A39-B4-C13-D34
A65-B4-C13-D34
A66-B4-C13-D34
A2-B5-C13-D34
A3-B5-C13-D34
A9-B5-C13-D34
A13-B5-C13-D34
A24-B5-C13-D34
A69-B5-C13-D34
A67-B5-C13-D34
A39-B5-C13-D34
A65-B5-C13-D34
A66-B5-C13-D34
A2-B6-C13-D34
A3-B6-C13-D34
A9-B6-C13-D34
A13-B6-C13-D34
A24-B6-C13-D34
A69-B6-C13-D34
A67-B6-C13-D34
A39-B6-C13-D34
A65-B6-C13-D34
A66-B6-C13-D34
A2-B32-C13-D34
A3-B32-C13-D34
A9-B32-C13-D34
A13-B32-C13-D34
A24-B32-C13-D34
A69-B32-C13-D34
A67-B32-C13-D34
A39-B32-C13-D34
A65-B32-C13-D34
A66-B32-C13-D34
A2-B39-C13-D34
A3-B39-C13-D34
A9-B39-C13-D34
A13-B39-C13-D34
A24-B39-C13-D34
A69-B39-C13-D34
A67-B39-C13-D34
A39-B39-C13-D34
A65-B39-C13-D34
A66-B39-C13-D34
A2-B45-C13-D34
A3-B45-C13-D34
A9-B45-C13-D34
A13-B45-C13-D34
A24-B45-C13-D34
A69-B45-C13-D34
A67-B45-C13-D34
A39-B45-C13-D34
A65-B45-C13-D34
A66-B45-C13-D34
A2-B53-C13-D34
A3-B53-C13-D34
A9-B53-C13-D34
A13-B53-C13-D34
A24-B53-C13-D34
A69-B53-C13-D34
A67-B53-C13-D34
A39-B53-C13-D34
A65-B53-C13-D34
A66-B53-C13-D34
A2-B79-C13-D34
A3-B79-C13-D34
A9-B79-C13-D34
A13-B79-C13-D34
A24-B79-C13-D34
A69-B79-C13-D34
A67-B79-C13-D34
A39-B79-C13-D34
A65-B79-C13-D34
A66-B79-C13-D34
A2-B80-C13-D34
A3-B80-C13-D34
A9-B80-C13-D34
A13-B80-C13-D34
A24-B80-C13-D34
A69-B80-C13-D34
A67-B80-C13-D34

-continued
A39-B80-C13-D34
A65-B80-C13-D34
A66-B80-C13-D34
A2-B85-C13-D34
A3-B85-C13-D34
A9-B85-C13-D34
A13-B85-C13-D34
A24-B85-C13-D34
A69-B85-C13-D34
A67-B85-C13-D34
A39-B85-C13-D34
A65-B85-C13-D34
A66-B85-C13-D34
A2-B86-C13-D34
A3-B86-C13-D34
A9-B86-C13-D34
A13-B86-C13-D34
A24-B86-C13-D34
A69-B86-C13-D34
A67-B86-C13-D34
A39-B86-C13-D34
A65-B86-C13-D34
A66-B86-C13-D34
A2-B87-C13-D34
A3-B87-C13-D34
A9-B87-C13-D34
A13-B87-C13-D34
A24-B87-C13-D34
A69-B87-C13-D34
A67-B87-C13-D34
A39-B87-C13-D34
A65-B87-C13-D34
A66-B87-C13-D34
A2-B89-C13-D34
A3-B89-C13-D34
A9-B89-C13-D34
A13-B89-C13-D34
A24-B89-C13-D34
A69-B89-C13-D34
A67-B89-C13-D34
A39-B89-C13-D34
A65-B89-C13-D34
A66-B89-C13-D34
A2-B92-C13-D34
A3-B92-C13-D34
A9-B92-C13-D34
A13-B92-C13-D34
A24-B92-C13-D34
A69-B92-C13-D34
A67-B92-C13-D34
A39-B92-C13-D34
A65-B92-C13-D34
A66-B92-C13-D34
A2-B4-C1-D35
A3-B4-C1-D35
A9-B4-C1-D35
A13-B4-C1-D35
A24-B4-C1-D35
A69-B4-C1-D35
A67-B4-C1-D35
A39-B4-C1-D35
A65-B4-C1-D35
A66-B4-C1-D35
A2-B5-C1-D35
A3-B5-C1-D35
A9-B5-C1-D35
A13-B5-C1-D35
A24-B5-C1-D35
A69-B5-C1-D35
A67-B5-C1-D35
A39-B5-C1-D35
A65-B5-C1-D35
A66-B5-C1-D35
A2-B6-C1-D35
A3-B6-C1-D35
A9-B6-C1-D35
A13-B6-C1-D35
A24-B6-C1-D35
A69-B6-C1-D35
A67-B6-C1-D35

-continued
A39-B6-C1-D35
A65-B6-C1-D35
A66-B6-C1-D35
A2-B32-C1-D35
A3-B32-C1-D35
A9-B32-C1-D35
A13-B32-C1-D35
A24-B32-C1-D35
A69-B32-C1-D35
A67-B32-C1-D35
A39-B32-C1-D35
A65-B32-C1-D35
A66-B32-C1-D35
A2-B39-C1-D35
A3-B39-C1-D35
A9-B39-C1-D35
A13-B39-C1-D35
A24-B39-C1-D35
A69-B39-C1-D35
A67-B39-C1-D35
A39-B39-C1-D35
A65-B39-C1-D35
A66-B39-C1-D35
A2-B45-C1-D35
A3-B45-C1-D35
A9-B45-C1-D35
A13-B45-C1-D35
A24-B45-C1-D35
A69-B45-C1-D35
A67-B45-C1-D35
A39-B45-C1-D35
A65-B45-C1-D35
A66-B45-C1-D35
A2-B53-C1-D35
A3-B53-C1-D35
A9-B53-C1-D35
A13-B53-C1-D35
A24-B53-C1-D35
A69-B53-C1-D35
A67-B53-C1-D35
A39-B53-C1-D35
A65-B53-C1-D35
A66-B53-C1-D35
A2-B79-C1-D35
A3-B79-C1-D35
A9-B79-C1-D35
A13-B79-C1-D35
A24-B79-C1-D35
A69-B79-C1-D35
A67-B79-C1-D35
A39-B79-C1-D35
A65-B79-C1-D35
A66-B79-C1-D35
A2-B80-C1-D35
A3-B80-C1-D35
A9-B80-C1-D35
A13-B80-C1-D35
A24-B80-C1-D35
A69-B80-C1-D35
A67-B80-C1-D35
A39-B80-C1-D35
A65-B80-C1-D35
A66-B80-C1-D35
A2-B85-C1-D35
A3-B85-C1-D35
A9-B85-C1-D35
A13-B85-C1-D35
A24-B85-C1-D35
A69-B85-C1-D35
A67-B85-C1-D35
A39-B85-C1-D35
A65-B85-C1-D35
A66-B85-C1-D35
A2-B86-C1-D35
A3-B86-C1-D35
A9-B86-C1-D35
A13-B86-C1-D35
A24-B86-C1-D35
A69-B86-C1-D35
A67-B86-C1-D35

-continued
A39-B86-C1-D35
A65-B86-C1-D35
A66-B86-C1-D35
A2-B87-C1-D35
A3-B87-C1-D35
A9-B87-C1-D35
A13-B87-C1-D35
A24-B87-C1-D35
A69-B87-C1-D35
A67-B87-C1-D35
A39-B87-C1-D35
A65-B87-C1-D35
A66-B87-C1-D35
A2-B89-C1-D35
A3-B89-C1-D35
A9-B89-C1-D35
A13-B89-C1-D35
A24-B89-C1-D35
A69-B89-C1-D35
A67-B89-C1-D35
A39-B89-C1-D35
A65-B89-C1-D35
A66-B89-C1-D35
A2-B92-C1-D35
A3-B92-C1-D35
A9-B92-C1-D35
A13-B92-C1-D35
A24-B92-C1-D35
A69-B92-C1-D35
A67-B92-C1-D35
A39-B92-C1-D35
A65-B92-C1-D35
A66-B92-C1-D35
A2-B4-C2-D35
A3-B4-C2-D35
A9-B4-C2-D35
A13-B4-C2-D35
A24-B4-C2-D35
A69-B4-C2-D35
A67-B4-C2-D35
A39-B4-C2-D35
A65-B4-C2-D35
A66-B4-C2-D35
A2-B5-C2-D35
A3-B5-C2-D35
A9-B5-C2-D35
A13-B5-C2-D35
A24-B5-C2-D35
A69-B5-C2-D35
A67-B5-C2-D35
A39-B5-C2-D35
A65-B5-C2-D35
A66-B5-C2-D35
A2-B6-C2-D35
A3-B6-C2-D35
A9-B6-C2-D35
A13-B6-C2-D35
A24-B6-C2-D35
A69-B6-C2-D35
A67-B6-C2-D35
A39-B6-C2-D35
A65-B6-C2-D35
A66-B6-C2-D35
A2-B32-C2-D35
A3-B32-C2-D35
A9-B32-C2-D35
A13-B32-C2-D35
A24-B32-C2-D35
A69-B32-C2-D35
A67-B32-C2-D35
A39-B32-C2-D35
A65-B32-C2-D35
A66-B32-C2-D35
A2-B39-C2-D35
A3-B39-C2-D35
A9-B39-C2-D35
A13-B39-C2-D35
A24-B39-C2-D35
A69-B39-C2-D35
A67-B39-C2-D35

-continued
A39-B39-C2-D35
A65-B39-C2-D35
A66-B39-C2-D35
A2-B45-C2-D35
A3-B45-C2-D35
A9-B45-C2-D35
A13-B45-C2-D35
A24-B45-C2-D35
A69-B45-C2-D35
A67-B45-C2-D35
A39-B45-C2-D35
A65-B45-C2-D35
A66-B45-C2-D35
A2-B53-C2-D35
A3-B53-C2-D35
A9-B53-C2-D35
A13-B53-C2-D35
A24-B53-C2-D35
A69-B53-C2-D35
A67-B53-C2-D35
A39-B53-C2-D35
A65-B53-C2-D35
A66-B53-C2-D35
A2-B79-C2-D35
A3-B79-C2-D35
A9-B79-C2-D35
A13-B79-C2-D35
A24-B79-C2-D35
A69-B79-C2-D35
A67-B79-C2-D35
A39-B79-C2-D35
A65-B79-C2-D35
A66-B79-C2-D35
A2-B80-C2-D35
A3-B80-C2-D35
A9-B80-C2-D35
A13-B80-C2-D35
A24-B80-C2-D35
A69-B80-C2-D35
A67-B80-C2-D35
A39-B80-C2-D35
A65-B80-C2-D35
A66-B80-C2-D35
A2-B85-C2-D35
A3-B85-C2-D35
A9-B85-C2-D35
A13-B85-C2-D35
A24-B85-C2-D35
A69-B85-C2-D35
A67-B85-C2-D35
A39-B85-C2-D35
A65-B85-C2-D35
A66-B85-C2-D35
A2-B86-C2-D35
A3-B86-C2-D35
A9-B86-C2-D35
A13-B86-C2-D35
A24-B86-C2-D35
A69-B86-C2-D35
A67-B86-C2-D35
A39-B86-C2-D35
A65-B86-C2-D35
A66-B86-C2-D35
A2-B87-C2-D35
A3-B87-C2-D35
A9-B87-C2-D35
A13-B87-C2-D35
A24-B87-C2-D35
A69-B87-C2-D35
A67-B87-C2-D35
A39-B87-C2-D35
A65-B87-C2-D35
A66-B87-C2-D35
A2-B89-C2-D35
A3-B89-C2-D35
A9-B89-C2-D35
A13-B89-C2-D35
A24-B89-C2-D35
A69-B89-C2-D35
A67-B89-C2-D35

-continued
A39-B89-C2-D35
A65-B89-C2-D35
A66-B89-C2-D35
A2-B92-C2-D35
A3-B92-C2-D35
A9-B92-C2-D35
A13-B92-C2-D35
A24-B92-C2-D35
A69-B92-C2-D35
A67-B92-C2-D35
A39-B92-C2-D35
A65-B92-C2-D35
A66-B92-C2-D35
A2-B4-C3-D35
A3-B4-C3-D35
A9-B4-C3-D35
A13-B4-C3-D35
A24-B4-C3-D35
A69-B4-C3-D35
A67-B4-C3-D35
A39-B4-C3-D35
A65-B4-C3-D35
A66-B4-C3-D35
A2-B5-C3-D35
A3-B5-C3-D35
A9-B5-C3-D35
A13-B5-C3-D35
A24-B5-C3-D35
A69-B5-C3-D35
A67-B5-C3-D35
A39-B5-C3-D35
A65-B5-C3-D35
A66-B5-C3-D35
A2-B6-C3-D35
A3-B6-C3-D35
A9-B6-C3-D35
A13-B6-C3-D35
A24-B6-C3-D35
A69-B6-C3-D35
A67-B6-C3-D35
A39-B6-C3-D35
A65-B6-C3-D35
A66-B6-C3-D35
A2-B32-C3-D35
A3-B32-C3-D35
A9-B32-C3-D35
A13-B32-C3-D35
A24-B32-C3-D35
A69-B32-C3-D35
A67-B32-C3-D35
A39-B32-C3-D35
A65-B32-C3-D35
A66-B32-C3-D35
A2-B39-C3-D35
A3-B39-C3-D35
A9-B39-C3-D35
A13-B39-C3-D35
A24-B39-C3-D35
A69-B39-C3-D35
A67-B39-C3-D35
A39-B39-C3-D35
A65-B39-C3-D35
A66-B39-C3-D35
A2-B45-C3-D35
A3-B45-C3-D35
A9-B45-C3-D35
A13-B45-C3-D35
A24-B45-C3-D35
A69-B45-C3-D35
A67-B45-C3-D35
A39-B45-C3-D35
A65-B45-C3-D35
A66-B45-C3-D35
A2-B53-C3-D35
A3-B53-C3-D35
A9-B53-C3-D35
A13-B53-C3-D35
A24-B53-C3-D35
A69-B53-C3-D35
A67-B53-C3-D35

-continued
A39-B53-C3-D35
A65-B53-C3-D35
A66-B53-C3-D35
A2-B79-C3-D35
A3-B79-C3-D35
A9-B79-C3-D35
A13-B79-C3-D35
A24-B79-C3-D35
A69-B79-C3-D35
A67-B79-C3-D35
A39-B79-C3-D35
A65-B79-C3-D35
A66-B79-C3-D35
A2-B80-C3-D35
A3-B80-C3-D35
A9-B80-C3-D35
A13-B80-C3-D35
A24-B80-C3-D35
A69-B80-C3-D35
A67-B80-C3-D35
A39-B80-C3-D35
A65-B80-C3-D35
A66-B80-C3-D35
A2-B85-C3-D35
A3-B85-C3-D35
A9-B85-C3-D35
A13-B85-C3-D35
A24-B85-C3-D35
A69-B85-C3-D35
A67-B85-C3-D35
A39-B85-C3-D35
A65-B85-C3-D35
A66-B85-C3-D35
A2-B86-C3-D35
A3-B86-C3-D35
A9-B86-C3-D35
A13-B86-C3-D35
A24-B86-C3-D35
A69-B86-C3-D35
A67-B86-C3-D35
A39-B86-C3-D35
A65-B86-C3-D35
A66-B86-C3-D35
A2-B87-C3-D35
A3-B87-C3-D35
A9-B87-C3-D35
A13-B87-C3-D35
A24-B87-C3-D35
A69-B87-C3-D35
A67-B87-C3-D35
A39-B87-C3-D35
A65-B87-C3-D35
A66-B87-C3-D35
A2-B89-C3-D35
A3-B89-C3-D35
A9-B89-C3-D35
A13-B89-C3-D35
A24-B89-C3-D35
A69-B89-C3-D35
A67-B89-C3-D35
A39-B89-C3-D35
A65-B89-C3-D35
A66-B89-C3-D35
A2-B92-C3-D35
A3-B92-C3-D35
A9-B92-C3-D35
A13-B92-C3-D35
A24-B92-C3-D35
A69-B92-C3-D35
A67-B92-C3-D35
A39-B92-C3-D35
A65-B92-C3-D35
A66-B92-C3-D35
A2-B4-C4-D35
A3-B4-C4-D35
A9-B4-C4-D35
A13-B4-C4-D35
A24-B4-C4-D35
A69-B4-C4-D35
A67-B4-C4-D35

-continued

| | |
|---|---|
| A39-B4-C4-D35 | A39-B80-C4-D35 |
| A65-B4-C4-D35 | A65-B80-C4-D35 |
| A66-B4-C4-D35 | A66-B80-C4-D35 |
| A2-B5-C4-D35 | A2-B85-C4-D35 |
| A3-B5-C4-D35 | A3-B85-C4-D35 |
| A9-B5-C4-D35 | A9-B85-C4-D35 |
| A13-B5-C4-D35 | A13-B85-C4-D35 |
| A24-B5-C4-D35 | A24-B85-C4-D35 |
| A69-B5-C4-D35 | A69-B85-C4-D35 |
| A67-B5-C4-D35 | A67-B85-C4-D35 |
| A39-B5-C4-D35 | A39-B85-C4-D35 |
| A65-B5-C4-D35 | A65-B85-C4-D35 |
| A66-B5-C4-D35 | A66-B85-C4-D35 |
| A2-B6-C4-D35 | A2-B86-C4-D35 |
| A3-B6-C4-D35 | A3-B86-C4-D35 |
| A9-B6-C4-D35 | A9-B86-C4-D35 |
| A13-B6-C4-D35 | A13-B86-C4-D35 |
| A24-B6-C4-D35 | A24-B86-C4-D35 |
| A69-B6-C4-D35 | A69-B86-C4-D35 |
| A67-B6-C4-D35 | A67-B86-C4-D35 |
| A39-B6-C4-D35 | A39-B86-C4-D35 |
| A65-B6-C4-D35 | A65-B86-C4-D35 |
| A66-B6-C4-D35 | A66-B86-C4-D35 |
| A2-B32-C4-D35 | A2-B87-C4-D35 |
| A3-B32-C4-D35 | A3-B87-C4-D35 |
| A9-B32-C4-D35 | A9-B87-C4-D35 |
| A13-B32-C4-D35 | A13-B87-C4-D35 |
| A24-B32-C4-D35 | A24-B87-C4-D35 |
| A69-B32-C4-D35 | A69-B87-C4-D35 |
| A67-B32-C4-D35 | A67-B87-C4-D35 |
| A39-B32-C4-D35 | A39-B87-C4-D35 |
| A65-B32-C4-D35 | A65-B87-C4-D35 |
| A66-B32-C4-D35 | A66-B87-C4-D35 |
| A2-B39-C4-D35 | A2-B89-C4-D35 |
| A3-B39-C4-D35 | A3-B89-C4-D35 |
| A9-B39-C4-D35 | A9-B89-C4-D35 |
| A13-B39-C4-D35 | A13-B89-C4-D35 |
| A24-B39-C4-D35 | A24-B89-C4-D35 |
| A69-B39-C4-D35 | A69-B89-C4-D35 |
| SA67-B39-C4-D35 | A67-B89-C4-D35 |
| A39-B39-C4-D35 | A39-B89-C4-D35 |
| A65-B39-C4-D35 | A65-B89-C4-D35 |
| A66-B39-C4-D35 | A66-B89-C4-D35 |
| A2-B45-C4-D35 | A2-B92-C4-D35 |
| A3-B45-C4-D35 | A3-B92-C4-D35 |
| A9-B45-C4-D35 | A9-B92-C4-D35 |
| A13-B45-C4-D35 | A13-B92-C4-D35 |
| A24-B45-C4-D35 | A24-B92-C4-D35 |
| A69-B45-C4-D35 | A69-B92-C4-D35 |
| A67-B45-C4-D35 | A67-B92-C4-D35 |
| A39-B45-C4-D35 | A39-B92-C4-D35 |
| A65-B45-C4-D35 | A65-B92-C4-D35 |
| A66-B45-C4-D35 | A66-B92-C4-D35 |
| A2-B53-C4-D35 | A2-B4-C5-D35 |
| A3-B53-C4-D35 | A3-B4-C5-D35 |
| A9-B53-C4-D35 | A9-B4-C5-D35 |
| A13-B53-C4-D35 | A13-B4-C5-D35 |
| A24-B53-C4-D35 | A24-B4-C5-D35 |
| A69-B53-C4-D35 | A69-B4-C5-D35 |
| A67-B53-C4-D35 | A67-B4-C5-D35 |
| A39-B53-C4-D35 | A39-B4-C5-D35 |
| A65-B53-C4-D35 | A65-B4-C5-D35 |
| A66-B53-C4-D35 | A66-B4-C5-D35 |
| A2-B79-C4-D35 | A2-B5-C5-D35 |
| A3-B79-C4-D35 | A3-B5-C5-D35 |
| A9-B79-C4-D35 | A9-B5-C5-D35 |
| A13-B79-C4-D35 | A13-B5-C5-D35 |
| A24-B79-C4-D35 | A24-B5-C5-D35 |
| A69-B79-C4-D35 | A69-B5-C5-D35 |
| A67-B79-C4-D35 | A67-B5-C5-D35 |
| A39-B79-C4-D35 | A39-B5-C5-D35 |
| A65-B79-C4-D35 | A65-B5-C5-D35 |
| A66-B79-C4-D35 | A66-B5-C5-D35 |
| A2-B80-C4-D35 | A2-B6-C5-D35 |
| A3-B80-C4-D35 | A3-B6-C5-D35 |
| A9-B80-C4-D35 | A9-B6-C5-D35 |
| A13-B80-C4-D35 | A13-B6-C5-D35 |
| A24-B80-C4-D35 | A24-B6-C5-D35 |
| A69-B80-C4-D35 | A69-B6-C5-D35 |
| A67-B80-C4-D35 | A67-B6-C5-D35 |

-continued

| | |
|---|---|
| A39-B6-C5-D35 | A39-B86-C5-D35 |
| A65-B6-C5-D35 | A65-B86-C5-D35 |
| A66-B6-C5-D35 | A66-B86-C5-D35 |
| A2-B32-C5-D35 | A2-B87-C5-D35 |
| A3-B32-C5-D35 | A3-B87-C5-D35 |
| A9-B32-C5-D35 | A9-B87-C5-D35 |
| A13-B32-C5-D35 | A13-B87-C5-D35 |
| A24-B32-C5-D35 | A24-B87-C5-D35 |
| A69-B32-C5-D35 | A69-B87-C5-D35 |
| A67-B32-C5-D35 | A67-B87-C5-D35 |
| A39-B32-C5-D35 | A39-B87-C5-D35 |
| A65-B32-C5-D35 | A65-B87-C5-D35 |
| A66-B32-C5-D35 | A66-B87-C5-D35 |
| A2-B39-C5-D35 | A2-B89-C5-D35 |
| A3-B39-C5-D35 | A3-B89-C5-D35 |
| A9-B39-C5-D35 | A9-B89-C5-D35 |
| A13-B39-C5-D35 | A13-B89-C5-D35 |
| A24-B39-C5-D35 | A24-B89-C5-D35 |
| A69-B39-C5-D35 | A69-B89-C5-D35 |
| A67-B39-C5-D35 | A67-B89-C5-D35 |
| A39-B39-C5-D35 | A39-B89-C5-D35 |
| A65-B39-C5-D35 | A65-B89-C5-D35 |
| A66-B39-C5-D35 | A66-B89-C5-D35 |
| A2-B45-C5-D35 | A2-B92-C5-D35 |
| A3-B45-C5-D35 | A3-B92-C5-D35 |
| A9-B45-C5-D35 | A9-B92-C5-D35 |
| A13-B45-C5-D35 | A13-B92-C5-D35 |
| A24-B45-C5-D35 | A24-B92-C5-D35 |
| A69-B45-C5-D35 | A69-B92-C5-D35 |
| A67-B45-C5-D35 | A67-B92-C5-D35 |
| A39-B45-C5-D35 | A39-B92-C5-D35 |
| A65-B45-C5-D35 | A65-B92-C5-D35 |
| A66-B45-C5-D35 | A66-B92-C5-D35 |
| A2-B53-C5-D35 | A2-B4-C6-D35 |
| A3-B53-C5-D35 | A3-B4-C6-D35 |
| A9-B53-C5-D35 | A9-B4-C6-D35 |
| A13-B53-C5-D35 | A13-B4-C6-D35 |
| A24-B53-C5-D35 | A24-B4-C6-D35 |
| A69-B53-C5-D35 | A69-B4-C6-D35 |
| A67-B53-C5-D35 | A67-B4-C6-D35 |
| A39-B53-C5-D35 | A39-B4-C6-D35 |
| A65-B53-C5-D35 | A65-B4-C6-D35 |
| A66-B53-C5-D35 | A66-B4-C6-D35 |
| A2-B79-C5-D35 | A2-B5-C6-D35 |
| A3-B79-C5-D35 | A3-B5-C6-D35 |
| A9-B79-C5-D35 | A9-B5-C6-D35 |
| A13-B79-C5-D35 | A13-B5-C6-D35 |
| A24-B79-C5-D35 | A24-B5-C6-D35 |
| A69-B79-C5-D35 | A69-B5-C6-D35 |
| A67-B79-C5-D35 | A67-B5-C6-D35 |
| A39-B79-C5-D35 | A39-B5-C6-D35 |
| A65-B79-C5-D35 | A65-B5-C6-D35 |
| A66-B79-C5-D35 | A66-B5-C6-D35 |
| A2-B80-C5-D35 | A2-B6-C6-D35 |
| A3-B80-C5-D35 | A3-B6-C6-D35 |
| A9-B80-C5-D35 | A9-B6-C6-D35 |
| A13-B80-C5-D35 | A13-B6-C6-D35 |
| A24-B80-C5-D35 | A24-B6-C6-D35 |
| A69-B80-C5-D35 | A69-B6-C6-D35 |
| A67-B80-C5-D35 | A67-B6-C6-D35 |
| A39-B80-C5-D35 | A39-B6-C6-D35 |
| A65-B80-C5-D35 | A65-B6-C6-D35 |
| A66-B80-C5-D35 | A66-B6-C6-D35 |
| A2-B85-C5-D35 | A2-B32-C6-D35 |
| A3-B85-C5-D35 | A3-B32-C6-D35 |
| A9-B85-C5-D35 | A9-B32-C6-D35 |
| A13-B85-C5-D35 | A13-B32-C6-D35 |
| A24-B85-C5-D35 | A24-B32-C6-D35 |
| A69-B85-C5-D35 | A69-B32-C6-D35 |
| A67-B85-C5-D35 | A67-B32-C6-D35 |
| A39-B85-C5-D35 | A39-B32-C6-D35 |
| A65-B85-C5-D35 | A65-B32-C6-D35 |
| A66-B85-C5-D35 | A66-B32-C6-D35 |
| A2-B86-C5-D35 | A2-B39-C6-D35 |
| A3-B86-C5-D35 | A3-B39-C6-D35 |
| A9-B86-C5-D35 | A9-B39-C6-D35 |
| A13-B86-C5-D35 | A13-B39-C6-D35 |
| A24-B86-C5-D35 | A24-B39-C6-D35 |
| A69-B86-C5-D35 | A69-B39-C6-D35 |
| A67-B86-C5-D35 | A67-B39-C6-D35 |

-continued
A39-B39-C6-D35
A65-B39-C6-D35
A66-B39-C6-D35
A2-B45-C6-D35
A3-B45-C6-D35
A9-B45-C6-D35
A13-B45-C6-D35
A24-B45-C6-D35
A69-B45-C6-D35
A67-B45-C6-D35
A39-B45-C6-D35
A65-B45-C6-D35
A66-B45-C6-D35
A2-B53-C6-D35
A3-B53-C6-D35
A9-B53-C6-D35
A13-B53-C6-D35
A24-B53-C6-D35
A69-B53-C6-D35
A67-B53-C6-D35
A39-B53-C6-D35
A65-B53-C6-D35
A66-B53-C6-D35
A2-B79-C6-D35
A3-B79-C6-D35
A9-B79-C6-D35
A13-B79-C6-D35
A24-B79-C6-D35
A69-B79-C6-D35
A67-B79-C6-D35
A39-B79-C6-D35
A65-B79-C6-D35
A66-B79-C6-D35
A2-B80-C6-D35
A3-B80-C6-D35
A9-B80-C6-D35
A13-B80-C6-D35
A24-B80-C6-D35
A69-B80-C6-D35
A67-B80-C6-D35
A39-B80-C6-D35
A65-B80-C6-D35
A66-B80-C6-D35
A2-B85-C6-D35
A3-B85-C6-D35
A9-B85-C6-D35
A13-B85-C6-D35
A24-B85-C6-D35
A69-B85-C6-D35
A67-B85-C6-D35
A39-B85-C6-D35
A65-B85-C6-D35
A66-B85-C6-D35
A2-B86-C6-D35
A3-B86-C6-D35
A9-B86-C6-D35
A13-B86-C6-D35
A24-B86-C6-D35
A69-B86-C6-D35
A67-B86-C6-D35
A39-B86-C6-D35
A65-B86-C6-D35
A66-B86-C6-D35
A2-B87-C6-D35
A3-B87-C6-D35
A9-B87-C6-D35
A13-B87-C6-D35
A24-B87-C6-D35
A69-B87-C6-D35
A67-B87-C6-D35
A39-B87-C6-D35
A65-B87-C6-D35
A66-B87-C6-D35
A2-B89-C6-D35
A3-B89-C6-D35
A9-B89-C6-D35
A13-B89-C6-D35
A24-B89-C6-D35
A69-B89-C6-D35
A67-B89-C6-D35

-continued
A39-B89-C6-D35
A65-B89-C6-D35
A66-B89-C6-D35
A2-B92-C6-D35
A3-B92-C6-D35
A9-B92-C6-D35
A13-B92-C6-D35
A24-B92-C6-D35
A69-B92-C6-D35
A67-B92-C6-D35
A39-B92-C6-D35
A65-B92-C6-D35
A66-B92-C6-D35
A2-B4-C7-D35
A3-B4-C7-D35
A9-B4-C7-D35
A13-B4-C7-D35
A24-B4-C7-D35
A69-B4-C7-D35
A67-B4-C7-D35
A39-B4-C7-D35
A65-B4-C7-D35
A66-B4-C7-D35
A2-B5-C7-D35
A3-B5-C7-D35
A9-B5-C7-D35
A13-B5-C7-D35
A24-B5-C7-D35
A69-B5-C7-D35
A67-B5-C7-D35
A39-B5-C7-D35
A65-B5-C7-D35
A66-B5-C7-D35
A2-B6-C7-D35
A3-B6-C7-D35
A9-B6-C7-D35
A13-B6-C7-D35
A24-B6-C7-D35
A69-B6-C7-D35
A67-B6-C7-D35
A39-B6-C7-D35
A65-B6-C7-D35
A66-B6-C7-D35
A2-B32-C7-D35
A3-B32-C7-D35
A9-B32-C7-D35
A13-B32-C7-D35
A24-B32-C7-D35
A69-B32-C7-D35
A67-B32-C7-D35
A39-B32-C7-D35
A65-B32-C7-D35
A66-B32-C7-D35
A2-B39-C7-D35
A3-B39-C7-D35
A9-B39-C7-D35
A13-B39-C7-D35
A24-B39-C7-D35
A69-B39-C7-D35
A67-B39-C7-D35
A39-B39-C7-D35
A65-B39-C7-D35
A66-B39-C7-D35
A2-B45-C7-D35
A3-B45-C7-D35
A9-B45-C7-D35
A13-B45-C7-D35
A24-B45-C7-D35
A69-B45-C7-D35
A67-B45-C7-D35
A39-B45-C7-D35
A65-B45-C7-D35
A66-B45-C7-D35
A2-B53-C7-D35
A3-B53-C7-D35
A9-B53-C7-D35
A13-B53-C7-D35
A24-B53-C7-D35
A69-B53-C7-D35
A67-B53-C7-D35

-continued
A39-B53-C7-D35
A65-B53-C7-D35
A66-B53-C7-D35
A2-B79-C7-D35
A3-B79-C7-D35
A9-B79-C7-D35
A13-B79-C7-D35
A24-B79-C7-D35
A69-B79-C7-D35
A67-B79-C7-D35
A39-B79-C7-D35
A65-B79-C7-D35
A66-B79-C7-D35
A2-B80-C7-D35
A3-B80-C7-D35
A9-B80-C7-D35
A13-B80-C7-D35
A24-B80-C7-D35
A69-B80-C7-D35
A67-B80-C7-D35
A39-B80-C7-D35
A65-B80-C7-D35
A66-B80-C7-D35
A2-B85-C7-D35
A3-B85-C7-D35
A9-B85-C7-D35
A13-B85-C7-D35
A24-B85-C7-D35
A69-B85-C7-D35
A67-B85-C7-D35
A39-B85-C7-D35
A65-B85-C7-D35
A66-B85-C7-D35
A2-B86-C7-D35
A3-B86-C7-D35
A9-B86-C7-D35
A13-B86-C7-D35
A24-B86-C7-D35
A69-B86-C7-D35
A67-B86-C7-D35
A39-B86-C7-D35
A65-B86-C7-D35
A66-B86-C7-D35
A2-B87-C7-D35
A3-B87-C7-D35
A9-B87-C7-D35
A13-B87-C7-D35
A24-B87-C7-D35
A69-B87-C7-D35
A67-B87-C7-D35
A39-B87-C7-D35
A65-B87-C7-D35
A66-B87-C7-D35
A2-B89-C7-D35
A3-B89-C7-D35
A9-B89-C7-D35
A13-B89-C7-D35
A24-B89-C7-D35
A69-B89-C7-D35
A67-B89-C7-D35
A39-B89-C7-D35
A65-B89-C7-D35
A66-B89-C7-D35
A2-B92-C7-D35
A3-B92-C7-D35
A9-B92-C7-D35
A13-B92-C7-D35
A24-B92-C7-D35
A69-B92-C7-D35
A67-B92-C7-D35
A39-B92-C7-D35
A65-B92-C7-D35
A66-B92-C7-D35
A2-B4-C8-D35
A3-B4-C8-D35
A9-B4-C8-D35
A13-B4-C8-D35
A24-B4-C8-D35
A69-B4-C8-D35
A67-B4-C8-D35

-continued
A39-B4-C8-D35
A65-B4-C8-D35
A66-B4-C8-D35
A2-B5-C8-D35
A3-B5-C8-D35
A9-B5-C8-D35
A13-B5-C8-D35
A24-B5-C8-D35
A69-B5-C8-D35
A67-B5-C8-D35
A39-B5-C8-D35
A65-B5-C8-D35
A66-B5-C8-D35
A2-B6-C8-D35
A3-B6-C8-D35
A9-B6-C8-D35
A13-B6-C8-D35
A24-B6-C8-D35
A69-B6-C8-D35
A67-B6-C8-D35
A39-B6-C8-D35
A65-B6-C8-D35
A66-B6-C8-D35
A2-B32-C8-D35
A3-B32-C8-D35
A9-B32-C8-D35
A13-B32-C8-D35
A24-B32-C8-D35
A69-B32-C8-D35
A67-B32-C8-D35
A39-B32-C8-D35
A65-B32-C8-D35
A66-B32-C8-D35
A2-B39-C8-D35
A3-B39-C8-D35
A9-B39-C8-D35
A13-B39-C8-D35
A24-B39-C8-D35
A69-B39-C8-D35
A67-B39-C8-D35
A39-B39-C8-D35
A65-B39-C8-D35
A66-B39-C8-D35
A2-B45-C8-D35
A3-B45-C8-D35
A9-B45-C8-D35
A13-B45-C8-D35
A24-B45-C8-D35
A69-B45-C8-D35
A67-B45-C8-D35
A39-B45-C8-D35
A65-B45-C8-D35
A66-B45-C8-D35
A2-B53-C8-D35
A3-B53-C8-D35
A9-B53-C8-D35
A13-B53-C8-D35
A24-B53-C8-D35
A69-B53-C8-D35
A67-B53-C8-D35
A39-B53-C8-D35
A65-B53-C8-D35
A66-B53-C8-D35
A2-B79-C8-D35
A3-B79-C8-D35
A9-B79-C8-D35
A13-B79-C8-D35
A24-B79-C8-D35
A69-B79-C8-D35
A67-B79-C8-D35
A39-B79-C8-D35
A65-B79-C8-D35
A66-B79-C8-D35
A2-B80-C8-D35
A3-B80-C8-D35
A9-B80-C8-D35
A13-B80-C8-D35
A24-B80-C8-D35
A69-B80-C8-D35
A67-B80-C8-D35

-continued

A39-B80-C8-D35
A65-B80-C8-D35
A66-B80-C8-D35
A2-B85-C8-D35
A3-B85-C8-D35
A9-B85-C8-D35
A13-B85-C8-D35
A24-B85-C8-D35
A69-B85-C8-D35
A67-B85-C8-D35
A39-B85-C8-D35
A65-B85-C8-D35
A66-B85-C8-D35
A2-B86-C8-D35
A3-B86-C8-D35
A9-B86-C8-D35
A13-B86-C8-D35
A24-B86-C8-D35
A69-B86-C8-D35
A67-B86-C8-D35
A39-B86-C8-D35
A65-B86-C8-D35
A66-B86-C8-D35
A2-B87-C8-D35
A3-B87-C8-D35
A9-B45-C10-D35
A13-B45-C10-D35
A24-B45-C10-D35
A69-B45-C10-D35
A67-B45-C10-D35
A39-B45-C10-D35
A65-B45-C10-D35
A66-B45-C10-D35
A2-B53-C10-D35
A3-B53-C10-D35
A9-B53-C10-D35
A13-B53-C10-D35
A24-B53-C10-D35
A69-B53-C10-D35
A67-B53-C10-D35
A39-B53-C10-D35
A65-B53-C10-D35
A66-B53-C10-D35
A2-B79-C10-D35
A3-B79-C10-D35
A9-B79-C10-D35
A13-B79-C10-D35
A24-B79-C10-D35
A69-B79-C10-D35
A67-B79-C10-D35
A39-B79-C10-D35
A65-B79-C10-D35
A66-B79-C10-D35
A2-B80-C10-D35
A3-B80-C10-D35
A9-B80-C10-D35
A13-B80-C10-D35
A24-B80-C10-D35
A69-B80-C10-D35
A67-B80-C10-D35
A39-B80-C10-D35
A65-B80-C10-D35
A66-B80-C10-D35
A2-B85-C10-D35
A3-B85-C10-D35
A9-B85-C10-D35
A13-B85-C10-D35
A24-B85-C10-D35
A69-B85-C10-D35
A67-B85-C10-D35
A39-B85-C10-D35
A65-B85-C10-D35
A66-B85-C10-D35
A2-B86-C10-D35
A3-B86-C10-D35
A9-B86-C10-D35
A13-B86-C10-D35
A24-B86-C10-D35
A69-B86-C10-D35
A67-B86-C10-D35

-continued

A39-B86-C10-D35
A65-B86-C10-D35
A66-B86-C10-D35
A2-B87-C10-D35
A3-B87-C10-D35
A9-B87-C10-D35
A13-B87-C10-D35
A24-B87-C10-D35
A69-B87-C10-D35
A67-B87-C10-D35
A39-B87-C10-D35
A65-B87-C10-D35
A66-B87-C10-D35
A2-B89-C10-D35
A3-B89-C10-D35
A9-B89-C10-D35
A13-B89-C10-D35
A24-B89-C10-D35
A69-B89-C10-D35
A67-B89-C10-D35
A39-B89-C10-D35
A65-B89-C10-D35
A66-B89-C10-D35
A2-B92-C10-D35
A3-B92-C10-D35
A9-B92-C10-D35
A13-B92-C10-D35
A24-B92-C10-D35
A69-B92-C10-D35
A67-B92-C10-D35
A39-B92-C10-D35
A65-B92-C10-D35
A66-B92-C10-D35
A2-B4-C11-D35
A3-B4-C11-D35
A9-B4-C11-D35
A13-B4-C11-D35
A24-B4-C11-D35
A69-B4-C11-D35
A67-B4-C11-D35
A39-B4-C11-D35
A65-B4-C11-D35
A66-B4-C11-D35
A2-B5-C11-D35
A3-B5-C11-D35
A9-B5-C11-D35
A13-B5-C11-D35
A24-B5-C11-D35
A69-B5-C11-D35
A67-B5-C11-D35
A39-B5-C11-D35
A65-B5-C11-D35
A66-B5-C11-D35
A2-B6-C11-D35
A3-B6-C11-D35
A9-B6-C11-D35
A13-B6-C11-D35
A24-B6-C11-D35
A69-B6-C11-D35
A67-B6-C11-D35
A39-B6-C11-D35
A65-B6-C11-D35
A66-B6-C11-D35
A2-B32-C11-D35
A3-B32-C11-D35
A9-B32-C11-D35
A13-B32-C11-D35
A24-B32-C11-D35
A69-B32-C11-D35
A67-B32-C11-D35
A39-B32-C11-D35
A65-B32-C11-D35
A66-B32-C11-D35
A2-B39-C11-D35
A3-B39-C11-D35
A9-B39-C11-D35
A13-B39-C11-D35
A24-B39-C11-D35
A69-B39-C11-D35
A67-B39-C11-D35

-continued

A39-B39-C11-D35
A65-B39-C11-D35
A66-B39-C11-D35
A2-B45-C11-D35
A3-B45-C11-D35
A9-B45-C11-D35
A13-B45-C11-D35
A24-B45-C11-D35
A69-B45-C11-D35
A67-B45-C11-D35
A39-B45-C11-D35
A65-B45-C11-D35
A66-B45-C11-D35
A2-B53-C11-D35
A3-B53-C11-D35
A9-B53-C11-D35
A13-B53-C11-D35
A24-B53-C11-D35
A69-B53-C11-D35
A67-B53-C11-D35
A39-B53-C11-D35
A65-B53-C11-D35
A66-B53-C11-D35
A2-B79-C11-D35
A3-B79-C11-D35
A9-B79-C11-D35
A13-B79-C11-D35
A24-B79-C11-D35
A69-B79-C11-D35
A67-B79-C11-D35
A39-B79-C11-D35
A65-B79-C11-D35
A66-B79-C11-D35
A2-B80-C11-D35
A3-B80-C11-D35
A9-B80-C11-D35
A13-B80-C11-D35
A24-B80-C11-D35
A69-B80-C11-D35
A67-B80-C11-D35
A39-B80-C11-D35
A65-B80-C11-D35
A66-B80-C11-D35
A2-B85-C11-D35
A3-B85-C11-D35
A9-B85-C11-D35
A13-B85-C11-D35
A24-B85-C11-D35
A69-B85-C11-D35
A67-B85-C11-D35
A39-B85-C11-D35
A65-B85-C11-D35
A66-B85-C11-D35
A2-B86-C11-D35
A3-B86-C11-D35
A9-B86-C11-D35
A13-B86-C11-D35
A24-B86-C11-D35
A69-B86-C11-D35
A67-B86-C11-D35
A39-B86-C11-D35
A65-B86-C11-D35
A66-B86-C11-D35
A2-B87-C11-D35
A3-B87-C11-D35
A9-B87-C11-D35
A13-B87-C11-D35
A24-B87-C11-D35
A69-B87-C11-D35
A67-B87-C11-D35
A39-B87-C11-D35
A65-B87-C11-D35
A66-B87-C11-D35
A2-B89-C11-D35
A3-B89-C11-D35
A9-B89-C11-D35
A13-B89-C11-D35
A24-B89-C11-D35
A69-B89-C11-D35
A67-B89-C11-D35

-continued

A39-B89-C11-D35
A65-B89-C11-D35
A66-B89-C11-D35
A2-B92-C11-D35
A3-B92-C11-D35
A9-B87-C8-D35
A13-B87-C8-D35
A24-B87-C8-D35
A69-B87-C8-D35
A67-B87-C8-D35
A39-B87-C8-D35
A65-B87-C8-D35
A66-B87-C8-D35
A2-B89-C8-D35
A3-B89-C8-D35
A9-B89-C8-D35
A13-B89-C8-D35
A24-B89-C8-D35
A69-B89-C8-D35
A67-B89-C8-D35
A39-B89-C8-D35
A65-B89-C8-D35
A66-B89-C8-D35
A2-B92-C8-D35
A3-B92-C8-D35
A9-B92-C8-D35
A13-B92-C8-D35
A24-B92-C8-D35
A69-B92-C8-D35
A67-B92-C8-D35
A39-B92-C8-D35
A65-B92-C8-D35
A66-B92-C8-D35
A2-B4-C9-D35
A3-B4-C9-D35
A9-B4-C9-D35
A13-B4-C9-D35
A24-B4-C9-D35
A69-B4-C9-D35
A67-B4-C9-D35
A39-B4-C9-D35
A65-B4-C9-D35
A66-B4-C9-D35
A2-B5-C9-D35
A3-B5-C9-D35
A9-B5-C9-D35
A13-B5-C9-D35
A24-B5-C9-D35
A69-B5-C9-D35
A67-B5-C9-D35
A39-B5-C9-D35
A65-B5-C9-D35
A66-B5-C9-D35
A2-B6-C9-D35
A3-B6-C9-D35
A9-B6-C9-D35
A13-B6-C9-D35
A24-B6-C9-D35
A69-B6-C9-D35
A67-B6-C9-D35
A39-B6-C9-D35
A65-B6-C9-D35
A66-B6-C9-D35
A2-B32-C9-D35
A3-B32-C9-D35
A9-B32-C9-D35
A13-B32-C9-D35
A24-B32-C9-D35
A69-B32-C9-D35
A67-B32-C9-D35
A39-B32-C9-D35
A65-B32-C9-D35
A66-B32-C9-D35
A2-B39-C9-D35
A3-B39-C9-D35
A9-B39-C9-D35
A13-B39-C9-D35
A24-B39-C9-D35
A69-B39-C9-D35
A67-B39-C9-D35

-continued
A39-B39-C9-D35
A65-B39-C9-D35
A66-B39-C9-D35
A2-B45-C9-D35
A3-B45-C9-D35
A9-B45-C9-D35
A13-B45-C9-D35
A24-B45-C9-D35
A69-B45-C9-D35
A67-B45-C9-D35
A39-B45-C9-D35
A65-B45-C9-D35
A66-B45-C9-D35
A2-B53-C9-D35
A3-B53-C9-D35
A9-B53-C9-D35
A13-B53-C9-D35
A24-B53-C9-D35
A69-B53-C9-D35
A67-B53-C9-D35
A39-B53-C9-D35
A65-B53-C9-D35
A66-B53-C9-D35
A2-B79-C9-D35
A3-B79-C9-D35
A9-B79-C9-D35
A13-B79-C9-D35
A24-B79-C9-D35
A69-B79-C9-D35
A67-B79-C9-D35
A39-B79-C9-D35
A65-B79-C9-D35
A66-B79-C9-D35
A2-B80-C9-D35
A3-B80-C9-D35
A9-B80-C9-D35
A13-B80-C9-D35
A24-B80-C9-D35
A69-B80-C9-D35
A67-B80-C9-D35
A39-B80-C9-D35
A65-B80-C9-D35
A66-B80-C9-D35
A2-B85-C9-D35
A3-B85-C9-D35
A9-B85-C9-D35
A13-B85-C9-D35
A24-B85-C9-D35
A69-B85-C9-D35
A67-B85-C9-D35
A39-B85-C9-D35
A65-B85-C9-D35
A66-B85-C9-D35
A2-B86-C9-D35
A3-B86-C9-D35
A9-B86-C9-D35
A13-B86-C9-D35
A24-B86-C9-D35
A69-B86-C9-D35
A67-B86-C9-D35
A39-B86-C9-D35
A65-B86-C9-D35
A66-B86-C9-D35
A2-B87-C9-D35
A3-B87-C9-D35
A9-B87-C9-D35
A13-B87-C9-D35
A24-B87-C9-D35
A69-B87-C9-D35
A67-B87-C9-D35
A39-B87-C9-D35
A65-B87-C9-D35
A66-B87-C9-D35
A2-B89-C9-D35
A3-B89-C9-D35
A9-B89-C9-D35
A13-B89-C9-D35
A24-B89-C9-D35
A69-B89-C9-D35
A67-B89-C9-D35

-continued
A39-B89-C9-D35
A65-B89-C9-D35
A66-B89-C9-D35
A2-B92-C9-D35
A3-B92-C9-D35
A9-B92-C9-D35
A13-B92-C9-D35
A24-B92-C9-D35
A69-B92-C9-D35
A67-B92-C9-D35
A39-B92-C9-D35
A65-B92-C9-D35
A66-B92-C9-D35
A2-B4-C10-D35
A3-B4-C10-D35
A9-B4-C10-D35
A13-B4-C10-D35
A24-B4-C10-D35
A69-B4-C10-D35
A67-B4-C10-D35
A39-B4-C10-D35
A65-B4-C10-D35
A66-B4-C10-D35
A2-B5-C10-D35
A3-B5-C10-D35
A9-B5-C10-D35
A13-B5-C10-D35
A24-B5-C10-D35
A69-B5-C10-D35
A67-B5-C10-D35
A39-B5-C10-D35
A65-B5-C10-D35
A66-B5-C10-D35
A2-B6-C10-D35
A3-B6-C10-D35
A9-B6-C10-D35
A13-B6-C10-D35
A24-B6-C10-D35
A69-B6-C10-D35
A67-B6-C10-D35
A39-B6-C10-D35
A65-B6-C10-D35
A66-B6-C10-D35
A2-B32-C10-D35
A3-B32-C10-D35
A9-B32-C10-D35
A13-B32-C10-D35
A24-B32-C10-D35
A69-B32-C10-D35
A67-B32-C10-D35
A39-B32-C10-D35
A65-B32-C10-D35
A66-B32-C10-D35
A2-B39-C10-D35
A3-B39-C10-D35
A9-B39-C10-D35
A13-B39-C10-D35
A24-B39-C10-D35
A69-B39-C10-D35
A67-B39-C10-D35
A39-B39-C10-D35
A65-B39-C10-D35
A66-B39-C10-D35
A2-B45-C10-D35
A3-B45-C10-D35
A9-B92-C11-D35
A13-B92-C11-D35
A24-B92-C11-D35
A69-B92-C11-D35
A67-B92-C11-D35
A39-B92-C11-D35
A65-B92-C11-D35
A66-B92-C11-D35
A2-B4-C12-D35
A3-B4-C12-D35
A9-B4-C12-D35
A13-B4-C12-D35
A24-B4-C12-D35
A69-B4-C12-D35
A67-B4-C12-D35

-continued
A39-B4-C12-D35
A65-B4-C12-D35
A66-B4-C12-D35
A2-B5-C12-D35
A3-B5-C12-D35
A9-B5-C12-D35
A13-B5-C12-D35
A24-B5-C12-D35
A69-B5-C12-D35
A67-B5-C12-D35
A39-B5-C12-D35
A65-B5-C12-D35
A66-B5-C12-D35
A2-B6-C12-D35
A3-B6-C12-D35
A9-B6-C12-D35
A13-B6-C12-D35
A24-B6-C12-D35
A69-B6-C12-D35
A67-B6-C12-D35
A39-B6-C12-D35
A65-B6-C12-D35
A66-B6-C12-D35
A2-B32-C12-D35
A3-B32-C12-D35
A9-B32-C12-D35
A13-B32-C12-D35
A24-B32-C12-D35
A69-B32-C12-D35
A67-B32-C12-D35
A39-B32-C12-D35
A65-B32-C12-D35
A66-B32-C12-D35
A2-B39-C12-D35
A3-B39-C12-D35
A9-B39-C12-D35
A13-B39-C12-D35
A24-B39-C12-D35
A69-B39-C12-D35
A67-B39-C12-D35
A39-B39-C12-D35
A65-B39-C12-D35
A66-B39-C12-D35
A2-B45-C12-D35
A3-B45-C12-D35
A9-B45-C12-D35
A13-B45-C12-D35
A24-B45-C12-D35
A69-B45-C12-D35
A67-B45-C12-D35
A39-B45-C12-D35
A65-B45-C12-D35
A66-B45-C12-D35
A2-B53-C12-D35
A3-B53-C12-D35
A9-B53-C12-D35
A13-B53-C12-D35
A24-B53-C12-D35
A69-B53-C12-D35
A67-B53-C12-D35
A39-B53-C12-D35
A65-B53-C12-D35
A66-B53-C12-D35
A2-B79-C12-D35
A3-B79-C12-D35
A9-B79-C12-D35
A13-B79-C12-D35
A24-B79-C12-D35
A69-B79-C12-D35
A67-B79-C12-D35
A39-B79-C12-D35
A65-B79-C12-D35
A66-B79-C12-D35
A2-B80-C12-D35
A3-B80-C12-D35
A9-B80-C12-D35
A13-B80-C12-D35
A24-B80-C12-D35
A69-B80-C12-D35
A67-B80-C12-D35

-continued
A39-B80-C12-D35
A65-B80-C12-D35
A66-B80-C12-D35
A2-B85-C12-D35
A3-B85-C12-D35
A9-B85-C12-D35
A13-B85-C12-D35
A24-B85-C12-D35
A69-B85-C12-D35
A67-B85-C12-D35
A39-B85-C12-D35
A65-B85-C12-D35
A66-B85-C12-D35
A2-B86-C12-D35
A3-B86-C12-D35
A9-B86-C12-D35
A13-B86-C12-D35
A24-B86-C12-D35
A69-B86-C12-D35
A67-B86-C12-D35
A39-B86-C12-D35
A65-B86-C12-D35
A66-B86-C12-D35
A2-B87-C12-D35
A3-B87-C12-D35
A9-B87-C12-D35
A13-B87-C12-D35
A24-B87-C12-D35
A69-B87-C12-D35
A67-B87-C12-D35
A39-B87-C12-D35
A65-B87-C12-D35
A66-B87-C12-D35
A2-B89-C12-D35
A3-B89-C12-D35
A9-B89-C12-D35
A13-B89-C12-D35
A24-B89-C12-D35
A69-B89-C12-D35
A67-B89-C12-D35
A39-B89-C12-D35
A65-B89-C12-D35
A66-B89-C12-D35
A2-B92-C12-D35
A3-B92-C12-D35
A9-B92-C12-D35
A13-B92-C12-D35
A24-B92-C12-D35
A69-B92-C12-D35
A67-B92-C12-D35
A39-B92-C12-D35
A65-B92-C12-D35
A66-B92-C12-D35
A2-B4-C13-D35
A3-B4-C13-D35
A9-B4-C13-D35
A13-B4-C13-D35
A24-B4-C13-D35
A69-B4-C13-D35
A67-B4-C13-D35
A39-B4-C13-D35
A65-B4-C13-D35
A66-B4-C13-D35
A2-B5-C13-D35
A3-B5-C13-D35
A9-B5-C13-D35
A13-B5-C13-D35
A24-B5-C13-D35
A69-B5-C13-D35
A67-B5-C13-D35
A39-B5-C13-D35
A65-B5-C13-D35
A66-B5-C13-D35
A2-B6-C13-D35
A3-B6-C13-D35
A9-B6-C13-D35
A13-B6-C13-D35
A24-B6-C13-D35
A69-B6-C13-D35
A67-B6-C13-D35

-continued

A39-B6-C13-D35
A65-B6-C13-D35
A66-B6-C13-D35
A2-B32-C13-D35
A3-B32-C13-D35
A9-B32-C13-D35
A13-B32-C13-D35
A24-B32-C13-D35
A69-B32-C13-D35
A67-B32-C13-D35
A39-B32-C13-D35
A65-B32-C13-D35
A66-B32-C13-D35
A2-B39-C13-D35
A3-B39-C13-D35
A9-B39-C13-D35
A13-B39-C13-D35
A24-B39-C13-D35
A69-B39-C13-D35
A67-B39-C13-D35
A39-B39-C13-D35
A65-B39-C13-D35
A66-B39-C13-D35
A2-B45-C13-D35
A3-B45-C13-D35
A9-B45-C13-D35
A13-B45-C13-D35
A24-B45-C13-D35
A69-B45-C13-D35
A67-B45-C13-D35
A39-B45-C13-D35
A65-B45-C13-D35
A66-B45-C13-D35
A2-B53-C13-D35
A3-B53-C13-D35
A9-B53-C13-D35
A13-B53-C13-D35
A24-B53-C13-D35
A69-B53-C13-D35
A67-B53-C13-D35
A39-B53-C13-D35
A65-B53-C13-D35
A66-B53-C13-D35
A2-B79-C13-D35
A3-B79-C13-D35
A9-B79-C13-D35
A13-B79-C13-D35
A24-B79-C13-D35
A69-B79-C13-D35
A67-B79-C13-D35
A39-B79-C13-D35
A65-B79-C13-D35
A66-B79-C13-D35
A2-B80-C13-D35
A3-B80-C13-D35
A9-B80-C13-D35
A13-B80-C13-D35
A24-B80-C13-D35
A69-B80-C13-D35
A67-B80-C13-D35
A39-B80-C13-D35
A65-B80-C13-D35
A66-B80-C13-D35
A2-B85-C13-D35
A3-B85-C13-D35
A9-B85-C13-D35
A13-B85-C13-D35
A24-B85-C13-D35
A69-B85-C13-D35
A67-B85-C13-D35
A39-B85-C13-D35
A65-B85-C13-D35
A66-B85-C13-D35
A2-B86-C13-D35
A3-B86-C13-D35
A9-B86-C13-D35
A13-B86-C13-D35
A24-B86-C13-D35
A69-B86-C13-D35
A67-B86-C13-D35

-continued

A39-B86-C13-D35
A65-B86-C13-D35
A66-B86-C13-D35
A2-B87-C13-D35
A3-B87-C13-D35
A9-B87-C13-D35
A13-B87-C13-D35
A24-B87-C13-D35
A69-B87-C13-D35
A67-B87-C13-D35
A39-B87-C13-D35
A65-B87-C13-D35
A66-B87-C13-D35
A2-B89-C13-D35
A3-B89-C13-D35
A9-B89-C13-D35
A13-B89-C13-D35
A24-B89-C13-D35
A69-B89-C13-D35
A67-B89-C13-D35
A39-B89-C13-D35
A65-B89-C13-D35
A66-B89-C13-D35
A2-B92-C13-D35
A3-B92-C13-D35
A9-B92-C13-D35
A13-B92-C13-D35
A24-B92-C13-D35
A69-B92-C13-D35
A67-B92-C13-D35
A39-B92-C13-D35
A65-B92-C13-D35
A66-B92-C13-D35
A2-B4-C1-D36
A3-B4-C1-D36
A9-B4-C1-D36
A13-B4-C1-D36
A24-B4-C1-D36
A69-B4-C1-D36
A67-B4-C1-D36
A39-B4-C1-D36
A65-B4-C1-D36
A66-B4-C1-D36
A2-B5-C1-D36
A3-B5-C1-D36
A9-B5-C1-D36
A13-B5-C1-D36
A24-B5-C1-D36
A69-B5-C1-D36
A67-B5-C1-D36
A39-B5-C1-D36
A65-B5-C1-D36
A66-B5-C1-D36
A2-B6-C1-D36
A3-B6-C1-D36
A9-B6-C1-D36
A13-B6-C1-D36
A24-B6-C1-D36
A69-B6-C1-D36
A67-B6-C1-D36
A39-B6-C1-D36
A65-B6-C1-D36
A66-B6-C1-D36
A2-B32-C1-D36
A3-B32-C1-D36
A9-B32-C1-D36
A13-B32-C1-D36
A24-B32-C1-D36
A69-B32-C1-D36
A67-B32-C1-D36
A39-B32-C1-D36
A65-B32-C1-D36
A66-B32-C1-D36
A2-B39-C1-D36
A3-B39-C1-D36
A9-B39-C1-D36
A13-B39-C1-D36
A24-B39-C1-D36
A69-B39-C1-D36
A67-B39-C1-D36

-continued

A39-B39-C1-D36
A65-B39-C1-D36
A66-B39-C1-D36
A2-B45-C1-D36
A3-B45-C1-D36
A9-B45-C1-D36
A13-B45-C1-D36
A24-B45-C1-D36
A69-B45-C1-D36
A67-B45-C1-D36
A39-B45-C1-D36
A65-B45-C1-D36
A66-B45-C1-D36
A2-B53-C1-D36
A3-B53-C1-D36
A9-B53-C1-D36
A13-B53-C1-D36
A24-B53-C1-D36
A69-B53-C1-D36
A67-B53-C1-D36
A39-B53-C1-D36
A65-B53-C1-D36
A66-B53-C1-D36
A2-B79-C1-D36
A3-B79-C1-D36
A9-B79-C1-D36
A13-B79-C1-D36
A24-B79-C1-D36
A69-B79-C1-D36
A67-B79-C1-D36
A39-B79-C1-D36
A65-B79-C1-D36
A66-B79-C1-D36
A2-B80-C1-D36
A3-B80-C1-D36
A9-B80-C1-D36
A13-B80-C1-D36
A24-B80-C1-D36
A69-B80-C1-D36
A67-B80-C1-D36
A39-B80-C1-D36
A65-B80-C1-D36
A66-B80-C1-D36
A2-B85-C1-D36
A3-B85-C1-D36
A9-B85-C1-D36
A13-B85-C1-D36
A24-B85-C1-D36
A69-B85-C1-D36
A67-B85-C1-D36
A39-B85-C1-D36
A65-B85-C1-D36
A66-B85-C1-D36
A2-B86-C1-D36
A3-B86-C1-D36
A9-B86-C1-D36
A13-B86-C1-D36
A24-B86-C1-D36
A69-B86-C1-D36
A67-B86-C1-D36
A39-B86-C1-D36
A65-B86-C1-D36
A66-B86-C1-D36
A2-B87-C1-D36
A3-B87-C1-D36
A9-B87-C1-D36
A13-B87-C1-D36
A24-B87-C1-D36
A69-B87-C1-D36
A67-B87-C1-D36
A39-B87-C1-D36
A65-B87-C1-D36
A66-B87-C1-D36
A2-B89-C1-D36
A3-B89-C1-D36
A9-B89-C1-D36
A13-B89-C1-D36
A24-B89-C1-D36
A69-B89-C1-D36
A67-B89-C1-D36

-continued

A39-B89-C1-D36
A65-B89-C1-D36
A66-B89-C1-D36
A2-B92-C1-D36
A3-B92-C1-D36
A9-B92-C1-D36
A13-B92-C1-D36
A24-B92-C1-D36
A69-B92-C1-D36
A67-B92-C1-D36
A39-B92-C1-D36
A65-B92-C1-D36
A66-B92-C1-D36
A2-B4-C2-D36
A3-B4-C2-D36
A9-B4-C2-D36
A13-B4-C2-D36
A24-B4-C2-D36
A69-B4-C2-D36
A67-B4-C2-D36
A39-B4-C2-D36
A65-B4-C2-D36
A66-B4-C2-D36
A2-B5-C2-D36
A3-B5-C2-D36
A9-B5-C2-D36
A13-B5-C2-D36
A24-B5-C2-D36
A69-B5-C2-D36
A67-B5-C2-D36
A39-B5-C2-D36
A65-B5-C2-D36
A66-B5-C2-D36
A2-B6-C2-D36
A3-B6-C2-D36
A9-B6-C2-D36
A13-B6-C2-D36
A24-B6-C2-D36
A69-B6-C2-D36
A67-B6-C2-D36
A39-B6-C2-D36
A65-B6-C2-D36
A66-B6-C2-D36
A2-B32-C2-D36
A3-B32-C2-D36
A9-B32-C2-D36
A13-B32-C2-D36
A24-B32-C2-D36
A69-B32-C2-D36
A67-B32-C2-D36
A39-B32-C2-D36
A65-B32-C2-D36
A66-B32-C2-D36
A2-B39-C2-D36
A3-B39-C2-D36
A9-B39-C2-D36
A13-B39-C2-D36
A24-B39-C2-D36
A69-B39-C2-D36
A67-B39-C2-D36
A39-B39-C2-D36
A65-B39-C2-D36
A66-B39-C2-D36
A2-B45-C2-D36
A3-B45-C2-D36
A9-B45-C2-D36
A13-B45-C2-D36
A24-B45-C2-D36
A69-B45-C2-D36
A67-B45-C2-D36
A39-B45-C2-D36
A65-B45-C2-D36
A66-B45-C2-D36
A2-B53-C2-D36
A3-B53-C2-D36
A9-B53-C2-D36
A13-B53-C2-D36
A24-B53-C2-D36
A69-B53-C2-D36
A67-B53-C2-D36

-continued
A39-B53-C2-D36
A65-B53-C2-D36
A66-B53-C2-D36
A2-B79-C2-D36
A3-B79-C2-D36
A9-B79-C2-D36
A13-B79-C2-D36
A24-B79-C2-D36
A69-B79-C2-D36
A67-B79-C2-D36
A39-B79-C2-D36
A65-B79-C2-D36
A66-B79-C2-D36
A2-B80-C2-D36
A3-B80-C2-D36
A9-B80-C2-D36
A13-B80-C2-D36
A24-B80-C2-D36
A69-B80-C2-D36
A67-B80-C2-D36
A39-B80-C2-D36
A65-B80-C2-D36
A66-B80-C2-D36
A2-B85-C2-D36
A3-B85-C2-D36
A9-B85-C2-D36
A13-B85-C2-D36
A24-B85-C2-D36
A69-B85-C2-D36
A67-B85-C2-D36
A39-B85-C2-D36
A65-B85-C2-D36
A66-B85-C2-D36
A2-B86-C2-D36
A3-B86-C2-D36
A9-B86-C2-D36
A13-B86-C2-D36
A24-B86-C2-D36
A69-B86-C2-D36
A67-B86-C2-D36
A39-B86-C2-D36
A65-B86-C2-D36
A66-B86-C2-D36
A2-B87-C2-D36
A3-B87-C2-D36
A9-B87-C2-D36
A13-B87-C2-D36
A24-B87-C2-D36
A69-B87-C2-D36
A67-B87-C2-D36
A39-B87-C2-D36
A65-B87-C2-D36
A66-B87-C2-D36
A2-B89-C2-D36
A3-B89-C2-D36
A9-B89-C2-D36
A13-B89-C2-D36
A24-B89-C2-D36
A69-B89-C2-D36
A67-B89-C2-D36
A39-B89-C2-D36
A65-B89-C2-D36
A66-B89-C2-D36
A2-B92-C2-D36
A3-B92-C2-D36
A9-B92-C2-D36
A13-B92-C2-D36
A24-B92-C2-D36
A69-B92-C2-D36
A67-B92-C2-D36
A39-B92-C2-D36
A65-B92-C2-D36
A66-B92-C2-D36
A2-B4-C3-D36
A3-B4-C3-D36
A9-B4-C3-D36
A13-B4-C3-D36
A24-B4-C3-D36
A69-B4-C3-D36
A67-B4-C3-D36

-continued
A39-B4-C3-D36
A65-B4-C3-D36
A66-B4-C3-D36
A2-B5-C3-D36
A3-B5-C3-D36
A9-B5-C3-D36
A13-B5-C3-D36
A24-B5-C3-D36
A69-B5-C3-D36
A67-B5-C3-D36
A39-B5-C3-D36
A65-B5-C3-D36
A66-B5-C3-D36
A2-B6-C3-D36
A3-B6-C3-D36
A9-B6-C3-D36
A13-B6-C3-D36
A24-B6-C3-D36
A69-B6-C3-D36
A67-B6-C3-D36
A39-B6-C3-D36
A65-B6-C3-D36
A66-B6-C3-D36
A2-B32-C3-D36
A3-B32-C3-D36
A9-B32-C3-D36
A13-B32-C3-D36
A24-B32-C3-D36
A69-B32-C3-D36
A67-B32-C3-D36
A39-B32-C3-D36
A65-B32-C3-D36
A66-B32-C3-D36
A2-B39-C3-D36
A3-B39-C3-D36
A9-B39-C3-D36
A13-B39-C3-D36
A24-B39-C3-D36
A69-B39-C3-D36
A67-B39-C3-D36
A39-B39-C3-D36
A65-B39-C3-D36
A66-B39-C3-D36
A2-B45-C3-D36
A3-B45-C3-D36
A9-B45-C3-D36
A13-B45-C3-D36
A24-B45-C3-D36
A69-B45-C3-D36
A67-B45-C3-D36
A39-B45-C3-D36
A65-B45-C3-D36
A66-B45-C3-D36
A2-B53-C3-D36
A3-B53-C3-D36
A9-B53-C3-D36
A13-B53-C3-D36
A24-B53-C3-D36
A69-B53-C3-D36
A67-B53-C3-D36
A39-B53-C3-D36
A65-B53-C3-D36
A66-B53-C3-D36
A2-B79-C3-D36
A3-B79-C3-D36
A9-B79-C3-D36
A13-B79-C3-D36
A24-B79-C3-D36
A69-B79-C3-D36
A67-B79-C3-D36
A39-B79-C3-D36
A65-B79-C3-D36
A66-B79-C3-D36
A2-B80-C3-D36
A3-B80-C3-D36
A9-B80-C3-D36
A13-B80-C3-D36
A24-B80-C3-D36
A69-B80-C3-D36
A67-B80-C3-D36

-continued
A39-B80-C3-D36
A65-B80-C3-D36
A66-B80-C3-D36
A2-B85-C3-D36
A3-B85-C3-D36
A9-B85-C3-D36
A13-B85-C3-D36
A24-B85-C3-D36
A69-B85-C3-D36
A67-B85-C3-D36
A39-B85-C3-D36
A65-B85-C3-D36
A66-B85-C3-D36
A2-B86-C3-D36
A3-B86-C3-D36
A9-B86-C3-D36
A13-B86-C3-D36
A24-B86-C3-D36
A69-B86-C3-D36
A67-B86-C3-D36
A39-B86-C3-D36
A65-B86-C3-D36
A66-B86-C3-D36
A2-B87-C3-D36
A3-B87-C3-D36
A9-B87-C3-D36
A13-B87-C3-D36
A24-B87-C3-D36
A69-B87-C3-D36
A67-B87-C3-D36
A39-B87-C3-D36
A65-B87-C3-D36
A66-B87-C3-D36
A2-B89-C3-D36
A3-B89-C3-D36
A9-B89-C3-D36
A13-B89-C3-D36
A24-B89-C3-D36
A69-B89-C3-D36
A67-B89-C3-D36
A39-B89-C3-D36
A65-B89-C3-D36
A66-B89-C3-D36
A2-B92-C3-D36
A3-B92-C3-D36
A9-B92-C3-D36
A13-B92-C3-D36
A24-B92-C3-D36
A69-B92-C3-D36
A67-B92-C3-D36
A39-B92-C3-D36
A65-B92-C3-D36
A66-B92-C3-D36
A2-B4-C4-D36
A3-B4-C4-D36
A9-B4-C4-D36
A13-B4-C4-D36
A24-B4-C4-D36
A69-B4-C4-D36
A67-B4-C4-D36
A39-B4-C4-D36
A65-B4-C4-D36
A66-B4-C4-D36
A2-B5-C4-D36
A3-B5-C4-D36
A9-B5-C4-D36
A13-B5-C4-D36
A24-B5-C4-D36
A69-B5-C4-D36
A67-B5-C4-D36
A39-B5-C4-D36
A65-B5-C4-D36
A66-B5-C4-D36
A2-B6-C4-D36
A3-B6-C4-D36
A9-B6-C4-D36
A13-B6-C4-D36
A24-B6-C4-D36
A69-B6-C4-D36
A67-B6-C4-D36

-continued
A39-B6-C4-D36
A65-B6-C4-D36
A66-B6-C4-D36
A2-B32-C4-D36
A3-B32-C4-D36
A9-B32-C4-D36
A13-B32-C4-D36
A24-B32-C4-D36
A69-B32-C4-D36
A67-B32-C4-D36
A39-B32-C4-D36
A65-B32-C4-D36
A66-B32-C4-D36
A2-B39-C4-D36
A3-B39-C4-D36
A9-B39-C4-D36
A13-B39-C4-D36
A24-B39-C4-D36
A69-B39-C4-D36
A67-B39-C4-D36
A39-B39-C4-D36
A65-B39-C4-D36
A66-B39-C4-D36
A2-B45-C4-D36
A3-B45-C4-D36
A9-B45-C4-D36
A13-B45-C4-D36
A24-B45-C4-D36
A69-B45-C4-D36
A67-B45-C4-D36
A39-B45-C4-D36
A65-B45-C4-D36
A66-B45-C4-D36
A2-B53-C4-D36
A3-B53-C4-D36
A9-B53-C4-D36
A13-B53-C4-D36
A24-B53-C4-D36
A69-B53-C4-D36
A67-B53-C4-D36
A39-B53-C4-D36
A65-B53-C4-D36
A66-B53-C4-D36
A2-B79-C4-D36
A3-B79-C4-D36
A9-B79-C4-D36
A13-B79-C4-D36
A24-B79-C4-D36
A69-B79-C4-D36
A67-B79-C4-D36
A39-B79-C4-D36
A65-B79-C4-D36
A66-B79-C4-D36
A2-B80-C4-D36
A3-B80-C4-D36
A9-B80-C4-D36
A13-B80-C4-D36
A24-B80-C4-D36
A69-B80-C4-D36
A67-B80-C4-D36
A39-B80-C4-D36
A65-B80-C4-D36
A66-B80-C4-D36
A2-B85-C4-D36
A3-B85-C4-D36
A9-B85-C4-D36
A13-B85-C4-D36
A24-B85-C4-D36
A69-B85-C4-D36
A67-B85-C4-D36
A39-B85-C4-D36
A65-B85-C4-D36
A66-B85-C4-D36
A2-B86-C4-D36
A3-B86-C4-D36
A9-B86-C4-D36
A13-B86-C4-D36
A24-B86-C4-D36
A69-B86-C4-D36
A67-B86-C4-D36

-continued
A39-B86-C4-D36
A65-B86-C4-D36
A66-B86-C4-D36
A2-B87-C4-D36
A3-B87-C4-D36
A9-B87-C4-D36
A13-B87-C4-D36
A24-B87-C4-D36
A69-B87-C4-D36
A67-B87-C4-D36
A39-B87-C4-D36
A65-B87-C4-D36
A66-B87-C4-D36
A2-B89-C4-D36
A3-B89-C4-D36
A9-B89-C4-D36
A13-B89-C4-D36
A24-B89-C4-D36
A69-B89-C4-D36
A67-B89-C4-D36
A39-B89-C4-D36
A65-B89-C4-D36
A66-B89-C4-D36
A2-B92-C4-D36
A3-B92-C4-D36
A9-B92-C4-D36
A13-B92-C4-D36
A24-B92-C4-D36
A69-B92-C4-D36
A67-B92-C4-D36
A39-B92-C4-D36
A65-B92-C4-D36
A66-B92-C4-D36
A2-B4-C5-D36
A3-B4-C5-D36
A9-B4-C5-D36
A13-B4-C5-D36
A24-B4-C5-D36
A69-B4-C5-D36
A67-B4-C5-D36
A39-B4-C5-D36
A65-B4-C5-D36
A66-B4-C5-D36
A2-B5-C5-D36
A3-B5-C5-D36
A9-B5-C5-D36
A13-B5-C5-D36
A24-B5-C5-D36
A69-B5-C5-D36
A67-B5-C5-D36
A39-B5-C5-D36
A65-B5-C5-D36
A66-B5-C5-D36
A2-B6-C5-D36
A3-B6-C5-D36
A9-B6-C5-D36
A13-B6-C5-D36
A24-B6-C5-D36
A69-B6-C5-D36
A67-B6-C5-D36
A39-B6-C5-D36
A65-B6-C5-D36
A66-B6-C5-D36
A2-B32-C5-D36
A3-B32-C5-D36
A9-B32-C5-D36
A13-B32-C5-D36
A24-B32-C5-D36
A69-B32-C5-D36
A67-B32-C5-D36
A39-B32-C5-D36
A65-B32-C5-D36
A66-B32-C5-D36
A2-B39-C5-D36
A3-B39-C5-D36
A9-B39-C5-D36
A13-B39-C5-D36
A24-B39-C5-D36
A69-B39-C5-D36
A67-B39-C5-D36

-continued
A39-B39-C5-D36
A65-B39-C5-D36
A66-B39-C5-D36
A2-B45-C5-D36
A3-B45-C5-D36
A9-B45-C5-D36
A13-B45-C5-D36
A24-B45-C5-D36
A69-B45-C5-D36
A67-B45-C5-D36
A39-B45-C5-D36
A65-B45-C5-D36
A66-B45-C5-D36
A2-B53-C5-D36
A3-B53-C5-D36
A9-B53-C5-D36
A13-B53-C5-D36
A24-B53-C5-D36
A69-B53-C5-D36
A67-B53-C5-D36
A39-B53-C5-D36
A65-B53-C5-D36
A66-B53-C5-D36
A2-B79-C5-D36
A3-B79-C5-D36
A9-B79-C5-D36
A13-B79-C5-D36
A24-B79-C5-D36
A69-B79-C5-D36
A67-B79-C5-D36
A39-B79-C5-D36
A65-B79-C5-D36
A66-B79-C5-D36
A2-B80-C5-D36
A3-B80-C5-D36
A9-B80-C5-D36
A13-B80-C5-D36
A24-B80-C5-D36
A69-B80-C5-D36
A67-B80-C5-D36
A39-B80-C5-D36
A65-B80-C5-D36
A66-B80-C5-D36
A2-B85-C5-D36
A3-B85-C5-D36
A9-B85-C5-D36
A13-B85-C5-D36
A24-B85-C5-D36
A69-B85-C5-D36
A67-B85-C5-D36
A39-B85-C5-D36
A65-B85-C5-D36
A66-B85-C5-D36
A2-B86-C5-D36
A3-B86-C5-D36
A9-B86-C5-D36
A13-B86-C5-D36
A24-B86-C5-D36
A69-B86-C5-D36
A67-B86-C5-D36
A39-B86-C5-D36
A65-B86-C5-D36
A66-B86-C5-D36
A2-B87-C5-D36
A3-B87-C5-D36
A9-B87-C5-D36
A13-B87-C5-D36
A24-B87-C5-D36
A69-B87-C5-D36
A67-B87-C5-D36
A39-B87-C5-D36
A65-B87-C5-D36
A66-B87-C5-D36
A2-B89-C5-D36
A3-B89-C5-D36
A9-B89-C5-D36
A13-B89-C5-D36
A24-B89-C5-D36
A69-B89-C5-D36
A67-B89-C5-D36

-continued

A39-B89-C5-D36
A65-B89-C5-D36
A66-B89-C5-D36
A2-B92-C5-D36
A3-B92-C5-D36
A9-B92-C5-D36
A13-B92-C5-D36
A24-B92-C5-D36
A69-B92-C5-D36
A67-B92-C5-D36
A39-B92-C5-D36
A65-B92-C5-D36
A66-B92-C5-D36
A2-B4-C6-D36
A3-B4-C6-D36
A9-B4-C6-D36
A13-B4-C6-D36
A24-B4-C6-D36
A69-B4-C6-D36
A67-B4-C6-D36
A39-B4-C6-D36
A65-B4-C6-D36
A66-B4-C6-D36
A2-B5-C6-D36
A3-B5-C6-D36
A9-B5-C6-D36
A13-B5-C6-D36
A24-B5-C6-D36
A69-B5-C6-D36
A67-B5-C6-D36
A39-B5-C6-D36
A65-B5-C6-D36
A66-B5-C6-D36
A2-B6-C6-D36
A3-B6-C6-D36
A9-B6-C6-D36
A13-B6-C6-D36
A24-B6-C6-D36
A69-B6-C6-D36
A67-B6-C6-D36
A39-B6-C6-D36
A65-B6-C6-D36
A66-B6-C6-D36
A2-B32-C6-D36
A3-B32-C6-D36
A9-B32-C6-D36
A13-B32-C6-D36
A24-B32-C6-D36
A69-B32-C6-D36
A67-B32-C6-D36
A39-B32-C6-D36
A65-B32-C6-D36
A66-B32-C6-D36
A2-B39-C6-D36
A3-B39-C6-D36
A9-B39-C6-D36
A13-B39-C6-D36
A24-B39-C6-D36
A69-B39-C6-D36
A67-B39-C6-D36
A39-B39-C6-D36
A65-B39-C6-D36
A66-B39-C6-D36
A2-B45-C6-D36
A3-B45-C6-D36
A9-B45-C6-D36
A13-B45-C6-D36
A24-B45-C6-D36
A69-B45-C6-D36
A67-B45-C6-D36
A39-B45-C6-D36
A65-B45-C6-D36
A66-B45-C6-D36
A2-B53-C6-D36
A3-B53-C6-D36
A9-B53-C6-D36
A13-B53-C6-D36
A24-B53-C6-D36
A69-B53-C6-D36
A67-B53-C6-D36

-continued

A39-B53-C6-D36
A65-B53-C6-D36
A66-B53-C6-D36
A2-B79-C6-D36
A3-B79-C6-D36
A9-B79-C6-D36
A13-B79-C6-D36
A24-B79-C6-D36
A69-B79-C6-D36
A67-B79-C6-D36
A39-B79-C6-D36
A65-B79-C6-D36
A66-B79-C6-D36
A2-B80-C6-D36
A3-B80-C6-D36
A9-B80-C6-D36
A13-B80-C6-D36
A24-B80-C6-D36
A69-B80-C6-D36
A67-B80-C6-D36
A39-B80-C6-D36
A65-B80-C6-D36
A66-B80-C6-D36
A2-B85-C6-D36
A3-B85-C6-D36
A9-B85-C6-D36
A13-B85-C6-D36
A24-B85-C6-D36
A69-B85-C6-D36
A67-B85-C6-D36
A39-B85-C6-D36
A65-B85-C6-D36
A66-B85-C6-D36
A2-B86-C6-D36
A3-B86-C6-D36
A9-B86-C6-D36
A13-B86-C6-D36
A24-B86-C6-D36
A69-B86-C6-D36
A67-B86-C6-D36
A39-B86-C6-D36
A65-B86-C6-D36
A66-B86-C6-D36
A2-B87-C6-D36
A3-B87-C6-D36
A9-B87-C6-D36
A13-B87-C6-D36
A24-B87-C6-D36
A69-B87-C6-D36
A67-B87-C6-D36
A39-B87-C6-D36
A65-B87-C6-D36
A66-B87-C6-D36
A2-B89-C6-D36
A3-B89-C6-D36
A9-B89-C6-D36
A13-B89-C6-D36
A24-B89-C6-D36
A69-B89-C6-D36
A67-B89-C6-D36
A39-B89-C6-D36
A65-B89-C6-D36
A66-B89-C6-D36
A2-B92-C6-D36
A3-B92-C6-D36
A9-B92-C6-D36
A13-B92-C6-D36
A24-B92-C6-D36
A69-B92-C6-D36
A67-B92-C6-D36
A39-B92-C6-D36
A65-B92-C6-D36
A66-B92-C6-D36
A2-B4-C7-D36
A3-B4-C7-D36
A9-B4-C7-D36
A13-B4-C7-D36
A24-B4-C7-D36
A69-B4-C7-D36
A67-B4-C7-D36

-continued
A39-B4-C7-D36
A65-B4-C7-D36
A66-B4-C7-D36
A2-B5-C7-D36
A3-B5-C7-D36
A9-B5-C7-D36
A13-B5-C7-D36
A24-B5-C7-D36
A69-B5-C7-D36
A67-B5-C7-D36
A39-B5-C7-D36
A65-B5-C7-D36
A66-B5-C7-D36
A2-B6-C7-D36
A3-B6-C7-D36
A9-B6-C7-D36
A13-B6-C7-D36
A24-B6-C7-D36
A69-B6-C7-D36
A67-B6-C7-D36
A39-B6-C7-D36
A65-B6-C7-D36
A66-B6-C7-D36
A2-B32-C7-D36
A3-B32-C7-D36
A9-B32-C7-D36
A13-B32-C7-D36
A24-B32-C7-D36
A69-B32-C7-D36
A67-B32-C7-D36
A39-B32-C7-D36
A65-B32-C7-D36
A66-B32-C7-D36
A2-B39-C7-D36
A3-B39-C7-D36
A9-B39-C7-D36
A13-B39-C7-D36
A24-B39-C7-D36
A69-B39-C7-D36
A67-B39-C7-D36
A39-B39-C7-D36
A65-B39-C7-D36
A66-B39-C7-D36
A2-B45-C7-D36
A3-B45-C7-D36
A9-B45-C7-D36
A13-B45-C7-D36
A24-B45-C7-D36
A69-B45-C7-D36
A67-B45-C7-D36
A39-B45-C7-D36
A65-B45-C7-D36
A66-B45-C7-D36
A2-B53-C7-D36
A3-B53-C7-D36
A9-B53-C7-D36
A13-B53-C7-D36
A24-B53-C7-D36
A69-B53-C7-D36
A67-B53-C7-D36
A39-B53-C7-D36
A65-B53-C7-D36
A66-B53-C7-D36
A2-B79-C7-D36
A3-B79-C7-D36
A9-B79-C7-D36
A13-B79-C7-D36
A24-B79-C7-D36
A69-B79-C7-D36
A67-B79-C7-D36
A39-B79-C7-D36
A65-B79-C7-D36
A66-B79-C7-D36
A2-B80-C7-D36
A3-B80-C7-D36
A9-B80-C7-D36
A13-B80-C7-D36
A24-B80-C7-D36
A69-B80-C7-D36
A67-B80-C7-D36

-continued
A39-B80-C7-D36
A65-B80-C7-D36
A66-B80-C7-D36
A2-B85-C7-D36
A3-B85-C7-D36
A9-B85-C7-D36
A13-B85-C7-D36
A24-B85-C7-D36
A69-B85-C7-D36
A67-B85-C7-D36
A39-B85-C7-D36
A65-B85-C7-D36
A66-B85-C7-D36
A2-B86-C7-D36
A3-B86-C7-D36
A9-B86-C7-D36
A13-B86-C7-D36
A24-B86-C7-D36
A69-B86-C7-D36
A67-B86-C7-D36
A39-B86-C7-D36
A65-B86-C7-D36
A66-B86-C7-D36
A2-B87-C7-D36
A3-B87-C7-D36
A9-B87-C7-D36
A13-B87-C7-D36
A24-B87-C7-D36
A69-B87-C7-D36
A67-B87-C7-D36
A39-B87-C7-D36
A65-B87-C7-D36
A66-B87-C7-D36
A2-B89-C7-D36
A3-B89-C7-D36
A9-B89-C7-D36
A13-B89-C7-D36
A24-B89-C7-D36
A69-B89-C7-D36
A67-B89-C7-D36
A39-B89-C7-D36
A65-B89-C7-D36
A66-B89-C7-D36
A2-B92-C7-D36
A3-B92-C7-D36
A9-B92-C7-D36
A13-B92-C7-D36
A24-B92-C7-D36
A69-B92-C7-D36
A67-B92-C7-D36
A39-B92-C7-D36
A65-B92-C7-D36
A66-B92-C7-D36
A2-B4-C8-D36
A3-B4-C8-D36
A9-B4-C8-D36
A13-B4-C8-D36
A24-B4-C8-D36
A69-B4-C8-D36
A67-B4-C8-D36
A39-B4-C8-D36
A65-B4-C8-D36
A66-B4-C8-D36
A2-B5-C8-D36
A3-B5-C8-D36
A9-B5-C8-D36
A13-B5-C8-D36
A24-B5-C8-D36
A69-B5-C8-D36
A67-B5-C8-D36
A39-B5-C8-D36
A65-B5-C8-D36
A66-B5-C8-D36
A2-B6-C8-D36
A3-B6-C8-D36
A9-B6-C8-D36
A13-B6-C8-D36
A24-B6-C8-D36
A69-B6-C8-D36
A67-B6-C8-D36

-continued

A39-B6-C8-D36
A65-B6-C8-D36
A66-B6-C8-D36
A2-B32-C8-D36
A3-B32-C8-D36
A9-B32-C8-D36
A13-B32-C8-D36
A24-B32-C8-D36
A69-B32-C8-D36
A67-B32-C8-D36
A39-B32-C8-D36
A65-B32-C8-D36
A66-B32-C8-D36
A2-B39-C8-D36
A3-B39-C8-D36
A9-B39-C8-D36
A13-B39-C8-D36
A24-B39-C8-D36
A69-B39-C8-D36
A67-B39-C8-D36
A39-B39-C8-D36
A65-B39-C8-D36
A66-B39-C8-D36
A2-B45-C8-D36
A3-B45-C8-D36
A9-B45-C8-D36
A13-B45-C8-D36
A24-B45-C8-D36
A69-B45-C8-D36
A67-B45-C8-D36
A39-B45-C8-D36
A65-B45-C8-D36
A66-B45-C8-D36
A2-B53-C8-D36
A3-B53-C8-D36
A9-B53-C8-D36
A13-B53-C8-D36
A24-B53-C8-D36
A69-B53-C8-D36
A67-B53-C8-D36
A39-B53-C8-D36
A65-B53-C8-D36
A66-B53-C8-D36
A2-B79-C8-D36
A3-B79-C8-D36
A9-B79-C8-D36
A13-B79-C8-D36
A24-B79-C8-D36
A69-B79-C8-D36
A67-B79-C8-D36
A39-B79-C8-D36
A65-B79-C8-D36
A66-B79-C8-D36
A2-B80-C8-D36
A3-B80-C8-D36
A9-B80-C8-D36
A13-B80-C8-D36
A24-B80-C8-D36
A69-B80-C8-D36
A67-B80-C8-D36
A39-B80-C8-D36
A65-B80-C8-D36
A66-B80-C8-D36
A2-B85-C8-D36
A3-B85-C8-D36
A9-B85-C8-D36
A13-B85-C8-D36
A24-B85-C8-D36
A69-B85-C8-D36
A67-B85-C8-D36
A39-B85-C8-D36
A65-B85-C8-D36
A66-B85-C8-D36
A2-B86-C8-D36
A3-B86-C8-D36
A9-B86-C8-D36
A13-B86-C8-D36
A24-B86-C8-D36
A69-B86-C8-D36
A67-B86-C8-D36

-continued

A39-B86-C8-D36
A65-B86-C8-D36
A66-B86-C8-D36
A2-B87-C8-D36
A3-B87-C8-D36
A9-B87-C8-D36
A13-B87-C8-D36
A24-B87-C8-D36
A69-B87-C8-D36
A67-B87-C8-D36
A39-B87-C8-D36
A65-B87-C8-D36
A66-B87-C8-D36
A2-B89-C8-D36
A3-B89-C8-D36
A9-B89-C8-D36
A13-B89-C8-D36
A24-B89-C8-D36
A69-B89-C8-D36
A67-B89-C8-D36
A39-B89-C8-D36
A65-B89-C8-D36
A66-B89-C8-D36
A2-B92-C8-D36
A3-B92-C8-D36
A9-B92-C8-D36
A13-B92-C8-D36
A24-B92-C8-D36
A69-B92-C8-D36
A67-B92-C8-D36
A39-B92-C8-D36
A65-B92-C8-D36
A66-B92-C8-D36
A2-B4-C9-D36
A3-B4-C9-D36
A9-B4-C9-D36
A13-B4-C9-D36
A24-B4-C9-D36
A69-B4-C9-D36
A67-B4-C9-D36
A39-B4-C9-D36
A65-B4-C9-D36
A66-B4-C9-D36
A2-B5-C9-D36
A3-B5-C9-D36
A9-B5-C9-D36
A13-B5-C9-D36
A24-B5-C9-D36
A69-B5-C9-D36
A67-B5-C9-D36
A39-B5-C9-D36
A65-B5-C9-D36
A66-B5-C9-D36
A2-B6-C9-D36
A3-B6-C9-D36
A9-B6-C9-D36
A13-B6-C9-D36
A24-B6-C9-D36
A69-B6-C9-D36
A67-B6-C9-D36
A39-B6-C9-D36
A65-B6-C9-D36
A66-B6-C9-D36
A2-B32-C9-D36
A3-B32-C9-D36
A9-B32-C9-D36
A13-B32-C9-D36
A24-B32-C9-D36
A69-B32-C9-D36
A67-B32-C9-D36
A39-B32-C9-D36
A65-B32-C9-D36
A66-B32-C9-D36
A2-B39-C9-D36
A3-B39-C9-D36
A9-B39-C9-D36
A13-B39-C9-D36
A24-B39-C9-D36
A69-B39-C9-D36
A67-B39-C9-D36

-continued
A39-B39-C9-D36
A65-B39-C9-D36
A66-B39-C9-D36
A2-B45-C9-D36
A3-B45-C9-D36
A9-B45-C9-D36
A13-B45-C9-D36
A24-B45-C9-D36
A69-B45-C9-D36
A67-B45-C9-D36
A39-B45-C9-D36
A65-B45-C9-D36
A66-B45-C9-D36
A2-B53-C9-D36
A3-B53-C9-D36
A9-B53-C9-D36
A13-B53-C9-D36
A24-B53-C9-D36
A69-B53-C9-D36
A67-B53-C9-D36
A39-B53-C9-D36
A65-B53-C9-D36
A66-B53-C9-D36
A2-B79-C9-D36
A3-B79-C9-D36
A9-B79-C9-D36
A13-B79-C9-D36
A24-B79-C9-D36
A69-B79-C9-D36
A67-B79-C9-D36
A39-B79-C9-D36
A65-B79-C9-D36
A66-B79-C9-D36
A2-B80-C9-D36
A3-B80-C9-D36
A9-B80-C9-D36
A13-B80-C9-D36
A24-B80-C9-D36
A69-B80-C9-D36
A67-B80-C9-D36
A39-B80-C9-D36
A65-B80-C9-D36
A66-B80-C9-D36
A2-B85-C9-D36
A3-B85-C9-D36
A9-B85-C9-D36
A13-B85-C9-D36
A24-B85-C9-D36
A69-B85-C9-D36
A67-B85-C9-D36
A39-B85-C9-D36
A65-B85-C9-D36
A66-B85-C9-D36
A2-B86-C9-D36
A3-B86-C9-D36
A9-B86-C9-D36
A13-B86-C9-D36
A24-B86-C9-D36
A69-B86-C9-D36
A67-B86-C9-D36
A39-B86-C9-D36
A65-B86-C9-D36
A66-B86-C9-D36
A2-B87-C9-D36
A3-B87-C9-D36
A9-B87-C9-D36
A13-B87-C9-D36
A24-B87-C9-D36
A69-B87-C9-D36
A67-B87-C9-D36
A39-B87-C9-D36
A65-B87-C9-D36
A66-B87-C9-D36
A2-B89-C9-D36
A3-B89-C9-D36
A9-B89-C9-D36
A13-B89-C9-D36
A24-B89-C9-D36
A69-B89-C9-D36
A67-B89-C9-D36

-continued
A39-B89-C9-D36
A65-B89-C9-D36
A66-B89-C9-D36
A2-B92-C9-D36
A3-B92-C9-D36
A9-B92-C9-D36
A13-B92-C9-D36
A24-B92-C9-D36
A69-B92-C9-D36
A67-B92-C9-D36
A39-B92-C9-D36
A65-B92-C9-D36
A66-B92-C9-D36
A2-B4-C10-D36
A3-B4-C10-D36
A9-B4-C10-D36
A13-B4-C10-D36
A24-B4-C10-D36
A69-B4-C10-D36
A67-B4-C10-D36
A39-B4-C10-D36
A65-B4-C10-D36
A66-B4-C10-D36
A2-B5-C10-D36
A3-B5-C10-D36
A9-B5-C10-D36
A13-B5-C10-D36
A24-B5-C10-D36
A69-B5-C10-D36
A67-B5-C10-D36
A39-B5-C10-D36
A65-B5-C10-D36
A66-B5-C10-D36
A2-B6-C10-D36
A3-B6-C10-D36
A9-B6-C10-D36
A13-B6-C10-D36
A24-B6-C10-D36
A69-B6-C10-D36
A67-B6-C10-D36
A39-B6-C10-D36
A65-B6-C10-D36
A66-B6-C10-D36
A2-B32-C10-D36
A3-B32-C10-D36
A9-B32-C10-D36
A13-B32-C10-D36
A24-B32-C10-D36
A69-B32-C10-D36
A67-B32-C10-D36
A39-B32-C10-D36
A65-B32-C10-D36
A66-B32-C10-D36
A2-B39-C10-D36
A3-B39-C10-D36
A9-B39-C10-D36
A13-B39-C10-D36
A24-B39-C10-D36
A69-B39-C10-D36
A67-B39-C10-D36
A39-B39-C10-D36
A65-B39-C10-D36
A66-B39-C10-D36
A2-B45-C10-D36
A3-B45-C10-D36
A9-B45-C10-D36
A13-B45-C10-D36
A24-B45-C10-D36
A69-B45-C10-D36
A67-B45-C10-D36
A39-B45-C10-D36
A65-B45-C10-D36
A66-B45-C10-D36
A2-B53-C10-D36
A3-B53-C10-D36
A9-B53-C10-D36
A13-B53-C10-D36
A24-B53-C10-D36
A69-B53-C10-D36
A67-B53-C10-D36

-continued
A39-B53-C10-D36
A65-B53-C10-D36
A66-B53-C10-D36
A2-B79-C10-D36
A3-B79-C10-D36
A9-B79-C10-D36
A13-B79-C10-D36
A24-B79-C10-D36
A69-B79-C10-D36
A67-B79-C10-D36
A39-B79-C10-D36
A65-B79-C10-D36
A66-B79-C10-D36
A2-B80-C10-D36
A3-B80-C10-D36
A9-B80-C10-D36
A13-B80-C10-D36
A24-B80-C10-D36
A69-B80-C10-D36
A67-B80-C10-D36
A39-B80-C10-D36
A65-B80-C10-D36
A66-B80-C10-D36
A2-B85-C10-D36
A3-B85-C10-D36
A9-B85-C10-D36
A13-B85-C10-D36
A24-B85-C10-D36
A69-B85-C10-D36
A67-B85-C10-D36
A39-B85-C10-D36
A65-B85-C10-D36
A66-B85-C10-D36
A2-B86-C10-D36
A3-B86-C10-D36
A9-B86-C10-D36
A13-B86-C10-D36
A24-B86-C10-D36
A69-B86-C10-D36
A67-B86-C10-D36
A39-B86-C10-D36
A65-B86-C10-D36
A66-B86-C10-D36
A2-B87-C10-D36
A3-B87-C10-D36
A9-B87-C10-D36
A13-B87-C10-D36
A24-B87-C10-D36
A69-B87-C10-D36
A67-B87-C10-D36
A39-B87-C10-D36
A65-B87-C10-D36
A66-B87-C10-D36
A2-B89-C10-D36
A3-B89-C10-D36
A9-B89-C10-D36
A13-B89-C10-D36
A24-B89-C10-D36
A69-B89-C10-D36
A67-B89-C10-D36
A39-B89-C10-D36
A65-B89-C10-D36
A66-B89-C10-D36
A2-B92-C10-D36
A3-B92-C10-D36
A9-B92-C10-D36
A13-B92-C10-D36
A24-B92-C10-D36
A69-B92-C10-D36
A67-B92-C10-D36
A39-B92-C10-D36
A65-B92-C10-D36
A66-B92-C10-D36
A2-B4-C11-D36
A3-B4-C11-D36
A9-B4-C11-D36
A13-B4-C11-D36
A24-B4-C11-D36
A69-B4-C11-D36
A67-B4-C11-D36

-continued
A39-B4-C11-D36
A65-B4-C11-D36
A66-B4-C11-D36
A2-B5-C11-D36
A3-B5-C11-D36
A9-B5-C11-D36
A13-B5-C11-D36
A24-B5-C11-D36
A69-B5-C11-D36
A67-B5-C11-D36
A39-B5-C11-D36
A65-B5-C11-D36
A66-B5-C11-D36
A2-B6-C11-D36
A3-B6-C11-D36
A9-B6-C11-D36
A13-B6-C11-D36
A24-B6-C11-D36
A69-B6-C11-D36
A67-B6-C11-D36
A39-B6-C11-D36
A65-B6-C11-D36
A66-B6-C11-D36
A2-B32-C11-D36
A3-B32-C11-D36
A9-B32-C11-D36
A13-B32-C11-D36
A24-B32-C11-D36
A69-B32-C11-D36
A67-B32-C11-D36
A39-B32-C11-D36
A65-B32-C11-D36
A66-B32-C11-D36
A2-B39-C11-D36
A3-B39-C11-D36
A9-B39-C11-D36
A13-B39-C11-D36
A24-B39-C11-D36
A69-B39-C11-D36
A67-B39-C11-D36
A39-B39-C11-D36
A65-B39-C11-D36
A66-B39-C11-D36
A2-B45-C11-D36
A3-B45-C11-D36
A9-B45-C11-D36
A13-B45-C11-D36
A24-B45-C11-D36
A69-B45-C11-D36
A67-B45-C11-D36
A39-B45-C11-D36
A65-B45-C11-D36
A66-B45-C11-D36
A2-B53-C11-D36
A3-B53-C11-D36
A9-B53-C11-D36
A13-B53-C11-D36
A24-B53-C11-D36
A69-B53-C11-D36
A67-B53-C11-D36
A39-B53-C11-D36
A65-B53-C11-D36
A66-B53-C11-D36
A2-B79-C11-D36
A3-B79-C11-D36
A9-B79-C11-D36
A13-B79-C11-D36
A24-B79-C11-D36
A69-B79-C11-D36
A67-B79-C11-D36
A39-B79-C11-D36
A65-B79-C11-D36
A66-B79-C11-D36
A2-B80-C11-D36
A3-B80-C11-D36
A9-B80-C11-D36
A13-B80-C11-D36
A24-B80-C11-D36
A69-B80-C11-D36
A67-B80-C11-D36

-continued

A39-B80-C11-D36
A65-B80-C11-D36
A66-B80-C11-D36
A2-B85-C11-D36
A3-B85-C11-D36
A9-B85-C11-D36
A13-B85-C11-D36
A24-B85-C11-D36
A69-B85-C11-D36
A67-B85-C11-D36
A39-B85-C11-D36
A65-B85-C11-D36
A66-B85-C11-D36
A2-B86-C11-D36
A3-B86-C11-D36
A9-B86-C11-D36
A13-B86-C11-D36
A24-B86-C11-D36
A69-B86-C11-D36
A67-B86-C11-D36
A39-B86-C11-D36
A65-B86-C11-D36
A66-B86-C11-D36
A2-B87-C11-D36
A3-B87-C11-D36
A9-B87-C11-D36
A13-B87-C11-D36
A24-B87-C11-D36
A69-B87-C11-D36
A67-B87-C11-D36
A39-B87-C11-D36
A65-B87-C11-D36
A66-B87-C11-D36
A2-B89-C11-D36
A3-B89-C11-D36
A9-B89-C11-D36
A13-B89-C11-D36
A24-B89-C11-D36
A69-B89-C11-D36
A67-B89-C11-D36
A39-B89-C11-D36
A65-B89-C11-D36
A66-B89-C11-D36
A2-B92-C11-D36
A3-B92-C11-D36
A9-B92-C11-D36
A13-B92-C11-D36
A24-B92-C11-D36
A69-B92-C11-D36
A67-B92-C11-D36
A39-B92-C11-D36
A65-B92-C11-D36
A66-B92-C11-D36
A2-B4-C12-D36
A3-B4-C12-D36
A9-B4-C12-D36
A13-B4-C12-D36
A24-B4-C12-D36
A69-B4-C12-D36
A67-B4-C12-D36
A39-B4-C12-D36
A65-B4-C12-D36
A66-B4-C12-D36
A2-B5-C12-D36
A3-B5-C12-D36
A9-B5-C12-D36
A13-B5-C12-D36
A24-B5-C12-D36
A69-B5-C12-D36
A67-B5-C12-D36
A39-B5-C12-D36
A65-B5-C12-D36
A66-B5-C12-D36
A2-B6-C12-D36
A3-B6-C12-D36
A9-B6-C12-D36
A13-B6-C12-D36
A24-B6-C12-D36
A69-B6-C12-D36
A67-B6-C12-D36

-continued

A39-B6-C12-D36
A65-B6-C12-D36
A66-B6-C12-D36
A2-B32-C12-D36
A3-B32-C12-D36
A9-B32-C12-D36
A13-B32-C12-D36
A24-B32-C12-D36
A69-B32-C12-D36
A67-B32-C12-D36
A39-B32-C12-D36
A65-B32-C12-D36
A66-B32-C12-D36
A2-B39-C12-D36
A3-B39-C12-D36
A9-B39-C12-D36
A13-B39-C12-D36
A24-B39-C12-D36
A69-B39-C12-D36
A67-B39-C12-D36
A39-B39-C12-D36
A65-B39-C12-D36
A66-B39-C12-D36
A2-B45-C12-D36
A3-B45-C12-D36
A9-B45-C12-D36
A13-B45-C12-D36
A24-B45-C12-D36
A69-B45-C12-D36
A67-B45-C12-D36
A39-B45-C12-D36
A65-B45-C12-D36
A66-B45-C12-D36
A2-B53-C12-D36
A3-B53-C12-D36
A9-B53-C12-D36
A13-B53-C12-D36
A24-B53-C12-D36
A69-B53-C12-D36
A67-B53-C12-D36
A39-B53-C12-D36
A65-B53-C12-D36
A66-B53-C12-D36
A2-B79-C12-D36
A3-B79-C12-D36
A9-B79-C12-D36
A13-B79-C12-D36
A24-B79-C12-D36
A69-B79-C12-D36
A67-B79-C12-D36
A39-B79-C12-D36
A65-B79-C12-D36
A66-B79-C12-D36
A2-B80-C12-D36
A3-B80-C12-D36
A9-B80-C12-D36
A13-B80-C12-D36
A24-B80-C12-D36
A69-B80-C12-D36
A67-B80-C12-D36
A39-B80-C12-D36
A65-B80-C12-D36
A66-B80-C12-D36
A2-B85-C12-D36
A3-B85-C12-D36
A9-B85-C12-D36
A13-B85-C12-D36
A24-B85-C12-D36
A69-B85-C12-D36
A67-B85-C12-D36
A39-B85-C12-D36
A65-B85-C12-D36
A66-B85-C12-D36
A2-B86-C12-D36
A3-B86-C12-D36
A9-B86-C12-D36
A13-B86-C12-D36
A24-B86-C12-D36
A69-B86-C12-D36
A67-B86-C12-D36

-continued
A39-B86-C12-D36
A65-B86-C12-D36
A66-B86-C12-D36
A2-B87-C12-D36
A3-B87-C12-D36
A9-B87-C12-D36
A13-B87-C12-D36
A24-B87-C12-D36
A69-B87-C12-D36
A67-B87-C12-D36
A39-B87-C12-D36
A65-B87-C12-D36
A66-B87-C12-D36
A2-B89-C12-D36
A3-B89-C12-D36
A9-B89-C12-D36
A13-B89-C12-D36
A24-B89-C12-D36
A69-B89-C12-D36
A67-B89-C12-D36
A39-B89-C12-D36
A65-B89-C12-D36
A66-B89-C12-D36
A2-B92-C12-D36
A3-B92-C12-D36
A9-B92-C12-D36
A13-B92-C12-D36
A24-B92-C12-D36
A69-B92-C12-D36
A67-B92-C12-D36
A39-B92-C12-D36
A65-B92-C12-D36
A66-B92-C12-D36
A2-B4-C13-D36
A3-B4-C13-D36
A9-B4-C13-D36
A13-B4-C13-D36
A24-B4-C13-D36
A69-B4-C13-D36
A67-B4-C13-D36
A39-B4-C13-D36
A65-B4-C13-D36
A66-B4-C13-D36
A2-B5-C13-D36
A3-B5-C13-D36
A9-B5-C13-D36
A13-B5-C13-D36
A24-B5-C13-D36
A69-B5-C13-D36
A67-B5-C13-D36
A39-B5-C13-D36
A65-B5-C13-D36
A66-B5-C13-D36
A2-B6-C13-D36
A3-B6-C13-D36
A9-B6-C13-D36
A13-B6-C13-D36
A24-B6-C13-D36
A69-B6-C13-D36
A67-B6-C13-D36
A39-B6-C13-D36
A65-B6-C13-D36
A66-B6-C13-D36
A2-B32-C13-D36
A3-B32-C13-D36
A9-B32-C13-D36
A13-B32-C13-D36
A24-B32-C13-D36
A69-B32-C13-D36
A67-B32-C13-D36
A39-B32-C13-D36
A65-B32-C13-D36
A66-B32-C13-D36
A2-B39-C13-D36
A3-B39-C13-D36
A9-B39-C13-D36
A13-B39-C13-D36
A24-B39-C13-D36
A69-B39-C13-D36
A67-B39-C13-D36

-continued
A39-B39-C13-D36
A65-B39-C13-D36
A66-B39-C13-D36
A2-B45-C13-D36
A3-B45-C13-D36
A9-B45-C13-D36
A13-B45-C13-D36
A24-B45-C13-D36
A69-B45-C13-D36
A67-B45-C13-D36
A39-B45-C13-D36
A65-B45-C13-D36
A66-B45-C13-D36
A2-B53-C13-D36
A3-B53-C13-D36
A9-B53-C13-D36
A13-B53-C13-D36
A24-B53-C13-D36
A69-B53-C13-D36
A67-B53-C13-D36
A39-B53-C13-D36
A65-B53-C13-D36
A66-B53-C13-D36
A2-B79-C13-D36
A3-B79-C13-D36
A9-B79-C13-D36
A13-B79-C13-D36
A24-B79-C13-D36
A69-B79-C13-D36
A67-B79-C13-D36
A39-B79-C13-D36
A65-B79-C13-D36
A66-B79-C13-D36
A2-B80-C13-D36
A3-B80-C13-D36
A9-B80-C13-D36
A13-B80-C13-D36
A24-B80-C13-D36
A69-B80-C13-D36
A67-B80-C13-D36
A39-B80-C13-D36
A65-B80-C13-D36
A66-B80-C13-D36
A2-B85-C13-D36
A3-B85-C13-D36
A9-B85-C13-D36
A13-B85-C13-D36
A24-B85-C13-D36
A69-B85-C13-D36
A67-B85-C13-D36
A39-B85-C13-D36
A65-B85-C13-D36
A66-B85-C13-D36
A2-B86-C13-D36
A3-B86-C13-D36
A9-B86-C13-D36
A13-B86-C13-D36
A24-B86-C13-D36
A69-B86-C13-D36
A67-B86-C13-D36
A39-B86-C13-D36
A65-B86-C13-D36
A66-B86-C13-D36
A2-B87-C13-D36
A3-B87-C13-D36
A9-B87-C13-D36
A13-B87-C13-D36
A24-B87-C13-D36
A69-B87-C13-D36
A67-B87-C13-D36
A39-B87-C13-D36
A65-B87-C13-D36
A66-B87-C13-D36
A2-B89-C13-D36
A3-B89-C13-D36
A9-B89-C13-D36
A13-B89-C13-D36
A24-B89-C13-D36
A69-B89-C13-D36
A67-B89-C13-D36

-continued
A39-B89-C13-D36
A65-B89-C13-D36
A66-B89-C13-D36
A2-B92-C13-D36
A3-B92-C13-D36
A9-B92-C13-D36
A13-B92-C13-D36
A24-B92-C13-D36
A69-B92-C13-D36
A67-B92-C13-D36
A39-B92-C13-D36
A65-B92-C13-D36
A66-B92-C13-D36
A2-B4-C1-D37
A3-B4-C1-D37
A9-B4-C1-D37
A13-B4-C1-D37
A24-B4-C1-D37
A69-B4-C1-D37
A67-B4-C1-D37
A39-B4-C1-D37
A65-B4-C1-D37
A66-B4-C1-D37
A2-B5-C1-D37
A3-B5-C1-D37
A9-B5-C1-D37
A13-B5-C1-D37
A24-B5-C1-D37
A69-B5-C1-D37
A67-B5-C1-D37
A39-B5-C1-D37
A65-B5-C1-D37
A66-B5-C1-D37
A2-B6-C1-D37
A3-B6-C1-D37
A9-B6-C1-D37
A13-B6-C1-D37
A24-B6-C1-D37
A69-B6-C1-D37
A67-B6-C1-D37
A39-B6-C1-D37
A65-B6-C1-D37
A66-B6-C1-D37
A2-B32-C1-D37
A3-B32-C1-D37
A9-B32-C1-D37
A13-B32-C1-D37
A24-B32-C1-D37
A69-B32-C1-D37
A67-B32-C1-D37
A39-B32-C1-D37
A65-B32-C1-D37
A66-B32-C1-D37
A2-B39-C1-D37
A3-B39-C1-D37
A9-B39-C1-D37
A13-B39-C1-D37
A24-B39-C1-D37
A69-B39-C1-D37
A67-B39-C1-D37
A39-B39-C1-D37
A65-B39-C1-D37
A66-B39-C1-D37
A2-B45-C1-D37
A3-B45-C1-D37
A9-B45-C1-D37
A13-B45-C1-D37
A24-B45-C1-D37
A69-B45-C1-D37
A67-B45-C1-D37
A39-B45-C1-D37
A65-B45-C1-D37
A66-B45-C1-D37
A2-B53-C1-D37
A3-B53-C1-D37
A9-B53-C1-D37
A13-B53-C1-D37
A24-B53-C1-D37
A69-B53-C1-D37
A67-B53-C1-D37

-continued
A39-B53-C1-D37
A65-B53-C1-D37
A66-B53-C1-D37
A2-B79-C1-D37
A3-B79-C1-D37
A9-B79-C1-D37
A13-B79-C1-D37
A24-B79-C1-D37
A69-B79-C1-D37
A67-B79-C1-D37
A39-B79-C1-D37
A65-B79-C1-D37
A66-B79-C1-D37
A2-B80-C1-D37
A3-B80-C1-D37
A9-B80-C1-D37
A13-B80-C1-D37
A24-B80-C1-D37
A69-B80-C1-D37
A67-B80-C1-D37
A39-B80-C1-D37
A65-B80-C1-D37
A66-B80-C1-D37
A2-B85-C1-D37
A3-B85-C1-D37
A9-B85-C1-D37
A13-B85-C1-D37
A24-B85-C1-D37
A69-B85-C1-D37
A67-B85-C1-D37
A39-B85-C1-D37
A65-B85-C1-D37
A66-B85-C1-D37
A2-B86-C1-D37
A3-B86-C1-D37
A9-B86-C1-D37
A13-B86-C1-D37
A24-B86-C1-D37
A69-B86-C1-D37
A67-B86-C1-D37
A39-B86-C1-D37
A65-B86-C1-D37
A66-B86-C1-D37
A2-B87-C1-D37
A3-B87-C1-D37
A9-B87-C1-D37
A13-B87-C1-D37
A24-B87-C1-D37
A69-B87-C1-D37
A67-B87-C1-D37
A39-B87-C1-D37
A65-B87-C1-D37
A66-B87-C1-D37
A2-B89-C1-D37
A3-B89-C1-D37
A9-B89-C1-D37
A13-B89-C1-D37
A24-B89-C1-D37
A69-B89-C1-D37
A67-B89-C1-D37
A39-B89-C1-D37
A65-B89-C1-D37
A66-B89-C1-D37
A2-B92-C1-D37
A3-B92-C1-D37
A9-B92-C1-D37
A13-B92-C1-D37
A24-B92-C1-D37
A69-B92-C1-D37
A67-B92-C1-D37
A39-B92-C1-D37
A65-B92-C1-D37
A66-B92-C1-D37
A2-B4-C2-D37
A3-B4-C2-D37
A9-B4-C2-D37
A13-B4-C2-D37
A24-B4-C2-D37
A69-B4-C2-D37
A67-B4-C2-D37

-continued
A39-B4-C2-D37
A65-B4-C2-D37
A66-B4-C2-D37
A2-B5-C2-D37
A3-B5-C2-D37
A9-B5-C2-D37
A13-B5-C2-D37
A24-B5-C2-D37
A69-B5-C2-D37
A67-B5-C2-D37
A39-B5-C2-D37
A65-B5-C2-D37
A66-B5-C2-D37
A2-B6-C2-D37
A3-B6-C2-D37
A9-B6-C2-D37
A13-B6-C2-D37
A24-B6-C2-D37
A69-B6-C2-D37
A67-B6-C2-D37
A39-B6-C2-D37
A65-B6-C2-D37
A66-B6-C2-D37
A2-B32-C2-D37
A3-B32-C2-D37
A9-B32-C2-D37
A13-B32-C2-D37
A24-B32-C2-D37
A69-B32-C2-D37
A67-B32-C2-D37
A39-B32-C2-D37
A65-B32-C2-D37
A66-B32-C2-D37
A2-B39-C2-D37
A3-B39-C2-D37
A9-B39-C2-D37
A13-B39-C2-D37
A24-B39-C2-D37
A69-B39-C2-D37
A67-B39-C2-D37
A39-B39-C2-D37
A65-B39-C2-D37
A66-B39-C2-D37
A2-B45-C2-D37
A3-B45-C2-D37
A9-B45-C2-D37
A13-B45-C2-D37
A24-B45-C2-D37
A69-B45-C2-D37
A67-B45-C2-D37
A39-B45-C2-D37
A65-B45-C2-D37
A66-B45-C2-D37
A2-B53-C2-D37
A3-B53-C2-D37
A9-B53-C2-D37
A13-B53-C2-D37
A24-B53-C2-D37
A69-B53-C2-D37
A67-B53-C2-D37
A39-B53-C2-D37
A65-B53-C2-D37
A66-B53-C2-D37
A2-B79-C2-D37
A3-B79-C2-D37
A9-B79-C2-D37
A13-B79-C2-D37
A24-B79-C2-D37
A69-B79-C2-D37
A67-B79-C2-D37
A39-B79-C2-D37
A65-B79-C2-D37
A66-B79-C2-D37
A2-B80-C2-D37
A3-B80-C2-D37
A9-B80-C2-D37
A13-B80-C2-D37
A24-B80-C2-D37
A69-B80-C2-D37
A67-B80-C2-D37

-continued
A39-B80-C2-D37
A65-B80-C2-D37
A66-B80-C2-D37
A2-B85-C2-D37
A3-B85-C2-D37
A9-B85-C2-D37
A13-B85-C2-D37
A24-B85-C2-D37
A69-B85-C2-D37
A67-B85-C2-D37
A39-B85-C2-D37
A65-B85-C2-D37
A66-B85-C2-D37
A2-B86-C2-D37
A3-B86-C2-D37
A9-B86-C2-D37
A13-B86-C2-D37
A24-B86-C2-D37
A69-B86-C2-D37
A67-B86-C2-D37
A39-B86-C2-D37
A65-B86-C2-D37
A66-B86-C2-D37
A2-B87-C2-D37
A3-B87-C2-D37
A9-B87-C2-D37
A13-B87-C2-D37
A24-B87-C2-D37
A69-B87-C2-D37
A67-B87-C2-D37
A39-B87-C2-D37
A65-B87-C2-D37
A66-B87-C2-D37
A2-B89-C2-D37
A3-B89-C2-D37
A9-B89-C2-D37
A13-B89-C2-D37
A24-B89-C2-D37
A69-B89-C2-D37
A67-B89-C2-D37
A39-B89-C2-D37
A65-B89-C2-D37
A66-B89-C2-D37
A2-B92-C2-D37
A3-B92-C2-D37
A9-B92-C2-D37
A13-B92-C2-D37
A24-B92-C2-D37
A69-B92-C2-D37
A67-B92-C2-D37
A39-B92-C2-D37
A65-B92-C2-D37
A66-B92-C2-D37
A2-B4-C3-D37
A3-B4-C3-D37
A9-B4-C3-D37
A13-B4-C3-D37
A24-B4-C3-D37
A69-B4-C3-D37
A67-B4-C3-D37
A39-B4-C3-D37
A65-B4-C3-D37
A66-B4-C3-D37
A2-B5-C3-D37
A3-B5-C3-D37
A9-B5-C3-D37
A13-B5-C3-D37
A24-B5-C3-D37
A69-B5-C3-D37
A67-B5-C3-D37
A39-B5-C3-D37
A65-B5-C3-D37
A66-B5-C3-D37
A2-B6-C3-D37
A3-B6-C3-D37
A9-B6-C3-D37
A13-B6-C3-D37
A24-B6-C3-D37
A69-B6-C3-D37
A67-B6-C3-D37

-continued

A39-B6-C3-D37
A65-B6-C3-D37
A66-B6-C3-D37
A2-B32-C3-D37
A3-B32-C3-D37
A9-B32-C3-D37
A13-B32-C3-D37
A24-B32-C3-D37
A69-B32-C3-D37
A67-B32-C3-D37
A39-B32-C3-D37
A65-B32-C3-D37
A66-B32-C3-D37
A2-B39-C3-D37
A3-B39-C3-D37
A9-B39-C3-D37
A13-B39-C3-D37
A24-B39-C3-D37
A69-B39-C3-D37
A67-B39-C3-D37
A39-B39-C3-D37
A65-B39-C3-D37
A66-B39-C3-D37
A2-B45-C3-D37
A3-B45-C3-D37
A9-B45-C3-D37
A13-B45-C3-D37
A24-B45-C3-D37
A69-B45-C3-D37
A67-B45-C3-D37
A39-B45-C3-D37
A65-B45-C3-D37
A66-B45-C3-D37
A2-B53-C3-D37
A3-B53-C3-D37
A9-B53-C3-D37
A13-B53-C3-D37
A24-B53-C3-D37
A69-B53-C3-D37
A67-B53-C3-D37
A39-B53-C3-D37
A65-B53-C3-D37
A66-B53-C3-D37
A2-B79-C3-D37
A3-B79-C3-D37
A9-B79-C3-D37
A13-B79-C3-D37
A24-B79-C3-D37
A69-B79-C3-D37
A67-B79-C3-D37
A39-B79-C3-D37
A65-B79-C3-D37
A66-B79-C3-D37
A2-B80-C3-D37
A3-B80-C3-D37
A9-B80-C3-D37
A13-B80-C3-D37
A24-B80-C3-D37
A69-B80-C3-D37
A67-B80-C3-D37
A39-B80-C3-D37
A65-B80-C3-D37
A66-B80-C3-D37
A2-B85-C3-D37
A3-B85-C3-D37
A9-B85-C3-D37
A13-B85-C3-D37
A24-B85-C3-D37
A69-B85-C3-D37
A67-B85-C3-D37
A39-B85-C3-D37
A65-B85-C3-D37
A66-B85-C3-D37
A2-B86-C3-D37
A3-B86-C3-D37
A9-B86-C3-D37
A13-B86-C3-D37
A24-B86-C3-D37
A69-B86-C3-D37
A67-B86-C3-D37

-continued

A39-B86-C3-D37
A65-B86-C3-D37
A66-B86-C3-D37
A2-B87-C3-D37
A3-B87-C3-D37
A9-B87-C3-D37
A13-B87-C3-D37
A24-B87-C3-D37
A69-B87-C3-D37
A67-B87-C3-D37
A39-B87-C3-D37
A65-B87-C3-D37
A66-B87-C3-D37
A2-B89-C3-D37
A3-B89-C3-D37
A9-B89-C3-D37
A13-B89-C3-D37
A24-B89-C3-D37
A69-B89-C3-D37
A67-B89-C3-D37
A39-B89-C3-D37
A65-B89-C3-D37
A66-B89-C3-D37
A2-B92-C3-D37
A3-B92-C3-D37
A9-B92-C3-D37
A13-B92-C3-D37
A24-B92-C3-D37
A69-B92-C3-D37
A67-B92-C3-D37
A39-B92-C3-D37
A65-B92-C3-D37
A66-B92-C3-D37
A2-B4-C4-D37
A3-B4-C4-D37
A9-B4-C4-D37
A13-B4-C4-D37
A24-B4-C4-D37
A69-B4-C4-D37
A67-B4-C4-D37
A39-B4-C4-D37
A65-B4-C4-D37
A66-B4-C4-D37
A2-B5-C4-D37
A3-B5-C4-D37
A9-B5-C4-D37
A13-B5-C4-D37
A24-B5-C4-D37
A69-B5-C4-D37
A67-B5-C4-D37
A39-B5-C4-D37
A65-B5-C4-D37
A66-B5-C4-D37
A2-B6-C4-D37
A3-B6-C4-D37
A9-B6-C4-D37
A13-B6-C4-D37
A24-B6-C4-D37
A69-B6-C4-D37
A67-B6-C4-D37
A39-B6-C4-D37
A65-B6-C4-D37
A66-B6-C4-D37
A2-B32-C4-D37
A3-B32-C4-D37
A9-B32-C4-D37
A13-B32-C4-D37
A24-B32-C4-D37
A69-B32-C4-D37
A67-B32-C4-D37
A39-B32-C4-D37
A65-B32-C4-D37
A66-B32-C4-D37
A2-B39-C4-D37
A3-B39-C4-D37
A9-B39-C4-D37
A13-B39-C4-D37
A24-B39-C4-D37
A69-B39-C4-D37
A67-B39-C4-D37

-continued

A39-B39-C4-D37
A65-B39-C4-D37
A66-B39-C4-D37
A2-B45-C4-D37
A3-B45-C4-D37
A9-B45-C4-D37
A13-B45-C4-D37
A24-B45-C4-D37
A69-B45-C4-D37
A67-B45-C4-D37
A39-B45-C4-D37
A65-B45-C4-D37
A66-B45-C4-D37
A2-B53-C4-D37
A3-B53-C4-D37
A9-B53-C4-D37
A13-B53-C4-D37
A24-B53-C4-D37
A69-B53-C4-D37
A67-B53-C4-D37
A39-B53-C4-D37
A65-B53-C4-D37
A66-B53-C4-D37
A2-B79-C4-D37
A3-B79-C4-D37
A9-B79-C4-D37
A13-B79-C4-D37
A24-B79-C4-D37
A69-B79-C4-D37
A67-B79-C4-D37
A39-B79-C4-D37
A65-B79-C4-D37
A66-B79-C4-D37
A2-B80-C4-D37
A3-B80-C4-D37
A9-B80-C4-D37
A13-B80-C4-D37
A24-B80-C4-D37
A69-B80-C4-D37
A67-B80-C4-D37
A39-B80-C4-D37
A65-B80-C4-D37
A66-B80-C4-D37
A2-B85-C4-D37
A3-B85-C4-D37
A9-B85-C4-D37
A13-B85-C4-D37
A24-B85-C4-D37
A69-B85-C4-D37
A67-B85-C4-D37
A39-B85-C4-D37
A65-B85-C4-D37
A66-B85-C4-D37
A2-B86-C4-D37
A3-B86-C4-D37
A9-B86-C4-D37
A13-B86-C4-D37
A24-B86-C4-D37
A69-B86-C4-D37
A67-B86-C4-D37
A39-B86-C4-D37
A65-B86-C4-D37
A66-B86-C4-D37
A2-B87-C4-D37
A3-B87-C4-D37
A9-B87-C4-D37
A13-B87-C4-D37
A24-B87-C4-D37
A69-B87-C4-D37
A67-B87-C4-D37
A39-B87-C4-D37
A65-B87-C4-D37
A66-B87-C4-D37
A2-B89-C4-D37
A3-B89-C4-D37
A9-B89-C4-D37
A13-B89-C4-D37
A24-B89-C4-D37
A69-B89-C4-D37
A67-B89-C4-D37

-continued

A39-B89-C4-D37
A65-B89-C4-D37
A66-B89-C4-D37
A2-B92-C4-D37
A3-B92-C4-D37
A9-B92-C4-D37
A13-B92-C4-D37
A24-B92-C4-D37
A69-B92-C4-D37
A67-B92-C4-D37
A39-B92-C4-D37
A65-B92-C4-D37
A66-B92-C4-D37
A2-B4-C5-D37
A3-B4-C5-D37
A9-B4-C5-D37
A13-B4-C5-D37
A24-B4-C5-D37
A69-B4-C5-D37
A67-B4-C5-D37
A39-B4-C5-D37
A65-B4-C5-D37
A66-B4-C5-D37
A2-B5-C5-D37
A3-B5-C5-D37
A9-B5-C5-D37
A13-B5-C5-D37
A24-B5-C5-D37
A69-B5-C5-D37
A67-B5-C5-D37
A39-B5-C5-D37
A65-B5-C5-D37
A66-B5-C5-D37
A2-B6-C5-D37
A3-B6-C5-D37
A9-B6-C5-D37
A13-B6-C5-D37
A24-B6-C5-D37
A69-B6-C5-D37
A67-B6-C5-D37
A39-B6-C5-D37
A65-B6-C5-D37
A66-B6-C5-D37
A2-B32-C5-D37
A3-B32-C5-D37
A9-B32-C5-D37
A13-B32-C5-D37
A24-B32-C5-D37
A69-B32-C5-D37
A67-B32-C5-D37
A39-B32-C5-D37
A65-B32-C5-D37
A66-B32-C5-D37
A2-B39-C5-D37
A3-B39-C5-D37
A9-B39-C5-D37
A13-B39-C5-D37
A24-B39-C5-D37
A69-B39-C5-D37
A67-B39-C5-D37
A39-B39-C5-D37
A65-B39-C5-D37
A66-B39-C5-D37
A2-B45-C5-D37
A3-B45-C5-D37
A9-B45-C5-D37
A13-B45-C5-D37
A24-B45-C5-D37
A69-B45-C5-D37
A67-B45-C5-D37
A39-B45-C5-D37
A65-B45-C5-D37
A66-B45-C5-D37
A2-B53-C5-D37
A3-B53-C5-D37
A9-B53-C5-D37
A13-B53-C5-D37
A24-B53-C5-D37
A69-B53-C5-D37
A67-B53-C5-D37

-continued
A39-B53-C5-D37
A65-B53-C5-D37
A66-B53-C5-D37
A2-B79-C5-D37
A3-B79-C5-D37
A9-B79-C5-D37
A13-B79-C5-D37
A24-B79-C5-D37
A69-B79-C5-D37
A67-B79-C5-D37
A39-B79-C5-D37
A65-B79-C5-D37
A66-B79-C5-D37
A2-B80-C5-D37
A3-B80-C5-D37
A9-B80-C5-D37
A13-B80-C5-D37
A24-B80-C5-D37
A69-B80-C5-D37
A67-B80-C5-D37
A39-B80-C5-D37
A65-B80-C5-D37
A66-B80-C5-D37
A2-B85-C5-D37
A3-B85-C5-D371
A9-B85-C5-D37
A13-B85-C5-D37
A24-B85-C5-D37
A69-B85-C5-D37
A67-B85-C5-D37
A39-B85-C5-D37
A65-B85-C5-D37
A66-B85-C5-D37
A2-B86-C5-D37
A3-B86-C5-D371
A9-B86-C5-D37
A13-B86-C5-D37
A24-B86-C5-D37
A69-B86-C5-D37
A67-B86-C5-D37
A39-B86-C5-D37
A65-B86-C5-D37
A66-B86-C5-D37
A2-B87-C5-D37
A3-B87-C5-D37
A9-B87-C5-D37
A13-B87-C5-D37
A24-B87-C5-D37
A69-B87-C5-D37
A67-B87-C5-D37
A39-B87-C5-D37
A65-B87-C5-D37
A66-B87-C5-D37
A2-B89-C5-D37
A3-B89-C5-D37
A9-B89-C5-D37
A13-B89-C5-D37
A24-B89-C5-D37
A69-B89-C5-D37
A67-B89-C5-D37
A39-B89-C5-D37
A65-B89-C5-D37
A66-B89-C5-D37
A2-B92-C5-D37
A3-B92-C5-D37
A9-B92-C5-D37
A13-B92-C5-D37
A24-B92-C5-D37
A69-B92-C5-D37
A67-B92-C5-D37
A39-B92-C5-D37
A65-B92-C5-D37
A66-B92-C5-D37
A2-B4-C6-D37
A3-B4-C6-D37
A9-B4-C6-D37
A13-B4-C6-D37
A24-B4-C6-D37
A69-B4-C6-D37
A67-B4-C6-D37

-continued
A39-B4-C6-D37
A65-B4-C6-D37
A66-B4-C6-D37
A2-B5-C6-D37
A3-B5-C6-D37
A9-B5-C6-D37
A13-B5-C6-D37
A24-B5-C6-D37
A69-B5-C6-D37
A67-B5-C6-D37
A39-B5-C6-D37
A65-B5-C6-D37
A66-B5-C6-D37
A2-B6-C6-D37
A3-B6-C6-D37
A9-B6-C6-D37
A13-B6-C6-D37
A24-B6-C6-D37
A69-B6-C6-D37
A67-B6-C6-D37
A39-B6-C6-D37
A65-B6-C6-D37
A66-B6-C6-D37
A2-B32-C6-D37
A3-B32-C6-D37
A9-B32-C6-D37
A13-B32-C6-D37
A24-B32-C6-D37
A69-B32-C6-D37
A67-B32-C6-D37
A39-B32-C6-D37
A65-B32-C6-D37
A66-B32-C6-D37
A2-B39-C6-D37
A3-B39-C6-D37
A9-B39-C6-D37
A13-B39-C6-D37
A24-B39-C6-D37
A69-B39-C6-D37
A67-B39-C6-D37
A39-B39-C6-D37
A65-B39-C6-D37
A66-B39-C6-D37
A2-B45-C6-D37
A3-B45-C6-D37
A9-B45-C6-D37
A13-B45-C6-D37
A24-B45-C6-D37
A69-B45-C6-D37
A67-B45-C6-D37
A39-B45-C6-D37
A65-B45-C6-D37
A66-B45-C6-D37
A2-B53-C6-D37
A3-B53-C6-D37
A9-B53-C6-D37
A13-B53-C6-D37
A24-B53-C6-D37
A69-B53-C6-D37
A67-B53-C6-D37
A39-B53-C6-D37
A65-B53-C6-D37
A66-B53-C6-D37
A2-B79-C6-D37
A3-B79-C6-D37
A9-B79-C6-D37
A13-B79-C6-D37
A24-B79-C6-D37
A69-B79-C6-D37
A67-B79-C6-D37
A39-B79-C6-D37
A65-B79-C6-D37
A66-B79-C6-D37
A2-B80-C6-D37
A3-B80-C6-D37
A9-B80-C6-D37
A13-B80-C6-D37
A24-B80-C6-D37
A69-B80-C6-D37
A67-B80-C6-D37

-continued
A39-B80-C6-D37
A65-B80-C6-D37
A66-B80-C6-D37
A2-B85-C6-D37
A3-B85-C6-D37
A9-B85-C6-D37
A13-B85-C6-D37
A24-B85-C6-D37
A69-B85-C6-D37
A67-B85-C6-D37
A39-B85-C6-D37
A65-B85-C6-D37
A66-B85-C6-D37
A2-B86-C6-D37
A3-B86-C6-D37
A9-B86-C6-D37
A13-B86-C6-D37
A24-B86-C6-D37
A69-B86-C6-D37
A67-B86-C6-D37
A39-B86-C6-D37
A65-B86-C6-D37
A66-B86-C6-D37
A2-B87-C6-D37
A3-B87-C6-D37
A9-B87-C6-D37
A13-B87-C6-D37
A24-B87-C6-D37
A69-B87-C6-D37
A67-B87-C6-D37
A39-B87-C6-D37
A65-B87-C6-D37
A66-B87-C6-D37
A2-B89-C6-D37
A3-B89-C6-D37
A9-B89-C6-D37
A13-B89-C6-D37
A24-B89-C6-D37
A69-B89-C6-D37
A67-B89-C6-D37
A39-B89-C6-D37
A65-B89-C6-D37
A66-B89-C6-D37
A2-B92-C6-D37
A3-B92-C6-D37
A9-B92-C6-D37
A13-B92-C6-D37
A24-B92-C6-D37
A69-B92-C6-D37
A67-B92-C6-D37
A39-B92-C6-D37
A65-B92-C6-D37
A66-B92-C6-D37
A2-B4-C7-D37
A3-B4-C7-D37
A9-B4-C7-D37
A13-B4-C7-D37
A24-B4-C7-D37
A69-B4-C7-D37
A67-B4-C7-D37
A39-B4-C7-D37
A65-B4-C7-D37
A66-B4-C7-D37
A2-B5-C7-D37
A3-B5-C7-D37
A9-B5-C7-D37
A13-B5-C7-D37
A24-B5-C7-D37
A69-B5-C7-D37
A67-B5-C7-D37
A39-B5-C7-D37
A65-B5-C7-D37
A66-B5-C7-D37
A2-B6-C7-D37
A3-B6-C7-D37
A9-B6-C7-D37
A13-B6-C7-D37
A24-B6-C7-D37
A69-B6-C7-D37
A67-B6-C7-D37

-continued
A39-B6-C7-D37
A65-B6-C7-D37
A66-B6-C7-D37
A2-B32-C7-D37
A3-B32-C7-D37
A9-B32-C7-D37
A13-B32-C7-D37
A24-B32-C7-D37
A69-B32-C7-D37
A67-B32-C7-D37
A39-B32-C7-D37
A65-B32-C7-D37
A66-B32-C7-D37
A2-B39-C7-D37
A3-B39-C7-D37
A9-B39-C7-D37
A13-B39-C7-D37
A24-B39-C7-D37
A69-B39-C7-D37
A67-B39-C7-D37
A39-B39-C7-D37
A65-B39-C7-D37
A66-B39-C7-D37
A2-B45-C7-D37
A3-B45-C7-D37
A9-B45-C7-D37
A13-B45-C7-D37
A24-B45-C7-D37
A69-B45-C7-D37
A67-B45-C7-D37
A39-B45-C7-D37
A65-B45-C7-D37
A66-B45-C7-D37
A2-B53-C7-D37
A3-B53-C7-D37
A9-B53-C7-D37
A13-B53-C7-D37
A24-B53-C7-D37
A69-B53-C7-D37
A67-B53-C7-D37
A39-B53-C7-D37
A65-B53-C7-D37
A66-B53-C7-D37
A2-B79-C7-D37
A3-B79-C7-D37
A9-B79-C7-D37
A13-B79-C7-D37
A24-B79-C7-D37
A69-B79-C7-D37
A67-B79-C7-D37
A39-B79-C7-D37
A65-B79-C7-D37
A66-B79-C7-D37
A2-B80-C7-D37
A3-B80-C7-D37
A9-B80-C7-D37
A13-B80-C7-D37
A24-B80-C7-D37
A69-B80-C7-D37
A67-B80-C7-D37
A39-B80-C7-D37
A65-B80-C7-D37
A66-B80-C7-D37
A2-B85-C7-D37
A3-B85-C7-D37
A9-B85-C7-D37
A13-B85-C7-D37
A24-B85-C7-D37
A69-B85-C7-D37
A67-B85-C7-D37
A39-B85-C7-D37
A65-B85-C7-D37
A66-B85-C7-D37
A2-B86-C7-D37
A3-B86-C7-D37
A9-B86-C7-D37
A13-B86-C7-D37
A24-B86-C7-D37
A69-B86-C7-D37
A67-B86-C7-D37

-continued

A39-B86-C7-D37
A65-B86-C7-D37
A66-B86-C7-D37
A2-B87-C7-D37
A3-B87-C7-D37
A9-B87-C7-D37
A13-B87-C7-D37
A24-B87-C7-D37
A69-B87-C7-D37
A67-B87-C7-D37
A39-B87-C7-D37
A65-B87-C7-D37
A66-B87-C7-D37
A2-B89-C7-D37
A3-B89-C7-D37
A9-B89-C7-D37
A13-B89-C7-D37
A24-B89-C7-D37
A69-B89-C7-D37
A67-B89-C7-D37
A39-B89-C7-D37
A65-B89-C7-D37
A66-B89-C7-D37
A2-B92-C7-D37
A3-B92-C7-D37
A9-B92-C7-D37
A13-B92-C7-D37
A24-B92-C7-D37
A69-B92-C7-D37
A67-B92-C7-D37
A39-B92-C7-D37
A65-B92-C7-D37
A66-B92-C7-D37
A2-B4-C8-D37
A3-B4-C8-D37
A9-B4-C8-D37
A13-B4-C8-D37
A24-B4-C8-D37
A69-B4-C8-D37
A67-B4-C8-D37
A39-B4-C8-D37
A65-B4-C8-D37
A66-B4-C8-D37
A2-B5-C8-D37
A3-B5-C8-D37
A9-B5-C8-D37
A13-B5-C8-D37
A24-B5-C8-D37
A69-B5-C8-D37
A67-B5-C8-D37
A39-B5-C8-D37
A65-B5-C8-D37
A66-B5-C8-D37
A2-B6-C8-D37
A3-B6-C8-D37
A9-B6-C8-D37
A13-B6-C8-D37
A24-B6-C8-D37
A69-B6-C8-D37
A67-B6-C8-D37
A39-B6-C8-D37
A65-B6-C8-D37
A66-B6-C8-D37
A2-B32-C8-D37
A3-B32-C8-D37
A9-B32-C8-D37
A13-B32-C8-D37
A24-B32-C8-D37
A69-B32-C8-D37
A67-B32-C8-D37
A39-B32-C8-D37
A65-B32-C8-D37
A66-B32-C8-D37
A2-B39-C8-D37
A3-B39-C8-D37
A9-B39-C8-D37
A13-B39-C8-D37
A24-B39-C8-D37
A69-B39-C8-D37
A67-B39-C8-D37

-continued

A39-B39-C8-D37
A65-B39-C8-D37
A66-B39-C8-D37
A2-B45-C8-D37
A3-B45-C8-D37
A9-B45-C8-D37
A13-B45-C8-D37
A24-B45-C8-D37
A69-B45-C8-D37
A67-B45-C8-D37
A39-B45-C8-D37
A65-B45-C8-D37
A66-B45-C8-D37
A2-B53-C8-D37
A3-B53-C8-D37
A9-B53-C8-D37
A13-B53-C8-D37
A24-B53-C8-D37
A69-B53-C8-D37
A67-B53-C8-D37
A39-B53-C8-D37
A65-B53-C8-D37
A66-B53-C8-D37
A2-B79-C8-D37
A3-B79-C8-D37
A9-B79-C8-D37
A13-B79-C8-D37
A24-B79-C8-D37
A69-B79-C8-D37
A67-B79-C8-D37
A39-B79-C8-D37
A65-B79-C8-D37
A66-B79-C8-D37
A2-B80-C8-D37
A3-B80-C8-D37
A9-B80-C8-D37
A13-B80-C8-D37
A24-B80-C8-D37
A69-B80-C8-D37
A67-B80-C8-D37
A39-B80-C8-D37
A65-B80-C8-D37
A66-B80-C8-D37
A2-B85-C8-D37
A3-B85-C8-D37
A9-B85-C8-D37
A13-B85-C8-D37
A24-B85-C8-D37
A69-B85-C8-D37
A67-B85-C8-D37
A39-B85-C8-D37
A65-B85-C8-D37
A66-B85-C8-D37
A2-B86-C8-D37
A3-B86-C8-D37
A9-B86-C8-D37
A13-B86-C8-D37
A24-B86-C8-D37
A69-B86-C8-D37
A67-B86-C8-D37
A39-B86-C8-D37
A65-B86-C8-D37
A66-B86-C8-D37
A2-B87-C8-D37
A3-B87-C8-D37
A9-B87-C8-D37
A13-B87-C8-D37
A24-B87-C8-D37
A69-B87-C8-D37
A67-B87-C8-D37
A39-B87-C8-D37
A65-B87-C8-D37
A66-B87-C8-D37
A2-B89-C8-D37
A3-B89-C8-D37
A9-B89-C8-D37
A13-B89-C8-D37
A24-B89-C8-D37
A69-B89-C8-D37
A67-B89-C8-D37

-continued
A39-B89-C8-D37
A65-B89-C8-D37
A66-B89-C8-D37
A2-B92-C8-D37
A3-B92-C8-D37
A9-B92-C8-D37
A13-B92-C8-D37
A24-B92-C8-D37
A69-B92-C8-D37
A67-B92-C8-D37
A39-B92-C8-D37
A65-B92-C8-D37
A66-B92-C8-D37
A2-B4-C9-D37
A3-B4-C9-D37
A9-B4-C9-D37
A13-B4-C9-D37
A24-B4-C9-D37
A69-B4-C9-D37
A67-B4-C9-D37
A39-B4-C9-D37
A65-B4-C9-D37
A66-B4-C9-D37
A2-B5-C9-D37
A3-B5-C9-D37
A9-B5-C9-D37
A13-B5-C9-D37
A24-B5-C9-D37
A69-B5-C9-D37
A67-B5-C9-D37
A39-B5-C9-D37
A65-B5-C9-D37
A66-B5-C9-D37
A2-B6-C9-D37
A3-B6-C9-D37
A9-B6-C9-D37
A13-B6-C9-D37
A24-B6-C9-D37
A69-B6-C9-D37
A67-B6-C9-D37
A39-B6-C9-D37
A65-B6-C9-D37
A66-B6-C9-D37
A2-B32-C9-D37
A3-B32-C9-D37
A9-B32-C9-D37
A13-B32-C9-D37
A24-B32-C9-D37
A69-B32-C9-D37
A67-B32-C9-D37
A39-B32-C9-D37
A65-B32-C9-D37
A66-B32-C9-D37
A2-B39-C9-D37
A3-B39-C9-D37
A9-B39-C9-D37
A13-B39-C9-D37
A24-B39-C9-D37
A69-B39-C9-D37
A67-B39-C9-D37
A39-B39-C9-D37
A65-B39-C9-D37
A66-B39-C9-D37
A2-B45-C9-D37
A3-B45-C9-D37
A9-B45-C9-D37
A13-B45-C9-D37
A24-B45-C9-D37
A69-B45-C9-D37
A67-B45-C9-D37
A39-B45-C9-D37
A65-B45-C9-D37
A66-B45-C9-D37
A2-B53-C9-D37
A3-B53-C9-D37
A9-B53-C9-D37
A13-B53-C9-D37
A24-B53-C9-D37
A69-B53-C9-D37
A67-B53-C9-D37

-continued
A39-B53-C9-D37
A65-B53-C9-D37
A66-B53-C9-D37
A2-B79-C9-D37
A3-B79-C9-D37
A9-B79-C9-D37
A13-B79-C9-D37
A24-B79-C9-D37
A69-B79-C9-D37
A67-B79-C9-D37
A39-B79-C9-D37
A65-B79-C9-D37
A66-B79-C9-D37
A2-B80-C9-D37
A3-B80-C9-D37
A9-B80-C9-D37
A13-B80-C9-D37
A24-B80-C9-D37
A69-B80-C9-D37
A67-B80-C9-D37
A39-B80-C9-D37
A65-B80-C9-D37
A66-B80-C9-D37
A2-B85-C9-D37
A3-B85-C9-D37
A9-B85-C9-D37
A13-B85-C9-D37
A24-B85-C9-D37
A69-B85-C9-D37
A67-B85-C9-D37
A39-B85-C9-D37
A65-B85-C9-D37
A66-B85-C9-D37
A2-B86-C9-D37
A3-B86-C9-D37
A9-B86-C9-D37
A13-B86-C9-D37
A24-B86-C9-D37
A69-B86-C9-D37
A67-B86-C9-D37
A39-B86-C9-D37
A65-B86-C9-D37
A66-B86-C9-D37
A2-B87-C9-D37
A3-B87-C9-D37
A9-B87-C9-D37
A13-B87-C9-D37
A24-B87-C9-D37
A69-B87-C9-D37
A67-B87-C9-D37
A39-B87-C9-D37
A65-B87-C9-D37
A66-B87-C9-D37
A2-B89-C9-D37
A3-B89-C9-D37
A9-B89-C9-D37
A13-B89-C9-D37
A24-B89-C9-D37
A69-B89-C9-D37
A67-B89-C9-D37
A39-B89-C9-D37
A65-B89-C9-D37
A66-B89-C9-D37
A2-B92-C9-D37
A3-B92-C9-D37
A9-B92-C9-D37
A13-B92-C9-D37
A24-B92-C9-D37
A69-B92-C9-D37
A67-B92-C9-D37
A39-B92-C9-D37
A65-B92-C9-D37
A66-B92-C9-D37
A2-B4-C10-D37
A3-B4-C10-D37
A9-B4-C10-D37
A13-B4-C10-D37
A24-B4-C10-D37
A69-B4-C10-D37
A67-B4-C10-D37

-continued

A39-B4-C10-D37
A65-B4-C10-D37
A66-B4-C10-D37
A2-B5-C10-D37
A3-B5-C10-D37
A9-B5-C10-D37
A13-B5-C10-D37
A24-B5-C10-D37
A69-B5-C10-D37
A67-B5-C10-D37
A39-B5-C10-D37
A65-B5-C10-D37
A66-B5-C10-D37
A2-B6-C10-D37
A3-B6-C10-D37
A9-B6-C10-D37
A13-B6-C10-D37
A24-B6-C10-D37
A69-B6-C10-D37
A67-B6-C10-D37
A39-B6-C10-D37
A65-B6-C10-D37
A66-B6-C10-D37
A2-B32-C10-D37
A3-B32-C10-D37
A9-B32-C10-D37
A13-B32-C10-D37
A24-B32-C10-D37
A69-B32-C10-D37
A67-B32-C10-D37
A39-B32-C10-D37
A65-B32-C10-D37
A66-B32-C10-D37
A2-B39-C10-D37
A3-B39-C10-D37
A9-B39-C10-D37
A13-B39-C10-D37
A24-B39-C10-D37
A69-B39-C10-D37
A67-B39-C10-D37
A39-B39-C10-D37
A65-B39-C10-D37
A66-B39-C10-D37
A2-B45-C10-D37
A3-B45-C10-D37
A9-B45-C10-D37
A13-B45-C10-D37
A24-B45-C10-D37
A69-B45-C10-D37
A67-B45-C10-D37
A39-B45-C10-D37
A65-B45-C10-D37
A66-B45-C10-D37
A2-B53-C10-D37
A3-B53-C10-D37
A9-B53-C10-D37
A13-B53-C10-D37
A24-B53-C10-D37
A69-B53-C10-D37
A67-B53-C10-D37
A39-B53-C10-D37
A65-B53-C10-D37
A66-B53-C10-D37
A2-B79-C10-D37
A3-B79-C10-D37
A9-B79-C10-D37
A13-B79-C10-D37
A24-B79-C10-D37
A69-B79-C10-D37
A67-B79-C10-D37
A39-B79-C10-D37
A65-B79-C10-D37
A66-B79-C10-D37
A2-B80-C10-D37
A3-B80-C10-D37
A9-B80-C10-D37
A13-B80-C10-D37
A24-B80-C10-D37
A69-B80-C10-D37
A67-B80-C10-D37

-continued

A39-B80-C10-D37
A65-B80-C10-D37
A66-B80-C10-D37
A2-B85-C10-D37
A3-B85-C10-D37
A9-B85-C10-D37
A13-B85-C10-D37
A24-B85-C10-D37
A69-B85-C10-D37
A67-B85-C10-D37
A39-B85-C10-D37
A65-B85-C10-D37
A66-B85-C10-D37
A2-B86-C10-D37
A3-B86-C10-D37
A9-B86-C10-D37
A13-B86-C10-D37
A24-B86-C10-D37
A69-B86-C10-D37
A67-B86-C10-D37
A39-B86-C10-D37
A65-B86-C10-D37
A66-B86-C10-D37
A2-B87-C10-D37
A3-B87-C10-D37
A9-B87-C10-D37
A13-B87-C10-D37
A24-B87-C10-D37
A69-B87-C10-D37
A67-B87-C10-D37
A39-B87-C10-D37
A65-B87-C10-D37
A66-B87-C10-D37
A2-B89-C10-D37
A3-B89-C10-D37
A9-B89-C10-D37
A13-B89-C10-D37
A24-B89-C10-D37
A69-B89-C10-D37
A67-B89-C10-D37
A39-B89-C10-D37
A65-B89-C10-D37
A66-B89-C10-D37
A2-B92-C10-D37
A3-B92-C10-D37
A9-B92-C10-D37
A13-B92-C10-D37
A24-B92-C10-D37
A69-B92-C10-D37
A67-B92-C10-D37
A39-B92-C10-D37
A65-B92-C10-D37
A66-B92-C10-D37
A2-B4-C11-D37
A3-B4-C11-D37
A9-B4-C11-D37
A13-B4-C11-D37
A24-B4-C11-D37
A69-B4-C11-D37
A67-B4-C11-D37
A39-B4-C11-D37
A65-B4-C11-D37
A66-B4-C11-D37
A2-B5-C11-D37
A3-B5-C11-D37
A9-B5-C11-D37
A13-B5-C11-D37
A24-B5-C11-D37
A69-B5-C11-D37
A67-B5-C11-D37
A39-B5-C11-D37
A65-B5-C11-D37
A66-B5-C11-D37
A2-B6-C11-D37
A3-B6-C11-D37
A9-B6-C11-D37
A13-B6-C11-D37
A24-B6-C11-D37
A69-B6-C11-D37
A67-B6-C11-D37

-continued

A39-B6-C11-D37
A65-B6-C11-D37
A66-B6-C11-D37
A2-B32-C11-D37
A3-B32-C11-D37
A9-B32-C11-D37
A13-B32-C11-D37
A24-B32-C11-D37
A69-B32-C11-D37
A67-B32-C11-D37
A39-B32-C11-D37
A65-B32-C11-D37
A66-B32-C11-D37
A2-B39-C11-D37
A3-B39-C11-D37
A9-B39-C11-D37
A13-B39-C11-D37
A24-B39-C11-D37
A69-B39-C11-D37
A67-B39-C11-D37
A39-B39-C11-D37
A65-B39-C11-D37
A66-B39-C11-D37
A2-B45-C11-D37
A3-B45-C11-D37
A9-B45-C11-D37
A13-B45-C11-D37
A24-B45-C11-D37
A69-B45-C11-D37
A67-B45-C11-D37
A39-B45-C11-D37
A65-B45-C11-D37
A66-B45-C11-D37
A2-B53-C11-D37
A3-B53-C11-D37
A9-B53-C11-D37
A13-B53-C11-D37
A24-B53-C11-D37
A69-B53-C11-D37
A67-B53-C11-D37
A39-B53-C11-D37
A65-B53-C11-D37
A66-B53-C11-D37
A2-B79-C11-D37
A3-B79-C11-D37
A9-B79-C11-D37
A13-B79-C11-D37
A24-B79-C11-D37
A69-B79-C11-D37
A67-B79-C11-D37
A39-B79-C11-D37
A65-B79-C11-D37
A66-B79-C11-D37
A2-B80-C11-D37
A3-B80-C11-D37
A9-B80-C11-D37
A13-B80-C11-D37
A24-B80-C11-D37
A69-B80-C11-D37
A67-B80-C11-D37
A39-B80-C11-D37
A65-B80-C11-D37
A66-B80-C11-D37
A2-B85-C11-D37
A3-B85-C11-D37
A9-B85-C11-D37
A13-B85-C11-D37
A24-B85-C11-D37
A69-B85-C11-D37
A67-B85-C11-D37
A39-B85-C11-D37
A65-B85-C11-D37
A66-B85-C11-D37
A2-B86-C11-D37
A3-B86-C11-D37
A9-B86-C11-D37
A13-B86-C11-D37
A24-B86-C11-D37
A69-B86-C11-D37
A67-B86-C11-D37

-continued

A39-B86-C11-D37
A65-B86-C11-D37
A66-B86-C11-D37
A2-B87-C11-D37
A3-B87-C11-D37
A9-B87-C11-D37
A13-B87-C11-D37
A24-B87-C11-D37
A69-B87-C11-D37
A67-B87-C11-D37
A39-B87-C11-D37
A65-B87-C11-D37
A66-B87-C11-D37
A2-B89-C11-D37
A3-B89-C11-D37
A9-B89-C11-D37
A13-B89-C11-D37
A24-B89-C11-D37
A69-B89-C11-D37
A67-B89-C11-D37
A39-B89-C11-D37
A65-B89-C11-D37
A66-B89-C11-D37
A2-B92-C11-D37
A3-B92-C11-D37
A9-B92-C11-D37
A13-B92-C11-D37
A24-B92-C11-D37
A69-B92-C11-D37
A67-B92-C11-D37
A39-B92-C11-D37
A65-B92-C11-D37
A66-B92-C11-D37
A2-B4-C12-D37
A3-B4-C12-D37
A9-B4-C12-D37
A13-B4-C12-D37
A24-B4-C12-D37
A69-B4-C12-D37
A67-B4-C12-D37
A39-B4-C12-D37
A65-B4-C12-D37
A66-B4-C12-D37
A2-B5-C12-D37
A3-B5-C12-D37
A9-B5-C12-D37
A13-B5-C12-D37
A24-B5-C12-D37
A69-B5-C12-D37
A67-B5-C12-D37
A39-B5-C12-D37
A65-B5-C12-D37
A66-B5-C12-D37
A2-B6-C12-D37
A3-B6-C12-D37
A9-B6-C12-D37
A13-B6-C12-D37
A24-B6-C12-D37
A69-B6-C12-D37
A67-B6-C12-D37
A39-B6-C12-D37
A65-B6-C12-D37
A66-B6-C12-D37
A2-B32-C12-D37
A3-B32-C12-D37
A9-B32-C12-D37
A13-B32-C12-D37
A24-B32-C12-D37
A69-B32-C12-D37
A67-B32-C12-D37
A39-B32-C12-D37
A65-B32-C12-D37
A66-B32-C12-D37
A2-B39-C12-D37
A3-B39-C12-D37
A9-B39-C12-D37
A13-B39-C12-D37
A24-B39-C12-D37
A69-B39-C12-D37
A67-B39-C12-D37

-continued
A39-B39-C12-D37
A65-B39-C12-D37
A66-B39-C12-D37
A2-B45-C12-D37
A3-B45-C12-D37
A9-B45-C12-D37
A13-B45-C12-D37
A24-B45-C12-D37
A69-B45-C12-D37
A67-B45-C12-D37
A39-B45-C12-D37
A65-B45-C12-D37
A66-B45-C12-D37
A2-B53-C12-D37
A3-B53-C12-D37
A9-B53-C12-D37
A13-B53-C12-D37
A24-B53-C12-D37
A69-B53-C12-D37
A67-B53-C12-D37
A39-B53-C12-D37
A65-B53-C12-D37
A66-B53-C12-D37
A2-B79-C12-D37
A3-B79-C12-D37
A9-B79-C12-D37
A13-B79-C12-D37
A24-B79-C12-D37
A69-B79-C12-D37
A67-B79-C12-D37
A39-B79-C12-D37
A65-B79-C12-D37
A66-B79-C12-D37
A2-B80-C12-D37
A3-B80-C12-D37
A9-B80-C12-D37
A13-B80-C12-D37
A24-B80-C12-D37
A69-B80-C12-D37
A67-B80-C12-D37
A39-B80-C12-D37
A65-B80-C12-D37
A66-B80-C12-D37
A2-B85-C12-D37
A3-B85-C12-D37
A9-B85-C12-D37
A13-B85-C12-D37
A24-B85-C12-D37
A69-B85-C12-D37
A67-B85-C12-D37
A39-B85-C12-D37
A65-B85-C12-D37
A66-B85-C12-D37
A2-B86-C12-D37
A3-B86-C12-D37
A9-B86-C12-D37
A13-B86-C12-D37
A24-B86-C12-D37
A69-B86-C12-D37
A67-B86-C12-D37
A39-B86-C12-D37
A65-B86-C12-D37
A66-B86-C12-D37
A2-B87-C12-D37
A3-B87-C12-D37
A9-B87-C12-D37
A13-B87-C12-D37
A24-B87-C12-D37
A69-B87-C12-D37
A67-B87-C12-D37
A39-B87-C12-D37
A65-B87-C12-D37
A66-B87-C12-D37
A2-B89-C12-D37
A3-B89-C12-D37
A9-B89-C12-D37
A13-B89-C12-D37
A24-B89-C12-D37
A69-B89-C12-D37
A67-B89-C12-D37

-continued
A39-B89-C12-D37
A65-B89-C12-D37
A66-B89-C12-D37
A2-B92-C12-D37
A3-B92-C12-D37
A9-B92-C12-D37
A13-B92-C12-D37
A24-B92-C12-D37
A69-B92-C12-D37
A67-B92-C12-D37
A39-B92-C12-D37
A65-B92-C12-D37
A66-B92-C12-D37
A2-B4-C13-D37
A3-B4-C13-D37
A9-B4-C13-D37
A13-B4-C13-D37
A24-B4-C13-D37
A69-B4-C13-D37
A67-B4-C13-D37
A39-B4-C13-D37
A65-B4-C13-D37
A66-B4-C13-D37
A2-B5-C13-D37
A3-B5-C13-D37
A9-B5-C13-D37
A13-B5-C13-D37
A24-B5-C13-D37
A69-B5-C13-D37
A67-B5-C13-D37
A39-B5-C13-D37
A65-B5-C13-D37
A66-B5-C13-D37
A2-B6-C13-D37
A3-B6-C13-D37
A9-B6-C13-D37
A13-B6-C13-D37
A24-B6-C13-D37
A69-B6-C13-D37
A67-B6-C13-D37
A39-B6-C13-D37
A65-B6-C13-D37
A66-B6-C13-D37
A2-B32-C13-D37
A3-B32-C13-D37
A9-B32-C13-D37
A13-B32-C13-D37
A24-B32-C13-D37
A69-B32-C13-D37
A67-B32-C13-D37
A39-B32-C13-D37
A65-B32-C13-D37
A66-B32-C13-D37
A2-B39-C13-D37
A3-B39-C13-D37
A9-B39-C13-D37
A13-B39-C13-D37
A24-B39-C13-D37
A69-B39-C13-D37
A67-B39-C13-D37
A39-B39-C13-D37
A65-B39-C13-D37
A66-B39-C13-D37
A2-B45-C13-D37
A3-B45-C13-D37
A9-B45-C13-D37
A13-B45-C13-D37
A24-B45-C13-D37
A69-B45-C13-D37
A67-B45-C13-D37
A39-B45-C13-D37
A65-B45-C13-D37
A66-B45-C13-D37
A2-B53-C13-D37
A3-B53-C13-D37
A9-B53-C13-D37
A13-B53-C13-D37
A24-B53-C13-D37
A69-B53-C13-D37
A67-B53-C13-D37

-continued

A39-B53-C13-D37
A65-B53-C13-D37
A66-B53-C13-D37
A2-B79-C13-D37
A3-B79-C13-D37
A9-B79-C13-D37
A13-B79-C13-D37
A24-B79-C13-D37
A69-B79-C13-D37
A67-B79-C13-D37
A39-B79-C13-D37
A65-B79-C13-D37
A66-B79-C13-D37
A2-B80-C13-D37
A3-B80-C13-D37
A9-B80-C13-D37
A13-B80-C13-D37
A24-B80-C13-D37
A69-B80-C13-D37
A67-B80-C13-D37
A39-B80-C13-D37
A65-B80-C13-D37
A66-B80-C13-D37
A2-B85-C13-D37
A3-B85-C13-D37
A9-B85-C13-D37
A13-B85-C13-D37
A24-B85-C13-D37
A69-B85-C13-D37
A67-B85-C13-D37
A39-B85-C13-D37
A65-B85-C13-D37
A66-B85-C13-D37
A2-B86-C13-D37
A3-B86-C13-D37
A9-B86-C13-D37
A13-B86-C13-D37
A24-B86-C13-D37
A69-B86-C13-D37
A67-B86-C13-D37
A39-B86-C13-D37
A65-B86-C13-D37
A66-B86-C13-D37
A2-B87-C13-D37
A3-B87-C13-D37
A9-B87-C13-D37
A13-B87-C13-D37
A24-B87-C13-D37
A69-B87-C13-D37
A67-B87-C13-D37
A39-B87-C13-D37
A65-B87-C13-D37
A66-B87-C13-D37
A2-B89-C13-D37
A3-B89-C13-D37
A9-B89-C13-D37
A13-B89-C13-D37
A24-B89-C13-D37
A69-B89-C13-D37
A67-B89-C13-D37
A39-B89-C13-D37
A65-B89-C13-D37
A66-B89-C13-D37
A2-B92-C13-D37
A3-B92-C13-D37
A9-B92-C13-D37
A13-B92-C13-D37
A24-B92-C13-D37
A69-B92-C13-D37
A67-B92-C13-D37
A39-B92-C13-D37
A65-B92-C13-D37
A66-B92-C13-D37
A2-B4-C1-D38
A3-B4-C1-D38
A9-B4-C1-D38
A13-B4-C1-D38
A24-B4-C1-D38
A69-B4-C1-D38
A67-B4-C1-D38

-continued

A39-B4-C1-D38
A65-B4-C1-D38
A66-B4-C1-D38
A2-B5-C1-D38
A3-B5-C1-D38
A9-B5-C1-D38
A13-B5-C1-D38
A24-B5-C1-D38
A69-B5-C1-D38
A67-B5-C1-D38
A39-B5-C1-D38
A65-B5-C1-D38
A66-B5-C1-D38
A2-B6-C1-D38
A3-B6-C1-D38
A9-B6-C1-D38
A13-B6-C1-D38
A24-B6-C1-D38
A69-B6-C1-D38
A67-B6-C1-D38
A39-B6-C1-D38
A65-B6-C1-D38
A66-B6-C1-D38
A2-B32-C1-D38
A3-B32-C1-D38
A9-B32-C1-D38
A13-B32-C1-D38
A24-B32-C1-D38
A69-B32-C1-D38
A67-B32-C1-D38
A39-B32-C1-D38
A65-B32-C1-D38
A66-B32-C1-D38
A2-B39-C1-D38
A3-B39-C1-D38
A9-B39-C1-D38
A13-B39-C1-D38
A24-B39-C1-D38
A69-B39-C1-D38
A67-B39-C1-D38
A39-B39-C1-D38
A65-B39-C1-D38
A66-B39-C1-D38
A2-B45-C1-D38
A3-B45-C1-D38
A9-B45-C1-D38
A13-B45-C1-D38
A24-B45-C1-D38
A69-B45-C1-D38
A67-B45-C1-D38
A39-B45-C1-D38
A65-B45-C1-D38
A66-B45-C1-D38
A2-B53-C1-D38
A3-B53-C1-D38
A9-B53-C1-D38
A13-B53-C1-D38
A24-B53-C1-D38
A69-B53-C1-D38
A67-B53-C1-D38
A39-B53-C1-D38
A65-B53-C1-D38
A66-B53-C1-D38
A2-B79-C1-D38
A3-B79-C1-D38
A9-B79-C1-D38
A13-B79-C1-D38
A24-B79-C1-D38
A69-B79-C1-D38
A67-B79-C1-D38
A39-B79-C1-D38
A65-B79-C1-D38
A66-B79-C1-D38
A2-B80-C1-D38
A3-B80-C1-D38
A9-B80-C1-D38
A13-B80-C1-D38
A24-B80-C1-D38
A69-B80-C1-D38
A67-B80-C1-D38

-continued

A39-B80-C1-D38
A65-B80-C1-D38
A66-B80-C1-D38
A2-B85-C1-D38
A3-B85-C1-D38
A9-B85-C1-D38
A13-B85-C1-D38
A24-B85-C1-D38
A69-B85-C1-D38
A67-B85-C1-D38
A39-B85-C1-D38
A65-B85-C1-D38
A66-B85-C1-D38
A2-B86-C1-D38
A3-B86-C1-D38
A9-B86-C1-D38
A13-B86-C1-D38
A24-B86-C1-D38
A69-B86-C1-D38
A67-B86-C1-D38
A39-B86-C1-D38
A65-B86-C1-D38
A66-B86-C1-D38
A2-B87-C1-D38
A3-B87-C1-D38
A9-B87-C1-D38
A13-B87-C1-D38
A24-B87-C1-D38
A69-B87-C1-D38
A67-B87-C1-D38
A39-B87-C1-D38
A65-B87-C1-D38
A66-B87-C1-D38
A2-B89-C1-D38
A3-B89-C1-D38
A9-B89-C1-D38
A13-B89-C1-D38
A24-B89-C1-D38
A69-B89-C1-D38
A67-B89-C1-D38
A39-B89-C1-D38
A65-B89-C1-D38
A66-B89-C1-D38
A2-B92-C1-D38
A3-B92-C1-D38
A9-B92-C1-D38
A13-B92-C1-D38
A24-B92-C1-D38
A69-B92-C1-D38
A67-B92-C1-D38
A39-B92-C1-D38
A65-B92-C1-D38
A66-B92-C1-D38
A2-B4-C2-D38
A3-B4-C2-D38
A9-B4-C2-D38
A13-B4-C2-D38
A24-B4-C2-D38
A69-B4-C2-D38
A67-B4-C2-D38
A39-B4-C2-D38
A65-B4-C2-D38
A66-B4-C2-D38
A2-B5-C2-D38
A3-B5-C2-D38
A9-B5-C2-D38
A13-B5-C2-D38
A24-B5-C2-D38
A69-B5-C2-D38
A67-B5-C2-D38
A39-B5-C2-D38
A65-B5-C2-D38
A66-B5-C2-D38
A2-B6-C2-D38
A3-B6-C2-D38
A9-B6-C2-D38
A13-B6-C2-D38
A24-B6-C2-D38
A69-B6-C2-D38
A67-B6-C2-D38

-continued

A39-B6-C2-D38
A65-B6-C2-D38
A66-B6-C2-D38
A2-B32-C2-D38
A3-B32-C2-D38
A9-B32-C2-D38
A13-B32-C2-D38
A24-B32-C2-D38
A69-B32-C2-D38
A67-B32-C2-D38
A39-B32-C2-D38
A65-B32-C2-D38
A66-B32-C2-D38
A2-B39-C2-D38
A3-B39-C2-D38
A9-B39-C2-D38
A13-B39-C2-D38
A24-B39-C2-D38
A69-B39-C2-D38
A67-B39-C2-D38
A39-B39-C2-D38
A65-B39-C2-D38
A66-B39-C2-D38
A2-B45-C2-D38
A3-B45-C2-D38
A9-B45-C2-D38
A13-B45-C2-D38
A24-B45-C2-D38
A69-B45-C2-D38
A67-B45-C2-D38
A39-B45-C2-D38
A65-B45-C2-D38
A66-B45-C2-D38
A2-B53-C2-D38
A3-B53-C2-D38
A9-B53-C2-D38
A13-B53-C2-D38
A24-B53-C2-D38
A69-B53-C2-D38
A67-B53-C2-D38
A39-B53-C2-D38
A65-B53-C2-D38
A66-B53-C2-D38
A2-B79-C2-D38
A3-B79-C2-D38
A9-B79-C2-D38
A13-B79-C2-D38
A24-B79-C2-D38
A69-B79-C2-D38
A67-B79-C2-D38
A39-B79-C2-D38
A65-B79-C2-D38
A66-B79-C2-D38
A2-B80-C2-D38
A3-B80-C2-D38
A9-B80-C2-D38
A13-B80-C2-D38
A24-B80-C2-D38
A69-B80-C2-D38
A67-B80-C2-D38
A39-B80-C2-D38
A65-B80-C2-D38
A66-B80-C2-D38
A2-B85-C2-D38
A3-B85-C2-D38
A9-B85-C2-D38
A13-B85-C2-D38
A24-B85-C2-D38
A69-B85-C2-D38
A67-B85-C2-D38
A39-B85-C2-D38
A65-B85-C2-D38
A66-B85-C2-D38
A2-B86-C2-D38
A3-B86-C2-D38
A9-B86-C2-D38
A13-B86-C2-D38
A24-B86-C2-D38
A69-B86-C2-D38
A67-B86-C2-D38

-continued
A39-B86-C2-D38
A65-B86-C2-D38
A66-B86-C2-D38
A2-B87-C2-D38
A3-B87-C2-D38
A9-B87-C2-D38
A13-B87-C2-D38
A24-B87-C2-D38
A69-B87-C2-D38
A67-B87-C2-D38
A39-B87-C2-D38
A65-B87-C2-D38
A66-B87-C2-D38
A2-B89-C2-D38
A3-B89-C2-D38
A9-B89-C2-D38
A13-B89-C2-D38
A24-B89-C2-D38
A69-B89-C2-D38
A67-B89-C2-D38
A39-B89-C2-D38
A65-B89-C2-D38
A66-B89-C2-D38
A2-B92-C2-D38
A3-B92-C2-D38
A9-B92-C2-D38
A13-B92-C2-D38
A24-B92-C2-D38
A69-B92-C2-D38
A67-B92-C2-D38
A39-B92-C2-D38
A65-B92-C2-D38
A66-B92-C2-D38
A2-B4-C3-D38
A3-B4-C3-D38
A9-B4-C3-D38
A13-B4-C3-D38
A24-B4-C3-D38
A69-B4-C3-D38
A67-B4-C3-D38
A39-B4-C3-D38
A65-B4-C3-D38
A66-B4-C3-D38
A2-B5-C3-D38
A3-B5-C3-D38
A9-B5-C3-D38
A13-B5-C3-D38
A24-B5-C3-D38
A69-B5-C3-D38
A67-B5-C3-D38
A39-B5-C3-D38
A65-B5-C3-D38
A66-B5-C3-D38
A2-B6-C3-D38
A3-B6-C3-D38
A9-B6-C3-D38
A13-B6-C3-D38
A24-B6-C3-D38
A69-B6-C3-D38
A67-B6-C3-D38
A39-B6-C3-D38
A65-B6-C3-D38
A66-B6-C3-D38
A2-B32-C3-D38
A3-B32-C3-D38
A9-B32-C3-D38
A13-B32-C3-D38
A24-B32-C3-D38
A69-B32-C3-D38
A67-B32-C3-D38
A39-B32-C3-D38
A65-B32-C3-D38
A66-B32-C3-D38
A2-B39-C3-D38
A3-B39-C3-D38
A9-B39-C3-D38
A13-B39-C3-D38
A24-B39-C3-D38
A69-B39-C3-D38
A67-B39-C3-D38

-continued
A39-B39-C3-D38
A65-B39-C3-D38
A66-B39-C3-D38
A2-B45-C3-D38
A3-B45-C3-D38
A9-B45-C3-D38
A13-B45-C3-D38
A24-B45-C3-D38
A69-B45-C3-D38
A67-B45-C3-D38
A39-B45-C3-D38
A65-B45-C3-D38
A66-B45-C3-D38
A2-B53-C3-D38
A3-B53-C3-D38
A9-B53-C3-D38
A13-B53-C3-D38
A24-B53-C3-D38
A69-B53-C3-D38
A67-B53-C3-D38
A39-B53-C3-D38
A65-B53-C3-D38
A66-B53-C3-D38
A2-B79-C3-D38
A3-B79-C3-D38
A9-B79-C3-D38
A13-B79-C3-D38
A24-B79-C3-D38
A69-B79-C3-D38
A67-B79-C3-D38
A39-B79-C3-D38
A65-B79-C3-D38
A66-B79-C3-D38
A2-B80-C3-D38
A3-B80-C3-D38
A9-B80-C3-D38
A13-B80-C3-D38
A24-B80-C3-D38
A69-B80-C3-D38
A67-B80-C3-D38
A39-B80-C3-D38
A65-B80-C3-D38
A66-B80-C3-D38
A2-B85-C3-D38
A3-B85-C3-D38
A9-B85-C3-D38
A13-B85-C3-D38
A24-B85-C3-D38
A69-B85-C3-D38
A67-B85-C3-D38
A39-B85-C3-D38
A65-B85-C3-D38
A66-B85-C3-D38
A2-B86-C3-D38
A3-B86-C3-D38
A9-B86-C3-D38
A13-B86-C3-D38
A24-B86-C3-D38
A69-B86-C3-D38
A67-B86-C3-D38
A39-B86-C3-D38
A65-B86-C3-D38
A66-B86-C3-D38
A2-B87-C3-D38
A3-B87-C3-D38
A9-B87-C3-D38
A13-B87-C3-D38
A24-B87-C3-D38
A69-B87-C3-D38
A67-B87-C3-D38
A39-B87-C3-D38
A65-B87-C3-D38
A66-B87-C3-D38
A2-B89-C3-D38
A3-B89-C3-D38
A9-B89-C3-D38
A13-B89-C3-D38
A24-B89-C3-D38
A69-B89-C3-D38
A67-B89-C3-D38

-continued

A39-B89-C3-D38
A65-B89-C3-D38
A66-B89-C3-D38
A2-B92-C3-D38
A3-B92-C3-D38
A9-B92-C3-D38
A13-B92-C3-D38
A24-B92-C3-D38
A69-B92-C3-D38
A67-B92-C3-D38
A39-B92-C3-D38
A65-B92-C3-D38
A66-B92-C3-D38
A2-B4-C4-D38
A3-B4-C4-D38
A9-B4-C4-D38
A13-B4-C4-D38
A24-B4-C4-D38
A69-B4-C4-D38
A67-B4-C4-D38
A39-B4-C4-D38
A65-B4-C4-D38
A66-B4-C4-D38
A2-B5-C4-D38
A3-B5-C4-D38
A9-B5-C4-D38
A13-B5-C4-D38
A24-B5-C4-D38
A69-B5-C4-D38
A67-B5-C4-D38
A39-B5-C4-D38
A65-B5-C4-D38
A66-B5-C4-D38
A2-B6-C4-D38
A3-B6-C4-D38
A9-B6-C4-D38
A13-B6-C4-D38
A24-B6-C4-D38
A69-B6-C4-D38
A67-B6-C4-D38
A39-B6-C4-D38
A65-B6-C4-D38
A66-B6-C4-D38
A2-B32-C4-D38
A3-B32-C4-D38
A9-B32-C4-D38
A13-B32-C4-D38
A24-B32-C4-D38
A69-B32-C4-D38
A67-B32-C4-D38
A39-B32-C4-D38
A65-B32-C4-D38
A66-B32-C4-D38
A2-B39-C4-D38
A3-B39-C4-D38
A9-B39-C4-D38
A13-B39-C4-D38
A24-B39-C4-D38
A69-B39-C4-D38
A67-B39-C4-D38
A39-B39-C4-D38
A65-B39-C4-D38
A66-B39-C4-D38
A2-B45-C4-D38
A3-B45-C4-D38
A9-B45-C4-D38
A13-B45-C4-D38
A24-B45-C4-D38
A69-B45-C4-D38
A67-B45-C4-D38
A39-B45-C4-D38
A65-B45-C4-D38
A66-B45-C4-D38
A2-B53-C4-D38
A3-B53-C4-D38
A9-B53-C4-D38
A13-B53-C4-D38
A24-B53-C4-D38
A69-B53-C4-D38
A67-B53-C4-D38

-continued

A39-B53-C4-D38
A65-B53-C4-D38
A66-B53-C4-D38
A2-B79-C4-D38
A3-B79-C4-D38
A9-B79-C4-D38
A13-B79-C4-D38
A24-B79-C4-D38
A69-B79-C4-D38
A67-B79-C4-D38
A39-B79-C4-D38
A65-B79-C4-D38
A66-B79-C4-D38
A2-B80-C4-D38
A3-B80-C4-D38
A9-B80-C4-D38
A13-B80-C4-D38
A24-B80-C4-D38
A69-B80-C4-D38
A67-B80-C4-D38
A39-B80-C4-D38
A65-B80-C4-D38
A66-B80-C4-D38
A2-B85-C4-D38
A3-B85-C4-D38
A9-B85-C4-D38
A13-B85-C4-D38
A24-B85-C4-D38
A69-B85-C4-D38
A67-B85-C4-D38
A39-B85-C4-D38
A65-B85-C4-D38
A66-B85-C4-D38
A2-B86-C4-D38
A3-B86-C4-D38
A9-B86-C4-D38
A13-B86-C4-D38
A24-B86-C4-D38
A69-B86-C4-D38
A67-B86-C4-D38
A39-B86-C4-D38
A65-B86-C4-D38
A66-B86-C4-D38
A2-B87-C4-D38
A3-B87-C4-D38
A9-B87-C4-D38
A13-B87-C4-D38
A24-B87-C4-D38
A69-B87-C4-D38
A67-B87-C4-D38
A39-B87-C4-D38
A65-B87-C4-D38
A66-B87-C4-D38
A2-B89-C4-D38
A3-B89-C4-D38
A9-B89-C4-D38
A13-B89-C4-D38
A24-B89-C4-D38
A69-B89-C4-D38
A67-B89-C4-D38
A39-B89-C4-D38
A65-B89-C4-D38
A66-B89-C4-D38
A2-B92-C4-D38
A3-B92-C4-D38
A9-B92-C4-D38
A13-B92-C4-D38
A24-B92-C4-D38
A69-B92-C4-D38
A67-B92-C4-D38
A39-B92-C4-D38
A65-B92-C4-D38
A66-B92-C4-D38
A2-B4-C5-D38
A3-B4-C5-D38
A9-B4-C5-D38
A13-B4-C5-D38
A24-B4-C5-D38
A69-B4-C5-D38
A67-B4-C5-D38

-continued
A39-B4-C5-D38
A65-B4-C5-D38
A66-B4-C5-D38
A2-B5-C5-D38
A3-B5-C5-D38
A9-B5-C5-D38
A13-B5-C5-D38
A24-B5-C5-D38
A69-B5-C5-D38
A67-B5-C5-D38
A39-B5-C5-D38
A65-B5-C5-D38
A66-B5-C5-D38
A2-B6-C5-D38
A3-B6-C5-D38
A9-B6-C5-D38
A13-B6-C5-D38
A24-B6-C5-D38
A69-B6-C5-D38
A67-B6-C5-D38
A39-B6-C5-D38
A65-B6-C5-D38
A66-B6-C5-D38
A2-B32-C5-D38
A3-B32-C5-D38
A9-B32-C5-D38
A13-B32-C5-D38
A24-B32-C5-D38
A69-B32-C5-D38
A67-B32-C5-D38
A39-B32-C5-D38
A65-B32-C5-D38
A66-B32-C5-D38
A2-B39-C5-D38
A3-B39-C5-D38
A9-B39-C5-D38
A13-B39-C5-D38
A24-B39-C5-D38
A69-B39-C5-D38
A67-B39-C5-D38
A39-B39-C5-D38
A65-B39-C5-D38
A66-B39-C5-D38
A2-B45-C5-D38
A3-B45-C5-D38
A9-B45-C5-D38
A13-B45-C5-D38
A24-B45-C5-D38
A69-B45-C5-D38
A67-B45-C5-D38
A39-B45-C5-D38
A65-B45-C5-D38
A66-B45-C5-D38
A2-B53-C5-D38
A3-B53-C5-D38
A9-B53-C5-D38
A13-B53-C5-D38
A24-B53-C5-D38
A69-B53-C5-D38
A67-B53-C5-D38
A39-B53-C5-D38
A65-B53-C5-D38
A66-B53-C5-D38
A2-B79-C5-D38
A3-B79-C5-D38
A9-B79-C5-D38
A13-B79-C5-D38
A24-B79-C5-D38
A69-B79-C5-D38
A67-B79-C5-D38
A39-B79-C5-D38
A65-B79-C5-D38
A66-B79-C5-D38
A2-B80-C5-D38
A3-B80-C5-D38
A9-B80-C5-D38
A13-B80-C5-D38
A24-B80-C5-D38
A69-B80-C5-D38
A67-B80-C5-D38

-continued
A39-B80-C5-D38
A65-B80-C5-D38
A66-B80-C5-D38
A2-B85-C5-D38
A3-B85-C5-D38
A9-B85-C5-D38
A13-B85-C5-D38
A24-B85-C5-D38
A69-B85-C5-D38
A67-B85-C5-D38
A39-B85-C5-D38
A65-B85-C5-D38
A66-B85-C5-D38
A2-B86-C5-D38
A3-B86-C5-D38
A9-B86-C5-D38
A13-B86-C5-D38
A24-B86-C5-D38
A69-B86-C5-D38
A67-B86-C5-D38
A39-B86-C5-D38
A65-B86-C5-D38
A66-B86-C5-D38
A2-B87-C5-D38
A3-B87-C5-D38
A9-B87-C5-D38
A13-B87-C5-D38
A24-B87-C5-D38
A69-B87-C5-D38
A67-B87-C5-D38
A39-B87-C5-D38
A65-B87-C5-D38
A66-B87-C5-D38
A2-B89-C5-D38
A3-B89-C5-D38
A9-B89-C5-D38
A13-B89-C5-D38
A24-B89-C5-D38
A69-B89-C5-D38
A67-B89-C5-D38
A39-B89-C5-D38
A65-B89-C5-D38
A66-B89-C5-D38
A2-B92-C5-D38
A3-B92-C5-D38
A9-B92-C5-D38
A13-B92-C5-D38
A24-B92-C5-D38
A69-B92-C5-D38
A67-B92-C5-D38
A39-B92-C5-D38
A65-B92-C5-D38
A66-B92-C5-D38
A2-B4-C6-D38
A3-B4-C6-D38
A9-B4-C6-D38
A13-B4-C6-D38
A24-B4-C6-D38
A69-B4-C6-D38
A67-B4-C6-D38
A39-B4-C6-D38
A65-B4-C6-D38
A66-B4-C6-D38
A2-B5-C6-D38
A3-B5-C6-D38
A9-B5-C6-D38
A13-B5-C6-D38
A24-B5-C6-D38
A69-B5-C6-D38
A67-B5-C6-D38
A39-B5-C6-D38
A65-B5-C6-D38
A66-B5-C6-D38
A2-B6-C6-D38
A3-B6-C6-D38
A9-B6-C6-D38
A13-B6-C6-D38
A24-B6-C6-D38
A69-B6-C6-D38
A67-B6-C6-D38

-continued
A39-B6-C6-D38
A65-B6-C6-D38
A66-B6-C6-D38
A2-B32-C6-D38
A3-B32-C6-D38
A9-B32-C6-D38
A13-B32-C6-D38
A24-B32-C6-D38
A69-B32-C6-D38
A67-B32-C6-D38
A39-B32-C6-D38
A65-B32-C6-D38
A66-B32-C6-D38
A2-B39-C6-D38
A3-B39-C6-D38
A9-B39-C6-D38
A13-B39-C6-D38
A24-B39-C6-D38
A69-B39-C6-D38
A67-B39-C6-D38
A39-B39-C6-D38
A65-B39-C6-D38
A66-B39-C6-D38
A2-B45-C6-D38
A3-B45-C6-D38
A9-B45-C6-D38
A13-B45-C6-D38
A24-B45-C6-D38
A69-B45-C6-D38
A67-B45-C6-D38
A39-B45-C6-D38
A65-B45-C6-D38
A66-B45-C6-D38
A2-B53-C6-D38
A3-B53-C6-D38
A9-B53-C6-D38
A13-B53-C6-D38
A24-B53-C6-D38
A69-B53-C6-D38
A67-B53-C6-D38
A39-B53-C6-D38
A65-B53-C6-D38
A66-B53-C6-D38
A2-B79-C6-D38
A3-B79-C6-D38
A9-B79-C6-D38
A13-B79-C6-D38
A24-B79-C6-D38
A69-B79-C6-D38
A67-B79-C6-D38
A39-B79-C6-D38
A65-B79-C6-D38
A66-B79-C6-D38
A2-B80-C6-D38
A3-B80-C6-D38
A9-B80-C6-D38
A13-B80-C6-D38
A24-B80-C6-D38
A69-B80-C6-D38
A67-B80-C6-D38
A39-B80-C6-D38
A65-B80-C6-D38
A66-B80-C6-D38
A2-B85-C6-D38
A3-B85-C6-D38
A9-B85-C6-D38
A13-B85-C6-D38
A24-B85-C6-D38
A69-B85-C6-D38
A67-B85-C6-D38
A39-B85-C6-D38
A65-B85-C6-D38
A66-B85-C6-D38
A2-B86-C6-D38
A3-B86-C6-D38
A9-B86-C6-D38
A13-B86-C6-D38
A24-B86-C6-D38
A69-B86-C6-D38
A67-B86-C6-D38

-continued
A39-B86-C6-D38
A65-B86-C6-D38
A66-B86-C6-D38
A2-B87-C6-D38
A3-B87-C6-D38
A9-B87-C6-D38
A13-B87-C6-D38
A24-B87-C6-D38
A69-B87-C6-D38
A67-B87-C6-D38
A39-B87-C6-D38
A65-B87-C6-D38
A66-B87-C6-D38
A2-B89-C6-D38
A3-B89-C6-D38
A9-B89-C6-D38
A13-B89-C6-D38
A24-B89-C6-D38
A69-B89-C6-D38
A67-B89-C6-D38
A39-B89-C6-D38
A65-B89-C6-D38
A66-B89-C6-D38
A2-B92-C6-D38
A3-B92-C6-D38
A9-B92-C6-D38
A13-B92-C6-D38
A24-B92-C6-D38
A69-B92-C6-D38
A67-B92-C6-D38
A39-B92-C6-D38
A65-B92-C6-D38
A66-B92-C6-D38
A2-B4-C7-D38
A3-B4-C7-D38
A9-B4-C7-D38
A13-B4-C7-D38
A24-B4-C7-D38
A69-B4-C7-D38
A67-B4-C7-D38
A39-B4-C7-D38
A65-B4-C7-D38
A66-B4-C7-D38
A2-B5-C7-D38
A3-B5-C7-D382
A9-B5-C7-D38
A13-B5-C7-D38
A24-B5-C7-D38
A69-B5-C7-D38
A67-B5-C7-D38
A39-B5-C7-D38
A65-B5-C7-D38
A66-B5-C7-D38
A2-B6-C7-D38
A3-B6-C7-D38
A9-B6-C7-D38
A13-B6-C7-D38
A24-B6-C7-D38
A69-B6-C7-D38
A67-B6-C7-D38
A39-B6-C7-D38
A65-B6-C7-D38
A66-B6-C7-D38
A2-B32-C7-D38
A3-B32-C7-D38
A9-B32-C7-D38
A13-B32-C7-D38
A24-B32-C7-D38
A69-B32-C7-D38
A67-B32-C7-D38
A39-B32-C7-D38
A65-B32-C7-D38
A66-B32-C7-D38
A2-B39-C7-D38
A3-B39-C7-D38
A9-B39-C7-D38
A13-B39-C7-D38
A24-B39-C7-D38
A69-B39-C7-D38
A67-B39-C7-D38

-continued
A39-B39-C7-D38
A65-B39-C7-D38
A66-B39-C7-D38
A2-B45-C7-D38
A3-B45-C7-D38
A9-B45-C7-D38
A13-B45-C7-D38
A24-B45-C7-D38
A69-B45-C7-D38
A67-B45-C7-D38
A39-B45-C7-D38
A65-B45-C7-D38
A66-B45-C7-D38
A2-B53-C7-D38
A3-B53-C7-D38
A9-B53-C7-D38
A13-B53-C7-D38
A24-B53-C7-D38
A69-B53-C7-D38
A67-B53-C7-D38
A39-B53-C7-D38
A65-B53-C7-D38
A66-B53-C7-D38
A2-B79-C7-D38
A3-B79-C7-D38
A9-B79-C7-D38
A13-B79-C7-D38
A24-B79-C7-D38
A69-B79-C7-D38
A67-B79-C7-D38
A39-B79-C7-D38
A65-B79-C7-D38
A66-B79-C7-D38
A2-B80-C7-D38
A3-B80-C7-D38
A9-B80-C7-D38
A13-B80-C7-D38
A24-B80-C7-D38
A69-B80-C7-D38
A67-B80-C7-D38
A39-B80-C7-D38
A65-B80-C7-D38
A66-B80-C7-D38
A2-B85-C7-D38
A3-B85-C7-D387
A9-B85-C7-D38
A13-B85-C7-D38
A24-B85-C7-D38
A69-B85-C7-D38
A67-B85-C7-D38
A39-B85-C7-D38
A65-B85-C7-D38
A66-B85-C7-D38
A2-B86-C7-D38
A3-B86-C7-D38
A9-B86-C7-D38
A13-B86-C7-D38
A24-B86-C7-D38
A69-B86-C7-D38
A67-B86-C7-D38
A39-B86-C7-D38
A65-B86-C7-D38
A66-B86-C7-D38
A2-B87-C7-D38
A3-B87-C7-D38
A9-B87-C7-D38
A13-B87-C7-D38
A24-B87-C7-D38
A69-B87-C7-D38
A67-B87-C7-D38
A39-B87-C7-D38
A65-B87-C7-D38
A66-B87-C7-D38
A2-B89-C7-D38
A3-B89-C7-D38
A9-B89-C7-D38
A13-B89-C7-D38
A24-B89-C7-D38
A69-B89-C7-D38
A67-B89-C7-D38

-continued
A39-B89-C7-D38
A65-B89-C7-D38
A66-B89-C7-D38
A2-B92-C7-D38
A3-B92-C7-D38
A9-B92-C7-D38
A13-B92-C7-D38
A24-B92-C7-D38
A69-B92-C7-D38
A67-B92-C7-D38
A39-B92-C7-D38
A65-B92-C7-D38
A66-B92-C7-D38
A2-B4-C8-D38
A3-B4-C8-D38
A9-B4-C8-D38
A13-B4-C8-D38
A24-B4-C8-D38
A69-B4-C8-D38
A67-B4-C8-D38
A39-B4-C8-D38
A65-B4-C8-D38
A66-B4-C8-D38
A2-B5-C8-D38
A3-B5-C8-D38
A9-B5-C8-D38
A13-B5-C8-D38
A24-B5-C8-D38
A69-B5-C8-D38
A67-B5-C8-D38
A39-B5-C8-D38
A65-B5-C8-D38
A66-B5-C8-D38
A2-B6-C8-D38
A3-B6-C8-D38
A9-B6-C8-D38
A13-B6-C8-D38
A24-B6-C8-D38
A69-B6-C8-D38
A67-B6-C8-D38
A39-B6-C8-D38
A65-B6-C8-D38
A66-B6-C8-D38
A2-B32-C8-D38
A3-B32-C8-D38
A9-B32-C8-D38
A13-B32-C8-D38
A24-B32-C8-D38
A69-B32-C8-D38
A67-B32-C8-D38
A39-B32-C8-D38
A65-B32-C8-D38
A66-B32-C8-D38
A2-B39-C8-D38
A3-B39-C8-D38
A9-B39-C8-D38
A13-B39-C8-D38
A24-B39-C8-D38
A69-B39-C8-D38
A67-B39-C8-D38
A39-B39-C8-D38
A65-B39-C8-D38
A66-B39-C8-D38
A2-B45-C8-D38
A3-B45-C8-D38
A9-B45-C8-D38
A13-B45-C8-D38
A24-B45-C8-D38
A69-B45-C8-D38
A67-B45-C8-D38
A39-B45-C8-D38
A65-B45-C8-D38
A66-B45-C8-D38
A2-B53-C8-D38
A3-B53-C8-D38
A9-B53-C8-D38
A13-B53-C8-D38
A24-B53-C8-D38
A69-B53-C8-D38
A67-B53-C8-D38

-continued
A39-B53-C8-D38
A65-B53-C8-D38
A66-B53-C8-D38
A2-B79-C8-D38
A3-B79-C8-D38
A9-B79-C8-D38
A13-B79-C8-D38
A24-B79-C8-D38
A69-B79-C8-D38
A67-B79-C8-D38
A39-B79-C8-D38
A65-B79-C8-D38
A66-B79-C8-D38
A2-B80-C8-D38
A3-B80-C8-D38
A9-B80-C8-D38
A13-B80-C8-D38
A24-B80-C8-D38
A69-B80-C8-D38
A67-B80-C8-D38
A39-B80-C8-D38
A65-B80-C8-D38
A66-B80-C8-D38
A2-B85-C8-D38
A3-B85-C8-D38
A9-B85-C8-D38
A13-B85-C8-D38
A24-B85-C8-D38
A69-B85-C8-D38
A67-B85-C8-D38
A39-B85-C8-D38
A65-B85-C8-D38
A66-B85-C8-D38
A2-B86-C8-D38
A3-B86-C8-D38
A9-B86-C8-D38
A13-B86-C8-D38
A24-B86-C8-D38
A69-B86-C8-D38
A67-B86-C8-D38
A39-B86-C8-D38
A65-B86-C8-D38
A66-B86-C8-D38
A2-B87-C8-D38
A3-B87-C8-D38
A9-B87-C8-D38
A13-B87-C8-D38
A24-B87-C8-D38
A69-B87-C8-D38
A67-B87-C8-D38
A39-B87-C8-D38
A65-B87-C8-D38
A66-B87-C8-D38
A2-B89-C8-D38
A3-B89-C8-D38
A9-B89-C8-D38
A13-B89-C8-D38
A24-B89-C8-D38
A69-B89-C8-D38
A67-B89-C8-D38
A39-B89-C8-D38
A65-B89-C8-D38
A66-B89-C8-D38
A2-B92-C8-D38
A3-B92-C8-D38
A9-B92-C8-D38
A13-B92-C8-D38
A24-B92-C8-D38
A69-B92-C8-D38
A67-B92-C8-D38
A39-B92-C8-D38
A65-B92-C8-D38
A66-B92-C8-D38
A2-B4-C9-D38
A3-B4-C9-D38
A9-B4-C9-D38
A13-B4-C9-D38
A24-B4-C9-D38
A69-B4-C9-D38
A67-B4-C9-D38

-continued
A39-B4-C9-D38
A65-B4-C9-D38
A66-B4-C9-D38
A2-B5-C9-D38
A3-B5-C9-D38
A9-B5-C9-D38
A13-B5-C9-D38
A24-B5-C9-D38
A69-B5-C9-D38
A67-B5-C9-D38
A39-B5-C9-D38
A65-B5-C9-D38
A66-B5-C9-D38
A2-B6-C9-D38
A3-B6-C9-D38
A9-B6-C9-D38
A13-B6-C9-D38
A24-B6-C9-D38
A69-B6-C9-D38
A67-B6-C9-D38
A39-B6-C9-D38
A65-B6-C9-D38
A66-B6-C9-D38
A2-B32-C9-D38
A3-B32-C9-D38
A9-B32-C9-D38
A13-B32-C9-D38
A24-B32-C9-D38
A69-B32-C9-D38
A67-B32-C9-D38
A39-B32-C9-D38
A65-B32-C9-D38
A66-B32-C9-D38
A2-B39-C9-D38
A3-B39-C9-D38
A9-B39-C9-D38
A13-B39-C9-D38
A24-B39-C9-D38
A69-B39-C9-D38
A67-B39-C9-D38
A39-B39-C9-D38
A65-B39-C9-D38
A66-B39-C9-D38
A2-B45-C9-D38
A3-B45-C9-D38
A9-B45-C9-D38
A13-B45-C9-D38
A24-B45-C9-D38
A69-B45-C9-D38
A67-B45-C9-D38
A39-B45-C9-D38
A65-B45-C9-D38
A66-B45-C9-D38
A2-B53-C9-D38
A3-B53-C9-D38
A9-B53-C9-D38
A13-B53-C9-D38
A24-B53-C9-D38
A69-B53-C9-D38
A67-B53-C9-D38
A39-B53-C9-D38
A65-B53-C9-D38
A66-B53-C9-D38
A2-B79-C9-D38
A3-B79-C9-D38
A9-B79-C9-D38
A13-B79-C9-D38
A24-B79-C9-D38
A69-B79-C9-D38
A67-B79-C9-D38
A39-B79-C9-D38
A65-B79-C9-D38
A66-B79-C9-D38
A2-B80-C9-D38
A3-B80-C9-D38
A9-B80-C9-D38
A13-B80-C9-D38
A24-B80-C9-D38
A69-B80-C9-D38
A67-B80-C9-D38

-continued
A39-B80-C9-D38
A65-B80-C9-D38
A66-B80-C9-D38
A2-B85-C9-D38
A3-B85-C9-D38
A9-B85-C9-D38
A13-B85-C9-D38
A24-B85-C9-D38
A69-B85-C9-D38
A67-B85-C9-D38
A39-B85-C9-D38
A65-B85-C9-D38
A66-B85-C9-D38
A2-B86-C9-D38
A3-B86-C9-D38
A9-B86-C9-D38
A13-B86-C9-D38
A24-B86-C9-D38
A69-B86-C9-D38
A67-B86-C9-D38
A39-B86-C9-D38
A65-B86-C9-D38
A66-B86-C9-D38
A2-B87-C9-D38
A3-B87-C9-D38
A9-B87-C9-D38
A13-B87-C9-D38
A24-B87-C9-D38
A69-B87-C9-D38
A67-B87-C9-D38
A39-B87-C9-D38
A65-B87-C9-D38
A66-B87-C9-D38
A2-B89-C9-D38
A3-B89-C9-D38
A9-B89-C9-D38
A13-B89-C9-D38
A24-B89-C9-D38
A69-B89-C9-D38
A67-B89-C9-D38
A39-B89-C9-D38
A65-B89-C9-D38
A66-B89-C9-D38
A2-B92-C9-D38
A3-B92-C9-D38
A9-B92-C9-D38
A13-B92-C9-D38
A24-B92-C9-D38
A69-B92-C9-D38
A67-B92-C9-D38
A39-B92-C9-D38
A65-B92-C9-D38
A66-B92-C9-D38
A2-B4-C10-D38
A3-B4-C10-D38
A9-B4-C10-D38
A13-B4-C10-D38
A24-B4-C10-D38
A69-B4-C10-D38
A67-B4-C10-D38
A39-B4-C10-D38
A65-B4-C10-D38
A66-B4-C10-D38
A2-B5-C10-D38
A3-B5-C10-D38
A9-B5-C10-D38
A13-B5-C10-D38
A24-B5-C10-D38
A69-B5-C10-D38
A67-B5-C10-D38
A39-B5-C10-D38
A65-B5-C10-D38
A66-B5-C10-D38
A2-B6-C10-D38
A3-B6-C10-D38
A9-B6-C10-D38
A13-B6-C10-D38
A24-B6-C10-D38
A69-B6-C10-D38
A67-B6-C10-D38

-continued
A39-B6-C10-D38
A65-B6-C10-D38
A66-B6-C10-D38
A2-B32-C10-D38
A3-B32-C10-D38
A9-B32-C10-D38
A13-B32-C10-D38
A24-B32-C10-D38
A69-B32-C10-D38
A67-B32-C10-D38
A39-B32-C10-D38
A65-B32-C10-D38
A66-B32-C10-D38
A2-B39-C10-D38
A3-B39-C10-D38
A9-B39-C10-D38
A13-B39-C10-D38
A24-B39-C10-D38
A69-B39-C10-D38
A67-B39-C10-D38
A39-B39-C10-D38
A65-B39-C10-D38
A66-B39-C10-D38
A2-B45-C10-D38
A3-B45-C10-D38
A9-B45-C10-D38
A13-B45-C10-D38
A24-B45-C10-D38
A69-B45-C10-D38
A67-B45-C10-D38
A39-B45-C10-D38
A65-B45-C10-D38
A66-B45-C10-D38
A2-B53-C10-D38
A3-B53-C10-D38
A9-B53-C10-D38
A13-B53-C10-D38
A24-B53-C10-D38
A69-B53-C10-D38
A67-B53-C10-D38
A39-B53-C10-D38
A65-B53-C10-D38
A66-B53-C10-D38
A2-B79-C10-D38
A3-B79-C10-D38
A9-B79-C10-D38
A13-B79-C10-D38
A24-B79-C10-D38
A69-B79-C10-D38
A67-B79-C10-D38
A39-B79-C10-D38
A65-B79-C10-D38
A66-B79-C10-D38
A2-B80-C10-D38
A3-B80-C10-D38
A9-B80-C10-D38
A13-B80-C10-D38
A24-B80-C10-D38
A69-B80-C10-D38
A67-B80-C10-D38
A39-B80-C10-D38
A65-B80-C10-D38
A66-B80-C10-D38
A2-B85-C10-D38
A3-B85-C10-D38
A9-B85-C10-D38
A13-B85-C10-D38
A24-B85-C10-D38
A69-B85-C10-D38
A67-B85-C10-D38
A39-B85-C10-D38
A65-B85-C10-D38
A66-B85-C10-D38
A2-B86-C10-D38
A3-B86-C10-D38
A9-B86-C10-D38
A13-B86-C10-D38
A24-B86-C10-D38
A69-B86-C10-D38
A67-B86-C10-D38

-continued

A39-B86-C10-D38
A65-B86-C10-D38
A66-B86-C10-D38
A2-B87-C10-D38
A3-B87-C10-D38
A9-B87-C10-D38
A13-B87-C10-D38
A24-B87-C10-D38
A69-B87-C10-D38
A67-B87-C10-D38
A39-B87-C10-D38
A65-B87-C10-D38
A66-B87-C10-D38
A2-B89-C10-D38
A3-B89-C10-D38
A9-B89-C10-D38
A13-B89-C10-D38
A24-B89-C10-D38
A69-B89-C10-D38
A67-B89-C10-D38
A39-B89-C10-D38
A65-B89-C10-D38
A66-B89-C10-D38
A2-B92-C10-D38
A3-B92-C10-D38
A9-B92-C10-D38
A13-B92-C10-D38
A24-B92-C10-D38
A69-B92-C10-D38
A67-B92-C10-D38
A39-B92-C10-D38
A65-B92-C10-D38
A66-B92-C10-D38
A2-B4-C11-D38
A3-B4-C11-D38
A9-B4-C11-D38
A13-B4-C11-D38
A24-B4-C11-D38
A69-B4-C11-D38
A67-B4-C11-D38
A39-B4-C11-D38
A65-B4-C11-D38
A66-B4-C11-D38
A2-B5-C11-D38
A3-B5-C11-D38
A9-B5-C11-D38
A13-B5-C11-D38
A24-B5-C11-D38
A69-B5-C11-D38
A67-B5-C11-D38
A39-B5-C11-D38
A65-B5-C11-D38
A66-B5-C11-D38
A2-B6-C11-D38
A3-B6-C11-D38
A9-B6-C11-D38
A13-B6-C11-D38
A24-B6-C11-D38
A69-B6-C11-D38
A67-B6-C11-D38
A39-B6-C11-D38
A65-B6-C11-D38
A66-B6-C11-D38
A2-B32-C11-D38
A3-B32-C11-D38
A9-B32-C11-D38
A13-B32-C11-D38
A24-B32-C11-D38
A69-B32-C11-D38
A67-B32-C11-D38
A39-B32-C11-D38
A65-B32-C11-D38
A66-B32-C11-D38
A2-B39-C11-D38
A3-B39-C11-D38
A9-B39-C11-D38
A13-B39-C11-D38
A24-B39-C11-D38
A69-B39-C11-D38
A67-B39-C11-D38

-continued

A39-B39-C11-D38
A65-B39-C11-D38
A66-B39-C11-D38
A2-B45-C11-D38
A3-B45-C11-D38
A9-B45-C11-D38
A13-B45-C11-D38
A24-B45-C11-D38
A69-B45-C11-D38
A67-B45-C11-D38
A39-B45-C11-D38
A65-B45-C11-D38
A66-B45-C11-D38
A2-B53-C11-D38
A3-B53-C11-D38
A9-B53-C11-D38
A13-B53-C11-D38
A24-B53-C11-D38
A69-B53-C11-D38
A67-B53-C11-D38
A39-B53-C11-D38
A65-B53-C11-D38
A66-B53-C11-D38
A2-B79-C11-D38
A3-B79-C11-D38
A9-B79-C11-D38
A13-B79-C11-D38
A24-B79-C11-D38
A69-B79-C11-D38
A67-B79-C11-D38
A39-B79-C11-D38
A65-B79-C11-D38
A66-B79-C11-D38
A2-B80-C11-D38
A3-B80-C11-D38
A9-B80-C11-D38
A13-B80-C11-D38
A24-B80-C11-D38
A69-B80-C11-D38
A67-B80-C11-D38
A39-B80-C11-D38
A65-B80-C11-D38
A66-B80-C11-D38
A2-B85-C11-D38
A3-B85-C11-D38
A9-B85-C11-D38
A13-B85-C11-D38
A24-B85-C11-D38
A69-B85-C11-D38
A67-B85-C11-D38
A39-B85-C11-D38
A65-B85-C11-D38
A66-B85-C11-D38
A2-B86-C11-D38
A3-B86-C11-D38
A9-B86-C11-D38
A13-B86-C11-D38
A24-B86-C11-D38
A69-B86-C11-D38
A67-B86-C11-D38
A39-B86-C11-D38
A65-B86-C11-D38
A66-B86-C11-D38
A2-B87-C11-D38
A3-B87-C11-D38
A9-B87-C11-D38
A13-B87-C11-D38
A24-B87-C11-D38
A69-B87-C11-D38
A67-B87-C11-D38
A39-B87-C11-D38
A65-B87-C11-D38
A66-B87-C11-D38
A2-B89-C11-D38
A3-B89-C11-D38
A9-B89-C11-D38
A13-B89-C11-D38
A24-B89-C11-D38
A69-B89-C11-D38
A67-B89-C11-D38

-continued
A39-B89-C11-D38
A65-B89-C11-D38
A66-B89-C11-D38
A2-B92-C11-D38
A3-B92-C11-D38
A9-B92-C11-D38
A13-B92-C11-D38
A24-B92-C11-D38
A69-B92-C11-D38
A67-B92-C11-D38
A39-B92-C11-D38
A65-B92-C11-D38
A66-B92-C11-D38
A2-B4-C12-D38
A3-B4-C12-D38
A9-B4-C12-D38
A13-B4-C12-D38
A24-B4-C12-D38
A69-B4-C12-D38
A67-B4-C12-D38
A39-B4-C12-D38
A65-B4-C12-D38
A66-B4-C12-D38
A2-B5-C12-D38
A3-B5-C12-D38
A9-B5-C12-D38
A13-B5-C12-D38
A24-B5-C12-D38
A69-B5-C12-D38
A67-B5-C12-D38
A39-B5-C12-D38
A65-B5-C12-D38
A66-B5-C12-D38
A2-B6-C12-D38
A3-B6-C12-D38
A9-B6-C12-D38
A13-B6-C12-D38
A24-B6-C12-D38
A69-B6-C12-D38
A67-B6-C12-D38
A39-B6-C12-D38
A65-B6-C12-D38
A66-B6-C12-D38
A2-B32-C12-D38
A3-B32-C12-D38
A9-B32-C12-D38
A13-B32-C12-D38
A24-B32-C12-D38
A69-B32-C12-D38
A67-B32-C12-D38
A39-B32-C12-D38
A65-B32-C12-D38
A66-B32-C12-D38
A2-B39-C12-D38
A3-B39-C12-D38
A9-B39-C12-D38
A13-B39-C12-D38
A24-B39-C12-D38
A69-B39-C12-D38
A67-B39-C12-D38
A39-B39-C12-D38
A65-B39-C12-D38
A66-B39-C12-D38
A2-B45-C12-D38
A3-B45-C12-D38
A9-B45-C12-D38
A13-B45-C12-D38
A24-B45-C12-D38
A69-B45-C12-D38
A67-B45-C12-D38
A39-B45-C12-D38
A65-B45-C12-D38
A66-B45-C12-D38
A2-B53-C12-D38
A3-B53-C12-D38
A9-B53-C12-D38
A13-B53-C12-D38
A24-B53-C12-D38
A69-B53-C12-D38
A67-B53-C12-D38

-continued
A39-B53-C12-D38
A65-B53-C12-D38
A66-B53-C12-D38
A2-B79-C12-D38
A3-B79-C12-D38
A9-B79-C12-D38
A13-B79-C12-D38
A24-B79-C12-D38
A69-B79-C12-D38
A67-B79-C12-D38
A39-B79-C12-D38
A65-B79-C12-D38
A66-B79-C12-D38
A2-B80-C12-D38
A3-B80-C12-D38
A9-B80-C12-D38
A13-B80-C12-D38
A24-B80-C12-D38
A69-B80-C12-D38
A67-B80-C12-D38
A39-B80-C12-D38
A65-B80-C12-D38
A66-B80-C12-D38
A2-B85-C12-D38
A3-B85-C12-D38
A9-B85-C12-D38
A13-B85-C12-D38
A24-B85-C12-D38
A69-B85-C12-D38
A67-B85-C12-D38
A39-B85-C12-D38
A65-B85-C12-D38
A66-B85-C12-D38
A2-B86-C12-D38
A3-B86-C12-D38
A9-B86-C12-D38
A13-B86-C12-D38
A24-B86-C12-D38
A69-B86-C12-D38
A67-B86-C12-D38
A39-B86-C12-D38
A65-B86-C12-D38
A66-B86-C12-D38
A2-B87-C12-D38
A3-B87-C12-D38
A9-B87-C12-D38
A13-B87-C12-D38
A24-B87-C12-D38
A69-B87-C12-D38
A67-B87-C12-D38
A39-B87-C12-D38
A65-B87-C12-D38
A66-B87-C12-D38
A2-B89-C12-D38
A3-B89-C12-D38
A9-B89-C12-D38
A13-B89-C12-D38
A24-B89-C12-D38
A69-B89-C12-D38
A67-B89-C12-D38
A39-B89-C12-D38
A65-B89-C12-D38
A66-B89-C12-D38
A2-B92-C12-D38
A3-B92-C12-D38
A9-B92-C12-D38
A13-B92-C12-D38
A24-B92-C12-D38
A69-B92-C12-D38
A67-B92-C12-D38
A39-B92-C12-D38
A65-B92-C12-D38
A66-B92-C12-D38
A2-B4-C13-D38
A3-B4-C13-D38
A9-B4-C13-D38
A13-B4-C13-D38
A24-B4-C13-D38
A69-B4-C13-D38
A67-B4-C13-D38

-continued
A39-B4-C13-D38
A65-B4-C13-D38
A66-B4-C13-D38
A2-B5-C13-D38
A3-B5-C13-D38
A9-B5-C13-D38
A13-B5-C13-D38
A24-B5-C13-D38
A69-B5-C13-D38
A67-B5-C13-D38
A39-B5-C13-D38
A65-B5-C13-D38
A66-B5-C13-D38
A2-B6-C13-D38
A3-B6-C13-D38
A9-B6-C13-D38
A13-B6-C13-D38
A24-B6-C13-D38
A69-B6-C13-D38
A67-B6-C13-D38
A39-B6-C13-D38
A65-B6-C13-D38
A66-B6-C13-D38
A2-B32-C13-D38
A3-B32-C13-D38
A9-B32-C13-D38
A13-B32-C13-D38
A24-B32-C13-D38
A69-B32-C13-D38
A67-B32-C13-D38
A39-B32-C13-D38
A65-B32-C13-D38
A66-B32-C13-D38
A2-B39-C13-D38
A3-B39-C13-D38
A9-B39-C13-D38
A13-B39-C13-D38
A24-B39-C13-D38
A69-B39-C13-D38
A67-B39-C13-D38
A39-B39-C13-D38
A65-B39-C13-D38
A66-B39-C13-D38
A2-B45-C13-D38
A3-B45-C13-D38
A9-B45-C13-D38
A13-B45-C13-D38
A24-B45-C13-D38
A69-B45-C13-D38
A67-B45-C13-D38
A39-B45-C13-D38
A65-B45-C13-D38
A66-B45-C13-D38
A2-B53-C13-D38
A3-B53-C13-D38
A9-B53-C13-D38
A13-B53-C13-D38
A24-B53-C13-D38
A69-B53-C13-D38
A67-B53-C13-D38
A39-B53-C13-D38
A65-B53-C13-D38
A66-B53-C13-D38
A2-B79-C13-D38
A3-B79-C13-D38
A9-B79-C13-D38
A13-B79-C13-D38
A24-B79-C13-D38
A69-B79-C13-D38
A67-B79-C13-D38
A39-B79-C13-D38
A65-B79-C13-D38
A66-B79-C13-D38
A2-B80-C13-D38
A3-B80-C13-D38
A9-B80-C13-D38
A13-B80-C13-D38
A24-B80-C13-D38
A69-B80-C13-D38
A67-B80-C13-D38

-continued
A39-B80-C13-D38
A65-B80-C13-D38
A66-B80-C13-D38
A2-B85-C13-D38
A3-B85-C13-D38
A9-B85-C13-D38
A13-B85-C13-D38
A24-B85-C13-D38
A69-B85-C13-D38
A67-B85-C13-D38
A39-B85-C13-D38
A65-B85-C13-D38
A66-B85-C13-D38
A2-B86-C13-D38
A3-B86-C13-D38
A9-B86-C13-D38
A13-B86-C13-D38
A24-B86-C13-D38
A69-B86-C13-D38
A67-B86-C13-D38
A39-B86-C13-D38
A65-B86-C13-D38
A66-B86-C13-D38
A2-B87-C13-D38
A3-B87-C13-D38
A9-B87-C13-D38
A13-B87-C13-D38
A24-B87-C13-D38
A69-B87-C13-D38
A67-B87-C13-D38
A39-B87-C13-D38
A65-B87-C13-D38
A66-B87-C13-D38
A2-B89-C13-D38
A3-B89-C13-D38
A9-B89-C13-D38
A13-B89-C13-D38
A24-B89-C13-D38
A69-B89-C13-D38
A67-B89-C13-D38
A39-B89-C13-D38
A65-B89-C13-D38
A66-B89-C13-D38
A2-B92-C13-D38
A3-B92-C13-D38
A9-B92-C13-D38
A13-B92-C13-D38
A24-B92-C13-D38
A69-B92-C13-D38
A67-B92-C13-D38
A39-B92-C13-D38
A65-B92-C13-D38
A66-B92-C13-D38
A2-B4-C1-D39
A3-B4-C1-D39
A9-B4-C1-D39
A13-B4-C1-D39
A24-B4-C1-D39
A69-B4-C1-D39
A67-B4-C1-D39
A39-B4-C1-D39
A65-B4-C1-D39
A66-B4-C1-D39
A2-B5-C1-D39
A3-B5-C1-D39
A9-B5-C1-D39
A13-B5-C1-D39
A24-B5-C1-D39
A69-B5-C1-D39
A67-B5-C1-D39
A39-B5-C1-D39
A65-B5-C1-D39
A66-B5-C1-D39
A2-B6-C1-D39
A3-B6-C1-D39
A9-B6-C1-D39
A13-B6-C1-D39
A24-B6-C1-D39
A69-B6-C1-D39
A67-B6-C1-D39

-continued

A39-B6-C1-D39
A65-B6-C1-D39
A66-B6-C1-D39
A2-B32-C1-D39
A3-B32-C1-D39
A9-B32-C1-D39
A13-B32-C1-D39
A24-B32-C1-D39
A69-B32-C1-D39
A67-B32-C1-D39
A39-B32-C1-D39
A65-B32-C1-D39
A66-B32-C1-D39
A2-B39-C1-D39
A3-B39-C1-D39
A9-B39-C1-D39
A13-B39-C1-D39
A24-B39-C1-D39
A69-B39-C1-D39
A67-B39-C1-D39
A39-B39-C1-D39
A65-B39-C1-D39
A66-B39-C1-D39
A2-B45-C1-D39
A3-B45-C1-D39
A9-B45-C1-D39
A13-B45-C1-D39
A24-B45-C1-D39
A69-B45-C1-D39
A67-B45-C1-D39
A39-B45-C1-D39
A65-B45-C1-D39
A66-B45-C1-D39
A2-B53-C1-D39
A3-B53-C1-D39
A9-B53-C1-D39
A13-B53-C1-D39
A24-B53-C1-D39
A69-B53-C1-D39
A67-B53-C1-D39
A39-B53-C1-D39
A65-B53-C1-D39
A66-B53-C1-D39
A2-B79-C1-D39
A3-B79-C1-D39
A9-B79-C1-D39
A13-B79-C1-D39
A24-B79-C1-D39
A69-B79-C1-D39
A67-B79-C1-D39
A39-B79-C1-D39
A65-B79-C1-D39
A66-B79-C1-D39
A2-B80-C1-D39
A3-B80-C1-D39
A9-B80-C1-D39
A13-B80-C1-D39
A24-B80-C1-D39
A69-B80-C1-D39
A67-B80-C1-D39
A39-B80-C1-D39
A65-B80-C1-D39
A66-B80-C1-D39
A2-B85-C1-D39
A3-B85-C1-D39
A9-B85-C1-D39
A13-B85-C1-D39
A24-B85-C1-D39
A69-B85-C1-D39
A67-B85-C1-D39
A39-B85-C1-D39
A65-B85-C1-D39
A66-B85-C1-D39
A2-B86-C1-D39
A3-B86-C1-D39
A9-B86-C1-D39
A13-B86-C1-D39
A24-B86-C1-D39
A69-B86-C1-D39
A67-B86-C1-D39

-continued

A39-B86-C1-D39
A65-B86-C1-D39
A66-B86-C1-D39
A2-B87-C1-D39
A3-B87-C1-D39
A9-B87-C1-D39
A13-B87-C1-D39
A24-B87-C1-D39
A69-B87-C1-D39
A67-B87-C1-D39
A39-B87-C1-D39
A65-B87-C1-D39
A66-B87-C1-D39
A2-B89-C1-D39
A3-B89-C1-D39
A9-B89-C1-D39
A13-B89-C1-D39
A24-B89-C1-D39
A69-B89-C1-D39
A67-B89-C1-D39
A39-B89-C1-D39
A65-B89-C1-D39
A66-B89-C1-D39
A2-B92-C1-D39
A3-B92-C1-D39
A9-B92-C1-D39
A13-B92-C1-D39
A24-B92-C1-D39
A69-B92-C1-D39
A67-B92-C1-D39
A39-B92-C1-D39
A65-B92-C1-D39
A66-B92-C1-D39
A2-B4-C2-D39
A3-B4-C2-D39
A9-B4-C2-D39
A13-B4-C2-D39
A24-B4-C2-D39
A69-B4-C2-D39
A67-B4-C2-D39
A39-B4-C2-D39
A65-B4-C2-D39
A66-B4-C2-D39
A2-B5-C2-D39
A3-B5-C2-D39
A9-B5-C2-D39
A13-B5-C2-D39
A24-B5-C2-D39
A69-B5-C2-D39
A67-B5-C2-D39
A39-B5-C2-D39
A65-B5-C2-D39
A66-B5-C2-D39
A2-B6-C2-D39
A3-B6-C2-D39
A9-B6-C2-D39
A13-B6-C2-D39
A24-B6-C2-D39
A69-B6-C2-D39
A67-B6-C2-D39
A39-B6-C2-D39
A65-B6-C2-D39
A66-B6-C2-D39
A2-B32-C2-D39
A3-B32-C2-D39
A9-B32-C2-D39
A13-B32-C2-D39
A24-B32-C2-D39
A69-B32-C2-D39
A67-B32-C2-D39
A39-B32-C2-D39
A65-B32-C2-D39
A66-B32-C2-D39
A2-B39-C2-D39
A3-B39-C2-D39
A9-B39-C2-D39
A13-B39-C2-D39
A24-B39-C2-D39
A69-B39-C2-D39
A67-B39-C2-D39

-continued
A39-B39-C2-D39
A65-B39-C2-D39
A66-B39-C2-D39
A2-B45-C2-D39
A3-B45-C2-D39
A9-B45-C2-D39
A13-B45-C2-D39
A24-B45-C2-D39
A69-B45-C2-D39
A67-B45-C2-D39
A39-B45-C2-D39
A65-B45-C2-D39
A66-B45-C2-D39
A2-B53-C2-D39
A3-B53-C2-D39
A9-B53-C2-D39
A13-B53-C2-D39
A24-B53-C2-D39
A69-B53-C2-D39
A67-B53-C2-D39
A39-B53-C2-D39
A65-B53-C2-D39
A66-B53-C2-D39
A2-B79-C2-D39
A3-B79-C2-D39
A9-B79-C2-D39
A13-B79-C2-D39
A24-B79-C2-D39
A69-B79-C2-D39
A67-B79-C2-D39
A39-B79-C2-D39
A65-B79-C2-D39
A66-B79-C2-D39
A2-B80-C2-D39
A3-B80-C2-D39
A9-B80-C2-D39
A13-B80-C2-D39
A24-B80-C2-D39
A69-B80-C2-D39
A67-B80-C2-D39
A39-B80-C2-D39
A65-B80-C2-D39
A66-B80-C2-D39
A2-B85-C2-D39
A3-B85-C2-D39
A9-B85-C2-D39
A13-B85-C2-D39
A24-B85-C2-D39
A69-B85-C2-D39
A67-B85-C2-D39
A39-B85-C2-D39
A65-B85-C2-D39
A66-B85-C2-D39
A2-B86-C2-D39
A3-B86-C2-D39
A9-B86-C2-D39
A13-B86-C2-D39
A24-B86-C2-D39
A69-B86-C2-D39
A67-B86-C2-D39
A39-B86-C2-D39
A65-B86-C2-D39
A66-B86-C2-D39
A2-B87-C2-D39
A3-B87-C2-D39
A9-B87-C2-D39
A13-B87-C2-D39
A24-B87-C2-D39
A69-B87-C2-D39
A67-B87-C2-D39
A39-B87-C2-D39
A65-B87-C2-D39
A66-B87-C2-D39
A2-B89-C2-D39
A3-B89-C2-D39
A9-B89-C2-D39
A13-B89-C2-D39
A24-B89-C2-D39
A69-B89-C2-D39
A67-B89-C2-D39

-continued
A39-B89-C2-D39
A65-B89-C2-D39
A66-B89-C2-D39
A2-B92-C2-D39
A3-B92-C2-D39
A9-B92-C2-D39
A13-B92-C2-D39
A24-B92-C2-D39
A69-B92-C2-D39
A67-B92-C2-D39
A39-B92-C2-D39
A65-B92-C2-D39
A66-B92-C2-D39
A2-B4-C3-D39
A3-B4-C3-D39
A9-B4-C3-D39
A13-B4-C3-D39
A24-B4-C3-D39
A69-B4-C3-D39
A67-B4-C3-D39
A39-B4-C3-D39
A65-B4-C3-D39
A66-B4-C3-D39
A2-B5-C3-D39
A3-B5-C3-D39
A9-B5-C3-D39
A13-B5-C3-D39
A24-B5-C3-D39
A69-B5-C3-D39
A67-B5-C3-D39
A39-B5-C3-D39
A65-B5-C3-D39
A66-B5-C3-D39
A2-B6-C3-D39
A3-B6-C3-D39
A9-B6-C3-D39
A13-B6-C3-D39
A24-B6-C3-D39
A69-B6-C3-D39
A67-B6-C3-D39
A39-B6-C3-D39
A65-B6-C3-D39
A66-B6-C3-D39
A2-B32-C3-D39
A3-B32-C3-D39
A9-B32-C3-D39
A13-B32-C3-D39
A24-B32-C3-D39
A69-B32-C3-D39
A67-B32-C3-D39
A39-B32-C3-D39
A65-B32-C3-D39
A66-B32-C3-D39
A2-B39-C3-D39
A3-B39-C3-D39
A9-B39-C3-D39
A13-B39-C3-D39
A24-B39-C3-D39
A69-B39-C3-D39
A67-B39-C3-D39
A39-B39-C3-D39
A65-B39-C3-D39
A66-B39-C3-D39
A2-B45-C3-D39
A3-B45-C3-D39
A9-B45-C3-D39
A13-B45-C3-D39
A24-B45-C3-D39
A69-B45-C3-D39
A67-B45-C3-D39
A39-B45-C3-D39
A65-B45-C3-D39
A66-B45-C3-D39
A2-B53-C3-D39
A3-B53-C3-D39
A9-B53-C3-D39
A13-B53-C3-D39
A24-B53-C3-D39
A69-B53-C3-D39
A67-B53-C3-D39

-continued
A39-B53-C3-D39
A65-B53-C3-D39
A66-B53-C3-D39
A2-B79-C3-D39
A3-B79-C3-D39
A9-B79-C3-D39
A13-B79-C3-D39
A24-B79-C3-D39
A69-B79-C3-D39
A67-B79-C3-D39
A39-B79-C3-D39
A65-B79-C3-D39
A66-B79-C3-D39
A2-B80-C3-D39
A3-B80-C3-D39
A9-B80-C3-D39
A13-B80-C3-D39
A24-B80-C3-D39
A69-B80-C3-D39
A67-B80-C3-D39
A39-B80-C3-D39
A65-B80-C3-D39
A66-B80-C3-D39
A2-B85-C3-D39
A3-B85-C3-D39
A9-B85-C3-D39
A13-B85-C3-D39
A24-B85-C3-D39
A69-B85-C3-D39
A67-B85-C3-D39
A39-B85-C3-D39
A65-B85-C3-D39
A66-B85-C3-D39
A2-B86-C3-D39
A3-B86-C3-D39
A9-B86-C3-D39
A13-B86-C3-D39
A24-B86-C3-D39
A69-B86-C3-D39
A67-B86-C3-D39
A39-B86-C3-D39
A65-B86-C3-D39
A66-B86-C3-D39
A2-B87-C3-D39
A3-B87-C3-D39
A9-B87-C3-D39
A13-B87-C3-D39
A24-B87-C3-D39
A69-B87-C3-D39
A67-B87-C3-D39
A39-B87-C3-D39
A65-B87-C3-D39
A66-B87-C3-D39
A2-B89-C3-D39
A3-B89-C3-D39
A9-B89-C3-D39
A13-B89-C3-D39
A24-B89-C3-D39
A69-B89-C3-D39
A67-B89-C3-D39
A39-B89-C3-D39
A65-B89-C3-D39
A66-B89-C3-D39
A2-B92-C3-D39
A3-B92-C3-D39
A9-B92-C3-D39
A13-B92-C3-D39
A24-B92-C3-D39
A69-B92-C3-D39
A67-B92-C3-D39
A39-B92-C3-D39
A65-B92-C3-D39
A66-B92-C3-D39
A2-B4-C4-D39
A3-B4-C4-D39
A9-B4-C4-D39
A13-B4-C4-D39
A24-B4-C4-D39
A69-B4-C4-D39
A67-B4-C4-D39

-continued
A39-B4-C4-D39
A65-B4-C4-D39
A66-B4-C4-D39
A2-B5-C4-D39
A3-B5-C4-D39
A9-B5-C4-D39
A13-B5-C4-D39
A24-B5-C4-D39
A69-B5-C4-D39
A67-B5-C4-D39
A39-B5-C4-D39
A65-B5-C4-D39
A66-B5-C4-D39
A2-B6-C4-D39
A3-B6-C4-D39
A9-B6-C4-D39
A13-B6-C4-D39
A24-B6-C4-D39
A69-B6-C4-D39
A67-B6-C4-D39
A39-B6-C4-D39
A65-B6-C4-D39
A66-B6-C4-D39
A2-B32-C4-D39
A3-B32-C4-D39
A9-B32-C4-D39
A13-B32-C4-D39
A24-B32-C4-D39
A69-B32-C4-D39
A67-B32-C4-D39
A39-B32-C4-D39
A65-B32-C4-D39
A66-B32-C4-D39
A2-B39-C4-D39
A3-B39-C4-D39
A9-B39-C4-D39
A13-B39-C4-D39
A24-B39-C4-D39
A69-B39-C4-D39
A67-B39-C4-D39
A39-B39-C4-D39
A65-B39-C4-D39
A66-B39-C4-D39
A2-B45-C4-D39
A3-B45-C4-D39
A9-B45-C4-D39
A13-B45-C4-D39
A24-B45-C4-D39
A69-B45-C4-D39
A67-B45-C4-D39
A39-B45-C4-D39
A65-B45-C4-D39
A66-B45-C4-D39
A2-B53-C4-D39
A3-B53-C4-D39
A9-B53-C4-D39
A13-B53-C4-D39
A24-B53-C4-D39
A69-B53-C4-D39
A67-B53-C4-D39
A39-B53-C4-D39
A65-B53-C4-D39
A66-B53-C4-D39
A2-B79-C4-D39
A3-B79-C4-D39
A9-B79-C4-D39
A13-B79-C4-D39
A24-B79-C4-D39
A69-B79-C4-D39
A67-B79-C4-D39
A39-B79-C4-D39
A65-B79-C4-D39
A66-B79-C4-D39
A2-B80-C4-D39
A3-B80-C4-D39
A9-B80-C4-D39
A13-B80-C4-D39
A24-B80-C4-D39
A69-B80-C4-D39
A67-B80-C4-D39

-continued
A39-B80-C4-D39
A65-B80-C4-D39
A66-B80-C4-D39
A2-B85-C4-D39
A3-B85-C4-D39
A9-B85-C4-D39
A13-B85-C4-D39
A24-B85-C4-D39
A69-B85-C4-D39
A67-B85-C4-D39
A39-B85-C4-D39
A65-B85-C4-D39
A66-B85-C4-D39
A2-B86-C4-D39
A3-B86-C4-D39
A9-B86-C4-D39
A13-B86-C4-D39
A24-B86-C4-D39
A69-B86-C4-D39
A67-B86-C4-D39
A39-B86-C4-D39
A65-B86-C4-D39
A66-B86-C4-D39
A2-B87-C4-D39
A3-B87-C4-D39
A9-B87-C4-D39
A13-B87-C4-D39
A24-B87-C4-D39
A69-B87-C4-D39
A67-B87-C4-D39
A39-B87-C4-D39
A65-B87-C4-D39
A66-B87-C4-D39
A2-B89-C4-D39
A3-B89-C4-D39
A9-B89-C4-D39
A13-B89-C4-D39
A24-B89-C4-D39
A69-B89-C4-D39
A67-B89-C4-D39
A39-B89-C4-D39
A65-B89-C4-D39
A66-B89-C4-D39
A2-B92-C4-D39
A3-B92-C4-D39
A9-B92-C4-D39
A13-B92-C4-D39
A24-B92-C4-D39
A69-B92-C4-D39
A67-B92-C4-D39
A39-B92-C4-D39
A65-B92-C4-D39
A66-B92-C4-D39
A2-B4-C5-D39
A3-B4-C5-D39
A9-B4-C5-D39
A13-B4-C5-D39
A24-B4-C5-D39
A69-B4-C5-D39
A67-B4-C5-D39
A39-B4-C5-D39
A65-B4-C5-D39
A66-B4-C5-D39
A2-B5-C5-D39
A3-B5-C5-D39
A9-B5-C5-D39
A13-B5-C5-D39
A24-B5-C5-D39
A69-B5-C5-D39
A67-B5-C5-D39
A39-B5-C5-D39
A65-B5-C5-D39
A66-B5-C5-D39
A2-B6-C5-D39
A3-B6-C5-D39
A9-B6-C5-D39
A13-B6-C5-D39
A24-B6-C5-D39
A69-B6-C5-D39
A67-B6-C5-D39

-continued
A39-B6-C5-D39
A65-B6-C5-D39
A66-B6-C5-D39
A2-B32-C5-D39
A3-B32-C5-D39
A9-B32-C5-D39
A13-B32-C5-D39
A24-B32-C5-D39
A69-B32-C5-D39
A67-B32-C5-D39
A39-B32-C5-D39
A65-B32-C5-D39
A66-B32-C5-D39
A2-B39-C5-D39
A3-B39-C5-D39
A9-B39-C5-D39
A13-B39-C5-D39
A24-B39-C5-D39
A69-B39-C5-D39
A67-B39-C5-D39
A39-B39-C5-D39
A65-B39-C5-D39
A66-B39-C5-D39
A2-B45-C5-D39
A3-B45-C5-D39
A9-B45-C5-D39
A13-B45-C5-D39
A24-B45-C5-D39
A69-B45-C5-D39
A67-B45-C5-D39
A39-B45-C5-D39
A65-B45-C5-D39
A66-B45-C5-D39
A2-B53-C5-D39
A3-B53-C5-D39
A9-B53-C5-D39
A13-B53-C5-D39
A24-B53-C5-D39
A69-B53-C5-D39
A67-B53-C5-D39
A39-B53-C5-D39
A65-B53-C5-D39
A66-B53-C5-D39
A2-B79-C5-D39
A3-B79-C5-D39
A9-B79-C5-D39
A13-B79-C5-D39
A24-B79-C5-D39
A69-B79-C5-D39
A67-B79-C5-D39
A39-B79-C5-D39
A65-B79-C5-D39
A66-B79-C5-D39
A2-B80-C5-D39
A3-B80-C5-D39
A9-B80-C5-D39
A13-B80-C5-D39
A24-B80-C5-D39
A69-B80-C5-D39
A67-B80-C5-D39
A39-B80-C5-D39
A65-B80-C5-D39
A66-B80-C5-D39
A2-B85-C5-D39
A3-B85-C5-D39
A9-B85-C5-D39
A13-B85-C5-D39
A24-B85-C5-D39
A69-B85-C5-D39
A67-B85-C5-D39
A39-B85-C5-D39
A65-B85-C5-D39
A66-B85-C5-D39
A2-B86-C5-D39
A3-B86-C5-D39
A9-B86-C5-D39
A13-B86-C5-D39
A24-B86-C5-D39
A69-B86-C5-D39
A67-B86-C5-D39

-continued

A39-B86-C5-D39
A65-B86-C5-D39
A66-B86-C5-D39
A2-B87-C5-D39
A3-B87-C5-D39
A9-B87-C5-D39
A13-B87-C5-D39
A24-B87-C5-D39
A69-B87-C5-D39
A67-B87-C5-D39
A39-B87-C5-D39
A65-B87-C5-D39
A66-B87-C5-D39
A2-B89-C5-D39
A3-B89-C5-D39
A9-B89-C5-D39
A13-B89-C5-D39
A24-B89-C5-D39
A69-B89-C5-D39
A67-B89-C5-D39
A39-B89-C5-D39
A65-B89-C5-D39
A66-B89-C5-D39
A2-B92-C5-D39
A3-B92-C5-D39
A9-B92-C5-D39
A13-B92-C5-D39
A24-B92-C5-D39
A69-B92-C5-D39
A67-B92-C5-D39
A39-B92-C5-D39
A65-B92-C5-D39
A66-B92-C5-D39
A2-B4-C6-D39
A3-B4-C6-D39
A9-B4-C6-D39
A13-B4-C6-D39
A24-B4-C6-D39
A69-B4-C6-D39
A67-B4-C6-D39
A39-B4-C6-D39
A65-B4-C6-D39
A66-B4-C6-D39
A2-B5-C6-D39
A3-B5-C6-D39
A9-B5-C6-D39
A13-B5-C6-D39
A24-B5-C6-D39
A69-B5-C6-D39
A67-B5-C6-D39
A39-B5-C6-D39
A65-B5-C6-D39
A66-B5-C6-D39
A2-B6-C6-D39
A3-B6-C6-D39
A9-B6-C6-D39
A13-B6-C6-D39
A24-B6-C6-D39
A69-B6-C6-D39
A67-B6-C6-D39
A39-B6-C6-D39
A65-B6-C6-D39
A66-B6-C6-D39
A2-B32-C6-D39
A3-B32-C6-D39
A9-B32-C6-D39
A13-B32-C6-D39
A24-B32-C6-D39
A69-B32-C6-D39
A67-B32-C6-D39
A39-B32-C6-D39
A65-B32-C6-D39
A66-B32-C6-D39
A2-B39-C6-D39
A3-B39-C6-D39
A9-B39-C6-D39
A13-B39-C6-D39
A24-B39-C6-D39
A69-B39-C6-D39
A67-B39-C6-D39

-continued

A39-B39-C6-D39
A65-B39-C6-D39
A66-B39-C6-D39
A2-B45-C6-D39
A3-B45-C6-D39
A9-B45-C6-D39
A13-B45-C6-D39
A24-B45-C6-D39
A69-B45-C6-D39
A67-B45-C6-D39
A39-B45-C6-D39
A65-B45-C6-D39
A66-B45-C6-D39
A2-B53-C6-D39
A3-B53-C6-D39
A9-B53-C6-D39
A13-B53-C6-D39
A24-B53-C6-D39
A69-B53-C6-D39
A67-B53-C6-D39
A39-B53-C6-D39
A65-B53-C6-D39
A66-B53-C6-D39
A2-B79-C6-D39
A3-B79-C6-D39
A9-B79-C6-D39
A13-B79-C6-D39
A24-B79-C6-D39
A69-B79-C6-D39
A67-B79-C6-D39
A39-B79-C6-D39
A65-B79-C6-D39
A66-B79-C6-D39
A2-B80-C6-D39
A3-B80-C6-D39
A9-B80-C6-D39
A13-B80-C6-D39
A24-B80-C6-D39
A69-B80-C6-D39
A67-B80-C6-D39
A39-B80-C6-D39
A65-B80-C6-D39
A66-B80-C6-D39
A2-B85-C6-D39
A3-B85-C6-D39
A9-B85-C6-D39
A13-B85-C6-D39
A24-B85-C6-D39
A69-B85-C6-D39
A67-B85-C6-D39
A39-B85-C6-D39
A65-B85-C6-D39
A66-B85-C6-D39
A2-B86-C6-D39
A3-B86-C6-D39
A9-B86-C6-D39
A13-B86-C6-D39
A24-B86-C6-D39
A69-B86-C6-D39
A67-B86-C6-D39
A39-B86-C6-D39
A65-B86-C6-D39
A66-B86-C6-D39
A2-B87-C6-D39
A3-B87-C6-D39
A9-B87-C6-D39
A13-B87-C6-D39
A24-B87-C6-D39
A69-B87-C6-D39
A67-B87-C6-D39
A39-B87-C6-D39
A65-B87-C6-D39
A66-B87-C6-D39
A2-B89-C6-D39
A3-B89-C6-D39
A9-B89-C6-D39
A13-B89-C6-D39
A24-B89-C6-D39
A69-B89-C6-D39
A67-B89-C6-D39

-continued
A39-B89-C6-D39
A65-B89-C6-D39
A66-B89-C6-D39
A2-B92-C6-D39
A3-B92-C6-D39
A9-B92-C6-D39
A13-B92-C6-D39
A24-B92-C6-D39
A69-B92-C6-D39
A67-B92-C6-D39
A39-B92-C6-D39
A65-B92-C6-D39
A66-B92-C6-D39
A2-B4-C7-D39
A3-B4-C7-D39
A9-B4-C7-D39
A13-B4-C7-D39
A24-B4-C7-D39
A69-B4-C7-D39
A67-B4-C7-D39
A39-B4-C7-D39
A65-B4-C7-D39
A66-B4-C7-D39
A2-B5-C7-D39
A3-B5-C7-D39
A9-B5-C7-D39
A13-B5-C7-D39
A24-B5-C7-D39
A69-B5-C7-D39
A67-B5-C7-D39
A39-B5-C7-D39
A65-B5-C7-D39
A66-B5-C7-D39
A2-B6-C7-D39
A3-B6-C7-D39
A9-B6-C7-D39
A13-B6-C7-D39
A24-B6-C7-D39
A69-B6-C7-D39
A67-B6-C7-D39
A39-B6-C7-D39
A65-B6-C7-D39
A66-B6-C7-D39
A2-B32-C7-D39
A3-B32-C7-D39
A9-B32-C7-D39
A13-B32-C7-D39
A24-B32-C7-D39
A69-B32-C7-D39
A67-B32-C7-D39
A39-B32-C7-D39
A65-B32-C7-D39
A66-B32-C7-D39
A2-B39-C7-D39
A3-B39-C7-D39
A9-B39-C7-D39
A13-B39-C7-D39
A24-B39-C7-D39
A69-B39-C7-D39
A67-B39-C7-D39
A39-B39-C7-D39
A65-B39-C7-D39
A66-B39-C7-D39
A2-B45-C7-D39
A3-B45-C7-D39
A9-B45-C7-D39
A13-B45-C7-D39
A24-B45-C7-D39
A69-B45-C7-D39
A67-B45-C7-D39
A39-B45-C7-D39
A65-B45-C7-D39
A66-B45-C7-D39
A2-B53-C7-D39
A3-B53-C7-D39
A9-B53-C7-D39
A13-B53-C7-D39
A24-B53-C7-D39
A69-B53-C7-D39
A67-B53-C7-D39

-continued
A39-B53-C7-D39
A65-B53-C7-D39
A66-B53-C7-D39
A2-B79-C7-D39
A3-B79-C7-D39
A9-B79-C7-D39
A13-B79-C7-D39
A24-B79-C7-D39
A69-B79-C7-D39
A67-B79-C7-D39
A39-B79-C7-D39
A65-B79-C7-D39
A66-B79-C7-D39
A2-B80-C7-D39
A3-B80-C7-D39
A9-B80-C7-D39
A13-B80-C7-D39
A24-B80-C7-D39
A69-B80-C7-D39
A67-B80-C7-D39
A39-B80-C7-D39
A65-B80-C7-D39
A66-B80-C7-D39
A2-B85-C7-D39
A3-B85-C7-D39
A9-B85-C7-D39
A13-B85-C7-D39
A24-B85-C7-D39
A69-B85-C7-D39
A67-B85-C7-D39
A39-B85-C7-D39
A65-B85-C7-D39
A66-B85-C7-D39
A2-B86-C7-D39
A3-B86-C7-D39
A9-B86-C7-D39
A13-B86-C7-D39
A24-B86-C7-D39
A69-B86-C7-D39
A67-B86-C7-D39
A39-B86-C7-D39
A65-B86-C7-D39
A66-B86-C7-D39
A2-B87-C7-D39
A3-B87-C7-D39
A9-B87-C7-D39
A13-B87-C7-D39
A24-B87-C7-D39
A69-B87-C7-D39
A67-B87-C7-D39
A39-B87-C7-D39
A65-B87-C7-D39
A66-B87-C7-D39
A2-B89-C7-D39
A3-B89-C7-D39
A9-B89-C7-D39
A13-B89-C7-D39
A24-B89-C7-D39
A69-B89-C7-D39
A67-B89-C7-D39
A39-B89-C7-D39
A65-B89-C7-D39
A66-B89-C7-D39
A2-B92-C7-D39
A3-B92-C7-D39
A9-B92-C7-D39
A13-B92-C7-D39
A24-B92-C7-D39
A69-B92-C7-D39
A67-B92-C7-D39
A39-B92-C7-D39
A65-B92-C7-D39
A66-B92-C7-D39
A2-B4-C8-D39
A3-B4-C8-D39
A9-B4-C8-D39
A13-B4-C8-D39
A24-B4-C8-D39
A69-B4-C8-D39
A67-B4-C8-D39

-continued
A39-B4-C8-D39
A65-B4-C8-D39
A66-B4-C8-D39
A2-B5-C8-D39
A3-B5-C8-D39
A9-B5-C8-D39
A13-B5-C8-D39
A24-B5-C8-D39
A69-B5-C8-D39
A67-B5-C8-D39
A39-B5-C8-D39
A65-B5-C8-D39
A66-B5-C8-D39
A2-B6-C8-D39
A3-B6-C8-D39
A9-B6-C8-D39
A13-B6-C8-D39
A24-B6-C8-D39
A69-B6-C8-D39
A67-B6-C8-D39
A39-B6-C8-D39
A65-B6-C8-D39
A66-B6-C8-D39
A2-B32-C8-D39
A3-B32-C8-D39
A9-B32-C8-D39
A13-B32-C8-D39
A24-B32-C8-D39
A69-B32-C8-D39
A67-B32-C8-D39
A39-B32-C8-D39
A65-B32-C8-D39
A66-B32-C8-D39
A2-B39-C8-D39
A3-B39-C8-D39
A9-B39-C8-D39
A13-B39-C8-D39
A24-B39-C8-D39
A69-B39-C8-D39
A67-B39-C8-D39
A39-B39-C8-D39
A65-B39-C8-D39
A66-B39-C8-D39
A2-B45-C8-D39
A3-B45-C8-D39
A9-B45-C8-D39
A13-B45-C8-D39
A24-B45-C8-D39
A69-B45-C8-D39
A67-B45-C8-D39
A39-B45-C8-D39
A65-B45-C8-D39
A66-B45-C8-D39
A2-B53-C8-D39
A3-B53-C8-D39
A9-B53-C8-D39
A13-B53-C8-D39
A24-B53-C8-D39
A69-B53-C8-D39
A67-B53-C8-D39
A39-B53-C8-D39
A65-B53-C8-D39
A66-B53-C8-D39
A2-B79-C8-D39
A3-B79-C8-D39
A9-B79-C8-D39
A13-B79-C8-D39
A24-B79-C8-D39
A69-B79-C8-D39
A67-B79-C8-D39
A39-B79-C8-D39
A65-B79-C8-D39
A66-B79-C8-D39
A2-B80-C8-D39
A3-B80-C8-D39
A9-B80-C8-D39
A13-B80-C8-D39
A24-B80-C8-D39
A69-B80-C8-D39
A67-B80-C8-D39

-continued
A39-B80-C8-D39
A65-B80-C8-D39
A66-B80-C8-D39
A2-B85-C8-D39
A3-B85-C8-D39
A9-B85-C8-D39
A13-B85-C8-D39
A24-B85-C8-D39
A69-B85-C8-D39
A67-B85-C8-D39
A39-B85-C8-D39
A65-B85-C8-D39
A66-B85-C8-D39
A2-B86-C8-D39
A3-B86-C8-DD39
A9-B86-C8-D39
A13-B86-C8-D39
A24-B86-C8-D39
A69-B86-C8-D39
A67-B86-C8-D39
A39-B86-C8-D39
A65-B86-C8-D39
A66-B86-C8-D39
A2-B87-C8-D39
A3-B87-C8-D39
A9-B87-C8-D39
A13-B87-C8-D39
A24-B87-C8-D39
A69-B87-C8-D39
A67-B87-C8-D39
A39-B87-C8-D39
A65-B87-C8-D39
A66-B87-C8-D39
A2-B89-C8-D39
A3-B89-C8-D39
A9-B89-C8-D39
A13-B89-C8-D39
A24-B89-C8-D39
A69-B89-C8-D39
A67-B89-C8-D39
A39-B89-C8-D39
A65-B89-C8-D39
A66-B89-C8-D39
A2-B92-C8-D39
A3-B92-C8-D39
A9-B92-C8-D39
A13-B92-C8-D39
A24-B92-C8-D39
A69-B92-C8-D39
A67-B92-C8-D39
A39-B92-C8-D39
A65-B92-C8-D39
A66-B92-C8-D39
A2-B4-C9-D39
A3-B4-C9-D39
A9-B4-C9-D39
A13-B4-C9-D39
A24-B4-C9-D39
A69-B4-C9-D39
A67-B4-C9-D39
A39-B4-C9-D39
A65-B4-C9-D39
A66-B4-C9-D39
A2-B5-C9-D39
A3-B5-C9-D39
A9-B5-C9-D39
A13-B5-C9-D39
A24-B5-C9-D39
A69-B5-C9-D39
A67-B5-C9-D39
A39-B5-C9-D39
A65-B5-C9-D39
A66-B5-C9-D39
A2-B6-C9-D39
A3-B6-C9-D39
A9-B6-C9-D39
A13-B6-C9-D39
A24-B6-C9-D39
A69-B6-C9-D39
A67-B6-C9-D39

-continued
A39-B6-C9-D39
A65-B6-C9-D39
A66-B6-C9-D39
A2-B32-C9-D39
A3-B32-C9-D39
A9-B32-C9-D39
A13-B32-C9-D39
A24-B32-C9-D39
A69-B32-C9-D39
A67-B32-C9-D39
A39-B32-C9-D39
A65-B32-C9-D39
A66-B32-C9-D39
A2-B39-C9-D39
A3-B39-C9-D39
A9-B39-C9-D39
A13-B39-C9-D39
A24-B39-C9-D39
A69-B39-C9-D39
A67-B39-C9-D39
A39-B39-C9-D39
A65-B39-C9-D39
A66-B39-C9-D39
A2-B45-C9-D39
A3-B45-C9-D39
A9-B45-C9-D39
A13-B45-C9-D39
A24-B45-C9-D39
A69-B45-C9-D39
A67-B45-C9-D39
A39-B45-C9-D39
A65-B45-C9-D39
A66-B45-C9-D39
A2-B53-C9-D39
A3-B53-C9-D39
A9-B53-C9-D39
A13-B53-C9-D39
A24-B53-C9-D39
A69-B53-C9-D39
A67-B53-C9-D39
A39-B53-C9-D39
A65-B53-C9-D39
A66-B53-C9-D39
A2-B79-C9-D39
A3-B79-C9-D39
A9-B79-C9-D39
A13-B79-C9-D39
A24-B79-C9-D39
A69-B79-C9-D39
A67-B79-C9-D39
A39-B79-C9-D39
A65-B79-C9-D39
A66-B79-C9-D39
A2-B80-C9-D39
A3-B80-C9-D39
A9-B80-C9-D39
A13-B80-C9-D39
A24-B80-C9-D39
A69-B80-C9-D39
A67-B80-C9-D39
A39-B80-C9-D39
A65-B80-C9-D39
A66-B80-C9-D39
A2-B85-C9-D39
A3-B85-C9-D39
A9-B85-C9-D39
A13-B85-C9-D39
A24-B85-C9-D39
A69-B85-C9-D39
A67-B85-C9-D39
A39-B85-C9-D39
A65-B85-C9-D39
A66-B85-C9-D39
A2-B86-C9-D39
A3-B86-C9-D39
A9-B86-C9-D39
A13-B86-C9-D39
A24-B86-C9-D39
A69-B86-C9-D39
A67-B86-C9-D39

-continued
A39-B86-C9-D39
A65-B86-C9-D39
A66-B86-C9-D39
A2-B87-C9-D39
A3-B87-C9-D39
A9-B87-C9-D39
A13-B87-C9-D39
A24-B87-C9-D39
A69-B87-C9-D39
A67-B87-C9-D39
A39-B87-C9-D39
A65-B87-C9-D39
A66-B87-C9-D39
A2-B89-C9-D39
A3-B89-C9-D39
A9-B89-C9-D39
A13-B89-C9-D39
A24-B89-C9-D39
A69-B89-C9-D39
A67-B89-C9-D39
A39-B89-C9-D39
A65-B89-C9-D39
A66-B89-C9-D39
A2-B92-C9-D39
A3-B92-C9-D39
A9-B92-C9-D39
A13-B92-C9-D39
A24-B92-C9-D39
A69-B92-C9-D39
A67-B92-C9-D39
A39-B92-C9-D39
A65-B92-C9-D39
A66-B92-C9-D39
A2-B4-C10-D39
A3-B4-C10-D39
A9-B4-C10-D39
A13-B4-C10-D39
A24-B4-C10-D39
A69-B4-C10-D39
A67-B4-C10-D39
A39-B4-C10-D39
A65-B4-C10-D39
A66-B4-C10-D39
A2-B5-C10-D39
A3-B5-C10-D39
A9-B5-C10-D39
A13-B5-C10-D39
A24-B5-C10-D39
A69-B5-C10-D39
A67-B5-C10-D39
A39-B5-C10-D39
A65-B5-C10-D39
A66-B5-C10-D39
A2-B6-C10-D39
A3-B6-C10-D39
A9-B6-C10-D39
A13-B6-C10-D39
A24-B6-C10-D39
A69-B6-C10-D39
A67-B6-C10-D39
A39-B6-C10-D39
A65-B6-C10-D39
A66-B6-C10-D39
A2-B32-C10-D39
A3-B32-C10-D39
A9-B32-C10-D39
A13-B32-C10-D39
A24-B32-C10-D39
A69-B32-C10-D39
A67-B32-C10-D39
A39-B32-C10-D39
A65-B32-C10-D39
A66-B32-C10-D39
A2-B39-C10-D39
A3-B39-C10-D39
A9-B39-C10-D39
A13-B39-C10-D39
A24-B39-C10-D39
A69-B39-C10-D39
A67-B39-C10-D39

-continued

A39-B39-C10-D39
A65-B39-C10-D39
A66-B39-C10-D39
A2-B45-C10-D39
A3-B45-C10-D39
A9-B45-C10-D39
A13-B45-C10-D39
A24-B45-C10-D39
A69-B45-C10-D39
A67-B45-C10-D39
A39-B45-C10-D39
A65-B45-C10-D39
A66-B45-C10-D39
A2-B53-C10-D39
A3-B53-C10-D39
A9-B53-C10-D39
A13-B53-C10-D39
A24-B53-C10-D39
A69-B53-C10-D39
A67-B53-C10-D39
A39-B53-C10-D39
A65-B53-C10-D39
A66-B53-C10-D39
A2-B79-C10-D39
A3-B79-C10-D39
A9-B79-C10-D39
A13-B79-C10-D39
A24-B79-C10-D39
A69-B79-C10-D39
A67-B79-C10-D39
A39-B79-C10-D39
A65-B79-C10-D39
A66-B79-C10-D39
A2-B80-C10-D39
A3-B80-C10-D39
A9-B80-C10-D39
A13-B80-C10-D39
A24-B80-C10-D39
A69-B80-C10-D39
A67-B80-C10-D39
A39-B80-C10-D39
A65-B80-C10-D39
A66-B80-C10-D39
A2-B85-C10-D39
A3-B85-C10-D39
A9-B85-C10-D39
A13-B85-C10-D39
A24-B85-C10-D39
A69-B85-C10-D39
A67-B85-C10-D39
A39-B85-C10-D39
A65-B85-C10-D39
A66-B85-C10-D39
A2-B86-C10-D39
A3-B86-C10-D39
A9-B86-C10-D39
A13-B86-C10-D39
A24-B86-C10-D39
A69-B86-C10-D39
A67-B86-C10-D39
A39-B86-C10-D39
A65-B86-C10-D39
A66-B86-C10-D39
A2-B87-C10-D39
A3-B87-C10-D39
A9-B87-C10-D39
A13-B87-C10-D39
A24-B87-C10-D39
A69-B87-C10-D39
A67-B87-C10-D39
A39-B87-C10-D39
A65-B87-C10-D39
A66-B87-C10-D39
A2-B89-C10-D39
A3-B89-C10-D39
A9-B89-C10-D39
A13-B89-C10-D39
A24-B89-C10-D39
A69-B89-C10-D39
A67-B89-C10-D39

-continued

A39-B89-C10-D39
A65-B89-C10-D39
A66-B89-C10-D39
A2-B92-C10-D39
A3-B92-C10-D39
A9-B92-C10-D39
A13-B92-C10-D39
A24-B92-C10-D39
A69-B92-C10-D39
A67-B92-C10-D39
A39-B92-C10-D39
A65-B92-C10-D39
A66-B92-C10-D39
A2-B4-C11-D39
A3-B4-C11-D39
A9-B4-C11-D39
A13-B4-C11-D39
A24-B4-C11-D39
A69-B4-C11-D39
A67-B4-C11-D39
A39-B4-C11-D39
A65-B4-C11-D39
A66-B4-C11-D39
A2-B5-C11-D39
A3-B5-C11-D39
A9-B5-C11-D39
A13-B5-C11-D39
A24-B5-C11-D39
A69-B5-C11-D39
A67-B5-C11-D39
A39-B5-C11-D39
A65-B5-C11-D39
A66-B5-C11-D39
A2-B6-C11-D39
A3-B6-C11-D39
A9-B6-C11-D39
A13-B6-C11-D39
A24-B6-C11-D39
A69-B6-C11-D39
A67-B6-C11-D39
A39-B6-C11-D39
A65-B6-C11-D39
A66-B6-C11-D39
A2-B32-C11-D39
A3-B32-C11-D39
A9-B32-C11-D39
A13-B32-C11-D39
A24-B32-C11-D39
A69-B32-C11-D39
A67-B32-C11-D39
A39-B32-C11-D39
A65-B32-C11-D39
A66-B32-C11-D39
A2-B39-C11-D39
A3-B39-C11-D39
A9-B39-C11-D39
A13-B39-C11-D39
A24-B39-C11-D39
A69-B39-C11-D39
A67-B39-C11-D39
A39-B39-C11-D39
A65-B39-C11-D39
A66-B39-C11-D39
A2-B45-C11-D39
A3-B45-C11-D39
A9-B45-C11-D39
A13-B45-C11-D39
A24-B45-C11-D39
A69-B45-C11-D39
A67-B45-C11-D39
A39-B45-C11-D39
A65-B45-C11-D39
A66-B45-C11-D39
A2-B53-C11-D39
A3-B53-C11-D39
A9-B53-C11-D39
A13-B53-C11-D39
A24-B53-C11-D39
A69-B53-C11-D39
A67-B53-C11-D39

-continued

A39-B53-C11-D39
A65-B53-C11-D39
A66-B53-C11-D39
A2-B79-C11-D39
A3-B79-C11-D39
A9-B79-C11-D39
A13-B79-C11-D39
A24-B79-C11-D39
A69-B79-C11-D39
A67-B79-C11-D39
A39-B79-C11-D39
A65-B79-C11-D39
A66-B79-C11-D39
A2-B80-C11-D39
A3-B80-C11-D39
A9-B80-C11-D39
A13-B80-C11-D39
A24-B80-C11-D39
A69-B80-C11-D39
A67-B80-C11-D39
A39-B80-C11-D39
A65-B80-C11-D39
A66-B80-C11-D39
A2-B85-C11-D39
A3-B85-C11-D39
A9-B85-C11-D39
A13-B85-C11-D39
A24-B85-C11-D39
A69-B85-C11-D39
A67-B85-C11-D39
A39-B85-C11-D39
A65-B85-C11-D39
A66-B85-C11-D39
A2-B86-C11-D39
A3-B86-C11-D39
A9-B86-C11-D39
A13-B86-C11-D39
A24-B86-C11-D39
A69-B86-C11-D39
A67-B86-C11-D39
A39-B86-C11-D39
A65-B86-C11-D39
A66-B86-C11-D39
A2-B87-C11-D39
A3-B87-C11-D39
A9-B87-C11-D39
A13-B87-C11-D39
A24-B87-C11-D39
A69-B87-C11-D39
A67-B87-C11-D39
A39-B87-C11-D39
A65-B87-C11-D39
A66-B87-C11-D39
A2-B89-C11-D39
A3-B89-C11-D39
A9-B89-C11-D39
A13-B89-C11-D39
A24-B89-C11-D39
A69-B89-C11-D39
A67-B89-C11-D39
A39-B89-C11-D39
A65-B89-C11-D39
A66-B89-C11-D39
A2-B92-C11-D39
A3-B92-C11-D39
A9-B92-C11-D39
A13-B92-C11-D39
A24-B92-C11-D39
A69-B92-C11-D39
A67-B92-C11-D39
A39-B92-C11-D39
A65-B92-C11-D39
A66-B92-C11-D39
A2-B4-C12-D39
A3-B4-C12-D39
A9-B4-C12-D39
A13-B4-C12-D39
A24-B4-C12-D39
A69-B4-C12-D39
A67-B4-C12-D39

-continued

A39-B4-C12-D39
A65-B4-C12-D39
A66-B4-C12-D39
A2-B5-C12-D39
A3-B5-C12-D39
A9-B5-C12-D39
A13-B5-C12-D39
A24-B5-C12-D39
A69-B5-C12-D39
A67-B5-C12-D39
A39-B5-C12-D39
A65-B5-C12-D39
A66-B5-C12-D39
A2-B6-C12-D39
A3-B6-C12-D39
A9-B6-C12-D39
A13-B6-C12-D39
A24-B6-C12-D39
A69-B6-C12-D39
A67-B6-C12-D39
A39-B6-C12-D39
A65-B6-C12-D39
A66-B6-C12-D39
A2-B32-C12-D39
A3-B32-C12-D39
A9-B32-C12-D39
A13-B32-C12-D39
A24-B32-C12-D39
A69-B32-C12-D39
A67-B32-C12-D39
A39-B32-C12-D39
A65-B32-C12-D39
A66-B32-C12-D39
A2-B39-C12-D39
A3-B39-C12-D39
A9-B39-C12-D39
A13-B39-C12-D39
A24-B39-C12-D39
A69-B39-C12-D39
A67-B39-C12-D39
A39-B39-C12-D39
A65-B39-C12-D39
A66-B39-C12-D39
A2-B45-C12-D39
A3-B45-C12-D39
A9-B45-C12-D39
A13-B45-C12-D39
A24-B45-C12-D39
A69-B45-C12-D39
A67-B45-C12-D39
A39-B45-C12-D39
A65-B45-C12-D39
A66-B45-C12-D39
A2-B53-C12-D39
A3-B53-C12-D39
A9-B53-C12-D39
A13-B53-C12-D39
A24-B53-C12-D39
A69-B53-C12-D39
A67-B53-C12-D39
A39-B53-C12-D39
A65-B53-C12-D39
A66-B53-C12-D39
A2-B79-C12-D39
A3-B79-C12-D39
A9-B79-C12-D39
A13-B79-C12-D39
A24-B79-C12-D39
A69-B79-C12-D39
A67-B79-C12-D39
A39-B79-C12-D39
A65-B79-C12-D39
A66-B79-C12-D39
A2-B80-C12-D39
A3-B80-C12-D39
A9-B80-C12-D39
A13-B80-C12-D39
A24-B80-C12-D39
A69-B80-C12-D39
A67-B80-C12-D39

-continued
A39-B80-C12-D39
A65-B80-C12-D39
A66-B80-C12-D39
A2-B85-C12-D39
A3-B85-C12-D39
A9-B85-C12-D39
A13-B85-C12-D39
A24-B85-C12-D39
A69-B85-C12-D39
A67-B85-C12-D39
A39-B85-C12-D39
A65-B85-C12-D39
A66-B85-C12-D39
A2-B86-C12-D39
A3-B86-C12-D39
A9-B86-C12-D39
A13-B86-C12-D39
A24-B86-C12-D39
A69-B86-C12-D39
A67-B86-C12-D39
A39-B86-C12-D39
A65-B86-C12-D39
A66-B86-C12-D39
A2-B87-C12-D39
A3-B87-C12-D39
A9-B87-C12-D39
A13-B87-C12-D39
A24-B87-C12-D39
A69-B87-C12-D39
A67-B87-C12-D39
A39-B87-C12-D39
A65-B87-C12-D39
A66-B87-C12-D39
A2-B89-C12-D39
A3-B89-C12-D39
A9-B89-C12-D39
A13-B89-C12-D39
A24-B89-C12-D39
A69-B89-C12-D39
A67-B89-C12-D39
A39-B89-C12-D39
A65-B89-C12-D39
A66-B89-C12-D39
A2-B92-C12-D39
A3-B92-C12-D39
A9-B92-C12-D39
A13-B92-C12-D39
A24-B92-C12-D39
A69-B92-C12-D39
A67-B92-C12-D39
A39-B92-C12-D39
A65-B92-C12-D39
A66-B92-C12-D39
A2-B4-C13-D39
A3-B4-C13-D39
A9-B4-C13-D39
A13-B4-C13-D39
A24-B4-C13-D39
A69-B4-C13-D39
A67-B4-C13-D39
A39-B4-C13-D39
A65-B4-C13-D39
A66-B4-C13-D39
A2-B5-C13-D39
A3-B5-C13-D39
A9-B5-C13-D39
A13-B5-C13-D39
A24-B5-C13-D39
A69-B5-C13-D39
A67-B5-C13-D39
A39-B5-C13-D39
A65-B5-C13-D39
A66-B5-C13-D39
A2-B6-C13-D39
A3-B6-C13-D39
A9-B6-C13-D39
A13-B6-C13-D39
A24-B6-C13-D39
A69-B6-C13-D39
A67-B6-C13-D39

-continued
A39-B6-C13-D39
A65-B6-C13-D39
A66-B6-C13-D39
A2-B32-C13-D39
A3-B32-C13-D39
A9-B32-C13-D39
A13-B32-C13-D39
A24-B32-C13-D39
A69-B32-C13-D39
A67-B32-C13-D39
A39-B32-C13-D39
A65-B32-C13-D39
A66-B32-C13-D39
A2-B39-C13-D39
A3-B39-C13-D39
A9-B39-C13-D39
A13-B39-C13-D39
A24-B39-C13-D39
A69-B39-C13-D39
A67-B39-C13-D39
A39-B39-C13-D39
A65-B39-C13-D39
A66-B39-C13-D39
A2-B45-C13-D39
A3-B45-C13-D39
A9-B45-C13-D39
A13-B45-C13-D39
A24-B45-C13-D39
A69-B45-C13-D39
A67-B45-C13-D39
A39-B45-C13-D39
A65-B45-C13-D39
A66-B45-C13-D39
A2-B53-C13-D39
A3-B53-C13-D39
A9-B53-C13-D39
A13-B53-C13-D39
A24-B53-C13-D39
A69-B53-C13-D39
A67-B53-C13-D39
A39-B53-C13-D39
A65-B53-C13-D39
A66-B53-C13-D39
A2-B79-C13-D39
A3-B79-C13-D39
A9-B79-C13-D39
A13-B79-C13-D39
A24-B79-C13-D39
A69-B79-C13-D39
A67-B79-C13-D39
A39-B79-C13-D39
A65-B79-C13-D39
A66-B79-C13-D39
A2-B80-C13-D39
A3-B80-C13-D39
A9-B80-C13-D39
A13-B80-C13-D39
A24-B80-C13-D39
A69-B80-C13-D39
A67-B80-C13-D39
A39-B80-C13-D39
A65-B80-C13-D39
A66-B80-C13-D39
A2-B85-C13-D39
A3-B85-C13-D39
A9-B85-C13-D39
A13-B85-C13-D39
A24-B85-C13-D39
A69-B85-C13-D39
A67-B85-C13-D39
A39-B85-C13-D39
A65-B85-C13-D39
A66-B85-C13-D39
A2-B86-C13-D39
A3-B86-C13-D39
A9-B86-C13-D39
A13-B86-C13-D39
A24-B86-C13-D39
A69-B86-C13-D39
A67-B86-C13-D39

-continued

A39-B86-C13-D39
A65-B86-C13-D39
A66-B86-C13-D39
A2-B87-C13-D39
A3-B87-C13-D39
A9-B87-C13-D39
A13-B87-C13-D39
A24-B87-C13-D39
A69-B87-C13-D39
A67-B87-C13-D39
A39-B87-C13-D39
A65-B87-C13-D39
A66-B87-C13-D39
A2-B89-C13-D39
A3-B89-C13-D39
A9-B89-C13-D39
A13-B89-C13-D39
A24-B89-C13-D39
A69-B89-C13-D39
A67-B89-C13-D39
A39-B89-C13-D39
A65-B89-C13-D39
A66-B89-C13-D39
A2-B92-C13-D39
A3-B92-C13-D39
A9-B92-C13-D39
A13-B92-C13-D39
A24-B92-C13-D39
A69-B92-C13-D39
A67-B92-C13-D39
A39-B92-C13-D39
A65-B92-C13-D39
A66-B92-C13-D39
A2-B4-C1-D40
A3-B4-C1-D40
A9-B4-C1-D40
A13-B4-C1-D40
A24-B4-C1-D40
A69-B4-C1-D40
A67-B4-C1-D40
A39-B4-C1-D40
A65-B4-C1-D40
A66-B4-C1-D40
A2-B5-C1-D40
A3-B5-C1-D40
A9-B5-C1-D40
A13-B5-C1-D40
A24-B5-C1-D40
A69-B5-C1-D40
A67-B5-C1-D40
A39-B5-C1-D40
A65-B5-C1-D40
A66-B5-C1-D40
A2-B6-C1-D40
A3-B6-C1-D40
A9-B6-C1-D40
A13-B6-C1-D40
A24-B6-C1-D40
A69-B6-C1-D40
A67-B6-C1-D40
A39-B6-C1-D40
A65-B6-C1-D40
A66-B6-C1-D40
A2-B32-C1-D40
A3-B32-C1-D40
A9-B32-C1-D40
A13-B32-C1-D40
A24-B32-C1-D40
A69-B32-C1-D40
A67-B32-C1-D40
A39-B32-C1-D40
A65-B32-C1-D40
A66-B32-C1-D40
A2-B39-C1-D40
A3-B39-C1-D40
A9-B39-C1-D40
A13-B39-C1-D40
A24-B39-C1-D40
A69-B39-C1-D40
A67-B39-C1-D40

-continued

A39-B39-C1-D40
A65-B39-C1-D40
A66-B39-C1-D40
A2-B45-C1-D40
A3-B45-C1-D40
A9-B45-C1-D40
A13-B45-C1-D40
A24-B45-C1-D40
A69-B45-C1-D40
A67-B45-C1-D40
A39-B45-C1-D40
A65-B45-C1-D40
A66-B45-C1-D40
A2-B53-C1-D40
A3-B53-C1-D40
A9-B53-C1-D40
A13-B53-C1-D40
A24-B53-C1-D40
A69-B53-C1-D40
A67-B53-C1-D40
A39-B53-C1-D40
A65-B53-C1-D40
A66-B53-C1-D40
A2-B79-C1-D40
A3-B79-C1-D40
A9-B79-C1-D40
A13-B79-C1-D40
A24-B79-C1-D40
A69-B79-C1-D40
A67-B79-C1-D40
A39-B79-C1-D40
A65-B79-C1-D40
A66-B79-C1-D40
A2-B80-C1-D40
A3-B80-C1-D40
A9-B80-C1-D40
A13-B80-C1-D40
A24-B80-C1-D40
A69-B80-C1-D40
A67-B80-C1-D40
A39-B80-C1-D40
A65-B80-C1-D40
A66-B80-C1-D40
A2-B85-C1-D40
A3-B85-C1-D40
A9-B85-C1-D40
A13-B85-C1-D40
A24-B85-C1-D40
A69-B85-C1-D40
A67-B85-C1-D40
A39-B85-C1-D40
A65-B85-C1-D40
A66-B85-C1-D40
A2-B86-C1-D40
A3-B86-C1-D40
A9-B86-C1-D40
A13-B86-C1-D40
A24-B86-C1-D40
A69-B86-C1-D40
A67-B86-C1-D40
A39-B86-C1-D40
A65-B86-C1-D40
A66-B86-C1-D40
A2-B87-C1-D40
A3-B87-C1-D40
A9-B87-C1-D40
A13-B87-C1-D40
A24-B87-C1-D40
A69-B87-C1-D40
A67-B87-C1-D40
A39-B87-C1-D40
A65-B87-C1-D40
A66-B87-C1-D40
A2-B89-C1-D40
A3-B89-C1-D40
A9-B89-C1-D40
A13-B89-C1-D40
A24-B89-C1-D40
A69-B89-C1-D40
A67-B89-C1-D40

-continued
A39-B89-C1-D40
A65-B89-C1-D40
A66-B89-C1-D40
A2-B92-C1-D40
A3-B92-C1-D40
A9-B92-C1-D40
A13-B92-C1-D40
A24-B92-C1-D40
A69-B92-C1-D40
A67-B92-C1-D40
A39-B92-C1-D40
A65-B92-C1-D40
A66-B92-C1-D40
A2-B4-C2-D40
A3-B4-C2-D40
A9-B4-C2-D40
A13-B4-C2-D40
A24-B4-C2-D40
A69-B4-C2-D40
A67-B4-C2-D40
A39-B4-C2-D40
A65-B4-C2-D40
A66-B4-C2-D40
A2-B5-C2-D40
A3-B5-C2-D40
A9-B5-C2-D40
A13-B5-C2-D40
A24-B5-C2-D40
A69-B5-C2-D40
A67-B5-C2-D40
A39-B5-C2-D40
A65-B5-C2-D40
A66-B5-C2-D40
A2-B6-C2-D40
A3-B6-C2-D40
A9-B6-C2-D40
A13-B6-C2-D40
A24-B6-C2-D40
A69-B6-C2-D40
A67-B6-C2-D40
A39-B6-C2-D40
A65-B6-C2-D40
A66-B6-C2-D40
A2-B32-C2-D40
A3-B32-C2-D40
A9-B32-C2-D40
A13-B32-C2-D40
A24-B32-C2-D40
A69-B32-C2-D40
A67-B32-C2-D40
A39-B32-C2-D40
A65-B32-C2-D40
A66-B32-C2-D40
A2-B39-C2-D40
A3-B39-C2-D40
A9-B39-C2-D40
A13-B39-C2-D40
A24-B39-C2-D40
A69-B39-C2-D40
A67-B39-C2-D40
A39-B39-C2-D40
A65-B39-C2-D40
A66-B39-C2-D40
A2-B45-C2-D40
A3-B45-C2-D40
A9-B45-C2-D40
A13-B45-C2-D40
A24-B45-C2-D40
A69-B45-C2-D40
A67-B45-C2-D40
A39-B45-C2-D40
A65-B45-C2-D40
A66-B45-C2-D40
A2-B53-C2-D40
A3-B53-C2-D40
A9-B53-C2-D40
A13-B53-C2-D40
A24-B53-C2-D40
A69-B53-C2-D40
A67-B53-C2-D40

-continued
A39-B53-C2-D40
A65-B53-C2-D40
A66-B53-C2-D40
A2-B79-C2-D40
A3-B79-C2-D40
A9-B79-C2-D40
A13-B79-C2-D40
A24-B79-C2-D40
A69-B79-C2-D40
A67-B79-C2-D40
A39-B79-C2-D40
A65-B79-C2-D40
A66-B79-C2-D40
A2-B80-C2-D40
A3-B80-C2-D40
A9-B80-C2-D40
A13-B80-C2-D40
A24-B80-C2-D40
A69-B80-C2-D40
A67-B80-C2-D40
A39-B80-C2-D40
A65-B80-C2-D40
A66-B80-C2-D40
A2-B85-C2-D40
A3-B85-C2-D40
A9-B85-C2-D40
A13-B85-C2-D40
A24-B85-C2-D40
A69-B85-C2-D40
A67-B85-C2-D40
A39-B85-C2-D40
A65-B85-C2-D40
A66-B85-C2-D40
A2-B86-C2-D40
A3-B86-C2-D40
A9-B86-C2-D40
A13-B86-C2-D40
A24-B86-C2-D40
A69-B86-C2-D40
A67-B86-C2-D40
A39-B86-C2-D40
A65-B86-C2-D40
A66-B86-C2-D40
A2-B87-C2-D40
A3-B87-C2-D40
A9-B87-C2-D40
A13-B87-C2-D40
A24-B87-C2-D40
A69-B87-C2-D40
A67-B87-C2-D40
A39-B87-C2-D40
A65-B87-C2-D40
A66-B87-C2-D40
A2-B89-C2-D40
A3-B89-C2-D40
A9-B89-C2-D40
A13-B89-C2-D40
A24-B89-C2-D40
A69-B89-C2-D40
A67-B89-C2-D40
A39-B89-C2-D40
A65-B89-C2-D40
A66-B89-C2-D40
A2-B92-C2-D40
A3-B92-C2-D40
A9-B92-C2-D40
A13-B92-C2-D40
A24-B92-C2-D40
A69-B92-C2-D40
A67-B92-C2-D40
A39-B92-C2-D40
A65-B92-C2-D40
A66-B92-C2-D40
A2-B4-C3-D40
A3-B4-C3-D40
A9-B4-C3-D40
A13-B4-C3-D40
A24-B4-C3-D40
A69-B4-C3-D40
A67-B4-C3-D40

-continued

A39-B4-C3-D40
A65-B4-C3-D40
A66-B4-C3-D40
A2-B5-C3-D40
A3-B5-C3-D40
A9-B5-C3-D40
A13-B5-C3-D40
A24-B5-C3-D40
A69-B5-C3-D40
A67-B5-C3-D40
A39-B5-C3-D40
A65-B5-C3-D40
A66-B5-C3-D40
A2-B6-C3-D40
A3-B6-C3-D40
A9-B6-C3-D40
A13-B6-C3-D40
A24-B6-C3-D40
A69-B6-C3-D40
A67-B6-C3-D40
A39-B6-C3-D40
A65-B6-C3-D40
A66-B6-C3-D40
A2-B32-C3-D40
A3-B32-C3-D40
A9-B32-C3-D40
A13-B32-C3-D40
A24-B32-C3-D40
A69-B32-C3-D40
A67-B32-C3-D40
A39-B32-C3-D40
A65-B32-C3-D40
A66-B32-C3-D40
A2-B39-C3-D40
A3-B39-C3-D40
A9-B39-C3-D40
A13-B39-C3-D40
A24-B39-C3-D40
A69-B39-C3-D40
A67-B39-C3-D40
A39-B39-C3-D40
A65-B39-C3-D40
A66-B39-C3-D40
A2-B45-C3-D40
A3-B45-C3-D40
A9-B45-C3-D40
A13-B45-C3-D40
A24-B45-C3-D40
A69-B45-C3-D40
A67-B45-C3-D40
A39-B45-C3-D40
A65-B45-C3-D40
A66-B45-C3-D40
A2-B53-C3-D40
A3-B53-C3-D40
A9-B53-C3-D40
A13-B53-C3-D40
A24-B53-C3-D40
A69-B53-C3-D40
A67-B53-C3-D40
A39-B53-C3-D40
A65-B53-C3-D40
A66-B53-C3-D40
A2-B79-C3-D40
A3-B79-C3-D40
A9-B79-C3-D40
A13-B79-C3-D40
A24-B79-C3-D40
A69-B79-C3-D40
A67-B79-C3-D40
A39-B79-C3-D40
A65-B79-C3-D40
A66-B79-C3-D40
A2-B80-C3-D40
A3-B80-C3-D40
A9-B80-C3-D40
A13-B80-C3-D40
A24-B80-C3-D40
A69-B80-C3-D40
A67-B80-C3-D40

-continued

A39-B80-C3-D40
A65-B80-C3-D40
A66-B80-C3-D40
A2-B85-C3-D40
A3-B85-C3-D40
A9-B85-C3-D40
A13-B85-C3-D40
A24-B85-C3-D40
A69-B85-C3-D40
A67-B85-C3-D40
A39-B85-C3-D40
A65-B85-C3-D40
A66-B85-C3-D40
A2-B86-C3-D40
A3-B86-C3-D40
A9-B86-C3-D40
A13-B86-C3-D40
A24-B86-C3-D40
A69-B86-C3-D40
A67-B86-C3-D40
A39-B86-C3-D40
A65-B86-C3-D40
A66-B86-C3-D40
A2-B87-C3-D40
A3-B87-C3-D40
A9-B87-C3-D40
A13-B87-C3-D40
A24-B87-C3-D40
A69-B87-C3-D40
A67-B87-C3-D40
A39-B87-C3-D40
A65-B87-C3-D40
A66-B87-C3-D40
A2-B89-C3-D40
A3-B89-C3-D40
A9-B89-C3-D40
A13-B89-C3-D40
A24-B89-C3-D40
A69-B89-C3-D40
A67-B89-C3-D40
A39-B89-C3-D40
A65-B89-C3-D40
A66-B89-C3-D40
A2-B92-C3-D40
A3-B92-C3-D40
A9-B92-C3-D40
A13-B92-C3-D40
A24-B92-C3-D40
A69-B92-C3-D40
A67-B92-C3-D40
A39-B92-C3-D40
A65-B92-C3-D40
A66-B92-C3-D40
A2-B4-C4-D40
A3-B4-C4-D40
A9-B4-C4-D40
A13-B4-C4-D40
A24-B4-C4-D40
A69-B4-C4-D40
A67-B4-C4-D40
A39-B4-C4-D40
A65-B4-C4-D40
A66-B4-C4-D40
A2-B5-C4-D40
A3-B5-C4-D40
A9-B5-C4-D40
A13-B5-C4-D40
A24-B5-C4-D40
A69-B5-C4-D40
A67-B5-C4-D40
A39-B5-C4-D40
A65-B5-C4-D40
A66-B5-C4-D40
A2-B6-C4-D40
A3-B6-C4-D40
A9-B6-C4-D40
A13-B6-C4-D40
A24-B6-C4-D40
A69-B6-C4-D40
A67-B6-C4-D40

-continued

A39-B6-C4-D40
A65-B6-C4-D40
A66-B6-C4-D40
A2-B32-C4-D40
A3-B32-C4-D40
A9-B32-C4-D40
A13-B32-C4-D40
A24-B32-C4-D40
A69-B32-C4-D40
A67-B32-C4-D40
A39-B32-C4-D40
A65-B32-C4-D40
A66-B32-C4-D40
A2-B39-C4-D40
A3-B39-C4-D40
A9-B39-C4-D40
A13-B39-C4-D40
A24-B39-C4-D40
A69-B39-C4-D40
A67-B39-C4-D40
A39-B39-C4-D40
A65-B39-C4-D40
A66-B39-C4-D40
A2-B45-C4-D40
A3-B45-C4-D40
A9-B45-C4-D40
A13-B45-C4-D40
A24-B45-C4-D40
A69-B45-C4-D40
A67-B45-C4-D40
A39-B45-C4-D40
A65-B45-C4-D40
A66-B45-C4-D40
A2-B53-C4-D40
A3-B53-C4-D40
A9-B53-C4-D40
A13-B53-C4-D40
A24-B53-C4-D40
A69-B53-C4-D40
A67-B53-C4-D40
A39-B53-C4-D40
A65-B53-C4-D40
A66-B53-C4-D40
A2-B79-C4-D40
A3-B79-C4-D40
A9-B79-C4-D40
A13-B79-C4-D40
A24-B79-C4-D40
A69-B79-C4-D40
A67-B79-C4-D40
A39-B79-C4-D40
A65-B79-C4-D40
A66-B79-C4-D40
A2-B80-C4-D40
A3-B80-C4-D40
A9-B80-C4-D40
A13-B80-C4-D40
A24-B80-C4-D40
A69-B80-C4-D40
A67-B80-C4-D40
A39-B80-C4-D40
A65-B80-C4-D40
A66-B80-C4-D40
A2-B85-C4-D40
A3-B85-C4-D40
A9-B85-C4-D40
A13-B85-C4-D40
A24-B85-C4-D40
A69-B85-C4-D40
A67-B85-C4-D40
A39-B85-C4-D40
A65-B85-C4-D40
A66-B85-C4-D40
A2-B86-C4-D40
A3-B86-C4-D40
A9-B86-C4-D40
A13-B86-C4-D40
A24-B86-C4-D40
A69-B86-C4-D40
A67-B86-C4-D40

-continued

A39-B86-C4-D40
A65-B86-C4-D40
A66-B86-C4-D40
A2-B87-C4-D40
A3-B87-C4-D40
A9-B87-C4-D40
A13-B87-C4-D40
A24-B87-C4-D40
A69-B87-C4-D40
A67-B87-C4-D40
A39-B87-C4-D40
A65-B87-C4-D40
A66-B87-C4-D40
A2-B89-C4-D40
A3-B89-C4-D40
A9-B89-C4-D40
A13-B89-C4-D40
A24-B89-C4-D40
A69-B89-C4-D40
A67-B89-C4-D40
A39-B89-C4-D40
A65-B89-C4-D40
A66-B89-C4-D40
A2-B92-C4-D40
A3-B92-C4-D40
A9-B92-C4-D40
A13-B92-C4-D40
A24-B92-C4-D40
A69-B92-C4-D40
A67-B92-C4-D40
A39-B92-C4-D40
A65-B92-C4-D40
A66-B92-C4-D40
A2-B4-C5-D40
A3-B4-C5-D40
A9-B4-C5-D40
A13-B4-C5-D40
A24-B4-C5-D40
A69-B4-C5-D40
A67-B4-C5-D40
A39-B4-C5-D40
A65-B4-C5-D40
A66-B4-C5-D40
A2-B5-C5-D40
A3-B5-C5-D40
A9-B5-C5-D40
A13-B5-C5-D40
A24-B5-C5-D40
A69-B5-C5-D40
A67-B5-C5-D40
A39-B5-C5-D40
A65-B5-C5-D40
A66-B5-C5-D40
A2-B6-C5-D40
A3-B6-C5-D40
A9-B6-C5-D40
A13-B6-C5-D40
A24-B6-C5-D40
A69-B6-C5-D40
A67-B6-C5-D40
A39-B6-C5-D40
A65-B6-C5-D40
A66-B6-C5-D40
A2-B32-C5-D40
A3-B32-C5-D40
A9-B32-C5-D40
A13-B32-C5-D40
A24-B32-C5-D40
A69-B32-C5-D40
A67-B32-C5-D40
A39-B32-C5-D40
A65-B32-C5-D40
A66-B32-C5-D40
A2-B39-C5-D40
A3-B39-C5-D40
A9-B39-C5-D40
A13-B39-C5-D40
A24-B39-C5-D40
A69-B39-C5-D40
A67-B39-C5-D40

-continued
A39-B39-C5-D40
A65-B39-C5-D40
A66-B39-C5-D40
A2-B45-C5-D40
A3-B45-C5-D40
A9-B45-C5-D40
A13-B45-C5-D40
A24-B45-C5-D40
A69-B45-C5-D40
A67-B45-C5-D40
A39-B45-C5-D40
A65-B45-C5-D40
A66-B45-C5-D40
A2-B53-C5-D40
A3-B53-C5-D40
A9-B53-C5-D40
A13-B53-C5-D40
A24-B53-C5-D40
A69-B53-C5-D40
A67-B53-C5-D40
A39-B53-C5-D40
A65-B53-C5-D40
A66-B53-C5-D40
A2-B79-C5-D40
A3-B79-C5-D40
A9-B79-C5-D40
A13-B79-C5-D40
A24-B79-C5-D40
A69-B79-C5-D40
A67-B79-C5-D40
A39-B79-C5-D40
A65-B79-C5-D40
A66-B79-C5-D40
A2-B80-C5-D40
A3-B80-C5-D40
A9-B80-C5-D40
A13-B80-C5-D40
A24-B80-C5-D40
A69-B80-C5-D40
A67-B80-C5-D40
A39-B80-C5-D40
A65-B80-C5-D40
A66-B80-C5-D40
A2-B85-C5-D40
A3-B85-C5-D40
A9-B85-C5-D40
A13-B85-C8-D40
A24-B85-C5-D40
A69-B85-C5-D40
A67-B85-C5-D40
A39-B85-C5-D40
A65-B85-C5-D40
A66-B85-C5-D40
A2-B86-C5-D40
A3-B86-C5-D40
A9-B86-C5-D40
A13-B86-C5-D40
A24-B86-C5-D40
A69-B86-C5-D40
A67-B86-C5-D40
A39-B86-C5-D40
A65-B86-C5-D40
A66-B86-C5-D40
A2-B87-C5-D40
A3-B87-C5-D40
A9-B87-C5-D40
A13-B87-C5-D40
A24-B87-C5-D40
A69-B87-C5-D40
A67-B87-C5-D40
A39-B87-C5-D40
A65-B87-C5-D40
A66-B87-C5-D40
A2-B89-C5-D40
A3-B89-C5-D40
A9-B89-C5-D40
A13-B89-C5-D40
A24-B89-C5-D40
A69-B89-C5-D40
A67-B89-C5-D40

-continued
A39-B89-C5-D40
A65-B89-C5-D40
A66-B89-C5-D40
A2-B92-C5-D40
A3-B92-C5-D40
A9-B92-C5-D40
A13-B92-C5-D40
A24-B92-C5-D40
A69-B92-C5-D40
A67-B92-C5-D40
A39-B92-C5-D40
A65-B92-C5-D40
A66-B92-C5-D40
A2-B4-C6-D40
A3-B4-C6-D40
A9-B4-C6-D40
A13-B4-C6-D40
A24-B4-C6-D40
A69-B4-C6-D40
A67-B4-C6-D40
A39-B4-C6-D40
A65-B4-C6-D40
A66-B4-C6-D40
A2-B5-C6-D40
A3-B5-C6-D40
A9-B5-C6-D40
A13-B5-C6-D40
A24-B5-C6-D40
A69-B5-C6-D40
A67-B5-C6-D40
A39-B5-C6-D40
A65-B5-C6-D40
A66-B5-C6-D40
A2-B6-C6-D40
A3-B6-C6-D40
A9-B6-C6-D40
A13-B6-C6-D40
A24-B6-C6-D40
A69-B6-C6-D40
A67-B6-C6-D40
A39-B6-C6-D40
A65-B6-C6-D40
A66-B6-C6-D40
A2-B32-C6-D40
A3-B32-C6-D40
A9-B32-C6-D40
A13-B32-C6-D40
A24-B32-C6-D40
A69-B32-C6-D40
A67-B32-C6-D40
A39-B32-C6-D40
A65-B32-C6-D40
A66-B32-C6-D40
A2-B39-C6-D40
A3-B39-C6-D40
A9-B39-C6-D40
A13-B39-C6-D40
A24-B39-C6-D40
A69-B39-C6-D40
A67-B39-C6-D40
A39-B39-C6-D40
A65-B39-C6-D40
A66-B39-C6-D40
A2-B45-C6-D40
A3-B45-C6-D40
A9-B45-C6-D40
A13-B45-C6-D40
A24-B45-C6-D40
A69-B45-C6-D40
A67-B45-C6-D40
A39-B45-C6-D40
A65-B45-C6-D40
A66-B45-C6-D40
A2-B53-C6-D40
A3-B53-C6-D40
A9-B53-C6-D40
A13-B53-C6-D40
A24-B53-C6-D40
A69-B53-C6-D40
A67-B53-C6-D40

-continued

A39-B53-C6-D40
A65-B53-C6-D40
A66-B53-C6-D40
A2-B79-C6-D40
A3-B79-C6-D40
A9-B79-C6-D40
A13-B79-C6-D40
A24-B79-C6-D40
A69-B79-C6-D40
A67-B79-C6-D40
A39-B79-C6-D40
A65-B79-C6-D40
A66-B79-C6-D40
A2-B80-C6-D40
A3-B80-C6-D40
A9-B80-C6-D40
A13-B80-C6-D40
A24-B80-C6-D40
A69-B80-C6-D40
A67-B80-C6-D40
A39-B80-C6-D40
A65-B80-C6-D40
A66-B80-C6-D40
A2-B85-C6-D40
A3-B85-C6-D40
A9-B85-C6-D40
A13-B85-C6-D40
A24-B85-C6-D40
A69-B85-C6-D40
A67-B85-C6-D40
A39-B85-C6-D40
A65-B85-C6-D40
A66-B85-C6-D40
A2-B86-C6-D40
A3-B86-C6-D40
A9-B86-C6-D40
A13-B86-C6-D40
A24-B86-C6-D40
A69-B86-C6-D40
A67-B86-C6-D40
A39-B86-C6-D40
A65-B86-C6-D40
A66-B86-C6-D40
A2-B87-C6-D40
A3-B87-C6-D40
A9-B87-C6-D40
A13-B87-C6-D40
A24-B87-C6-D40
A69-B87-C6-D40
A67-B87-C6-D40
A39-B87-C6-D40
A65-B87-C6-D40
A66-B87-C6-D40
A2-B89-C6-D40
A3-B89-C6-D40
A9-B89-C6-D40
A13-B89-C6-D40
A24-B89-C6-D40
A69-B89-C6-D40
A67-B89-C6-D40
A39-B89-C6-D40
A65-B89-C6-D40
A66-B89-C6-D40
A2-B92-C6-D40
A3-B92-C6-D40
A9-B92-C6-D40
A13-B92-C6-D40
A24-B92-C6-D40
A69-B92-C6-D40
A67-B92-C6-D40
A39-B92-C6-D40
A65-B92-C6-D40
A66-B92-C6-D40
A2-B4-C7-D40
A3-B4-C7-D40
A9-B4-C7-D40
A13-B4-C7-D40
A24-B4-C7-D40
A69-B4-C7-D40
A67-B4-C7-D40

-continued

A39-B4-C7-D40
A65-B4-C7-D40
A66-B4-C7-D40
A2-B5-C7-D40
A3-B5-C7-D40
A9-B5-C7-D40
A13-B5-C7-D40
A24-B5-C7-D40
A69-B5-C7-D40
A67-B5-C7-D40
A39-B5-C7-D40
A65-B5-C7-D40
A66-B5-C7-D40
A2-B6-C7-D40
A3-B6-C7-D40
A9-B6-C7-D40
A13-B6-C7-D40
A24-B6-C7-D40
A69-B6-C7-D40
A67-B6-C7-D40
A39-B6-C7-D40
A65-B6-C7-D40
A66-B6-C7-D40
A2-B32-C7-D40
A3-B32-C7-D40
A9-B32-C7-D40
A13-B32-C7-D40
A24-B32-C7-D40
A69-B32-C7-D40
A67-B32-C7-D40
A39-B32-C7-D40
A65-B32-C7-D40
A66-B32-C7-D40
A2-B39-C7-D40
A3-B39-C7-D4A0
A9-B39-C7-D40
A13-B39-C7-D40
A24-B39-C7-D40
A69-B39-C7-D40
A67-B39-C7-D40
A39-B39-C7-D40
A65-B39-C7-D40
A66-B39-C7-D40
A2-B45-C7-D40
A3-B45-C7-D40
A9-B45-C7-D40
A13-B45-C7-D40
A24-B45-C7-D40
A69-B45-C7-D40
A67-B45-C7-D40
A39-B45-C7-D40
A65-B45-C7-D40
A66-B45-C7-D40
A2-B53-C7-D40
A3-B53-C7-D40
A9-B53-C7-D40
A13-B53-C7-D40
A24-B53-C7-D40
A69-B53-C7-D40
A67-B53-C7-D40
A39-B53-C7-D40
A65-B53-C7-D40
A66-B53-C7-D40
A2-B79-C7-D40
A3-B79-C7-D40
A9-B79-C7-D40
A13-B79-C7-D40
A24-B79-C7-D40
A69-B79-C7-D40
A67-B79-C7-D40
A39-B79-C7-D40
A65-B79-C7-D40
A66-B79-C7-D40
A2-B80-C7-D40
A3-B80-C7-D40
A9-B80-C7-D40
A13-B80-C7-D40
A24-B80-C7-D40
A69-B80-C7-D40
A67-B80-C7-D40

-continued
A39-B80-C7-D40
A65-B80-C7-D40
A66-B80-C7-D40
A2-B85-C7-D40
A3-B85-C7-D40
A9-B85-C7-D40
A13-B85-C7-D40
A24-B85-C7-D40
A69-B85-C7-D40
67-B85-C7-D40
A39-B85-C7-D40
A65-B85-C7-D40
A66-B85-C7-D40
A2-B86-C7-D40
A3-B86-C7-D40
A9-B86-C7-D40
A13-B86-C7-D40
A24-B86-C7-D40
A69-B86-C7-D40
A67-B86-C7-D40
A39-B86-C7-D40
A65-B86-C7-D40
A66-B86-C7-D40
A2-B87-C7-D40
A3-B87-C7-D40
A9-B87-C7-D40
A13-B87-C7-D40
A24-B87-C7-D40
A69-B87-C7-D40
A67-B87-C7-D40
A39-B87-C7-D40
A65-B87-C7-D40
A66-B87-C7-D40
A2-B89-C7-D40
A3-B89-C7-D40
A9-B89-C7-D40
A13-B89-C7-D40
A24-B89-C7-D40
A69-B89-C7-D40
A67-B89-C7-D40
A39-B89-C7-D40
A65-B89-C7-D40
A66-B89-C7-D40
A2-B92-C7-D40
A3-B92-C7-D40
A9-B92-C7-D40
A13-B92-C7-D40
A24-B92-C7-D40
A69-B92-C7-D40
A67-B92-C7-D40
A39-B92-C7-D40
A65-B92-C7-D40
A66-B92-C7-D40
A2-B4-C8-D40
A3-B4-C8-D40
A9-B4-C8-D40
A13-B4-C8-D40
A24-B4-C8-D40
A69-B4-C8-D40
A67-B4-C8-D40
A39-B4-C8-D40
A65-B4-C8-D40
A66-B4-C8-D40
A2-B5-C8-D40
A3-B5-C8-D40
A9-B5-C8-D40
A13-B5-C8-D40
A24-B5-C8-D40
A69-B5-C8-D40
A67-B5-C8-D40
A39-B5-C8-D40
A65-B5-C8-D40
A66-B5-C8-D40
A2-B6-C8-D40
A3-B6-C8-D40
A9-B6-C8-D40
A13-B6-C8-D40
A24-B6-C8-D40
A69-B6-C8-D40
A67-B6-C8-D40

-continued
A39-B6-C8-D40
A65-B6-C8-D40
A66-B6-C8-D40
A2-B32-C8-D40
A3-B32-C8-D40
A9-B32-C8-D40
A13-B32-C8-D40
A24-B32-C8-D40
A69-B32-C8-D40
A67-B32-C8-D40
A39-B32-C8-D40
A65-B32-C8-D40
A66-B32-C8-D40
A2-B39-C8-D40
A3-B39-C8-D40
A9-B39-C8-D40
A13-B39-C8-D40
A24-B39-C8-D40
A69-B39-C8-D40
A67-B39-C8-D40
A39-B39-C8-D40
A65-B39-C8-D40
A66-B39-C8-D40
A2-B45-C8-D40
A3-B45-C8-D40
A9-B45-C8-D40
A13-B45-C8-D40
A24-B45-C8-D40
A69-B45-C8-D40
A67-B45-C8-D40
A39-B45-C8-D40
A65-B45-C8-D40
A66-B45-C8-D40
A2-B53-C8-D40
A3-B53-C8-D40
A9-B53-C8-D40
A13-B53-C8-D40
A24-B53-C8-D40
A69-B53-C8-D40
A67-B53-C8-D40
A39-B53-C8-D40
A65-B53-C8-D40
A66-B53-C8-D40
A2-B79-C8-D40
A3-B79-C8-D40
A9-B79-C8-D40
A13-B79-C8-D40
A24-B79-C8-D40
A69-B79-C8-D40
A67-B79-C8-D40
A39-B79-C8-D40
A65-B79-C8-D40
A66-B79-C8-D40
A2-B80-C8-D40
A3-B80-C8-D40
A9-B80-C8-D40
A13-B80-C8-D40
A24-B80-C8-D40
A69-B80-C8-D40
A67-B80-C8-D40
A39-B80-C8-D40
A65-B80-C8-D40
A66-B80-C8-D40
A2-B85-C8-D40
A3-B85-C8-D40
A9-B85-C8-D40
A13-B85-C8-D40
A24-B85-C8-D40
A69-B85-C8-D40
A67-B85-C8-D40
A39-B85-C8-D40
A65-B85-C8-D40
A66-B85-C8-D40
A2-B86-C8-D40
A3-B86-C8-D40
A9-B86-C8-D40
A13-B86-C8-D40
A24-B86-C8-D40
A69-B86-C8-D40
A67-B86-C8-D40

-continued
A39-B86-C8-D40
A65-B86-C8-D40
A66-B86-C8-D40
A2-B87-C8-D40
A3-B87-C8-D40
A9-B87-C8-D40
A13-B87-C8-D40
A24-B87-C8-D40
A69-B87-C8-D40
A67-B87-C8-D40
A39-B87-C8-D40
A65-B87-C8-D40
A66-B87-C8-D40
A2-B89-C8-D40
A3-B89-C8-D40
A9-B89-C8-D40
A13-B89-C8-D40
A24-B89-C8-D40
A69-B89-C8-D40
A67-B89-C8-D40
A39-B89-C8-D40
A65-B89-C8-D40
A66-B89-C8-D40
A2-B92-C8-D40
A3-B92-C8-D40
A9-B92-C8-D40
A13-B92-C8-D40
A24-B92-C8-D40
A69-B92-C8-D40
A67-B92-C8-D40
A39-B92-C8-D40
A65-B92-C8-D40
A66-B92-C8-D40
A2-B4-C9-D40
A3-B4-C9-D40
A9-B4-C9-D40
A13-B4-C9-D40
A24-B4-C9-D40
A69-B4-C9-D40
A67-B4-C9-D40
A39-B4-C9-D40
A65-B4-C9-D40
A66-B4-C9-D40
A2-B5-C9-D40
A3-B5-C9-D40
A9-B5-C9-D40
A13-B5-C9-D40
A24-B5-C9-D40
A69-B5-C9-D40
A67-B5-C9-D40
A39-B5-C9-D40
A65-B5-C9-D40
A66-B5-C9-D40
A2-B6-C9-D40
A3-B6-C9-D40
A9-B6-C9-D40
A13-B6-C9-D40
A24-B6-C9-D40
A69-B6-C9-D40
A67-B6-C9-D40
A39-B6-C9-D40
A65-B6-C9-D40
A66-B6-C9-D40
A2-B32-C9-D40
A3-B32-C9-D40
A9-B32-C9-D40
A13-B32-C9-D40
A24-B32-C9-D40
A69-B32-C9-D40
A67-B32-C9-D40
A39-B32-C9-D40
A65-B32-C9-D40
A66-B32-C9-D40
A2-B39-C9-D40
A3-B39-C9-D40
A9-B39-C9-D40
A13-B39-C9-D40
A24-B39-C9-D40
A69-B39-C9-D40
A67-B39-C9-D40

-continued
A39-B39-C9-D40
A65-B39-C9-D40
A66-B39-C9-D40
A2-B45-C9-D40
A3-B45-C9-D40
A9-B45-C9-D40
A13-B45-C9-D40
A24-B45-C9-D40
A69-B45-C9-D40
A67-B45-C9-D40
A39-B45-C9-D40
A65-B45-C9-D40
A66-B45-C9-D40
A2-B53-C9-D40
A3-B53-C9-D40
A9-B53-C9-D40
A13-B53-C9-D40
A24-B53-C9-D40
A69-B53-C9-D40
A67-B53-C9-D40
A39-B53-C9-D40
A65-B53-C9-D40
A66-B53-C9-D40
A2-B79-C9-D40
A3-B79-C9-D40
A9-B79-C9-D40
A13-B79-C9-D40
A24-B79-C9-D40
A69-B79-C9-D40
A67-B79-C9-D40
A39-B79-C9-D40
A65-B79-C9-D40
A66-B79-C9-D40
A2-B80-C9-D40
A3-B80-C9-D40
A9-B80-C9-D40
A13-B80-C9-D40
A24-B80-C9-D40
A69-B80-C9-D40
A67-B80-C9-D40
A39-B80-C9-D40
A65-B80-C9-D40
A66-B80-C9-D40
A2-B85-C9-D40
A3-B85-C9-D40
A9-B85-C9-D40
A13-B85-C9-D40
A24-B85-C9-D40
A69-B85-C9-D40
A67-B85-C9-D40
A39-B85-C9-D40
A65-B85-C9-D40
A66-B85-C9-D40
A2-B86-C9-D40
A3-B86-C9-D40
A9-B86-C9-D40
A13-B86-C9-D40
A24-B86-C9-D40
A69-B86-C9-D40
A67-B86-C9-D40
A39-B86-C9-D40
A65-B86-C9-D40
A66-B86-C9-D40
A2-B87-C9-D40
A3-B87-C9-D40
A9-B87-C9-D40
A13-B87-C9-D40
A24-B87-C9-D40
A69-B87-C9-D40
A67-B87-C9-D40
A39-B87-C9-D40
A65-B87-C9-D40
A66-B87-C9-D40
A2-B89-C9-D40
A3-B89-C9-D40
A9-B89-C9-D40
A13-B89-C9-D40
A24-B89-C9-D40
A69-B89-C9-D40
A67-B89-C9-D40

-continued

A39-B89-C9-D40
A65-B89-C9-D40
A66-B89-C9-D40
A2-B92-C9-D40
A3-B92-C9-D40
A9-B92-C9-D40
A13-B92-C9-D40
A24-B92-C9-D40
A69-B92-C9-D40
A67-B92-C9-O40
A39-B92-C9-D40
A65-B92-C9-D40
A66-B92-C9-D40
A2-B4-C10-D40
A3-B4-C10-D40
A9-B4-C10-D40
A13-B4-C10-D40
A24-B4-C10-D40
A69-B4-C10-D40
A67-B4-C10-D40
A39-B4-C10-D40
A65-B4-C10-D40
A66-B4-C10-D40
A2-B5-C10-D40
A3-B5-C10-D40
A9-B5-C10-D40
A13-B5-C10-D40
A24-B5-C10-D40
A69-B5-C10-D40
A67-B5-C10-D40
A39-B5-C10-D40
A65-B5-C10-D40
A66-B5-C10-D40
A2-B6-C10-D40
A3-B6-C10-D40
A9-B6-C10-D40
A13-B6-C10-D40
A24-B6-C10-D40
A69-B6-C10-D40
A67-B6-C10-D40
A39-B6-C10-D40
A65-B6-C10-D40
A66-B6-C10-D40
A2-B32-C10-D40
A3-B32-C10-D40
A9-B32-C10-D40
A13-B32-C10-D40
A24-B32-C10-D40
A69-B32-C10-D40
A67-B32-C10-D40
A39-B32-C10-D40
A65-B32-C10-D40
A66-B32-C10-D40
A2-B39-C10-D40
A3-B39-C10-D40
A9-B39-C10-D40
A13-B39-C10-D40
A24-B39-C10-D40
A69-B39-C10-D40
A67-B39-C10-D40
A39-B39-C10-D40
A65-B39-C10-D40
A66-B39-C10-D40
A2-B45-C10-D40
A3-B45-C10-D40
A9-B45-C10-D40
A13-B45-C10-D40
A24-B45-C10-D40
A69-B45-C10-D40
A67-B45-C10-D40
A39-B45-C10-D40
A65-B45-C10-D40
A66-B45-C10-D40
A2-B53-C10-D40
A3-B53-C10-D40
A9-B53-C10-D40
A13-B53-C10-D40
A24-B53-C10-D40
A69-B53-C10-D40
A67-B53-C10-D40

-continued

A39-B53-C10-D40
A65-B53-C10-D40
A66-B53-C10-D40
A2-B79-C10-D40
A3-B79-C10-D40
A9-B79-C10-D40
A13-B79-C10-D40
A24-B79-C10-D40
A69-B79-C10-D40
A67-B79-C10-D40
A39-B79-C10-D40
A65-B79-C10-D40
A66-B79-C10-D40
A2-B80-C10-D40
A3-B80-C10-D40
A9-B80-C10-D40
A13-B80-C10-D40
A24-B80-C10-D40
A69-B80-C10-D40
A67-B80-C10-D40
A39-B80-C10-D40
A65-B80-C10-D40
A66-B80-C10-D40
A2-B85-C10-D40
A3-B85-C10-D40
A9-B85-C10-D40
A13-B85-C10-D40
A24-B85-C10-D40
A69-B85-C10-D40
A67-B85-C10-D40
A39-B85-C10-D40
A65-B85-C10-D40
A66-B85-C10-D40
A2-B86-C10-D40
A3-B86-C10-D40
A9-B86-C10-D40
A13-B86-C10-D40
A24-B86-C10-D40
A69-B86-C10-D40
A67-B86-C10-D40
A39-B86-C10-D40
A65-B86-C10-D40
A66-B86-C10-D40
A2-B87-C10-D40
A3-B87-C10-D40
A9-B87-C10-D40
A13-B87-C10-D40
A24-B87-C10-D40
A69-B87-C10-D40
A67-B87-C10-D40
A39-B87-C10-D40
A65-B87-C10-D40
A66-B87-C10-D40
A2-B89-C10-D40
A3-B89-C10-D40
A9-B89-C10-D40
A13-B89-C10-D40
A24-B89-C10-D40
A69-B89-C10-D40
A67-B89-C10-D40
A39-B89-C10-D40
A65-B89-C10-D40
A66-B89-C10-D40
A2-B92-C10-D40
A3-B92-C10-D40
A9-B92-C10-D40
A13-B92-C10-D40
A24-B92-C10-D40
A69-B92-C10-D40
A67-B92-C10-D40
A39-B92-C10-D40
A65-B92-C10-D40
A66-B92-C10-D40
A2-B4-C11-D40
A3-B4-C11-D40
A9-B4-C11-D40
A13-B4-C11-D40
A24-B4-C11-D40
A69-B4-C11-D40
A67-B4-C11-D40

-continued

A39-B4-C11-D40
A65-B4-C11-D40
A66-B4-C11-D40
A2-B5-C11-D40
A3-B5-C11-D40
A9-B5-C11-D40
A13-B5-C11-D40
A24-B5-C11-D40
A69-B5-C11-D40
A67-B5-C11-D40
A39-B5-C11-D40
A65-B5-C11-D40
A66-B5-C11-D40
A2-B6-C11-D40
A3-B6-C11-D40
A9-B6-C11-D40
A13-B6-C11-D40
A24-B6-C11-D40
A69-B6-C11-D40
A67-B6-C11-D40
A39-B6-C11-D40
A65-B6-C11-D40
A66-B6-C11-D40
A2-B32-C11-D40
A3-B32-C11-D40
A9-B32-C11-D40
A13-B32-C11-D40
A24-B32-C11-D40
A69-B32-C11-D40
A67-B32-C11-D40
A39-B32-C11-D40
A65-B32-C11-D40
A66-B32-C11-D40
A2-B39-C11-D40
A3-B39-C11-D40
A9-B39-C11-D40
A13-B39-C11-D40
A24-B39-C11-D40
A69-B39-C11-D40
A67-B39-C11-D40
A39-B39-C11-D40
A65-B39-C11-D40
A66-B39-C11-D40
A2-B45-C11-D40
A3-B45-C11-D40
A9-B45-C11-D40
A13-B45-C11-D40
A24-B45-C11-D40
A69-B45-C11-D40
A67-B45-C11-D40
A39-B45-C11-D40
A65-B45-C11-D40
A66-B45-C11-D40
A2-B53-C11-D40
A3-B53-C11-D40
A9-B53-C11-D40
A13-B53-C11-D40
A24-B53-C11-D40
A69-B53-C11-D40
A67-B53-C11-D40
A39-B53-C11-D40
A65-B53-C11-D40
A66-B53-C11-D40
A2-B79-C11-D40
A3-B79-C11-D40
A9-B79-C11-D40
A13-B79-C11-D40
A24-B79-C11-D40
A69-B79-C11-D40
A67-B79-C11-D40
A39-B79-C11-D40
A65-B79-C11-D40
A66-B79-C11-D40
A2-B80-C11-D40
A3-B80-C11-D40
A9-B80-C11-D40
A13-B80-C11-D40
A24-B80-C11-D40
A69-B80-C11-D40
A67-B80-C11-D40

-continued

A39-B80-C11-D40
A65-B80-C11-D40
A66-B80-C11-D40
A2-B85-C11-D40
A3-B85-C11-D40
A9-B85-C11-D40
A13-B85-C11-D40
A24-B85-C11-D40
A69-B85-C11-D40
A67-B85-C11-D40
A39-B85-C11-D40
A65-B85-C11-D40
A66-B85-C11-D40
A2-B86-C11-D40
A3-B86-C11-D40
A9-B86-C11-D40
A13-B86-C11-D40
A24-B86-C11-D40
A69-B86-C11-D40
A67-B86-C11-D40
A39-B86-C11-D40
A65-B86-C11-D40
A66-B86-C11-D40
A2-B87-C11-D40
A3-B87-C11-D40
A9-B87-C11-D40
A13-B87-C11-D40
A24-B87-C11-D40
A69-B87-C11-D40
A67-B87-C11-D40
A39-B87-C11-D40
A65-B87-C11-D40
A66-B87-C11-D40
A2-B89-C11-D40
A3-B89-C11-D40
A9-B89-C11-D40
A13-B89-C11-D40
A24-B89-C11-D40
A69-B89-C11-D40
A67-B89-C11-D40
A39-B89-C11-D40
A65-B89-C11-D40
A66-B89-C11-D40
A2-B92-C11-D40
A3-B92-C11-D40
A9-B92-C11-D40
A13-B92-C11-D40
A24-B92-C11-D40
A69-B92-C11-D40
A67-B92-C11-D40
A39-B92-C11-D40
A65-B92-C11-D40
A66-B92-C11-D40
A2-B4-C12-D40
A3-B4-C12-D40
A9-B4-C12-D40
A13-B4-C12-D40
A24-B4-C12-D40
A69-B4-C12-D40
A67-B4-C12-D40
A39-B4-C12-D40
A65-B4-C12-D40
A66-B4-C12-D40
A2-B5-C12-D40
A3-B5-C12-D40
A9-B5-C12-D40
A13-B5-C12-D40
A24-B5-C12-D40
A69-B5-C12-D40
A67-B5-C12-D40
A39-B5-C12-D40
A65-B5-C12-D40
A66-B5-C12-D40
A2-B6-C12-D40
A3-B6-C12-D40
A9-B6-C12-D40
A13-B6-C12-D40
A24-B6-C12-D40
A69-B6-C12-D40
A67-B6-C12-D40

-continued
A39-B6-C12-D40
A65-B6-C12-D40
A66-B6-C12-D40
A2-B32-C12-D40
A3-B32-C12-D40
A9-B32-C12-D40
A13-B32-C12-D40
A24-B32-C12-D40
A69-B32-C12-D40
A67-B32-C12-D40
A39-B32-C12-D40
A65-B32-C12-D40
A66-B32-C12-D40
A2-B39-C12-D40
A3-B39-C12-D40
A9-B39-C12-D40
A13-B39-C12-D40
A24-B39-C12-D40
A69-B39-C12-D40
A67-B39-C12-D40
A39-B39-C12-D40
A65-B39-C12-D40
A66-B39-C12-D40
A2-B45-C12-D40
A3-B45-C12-D40
A9-B45-C12-D40
A13-B45-C12-D40
A24-B45-C12-D40
A69-B45-C12-D40
A67-B45-C12-D40
A39-B45-C12-D40
A65-B45-C12-D40
A66-B45-C12-D40
A2-B53-C12-D40
A3-B53-C12-D40
A9-B53-C12-D40
A13-B53-C12-D40
A24-B53-C12-D40
A69-B53-C12-D40
A67-B53-C12-D40
A39-B53-C12-D40
A65-B53-C12-D40
A66-B53-C12-D40
A2-B79-C12-D40
A3-B79-C12-D40
A9-B79-C12-D40
A13-B79-C12-D40
A24-B79-C12-D40
A69-B79-C12-D40
A67-B79-C12-D40
A39-B79-C12-D40
A65-B79-C12-D40
A66-B79-C12-D40
A2-B80-C12-D40
A3-B80-C12-D40
A9-B80-C12-D40
A13-B80-C12-D40
A24-B80-C12-D40
A69-B80-C12-D40
A67-B80-C12-D40
A39-B80-C12-D40
A65-B80-C12-D40
A66-B80-C12-D40
A2-B85-C12-D40
A3-B85-C12-D40
A9-B85-C12-D40
A13-B85-C12-D40
A24-B85-C12-D40
A69-B85-C12-D40
A67-B85-C12-D40
A39-B85-C12-D40
A65-B85-C12-D40
A66-B85-C12-D40
A2-B86-C12-D40
A3-B86-C12-D40
A9-B86-C12-D40
A13-B86-C12-D40
A24-B86-C12-D40
A69-B86-C12-D40
A67-B86-C12-D40

-continued
A39-B86-C12-D40
A65-B86-C12-D40
A66-B86-C12-D40
A2-B87-C12-D40
A3-B87-C12-D40
A9-B87-C12-D40
A13-B87-C12-D40
A24-B87-C12-D40
A69-B87-C12-D40
A67-B87-C12-D40
A39-B87-C12-D40
A65-B87-C12-D40
A66-B87-C12-D40
A2-B89-C12-D40
A3-B89-C12-D40
A9-B89-C12-D40
A13-B89-C12-D40
A24-B89-C12-D40
A69-B89-C12-D40
A67-B89-C12-D40
A39-B89-C12-D40
A65-B89-C12-D40
A66-B89-C12-D40
A2-B92-C12-D40
A3-B92-C12-D40
A9-B92-C12-D40
A13-B92-C12-D40
A24-B92-C12-D40
A69-B92-C12-D40
A67-B92-C12-D40
A39-B92-C12-D40
A65-B92-C12-D40
A66-B92-C12-D40
A2-B4-C13-D40
A3-B4-C13-D40
A9-B4-C13-D40
A13-B4-C13-D40
A24-B4-C13-D40
A69-B4-C13-D40
A67-B4-C13-D40
A39-B4-C13-D40
A65-B4-C13-D40
A66-B4-C13-D40
A2-B5-C13-D40
A3-B5-C13-D40
A9-B5-C13-D40
A13-B5-C13-D40
A24-B5-C13-D40
A69-B5-C13-D40
A67-B5-C13-D40
A39-B5-C13-D40
A65-B5-C13-D40
A66-B5-C13-D40
A2-B6-C13-D40
A3-B6-C13-D40
A9-B6-C13-D40
A13-B6-C13-D40
A24-B6-C13-D40
A69-B6-C13-D40
A67-B6-C13-D40
A39-B6-C13-D40
A65-B6-C13-D40
A66-B6-C13-D40
A2-B32-C13-D40
A3-B32-C13-D40
A9-B32-C13-D40
A13-B32-C13-D40
A24-B32-C13-D40
A69-B32-C13-D40
A67-B32-C13-D40
A39-B32-C13-D40
A65-B32-C13-D40
A66-B32-C13-D40
A2-B39-C13-D40
A3-B39-C13-D40
A9-B39-C13-D40
A13-B39-C13-D40
A24-B39-C13-D40
A69-B39-C13-D40
A67-B39-C13-D40

-continued

A39-B39-C13-D40
A65-B39-C13-D40
A66-B39-C13-D40
A2-B45-C13-D40
A3-B45-C13-D40
A9-B45-C13-D40
A13-B45-C13-D40
A24-B45-C13-D40
A69-B45-C13-D40
A67-B45-C13-D40
A39-B45-C13-D40
A65-B45-C13-D40
A66-B45-C13-D40
A2-B53-C13-D40
A3-B53-C13-D40
A9-B53-C13-D40
A13-B53-C13-D40
A24-B53-C13-D40
A69-B53-C13-D40
A67-B53-C13-D40
A39-B53-C13-D40
A65-B53-C13-D40
A66-B53-C13-D40
A2-B79-C13-D40
A3-B79-C13-D40
A9-B79-C13-D40
A13-B79-C13-D40
A24-B79-C13-D40
A69-B79-C13-D40
A67-B79-C13-D40
A39-B79-C13-D40
A65-B79-C13-D40
A66-B79-C13-D40
A2-B80-C13-D40
A3-B80-C13-D40
A9-B80-C13-D40
A13-B80-C13-D40
A24-B80-C13-D40
A69-B80-C13-D40
A67-B80-C13-D40
A39-B80-C13-D40
A65-B80-C13-D40
A66-B80-C13-D40
A2-B85-C13-D40
A3-B85-C13-D40
A9-B85-C13-D40
A13-B85-C13-D40
A24-B85-C13-D40
A69-B85-C13-D40
A67-B85-C13-D40
A39-B85-C13-D40
A65-B85-C13-D40
A66-B85-C13-D40
A2-B86-C13-D40
A3-B86-C13-D40
A9-B86-C13-D40
A13-B86-C13-D40
A24-B86-C13-D40
A69-B86-C13-D40
A67-B86-C13-D40
A39-B86-C13-D40
A65-B86-C13-D40
A66-B86-C13-D40
A2-B87-C13-D40
A3-B87-C13-D40
A9-B87-C13-D40
A13-B87-C13-D40
A24-B87-C13-D40
A69-B87-C13-D40
A67-B87-C13-D40
A39-B87-C13-D40
A65-B87-C13-D40
A66-B87-C13-D40
A2-B89-C13-D40
A3-B89-C13-D40
A9-B89-C13-D40
A13-B89-C13-D40
A24-B89-C13-D40
A69-B89-C13-D40
A67-B89-C13-D40

-continued

A39-B89-C13-D40
A65-B89-C13-D40
A66-B89-C13-D40
A2-B92-C13-D40
A3-B92-C13-D40
A9-B92-C13-D40
A13-B92-C13-D40
A24-B92-C13-D40
A69-B92-C13-D40
A67-B92-C13-D40
A39-B92-C13-D40
A65-B92-C13-D40
A66-B92-C13-D40
A2-B4-C1-D41
A3-B4-C1-D41
A9-B4-C1-D41
A13-B4-C1-D41
A24-B4-C1-D41
A69-B4-C1-D41
A67-B4-C1-D41
A39-B4-C1-D41
A65-B4-C1-D41
A66-B4-C1-D41
A2-B5-C1-D41
A3-B5-C1-D41
A9-B5-C1-D41
A13-B5-C1-D41
A24-B5-C1-D41
A69-B5-C1-D41
A67-B5-C1-D41
A39-B5-C1-D41
A65-B5-C1-D41
A66-B5-C1-D41
A2-B6-C1-D41
A3-B6-C1-D41
A9-B6-C1-D41
A13-B6-C1-D41
A24-B6-C1-D41
A69-B6-C1-D41
A67-B6-C1-D41
A39-B6-C1-D41
A65-B6-C1-D41
A66-B6-C1-D41
A2-B32-C1-D41
A3-B32-C1-D41
A9-B32-C1-D41
A13-B32-C1-D41
A24-B32-C1-D41
A69-B32-C1-D41
A67-B32-C1-D41
A39-B32-C1-D41
A65-B32-C1-D41
A66-B32-C1-D41
A2-B39-C1-D41
A3-B39-C1-D41
A9-B39-C1-D41
A13-B39-C1-D41
A24-B39-C1-D41
A69-B39-C1-D41
A67-B39-C1-D41
A39-B39-C1-D41
A65-B39-C1-D41
A66-B39-C1-D41
A2-B45-C1-D41
A3-B45-C1-D41
A9-B45-C1-D41
A13-B45-C1-D41
A24-B45-C1-D41
A69-B45-C1-D41
A67-B45-C1-D41
A39-B45-C1-D41
A65-B45-C1-D41
A66-B45-C1-D41
A2-B53-C1-D41
A3-B53-C1-D41
A9-B53-C1-D41
A13-B53-C1-D41
A24-B53-C1-D41
A69-B53-C1-D41
A67-B53-C1-D41

-continued

A39-B53-C1-D41
A65-B53-C1-D41
A66-B53-C1-D41
A2-B79-C1-D41
A3-B79-C1-D41
A9-B79-C1-D41
A13-B79-C1-D41
A24-B79-C1-D41
A69-B79-C1-D41
A67-B79-C1-D41
A39-B79-C1-D41
A65-B79-C1-D41
A66-B79-C1-D41
A2-B80-C1-D41
A3-B80-C1-D41
A9-B80-C1-D41
A13-B80-C1-D41
A24-B80-C1-D41
A69-B80-C1-D41
A67-B80-C1-D41
A39-B80-C1-D41
A65-B80-C1-D41
A66-B80-C1-D41
A2-B85-C1-D41
A3-B85-C1-D41
A9-B85-C1-D41
A13-B85-C1-D41
A24-B85-C1-D41
A69-B85-C1-D41
A67-B85-C1-D41
A39-B85-C1-D41
A65-B85-C1-D41
A66-B85-C1-D41
A2-B86-C1-D41
A3-B86-C1-D41
A9-B86-C1-D41
A13-B86-C1-D41
A24-B86-C1-D41
A69-B86-C1-D41
A67-B86-C1-D41
A39-B86-C1-D41
A65-B86-C1-D41
A66-B86-C1-D41
A2-B87-C1-D41
A3-B87-C1-D41
A9-B87-C1-D41
A13-B87-C1-D41
A24-B87-C1-D41
A69-B87-C1-D41
A67-B87-C1-D41
A39-B87-C1-D41
A65-B87-C1-D41
A66-B87-C1-D41
A2-B89-C1-D41
A3-B89-C1-D41
A9-B89-C1-D41
A13-B89-C1-D41
A24-B89-C1-D41
A69-B89-C1-D41
A67-B89-C1-D41
A39-B89-C1-D41
A65-B89-C1-D41
A66-B89-C1-D41
A2-B92-C1-D41
A3-B92-C1-D41
A9-B92-C1-D41
A13-B92-C1-D41
A24-B92-C1-D41
A69-B92-C1-D41
A67-B92-C1-D41
A39-B92-C1-D41
A65-B92-C1-D41
A66-B92-C1-D41
A2-B4-C2-D41
A3-B4-C2-D41
A9-B4-C2-D41

-continued

A13-B4-C2-D41
A24-B4-C2-D41
A69-B4-C2-D41
A67-B4-C2-D41
A39-B4-C2-D41
A65-B4-C2-D41
A66-B4-C2-D41
A2-B5-C2-D41
A3-B5-C2-D41
A9-B5-C2-D41
A13-B5-C2-D41
A24-B5-C2-D41
A69-B5-C2-D41
A67-B5-C2-D41
A39-B5-C2-D41
A65-B5-C2-D41
A66-B5-C2-D41
A2-B6-C2-D41
A3-B6-C2-D41
A9-B6-C2-D41
A13-B6-C2-D41
A24-B6-C2-D41
A69-B6-C2-D41
A67-B6-C2-D41
A39-B6-C2-D41
A65-B6-C2-D41
A66-B6-C2-D41
A2-B32-C2-D41
A3-B32-C2-D41
A9-B32-C2-D41
A13-B32-C2-D41
A24-B32-C2-D41
A69-B32-C2-D41
A67-B32-C2-D41
A39-B32-C2-D41
A65-B32-C2-D41
A66-B32-C2-D41
A2-B39-C2-D41
A3-B39-C2-D41
A9-B39-C2-D41
A13-B39-C2-D41
A24-B39-C2-D41
A69-B39-C2-D41
A67-B39-C2-D41
A39-B39-C2-D41
A65-B39-C2-D41
A66-B39-C2-D41
A2-B45-C2-D41
A3-B45-C2-D41
A9-B45-C2-D41
A13-B45-C2-D41
A24-B45-C2-D41
A69-B45-C2-D41
A67-B45-C2-D41
A39-B45-C2-D41
A65-B45-C2-D41
A66-B45-C2-D41
A2-B53-C2-D41
A3-B53-C2-D41
A9-B53-C2-D41
A13-B53-C2-D41
A24-B53-C2-D41
A69-B53-C2-D41
A67-B53-C2-D41
A39-B53-C2-D41
A65-B53-C2-D41
A66-B53-C2-D41
A2-B79-C2-D41
A3-B79-C2-D41
A9-B79-C2-D41
A13-B79-C2-D41
A24-B79-C2-D41
A69-B79-C2-D41
A67-B79-C2-D41
A39-B79-C2-D41
A65-B79-C2-D41
A66-B79-C2-D41
A2-B80-C2-D41
A3-B80-C2-D41
A9-B80-C2-D41

-continued
A13-B80-C2-D41
A24-B80-C2-D41
A69-B80-C2-D41
A67-B80-C2-D41
A39-B80-C2-D41
A65-B80-C2-D41
A66-B80-C2-D41
A2-B85-C2-D41
A3-B85-C2-D41
A9-B85-C2-D41
A13-B85-C2-D41
A24-B85-C2-D41
A69-B85-C2-D41
A67-B85-C2-D41
A39-B85-C2-D41
A65-B85-C2-D41
A66-B85-C2-D41
A2-B86-C2-D41
A3-B86-C2-D41
A9-B86-C2-D41
A13-B86-C2-D41
A24-B86-C2-D41
A69-B86-C2-D41
A67-B86-C2-D41
A39-B86-C2-D41
A65-B86-C2-D41
A66-B86-C2-D41
A2-B87-C2-D41
A3-B87-C2-D41
A9-B87-C2-D41
A13-B87-C2-D41
A24-B87-C2-D41
A69-B87-C2-D41
A67-B87-C2-D41
A39-B87-C2-D41
A65-B87-C2-D41
A66-B87-C2-D41
A2-B89-C2-D41
A3-B89-C2-D41
A9-B89-C2-D41
A13-B89-C2-D41
A24-B89-C2-D41
A69-B89-C2-D41
A67-B89-C2-D41
A39-B89-C2-D41
A65-B89-C2-D41
A66-B89-C2-D41
A2-B92-C2-D41
A3-B92-C2-D41
A9-B92-C2-D41
A13-B92-C2-D41
A24-B92-C2-D41
A69-B92-C2-D41
A67-B92-C2-D41
A39-B92-C2-D41
A65-B92-C2-D41
A66-B92-C2-D41
A2-B4-C3-D41
A3-B4-C3-D41
A9-B4-C3-D41
A13-B4-C3-D41
A24-B4-C3-D41
A69-B4-C3-D41
A67-B4-C3-D41
A39-B4-C3-D41
A65-B4-C3-D41
A66-B4-C3-D41
A2-B5-C3-D41
A3-B5-C3-D41
A9-B5-C3-D41
A13-B5-C3-D41
A24-B5-C3-D41
A69-B5-C3-D41
A67-B5-C3-D41
A39-B5-C3-D41
A65-B5-C3-D41
A66-B5-C3-D41
A2-B6-C3-D41
A3-B6-C3-D41
A9-B6-C3-D41

-continued
A13-B6-C3-D41
A24-B6-C3-D41
A69-B6-C3-D41
A67-B6-C3-D41
A39-B6-C3-D41
A65-B6-C3-D41
A66-B6-C3-D41
A2-B32-C3-D41
A3-B32-C3-D41
A9-B32-C3-D41
A13-B32-C3-D41
A24-B32-C3-D41
A69-B32-C3-D41
A67-B32-C3-D41
A39-B32-C3-D41
A65-B32-C3-D41
A66-B32-C3-D41
A2-B39-C3-D41
A3-B39-C3-D41
A9-B39-C3-D41
A13-B39-C3-D41
A24-B39-C3-D41
A69-B39-C3-D41
A67-B39-C3-D41
A39-B39-C3-D41
A65-B39-C3-D41
A66-B39-C3-D41
A2-B45-C3-D41
A3-B45-C3-D41
A9-B45-C3-D41
A13-B45-C3-D41
A24-B45-C3-D41
A69-B45-C3-D41
A67-B45-C3-D41
A39-B45-C3-D41
A65-B45-C3-D41
A66-B45-C3-D41
A2-B53-C3-D41
A3-B53-C3-D41
A9-B53-C3-D41
A13-B53-C3-D41
A24-B53-C3-D41
A69-B53-C3-D41
A67-B53-C3-D41
A39-B53-C3-D41
A65-B53-C3-D41
A66-B53-C3-D41
A2-B79-C3-D41
A3-B79-C3-D41
A9-B79-C3-D41
A13-B79-C3-D41
A24-B79-C3-D41
A69-B79-C3-D41
A67-B79-C3-D41
A39-B79-C3-D41
A65-B79-C3-D41
A66-B79-C3-D41
A2-B80-C3-D41
A3-B80-C3-D41
A9-B80-C3-D41
A13-B80-C3-D41
A24-B80-C3-D41
A69-B80-C3-D41
A67-B80-C3-D41
A39-B80-C3-D41
A65-B80-C3-D41
A66-B80-C3-D41
A2-B85-C3-D41
A3-B85-C3-D41
A9-B85-C3-D41
A13-B85-C3-D41
A24-B85-C3-D41
A69-B85-C3-D41
A67-B85-C3-D41
A39-B85-C3-D41
A65-B85-C3-D41
A66-B85-C3-D41
A2-B86-C3-D41
A3-B86-C3-D41
A9-B86-C3-D41

-continued
A13-B86-C3-D41
A24-B86-C3-D41
A69-B86-C3-D41
A67-B86-C3-D41
A39-B86-C3-D41
A65-B86-C3-D41
A66-B86-C3-D41
A2-B87-C3-D41
A3-B87-C3-D41
A9-B87-C3-D41
A13-B87-C3-D41
A24-B87-C3-D41
A69-B87-C3-D41
A67-B87-C3-D41
A39-B87-C3-D41
A65-B87-C3-D41
A66-B87-C3-D41
A2-B89-C3-D41
A3-B89-C3-D41
A9-B89-C3-D41
A13-B89-C3-D41
A24-B89-C3-D41
A69-B89-C3-D41
A67-B89-C3-D41
A39-B89-C3-D41
A65-B89-C3-D41
A66-B89-C3-D41
A2-B92-C3-D41
A3-B92-C3-D41
A9-B92-C3-D41
A13-B92-C3-D41
A24-B92-C3-D41
A69-B92-C3-D41
A67-B92-C3-D41
A39-B92-C3-D41
A65-B92-C3-D41
A66-B92-C3-D41
A2-B4-C4-D41
A3-B4-C4-D41
A9-B4-C4-D41
A13-B4-C4-D41
A24-B4-C4-D41
A69-B4-C4-D41
A67-B4-C4-D41
A39-B4-C4-D41
A65-B4-C4-D41
A66-B4-C4-D41
A2-B5-C4-D41
A3-B5-C4-D41
A9-B5-C4-D41
A13-B5-C4-D41
A24-B5-C4-D41
A69-B5-C4-D41
A67-B5-C4-D41
A39-B5-C4-D41
A65-B5-C4-D41
A66-B5-C4-D41
A2-B6-C4-D41
A3-B6-C4-D41
A9-B6-C4-D41
A13-B6-C4-D41
A24-B6-C4-D41
A69-B6-C4-D41
A67-B6-C4-D41
A39-B6-C4-D41
A65-B6-C4-D41
A66-B6-C4-D41
A2-B32-C4-D41
A3-B32-C4-D41
A9-B32-C4-D41
A13-B32-C4-D41
A24-B32-C4-D41
A69-B32-C4-D41
A67-B32-C4-D41
A39-B32-C4-D41
A65-B32-C4-D41
A66-B32-C4-D41
A2-B39-C4-D41
A3-B39-C4-D41
A9-B39-C4-D41

-continued
A13-B39-C4-D41
A24-B39-C4-D41
A69-B39-C4-D41
A67-B39-C4-D41
A39-B39-C4-D41
A65-B39-C4-D41
A66-B39-C4-D41
A2-B45-C4-D41
A3-B45-C4-D41
A9-B45-C4-D41
A13-B45-C4-D41
A24-B45-C4-D41
A69-B45-C4-D41
A67-B45-C4-D41
A39-B45-C4-D41
A65-B45-C4-D41
A66-B45-C4-D41
A2-B53-C4-D41
A3-B53-C4-D41
A9-B53-C4-D41
A13-B53-C4-D41
A24-B53-C4-D41
A69-B53-C4-D41
A67-B53-C4-D41
A39-B53-C4-D41
A65-B53-C4-D41
A66-B53-C4-D41
A2-B79-C4-D41
A3-B79-C4-D41
A9-B79-C4-D41
A13-B79-C4-D41
A24-B79-C4-D41
A69-B79-C4-D41
A67-B79-C4-D41
A39-B79-C4-D41
A65-B79-C4-D41
A66-B79-C4-D41
A2-B80-C4-D41
A3-B80-C4-D41
A9-B80-C4-D41
A13-B80-C4-D41
A24-B80-C4-D41
A69-B80-C4-D41
A67-B80-C4-D41
A39-B80-C4-D41
A65-B80-C4-D41
A66-B80-C4-D41
A2-B85-C4-D41
A3-B85-C4-D41
A9-B85-C4-D41
A13-B85-C4-D41
A24-B85-C4-D41
A69-B85-C4-D41
A67-B85-C4-D41
A39-B85-C4-D41
A65-B85-C4-D41
A66-B85-C4-D41
A2-B86-C4-D41
A3-B86-C4-D41
A9-B86-C4-D41
A13-B86-C4-D41
A24-B86-C4-D41
A69-B86-C4-D41
A67-B86-C4-D41
A39-B86-C4-D41
A65-B86-C4-D41
A66-B86-C4-D41
A2-B87-C4-D41
A3-B87-C4-D41
A9-B87-C4-D41
A13-B87-C4-D41
A24-B87-C4-D41
A69-B87-C4-D41
A67-B87-C4-D41
A39-B87-C4-D41
A65-B87-C4-D41
A66-B87-C4-D41
A2-B89-C4-D41
A3-B89-C4-D41
A9-B89-C4-D41

-continued
A13-B89-C4-D41
A24-B89-C4-D41
A69-B89-C4-D41
A67-B89-C4-D41
A39-B89-C4-D41
A65-B89-C4-D41
A66-B89-C4-D41
A2-B92-C4-D41
A3-B92-C4-D41
A9-B92-C4-D41
A13-B92-C4-D41
A24-B92-C4-D41
A69-B92-C4-D41
A67-B92-C4-D41
A39-B92-C4-D41
A65-B92-C4-D41
A66-B92-C4-D41
A2-B4-C5-D41
A3-B4-C5-D41
A9-B4-C5-D41
A13-B4-C5-D41
A24-B4-C5-D41
A69-B4-C5-D41
A67-B4-C5-D41
A39-B4-C5-D41
A65-B4-C5-D41
A66-B4-C5-D41
A2-B5-C5-D41
A3-B5-C5-D41
A9-B5-C5-D41
A13-B5-C5-D41
A24-B5-C5-D41
A69-B5-C5-D41
A67-B5-C5-D41
A39-B5-C5-D41
A65-B5-C5-D41
A66-B5-C5-D41
A2-B6-C5-D41
A3-B6-C5-D41
A9-B6-C5-D41
A13-B6-C5-D41
A24-B6-C5-D41
A69-B6-C5-D41
A67-B6-C5-D41
A39-B6-C5-D41
A65-B6-C5-D41
A66-B6-C5-D41
A2-B32-C5-D41
A3-B32-C5-D41
A9-B32-C5-D41
A13-B32-C5-D41
A24-B32-C5-D41
A69-B32-C5-D41
A67-B32-C5-D41
A39-B32-C5-D41
A65-B32-C5-D41
A66-B32-C5-D41
A2-B39-C5-D41
A3-B39-C5-D41
A9-B39-C5-D41
A13-B39-C5-D41
A24-B39-C5-D41
A69-B39-C5-D41
A67-B39-C5-D41
A39-B39-C5-D41
A65-B39-C5-D41
A66-B39-C5-D41
A2-B45-C5-D41
A3-B45-C5-D41
A9-B45-C5-D41
A13-B45-C5-D41
A24-B45-C5-D41
A69-B45-C5-D41
A67-B45-C5-D41
A39-B45-C5-D41
A65-B45-C5-D41
A66-B45-C5-D41
A2-B53-C5-D41
A3-B53-C5-D41
A9-B53-C5-D41

-continued
A13-B53-C5-D41
A24-B53-C5-D41
A69-B53-C5-D41
A67-B53-C5-D41
A39-B53-C5-D41
A65-B53-C5-D41
A66-B53-C5-D41
A2-B79-C5-D41
A3-B79-C5-D41
A9-B79-C5-D41
A13-B79-C5-D41
A24-B79-C5-D41
A69-B79-C5-D41
A67-B79-C5-D41
A39-B79-C5-D41
A65-B79-C5-D41
A66-B79-C5-D41
A2-B80-C5-D41
A3-B80-C5-D41
A9-B80-C5-D41
A13-B80-C5-D41
A24-B80-C5-D41
A69-B80-C5-D41
A67-B80-C5-D41
A39-B80-C5-D41
A65-B80-C5-D41
A66-B80-C5-D41
A2-B85-C5-D41
A3-B85-C5-D41
A9-B85-C5-D41
A13-B85-C5-D41
A24-B85-C5-D41
A69-B85-C5-D41
A67-B85-C5-D41
A39-B85-C5-D41
A65-B85-C5-D41
A66-B85-C5-D41
A2-B86-C5-D41
A3-B86-C5-D41
A9-B86-C5-D41
A13-B86-C5-D41
A24-B86-C5-D41
A69-B86-C5-D41
A67-B86-C5-D41
A39-B86-C5-D41
A65-B86-C5-D41
A66-B86-C5-D41
A2-B87-C5-D41
A3-B87-C5-D41
A9-B87-C5-D41
A13-B87-C5-D41
A24-B87-C5-D41
A69-B87-C5-D41
A67-B87-C5-D41
A39-B87-C5-D41
A65-B87-C5-D41
A66-B87-C5-D41
A2-B89-C5-D41
A3-B89-C5-D41
A9-B89-C5-D41
A13-B89-C5-D41
A24-B89-C5-D41
A69-B89-C5-D41
A67-B89-C5-D41
A39-B89-C5-D41
A65-B89-C5-D41
A66-B89-C5-D41
A2-B92-C5-D41
A3-B92-C5-D41
A9-B92-C5-D41
A13-B92-C5-D41
A24-B92-C5-D41
A69-B92-C5-D41
A67-B92-C5-D41
A39-B92-C5-D41
A65-B92-C5-D41
A66-B92-C5-D41
A2-B4-C6-D41
A3-B4-C6-D41
A9-B4-C6-D41

-continued

A13-B4-C6-D41
A24-B4-C6-D41
A69-B4-C6-D41
A67-B4-C6-D41
A39-B4-C6-D41
A65-B4-C6-D41
A66-B4-C6-D41
A2-B5-C6-D41
A3-B5-C6-D41
A9-B5-C6-D41
A13-B5-C6-D41
A24-B5-C6-D41
A69-B5-C6-D41
A67-B5-C6-D41
A39-B5-C6-D41
A65-B5-C6-D41
A66-B5-C6-D41
A2-B6-C6-D41
A3-B6-C6-D41
A9-B6-C6-D41
A13-B6-C6-D41
A24-B6-C6-D41
A69-B6-C6-D41
A67-B6-C6-D41
A39-B6-C6-D41
A65-B6-C6-D41
A66-B6-C6-D41
A2-B32-C6-D41
A3-B32-C6-D41
A9-B32-C6-D41
A13-B32-C6-D41
A24-B32-C6-D41
A69-B32-C6-D41
A67-B32-C6-D41
A39-B32-C6-D41
A65-B32-C6-D41
A66-B32-C6-D41
A2-B39-C6-D41
A3-B39-C6-D41
A9-B39-C6-D41
A13-B39-C6-D41
A24-B39-C6-D41
A69-B39-C6-D41
A67-B39-C6-D41
A39-B39-C6-D41
A65-B39-C6-D41
A66-B39-C6-D41
A2-B45-C6-D41
A3-B45-C6-D41
A9-B45-C6-D41
A13-B45-C6-D41
A24-B45-C6-D41
A69-B45-C6-D41
A67-B45-C6-D41
A39-B45-C6-D41
A65-B45-C6-D41
A66-B45-C6-D41
A2-B53-C6-D41
A3-B53-C6-D41
A9-B53-C6-D41
A13-B53-C6-D41
A24-B53-C6-D41
A69-B53-C6-D41
A67-B53-C6-D41
A39-B53-C6-D41
A65-B53-C6-D41
A66-B53-C6-D41
A2-B79-C6-D41
A3-B79-C6-D41
A9-B79-C6-D41
A13-B79-C6-D41
A24-B79-C6-D41
A69-B79-C6-D41
A67-B79-C6-D41
A39-B79-C6-D41
A65-B79-C6-D41
A66-B79-C6-D41
A2-B80-C6-D41
A3-B80-C6-D41
A9-B80-C6-D41

-continued

A13-B80-C6-D41
A24-B80-C6-D41
A69-B80-C6-D41
A67-B80-C6-D41
A39-B80-C6-D41
A65-B80-C6-D41
A66-B80-C6-D41
A2-B85-C6-D41
A3-B85-C6-D41
A9-B85-C6-D41
A13-B85-C6-D41
A24-B85-C6-D41
A69-B85-C6-D41
A67-B85-C6-D41
A39-B85-C6-D41
A65-B85-C6-D41
A66-B85-C6-D41
A2-B86-C6-D41
A3-B86-C6-D41
A9-B86-C6-D41
A13-B86-C6-D41
A24-B86-C6-D41
A69-B86-C6-D41
A67-B86-C6-D41
A39-B86-C6-D41
A65-B86-C6-D41
A66-B86-C6-D41
A2-B87-C6-D41
A3-B87-C6-D41
A9-B87-C6-D41
A13-B87-C6-D41
A24-B87-C6-D41
A69-B87-C6-D41
A67-B87-C6-D41
A39-B87-C6-D41
A65-B87-C6-D41
A66-B87-C6-D41
A2-B89-C6-D41
A3-B89-C6-D41
A9-B89-C6-D41
A13-B89-C6-D41
A24-B89-C6-D41
A69-B89-C6-D41
A67-B89-C6-D41
A39-B89-C6-D41
A65-B89-C6-D41
A66-B89-C6-D41
A2-B92-C6-D41
A3-B92-C6-D41
A9-B92-C6-D41
A13-B92-C6-D41
A24-B92-C6-D41
A69-B92-C6-D41
A67-B92-C6-D41
A39-B92-C6-D41
A65-B92-C6-D41
A66-B92-C6-D41
A2-B4-C7-D41
A3-B4-C7-D41
A9-B4-C7-D41
A13-B4-C7-D41
A24-B4-C7-D41
A69-B4-C7-D41
A67-B4-C7-D41
A39-B4-C7-D41
A65-B4-C7-D41
A66-B4-C7-D41
A2-B5-C7-D41
A3-B5-C7-D41
A9-B5-C7-D41
A13-B5-C7-D41
A24-B5-C7-D41
A69-B5-C7-D41
A67-B5-C7-D41
A39-B5-C7-D41
A65-B5-C7-D41
A66-B5-C7-D41
A2-B6-C7-D41
A3-B6-C7-D41
A9-B6-C7-D41

-continued
A13-B6-C7-D41
A24-B6-C7-D41
A69-B6-C7-D41
A67-B6-C7-D41
A39-B6-C7-D41
A65-B6-C7-D41
A66-B6-C7-D41
A2-B32-C7-D41
A3-B32-C7-D41
A9-B32-C7-D41
A13-B32-C7-D41
A24-B32-C7-D41
A69-B32-C7-D41
A67-B32-C7-D41
A39-B32-C7-D41
A65-B32-C7-D41
A66-B32-C7-D41
A2-B39-C7-D41
A3-B39-C7-D41
A9-B39-C7-D41
A13-B39-C7-D41
A24-B39-C7-D41
A69-B39-C7-D41
A67-B39-C7-D41
A39-B39-C7-D41
A65-B39-C7-D41
A66-B39-C7-D41
A2-B45-C7-D41
A3-B45-C7-D41
A9-B45-C7-D41
A13-B45-C7-D41
A24-B45-C7-D41
A69-B45-C7-D41
A67-B45-C7-D41
A39-B45-C7-D41
A65-B45-C7-D41
A66-B45-C7-D41
A2-B53-C7-D41
A3-B53-C7-D41
A9-B53-C7-D41
A13-B53-C7-D41
A24-B53-C7-D41
A69-B53-C7-D41
A67-B53-C7-D41
A39-B53-C7-D41
A65-B53-C7-D41
A66-B53-C7-D41
A2-B79-C7-D41
A3-B79-C7-D41
A9-B79-C7-D41
A13-B79-C7-D41
A24-B79-C7-D41
A69-B79-C7-D41
A67-B79-C7-D41
A39-B79-C7-D41
A65-B79-C7-D41
A66-B79-C7-D41
A2-B80-C7-D41
A3-B80-C7-D41
A9-B80-C7-D41
A13-B80-C7-D41
A24-B80-C7-D41
A69-B80-C7-D41
A67-B80-C7-D41
A39-B80-C7-D41
A65-B80-C7-D41
A66-B80-C7-D41
A2-B85-C7-D41
A3-B85-C7-D41
A9-B85-C7-D41
A13-B85-C7-D41
A24-B85-C7-D41
A69-B85-C7-D41
A67-B85-C7-D41
A39-B85-C7-D41
A65-B85-C7-D41
A66-B85-C7-D41
A2-B86-C7-D41
A3-B86-C7-D41
A9-B86-C7-D41

-continued
A13-B86-C7-D41
A24-B86-C7-D41
A69-B86-C7-D41
A67-B86-C7-D41
A39-B86-C7-D41
A65-B86-C7-D41
A66-B86-C7-D41
A2-B87-C7-D41
A3-B87-C7-D41
A9-B87-C7-D41
A13-B87-C7-D41
A24-B87-C7-D41
A69-B87-C7-D41
A67-B87-C7-D41
A39-B87-C7-D41
A65-B87-C7-D41
A66-B87-C7-D41
A2-B89-C7-D41
A3-B89-C7-D41
A9-B89-C7-D41
A13-B89-C7-D41
A24-B89-C7-D41
A69-B89-C7-D41
A67-B89-C7-D41
A39-B89-C7-D41
A65-B89-C7-D41
A66-B89-C7-D41
A2-B92-C7-D41
A3-B92-C7-D41
A9-B92-C7-D41
A13-B92-C7-D41
A24-B92-C7-D41
A69-B92-C7-D41
A67-B92-C7-D41
A39-B92-C7-D41
A65-B92-C7-D41
A66-B92-C7-D41
A2-B4-C8-D41
A3-B4-C8-D41
A9-B4-C8-D41
A13-B4-C8-D41
A24-B4-C8-D41
A69-B4-C8-D41
A67-B4-C8-D41
A39-B4-C8-D41
A65-B4-C8-D41
A66-B4-C8-D41
A2-B5-C8-D41
A3-B5-C8-D41
A9-B5-C8-D41
A13-B5-C8-D41
A24-B5-C8-D41
A69-B5-C8-D41
A67-B5-C8-D41
A39-B5-C8-D41
A65-B5-C8-D41
A66-B5-C8-D41
A2-B6-C8-D41
A3-B6-C8-D41
A9-B6-C8-D41
A13-B6-C8-D41
A24-B6-C8-D41
A69-B6-C8-D41
A67-B6-C8-D41
A39-B6-C8-D41
A65-B6-C8-D41
A66-B6-C8-D41
A2-B32-C8-D41
A3-B32-C8-D41
A9-B32-C8-D41
A13-B32-C8-D41
A24-B32-C8-D41
A69-B32-C8-D41
A67-B32-C8-D41
A39-B32-C8-D41
A65-B32-C8-D41
A66-B32-C8-D41
A2-B39-C8-D41
A3-B39-C8-D41
A9-B39-C8-D41

-continued
A13-B39-C8-D41
A24-B39-C8-D41
A69-B39-C8-D41
A67-B39-C8-D41
A39-B39-C8-D41
A65-B39-C8-D41
A66-B39-C8-D41
A2-B45-C8-D41
A3-B45-C8-D41
A9-B45-C8-D41
A13-B45-C8-D41
A24-B45-C8-D41
A69-B45-C8-D41
A67-B45-C8-D41
A39-B45-C8-D41
A65-B45-C8-D41
A66-B45-C8-D41
A2-B53-C8-D41
A3-B53-C8-D41
A9-B53-C8-D41
A13-B53-C8-D41
A24-B53-C8-D41
A69-B53-C8-D41
A67-B53-C8-D41
A39-B53-C8-D41
A65-B53-C8-D41
A66-B53-C8-D41
A2-B79-C8-D41
A3-B79-C8-D41
A9-B79-C8-D41
A13-B79-C8-D41
A24-B79-C8-D41
A69-B79-C8-D41
A67-B79-C8-D41
A39-B79-C8-D41
A65-B79-C8-D41
A66-B79-C8-D41
A2-B80-C8-D41
A3-B80-C8-D41
A9-B80-C8-D41
A13-B80-C8-D41
A24-B80-C8-D41
A69-B80-C8-D41
A67-B80-C8-D41
A39-B80-C8-D41
A65-B80-C8-D41
A66-B80-C8-D41
A2-B85-C8-D41
A3-B85-C8-D41
A9-B85-C8-D41
A13-B85-C8-D41
A24-B85-C8-D41
A69-B85-C8-D41
A67-B85-C8-D41
A39-B85-C8-D41
A65-B85-C8-D41
A66-B85-C8-D41
A2-B86-C8-D41
A3-B86-C8-D41
A9-B86-C8-D41
A13-B86-C8-D41
A24-B86-C8-D41
A69-B86-C8-D41
A67-B86-C8-D41
A39-B86-C8-D41
A65-B86-C8-D41
A66-B86-C8-D41
A2-B87-C8-D41
A3-B87-C8-D41
A9-B87-C8-D41
A13-B87-C8-D41
A24-B87-C8-D41
A69-B87-C8-D41
A67-B87-C8-D41
A39-B87-C8-D41
A65-B87-C8-D41
A66-B87-C8-D41
A2-B89-C8-D41
A3-B89-C8-D41
A9-B89-C8-D41

-continued
A13-B89-C8-D41
A24-B89-C8-D41
A69-B89-C8-D41
A67-B89-C8-D41
A39-B89-C8-D41
A65-B89-C8-D41
A66-B89-C8-D41
A2-B92-C8-D41
A3-B92-C8-D41
A9-B92-C8-D41
A13-B92-C8-D41
A24-B92-C8-D41
A69-B92-C8-D41
A67-B92-C8-D41
A39-B92-C8-D41
A65-B92-C8-D41
A66-B92-C8-D41
A2-B4-C9-D41
A3-B4-C9-D41
A9-B4-C9-D41
A13-B4-C9-D41
A24-B4-C9-D41
A69-B4-C9-D41
A67-B4-C9-D41
A39-B4-C9-D41
A65-B4-C9-D41
A66-B4-C9-D41
A2-B5-C9-D41
A3-B5-C9-D41
A9-B5-C9-D41
A13-B5-C9-D41
A24-B5-C9-D41
A69-B5-C9-D41
A67-B5-C9-D41
A39-B5-C9-D41
A65-B5-C9-D41
A66-B5-C9-D41
A2-B6-C9-D41
A3-B6-C9-D41
A9-B6-C9-D41
A13-B6-C9-D41
A24-B6-C9-D41
A69-B6-C9-D41
A67-B6-C9-D41
A39-B6-C9-D41
A65-B6-C9-D41
A66-B6-C9-D41
A2-B32-C9-D41
A3-B32-C9-D41
A9-B32-C9-D41
A13-B32-C9-D41
A24-B32-C9-D41
A69-B32-C9-D41
A67-B32-C9-D41
A39-B32-C9-D41
A65-B32-C9-D41
A66-B32-C9-D41
A2-B39-C9-D41
A3-B39-C9-D41
A9-B39-C9-D41
A13-B39-C9-D41
A24-B39-C9-D41
A69-B39-C9-D41
A67-B39-C9-D41
A39-B39-C9-D41
A65-B39-C9-D41
A66-B39-C9-D41
A2-B45-C9-D41
A3-B45-C9-D41
A9-B45-C9-D41
A13-B45-C9-D41
A24-B45-C9-D41
A69-B45-C9-D41
A67-B45-C9-D41
A39-B45-C9-D41
A65-B45-C9-D41
A66-B45-C9-D41
A2-B53-C9-D41
A3-B53-C9-D41
A9-B53-C9-D41

-continued
A13-B53-C9-D41
A24-B53-C9-D41
A69-B53-C9-D41
A67-B53-C9-D41
A39-B53-C9-D41
A65-B53-C9-D41
A66-B53-C9-D41
A2-B79-C9-D41
A3-B79-C9-D41
A9-B79-C9-D41
A13-B79-C9-D41
A24-B79-C9-D41
A69-B79-C9-D41
A67-B79-C9-D41
A39-B79-C9-D41
A65-B79-C9-D41
A66-B79-C9-D41
A2-B80-C9-D41
A3-B80-C9-D41
A9-B80-C9-D41
A13-B80-C9-D41
A24-B80-C9-D41
A69-B80-C9-D41
A67-B80-C9-D41
A39-B80-C9-D41
A65-B80-C9-D41
A66-B80-C9-D41
A2-B85-C9-D41
A3-B85-C9-D41
A9-B85-C9-D41
A13-B85-C9-D41
A24-B85-C9-D41
A69-B85-C9-D41
A67-B85-C9-D41
A39-B85-C9-D41
A65-B85-C9-D41
A66-B85-C9-D41
A2-B86-C9-D41
A3-B86-C9-D41
A9-B86-C9-D41
A13-B86-C9-D41
A24-B86-C9-D41
A69-B86-C9-D41
A67-B86-C9-D41
A39-B86-C9-D41
A65-B86-C9-D41
A66-B86-C9-D41
A2-B87-C9-D41
A3-B87-C9-D41
A9-B87-C9-D41
A13-B87-C9-D41
A24-B87-C9-D41
A69-B87-C9-D41
A67-B87-C9-D41
A39-B87-C9-D41
A65-B87-C9-D41
A66-B87-C9-D41
A2-B89-C9-D41
A3-B89-C9-D41
A9-B89-C9-D41
A13-B89-C9-D41
A24-B89-C9-D41
A69-B89-C9-D41
A67-B89-C9-D41
A39-B89-C9-D41
A65-B89-C9-D41
A66-B89-C9-D41
A2-B92-C9-D41
A3-B92-C9-D41
A9-B92-C9-D41
A13-B92-C9-D41
A24-B92-C9-D41
A69-B92-C9-D41
A67-B92-C9-D41
A39-B92-C9-D41
A65-B92-C9-D41
A66-B92-C9-D41
A2-B4-C10-D41
A3-B4-C10-D41
A9-B4-C10-D41

-continued
A13-B4-C10-D41
A24-B4-C10-D41
A69-B4-C10-D41
A67-B4-C10-D41
A39-B4-C10-D41
A65-B4-C10-D41
A66-B4-C10-D41
A2-B5-C10-D41
A3-B5-C10-D41
A9-B5-C10-D41
A13-B5-C10-D41
A24-B5-C10-D41
A69-B5-C10-D41
A67-B5-C10-D41
A39-B5-C10-D41
A65-B5-C10-D41
A66-B5-C10-D41
A2-B6-C10-D41
A3-B6-C10-D41
A9-B6-C10-D41
A13-B6-C10-D41
A24-B6-C10-D41
A69-B6-C10-D41
A67-B6-C10-D41
A39-B6-C10-D41
A65-B6-C10-D41
A66-B6-C10-D41
A2-B32-C10-D41
A3-B32-C10-D41
A9-B32-C10-D41
A13-B32-C10-D41
A24-B32-C10-D41
A69-B32-C10-D41
A67-B32-C10-D41
A39-B32-C10-D41
A65-B32-C10-D41
A66-B32-C10-D41
A2-B39-C10-D41
A3-B39-C10-D41
A9-B39-C10-D41
A13-B39-C10-D41
A24-B39-C10-D41
A69-B39-C10-D41
A67-B39-C10-D41
A39-B39-C10-D41
A65-B39-C10-D41
A66-B39-C10-D41
A2-B45-C10-D41
A3-B45-C10-D41
A9-B45-C10-D41
A13-B45-C10-D41
A24-B45-C10-D41
A69-B45-C10-D41
A67-B45-C10-D41
A39-B45-C10-D41
A65-B45-C10-D41
A66-B45-C10-D41
A2-B53-C10-D41
A3-B53-C10-D41
A9-B53-C10-D41
A13-B53-C10-D41
A24-B53-C10-D41
A69-B53-C10-D41
A67-B53-C10-D41
A39-B53-C10-D41
A65-B53-C10-D41
A66-B53-C10-D41
A2-B79-C10-D41
A3-B79-C10-D41
A9-B79-C10-D41
A13-B79-C10-D41
A24-B79-C10-D41
A69-B79-C10-D41
A67-B79-C10-D41
A39-B79-C10-D41
A65-B79-C10-D41
A66-B79-C10-D41
A2-B80-C10-D41
A3-B80-C10-D41
A9-B80-C10-D41

-continued
A13-B80-C10-D41
A24-B80-C10-D41
A69-B80-C10-D41
A67-B80-C10-D41
A39-B80-C10-D41
A65-B80-C10-D41
A66-B80-C10-D41
A2-B85-C10-D41
A3-B85-C10-D41
A9-B85-C10-D41
A13-B85-C10-D41
A24-B85-C10-D41
A69-B85-C10-D41
A67-B85-C10-D41
A39-B85-C10-D41
A65-B85-C10-D41
A66-B85-C10-D41
A2-B86-C10-D41
A3-B86-C10-D41
A9-B86-C10-D41
A13-B86-C10-D41
A24-B86-C10-D41
A69-B86-C10-D41
A67-B86-C10-D41
A39-B86-C10-D41
A65-B86-C10-D41
A66-B86-C10-D41
A2-B87-C10-D41
A3-B87-C10-D41
A9-B87-C10-D41
A13-B87-C10-D41
A24-B87-C10-D41
A69-B87-C10-D41
A67-B87-C10-D41
A39-B87-C10-D41
A65-B87-C10-D41
A66-B87-C10-D41
A2-B89-C10-D41
A3-B89-C10-D41
A9-B89-C10-D41
A13-B89-C10-D41
A24-B89-C10-D41
A69-B89-C10-D41
A67-B89-C10-D41
A39-B89-C10-D41
A65-B89-C10-D41
A66-B89-C10-D41
A2-B92-C10-D41
A3-B92-C10-D41
A9-B92-C10-D41
A13-B92-C10-D41
A24-B92-C10-D41
A69-B92-C10-D41
A67-B92-C10-D41
A39-B92-C10-D41
A65-B92-C10-D41
A66-B92-C10-D41
A2-B4-C11-D41
A3-B4-C11-D41
A9-B4-C11-D41
A13-B4-C11-D41
A24-B4-C11-D41
A69-B4-C11-D41
A67-B4-C11-D41
A39-B4-C11-D41
A65-B4-C11-D41
A66-B4-C11-D41
A2-B5-C11-D41
A3-B5-C11-D41
A9-B5-C11-D41
A13-B5-C11-D41
A24-B5-C11-D41
A69-B5-C11-D41
A67-B5-C11-D41
A39-B5-C11-D41
A65-B5-C11-D41
A66-B5-C11-D41
A2-B6-C11-D41
A3-B6-C11-D41
A9-B6-C11-D41

-continued
A13-B6-C11-D41
A24-B6-C11-D41
A69-B6-C11-D41
A67-B6-C11-D41
A39-B6-C11-D41
A65-B6-C11-D41
A66-B6-C11-D41
A2-B32-C11-D41
A3-B32-C11-D41
A9-B32-C11-D41
A13-B32-C11-D41
A24-B32-C11-D41
A69-B32-C11-D41
A67-B32-C11-D41
A39-B32-C11-D41
A65-B32-C11-D41
A66-B32-C11-D41
A2-B39-C11-D41
A3-B39-C11-D41
A9-B39-C11-D41
A13-B39-C11-D41
A24-B39-C11-D41
A69-B39-C11-D41
A67-B39-C11-D41
A39-B39-C11-D41
A65-B39-C11-D41
A66-B39-C11-D41
A2-B45-C11-D41
A3-B45-C11-D41
A9-B45-C11-D41
A13-B45-C11-D41
A24-B45-C11-D41
A69-B45-C11-D41
A67-B45-C11-D41
A39-B45-C11-D41
A65-B45-C11-D41
A66-B45-C11-D41
A2-B53-C11-D41
A3-B53-C11-D41
A9-B53-C11-D41
A13-B53-C11-D41
A24-B53-C11-D41
A69-B53-C11-D41
A67-B53-C11-D41
A39-B53-C11-D41
A65-B53-C11-D41
A66-B53-C11-D41
A2-B79-C11-D41
A3-B79-C11-D41
A9-B79-C11-D41
A13-B79-C11-D41
A24-B79-C11-D41
A69-B79-C11-D41
A67-B79-C11-D41
A39-B79-C11-D41
A65-B79-C11-D41
A66-B79-C11-D41
A2-B80-C11-D41
A3-B80-C11-D41
A9-B80-C11-D41
A13-B80-C11-D41
A24-B80-C11-D41
A69-B80-C11-D41
A67-B80-C11-D41
A39-B80-C11-D41
A65-B80-C11-D41
A66-B80-C11-D41
A2-B85-C11-D41
A3-B85-C11-D41
A9-B85-C11-D41
A13-B85-C11-D41
A24-B85-C11-D41
A69-B85-C11-D41
A67-B85-C11-D41
A39-B85-C11-D41
A65-B85-C11-D41
A66-B85-C11-D41
A2-B86-C11-D41
A3-B86-C11-D41
A9-B86-C11-D41

-continued

A13-B86-C11-D41
A24-B86-C11-D41
A69-B86-C11-D41
A67-B86-C11-D41
A39-B86-C11-D41
A65-B86-C11-D41
A66-B86-C11-D41
A2-B87-C11-D41
A3-B87-C11-D41
A9-B87-C11-D41
A13-B87-C11-D41
A24-B87-C11-D41
A69-B87-C11-D41
A67-B87-C11-D41
A39-B87-C11-D41
A65-B87-C11-D41
A66-B87-C11-D41
A2-B89-C11-D41
A3-B89-C11-D41
A9-B89-C11-D41
A13-B89-C11-D41
A24-B89-C11-D41
A69-B89-C11-D41
A67-B89-C11-D41
A39-B89-C11-D41
A65-B89-C11-D41
A66-B89-C11-D41
A2-B92-C11-D41
A3-B92-C11-D41
A9-B92-C11-D41
A13-B92-C11-D41
A24-B92-C11-D41
A69-B92-C11-D41
A67-B92-C11-D41
A39-B92-C11-D41
A65-B92-C11-D41
A66-B92-C11-D41
A2-B4-C12-D41
A3-B4-C12-D41
A9-B4-C12-D41
A13-B4-C12-D41
A24-B4-C12-D41
A69-B4-C12-D41
A67-B4-C12-D41
A39-B4-C12-D41
A65-B4-C12-D41
A66-B4-C12-D41
A2-B5-C12-D41
A3-B5-C12-D41
A9-B5-C12-D41
A13-B5-C12-D41
A24-B5-C12-D41
A69-B5-C12-D41
A67-B5-C12-D41
A39-B5-C12-D41
A65-B5-C12-D41
A66-B5-C12-D41
A2-B6-C12-D41
A3-B6-C12-D41
A9-B6-C12-D41
A13-B6-C12-D41
A24-B6-C12-D41
A69-B6-C12-D41
A67-B6-C12-D41
A39-B6-C12-D41
A65-B6-C12-D41
A66-B6-C12-D41
A2-B32-C12-D41
A3-B32-C12-D41
A9-B32-C12-D41
A13-B32-C12-D41
A24-B32-C12-D41
A69-B32-C12-D41
A67-B32-C12-D4
A39-B32-C12-D41
A65-B32-C12-D41
A66-B32-C12-D41
A2-B39-C12-D41
A3-B39-C12-D41
A9-B39-C12-D41

-continued

A13-B39-C12-D41
A24-B39-C12-D41
A69-B39-C12-D41
A67-B39-C12-D41
A39-B39-C12-D41
A65-B39-C12-D41
A66-B39-C12-D41
A2-B45-C12-D41
A3-B45-C12-D41
A9-B45-C12-D41
A13-B45-C12-D41
A24-B45-C12-D41
A69-B45-C12-D41
A67-B45-C12-D41
A39-B45-C12-D41
A65-B45-C12-D41
A66-B45-C12-D41
A2-B53-C12-D41
A3-B53-C12-D41
A9-B53-C12-D41
A13-B53-C12-D41
A24-B53-C12-D41
A69-B53-C12-D41
A67-B53-C12-D41
A39-B53-C12-D41
A65-B53-C12-D41
A66-B53-C12-D41
A2-B79-C12-D41
A3-B79-C12-D41
A9-B79-C12-D41
A13-B79-C12-D41
A24-B79-C12-D41
A69-B79-C12-D41
A67-B79-C12-D41
A39-B79-C12-D41
A65-B79-C12-D41
A66-B79-C12-D41
A2-B80-C12-D41
A3-B80-C12-D41
A9-B80-C12-D41
A13-B80-C12-D41
A24-B80-C12-D41
A69-B80-C12-D41
A67-B80-C12-D41
A39-B80-C12-D41
A65-B80-C12-D41
A66-B80-C12-D41
A2-B85-C12-D41
A3-B85-C12-D41
A9-B85-C12-D41
A13-B85-C12-D41
A24-B85-C12-D41
A69-B85-C12-D41
A67-B85-C12-D41
A39-B85-C12-D41
A65-B85-C12-D41
A66-B85-C12-D41
A2-B86-C12-D41
A3-B86-C12-D41
A9-B86-C12-D41
A13-B86-C12-D41
A24-B86-C12-D41
A69-B86-C12-D41
A67-B86-C12-D41
A39-B86-C12-D41
A65-B86-C12-D41
A66-B86-C12-D41
A2-B87-C12-D41
A3-B87-C12-D41
A9-B87-C12-D41
A13-B87-C12-D41
A24-B87-C12-D41
A69-B87-C12-D41
A67-B87-C12-D41
A39-B87-C12-D41
A65-B87-C12-D41
A66-B87-C12-D41
A2-B89-C12-D41
A3-B89-C12-D41
A9-B89-C12-D41

-continued
A13-B89-C12-D41
A24-B89-C12-D41
A69-B89-C12-D41
A67-B89-C12-D41
A39-B89-C12-D41
A65-B89-C12-D41
A66-B89-C12-D41
A2-B92-C12-D41
A3-B92-C12-D41
A9-B92-C12-D41
A13-B92-C12-D41
A24-B92-C12-D41
A69-B92-C12-D41
A67-B92-C12-D41
A39-B92-C12-D41
A65-B92-C12-D41
A66-B92-C12-D41
A2-B4-C13-D41
A3-B4-C13-D41
A9-B4-C13-D41
A13-B4-C13-D41
A24-B4-C13-D41
A69-B4-C13-D41
A67-B4-C13-D41
A39-B4-C13-D41
A65-B4-C13-D41
A66-B4-C13-D41
A2-B5-C13-D41
A3-B5-C13-D41
A9-B5-C13-D41
A13-B5-C13-D41
A24-B5-C13-D41
A69-B5-C13-D41
A67-B5-C13-D41
A39-B5-C13-D41
A65-B5-C13-D41
A66-B5-C13-D41
A2-B6-C13-D41
A3-B6-C13-D41
A9-B6-C13-D41
A13-B6-C13-D41
A24-B6-C13-D41
A69-B6-C13-D41
A67-B6-C13-D41
A39-B6-C13-D41
A65-B6-C13-D41
A66-B6-C13-D41
A2-B32-C13-D41
A3-B32-C13-D41
A9-B32-C13-D41
A13-B32-C13-D41
A24-B32-C13-D41
A69-B32-C13-D41
A67-B32-C13-D41
A39-B32-C13-D41
A65-B32-C13-D41
A66-B32-C13-D41
A2-B39-C13-D41
A3-B39-C13-D41
A9-B39-C13-D41
A13-B39-C13-D41
A24-B39-C13-D41
A69-B39-C13-D41
A67-B39-C13-D41
A39-B39-C13-D41
A65-B39-C13-D41
A66-B39-C13-D41
A2-B45-C13-D41
A3-B45-C13-D41
A9-B45-C13-D41
A13-B45-C13-D41
A24-B45-C13-D41
A69-B45-C13-D41
A67-B45-C13-D41
A39-B45-C13-D41
A65-B45-C13-D41
A66-B45-C13-D41
A2-B53-C13-D41
A3-B53-C13-D41
A9-B53-C13-D41

-continued
A13-B53-C13-D41
A24-B53-C13-D41
A69-B53-C13-D41
A67-B53-C13-D41
A39-B53-C13-D41
A65-B53-C13-D41
A66-B53-C13-D41
A2-B79-C13-D41
A3-B79-C13-D41
A9-B79-C13-D41
A13-B79-C13-D41
A24-B79-C13-D41
A69-B79-C13-D41
A67-B79-C13-D41
A39-B79-C13-D41
A65-B79-C13-D41
A66-B79-C13-D41
A2-B80-C13-D41
A3-B80-C13-D41
A9-B80-C13-D41
A13-B80-C13-D41
A24-B80-C13-D41
A69-B80-C13-D41
A67-B80-C13-D41
A39-B80-C13-D41
A65-B80-C13-D41
A66-B80-C13-D41
A2-B85-C13-D41
A3-B85-C13-D41
A9-B85-C13-D41
A13-B85-C13-D41
A24-B85-C13-D41
A69-B85-C13-D41
A67-B85-C13-D41
A39-B85-C13-D41
A65-B85-C13-D41
A66-B85-C13-D41
A2-B86-C13-D41
A3-B86-C13-D41
A9-B86-C13-D41
A13-B86-C13-D41
A24-B86-C13-D41
A69-B86-C13-D41
A67-B86-C13-D41
A39-B86-C13-D41
A65-B86-C13-D41
A66-B86-C13-D41
A2-B87-C13-D41
A3-B87-C13-D41
A9-B87-C13-D41
A13-B87-C13-D41
A24-B87-C13-D41
A69-B87-C13-D41
A67-B87-C13-D41
A39-B87-C13-D41
A65-B87-C13-D41
A66-B87-C13-D41
A2-B89-C13-D41
A3-B89-C13-D41
A9-B89-C13-D41
A13-B89-C13-D41
A24-B89-C13-D41
A69-B89-C13-D41
A67-B89-C13-D41
A39-B89-C13-D41
A65-B89-C13-D41
A66-B89-C13-D41
A2-B92-C13-D41
A3-B92-C13-D41
A9-B92-C13-D41
A13-B92-C13-D41
A24-B92-C13-D41
A69-B92-C13-D41
A67-B92-C13-D41
A39-B92-C13-D41
A65-B92-C13-D41
A66-B92-C13-D41
A2-B4-C1-D42
A3-B4-C1-D42
A9-B4-C1-D42

-continued
A13-B4-C1-D42
A24-B4-C1-D42
A69-B4-C1-D42
A67-B4-C1-D42
A39-B4-C1-D42
A65-B4-C1-D42
A66-B4-C1-D42
A2-B5-C1-D42
A3-B5-C1-D42
A9-B5-C1-D42
A13-B5-C1-D42
A24-B5-C1-D42
A69-B5-C1-D42
A67-B5-C1-D42
A39-B5-C1-D42
A65-B5-C1-D42
A66-B5-C1-D42
A2-B6-C1-D42
A3-B6-C1-D42
A9-B6-C1-D42
A13-B6-C1-D42
A24-B6-C1-D42
A69-B6-C1-D42
A67-B6-C1-D42
A39-B6-C1-D42
A65-B6-C1-D42
A66-B6-C1-D42
A2-B32-C1-D42
A3-B32-C1-D427
A9-B32-C1-D42
A13-B32-C1-D42
A24-B32-C1-D42
A69-B32-C1-D42
A67-B32-C1-D42
A39-B32-C1-D42
A65-B32-C1-D42
A66-B32-C1-D42
A2-B39-C1-D42
A3-B39-C1-D42
A9-B39-C1-D42
A13-B39-C1-D42
A24-B39-C1-D42
A69-B39-C1-D42
A67-B39-C1-D42
A39-B39-C1-D42
A65-B39-C1-D42
A66-B39-C1-D42
A2-B45-C1-D42
A3-B45-C1-D429
A9-B45-C1-D42
A13-B45-C1-D42
A24-B45-C1-D42
A69-B45-C1-D42
A67-B45-C1-D42
A39-B45-C1-D42
A65-B45-C1-D42
A66-B45-C1-D42
A2-B53-C1-D42
A3-B53-C1-D42
A9-B53-C1-D42
A13-B53-C1-D42
A24-B53-C1-D42
A69-B53-C1-D42
A67-B53-C1-D42
A39-B53-C1-D42
A65-B53-C1-D42
A66-B53-C1-D42
A2-B79-C1-D42
A3-B79-C1-D42
A9-B79-C1-D42
A13-B79-C1-D42
A24-B79-C1-D42
A69-B79-C1-D42
A67-B79-C1-D42
A39-B79-C1-D42
A65-B79-C1-D42
A66-B79-C1-D42
A2-B80-C1-D42
A3-B80-C1-D42
A9-B80-C1-D42

-continued
A13-B80-C1-D42
A24-B80-C1-D42
A69-B80-C1-D42
A67-B80-C1-D42
A39-B80-C1-D42
A65-B80-C1-D42
A66-B80-C1-D42
A2-B85-C1-D42
A3-B85-C1-D42
A9-B85-C1-D42
A13-B85-C1-D42
A24-B85-C1-D42
A69-B85-C1-D42
A67-B85-C1-D42
A39-B85-C1-D42
A65-B85-C1-D42
A66-B85-C1-D42
A2-B86-C1-D42
A3-B86-C1-D42
A9-B86-C1-D42
A13-B86-C1-D42
A24-B86-C1-D42
A69-B86-C1-D42
A67-B86-C1-D42
A39-B86-C1-D42
A65-B86-C1-D42
A66-B86-C1-D42
A2-B87-C1-D42
A3-B87-C1-D42
A9-B87-C1-D42
A13-B87-C1-D42
A24-B87-C1-D42
A69-B87-C1-D42
A67-B87-C1-D42
A39-B87-C1-D42
A65-B87-C1-D42
A66-B87-C1-D42
A2-B89-C1-D42
A3-B89-C1-D42
A9-B89-C1-D42
A13-B89-C1-D42
A24-B89-C1-D42
A69-B89-C1-D42
A67-B89-C1-D42
A39-B89-C1-D42
A65-B89-C1-D42
A66-B89-C1-D42
A2-B92-C1-D42
A3-B92-C1-D42
A9-B92-C1-D42
A13-B92-C1-D42
A24-B92-C1-D42
A69-B92-C1-D42
A67-B92-C1-D42
A39-B92-C1-D42
A65-B92-C1-D42
A66-B92-C1-D42
A2-B4-C2-D42
A3-B4-C2-D42
A9-B4-C2-D42
A13-B4-C2-D42
A24-B4-C2-D42
A69-B4-C2-D42
A67-B4-C2-D42
A39-B4-C2-D42
A65-B4-C2-D42
A66-B4-C2-D42
A2-B5-C2-D42
A3-B5-C2-D42
A9-B5-C2-D42
A13-B5-C2-D42
A24-B5-C2-D42
A69-B5-C2-D42
A67-B5-C2-D42
A39-B5-C2-D42
A65-B5-C2-D42
A66-B5-C2-D42
A2-B6-C2-D42
A3-B6-C2-D42
A9-B6-C2-D42

-continued
A13-B6-C2-D42
A24-B6-C2-D42
A69-B6-C2-D42
A67-B6-C2-D42
A39-B6-C2-D42
A65-B6-C2-D42
A66-B6-C2-D42
A2-B32-C2-D42
A3-B32-C2-D42
A9-B32-C2-D42
A13-B32-C2-D42
A24-B32-C2-D42
A69-B32-C2-D42
A67-B32-C2-D42
A39-B32-C2-D42
A65-B32-C2-D42
A66-B32-C2-D42
A2-B39-C2-D42
A3-B39-C2-D42
A9-B39-C2-D42
A13-B39-C2-D42
A24-B39-C2-D42
A69-B39-C2-D42
A67-B39-C2-D42
A39-B39-C2-D42
A65-B39-C2-D42
A66-B39-C2-D42
A2-B45-C2-D42
A3-B45-C2-D42
A9-B45-C2-D42
A13-B45-C2-D42
A24-B45-C2-D42
A69-B45-C2-D42
A67-B45-C2-D42
A39-B45-C2-D42
A65-B45-C2-D42
A66-B45-C2-D42
A2-B53-C2-D42
A3-B53-C2-D42
A9-B53-C2-D42
A13-B53-C2-D42
A24-B53-C2-D42
A69-B53-C2-D42
A67-B53-C2-D42
A39-B53-C2-D42
A65-B53-C2-D42
A66-B53-C2-D42
A2-B79-C2-D42
A3-B79-C2-D42
A9-B79-C2-D42
A13-B79-C2-D42
A24-B79-C2-D42
A69-B79-C2-D42
A67-B79-C2-D42
A39-B79-C2-D42
A65-B79-C2-D42
A66-B79-C2-D42
A2-B80-C2-D42
A3-B80-C2-D42
A9-B80-C2-D42
A13-B80-C2-D42
A24-B80-C2-D42
A69-B80-C2-D42
A67-B80-C2-D42
A39-B80-C2-D42
A65-B80-C2-D42
A66-B80-C2-D42
A2-B85-C2-D42
A3-B85-C2-D42
A9-B85-C2-D42
A13-B85-C2-D42
A24-B85-C2-D42
A69-B85-C2-D42
A67-B85-C2-D42
A39-B85-C2-D42
A65-B85-C2-D42
A66-B85-C2-D42
A2-B86-C2-D42
A3-B86-C27-D42
A9-B86-C2-D42

-continued
A13-B86-C2-D42
A24-B86-C2-D42
A69-B86-C2-D42
A67-B86-C2-D42
A39-B86-C2-D42
A65-B86-C2-D42
A66-B86-C2-D42
A2-B87-C2-D42
A3-B87-C2-D42
A9-B87-C2-D42
A13-B87-C2-D42
A24-B87-C2-D42
A69-B87-C2-D42
A67-B87-C2-D42
A39-B87-C2-D42
A65-B87-C2-D42
A66-B87-C2-D42
A2-B89-C2-D42
A3-B89-C2-D42
A9-B89-C2-D42
A13-B89-C2-D42
A24-B89-C2-D42
A69-B89-C2-D42
A67-B89-C2-D42
A39-B89-C2-D42
A65-B89-C2-D42
A66-B89-C2-D42
A2-B92-C2-D42
A3-B92-C2-D42
A9-B92-C2-D42
A13-B92-C2-D42
A24-B92-C2-D42
A69-B92-C2-D42
A67-B92-C2-D42
A39-B92-C2-D42
A65-B92-C2-D42
A66-B92-C2-D42
A2-B4-C3-D42
A3-B4-C3-D42
A9-B4-C3-D42
A13-B4-C3-D42
A24-B4-C3-D42
A69-B4-C3-D42
A67-B4-C3-D42
A39-B4-C3-D42
A65-B4-C3-D42
A66-B4-C3-D42
A2-B5-C3-D42
A3-B5-C3-D42
A9-B5-C3-D42
A13-B5-C3-D42
A24-B5-C3-D42
A69-B5-C3-D42
A67-B5-C3-D42
A39-B5-C3-D42
A65-B5-C3-D42
A66-B5-C3-D42
A2-B6-C3-D42
A3-B6-C3-D42
A9-B6-C3-D42
A13-B6-C3-D42
A24-B6-C3-D42
A69-B6-C3-D42
A67-B6-C3-D42
A39-B6-C3-D42
A65-B6-C3-D42
A66-B6-C3-D42
A2-B32-C3-D42
A3-B32-C3-D42
A9-B32-C3-D42
A13-B32-C3-D42
A24-B32-C3-D42
A69-B32-C3-D42
A67-B32-C3-D42
A39-B32-C3-D42
A65-B32-C3-D42
A66-B32-C3-D42
A2-B39-C3-D42
A3-B39-C3-D42
A9-B39-C3-D42

-continued

A13-B39-C3-D42
A24-B39-C3-D42
A69-B39-C3-D42
A67-B39-C3-D42
A39-B39-C3-D42
A65-B39-C3-D42
A66-B39-C3-D42
A2-B45-C3-D42
A3-B45-C3-D42
A9-B45-C3-D42
A13-B45-C3-D42
A24-B45-C3-D42
A69-B45-C3-D42
A67-B45-C3-D42
A39-B45-C3-D42
A65-B45-C3-D42
A66-B45-C3-D42
A2-B53-C3-D42
A3-B53-C3-D42
A9-B53-C3-D42
A13-B53-C3-D42
A24-B53-C3-D42
A69-B53-C3-D42
A67-B53-C3-D42
A39-B53-C3-D42
A65-B53-C3-D42
A66-B53-C3-D42
A2-B79-C3-D42
A3-B79-C3-D42
A9-B79-C3-D42
A13-B79-C3-D42
A24-B79-C3-D42
A69-B79-C3-D42
A67-B79-C3-D42
A39-B79-C3-D42
A65-B79-C3-D42
A66-B79-C3-D42
A2-B80-C3-D42
A3-B80-C3-D42
A9-B80-C3-D42
A13-B80-C3-D42
A24-B80-C3-D42
A69-B80-C3-D42
A67-B80-C3-D42
A39-B80-C3-D42
A65-B80-C3-D42
A66-B80-C3-D42
A2-B85-C3-D42
A3-B85-C3-D42
A9-B85-C3-D42
A13-B85-C3-D42
A24-B85-C3-D42
A69-B85-C3-D42
A67-B85-C3-D42
A39-B85-C3-D42
A65-B85-C3-D42
A66-B85-C3-D42
A2-B86-C3-D42
A3-B86-C3-D42
A9-B86-C3-D42
A13-B86-C3-D42
A24-B86-C3-D42
A69-B86-C3-D42
A67-B86-C3-D42
A39-B86-C3-D42
A65-B86-C3-D42
A66-B86-C3-D42
A2-B87-C3-D42
A3-B87-C3-D42
A9-B87-C3-D42
A13-B87-C3-D42
A24-B87-C3-D42
A69-B87-C3-D42
A67-B87-C3-D42
A39-B87-C3-D42
A65-B87-C3-D42
A66-B87-C3-D42
A2-B89-C3-D42
A3-B89-C3-D42
A9-B89-C3-D42

-continued

A13-B89-C3-D42
A24-B89-C3-D42
A69-B89-C3-D42
A67-B89-C3-D42
A39-B89-C3-D42
A65-B89-C3-D42
A66-B89-C3-D42
A2-B92-C3-D42
A3-B92-C3-D42
A9-B92-C3-D42
A13-B92-C3-D42
A24-B92-C3-D42
A69-B92-C3-D42
A67-B92-C3-D42
A39-B92-C3-D42
A65-B92-C3-D42
A66-B92-C3-D42
A2-B4-C4-D42
A3-B4-C4-D42
A9-B4-C4-D42
A13-B4-C4-D42
A24-B4-C4-D42
A69-B4-C4-D42
A67-B4-C4-D42
A39-B4-C4-D42
A65-B4-C4-D42
A66-B4-C4-D42
A2-B5-C4-D42
A3-B5-C4-D42
A9-B5-C4-D42
A13-B5-C4-D42
A24-B5-C4-D42
A69-B5-C4-D42
A67-B5-C4-D42
A39-B5-C4-D42
A65-B5-C4-D42
A66-B5-C4-D42
A2-B6-C4-D42
A3-B6-C4-D42
A9-B6-C4-D42
A13-B6-C4-D42
A24-B6-C4-D42
A69-B6-C4-D42
A67-B6-C4-D42
A39-B6-C4-D42
A65-B6-C4-D42
A66-B6-C4-D42
A2-B32-C4-D42
A3-B32-C4-D42
A9-B32-C4-D42
A13-B32-C4-D42
A24-B32-C4-D42
A69-B32-C4-D42
A67-B32-C4-D42
A39-B32-C4-D42
A65-B32-C4-D42
A66-B32-C4-D42
A2-B39-C4-D42
A3-B39-C4-D42
A9-B39-C4-D42
A13-B39-C4-D42
A24-B39-C4-D42
A69-B39-C4-D42
A67-B39-C4-D42
A39-B39-C4-D42
A65-B39-C4-D42
A66-B39-C4-D42
A2-B45-C4-D42
A3-B45-C4-D42
A9-B45-C4-D42
A13-B45-C4-D42
A24-B45-C4-D42
A69-B45-C4-D42
A67-B45-C4-D42
A39-B45-C4-D42
A65-B45-C4-D42
A66-B45-C4-D42
A2-B53-C4-D42
A3-B53-C4-D42
A9-B53-C4-D42

-continued
A13-B53-C4-D42
A24-B53-C4-D42
A69-B53-C4-D42
A67-B53-C4-D42
A39-B53-C4-D42
A65-B53-C4-D42
A66-B53-C4-D42
A2-B79-C4-D42
A3-B79-C4-D42
A9-B79-C4-D42
A13-B79-C4-D42
A24-B79-C4-D42
A69-B79-C4-D42
A67-B79-C4-D42
A39-B79-C4-D42
A65-B79-C4-D42
A66-B79-C4-D42
A2-B80-C4-D42
A3-B80-C4-D42
A9-B80-C4-D42
A13-B80-C4-D42
A24-B80-C4-D42
A69-B80-C4-D42
A67-B80-C4-D42
A39-B80-C4-D42
A65-B80-C4-D42
A66-B80-C4-D42
A2-B85-C4-D42
A3-B85-C4-D42
A9-B85-C4-D42
A13-B85-C4-D42
A24-B85-C4-D42
A69-B85-C4-D42
A67-B85-C4-D42
A39-B85-C4-D42
A65-B85-C4-D42
A66-B85-C4-D42
A2-B86-C4-D42
A3-B86-C4-D42
A9-B86-C4-D42
A13-B86-C4-D42
A24-B86-C4-D42
A69-B86-C4-D42
A67-B86-C4-D42
A39-B86-C4-D42
A65-B86-C4-D42
A66-B86-C4-D42
A2-B87-C4-D42
A3-B87-C4-D42
A9-B87-C4-D42
A13-B87-C4-D42
A24-B87-C4-D42
A69-B87-C4-D42
A67-B87-C4-D42
A39-B87-C4-D42
A65-B87-C4-D42
A66-B87-C4-D42
A2-B89-C4-D42
A3-B89-C4-D42
A9-B89-C4-D42
A13-B89-C4-D42
A24-B89-C4-D42
A69-B89-C4-D42
A67-B89-C4-D42
A39-B89-C4-D42
A65-B89-C4-D42
A66-B89-C4-D42
A2-B92-C4-D42
A3-B92-C4-D42
A9-B92-C4-D42
A13-B92-C4-D42
A24-B92-C4-D42
A69-B92-C4-D42
A67-B92-C4-D42
A39-B92-C4-D42
A65-B92-C4-D42
A66-B92-C4-D42
A2-B4-C5-D42
A3-B4-C5-D42
A9-B4-C5-D42

-continued
A13-B4-C5-D42
A24-B4-C5-D42
A69-B4-C5-D42
A67-B4-C5-D42
A39-B4-C5-D42
A65-B4-C5-D42
A66-B4-C5-D42
A2-B5-C5-D42
A3-B5-C5-D42
A9-B5-C5-D42
A13-B5-C5-D42
A24-B5-C5-D42
A69-B5-C5-D42
A67-B5-C5-D42
A39-B5-C5-D42
A65-B5-C5-D42
A66-B5-C5-D42
A2-B6-C5-D42
A3-B6-C5-D42
A9-B6-C5-D42
A13-B6-C5-D42
A24-B6-C5-D42
A69-B6-C5-D42
A67-B6-C5-D42
A39-B6-C5-D42
A65-B6-C5-D42
A66-B6-C5-D42
A2-B32-C5-D42
A3-B32-C5-D42
A9-B32-C5-D42
A13-B32-C5-D42
A24-B32-C5-D42
A69-B32-C5-D42
A67-B32-C5-D42
A39-B32-C5-D42
A65-B32-C5-D42
A66-B32-C5-D42
A2-B39-C5-D42
A3-B39-C5-D42
A9-B39-C5-D42
A13-B39-C5-D42
A24-B39-C5-D42
A69-B39-C5-D42
A67-B39-C5-D42
A39-B39-C5-D42
A65-B39-C5-D42
A66-B39-C5-D42
A2-B45-C5-D42
A3-B45-C5-D42
A9-B45-C5-D42
A13-B45-C5-D42
A24-B45-C5-D42
A69-B45-C5-D42
A67-B45-C5-D42
A39-B45-C5-D42
A65-B45-C5-D42
A66-B45-C5-D42
A2-B53-C5-D42
A3-B53-C5-D42
A9-B53-C5-D42
A13-B53-C5-D42
A24-B53-C5-D42
A69-B53-C5-D42
A67-B53-C5-D42
A39-B53-C5-D42
A65-B53-C5-D42
A66-B53-C5-D42
A2-B79-C5-D42
A3-B79-C5-D42
A9-B79-C5-D42
A13-B79-C5-D42
A24-B79-C5-D42
A69-B79-C5-D42
A67-B79-C5-D42
A39-B79-C5-D42
A65-B79-C5-D42
A66-B79-C5-D42
A2-B80-C5-D42
A3-B80-C5-D42
A9-B80-C5-D42

-continued

A13-B80-C5-D42
A24-B80-C5-D42
A69-B80-C5-D42
A67-B80-C5-D42
A39-B80-C5-D42
A65-B80-C5-D42
A66-B80-C5-D42
A2-B85-C5-D42
A3-B85-C5-D42
A9-B85-C5-D42
A13-B85-C5-D42
A24-B85-C5-D42
A69-B85-C5-D42
A67-B85-C5-D42
A39-B85-C5-D42
A65-B85-C5-D42
A66-B85-C5-D42
A2-B86-C5-D42
A3-B86-C5-D42
A9-B86-C5-D42
A13-B86-C5-D42
A24-B86-C5-D42
A69-B86-C5-D42
A67-B86-C5-D42
A39-B86-C5-D42
A65-B86-C5-D42
A66-B86-C5-D42
A2-B87-C5-D42
A3-B87-C5-D42
A9-B87-C5-D42
A13-B87-C5-D42
A24-B87-C5-D42
A69-B87-C5-D42
A67-B87-C5-D42
A39-B87-C5-D42
A65-B87-C5-D42
A66-B87-C5-D42
A2-B89-C5-D42
A3-B89-C5-D42
A9-B89-C5-D42
A13-B89-C5-D42
A24-B89-C5-D42
A69-B89-C5-D42
A67-B89-C5-D42
A39-B89-C5-D42
A65-B89-C5-D42
A66-B89-C5-D42
A2-B92-C5-D42
A3-B92-C5-D42
A9-B92-C5-D42
A13-B92-C5-D42
A24-B92-C5-D42
A69-B92-C5-D42
A67-B92-C5-D42
A39-B92-C5-D42
A65-B92-C5-D42
A66-B92-C5-D42
A2-B4-C6-D42
A3-B4-C6-D42
A9-B4-C6-D42
A13-B4-C6-D42
A24-B4-C6-D42
A69-B4-C6-D42
A67-B4-C6-D42
A39-B4-C6-D42
A65-B4-C6-D42
A66-B4-C6-D42
A2-B5-C6-D42
A3-B5-C6-D42
A9-B5-C6-D42
A13-B5-C6-D42
A24-B5-C6-D42
A69-B5-C6-D42
A67-B5-C6-D42
A39-B5-C6-D42
A65-B5-C6-D42
A66-B5-C6-D42
A2-B6-C6-D42
A3-B6-C6-D42
A9-B6-C6-D42

-continued

A13-B6-C6-D42
A24-B6-C6-D42
A69-B6-C6-D42
A67-B6-C6-D42
A39-B6-C6-D42
A65-B6-C6-D42
A66-B6-C6-D42
A2-B32-C6-D42
A3-B32-C6-D42
A9-B32-C6-D42
A13-B32-C6-D42
A24-B32-C6-D42
A69-B32-C6-D42
A67-B32-C6-D42
A39-B32-C6-D42
A65-B32-C6-D42
A66-B32-C6-D42
A2-B39-C6-D42
A3-B39-C6-D42
A9-B39-C6-D42
A13-B39-C6-D42
A24-B39-C6-D42
A69-B39-C6-D42
A67-B39-C6-D42
A39-B39-C6-D42
A65-B39-C6-D42
A66-B39-C6-D42
A2-B45-C6-D42
A3-B45-C6-D42
A9-B45-C6-D42
A13-B45-C6-D42
A24-B45-C6-D42
A69-B45-C6-D42
A67-B45-C6-D42
A39-B45-C6-D42
A65-B45-C6-D42
A66-B45-C6-D42
A2-B53-C6-D42
A3-B53-C6-D42
A9-B53-C6-D42
A13-B53-C6-D42
A24-B53-C6-D42
A69-B53-C6-D42
A67-B53-C6-D42
A39-B53-C6-D42
A65-B53-C6-D42
A66-B53-C6-D42
A2-B79-C6-D42
A3-B79-C6-D42
A9-B79-C6-D42
A13-B79-C6-D42
A24-B79-C6-D42
A69-B79-C6-D42
A67-B79-C6-D42
A39-B79-C6-D42
A65-B79-C6-D42
A66-B79-C6-D42
A2-B80-C6-D42
A3-B80-C6-D42
A9-B80-C6-D42
A13-B80-C6-D42
A24-B80-C6-D42
A69-B80-C6-D42
A67-B80-C6-D42
A39-B80-C6-D42
A65-B80-C6-D42
A66-B80-C6-D42
A2-B85-C6-D42
A3-B85-C6-D42
A9-B85-C6-D42
A13-B85-C6-D42
A24-B85-C6-D42
A69-B85-C6-D42
A67-B85-C6-D42
A39-B85-C6-D42
A65-B85-C6-D42
A66-B85-C6-D42
A2-B86-C6-D42
A3-B86-C6-D42
A9-B86-C6-D42

-continued
A13-B86-C6-D42
A24-B86-C6-D42
A69-B86-C6-D42
A67-B86-C6-D42
A39-B86-C6-D42
A65-B86-C6-D42
A66-B86-C6-D42
A2-B87-C6-D42
A3-B87-C6-D42
A9-B87-C6-D42
A13-B87-C6-D42
A24-B87-C6-D42
A69-B87-C6-D42
A67-B87-C6-D42
A39-B87-C6-D42
A65-B87-C6-D42
A66-B87-C6-D42
A2-B89-C6-D42
A3-B89-C6-D42
A9-B89-C6-D42
A13-B89-C6-D42
A24-B89-C6-D42
A69-B89-C6-D42
A67-B89-C6-D42
A39-B89-C6-D42
A65-B89-C6-D42
A66-B89-C6-D42
A2-B92-C6-D42
A3-B92-C6-D42
A9-B92-C6-D42
A13-B92-C6-D42
A24-B92-C6-D42
A69-B92-C6-D42
A67-B92-C6-D42
A39-B92-C6-D42
A65-B92-C6-D42
A66-B92-C6-D42
A2-B4-C7-D42
A3-B4-C7-D42
A9-B4-C7-D42
A13-B4-C7-D42
A24-B4-C7-D42
A69-B4-C7-D42
A67-B4-C7-D42
A39-B4-C7-D42
A65-B4-C7-D42
A66-B4-C7-D42
A2-B5-C7-D42
A3-B5-C7-D42
A9-B5-C7-D42
A13-B5-C7-D42
A24-B5-C7-D42
A69-B5-C7-D42
A67-B5-C7-D42
A39-B5-C7-D42
A65-B5-C7-D42
A66-B5-C7-D42
A2-B6-C7-D42
A3-B6-C7-D42
A9-B6-C7-D42
A13-B6-C7-D42
A24-B6-C7-D42
A69-B6-C7-D42
A67-B6-C7-D42
A39-B6-C7-D42
A65-B6-C7-D42
A66-B6-C7-D42
A2-B32-C7-D42
A3-B32-C7-D42
A9-B32-C7-D42
A13-B32-C7-D42
A24-B32-C7-D42
A69-B32-C7-D42
A67-B32-C7-D42
A39-B32-C7-D42
A65-B32-C7-D42
A66-B32-C7-D42
A2-B39-C7-D42
A3-B39-C7-D42
A9-B39-C7-D42

-continued
A13-B39-C7-D42
A24-B39-C7-D42
A69-B39-C7-D42
A67-B39-C7-D42
A39-B39-C7-D42
A65-B39-C7-D42
A66-B39-C7-D42
A2-B45-C7-D42
A3-B45-C7-D42
A9-B45-C7-D42
A13-B45-C7-D42
A24-B45-C7-D42
A69-B45-C7-D42
A67-B45-C7-D42
A39-B45-C7-D42
A65-B45-C7-D42
A66-B45-C7-D42
A2-B53-C7-D42
A3-B53-C7-D42
A9-B53-C7-D42
A13-B53-C7-D42
A24-B53-C7-D42
A69-B53-C7-D42
A67-B53-C7-D42
A39-B53-C7-D42
A65-B53-C7-D42
A66-B53-C7-D42
A2-B79-C7-D42
A3-B79-C7-D42
A9-B79-C7-D42
A13-B79-C7-D42
A24-B79-C7-D42
A69-B79-C7-D42
A67-B79-C7-D42
A39-B79-C7-D42
A65-B79-C7-D42
A66-B79-C7-D42
A2-B80-C7-D42
A3-B80-C7-D42
A9-B80-C7-D42
A13-B80-C7-D42
A24-B80-C7-D42
A69-B80-C7-D42
A67-B80-C7-D42
A39-B80-C7-D42
A65-B80-C7-D42
A66-B80-C7-D42
A2-B85-C7-D42
A3-B85-C7-D42
A9-B85-C7-D42
A13-B85-C7-D42
A24-B85-C7-D42
A69-B85-C7-D42
A67-B85-C7-D42
A39-B85-C7-D42
A65-B85-C7-D42
A66-B85-C7-D42
A2-B86-C7-D42
A3-B86-C7-D42
A9-B86-C7-D42
A13-B86-C7-D42
A24-B86-C7-D42
A69-B86-C7-D42
A67-B86-C7-D42
A39-B86-C7-D42
A65-B86-C7-D42
A66-B86-C7-D42
A2-B87-C7-D42
A3-B87-C7-D42
A9-B87-C7-D42
A13-B87-C7-D42
A24-B87-C7-D42
A69-B87-C7-D42
A67-B87-C7-D42
A39-B87-C7-D42
A65-B87-C7-D42
A66-B87-C7-D42
A2-B89-C7-D42
A3-B89-C7-D42
A9-B89-C7-D42

-continued
A13-B89-C7-D42
A24-B89-C7-D42
A69-B89-C7-D42
A67-B89-C7-D42
A39-B89-C7-D42
A65-B89-C7-D42
A66-B89-C7-D42
A2-B92-C7-D42
A3-B92-C7-D42
A9-B92-C7-D42
A13-B92-C7-D42
A24-B92-C7-D42
A69-B92-C7-D42
A67-B92-C7-D42
A39-B92-C7-D42
A65-B92-C7-D42
A66-B92-C7-D42
A2-B4-C8-D42
A3-B4-C8-D42
A9-B4-C8-D42
A13-B4-C8-D42
A24-B4-C8-D42
A69-B4-C8-D42
A67-B4-C8-D42
A39-B4-C8-D42
A65-B4-C8-D42
A66-B4-C8-D42
A2-B5-C8-D42
A3-B5-C8-D42
A9-B5-C8-D42
A13-B5-C8-D42
A24-B5-C8-D42
A69-B5-C8-D42
A67-B5-C8-D42
A39-B5-C8-D42
A65-B5-C8-D42
A66-B5-C8-D42
A2-B6-C8-D42
A3-B6-C8-D42
A9-B6-C8-D42
A13-B6-C8-D42
A24-B6-C8-D42
A69-B6-C8-D42
A67-B6-C8-D42
A39-B6-C8-D42
A65-B6-C8-D42
A66-B6-C8-D42
A2-B32-C8-D42
A3-B32-C8-D42
A9-B32-C8-D42
A13-B32-C8-D42
A24-B32-C8-D42
A69-B32-C8-D42
A67-B32-C8-D42
A39-B32-C8-D42
A65-B32-C8-D42
A66-B32-C8-D42
A2-B39-C8-D42
A3-B39-C8-D42
A9-B39-C8-D42
A13-B39-C8-D42
A24-B39-C8-D42
A69-B39-C8-D42
A67-B39-C8-D42
A39-B39-C8-D42
A65-B39-C8-D42
A66-B39-C8-D42
A2-B45-C8-D42
A3-B45-C8-D42
A9-B45-C8-D42
A13-B45-C8-D42
A24-B45-C8-D42
A69-B45-C8-D42
A67-B45-C8-D42
A39-B45-C8-D42
A65-B45-C8-D42
A66-B45-C8-D42
A2-B53-C8-D42
A3-B53-C8-D42
A9-B53-C8-D42

-continued
A13-B53-C8-D42
A24-B53-C8-D42
A69-B53-C8-D42
A67-B53-C8-D42
A39-B53-C8-D42
A65-B53-C8-D42
A66-B53-C8-D42
A2-B79-C8-D42
A3-B79-C8-D42
A9-B79-C8-D42
A13-B79-C8-D42
A24-B79-C8-D42
A69-B79-C8-D42
A67-B79-C8-D42
A39-B79-C8-D42
A65-B79-C8-D42
A66-B79-C8-D42
A2-B80-C8-D42
A3-B80-C8-D42
A9-B80-C8-D42
A13-B80-C8-D42
A24-B80-C8-D42
A69-B80-C8-D42
A67-B80-C8-D42
A39-B80-C8-D42
A65-B80-C8-D42
A66-B80-C8-D42
A2-B85-C8-D42
A3-B85-C8-D42
A9-B85-C8-D42
A13-B85-C8-D42
A24-B85-C8-D42
A69-B85-C8-D42
A67-B85-C8-D42
A39-B85-C8-D42
A65-B85-C8-D42
A66-B85-C8-D42
A2-B86-C8-D42
A3-B86-C8-D42
A9-B86-C8-D42
A13-B86-C8-D42
A24-B86-C8-D42
A69-B86-C8-D42
A67-B86-C8-D42
A39-B86-C8-D42
A65-B86-C8-D42
A66-B86-C8-D42
A2-B87-C8-D42
A3-B87-C8-D42
A9-B87-C8-D42
A13-B87-C8-D42
A24-B87-C8-D42
A69-B87-C8-D42
A67-B87-C8-D42
A39-B87-C8-D42
A65-B87-C8-D42
A66-B87-C8-D42
A2-B89-C8-D42
A3-B89-C8-D42
A9-B89-C8-D42
A13-B89-C8-D42
A24-B89-C8-D42
A69-B89-C8-D42
A67-B89-C8-D42
A39-B89-C8-D42
A65-B89-C8-D42
A66-B89-C8-D42
A2-B92-C8-D42
A3-B92-C8-D42
A9-B92-C8-D42
A13-B92-C8-D42
A24-B92-C8-D42
A69-B92-C8-D42
A67-B92-C8-D42
A39-B92-C8-D42
A65-B92-C8-D42
A66-B92-C8-D42
A2-B4-C9-D42
A3-B4-C9-D42
A9-B4-C9-D42

-continued

A13-B4-C9-D42
A24-B4-C9-D42
A69-B4-C9-D42
A67-B4-C9-D42
A39-B4-C9-D42
A65-B4-C9-D42
A66-B4-C9-D42
A2-B5-C9-D42
A3-B5-C9-D427
A9-B5-C9-D42
A13-B5-C9-D42
A24-B5-C9-D42
A69-B5-C9-D42
A67-B5-C9-D42
A39-B5-C9-D42
A65-B5-C9-D42
A66-B5-C9-D42
A2-B6-C9-D42
A3-B6-C9-D42
A9-B6-C9-D42
A13-B6-C9-D42
A24-B6-C9-D42
A69-B6-C9-D42
A67-B6-C9-D42
A39-B6-C9-D42
A65-B6-C9-D42
A66-B6-C9-D42
A2-B32-C9-D42
A3-B32-C9-D42
A9-B32-C9-D42
A13-B32-C9-D42
A24-B32-C9-D42
A69-B32-C9-D42
A67-B32-C9-D42
A39-B32-C9-D42
A65-B32-C9-D42
A66-B32-C9-D42
A2-B39-C9-D42
A3-B39-C9-D42
A9-B39-C9-D42
A13-B39-C9-D42
A24-B39-C9-D42
A69-B39-C9-D42
A67-B39-C9-D42
A39-B39-C9-D42
A65-B39-C9-D42
A66-B39-C9-D42
A2-B45-C9-D42
A3-B45-C9-D42
A9-B45-C9-D42
A13-B45-C9-D42
A24-B45-C9-D42
A69-B45-C9-D42
A67-B45-C9-D42
A39-B45-C9-D42
A65-B45-C9-D42
A66-B45-C9-D42
A2-B53-C9-D42
A3-B53-C9-D42
A9-B53-C9-D42
A13-B53-C9-D42
A24-B53-C9-D42
A69-B53-C9-D42
A67-B53-C9-D42
A39-B53-C9-D42
A65-B53-C9-D42
A66-B53-C9-D42
A2-B79-C9-D42
A3-B79-C9-D42
A9-B79-C9-D42
A13-B79-C9-D42
A24-B79-C9-D42
A69-B79-C9-D42
A67-B79-C9-D42
A39-B79-C9-D42
A65-B79-C9-D42
A66-B79-C9-D42
A2-B80-C9-D42
A3-B80-C9-D42
A9-B80-C9-D42

-continued

A13-B80-C9-D42
A24-B80-C9-D42
A69-B80-C9-D42
A67-B80-C9-D42
A39-B80-C9-D42
A65-B80-C9-D42
A66-B80-C9-D42
A2-B85-C9-D42
A3-B85-C9-D42
A9-B85-C9-D42
A13-B85-C9-D42
A24-B85-C9-D42
A69-B85-C9-D42
A67-B85-C9-D42
A39-B85-C9-D42
A65-B85-C9-D42
A66-B85-C9-D42
A2-B86-C9-D42
A3-B86-C9-D42
A9-B86-C9-D42
A13-B86-C9-D42
A24-B86-C9-D42
A69-B86-C9-D42
A67-B86-C9-D42
A39-B86-C9-D42
A65-B86-C9-D42
A66-B86-C9-D42
A2-B87-C9-D42
A3-B87-C9-D42
A9-B87-C9-D42
A13-B87-C9-D42
A24-B87-C9-D42
A69-B87-C9-D42
A67-B87-C9-D42
A39-B87-C9-D42
A65-B87-C9-D42
A66-B87-C9-D42
A2-B89-C9-D42
A3-B89-C9-D42
A9-B89-C9-D42
A13-B89-C9-D42
A24-B89-C9-D42
A69-B89-C9-D42
A67-B89-C9-D42
A39-B89-C9-D42
A65-B89-C9-D42
A66-B89-C9-D42
A2-B92-C9-D42
A3-B92-C9-D42
A9-B92-C9-D42
A13-B92-C9-D42
A24-B92-C9-D42
A69-B92-C9-D42
A67-B92-C9-D42
A39-B92-C9-D42
A65-B92-C9-D42
A66-B92-C9-D42
A2-B4-C10-D42
A3-B4-C10-D42
A9-B4-C10-D42
A13-B4-C10-D42
A24-B4-C10-D42
A69-B4-C10-D42
A67-B4-C10-D42
A39-B4-C10-D42
A65-B4-C10-D42
A66-B4-C10-D42
A2-B5-C10-D42
A3-B5-C10-D42
A9-B5-C10-D42
A13-B5-C10-D42
A24-B5-C10-D42
A69-B5-C10-D42
A67-B5-C10-D42
A39-B5-C10-D42
A65-B5-C10-D42
A66-B5-C10-D42
A2-B6-C10-D42
A3-B6-C10-D42
A9-B6-C10-D42

-continued

A13-B6-C10-D42
A24-B6-C10-D42
A69-B6-C10-D42
A67-B6-C10-D42
A39-B6-C10-D42
A65-B6-C10-D42
A66-B6-C10-D42
A2-B32-C10-D42
A3-B32-C10-D42
A9-B32-C10-D42
A13-B32-C10-D42
A24-B32-C10-D42
A69-B32-C10-D42
A67-B32-C10-D42
A39-B32-C10-D42
A65-B32-C10-D42
A66-B32-C10-D42
A2-B39-C10-D42
A3-B39-C10-D42
A9-B39-C10-D42
A13-B39-C10-D42
A24-B39-C10-D42
A69-B39-C10-D42
A67-B39-C10-D42
A39-B39-C10-D42
A65-B39-C10-D42
A66-B39-C10-D42
A2-B45-C10-D42
A3-B45-C10-D42
A9-B45-C10-D42
A13-B45-C10-D42
A24-B45-C10-D42
A69-B45-C10-D42
A67-B45-C10-D42
A39-B45-C10-D42
A65-B45-C10-D42
A66-B45-C10-D42
A2-B53-C10-D42
A3-B53-C10-D42
A9-B53-C10-D42
A13-B53-C10-D42
A24-B53-C10-D42
A69-B53-C10-D42
A67-B53-C10-D42
A39-B53-C10-D42
A65-B53-C10-D42
A66-B53-C10-D42
A2-B79-C10-D42
A3-B79-C10-D42
A9-B79-C10-D42
A13-B79-C10-D42
A24-B79-C10-D42
A69-B79-C10-D42
A67-B79-C10-D42
A39-B79-C10-D42
A65-B79-C10-D42
A66-B79-C10-D42
A2-B80-C10-D42
A3-B80-C10-D42
A9-B80-C10-D42
A13-B80-C10-D42
A24-B80-C10-D42
A69-B80-C10-D42
A67-B80-C10-D42
A39-B80-C10-D42
A65-B80-C10-D42
A66-B80-C10-D42
A2-B85-C10-D42
A3-B85-C10-D42
A9-B85-C10-D42
A13-B85-C10-D42
A24-B85-C10-D42
A69-B85-C10-D42
A67-B85-C10-D42
A39-B85-C10-D42
A65-B85-C10-D42
A66-B85-C10-D42
A2-B86-C10-D42
A3-B86-C10-D42
A9-B86-C10-D42

-continued

A13-B86-C10-D42
A24-B86-C10-D42
A69-B86-C10-D42
A67-B86-C10-D42
A39-B86-C10-D42
A65-B86-C10-D42
A66-B86-C10-D42
A2-B87-C10-D42
A3-B87-C10-D42
A9-B87-C10-D42
A13-B87-C10-D42
A24-B87-C10-D42
A69-B87-C10-D42
A67-B87-C10-D42
A39-B87-C10-D42
A65-B87-C10-D42
A66-B87-C10-D42
A2-B89-C10-D42
A3-B89-C10-D42
A9-B89-C10-D42
A13-B89-C10-D42
A24-B89-C10-D42
A69-B89-C10-D42
A67-B89-C10-D42
A39-B89-C10-D42
A65-B89-C10-D42
A66-B89-C10-D42
A2-B92-C10-D42
A3-B92-C10-D42
A9-B92-C10-D42
A13-B92-C10-D42
A24-B92-C10-D42
A69-B92-C10-D42
A67-B92-C10-D42
A39-B92-C10-D42
A65-B92-C10-D42
A66-B92-C10-D42
A2-B4-C11-D42
A3-B4-C11-D42
A9-B4-C11-D42
A13-B4-C11-D42
A24-B4-C11-D42
A69-B4-C11-D42
A67-B4-C11-D42
A39-B4-C11-D42
A65-B4-C11-D42
A66-B4-C11-D42
A2-B5-C11-D42
A3-B5-C11-D42
A9-B5-C11-D42
A13-B5-C11-D42
A24-B5-C11-D42
A69-B5-C11-D42
A67-B5-C11-D42
A39-B5-C11-D42
A65-B5-C11-D42
A66-B5-C11-D42
A2-B6-C11-D42
A3-B6-C11-D42
A9-B6-C11-D42
A13-B6-C11-D42
A24-B6-C11-D42
A69-B6-C11-D42
A67-B6-C11-D42
A39-B6-C11-D42
A65-B6-C11-D42
A66-B6-C11-D42
A2-B32-C11-D42
A3-B32-C11-D42
A9-B32-C11-D42
A13-B32-C11-D42
A24-B32-C11-D42
A69-B32-C11-D42
A67-B32-C11-D42
A39-B32-C11-D42
A65-B32-C11-D42
A66-B32-C11-D42
A2-B39-C11-D42
A3-B39-C11-D42
A9-B39-C11-D42

-continued

| 1021 | 1022 |
|---|---|
| A13-B39-C11-D42 | A13-B89-C11-D42 |
| A24-B39-C11-D42 | A24-B89-C11-D42 |
| A69-B39-C11-D42 | A69-B89-C11-D42 |
| A67-B39-C11-D42 | A67-B89-C11-D42 |
| A39-B39-C11-D42 | A39-B89-C11-D42 |
| A65-B39-C11-D42 | A65-B89-C11-D42 |
| A66-B39-C11-D42 | A66-B89-C11-D42 |
| A2-B45-C11-D42 | A2-B92-C11-D42 |
| A3-B45-C11-D42 | A3-B92-C11-D42 |
| A9-B45-C11-D42 | A9-B92-C11-D42 |
| A13-B45-C11-D42 | A13-B92-C11-D42 |
| A24-B45-C11-D42 | A24-B92-C11-D42 |
| A69-B45-C11-D42 | A69-B92-C11-D42 |
| A67-B45-C11-D42 | A67-B92-C11-D42 |
| A39-B45-C11-D42 | A39-B92-C11-D42 |
| A65-B45-C11-D42 | A65-B92-C11-D42 |
| A66-B45-C11-D42 | A66-B92-C11-D42 |
| A2-B53-C11-D42 | A2-B4-C12-D42 |
| A3-B53-C11-D42 | A3-B4-C12-D42 |
| A9-B53-C11-D42 | A9-B4-C12-D42 |
| A13-B53-C11-D42 | A13-B4-C12-D42 |
| A24-B53-C11-D42 | A24-B4-C12-D42 |
| A69-B53-C11-D42 | A69-B4-C12-D42 |
| A67-B53-C11-D42 | A67-B4-C12-D42 |
| A39-B53-C11-D42 | A39-B4-C12-D42 |
| A65-B53-C11-D42 | A65-B4-C12-D42 |
| A66-B53-C11-D42 | A66-B4-C12-D42 |
| A2-B79-C11-D42 | A2-B5-C12-D42 |
| A3-B79-C11-D42 | A3-B5-C12-D42 |
| A9-B79-C11-D42 | A9-B5-C12-D42 |
| A13-B79-C11-D42 | A13-B5-C12-D42 |
| A24-B79-C11-D42 | A24-B5-C12-D42 |
| A69-B79-C11-D42 | A69-B5-C12-D42 |
| A67-B79-C11-D42 | A67-B5-C12-D42 |
| A39-B79-C11-D42 | A39-B5-C12-D42 |
| A65-B79-C11-D42 | A65-B5-C12-D42 |
| A66-B79-C11-D42 | A66-B5-C12-D42 |
| A2-B80-C11-D42 | A2-B6-C12-D42 |
| A3-B80-C11-D42 | A3-B6-C12-D42 |
| A9-B80-C11-D42 | A9-B6-C12-D42 |
| A13-B80-C11-D42 | A13-B6-C12-D42 |
| A24-B80-C11-D42 | A24-B6-C12-D42 |
| A69-B80-C11-D42 | A69-B6-C12-D42 |
| A67-B80-C11-D42 | A67-B6-C12-D42 |
| A39-B80-C11-D42 | A39-B6-C12-D42 |
| A65-B80-C11-D42 | A65-B6-C12-D42 |
| A66-B80-C11-D42 | A66-B6-C12-D42 |
| A2-B85-C11-D42 | A2-B32-C12-D42 |
| A3-B85-C11-D42 | A3-B32-C12-D42 |
| A9-B85-C11-D42 | A9-B32-C12-D42 |
| A13-B85-C11-D42 | A13-B32-C12-D42 |
| A24-B85-C11-D42 | A24-B32-C12-D42 |
| A69-B85-C11-D42 | A69-B32-C12-D42 |
| A67-B85-C11-D42 | A67-B32-C12-D42 |
| A39-B85-C11-D42 | A39-B32-C12-D42 |
| A65-B85-C11-D42 | A65-B32-C12-D42 |
| A66-B85-C11-D42 | A66-B32-C12-D42 |
| A2-B86-C11-D42 | A2-B39-C12-D42 |
| A3-B86-C11-D42 | A3-B39-C12-D42 |
| A9-B86-C11-D42 | A9-B39-C12-D42 |
| A13-B86-C11-D42 | A13-B39-C12-D42 |
| A24-B86-C11-D42 | A24-B39-C12-D42 |
| A69-B86-C11-D42 | A69-B39-C12-D42 |
| A67-B86-C11-D42 | A67-B39-C12-D42 |
| A39-B86-C11-D42 | A39-B39-C12-D42 |
| A65-B86-C11-D42 | A65-B39-C12-D42 |
| A66-B86-C11-D42 | A66-B39-C12-D42 |
| A2-B87-C11-D42 | A2-B45-C12-D42 |
| A3-B87-C11-D42 | A3-B45-C12-D42 |
| A9-B87-C11-D42 | A9-B45-C12-D42 |
| A13-B87-C11-D42 | A13-B45-C12-D42 |
| A24-B87-C11-D42 | A24-B45-C12-D42 |
| A69-B87-C11-D42 | A69-B45-C12-D42 |
| A67-B87-C11-D42 | A67-B45-C12-D42 |
| A39-B87-C11-D42 | A39-B45-C12-D42 |
| A65-B87-C11-D42 | A65-B45-C12-D42 |
| A66-B87-C11-D42 | A66-B45-C12-D42 |
| A2-B89-C11-D42 | A2-B5 3-C12-D42 |
| A3-B89-C11-D42 | A3-B53-C12-D42 |
| A9-B89-C11-D42 | A9-B53-C12-D42 |

-continued

A13-B53-C12-D42
A24-B53-C12-D42
A69-B53-C12-D42
A67-B53-C12-D42
A39-B53-C12-D42
A65-B53-C12-D42
A66-B53-C12-D42
A2-B79-C12-D42
A3-B79-C12-D42
A9-B79-C12-D42
A13-B79-C12-D42
A24-B79-C12-D42
A69-B79-C12-D42
A67-B79-C12-D42
A39-B79-C12-D42
A65-B79-C12-D42
A66-B79-C12-D42
A2-B80-C12-D42
A3-B80-C12-D42
A9-B80-C12-D42
A13-B80-C12-D42
A24-B80-C12-D42
A69-B80-C12-D42
A67-B80-C12-D42
A39-B80-C12-D42
A65-B80-C12-D42
A66-B80-C12-D42
A2-B85-C12-D42
A3-B85-C12-D42
A9-B85-C12-D42
A13-B85-C12-D42
A24-B85-C12-D42
A69-B85-C12-D42
A67-B85-C12-D42
A39-B85-C12-D42
A65-B85-C12-D42
A66-B85-C12-D42
A2-B86-C12-D42
A3-B86-C12-D42
A9-B86-C12-D42
A13-B86-C12-D42
A24-B86-C12-D42
A69-B86-C12-D42
A67-B86-C12-D42
A39-B86-C12-D42
A65-B86-C12-D42
A66-B86-C12-D42
A2-B87-C12-D42
A3-B87-C12-D42
A9-B87-C12-D42
A13-B87-C12-D42
A24-B87-C12-D42
A69-B87-C12-D42
A67-B87-C12-D42
A39-B87-C12-D42
A65-B87-C12-D42
A66-B87-C12-D42
A2-B89-C12-D42
A3-B89-C12-D42
A9-B89-C12-D42
A13-B89-C12-D42
A24-B89-C12-D42
A69-B89-C12-D42
A67-B89-C12-D42
A39-B89-C12-D42
A65-B89-C12-D42
A66-B89-C12-D42
A2-B92-C12-D42
A3-B92-C12-D42
A9-B92-C12-D42
A13-B92-C12-D42
A24-B92-C12-D42
A69-B92-C12-D42
A67-B92-C12-D42
A39-B92-C12-D42
A65-B92-C12-D42
A66-B92-C12-D42
A2-B4-C13-D42
A3-B4-C13-D42
A9-B4-C13-D42

-continued

A13-B4-C13-D42
A24-B4-C13-D42
A69-B4-C13-D42
A67-B4-C13-D42
A39-B4-C13-D42
A65-B4-C13-D42
A66-B4-C13-D42
A2-B5-C13-D42
A3-B5-C13-D42
A9-B5-C13-D42
A13-B5-C13-D42
A24-B5-C13-D42
A69-B5-C13-D42
A67-B5-C13-D42
A39-B5-C13-D42
A65-B5-C13-D42
A66-B5-C13-D42
A2-B6-C13-D42
A3-B6-C13-D42
A9-B6-C13-D42
A13-B6-C13-D42
A24-B6-C13-D42
A69-B6-C13-D42
A67-B6-C13-D42
A39-B6-C13-D42
A65-B6-C13-D42
A66-B6-C13-D42
A2-B32-C13-D42
A3-B32-C13-D42
A9-B32-C13-D42
A13-B32-C13-D42
A24-B32-C13-D42
A69-B32-C13-D42
A67-B32-C13-D42
A39-B32-C13-D42
A65-B32-C13-D42
A66-B32-C13-D42
A2-B39-C13-D42
A3-B39-C13-D42
A9-B39-C13-D42
A13-B39-C13-D42
A24-B39-C13-D42
A69-B39-C13-D42
A67-B39-C13-D42
A39-B39-C13-D42
A65-B39-C13-D42
A66-B39-C13-D42
A2-B45-C13-D42
A3-B45-C13-D42
A9-B45-C13-D42
A13-B45-C13-D42
A24-B45-C13-D42
A69-B45-C13-D42
A67-B45-C13-D42
A39-B45-C13-D42
A65-B45-C13-D42
A66-B45-C13-D42
A2-B53-C13-D42
A3-B53-C13-D42
A9-B53-C13-D42
A13-B53-C13-D42
A24-B53-C13-D42
A69-B53-C13-D42
A67-B53-C13-D42
A39-B53-C13-D42
A65-B53-C13-D42
A66-B53-C13-D42
A2-B79-C13-D42
A3-B79-C13-D42
A9-B79-C13-D42
A13-B79-C13-D42
A24-B79-C13-D42
A69-B79-C13-D42
A67-B79-C13-D42
A39-B79-C13-D42
A65-B79-C13-D42
A66-B79-C13-D42
A2-B80-C13-D42
A3-B80-C13-D42
A9-B80-C13-D42

-continued

A13-B80-C13-D42
A24-B80-C13-D42
A69-B80-C13-D42
A67-B80-C13-D42
A39-B80-C13-D42
A65-B80-C13-D42
A66-B80-C13-D42
A2-B85-C13-D42
A3-B85-C13-D42
A9-B85-C13-D42
A13-B85-C13-D42
A24-B85-C13-D42
A69-B85-C13-D42
A67-B85-C13-D42
A39-B85-C13-D42
A65-B85-C13-D42
A66-B85-C13-D42
A2-B86-C13-D42
A3-B86-C13-D42
A9-B86-C13-D42
A13-B86-C13-D42
A24-B86-C13-D42
A69-B86-C13-D42
A67-B86-C13-D42
A39-B86-C13-D42
A65-B86-C13-D42
A66-B86-C13-D42
A2-B87-C13-D42
A3-B87-C13-D42
A9-B87-C13-D42
A13-B87-C13-D42
A24-B87-C13-D42
A69-B87-C13-D42
A67-B87-C13-D42
A39-B87-C13-D42
A65-B87-C13-D42
A66-B87-C13-D42
A2-B89-C13-D42
A3-B89-C13-D42
A9-B89-C13-D42
A13-B89-C13-D42
A24-B89-C13-D42
A69-B89-C13-D42
A67-B89-C13-D42
A39-B89-C13-D42
A65-B89-C13-D42
A66-B89-C13-D42
A2-B92-C13-D42
A3-B92-C13-D42
A9-B92-C13-D42
A13-B92-C13-D42
A24-B92-C13-D42
A69-B92-C13-D42
A67-B92-C13-D42
A39-B92-C13-D42
A65-B92-C13-D42
A66-B92-C13-D42
A2-B4-C1-D43
A3-B4-C1-D43
A9-B4-C1-D43
A13-B4-C1-D43
A24-B4-C1-D43
A69-B4-C1-D43
A67-B4-C1-D43
A39-B4-C1-D43
A65-B4-C1-D43
A66-B4-C1-D43
A2-B5-C1-D43
A3-B5-C1-D43
A9-B5-C1-D43
A13-B5-C1-D43
A24-B5-C1-D43
A69-B5-C1-D43
A67-B5-C1-D43
A39-B5-C1-D43
A65-B5-C1-D43
A66-B5-C1-D43
A2-B6-C1-D43
A3-B6-C1-D43
A9-B6-C1-D43

-continued

A13-B6-C1-D43
A24-B6-C1-D43
A69-B6-C1-D43
A67-B6-C1-D43
A39-B6-C1-D43
A65-B6-C1-D43
A66-B6-C1-D43
A2-B32-C1-D43
A3-B32-C1-D43
A9-B32-C1-D43
A13-B32-C1-D43
A24-B32-C1-D43
A69-B32-C1-D43
A67-B32-C1-D43
A39-B32-C1-D43
A65-B32-C1-D43
A66-B32-C1-D43
A2-B39-C1-D43
A3-B39-C1-D43
A9-B39-C1-D43
A13-B39-C1-D43
A24-B39-C1-D43
A69-B39-C1-D43
A67-B39-C1-D43
A39-B39-C1-D43
A65-B39-C1-D43
A66-B39-C1-D43
A2-B45-C1-D43
A3-B45-C1-D43
A9-B45-C1-D43
A13-B45-C1-D43
A24-B45-C1-D43
A69-B45-C1-D43
A67-B45-C1-D43
A39-B45-C1-D43
A65-B45-C1-D43
A66-B45-C1-D43
A2-B53-C1-D43
A3-B53-C1-D43
A9-B53-C1-D43
A13-B53-C1-D43
A24-B53-C1-D43
A69-B53-C1-D43
A67-B53-C1-D43
A39-B53-C1-D43
A65-B53-C1-D43
A66-B53-C1-D43
A2-B79-C1-D43
A3-B79-C1-D43
A9-B79-C1-D43
A13-B79-C1-D43
A24-B79-C1-D43
A69-B79-C1-D43
A67-B79-C1-D43
A39-B79-C1-D43
A65-B79-C1-D43
A66-B79-C1-D43
A2-B80-C1-D43
A3-B80-C1-D43
A9-B80-C1-D43
A13-B80-C1-D43
A24-B80-C1-D43
A69-B80-CL-D43
A67-B80-C1-D43
A39-B80-C1-D43
A65-B80-C1-D43
A66-B80-C1-D43
A2-B85-C1-D43
A3-B85-C1-D43
A9-B85-C1-D43
A13-B85-C1-D43
A24-B85-C1-D43
A69-B85-C1-D43
A67-B85-C1-D43
A39-B85-C1-D43
A65-B85-C1-D43
A66-B85-C1-D43
A2-B86-C1-D43
A3-B86-C1-D43
A9-B86-C1-D43

-continued

```
A13-B86-C1-D43
A24-B86-C1-D43
A69-B86-C1-D43
A67-B86-C1-D43
A39-B86-C1-D43
A65-B86-C1-D43
A66-B86-C1-D43
A2-B87-C1-D43
A3-B87-C1-D43
A9-B87-C1-D43
A13-B87-C1-D43
A24-B87-C1-D43
A69-B87-C1-D43
A67-B87-C1-D43
A39-B87-C1-D43
A65-B87-C1-D43
A66-B87-C1-D43
A2-B89-C1-D43
A3-B89-C1-D43
A9-B89-C1-D43
A13-B89-C1-D43
A24-B89-C1-D43
A69-B89-C1-D43
A67-B89-C1-D43
A39-B89-C1-D43
A65-B89-C1-D43
A66-B89-C1-D43
A2-B92-C1-D43
A3-B92-C1-D43
A9-B92-C1-D43
A13-B92-C1-D43
A24-B92-C1-D43
A69-B92-C1-D43
A67-B92-C1-D43
A39-B92-C1-D43
A65-B92-C1-D43
A66-B92-C1-D43
A2-B4-C2-D43
A3-B4-C2-D43
A9-B4-C2-D43
A13-B4-C2-D43
A24-B4-C2-D43
A69-B4-C2-D43
A67-B4-C2-D43
A39-B4-C2-D43
A65-B4-C2-D43
A66-B4-C2-D43
A2-B5-C2-D43
A3-B5-C2-D43
A9-B5-C2-D43
A13-B5-C2-D43
A24-B5-C2-D43
A69-B5-C2-D43
A67-B5-C2-D43
A39-B5-C2-D43
A65-B5-C2-D43
A66-B5-C2-D43
A2-B6-C2-D43
A3-B6-C2-D43
A9-B6-C2-D43
A13-B6-C2-D43
A24-B6-C2-D43
A69-B6-C2-D43
A67-B6-C2-D43
A39-B6-C2-D43
A65-B6-C2-D43
A66-B6-C2-D43
A2-B32-C2-D43
A3-B32-C2-D43
A9-B32-C2-D43
A13-B32-C2-D43
A24-B32-C2-D43
A69-B32-C2-D43
A67-B32-C2-D43
A39-B32-C2-D43
A65-B32-C2-D43
A66-B32-C2-D43
A2-B39-C2-D43
A3-B39-C2-D43
A9-B39-C2-D43
```

-continued

```
A13-B39-C2-D43
A24-B39-C2-D43
A69-B39-C2-D43
A67-B39-C2-D43
A39-B39-C2-D43
A65-B39-C2-D43
A66-B39-C2-D43
A2-B45-C2-D43
A3-B45-C2-D43
A9-B45-C2-D43
A13-B45-C2-D43
A24-B45-C2-D43
A69-B45-C2-D43
A67-B45-C2-D43
A39-B45-C2-D43
A65-B45-C2-D43
A66-B45-C2-D43
A2-B53-C2-D43
A3-B53-C2-D43
A9-B53-C2-D43
A13-B53-C2-D43
A24-B53-C2-D43
A69-B53-C2-D43
A67-B53-C2-D43
A39-B53-C2-D43
A65-B53-C2-D43
A66-B53-C2-D43
A2-B79-C2-D43
A3-B79-C2-D43
A9-B79-C2-D43
A13-B79-C2-D43
A24-B79-C2-D43
A69-B79-C2-D43
A67-B79-C2-D43
A39-B79-C2-D43
A65-B79-C2-D43
A66-B79-C2-D43
A2-B80-C2-D43
A3-B80-C2-D43
A9-B80-C2-D43
A13-B80-C2-D43
A24-B80-C2-D43
A69-B80-C2-D43
A67-B80-C2-D43
A39-B80-C2-D43
A65-B80-C2-D43
A66-B80-C2-D43
A2-B85-C2-D43
A3-B85-C2-D43
A9-B85-C2-D43
A13-B85-C2-D43
A24-B85-C2-D43
A69-B85-C2-D43
A67-B85-C2-D43
A39-B85-C2-D43
A65-B85-C2-D43
A66-B85-C2-D43
A2-B86-C2-D43
A3-B86-C2-D43
A9-B86-C2-D43
A13-B86-C2-D43
A24-B86-C2-D43
A69-B86-C2-D43
A67-B86-C2-D43
A39-B86-C2-D43
A65-B86-C2-D43
A66-B86-C2-D43
A2-B87-C2-D43
A3-B87-C2-D43
A9-B87-C2-D43
A13-B87-C2-D43
A24-B87-C2-D43
A69-B87-C2-D43
A67-B87-C2-D43
A39-B87-C2-D43
A65-B87-C2-D43
A66-B87-C2-D43
A2-B89-C2-D43
A3-B89-C2-D43
A9-B89-C2-D43
```

-continued
A13-B89-C2-D43
A24-B89-C2-D43
A69-B89-C2-D43
A67-B89-C2-D43
A39-B89-C2-D43
A65-B89-C2-D43
A66-B89-C2-D43
A2-B92-C2-D43
A3-B92-C2-D43
A9-B92-C2-D43
A13-B92-C2-D43
A24-B92-C2-D43
A69-B92-C2-D43
A67-B92-C2-D43
A39-B92-C2-D43
A65-B92-C2-D43
A66-B92-C2-D43
A2-B4-C3-D43
A3-B4-C3-D43
A9-B4-C3-D43
A13-B4-C3-D43
A24-B4-C3-D43
A69-B4-C3-D43
A67-B4-C3-D43
A39-B4-C3-D43
A65-B4-C3-D43
A66-B4-C3-D43
A2-B5-C3-D43
A3-B5-C3-D43
A9-B5-C3-D43
A13-B5-C3-D43
A24-B5-C3-D43
A69-B5-C3-D43
A67-B5-C3-D43
A39-B5-C3-D43
A65-B5-C3-D43
A66-B5-C3-D43
A2-B6-C3-D43
A3-B6-C3-D43
A9-B6-C3-D43
A13-B6-C3-D43
A24-B6-C3-D43
A69-B6-C3-D43
A67-B6-C3-D43
A39-B6-C3-D43
A65-B6-C3-D43
A66-B6-C3-D43
A2-B32-C3-D43
A3-B32-C3-D43
A9-B32-C3-D43
A13-B32-C3-D43
A24-B32-C3-D43
A69-B32-C3-D43
A67-B32-C3-D43
A39-B32-C3-D43
A65-B32-C3-D43
A66-B32-C3-D43
A2-B39-C3-D43
A3-B39-C3-D43
A9-B39-C3-D43
A13-B39-C3-D43
A24-B39-C3-D43
A69-B39-C3-D43
A67-B39-C3-D43
A39-B39-C3-D43
A65-B39-C3-D43
A66-B39-C3-D43
A2-B45-C3-D43
A3-B45-C3-D43
A9-B45-C3-D43
A13-B45-C3-D43
A24-B45-C3-D43
A69-B45-C3-D43
A67-B45-C3-D43
A39-B45-C3-D43
A65-B45-C3-D43
A66-B45-C3-D43
A2-B53-C3-D43
A3-B53-C3-D43
A9-B53-C3-D43

-continued
A13-B53-C3-D43
A24-B53-C3-D43
A69-B53-C3-D43
A67-B53-C3-D43
A39-B53-C3-D43
A65-B53-C3-D43
A66-B53-C3-D43
A2-B79-C3-D43
A3-B79-C3-D43
A9-B79-C3-D43
A13-B79-C3-D43
A24-B79-C3-D43
A69-B79-C3-D43
A67-B79-C3-D43
A39-B79-C3-D43
A65-B79-C3-D43
A66-B79-C3-D43
A2-B80-C3-D43
A3-B80-C3-D43
A9-B80-C3-D43
A13-B80-C3-D43
A24-B80-C3-D43
A69-B80-C3-D43
A67-B80-C3-D43
A39-B80-C3-D43
A65-B80-C3-D43
A66-B80-C3-D43
A2-B85-C3-D43
A3-B85-C3-D43
A9-B85-C3-D43
A13-B85-C3-D43
A24-B85-C3-D43
A69-B85-C3-D43
A67-B85-C3-D43
A39-B85-C3-D43
A65-B85-C3-D43
A66-B85-C3-D43
A2-B86-C3-D43
A3-B86-C3-D43
A9-B86-C3-D43
A13-B86-C3-D43
A24-B86-C3-D43
A69-B86-C3-D43
A67-B86-C3-D43
A39-B86-C3-D43
A65-B86-C3-D43
A66-B86-C3-D43
A2-B87-C3-D43
A3-B87-C3-D43
A9-B87-C3-D43
A13-B87-C3-D43
A24-B87-C3-D43
A69-B87-C3-D43
A67-B87-C3-D43
A39-B87-C3-D43
A65-B87-C3-D43
A66-B87-C3-D43
A2-B89-C3-D43
A3-B89-C3-D43
A9-B89-C3-D43
A13-B89-C3-D43
A24-B89-C3-D43
A69-B89-C3-D43
A67-B89-C3-D43
A39-B89-C3-D43
A65-B89-C3-D43
A66-B89-C3-D43
A2-B92-C3-D43
A3-B92-C3-D43
A9-B92-C3-D43
A13-B92-C3-D43
A24-B92-C3-D43
A69-B92-C3-D43
A67-B92-C3-D43
A39-B92-C3-D43
A65-B92-C3-D43
A66-B92-C3-D43
A2-B4-C4-D43
A3-B4-C4-D43
A9-B4-C4-D43

-continued

A13-B4-C4-D43
A24-B4-C4-D43
A69-B4-C4-D43
A67-B4-C4-D43
A39-B4-C4-D43
A65-B4-C4-D43
A66-B4-C4-D43
A2-B5-C4-D43
A3-B5-C4-D43
A9-B5-C4-D43
A13-B5-C4-D43
A24-B5-C4-D43
A69-B5-C4-D43
A67-B5-C4-D43
A39-B5-C4-D43
A65-B5-C4-D43
A66-B5-C4-D43
A2-B6-C4-D43
A3-B6-C4-D43
A9-B6-C4-D43
A13-B6-C4-D43
A24-B6-C4-D43
A69-B6-C4-D43
A67-B6-C4-D43
A39-B6-C4-D43
A65-B6-C4-D43
A66-B6-C4-D43
A2-B32-C4-D43
A3-B32-C4-D43
A9-B32-C4-D43
A13-B32-C4-D43
A24-B32-C4-D43
A69-B32-C4-D43
A67-B32-C4-D43
A39-B32-C4-D43
A65-B32-C4-D43
A66-B32-C4-D43
A2-B39-C4-D43
A3-B39-C4-D43
A9-B39-C4-D43
A13-B39-C4-D43
A24-B39-C4-D43
A69-B39-C4-D43
A67-B39-C4-D43
A39-B39-C4-D43
A65-B39-C4-D43
A66-B39-C4-D43
A2-B45-C4-D43
A3-B45-C4-D43
A9-B45-C4-D43
A13-B45-C4-D43
A24-B45-C4-D43
A69-B45-C4-D43
A67-B45-C4-D43
A39-B45-C4-D43
A65-B45-C4-D43
A66-B45-C4-D43
A2-B53-C4-D43
A3-B53-C4-D43
A9-B53-C4-D43
A13-B53-C4-D43
A24-B53-C4-D43
A69-B53-C4-D43
A67-B53-C4-D43
A39-B53-C4-D43
A65-B53-C4-D43
A66-B53-C4-D43
A2-B79-C4-D43
A3-B79-C4-D43
A9-B79-C4-D43
A13-B79-C4-D43
A24-B79-C4-D43
A69-B79-C4-D43
A67-B79-C4-D43
A39-B79-C4-D43
A65-B79-C4-D43
A66-B79-C4-D43
A2-B80-C4-D43
A3-B80-C4-D43
A9-B80-C4-D43

-continued

A13-B80-C4-D43
A24-B80-C4-D43
A69-B80-C4-D43
A67-B80-C4-D43
A39-B80-C4-D43
A65-B80-C4-D43
A66-B80-C4-D43
A2-B85-C4-D43
A3-B85-C4-D43
A9-B85-C4-D43
A13-B85-C4-D43
A24-B85-C4-D43
A69-B85-C4-D43
A67-B85-C4-D43
A39-B85-C4-D43
A65-B85-C4-D43
A66-B85-C4-D43
A2-B86-C4-D43
A3-B86-C4-D43
A9-B86-C4-D43
A13-B86-C4-D43
A24-B86-C4-D43
A69-B86-C4-D43
A67-B86-C4-D43
A39-B86-C4-D43
A65-B86-C4-D43
A66-B86-C4-D43
A2-B87-C4-D43
A3-B87-C4-D43
A9-B87-C4-D43
A13-B87-C4-D43
A24-B87-C4-D43
A69-B87-C4-D43
A67-B87-C4-D43
A39-B87-C4-D43
A65-B87-C4-D43
A66-B87-C4-D43
A2-B89-C4-D43
A3-B89-C4-D43
A9-B89-C4-D43
A13-B89-C4-D43
A24-B89-C4-D43
A69-B89-C4-D43
A67-B89-C4-D43
A39-B89-C4-D43
A65-B89-C4-D43
A66-B89-C4-D43
A2-B92-C4-D43
A3-B92-C4-D43
A9-B92-C4-D43
A13-B92-C4-D43
A24-B92-C4-D43
A69-B92-C4-D43
A67-B92-C4-D43
A39-B92-C4-D43
A65-B92-C4-D43
A66-B92-C4-D43
A2-B4-C5-D43
A3-B4-C5-D43
A9-B4-C5-D43
A13-B4-C5-D43
A24-B4-C5-D43
A69-B4-C5-D43
A67-B4-C5-D43
A39-B4-C5-D43
A65-B4-C5-D43
A66-B4-C5-D43
A2-B5-C5-D43
A3-B5-C5-D43
A9-B5-C5-D43
A13-B5-C5-D43
A24-B5-C5-D43
A69-B5-C5-D43
A67-B5-C5-D43
A39-B5-C5-D43
A65-B5-C5-D43
A66-B5-C5-D43
A2-B6-C5-D43
A3-B6-C5-D43
A9-B6-C5-D43

-continued

A13-B6-C5-D43
A24-B6-C5-D43
A69-B6-C5-D43
A67-B6-C5-D43
A39-B6-C5-D43
A65-B6-C5-D43
A66-B6-C5-D43
A2-B32-C5-D43
A3-B32-C5-D43
A9-B32-C5-D43
A13-B32-C5-D43
A24-B32-C5-D43
A69-B32-C5-D43
A67-B32-C5-D43
A39-B32-C5-D43
A65-B32-C5-D43
A66-B32-C5-D43
A2-B39-C5-D43
A3-B39-C5-D43
A9-B39-C5-D43
A13-B39-C5-D43
A24-B39-C5-D43
A69-B39-C5-D43
A67-B39-C5-D43
A39-B39-C5-D43
A65-B39-C5-D43
A66-B39-C5-D43
A2-B45-C5-D43
A3-B45-C5-D43
A9-B45-C5-D43
A13-B45-C5-D43
A24-B45-C5-D43
A69-B45-C5-D43
A67-B45-C5-D43
A39-B45-C5-D43
A65-B45-C5-D43
A66-B45-C5-D43
A2-B53-C5-D43
A3-B53-C5-D436
A9-B53-C5-D43
A13-B53-C5-D43
A24-B53-C5-D43
A69-B53-C5-D43
A67-B53-C5-D43
A39-B53-C5-D43
A65-B53-C5-D43
A66-B53-C5-D43
A2-B79-C5-D43
A3-B79-C5-D43
A9-B79-C5-D43
A13-B79-C5-D43
A24-B79-C5-D43
A69-B79-C5-D43
A67-B79-C5-D43
A39-B79-C5-D43
A65-B79-C5-D43
A66-B79-C5-D43
A2-B80-C5-D43
A3-B80-C5-D43
A9-B80-C5-D43
A13-B80-C5-D43
A24-B80-C5-D43
A69-B80-C5-D43
A67-B80-C5-D43
A39-B80-C5-D43
A65-B80-C5-D43
A66-B80-C5-D43
A2-B85-C5-D43
A3-B85-C5-D43
A9-B85-C5-D43
A13-B85-C5-D43
A24-B85-C5-D43
A69-B85-C5-D43
A67-B85-C5-D43
A39-B85-C5-D43
A65-B85-C5-D43
A66-B85-C5-D43
A2-B86-C5-D43
A3-B86-C5-D43
A9-B86-C5-D43

-continued

A13-B86-C5-D43
A24-B86-C5-D43
A69-B86-C5-D43
A67-B86-C5-D43
A39-B86-C5-D43
A65-B86-C5-D43
A66-B86-C5-D43
A2-B87-C5-D43
A3-B87-C5-D43
A9-B87-C5-D43
A13-B87-C5-D43
A24-B87-C5-D43
A69-B87-C5-D43
A67-B87-C5-D43
A39-B87-C5-D43
A65-B87-C5-D43
A66-B87-C5-D43
A2-B89-C5-D43
A3-B89-C5-D43
A9-B89-C5-D43
A13-B89-C5-D43
A24-B89-C5-D43
A69-B89-C5-D43
A67-B89-C5-D43
A39-B89-C5-D43
A65-B89-C5-D43
A66-B89-C5-D43
A2-B92-C5-D43
A3-B92-C5-D43
A9-B92-C5-D43
A13-B92-C5-D43
A24-B92-C5-D43
A69-B92-C5-D43
A67-B92-C5-D43
A39-B92-C5-D43
A65-B92-C5-D43
A66-B92-C5-D43
A2-B4-C6-D43
A3-B4-C6-D43
A9-B4-C6-D43
A13-B4-C6-D43
A24-B4-C6-D43
A69-B4-C6-D43
A67-B4-C6-D43
A39-B4-C6-D43
A65-B4-C6-D43
A66-B4-C6-D43
A2-B5-C6-D43
A3-B5-C6-D43
A9-B5-C6-D43
A13-B5-C6-D43
A24-B5-C6-D43
A69-B5-C6-D43
A67-B5-C6-D43
A39-B5-C6-D43
A65-B5-C6-D43
A66-B5-C6-D43
A2-B6-C6-D43
A3-B6-C6-D43
A9-B6-C6-D43
A13-B6-C6-D43
A24-B6-C6-D43
A69-B6-C6-D43
A67-B6-C6-D43
A39-B6-C6-D43
A65-B6-C6-D43
A66-B6-C6-D43
A2-B32-C6-D43
A3-B32-C6-D43
A9-B32-C6-D43
A13-B32-C6-D43
A24-B32-C6-D43
A69-B32-C6-D43
A67-B32-C6-D43
A39-B32-C6-D43
A65-B32-C6-D43
A66-B32-C6-D43
A2-B39-C6-D43
A3-B39-C6-D43
A9-B39-C6-D43

-continued

A13-B39-C6-D43
A24-B39-C6-D43
A69-B39-C6-D43
A67-B39-C6-D43
A39-B39-C6-D43
A65-B39-C6-D43
A66-B39-C6-D43
A2-B45-C6-D43
A3-B45-C6-D43
A9-B45-C6-D43
A13-B45-C6-D43
A24-B45-C6-D43
A69-B45-C6-D43
A67-B45-C6-D43
A39-B45-C6-D43
A65-B45-C6-D43
A66-B45-C6-D43
A2-B53-C6-D43
A3-B53-C6-D43
A9-B53-C6-D43
A13-B53-C6-D43
A24-B53-C6-D43
A69-B53-C6-D43
A67-B53-C6-D43
A39-B53-C6-D43
A65-B53-C6-D43
A66-B53-C6-D43
A2-B79-C6-D43
A3-B79-C6-D43
A9-B79-C6-D43
A13-B79-C6-D43
A24-B79-C6-D43
A69-B79-C6-D43
A67-B79-C6-D43
A39-B79-C6-D43
A65-B79-C6-D43
A66-B79-C6-D43
A2-B80-C6-D43
A3-B80-C6-D43
A9-B80-C6-D43
A13-B80-C6-D43
A24-B80-C6-D43
A69-B80-C6-D43
A67-B80-C6-D43
A39-B80-C6-D43
A65-B80-C6-D43
A66-B80-C6-D43
A2-B85-C6-D43
A3-B85-C6-D43
A9-B85-C6-D43
A13-B85-C6-D43
A24-B85-C6-D43
A69-B85-C6-D43
A67-B85-C6-D43
A39-B85-C6-D43
A65-B85-C6-D43
A66-B85-C6-D43
A2-B86-C6-D43
A3-B86-C6-D43
A9-B86-C6-D43
A13-B86-C6-D43
A24-B86-C6-D43
A69-B86-C6-D43
A67-B86-C6-D43
A39-B86-C6-D43
A65-B86-C6-D43
A66-B86-C6-D43
A2-B87-C6-D43
A3-B87-C6-D43
A9-B87-C6-D43
A13-B87-C6-D43
A24-B87-C6-D43
A69-B87-C6-D43
A67-B87-C6-D43
A39-B87-C6-D43
A65-B87-C6-D43
A66-B87-C6-D43
A2-B89-C6-D43
A3-B89-C6-D43
A9-B89-C6-D43

-continued

A13-B89-C6-D43
A24-B89-C6-D43
A69-B89-C6-D43
A67-B89-C6-D43
A39-B89-C6-D43
A65-B89-C6-D43
A66-B89-C6-D43
A2-B92-C6-D43
A3-B92-C6-D43
A9-B92-C6-D43
A13-B92-C6-D43
A24-B92-C6-D43
A69-B92-C6-D43
A67-B92-C6-D43
A39-B92-C6-D43
A65-B92-C6-D43
A66-B92-C6-D43
A2-B4-C7-D43
A3-B4-C7-D43
A9-B4-C7-D43
A13-B4-C7-D43
A24-B4-C7-D43
A69-B4-C7-D43
A67-B4-C7-D43
A39-B4-C7-D43
A65-B4-C7-D43
A66-B4-C7-D43
A2-B5-C7-D43
A3-B5-C7-D43
A9-B5-C7-D43
A13-B5-C7-D43
A24-B5-C7-D43
A69-B5-C7-D43
A67-B5-C7-D43
A39-B5-C7-D43
A65-B5-C7-D43
A66-B5-C7-D43
A2-B6-C7-D43
A3-B6-C7-D43
A9-B6-C7-D43
A13-B6-C7-D43
A24-B6-C7-D43
A69-B6-C7-D43
A67-B6-C7-D43
A39-B6-C7-D43
A65-B6-C7-D43
A66-B6-C7-D43
A2-B32-C7-D43
A3-B32-C7-D43
A9-B32-C7-D43
A13-B32-C7-D43
A24-B32-C7-D43
A69-B32-C7-D43
A67-B32-C7-D43
A39-B32-C7-D43
A65-B32-C7-D43
A66-B32-C7-D43
A2-B39-C7-D43
A3-B39-C7-D43
A9-B39-C7-D43
A13-B39-C7-D43
A24-B39-C7-D43
A69-B39-C7-D43
A67-B39-C7-D43
A39-B39-C7-D43
A65-B39-C7-D43
A66-B39-C7-D43
A2-B45-C7-D43
A3-B45-C7-D43
A9-B45-C7-D43
A13-B45-C7-D43
A24-B45-C7-D43
A69-B45-C7-D43
A67-B45-C7-D43
A39-B45-C7-D43
A65-B45-C7-D43
A66-B45-C7-D43
A2-B53-C7-D43
A3-B53-C7-D43
A9-B53-C7-D43

-continued

A13-B53-C7-D43
A24-B53-C7-D43
A69-B53-C7-D43
A67-B53-C7-D43
A39-B53-C7-D43
A65-B53-C7-D43
A66-B53-C7-D43
A2-B79-C7-D43
A3-B79-C7-D43
A9-B79-C7-D43
A13-B79-C7-D43
A24-B79-C7-D43
A69-B79-C7-D43
A67-B79-C7-D43
A39-B79-C7-D43
A65-B79-C7-D43
A66-B79-C7-D43
A2-B80-C7-D43
A3-B80-C7-D43
A9-B80-C7-D43
A13-B80-C7-D43
A24-B80-C7-D43
A69-B80-C7-D43
A67-B80-C7-D43
A39-B80-C7-D43
A65-B80-C7-D43
A66-B80-C7-D43
A2-B85-C7-D43
A3-B85-C7-D43
A9-B85-C7-D43
A13-B85-C7-D43
A24-B85-C7-D43
A69-B85-C7-D43
A67-B85-C7-D43
A39-B85-C7-D43
A65-B85-C7-D43
A66-B85-C7-D43
A2-B86-C7-D43
A3-B86-C7-D43
A9-B86-C7-D43
A13-B86-C7-D43
A24-B86-C7-D43
A69-B86-C7-D43
A67-B86-C7-D43
A39-B86-C7-D43
A65-B86-C7-D43
A66-B86-C7-D43
A2-B87-C7-D43
A3-B87-C7-D43
A9-B87-C7-D43
A13-B87-C7-D43
A24-B87-C7-D43
A69-B87-C7-D43
A67-B87-C7-D43
A39-B87-C7-D43
A65-B87-C7-D43
A66-B87-C7-D43
A2-B89-C7-D43
A3-B89-C7-D43
A9-B89-C7-D43
A13-B89-C7-D43
A24-B89-C7-D43
A69-B89-C7-D43
A67-B89-C7-D43
A39-B89-C7-D43
A65-B89-C7-D43
A66-B89-C7-D43
A2-B92-C7-D43
A3-B92-C7-D43
A9-B92-C7-D43
A13-B92-C7-D43
A24-B92-C7-D43
A69-B92-C7-D43
A67-B92-C7-D43
A39-B92-C7-D43
A65-B92-C7-D43
A66-B92-C7-D43
A2-B4-C8-D43
A3-B4-C8-D43
A9-B4-C8-D43

-continued

A13-B4-C8-D43
A24-B4-C8-D43
A69-B4-C8-D43
A67-B4-C8-D43
A39-B4-C8-D43
A65-B4-C8-D43
A66-B4-C8-D43
A2-B5-C8-D43
A3-B5-C8-D43
A9-B5-C8-D43
A13-B5-C8-D43
A24-B5-C8-D43
A69-B5-C8-D43
A67-B5-C8-D43
A39-B5-C8-D43
A65-B5-C8-D43
A66-B5-C8-D43
A2-B6-C8-D43
A3-B6-C8-D43
A9-B6-C8-D43
A13-B6-C8-D43
A24-B6-C8-D43
A69-B6-C8-D43
A67-B6-C8-D43
A39-B6-C8-D43
A65-B6-C8-D43
A66-B6-C8-D43
A2-B32-C8-D43
A3-B32-C8-D43
A9-B32-C8-D43
A13-B32-C8-D43
A24-B32-C8-D43
A69-B32-C8-D43
A67-B32-C8-D43
A39-B32-C8-D43
A65-B32-C8-D43
A66-B32-C8-D43
A2-B39-C8-D43
A3-B39-C8-D43
A9-B39-C8-D43
A13-B39-C8-D43
A24-B39-C8-D43
A69-B39-C8-D43
A67-B39-C8-D43
A39-B39-C8-D43
A65-B39-C8-D43
A66-B39-C8-D43
A2-B45-C8-D43
A3-B45-C8-D43
A9-B45-C8-D43
A13-B45-C8-D43
A24-B45-C8-D43
A69-B45-C8-D43
A67-B45-C8-D43
A39-B45-C8-D43
A65-B45-C8-D43
A66-B45-C8-D43
A2-B53-C8-D43
A3-B53-C8-D43
A9-B53-C8-D43
A13-B53-C8-D43
A24-B53-C8-D43
A69-B53-C8-D43
A67-B53-C8-D43
A39-B53-C8-D43
A65-B53-C8-D43
A66-B53-C8-D43
A2-B79-C8-D43
A3-B79-C8-D43
A9-B79-C8-D43
A13-B79-C8-D43
A24-B79-C8-D43
A69-B79-C8-D43
A67-B79-C8-D43
A39-B79-C8-D43
A65-B79-C8-D43
A66-B79-C8-D43
A2-B80-C8-D43
A3-B80-C8-D43
A9-B80-C8-D43

-continued

```
A13-B80-C8-D43
A24-B80-C8-D43
A69-B80-C8-D43
A67-B80-C8-D43
A39-B80-C8-D43
A65-B80-C8-D43
A66-B80-C8-D43
A2-B85-C8-D43
A3-B85-C8-D43
A9-B85-C8-D43
A13-B85-C8-D43
A24-B85-C8-D43
A69-B85-C8-D43
A67-B85-C8-D43
A39-B85-C8-D43
A65-B85-C8-D43
A66-B85-C8-D43
A2-B86-C8-D43
A3-B86-C8-D43
A9-B86-C8-D43
A13-B86-C8-D43
A24-B86-C8-D43
A69-B86-C8-D43
A67-B86-C8-D43
A39-B86-C8-D43
A65-B86-C8-D43
A66-B86-C8-D43
A2-B87-C8-D43
A3-B87-C8-D43
A9-B87-C8-D43
A13-B87-C8-D43
A24-B87-C8-D43
A69-B87-C8-D43
A67-B87-C8-D43
A39-B87-C8-D43
A65-B87-C8-D43
A66-B87-C8-D43
A2-B89-C8-D43
A3-B89-C8-D43
A9-B89-C8-D43
A13-B89-C8-D43
A24-B89-C8-D43
A69-B89-C8-D43
A67-B89-C8-D43
A39-B89-C8-D43
A65-B89-C8-D43
A66-B89-C8-D43
A2-B92-C8-D43
A3-B92-C8-D43
A9-B92-C8-D43
A13-B92-C8-D43
A24-B92-C8-D43
A69-B92-C8-D43
A67-B92-C8-D43
A39-B92-C8-D43
A65-B92-C8-D43
A66-B92-C8-D43
A2-B4-C9-D43
A3-B4-C9-D43
A9-B4-C9-D43
A13-B4-C9-D43
A24-B4-C9-D43
A69-B4-C9-D43
A67-B4-C9-D43
A39-B4-C9-D43
A65-B4-C9-D43
A66-B4-C9-D43
A2-B5-C9-D43
A3-B5-C9-D43
A9-B5-C9-D43
A13-B5-C9-D43
A24-B5-C9-D43
A69-B5-C9-D43
A67-B5-C9-D43
A39-B5-C9-D43
A65-B5-C9-D43
A66-B5-C9-D43
A2-B6-C9-D43
A3-B6-C9-D43
A9-B6-C9-D43
```

-continued

```
A13-B6-C9-D43
A24-B6-C9-D43
A69-B6-C9-D43
A67-B6-C9-D43
A39-B6-C9-D43
A65-B6-C9-D43
A66-B6-C9-D43
A2-B32-C9-D43
A3-B32-C9-D43
A9-B32-C9-D43
A13-B32-C9-D43
A24-B32-C9-D43
A69-B32-C9-D43
A67-B32-C9-D43
A39-B32-C9-D43
A65-B32-C9-D43
A66-B32-C9-D43
A2-B39-C9-D43
A3-B39-C9-D43
A9-B39-C9-D43
A13-B39-C9-D43
A24-B39-C9-D43
A69-B39-C9-D43
A67-B39-C9-D43
A39-B39-C9-D43
A65-B39-C9-D43
A66-B39-C9-D43
A2-B45-C9-D43
A3-B45-C9-D43
A9-B45-C9-D43
A13-B45-C9-D43
A24-B45-C9-D43
A69-B45-C9-D43
A67-B45-C9-D43
A39-B45-C9-D43
A65-B45-C9-D43
A66-B45-C9-D43
A2-B53-C9-D43
A3-B53-C9-D43
A9-B53-C9-D43
A13-B53-C9-D43
A24-B53-C9-D43
A69-B53-C9-D43
A67-B53-C9-D43
A39-B53-C9-D43
A65-B53-C9-D43
A66-B53-C9-D43
A2-B79-C9-D43
A3-B79-C9-D43
A9-B79-C9-D43
A13-B79-C9-D43
A24-B79-C9-D43
A69-B79-C9-D43
A67-B79-C9-D43
A39-B79-C9-D43
A65-B79-C9-D43
A66-B79-C9-D43
A2-B80-C9-D43
A3-B80-C9-D43
A9-B80-C9-D43
A13-B80-C9-D43
A24-B80-C9-D43
A69-B80-C9-D43
A67-B80-C9-D43
A39-B80-C9-D43
A65-B80-C9-D43
A66-B80-C9-D43
A2-B85-C9-D43
A3-B85-C9-D43
A9-B85-C9-D43
A13-B85-C9-D43
A24-B85-C9-D43
A69-B85-C9-D43
A67-B85-C9-D43
A39-B85-C9-D43
A65-B85-C9-D43
A66-B85-C9-D43
A2-B86-C9-D43
A3-B86-C9-D43
A9-B86-C9-D43
```

-continued

| | |
|---|---|
| A13-B86-C9-D43 | A13-B39-C10-D43 |
| A24-B86-C9-D43 | A24-B39-C10-D43 |
| A69-B86-C9-D43 | A69-B39-C10-D43 |
| A67-B86-C9-D43 | A67-B39-C10-D43 |
| A39-B86-C9-D43 | A39-B39-C10-D43 |
| A65-B86-C9-D43 | A65-B39-C10-D43 |
| A66-B86-C9-D43 | A66-B39-C10-D43 |
| A2-B87-C9-D43 | A2-B45-C10-D43 |
| A3-B87-C9-D43 | A3-B45-C10-D43 |
| A9-B87-C9-D43 | A9-B45-C10-D43 |
| A13-B87-C9-D43 | A13-B45-C10-D43 |
| A24-B87-C9-D43 | A24-B45-C10-D43 |
| A69-B87-C9-D43 | A69-B45-C10-D43 |
| A67-B87-C9-D43 | A67-B45-C10-D43 |
| A39-B87-C9-D43 | A39-B45-C10-D43 |
| A65-B87-C9-D43 | A65-B45-C10-D43 |
| A66-B87-C9-D43 | A66-B45-C10-D43 |
| A2-B89-C9-D43 | A2-B53-C10-D43 |
| A3-B89-C9-D43 | A3-B53-C10-D43 |
| A9-B89-C9-D43 | A9-B53-C10-D43 |
| A13-B89-C9-D43 | A13-B53-C10-D43 |
| A24-B89-C9-D43 | A24-B53-C10-D43 |
| A69-B89-C9-D43 | A69-B53-C10-D43 |
| A67-B89-C9-D43 | A67-B53-C10-D43 |
| A39-B89-C9-D43 | A39-B53-C10-D43 |
| A65-B89-C9-D43 | A65-B53-C10-D43 |
| A66-B89-C9-D43 | A66-B53-C10-D43 |
| A2-B92-C9-D43 | A2-B79-C10-D43 |
| A3-B92-C9-D43 | A3-B79-C10-D43 |
| A9-B92-C9-D43 | A9-B79-C10-D43 |
| A13-B92-C9-D43 | A13-B79-C10-D43 |
| A24-B92-C9-D43 | A24-B79-C10-D43 |
| A69-B92-C9-D43 | A69-B79-C10-D43 |
| A67-B92-C9-D43 | A67-B79-C10-D43 |
| A39-B92-C9-D43 | A39-B79-C10-D43 |
| A65-B92-C9-D43 | A65-B79-C10-D43 |
| A66-B92-C9-D43 | A66-B79-C10-D43 |
| A2-B4-C10-D43 | A2-B80-C10-D43 |
| A3-B4-C10-D43 | A3-B80-C10-D43 |
| A9-B4-C10-D43 | A9-B80-C10-D43 |
| A13-B4-C10-D43 | A13-B80-C10-D43 |
| A24-B4-C10-D43 | A24-B80-C10-D43 |
| A69-B4-C10-D43 | A69-B80-C10-D43 |
| A67-B4-C10-D43 | A67-B80-C10-D43 |
| A39-B4-C10-D43 | A39-B80-C10-D43 |
| A65-B4-C10-D43 | A65-B80-C10-D43 |
| A66-B4-C10-D43 | A66-B80-C10-D43 |
| A2-B5-C10-D43 | A2-B85-C10-D43 |
| A3-B5-C10-D43 | A3-B85-C10-D43 |
| A9-B5-C10-D43 | A9-B85-C10-D43 |
| A13-B5-C10-D43 | A13-B85-C10-D43 |
| A24-B5-C10-D43 | A24-B85-C10-D43 |
| A69-B5-C10-D43 | A69-B85-C10-D43 |
| A67-B5-C10-D43 | A67-B85-C10-D43 |
| A39-B5-C10-D43 | A39-B85-C10-D43 |
| A65-B5-C10-D43 | A65-B85-C10-D43 |
| A66-B5-C10-D43 | A66-B85-C10-D43 |
| A2-B6-C10-D43 | A2-B86-C10-D43 |
| A3-B6-C10-D43 | A3-B86-C10-D43 |
| A9-B6-C10-D43 | A9-B86-C10-D43 |
| A13-B6-C10-D43 | A13-B86-C10-D43 |
| A24-B6-C10-D43 | A24-B86-C10-D43 |
| A69-B6-C10-D43 | A69-B86-C10-D43 |
| A67-B6-C10-D43 | A67-B86-C10-D43 |
| A39-B6-C10-D43 | A39-B86-C10-D43 |
| A65-B6-C10-D43 | A65-B86-C10-D43 |
| A66-B6-C10-D43 | A66-B86-C10-D43 |
| A2-B32-C10-D43 | A2-B87-C10-D43 |
| A3-B32-C10-D43 | A3-B87-C10-D43 |
| A9-B32-C10-D43 | A9-B87-C10-D43 |
| A13-B32-C10-D43 | A13-B87-C10-D43 |
| A24-B32-C10-D43 | A24-B87-C10-D43 |
| A69-B32-C10-D43 | A69-B87-C10-D43 |
| A67-B32-C10-D43 | A67-B87-C10-D43 |
| A39-B32-C10-D43 | A39-B87-C10-D43 |
| A65-B32-C10-D43 | A65-B87-C10-D43 |
| A66-B32-C10-D43 | A66-B87-C10-D43 |
| A2-B39-C10-D43 | A2-B89-C10-D43 |
| A3-B39-C10-D43 | A3-B89-C10-D43 |
| A9-B39-C10-D43 | A9-B89-C10-D43 |

-continued

A13-B89-C10-D43
A24-B89-C10-D43
A69-B89-C10-D43
A67-B89-C10-D43
A39-B89-C10-D43
A65-B89-C10-D43
A66-B89-C10-D43
A2-B92-C10-D43
A3-B92-C10-D43
A9-B92-C10-D43
A13-B92-C10-D43
A24-B92-C10-D43
A69-B92-C10-D43
A67-B92-C10-D43
A39-B92-C10-D43
A65-B92-C10-D43
A66-B92-C10-D43
A2-B4-C11-D43
A3-B4-C11-D43
A9-B4-C11-D43
A13-B4-C11-D43
A24-B4-C11-D43
A69-B4-C11-D43
A67-B4-C11-D43
A39-B4-C11-D43
A65-B4-C11-D43
A66-B4-C11-D43
A2-B5-C11-D43
A3-B5-C11-D43
A9-B5-C11-D43
A13-B5-C11-D43
A24-B5-C11-D43
A69-B5-C11-D43
A67-B5-C11-D43
A39-B5-C11-D43
A65-B5-C11-D43
A66-B5-C11-D43
A2-B6-C11-D43
A3-B6-C11-D43
A9-B6-C11-D43
A13-B6-C11-D43
A24-B6-C11-D43
A69-B6-C11-D43
A67-B6-C11-D43
A39-B6-C11-D43
A65-B6-C11-D43
A66-B6-C11-D43
A2-B32-C11-D43
A3-B32-C11-D43
A9-B32-C11-D43
A13-B32-C11-D43
A24-B32-C11-D43
A69-B32-C11-D43
A67-B32-C11-D43
A39-B32-C11-D43
A65-B32-C11-D43
A66-B32-C11-D43
A2-B39-C11-D43
A3-B39-C11-D43
A9-B39-C11-D43
A13-B39-C11-D43
A24-B39-C11-D43
A69-B39-C11-D43
A67-B39-C11-D43
A39-B39-C11-D43
A65-B39-C11-D43
A66-B39-C11-D43
A2-B45-C11-D43
A3-B45-C11-D43
A9-B45-C11-D43
A13-B45-C11-D43
A24-B45-C11-D43
A69-B45-C11-D43
A67-B45-C11-D43
A39-B45-C11-D43
A65-B45-C11-D43
A66-B45-C11-D43
A2-B53-C11-D43
A3-B53-C11-D43
A9-B53-C11-D43

-continued

A13-B53-C11-D43
A24-B53-C11-D43
A69-B53-C11-D43
A67-B53-C11-D43
A39-B53-C11-D43
A65-B53-C11-D43
A66-B53-C11-D43
A2-B79-C11-D43
A3-B79-C11-D43
A9-B79-C11-D43
A13-B79-C11-D43
A24-B79-C11-D43
A69-B79-C11-D43
A67-B79-C11-D43
A39-B79-C11-D43
A65-B79-C11-D43
A66-B79-C11-D43
A2-B80-C11-D43
A3-B80-C11-D43
A9-B80-C11-D43
A13-B80-C11-D43
A24-B80-C11-D43
A69-B80-C11-D43
A67-B80-C11-D43
A39-B80-C11-D43
A65-B80-C11-D43
A66-B80-C11-D43
A2-B85-C11-D43
A3-B85-C11-D43
A9-B85-C11-D43
A13-B85-C11-D43
A24-B85-C11-D43
A69-B85-C11-D43
A67-B85-C11-D43
A39-B85-C11-D43
A65-B85-C11-D43
A66-B85-C11-D43
A2-B86-C11-D43
A3-B86-C11-D43
A9-B86-C11-D43
A13-B86-C11-D43
A24-B86-C11-D43
A69-B86-C11-D43
A67-B86-C11-D43
A39-B86-C11-D43
A65-B86-C11-D43
A66-B86-C11-D43
A2-B87-C11-D43
A3-B87-C11-D43
A9-B87-C11-D43
A13-B87-C11-D43
A24-B87-C11-D43
A69-B87-C11-D43
A67-B87-C11-D43
A39-B87-C11-D43
A65-B87-C11-D43
A66-B87-C11-D43
A2-B89-C11-D43
A3-B89-C11-D43
A9-B89-C11-D43
A13-B89-C11-D43
A24-B89-C11-D43
A69-B89-C11-D43
A67-B89-C11-D43
A39-B89-C11-D43
A65-B89-C11-D43
A66-B89-C11-D43
A2-B92-C11-D43
A3-B92-C11-D43
A9-B92-C11-D43
A13-B92-C11-D43
A24-B92-C11-D43
A69-B92-C11-D43
A67-B92-C11-D43
A39-B92-C11-D43
A65-B92-C11-D43
A66-B92-C11-D43
A2-B4-C12-D43
A3-B4-C12-D43
A9-B4-C12-D43

-continued
A13-B4-C12-D43
A24-B4-C12-D43
A69-B4-C12-D43
A67-B4-C12-D43
A39-B4-C12-D43
A65-B4-C12-D43
A66-B4-C12-D43
A2-B5-C12-D43
A3-B5-C12-D43
A9-B5-C12-D43
A13-B5-C12-D43
A24-B5-C12-D43
A69-B5-C12-D43
A67-B5-C12-D43
A39-B5-C12-D43
A65-B5-C12-D43
A66-B5-C12-D43
A2-B6-C12-D43
A3-B6-C12-D43
A9-B6-C12-D43
A13-B6-C12-D43
A24-B6-C12-D43
A69-B6-C12-D43
A67-B6-C12-D43
A39-B6-C12-D43
A65-B6-C12-D43
A66-B6-C12-D43
A2-B32-C12-D43
A3-B32-C12-D43
A9-B32-C12-D43
A13-B32-C12-D43
A24-B32-C12-D43
A69-B32-C12-D43
A67-B32-C12-D43
A39-B32-C12-D43
A65-B32-C12-D43
A66-B32-C12-D43
A2-B39-C12-D43
A3-B39-C12-D43
A9-B39-C12-D43
A13-B39-C12-D43
A24-B39-C12-D43
A69-B39-C12-D43
A67-B39-C12-D43
A39-B39-C12-D43
A65-B39-C12-D43
A66-B39-C12-D43
A2-B45-C12-D43
A3-B45-C12-D43
A9-B45-C12-D43
A13-B45-C12-D43
A24-B45-C12-D43
A69-B45-C12-D43
A67-B45-C12-D43
A39-B45-C12-D43
A65-B45-C12-D43
A66-B45-C12-D43
A2-B53-C12-D43
A3-B53-C12-D43
A9-B53-C12-D43
A13-B53-C12-D43
A24-B53-C12-D43
A69-B53-C12-D43
A67-B53-C12-D43
A39-B53-C12-D43
A65-B53-C12-D43
A66-B53-C12-D43
A2-B79-C12-D43
A3-B79-C12-D43
A9-B79-C12-D43
A13-B79-C12-D43
A24-B79-C12-D43
A69-B79-C12-D43
A67-B79-C12-D43
A39-B79-C12-D43
A65-B79-C12-D43
A66-B79-C12-D43
A2-B80-C12-D43
A3-B80-C12-D43
A9-B80-C12-D43

-continued
A13-B80-C12-D43
A24-B80-C12-D43
A69-B80-C12-D43
A67-B80-C12-D43
A39-B80-C12-D43
A65-B80-C12-D43
A66-B80-C12-D43
A2-B85-C12-D43
A3-B85-C12-D43
A9-B85-C12-D43
A13-B85-C12-D43
A24-B85-C12-D43
A69-B85-C12-D43
A67-B85-C12-D43
A39-B85-C12-D43
A65-B85-C12-D43
A66-B85-C12-D43
A2-B86-C12-D43
A3-B86-C12-D43
A9-B86-C12-D43
A13-B86-C12-D43
A24-B86-C12-D43
A69-B86-C12-D43
A67-B86-C12-D43
A39-B86-C12-D43
A65-B86-C12-D43
A66-B86-C12-D43
A2-B87-C12-D43
A3-B87-C12-D43
A9-B87-C12-D43
A13-B87-C12-D43
A24-B87-C12-D43
A69-B87-C12-D43
A67-B87-C12-D43
A39-B87-C12-D43
A65-B87-C12-D43
A66-B87-C12-D43
A2-B89-C12-D43
A3-B89-C12-D43
A9-B89-C12-D43
A13-B89-C12-D43
A24-B89-C12-D43
A69-B89-C12-D43
A67-B89-C12-D43
A39-B89-C12-D43
A65-B89-C12-D43
A66-B89-C12-D43
A2-B92-C12-D43
A3-B92-C12-D43
A9-B92-C12-D43
A13-B92-C12-D43
A24-B92-C12-D43
A69-B92-C12-D43
A67-B92-C12-D43
A39-B92-C12-D43
A65-B92-C12-D43
A66-B92-C12-D43
A2-B4-C13-D43
A3-B4-C13-D43
A9-B4-C13-D43
A13-B4-C13-D43
A24-B4-C13-D43
A69-B4-C13-D43
A67-B4-C13-D43
A39-B4-C13-D43
A65-B4-C13-D43
A66-B4-C13-D43
A2-B5-C13-D43
A3-B5-C13-D43
A9-B5-C13-D43
A13-B5-C13-D43
A24-B5-C13-D43
A69-B5-C13-D43
A67-B5-C13-D43
A39-B5-C13-D43
A65-B5-C13-D43
A66-B5-C13-D43
A2-B6-C13-D43
A3-B6-C13-D43
A9-B6-C13-D43

-continued

A13-B6-C13-D43
A24-B6-C13-D43
A69-B6-C13-D43
A67-B6-C13-D43
A39-B6-C13-D43
A65-B6-C13-D43
A66-B6-C13-D43
A2-B32-C13-D43
A3-B32-C13-D43
A9-B32-C13-D43
A13-B32-C13-D43
A24-B32-C13-D43
A69-B32-C13-D43
A67-B32-C13-D43
A39-B32-C13-D43
A65-B32-C13-D43
A66-B32-C13-D43
A2-B39-C13-D43
A3-B39-C13-D43
A9-B39-C13-D43
A13-B39-C13-D43
A24-B39-C13-D43
A69-B39-C13-D43
A67-B39-C13-D43
A39-B39-C13-D43
A65-B39-C13-D43
A66-B39-C13-D43
A2-B45-C13-D43
A3-B45-C13-D43
A9-B45-C13-D43
A13-B45-C13-D43
A24-B45-C13-D43
A69-B45-C13-D43
A67-B45-C13-D43
A39-B45-C13-D43
A65-B45-C13-D43
A66-B45-C13-D43
A2-B53-C13-D43
A3-B53-C13-D43
A9-B53-C13-D43
A13-B53-C13-D43
A24-B53-C13-D43
A69-B53-C13-D43
A67-B53-C13-D43
A39-B53-C13-D43
A65-B53-C13-D43
A66-B53-C13-D43
A2-B79-C13-D43
A3-B79-C13-D43
A9-B79-C13-D43
A13-B79-C13-D43
A24-B79-C13-D43
A69-B79-C13-D43
A67-B79-C13-D43
A39-B79-C13-D43
A65-B79-C13-D43
A66-B79-C13-D43
A2-B80-C13-D43
A3-B80-C13-D43
A9-B80-C13-D43
A13-B80-C13-D43
A24-B80-C13-D43
A69-B80-C13-D43
A67-B80-C13-D43
A39-B80-C13-D43
A65-B80-C13-D43
A66-B80-C13-D43
A2-B85-C13-D43
A3-B85-C13-D43
A9-B85-C13-D43
A13-B85-C13-D43
A24-B85-C13-D43
A69-B85-C13-D43
A67-B85-C13-D43
A39-B85-C13-D43
A65-B85-C13-D43
A66-B85-C13-D43
A2-B86-C13-D43
A3-B86-C13-D43
A9-B86-C13-D43

-continued

A13-B86-C13-D43
A24-B86-C13-D43
A69-B86-C13-D43
A67-B86-C13-D43
A39-B86-C13-D43
A65-B86-C13-D43
A66-B86-C13-D43
A2-B87-C13-D43
A3-B87-C13-D43
A9-B87-C13-D43
A13-B87-C13-D43
A24-B87-C13-D43
A69-B87-C13-D43
A67-B87-C13-D43
A39-B87-C13-D43
A65-B87-C13-D43
A66-B87-C13-D43
A2-B89-C13-D43
A3-B89-C13-D43
A9-B89-C13-D43
A13-B89-C13-D43
A24-B89-C13-D43
A69-B89-C13-D43
A67-B89-C13-D43
A39-B89-C13-D43
A65-B89-C13-D43
A66-B89-C13-D43
A2-B92-C13-D43
A3-B92-C13-D43
A9-B92-C13-D43
A13-B92-C13-D43
A24-B92-C13-D43
A69-B92-C13-D43
A67-B92-C13-D43
A39-B92-C13-D43
A65-B92-C13-D43
A66-B92-C13-D43
A2-B4-C1-D44
A3-B4-C1-D44
A9-B4-C1-D44
A13-B4-C1-D44
A24-B4-C1-D44
A69-B4-C1-D44
A67-B4-C1-D44
A39-B4-C1-D44
A65-B4-C1-D44
A66-B4-C1-D44
A2-B5-C1-D44
A3-B5-C1-D44
A9-B5-C1-D44
A13-B5-C1-D44
A24-B5-C1-D44
A69-B5-C1-D44
A67-B5-C1-D44
A39-B5-C1-D44
A65-B5-C1-D44
A66-B5-C1-D44
A2-B6-C1-D44
A3-B6-C1-D44
A9-B6-C1-D44
A13-B6-C1-D44
A24-B6-C1-D44
A69-B6-C1-D44
A67-B6-C1-D44
A39-B6-C1-D44
A65-B6-C1-D44
A66-B6-C1-D44
A2-B32-C1-D44
A3-B32-C1-D44
A9-B32-C1-D44
A13-B32-C1-D44
A24-B32-C1-D44
A69-B32-C1-D44
A67-B32-C1-D44
A39-B32-C1-D44
A65-B32-C1-D44
A66-B32-C1-D44
A2-B39-C1-D44
A3-B39-C1-D44
A9-B39-C1-D44

-continued
A13-B39-C1-D44
A24-B39-C1-D44
A69-B39-C1-D44
A67-B39-C1-D44
A39-B39-C1-D44
A65-B39-C1-D44
A66-B39-C1-D44
A2-B45-C1-D44
A3-B45-C1-D44
A9-B45-C1-D44
A13-B45-C1-D44
A24-B45-C1-D44
A69-B45-C1-D44
A67-B45-C1-D44
A39-B45-C1-D44
A65-B45-C1-D44
A66-B45-C1-D44
A2-B53-C1-D44
A3-B53-C1-D44
A9-B53-C1-D44
A13-B53-C1-D44
A24-B5 3-C1-D44
A69-B53-C1-D44
A67-B53-C1-D44
A39-B53-C1-D44
A65-B53-C1-D44
A66-B53-C1-D44
A2-B79-C1-D44
A3-B79-C1-D44
A9-B79-C1-D44
A13-B79-C1-D44
A24-B79-C1-D44
A69-B79-C1-D44
A67-B79-C1-D44
A39-B79-C1-D44
A65-B79-C1-D44
A66-B79-C1-D44
A2-B80-C1-D44
A3-B80-C1-D44
A9-B80-C1-D44
A13-B80-C1-D44
A24-B80-C1-D44
A69-B80-C1-D44
A67-B80-C1-D44
A39-B80-C1-D44
A65-B80-C1-D44
A66-B80-C1-D44
A2-B85-C1-D44
A3-B85-C1-D44
A9-B85-C1-D44
A13-B85-C1-D44
A24-B85-C1-D44
A69-B85-C1-D44
A67-B85-C1-D44
A39-B85-C1-D44
A65-B85-C1-D44
A66-B85-C1-D44
A2-B86-C1-D44
A3-B86-C1-D44
A9-B86-C1-D44
A13-B86-C1-D44
A24-B86-C1-D44
A69-B86-C1-D44
A67-B86-C1-D44
A39-B86-C1-D44
A65-B86-C1-D44
A66-B86-C1-D44
A2-B87-C1-D44
A3-B87-C1-D44
A9-B87-C1-D44
A13-B87-C1-D44
A24-B87-C1-D44
A69-B87-C1-D44
A67-B87-C1-D44
A39-B87-C1-D44
A65-B87-C1-D44
A66-B87-C1-D44
A2-B89-C1-D44
A3-B89-C1-D44
A9-B89-C1-D44

-continued
A13-B89-C1-D44
A24-B89-C1-D44
A69-B89-C1-D44
A67-B89-C1-D44
A39-B89-C1-D44
A65-B89-C1-D44
A66-B89-C1-D44
A2-B92-C1-D44
A3-B92-C1-D44
A9-B92-C1-D44
A13-B92-C1-D44
A24-B92-C1-D44
A69-B92-C1-D44
A67-B92-C1-D44
A39-B92-C1-D44
A65-B92-C1-D44
A66-B92-C1-D44
A2-B4-C2-D44
A3-B4-C2-D44
A9-B4-C2-D44
A13-B4-C2-D44
A24-B4-C2-D44
A69-B4-C2-D44
A67-B4-C2-D44
A39-B4-C2-D44
A65-B4-C2-D44
A66-B4-C2-D44
A2-B5-C2-D44
A3-B5-C2-D44
A9-B5-C2-D44
A13-B5-C2-D44
A24-B5-C2-D44
A69-B5-C2-D44
A67-B5-C2-D44
A39-B5-C2-D44
A65-B5-C2-D44
A66-B5-C2-D44
A2-B6-C2-D44
A3-B6-C2-D44
A9-B6-C2-D44
A13-B6-C2-D44
A24-B6-C2-D44
A69-B6-C2-D44
A67-B6-C2-D44
A39-B6-C2-D44
A65-B6-C2-D44
A66-B6-C2-D44
A2-B32-C2-D44
A3-B32-C2-D44
A9-B32-C2-D44
A13-B32-C2-D44
A24-B32-C2-D44
A69-B32-C2-D44
A67-B32-C2-D44
A39-B32-C2-D44
A65-B32-C2-D44
A66-B32-C2-D44
A2-B39-C2-D44
A3-B39-C2-D44
A9-B39-C2-D44
A13-B39-C2-D44
A24-B39-C2-D44
A69-B39-C2-D44
A67-B39-C2-D44
A39-B39-C2-D44
A65-B39-C2-D44
A66-B39-C2-D44
A2-B45-C2-D44
A3-B45-C2-D44
A9-B45-C2-D44
A13-B45-C2-D44
A24-B45-C2-D44
A69-B45-C2-D44
A67-B45-C2-D44
A39-B45-C2-D44
A65-B45-C2-D44
A66-B45-C2-D44
A2-B53-C2-D44
A3-B53-C2-D44
A9-B53-C2-D44

-continued

| 1051 | 1052 |
|---|---|
| A13-B53-C2-D44 | A13-B4-C3-D44 |
| A24-B53-C2-D44 | A24-B4-C3-D44 |
| A69-B53-C2-D44 | A69-B4-C3-D44 |
| A67-B53-C2-D44 | A67-B4-C3-D44 |
| A39-B53-C2-D44 | A39-B4-C3-D44 |
| A65-B53-C2-D44 | A65-B4-C3-D44 |
| A66-B53-C2-D44 | A66-B4-C3-D44 |
| A2-B79-C2-D44 | A2-B5-C3-D44 |
| A3-B79-C2-D44 | A3-B5-C3-D44 |
| A9-B79-C2-D44 | A9-B5-C3-D44 |
| A13-B79-C2-D44 | A13-B5-C3-D44 |
| A24-B79-C2-D44 | A24-B5-C3-D44 |
| A69-B79-C2-D44 | A69-B5-C3-D44 |
| A67-B79-C2-D44 | A67-B5-C3-D44 |
| A39-B79-C2-D44 | A39-B5-C3-D44 |
| A65-B79-C2-D44 | A65-B5-C3-D44 |
| A66-B79-C2-D44 | A66-B5-C3-D44 |
| A2-B80-C2-D44 | A2-B6-C3-D44 |
| A3-B80-C2-D44 | A3-B6-C3-D44 |
| A9-B80-C2-D44 | A9-B6-C3-D44 |
| A13-B80-C2-D44 | A13-B6-C3-D44 |
| A24-B80-C2-D44 | A24-B6-C3-D44 |
| A69-B80-C2-D44 | A69-B6-C3-D44 |
| A67-B80-C2-D44 | A67-B6-C3-D44 |
| A39-B80-C2-D44 | A39-B6-C3-D44 |
| A65-B80-C2-D44 | A65-B6-C3-D44 |
| A66-B80-C2-D44 | A66-B6-C3-D44 |
| A2-B85-C2-D44 | A2-B32-C3-D44 |
| A3-B85-C2-D44 | A3-B32-C3-D44 |
| A9-B85-C2-D44 | A9-B32-C3-D44 |
| A13-B85-C2-D44 | A13-B32-C3-D44 |
| A24-B85-C2-D44 | A24-B32-C3-D44 |
| A69-B85-C2-D44 | A69-B32-C3-D44 |
| A67-B85-C2-D44 | A67-B32-C3-D44 |
| A39-B85-C2-D44 | A39-B32-C3-D44 |
| A65-B85-C2-D44 | A65-B32-C3-D44 |
| A66-B85-C2-D44 | A66-B32-C3-D44 |
| A2-B86-C2-D44 | A2-B39-C3-D44 |
| A3-B86-C2-D44 | A3-B39-C3-D44 |
| A9-B86-C2-D44 | A9-B39-C3-D44 |
| A13-B86-C2-D44 | A13-B39-C3-D44 |
| A24-B86-C2-D44 | A24-B39-C3-D44 |
| A69-B86-C2-D44 | A69-B39-C3-D44 |
| A67-B86-C2-D44 | A67-B39-C3-D44 |
| A39-B86-C2-D44 | A39-B39-C3-D44 |
| A65-B86-C2-D44 | A65-B39-C3-D44 |
| A66-B86-C2-D44 | A66-B39-C3-D44 |
| A2-B87-C2-D44 | A2-B45-C3-D44 |
| A3-B87-C2-D44 | A3-B45-C3-D44 |
| A9-B87-C2-D44 | A9-B45-C3-D44 |
| A13-B87-C2-D44 | A13-B45-C3-D44 |
| A24-B87-C2-D44 | A24-B45-C3-D44 |
| A69-B87-C2-D44 | A69-B45-C3-D44 |
| A67-B87-C2-D44 | A67-B45-C3-D44 |
| A39-B87-C2-D44 | A39-B45-C3-D44 |
| A65-B87-C2-D44 | A65-B45-C3-D44 |
| A66-B87-C2-D44 | A66-B45-C3-D44 |
| A2-B89-C2-D44 | A2-B53-C3-D44 |
| A3-B89-C2-D44 | A3-B53-C3-D44 |
| A9-B89-C2-D44 | A9-B53-C3-D44 |
| A13-B89-C2-D44 | A13-B53-C3-D44 |
| A24-B89-C2-D44 | A24-B53-C3-D44 |
| A69-B89-C2-D44 | A69-B53-C3-D44 |
| A67-B89-C2-D44 | A67-B53-C3-D44 |
| A39-B89-C2-D44 | A39-B53-C3-D44 |
| A65-B89-C2-D44 | A65-B53-C3-D44 |
| A66-B89-C2-D44 | A66-B53-C3-D44 |
| A2-B92-C2-D44 | A2-B79-C3-D44 |
| A3-B92-C2-D44 | A3-B79-C3-D44 |
| A9-B92-C2-D44 | A9-B79-C3-D44 |
| A13-B92-C2-D44 | A13-B79-C3-D44 |
| A24-B92-C2-D44 | A24-B79-C3-D44 |
| A69-B92-C2-D44 | A69-B79-C3-D44 |
| A67-B92-C2-D44 | A67-B79-C3-D44 |
| A39-B92-C2-D44 | A39-B79-C3-D44 |
| A65-B92-C2-D44 | A65-B79-C3-D44 |
| A66-B92-C2-D44 | A66-B79-C3-D44 |
| A2-B4-C3-D44 | A2-B80-C3-D44 |
| A3-B4-C3-D44 | A3-B80-C3-D44 |
| A9-B4-C3-D44 | A9-B80-C3-D44 |

-continued
A13-B80-C3-D44
A24-B80-C3-D44
A69-B80-C3-D44
A67-B80-C3-D44
A39-B80-C3-D44
A65-B80-C3-D44
A66-B80-C3-D44
A2-B85-C3-D44
A3-B85-C3-D44
A9-B85-C3-D44
A13-B85-C3-D44
A24-B85-C3-D44
A69-B85-C3-D44
A67-B85-C3-D44
A39-B85-C3-D44
A65-B85-C3-D44
A66-B85-C3-D44
A2-B86-C3-D44
A3-B86-C3-D44
A9-B86-C3-D44
A13-B86-C3-D44
A24-B86-C3-D44
A69-B86-C3-D44
A67-B86-C3-D44
A39-B86-C3-D44
A65-B86-C3-D44
A66-B86-C3-D44
A2-B87-C3-D44
A3-B87-C3-D44
A9-B87-C3-D44
A13-B87-C3-D44
A24-B87-C3-D44
A69-B87-C3-D44
A67-B87-C3-D44
A39-B87-C3-D44
A65-B87-C3-D44
A66-B87-C3-D44
A2-B89-C3-D44
A3-B89-C3-D44
A9-B89-C3-D44
A13-B89-C3-D44
A24-B89-C3-D44
A69-B89-C3-D44
A67-B89-C3-D44
A39-B89-C3-D44
A65-B89-C3-D44
A66-B89-C3-D44
A2-B92-C3-D44
A3-B92-C3-D44
A9-B92-C3-D44
A13-B92-C3-D44
A24-B92-C3-D44
A69-B92-C3-D44
A67-B92-C3-D44
A39-B92-C3-D44
A65-B92-C3-D44
A66-B92-C3-D44
A2-B4-C4-D44
A3-B4-C4-D44
A9-B4-C4-D44
A13-B4-C4-D44
A24-B4-C4-D44
A69-B4-C4-D44
A67-B4-C4-D44
A39-B4-C4-D44
A65-B4-C4-D44
A66-B4-C4-D44
A2-B5-C4-D44
A3-B5-C4-D44
A9-B5-C4-D44
A13-B5-C4-D44
A24-B5-C4-D44
A69-B5-C4-D44
A67-B5-C4-D44
A39-B5-C4-D44
A65-B5-C4-D44
A66-B5-C4-D44
A2-B6-C4-D44
A3-B6-C4-D44
A9-B6-C4-D44

-continued
A13-B6-C4-D44
A24-B6-C4-D44
A69-B6-C4-D44
A67-B6-C4-D44
A39-B6-C4-D44
A65-B6-C4-D44
A66-B6-C4-D44
A2-B32-C4-D44
A3-B32-C4-D44
A9-B32-C4-D44
A13-B32-C4-D44
A24-B32-C4-D44
A69-B32-C4-D44
A67-B32-C4-D44
A39-B32-C4-D44
A65-B32-C4-D44
A66-B32-C4-D44
A2-B39-C4-D44
A3-B39-C4-D44
A9-B39-C4-D44
A13-B39-C4-D44
A24-B39-C4-D44
A69-B39-C4-D44
A67-B39-C4-D44
A39-B39-C4-D44
A65-B39-C4-D44
A66-B39-C4-D44
A2-B45-C4-D44
A3-B45-C4-D44
A9-B45-C4-D44
A13-B45-C4-D44
A24-B45-C4-D44
A69-B45-C4-D44
A67-B45-C4-D44
A39-B45-C4-D44
A65-B45-C4-D44
A66-B45-C4-D44
A2-B53-C4-D44
A3-B53-C4-D44
A9-B53-C4-D44
A13-B53-C4-D44
A24-B53-C4-D44
A69-B53-C4-D44
A67-B53-C4-D44
A39-B53-C4-D44
A65-B53-C4-D44
A66-B53-C4-D44
A2-B79-C4-D44
A3-B79-C4-D44
A9-B79-C4-D44
A13-B79-C4-D44
A24-B79-C4-D44
A69-B79-C4-D44
A67-B79-C4-D44
A39-B79-C4-D44
A65-B79-C4-D44
A66-B79-C4-D44
A2-B80-C4-D44
A3-B80-C4-D44
A9-B80-C4-D44
A13-B80-C4-D44
A24-B80-C4-D44
A69-B80-C4-D44
A67-B80-C4-D44
A39-B80-C4-D44
A65-B80-C4-D44
A66-B80-C4-D44
A2-B85-C4-D44
A3-B85-C4-D44
A9-B85-C4-D44
A13-B85-C4-D44
A24-B85-C4-D44
A69-B85-C4-D44
A67-B85-C4-D44
A39-B85-C4-D44
A65-B85-C4-D44
A66-B85-C4-D44
A2-B86-C4-D44
A3-B86-C4-D44
A9-B86-C4-D44

-continued
A13-B86-C4-D44
A24-B86-C4-D44
A69-B86-C4-D44
A67-B86-C4-D44
A39-B86-C4-D44
A65-B86-C4-D44
A66-B86-C4-D44
A2-B87-C4-D44
A3-B87-C4-D44
A9-B87-C4-D44
A13-B87-C4-D44
A24-B87-C4-D44
A69-B87-C4-D44
A67-B87-C4-D44
A39-B87-C4-D44
A65-B87-C4-D44
A66-B87-C4-D44
A2-B89-C4-D44
A3-B89-C4-D44
A9-B89-C4-D44
A13-B89-C4-D44
A24-B89-C4-D44
A69-B89-C4-D44
A67-B89-C4-D44
A39-B89-C4-D44
A65-B89-C4-D44
A66-B89-C4-D44
A2-B92-C4-D44
A3-B92-C4-D44
A9-B92-C4-D44
A13-B92-C4-D44
A24-B92-C4-D44
A69-B92-C4-D44
A67-B92-C4-D44
A39-B92-C4-D44
A65-B92-C4-D44
A66-B92-C4-D44
A2-B4-C5-D44
A3-B4-C5-D44
A9-B4-C5-D44
A13-B4-C5-D44
A24-B4-C5-D44
A69-B4-C5-D44
A67-B4-C5-D44
A39-B4-C5-D44
A65-B4-C5-D44
A66-B4-C5-D44
A2-B5-C5-D44
A3-B5-C5-D44
A9-B5-C5-D44
A13-B5-C5-D44
A24-B5-C5-D44
A69-B5-C5-D44
A67-B5-C5-D44
A39-B5-C5-D44
A65-B5-C5-D44
A66-B5-C5-D44
A2-B6-C5-D44
A3-B6-C5-D44
A9-B6-C5-D44
A13-B6-C5-D44
A24-B6-C5-D44
A69-B6-C5-D44
A67-B6-C5-D44
A39-B6-C5-D44
A65-B6-C5-D44
A66-B6-C5-D44
A2-B32-C5-D44
A3-B32-C5-D44
A9-B32-C5-D44
A13-B32-C5-D44
A24-B32-C5-D44
A69-B32-C5-D44
A67-B32-C5-D44
A39-B32-C5-D44
A65-B32-C5-D44
A66-B32-C5-D44
A2-B39-C5-D44
A3-B39-C5-D44
A9-B39-C5-D44

-continued
A13-B39-C5-D44
A24-B39-C5-D44
A69-B39-C5-D44
A67-B39-C5-D44
A39-B39-C5-D44
A65-B39-C5-D44
A66-B39-C5-D44
A2-B45-C5-D44
A3-B45-C5-D44
A9-B45-C5-D44
A13-B45-C5-D44
A24-B45-C5-D44
A69-B45-C5-D44
A67-B45-C5-D44
A39-B45-C5-D44
A65-B45-C5-D44
A66-B45-C5-D44
A2-B53-C5-D44
A3-B53-C5-D44
A9-B53-C5-D44
A13-B53-C5-D44
A24-B53-C5-D44
A69-B53-C5-D44
A67-B53-C5-D44
A39-B53-C5-D44
A65-B53-C5-D44
A66-B53-C5-D44
A2-B79-C5-D44
A3-B79-C5-D44
A9-B79-C5-D44
A13-B79-C5-D44
A24-B79-C5-D44
A69-B79-C5-D44
A67-B79-C5-D44
A39-B79-C5-D44
A65-B79-C5-D44
A66-B79-C5-D44
A2-B80-C5-D44
A3-B80-C5-D44
A9-B80-C5-D44
A13-B80-C5-D44
A24-B80-C5-D44
A69-B80-C5-D44
A67-B80-C5-D44
A39-B80-C5-D44
A65-B80-C5-D44
A66-B80-C5-D44
A2-B85-C5-D44
A3-B85-C5-D44
A9-B85-C5-D44
A13-B85-C5-D44
A24-B85-C5-D44
A69-B85-C5-D44
A67-B85-C5-D44
A39-B85-C5-D44
A65-B85-C5-D44
A66-B85-C5-D44
A2-B86-C5-D44
A3-B86-C5-D44
A9-B86-C5-D44
A13-B86-C5-D44
A24-B86-C5-D44
A69-B86-C5-D44
A67-B86-C5-D44
A39-B86-C5-D44
A65-B86-C5-D44
A66-B86-C5-D44
A2-B87-C5-D44
A3-B87-C5-D44
A9-B87-C5-D44
A13-B87-C5-D44
A24-B87-C5-D44
A69-B87-C5-D44
A67-B87-C5-D44
A39-B87-C5-D44
A65-B87-C5-D44
A66-B87-C5-D44
A2-B89-C5-D44
A3-B89-C5-D44
A9-B89-C5-D44

-continued
A13-B89-C5-D44
A24-B89-C5-D44
A69-B89-C5-D44
A67-B89-C5-D44
A39-B89-C5-D44
A65-B89-C5-D44
A66-B89-C5-D44
A2-B92-C5-D44
A3-B92-C5-D44
A9-B92-C5-D44
A13-B92-C5-D44
A24-B92-C5-D44
A69-B92-C5-D44
A67-B92-C5-D44
A39-B92-C5-D44
A65-B92-C5-D44
A66-B92-C5-D44
A2-B4-C6-D44
A3-B4-C6-D44
A9-B4-C6-D44
A13-B4-C6-D44
A24-B4-C6-D44
A69-B4-C6-D44
A67-B4-C6-D44
A39-B4-C6-D44
A65-B4-C6-D44
A66-B4-C6-D44
A2-B5-C6-D44
A3-B5-C6-D44
A9-B5-C6-D44
A13-B5-C6-D44
A24-B5-C6-D44
A69-B5-C6-D44
A67-B5-C6-D44
A39-B5-C6-D44
A65-B5-C6-D44
A66-B5-C6-D44
A2-B6-C6-D44
A3-B6-C6-D44
A9-B6-C6-D44
A13-B6-C6-D44
A24-B6-C6-D44
A69-B6-C6-D44
A67-B6-C6-D44
A39-B6-C6-D44
A65-B6-C6-D44
A66-B6-C6-D44
A2-B32-C6-D44
A3-B32-C6-D44
A9-B32-C6-D44
A13-B32-C6-D44
A24-B32-C6-D44
A69-B32-C6-D44
A67-B32-C6-D44
A39-B32-C6-D44
A65-B32-C6-D44
A66-B32-C6-D44
A2-B39-C6-D44
A3-B39-C6-D44
A9-B39-C6-D44
A13-B39-C6-D44
A24-B39-C6-D44
A69-B39-C6-D44
A67-B39-C6-D44
A39-B39-C6-D44
A65-B39-C6-D44
A66-B39-C6-D44
A2-B45-C6-D44
A3-B45-C6-D44
A9-B45-C6-D44
A13-B45-C6-D44
A24-B45-C6-D44
A69-B45-C6-D44
A67-B45-C6-D44
A39-B45-C6-D44
A65-B45-C6-D44
A66-B45-C6-D44
A2-B53-C6-D44
A3-B53-C6-D44
A9-B53-C6-D44

-continued
A13-B53-C6-D44
A24-B53-C6-D44
A69-B53-C6-D44
A67-B53-C6-D44
A39-B53-C6-D44
A65-B53-C6-D44
A66-B53-C6-D44
A2-B79-C6-D44
A3-B79-C6-D44
A9-B79-C6-D44
A13-B79-C6-D44
A24-B79-C6-D44
A69-B79-C6-D44
A67-B79-C6-D44
A39-B79-C6-D44
A65-B79-C6-D44
A66-B79-C6-D44
A2-B80-C6-D44
A3-B80-C6-D44
A9-B80-C6-D44
A13-B80-C6-D44
A24-B80-C6-D44
A69-B80-C6-D44
A67-B80-C6-D44
A39-B80-C6-D44
A65-B80-C6-D44
A66-B80-C6-D44
A2-B85-C6-D44
A3-B85-C6-D44
A9-B85-C6-D44
A13-B85-C6-D44
A24-B85-C6-D44
A69-B85-C6-D44
A67-B85-C6-D44
A39-B85-C6-D44
A65-B85-C6-D44
A66-B85-C6-D44
A2-B86-C6-D44
A3-B86-C6-D44
A9-B86-C6-D44
A13-B86-C6-D44
A24-B86-C6-D44
A69-B86-C6-D44
A67-B86-C6-D44
A39-B86-C6-D44
A65-B86-C6-D44
A66-B86-C6-D44
A2-B87-C6-D44
A3-B87-C6-D44
A9-B87-C6-D44
A13-B87-C6-D44
A24-B87-C6-D44
A69-B87-C6-D44
A67-B87-C6-D44
A39-B87-C6-D44
A65-B87-C6-D44
A66-B87-C6-D44
A2-B89-C6-D44
A3-B89-C6-D44
A9-B89-C6-D44
A13-B89-C6-D44
A24-B89-C6-D44
A69-B89-C6-D44
A67-B89-C6-D44
A39-B89-C6-D44
A65-B89-C6-D44
A66-B89-C6-D44
A2-B92-C6-D44
A3-B92-C6-D44
A9-B92-C6-D44
A13-B92-C6-D44
A24-B92-C6-D44
A69-B92-C6-D44
A67-B92-C6-D44
A39-B92-C6-D44
A65-B92-C6-D44
A66-B92-C6-D44
A2-B4-C7-D44
A3-B4-C7-D44
A9-B4-C7-D44

-continued
A13-B4-C7-D44
A24-B4-C7-D44
A69-B4-C7-D44
A67-B4-C7-D44
A39-B4-C7-D44
A65-B4-C7-D44
A66-B4-C7-D44
A2-B5-C7-D44
A3-B5-C7-D44
A9-B5-C7-D44
A13-B5-C7-D44
A24-B5-C7-D44
A69-B5-C7-D44
A67-B5-C7-D44
A39-B5-C7-D44
A65-B5-C7-D44
A66-B5-C7-D44
A2-B6-C7-D44
A3-B6-C7-D44
A9-B6-C7-D44
A13-B6-C7-D44
A24-B6-C7-D44
A69-B6-C7-D44
A67-B6-C7-D44
A39-B6-C7-D44
A65-B6-C7-D44
A66-B6-C7-D44
A2-B32-C7-D44
A3-B32-C7-D44
A9-B32-C7-D44
A13-B32-C7-D44
A24-B32-C7-D44
A69-B32-C7-D44
A67-B32-C7-D44
A39-B32-C7-D44
A65-B32-C7-D44
A66-B32-C7-D44
A2-B39-C7-D44
A3-B39-C7-D44
A9-B39-C7-D44
A13-B39-C7-D44
A24-B39-C7-D44
A69-B39-C7-D44
A67-B39-C7-D44
A39-B39-C7-D44
A65-B39-C7-D44
A66-B39-C7-D44
A2-B45-C7-D44
A3-B45-C7-D44
A9-B45-C7-D44
A13-B45-C7-D44
A24-B45-C7-D44
A69-B45-C7-D44
A67-B45-C7-D44
A39-B45-C7-D44
A65-B45-C7-D44
A66-B45-C7-D44
A2-B53-C7-D44
A3-B53-C7-D44
A9-B53-C7-D44
A13-B53-C7-D44
A24-B53-C7-D44
A69-B53-C7-D44
A67-B53-C7-D44
A39-B53-C7-D44
A65-B53-C7-D44
A66-B53-C7-D44
A2-B79-C7-D44
A3-B79-C7-D44
A9-B79-C7-D44
A13-B79-C7-D44
A24-B79-C7-D44
A69-B79-C7-D44
A67-B79-C7-D44
A39-B79-C7-D44
A65-B79-C7-D44
A66-B79-C7-D44
A2-B80-C7-D44
A3-B80-C7-D44
A9-B80-C7-D44

-continued
A13-B80-C7-D44
A24-B80-C7-D44
A69-B80-C7-D44
A67-B80-C7-D44
A39-B80-C7-D44
A65-B80-C7-D44
A66-B80-C7-D44
A2-B85-C7-D44
A3-B85-C7-D44
A9-B85-C7-D44
A13-B85-C7-D44
A24-B85-C7-D44
A69-B85-C7-D44
A67-B85-C7-D44
A39-B85-C7-D44
A65-B85-C7-D44
A66-B85-C7-D44
A2-B86-C7-D44
A3-B86-C7-D44
A9-B86-C7-D44
A13-B86-C7-D44
A24-B86-C7-D44
A69-B86-C7-D44
A67-B86-C7-D44
A39-B86-C7-D44
A65-B86-C7-D44
A66-B86-C7-D44
A2-B87-C7-D44
A3-B87-C7-D44
A9-B87-C7-D44
A13-B87-C7-D44
A24-B87-C7-D44
A69-B87-C7-D44
A67-B87-C7-D44
A39-B87-C7-D44
A65-B87-C7-D44
A66-B87-C7-D44
A2-B89-C7-D44
A3-B89-C7-D44
A9-B89-C7-D44
A13-B89-C7-D44
A24-B89-C7-D44
A69-B89-C7-D44
A67-B89-C7-D44
A39-B89-C7-D44
A65-B89-C7-D44
A66-B89-C7-D44
A2-B92-C7-D44
A3-B92-C7-D44
A9-B92-C7-D44
A13-B92-C7-D44
A24-B92-C7-D44
A69-B92-C7-D44
A67-B92-C7-D44
A39-B92-C7-D44
A65-B92-C7-D44
A66-B92-C7-D44
A2-B4-C8-D44
A3-B4-C8-D44
A9-B4-C8-D44
A13-B4-C8-D44
A24-B4-C8-D44
A69-B4-C8-D44
A67-B4-C8-D44
A39-B4-C8-D44
A65-B4-C8-D44
A66-B4-C8-D44
A2-B5-C8-D44
A3-B5-C8-D44
A9-B5-C8-D44
A13-B5-C8-D44
A24-B5-C8-D44
A69-B5-C8-D44
A67-B5-C8-D44
A39-B5-C8-D44
A65-B5-C8-D44
A66-B5-C8-D44
A2-B6-C8-D44
A3-B6-C8-D44
A9-B6-C8-D44

-continued
A13-B6-C8-D44
A24-B6-C8-D44
A69-B6-C8-D44
A67-B6-C8-D44
A39-B6-C8-D44
A65-B6-CB-D44
A66-B6-C8-D44
A2-B32-C8-D44
A3-B32-C8-D44
A9-B32-C8-D44
A13-B32-C8-D44
A24-B32-C8-D44
A69-B32-C8-D44
A67-B32-C8-D44
A39-B32-C8-D44
A65-B32-C8-D44
A66-B32-C8-D44
A2-B39-C8-D44
A3-B39-C8-D44
A9-B39-C8-D44
A13-B39-C8-D44
A24-B39-C8-D44
A69-B39-C8-D44
A67-B39-C8-D44
A39-B39-C8-D44
A65-B39-C8-D44
A66-B39-C8-D44
A2-B45-C8-D44
A3-B45-C8-D44
A9-B45-C8-D44
A13-B45-C8-D44
A24-B45-C8-D44
A69-B45-C8-D44
A67-B45-C8-D44
A39-B45-C8-D44
A65-B45-C8-D44
A66-B45-C8-D44
A2-B53-C8-D44
A3-B53-C8-D44
A9-B53-C8-D44
A13-B53-C8-D44
A24-B53-C8-D44
A69-B53-C8-D44
A67-B53-C8-D44
A39-B53-C8-D44
A65-B53-C8-D44
A66-B53-C8-D44
A2-B79-C8-D44
A3-B79-C8-D44
A9-B79-C8-D44
A13-B79-C8-D44
A24-B79-C8-D44
A69-B79-C8-D44
A67-B79-C8-D44
A39-B79-C8-D44
A65-B79-C8-D44
A66-B79-C8-D44
A2-B80-C8-D44
A3-B80-C8-D44
A9-B80-C8-D44
A13-B80-C8-D44
A24-B80-C8-D44
A69-B80-C8-D44
A67-B80-C8-D44
A39-B80-C8-D44
A65-B80-C8-D44
A66-B80-C8-D44
A2-B85-C8-D44
A3-B85-C8-D44
A9-B85-C8-D44
A13-B85-C8-D44
A24-B85-C8-D44
A69-B85-C8-D44
A67-B85-C8-D44
A39-B85-C8-D44
A65-B85-C8-D44
A66-B85-C8-D44
A2-B86-C8-D44
A3-B86-C8-D44
A9-B86-C8-D44

-continued
A13-B86-C8-D44
A24-B86-C8-D44
A69-B86-C8-D44
A67-B86-C8-D44
A39-B86-C8-D44
A65-B86-C8-D44
A66-B86-C8-D44
A2-B87-C8-D44
A3-B87-C8-D44
A9-B87-C8-D44
A13-B87-C8-D44
A24-B87-C8-D44
A69-B87-C8-D44
A67-B87-C8-D44
A39-B87-C8-D44
A65-B87-C8-D44
A66-B87-C8-D44
A2-B89-C8-D44
A3-B89-C8-D44
A9-B89-C8-D44
A13-B89-C8-D44
A24-B89-C8-D44
A69-B89-C8-D44
A67-B89-C8-D44
A39-B89-C8-D44
A65-B89-C8-D44
A66-B89-C8-D44
A2-B92-C8-D44
A3-B92-C8-D44
A9-B92-C8-D44
A13-B92-C8-D44
A24-B92-C8-D44
A69-B92-C8-D44
A67-B92-C8-D44
A39-B92-C8-D44
A65-B92-C8-D44
A66-B92-C8-D44
A2-B4-C9-D44
A3-B4-C9-D44
A9-B4-C9-D44
A13-B4-C9-D44
A24-B4-C9-D44
A69-B4-C9-D44
A67-B4-C9-D44
A39-B4-C9-D44
A65-B4-C9-D44
A66-B4-C9-D44
A2-B5-C9-D44
A3-B5-C9-D44
A9-B5-C9-D44
A13-B5-C9-D44
A24-B5-C9-D44
A69-B5-C9-D44
A67-B5-C9-D44
A39-B5-C9-D44
A65-B5-C9-D44
A66-B5-C9-D44
A2-B6-C9-D44
A3-B6-C9-D44
A9-B6-C9-D44
A13-B6-C9-D44
A24-B6-C9-D44
A69-B6-C9-D44
A67-B6-C9-D44
A39-B6-C9-D44
A65-B6-C9-D44
A66-B6-C9-D44
A2-B32-C9-D44
A3-B32-C9-D44
A9-B32-C9-D44
A13-B32-C9-D44
A24-B32-C9-D44
A69-B32-C9-D44
A67-B32-C9-D44
A39-B32-C9-D44
A65-B32-C9-D44
A66-B32-C9-D44
A2-B39-C9-D44
A3-B39-C9-D44
A9-B39-C9-D44

-continued
A13-B39-C9-D44
A24-B39-C9-D44
A69-B39-C9-D44
A67-B39-C9-D44
A39-B39-C9-D44
A65-B39-C9-D44
A66-B39-C9-D44
A2-B45-C9-D44
A3-B45-C9-D44
A9-B45-C9-D44
A13-B45-C9-D44
A24-B45-C9-D44
A69-B45-C9-D44
A67-B45-C9-D44
A39-B45-C9-D44
A65-B45-C9-D44
A66-B45-C9-D44
A2-B53-C9-D44
A3-B53-C9-D44
A9-B53-C9-D44
A13-B53-C9-D44
A24-B53-C9-D44
A69-B53-C9-D44
A67-B53-C9-D44
A39-B53-C9-D44
A65-B53-C9-D44
A66-B53-C9-D44
A2-B79-C9-D44
A3-B79-C9-D44
A9-B79-C9-D44
A13-B79-C9-D44
A24-B79-C9-D44
A69-B79-C9-D44
A67-B79-C9-D44
A39-B79-C9-D44
A65-B79-C9-D44
A66-B79-C9-D44
A2-B80-C9-D44
A3-B80-C9-D44
A9-B80-C9-D44
A13-B80-C9-D44
A24-B80-C9-D44
A69-B80-C9-D44
A67-B80-C9-D44
A39-B80-C9-D44
A65-B80-C9-D44
A66-B80-C9-D44
A2-B85-C9-D44
A3-B85-C9-D44
A9-B85-C9-D44
A13-B85-C9-D44
A24-B85-C9-D44
A69-B85-C9-D44
A67-B85-C9-D44
A39-B85-C9-D44
A65-B85-C9-D44
A66-B85-C9-D44
A2-B86-C9-D44
A3-B86-C9-D44
A9-B86-C9-D44
A13-B86-C9-D44
A24-B86-C9-D44
A69-B86-C9-D44
A67-B86-C9-D44
A39-B86-C9-D44
A65-B86-C9-D44
A66-B86-C9-D44
A2-B87-C9-D44
A3-B87-C9-D44
A9-B87-C9-D44
A13-B87-C9-D44
A24-B87-C9-D44
A69-B87-C9-D44
A67-B87-C9-D44
A39-B87-C9-D44
A65-B87-C9-D44
A66-B87-C9-D44
A2-B89-C9-D44
A3-B89-C9-D44
A9-B89-C9-D44

-continued
A13-B89-C9-D44
A24-B89-C9-D44
A69-B89-C9-D44
A67-B89-C9-D44
A39-B89-C9-D44
A65-B89-C9-D44
A66-B89-C9-D44
A2-B92-C9-D44
A3-B92-C9-D44
A9-B92-C9-D44
A13-B92-C9-D44
A24-B92-C9-D44
A69-B92-C9-D44
A67-B92-C9-D44
A39-B92-C9-D44
A65-B92-C9-D44
A66-B92-C9-D44
A2-B4-C10-D44
A3-B4-C10-D44
A9-B4-C10-D44
A13-B4-C10-D44
A24-B4-C10-D44
A69-B4-C10-D44
A67-B4-C10-D44
A39-B4-C10-D44
A65-B4-C10-D44
A66-B4-C10-D44
A2-B5-C10-D44
A3-B5-C10-D44
A9-B5-C10-D44
A13-B5-C10-D44
A24-B5-C10-D44
A69-B5-C10-D44
A67-B5-C10-D44
A39-B5-C10-D44
A65-B5-C10-D44
A66-B5-C10-D44
A2-B6-C10-D44
A3-B6-C10-D44
A9-B6-C10-D44
A13-B6-C10-D44
A24-B6-C10-D44
A69-B6-C10-D44
A67-B6-C10-D44
A39-B6-C10-D44
A65-B6-C10-D44
A66-B6-C10-D44
A2-B32-C10-D44
A3-B32-C10-D44
A9-B32-C10-D44
A13-B32-C10-D44
A24-B32-C10-D44
A69-B32-C10-D44
A67-B32-C10-D44
A39-B32-C10-D44
A65-B32-C10-D44
A66-B32-C10-D44
A2-B39-C10-D44
A3-B39-C10-D44
A9-B39-C10-D44
A13-B39-C10-D44
A24-B39-C10-D44
A69-B39-C10-D44
A67-B39-C10-D44
A39-B39-C10-D44
A65-B39-C10-D44
A66-B39-C10-D44
A2-B45-C10-D44
A3-B45-C10-D44
A9-B45-C10-D44
A13-B45-C10-D44
A24-B45-C10-D44
A69-B45-C10-D44
A67-B45-C10-D44
A39-B45-C10-D44
A65-B45-C10-D44
A66-B45-C10-D44
A2-B53-C10-D44
A3-B53-C10-D44
A9-B53-C10-D44

-continued
A13-B53-C10-D44
A24-B53-C10-D44
A69-B53-C10-D44
A67-B53-C10-D44
A39-B53-C10-D44
A65-B53-C10-D44
A66-B53-C10-D44
A2-B79-C10-D44
A3-B79-C10-D44
A9-B79-C10-D44
A13-B79-C10-D44
A24-B79-C10-D44
A69-B79-C10-D44
A67-B79-C10-D44
A39-B79-C10-D44
A65-B79-C10-D44
A66-B79-C10-D44
A2-B80-C10-D44
A3-B80-C10-D44
A9-B80-C10-D44
A13-B80-C10-D44
A24-B80-C10-D44
A69-B80-C10-D44
A67-B80-C10-D44
A39-B80-C10-D44
A65-B80-C10-D44
A66-B80-C10-D44
A2-B85-C10-D44
A3-B85-C10-D44
A9-B85-C10-D44
A13-B85-C10-D44
A24-B85-C10-D44
A69-B85-C10-D44
A67-B85-C10-D44
A39-B85-C10-D44
A65-B85-C10-D44
A66-B85-C10-D44
A2-B86-C10-D44
A3-B86-C10-D44
A9-B86-C10-D44
A13-B86-C10-D44
A24-B86-C10-D44
A69-B86-C10-D44
A67-B86-C10-D44
A39-B86-C10-D44
A65-B86-C10-D44
A66-B86-C10-D44
A2-B87-C10-D44
A3-B87-C10-D44
A9-B87-C10-D44
A13-B87-C10-D44
A24-B87-C10-D44
A69-B87-C10-D44
A67-B87-C10-D44
A39-B87-C10-D44
A65-B87-C10-D44
A66-B87-C10-D44
A2-B89-C10-D44
A3-B89-C10-D44
A9-B89-C10-D44
A13-B89-C10-D44
A24-B89-C10-D44
A69-B89-C10-D44
A67-B89-C10-D44
A39-B89-C10-D44
A65-B89-C10-D44
A66-B89-C10-D44
A2-B92-C10-D44
A3-B92-C10-D44
A9-B92-C10-D44
A13-B92-C10-D44
A24-B92-C10-D44
A69-B92-C10-D44
A67-B92-C10-D44
A39-B92-C10-D44
A65-B92-C10-D44
A66-B92-C10-D44
A2-B4-C11-D44
A3-B4-C11-D44
A9-B4-C11-D44

-continued
A13-B4-C11-D44
A24-B4-C11-D44
A69-B4-C11-D44
A67-B4-C11-D44
A39-B4-C11-D44
A65-B4-C11-D44
A66-B4-C11-D44
A2-B5-C11-D44
A3-B5-C11-D44
A9-B5-C11-D44
A13-B5-C11-D44
A24-B5-C11-D44
A69-B5-C11-D44
A67-B5-C11-D44
A39-B5-C11-D44
A65-B5-C11-D44
A66-B5-C11-D44
A2-B6-C11-D44
A3-B6-C11-D44
A9-B6-C11-D44
A13-B6-C11-D44
A24-B6-C11-D44
A69-B6-C11-D44
A67-B6-C11-D44
A39-B6-C11-D44
A65-B6-C11-D44
A66-B6-C11-D44
A2-B32-C11-D44
A3-B32-C11-D44
A9-B32-C11-D44
A13-B32-C11-D44
A24-B32-C11-D44
A69-B32-C11-D44
A67-B32-C11-D44
A39-B32-C11-D44
A65-B32-C11-D44
A66-B32-C11-D44
A2-B39-C11-D44
A3-B39-C11-D44
A9-B39-C11-D44
A13-B39-C11-D44
A24-B39-C11-D44
A69-B39-C11-D44
A67-B39-C11-D44
A39-B39-C11-D44
A65-B39-C11-D44
A66-B39-C11-D44
A2-B45-C11-D44
A3-B45-C11-D44
A9-B45-C11-D44
A13-B45-C11-D44
A24-B45-C11-D44
A69-B45-C11-D44
A67-B45-C11-D44
A39-B45-C11-D44
A65-B45-C11-D44
A66-B45-C11-D44
A2-B53-C11-D44
A3-B53-C11-D44
A9-B53-C11-D44
A13-B53-C11-D44
A24-B53-C11-D44
A69-B53-C11-D44
A67-B53-C11-D44
A39-B53-C11-D44
A65-B53-C11-D44
A66-B53-C11-D44
A2-B79-C11-D44
A3-B79-C11-D44
A9-B79-C11-D44
A13-B79-C11-D44
A24-B79-C11-D44
A69-B79-C11-D44
A67-B79-C11-D44
A39-B79-C11-D44
A65-B79-C11-D44
A66-B79-C11-D44
A2-B80-C11-D44
A3-B80-C11-D44
A9-B80-C11-D44

-continued

A13-B80-C11-D44
A24-B80-C11-D44
A69-B80-C11-D44
A67-B80-C11-D44
A39-B80-C11-D44
A65-B80-C11-D44
A66-B80-C11-D44
A2-B85-C11-D44
A3-B85-C11-D44
A9-B85-C11-D44
A13-B85-C11-D44
A24-B85-C11-D44
A69-B85-C11-D44
A67-B85-C11-D44
A39-B85-C11-D44
A65-B85-C11-D44
A66-B85-C11-D44
A2-B86-C11-D44
A3-B86-C11-D44
A9-B86-C11-D44
A13-B86-C11-D44
A24-B86-C11-D44
A69-B86-C11-D44
A67-B86-C11-D44
A39-B86-C11-D44
A65-B86-C11-D44
A66-B86-C11-D44
A2-B87-C11-D44
A3-B87-C11-D44
A9-B87-C11-D44
A13-B87-C11-D44
A24-B87-C11-D44
A69-B87-C11-D44
A67-B87-C11-D44
A39-B87-C11-D44
A65-B87-C11-D44
A66-B87-C11-D44
A2-B89-C11-D44
A3-B89-C11-D44
A9-B89-C11-D44
A13-B89-C11-D44
A24-B89-C11-D44
A69-B89-C11-D44
A67-B89-C11-D44
A39-B89-C11-D44
A65-B89-C11-D44
A66-B89-C11-D44
A2-B92-C11-D44
A3-B92-C11-D44
A9-B92-C11-D44
A13-B92-C11-D44
A24-B92-C11-D44
A69-B92-C11-D44
A67-B92-C11-D44
A39-B92-C11-D44
A65-B92-C11-D44
A66-B92-C11-D44
A2-B4-C12-D44
A3-B4-C12-D44
A9-B4-C12-D44
A13-B4-C12-D44
A24-B4-C12-D44
A69-B4-C12-D44
A67-B4-C12-D44
A39-B4-C12-D44
A65-B4-C12-D44
A66-B4-C12-D44
A2-B5-C12-D44
A3-B5-C12-D44
A9-B5-C12-D44
A13-B5-C12-D44
A24-B5-C12-D44
A69-B5-C12-D44
A67-B5-C12-D44
A39-B5-C12-D44
A65-B5-C12-D44
A66-B5-C12-D44
A2-B6-C12-D44
A3-B6-C12-D44
A9-B6-C12-D44

-continued

A13-B6-C12-D44
A24-B6-C12-D44
A69-B6-C12-D44
A67-B6-C12-D44
A39-B6-C12-D44
A65-B6-C12-D44
A66-B6-C12-D44
A2-B32-C12-D44
A3-B32-C12-D44
A9-B32-C12-D44
A13-B32-C12-D44
A24-B32-C12-D44
A69-B32-C12-D44
A67-B32-C12-D44
A39-B32-C12-D44
A65-B32-C12-D44
A66-B32-C12-D44
A2-B39-C12-D44
A3-B39-C12-D44
A9-B39-C12-D44
A13-B39-C12-D44
A24-B39-C12-D44
A69-B39-C12-D44
A67-B39-C12-D44
A39-B39-C12-D44
A65-B39-C12-D44
A66-B39-C12-D44
A2-B45-C12-D44
A3-B45-C12-D44
A9-B45-C12-D44
A13-B45-C12-D44
A24-B45-C12-D44
A69-B45-C12-D44
A67-B45-C12-D44
A39-B45-C12-D44
A65-B45-C12-D44
A66-B45-C12-D44
A2-B53-C12-D44
A3-B53-C12-D44
A9-B53-C12-D44
A13-B53-C12-D44
A24-B53-C12-D44
A69-B53-C12-D44
A67-B53-C12-D44
A39-B53-C12-D44
A65-B53-C12-D44
A66-B53-C12-D44
A2-B79-C12-D44
A3-B79-C12-D44
A9-B79-C12-D44
A13-B79-C12-D44
A24-B79-C12-D44
A69-B79-C12-D44
A67-B79-C12-D44
A39-B79-C12-D44
A65-B79-C12-D44
A66-B79-C12-D44
A2-B80-C12-D44
A3-B80-C12-D44
A9-B80-C12-D44
A13-B80-C12-D44
A24-B80-C12-D44
A69-B80-C12-D44
A67-B80-C12-D44
A39-B80-C12-D44
A65-B80-C12-D44
A66-B80-C12-D44
A2-B85-C12-D44
A3-B85-C12-D44
A9-B85-C12-D44
A13-B85-C12-D44
A24-B85-C12-D44
A69-B85-C12-D44
A67-B85-C12-D44
A39-B85-C12-D44
A65-B85-C12-D44
A66-B85-C12-D44
A2-B86-C12-D44
A3-B86-C12-D44
A9-B86-C12-D44

-continued

A13-B86-C12-D44
A24-B86-C12-D44
A69-B86-C12-D44
A67-B86-C12-D44
A39-B86-C12-D44
A65-B86-C12-D44
A66-B86-C12-D44
A2-B87-C12-D44
A3-B87-C12-D44
A9-B87-C12-D44
A13-B87-C12-D44
A24-B87-C12-D44
A69-B87-C12-D44
A67-B87-C12-D44
A39-B87-C12-D44
A65-B87-C12-D44
A66-B87-C12-D44
A2-B89-C12-D44
A3-B89-C12-D44
A9-B89-C12-D44
A13-B89-C12-D44
A24-B89-C12-D44
A69-B89-C12-D44
A67-B89-C12-D44
A39-B89-C12-D44
A65-B89-C12-D44
A66-B89-C12-D44
A2-B92-C12-D44
A3-B92-C12-D44
A9-B92-C12-D44
A13-B92-C12-D44
A24-B92-C12-D44
A69-B92-C12-D44
A67-B92-C12-D44
A39-B92-C12-D44
A65-B92-C12-D44
A66-B92-C12-D44
A2-B4-C13-D44
A3-B4-C13-D44
A9-B4-C13-D44
A13-B4-C13-D44
A24-B4-C13-D44
A69-B4-C13-D44
A67-B4-C13-D44
A39-B4-C13-D44
A65-B4-C13-D44
A66-B4-C13-D44
A2-B5-C13-D44
A3-B5-C13-D44
A9-B5-C13-D44
A13-B5-C13-D44
A24-B5-C13-D44
A69-B5-C13-D44
A67-B5-C13-D44
A39-B5-C13-D44
A65-B5-C13-D44
A66-B5-C13-D44
A2-B6-C13-D44
A3-B6-C13-D44
A9-B6-C13-D44
A13-B6-C13-D44
A24-B6-C13-D44
A69-B6-C13-D44
A67-B6-C13-D44
A39-B6-C13-D44
A65-B6-C13-D44
A66-B6-C13-D44
A2-B32-C13-D44
A3-B32-C13-D44
A9-B32-C13-D44
A13-B32-C13-D44
A24-B32-C13-D44
A69-B32-C13-D44
A67-B32-C13-D44
A39-B32-C13-D44
A65-B32-C13-D44
A66-B32-C13-D44
A2-B39-C13-D44
A3-B39-C13-D44
A9-B39-C13-D44

-continued

A13-B39-C13-D44
A24-B39-C13-D44
A69-B39-C13-D44
A67-B39-C13-D44
A39-B39-C13-D44
A65-B39-C13-D44
A66-B39-C13-D44
A2-B45-C13-D44
A3-B45-C13-D44
A9-B45-C13-D44
A13-B45-C13-D44
A24-B45-C13-D44
A69-B45-C13-D44
A67-B45-C13-D44
A39-B45-C13-D44
A65-B45-C13-D44
A66-B45-C13-D44
A2-B53-C13-D44
A3-B53-C13-D44
A9-B53-C13-D44
A13-B53-C13-D44
A24-B53-C13-D44
A69-B53-C13-D44
A67-B53-C13-D44
A39-B53-C13-D44
A65-B53-C13-D44
A66-B53-C13-D44
A2-B79-C13-D44
A3-B79-C13-D44
A9-B79-C13-D44
A13-B79-C13-D44
A24-B79-C13-D44
A69-B79-C13-D44
A67-B79-C13-D44
A39-B79-C13-D44
A65-B79-C13-D44
A66-B79-C13-D44
A2-B80-C13-D44
A3-B80-C13-D44
A9-B80-C13-D44
A13-B80-C13-D44
A24-B80-C13-D44
A69-B80-C13-D44
A67-B80-C13-D44
A39-B80-C13-D44
A65-B80-C13-D44
A66-B80-C13-D44
A2-B85-C13-D44
A3-B85-C13-D44
A9-B85-C13-D44
A13-B85-C13-D44
A24-B85-C13-D44
A69-B85-C13-D44
A67-B85-C13-D44
A39-B85-C13-D44
A65-B85-C13-D44
A66-B85-C13-D44
A2-B86-C13-D44
A3-B86-C13-D44
A9-B86-C13-D44
A13-B86-C13-D44
A24-B86-C13-D44
A69-B86-C13-D44
A67-B86-C13-D44
A39-B86-C13-D44
A65-B86-C13-D44
A66-B86-C13-D44
A2-B87-C13-D44
A3-B87-C13-D44
A9-B87-C13-D44
A13-B87-C13-D44
A24-B87-C13-D44
A69-B87-C13-D44
A67-B87-C13-D44
A39-B87-C13-D44
A65-B87-C13-D44
A66-B87-C13-D44
A2-B89-C13-D44
A3-B89-C13-D44
A9-B89-C13-D44

-continued

A13-B89-C13-D44
A24-B89-C13-D44
A69-B89-C13-D44
A67-B89-C13-D44
A39-B89-C13-D44
A65-B89-C13-D44
A66-B89-C13-D44
A2-B92-C13-D44
A3-B92-C13-D44
A9-B92-C13-D44
A13-B92-C13-D44
A24-B92-C13-D44
A69-B92-C13-D44
A67-B92-C13-D44
A39-B92-C13-D44
A65-B92-C13-D44
A66-B92-C13-D44
A2-B4-C1-D45
A3-B4-C1-D45
A9-B4-C1-D45
A13-B4-C1-D45
A24-B4-C1-D45
A69-B4-C1-D45
A67-B4-C1-D45
A39-B4-C1-D45
A65-B4-C1-D45
A66-B4-C1-D45
A2-B5-C1-D45
A3-B5-C1-D45
A9-B5-C1-D45
A13-B5-C1-D45
A24-B5-C1-D45
A69-B5-C1-D45
A67-B5-C1-D45
A39-B5-C1-D45
A65-B5-C1-D45
A66-B5-C1-D45
A2-B6-C1-D45
A3-B6-C1-D45
A9-B6-C1-D45
A13-B6-C1-D45
A24-B6-C1-D45
A69-B6-C1-D45
A67-B6-C1-D45
A39-B6-C1-D45
A65-B6-C1-D45
A66-B6-C1-D45
A2-B32-C1-D45
A3-B32-C1-D45
A9-B32-C1-D45
A13-B32-C1-D45
A24-B32-C1-D45
A69-B32-C1-D45
A67-B32-C1-D45
A39-B32-C1-D45
A65-B32-C1-D45
A66-B32-C1-D45
A2-B39-C1-D45
A3-B39-C1-D45
A9-B39-C1-D45
A13-B39-C1-D45
A24-B39-C1-D45
A69-B39-C1-D45
A67-B39-C1-D45
A39-B39-C1-D45
A65-B39-C1-D45
A66-B39-C1-D45
A2-B45-C1-D45
A3-B45-C1-D45
A9-B45-C1-D45
A13-B45-C1-D45
A24-B45-C1-D45
A69-B45-C1-D45
A67-B45-C1-D45
A39-B45-C1-D45
A65-B45-C1-D45
A66-B45-C1-D45
A2-B53-C1-D45
A3-B53-C1-D45
A9-B53-C1-D45

-continued

A13-B53-C1-D45
A24-B53-C1-D45
A69-B53-C1-D45
A67-B53-C1-D45
A39-B53-C1-D45
A65-B53-C1-D45
A66-B53-C1-D45
A2-B79-C1-D45
A3-B79-C1-D457
A9-B79-C1-D45
A13-B79-C1-D45
A24-B79-C1-D45
A69-B79-C1-D45
A67-B79-C1-D45
A39-B79-C1-D45
A65-B79-C1-D45
A66-B79-C1-D45
A2-B80-C1-D45
A3-B80-C1-D45
A9-B80-C1-D45
A13-B80-C1-D45
A24-B80-C1-D45
A69-B80-C1-D45
A67-B80-C1-D45
A39-B80-C1-D45
A65-B80-C1-D45
A66-B80-C1-D45
A2-B85-C1-D45
A3-B85-C1-D45
A9-B85-C1-D45
A13-B85-C1-D45
A24-B85-C1-D45
A69-B85-C1-D45
A67-B85-C1-D45
A39-B85-C1-D45
A65-B85-C1-D45
A66-B85-C1-D45
A2-B86-C1-D45
A3-B86-C1-D45
A9-B86-C1-D45
A13-B86-C1-D45
A24-B86-C1-D45
A69-B86-C1-D45
A67-B86-C1-D45
A39-B86-C1-D45
A65-B86-C1-D45
A66-B86-C1-D45
A2-B87-C1-D45
A3-B87-C1-D45
A9-B87-C1-D45
A13-B87-C1-D45
A24-B87-C1-D45
A69-B87-C1-D45
A67-B87-C1-D45
A39-B87-C1-D45
A65-B87-C1-D45
A66-B87-C1-D45
A2-B89-C1-D45
A3-B89-C1-D45
A9-B89-C1-D45
A13-B89-C1-D45
A24-B89-C1-D45
A69-B89-C1-D45
A67-B89-C1-D45
A39-B89-C1-D45
A65-B89-C1-D45
A66-B89-C1-D45
A2-B92-C1-D45
A3-B92-C1-D45
A9-B92-C1-D45
A13-B92-C1-D45
A24-B92-C1-D45
A69-B92-C1-D45
A67-B92-C1-D45
A39-B92-C1-D45
A65-B92-C1-D45
A66-B92-C1-D45
A2-B4-C2-D45
A3-B4-C2-D45
A9-B4-C2-D45

-continued

A13-B4-C2-D45
A24-B4-C2-D45
A69-B4-C2-D45
A67-B4-C2-D45
A39-B4-C2-D45
A65-B4-C2-D45
A66-B4-C2-D45
A2-B5-C2-D45
A3-B5-C2-D45
A9-B5-C2-D45
A13-B5-C2-D45
A24-B5-C2-D45
A69-B5-C2-D45
A67-B5-C2-D45
A39-B5-C2-D45
A65-B5-C2-D45
A66-B5-C2-D45
A2-B6-C2-D45
A3-B6-C2-D45
A9-B6-C2-D45
A13-B6-C2-D45
A24-B6-C2-D45
A69-B6-C2-D45
A67-B6-C2-D45
A39-B6-C2-D45
A65-B6-C2-D45
A66-B6-C2-D45
A2-B32-C2-D45
A3-B32-C2-D45
A9-B32-C2-D45
A13-B32-C2-D45
A24-B32-C2-D45
A69-B32-C2-D45
A67-B32-C2-D45
A39-B32-C2-D45
A65-B32-C2-D45
A66-B32-C2-D45
A2-B39-C2-D45
A3-B39-C2-D45
A9-B39-C2-D45
A13-B39-C2-D45
A24-B39-C2-D45
A69-B39-C2-D45
A67-B39-C2-D45
A39-B39-C2-D45
A65-B39-C2-D45
A66-B39-C2-D45
A2-B45-C2-D45
A3-B45-C2-D45
A9-B45-C2-D45
A13-B45-C2-D45
A24-B45-C2-D45
A69-B45-C2-D45
A67-B45-C2-D45
A39-B45-C2-D45
A65-B45-C2-D45
A66-B45-C2-D45
A2-B53-C2-D45
A3-B53-C2-D45
A9-B53-C2-D45
A13-B53-C2-D45
A24-B53-C2-D45
A69-B53-C2-D45
A67-B53-C2-D45
A39-B53-C2-D45
A65-B53-C2-D45
A66-B53-C2-D45
A2-B79-C2-D45
A3-B79-C2-D45
A9-B79-C2-D45
A13-B79-C2-D45
A24-B79-C2-D45
A69-B79-C2-D45
A67-B79-C2-D45
A39-B79-C2-D45
A65-B79-C2-D45
A66-B79-C2-D45
A2-B80-C2-D45
A3-B80-C2-D45
A9-B80-C2-D45

-continued

A13-B80-C2-D45
A24-B80-C2-D45
A69-B80-C2-D45
A67-B80-C2-D45
A39-B80-C2-D45
A65-B80-C2-D45
A66-B80-C2-D45
A2-B85-C2-D45
A3-B85-C2-D45
A9-B85-C2-D45
A13-B85-C2-D45
A24-B85-C2-D45
A69-B85-C2-D45
A67-B85-C2-D45
A39-B85-C2-D45
A65-B85-C2-D45
A66-B85-C2-D45
A2-B86-C2-D45
A3-B86-C2-D45
A9-B86-C2-D45
A13-B86-C2-D45
A24-B86-C2-D45
A69-B86-C2-D45
A67-B86-C2-D45
A39-B86-C2-D45
A65-B86-C2-D45
A66-B86-C2-D45
A2-B87-C2-D45
A3-B87-C2-D45
A9-B87-C2-D45
A13-B87-C2-D45
A24-B87-C2-D45
A69-B87-C2-D45
A67-B87-C2-D45
A39-B87-C2-D45
A65-B87-C2-D45
A66-B87-C2-D45
A2-B89-C2-D45
A3-B89-C2-D45
A9-B89-C2-D45
A13-B89-C2-D45
A24-B89-C2-D45
A69-B89-C2-D45
A67-B89-C2-D45
A39-B89-C2-D45
A65-B89-C2-D45
A66-B89-C2-D45
A2-B92-C2-D45
A3-B92-C2-D45
A9-B92-C2-D45
A13-B92-C2-D45
A24-B92-C2-D45
A69-B92-C2-D45
A67-B92-C2-D45
A39-B92-C2-D45
A65-B92-C2-D45
A66-B92-C2-D45
A2-B4-C3-D45
A3-B4-C3-D45
A9-B4-C3-D45
A13-B4-C3-D45
A24-B4-C3-D45
A69-B4-C3-D45
A67-B4-C3-D45
A39-B4-C3-D45
A65-B4-C3-D45
A66-B4-C3-D45
A2-B5-C3-D45
A3-B5-C3-D45
A9-B5-C3-D45
A13-B5-C3-D45
A24-B5-C3-D45
A69-B5-C3-D45
A67-B5-C3-D45
A39-B5-C3-D45
A65-B5-C3-D45
A66-B5-C3-D45
A2-B6-C3-D45
A3-B6-C3-D45
A9-B6-C3-D45

-continued

A13-B6-C3-D45
A24-B6-C3-D45
A69-B6-C3-D45
A67-B6-C3-D45
A39-B6-C3-D45
A65-B6-C3-D45
A66-B6-C3-D45
A2-B32-C3-D45
A3-B32-C3-D45
A9-B32-C3-D45
A13-B32-C3-D45
A24-B32-C3-D45
A69-B32-C3-D45
A67-B32-C3-D45
A39-B32-C3-D45
A65-B32-C3-D45
A66-B32-C3-D45
A2-B39-C3-D45
A3-B39-C3-D45
A9-B39-C3-D45
A13-B39-C3-D45
A24-B39-C3-D45
A69-B39-C3-D45
A67-B39-C3-D45
A39-B39-C3-D45
A65-B39-C3-D45
A66-B39-C3-D45
A2-B45-C3-D45
A3-B45-C3-D45
A9-B45-C3-D45
A13-B45-C3-D45
A24-B45-C3-D45
A69-B45-C3-D45
A67-B45-C3-D45
A39-B45-C3-D45
A65-B45-C3-D45
A66-B45-C3-D45
A2-B53-C3-D45
A3-B53-C3-D45
A9-B53-C3-D45
A13-B53-C3-D45
A24-B53-C3-D45
A69-B53-C3-D45
A67-B53-C3-D45
A39-B53-C3-D45
A65-B53-C3-D45
A66-B53-C3-D45
A2-B79-C3-D45
A3-B79-C3-D45
A9-B79-C3-D45
A13-B79-C3-D45
A24-B79-C3-D45
A69-B79-C3-D45
A67-B79-C3-D45
A39-B79-C3-D45
A65-B79-C3-D45
A66-B79-C3-D45
A2-B80-C3-D45
A3-B80-C3-D45
A9-B80-C3-D45
A13-B80-C3-D45
A24-B80-C3-D45
A69-B80-C3-D45
A67-B80-C3-D45
A39-B80-C3-D45
A65-B80-C3-D45
A66-B80-C3-D45
A2-B85-C3-D45
A3-B85-C3-D45
A9-B85-C3-D45
A13-B85-C3-D45
A24-B85-C3-D45
A69-B85-C3-D45
A67-B85-C3-D45
A39-B85-C3-D45
A65-B85-C3-D45
A66-B85-C3-D45
A2-B86-C3-D45
A3-B86-C3-D45
A9-B86-C3-D45

-continued

A13-B86-C3-D45
A24-B86-C3-D45
A69-B86-C3-D45
A67-B86-C3-D45
A39-B86-C3-D45
A65-B86-C3-D45
A66-B86-C3-D45
A2-B87-C3-D45
A3-B87-C3-D45
A9-B87-C3-D45
A13-B87-C3-D45
A24-B87-C3-D45
A69-B87-C3-D45
A67-B87-C3-D45
A39-B87-C3-D45
A65-B87-C3-D45
A66-B87-C3-D45
A2-B89-C3-D45
A3-B89-C3-D45
A9-B89-C3-D45
A13-B89-C3-D45
A24-B89-C3-D45
A69-B89-C3-D45
A67-B89-C3-D45
A39-B89-C3-D45
A65-B89-C3-D45
A66-B89-C3-D45
A2-B92-C3-D45
A3-B92-C3-D45
A9-B92-C3-D45
A13-B92-C3-D45
A24-B92-C3-D45
A69-B92-C3-D45
A67-B92-C3-D45
A39-B92-C3-D45
A65-B92-C3-D45
A66-B92-C3-D45
A2-B4-C4-D45
A3-B4-C4-D45
A9-B4-C4-D45
A13-B4-C4-D45
A24-B4-C4-D45
A69-B4-C4-D45
A67-B4-C4-D45
A39-B4-C4-D45
A65-B4-C4-D45
A66-B4-C4-D45
A2-B5-C4-D45
A3-B5-C4-D45
A9-B5-C4-D45
A13-B5-C4-D45
A24-B5-C4-D45
A69-B5-C4-D45
A67-B5-C4-D45
A39-B5-C4-D45
A65-B5-C4-D45
A66-B5-C4-D45
A2-B6-C4-D45
A3-B6-C4-D45
A9-B6-C4-D45
A13-B6-C4-D45
A24-B6-C4-D45
A69-B6-C4-D45
A67-B6-C4-D45
A39-B6-C4-D45
A65-B6-C4-D45
A66-B6-C4-D45
A2-B32-C4-D45
A3-B32-C4-D45
A9-B32-C4-D45
A13-B32-C4-D45
A24-B32-C4-D45
A69-B32-C4-D45
A67-B32-C4-D45
A39-B32-C4-D45
A65-B32-C4-D45
A66-B32-C4-D45
A2-B39-C4-D45
A3-B39-C4-D45
A9-B39-C4-D45

-continued

A13-B39-C4-D45
A24-B39-C4-D45
A69-B39-C4-D45
A67-B39-C4-D45
A39-B39-C4-D45
A65-B39-C4-D45
A66-B39-C4-D45
A2-B45-C4-D45
A3-B45-C4-D45
A9-B45-C4-D45
A13-B45-C4-D45
A24-B45-C4-D45
A69-B45-C4-D45
A67-B45-C4-D45
A39-B45-C4-D45
A65-B45-C4-D45
A66-B45-C4-D45
A2-B53-C4-D45
A3-B53-C4-D45
A9-B53-C4-D45
A13-B53-C4-D45
A24-B53-C4-D45
A69-B53-C4-D45
A67-B53-C4-D45
A39-B53-C4-D45
A65-B53-C4-D45
A66-B53-C4-D45
A2-B79-C4-D45
A3-B79-C4-D45
A9-B79-C4-D45
A13-B79-C4-D45
A24-B79-C4-D45
A69-B79-C4-D45
A67-B79-C4-D45
A39-B79-C4-D45
A65-B79-C4-D45
A66-B79-C4-D45
A2-B80-C4-D45
A3-B80-C4-D45
A9-B80-C4-D45
A13-B80-C4-D45
A24-B80-C4-D45
A69-B80-C4-D45
A67-B80-C4-D45
A39-B80-C4-D45
A65-B80-C4-D45
A66-B80-C4-D45
A2-B85-C4-D45
A3-B85-C4-D45
A9-B85-C4-D45
A13-B85-C4-D45
A24-B85-C4-D45
A69-B85-C4-D45
A67-B85-C4-D45
A39-B85-C4-D45
A65-B85-C4-D45
A66-B85-C4-D45
A2-B86-C4-D45
A3-B86-C4-D45
A9-B86-C4-D45
A13-B86-C4-D45
A24-B86-C4-D45
A69-B86-C4-D45
A67-B86-C4-D45
A39-B86-C4-D45
A65-B86-C4-D45
A66-B86-C4-D45
A2-B87-C4-D45
A3-B87-C4-D45
A9-B87-C4-D45
A13-B87-C4-D45
A24-B87-C4-D45
A69-B87-C4-D45
A67-B87-C4-D45
A39-B87-C4-D45
A65-B87-C4-D45
A66-B87-C4-D45
A2-B89-C4-D45
A3-B89-C4-D45
A9-B89-C4-D45

-continued

A13-B89-C4-D45
A24-B89-C4-D45
A69-B89-C4-D45
A67-B89-C4-D45
A39-B89-C4-D45
A65-B89-C4-D45
A66-B89-C4-D45
A2-B92-C4-D45
A3-B92-C4-D45
A9-B92-C4-D45
A13-B92-C4-D45
A24-B92-C4-D45
A69-B92-C4-D45
A67-B92-C4-D45
A39-B92-C4-D45
A65-B92-C4-D45
A66-B92-C4-D45
A2-B4-C5-D45
A3-B4-C5-D45
A9-B4-C5-D45
A13-B4-C5-D45
A24-B4-C5-D45
A69-B4-C5-D45
A67-B4-C5-D45
A39-B4-C5-D45
A65-B4-C5-D45
A66-B4-C5-D45
A2-B5-C5-D45
A3-B5-C5-D45
A9-B5-C5-D45
A13-B5-C5-D45
A24-B5-C5-D45
A69-B5-C5-D45
A67-B5-C5-D45
A39-B5-C5-D45
A65-B5-C5-D45
A66-B5-C5-D45
A2-B6-C5-D45
A3-B6-C5-D45
A9-B6-C5-D45
A13-B6-C5-D45
A24-B6-C5-D45
A69-B6-C5-D45
A67-B6-C5-D45
A39-B6-C5-D45
A65-B6-C5-D45
A66-B6-C5-D45
A2-B32-C5-D45
A3-B32-C5-D45
A9-B32-C5-D45
A13-B32-C5-D45
A24-B32-C5-D45
A69-B32-C5-D45
A67-B32-C5-D45
A39-B32-C5-D45
A65-B32-C5-D45
A66-B32-C5-D45
A2-B39-C5-D45
A3-B39-C5-D45
A9-B39-C5-D45
A13-B39-C5-D45
A24-B39-C5-D45
A69-B39-C5-D45
A67-B39-C5-D45
A39-B39-C5-D45
A65-B39-C5-D45
A66-B39-C5-D45
A2-B45-C5-D45
A3-B45-C5-D45
A9-B45-C5-D45
A13-B45-C5-D45
A24B45-C5-D45
A69-B45-C5-D45
A67-B45-C5-D45
A39-B45-C5-D45
A65-B45-C5-D45
A66-B45-C5-D45
A2-B53-C5-D45
A3-B53-C5-D45
A9-B53-C5-D45

-continued
A13-B53-C5-D45
A24-B53-C5-D45
A69-B53-C5-D45
A67-B53-C5-D45
A39-B53-C5-D45
A65-B53-C5-D45
A66-B53-C5-D45
A2-B79-C5-D45
A3-B79-C5-D45
A9-B79-C5-D45
A13-B79-C5-D45
A24-B79-C5-D45
A69-B79-C5-D45
A67-B79-C5-D45
A39-B79-C5-D45
A65-B79-C5-D45
A66-B79-C5-D45
A2-B80-C5-D45
A3-B80-C5-D45
A9-B80-C5-D45
A13-B80-C5-D45
A24-B80-C5-D45
A69-B80-C5-D45
A67-B80-C5-D45
A39-B80-C5-D45
A65-B80-C5-D45
A66-B80-C5-D45
A2-B85-C5-D45
A3-B85-C5-D45
A9-B85-C5-D45
A13-B85-C5-D45
A24-B85-C5-D45
A69-B85-C5-D45
A67-B85-C5-D45
A39-B85-C5-D45
A65-B85-C5-D45
A66-B85-C5-D45
A2-B86-C5-D45
A3-B86-C5-D45
A9-B86-C5-D45
A13-B86-C5-D45
A24-B86-C5-D45
A69-B86-C5-D45
A67-B86-C5-D45
A39-B86-C5-D45
A65-B86-C5-D45
A66-B86-C5-D45
A2-B87-C5-D45
A3-B87-C5-D45
A9-B87-C5-D45
A13-B87-C5-D45
A24-B87-C5-D45
A69-B87-C5-D45
A67-B87-C5-D45
A39-B87-C5-D45
A65-B87-C5-D45
A66-B87-C5-D45
A2-B89-C5-D45
A3-B89-C5-D45
A9-B89-C5-D45
A13-B89-C5-D45
A24-B89-C5-D45
A69-B89-C5-D45
A67-B89-C5-D45
A39-B89-C5-D45
A65-B89-C5-D45
A66-B89-C5-D45
A2-B92-C5-D45
A3-B92-C5-D45
A9-B92-C5-D45
A13-B92-C5-D45
A24-B92-C5-D45
A69-B92-C5-D45
A67-B92-C5-D45
A39-B92-C5-D45
A65-B92-C5-D45
A66-B92-C5-D45
A2-B4-C6-D45
A3-B4-C6-D45
A9-B4-C6-D45

-continued
A13-B4-C6-D45
A24-B4-C6-D45
A69-B4-C6-D45
A67-B4-C6-D45
A39-B4-C6-D45
A65-B4-C6-D45
A66-B4-C6-D45
A2-B5-C6-D45
A3-B5-C6-D45
A9-B5-C6-D45
A13-B5-C6-D45
A24-B5-C6-D45
A69-B5-C6-D45
A67-B5-C6-D45
A39-B5-C6-D45
A65-B5-C6-D45
A66-B5-C6-D45
A2-B6-C6-D45
A3-B6-C6-D45
A9-B6-C6-D45
A13-B6-C6-D45
A24-B6-C6-D45
A69-B6-C6-D45
A67-B6-C6-D45
A39-B6-C6-D45
A65-B6-C6-D45
A66-B6-C6-D45
A2-B32-C6-D45
A3-B32-C6-D457
A9-B32-C6-D45
A13-B32-C6-D45
A24-B32-C6-D45
A69-B32-C6-D45
A67-B32-C6-D45
A39-B32-C6-D45
A65-B32-C6-D45
A66-B32-C6-D45
A2-B39-C6-D45
DA3-B39-C6-D45
A9-B39-C6-D45
A13-B39-C6-D45
A24-B39-C6-D45
A69-B39-C6-D45
A67-B39-C6-D45
A39-B39-C6-D45
A65-B39-C6-D45
A66-B39-C6-D45
A2-B45-C6-D45
A3-B45-C6-D45
A9-B45-C6-D45
A13-B45-C6-D45
A24-B45-C6-D45
A69-B45-C6-D45
A67-B45-C6-D45
A39-B45-C6-D45
A65-B45-C6-D45
A66-B45-C6-D45
A2-B53-C6-D45
A3-B53-C6-D45
A9-B53-C6-D45
A13-B53-C6-D45
A24-B53-C6-D45
A69-B53-C6-D45
A67-B53-C6-D45
A39-B53-C6-D45
A65-B53-C6-D45
A66-B53-C6-D45
A2-B79-C6-D45
A3-B79-C6-D45
A9-B79-C6-D45
A13-B79-C6-D45
A24-B79-C6-D45
A69-B79-C6-D45
A67-B79-C6-D45
A39-B79-C6-D45
A65-B79-C6-D45
A66-B79-C6-D45
A2-B80-C6-D45
A3-B80-C6-D45
A9-B80-C6-D45

-continued
A13-B80-C6-D45
A24-B80-C6-D45
A69-B80-C6-D45
A67-B80-C6-D45
A39-B80-C6-D45
A65-B80-C6-D45
A66-B80-C6-D45
A2-B85-C6-D45
A3-B85-C6-D45
A9-B85-C6-D45
A13-B85-C6-D45
A24-B85-C6-D45
A69-B85-C6-D45
A67-B85-C6-D45
A39-B85-C6-D45
A65-B85-C6-D45
A66-B85-C6-D45
A2-B86-C6-D45
A3-B86-C6-D45
A9-B86-C6-D45
A13-B86-C6-D45
A24-B86-C6-D45
A69-B86-C6-D45
A67-B86-C6-D45
A39-B86-C6-D45
A65-B86-C6-D45
A66-B86-C6-D45
A2-B87-C6-D45
A3-B87-C6-D45
A9-B87-C6-D45
A13-B87-C6-D45
A24-B87-C6-D45
A69-B87-C6-D45
A67-B87-C6-D45
A39-B87-C6-D45
A65-B87-C6-D45
A66-B87-C6-D45
A2-B89-C6-D45
A3-B89-C6-D45
A9-B89-C6-D45
A13-B89-C6-D45
A24-B89-C6-D45
A69-B89-C6-D45
A67-B89-C6-D45
A39-B89-C6-D45
A65-B89-C6-D45
A66-B89-C6-D45
A2-B92-C6-D45
A3-B92-C6-D45
A9-B92-C6-D45
A13-B92-C6-D45
A24-B92-C6-D45
A69-B92-C6-D45
A67-B92-C6-D45
A39-B92-C6-D45
A65-B92-C6-D45
A66-B92-C6-D45
A2-B4-C7-D45
A3-B4-C7-D45
A9-B4-C7-D45
A13-B4-C7-D45
A24-B4-C7-D45
A69-B4-C7-D45
A67-B4-C7-D45
A39-B4-C7-D45
A65-B4-C7-D45
A66-B4-C7-D45
A2-B5-C7-D45
A3-B5-C7-D45
A9-B5-C7-D45
A13-B5-C7-D45
A24-B5-C7-D45
A69-B5-C7-D45
A67-B5-C7-D45
A39-B5-C7-D45
A65-B5-C7-D45
A66-B5-C7-D45
A2-B6-C7-D45
A3-B6-C7-D45
A9-B6-C7-D45

-continued
A13-B6-C7-D45
A24-B6-C7-D45
A69-B6-C7-D45
A67-B6-C7-D45
A39-B6-C7-D45
A65-B6-C7-D45
A66-B6-C7-D45
A2-B32-C7-D45
A3-B32-C7-D45
A9-B32-C7-D45
A13-B32-C7-D45
A24-B32-C7-D45
A69-B32-C7-D45
A67-B32-C7-D45
A39-B32-C7-D45
A65-B32-C7-D45
A66-B32-C7-D45
A2-B39-C7-D45
A3-B39-C7-D45
A9-B39-C7-D45
A13-B39-C7-D45
A24-B39-C7-D45
A69-B39-C7-D45
A67-B39-C7-D45
A39-B39-C7-D45
A65-B39-C7-D45
A66-B39-C7-D45
A2-B45-C7-D45
A3-B45-C7-D45
A9-B45-C7-D45
A13-B45-C7-D45
A24-B45-C7-D45
A69-B45-C7-D45
A67-B45-C7-D45
A39-B45-C7-D45
A65-B45-C7-D45
A66-B45-C7-D45
A2-B53-C7-D45
A3-B53-C7-D45
A9-B53-C7-D45
A13-B53-C7-D45
A24-B53-C7-D45
A69-B53-C7-D45
A67-B53-C7-D45
A39-B53-C7-D45
A65-B53-C7-D45
A66-B53-C7-D45
A2-B79-C7-D45
A3-B79-C7-D45
A9-B79-C7-D45
A13-B79-C7-D45
A24-B79-C7-D45
A69-B79-C7-D45
A67-B79-C7-D45
A39-B79-C7-D45
A65-B79-C7-D45
A66-B79-C7-D45
A2-B80-C7-D45
A3-B80-C7-D45
A9-B80-C7-D45
A13-B80-C7-D45
A24-B80-C7-D45
A69-B80-C7-D45
A67-B80-C7-D45
A39-B80-C7-D45
A65-B80-C7-D45
A66-B80-C7-D45
A2-B85-C7-D45
A3-B85-C7-D45
A9-B85-C7-D45
A13-B85-C7-D45
A24-B85-C7-D45
A69-B85-C7-D45
A67-B85-C7-D45
A39-B85-C7-D45
A65-B85-C7-D45
A66-B85-C7-D45
A2-B86-C7-D45
A3-B86-C7-D45
A9-B86-C7-D45

-continued
A13-B86-C7-D45
A24-B86-C7-D45
A69-B86-C7-D45
A67-B86-C7-D45
A39-B86-C7-D45
A65-B86-C7-D45
A66-B86-C7-D45
A2-B87-C7-D45
A3-B87-C7-D45
A9-B87-C7-D45
A13-B87-C7-D45
A24-B87-C7-D45
A69-B87-C7-D45
A67-B87-C7-D45
A39-B87-C7-D45
A65-B87-C7-D45
A66-B87-C7-D45
A2-B89-C7-D45
A3-B89-C7-D45
A9-B89-C7-D45
A13-B89-C7-D45
A24-B89-C7-D45
A69-B89-C7-D45
A67-B89-C7-D45
A39-B89-C7-D45
A65-B89-C7-D45
A66-B89-C7-D45
A2-B92-C7-D45
A3-B92-C7-D45
A9-B92-C7-D45
A13-B92-C7-D45
A24-B92-C7-D45
A69-B92-C7-D45
A67-B92-C7-D45
A39-B92-C7-D45
A65-B92-C7-D45
A66-B92-C7-D45
A2-B4-C8-D45
A3-B4-C8-D45
A9-B4-C8-D45
A13-B4-C8-D45
A24-B4-C8-D45
A69-B4-C8-D45
A67-B4-C8-D45
A39-B4-C8-D45
A65-B4-C8-D45
A66-B4-C8-D45
A2-B5-C8-D45
A3-B5-C8-D45
A9-B5-C8-D45
A13-B5-C8-D45
A24-B5-C8-D45
A69-B5-C8-D45
A67-B5-C8-D45
A39-B5-C8-D45
A65-B5-C8-D45
A66-B5-C8-D45
A2-B6-C8-D45
A3-B6-C8-D45
A9-B6-C8-D45
A13-B6-C8-D45
A24-B6-C8-D45
A69-B6-C8-D45
A67-B6-C8-D45
A39-B6-C8-D45
A65-B6-C8-D45
A66-B6-C8-D45
A2-B32-C8-D45
A3-B32-C8-D45
A9-B32-C8-D45
A13-B32-C8-D45
A24-B32-C8-D45
A69-B32-C8-D45
A67-B32-C8-D45
A39-B32-C8-D45
A65-B32-C8-D45
A66-B32-C8-D45
A2-B39-C8-D45
A3-B39-C8-D45
A9-B39-C8-D45

-continued
A13-B39-C8-D45
A24-B39-C8-D45
A69-B39-C8-D45
A67-B39-C8-D45
A39-B39-C8-D45
A65-B39-C8-D45
A66-B39-C8-D45
A2-B45-C8-D45
A3-B45-C8-D45
A9-B45-C8-D45
A13-B45-C8-D45
A24-B45-C8-D45
A69-B45-C8-D45
A67-B45-C8-D45
A39-B45-C8-D45
A65-B45-C8-D45
A66-B45-C8-D45
A2-B53-C8-D45
A3-B53-C8-D45
A9-B53-C8-D45
A13-B53-C8-D45
A24-B53-C8-D45
A69-B53-C8-D45
A67-B53-C8-D45
A39-B53-C8-D45
A65-B53-C8-D45
A66-B53-C8-D45
A2-B79-C8-D45
A3-B79-C8-D45
A9-B79-C8-D45
A13-B79-C8-D45
A24-B79-C8-D45
A69-B79-C8-D45
A67-B79-C8-D45
A39-B79-C8-D45
A65-B79-C8-D45
A66-B79-C8-D45
A2-B80-C8-D45
A3-B80-C8-D45
A9-B80-C8-D45
A13-B80-C8-D45
A24-B80-C8-D45
A69-B80-C8-D45
A67-B80-C8-D45
A39-B80-C8-D45
A65-B80-C8-D45
A66-B80-C8-D45
A2-B85-C8-D45
A3-B85-C8-D45
A9-B85-C8-D45
A13-B85-C8-D45
A24-B85-C8-D45
A69-B85-C8-D45
A67-B85-C8-D45
A39-B85-C8-D45
A65-B85-C8-D45
A66-B85-C8-D45
A2-B86-C8-D45
A3-B86-C8-D45
A9-B86-C8-D45
A13-B86-C8-D45
A24-B86-C8-D45
A69-B86-C8-D45
A67-B86-C8-D45
A39-B86-C8-D45
A65-B86-C8-D45
A66-B86-C8-D45
A2-B87-C8-D45
A3-B87-C8-D45
A9-B87-C8-D45
A13-B87-C8-D45
A24-B87-C8-D45
A69-B87-C8-D45
A67-B87-C8-D45
A39-B87-C8-D45
A65-B87-C8-D45
A66-B87-C8-D45
A2-B89-C8-D45
A3-B89-C8-D45
A9-B89-C8-D45

-continued
A13-B89-C8-D45
A24-B89-C8-D45
A69-B89-C8-D45
A67-B89-C8-D45
A39-B89-C8-D45
A65-B89-C8-D45
A66-B89-C8-D45
A2-B92-C8-D45
A3-B92-C8-O45
A9-B92-C8-D45
A13-B92-C8-D45
A24-B92-C8-D45
A69-B92-C8-D45
A67-B92-C8-D45
A39-B92-C8-D45
A65-B92-C8-D45
A66-B92-C8-D45
A2-B4-C9-D45
A3-B4-C9-D45
A9-B4-C9-D45
A13-B4-C9-D45
A24-B4-C9-D45
A69-B4-C9-D45
A67-B4-C9-D45
A39-B4-C9-D45
A65-B4-C9-D45
A66-B4-C9-D45
A2-B5-C9-D45
A3-B5-C9-D45
A9-B5-C9-D45
A13-B5-C9-D45
A24-B5-C9-D45
A69-B5-C9-D45
A67-B5-C9-D45
A39-B5-C9-D45
A65-B5-C9-D45
A66-B5-C9-D45
A2-B6-C9-D45
A3-B6-C9-D45
A9-B6-C9-D45
A13-B6-C9-D45
A24-B6-C9-D45
A69-B6-C9-D45
A67-B6-C9-D45
A39-B6-C9-D45
A65-B6-C9-D45
A66-B6-C9-D45
A2-B32-C9-D45
A3-B32-C9-D45
A9-B32-C9-D45
A13-B32-C9-D45
A24-B32-C9-D45
A69-B32-C9-D45
A67-B32-C9-D45
A39-B32-C9-D45
A65-B32-C9-D45
A66-B32-C9-D45
A2-B39-C9-D45
A3-B39-C9-D45
A9-B39-C9-D45
A13-B39-C9-D45
A24-B39-C9-D45
A69-B39-C9-D45
A67-B39-C9-D45
A39-B39-C9-D45
A65-B39-C9-D45
A66-B39-C9-D45
A2-B45-C9-D45
A3-B45-C9-D45
A9-B45-C9-D45
A13-B45-C9-D45
A24-B45-C9-D45
A69-B45-C9-D45
A67-B45-C9-D45
A39-B45-C9-D45
A65-B45-C9-D45
A66-B45-C9-D45
A2-B53-C9-D45
A3-B53-C9-D45
A9-B53-C9-D45

-continued
A13-B53-C9-D45
A24-B53-C9-D45
A69-B53-C9-D45
A67-B53-C9-D45
A39-B53-C9-D45
A65-B53-C9-D45
A66-B53-C9-D45
A2-B79-C9-D45
A3-B79-C9-D45
A9-B79-C9-D45
A13-B79-C9-D45
A24-B79-C9-D45
A69-B79-C9-D45
A67-B79-C9-D45
A39-B79-C9-D45
A65-B79-C9-D45
A66-B79-C9-D45
A2-B80-C9-D45
A3-B80-C9-D45
A9-B80-C9-D45
A13-B80-C9-D45
A24-B80-C9-D45
A69-B80-C9-D45
A67-B80-C9-D45
A39-B80-C9-D45
A65-B80-C9-D45
A66-B80-C9-D45
A2-B85-C9-D45
A3-B85-C9-D45
A9-B85-C9-D45
A13-B85-C9-D45
A24-B85-C9-D45
A69-B85-C9-D45
A67-B85-C9-D45
A39-B85-C9-D45
A65-B85-C9-D45
A66-B85-C9-D45
A2-B86-C9-D45
A3-B86-C9-D45
A9-B86-C9-D45
A13-B86-C9-D45
A24-B86-C9-D45
A69-B86-C9-D45
A67-B86-C9-D45
A39-B86-C9-D45
A65-B86-C9-D45
A66-B86-C9-D45
A2-B87-C9-D45
A3-B87-C9-D45
A9-B87-C9-D45
A13-B87-C9-D45
A24-B87-C9-D45
A69-B87-C9-D45
A67-B87-C9-D45
A39-B87-C9-D45
A65-B87-C9-D45
A66-B87-C9-D45
A2-B89-C9-D45
A3-B89-C9-D45
A9-B89-C9-D45
A13-B89-C9-D45
A24-B89-C9-D45
A69-B89-C9-D45
A67-B89-C9-D45
A39-B89-C9-D45
A65-B89-C9-D45
A66-B89-C9-D45
A2-B92-C9-D45
A3-B92-C9-D45
A9-B92-C9-D45
A13-B92-C9-D45
A24-B92-C9-D45
A69-B92-C9-D45
A67-B92-C9-D45
A39-B92-C9-D45
A65-B92-C9-D45
A66-B92-C9-D45
A2-B4-C10-D45
A3-B4-C10-D45
A9-B4-C10-D45

-continued

A13-B4-C10-D45
A24-B4-C10-D45
A69-B4-C10-D45
A67-B4-C10-D45
A39-B4-C10-D45
A65-B4-C10-D45
A66-B4-C10-D45
A2-B5-C10-D45
A3-B5-C10-D45
A9-B5-C10-D45
A13-B5-C10-D45
A24-B5-C10-D45
A69-B5-C10-D45
A67-B5-C10-D45
A39-B5-C10-D45
A65-B5-C10-D45
A66-B5-C10-D45
A2-B6-C10-D45
A3-B6-C10-D45
A9-B6-C10-D45
A13-B6-C10-D45
A24-B6-C10-D45
A69-B6-C10-D45
A67-B6-C10-D45
A39-B6-C10-D45
A65-B6-C10-D45
A66-B6-C10-D45
A2-B32-C10-D45
A3-B32-C10-D45
A9-B32-C10-D45
A13-B32-C10-D45
A24-B32-C10-D45
A69-B32-C10-D45
A67-B32-C10-D45
A39-B32-C10-D45
A65-B32-C10-D45
A66-B32-C10-D45
A2-B39-C10-D45
A3-B39-C10-D45
A9-B39-C10-D45
A13-B39-C10-D45
A24-B39-C10-D45
A69-B39-C10-D45
A67-B39-C10-D45
A39-B39-C10-D45
A65-B39-C10-D45
A66-B39-C10-D45
A2-B45-C10-D45
A3-B45-C10-D45
A9-B45-C10-D45
A13-B45-C10-D45
A24-B45-C10-D45
A69-B45-C10-D45
A67-B45-C10-D45
A39-B45-C10-D45
A65-B45-C10-D45
A66-B45-C10-D45
A2-B53-C10-D45
A3-B53-C10-D45
A9-B53-C10-D45
A13-B53-C10-D45
A24-B53-C10-D45
A69-B53-C10-D45
A67-B53-C10-D45
A39-B53-C10-D45
A65-B53-C10-D45
A66-B53-C10-D45
A2-B79-C10-D45
A3-B79-C10-D45
A9-B79-C10-D45
A13-B79-C10-D45
A24-B79-C10-D45
A69-B79-C10-D45
A67-B79-C10-D45
A39-B79-C10-D45
A65-B79-C10-D45
A66-B79-C10-D45
A2-B80-C10-D45
A3-B80-C10-D45
A9-B80-C10-D45

-continued

A13-B80-C10-D45
A24-B80-C10-D45
A69-B80-C10-D45
A67-B80-C10-D45
A39-B80-C10-D45
A65-B80-C10-D45
A66-B80-C10-D45
A2-B85-C10-D45
A3-B85-C10-D45
A9-B85-C10-D45
A13-B85-C10-D45
A24-B85-C10-D45
A69-B85-C10-D45
A67-B85-C10-D45
A39-B85-C10-D45
A65-B85-C10-D45
A66-B85-C10-D45
A2-B86-C10-D45
A3-B86-C10-D45
A9-B86-C10-D45
A13-B86-C10-D45
A24-B86-C10-D45
A69-B86-C10-D45
A67-B86-C10-D45
A39-B86-C10-D45
A65-B86-C10-D45
A66-B86-C10-D45
A2-B87-C10-D45
A3-B87-C10-D45
A13-B87-C10-D45
A24-B87-C10-D45
A69-B87-C10-D45
A67-B87-C10-D45
A39-B87-C10-D45
A65-B87-C10-D45
A66-B87-C10-D45
A2-B89-C10-D45
A3-B89-C10-D45
A9-B89-C10-D45
A13-B89-C10-D45
A24-B89-C10-D45
A69-B89-C10-D45
A67-B89-C10-D45
A39-B89-C10-D45
A65-B89-C10-D45
A66-B89-C10-D45
A2-B92-C10-D45
A3-B92-C10-D45
A9-B92-C10-D45
A13-B92-C10-D45
A24-B92-C10-D45
A69-B92-C10-D45
A67-B92-C10-D45
A39-B92-C10-D45
A65-B92-C10-D45
A66-B92-C10-D45
A2-B4-C11-D45
A3-B4-C11-D45
A9-B4-C11-D45
A13-B4-C11-D45
A24-B4-C11-D45
A69-B4-C11-D45
A67-B4-C11-D45
A39-B4-C11-D45
A65-B4-C11-D45
A66-B4-C11-D45
A2-B5-C11-D45
A3-B5-C11-D45
A9-B5-C11-D45
A13-B5-C11-D45
A24-B5-C11-D45
A69-B5-C11-D45
A67-B5-C11-D45
A39-B5-C11-D45
A65-B5-C11-D45
A66-B5-C11-D45
A2-B6-C11-D45
A3-B6-C11-D45
A9-B6-C11-D45
A13-B6-C11-D45

-continued
A24-B6-C11-D45
A69-B6-C11-D45
A67-B6-C11-D45
A65-B6-C11-D45
A66-B6-C11-D45
A2-B32-C11-D45
A3-B32-C11-D45
A9-B32-C11-D45
A13-B32-C11-D45
A24-B32-C11-D45
A69-B32-C11-D45
A67-B32-C11-D45
A39-B32-C11-D45
A65-B32-C11-D45
A66-B32-C11-D45
A2-B39-C11-D45
A3-B39-C11-D45
A9-B39-C11-D45
A13-B39-C11-D45
A24-B39-C11-D45
A69-B39-C11-D45
A67-B39-C11-D45
A39-B39-C11-D45
A65-B39-C11-D45
A66-B39-C11-D45
A2-B45-C11-D45
A3-B45-C11-D45
A9-B45-C11-D45
A13-B45-C11-D45
A24-B45-C11-D45
A69-B45-C11-D45
A67-B45-C11-D45
A39-B45-C11-D45
A65-B45-C11-D45
A66-B45-C11-D45
A2-B53-C11-D45
A3-B53-C11-D45
A9-B53-C11-D45
A13-B53-C11-D45
A24-B53-C11-D45
A69-B53-C11-D45
A67-B53-C11-D45
A39-B53-C11-D45
A65-B53-C11-D45
A66-B53-C11-D45
A2-B79-C11-D45
A3-B79-C11-D45
A9-B79-C11-D45
A13-B79-C11-D45
A24-B79-C11-D45
A69-B79-C11-D45
A67-B79-C11-D45
A39-B79-C11-D45
A65-B79-C11-D45
A66-B79-C11-D45
A2-B80-C11-D45
A3-B80-C11-D45
A13-B80-C11-D45
A24-B80-C11-D45
A69-B80-C11-D45
A67-B80-C11-D45
A39-B80-C11-D45
A65-B80-C11-D45
A66-B80-C11-D45
A2-B85-C11-D45
A3-B85-C11-D45
A9-B85-C11-D45
A13-B85-C11-D45
A24-B85-C11-D45
A69-B85-C11-D45
A67-B85-C11-D45
A39-B85-C11-D45
A65-B85-C11-D45
A66-B85-C11-D45
A2-B86-C11-D45
A3-B86-C11-D45
A9-B86-C11-D45
A13-B86-C11-D45
A24-B86-C11-D45
A69-B86-C11-D45

-continued
A67-B86-C11-D45
A39-B86-C11-D45
A65-B86-C11-D45
A66-B86-C11-D45
A2-B87-C11-D45
A3-B87-C11-D45
A9-B87-C11-D45
A13-B87-C11-D45
A24-B87-C11-D45
A69-B87-C11-D45
A67-B87-C11-D45
A39-B87-C11-D45
A65-B87-C11-D45
A66-B87-C11-D45
A2-B89-C11-D45
A3-B89-C11-D45
A9-B89-C11-D45
A13-B89-C11-D45
A24-B89-C11-D45
A69-B89-C11-D45
A67-B89-C11-D45
A39-B89-C11-D45
A65-B89-C11-D45
A66-B89-C11-D45
A2-B92-C11-D45
A3-B92-C11-D45
A9-B92-C11-D45
A13-B92-C11-D45
A24-B92-C11-D45
A69-B92-C11-D45
A67-B92-C11-D45
A65-B92-C11-D45
A66-B92-C11-D45
A2-B4-C12-D45
A3-B4-C12-D45
A9-B4-C12-D45
A13-B4-C12-D45
A24-B4-C12-D45
A69-B4-C12-D45
A67-B4-C12-D45
A39-B4-C12-D45
A65-B4-C12-D45
A66-B4-C12-D45
A2-B5-C12-D45
A3-B5-C12-D45
A9-B5-C12-D45
A13-B5-C12-D45
A24-B5-C12-D45
A69-B5-C12-D45
A67-B5-C12-D45
A39-B5-C12-D45
A65-B5-C12-D45
A66-B5-C12-D45
A2-B6-C12-D45
A3-B6-C12-D45
A9-B6-C12-D45
A13-B6-C12-D45
A24-B6-C12-D45
A69-B6-C12-D45
A67-B6-C12-D45
A39-B6-C12-D45
A65-B6-C12-D45
A66-B6-C12-D45
A2-B32-C12-D45
A3-B32-C12-D45
A9-B32-C12-D45
A13-B32-C12-D45
A24-B32-C12-D45
A69-B32-C12-D45
A67-B32-C12-D45
A39-B32-C12-D45
A65-B32-C12-D45
A66-B32-C12-D45
A2-B39-C12-D45
A3-B39-C12-D45
A9-B39-C12-D45
A13-B39-C12-D45
A24-B39-C12-D45
A69-B39-C12-D45
A67-B39-C12-D45

-continued

A39-B39-C12-D45
A65-B39-C12-D45
A66-B39-C12-D45
A2-B45-C12-D45
A3-B45-C12-D45
A9-B45-C12-D45
A13-B45-C12-D45
A24-B45-C12-D45
A69-B45-C12-D45
A67-B45-C12-D45
A39-B45-C12-D45
A65-B45-C12-D45
A66-B45-C12-D45
A2-B5 3-C12-D45
A3-B53-C12-D45
A9-B53-C12-D45
A13-B53-C12-D45
A24-B53-C12-D45
A69-B53-C12-D45
A67-B53-C12-D45
A39-B53-C12-D45
A65-B53-C12-D45
A66-B53-C12-D45
A2-B79-C12-D45
A3-B79-C12-D45
A9-B79-C12-D45
A13-B79-C12-D45
A24-B79-C12-D45
A69-B79-C12-D45
A67-B79-C12-D45
A39-B79-C12-D45
A65-B79-C12-D45
A66-B79-C12-D45
A2-B80-C12-D45
A3-B80-C12-D45
A9-B80-C12-D45
A13-B80-C12-D45
A24-B80-C12-D45
A69-B80-C12-D45
A67-B80-C12-D45
A39-B80-C12-D45
A65-B80-C12-D45
A66-B80-C12-D45
A2-B85-C12-D45
A3-B85-C12-D45
A9-B85-C12-D45
A13-B85-C12-D45
A24-B85-C12-D45
A69-B85-C12-D45
A67-B85-C12-D45
A39-B85-C12-D45
A65-B85-C12-D45
A66-B85-C12-D45
A2-B86-C12-D45
A3-B86-C12-D45
A9-B86-C12-D45
A13-B86-C12-D45
A24-B86-C12-D45
A69-B86-C12-D45
A67-B86-C12-D45
A39-B86-C12-D45
A65-B86-C12-D45
A66-B86-C12-D45
A2-B87-C12-D45
A3-B87-C12-D45
A9-B87-C12-D45
A13-B87-C12-D45
A24-B87-C12-D45
A69-B87-C12-D45
A67-B87-C12-D45
A39-B87-C12-D45
A65-B87-C12-D45
A66-B87-C12-D45
A2-B89-C12-D45
A3-B89-C12-D45
A9-B89-C12-D45
A13-B89-C12-D45
A24-B89-C12-D45
A69-B89-C12-D45
A67-B89-C12-D45

-continued

A39-B89-C12-D45
A65-B89-C12-D45
A66-B89-C12-D45
A2-B92-C12-D45
A3-B92-C12-D45
A9-B92-C12-D45
A13-B92-C12-D45
A24-B92-C12-D45
A69-B92-C12-D45
A67-B92-C12-D45
A39-B92-C12-D45
A65-B92-C12-D45
A66-B92-C12-D45
A2-B4-C13-D45
A3-B4-C13-D45
A9-B4-C13-D45
A13-B4-C13-D45
A24-B4-C13-D45
A69-B4-C13-D45
A67-B4-C13-D45
A39-B4-C13-D45
A65-B4-C13-D45
A66-B4-C13-D45
A2-B5-C13-D45
A3-B5-C13-D45
A9-B5-C13-D45
A13-B5-C13-D45
A24-B5-C13-D45
A69-B5-C13-D45
A67-B5-C13-D45
A39-B5-C13-D45
A65-B5-C13-D45
A66-B5-C13-D45
A2-B6-C13-D45
A3-B6-C13-D45
A9-B6-C13-D45
A13-B6-C13-D45
A24-B6-C13-D45
A69-B6-C13-D45
A67-B6-C13-D45
A39-B6-C13-D45
A65-B6-C13-D45
A66-B6-C13-D45
A2-B32-C13-D45
A3-B32-C13-D45
A9-B32-C13-D45
A13-B32-C13-D45
A24-B32-C13-D45
A69-B32-C13-D45
A67-B32-C13-D45
A39-B32-C13-D45
A65-B32-C13-D45
A66-B32-C13-D45
A2-B39-C13-D45
A3-B39-C13-D45
A9-B39-C13-D45
A13-B39-C13-D45
A24-B39-C13-D45
A69-B39-C13-D45
A67-B39-C13-D45
A39-B39-C13-D45
A65-B39-C13-D45
A66-B39-C13-D45
A2-B45-C13-D45
A3-B45-C13-D45
A9-B45-C13-D45
A13-B45-C13-D45
A24-B45-C13-D45
A69-B45-C13-D45
A67-B45-C13-D45
A39-B45-C13-D45
A65-B45-C13-D45
A66-B45-C13-D45
A2-B53-C13-D45
A3-B53-C13-D45
A9-B53-C13-D45
A13-B53-C13-D45
A24-B53-C13-D45
A69-B53-C13-D45
A67-B53-C13-D45

-continued

A39-B53-C13-D45
A65-B53-C13-D45
A66-B53-C13-D45
A2-B79-C13-D45
A3-B79-C13-D45
A9-B79-C13-D45
A13-B79-C13-D45
A24-B79-C13-D45
A69-B79-C13-D45
A67-B79-C13-D45
A39-B79-C13-D45
A65-B79-C13-D45
A66-B79-C13-D45
A2-B80-C13-D45
A3-B80-C13-D45
A9-B80-C13-D45
A13-B80-C13-D45
A24-B80-C13-D45
A69-B80-C13-D45
A67-B80-C13-D45
A39-B80-C13-D45
A65-B80-C13-D45
A66-B80-C13-D45
A2-B85-C13-D45
A3-B85-C13-D45
A9-B85-C13-D45
A13-B85-C13-D45
A24-B85-C13-D45
A69-B85-C13-D45
A67-B85-C13-D45
A39-B85-C13-D45
A65-B85-C13-D45
A66-B85-C13-D45
A2-B86-C13-D45
A3-B86-C13-D45
A9-B86-C13-D45
A13-B86-C13-D45
A24-B86-C13-D45
A69-B86-C13-D45
A67-B86-C13-D45
A39-B86-C13-D45
A65-B86-C13-D45
A66-B86-C13-D45
A2-B87-C13-D45
A3-B87-C13-D45
A9-B87-C13-D45
A13-B87-C13-D45
A24-B87-C13-D45
A69-B87-C13-D45
A67-B87-C13-D45
A39-B87-C13-D45
A65-B87-C13-D45
A66-B87-C13-D45
A2-B89-C13-D45
A3-B89-C13-D45
A9-B89-C13-D45
A13-B89-C13-D45
A24-B89-C13-D45
A69-B89-C13-D45
A67-B89-C13-D45
A39-B89-C13-D45
A65-B89-C13-D45
A66-B89-C13-D45
A2-B92-C13-D45
A3-B92-C13-D45
A9-B92-C13-D45
A13-B92-C13-D45
A24-B92-C13-D45
A69-B92-C13-D45
A67-B92-C13-D45
A39-B92-C13-D45
A65-B92-C13-D45
A66-B92-C13-D45
A2-B4-C1-D46
A3-B4-C1-D46
A9-B4-C1-D46
A13-B4-C1-D46
A24-B4-C1-D46
A69-B4-C1-D46
A67-B4-C1-D46

-continued

A39-B4-C1-D46
A65-B4-C1-D46
A66-B4-C1-D46
A2-B5-C1-D46
A3-B5-C1-D46
A9-B5-C1-D46
A13-B5-C1-D46
A24-B5-C1-D46
A69-B5-C1-D46
A67-B5-C1-D46
A39-B5-C1-D46
A65-B5-C1-D46
A66-B5-C1-D46
A2-B6-C1-D46
A3-B6-C1-D46
A9-B6-C1-D46
A13-B6-C1-D46
A24-B6-C1-D46
A69-B6-C1-D46
A67-B6-C1-D46
A39-B6-C1-D46
A65-B6-C1-D46
A66-B6-C1-D46
A2-B32-C1-D46
A3-B32-C1-D46
A9-B32-C1-D46
A13-B32-C1-D46
A24-B32-C1-D46
A69-B32-C1-D46
A67-B32-C1-D46
A39-B32-C1-D46
A65-B32-C1-D46
A66-B32-C1-D46
A2-B39-C1-D46
A3-B39-C1-D46
A9-B39-C1-D46
A13-B39-C1-D46
A24-B39-C1-D46
A69-B39-C1-D46
A67-B39-C1-D46
A39-B39-C1-D46
A65-B39-C1-D46
A66-B39-C1-D46
A2-B45-C1-D46
A3-B45-C1-D46
A9-B45-C1-D46
A13-B45-C1-D46
A24-B45-C1-D46
A69-B45-C1-D46
A67-B45-C1-D46
A39-B45-C1-D46
A65-B45-C1-D46
A66-B45-C1-D46
A2-B53-C1-D46
A3-B53-C1-D46
A9-B53-C1-D46
A13-B53-C1-D46
A24-B53-C1-D46
A69-B53-C1-D46
A67-B53-C1-D46
A39-B53-C1-D46
A65-B53-C1-D46
A66-B53-C1-D46
A2-B79-C1-D46
A3-B79-C1-D46
A9-B79-C1-D46
A13-B79-C1-D46
A24-B79-C1-D46
A69-B79-C1-D46
A67-B79-C1-D46
A39-B79-C1-D46
A65-B79-C1-D46
A66-B79-C1-D46
A2-B80-C1-D46
A3-B80-C1-D46
A9-B80-C1-D46
A13-B80-C1-D46
A24-B80-C1-D46
A69-B80-C1-D46
A67-B80-C1-D46

-continued
A39-B80-C1-D46
A65-B80-C1-D46
A66-B80-C1-D46
A2-B85-C1-D46
A3-B85-C1-D46
A9-B85-C1-D46
A13-B85-C1-D46
A24-B85-C1-D46
A69-B85-C1-D46
A67-B85-C1-D46
A39-B85-C1-D46
A65-B85-C1-D46
A66-B85-C1-D46
A2-B86-C1-D46
A3-B86-C1-D46
A9-B86-C1-D46
A13-B86-C1-D46
A24-B86-C1-D46
A69-B86-C1-D46
A67-B86-C1-D46
A39-B86-C1-D46
A65-B86-C1-D46
A66-B86-C1-D46
A2-B87-C1-D46
A3-B87-C1-D46
A9-B87-C1-D46
A13-B87-C1-D46
A24-B87-C1-D46
A69-B87-C1-D46
A67-B87-C1-D46
A39-B87-C1-D46
A65-B87-C1-D46
A66-B87-C1-D46
A2-B89-C1-D46
A3-B89-C1-D46
A9-B89-C1-D46
A13-B89-C1-D46
A24-B89-C1-D46
A69-B89-C1-D46
A67-B89-C1-D46
A39-B89-C1-D46
A65-B89-C1-D46
A66-B89-C1-D46
A2-B92-C1-D46
A3-B92-C1-D46
A9-B92-C1-D46
A13-B92-C1-D46
A24-B92-C1-D46
A69-B92-C1-D46
A67-B92-C1-D46
A39-B92-C1-D46
A65-B92-C1-D46
A66-B92-C1-D46
A2-B4-C2-D46
A3-B4-C2-D46
A9-B4-C2-D46
A13-B4-C2-D46
A24-B4-C2-D46
A69-B4-C2-D46
A67-B4-C2-D46
A39-B4-C2-D46
A65-B4-C2-D46
A66-B4-C2-D46
A2-B5-C2-D46
A3-B5-C2-D46
A9-B5-C2-D46
A13-B5-C2-D46
A24-B5-C2-D46
A69-B5-C2-D46
A67-B5-C2-D46
A39-B5-C2-D46
A65-B5-C2-D46
A66-B5-C2-D46
A2-B6-C2-D46
A3-B6-C2-D46
A9-B6-C2-D46
A13-B6-C2-D46
A24-B6-C2-D46
A69-B6-C2-D46
A67-B6-C2-D46

-continued
A39-B6-C2-D46
A65-B6-C2-D46
A66-B6-C2-D46
A2-B32-C2-D46
A3-B32-C2-D46
A9-B32-C2-D46
A13-B32-C2-D46
A24-B32-C2-D46
A69-B32-C2-D46
A67-B32-C2-D46
A39-B32-C2-D46
A65-B32-C2-D46
A66-B32-C2-D46
A2-B39-C2-D46
A3-B39-C2-D46
A9-B39-C2-D46
A13-B39-C2-D46
A24-B39-C2-D46
A69-B39-C2-D46
A67-B39-C2-D46
A39-B39-C2-D46
A65-B39-C2-D46
A66-B39-C2-D46
A2-B45-C2-D46
A3-B45-C2-D46
A9-B45-C2-D46
A13-B45-C2-D46
A24-B45-C2-D46
A69-B45-C2-D46
A67-B45-C2-D46
A39-B45-C2-D46
A65-B45-C2-D46
A66-B45-C2-D46
A2-B53-C2-D46
A3-B53-C2-D46
A9-B53-C2-D46
A13-B53-C2-D46
A24-B53-C2-D46
A69-B53-C2-D46
A67-B53-C2-D46
A39-B53-C2-D46
A65-B53-C2-D46
A66-B53-C2-D46
A2-B79-C2-D46
A3-B79-C2-D46
A9-B79-C2-D46
A13-B79-C2-D46
A24-B79-C2-D46
A69-B79-C2-D46
A67-B79-C2-D46
A39-B79-C2-D46
A65-B79-C2-D46
A66-B79-C2-D46
A2-B80-C2-D46
A3-B80-C2-D46
A9-B80-C2-D46
A13-B80-C2-D46
A24-B80-C2-D46
A69-B80-C2-D46
A67-B80-C2-D46
A39-B80-C2-D46
A65-B80-C2-D46
A66-B80-C2-D46
A2-B85-C2-D46
A3-B85-C2-D46
A9-B85-C2-D46
A13-B85-C2-D46
A24-B85-C2-D46
A69-B85-C2-D46
A67-B85-C2-D46
A39-B85-C2-D46
A65-B85-C2-D46
A66-B85-C2-D46
A2-B86-C2-D46
A3-B86-C2-D46
A9-B86-C2-D46
A13-B86-C2-D46
A24-B86-C2-D46
A69-B86-C2-D46
A67-B86-C2-D46

-continued
A39-B86-C2-D46
A65-B86-C2-D46
A66-B86-C2-D46
A2-B87-C2-D46
A3-B87-C2-D46
A9-B87-C2-D46
A13-B87-C2-D46
A24-B87-C2-D46
A69-B87-C2-D46
A67-B87-C2-D46
A39-B87-C2-D46
A65-B87-C2-D46
A66-B87-C2-D46
A2-B89-C2-D46
A3-B89-C2-D46
A9-B89-C2-D46
A13-B89-C2-D46
A24-B89-C2-D46
A69-B89-C2-D46
A67-B89-C2-D46
A39-B89-C2-D46
A65-B89-C2-D46
A66-B89-C2-D46
A2-B92-C2-D46
A3-B92-C2-D46
A9-B92-C2-D46
A13-B92-C2-D46
A24-B92-C2-D46
A69-B92-C2-D46
A67-B92-C2-D46
A39-B92-C2-D46
A65-B92-C2-D46
A66-B92-C2-D46
A2-B4-C3-D46
A3-B4-C3-D46
A9-B4-C3-D46
A13-B4-C3-D46
A24-B4-C3-D46
A69-B4-C3-D46
A67-B4-C3-D46
A39-B4-C3-D46
A65-B4-C3-D46
A66-B4-C3-D46
A2-B5-C3-D46
A3-B5-C3-D46
A9-B5-C3-D46
A13-B5-C3-D46
A24-B5-C3-D46
A69-B5-C3-D46
A67-B5-C3-D46
A39-B5-C3-D46
A65-B5-C3-D46
A66-B5-C3-D46
A2-B6-C3-D46
A3-B6-C3-D46
A9-B6-C3-D46
A13-B6-C3-D46
A24-B6-C3-D46
A69-B6-C3-D46
A67-B6-C3-D46
A39-B6-C3-D46
A65-B6-C3-D46
A66-B6-C3-D46
A2-B32-C3-D46
A3-B32-C3-D46
A9-B32-C3-D46
A13-B32-C3-D46
A24-B32-C3-D46
A69-B32-C3-D46
A67-B32-C3-D46
A39-B32-C3-D46
A65-B32-C3-D46
A66-B32-C3-D46
A2-B39-C3-D46
A3-B39-C3-D46
A9-B39-C3-D46
A13-B39-C3-D46
A24-B39-C3-D46
A69-B39-C3-D46
A67-B39-C3-D46

-continued
A39-B39-C3-D46
A65-B39-C3-D46
A66-B39-C3-D46
A2-B45-C3-D46
A3-B45-C3-D46
A9-B45-C3-D46
A13-B45-C3-D46
A24-B45-C3-D46
A69-B45-C3-D46
A67-B45-C3-D46
A39-B45-C3-D46
A65-B45-C3-D46
A66-B45-C3-D46
A2-B53-C3-D46
A3-B53-C3-D46
A9-B53-C3-D46
A13-B53-C3-D46
A24-B53-C3-D46
A69-B53-C3-D46
A67-B53-C3-D46
A39-B53-C3-D46
A65-B53-C3-D46
A66-B53-C3-D46
A2-B79-C3-D46
A3-B79-C3-D46
A9-B79-C3-D46
A13-B79-C3-D46
A24-B79-C3-D46
A69-B79-C3-D46
A67-B79-C3-D46
A39-B79-C3-D46
A65-B79-C3-D46
A66-B79-C3-D46
A2-B80-C3-D46
A3-B80-C3-D46
A9-B80-C3-D46
A13-B80-C3-D46
A24-B80-C3-D46
A69-B80-C3-D46
A67-B80-C3-D46
A39-B80-C3-D46
A65-B80-C3-D46
A66-B80-C3-D46
A2-B85-C3-D46
A3-B85-C3-D46
A9-B85-C3-D46
A13-B85-C3-D46
A24-B85-C3-D46
A69-B85-C3-D46
A67-B85-C3-D46
A39-B85-C3-D46
A65-B85-C3-D46
A66-B85-C3-D46
A2-B86-C3-D46
A3-B86-C3-D46
A9-B86-C3-D46
A13-B86-C3-D46
A24-B86-C3-D46
A69-B86-C3-D46
A67-B86-C3-D46
A39-B86-C3-D46
A65-B86-C3-D46
A66-B86-C3-D46
A2-B87-C3-D46
A3-B87-C3-D46
A9-B87-C3-D46
A13-B87-C3-D46
A24-B87-C3-D46
A69-B87-C3-D46
A67-B87-C3-D46
A39-B87-C3-D46
A65-B87-C3-D46
A66-B87-C3-D46
A2-B89-C3-D46
A3-B89-C3-D46
A9-B89-C3-D46
A13-B89-C3-D46
A24-B89-C3-D46
A69-B89-C3-D46
A67-B89-C3-D46

-continued
A39-B89-C3-D46
A65-B89-C3-D46
A66-B89-C3-D46
A2-B92-C3-D46
A3-B92-C3-D46
A9-B92-C3-D46
A13-B92-C3-D46
A24-B92-C3-D46
A69-B92-C3-D46
A67-B92-C3-D46
A39-B92-C3-D46
A65-B92-C3-D46
A66-B92-C3-D46
A2-B4-C4-D46
A3-B4-C4-D46
A9-B4-C4-D46
A13-B4-C4-D46
A24-B4-C4-D46
A69-B4-C4-D46
A67-B4-C4-D46
A39-B4-C4-D46
A65-B4-C4-D46
A66-B4-C4-D46
A2-B5-C4-D46
A3-B5-C4-D46
A9-B5-C4-D46
A13-B5-C4-D46
A24-B5-C4-D46
A69-B5-C4-D46
A67-B5-C4-D46
A39-B5-C4-D46
A65-B5-C4-D46
A66-B5-C4-D46
A2-B6-C4-D46
A3-B6-C4-D46
A9-B6-C4-D46
A13-B6-C4-D46
A24-B6-C4-D46
A69-B6-C4-D46
A67-B6-C4-D46
A39-B6-C4-D46
A65-B6-C4-D46
A66-B6-C4-D46
A2-B32-C4-D46
A3-B32-C4-D46
A9-B32-C4-D46
A13-B32-C4-D46
A24-B32-C4-D46
A69-B32-C4-D46
A67-B32-C4-D46
A39-B32-C4-D46
A65-B32-C4-D46
A66-B32-C4-D46
A2-B39-C4-D46
A3-B39-C4-D46
A9-B39-C4-D46
A13-B39-C4-D46
A24-B39-C4-D46
A69-B39-C4-D46
A67-B39-C4-D46
A39-B39-C4-D46
A65-B39-C4-D46
A66-B39-C4-D46
A2-B45-C4-D46
A3-B45-C4-D46
A9-B45-C4-D46
A13-B45-C4-D46
A24-B45-C4-D46
A69-B45-C4-D46
A67-B45-C4-D46
A39-B45-C4-D46
A65-B45-C4-D46
A66-B45-C4-D46
A2-B53-C4-D46
A3-B53-C4-D46
A9-B53-C4-D46
A13-B53-C4-D46
A24-B53-C4-D46
A69-B53-C4-D46
A67-B53-C4-D46

-continued
A39-B53-C4-D46
A65-B53-C4-D46
A66-B53-C4-D46
A2-B79-C4-D46
A3-B79-C4-D46
A9-B79-C4-D46
A13-B79-C4-D46
A24-B79-C4-D46
A69-B79-C4-D46
A67-B79-C4-D46
A39-B79-C4-D46
A65-B79-C4-D46
A66-B79-C4-D46
A2-B80-C4-D46
A3-B80-C4-D46
A9-B80-C4-D46
A13-B80-C4-D46
A24-B80-C4-D46
A69-B80-C4-D46
A67-B80-C4-D46
A39-B80-C4-D46
A65-B80-C4-D46
A66-B80-C4-D46
A2-B85-C4-D46
A3-B85-C4-D46
A9-B85-C4-D46
A13-B85-C4-D46
A24-B85-C4-D46
A69-B85-C4-D46
A67-B85-C4-D46
A39-B85-C4-D46
A65-B85-C4-D46
A66-B85-C4-D46
A2-B86-C4-D46
A3-B86-C4-D46
A9-B86-C4-D46
A13-B86-C4-D46
A24-B86-C4-D46
A69-B86-C4-D46
A67-B86-C4-D46
A39-B86-C4-D46
A65-B86-C4-D46
A66-B86-C4-D46
A2-B87-C4-D46
A3-B87-C4-D46
A9-B87-C4-D46
A13-B87-C4-D46
A24-B87-C4-D46
A69-B87-C4-D46
A67-B87-C4-D46
A39-B87-C4-D46
A65-B87-C4-D46
A66-B87-C4-D46
A2-B89-C4-D46
A3-B89-C4-D46
A9-B89-C4-D46
A13-B89-C4-D46
A24-B89-C4-D46
A69-B89-C4-D46
A67-B89-C4-D46
A39-B89-C4-D46
A65-B89-C4-D46
A66-B89-C4-D46
A2-B92-C4-D46
A3-B92-C4-D46
A9-B92-C4-D46
A13-B92-C4-D46
A24-B92-C4-D46
A69-B92-C4-D46
A67-B92-C4-D46
A39-B92-C4-D46
A65-B92-C4-D46
A66-B92-C4-D46
A2-B4-C5-D46
A3-B4-C5-D46
A9-B4-C5-D46
A13-B4-C5-D46
A24-B4-C5-D46
A69-B4-C5-D46
A67-B4-C5-D46

-continued
A39-B4-C5-D46
A65-B4-C5-D46
A66-B4-C5-D46
A2-B5-C5-D46
A3-B5-C5-D46
A9-B5-C5-D46
A13-B5-C5-D46
A24-B5-C5-D46
A69-B5-C5-D46
A67-B5-C5-D46
A39-B5-C5-D46
A65-B5-C5-D46
A66-B5-C5-D46
A2-B6-C5-D46
A3-B6-C5-D46
A9-B6-C5-D46
A13-B6-C5-D46
A24-B6-C5-D46
A69-B6-C5-D46
A67-B6-C5-D46
A39-B6-C5-D46
A65-B6-C5-D46
A66-B6-C5-D46
A2-B32-C5-D46
A3-B32-C5-D46
A9-B32-C5-D46
A13-B32-C5-D46
A24-B32-C5-D46
A69-B32-C5-D46
A67-B32-C5-D46
A39-B32-C5-D46
A65-B32-C5-D46
A66-B32-C5-D46
A2-B39-C5-D46
A3-B39-C5-D46
A9-B39-C5-D46
A13-B39-C5-D46
A24-B39-C5-D46
A69-B39-C5-D46
A67-B39-C5-D46
A39-B39-C5-D46
A65-B39-C5-D46
A66-B39-C5-D46
A2-B45-C5-D46
A3-B45-C5-D46
A9-B45-C5-D46
A13-B45-C5-D46
A24-B45-C5-D46
A69-B45-C5-D46
A67-B45-C5-D46
A39-B45-C5-D46
A65-B45-C5-D46
A66-B45-C5-D46
A2-B53-C5-D46
A3-B53-C5-D46
A9-B53-C5-D46
A13-B53-C5-D46
A24-B53-C5-D46
A69-B53-C5-D46
A67-B53-C5-D46
A39-B53-C5-D46
A65-B53-C5-D46
A66-B53-C5-D46
A2-B79-C5-D46
A3-B79-C5-D46
A9-B79-C5-D46
A13-B79-C5-D46
A24-B79-C5-D46
A69-B79-C5-D46
A67-B79-C5-D46
A39-B79-C5-D46
A65-B79-C5-D46
A66-B79-C5-D46
A2-B80-C5-D46
A3-B80-C5-D46
A9-B80-C5-D46
A13-B80-C5-D46
A24-B80-C5-D46
A69-B80-C5-D46
A67-B80-C5-D46

-continued
A39-B80-C5-D46
A65-B80-C5-D46
A66-B80-C5-D46
A2-B85-C5-D46
A3-B85-C5-D46
A9-B85-C5-D46
A13-B85-C5-D46
A24-B85-C5-D46
A69-B85-C5-D46
A67-B85-C5-D46
A39-B85-C5-D46
A65-B85-C5-D46
A66-B85-C5-D46
A2-B86-C5-D46
A3-B86-C5-D46
A9-B86-C5-D46
A13-B86-C5-D46
A24-B86-C5-D46
A69-B86-C5-D46
A67-B86-C5-D46
A39-B86-C5-D46
A65-B86-C5-D46
A66-B86-C5-D46
A2-B87-C5-D46
A3-B87-C5-D46
A9-B87-C5-D46
A13-B87-C5-D46
A24-B87-C5-D46
A69-B87-C5-D46
A67-B87-C5-D46
A39-B87-C5-D46
A65-B87-C5-D46
A66-B87-C5-D46
A2-B89-C5-D46
A3-B89-C5-D46
A9-B89-C5-D46
A13-B89-C5-D46
A24-B89-C5-D46
A69-B89-C5-D46
A67-B89-C5-D46
A39-B89-C5-D46
A65-B89-C5-D46
A66-B89-C5-D46
A2-B92-C5-D46
A3-B92-C5-D46
A9-B92-C5-D46
A13-B92-C5-D46
A24-B92-C5-D46
A69-B92-C5-D46
A67-B92-C5-D46
A39-B92-C5-D46
A65-B92-C5-D46
A66-B92-C5-D46
A2-B4-C6-D46
A3-B4-C6-D46
A9-B4-C6-D46
A13-B4-C6-D46
A24-B4-C6-D46
A69-B4-C6-D46
A67-B4-C6-D46
A39-B4-C6-D46
A65-B4-C6-D46
A66-B4-C6-D46
A2-B5-C6-D46
A3-B5-C6-D46
A9-B5-C6-D46
A13-B5-C6-D46
A24-B5-C6-D46
A69-B5-C6-D46
A67-B5-C6-D46
A39-B5-C6-D46
A65-B5-C6-D46
A66-B5-C6-D46
A2-B6-C6-D46
A3-B6-C6-D46
A9-B6-C6-D46
A13-B6-C6-D46
A24-B6-C6-D46
A69-B6-C6-D46
A67-B6-C6-D46

-continued

A39-B6-C6-D46
A65-B6-C6-D46
A66-B6-C6-D46
A2-B32-C6-D46
A3-B32-C6-D46
A9-B32-C6-D46
A13-B32-C6-D46
A24-B32-C6-D46
A69-B32-C6-D46
A67-B32-C6-D46
A39-B32-C6-D46
A65-B32-C6-D46
A66-B32-C6-D46
A2-B39-C6-D46
A3-B39-C6-D46
A9-B39-C6-D46
A13-B39-C6-D46
A24-B39-C6-D46
A69-B39-C6-D46
A67-B39-C6-D46
A39-B39-C6-D46
A65-B39-C6-D46
A66-B39-C6-D46
A2-B45-C6-D46
A3-B45-C6-D46
A9-B45-C6-D46
A13-B45-C6-D46
A24-B45-C6-D46
A69-B45-C6-D46
A67-B45-C6-D46
A39-B45-C6-D46
A65-B45-C6-D46
A66-B45-C6-D46
A2-B53-C6-D46
A3-B53-C6-D46
A9-B53-C6-D46
A13-B53-C6-D46
A24-B53-C6-D46
A69-B53-C6-D46
A67-B53-C6-D46
A39-B53-C6-D46
A65-B53-C6-D46
A66-B53-C6-D46
A2-B79-C6-D46
A3-B79-C6-D46
A9-B79-C6-D46
A13-B79-C6-D46
A24-B79-C6-D46
A69-B79-C6-D46
A67-B79-C6-D46
A39-B79-C6-D46
A65-B79-C6-D46
A66-B79-C6-D46
A2-B80-C6-D46
A3-B80-C6-D46
A9-B80-C6-D46
A13-B80-C6-D46
A24-B80-C6-D46
A69-B80-C6-D46
A67-B80-C6-D46
A39-B80-C6-D46
A65-B80-C6-D46
A66-B80-C6-D46
A2-B85-C6-D46
A3-B85-C6-D46
A9-B85-C6-D46
A13-B85-C6-D46
A24-B85-C6-D46
A69-B85-C6-D46
A67-B85-C6-D46
A39-B85-C6-D46
A65-B85-C6-D46
A66-B85-C6-D46
A2-B86-C6-D46
A3-B86-C6-D46
A9-B86-C6-D46
A13-B86-C6-D46
A24-B86-C6-D46
A69-B86-C6-D46
A67-B86-C6-D46

-continued

A39-B86-C6-D46
A65-B86-C6-D46
A66-B86-C6-D46
A2-B87-C6-D46
A3-B87-C6-D46
A9-B87-C6-D46
A13-B87-C6-D46
A24-B87-C6-D46
A69-B87-C6-D46
A67-B87-C6-D46
A39-B87-C6-D46
A65-B87-C6-D46
A66-B87-C6-D46
A2-B89-C6-D46
A3-B89-C6-D46
A9-B89-C6-D46
A13-B89-C6-D46
A24-B89-C6-D46
A69-B89-C6-D46
A67-B89-C6-D46
A39-B89-C6-D46
A65-B89-C6-D46
A66-B89-C6-D46
A2-B92-C6-D46
A3-B92-C6-D46
A9-B92-C6-D46
A13-B92-C6-D46
A24-B92-C6-D46
A69-B92-C6-D46
A67-B92-C6-D46
A39-B92-C6-D46
A65-B92-C6-D46
A66-B92-C6-D46
A2-B4-C7-D46
A3-B4-C7-D46
A9-B4-C7-D46
A13-B4-C7-D46
A24-B4-C7-D46
A69-B4-C7-D46
A67-B4-C7-D46
A39-B4-C7-D46
A65-B4-C7-D46
A66-B4-C7-D46
A2-B5-C7-D46
A3-B5-C7-D46
A9-B5-C7-D46
A13-B5-C7-D46
A24-B5-C7-D46
A69-B5-C7-D46
A67-B5-C7-D46
A39-B5-C7-D46
A65-B5-C7-D46
A66-B5-C7-D46
A2-B6-C7-D46
A3-B6-C7-D46
A9-B6-C7-D46
A13-B6-C7-D46
A24-B6-C7-D46
A69-B6-C7-D46
A67-B6-C7-D46
A39-B6-C7-D46
A65-B6-C7-D46
A66-B6-C7-D46
A2-B32-C7-D46
A3-B32-C7-D46
A9-B32-C7-D46
A13-B32-C7-D46
A24-B32-C7-D46
A69-B32-C7-D46
A67-B32-C7-D46
A39-B32-C7-D46
A65-B32-C7-D46
A66-B32-C7-D46
A2-B39-C7-D46
A3-B39-C7-D46
A9-B39-C7-D46
A13-B39-C7-D46
A24-B39-C7-D46
A69-B39-C7-D46
A67-B39-C7-D46

-continued
A39-B39-C7-D46
A65-B39-C7-D46
A66-B39-C7-D46
A2-B45-C7-D46
A3-B45-C7-D46
A9-B45-C7-D46
A13-B45-C7-D46
A24-B45-C7-D46
A69-B45-C7-D46
A67-B45-C7-D46
A39-B45-C7-D46
A65-B45-C7-D46
A66-B45-C7-D46
A2-B53-C7-D46
A3-B53-C7-D46
A9-B53-C7-D46
A13-B53-C7-D46
A24-B53-C7-D46
A69-B53-C7-D46
A67-B53-C7-D46
A39-B53-C7-D46
A65-B53-C7-D46
A66-B53-C7-D46
A2-B79-C7-D46
A3-B79-C7-D46
A9-B79-C7-D46
A13-B79-C7-D46
A24-B79-C7-D46
A69-B79-C7-D46
A67-B79-C7-D46
A39-B79-C7-D46
A65-B79-C7-D46
A66-B79-C7-D46
A2-B80-C7-D46
A3-B80-C7-D46
A9-B80-C7-D46
A13-B80-C7-D46
A24-B80-C7-D46
A69-B80-C7-D46
A67-B80-C7-D46
A39-B80-C7-D46
A65-B80-C7-D46
A66-B80-C7-D46
A2-B85-C7-D46
A3-B85-C7-D46
A9-B85-C7-D46
A13-B85-C7-D46
A24-B85-C7-D46
A69-B85-C7-D46
A67-B85-C7-D46
A39-B85-C7-D46
A65-B85-C7-D46
A66-B85-C7-D46
A2-B86-C7-D46
A3-B86-C7-D46
A9-B86-C7-D46
A13-B86-C7-D46
A24-B86-C7-D46
A69-B86-C7-D46
67-B86-C7-D46
A39-B86-C7-D46
A65-B86-C7-D46
A66-B86-C7-D46
A2-B87-C7-D46
A3-B87-C7-D46
A9-B87-C7-D46
A13-B87-C7-D46
A24-B87-C7-D46
A69-B87-C7-D46
A67-B87-C7-D46
A39-B87-C7-D46
A65-B87-C7-D46
A66-B87-C7-D46
A2-B89-C7-D46
A3-B89-C7-D46
A9-B89-C7-D46
A13-B89-C7-D46
A24-B89-C7-D46
A69-B89-C7-D46
A67-B89-C7-D46

-continued
A39-B89-C7-D46
A65-B89-C7-D46
A66-B89-C7-D46
A2-B92-C7-D46
A3-B92-C7-D46
A9-B92-C7-D46
A13-B92-C7-D46
A24-B92-C7-D46
A69-B92-C7-D46
A67-B92-C7-D46
A39-B92-C7-D46
A65-B92-C7-D46
A66-B92-C7-D46
A2-B4-C8-D46
A3-B4-C8-D46
A9-B4-C8-D46
A13-B4-C8-D46
A24-B4-C8-D46
A69-B4-C8-D46
A67-B4-C8-D46
A39-B4-C8-D46
A65-B4-C8-D46
A66-B4-C8-D46
A2-B5-C8-D46
A3-B5-C8-D46
A9-B5-C8-D46
A13-B5-C8-D46
A24-B5-C8-D46
A69-B5-C8-D46
A67-B5-C8-D46
A39-B5-C8-D46
A65-B5-C8-D46
A66-B5-C8-D46
A2-B6-C8-D46
A3-B6-C8-D46
A9-B6-C8-D46
A13-B6-C8-D46
A24-B6-C8-D46
A69-B6-C8-D46
A67-B6-C8-D46
A39-B6-C8-D46
A65-B6-C8-D46
A66-B6-C8-D46
A2-B32-C8-D46
A3-B32-C8-D46
A9-B32-C8-D46
A13-B32-C8-D46
A24-B32-C8-D46
A69-B32-C8-D46
A67-B32-C8-D46
A39-B32-C8-D46
A65-B32-C8-D46
A66-B32-C8-D46
A2-B39-C8-D46
A3-B39-C8-D46
A9-B39-C8-D46
A13-B39-C8-D46
A24-B39-C8-D46
A69-B39-C8-D46
A67-B39-C8-D46
A39-B39-C8-D46
A65-B39-C8-D46
A66-B39-C8-D46
A2-B45-C8-D46
A3-B45-C8-D46
A9-B45-C8-D46
A13-B45-C8-D46
A24-B45-C8-D46
A69-B45-C8-D46
A67-B45-C8-D46
A39-B45-C8-D46
A65-B45-C8-D46
A66-B45-C8-D46
A2-B53-C8-D46
A3-B53-C8-D46
A9-B53-C8-D46
A13-B53-C8-D46
A24-B53-C8-D46
A69-B53-C8-D46
A67-B53-C8-D46

-continued
A39-B53-C8-D46
A65-B53-C8-D46
A66-B53-C8-D46
A2-B79-C8-D46
A3-B79-C8-D46
A9-B79-C8-D46
A13-B79-C8-D46
A24-B79-C8-D46
A69-B79-C8-D46
A67-B79-C8-D46
A39-B79-C8-D46
A65-B79-C8-D46
A66-B79-C8-D46
A2-B80-C8-D46
A3-B80-C8-D46
A9-B80-C8-D46
A13-B80-C8-D46
A24-B80-C8-D46
A69-B80-C8-D46
A67-B80-C8-D46
A39-B80-C8-D46
A65-B80-C8-D46
A66-B80-C8-D46
A2-B85-C8-D46
A3-B85-C8-D46
A9-B85-C8-D46
A13-B85-C8-D46
A24-B85-C8-D46
A69-B85-C8-D46
A67-B85-C8-D46
A39-B85-C8-D46
A65-B85-C8-D46
A66-B85-C8-D46
A2-B86-C8-D46
A3-B86-C8-D46
A9-B86-C8-D46
A13-B86-C8-D46
A24-B86-C8-D46
A69-B86-C8-D46
A67-B86-C8-D46
A39-B86-C8-D46
A65-B86-C8-D46
A66-B86-C8-D46
A2-B87-C8-D46
A3-B87-C8-D46
A9-B87-C8-D46
A13-B87-C8-D46
A24-B87-C8-D46
A69-B87-C8-D46
A67-B87-C8-D46
A39-B87-C8-D46
A65-B87-C8-D46
A66-B87-C8-D46
A2-B89-C8-D46
A3-B89-C8-D46
A9-B89-C8-D46
A13-B89-C8-D46
A24-B89-C8-D46
A69-B89-C8-D46
A67-B89-C8-D46
A39-B89-C8-D46
A65-B89-C8-D46
A66-B89-C8-D46
A2-B92-C8-D46
A3-B92-C8-D467
A9-B92-C8-D46
A13-B92-C8-D46
A24-B92-C8-D46
A69-B92-C8-D46
A67-B92-C8-D46
A39-B92-C8-D46
A65-B92-C8-D46
A66-B92-C8-D46
A2-B4-C9-D46
A3-B4-C9-D46
A9-B4-C9-D46
A13-B4-C9-D46
A24-B4-C9-D46
A69-B4-C9-D46
A67-B4-C9-D46

-continued
A39-B4-C9-D46
A65-B4-C9-D46
A66-B4-C9-D46
A2-B5-C9-D46
A3-B5-C9-D46
A9-B5-C9-D46
A13-B5-C9-D46
A24-B5-C9-D46
A69-B5-C9-D46
A67-B5-C9-D46
A39-B5-C9-D46
A65-B5-C9-D46
A66-B5-C9-D46
A2-B6-C9-D46
A3-B6-C9-D46
A9-B6-C9-D46
A13-B6-C9-D46
A24-B6-C9-D46
A69-B6-C9-D46
A67-B6-C9-D46
A39-B6-C9-D46
A65-B6-C9-D46
A66-B6-C9-D46
A2-B32-C9-D46
A3-B32-C9-D46
A9-B32-C9-D46
A13-B32-C9-D46
A24-B32-C9-D46
A69-B32-C9-D46
A67-B32-C9-D46
A39-B32-C9-D46
A65-B32-C9-D46
A66-B32-C9-D46
A2-B39-C9-D46
A3-B39-C9-D46
A9-B39-C9-D46
A13-B39-C9-D46
A24-B39-C9-D46
A69-B39-C9-D46
A67-B39-C9-D46
A39-B39-C9-D46
A65-B39-C9-D46
A66-B39-C9-D46
A2-B45-C9-D46
A3-B45-C9-D46
A9-B45-C9-D46
A13-B45-C9-D46
A24-B45-C9-D46
A69-B45-C9-D46
A67-B45-C9-D46
A39-B45-C9-D46
A65-B45-C9-D46
A66-B45-C9-D46
A2-B53-C9-D46
A3-B53-C9-D46
A9-B53-C9-D46
A13-B53-C9-D46
A24-B53-C9-D46
A69-B53-C9-D46
A67-B53-C9-D46
A39-B53-C9-D46
A65-B53-C9-D46
A66-B53-C9-D46
A2-B79-C9-D46
A3-B79-C9-D46
A9-B79-C9-D46
A13-B79-C9-D46
A24-B79-C9-D46
A69-B79-C9-D46
A67-B79-C9-D46
A39-B79-C9-D46
A65-B79-C9-D46
A66-B79-C9-D46
A2-B80-C9-D46
A3-B80-C9-D46
A9-B80-C9-D46
A13-B80-C9-D46
A24-B80-C9-D46
A69-B80-C9-D46
A67-B80-C9-D46

-continued
A39-B80-C9-D46
A65-B80-C9-D46
A66-B80-C9-D46
A2-B85-C9-D46
A3-B85-C9-D46
A9-B85-C9-D46
A13-B85-C9-D46
A24-B85-C9-D46
A69-B85-C9-D46
A67-B85-C9-D46
A39-B85-C9-D46
A65-B85-C9-D46
A66-B85-C9-D46
A2-B86-C9-D46
A3-B86-C9-D46
A9-B86-C9-D46
A13-B86-C9-D46
A24-B86-C9-D46
A69-B86-C9-D46
A67-B86-C9-D46
A39-B86-C9-D46
A65-B86-C9-D46
A66-B86-C9-D46
A2-B87-C9-D46
A3-B87-C9-D46
A9-B87-C9-D46
A13-B87-C9-D46
A24-B87-C9-D46
A69-B87-C9-D46
A67-B87-C9-D46
A39-B87-C9-D46
A65-B87-C9-D46
A66-B87-C9-D46
A2-B89-C9-D46
A3-B89-C9-D46
A9-B89-C9-D46
A13-B89-C9-D46
A24-B89-C9-D46
A69-B89-C9-D46
A67-B89-C9-D46
A39-B89-C9-D46
A65-B89-C9-D46
A66-B89-C9-D46
A2-B92-C9-D46
A3-B92-C9-D46
A9-B92-C9-D46
A13-B92-C9-D46
A24-B92-C9-D46
A69-B92-C9-D46
A67-B92-C9-D46
A39-B92-C9-D46
A65-B92-C9-D46
A66-B92-C9-D46
A2-B4-C10-D46
A3-B4-C10-D46
A9-B4-C10-D46
A13-B4-C10-D46
A24-B4-C10-D46
A69-B4-C10-D46
A67-B4-C10-D46
A39-B4-C10-D46
A65-B4-C10-D46
A66-B4-C10-D46
A2-B5-C10-D46
A3-B5-C10-D46
A9-B5-C10-D46
A13-B5-C10-D46
A24-B5-C10-D46
A69-B5-C10-D46
A67-B5-C10-D46
A39-B5-C10-D46
A65-B5-C10-D46
A66-B5-C10-D46
A2-B6-C10-D46
A3-B6-C10-D46
A9-B6-C10-D46
A13-B6-C10-D46
A24-B6-C10-D46
A69-B6-C10-D46
A67-B6-C10-D46

-continued
A39-B6-C10-D46
A65-B6-C10-D46
A66-B6-C10-D46
A2-B32-C10-D46
A3-B32-C10-D46
A9-B32-C10-D46
A13-B32-C10-D46
A24-B32-C10-D46
A69-B32-C10-D46
A67-B32-C10-D46
A39-B32-C10-D46
A65-B32-C10-D46
A66-B32-C10-D46
A2-B39-C10-D46
A3-B39-C10-D46
A9-B39-C10-D46
A13-B39-C10-D46
A24-B39-C10-D46
A69-B39-C10-D46
A67-B39-C10-D46
A39-B39-C10-D46
A65-B39-C10-D46
A66-B39-C10-D46
A2-B45-C10-D46
A3-B45-C10-D46
A9-B45-C10-D46
A13-B45-C10-D46
A24-B45-C10-D46
A69-B45-C10-D46
A67-B45-C10-D46
A39-B45-C10-D46
A65-B45-C10-D46
A66-B45-C10-D46
A2-B53-C10-D46
A3-B53-C10-D46
A9-B53-C10-D46
A13-B53-C10-D46
A24-B53-C10-D46
A69-B53-C10-D46
A67-B53-C10-D46
A39-B53-C10-D46
A65-B53-C10-D46
A66-B53-C10-D46
A2-B79-C10-D46
A3-B79-C10-D46
A9-B79-C10-D46
A13-B79-C10-D46
A24-B79-C10-D46
A69-B79-C10-D46
A67-B79-C10-D46
A39-B79-C10-D46
A65-B79-C10-D46
A66-B79-C10-D46
A2-B80-C10-D46
A3-B80-C10-D46
A9-B80-C10-D46
A13-B80-C10-D46
A24-B80-C10-D46
A69-B80-C10-D46
A67-B80-C10-D46
A39-B80-C10-D46
A65-B80-C10-D46
A66-B80-C10-D46
A2-B85-C10-D46
A3-B85-C10-D46
A9-B85-C10-D46
A13-B85-C10-D46
A24-B85-C10-D46
A69-B85-C10-D46
A67-B85-C10-D46
A39-B85-C10-D46
A65-B85-C10-D46
A66-B85-C10-D46
A2-B86-C10-D46
A3-B86-C10-D46
A9-B86-C10-D46
A13-B86-C10-D46
A24-B86-C10-D46
A69-B86-C10-D46
A67-B86-C10-D46

-continued
A39-B86-C10-D46
A65-B86-C10-D46
A66-B86-C10-D46
A2-B87-C10-D46
A3-B87-C10-D46
A9-B87-C10-D46
A13-B87-C10-D46
A24-B87-C10-D46
A69-B87-C10-D46
A67-B87-C10-D46
A39-B87-C10-D46
A65-B87-C10-D46
A66-B87-C10-D46
A2-B89-C10-D46
A3-B89-C10-D46
A9-B89-C10-D46
A13-B89-C10-D46
A24-B89-C10-D46
A69-B89-C10-D46
A67-B89-C10-D46
A39-B89-C10-D46
A65-B89-C10-D46
A66-B89-C10-D46
A2-B92-C10-D46
A3-B92-C10-D46
A9-B92-C10-D46
A13-B92-C10-D46
A24-B92-C10-D46
A69-B92-C10-D46
A67-B92-C10-D46
A39-B92-C10-D46
A65-B92-C10-D46
A66-B92-C10-D46
A2-B4-C11-D46
A3-B4-C11-D46
A9-B4-C11-D46
A13-B4-C11-D46
A24-B4-C11-D46
A69-B4-C11-D46
A67-B4-C11-D46
A39-B4-C11-D46
A65-B4-C11-D46
A66-B4-C11-D46
A2-B5-C11-D46
A3-B5-C11-D46
A9-B5-C11-D46
A13-B5-C11-D46
A24-B5-C11-D46
A69-B5-C11-D46
A67-B5-C11-D46
A39-B5-C11-D46
A65-B5-C11-D46
A66-B5-C11-D46
A2-B6-C11-D46
A3-B6-C11-D46
A9-B6-C11-D46
A13-B6-C11-D46
A24-B6-C11-D46
A69-B6-C11-D46
A67-B6-C11-D46
A39-B6-C11-D46
A65-B6-C11-D46
A66-B6-C11-D46
A2-B32-C11-D46
A3-B32-C11-D46
A9-B32-C11-D46
A13-B32-C11-D46
A24-B32-C11-D46
A69-B32-C11-D46
A67-B32-C11-D46
A39-B32-C11-D46
A65-B32-C11-D46
A66-B32-C11-D46
A2-B39-C11-D46
A3-B39-C11-D46
A9-B39-C11-D46
A13-B39-C11-D46
A24-B39-C11-D46
A69-B39-C11-D46
A67-B39-CL1-D46

-continued
A39-B39-C11-D46
A65-B39-C11-D46
A66-B39-C11-D46
A2-B45-C11-D46
A3-B45-C11-D46
A9-B45-C11-D46
A13-B45-C11-D46
A24-B45-C11-D46
A69-B45-C11-D46
A67-B45-C11-D46
A39-B45-C11-D46
A65-B45-C11-D46
A66-B45-C11-D46
A2-B53-C11-D46
A3-B53-C11-D46
A9-B53-C11-D46
A13-B53-C11-D46
A24-B53-C11-D46
A69-B53-C11-D46
A67-B53-C11-D46
A39-B53-C11-D46
A65-B53-C11-D46
A66-B53-C11-D46
A2-B79-C11-D46
A3-B79-C11-D46
A9-B79-C11-D46
A13-B79-C11-D46
A24-B79-C11-D46
A69-B79-C11-D46
A67-B79-C11-D46
A39-B79-C11-D46
A65-B79-C11-D46
A66-B79-C11-D46
A2-B80-C11-D46
A3-B80-C11-D46
A9-B80-C11-D46
A13-B80-C11-D46
A24-B80-C11-D46
A69-B80-C11-D46
A67-B80-C11-D46
A39-B80-C11-D46
A65-B80-C11-D46
A66-B80-C11-D46
A2-B85-C11-D46
A3-B85-C11-D46
A9-B85-C11-D46
A13-B85-C11-D46
A24-B85-C11-D46
A69-B85-C11-D46
A67-B85-C11-D46
A39-B85-C11-D46
A65-B85-C11-D46
A66-B85-C11-D46
A2-B86-C11-D46
A3-B86-C11-D46
A9-B86-C11-D46
A13-B86-C11-D46
A24-B86-C11-D46
A69-B86-C11-D46
A67-B86-C11-D46
A39-B86-C11-D46
A65-B86-C11-D46
A66-B86-C11-D46
A2-B87-C11-D46
A3-B87-C11-D46
A9-B87-C11-D46
A13-B87-C11-D46
A24-B87-C11-D46
A69-B87-C11-D46
A67-B87-C11-D46
A39-B87-C11-D46
A65-B87-C11-D46
A66-B87-C11-D46
A2-B89-C11-D46
A3-B89-C11-D46
A9-B89-C11-D46
A13-B89-C11-D46
A24-B89-C11-D46
A69-B89-C11-D46
A67-B89-C11-D46

-continued
A39-B89-C11-D46
A65-B89-C11-D46
A66-B89-C11-D46
A2-B92-C11-D46
A3-B92-C11-D46
A9-B92-C11-D46
A13-B92-C11-D46
A24-B92-C11-D46
A69-B92-C11-D46
A67-B92-C11-D46
A39-B92-C11-D46
A65-B92-C11-D46
A66-B92-C11-D46
A2-B4-C12-D46
A3-B4-C12-D46
A9-B4-C12-D46
A13-B4-C12-D46
A24-B4-C12-D46
A69-B4-C12-D46
A67-B4-C12-D46
A39-B4-C12-D46
A65-B4-C12-D46
A66-B4-C12-D46
A2-B5-C12-D46
A3-B5-C12-D46
A9-B5-C12-D46
A13-B5-C12-D46
A24-B5-C12-D46
A69-B5-C12-D46
A67-B5-C12-D46
A39-B5-C12-D46
A65-B5-C12-D46
A66-B5-C12-D46
A2-B6-C12-D46
A3-B6-C12-D46
A9-B6-C12-D46
A13-B6-C12-D46
A24-B6-C12-D46
A69-B6-C12-D46
A67-B6-C12-D46
A39-B6-C12-D46
A65-B6-C12-D46
A66-B6-C12-D46
A2-B32-C12-D46
A3-B32-C12-D46
A9-B32-C12-D46
A13-B32-C12-D46
A24-B32-C12-D46
A69-B32-C12-D46
A67-B32-C12-D46
A39-B32-C12-D46
A65-B32-C12-D46
A66-B32-C12-D46
A2-B39-C12-D46
A3-B39-C12-D46
A9-B39-C12-D46
A13-B39-C12-D46
A24-B39-C12-D46
A69-B39-C12-D46
A67-B39-C12-D46
A39-B39-C12-D46
A65-B39-C12-D46
A66-B39-C12-D46
A2-B45-C12-D46
A3-B45-C12-D46
A9-B45-C12-D46
A13-B45-C12-D46
A24-B45-C12-D46
A69-B45-C12-D46
A67-B45-C12-D46
A39-B45-C12-D46
A65-B45-C12-D46
A66-B45-C12-D46
A2-B53-C12-D46
A3-B53-C12-D46
A9-B53-C12-D46
A13-B53-C12-D46
A24-B53-C12-D46
A69-B53-C12-D46
A67-B53-C12-D46

-continued
A39-B53-C12-D46
A65-B53-C12-D46
A66-B53-C12-D46
A2-B79-C12-D46
A3-B79-C12-D46
A9-B79-C12-D46
A13-B79-C12-D46
A24-B79-C12-D46
A69-B79-C12-D46
A67-B79-C12-D46
A39-B79-C12-D46
A65-B79-C12-D46
A66-B79-C12-D46
A2-B80-C12-D46
A3-B80-C12-D46
A9-B80-C12-D46
A13-B80-C12-D46
A24-B80-C12-D46
A69-B80-C12-D46
A67-B80-C12-D46
A39-B80-C12-D46
A65-B80-C12-D46
A66-B80-C12-D46
A2-B85-C12-D46
A3-B85-C12-D46
A9-B85-C12-D46
A13-B85-C12-D46
A24-B85-C12-D46
A69-B85-C12-D46
A67-B85-C12-D46
A39-B85-C12-D46
A65-B85-C12-D46
A66-B85-C12-D46
A2-B86-C12-D46
A3-B86-C12-D46
A9-B86-C12-D46
A13-B86-C12-D46
A24-B86-C12-D46
A69-B86-C12-D46
A67-B86-C12-D46
A39-B86-C12-D46
A65-B86-C12-D46
A66-B86-C12-D46
A2-B87-C12-D46
A3-B87-C12-D46
A9-B87-C12-D46
A13-B87-C12-D46
A24-B87-C12-D46
A69-B87-C12-D46
A67-B87-C12-D46
A39-B87-C12-D46
A65-B87-C12-D46
A66-B87-C12-D46
A2-B89-C12-D46
A3-B89-C12-D46
A9-B89-C12-D46
A13-B89-C12-D46
A24-B89-C12-D46
A69-B89-C12-D46
A67-B89-C12-D46
A39-B89-C12-D46
A65-B89-C12-D46
A66-B89-C12-D46
A2-B92-C12-D46
A3-B92-C12-D46
A9-B92-C12-D46
A13-B92-C12-D46
A24-B92-C12-D46
A69-B92-C12-D46
A67-B92-C12-D46
A39-B92-C12-D46
A65-B92-C12-D46
A66-B92-C12-D46
A2-B4-C13-D46
A3-B4-C13-D46
A9-B4-C13-D46
A13-B4-C13-D46
A24-B4-C13-D46
A69-B4-C13-D46
A67-B4-C13-D46

-continued
A39-B4-C13-D46
A65-B4-C13-D46
A66-B4-C13-D46
A2-B5-C13-D46
A3-B5-C13-D46
A9-B5-C13-D46
A13-B5-C13-D46
A24-B5-C13-D46
A69-B5-C13-D46
A67-B5-C13-D46
A39-B5-C13-D46
A65-B5-C13-D46
A66-B5-C13-D46
A2-B6-C13-D46
A3-B6-C13-D46
A9-B6-C13-D46
A13-B6-C13-D46
A24-B6-C13-D46
A69-B6-C13-D46
A67-B6-C13-D46
A39-B6-C13-D46
A65-B6-C13-D46
A66-B6-C13-D46
A2-B32-C13-D46
A3-B32-C13-D46
A9-B32-C13-D46
A13-B32-C13-D46
A24-B32-C13-D46
A69-B32-C13-D46
A67-B32-C13-D46
A39-B32-C13-D46
A65-B32-C13-D46
A66-B32-C13-D46
A2-B39-C13-D46
A3-B39-C13-D46
A9-B39-C13-D46
A13-B39-C13-D46
A24-B39-C13-D46
A69-B39-C13-D46
A67-B39-C13-D46
A39-B39-C13-D46
A65-B39-C13-D46
A66-B39-C13-D46
A2-B45-C13-D46
A3-B45-C13-D46
A9-B45-C13-D46
A13-B45-C13-D46
A24-B45-C13-D46
A69-B45-C13-D46
A67-B45-C13-D46
A39-B45-C13-D46
A65-B45-C13-D46
A66-B45-C13-D46
A2-B53-C13-D46
A3-B53-C13-D46
A9-B53-C13-D46
A13-B53-C13-D46
A24-B53-C13-D46
A69-B53-C13-D46
A67-B53-C13-D46
A39-B53-C13-D46
A65-B53-C13-D46
A66-B53-C13-D46
A2-B79-C13-D46
A3-B79-C13-D46
A9-B79-C13-D46
A13-B79-C13-D46
A24-B79-C13-D46
A69-B79-C13-D46
A67-B79-C13-D46
A39-B79-C13-D46
A65-B79-C13-D46
A66-B79-C13-D46
A2-B80-C13-D46
A3-B80-C13-D46
A9-B80-C13-D46
A13-B80-C13-D46
A24-B80-C13-D46
A69-B80-C13-D46
A67-B80-C13-D46

-continued
A39-B80-C13-D46
A65-B80-C13-D46
A66-B80-C13-D46
A2-B85-C13-D46
A3-B85-C13-D46
A9-B85-C13-D46
A13-B85-C13-D46
A24-B85-C13-D46
A69-B85-C13-D46
A67-B85-C13-D46
A39-B85-C13-D46
A65-B85-C13-D46
A66-B85-C13-D46
A2-B86-C13-D46
A3-B86-C13-D46
A9-B86-C13-D46
A13-B86-C13-D46
A24-B86-C13-D46
A69-B86-C13-D46
A67-B86-C13-D46
A39-B86-C13-D46
A65-B86-C13-D46
A66-B86-C13-D46
A2-B87-C13-D46
A3-B87-C13-D46
A9-B87-C13-D46
A13-B87-C13-D46
A24-B87-C13-D46
A69-B87-C13-D46
A67-B87-C13-D46
A39-B87-C13-D46
A65-B87-C13-D46
A66-B87-C13-D46
A2-B89-C13-D46
A3-B89-C13-D46
A9-B89-C13-D46
A13-B89-C13-D46
A24-B89-C13-D46
A69-B89-C13-D46
A67-B89-C13-D46
A39-B89-C13-D46
A65-B89-C13-D46
A66-B89-C13-D46
A2-B92-C13-D46
A3-B92-C13-D46
A9-B92-C13-D46
A13-B92-C13-D46
A24-B92-C13-D46
A69-B92-C13-D46
A67-B92-C13-D46
A39-B92-C13-D46
A65-B92-C13-D46
A66-B92-C13-D46
A2-B4-C1-D47
A3-B4-C1-D47
A9-B4-C1-D47
A13-B4-C1-D47
A24-B4-C1-D47
A69-B4-C1-D47
A67-B4-C1-D47
A39-B4-C1-D47
A65-B4-C1-D47
A66-B4-C1-D47
A2-B5-C1-D47
A3-B5-C1-D47
A9-B5-C1-D47
A13-B5-C1-D47
A24-B5-C1-D47
A69-B5-C1-D47
A67-B5-C1-D47
A39-B5-C1-D47
A65-B5-C1-D47
A66-B5-C1-D47
A2-B6-C1-D47
A3-B6-C1-D47
A9-B6-C1-D47
A13-B6-C1-D47
A24-B6-C1-D47
A69-B6-C1-D47
A67-B6-C1-D47

-continued
A39-B6-C1-D47
A65-B6-C1-D47
A66-B6-C1-D47
A2-B32-C1-D47
A3-B32-C1-D47
A9-B32-C1-D47
A13-B32-C1-D47
A24-B32-C1-D47
A69-B32-C1-D47
A67-B32-C1-D47
A39-B32-C1-D47
A65-B32-C1-D47
A66-B32-C1-D47
A2-B39-C1-D47
A3-B39-C1-D47
A9-B39-C1-D47
A13-B39-C1-D47
A24-B39-C1-D47
A69-B39-C1-D47
A67-B39-C1-D47
A39-B39-C1-D47
A65-B39-C1-D47
A66-B39-C1-D47
A2-B45-C1-D47
A3-B45-C1-D47
A9-B45-C1-D47
A13-B45-C1-D47
A24-B45-C1-D47
A69-B45-C1-D47
A67-B45-C1-D47
A39-B45-C1-D47
A65-B45-C1-D47
A66-B45-C1-D47
A2-B53-C1-D47
A3-B53-C1-D47
A9-B53-C1-D47
A13-B53-C1-D47
A24-B53-C1-D47
A69-B53-C1-D47
A67-B53-C1-D47
A39-B53-C1-D47
A65-B53-C1-D47
A66-B53-C1-D47
A2-B79-C1-D47
A3-B79-C1-D47
A9-B79-C1-D47
A13-B79-C1-D47
A24-B79-C1-D47
A69-B79-C1-D47
A67-B79-C1-D47
A39-B79-C1-D47
A65-B79-C1-D47
A66-B79-C1-D47
A2-B80-C1-D47
A3-B80-C1-D47
A9-B80-C1-D47
A13-B80-C1-D47
A24-B80-C1-D47
A69-B80-C1-D47
A67-B80-C1-D47
A39-B80-C1-D47
A65-B80-C1-D47
A66-B80-C1-D47
A2-B85-C1-D47
A3-B85-C1-D47
A9-B85-C1-D47
A13-B85-C1-D47
A24-B85-C1-D47
A69-B85-C1-D47
A67-B85-C1-D47
A39-B85-C1-D47
A65-B85-C1-D47
A66-B85-C1-D47
A2-B86-C1-D47
A3-B86-C1-D47
A9-B86-C1-D47
A13-B86-C1-D47
A24-B86-C1-D47
A69-B86-C1-D47
A67-B86-C1-D47

-continued
A39-B86-C1-D47
A65-B86-C1-D47
A66-B86-C1-D47
A2-B87-C1-D47
A3-B87-C1-D47
A9-B87-C1-D47
A13-B87-C1-D47
A24-B87-C1-D47
A69-B87-C1-D47
A67-B87-C1-D47
A39-B87-C1-D47
A65-B87-C1-D47
A66-B87-C1-D47
A2-B89-C1-D47
A3-B89-C1-D47
A9-B89-C1-D47
A13-B89-C1-D47
A24-B89-C1-D47
A69-B89-C1-D47
A67-B89-C1-D47
A39-B89-C1-D47
A65-B89-C1-D47
A66-B89-C1-D47
A2-B92-C1-D47
A3-B92-C1-D47
A9-B92-C1-D47
A13-B92-C1-D47
A24-B92-C1-D47
A69-B92-C1-D47
A67-B92-C1-D47
A39-B92-C1-D47
A65-B92-C1-D47
A66-B92-C1-D47
A2-B4-C2-D47
A3-B4-C2-D47
A9-B4-C2-D47
A13-B4-C2-D47
A24-B4-C2-D47
A69-B4-C2-D47
A67-B4-C2-D47
A39-B4-C2-D47
A65-B4-C2-D47
A66-B4-C2-D47
A2-B5-C2-D47
A3-B5-C2-D47
A9-B5-C2-D47
A13-B5-C2-D47
A24-B5-C2-D47
A69-B5-C2-D47
A67-B5-C2-D47
A39-B5-C2-D47
A65-B5-C2-D47
A66-B5-C2-D47
A2-B6-C2-D47
A3-B6-C2-D47
A9-B6-C2-D47
A13-B6-C2-D47
A24-B6-C2-D47
A69-B6-C2-D47
A67-B6-C2-D47
A39-B6-C2-D47
A65-B6-C2-D47
A66-B6-C2-D47
A2-B32-C2-D47
A3-B32-C2-D47
A9-B32-C2-D47
A13-B32-C2-D47
A24-B32-C2-D47
A69-B32-C2-D47
A67-B32-C2-D47
A39-B32-C2-D47
A65-B32-C2-D47
A66-B32-C2-D47
A2-B39-C2-D47
A3-B39-C2-D47
A9-B39-C2-D47
A13-B39-C2-D47
A24-B39-C2-D47
A69-B39-C2-D47
A67-B39-C2-D47

-continued
A39-B39-C2-D47
A65-B39-C2-D47
A66-B39-C2-D47
A2-B45-C2-D47
A3-B45-C2-D47
A9-B45-C2-D47
A13-B45-C2-D47
A24-B45-C2-D47
A69-B45-C2-D47
A67-B45-C2-D47
A39-B45-C2-D47
A65-B45-C2-D47
A66-B45-C2-D47
A2-B53-C2-D47
A3-B53-C2-D47
A9-B53-C2-D47
A13-B53-C2-D47
A24-B53-C2-D47
A69-B53-C2-D47
A67-B53-C2-D47
A39-B53-C2-D47
A65-B53-C2-D47
A66-B53-C2-D47
A2-B79-C2-D47
A3-B79-C2-D47
A9-B79-C2-D47
A13-B79-C2-D47
A24-B79-C2-D47
A69-B79-C2-D47
A67-B79-C2-D47
A39-B79-C2-D47
A65-B79-C2-D47
A66-B79-C2-D47
A2-B80-C2-D47
A3-B80-C2-D47
A9-B80-C2-D47
A13-B80-C2-D47
A24-B80-C2-D47
A69-B80-C2-D47
A67-B80-C2-D47
A39-B80-C2-D47
A65-B80-C2-D47
A66-B80-C2-D47
A2-B85-C2-D47
A3-B85-C2-D47
A9-B85-C2-D47
A13-B85-C2-D47
A24-B85-C2-D47
A69-B85-C2-D47
A67-B85-C2-D47
A39-B85-C2-D47
A65-B85-C2-D47
A66-B85-C2-D47
A2-B86-C2-D47
A3-B86-C2-D47
A9-B86-C2-D47
A13-B86-C2-D47
A24-B86-C2-D47
A69-B86-C2-D47
A67-B86-C2-D47
A39-B86-C2-D47
A65-B86-C2-D47
A66-B86-C2-D47
A2-B87-C2-D47
A3-B87-C2-D47
A9-B87-C2-D47
A13-B87-C2-D47
A24-B87-C2-D47
A69-B87-C2-D47
A67-B87-C2-D47
A39-B87-C2-D47
A65-B87-C2-D47
A66-B87-C2-D47
A2-B89-C2-D47
A3-B89-C2-D47
A9-B89-C2-D47
A13-B89-C2-D47
A24-B89-C2-D47
A69-B89-C2-D47
A67-B89-C2-D47

-continued
A39-B89-C2-D47
A65-B89-C2-D47
A66-B89-C2-D47
A2-B92-C2-D47
A3-B92-C2-D47
A9-B92-C2-D47
A13-B92-C2-D47
A24-B92-C2-D47
A69-B92-C2-D47
A67-B92-C2-D47
A39-B92-C2-D47
A65-B92-C2-D47
A66-B92-C2-D47
A2-B4-C3-D47
A3-B4-C3-D47
A9-B4-C3-D47
A13-B4-C3-D47
A24-B4-C3-D47
A69-B4-C3-D47
A67-B4-C3-D47
A39-B4-C3-D47
A65-B4-C3-D47
A66-B4-C3-D47
A2-B5-C3-D47
A3-B5-C3-D47
A9-B5-C3-D47
A13-B5-C3-D47
A24-B5-C3-D47
A69-B5-C3-D47
A67-B5-C3-D47
A39-B5-C3-D47
A65-B5-C3-D47
A66-B5-C3-D47
A2-B6-C3-D47
A3-B6-C3-D47
A9-B6-C3-D47
A13-B6-C3-D47
A24-B6-C3-D47
A69-B6-C3-D47
A67-B6-C3-D47
A39-B6-C3-D47
A65-B6-C3-D47
A66-B6-C3-D47
A2-B32-C3-D47
A3-B32-C3-D47
A9-B32-C3-D47
A13-B32-C3-D47
A24-B32-C3-D47
A69-B32-C3-D47
A67-B32-C3-D47
A39-B32-C3-D47
A65-B32-C3-D47
A66-B32-C3-D47
A2-B39-C3-D47
A3-B39-C3-D47
A9-B39-C3-D47
A13-B39-C3-D47
A24-B39-C3-D47
A69-B39-C3-D47
A67-B39-C3-D47
A39-B39-C3-D47
A65-B39-C3-D47
A66-B39-C3-D47
A2-B45-C3-D47
A3-B45-C3-D47
A9-B45-C3-D47
A13-B45-C3-D47
A24-B45-C3-D47
A69-B45-C3-D47
A67-B45-C3-D47
A39-B45-C3-D47
A65-B45-C3-D47
A66-B45-C3-D47
A2-B53-C3-D47
A3-B53-C3-D47
A9-B53-C3-D47
A13-B53-C3-D47
A24-B53-C3-D47
A69-B53-C3-D47
A67-B53-C3-D47

-continued

A39-B53-C3-D47
A65-B53-C3-D47
A66-B53-C3-D47
A2-B79-C3-D47
A3-B79-C3-D47
A9-B79-C3-D47
A13-B79-C3-D47
A24-B79-C3-D47
A69-B79-C3-D47
A67-B79-C3-D47
A39-B79-C3-D47
A65-B79-C3-D47
A66-B79-C3-D47
A2-B80-C3-D47
A3-B80-C3-D47
A9-B80-C3-D47
A13-B80-C3-D47
A24-B80-C3-D47
A69-B80-C3-D47
A67-B80-C3-D47
A39-B80-C3-D47
A65-B80-C3-D47
A66-B80-C3-D47
A2-B85-C3-D47
A3-B85-C3-D47
A9-B85-C3-D47
A13-B85-C3-D47
A24-B85-C3-D47
A69-B85-C3-D47
A67-B85-C3-D47
A39-B85-C3-D47
A65-B85-C3-D47
A66-B85-C3-D47
A2-B86-C3-D47
A3-B86-C3-D47
A9-B86-C3-D47
A13-B86-C3-D47
A24-B86-C3-D47
A69-B86-C3-D47
A67-B86-C3-D47
A39-B86-C3-D47
A65-B86-C3-D47
A66-B86-C3-D47
A2-B87-C3-D47
A3-B87-C3-D47
A9-B87-C3-D47
A13-B87-C3-D47
A24-B87-C3-D47
A69-B87-C3-D47
A67-B87-C3-D47
A39-B87-C3-D47
A65-B87-C3-D47
A66-B87-C3-D47
A2-B89-C3-D47
A3-B89-C3-D47
A9-B89-C3-D47
A13-B89-C3-D47
A24-B89-C3-D47
A69-B89-C3-D47
A67-B89-C3-D47
A39-B89-C3-D47
A65-B89-C3-D47
A66-B89-C3-D47
A2-B92-C3-D47
A3-B92-C3-D47
A9-B92-C3-D47
A13-B92-C3-D47
A24-B92-C3-D47
A69-B92-C3-D47
A67-B92-C3-D47
A39-B92-C3-D47
A65-B92-C3-D47
A66-B92-C3-D47
A2-B4-C4-D47
A3-B4-C4-D47
A9-B4-C4-D47
A13-B4-C4-D47
A24-B4-C4-D47
A69-B4-C4-D47
A67-B4-C4-D47

-continued

A39-B4-C4-D47
A65-B4-C4-D47
A66-B4-C4-D47
A2-B5-C4-D47
A3-B5-C4-D47
A9-B5-C4-D47
A13-B5-C4-D47
A24-B5-C4-D47
A69-B5-C4-D47
A67-B5-C4-D47
A39-B5-C4-D47
A65-B5-C4-D47
A66-B5-C4-D47
A2-B6-C4-D47
A3-B6-C4-D47
A9-B6-C4-D47
A13-B6-C4-D47
A24-B6-C4-D47
A69-B6-C4-D47
A67-B6-C4-D47
A39-B6-C4-D47
A65-B6-C4-D47
A66-B6-C4-D47
A2-B32-C4-D47
A3-B32-C4-D47
A9-B32-C4-D47
A13-B32-C4-D47
A24-B32-C4-D47
A69-B32-C4-D47
A67-B32-C4-D47
A39-B32-C4-D47
A65-B32-C4-D47
A66-B32-C4-D47
A2-B39-C4-D47
A3-B39-C4-D47
A9-B39-C4-D47
A13-B39-C4-D47
A24-B39-C4-D47
A69-B39-C4-D47
A67-B39-C4-D47
A39-B39-C4-D47
A65-B39-C4-D47
A66-B39-C4-D47
A2-B45-C4-D47
A3-B45-C4-D47
A9-B45-C4-D47
A13-B45-C4-D47
A24-B45-C4-D47
A69-B45-C4-D47
A67-B45-C4-D47
A39-B45-C4-D47
A65-B45-C4-D47
A66-B45-C4-D47
A2-B53-C4-D47
A3-B53-C4-D47
A9-B53-C4-D47
A13-B53-C4-D47
A24-B53-C4-D47
A69-B53-C4-D47
A67-B53-C4-D47
A39-B53-C4-D47
A65-B53-C4-D47
A66-B53-C4-D47
A2-B79-C4-D47
A3-B79-C4-D47
A9-B79-C4-D47
A13-B79-C4-D47
A24-B79-C4-D47
A69-B79-C4-D47
A67-B79-C4-D47
A39-B79-C4-D47
A65-B79-C4-D47
A66-B79-C4-D47
A2-B80-C4-D47
A3-B80-C4-D47
A9-B80-C4-D47
A13-B80-C4-D47
A24-B80-C4-D47
A69-B80-C4-D47
A67-B80-C4-D47

-continued
A39-B80-C4-D47
A65-B80-C4-D47
A66-B80-C4-D47
A2-B85-C4-D47
A3-B85-C4-D47
A9-B85-C4-D47
A13-B85-C4-D47
A24-B85-C4-D47
A69-B85-C4-D47
A67-B85-C4-D47
A39-B85-C4-D47
A65-B85-C4-D47
A66-B85-C4-D47
A2-B86-C4-D47
A3-B86-C4-D47
A9-B86-C4-D47
A13-B86-C4-D47
A24-B86-C4-D47
A69-B86-C4-D47
A67-B86-C4-D47
A39-B86-C4-D47
A65-B86-C4-D47
A66-B86-C4-D47
A2-B87-C4-D47
A3-B87-C4-D47
A9-B87-C4-D47
A13-B87-C4-D47
A24-B87-C4-D47
A69-B87-C4-D47
A67-B87-C4-D47
A39-B87-C4-D47
A65-B87-C4-D47
A66-B87-C4-D47
A2-B89-C4-D47
A3-B89-C4-D47
A9-B89-C4-D47
A13-B89-C4-D47
A24-B89-C4-D47
A69-B89-C4-D47
A67-B89-C4-D47
A39-B89-C4-D47
A65-B89-C4-D47
A66-B89-C4-D47
A2-B92-C4-D47
A3-B92-C4-D47
A9-B92-C4-D47
A13-B92-C4-D47
A24-B92-C4-D47
A69-B92-C4-D47
A67-B92-C4-D47
A39-B92-C4-D47
A65-B92-C4-D47
A66-B92-C4-D47
A2-B4-C5-D47
A3-B4-C5-D47
A9-B4-C5-D47
A13-B4-C5-D47
A24-B4-C5-D47
A69-B4-C5-D47
A67-B4-C5-D47
A39-B4-C5-D47
A65-B4-C5-D47
A66-B4-C5-D47
A2-B5-C5-D47
A3-B5-C5-D47
A9-B5-C5-D47
A13-B5-C5-D47
A24-B5-C5-D47
A69-B5-C5-D47
A67-B5-C5-D47
A39-B5-C5-D47
A65-B5-C5-D47
A66-B5-C5-D47
A2-B6-C5-D47
A3-B6-C5-D47
A9-B6-C5-D47
A13-B6-C5-D47
A24-B6-C5-D47
A69-B6-C5-D47
A67-B6-C5-D47

-continued
A39-B6-C5-D47
A65-B6-C5-D47
A66-B6-C5-D47
A2-B32-C5-D47
A3-B32-C5-D47
A9-B32-C5-D47
A13-B32-C5-D47
A24-B32-C5-D47
A69-B32-C5-D47
A67-B32-C5-D47
A39-B32-C5-D47
A65-B32-C5-D47
A66-B32-C5-D47
A2-B39-C5-D47
A3-B39-C5-D47
A9-B39-C5-D47
A13-B39-C5-D47
A24-B39-C5-D47
A69-B39-C5-D47
A67-B39-C5-D47
A39-B39-C5-D47
A65-B39-C5-D47
A66-B39-C5-D47
A2-B45-C5-D47
A3-B45-C5-D47
A9-B45-C5-D47
A13-B45-C5-D47
A24-B45-C5-D47
A69-B45-C5-D47
A67-B45-C5-D47
A39-B45-C5-D47
A65-B45-C5-D47
A66-B45-C5-D47
A2-B53-C5-D47
A3-B53-C5-D47
A9-B53-C5-D47
A13-B53-C5-D47
A24-B53-C5-D47
A69-B53-C5-D47
A67-B53-C5-D47
A39-B53-C5-D47
A65-B53-C5-D47
A66-B53-C5-D47
A2-B79-C5-D47
A3-B79-C5-D47
A9-B79-C5-D47
A13-B79-C5-D47
A24-B79-C5-D47
A69-B79-C5-D47
A67-B79-C5-D47
A39-B79-C5-D47
A65-B79-C5-D47
A66-B79-C5-D47
A2-B80-C5-D47
A3-B80-C5-D47
A9-B80-C5-D47
A13-B80-C5-D47
A24-B80-C5-D47
A69-B80-C5-D47
A67-B80-C5-D47
A39-B80-C5-D47
A65-B80-C5-D47
A66-B80-C5-D47
A2-B85-C5-D47
A3-B85-C5-D47
A9-B85-C5-D47
A13-B85-C5-D47
A24-B85-C5-D47
A69-B85-C5-D47
A67-B85-C5-D47
A39-B85-C5-D47
A65-B85-C5-D47
A66-B85-C5-D47
A2-B86-C5-D47
A3-B86-C5-D47
A9-B86-C5-D47
A13-B86-C5-D47
A24-B86-C5-D47
A69-B86-C5-D47
A67-B86-C5-D47

-continued

A39-B86-C5-D47
A65-B86-C5-D47
A66-B86-C5-D47
A2-B87-C5-D47
A3-B87-C5-D47
A9-B87-C5-D47
A13-B87-C5-D47
A24-B87-C5-D47
A69-B87-C5-D47
A67-B87-C5-D47
A39-B87-C5-D47
A65-B87-C5-D47
A66-B87-C5-D47
A2-B89-C5-D47
A3-B89-C5-D47
A9-B89-C5-D47
A13-B89-C5-D47
A24-B89-C5-D47
A69-B89-C5-D47
A67-B89-C5-D47
A39-B89-C5-D47
A65-B89-C5-D47
A66-B89-C5-D47
A2-B92-C5-D47
A3-B92-C5-D47
A9-B92-C5-D47
A13-B92-C5-D47
A24-B92-C5-D47
A69-B92-C5-D47
A67-B92-C5-D47
A39-B92-C5-D47
A65-B92-C5-D47
A66-B92-C5-D47
A2-B4-C6-D47
A3-B4-C6-D47
A9-B4-C6-D47
A13-B4-C6-D47
A24-B4-C6-D47
A69-B4-C6-D47
A67-B4-C6-D47
A39-B4-C6-D47
A65-B4-C6-D47
A66-B4-C6-D47
A2-B5-C6-D47
A3-B5-C6-D47
A9-B5-C6-D47
A13-B5-C6-D47
A24-B5-C6-D47
A69-B5-C6-D47
A67-B5-C6-D47
A39-B5-C6-D47
A65-B5-C6-D47
A66-B5-C6-D47
A2-B6-C6-D47
A3-B6-C6-D47
A9-B6-C6-D47
A13-B6-C6-D47
A24-B6-C6-D47
A69-B6-C6-D47
A67-B6-C6-D47
A39-B6-C6-D47
A65-B6-C6-D47
A66-B6-C6-D47
A2-B32-C6-D47
A3-B32-C6-D47
A9-B32-C6-D47
A13-B32-C6-D47
A24-B32-C6-D47
A69-B32-C6-D47
A67-B32-C6-D47
A39-B32-C6-D47
A65-B32-C6-D47
A66-B32-C6-D47
A2-B39-C6-D47
A3-B39-C6-D47
A9-B39-C6-D47
A13-B39-C6-D47
A24-B39-C6-D47
A69-B39-C6-D47
A67-B39-C6-D47

-continued

A39-B39-C6-D47
A65-B39-C6-D47
A66-B39-C6-D47
A2-B45-C6-D47
A3-B45-C6-D47
A9-B45-C6-D47
A13-B45-C6-D47
A24-B45-C6-D47
A69-B45-C6-D47
A67-B45-C6-D47
A39-B45-C6-D47
A65-B45-C6-D47
A66-B45-C6-D47
A2-B53-C6-D47
A3-B53-C6-D47
A9-B53-C6-D47
A13-B53-C6-D47
A24-B53-C6-D47
A69-B53-C6-D47
A67-B53-C6-D47
A39-B53-C6-D47
A65-B53-C6-D47
A66-B53-C6-D47
A2-B79-C6-D47
A3-B79-C6-D47
A9-B79-C6-D47
A13-B79-C6-D47
A24-B79-C6-D47
A69-B79-C6-D47
A67-B79-C6-D47
A39-B79-C6-D47
A65-B79-C6-D47
A66-B79-C6-D47
A2-B80-C6-D47
A3-B80-C6-D47
A9-B80-C6-D47
A13-B80-C6-D47
A24-B80-C6-D47
A69-B80-C6-D47
A67-B80-C6-D47
A39-B80-C6-D47
A65-B80-C6-D47
A66-B80-C6-D47
A2-B85-C6-D47
A3-B85-C6-D47
A9-B85-C6-D47
A13-B85-C6-D47
A24-B85-C6-D47
A69-B85-C6-D47
A67-B85-C6-D47
A39-B85-C6-D47
A65-B85-C6-D47
A66-B85-C6-D47
A2-B86-C6-D47
A3-B86-C6-D47
A9-B86-C6-D47
A13-B86-C6-D47
A24-B86-C6-D47
A69-B86-C6-D47
A67-B86-C6-D47
A39-B86-C6-D47
A65-B86-C6-D47
A66-B86-C6-D47
A2-B87-C6-D47
A3-B87-C6-D47
A9-B87-C6-D47
A13-B87-C6-D47
A24-B87-C6-D47
A69-B87-C6-D47
A67-B87-C6-D47
A39-B87-C6-D47
A65-B87-C6-D47
A66-B87-C6-D47
A2-B89-C6-D47
A3-B89-C6-D47
A9-B89-C6-D47
A13-B89-C6-D47
A24-B89-C6-D47
A69-B89-C6-D47
A67-B89-C6-D47

-continued
A39-B89-C6-D47
A65-B89-C6-D47
A66-B89-C6-D47
A2-B92-C6-D47
A3-B92-C6-D47
A9-B92-C6-D47
A13-B92-C6-D47
A24-B92-C6-D47
A69-B92-C6-D47
A67-B92-C6-D47
A39-B92-C6-D47
A65-B92-C6-D47
A66-B92-C6-D47
A2-B4-C7-D47
A3-B4-C7-D47
A9-B4-C7-D47
A13-B4-C7-D47
A24-B4-C7-D47
A69-B4-C7-D47
A67-B4-C7-D47
A39-B4-C7-D47
A65-B4-C7-D47
A66-B4-C7-D47
A2-B5-C7-D47
A3-B5-C7-D47
A9-B5-C7-D47
A13-B5-C7-D47
A24-B5-C7-D47
A69-B5-C7-D47
A67-B5-C7-D47
A39-B5-C7-D47
A65-B5-C7-D47
A66-B5-C7-D47
A2-B6-C7-D47
A3-B6-C7-D47
A9-B6-C7-D47
A13-B6-C7-D47
A24-B6-C7-D47
A69-B6-C7-D47
A67-B6-C7-D47
A39-B6-C7-D47
A65-B6-C7-D47
A66-B6-C7-D47
A2-B32-C7-D47
A3-B32-C7-D47
A9-B32-C7-D47
A13-B32-C7-D47
A24-B32-C7-D47
A69-B32-C7-D47
A67-B32-C7-D47
A39-B32-C7-D47
A65-B32-C7-D47
A66-B32-C7-D47
A2-B39-C7-D47
A3-B39-C7-D47
A9-B39-C7-D47
A13-B39-C7-D47
A24-B39-C7-D47
A69-B39-C7-D47
A67-B39-C7-D47
A39-B39-C7-D47
A65-B39-C7-D47
A66-B39-C7-D47
A2-B45-C7-D47
A3-B45-C7-D47
A9-B45-C7-D47
A13-B45-C7-D47
A24-B45-C7-D47
A69-B45-C7-D47
A67-B45-C7-D47
A39-B45-C7-D47
A65-B45-C7-D47
A66-B45-C7-D47
A2-B53-C7-D47
A3-B53-C7-D47
A9-B53-C7-D47
A13-B53-C7-D47
A24-B53-C7-D47
A69-B53-C7-D47
A67-B53-C7-D47

-continued
A39-B53-C7-D47
A65-B53-C7-D47
A66-B53-C7-D47
A2-B79-C7-D47
A3-B79-C7-D47
A9-B79-C7-D47
A13-B79-C7-D47
A24-B79-C7-D47
A69-B79-C7-D47
A67-B79-C7-D47
A39-B79-C7-D47
A65-B79-C7-D47
A66-B79-C7-D47
A2-B80-C7-D47
A3-B80-C7-D47
A9-B80-C7-D47
A13-B80-C7-D47
A24-B80-C7-D47
A69-B80-C7-D47
A67-B80-C7-D47
A39-B80-C7-D47
A65-B80-C7-D47
A66-B80-C7-D47
A2-B85-C7-D47
A3-B85-C7-D47
A9-B85-C7-D47
A13-B85[ ]C7-D47
A24-B85-C7-D47
A69-B85-C7-D47
A67-B85-C7-D47
A39-B85-C7-D47
A65-B85-C7-D47
A66-B85-C7-D47
A2-B86-C7-D47
A3-B86-C7-D47
A9-B86-C7-D47
A13-B86-C7-D47
A24-B86-C7-D47
A69-B86-C7-D47
A67-B86-C7-D47
A39-B86-C7-D47
A65-B86-C7-D47
A66-B86-C7-D47
A2-B87-C7-D47
A3-B87-C7-D47
A9-B87-C7-D47
A13-B87-C7-D47
A24-B87-C7-D47
A69-B87-C7-D47
A67-B87-C7-D47
A39-B87-C7-D47
A65-B87-C7-D47
A66-B87-C7-D47
A2-B89-C7-D47
A3-B89-C7-D47
A9-B89-C7-D47
A13-B89-C7-D47
A24-B89-C7-D47
A69-B89-C7-D47
A67-B89-C7-D47
A39-B89-C7-D47
A65-B89-C7-D47
A66-B89-C7-D47
A2-B92-C7-D47
A3-B92-C7-D472
A9-B92-C7-D47
A13-B92-C7-D47
A24-B92-C7-D47
A69-B92-C7-D47
A67-B92-C7-D47
A39-B92-C7-D47
A65-B92-C7-D47
A66-B92-C7-D47
A2-B4-C8-D47
A3-B4-C8-D47
A9-B4-C8-D47
A13-B4-C8-D47
A24-B4-C8-D47
A69-B4-C8-D47
A67-B4-C8-D47

-continued

A39-B4-C8-D47
A65-B4-C8-D47
A66-B4-C8-D47
A2-B5-C8-D47
A3-B5-C8-D47
A9-B5-C8-D47
A13-B5-C8-D47
A24-B5-C8-D47
A69-B5-C8-D47
A67-B5-C8-D47
A39-B5-C8-D47
A65-B5-C8-D47
A66-B5-C8-D47
A2-B6-C8-D47
A3-B6-C8-D47
A9-B6-C8-D47
A13-B6-C8-D47
A24-B6-C8-D47
A69-B6-C8-D47
A67-B6-C8-D47
A39-B6-C8-D47
A65-B6-C8-D47
A66-B6-C8-D47
A2-B32-C8-D47
A3-B32-C8-D47
A9-B32-C8-D47
A13-B32-C8-D47
A24-B32-C8-D47
A69-B32-C8-D47
A67-B32-C8-D47
A39-B32-C8-D47
A65-B32-C8-D47
A66-B32-C8-D47
A2-B39-C8-D47
A3-B39-C8-D47
A9-B39-C8-D47
A13-B39-C8-D47
A24-B39-C8-D47
A69-B39-C8-D47
A67-B39-C8-D47
A39-B39-C8-D47
A65-B39-C8-D47
A66-B39-C8-D47
A2-B45-C8-D47
A3-B45-C8-D47
A9-B45-C8-D47
A13-B45-C8-D47
A24-B45-C8-D47
A69-B45-C8-D47
A67-B45-C8-D47
A39-B45-C8-D47
A65-B45-C8-D47
A66-B45-C8-D47
A2-B53-C8-D47
A3-B53-C8-D47
A9-B53-C8-D47
A13-B53-C8-D47
A24-B53-C8-D47
A69-B53-C8-D47
A67-B53-C8-D47
A39-B53-C8-D47
A65-B53-C8-D47
A66-B53-C8-D47
A2-B79-C8-D47
A3-B79-C8-D47
A9-B79-C8-D47
A13-B79-C8-D47
A24-B79-C8-D47
A69-B79-C8-D47
A67-B79-C8-D47
A39-B79-C8-D47
A65-B79-C8-D47
A66-B79-C8-D47
A2-B80-C8-D47
A3-B80-C8-D47
A9-B80-C8-D47
A13-B80-C8-D47
A24-B80-C8-D47
A69-B80-C8-D47
A67-B80-C8-D47

-continued

A39-B80-C8-D47
A65-B80-C8-D47
A66-B80-C8-D47
A2-B85-C8-D47
A3-B85-C8-D47
A9-B85-C8-D47
A13-B85-C8-D47
A24-B85-C8-D47
A69-B85-C8-D47
A67-B85-C8-D47
A39-B85-C8-D47
A65-B85-C8-D47
A66-B85-C8-D47
A2-B86-C8-D47
A3-B86-C8-D47
A9-B86-C8-D47
A13-B86-C8-D47
A24-B86-C8-D47
A69-B86-C8-D47
A67-B86-C8-D47
A39-B86-C8-D47
A65-B86-C8-D47
A66-B86-C8-D47
A2-B87-C8-D47
A3-B87-C8-D47
A9-B87-C8-D47
A13-B87-C8-D47
A24-B87-C8-D47
A69-B87-C8-D47
A67-B87-C8-D47
A39-B87-C8-D47
A65-B87-C8-D47
A66-B87-C8-D47
A2-B89-C8-D47
A3-B89-C8-D47
A9-B89-C8-D47
A13-B89-C8-D47
A24-B89-C8-D47
A69-B89-C8-D47
A67-B89-C8-D47
A39-B89-C8-D47
A65-B89-C8-D47
A66-B89-C8-D47
A2-B92-C8-D47
A3-B92-C8-D47
A9-B92-C8-D47
A13-B92-C8-D47
A24-B92-C8-D47
A69-B92-C8-D47
A67-B92-C8-D47
A39-B92-C8-D47
A65-B92-C8-D47
A66-B92-C8-D47
A2-B4-C9-D47
A3-B4-C9-D47
A9-B4-C9-D47
A13-B4-C9-D47
A24-B4-C9-D47
A69-B4-C9-D47
A67-B4-C9-D47
A39-B4-C9-D47
A65-B4-C9-D47
A66-B4-C9-D47
A2-B5-C9-D47
A3-B5-C9-D47
A9-B5-C9-D47
A13-B5-C9-D47
A24-B5-C9-D47
A69-B5-C9-D47
A67-B5-C9-D47
A39-B5-C9-D47
A65-B5-C9-D47
A66-B5-C9-D47
A2-B6-C9-D47
A3-B6-C9-D47
A9-B6-C9-D47
A13-B6-C9-D47
A24-B6-C9-D47
A69-B6-C9-D47
A67-B6-C9-D47

-continued
A39-B6-C9-D47
A65-B6-C9-D47
A66-B6-C9-D47
A2-B32-C9-D47
A3-B32-C9-D47
A9-B32-C9-D47
A13-B32-C9-D47
A24-B32-C9-D47
A69-B32-C9-D47
A67-B32-C9-D47
A39-B32-C9-D47
A65-B32-C9-D47
A66-B32-C9-D47
A2-B39-C9-D47
A3-B39-C9-D47
A9-B39-C9-D47
A13-B39-C9-D47
A24-B39-C9-D47
A69-B39-C9-D47
A67-B39-C9-D47
A39-B39-C9-D47
A65-B39-C9-D47
A66-B39-C9-D47
A2-B45-C9-D47
A3-B45-C9-D47
A9-B45-C9-D47
A13-B45-C9-D47
A24-B45-C9-D47
A69-B45-C9-D47
A67-B45-C9-D47
A39-B45-C9-D47
A65-B45-C9-D47
A66-B45-C9-D47
A2-B53-C9-D47
A3-B53-C9-D47
A9-B53-C9-D47
A13-B53-C9-D47
A24-B53-C9-D47
A69-B53-C9-D47
A67-B53-C9-D47
A39-B53-C9-D47
A65-B53-C9-D47
A66-B53-C9-D47
A2-B79-C9-D47
A3-B79-C9-D47
A9-B79-C9-D47
A13-B79-C9-D47
A24-B79-C9-D47
A69-B79-C9-D47
A67-B79-C9-D47
A39-B79-C9-D47
A65-B79-C9-D47
A66-B79-C9-D47
A2-B80-C9-D47
A3-B80-C9-D47
A9-B80-C9-D47
A13-B80-C9-D47
A24-B80-C9-D47
A69-B80-C9-D47
A67-B80-C9-D47
A39-B80-C9-D47
A65-B80-C9-D47
A66-B80-C9-D47
A2-B85-C9-D47
A3-B85-C9-D47
A9-B85-C9-D47
A13-B85-C9-D47
A24-B85-C9-D47
A69-B85-C9-D47
A67-B85-C9-D47
A39-B85-C9-D47
A65-B85-C9-D47
A66-B85-C9-D47
A2-B86-C9-D47
A3-B86-C9-D47
A9-B86-C9-D47
A13-B86-C9-D47
A24-B86-C9-D47
A69-B86-C9-D47
A67-B86-C9-D47

-continued
A39-B86-C9-D47
A65-B86-C9-D47
A66-B86-C9-D47
A2-B87-C9-D47
A3-B87-C9-D47
A9-B87-C9-D47
A13-B87-C9-D47
A24-B87-C9-D47
A69-B87-C9-D47
A67-B87-C9-D47
A39-B87-C9-D47
A65-B87-C9-D47
A66-B87-C9-D47
A2-B89-C9-D47
A3-B89-C9-D47
A9-B89-C9-D47
A13-B89-C9-D47
A24-B89-C9-D47
A69-B89-C9-D47
A67-B89-C9-D47
A39-B89-C9-D47
A65-B89-C9-D47
A66-B89-C9-D47
A2-B92-C9-D47
A3-B92-C9-D47
A9-B92-C9-D47
A13-B92-C9-D47
A24-B92-C9-D47
A69-B92-C9-D47
A67-B92-C9-D47
A39-B92-C9-D47
A65-B92-C9-D47
A66-B92-C9-D47
A2-B4-C10-D47
A3-B4-C10-D47
A9-B4-C10-D47
A13-B4-C10-D47
A24-B4-C10-D47
A69-B4-C10-D47
A67-B4-C10-D47
A39-B4-C10-D47
A65-B4-C10-D47
A66-B4-C10-D47
A2-B5-C10-D47
A3-B5-C10-D47
A9-B5-C10-D47
A13-B5-C10-D47
A24-B5-C10-D47
A69-B5-C10-D47
A67-B5-C10-D47
A39-B5-C10-D47
A65-B5-C10-D47
A66-B5-C10-D47
A2-B6-C10-D47
A3-B6-C10-D47
A9-B6-C10-D47
A13-B6-C10-D47
A24-B6-C10-D47
A69-B6-C10-D47
A67-B6-C10-D47
A39-B6-C10-D47
A65-B6-C10-D47
A66-B6-C10-D47
A2-B32-C10-D47
A3-B32-C10-D47
A9-B32-C10-D47
A13-B32-C10-D47
A24-B32-C10-D47
A69-B32-C10-D47
A67-B32-C10-D47
A39-B32-C10-D47
A65-B32-C10-D47
A66-B32-C10-D47
A2-B39-C10-D47
A3-B39-C10-D47
A9-B39-C10-D47
A13-B39-C10-D47
A24-B39-C10-D47
A69-B39-C10-D47
A67-B39-C10-D47

-continued

A39-B39-C10-D47
A65-B39-C10-D47
A66-B39-C10-D47
A2-B45-C10-D47
A3-B45-C10-D47
A9-B45-C10-D47
A13-B45-C10-D47
A24-B45-C10-D47
A69-B45-C10-D47
A67-B45-C10-D47
A39-B45-C10-D47
A65-B45-C10-D47
A66-B45-C10-D47
A2-B53-C10-D47
A3-B53-C10-D47
A9-B53-C10-D47
A13-B53-C10-D47
A24-B53-C10-D47
A69-B53-C10-D47
A67-B53-C10-D47
A39-B53-C10-D47
A65-B53-C10-D47
A66-B53-C10-D47
A2-B79-C10-D47
A3-B79-C10-D47
A9-B79-C10-D47
A13-B79-C10-D47
A24-B79-C10-D47
A69-B79-C10-D47
A67-B79-C10-D47
A39-B79-C10-D47
A65-B79-C10-D47
A66-B79-C10-D47
A2-B80-C10-D47
A3-B80-C10-D47
A9-B80-C10-D47
A13-B80-C10-D47
A24-B80-C10-D47
A69-B80-C10-D47
A67-B80-C10-D47
A39-B80-C10-D47
A65-B80-C10-D47
A66-B80-C10-D47
A2-B85-C10-D47
A3-B85-C10-D47
A9-B85-C10-D47
A13-B85-C10-D47
A24-B85-C10-D47
A69-B85-C10-D47
A67-B85-C10-D47
A39-B85-C10-D47
A65-B85-C10-D47
A66-B85-C10-D47
A2-B86-C10-D47
A3-B86-C10-D47
A9-B86-C10-D47
A13-B86-C10-D47
A24-B86-C10-D47
A69-B86-C10-D47
A67-B86-C10-D47
A39-B86-C10-D47
A65-B86-C10-D47
A66-B86-C10-D47
A2-B87-C10-D47
A3-B87-C10-D47
A9-B87-C10-D47
A13-B87-C10-D47
A24-B87-C10-D47
A69-B87-C10-D47
A67-B87-C10-D47
A39-B87-C10-D47
A65-B87-C10-D47
A66-B87-C10-D47
A2-B89-C10-D47
A3-B89-C10-D47
A9-B89-C10-D47
A13-B89-C10-D47
A24-B89-C10-D47
A69-B89-C10-D47
A67-B89-C10-D47

-continued

A39-B89-C10-D47
A65-B89-C10-D47
A66-B89-C10-D47
A2-B92-C10-D47
A3-B92-C10-D47
A9-B92-C10-D47
A13-B92-C10-D47
A24-B92-C10-D47
A69-B92-C10-D47
A67-B92-C10-D47
A39-B92-C10-D47
A65-B92-C10-D47
A66-B92-C10-D47
A2-B4-C11-D47
A3-B4-C11-D47
A9-B4-C11-D47
A13-B4-C11-D47
A24-B4-C11-D47
A69-B4-C11-D47
A67-B4-C11-D47
A39-B4-C11-D47
A65-B4-C11-D47
A66-B4-C11-D47
A2-B5-C11-D47
A3-B5-C11-D47
A9-B5-C11-D47
A13-B5-C11-D47
A24-B5-C11-D47
A69-B5-C11-D47
A67-B5-C11-D47
A39-B5-C11-D47
A65-B5-C11-D47
A66-B5-C11-D47
A2-B6-C11-D47
A3-B6-C11-D47
A9-B6-C11-D47
A13-B6-C11-D47
A24-B6-C11-D47
A69-B6-C11-D47
A67-B6-C11-D47
A39-B6-C11-D47
A65-B6-C11-D47
A66-B6-C11-D47
A2-B32-C11-D47
A3-B32-C11-D47
A9-B32-C11-D47
A13-B32-C11-D47
A24-B32-C11-D47
A69-B32-C11-D47
A67-B32-C11-D47
A39-B32-C11-D47
A65-B32-C11-D47
A66-B32-C11-D47
A2-B39-C11-D47
A3-B39-C11-D47
A9-B39-C11-D47
A13-B39-C11-D47
A24-B39-C11-D47
A69-B39-C11-D47
A67-B39-C11-D47
A39-B39-C11-D47
A65-B39-C11-D47
A66-B39-C11-D47
A2-B45-C11-D47
A3-B45-C11-D47
A9-B45-C11-D47
A13-B45-C11-D47
A24-B45-C11-D47
A69-B45-C11-D47
A67-B45-C11-D47
A39-B45-C11-D47
A65-B45-C11-D47
A66-B45-C11-D47
A2-B53-C11-D47
A3-B53-C11-D47
A9-B53-C11-D47
A13-B53-C11-D47
A24-B53-C11-D47
A69-B53-C11-D47
A67-B53-C11-D47

-continued

A39-B53-C11-D47
A65-B53-C11-D47
A66-B53-C11-D47
A2-B79-C11-D47
A3-B79-C11-D47
A9-B79-C11-D47
A13-B79-C11-D47
A24-B79-C11-D47
A69-B79-C11-D47
A67-B79-C11-D47
A39-B79-C11-D47
A65-B79-C11-D47
A66-B79-C11-D47
A2-B80-C11-D47
A3-B80-C11-D47
A9-B80-C11-D47
A13-B80-C11-D47
A24-B80-C11-D47
A69-B80-C11-D47
A67-B80-C11-D47
A39-B80-C11-D47
A65-B80-C11-D47
A66-B80-C11-D47
A2-B85-C11-D47
A3-B85-C11-D47
A9-B85-C11-D47
A13-B85-C11-D47
A24-B85-C11-D47
A69-B85-C11-D47
A67-B85-C11-D47
A39-B85-C11-D47
A65-B85-C11-D47
A66-B85-C11-D47
A2-B86-C11-D47
A3-B86-C11-D47
A9-B86-C11-D47
A13-B86-C11-D47
A24-B86-C11-D47
A69-B86-C11-D47
A67-B86-C11-D47
A39-B86-C11-D47
A65-B86-C11-D47
A66-B86-C11-D47
A2-B87-C11-D47
A3-B87-C11-D47
A9-B87-C11-D47
A13-B87-C11-D47
A24-B87-C11-D47
A69-B87-C11-D47
A67-B87-C11-D47
A39-B87-C11-D47
A65-B87-C11-D47
A66-B87-C11-D47
A2-B89-C11-D47
A3-B89-C11-D47
A9-B89-C11-D47
A13-B89-C11-D47
A24-B89-C11-D47
A69-B89-C11-D47
A67-B89-C11-D47
A39-B89-C11-D47
A65-B89-C11-D47
A66-B89-C11-D47
A2-B92-C11-D47
A3-B92-C11-D47
A9-B92-C11-D47
A13-B92-C11-D47
A24-B92-C11-D47
A69-B92-C11-D47
A67-B92-C11-D47
A39-B92-C11-D47
A65-B92-C11-D47
A66-B92-C11-D47
A2-B4-C12-D47
A3-B4-C12-D47
A9-B4-C12-D47
A13-B4-C12-D47
A24-B4-C12-D47
A69-B4-C12-D47
A67-B4-C12-D47

-continued

A39-B4-C12-D47
A65-B4-C12-D47
A66-B4-C12-D47
A2-B5-C12-D47
A3-B5-C12-D47
A9-B5-C12-D47
A13-B5-C12-D47
A24-B5-C12-D47
A69-B5-C12-D47
A67-B5-C12-D47
A39-B5-C12-D47
A65-B5-C12-D47
A66-B5-C12-D47
A2-B6-C12-D47
A3-B6-C12-D47
A9-B6-C12-D47
A13-B6-C12-D47
A24-B6-C12-D47
A69-B6-C12-D47
A67-B6-C12-D47
A39-B6-C12-D47
A65-B6-C12-D47
A66-B6-C12-D47
A2-B32-C12-D47
A3-B32-C12-D47155
A9-B32-C12-D47
A13-B32-C12-D47
A24-B32-C12-D47
A69-B32-C12-D47
A67-B32-C12-D47
A39-B32-C12-D47
A65-B32-C12-D47
A66-B32-C12-D47
A2-B39-C12-D47
A3-B39-C12-D47
A9-B39-C12-D47
A13-B39-C12-D47
A24-B39-C12-D47
A69-B39-C12-D47
A67-B39-C12-D47
A39-B39-C12-D47
A65-B39-C12-D47
A66-B39-C12-D47
A2-B45-C12-D47
A3-B45-C12-D47
A9-B45-C12-D47
A13-B45-C12-D47
A24-B45-C12-D47
A69-B45-C12-D47
A67-B45-C12-D47
A39-B45-C12-D47
A65-B45-C12-D47
A66-B45-C12-D47
A2-B53-C12-D47
A3-B53-C12-D47
A9-B53-C12-D47
A13-B53-C12-D47
A24-B53-C12-D47
A69-B53-C12-D47
A67-B53-C12-D47
A39-B53-C12-D47
A65-B53-C12-D47
A66-B53-C12-D47
A2-B79-C12-D47
A3-B79-C12-D47
A9-B79-C12-D47
A13-B79-C12-D47
A24-B79-C12-D47
A69-B79-C12-D47
A67-B79-C12-D47
A39-B79-C12-D47
A65-B79-C12-D47
A66-B79-C12-D47
A2-B80-C12-D47
A3-B80-C12-D47
A9-B80-C12-D47
A13-B80-C12-D47
A24-B80-C12-D47
A69-B80-C12-D47
A67-B80-C12-D47

-continued
A39-B80-C12-D47
A65-B80-C12-D47
A66-B80-C12-D47
A2-B85-C12-D47
A3-B85-C12-D47
A9-B85-C12-D47
A13-B85-C12-D47
A24-B85-C12-D47
A69-B85-C12-D47
A67-B85-C12-D47
A39-B85-C12-D47
A65-B85-C12-D47
A66-B85-C12-D47
A2-B86-C12-D47
A3-B86-C12-D47
A9-B86-C12-D47
A13-B86-C12-D47
A24-B86-C12-D47
A69-B86-C12-D47
A67-B86-C12-D47
A39-B86-C12-D47
A65-B86-C12-D47
A66-B86-C12-D47
A2-B87-C12-D47
A3-B87-C12-D47
A9-B87-C12-D47
A13-B87-C12-D47
A24-B87-C12-D47
A69-B87-C12-D47
A67-B87-C12-D47
A39-B87-C12-D47
A65-B87-C12-D47
A66-B87-C12-D47
A2-B89-C12-D47
A3-B89-C12-D47
A9-B89-C12-D47
A13-B89-C12-D47
A24-B89-C12-D47
A69-B89-C12-D47
A67-B89-C12-D47
A39-B89-C12-D47
A65-B89-C12-D47
A66-B89-C12-D47
A2-B92-C12-D47
A3-B92-C12-D47
A9-B92-C12-D47
A13-B92-C12-D47
A24-B92-C12-D47
A69-B92-C12-D47
A67-B92-C12-D47
A39-B92-C12-D47
A65-B92-C12-D47
A66-B92-C12-D47
A2-B4-C13-D47
A3-B4-C13-D47
A9-B4-C13-D47
A13-B4-C13-D47
A24-B4-C13-D47
A69-B4-C13-D47
A67-B4-C13-D47
A39-B4-C13-D47
A65-B4-C13-D47
A66-B4-C13-D47
A2-B5-C13-D47
A3-B5-C13-D47
A9-B5-C13-D47
A13-B5-C13-D47
A24-B5-C13-D47
A69-B5-C13-D47
A67-B5-C13-D47
A39-B5-C13-D47
A65-B5-C13-D47
A66-B5-C13-D47
A2-B6-C13-D47
A3-B6-C13-D47
A9-B6-C13-D47
A13-B6-C13-D47
A24-B6-C13-D47
A69-B6-C13-D47
A67-B6-C13-D47

-continued
A39-B6-C13-D47
A65-B6-C13-D47
A66-B6-C13-D47
A2-B32-C13-D47
A3-B32-C13-D47
A9-B32-C13-D47
A13-B32-C13-D47
A24-B32-C13-D47
A69-B32-C13-D47
A67-B32-C13-D47
A39-B32-C13-D47
A65-B32-C13-D47
A66-B32-C13-D47
A2-B39-C13-D47
A3-B39-C13-D47
A9-B39-C13-D47
A13-B39-C13-D47
A24-B39-C13-D47
A69-B39-C13-D47
A67-B39-C13-D47
A39-B39-C13-D47
A65-B39-C13-D47
A66-B39-C13-D47
A2-B45-C13-D47
A3-B45-C13-D47
A9-B45-C13-D47
A13-B45-C13-D47
A24-B45-C13-D47
A69-B45-C13-D47
A67-B45-C13-D47
A39-B45-C13-D47
A65-B45-C13-D47
A66-B45-C13-D47
A2-B53-C13-D47
A3-B53-C13-D47
A9-B53-C13-D47
A13-B53-C13-D47
A24-B53-C13-D47
A69-B53-C13-D47
A67-B53-C13-D47
A39-B53-C13-D47
A65-B53-C13-D47
A66-B53-C13-D47
A2-B79-C13-D47
A3-B79-C13-D47
A9-B79-C13-D47
A13-B79-C13-D47
A24-B79-C13-D47
A69-B79-C13-D47
A67-B79-C13-D47
A39-B79-C13-D47
A65-B79-C13-D47
A66-B79-C13-D47
A2-B80-C13-D47
A3-B80-C13-D47
A9-B80-C13-D47
A13-B80-C13-D47
A24-B80-C13-D47
A69-B80-C13-D47
A67-B80-C13-D47
A39-B80-C13-D47
A65-B80-C13-D47
A66-B80-C13-D47
A2-B85-C13-D47
A3-B85-C13-D47
A9-B85-C13-D47
A13-B85-C13-D47
A24-B85-C13-D47
A69-B85-C13-D47
A67-B85-C13-D47
A39-B85-C13-D47
A65-B85-C13-D47
A66-B85-C13-D47
A2-B86-C13-D47
A3-B86-C13-D47
A9-B86-C13-D47
A13-B86-C13-D47
A24-B86-C13-D47
A69-B86-C13-D47
A67-B86-C13-D47

-continued

A39-B86-C13-D47
A65-B86-C13-D47
A66-B86-C13-D47
A2-B87-C13-D47
A3-B87-C13-D47
A9-B87-C13-D47
A13-B87-C13-D47
A24-B87-C13-D47
A69-B87-C13-D47
A67-B87-C13-D47
A39-B87-C13-D47
A65-B87-C13-D47
A66-B87-C13-D47
A2-B89-C13-D47
A3-B89-C13-D47
A9-B89-C13-D47
A13-B89-C13-D47
A24-B89-C13-D47
A69-B89-C13-D47
A67-B89-C13-D47
A39-B89-C13-D47
A65-B89-C13-D47
A66-B89-C13-D47
A2-B92-C13-D47
A3-B92-C13-D47
A9-B92-C13-D47
A13-B92-C13-D47
A24-B92-C13-D47
A69-B92-C13-D47
A67-B92-C13-D47
A39-B92-C13-D47
A65-B92-C13-D47
A66-B92-C13-D47
A2-B4-C1-D48
A3-B4-C1-D48
A9-B4-C1-D48
A13-B4-C1-D48
A24-B4-C1-D48
A69-B4-C1-D48
A67-B4-C1-D48
A39-B4-C1-D48
A65-B4-C1-D48
A66-B4-C1-D48
A2-B5-C1-D48
A3-B5-C1-D48
A9-B5-C1-D48
A13-B5-C1-D48
A24-B5-C1-D48
A69-B5-C1-D48
A67-B5-C1-D48
A39-B5-C1-D48
A65-B5-C1-D48
A66-B5-C1-D48
A2-B6-C1-D48
A3-B6-C1-D48
A9-B6-C1-D48
A13-B6-C1-D48
A24-B6-C1-D48
A69-B6-C1-D48
A67-B6-C1-D48
A39-B6-C1-D48
A65-B6-C1-D48
A66-B6-C1-D48
A2-B32-C1-D48
A3-B32-C1-D48
A9-B32-C1-D48
A13-B32-C1-D48
A24-B32-C1-D48
A69-B32-C1-D48
A67-B32-C1-D48
A39-B32-C1-D48
A65-B32-C1-D48
A66-B32-C1-D48
A2-B39-C1-D48
A3-B39-C1-D48
A9-B39-C1-D48
A13-B39-C1-D48
A24-B39-C1-D48
A69-B39-C1-D48
A67-B39-C1-D48

-continued

A39-B39-C1-D48
A65-B39-C1-D48
A66-B39-C1-D48
A2-B45-C1-D48
A3-B45-C1-D48
A9-B45-C1-D48
A13-B45-C1-D48
A24-B45-C1-D48
A69-B45-C1-D48
A67-B45-C1-D48
A39-B45-C1-D48
A65-B45-C1-D48
A66-B45-C1-D48
A2-B53-C1-D48
A3-B53-C1-D48
A9-B53-C1-D48
A13-B53-C1-D48
A24-B53-C1-D48
A69-B53-C1-D48
A67-B53-C1-D48
A39-B53-C1-D48
A65-B53-C1-D48
A66-B53-C1-D48
A2-B79-C1-D48
A3-B79-C1-D48
A9-B79-C1-D48
A13-B79-C1-D48
A24-B79-C1-D48
A69-B79-C1-D48
A67-B79-C1-D48
A39-B79-C1-D48
A65-B79-C1-D48
A66-B79-C1-D48
A2-B80-C1-D48
A3-B80-C1-D48
A9-B80-C1-D48
A13-B80-C1-D48
A24-B80-C1-D48
A69-B80-C1-D48
A67-B80-C1-D48
A39-B80-C1-D48
A65-B80-C1-D48
A66-B80-C1-D48
A2-B85-C1-D48
A3-B85-C1-D48
A9-B85-C1-D48
A13-B85-C1-D48
A24-B85-C1-D48
A69-B85-C1-D48
A67-B85-C1-D48
A39-B85-C1-D48
A65-B85-C1-D48
A66-B85-C1-D48
A2-B86-C1-D48
A3-B86-C1-D48
A9-B86-C1-D48
A13-B86-C1-D48
A24-B86-C1-D48
A69-B86-C1-D48
A67-B86-C1-D48
A39-B86-C1-D48
A65-B86-C1-D48
A66-B86-C1-D48
A2-B87-C1-D48
A3-B87-C1-D48
A9-B87-C1-D48
A13-B87-C1-D48
A24-B87-C1-D48
A69-B87-C1-D48
A67-B87-C1-D48
A39-B87-C1-D48
A65-B87-C1-D48
A66-B87-C1-D48
A2-B89-C1-D48
A3-B89-C1-D48
A9-B89-C1-D48
A13-B89-C1-D48
A24-B89-C1-D48
A69-B89-C1-D48
A67-B89-C1-D48

-continued
A39-B89-C1-D48
A65-B89-C1-D48
A66-B89-C1-D48
A2-B92-C1-D48
A3-B92-C1-D48
A9-B92-C1-D48
A13-B92-C1-D48
A24-B92-C1-D48
A69-B92-C1-D48
A67-B92-C1-D48
A39-B92-C1-D48
A65-B92-C1-D48
A66-B92-C1-D48
A2-B4-C2-D48
A3-B4-C2-D48
A9-B4-C2-D48
A13-B4-C2-D48
A24-B4-C2-D48
A69-B4-C2-D48
A67-B4-C2-D48
A39-B4-C2-D48
A65-B4-C2-D48
A66-B4-C2-D48
A2-B5-C2-D48
A3-B5-C2-D48
A9-B5-C2-D48
A13-B5-C2-D48
A24-B5-C2-D48
A69-B5-C2-D48
A67-B5-C2-D48
A39-B5-C2-D48
A65-B5-C2-D48
A66-B5-C2-D48
A2-B6-C2-D48
A3-B6-C2-D48
A9-B6-C2-D48
A13-B6-C2-D48
A24-B6-C2-D48
A69-B6-C2-D48
A67-B6-C2-D48
A39-B6-C2-D48
A65-B6-C2-D48
A66-B6-C2-D48
A2-B32-C2-D48
A3-B32-C2-D48
A9-B32-C2-D48
A13-B32-C2-D48
A24-B32-C2-D48
A69-B32-C2-D48
A67-B32-C2-D48
A39-B32-C2-D48
A65-B32-C2-D48
A66-B32-C2-D48
A2-B39-C2-D48
A3-B39-C2-D48
A9-B39-C2-D48
A13-B39-C2-D48
A24-B39-C2-D48
A69-B39-C2-D48
A67-B39-C2-D48
A39-B39-C2-D48
A65-B39-C2-D48
A66-B39-C2-D48
A2-B45-C2-D48
A3-B45-C2-D48
A9-B45-C2-D48
A13-B45-C2-D48
A24-B45-C2-D48
A69-B45-C2-D48
A67-B45-C2-D48
A39-B45-C2-D48
A65-B45-C2-D48
A66-B45-C2-D48
A2-B53-C2-D48
A3-B53-C2-D48
A9-B53-C2-D48
A13-B53-C2-D48
A24-B53-C2-D48
A69-B53-C2-D48
A67-B53-C2-D48

-continued
A39-B53-C2-D48
A65-B53-C2-D48
A66-B53-C2-D48
A2-B79-C2-D48
A3-B79-C2-D48
A9-B79-C2-D48
A13-B79-C2-D48
A24-B79-C2-D48
A69-B79-C2-D48
A67-B79-C2-D48
A39-B79-C2-D48
A65-B79-C2-D48
A66-B79-C2-D48
A2-B80-C2-D48
A3-B80-C2-D48
A9-B80-C2-D48
A13-B80-C2-D48
A24-B80-C2-D48
A69-B80-C2-D48
A67-B80-C2-D48
A39-B80-C2-D48
A65-B80-C2-D48
A66-B80-C2-D48
A2-B85-C2-D48
A3-B85-C2-D48
A9-B85-C2-D48
A13-B85-C2-D48
A24-B85-C2-D48
A69-B85-C2-D48
A67-B85-C2-D48
A39-B85-C2-D48
A65-B85-C2-D48
A66-B85-C2-D48
A2-B86-C2-D48
A3-B86-C2-D48
A9-B86-C2-D48
A13-B86-C2-D48
A24-B86-C2-D48
A69-B86-C2-D48
A67-B86-C2-D48
A39-B86-C2-D48
A65-B86-C2-D48
A66-B86-C2-D48
A2-B87-C2-D48
A3-B87-C2-D48
A9-B87-C2-D48
A13-B87-C2-D48
A24-B87-C2-D48
A69-B87-C2-D48
A67-B87-C2-D48
A39-B87-C2-D48
A65-B87-C2-D48
A66-B87-C2-D48
A2-B89-C2-D48
A3-B89-C2-D48
A9-B89-C2-D48
A13-B89-C2-D48
A24-B89-C2-D48
A69-B89-C2-D48
A67-B89-C2-D48
A39-B89-C2-D48
A65-B89-C2-D48
A66-B89-C2-D48
A2-B92-C2-D48
A3-B92-C2-D48
A9-B92-C2-D48
A13-B92-C2-D48
A24-B92-C2-D48
A69-B92-C2-D48
A67-B92-C2-D48
A39-B92-C2-D48
A6S-B92-C2-D48
A66-B92-C2-D48
A2-B4-C3-D48
A3-B4-C3-D48
A9-B4-C3-D48
A13-B4-C3-D48
A24-B4-C3-D48
A69-B4-C3-D48
A67-B4-C3-D48

-continued
A39-B4-C3-D48
A65-B4-C3-D48
A66-B4-C3-D48
A2-B5-C3-D48
A3-B5-C3-D48
A9-B5-C3-D48
A13-B5-C3-D48
A24-B5-C3-D48
A69-B5-C3-D48
A67-B5-C3-D48
A39-B5-C3-D48
A65-B5-C3-D48
A66-B5-C3-D48
A2-B6-C3-D48
A3-B6-C3-D48
A9-B6-C3-D48
A13-B6-C3-D48
A24-B6-C3-D48
A69-B6-C3-D48
A67-B6-C3-D48
A39-B6-C3-D48
A65-B6-C3-D48
A66-B6-C3-D48
A2-B32-C3-D48
A3-B32-C3-D48
A9-B32-C3-D48
A13-B32-C3-D48
A24-B32-C3-D48
A69-B32-C3-D48
A67-B32-C3-D48
A39-B32-C3-D48
A65-B32-C3-D48
A66-B32-C3-D48
A2-B39-C3-D48
A3-B39-C3-D48
A9-B39-C3-D48
A13-B39-C3-D48
A24-B39-C3-D48
A69-B39-C3-D48
A67-B39-C3-D48
A39-B39-C3-D48
A65-B39-C3-D48
A66-B39-C3-D48
A2-B45-C3-D48
A3-B45-C3-D48
A9-B45-C3-D48
A13-B45-C3-D48
A24-B45-C3-D48
A69-B45-C3-D48
A67-B45-C3-D48
A39-B45-C3-D48
A65-B45-C3-D48
A66-B45-C3-D48
A2-B53-C3-D48
A3-B53-C3-D48
A9-B53-C3-D48
A13-B53-C3-D48
A24-B53-C3-D48
A69-B53-C3-D48
A67-B53-C3-D48
A39-B53-C3-D48
A65-B53-C3-D48
A66-B53-C3-D48
A2-B79-C3-D48
A3-B79-C3-D48
A9-B79-C3-D48
A13-B79-C3-D48
A24-B79-C3-D48
A69-B79-C3-D48
A67-B79-C3-D48
A39-B79-C3-D48
A65-B79-C3-D48
A66-B79-C3-D48
A2-B80-C3-D48
A3-B80-C3-D48
A9-B80-C3-D48
A13-B80-C3-D48
A24-B80-C3-D48
A69-B80-C3-D48
A67-B80-C3-D48

-continued
A39-B80-C3-D48
A65-B80-C3-D48
A66-B80-C3-D48
A2-B85-C3-D48
A3-B85-C3-D48
A9-B85-C3-D48
A13-B85-C3-D48
A24-B85-C3-D48
A69-B85-C3-D48
A67-B85-C3-D48
A39-B85-C3-D48
A65-B85-C3-D48
A66-B85-C3-D48
A2-B86-C3-D48
A3-B86-C3-D48
A9-B86-C3-D48
A13-B86-C3-D48
A24-B86-C3-D48
A69-B86-C3-D48
A67-B86-C3-D48
A39-B86-C3-D48
A65-B86-C3-D48
A66-B86-C3-D48
A2-B87-C3-D48
A3-B87-C3-D48
A9-B87-C3-D48
A13-B87-C3-D48
A24-B87-C3-D48
A69-B87-C3-D48
A67-B87-C3-D48
A39-B87-C3-D48
A65-B87-C3-D48
A66-B87-C3-D48
A2-B89-C3-D48
A3-B89-C3-D48
A9-B89-C3-D48
A13-B89-C3-D48
A24-B89-C3-D48
A69-B89-C3-D48
A67-B89-C3-D48
A39-B89-C3-D48
A65-B89-C3-D48
A66-B89-C3-D48
A2-B92-C3-D48
A3-B92-C3-D48
A9-B92-C3-D48
A13-B92-C3-D48
A24-B92-C3-D48
A69-B92-C3-D48
A67-B92-C3-D48
A39-B92-C3-D48
A65-B92-C3-D48
A66-B92-C3-D48
A2-B4-C4-D48
A3-B4-C4-D48
A9-B4-C4-D48
A13-B4-C4-D48
A24-B4-C4-D48
A69-B4-C4-D48
A67-B4-C4-D48
A39-B4-C4-D48
A65-B4-C4-D48
A66-B4-C4-D48
A2-B5-C4-D48
A3-B5-C4-D48
A9-B5-C4-D48
A13-B5-C4-D48
A24-B5-C4-D48
A69-B5-C4-D48
A67-B5-C4-D48
A39-B5-C4-D48
A65-B5-C4-D48
A66-B5-C4-D48
A2-B6-C4-D48
A3-B6-C4-D48
A9-B6-C4-D48
A13-B6-C4-D48
A24-B6-C4-D48
A69-B6-C4-D48
A67-B6-C4-D48

-continued

A39-B6-C4-D48
A65-B6-C4-D48
A66-B6-C4-D48
A2-B32-C4-D48
A3-B32-C4-D48
A9-B32-C4-D48
A13-B32-C4-D48
A24-B32-C4-D48
A69-B32-C4-D48
A67-B32-C4-D48
A39-B32-C4-D48
A65-B32-C4-D48
A66-B32-C4-D48
A2-B39-C4-D48
A3-B39-C4-D48
A9-B39-C4-D48
A13-B39-C4-D48
A24-B39-C4-D48
A69-B39-C4-D48
A67-B39-C4-D48
A39-B39-C4-D48
A65-B39-C4-D48
A66-B39-C4-D48
A2-B45-C4-D48
A3-B45-C4-D48
A9-B45-C4-D48
A13-B45-C4-D48
A24-B45-C4-D48
A69-B45-C4-D48
A67-B45-C4-D48
A39-B45-C4-D48
A65-B45-C4-D48
A66-B45-C4-D48
A2-B53-C4-D48
A3-B53-C4-D48
A9-B53-C4-D48
A13-B53-C4-D48
A24-B53-C4-D48
A69-B53-C4-D48
A67-B53-C4-D48
A39-B53-C4-D48
A65-B53-C4-D48
A66-B53-C4-D48
A2-B79-C4-D48
A3-B79-C4-D48
A9-B79-C4-D48
A13-B79-C4-D48
A24-B79-C4-D48
A69-B79-C4-D48
A67-B79-C4-D48
A39-B79-C4-D48
A65-B79-C4-D48
A66-B79-C4-D48
A2-B80-C4-D48
A3-B80-C4-D48
A9-B80-C4-D48
A13-B80-C4-D48
A24-B80-C4-D48
A69-B80-C4-D48
A67-B80-C4-D48
A39-B80-C4-D48
A65-B80-C4-D48
A66-B80-C4-D48
A2-B85-C4-D48
A3-B85-C4-D48
A9-B85-C4-D48
A13-B85-C4-D48
A24-B85-C4-D48
A69-B85-C4-D48
A67-B85-C4-D48
A39-B85-C4-D48
A65-B85-C4-D48
A66-B85-C4-D48
A2-B86-C4-D48
A3-B86-C4-D48
A9-B86-C4-D48
A13-B86-C4-D48
A24-B86-C4-D48
A69-B86-C4-D48
A67-B86-C4-D48

-continued

A39-B86-C4-D48
A65-B86-C4-D48
A66-B86-C4-D48
A2-B87-C4-D48
A3-B87-C4-D48
A9-B87-C4-D48
A13-B87-C4-D48
A24-B87-C4-D48
A69-B87-C4-D48
A67-B87-C4-D48
A39-B87-C4-D48
A65-B87-C4-D48
A66-B87-C4-D48
A2-B89-C4-D48
A3-B89-C4-D48
A9-B89-C4-D48
A13-B89-C4-D48
A24-B89-C4-D48
A69-B89-C4-D48
A67-B89-C4-D48
A39-B89-C4-D48
A65-B89-C4-D48
A66-B89-C4-D48
A2-B92-C4-D48
A3-B92-C4-D48
A9-B92-C4-D48
A13-B92-C4-D48
A24-B92-C4-D48
A69-B92-C4-D48
A67-B92-C4-D48
A39-B92-C4-D48
A65-B92-C4-D48
A66-B92-C4-D48
A2-B4-C5-D48
A3-B4-C5-D48
A9-B4-C5-D48
A13-B4-C5-D48
A24-B4-C5-D48
A69-B4-C5-D48
A67-B4-C5-D48
A39-B4-C5-D48
A65-B4-C5-D48
A66-B4-C5-D48
A2-B5-C5-D48
A3-B5-C5-D48
A9-B5-C5-D48
A13-B5-C5-D48
A24-B5-C5-D48
A69-B5-C5-D48
A67-B5-C5-D48
A39-B5-C5-D48
A65-B5-C5-D48
A66-B5-C5-D48
A2-B6-C5-D48
A3-B6-C5-D48
A9-B6-C5-D48
A13-B6-C5-D48
A24-B6-C5-D48
A69-B6-C5-D48
A67-B6-C5-D48
A39-B6-C5-D48
A65-B6-C5-D48
A66-B6-C5-D48
A2-B32-C5-D48
A3-B32-C5-D48
A9-B32-C5-D48
A13-B32-C5-D48
A24-B32-C5-D48
A69-B32-C5-D48
A67-B32-C5-D48
A39-B32-C5-D48
A65-B32-C5-D48
A66-B32-C5-D48
A2-B39-C5-D48
A3-B39-C5-D48
A9-B39-C5-D48
A13-B39-C5-D48
A24-B39-C5-D48
A69-B39-C5-D48
A67-B39-C5-D48

-continued

A39-B39-C5-D48
A65-B39-C5-D48
A66-B39-C5-D48
A2-B45-C5-D48
A3-B45-C5-D48
A9-B45-C5-D48
A13-B45-C5-D48
A24-B45-C5-D48
A69-B45-C5-D48
A67-B45-C5-D48
A39-B45-C5-D48
A65-B45-C5-D48
A66-B45-C5-D48
A2-B53-C5-D48
A3-B53-C5-D48
A9-B53-C5-D48
A13-B53-C5-D48
A24-B53-C5-D48
A69-B53-C5-D48
A67-B53-C5-D48
A39-B53-C5-D48
A65-B53-C5-D48
A66-B53-C5-D48
A2-B79-C5-D48
A3-B79-C5-D48
A9-B79-C5-D48
A13-B79-C5-D48
A24-B79-C5-D48
A69-B79-C5-D48
A67-B79-C5-D48
A39-B79-C5-D48
A65-B79-C5-D48
A66-B79-C5-D48
A2-B80-C5-D48
A3-B80-C5-D48
A9-B80-C5-D48
A13-B80-C5-D48
A24-B80-C5-D48
A69-B80-C5-D48
A67-B80-C5-D48
A39-B80-C5-D48
A65-B80-C5-D48
A66-B80-C5-D48
A2-B85-C5-D48
A3-B85-C5-D48
A9-B85-C5-D48
A13-B85-C5-D48
A24-B85-C5-D48
A69-B85-C5-D48
A67-B85-C5-D48
A39-B85-C5-D48
A65-B85-C5-D48
A66-B85-C5-D48
A2-B86-C5-D48
A3-B86-C5-D48
A9-B86-C5-D48
A13-B86-C5-D48
A24-B86-C5-D48
A69-B86-C5-D48
A67-B86-C5-D48
A39-B86-C5-D48
A65-B86-C5-D48
A66-B86-C5-D48
A2-B87-C5-D48
A3-B87-C5-D48
A9-B87-C5-D48
A13-B87-C5-D48
A24-B87-C5-D48
A69-B87-C5-D48
A67-B87-C5-D48
A39-B87-C5-D48
A65-B87-C5-D48
A66-B87-C5-D48
A2-B89-C5-D48
A3-B89-C5-D48
A9-B89-C5-D48
A13-B89-C5-D48
A24-B89-C5-D48
A69-B89-C5-D48
A67-B89-C5-D48

-continued

A39-B89-C5-D48
A65-B89-C5-D48
A66-B89-C5-D48
A2-B92-C5-D48
A3-B92-C5-D48
A9-B92-C5-D48
A13-B92-C5-D48
A24-B92-C5-D48
A69-B92-C5-D48
A67-B92-C5-D48
A39-B92-C5-D48
A65-B92-C5-D48
A66-B92-C5-D48
A2-B4-C6-D48
A3-B4-C6-D48
A9-B4-C6-D48
A13-B4-C6-D48
A24-B4-C6-D48
A69-B4-C6-D48
A67-B4-C6-D48
A39-B4-C6-D48
A65-B4-C6-D48
A66-B4-C6-D48
A2-B5-C6-D48
A3-B5-C6-D48
A9-B5-C6-D48
A13-B5-C6-D48
A24-B5-C6-D48
A69-B5-C6-D48
A67-B5-C6-D48
A39-B5-C6-D48
A65-B5-C6-D48
A66-B5-C6-D48
A2-B6-C6-D48
A3-B6-C6-D48
A9-B6-C6-D48
A13-B6-C6-D48
A24-B6-C6-D48
A69-B6-C6-D48
A67-B6-C6-D48
A39-B6-C6-D48
A65-B6-C6-D48
A66-B6-C6-D48
A2-B32-C6-D48
A3-B32-C6-D48
A9-B32-C6-D48
A13-B32-C6-D48
A24-B32-C6-D48
A69-B32-C6-D48
A67-B32-C6-D48
A39-B32-C6-D48
A65-B32-C6-D48
A66-B32-C6-D48
A2-B39-C6-D48
A3-B39-C6-D48
A9-B39-C6-D48
A13-B39-C6-D48
A24-B39-C6-D48
A69-B39-C6-D48
A67-B39-C6-D48
A39-B39-C6-D48
A65-B39-C6-D48
A66-B39-C6-D48
A2-B45-C6-D48
A3-B45-C6-D48
A9-B45-C6-D48
A13-B45-C6-D48
A24-B45-C6-D48
A69-B45-C6-D48
A67-B45-C6-D48
A39-B45-C6-D48
A65-B45-C6-D48
A66-B45-C6-D48
A2-B53-C6-D48
A3-B53-C6-D48
A9-B53-C6-D48
A13-B53-C6-D48
A24-B53-C6-D48
A69-B53-C6-D48
A67-B53-C6-D48

-continued
A39-B53-C6-D48
A65-B53-C6-D48
A66-B53-C6-D48
A2-B79-C6-D48
A3-B79-C6-D48
A9-B79-C6-D48
A13-B79-C6-D48
A24-B79-C6-D48
A69-B79-C6-D48
A67-B79-C6-D48
A39-B79-C6-D48
A65-B79-C6-D48
A66-B79-C6-D48
A2-B80-C6-D48
A3-B80-C6-D48
A9-B80-C6-D48
A13-B80-C6-D48
A24-B80-C6-D48
A69-B80-C6-D48
A67-B80-C6-D48
A39-B80-C6-D48
A65-B80-C6-D48
A66-B80-C6-D48
A2-B85-C6-D48
A3-B85-C6-D48
A9-B85-C6-D48
A13-B85-C6-D48
A24-B85-C6-D48
A69-B85-C6-D48
A67-B85-C6-D48
A39-B85-C6-D48
A65-B85-C6-D48
A66-B85-C6-D48
A2-B86-C6-D48
A3-B86-C6-D48
A9-B86-C6-D48
A13-B86-C6-D48
A24-B86-C6-D48
A69-B86-C6-D48
A67-B86-C6-D48
A39-B86-C6-D48
A65-B86-C6-D48
A66-B86-C6-D48
A2-B87-C6-D48
A3-B87-C6-D48
A9-B87-C6-D48
A13-B87-C6-D48
A24-B87-C6-D48
A69-B87-C6-D48
A67-B87-C6-D48
A39-B87-C6-D48
A65-B87-C6-D48
A66-B87-C6-D48
A2-B89-C6-D48
A3-B89-C6-D48
A9-B89-C6-D48
A13-B89-C6-D48
A24-B89-C6-D48
A69-B89-C6-D48
A67-B89-C6-D48
A39-B89-C6-D48
A65-B89-C6-D48
A66-B89-C6-D48
A2-B92-C6-D48
A3-B92-C6-D48
A9-B92-C6-D48
A13-B92-C6-D48
A24-B92-C6-D48
A69-B92-C6-D48
A67-B92-C6-D48
A39-B92-C6-D48
A65-B92-C6-D48
A66-B92-C6-D48
A2-B4-C7-D48
A3-B4-C7-D48
A9-B4-C7-D48
A13-B4-C7-D48
A24-B4-C7-D48
A69-B4-C7-D48
A67-B4-C7-D48

-continued
A39-B4-C7-D48
A65-B4-C7-D48
A66-B4-C7-D48
A2-B5-C7-D48
A3-B5-C7-D48
A9-B5-C7-D48
A13-B5-C7-D48
A24-B5-C7-D48
A69-B5-C7-D48
A67-B5-C7-D48
A39-B5-C7-D48
A65-B5-C7-D48
A66-B5-C7-D48
A2-B6-C7-D48
A3-B6-C7-D48
A9-B6-C7-D48
A13-B6-C7-D48
A24-B6-C7-D48
A69-B6-C7-D48
A67-B6-C7-D48
A39-B6-C7-D48
A65-B6-C7-D48
A66-B6-C7-D48
A2-B32-C7-D48
A3-B32-C7-D48
A9-B32-C7-D48
A13-B32-C7-D48
A24-B32-C7-D48
A69-B32-C7-D48
A67-B32-C7-D48
A39-B32-C7-D48
A65-B32-C7-D48
A66-B32-C7-D48
A2-B39-C7-D48
A3-B39-C7-D48
A9-B39-C7-D48
A13-B39-C7-D48
A24-B39-C7-D48
A69-B39-C7-D48
A67-B39-C7-D48
A39-B39-C7-D48
A65-B39-C7-D48
A66-B39-C7-D48
A2-B45-C7-D48
A3-B45-C7-D48
A9-B45-C7-D48
A13-B45-C7-D48
A24-B45-C7-D48
A69-B45-C7-D48
A67-B45-C7-D48
A39-B45-C7-D48
A65-B45-C7-D48
A66-B45-C7-D48
A2-B53-C7-D48
A3-B53-C7-D48
A9-B53-C7-D48
A13-B53-C7-D48
A24-B53-C7-D48
A69-B53-C7-D48
A67-B53-C7-D48
A39-B53-C7-D48
A65-B53-C7-D48
A66-B53-C7-D48
A2-B79-C7-D48
A3-B79-C7-D48
A9-B79-C7-D48
A13-B79-C7-D48
A24-B79-C7-D48
A69-B79-C7-D48
A67-B79-C7-D48
A39-B79-C7-D48
A65-B79-C7-D48
A66-B79-C7-D48
A2-B80-C7-D48
A3-B80-C7-D48
A9-B80-C7-D48
A13-B80-C7-D48
A24-B80-C7-D48
A69-B80-C7-D48
A67-B80-C7-D48

-continued
A39-B80-C7-D48
A65-B80-C7-D48
A66-B80-C7-D48
A2-B85-C7-D48
A3-B85-C7-D48
A9-B85-C7-D48
A13-B85-C7-D48
A24-B85-C7-D48
A69-B85-C7-D48
A67-B85-C7-D48
A39-B85-C7-D48
A65-B85-C7-D48
A66-B85-C7-D48
A2-B86-C7-D48
A3-B86-C7-D48
A9-B86-C7-D48
A13-B86-C7-D48
A24-B86-C7-D48
A69-B86-C7-D48
A67-B86-C7-D48
A39-B86-C7-D48
A65-B86-C7-D48
A66-B86-C7-D48
A2-B87-C7-D48
A3-B87-C7-D48
A9-B87-C7-D48
A13-B87-C7-D48
A24-B87-C7-D48
A69-B87-C7-D48
A67-B87-C7-D48
A39-B87-C7-D48
A65-B87-C7-D48
A66-B87-C7-D48
A2-B89-C7-D48
A3-B89-C7-D48
A9-B89-C7-D48
A13-B89-C7-D48
A24-B89-C7-D48
A69-B89-C7-D48
A67-B89-C7-D48
A39-B89-C7-D48
A65-B89-C7-D48
A66-B89-C7-D48
A2-B92-C7-D48
A3-B92-C7-D48
A9-B92-C7-D48
A13-B92-C7-D48
A24-B92-C7-D48
A69-B92-C7-D48
A67-B92-C7-D48
A39-B92-C7-D48
A65-B92-C7-D48
A66-B92-C7-D48
A2-B4-C8-D48
A3-B4-C8-D48
A9-B4-C8-D48
A13-B4-C8-D48
A24-B4-C8-D48
A69-B4-C8-D48
A67-B4-C8-D48
A39-B4-C8-D48
A65-B4-C8-D48
A66-B4-C8-D48
A2-B5-C8-D48
A3-B5-C8-D48
A9-B5-C8-D48
A13-B5-C8-D48
A24-B5-C8-D48
A69-B5-C8-D48
A67-B5-C8-D48
A39-B5-C8-D48
A65-B5-C8-D48
A66-B5-C8-D48
A2-B6-C8-D48
A3-B6-C8-D48
A9-B6-C8-D48
A13-B6-C8-D48
A24-B6-C8-D48
A69-B6-C8-D48
A67-B6-C8-D48

-continued
A39-B6-C8-D48
A65-B6-C8-D48
A66-B6-C8-D48
A2-B32-C8-D48
A3-B32-C8-D48
A9-B32-C8-D48
A13-B32-C8-D48
A24-B32-C8-D48
A69-B32-C8-D48
A67-B32-C8-D48
A39-B32-C8-D48
A65-B32-C8-D48
A66-B32-C8-D48
A2-B39-C8-D48
A3-B39-C8-D48
A9-B39-C8-D48
A13-B39-C8-D48
A24-B39-C8-D48
A69-B39-C8-D48
A67-B39-C8-D48
A39-B39-C8-D48
A65-B39-C8-D48
A66-B39-C8-D48
A2-B45-C8-D48
A3-B45-C8-D48
A9-B45-C8-D48
A13-B45-C8-D48
A24-B45-C8-D48
A69-B45-C8-D48
A67-B45-C8-D48
A39-B45-C8-D48
A65-B45-C8-D48
A66-B45-C8-D48
A2-B53-C8-D48
A3-B53-C8-D48
A9-B53-C8-D48
A13-B53-C8-D48
A24-B53-C8-D48
A69-B53-C8-D48
A67-B53-C8-D48
A39-B53-C8-D48
A65-B53-C8-D48
A66-B53-C8-D48
A2-B79-C8-D48
A3-B79-C8-D48
A9-B79-C8-D48
A13-B79-C8-D48
A24-B79-C8-D48
A69-B79-C8-D48
A67-B79-C8-D48
A39-B79-C8-D48
A65-B79-C8-D48
A66-B79-C8-D48
A2-B80-C8-D48
A3-B80-C8-D48
A9-B80-C8-D48
A13-B80-C8-D48
A24-B80-C8-D48
A69-B80-C8-D48
A67-B80-C8-D48
A39-B80-C8-D48
A65-B80-C8-D48
A66-B80-C8-D48
A2-B85-C8-D48
A3-B85-C8-D48
A9-B85-C8-D48
A13-B85-C8-D48
A24-B85-C8-D48
A69-B85-C8-D48
A67-B85-C8-D48
A39-B85-C8-D48
A65-B85-C8-D48
A66-B85-C8-D48
A2-B86-C8-D48
A3-B86-C8-D48
A9-B86-C8-D48
A13-B86-C8-D48
A24-B86-C8-D48
A69-B86-C8-D48
A67-B86-C8-D48

-continued

A39-B86-C8-D48
A65-B86-C8-D48
A66-B86-C8-D48
A2-B87-C8-D48
A3-B87-C8-D48
A9-B87-C8-D48
A13-B87-C8-D48
A24-B87-C8-D48
A69-B87-C8-D48
A67-B87-C8-D48
A39-B87-C8-D48
A65-B87-C8-D48
A66-B87-C8-D48
A2-B89-C8-D48
A3-B89-C8-D48
A9-B89-C8-D48
A13-B89-C8-D48
A24-B89-C8-D48
A69-B89-C8-D48
A67-B89-C8-D48
A39-B89-C8-D48
A65-B89-C8-D48
A66-B89-C8-D48
A2-B92-C8-D48
A3-B92-C8-D48
A9-B92-C8-D48
A13-B92-C8-D48
A24-B92-C8-D48
A69-B92-C8-D48
A67-B92-C8-D48
A39-B92-C8-D48
A65-B92-C8-D48
A66-B92-C8-D48
A2-B4-C9-D48
A3-B4-C9-D48
A9-B4-C9-D48
A13-B4-C9-D48
A24-B4-C9-D48
A69-B4-C9-D48
A67-B4-C9-D48
A39-B4-C9-D48
A65-B4-C9-D48
A66-B4-C9-D48
A2-B5-C9-D48
A3-B5-C9-D48
A9-B5-C9-D48
A13-B5-C9-D48
A24-B5-C9-D48
A69-B5-C9-D48
A67-B5-C9-D48
A39-B5-C9-D48
A65-B5-C9-D48
A66-B5-C9-D48
A2-B6-C9-D48
A3-B6-C9-D48
A9-B6-C9-D48
A13-B6-C9-D48
A24-B6-C9-D48
A69-B6-C9-D48
A67-B6-C9-D48
A39-B6-C9-D48
A65-B6-C9-D48
A66-B6-C9-D48
A2-B32-C9-D48
A3-B32-C9-D48
A9-B32-C9-D48
A13-B32-C9-D48
A24-B32-C9-D48
A69-B32-C9-D48
A67-B32-C9-D48
A39-B32-C9-D48
A65-B32-C9-D48
A66-B32-C9-D48
A2-B39-C9-D48
A3-B39-C9-D48
A9-B39-C9-D48
A13-B39-C9-D48
A24-B39-C9-D48
A69-B39-C9-D48
A67-B39-C9-D48

-continued

A39-B39-C9-D48
A65-B39-C9-D48
A66-B39-C9-D48
A2-B45-C9-D48
A3-B45-C9-D48
A9-B45-C9-D48
A13-B45-C9-D48
A24-B45-C9-D48
A69-B45-C9-D48
A67-B45-C9-D48
A39-B45-C9-D48
A65-B45-C9-D48
A66-B45-C9-D48
A2-B53-C9-D48
A3-B53-C9-D48
A9-B53-C9-D48
A13-B53-C9-D48
A24-B53-C9-D48
A69-B53-C9-D48
A67-B53-C9-D48
A39-B53-C9-D48
A65-B53-C9-D48
A66-B53-C9-D48
A2-B79-C9-D48
A3-B79-C9-D48
A9-B79-C9-D48
A13-B79-C9-D48
A24-B79-C9-D48
A69-B79-C9-D48
A67-B79-C9-D48
A39-B79-C9-D48
A65-B79-C9-D48
A66-B79-C9-D48
A2-B80-C9-D48
A3-B80-C9-D48
A9-B80-C9-D48
A13-B80-C9-D48
A24-B80-C9-D48
A69-B80-C9-D48
A67-B80-C9-D48
A39-B80-C9-D48
A65-B80-C9-D48
A66-B80-C9-D48
A2-B85-C9-D48
A3-B85-C9-D48
A9-B85-C9-D48
A13-B85-C9-D48
A24-B85-C9-D48
A69-B85-C9-D48
A67-B85-C9-D48
A39-B85-C9-D48
A65-B85-C9-D48
A66-B85-C9-D48
A2-B86-C9-D48
A3-B86-C9-D48
A9-B86-C9-D48
A13-B86-C9-D48
A24-B86-C9-D48
A69-B86-C9-D48
A67-B86-C9-D48
A39-B86-C9-D48
A65-B86-C9-D48
A66-B86-C9-D48
A2-B87-C9-D48
A3-B87-C9-D48
A9-B87-C9-D48
A13-B87-C9-D48
A24-B87-C9-D48
A69-B87-C9-D48
A67-B87-C9-D48
A39-B87-C9-D48
A65-B87-C9-D48
A66-B87-C9-D48
A2-B89-C9-D48
A3-B89-C9-D48
A9-B89-C9-D48
A13-B89-C9-D48
A24-B89-C9-D48
A69-B89-C9-D48
A67-B89-C9-D48

-continued
A39-B89-C9-D48
A65-B89-C9-D48
A66-B89-C9-D48
A2-B92-C9-D48
A3-B92-C9-D48
A9-B92-C9-D48
A13-B92-C9-D48
A24-B92-C9-D48
A69-B92-C9-D48
A67-B92-C9-D48
A39-B92-C9-D48
A65-B92-C9-D48
A66-B92-C9-D48
A2-B4-C10-D48
A3-B4-C10-D48
A9-B4-C10-D48
A13-B4-C10-D48
A24-B4-C10-D48
A69-B4-C10-D48
A67-B4-C10-D48
A39-B4-C10-D48
A65-B4-C10-D48
A66-B4-C10-D48
A2-B5-C10-D48
A3-B5-C10-D48
A9-B5-C10-D48
A13-B5-C10-D48
A24-B5-C10-D48
A69-B5-C10-D48
A67-B5-C10-D48
A39-B5-C10-D48
A65-B5-C10-D48
A66-B5-C10-D48
A2-B6-C10-D48
A3-B6-C10-D48
A9-B6-C10-D48
A13-B6-C10-D48
A24-B6-C10-D48
A69-B6-C10-D48
A67-B6-C10-D48
A39-B6-C10-D48
A65-B6-C10-D48
A66-B6-C10-D48
A2-B32-C10-D48
A3-B32-C10-D48
A9-B32-C10-D48
A13-B32-C10-D48
A24-B32-C10-D48
A69-B32-C10-D48
A67-B32-C10-D48
A39-B32-C10-D48
A65-B32-C10-D48
A66-B32-C10-D48
A2-B39-C10-D48
A3-B39-C10-D48
A9-B39-C10-D48
A13-B39-C10-D48
A24-B39-C10-D48
A69-B39-C10-D48
A67-B39-C10-D48
A39-B39-C10-D48
A65-B39-C10-D48
A66-B39-C10-D48
A2-B45-C10-D48
A3-B45-C10-D48
A9-B45-C10-D48
A13-B45-C10-D48
A24-B45-C10-D48
A69-B45-C10-D48
A67-B45-C10-D48
A39-B45-C10-D48
A65-B45-C10-D48
A66-B45-C10-D48
A2-B53-C10-D48
A3-B53-C10-D48
A9-B53-C10-D48
A13-B53-C10-D48
A24-B53-C10-D48
A69-B53-C10-D48
A67-B53-C10-D48

-continued
A39-B53-C10-D48
A65-B53-C10-D48
A66-B53-C10-D48
A2-B79-C10-D48
A3-B79-C10-D48
A9-B79-C10-D48
A13-B79-C10-D48
A24-B79-C10-D48
A69-B79-C10-D48
A67-B79-C10-D48
A39-B79-C10-D48
A65-B79-C10-D48
A66-B79-C10-D48
A2-B80-C10-D48
A3-B80-C10-D48
A9-B80-C10-D48
A13-B80-C10-D48
A24-B80-C10-D48
A69-B80-C10-D48
A67-B80-C10-D48
A39-B80-C10-D48
A65-B80-C10-D48
A66-B80-C10-D48
A2-B85-C10-D48
A3-B85-C10-D48
A9-B85-C10-D48
A13-B85-C10-D48
A24-B85-C10-D48
A69-B85-C10-D48
A67-B85-C10-D48
A39-B85-C10-D48
A65-B85-C10-D48
A66-B85-C10-D48
A2-B86-C10-D48
A3-B86-C10-D48
A9-B86-C10-D48
A13-B86-C10-D48
A24-B86-C10-D48
A69-B86-C10-D48
A67-B86-C10-D48
A39-B86-C10-D48
A65-B86-C10-D48
A66-B86-C10-D48
A2-B87-C10-D48
A3-B87-C10-D48
A9-B87-C10-D48
A13-B87-C10-D48
A24-B87-C10-D48
A69-B87-C10-D48
A67-B87-C10-D48
A39-B87-C10-D48
A65-B87-C10-D48
A66-B87-C10-D48
A2-B89-C10-D48
A3-B89-C10-D48
A9-B89-C10-D48
A13-B89-C10-D48
A24-B89-C10-D48
A69-B89-C10-D48
A67-B89-C10-D48
A39-B89-C10-D48
A65-B89-C10-D48
A66-B89-C10-D48
A2-B92-C10-D48
A3-B92-C10-D48
A9-B92-C10-D48
A13-B92-C10-D48
A24-B92-C10-D48
A69-B92-C10-D48
A67-B92-C10-D48
A39-B92-C10-D48
A65-B92-C10-D48
A66-B92-C1 0-D48
A2-B4-C11-D48
A3-B4-C11-D48
A9-B4-C11-D48
A13-B4-C11-D48
A24-B4-C11-D48
A69-B4-C11-D48
A67-B4-C11-D48

-continued
A39-B4-C11-D48
A65-B4-C11-D48
A66-B4-C11-D48
A2-B5-C11-D48
A3-B5-C11-D48
A9-B5-C11-D48
A13-B5-C11-D48
A24-B5-C11-D48
A69-B5-C11-D48
A67-B5-C11-D48
A39-B5-C11-D48
A65-B5-C11-D48
A66-B5-C11-D48
A2-B6-C11-D48
A3-B6-C11-D48
A9-B6-C11-D48
A13-B6-C11-D48
A24-B6-C11-D48
A69-B6-C11-D48
A67-B6-C11-D48
A39-B6-C11-D48
A65-B6-C11-D48
A66-B6-C11-D48
A2-B32-C11-D48
A3-B32-C11-D48
A9-B32-C11-D48
A13-B32-C11-D48
A24-B32-C11-D48
A69-B32-C11-D48
A67-B32-C11-D48
A39-B32-C11-D48
A65-B32-C11-D48
A66-B32-C11-D48
A2-B39-C11-D48
A3-B39-C11-D48
A9-B39-C11-D48
A13-B39-C11-D48
A24-B39-C11-D48
A69-B39-C11-D48
A67-B39-C11-D48
A39-B39-C11-D48
A65-B39-C11-D48
A66-B39-C11-D48
A2-B45-C11-D48
A3-B45-C11-D48
A9-B45-C11-D48
A13-B45-C11-D48
A24-B45-C11-D48
A69-B45-C11-D48
A67-B45-C11-D48
A39-B45-C11-D48
A65-B45-C11-D48
A66-B45-C11-D48
A2-B53-C11-D48
A3-B53-C11-D48
A9-B53-C11-D48
A13-B53-C11-D48
A24-B53-C11-D48
A69-B53-C11-D48
A67-B53-C11-D48
A39-B53-C11-D48
A65-B53-C11-D48
A66-B53-C11-D48
A2-B79-C11-D48
A3-B79-C11-D48
A9-B79-C11-D48
A13-B79-C11-D48
A24-B79-C11-D48
A69-B79-C11-D48
A67-B79-C11-D48
A39-B79-C11-D48
A65-B79-C11-D48
A66-B79-C11-D48
A2-B80-C11-D48
A3-B80-C11-D48
A9-B80-C11-D48
A13-B80-C11-D48
A24-B80-C11-D48
A69-B80-C11-D48
A67-B80-C11-D48

-continued
A39-B80-C11-D48
A65-B80-C11-D48
A66-B80-C11-D48
A2-B85-C11-D48
A3-B85-C11-D48
A9-B85-C11-D48
A13-B85-C11-D48
A24-B85-C11-D48
A69-B85-C11-D48
A67-B85-C11-D48
A39-B85-C11-D48
A65-B85-C11-D48
A66-B85-C11-D48
A2-B86-C11-D48
A3-B86-C11-D48
A9-B86-C11-D48
A13-B86-C11-D48
A24-B86-C11-D48
A69-B86-C11-D48
A67-B86-C11-D48
A39-B86-C11-D48
A65-B86-C11-D48
A66-B86-C11-D48
A2-B87-C11-D48
A3-B87-C11-D48
A9-B87-C11-D48
A13-B87-C11-D48
A24-B87-C11-D48
A69-B87-C11-D48
A67-B87-C11-D48
A39-B87-C11-D48
A65-B87-C11-D48
A66-B87-C11-D48
A2-B89-C11-D48
A3-B89-C11-D48
A9-B89-C11-D48
A13-B89-C11-D48
A24-B89-C11-D48
A69-B89-C11-D48
A67-B89-C11-D48
A39-B89-C11-D48
A65-B89-C11-D48
A66-B89-C11-D48
A2-B92-C11-D48
A3-B92-C11-D48
A9-B92-C11-D48
A13-B92-C11-D48
A24-B92-C11-D48
A69-B92-C11-D48
A67-B92-C11-D48
A39-B92-C11-D48
A65-B92-C11-D48
A66-B92-C11-D48
A2-B4-C12-D48
A3-B4-C12-D48
A9-B4-C12-D48
A13-B4-C12-D48
A24-B4-C12-D48
A69-B4-C12-D48
A67-B4-C12-D48
A39-B4-C12-D48
A65-B4-C12-D48
A66-B4-C12-D48
A2-B5-C12-D48
A3-B5-C12-D48
A9-B5-C12-D48
A13-B5-C12-D48
A24-B5-C12-D48
A69-B5-C12-D48
A67-B5-C12-D48
A39-B5-C12-D48
A65-B5-C12-D48
A66-B5-C12-D48
A2-B6-C12-D48
A3-B6-C12-D48
A9-B6-C12-D48
A13-B6-C12-D48
A24-B6-C12-D48
A69-B6-C12-D48
A67-B6-C12-D48

-continued

A39-B6-C12-D48
A65-B6-C12-D48
A66-B6-C12-D48
A2-B32-C12-D48
A3-B32-C12-D48
A9-B32-C12-D48
A13-B32-C12-D48
A24-B32-C12-D48
A69-B32-C12-D48
A67-B32-C12-D48
A39-B32-C12-D48
A65-B32-C12-D48
A66-B32-C12-D48
A2-B39-C12-D48
A3-B39-C12-D48
A9-B39-C12-D48
A13-B39-C12-D48
A24-B39-C12-D48
A69-B39-C12-D48
A67-B39-C12-D48
A39-B39-C12-D48
A65-B39-C12-D48
A66-B39-C12-D48
A2-B45-C12-D48
A3-B45-C12-D48
A9-B45-C12-D48
A13-B45-C12-D48
A24-B45-C12-D48
A69-B45-C12-D48
A67-B45-C12-D48
A39-B45-C12-D48
A65-B45-C12-D48
A66-B45-C12-D48
A2-B53-C12-D48
A3-B53-C12-D48
A9-B53-C12-D48
A13-B53-C12-D48
A24-B53-C12-D48
A69-B53-C12-D48
A67-B53-C12-D48
A39-B53-C12-D48
A65-B53-C12-D48
A66-B53-C12-D48
A2-B79-C12-D48
A3-B79-C12-D48
A9-B79-C12-D48
A13-B79-C12-D48
A24-B79-C12-D48
A69-B79-C12-D48
A67-B79-C12-D48
A39-B79-C12-D48
A65-B79-C12-D48
A66-B79-C12-D48
A2-B80-C12-D48
A3-B80-C12-D48
A9-B80-C12-D48
A13-B80-C12-D48
A24-B80-C12-D48
A69-B80-C12-D48
A67-B80-C12-D48
A39-B80-C12-D48
A65-B80-C12-D48
A66-B80-C12-D48
A2-B85-C12-D48
A3-B85-C12-D48
A9-B85-C12-D48
A13-B85-C12-D48
A24-B85-C12-D48
A69-B85-C12-D48
A67-B85-C12-D48
A39-B85-C12-D48
A65-B85-C12-D48
A66-B85-C12-D48
A2-B86-C12-D48
A3-B86-C12-D48
A9-B86-C12-D48
A13-B86-C12-D48
A24-B86-C12-D48
A69-B86-C12-D48
A67-B86-C12-D48

-continued

A39-B86-C12-D48
A65-B86-C12-D48
A66-B86-C12-D48
A2-B87-C12-D48
A3-B87-C12-D48
A9-B87-C12-D48
A13-B87-C12-D48
A24-B87-C12-D48
A69-B87-C12-D48
A67-B87-C12-D48
A39-B87-C12-D48
A65-B87-C12-D48
A66-B87-C12-D48
A2-B89-C12-D48
A3-B89-C12-D48
A9-B89-C12-D48
A13-B89-C12-D48
A24-B89-C12-D48
A69-B89-C12-D48
A67-B89-C12-D48
A39-B89-C12-D48
A65-B89-C12-D48
A66-B89-C12-D48
A2-B92-C12-D48
A3-B92-C12-D48
A9-B92-C12-D48
A13-B92-C12-D48
A24-B92-C12-D48
A69-B92-C12-D48
A67-B92-C12-D48
A39-B92-C12-D48
A65-B92-C12-D48
A66-B92-C12-D48
A2-B4-C13-D48
A3-B4-C13-D48
A9-B4-C13-D48
A13-B4-C13-D48
A24-B4-C13-D48
A69-B4-C13-D48
A67-B4-C13-D48
A39-B4-C13-D48
A65-B4-C13-D48
A66-B4-C13-D48
A2-B5-C13-D48
A3-B5-C13-D48
A9-B5-C13-D48
A13-B5-C13-D48
A24-B5-C13-D48
A69-B5-C13-D48
A67-B5-C13-D48
A39-B5-C13-D48
A65-B5-C13-D48
A66-B5-C13-D48
A2-B6-C13-D48
A3-B6-C13-D48
A9-B6-C13-D48
A13-B6-C13-D48
A24-B6-C13-D48
A69-B6-C13-D48
A67-B6-C13-D48
A39-B6-C13-D48
A65-B6-C13-D48
A66-B6-C13-D48
A2-B32-C13-D48
A3-B32-C13-D48
A9-B32-C13-D48
A13-B32-C13-D48
A24-B32-C13-D48
A69-B32-C13-D48
A67-B32-C13-D48
A39-B32-C13-D48
A65-B32-C13-D48
A66-B32-C13-D48
A2-B39-C13-D48
A3-B39-C13-D48
A9-B39-C13-D48
A13-B39-C13-D48
A24-B39-C13-D48
A69-B39-C13-D48
A67-B39-C13-D48

-continued
A39-B39-C13-D48
A65-B39-C13-D48
A66-B39-C13-D48
A2-B45-C13-D48
A3-B45-C13-D48
A9-B45-C13-D48
A13-B45-C13-D48
A24-B45-C13-D48
A69-B45-C13-D48
A67-B45-C13-D48
A39-B45-C13-D48
A65-B45-C13-D48
A66-B45-C13-D48
A2-B53-C13-D48
A3-B53-C13-D48
A9-B53-C13-D48
A13-B53-C13-D48
A24-B53-C13-D48
A69-B53-C13-D48
A67-B53-C13-D48
A39-B53-C13-D48
A65-B53-C13-D48
A66-B53-C13-D48
A2-B79-C13-D48
A3-B79-C13-D48
A9-B79-C13-D48
A13-B79-C13-D48
A24-B79-C13-D48
A69-B79-C13-D48
A67-B79-C13-D48
A39-B79-C13-D48
A65-B79-C13-D48
A66-B79-C13-D48
A2-B80-C13-D48
A3-B80-C13-D48
A9-B80-C13-D48
A13-B80-C13-D48
A24-B80-C13-D48
A69-B80-C13-D48
A67-B80-C13-D48
A39-B80-C13-D48
A65-B80-C13-D48
A66-B80-C13-D48
A2-B85-C13-D48
A3-B85-C13-D48
A9-B85-C13-D48
A13-B85-C13-D48
A24-B85-C13-D48
A69-B85-C13-D48
A67-B85-C13-D48
A39-B85-C13-D48
A65-B85-C13-D48
A66-B85-C13-D48
A2-B86-C13-D48
A3-B86-C13-D48
A9-B86-C13-D48
A13-B86-C13-D48
A24-B86-C13-D48
A69-B86-C13-D48
A67-B86-C13-D48
A39-B86-C13-D48
A65-B86-C13-D48
A66-B86-C13-D48
A2-B87-C13-D48
A3-B87-C13-D48
A9-B87-C13-D48
A13-B87-C13-D48
A24-B87-C13-D48
A69-B87-C13-D48
A67-B87-C13-D48
A39-B87-C13-D48
A65-B87-C13-D48
A66-B87-C13-D48
A2-B89-C13-D48
A3-B89-C13-D48
A9-B89-C13-D48
A13-B89-C13-D48
A24-B89-C13-D48
A69-B89-C13-D48
A67-B89-C13-D48

-continued
A39-B89-C13-D48
A65-B89-C13-D48
A66-B89-C13-D48
A2-B92-C13-D48
A3-B92-C13-D48
A9-B92-C13-D48
A13-B92-C13-D48
A24-B92-C13-D48
A69-B92-C13-D48
A67-B92-C13-D48
A39-B92-C13-D48
A65-B92-C13-D48
A66-B92-C13-D48
A2-B4-C1-D49
A3-B4-C1-D49
A9-B4-C1-D49
A13-B4-C1-D49
A24-B4-C1-D49
A69-B4-C1-D49
A67-B4-C1-D49
A39-B4-C1-D49
A65-B4-C1-D49
A66-B4-C1-D49
A2-B5-C1-D49
A3-B5-C1-D49
A9-B5-C1-D49
A13-B5-C1-D49
A24-B5-C1-D49
A69-B5-C1-D49
A67-B5-C1-D49
A39-B5-C1-D49
A65-B5-C1-D49
A66-B5-C1-D49
A2-B6-C1-D49
A3-B6-C1-D49
A9-B6-C1-D49
A13-B6-C1-D49
A24-B6-C1-D49
A69-B6-C1-D49
A67-B6-C1-D49
A39-B6-C1-D49
A65-B6-C1-D49
A66-B6-C1-D49
A2-B32-C1-D49
A3-B32-C1-D49
A9-B32-C1-D49
A13-B32-C1-D49
A24-B32-C1-D49
A69-B32-C1-D49
A67-B32-C1-D49
A39-B32-C1-D49
A65-B32-C1-D49
A66-B32-C1-D49
A2-B39-C1-D49
A3-B39-C1-D49
A9-B39-C1-D49
A13-B39-C1-D49
A24-B39-C1-D49
A69-B39-C1-D49
A67-B39-C1-D49
A39-B39-C1-D49
A65-B39-C1-D49
A66-B39-C1-D49
A2-B45-C1-D49
A3-B45-C1-D49
A9-B45-C1-D49
A13-B45-C1-D49
A24-B45-C1-D49
A69-B45-C1-D49
A67-B45-C1-D49
A39-B45-C1-D49
A65-B45-C1-D49
A66-B45-C1-D49
A2-B53-C1-D49
A3-B53-C1-D49
A9-B53-C1-D49
A13-B53-C1-D49
A24-B53-C1-D49
A69-B53-C1-D49
A67-B53-C1-D49

-continued
A39-B53-C1-D49
A65-B53-C1-D49
A66-B53-C1-D49
A2-B79-C1-D49
A3-B79-C1-D49
A9-B79-C1-D49
A13-B79-C1-D49
A24-B79-C1-D49
A69-B79-C1-D49
A67-B79-C1-D49
A39-B79-C1-D49
A65-B79-C1-D49
A66-B79-C1-D49
A2-B80-C1-D49
A3-B80-C1-D49
A9-B80-C1-D49
A13-B80-C1-D49
A24-B80-C1-D49
A69-B80-C1-D49
A67-B80-C1-D49
A39-B80-C1-D49
A65-B80-C1-D49
A66-B80-C1-D49
A2-B85-C1-D49
A3-B85-C1-D49
A9-B85-C1-D49
A13-B85-C1-D49
A24-B85-C1-D49
A69-B85-C1-D49
A67-B85-C1-D49
A39-B85-C1-D49
A65-B85-C1-D49
A66-B85-C1-D49
A2-B86-C1-D49
A3-B86-C1-D49
A9-B86-C1-D49
A13-B86-C1-D49
A24-B86-C1-D49
A69-B86-C1-D49
A67-B86-C1-D49
A39-B86-C1-D49
A65-B86-C1-D49
A66-B86-C1-D49
A2-B87-C1-D49
A3-B87-C1-D49
A9-B87-C1-D49
A13-B87-C1-D49
A24-B87-C1-D49
A69-B87-C1-D49
A67-B87-C1-D49
A39-B87-C1-D49
A65-B87-C1-D49
A66-B87-C1-D49
A2-B89-C1-D49
A3-B89-C1-D49
A9-B89-C1-D49
A13-B89-C1-D49
A24-B89-C1-D49
A69-B89-C1-D49
A67-B89-C1-D49
A39-B89-C1-D49
A65-B89-C1-D49
A66-B89-C1-D49
A2-B92-C1-D49
A3-B92-C1-D49
A9-B92-C1-D49
A13-B92-C1-D49
A24-B92-C1-D49
A69-B92-C1-D49
A67-B92-C1-D49
A39-B92-C1-D49
A65-B92-C1-D49
A66-B92-C1-D49
A2-B4-C2-D49
A3-B4-C2-D49
A9-B4-C2-D49
A13-B4-C2-D49
A24-B4-C2-D49
A69-B4-C2-D49
A67-B4-C2-D49

-continued
A39-B4-C2-D49
A65-B4-C2-D49
A66-B4-C2-D49
A2-B5-C2-D49
A3-B5-C2-D49
A9-B5-C2-D49
A13-B5-C2-D49
A24-B5-C2-D49
A69-B5-C2-D49
A67-B5-C2-D49
A39-B5-C2-D49
A65-B5-C2-D49
A66-B5-C2-D49
A2-B6-C2-D49
A3-B6-C2-D49
A9-B6-C2-D49
A13-B6-C2-D49
A24-B6-C2-D49
A69-B6-C2-D49
A67-B6-C2-D49
A39-B6-C2-D49
A65-B6-C2-D49
A66-B6-C2-D49
A2-B32-C2-D49
A3-B32-C2-D49
A9-B32-C2-D49
A13-B32-C2-D49
A24-B32-C2-D49
A69-B32-C2-D49
A67-B32-C2-D49
A39-B32-C2-D49
A65-B32-C2-D49
A66-B32-C2-D49
A2-B39-C2-D49
A3-B39-C2-D49
A9-B39-C2-D49
A13-B39-C2-D49
A24-B39-C2-D49
A69-B39-C2-D49
A67-B39-C2-D49
A39-B39-C2-D49
A65-B39-C2-D49
A66-B39-C2-D49
A2-B45-C2-D49
A3-B45-C2-D49
A9-B45-C2-D49
A13-B45-C2-D49
A24-B45-C2-D49
A69-B45-C2-D49
A67-B45-C2-D49
A39-B45-C2-D49
A65-B45-C2-D49
A66-B45-C2-D49
A2-B53-C2-D49
A3-B53-C2-D49
A9-B53-C2-D49
A13-B53-C2-D49
A24-B53-C2-D49
A69-B53-C2-D49
A67-B53-C2-D49
A39-B53-C2-D49
A65-B53-C2-D49
A66-B53-C2-D49
A2-B79-C2-D49
A3-B79-C2-D49
A9-B79-C2-D49
A13-B79-C2-D49
A24-B79-C2-D49
A69-B79-C2-D49
A67-B79-C2-D49
A39-B79-C2-D49
A65-B79-C2-D49
A66-B79-C2-D49
A2-B80-C2-D49
A3-B80-C2-D49
A9-B80-C2-D49
A13-B80-C2-D49
A24-B80-C2-D49
A69-B80-C2-D49
A67-B80-C2-D49

-continued
A39-B80-C2-D49
A65-B80-C2-D49
A66-B80-C2-D49
A2-B85-C2-D49
A3-B85-C2-D49
A9-B85-C2-D49
A13-B85-C2-D49
A24-B85-C2-D49
A69-B85-C2-D49
A67-B85-C2-D49
A39-B85-C2-D49
A65-B85-C2-D49
A66-B85-C2-D49
A2-B86-C2-D49
A3-B86-C2-D49
A9-B86-C2-D49
A13-B86-C2-D49
A24-B86-C2-D49
A69-B86-C2-D49
A67-B86-C2-D49
A39-B86-C2-D49
A65-B86-C2-D49
A66-B86-C2-D49
A2-B87-C2-D49
A3-B87-C2-D49
A9-B87-C2-D49
A13-B87-C2-D49
A24-B87-C2-D49
A69-B87-C2-D49
A67-B87-C2-D49
A39-B87-C2-D49
A65-B87-C2-D49
A66-B87-C2-D49
A2-B89-C2-D49
A3-B89-C2-D49
A9-B89-C2-D49
A13-B89-C2-D49
A24-B89-C2-D49
A69-B89-C2-D49
A67-B89-C2-D49
A39-B89-C2-D49
A65-B89-C2-D49
A66-B89-C2-D49
A2-B92-C2-D49
A3-B92-C2-D49
A9-B92-C2-D49
A13-B92-C2-D49
A24-B92-C2-D49
A69-B92-C2-D49
A67-B92-C2-D49
A39-B92-C2-D49
A65-B92-C2-D49
A66-B92-C2-D49
A2-B4-C3-D49
A3-B4-C3-D49
A9-B4-C3-D49
A13-B4-C3-D49
A24-B4-C3-D49
A69-B4-C3-D49
A67-B4-C3-D49
A39-B4-C3-D49
A65-B4-C3-D49
A66-B4-C3-D49
A2-B5-C3-D49
A3-B5-C3-D49
A9-B5-C3-D49
A13-B5-C3-D49
A24-B5-C3-D49
A69-B5-C3-D49
A67-B5-C3-D49
A39-B5-C3-D49
A65-B5-C3-D49
A66-B5-C3-D49
A2-B6-C3-D49
A3-B6-C3-D49
A9-B6-C3-D49
A13-B6-C3-D49
A24-B6-C3-D49
A69-B6-C3-D49
A67-B6-C3-D49

-continued
A39-B6-C3-D49
A65-B6-C3-D49
A66-B6-C3-D49
A2-B32-C3-D49
A3-B32-C3-D49
A9-B32-C3-D49
A13-B32-C3-D49
A24-B32-C3-D49
A69-B32-C3-D49
A67-B32-C3-D49
A39-B32-C3-D49
A65-B32-C3-D49
A66-B32-C3-D49
A2-B39-C3-D49
A3-B39-C3-D49
A9-B39-C3-D49
A13-B39-C3-D49
A24-B39-C3-D49
A69-B39-C3-D49
A67-B39-C3-D49
A39-B39-C3-D49
A65-B39-C3-D49
A66-B39-C3-D49
A2-B45-C3-D49
A3-B45-C3-D49
A9-B45-C3-D49
A13-B45-C3-D49
A24-B45-C3-D49
A69-B45-C3-D49
A67-B45-C3-D49
A39-B45-C3-D49
A65-B45-C3-D49
A66-B45-C3-D49
A2-B53-C3-D49
A3-B53-C3-D49
A9-B53-C3-D49
A13-B53-C3-D49
A24-B53-C3-D49
A69-B53-C3-D49
A67-B53-C3-D49
A39-B53-C3-D49
A65-B53-C3-D49
A66-B53-C3-D49
A2-B79-C3-D49
A3-B79-C3-D49
A9-B79-C3-D49
A13-B79-C3-D49
A24-B79-C3-D49
A69-B79-C3-D49
A67-B79-C3-D49
A39-B79-C3-D49
A65-B79-C3-D49
A66-B79-C3-D49
A2-B80-C3-D49
A3-B80-C3-D49
A9-B80-C3-D49
A13-B80-C3-D49
A24-B80-C3-D49
A69-B80-C3-D49
A67-B80-C3-D49
A39-B80-C3-D49
A65-B80-C3-D49
A66-B80-C3-D49
A2-B85-C3-D49
A3-B85-C3-D49
A9-B85-C3-D49
A13-B85-C3-D49
A24-B85-C3-D49
A69-B85-C3-D49
A67-B85-C3-D49
A39-B85-C3-D49
A65-B85-C3-D49
A66-B85-C3-D49
A2-B86-C3-D49
A3-B86-C3-D49
A9-B86-C3-D49
A13-B86-C3-D49
A24-B86-C3-D49
A69-B86-C3-D49
A67-B86-C3-D49

-continued
A39-B86-C3-D49
A65-B86-C3-D49
A66-B86-C3-D49
A2-B87-C3-D49
A3-B87-C3-D49
A9-B87-C3-D49
A13-B87-C3-D49
A24-B87-C3-D49
A69-B87-C3-D49
A67-B87-C3-D49
A39-B87-C3-D49
A65-B87-C3-D49
A66-B87-C3-D49
A2-B89-C3-D49
A3-B89-C3-D49
A9-B89-C3-D49
A13-B89-C3-D49
A24-B89-C3-D49
A69-B89-C3-D49
A67-B89-C3-D49
A39-B89-C3-D49
A65-B89-C3-D49
A66-B89-C3-D49
A2-B92-C3-D49
A3-B92-C3-D49
A9-B92-C3-D49
A13-B92-C3-D49
A24-B92-C3-D49
A69-B92-C3-D49
A67-B92-C3-D49
A39-B92-C3-D49
A65-B92-C3-D49
A66-B92-C3-D49
A2-B4-C4-D49
A3-B4-C4-D49
A9-B4-C4-D49
A13-B4-C4-D49
A24-B4-C4-D49
A69-B4-C4-D49
A67-B4-C4-D49
A39-B4-C4-D49
A65-B4-C4-D49
A66-B4-C4-D49
A2-B5-C4-D49
A3-B5-C4-D49
A9-B5-C4-D49
A13-B5-C4-D49
A24-B5-C4-D49
A69-B5-C4-D49
A67-B5-C4-D49
A39-B5-C4-D49
A65-B5-C4-D49
A66-B5-C4-D49
A2-B6-C4-D49
A3-B6-C4-D49
A9-B6-C4-D49
A13-B6-C4-D49
A24-B6-C4-D49
A69-B6-C4-D49
A67-B6-C4-D49
A39-B6-C4-D49
A65-B6-C4-D49
A66-B6-C4-D49
A2-B32-C4-D49
A3-B32-C4-D49
A9-B32-C4-D49
A13-B32-C4-D49
A24-B32-C4-D49
A69-B32-C4-D49
A67-B32-C4-D49
A39-B32-C4-D49
A65-B32-C4-D49
A66-B32-C4-D49
A2-B39-C4-D49
A3-B39-C4-D49
A9-B39-C4-D49
A13-B39-C4-D49
A24-B39-C4-D49
A69-B39-C4-D49
A67-B39-C4-D49

-continued
A39-B39-C4-D49
A65-B39-C4-D49
A66-B39-C4-D49
A2-B45-C4-D49
A3-B45-C4-D49
A9-B45-C4-D49
A13-B45-C4-D49
A24-B45-C4-D49
A69-B45-C4-D49
A67-B45-C4-D496
A39-B45-C4-D49
A65-B45-C4-D49
A66-B45-C4-D49
A2-B53-C4-D49
A3-B53-C4-D49
A9-B53-C4-D49
A13-B53-C4-D49
A24-B53-C4-D49
A69-B53-C4-D49
A67-B53-C4-D49
A39-B53-C4-D49
A65-B53-C4-D49
A66-B53-C4-D49
A2-B79-C4-D49
A3-B79-C4-D49
A9-B79-C4-D49
A13-B79-C4-D49
A24-B79-C4-D49
A69-B79-C4-D49
A67-B79-C4-D49
A39-B79-C4-D49
A65-B79-C4-D49
A66-B79-C4-D49
A2-B80-C4-D49
A3-B80-C4-D49
A9-B80-C4-D49
A13-B80-C4-D49
A24-B80-C4-D49
A69-B80-C4-D49
A67-B80-C4-D49
A39-B80-C4-D49
A65-B80-C4-D49
A66-B80-C4-D49
A2-B85-C4-D49
A3-B85-C4-D49
A9-B85-C4-D49
A13-B85-C4-D49
A24-B85-C4-D49
A69-B85-C4-D49
A67-B85-C4-D49
A39-B85-C4-D49
A65-B85-C4-D49
A66-B85-C4-D49
A2-B86-C4-D49
A3-B86-C4-D49
A9-B86-C4-D49
A13-B86-C4-D49
A24-B86-C4-D49
A69-B86-C4-D49
A67-B86-C4-D49
A39-B86-C4-D49
A65-B86-C4-D49
A66-B86-C4-D49
A2-B87-C4-D49
A3-B87-C4-D49
A9-B87-C4-D49
A13-B87-C4-D49
A24-B87-C4-D49
A69-B87-C4-D49
A67-B87-C4-D49
A39-B87-C4-D49
A65-B87-C4-D49
A66-B87-C4-D49
A2-B89-C4-D49
A3-B89-C4-D49
A9-B89-C4-D49
A13-B89-C4-D49
A24-B89-C4-D49
A69-B89-C4-D49
A67-B89-C4-D49

-continued
A39-B89-C4-D49
A65-B89-C4-D49
A66-B89-C4-D49
A2-B92-C4-D49
A3-B92-C4-D49
A9-B92-C4-D49
A13-B92-C4-D49
A24-B92-C4-D49
A69-B92-C4-D49
A67-B92-C4-D49
A39-B92-C4-D49
A65-B92-C4-D49
A66-B92-C4-D49
A2-B4-C5-D49
A3-B4-C5-D49
A9-B4-C5-D49
A13-B4-C5-D49
A24-B4-C5-D49
A69-B4-C5-D49
A67-B4-C5-D49
A39-B4-C5-D49
A65-B4-C5-D49
A66-B4-C5-D49
A2-B5-C5-D49
A3-B5-C5-D49
A9-B5-C5-D49
A13-B5-C5-D49
A24-B5-C5-D49
A69-B5-C5-D49
A67-B5-C5-D49
A39-B5-C5-D49
A65-B5-C5-D49
A66-B5-C5-D49
A2-B6-C5-D49
A3-B6-C5-D49
A9-B6-C5-D49
A13-B6-C5-D49
A24-B6-C5-D49
A69-B6-C5-D49
A67-B6-C5-D49
A39-B6-C5-D49
A65-B6-C5-D49
A66-B6-C5-D49
A2-B32-C5-D49
A3-B32-C5-D49
A9-B32-C5-D49
A13-B32-C5-D49
A24-B32-C5-D49
A69-B32-C5-D49
A67-B32-C5-D49
A39-B32-C5-D49
A65-B32-C5-D49
A66-B32-C5-D49
A2-B39-C5-D49
A3-B39-C5-D49
A9-B39-C5-D49
A13-B39-C5-D49
A24-B39-C5-D49
A69-B39-C5-D49
A67-B39-C5-D49
A39-B39-C5-D49
A65-B39-C5-D49
A66-B39-C5-D49
A2-B45-C5-D49
A3-B45-C5-D49
A9-B45-C5-D49
A13-B45-C5-D49
A24-B45-C5-D49
A69-B45-C5-D49
A67-B45-C5-D49
A39-B45-C5-D49
A65-B45-C5-D49
A66-B45-C5-D49
A2-B53-C5-D49
A3-B53-C5-D49
A9-B53-C5-D49
A13-B53-C5-D49
A24-B53-C5-D49
A69-B53-C5-D49
A67-B53-C5-D49

-continued
A39-B53-C5-D49
A65-B53-C5-D49
A66-B53-C5-D49
A2-B79-C5-D49
A3-B79-C5-D49
A9-B79-C5-D49
A13-B79-C5-D49
A24-B79-C5-D49
A69-B79-C5-D49
A67-B79-C5-D49
A39-B79-C5-D49
A65-B79-C5-D49
A66-B79-C5-D49
A2-B80-C5-D49
A3-B80-C5-D49
A9-B80-C5-D49
A13-B80-C5-D49
A24-B80-C5-D49
A69-B80-C5-D49
A67-B80-C5-D49
A39-B80-C5-D49
A65-B80-C5-D49
A66-B80-C5-D49
A2-B85-C5-D49
A3-B85-C5-D49
A9-B85-C5-D49
A13-B85-C5-D49
A24B85-C5-D49
A69-B85-C5-D49
A67-B85-C5-D49
A39-B85-C5-D49
A65-B85-C5-D49
A66-B85-C5-D49
A2-B86-C5-D49
A3-B86-C5-D49
A9-B86-C5-D49
A13-B86-C5-D49
A24-B86-C5-D49
A69-B86-C5-D49
A67-B86-C5-D49
A39-B86-C5-D49
A65-B86-C5-D49
A66-B86-C5-D49
A2-B87-C5-D49
A3-B87-C5-D49
A9-B87-C5-D49
A13-B87-C5-D49
A24-B87-C5-D49
A69-B87-C5-D49
A67-B87-C5-D49
A39-B87-C5-D49
A65-B87-C5-D49
A66-B87-C5-D49
A2-B89-C5-D49
A3-B89-C5-D49
A9-B89-C5-D49
A13-B89-C5-D49
A24-B89-C5-D49
A69-B89-C5-D49
A67-B89-C5-D49
A39-B89-C5-D49
A65-B89-C5-D49
A66-B89-C5-D49
A2-B92-C5-D49
A3-B92-C5-D49
A9-B92-C5-D49
A13-B92-C5-D49
A24-B92-C5-D49
A69-B92-C5-D49
A67-B92-C5-D49
A39-B92-C5-D49
A65-B92-C5-D49
A66-B92-C5-D49
A2-B4-C6-D49
A3-B4-C6-D49
A9-B4-C6-D49
A13-B4-C6-D49
A24-B4-C6-D49
A69-B4-C6-D49
A67-B4-C6-D49

-continued
A39-B4-C6-D49
A65-B4-C6-D49
A66-B4-C6-D49
A2-B5-C6-D49
A3-B5-C6-D49
A9-B5-C6-D49
A13-B5-C6-D49
A24-B5-C6-D49
A69-B5-C6-D49
A67-B5-C6-D49
A39-B5-C6-D49
A65-B5-C6-D49
A66-B5-C6-D49
A2-B6-C6-D49
A3-B6-C6-D49
A9-B6-C6-D49
A13-B6-C6-D49
A24-B6-C6-D49
A69-B6-C6-D49
A67-B6-C6-D49
A39-B6-C6-D49
A65-B6-C6-D49
A66-B6-C6-D49
A2-B32-C6-D49
A3-B32-C6-D49
A9-B32-C6-D49
A13-B32-C6-D49
A24-B32-C6-D49
A69-B32-C6-D49
A67-B32-C6-D49
A39-B32-C6-D49
A65-B32-C6-D49
A66-B32-C6-D49
A2-B39-C6-D49
A3-B39-C6-D49
A9-B39-C6-D49
A13-B39-C6-D49
A24-B39-C6-D49
A69-B39-C6-D49
A67-B39-C6-D49
A39-B39-C6-D49
A65-B39-C6-D49
A66-B39-C6-D49
A2-B45-C6-D49
A3-B45-C6-D49
A9-B45-C6-D49
A13-B45-C6-D49
A24-B45-C6-D49
A69-B45-C6-D49
A67-B45-C6-D49
A39-B45-C6-D49
A65-B45-C6-D49
A66-B45-C6-D49
A2-B53-C6-D49
A3-B53-C6-D49
A9-B53-C6-D49
A13-B53-C6-D49
A24-B53-C6-D49
A69-B53-C6-D49
A67-B53-C6-D49
A39-B53-C6-D49
A65-B53-C6-D49
A66-B53-C6-D49
A2-B79-C6-D49
A3-B79-C6-D49
A9-B79-C6-D49
A13-B79-C6-D49
A24-B79-C6-D49
A69-B79-C6-D49
A67-B79-C6-D49
A39-B79-C6-D49
A65-B79-C6-D49
A66-B79-C6-D49
A2-B80-C6-D49
A3-B80-C6-D49
A9-B80-C6-D49
A13-B80-C6-D49
A24-B80-C6-D49
A69-B80-C6-D49
A67-B80-C6-D49

-continued
A39-B80-C6-D49
A65-B80-C6-D49
A66-B80-C6-D49
A2-B85-C6-D49
A3-B85-C6-D49
A9-B85-C6-D49
A13-B85-C6-D49
A24-B85-C6-D49
A69-B85-C6-D49
A67-B85-C6-D49
A39-B85-C6-D49
A65-B85-C6-D49
A66-B85-C6-D49
A2-B86-C6-D49
A3-B86-C6-D49
A9-B86-C6-D49
A13-B86-C6-D49
A24-B86-C6-D49
A69-B86-C6-D49
A67-B86-C6-D49
A39-B86-C6-D49
A65-B86-C6-D49
A66-B86-C6-D49
A2-B87-C6-D49
A3-B87-C6-D49
A9-B87-C6-D49
A13-B87-C6-D49
A24-B87-C6-D49
A69-B87-C6-D49
A67-B87-C6-D49
A39-B87-C6-D49
A65-B87-C6-D49
A66-B87-C6-D49
A2-B89-C6-D49
A3-B89-C6-D49
A9-B89-C6-D49
A13-B89-C6-D49
A24-B89-C6-D49
A69-B89-C6-D49
A67-B89-C6-D49
A39-B89-C6-D49
A65-B89-C6-D49
A66-B89-C6-D49
A2-B92-C6-D49
A3-B92-C6-D49
A9-B92-C6-D49
A13-B92-C6-D49
A24-B92-C6-D49
A69-B92-C6-D49
A67-B92-C6-D49
A39-B92-C6-D49
A65-B92-C6-D49
A66-B92-C6-D49
A2-B4-C7-D49
A3-B4-C7-D49
A9-B4-C7-D49
A13-B4-C7-D49
A24-B4-C7-D49
A69-B4-C7-D49
A67-B4-C7-D49
A39-B4-C7-D49
A65-B4-C7-D49
A66-B4-C7-D49
A2-B5-C7-D49
A3-B5-C7-D49
A9-B5-C7-D49
A13-B5-C7-D49
A24-B5-C7-D49
A69-B5-C7-D49
A67-B5-C7-D49
A39-B5-C7-D49
A65-B5-C7-D49
A66-B5-C7-D49
A2-B6-C7-D49
A3-B6-C7-D49
A9-B6-C7-D49
A13-B6-C7-D49
A24-B6-C7-D49
A69-B6-C7-D49
A67-B6-C7-D49

-continued
A39-B6-C7-D49
A65-B6-C7-D49
A66-B6-C7-D49
A2-B32-C7-D49
A3-B32-C7-D49
A9-B32-C7-D49
A13-B32-C7-D49
A24-B32-C7-D49
A69-B32-C7-D49
A67-B32-C7-D49
A39-B32-C7-D49
A65-B32-C7-D49
A66-B32-C7-D49
A2-B39-C7-D49
A3-B39-C7-D49
A9-B39-C7-D49
A13-B39-C7-D49
A24-B39-C7-D49
A69-B39-C7-D49
A67-B39-C7-D49
A39-B39-C7-D49
A65-B39-C7-D49
A66-B39-C7-D49
A2-B45-C7-D49
A3-B45-C7-D49
A9-B45-C7-D49
A13-B45-C7-D49
A24-B45-C7-D49
A69-B45-C7-D49
A67-B45-C7-D49
A39-B45-C7-D49
A65-B45-C7-D49
A66-B45-C7-D49
A2-B53-C7-D49
A3-B53-C7-D49
A9-B53-C7-D49
A13-B53-C7-D49
A24-B53-C7-D49
A69-B53-C7-D49
A67-B53-C7-D49
A39-B53-C7-D49
A65-B53-C7-D49
A66-B53-C7-D49
A2-B79-C7-D49
A3-B79-C7-D49
A9-B79-C7-D49
A13-B79-C7-D49
A24-B79-C7-D49
A69-B79-C7-D49
A67-B79-C7-D49
A39-B79-C7-D49
A65-B79-C7-D49
A66-B79-C7-D49
A2-B80-C7-D49
A3-B80-C7-D49
A9-B80-C7-D49
A13-B80-C7-D49
A24-B80-C7-D49
A69-B80-C7-D49
A67-B80-C7-D49
A39-B80-C7-D49
A65-B80-C7-D49
A66-B80-C7-D49
A2-B85-C7-D49
A3-B85-C7-D49
A9-B85-C7-D49
A13-B85-C7-D49
A24-B85-C7-D49
A69-B85-C7-D49
A67-B85-C7-D49
A39-B85-C7-D49
A65-B85-C7-D49
A66-B85-C7-D49
A2-B86-C7-D49
A3-B86-C7-D49
A9-B86-C7-D49
A13-B86-C7-D49
A24-B86-C7-D49
A69-B86-C7-D49
A67-B86-C7-D49

-continued
A39-B86-C7-D49
A65-B86-C7-D49
A66-B86-C7-D49
A2-B87-C7-D49
A3-B87-C7-D49
A9-B87-C7-D49
A13-B87-C7-D49
A24-B87-C7-D49
A69-B87-C7-D49
A67-B87-C7-D49
A39-B87-C7-D49
A65-B87-C7-D49
A66-B87-C7-D49
A2-B89-C7-D49
A3-B89-C7-D49
A9-B89-C7-D49
A13-B89-C7-D49
A24-B89-C7-D49
A69-B89-C7-D49
A67-B89-C7-D49
A39-B89-C7-D49
A65-B89-C7-D49
A66-B89-C7-D49
A2-B92-C7-D49
A3-B92-C7-D49
A9-B92-C7-D49
A13-B92-C7-D49
A24-B92-C7-D49
A69-B92-C7-D49
A67-B92-C7-D49
A39-B92-C7-D49
A65-B92-C7-D49
A66-B92-C7-D49
A2-B4-C8-D49
A3-B4-C8-D49
A9-B4-C8-D49
A13-B4-C8-D49
A24-B4-C8-D49
A69-B4-C8-D49
A67-B4-C8-D49
A39-B4-C8-D49
A65-B4-C8-D49
A66-B4-C8-D49
A2-B5-C8-D49
A3-B5-C8-D49
A9-B5-C8-D49
A13-B5-C8-D49
A24-B5-C8-D49
A69-B5-C8-D49
A67-B5-C8-D49
A39-B5-C8-D49
A65-B5-C8-D49
A66-B5-C8-D49
A2-B6-C8-D49
A3-B6-C8-D49
A9-B6-C8-D49
A13-B6-C8-D49
A24-B6-C8-D49
A69-B6-C8-D49
A67-B6-C8-D49
A39-B6-C8-D49
A65-B6-C8-D49
A66-B6-C8-D49
A2-B32-C8-D49
A3-B32-C8-D49
A9-B32-C8-D49
A13-B32-C8-D49
A24-B32-C8-D49
A69-B32-C8-D49
A67-B32-C8-D49
A39-B32-C8-D49
A65-B32-C8-D49
A66-B32-C8-D49
A2-B39-C8-D49
A3-B39-C8-D49
A9-B39-C8-D49
A13-B39-C8-D49
A24-B39-C8-D49
A69-B39-C8-D49
A67-B39-C8-D49

-continued
A39-B39-C8-D49
A65-B39-C8-D49
A66-B39-C8-D49
A2-B45-C8-D49
A3-B45-C8-D49
A9-B45-C8-D49
A13-B45-C8-D49
A24-B45-C8-D49
A69-B45-C8-D49
A67-B45-C8-D49
A39-B45-C8-D49
A65-B45-C8-D49
A66-B45-C8-D49
A2-B53-C8-D49
A3-B53-C8-D49
A9-B53-C8-D49
A13-B53-C8-D49
A24-B53-C8-D49
A69-B53-C8-D49
A67-B53-C8-D49
A39-B53-C8-D49
A65-B53-C8-D49
A66-B53-C8-D49
A2-B79-C8-D49
A3-B79-C8-D49
A9-B79-C8-D49
A13-B79-C8-D49
A24-B79-C8-D49
A69-B79-C8-D49
A67-B79-C8-D49
A39-B79-C8-D49
A65-B79-C8-D49
A66-B79-C8-D49
A2-B80-C8-D49
A3-B80-C8-D49
A9-B80-C8-D49
A13-B80-C8-D49
A24-B80-C8-D49
A69-B80-C8-D49
A67-B80-C8-D49
A39-B80-C8-D49
A65-B80-C8-D49
A66-B80-C8-D49
A2-B85-C8-D49
A3-B85-C8-D49
A9-B85-C8-D49
A13-B85-C8-D49
A24-B85-C8-D49
A69-B85-C8-D49
A67-B85-C8-D49
A39-B85-C8-D49
A65-B85-C8-D49
A66-B85-C8-D49
A2-B86-C8-D49
A3-B86-C8-D49
A9-B86-C8-D49
A13-B86-C8-D49
A24-B86-C8-D49
A69-B86-C8-D49
A67-B86-C8-D49
A39-B86-C8-D49
A65-B86-C8-D49
A66-B86-C8-D49
A2-B87-C8-D49
A3-B87-C8-D49
A9-B87-C8-D49
A13-B87-C8-D49
A24-B87-C8-D49
A69-B87-C8-D49
A67-B87-C8-D49
A39-B87-C8-D49
A65-B87-C8-D49
A66-B87-C8-D49
A2-B89-C8-D49
A3-B89-C8-D49
A9-B89-C8-D49
A13-B89-C8-D49
A24-B89-C8-D49
A69-B89-C8-D49
A67-B89-C8-D49

-continued
A39-B89-C8-D49
A65-B89-C8-D49
A66-B89-C8-D49
A2-B92-C8-D49
A3-B92-C8-D49
A9-B92-C8-D49
A13-B92-C8-D49
A24-B92-C8-D49
A69-B92-C8-D49
A67-B92-C8-D49
A39-B92-C8-D49
A65-B92-C8-D49
A66-B92-C8-D49
A2-B4-C9-D49
A3-B4-C9-D49
A9-B4-C9-D49
A13-B4-C9-D49
A24-B4-C9-D49
A69-B4-C9-D49
A67-B4-C9-D49
A39-B4-C9-D49
A65-B4-C9-D49
A66-B4-C9-D49
A2-B5-C9-D49
A3-B5-C9-D49
A9-B5-C9-D49
A13-B5-C9-D49
A24-B5-C9-D49
A69-B5-C9-D49
A67-B5-C9-D49
A39-B5-C9-D49
A65-B5-C9-D49
A66-B5-C9-D49
A2-B6-C9-D49
A3-B6-C9-D49
A9-B6-C9-D49
A13-B6-C9-D49
A24-B6-C9-D49
A69-B6-C9-D49
A67-B6-C9-D49
A39-B6-C9-D49
A65-B6-C9-D49
A66-B6-C9-D49
A2-B32-C9-D49
A3-B32-C9-D49
A9-B32-C9-D49
A13-B32-C9-D49
A24-B32-C9-D49
A69-B32-C9-D49
A67-B32-C9-D49
A39-B32-C9-D49
A65-B32-C9-D49
A66-B32-C9-D49
A2-B39-C9-D49
A3-B39-C9-D49
A9-B39-C9-D49
A13-B39-C9-D49
A24-B39-C9-D49
A69-B39-C9-D49
A67-B39-C9-D49
A39-B39-C9-D49
A65-B39-C9-D49
A66-B39-C9-D49
A2-B45-C9-D49
A3-B45-C9-D49
A9-B45-C9-D49
A13-B45-C9-D49
A24-B45-C9-D49
A69-B45-C9-D49
A67-B45-C9-D49
A39-B45-C9-D49
A65-B45-C9-D49
A66-B45-C9-D49
A2-B53-C9-D49
A3-B53-C9-D49
A9-B53-C9-D49
A13-B53-C9-D49
A24-B53-C9-D49
A69-B53-C9-D49
A67-B53-C9-D49

-continued
A39-B53-C9-D49
A65-B53-C9-D49
A66-B53-C9-D49
A2-B79-C9-D49
A3-B79-C9-D49
A9-B79-C9-D49
A13-B79-C9-D49
A24-B79-C9-D49
A69-B79-C9-D49
A67-B79-C9-D49
A39-B79-C9-D49
A65-B79-C9-D49
A66-B79-C9-D49
A2-B80-C9-D49
A3-B80-C9-D49
A9-B80-C9-D49
A13-B80-C9-D49
A24-B80-C9-D49
A69-B80-C9-D49
A67-B80-C9-D49
A39-B80-C9-D49
A65-B80-C9-D49
A66-B80-C9-D49
A2-B85-C9-D49
A3-B85-C9-D49
A9-B85-C9-D49
A13-B85-C9-D49
A24-B85-C9-D49
A69-B85-C9-D49
A67-B85-C9-D49
A39-B85-C9-D49
A65-B85-C9-D49
A66-B85-C9-D49
A2-B86-C9-D49
A3-B86-C9-D49
A9-B86-C9-D49
A13-B86-C9-D49
A24-B86-C9-D49
A69-B86-C9-D49
A67-B86-C9-D49
A39-B86-C9-D49
A65-B86-C9-D49
A66-B86-C9-D49
A2-B87-C9-D49
A3-B87-C9-D49
A9-B87-C9-D49
A13-B87-C9-D49
A24-B87-C9-D49
A69-B87-C9-D49
A67-B87-C9-D49
A39-B87-C9-D49
A65-B87-C9-D49
A66-B87-C9-D49
A2-B89-C9-D49
A3-B89-C9-D49
A9-B89-C9-D49
A13-B89-C9-D49
A24-B89-C9-D49
A69-B89-C9-D49
A67-B89-C9-D49
A39-B89-C9-D49
A65-B89-C9-D49
A66-B89-C9-D49
A2-B92-C9-D49
A3-B92-C9-D49
A9-B92-C9-D49
A13-B92-C9-D49
A24-B92-C9-D49
A69-B92-C9-D49
A67-B92-C9-D49
A39-B92-C9-D49
A65-B92-C9-D49
A66-B92-C9-D49
A2-B4-C10-D49
A3-B4-C10-D49
A9-B4-C10-D49
A13-B4-C10-D49
A24-B4-C10-D49
A69-B4-C10-D49
A67-B4-C10-D49

-continued
A39-B4-C10-D49
A65-B4-C10-D49
A66-B4-C10-D49
A2-B5-C10-D49
A3-B5-C10-D49
A9-B5-C10-D49
A13-B5-C10-D49
A24-B5-C10-D49
A69-B5-C10-D49
A67-B5-C10-D49
A39-B5-C10-D49
A65-B5-C10-D49
A66-B5-C10-D49
A2-B6-C10-D49
A3-B6-C10-D49
A9-B6-C10-D49
A13-B6-C10-D49
A24-B6-C10-D49
A69-B6-C10-D49
A67-B6-C10-D49
A39-B6-C10-D49
A65-B6-C10-D49
A66-B6-C10-D49
A2-B32-C10-D49
A3-B32-C10-D49
A9-B32-C10-D49
A13-B32-C10-D49
A24-B32-C10-D49
A69-B32-C10-D49
A67-B32-C10-D49
A39-B32-C10-D49
A65-B32-C10-D49
A66-B32-C10-D49
A2-B39-C10-D49
A3-B39-C10-D49
A9-B39-C10-D49
A13-B39-C10-D49
A24-B39-C10-D49
A69-B39-C10-D49
A67-B39-C10-D49
A39-B39-C10-D49
A65-B39-C10-D49
A66-B39-C10-D49
A2-B45-C10-D49
A3-B45-C10-D49
A9-B45-C10-D49
A13-B45-C10-D49
A24-B45-C10-D49
A69-B45-C10-D49
A67-B45-C10-D49
A39-B45-C10-D49
A65-B45-C10-D49
A66-B45-C10-D49
A2-B53-C10-D49
A3-B53-C10-D49
A9-B53-C10-D49
A13-B53-C10-D49
A24-B53-C10-D49
A69-B53-C10-D49
A67-B53-C10-D49
A39-B53-C10-D49
A65-B53-C10-D49
A66-B53-C10-D49
A2-B79-C10-D49
A3-B79-C10-D49
A9-B79-C10-D49
A13-B79-C10-D49
A24-B79-C10-D49
A69-B79-C10-D49
A67-B79-C10-D49
A39-B79-C10-D49
A65-B79-C10-D49
A66-B79-C10-D49
A2-B80-C10-D49
A3-B80-C10-D49
A9-B80-C10-D49
A13-B80-C10-D49
A24-B80-C10-D49
A69-B80-C10-D49
A67-B80-C10-D49

-continued

A39-B80-C10-D49
A65-B80-C10-D49
A66-B80-C10-D49
A2-B85-C10-D49
A3-B85-C10-D49
A9-B85-C10-D49
A13-B85-C10-D49
A24-B85-C10-D49
A69-B85-C10-D49
A67-B85-C10-D49
A39-B85-C10-D49
A65-B85-C10-D49
A66-B85-C10-D49
A2-B86-C10-D49
A3-B86-C10-D49
A9-B86-C10-D49
A13-B86-C10-D49
A24-B86-C10-D49
A69-B86-C10-D49
A67-B86-C10-D49
A39-B86-C10-D49
A65-B86-C10-D49
A66-B86-C10-D49
A2-B87-C10-D49
A3-B87-C10-D49
A9-B87-C10-D49
A13-B87-C10-D49
A24-B87-C10-D49
A69-B87-C10-D49
A67-B87-C10-D49
A39-B87-C10-D49
A65-B87-C10-D49
A66-B87-C10-D49
A2-B89-C10-D49
A3-B89-C10-D49
A9-B89-C10-D49
A13-B89-C10-D49
A24-B89-C10-D49
A69-B89-C10-D49
A67-B89-C10-D49
A39-B89-C10-D49
A65-B89-C10-D49
A66-B89-C10-D49
A2-B92-C10-D49
A3-B92-C10-D49
A9-B92-C10-D49
A13-B92-C10-D49
A24-B92-C10-D49
A69-B92-C10-D49
A67-B92-C10-D49
A39-B92-C10-D49
A65-B92-C10-D49
A66-B92-C10-D49
A2-B4-C11-D49
A3-B4-C11-D49
A9-B4-C11-D49
A13-B4-C11-D49
A24-B4-C11-D49
A69-B4-C11-D49
A67-B4-C11-D49
A39-B4-C11-D49
A65-B4-C11-D49
A66-B4-C11-D49
A2-B5-C11-D49
A3-B5-C11-D49
A9-B5-C11-D49
A13-B5-C11-D49
A24-B5-C11-D49
A69-B5-C11-D49
A67-B5-C11-D49
A39-B5-C11-D49
A65-B5-C11-D49
A66-B5-C11-D49
A2-B6-C11-D49
A3-B6-C11-D49
A9-B6-C11-D49
A13-B6-C11-D49
A24-B6-C11-D49
A69-B6-C11-D49
A67-B6-C11-D49

-continued

A39-B6-C11-D49
A65-B6-C11-D49
A66-B6-C11-D49
A2-B32-C11-D49
A3-B32-C11-D49
A9-B32-C11-D49
A13-B32-C11-D49
A24-B32-C11-D49
A69-B32-C11-D49
A67-B32-C11-D49
A39-B32-C11-D49
A65-B32-C11-D49
A66-B32-C11-D49
A2-B39-C11-D49
A3-B39-C11-D49
A9-B39-C11-D49
A13-B39-C11-D49
A24-B39-C11-D49
A69-B39-C11-D49
A67-B39-C11-D49
A39-B39-C11-D49
A65-B39-C11-D49
A66-B39-C11-D49
A2-B45-C11-D49
A3-B45-C11-D49
A9-B45-C11-D49
A13-B45-C11-D49
A24-B45-C11-D49
A69-B45-C11-D49
A67-B45-C11-D49
A39-B45-C11-D49
A65-B45-C11-D49
A66-B45-C11-D49
A2-B53-C11-D49
A3-B53-C11-D49
A9-B53-C11-D49
A13-B53-C11-D49
A24-B53-C11-D49
A69-B53-C11-D49
A67-B53-C11-D49
A39-B53-C11-D49
A65-B53-C11-D49
A66-B53-C11-D49
A2-B79-C11-D49
A3-B79-C11-D49
A9-B79-C11-D49
A13-B79-C11-D49
A24-B79-C11-D49
A69-B79-C11-D49
A67-B79-C11-D49
A39-B79-C11-D49
A65-B79-C11-D49
A66-B79-C11-D49
A2-B80-C11-D49
A3-B80-C11-D49
A9-B80-C11-D49
A13-B80-C11-D49
A24-B80-C11-D49
A69-B80-C11-D49
A67-B80-C11-D49
A39-B80-C11-D49
A65-B80-C11-D49
A66-B80-C11-D49
A2-B85-C11-D49
A3-B85-C11-D49
A9-B85-C11-D49
A13-B85-C11-D49
A24-B85-C11-D49
A69-B85-C11-D49
A67-B85-C11-D49
A39-B85-C11-D49
A65-B85-C11-D49
A66-B85-C11-D49
A2-B86-C11-D49
A3-B86-C11-D49
A9-B86-C11-D49
A13-B86-C11-D49
A24-B86-C11-D49
A69-B86-C11-D49
A67-B86-C11-D49

-continued

A39-B86-C11-D49
A65-B86-C11-D49
A66-B86-C11-D49
A2-B87-C11-D49
A3-B87-C11-D49
A9-B87-C11-D49
A13-B87-C11-D49
A24-B87-C11-D49
A69-B87-C11-D49
A67-B87-C11-D49
A39-B87-C11-D49
A65-B87-C11-D49
A66-B87-C11-D49
A2-B89-C11-D49
A3-B89-C11-D49
A9-B89-C11-D49
A13-B89-C11-D49
A24-B89-C11-D49
A69-B89-C11-D49
A67-B89-C1L-D49
A39-B89-C11-D49
A65-B89-C11-D49
A66-B89-C11-D49
A2-B92-C11-D49
A3-B92-C11-D49
A9-B92-C11-D49
A13-B92-C11-D49
A24-B92-C11-D49
A69-B92-C11-D49
A67-B92-C11-D49
A39-B92-C11-D49
A65-B92-C11-D49
A66-B92-C11-D49
A2-B4-C12-D49
A3-B4-C12-D49
A9-B4-C12-D49
A13-B4-C12-D49
A24-B4-C12-D49
A69-B4-C12-D49
A67-B4-C12-D49
A39-B4-C12-D49
A65-B4-C12-D49
A66-B4-C12-D49
A2-B5-C12-D49
A3-B5-C12-D49
A9-B5-C12-D49
A13-B5-C12-D49
A24-B5-C12-D49
A69-B5-C12-D49
A67-B5-C12-D49
A39-B5-C12-D49
A65-B5-C12-D49
A66-B5-C12-D49
A2-B6-C12-D49
A3-B6-C12-D49
A9-B6-C12-D49
A13-B6-C12-D49
A24-B6-C12-D49
A69-B6-C12-D49
A67-B6-C12-D49
A39-B6-C12-D49
A65-B6-C12-D49
A66-B6-C12-D49
A2-B32-C12-D49
A3-B32-C12-D49
A9-B32-C12-D49
A13-B32-C12-D49
A24-B32-C12-D49
A69-B32-C12-D49
A67-B32-C12-D49
A39-B32-C12-D49
A65-B32-C12-D49
A66-B32-C12-D49
A2-B39-C12-D49
A3-B39-C12-D49
A9-B39-C12-D49
A13-B39-C12-D49
A24-B39-C12-D49
A69-B39-C12-D49
A67-B39-C12-D49

-continued

A39-B39-C12-D49
A65-B39-C12-D49
A66-B39-C12-D49
A2-B45-C12-D49
A3-B45-C12-D49
A9-B45-C12-D49
A13-B45-C12-D49
A24-B45-C12-D49
A69-B45-C12-D49
A67-B45-C12-D49
A39-B45-C12-D49
A65-B45-C12-D49
A66-B45-C12-D49
A2-B53-C12-D49
A3-B53-C12-D49
A9-B53-C12-D49
A13-B53-C12-D49
A24-B53-C12-D49
A69-B53-C12-D49
A67-B53-C12-D49
A39-B53-C12-D49
A65-B53-C12-D49
A66-B53-C12-D49
A2-B79-C12-D49
A3-B79-C12-D49
A9-B79-C12-D49
A13-B79-C12-D49
A24-B79-C12-D49
A69-B79-C12-D49
A67-B79-C12-D49
A39-B79-C12-D49
A65-B79-C12-D49
A66-B79-C12-D49
A2-B80-C12-D49
A3-B80-C12-D49
A9-B80-C12-D49
A13-B80-C12-D49
A24-B80-C12-D49
A69-B80-C12-D49
A67-B80-C12-D49
A39-B80-C12-D49
A65-B80-C12-D49
A66-B80-C12-D49
A2-B85-C12-D49
A3-B85-C12-D49
A9-B85-C12-D49
A13-B85-C12-D49
A24-B85-C12-D49
A69-B85-C12-D49
A67-B85-C12-D49
A39-B85-C12-D49
A65-B85-C12-D49
A66-B85-C12-D49
A2-B86-C12-D49
A3-B86-C12-D49
A9-B86-C12-D49
A13-B86-C12-D49
A24-B86-C12-D49
A69-B86-C12-D49
A67-B86-C12-D49
A39-B86-C12-D49
A65-B86-C12-D49
A66-B86-C12-D49
A2-B87-C12-D49
A3-B87-C12-D49
A9-B87-C12-D49
A13-B87-C12-D49
A24-B87-C12-D49
A69-B87-C12-D49
A67-B87-C12-D49
A39-B87-C12-D49
A65-B87-C12-D49
A66-B87-C12-D49
A2-B89-C12-D49
A3-B89-C12-D49
A9-B89-C12-D49
A13-B89-C12-D49
A24-B89-C12-D49
A69-B89-C12-D49
A67-B89-C12-D49

-continued
A39-B89-C12-D49
A65-B89-C12-D49
A66-B89-C12-D49
A2-B92-C12-D49
A3-B92-C12-D49
A9-B92-C12-D49
A13-B92-C12-D49
A24-B92-C12-D49
A69-B92-C12-D49
A67-B92-C12-D49
A39-B92-C12-D49
A65-B92-C12-D49
A66-B92-C12-D49
A2-B4-C13-D49
A3-B4-C13-D49
A9-B4-C13-D49
A13-B4-C13-D49
A24-B4-C13-D49
A69-B4-C13-D49
A67-B4-C13-D49
A39-B4-C13-D49
A65-B4-C13-D49
A66-B4-C13-D49
A2-B5-C13-D49
A3-B5-C13-D49
A9-B5-C13-D49
A13-B5-C13-D49
A24-B5-C13-D49
A69-B5-C13-D49
A67-B5-C13-D49
A39-B5-C13-D49
A65-B5-C13-D49
A66-B5-C13-D49
A2-B6-C13-D49
A3-B6-C13-D49
A9-B6-C13-D49
A13-B6-C13-D49
A24-B6-C13-D49
A69-B6-C13-D49
A67-B6-C13-D49
A39-B6-C13-D49
A65-B6-C13-D49
A66-B6-C13-D49
A2-B32-C13-D49
A3-B32-C13-D49
A9-B32-C13-D49
A13-B32-C13-D49
A24-B32-C13-D49
A69-B32-C13-D49
A67-B32-C13-D49
A39-B32-C13-D49
A65-B32-C13-D49
A66-B32-C13-D49
A2-B39-C13-D49
A3-B39-C13-D49
A9-B39-C13-D49
A13-B39-C13-D49
A24-B39-C13-D49
A69-B39-C13-D49
A67-B39-C13-D49
A39-B39-C13-D49
A65-B39-C13-D49
A66-B39-C13-D49
A2-B45-C13-D49
A3-B45-C13-D49
A9-B45-C13-D49
A13-B45-C13-D49
A24-B45-C13-D49
A69-B45-C13-D49
A67-B45-C13-D49
A39-B45-C13-D49
A65-B45-C13-D49
A66-B45-C13-D49
A2-B53-C13-D49
A3-B53-C13-D49
A9-B53-C13-D49
A13-B53-C13-D49
A24-B53-C13-D49
A69-B53-C13-D49
A67-B53-C13-D49

-continued
A39-B53-C13-D49
A65-B53-C13-D49
A66-B53-C13-D49
A2-B79-C13-D49
A3-B79-C13-D49
A9-B79-C13-D49
A13-B79-C13-D49
A24-B79-C13-D49
A69-B79-C13-D49
A67-B79-C13-D49
A39-B79-C13-D49
A65-B79-C13-D49
A66-B79-C13-D49
A2-B80-C13-D49
A3-B80-C13-D49
A9-B80-C13-D49
A13-B80-C13-D49
A24-B80-C13-D49
A69-B80-C13-D49
A67-B80-C13-D49
A39-B80-C13-D49
A65-B80-C13-D49
A66-B80-C13-D49
A2-B85-C13-D49
A3-B85-C13-D49
A9-B85-C13-D49
A13-B85-C13-D49
A24-B85-C13-D49
A69-B85-C13-D49
A67-B85-C13-D49
A39-B85-C13-D49
A65-B85-C13-D49
A66-B85-C13-D49
A2-B86-C13-D49
A3-B86-C13-D49
A9-B86-C13-D49
A13-B86-C13-D49
A24-B86-C13-D49
A69-B86-C13-D49
A67-B86-C13-D49
A39-B86-C13-D49
A65-B86-C13-D49
A66-B86-C13-D49
A2-B87-C13-D49
A3-B87-C13-D49
A9-B87-C13-D49
A13-B87-C13-D49
A24-B87-C13-D49
A69-B87-C13-D49
A67-B87-C13-D49
A39-B87-C13-D49
A65-B87-C13-D49
A66-B87-C13-D49
A2-B89-C13-D49
A3-B89-C13-D49
A9-B89-C13-D49
A13-B89-C13-D49
A24-B89-C13-D49
A69-B89-C13-D49
A67-B89-C13-D49
A39-B89-C13-D49
A65-B89-C13-D49
A66-B89-C13-D49
A2-B92-C13-D49
A3-B92-C13-D49
A9-B92-C13-D49
A13-B92-C13-D49
A24-B92-C13-D49
A69-B92-C13-D49
A67-B92-C13-D49
A39-B92-C13-D49
A65-B92-C13-D49
A66-B92-C13-D49
A2-B4-C1-D50
A3-B4-C1-D50
A9-B4-C1-D50
A13-B4-C1-D50
A24-B4-C1-D50
A69-B4-C1-D50
A67-B4-C1-D50

-continued

A39-B4-C1-D50
A65-B4-C1-D50
A66-B4-C1-D50
A2-B5-C1-D50
A3-B5-C1-D50
A9-B5-C1-D50
A13-B5-C1-D50
A24-B5-C1-D50
A69-B5-C1-D50
A67-B5-C1-D50
A39-B5-C1-D50
A65-B5-C1-D50
A66-B5-C1-D50
A12-B6-C1-D50
A3-B6-C1-D50
A9-B6-C1-D50
A13-B6-C1-D50
A24-B6-C1-D50
A69-B6-C1-D50
A67-B6-C1-D50
A39-B6-C1-D50
A65-B6-C1-D50
A66-B6-C1-D50
A2-B32-C1-D50
A3-B32-C1-D50
A9-B32-C1-D5
A13-B32-C1-D50
A24-B32-C1-D50
A69-B32-C1-D50
A67-B32-C1-D50
A39-B32-C1-D50
A65-B32-C1-D50
A66-B32-C1-D50
A2-B39-C1-D50
A3-B39-C1-D50
A9-B39-C1-D50
A13-B39-C1-D50
A24-B39-C1-D50
A69-B39-C1-D50
A67-B39-C1-D50
A39-B39-C1-D50
A65-B39-C1-D50
A66-B39-C1-D50
A2-B45-C1-D50
A3-B45-C1-D50
A9-B45-C1-D50
A13-B45-C1-D50
A24-B45-C1-D50
A69-B45-C1-D50
A67-B45-C1-D50
A39-B45-C1-D50
A65-B45-C1-D50
A66-B45-C1-D50
A2-B53-C1-D50
A3-B53-C1-D50
A9-B53-C1-D50
A13-B53-C1-D50
A24-B53-C1-D50
A69-B53-C1-D50
A67-B53-C1-D50
A39-B53-C1-D50
A65-B53-C1-D50
A66-B53-C1-D50
A2-B79-C1-D50
A3-B79-C1-D50
A9-B79-C1-D50
A13-B79-C1-D50
A24-B79-C1-D50
A69-B79-C1-D50
A67-B79-C1-D50
A39-B79-C1-D50
A65-B79-C1-D50
A66-B79-C1-D50
A2-B80-C1-D50
A3-B80-C1-D50
A9-B80-C1-D50
A13-B80-C1-D50
A24-B80-C1-D50
A69-B80-C1-D50
A67-B80-C1-D50

-continued

A39-B80-C1-D50
A65-B80-C1-D50
A66-B80-C1-D50
A2-B85-C1-D50
A3-B85-C1-D50
A9-B85-C1-D50
A13-B85-C1-D50
A24-B85-C1-D50
A69-B85-C1-D50
A67-B85-C1-D50
A39-B85-C1-D50
A65-B85-C1-D50
A66-B85-C1-D50
A2-B86-C1-D50
A3-B86-C1-D50
A9-B86-C1-D50
A13-B86-C1-D50
A24-B86-C1-D50
A69-B86-C1-D50
A67-B86-C1-D50
A39-B86-C1-D50
A65-B86-C1-D50
A66-B86-C1-D50
A2-B87-C1-D50
A3-B87-C1-D50
A9-B87-C1-D50
A13-B87-C1-D50
A24-B87-C1-D50
A69-B87-C1-D50
A67-B87-C1-D50
A39-B87-C1-D50
A65-B87-C1-D50
A66-B87-C1-D50
A2-B89-C1-D50
A3-B89-C1-D50
A9-B89-C1-D50
A13-B89-C1-D50
A24-B89-C1-D50
A69-B89-C1-D50
A67-B89-C1-D50
A39-B89-C1-D50
A65-B89-C1-D50
A66-B89-C1-D50
A2-B92-C1-D50
A3-B92-C1-D50
A9-B92-C1-D50
A13-B92-C1-D50
A24-B92-C1-D50
A69-B92-C1-D50
A67-B92-C1-D50
A39-B92-C1-D50
A65-B92-C1-D50
A66-B92-C1-D50
A2-B4-C2-D50
A3-B4-C2-D50
A9-B4-C2-D50
A13-B4-C2-D50
A24-B4-C2-D50
A69-B4-C2-D50
A67-B4-C2-D50
A39-B4-C2-D50
A65-B4-C2-D50
A66-B4-C2-D50
A2-B5-C2-D50
A3-B5-C2-D50
A9-B5-C2-D50
A13-B5-C2-D50
A24-B5-C2-D50
A69-B5-C2-D50
A67-B5-C2-D50
A39-B5-C2-D50
A65-B5-C2-D50
A66-B5-C2-D50
A2-B6-C2-D50
A3-B6-C2-D50
A9-B6-C2-D50
A13-B6-C2-D50
A24-B6-C2-D50
A69-B6-C2-D50
A67-B6-C2-D50

-continued

A39-B6-C2-D50
A65-B6-C2-D50
A66-B6-C2-D50
A2-B32-C2-D50
A3-B32-C2-D50
A9-B32-C2-D50
A13-B32-C2-D50
A24-B32-C2-D50
A69-B32-C2-D50
A67-B32-C2-D50
A39-B32-C2-D50
A65-B32-C2-D50
A66-B32-C2-D50
A2-B39-C2-D50
A3-B39-C2-D50
A9-B39-C2-D50
A13-B39-C2-D50
A24-B39-C2-D50
A69-B39-C2-D50
A67-B39-C2-D50
A39-B39-C2-D50
A65-B39-C2-D50
A66-B39-C2-D50
A2-B45-C2-D50
A3-B45-C2-D50
A9-B45-C2-D50
A13-B45-C2-D50
A24-B45-C2-D50
A69-B45-C2-D50
A67-B45-C2-D50
A39-B45-C2-D50
A65-B45-C2-D50
A66-B45-C2-D50
A2-B53-C2-D50
A3-B53-C2-D50
A9-B53-C2-D50
A13-B53-C2-D50
A24-B53-C2-D50
A69-B53-C2-D50
A67-B53-C2-D50
A39-B53-C2-D50
A65-B53-C2-D50
A66-B53-C2-D50
A2-B79-C2-D50
A3-B79-C2-D50
A9-B79-C2-D50
A13-B79-C2-D50
A24-B79-C2-D50
A69-B79-C2-D50
A67-B79-C2-D50
A39-B79-C2-D50
A65-B79-C2-D50
A66-B79-C2-D50
A2-B80-C2-D50
A3-B80-C2-D50
A9-B80-C2-D50
A13-B80-C2-D50
A24-B80-C2-D50
A69-B80-C2-D50
A67-B80-C2-D50
A39-B80-C2-D50
A65-B80-C2-D50
A66-B80-C2-D50
A2-B85-C2-D50
A3-B85-C2-D50
A9-B85-C2-D50
A13-B85-C2-D50
A24-B85-C2-D50
A69-B85-C2-D50
A67-B85-C2-D50
A39-B85-C2-D50
A65-B85-C2-D50
A66-B85-C2-D50
A2-B86-C2-D50
A3-B86-C2-D50
A9-B86-C2-D50
A13-B86-C2-D50
A24-B86-C2-D50
A69-B86-C2-D50
A67-B86-C2-D50

-continued

A39-B86-C2-D50
A65-B86-C2-D50
A66-B86-C2-D50
A2-B87-C2-D50
A3-B87-C2-D50
A9-B87-C2-D50
A13-B87-C2-D50
A24-B87-C2-D50
A69-B87-C2-D50
A67-B87-C2-D50
A39-B87-C2-D50
A65-B87-C2-D50
A66-B87-C2-D50
A2-B89-C2-D50
A3-B89-C2-D50
A9-B89-C2-D50
A13-B89-C2-D50
A24-B89-C2-D50
A69-B89-C2-D50
A67-B89-C2-D50
A39-B89-C2-D50
A65-B89-C2-D50
A66-B89-C2-D50
A2-B92-C2-D50
A3-B92-C2-D50
A9-B92-C2-D50
A13-B92-C2-D50
A24-B92-C2-D50
A69-B92-C2-D50
A67-B92-C2-D50
A39-B92-C2-D50
A65-B92-C2-D50
A66-B92-C2-D50
A2-B4-C3-D50
A3-B4-C3-D50
A9-B4-C3-D50
A13-B4-C3-D50
A24-B4-C3-D50
A69-B4-C3-D50
A67-B4-C3-D50
A39-B4-C3-D50
A65-B4-C3-D50
A66-B4-C3-D50
A2-B5-C3-D50
A3-B5-C3-D50
A9-B5-C3-D50
A13-B5-C3-D50
A24-B5-C3-D50
A69-B5-C3-D50
A67-B5-C3-D50
A39-B5-C3-D50
A65-B5-C3-D50
A66-B5-C3-D50
A2-B6-C3-D50
A3-B6-C3-D50
A9-B6-C3-D50
A13-B6-C3-D50
A24-B6-C3-D50
A69-B6-C3-D50
A67-B6-C3-D50
A39-B6-C3-D50
A65-B6-C3-D50
A66-B6-C3-D50
A2-B32-C3-D50
A3-B32-C3-D50
A9-B32-C3-D50
A13-B32-C3-D50
A24-B32-C3-D50
A69-B32-C3-D50
A67-B32-C3-D50
A39-B32-C3-D50
A65-B32-C3-D50
A66-B32-C3-D50
A2-B39-C3-D50
A3-B39-C3-D50
A9-B39-C3-D50
A13-B39-C3-D50
A24-B39-C3-D50
A69-B39-C3-D50
A67-B39-C3-D50

-continued

A39-B39-C3-D50
A65-B39-C3-D50
A66-B39-C3-D50
A2-B45-C3-D50
A3-B45-C3-D50
A9-B45-C3-D50
A13-B45-C3-D50
A24-B45-C3-D50
A69-B45-C3-D50
A67-B45-C3-D50
A39-B45-C3-D50
A65-B45-C3-D50
A66-B45-C3-D50
A2-B53-C3-D50
A3-B53-C3-D50
A9-B53-C3-D50
A13-B53-C3-D50
A24-B53-C3-D50
A69-B53-C3-D50
A67-B53-C3-D50
A39-B53-C3-D50
A65-B53-C3-D50
A66-B53-C3-D50
A2-B79-C3-D50
A3-B79-C3-D50
A9-B79-C3-D50
A13-B79-C3-D50
A24-B79-C3-D50
A69-B79-C3-D50
A67-B79-C3-D50
A39-B79-C3-D50
A65-B79-C3-D50
A66-B79-C3-D50
A2-B80-C3-D50
A3-B80-C3-D50
A9-B80-C3-D50
A13-B80-C3-D50
A24-B80-C3-D50
A69-B80-C3-D50
A67-B80-C3-D50
A39-B80-C3-D50
A65-B80-C3-D50
A66-B80-C3-D50
A2-B85-C3-D50
A3-B85-C3-D50
A9-B85-C3-D50
A13-B85-C3-D50
A24-B85-C3-D50
A69-B85-C3-D50
A67-B85-C3-D50
A39-B85-C3-D50
A65-B85-C3-D50
A66-B85-C3-D50
A2-B86-C3-D50
A3-B86-C3-D50
A9-B86-C3-D50
A13-B86-C3-D50
A24-B86-C3-D50
A69-B86-C3-D50
A67-B86-C3-D50
A39-B86-C3-D50
A65-B86-C3-D50
A66-B86-C3-D50
A2-B87-C3-D50
A3-B87-C3-D50
A9-B87-C3-D50
A13-B87-C3-D50
A24-B87-C3-D50
A69-B87-C3-D50
A67-B87-C3-D50
A39-B87-C3-D50
A65-B87-C3-D50
A66-B87-C3-D50
A2-B89-C3-D50
A3-B89-C3-D50
A9-B89-C3-D50
A13-B89-C3-D50
A24-B89-C3-D50
A69-B89-C3-D50
A67-B89-C3-D50

-continued

A39-B89-C3-D50
A65-B89-C3-D50
A66-B89-C3-D50
A2-B92-C3-D50
A3-B92-C3-D50
A9-B92-C3-D50
A13-B92-C3-D50
A24-B92-C3-D50
A69-B92-C3-D50
A67-B92-C3-D50
A39-B92-C3-D50
A65-B92-C3-D50
A66-B92-C3-D50
A2-B4-C4-D50
A3-B4-C4-D50
A9-B4-C4-D50
A13-B4-C4-D50
A24-B4-C4-D50
A69-B4-C4-D50
A67-B4-C4-D507
A39-B4-C4-D50
A65-B4-C4-D50
A66-B4-C4-D50
A2-B5-C4-D50
A3-B5-C4-D50
A9-B5-C4-D50
A13-B5-C4-D50
A24-B5-C4-D50
A69-B5-C4-D50
A67-B5-C4-D508
A39-B5-C4-D50
A65-B5-C4-D50
A66-B5-C4-D50
A2-B6-C4-D50
A3-B6-C4-D50
A9-B6-C4-D50
A13-B6-C4-D50
A24-B6-C4-D50
A69-B6-C4-D50
A67-B6-C4-D50
A39-B6-C4-D50
A65-B6-C4-D50
A66-B6-C4-D50
A2-B32-C4-D50
A3-B32-C4-D50
A9-B32-C4-D50
A13-B32-C4-D50
A24-B32-C4-D50
A69-B32-C4-D50
A67-B32-C4-D50
A39-B32-C4-D50
A65-B32-C4-D50
A66-B32-C4-D50
A2-B39-C4-D50
A3-B39-C4-D50
A9-B39-C4-D50
A13-B39-C4-D50
A24-B39-C4-D50
A69-B39-C4-D50
A67-B39-C4-D50
A39-B39-C4-D50
A65-B39-C4-D50
A66-B39-C4-D50
A2-B45-C4-D50
A3-B45-C4-D50
A9-B45-C4-D50
A13-B45-C4-D50
A24-B45-C4-D50
A69-B45-C4-D50
A67-B45-C4-D50
A39-B45-C4-D50
A65-B45-C4-D50
A66-B45-C4-D50
A2-B53-C4-D50
A3-B53-C4-D50
A9-B53-C4-D50
A13-B53-C4-D50
A24-B53-C4-D50
A69-B53-C4-D50
A67-B53-C4-D50

-continued
A39-B53-C4-D50
A65-B53-C4-D50
A66-B53-C4-D50
A2-B79-C4-D50
A3-B79-C4-D50
A9-B79-C4-D50
A13-B79-C4-D50
A24-B79-C4-D50
A69-B79-C4-D50
A67-B79-C4-D50
A39-B79-C4-D50
A65-B79-C4-D50
A66-B79-C4-D50
A2-B80-C4-D50
A3-B80-C4-D50
A9-B80-C4-D50
A13-B80-C4-D50
A24-B80-C4-D50
A69-B80-C4-D50
A67-B80-C4-D50
A39-B80-C4-D50
A65-B80-C4-D50
A66-B80-C4-D50
A2-B85-C4-D50
A3-B85-C4-D50
A9-B85-C4-D50
A13-B85-C4-D50
A24-B85-C4-D50
A69-B85-C4-D50
A67-B85-C4-D50
A39-B85-C4-D50
A65-B85-C4-D50
A66-B85-C4-D50
A2-B86-C4-D50
A3-B86-C4-D50
A9-B86-C4-D50
A13-B86-C4-D50
A24-B86-C4-D50
A69-B86-C4-D50
A67-B86-C4-D50
A39-B86-C4-D50
A65-B86-C4-D50
A66-B86-C4-D50
A2-B87-C4-D50
A3-B87-C4-D50
A9-B87-C4-D50
A13-B87-C4-D50
A24-B87-C4-D50
A69-B87-C4-D50
A67-B87-C4-D50
A39-B87-C4-D50
A65-B87-C4-D50
A66-B87-C4-D50
A2-B89-C4-D50
A3-B89-C4-D50
A9-B89-C4-D50
A13-B89-C4-D50
A24-B89-C4-D50
A69-B89-C4-D50
A67-B89-C4-D50
A39-B89-C4-D50
A65-B89-C4-D50
A66-B89-C4-D50
A2-B92-C4-D50
A3-B92-C4-D50
A9-B92-C4-D50
A13-B92-C4-D50
A24-B92-C4-D50
A69-B92-C4-D50
A67-B92-C4-D50
A39-B92-C4-D50
A65-B92-C4-D50
A66-B92-C4-D50
A2-B4-C5-D50
A3-B4-C5-D50
A9-B4-C5-D50
A13-B4-C5-D50
A24-B4-C5-D50
A69-B4-C5-D50
A67-B4-C5-D50

-continued
A39-B4-C5-D50
A65-B4-C5-D50
A66-B4-C5-D50
A2-B5-C5-D50
A3-B5-C5-D50
A9-B5-C5-D50
A13-B5-C5-D50
A24-B5-C5-D50
A69-B5-C5-D50
A67-B5-C5-D50
A39-B5-C5-D50
A65-B5-C5-D50
A66-B5-C5-D50
A2-B6-C5-D50
A3-B6-C5-D50
A9-B6-C5-D50
A13-B6-C5-D50
A24-B6-C5-D50
A69-B6-C5-D50
A67-B6-C5-D50
A39-B6-C5-D50
A65-B6-C5-D50
A66-B6-C5-D50
A2-B32-C5-D50
A3-B32-C5-D50
A9-B32-C5-D50
A13-B32-C5-D50
A24-B32-C5-D50
A69-B32-C5-D50
A67-B32-C5-D50
A39-B32-C5-D50
A65-B32-C5-D50
A66-B32-C5-D50
A2-B39-C5-D50
A3-B39-C5-D50
A9-B39-C5-D50
A13-B39-C5-D50
A24-B39-C5-D50
A69-B39-C5-D50
A67-B39-C5-D50
A39-B39-C5-D50
A65-B39-C5-D50
A66-B39-C5-D50
A2-B45-C5-D50
A3-B45-C5-D50
A9-B45-C5-D50
A13-B45-C5-D50
A24-B45-C5-D50
A69-B45-C5-D50
A67-B45-C5-D50
A39-B45-C5-D50
A65-B45-C5-D50
A66-B45-C5-D50
A2-B53-C5-D50
A3-B53-C5-D50
A9-B53-C5-D50
A13-B53-C5-D50
A24-B53-C5-D50
A69-B53-C5-D50
A67-B53-C5-D50
A39-B53-C5-D50
A65-B53-C5-D50
A66-B53-C5-D50
A2-B79-C5-D50
A3-B79-C5-D50
A9-B79-C5-D50
A13-B79-C5-D50
A24-B79-C5-D50
A69-B79-C5-D50
A67-B79-C5-D50
A39-B79-C5-D50
A65-B79-C5-D50
A66-B79-C5-D50
A2-B80-C5-D50
A3-B80-C5-D50
A9-B80-C5-D50
A13-B80-C5-D50
A24-B80-C5-D50
A69-B80-C5-D50
A67-B80-C5-D507

-continued
A39-B80-C5-D50
A65-B80-C5-D50
A66-B80-C5-D50
A2-B85-C5-D50
A3-B85-C5-D50
A9-B85-C5-D50
A13-B85-C5-D50
A24-B85-C5-D50
A69-B85-C5-D50
A67-B85-C5-D508
A39-B85-C5-D50
A65-B85-C5-D50
A66-B85-C5-D50
A2-B86-C5-D50
A3-B86-C5-D50
A9-B86-C5-D50
A13-B86-C5-D50
A24-B86-C5-D50
A69-B86-C5-D50
A67-B86-C5-D50
A39-B86-C5-D50
A65-B86-C5-D50
A66-B86-C5-D50
A2-B87-C5-D50
A3-B87-C5-D50
A9-B87-C5-D50
A13-B87-C5-D50
A24-B87-C5-D50
A69-B87-C5-D50
A67-B87-C5-D50
A39-B87-C5-D50
A65-B87-C5-D50
A66-B87-C5-D50
A2-B89-C5-D50
A3-B89-C5-D50
A9-B89-C5-D50
A13-B89-C5-D50
A24-B89-C5-D50
A69-B89-C5-D50
A67-B89-C5-D50
A39-B89-C5-D50
A65-B89-C5-D50
A66-B89-C5-D50
A2-B92-C5-D50
A3-B92-C5-D50
A9-B92-C5-D50
A13-B92-C5-D50
A24-B92-C5-D50
A69-B92-C5-D50
A67-B92-C5-D50
A39-B92-C5-D50
A65-B92-C5-D50
A66-B92-C5-D50
A2-B4-C6-D50
A3-B4-C6-D50
A9-B4-C6-D50
A13-B4-C6-D50
A24-B4-C6-D50
A69-B4-C6-D50
A67-B4-C6-D50
A39-B4-C6-D50
A65-B4-C6-D50
A66-B4-C6-D50
A2-B5-C6-D50
A3-B5-C6-D50
A9-B5-C6-D50
A13-B5-C6-D50
A24-B5-C6-D50
A69-B5-C6-D50
A67-B5-C6-D50
A39-B5-C6-D50
A65-B5-C6-D50
A66-B5-C6-D50
A2-B6-C6-D50
A3-B6-C6-D50
A9-B6-C6-D50
A13-B6-C6-D50
A24-B6-C6-D50
A69-B6-C6-D50
A67-B6-C6-D50

-continued
A39-B6-C6-D50
A65-B6-C6-D50
A66-B6-C6-D50
A2-B32-C6-D50
A3-B32-C6-D50
A9-B32-C6-D50
A13-B32-C6-D50
A24-B32-C6-D50
A69-B32-C6-D50
A67-B32-C6-D50
A39-B32-C6-D50
A65-B32-C6-D50
A66-B32-C6-D50
A2-B39-C6-D50
A3-B39-C6-D50
A9-B39-C6-D50
A13-B39-C6-D50
A24-B39-C6-D50
A69-B39-C6-D50
A67-B39-C6-D50
A39-B39-C6-D50
A65-B39-C6-D50
A66-B39-C6-D50
A2-B45-C6-D50
A3-B45-C6-D50
A9-B45-C6-D50
A13-B45-C6-D50
A24-B45-C6-D50
A69-B45-C6-D50
A67-B45-C6-D50
A39-B45-C6-D50
A65-B45-C6-D50
A66-B45-C6-D50
A2-B53-C6-D50
A3-B53-C6-D50
A9-B53-C6-D50
A13-B53-C6-D50
A24-B53-C6-D50
A69-B53-C6-D50
A67-B53-C6-D50
A39-B53-C6-D50
A65-B53-C6-D50
A66-B53-C6-D50
A2-B79-C6-D50
A3-B79-C6-D50
A9-B79-C6-D50
A13-B79-C6-D50
A24-B79-C6-D50
A69-B79-C6-D50
A67-B79-C6-D50
A39-B79-C6-D50
A65-B79-C6-D50
A66-B79-C6-D50
A2-B80-C6-D50
A3-B80-C6-D50
A9-B80-C6-D50
A13-B80-C6-D50
A24-B80-C6-D50
A69-B80-C6-D50
A67-B80-C6-D50
A39-B80-C6-D50
A65-B80-C6-D50
A66-B80-C6-D50
A2-B85-C6-D50
A3-B85-C6-D50
A9-B85-C6-D50
A13-B85-C6-D50
A24-B85-C6-D50
A69-B85-C6-D50
A67-B85-C6-D50
A39-B85-C6-D50
A65-B85-C6-D50
A66-B85-C6-D50
A2-B86-C6-D50
A3-B86-C6-D50
A9-B86-C6-D50
A13-B86-C6-D50
A24-B86-C6-D50
A69-B86-C6-D50
A67-B86-C6-D50

-continued
A39-B86-C6-D50
A65-B86-C6-D50
A66-B86-C6-D50
A2-B87-C6-D50
A3-B87-C6-D50
A9-B87-C6-D50
A13-B87-C6-D50
A24-B87-C6-D50
A69-B87-C6-D50
A67-B87-C6-D50
A39-B87-C6-D50
A65-B87-C6-D50
A66-B87-C6-D50
A2-B89-C6-D50
A3-B89-C6-D50
A9-B89-C6-D50
A13-B89-C6-D50
A24-B89-C6-D50
A69-B89-C6-D50
A67-B89-C6-D50
A39-B89-C6-D50
A65-B89-C6-D50
A66-B89-C6-D50
A2-B92-C6-D50
A3-B92-C6-D50
A9-B92-C6-D50
A13-B92-C6-D50
A24-B92-C6-D50
A69-B92-C6-D50
A67-B92-C6-D50
A39-B92-C6-D50
A65-B92-C6-D50
A66-B92-C6-D50
A2-B4-C7-D50
A3-B4-C7-D50
A9-B4-C7-D50
A13-B4-C7-D50
A24-B4-C7-D50
A69-B4-C7-D50
A67-B4-C7-D50
A39-B4-C7-D50
A65-B4-C7-D50
A66-B4-C7-D50
A2-B5-C7-D50
A3-B5-C7-D50
A9-B5-C7-D50
A13-B5-C7-D50
A24-B5-C7-D50
A69-B5-C7-D50
A67-B5-C7-D506
A39-B5-C7-D50
A65-B5-C7-D50
A66-B5-C7-D50
A2-B6-C7-D50
A3-B6-C7-D50
A9-B6-C7-D50
A13-B6-C7-D50
A24-B6-C7-D50
A69-B6-C7-D50
A67-B6-C7-D507
A39-B6-C7-D50
A65-B6-C7-D50
A66-B6-C7-D50
A2-B32-C7-D50
A3-B32-C7-D50
A9-B32-C7-D50
A13-B32-C7-D50
A24-B32-C7-D50
A69-B32-C7-D50
A67-B32-C7-D50
A39-B32-C7-D50
A65-B32-C7-D50
A66-B32-C7-D50
A2-B39-C7-D50
A3-B39-C7-D50
A9-B39-C7-D50
A13-B39-C7-D50
A24-B39-C7-D50
A69-B39-C7-D50
A67-B39-C7-D50

-continued
A39-B39-C7-D50
A65-B39-C7-D50
A66-B39-C7-D50
A2-B45-C7-D50
A3-B45-C7-D50
A9-B45-C7-D50
A13-B45-C7-D50
A24-B45-C7-D50
A69-B45-C7-D50
A67-B45-C7-D50
A39-B45-C7-D50
A65-B45-C7-D50
A66-B45-C7-D50
A2-B53-C7-D50
A3-B53-C7-D50
A9-B53-C7-D50
A13-B53-C7-D50
A24-B53-C7-D50
A69-B53-C7-D50
A67-B53-C7-D50
A39-B53-C7-D50
A65-B53-C7-D50
A66-B53-C7-D50
A2-B79-C7-D50
A3-B79-C7-D50
A9-B79-C7-D50
A13-B79-C7-D50
A24-B79-C7-D50
A69-B79-C7-D50
A67-B79-C7-D50
A39-B79-C7-D50
A65-B79-C7-D50
A66-B79-C7-D50
A2-B80-C7-D50
A3-B80-C7-D50
A9-B80-C7-D50
A13-B80-C7-D50
A24-B80-C7-D50
A69-B80-C7-D50
A67-B80-C7-D50
A39-B80-C7-D50
A65-B80-C7-D50
A66-B80-C7-D50
A2-B85-C7-D50
A3-B85-C7-D50
A9-B85-C7-D50
A13-B85-C7-D50
A24-B85-C7-D50
A69-B85-C7-D50
A67-B85-C7-D50
A39-B85-C7-D50
A65-B85-C7-D50
A66-B85-C7-D50
A2-B86-C7-D50
A3-B86-C7-D50
A9-B86-C7-D50
A13-B86-C7-D50
A24-B86-C7-D50
A69-B86-C7-D50
A67-B86-C7-D50
A39-B86-C7-D50
A65-B86-C7-D50
A66-B86-C7-D50
A2-B87-C7-D50
A3-B87-C7-D50
A9-B87-C7-D50
A13-B87-C7-D50
A24-B87-C7-D50
A69-B87-C7-D50
A67-B87-C7-D50
A39-B87-C7-D50
A65-B87-C7-D50
A66-B87-C7-D50
A2-B89-C7-D50
A3-B89-C7-D50
A9-B89-C7-D50
A13-B89-C7-D50
A24-B89-C7-D50
A69-B89-C7-D50
A67-B89-C7-D50

-continued
A39-B89-C7-D50
A65-B89-C7-D50
A66-B89-C7-D50
A2-B92-C7-D50
A3-B92-C7-D50
A9-B92-C7-D50
A13-B92-C7-D50
A24-B92-C7-D50
A69-B92-C7-D50
A67-B92-C7-D50
A39-B92-C7-D50
A65-B92-C7-D50
A66-B92-C7-D50
A2-B4-C8-D50
A3-B4-C8-D50
A9-B4-C8-D50
A13-B4-C8-D50
A24-B4-C8-D50
A69-B4-C8-D50
A67-B4-C8-D50
A39-B4-C8-D50
A65-B4-C8-D50
A66-B4-C8-D50
A2-B5-C8-D50
A3-B5-C8-D50
A9-B5-C8-D50
A13-B5-C8-D50
A24-B5-C8-D50
A69-B5-C8-D50
A67-B5-C8-D50
A39-B5-C8-D50
A65-B5-C8-D50
A66-B5-C8-D50
A2-B6-C8-D50
A3-B6-C8-D50
A9-B6-C8-D50
A13-B6-C8-D50
A24-B6-C8-D50
A69-B6-C8-D50
A67-B6-C8-D50
A39-B6-C8-D50
A65-B6-C8-D50
A66-B6-C8-D50
A2-B32-C8-D50
A3-B32-C8-D50
A9-B32-C8-D50
A13-B32-C8-D50
A24-B32-C8-D50
A69-B32-C8-D50
A67-B32-C8-D50
A39-B32-C8-D50
A65-B32-C8-D50
A66-B32-C8-D50
A2-B39-C8-D50
A3-B39-C8-D50
A9-B39-C8-D50
A13-B39-C8-D50
A24-B39-C8-D50
A69-B39-C8-D50
A67-B39-C8-D50
A39-B39-C8-D50
A65-B39-C8-D50
A66-B39-C8-D50
A2-B45-C8-D50
A3-B45-C8-D50
A9-B45-C8-D50
A13-B45-C8-D50
A24-B45-C8-D50
A69-B45-C8-D50
A67-B45-C8-D50
A39-B45-C8-D50
A65-B45-C8-D50
A66-B45-C8-D50
A2-B53-C8-D50
A3-B53-C8-D50
A9-B53-C8-D50
A13-B53-C8-D50
A24-B53-C8-D50
A69-B53-C8-D50
A67-B53-C8-D50

-continued
A39-B53-C8-D50
A65-B53-C8-D50
A66-B53-C8-D50
A2-B79-C8-D50
A3-B79-C8-D50
A9-B79-C8-D50
A13-B79-C8-D50
A24-B79-C8-D50
A69-B79-C8-D50
A67-B79-C8-D50
A39-B79-C8-D50
A65-B79-C8-D50
A66-B79-C8-D50
A2-B80-C8-D50
A3-B80-C8-D50
A9-B80-C8-D50
A13-B80-C8-D50
A24-B80-C8-D50
A69-B80-C8-D50
A67-B80-C8-D50
A39-B80-C8-D50
A65-B80-C8-D50
A66-B80-C8-D50
A2-B85-C8-D50
A3-B85-C8-D50
A9-B85-C8-D50
A13-B85-C8-D50
A24-B85-C8-D50
A69-B85-C8-D50
A67-B85-C8-D50
A39-B85-C8-D50
A65-B85-C8-D50
A66-B85-C8-D50
A2-B86-C8-D50
A3-B86-C8-D50
A9-B86-C8-D50
A13-B86-C8-D50
A24-B86-C8-D50
A69-B86-C8-D50
A67-B86-C8-D50
A39-B86-C8-D50
A65-B86-C8-D50
A66-B86-C8-D50
A2-B87-C8-D50
A3-B87-C8-D50
A9-B87-C8-D50
A13-B87-C8-D50
A24-B87-C8-D50
A69-B87-C8-D50
A67-B87-C8-D50
A39-B87-C8-D50
A65-B87-C8-D50
A66-B87-C8-D50
A2-B89-C8-D50
A3-B89-C8-D50
A9-B89-C8-D50
A13-B89-C8-D50
A24-B89-C8-D50
A69-B89-C8-D50
A67-B89-C8-D50
A39-B89-C8-D50
A65-B89-C8-D50
A66-B89-C8-D50
A2-B92-C8-D50
A3-B92-C8-D50
A9-B92-C8-D50
A13-B92-C8-D50
A24-B92-C8-D50
A69-B92-C8-D50
A67-B92-C8-D50
A39-B92-C8-D50
A65-B92-C8-D50
A66-B92-C8-D50
A2-B4-C9-D50
A3-B4-C9-D50
A9-B4-C9-D50
A13-B4-C9-D50
A24-B4-C9-D50
A69-B4-C9-D50
A67-B4-C9-D50

-continued
A39-B4-C9-D50
A65-B4-C9-D50
A66-B4-C9-D50
A2-B5-C9-D50
A3-B5-C9-D50
A9-B5-C9-D50
A13-B5-C9-D50
A24-B5-C9-D50
A69-B5-C9-D50
A67-B5-C9-D50
A39-B5-C9-D50
A65-B5-C9-D50
A66-B5-C9-D50
A2-B6-C9-D50
A3-B6-C9-D50
A9-B6-C9-D50
A13-B6-C9-D50
A24-B6-C9-D50
A69-B6-C9-D50
A67-B6-C9-D50
A39-B6-C9-D50
A65-B6-C9-D50
A66-B6-C9-D50
A2-B32-C9-D50
A3-B32-C9-D50
A9-B32-C9-D50
A13-B32-C9-D50
A24-B32-C9-D50
A69-B32-C9-D50
A67-B32-C9-D50
A39-B32-C9-D50
A65-B32-C9-D50
A66-B32-C9-D50
A2-B39-C9-D50
A3-B39-C9-D50
A9-B39-C9-D50
A13-B39-C9-D50
A24-B39-C9-D50
A69-B39-C9-D50
A67-B39-C9-D50
A39-B39-C9-D50
A65-B39-C9-D50
A66-B39-C9-D50
A2-B45-C9-D50
A3-B45-C9-D50
A9-B45-C9-D50
A13-B45-C9-D50
A24-B45-C9-D50
A69-B45-C9-D50
A67-B45-C9-D50
A39-B45-C9-D50
A65-B45-C9-D50
A66-B45-C9-D50
A2-B53-C9-D50
A3-B53-C9-D50
A9-B53-C9-D50
A13-B53-C9-D50
A24-B53-C9-D50
A69-B53-C9-D50
A67-B53-C9-D50
A39-B53-C9-D50
A65-B53-C9-D50
A66-B53-C9-D50
A2-B79-C9-D50
A3-B79-C9-D50
A9-B79-C9-D50
A13-B79-C9-D50
A24-B79-C9-D50
A69-B79-C9-D50
A67-B79-C9-D50
A39-B79-C9-D50
A65-B79-C9-D50
A66-B79-C9-D50
A2-B80-C9-D50
A3-B80-C9-D50
A9-B80-C9-D50
A13-B80-C9-D50
A24-B80-C9-D50
A69-B80-C9-D50
A67-B80-C9-D50

-continued
A39-B80-C9-D50
A65-B80-C9-D50
A66-B80-C9-D50
A2-B85-C9-D50
A3-B85-C9-D50
A9-B85-C9-D50
A13-B85-C9-D50
A24-B85-C9-D50
A69-B85-C9-D50
A67-B85-C9-D50
A39-B85-C9-D50
A65-B85-C9-D50
A66-B85-C9-D50
A2-B86-C9-D50
A3-B86-C9-D50
A9-B86-C9-D50
A13-B86-C9-D50
A24-B86-C9-D50
A69-B86-C9-D50
A67-B86-C9-D50
A39-B86-C9-D50
A65-B86-C9-D50
A66-B86-C9-D50
A2-B87-C9-D50
A3-B87-C9-D50
A9-B87-C9-D50
A13-B87-C9-D50
A24-B87-C9-D50
A69-B87-C9-D50
A67-B87-C9-D50
A39-B87-C9-D50
A65-B87-C9-D50
A66-B87-C9-D50
A2-B89-C9-D50
A3-B89-C9-D50
A9-B89-C9-D50
A13-B89-C9-D50
A24-B89-C9-D50
A69-B89-C9-D50
A67-B89-C9-D50
A39-B89-C9-D50
A65-B89-C9-D50
A66-B89-C9-D50
A2-B92-C9-D50
A3-B92-C9-D50
A9-B92-C9-D50
A13-B92-C9-D50
A24-B92-C9-D50
A69-B92-C9-D50
A67-B92-C9-D50
A39-B92-C9-D50
A65-B92-C9-D50
A66-B92-C9-D50
A2-B4-C10-D50
A3-B4-C10-D50
A9-B4-C10-D50
A13-B4-C10-D50
A24-B4-C10-D50
A69-B4-C10-D50
A67-B4-C10-D50
A39-B4-C10-D50
A65-B4-C10-D50
A66-B4-C10-D50
A2-B5-C10-D50
A3-B5-C10-D50
A9-B5-C10-D50
A13-B5-C10-D50
A24-B5-C10-D50
A69-B5-C10-D50
A67-B5-C10-D50
A39-B5-C10-D50
A65-B5-C10-D50
A66-B5-C10-D50
A2-B6-C10-D50
A3-B6-C10-D50
A9-B6-C10-D50
A13-B6-C10-D50
A24-B6-C10-D50
A69-B6-C10-D50
A67-B6-C10-D50

-continued
A39-B6-C10-D50
A65-B6-C10-D50
A66-B6-C10-D50
A2-B32-C10-D50
A3-B32-C10-D50
A9-B32-C10-D50
A13-B32-C10-D50
A24-B32-C10-D50
A69-B32-C10-D50
A67-B32-C10-D50
A39-B32-C10-D50
A65-B32-C10-D50
A66-B32-C10-D50
A2-B39-C10-D50
A3-B39-C10-D50
A9-B39-C10-D50
A13-B39-C10-D50
A24-B39-C10-D50
A69-B39-C10-D50
A67-B39-C10-D50
A39-B39-C10-D50
A65-B39-C10-D50
A66-B39-C10-D50
A2-B45-C10-D50
A3-B45-C10-D50
A9-B45-C10-D50
A13-B45-C10-D50
A24-B45-C10-D50
A69-B45-C10-D50
A67-B45-C10-D50
A39-B45-C10-D50
A65-B45-C10-D50
A66-B45-C10-D50
A2-B53-C10-D50
A3-B53-C10-D50
A9-B53-C10-D50
A13-B53-C10-D50
A24-B53-C10-D50
A69-B53-C10-D50
A67-B53-C10-D50
A39-B53-C10-D50
A65-B53-C10-D50
A66-B53-C10-D50
A2-B79-CT0-D50
A3-B79-C10-D50
A9-B79-C10-D50
A13-B79-C10-D50
A24-B79-C10-D50
A69-B79-C10-D50
A67-B79-C10-D50
A39-B79-C10-D50
A65-B79-C10-D50
A66-B79-C10-D50
A2-B80-C10-D50
A3-B80-C10-D50
A9-B80-C10-D50
A13-B80-C10-D50
A24-B80-C10-D50
A69-B80-C10-D50
A67-B80-C10-D50
A39-B80-C10-D50
A65-B80-C10-D50
A66-B80-C10-D50
A2-B85-C10-D50
A3-B85-C10-D50
A9-B85-C10-D50
A13-B85-C10-D50
A24-B85-C10-D50
A69-B85-C10-D50
A67-B85-C10-D50
A39-B85-C10-D50
A65-B85-C10-D50
A66-B85-C10-D50
A2-B86-C10-D50
A3-B86-C10-D50
A9-B86-C10-D50
A13-B86-C10-D50
A24-B86-C10-D50
A69-B86-C10-D50
A67-B86-C10-D50

-continued
A39-B86-C10-D50
A65-B86-C10-D50
A66-B86-C10-D50
A2-B87-C10-D50
A3-B87-C10-D50
A9-B87-C10-D50
A13-B87-C10-D50
A24-B87-C10-D50
A69-B87-C10-D50
A67-B87-C10-D50
A39-B87-C10-D50
A65-B87-C10-D50
A66-B87-C10-D50
A2-B89-C10-D50
A3-B89-C10-D50
A9-B89-C10-D50
A13-B89-C10-D50
A24-B89-C10-D50
A69-B89-C10-D50
A67-B89-C10-D50
A39-B89-C10-D50
A65-B89-C10-D50
A66-B89-C10-D50
A2-B92-C10-D50
A3-B92-C10-D50
A9-B92-C10-D50
A13-B92-C10-D50
A24-B92-C10-D50
A69-B92-C10-D50
A67-B92-C10-D50
A39-B92-C10-D50
A65-B92-C10-D50
A66-B92-C10-D50
A2-B4-C11-D50
A3-B4-C11-D50
A9-B4-C11-D50
A13-B4-C11-D50
A24-B4-C11-D50
A69-B4-C11-D50
A67-B4-C11-D50
A39-B4-C11-D50
A65-B4-C11-D50
A66-B4-C11-D50
A2-B5-C11-D50
A3-B5-C11-D50
A9-B5-C11-D50
A13-B5-C11-D50
A24-B5-C11-D50
A69-B5-C11-D50
A67-B5-C11-D50
A39-B5-C11-D50
A65-B5-C11-D50
A66-B5-C11-D50
A2-B6-C11-D50
A3-B6-C11-D50
A9-B6-C11-D50
A13-B6-C11-D50
A24-B6-C11-D50
A69-B6-C11-D50
A67-B6-C11-D50
A39-B6-C11-D50
A65-B6-C11-D50
A66-B6-C11-D50
A2-B32-C11-D50
A3-B32-C11-D50
A9-B32-C11-D50
A13-B32-C11-D50
A24-B32-C11-D50
A69-B32-C11-D50
A67-B32-C11-D50
A39-B32-C11-D50
A65-B32-C11-D50
A66-B32-C11-D50
A2-B39-C11-D50
A3-B39-C11-D50
A9-B39-C11-D50
A13-B39-C11-D50
A24-B39-C11-D50
A69-B39-C11-D50
A67-B39-C11-D50

-continued
A39-B39-C11-D50
A65-B39-C11-D50
A66-B39-C11-D50
A2-B45-C11-D50
A3-B45-C11-D50
A9-B45-C11-D50
A13-B45-C11-D50
A24-B45-C11-D50
A69-B45-C11-D50
A67-B45-C11-D50
A39-B45-C11-D50
A65-B45-C11-D50
A66-B45-C11-D50
A2-B53-C11-D50
A3-B53-C11-D50
A9-B53-C11-D50
A13-B53-C11-D50
A24-B53-C11-D50
A69-B53-C11-D50
A67-B53-C11-D50
A39-B53-C11-D50
A65-B53-C11-D50
A66-B53-C11-D50
A2-B79-C11-D50
A3-B79-C11-D50
A9-B79-C11-D50
A13-B79-C11-D50
A24-B79-C11-D50
A69-B79-C11-D50
A67-B79-C11-D50
A39-B79-C11-D50
A65-B79-C11-D50
A66-B79-C11-D50
A2-B80-C11-D50
A3-B80-C11-D50
A9-B80-C11-D50
A13-B80-C11-D50
A24-B80-C11-D50
A69-B80-C11-D50
A67-B80-C11-D50
A39-B80-C11-D50
A65-B80-C11-D50
A66-B80-C11-D50
A2-B85-C11-D50
A3-B85-C11-D50
A9-B85-C11-D50
A13-B85-C11-D50
A24-B85-C11-D50
A69-B85-C11-D50
A67-B85-C11-D50
A39-B85-C11-D50
A65-B85-C11-D50
A66-B85-C11-D50
A2-B86-C11-D50
A3-B86-C11-D50
A9-B86-C11-D50
A13-B86-C11-D50
A24-B86-C11-D50
A69-B86-C11-D50
A67-B86-C11-D50
A39-B86-C11-D50
A65-B86-C11-D50
A66-B86-C11-D50
A2-B87-C11-D50
A3-B87-C11-D50
A9-B87-C11-D50
A13-B87-C11-D50
A24-B87-C11-D50
A69-B87-C11-D50
A67-B87-C11-D50
A39-B87-C11-D50
A65-B87-C11-D50
A66-B87-C11-D50
A2-B89-C11-D50
A3-B89-C11-D50
A9-B89-C11-D50

-continued
A13-B89-C11-D50
A24-B89-C11-D50
A69-B89-C11-D50
A67-B89-C11-D50
A39-B89-C11-D50
A65-B89-C11-D50
A66-B89-C11-D50
A2-B92-C11-D50
A3-B92-C11-D50
A9-B92-C11-D50
A13-B92-C11-D50
A24-B92-C11-D50
A69-B92-C11-D50
A67-B92-C11-D50
A39-B92-C11-D50
A65-B92-C11-D50
A66-B92-C11-D50
A2-B4-C12-D50
A3-B4-C12-D50
A9-B4-C12-D50
A13-B4-C12-D50
A24-B4-C12-D50
A69-B4-C12-D50
A67-B4-C12-D50
A39-B4-C12-D50
A65-B4-C12-D50
A66-B4-C12-D50
A2-B5-C12-D50
A3-B5-C12-D50
A9-B5-C12-D50
A13-B5-C12-D50
A24-B5-C12-D50
A69-B5-C12-D50
A67-B5-C12-D50
A39-B5-C12-D50
A65-B5-C12-D50
A66-B5-C12-D50
A2-B6-C12-D50
A3-B6-C12-D50
A9-B6-C12-D50
A13-B6-C12-D50
A24-B6-C12-D50
A69-B6-C12-D50
A67-B6-C12-D50
A39-B6-C12-D50
A65-B6-C12-D50
A66-B6-C12-D50
A2-B32-C12-D50
A3-B32-C12-D50
A9-B32-C12-D50
A13-B32-C12-D50
A24-B32-C12-D50
A69-B32-C12-D50
A67-B32-C12-D50
A39-B32-C12-D50
A65-B32-C12-D50
A66-B32-C12-D50
A2-B39-C12-D50
A3-B39-C12-D50
A9-B39-C12-D50
A13-B39-C12-D50
A24-B39-C12-D50
A69-B39-C12-D50
A67-B39-C12-D50
A39-B39-C12-D50
A65-B39-C12-D50
A66-B39-C12-D50
A2-B45-C12-D50
A3-B45-C12-D50
A9-B45-C12-D50
A13-B45-C12-D50
A24-B45-C12-D50
A69-B45-C12-D50
A67-B45-C12-D50
A39-B45-C12-D50
A65-B45-C12-D50
A66-B45-C12-D50
A2-B53-C12-D50
A3-B53-C12-D50
A9-B53-C12-D50

-continued

A13-B53-C12-D50
A24-B53-C12-D50
A69-B53-C12-D50
A67-B53-C12-D50
A39-B53-C12-D50
A65-B53-C12-D50
A66-B53-C12-D50
A2-B79-C12-D50
A3-B79-C12-D50
A9-B79-C12-D50
A13-B79-C12-D50
A24-B79-C12-D50
A69-B79-C12-D50
A67-B79-C12-D50
A39-B79-C12-D50
A65-B79-C12-D50
A66-B79-C12-D50
A2-B80-C12-D50
A3-B80-C12-D50
A9-B80-C12-D50
A13-B80-C12-D50
A24-B80-C12-D50
A69-B80-C12-D50
A67-B80-C12-D50
A39-B80-C12-D50
A65-B80-C12-D50
A66-B80-C12-D50
A2-B85-C12-D50
A3-B85-C12-D50
A9-B85-C12-D50
A13-B85-C12-D50
A24-B85-C12-D50
A69-B85-C12-D50
A67-B85-C12-D50
A39-B85-C12-D50
A65-B85-C12-D50
A66-B85-C12-D50
A2-B86-C12-D50
A3-B86-C12-D50
A9-B86-C12-D50
A13-B86-C12-D50
A24-B86-C12-D50
A69-B86-C12-D50
A67-B86-C12-D50
A39-B86-C12-D50
A65-B86-C12-D50
A66-B86-C12-D50
A2-B87-C12-D50
A3-B87-C12-D50
A9-B87-C12-D50
A13-B87-C12-D50
A24-B87-C12-D50
A69-B87-C12-D50
A67-B87-C12-D50
A39-B87-C12-D50
A65-B87-C12-D50
A66-B87-C12-D50
A2-B89-C12-D50
A3-B89-C12-D50
A9-B89-C12-D50
A13-B89-C12-D50
A24-B89-C12-D50
A69-B89-C12-D50
A67-B89-C12-D50
A39-B89-C12-D50
A65-B89-C12-D50
A66-B89-C12-D50
A2-B92-C12-D50
A3-B92-C12-D50
A9-B92-C12-D50
A13-B92-C12-D50
A24-B92-C12-D50
A69-B92-C12-D50
A67-B92-C12-D50
A39-B92-C12-D50
A65-B92-C12-D50
A66-B92-C12-D50
A2-B4-C13-D50
A3-B4-C13-D50
A9-B4-C13-D50

-continued

A13-B4-C13-D50
A24-B4-C13-D50
A69-B4-C13-D50
A67-B4-C13-D50
A39-B4-C13-D50
A65-B4-C13-D50
A66-B4-C13-D50
A2-B5-C13-D50
A3-B5-C13-D50
A9-B5-C13-D50
A13-B5-C13-D50
A24-B5-C13-D50
A69-B5-C13-D50
A67-B5-C13-D50
A39-B5-C13-D50
A65-B5-C13-D50
A66-B5-C13-D50
A2-B6-C13-D50
A3-B6-C13-D50
A9-B6-C13-D50
A13-B6-C13-D50
A24-B6-C13-D50
A69-B6-C13-D50
A67-B6-C13-D50
A39-B6-C13-D50
A65-B6-C13-D50
A66-B6-C13-D50
A2-B32-C13-D50
A3-B32-C13-D50
A9-B32-C13-D50
A13-B32-C13-D50
A24-B32-C13-D50
A69-B32-C13-D50
A67-B32-C13-D50
A39-B32-C13-D50
A65-B32-C13-D50
A66-B32-C13-D50
A2-B39-C13-D50
A3-B39-C13-D50
A9-B39-C13-D50
A13-B39-C13-D50
A24-B39-C13-D50
A69-B39-C13-D50
A67-B39-C13-D50
A39-B39-C13-D50
A65-B39-C13-D50
A66-B39-C13-D50
A2-B45-C13-D50
A3-B45-C13-D50
A9-B45-C13-D50
A13-B45-C13-D50
A24-B45-C13-D50
A69-B45-C13-D50
A67-B45-C13-D50
A39-B45-C13-D50
A65-B45-C13-D50
A66-B45-C13-D50
A2-B53-C13-D50
A3-B53-C13-D50
A9-B53-C13-D50
A13-B53-C13-D50
A24-B53-C13-D50
A69-B53-C13-D50
A67-B53-C13-D50
A39-B53-C13-D50
A65-B53-C13-D50
A66-B53-C13-D50
A2-B79-C13-D50
A3-B79-C13-D50
A9-B79-C13-D50
A13-B79-C13-D50
A24-B79-C13-D50
A69-B79-C13-D50
A67-B79-C13-D50
A39-B79-C13-D50
A65-B79-C13-D50
A66-B79-C13-D50
A2-B80-C13-D50
A3-B80-C13-D50
A9-B80-C13-D50

-continued
A13-B80-C13-D50
A24-B80-C13-D50
A69-B80-C13-D50
A67-B80-C13-D50
A39-B80-C13-D50
A65-B80-C13-D50
A66-B80-C13-D50
A2-B85-C13-D50
A3-B85-C13-D50
A9-B85-C13-D50
A13-B85-C13-D50
A24-B85-C13-D50
A69-B85-C13-D50
A67-B85-C13-D50
A39-B85-C13-D50
A65-B85-C13-D50
A66-B85-C13-D50
A2-B86-C13-D50
A3-B86-C13-D50
A9-B86-C13-D50
A13-B86-C13-D50
A24-B86-C13-D50
A69-B86-C13-D50
A67-B86-C13-D50
A39-B86-C13-D50
A65-B86-C13-D50
A66-B86-C13-D50
A2-B87-C13-D50
A3-B87-C13-D50
A9-B87-C13-D50
A13-B87-C13-D50
A24-B87-C13-D50
A69-B87-C13-D50
A67-B87-C13-D50
A39-B87-C13-D50
A65-B87-C13-D50
A66-B87-C13-D50
A2-B89-C13-D50
A3-B89-C13-D50
A9-B89-C13-D50
A13-B89-C13-D50
A24-B89-C13-D50
A69-B89-C13-D50
A67-B89-C13-D50
A39-B89-C13-D50
A65-B89-C13-D50
A66-B89-C13-D50
A2-B92-C13-D50
A3-B92-C13-D50
A9-B92-C13-D50
A13-B92-C13-D50
A24-B92-C13-D50
A69-B92-C13-D50
A67-B92-C13-D50
A39-B92-C13-D50
A65-B92-C13-D50
A66-B92-C13-D50
A2-B4-C1-D51
A3-B4-C1-D51
A9-B4-C1-D51
A13-B4-C1-D51
A24-B4-C1-D51
A69-B4-C1-D51
A67-B4-C1-D51
A39-B4-C1-D51
A65-B4-C1-D51
A66-B4-C1-D51
A2-B5-C1-D51
A3-B5-C1-D51
A9-B5-C1-D51
A13-B5-C1-D51
A24-B5-C1-D51
A69-B5-C1-D51
A67-B5-C1-D51
A39-B5-C1-D51
A65-B5-C1-D51
A66-B5-C1-D51
A2-B6-C1-D51
A3-B6-C1-D51
A9-B6-C1-D51

-continued
A13-B6-C1-D51
A24-B6-C1-D51
A69-B6-C1-D51
A67-B6-C1-D51
A39-B6-C1-D51
A65-B6-C1-D51
A66-B6-C1-D51
A2-B32-C1-D51
A3-B32-C1-D51
A9-B32-C1-D51
A13-B32-C1-D51
A24-B32-C1-D51
A69-B32-C1-D51
A67-B32-C1-D51
A39-B32-C1-D51
A65-B32-C1-D51
A66-B32-C1-D51
A2-B39-C1-D51
A3-B39-C1-D51
A9-B39-C1-D51
A13-B39-C1-D51
A24-B39-C1-D51
A69-B39-C1-D51
A67-B39-C1-D51
A39-B39-C1-D51
A65-B39-C1-D51
A66-B39-C1-D51
A2-B45-C1-D51
A3-B45-C1-D51
A9-B45-C1-D51
A13-B45-C1-D51
A24-B45-C1-D51
A69-B45-C1-D51
A67-B45-C1-D51
A39-B45-C1-D51
A65-B45-C1-D51
A66-B45-C1-D51
A2-B53-C1-D51
A3-B53-C1-D51
A9-B53-C1-D51
A13-B53-C1-D51
A24-B53-C1-D51
A69-B53-C1-D51
A67-B53-C1-D51
A39-B53-C1-D51
A65-B53-C1-D51
A66-B53-C1-D51
A2-B79-C1-D51
A3-B79-C1-D51
A9-B79-C1-D51
A13-B79-C1-D51
A24-B79-C1-D51
A69-B79-C1-D51
A67-B79-C1-D51
A39-B79-C1-D51
A65-B79-C1-D51
A66-B79-C1-D51
A2-B80-C1-D51
A3-B80-C1-D51
A9-B80-C1-D51
A13-B80-C1-D51
A24-B80-C1-D51
A69-B80-C1-D51
A67-B80-C1-D51
A39-B80-C1-D51
A65-B80-C1-D51
A66-B80-C1-D51
A2-B85-C1-D51
A3-B85-C1-D51
A9-B85-C1-D51
A13-B85-C1-D51
A24-B85-C1-D51
A69-B85-C1-D51
A67-B85-C1-D51
A39-B85-C1-D51
A65-B85-C1-D51
A66-B85-C1-D51
A2-B86-C1-D51
A3-B86-C1-D51
A9-B86-C1-D51

1209

-continued

A13-B86-C1-D51
A24-B86-C1-D51
A69-B86-C1-D51
A67-B86-C1-D51
A39-B86-C1-D51
A65-B86-C1-D51
A66-B86-C1-D51
A2-B87-C1-D51
A3-B87-C1-D51
A9-B87-C1-D51
A13-B87-C1-D51
A24-B87-C1-D51
A69-B87-C1-D51
A67-B87-C1-D51
A39-B87-C1-D51
A65-B87-C1-D51
A66-B87-C1-D51
A2-B89-C1-D51
A3-B89-C1-D51
A9-B89-C1-D51
A13-B89-C1-D51
A24-B89-C1-D51
A69-B89-C1-D51
A67-B89-C1-D51
A39-B89-C1-D51
A65-B89-C1-D51
A66-B89-C1-D51
A2-B92-C1-D51
A3-B92-C1-D51
A9-B92-C1-D51
A13-B92-C1-D51
A24-B92-C1-D51
A69-B92-C1-D51
A67-B92-C1-D51
A39-B92-C1-D51
A65-B92-C1-D51
A66-B92-C1-D51
A2-B4-C2-D51
A3-B4-C2-D51
A9-B4-C2-D51
A13-B4-C2-D51
A24-B4-C2-D51
A69-B4-C2-D51
A67-B4-C2-D51
A39-B4-C2-D51
A65-B4-C2-D51
A66-B4-C2-D51
A2-B5-C2-D51
A3-B5-C2-D51
A9-B5-C2-D51
A13-B5-C2-D51
A24-B5-C2-D51
A69-B5-C2-D51
A67-B5-C2-D51
A39-B5-C2-D51
A65-B5-C2-D51
A66-B5-C2-D51
A2-B6-C2-D51
A3-B6-C2-D51
A9-B6-C2-D51
A13-B6-C2-D51
A24-B6-C2-D51
A69-B6-C2-D51
A67-B6-C2-D51
A39-B6-C2-D51
A65-B6-C2-D51
A66-B6-C2-D51
A2-B32-C2-D51
A3-B32-C2-D51
A9-B32-C2-D51
A13-B32-C2-D51
A24-B32-C2-D51
A69-B32-C2-D51
A67-B32-C2-D51
A39-B32-C2-D51
A65-B32-C2-D51
A66-B32-C2-D51
A2-B39-C2-D51
A3-B39-C2-D51
A9-B39-C2-D51

1210

-continued

A13-B39-C2-D51
A24-B39-C2-D51
A69-B39-C2-D51
A67-B39-C2-D51
A39-B39-C2-D51
A65-B39-C2-D51
A66-B39-C2-D51
A2-B45-C2-D51
A3-B45-C2-D51
A9-B45-C2-D51
A13-B45-C2-D51
A24-B45-C2-D51
A69-B45-C2-D51
A67-B45-C2-D51
A39-B45-C2-D51
A65-B45-C2-D51
A66-B45-C2-D51
A2-B53-C2-D51
A3-B53-C2-D51
A9-B53-C2-D51
A13-B53-C2-D51
A24-B53-C2-D51
A69-B53-C2-D51
A67-B53-C2-D51
A39-B53-C2-D51
A65-B53-C2-D51
A66-B53-C2-D51
A2-B79-C2-D51
A3-B79-C2-D51
A9-B79-C2-D51
A13-B79-C2-D51
A24-B79-C2-D51
A69-B79-C2-D51
A67-B79-C2-D51
A39-B79-C2-D51
A65-B79-C2-D51
A66-B79-C2-D51
A2-B80-C2-D51
A3-B80-C2-D51
A9-B80-C2-D51
A13-B80-C2-D51
A24-B80-C2-D51
A69-B80-C2-D51
A67-B80-C2-D51
A39-B80-C2-D51
A65-B80-C2-D51
A66-B80-C2-D51
A2-B85-C2-D51
A3-B85-C2-D51
A9-B85-C2-D51
A13-B85-C2-D51
A24-B85-C2-D51
A69-B85-C2-D51
A67-B85-C2-D51
A39-B85-C2-D51
A65-B85-C2-D51
A66-B85-C2-D51
A2-B86-C2-D51
A3-B86-C2-D51
A9-B86-C2-D51
A13-B86-C2-D51
A24-B86-C2-D51
A69-B86-C2-D51
A67-B86-C2-D51
A39-B86-C2-D51
A65-B86-C2-D51
A66-B86-C2-D51
A2-B87-C2-D51
A3-B87-C2-D51
A9-B87-C2-D51
A13-B87-C2-D51
A24-B87-C2-D51
A69-B87-C2-D51
A67-B87-C2-D51
A39-B87-C2-D51
A65-B87-C2-D51
A66-B87-C2-D51
A2-B89-C2-D51
A3-B89-C2-D51
A9-B89-C2-D51

-continued

A13-B89-C2-D51
A24-B89-C2-D51
A69-B89-C2-D51
A67-B89-C2-D51
A39-B89-C2-D51
A65-B89-C2-D51
A66-B89-C2-D51
A2-B92-C2-D51
A3-B92-C2-D51
A9-B92-C2-D51
A13-B92-C2-D51
A24-B92-C2-D51
A69-B92-C2-D51
A67-B92-C2-D51
A39-B92-C2-D51
A65-B92-C2-D51
A66-B92-C2-D51
A2-B4-C3-D51
A3-B4-C3-D51
A9-B4-C3-D51
A13-B4-C3-D51
A24-B4-C3-D51
A69-B4-C3-D51
A67-B4-C3-D51
A39-B4-C3-D51
A65-B4-C3-D51
A66-B4-C3-D51
A2-B5-C3-D51
A3-B5-C3-D51
A9-B5-C3-D51
A13-B5-C3-D51
A24-B5-C3-D51
A69-B5-C3-D51
A67-B5-C3-D51
A39-B5-C3-D51
A65-B5-C3-D51
A66-B5-C3-D51
A2-B6-C3-D51
A3-B6-C3-D51
A9-B6-C3-D51
A13-B6-C3-D51
A24-B6-C3-D51
A69-B6-C3-D51
A67-B6-C3-D51
A39-B6-C3-D51
A65-B6-C3-D51
A66-B6-C3-D51
A2-B32-C3-D51
A3-B32-C3-D51
A9-B32-C3-D51
A13-B32-C3-D51
A24-B32-C3-D51
A69-B32-C3-D51
A67-B32-C3-D51
A39-B32-C3-D51
A65-B32-C3-D51
A66-B32-C3-D51
A2-B39-C3-D51
A3-B39-C3-D51
A9-B39-C3-D51
A13-B39-C3-D51
A24-B39-C3-D51
A69-B39-C3-D51
A67-B39-C3-D51
A39-B39-C3-D51
A65-B39-C3-D51
A66-B39-C3-D51
A2-B45-C3-D51
A3-B45-C3-D51
A9-B45-C3-D51
A13-B45-C3-D51
A24-B45-C3-D51
A69-B45-C3-D51
A67-B45-C3-D51
A39-B45-C3-D51
A65-B45-C3-D51
A66-B45-C3-D51
A2-B53-C3-D51
A3-B53-C3-D51
A9-B53-C3-D51

-continued

A13-B53-C3-D51
A24-B53-C3-D51
A69-B53-C3-D51
A67-B53-C3-D51
A39-B53-C3-D51
A65-B53-C3-D51
A66-B53-C3-D51
A2-B79-C3-D51
A3-B79-C3-D51
A9-B79-C3-D51
A13-B79-C3-D51
A24-B79-C3-D51
A69-B79-C3-D51
A67-B79-C3-D51
A39-B79-C3-D51
A65-B79-C3-D51
A66-B79-C3-D51
A2-B80-C3-D51
A3-B80-C3-D51
A9-B80-C3-D51
A13-B80-C3-D51
A24-B80-C3-D51
A69-B80-C3-D51
A67-B80-C3-D51
A39-B80-C3-D51
A65-B80-C3-D51
A66-B80-C3-D51
A2-B85-C3-D51
A3-B85-C3-D51
A9-B85-C3-D51
A13-B85-C3-D51
A24-B85-C3-D51
A69-B85-C3-D51
A67-B85-C3-D51
A39-B85-C3-D51
A65-B85-C3-D51
A66-B85-C3-D51
A2-B86-C3-D51
A3-B86-C3-D51
A9-B86-C3-D51
A13-B86-C3-D51
A24-B86-C3-D51
A69-B86-C3-D51
A67-B86-C3-D51
A39-B86-C3-D51
A65-B86-C3-D51
A66-B86-C3-D51
A2-B87-C3-D51
A3-B87-C3-D51
A9-B87-C3-D51
A13-B87-C3-D51
A24-B87-C3-D51
A69-B87-C3-D51
A67-B87-C3-D51
A39-B87-C3-D51
A65-B87-C3-D51
A66-B87-C3-D51
A2-B89-C3-D51
A3-B89-C3-D51
A9-B89-C3-D51
A13-B89-C3-D51
A24-B89-C3-D51
A69-B89-C3-D51
A67-B89-C3-D51
A39-B89-C3-D51
A65-B89-C3-D51
A66-B89-C3-D51
A2-B92-C3-D51
A3-B92-C3-D51
A9-B92-C3-D51
A13-B92-C3-D51
A24-B92-C3-D51
A69-B92-C3-D51
A67-B92-C3-D51
A39-B92-C3-D51
A65-B92-C3-D51
A66-B92-C3-D51
A2-B4-C4-D51
A3-B4-C4-D51
A9-B4-C4-D51

-continued

A13-B4-C4-D51
A24-B4-C4-D51
A69-B4-C4-D51
A67-B4-C4-D51
A39-B4-C4-D51
A65-B4-C4-D51
A66-B4-C4-D51
A2-B5-C4-D51
A3-B5-C4-D51
A9-B5-C4-D51
A13-B5-C4-D51
A24-B5-C4-D51
A69-B5-C4-D51
A67-B5-C4-D51
A39-B5-C4-D51
A65-B5-C4-D51
A66-B5-C4-D51
A2-B6-C4-D51
A3-B6-C4-D51
A9-B6-C4-D51
A13-B6-C4-D51
A24-B6-C4-D51
A69-B6-C4-D51
A67-B6-C4-D51
A39-B6-C4-D51
A65-B6-C4-D51
A66-B6-C4-D51
A2-B32-C4-D51
A3-B32-C4-D51
A9-B32-C4-D51
A13-B32-C4-D51
A24-B32-C4-D51
A69-B32-C4-D51
A67-B32-C4-D51
A39-B32-C4-D51
A65-B32-C4-D51
A66-B32-C4-D51
A2-B39-C4-D51
A3-B39-C4-D51
A9-B39-C4-D51
A13-B39-C4-D51
A24-B39-C4-D51
A69-B39-C4-D51
A67-B39-C4-D51
A39-B39-C4-D51
A65-B39-C4-D51
A66-B39-C4-D51
A2-B45-C4-D51
A3-B45-C4-D51
A9-B45-C4-D51
A13-B45-C4-D51
A24-B45-C4-D51
A69-B45-C4-D51
A67-B45-C4-D51
A39-B45-C4-D51
A65-B45-C4-D51
A66-B45-C4-D51
A2-B53-C4-D51
A3-B53-C4-D51
A9-B53-C4-D51
A13-B53-C4-D51
A24-B53-C4-D51
A69-B53-C4-D51
A67-B53-C4-D51
A39-B53-C4-D51
A65-B53-C4-D51
A66-B53-C4-D51
A2-B79-C4-D51
A3-B79-C4-D51
A9-B79-C4-D51
A13-B79-C4-D51
A24-B79-C4-D51
A69-B79-C4-D51
A67-B79-C4-D51
A39-B79-C4-D51
A65-B79-C4-D51
A66-B79-C4-D51
A2-B80-C4-D51
A3-B80-C4-D51
A9-B80-C4-D51

-continued

A13-B80-C4-D51
A24-B80-C4-D51
A69-B80-C4-D51
A67-B80-C4-D51
A39-B80-C4-D51
A65-B80-C4-D51
A66-B80-C4-D51
A2-B85-C4-D51
A3-B85-C4-D51
A9-B85-C4-D51
A13-B85-C4-D51
A24-B85-C4-D51
A69-B85-C4-D51
A67-B85-C4-D51
A39-B85-C4-D51
A65-B85-C4-D51
A66-B85-C4-D51
A2-B86-C4-D51
A3-B86-C4-D51
A9-B86-C4-D51
A13-B86-C4-D51
A24-B86-C4-D51
A69-B86-C4-D51
A67-B86-C4-D51
A39-B86-C4-D51
A65-B86-C4-D51
A66-B86-C4-D51
A2-B87-C4-D51
A3-B87-C4-D51
A9-B87-C4-D51
A13-B87-C4-D51
A24-B87-C4-D51
A69-B87-C4-D51
A67-B87-C4-D51
A39-B87-C4-D51
A65-B87-C4-D51
A66-B87-C4-D51
A2-B89-C4-D51
A3-B89-C4-D51
A9-B89-C4-D51
A13-B89-C4-D51
A24-B89-C4-D51
A69-B89-C4-D51
A67-B89-C4-D51
A39-B89-C4-D51
A65-B89-C4-D51
A66-B89-C4-D51
A2-B92-C4-D51
A3-B92-C4-D51
A9-B92-C4-D51
A13-B92-C4-D51
A24-B92-C4-D51
A69-B92-C4-D51
A67-B92-C4-D51
A39-B92-C4-D51
A65-B92-C4-D51
A66-B92-C4-D51
A2-B4-C5-D51
A3-B4-C5-D51
A9-B4-C5-D51
A13-B4-C5-D51
A24-B4-C5-D51
A69-B4-C5-D51
A67-B4-C5-D51
A39-B4-C5-D51
A65-B4-C5-D51
A66-B4-C5-D51
A2-B5-C5-D51
A3-B5-C5-D51
A9-B5-C5-D51
A13-B5-C5-D51
A24-B5-C5-D51
A69-B5-C5-D51
A67-B5-C5-D51
A39-B5-C5-D51
A65-B5-C5-D51
A66-B5-C5-D51
A2-B6-C5-D51
A3-B6-C5-D51
A9-B6-C5-D51

-continued
A13-B6-C5-D51
A24-B6-C5-D51
A69-B6-C5-D51
A67-B6-C5-D51
A39-B6-C5-D51
A65-B6-C5-D51
A66-B6-C5-D51
A2-B32-C5-D51
A3-B32-C5-D51
A9-B32-C5-D51
A13-B32-C5-D51
A24-B32-C5-D51
A69-B32-C5-D51
A67-B32-C5-D51
A39-B32-C5-D51
A65-B32-C5-D51
A66-B32-C5-D51
A2-B39-C5-D51
A3-B39-C5-D51
A9-B39-C5-D51
A13-B39-C5-D51
A24-B39-C5-D51
A69-B39-C5-D51
A67-B39-C5-D51
A39-B39-C5-D51
A65-B39-C5-D51
A66-B39-C5-D51
A2-B45-C5-D51
A3-B45-C5-D51
A9-B45-C5-D51
A13-B45-C5-D51
A24-B45-C5-D51
A69-B45-C5-D51
A67-B45-C5-D51
A39-B45-C5-D51
A65-B45-C5-D51
A66-B45-C5-D51
A2-B53-C5-D51
A3-B53-C5-D51
A9-B53-C5-D51
A13-B53-C5-D51
A24-B53-C5-D51
A69-B53-C5-D51
A67-B53-C5-D51
A39-B53-C5-D51
A65-B53-C5-D51
A66-B53-C5-D51
A2-B79-C5-D51
A3-B79-C5-D51
A9-B79-C5-D51
A13-B79-C5-D51
A24-B79-C5-D51
A69-B79-C5-D51
A67-B79-C5-D51
A39-B79-C5-D51
A65-B79-C5-D51
A66-B79-C5-D51
A2-B80-C5-D51
A3-B80-C5-D51
A9-B80-C5-D51
A13-B80-C5-D51
A24-B80-C5-D51
A69-B80-C5-D51
A67-B80-C5-D51
A39-B80-C5-D51
A65-B80-C5-D51
A66-B80-C5-D51
A2-B85-C5-D51
A3-B85-C5-D51
A9-B85-C5-D51
A13-B85-C5-D51
A24-B85-C5-D51
A69-B85-C5-D51
A67-B85-C5-D51
A39-B85-C5-D51
A65-B85-C5-D51
A66-B85-C5-D51
A2-B86-C5-D51
A3-B86-C5-D51
A9-B86-C5-D51

-continued
A13-B86-C5-D51
A24-B86-C5-D51
A69-B86-C5-D51
A67-B86-C5-D51
A39-B86-C5-D51
A65-B86-C5-D51
A66-B86-C5-D51
A2-B87-C5-D51
A3-B87-C5-D51
A9-B87-C5-D51
A13-B87-C5-D51
A24-B87-C5-D51
A69-B87-C5-D51
A67-B87-C5-D51
A39-B87-C5-D51
A65-B87-C5-D51
A66-B87-C5-D51
A2-B89-C5-D51
A3-B89-C5-D51
A9-B89-C5-D51
A13-B89-C5-D51
A24-B89-C5-D51
A69-B89-C5-D51
A67-B89-C5-D51
A39-B89-C5-D51
A65-B89-C5-D51
A66-B89-C5-D51
A2-B92-C5-D51
A3-B92-C5-D51
A9-B92-C5-D51
A13-B92-C5-D51
A24-B92-C5-D51
A69-B92-C5-D51
A67-B92-C5-D51
A39-B92-C5-D51
A65-B92-C5-D51
A66-B92-C5-D51
A2-B4-C6-D51
A3-B4-C6-D51
A9-B4-C6-D51
A13-B4-C6-D51
A24-B4-C6-D51
A69-B4-C6-D51
A67-B4-C6-D51
A39-B4-C6-D51
A65-B4-C6-D51
A66-B4-C6-D51
A2-B5-C6-D51
A3-B5-C6-D51
A9-B5-C6-D51
A13-B5-C6-D51
A24-B5-C6-D51
A69-B5-C6-D51
A67-B5-C6-D51
A39-B5-C6-D51
A65-B5-C6-D51
A66-B5-C6-D51
A2-B6-C6-D51
A3-B6-C6-D51
A9-B6-C6-D51
A13-B6-C6-D51
A24-B6-C6-D51
A69-B6-C6-D51
A67-B6-C6-D51
A39-B6-C6-D51
A65-B6-C6-D51
A66-B6-C6-D51
A2-B32-C6-D51
A3-B32-C6-D51
A9-B32-C6-D51
A13-B32-C6-D51
A24-B32-C6-D51
A69-B32-C6-D51
A67-B32-C6-D51
A39-B32-C6-D51
A65-B32-C6-D51
A66-B32-C6-D51
A2-B39-C6-D51
A3-B39-C6-D51
A9-B39-C6-D51

-continued

A13-B39-C6-D51
A24-B39-C6-D51
A69-B39-C6-D51
A67-B39-C6-D51
A39-B39-C6-D51
A65-B39-C6-D51
A66-B39-C6-D51
A2-B45-C6-D51
A3-B45-C6-D51
A9-B45-C6-D51
A13-B45-C6-D51
A24-B45-C6-D51
A69-B45-C6-D51
A67-B45-C6-D51
A39-B45-C6-D51
A65-B45-C6-D51
A66-B45-C6-D51
A2-B53-C6-D51
A3-B53-C6-D51
A9-B53-C6-D51
A13-B53-C6-D51
A24-B53-C6-D51
A69-B53-C6-D51
A67-B53-C6-D51
A39-B53-C6-D51
A65-B53-C6-D51
A66-B53-C6-D51
A2-B79-C6-D51
A3-B79-C6-D51
A9-B79-C6-D51
A13-B79-C6-D51
A24-B79-C6-D51
A69-B79-C6-D51
A67-B79-C6-D51
A39-B79-C6-D51
A65-B79-C6-D51
A66-B79-C6-D51
A2-B80-C6-D51
A3-B80-C6-D51
A9-B80-C6-D51
A13-B80-C6-D51
A24-B80-C6-D51
A69-B80-C6-D51
A67-B80-C6-D51
A39-B80-C6-D51
A65-B80-C6-D51
A66-B80-C6-D51
A2-B85-C6-D51
A3-B85-C6-D51
A9-B85-C6-D51
A13-B85-C6-D51
A24-B85-C6-D51
A69-B85-C6-D51
A67-B85-C6-D51
A39-B85-C6-D51
A65-B85-C6-D51
A66-B85-C6-D51
A2-B86-C6-D51
A3-B86-C6-D51
A9-B86-C6-D51
A13-B86-C6-D51
A24-B86-C6-D51
A69-B86-C6-D51
A67-B86-C6-D51
A39-B86-C6-D51
A65-B86-C6-D51
A66-B86-C6-D51
A2-B87-C6-D51
A3-B87-C6-D51
A9-B87-C6-D51
A13-B87-C6-D51
A24-B87-C6-D51
A69-B87-C6-D51
A67-B87-C6-D51
A39-B87-C6-D51
A65-B87-C6-D51
A66-B87-C6-D51
A2-B89-C6-D51
A3-B89-C6-D51
A9-B89-C6-D51

-continued

A13-B89-C6-D51
A24-B89-C6-D51
A69-B89-C6-D51
A67-B89-C6-D51
A39-B89-C6-D51
A65-B89-C6-D51
A66-B89-C6-D51
A2-B92-C6-D51
A3-B92-C6-D51
A9-B92-C6-D51
A13-B92-C6-D51
A24-B92-C6-D51
A69-B92-C6-D51
A67-B92-C6-D51
A39-B92-C6-D51
A65-B92-C6-D51
A66-B92-C6-D51
A2-B4-C7-D51
A3-B4-C7-D51
A9-B4-C7-D51
A13-B4-C7-D51
A24-B4-C7-D51
A69-B4-C7-D51
A67-B4-C7-D51
A39-B4-C7-D51
A65-B4-C7-D51
A66-B4-C7-D51
A2-B5-C7-D51
A3-B5-C7-D51
A9-B5-C7-D51
A13-B5-C7-D51
A24-B5-C7-D51
A69-B5-C7-D51
A67-B5-C7-D51
A39-B5-C7-D51
A65-B5-C7-D51
A66-B5-C7-D51
A2-B6-C7-D51
A3-B6-C7-D51
A9-B6-C7-D51
A13-B6-C7-D51
A24-B6-C7-D51
A69-B6-C7-D51
A67-B6-C7-D51
A39-B6-C7-D51
A65-B6-C7-D51
A66-B6-C7-D51
A2-B32-C7-D51
A3-B32-C7-D51
A9-B32-C7-D51
A13-B32-C7-D51
A24-B32-C7-D51
A69-B32-C7-D51
A67-B32-C7-D51
A39-B32-C7-D51
A65-B32-C7-D51
A66-B32-C7-D51
A2-B39-C7-D51
A3-B39-C7-D51
A9-B39-C7-D51
A13-B39-C7-D51
A24-B39-C7-D51
A69-B39-C7-D51
A67-B39-C7-D51
A39-B39-C7-D51
A65-B39-C7-D51
A66-B39-C7-D51
A2-B45-C7-D51
A3-B45-C7-D51
A9-B45-C7-D51
A13-B45-C7-D51
A24-B45-C7-D51
A69-B45-C7-D51
A67-B45-C7-D51
A39-B45-C7-D51
A65-B45-C7-D51
A66-B45-C7-D51
A2-B53-C7-D51
A3-B53-C7-D51
A9-B53-C7-D51

-continued

A13-B53-C7-D51
A24-B53-C7-D51
A69-B53-C7-D51
A67-B53-C7-D51
A39-B53-C7-D51
A65-B53-C7-D51
A66-B53-C7-D51
A2-B79-C7-D51
A3-B79-C7-D51
A9-B79-C7-D51
A13-B79-C7-D51
A24-B79-C7-D51
A69-B79-C7-D51
A67-B79-C7-D51
A39-B79-C7-D51
A65-B79-C7-D51
A66-B79-C7-D51
A2-B80-C7-D51
A3-B80-C7-D51
A9-B80-C7-D51
A13-B80-C7-D51
A24-B80-C7-D51
A69-B80-C7-D51
A67-B80-C7-D51
A39-B80-C7-D51
A65-B80-C7-D51
A66-B80-C7-D51
A2-B85-C7-D51
A3-B85-C7-D51
A9-B85-C7-D51
A13-B85-C7-D51
A24-B85-C7-D51
A69-B85-C7-D51
A67-B85-C7-D51
A39-B85-C7-D51
A65-B85-C7-D51
A66-B85-C7-D51
A2-B86-C7-D51
A3-B86-C7-D51
A9-B86-C7-D51
A13-B86-C7-D51
A24-B86-C7-D51
A69-B86-C7-D51
A67-B86-C7-D51
A39-B86-C7-D51
A65-B86-C7-D51
A66-B86-C7-D51
A2-B87-C7-D51
A3-B87-C7-D51
A9-B87-C7-D51
A13-B87-C7-D51
A24-B87-C7-D51
A69-B87-C7-D51
A67-B87-C7-D51
A39-B87-C7-D51
A65-B87-C7-D51
A66-B87-C7-D51
A2-B89-C7-D51
A3-B89-C7-D51
A9-B89-C7-D51
A13-B89-C7-D51
A24-B89-C7-D51
A69-B89-C7-D51
A67-B89-C7-D51
A39-B89-C7-D51
A65-B89-C7-D51
A66-B89-C7-D51
A2-B92-C7-D51
A3-B92-C7-D51
A9-B92-C7-D51
A13-B92-C7-D51
A24-B92-C7-D51
A69-B92-C7-D51
A67-B92-C7-D51
A39-B92-C7-D51
A65-B92-C7-D51
A66-B92-C7-D51
A2-B4-C8-D51
A3-B4-C8-D51
A9-B4-C8-D51

-continued

A13-B4-C8-D51
A24-B4-C8-D51
A69-B4-C8-D51
A67-B4-C8-D51
A39-B4-C8-D51
A65-B4-C8-D51
A66-B4-C8-D51
A2-B5-C8-D51
A3-B5-C8-D51
A9-B5-C8-D51
A13-B5-C8-D51
A24-B5-C8-D51
A69-B5-C8-D51
A67-B5-C8-D51
A39-B5-C8-D51
A65-B5-C8-D51
A66-B5-C8-D51
A2-B6-C8-D51
A3-B6-C8-D51
A9-B6-C8-D51
A13-B6-C8-D51
A24-B6-C8-D51
A69-B6-C8-D51
A67-B6-C8-D51
A39-B6-C8-D51
A65-B6-C8-D51
A66-B6-C8-D51
A2-B32-C8-D51
A3-B32-C8-D51
A9-B32-C8-D51
A13-B32-C8-D51
A24-B32-C8-D51
A69-B32-C8-D51
A67-B32-C8-D51
A39-B32-C8-D51
A65-B32-C8-D51
A66-B32-C8-D51
A2-B39-C8-D51
A3-B39-C8-D51
A9-B39-C8-D51
A13-B39-C8-D51
A24-B39-C8-D51
A69-B39-C8-D51
A67-B39-C8-D51
A39-B39-C8-D51
A65-B39-C8-D51
A66-B39-C8-D51
A2-B45-C8-D51
A3-B45-C8-D51
A9-B45-C8-D51
A13-B45-C8-D51
A24-B45-C8-D51
A69-B45-C8-D51
A67-B45-C8-D51
A39-B45-C8-D51
A65-B45-C8-D51
A66-B45-C8-D51
A2-B53-C8-D51
A3-B53-C8-D51
A9-B53-C8-D51
A13-B53-C8-D51
A24-B53-C8-D51
A69-B53-C8-D51
A67-B53-C8-D51
A39-B53-C8-D51
A65-B53-C8-D51
A66-B53-C8-D51
A2-B79-C8-D51
A3-B79-C8-D51
A9-B79-C8-D51
A13-B79-C8-D51
A24-B79-C8-D51
A69-B79-C8-D51
A67-B79-C8-D51
A39-B79-C8-D51
A65-B79-C8-D51
A66-B79-C8-D51
A2-B80-C8-D51
A3-B80-C8-D51
A9-B80-C8-D51

-continued

A13-B80-C8-D51
A24-B80-C8-D51
A69-B80-C8-D51
A67-B80-C8-D51
A39-B80-C8-D51
A65-B80-C8-D51
A66-B80-C8-D51
A2-B85-C8-D51
A3-B85-C8-D51
A9-B85-C8-D51
A13-B85-C8-D51
A24-B85-C8-D51
A69-B85-C8-D51
A67-B85-C8-D51
A39-B85-C8-D51
A65-B85-C8-D51
A66-B85-C8-D51
A2-B86-C8-D51
A3-B86-C8-D51
A9-B86-C8-D51
A13-B86-C8-D51
A24-B86-C8-D51
A69-B86-C8-D51
A67-B86-C8-D51
A39-B86-C8-D51
A65-B86-C8-D51
A66-B86-C8-D51
A2-B87-C8-D51
A3-B87-C8-D51
A9-B87-C8-D51
A13-B87-C8-D51
A24-B87-C8-D51
A69-B87-C8-D51
A67-B87-C8-D51
A39-B87-C8-D51
A65-B87-C8-D51
A66-B87-C8-D51
A2-B89-C8-D51
A3-B89-C8-D51
A9-B89-C8-D51
A13-B89-C8-D51
A24-B89-C8-D51
A69-B89-C8-D51
A67-B89-C8-D51
A39-B89-C8-D51
A65-B89-C8-D51
A66-B89-C8-D51
A2-B92-C8-D51
A3-B92-C8-D51
A9-B92-C8-D51
A13-B92-C8-D51
A24-B92-C8-D51
A69-B92-C8-D51
A67-B92-C8-D51
A39-B92-C8-D51
A65-B92-C8-D51
A66-B92-C8-D51
A2-B4-C9-D51
A3-B4-C9-D51
A9-B4-C9-D51
A13-B4-C9-D51
A24-B4-C9-D51
A69-B4-C9-D51
A67-B4-C9-D51
A39-B4-C9-D51
A65-B4-C9-D51
A66-B4-C9-D51
A2-B5-C9-D51
A3-B5-C9-D51
A9-B5-C9-D51
A13-B5-C9-D51
A24-B5-C9-D51
A69-B5-C9-D51
A67-B5-C9-D51
A39-B5-C9-D51
A65-B5-C9-D51
A66-B5-C9-D51
A2-B6-C9-D51
A3-B6-C9-D51
A9-B6-C9-D51

-continued

A13-B6-C9-D51
A24-B6-C9-D51
A69-B6-C9-D51
A67-B6-C9-D51
A39-B6-C9-D51
A65-B6-C9-D51
A66-B6-C9-D51
A2-B32-C9-D51
A3-B32-C9-D51
A9-B32-C9-D51
A13-B32-C9-D51
A24-B32-C9-D51
A69-B32-C9-D51
A67-B32-C9-D51
A39-B32-C9-D51
A65-B32-C9-D51
A66-B32-C9-D51
A2-B39-C9-D51
A3-B39-C9-D51
A9-B39-C9-D51
A13-B39-C9-D51
A24-B39-C9-D51
A69-B39-C9-D51
A67-B39-C9-D51
A39-B39-C9-D51
A65-B39-C9-D51
A66-B39-C9-D51
A2-B45-C9-D51
A3-B45-C9-D51
A9-B45-C9-D51
A13-B45-C9-D51
A24-B45-C9-D51
A69-B45-C9-D51
A67-B45-C9-D51
A39-B45-C9-D51
A65-B45-C9-D51
A66-B45-C9-D51
A2-B53-C9-D51
A3-B53-C9-D51
A9-B53-C9-D51
A13-B53-C9-D51
A24-B53-C9-D51
A69-B53-C9-D51
A67-B53-C9-D51
A39-B53-C9-D51
A65-B53-C9-D51
A66-B53-C9-D51
A2-B79-C9-D51
A3-B79-C9-D51
A9-B79-C9-D51
A13-B79-C9-D51
A24-B79-C9-D51
A69-B79-C9-D51
A67-B79-C9-D51
A39-B79-C9-D51
A65-B79-C9-D51
A66-B79-C9-D51
A2-B80-C9-D51
A3-B80-C9-D51
A9-B80-C9-D51
A13-B80-C9-D51
A24-B80-C9-D51
A69-B80-C9-D51
A67-B80-C9-D51
A39-B80-C9-D51
A65-B80-C9-D51
A66-B80-C9-D51
A2-B85-C9-D51
A3-B85-C9-D51
A9-B85-C9-D51
A13-B85-C9-D51
A24-B85-C9-D51
A69-B85-C9-D51
A67-B85-C9-D51
A39-B85-C9-D51
A65-B85-C9-D51
A66-B85-C9-D51
A2-B86-C9-D51
A3-B86-C9-D51
A9-B86-C9-D51

-continued

A13-B86-C9-D51
A24-B86-C9-D51
A69-B86-C9-D51
A67-B86-C9-D51
A39-B86-C9-D51
A65-B86-C9-D51
A66-B86-C9-D51
A2-B87-C9-D51
A3-B87-C9-D51
A9-B87-C9-D51
A13-B87-C9-D51
A24-B87-C9-D51
A69-B87-C9-D51
A67-B87-C9-D51
A39-B87-C9-D51
A65-B87-C9-D51
A66-B87-C9-D51
A2-B89-C9-D51
A3-B89-C9-D51
A9-B89-C9-D51
A13-B89-C9-D51
A24-B89-C9-D51
A69-B89-C9-D51
A67-B89-C9-D51
A39-B89-C9-D51
A65-B89-C9-D51
A66-B89-C9-D51
A2-B92-C9-D51
A3-B92-C9-D51
A9-B92-C9-D51
A13-B92-C9-D51
A24-B92-C9-D51
A69-B92-C9-D51
A67-B92-C9-D51
A39-B92-C9-D51
A65-B92-C9-D51
A66-B92-C9-D51
A2-B4-C10-D51
A3-B4-C10-D51
A9-B4-C10-D51
A13-B4-C10-D51
A24-B4-C10-D51
A69-B4-C10-D51
A67-B4-C10-D51
A39-B4-C10-D51
A65-B4-C10-D51
A66-B4-C10-D51
A2-B5-C10-D51
A3-B5-C10-D51
A9-B5-C10-D51
A13-B5-C10-D51
A24-B5-C10-D51
A69-B5-C10-D51
A67-B5-C10-D51
A39-B5-C10-D51
A65-B5-C10-D51
A66-B5-C10-D51
A2-B6-C10-D51
A3-B6-C10-D51
A9-B6-C10-D51
A13-B6-C10-D51
A24-B6-C10-D51
A69-B6-C10-D51
A67-B6-C10-D51
A39-B6-C10-D51
A65-B6-C10-D51
A66-B6-C10-D51
A2-B32-C10-D51
A3-B32-C10-D51
A9-B32-C10-D51
A13-B32-C10-D51
A24-B32-C10-D51
A69-B32-C10-D51
A67-B32-C10-D51
A39-B32-C10-D51
A65-B32-C10-D51
A66-B32-C10-D51
A2-B39-C10-D51
A3-B39-C10-D51
A9-B39-C10-D51

-continued

A13-B39-C10-D51
A24-B39-C10-D51
A69-B39-C10-D51
A67-B39-C10-D51
A39-B39-C10-D51
A65-B39-C10-D51
A66-B39-C10-D51
A2-B45-C10-D51
A3-B45-C10-D51
A9-B45-C10-D51
A13-B45-C10-D51
A24-B45-C10-D51
A69-B45-C10-D51
A67-B45-C10-D51
A39-B45-C10-D51
A65-B45-C10-D51
A66-B45-C10-D51
A2-B53-C10-D51
A3-B53-C10-D51
A9-B53-C10-D51
A13-B53-C10-D51
A24-B53-C10-D51
A69-B53-C10-D51
A67-B53-C10-D51
A39-B53-C10-D51
A65-B53-C10-D51
A66-B53-C10-D51
A2-B79-C10-D51
A3-B79-C10-D51
A9-B79-C10-D51
A13-B79-C10-D51
A24-B79-C10-D51
A69-B79-C10-D51
A67-B79-C10-D51
A39-B79-C10-D51
A65-B79-C10-D51
A66-B79-C10-D51
A2-B80-C10-D51
A3-B80-C10-D51
A9-B80-C10-D51
A13-B80-C10-D51
A24-B80-C10-D51
A69-B80-C10-D51
A67-B80-C10-D51
A39-B80-C10-D51
A65-B80-C10-D51
A66-B80-C10-D51
A2-B85-C10-D51
A3-B85-C10-D51
A9-B85-C10-D51
A13-B85-C10-D51
A24-B85-C10-D51
A69-B85-C10-D51
A67-B85-C10-D51
A39-B85-C10-D51
A65-B85-C10-D51
A66-B85-C10-D51
A2-B86-C10-D51
A3-B86-C10-D51
A9-B86-C10-D51
A13-B86-C10-D51
A24-B86-C10-D51
A69-B86-C10-D51
A67-B86-C10-D51
A39-B86-C10-D51
A65-B86-C10-D51
A66-B86-C10-D51
A2-B87-C10-D51
A3-B87-C10-D51
A9-B87-C10-D51
A13-B87-C10-D51
A24-B87-C10-D51
A69-B87-C10-D51
A67-B87-C10-D51
A39-B87-C10-D51
A65-B87-C10-D51
A66-B87-C10-D51
A2-B89-C10-D51
A3-B89-C10-D51
A9-B89-C10-D51

-continued
A13-B89-C10-D51
A24-B89-C10-D51
A69-B89-C10-D51
A67-B89-C10-D51
A39-B89-C10-D51
A65-B89-C10-D51
A66-B89-C10-D51
A2-B92-C10-D51
A3-B92-C10-D51
A9-B92-C10-D51
A13-B92-C10-D51
A24-B92-C10-D51
A69-B92-C10-D51
A67-B92-C10-D51
A39-B92-C10-D51
A65-B92-C10-D51
A66-B92-C10-D51
A2-B4-C11-D51
A3-B4-C11-D51
A9-B4-C11-D51
A13-B4-C11-D51
A24-B4-C11-D51
A69-B4-C11-D51
A67-B4-C11-D51
A39-B4-C11-D51
A65-B4-C11-D51
A66-B4-C11-D51
A2-B5-C11-D51
A3-B5-C11-D51
A9-B5-C11-D51
A13-B5-C11-D51
A24-B5-C11-D51
A69-B5-C11-D51
A67-B5-C11-D51
A39-B5-C11-D51
A65-B5-C11-D51
A66-B5-C11-D51
A2-B6-C11-D51
A3-B6-C11-D51
A9-B6-C11-D51
A13-B6-C11-D51
A24-B6-C11-D51
A69-B6-C11-D51
A67-B6-C11-D51
A39-B6-C11-D51
A65-B6-C11-D51
A66-B6-C11-D51
A2-B32-C11-D51
A3-B32-C11-D51
A9-B32-C11-D51
A13-B32-C11-D51
A24-B32-C11-D51
A69-B32-C11-D51
A67-B32-C11-D51
A39-B32-C11-D51
A65-B32-C11-D51
A66-B32-C11-D51
A2-B39-C11-D51
A3-B39-C11-D51
A9-B39-C11-D51
A13-B39-C11-D51
A24-B39-C11-D51
A69-B39-C11-D51
A67-B39-C11-D51
A39-B39-C11-D51
A65-B39-C11-D51
A66-B39-C11-D51
A2-B45-C11-D51
A3-B45-C11-D51
A9-B45-C11-D51
A13-B45-C11-D51
A24-B45-C11-D51
A69-B45-C11-D51
A67-B45-C11-D51
A39-B45-C11-D51
A65-B45-C11-D51
A66-B45-C11-D51
A2-B53-C11-D51
A3-B53-C11-D51
A9-B53-C11-D51

-continued
A13-B53-C11-D51
A24-B53-C11-D51
A69-B53-C11-D51
A67-B53-C11-D51
A39-B53-C11-D51
A65-B53-C11-D51
A66-B53-C11-D51
A2-B79-C11-D51
A3-B79-C11-D51
A9-B79-C11-D51
A13-B79-C11-D51
A24-B79-C11-D51
A69-B79-C11-D51
A67-B79-C11-D51
A39-B79-C11-D51
A65-B79-C11-D51
A66-B79-C11-D51
A2-B80-C11-D51
A3-B80-C11-D51
A9-B80-C11-D51
A13-B80-C11-D51
A24-B80-C11-D51
A69-B80-C11-D51
A67-B80-C11-D51
A39-B80-C11-D51
A65-B80-C11-D51
A66-B80-C11-D51
A2-B85-C11-D51
A3-B85-C11-D51
A9-B85-C11-D51
A13-B85-C11-D51
A24-B85-C11-D51
A69-B85-C11-D51
A67-B85-C11-D51
A39-B85-C11-D51
A65-B85-C11-D51
A66-B85-C11-D51
A2-B86-C11-D51
A3-B86-C11-D51
A9-B86-C11-D51
A13-B86-C11-D51
A24-B86-C11-D51
A69-B86-C11-D51
A67-B86-C11-D51
A39-B86-C11-D51
A65-B86-C11-D51
A66-B86-C11-D51
A2-B87-C11-D51
A3-B87-C11-D51
A9-B87-C11-D51
A13-B87-C11-D51
A24-B87-C11-D51
A69-B87-C11-D51
A67-B87-C11-D51
A39-B87-C11-D51
A65-B87-C11-D51
A66-B87-C11-D51
A2-B89-C11-D51
A3-B89-C11-D51
A9-B89-C11-D51
A13-B89-C11-D51
A24-B89-C11-D51
A69-B89-C11-D51
A67-B89-C11-D51
A39-B89-C11-D51
A65-B89-C11-D51
A66-B89-C11-D51
A2-B92-C11-D51
A3-B92-C11-D51
A9-B92-C11-D51
A13-B92-C11-D51
A24-B92-C11-D51
A69-B92-C11-D51
A67-B92-C11-D51
A39-B92-C11-D51
A65-B92-C11-D51
A66-B92-C11-D51
A2-B4-C12-D51
A3-B4-C12-D51
A9-B4-C12-D51

-continued

A13-B4-C12-D51
A24-B4-C12-D51
A69-B4-C12-D51
A67-B4-C12-D51
A39-B4-C12-D51
A65-B4-C12-D51
A66-B4-C12-D51
A2-B5-C12-D51
A3-B5-C12-D51
A9-B5-C12-D51
A13-B5-C12-D51
A24-B5-C12-D51
A69-B5-C12-D51
A67-B5-C12-D51
A39-B5-C12-D51
A65-B5-C12-D51
A66-B5-C12-D51
A2-B6-C12-D51
A3-B6-C12-D51
A9-B6-C12-D51
A13-B6-C12-D51
A24-B6-C12-D51
A69-B6-C12-D51
A67-B6-C12-D51
A39-B6-C12-D51
A65-B6-C12-D51
A66-B6-C12-D51
A2-B32-C12-D51
A3-B32-C12-D51
A9-B32-C12-D51
A13-B32-C12-D51
A24-B32-C12-D51
A69-B32-C12-D51
A67-B32-C12-D51
A39-B32-C12-D51
A65-B32-C12-D51
A66-B32-C12-D51
A2-B39-C12-D51
A3-B39-C12-D51
A9-B39-C12-D51
A13-B39-C12-D51
A24-B39-C12-D51
A69-B39-C12-D51
A67-B39-C12-D51
A39-B39-C12-D51
A65-B39-C12-D51
A66-B39-C12-D51
A2-B45-C12-D51
A3-B45-C12-D51
A9-B45-C12-D51
A13-B45-C12-D51
A24-B45-C12-D51
A69-B45-C12-D51
A67-B45-C12-D51
A39-B45-C12-D51
A65-B45-C12-D51
A66-B45-C12-D51
A2-B53-C12-D51
A3-B53-C12-D51
A9-B53-C12-D51
A13-B53-C12-D51
A24-B53-C12-D51
A69-B53-C12-D51
A67-B53-C12-D51
A39-B53-C12-D51
A65-B53-C12-D51
A66-B53-C12-D51
A2-B79-C12-D51
A3-B79-C12-D51
A9-B79-C12-D51
A13-B79-C12-D51
A24-B79-C12-D51
A69-B79-C12-D51
A67-B79-C12-D51
A39-B79-C12-D51
A65-B79-C12-D51
A66-B79-C12-D51
A2-B80-C12-D51
A3-B80-C12-D51
A9-B80-C12-D51

-continued

A13-B80-C12-D51
A24-B80-C12-D51
A69-B80-C12-D51
A67-B80-C12-D51
A39-B80-C12-D51
A65-B80-C12-D51
A66-B80-C12-D51
A2-B85-C12-D51
A3-B85-C12-D51
A9-B85-C12-D51
A13-B85-C12-D51
A24-B85-C12-D51
A69-B85-C12-D51
A67-B85-C12-D51
A39-B85-C12-D51
A65-B85-C12-D51
A66-B85-C12-D51
A2-B86-C12-D51
A3-B86-C12-D51
A9-B86-C12-D51
A13-B86-C12-D51
A24-B86-C12-D51
A69-B86-C12-D51
A67-B86-C12-D51
A39-B86-C12-D51
A65-B86-C12-D51
A66-B86-C12-D51
A2-B87-C12-D51
A3-B87-C12-D51
A9-B87-C12-D51
A13-B87-C12-D51
A24-B87-C12-D51
A69-B87-C12-D51
A67-B87-C12-D51
A39-B87-C12-D51
A65-B87-C12-D51
A66-B87-C12-D51
A2-B89-C12-D51
A3-B89-C12-D51
A9-B89-C12-D51
A13-B89-C12-D51
A24-B89-C12-D51
A69-B89-C12-D51
A67-B89-C12-D51
A39-B89-C12-D51
A65-B89-C12-D51
A66-B89-C12-D51
A2-B92-C12-D51
A3-B92-C12-D51
A9-B92-C12-D51
A13-B92-C12-D51
A24-B92-C12-D51
A69-B92-C12-D51
A67-B92-C12-D51
A39-B92-C12-D51
A65-B92-C12-D51
A66-B92-C12-D51
A2-B4-C13-D51
A3-B4-C13-D51
A9-B4-C13-D51
A13-B4-C13-D51
A24-B4-C13-D51
A69-B4-C13-D51
A67-B4-C13-D51
A39-B4-C13-D51
A65-B4-C13-D51
A66-B4-C13-D51
A2-B5-C13-D51
A3-B5-C13-D51
A9-B5-C13-D51
A13-B5-C13-D51
A24-B5-C13-D51
A69-B5-C13-D51
A67-B5-C13-D51
A39-B5-C13-D51
A65-B5-C13-D51
A66-B5-C13-D51
A2-B6-C13-D51
A3-B6-C13-D51
A9-B6-C13-D51

-continued
A13-B6-C13-D51
A24-B6-C13-D51
A69-B6-C13-D51
A67-B6-C13-D51
A39-B6-C13-D51
A65-B6-C13-D51
A66-B6-C13-D51
A2-B32-C13-D51
A3-B32-C13-D51
A9-B32-C13-D51
A13-B32-C13-D51
A24-B32-C13-D51
A69-B32-C13-D51
A67-B32-C13-D51
A39-B32-C13-D51
A65-B32-C13-D51
A66-B32-C13-D51
A2-B39-C13-D51
A3-B39-C13-D51
A9-B39-C13-D51
A13-B39-C13-D51
A24-B39-C13-D51
A69-B39-C13-D51
A67-B39-C13-D51
A39-B39-C13-D51
A65-B39-C13-D51
A66-B39-C13-D51
A2-B45-C13-D51
A3-B45-C13-D51
A9-B45-C13-D51
A13-B45-C13-D51
A24-B45-C13-D51
A69-B45-C13-D51
A67-B45-C13-D51
A39-B45-C13-D51
A65-B45-C13-D51
A66-B45-C13-D51
A2-B53-C13-D51
A3-B53-C13-D51
A9-B53-C13-D51
A13-B53-C13-D51
A24-B53-C13-D51
A69-B53-C13-D51
A67-B53-C13-D51
A39-B53-C13-D51
A65-B53-C13-D51
A66-B53-C13-D51
A2-B79-C13-D51
A3-B79-C13-D51
A9-B79-C13-D51
A13-B79-C13-D51
A24-B79-C13-D51
A69-B79-C13-D51
A67-B79-C13-D51
A39-B79-C13-D51
A65-B79-C13-D51
A66-B79-C13-D51
A2-B80-C13-D51
A3-B80-C13-D51
A9-B80-C13-D51
A13-B80-C13-D51
A24-B80-C13-D51
A69-B80-C13-D51
A67-B80-C13-D51
A39-B80-C13-D51
A65-B80-C13-D51
A66-B80-C13-D51
A2-B85-C13-D51
A3-B85-C13-D51
A9-B85-C13-D51
A13-B85-C13-D51
A24-B85-C13-D51
A69-B85-C13-D51
A67-B85-C13-D51
A39-B85-C13-D51
A65-B85-C13-D51
A66-B85-C13-D51
A2-B86-C13-D51
A3-B86-C13-D51
A9-B86-C13-D51

-continued
A13-B86-C13-D51
A24-B86-C13-D51
A69-B86-C13-D51
A67-B86-C13-D51
A39-B86-C13-D51
A65-B86-C13-D51
A66-B86-C13-D51
A2-B87-C13-D51
A3-B87-C13-D51
A9-B87-C13-D51
A13-B87-C13-D51
A24-B87-C13-D51
A69-B87-C13-D51
A67-B87-C13-D51
A39-B87-C13-D51
A65-B87-C13-D51
A66-B87-C13-D51
A2-B89-C13-D51
A3-B89-C13-D51
A9-B89-C13-D51
A13-B89-C13-D51
A24-B89-C13-D51
A69-B89-C13-D51
A67-B89-C13-D51
A39-B89-C13-D51
A65-B89-C13-D51
A66-B89-C13-D51
A2-B92-C13-D51
A3-B92-C13-D51
A9-B92-C13-D51
A13-B92-C13-D51
A24-B92-C13-D51
A69-B92-C13-D51
A67-B92-C13-D51
A39-B92-C13-D51
A65-B92-C13-D51
A66-B92-C13-D51
A2-B4-C1-D52
A3-B4-C1-D52
A9-B4-C1-D52
A13-B4-C1-D52
A24-B4-C1-D52
A69-B4-C1-D52
A67-B4-C1-D52
A39-B4-C1-D52
A65-B4-C1-D52
A66-B4-C1-D52
A2-B5-C1-D52
A3-B5-C1-D52
A9-B5-C1-D52
A13-B5-C1-D52
A24-B5-C1-D52
A69-B5-C1-D52
A67-B5-C1-D52
A39-B5-C1-D52
A65-B5-C1-D52
A66-B5-C1-D52
A2-B6-C1-D52
A3-B6-C1-D52
A9-B6-C1-D52
A13-B6-C1-D52
A24-B6-C1-D52
A69-B6-C1-D52
A67-B6-C1-D52
A39-B6-C1-D52
A65-B6-C1-D52
A66-B6-C1-D52
A2-B32-C1-D52
A3-B32-C1-D52
A9-B32-C1-D52
A13-B32-C1-D52
A24-B32-C1-D52
A69-B32-C1-D52
A67-B32-C1-D52
A39-B32-C1-D52
A65-B32-C1-D52
A66-B32-C1-D52
A2-B39-C1-D52
A3-B39-C1-D52
A9-B39-C1-D52

-continued

A13-B39-C1-D52
A24-B39-C1-D52
A69-B39-C1-D52
A67-B39-C1-D52
A39-B39-C1-D52
A65-B39-C1-D52
A66-B39-C1-D52
A2-B45-C1-D52
A3-B45-C1-D52
A9-B45-C1-D52
A13-B45-C1-D52
A24-B45-C1-D52
A69-B45-C1-D52
A67-B45-C1-D52
A39-B45-C1-D52
A65-B45-C1-D52
A66-B45-C1-D52
A2-B53-C1-D52
A3-B53-C1-D52
A9-B53-C1-D52
A13-B53-C1-D52
A24-B53-C1-D52
A69-B53-C1-D52
A67-B53-C1-D52
A39-B53-C1-D52
A65-B53-C1-D52
A66-B53-C1-D52
A2-B79-C1-D52
A3-B79-C1-D52
A9-B79-C1-D52
A13-B79-C1-D52
A24-B79-C1-D52
A69-B79-C1-D52
A67-B79-C1-D52
A39-B79-C1-D52
A65-B79-C1-D52
A66-B79-C1-D52
A2-B80-C1-D52
A3-B80-C1-D52
A9-B80-C1-D52
A13-B80-C1-D52
A24-B80-C1-D52
A69-B80-C1-D52
A67-B80-C1-D52
A39-B80-C1-D52
A65-B80-C1-D52
A66-B80-C1-D52
A2-B85-C1-D52
A3-B85-C1-D52
A9-B85-C1-D52
A13-B85-C1-D52
A24-B85-C1-D52
A69-B85-C1-D52
A67-B85-C1-D52
A39-B85-C1-D52
A65-B85-C1-D52
A66-B85-C1-D52
A2-B86-C1-D52
A3-B86-C1-D52
A9-B86-C1-D52
A13-B86-C1-D52
A24-B86-C1-D52
A69-B86-C1-D52
A67-B86-C1-D52
A39-B86-C1-D52
A65-B86-C1-D52
A66-B86-C1-D52
A2-B87-C1-D52
A3-B87-C1-D52
A9-B87-C1-D52
A13-B87-C1-D52
A24-B87-C1-D52
A69-B87-C1-D52
A67-B87-C1-D52
A39-B87-C1-D52
A65-B87-C1-D52
A66-B87-C1-D52
A2-B89-C1-D52
A3-B89-C1-D52
A9-B89-C1-D52

-continued

A13-B89-C1-D52
A24-B89-C1-D52
A69-B89-C1-D52
A67-B89-C1-D52
A39-B89-C1-D52
A65-B89-C1-D52
A66-B89-C1-D52
A2-B92-C1-D52
A3-B92-C1-D52
A9-B92-C1-D52
A13-B92-C1-D52
A24-B92-C1-D52
A69-B92-C1-D52
A67-B92-C1-D52
A39-B92-C1-D52
A65-B92-C1-D52
A66-B92-C1-D52
A2-B4-C2-D52
A3-B4-C2-D52
A9-B4-C2-D52
A13-B4-C2-D52
A24-B4-C2-D52
A69-B4-C2-D52
A67-B4-C2-D52
A39-B4-C2-D52
A65-B4-C2-D52
A66-B4-C2-D52
A2-B5-C2-D52
A3-B5-C2-D52
A9-B5-C2-D52
A13-B5-C2-D52
A24-B5-C2-D52
A69-B5-C2-D52
A67-B5-C2-D52
A39-B5-C2-D52
A65-B5-C2-D52
A66-B5-C2-D52
A2-B6-C2-D52
A3-B6-C2-D52
A9-B6-C2-D52
A13-B6-C2-D52
A24-B6-C2-D52
A69-B6-C2-D52
A67-B6-C2-D52
A39-B6-C2-D52
A65-B6-C2-D52
A66-B6-C2-D52
A2-B32-C2-D52
A3-B32-C2-D52
A9-B32-C2-D52
A13-B32-C2-D52
A24-B32-C2-D52
A69-B32-C2-D52
A67-B32-C2-D52
A39-B32-C2-D52
A65-B32-C2-D52
A66-B32-C2-D52
A2-B39-C2-D52
A3-B39-C2-D52
A9-B39-C2-D52
A13-B39-C2-D52
A24-B39-C2-D52
A69-B39-C2-D52
A67-B39-C2-D52
A39-B39-C2-D52
A65-B39-C2-D52
A66-B39-C2-D52
A2-B45-C2-D52
A3-B45-C2-D52
A9-B45-C2-D52
A13-B45-C2-D52
A24-B45-C2-D52
A69-B45-C2-D52
A67-B45-C2-D52
A39-B45-C2-D52
A65-B45-C2-D52
A66-B45-C2-D52
A2-B53-C2-D52
A3-B53-C2-D52
A9-B53-C2-D52

-continued
A13-B53-C2-D52
A24-B53-C2-D52
A69-B53-C2-D52
A67-B53-C2-D52
A39-B53-C2-D52
A65-B53-C2-D52
A66-B53-C2-D52
A2-B79-C2-D52
A3-B79-C2-D52
A9-B79-C2-D52
A13-B79-C2-D52
A24-B79-C2-D52
A69-B79-C2-D52
A67-B79-C2-D52
A39-B79-C2-D52
A65-B79-C2-D52
A66-B79-C2-D52
A2-B80-C2-D52
A3-B80-C2-D52
A9-B80-C2-D52
A13-B80-C2-D52
A24-B80-C2-D52
A69-B80-C2-D52
A67-B80-C2-D52
A39-B80-C2-D52
A65-B80-C2-D52
A66-B80-C2-D52
A2-B85-C2-D52
A3-B85-C2-D52
A9-B85-C2-D52
A13-B85-C2-D52
A24-B85-C2-D52
A69-B85-C2-D52
A67-B85-C2-D52
A39-B85-C2-D52
A65-B85-C2-D52
A66-B85-C2-D52
A2-B86-C2-D52
A3-B86-C2-D52
A9-B86-C2-D52
A13-B86-C2-D52
A24-B86-C2-D52
A69-B86-C2-D52
A67-B86-C2-D52
A39-B86-C2-D52
A65-B86-C2-D52
A66-B86-C2-D52
A2-B87-C2-D52
A3-B87-C2-D52
A9-B87-C2-D52
A13-B87-C2-D52
A24-B87-C2-D52
A69-B87-C2-D52
A67-B87-C2-D52
A39-B87-C2-D52
A65-B87-C2-D52
A66-B87-C2-D52
A2-B89-C2-D52
A3-B89-C2-D52
A9-B89-C2-D52
A13-B89-C2-D52
A24-B89-C2-D52
A69-B89-C2-D52
A67-B89-C2-D52
A39-B89-C2-D52
A65-B89-C2-D52
A66-B89-C2-D52
A2-B92-C2-D52
A3-B92-C2-D52
A9-B92-C2-D52
A13-B92-C2-D52
A24-B92-C2-D52
A69-B92-C2-D52
A67-B92-C2-D52
A39-B92-C2-D52
A65-B92-C2-D52
A66-B92-C2-D52
A2-B4-C3-D52
A3-B4-C3-D52
A9-B4-C3-D52

-continued
A13-B4-C3-D52
A24-B4-C3-D52
A69-B4-C3-D52
A67-B4-C3-D52
A39-B4-C3-D52
A65-B4-C3-D52
A66-B4-C3-D52
A2-B5-C3-D52
A3-B5-C3-D52
A9-B5-C3-D52
A13-B5-C3-D52
A24-B5-C3-D52
A69-B5-C3-D52
A67-B5-C3-D52
A39-B5-C3-D52
A65-B5-C3-D52
A66-B5-C3-D52
A2-B6-C3-D52
A3-B6-C3-D52
A9-B6-C3-D52
A13-B6-C3-D52
A24-B6-C3-D52
A69-B6-C3-D52
A67-B6-C3-D52
A39-B6-C3-D52
A65-B6-C3-D52
A66-B6-C3-D52
A2-B32-C3-D52
A3-B32-C3-D52
A9-B32-C3-D52
A13-B32-C3-D52
A24-B32-C3-D52
A69-B32-C3-D52
A67-B32-C3-D52
A39-B32-C3-D52
A65-B32-C3-D52
A66-B32-C3-D52
A2-B39-C3-D52
A3-B39-C3-D52
A9-B39-C3-D52
A13-B39-C3-D52
A24-B39-C3-D52
A69-B39-C3-D52
A67-B39-C3-D52
A39-B39-C3-D52
A65-B39-C3-D52
A66-B39-C3-D52
A2-B45-C3-D52
A3-B45-C3-D52
A9-B45-C3-D52
A13-B45-C3-D52
A24-B45-C3-D52
A69-B45-C3-D52
A67-B45-C3-D52
A39-B45-C3-D52
A65-B45-C3-D52
A66-B45-C3-D52
A2-B53-C3-D52
A3-B53-C3-D52
A9-B53-C3-D52
A13-B53-C3-D52
A24-B53-C3-D52
A69-B53-C3-D52
A67-B53-C3-D52
A39-B53-C3-D52
A65-B53-C3-D52
A66-B53-C3-D52
A2-B79-C3-D52
A3-B79-C3-D52
A9-B79-C3-D52
A13-B79-C3-D52
A24-B79-C3-D52
A69-B79-C3-D52
A67-B79-C3-D52
A39-B79-C3-D52
A65-B79-C3-D52
A66-B79-C3-D52
A2-B80-C3-D52
A3-B80-C3-D52
A9-B80-C3-D52

-continued
A13-B80-C3-D52
A24-B80-C3-D52
A69-B80-C3-D52
A67-B80-C3-D52
A39-B80-C3-D52
A65-B80-C3-D52
A66-B80-C3-D52
A2-B85-C3-D52
A3-B85-C3-D52
A9-B85-C3-D52
A13-B85-C3-D52
A24-B85-C3-D52
A69-B85-C3-D52
A67-B85-C3-D52
A39-B85-C3-D52
A65-B85-C3-D52
A66-B85-C3-D52
A2-B86-C3-D52
A3-B86-C3-D52
A9-B86-C3-D52
A13-B86-C3-D52
A24-B86-C3-D52
A69-B86-C3-D52
A67-B86-C3-D52
A39-B86-C3-D52
A65-B86-C3-D52
A66-B86-C3-D52
A2-B87-C3-D52
A3-B87-C3-D52
A9-B87-C3-D52
A13-B87-C3-D52
A24-B87-C3-D52
A69-B87-C3-D52
A67-B87-C3-D52
A39-B87-C3-D52
A65-B87-C3-D52
A66-B87-C3-D52
A2-B89-C3-D52
A3-B89-C3-D52
A9-B89-C3-D52
A13-B89-C3-D52
A24-B89-C3-D52
A69-B89-C3-D52
A67-B89-C3-D52
A39-B89-C3-D52
A65-B89-C3-D52
A66-B89-C3-D52
A2-B92-C3-D52
A3-B92-C3-D52
A9-B92-C3-D52
A13-B92-C3-D52
A24-B92-C3-D52
A69-B92-C3-D52
A67-B92-C3-D52
A39-B92-C3-D52
A65-B92-C3-D52
A66-B92-C3-D52
A2-B4-C4-D52
A3-B4-C4-D52
A9-B4-C4-D52
A13-B4-C4-D52
A24-B4-C4-D52
A69-B4-C4-D52
A67-B4-C4-D52
A39-B4-C4-D52
A65-B4-C4-D52
A66-B4-C4-D52
A2-B5-C4-D52
A3-B5-C4-D52
A9-B5-C4-D52
A13-B5-C4-D52
A24-B5-C4-D52
A69-B5-C4-D52
A67-B5-C4-D52
A39-B5-C4-D52
A65-B5-C4-D52
A66-B5-C4-D52
A2-B6-C4-D52
A3-B6-C4-D52
A9-B6-C4-D52

-continued
A13-B6-C4-D52
A24-B6-C4-D52
A69-B6-C4-D52
A67-B6-C4-D52
A39-B6-C4-D52
A65-B6-C4-D52
A66-B6-C4-D52
A2-B32-C4-D52
A3-B32-C4-D52
A9-B32-C4-D52
A13-B32-C4-D52
A24-B32-C4-D52
A69-B32-C4-D52
A67-B32-C4-D52
A39-B32-C4-D52
A65-B32-C4-D52
A66-B32-C4-D52
A2-B39-C4-D52
A3-B39-C4-D52
A9-B39-C4-D52
A13-B39-C4-D52
A24-B39-C4-D52
A69-B39-C4-D52
A67-B39-C4-D52
A39-B39-C4-D52
A65-B39-C4-D52
A66-B39-C4-D52
A2-B45-C4-D52
A3-B45-C4-D52
A9-B45-C4-D52
A13-B45-C4-D52
A24-B45-C4-D52
A69-B45-C4-D52
A67-B45-C4-D52
A39-B45-C4-D52
A65-B45-C4-D52
A66-B45-C4-D52
A2-B53-C4-D52
A3-B53-C4-D52
A9-B53-C4-D52
A13-B53-C4-D52
A24-B53-C4-D52
A69-B53-C4-D52
A67-B53-C4-D52
A39-B53-C4-D52
A65-B53-C4-D52
A66-B53-C4-D52
A2-B79-C4-D52
A3-B79-C4-D52
A9-B79-C4-D52
A13-B79-C4-D52
A24-B79-C4-D52
A69-B79-C4-D52
A67-B79-C4-D52
A39-B79-C4-D52
A65-B79-C4-D52
A66-B79-C4-D52
A2-B80-C4-D52
A3-B80-C4-D52
A9-B80-C4-D52
A13-B80-C4-D52
A24-B80-C4-D52
A69-B80-C4-D52
A67-B80-C4-D52
A39-B80-C4-D52
A65-B80-C4-D52
A66-B80-C4-D52
A2-B85-C4-D52
A3-B85-C4-D52
A9-B85-C4-D52
A13-B85-C4-D52
A24-B85-C4-D52
A69-B85-C4-D52
A67-B85-C4-D52
A39-B85-C4-D52
A65-B85-C4-D52
A66-B85-C4-D52
A2-B86-C4-D52
A3-B86-C4-D52
A9-B86-C4-D52

-continued

A13-B86-C4-D52
A24-B86-C4-D52
A69-B86-C4-D52
A67-B86-C4-D52
A39-B86-C4-D52
A65-B86-C4-D52
A66-B86-C4-D52
A2-B87-C4-D52
A3-B87-C4-D52
A9-B87-C4-D52
A13-B87-C4-D52
A24-B87-C4-D52
A69-B87-C4-D52
A67-B87-C4-D52
A39-B87-C4-D52
A65-B87-C4-D52
A66-B87-C4-D52
A2-B89-C4-D52
A3-B89-C4-D52
A9-B89-C4-D52
A13-B89-C4-D52
A24-B89-C4-D52
A69-B89-C4-D52
A67-B89-C4-D52
A39-B89-C4-D52
A65-B89-C4-D52
A66-B89-C4-D52
A2-B92-C4-D52
A3-B92-C4-D52
A9-B92-C4-D52
A13-B92-C4-D52
A24-B92-C4-D52
A69-B92-C4-D52
A67-B92-C4-D52
A39-B92-C4-D52
A65-B92-C4-D52
A66-B92-C4-D52
A2-B4-C5-D52
A3-B4-C5-D52
A9-B4-C5-D52
A13-B4-C8-D52
A24-B4-C5-D52
A69-B4-C5-D52
A67-B4-C5-D52
A39-B4-C5-D52
A65-B4-C5-D52
A66-B4-C5-D52
A2-B5-C5-D52
A3-B5-C5-D52
A9-B5-C5-D52
A13-B5-C5-D52
A24-B5-C5-D52
A69-B5-C5-D52
A67-B5-C5-D52
A39-B5-C5-D52
A65-B5-C5-D52
A66-B5-C5-D52
A2-B6-C5-D52
A3-B6-C5-D52
A9-B6-C5-D52
A13-B6-C5-D52
A24-B6-C5-D52
A69-B6-C5-D52
A67-B6-C5-D52
A39-B6-C5-D52
A65-B6-C5-D52
A66-B6-C5-D52
A2-B32-C5-D52
A3-B32-C5-D52
A9-B32-C5-D52
A13-B32-C5-D52
A24-B32-C5-D52
A69-B32-C5-D52
A67-B32-C5-D52
A39-B32-C5-D52
A65-B32-C5-D52
A66-B32-C5-D52
A2-B39-C5-D52
A3-B39-C5-D52
A9-B39-C5-D52

-continued

A13-B39-C5-D52
A24-B39-C5-D52
A69-B39-C5-D52
A67-B39-C5-D52
A39-B39-C5-D52
A65-B39-C5-D52
A66-B39-C5-D52
A2-B45-C5-D52
A3-B45-C5-D52
A9-B45-C5-D52
A13-B45-C5-D52
A24-B45-C5-D52
A69-B45-C5-D52
A67-B45-C5-D52
A39-B45-C5-D52
A65-B45-C5-D52
A66-B45-C5-D52
A2-B53-C5-D52
A3-B53-C5-D52
A9-B53-C5-D52
A13-B53-C5-D52
A24-B53-C5-D52
A69-B53-C5-D52
A67-B53-C5-D52
A39-B53-C5-D52
A65-B53-C5-D52
A66-B53-C5-D52
A2-B79-C5-D52
A3-B79-C5-D52
A9-B79-C5-D52
A13-B79-C5-D52
A24-B79-C5-D52
A69-B79-C5-D52
A67-B79-C5-D52
A39-B79-C5-D52
A65-B79-C5-D52
A66-B79-C5-D52
A2-B80-C5-D52
A3-B80-C5-D52
A9-B80-C5-D52
A13-B80-C5-D52
A24-B80-C5-D52
A69-B80-C5-D52
A67-B80-C5-D52
A39-B80-C5-D52
A65-B80-C5-D52
A66-B80-C5-D52
A2-B85-C5-D52
A3-B85-C5-D52
A9-B85-C5-D52
A13-B85-C5-D52
A24-B85-C5-D52
A69-B85-C5-D52
A67-B85-C5-D52
A39-B85-C5-D52
A65-B85-C5-D52
A66-B85-C5-D52
A2-B86-C5-D52
A3-B86-C5-D52
A9-B86-C5-D52
A13-B86-C5-D52
A24-B86-C5-D52
A69-B86-C5-D52
A67-B86-C5-D52
A39-B86-C5-D52
A65-B86-C5-D52
A66-B86-C5-D52
A2-B87-C5-D52
A3-B87-C5-D52
A9-B87-C5-D52
A13-B87-C5-D52
A24-B87-C5-D52
A69-B87-C5-D52
A67-B87-C5-D52
A39-B87-C5-D52
A65-B87-C5-D52
A66-B87-C5-D52
A2-B89-C5-D52
A3-B89-C5-D52
A9-B89-C5-D52

-continued

| 1239 | 1240 |
|---|---|
| A13-B89-C5-D52 | A13-B53-C6-D52 |
| A24-B89-C5-D52 | A24-B53-C6-D52 |
| A69-B89-C5-D52 | A69-B53-C6-D52 |
| A67-B89-C5-D52 | A67-B53-C6-D52 |
| A39-B89-C5-D52 | A39-B53-C6-D52 |
| A65-B89-C5-D52 | A65-B53-C6-D52 |
| A66-B89-C5-D52 | A66-B53-C6-D52 |
| A2-B92-C5-D52 | A2-B79-C6-D52 |
| A3-B92-C5-D52 | A3-B79-C6-D52 |
| A9-B92-C5-D52 | A9-B79-C6-D52 |
| A13-B92-C5-D52 | A13-B79-C6-D52 |
| A24-B92-C5-D52 | A24-B79-C6-D52 |
| A69-B92-C5-D52 | A69-B79-C6-D52 |
| A67-B92-C5-D52 | A67-B79-C6-D52 |
| A39-B92-C5-D52 | A39-B79-C6-D52 |
| A65-B92-C5-D52 | A65-B79-C6-D52 |
| A66-B92-C5-D52 | A66-B79-C6-D52 |
| A2-B4-C6-D52 | A2-B80-C6-D52 |
| A3-B4-C6-D52 | A3-B80-C6-D52 |
| A9-B4-C6-D52 | A9-B80-C6-D52 |
| A13-B4-C6-D52 | A13-B80-C6-D52 |
| A24-B4-C6-D52 | A24-B80-C6-D52 |
| A69-B4-C6-D52 | A69-B80-C6-D52 |
| A67-B4-C6-D52 | A67-B80-C6-D52 |
| A39-B4-C6-D52 | A39-B80-C6-D52 |
| A65-B4-C6-D52 | A65-B80-C6-D52 |
| A66-B4-C6-D52 | A66-B80-C6-D52 |
| A2-B5-C6-D52 | A2-B85-C6-D52 |
| A3-B5-C6-D52 | A3-B85-C6-D52 |
| A9-B5-C6-D52 | A9-B85-C6-D52 |
| A13-B5-C6-D52 | A13-B85-C6-D52 |
| A24-B5-C6-D52 | A24-B85-C6-D52 |
| A69-B5-C6-D52 | A69-B85-C6-D52 |
| A67-B5-C6-D52 | A67-B85-C6-D52 |
| A39-B5-C6-D52 | A39-B85-C6-D52 |
| A65-B5-C6-D52 | A65-B85-C6-D52 |
| A66-B5-C6-D52 | A66-B85-C6-D52 |
| A2-B6-C6-D52 | A2-B86-C6-D52 |
| A3-B6-C6-D52 | A3-B86-C6-D52 |
| A9-B6-C6-D52 | A9-B86-C6-D52 |
| A13-B6-C6-D52 | A13-B86-C6-D52 |
| A24-B6-C6-D52 | A24-B86-C6-D52 |
| A69-B6-C6-D52 | A69-B86-C6-D52 |
| A67-B6-C6-D52 | A67-B86-C6-D52 |
| A39-B6-C6-D52 | A39-B86-C6-D52 |
| A65-B6-C6-D52 | A65-B86-C6-D52 |
| A66-B6-C6-D52 | A66-B86-C6-D52 |
| A2-B32-C6-D52 | A2-B87-C6-D52 |
| A3-B32-C6-D52 | A3-B87-C6-D52 |
| A9-B32-C6-D52 | A9-B87-C6-D52 |
| A13-B32-C6-D52 | A13-B87-C6-D52 |
| A24-B32-C6-D52 | A24-B87-C6-D52 |
| A69-B32-C6-D52 | A69-B87-C6-D52 |
| A67-B32-C6-D52 | A67-B87-C6-D52 |
| A39-B32-C6-D52 | A39-B87-C6-D52 |
| A65-B32-C6-D52 | A65-B87-C6-D52 |
| A66-B32-C6-D52 | A66-B87-C6-D52 |
| A2-B39-C6-D52 | A2-B89-C6-D52 |
| A3-B39-C6-D52 | A3-B89-C6-D52 |
| A9-B39-C6-D52 | A9-B89-C6-D52 |
| A13-B39-C6-D52 | A13-B89-C6-D52 |
| A24-B39-C6-D52 | A24-B89-C6-D52 |
| A69-B39-C6-D52 | A69-B89-C6-D52 |
| A67-B39-C6-D52 | A67-B89-C6-D52 |
| A39-B39-C6-D52 | A39-B89-C6-D52 |
| A65-B39-C6-D52 | A65-B89-C6-D52 |
| A66-B39-C6-D52 | A66-B89-C6-D52 |
| A2-B45-C6-D52 | A2-B92-C6-D52 |
| A3-B45-C6-D52 | A3-B92-C6-D52 |
| A9-B45-C6-D52 | A9-B92-C6-D52 |
| A13-B45-C6-D52 | A13-B92-C6-D52 |
| A24-B45-C6-D52 | A24-B92-C6-D52 |
| A69-B45-C6-D52 | A69-B92-C6-D52 |
| A67-B45-C6-D52 | A67-B92-C6-D52 |
| A39-B45-C6-D52 | A39-B92-C6-D52 |
| A65-B45-C6-D52 | A65-B92-C6-D52 |
| A66-B45-C6-D52 | A66-B92-C6-D52 |
| A2-B53-C6-D52 | A2-B4-C7-D52 |
| A3-B53-C6-D52 | A3-B4-C7-D52 |
| A9-B53-C6-D52 | A9-B4-C7-D52 |

-continued

A13-B4-C7-D52
A24-B4-C7-D52
A69-B4-C7-D52
A67-B4-C7-D52
A39-B4-C7-D52
A65-B4-C7-D52
A66-B4-C7-D52
A2-B5-C7-D52
A3-B5-C7-D52
A9-B5-C7-D52
A13-B5-C7-D52
A24-B5-C7-D52
A69-B5-C7-D52
A67-B5-C7-D52
A39-B5-C7-D52
A65-B5-C7-D52
A66-B5-C7-D52
A2-B6-C7-D52
A3-B6-C7-D52
A9-B6-C7-D52
A13-B6-C7-D52
A24-B6-C7-D52
A69-B6-C7-D52
A67-B6-C7-D52
A39-B6-C7-D52
A65-B6-C7-D52
A66-B6-C7-D52
A2-B32-C7-D52
A3-B32-C7-D52
A9-B32-C7-D52
A13-B32-C7-D52
A24-B32-C7-D52
A69-B32-C7-D52
A67-B32-C7-D52
A39-B32-C7-D52
A65-B32-C7-D52
A66-B32-C7-D52
A2-B39-C7-D52
A3-B39-C7-D52
A9-B39-C7-D52
A13-B39-C7-D52
A24-B39-C7-D52
A69-B39-C7-D52
A67-B39-C7-D52
A39-B39-C7-D52
A65-B39-C7-D52
A66-B39-C7-D52
A2-B45-C7-D52
A3-B45-C7-D52
A9-B45-C7-D52
A13-B45-C7-D52
A24-B45-C7-D52
A69-B45-C7-D52
A67-B45-C7-D52
A39-B45-C7-D52
A65-B45-C7-D52
A66-B45-C7-D52
A2-B53-C7-D52
A3-B53-C7-D52
A9-B53-C7-D52
A13-B53-C7-D52
A24-B53-C7-D52
A69-B53-C7-D52
A67-B53-C7-D52
A39-B53-C7-D52
A65-B53-C7-D52
A66-B53-C7-D52
A2-B79-C7-D52
A3-B79-C7-D52
A9-B79-C7-D52
A13-B79-C7-D52
A24-B79-C7-D52
A69-B79-C7-D52
A67-B79-C7-D52
A39-B79-C7-D52
A65-B79-C7-D52
A66-B79-C7-D52
A2-B80-C7-D52
A3-B80-C7-D52
A9-B80-C7-D52

-continued

A13-B80-C7-D52
A24-B80-C7-D52
A69-B80-C7-D52
A67-B80-C7-D52
A39-B80-C7-D52
A65-B80-C7-D52
A66-B80-C7-D52
A2-B85-C7-D52
A3-B85-C7-D52
A9-B85-C7-D52
A13-B85-C7-D52
A24-B85-C7-D52
A69-B85-C7-D52
A67-B85-C7-D52
A39-B85-C7-D52
A65-B85-C7-D52
A66-B85-C7-D52
A2-B86-C7-D52
A3-B86-C7-D52
A9-B86-C7-D52
A13-B86-C7-D52
A24-B86-C7-D52
A69-B86-C7-D52
A67-B86-C7-D52
A39-B86-C7-D52
A65-B86-C7-D52
A66-B86-C7-D52
A2-B87-C7-D52
A3-B87-C7-D52
A9-B87-C7-D52
A13-B87-C7-D52
A24-B87-C7-D52
A69-B87-C7-D52
A67-B87-C7-D52
A39-B87-C7-D52
A65-B87-C7-D52
A66-B87-C7-D52
A2-B89-C7-D52
A3-B89-C7-D52
A9-B89-C7-D52
A13-B89-C7-D52
A24-B89-C7-D52
A69-B89-C7-D52
A67-B89-C7-D52
A39-B89-C7-D52
A65-B89-C7-D52
A66-B89-C7-D52
A2-B92-C7-D52
A3-B92-C7-D52
A9-B92-C7-D52
A13-B92-C7-D52
A24-B92-C7-D52
A69-B92-C7-D52
A67-B92-C7-D52
A39-B92-C7-D52
A65-B92-C7-D52
A66-B92-C7-D52
A2-B4-C8-D52
A3-B4-C8-D52
A9-B4-C8-D52
A13-B4-C8-D52
A24-B4-C8-D52
A69-B4-C8-D52
A67-B4-C8-D52
A39-B4-C8-D52
A65-B4-C8-D52
A66-B4-C8-D52
A2-B5-C8-D52
A3-B5-C8-D52
A9-B5-C8-D52
A13-B5-C8-D52
A24-B5-C8-D52
A69-B5-C8-D52
A67-B5-C8-D52
A39-B5-C8-D52
A65-B5-C8-D52
A66-B5-C8-D52
A2-B6-C8-D52
A3-B6-C8-D52
A9-B6-C8-D52

-continued
A13-B6-C8-D52
A24-B6-C8-D52
A69-B6-C8-D52
A67-B6-C8-D52
A39-B6-C8-D52
A65-B6-C8-D52
A66-B6-C8-D52
A2-B32-C8-D52
A3-B32-C8-D52
A9-B32-C8-D52
A13-B32-C8-D52
A24-B32-C8-D52
A69-B32-C8-D52
A67-B32-C8-D52
A39-B32-C8-D52
A65-B32-C8-D52
A66-B32-C8-D52
A2-B39-C8-D52
A3-B39-C8-D52
A9-B39-C8-D52
A13-B39-C8-D52
A24-B39-C8-D52
A69-B39-C8-D52
A67-B39-C8-D52
A39-B39-C8-D52
A65-B39-C8-D52
A66-B39-C8-D52
A2-B45-C8-D52
A3-B45-C8-D52
A9-B45-C8-D52
A13-B45-C8-D52
A24-B45-C8-D52
A69-B45-C8-D52
A67-B45-C8-D52
A39-B45-C8-D52
A65-B45-C8-D52
A66-B45-C8-D52
A2-B53-C8-D52
A3-B53-C8-D52
A9-B53-C8-D52
A13-B53-C8-D52
A24-B53-C8-D52
A69-B53-C8-D52
A67-B53-C8-D52
A39-B53-C8-D52
A65-B53-C8-D52
A66-B53-C8-D52
A2-B79-C8-D52
A3-B79-C8-D52
A9-B79-C8-D52
A13-B79-C8-D52
A24-B79-C8-D52
A69-B79-C8-D52
A67-B79-C8-D52
A39-B79-C8-D52
A65-B79-C8-D52
A66-B79-C8-D52
A2-B80-C8-D52
A3-B80-C8-D52
A9-B80-C8-D52
A13-B80-C8-D52
A24-B80-C8-D52
A69-B80-C8-D52
A67-B80-C8-D52
A39-B80-C8-D52
A65-B80-C8-D52
A66-B80-C8-D52
A2-B85-C8-D52
A3-B85-C8-D52
A9-B85-C8-D52
A13-B85-C8-D52
A24-B85-C8-D52
A69-B85-C8-D52
A67-B85-C8-D52
A39-B85-C8-D52
A65-B85-C8-D52
A66-B85-C8-D52
A2-B86-C8-D52
A3-B86-C8-D52
A9-B86-C8-D52

-continued
A13-B86-C8-D52
A24-B86-C8-D52
A69-B86-C8-D52
A67-B86-C8-D52
A39-B86-C8-D52
A65-B86-C8-D52
A66-B86-C8-D52
A2-B87-C8-D52
A3-B87-C8-D52
A9-B87-C8-D52
A13-B87-C8-D52
A24-B87-C8-D52
A69-B87-C8-D52
A67-B87-C8-D52
A39-B87-C8-D52
A65-B87-C8-D52
A66-B87-C8-D52
A2-B89-C8-D52
A3-B89-C8-D52
A9-B89-C8-D52
A13-B89-C8-D52
A24-B89-C8-D52
A69-B89-C8-D52
A67-B89-C8-D52
A39-B89-C8-D52
A65-B89-C8-D52
A66-B89-C8-D52
A2-B92-C8-D52
A3-B92-C8-D52
A9-B92-C8-D52
A13-B92-C8-D52
A24-B92-C8-D52
A69-B92-C8-D52
A67-B92-C8-D52
A39-B92-C8-D52
A65-B92-C8-D52
A66-B92-C8-D52
A2-B4-C9-D52
A3-B4-C9-D52
A9-B4-C9-D52
A13-B4-C9-D52
A24-B4-C9-D52
A69-B4-C9-D52
A67-B4-C9-D52
A39-B4-C9-D52
A65-B4-C9-D52
A66-B4-C9-D52
A2-B5-C9-D52
A3-B5-C9-D52
A9-B5-C9-D52
A13-B5-C9-D52
A24-B5-C9-D52
A69-B5-C9-D52
A67-B5-C9-D52
A39-B5-C9-D52
A65-B5-C9-D52
A66-B5-C9-D52
A2-B6-C9-D52
A3-B6-C9-D52
A9-B6-C9-D52
A13-B6-C9-D52
A24-B6-C9-D52
A69-B6-C9-D52
A67-B6-C9-D52
A39-B6-C9-D52
A65-B6-C9-D52
A66-B6-C9-D52
A2-B32-C9-D52
A3-B32-C9-D52
A9-B32-C9-D52
A13-B32-C9-D52
A24-B32-C9-D52
A69-B32-C9-D52
A67-B32-C9-D52
A39-B32-C9-D52
A65-B32-C9-D52
A66-B32-C9-D52
A2-B39-C9-D52
A3-B39-C9-D52
A9-B39-C9-D52

-continued
A13-B39-C9-D52
A24-B39-C9-D52
A69-B39-C9-D52
A67-B39-C9-D52
A39-B39-C9-D52
A65-B39-C9-D52
A66-B39-C9-D52
A2-B45-C9-D52
A3-B45-C9-D52
A9-B45-C9-D52
A13-B45-C9-D52
A24-B45-C9-D52
A69-B45-C9-D52
A67-B45-C9-D52
A39-B45-C9-D52
A65-B45-C9-D52
A66-B45-C9-D52
A2-B53-C9-D52
A3-B53-C9-D52
A9-B53-C9-D52
A13-B53-C9-D52
A24-B53-C9-D52
A69-B53-C9-D52
A67-B53-C9-D52
A39-B53-C9-D52
A65-B53-C9-D52
A66-B53-C9-D52
A2-B79-C9-D52
A3-B79-C9-D52
A9-B79-C9-D52
A13-B79-C9-D52
A24-B79-C9-D52
A69-B79-C9-D52
A67-B79-C9-D52
A39-B79-C9-D52
A65-B79-C9-D52
A66-B79-C9-D52
A2-B80-C9-D52
A3-B80-C9-D52
A9-B80-C9-D52
A13-B80-C9-D52
A24-B80-C9-D52
A69-B80-C9-D52
A67-B80-C9-D52
A39-B80-C9-D52
A65-B80-C9-D52
A66-B80-C9-D52
A2-B85-C9-D52
A3-B85-C9-D52
A9-B85-C9-D52
A13-B85-C9-D52
A24-B85-C9-D52
A69-B85-C9-D52
A67-B85-C9-D52
A39-B85-C9-D52
A65-B85-C9-D52
A66-B85-C9-D52
A2-B86-C9-D52
A3-B86-C9-D52
A9-B86-C9-D52
A13-B86-C9-D52
A24-B86-C9-D52
A69-B86-C9-D52
A67-B86-C9-D52
A39-B86-C9-D52
A65-B86-C9-D52
A66-B86-C9-D52
A2-B87-C9-D52
A3-B87-C9-D52
A9-B87-C9-D52
A13-B87-C9-D52
A24-B87-C9-D52
A69-B87-C9-D52
A67-B87-C9-D52
A39-B87-C9-D52
A65-B87-C9-D52
A66-B87-C9-D52
A2-B89-C9-D52
A3-B89-C9-D52
A9-B89-C9-D52

-continued
A13-B89-C9-D52
A24-B89-C9-D52
A69-B89-C9-D52
A67-B89-C9-D52
A39-B89-C9-D52
A65-B89-C9-D52
A66-B89-C9-D52
A2-B92-C9-D52
A3-B92-C9-D52
A9-B92-C9-D52
A13-B92-C9-D52
A24-B92-C9-D52
A69-B92-C9-D52
A67-B92-C9-D52
A39-B92-C9-D52
A65-B92-C9-D52
A66-B92-C9-D52
A2-B4-C10-D52
A3-B4-C10-D52
A9-B4-C10-D52
A13-B4-C10-D52
A24-B4-C10-D52
A69-B4-C10-D52
A67-B4-C10-D52
A39-B4-C10-D52
A65-B4-C10-D52
A66-B4-C10-D52
A2-B5-C10-D52
A3-B5-C10-D52
A9-B5-C10-D52
A13-B5-C10-D52
A24-B5-C10-D52
A69-B5-C10-D52
A67-B5-C10-D52
A39-B5-C10-D52
A65-B5-C10-D52
A66-B5-C10-D52
A2-B6-C10-D52
A3-B6-C10-D52
A9-B6-C10-D52
A13-B6-C10-D52
A24-B6-C10-D52
A69-B6-C10-D52
A67-B6-C10-D52
A39-B6-C10-D52
A65-B6-C10-D52
A66-B6-C10-D52
A2-B32-C10-D52
A3-B32-C10-D52
A9-B32-C10-D52
A13-B32-C10-D52
A24-B32-C10-D52
A69-B32-C10-D52
A67-B32-C10-D52
A39-B32-C10-D52
A65-B32-C10-D52
A66-B32-C10-D52
A2-B39-C10-D52
A3-B39-C10-D52
A9-B39-C10-D52
A13-B39-C10-D52
A24-B39-C10-D52
A69-B39-C10-D52
A67-B39-C10-D52
A39-B39-C10-D52
A65-B39-C10-D52
A66-B39-C10-D52
A2-B45-C10-D52
A3-B45-C10-D52
A9-B45-C10-D52
A13-B45-C10-D52
A24-B45-C10-D52
A69-B45-C10-D52
A67-B45-C10-D52
A39-B45-C10-D52
A65-B45-C10-D52
A66-B45-C10-D52
A2-B53-C10-D52
A3-B53-C10-D52
A9-B53-C10-D52

-continued
A13-B53-C10-D52
A24-B53-C10-D52
A69-B53-C10-D52
A67-B53-C10-D52
A39-B53-C10-D52
A65-B53-C10-D52
A66-B53-C10-D52
A2-B79-C10-D52
A3-B79-C10-D52
A9-B79-C10-D52
A13-B79-C10-D52
A24-B79-C10-D52
A69-B79-C10-D52
A67-B79-C10-D52
A39-B79-C10-D52
A65-B79-C10-D52
A66-B79-C10-D52
A2-B80-C10-D52
A3-B80-C10-D52
A9-B80-C10-D52
A13-B80-C10-D52
A24-B80-C10-D52
A69-B80-C10-D52
A67-B80-C10-D52
A39-B80-C10-D52
A65-B80-C10-D52
A66-B80-C10-D52
A2-B85-C10-D52
A3-B85-C10-D52
A9-B85-C10-D52
A13-B85-C10-D52
A24-B85-C10-D52
A69-B85-C10-D52
A67-B85-C10-D52
A39-B85-C10-D52
A65-B85-C10-D52
A66-B85-C10-D52
A2-B86-C10-D52
A3-B86-C10-D52
A9-B86-C10-D52
A13-B86-C10-D52
A24-B86-C10-D52
A69-B86-C10-D52
A67-B86-C10-D52
A39-B86-C10-D52
A65-B86-C10-D52
A66-B86-C10-D52
A2-B87-C10-D52
A3-B87-C10-D52
A9-B87-C10-D52
A13-B87-C10-D52
A24-B87-C10-D52
A69-B87-C10-D52
A67-B87-C10-D52
A39-B87-C10-D52
A65-B87-C10-D52
A66-B87-C10-D52
A2-B89-C10-D52
A3-B89-C10-D52
A9-B89-C10-D52
A13-B89-C10-D52
A24-B89-C10-D52
A69-B89-C10-D52
A67-B89-C10-D52
A39-B89-C10-D52
A65-B89-C10-D52
A66-B89-C10-D52
A2-B92-C10-D52
A3-B92-C10-D52
A9-B92-C10-D52
A13-B92-C10-D52
A24-B92-C10-D52
A69-B92-C10-D52
A67-B92-C10-D52
A39-B92-C10-D52
A65-B92-C10-D52
A66-B92-C10-D52
A2-B4-C11-D52
A3-B4-C11-D52
A9-B4-C11-D52

-continued
A13-B4-C11-D52
A24-B4-C11-D52
A69-B4-C11-D52
A67-B4-C11-D52
A39-B4-C11-D52
A65-B4-C11-D52
A66-B4-C11-D52
A2-B5-C11-D52
A3-B5-C11-D52
A9-B5-C11-D52
A13-B5-C11-D52
A24-B5-C11-D52
A69-B5-C11-D52
A67-B5-C11-D52
A39-B5-C11-D52
A65-B5-C11-D52
A66-B5-C11-D52
A2-B6-C11-D52
A3-B6-C11-D52
A9-B6-C11-D52
A13-B6-C11-D52
A24-B6-C11-D52
A69-B6-C11-D52
A67-B6-C11-D52
A39-B6-C11-D52
A65-B6-C11-D52
A66-B6-C11-D52
A2-B32-C11-D52
A3-B32-C11-D52
A9-B32-C11-D52
A13-B32-C11-D52
A24-B32-C11-D52
A69-B32-C11-D52
A67-B32-C11-D52
A39-B32-C11-D52
A65-B32-C11-D52
A66-B32-C11-D52
A2-B39-C11-D52
A3-B39-C11-D52
A9-B39-C11-D52
A13-B39-C11-D52
A24-B39-C11-D52
A69-B39-C11-D52
A67-B39-C11-D52
A39-B39-C11-D52
A65-B39-C11-D52
A66-B39-C11-D52
A2-B45-C11-D52
A3-B45-C11-D52
A9-B45-C11-D52
A13-B45-C11-D52
A24-B45-C11-D52
A69-B45-C11-D52
A67-B45-C11-D52
A39-B45-C11-D52
A65-B45-C11-D52
A66-B45-C11-D52
A2-B53-C11-D52
A3-B53-C11-D52
A9-B53-C11-D52
A13-B53-C11-D52
A24-B53-C11-D52
A69-B53-C11-D52
A67-B53-C11-D52
A39-B53-C11-D52
A65-B53-C11-D52
A66-B53-C11-D52
A2-B79-C11-D52
A3-B79-C11-D52
A9-B79-C11-D52
A13-B79-C11-D52
A24-B79-C11-D52
A69-B79-C11-D52
A67-B79-C11-D52
A39-B79-C11-D52
A65-B79-C11-D52
A66-B79-C11-D52
A2-B80-C11-D52
A3-B80-C11-D52
A9-B80-C11-D52

-continued

A13-B80-C11-D52
A24-B80-C11-D52
A69-B80-C11-D52
A67-B80-C11-D52
A39-B80-C11-D52
A65-B80-C11-D52
A66-B80-C11-D52
A2-B85-C11-D52
A3-B85-C11-D52
A9-B85-C11-D52
A13-B85-C11-D52
A24-B85-C11-D52
A69-B85-C11-D52
A67-B85-C11-D52
A39-B85-C11-D52
A65-B85-C11-D52
A66-B85-C11-D52
A2-B86-C11-D52
A3-B86-C11-D52
A9-B86-C11-D52
A13-B86-C11-D52
A24-B86-C11-D52
A69-B86-C11-D52
A67-B86-C11-D52
A39-B86-C11-D52
A65-B86-C11-D52
A66-B86-C11-D52
A2-B87-C11-D52
A3-B87-C11-D52
A9-B87-C11-D52
A13-B87-C11-D52
A24-B87-C11-D52
A69-B87-C11-D52
A67-B87-C11-D52
A39-B87-C11-D52
A65-B87-C11-D52
A66-B87-C11-D52
A2-B89-C11-D52
A3-B89-C11-D52
A9-B89-C11-D52
A13-B89-C11-D52
A24-B89-C11-D52
A69-B89-C11-D52
A67-B89-C11-D52
A39-B89-C11-D52
A65-B89-C11-D52
A66-B89-C11-D52
A2-B92-C11-D52
A3-B92-C11-D52
A9-B92-C11-D52
A13-B92-C11-D52
A24-B92-C11-D52
A69-B92-C11-D52
A67-B92-C11-D52
A39-B92-C11-D52
A65-B92-C11-D52
A66-B92-C11-D52
A2-B4-C12-D52
A3-B4-C12-D52
A9-B4-C12-D52
A13-B4-C12-D52
A24-B4-C12-D52
A69-B4-C12-D52
A67-B4-C12-D52
A39-B4-C12-D52
A65-B4-C12-D52
A66-B4-C12-D52
A2-B5-C12-D52
A3-B5-C12-D52
A9-B5-C12-D52
A13-B5-C12-D52
A24-B5-C12-D52
A69-B5-C12-D52
A67-B5-C12-D52
A39-B5-C12-D52
A65-B5-C12-D52
A66-B5-C12-D52
A2-B6-C12-D52
A3-B6-C12-D52
A9-B6-C12-D52

-continued

A13-B6-C12-D52
A24-B6-C12-D52
A69-B6-C12-D52
A67-B6-C12-D52
A39-B6-C12-D52
A65-B6-C12-D52
A66-B6-C12-D52
A2-B32-C12-D52
A3-B32-C12-D52
A9-B32-C12-D52
A13-B32-C12-D52
A24-B32-C12-D52
A69-B32-C12-D52
A67-B32-C12-D52
A39-B32-C12-D52
A65-B32-C12-D52
A66-B32-C12-D52
A2-B39-C12-D52
A3-B39-C12-D52
A9-B39-C12-D52
A13-B39-C12-D52
A24-B39-C12-D52
A69-B39-C12-D52
A67-B39-C12-D52
A39-B39-C12-D52
A65-B39-C12-D52
A66-B39-C12-D52
A2-B45-C12-D52
A3-B45-C12-D52
A9-B45-C12-D52
A13-B45-C12-D52
A24-B45-C12-D52
A69-B45-C12-D52
A67-B45-C12-D52
A39-B45-C12-D52
A65-B45-C12-D52
A66-B45-C12-D52
A2-B53-C12-D52
A3-B53-C12-D52
A9-B53-C12-D52
A13-B53-C12-D52
A24-B53-C12-D52
A69-B53-C12-D52
A67-B53-C12-D52
A39-B53-C12-D52
A65-B53-C12-D52
A66-B53-C12-D52
A2-B79-C12-D52
A3-B79-C12-D52
A9-B79-C12-D52
A13-B79-C12-D52
A24-B79-C12-D52
A69-B79-C12-D52
A67-B79-C12-D52
A39-B79-C12-D52
A65-B79-C12-D52
A66-B79-C12-D52
A2-B80-C12-D52
A3-B80-C12-D52
A9-B80-C12-D52
A13-B80-C12-D52
A24-B80-C12-D52
A69-B80-C12-D52
A67-B80-C12-D52
A39-B80-C12-D52
A65-B80-C12-D52
A66-B80-C12-D52
A2-B85-C12-D52
A3-B85-C12-D52
A9-B85-C12-D52
A13-B85-C12-D52
A24-B85-C12-D52
A69-B85-C12-D52
A67-B85-C12-D52
A39-B85-C12-D52
A65-B85-C12-D52
A66-B85-C12-D52
A2-B86-C12-D52
A3-B86-C12-D52
A9-B86-C12-D52

-continued

A13-B86-C12-D52
A24-B86-C12-D52
A69-B86-C12-D52
A67-B86-C12-D52
A39-B86-C12-D52
A65-B86-C12-D52
A66-B86-C12-D52
A2-B87-C12-D52
A3-B87-C12-D52
A9-B87-C12-D52
A13-B87-C12-D52
A24-B87-C12-D52
A69-B87-C12-D52
A67-B87-C12-D52
A39-B87-C12-D52
A65-B87-C12-D52
A66-B87-C12-D52
A2-B89-C12-D52
A3-B89-C12-D52
A9-B89-C12-D52
A13-B89-C12-D52
A24-B89-C12-D52
A69-B89-C12-D52
A67-B89-C12-D52
A39-B89-C12-D52
A65-B89-C12-D52
A66-B89-C12-D52
A2-B92-C12-D52
A3-B92-C12-D52
A9-B92-C12-D52
A13-B92-C12-D52
A24-B92-C12-D52
A69-B92-C12-D52
A67-B92-C12-D52
A39-B92-C12-D52
A65-B92-C12-D52
A66-B92-C12-D52
A2-B4-C13-D52
A3-B4-C13-D52
A9-B4-C13-D52
A13-B4-C13-D52
A24-B4-C13-D52
A69-B4-C13-D52
A67-B4-C13-D52
A39-B4-C13-D52
A65-B4-C13-D52
A66-B4-C13-D52
A2-B5-C13-D52
A3-B5-C13-D52
A9-B5-C13-D52
A13-B5-C13-D52
A24-B5-C13-D52
A69-B5-C13-D52
A67-B5-C13-D52
A39-B5-C13-D52
A65-B5-C13-D52
A66-B5-C13-D52
A2-B6-C13-D52
A3-B6-C13-D52
A9-B6-C13-D52
A13-B6-C13-D52
A24-B6-C13-D52
A69-B6-C13-D52
A67-B6-C13-D52
A39-B6-C13-D52
A65-B6-C13-D52
A66-B6-C13-D52
A2-B32-C13-D52
A3-B32-C13-D52
A9-B32-C13-D52
A13-B32-C13-D52
A24-B32-C13-D52
A69-B32-C13-D52
A67-B32-C13-D52
A39-B32-C13-D52
A65-B32-C13-D52
A66-B32-C13-D52
A2-B39-C13-D52
A3-B39-C13-D52
A9-B39-C13-D52

-continued

A13-B39-C13-D52
A24-B39-C13-D52
A69-B39-C13-D52
A67-B39-C13-D52
A39-B39-C13-D52
A65-B39-C13-D52
A66-B39-C13-D52
A2-B45-C13-D52
A3-B45-C13-D52
A9-B45-C13-D52
A13-B45-C13-D52
A24-B45-C13-D52
A69-B45-C13-D52
A67-B45-C13-D52
A39-B45-C13-D52
A65-B45-C13-D52
A66-B45-C13-D52
A2-B53-C13-D52
A3-B53-C13-D52
A9-B53-C13-D52
A13-B53-C13-D52
A24-B53-C13-D52
A69-B53-C13-D52
A67-B53-C13-D52
A39-B53-C13-D52
A65-B53-C13-D52
A66-B53-C13-D52
A2-B79-C13-D52
A3-B79-C13-D52
A9-B79-C13-D52
A13-B79-C13-D52
A24-B79-C13-D52
A69-B79-C13-D52
A67-B79-C13-D52
A39-B79-C13-D52
A65-B79-C13-D52
A66-B79-C13-D52
A2-B80-C13-D52
A3-B80-C13-D52
A9-B80-C13-D52
A13-B80-C13-D52
A24-B80-C13-D52
A69-B80-C13-D52
A67-B80-C13-D52
A39-B80-C13-D52
A65-B80-C13-D52
A66-B80-C13-D52
A2-B85-C13-D52
A3-B85-C13-D52
A9-B85-C13-D52
A13-B85-C13-D52
A24-B85-C13-D52
A69-B85-C13-D52
A67-B85-C13-D52
A39-B85-C13-D52
A65-B85-C13-D52
A66-B85-C13-D52
A2-B86-C13-D52
A3-B86-C13-D52
A9-B86-C13-D52
A13-B86-C13-D52
A24-B86-C13-D52
A69-B86-C13-D52
A67-B86-C13-D52
A39-B86-C13-D52
A65-B86-C13-D52
A66-B86-C13-D52
A2-B87-C13-D52
A3-B87-C13-D52
A9-B87-C13-D52
A13-B87-C13-D52
A24-B87-C13-D52
A69-B87-C13-D52
A67-B87-C13-D52
A39-B87-C13-D52
A65-B87-C13-D52
A66-B87-C13-D52
A2-B89-C13-D52
A3-B89-C13-D52
A9-B89-C13-D52

-continued

A13-B89-C13-D52
A24-B89-C13-D52
A69-B89-C13-D52
A67-B89-C13-D52
A39-B89-C13-D52
A65-B89-C13-D52
A66-B89-C13-D52
A2-B92-C13-D52
A3-B92-C13-D52
A9-B92-C13-D52
A13-B92-C13-D52
A24-B92-C13-D52
A69-B92-C13-D52
A67-B92-C13-D52
A39-B92-C13-D52
A65-B92-C13-D52
A66-B92-C13-D52
A2-B4-C1-D53
A3-B4-C1-D53
A9-B4-C1-D53
A13-B4-C1-D53
A24-B4-C1-D53
A69-B4-C1-D53
A67-B4-C1-D53
A39-B4-C1-D53
A65-B4-C1-D53
A66-B4-C1-D53
A2-B5-C1-D53
A3-B5-C1-D53
A9-B5-C1-D53
A13-B5-C1-D53
A24-B5-C1-D53
A69-B5-C1-D53
A67-B5-C1-D53
A39-B5-C1-D53
A65-B5-C1-D53
A66-B5-C1-D53
A2-B6-C1-D53
A3-B6-C1-D53
A9-B6-C1-D53
A13-B6-C1-D53
A24-B6-C1-D53
A69-B6-C1-D53
A67-B6-C1-D53
A39-B6-C1-D53
A65-B6-C1-D53
A66-B6-C1-D53
A2-B32-C1-D53
A3-B32-C1-D53
A9-B32-C1-D53
A13-B32-C1-D53
A24-B32-C1-D53
A69-B32-C1-D53
A67-B32-C1-D53
A39-B32-C1-D53
A65-B32-C1-D53
A66-B32-C1-D53
A2-B39-C1-D53
A3-B39-C1-D53
A9-B39-C1-D53
A13-B39-C1-D53
A24-B39-C1-D53
A69-B39-C1-D53
A67-B39-C1-D53
A39-B39-C1-D53
A65-B39-C1-D53
A66-B39-C1-D53
A2-B45-C1-D53
A3-B45-C1-D53
A9-B45-C1-D53
A13-B45-C1-D53
A24-B45-C1-D53
A69-B45-C1-D53
A67-B45-C1-D53
A39-B45-C1-D53
A65-B45-C1-D53
A66-B45-C1-D53
A2-B53-C1-D53
A3-B53-C1-D53
A9-B53-C1-D53

-continued

A13-B53-C1-D53
A24-B53-C1-D53
A69-B53-C1-D53
A67-B53-C1-D53
A39-B53-C1-D53
A65-B53-C1-D53
A66-B53-C1-D53
A2-B79-C1-D53
A3-B79-C1-D53
A9-B79-C1-D53
A13-B79-C1-D53
A24-B79-C1-D53
A69-B79-C1-D53
A67-B79-C1-D53
A39-B79-C1-D53
A65-B79-C1-D53
A66-B79-C1-D53
A2-B80-C1-D53
A3-B80-C1-D53
A9-B80-C1-D53
A13-B80-C1-D53
A24-B80-C1-D53
A69-B80-C1-D53
A67-B80-C1-D53
A39-B80-C1-D53
A65-B80-C1-D53
A66-B80-C1-D53
A2-B85-C1-D53
A3-B85-C1-D53
A9-B85-C1-D53
A13-B85-C1-D53
A24-B85-C1-D53
A69-B85-C1-D53
A67-B85-C1-D53
A39-B85-C1-D53
A65-B85-C1-D53
A66-B85-C1-D53
A2-B86-C1-D53
A3-B86-C1-D53
A9-B86-C1-D53
A13-B86-C1-D53
A24-B86-C1-D53
A69-B86-C1-D53
A67-B86-C1-D53
A39-B86-C1-D53
A65-B86-C1-D53
A66-B86-C1-D53
A2-B87-C1-D53
A3-B87-C1-D53
A9-B87-C1-D53
A13-B87-C1-D53
A24-B87-C1-D53
A69-B87-C1-D53
A67-B87-C1-D53
A39-B87-C1-D53
A65-B87-C1-D53
A66-B87-C1-D53
A2-B89-C1-D53
A3-B89-C1-D53
A9-B89-C1-D53
A13-B89-C1-D53
A24-B89-C1-D53
A69-B89-C1-D53
A67-B89-C1-D53
A39-B89-C1-D53
A65-B89-C1-D53
A66-B89-C1-D53
A2-B92-C1-D53
A3-B92-C1-D53
A9-B92-C1-D53
A13-B92-C1-D53
A24-B92-C1-D53
A69-B92-C1-D53
A67-B92-C1-D53
A39-B92-C1-D53
A65-B92-C1-D53
A66-B92-C1-D53
A2-B4-C2-D53
A3-B4-C2-D53
A9-B4-C2-D53

-continued
A13-B4-C2-D53
A24-B4-C2-D53
A69-B4-C2-D53
A67-B4-C2-D53
A39-B4-C2-D53
A65-B4-C2-D53
A66-B4-C2-D53
A2-B5-C2-D53
A3-B5-C2-D53
A9-B5-C2-D53
A13-B5-C2-D53
A24-B5-C2-D53
A69-B5-C2-D53
A67-B5-C2-D53
A39-B5-C2-D53
A65-B5-C2-D53
A66-B5-C2-D53
A2-B6-C2-D53
A3-B6-C2-D53
A9-B6-C2-D53
A13-B6-C2-D53
A24-B6-C2-D53
A69-B6-C2-D53
A67-B6-C2-D53
A39-B6-C2-D53
A65-B6-C2-D53
A66-B6-C2-D53
A2-B32-C2-D53
A3-B32-C2-D53
A9-B32-C2-D53
A13-B32-C2-D53
A24-B32-C2-D53
A69-B32-C2-D53
A67-B32-C2-D53
A39-B32-C2-D53
A65-B32-C2-D53
A66-B32-C2-D53
A2-B39-C2-D53
A3-B39-C2-D53
A9-B39-C2-D53
A13-B39-C2-D53
A24-B39-C2-D53
A69-B39-C2-D53
A67-B39-C2-D53
A39-B39-C2-D53
A65-B39-C2-D53
A66-B39-C2-D53
A2-B45-C2-D53
A3-B45-C2-D53
A9-B45-C2-D53
A13-B45-C2-D53
A24-B45-C2-D53
A69-B45-C2-D53
A67-B45-C2-D53
A39-B45-C2-D53
A65-B45-C2-D53
A66-B45-C2-D53
A2-B53-C2-D53
A3-B53-C2-D53
A9-B53-C2-D53
A13-B53-C2-D53
A24-B53-C2-D53
A69-B53-C2-D53
A67-B53-C2-D53
A39-B53-C2-D53
A65-B53-C2-D53
A66-B53-C2-D53
A2-B79-C2-D53
A3-B79-C2-D53
A9-B79-C2-D53
A13-B79-C2-D53
A24-B79-C2-D53
A69-B79-C2-D53
A67-B79-C2-D53
A39-B79-C2-D53
A65-B79-C2-D53
A66-B79-C2-D53
A2-B80-C2-D53
A3-B80-C2-D53
A9-B80-C2-D53

-continued
A13-B80-C2-D53
A24-B80-C2-D53
A69-B80-C2-D53
A67-B80-C2-D53
A39-B80-C2-D53
A65-B80-C2-D53
A66-B80-C2-D53
A2-B85-C2-D53
A3-B85-C2-D53
A9-B85-C2-D53
A13-B85-C2-D53
A24-B85-C2-D53
A69-B85-C2-D53
A67-B85-C2-D53
A39-B85-C2-D53
A65-B85-C2-D53
A66-B85-C2-D53
A2-B86-C2-D53
A3-B86-C2-D53
A9-B86-G2-D53
A13-B86-C2-D53
A24-B86-C2-D53
A69-B86-C2-D53
A67-B86-C2-D53
A39-B86-C2-D53
A65-B86-C2-D53
A66-B86-C2-D53
A2-B87-C2-D53
A3-B87-C2-D53
A9-B87-C2-D53
A13-B87-C2-D53
A24-B87-C2-D53
A69-B87-C2-D53
A67-B87-C2-D53
A39-B87-C2-D53
A65-B87-C2-D53
A66-B87-C2-D53
A2-B89-C2-D53
A3-B89-C2-D53
A9-B89-C2-D53
A13-B89-C2-D53
A24-B89-C2-D53
A69-B89-C2-D53
A67-B89-C2-D53
A39-B89-C2-D53
A65-B89-C2-D53
A66-B89-C2-D53
A2-B92-C2-D53
A3-B92-C2-D53
A9-B92-C2-D53
A13-B92-C2-D53
A24-B92-C2-D53
A69-B92-C2-D53
A67-B92-C2-D53
A39-B92-C2-D53
A65-B92-C2-D53
A66-B92-C2-D53
A2-B4-C3-D53
A3-B4-C3-D53
A9-B4-C3-D53
A13-B4-C3-D53
A24-B4-C3-D53
A69-B4-C3-D53
A67-B4-C3-D53
A39-B4-C3-D53
A65-B4-C3-D53
A66-B4-C3-D53
A2-B5-C3-D53
A3-B5-C3-D53
A9-B5-C3-D53
A13-B5-C3-D53
A24-B5-C3-D53
A69-B5-C3-D53
A67-B5-C3-D53
A39-B5-C3-D53
A65-B5-C3-D53
A66-B5-C3-D53
A2-B6-C3-D53
A3-B6-C3-D53
A9-B6-C3-D53

-continued

A13-B6-C3-D53
A24-B6-C3-D53
A69-B6-C3-D53
A67-B6-C3-D53
A39-B6-C3-D53
A65-B6-C3-D53
A66-B6-C3-D53
A2-B32-C3-D53
A3-B32-C3-D53
A9-B32-C3-D53
A13-B32-C3-D53
A24-B32-C3-D53
A69-B32-C3-D53
A67-B32-C3-D53
A39-B32-C3-D53
A65-B32-C3-D53
A66-B32-C3-D53
A2-B39-C3-D53
A3-B39-C3-D53
A9-B39-C3-D53
A13-B39-C3-D53
A24-B39-C3-D53
A69-B39-C3-D53
A67-B39-C3-D53
A39-B39-C3-D53
A65-B39-C3-D53
A66-B39-C3-D53
A2-B45-C3-D53
A3-B45-C3-D53
A9-B45-C3-D53
A13-B45-C3-D53
A24-B45-C3-D53
A69-B45-C3-D53
A67-B45-C3-D53
A39-B45-C3-D53
A65-B45-C3-D53
A66-B45-C3-D53
A2-B53-C3-D53
A3-B53-C3-D53
A9-B53-C3-D53
A13-B53-C3-D53
A24-B53-C3-D53
A69-B53-C3-D53
A67-B53-C3-D53
A39-B53-C3-D53
A65-B53-C3-D53
A66-B53-C3-D53
A2-B79-C3-D53
A3-B79-C3-D53
A9-B79-C3-D53
A13-B79-C3-D53
A24-B79-C3-D53
A69-B79-C3-D53
A67-B79-C3-D53
A39-B79-C3-D53
A65-B79-C3-D53
A66-B79-C3-D53
A2-B80-C3-D53
A3-B80-C3-D53
A9-B80-C3-D53
A13-B80-C3-D53
A24-B80-C3-D53
A69-B80-C3-D53
A67-B80-C3-D53
A39-B80-C3-D53
A65-B80-C3-D53
A66-B80-C3-D53
A2-B85-C3-D53
A3-B85-C3-D53
A9-B85-C3-D53
A13-B85-C3-D53
A24-B85-C3-D53
A69-B85-C3-D53
A67-B85-C3-D53
A39-B85-C3-D53
A65-B85-C3-D53
A66-B85-C3-D53
A2-B86-C3-D53
A3-B86-C3-D53
A9-B86-C3-D53

-continued

A13-B86-C3-D53
A24-B86-C3-D53
A69-B86-C3-D53
A67-B86-C3-D53
A39-B86-C3-D53
A65-B86-C3-D53
A66-B86-C3-D53
A2-B87-C3-D53
A3-B87-C3-D53
A9-B87-C3-D53
A13-B87-C3-D53
A24-B87-C3-D53
A69-B87-C3-D53
A67-B87-C3-D53
A39-B87-C3-D53
A65-B87-C3-D53
A66-B87-C3-D53
A2-B89-C3-D53
A3-B89-C3-D53
A9-B89-C3-D53
A13-B89-C3-D53
A24-B89-C3-D53
A69-B89-C3-D53
A67-B89-C3-D53
A39-B89-C3-D53
A65-B89-C3-D53
A66-B89-C3-D53
A2-B92-C3-D53
A3-B92-C3-D53
A9-B92-C3-D53
A13-B92-C3-D53
A24-B92-C3-D53
A69-B92-C3-D53
A67-B92-C3-D53
A39-B92-C3-D53
A65-B92-C3-D53
A66-B92-C3-D53
A2-B4-C4-D53
A3-B4-C4-D53
A9-B4-C4-D53
A13-B4-C4-D53
A24-B4-C4-D53
A69-B4-C4-D53
A67-B4-C4-D53
A39-B4-C4-D53
A65-B4-C4-D53
A66-B4-C4-D53
A2-B5-C4-D53
A3-B5-C4-D53
A9-B5-C4-D53
A13-B5-C4-D53
A24-B5-C4-D53
A69-B5-C4-D53
A67-B5-C4-D53
A39-B5-C4-D53
A65-B5-C4-D53
A66-B5-C4-D53
A2-B6-C4-D53
A3-B6-C4-D53
A9-B6-C4-D53
A13-B6-C4-D53
A24-B6-C4-D53
A69-B6-C4-D53
A67-B6-C4-D53
A39-B6-C4-D53
A65-B6-C4-D53
A66-B6-C4-D53
A2-B32-C4-D53
A3-B32-C4-D53
A9-B32-C4-D53
A13-B32-C4-D53
A24-B32-C4-D53
A69-B32-C4-D53
A67-B32-C4-D53
A39-B32-C4-D53
A65-B32-C4-D53
A66-B32-C4-D53
A2-B39-C4-D53
A3-B39-C4-D53
A9-B39-C4-D53

-continued
A13-B39-C4-D53
A24-B39-C4-D53
A69-B39-C4-D53
A67-B39-C4-D53
A39-B39-C4-D53
A65-B39-C4-D53
A66-B39-C4-D53
A2-B45-C4-D53
A3-B45-C4-D53
A9-B45-C4-D53
A13-B45-C4-D53
A24-B45-C4-D53
A69-B45-C4-D53
A67-B45-C4-D53
A39-B45-C4-D53
A65-B45-C4-D53
A66-B45-C4-D53
A2-B53-C4-D53
A3-B53-C4-D53
A9-B53-C4-D53
A13-B53-C4-D53
A24-B53-C4-D53
A69-B53-C4-D53
A67-B53-C4-D53
A39-B53-C4-D53
A65-B53-C4-D53
A66-B53-C4-D53
A2-B79-C4-D53
A3-B79-C4-D53
A9-B79-C4-D53
A13-B79-C4-D53
A24-B79-C4-D53
A69-B79-C4-D53
A67-B79-C4-D53
A39-B79-C4-D53
A65-B79-C4-D53
A66-B79-C4-D53
A2-B80-C4-D53
A3-B80-C4-D53
A9-B80-C4-D53
A13-B80-C4-D53
A24-B80-C4-D53
A69-B80-C4-D53
A67-B80-C4-D53
A39-B80-C4-D53
A65-B80-C4-D53
A66-B80-C4-D53
A2-B85-C4-D53
A3-B85-C4-D53
A9-B85-C4-D53
A13-B85-C4-D53
A24-B85-C4-D53
A69-B85-C4-D53
A67-B85-C4-D53
A39-B85-C4-D53
A65-B85-C4-D53
A66-B85-C4-D53
A2-B86-C4-D53
A3-B86-C4-D53
A9-B86-C4-D53
A13-B86-C4-D53
A24-B86-C4-D53
A69-B86-C4-D53
A67-B86-C4-D53
A39-B86-C4-D53
A65-B86-C4-D53
A66-B86-C4-D53
A2-B87-C4-D53
A3-B87-C4-D53
A9-B87-C4-D53
A13-B87-C4-D53
A24-B87-C4-D53
A69-B87-C4-D53
A67-B87-C4-D53
A39-B87-C4-D53
A65-B87-C4-D53
A66-B87-C4-D53
A2-B89-C4-D53
A3-B89-C4-D53
A9-B89-C4-D53

-continued
A13-B89-C4-D53
A24-B89-C4-D53
A69-B89-C4-D53
A67-B89-C4-D53
A39-B89-C4-D53
A65-B89-C4-D53
A66-B89-C4-D53
A2-B92-C4-D53
A3-B92-C4-D53
A9-B92-C4-D53
A13-B92-C4-D53
A24-B92-C4-D53
A69-B92-C4-D53
A67-B92-C4-D53
A39-B92-C4-D53
A65-B92-C4-D53
A66-B92-C4-D53
A2-B4-C5-D53
A3-B4-C5-D53
A9-B4-C5-D53
A13-B4-C5-D53
A24-B4-C5-D53
A69-B4-C5-D53
A67-B4-C5-D53
A39-B4-C5-D53
A65-B4-C5-D53
A66-B4-C5-D53
A2-B5-C5-D53
A3-B5-C5-D53
A9-B5-C5-D53
A13-B5-C5-D53
A24-B5-C5-D53
A69-B5-C5-D53
A67-B5-C5-D53
A39-B5-C5-D53
A65-B5-C5-D53
A66-B5-C5-D53
A2-B6-C5-D53
A3-B6-C5-D53
A9-B6-C5-D53
A13-B6-C5-D53
A24-B6-C5-D53
A69-B6-C5-D53
A67-B6-C5-D53
A39-B6-C5-D53
A65-B6-C5-D53
A66-B6-C5-D53
A2-B32-C5-D53
A3-B32-C5-D53
A9-B32-C5-D53
A13-B32-C5-D53
A24-B32-C5-D53
A69-B32-C5-D53
A67-B32-C5-D53
A39-B32-C5-D53
A65-B32-C5-D53
A66-B32-C5-D53
A2-B39-C5-D53
A3-B39-C5-D53
A9-B39-C5-D53
A13-B39-C5-D53
A24-B39-C5-D53
A69-B39-C5-D53
A67-B39-C5-D53
A39-B39-C5-D53
A65-B39-C5-D53
A66-B39-C5-D53
A2-B45-C5-D53
A3-B45-C5-D53
A9-B45-C5-D53
A13-B45-C5-D53
A24-B45-C5-D53
A69-B45-C5-D53
A67-B45-C5-D53
A39-B45-C5-D53
A65-B45-C5-D53
A66-B45-C5-D53
A2-B53-C5-D53
A3-B53-C5-D53
A9-B53-C5-D53

-continued
A13-B53-C5-D53
A24-B53-C5-D53
A69-B53-C5-D53
A67-B53-C5-D53
A39-B53-C5-D53
A65-B53-C5-D53
A66-B53-C5-D53
A2-B79-C5-D53
A3-B79-C5-D53
A9-B79-C5-D53
A13-B79-C5-D53
A24-B79-C5-D53
A69-B79-C5-D53
A67-B79-C5-D53
A39-B79-C5-D53
A65-B79-C5-D53
A66-B79-C5-D53
A2-B80-C5-D53
A3-B80-C5-D53
A9-B80-C5-D53
A13-B80-C5-D53
A24-B80-C5-D53
A69-B80-C5-D53
A67-B80-C5-D53
A39-B80-C5-D53
A65-B80-C5-D53
A66-B80-C5-D53
A2-B85-C5-D53
A3-B85-C5-D53
A9-B85-C5-D53
A13-B85-C5-D53
A24-B85-C5-D53
A69-B85-C5-D53
A67-B85-C5-D53
A39-B85-C5-D53
A65-B85-C5-D53
A66-B85-C5-D53
A2-B86-C5-D53
A3-B86-C5-D53
A9-B86-C5-D53
A13-B86-C5-D53
A24-B86-C5-D53
A69-B86-C5-D53
A67-B86-C5-D53
A39-B86-C5-D53
A65-B86-C5-D53
A66-B86-C5-D53
A2-B87-C5-D53
A3-B87-C5-D53
A9-B87-C5-D53
A13-B87-C5-D53
A24-B87-C5-D53
A69-B87-C5-D53
A67-B87-C5-D53
A39-B87-C5-D53
A65-B87-C5-D53
A66-B87-C5-D53
A2-B89-C5-D53
A3-B89-C5-D53
A9-B89-C5-D53
A13-B89-C5-D53
A24-B89-C5-D53
A69-B89-C5-D53
A67-B89-C5-D53
A39-B89-C5-D53
A65-B89-C5-D53
A66-B89-C5-D53
A2-B92-C5-D53
A3-B92-C5-D53
A9-B92-C5-D53
A13-B92-C5-D53
A24-B92-C5-D53
A69-B92-C5-D53
A67-B92-C5-D53
A39-B92-C5-D53
A65-B92-C5-D53
A66-B92-C5-D53
A2-B4-C6-D53
A3-B4-C6-D53
A9-B4-C6-D53

-continued
A13-B4-C6-D53
A24-B4-C6-D53
A69-B4-C6-D53
A67-B4-C6-D53
A39-B4-C6-D53
A65-B4-C6-D53
A66-B4-C6-D53
A2-B5-C6-D53
A3-B5-C6-D53
A9-B5-C6-D53
A13-B5-C6-D53
A24-B5-C6-D53
A69-B5-C6-D53
A67-B5-C6-D53
A39-B5-C6-D53
A65-B5-C6-D53
A66-B5-C6-D53
A2-B6-C6-D53
A3-B6-C6-D53
A9-B6-C6-D53
A13-B6-C6-D53
A24-B6-C6-D53
A69-B6-C6-D53
A67-B6-C6-D53
A39-B6-C6-D53
A65-B6-C6-D53
A66-B6-C6-D53
A2-B32-C6-D53
A3-B32-C6-D53
A9-B32-C6-D53
A13-B32-C6-D53
A24-B32-C6-D53
A69-B32-C6-D53
A67-B32-C6-D53
A39-B32-C6-D53
A65-B32-C6-D53
A66-B32-C6-D53
A2-B39-C6-D53
A3-B39-C6-D53
A9-B39-C6-D53
A13-B39-C6-D53
A24-B39-C6-D53
A69-B39-C6-D53
A67-B39-C6-D53
A39-B39-C6-D53
A65-B39-C6-D53
A66-B39-C6-D53
A2-B45-C6-D53
A3-B45-C6-D53
A9-B45-C6-D53
A13-B45-C6-D53
A24-B45-C6-D53
A69-B45-C6-D53
A67-B45-C6-D53
A39-B45-C6-D53
A65-B45-C6-D53
A66-B45-C6-D53
A2-B53-C6-D53
A3-B53-C6-D53
A9-B53-C6-D53
A13-B53-C6-D53
A24-B53-C6-D53
A69-B53-C6-D53
A67-B53-C6-D53
A39-B53-C6-D53
A65-B53-C6-D53
A66-B53-C6-D53
A2-B79-C6-D53
A3-B79-C6-D53
A9-B79-C6-D53
A13-B79-C6-D53
A24-B79-C6-D53
A69-B79-C6-D53
A67-B79-C6-D53
A39-B79-C6-D53
A65-B79-C6-D53
A66-B79-C6-D53
A2-B80-C6-D53
A3-B80-C6-D53
A9-B80-C6-D53

-continued
A13-B80-C6-D53
A24-B80-C6-D53
A69-B80-C6-D53
A67-B80-C6-D53
A39-B80-C6-D53
A65-B80-C6-D53
A66-B80-C6-D53
A2-B85-C6-D53
A3-B85-C6-D53
A9-B85-C6-D53
A13-B85-C6-D53
A24-B85-C6-D53
A69-B85-C6-D53
A67-B85-C6-D53
A39-B85-C6-D53
A65-B85-C6-D53
A66-B85-C6-D53
A2-B86-C6-D53
A3-B86-C6-D53
A9-B86-C6-D53
A13-B86-C6-D53
A24-B86-C6-D53
A69-B86-C6-D53
A67-B86-C6-D53
A39-B86-C6-D53
A65-B86-C6-D53
A66-B86-C6-D53
A2-B87-C6-D53
A3-B87-C6-D53
A9-B87-C6-D53
A13-B87-C6-D53
A24-B87-C6-D53
A69-B87-C6-D53
A67-B87-C6-D53
A39-B87-C6-D53
A65-B87-C6-D53
A66-B87-C6-D53
A2-B89-C6-D53
A3-B89-C6-D53
A9-B89-C6-D53
A13-B89-C6-D53
A24-B89-C6-D53
A69-B89-C6-D53
A67-B89-C6-D53
A39-B89-C6-D53
A65-B89-C6-D53
A66-B89-C6-D53
A2-B92-C6-D53
A3-B92-C6-D53
A9-B92-C6-D53
A13-B92-C6-D53
A24-B92-C6-D53
A69-B92-C6-D53
A67-B92-C6-D53
A39-B92-C6-D53
A65-B92-C6-D53
A66-B92-C6-D53
A2-B4-C7-D53
A3-B4-C7-D53
A9-B4-C7-D53
A13-B4-C7-D53
A24-B4-C7-D53
A69-B4-C7-D53
A67-B4-C7-D53
A39-B4-C7-D53
A65-B4-C7-D53
A66-B4-C7-D53
A2-B5-C7-D53
A3-B5-C7-D53
A9-B5-C7-D53
A13-B5-C7-D53
A24-B5-C7-D53
A69-B5-C7-D53
A67-B5-C7-D53
A39-B5-C7-D53
A65-B5-C7-D53
A66-B5-C7-D53
A2-B6-C7-D53
A3-B6-C7-D53
A9-B6-C7-D53

-continued
A13-B6-C7-D53
A24-B6-C7-D53
A69-B6-C7-D53
A67-B6-C7-D53
A39-B6-C7-D53
A65-B6-C7-D53
A66-B6-C7-D53
A2-B32-C7-D53
A3-B32-C7-D53
A9-B32-C7-D53
A13-B32-C7-D53
A24-B32-C7-D53
A69-B32-C7-D53
A67-B32-C7-D53
A39-B32-C7-D53
A65-B32-C7-D53
A66-B32-C7-D53
A2-B39-C7-D53
A3-B39-C7-D53
A9-B39-C7-D53
A13-B39-C7-D53
A24-B39-C7-D53
A69-B39-C7-D53
A67-B39-C7-D53
A39-B39-C7-D53
A65-B39-C7-D53
A66-B39-C7-D53
A2-B45-C7-D53
A3-B45-C7-D53
A9-B45-C7-D53
A13-B45-C7-D53
A24-B45-C7-D53
A69-B45-C7-D53
A67-B45-C7-D53
A39-B45-C7-D53
A65-B45-C7-D53
A66-B45-C7-D53
A2-B53-C7-D53
A3-B53-C7-D53
A9-B53-C7-D53
A13-B53-C7-D53
A24-B53-C7-D53
A69-B53-C7-D53
A67-B53-C7-D53
A39-B53-C7-D53
A65-B53-C7-D53
A66-B53-C7-D53
A2-B79-C7-D53
A3-B79-C7-D53
A9-B79-C7-D53
A13-B79-C7-D53
A24-B79-C7-D53
A69-B79-C7-D53
A67-B79-C7-D53
A39-B79-C7-D53
A65-B79-C7-D53
A66-B79-C7-D53
A2-B80-C7-D53
A3-B80-C7-D53
A9-B80-C7-D53
A13-B80-C7-D53
A24-B80-C7-D53
A69-B80-C7-D53
A67-B80-C7-D53
A39-B80-C7-D53
A65-B80-C7-D53
A66-B80-C7-D53
A2-B85-C7-D53
A3-B85-C7-D53
A9-B85-C7-D53
A13-B85-C7-D53
A24-B85-C7-D53
A69-B85-C7-D53
A67-B85-C7-D53
A39-B85-C7-D53
A65-B85-C7-D53
A66-B85-C7-D53
A2-B86-C7-D53
A3-B86-C7-D53
A9-B86-C7-D53

-continued

| | |
|---|---|
| A13-B86-C7-D53 | A13-B39-C8-D53 |
| A24-B86-C7-D53 | A24-B39-C8-D53 |
| A69-B86-C7-D53 | A69-B39-C8-D53 |
| A67-B86-C7-D53 | A67-B39-C8-D53 |
| A39-B86-C7-D53 | A39-B39-C8-D53 |
| A65-B86-C7-D53 | A65-B39-C8-D53 |
| A66-B86-C7-D53 | A66-B39-C8-D53 |
| A2-B87-C7-D53 | A2-B45-C8-D53 |
| A3-B87-C7-D53 | A3-B45-C8-D53 |
| A9-B87-C7-D53 | A9-B45-C8-D53 |
| A13-B87-C7-D53 | A13-B45-C8-D53 |
| A24-B87-C7-D53 | A24-B45-C8-D53 |
| A69-B87-C7-D53 | A69-B45-C8-D53 |
| A67-B87-C7-D53 | A67-B45-C8-D53 |
| A39-B87-C7-D53 | A39-B45-C8-D53 |
| A65-B87-C7-D53 | A65-B45-C8-D53 |
| A66-B87-C7-D53 | A66-B45-C8-D53 |
| A2-B89-C7-D53 | A2-B53-C8-D53 |
| A3-B89-C7-D53 | A3-B53-C8-D53 |
| A9-B89-C7-D53 | A9-B53-C8-D53 |
| A13-B89-C7-D53 | A13-B53-C8-D53 |
| A24-B89-C7-D53 | A24-B53-C8-D53 |
| A69-B89-C7-D53 | A69-B53-C8-D53 |
| A67-B89-C7-D53 | A67-B53-C8-D53 |
| A39-B89-C7-D53 | A39-B53-C8-D53 |
| A65-B89-C7-D53 | A65-B53-C8-D53 |
| A66-B89-C7-D53 | A66-B53-C8-D53 |
| A2-B92-C7-D53 | A2-B79-C8-D53 |
| A3-B92-C7-D53 | A3-B79-C8-D53 |
| A9-B92-C7-D53 | A9-B79-C8-D53 |
| A13-B92-C7-D53 | A13-B79-C8-D53 |
| A24-B92-C7-D53 | A24-B79-C8-D53 |
| A69-B92-C7-D53 | A69-B79-C8-D53 |
| A67-B92-C7-D53 | A67-B79-C8-D53 |
| A39-B92-C7-D53 | A39-B79-C8-D53 |
| A65-B92-C7-D53 | A65-B79-C8-D53 |
| A66-B92-C7-D53 | A66-B79-C8-D53 |
| A2-B4-C8-D53 | A2-B80-C8-D53 |
| A3-B4-C8-D53 | A3-B80-C8-D53 |
| A9-B4-C8-D53 | A9-B80-C8-D53 |
| A13-B4-C8-D53 | A13-B80-C8-D53 |
| A24-B4-C8-D53 | A24-B80-C8-D53 |
| A69-B4-C8-D53 | A69-B80-C8-D53 |
| A67-B4-C8-D53 | A67-B80-C8-D53 |
| A39-B4-C8-D53 | A39-B80-C8-D53 |
| A65-B4-C8-D53 | A65-B80-C8-D53 |
| A66-B4-C8-D53 | A66-B80-C8-D53 |
| A2-B5-C8-D53 | A2-B85-C8-D53 |
| A3-B5-C8-D53 | A3-B85-C8-D53 |
| A9-B5-C8-D53 | A9-B85-C8-D53 |
| A13-B5-C8-D53 | A13-B85-C8-D53 |
| A24-B5-C8-D53 | A24-B85-C8-D53 |
| A69-B5-C8-D53 | A69-B85-C8-D53 |
| A67-B5-C8-D53 | A67-B85-C8-D53 |
| A39-B5-C8-D53 | A39-B85-C8-D53 |
| A65-B5-C8-D53 | A65-B85-C8-D53 |
| A66-B5-C8-D53 | A66-B85-C8-D53 |
| A2-B6-C8-D53 | A2-B86-C8-D53 |
| A3-B6-C8-D53 | A3-B86-C8-D53 |
| A9-B6-C8-D53 | A9-B86-C8-D53 |
| A13-B6-C8-D53 | A13-B86-C8-D53 |
| A24-B6-C8-D53 | A24-B86-C8-D53 |
| A69-B6-C8-D53 | A69-B86-C8-D53 |
| A67-B6-C8-D53 | A67-B86-C8-D53 |
| A39-B6-C8-D53 | A39-B86-C8-D53 |
| A65-B6-C8-D53 | A65-B86-C8-D53 |
| A66-B6-C8-D53 | A66-B86-C8-D53 |
| A2-B32-C8-D53 | A2-B87-C8-D53 |
| A3-B32-C8-D53 | A3-B87-C8-D53 |
| A9-B32-C8-D53 | A9-B87-C8-D53 |
| A13-B32-C8-D53 | A13-B87-C8-D53 |
| A24-B32-C8-D53 | A24-B87-C8-D53 |
| A69-B32-C8-D53 | A69-B87-C8-D53 |
| A67-B32-C8-D53 | A67-B87-C8-D53 |
| A39-B32-C8-D53 | A39-B87-C8-D53 |
| A65-B32-C8-D53 | A65-B87-C8-D53 |
| A66-B32-C8-D53 | A66-B87-C8-D53 |
| A2-B39-C8-D53 | A2-B89-C8-D53 |
| A3-B39-C8-D53 | A3-B89-C8-D53 |
| A9-B39-C8-D53 | A9-B89-C8-D53 |

-continued
A13-B89-C8-D53
A24-B89-C8-D53
A69-B89-C8-D53
A67-B89-C8-D53
A39-B89-C8-D53
A65-B89-C8-D53
A66-B89-C8-D53
A2-B92-C8-D53
A3-B92-C8-D53
A9-B92-C8-D53
A13-B92-C8-D53
A24-B92-C8-D53
A69-B92-C8-D53
A67-B92-C8-D53
A39-B92-C8-D53
A65-B92-C8-D53
A66-B92-C8-D53
A2-B4-C9-D53
A3-B4-C9-D53
A9-B4-C9-D53
A13-B4-C9-D53
A24-B4-C9-D53
A69-B4-C9-D53
A67-B4-C9-D53
A39-B4-C9-D53
A65-B4-C9-D53
A66-B4-C9-D53
A2-B5-C9-D53
A3-B5-C9-D53
A9-B5-C9-D53
A13-B5-C9-D53
A24-B5-C9-D53
A69-B5-C9-D53
A67-B5-C9-D53
A39-B5-C9-D53
A65-B5-C9-D53
A66-B5-C9-D53
A2-B6-C9-D53
A3-B6-C9-D53
A9-B6-C9-D53
A13-B6-C9-D53
A24-B6-C9-D53
A69-B6-C9-D53
A67-B6-C9-D53
A39-B6-C9-D53
A65-B6-C9-D53
A66-B6-C9-D53
A2-B32-C9-D53
A3-B32-C9-D53
A9-B32-C9-D53
A13-B32-C9-D53
A24-B32-C9-D53
A69-B32-C9-D53
A67-B32-C9-D53
A39-B32-C9-D53
A65-B32-C9-D53
A66-B32-C9-D53
A2-B39-C9-D53
A3-B39-C9-D53
A9-B39-C9-D53
A13-B39-C9-D53
A24-B39-C9-D53
A69-B39-C9-D53
A67-B39-C9-D53
A39-B39-C9-D53
A65-B39-C9-D53
A66-B39-C9-D53
A2-B45-C9-D53
A3-B45-C9-D53
A9-B45-C9-D53
A13-B45-C9-D53
A24-B45-C9-D53
A69-B45-C9-D53
A67-B45-C9-D53
A39-B45-C9-D53
A65-B45-C9-D53
A66-B45-C9-D53
A2-B53-C9-D53
A3-B53-C9-D53
A9-B53-C9-D53

-continued
A13-B53-C9-D53
A24-B53-C9-D53
A69-B53-C9-D53
A67-B53-C9-D53
A39-B53-C9-D53
A65-B53-C9-D53
A66-B53-C9-D53
A2-B79-C9-D53
A3-B79-C9-D53
A9-B79-C9-D53
A13-B79-C9-D53
A24-B79-C9-D53
A69-B79-C9-D53
A67-B79-C9-D53
A39-B79-C9-D53
A65-B79-C9-D53
A66-B79-C9-D53
A2-B80-C9-D53
A3-B80-C9-D53
A9-B80-C9-D53
A13-B80-C9-D53
A24-B80-C9-D53
A69-B80-C9-D53
A67-B80-C9-D53
A39-B80-C9-D53
A65-B80-C9-D53
A66-B80-C9-D53
A2-B85-C9-D53
A3-B85-C9-D53
A9-B85-C9-D53
A13-B85-C9-D53
A24-B85-C9-D53
A69-B85-C9-D53
A67-B85-C9-D53
A39-B85-C9-D53
A65-B85-C9-D53
A66-B85-C9-D53
A2-B86-C9-D53
A3-B86-C9-D53
A9-B86-C9-D53
A13-B86-C9-D53
A24-B86-C9-D53
A69-B86-C9-D53
A67-B86-C9-D53
A39-B86-C9-D53
A65-B86-C9-D53
A66-B86-C9-D53
A2-B87-C9-D53
A3-B87-C9-D53
A9-B87-C9-D53
A13-B87-C9-D53
A24-B87-C9-D53
A69-B87-C9-D53
A67-B87-C9-D53
A39-B87-C9-D53
A65-B87-C9-D53
A66-B87-C9-D53
A2-B89-C9-D53
A3-B89-C9-D53
A9-B89-C9-D53
A13-B89-C9-D53
A24-B89-C9-D53
A69-B89-C9-D53
A67-B89-C9-D53
A39-B89-C9-D53
A65-B89-C9-D53
A66-B89-C9-D53
A2-B92-C9-D53
A3-B92-C9-D53
A9-B92-C9-D53
A13-B92-C9-D53
A24-B92-C9-D53
A69-B92-C9-D53
A67-B92-C9-D53
A39-B92-C9-D53
A65-B92-C9-D53
A66-B92-C9-D53
A2-B4-C10-D53
A3-B4-C10-D53
A9-B4-C10-D53

-continued
A13-B4-C10-D53
A24-B4-C10-D53
A69-B4-C10-D53
A67-B4-C10-D53
A39-B4-C10-D53
A65-B4-C10-D53
A66-B4-C10-D53
A2-B5-C10-D53
A3-B5-C10-D53
A9-B5-C10-D53
A13-B5-C10-D53
A24-B5-C10-D53
A69-B5-C10-D53
A67-B5-C10-D53
A39-B5-C10-D53
A65-B5-C10-D53
A66-B5-C10-D53
A2-B6-C10-D53
A3-B6-C10-D53
A9-B6-C10-D53
A13-B6-C10-D53
A24-B6-C10-D53
A69-B6-C10-D53
A67-B6-C10-D53
A39-B6-C10-D53
A65-B6-C10-D53
A66-B6-C10-D53
A2-B32-C10-D53
A3-B32-C10-D53
A9-B32-C10-D53
A13-B32-C10-D53
A24-B32-C10-D53
A69-B32-C10-D53
A67-B32-C10-D53
A39-B32-C10-D53
A65-B32-C10-D53
A66-B32-C10-D53
A2-B39-C10-D53
A3-B39-C10-D53
A9-B39-C10-D53
A13-B39-C10-D53
A24-B39-C10-D53
A69-B39-C10-D53
A67-B39-C10-D53
A39-B39-C10-D53
A65-B39-C10-D53
A66-B39-C10-D53
A2-B45-C10-D53
A3-B45-C10-D53
A9-B45-C10-D53
A13-B45-C10-D53
A24-B45-C10-D53
A69-B45-C10-D53
A67-B45-C10-D53
A39-B45-C10-D53
A65-B45-C10-D53
A66-B45-C10-D53
A2-B53-C10-D53
A3-B53-C10-D53
A9-B53-C10-D53
A13-B53-C10-D53
A24-B53-C10-D53
A69-B53-C10-D53
A67-B53-C10-D53
A39-B53-C10-D53
A65-B53-C10-D53
A66-B53-C10-D53
A2-B79-C10-D53
A3-B79-C10-D53
A9-B79-C10-D53
A13-B79-C10-D53
A24-B79-C10-D53
A69-B79-C10-D53
A67-B79-C10-D53
A39-B79-C10-D53
A65-B79-C10-D53
A66-B79-C10-D53
A2-B80-C10-D53
A3-B80-C10-D53
A9-B80-C10-D53

-continued
A13-B80-C10-D53
A24-B80-C10-D53
A69-B80-C10-D53
A67-B80-C10-D53
A39-B80-C10-D53
A65-B80-C10-D53
A66-B80-C10-D53
A2-B85-C10-D53
A3-B85-C10-D53
A9-B85-C10-D53
A13-B85-C10-D53
A24-B85-C10-D53
A69-B85-C10-D53
A67-B85-C10-D53
A39-B85-C10-D53
A65-B85-C10-D53
A66-B85-C10-D53
A2-B86-C10-D53
A3-B86-C10-D53
A9-B86-C10-D53
A13-B86-C10-D53
A24-B86-C10-D53
A69-B86-C10-D53
A67-B86-C10-D53
A39-B86-C10-D53
A65-B86-C10-D53
A66-B86-C10-D53
A2-B87-C10-D53
A3-B87-C10-D53
A9-B87-C10-D53
A13-B87-C10-D53
A24-B87-C10-D53
A69-B87-C10-D53
A67-B87-C10-D53
A39-B87-C10-D53
A65-B87-C10-D53
A66-B87-C10-D53
A2-B89-C10-D53
A3-B89-C10-D53
A9-B89-C10-D53
A13-B89-C10-D53
A24-B89-C10-D53
A69-B89-C10-D53
A67-B89-C10-D53
A39-B89-C10-D53
A65-B89-C10-D53
A66-B89-C10-D53
A2-B92-C10-D53
A3-B92-C10-D53
A9-B92-C10-D53
A13-B92-C10-D53
A24-B92-C10-D53
A69-B92-C10-D53
A67-B92-C10-D53
A39-B92-C10-D53
A65-B92-C10-D53
A66-B92-C10-D53
A2-B4-C11-D53
A3-B4-C11-D53
A9-B4-C11-D53
A13-B4-C11-D53
A24-B4-C11-D53
A69-B4-C11-D53
A67-B4-C11-D53
A39-B4-C11-D53
A65-B4-C11-D53
A66-B4-C11-D53
A2-B5-C11-D53
A3-B5-C11-D53
A9-B5-C11-D53
A13-B5-C11-D53
A24-B5-C11-D53
A69-B5-C11-D53
A67-B5-C11-D53
A39-B5-C11-D53
A65-B5-C11-D53
A66-B5-C11-D53
A2-B6-C11-D53
A3-B6-C11-D53
A9-B6-C11-D53

-continued

A13-B6-C11-D53
A24-B6-C11-D53
A69-B6-C11-D53
A67-B6-C11-D53
A39-B6-C11-D53
A65-B6-C11-D53
A66-B6-C11-D53
A2-B32-C11-D53
A3-B32-C11-D53
A9-B32-C11-D53
A13-B32-C11-D53
A24-B32-C11-D53
A69-B32-C11-D53
A67-B32-C11-D53
A39-B32-C11-D53
A65-B32-C11-D53
A66-B32-C11-D53
A2-B39-C11-D53
A3-B39-C11-D53
A9-B39-C11-D53
A13-B39-C11-D53
A24-B39-C11-D53
A69-B39-C11-D53
A67-B39-C11-D53
A39-B39-C11-D53
A65-B39-C11-D53
A66-B39-C11-D53
A2-B45-C11-D53
A3-B45-C11-D53
A9-B45-C11-D53
A13-B45-C11-D53
A24-B45-C11-D53
A69-B45-C11-D53
A67-B45-C11-D53
A39-B45-C11-D53
A65-B45-C11-D53
A66-B45-C11-D53
A2-B53-C11-D53
A3-B53-C11-D53
A9-B53-C11-D53
A13-B53-C11-D53
A24-B53-C11-D53
A69-B53-C11-D53
A67-B53-C11-D53
A39-B53-C11-D53
A65-B53-C11-D53
A66-B53-C11-D53
A2-B79-C11-D53
A3-B79-C11-D53
A9-B79-C11-D53
A13-B79-C11-D53
A24-B79-C11-D53
A69-B79-C11-D53
A67-B79-C11-D53
A39-B79-C11-D53
A65-B79-C11-D53
A66-B79-C11-D53
A2-B80-C11-D53
A3-B80-C11-D53
A9-B80-C11-D53
A13-B80-C11-D53
A24-B80-C11-D53
A69-B80-C11-D53
A67-B80-C11-D53
A39-B80-C11-D53
A65-B80-C11-D53
A66-B80-C11-D53
A2-B85-C11-D53
A3-B85-C11-D53
A9-B85-C11-D53
A13-B85-C11-D53
A24-B85-C11-D53
A69-B85-C11-D53
A67-B85-C11-D53
A39-B85-C11-D53
A65-B85-C11-D53
A66-B85-C11-D53
A2-B86-C11-D53
A3-B86-C11-D53
A9-B86-C11-D53

-continued

A13-B86-C11-D53
A24-B86-C11-D53
A69-B86-C11-D53
A67-B86-C11-D53
A39-B86-C11-D53
A65-B86-C11-D53
A66-B86-C11-D53
A2-B87-C11-D53
A3-B87-C11-D53
A9-B87-C11-D53
A13-B87-C11-D53
A24-B87-C11-D53
A69-B87-C11-D53
A67-B87-C11-D53
A39-B87-C11-D53
A65-B87-C11-D53
A66-B87-C11-D53
A2-B89-C11-D53
A3-B89-C11-D53
A9-B89-C11-D53
A13-B89-C11-D53
A24-B89-C11-D53
A69-B89-C11-D53
A67-B89-C11-D53
A39-B89-C11-D53
A65-B89-C11-D53
A66-B89-C11-D53
A2-B92-C11-D53
A3-B92-C11-D53
A9-B92-C11-D53
A13-B92-C11-D53
A24-B92-C11-D53
A69-B92-C11-D53
A67-B92-C11-D53
A39-B92-C11-D53
A65-B92-C11-D53
A66-B92-C11-D53
A2-B4-C12-D53
A3-B4-C12-D53
A9-B4-C12-D53
A13-B4-C12-D53
A24-B4-C12-D53
A69-B4-C12-D53
A67-B4-C12-D53
A39-B4-C12-D53
A65-B4-C12-D53
A66-B4-C12-D53
A2-B5-C12-D53
A3-B5-C12-D53
A9-B5-C12-D53
A13-B5-C12-D53
A24-B5-C12-D53
A69-B5-C12-D53
A67-B5-C12-D53
A39-B5-C12-D53
A65-B5-C12-D53
A66-B5-C12-D53
A2-B6-C12-D53
A3-B6-C12-D53
A9-B6-C12-D53
A13-B6-C12-D53
A24-B6-C12-D53
A69-B6-C12-D53
A67-B6-C12-D53
A39-B6-C12-D53
A65-B6-C12-D53
A66-B6-C12-D53
A2-B32-C12-D53
A3-B32-C12-D53
A9-B32-C12-D53
A13-B32-C12-D53
A24-B32-C12-D53
A69-B32-C12-D53
A67-B32-C12-D53
A39-B32-C12-D53
A65-B32-C12-D53
A66-B32-C12-D53
A2-B39-C12-D53
A3-B39-C12-D53
A9-B39-C12-D53

-continued

A13-B39-C12-D53
A24-B39-C12-D53
A69-B39-C12-D53
A67-B39-C12-D53
A39-B39-C12-D53
A65-B39-C12-D53
A66-B39-C12-D53
A2-B45-C12-D53
A3-B45-C12-D53
A9-B45-C12-D53
A13-B45-C12-D53
A24-B45-C12-D53
A69-B45-C12-D53
A67-B45-C12-D53
A39-B45-C12-D53
A65-B45-C12-D53
A66-B45-C12-D53
A2-B53-C12-D53
A3-B53-C12-D53
A9-B53-C12-D53
A13-B53-C12-D53
A24-B53-C12-D53
A69-B53-C12-D53
A67-B53-C12-D53
A39-B53-C12-D53
A65-B53-C12-D53
A66-B53-C12-D53
A2-B79-C12-D53
A3-B79-C12-D53
A9-B79-C12-D53
A13-B79-C12-D53
A24-B79-C12-D53
A69-B79-C12-D53
A67-B79-C12-D53
A39-B79-C12-D53
A65-B79-C12-D53
A66-B79-C12-D53
A2-B80-C12-D53
A3-B80-C12-D53
A9-B80-C12-D53
A13-B80-C12-D53
A24-B80-C12-D53
A69-B80-C12-D53
A67-B80-C12-D53
A39-B80-C12-D53
A65-B80-C12-D53
A66-B80-C12-D53
A2-B85-C12-D53
A3-B85-C12-D53
A9-B85-C12-D53
A13-B85-C12-D53
A24-B85-C12-D53
A69-B85-C12-D53
A67-B85-C12-D53
A39-B85-C12-D53
A65-B85-C12-D53
A66-B85-C12-D53
A2-B86-C12-D53
A3-B86-C12-D53
A9-B86-C12-D53
A13-B86-C12-D53
A24-B86-C12-D53
A69-B86-C12-D53
A67-B86-C12-D53
A39-B86-C12-D53
A65-B86-C12-D53
A66-B86-C12-D53
A2-B87-C12-D53
A3-B87-C12-D53
A9-B87-C12-D53
A13-B87-C12-D53
A24-B87-C12-D53
A69-B87-C12-D53
A67-B87-C12-D53
A39-B87-C12-D53
A65-B87-C12-D53
A66-B87-C12-D53
A2-B89-C12-D53
A3-B89-C12-D53
A9-B89-C12-D53

-continued

A13-B89-C12-D53
A24-B89-C12-D53
A69-B89-C12-D53
A67-B89-C12-D53
A39-B89-C12-D53
A65-B89-C12-D53
A66-B89-C12-D53
A2-B92-C12-D53
A3-B92-C12-D53
A9-B92-C12-D53
A13-B92-C12-D53
A24-B92-C12-D53
A69-B92-C12-D53
A67-B92-C12-D53
A39-B92-C12-D53
A65-B92-C12-D53
A66-B92-C12-D53
A2-B4-C13-D53
A3-B4-C13-D53
A9-B4-C13-D53
A13-B4-C13-D53
A24-B4-C13-D53
A69-B4-C13-D53
A67-B4-C13-D53
A39-B4-C13-D53
A65-B4-C13-D53
A66-B4-C13-D53
A2-B5-C13-D53
A3-B5-C13-D53
A9-B5-C13-D53
A13-B5-C13-D53
A24-B5-C13-D53
A69-B5-C13-D53
A67-B5-C13-D53
A39-B5-C13-D53
A65-B5-C13-D53
A66-B5-C13-D53
A2-B6-C13-D53
A3-B6-C13-D53
A9-B6-C13-D53
A13-B6-C13-D53
A24-B6-C13-D53
A69-B6-C13-D53
A67-B6-C13-D53
A39-B6-C13-D53
A65-B6-C13-D53
A66-B6-C13-D53
A2-B32-C13-D53
A3-B32-C13-D53
A9-B32-C13-D53
A13-B32-C13-D53
A24-B32-C13-D53
A69-B32-C13-D53
A67-B32-C13-D53
A39-B32-C13-D53
A65-B32-C13-D53
A66-B32-C13-D53
A2-B39-C13-D53
A3-B39-C13-D53
A9-B39-C13-D53
A13-B39-C13-D53
A24-B39-C13-D53
A69-B39-C13-D53
A67-B39-C13-D53
A39-B39-C13-D53
A65-B39-C13-D53
A66-B39-C13-D53
A2-B45-C13-D53
A3-B45-C13-D53
A9-B45-C13-D53
A13-B45-C13-D53
A24-B45-C13-D53
A69-B45-C13-D53
A67-B45-C13-D53
A39-B45-C13-D53
A65-B45-C13-D53
A66-B45-C13-D53
A2-B53-C13-D53
A3-B53-C13-D53
A9-B53-C13-D53

-continued

A13-B53-C13-D53
A24-B53-C13-D53
A69-B53-C13-D53
A67-B53-C13-D53
A39-B53-C13-D53
A65-B53-C13-D53
A66-B53-C13-D53
A2-B79-C13-D53
A3-B79-C13-D53
A9-B79-C13-D53
A13-B79-C13-D53
A24-B79-C13-D53
A69-B79-C13-D53
A67-B79-C13-D53
A39-B79-C13-D53
A65-B79-C13-D53
A66-B79-C13-D53
A2-B80-C13-D53
A3-B80-C13-D53
A9-B80-C13-D53
A13-B80-C13-D53
A24-B80-C13-D53
A69-B80-C13-D53
A67-B80-C13-D53
A39-B80-C13-D53
A65-B80-C13-D53
A66-B80-C13-D53
A2-B85-C13-D53
A3-B85-C13-D53
A9-B85-C13-D53
A13-B85-C13-D53
A24-B85-C13-D53
A69-B85-C13-D53
A67-B85-C13-D53
A39-B85-C13-D53
A65-B85-C13-D53
A66-B85-C13-D53
A2-B86-C13-D53
A3-B86-C13-D53
A9-B86-C13-D53
A13-B86-C13-D53
A24-B86-C13-D53
A69-B86-C13-D53
A67-B86-C13-D53
A39-B86-C13-D53
A65-B86-C13-D53
A66-B86-C13-D53
A2-B87-C13-D53
A3-B87-C13-D53
A9-B87-C13-D53
A13-B87-C13-D53
A24-B87-C13-D53
A69-B87-C13-D53
A67-B87-C13-D53
A39-B87-C13-D53
A65-B87-C13-D53
A66-B87-C13-D53
A2-B89-C13-D53
A3-B89-C13-D53
A9-B89-C13-D53
A13-B89-C13-D53
A24-B89-C13-D53
A69-B89-C13-D53
A67-B89-C13-D53
A39-B89-C13-D53
A65-B89-C13-D53
A66-B89-C13-D53
A2-B92-C13-D53
A3-B92-C13-D53
A9-B92-C13-D53
A13-B92-C13-D53
A24-B92-C13-D53
A69-B92-C13-D53
A67-B92-C13-D53
A39-B92-C13-D53
A65-B92-C13-D53
A66-B92-C13-D53
A2-B4-C1-D54
A3-B4-C1-D54
A9-B4-C1-D54

-continued

A13-B4-C1-D54
A24-B4-C1-D54
A69-B4-C1-D54
A67-B4-C1-D54
A39-B4-C1-D54
A65-B4-C1-D54
A66-B4-C1-D54
A2-B5-C1-D54
A3-B5-C1-D54
A9-B5-C1-D54
A13-B5-C1-D54
A24-B5-C1-D54
A69-B5-C1-D54
A67-B5-C1-D54
A39-B5-C1-D54
A65-B5-C1-D54
A66-B5-C1-D54
A2-B6-C1-D54
A3-B6-C1-D54
A9-B6-C1-D54
A13-B6-C1-D54
A24-B6-C1-D54
A69-B6-C1-D54
A67-B6-C1-D54
A39-B6-C1-D54
A65-B6-C1-D54
A66-B6-C1-D54
A2-B32-C1-D54
A3-B32-C1-D54
A9-B32-C1-D54
A13-B32-C1-D54
A24-B32-C1-D54
A69-B32-C1-D54
A67-B32-C1-D54
A39-B32-C1-D54
A65-B32-C1-D54
A66-B32-C1-D54
A2-B39-C1-D54
A3-B39-C1-D54
A9-B39-C1-D54
A13-B39-C1-D54
A24-B39-C1-D54
A69-B39-C1-D54
A67-B39-C1-D54
A39-B39-C1-D54
A65-B39-C1-D54
A66-B39-C1-D54
A2-B45-C1-D54
A3-B45-C1-D54
A9-B45-C1-D54
A13-B45-C1-D54
A24-B45-C1-D54
A69-B45-C1-D54
A67-B45-C1-D54
A39-B45-C1-D54
A65-B45-C1-D54
A66-B45-C1-D54
A2-B53-C1-D54
A3-B53-C1-D54
A9-B53-C1-D54
A13-B53-C1-D54
A24-B53-C1-D54
A69-B53-C1-D54
A67-B53-C1-D54
A39-B53-C1-D54
A65-B53-C1-D54
A66-B53-C1-D54
A2-B79-C1-D54
A3-B79-C1-D54
A9-B79-C1-D54
A13-B79-C1-D54
A24-B79-C1-D54
A69-B79-C1-D54
A67-B79-C1-D54
A39-B79-C1-D54
A65-B79-C1-D54
A66-B79-C1-D54
A2-B80-C1-D54
A3-B80-C1-D54
A9-B80-C1-D54

-continued

A13-B80-C1-D54
A24-B80-C1-D54
A69-B80-C1-D54
A67-B80-C1-D54
A39-B80-C1-D54
A65-B80-C1-D54
A66-B80-C1-D54
A2-B85-C1-D54
A3-B85-C1-D54
A9-B85-C1-D54
A13-B85-C1-D54
A24-B85-C1-D54
A69-B85-C1-D54
A67-B85-C1-D54
A39-B85-C1-D54
A65-B85-C1-D54
A66-B85-C1-D54
A2-B86-C1-D54
A3-B86-C1-D54
A9-B86-C1-D54
A13-B86-C1-D54
A24-B86-C1-D54
A69-B86-C1-D54
A67-B86-C1-D54
A39-B86-C1-D54
A65-B86-C1-D54
A66-B86-C1-D54
A2-B87-C1-D54
A3-B87-CL-D54
A9-B87-C1-D54
A13-B87-C1-D54
A24-B87-C1-D54
A69-B87-C1-D54
A67-B87-C1-D54
A39-B87-C1-D54
A65-B87-C1-D54
A66-B87-C1-D54
A2-B89-C1-D54
A3-B89-C1-D54
A9-B89-C1-D54
A13-B89-C1-D54
A24-B89-C1-D54
A69-B89-C1-D54
A67-B89-C1-D54
A39-B89-C1-D54
A65-B89-C1-D54
A66-B89-C1-D54
A2-B92-C1-D54
A3-B92-C1-D54
A9-B92-C1-D54
A13-B92-C1-D54
A24-B92-C1-D54
A69-B92-C1-D54
A67-B92-C1-D54
A39-B92-C1-D54
A65-B92-C1-D54
A66-B92-C1-D54
A2-B4-C2-D54
A3-B4-C2-D54
A9-B4-C2-D54
A13-B4-C2-D54
A24-B4-C2-D54
A69-B4-C2-D54
A67-B4-C2-D54
A39-B4-C2-D54
A65-B4-C2-D54
A66-B4-C2-D54
A2-B5-C2-D54
A3-B5-C2-D54
A9-B5-C2-D54
A13-B5-C2-D54
A24-B5-C2-D54
A69-B5-C2-D54
A67-B5-C2-D54
A39-B5-C2-D54
A65-B5-C2-D54
A66-B5-C2-D54
A2-B6-C2-D54
A3-B6-C2-D54
A9-B6-C2-D54

-continued

A13-B67C2-D54
A24-B6-C2-D54
A69-B6-C2-D54
A67-B6-C2-D54
A39-B6-C2-D54
A65-B6-C2-D54
A66-B6-C2-D54
A2-B32-C2-D54
A3-B32-C2-D54
A9-B32-C2-D54
A13-B32-C2-D54
A24-B32-C2-D54
A69-B32-C2-D54
A67-B32-C2-D54
A39-B32-C2-D54
A65-B32-C2-D54
A66-B32-C2-D54
A2-B39-C2-D54
A3-B39-C2-D54
A9-B39-C2-D54
A13-B39-C2-D54
A24-B39-C2-D54
A69-B39-C2-D54
A67-B39-C2-D54
A39-B39-C2-D54
A65-B39-C2-D54
A66-B39-C2-D54
A2-B45-C2-D54
A3-B45-C2-D54
A9-B45-C2-D54
A13-B45-C2-D54
A24-B45-C2-D54
A69-B45-C2-D54
A67-B45-C2-D54
A39-B45-C2-D54
A65-B45-C2-D54
A66-B45-C2-D54
A2-B53-C2-D54
A3-B53-C2-D54
A9-B53-C2-D54
A13-B53-C2-D54
A24-B53-C2-D54
A69-B53-C2-D54
A67-B53-C2-D54
A39-B53-C2-D54
A65-B53-C2-D54
A66-B53-C2-D54
A2-B79-C2-D54
A3-B79-C2-D54
A9-B79-C2-D54
A13-B79-C2-D54
A24-B79-C2-D54
A69-B79-C2-D54
A67-B79-C2-D54
A39-B79-C2-D54
A65-B79-C2-D54
A66-B79-C2-D54
A2-B80-C2-D54
A3-B80-C2-D54
A9-B80-C2-D54
A13-B80-C2-D54
A24-B80-C2-D54
A69-B80-C2-D54
A67-B80-C2-D54
A39-B80-C2-D54
A65-B80-C2-D54
A66-B80-C2-D54
A2-B85-C2-D54
A3-B85-C2-D54
A9-B85-C2-D54
A13-B85-C2-D54
A24-B85-C2-D54
A69-B85-C2-D54
A67-B85-C2-D54
A39-B85-C2-D54
A65-B85-C2-D54
A66-B85-C2-D54
A2-B86-C2-D54
A3-B86-C2-D54
A9-B86-C2-D54

-continued
A13-B86-C2-D54
A24-B86-C2-D54
A69-B86-C2-D54
A67-B86-C2-D54
A39-B86-C2-D54
A65-B86-C2-D54
A66-B86-C2-D54
A2-B87-C2-D54
A3-B87-C2-D54
A9-B87-C2-D54
A13-B87-C2-D54
A24-B87-C2-D54
A69-B87-C2-D54
A67-B87-C2-D54
A39-B87-C2-D54
A65-B87-C2-D54
A66-B87-C2-D54
A2-B89-C2-D54
A3-B89-C2-D54
A9-B89-C2-D54
A13-B89-C2-D54
A24-B89-C2-D54
A69-B89-C2-D54
A67-B89-C2-D54
A39-B89-C2-D54
A65-B89-C2-D54
A66-B89-C2-D54
A2-B92-C2-D54
A3-B92-C2-D54
A9-B92-C2-D54
A13-B92-C2-D54
A24-B92-C2-D54
A69-B92-C2-D54
A67-B92-C2-D54
A39-B92-C2-D54
A65-B92-C2-D54
A66-B92-C2-D54
A2-B4-C3-D54
A3-B4-C3-D54
A9-B4-C3-D54
A13-B4-C3-D54
A24-B4-C3-D54
A69-B4-C3-D54
A67-B4-C3-D54
A39-B4-C3-D54
A65-B4-C3-D54
A66-B4-C3-D54
A2-B5-C3-D54
A3-B5-C3-D54
A9-B5-C3-D54
A13-B5-C3-D54
A24-B5-C3-D54
A69-B5-C3-D54
A67-B5-C3-D54
A39-B5-C3-D54
A65-B5-C3-D54
A66-B5-C3-D54
A2-B6-C3-D54
A3-B6-C3-D54
A9-B6-C3-D54
A13-B6-C3-D54
A24-B6-C3-D54
A69-B6-C3-D54
A67-B6-C3-D54
A39-B6-C3-D54
A65-B6-C3-D54
A66-B6-C3-D54
A2-B32-C3-D54
A3-B32-C3-D54
A9-B32-C3-D54
A13-B32-C3-D54
A24-B32-C3-D54
A69-B32-C3-D54
A67-B32-C3-D54
A39-B32-C3-D54
A65-B32-C3-D54
A66-B32-C3-D54
A2-B39-C3-D54
A3-B39-C3-D54
A9-B39-C3-D54

-continued
A13-B39-C3-D54
A24-B39-C3-D54
A69-B39-C3-D54
A67-B39-C3-D54
A39-B39-C3-D54
A65-B39-C3-D54
A66-B39-C3-D54
A2-B45-C3-D54
A3-B45-C3-D54
A9-B45-C3-D54
A13-B45-C3-D54
A24-B45-C3-D54
A69-B45-C3-D54
A67-B45-C3-D54
A39-B45-C3-D54
A65-B45-C3-D54
A66-B45-C3-D54
A2-B53-C3-D54
A3-B53-C3-D54
A9-B53-C3-D54
A13-B53-C3-D54
A24-B53-C3-D54
A69-B53-C3-D54
A67-B53-C3-D54
A39-B53-C3-D54
A65-B53-C3-D54
A66-B53-C3-D54
A2-B79-C3-D54
A3-B79-C3-D54
A9-B79-C3-D54
A13-B79-C3-D54
A24-B79-C3-D54
A69-B79-C3-D54
A67-B79-C3-D54
A39-B79-C3-D54
A65-B79-C3-D54
A66-B79-C3-D54
A2-B80-C3-D54
A3-B80-C3-D54
A9-B80-C3-D54
A13-B80-C3-D54
A24-B80-C3-D54
A69-B80-C3-D54
A67-B80-C3-D54
A39-B80-C3-D54
A65-B80-C3-D54
A66-B80-C3-D54
A2-B85-C3-D54
A3-B85-C3-D54
A9-B85-C3-D54
A13-B85-C3-D54
A24-B85-C3-D54
A69-B85-C3-D54
A67-B85-C3-D54
A39-B85-C3-D54
A65-B85-C3-D54
A66-B85-C3-D54
A2-B86-C3-D54
A3-B86-C3-D54
A9-B86-C3-D54
A13-B86-C3-D54
A24-B86-C3-D54
A69-B86-C3-D54
A67-B86-C3-D54
A39-B86-C3-D54
A65-B86-C3-D54
A66-B86-C3-D54
A2-B87-C3-D54
A3-B87-C3-D54
A9-B87-C3-D54
A13-B87-C3-D54
A24-B87-C3-D54
A69-B87-C3-D54
A67-B87-C3-D54
A39-B87-C3-D54
A65-B87-C3-D54
A66-B87-C3-D54
A2-B89-C3-D54
A3-B89-C3-D54
A9-B89-C3-D54

-continued

A13-B89-C3-D54
A24-B89-C3-D54
A69-B89-C3-D54
A67-B89-C3-D54
A39-B89-C3-D54
A65-B89-C3-D54
A66-B89-C3-D54
A2-B92-C3-D54
A3-B92-C3-D54
A9-B92-C3-D54
A13-B92-C3-D54
A24-B92-C3-D54
A69-B92-C3-D54
A67-B92-C3-D54
A39-B92-C3-D54
A65-B92-C3-D54
A66-B92-C3-D54
A2-B4-C4-D54
A3-B4-C4-D54
A9-B4-C4-D54
A13-B4-C4-D54
A24-B4-C4-D54
A69-B4-C4-D54
A67-B4-C4-D54
A39-B4-C4-D54
A65-B4-C4-D54
A66-B4-C4-D54
A2-B5-C4-D54
A3-B5-C4-D54
A9-B5-C4-D54
A13-B5-C4-D54
A24-B5-C4-D54
A69-B5-C4-D54
A67-B5-C4-D54
A39-B5-C4-D54
A65-B5-C4-D54
A66-B5-C4-D54
A2-B6-C4-D54
A3-B6-C4-D54
A9-B6-C4-D54
A13-B6-C4-D54
A24-B6-C4-D54
A69-B6-C4-D54
A67-B6-C4-D54
A39-B6-C4-D54
A65-B6-C4-D54
A66-B6-C4-D54
A2-B32-C4-D54
A3-B32-C4-D54
A9-B32-C4-D54
A13-B32-C4-D54
A24-B32-C4-D54
A69-B32-C4-D54
A67-B32-C4-D54
A39-B32-C4-D54
A65-B32-C4-D54
A66-B32-C4-D54
A2-B39-C4-D54
A3-B39-C4-D54
A9-B39-C4-D54
A13-B39-C4-D54
A24-B39-C4-D54
A69-B39-C4-D54
A67-B39-C4-D54
A39-B39-C4-D54
A65-B39-C4-D54
A66-B39-C4-D54
A2-B45-C4-D54
A3-B45-C4-D54
A9-B45-C4-D54
A13-B45-C4-D54
A24-B45-C4-D54
A69-B45-C4-D54
A67-B45-C4-D54
A39-B45-C4-D54
A65-B45-C4-D54
A66-B45-C4-D54
A2-B53-C4-D54
A3-B53-C4-D54
A9-B53-C4-D54

-continued

A13-B53-C4-D54
A24-B53-C4-D54
A69-B53-C4-D54
A67-B53-C4-D54
A39-B53-C4-D54
A65-B53-C4-D54
A66-B53-C4-D54
A2-B79-C4-D54
A3-B79-C4-D54
A9-B79-C4-D54
A13-B79-C4-D54
A24-B79-C4-D54
A69-B79-C4-D54
A67-B79-C4-D54
A39-B79-C4-D54
A65-B79-C4-D54
A66-B79-C4-D54
A2-B80-C4-D54
A3-B80-C4-D54
A9-B80-C4-D54
A13-B80-C4-D54
A24-B80-C4-D54
A69-B80-C4-D54
A67-B80-C4-D54
A39-B80-C4-D54
A65-B80-C4-D54
A66-B80-C4-D54
A2-B85-C4-D54
A3-B85-C4-D54
A9-B85-C4-D54
A13-B85-C4-D54
A24-B85-C4-D54
A69-B85-C4-D54
A67-B85-C4-D54
A39-B85-C4-D54
A65-B85-C4-D54
A66-B85-C4-D54
A2-B86-C4-D54
A3-B86-C4-D54
A9-B86-C4-D54
A13-B86-C4-D54
A24-B86-C4-D54
A69-B86-C4-D54
A67-B86-C4-D54
A39-B86-C4-D54
A65-B86-C4-D54
A66-B86-C4-D54
A2-B87-C4-D54
A3-B87-C4-D54
A9-B87-C4-D54
A13-B87-C4-D54
A24-B87-C4-D54
A69-B87-C4-D54
A67-B87-C4-D54
A39-B87-C4-D54
A65-B87-C4-D54
A66-B87-C4-D54
A2-B89-C4-D54
A3-B89-C4-D54
A9-B89-C4-D54
A13-B89-C4-D54
A24-B89-C4-D54
A69-B89-C4-D54
A67-B89-C4-D54
A39-B89-C4-D54
A65-B89-C4-D54
A66-B89-C4-D54
A2-B92-C4-D54
A3-B92-C4-D54
A9-B92-C4-D54
A13-B92-C4-D54
A24-B92-C4-D54
A69-B92-C4-D54
A67-B92-C4-D54
A39-B92-C4-D54
A65-B92-C4-D54
A66-B92-C4-D54
A2-B4-C5-D54
A3-B4-C5-D54
A9-B4-C5-D54

-continued
A13-B4-C5-D54
A24-B4-C5-D54
A69-B4-C5-D54
A67-B4-C5-D54
A39-B4-C5-D54
A65-B4-C5-D54
A66-B4-C5-D54
A2-B5-C5-D54
A3-B5-C5-D54
A9-B5-C5-D54
A13-B5-C5-D54
A24-B5-C5-D54
A69-B5-C5-D54
A67-B5-C5-D54
A39-B5-C5-D54
A65-B5-C5-D54
A66-B5-C5-D54
A2-B6-C5-D54
A3-B6-C5-D54
A9-B6-C5-D54
A13-B6-C5-D54
A24-B6-C5-D54
A69-B6-C5-D54
A67-B6-C5-D54
A39-B6-C5-D54
A65-B6-C5-D54
A66-B6-C5-D54
A2-B32-C5-D54
A3-B32-C5-D54
A9-B32-C5-D54
A13-B32-C5-D54
A24-B32-C5-D54
A69-B32-C5-D54
A67-B32-C5-D54
A39-B32-C5-D54
A65-B32-C5-D54
A66-B32-C5-D54
A2-B39-C5-D54
A3-B39-C5-D54
A9-B39-C5-D54
A13-B39-C5-D54
A24-B39-C5-D54
A69-B39-C5-D54
A67-B39-C5-D54
A39-B39-C5-D54
A65-B39-C5-D54
A66-B39-C5-D54
A2-B45-C5-D54
A3-B45-C5-D54
A9-B45-C5-D54
A13-B45-C5-D54
A24-B45-C5-D54
A69-B45-C5-D54
A67-B45-C5-D54
A39-B45-C5-D54
A65-B45-C5-D54
A66-B45-C5-D54
A2-B53-C5-D54
A3-B53-C5-D54
A9-B53-C5-D54
A13-B53-C5-D54
A24-B53-C5-D54
A69-B53-C5-D54
A67-B53-C5-D54
A39-B53-C5-D54
A65-B53-C5-D54
A66-B53-C5-D54
A2-B79-C5-D54
A3-B79-C5-D54
A9-B79-C5-D54
A13-B79-C5-D54
A24-B79-C5-D54
A69-B79-C5-D54
A67-B79-C5-D54
A39-B79-C5-D54
A65-B79-C5-D54
A66-B79-C5-D54
A2-B80-C5-D54
A3-B80-C5-D54
A9-B80-C5-D54

-continued
A13-B80-C5-D54
A24-B80-C5-D54
A69-B80-C5-D54
A67-B80-C5-D54
A39-B80-C5-D54
A65-B80-C5-D54
A66-B80-C5-D54
A2-B85-C5-D54
A3-B85-C5-D54
A9-B85-C5-D54
A13-B85-C5-D54
A24-B85-C5-D54
A69-B85-C5-D54
A67-B85-C5-D54
A39-B85-C5-D54
A65-B85-C5-D54
A66-B85-C5-D54
A2-B86-C5-D54
A3-B86-C5-D54
A9-B86-C5-D54
A13-B86-C5-D54
A24-B86-C5-D54
A69-B86-C5-D54
A67-B86-C5-D54
A39-B86-C5-D54
A65-B86-C5-D54
A66-B86-C5-D54
A2-B87-C5-D54
A3-B87-C5-D54
A9-B87-C5-D54
A13-B87-C5-D54
A24-B87-C5-D54
A69-B87-C5-D54
A67-B87-C5-D54
A39-B87-C5-D54
A65-B87-C5-D54
A66-B87-C5-D54
A2-B89-C5-D54
A3-B89-C5-D54
A9-B89-C5-D54
A13-B89-C5-D54
A24-B89-C5-D54
A69-B89-C5-D54
A67-B89-C5-D54
A39-B89-C5-D54
A65-B89-C5-D54
A66-B89-C5-D54
A2-B92-C5-D54
A3-B92-C5-D54
A9-B92-C5-D54
A13-B92-C5-D54
A24-B92-C5-D54
A69-B92-C5-D54
A67-B92-C5-D54
A39-B92-C5-D54
A65-B92-C5-D54
A66-B92-C5-D54
A2-B4-C6-D54
A3-B4-C6-D54
A9-B4-C6-D54
A13-B4-C6-D54
A24-B4-C6-D54
A69-B4-C6-D54
A67-B4-C6-D54
A39-B4-C6-D54
A65-B4-C6-D54
A66-B4-C6-D54
A2-B5-C6-D54
A3-B5-C6-D54
A9-B5-C6-D54
A13-B5-C6-D54
A24-B5-C6-D54
A69-B5-C6-D54
A67-B5-C6-D54
A39-B5-C6-D54
A65-B5-C6-D54
A66-B5-C6-D54
A2-B6-C6-D54
A3-B6-C6-D54
A9-B6-C6-D54

-continued

A13-B6-C6-D54
A24-B6-C6-D54
A69-B6-C6-D54
A67-B6-C6-D54
A39-B6-C6-D54
A65-B6-C6-D54
A66-B6-C6-D54
A2-B32-C6-D54
A3-B32-C6-D54
A9-B32-C6-D54
A13-B32-C6-D54
A24-B32-C6-D54
A69-B32-C6-D54
A67-B32-C6-D54
A39-B32-C6-D54
A65-B32-C6-D54
A66-B32-C6-D54
A2-B39-C6-D54
A3-B39-C6-D54
A9-B39-C6-D54
A13-B39-C6-D54
A24-B39-C6-D54
A69-B39-C6-D54
A67-B39-C6-D54
A39-B39-C6-D54
A65-B39-C6-D54
A66-B39-C6-D54
A2-B45-C6-D54
A3-B45-C6-D54
A9-B45-C6-D54
A13-B45-C6-D54
A24-B45-C6-D54
A69-B45-C6-D54
A67-B45-C6-D54
A39-B45-C6-D54
A65-B45-C6-D54
A66-B45-C6-D54
A2-B53-C6-D54
A3-B53-C6-D54
A9-B53-C6-D54
A13-B53-C6-D54
A24-B53-C6-D54
A69-B53-C6-D54
A67-B53-C6-D54
A39-B53-C6-D54
A65-B53-C6-D54
A66-B53-C6-D54
A2-B79-C6-D54
A3-B79-C6-D54
A9-B79-C6-D54
A13-B79-C6-D54
A24-B79-C6-D54
A69-B79-C6-D54
A67-B79-C6-D54
A39-B79-C6-D54
A65-B79-C6-D54
A66-B79-C6-D54
A2-B80-C6-D54
A3-B80-C6-D54
A9-B80-C6-D54
A13-B80-C6-D54
A24-B80-C6-D54
A69-B80-C6-D54
A67-B80-C6-D54
A39-B80-C6-D54
A65-B80-C6-D54
A66-B80-C6-D54
A2-B85-C6-D54
A3-B85-C6-D54
A9-B85-C6-D54
A13-B85-C6-D54
A24-B85-C6-D54
A69-B85-C6-D54
A67-B85-C6-D54
A39-B85-C6-D54
A65-B85-C6-D54
A66-B85-C6-D54
A2-B86-C6-D54
A3-B86-C6-D54
A9-B86-C6-D54

-continued

A13-B86-C6-D54
A24-B86-C6-D54
A69-B86-C6-D54
A67-B86-C6-D54
A39-B86-C6-D54
A65-B86-C6-D54
A66-B86-C6-D54
A2-B87-C6-D54
A3-B87-C6-D54
A9-B87-C6-D54
A13-B87-C6-D54
A24-B87-C6-D54
A69-B87-C6-D54
A67-B87-C6-D54
A39-B87-C6-D54
A65-B87-C6-D54
A66-B87-C6-D54
A2-B89-C6-D54
A3-B89-C6-D54
A9-B89-C6-D54
A13-B89-C6-D54
A24-B89-C6-D54
A69-B89-C6-D54
A67-B89-C6-D54
A39-B89-C6-D54
A65-B89-C6-D54
A66-B89-C6-D54
A2-B92-C6-D54
A3-B92-C6-D54
A9-B92-C6-D54
A13-B92-C6-D54
A24-B92-C6-D54
A69-B92-C6-D54
A67-B92-C6-D54
A39-B92-C6-D54
A65-B92-C6-D54
A66-B92-C6-D54
A2-B4-C7-D54
A3-B4-C7-D54
A9-B4-C7-D54
A13-B4-C7-D54
A24-B4-C7-D54
A69-B4-C7-D54
A67-B4-C7-D54
A39-B4-C7-D54
A65-B4-C7-D54
A66-B4-C7-D54
A2-B5-C7-D54
A3-B5-C7-D54
A9-B5-C7-D54
A13-B5-C7-D54
A24-B5-C7-D54
A69-B5-C7-D54
A67-B5-C7-D54
A39-B5-C7-D54
A65-B5-C7-D54
A66-B5-C7-D54
A2-B6-C7-D54
A3-B6-C7-D54
A9-B6-C7-D54
A13-B6-C7-D54
A24-B6-C7-D54
A69-B6-C7-D54
A67-B6-C7-D54
A39-B6-C7-D54
A65-B6-C7-D54
A66-B6-C7-D54
A2-B32-C7-D54
A3-B32-C7-D54
A9-B32-C7-D54
A13-B32-C7-D54
A24-B32-C7-D54
A69-B32-C7-D54
A67-B32-C7-D54
A39-B32-C7-D54
A65-B32-C7-D54
A66-B32-C7-D54
A2-B39-C7-D54
A3-B39-C7-D54
A9-B39-C7-D54

-continued
A13-B39-C7-D54
A24-B39-C7-D54
A69-B39-C7-D54
A67-B39-C7-D54
A39-B39-C7-D54
A65-B39-C7-D54
A66-B39-C7-D54
A2-B45-C7-D54
A3-B45-C7-D54
A9-B45-C7-D54
A13-B45-C7-D54
A24-B45-C7-D54
A69-B45-C7-D54
A67-B45-C7-D54
A39-B45-C7-D54
A65-B45-C7-D54
A66-B45-C7-D54
A2-B53-C7-D54
A3-B53-C7-D54
A9-B53-C7-D54
A13-B53-C7-D54
A24-B53-C7-D54
A69-B53-C7-D54
A67-B53-C7-D54
A39-B53-C7-D54
A65-B53-C7-D54
A66-B53-C7-D54
A2-B79-C7-D54
A3-B79-C7-D54
A9-B79-C7-D54
A13-B79-C7-D54
A24-B79-C7-D54
A69-B79-C7-D54
A67-B79-C7-D54
A39-B79-C7-D54
A65-B79-C7-D54
A66-B79-C7-D54
A2-B80-C7-D54
A3-B80-C7-D54
A9-B80-C7-D54
A13-B80-C7-D54
A24-B80-C7-D54
A69-B80-C7-D54
A67-B80-C7-D54
A39-B80-C7-D54
A65-B80-C7-D54
A66-B80-C7-D54
A2-B85-C7-D54
A3-B85-C7-D54
A9-B85-C7-D54
A13-B85-C7-D54
A24-B85-C7-D54
A69-B85-C7-D54
A67-B85-C7-D54
A39-B85-C7-D54
A65-B85-C7-D54
A66-B85-C7-D54
A2-B86-C7-D54
A3-B86-C7-D54
A9-B86-C7-D54
A13-B86-C7-D54
A24-B86-C7-D54
A69-B86-C7-D54
A67-B86-C7-D54
A39-B86-C7-D54
A65-B86-C7-D54
A66-B86-C7-D54
A2-B87-C7-D54
A3-B87-C7-D54
A9-B87-C7-D54
A13-B87-C7-D54
A24-B87-C7-D54
A69-B87-C7-D54
A67-B87-C7-D54
A39-B87-C7-D54
A65-B87-C7-D54
A66-B87-C7-D54
A2-B89-C7-D54
A3-B89-C7-D54
A9-B89-C7-D54

-continued
A13-B89-C7-D54
A24-B89-C7-D54
A69-B89-C7-D54
A67-B89-C7-D54
A39-B89-C7-D54
A65-B89-C7-D54
A66-B89-C7-D54
A2-B92-C7-D54
A3-B92-C7-D54
A9-B92-C7-D54
A13-B92-C7-D54
A24-B92-C7-D54
A69-B92-C7-D54
A67-B92-C7-D54
A39-B92-C7-D54
A65-B92-C7-D54
A66-B92-C7-D54
A2-B4-C8-D54
A3-B4-C8-D54
A9-B4-C8-D54
A13-B4-C8-D54
A24-B4-C8-D54
A69-B4-C8-D54
A67-B4-C8-D54
A39-B4-C8-D54
A65-B4-C8-D54
A66-B4-C8-D54
A2-B5-C8-D54
A3-B5-C8-D54
A9-B5-C8-D54
A13-B5-C8-D54
A24-B5-C8-D54
A69-B5-C8-D54
A67-B5-C8-D54
A39-B5-C8-D54
A65-B5-C8-D54
A66-B5-C8-D54
A2-B6-C8-D54
A3-B6-C8-D54
A9-B6-C8-D54
A13-B6-C8-D54
A24-B6-C8-D54
A69-B6-C8-D54
A67-B6-C8-D54
A39-B6-C8-D54
A65-B6-C8-D54
A66-B6-C8-D54
A2-B32-C8-D54
A3-B32-C8-D54
A9-B32-C8-D54
A13-B32-C8-D54
A24-B32-C8-D54
A69-B32-C8-D54
A67-B32-C8-D54
A39-B32-C8-D54
A65-B32-C8-D54
A66-B32-C8-D54
A2-B39-C8-D54
A3-B39-C8-D54
A9-B39-C8-D54
A13-B39-C8-D54
A24-B39-C8-D54
A69-B39-C8-D54
A67-B39-C8-D54
A39-B39-C8-D54
A65-B39-C8-D54
A66-B39-C8-D54
A2-B45-C8-D54
A3-B45-C8-D54
A9-B45-C8-D54
A13-B45-C8-D54
A24-B45-C8-D54
A69-B45-C8-D54
A67-B45-C8-D54
A39-B45-C8-D54
A65-B45-C8-D54
A66-B45-C8-D54
A2-B53-C8-D54
A3-B53-C8-D54
A9-B53-C8-D54

-continued

A13-B53-C8-D54
A24-B53-C8-D54
A69-B53-C8-D54
A67-B53-C8-D54
A39-B53-C8-D54
A65-B53-C8-D54
A66-B53-C8-D54
A2-B79-C8-D54
A3-B79-C8-D54
A9-B79-C8-D54
A13-B79-C8-D54
A24-B79-C8-D54
A69-B79-C8-D54
A67-B79-C8-D54
A39-B79-C8-D54
A65-B79-C8-D54
A66-B79-C8-D54
A2-B80-C8-D54
A3-B80-C8-D54
A9-B80-C8-D54
A13-B80-C8-D54
A24-B80-C8-D54
A69-B80-C8-D54
A67-B80-C8-D54
A39-B80-C8-D54
A65-B80-C8-D54
A66-B80-C8-D54
A2-B85-C8-D54
A3-B85-C8-D54
A9-B85-C8-D54
A13-B85-C8-D54
A24-B85-C8-D54
A69-B85-C8-D54
A67-B85-C8-D54
A39-B85-C8-D54
A65-B85-C8-D54
A66-B85-C8-D54
A2-B86-C8-D54
A3-B86-C8-D54
A9-B86-C8-D54
A13-B86-C8-D54
A24-B86-C8-D54
A69-B86-C8-D54
A67-B86-C8-D54
A39-B86-C8-D54
A65-B86-C8-D54
A66-B86-C8-D54
A2-B87-C8-D54
A3-B87-C8-D54
A9-B87-C8-D54
A13-B87-C8-D54
A24-B87-C8-D54
A69-B87-C8-D54
A67-B87-C8-D54
A39-B87-C8-D54
A65-B87-C8-D54
A66-B87-C8-D54
A2-B89-C8-D54
A3-B89-C8-D54
A9-B89-C8-D54
A13-B89-C8-D54
A24-B89-C8-D54
A69-B89-C8-D54
A67-B89-C8-D54
A39-B89-C8-D54
A65-B89-C8-D54
A66-B89-C8-D54
A2-B92-C8-D54
A3-B92-C8-D54
A9-B92-C8-D54
A13-B92-C8-D54
A24-B92-C8-D54
A69-B92-C8-D54
A67-B92-C8-D54
A39-B92-C8-D54
A65-B92-C8-D54
A66-B92-C8-D54
A2-B4-C9-D54
A3-B4-C9-D54
A9-B4-C9-D54

-continued

A13-B4-C9-D54
A24-B4-C9-D54
A69-B4-C9-D54
A67-B4-C9-D54
A39-B4-C9-D54
A65-B4-C9-D54
A66-B4-C9-D54
A2-B5-C9-D54
A3-B5-C9-D54
A9-B5-C9-D54
A13-B5-C9-D54
A24-B5-C9-D54
A69-B5-C9-D54
A67-B5-C9-D54
A39-B5-C9-D54
A65-B5-C9-D54
A66-B5-C9-D54
A2-B6-C9-D54
A3-B6-C9-D54
A9-B6-C9-D54
A13-B6-C9-D54
A24-B6-C9-D54
A69-B6-C9-D54
A67-B6-C9-D54
A39-B6-C9-D54
A65-B6-C9-D54
A66-B6-C9-D54
A2-B32-C9-D54
A3-B32-C9-D54
A9-B32-C9-D54
A13-B32-C9-D54
A24-B32-C9-D54
A69-B32-C9-D54
A67-B32-C9-D54
A39-B32-C9-D54
A65-B32-C9-D54
A66-B32-C9-D54
A2-B39-C9-D54
A3-B39-C9-D54
A9-B39-C9-D54
A13-B39-C9-D54
A24-B39-C9-D54
A69-B39-C9-D54
A67-B39-C9-D54
A39-B39-C9-D54
A65-B39-C9-D54
A66-B39-C9-D54
A2-B45-C9-D54
A3-B45-C9-D54
A9-B45-C9-D54
A13-B45-C9-D54
A24-B45-C9-D54
A69-B45-C9-D54
A67-B45-C9-D54
A39-B45-C9-D54
A65-B45-C9-D54
A66-B45-C9-D54
A2-B53-C9-D54
A3-B53-C9-D54
A9-B53-C9-D54
A13-B53-C9-D54
A24-B53-C9-D54
A69-B53-C9-D54
A67-B53-C9-D54
A39-B53-C9-D54
A65-B53-C9-D54
A66-B53-C9-D54
A2-B79-C9-D54
A3-B79-C9-D54
A9-B79-C9-D54
A13-B79-C9-D54
A24-B79-C9-D54
A69-B79-C9-D54
A67-B79-C9-D54
A39-B79-C9-D54
A65-B79-C9-D54
A66-B79-C9-D54
A2-B80-C9-D54
A3-B80-C9-D54
A9-B80-C9-D54

-continued
A13-B80-C9-D54
A24-B80-C9-D54
A69-B80-C9-D54
A67-B80-C9-D54
A39-B80-C9-D54
A65-B80-C9-D54
A66-B80-C9-D54
A2-B85-C9-D54
A3-B85-C9-D54
A9-B85-C9-D54
A13-B85-C9-D54
A24-B85-C9-D54
A69-B85-C9-D54
A67-B85-C9-D54
A39-B85-C9-D54
A65-B85-C9-D54
A66-B85-C9-D54
A2-B86-C9-D54
A3-B86-C9-D54
A9-B86-C9-D54
A13-B86-C9-D54
A24-B86-C9-D54
A69-B86-C9-D54
A67-B86-C9-D54
A39-B86-C9-D54
A65-B86-C9-D54
A66-B86-C9-D54
A2-B87-C9-D54
A3-B87-C9-D54
A9-B87-C9-D54
A13-B87-C9-D54
A24-B87-C9-D54
A69-B87-C9-D54
A67-B87-C9-D54
A39-B87-C9-D54
A65-B87-C9-D54
A66-B87-C9-D54
A2-B89-C9-D54
A3-B89-C9-D54
A9-B89-C9-D54
A13-B89-C9-D54
A24-B89-C9-D54
A69-B89-C9-D54
A67-B89-C9-D54
A39-B89-C9-D54
A65-B89-C9-D54
A66-B89-C9-D54
A2-B92-C9-D54
A3-B92-C9-D54
A9-B92-C9-D54
A13-B92-C9-D54
A24-B92-C9-D54
A69-B92-C9-D54
A67-B92-C9-D54
A39-B92-C9-D54
A65-B92-C9-D54
A66-B92-C9-D54
A2-B4-C10-D54
A3-B4-C10-D54
A9-B4-C10-D54
A13-B4-C10-D54
A24-B4-C10-D54
A69-B4-C10-D54
A67-B4-C10-D54
A39-B4-C10-D54
A65-B4-C10-D54
A66-B4-C10-D54
A2-B5-C10-D54
A3-B5-C10-D54
A9-B5-C10-D54
A13-B5-C10-D54
A24-B5-C10-D54
A69-B5-C10-D54
A67-B5-C10-D54
A39-B5-C10-D54
A65-B5-C10-D54
A66-B5-C10-D54
A2-B6-C10-D54
A3-B6-C10-D54
A9-B6-C10-D54

-continued
A13-B6-C10-D54
A24-B6-C10-D54
A69-B6-C10-D54
A67-B6-C10-D54
A39-B6-C10-D54
A65-B6-C10-D54
A66-B6-C10-D54
A2-B32-C10-D54
A3-B32-C10-D54
A9-B32-C10-D54
A13-B32-C10-D54
A24-B32-C10-D54
A69-B32-C10-D54
A67-B32-C10-D54
A39-B32-C10-D54
A65-B32-C10-D54
A66-B32-C10-D54
A2-B39-C10-D54
A3-B39-C10-D54
A9-B39-C10-D54
A13-B39-C10-D54
A24-B39-C10-D54
A69-B39-C10-D54
A67-B39-C10-D54
A39-B39-C10-D54
A65-B39-C10-D54
A66-B39-C10-D54
A2-B45-C10-D54
A3-B45-C10-D54
A9-B45-C10-D54
A13-B45-C10-D54
A24-B45-C10-D54
A69-B45-C10-D54
A67-B45-C10-D54
A39-B45-C10-D54
A65-B45-C10-D54
A66-B45-C10-D54
A2-B53-C10-D54
A3-B53-C10-D54
A9-B53-C10-D54
A13-B53-C10-D54
A24-B53-C10-D54
A69-B53-C10-D54
A67-B53-C10-D54
A39-B53-C10-D54
A65-B53-C10-D54
A66-B53-C10-D54
A2-B79-C10-D54
A3-B79-C10-D54
A9-B79-C10-D54
A13-B79-C10-D54
A24-B79-C10-D54
A69-B79-C10-D54
A67-B79-C10-D54
A39-B79-C10-D54
A65-B79-C10-D54
A66-B79-C10-D54
A2-B80-C10-D54
A3-B80-C10-D54
A9-B80-C10-D54
A13-B80-C10-D54
A24-B80-C10-D54
A69-B80-C10-D54
A67-B80-C10-D54
A39-B80-C10-D54
A65-B80-C10-D54
A66-B80-C10-D54
A2-B85-C10-D54
A3-B85-C10-D54
A9-B85-C10-D54
A13-B85-C10-D54
A24-B85-C10-D54
A69-B85-C10-D54
A67-B85-C10-D54
A39-B85-C10-D54
A65-B85-C10-D54
A66-B85-C10-D54
A2-B86-C10-D54
A3-B86-C10-D54
A9-B86-C10-D54

-continued

A13-B86-C10-D54
A24-B86-C10-D54
A69-B86-C10-D54
A67-B86-C10-D54
A39-B86-C10-D54
A65-B86-C10-D54
A66-B86-C10-D54
A2-B87-C10-D54
A3-B87-C10-D54
A9-B87-C10-D54
A13-B87-C10-D54
A24-B87-C10-D54
A69-B87-C10-D54
A67-B87-C10-D54
A39-B87-C10-D54
A65-B87-C10-D54
A66-B87-C10-D54
A2-B89-C10-D54
A3-B89-C10-D54
A9-B89-C10-D54
A13-B89-C10-D54
A24-B89-C10-D54
A69-B89-C10-D54
A67-B89-C10-D54
A39-B89-C10-D54
A65-B89-C10-D54
A66-B89-C10-D54
A2-B92-C10-D54
A3-B92-C10-D54
A9-B92-C10-D54
A13-B92-C10-D54
A24-B92-C10-D54
A69-B92-C10-D54
A67-B92-C10-D54
A39-B92-C10-D54
A65-B92-C10-D54
A66-B92-C10-D54
A2-B4-C11-D54
A3-B4-C11-D54
A9-B4-C11-D54
A13-B4-C11-D54
A24-B4-C11-D54
A69-B4-C11-D54
A67-B4-C11-D54
A39-B4-C11-D54
A65-B4-C11-D54
A66-B4-C11-D54
A2-B5-C11-D54
A3-B5-C11-D54
A9-B5-C11-D54
A13-B5-C11-D54
A24-B5-C11-D54
A69-B5-C11-D54
A67-B5-C11-D54
A39-B5-C11-D54
A65-B5-C11-D54
A66-B5-C11-D54
A2-B6-C11-D54
A3-B6-C11-D54
A9-B6-C11-D54
A13-B6-C11-D54
A24-B6-C11-D54
A69-B6-C11-D54
A67-B6-C11-D54
A39-B6-C11-D54
A65-B6-C11-D54
A66-B6-C11-D54
A2-B32-C11-D54
A3-B32-C11-D54
A9-B32-C11-D54
A13-B32-C11-D54
A24-B32-C11-D54
A69-B32-C11-D54
A67-B32-C11-D54
A39-B32-C11-D54
A65-B32-C11-D54
A66-B32-C11-D54
A2-B39-C11-D54
A3-B39-C11-D54
A9-B39-C11-D54

-continued

A13-B39-C11-D54
A24-B39-C11-D54
A69-B39-C11-D54
A67-B39-C11-D54
A39-B39-C11-D54
A65-B39-C11-D54
A66-B39-C11-D54
A2-B45-C11-D54
A3-B45-C11-D54
A9-B45-C11-D54
A13-B45-C11-D54
A24-B45-C11-D54
A69-B45-C11-D54
A67-B45-C11-D54
A39-B45-C11-D54
A65-B45-C11-D54
A66-B45-C11-D54
A2-B53-C11-D54
A3-B53-C11-D54
A9-B53-C11-D54
A13-B53-C11-D54
A24-B53-C11-D54
A69-B53-C11-D54
A67-B53-C11-D54
A39-B53-C11-D54
A65-B53-C11-D54
A66-B53-C11-D54
A2-B79-C11-D54
A3-B79-C11-D54
A9-B79-C11-D54
A13-B79-C11-D54
A24-B79-C11-D54
A69-B79-C11-D54
A67-B79-C11-D54
A39-B79-C11-D54
A65-B79-C11-D54
A66-B79-C11-D54
A2-B80-C11-D54
A3-B80-C11-D54
A9-B80-C11-D54
A13-B80-C11-D54
A24-B80-C11-D54
A69-B80-C11-D54
A67-B80-C11-D54
A39-B80-C11-D54
A65-B80-C11-D54
A66-B80-C11-D54
A2-B85-C11-D54
A3-B85-C11-D54
A9-B85-C11-D54
A13-B85-C11-D54
A24-B85-C11-D54
A69-B85-C11-D54
A67-B85-C11-D54
A39-B85-C11-D54
A65-B85-C11-D54
A66-B85-C11-D54
A2-B86-C11-D54
A3-B86-C11-D54
A9-B86-C11-D54
A13-B86-C11-D54
A24-B86-C11-D54
A69-B86-C11-D54
A67-B86-C11-D54
A39-B86-C11-D54
A65-B86-C11-D54
A66-B86-C11-D54
A2-B87-C11-D54
A3-B87-C11-D54
A9-B87-C11-D54
A13-B87-C11-D54
A24-B87-C11-D54
A69-B87-C11-D54
A67-B87-C11-D54
A39-B87-C11-D54
A65-B87-C11-D54
A66-B87-C11-D54
A2-B89-C11-D54
A3-B89-C11-D54
A9-B89-C11-D54

-continued

A13-B89-C11-D54
A24-B89-C11-D54
A69-B89-C11-D54
A67-B89-C11-D54
A39-B89-C11-D54
A65-B89-C11-D54
A66-B89-C11-D54
A2-B92-C11-D54
A3-B92-C11-D54
A9-B92-C11-D54
A13-B92-C11-D54
A24-B92-C11-D54
A69-B92-C11-D54
A67-B92-C11-D54
A39-B92-C11-D54
A65-B92-C11-D54
A66-B92-C11-D54
A2-B4-C12-D54
A3-B4-C12-D54
A9-B4-C12-D54
A13-B4-C12-D54
A24-B4-C12-D54
A69-B4-C12-D54
A67-B4-C12-D54
A39-B4-C12-D54
A65-B4-C12-D54
A66-B4-C12-D54
A2-B5-C12-D54
A3-B5-C12-D54
A9-B5-C12-D54
A13-B5-C12-D54
A24-B5-C12-D54
A69-B5-C12-D54
A67-B5-C12-D54
A39-B5-C12-D54
A65-B5-C12-D54
A66-B5-C12-D54
A2-B6-C12-D54
A3-B6-C12-D54
A9-B6-C12-D54
A13-B6-C12-D54
A24-B6-C12-D54
A69-B6-C12-D54
A67-B6-C12-D54
A39-B6-C12-D54
A65-B6-C12-D54
A66-B6-C12-D54
A2-B32-C12-D54
A3-B32-C12-D54
A9-B32-C12-D54
A13-B32-C12-D54
A24-B32-C12-D54
A69-B32-C12-D54
A67-B32-C12-D54
A39-B32-C12-D54
A65-B32-C12-D54
A66-B32-C12-D54
A2-B39-C12-D54
A3-B39-C12-D54
A9-B39-C12-D54
A13-B39-C12-D54
A24-B39-C12-D54
A69-B39-C12-D54
A67-B39-C12-D54
A39-B39-C12-D54
A65-B39-C12-D54
A66-B39-C12-D54
A2-B45-C12-D54
A3-B45-C12-D54
A9-B45-C12-D54
A13-B45-C12-D54
A24-B45-C12-D54
A69-B45-C12-D54
A67-B45-C12-D54
A39-B45-C12-D54
A65-B45-C12-D54
A66-B45-C12-D54
A2-B53-C12-D54
A3-B53-C12-D54
A9-B53-C12-D54

-continued

A13-B53-C12-D54
A24-B53-C12-D54
A69-B53-C12-D54
A67-B53-C12-D54
A39-B53-C12-D54
A65-B53-C12-D54
A66-B53-C12-D54
A2-B79-C12-D54
A3-B79-C12-D54
A9-B79-C12-D54
A13-B79-C12-D54
A24-B79-C12-D54
A69-B79-C12-D54
A67-B79-C12-D54
A39-B79-C12-D54
A65-B79-C12-D54
A66-B79-C12-D54
A2-B80-C12-D54
A3-B80-C12-D54
A9-B80-C12-D54
A13-B80-C12-D54
A24-B80-C12-D54
A69-B80-C12-D54
A67-B80-C12-D54
A39-B80-C12-D54
A65-B80-C12-D54
A66-B80-C12-D54
A2-B85-C12-D54
A3-B85-C12-D54
A9-B85-C12-D54
A13-B85-C12-D54
A24-B85-C12-D54
A69-B85-C12-D54
A67-B85-C12-D54
A39-B85-C12-D54
A65-B85-C12-D54
A66-B85-C12-D54
A2-B86-C12-D54
A3-B86-C12-D54
A9-B86-C12-D54
A13-B86-C12-D54
A24-B86-C12-D54
A69-B86-C12-D54
A67-B86-C12-D54
A39-B86-C12-D54
A65-B86-C12-D54
A66-B86-C12-D54
A2-B87-C12-D54
A3-B87-C12-D54
A9-B87-C12-D54
A13-B87-C12-D54
A24-B87-C12-D54
A69-B87-C12-D54
A67-B87-C12-D54
A39-B87-C12-D54
A65-B87-C12-D54
A66-B87-C12-D54
A2-B89-C12-D54
A3-B89-C12-D54
A9-B89-C12-D54
A13-B89-C12-D54
A24-B89-C12-D54
A69-B89-C12-D54
A67-B89-C12-D54
A39-B89-C12-D54
A65-B89-C12-D54
A66-B89-C12-D54
A2-B92-C12-D54
A3-B92-C12-D54
A9-B92-C12-D54
A13-B92-C12-D54
A24-B92-C12-D54
A69-B92-C12-D54
A67-B92-C12-D54
A39-B92-C12-D54
A65-B92-C12-D54
A66-B92-C12-D54
A2-B4-C13-D54
A3-B4-C13-D54
A9-B4-C13-D54

-continued

A13-B4-C13-D54
A24-B4-C13-D54
A69-B4-C13-D54
A67-B4-C13-D54
A39-B4-C13-D54
A65-B4-C13-D54
A66-B4-C13-D54
A2-B5-C13-D54
A3-B5-C13-D54
A9-B5-C13-D54
A13-B5-C13-D54
A24-B5-C13-D54
A69-B5-C13-D54
A67-B5-C13-D54
A39-B5-C13-D54
A65-B5-C13-D54
A66-B5-C13-D54
A2-B6-C13-D54
A3-B6-C13-D54
A9-B6-C13-D54
A13-B6-C13-D54
A24-B6-C13-D54
A69-B6-C13-D54
A67-B6-C13-D54
A39-B6-C13-D54
A65-B6-C13-D54
A66-B6-C13-D54
A2-B32-C13-D54
A3-B32-C13-D54
A9-B32-C13-D54
A13-B32-C13-D54
A24-B32-C13-D54
A69-B32-C13-D54
A67-B32-C13-D54
A39-B32-C13-D54
A65-B32-C13-D54
A66-B32-C13-D54
A2-B39-C13-D54
A3-B39-C13-D54
A9-B39-C13-D54
A13-B39-C13-D54
A24-B39-C13-D54
A69-B39-C13-D54
A67-B39-C13-D54
A39-B39-C13-D54
A65-B39-C13-D54
A66-B39-C13-D54
A2-B45-C13-D54
A3-B45-C13-D54
A9-B45-C13-D54
A13-B45-C13-D54
A24-B45-C13-D54
A69-B45-C13-D54
A67-B45-C13-D54
A39-B45-C13-D54
A65-B45-C13-D54
A66-B45-C13-D54
A2-B53-C13-D54
A3-B53-C13-D54
A9-B53-C13-D54
A13-B53-C13-D54
A24-B5 3-C13-D54
A69-B53-C13-D54
A67-B53-C13-D54
A39-B53-C13-D54
A65-B53-C13-D54
A66-B53-C13-D54
A2-B79-C13-D54
A3-B79-C13-D54
A9-B79-C13-D54
A13-B79-C13-D54
A24-B79-C13-D54
A69-B79-C13-D54
A67-B79-C13-D54
A39-B79-C13-D54
A65-B79-C13-D54
A66-B79-C13-D54
A2-B80-C13-D54
A3-B80-C13-D54
A9-B80-C13-D54

-continued

A13-B80-C13-D54
A24-B80-C13-D54
A69-B80-C13-D54
A67-B80-C13-D54
A39-B80-C13-D54
A65-B80-C13-D54
A66-B80-C13-D54
A2-B85-C13-D54
A3-B85-C13-D54
A9-B85-C13-D54
A13-B85-C13-D54
A24-B85-C13-D54
A69-B85-C13-D54
A67-B85-C13-D54
A39-B85-C13-D54
A65-B85-C13-D54
A66-B85-C13-D54
A2-B86-C13-D54
A3-B86-C13-D54
A9-B86-C13-D54
A13-B86-C13-D54
A24-B86-C13-D54
A69-B86-C13-D54
A67-B86-C13-D54
A39-B86-C13-D54
A65-B86-C13-D54
A66-B86-C13-D54
A2-B87-C13-D54
A3-B87-C13-D54
A9-B87-C13-D54
A13-B87-C13-D54
A24-B87-C13-D54
A69-B87-C13-D54
A67-B87-C13-D54
A39-B87-C13-D54
A65-B87-C13-D54
A66-B87-C13-D54
A2-B89-C13-D54
A3-B89-C13-D54
A9-B89-C13-D54
A13-B89-C13-D54
A24-B89-C13-D54
A69-B89-C13-D54
A67-B89-C13-D54
A39-B89-C13-D54
A65-B89-C13-D54
A66-B89-C13-D54
A2-B92-C13-D54
A3-B92-C13-D54
A9-B92-C13-D54
A13-B92-C13-D54
A24-B92-C13-D54
A69-B92-C13-D54
A67-B92-C13-D54
A39-B92-C13-D54
A65-B92-C13-D54
A66-B92-C13-D54
A2-B4-C1-D55
A3-B4-C1-D55
A9-B4-C1-D55
A13-B4-C1-D55
A24-B4-C1-D55
A69-B4-C1-D55
A67-B4-C1-D55
A39-B4-C1-D55
A65-B4-C1-D55
A66-B4-C1-D55
A2-B5-C1-D55
A3-B5-C1-D55
A9-B5-C1-D55
A13-B5-C1-D55
A24-B5-C1-D55
A69-B5-C1-D55
A67-B5-C1-D55
A39-B5-C1-D55
A65-B5-C1-D55
A66-B5-C1-D55
A2-B6-CL-D55
A3-B6-C1-D55
A9-B6-C1-D55

-continued
A13-B6-C1-D55
A24-B6-C1-D55
A69-B6-C1-D55
A67-B6-C1-D55
A39-B6-C1-D55
A65-B6-C1-D55
A66-B6-C1-D55
A2-B32-C1-D55
A3-B32-C1-D55
A9-B32-C1-D55
A13-B32-C1-D55
A24-B32-C1-D55
A69-B32-C1-D55
A67-B32-C1-D55
A39-B32-C1-D55
A65-B32-C1-D55
A66-B32-C1-D55
A2-B39-C1-D55
A3-B39-C1-D55
A9-B39-C1-D55
A13-B39-C1-D55
A24-B39-C1-D55
A69-B39-C1-D55
A67-B39-C1-D55
A39-B39-C1-D55
A65-B39-C1-D55
A66-B39-C1-D55
A2-B45-C1-D55
A3-B45-C1-D55
A9-B45-C1-D55
A13-B45-C1-D55
A24-B45-C1-D55
A69-B45-C1-D55
A67-B45-C1-D55
A39-B45-C1-D55
A65-B45-C1-D55
A66-B45-C1-D55
A2-B53-C1-D55
A3-B53-C1-D55
A9-B53-C1-D55
A13-B53-C1-D55
A24-B53-C1-D55
A69-B53-C1-D55
A67-B53-C1-D55
A39-B53-C1-D55
A65-B53-C1-D55
A66-B53-C1-D55
A2-B79-C1-D55
A3-B79-C1-D55
A9-B79-C1-D55
A13-B79-C1-D55
A24-B79-C1-D55
A69-B79-C1-D55
A67-B79-C1-D55
A39-B79-C1-D55
A65-B79-C1-D55
A66-B79-C1-D55
A2-B80-C1-D55
A3-B80-C1-D55
A9-B80-C1-D55
A13-B80-C1-D55
A24-B80-C1-D55
A69-B80-C1-D55
A67-B80-C1-D55
A39-B80-C1-D55
A65-B80-C1-D55
A66-B80-C1-D55
A2-B85-C1-D55
A3-B85-C1-D55
A9-B85-C1-D55
A13-B85-C1-D55
A24-B85-C1-D55
A69-B85-C1-D55
A67-B85-C1-D55
A39-B85-C1-D55
A65-B85-C1-D55
A66-B85-C1-D55
A2-B86-C1-D55
A3-B86-C1-D55
A9-B86-C1-D55

-continued
A13-B86-C1-D55
A24-B86-C1-D55
A69-B86-C1-D55
A67-B86-C1-D55
A39-B86-C1-D55
A65-B86-C1-D55
A66-B86-C1-D55
A2-B86-C1-D55
A3-B86-C1-D55
A9-B87-C1-D55
A13-B87-C1-D55
A24-B87-C1-D55
A69-B87-C1-D55
A67-B87-C1-D55
A39-B87-C1-D55
A65-B87-C1-D55
A66-B87-C1-D55
A2-B89-C1-D55
A3-B89-C1-D55
A9-B89-C1-D55
A13-B89-C1-D55
A24-B89-C1-D55
A69-B89-C1-D55
A67-B89-C1-D55
A39-B89-C1-D55
A65-B89-C1-D55
A66-B89-C1-D55
A2-B92-C1-D55
A3-B92-C1-D55
A9-B92-C1-D55
A13-B92-C1-D55
A24-B92-C1-D55
A69-B92-C1-D55
A67-B92-C1-D55
A39-B92-C1-D55
A65-B92-C1-D55
A66-B92-C1-D55
A2-B4-C2-D55
A3-B4-C2-D55
A9-B4-C2-D55
A13-B4-C2-D55
A24-B4-C2-D55
A69-B4-C2-D55
A67-B4-C2-D55
A39-B4-C2-D55
A65-B4-C2-D55
A66-B4-C2-D55
A2-B5-C2-D55
A3-B5-C2-D55
A9-B5-C2-D55
A13-B5-C2-D55
A24-B5-C2-D55
A69-B5-C2-D55
A67-B5-C2-D55
A39-B5-C2-D55
A65-B5-C2-D55
A66-B5-C2-D55
A2-B6-C2-D55
A3-B6-C2-D55
A9-B6-C2-D55
A13-B6-C2-D55
A24-B6-C2-D55
A69-B6-C2-D55
A67-B6-C2-D55
A39-B6-C2-D55
A65-B6-C2-D55
A66-B6-C2-D55
A2-B32-C2-D55
A3-B32-C2-D55
A9-B32-C2-D55
A13-B32-C2-D55
A24-B32-C2-D55
A69-B32-C2-D55
A67-B32-C2-D55
A39-B32-C2-D55
A65-B32-C2-D55
A66-B32-C2-D55
A2-B39-C2-D55
A3-B39-C2-D55
A9-B39-C2-D55

1301

-continued
A13-B39-C2-D55
A24-B39-C2-D55
A69-B39-C2-D55
A67-B39-C2-D55
A39-B39-C2-D55
A65-B39-C2-D55
A66-B39-C2-D55
A2-B45-C2-D55
A3-B45-C2-D55
A9-B45-C2-D55
A13-B45-C2-D55
A24-B45-C2-D55
A69-B45-C2-D55
A67-B45-C2-D55
A39-B45-C2-D55
A65-B45-C2-D55
A66-B45-C2-D55
A2-B53-C2-D55
A3-B53-C2-D55
A9-B53-C2-D55
A13-B53-C2-D55
A24-B53-C2-D55
A69-B53-C2-D55
A67-B53-C2-D55
A39-B53-C2-D55
A65-B53-C2-D55
A66-B53-C2-D55
A2-B79-C2-D55
A3-B79-C2-D55
A9-B79-C2-D55
A13-B79-C2-D55
A24-B79-C2-D55
A69-B79-C2-D55
A67-B79-C2-D55
A39-B79-C2-D55
A65-B79-C2-D55
A66-B79-C2-D55
A2-B80-C2-D55
A3-B80-C2-D55
A9-B80-C2-D55
A13-B80-C2-D55
A24-B80-C2-D55
A69-B80-C2-D55
A67-B80-C2-D55
A39-B80-C2-D55
A65-B80-C2-D55
A66-B80-C2-D55
A2-B85-C2-D55
A3-B85-C2-D55
A9-B85-C2-D55
A13-B85-C2-D55
A24-B85-C2-D55
A69-B85-C2-D55
A67-B85-C2-D55
A39-B85-C2-D55
A65-B85-C2-D55
A66-B85-C2-D55
A2-B86-C2-D55
A3-B86-C2-D55
A9-B86-C2-D55
A13-B86-C2-D55
A24-B86-C2-D55
A69-B86-C2-D55
A67-B86-C2-D55
A39-B86-C2-D55
A65-B86-C2-D55
A66-B86-C2-D55
A2-B87-C2-D55
A3-B87-C2-D55
A9-B87-C2-D55
A13-B87-C2-D55
A24-B87-C2-D55
A69-B87-C2-D55
A67-B87-C2-D55
A39-B87-C2-D55
A65-B87-C2-D55
A66-B87-C2-D55
A2-B89-C2-D55
A3-B89-C2-D55
A9-B89-C2-D55

1302

-continued
A13-B89-C2-D55
A24-B89-C2-D55
A69-B89-C2-D55
A67-B89-C2-D55
A39-B89-C2-D55
A65-B89-C2-D55
A66-B89-C2-D55
A2-B92-C2-D55
A3-B92-C2-D55
A9-B92-C2-D55
A13-B92-C2-D55
A24-B92-C2-D55
A69-B92-C2-D55
A67-B92-C2-D55
A39-B92-C2-D55
A65-B92-C2-D55
A66-B92-C2-D55
A2-B4-C3-D55
A3-B4-C3-D55
A9-B4-C3-D55
A13-B4-C3-D55
A24-B4-C3-D55
A69-B4-C3-D55
A67-B4-C3-D55
A39-B4-C3-D55
A65-B4-C3-D55
A66-B4-C3-D55
A2-B5-C3-D55
A3-B5-C3-D55
A9-B5-C3-D55
A13-B5-C3-D55
A24-B5-C3-D55
A69-B5-C3-D55
A67-B5-C3-D55
A39-B5-C3-D55
A65-B5-C3-D55
A66-B5-C3-D55
A2-B6-C3-D55
A3-B6-C3-D55
A9-B6-C3-D55
A13-B6-C3-D55
A24-B6-C3-D55
A69-B6-C3-D55
A67-B6-C3-D55
A39-B6-C3-D55
A65-B6-C3-D55
A66-B6-C3-D55
A2-B32-C3-D55
A3-B32-C3-D55
A9-B32-C3-D55
A13-B32-C3-D55
A24-B32-C3-D55
A69-B32-C3-D55
A67-B32-C3-D55
A39-B32-C3-D55
A65-B32-C3-D55
A66-B32-C3-D55
A2-B39-C3-D55
A3-B39-C3-D55
A9-B39-C3-D55
A13-B39-C3-D55
A24-B39-C3-D55
A69-B39-C3-D55
A67-B39-C3-D55
A39-B39-C3-D55
A65-B39-C3-D55
A66-B39-C3-D55
A2-B45-C3-D55
A3-B45-C3-D55
A9-B45-C3-D55
A13-B45-C3-D55
A24-B45-C3-D55
A69-B45-C3-D55
A67-B45-C3-D55
A39-B45-C3-D55
A65-B45-C3-D55
A66-B45-C3-D55
A2-B53-C3-D55
A3-B53-C3-D55
A9-B53-C3-D55

-continued
A13-B53-C3-D55
A24-B53-C3-D55
A69-B53-C3-D55
A67-B53-C3-D55
A39-B53-C3-D55
A65-B53-C3-D55
A66-B53-C3-D55
A2-B79-C3-D55
A3-B79-C3-D55
A9-B79-C3-D55
A13-B79-C3-D55
A24-B79-C3-D55
A69-B79-C3-D55
A67-B79-C3-D55
A39-B79-C3-D55
A65-B79-C3-D55
A66-B79-C3-D55
A2-B80-C3-D55
A3-B80-C3-D55
A9-B80-C3-D55
A13-B80-C3-D55
A24-B80-C3-D55
A69-B80-C3-D55
A67-B80-C3-D55
A39-B80-C3-D55
A65-B80-C3-D55
A66-B80-C3-D55
A2-B85-C3-D55
A3-B85-C3-D55
A9-B85-C3-D55
A13-B85-C3-D55
A24-B85-C3-D55
A69-B85-C3-D55
A67-B85-C3-D55
A39-B85-C3-D55
A65-B85-C3-D55
A66-B85-C3-D55
A2-B86-C3-D55
A3-B86-C3-D55
A9-B86-C3-D55
A13-B86-C3-D55
A24-B86-C3-D55
A69-B86-C3-D55
A67-B86-C3-D55
A39-B86-C3-D55
A65-B86-C3-D55
A66-B86-C3-D55
A2-B87-C3-D55
A3-B87-C3-D55
A9-B87-C3-D55
A13-B87-C3-D55
A24-B87-C3-D55
A69-B87-C3-D55
A67-B87-C3-D55
A39-B87-C3-D55
A65-B87-C3-D55
A66-B87-C3-D55
A2-B89-C3-D55
A3-B89-C3-D55
A9-B89-C3-D55
A13-B89-C3-D55
A24-B89-C3-D55
A69-B89-C3-D55
A67-B89-C3-D55
A39-B89-C3-D55
A65-B89-C3-D55
A66-B89-C3-D55
A2-B92-C3-D55
A3-B92-C3-D55
A9-B92-C3-D55
A13-B92-C3-D55
A24-B92-C3-D55
A69-B92-C3-D55
A67-B92-C3-D55
A39-B92-C3-D55
A65-B92-C3-D55
A66-B92-C3-D55
A2-B4-C4-D55
A3-B4-C4-D55
A9-B4-C4-D55

-continued
A13-B4-C4-D55
A24-B4-C4-D55
A69-B4-C4-D55
A67-B4-C4-D55
A39-B4-C4-D55
A65-B4-C4-D55
A66-B4-C4-D55
A2-B5-C4-D55
A3-B5-C4-D55
A9-B5-C4-D55
A13-B5-C4-D55
A24-B5-C4-D55
A69-B5-C4-D55
A67-B5-C4-D55
A39-B5-C4-D55
A65-B5-C4-D55
A66-B5-C4-D55
A2-B6-C4-D55
A3-B6-C4-D55
A9-B6-C4-D55
A13-B6-C4-D55
A24-B6-C4-D55
A69-B6-C4-D55
A67-B6-C4-D55
A39-B6-C4-D55
A65-B6-C4-D55
A66-B6-C4-D55
A2-B32-C4-D55
A3-B32-C4-D55
A9-B32-C4-D55
A13-B32-C4-D55
A24-B32-C4-D55
A69-B32-C4-D55
A67-B32-C4-D55
A39-B32-C4-D55
A65-B32-C4-D55
A66-B32-C4-D55
A2-B39-C4-D55
A3-B39-C4-D55
A9-B39-C4-D55
A13-B39-C4-D55
A24-B39-C4-D55
A69-B39-C4-D55
A67-B39-C4-D55
A39-B39-C4-D55
A65-B39-C4-D55
A66-B39-C4-D55
A2-B45-C4-D55
A3-B45-C4-D55
A9-B45-C4-D55
A13-B45-C4-D55
A24-B45-C4-D55
A69-B45-C4-D55
A67-B45-C4-D55
A39-B45-C4-D55
A65-B45-C4-D55
A66-B45-C4-D55
A2-B53-C4-D55
A3-B53-C4-D55
A9-B53-C4-D55
A13-B53-C4-D55
A24-B53-C4-D55
A69-B53-C4-D55
A67-B53-C4-D55
A39-B53-C4-D55
A65-B53-C4-D55
A66-B53-C4-D55
A2-B79-C4-D55
A3-B79-C4-D55
A9-B79-C4-D55
A13-B79-C4-D55
A24-B79-C4-D55
A69-B79-C4-D55
A67-B79-C4-D55
A39-B79-C4-D55
A65-B79-C4-D55
A66-B79-C4-D55
A2-B80-C4-D55
A3-B80-C4-D55
A9-B80-C4-D55

-continued

A13-B80-C4-D55
A24-B80-C4-D55
A69-B80-C4-D55
A67-B80-C4-D55
A39-B80-C4-D55
A65-B80-C4-D55
A66-B80-C4-D55
A2-B85-C4-D55
A3-B85-C4-D55
A9-B85-C4-D55
A13-B85-C4-D55
A24-B85-C4-D55
A69-B85-C4-D55
A67-B85-C4-D55
A39-B85-C4-D55
A65-B85-C4-D55
A66-B85-C4-D55
A2-B86-C4-D55
A3-B86-C4-D55
A9-B86-C4-D55
A13-B86-C4-D55
A24-B86-C4-D55
A69-B86-C4-D55
A67-B86-C4-D55
A39-B86-C4-D55
A65-B86-C4-D55
A66-B86-C4-D55
A2-B87-C4-D55
A3-B87-C4-D55
A9-B87-C4-D55
A13-B87-C4-D55
A24-B87-C4-D55
A69-B87-C4-D55
A67-B87-C4-D55
A39-B87-C4-D55
A65-B87-C4-D55
A66-B87-C4-D55
A2-B89-C4-D55
A3-B89-C4-D55
A9-B89-C4-D55
A13-B89-C4-D55
A24-B89-C4-D55
A69-B89-C4-D55
A67-B89-C4-D55
A39-B89-C4-D55
A65-B89-C4-D55
A66-B89-C4-D55
A2-B92-C4-D55
A3-B92-C4-D55
A9-B92-C4-D55
A13-B92-C4-D55
A24-B92-C4-D55
A69-B92-C4-D55
A67-B92-C4-D55
A39-B92-C4-D55
A65-B92-C4-D55
A66-B92-C4-D55
A2-B4-C5-D55
A3-B4-C5-D55
A9-B4-C5-D55
A13-B4-C5-D55
A24-B4-C5-D55
A69-B4-C5-D55
A67-B4-C5-D55
A39-B4-C5-D55
A65-B4-C5-D55
A66-B4-C5-D55
A2-B5-C5-D55
A3-B5-C5-D55
A9-B5-C5-D55
A13-B5-C5-D55
A24-B5-C5-D55
A69-B5-C5-D55
A67-B5-C5-D55
A39-B5-C5-D55
A65-B5-C5-D55
A66-B5-C5-D55
A2-B6-C5-D55
A3-B6-C5-D55
A9-B6-C5-D55

-continued

A13-B6-C5-D55
A24-B6-C5-D55
A69-B6-C5-D55
A67-B6-C5-D55
A39-B6-C5-D55
A65-B6-C5-D55
A66-B6-C5-D55
A2-B32-C5-D55
A3-B32-C5-D55
A9-B32-C5-D55
A13-B32-C5-D55
A24-B32-C5-D55
A69-B32-C5-D55
A67-B32-C5-D55
A39-B32-C5-D55
A65-B32-C5-D55
A66-B32-C5-D55
A2-B39-C5-D55
A3-B39-C5-D55
A9-B39-C5-D55
A13-B39-C5-D55
A24-B39-C5-D55
A69-B39-C5-D55
A67-B39-C5-D55
A39-B39-C5-D55
A65-B39-C5-D55
A66-B39-C5-D55
A2-B45-C5-D55
A3-B45-C5-D55
A9-B45-C5-D55
A13-B45-C5-D55
A24-B45-C5-D55
A69-B45-C5-D55
A67-B45-C5-D55
A39-B45-C5-D55
A65-B45-C5-D55
A66-B45-C5-D55
A2-B53-C5-D55
A3-B53-C5-D55
A9-B53-C5-D55
A13-B53-C5-D55
A24-B53-C5-D55
A69-B53-C5-D55
A67-B53-C5-D55
A39-B53-C5-D55
A65-B53-C5-D55
A66-B53-C5-D55
A2-B79-C5-D55
A3-B79-C5-D55
A9-B79-C5-D55
A13-B79-C5-D55
A24-B79-C5-D55
A69-B79-C5-D55
A67-B79-C5-D55
A39-B79-C5-D55
A65-B79-C5-D55
A66-B79-C5-D55
A2-B80-C5-D55
A3-B80-C5-D55
A9-B80-C5-D55
A13-B80-C5-D55
A24-B80-C5-D55
A69-B80-C5-D55
A67-B80-C5-D55
A39-B80-C5-D55
A65-B80-C5-D55
A66-B80-C5-D55
A2-B85-C5-D55
A3-B85-C5-D55
A9-B85-C5-D55
A13-B85-C5-D55
A24-B85-C5-D55
A69-B85-C5-D55
A67-B85-C5-D55
A39-B85-C5-D55
A65-B85-C5-D55
A66-B85-C5-D55
A2-B86-C5-D55
A3-B86-C5-D55
A9-B86-C5-D55

1307

-continued

A13-B86-C5-D55
A24-B86-C5-D55
A69-B86-C5-D55
A67-B86-C5-D55
A39-B86-C5-D55
A65-B86-C5-D55
A66-B86-C5-D55
A2-B87-C5-D55
A3-B87-C5-D55
A9-B87-C5-D55
A13-B87-C5-D55
A24-B87-C5-D55
A69-B87-C5-D55
A67-B87-C5-D55
A39-B87-C5-D55
A65-B87-C5-D55
A66-B87-C5-D55
A2-B89-C5-D55
A3-B89-C5-D55
A9-B89-C5-D55
A13-B89-C5-D55
A24-B89-C5-D55
A69-B89-C5-D55
A67-B89-C5-D55
A39-B89-C5-D55
A65-B89-C5-D55
A66-B89-C5-D55
A2-B92-C5-D55
A3-B92-C5-D55
A9-B92-C5-D55
A13-B92-C5-D55
A24-B92-C5-D55
A69-B92-C5-D55
A67-B92-C5-D55
A39-B92-C5-D55
A65-B92-C5-D55
A66-B92-C5-D55
A2-B4-C6-D55
A3-B4-C6-D55
A9-B4-C6-D55
A13-B4-C6-D55
A24-B4-C6-D55
A69-B4-C6-D55
A67-B4-C6-D55
A39-B4-C6-D55
A65-B4-C6-D55
A66-B4-C6-D55
A2-B5-C6-D55
A3-B5-C6-D55
A9-B5-C6-D55
A13-B5-C6-D55
A24-B5-C6-D55
A69-B5-C6-D55
A67-B5-C6-D55
A39-B5-C6-D55
A65-B5-C6-D55
A66-B5-C6-D55
A2-B6-C6-D55
A3-B6-C6-D55
A9-B6-C6-D55
A13-B6-C6-D55
A24-B6-C6-D55
A69-B6-C6-D55
A67-B6-C6-D55
A39-B6-C6-D55
A65-B6-C6-D55
A66-B6-C6-D55
A2-B32-C6-D55
A3-B32-C6-D55
A9-B32-C6-D55
A13-B32-C6-D55
A24-B32-C6-D55
A69-B32-C6-D55
A67-B32-C6-D55
A39-B32-C6-D55
A65-B32-C6-D55
A66-B32-C6-D55
A2-B39-C6-D55
A3-B39-C6-D55
A9-B39-C6-D55

1308

-continued

A13-B39-C6-D55
A24-B39-C6-D55
A69-B39-C6-D55
A67-B39-C6-D55
A39-B39-C6-D55
A65-B39-C6-D55
A66-B39-C6-D55
A2-B45-C6-D55
A3-B45-C6-D55
A9-B45-C6-D55
A13-B45-C6-D55
A24-B45-C6-D55
A69-B45-C6-D55
A67-B45-C6-D55
A39-B45-C6-D55
A65-B45-C6-D55
A66-B45-C6-D55
A2-B53-C6-D55
A3-B53-C6-D55
A9-B53-C6-D55
A13-B53-C6-D55
A24-B53-C6-D55
A69-B53-C6-D55
A67-B53-C6-D55
A39-B53-C6-D55
A65-B53-C6-D55
A66-B53-C6-D55
A2-B79-C6-D55
A3-B79-C6-D55
A9-B79-C6-D55
A13-B79-C6-D55
A24-B79-C6-D55
A69-B79-C6-D55
A67-B79-C6-D55
A39-B79-C6-D55
A65-B79-C6-D55
A66-B79-C6-D55
A2-B80-C6-D55
A3-B80-C6-D55
A9-B80-C6-D55
A13-B80-C6-D55
A24-B80-C6-D55
A69-B80-C6-D55
A67-B80-C6-D55
A39-B80-C6-D55
A65-B80-C6-D55
A66-B80-C6-D55
A2-B85-C6-D55
A3-B85-C6-D55
A9-B85-C6-D55
A13-B85-C6-D55
A24-B85-C6-D55
A69-B85-C6-D55
A67-B85-C6-D55
A39-B85-C6-D55
A65-B85-C6-D55
A66-B85-C6-D55
A2-B86-C6-D55
A3-B86-C6-D55
A9-B86-C6-D55
A13-B86-C6-D55
A24-B86-C6-D55
A69-B86-C6-D55
A67-B86-C6-D55
A39-B86-C6-D55
A65-B86-C6-D55
A66-B86-C6-D55
A2-B87-C6-D55
A3-B87-C6-D55
A9-B87-C6-D55
A13-B87-C6-D55
A24-B87-C6-D55
A69-B87-C6-D55
A67-B87-C6-D55
A39-B87-C6-D55
A65-B87-C6-D55
A66-B87-C6-D55
A2-B89-C6-D55
A3-B89-C6-D55
A9-B89-C6-D55

-continued
A13-B89-C6-D55
A24-B89-C6-D55
A69-B89-C6-D55
A67-B89-C6-D55
A39-B89-C6-D55
A65-B89-C6-D55
A66-B89-C6-D55
A2-B92-C6-D55
A3-B92-C6-D55
A9-B92-C6-D55
A13-B92-C6-D55
A24-B92-C6-D55
A69-B92-C6-D55
A67-B92-C6-D55
A39-B92-C6-D55
A65-B92-C6-D55
A66-B92-C6-D55
A2-B4-C7-D55
A3-B4-C7-D55
A9-B4-C7-D55
A13-B4-C7-D55
A24-B4-C7-D55
A69-B4-C7-D55
A67-B4-C7-D55
A39-B4-C7-D55
A65-B4-C7-D55
A66-B4-C7-D55
A2-B5-C7-D55
A3-B5-C7-D55
A9-B5-C7-D55
A13-B5-C7-D55
A24-B5-C7-D55
A69-B5-C7-D55
A67-B5-C7-D55
A39-B5-C7-D55
A65-B5-C7-D55
A66-B5-C7-D55
A2-B6-C7-D55
A3-B6-C7-D55
A9-B6-C7-D55
A13-B6-C7-D55
A24-B6-C7-D55
A69-B6-C7-D55
A67-B6-C7-D55
A39-B6-C7-D55
A65-B6-C7-D55
A66-B6-C7-D55
A2-B32-C7-D55
A3-B32-C7-D55
A9-B32-C7-D55
A13-B32-C7-D55
A24-B32-C7-D55
A69-B32-C7-D55
A67-B32-C7-D55
A39-B32-C7-D55
A65-B32-C7-D55
A66-B32-C7-D55
A2-B39-C7-D55
A3-B39-C7-D55
A9-B39-C7-D55
A13-B39-C7-D55
A24-B39-C7-D55
A69-B39-C7-D55
A67-B39-C7-D55
A39-B39-C7-D55
A65-B39-C7-D55
A66-B39-C7-D55
A2-B45-C7-D55
A3-B45-C7-D55
A9-B45-C7-D55
A13-B45-C7-D55
A24-B45-C7-D55
A69-B45-C7-D55
A67-B45-C7-D55
A39-B45-C7-D55
A65-B45-C7-D55
A66-B45-C7-D55
A2-B53-C7-D55
A3-B53-C7-D55
A9-B53-C7-D55

-continued
A13-B53-C7-D55
A24-B53-C7-D55
A69-B53-C7-D55
A67-B53-C7-D55
A39-B53-C7-D55
A65-B53-C7-D55
A66-B53-C7-D55
A2-B79-C7-D55
A3-B79-C7-D55
A9-B79-C7-D55
A13-B79-C7-D55
A24-B79-C7-D55
A69-B79-C7-D55
A67-B79-C7-D55
A39-B79-C7-D55
A65-B79-C7-D55
A66-B79-C7-D55
A2-B80-C7-D55
A3-B80-C7-D55
A9-B80-C7-D55
A13-B80-C7-D55
A24-B80-C7-D55
A69-B80-C7-D55
A67-B80-C7-D55
A39-B80-C7-D55
A65-B80-C7-D55
A66-B80-C7-D55
A2-B85-C7-D55
A3-B85-C7-D55
A9-B85-C7-D55
A13-B85-C7-D55
A24-B85-C7-D55
A69-B85-C7-D55
A67-B85-C7-D55
A39-B85-C7-D55
A65-B85-C7-D55
A66-B85-C7-D55
A2-B86-C7-D55
A3-B86-C7-D55
A9-B86-C7-D55
A13-B86-C7-D55
A24-B86-C7-D55
A69-B86-C7-D55
A67-B86-C7-D55
A39-B86-C7-D55
A65-B86-C7-D55
A66-B86-C7-D55
A2-B87-C7-D55
A3-B87-C7-D55
A9-B87-C7-D55
A13-B87-C7-D55
A24-B87-C7-D55
A69-B87-C7-D55
A67-B87-C7-D55
A39-B87-C7-D55
A65-B87-C7-D55
A66-B87-C7-D55
A2-B89-C7-D55
A3-B89-C7-D55
A9-B89-C7-D55
A13-B89-C7-D55
A24-B89-C7-D55
A69-B89-C7-D55
A67-B89-C7-D55
A39-B89-C7-D55
A65-B89-C7-D55
A66-B89-C7-D55
A2-B92-C7-D55
A3-B92-C7-D55
A9-B92-C7-D55
A13-B92-C7-D55
A24-B92-C7-D55
A69-B92-C7-D55
A67-B92-C7-D55
A39-B92-C7-D55
A65-B92-C7-D55
A66-B92-C7-D55
A2-B4-C8-D55
A3-B4-C8-D55
A9-B4-C8-D55

-continued

A13-B4-C8-D55
A24-B4-C8-D55
A69-B4-C8-D55
A67-B4-C8-D55
A39-B4-C8-D55
A65-B4-C8-D55
A66-B4-C8-D55
A2-B5-C8-D55
A3-B5-C8-D55
A9-B5-C8-D55
A13-B5-C8-D55
A24-B5-C8-D55
A69-B5-C8-D55
A67-B5-C8-D55
A39-B5-C8-D55
A65-B5-C8-D55
A66-B5-C8-D55
A2-B6-C8-D55
A3-B6-C8-D55
A9-B6-C8-D55
A13-B6-C8-D55
A24-B6-C8-D55
A69-B6-C8-D55
A67-B6-C8-D55
A39-B6-C8-D55
A65-B6-C8-D55
A66-B6-C8-D55
A2-B32-C8-D55
A3-B32-C8-D55
A9-B32-C8-D55
A13-B32-C8-D55
A24-B32-C8-D55
A69-B32-C8-D55
A67-B32-C8-D55
A39-B32-C8-D55
A65-B32-C8-D55
A66-B32-C8-D55
A2-B39-C8-D55
A3-B39-C8-D55
A9-B39-C8-D55
A13-B39-C8-D55
A24-B39-C8-D55
A69-B39-C8-D55
A67-B39-C8-D55
A39-B39-C8-D55
A65-B39-C8-D55
A66-B39-C8-D55
A2-B45-C8-D55
A3-B45-C8-D55
A9-B45-C8-D55
A13-B45-C8-D55
A24-B45-C8-D55
A69-B45-C8-D55
A67-B45-C8-D55
A39-B45-C8-D55
A65-B45-C8-D55
A66-B45-C8-D55
A2-B53-C8-D55
A3-B53-C8-D55
A9-B53-C8-D55
A13-B53-C8-D55
A24-B53-C8-D55
A69-B53-C8-D55
A67-B53-C8-D55
A39-B53-C8-D55
A65-B53-C8-D55
A66-B53-C8-D55
A2-B79-C8-D55
A3-B79-C8-D55
A9-B79-C8-D55
A13-B79-C8-D55
A24-B79-C8-D55
A69-B79-C8-D55
A67-B79-C8-D55
A39-B79-C8-D55
A65-B79-C8-D55
A66-B79-C8-D55
A2-B80-C8-D55
A3-B80-C8-D55
A9-B80-C8-D55

-continued

A13-B80-C8-D55
A24-B80-C8-D55
A69-B80-C8-D55
A67-B80-C8-D55
A39-B80-C8-D55
A65-B80-C8-D55
A66-B80-C8-D55
A2-B85-C8-D55
A3-B85-C8-D55
A9-B85-C8-D55
A13-B85-C8-D55
A24-B85-C8-D55
A69-B85-C8-D55
A67-B85-C8-D55
A39-B85-C8-D55
A65-B85-C8-D55
A66-B85-C8-D55
A2-B86-C8-D55
A3-B86-C8-D55
A9-B86-C8-D55
A13-B86-C8-D55
A24-B86-C8-D55
A69-B86-C8-D55
A67-B86-C8-D55
A39-B86-C8-D55
A65-B86-C8-D55
A66-B86-C8-D55
A2-B87-C8-D55
A3-B87-C8-D55
A9-B87-C8-D55
A13-B87-C8-D55
A24-B87-C8-D55
A69-B87-C8-D55
A67-B87-C8-D55
A39-B87-C8-D55
A65-B87-C8-D55
A66-B87-C8-D55
A2-B89-C8-D55
A3-B89-C8-D55
A9-B89-C8-D55
A13-B89-C8-D55
A24-B89-C8-D55
A69-B89-C8-D55
A67-B89-C8-D55
A39-B89-C8-D55
A65-B89-C8-D55
A66-B89-C8-D55
A2-B92-C8-D55
A3-B92-C8-D55
A9-B92-C8-D55
A13-B92-C8-D55
A24-B92-C8-D55
A69-B92-C8-D55
A67-B92-C8-D55
A39-B92-C8-D55
A65-B92-C8-D55
A66-B92-C8-D55
A2-B4-C9-D55
A3-B4-C9-D55
A9-B4-C9-D55
A13-B4-C9-D55
A24-B4-C9-D55
A69-B4-C9-D55
A67-B4-C9-D55
A39-B4-C9-D55
A65-B4-C9-D55
A66-B4-C9-D55
A2-B5-C9-D55
A3-B5-C9-D55
A9-B5-C9-D55
A13-B5-C9-D55
A24-B5-C9-D55
A69-B5-C9-D55
A67-B5-C9-D55
A39-B5-C9-D55
A65-B5-C9-D55
A66-B5-C9-D55
A2-B6-C9-D55
A3-B6-C9-D55
A9-B6-C9-D55

-continued

A13-B6-C9-D55
A24-B6-C9-D55
A69-B6-C9-D55
A67-B6-C9-D55
A39-B6-C9-D55
A65-B6-C9-D55
A66-B6-C9-D55
A2-B32-C9-D55
A3-B32-C9-D55
A9-B32-C9-D55
A13-B32-C9-D55
A24-B32-C9-D55
A69-B32-C9-D55
A67-B32-C9-D55
A39-B32-C9-D55
A65-B32-C9-D55
A66-B32-C9-D55
A2-B39-C9-D55
A3-B39-C9-D55
A9-B39-C9-D55
A13-B39-C9-D55
A24-B39-C9-D55
A69-B39-C9-D55
A67-B39-C9-D55
A39-B39-C9-D55
A65-B39-C9-D55
A66-B39-C9-D55
A2-B45-C9-D55
A3-B45-C9-D55
A9-B45-C9-D55
A13-B45-C9-D55
A24-B45-C9-D55
A69-B45-C9-D55
A67-B45-C9-D55
A39-B45-C9-D55
A65-B45-C9-D55
A66-B45-C9-D55
A2-B53-C9-D55
A3-B53-C9-D55
A9-B53-C9-D55
A13-B53-C9-D55
A24-B53-C9-D55
A69-B53-C9-D55
A67-B53-C9-D55
A39-B53-C9-D55
A65-B53-C9-D55
A66-B53-C9-D55
A2-B79-C9-D55
A3-B79-C9-D55
A9-B79-C9-D55
A13-B79-C9-D55
A24-B79-C9-D55
A69-B79-C9-D55
A67-B79-C9-D55
A39-B79-C9-D55
A65-B79-C9-D55
A66-B79-C9-D55
A2-B80-C9-D55
A3-B80-C9-D55
A9-B80-C9-D55
A13-B80-C9-D55
A24-B80-C9-D55
A69-B80-C9-D55
A67-B80-C9-D55
A39-B80-C9-D55
A65-B80-C9-D55
A66-B80-C9-D55
A2-B85-C9-D55
A3-B85-C9-D55
A9-B85-C9-D55
A13-B85-C9-D55
A24-B85-C9-D55
A69-B85-C9-D55
A67-B85-C9-D55
A39-B85-C9-D55
A65-B85-C9-D55
A66-B85-C9-D55
A2-B86-C9-D55
A3-B86-C9-D55
A9-B86-C9-D55

-continued

A13-B86-C9-D55
A24-B86-C9-D55
A69-B86-C9-D55
A67-B86-C9-D55
A39-B86-C9-D55
A65-B86-C9-D55
A66-B86-C9-D55
A2-B87-C9-D55
A3-B87-C9-D55
A9-B87-C9-D55
A13-B87-C9-D55
A24-B87-C9-D55
A69-B87-C9-D55
A67-B87-C9-D55
A39-B87-C9-D55
A65-B87-C9-D55
A66-B87-C9-D55
A2-B89-C9-D55
A3-B89-C9-D55
A9-B89-C9-D55
A13-B89-C9-D55
A24-B89-C9-D55
A69-B89-C9-D55
A67-B89-C9-D55
A39-B89-C9-D55
A65-B89-C9-D55
A66-B89-C9-D55
A2-B92-C9-D55
A3-B92-C9-D55
A9-B92-C9-D55
A13-B92-C9-D55
A24-B92-C9-D55
A69-B92-C9-D55
A67-B92-C9-D55
A39-B92-C9-D55
A65-B92-C9-D55
A66-B92-C9-D55
A2-B4-C10-D55
A3-B4-C10-D55
A9-B4-C10-D55
A13-B4-C10-D55
A24-B4-C10-D55
A69-B4-C10-D55
A67-B4-C10-D55
A39-B4-C10-D55
A65-B4-C10-D55
A66-B4-C10-D55
A2-B5-C10-D55
A3-B5-C10-D55
A9-B5-C10-D55
A13-B5-C10-D55
A24-B5-G10-D55
A69-B5-C10-D55
A67-B5-C10-D55
A39-B5-C10-D55
A65-B5-C10-D55
A66-B5-C10-D55
A2-B6-C10-D55
A3-B6-C10-D55
A9-B6-C10-D55
A13-B6-C10-D55
A24-B6-C10-D55
A69-B6-C10-D55
A67-B6-C10-D55
A39-B6-C10-D55
A65-B6-C10-D55
A66-B6-C10-D55
A2-B32-C10-D55
A3-B32-C10-D55
A9-B32-C10-D55
A13-B32-C10-D55
A24-B32-C10-D55
A69-B32-C10-D55
A67-B32-C10-D55
A39-B32-C10-D55
A65-B32-C10-D55
A66-B32-C10-D55
A2-B39-C10-D55
A3-B39-C10-D55
A9-B39-C10-D55

-continued
A13-B39-C10-D55
A24-B39-C10-D55
A69-B39-C10-D55
A67-B39-C10-D55
A39-B39-C10-D55
A65-B39-C10-D55
A66-B39-C10-D55
A2-B45-C10-D55
A3-B45-C10-D55
A9-B45-C10-D55
A13-B45-C10-D55
A24-B45-C10-D55
A69-B45-C10-D55
A67-B45-C10-D55
A39-B45-C10-D55
A65-B45-C10-D55
A66-B45-C10-D55
A2-B53-C10-D55
A3-B53-C10-D55
A9-B53-C10-D55
A13-B53-C10-D55
A24-B53-C10-D55
A69-B53-C10-D55
A67-B53-C10-D55
A39-B53-C10-D55
A65-B53-C10-D55
A66-B53-C10-D55
A2-B79-C10-D55
A3-B79-C10-D55
A9-B79-C10-D55
A13-B79-C10-D55
A24-B79-C10-D55
A69-B79-C10-D55
A67-B79-C10-D55
A39-B79-C10-D55
A65-B79-C10-D55
A66-B79-C10-D55
A2-B80-C10-D55
A3-B80-C10-D55
A9-B80-C10-D55
A13-B80-C10-D55
A24-B80-C10-D55
A69-B80-C10-D55
A67-B80-C10-D55
A39-B80-C10-D55
A65-B80-C10-D55
A66-B80-C10-D55
A2-B85-C10-D55
A3-B85-C10-D55
A9-B85-C10-D55
A13-B85-C10-D55
A24-B85-C10-D55
A69-B85-C10-D55
A67-B85-C10-D55
A39-B85-C10-D55
A65-B85-C10-D55
A66-B85-C10-D55
A2-B86-C10-D55
A3-B86-C10-D55
A9-B86-C10-D55
A13-B86-C10-D55
A24-B86-C10-D55
A69-B86-C10-D55
A67-B86-C10-D55
A39-B86-C10-D55
A65-B86-C10-D55
A66-B86-C10-D55
A2-B87-C10-D55
A3-B87-C10-D55
A9-B87-C10-D55
A13-B87-C10-D55
A24-B87-C10-D55
A69-B87-C10-D55
A67-B87-C10-D55
A39-B87-C10-D55
A65-B87-C10-D55
A66-B87-C10-D55
A2-B89-C10-D55
A3-B89-C10-D55
A9-B89-C10-D55

-continued
A13-B89-C10-D55
A24-B89-C10-D55
A69-B89-C10-D55
A67-B89-C10-D55
A39-B89-C10-D55
A65-B89-C10-D55
A66-B89-C10-D55
A2-B92-C10-D55
A3-B92-C10-D55
A9-B92-C10-D55
A13-B92-C10-D55
A24-B92-C10-D55
A69-B92-C10-D55
A67-B92-C10-D55
A39-B92-C10-D55
A65-B92-C10-D55
A66-B92-C10-D55
A2-B4-C11-D55
A3-B4-C11-D55
A9-B4-C11-D55
A13-B4-C11-D55
A24-B4-C11-D55
A69-B4-C11-D55
A67-B4-C11-D55
A39-B4-C11-D55
A65-B4-C11-D55
A66-B4-C11-D55
A2-B5-C11-D55
A3-B5-C11-D55
A9-B5-C11-D55
A13-B5-C11-D55
A24-B5-C11-D55
A69-B5-C11-D55
A67-B5-C11-D55
A39-B5-C11-D55
A65-B5-C11-D55
A66-B5-C11-D55
A2-B6-C11-D55
A3-B6-C11-D55
A9-B6-C11-D55
A13-B6-C11-D55
A24-B6-C11-D55
A69-B6-C11-D55
A67-B6-C11-D55
A39-B6-C11-D55
A65-B6-C11-D55
A66-B6-C11-D55
A2-B32-C11-D55
A3-B32-C11-D55
A9-B32-C11-D55
A13-B32-C11-D55
A24-B32-C11-D55
A69-B32-C11-D55
A67-B32-C11-D55
A39-B32-C11-D55
A65-B32-C11-D55
A66-B32-C11-D55
A2-B39-C11-D55
A3-B39-C11-D55
A9-B39-C11-D55
A13-B39-C11-D55
A24-B39-C11-D55
A69-B39-C11-D55
A67-B39-C11-D55
A39-B39-C11-D55
A65-B39-C11-D55
A66-B39-C11-D55
A2-B45-C11-D55
A3-B45-C11-D55
A9-B45-C11-D55
A13-B45-C11-D55
A24-B45-C11-D55
A69-B45-C11-D55
A67-B45-C11-D55
A39-B45-C11-D55
A65-B45-C11-D55
A66-B45-C11-D55
A2-B53-C11-D55
A3-B53-C11-D55
A9-B53-C11-D55

-continued

A13-B53-C11-D55
A24-B53-C11-D55
A69-B53-C11-D55
A67-B53-C11-D55
A39-B53-C11-D55
A65-B53-C11-D55
A66-B53-C11-D55
A2-B79-C11-D55
A3-B79-C11-D55
A9-B79-C11-D55
A13-B79-C11-D55
A24-B79-C11-D55
A69-B79-C11-D55
A67-B79-C11-D55
A39-B79-C11-D55
A65-B79-C11-D55
A66-B79-C11-D55
A2-B80-C11-D55
A3-B80-C11-D55
A9-B80-C11-D55
A13-B80-C11-D55
A24-B80-C11-D55
A69-B80-C11-D55
A67-B80-C11-D55
A39-B80-C11-D55
A65-B80-C11-D55
A66-B80-C11-D55
A2-B85-C11-D55
A3-B85-C11-D55
A9-B85-C11-D55
A13-B85-C11-D55
A24-B85-C11-D55
A69-B85-C11-D55
A67-B85-C11-D55
A39-B85-C11-D55
A65-B85-C11-D55
A66-B85-C11-D55
A2-B86-C11-D55
A3-B86-C11-D55
A9-B86-C11-D55
A13-B86-C11-D55
A24-B86-C11-D55
A69-B86-C11-D55
A67-B86-C11-D55
A39-B86-C11-D55
A65-B86-C11-D55
A66-B86-C11-D55
A2-B87-C11-D55
A3-B87-C11-D55
A9-B87-C11-D55
A13-B87-C11-D55
A24-B87-C11-D55
A69-B87-C11-D55
A67-B87-C11-D55
A39-B87-C11-D55
A65-B87-C11-D55
A66-B87-C11-D55
A2-B89-C11-D55
A3-B89-C11-D55
A9-B89-C11-D55
A13-B89-C11-D55
A24-B89-C11-D55
A69-B89-C11-D55
A67-B89-C11-D55
A39-B89-C11-D55
A65-B89-C11-D55
A66-B89-C11-D55
A2-B92-C11-D55
A3-B92-C11-D55
A9-B92-C11-D55
A13-B92-C11-D55
A24-B92-C11-D55
A69-B92-C11-D55
A67-B92-C11-D55
A39-B92-C11-D55
A65-B92-C11-D55
A66-B92-C11-D55
A2-B4-C12-D55
A3-B4-C12-D55
A9-B4-C12-D55

-continued

A13-B4-C12-D55
A24-B4-C12-D55
A69-B4-C12-D55
A67-B4-C12-D55
A39-B4-C12-D55
A65-B4-C12-D55
A66-B4-C12-D55
A2-B5-C12-D55
A3-B5-C12-D55
A9-B5-C12-D55
A13-B5-C12-D55
A24-B5-C12-D55
A69-B5-C12-D55
A67-B5-C12-D55
A39-B5-C12-D55
A65-B5-C12-D55
A66-B5-C12-D55
A2-B6-C12-D55
A3-B6-C12-D55
A9-B6-C12-D55
A13-B6-C12-D55
A24-B6-C12-D55
A69-B6-C12-D55
A67-B6-C12-D55
A39-B6-C12-D55
A65-B6-C12-D55
A66-B6-C12-D55
A2-B32-C12-D55
A3-B32-C12-D55
A9-B32-C12-D55
A13-B32-C12-D55
A24-B32-C12-D55
A69-B32-C12-D55
A67-B32-C12-D55
A39-B32-C12-D55
A65-B32-C12-D55
A66-B32-C12-D55
A2-B39-C12-D55
A3-B39-C12-D55
A9-B39-C12-D55
A13-B39-C12-D55
A24-B39-C12-D55
A69-B39-C12-D55
A67-B39-C12-D55
A39-B39-C12-D55
A65-B39-C12-D55
A66-B39-C12-D55
A2-B45-C12-D55
A3-B45-C12-D55
A9-B45-C12-D55
A13-B45-C12-D55
A24-B45-C12-D55
A69-B45-C12-D55
A67-B45-C12-D55
A39-B45-C12-D55
A65-B45-C12-D55
A66-B45-C12-D55
A2-B53-C12-D55
A3-B53-C12-D55
A9-B53-C12-D55
A13-B53-C12-D55
A24-B53-C12-D55
A69-B53-C12-D55
A67-B53-C12-D55
A39-B53-C12-D55
A65-B53-C12-D55
A66-B53-C12-D55
A2-B79-C12-D55
A3-B79-C12-D55
A9-B79-C12-D55
A13-B79-C12-D55
A24-B79-C12-D55
A69-B79-C12-D55
A67-B79-C12-D55
A39-B79-C12-D55
A65-B79-C12-D55
A66-B79-C12-D55
A2-B80-C12-D55
A3-B80-C12-D55
A9-B80-C12-D55

-continued
A13-B80-C12-D55
A24-B80-C12-D55
A69-B80-C12-D55
A67-B80-C12-D55
A39-B80-C12-D55
A65-B80-C12-D55
A66-B80-C12-D55
A2-B85-C12-D55
A3-B85-C12-D55
A9-B85-C12-D55
A13-B85-C12-D55
A24-B85-C12-D55
A69-B85-C12-D55
A67-B85-C12-D55
A39-B85-C12-D55
A65-B85-C12-D55
A66-B85-C12-D55
A2-B86-C12-D55
A3-B86-C12-D55
A9-B86-C12-D55
A13-B86-C12-D55
A24-B86-C12-D55
A69-B86-C12-D55
A67-B86-C12-D55
A39-B86-C12-D55
A65-B86-C12-D55
A66-B86-C12-D55
A2-B87-C12-D55
A3-B87-C12-D55
A9-B87-C12-D55
A13-B87-C12-D55
A24-B87-C12-D55
A69-B87-C12-D55
A67-B87-C12-D55
A39-B87-C12-D55
A65-B87-C12-D55
A66-B87-C12-D55
A2-B89-C12-D55
A3-B89-C12-D55
A9-B89-C12-D55
A13-B89-C12-D55
A24-B89-C12-D55
A69-B89-C12-D55
A67-B89-C12-D55
A39-B89-C12-D55
A65-B89-C12-D55
A66-B89-C12-D55
A2-B92-C12-D55
A3-B92-C12-D55
A9-B92-C12-D55
A13-B92-C12-D55
A24-B92-C12-D55
A69-B92-C12-D55
A67-B92-C12-D55
A39-B92-C12-D55
A65-B92-C12-D55
A66-B92-C12-D55
A2-B4-C13-D55
A3-B4-C13-D55
A9-B4-C13-D55
A13-B4-C13-D55
A24-B4-C13-D55
A69-B4-C13-D55
A67-B4-C13-D55
A39-B4-C13-D55
A65-B4-C13-D55
A66-B4-C13-D55
A2-B5-C13-D55
A3-B5-C13-D55
A9-B5-C13-D55
A13-B5-C13-D55
A24-B5-C13-D55
A69-B5-C13-D55
A67-B5-C13-D55
A39-B5-C13-D55
A65-B5-C13-D55
A66-B5-C13-D55
A2-B6-C13-D55
A3-B6-C13-D55
A9-B6-C13-D55

-continued
A13-B6-C13-D55
A24-B6-C13-D55
A69-B6-C13-D55
A67-B6-C13-D55
A39-B6-C13-D55
A65-B6-C13-D55
A66-B6-C13-D55
A2-B32-C13-D55
A3-B32-C13-D55
A9-B32-C13-D55
A13-B32-C13-D55
A24-B32-C13-D55
A69-B32-C13-D55
A67-B32-C13-D55
A39-B32-C13-D55
A65-B32-C13-D55
A66-B32-C13-D55
A2-B39-C13-D55
A3-B39-C13-D55
A9-B39-C13-D55
A13-B39-C13-D55
A24-B39-C13-D55
A69-B39-C13-D55
A67-B39-C13-D55
A39-B39-C13-D55
A65-B39-C13-D55
A66-B39-C13-D55
A2-B45-C13-D55
A3-B45-C13-D55
A9-B45-C13-D55
A13-B45-C13-D55
A24-B45-C13-D55
A69-B45-C13-D55
A67-B45-C13-D55
A39-B45-C13-D55
A65-B45-C13-D55
A66-B45-C13-D55
A2-B53-C13-D55
A3-B53-C13-D55
A9-B53-C13-D55
A13-B53-C13-D55
A24-B53-C13-D55
A69-B53-C13-D55
A67-B53-C13-D55
A39-B53-C13-D55
A65-B53-C13-D55
A66-B53-C13-D55
A2-B79-C13-D55
A3-B79-C13-D55
A9-B79-C13-D55
A13-B79-C13-D55
A24-B79-C13-D55
A69-B79-C13-D55
A67-B79-C13-D55
A39-B79-C13-D55
A65-B79-C13-D55
A66-B79-C13-D55
A2-B80-C13-D55
A3-B80-C13-D55
A9-B80-C13-D55
A13-B80-C13-D55
A24-B80-C13-D55
A69-B80-C13-D55
A67-B80-C13-D55
A39-B80-C13-D55
A65-B80-C13-D55
A66-B80-C13-D55
A2-B85-C13-D55
A3-B85-C13-D55
A9-B85-C13-D55
A13-B85-C13-D55
A24-B85-C13-D55
A69-B85-C13-D55
A67-B85-C13-D55
A39-B85-C13-D55
A65-B85-C13-D55
A66-B85-C13-D55
A2-B86-C13-D55
A3-B86-C13-D55
A9-B86-C13-D55

-continued
A13-B86-C13-D55
A24-B86-C13-D55
A69-B86-C13-D55
A67-B86-C13-D55
A39-B86-C13-D55
A65-B86-C13-D55
A66-B86-C13-D55
A2-B87-C13-D55
A3-B87-C13-D55
A9-B87-C13-D55
A13-B87-C13-D55
A24-B87-C13-D55
A69-B87-C13-D55
A67-B87-C13-D55
A39-B87-C13-D55
A65-B87-C13-D55
A66-B87-C13-D55
A2-B89-C13-D55
A3-B89-C13-D55
A9-B89-C13-D55
A13-B89-C13-D55
A24-B89-C13-D55
A69-B89-C13-D55
A67-B89-C13-D55
A39-B89-C13-D55
A65-B89-C13-D55
A66-B89-C13-D55
A2-B92-C13-D55
A3-B92-C13-D55
A9-B92-C13-D55
A13-B92-C13-D55
A24-B92-C13-D55
A69-B92-C13-D55
A67-B92-C13-D55
A39-B92-C13-D55
A65-B92-C13-D55
A66-B92-C13-D55
A2-B4-C1-D56
A3-B4-C1-D56
A9-B4-C1-D56
A13-B4-C1-D56
A24-B4-C1-D56
A69-B4-C1-D56
A67-B4-C1-D56
A39-B4-C1-D56
A65-B4-C1-D56
A66-B4-C1-D56
A2-B5-C1-D56
A3-B5-C1-D56
A9-B5-C1-D56
A13-B5-C1-D56
A24-B5-C1-D56
A69-B5-C1-D56
A67-B5-C1-D56
A39-B5-C1-D56
A65-B5-C1-D56
A66-B5-C1-D56
A2-B6-C1-D56
A3-B6-C1-D56
A9-B6-C1-D56
A13-B6-C1-D56
A24-B6-C1-D56
A69-B6-C1-D56
A67-B6-C1-D56
A39-B6-C1-D56
A65-B6-C1-D56
A66-B6-C1-D56
A2-B32-C1-D56
A3-B32-C1-D56
A9-B32-C1-D56
A13-B32-C1-D56
A24-B32-C1-D56
A69-B32-C1-D56
A67-B32-C1-D56
A39-B32-C1-D56
A65-B32-C1-D56
A66-B32-C1-D56
A2-B39-C1-D56
A3-B39-C1-D56
A9-B39-C1-D56

-continued
A13-B39-C1-D56
A24-B39-C1-D56
A69-B39-C1-D56
A67-B39-C1-D56
A39-B39-C1-D56
A65-B39-C1-D56
A66-B39-C1-D56
A2-B45-C1-D56
A3-B45-C1-D56
A9-B45-C1-D56
A13-B45-C1-D56
A24-B45-C1-D56
A69-B45-C1-D56
A67-B45-C1-D56
A39-B45-C1-D56
A65-B45-C1-D56
A66-B45-C1-D56
A2-B53-C1-D56
A3-B53-C1-D56
A9-B53-C1-D56
A13-B53-C1-D56
A24-B53-C1-D56
A69-B53-C1-D56
A67-B53-C1-D56
A39-B53-C1-D56
A65-B53-C1-D56
A66-B53-C1-D56
A2-B79-C1-D56
A3-B79-C1-D56
A9-B79-C1-D56
A13-B79-C1-D56
A24-B79-C1-D56
A69-B79-C1-D56
A67-B79-C1-D56
A39-B79-C1-D56
A65-B79-C1-D56
A66-B79-C1-D56
A2-B80-C1-D56
A3-B80-C1-D56
A9-B80-C1-D56
A13-B80-C1-D56
A24-B80-C1-D56
A69-B80-C1-D56
A67-B80-C1-D56
A39-B80-C1-D56
A65-B80-C1-D56
A66-B80-C1-D56
A2-B85-C1-D56
A3-B85-C1-D56
A9-B85-C1-D56
A13-B85-C1-D56
A24-B85-C1-D56
A69-B85-C1-D56
A67-B85-C1-D56
A39-B85-C1-D56
A65-B85-C1-D56
A66-B85-C1-D56
A2-B86-C1-D56
A3-B86-C1-D56
A9-B86-C1-D56
A13-B86-C1-D56
A24-B86-C1-D56
A69-B86-C1-D56
A67-B86-C1-D56
A39-B86-C1-D56
A65-B86-C1-D56
A66-B86-C1-D56
A2-B87-C1-D56
A3-B87-C1-D56
A9-B87-C1-D56
A13-B87-C1-D56
A24-B87-C1-D56
A69-B87-C1-D56
A67-B87-C1-D56
A39-B87-C1-D56
A65-B87-C1-D56
A66-B87-C1-D56
A2-B89-C1-D56
A3-B89-C1-D56
A9-B89-C1-D56

-continued
A13-B89-C1-D56
A24-B89-C1-D56
A69-B89-C1-D56
A67-B89-C1-D56
A39-B89-C1-D56
A65-B89-C1-D56
A66-B89-C1-D56
A2-B92-C1-D56
A3-B92-C1-D56
A9-B92-C1-D56
A13-B92-C1-D56
A24-B92-C1-D56
A69-B92-C1-D56
A67-B92-C1-D56
A39-B92-C1-D56
A65-B92-C1-D56
A66-B92-C1-D56
A2-B4-C2-D56
A3-B4-C2-D56
A9-B4-C2-D56
A13-B4-C2-D56
A24-B4-C2-D56
A69-B4-C2-D56
A67-B4-C2-D56
A39-B4-C2-D56
A65-B4-C2-D56
A66-B4-C2-D56
A2-B5-C2-D56
A3-B5-C2-D56
A9-B5-C2-D56
A13-B5-C2-D56
A24-B5-C2-D56
A69-B5-C2-D56
A67-B5-C2-D56
A39-B5-C2-D56
A65-B5-C2-D56
A66-B5-C2-D56
A2-B6-C2-D56
A3-B6-C2-D56
A9-B6-C2-D56
A13-B6-C2-D56
A24-B6-C2-D56
A69-B6-C2-D56
A67-B6-C2-D56
A39-B6-C2-D56
A65-B6-C2-D56
A66-B6-C2-D56
A2-B32-C2-D56
A3-B32-C2-D56
A9-B32-C2-D56
A13-B32-C2-D56
A24-B32-C2-D56
A69-B32-C2-D56
A67-B32-C2-D56
A39-B32-C2-D56
A65-B32-C2-D56
A66-B32-C2-D56
A2-B39-C2-D56
A3-B39-C2-D56
A9-B39-C2-D56
A13-B39-C2-D56
A24-B39-C2-D56
A69-B39-C2-D56
A67-B39-C2-D56
A39-B39-C2-D56
A65-B39-C2-D56
A66-B39-C2-D56
A2-B45-C2-D56
A3-B45-C2-D56
A9-B45-C2-D56
A13-B45-C2-D56
A24-B45-C2-D56
A69-B45-C2-D56
A67-B45-C2-D56
A39-B45-C2-D56
A65-B45-C2-D56
A66-B45-C2-D56
A2-B53-C2-D56
A3-B53-C2-D56
A9-B53-C2-D56

-continued
A13-B53-C2-D56
A24-B53-C2-D56
A69-B53-C2-D56
A67-B53-C2-D56
A39-B53-C2-D56
A65-B53-C2-D56
A66-B53-C2-D56
A2-B79-C2-D56
A3-B79-C2-D56
A9-B79-C2-D56
A13-B79-C2-D56
A24-B79-C2-D56
A69-B79-C2-D56
A67-B79-C2-D56
A39-B79-C2-D56
A65-B79-C2-D56
A66-B79-C2-D56
A2-B80-C2-D56
A3-B80-C2-D56
A9-B80-C2-D56
A13-B80-C2-D56
A24-B80-C2-D56
A69-B80-C2-D56
A67-B80-C2-D56
A39-B80-C2-D56
A65-B80-C2-D56
A66-B80-C2-D56
A2-B85-C2-D56
A3-B85-C2-D56
A9-B85-C2-D56
A13-B85-C2-D56
A24-B85-C2-D56
A69-B85-C2-D56
A67-B85-C2-D56
A39-B85-C2-D56
A65-B85-C2-D56
A66-B85-C2-D56
A2-B86-C2-D56
A3-B86-C2-D56
A9-B86-C2-D56
A13-B86-C2-D56
A24-B86-C2-D56
A69-B86-C2-D56
A67-B86-C2-D56
A39-B86-C2-D56
A65-B86-C2-D56
A66-B86-C2-D56
A2-B87-C2-D56
A3-B87-C2-D56
A9-B87-C2-D56
A13-B87-C2-D56
A24-B87-C2-D56
A69-B87-C2-D56
A67-B87-C2-D56
A39-B87-C2-D56
A65-B87-C2-D56
A66-B87-C2-D56
A2-B89-C2-D56
A3-B89-C2-D56
A9-B89-C2-D56
A13-B89-C2-D56
A24-B89-C2-D56
A69-B89-C2-D56
A67-B89-C2-D56
A39-B89-C2-D56
A65-B89-C2-D56
A66-B89-C2-D56
A2-B92-C2-D56
A3-B92-C2-D56
A9-B92-C2-D56
A13-B92-C2-D56
A24-B92-C2-D56
A69-B92-C2-D56
A67-B92-C2-D56
A39-B92-C2-D56
A65-B92-C2-D56
A66-B92-C2-D56
A2-B4-C3-D56
A3-B4-C3-D56
A9-B4-C3-D56

-continued

A13-B4-C3-D56
A24-B4-C3-D56
A69-B4-C3-D56
A67-B4-C3-D56
A39-B4-C3-D56
A65-B4-C3-D56
A66-B4-C3-D56
A2-B5-C3-D56
A3-B5-C3-D56
A9-B5-C3-D56
A13-B5-C3-D56
A24-B5-C3-D56
A69-B5-C3-D56
A67-B5-C3-D56
A39-B5-C3-D56
A65-B5-C3-D56
A66-B5-C3-D56
A2-B6-C3-D56
A3-B6-C3-D56
A9-B6-C3-D56
A13-B6-C3-D56
A24-B6-C3-D56
A69-B6-C3-D56
A67-B6-C3-D56
A39-B6-C3-D56
A65-B6-C3-D56
A66-B6-C3-D56
A2-B32-C3-D56
A3-B32-C3-D56
A9-B32-C3-D56
A13-B32-C3-D56
A24-B32-C3-D56
A69-B32-C3-D56
A67-B32-C3-D56
A39-B32-C3-D56
A65-B32-C3-D56
A66-B32-C3-D56
A2-B39-C3-D56
A3-B39-C3-D56
A9-B39-C3-D56
A13-B39-C3-D56
A24-B39-C3-D56
A69-B39-C3-D56
A67-B39-C3-D56
A39-B39-C3-D56
A65-B39-C3-D56
A66-B39-C3-D56
A2-B45-C3-D56
A3-B45-C3-D56
A9-B45-C3-D56
A13-B45-C3-D56
A24-B45-C3-D56
A69-B45-C3-D56
A67-B45-C3-D56
A39-B45-C3-D56
A65-B45-C3-D56
A66-B45-C3-D56
A2-B53-C3-D56
A3-B53-C3-D56
A9-B53-C3-D56
A13-B53-C3-D56
A24-B53-C3-D56
A69-B53-C3-D56
A67-B53-C3-D56
A39-B53-C3-D56
A65-B53-C3-D56
A66-B53-C3-D56
A2-B79-C3-D56
A3-B79-C3-D56
A9-B79-C3-D56
A13-B79-C3-D56
A24-B79-C3-D56
A69-B79-C3-D56
A67-B79-C3-D56
A39-B79-C3-D56
A65-B79-C3-D56
A66-B79-C3-D56
A2-B80-C3-D56
A3-B80-C3-D56
A9-B80-C3-D56

-continued

A13-B80-C3-D56
A24-B80-C3-D56
A69-B80-C3-D56
A67-B80-C3-D56
A39-B80-C3-D56
A65-B80-C3-D56
A66-B80-C3-D56
A2-B85-C3-D56
A3-B85-C3-D56
A9-B85-C3-D56
A13-B85-C3-D56
A24-B85-C3-D56
A69-B85-C3-D56
A67-B85-C3-D56
A39-B85-C3-D56
A65-B85-C3-D56
A66-B85-C3-D56
A2-B86-C3-D56
A3-B86-C3-D56
A9-B86-C3-D56
A13-B86-C3-D56
A24-B86-C3-D56
A69-B86-C3-D56
A67-B86-C3-D56
A39-B86-C3-D56
A65-B86-C3-D56
A66-B86-C3-D56
A2-B87-C3-D56
A3-B87-C3-D56
A9-B87-C3-D56
A13-B87-C3-D56
A24-B87-C3-D56
A69-B87-C3-D56
A67-B87-C3-D56
A39-B87-C3-D56
A65-B87-C3-D56
A66-B87-C3-D56
A2-B89-C3-D56
A3-B89-C3-D56
A9-B89-C3-D56
A13-B89-C3-D56
A24-B89-C3-D56
A69-B89-C3-D56
A67-B89-C3-D56
A39-B89-C3-D56
A65-B89-C3-D56
A66-B89-C3-D56
A2-B92-C3-D56
A3-B92-C3-D56
A9-B92-C3-D56
A13-B92-C3-D56
A24-B92-C3-D56
A69-B92-C3-D56
A67-B92-C3-D56
A39-B92-C3-D56
A65-B92-C3-D56
A66-B92-C3-D56
A2-B4-C4-D56
A3-B4-C4-D56
A9-B4-C4-D56
A13-B4-C4-D56
A24-B4-C4-D56
A69-B4-C4-D56
A67-B4-C4-D56
A39-B4-C4-D56
A65-B4-C4-D56
A66-B4-C4-D56
A2-B5-C4-D56
A3-B5-C4-D56
A9-B5-C4-D56
A13-B5-C4-D56
A24-B5-C4-D56
A69-B5-C4-D56
A67-B5-C4-D56
A39-B5-C4-D56
A65-B5-C4-D56
A66-B5-C4-D56
A2-B6-C4-D56
A3-B6-C4-D56
A9-B6-C4-D56

-continued

A13-B6-C4-D56
A24-B6-C4-D56
A69-B6-C4-D56
A67-B6-C4-D56
A39-B6-C4-D56
A65-B6-C4-D56
A66-B6-C4-D56
A2-B32-C4-D56
A3-B32-C4-D56
A9-B32-C4-D56
A13-B32-C4-D56
A24-B32-C4-D56
A69-B32-C4-D56
A67-B32-C4-D56
A39-B32-C4-D56
A65-B32-C4-D56
A66-B32-C4-D56
A2-B39-C4-D56
A3-B39-C4-D56
A9-B39-C4-D56
A13-B39-C4-D56
A24-B39-C4-D56
A69-B39-C4-D56
A67-B39-C4-D56
A39-B39-C4-D56
A65-B39-C4-D56
A66-B39-C4-D56
A2-B45-C4-D56
A3-B45-C4-D56
A9-B45-C4-D56
A13-B45-C4-D56
A24-B45-C4-D56
A69-B45-C4-D56
A67-B45-C4-D56
A39-B45-C4-D56
A65-B45-C4-D56
A66-B45-C4-D56
A2-B53-C4-D56
A3-B53-C4-D56
A9-B53-C4-D56
A13-B53-C4-D56
A24-B53-C4-D56
A69-B53-C4-D56
A67-B53-C4-D56
A39-B53-C4-D56
A65-B53-C4-D56
A66-B53-C4-D56
A2-B79-C4-D56
A3-B79-C4-D56
A9-B79-C4-D56
A13-B79-C4-D56
A24-B79-C4-D56
A69-B79-C4-D56
A67-B79-C4-D56
A39-B79-C4-D56
A65-B79-C4-D56
A66-B79-C4-D56
A2-B80-C4-D56
A3-B80-C4-D56
A9-B80-C4-D56
A13-B80-C4-D56
A24-B80-C4-D56
A69-B80-C4-D56
A67-B80-C4-D56
A39-B80-C4-D56
A65-B80-C4-D56
A66-B80-C4-D56
A2-B85-C4-D56
A3-B85-C4-D56
A9-B85-C4-D56
A13-B85-C4-D56
A24-B85-C4-D56
A69-B85-C4-D56
A67-B85-C4-D56
A39-B85-C4-D56
A65-B85-C4-D56
A66-B85-C4-D56
A2-B86-C4-D56
A3-B86-C4-D56
A9-B86-C4-D56

-continued

A13-B86-C4-D56
A24-B86-C4-D56
A69-B86-C4-D56
A67-B86-C4-D56
A39-B86-C4-D56
A65-B86-C4-D56
A66-B86-C4-D56
A2-B87-C4-D56
A3-B87-C4-D56
A9-B87-C4-D56
A13-B87-C4-D56
A24-B87-C4-D56
A69-B87-C4-D56
A67-B87-C4-D56
A39-B87-C4-D56
A65-B87-C4-D56
A66-B87-C4-D56
A2-B89-C4-D56
A3-B89-C4-D56
A9-B89-C4-D56
A13-B89-C4-D56
A24-B89-C4-D56
A69-B89-C4-D56
A67-B89-C4-D56
A39-B89-C4-D56
A65-B89-C4-D56
A66-B89-C4-D56
A2-B92-C4-D56
A3-B92-C4-D56
A9-B92-C4-D56
A13-B92-C4-D56
A24-B92-C4-D56
A69-B92-C4-D56
A67-B92-C4-D56
A39-B92-C4-D56
A65-B92-C4-D56
A66-B92-C4-D56
A2-B4-C5-D56
A3-B4-C5-D56
A9-B4-C5-D56
A13-B4-C5-D56
A24-B4-C5-D56
A69-B4-C5-D56
A67-B4-C5-D56
A39-B4-C5-D56
A65-B4-C5-D56
A66-B4-C5-D56
A2-B5-C5-D56
A3-B5-C5-D56
A9-B5-C5-D56
A13-B5-C5-D56
A24-B5-C5-D56
A69-B5-C5-D56
A67-B5-C5-D56
A39-B5-C5-D56
A65-B5-C5-D56
A66-B5-C5-D56
A2-B6-C5-D56
A3-B6-C5-D56
A9-B6-C5-D56
A13-B6-C5-D56
A24-B6-C5-D56
A69-B6-C5-D56
A67-B6-C5-D56
A39-B6-C5-D56
A65-B6-C5-D56
A66-B6-C5-D56
A2-B32-C5-D56
A3-B32-C5-D56
A9-B32-C5-D56
A13-B32-C5-D56
A24-B32-C5-D56
A69-B32-C5-D56
A67-B32-C5-D56
A39-B32-C5-D56
A65-B32-C5-D56
A66-B32-C5-D56
A2-B39-C5-D56
A3-B39-C5-D56
A9-B39-C5-D56

-continued
A13-B39-C5-D56
A24-B39-C5-D56
A69-B39-C5-D56
A67-B39-C5-D56
A39-B39-C5-D56
A65-B39-C5-D56
A66-B39-C5-D56
A2-B45-C5-D56
A3-B45-C5-D56
A9-B45-C5-D56
A13-B45-C5-D56
A24-B45-C5-D56
A69-B45-C5-D56
A67-B45-C5-D56
A39-B45-C5-D56
A65-B45-C5-D56
A66-B45-C5-D56
A2-B53-C5-D56
A3-B53-C5-D56
A9-B53-C5-D56
A13-B53-C5-D56
A24-B53-C5-D56
A69-B53-C5-D56
A67-B53-C5-D56
A39-B53-C5-D56
A65-B53-C5-D56
A66-B53-C5-D56
A2-B79-C5-D56
A3-B79-C5-D56
A9-B79-C5-D56
A13-B79-C5-D56
A24-B79-C5-D56
A69-B79-C5-D56
A67-B79-C5-D56
A39-B79-C5-D56
A65-B79-C5-D56
A66-B79-C5-D56
A2-B80-C5-D56
A3-B80-C5-D56
A9-B80-C5-D56
A13-B80-C5-D56
A24-B80-C5-D56
A69-B80-C5-D56
A67-B80-C5-D56
A39-B80-C5-D56
A65-B80-C5-D56
A66-B80-C5-D56
A2-B85-C5-D56
A3-B85-C5-D56
A9-B85-C5-D56
A13-B85-C5-D56
A24-B85-C5-D56
A69-B85-C5-D56
A67-B85-C5-D56
A39-B85-C5-D56
A65-B85-C5-D56
A66-B85-C5-D56
A2-B86-C5-D56
A3-B86-C5-D56
A9-B86-C5-D56
A13-B86-C5-D56
A24-B86-C5-D56
A69-B86-C5-D56
A67-B86-C5-D56
A39-B86-C5-D56
A65-B86-C5-D56
A66-B86-C5-D56
A2-B87-C5-D56
A3-B87-C5-D56
A9-B87-C5-D56
A13-B87-C5-D56
A24-B87-C5-D56
A69-B87-C5-D56
A67-B87-C5-D56
A39-B87-C5-D56
A65-B87-C5-D56
A66-B87-C5-D56
A2-B89-C5-D56
A3-B89-C5-D56
A9-B89-C5-D56

-continued
A13-B89-C5-D56
A24-B89-C5-D56
A69-B89-C5-D56
A67-B89-C5-D56
A39-B89-C5-D56
A65-B89-C5-D56
A66-B89-C5-D56
A2-B92-C5-D56
A3-B92-C5-D56
A9-B92-C5-D56
A13-B92-C5-D56
A24-B92-C5-D56
A69-B92-C5-D56
A67-B92-C5-D56
A39-B92-C5-D56
A65-B92-C5-D56
A66-B92-C5-D56
A2-B4-C6-D56
A3-B4-C6-D56
A9-B4-C6-D56
A13-B4-C6-D56
A24-B4-C6-D56
A69-B4-C6-D56
A67-B4-C6-D56
A39-B4-C6-D56
A65-B4-C6-D56
A66-B4-C6-D56
A2-B5-C6-D56
A3-B5-C6-D56
A9-B5-C6-D56
A13-B5-C6-D56
A24-B5-C6-D56
A69-B5-C6-D56
A67-B5-C6-D56
A39-B5-C6-D56
A65-B5-C6-D56
A66-B5-C6-D56
A2-B6-C6-D56
A3-B6-C6-D56
A9-B6-C6-D56
A13-B6-C6-D56
A24-B6-C6-D56
A69-B6-C6-D56
A67-B6-C6-D56
A39-B6-C6-D56
A65-B6-C6-D56
A66-B6-C6-D56
A2-B32-C6-D56
A3-B32-C6-D56
A9-B32-C6-D56
A13-B32-C6-D56
A24-B32-C6-D56
A69-B32-C6-D56
A67-B32-C6-D56
A39-B32-C6-D56
A65-B32-C6-D56
A66-B32-C6-D56
A2-B39-C6-D56
A3-B39-C6-D56
A9-B39-C6-D56
A13-B39-C6-D56
A24-B39-C6-D56
A69-B39-C6-D56
A67-B39-C6-D56
A39-B39-C6-D56
A65-B39-C6-D56
A66-B39-C6-D56
A2-B45-C6-D56
A3-B45-C6-D56
A9-B45-C6-D56
A13-B45-C6-D56
A24-B45-C6-D56
A69-B45-C6-D56
A67-B45-C6-D56
A39-B45-C6-D56
A65-B45-C6-D56
A66-B45-C6-D56
A2-B53-C6-D56
A3-B53-C6-D56
A9-B53-C6-D56

-continued

A13-B53-C6-D56
A24-B53-C6-D56
A69-B53-C6-D56
A67-B53-C6-D56
A39-B53-C6-D56
A65-B53-C6-D56
A66-B53-C6-D56
A2-B79-C6-D56
A3-B79-C6-D56
A9-B79-C6-D56
A13-B79-C6-D56
A24-B79-C6-D56
A69-B79-C6-D56
A67-B79-C6-D56
A39-B79-C6-D56
A65-B79-C6-D56
A66-B79-C6-D56
A2-B80-C6-D56
A3-B80-C6-D56
A9-B80-C6-D56
A13-B80-C6-D56
A24-B80-C6-D56
A69-B80-C6-D56
A67-B80-C6-D56
A39-B80-C6-D56
A65-B80-C6-D56
A66-B80-C6-D56
A2-B85-C6-D56
A3-B85-C6-D56
A9-B85-C6-D56
A13-B85-C6-D56
A24-B85-C6-D56
A69-B85-C6-D56
A67-B85-C6-D56
A39-B85-C6-D56
A65-B85-C6-D56
A66-B85-C6-D56
A2-B86-C6-D56
A3-B86-C6-D56
A9-B86-C6-D56
A13-B86-C6-D56
A24-B86-C6-D56
A69-B86-C6-D56
A67-B86-C6-D56
A39-B86-C6-D56
A65-B86-C6-D56
A66-B86-C6-D56
A2-B87-C6-D56
A3-B87-C6-D56
A9-B87-C6-D56
A13-B87-C6-D56
A24-B87-C6-D56
A69-B87-C6-D56
A67-B87-C6-D56
A39-B87-C6-D56
A65-B87-C6-D56
A66-B87-C6-D56
A2-B89-C6-D56
A3-B89-C6-D56
A9-B89-C6-D56
A13-B89-C6-D56
A24-B89-C6-D56
A69-B89-C6-D56
A67-B89-C6-D56
A39-B89-C6-D56
A65-B89-C6-D56
A66-B89-C6-D56
A2-B92-C6-D56
A3-B92-C6-D56
A9-B92-C6-D56
A13-B92-C6-D56
A24-B92-C6-D56
A69-B92-C6-D56
A67-B92-C6-D56
A39-B92-C6-D56
A65-B92-C6-D56
A66-B92-C6-D56
A2-B4-C7-D56
A3-B4-C7-D56
A9-B4-C7-D56

-continued

A13-B4-C7-D56
A24-B4-C7-D56
A69-B4-C7-D56
A67-B4-C7-D56
A39-B4-C7-D56
A65-B4-C7-D56
A66-B4-C7-D56
A2-B5-C7-D56
A3-B5-C7-D56
A9-B5-C7-D56
A13-B5-C7-D56
A24-B5-C7-D56
A69-B5-C7-D56
A67-B5-C7-D56
A39-B5-C7-D56
A65-B5-C7-D56
A66-B5-C7-D56
A2-B6-C7-D56
A3-B6-C7-D56
A9-B6-C7-D56
A13-B6-C7-D56
A24-B6-C7-D56
A69-B6-C7-D56
A67-B6-C7-D56
A39-B6-C7-D56
A65-B6-C7-D56
A66-B6-C7-D56
A2-B32-C7-D56
A3-B32-C7-D56
A9-B32-C7-D56
A13-B32-C7-D56
A24-B32-C7-D56
A69-B32-C7-D56
A67-B32-C7-D56
A39-B32-C7-D56
A65-B32-C7-D56
A66-B32-C7-D56
A2-B39-C7-D56
A3-B39-C7-D56
A9-B39-C7-D56
A13-B39-C7-D56
A24-B39-C7-D56
A69-B39-C7-D56
A67-B39-C7-D56
A39-B39-C7-D56
A65-B39-C7-D56
A66-B39-C7-D56
A2-B45-C7-D56
A3-B45-C7-D56
A9-B45-C7-D56
A13-B45-C7-D56
A24-B45-C7-D56
A69-B45-C7-D56
A67-B45-C7-D56
A39-B45-C7-D56
A65-B45-C7-D56
A66-B45-C7-D56
A2-B53-C7-D56
A3-B53-C7-D56
A9-B53-C7-D56
A13-B53-C7-D56
A24-B53-C7-D56
A69-B53-C7-D56
A67-B53-C7-D56
A39-B53-C7-D56
A65-B53-C7-D56
A66-B53-C7-D56
A2-B79-C7-D56
A3-B79-C7-D56
A9-B79-C7-D56
A13-B79-C7-D56
A24-B79-C7-D56
A69-B79-C7-D56
A39-B79-C7-D56
A65-B79-C7-D56
A66-B79-C7-D56
A2-B80-C7-D56
A3-B80-C7-D56
A9-B80-C7-D56

-continued

A13-B80-C7-D56
A24-B80-C7-D56
A69-B80-C7-D56
A67-B80-C7-D56
A39-B80-C7-D56
A65-B80-C7-D56
A66-B80-C7-D56
A2-B85-C7-D56
A3-B85-C7-D56
A9-B85-C7-D56
A13-B85-C7-D56
A24-B85-C7-D56
A69-B85-C7-D56
A67-B85-C7-D56
A39-B85-C7-D56
A65-B85-C7-D56
A66-B85-C7-D56
A2-B86-C7-D56
A3-B86-C7-D56
A9-B86-C7-D56
A13-B86-C7-D56
A24-B86-C7-D56
A69-B86-C7-D56
A67-B86-C7-D56
A39-B86-C7-D56
A65-B86-C7-D56
A66-B86-C7-D56
A2-B87-C7-D56
A3-B87-C7-D56
A9-B87-C7-D56
A13-B87-C7-D56
A24-B87-C7-D56
A69-B87-C7-D56
A67-B87-C7-D56
A39-B87-C7-D56
A65-B87-C7-D56
A66-B87-C7-D56
A2-B89-C7-D56
A3-B89-C7-D56
A9-B89-C7-D56
A13-B89-C7-D56
A24-B89-C7-D56
A69-B89-C7-D56
A67-B89-C7-D56
A39-B89-C7-D56
A65-B89-C7-D56
A66-B89-C7-D56
A2-B92-C7-D56
A3-B92-C7-D56
A9-B92-C7-D56
A13-B92-C7-D56
A24-B92-C7-D56
A69-B92-C7-D56
A67-B92-C7-D56
A39-B92-C7-D56
A65-B92-C7-D56
A66-B92-C7-D56
A2-B4-C8-D56
A3-B4-C8-D56
A9-B4-C8-D56
A13-B4-C8-D56
A24-B4-C8-D56
A69-B4-C8-D56
A67-B4-C8-D56
A39-B4-C8-D56
A65-B4-C8-D56
A66-B4-C8-D56
A2-B5-C8-D56
A3-B5-C8-D56
A9-B5-C8-D56
A13-B5-C8-D56
A24-B5-C8-D56
A69-B5-C8-D56
A67-B5-C8-D56
A39-B5-C8-D56
A65-B5-C8-D56
A66-B5-C8-D56
A2-B6-C8-D56
A3-B6-C8-D56
A9-B6-C8-D56

-continued

A13-B6-C8-D56
A24-B6-C8-D56
A69-B6-C8-D56
A67-B6-C8-D56
A39-B6-C8-D56
A65-B6-C8-D56
A66-B6-C8-D56
A2-B32-C8-D56
A3-B32-C8-D56
A9-B32-C8-D56
A13-B32-C8-D56
A24-B32-C8-D56
A69-B32-C8-D56
A67-B32-C8-D56
A39-B32-C8-D56
A65-B32-C8-D56
A66-B32-C8-D56
A2-B39-C8-D56
A3-B39-C8-D56
A9-B39-C8-D56
A13-B39-C8-D56
A24-B39-C8-D56
A69-B39-C8-D56
A67-B39-C8-D56
A39-B39-C8-D56
A65-B39-C8-D56
A66-B39-C8-D56
A2-B45-C8-D56
A3-B45-C8-D56
A9-B45-C8-D56
A13-B45-C8-D56
A24-B45-C8-D56
A69-B45-C8-D56
A67-B45-C8-D56
A39-B45-C8-D56
A65-B45-C8-D56
A66-B45-C8-D56
A2-B53-C8-D56
A3-B53-C8-D56
A9-B53-C8-D56
A13-B53-C8-D56
A24-B53-C8-D56
A69-B53-C8-D56
A67-B53-C8-D56
A39-B53-C8-D56
A65-B53-C8-D56
A66-B53-C8-D56
A2-B79-C8-D56
A3-B79-C8-D56
A9-B79-C8-D56
A13-B79-C8-D56
A24-B79-C8-D56
A69-B79-C8-D56
A67-B79-C8-D56
A39-B79-C8-D56
A65-B79-C8-D56
A66-B79-C8-D56
A2-B80-C8-D56
A3-B80-C8-D56
A9-B80-C8-D56
A13-B80-C8-D56
A24-B80-C8-D56
A69-B80-C8-D56
A67-B80-C8-D56
A39-B80-C8-D56
A65-B80-C8-D56
A66-B80-C8-D56
A2-B85-C8-D56
A3-B85-C8-D56
A9-B85-C8-D56
A13-B85-C8-D56
A24-B85-C8-D56
A69-B85-C8-D56
A67-B85-C8-D56
A39-B85-C8-D56
A65-B85-C8-D56
A66-B85-C8-D56
A2-B86-C8-D56
A3-B86-C8-D56
A9-B86-C8-D56

-continued

A13-B86-C8-D56
A24-B86-C8-D56
A69-B86-C8-D56
A67-B86-C8-D56
A39-B86-C8-D56
A65-B86-C8-D56
A66-B86-C8-D56
A2-B87-C8-D56
A3-B87-C8-D56
A9-B87-C8-D56
A13-B87-C8-D56
A24-B87-C8-D56
A69-B87-C8-D56
A67-B87-C8-D56
A39-B87-C8-D56
A65-B87-C8-D56
A66-B87-C8-D56
A2-B89-C8-D56
A3-B89-C8-D56
A9-B89-C8-D56
A13-B89-C8-D56
A24-B89-C8-D56
A69-B89-C8-D56
A67-B89-C8-D56
A39-B89-C8-D56
A65-B89-C8-D56
A66-B89-C8-D56
A2-B92-C8-D56
A3-B92-C8-D56
A9-B92-C8-D56
A13-B92-C8-D56
A24-B92-C8-D56
A69-B92-C8-D56
A67-B92-C8-D56
A39-B92-C8-D56
A65-B92-C8-D56
A66-B92-C8-D56
A2-B4-C9-D56
A3-B4-C9-D56
A9-B4-C9-D56
A13-B4-C9-D56
A24-B4-C9-D56
A69-B4-C9-D56
A67-B4-C9-D56
A39-B4-C9-D56
A65-B4-C9-D56
A66-B4-C9-D56
A2-B5-C9-D56
A3-B5-C9-D56
A9-B5-C9-D56
A13-B5-C9-D56
A24-B5-C9-D56
A69-B5-C9-D56
A67-B5-C9-D56
A39-B5-C9-D56
A65-B5-C9-D56
A66-B5-C9-D56
A2-B6-C9-D56
A3-B6-C9-D56
A9-B6-C9-D56
A13-B6-C9-D56
A24-B6-C9-D56
A69-B6-C9-D56
A67-B6-C9-D56
A39-B6-C9-D56
A65-B6-C9-D56
A66-B6-C9-D56
A2-B32-C9-D56
A3-B32-C9-D56
A9-B32-C9-D56
A13-B32-C9-D56
A24-B32-C9-D56
A69-B32-C9-D56
A67-B32-C9-D56
A39-B32-C9-D56
A65-B32-C9-D56
A66-B32-C9-D56
A2-B39-C9-D56
A3-B39-C9-D566
A9-B39-C9-D56

-continued

A13-B39-C9-D56
A24-B39-C9-D56
A69-B39-C9-D56
A67-B39-C9-D56
A39-B39-C9-D56
A65-B39-C9-D56
A66-B39-C9-D56
A2-B45-C9-D56
A3-B45-C9-D56
A9-B45-C9-D56
A13-B45-C9-D56
A24-B45-C9-D56
A69-B45-C9-D56
A67-B45-C9-D56
A39-B45-C9-D56
A65-B45-C9-D56
A66-B45-C9-D56
A2-B53-C9-D56
A3-B53-C9-D56
A9-B53-C9-D56
A13-B53-C9-D56
A24-B53-C9-D56
A69-B53-C9-D56
A67-B53-C9-D56
A39-B53-C9-D56
A65-B53-C9-D56
A66-B53-C9-D56
A2-B79-C9-D56
A3-B79-C9-D56
A9-B79-C9-D56
A13-B79-C9-D56
A24-B79-C9-D56
A69-B79-C9-D56
A67-B79-C9-D56
A39-B79-C9-D56
A65-B79-C9-D56
A66-B79-C9-D56
A2-B80-C9-D56
A3-B80-C9-D56
A9-B80-C9-D56
A13-B80-C9-D56
A24-B80-C9-D56
A69-B80-C9-D56
A67-B80-C9-D56
A39-B80-C9-D56
A65-B80-C9-D56
A66-B80-C9-D56
A2-B85-C9-D56
A3-B85-C9-D56
A9-B85-C9-D56
A13-B85-C9-D56
A24-B85-C9-D56
A69-B85-C9-D56
A67-B85-C9-D56
A39-B85-C9-D56
A65-B85-C9-D56
A66-B85-C9-D56
A2-B86-C9-D56
A3-B86-C9-D56
A9-B86-C9-D56
A13-B86-C9-D56
A24-B86-C9-D56
A69-B86-C9-D56
A67-B86-C9-D56
A39-B86-C9-D56
A65-B86-C9-D56
A66-B86-C9-D56
A2-B87-C9-D56
A3-B87-C9-D56
A9-B87-C9-D56
A13-B87-C9-D56
A24-B87-C9-D56
A69-B87-C9-D56
A67-B87-C9-D56
A39-B87-C9-D56
A65-B87-C9-D56
A66-B87-C9-D56
A2-B89-C9-D56
A3-B89-C9-D56
A9-B89-C9-D56

-continued

A13-B89-C9-D56
A24-B89-C9-D56
A69-B89-C9-D56
A67-B89-C9-D56
A39-B89-C9-D56
A65-B89-C9-D56
A66-B89-C9-D56
A2-B92-C9-D56
A3-B92-C9-D56
A9-B92-C9-D56
A13-B92-C9-D56
A24-B92-C9-D56
A69-B92-C9-D56
A67-B92-C9-D56
A39-B92-C9-D56
A65-B92-C9-D56
A66-B92-C9-D56
A2-B4-C10-D56
A3-B4-C10-D56
A9-B4-C10-D56
A13-B4-C10-D56
A24-B4-C10-D56
A69-B4-C10-D56
A67-B4-C10-D56
A39-B4-C10-D56
A65-B4-C10-D56
A66-B4-C10-D56
A2-B5-C10-D56
A3-B5-C10-D56
A9-B5-C10-D56
A13-B5-C10-D56
A24-B5-C10-D56
A69-B5-C10-D56
A67-B5-C10-D56
A39-B5-C10-D56
A65-B5-C10-D56
A66-B5-C10-D56
A2-B6-C10-D56
A3-B6-C10-D56
A9-B6-C10-D56
A13-B6-C10-D56
A24-B6-C10-D56
A69-B6-C10-D56
A67-B6-C10-D56
A39-B6-C10-D56
A65-B6-C10-D56
A66-B6-C10-D56
A2-B32-C10-D56
A3-B32-C10-D56
A9-B32-C10-D56
A13-B32-C10-D56
A24-B32-C10-D56
A69-B32-C10-D56
A67-B32-C10-D56
A39-B32-C10-D56
A65-B32-C10-D56
A66-B32-C10-D56
A2-B39-C10-D56
A3-B39-C10-D56
A9-B39-C10-D56
A13-B39-C10-D56
A24-B39-C10-D56
A69-B39-C10-D56
A67-B39-C10-D56
A39-B39-C10-D56
A65-B39-C10-D56
A66-B39-C10-D56
A2-B45-C10-D56
A3-B45-C10-D56
A9-B45-C10-D56
A13-B45-C10-D56
A24-B45-C10-D56
A69-B45-C10-D56
A67-B45-C10-D56
A39-B45-C10-D56
A65-B45-C10-D56
A66-B45-C10-D56
A2-B53-C10-D56
A3-B53-C10-D56
A9-B53-C10-D56

-continued

A13-B53-C10-D56
A24-B53-C10-D56
A69-B53-C10-D56
A67-B53-C10-D56
A39-B53-C10-D56
A65-B53-C10-D56
A66-B53-C10-D56
A2-B79-C10-D56
A3-B79-C10-D56
A9-B79-C10-D56
A13-B79-C10-D56
A24-B79-C10-D56
A69-B79-C10-D56
A67-B79-C10-D56
A39-B79-C10-D56
A65-B79-C10-D56
A66-B79-C10-D56
A2-B80-C10-D56
A3-B80-C10-D56
A9-B80-C10-D56
A13-B80-C10-D56
A24-B80-C10-D56
A69-B80-C10-D56
A67-B80-C10-D56
A39-B80-C10-D56
A65-B80-C10-D56
A66-B80-C10-D56
A2-B85-C10-D56
A3-B85-C10-D56
A9-B85-C10-D56
A13-B85-C10-D56
A24-B85-C10-D56
A69-B85-C10-D56
A67-B85-C10-D56
A39-B85-C10-D56
A65-B85-C10-D56
A66-B85-C10-D56
A2-B86-C10-D56
A3-B86-C10-D56
A9-B86-C10-D56
A13-B86-C10-D56
A24-B86-C10-D56
A69-B86-C10-D56
A67-B86-C10-D56
A39-B86-C10-D56
A65-B86-C10-D56
A66-B86-C10-D56
A2-B87-C10-D56
A3-B87-C10-D56
A9-B87-C10-D56
A13-B87-C10-D56
A24-B87-C10-D56
A69-B87-C10-D56
A67-B87-C10-D56
A39-B87-C10-D56
A65-B87-C10-D56
A66-B87-C10-D56
A2-B89-C10-D56
A3-B89-C10-D566
A9-B89-C10-D56
A13-B89-C10-D56
A24-B89-C10-D56
A69-B89-C10-D56
A67-B89-C10-D56
A39-B89-C10-D56
A65-B89-C10-D56
A66-B89-C10-D56
A2-B92-C10-D56
A3-B92-C10-D56
A9-B92-C10-D56
A13-B92-C10-D56
A24-B92-C10-D56
A69-B92-C10-D56
A67-B92-C10-D56
A39-B92-C10-D56
A65-B92-C10-D56
A66-B92-C10-D56
A2-B4-C11-D56
A3-B4-C11-D56
A9-B4-C11-D56

-continued

A13-B4-C11-D56
A24-B4-C11-D56
A69-B4-C11-D56
A67-B4-C11-D56
A39-B4-C11-D56
A65-B4-C11-D56
A66-B4-C11-D56
A2-B5-C11-D56
A3-B5-C11-D56
A9-B5-C11-D56
A13-B5-C11-D56
A24-B5-C11-D56
A69-B5-C11-D56
A67-B5-C11-D56
A39-B5-C11-D56
A65-B5-C11-D56
A66-B5-C11-D56
A2-B6-C11-D56
A3-B6-C11-D56
A9-B6-C11-D56
A13-B6-C11-D56
A24-B6-C11-D56
A69-B6-C11-D56
A67-B6-C11-D56
A39-B6-C11-D56
A65-B6-C11-D56
A66-B6-C11-D56
A2-B32-C11-D56
A3-B32-C11-D56
A9-B32-C11-D56
A13-B32-C11-D56
A24-B32-C11-D56
A69-B32-C11-D56
A67-B32-C11-D56
A39-B32-C11-D56
A65-B32-C11-D56
A66-B32-C11-D56
A2-B39-C11-D56
A3-B39-C11-D56
A9-B39-C11-D56
A13-B39-C11-D56
A24-B39-C11-D56
A69-B39-C11-D56
A67-B39-C11-D56
A39-B39-C11-D56
A65-B39-C11-D56
A66-B39-C11-D56
A2-B45-C11-D56
A3-B45-C11-D56
A9-B45-C11-D56
A13-B45-C11-D56
A24-B45-C11-D56
A69-B45-C11-D56
A67-B45-C11-D56
A39-B45-C11-D56
A65-B45-C11-D56
A66-B45-C11-D56
A2-B53-C11-D56
A3-B53-C11-D56
A9-B53-C11-D56
A13-B53-C11-D56
A24-B53-C11-D56
A69-B53-C11-D56
A67-B53-C11-D56
A39-B53-C11-D56
A65-B53-C11-D56
A66-B53-C11-D56
A2-B79-C11-D56
A3-B79-C11-D56
A9-B79-C11-D56
A13-B79-C11-D56
A24-B79-C11-D56
A69-B79-C11-D56
A67-B79-C11-D56
A39-B79-C11-D56
A65-B79-C11-D56
A66-B79-C11-D56
A2-B80-C11-D56
A3-B80-C11-D56
A9-B80-C11-D56

-continued

A13-B80-C11-D56
A24-B80-C11-D56
A69-B80-C11-D56
A67-B80-C11-D56
A39-B80-C11-D56
A65-B80-C11-D56
A66-B80-C11-D56
A2-B85-C11-D56
A3-B85-C11-D56
A9-B85-C11-D56
A13-B85-C11-D56
A24-B85-C11-D56
A69-B85-C11-D56
A67-B85-C11-D56
A39-B85-C11-D56
A65-B85-C11-D56
A66-B85-C11-D56
A2-B86-C11-D56
A3-B86-C11-D56
A9-B86-C11-D56
A13-B86-C11-D56
A24-B86-C11-D56
A69-B86-C11-D56
A67-B86-C11-D56
A39-B86-C11-D56
A65-B86-C11-D56
A66-B86-C11-D56
A2-B87-C11-D56
A3-B87-C11-D56
A9-B87-C11-D56
A13-B87-C11-D56
A24-B87-C11-D56
A69-B87-C11-D56
A67-B87-C11-D56
A39-B87-C11-D56
A65-B87-C11-D56
A66-B87-C11-D56
A2-B89-C11-D56
A3-B89-C11-D56
A9-B89-C11-D56
A13-B89-C11-D56
A24-B89-C11-D56
A69-B89-C11-D56
A67-B89-C11-D56
A39-B89-C11-D56
A65-B89-C11-D56
A66-B89-C11-D56
A2-B92-C11-D56
A3-B92-C11-D56
A9-B92-C11-D56
A13-B92-C11-D56
A24-B92-C11-D56
A69-B92-C11-D56
A67-B92-C11-D56
A39-B92-C11-D56
A65-B92-C11-D56
A66-B92-C11-D56
A2-B4-C12-D56
A3-B4-C12-D56
A9-B4-C12-D56
A13-B4-C12-D56
A24-B4-C12-D56
A69-B4-C12-D56
A67-B4-C12-D56
A39-B4-C12-D56
A65-B4-C12-D56
A66-B4-C12-D56
A2-B5-C12-D56
A3-B5-C12-D56
A9-B5-C12-D56
A13-B5-C12-D56
A24-B5-C12-D56
A69-B5-C12-D56
A67-B5-C12-D56
A39-B5-C12-D56
A65-B5-C12-D56
A66-B5-C12-D56
A2-B6-C12-D56
A3-B6-C12-D56
A9-B6-C12-D56

-continued

A13-B6-C12-D56
A24-B6-C12-D56
A69-B6-C12-D56
A67-B6-C12-D56
A39-B6-C12-D56
A65-B6-C12-D56
A66-B6-C12-D56
A2-B32-C12-D56
A3-B32-C12-D56
A9-B32-C12-D56
A13-B32-C12-D56
A24-B32-C12-D56
A69-B32-C12-D56
A67-B32-C12-D56
A39-B32-C12-D56
A65-B32-C12-D56
A66-B32-C12-D56
A2-B39-C12-D56
A3-B39-C12-D56
A9-B39-C12-D56
A13-B39-C12-D56
A24-B39-C12-D56
A69-B39-C12-D56
A67-B39-C12-D56
A39-B39-C12-D56
A65-B39-C12-D56
A66-B39-C12-D56
A2-B45-C12-D56
A3-B45-C12-D56
A9-B45-C12-D56
A13-B45-C12-D56
A24-B45-C12-D56
A69-B45-C12-D56
A67-B45-C12-D56
A39-B45-C12-D56
A65-B45-C12-D56
A66-B45-C12-D56
A2-B53-C12-D56
A3-B53-C12-D56
A9-B53-C12-D56
A13-B53-C12-D56
A24-B53-C12-D56
A69-B53-C12-D56
A67-B53-C12-D56
A39-B53-C12-D56
A65-B53-C12-D56
A66-B53-C12-D56
A2-B79-C12-D56
A3-B79-C12-D56
A9-B79-C12-D56
A13-B79-C12-D56
A24-B79-C12-D56
A69-B79-C12-D56
A67-B79-C12-D56
A39-B79-C12-D56
A65-B79-C12-D56
A66-B79-C12-D56
A2-B80-C12-D56
A3-B80-C12-D56
A9-B80-C12-D56
A13-B80-C12-D56
A24-B80-C12-D56
A69-B80-C12-D56
A67-B80-C12-D56
A39-B80-C12-D56
A65-B80-C12-D56
A66-B80-C12-D56
A2-B85-C12-D56
A3-B85-C12-D56
A9-B85-C12-D56
A13-B85-C12-D56
A24-B85-C12-D56
A69-B85-C12-D56
A67-B85-C12-D56
A39-B85-C12-D56
A65-B85-C12-D56
A66-B85-C12-D56
A2-B86-C12-D56
A3-B86-C12-D56
A9-B86-C12-D56

-continued

A13-B8-C12-D56
A24-B86-C12-D56
A69-B86-C12-D56
A67-B86-C12-D56
A39-B86-C12-D56
A65-B86-C12-D56
A66-B86-C12-D56
A2-B87-C12-D56
A3-B87-C12-D56
A9-B87-C12-D56
A13-B87-C12-D56
A24-B87-C12-D56
A69-B87-C12-D56
A67-B87-C12-D56
A39-B87-C12-D56
A65-B87-C12-D56
A66-B87-C12-D56
A2-B89-C12-D56
A3-B89-C12-D56
A9-B89-C12-D56
A13-B89-C12-D56
A24-B89-C12-D56
A69-B89-C12-D56
A67-B89-C12-D56
A39-B89-C12-D56
A65-B89-C12-D56
A66-B89-C12-D56
A2-B92-C12-D56
A3-B92-C12-D56
A9-B92-C12-D56
A13-B92-C12-D56
A24-B92-C12-D56
A69-B92-C12-D56
A67-B92-C12-D56
A39-B92-C12-D56
A65-B92-C12-D56
A66-B92-C12-D56
A2-B4-C13-D56
A3-B4-C13-D56
A9-B4-C13-D56
A13-B4-C13-D56
A24-B4-C13-D56
A69-B4-C13-D56
A67-B4-C13-D56
A39-B4-C13-D56
A65-B4-C13-D56
A66-B4-C13-D56
A2-B5-C13-D56
A3-B5-C13-D56
A9-B5-C13-D56
A13-B5-C13-D56
A24-B5-C13-D56
A69-B5-C13-D56
A67-B5-C13-D56
A39-B5-C13-D56
A65-B5-C13-D56
A66-B5-C13-D56
A2-B6-C13-D56
A3-B6-C13-D56
A9-B6-C13-D56
A13-B6-C13-D56
A24-B6-C13-D56
A69-B6-C13-D56
A67-B6-C13-D56
A39-B6-C13-D56
A65-B6-C13-D56
A66-B6-C13-D56
A2-B32-C13-D56
A3-B32-C13-D56
A9-B32-C13-D56
A13-B32-C13-D56
A24-B32-C13-D56
A69-B32-C13-D56
A67-B32-C13-D56
A39-B32-C13-D56
A65-B32-C13-D56
A66-B32-C13-D56
A2-B39-C13-D56
A3-B39-C13-D56
A9-B39-C13-D56

-continued
A13-B39-C13-D56
A24-B39-C13-D56
A69-B39-C13-D56
A67-B39-C13-D56
A39-B39-C13-D56
A65-B39-C13-D56
A66-B39-C13-D56
A2-B45-C13-D56
A3-B45-C13-D56
A9-B45-C13-D56
A13-B45-C13-D56
A24-B45-C13-D56
A69-B45-C13-D56
A67-B45-C13-D56
A39-B45-C13-D56
A65-B45-C13-D56
A66-B45-C13-D56
A2-B53-C13-D56
A3-B53-C13-D56
A9-B53-C13-D56
A13-B53-C13-D56
A24-B53-C13-D56
A69-B53-C13-D56
A67-B53-C13-D56
A39-B53-C13-D56
A65-B53-C13-D56
A66-B53-C13-D56
A2-B79-C13-D56
A3-B79-C13-D56
A9-B79-C13-D56
A13-B79-C13-D56
A24-B79-C13-D56
A69-B79-C13-D56
A67-B79-C13-D56
A39-B79-C13-D56
A65-B79-C13-D56
A66-B79-C13-D56
A2-B80-C13-D56
A3-B80-C13-D56
A9-B80-C13-D56
A13-B80-C13-D56
A24-B80-C13-D56
A69-B80-C13-D56
A67-B80-C13-D56
A39-B80-C13-D56
A65-B80-C13-D56
A66-B80-C13-D56
A2-B85-C13-D56
A3-B85-C13-D56
A9-B85-C13-D56
A13-B85-C13-D56
A24-B85-C13-D56
A69-B85-C13-D56
A67-B85-C13-D56
A39-B85-C13-D56
A65-B85-C13-D56
A66-B85-C13-D56
A2-B86-C13-D56
A3-B86-C13-D56
A9-B86-C13-D56
A13-B86-C13-D56
A24-B86-C13-D56
A69-B86-C13-D56
A67-B86-C13-D56
A39-B86-C13-D56
A65-B86-C13-D56
A66-B86-C13-D56
A2-B87-C13-D56
A3-B87-C13-D56
A9-B87-C13-D56
A13-B87-C13-D56
A24-B87-C13-D56
A69-B87-C13-D56
A67-B87-C13-D56
A39-B87-C13-D56
A65-B87-C13-D56
A66-B87-C13-D56
A2-B89-C13-D56
A3-B89-C13-D56
A9-B89-C13-D56

-continued
A13-B89-C13-D56
A24-B89-C13-D56
A69-B89-C13-D56
A67-B89-C13-D56
A39-B89-C13-D56
A65-B89-C13-D56
A66-B89-C13-D56
A2-B92-C13-D56
A3-B92-C13-D56
A9-B92-C13-D56
A13-B92-C13-D56
A24-B92-C13-D56
A69-B92-C13-D56
A67-B92-C13-D56
A39-B92-C13-D56
A65-B92-C13-D56
A66-B92-C13-D56
A2-B4-E1
A3-B4-E1
A9-B4-E1
A13-B4-E1
A24-B4-E1
A69-B4-E1
A67-B4-E1
A39-B4-E1
A65-B4-E1
A66-B4-E1
A2-B5-E1
A3-B5-E1
A9-B5-E1
A13-B5-E1
A24-B5-E1
A69-B5-E1
A67-B5-E1
A39-B5-E1
A65-B5-E1
A66-B5-E1
A2-B6-E1
A3-B6-E1
A9-B6-E1
A13-B6-E1
A24-B6-E1
A69-B6-E1
A67-B6-E1
A39-B6-E1
A65-B6-E1
A66-B6-E1
A2-B32-E1
A3-B32-E1
A9-B32-E1
A13-B32-E1
A24-B32-E1
A69-B32-E1
A67-B32-E1
A39-B32-E1
A65-B32-E1
A66-B32-E1
A2-B39-E1
A3-B39-E1
A9-B39-E1
A13-B39-E1
A24-B39-E1
A69-B39-E1
A67-B39-E1
A39-B39-E1
A65-B39-E1
A66-B39-E1
A2-B45-E1
A3-B45-E1
A9-B45-E1
A13-B45-E1
A24-B45-E1
A69-B45-E1
A67-B45-E1
A39-B45-E1
A65-B45-E1
A66-B45-E1
A2-B53-E1
A3-B53-E1
A9-B53-E1

-continued

A13-B53-E1
A24-B53-E1
A69-B53-E1
A67-B53-E1
A39-B53-E1
A65-B53-E1
A66-B53-E1
A2-B79-E1
A3-B79-E1
A9-B79-E1
A13-B79-E1
A24-B79-E1
A69-B79-E1
A67-B79-E1
A39-B79-E1
A65-B79-E1
A66-B79-E1
A2-B80-E1
A3-B80-E1
A9-B80-E1
A13-B80-E1
A24-B80-E1
A69-B80-E1
A67-B80-E1
A39-B80-E1
A65-B80-E1
A66-B80-E1
A2-B85-E1
A3-B85-E1
A9-B85-E1
A13-B85-E1
A24-B85-E1
A69-B85-E1
A67-B85-E1
A39-B85-E1
A65-B85-E1
A66-B85-E1
A2-B86-E1
A3-B86-E1
A9-B86-E1
A13-B86-E1
A24-B86-E1
A69-B86-E1
A67-B86-E1
A39-B86-E1
A65-B86-E1
A66-B86-E1
A2-B87-E1
A3-B87-E1
A9-B87-E1
A13-B87-E1
A24-B87-E1
A69-B87-E1
A67-B87-E1
A39-B87-E1
A65-B87-E1
A66-B87-E1
A2-B89-E1
A3-B89-E1
A9-B89-E1
A13-B89-E1
A24-B89-E1
A69-B89-E1
A67-B89-E1
A39-B89-E1
A65-B89-E1
A66-B89-E1
A2-B92-E1
A3-B92-E1
A9-B92-E1
A13-B92-E1
A24-B92-E1
A69-B92-E1
A67-B92-E1
A39-B92-E1
A65-B92-E1
A66-B92-E1
A2-B4-E2
A3-B4-E2
A9-B4-E2

-continued

A13-B4-E2
A24-B4-E2
A69-B4-E2
A67-B4-E2
A39-B4-E2
A65-B4-E2
A66-B4-E2
A2-B5-E2
A3-B5-E2
A9-B5-E2
A13-B5-E2
A24-B5-E2
A69-B5-E2
A67-B5-E2
A39-B5-E2
A65-B5-E2
A66-B5-E2
A2-B6-E2
A3-B6-E2
A9-B6-E2
A13-B6-E2
A24-B6-E2
A69-B6-E2
A67-B6-E2
A39-B6-E2
A65-B6-E2
A66-B6-E2
A2-B32-E2
A3-B32-E2
A9-B32-E2
A13-B32-E2
A24-B32-E2
A69-B32-E2
A67-B32-E2
A39-B32-E2
A65-B32-E2
A66-B32-E2
A2-B39-E2
A3-B39-E2
A9-B39-E2
A13-B39-E2
A24-B39-E2
A69-B39-E2
A67-B39-E2
A39-B39-E2
A65-B39-E2
A66-B39-E2
A2-B45-E2
A3-B45-E2
A9-B45-E2
A13-B45-E2
A24-B45-E2
A69-B45-E2
A67-B45-E2
A39-B45-E2
A65-B45-E2
A66-B45-E2
A2-B53-E2
A3-B53-E2
A9-B53-E2
A13-B53-E2
A24-B53-E2
A69-B53-E2
A67-B53-E2
A39-B53-E2
A65-B53-E2
A66-B53-E2
A2-B79-E2
A3-B79-E2
A9-B79-E2
A13-B79-E2
A24-B79-E2
A69-B79-E2
A67-B79-E2
A39-B79-E2
A65-B79-E2
A66-B79-E2
A2-B80-E2
A3-B80-E2
A9-B80-E2

-continued

| | |
|---|---|
| A13-B80-E2 | A13-B6-E3 |
| A24-B80-E2 | A24-B6-E3 |
| A69-B80-E2 | A69-B6-E3 |
| A67-B80-E2 | A67-B6-E3 |
| A39-B80-E2 | A39-B6-E3 |
| A65-B80-E2 | A65-B6-E3 |
| A66-B80-E2 | A66-B6-E3 |
| A2-B85-E2 | A2-B32-E3 |
| A3-B85-E2 | A3-B32-E3 |
| A9-B85-E2 | A9-B32-E3 |
| A13-B85-E2 | A13-B32-E3 |
| A24-B85-E2 | A24-B32-E3 |
| A69-B85-E2 | A69-B32-E3 |
| A67-B85-E2 | A67-B32-E3 |
| A39-B85-E2 | A39-B32-E3 |
| A65-B85-E2 | A65-B32-E3 |
| A66-B85-E2 | A66-B32-E3 |
| A2-B86-E2 | A2-B39-E3 |
| A3-B86-E2 | A3-B39-E3 |
| A9-B86-E2 | A9-B39-E3 |
| A13-B86-E2 | A13-B39-E3 |
| A24-B86-E2 | A24-B39-E3 |
| A69-B86-E2 | A69-B39-E3 |
| A67-B86-E2 | A67-B39-E3 |
| A39-B86-E2 | A39-B39-E3 |
| A65-B86-E2 | A65-B39-E3 |
| A66-B86-E2 | A66-B39-E3 |
| A2-B87-E2 | A2-B45-E3 |
| A3-B87-E2 | A3-B45-E3 |
| A9-B87-E2 | A9-B45-E3 |
| A13-B87-E2 | A13-B45-E3 |
| A24-B87-E2 | A24-B45-E3 |
| A69-B87-E2 | A69-B45-E3 |
| A67-B87-E2 | A67-B45-E3 |
| A39-B87-E2 | A39-B45-E3 |
| A65-B87-E2 | A65-B45-E3 |
| A66-B87-E2 | A66-B45-E3 |
| A2-B89-E2 | A2-B53-E3 |
| A3-B89-E2 | A3-B53-E3 |
| A9-B89-E2 | A9-B53-E3 |
| A13-B89-E2 | A13-B53-E3 |
| A24-B89-E2 | A24-B53-E3 |
| A69-B89-E2 | A69-B53-E3 |
| A67-B89-E2 | A67-B53-E3 |
| A39-B89-E2 | A39-B53-E3 |
| A65-B89-E2 | A65-B53-E3 |
| A66-B89-E2 | A66-B53-E3 |
| A2-B92-E2 | A2-B79-E3 |
| A3-B92-E2 | A3-B79-E3 |
| A9-B92-E2 | A9-B79-E3 |
| A13-B92-E2 | A13-B79-E3 |
| A24-B92-E2 | A24-B79-E3 |
| A69-B92-E2 | A69-B79-E3 |
| A67-B92-E2 | A67-B79-E3 |
| A39-B92-E2 | A39-B79-E3 |
| A65-B92-E2 | A65-B79-E3 |
| A66-B92-E2 | A66-B79-E3 |
| A2-B4-E3 | A2-B80-E3 |
| A3-B4-E3 | A3-B80-E3 |
| A9-B4-E3 | A9-B80-E3 |
| A13-B4-E3 | A13-B80-E3 |
| A24-B4-E3 | A24-B80-E3 |
| A69-B4-E3 | A69-B80-E3 |
| A67-B4-E3 | A67-B80-E3 |
| A39-B4-E3 | A39-B80-E3 |
| A65-B4-E3 | A65-B80-E3 |
| A66-B4-E3 | A66-B80-E3 |
| A2-B5-E3 | A2-B85-E3 |
| A3-B5-E3 | A3-B85-E3 |
| A9-B5-E3 | A9-B85-E3 |
| A13-B5-E3 | A13-B85-E3 |
| A24-B5-E3 | A24-B85-E3 |
| A69-B5-E3 | A69-B85-E3 |
| A67-B5-E3 | A67-B85-E3 |
| A39-B5-E3 | A39-B85-E3 |
| A65-B5-E3 | A65-B85-E3 |
| A66-B5-E3 | A66-B85-E3 |
| A2-B6-E3 | A2-B86-E3 |
| A3-B6-E3 | A3-B86-E3 |
| A9-B6-E3 | A9-B86-E3 |

-continued

A13-B86-E3
A24-B86-E3
A69-B86-E3
A67-B86-E3
A39-B86-E3
A65-B86-E3
A66-B86-E3
A2-B87-E3
A3-B87-E3
A9-B87-E3
A13-B87-E3
A24-B87-E3
A69-B87-E3
A67-B87-E3
A39-B87-E3
A65-B87-E3
A66-B87-E3
A2-B89-E3
A3-B89-E3
A9-B89-E3
A13-B89-E3
A24-B89-E3
A69-B89-E3
A67-B89-E3
A39-B89-E3
A65-B89-E3
A66-B89-E3
A2-B92-E3
A3-B92-E3
A9-B92-E3
A13-B92-E3
A24-B92-E3
A69-B92-E3
A67-B92-E3
A39-B92-E3
A65-B92-E3
A66-B92-E3
A2-B4-E4
A3-B4-E4
A9-B4-E4
A13-B4-E4
A24-B4-E4
A69-B4-E4
A67-B4-E4
A39-B4-E4
A65-B4-E4
A66-B4-E4
A2-B5-E4
A3-B5-E4
A9-B5-E4
A13-B5-E4
A24-B5-E4
A69-B5-E4
A67-B5-E4
A39-B5-E4
A65-B5-E4
A66-B5-E4
A2-B6-E4
A3-B6-E4
A9-B6-E4
A13-B6-E4
A24-B6-E4
A69-B6-E4
A67-B6-E4
A39-B6-E4
A65-B6-E4
A66-B6-E4
A2-B32-E4
A3-B32-E4
A9-B32-E4
A13-B32-E4
A24-B32-E4
A69-B32-E4
A67-B32-E4
A39-B32-E4
A65-B32-E4
A66-B32-E4
A2-B39-E4
A3-B39-E4
A9-B39-E4

-continued

A13-B39-E4
A24-B39-E4
A69-B39-E4
A67-B39-E4
A39-B39-E4
A65-B39-E4
A66-B39-E4
A2-B45-E4
A3-B45-E4
A9-B45-E4
A13-B45-E4
A24-B45-E4
A69-B45-E4
A67-B45-E4
A39-B45-E4
A65-B45-E4
A66-B45-E4
A2-B53-E4
A3-B53-E4
A9-B53-E4
A13-B53-E4
A24-B53-E4
A69-B53-E4
A67-B53-E4
A39-B53-E4
A65-B53-E4
A66-B53-E4
A2-B79-E4
A3-B79-E4
A9-B79-E4
A13-B79-E4
A24-B79-E4
A69-B79-E4
A67-B79-E4
A39-B79-E4
A65-B79-E4
A66-B79-E4
A2-B80-E4
A3-B80-E4
A9-B80-E4
A13-B80-E4
A24-B80-E4
A69-B80-E4
A67-B80-E4
A39-B80-E4
A65-B80-E4
A66-B80-E4
A2-B85-E4
A3-B85-E4
A9-B85-E4
A13-B85-E4
A24-B85-E4
A69-B85-E4
A67-B85-E4
A39-B85-E4
A65-B85-E4
A66-B85-E4
A2-B86-E4
A3-B86-E4
A9-B86-E4
A13-B86-E4
A24-B86-E4
A69-B86-E4
A67-B86-E4
A39-B86-E4
A65-B86-E4
A66-B86-E4
A2-B87-E4
A3-B87-E4
A9-B87-E4
A13-B87-E4
A24-B87-E4
A69-B87-E4
A67-B87-E4
A39-B87-E4
A65-B87-E4
A66-B87-E4
A2-B89-E4
A3-B89-E4
A9-B89-E4

-continued

A13-B89-E4
A24-B89-E4
A69-B89-E4
A67-B89-E4
A39-B89-E4
A65-B89-E4
A66-B89-E4
A2-B92-E4
A3-B92-E4
A9-B92-E4
A13-B92-E4
A24-B92-E4
A69-B92-E4
A67-B92-E4
A39-B92-E4
A65-B92-E4
A66-B92-E4
A2-B4-E5
A3-B4-E5
A9-B4-E5
A13-B4-E5
A24-B4-E5
A69-B4-E5
A67-B4-E5
A39-B4-E5
A65-B4-E5
A66-B4-E5
A2-B5-E5
A3-B5-E5
A9-B5-E5
A13-B5-E5
A24-B5-E5
A69-B5-E5
A67-B5-E5
A39-B5-E5
A65-B5-E5
A66-B5-E5
A2-B6-E5
A3-B6-E5
A9-B6-E5
A13-B6-E5
A24-B6-E5
A69-B6-E5
A67-B6-E5
A39-B6-E5
A65-B6-E5
A66-B6-E5
A2-B32-E5
A3-B32-E5
A9-B32-E5
A13-B32-E5
A24-B32-E5
A69-B32-E5
A67-B32-E5
A39-B32-E5
A65-B32-E5
A66-B32-E5
A2-B39-E5
A3-B39-E5
A9-B39-E5
A13-B39-E5
A24-B39-E5
A69-B39-E5
A67-B39-E5
A39-B39-E5
A65-B39-E5
A66-B39-E5
A2-B45-E5
A3-B45-E5
A9-B45-E5
A13-B45-E5
A24-B45-E5
A69-B45-E5
A67-B45-E5
A39-B45-E5
A65-B45-E5
A66-B45-E5
A2-B53-E5
A3-B53-E5
A9-B53-E5

-continued

A13-B53-E5
A24-B53-E5
A69-B53-E5
A67-B53-E5
A39-B53-E5
A65-B53-E5
A66-B53-E5
A2-B79-E5
A3-B79-E5
A9-B79-E5
A13-B79-E5
A24-B79-E5
A69-B79-E5
A67-B79-E5
A39-B79-E5
A65-B79-E5
A66-B79-E5
A2-B80-E5
A3-B80-E5
A9-B80-E5
A13-B80-E5
A24-B80-E5
A69-B80-E5
A67-B80-E5
A39-B80-E5
A65-B80-E5
A66-B80-E5
A2-B85-E5
A3-B85-E5
A9-B85-E5
A13-B85-E5
A24-B85-E5
A69-B85-E5
A67-B85-E5
A39-B85-E5
A65-B85-E5
A66-B85-E5
A2-B86-E5
A3-B86-E5
A9-B86-E5
A13-B86-E5
A24-B86-E5
A69-B86-E5
A67-B86-E5
A39-B86-E5
A65-B86-E5
A66-B86-E5
A2-B87-E5
A3-B87-E5
A9-B87-E5
A13-B87-E5
A24-B87-E5
A69-B87-E5
A67-B87-E5
A39-B87-E5
A65-B87-E5
A66-B87-E5
A2-B89-E5
A3-B89-E5
A9-B89-E5
A13-B89-E5
A24-B89-E5
A69-B89-E5
A67-B89-E5
A39-B89-E5
A65-B89-E5
A66-B89-E5
A2-B92-E5
A3-B92-E5
A9-B92-E5
A13-B92-E5
A24-B92-E5
A69-B92-E5
A67-B92-E5
A39-B92-E5
A65-B92-E5
A66-B92-E5
A2-B4-E6
A3-B4-E6
A9-B4-E6

-continued
A13-B4-E6
A24-B4-E6
A69-B4-E6
A67-B4-E6
A39-B4-E6
A65-B4-E6
A66-B4-E6
A2-B5-E6
A3-B5-E6
A9-B5-E6
A13-B5-E6
A24-B5-E6
A69-B5-E6
A67-B5-E6
A39-B5-E6
A65-B5-E6
A66-B5-E6
A2-B6-E6
A3-B6-E6
A9-B6-E6
A13-B6-E6
A24-B6-E6
A69-B6-E6
A67-B6-E6
A39-B6-E6
A65-B6-E6
A66-B6-E6
A2-B32-E6
A3-B32-E6
A9-B32-E6
A13-B32-E6
A24-B32-E6
A69-B32-E6
A67-B32-E6
A39-B32-E6
A65-B32-E6
A66-B32-E6
A2-B39-E6
A3-B39-E6
A9-B39-E6
A13-B39-E6
A24-B39-E6
A69-B39-E6
A67-B39-E6
A39-B39-E6
A65-B39-E6
A66-B39-E6
A2-B45-E6
A3-B45-E6
A9-B45-E6
A13-B45-E6
A24-B45-E6
A69-B45-E6
A67-B45-E6
A39-B45-E6
A65-B45-E6
A66-B45-E6
A2-B53-E6
A3-B53-E6
A9-B53-E6
A13-B53-E6
A24-B53-E6
A69-B53-E6
A67-B53-E6
A39-B53-E6
A65-B53-E6
A66-B53-E6
A2-B79-E6
A3-B79-E6
A9-B79-E6
A13-B79-E6
A24-B79-E6
A69-B79-E6
A67-B79-E6
A39-B79-E6
A65-B79-E6
A66-B79-E6
A2-B80-E6
A3-B80-E6
A9-B80-E6

-continued
A13-B80-E6
A24-B80-E6
A69-B80-E6
A67-B80-E6
A39-B80-E6
A65-B80-E6
A66-B80-E6
A2-B85-E6
A3-B85-E6
A9-B85-E6
A13-B85-E6
A24-B85-E6
A69-B85-E6
A67-B85-E6
A39-B85-E6
A65-B85-E6
A66-B85-E6
A2-B86-E6
A3-B86-E6
A9-B86-E6
A13-B86-E6
A24-B86-E6
A69-B86-E6
A67-B86-E6
A39-B86-E6
A65-B86-E6
A66-B86-E6
A2-B87-E6
A3-B87-E6
A9-B87-E6
A13-B87-E6
A24-B87-E6
A69-B87-E6
A67-B87-E6
A39-B87-E6
A65-B87-E6
A66-B87-E6
A2-B89-E6
A3-B89-E6
A9-B89-E6
A13-B89-E6
A24-B89-E6
A69-B89-E6
A67-B89-E6
A39-B89-E6
A65-B89-E6
A66-B89-E6
A2-B92-E6
A3-B92-E6
A9-B92-E6
A13-B92-E6
A24-B92-E6
A69-B92-E6
A67-B92-E6
A39-B92-E6
A65-B92-E6
A66-B92-E6
A2-B4-E7
A3-B4-E7
A9-B4-E7
A13-B4-E7
A24-B4-E7
A69-B4-E7
A67-B4-E7
A39-B4-E7
A65-B4-E7
A66-B4-E7
A2-B5-E7
A3-B5-E7
A9-B5-E7
A13-B5-E7
A24-B5-E7
A69-B5-E7
A67-B5-E7
A39-B5-E7
A65-B5-E7
A66-B5-E7
A2-B6-E7
A3-B6-E7
A9-B6-E7

-continued

A13-B6-E7
A24-B6-E7
A69-B6-E7
A67-B6-E7
A39-B6-E7
A65-B6-E7
A66-B6-E7
A2-B32-E7
A3-B32-E7
A9-B32-E7
A13-B32-E7
A24-B32-E7
A69-B32-E7
A67-B32-E7
A39-B32-E7
A65-B32-E7
A66-B32-E7
A2-B39-E7
A3-B39-E7
A9-B39-E7
A13-B39-E7
A24-B39-E7
A69-B39-E7
A67-B39-E7
A39-B39-E7
A65-B39-E7
A66-B39-E7
A2-B45-E7
A3-B45-E7
A9-B45-E7
A13-B45-E7
A24-B45-E7
A69-B45-E7
A67-B45-E7
A39-B45-E7
A65-B45-E7
A66-B45-E7
A2-B53-E7
A3-B53-E7
A9-B53-E7
A13-B53-E7
A24-B53-E7
A69-B53-E7
A67-B53-E7
A39-B53-E7
A65-B53-E7
A66-B53-E7
A2-B79-E7
A3-B79-E7
A9-B79-E7
A13-B79-E7
A24-B79-E7
A69-B79-E7
A67-B79-E7
A39-B79-E7
A65-B79-E7
A66-B79-E7
A2-B80-E7
A3-B80-E7
A9-B80-E7
A13-B80-E7
A24-B80-E7
A69-B80-E7
A67-B80-E7
A39-B80-E7
A65-B80-E7
A66-B80-E7
A2-B85-E7
A3-B85-E7
A9-B85-E7
A13-B85-E7
A24-B85-E7
A69-B85-E7
A67-B85-E7
A39-B85-E7
A65-B85-E7
A66-B85-E7
A2-B86-E7
A3-B86-E7
A9-B86-E7

-continued

A13-B86-E7
A24-B86-E7
A69-B86-E7
A67-B86-E7
A39-B86-E7
A65-B86-E7
A66-B86-E7
A2-B87-E7
A3-B87-E7
A9-B87-E7
A13-B87-E7
A24-B87-E7
A69-B87-E7
A67-B87-E7
A39-B87-E7
A65-B87-E7
A66-B87-E7
A2-B89-E7
A3-B89-E7
A9-B89-E7
A13-B89-E7
A24-B89-E7
A69-B89-E7
A67-B89-E7
A39-B89-E7
A65-B89-E7
A66-B89-E7
A2-B92-E7
A3-B92-E7
A9-B92-E7
A13-B92-E7
A24-B92-E7
A69-B92-E7
A67-B92-E7
A39-B92-E7
A65-B92-E7
A66-B92-E7
A2-B4-E8
A3-B4-E8
A9-B4-E8
A13-B4-E8
A24-B4-E8
A69-B4-E8
A67-B4-E8
A39-B4-E8
A65-B4-E8
A66-B4-E8
A2-B5-E8
A3-B5-E8
A9-B5-E8
A13-B5-E8
A24-B5-E8
A69-B5-E8
A67-B5-E8
A39-B5-E8
A65-B5-E8
A66-B5-E8
A2-B6-E8
A3-B6-E8
A9-B6-E8
A13-B6-E8
A24-B6-E8
A69-B6-E8
A67-B6-E8
A39-B6-E8
A65-B6-E8
A66-B6-E8
A2-B32-E8
A3-B32-E8
A9-B32-E8
A13-B32-E8
A24-B32-E8
A69-B32-E8
A67-B32-E8
A39-B32-E8
A65-B32-E8
A66-B32-E8
A2-B39-E8
A3-B39-E8
A9-B39-E8

-continued

A13-B39-E8
A24-B39-E8
A69-B39-E8
A67-B39-E8
A39-B39-E8
A65-B39-E8
A66-B39-E8
A2-B45-E8
A3-B45-E8
A9-B45-E8
A13-B45-E8
A24-B45-E8
A69-B45-E8
A67-B45-E8
A39-B45-E8
A65-B45-E8
A66-B45-E8
A2-B53-E8
A3-B53-E8
A9-B53-E8
A13-B53-E8
A24-B53-E8
A69-B53-E8
A67-B53-E8
A39-B53-E8
A65-B53-E8
A66-B53-E8
A2-B79-E8
A3-B79-E8
A9-B79-E8
A13-B79-E8
A24-B79-E8
A69-B79-E8
A67-B79-E8
A39-B79-E8
A65-B79-E8
A66-B79-E8
A2-B80-E8
A3-B80-E8
A9-B80-E8
A13-B80-E8
A24-B80-E8
A69-B80-E8
A67-B80-E8
A39-B80-E8
A65-B80-E8
A66-B80-E8
A2-B85-E8
A3-B85-E8
A9-B85-E8
A13-B85-E8
A24-B85-E8
A69-B85-E8
A67-B85-E8
A39-B85-E8
A65-B85-E8
A66-B85-E8
A2-B86-E8
A3-B86-E8
A9-B86-E8
A13-B86-E8
A24-B86-E8
A69-B86-E8
A67-B86-E8
A39-B86-E8
A65-B86-E8
A66-B86-E8
A2-B87-E8
A3-B87-E8
A9-B87-E8
A13-B87-E8
A24-B87-E8
A69-B87-E8
A67-B87-E8
A39-B87-E8
A65-B87-E8
A66-B87-E8
A2-B89-E8
A3-B89-E8
A9-B89-E8

-continued

A13-B89-E8
A24-B89-E8
A69-B89-E8
A67-B89-E8
A39-B89-E8
A65-B89-E8
A66-B89-E8
A2-B92-E8
A3-B92-E8
A9-B92-E8
A13-B92-E8
A24-B92-E8
A69-B92-E8
A67-B92-E8
A39-B92-E8
A65-B92-E8
A66-B92-E8
A2-B4-E9
A3-B4-E9
A9-B4-E9
A13-B4-E9
A24-B4-E9
A69-B4-E9
A67-B4-E9
A39-B4-E9
A65-B4-E9
A66-B4-E9
A2-B5-E9
A3-B5-E9
A9-B5-E9
A13-B5-E9
A24-B5-E9
A69-B5-E9
A67-B5-E9
A39-B5-E9
A65-B5-E9
A66-B5-E9
A2-B6-E9
A3-B6-E9
A9-B6-E9
A13-B6-E9
A24-B6-E9
A69-B6-E9
A67-B6-E9
A39-B6-E9
A65-B6-E9
A66-B6-E9
A2-B32-E9
A3-B32-E9
A9-B32-E9
A13-B32-E9
A24-B32-E9
A69-B32-E9
A67-B32-E9
A39-B32-E9
A65-B32-E9
A66-B32-E9
A2-B39-E9
A3-B39-E9
A9-B39-E9
A13-B39-E9
A24-B39-E9
A69-B39-E9
A67-B39-E9
A39-B39-E9
A65-B39-E9
A66-B39-E9
A2-B45-E9
A3-B45-E9
A9-B45-E9
A13-B45-E9
A24-B45-E9
A69-B45-E9
A67-B45-E9
A39-B45-E9
A65-B45-E9
A66-B45-E9
A2-B53-E9
A3-B53-E9
A9-B53-E9

-continued

A13-B53-E9
A24-B53-E9
A69-B53-E9
A67-B53-E9
A39-B53-E9
A65-B53-E9
A66-B53-E9
A2-B79-E9
A3-B79-E9
A9-B79-E9
A13-B79-E9
A24-B79-E9
A69-B79-E9
A67-B79-E9
A39-B79-E9
A65-B79-E9
A66-B79-E9
A2-B80-E9
A3-B80-E9
A9-B80-E9
A13-B80-E9
A24-B80-E9
A69-B80-E9
A67-B80-E9
A39-B80-E9
A65-B80-E9
A66-B80-E9
A2-B85-E9
A3-B85-E9
A9-B85-E9
A13-B85-E9
A24-B85-E9
A69-B85-E9
A67-B85-E9
A39-B85-E9
A65-B85-E9
A66-B85-E9
A2-B86-E9
A3-B86-E9
A9-B86-E9
A13-B86-E9
A24-B86-E9
A69-B86-E9
A67-B86-E9
A39-B86-E9
A65-B86-E9
A66-B86-E9
A2-B87-E9
A3-B87-E9
A9-B87-E9
A13-B87-E9
A24-B87-E9
A69-B87-E9
A67-B87-E9
A39-B87-E9
A65-B87-E9
A66-B87-E9
A2-B89-E9
A3-B89-E9
A9-B89-E9
A13-B89-E9
A24-B89-E9
A69-B89-E9
A67-B89-E9
A39-B89-E9
A65-B89-E9
A66-B89-E9
A2-B92-E9
A3-B92-E9
A9-B92-E9
A13-B92-E9
A24-B92-E9
A69-B92-E9
A67-B92-E9
A39-B92-E9
A65-B92-E9
A66-B92-E9
A2-B4-E10
A3-B4-E10
A9-B4-E10

-continued

A13-B4-E10
A24-B4-E10
A69-B4-E10
A67-B4-E10
A39-B4-E10
A65-B4-E10
A66-B4-E10
A2-B5-E10
A3-B5-E10
A9-B5-E10
A13-B5-E10
A24-B5-E10
A69-B5-E10
A67-B5-E10
A39-B5-E10
A65-B5-E10
A66-B5-E10
A2-B6-E10
A3-B6-E10
A9-B6-E10
A13-B6-E10
A24-B6-E10
A69-B6-E10
A67-B6-E10
A39-B6-E10
A65-B6-E10
A66-B6-E10
A2-B32-E10
A3-B32-E10
A9-B32-E10
A13-B32-E10
A24-B32-E10
A69-B32-E10
A67-B32-E10
A39-B32-E10
A65-B32-E10
A66-B32-E10
A2-B39-E10
A3-B39-E10
A9-B39-E10
A13-B39-E10
A24-B39-E10
A69-B39-E10
A67-B39-E10
A39-B39-E10
A65-B39-E10
A66-B39-E10
A2-B45-E10
A3-B45-E10
A9-B45-E10
A13-B45-E10
A24-B45-E10
A69-B45-E10
A67-B45-E10
A39-B45-E10
A65-B45-E10
A66-B45-E10
A2-B53-E10
A3-B53-E10
A9-B53-E10
A13-B53-E10
A24-B53-E10
A69-B53-E10
A67-B53-E10
A39-B53-E10
A65-B53-E10
A66-B53-E10
A2-B79-E10
A3-B79-E10
A9-B79-E10
A13-B79-E10
A24-B79-E10
A69-B79-E10
A67-B79-E10
A39-B79-E10
A65-B79-E10
A66-B79-E10
A2-B80-E10
A3-B80-E10
A9-B80-E10

-continued
A13-B80-E10
A24-B80-E10
A69-B80-E10
A67-B80-E10
A39-B80-E10
A65-B80-E10
A66-B80-E10
A2-B85-E10
A3-B85-E10
A9-B85-E10
A13-B85-E10
A24-B85-E10
A69-B85-E10
A67-B85-E10
A39-B85-E10
A65-B85-E10
A66-B85-E10
A2-B86-E10
A3-B86-E1
A9-B86-E10
A13-B86-E10
A24-B86-E10
A69-B86-E10
A67-B86-E10
A39-B86-E10
A65-B86-E10
A66-B86-E10
A2-B87-E10
A3-B87-E10
A9-B87-E10
A13-B87-E10
A24-B87-E10
A69-B87-E10
A67-B87-E10
A39-B87-E10
A65-B87-E10
A66-B87-E10
A2-B89-E10
A3-B89-E10
A9-B89-E10
A13-B89-E10
A24-B89-E10
A69-B89-E10
A67-B89-E10
A39-B89-E10
A65-B89-E10
A66-B89-E10
A2-B92-E10
A3-B92-E10
A9-B92-E10
A13-B92-E10
A24-B92-E10
A69-B92-E10
A67-B92-E10
A39-B92-E10
A65-B92-E10
A66-B92-E10
A2-B4-E11
A3-B4-E11
A9-B4-E11
A13-B4-E11
A24-B4-E11
A69-B4-E11
A67-B4-E11
A39-B4-E11
A65-B4-E11
A66-B4-E11
A2-B5-E11
A3-B5-E11
A9-B5-E11
A13-B5-E11
A24-B5-E11
A69-B5-E11
A67-B5-E11
A39-B5-E11
A65-B5-E11
A66-B5-E11
A2-B6-E11
A3-B6-E11
A9-B6-E11

-continued
A13-B6-E11
A24-B6-E11
A69-B6-E11
A67-B6-E11
A39-B6-E11
A65-B6-E11
A66-B6-E11
A2-B32-E11
A3-B32-E11
A9-B32-E11
A13-B32-E11
A24-B32-E11
A69-B32-E11
A67-B32-E11
A39-B32-E11
A65-B32-E11
A66-B32-E11
A2-B39-E11
A3-B39-E11
A9-B39-E11
A13-B39-E11
A24-B39-E11
A69-B39-E11
A67-B39-E11
A39-B39-E11
A65-B39-E11
A66-B39-E11
A2-B45-E11
A3-B45-E11
A9-B45-E11
A13-B45-E11
A24-B45-E11
A69-B45-E11
A67-B45-E11
A39-B45-E11
A65-B45-E11
A66-B45-E11
A2-B53-E11
A3-B53-E11
A9-B53-E11
A13-B53-E11
A24-B53-E11
A69-B53-E11
A67-B53-E11
A39-B53-E11
A65-B53-E11
A66-B53-E11
A2-B79-E11
A3-B79-E11
A9-B79-E11
A13-B79-E11
A24-B79-E11
A69-B79-E11
A67-B79-E11
A39-B79-E11
A65-B79-E11
A66-B79-E11
A2-B80-E11
A3-B80-E11
A9-B80-E11
A13-B80-E11
A24-B80-E11
A69-B80-E11
A67-B80-E11
A39-B80-E11
A65-B80-E11
A66-B80-E11
A2-B85-E11
A3-B85-E11
A9-B85-E11
A13-B85-E11
A24-B85-E11
A69-B85-E11
A67-B85-E11
A39-B85-E11
A65-B85-E11
A66-B85-E11
A2-B86-E11
A3-B86-E11
A9-B86-E11

-continued

A13-B86-E11
A24-B86-E11
A69-B86-E11
A67-B86-E11
A39-B86-E11
A65-B86-E11
A66-B86-E11
A2-B87-E11
A3-B87-E11
A9-B87-E11
A13-B87-E11
A24-B87-E11
A69-B87-E11
A67-B87-E11
A39-B87-E11
A65-B87-E11
A66-B87-E11
A2-B89-E11
A3-B89-E11
A9-B89-E11
A13-B89-E11
A24-B89-E11
A69-B89-E11
A67-B89-E11
A39-B89-E11
A65-B89-E11
A66-B89-E11
A2-B92-E11
A3-B92-E11
A9-B92-E11
A13-B92-E11
A24-B92-E11
A69-B92-E11
A67-B92-E11
A39-B92-E11
A65-B92-E11
A66-B92-E11
A2-B4-E12
A3-B4-E12
A9-B4-E12
A13-B4-E12
A24-B4-E12
A69-B4-E12
A67-B4-E12
A39-B4-E12
A65-B4-E12
A66-B4-E12
A2-B5-E12
A3-B5-E12
A9-B5-E12
A13-B5-E12
A24-B5-E12
A69-B5-E12
A67-B5-E12
A39-B5-E12
A65-B5-E12
A66-B5-E12
A2-B6-E12
A3-B6-E12
A9-B6-E12
A13-B6-E12
A24-B6-E12
A69-B6-E12
A67-B6-E12
A39-B6-E12
A65-B6-E12
A66-B6-E12
A2-B32-E12
A3-B32-E12
A9-B32-E12
A13-B32-E12
A24-B32-E12
A69-B32-E12
A67-B32-E12
A39-B32-E12
A65-B32-E12
A66-B32-E12
A2-B39-E12
A3-B39-E12
A9-B39-E12

-continued

A13-B39-E12
A24-B39-E12
A69-B39-E12
A67-B39-E12
A39-B39-E12
A65-B39-E12
A66-B39-E12
A2-B45-E12
A3-B45-E12
A9-B45-E12
A13-B45-E12
A24-B45-E12
A69-B45-E12
A67-B45-E12
A39-B45-E12
A65-B45-E12
A66-B45-E12
A2-B53-E12
A3-B53-E12
A9-B53-E12
A13-B53-E12
A24-B53-E12
A69-B53-E12
A67-B53-E12
A39-B53-E12
A65-B53-E12
A66-B53-E12
A2-B79-E12
A3-B79-E12
A9-B79-E12
A13-B79-E12
A24-B79-E12
A69-B79-E12
A67-B79-E12
A39-B79-E12
A65-B79-E12
A66-B79-E12
A2-B80-E12
A3-B80-E12
A9-B80-E12
A13-B80-E12
A24-B80-E12
A69-B80-E12
A67-B80-E12
A39-B80-E12
A65-B80-E12
A66-B80-E12
A2-B85-E12
A3-B85-E12
A9-B85-E12
A13-B85-E12
A24-B85-E12
A69-B85-E12
A67-B85-E12
A39-B85-E12
A65-B85-E12
A66-B85-E12
A2-B86-E12
A3-B86-E12
A9-B86-E12
A13-B86-E12
A24-B86-E12
A69-B86-E12
A67-B86-E12
A39-B86-E12
A65-B86-E12
A66-B86-E12
A2-B87-E12
A3-B87-E12
A9-B87-E12
A13-B87-E12
A24-B87-E12
A69-B87-E12
A67-B87-E12
A39-B87-E12
A65-B87-E12
A66-B87-E12
A2-B89-E12
A3-B89-E12
A9-B89-E12

-continued

A13-B89-E12
A24-B89-E12
A69-B89-E12
A67-B89-E12
A39-B89-E12
A65-B89-E12
A66-B89-E12
A2-B92-E12
A3-B92-E12
A9-B92-E12
A13-B92-E12
A24-B92-E12
A69-B92-E12
A67-B92-E12
A39-B92-E12
A65-B92-E12
A66-B92-E12
A2-B4-E13
A3-B4-E13
A9-B4-E13
A13-B4-E13
A24-B4-E13
A69-B4-E13
A67-B4-E13
A39-B4-E13
A65-B4-E13
A66-B4-E13
A2-B5-E13
A3-B5-E13
A9-B5-E13
A13-B5-E13
A24-B5-E13
A69-B5-E13
A67-B5-E13
A39-B5-E13
A65-B5-E13
A66-B5-E13
A2-B6-E13
A3-B6-E13
A9-B6-E13
A13-B6-E13
A24-B6-E13
A69-B6-E13
A67-B6-E13
A39-B6-E13
A65-B6-E13
A66-B6-E13
A2-B32-E13
A3-B32-E13
A9-B32-E13
A13-B32-E13
A24-B32-E13
A69-B32-E13
A67-B32-E13
A39-B32-E13
A65-B32-E13
A66-B32-E13
A2-B39-E13
A3-B39-E13
A9-B39-E13
A13-B39-E13
A24-B39-E13
A69-B39-E13
A67-B39-E13
A39-B39-E13
A65-B39-E13
A66-B39-E13
A2-B45-E13
A3-B45-E13
A9-B45-E13
A13-B45-E13
A24-B45-E13
A69-B45-E13
A67-B45-E13
A39-B45-E13
A65-B45-E13
A66-B45-E13
A2-B53-E13
A3-B53-E13
A9-B53-E13

-continued

A13-B53-E13
A24-B53-E13
A69-B53-E13
A67-B53-E13
A39-B53-E13
A65-B53-E13
A66-B53-E13
A2-B79-E13
A3-B79-E13
A9-B79-E13
A13-B79-E13
A24-B79-E13
A69-B79-E13
A67-B79-E13
A39-B79-E13
A65-B79-E13
A66-B79-E13
A2-B80-E13
A3-B80-E13
A9-B80-E13
A13-B80-E13
A24-B80-E13
A69-B80-E13
A67-B80-E13
A39-B80-E13
A65-B80-E13
A66-B80-E13
A2-B85-E13
A3-B85-E13
A9-B85-E13
A13-B85-E13
A24-B85-E13
A69-B85-E13
A67-B85-E13
A39-B85-E13
A65-B85-E13
A66-B85-E13
A2-B86-E13
A3-B86-E13
A9-B86-E13
A13-B86-E13
A24-B86-E13
A69-B86-E13
A67-B86-E13
A39-B86-E13
A65-B86-E13
A66-B86-E13
A2-B87-E13
A3-B87-E13
A9-B87-E13
A13-B87-E13
A24-B87-E13
A69-B87-E13
A67-B87-E13
A39-B87-E13
A65-B87-E13
A66-B87-E13
A2-B89-E13
A3-B89-E13
A9-B89-E13
A13-B89-E13
A24-B89-E13
A69-B89-E13
A67-B89-E13
A39-B89-E13
A65-B89-E13
A66-B89-E13
A2-B92-E13
A3-B92-E13
A9-B92-E13
A13-B92-E13
A24-B92-E13
A69-B92-E13
A67-B92-E13
A39-B92-E13
A65-B92-E13
A66-B92-E13
A2-B4-E14
A3-B4-E14
A9-B4-E14

-continued

A13-B4-E14
A24-B4-E14
A69-B4-E14
A67-B4-E14
A39-B4-E14
A65-B4-E14
A66-B4-E14
A2-B5-E14
A3-B5-E14
A9-B5-E14
A13-B5-E14
A24-B5-E14
A69-B5-E14
A67-B5-E14
A39-B5-E14
A65-B5-E14
A66-B5-E14
A2-B6-E14
A3-B6-E14
A9-B6-E14
A13-B6-E14
A24-B6-E14
A69-B6-E14
A67-B6-E14
A39-B6-E14
A65-B6-E14
A66-B6-E14
A2-B32-E14
A3-B32-E14
A9-B32-E14
A13-B32-E14
A24-B32-E14
A69-B32-E14
A67-B32-E14
A39-B32-E14
A65-B32-E14
A66-B32-E14
A2-B39-E14
A3-B39-E14
A9-B39-E14
A13-B39-E14
A24-B39-E14
A69-B39-E14
A67-B39-E14
A39-B39-E14
A65-B39-E14
A66-B39-E14
A2-B45-E14
A3-B45-E14
A9-B45-E14
A13-B45-E14
A24-B45-E14
A69-B45-E14
A67-B45-E14
A39-B45-E14
A65-B45-E14
A66-B45-E14
A2-B53-E14
A3-B53-E14
A9-B53-E14
A13-B53-E14
A24-B53-E14
A69-B53-E14
A67-B53-E14
A39-B53-E14
A65-B53-E14
A66-B53-E14
A2-B79-E14
A3-B79-E14
A9-B79-E14
A13-B79-E14
A24-B79-E14
A69-B79-E14
A67-B79-E14
A39-B79-E14
A65-B79-E14
A66-B79-E14
A2-B80-E14
A3-B80-E14
A9-B80-E14

-continued

A13-B80-E14
A24-B80-E14
A69-B80-E14
A67-B80-E14
A39-B80-E14
A65-B80-E14
A66-B80-E14
A2-B85-E14
A3-B85-E14
A9-B85-E14
A13-B85-E14
A24-B85-E14
A69-B85-E14
A67-B85-E14
A39-B85-E14
A65-B85-E14
A66-B85-E14
A2-B86-E14
A3-B86-E14
A9-B86-E14
A13-B86-E14
A24-B86-E14
A69-B86-E14
A67-B86-E14
A39-B86-E14
A65-B86-E14
A66-B86-E14
A2-B87-E14
A3-B87-E14
A9-B87-E14
A13-B87-E14
A24-B87-E14
A69-B87-E14
A67-B87-E14
A39-B87-E14
A65-B87-E14
A66-B87-E14
A2-B89-E14
A3-B89-E14
A9-B89-E14
A13-B89-E14
A24-B89-E14
A69-B89-E14
A67-B89-E14
A39-B89-E14
A65-B89-E14
A66-B89-E14
A2-B92-E14
A3-B92-E14
A9-B92-E14
A13-B92-E14
A24-B92-E14
A69-B92-E14
A67-B92-E14
A39-B92-E14
A65-B92-E14
A66-B92-E14
A2-B4-E15
A3-B4-E15
A9-B4-E15
A13-B4-E15
A24-B4-E15
A69-B4-E15
A67-B4-E15
A39-B4-E15
A65-B4-E15
A66-B4-E15
A2-B5-E15
A3-B5-E15
A9-B5-E15
A13-B5-E15
A24-B5-E15
A69-B5-E15
A67-B5-E15
A39-B5-E15
A65-B5-E15
A66-B5-E15
A2-B6-E15
A3-B6-E15
A9-B6-E15

-continued
A13-B6-E15
A24-B6-E15
A69-B6-E15
A67-B6-E15
A39-B6-E15
A65-B6-E15
A66-B6-E15
A2-B32-E15
A3-B32-E15
A9-B32-E15
A13-B32-E15
A24-B32-E15
A69-B32-E15
A67-B32-E15
A39-B32-E15
A65-B32-E15
A66-B32-E15
A2-B39-E15
A3-B39-E15
A9-B39-E15
A13-B39-E15
A24-B39-E15
A69-B39-E15
A67-B39-E15
A39-B39-E15
A65-B39-E15
A66-B39-E15
A2-B45-E15
A3-B45-E15
A9-B45-E15
A13-B45-E15
A24-B45-E15
A69-B45-E15
A67-B45-E15
A39-B45-E15
A65-B45-E15
A66-B45-E15
A2-B53-E15
A3-B53-E15
A9-B53-E15
A13-B53-E15
A24-B53-E15
A69-B53-E15
A67-B53-E15
A39-B53-E15
A65-B53-E15
A66-B53-E15
A2-B79-E15
A3-B79-E15
A9-B79-E15
A13-B79-E15
A24-B79-E15
A69-B79-E15
A67-B79-E15
A39-B79-E15
A65-B79-E15
A66-B79-E15
A2-B80-E15
A3-B80-E15
A9-B80-E15
A13-B80-E15
A24-B80-E15
A69-B80-E15
A67-B80-E15
A39-B80-E15
A65-B80-E15
A66-B80-E15
A2-B85-E15
A3-B85-E15
A9-B85-E15
A13-B85-E15
A24-B85-E15
A69-B85-E15
A67-B85-E15
A39-B85-E15
A65-B85-E15
A66-B85-E15
A2-B86-E15
A3-B86-E15
A9-B86-E15

-continued
A13-B86-E15
A24-B86-E15
A69-B86-E15
A67-B86-E15
A39-B86-E15
A65-B86-E15
A66-B86-E15
A2-B87-E15
A3-B87-E15
A9-B87-E15
A13-B87-E15
A24-B87-E15
A69-B87-E15
A67-B87-E15
A39-B87-E15
A65-B87-E15
A66-B87-E15
A2-B89-E15
A3-B89-E15
A9-B89-E15
A13-B89-E15
A24-B89-E15
A69-B89-E15
A67-B89-E15
A39-B89-E15
A65-B89-E15
A66-B89-E15
A2-B92-E15
A3-B92-E15
A9-B92-E15
A13-B92-E15
A24-B92-E15
A69-B92-E15
A67-B92-E15
A39-B92-E15
A65-B92-E15
A66-B92-E15
A2-B4-E16
A3-B4-E16
A9-B4-E16
A13-B4-E16
A24-B4-E16
A69-B4-E16
A67-B4-E16
A39-B4-E16
A65-B4-E16
A66-B4-E16
A2-B5-E16
A3-B5-E16
A9-B5-E16
A13-B5-E16
A24-B5-E16
A69-B5-E16
A67-B5-E16
A39-B5-E16
A65-B5-E16
A66-B5-E16
A2-B6-E16
A3-B6-E16
A9-B6-E16
A13-B6-E16
A24-B6-E16
A69-B6-E16
A67-B6-E16
A39-B6-E16
A65-B6-E16
A66-B6-E16
A2-B32-E16
A3-B32-E16
A9-B32-E16
A13-B32-E16
A24-B32-E16
A69-B32-E16
A67-B32-E16
A39-B32-E16
A65-B32-E16
A66-B32-E16
A2-B39-E16
A3-B39-E16
A9-B39-E16

-continued

A13-B39-E16
A24-B39-E16
A69-B39-E16
A67-B39-E16
A39-B39-E16
A65-B39-E16
A66-B39-E16
A2-B45-E16
A3-B45-E16
A9-B45-E16
A13-B45-E16
A24-B45-E16
A69-B45-E16
A67-B45-E16
A39-B45-E16
A65-B45-E16
A66-B45-E16
A2-B53-E16
A3-B53-E16
A9-B53-E16
A13-B53-E16
A24-B53-E16
A69-B53-E16
A67-B53-E16
A39-B53-E16
A65-B53-E16
A66-B53-E16
A2-B79-E16
A3-B79-E16
A9-B79-E16
A13-B79-E16
A24-B79-E16
A69-B79-E16
A67-B79-E16
A39-B79-E16
A65-B79-E16
A66-B79-E16
A2-B80-E16
A3-B80-E16
A9-B80-E16
A13-B80-E16
A24-B80-E16
A69-B80-E16
A67-B80-E16
A39-B80-E16
A65-B80-E16
A66-B80-E16
A2-B85-E16
A3-B85-E16
A9-B85-E16
A13-B85-E16
A24-B85-E16
A69-B85-E16
A67-B85-E16
A39-B85-E16
A65-B85-E16
A66-B85-E16
A2-B86-E16
A3-B86-E16
A9-B86-E16
A13-B86-E16
A24-B86-E16
A69-B86-E16
A67-B86-E16
A39-B86-E16
A65-B86-E16
A66-B86-E16
A2-B87-E16
A3-B87-E16
A9-B87-E16
A13-B87-E16
A24-B87-E16
A69-B87-E16
A67-B87-E16
A39-B87-E16
A65-B87-E16
A66-B87-E16
A2-B89-E16
A3-B89-E16
A9-B89-E16

-continued

A13-B89-E16
A24-B89-E16
A69-B89-E16
A67-B89-E16
A39-B89-E16
A65-B89-E16
A66-B89-E16
A2-B92-E16
A3-B92-E16
A9-B92-E16
A13-B92-E16
A24-B92-E16
A69-B92-E16
A67-B92-E16
A39-B92-E16
A65-B92-E16
A66-B92-E16
A2-B4-E17
A3-B4-E17
A9-B4-E17
A13-B4-E17
A24-B4-E17
A69-B4-E17
A67-B4-E17
A39-B4-E17
A65-B4-E17
A66-B4-E17
A2-B5-E17
A3-B5-E17
A9-B5-E17
A13-B5-E17
A24-B5-E17
A69-B5-E17
A67-B5-E17
A39-B5-E17
A65-B5-E17
A66-B5-E17
A2-B6-E17
A3-B6-E17
A9-B6-E17
A13-B6-E17
A24-B6-E17
A69-B6-E17
A67-B6-E17
A39-B6-E17
A65-B6-E17
A66-B6-E17
A2-B32-E17
A3-B32-E17
A9-B32-E17
A13-B32-E17
A24-B32-E17
A69-B32-E17
A67-B32-E17
A39-B32-E17
A65-B32-E17
A66-B32-E17
A2-B39-E17
A3-B39-E17
A9-B39-E17
A13-B39-E17
A24-B39-E17
A69-B39-E17
A67-B39-E17
A39-B39-E17
A65-B39-E17
A66-B39-E17
A2-B45-E17
A3-B45-E17
A9-B45-E17
A13-B45-E17
A24-B45-E17
A69-B45-E17
A67-B45-E17
A39-B45-E17
A65-B45-E17
A66-B45-E17
A2-B53-E17
A3-B53-E17
A9-B53-E17

-continued
A13-B53-E17
A24-B53-E17
A69-B53-E17
A67-B53-E17
A39-B53-E17
A65-B53-E17
A66-B53-E17
A2-B79-E17
A3-B79-E17
A9-B79-E17
A13-B79-E17
A24-B79-E17
A69-B79-E17
A67-B79-E17
A39-B79-E17
A65-B79-E17
A66-B79-E17
A2-B80-E17
A3-B80-E17
A9-B80-E17
A13-B80-E17
A24-B80-E17
A69-B80-E17
A67-B80-E17
A39-B80-E17
A65-B80-E17
A66-B80-E17
A2-B85-E17
A3-B85-E17
A9-B85-E17
A13-B85-E17
A24-B85-E17
A69-B85-E17
A67-B85-E17
A39-B85-E17
A65-B85-E17
A66-B85-E17
A2-B86-E17
A3-B86-E17
A9-B86-E17
A13-B86-E17
A24-B86-E17
A69-B86-E17
A67-B86-E17
A39-B86-E17
A65-B86-E17
A66-B86-E17
A2-B87-E17
A3-B87-E17
A9-B87-E17
A13-B87-E17
A24-B87-E17
A69-B87-E17
A67-B87-E17
A39-B87-E17
A65-B87-E17
A66-B87-E17
A2-B89-E17
A3-B89-E17
A9-B89-E17
A13-B89-E17
A24-B89-E17
A69-B89-E17
A67-B89-E17
A39-B89-E17
A65-B89-E17
A66-B89-E17
A2-B92-E17
A3-B92-E17
A9-B92-E17
A13-B92-E17
A24-B92-E17
A69-B92-E17
A67-B92-E17
A39-B92-E17
A65-B92-E17
A66-B92-E17

Thus, for example, in table 6 the compound denoted as A2-B4-C6-D8 is the product of the combination of group A2 in Table 1 and B4 in Table 2 and C6 in Table 3 and D8 in Table 4, namely N-[(S)-1-(1-benzylcarbamoyl-methanoyl)-propyl]-4-morpholin-4-yl-4-oxo-2-benzylsulfonylmethyl-butyramide:

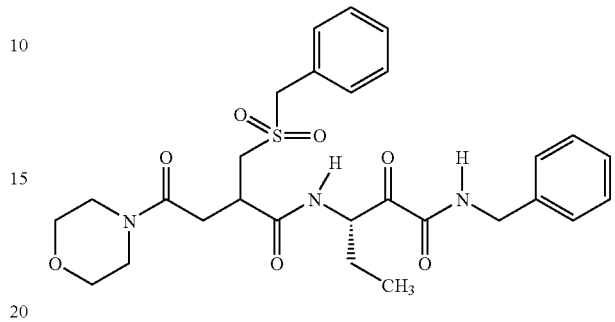

Particular compounds of the invention are:
3-biphenyl-3-yl-N-cyanomethyl-2-benzylsulfonylmethyl-propionamide;
3-biphenyl-4-yl-N-cyanomethyl-2-benzylsulfonylmethyl-propionamide;
3-(3-bromo-phenyl)-N-cyanomethyl-2-benzylsulfonylmethyl-propionamide;
N-cyanomethyl-3-(3-cyano-benzylsulfonyl)-2-benzylsulfonyl-methyl-propionamide;
N-cyanomethyl-2-[2-1,1-difluoro-methoxy)-benzylsulfanylmethyl]-3-benzylsulfanyl-propionamide;
N-cyanomethyl-3-(2-trifluoromethyl-benzylsulfanyl)-2-(2-trifluoro-methyl-benzylsulfanylmethyl)-propionamide;
N-cyanomethyl-3-isobutylsulfanyl-2-isobutylsulfanylmethyl-propionamide;
N-cyanomethyl-4-phenylsulfanyl-2-(2-phenylsulfanyl-ethyl)-butyramide;
N-cyanomethyl-3-[2-(1,1-difluoro-methoxy)-benzylsulfanyl]-2-[2-(1,1-difluoro-methoxy)-benzylsulfanylmethyl]-propionamide;
3-benzylsulfanyl-2-benzylsulfanylmethyl-N-cyanomethyl-propionamide;
N-cyanomethyl-2-[2-1,1-difluoro-methoxy)-benzylsulfonylmethyl]-3-benzylsulfonyl-propionamide;
N-cyanomethyl-3-(2-trifluoromethyl-benzylsulfonyl)-2-(2-trifluoromethyl-benzylsulfonylmethyl)-propionamide;
4-benzenesulfonyl-2-(2-benzenesulfonyl-ethyl)-N-cyanomethyl-butyramide;
N-cyanomethyl-3-[2-(1,1-difluoro-methoxy)-benzylsulfonyl]-2-[2-(1,1-difluoro-methoxy)-benzylsulfonylmethyl]-propionamide;
N-cyanomethyl-3-benzylsulfonyl-2-benzylsulfonylmethyl-propionamide;
N-cyanomethyl-3-(2-methyl-propane-1-sulfonyl)-2-(2-methyl-propane-1-sulfonylmethyl)-propionamide;
N-cyanomethyl-3-(2-methyl-thiazol-4-ylmethylsulfonyl)-2-benzyl-sulfonylmethyl-propionamide;
3-biphenyl-3-yl-N-cyanomethyl-2-[2-(1,1-difluoro-methoxy)-benzyl-sulfonylmethyl]-propionamide;
(3'-{2-(cyanomethyl-carbamoyl)-3-[2-(1,1-difluoro-methoxy)-benzyl-sulfonyl]-propyl}-biphenyl-4-yl)-carbamic acid ethyl ester;
N-cyanomethyl-2-[2-(1,1-difluoro-methoxy)-benzylsulfonylmethyl]-3-(4'-methylsulfonylamino-biphenyl-3-yl)-propionamide;

3-(3-bromo-phenyl)-N-cyanomethyl-2-[2-(1,1-difluoro-methoxy)-phenyl-methylsulfonylmethyl]-propionamide;
N-cyanomethyl-2-((E)-3-phenyl-allyl)-3-benzylsulfonyl-propionamide;
N-cyanomethyl-3-benzylsulfonyl-2-(3-phenyl-propyl)-propionamide;
N-[(S)-1-(1-Benzooxazol-2-yl-methanoyl)-butyl]-3-benzylsulfonyl-2-benzylsulfonylmethyl-propionamide;
N-[(S)-1-(1-Benzooxazol-2-yl-methanoyl)-butyl]-3-(2-trifluoromethyl-benzylsulfonyl)-2(2-trifluoromethyl-benzylsulfonylmethyl)-propionamide;
N-[(S)-1-(1-Benzooxazol-2-yl-methanoyl)-pentyl]-4-(2-methoxy-benzenesulfonyl)-2-[2-(2-methoxy-benzenesulfonyl)-ethyl]-butyramide;
4-Benzenesulfonyl-2-(2-benzenesulfonyl-ethyl)-N-[(S)-1-(1-benzooxazol-2-yl-methanoyl)-butyl]-butyramide;
(R)-N-[(S)-1-(1-benzooxazol-2-yl-methanoyl)-butyl]-2-cyclohexylmethyl-3-benzylsulfonyl-propionamide;
N-[(S)-1-(1-benzothiazol-2-yl-methanoyl)-propyl]-4-morpholin-4-yl-4-oxo-2-benzylsulfonylmethyl-butyramide;
N-[(S)-1-(1-benzooxazol-2-yl-methanoyl)-butyl]-3-cyclohexyl-2-cyclohexylmethyl-propionamide;
N-[(S)-1-(1-Benzooxazol-2-yl-methanoyl)-butyl]-3-isobutylsulfanyl-2-isobutylsulfanylmethyl-propionamide;
N-[(S)-1-(1-benzooxazol-2-yl-methanoyl)-butyl]-3-benzylsulfanyl-2-benzylsulfanylmethyl-propionamide;
N-[(S)-1-(1-benzooxazol-2-yl-methanoyl)-butyl]-4-phenylsulfanyl-2-(2-phenylsulfanyl-ethyl)-butyramide;
N-[(S)-1-(1-benzooxazol-2-yl-methanoyl)-propyl]-4-morpholin-4-yl-4-oxo-2-benzylsulfonylmethyl-butyramide;
N-[(S)-1-(1-Benzooxazol-2-yl-methanoyl)-pentyl]-4-morpholin-4-yl-4-oxo-2-benzylsulfonylmethyl-butyramide;
4-Morpholin-4-yl-4-oxo-2-benzylsulfonylmethyl-N-{(S)-1-[1-(3-phenyl-[1,2,4]oxadiazol-5-yl)-methanoyl]-propyl}-butyramide;
N-[(S)-1-(1-Benzooxazol-2-yl-methanoyl)-butyl]-2-[2-(1,1-difluoro-methoxy)-benzylsulfonylmethyl]-3-benzylsulfonyl-propionamide;
4-Morpholin-4-yl-4-oxo-N-[1-(2-oxo-2-phenyl-acetyl)-pentyl]-2-benzylsulfonylmethyl-butyramide;
N-(1,1-Dimethyl-2-oxazolo[4,5-b]pyridin-2-yl-2-oxoethyl)-4-morpholin-4-yl-4-oxo-2-benzylsulfonylmethyl-butyramide;
N-[1-(5-Ethyl-[1,3,4]oxadiazole-2-carbonyl)-butyl]-4-morpholin-4-yl-4-oxo-2-benzylsulfonylmethyl-butyramide;
N-[1-(5-Ethyl-[1,3,4]oxadiazole-2-carbonyl)-butyl]-4-oxo-2-benzylsulfonyl-methyl-4-piperidin-1-yl-butyramide;
N-[1-(5-Ethyl-[1,3,4]oxadiazole-2-carbonyl)-butyl]-4-oxo-2-benzylsulfonyl-methyl-4-pyrrolidin-1-yl-butyramide;
N-[1-(5-Methoxymethyl-[1,3,4]oxadiazole-2-carbonyl)-propyl]-4-morpholin-4-yl-4-oxo-2-benzylsulfonylmethyl-butyramide;
N-[1-(5-Methoxymethyl-[1,3,4]oxadiazole-2-carbonyl)-propyl]-4-oxo-2-benzylsulfonylmethyl-4-piperidin-1-yl-butyramide;
N-[1-(5-Methoxymethyl-[1,3,4]oxadiazole-2-carbonyl)-propyl]-4-oxo-2-benzylsulfonylmethyl-4-pyrrolidin-1-yl-butyramide;
4-Morpholin-4-yl-4-oxo-2-benzylsulfonylmethyl-N-[1-(5-phenyl-[1,3,4]oxadiazole-2-carbonyl)-propyl]-butyramide;
4-Oxo-2-benzylsulfonylmethyl-N-[1-(5-phenyl-[1,3,4]oxadiazole-2-carbonyl)-propyl]-4-piperidin-1-yl-butyramide;
4-Oxo-2-benzylsulfonylmethyl-N-[1-(5-phenyl-[1,3,4]oxadiazole-2-carbonyl)-propyl]-4-pyrrolidin-1-yl-butyramide;
4-Morpholin-4-yl-N-[1-(oxazolo[4,5-b]pyridine-2-carbonyl)-propyl]-4-oxo-2-benzylsulfonylmethyl-butyramide;
N-[1-(Oxazolo[4,5-b]pyridine-2-carbonyl)-propyl]-4-oxo-2-benzylsulfonyl-methyl-4-piperidin-1-yl-butyramide;
N-[1-(Oxazolo[4,5-b]pyridine-2-carbonyl)-propyl]-4-oxo-2-benzylsulfonyl-methyl-4-pyrrolidin-1-yl-butyramide;
4-Morpholin-4-yl-4-oxo-2-benzylsulfonylmethyl-N-[1-(5-pyridin-4-yl-[1,3,4]oxadiazole-2-carbonyl)-propyl]-butyramide;
4-Oxo-2-benzylsulfonylmethyl-4-piperidin-1-yl-N-[1-(5-pyridin-4-yl-[1,3,4]oxadiazole-2-carbonyl)-propyl]-butyramide;
4-Oxo-2-benzylsulfonylmethyl-N-[1-(5-pyridin-4-yl-[1,3,4]oxadiazole-2-carbonyl)-propyl]-4-pyrrolidin-1-yl-butyramide;
4-Morpholin-4-yl-4-oxo-2-benzylsulfonylmethyl-N-[1-(5-pyridin-3-yl-[1,3,4]oxadiazole-2-carbonyl)-propyl]-butyramide;
N-[1-(Benzooxazole-2-carbonyl)-propyl]-4-oxo-2-benzylsulfonylmethyl-4-piperidin-1-yl-butyramide;
N-[1-(Benzooxazole-2-carbonyl)-propyl]-4-oxo-2-benzylsulfonylmethyl-4-pyrrolidin-1-yl-butyramide;
N-[1-(Benzooxazole-2-carbonyl)-propyl]-2-cyclohexylmethyl-4-morpholin-4-yl-4-oxo-butyramide;
2-Cyclohexylmethyl-4-morpholin-4-yl-N-[1-(oxazolo[4,5-b]pyridine-2-carbonyl)-propyl]-4-oxo-butyramide;
2-Cyclohexylmethyl-N-[1-(5-ethyl-[1,3,4]oxadiazole-2-carbonyl)-butyl]-4-morpholin-4-yl-4-oxo-butyramide;
N-(2-Benzooxazol-2-yl-1-methoxymethyl-2-oxo-ethyl)-2-(2-difluoromethoxy-benzylsulfonylmethyl)-4-morpholin-4-yl-4-oxo-butyramide;
N-[1-(Benzooxazole-2-carbonyl)-propyl]-2-(2-cyclohexyl-ethyl)-4-morpholin-4-yl-4-oxo-butyramide;
2-(2-Cyclohexyl-ethyl)-4-morpholin-4-yl-N-[1-(oxazolo[4,5-b]pyridine-2-carbonyl)-propyl]-4-oxo-butyramide;
2-(2-Cyclohexyl-ethyl)-4-morpholin-4-yl-4-oxo-N-[1-(5-phenyl-[1,3,4]oxadiazole-2-carbonyl)-propyl]-butyramide;
2-(2-Difluoromethoxy-benzylsulfonylmethyl)-4-morpholin-4-yl-4-oxo-N-[1-(5-phenyl-[1,3,4]oxadiazole-2-carbonyl)-propyl]-butyramide;
2-(2-Difluoromethoxy-benzylsulfonylmethyl)-N-[1-(5-ethyl-[1,3,4]oxadiazole-2-carbonyl)-butyl]-4-morpholin-4-yl-4-oxo-butyramide;
N-[1-(Benzooxazole-2-carbonyl)-propyl]-2-(2-difluoromethoxy-benzyl-sulfonylmethyl)-4-morpholin-4-yl-4-oxo-butyramide;
2-(2-Morpholin-4-yl-2-oxo-ethyl)-5-phenyl-pentanoic acid, 1-(benzooxazole-2-carbonyl)-propyl]-amide;
(R)-2-Cyclohexylmethyl-4-morpholin-4-yl-4-oxo-N-[(S)-1-(5-phenyl-1,2,4-oxadiazole-3-carbonyl)-propyl]-butyramide;
2-(2-Morpholin-4-yl-2-oxo-ethyl)-5-phenyl-pentanoic acid, (S)-1-(5-phenyl-[1,2,4]oxadiazole-3-carbonyl)-propyl]-amide;
4-Morpholin-4-yl-4-oxo-2-benzylsulfonylmethyl-N-[(S)-1-(5-phenyl-1,2,4-oxadiazole-3-carbonyl)-propyl]-butyramide;
(R)-2-Cyclohexylmethyl-4-morpholin-4-yl-4-oxo-N-[(S)-1-(3-phenyl-1,2,4-oxadiazole-5-carbonyl)-propyl]-butyramide;
4-Morpholin-4-yl-N-[1-(oxazole-2-carbonyl)-3-phenyl-propyl]-4-oxo-2-benzylsulfonylmethyl-butyramide;
N-(1,1-Dimethyl-2-oxazol-2-yl-2-oxo-ethyl)-4-morpholin-4-yl-4-oxo-2-benzylsulfonylmethyl-butyramide;
N-4-Isopropyl-N-1-[1-(oxazole-2-carbonyl)-3-phenyl-propyl]-2-benzylsulfonylmethyl-succinamide;

2-(2-Difluoromethoxy-benzylsulfonylmethyl)-4-morpholin-4-yl-N-[1-(oxazole-2-carbonyl)-3-phenyl-propyl]-4-oxo-butyramide;

2-(2-Methyl-propane-1-sulfonylmethyl)-4-morpholin-4-yl-N-[1-(oxazole-2-carbonyl)-3-phenyl-propyl]-4-oxo-butyramide;

2-Cyclopropylmethylsulfonylmethyl-4-morpholin-4-yl-N-[1-(oxazole-2-carbonyl)-3-phenyl-propyl]-4-oxo-butyramide;

N-[1-(Benzooxazole-2-carbonyl)-butyl]-2-benzylsulfonyl-3-(tetrahydro-pyran-4-yloxymethyl)-propionamide;

N-[1-(Benzooxazole-2-carbonyl)-butyl]-3-ethanesulfonyl-2-(tetrahydro-pyran-4-yloxymethyl)-propionamide;

N-(1-Benzenesulfonyl-3-oxo-azepan-4-yl)-2-cyclopropylmethylsulfonyl-methyl-4-morpholin-4-yl-4-oxo-butyramide;

2-Cyclopropylmethylsulfonylmethyl-N-{(S)-1-[(R)-hydroxy-(3-phenyl-1,2,4-oxadiazol-5-yl)-methyl]-propyl}-4-morpholin-4-yl-4-oxo-butyramide;

N-{(S)-1-[(R)-hydroxy-(3-phenyl-1,2,4-oxadiazol-5-yl)-methyl]-propyl}-2-(2-methyl-propane-1-sulfonylmethyl)-4-morpholin-4-yl-4-oxo-butyramide;

2-(2-Morpholin-4-yl-2-oxo-ethyl)-5-phenyl-pentanoic acid {(S)-1-[(R)-hydroxy-(3-phenyl-1,2,4-oxadiazol-5-yl)-methyl]-propyl}-amide;

2-Cyclopropylmethylsulfonylmethyl-4-morpholin-4-yl-4-oxo-N-[(S)-1-(3-phenyl-1,2,4-oxadiazole-5-carbonyl)-propyl]-butyramide;

2-(2-methyl-propane-1-sulfonylmethyl)-4-morpholin-4-yl-4-oxo-N-[(S)-1-(3-phenyl-1,2,4-oxadiazole-5-carbonyl)-propyl]-butyramide;

2-(2-Morpholin-4-yl-2-oxo-ethyl)-5-phenyl-pentanoic acid, (S)-1-(3-phenyl-1,2,4-oxadiazole-5-carbonyl)-propyl}-amide;

N-[(1S)-1-(Benzooxazol-2-yl-hydroxy-methyl)-3-phenyl-propyl]-2-cyclopropylmethylsulfonylmethyl-4-morpholin-4-yl-4-oxo-butyramide;

(R)-2-((S)-1-Hydroxy-2-morpholin-4-yl-2-oxo-ethyl)-5-phenyl-pentanoic acid, 1-(benzoxazole-2-carbonyl)-propyl]-amide;

(R)-5-(2-Difluoromethoxy-phenyl)-2-((S)-1-hydroxy-2-morpholin-4-yl-2-oxo-ethyl)-pentanoic acid, 1-(benzoxazole-2-carbonyl)-propyl]-amide;

4-Morpholin-4-yl-N-[1-(oxazole-2-carbonyl)-cyclopropyl]-4-oxo-2-benzylsulfonyl methyl-butyramide;

N-[(S)-1-((E)-2-benzenesulfonyl-vinyl)-pentyl]-3-benzylsulfonyl-2-benzylsulfonylmethyl-propionamide N-(3-benzenesulfonyl-1-phenethyl-allyl)-3-benzylsulfonyl-2-benzylsulfonylmethyl-propionamide;

N-(3-benzenesulfonylamino-2-oxo-propyl)-4-morpholin-4-yl-4-oxo-2-benzylsulfonylmethyl-butyramide;

(S)-2,2-difluoro-4-(4-morpholin-4-yl-4-oxo-2-benzylsulfonylmethyl-butanoylamino)-3-oxo-hexanoic acid dimethylamide;

N-[(S)-1-(1-Benzylcarbamoyl-methanoyl)-propyl]-3-benzylsulfonyl-2-benzylsulfonylmethyl-propionamide;

N-[(S)-1-(1-Benzylcarbamoyl-methanoyl)-propyl]-4-morpholin-4-yl-4-oxo-2-benzylsulfonylmethyl-butyramide;

3-Hydroxy-4-(4-morpholin-4-yl-4-oxo-2-benzylsulfonylmethyl-butyrylamino)-azepane-1-carboxylic acid tert-butyl ester;

4-(2-Cyclopropylmethylsulfonylmethyl-4-morpholin-4-yl-4-oxo-butyrylamino)-3-hydroxy-azepane-1-carboxylic acid tert-butyl ester;

3-Hydroxy-4-[2-(2-methyl-propane-1-sulfonylmethyl)-4-morpholin-4-yl-4-oxo-butyrylamino]-azepane-1-carboxylic acid tert-butyl ester;

4-(4-Morpholin-4-yl-4-oxo-2-benzylsulfonylmethyl-butyrylamino)-3-oxo-azepane-1-carboxylic acid tert-butyl ester;

4-(2-Cyclopropylmethylsulfonylmethyl-4-morpholin-4-yl-4-oxo-butyrylamino)-3-oxo-azepane-1-carboxylic acid tert-butyl ester;

4-[2-(2-Methyl-propane-1-sulfonylmethyl)-4-morpholin-4-yl-4-oxo-butyrylamino]-3-oxo-azepane-1-carboxylic acid tert-butyl ester;

N-(1-Benzenesulfonyl-3-oxo-azepan-4-yl)-4-morpholin-4-yl-4-oxo-2-benzylsulfonylmethyl-butyramide;

N-(1-Benzenesulfonyl-3-oxo-azepan-4-yl)-2-(2-methyl-propane-1-sulfonylmethyl)-4-morpholin-4-yl-4-oxo-butyramide;

3-(4-Morpholin-4-yl-4-oxo-2-benzylsulfonylmethyl-butyrylamino)-4-oxo-pyrrolidine-1-carboxylic acid tert-butyl ester;

4-(4-Morpholin-4-yl-4-oxo-2-benzylsulfonylmethyl-butyrylamino)-3-oxo-azepane-1-carboxylic acid benzyl ester;

acetic acid (2S,3S)-3-(4-morpholin-4-yl-4-oxo-2-benzylsulfonylmethyl-butanoylamino)-4-oxo-azetidin-2-yl ester; and their corresponding N-oxides, and their prodrugs, and their protected derivatives, individual isomers and mixtures of isomers thereof; and the pharmaceutically acceptable salts and solvates (e.g. hydrates) of such compounds and their N-oxides and their prodrugs, and their protected derivatives, individual isomers and mixtures of isomers thereof.

Preferred compounds of the invention are:—

N-[(S)-1-(1-benzooxazol-2-yl-methanoyl)-butyl]-3-benzylsulfonyl-2-benzylsulfonylmethyl-propionamide (compound denoted as A64-B4-C11-D6), (Compound 1);

N-[(S)-1-(1-benzooxazol-2-yl-methanoyl)-butyl]-3-(2-trifluoromethyl-benzylsulfonyl)-2-(2-trifluoromethyl-benzylsulfonylmethyl)-propionamide, (compound denoted as A69-B32-C11-D6), (Compound 2);

N-[(S)-1-(1-benzooxazol-2-yl-methanoyl)-pentyl]-4-(2-methoxy-benzenesulfonyl)-2-[2-(2-methoxy-benzenesulfonyl)-ethyl]-butyramide, (compound denoted as A64-B85-C11-D6), (Compound 3);

4-benzenesulfonyl-2-(2-benzenesulfonyl-ethyl)-N-[(S)-1-(1-benzooxazol-2-yl-methanoyl)butyl]-butyramide, (compound denoted as A4-B6-C11-D6), (Compound 4);

(R)-N-[(S)-1-(1-benzooxazol-2-yl-methanoyl)-butyl]-2-cyclohexylmethyl-3-benzylsulfonyl-propionamide, (Compound 5);

N-[(S)-1-(1-benzooxazol-2-yl-methanoyl)-butyl]-3-isobutylsulfanyl-2-isobutylsulfanylmethyl-propionamide, (compound denoted as A68-B79-C11-D6), (Compound 8);

N-[(S)-1-(1-benzooxazol-2-yl-methanoyl)-butyl]-3-benzylsulfanyl-2-benzylsulfanylmethyl-propionamide, (compound denoted as A64-B85-C11-D6), (Compound 9);

N-[(S)-1-(1-benzooxazol-2-yl-methanoyl)-butyl]-4-phenylsulfanyl-2-(2-phenylsulfanyl-ethyl)-butyramide, (compound denoted as A70-B80-C6-D6), (Compound 10);

N-cyanomethyl-2-[2-(1,1-difluoro-methoxy)-benzylsulfonylmethyl]-4-morpholin-4-yl-4-oxo-butyramide, (compound denoted as A2-B39-C1-D1), (Compound 25);

N-[(S)-1-(1-benzooxazol-2-yl-methanoyl)-propyl]-4-morpholin-4-yl-4-oxo-2-benzylsulfonylmethyl-butyramide, (compound denoted as A2-B4-C6-D6), (Compound 29);

N-[(S)-1-(1-benzooxazol-2-yl-methanoyl)-pentyl]-4-morpholin-4-yl-4-oxo-2-benzylsulfonylmethyl-butyramide, (compound denoted as A2-B4-C9-D6), (Compound 30);

N-[(S)-1-(1-benzylcarbamoyl-methanoyl)-propyl]-4-morpholin-4-yl-4-oxo-2-benzylsulfonylmethyl-butyramide, (compound denoted as A2-B4-C6-D8), (Compound 32);

N-[(S)-1-((E)-2-benzenesulfonyl-vinyl)-pentyl]-3-benzylsulfonyl-2-benzylsulfonylmethyl-propionamide, (compound denoted as A13-B4-C9-D7), (Compound 38);

N-(3-Benzenesulfonyl-1-phenethyl-allyl)-3-benzylsulfonyl-2-benzylsulfonylmethyl-propionamide, (compound denoted as A13-B4-C10-D7), (Compound 39);

N-cyanomethyl-3-(3-cyano-benzylsulfonyl)-2-benzylsulfonyl-methyl-propionamide, (compound denoted as A89-B4-C1-D1), (Compound 40);

4-morpholin-4-yl-4-oxo-2-benzylsulfonylmethyl-N-{(S)-1-[1-(3-phenyl-[1,2,4]oxadiazol-5-yl)-methanoyl]-propyl}-butyramide, (compound denoted as A2-B4-C6-D10), (Compound 41);

N-cyanomethyl-2-[2-1,1-difluoro-methoxy)-benzylsulfonylmethyl]-3-benzylsulfonyl-propionamide, (compound denoted as A13-B39-C1-D1), (Compound 48);

N-cyanomethyl-3-[2-(1,1-difluoro-methoxy)-benzylsulfonyl]-2-[2-(1,1-difluoro-methoxy)-benzylsulfonylmethyl]-propionamide, (compound denoted as A5-B39-C1-D1), (Compound 51);

N-[(S)-1-(1-benzylcarbamoyl-methanoyl)-propyl]-3-benzylsulfonyl-2-benzylsulfonylmethyl-propionamide, (compound denoted as A13-B4-C6-D8), (Compound 53);

N-[(S)-1-(1-benzooxazol-2-yl-methanoyl)-butyl]-2-[2-(1,1-difluoro-methoxy)-benzylsulfonylmethyl]-3-benzylsulfonyl-propionamide, (compound denoted as A13-B39-C11-D6), (Compound 54);

acetic acid (2S,3S)-3-(4-morpholin-4-yl-4-oxo-2-benzylsulfonylmethyl-butanoylamino)-4-oxo-azetidin-2-yl ester, (compound denoted as A2-B4-E4), (Compound 58);

N-cyanomethyl-3-(2-methyl-thiazol-4-ylmethylsulfonyl)-2-benzyl-sulfonylmethyl-propionamide, (compound denoted as A114-B4-C1-D1), (Compound 59);

and the N-oxide derivatives, prodrug derivatives, protected derivatives, individual stereoisomers and mixtures of isomers thereof; and the pharmaceutically acceptable salts and solvates (e.g. hydrates) of such compounds and the N-oxide derivatives, prodrug derivatives, protected derivatives, individual isomers and mixtures of isomers thereof.

Especially preferred compounds of the invention are:—

N-[(S)-1-(1-benzooxazol-2-yl-methanoyl)-butyl]-3-benzylsulfonyl-2-benzylsulfonylmethyl-propionamide (compound denoted as A64-B4-C11-D6), (Compound 1);

4-benzenesulfonyl-2-(2-benzenesulfonyl-ethyl)-N-[(S)-1-(1-benzooxazol-2-yl-methanoyl)butyl]-butyramide, (compound denoted as A4-B6-C11-D6), (Compound 4);

N-[(S)-1-(1-benzooxazol-2-yl-methanoyl)-propyl]-4-morpholin-4-yl-4-oxo-2-benzylsulfonylmethyl-butyramide (compound denoted as A2-B4-C6-D6), (Compound 29);

N-[(S)-1-(1-benzooxazol-2-yl-methanoyl)-pentyl]-4-morpholin-4-yl-4-oxo-2-benzylsulfonylmethyl-butyramide, (compound denoted as A2-B4-C9-D6), (Compound 30);

N-[(S)-1-(1-benzylcarbamoyl-methanoyl)-propyl]-4-morpholin-4-yl-4-oxo-2-benzylsulfonylmethyl-butyramide, (compound denoted as A2-B4-C6-D8), (Compound 32);

N-[(S)-1-((E)-2-benzenesulfonyl-vinyl)-pentyl]-3-benzylsulfonyl-2-benzylsulfonylmethyl-propionamide, (compound denoted as A13-B4-C9-D7), (Compound 38);

N-(3-Benzenesulfonyl-1-phenethyl-allyl)-3-benzylsulfonyl-2-benzylsulfonylmethyl-propionamide, (compound denoted as A13-B4-C10-D7), (Compound 39);

4-morpholin-4-yl-4-oxo-2-benzylsulfonylmethyl-N-{(S)-1-[1-(3-phenyl-[1,2,4]oxadiazol-5-yl)-methanoyl]-propyl}-butyramide, (compound denoted as A2-B4-C6-D10), (Compound 41);

N-[(S)-1-(1-benzylcarbamoyl-methanoyl)-propyl]-3-benzylsulfonyl-2-benzylsulfonylmethyl-propionamide, (compound denoted as A113-B4-C6-D8), (Compound 53);

N-[(S)-1-(1-benzooxazol-2-yl-methanoyl)-butyl]-2-[2-(1,1-difluoro-methoxy)-benzylsulfonylmethyl]-3-benzylsulfonyl-propionamide, (compound denoted as A13-B39-C11-D6), (Compound 54);

and the N-oxide derivatives, prodrug derivatives, protected derivatives, individual stereoisomers and mixtures of isomers thereof; and the pharmaceutically acceptable salts and solvates (e.g. hydrates) of such compounds and the N-oxide derivatives, prodrug derivatives, protected derivatives, individual isomers and mixtures of isomers thereof.

Pharmacology and Utility:

The compounds of the invention are selective inhibitors of cathepsin S and, as such, are useful for treating diseases in which cathepsin S activity contributes to the pathology and/or symptomatology of the disease. For example, the compounds of the invention are useful in treating autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, and allogeneic immune responses, including, but not limited to, organ transplants or tissue grafts.

Cathepsin S also is implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Examples 69, 70, 71 and 72, infra.

Administration and Pharmaceutical Compositions:

In general, compounds of Formula I will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula I may range from about 1 micrograms per kilogram body weight (μg/kg) per day to about 1 milligram per kilogram body weight (mg/kg) per day, typically from about 10 μg/kg/day to about 0.1 mg/kg/day. Therefore, a therapeutically effective amount for a 80 kg human patient may range from about 100 μg/day to about 100 mg/day, typically from about 1 μg/day to about 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 73.

Chemistry:

Processes for Making Compounds of Formula I:

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of Formula I, where $X^1$ is —NHC($R^1$)($R^2$)$X^2$, can be prepared by proceeding as in the following Reaction Scheme 1:

Reaction Scheme 1

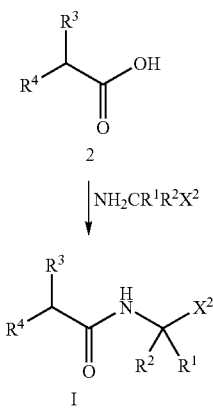

in which each $X^2$, $R^1$, $R^2$, $R^3$ and $R^4$ are as defined for Formula I in the Summary of the Invention.

Compounds of Formula I can be prepared by condensing an acid of Formula 2 with an amino compound of formula $NH_2CR^1R^2X^2$. The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotriazol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 5 to 10 hours to complete.

An oxidation step, if required, can be carried out with an oxidizing agent (e.g., Oxone®, metachloroperbenzoic acid or the like) in a suitable solvent (e.g., methanol, water, or the like, or any suitable combination thereof) at ambient temperature and requires 16 to 24 hours to complete. Detailed descriptions for the synthesis of a compound of Formula I by the processes in Reaction Scheme 1 are set forth in the Examples 1 to 6, infra.

Compounds of Formula I, where $X^1$ is —$NHX^3$, can be prepared by proceeding as in the following Reaction Scheme 2:

Reaction Scheme 2

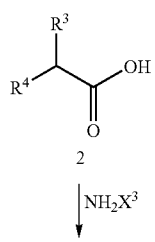

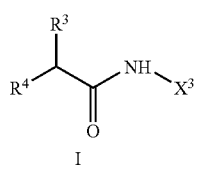

I in which each $X^3$, $R^3$ and $R^4$ are as defined for Formula I in the Summary of the Invention.

Compounds of Formula I can be prepared by condensing an acid of Formula 2 with an amino compound of formula $NH_2X^3$. The condensation reaction can be effected with an appropriate coupling agent (e.g., benzotriazol-1-yloxy-trispyrrolidinophosphonium hexafluorophosphate (Py-BOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotriazol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 5 to 10 hours to complete.

An oxidation step, if required, can be carried out with an oxidizing agent (e.g., Oxone® metachloroperbenzoic acid or the like) in a suitable solvent (e.g., methanol, water, or the like, or any suitable combination thereof) at ambient temperature and requires 16 to 24 hours to complete.

Compounds of Formula 2 can be prepared by reacting a compound of Formula 3 with a compound of Formula $R^3L$:

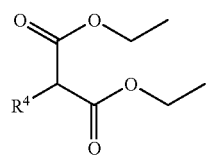

3 in which L is a leaving group and $R^3$ and $R^4$ are as defined in the Summary of the Invention. The reaction involves coupling (or alkylation) followed by alkaline hydrolysis at a temperature during which the dicarboxylic acid formed undergoes mono-decarboxylation. The coupling reaction can be carried out in the presence of a suitable base (e.g. triethylamine) in a suitable solvent (e.g. ethanol). The decarbalkoxylation can be effected under strongly basic conditions (e.g. in the presence of 1N aqueous sodium hydroxide) in a suitable solvent (e.g. ethanol). Detailed descriptions for the synthesis of compounds of Formula 2 by the process described above are set forth in the References, infra.

Compounds of Formula 2, in which $R^3$ and $R^4$ are benzylsulfonylmethyl, can be prepared by reacting a compound of Formula 4:

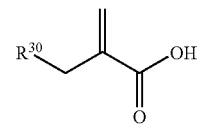

4 in which $R^{30}$ is a halo group, with benzyl mercaptan under strongly basic conditions to produce a compound of Formula 5:

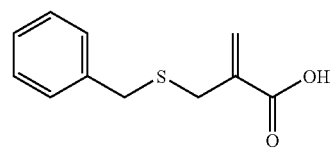

5 followed by reaction with benzyl mercaptan in the presence of a suitable coupling reagent (e.g. DMAP) and in a suitable solvent (e.g. DMF). A detailed description of the synthesis of a compound of Formula 2 by a similar process as that described above is set forth in the References, infra.

Compounds of Formula 2, in which $R^4$ is biaryl, can be prepared by coupling a compound of Formula 6:

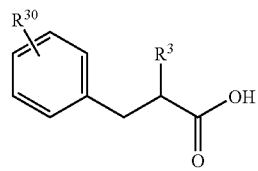

6 in which $R^{30}$ is a halo group and $R^3$ is as defined in the Summary of the Invention, with a compound of ArL, in which Ar is an aryl group and L is a leaving group, to produce a compound of Formula 2 in which $R^4$ is biaryl. The coupling reaction takes place in the presence of a suitable catalyst (e.g. tetrakis-triphenylphosphine palladium). A detailed description of the synthesis of a compound of Formula 2 by the process described above is set forth in the References, infra.

Additional Processes for Preparing Compounds of Formula I:

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this Application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, and the like). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethyl) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula I can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999. Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol. Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In summary, the compounds of Formula I are made by a process which comprises:

(A) reacting a compound of Formula 2:

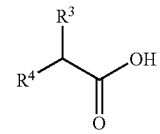

with a compound of the formula $NH_2CR^1R^2X^2$, in which $X^2$, $R^1$, $R^2$, $R^3$ and $R^4$ are as defined in the Summary of the Invention for Formula I; or (B) reacting a compound of Formula 2 with a compound of the formula $NH_2X^3$, in which $X^3$, $R^3$ and $R^4$ are as defined in the Summary of the Invention for Formula I; or (C) optionally converting a compound of Formula I into a pharmaceutically acceptable salt;

(D) optionally converting a salt form of a compound of Formula I to non-salt form;

(E) optionally converting an unoxidized form of a compound of Formula I into a pharmaceutically acceptable N-oxide;

(F) optionally converting an N-oxide form of a compound of Formula I its unoxidized form;

(G) optionally resolving an individual isomer of a compound of Formula I from a mixture of isomers;

(H) optionally converting a non-derivatized compound of Formula I into a pharmaceutically prodrug derivative; and (I) optionally converting a prodrug derivative of a compound of Formula I to its non-derivatized form.

EXAMPLES

The present invention is further exemplified, but not limited by, the following examples that illustrate the preparation of compounds of Formula I (Examples) and intermediates (References) according to the invention.

Reference 1

3-Benzylsulfanyl-2-benzylsulfanylmethyl-propionic acid

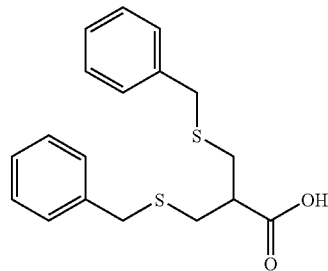

A solution of diethyl bis(hydroxymethyl)malonate (46.95 g, 0.21 moles) (prepared by the method of P. Block, Jr., Organic Synthesis, Collective Volume V, 381 (1973)) in methylene chloride (500 mL) was treated with triethyl amine (63 mL) and cooled to −30° C. A mixture of methylsulfonyl chloride (35 mL) in methylene chloride (40 mL) was added to the reaction mixture dropwise over 20 minutes and the reaction mixture was allowed to stir at room temperature for 18 hours. The reaction mixture was then poured into ice water and the product was extracted with methylene chloride. The organic extracts were washed with saturated aqueous sodium chloride and then dried over magnesium sulfate. The solvent was removed by rotary evaporation at reduced pressure and the residue was recrystallized from t-butylmethyl ether and hexane to give 2,2-bis-methylsulfonyloxymethyl-malonic acid diethyl ester (55.04 g).

Sodium (0.268 g, 11.6 mmol) was dissolved in ethanol (25 mL) and the resulting solution was treated with benzyl mercaptan (1.87 mL, 15.9 mmol). The reaction mixture was cooled on ice and the 2,2-bis-methylsulfonyloxymethyl-malonic acid diethyl ester (2.00 g, 5.31 mmol) was added. The reaction mixture was stirred at room temperature for 16 hours and then heated at 55° C. for 1.5 hours. The resulting solution was cooled to room temperature and poured into ice water. The product was extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give 3-benzylsulfanyl-2-benzylsulfanylmethyl-propionic acid ethyl ester (1.589 g, 83% yield).

3-Benzylsulfanyl-2-benzylsulfanylmethyl-propionic acid ethyl ester (1.589 g, 4.41 mmol) in a mixture of potassium hydroxide (1N, 7 mL), water (3 mL), dioxane (30 mL) and ethanol (10 mL) was stirred at room temperature for 18 hours. The solvents were removed form the reaction mixture by rotary evaporation at reduced pressure and the residue was dissolved in water and washed with ether. The aqueous layer was cooled on ice, acidified to pH 2 and the product extracted with ethyl acetate. The extracts were washed with saturated aqueous sodium chloride and then dried over magnesium sulfate. The solvent was removed by rotary evaporation at reduced pressure to give 3-benzylsulfanyl-2-benzylsulfanylmethyl-propionic acid (1.293 g, 88%).

Reference 2

2-Benzylsulfanylmethyl-3-[2-(1,1-difluoro-methoxy)-benzylsulfanyl]-propionic acid

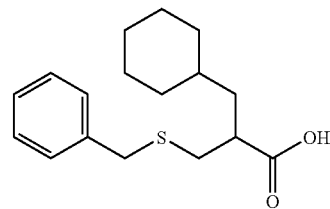

2-Bromomethylacrylic acid (3.00 g, 18.1 mmol) was dissolved in methanol (100 mL), cooled on an ice bath and treated with benzyl mercaptan. Aqueous sodium hydroxide (1N, 39.8 mL) was added dropwise and the reaction mixture was allowed to adjust to room temperature with stirring for 23 hours. Methanol was removed by rotary evaporation at reduced pressure and water (100 mL) was added to the residue, which was then washed with ether. The aqueous layer was cooled on ice and acidified to pH 2.5. The precipitated solid was isolated by filtration and dried to give 2-benzylsulfanylmethyl-acrylic acid (3.346 g, 89%).

A solution of 2-difluoromethoxybenzyl mercaptan (0.534 g, 2.81 mmol), 2-benzylsulfanylmethyl-acrylic acid (0.585 g, 2.81 mmol) and 4-dimethylaminopyridine (36 mg, 0.3 mmol) in DMF (1.5 ml) was stirred at room temperature for 20 hours. An additional amount of 2-difluoromethoxybenzyl mercaptan (0.201 g) was added to the reaction mixture and stirring was continued for another 24 hours. The reaction mixture was poured into dilute, cold, aqueous HCl and the product extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give 2-Benzylsulfanylmethyl-3-[2-(1,1-difluoromethoxy)-benzylsulfanyl]-propionic acid (0.706 g).

Reference 3

2-Benzylsulfanylmethyl-3-cyclohexyl-propionic acid

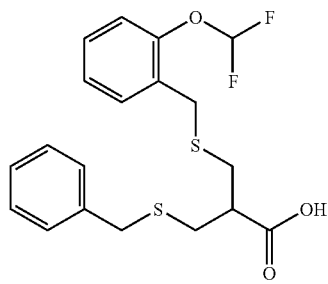

A solution of diethyl-2-cyclohexylmethyl malonate (2.56 g), 37% aqueous formaldehyde (0.80 mL), potassium bicarbonate (0.08 g) and ethanol (2.5 mL) was stirred at room temperature for 20 hours. Saturated aqueous ammonium sulfate (10 mL) was added to the reaction and the product extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give 2-cyclohexylmethyl-2-hydroxymethyl-malonic acid diethyl ester (1.31 g).

A solution of 2-cyclohexylmethyl-2-hydroxymethyl-malonic acid diethyl ester (1.31 g, 4.13 mmol) in methylene chloride (20 mL) and triethyl amine (1.16 mL, 8.00 mmol) was cooled to −40° C. A solution of methylsulfonyl chloride (0.402 mL, 5.2 mmol) in methylene chloride (4 mL) was added to the reaction mixture over 5 minutes. The reaction mixture was warmed to −10° C. over 1 hour and then poured into cold dilute aqueous HCl. The product was extracted with ethyl acetate, the extracts were washed with saturated aqueous sodium chloride and then dried over magnesium sulfate. The solvent was removed by rotary evaporation at reduced pressure to give 2-cyclohexylmethyl-2-methylsulfonyloxymethyl-malonic acid diethyl ester (1.505 g).

Sodium (0.097 g, 4.2 mmol) was dissolved in ethanol (10 mL) and the resulting solution was cooled to 0° C. and treated with a mixture comprising benzyl mercaptan (0.493 mL, 4.2 mmol) and 2-cyclohexylmethyl-2-methylsulfonyloxymethyl-malonic acid diethyl ester (1.466 g, 4.02 mmol). The reaction was stirred at room temperature for 17 hours, 53° C. for 20 hours and 73° C. for 24 hours. The ethanol was removed by rotary evaporation, the reaction mixture was poured into water and the product was extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give 2-benzylsulfanyl-methyl-3-cyclohexyl-propionic acid ethyl ester (0.237 g).

A mixture of 2-benzylsulfanylmethyl-3-cyclohexyl-propionic acid ethyl ester (0.230 g), dioxane (10 mL), sodium hydroxide (1N, 3 mL), water (2 mL) and ethanol (4 mL) was stirred for 20 hours at room temperature. The solvents were evaporated and the residue dissolved in water (50 mL). The aqueous solution was washed twice with ether and then acidified to pH2. The product was extracted from the aqueous solution with ethyl acetate and the extracts were washed with saturated aqueous sodium chloride and then dried over magnesium sulfate. The solvent was removed by rotary evaporation at reduced pressure to give acid 2-benzylsulfanylmethyl-3-cyclohexyl-propionic acid (0.210 g).

Reference 4

4-Benzenesulfonyl-2-(2-benzenesulfonyl-ethyl)-butyric acid

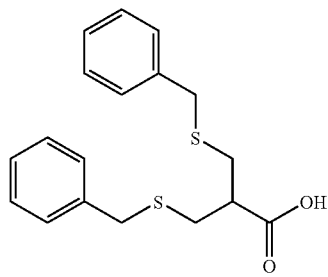

A mixture of 2-iodoethylphenyl sulfide (19.81 g, 75 mmol), diethyl malonate (4.80 g, 30 mmol), potassium carbonate (10.35 g, 75 mmol) and DMF (40 mL) was heated at 52° C. for 18 hours. More potassium carbonate (10 g) was added and the reaction was continued at 52° C. for another 8 hours. The reaction mixture was cooled, diluted with ice water and the product extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give 2,2-bis-(2-phenylsulfanyl-ethyl)-malonic acid diethyl ester (5.648 g).

A solution of 2,2-bis-(2-phenylsulfanyl-ethyl)-malonic acid diethyl ester (5.614 g) in ethanol (100 mL) was treated with lithium hydroxide (2.84 g) in water (10 mL). The reaction mixture was heated at 49° C. for 17 hours followed by 85° C. for 2 hours. The solvents were evaporated at reduced pressure to give a residue that was treated with water (100 mL) and washed with ether. The aqueous layer was cooled on ice, acidified and the product extracted with ethyl acetate. The extracts were dried over magnesium sulfate. The solvent was removed by rotary evaporation at reduced pressure to give acid 2,2-bis-(2-phenylsulfanyl-ethyl)-malonic acid (5.628 g).

2,2-Bis-(2-phenylsulfanyl-ethyl)-malonic acid (5.628 g) was heated at 150° C. for 30 minutes. The reaction mixture was cooled to room temperature, dissolved in ethyl acetate and washed with aqueous sodium bicarbonate. The ethyl acetate solution was washed with saturated aqueous sodium chloride and then dried over magnesium sulfate. The solvent was removed by rotary evaporation at reduced pressure and the residue was chromatographed on silica gel eluting with ethyl acetate/hexane to give 4-phenylsulfanyl-2-(2-phenylsulfanyl-ethyl)-butyric acid (1.831 g).

A solution of 4-phenylsulfanyl-2-(2-phenylsulfanyl-ethyl)-butyric acid (0.332 g) in methanol (10 mL) was treated with a solution of Oxone® (1.87 g in 10 mL of water). After stirring 18 hours at room temperature the reaction mixture was diluted with water (30 mL) and evaporated under reduced pressure to remove the methanol. The product was extracted with ethyl acetate. The extracts were washed with saturated aqueous sodium chloride and then dried over magnesium sulfate. The solvent was removed by rotary evaporation and the resulting oil was crystallized from t-butylmethyl ether to give 4-benzenesulfonyl-2-(2-benzenesulfonyl-ethyl)-butyric acid (0.315 g).

Reference 5

4-Morpholin-4-yl-4-oxo-2-(2-trifluoromethyl-benzylsulfonylmethyl)-butyric acid

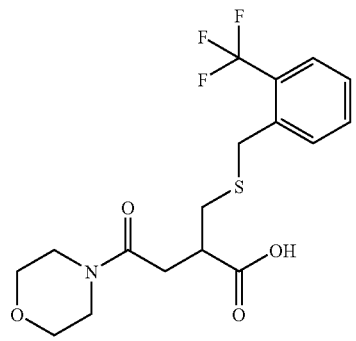

A solution of 3-methylene-dihydro-furan-2,5-dione (5.9 g, 52.7 mmol) in $CH_2Cl_2$ (200 mL) was cooled to 0° C. before adding morpholine (4.6 mL, 52.7 mmol) slowly over 5 minutes. The ice bath was removed and the mixture was stirred at room temperature for 1 hour. The solvent was evaporated under vacuum to 2-Methylene-4-morpholin-4-yl-4-oxo-butyric acid.

A mixture of 2-methylene-4-morpholin-4-yl-4-oxo-butyric acid (2 g, 10.03 mmol), in DMF (5 mL), 2-trifluoromethylbenzyl mercaptan (1.93 g, 10.03 mmol) and DMAP (122 mg, 1.0 mmol) was stirred at ambient temperature for 16 hours. Methanol (200 mL) and a saturated aqueous solution of Oxone® (20 g, 32.5 mmol) were added with continued stirring for 2 hours. Methanol was removed under vacuum and the aqueous residue was diluted with 200 mL of water. The crystallized product was filtered, washed with water, and dried under vacuum to yield 4-morpholin-4-yl-4-oxo-2-(2-trifluoromethyl-benzylsulfonylmethyl)-butyric acid (0.95 g) as a white solid.

Compounds of Formula I in which $R^3$ is —$CH_2SR^{14}$ ($R^{14}$ is as described in the summary of the invention) can be synthesized by the following reaction protocol:

 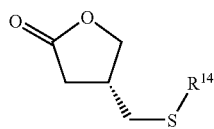

reference: JCS Perkin 1 1721, 1998

1

2

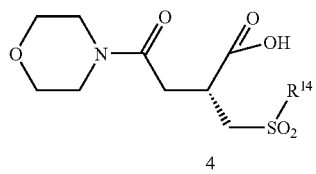 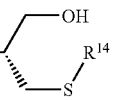

4

3

Compound 1 was prepared as S or R enantiomers using the method described by Crawforth et al. J. Chem. Soc., Perkin Trans. 1, 1721–1725, 1998.

Compound 2 was prepared by dissolving compound 1 in methylene chloride with triphenylphosphine (1.1 equivalents) followed by the slow addition of N-bromosuccinamide (1.95 equivalents) over a 5 minute period and the reaction was allowed to stir for 3–8 hours at room temperature. The mixture was then extracted with water and brine, then dried over sodium sulfate. After concentrating the residue was dissolved in ether and a small amount of heptane was added to remove unwanted solids. After filtering and concentration the resulting bromide was used without further purification. This intermediate was dissolved in THF then potassium thioacetate (1.1 equivalents) was added in one portion and the reaction was stirred for 3 to 24 hours at room temperature. The solvent was removed and the residue taken up in ethanol. Sodium hydroxide was added (2.2 equivalents) and the reaction was stiffed for 10 to 60 minutes at room temperature. 1 equivalent of a halo-substituted compound (eg. benzyl bromide, isobutyl bromide, cyclopropylmethyl bromide; see other elements from table 2, supra) was added with stirring for 6 to 24 hours at room temperature. The ethanol was removed under vacuum and the mixture was diluted with water and made acidic with 4 N HCl (pH=1 to 2). The aqueous layer was extracted with ethyl acetate 3 times and the organic layer was dried over sodium sulfate and concentrated. The product was purified on silica gel using a mixture of ethyl acetate and heptane (gradient 1:4 to 4:1) to give compound 2.

Compound 3 was made by stirring a solution of compound 2 in THF with morpholine (2 equivalents), which was heated, to reflux for 1 to 24 hours. Concentration of the mixture and redissolving in methylene chloride and extraction with diluted HCl removed the excess morpholine. The organic layer was washed with saturated sodium bicarbonate, dried over sodium sulfate and concentrated to dryness. The product was purified on silica gel using a mixture of ethyl acetate and heptane (gradient 1:4 to 4:1) to give compound 3.

Compound 4 was prepared from compound 3 by dissolving in a 1:1 mixture of methanol/water and adding oxone® (approximately 1 equivalent) over a period of 1 to 3 hours until a positive starch-iodine test was maintained. The solvent was removed under vacuum and the residue dissolved in a 1:1:1 mixture of water/acetonitrile/carbon tetrachloride. This was followed by the addition of sodium periodate and ruthenium (III) chloride which was vigorously stirred for 6 to 24 hours at a temperature below 40° C. The reaction was filtered through celite and concentrated to remove acetontrile and carbon tetrachloride. The aqueous layer was extracted with ethyl acetate 3 times and the organic layer dried over sodium sulfate and concentrated. The product was purified on silica gel using a mixture of ethyl acetate and heptane (1:4 to 4:1) to ethyl acetate and methanol (19:1 to 4:1) to give compound 4, which was obtained as R or S enantiomers.

Reference 6

(S)-4-Amino-2,2-difluoro-3-hydroxy-hexanoic acid dimethylamide

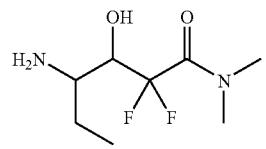

Activated zinc dust (2.16 g, 33 mmol) was suspended in dry THF (2 mL). A mixture of ethyl bromodifluoro acetate (6.5 g, 32 mmol) and (1S)-(1-formyl-propyl) carbamic acid tert-butyl ester (2 g, 10.7 mmol), in THF (10 mL), was added over 20 minutes while the mixture was sonicated. After complete addition, sonication was continued for a further 30 minutes. The mixture was then diluted with ethyl acetate (200 mL) and washed with 1N aqueous KHSO$_4$, brine, dried with magnesium sulfate and evaporated. The crude product was dissolved in ethanol (15 mL) and a solution of dimethylamine (40% in water; 2 mL) was added. After stirring for 16 hours at ambient temperature, the solvents were evaporated and the product was purified by flash chromatography on silica gel (hexane/ethyl acetate ratio of 3:1) to yield 200 mg of colorless oil.

The amide was dissolved in a mixture of TFA/dichloromethyl (1:1; 6 mL), stirred for 1 hour and evaporated to dryness. The product, (4S)-4-amino-2,2-difluoro-3-hydroxy-hexanoic acid dimethylamide, was obtained as the TFA salt and used without further purification.

Reference 7

(S)-3-Amino-2-hydroxy-pentanoic acid benzylamide

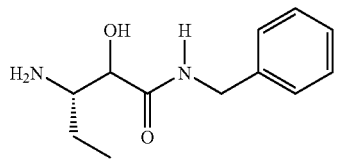

(1S)-(2-Cyano-1-ethyl-2-hydroxyethyl)carbamic acid tert-butyl ester (10 g, 46.7 mmol) was dissolved in 1,4-dioxane (100 mL). Anisole (5 mL) was added and then concentrated HCl (100 mL). The mixture was heated under reflux for 24 hours. The mixture was evaporated to dryness under vacuum and re-dissolved in 100 mL water. The solution was washed with ether and then neutralized with saturated aqueous $NaHCO_3$. Di-tert-butyl dicarbonate (10 g, 46 mmol) was added with 1,4-dioxane (200 mL), and the mixture was stirred at ambient temperature for 24 hours. The dioxane was removed under vacuum and the remaining aqueous solution was washed with ether. The solution was acidified with 1N HCl and extracted with ethyl acetate. The combined organic layers were washed with brine, dried with magnesium sulfate and evaporated to yield 3-tert-Butoxycarbonylamino-2-hydroxy-pentanoic acid (4.5 g) as yellowish oil.

3-tert-Butoxycarbonylamino-2-hydroxy-pentanoic acid (300 mg, 1.29 mmol) was combined with EDC (400 mg, 2.1 mmol) and HOBt (400 mg, 2.6 mmol). A solution of benzylamine (0.22 mL) and 4-methylmorpholine (0.5 mL) in dichloromethyl (4 mL) was added in one portion. The mixture was stirred at ambient temperature for 2 hours. After dilution with ethyl acetate (150 mL), the solution was washed with 1N aqueous HCl, water, saturated aqueous $NaHCO_3$ solution and brine. The resultant mixture was dried with magnesium sulfate and evaporated under vacuum to yield (S)-3-amino-2-hydroxy-pentanoic acid benzylamide (380 mg) as a white solid.

(S)-3-Amino-2-hydroxy-pentanoic acid benzylamide was dissolved in a mixture of TFA/dichloromethyl (1:1; 6 mL), stirred for 1 hour and evaporated to dryness. (3S)-3-Amino-2-hydroxy-pentanoic acid benzylamide was obtained as the TFA salt and used without further purification.

Reference 8

4-(4-Methylsulfonylamino-phenyl)-4-oxo-2-benzylsulfonylmethyl-butyric acid

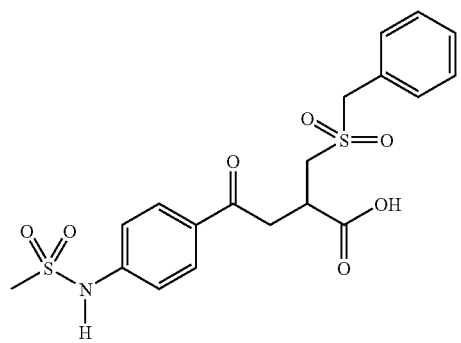

3-Methylene-dihydro-furan-2,5-dione (2 g, 17.8 mmol) and N-phenyl-methylsulfonamide (1.53 g, 8.92 mmol) were dissolved in anhydrous 1,2-dichloroethane. Aluminum trichloride (4.76 g, 35.7 mmol) was added and the mixture was stirred at 50° C. for 16 hours. Following dilution with ethyl acetate (400 mL), the solution was washed with 1N aqueous HCl, water and brine, dried with magnesium sulfate and evaporated. The product, 4-(4-methylsulfonylamino-phenyl)-2-methylene-4-oxo-butyric acid (1.70 g), was crystallized from ethylacetate/hexane.

4-(4-Methylsulfonylamino-phenyl)-2-methylene-4-oxo-butyric acid (800 mg, 2.83 mmol) was dissolved in DMF (5 mL). Benzyl mercaptan (0.5 mL, 4.25 mmol) and DMAP (200 mg, 1.6 mmol) were added. The mixture was stirred at ambient temperature for 16 hours. Methanol (200 mL) was added and, under vigorous stirring, a saturated aqueous solution of Oxone® (15 g, 24.4 mmol) was added in one portion. Stirring was continued for 2 hours. Methanol was removed under vacuum and the aqueous residue was diluted with 100 mL water. The crystallized product, 4-(4-Methylsulfonylamino-phenyl)-4-oxo-2-benzylsulfonylmethyl-butyric acid (380 mg), was filtered, washed with water, and dried under vacuum.

Reference 9

3-Biphenyl-3-yl-2-benzylsulfonylmethyl-propionic acid

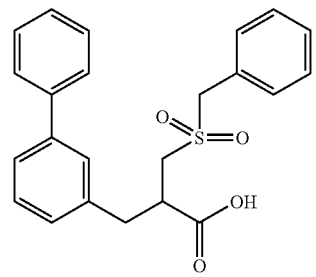

Sodium hydride (60% in oil, 1.36 g, 34 mmol) was dissolved in anhydrous ethanol (50 mL) under ice cooling. After the $H_2$ evolution ceased, diethylmalonate (5.15 mL, 34 mmol) was added and stirring was continued for 30 minutes at ambient temperature. Then 3-bromobenzyl bromide (4.24 g, 16.96 mmol) was added and stirring was continued for 2 hours. The reaction mixture was acidified with 1N aqueous HCl and extracted with ethyl acetate (3×150 mL). The combined organic layers were washed with brine, dried with magnesium sulfate and evaporated. The excess diethylmalonate was removed under high vacuum.

The crude product was dissolved in ethanol (50 mL) and 1N aqueous NaOH (20 mL) was added. After stirring for 16 hours, the mixture was acidified with 1N aqueous HCl and extracted with ethyl acetate. The combined organic layers were washed with brine, dried with magnesium sulfate and evaporated.

The crude monoacid was dissolved in 1,4-dioxane (20 mL). Diethylamine (2.48 mL, 24 mmol) was added and the solution was cooled to 0° C. Formaldehyde solution (37% in water, 2.44 mL) was added and stirring was continued for 24 hours at ambient temperature. After dilution with ethyl acetate (300 mL), the solution was washed with water, and brine, dried with magnesium sulfate and evaporated. The crude product, 2-(3-bromo-benzyl)-acrylic acid ethyl ester, was dissolved in ethanol (20 mL). Benzylmercaptan (2 mL, 17 mmol) and triethylamine (4 mL) were added. After stirring for 16 hours, 1N aqueous NaOH (50 mL) was added and enough 1,4-dioxane to get a homogenous solution. The reaction mixture was warmed to 50° C. for 5 hours. All organic solvents were removed under vacuum, and the aqueous residue was acidified to pH 1 with 1N aqueous HCl. The product was extracted with ethyl acetate (3×150 mL). The combined organic layers were washed with brine, dried with magnesium sulfate and evaporated. The residue was dissolved in methanol (250 mL) and Oxone® (35 g) was added. The reaction mixture was stirred at ambient temperature for 2 hours. Methanol was removed under vacuum. The precipitated product was filtered, washed with water, and dried under vacuum. Recrystallization from chloroform gave 3-(3-Bromo-phenyl)-2-benzylsulfonylmethyl-propionic acid (2.43 g) as white solid.

3-(3-Bromo-phenyl)-2-benzylsulfonylmethyl-propionic acid (0.5 g, 1.26 mmol) was dissolved in toluene (20 mL) and ethanol (5 mL). Tetrakistriphenylphosphine palladium (146 mg, 0.126 mmol) was added and the mixture was stirred at ambient temperature under nitrogen for 30 minutes. Powdered potassium carbonate (870 mg, 6.3 mmol) and phenylboronic acid (200 mg, 1.64 mmol) were added, and the reaction mixture was heated at 75° C. for 2 hours. After cooling, the mixture was acidified with 1N aqueous HCl and extracted with ethyl acetate (3×50 mL). The combined organic layers were washed with brine, dried with magnesium sulfate and evaporated. The acid was purified by flash chromatography on silica gel (ethyl acetate/hexane; 1:1) to yield 3-biphenyl-3-yl-2-benzylsulfonylmethyl-propionic acid (0.40 g).

Reference 10

3-Acetylsulfanyl-2-benzylsulfanylmethyl-propionic acid

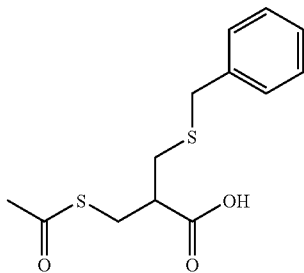

2-Bromomethylacrylic acid (3.00 g, 18.1 mmol) was dissolved in methanol (100 mL), cooled on an ice bath and treated with benzyl mercaptan. Aqueous sodium hydroxide (1N, 39.8 mL) was added dropwise and the reaction mixture was allowed to adjust to room temperature with stirring for 23 hours. Methanol was removed by rotary evaporation at reduced pressure and water (100 ml) was added to the residue, which was then washed with ether. The aqueous layer was cooled on ice and acidified to pH 2.5. The precipitated solid was isolated by filtration and dried to give 2-benzylsulfanylmethyl-acrylic acid (3.346 g, 89%).

A solution of 2-benzylsulfanylmethyl-acrylic acid (0.208 g) in methylene chloride (2.5 mL) was treated with thiolacetic acid and stirred at room temperature for 72 hours. The reaction mixture was diluted with ethyl acetate (50 mL) and then washed twice with water and once with saturated aqueous sodium chloride. After drying over magnesium sulfate the solvent was removed by rotary evaporation and the residue chromatographed on silica gel eluting with an ethyl acetate/hexane/acetic acid mixture to produce 3-acetylsulfanyl-2-benzylsulfanylmethyl-propionic acid (0.208 g).

Reference 11

(S)-2-Amino-1-(3-phenyl-[1,2,4]oxadiazol-5-yl)-butan-1-one

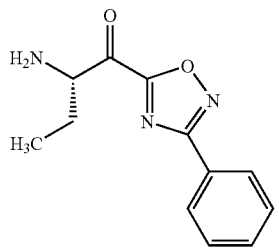

3-tert-Butoxycarbonylamino-2-hydroxy-pentanoic acid (500 mg, 2.14 mmol) was combined with EDC (600 mg, 3.14 mmol), HOBt (600 mg, 3.92 mmol), and N-hydroxybenzamidine (292 mg, 2.14 mmol). Dichloromethyl (10 mL) was added and then 4-methylmorpholine (1 mL). The mixture was stirred at ambient temperature for 16 hours. After dilution with ethyl acetate (200 mL), the solution was washed with water (30 mL), saturated aqueous NaHCO$_3$ solution and brine, dried with MgSO$_4$ and evaporated under vacuum. The crude product was dissolved in pyridine (10 mL) and heated at 80° C. for 15 hours. The pyridine was evaporated under vacuum and the residue was purified by flash chromatography on silica gel (eluent: ethyl acetate) to yield 290 mg (0.83 mmol). The oxadiazole (145 mg, 0.41 mmol) was dissolved in CH$_2$Cl$_2$ (4 mL) and TFA (4 mL) was added. After stirring for 1 hour, the mixture was evaporated to dryness to yield (S)-2-Amino-1-(3-phenyl-[1,2,4]oxadiazol-5-yl)-butan-1-one.

Reference 12

2-Amino-1-(2-phenyl-[1,3-dithian-2-yl)-hexan-1-ol

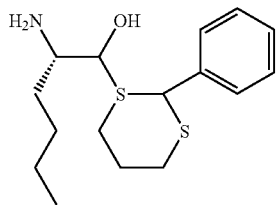

2-phenyl-1,3-dithiane (Aldrich) (3.79 g; 19.3 mmol) was mixed with dry distilled THF (20 mL) under a nitrogen atmosphere. The solution was cooled to −60° C. and n-butyl lithium (1.6M in pentane, 1.56 mmol, 9.74 mL) was added slowly by syringe. The reaction mixture was warmed to −20° C. and held at that temperature for 30 minutes, and then held at −10° C. for 15 minutes. The yellow solution was cooled to −78° C. and (1-Formyl-pentyl)-carbamic acid tert-butyl ester (1.6 g, 1.4 mmol, in 5 ml THF) was added rapidly (over 20 seconds) and 60 seconds later a mixture of 2 mL acetic acid and 5 mL THF was added rapidly. After warming to 23° C. the solution was concentrated at reduced pressure. Excess 2-phenyl-1,3-dithiane was removed by its crystallization away from the desired product using a minimum of ethyl acetate in hexane. The mother liquors were concentrated and chromatographed using a hexane-ethyl acetate gradient to afford 1.7 g of {1-[Hydroxy-(2-phenyl-[1,3]dithian-2-yl)-methyl]-pentyl}-carbamic acid tert-butyl ester. (56% yield).

To {1-[Hydroxy-(2-phenyl-[1,3]dithian-2-yl)-methyl]-pentyl}-carbamic acid tert-butyl ester (608 mg, 1.47 mmol) in 2.7 mL dioxane at 10° C. was added hydrochloric acid (2.7 mL, 4M in dioxane). The solution was warmed to 23° C. After 3 hours the solution was diluted with 5 ml toluene and concentrated under reduced pressure. The gummy solid was washed with diethyl ether resulting in the hydrochloride salt of 2-amino-1-(2-phenyl-[1,3]dithian-2-yl)-hexan-1-ol, 414 mg, 82% as a free flowing solid after removal of excess ether under reduced pressure.

Reference 13

3-Amino-4-hydroxo-pyrrolidine-1-carboxylic acid tert-butyl ester

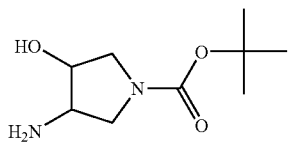

6-Oxa-3-aza-bicyclo[3.1.0]hexane-3-carboxylic acid tert-butyl ester (12.1 g, 65.3 mmol) was dissolved in a 8:1 methanol/water mixture (108 mL). Ammonium chloride (15 g) and sodium azide (21.4 g, 329 mmol) was added and the mixture was heated at 60° C. overnight. After dilution with ether (500 mL), the mixture was washed with saturated aqueous NaHCO$_3$ (200 mL) and brine (200 mL), dried with MgSO$_4$ and evaporated under vacuum. The crude product was dissolved in methanol (200 mL). 10% Palladium on activated carbon (1.5 g) was added and the mixture was stirred at ambient temperature under a hydrogen atmosphere until TLC analysis showed the disappearance of the starting material. The mixture was filtered through a pad of Celite and evaporated to dryness under vacuum. The product was purified by flash chromatography on silica gel. Eluent: 5% methanol in ethyl acetate to 20% methanol, 3% triethylamine in ethyl acetate. Yield: 4.3 g of 3-amino-4-hydroxy-pyrrolidine-1-carboxylic acid tert-butyl ester as yellowish solid.

Reference 14

2-Amino-2-methyl-1-oxazolo[4,5-b]pyridin-2-yl-propan-1-one

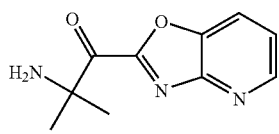

2-amino-2-methyl-1-propanol (17.8 g, 200 mmol) was dissolved in a mixture of water and 100 ml dioxane and cooled to 0° C. NaOH (8 g, 200 mmol) and di-t-butyl-dicarbonate (52.4 g, 240 mmol) were added and the reaction was allowed to warm to room temperature with stiffing for 2 hours. After removing the dioxane, the residue was extracted with EtOAc, washed with brine, dried with anhydrous MgSO$_4$, filtered and concentrated to yield 35 g of product.

A solution of oxylyl chloride (15.24 g, 120 mmol) in 200 ml of MeCl$_2$ was stiffed and cooled to −60° C. followed by the drop wise addition of dimethylsulfoxide (19.7 g, 252 mmol) in 60 ml of MeCl$_2$). After 10 minutes, a solution of 2-bocamino-2-methyl-1-propanol (118.9 g, 100 mmol) in 60 ml of MeCl$_2$, was added drop wise at −70° C. The reaction mixture was allowed to warm to −40° C. for 10 minutes followed by cooling to −70° C. before the addition of a solution of triethylamine (28.28 g, 280 mmol) in 60 ml of MeCl$_2$. The reaction mixture was allowed to warm to room temperature over a two-hour period and 40 ml of saturated sodium dihydrogen phosphate was added. The organic layer was washed with brine and dried over MgSO$_4$. The solvent was removed to yield 17.3 g of aldehyde.

A mixture of 2-amino-3-hydroxy pyridine (11 g, 100 mmol), triethylorthoformate (80 ml) and p-toluenesulfonic acid (61 mg) was heated at 140° C. for 8 hours. Excess triethylorthoformate was removed under vacuum. The product was crystallized from ethyl acetate to yield 9 g of pyridyloxazole; H$^1$ NMR (DMSO-δ): 9.26 (1H, s), 8.78 (1H, d), 8.45 (1H, d), 7.7(1H, dd); MS: 120.8 (M+1).

To a stirred solution of the pyridyloxazole (2.4 g, 20 mmol) in THF (100 ml) was added n-BuLi (1.6M solution in 12.5 ml of hexane) drop wise under N$_2$ at −78° C. After 1 hour, MgBr.Et$_2$O (5.16 g, 20 mmol) was added and the reaction mixture was allowed to warm to −45° C. for 1 hour before being treated with 2-boc-amino-2-methyl-propanyl-aldehyde (2.24 g, 12 mmol) in THF (20 ml). The reaction mixture was stirred for 1 hour, quenched with saturated NH$_4$Cl, and extracted with ethyl acetate. The organic layer was washed with brine, dried with MgSO$_4$ and concentrated. The residue was purified by silica gel column chromatography to yield 2-boc-amino-2-methyl-1-(5-pyridyloxazole-2-yl)-1-propanol (1.18 g); H$^1$ NMR (DMSO-δ): 8.5(1H, d,d, J=1.46 Hz, J=4.94 Hz), 8.14(1H, d,d, J1.49 Hz, J=8.16 Hz), 7.41(1H, d,d, J=4.7 Hz, J=8.18 Hz), 7.1–6.8(1H, d, d), 6.53(1H, br, NH), 6.24, 6.22(1H, s,s, OH), 5.23, 5.21(1H, s,s,, 1.37(3H, s, CH3), 1.33(9H, s, 3×CH3), 1.22(3H, s, CH3); MS: 308.2(M+1).

2-Boc-amino-2-methyl-1-(5-pyridyloxazole-2-yl)-1-propanol (156 mg, 0.508 mmol) and MeCl$_2$ (5 ml) were mixed and TFA (0.5 ml) was added at room temperature. After stirring for 1 hour, the solvent and excess TFA were removed under vacuum to produce 2-amino-2-methyl-1-oxazolo[4,5-b]pyridin-2-yl-propan-1-one TFA salt (165 mg).

Reference 15

2-Amino-1-(5-methoxymethyl-[1,3,4]oxadiazol-2-yl)-butan-1-one

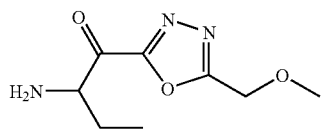

(S)-(+)-2-amino-1-butanol (50 g, 561 mmol) in 200 ml of water and 200 ml dioxane was cooled to 0° C. and mixed with NaOH (26.9 g, 673 mmol) and di-t-butyl-dicarbonate (146.96 g, 673 mmol). After the addition, the reaction was allowed to warm to room temperature. The reaction mixture was stirred for 2 hours. After removing the dioxane, the residue was extracted with EtOAc, then washed with brine and dried with anhydrous MgSO$_4$, filtered and concentrated. Without further purification, the crude product (120 g) was used for next step reaction.

A solution of oxylyl chloride (40.39 g, 265 mmol) in 700 ml of MeCl$_2$ was stirred and cooled to −60° C. Dimethylsulfoxide (51.7 g, 663 mmol) in 100 ml of MeCl$_2$ was added drop wise. After 10 minutes a solution of (S)-2-boc-amino-1-butanol (50 g, 265 mmol) in 100 ml of MeCl$_2$ was added drop wise at −70° C. The reaction mixture was allowed to warm to −40° C. for 10 minutes and then cooled to −70° C. again. A solution of triethylamine (74.9 g, 742 mmol) in 100 ml of MeCl$_2$ was added. The reaction mixture was allowed to warm to room temperature over 2 hours. 100 mls of saturated sodium dihydrogen phosphate was added, and then the organic layer was washed with brine and dried over MgSO$_4$. The solvent was removed to yield 45 g of (1-formyl-propyl)-carbamic acid tertbutyl ester; H$^1$ NMR (DMSO-δ): 9.4(1H, s), 7.29(1H, br.), 3.72(1H, m), 1.69(2H, m), 1.4–1.2(9H, s), 0.86(3H, t).

A mixture of methyl methoxyacetate (52 g, 500 mmol), hydrazine hydrate (30 ml) was heated to reflux for 8 hours. Excess hydrazine and water were removed under vacuum. The residue was extracted with n-butanol, dried with Na$_2$SO$_4$. Excess n-butanol was removed to yield 45 g of hydrazide.

A mixture of above hydrazide (45 g), triethylorthoformate (146 ml) and p-toluenesulfonic acid (61 mg) was heated at 140° C. for 8 hours. Excess triethylorthoformate was removed under vacuum. The product was purified by silica gel column chromatography to yield 4.6 g of 2-methoxymethyl-1,3,4-oxadiazole; H$^1$ NMR (DMSO-δ): 9.21(1H, s), 4.63(2H, s), 3.27(3H, s).

To a stirred solution of 2-methoxymethyl-1,3,4-oxadiazole (4.6 g, 40 mmol) in THF (100 ml) was added n-BuLi (1.6M solution in 25.2 ml of hexane) drop wise under N$_2$ at −78° C. After 1 hour, MgBr.Et$_2$O (10.4 g, 40.3 mmol) was added and the reaction mixture was allowed to warm to −45° C. for 1 hour before being treated with 2-boc-amino-propanyl aldehyde (5.28 g, 28.25 mmol) in THF (20 ml). The reaction mixture was stirred for 1 hour, quenched with saturated NH$_4$Cl, and extracted with ethyl acetate. The organic layer was washed with brine, dried with MgSO$_4$ and concentrated. The residue was purified by silica gel column chromatography to yield 2-boc-amino-1-(5-methoxymethyl-1,3,4-oxadiazole-2-yl)-1-propanol (500 mg); H$^1$ NMR (DMSO-δ): 6.7(½H, d, NH, diastereomeric), 6.5(½H, d, NH, diastereomeric), 6.2(½H, d, OH, diastereomeric), 6.0 (½H, d, OH, diastereomeric), 4.83–4.79 (1H, m), 4.55(2H, s), 4.05–3.5(1H, m), 3.31(3H, s), 1.9–1.4(2H, m), 1.4–1.2 (9H, m), 0.85–0.81(3H, m); MS: 300.4(M−1), 302.4(M+1).

2-Boc-amino-1-(5-methoxymethyl-1,3,4-oxadiazole-2-yl)-1-propanol (500 mg, 1.66 mmol), and MeCl$_2$ (5 ml) were mixed and TFA (0.5 ml) was added at room temperature. After stirring for 1 hour, the solvent and excess TFA were removed under vacuum to produce 2-amino-1-(5-methoxymethyl-[1,3,4]oxadiazol-2-yl)-butan-1-one TFA salt (340 mg).

Reference 16

2-Amino-1-(5-phenyl-[1,3,4]oxadiazol-2-yl)-1-butanol

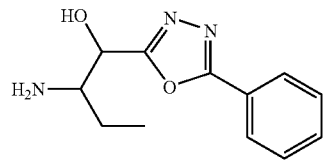

A mixture of the benzylhydrazide (22.5 g, 165 mmol), triethylorthoformide (150 ml) and p-toluenesulfonic acid (300 mg) was heated at 120° C. for 12 hours. Excess triethylorthoformide was removed under vacuum and the residue was purified by silica gel column chromatography to produce oxadiazole (14.5 g); H$^1$ NMR (DMSO-δ): 9.34(1H, s), 8.05–7.98(2H, m), 7.68–7.55(3H, m); MS: 147.4 (M+1).

To a stirred solution of the oxadiazole (10 g, 68.5 mmol) in THF (100 ml) was added n-BuLi (1.6M solution in 42.8 ml of hexane) drop wise under N$_2$ at −78° C. After 1 hour, MgBr.Et$_2$O (17.69 g, 68.5 mmol) was added and the reaction mixture was allowed to warm to −45° C. for 1 hour before being treated with 2-boc-amino-butyl-aldehyde (7.8 g, 41 mmol) in THF (20 ml). The reaction mixture was stirred for 1 hour, quenched with saturated NH$_4$Cl, and extracted with ethyl acetate. The organic layer was washed with brine, dried with MgSO$_4$ and concentrated. The residue was purified by silica gel column chromatography to yield 2-(2-boc-amino-1-hydroxydutyl)-5-benzyl-1,3,4-oxadiazole (9.7 g); H$^1$ NMR (DMSO-δ): 8–7.9(2H, m), 7.8–7.7(3H, m), 6.8–6.6 (1H, d,d, NH, diastereomeric), 6.4–6.1(1H, d,d, OH, diastereomeric), 5–4.4(1H, m), 1.9–1.3(2H, m), 1.3–1.1(9H, s), 0.84(3H, t); MS: 334.5(M+1).

2-(2-Boc-amino-1-hydroxybutyl)-5-benzyl-1,3,4-oxadiazole (505 mg, 1.5 mmol) and MeCl$_2$ (5 ml) were mixed and TFA (1 ml) was added at room temperature. After stirring for 1 hour, the solvent and excess TFA were removed under vacuum to produce 530 mg of 2-amino-1-(5-phenyl-[1,3,4] oxadiazol-2-yl)-1-butanol TFA salt.

Reference 17

2-Amino-1-oxazolo[4,5-b]pyridin-2-yl-butan-1-one

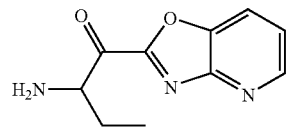

A mixture of 2-amino-3-hydroxy pyridine (25 g, 227 mmol), triethylorthoformate (75 ml) and p-toluenesulfonic acid (61 mg) was heated at 140° C. for 8 hours. Excess triethylorthoformate was removed under vacuum. The product was crystallized from ethyl acetate to yield 22.5 g of pyridyloxazole; H$^1$ NMR (DMSO-δ): 9.26 (1H, s), 8.78 (1H, d), 8.45 (1H, d), 7.7(1H, dd); MS: 120.8 (M+1).

Pyridyloxazole (600 mg, 5 mmol) in 30 ml THF was cooled to 0° C. before the addition of isopropanyl magnesium chloride (2M in THF, 2.5 ml, 5 mmol). After stirring for 1 hour at 0° C., the aldehyde (513 mg, 3 mmol) in 20 ml THF was added. The ice bath was removed and the reaction allowed to warm to room temperature. The reaction mixture was stirred for 2 hours and quenched with saturated ammonium chloride solution. Excess THF was removed and the residue was extracted with EtOAc, washed with brine, dried with anhydrous MgSO$_4$, filtered and concentrated. The crude residue was purified by chromatography to yield 383 mg product; H$^1$ NMR (DMSO-δ): 8.42(1H, m), 8.18(1H, m), 7.3(1H, m), 6.8, 6.6(1H, dd, d, OH, diastereomeric), 6.3, 6.02(1H, d, d, NH, diastereomeric), 4.82, 4.5(1H, m, m, diastereomeric), 1.8–1.3(2H, m), 1.2, 1.05(9H, s,s, diastereomeric), 0.89(3H, m); MS: 306.2(M−1), 308.6(M+1).

To a stirred solution of the pyridyloxazole (12 g, 100 mmol) in THF (300 ml) was added n-BuLi (1.6M solution in 62.5 ml of hexane) drop wise under N$_2$ at −78° C. After 1 hour, MgBr.Et$_2$O (25.8 g, 100 mmol) was added and the reaction mixture was allowed to warm to −45° C. for 1 hour before being treated with 2-boc-amino-butyl-aldehyde (11.46 g, 60 mmol) in THF (50 ml). The reaction mixture was stirred for 1 hour, quenched with saturated NH$_4$Cl, and extracted with ethyl acetate. The organic layer was washed with brine, dried with MgSO$_4$ and concentrated. The residue was purified by silica gel column chromatography to yield 2-boc-amino-1-(5-pyridyloxazole-2-yl)-1-butanol (14.1 g).

2-Boc-amino-1-(5-pyridyloxazole-2-yl)-1-butanol (311 mg, mmol) and MeCl$_2$ (5 ml) were mixed and TFA (1 ml) was added at room temperature. After stirring for 1 hour, the solvent and excess TFA were removed under vacuum to produce 355 mg of 2-amino-1-oxazolo[4,5-b]pyridin-2-yl-butan-1-one TFA salt.

Reference 18

2-Amino-1-(5-pyridin-4-yl-[1,3,4]oxadiazol-2-yl)-butan-1-one

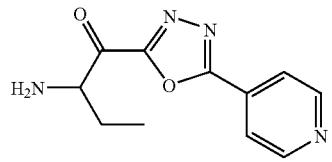

A mixture of the isonicotinic hydrazide (13.7 g, 100 mmol), triethylorthoformate (60 ml) and p-toluenesulfonic acid (30 mg) was heated at 130° C. for 12 hours. Excess triethylorthoformate was removed under vacuum. The product was crystallized from ethyl acetate to yield 14.8 g; H$^1$ NMR (DMSO-δ): 9.46 (1H, s), 8.8 (2H, dd), 7.9 (2H, dd).

To a stirred solution of the oxadiazole (11.5 g, 78.2 mmol) in THF (300 ml) was added 5 ml HMPA and n-BuLi (1.6M solution in 48.9 ml of hexane) drop wise under N$_2$ at −78° C. After 1 hour, MgBr.Et$_2$O (20.2 g, 78.2 mmol) was added and the reaction mixture was allowed to warm to −45° C. for 1 hour before being treated with 2-boc-amino-butylldehyde (9.7 g, 50.8 mmol) in THF (50 ml). The reaction mixture was stirred for 1 hour, quenched with saturated NH$_4$Cl, and extracted with ethyl acetate. The organic layer was washed with brine, dried with MgSO$_4$ and concentrated. The residue was purified with silica gel column chromatography to yield 2-bocamino-1-(5-pyridin-4-yl-[1,3,4]oxadiazol-2-yl)-butan-1-ol (3.5 g); H$^1$ NMR (DMSO-δ): 8.85–8.8(2H, m), 7.95–7.8(2H, m), 6.66(1H, d,), 6.19(1H, d), 4.96(1H, t), 3.75–3.6(1H, m), 1.72–1.6(1H, m), 1.5–1.35(1H, m), 1.27 (9H, s), 0.87(3H, t); MS: 333.2(M−1), 335.4 (M+1).

2-Bocamino-1-(5-pyridin-4-yl-[1,3,4]oxadiazol-2-yl)-butan-1-ol (334 mg, 1 mmol) and MeCl$_2$ (5 ml) were mixed and TFA (0.5 ml) was added at room temperature. After stirring for 1 hour, the solvent and excess TFA were removed under vacuum to produce 350 mg of 2-amino-1-(5-pyridin-4-yl-[1,3,4]oxadiazol-2-yl)-butan-1-one TFA salt.

Reference 19

2-Amino-1-(5-pyridin-3-yl-[1,3,4]oxadiazol-2-yl)-butan-1-one

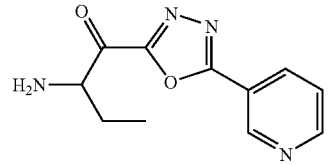

To a stirred solution of the 3-[1,3,4]-oxadiazol-2-yl-pyridine (5 g, 34 mmol) in THF (100 ml) was added 5 ml HMPA and n-BuLi (1.6M solution in hexane, 21.25 ml) drop wise under N$_2$ at −78° C. After 1 hour, MgBr.Et$_2$O (8.77 g, 34 mmol) was added and the reaction mixture was allowed to warm to −45° C. for 1 hour before being treated with 2-boc-amino-butylldehyde (4.22 g, 22.1 mmol) in THF (20 ml). The reaction mixture was stirred for 1 hour, quenched with saturated NH$_4$Cl, and extracted with ethyl acetate. The organic layer was washed with brine, dried with MgSO$_4$ and concentrated. The residue was purified with silica gel column chromatography to yield 2-boc-amino-1-(5-pyridin-3-yl-[1,3,4]oxadiazol-2-yl)-butan-1-ol (1.5 g); H$^1$ NMR (DMSO-δ): 9.2–9.1(1H, d), 8.82–8.76(1H, m), 8.4–8.3(1H, m), 7.68–7.6(1H, m), 6.78, 6.65(1H, dd, NH, diastereomeric), 6.38, 6.16(1H, d,d, OH, diastereomeric), 3.8–3.6 (1H, m), 1.9–1.2(2H, m), 1.3, 1.1(9H, s,s,), 0.84(3H, t); MS: 331.2 (M−1).

2-Boc-amino-1-(5-pyridin-3-yl-[1,3,4]oxadiazol-2-yl)-butan-1-ol (167 mg, 0.5 mmol) and MeCl$_2$ (5 ml) were mixed and TFA (0.5 ml) was added at room temperature. After stirring for 1 hour, the solvent and excess TFA were removed under vacuum to produce 180 mg of 2-amino-1-(5-pyridin-3-yl-[1,3,4]oxadiazol-2-yl)-butan-1-one TFA salt.

Reference 20

2-Amino-1-benzooxazol-2-yl-butan-1-one

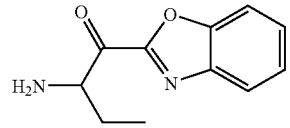

Benzoxazole (600 mg, 5 mmol) in 20 ml THF was cooled to −5° C. and isopropyl magnesium chloride (2 M in THF, 2.5 ml, 5 mmol) was added. After stirring for 1 hour at −5° C., the aldehyde (561 mg, 3 mmol), prepared as in reference 15, in 10 ml THF was added. The reaction was allowed to warm to room temperature with stirring for 2 hours. The reaction was quenched with saturated ammonium chloride solution, excess THF solvent removed. The residue was extracted with EtOAc, washed with brine, dried with anhydrous MgSO$_4$, filtered and concentrated. The crude residue was purified by chromatograph to yield 688 mg product (75%); LC-MS: 305.2 (M−1), 307.0 (M+1); H$^1$ NMR (DMSO-d$_6$): 7.72–7.6(2H, m), 7.38–7.28(2H, m), 6.7 (d)–6.52(d) (1H, NH, diastereomeric), 6.12(d)–5.92 (d) (1H, OH, diastereomeric), 4.81(dd)–4.57(dd) (1H, CH—OH), 3.74 (1H, m), 1.9–1.6 (1H, m), 1.6–1.3 (1H, m), 1.25(s)–1.1(s) (9H, diastereomeric), 0.85 (3H, t).

[1-(Benzooxazol-2-yl-hydroxy-methyl)-propyl]-carbamic acid tert-butyl ester (275 mg, 0.89 mmol) and MeCl₂ (5 ml) were mixed and TFA (1 ml) was added at room temperature. After stirring for 1 hour, the solvent and excess TFA were removed under vacuum to produce 260 mg of 2-amino-1-benzooxazol-2-yl-butan-1-one TFA salt.

Reference 21

2-Cyclohexylmethyl-4-morpholin-4-yl-4-oxo-butyric acid

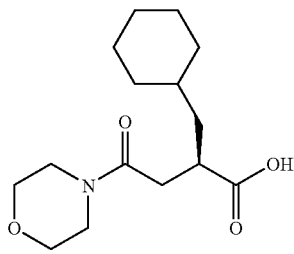

A 0.05 M solution of 1-(4-benzyl-2-oxo-oxazolidin-3-yl)-2-cyclohexylmethyl-4-morpholin-4-yl-butane-1,4-dione (1 g) in 3:1 —THF/H₂O was treated at 0° C. with 8 equivalents of 30% H₂O₂ followed by 2.0 equivalents of LiOH. The resulting mixture was stirred at 0–25° C. until the substrate had been consumed (approximately 1 hour). The excess peroxide was quenched at 0° C. with a 10% excess of 1.5 N aqueous Na₂SO₃. After buffering to pH 9–10 with aqueous NaHCO₃ and evaporation of the THF, the oxazolidone chiral auxiliary was recovered by MeCl₂ extraction. The carboxylic acid was isolated by EtOAc extraction of the acidified (pH 1–2) aqueous phase, then recrystallized from EtOAc and hexane to yield 0.58 g of 2-cyclohexylmethyl-4-morpholin-4-yl-4-oxo-butyric acid; H¹NMR (DMSO-δ): 12(1H, s, COOH), 3.6–3.3(8H, m), 2.8–2.3(3H, m), 1.8–1.1(1 1H, m), 0.9–0.7(2H, m); MS: 282.2(M−1), 284.1 (M+1).

Reference 22

2-(2-Cyclohexyl-ethyl)-4-morpholin-4-yl-4-oxo-butyric acid

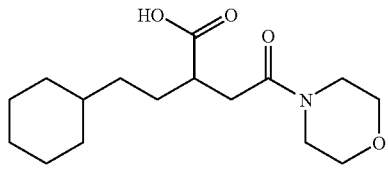

(S)-(−)-4-Benzyl-2-oxazolidinone (5 g, 28.2 mmol) was dissolved in THF (100 mL) and cooled to −78° C. under nitrogen. A 2.5M solution of n-butyllithium in hexane (12.4 mL) was added with a syringe and the mixture was stirred for 30 min. 4-Cyclohexyl-butyryl chloride (5.85 g, 31 mmol) was added at −78° C. The mixture was allowed to warm to 0° C. over two hours. 1N HCl (50 mL) was added and the product was extracted with ethyl acetate (3×100 mL). The combined organic layers were washed with saturated aqueous NaHCO₃ (200 ml) and brine (200 mL), dried with MgSO₄ and evaporated under vacuum. The product was recrystallized from hexane/ether and obtained as a white solid (5.6 g).

A solution of diisopropylamine (1.92 mL, 13.68 mmol) in dry THF (50 mL) was cooled to −20° C. A 2.5M solution of n-butyl lithium in hexane (4.4 mL) was added with a syringe. The mixture was stirred for 30 min and then cooled to −78° C. A solution of 4-benzyl-3-(4-cyclohexyl-butyryl)-oxazolidin-2-one (3 g, 9.12 mmol) in THF (10 mL) was added slowly over 3 min. Stirring was continued for 30 min, then a solution of 2-Bromo-1-morpholin-4-yl-ethanone (2.28 g, 10.94 mmol) in THF (4 mL) was added over 3 min. The mixture was allowed to come to room temperature over 5 h. 1N HCl (50 mL) was added and the product was extracted with ethyl acetate (3×100 mL). The combined organic layers were washed with saturated aqueous NaHCO₃ (200 mL) and brine (200 mL), dried with MgSO₄ and evaporated under vacuum. The product (1-(4-benzyl-2-oxo-oxazolidin-3-yl)-2-(2-cyclohexyl-ethyl)-4-morpholin-4-yl-butane-1,4-dione) was obtained after purification by flash chromatography as a single diastereomer (2.5 g). ¹H NMR: (CDCl₃) 7.35–7.22(m, 5H), 4.69–4.62 (m, 1H), 4.28–4.10 (m, 3H), 3.76–3.46 (m, 8H), 3.37 (d, J=13.6 Hz, 1H), 2.91 (ddd, J=16.4 Hz, J=13 Hz, J=3 Hz, 1H), 2.76 (ddd, J=13.5 Hz, J=11 Hz, J=3 Hz, 1H), 2.51 (dt, J=13.6 Hz, J=3 Hz, 1H), 1.76–0.80 (m, 15H). MS: (M+H)⁺ 457.

1-(4-Benzyl-2-oxo-oxazolidin-3-yl)-2-(2-cyclohexyl-ethyl)-4-morpholin-4-yl-butane-1,4-dione (2.5 g, 5.48 mmol) was dissolved in a 3:1-THF/H₂O mixture (50 mL) and cooled to 0° C. H₂O₂ (5 mL) was added followed by lithium hydroxyde monohydrate (462 mg, 11 mmol). The mixture was stirred at 0° C. for 30 min. Excess peroxide was quenched with 1.5N Na₂SO₃ solution and the THF was evaporated under vacuum. The chiral auxiliary was removed by extraction with diethyl ether. After acidification to pH 1 the product was isolated by extraction with ethyl acetate. The combined organic layers were washed with saturated aqueous NaHCO₃ (200 mL) and brine (200 mL), dried with MgSO₄ and evaporated under vacuum. The crude acid ((2R)-2-(2-Cyclohexyl-ethyl)-4-morpholin-4-yl-4-oxo-butyric acid) was used for coupling (EDC) and oxidation (Dess-Martin) as described in the examples, infra.

(2R)-1-((4S)-4-Benzyl-2-oxo-oxazolidin-3-yl)-2-cyclohexylmethyl-4-morpholin-4-yl-butane-1,4-dione was prepared by the same procedure as described for reference 22. 4-Cyclohexyl-butyryl chloride was substituted by 3-cyclohexyl-propionyl chloride. ¹H NMR: (DMSO) 7.35–7.22 (m, 5H), 4.63–4.56 (m, 1H), 4.28 (t, J=8.5 Hz, 1H), 4.17–4.06 (m, 2H), 3.70–3.35 (m, 8H), 2.94 (d, J=13.2 Hz, 1H), 2.82 (dd, J=13.2 Hz, J=8 Hz, 1H), 2.72 (dd, J=16 Hz, J=10.4 Hz, 1H), 2.51 (dd, J=16 Hz, J=3.2 Hz, 1H), 1.75–0.75 (m, 13H); MS: (M+H)⁺ 443.

Reference 23

N-Isopropyl-2-benzylsulfonylmethyl-succinamic acid

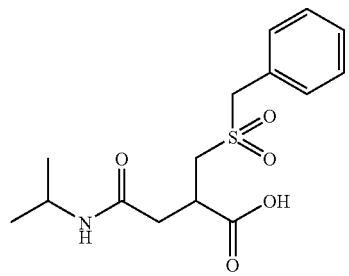

1405

To a stirring mixture of itacconic anhydride (1.1209 g, 10 mmol) in 10 ml of methylene chloride at 0° C. was added drop wise isopropyl amine (0.85 ml, 10 mmol). The reaction was stirred at room temperature for 1 hour and the solvent was removed under reduced pressure to give 2-(isopropyl-carbamoyl-methyl)-acrylic acid. The residue was dissolved in 10 ml of DMF, then benzyl mercaptan (1.17 g, 10.0 mmol) and DMAP (122 mg, 1 mmol) were added and the reaction was stirred at room temperature for overnight. The mixture containing 2-benzylsulfanylmethyl-N-isopropyl-succinamic acid was cooled to 0° C. and oxone® (4.9182 g, 8 mmol) in 20 ml of water was added and stirred for 2 hours at room temperature. More oxone® was added and the reaction was stirred at room temperature for 18 hours. The reaction was filtered and the white solid was washed with water, ether and dried under high vacuum to give 1.0 grams of N-isopropyl-2-benzylsulfonylmethyl-succinamic acid, which was used without further purification; LCMS retention time 2:32 minutes: MS+1 (328.1).

Reference 24

4-(4-Methyl-piperazin-1-yl)-4-oxo-2-benzylsulfonyl-methyl-butyric acid

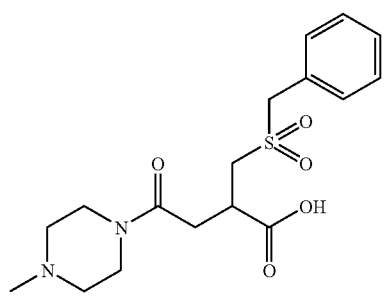

1406

To a stirring mixture of itacconic anhydride 1.1209 g, 10 mmol) in 10 ml of methylene chloride at 0° C. was added drop wise methyl piperizine (1.0 g, 10 mmol). The reaction was stirred at room temperature for 1 hour and the solvent was removed under reduced pressure to give compound 2-[2-(4-methyl-piperazin-1-yl)-2-oxo-ethyl]-acrylic acid. The residue was dissolved in 10 ml of DMF, then benzyl mercaptan (1.17 g, 10.0 mmol) and DMAP (122 mg, 1 mmol) were added and heated to 50–60° C. until reaction turned clear then the reaction was stirred at room temperature for overnight. Another 0.59 ml of benzyl mercapton (5 mmol) was added and the reaction was stirred overnight at room temperature. The mixture containing compound 2-benzylsulfanylmethyl-4-(4-methyl-piperazin-1-yl)-4-oxo-butyric acid was cooled to 0° C. and oxone® (6.1378 g, 10 mmol) in 20 ml of water was added and stirred for overnight at room temperature. More oxone® was added and the reaction was stirred at room temperature for 2 hours. The reaction was filtered and the product was in the aqueous phase and was purified on HPLC to give 0.2477 gram of pure 4-(4-methyl-piperazin-1-yl)-4-oxo-2-benzylsulfonylm-ethyl-butyric acid; LCMS retention time: 1.72 minutes; M+1 (369.3).

Reference 25

2-(2-Morpholin-4-yl-2-oxo-ethyl)-5-phenyl-pentanoic acid

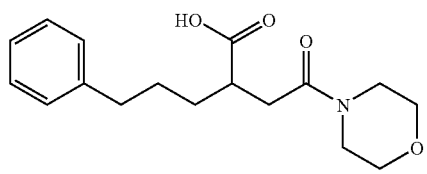

Reference 25 was synthesized as described in the following reaction protocol:

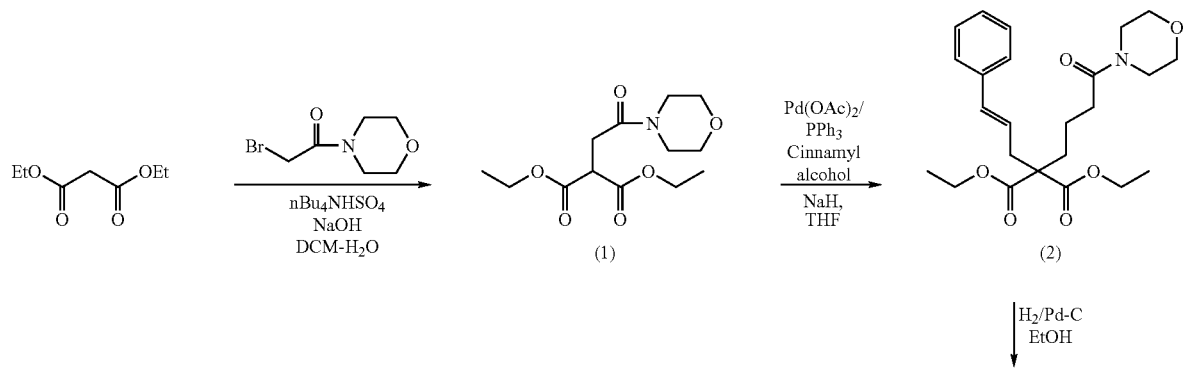

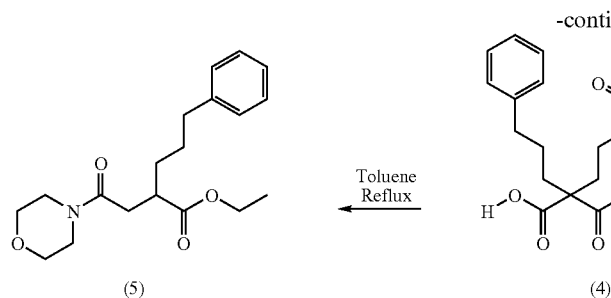

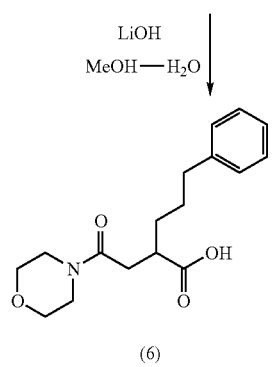

2-(2-Morpholin-4-yl-2-oxo-ethyl)-malonic acid diethyl ester (1)

To a solution of n-tetra butyl ammonium hydrogen sulfate (1.18 g, 3.48 mmol) and NaOH (560 mg, 13.9 mmol) in water (8 ml) was added a solution of 4-(2-bromoacetyl morpholine) (1.45 g, 6.97 mmol) and diethyl malonate (1.34 g, 8.36 mmol) in DCM (8 ml). The mixture was stirred at room temperature for 3 hours, diluted with water (30 ml) and extracted with DCM (2×30 ml). The organic layer was dried (MgSO$_4$) and concentrated in vacuum. The residue was purified by chromatography (silica) eluting with 1:2 v/v ethyl acetate-heptane to give 2-(2-morpholin-4-yl-2-oxo-ethyl)-malonic acid diethyl ester as a colorless oil (1.19 g, 59%); $^1$H NMR (CDCl$_3$) 4.25 (m, 4H), 4.0 (t, J=7.2 Hz, 1H), 3.8–3.45 (m, 8H), 3.0 (d, J=7.4 Hz, 2H), 1.3 (t, 1=7.1 Hz, 6H).

2-(2-Morpholin-4-yl-2-oxo-ethyl)-2-(3-phenyl-allyl)-malonic acid diethyl ester (2)

To a mixture of Pd(OAc)$_2$ (17.5 mg, 0.078 mmol) and PPh$_3$ (40.9 mg, 0.156 mmol) in dry THF (2 ml) under N$_2$, cinnamyl alcohol (105.1 mg, 0.78 mmol) was added followed by a solution of 2-(2-morpholin-4-yl-2-oxo-ethyl)-malonic acid diethyl ester (250 mg, 0.87 mmol) and NaH (17.4 mg, 0.43 mmol) in dry THF (3 ml). BF$_3$ (1M in THF, 1 ml, 1 mmol) was then added and the yellow solution was stirred at room temperature for 6.5 hours. The mixture was diluted with ethyl acetate (50 ml) and washed with 1N HCl (10 ml) and brine (2×20 ml). The organic layer was dried (MgSO$_4$), concentrated in vacuum and purified by chromatography eluting with 1:1 v/v ethyl acetate-heptane mixture to give 2-(2-morpholin-4-yl-2-oxo-ethyl)-2-(3-phenyl-allyl)-malonic acid diethyl ester as a thick, yellow oil (266.5 mg, 85%); $^1$H NMR (CDCl$_3$) 7.25 (m, 5H), 6.40 (d, J=15.6 Hz, 1H), 6.1 (dt, J=15.8, 7.7 Hz), 4.2 (q, J=7.1 Hz, 4H), 3.6 (m, 6H), 3.45 (m, 2H), 3.05 (d, J=7.6 Hz, 2H), 3.0 (s, 2H), 1.25 (t, J=7.1 Hz, 6H). MS: 404 (MH$^+$)

2-(2-Morpholin-4-yl-2-oxo-ethyl)-2-(3-phenyl-propyl)-malonic acid diethyl ester (3)

A solution of 2-(2-morpholin-4-yl-2-oxo-ethyl)-2-(3-phenyl-allyl)-malonic acid diethyl ester (257 mg, 0.637 mmol) in EtOH (15 ml) was hydrogenated over Pd/C at 55 Psi for 7.5 hrs. The catalyst filtered off over a pad of Celite and the filtrate evaporated under vacuum to give 2-(2-morpholin-4-yl-2-oxo-ethyl)-2-(3-phenyl-propyl)-malonic acid diethyl ester as a light yellow oil (260 mg); $^1$H NMR (CDCl$_3$) 7.4–7.1 (m, 5H), 4.20 (q, J=7.1 Hz, 4H), 3.7–3.4 (m, 8H), 3.0 (s, 2H), 2.6 (t, J=7.6 Hz, 2H), 2.2 (m, 2H), 2.55 (m, 2H), 1.20 (t, J=7.1 Hz, 6H). MS: 406 (MH$^+$).

2-(2-Morpholin-4-yl-2-oxo-ethyl)-2-(3-phenyl-propyl)-malonic acid monoethyl ester (4)

To a solution of 2-(2-morpholin-4-yl-2-oxo-ethyl)-2-(3-phenyl-propyl)-malonic acid diethyl ester (934 mg, 2.3 mmol) in a 2:1 mixture of ethanol and water (12 ml) LiOH.H$_2$O (193.3 mg, 4.61 mmol) was added and heated at 40° C. for 19 hrs. Ethanol was evaporated under reduced pressure, the residual aqueous mixture was acidified to pH 1 and extracted with methylene chloride (2×40 ml). The organic extract was dried with MgSO$_4$ and evaporated under reduced pressure to give 2-(2-morpholin-4-yl-2-oxo-ethyl)-2-(3-phenyl-propyl)-malonic acid monoethyl ester as a thick, yellow oil (831 mg); $^1$H NMR (CDCl$_3$) 7.4–7.1 (m, 6H), 4.25 (q, J=7.1 Hz, 2H), 3.8–3.4 (m, 8H), 3.20 (d, J=16.4 Hz, 1H), 2.9 (d, J=16.4 Hz, 1H), 2.6 (m, 2H), 2.1–1.8 (m, 4H), 1.25 (t, J=7.1 Hz, 3H). MS: 378 (MH$^+$).

2-(2-Morpholin-4-yl-2-oxo-ethyl)-5-phenyl-pentanoic acid ethyl ester (5)

A Solution of 2-(2-morpholin-4-yl-2-oxo-ethyl)-2-(3-phenyl-propyl)-malonic acid monoethyl ester (809 mg, 2.14 mmol) in toluene (25 ml) was heated under reflux for 23 hours. The colorless solution was concentrated under reduced pressure, the residue was taken up in diethyl ether (50 ml), washed with saturated NaHCO$_3$ and dried over MgSO$_4$. The solvent was evaporated under reduced pressure to give 2-(2-morpholin-4-yl-2-oxoethyl)-5-phenyl-pentanoic acid ethyl ester as yellow oil (617 mg); $^1$H NMR (CDCl$_3$) 7.37–7.1 (m, 5H), 4.2 (m, 2H), 3.8–3.4 (m, 8H), 3.0 (m, 1H), 2.75 (dd, J=15.9, 9.4 Hz, 1H), 2.65 (m, 2H), 2.35 (dd, J=15.9, 5.1 Hz, 1H), 1.8–1.55 (m, 4H), 1.29 (t, J=7.1 Hz, 3H). MS: 334 (MH$^+$).

2-(2-Morpholin-4-yl-2-oxo-ethyl)-5-phenyl-pentanoic acid (6)

To a solution of 2-(2-morpholin-4-yl-2-oxo-ethyl)-5-phenyl-pentanoic acid ethyl ester (604 mg, 1.81 mmol) in a 2:1 mixture of MeOH—H$_2$O (12 ml) LiOH.H$_2$O (228 mg, 5.43 mmol) was added and stirred overnight at room temperature. Ethanol was removed under reduced pressure, residue diluted with water (40 ml) and washed with ether. The aqueous layer was acidified to pH1 with 1N HCl and extracted with diethyl ether (3×25 ml). The combined organic extracts were dried with MgSO$_4$ and concentrated under reduced pressure to give 2-(2-morpholin-4-yl-2-oxo-ethyl)-5-phenyl-pentanoic acid as a white solid (492 mg); $^1$H NMR (CDCl$_3$) 8.0–7.5 (1H), 7.4–7.1 (m, 5H), 3.8–3.4 (m, 8H), 3.0 (m, 1H), 2.8 (dd, J=16.4, 9.6 Hz, 1H), 2.65 (t, J=7.2 Hz, 2H), 2.40 (dd, J=16.4, 4.3 Hz, 1H), 1.9–1.5 (m, 4H). MS: 306 (MH$^+$).

Reference 26

2-Amino-1-(5-phenyl-[1,2,4]oxadiazol-3-yl)-butan-1-ol

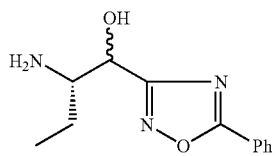

Reference 26 was synthesized as described in the following reaction protocol:

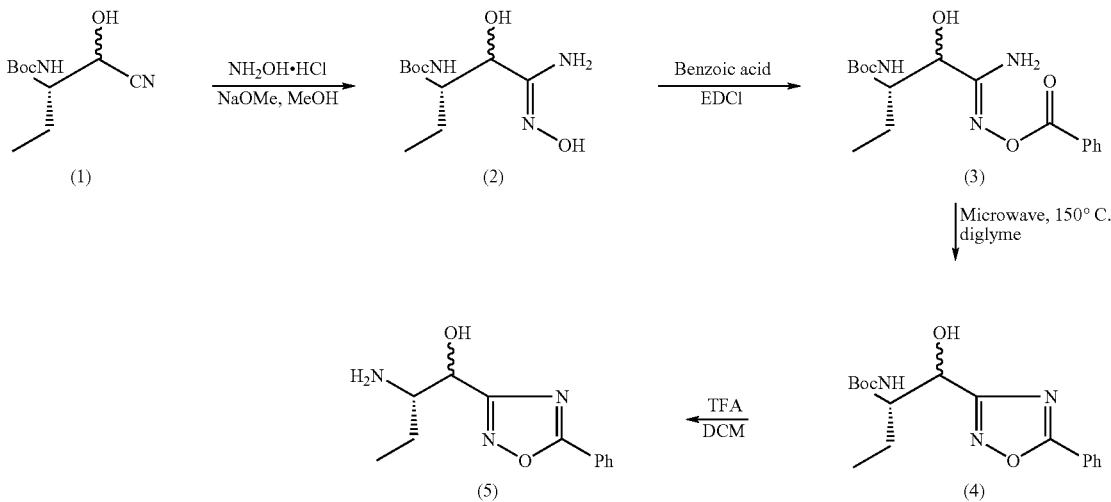

{1-[Hydroxy-(N-hydroxycarbamimidoyl)-methyl]-propyl}-carbamic acid tert-butyl ester (2)

A solution of (2-cyano-1-ethyl-2-hydroxy-ethyl)-carbamic acid tert-butyl ester (9.53 g, 44 mmol) in methanol (80 ml) was cooled to 0° C. and treated successively with hydroxylamine hydrochloride (3.05, 44 mmol) in methanol (80 ml) and 25% sodium methoxide solution in methanol (10.2 ml). Stirred at 0° C. for 5 minutes, cold bath removed and the reaction mixture stirred at room temperature for 5 hours. Methanol evaporated off under reduced pressure, crude partitioned between ethyl acetate and water. Organic layer separated, dried (MgSO$_4$) and evaporated under reduced pressure to give yellow oil. Purified by mplc, eluting with a mixture of ethyl acetate-heptane to give the title compound as white solid (3.5 g); MS: M(H$^+$) 248.

{1-[Hydroxy-(N-benzoyloxycarbamimidoyl)-methyl]-propyl}-carbamic acid tert-butyl ester (3)

A solution of {1-[hydroxy-(N-hydroxycarbamimidoyl)-methyl]-propyl}-carbamic acid tert-butyl ester (2) (2.5 g, 10 mmol) in dichloromethyl (125 ml) was treated with benzoic acid (1.36 g, 11 mmol), EDCI (2.14 g, 11 mmol), HOBT (1.37 g, 10 mmol) and triethylamine (1.35 ml, 11 mmol) and stirred at room temperature overnight. Reaction mixture was washed with saturated sodium bicarbonate solution and then water and dried over Na₂SO₄. Solvent evaporated under reduced pressure, crude purified by mplc eluting with 1% triethylamine in 2:3 v/v ethyl acetate and heptane mixture to give yellow solid (850 mg); MS: MH⁺ 352.

2-Amino-1-(5-phenyl-[1,2,4]oxadiazol-3-yl)-butan-1-ol (5)

A solution of (3) (1.5 g, 4.3 mmol) in diglyme was heated at 150° C. in a microwave (Smith Creator, S00219) for 40 minutes. Solvent evaporated under vacuum in Genevac Evaporator at 80° C. for 3 hours to give a brown solid. This was taken in dichloromethyl (40 ml) and treated with trifluoroacetic acid at room temperature for 2 hours. Solvent evaporated to dryness under reduced pressure, crude taken in water, washed with DCM, aqueous layer basified with 1M NaOH solution and extracted with dichloromethyl. Organic layer dried over Na₂SO₄ to give pale brown solid (300 mg); ¹HNMR (CDCl₃) 8.14–8.10 (m, 2H), 7.59–7.47 (m, 3H), 4.83 & 4.65 (d, J=5 Hz, 1H), 3.18–3.05 (2m, 1H), 1.71–1.20 (m, 2H), 1.05–0.97 (dt, J=7.2 Hz, 3H).

Reference 27

3-Benzylsulfonyl-2-(tetrahydro-pyran-4-yloxymethyl)-propionic acid (27a)

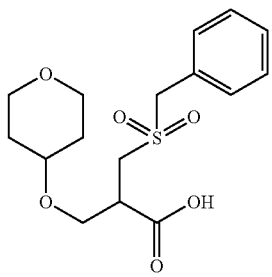

3-(Propane-1-sulfonyl)-2-(tetrahydro-pyran-4-yloxymethyl)-propionic acid (27b)

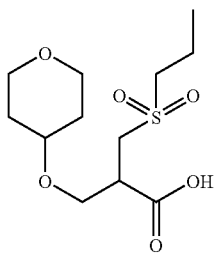

Compounds 27a and 27b were synthesized according to the following protocol:

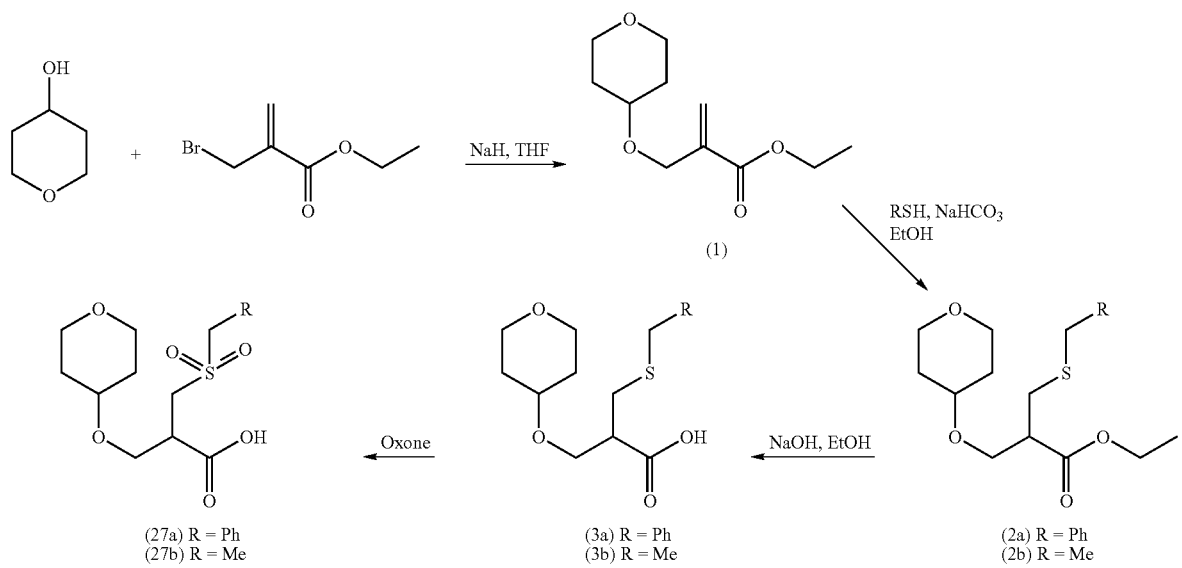

(27a) R = Ph
(27b) R = Me (3a) R = Ph
(3b) R = Me (2a) R = Ph
(2b) R = Me 2-(Tetrahydro-pyran-4-yloxymethyl)-acrylic acid ethyl ester (1)

NaH added to a solution of 4-hydroxy tetrahydropyran (5 g, 49 mmol) in THF (40 ml) stirred at room temperature for 30 minutes. A solution of ethyl 2-(bromomethyl) acrylate (9.6 g, 49 mmol) in THF (30 ml) was added and stiffed at room temperature overnight. Reaction mixture cooled in ice, quenched with saturated NH₄Cl solution and extracted with ethyl acetate. Organic extracts dried, (Na₂SO₄) and purified by mplc eluting with 1:9 to 2:8 v/v ethyl acetate-heptane mixture to give the title compound as yellow oil (6.56 g, 61%). MS: MH⁺ 215; LCMS retention time 3.29 minutes.

3-Benzylsulfanyl-2-(tetrahydro-pyran-4-yloxymethyl)-propionic acid ethyl ester (2a)

A suspension of 2-(tetrahydro-pyran-4-yloxymethyl)-acrylic acid ethyl ester (2.2 g, 10.2 mmol) in ethanol (100 ml) was treated with a solution of NaHCO₃ (0.86 g, 10.2 mmol) in water ml (10 ml) and benzyl mercaptan (1.21 ml, 10.2 mmol) at room temperature overnight. Ethanol evaporated off under reduced pressure, crude partitioned between ethyl acetate and water, organic layer separated and purified by mplc eluting with 1:9 to 2:8 v/v ethyl acetate-heptane mixture to give the title compound as pale yellow oil (1.27 g). MS: 339 (MH⁺); LCMS (Protocol B) retention time 4.3 minutes.

By using ethylmercapton 3-ethylsulfanyl-2-(tetrahydro-pyran-4-yloxymethyl)-propionic acid ethyl ester (2b) was similarly prepared; MS: 281 (MH⁺); LCMS retention time 3.9 minutes.

3-Benzylsulfanyl-2-(tetrahydro-pyran-4-yloxymethyl)-propionic acid (3a)

A solution of 3-benzylsulfanyl-2-(tetrahydro-pyran-4-yloxymethyl)-propionic acid ethyl ester (1.27 g) in ethanol (30 ml) was treated with 2N NaOH (9.4 ml) overnight. Usual water work up gave the title compound as white solid; MS: 333 (M+Na), 311 (M+1); LCMS retention time 3.7 minutes.

3-Ethylsulfanyl-2-(tetrahydro-pyran-4-yloxymethyl)-propionic acid (3b) was similarly prepared by using 3-ethylsulfanyl-2-(tetrahydro-pyran-4-yloxymethyl)-propionic acid ethyl ester.

3-Benzylsulfonyl-2-(tetrahydro-pyran-4-yloxymethyl)-propionic acid (27a)

A solution of 3-Benzylsulfanyl-2-(tetrahydro-pyran-4-yloxymethyl)-propionic acid (1.16 g, 3.7 mmol) in a mixture of MeOH (10 ml) and water (30 ml) was treated oxone (3.5 g, 5.6 mmol) overnight. Methanol evaporated off under reduced pressure, aqueous layer extracted with ethyl acetate, dried (Na₂SO₄) and evaporated under reduced pressure to give the title compound as white solid (1.36 g); MS: 365 (M+Na), 343 (MH⁺); LCMS retention time 3.1 minutes.

3-ethylsulfonyl-2-(tetrahydro-pyran-4-yloxymethyl)-propionic acid (27b) was similarly prepared from 3-ethylsulfanyl-2-(tetrahydro-pyran-4-yloxymethyl)-propionic acid; MS: 303 (M+Na), 281 (MH⁺); LCMS retention time 2.3 minutes.

Reference 28

4-Morpholin-4-yl-4-oxo-2-benzylsulfonylmethyl-butyric acid (28a); 2-(2-Methyl-propane-1-sulfonyl-methyl)-4-morpholin-4-yl-4-oxo-butyric acid (28b); 2-Cyclopropylmethylsulfonylmethyl-4-morpholin-4-yl-4-oxo-butyric acid (28c); and 2-(2-Difluoromethoxy-benzylsulfonylmethyl)-4-morpholin-4-yl-4-oxo-butyric acid (28d)

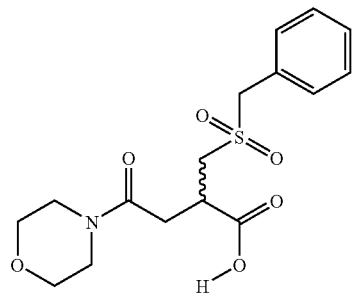
(28a)

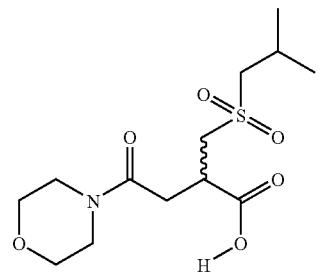
(28b)

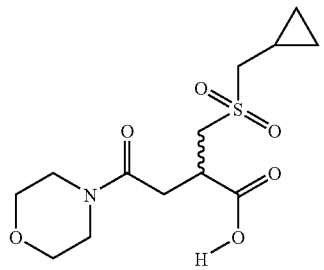
(28c)

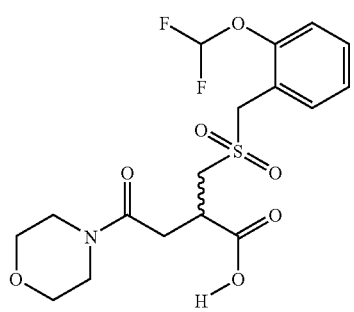
(28d)

4-Morpholin-4-yl-4-oxo-2-benzylsulfonylmethyl-butyric acid (28a) 2-(2-Methyl-propane-1-sulfonyl-methyl)-4-morpholin-4-yl-4-oxo-butyric acid (28b) 2-Cyclopropylmethylsulfonylmethyl-4-morpholin-4-yl-4-oxo-butyric acid (28c) 2-(2-Difluoromethoxy-benzylsulfonylmethyl)-4-morpholin-4-yl-4-oxo-butyric acid (28d)

Compounds 28a, b, c and d were synthesized according to the following protocol:

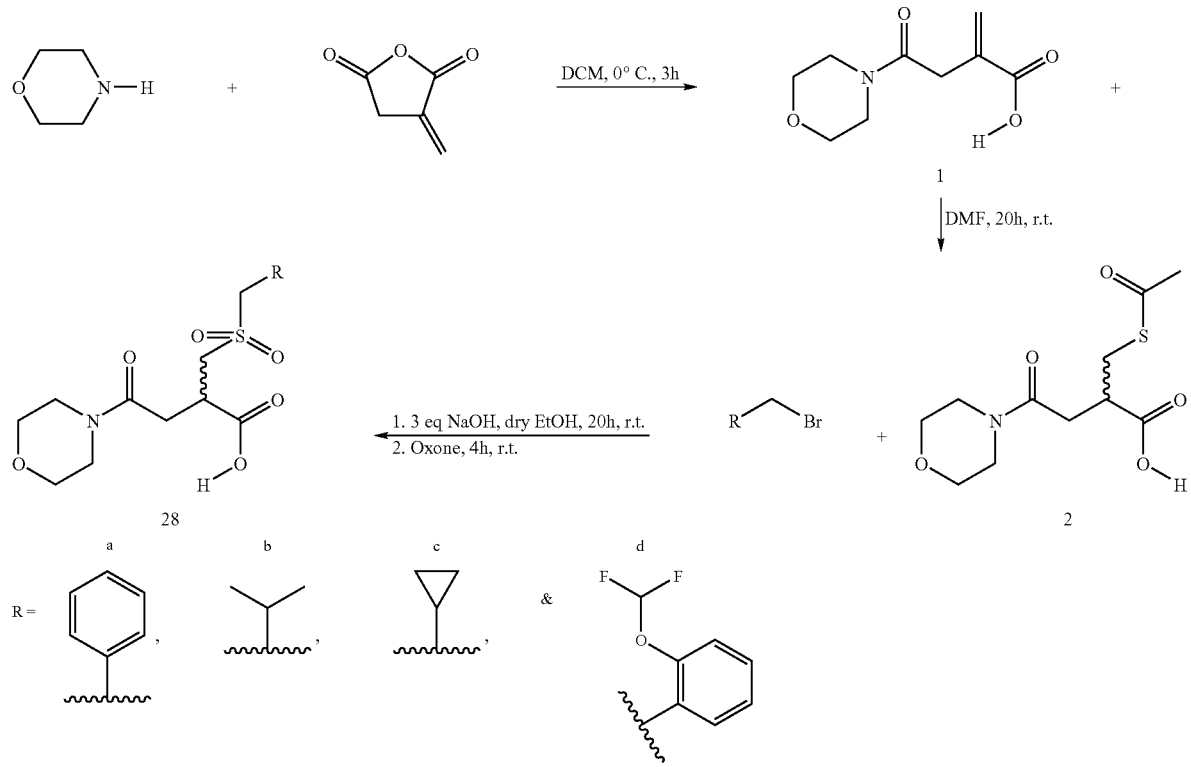

Synthesis of 2-(2-morpholin-4-yl-2-oxo-ethyl)-acrylic acid (1)

Morpholine (20 mL, 228.6 mmol) was slowly added to a stirring solution of itaconic anhydride (25.1 g, 228.6 mmol) suspended in dichloromethyl at 0° C. The reaction mixture was allowed to slowly warm to room temperature. Upon completion (LCMS), volatiles were removed by vacuum under reduced pressure. Crude yield: 44.96 g, 99%. Product was used without further purification.

Synthesis of 2-Acetylsulfanylmethyl-4-morpholin-4-yl-4-oxo-butyric acid (2)

2-(2-morpholin-4-yl-2-oxo-ethyl)-acrylic acid (55.19 g, 277.0 mmol) was dissolved in 120 mL DMF and set to stir at room temperature. Potassium thioacetate (25 g, 219.0 mmol) was added in one portion, and the reaction mixture was allowed to stir at ambient temperature for 20 hours. Upon completion (LCMS), DMF was removed by vacuum under reduced pressure. Crude Yield: 75 g. Percent Purity (LCMS): 40%. The crude product was used without further purification.

Synthesis of 4-morpholin-4-yl-4-oxo-2-benzylsulfonylmethyl-butyric acid (28a)

4-Morpholin-4-yl-4-oxo-2-benzylsulfonylmethyl-butyric acid (8.078 g, 29.37 mmol) was dissolved in 100 mL dry EtOH and set to stir at room temperature. NaOH pellets (3.52 g, 88.0 mmol) were added in one portion, and the reaction mixture was allowed to stir for 10 minutes. Benzyl bromide (3.18 mL, 26.7 mmol) was then added, and the reaction mixture was allowed to stir at ambient temperature for 20 hours. Upon completion (LCMS), the reaction mixture was diluted with water and the pH was lowered to ~pH2. The reaction mixture was then washed 3× with EtOAc. The organic phase was concentrated in vacuo and then diluted with 200 mL aqueous MeOH. Oxone® (10.78 g, 16.58 mmol) was added in one portion and the reaction was stirred at room temperature for 4 hours. Conversion of sulfide to sulfone was monitored via LCMS. Upon completion, reaction was quenched by the addition of sodium thiosulfate. Salts were filtered and the reaction mixture was washed 3× with ethyl acetate and dried over sodium sulfate. The organics were evaporated by vacuum under reduced pressure. The crude solid was crystallized from EtOAc.

Yield 1.3 g Percent Purity (NMR): 99%. m/z (LCMS) M⁺ 356.01. $\delta_H$ 12.6 (1H, br s), 7.4 (5H, m), 4.5 (2H, s), 3.5 (4H, m), 3.5 (1H, m), 3.4 (4H, m), 3.2 (2H, d), 2.75 (2H, d).

Synthesis of 2-(2-Methyl-propane-1-sulfonylmethyl)-4-morpholin-4-yl-4-oxo-butyric acid (28b)

4-Morpholin-4-yl-4-oxo-2-benzylsulfonylmethyl-butyric acid (10.90 g, 40.15 mmol) was dissolved in 100 mL dry EtOH and set to stir at room temperature. NaOH pellets (4.81 g, 120.45 mmol) were added in one portion, and the reaction mixture was allowed to stir for 10 minutes. 1-Bromo-2-methyl propane (5.0 g, 36.49 mmol) was then added, and the reaction mixture was allowed to stir at ambient temperature for 20 hours. Upon completion (LCMS), the reaction mixture was diluted with water and the pH was lowered to ~pH2. The reaction mixture was then washed 3× with EtOAc. The organic phase was concentrated in vacuo and then diluted with 200 mL aqueous MeOH. Oxone (10.02 g, 14.57 mmol) was added in one portion and the reaction was stirred at room temperature for 4 hours. Conversion of sulfide to sulfone was monitored via LCMS. Upon completion, reaction was quenched by the addition of sodium thiosulfate. Salts were filtered, and the reaction mixture was washed 3× with ethyl acetate and dried over sodium sulfate. The organics were evaporated by vacuum under reduced pressure. Product was purified via HPLC. Yield: 1.1 g, 23.1%. m/z (LCMS) M⁺ 322.01, $R_f$=2.03. $\delta_H$ 12.6 (1H, br s), 3.5 (4H, m), 3.5 (1H, m), 3.4 (4H, m), 3.25 (2H, d), 3.0 (2H, m), 2.9 (2H, d), 2.4 (1H, m), 1.3 (6H, d d).

Synthesis of 2-Cyclopropylmethylsulfonylmethyl-4-morpholin-4-yl-4-oxo-butyric acid (28c)

4-Morpholin-4-yl-4-oxo-2-benzylsulfonylmethyl-butyric acid (11.16 g, 40.74 mmol) was dissolved in 100 mL dry EtOH and set to stir at room temperature. NaOH pellets (4.81 g, 120.25 mmol) were added in one portion, and the reaction mixture was allowed to stir for 10 min. Bromomethylcyclopropane (5.0 g, 37.04 mmol) was then added, and the reaction mixture was allowed to stir at ambient temperature for 20 hours. Upon completion (LCMS), the reaction mixture was diluted with water and the pH was lowered to ~pH2. The reaction mixture was then washed 3× with EtOAc. The organic phase was concentrated in vacuo and then diluted with 200 mL aqueous MeOH. Oxone (15.6 g, 24.0 mmol) was added in one portion and the reaction was stirred at room temperature for 4 h. Conversion of sulfide to sulfone was monitored via LCMS. Upon completion, reaction was quenched by the addition of sodium thiosulfate. Salts were filtered, and the reaction mixture was washed 3× with ethyl acetate and dried over sodium sulfate. The organics were evaporated by vacuum under reduced pressure. Product was purified via HPLC. Yield: 1.2 g, 15.1%. m/z (LCMS) M⁺ 320.1, $R_f$=1.84. $\delta_H$ 12.6 (1H, br s), 3.5 (4H, m), 3.5 (1H, m), 3.4 (4H, m), 3.25 (2H, d), 3.0 (2H, m), 2.9 (2H, d), 2.4 (1H, m), 1.1 (1H, m), 0.62 (2H, q), 0.38 (2H, q).

Synthesis of 2-(2-Difluoromethoxy-benzylsulfonylmethyl)-4-morpholin-4-yl-4-oxo-butyric acid (28d)

4-Morpholin-4-yl-4-oxo-2-benzylsulfonylmethyl-butyric acid (1.27 g, 4.64 mmol) was dissolved in 50 mL dry EtOH and set to stir at room temperature. NaOH pellets (556 mg, 13.92 mmol) were added in one portion, and the reaction mixture was allowed to stir for 10 min. 2-(Difluoromethoxy)-benzyl bromide (1.00 g, 4.219 mmol) was then added, and the reaction mixture was allowed to stir at ambient temperature for 20 h. Upon completion (LCMS), the reaction mixture was diluted with water and the pH was lowered to ~2. The reaction mixture was then washed 3× with EtOAc. The organic phase was concentrated in vacuo and then diluted with 100 mL aqueous MeOH. Oxone (1.58 g, 2.43 mmol) was added in one portion and the reaction was stirred at room temperature for 4 h. Conversion of sulfide to sulfone was monitored via LCMS. Upon completion, reaction was quenched by the addition of sodium thiosulfate. Salts were filtered, and the reaction mixture was washed 3× with ethyl acetate and dried over sodium sulfate. The organics were evaporated by vacuum under reduced pressure. Product was purified via HPLC. Yield: 195 mg, 19.0%. m/z (LCMS) M⁺ 422.1. $R_f$=2.42. $\delta_H$ 12.6 (1H, br s), 7.6–7.2 (4H, m), 7.19 (1H, s) 4.5 (2H, s), 3.5 (4H, m), 3.5 (1H, m), 3.4 (4H, m), 3.2 (2H, d), 2.75 (2H, d).

Reference 29

(R)-2-((S)-1-Hydroxy-2-morpholin-4-yl-2-oxo-ethyl)-5-phenyl-pentanoic acid (5a) (R)-5-(2-Difluoromethoxy-phenyl)-2-((S)-1-hydroxy-2-morpholin-4-yl-2-oxo-ethyl)-pentanoic acid (5b)

(R)-2-((S)-1-Fluoro-2-morpholin-4-yl-2-oxo-ethyl)-5-phenyl-pentanoic acid (5c) (R)-5-(2-Difluoromethoxy-phenyl)-2-((S)-1-fluoro-2-morpholin-4-yl-2-oxo-ethyl)-pentanoic acid (5d)

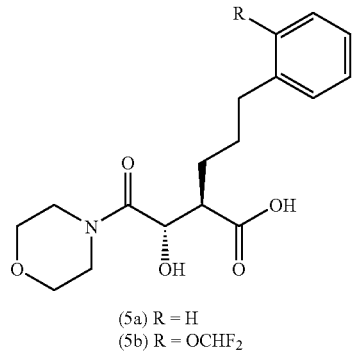

(5a) R = H
(5b) R = OCHF₂

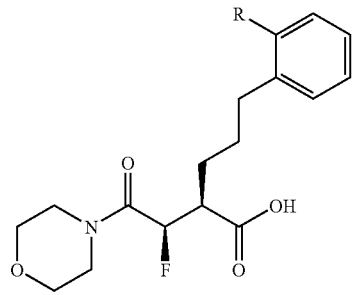

(5c) R = H
(5d) R = OCHF₂

Compounds 5a, 5b, 5c and 5d were prepared according to the following reaction protocol:
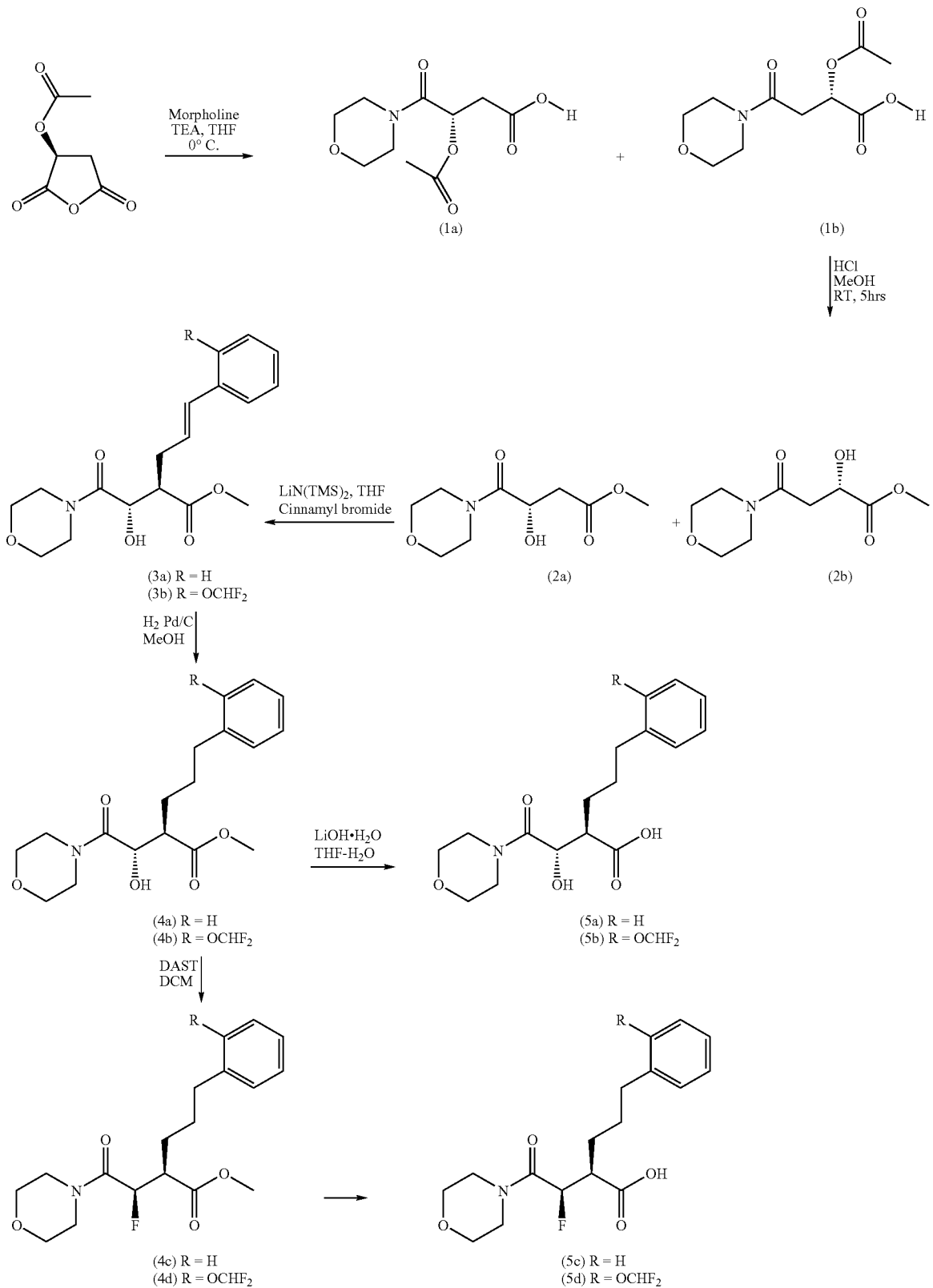

(S)-3-Acetoxy-4-morpholin-4-yl-4-oxo-butyric acid (1a) & (S)-2-Acetoxy-4-morpholin-4-yl-4-oxo-butyric acid (1b)

Morpholine (14.48 ml) and Triethylamine (23.14 ml, 166 mmol) were added to an ice-cold solution of acetic acid (S)-2,5-dioxo-tetrahydro-furan-3-yl ester (25 g, 158.12 mmol) in dry THF (600 ml) and the solution was stirred at room temperature over the week-end. Solvent was evaporated under reduced pressure, residue diluted with water, acidified to pH 2 with 1N HCl and extracted with ethyl acetate. Combined organic extracts were dried over $MgSO_4$ and evaporated under reduced pressure to give a mixture of (S)-3-acetoxy-4-morpholin-4-yl-4-oxo-butyric acid and 2-acetoxy-4-morpholin-4-yl-4-oxo-butyric acid (14 g) as colorless oil. MS: 246 ($MH^+$).

(S)-3-Hydroxy-4-morpholin-4-yl-4-oxo-butyric acid methyl ester (2a)

To a mixture of (S)-3-acetoxy-4-morpholin-4-yl-4-oxo-butyric acid and 2-Acetoxy-4-morpholin-4-yl-4-oxo-butyric acid (11 g, 44.8 mmol) in dry methanol (30 ml) HCl in dioxane (4M, 7.3 ml, 29.16 mmol) was added and stirred at room temperature for 5 hrs. The reaction mixture was neutralized with solid $NaHCO_3$, filtered through a mixture of Celite/$Na_2SO_4$ (1:1) and concentrated under reduced pressure to give a mixture of (S)-3-Hydroxy-4-morpholin-4-yl-4-oxo-butyric acid methyl ester and (S)-2-Hydroxy-4-morpholin-4-yl-4-oxo-butyric acid methyl ester. Column chromatography on silica eluting with a mixture of ethyl acetate and methylene chloride gave (S)-3-Hydroxy-4-morpholin-4-yl-4-oxo-butyric acid methyl ester, (6 g) as white solid; $^1H$ NMR ($CDCl_3$) δ 2.62 (d, J=8 Hz, 2H), 3.78–3.44 (m, 11H), 3.76 (d, J=9 Hz, 1H), 4.8–4.73 (m, 1H); MS: 218 ($MH^+$).

(E)-(R)-2-((S)-1-Hydroxy-2-morpholin-4-yl-2-oxo-ethyl)-5-phenyl-pent-4-enoic acid methyl ester (3a)

Lithium hexamethyldisilazide (1M in THF, 14.5 ml, 14.5 mmol) was added to a solution of (S)-3-Hydroxy-4-morpholin-4-yl-4-oxo-butyric acid methyl ester (1.5 g, 6.9 mmol) in dry THF (15 ml) at −78° C. under $N_2$ and stirred for 30 min. Cinnamyl bromide (1.6 g, 7.32 mmol) was then added, the reaction mixture stirred at −78° C. for 2 hrs, warmed up to room temperature and stirred overnight at room temperature. The reaction was quenched with saturated ammonium chloride solution, adjusted the pH to 6 with 1N HCl and extracted with ethyl acetate. Combined ethyl acetate extracts were dried over $MgSO_4$ and concentrated under reduced pressure to give pale brown solid. Column chromatography on silica eluting with a mixture of ethyl acetate and methylene chloride gave the title compound as pale, yellow solid (1.15 g).

(E)-(R)-5-(2-Difluoromethoxy-phenyl)-2-((S)-1-hydroxy-2-morpholin-4-yl-2-oxo-ethyl)-pent-4-enoic acid methyl ester (3b)

Similarly prepared according to the procedure above but replacing cinnamyl bromide with 1-((E)-3-Bromo-propenyl)-2-difluoromethoxy-benzene.

(2R,3S)-2-Benzyl-3-hydroxy-4-morpholin-4-yl-4-oxo-butyric acid methyl ester (3c)

Similarly prepared according to the procedure above but replacing cinnamyl bromide with benzyl bromide.

(R)-2-((S)-1-Hydroxy-2-morpholin-4-yl-2-oxo-ethyl)-5-phenyl-pentanoic acid methyl ester (4a)

A solution of (E)-(R)-2-((S)-1-Hydroxy-2-morpholin-4-yl-2-oxo-ethyl)-5-phenyl-pent-4-enoic acid methyl ester (1.55 g, 4.65 mmol) in methanol (15 ml) was hydrogenated at 50 psi over Pd/C for 4 hrs. The catalyst was removed by filtration through celite and the filtrate concentrated under reduced pressure to give (R)-2-((S)-1-Hydroxy-2-morpholin-4-yl-2-oxo-ethyl)-5-phenyl-pentanoic acid methyl ester as pale, brown solid (1.45 g); $^1H$ NMR ($CDCl_3$) δ 1.90–1.65 (m, 4H), 2.62–2.75 (m, 3H), 3.75–3.40 (m, 11H), 4.0 (d, J=15 Hz, 1H), 4.47–4.4.39 (m, 1H), 7.38–7.15 (m, 5H); MS: 336($M^+$).

(R)-5-(2-Difluoromethoxy-phenyl)-2-((S)-1-hydroxy-2-morpholin-4-yl-2-oxo-ethyl)pentanoic acid methyl ester (4b)

Similarly prepared according to the procedure above but using (E)-(R)-5-(2-Difluoromethoxy-phenyl)-2-((S)-1-hydroxy-2-morpholin-4-yl-2-oxo-ethyl)-pent-4-enoic acid methyl ester; $^1H$ NMR ($CDCl_3$) δ 1.93–1.58 (m, 4H), 2.78–2.58 (m, 3H), 3.80–3.42 (m, 11H), 4.03 (m, 1H), 4.44 (m, 1H), 6.53 (t, J=74 Hz, 1H), 7.25–7.04 (m, 4H); MS: 402 ($MH^+$).

(S)-2-((R)-1-Fluoro-2-morpholin-4-yl-2-oxo-ethyl)-5-phenyl-pentanoic acid methyl ester (4c)

(Diethylamino) sulfur trifluoride (2.0 ml, 15.2 mmol) was added to a ice cold solution of (R)-2-((S)-1-Hydroxy-2-morpholin-4-yl-2-oxo-ethyl)-5-phenyl-pentanoic acid methyl ester (4a) (0.85 g, 2.5 mmol) in dry methylene chloride (15 ml) and the reaction mixture was stirred overnight while warming to room temperature. The reaction was quenched with aqueous $NaHCO_3$ solution and extracted with methylene chloride. The organic extracts were dried over $Na2SO_4$ and concentrated under reduced pressure. Column chromatography on silica eluting with a mixture of ethyl acetate and methylene chloride gave the title compound as an off-white solid (230 mg). $^1H$ NMR ($CDCl_3$) δ 1.90–1.58 (m, 4H), 2.78–2.57 (m, 2H), 3.28–3.10 (m, 1H), 3.75 (s, 3H), 3.74–3.45 (m, 8H), 5.40–5.12 (m, 1H), 7.35–7.18 (m, 5H); MS: 338($MH^+$).

(R)-2-((S)-1-Hydroxy-2-morpholin-4-yl-2-oxo-ethyl)-5-phenyl-pentanoic acid (5a)

A solution of (R)-2-((S)-1-hydroxy-2-morpholin-4-yl-2-oxo-ethyl)-5-phenyl-pentanoic acid methyl ester (230 mg, 0.69 mmol) and $LiOH.H_2O$ (57.5 mg, 1.37 mmol) in a mixture of THF and water (2:1, 6 ml) was stirred at room temperature for 2.5 hrs. The reaction was diluted with water and THF removed under reduced pressure. The pH of the aqueous solution was adjusted to pH5 with 1N HCl and extracted with ethyl acetate. The combined organic extracts were dried over $MgSO_4$ and evaporated under reduced pressure to give the title compound as white solid (180 mg); $^1H$ NMR ($CDCl_3$) δ 1.92–1.60 (m, 4H), 2.75–2.60 (m, 3H), 3.78–3.45 (m, 9H), 4.5 (d, J=8 Hz, 1H), 7.35–7.18 (m, 5H); MS: 322($MH^+$).

1423

(R)-5-(2-Difluoromethoxy-phenyl)-2-((S)-1-hydroxy-2-morpholin-4-yl-2-oxo-ethyl)-pentanoic acid (5b)

Similarly prepared according to the procedure above but using (R)-5-(2-difluoromethoxy-phenyl)-2-((S)-1-hydroxy-2-morpholin-4-yl-2-oxo-ethyl)-pentanoic acid methyl ester; $^1$H NMR (CDCl$_3$) δ 1.90–1.65 (m, 4H), 2.77–2.68 (m, 3H), 3.70–3.53 (m, 9H), 4,51 (d, J=4.4 Hz, 1H), 6.52 (t, J=74 Hz, 1H), 7.28–7.14 (m, 4H); MS: 388(MH$^+$).

(2R,3S)-2-Benzyl-3-hydroxy-4-morpholin-4-yl-4-oxo-butyric acid (5e)

Similarly prepared according to the general procedure above but using (2R, 3S)-2-Benzyl-3-hydroxy-4-morpholin-4-yl-4-oxo-butyric acid methyl ester; $^1$H NMR (CDCl$_3$) δ 2.90 (m, 1H), 3.10 (m, 2H), 3.70–3.15 (m, 8H), 3.75 (m, 1H), 4.32 (d J=7.5 Hz, 1H), 7.38–7.25 (m, 5H); MS: 294 (MH$^+$).

Reference 30

2-Amino-1-benzooxazol-2-yl-butan-1-one

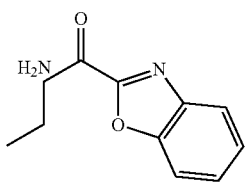

2-Amino-1-benzooxazol-2-yl-butan-1-one was prepared according to the following reaction protocol:

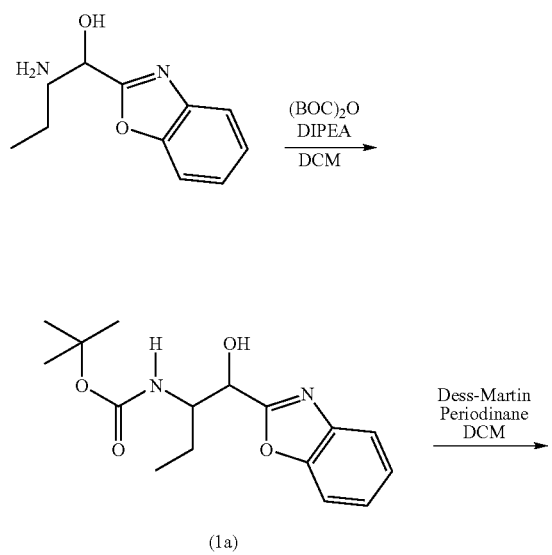

1424

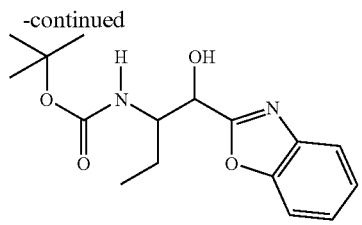

(2a)

↓ HCl

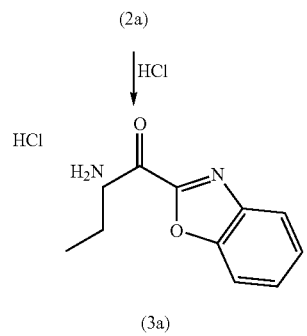

(3a)

[1-(Benzooxazol-2-yl-hydroxy-methyl)-propyl]-carbamic acid tert-butyl ester (1a)

DIPEA (0.35 ml, 2 mmol) and di-tret-butyl dicarbonate (355 mg, 1.63 mmol) were added to a solution of 2-Amino-1-benzooxazol-2-yl-butan-1-ol (320 mg, 1.55 mmol) in dry methylene chloride (10 ml) and stirred at room temperature for 4 hrs. The reaction was quenched with saturated aqueous NH$_4$Cl and the pH was adjusted to neutral. Oraganic layer separated and the aqueous layer extracted with methylene chloride. The combined organic extracts were dried over MgSO$_4$ and concentrated under reduced pressure to give, 1-(Benzooxazol-2-yl-hydroxy-methyl)-propyl]-carbamic acid tert-butyl ester (500 mg).

[1-(Benzooxazole-2-carbonyl)-propyl]-carbamic acid tert-butyl ester (2a)

Dess-Martin Periodinane (15% in DCM, 3.1 mmol) was added to a solution of, 1-(Benzooxazol-2-yl-hydroxy-methyl)-propyl]-carbamic acid tert-butyl ester in dry methylene chloride (15 ml) and stirred at room temperature for 4 hrs. A solution of Na$_2$S$_2$O$_3$ in aqueous NaHCO$_3$ was added and stirred at room temperature. Organic layer was separated and the aqueous was extracted with methylene chloride. The combined organic extracts were dried over Na$_2$SO$_4$ and concentrated under reduced pressure to give a pale brown solid. Column chromatography on silica eluting with a mixture of methylene chloride and heptane gave the title compound as off white solid (380 mg).

2-Amino-1-benzooxazol-2-yl-butan-1-one hydrochloride (3a)

Hydrogen chloride in dioxane (1M, 1 ml) was added to a solution of, 1-(Benzooxazole-2-carbonyl)-propyl]-carbamic acid tert-butyl ester (2a) in dry methylene chloride (3 ml) and stirred at room temperature for 4 hrs. Concentration under reduced pressure gave the title compound as white solid (65 mg); $^1$H NMR (CDCl$_3$) δ 0.99 (t, J=7.5 Hz, 3H), 2.20–2.05 (m, 2H), 4.96 (m, 1H), 7.58 (t, J=7.4 Hz, 1H), 7.69 (t, J=7.4 Hz, 1H), 7.94 (d, J=8.2 Hz, 1H), 8.04 (d, J=8.2 Hz, 1H), 8.75 (m, 3H); MS: 207(MH$^+$).

(1-Amino-cyclopropyl)-oxazol-2-yl-methanone hydrochloride (3b)

$^1$H NMR (DMSO) δ 1.79 (m, 2H), 1.22 (m, 2H), 7.58 (s, 1H), 8.49 (s, 1H), 9.22 (m, 3H); MS: 153(MH$^+$).

Reference 31

2-Amino-1-oxazol-2-yl-butan-1-ol

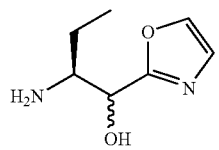

2-Amino-1-oxazol-2-yl-butan-1-ol was prepared according to the following reaction scheme:

Step 2

Compound 2 (8.4 g, 34.1 mmol) was then dissolved in 30 ml of dry THF and cooled to −50° C. under nitrogen, then LAH (1.0 M in THF, 37.5 ml, 37.51 mmol) was added drop wise over 30 minutes. The reaction was stirred for 1.5 hours at −50° C. then allowed to warm to 0° C. over 45 minutes. Then NaHSO4 (6.12 g, 44.33 mmol) was added slowly followed by cold water (2.0 ml) and stirring was continued for 30 minutes. The reaction was filtered through celite, which was washed with methylene chloride. The volatiles were removed from the filtrate in vacuo. The solid residue was dissolved in ethyl acetate and washed with cold 0.05N HCl, water and brine. The organic layer was dried over magnesium sulfate, filtered and concentrated to give 6.5 grams of compound 3 as colorless oil.

Step 3

Triethylborane (1.0 M in THF, 149.5 ml, 149.5 mmol) was added to oxazole (10.33 g, 149.5 mmol) and stirred for 45 minutes at room temperature. The mixture was then cooled to −78° C. and n-BuLi (2.5 M in hexane, 59.8 ml,

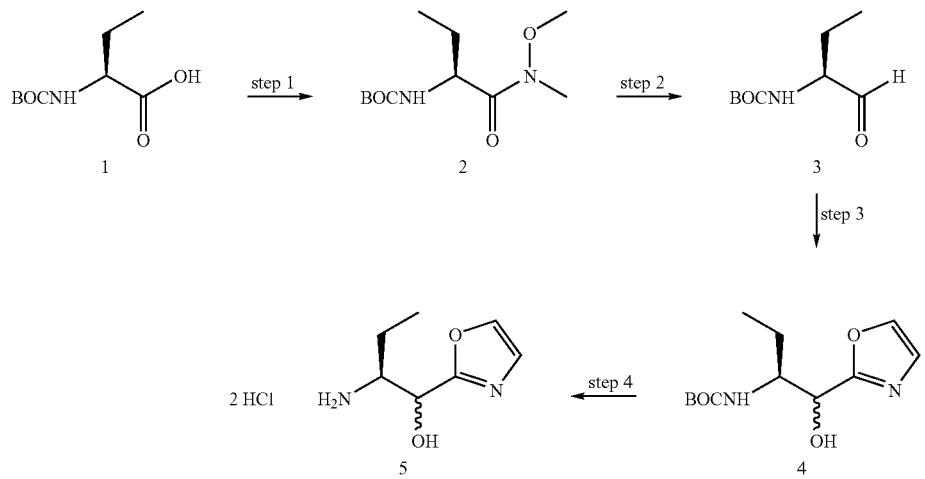

Step 1

To a stirring solution of of the BOC-L-α-aminobutyric acid (1, 17.75 g, 87.3 mmol) in dry methylene chloride (35 ml) was added DIEA (33.45 ml) followed by the N,O-dimethylhydroxylamine hydrochloride (9.37 g, 96.03 mmol) and PYBOP (50.0 g, 96.03 mmol). The reaction mixture was stirred overnight at room temperature. After the solvent was removed in vacuo, the oily residue was dissolved in ether and the precipitate which formed was filtered and the filtrate was concentrated to give 35.0 g of a brown oil. The residue was dissolved in ethyl acetate and washed twice with 0.05N HCl, saturated sodium bicarbonate and brine. The organic layer was dried over magnesium sulfate and concentrated to give 14.0 g of the product 2, which was used without further purification.

149.5 mmol) was added dropwise and allowed to stir for one hour under nitrogen. Compound 3 (8.0 g, 42.7 mmol) was dissolved in 25 ml of THF and added to the reaction mixture. The reaction was stirred for 5 hours at −78° C. then it was allowed to warm to 0° C. for one hour. The reaction was then cooled back to −78° C. and quenched with 7% acetic acid in ethanol (700 ml) which was allowed to stir overnight at room temperature. The mixture was concentrated in vacuo and the residue was dissolved in ether and filtered. The filtrate was concentrated in vacuo and the residue was dissolved in ethyl acetate washed twice with 0.005 N HCl, twice with sat'd sodium bicarbonate and brine. The organic layer was dried over magnesium sulfate, filtered and concentrated in vacuo. The residue was purified on silica using 10–40% ethyl acetate/heptane to give 3.85 grams of pure product 4.

1427

Step 4

To a solution of compound 4 (1.1 g, 4.29 mmol) in dry methylene chloride (10.0 ml), stirring under nitrogen at room temperature, was added 4M HCl (in dioxane, 10.73 ml) dropwise followed by 5 ml of methanol. The reaction was stirred overnight then concentrated in vacuo to give 1.2 grams of compound 5 as a brown solid.

The following reference compounds were prepared according to the protocol described in Reference 31:

2-Amino-3,3-dimethyl-1-oxazol-2-yl-butan-1-ol

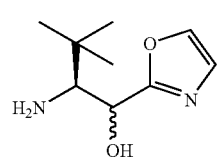

1428

2-Amino-1-oxazol-2-yl-4-phenyl-butan-1-ol

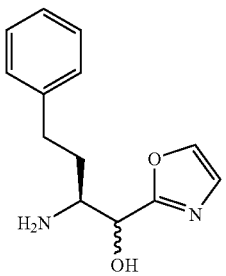

LCMS retention time 1.10 minutes; M+1 (233.1)

Reference 32

2-Amino-2-methyl-pentan-1-ol

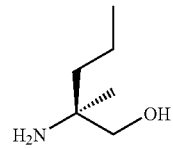

2-Amino-2-methyl-pentan-1-ol was prepared according to the following reaction scheme:

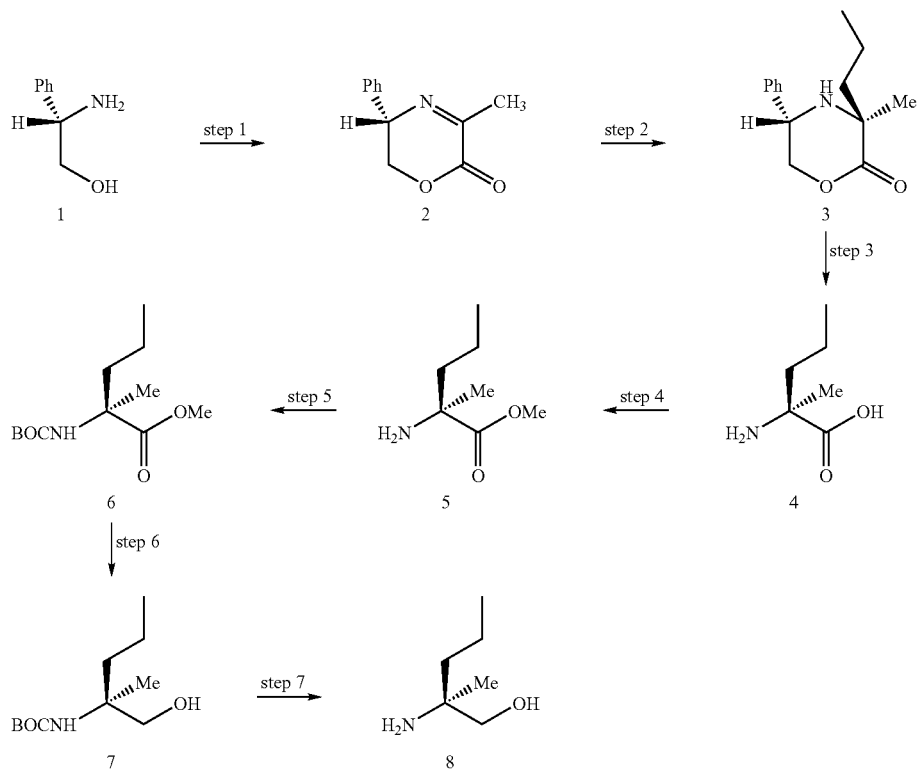

S-(+)-Phenylglycinol (1, 25 g, 182 mmol) was dissolved in trifluoroethanol (250 ml) and ethyl pyruvate (23.3 g, 200 mmol) was added (exothermic) followed by molecular seives (4 angstroms) and the reaction was refluxed overnight. The reaction was filtered and concentrated to an oil. The oil was purified on a 500 g silica gel column and eluted with 3:1 heptane/ethyl acetate to give 19.94 grams of compound 2.

Step 2

Compound 2 (15.0 g, 79 mmol) was dissolved in THF (400 ml) and cooled to −78 C., the boron trifluoride etherate (22.4 g, 158 mmol) was added over a 15 minute period. The reaction was allowed to stir at −78 degree C. for 2 hours and propyl magnesium chloride (2.0 M in ether, 79 ml, 158 mmol) was added over a one hour period and allowed to stir for 4 hours at −78° C. The reaction was allowed to warm to room temperature and stir overnight. The mixture was carefully quenched with sat'd NaHSO4 until pH of 8 was obtained. The reaction was extracted with ethyl acetate (2×200 ml), then washed with water, brine, dried over sodium sulfate and concentrated to dryness. The residue was purified on silica eluting with 4:1 heptane/ethyl acetate to give 12.2 grams of compound 3.

Steps 3 and 4

Compound 3 (9.0 g, 39 mmol) was dissolved in ethanol (100 ml) and water (20 ml) followed by the addition of 9 grams of Pd(OH)2 and TFA (4 ml). The mixture was hydrogenated at 50 psi for 48 hours, then the reaction was filtered through celite which was concentrated to give 9 grams of crude material 4 which was used without further purification. Compound 4 was dissolved in dry methanol (300 ml) and HCl gas was bubbled through for 15 minutes. The reaction was stirred at room temperature for three days and was concentrated. The crude product was purified on silica eluting With 1:1 heptane/ethyl acetate to give 3.9 grains of compound 5.

Step 5

A mixture of compound 5 (3.9 g, 27 mmol), (BOC)2O (5.88 g, 27 mmol), and TEA (7.56 ml, 54 mmol) in 100 ml of dioxane and 100 ml of water were stirred overnight at room temperature. The reaction mixture was concentrated and dissolved in ethyl acetate and washed with brine. The organic layer was dried over magnesium sulfate, filtered and concentrated in vacuo. The crude product was purified on silica eluting with 30 ethyl acetate/heptane to give 6.68 gram of pure product 6.

Step 6

A solution of compound 6 (6.68 g, 27 mmol) in 200 ml of THF was cooled to 0° C. and LAH (1.0M in THF, 32.4 ml, 32.4 mmol) was added dropwise and the reaction was stirred for 30 minutes then allowed to come to room temperature. The reaction was stirred for another 30 minutes and the reaction was quenched with a solution of NaHSO4, the THF was removed in vacuo and the residue was extracted with ethyl acetate which was washed with brine and concentrated. The product was purified on silica eluting with n-heptane to 5% methanol/ethyl acetate to give 2.8767 g of compound 7.

Step 7

Compound 7 (0.5 g) was dissolved in 5 ml of 4N HCL in dioxane and stirred for 1 hour at room temperature. The reaction was concentrated and dried under high vacuum to give 0.3859 g of compound 8, which was used without further purification.

The following reference compounds were prepared according to the protocol described in Reference 32:

2-Amino-2-methyl-4-phenyl-butan-1-ol

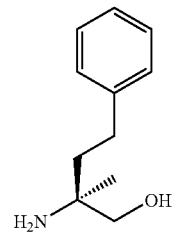

2-Amino-2-methyl-butan-1-ol

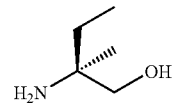

Reference 33

2-Amino-2-methyl-1-oxazol-2-yl-pentan-1-one

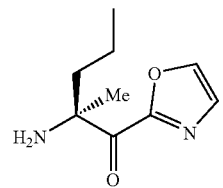

2-Amino-2-methyl-1-oxazol-2-yl-pentan-1-one was prepared according to the following reaction scheme:

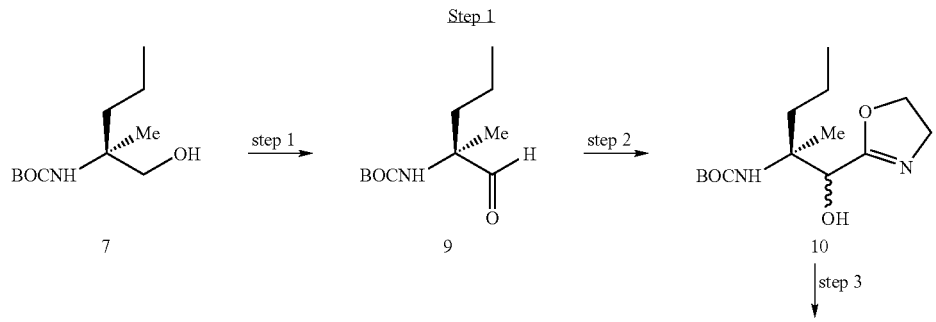

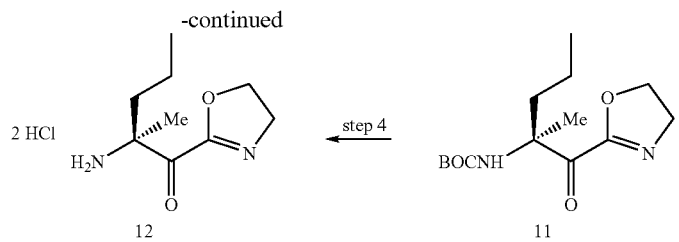

A solution of oxalyl chloride (2.0M in CH2Cl2, 1.5 ml, 3 mmol) in 5 ml of methylene chloride was cooled to −78° C., then DMSO (0.44 ml) was added drop wise to the mixture and allowed to stir for 5 minutes. A solution of compound 7 (Scheme 2, 0.4346 g, 2.0 mmol) in 10 ml of methylene chloride was added drop wise. The reaction was stirred at −78 degree C. for 15 minutes and TEA (1.12 ml, 8 mmol) was added dropwise and the reaction was stirred for 2 hours at room temperature. The reaction was quenched with water and the product was extracted with ethyl acetate, then organic layer was washed with brine and the solvent was removed in vacuo. The crude product was purified on silica eluting with heptane to 10% ethyl acetate/heptane to give 0.3131 g of pure compound 9.

Step 2

Triethylborane (1.0 M in THF, 4.84 ml, 4.84 mmol) was added to oxazole (0.3355 g, 4.84 mmol) in 4 ml of THF and stirred for 30 minutes at room temperature. The mixture was then cooled to −78° C. and n-BuLi (1.6 M in hexane, 3.025 ml, 4.84 mmol) was added dropwise and allowed to stir for one hour under nitrogen. Compound 9 (0.2615 g, 1.21 mmol) was dissolved in 5 ml of THF and added to the reaction mixture. The reaction was stirred for 5 hours at −78° C., then quenched with 5% acetic acid in ethanol (20 ml) which was allowed to stir overnight at room temperature and concentrated in vacuo. Ether was added and the solid was filtered and the filtrate was concentrated and the crude product was purified on silica using 0–20% ethyl acetate/heptane to give 0.2528 grams of pure product 10.

Step 3

Dess-Martin periodinane (15% in CH2Cl2, 4.95 g, 1.8 mmol) was added to a stirring added to a stirring solution of compound 10 (0.2528 g, 0.89 mmol) in 5 ml of methylene chloride. The reaction was stirred at room temperature for 3 hours, then the reaction was quenched with a solution of sodium thiosulfate in sat'd sodium bicarbonate. The product was extracted with ethyl acetate and the organic layer was washed with brine, dried over magnesium sulfate and concentrated in vacuo. The residue was purified on silica eluting with 1:1 ethyl acetate/heptane to 5% methanol/ethyl acetate to give 0.2307 g of pure compound 11.

Step 4

Compound 11 (0.2123 g, 0.75 mmol) was dissolved in 5 ml of 4N HCL in dioxane and stirred for 1 hour at room temperature. The reaction was concentrated and dried under high vacuum to give 0.1713 g of compound 8, which was used without further purification.

The following reference compounds were prepared according to the protocol described in Reference 33:

2-Amino-1-benzooxazol-2-yl-2-methyl-pentan-1-one

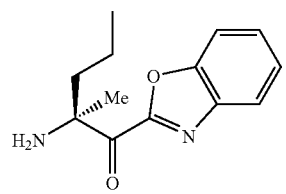

LCMS retention time 2.45 minutes; M+1 (233.1).

2-Amino-1-benzooxazol-2-yl-2-methyl-4-phenyl-butan-1-one

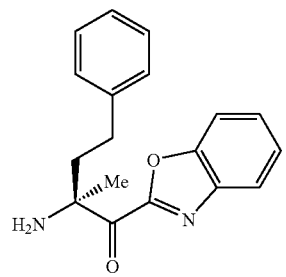

LCMS retention time 2.79 minutes; M+1 (295.1)

2-Amino-1-benzooxazol-2-yl-2-methyl-butan-1-one

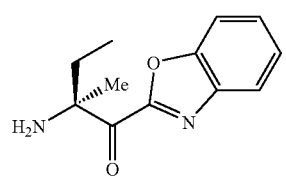

LCMS retention time 2.29 minutes; M+1 (219.1)

2-Amino-2-methyl-1-oxazol-2-yl-propan-1-one

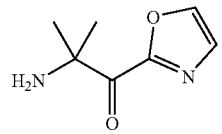

LCMS retention time 1.63 minutes; M+1 (155.1)

Reference 34

2-Amino-4-phenyl-butyramide

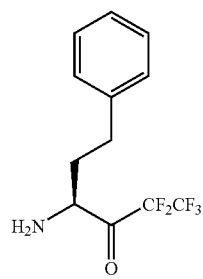

2-Amino-4-phenyl-butyramide was prepared according to the following reaction scheme:

Step 1

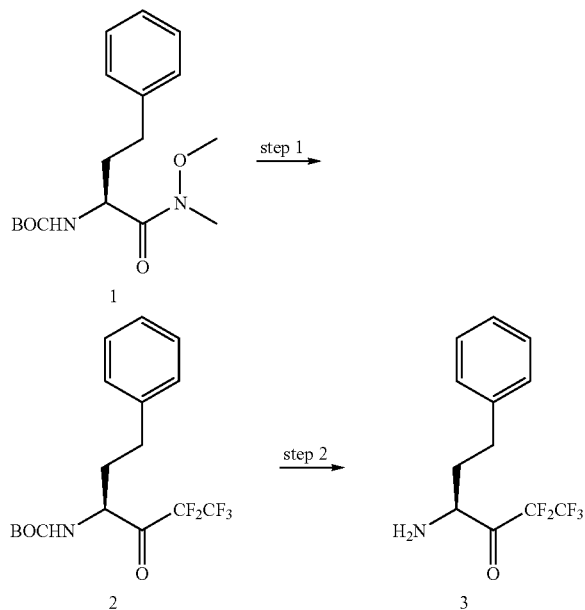

Compound 1 (5 g, 15.5 mmol) was dissolved in dry ether (150 ml) and cooled to −20° C., then perfluoroethyl iodide (25 g, 100 mmol) was bubbled into the mixture. The solution was then cooled to −50° C. and methyl lithium/lithium bromide complex was added over a 30 minute period. The reaction was stirred for 1.5 hours at this temperature and was then quenched with acetone. After stirring for 15 minutes the reaction was diluted with ether (100 ml) and poured onto 100 ml of water contain KHSO4. The organic layer was separated and washed with water, brine, dried over sodium sulfate and concentrated to dryness. The material was purified on silica eluting with 1:1 ethyl acetate/heptane to give 1.7 grams of compound 2.

Step 2

Compound 2 (0.35 g) was dissolved in 4 ml of 4N HCL in dioxane and stirred for 1 hour at room temperature. The reaction was concentrated and dried under high vacuum to give 0.2807 g of compound 3 which was used without further purification; LCMS retention time 4.19 minutes; M+1 (282.1).

Example 1

N-[(S)-1-(1-Benzooxazol-2-yl-methanoyl)-butyl]-3-benzylsulfonyl-2-benzylsulfonylmethyl-propionamide (Compound 1)

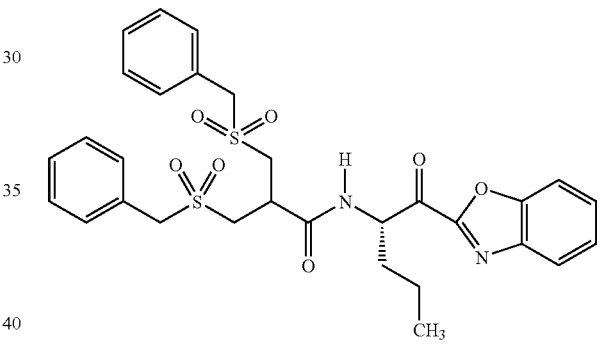

A mixture comprised of 3-benzylsulfanyl-2-benzylsulfanylmethyl-propionic acid (0.239 g, 0.719 mmol), prepared as in Reference 1, in methylene chloride (6 mL), HOBt hydrate (0.11 g, 0.719 mmol), EDC (0.18 g, 0.939 mmol), hydroxy amine (0.19 g, 0.86 mmol) and 4-methylmorpholine (0.075 mL) was stirred at room temperature for 1 hour and then poured into cold 1N aqueous hydrochloric. The product was extracted with ethyl acetate and the extracts were washed with saturated aqueous sodium chloride and then dried over magnesium sulfate. The solvent was removed by rotary evaporation at reduced pressure and the residue was chromatographed on silica gel eluting with ethyl acetate/hexane to give N-[(S)-1-(1-Benzooxazol-2-yl-1-hydroxy-methyl)-butyl]-3-benzylsulfanyl-2-benzylsulfanylmethyl-propionamide (0.217 g).

A solution of N-[(S)-1-(1-Benzooxazol-2-yl-1-hydroxymethyl)-butyl]-3-benzylsulfanyl-2-benzylsulfanylmethyl-propionamide (0.317 g, 0.594 mmol) in methanol (30 mL) was treated with a solution of Oxone® (0.913 g, 1.48 mmol) in water (20 mL) and then stirred at room temperature for 7 hours. The methanol was removed by evaporation at reduced pressure and the resulting suspension was diluted with water and the product extracted with ethyl acetate. The extracts were washed with saturated aqueous sodium chloride and then dried over magnesium sulfate. The solvent was removed by rotary evaporation at reduced pressure and the residue was chromatographed on silica gel eluting with ethyl acetate/hexane to give N-[(S)-1-(1-Benzooxazol-2-yl-1-hydroxy-methyl)-butyl]-3-benzylsulfonyl-2-benzylsulfonylmethyl-propionamide (0.143 g, 41% yield).

A solution of N-[(S)-1-(1-Benzooxazol-2-yl-1-hydroxymethyl)-butyl]-3-benzylsulfonyl-2-benzylsulfonylmethyl-propionamide (0.140 g, 0.234 mmol) in methylene chloride (5 mL) was treated with 1,1,1,1-triacetoxy-1,1-dihydro-1,2-benziodoxol-3(1H)-one (Dess-Martin periodinane) (0.127 g, 0.30 mmol.) and the resulting solution was stirred at room temperature for 30 minutes. Aqueous sodium thiosulfate and sodium bicarbonate (15 mL, 0.25 M) were added and the reaction mixture was stirred for 20 minutes. The product was extracted with ethyl acetate. The extracts were washed with saturated aqueous sodium chloride and then dried over magnesium sulfate. The solvent was removed by rotary evaporation at reduced pressure and the residue was crystallized from t-butylmethyl ether to give N-[(S)-1-(1-benzooxazol-2-yl-methanoyl)-butyl]-3-benzylsulfonyl-2-benzylsulfonylmethyl-propionamide (0.103 g, 74%); NMR (DMSO): 9.15 (d, J=6 Hz, 1H); 8.01 (d, J=7 Hz, 1H); 7.89 (d, J=8 Hz, 1H); 7.65 (t, J=7 Hz, 1H); 7.54 (t, J=8 Hz, 1H); 7.37 (m, 10H); 5.36 (m, 1H); 4.5 (m, 4H); 3.68 (m, 1H); 3.45–3.25 (m, 4H); 1.95 (m, 1H); 1.73 (m, 1H); 1.47 (m, 2H); 0.91 (t, J=7 Hz, 3H); MS: M(H+) 597.0 (596.17);

The following compounds were prepared by the method of Example 1 by substituting the required carboxylic acid in place of 3-benzylsulfanyl-2-benzylsulfanylmethyl-propionic acid:

N-[(S)-1-(1-Benzooxazol-2-yl-methanoyl)-butyl]-3-(2-trifluoromethyl-benzylsulfonyl)-2-(2-trifluoromethyl-benzylsulfonylmethyl)-propionamide (Compound 2); ¹H-NMR (CDCl₃) δ: 7.93 (m, 1H); 7.69 (m, 4H); 7.4–7.6 (m, 6H); 7.20 (m, 2H); 5.58 (m, 1H); 4.54 (m, 4H); 3.69 (m, 1H); 3.30–3.55 (m, 4H); 1.55–1.90 (m, 1H); 1.45 (m, 1H); 1.32 (m, 2H); 0.90 (m, 3H); MS: M(+) 733.0; M(−) 731.6;

N-[(S)-1-(1-Benzooxazol-2-yl-methanoyl)-pentyl]-4-(2-methoxy-benzenesulfonyl)-2-[2-(2-methoxy-benzenesulfonyl)-ethyl]-butyramide (Compound 3); ¹H-NMR (DMSO) δ: 8.65 (d, 1H); 7.99 (d, J=7 Hz, 1H); 7.89 (d, J=8 Hz, 1H); 7.8–7.5 (m, 6H); 7.3–7.1 (m, 4H); 5.25 (m, 1H); 3.90 (m, 9H); 3.3 (m, 6H); 1.6 (m, 4H); 1.3 (m, 2H); 0.85 (m, 3H); MS: (M+) 670.2, 670.19;

4-Benzenesulfonyl-2-(2-benzenesulfonyl-ethyl)-N-[(S)-1-(1-benzooxazol-2-yl-methanoyl)-butyl]-butyramide (Compound 4); ¹H-NMR (DMSO) δ: 8.61 (d, J=6 Hz, 1H); 7.99 (d, J=8 Hz, 1H); 7.91 (d, J=8 Hz, 1H); 7.82 (m, 4H); 7.74 (m, 2H); 7.64 (m, 5H); 7.55 (t, J=8 Hz, 1H); 5.21 (m, 1H); 3.3–3.0 (m, 5H); 1.8 (m, 1H); 1.6 (m, 5H); 1.3 (m, 2H); 0.86 (t, J=7 Hz, 3H); MS: (M+) 597.2, 596.17;

(R)-N-[(S)-1-(1-Benzooxazol-2-yl-methanoyl)-butyl]-2-cyclohexylmethyl-3-benzylsulfonyl-propionamide (Compound 5); ¹H NMR (DMSO): 8.96 (d, J=6 Hz, 1H), 8.73 (d, J=6 Hz, 1H), 7.99 (d, J=8H, 1H), 7.87 (m, 1H), 7.64 (m, 1H), 7.54 (m, 1H), 7.37 (m, 5H), 5.29 (m, 1H), 4.44 (s, 2H), 4.36 (s, 2H), 3.3–2.8 (m, 2H), 0.6–2.0 (m, 20H); MS: MH⁺ 525.4 (524.23); and N-[(S)-1-(1-Benzothiazol-2-yl-methanoyl)-propyl]-4-morpholin-4-yl-4-oxo-2-benzylsulfonylmethyl-butyramide (Compound 6); ¹H NMR: (DMSO), 8.79 (d, J=6.2 Hz), 8.72 (d, J=6.2 Hz), 1H], 8.30–8.22 (m, 2H), 7.71–7.61 (m, 2H), 7.43–7.33 (m, 5H), 5.46–5.33 (m, 1H), 4.53–4.38 (m, 2H), 3.57–3.30 (m, 10H), 3.13–3.02 (m, 1H), 2.66–2.54 (m, 2H), 2.04–1.90 (m, 1H), 1.83–1.68 (m, 1H), 0.97 (t, J=7.2 Hz, 3H); MS: (M⁺+1) 558.

The method of Example 1 can also be modified by omitting the Oxone® oxidation step to prepare the following compounds:

N-[(S)-1-(1-Benzooxazol-2-yl-methanoyl)-butyl]-3-cyclohexyl-2-cyclohexylmethyl-propionamide (Compound 7); ¹H NMR (DMSO): 8.50 (d, J=6 Hz, 1H); 8.00 (d, J=8 Hz, 1H); 7.89 (d, J=8 Hz, 1H); 7.62 (t, J=7 Hz, 1H); 7.53 (t, J=7 Hz, 1H); 5.2(m, 1H); 2.0–0.8 (m, 35H); MS: M(H+) 453.2 (452.3);

N-[(S)-1-(1-Benzooxazol-2-yl-methanoyl)-butyl]-3-isobutylsulfanyl-2-isobutylsulfanylmethyl-propionamide (Compound 8); ¹H NMR (DMSO): 8.73 (d, J=5 Hz, 1H); 7.76 (d, J=7 Hz, 1H); 7.87 (d, J=8 Hz, 1H); 7.62 (dt, J=7, 1 Hz, 1H); 7.52 (dt, J=8, 1 Hz, 1H); 5.26 (m, 1H); 2.7 (m, 1H); 2.55 (m, 4H); 2.34 (d, J=7 Hz, 2H); 2.29 (d, J=7 Hz, 2H); 1.9 (m, 1H); 1.66 (m, 3H); 1.45 (m, 2H); 0.91 (t, J=6 Hz, 3H), 0.90 (d, J=6 Hz, 6H), 0.88 (d, J=3 Hz, 3H), 0.84 (d, J=3 Hz, 3H); MS: M(H+) 465.0 (464.22);

N-[(S)-1-(1-Benzooxazol-2-yl-methanoyl)-butyl]-3-benzylsulfanyl-2-benzylsulfanylmethyl-propionamide (Compound 9); ¹H NMR (DMSO): 8.80 (d, J=7 Hz, 1H); 7.98 (d, J=8 Hz, 1H); 7.88 (d, J=8 Hz, 1H); 7.63 (t, J=7 Hz, 1H); 7.53 (t, J=7 Hz, 1H); 7.3–7.2 (m, 10H); 5.32 (m, 1H); 3.71 (s, 2H); 3.65 (d, J=3 Hz, 2H); 2.87 (m, 1H); 2.45–2.3 (m, 4H); 2.0–1.4 (m, 4H); 0.92 (t, J=7 Hz, 3H); MS: M(H+) 533.0 (532.19); and N-[(S)-1-(1-Benzooxazol-2-yl-methanoyl)-butyl]-4-phenylsulfanyl-2-(2-phenylsulfanyl-ethyl)-butyramide (Compound 10); ¹H NMR (DMSO): 8.73 (d, J=6 Hz, 1H); 7.99 (d, J=8 Hz, 1H); 7.88 (d, J=8 Hz, 1H); 7.65 (t, J=8 Hz, 1H); 7.53 (t, J=8 Hz, 1H); 7.35–7.1 (m, 10H); 5.3 (m, 1H); 2.85 (m, 4H); 2.65 (m, 1H); 2.0–1.3 (m, 8H); 0.91 (t, J=7 Hz, 3H); MS: M(H+) 533.0 (532.19).

Example 2

N-Cyanomethyl-4-morpholin-4-yl-4-oxo-2-(2-trifluoromethyl-benzyl-sulfonylmethyl)-butyramide

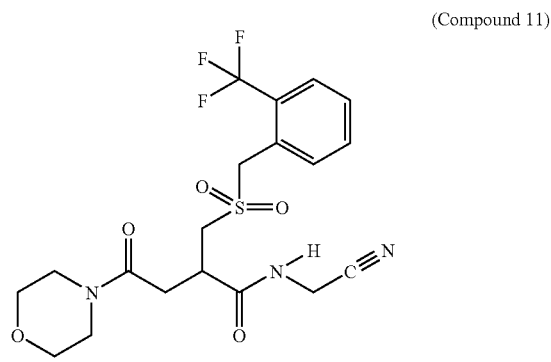

(Compound 11)

A mixture comprised of 4-morpholin-4-yl-4-oxo-2-(2-trifluoromethyl-benzylsulfonylmethyl)-butyric acid (200 mg, 0.47 mmol), prepared as in reference 5, EDC (200 mg, 1.05 mmol), HOBt (200 mg, 1.3 mmol), and aminoacetonitrile hydrochloride (150 mg, 1.6 mmol) was treated with dichloromethyl (4 mL) and 4-methylmorpholine (0.5 mL). The mixture was stirred at ambient temperature for 2 hours. After dilution with ethyl acetate (150 mL), the solution was washed with water (30 mL), saturated aqueous NaHCO₃ solution and brine, dried with magnesium sulfate and evaporated under vacuum. The product was crystallized from ethyl acetate/hexane to yield N-cyanomethyl-4-morpholin-4-yl-4-oxo-2-(2-trifluoromethyl-benzyl-sulfonylmethyl)-butyramide (156 mg) as a yellowish solid; $^1$H NMR: (DMSO) 8.87 (t, J=5.5 Hz, 1H), 7.81–7.57 (m, 4H), 4.74 (d, J=14.5 Hz, 1H), 4.67 (d, J=14.5 Hz, 1H), 4.13 (d, J=5.5 Hz, 2H), 3.63–3.26 (m, 11H), 2.75 (dd, J=6.4 Hz, J=16.8 Hz, 1H), 2.65 (dd, J=6.2 Hz, J=16.8 Hz, 1H); MS: (M$^+$+1) 462;

The following compounds of Formula I were provided by proceeding as in Example 2:

N$^4$-(4-Carbamoyl-phenyl)-N-1-cyanomethyl-2-benzyl-sulfonylmethyl-succinamide (Compound 19); $^1$H NMR: (DMSO) 10.24 (s, 1H), 8.93 (t, J=5.511z, 1H), 7.83 (s, 1H), 7.81 (d, J=8.4 Hz, 2H), 7.60 (d, J=8.4 Hz, 2H), 7.44–7.35 (m, 5H), 7.23 (s, 1H), 4.53 (d, J=13.6 Hz, 1H), 4.48 (d, J=13.6 Hz, 1H), 4.14 (m, 2H), 3.50–3.30 (m, 2H), 3.20 (dd, J=4.7 Hz, J=13.1 Hz, 1H), 2.73 (d, J=6.7 Hz, 2H); MS: (M$^+$+1) 443; and N-Cyanomethyl-2-[2-(1,1-difluoro-methoxy)-benzylsulfonylmethyl]-4-morpholin-4-yl-4-oxo-butyramide (Compound 25); $^1$H NMR: (DMSO) 8.85 (t, J=5.5 Hz, 1H), 7.52–7.43 (m, 2H), 7.31–7.22 (m, 2H), 7.13 (t, J$_{H,F}$=74 Hz, 1H), 4.53 (s, 2H), 4.11 (d, J=5.5 Hz, 2H), 3.58–3.20 (m, 11H), 2.72 (dd, J=6.7 Hz, J=16.8 Hz, 1H), 2.63 (dd, J=5.9 Hz, J=16.8 Hz, 1H); MS: (M$^+$+1) 460;

Example 3

N-[(S)-1-(1-Benzooxazol-2-yl-methanoyl)-propyl]-4-morpholin-4-yl-4-oxo-2-benzylsulfonylmethyl-butyramide (Compound 29)

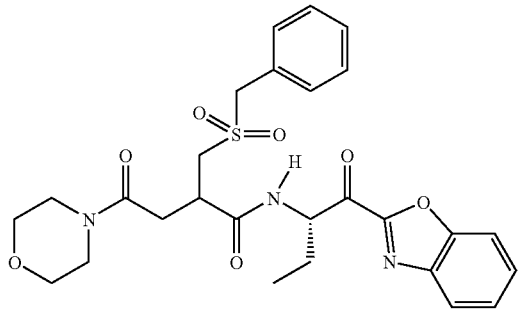

A mixture comprised of 4-Morpholin-4-yl-4-oxo-2-(benzyl-sulfonylmethyl)-butyric acid (300 mg, 0.84 mmol), EDC (250 mg, 1.3 mmol), HOBt (250 mg, 1.6 mmol) and (2S)-2-amino-1-benzooxazol-2-yl-butan-1-ol (250 mg, 1.2 mmol) was treated with dichloromethyl (4 mL) followed by 4-methylmorpholine (0.5 mL). The mixture was stirred at ambient temperature for 2 hours. After dilution with ethyl acetate (150 mL), the solution was washed with 1N aqueous HCl, water, saturated aqueous NaHCO$_3$ solution and brine, dried with magnesium sulfate and evaporated under vacuum. The crude product was dissolved in dry dichloromethyl (10 mL) and 1,1,1,1-triacetoxy-1,1-dihydro-1,2-benziodoxol-3(1H)-one (Dess-Martin periodinane) (500 mg, 1.2 mmol) was added. After stirring at ambient temperature for 1 hour, the mixture was diluted with ethyl acetate (150 mL) and treated with 0.26M Na$_2$SO$_3$ solution in saturated aqueous NaHCO$_3$. The organic phase was washed with saturated aqueous NaHCO3 and brine, dried with magnesium sulfate and evaporated to yield N-[(S)-1-(1-Benzooxazol-2-yl-methanoyl)-propyl]-4-morpholin-4-yl-4-oxo-2-benzylsulfonylmethyl-butyramide (377 mg) as mixture of diastereomers. The product was purified by flash chromatography on silica gel (hexane/ethyl acetate ratio of 1:2 to 1:4); $^1$H NMR: (DMSO), 8.85 (d, J=6.2 Hz), 8.77 (d, J=6.2 Hz), 1H],, 8.00 (d, J=7.7 Hz), 7.99 (d, J=7.7 Hz), 1H],, 7.90 (d, J=8.2 Hz), 7.89 (d, J=8.2 Hz), 1H], 7.64 (t, J=7.9 Hz, 1H), 7.54 (t, J=7.4 Hz, 1H), 7.42–7.34 (m, 5H), 5.25–5.12 (m, 1H), 4.55–4.38 (m, 2H), 3.60–3.28 (m, 10H), 3.12–3.02 (m, 1H), 2.64–2.50 (m, 2H), 2.08–1.91 (m, 1H), 1.82–1.65 (m, 1H), 0.98 (t, J=7.4 Hz, 3H); MS: (M$^+$+1) 542;

The following compounds of Formula I were provided by proceeding as in Example 3:

N-[(S)-1-(1-Benzooxazol-2-yl-methanoyl)-pentyl]-4-morpholin-4-yl-4-oxo-2-benzylsulfonylmethyl-butyramide (Compound 30); $^1$H NMR: (DMSO), 8.84 (d, J=6.4 Hz), 8.76 (d, J=6.4 Hz), 1H],, 8.00 (d, J=7.7 Hz), 7.98 (d, J=7.7 Hz), 1H],, 7.89 (d, J=8.2 Hz), 7.88 (d, J=8.2 Hz), 1H], 7.64 (t, J=7.9 Hz, 1H), 7.53 (t, J=7.4 Hz, 1H), 7.42–7.34 (m, 5H), 5.30–5.17 (m, 1H), 4.53–4.37 (m, 2H), 3.56–3.26 (m, 10H), 3.12–3.00 (m, 1H), 2.66–2.52 (m, 2H), 2.00–1.86 (m, 1H), 1.76–1.61 (m, 1H), 1.48–1.22 (m, 4H), 0.85 (t, J=6.9 Hz, 3H); MS: (M$^+$+1) 570;

(S)-2,2-Difluoro-4-(4-morpholin-4-yl-4-oxo-2-benzylsulfonylmethyl-butanoylamino)-3-oxo-hexanoic acid dimethylamide (Compound 31); $^1$H NMR: (DMSO) 8.63–8.57 (m, 1H), 7.43–7.34 (m, 5H), 4.69–4.57 (m, 1H), 4.55–4.41 (m, 2H), 3.59–3.30 (m, 10H), 3.14–3.04 (m, 1H),, 2.98 (s), 2.96 (s), 3H],, 2.90 (s), 2.88 (s), 3H], 2.70–2.58 (m, 2H), 1.90–1.72 (m, 1H), 1.66–1.50 (m, 1H), 0.89 (t, J=6.9 Hz, 3H); MS: (M$^+$+1) 546; and N-[(S)-1-(1-Benzylcarbamoyl-methanoyl)-propyl]-4-morpholin-4-yl-4-oxo-2-benzylsulfonylmethyl-butyramide (Compound 32); $^1$H NMR: (DMSO) 9.26–9.19 (m, 1H),, 8.56 (d, J=6.7 Hz), 8.51 (d, J=6.9 Hz), 1H], 7.44–7.19 (m, 10H), 4.96–4.85 (m, 1H), 4.53–4.40 (m, 2H), 4.38–4.22 (m, 2H), 3.57–3.30 (m, 10H), 3.11–2.99 (m, 1H), 2.65–2.52 (m, 2H), 1.86–1.71 (m, 1H), 1.61–1.48 (m, 1H), 0.89 (t, J=7.2 Hz, 3H); MS: (M$^+$+1) 558.

Example 5

3-Biphenyl-3-yl-N-cyanomethyl-2-benzylsulfonylmethyl-propionamide (Compound 35)

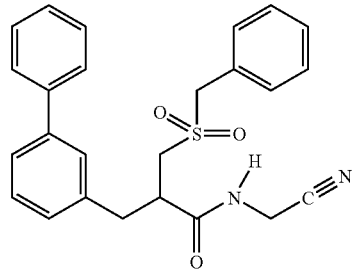

3-Biphenyl-3-yl-2-benzylsulfonylmethyl-propionic acid (300 mg, 0.76 mmol), prepared as in Reference 9, was combined with EDC (300 mg, 1.57 mmol), HOBt (300 mg, 1.96 mmol), and aminoacetonitrile hydrochloride (150 mg, 1.6 mmol). Dichloromethyl (4 mL) was added and then 4-methylmorpholine (0.5 mL). The mixture was stirred at ambient temperature for 2 hours. After dilution with ethyl acetate (150 mL), the solution was washed with water (30 mL), saturated aqueous NaHCO₃ solution and brine, dried with magnesium sulfate and evaporated under vacuum. The product, 3-biphenyl-3-yl-N-cyanomethyl-2-benzylsulfonylmethyl-propionamide (273 mg), was crystallized from ethyl acetate/hexane as a white solid; $^1$H NMR: (DMSO) 8.87 (t, J=5.5 Hz, 1H), 7.68–7.14 (m, 14H), 4.45 (d, J=13.8 Hz, 1H), 4.38 (d, J=13.8 Hz, 1H), 4.13 (m, 2H), 3.49 (dd, J=9.4 Hz, J=14.1 Hz, 1H), 3.28–3.11 (m, 1H), 3.04–2.76 (m, 3H). MS: (M$^+$+1) 433.

Proceeding as in Example 5 provided the following compound of Formula I:

3-Biphenyl-4-yl-N-cyanomethyl-2-benzylsulfonylmethyl-propionamide (Compound 36); $^1$H NMR: (DMSO) 8.86 (t, J=5.5 Hz, 1H), 7.65 (d, J=7.4 Hz, 2H), 7.59 (d, J=7.4 Hz, 2H), 7.47 (t, J=7.7 Hz, 2H), 7.39–7.24 (m, 8H), 4.47 (d, J=13.8 Hz, 1H), 4.40 (d, J=13.8 Hz, 1H), 4.13 (m, 2H), 3.48 (dd, J=9.4 Hz, J=14.1 Hz, 1H), 3.23–3.11 (m, 1H), 3.04–2.75 (m, 3H). MS: (M$^+$+1) 433; and 3-(3-Bromo-phenyl)-N-cyanomethyl-2-benzylsulfonylmethyl-propionamide (Compound 37); $^1$H NMR: (DMSO) 8.84 (t, J=5.5 Hz, 1H), 7.46–7.14 (m, 9H), 4.46 (d, J=13.8 Hz, 1H), 4.40 (d, J=13.8 Hz, 1H), 4.10 (m, 2H), 3.46 (dd, J=9.4 Hz, J=14.1 Hz, 1H), 3.18–3.07 (m, 1H), 2.97 (dd, J=14.1 Hz, J=3.4 Hz, 1H) 2.88–2.73 (m, 2H). MS: (M$^+$+1) 435/437.

Example 6

N-[(S)-1-((E)-2-Benzenesulfonyl-vinyl)-pentyl]-3-benzylsulfonyl-2-benzylsulfonylmethyl-propionamide (Compound 38)

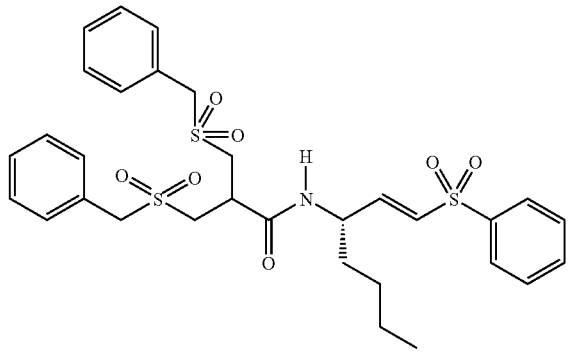

A mixture of 3-benzylsulfanyl-2-benzylsulfanylmethyl-propionic acid (161 mg), prepared as in Reference 1,3-benzenesulfonyl-1-n-butylallylamine tosylate (212 mg), HOBt monohydrate (77 mg) and EDC (125 mg) in methylene chloride (6 mL) was treated with N-methylmorpholine (0.25 mL) and stiffed at room temperature for 2.5 hours. The reaction mixture was poured into ice cold dilute hydrochloric acid. The product was extracted with ethyl acetate and the organic extracts were washed with aqueous sodium bicarbonate and then with saturated sodium chloride. After drying over magnesium sulfate the solvents were evaporated to give a residue which was crystallized from ethyl acetate/t-butylmethyl ether to yield N-[(S)-1-((E)-2-benzenesulfonyl-vinyl)-pentyl]-3-benzylsulfanyl-2-benzylsulfanylmethyl-propionamide (160 mg).

A solution of N-[(S)-1-((E)-2-benzenesulfonyl-vinyl)-pentyl]-3-benzylsulfanyl-2-benzylsulfanylmethyl-propionamide (50 mg) in methylene chloride (5 mL) was treated with m-chloroperbenzoic acid (108 mg) and then stirred at room temperature for 65 minutes. The reaction mixture was stirred with aqueous sodium bisulfite and sodium bicarbonate for 85 minutes and then extracted with methylene chloride. The organic extracts were washed with saturated aqueous sodium chloride and dried over magnesium sulfate. Evaporation of the solvent gave a residue which was precipitated from ethyl acetate/t-butylmethyl ether to give N-[(S)-1-((E)-2-benzenesulfonyl-vinyl)-pentyl]-3-benzylsulfonyl-2-benzylsulfonylmethyl-propionamide (37 mg); $^1$H NMR (DMSO): 8.61 (d, J=8 Hz, 1H), 7.80 (d, J=7 Hz, 2H), 7.69 (t, J=7H, 1H), 7.58 (t, J=8 Hz, 2H), 7.38 (m, 10H), 6.86 (m, 2H), 4.6–4.3 (m, 5H), 3.5–3.4 (m, 5H), 1.5 (m, 2H), 1.2 (m, 4H), 0.8 (m, 3H); MS: MH$^+$ 632.2 (631.17).

Proceeding as in Example 6 provided the following compound of Formula I:

N-(3-Benzenesulfonyl-1-phenethyl-allyl)-3-benzylsulfonyl-2-benzylsulfonylmethyl-propionamide (Compound 39); $^1$H NMR (DMSO): 8.75 (d, J=8 Hz, 1H), 7.80 (d, J=7 Hz, 2H), 7.70 (t, J=7H, 1H), 7.58 (t, J=8 Hz, 2H), 7.4–7.1 (m, 15H), 6.9 (m, 2H), 4.6–4.2 (m, 5H), 3.6–3.3 (m, 5H), 2.6 (m, 2H), 1.8 (m, 2H); MS: MH$^+$680.4 (679.17);

Example 7

N-Cyanomethyl-3-(3-cyano-benzylsulfonyl)-2-benzylsulfonyl-methyl-propionamide (Compound 40)

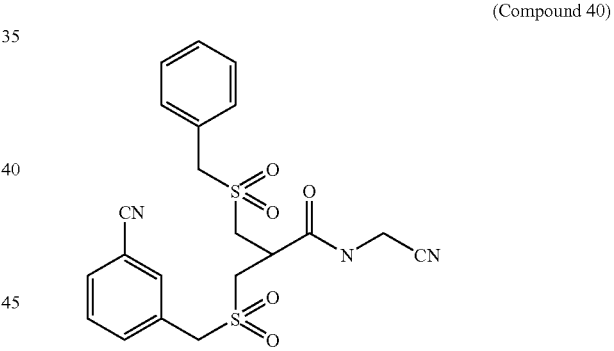

A mixture of 3-acetylsulfanyl-2-benzylsulfanylmethyl-propionic acid (0.200 g), prepared as in Reference 10, HOBt hydrate (0.13 g), aminoacetonitrile hydrochloride (0.15 g) and EDC (0.26 g) was treated with methylene chloride (6 mL) and N-methylmorpholine (0.35 mL). After stirring for 80 minutes at room temperature, the reaction mixture was diluted with ethyl acetate (50 mL) and washed sequentially with water, aqueous sodium bicarbonate and saturated aqueous sodium chloride. The solution was dried over magnesium sulfate and evaporated to give thioacetic acid S-[3-benzylsulfanyl-2-(cyanomethyl-carbamoyl)-propyl] ester (0.218 g).

A solution of thioacetic acid S-[3-benzylsulfanyl-2-(cyanomethyl-carbamoyl)propyl] ester (0.105 g) in dimethylformamide (1 mL) and water (0.8 mL) was cooled on ice and treated with 1 N aqueous potassium hydroxide (0.65 mL). 3-Cyanobenzylbromide (0.129 g) in dimethylformamide (0.8 mL) was added. The reaction mixture was allowed to warm to room temperature while stirring overnight. The reaction mixture was then poured into ice water and extracted with ethyl acetate (50 mL) and washed with water and saturated aqueous sodium chloride. The solution was dried over magnesium sulfate and evaporated to give 2-benzylsulfanylmethyl-3-(3-cyano-benzylsulfanyl)-N-cyanomethyl-propionamide (0.135 g).

2-Benzylsulfanylmethyl-3-(3-cyano-benzylsulfanyl)-N-cyanomethyl-propionamide (0.135 mg) in methanol (10 mL) was treated with a solution of Oxone® (0.615 g) in water (1.3 mL) and the resulting mixture was stirred at room temperature for 45 minutes. The reaction mixture was diluted with water (50 mL) and then the methanol was removed by rotary evaporation. The residue was diluted with ethyl acetate and water. The product was extracted with ethyl acetate and the organic layer washed with water and saturated aqueous sodium chloride. The solution was dried over magnesium sulfate and evaporated to give N-Cyanomethyl-3-(3-cyano-benzylsulfonyl)-2-benzylsulfonylmethyl-propionamide (0.138 g); $^1$H NMR: (DMSO) 9.19 (t, J=5 Hz, 1H), 7.88 (d, J=8 Hz, 1H), 7.82 (s, 1H), 7.72 (d, J=9 Hz, 1H), 7.62 (t, J=8 Hz, 1H), 7.38 (s, 5H), 4.65 (d, J=14 Hz, 1H), 4.58 (d, J=14 Hz, 1H), 4.53 (d, J=13 Hz, 1H), 4.47 (d, J=13 Hz, 1H), 4.17 (d, J=5 Hz, 2H), 3.5–3.3 (m, 5H); MS: (M$^+$+1) 460.2; 459.09.

Example 8

4-Morpholin-4-yl-4-oxo-2-benzylsulfonylmethyl-N-{(S)-1-[1-(3-phenyl-[1,2,4]oxadiazol-5-yl)-methanoyl]-propyl}-butyramide (Compound 41)

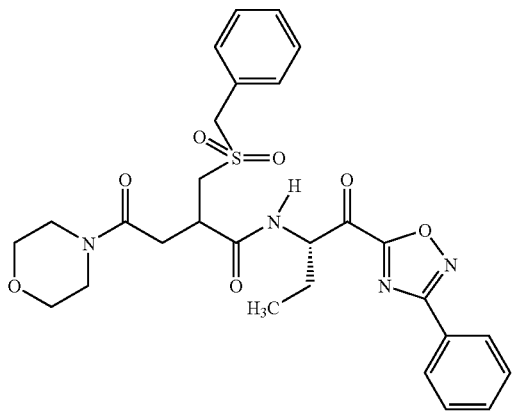

A mixture of (S)-2-amino-1-(3-phenyl-[1,2,4]oxadiazol-5-yl)-butan-1-one, prepared as in Reference 11, 4-morpholin-4-yl-4-oxo-2-benzylsulfonylmethyl-butyric acid (200 mg, 0.56 mmol), EDC (200 mg, 1.05 mmol), HOBt (200 mg, 1.30 mmol), CH$_2$Cl$_2$ (4 mL) and 4-methylmorpholine (0.5 mL) was stirred at ambient temperature for 2 hours. After dilution with ethyl acetate (150 mL), the solution was washed with water (30 mL), saturated aqueous NaHCO$_3$ solution and brine, dried with MgSO$_4$ and evaporated under vacuum. The crude product was dissolved in dry dichloromethyl (10 mL) and 1,1,1,1-triacetoxy-1,1-dihydro-1,2-benziodoxol-3(1H)-one (Dess-Martin periodinane) (500 mg, 1.2 mmol) was added. After stirring at ambient temperatures for 1 hour, the mixture was diluted with ethyl acetate (150 mL) and treated with Na$_2$S$_2$O$_3$ solution (0.26M) in saturated aqueous NaHCO$_3$. The organic phase was washed with saturated aqueous NaHCO$_3$ and brine, dried with MgSO$_4$ and evaporated. The product was purified by flash chromatography on silica gel (hexane/ethyl acetate in a 1:2 to 1:4 ratio) to yield 4-Morpholin-4-yl-4-oxo-2-benzylsulfonylmethyl-N-{-(S)-1[1-(3-phenyl-[1,2,4]oxadiazol-5-yl)-methanoyl]-propyl}-butyramide (150 mg) as mixture of diastereomers; $^1$H NMR: (DMSO), 9.03 (d, J=5.9 Hz), 8.89 (d, J=6.4 Hz), 1H], 8.09–8.03 (m, 2H), 7.66–7.55 (m, 3H), 7.42–7.33 (m, 5H), 4.97–4.78 (m, 1H), 4.53–4.35 (m, 2H), 3.58–3.02 (m, 1H), 2.65–2.50 (m, 2H), 2.06–1.90 (m, 1H), 1.83–1.66 (m, 1H), 0.97 (t, J=7.2 Hz, 3H); MS: (M$^+$+1) 569.

Example 9

N-Cyanomethyl-2-[2-1,1-difluoro-methoxy)-benzylsulfanylmethyl]-3-benzylsulfanyl-propionamide (Compound 42)

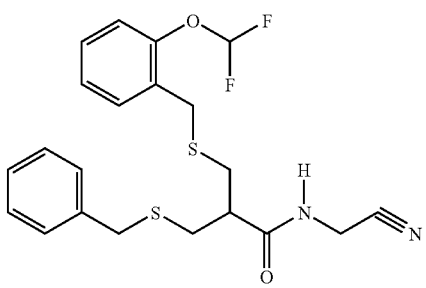

A mixture of 2-benzylsulfanylmethyl-3-[2-(1,1-difluoromethoxy)-benzyl-sulfanyl]-propionic acid (96 mg, 0.241 mmol)(prepared above in Reference 2), HOBt hydrate (37 mg, 0.24 mmol), aminoacetonitrile hydrochloride (33 mg, 0.36 mmol), EDC (69 mg, 0.36 mmol) and N-methylpyrolidinone (1 mL) was treated with N-methylmorpholine (0.050 mL) and then stirred at room temperature for 3 hours. The reaction mixture was then poured into cold dilute HCl and the product extracted with ethyl acetate, The organic extracts were washed with aqueous sodium bicarbonate then saturated sodium chloride and dried over magnesium sulfate. Evaporation of the solvent then gave N-cyanomethyl-2-[2-1,1-difluoro-methoxy)-benzylsulfanylmethyl]-3-benzylsulfanyl-propionamide (46 mg).

The following compounds of Formula 1 are provided by this method by substitution of 2-benzylsulfanylmethyl-3-[2-(1,1-difluoromethoxy)-benzylsulfanyl]-propionic acid with the appropriate carboxylic acid:

N-Cyanomethyl-3-(2-trifluoromethyl-benzylsulfanyl)-2-(2-trifluoro-methyl-benzylsulfanylmethyl)-propionamide (Compound 43); $^1$H-NMR (CDCl$_3$) δ: 7.57 (m, 6H); 7.36 (t, J=7.4 Hz, 2H); 6.01 (m, 1H); 4.16 (d, J=5.9 Hz, 2H); 3.86 (s, 4H); 2.70 (m, 4H); 3.35 (m, 1H); MS: (M+) 507.0, M(−) 504.2;

N-Cyanomethyl-3-isobutylsulfanyl-2-isobutylsulfanylmethyl-propionamide (Compound 44); $^1$H NMR (DMSO): 8.77 (t, J=6 Hz, 1H), 4.5 (d, J=6 Hz, 2H), 2.60 (s, 5H), 2.34 (d, J=7 Hz, 4H), 1.70 (hept, J=7 Hz, 2H), 0.91 (d, J=7 Hz, 12H); MS: M(H+) 303.0 (302.15);

N-Cyanomethyl-4-phenylsulfanyl-2-(2-Phenylsulfanyl-ethyl)-butyramide (Compound 45); $^1$H NMR (DMSO): 8.83 (t, J=5 Hz, 1H); 7.3 (m, 10H); 4.22 (d, J=6 Hz, 2H); 2.90 (m, 4H); 2.65 (m, 1H); 1.85 (m, 2H); 1.72 (m, 2H); MS: M(H+) 370.4 (370.12);

N-Cyanomethyl-3-[2-(1,1-difluoro-methoxy)-benzylsulfanyl]-2-[2-(1,1-difluoro-methoxy)-benzylsulfanylmethyl]- propionamide (Compound 46); ¹H NMR (DMSO): 8.88 (t, J=5 Hz, 1H); 7.4–7.1 (m, 8H); 7.15 (t, J=74 Hz, 2H); 4.18 (t, J=3 Hz, 2H); 3.74 (d, J=13 Hz, 4H); 2.75 (m, 1H); 2.65–2.5 (m, 4H); MS: M(H+) 504.1 (502.1); and 3-Benzylsulfanyl-2-benzylsulfanylmethyl-N-cyanomethyl-propionamide (Compound 47); ¹H NMR (DMSO): 8.86 (t, J=6 Hz, 1H); 7.26 (m, 10H); 4.20 (d, J=5 Hz, 2H); 3.7 (s, 4H); 2.73 (m, 1H); 2.55–2.37 (m, 4H); MS: M(H+) 370.4 (370.12).

Example 10

N-Cyanomethyl-2-[2-1,1-difluoro-methoxy)-benzyl-sulfonylmethyl]-3-benzylsulfonyl-propionamide (Compound 48)

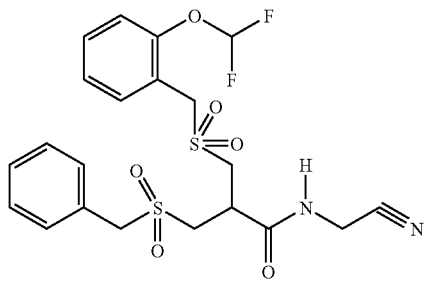

A solution of N-cyanomethyl-2-[2-(1,1-difluoro-methoxy)-benzyl-sulfanylmethyl]-3-benzylsulfanyl-propionamide (46 mg) in methanol (5 mL) was treated with Oxone® (184 mg in 2.5 mL of water) and stirred at ambient temperature for 18 hours. An additional portion of Oxone® (166 mg in 1.5 mL of water) was added along with more methanol (10 mL) and the reaction mixture was stirred again for 18 hours. Water was added to the reaction mixture and the methanol was removed by rotary evaporation and the product was extracted with ethyl acetate. The organic extracts were washed with aqueous sodium bicarbonate then saturated sodium chloride and dried over magnesium sulfate. Evaporation of the solvent then gave N-cyanomethyl-2-[2-(1,1-difluoro-methoxy)benzylsulfonylmethyl]-3-phenylmethylsulfonyl-propionamide (67 mg); ¹H NMR (DMSO): 9.19 (t, J=5 Hz, 1H), 7.47 (m, 2H), 7.38 (s, 5H), 7.25 (m, 2H), 7.13 (t, J=74 Hz, 1H), 4.54 (s, 2H), 4.53 (d, J=14 Hz, 1H), 4.46 (d, J=14 Hz, 1H), 4.16 (d, J=5 Hz, 2H), 3.5 (m, 5H); MS: M(H+) 501.0 (500.09).

The following compounds of Formula 1 are provided by this method by substitution of N-cyanomethyl-2-[2-(1,1-difluoro-methoxy)-benzyl-sulfanylmethyl]-3-benzylsulfanyl-propionamide with the appropriate N-cyanomethyl propionamide:

N-Cyanomethyl-3-(2-trifluoromethyl-benzylsulfonyl)-2-(2-trifluoromethyl-benzylsulfonylmethyl)-propionamide. (Compound 49); ¹H-NMR (DMSO) δ: 9.23 (t, J=5.4 Hz, 1H); 7.79 (m, 2H); 7.67 (m, 6H); 4.72 (m, 4H); 4.18 (t, J=2.7 Hz, 2H); 3.53–3.76 (m, 5H); MS: M(+) 539.0; M(−) 536.6;

4-Benzenesulfonyl-2-(2-benzenesulfonyl-ethyl)-N-cyanomethyl-butyramide (Compound 50); ¹H NMR (DMSO): 8.67 (t, J=5 Hz, 1H); 7.85 (m, 4H); 7.73 (m, 2H); 7.64 (m, 4H); 4.06 (m, 2H); 3.12 (m, 4H); 2.4 (m, 1H); 1.66 (m, 4H); MS: M(H+) 435.2 (434.10);

N-Cyanomethyl-3-[2-(1,1-difluoro-methoxy)-benzylsulfonyl]-2-[2-(1,1-difluoromethoxy)-benzylsulfonylmethyl]-propionamide (Compound 51); ¹H NMR (DMSO): 9.17 (t, J=5 Hz, 1H); 7.5–7.4 (m, 4H); 7.3–7.2 (m, 4H); 7.12 (t, J=74 Hz, 2H); 4.54 (s, 4H); 4.15 (m, 2H); 3.6–3.4 (m, 5H); MS: M(H+) 567.2 (566.08); and N-Cyanomethyl-3-benzylsulfonyl-2-benzylsulfonylmethyl-propionamide (Compound 52); ¹H NMR (DMSO): 9.19 (t, J=5 Hz, 1H); 7.38 (s, 10H); 4.53 (d, J=14 Hz, 2H); 4.46 (d, J=14 Hz, 2H); 4.17 (t, J=3 Hz, 2H); 3.5–3.3 (m, 5H); MS: M(H+) 435.2 (434.1).

The following compounds of Formula I are provided by the methods described in this application:

N-[(S)-1-(1-Benzylcarbamoyl-methanoyl)-propyl]-3-benzylsulfonyl-2-benzylsulfonylmethyl-propionamide (Compound 53); ¹H-NMR (DMSO) δ: 9.27 (t, J=6 Hz, 1H); 8.89 (d, J=6 Hz, 1H); 7.4–7.2 (m, 15H); 5 (m, 1H); 4.5 (m, 4H); 4.3 (m, 2H); 3.67 (m, 1H); 3.5–3.2 (m, 4H); 1.8 (m, 1H)1.6 (m, 1H); 0.91 (t, J=7 Hz, 3H); MS: (M+) 599.0, M(−) 598.18;

N-[(S)-1-(1-Benzooxazol-2-yl-methanoyl)-butyl]-2-[2-(1,1-difluoro-methoxy)-benzylsulfonylmethyl-3-benzylsulfonyl-propionamide (Compound 54); ¹H-NMR (DMSO) δ: 9.1 (t, J=6 Hz, 1H); 7.99 (d, J=8 Hz, 1H); 7.88 (d, J=8 Hz, 1H); 7.7–7.2 (m, 14H); 5.35 (m, 1H); 4.6–4.4 (m, 5H); 3.7–3.3 (m, 5H); 1.9 (m, 1H), 1.7 (m, 1H)1.45 (m, 2H); 0.90 (t, J=7 Hz, 3H); MS: (M+) 599.0, M(−) 598.18;

N-Cyanomethyl-3-(2-methyl-propane-1-sulfonyl)-2-(2-methyl-propane-1-sulfonylmethyl)-propionamide (Compound 55); ¹H-NMR (DMSO) δ: 9.13 (t, J=5 Hz, 1H); 4.14 (m, 2H); 3.5–3.3 (m, 5H), 3.1–2.95 (m, 4H), 2.17 (h, J=7 Hz, 2H)1.01 (d, J=7 Hz, 12H); MS: (M+) 367.0, 366.13;

Acetic acid (2S,3S)-3-(4-morpholin-4-yl-4-oxo-2-benzyl-sulfonylmethyl-butanoylamino)-4-oxo-azetidin-2-yl ester (Compound 58); ¹H NMR: (DMSO) 9.19 (d, J=5.9 Hz, 1H),, 8.94 (d, J=7.6 Hz), 8.90 (d, J=7.6 Hz), 1H], 7.42–7.35 (m, 5H), 5.70 (m, 1H), 4.60 (m, 1H), 4.56–4.40 (m, 2H), 3.58–3.06 (m, 11H), 2.70–2.50 (m, 2H), 2.07 (s, 3H); MS: (M⁺+1) 482;

N-Cyanomethyl-3-(2-methyl-thiazol-4-ylmethylsulfonyl)-2-benzyl-sulfonylmethyl-propionamide (Compound 59); ¹H NMR (DMSO): 9.14 (t, J=5 Hz, 1H), 7.52 (s, 1H), 7.38 (s, 5H), 4.64 (s, 2H), 4.53 (d, J=14 Hz, 1H), 4.46 (d, J=14 Hz, 1H), 4.16 (d, J=5 Hz, 2H), 3.5 (m, 5H), 2.63 (s, 3H); M=455.06, M(H+)=456.0;

N-(3-Benzenesulfonylamino-2-oxo-propyl)-4-morpholin-4-yl-4-oxo-2-benzylsulfonylmethyl-butyramide (Compound 60); ¹H NMR: (DMSO) 8.46 (t, J=5.2 Hz, 1H), 7.97 (t, J=5.7 Hz, 1H), 7.79 (d, J=7 Hz, 2H), 7.66–7.52 (m, 3H), 7.44–7.36 (m, 5H), 4.56–4.43 (m, 2H), 3.94 (d, J=5.2 Hz, 2H), 3.84 (d, J=5.7 Hz, 2H), 3.59–3.04 (m, 11H), 2.75–2.55 (m, 2H); MS: (M⁺+1) 566;

3-Biphenyl-3-yl-N-cyanomethyl-2-[2-(1,1-difluoro-methoxy)-benzyl-sulfonylmethyl]-propionamide (Compound 61); ¹H NMR: (DMSO) 8.86 (t, J=5.4 Hz, 1H), 7.70–7.10 (m, 13H), 7.12 (t, J=73.7 Hz, 1H), 4.46 (s, 2H), 4.13 (m, 2H), 4.10 (d, J=5.6 Hz, 2H), 3.57 (m, 1H), 3.20–3.00 (m, 2H), 3.00–2.80 (m, 2H); MS: (M⁺+1) 499;

(3-{2-(Cyanomethyl-carbamoyl)-3-[2-(1,1-difluoro-methoxy)-benzyl-sulfonyl]-propyl}-biphenyl-4-yl)-carbamic acid ethyl ester (Compound 62); ¹H NMR: (DMSO) 9.70 (s, 1H), 8.84 (t, J=5.4 Hz, 1H), 7.55 (s, 4H), 7.50–7.15 (m, 8H), 7.11 (t, J=73.7 Hz, 1H), 4.45 (s, 2H), 4.13 (m, 2H), 4.09 (d, J=5.5 Hz, 2H), 3.56 (m, 1H), 3.20–3.00 (m, 2H), 2.95–2.75 (m, 2H), 1.24 (t, J=6.9 Hz, 3H); MS: (M⁺+1) 586;

N-Cyanomethyl-2-[2-(1,1-difluoro-methoxy)-benzylsulfonylmethyl]-3-(4'-methylsulfonylamino-biphenyl-3-yl)-propionamide (Compound 63); ¹H NMR: (DMSO) 9.77 (s, 1H), 8.79 (t, J=5.4 Hz, 1H), 7.57 (d, J=8.6 Hz, 2H), 7.50–7.00

(m, 8H), 7.27 (d, J=8.6 Hz, 2H), 7.06 (t, J=73 Hz, 1H), 4.40 (s, 2H), 4.04 (d, J=5.6 Hz, 2H), 3.51 (m, 1H), 3.20–3.00 (m, 2H), 2.90–2.70 (m, 2H); MS: (M$^+$+1) 592;

3-(3-Bromo-phenyl)-N-cyanomethyl-2-[2-(1,1-difluoromethoxy)-phenyl-methylsulfonylmethyl]-propionamide (Compound 64); $^1$H NMR: (DMSO) 8.80 (t, J=5.4 Hz, 1H), 7.50–7.35 (m, 4H), 7.35–7.15 (m, 4H), 7.13 (t, J=73 Hz, 1H), 4.46 (s, 2H), 4.06 (d, J=5.4 Hz, 2H), 3.53 (m, 1H), 3.20–3.00 (m, 2H), 2.90–2.70 (m, 2H); MS: (M$^+$+1) 501;

N-Cyanomethyl-2-((E)-3-phenyl-allyl)-3-benzylsulfonyl-propionamide (Compound 65); $^1$H NMR: (DMSO) 8.85 (t, J=5.4 Hz, 1H), 7.40–7.10 (m, 10H), 6.35 (d, J=15 Hz, 1H), 6.15–5.95 (m, 1H), 4.41 (s, 2H), 4.08 (d, J=5.4 Hz, 2H), 3.56–3.35 (m, 2H), 3.25–2.90 (m, 3H); MS: (M$^+$+1) 383; and N-Cyanomethyl-3-benzylsulfonyl-2-(3-phenyl-propyl)-propionamide (Compound 66); $^1$H NMR: (DMSO) 8.91 (t, J=5.4 Hz, 1H), 7.45–7.10 (m, 10H), 4.41 (s, 2H), 4.08 (d, J=5.4 Hz, 2H), 3.30–2.80 (m, 3H), 2.34 (t, J=7.4 Hz, 2H), 2.22–2.12 (m, 2H), 2.10–1.85 (m, 2H); MS: (M$^+$+1) 385.

Example 11

4-Morpholin-4-yl-4-oxo-N-[1-(2-oxo-2-phenyl-acetyl)-pentyl]-2-benzylsulfonylmethyl-butyramide

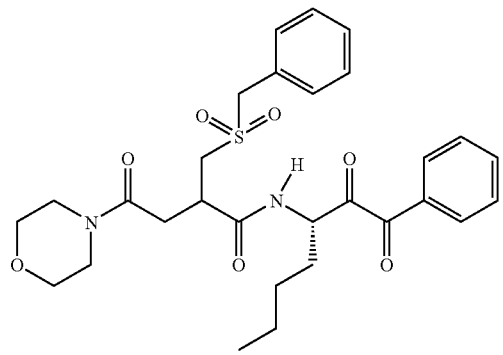

(Compound 67)

2-Amino-1-(2-phenyl-[1,3]dithian-2-yl)-hexan-1-ol, prepared as in reference 12, was coupled with 4-morpholin-4-yl-4-oxo-2-benzylsulfonylmethyl-butyric acid, according to the procedure outlined in example 8, resulting in N-{1-[Hydroxy-(2-phenyl[1,3]dithian-2-yl)-methyl]-pentyl}-4-morpholin-4-yl-4-oxo-2-benzylsulfonyl-methyl-butyramide as a mixture of diastereomers.

N-{1-[Hydroxy-(2-phenyl-[1,3]dithian-2-yl)-methyl]-pentyl}-4-morpholin-4-yl-4-oxo-2-benzylsulfonylmethyl-butyramide (0.23 g, 0.35 mmol) in 9 mL acetonitrile and 2.25 mL water at 23° C. was mixed with finely ground HgCl$_2$ (212 mg, 0.78 mmol) and finely ground calcium carbonate (90 mg, 0.89 mmol). The mixture was stirred for 25 minutes and then diluted with ethyl acetate. Water was added and the pH lowered to 6 by the addition of 1N HCl. After separation, the organic layer was washed sequentially with water and brine (twice). The organics were dried with magnesium sulfate, concentrated and chromatographed on silica gel using a hexane-ethyl acetate gradient to afford 150 mg of N-[1-(1-Hydroxy-2-oxo-2-phenyl-ethyl)-pentyl]-4-morpholin-4-yl-4-oxo-2-phenyl-methylsulfonylmethyl-butyramide as a mixture of diastereomers (76% yield).

N-[1-(1-Hydroxy-2-oxo-2-phenyl-ethyl)-pentyl]-4-morpholin-4-yl-4-oxo-2-benzylsulfonylmethyl-butyramide was oxidized by methods described in the above examples resulting in 4-morpholin-4-yl-4-oxo-N-[1-(oxo-phenyl-acetyl)-1-pentyl]-2-benzylsulfonylmethyl-butyramide as a mixture of diastereomers; $^1$H NMR: (DMSO), 8.9 (d, J=6 Hz), ½H diastereomeric],, 8.86 (d, J=6 Hz), ½H diastereomeric], 7.89–7.84 (m, 2H), 7.7–7.67 (m, 1H), 7.56–7.5 (m, 2H), 7.4–7.3 (m, 5H), 4.56–4.54 (m, 1H), 4.41–4.35 (m, 2H), 3.4–4.6 (m, 4H), 3.35–3.25 (m, 4H), 3.2–3.1 (m, 2H), 2.99–2.95 (m, 1H), 1.9–1.6 (m, 2H), 1.5–1.2 (m, 6H), 1.0–0.9 (m, 3H); MS: (M$^+$+1) 557.

Example 12

3-(4-Morpholin-4-yl-4-oxo-2-benzylsulfonylmethyl-butyrylamino)-4-oxo-pyrrolidine-1-carboxylic acid tert-butyl ester

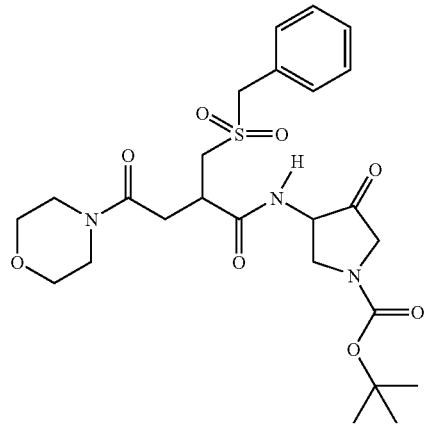

(Compound 68)

4-Morpholin-4-yl-4-oxo-2-benzylsulfonylmethyl-butyric acid (120 mg, 0.34 mmol), 3-amino-4-hydroxy-pyrrolidine-1-carboxylic acid tert-butyl ester (150 mg, 0.74 mmol), prepared as in reference 13, EDC (0.3 g, 1.6 mmol), and HOBt (150 mg, 0.96 mmol) were combined. Dichloromethyl (10 mL) was added and then 4-methylmorpholine (0.5 mL). The mixture was stirred at ambient temperature for 2 hours. After dilution with ethyl acetate (200 mL) the solution was washed with 1N aqueous HCl (50 mL), saturated aqueous NaHCO$_3$ (50 mL) and brine (50 mL), dried with MgSO$_4$ and evaporated under vacuum. The pyrrolidine-1-carboxylic acid tert-butyl ester was dissolved in DMSO (5 mL). Triethylamine (0.5 mL) and then SO$_3$ pyridine complex (150 mg) were added and the mixture was stirred at ambient temperature for 3 hours. After dilution with ethyl acetate (100 mL), the solution was washed with water (50 mL) and brine, dried with MgSO$_4$ and evaporated under vacuum. The residue was purified by flash chromatography on silica gel. Eluent: 5% methanol in ethyl acetate. Yield: 40 mg 3-(4-morpholin-4-yl-4-oxo-2-benzylsulfonylmethyl-butyrylamino)-4-oxo-1-pyrrolidine-1-carboxylic acid tert-butyl ester as white solid as mixture of diastereomers; $^1$H NMR: (DMSO) 8.80–8.66 (m, 1H), 7.42–7.34 (m, 5H), 4.52–4.41 (m, 2H), 4.34–4.20 (m, 1H), 3.98–3.88 (m, 1H), 3.82 (d, J=18.5 Hz, 1H), 3.70–3.05 (m, 13H), 2.70–2.52 (m, 2H), 1.41 (s, 9H); MS: (M+H)$^+$ 538.

Example 13

4-(4-Morpholin-4-yl-4-oxo-2-benzylsulfonylmethyl-butyrylamino)-3-oxo-azepane-1-carboxylic acid benzyl ester (Compound 69)

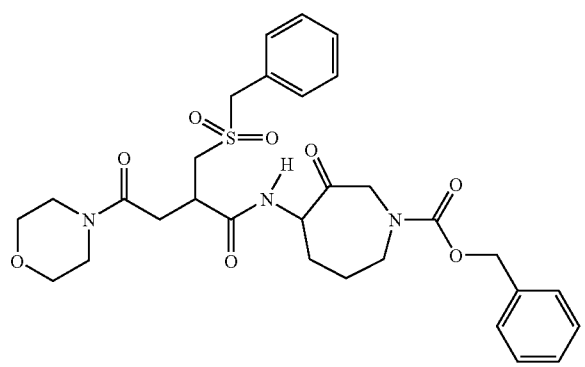

Sodium hydride (60% in mineral oil, 10 g, 250 mmol) was suspended in dry DMF. Allyl-carbamic acid benzyl ester (19.1 g, 100 mmol) was added drop wise at ambient temperature. After stirring for 5 minutes, 5-bromo-1-pentene (25 g, 168 mmol) was added drop wise. Stirring was continued at 50° C. for 1 hour. The reaction was quenched with water and then partitioned between diethyl ether and water. The ether layer was washed with water and brine, dried with $MgSO_4$ and evaporated under vacuum. Flash chromatography (ethyl acetate/hexane 1:9) gave 15.5 g allyl-pent-4-enyl-carbamic acid benzyl ester.

Allyl-pent-4-enyl-carbamic acid benzyl ester (15.5 g, 59.8 mmol) was dissolved in dichloromethyl and bis(tricyclohexylphosphine)benzylidene ruthenium (IV) dichloride (1 g) was added. The mixture was refluxed under a nitrogen atmosphere until TLC analysis showed complete reaction. The solvent was evaporated under vacuum and the residue was purified by flash chromatography (ethyl acetate/hexane 1:9). Yield: 7.8 g 2,3,4,7-Tetrahydro-azepine-1-carboxylic acid benzyl ester.

To a solution of 2,3,4,7-tetrahydro-azepine-1-carboxylic acid benzyl ester (4.5 g, 19.45 mmol) in dichloromethyl (50 mL) was added m-chloroperbenzoic acid (60 mmol). The mixture was stirred at ambient temperature for 16 hours. Saturated aqueous $K_2CO_3$ solution was added and the mixture was extracted with dichloromethyl. The combined organic layers were washed with saturated aqueous $NaHCO_3$ and brine, dried with $MgSO_4$ and evaporated under vacuum. The crude epoxide was dissolved in a 8:1 methanol/water mixture (100 mL). Ammonium chloride (3.2 g, 60 mmol) and sodium azide (3.9 g, 60 mmol) was added and the mixture was heated at 60° C. for 48 hours. Most of the solvent was removed under vacuum. The residue was extracted with ethyl acetate. The combined organic layers were washed with saturated aqueous $NaHCO_3$ (200 mL) and brine (200 mL), dried with $MgSO_4$ and evaporated under vacuum. Flash chromatography of the residue (hexane/ethyl acetate 3:1) gave 3.3 g of 4-azido-3-hydroxy-azepane-1-carboxylic acid benzyl ester.

To a solution of 4-azido-3-hydroxy-azepane-1-carboxylic acid benzyl ester (3.3 g, 11.37 mmol) in methanol (50 mL) was added triethylamine (5 mL) and 1,3-propanedithiol (3.42 mL, 35 mmol). The mixture was stirred at ambient temperature until TLC analysis showed complete consumption of the starting material. A white precipitate was removed by filtration and the filtrate was evaporated to dryness. The residue was triturated with a 1:1 hexane/diethyl ether mixture to remove excess dithiol and dried under vacuum.

The crude 4-amino-3-hydroxy-azepane-1-carboxylic acid benzyl ester was coupled to 4-morpholin-4-yl-4-oxo-2-benzylsulfonylmethyl-butyric acid and oxidized, as described above, to yield 4-(4-morpholin-4-yl-4-oxo-2-benzylsulfonylmethyl-butyrylamino)-3-oxo-azepane-1-carboxylic acid benzyl ester; $^1$H NMR: (DMSO) 8.46–8.42 (m, 1H), 7.44–7.24 (m, 10H), 5.18–5.04 (m, 2H), 4.52–4.33 (m, 4H), 4.04–3.76 (m, 2H), 3.58–3.30 (m, 11H), 3.11–3.03 (m, 1H), 2.96–2.78 (m, 1H), 2.72–2.57 (m, 1H), 1.84–1.55 (m, 4H); MS: $(M+H)^+$ 600.

Example 14

N-(1,1-Dimethyl-2-oxazolo[4,5-b]pyridin-2-yl-2-oxo-ethyl)-4-morpholin-4-yl-4-oxo-2-benzylsulfonylmethyl-butyramide (Compound 70)

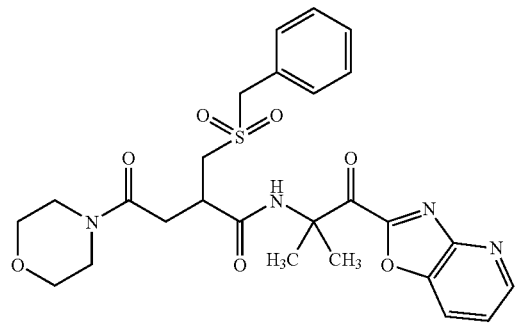

To a stirred mixture of 4-morpholin-4-yl-4-oxo-2-benzylsulfonylmethyl-butyric acid (142 mg, 0.4 mmol), 2-amino-2-methyl-1-oxazolo[4,5-b]pyridin-2-yl-propan-1-one TFA salt (165 mg), prepared as in reference 14, and HOBt (73 mg, 0.45 mmol) in $MeCl_2$ (5 ml) was added EDC (115 mg, 0.6 mmol) and N-methylmorpholine (0.25 ml) at room temperature. After stirring for 14 hours, the reaction mixture was extracted with ethyl acetate. The organic layer was washed with saturated $NaHCO_3$, brine, dried with $MgSO_4$ and concentrated. The residue was purified by silica gel column chromatography to yield 92 mg of N-{1-[(5-Ethyl-[1,3,4]oxadiazol-2-yl)-hydroxy-methyl]-butyl}-4-morpholin-4-yl-4-oxo-2-benzylsulfonylmethyl-butyramide.

This amide was treated with Dess-Martin periodinane (125.6 mg, 0.254 mmol) at room temperature. After stirring for 1 hour, 5 ml of saturated $Na_2S_2O_3$—$NaHCO_3$ were added. After a further 0.5 hours, the reaction mixture was extracted with ethyl acetate, washed with brine, dried with $MgSO_4$ and concentrated. The residue was purified with silica gel column chromatography to yield 31 mg of N-(1,1-dimethyl-2-oxazolo[4,5-b]pyridin-2-yl-2-oxo-ethyl)-4-morpholin-4-yl-4-oxo-2-benzylsulfonylmethyl-butyramide; H$^1$ NMR(DMSO-d): 9.36 (1H, s, NH), 8.68 (1H, d, J=4.7 Hz), 8.34 (1H, d, J=8.42 Hz), 7.62 (1H, dd, J=4.7 Hz, J=8.42 Hz), 7.4–7.4(5H, m), 4.41–4.3(2H, s), 3.5–3(12H, m), 2.2–2.1(1H, m), 1.6(3H, s), 1.51(3H, s); MS: 541.4(M−1), 543.4(M+1).

Example 15

N-[1-(5-Ethyl-[1,3,4]oxadiazole-2-carbonyl)-butyl]-4-morpholin-4-yl-4-oxo-2-benzylsulfonylmethyl-butyramide (Compound 71)

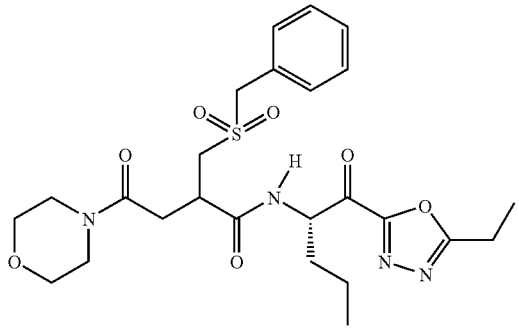

To a stirred mixture of 4-morpholin-4-yl-4-oxo-2-benzylsulfonylmethyl-butyric acid (177.7 mg, 0.5 mmol), 2-amino-1-(5-ethyl-1,3,4-oxadiazole-2-yl)-1-pentanol HCl salt (117.5 mg), and HOBt (91.8 mg, 0.6 mmol) in MeCl$_2$ (5 ml), was added EDC (144 mg, 0.75 mmol) and N-methylmorpholine (0.3 ml) at room temperature. After stirring for 14 hours, the reaction mixture was extracted with ethyl acetate. The organic layer was washed with saturated NaHCO$_3$, brine, dried with MgSO$_4$ and concentrated to yield 240 mg of crude product (MS: 536(M−1), 538.4(M+1)). Without further purification, the crude product was treated with Dess-Martin periodinane (334 mg, 0.67 mmol) at room temperature in 5 mL of MeCl$_2$. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 110 mg of N-[1-(5-ethyl-[113,4]oxadiazole-2-carbonyl)-butyl]-4-morpholin-4-yl-4-oxo-2-benzylsulfonylmethyl-butyramide; H$^1$ NMR(DMSO-d): 8.84(½H, d, NH, diastereomeric), 8.78(¼H, d, NH, diastereomeric), 7.45–7.2(5H, m), 5.05–4.9(1H, m), 4.48–4.3(2H, m), 3.6–3.4(4H, m), 3.4–3.2(4H, m), 3.1–2.4(6H, m), 1.9–1.75(1H, m), 1.7–1.55(2H, m), 1.25–1.2(2H, m), 1.2–1.1(3H, m), 0.9–0.8(3H, m); MS: 534M−1), 535.8 (M+1).

Example 16

N-[1-(5-Ethyl-[,1,3,4]oxadiazole-2-carbonyl)-butyl]-4-oxo-2-benzylsulfonyl-methyl-4-piperidin-1-yl-butyramide (Compound 72)

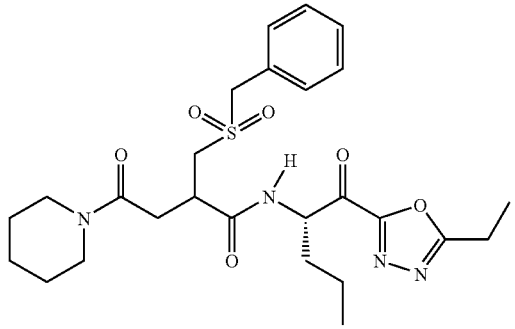

To a stirred mixture 4-oxo-2-benzylsulfonylmethyl-4-piperidin-1-yl-butyric acid (176.5 mg, 0.5 mmol), 2-amino-1-(5-ethyl-1,3,4-oxadiazole-2-yl)-1-pentanol HCl salt (117.5 mg), and HOBt (91.8 mg, 0.6 mmol) in MeCl$_2$ (5 ml), was added EDC (144 mg, 0.75 mmol) and N-methylmorpholine (0.3 ml) at room temperature. After stirring for 14 hours, the reaction mixture was extracted with ethyl acetate. The organic layer was washed with saturated NaHCO$_3$, brine, dried with MgSO$_4$ and concentrated to yield 270 mg of crude product; MS: 534.1(M−1), 535.7(M+1).

The amide was then treated with Dess-Martin periodinane (378.7 mg, 0.675 mmol) at room temperature in 5 ml of MeCl$_2$. After stirring for 1 hour, 5 ml of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 165 mg of N-[1-(5-Ethyl-[1,3,4]oxadiazole-2-carbonyl)-butyl]-4-oxo-2-benzyl-sulfonyl-methyl-4-piperidin-1-yl-butyramide; H$^1$ NMR (DMSO-d): 8.85(½H, d, NH, diastereomeric), 8.78(½, d, NH, diastereomeric), 7.4–7.2 (5H, m), 5.1–4.9(1H, m), 4.5–4.3(2H, m), 3.5–3.2(8H, m), 3.1–2.6(1H, m), 2.9(2H, m), 1.9–1.6(2H, m), 1.6–1.2(8H, m), 1.24(3H, m), 0.9–0.8(3H, m); MS: 531.6(M−1), 533.4 (M+1).

Example 17

N-[1-(5-Ethyl-[1,3,4]oxadiazole-2-carbonyl)-butyl]-4-oxo-2-benzylsulfonyl-methyl-4-pyrrolidin-1-yl-butyramide (Compound 73)

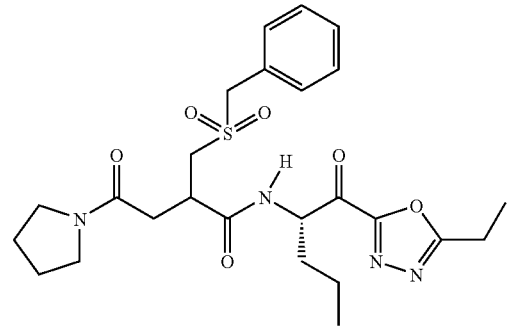

To a stirred mixture 4-cyclopentyl-4-oxo-2-benzylsulfonylmethyl-butyric acid (169.5 mg, 0.5 mmol), 2-amino-1-(5-ethyl-1,3,4-oxadiazole-2-yl)-1-pentanol HCl salt (117.5 mg), and HOBt (91.8 mg, 0.6 mmol) in MeCl$_2$ 5 ml), was added EDC (144 mg, 0.75 mmol) and N-methylmorpholine (0.3 ml) at room temperature. After stirring for 14 hours, the reaction mixture was extracted with ethyl acetate. The organic layer was washed with saturated NaHCO$_3$, brine, dried with MgSO$_4$ and concentrated to yield 240 mg of crude product. The crude product was treated with Dess-Martin periodinane (343 mg, 0.693 mmol) at room temperature in 5 mls of MeCl$_2$. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 145 mg of N-[1-(5-Ethyl-[1,3,4]oxadiazole-2-carbonyl)-butyl]-4-oxo-2-benzylsulfonyl-methyl-4-pyrrolidin-1-yl-butyramide; H$^1$NMR(DMSO-d): 8.85 (½H, d, NH, diastereomeric), 8.78 (½H, d, NH, diastereomeric), 7.5–7.3 (5H, m), 5.1–4.95(1H, m), 4.5–4.3 (2H, m), 3.5–3.2 (8H, m), 3.2–3(1H, m), 2.82(2H, m), 2–1.8(6H, m), 1.6–1.3(2H, m), 1.24(3H, m), 0.9–0.8(3H, m); MS: 518.2(M–1), 519.7 (M+1).

Example 18

N-[1-(5-Methoxymethyl-[1,3,4]oxadiazole-2-carbonyl)-propyl]-4-morpholin-4-yl-4-oxo-2-benzylsulfonylmethyl-butyramide (Compound 74)

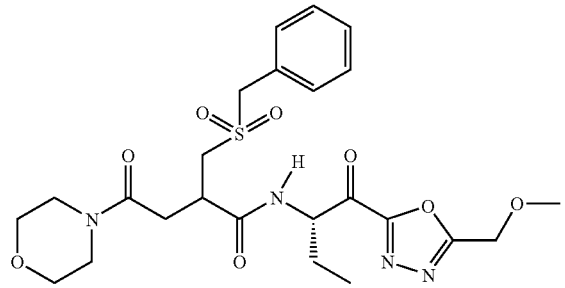

To a stirred mixture of 4-morpholin-4-yl-4-oxo-2-benzylsulfonylmethyl-butyric acid (230 mg, 0.65 mmol), 2-amino-1-(5-methoxymethyl-[1,3,4]oxadiazol-2-yl)-butan-1-one TFA salt (204 mg), prepared as in reference 15, and HOBt (119 mg, 0.78 mmol) in MeCl$_2$ (5 ml), was added EDC (187 mg, 0.98 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 82 mg of N-{1-[Hydroxy-(5-methoxymethyl-[1,3,4]oxadiazol-2-yl)-methyl]-propyl}-4-morpholin-4-yl-4-oxo-2-benzylsulfonyl-methyl-butyramide; MS: 537.6(M–1), 539.8 (M+1).

This amide then was treated with Dess-Martin periodinane (111 mg, 0.149 mmol) at room temperature. After stirring for 1 hour, 5 mls of saturated Na$_2$S$_2$O$_3$—NaHCO$_3$ was added. After a further 0.5 hours, the reaction mixture was extracted with ethyl acetate, washed with brine, dried with MgSO$_4$ and concentrated. The residue was purified with silica gel column chromatography to yield 13 mgs of N-[1-(5-Methoxymethyl-[1,3,4]oxadiazole-2-carbonyl)-propyl]-4-morpholin-4-yl-4-oxo-2-benzylsulfonyl-methyl-butyramide; H$^1$ NMR(CDCl$_3$): 7.8, 7.5(1H, d,d NH, diastereomeric), 7.4–7.2(5H, m), 5.3–5.1(1H, m), 4.6(2H, s, OCH$_2$), 4.3–4.1(3H, m), 3.8–3.1(13H, m), 3–2.4(2H, m), 2.2–1.5(2H, m), 0.95(3H, t); MS: 535.7(M–1), 537.5(M+1).

Example 19

N-[1-(5-Methoxymethyl-[1,3,4]oxadiazole-2-carbonyl)-propyl]-4-oxo-2-benzylsulfonylmethyl-4-piperidin-1-yl-butyramide (Compound 75)

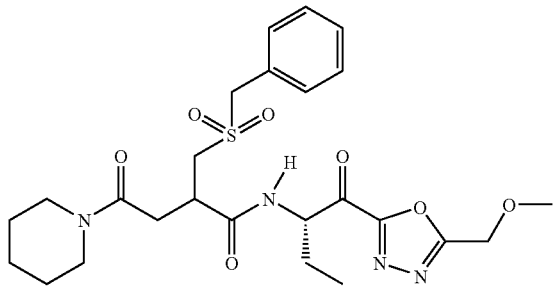

To a stirred mixture of 4-oxo-2-benzylsulfonylmethyl-4-piperidin-1-yl-butyric acid (229 mg, 0.65 mmol), 2-amino-1-(5-methoxymethyl-1,3,4-oxadiazole-2-yl)-1-propanol TFA salt (204 mg), prepared as in reference 15, and HOBt (119 mg, 0.78 mmol) in MeCl$_2$ (5 ml), was added EDC (187 mg, 0.98 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 130 mg of N-{1-[hydroxy-(5-methoxymethyl-[1,3,4]oxadiazol-2-yl)-methyl]-propyl}-4-oxo-2-benzylsulfonylmethyl-4-piperidin-1-yl-butyramide; MS: 535.4(M–1), 537.7(M+1).

The amide then was treated with Dess-Martin periodinane (180 mg, 0.364 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 26 mgs of N-[1-(5-Methoxymethyl-[1,3,4]oxadiazole-2-carbonyl)-propyl]-4-oxo-2-benzylsulfonylmethyl-4-piperidin-1-yl-butyramide; H$^1$ NMR(CDCl$_3$): 8, 7.7(1H, d,d NH, diastereomeric), 7.4–7.2(5H, m), 5.3–5.1(1H, m), 4.6(2H, s, OCH$_2$), 4.3–4.1(3H, m), 3.8–3.2(9H, m), 3–2.4(2H, m), 2.2–1.4(8H, m), 0.95(3H, t); MS: 535.7(M+1).

Example 20

N-[1-(5-Methoxymethyl-[1,3,4]oxadiazole-2-carbonyl)-propyl]-4-oxo-2-benzylsulfonylmethyl-4-pyrrolidin-1-yl-butyramide (Compound 76)

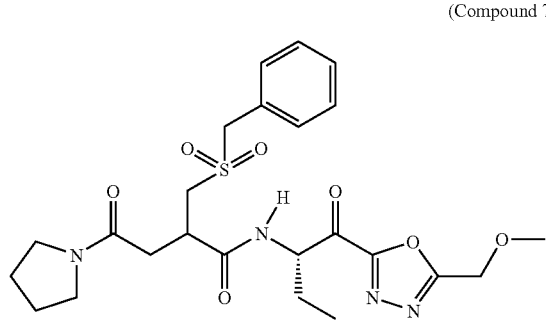

To a stirred mixture of 4-oxo-2-benzylsulfonylmethyl-4-pyrrolidin-1-yl-butyric acid (220 mg, 0.65 mmol), 2-amino-1-(5-methoxymethyl-1,3,4-oxadiazole-2-yl)-1-propanol TFA salt (204 mg), prepared as in reference 15, and HOBt (119 mg, 0.78 mmol) in MeCl$_2$ (5 ml), was added EDC (187 mg, 0.98 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 84 mg of N-{1-[Hydroxy-(5-methoxymethyl-[1,3,4]oxadiazol-2-yl)-methyl]-propyl}-4-oxo-2-benzylsulfonylmethyl-4-pyrrolidin-1-yl-butyramide. Without further purification, the crude product was used for next reaction; MS: 521.6(M−1), 523.2(M+1).

This amide was treated with Dess-Martin periodinane (114 mg, 0.153 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 17 mg of N-[1-(5-Methoxymethyl-[1,3,4]oxadiazole-2-carbonyl)-propyl]-4-oxo-2-benzylsulfonylmethyl-4-pyrrolidin-1-yl-butyramide; H$^1$ NMR (CDCl$_3$): 8.2, 8(1H, d,d, NH, diastereomeric), 7.6–7.2(5H, m), 5.3–5.1(1H, m), 4.6(2H, s, OCH$_2$), 4.3–4.1(3H, m), 3.8–3.2(9H, m), 3–2.4(2H, m), 2.2–1.4(6H, m), 0.95(3H, t); MS:519.6(M−1), 521.6(M+1).

Example 21

4-Morpholin-4-yl-4-oxo-2-benzylsulfonylmethyl-N-[1-(5-phenyl-[1,3,4]oxadiazole-2-carbonyl)-propyl]-butyramide (Compound 77)

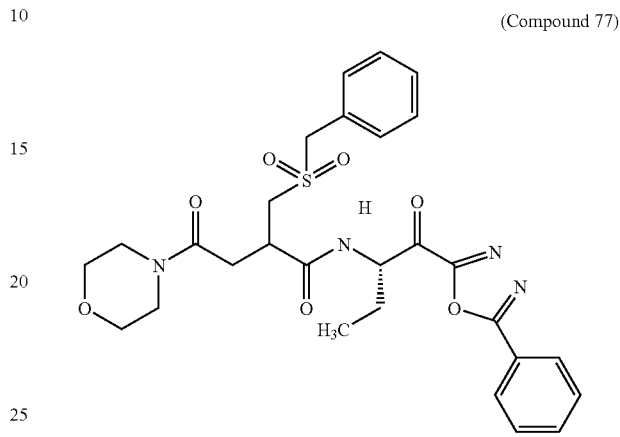

To a stirred mixture of 4-morpholin-4-yl-4-oxo-2-benzylsulfonylmethyl-butyric acid (177 mg, 0.5 mmol), 2-amino-1-(5-phenyl-[1,3,4]oxadiazol-2-yl)-1-butanol TFA salt (175 mg), prepared as in reference 16, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 308 mg of N-{1-[Hydroxy-(5-phenyl-[1,3,4]oxadiazol-2-yl)-methyl]-propyl}-4-morpholin-4-yl-4-oxo-2-benzylsulfonylmethyl-butyramide. Without further purification, the crude product was used for next reaction; MS: 569.6(M−1), 571.4(M+1).

This amide was treated with Dess-Martin periodinane (371 mg, 0.75 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 224 mg of 4-morpholin-4-yl-4-oxo-2-benzylsulfonylmethyl-N-[1-(5-phenyl-[1,3,4]oxadiazole-2-carbonyl)-propyl]-butyramide; H$^1$ NMR(DMSO-d): 8.9, 8.84 (1H, d, d, NH, diastereomeric), 8.1–8(2H, m), 7.7–7.6(3H, m), 7.4–7.3(5H, m),5.1–4.9(1H, m), 4.5–4.3 (2H, m), 3.6–3.3(11H, m), 3.12–3(1H, m), 2.65–2.5(1H, m), 2–1.9(1H, m), 1.8–1.7(1H, m), 0.96(3H, t); MS: 567.6(M−1), 569.4(M+1).

Example 22

4-Oxo-2-benzylsulfonylmethyl-N-[1-(5-phenyl-[1,3,4]oxadiazole-2-carbonyl)-propyl]-4-piperidin-1-yl-butyramide (Compound 78)

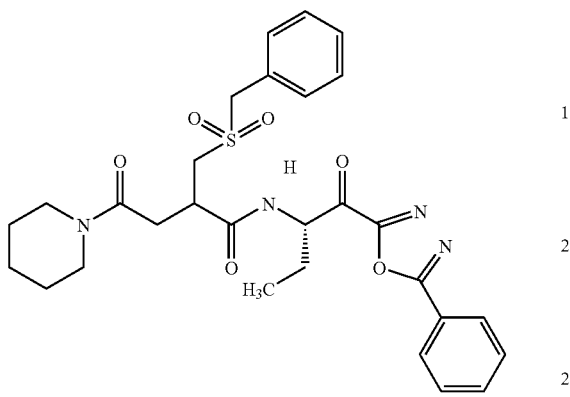

To a stirred mixture of 4-oxo-2-benzylsulfonylmethyl-4-piperidin-1-yl-butyric acid (177 mg, 0.5 mmol), 2-amino-1-(5-phenyl-[1,3,4]oxadiazol-2-yl)-1-butanol TFA salt (175 mg), prepared as in reference 16, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 284 mg of N-{1-[Hydroxy-(5-phenyl-[1,3,4]oxadiazol-2-yl)-methyl]propyl}-4-oxo-2-henylmethyl-sulfonylmethyl-4-piperidin-1-yl-butyramide. Without further purification, the crude product was used for next reaction; MS: 567.6(M−1), 569.6 (M+1).

This amide was treated with Dess-Martin periodinane (371 mg, 0.75 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 237 mg of 4-oxo-2-benzylsulfonylmethyl-N-[1-(5-phenyl[1,3,4]oxadiazole-2-carbonyl)-propyl]-4-piperidin-1-yl-butyramide; H$^1$ NMR (DMSO-d): 8.9, 8.84 (1H, d, d, NH, diastereomeric), 8.1–8 (2H, m), 7.7–7.6(3H, m), 7.4–7.3(5H, m),5.1–4.9(1H, m), 4.5–4.3(2H, m), 3.4–3.1(7H, m), 3.12–3(1H, m), 2.65–2.5 (1H, m), 2–1.9(1H, m), 1.8–1.7(1H, m), 1.6–1.2(6H, m), 0.96(3H, t); MS: 565.4(M−1), 567.6(M+1).

Example 23

4-Oxo-2-benzylsulfonylmethyl-N-[1-(5-phenyl-[1,3,4]oxadiazole-2-carbonyl)-propyl]-4-pyrrolidin-1-yl-butyramide (Compound 79)

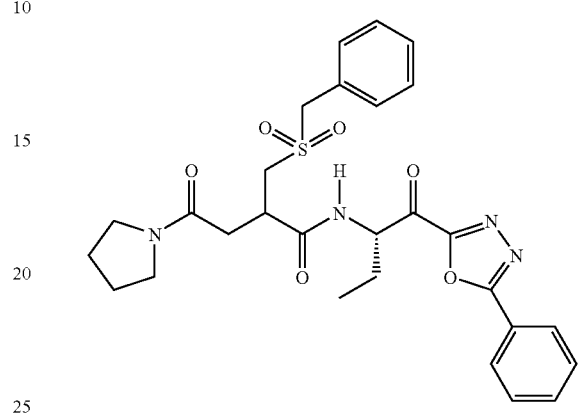

To a stiffed mixture of 4-Oxo-2-benzylsulfonylmethyl-4-pyrrolidin-1-yl-butyric acid (170 mg, 0.5 mmol), 2-amino-1-(5-phenyl-[1,3,4]oxadiazol-2-yl)-1-butanol TFA salt (175 mg), prepared as above, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 280 mg of N-{1-[Hydroxy-(5-phenyl-[1,3,4]oxadiazol-2-yl)-methyl]-propyl}-4-oxo-2-henylmethylsulfonylmethyl-4-pyrrolidin-1-yl-butyramide. Without further purification, the crude product was used for next reaction; MS: 553.6 (M−1), 555.4(M+1).

This amide was treated with Des s-Martin periodinane (371 mg, 0.75 mmol) at room temperature. After stirring for 1 hour, 5 mls of saturated Na$_2$SO$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 200 mg of 4-oxo-2-benzylsulfonylmethyl-N-[1-(5-phenyl-[1,3,4]oxadiazole-2-carbonyl)-propyl]-4-pyrrolidin-1-yl-butyramide; H$^1$ NMR (DMSO-d): 8.9, 8.84 (1H, d, d, NH, diastereomeric), 8.1–8 (2H, m), 7.7–7.6(3H, m), 7.4–7.3(5H, m),5.1–4.9(1H, m), 4.5–4.3(2H, m), 3.4–3.1(7H, m), 3.12–3(1H, m), 2.65–2.5 (1H, m), 2.1–1.6(6H, m), 0.96(3H, t); MS: 551.6(M−1), 553.6(M+1).

Example 24

4-Morpholin-4-yl-N-[1-(oxazolo[4,5-b]pyridine-2-carbonyl)-propyl]-4-oxo-2-benzylsulfonylmethyl-butyramide (Compound 80)

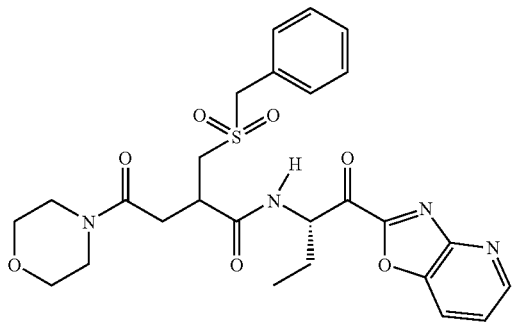

To a stirred mixture of 4-morpholin-4-yl-4-oxo-2-benzyl-sulfonylmethyl-butyric acid (177 mg, 0.5 mmol), 2-amino-1-(5-phenyl-[1,3,4]oxadiazol-2-yl)-1-butanol TFA salt (175 mg), prepared as in reference 17, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 308 mg of N-[1-(Hydroxy-oxazolo[4,5-b]pyridin-2-yl-methyl)-propyl]-4-morpholin-4-yl-4-oxo-2-benzylsulfonylmethyl-butyramide; MS: 543.6 (M−1), 545.6 (M+1)

This amide was treated with Dess-Martin periodinane (371 mg 0.75 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 224 mg of 4-morpholin-4-yl-N-[1-(oxazolo[4,5-b]pyridine-2-carbonyl)-propyl]-4-oxo-2-benzylsulfonylmethyl-butyramide; H$^1$ NMR (DMSO-d): 8.96, 8.85(1H, d,d, NH, diastereomeric), 8.75–8.7(1H, m), 8.42–8.3(1H, m), 7.7–7.6(1H, m), 7.4–7.3(5H, m), 5.15–5.04(1H, m), 4.5–4.3(2H, m), 3.6–3.2(11H, m), 3.15–3.0(1H, m), 2.7–2.5(1H, m), 2.1–1.9(1H, m), 1.8–1.7 (1H, m), 0.98(3H, t); MS: 541.2(M−1), 543.2(M+1).

Example 25

N-[1-(Oxazolo[4,5-b]pyridine-2-carbonyl)-propyl]-4-oxo-2-benzylsulfonyl-methyl-4-piperidin-1-yl-butyramide (Compound 81)

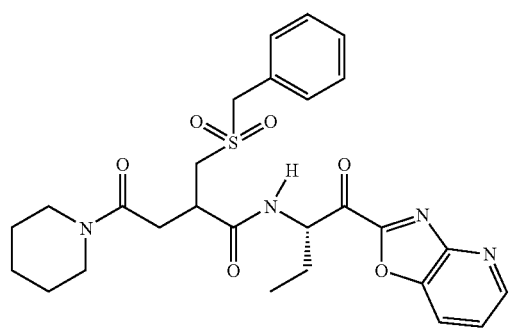

To a stirred mixture of 4-oxo-2-benzylsulfonylmethyl-4-piperidin-1-yl-butyric acid (177 mg, 0.5 mmol), 2-amino-1-(5-phenyl-[1,3,4]oxadiazol-2-yl)-1-butanol TFA salt (175 mg), prepared as in reference 17, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 284 mg of N-[1-(hydroxy-oxazolo[4,5-b]pyridin-2-yl-methyl)propyl]-4-oxo-2-henylmethylsulfonyl-methyl-4-piperidin-1-yl-butyramide; MS: 541.6 (MI), 543.4 (M+1).

This amide was treated with Dess-Martin periodinane (371 mg, 0.75 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 237 mg of N-[1-(Oxazolo[4,5-b]pyridine-2-carbonyl)propyl]-4-oxo-2-benzylsulfonyl-methyl-4-piperidin-1-yl-butyramide; H$^1$ NMR DMSO-d): 8.93, 8.83(1H, d,d, NH, diastereomeric), 8.75–8.72(1H, m), 8.4–8.37(1H, m), 7.7–7.6(1H, m), 7.4–7.3(5H, m), 5.15–5 (1H, m), 4.5–4.3(2H, m), 3.45–3.2(9H, m), 3.1–3(1H, m), 2.67–2.5(1H, m), 2.1–1.9(1H, m), 1.84–1.7(1H, m), 1.6–1.5 (2H, m), 1.5–1.3(4H, m), 0.98(3H, t); MS: 539.4(M−1), 541.2(M+1).

Example 26

N-[1-(Oxazolo[4,5-b]pyridine-2-carbonyl)-propyl]-4-oxo-2-benzylsulfonyl-methyl-4-pyrrolidin-1-yl-butyramide (Compound 82)

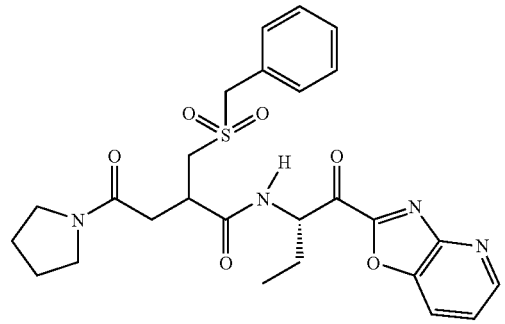

To a stirred mixture of 4-oxo-2-benzylsulfonylmethyl-4-pyrrolidin-1-yl-butyric acid (170 mg, 0.5 mmol), 2-amino-1-(5-phenyl-[1,3,4]oxadiazol-2-yl)-1-butanol TFA salt (175 mg), prepared as in reference 17, and HOBt (92 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 280 mg of N-[1 (Hydroxy-oxazolo[4,5-b]pyridin-2-yl-methyl)-propyl]-4-oxo-2-henylmethylsulfonyl-methyl-4-pyrrolidin-1-yl-butyramide. Without further purification, the crude product was used for next reaction; MS: 527.6(M−1), 529.4(M+1).

This amide was treated with Des s-Martin periodinane (371 mg, 0.75 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 200 mg of N-[1-(Oxazolo[4,5-b]pyridine-2-carbonyl)-propyl]-4-oxo-2-benzylsulfonyl-methyl-4-pyrrolidin-1-yl-butyramide; H$^1$ NMR (DMSO-d): 8.96, 8.87(1H, d,d, NH, diastereomeric), 8.75–8.72(1H, m), 8.45–8.3(1H, m), 7.7–7.6(1H, m), 7.45–7.3(5H, m), 5.2–5 (1H, m), 4.5–4.3(2H, m), 3.5–3.15(7H, m), 3.15–3(1H, m), 2.55–2.4(1H, m), 2.1–1.95(1H, m), 1.9–1.6(5H, m), 0.98 (3H, t); MS: 525.2(M−1), 526.8(M+1).

Example 27

4-Morpholin-4-yl-4-oxo-2-benzylsulfonylmethyl-N-[1-(5-pyridin-4-yl-[1,3,4]oxadiazole-2-carbonyl)-propyl]-butyramide (Compound 83)

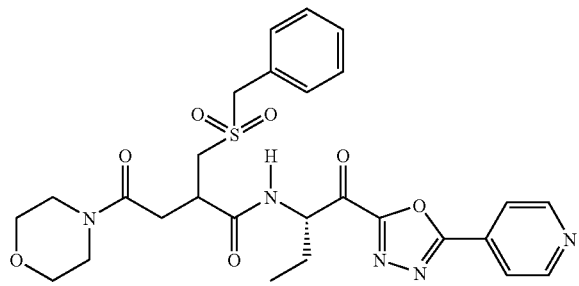

To a stiffed mixture of 4-morpholin-4-yl-4-oxo-2-benzyl-sulfonylmethyl-butyric acid (106.5 mg, 0.3 mmol), 2-Amino-1-(5-pyridin-4-yl-[1,3,4]oxadiazol-2-yl)-butan-1-ol TFA salt (105 mg), prepared as in reference 18, and HOBt (55 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated, yield 176 mg of N-{1-[hydroxy-(5-pyridin-4-yl-[1,3,4]oxadiazol-2-yl)-methyl]-propyl)}-4-oxo-2-benzylsulfonylmethyl-4-piperidin-1-yl-butyramide. MS: 568.4(M−1), 570(M+1)

This amide was treated with Dess-Martin periodinane (222.7 mg, 0.45 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 84 mg of 4-morpholin-4-yl-4-oxo-2-benzylsulfonylmethyl-N-[1-(5-pyridin-4-yl-[1,3,4]oxadiazole-2-carbonyl)-propyl]-butyramide; H$^1$NMR(DMSO-d): 8.95–8.85(3H, m), 8.1–8(2H, m), 7.44–7.3(5H, m), 5–4.9(1H, m), 4.5–4.3(2H, m), 3.4–3.(8H, m), 2.7–2.5(1H, m), 2.05–1.9(1H, m), 1.8–1.6(1H, m), 1.6–1.2(6H, m), 0.98(3H, t); MS: 566.6(M−1), 568.6(M+1).

Example 28

4-Oxo-2-benzylsulfonylmethyl-4-piperidin-1-yl-N-[1-(5-pyridin-4-yl-[1,3,4]oxadiazole-2-carbonyl)-propyl]-butyramide (Compound 84)

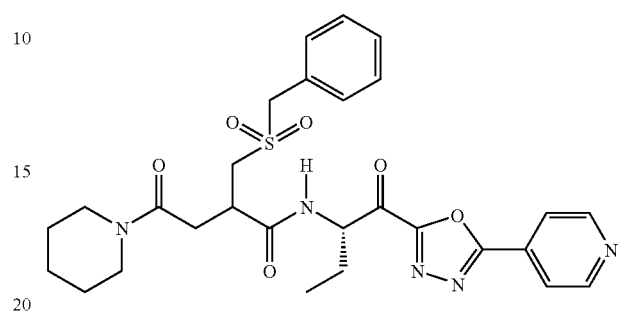

To a stiffed mixture of 4-oxo-2-benzylsulfonylmethyl-4-piperidin-1-yl-butyric acid (105.9 mg, 0.3 mmol), 2-amino-1-(5-pyridin-4-yl-[1,3,4]oxadiazol-2-yl)-butan-1-ol TFA salt (105 mg), prepared as in reference 18, and HOBt (55 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 176 mg of N-{1-[Hydroxy-(5-pyridin-4-yl-[1,3,4]oxadiazol-2-yl)-methyl]-propyl}-4-morpholin-4-yl-4-oxo-2-benzylsulfonyl-methyl-butyramide; MS: 570.2(M−1), 572(M+1).

This amide was treated with Dess-Martin periodinane (222.7 mg, 0.45 mmol) at room temperature. After stirring for 1 hour, 5 mls of saturated Na$_2$SO$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 78 mg of 4-oxo-2-benzylsulfonyl-methyl-4-piperidin-1-yl-N-[1-(5-pyridin-4-yl-[1,3,4]oxadiazole-2-carbonyl)-propyl]-butyramide; H$^1$ NMR(DMSO-d): 9.0–8.85(3H, m), 8.1–8(2H, m), 7.44–7.3 (5H, m), 5–4.9(1H, m), 4.5–4.3(2H, m), 3.6–3.2(11H, m), 3.15–3.05(1H, m), 2.7–2.5(1H, m), 2.05–1.9(1H, m), 1.8–1.7(1H, m), 0.96(3H, t); MS: 568.6(M−1), 570.6(M+1).

Example 29

4-Oxo-2-benzylsulfonylmethyl-N-[1-(5-pyridin-4-yl-[1,3,4]oxadiazole-2-carbonyl)-propyl]-4-pyrrolidin-1-yl-butyramide (Compound 85)

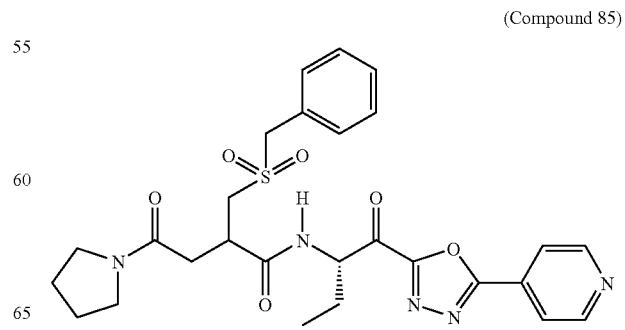

To a stirred mixture of 4-oxo-2-benzylsulfonylmethyl-4-pyrrolidin-1-yl-butyric acid (102 mg, 0.3 mmol), 2-amino-1-(5-pyridin-4-yl-[1,3,4]oxadiazol-2-yl)-butan-1-ol TFA salt (105 mg), prepared as in reference 18, and HOBt (55 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 210 mg of N-{1-[Hydroxy-(5-pyridin-4-yl-[1,3,4]oxadiazol-2-yl)-methyl]-propyl}-4-oxo-2-benzylsulfonylmethyl-4-pyrrolidin-1-yl-butyramide. MS: 554.2(M−1), 555.8(M+1).

This amide was treated with Dess-Martin periodinane (222.7 mg, 0.45 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 102 mg of 4-Oxo-2-benzylsulfonylmethyl-N-[1-(5-pyridin-4-yl-[1,3,4]oxadiazole-2-carbonyl)-propyl]-4-pyrrolidin-1-yl-butyramide; H$^1$NMR (DMSO-d): 9.0–8.85(3H, m), 8.1–8(2H, m), 7.44–7.3(5H, m), 5.05–4.9(1H, m), 4.55–4.35(2H, m), 3.4–3.(8H, m), 2.6–2.4(1H, m), 2.05–1.9(1H, m), 1.9–1.6 (5H, m), 0.96(3H, t); MS: 552.6(M−1), 554.6(M+1).

Example 30

4-Morpholin-4-yl-4-oxo-2-benzylsulfonylmethyl-N-[1-(5-pyridin-3-yl-[1,3,4]oxadiazole-2-carbonyl)-propyl]-butyramide (Compound 86)

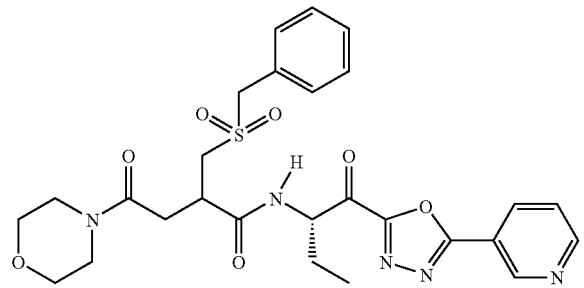

To a stirred mixture of 4-morpholin-4-yl-4-oxo-2-benzyl-sulfonylmethyl-butyric acid (177.7 mg, 0.5 mmol), 2-amino-1-(5-pyridin-3-yl-[1,3,4]oxadiazol-2-yl)-butan-1-ol TFA salt (180 mg), prepared as in reference 19, and HOBt (92 mg, 0.6 mmol) in MeCl$_2$ (5 ml), was added EDC (144 mg, 0.75 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated, yield 21.0 mg of N-{1-[Hydroxy-(5-pyridin-3-yl-[1,3,4]oxadiazol-2-yl)-methyl]-propyl}-4-morpholin-4-yl-4-oxo-2-benzylsulfonylmethyl-butyramide. Without further purification, the crude product was used for next reaction; MS: 570.4(M−1), 572.4(M+1).

This amide was treated with Dess-Martin periodinane (277 mg, 0.56 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 110 mg of 4-morpholin-4-yl-4-oxo-2-benzylsulfonylmethyl-N-[1-(5-pyridin-3-yl-[1,3,4]oxadiazole-2-carbonyl)-propyl]-butyramide; H$^1$ NMR (DMSO-d: 9.23 (1H, s), 8.94, 8.88 (1H, d,d, NH, diastereomeric), 8.87–8.8(1H, m), 8.46–8.4(1H, m), 7.7–7.6 (1H, m), 7.4–7.25(5H, m), 5.05–4.9(1H, m), 4.55–4.3(2H, m), 3.6–3.15(11H, m), 3.14–3(1H, m), 2.7–2.5(1H, m), 2.05–1.9(1H, m), 1.8–1.65(1H, m), 0.98(3H, t); MS: 568.5 (M−1), 570.3(M+1).

Example 31

N-[1-(Benzooxazole-2-carbonyl)-propyl]-4-oxo-2-benzylsulfonylmethyl-4-piperidin-1-yl-butyramide (Compound 87)

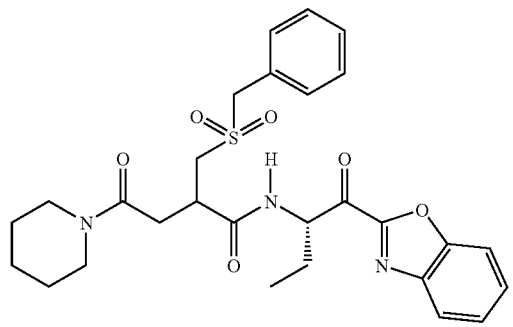

To a stirred mixture of 4-oxo-2-benzylsulfonylmethyl-4-piperidin-1-yl-butyric acid (141 mg, 0.4 mmol), 2-amino-1-benzooxazol-2-yl-butan-1-ol TFA salt. (129 mg), prepared as in reference 20, and HOBt (74 mg, 0.48 mmol) in MeCl$_2$ (5 mL), was added EDC (115 mg, 0.6 mmol) and N-methylmorpholine (0.25 ml) at room temperature. After stir-ring for 14 hours, the reaction mixture was extracted with ethyl acetate. The organic layer was washed with saturated NaHCO$_3$, brine, dried with MgSO$_4$ and concentrated to yield 157 mg of N-piperidin-1-yl-butyramide. Without further purification, the crude product was used for next reaction; MS: 540.4(M−1), 542.6(M+1).

This amide was treated with Dess-Martin periodinane (215.3 mg, 0.435 mmol) at room temperature. After stirring for 1 hour, 5 mls of saturated Na$_2$S$_2$) O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 103.3 mg of N-[1-(Benzooxazole-2-carbonyl)-propyl]-4-oxo-2-benzyl-sulfonylmethyl-4-piperidin-1-yl-butylamide; H$^1$ NMR (DMSO-d): 8.84, 8.76(1H, d,d, J=5.6 Hz, J=6.4 Hz, NH, diastereomeric), 8.02–7.96(1H, m), 7.92–7.86(1H, m), 7.68–7.62(1H, m), 7.58–7.52(1H, m), 7.44–7.32(5H, m), 5.24–5.12(1H, m), 4.52–4.38(2H, m), 3.5–3.22(7H, m), 3.12–3.02(1H, m), 2.64–2.52(1H, m), 2.04–1.94(1H, m), 1.8–1.68(1H, m), 1.6–1.48(2H, m), 1.48–1.32(4H, m), 0.98 (3H, t, J=7.6 Hz); MS: 540.4(M+1).

Example 32

N-[1-(Benzooxazole-2-carbonyl)-propyl]-4-oxo-2-benzylsulfonylmethyl-4-pyrrolidin-1-yl-butyramide (Compound 88)

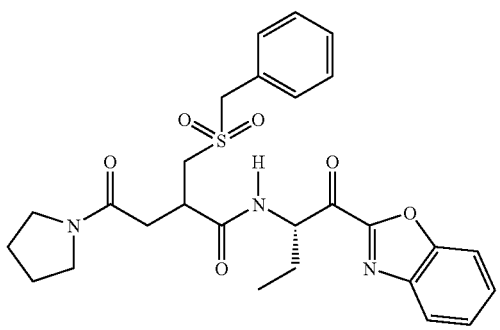

To a stirred mixture of 4-oxo-2-benzylsulfonylmethyl-4-pyrrolidin-1-yl-butyric acid (135.6 mg, 0.4 mmol), 2-amino-1-benzooxazol-2-yl-butan-1-ol TFA salt (129 mg), prepared as in reference 20, and HOBt (73.4 mg, 0.48 mmol) in MeCl$_2$) (5 ml), was added EDC (115.2 mg, 0.6 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 260 mg of N-[1-(Benzooxazol-2-yl-hydroxy-methyl)-propyl]-4-oxo-2-henylmethylsulfonylmethyl-4-pyrrolidin-1-yl-butyramide. Without further purification, the crude product was used for next reaction; MS: 526.6(M−1), 528.6(M+1).

This amide was treated with Dess-Martin periodinane (215 mg, 0.435 mmol) at room temperature. After stirring for 1 hour, 5 mls of saturated Na$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 199 mg of N-[1-(Benzooxazole-2-carbonyl)-propyl]-4-oxo-2-benzylsulfonylmethyl-4-pyrrolidin-1-yl-butyramide; H$^1$ NMR(DMSO-d): 8.87, 8.79(1, d,d, NH, J=6 Hz, J=6.4 Hz, diastereomeric), 8.04–7.96(1H, m), 7.92–7.86(1H, m), 7.68–7.62(1H, m), 7.58–7.5(1H, m), 7.44–7.32(5H, m), 5.25–5.14(1H, m), 4.52–4.38(2H, m), 3.5–3.04(7H, m), 3.03–3.01(1H, m), 2.52–2.4(1H, m), 2.05–1.9(1H, m), 1.9–1.65(5H, m), 0.98 (3H, m); MS: 526.3(M+1).

Example 33

N-[1-(Benzooxazole-2-carbonyl)-propyl]-2-cyclohexylmethyl-4-morpholin-4-yl-4-oxo-butyramide (Compound 89)

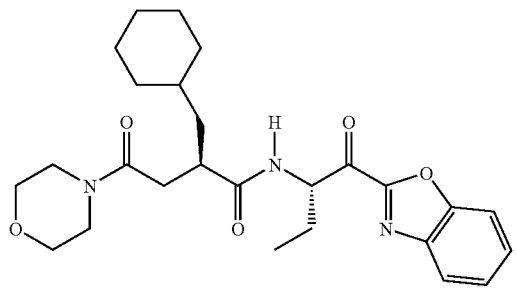

To a stirred mixture of 2-cyclohexylmethyl-4-morpholin-4-yl-4-oxo-butyric acid (84.9 mg, 0.3 mmol), 2-amino-1-benzooxazol-2-yl-butan-1-ol TFA salt (96.9 mg), prepared as in reference 21, and HOBt (55.1 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 150 mg of N-[1-(benzooxazol-2-yl-hydroxy-methyl)-propyl]-2-cyclohexylmethyl-4-morpholin-4-yl-4-oxo-butyramide; MS: 470.5(M−1), 472.4(M+1).

This amide was treated with Dess-Martin periodinane (237.6 mg, 0.48 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 76 mg of N-[1-(benzooxazole-2-carbonyl)-propyl]-2-cyclohexylmethyl-4-morpholin-4-yl-4-oxo-butyramide; H$^1$ NMR(DMSO-d): 8.49(1H, d, J=5.2 Hz, NH), 7.96(11H, d, J=7.6Hz), 7.86 (111, d, J=8.4), 7.6(1H, m), 7.5(1H, m), 5.14–5.04(1H, m), 3.6–3.25(8H, m), 2.9–2.75(1H, m), 2.5–2.4(1H, m), 2.25–2.15(1H, m), 2–1.8(1H, m), 1.8–1.7(2H, m), 1.7–1.6 (1H, m), 1.6–1.4(5H, m), 1.35–1.2(1H, m), 1.21–1(4H, m), 0.96(3H, t); MS: 468.6(M−1), 470.5(M+1), 492.3(M+Na).

Example 34

2-Cyclohexylmethyl-4-morpholin-4-yl-N-[1-(oxazolo[4,5-b]-pyridine-2-carbonyl)-propyl]-4-oxo-butyramide (Compound 90)

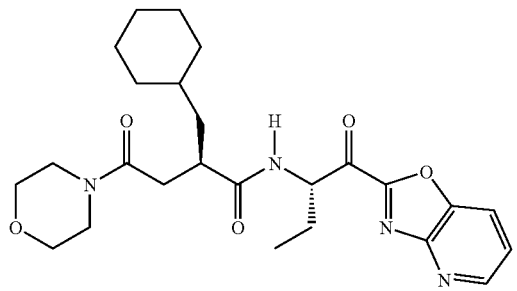

To a stirred mixture of 2-cyclohexylmethyl-4-morpholin-4-yl-4-oxo-butyric acid (84.9 mg, 0.3 mmol), 2-amino-1-(5-phenyl-[1,3,4]oxadiazol-2-yl)-1-butanol TFA salt (97.5 mg), prepared as in reference 21, and HOBt (55.1 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 153 mg of 2-cyclohexylmethyl-N-[1-(hydroxy-oxazolo[4,5-b]pyridin-2-yl-methyl)-propyl]-4-morpholin-4-yl-4-oxo-butyramide; MS: 471.6(M−1), 473.3(M+1).

This amide was treated with Dess-Martin periodinane (237.6 mg, 0.48 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 95 mg of 2-cyclohexylmethyl-4-morpholin-4-yl-N-[1-(oxazolo[4,5-b]pyridine-2-carbonyl)-propyl]-4-oxo-butyramide; H$^1$ NMR (DMSO-d): 8.72–8.68(1H, m), 8.6(1H, d, J=5.2 Hz, NH), 8.4–8.34(1H, m), 7.68–7.59(1H, m), 5.2–4.96(1H, m), 3.5–3.45(8H, m), 2.58(1H, m), 2.5–2.4(1H, m), 2.45–2.15 (1H, m), 2.05–1.9(1H, m), 1.85–1.65(2H, m), 1.6–1.4(5H, m), 1.3–1.2(1H, m), 1.25–1(4H, m), 0.97(3H, t); MS: 469.6 (M−1), 471.4(M+1), 493.2(M+Na).

Example 35

2-Cyclohexylmethyl-N-[1-(5-ethyl-[1,3,4]oxadiazole-2-carbonyl)-butyl]-4-morpholin-4-yl-4-oxo-butyramide (Compound 91)

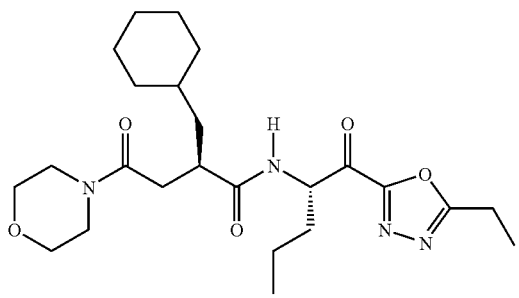

To a stirred mixture of 2-cyclohexylmethyl-4-morpholin-4-yl-4-oxo-butyric acid (84.9 mg, 0.3 mmol), 2-amino-1-(5-ethyl-1,3,4-oxadiazole-2-yl)-1-pentanol HCl salt (70.5 mg), prepared as in reference 21, and HOBt (55.1 mg, 0.36 mmol) in MeCl$_2$ (5 ml), was added EDC (86.4 mg, 0.45 mmol) and N-methylmorpholine (0.25 ml) at room temperature. After stirring for 14 hours, the reaction mixture was extracted with ethyl acetate. The organic layer was washed with saturated NaHCO$_3$, brine, dried with MgSO$_4$ and concentrated to yield 142 mg of 2-cyclohexylmethyl-N-{1-[(5-ethyl-[1,3,4]oxadiazol-2-yl)-hydroxy-methyl]-butyl}-4-morpholin-4-yl-4-oxo-butyramide; MS: 463.5(M−1), 465.3(M+1).

This amide was treated with Dess-Martin periodinane (239 mg, 0.48 mmol) at room temperature. After stirring for 1 hour, 5 mls of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 65 mg of 2-cyclohexylmethyl-N-[1-(5-ethyl-[1,3,4]oxadiazole-2-carbonyl)-butyl]-4-morpholin-4-yl-4-oxo-butyramide; H$^1$ NMR (DMSO-d): 8.6, 8.51(1H, dd, J=6.8 Hz, J=5.6 Hz, NH, diastereomeric), 4.98(−4.88 (1H, m), 3.6–3.25(8H, m), 3–2.9(2H, q, J=7.6 Hz), 2.9–2.75(1H, m), 2.5–2.4(1H, m), 2.3–2.1(1H, m), 1.9–1.7(2H, m), 1.7–1.4(7H, m), 1.4–1.2(2H, m), 1.28(3H, t), 1.2–1(6H, m), 0.88(3H, t); MS: 461.4(M−1), 463.4(M+1), 485.4(M+Na).

Example 36

N-(2-Benzooxazol-2-yl-1-methoxymethyl-2-oxo-ethyl)-2-(2-difluoromethoxy-benzylsulfonylmethyl)-4-morpholin-4-yl-4-oxo-butyramide (Compound 92)

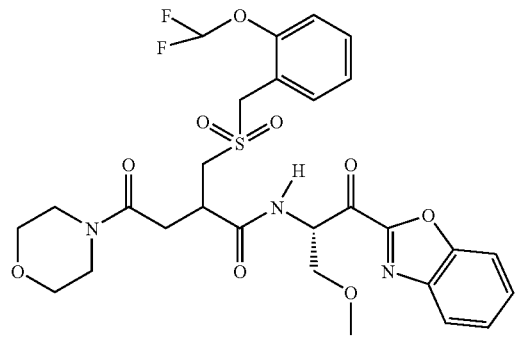

To a stirred mixture of 2-(2-difluoromethoxy-benzylsulfonylmethyl)-4-morpholin-4-yl-4-oxo-butyric acid (210.5 mg, 0.5 mmol), 2-amino-1-benzooxazol-2-yl-3-methoxy-propan-1-ol (112.5 mg), and HOBt (91.8 mg, 0.6 mmol) in MeCl$_2$ (5 ml), was added EDC (144 mg, 0.75 mmol) and N-methylmorpholine (0.35 ml) at room temperature. After stirring for 14 hours, the reaction mixture was extracted with ethyl acetate. The organic layer was washed with saturated NaHCO$_3$, brine, dried with MgSO$_4$ and concentrated to yield 301 mg of N-(2-benzooxazol-2-yl-2-hydroxy-1-methoxymethyl-ethyl)-2-(2-difluoromethoxy-benzylsulfonylmethyl)-4-morpholin-4-yl-4-oxo-butyramide; MS: 624.5(M−1), 626.3(M+1).

This amide (150 mg, 0.24 mmol) was treated with Dess-Martin periodinane (178 mg, 0.36 mmol) at room temperature. After stirring for 1 hour, 5 ml of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield 39 mg of N-(2-Benzooxazol-2-yl-1-methoxymethyl-2-oxo-ethyl)-2-(2-difluoromethoxy-benzylsulfonylmethyl)-4-morpholin-4-yl-4-oxo-butyramide; H$^1$ NMR(DMSO-d): 8.97, 8.8(1H, dd, J=5.6 Hz, J=5.6 Hz, NH, diastereomeric), 8.02–7.94(1H, m), 7.9–7.84(1H, m), 7.66–7.58(1H, m), 7.55–7.38(3H, m), 7.3–7.18(2H, m), 7.1(1H, t, J=73.6 Hz), 5.54–5.42(1H, m), 4.6–4.4(4H, m), 3.92–3.84(1H, m), 3.82–3.72(1H, m), 3.68–3.1(11H, m), 2.7–2.56(1H, m), 1.7–1.55(1H, m), 1.3–1 (1H, m); MS: 622.4(M−1), 624.3(M+1), 646.3(M+Na).

Example 37

N-[1-(Benzooxazole-2-carbonyl)-propyl]-2-(2-cyclohexyl-ethyl)-4-morpholin-4-yl-4-oxo-butyramide (Compound 93)

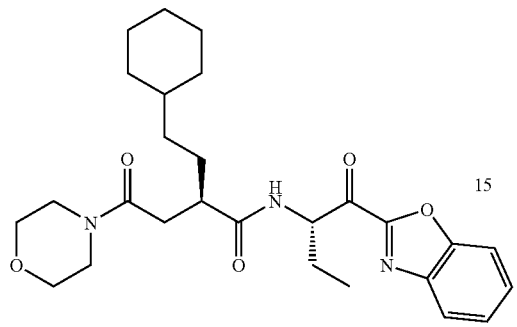

¹H NMR: (DMSO) 8.47 (d, J=6 Hz, 1H), 7.96 (d, J=8.2 Hz, 1H), 7.86 (d, J=8.2 Hz, 1H), 7.59 (t, J=8.2 Hz, 1H), 7.51 (t, J=8.2 Hz, 1H), 5.09–5.03 (m, 1H), 3.56–3.27 (m, 8H), 2.72–2.64 (m, 1H), 2.54–2.46 (m, 1H), 2.21 (dd, J=15.8Hz, J=5.3 Hz, 1H), 1.99–1.89 (m, 1H), 1.76–1.65 (m, 1H), 1.60–0.95 (m, 13H), 0.96 (t, J=7 Hz, 3H), 0.72–0.60 (m, 2H). MS: (M+H)⁺ 484.

Example 38

2-(2-Cyclohexyl-ethyl)-4-morpholin-4-yl-N-[1-(oxazolo[4,5-b]pyridine-2-carbonyl)-propyl]-4-oxo-butylamide (Compound 94)

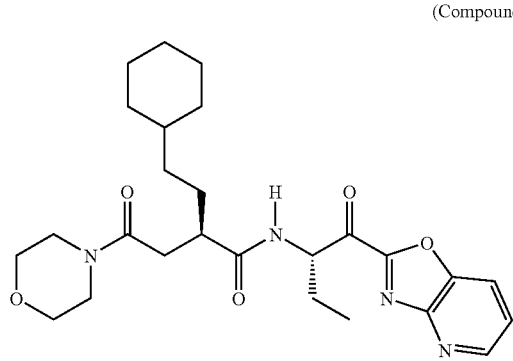

¹H NMR: (DMSO) 8.71–8.68 (m, 1H), 8.58 (d, J=4.7 Hz, 1H), 8.36 (d, J=8.5 Hz, 1H), 7.66–7.61 (m, 1H), 5.00–4.93 (m, 1H), 3.56–3.26 (m, 8H), 2.72–2.63 (m, 1H), 2.54–2.44 (m, 1H), 2.20 (dd, J=15.8 Hz, J=5.3 Hz, 1H), 2.02–1.92 (m, 1H), 1.78–1.67 (m, 1H), 1.60–0.95 (m, 13H), 0.97 (t, J=7 Hz, 3H), 0.68–0.57 (m, 2H). MS: (M+H)⁺ 485.

Example 39

2-(2-Cyclohexyl-ethyl)-4-morpholin-4-yl-4-oxo-N-[1-(5-phenyl-[1,3,4]oxadiazole-2-carbonyl)-propyl]-butyramide (Compound 95)

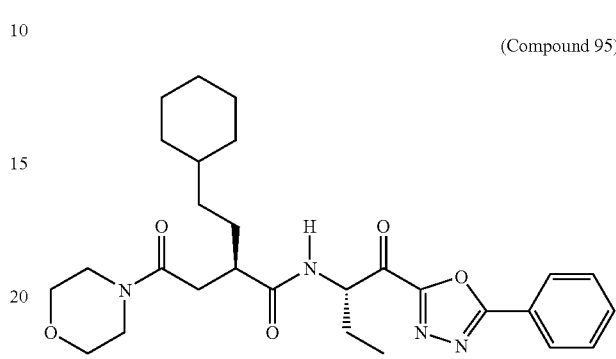

¹H NMR: (DMSO) 8.54 (d, J=4.7 Hz, 1H), 8.10–8.04 (m, 2H), 7.70–7.58 (m, 3H), 4.91–4.85 (m, 1H), 3.55–3.22 (m, 8H), 2.70–2.62 (m, 1H), 2.56–2.45 (m, 1H), 2.22 (dd, J=15.5 Hz, J=5 Hz, 1H), 1.98–1.88 (m, 1H), 1.77–1.66 (m, 1H), 1.60–0.95 (m, 13H), 0.96 (t, J=7 Hz, 3H), 0.75–0.60 (m, 2H). MS: (M+H)⁺ 511.

Example 40

2-(2-Difluoromethoxy-benzylsulfonylmethyl)-4-morpholin-4-yl-4-oxo-N-[1-(5-phenyl-[1,3,4]oxadiazole-2-carbonyl)-propyl]-butyramide (Compound 96)

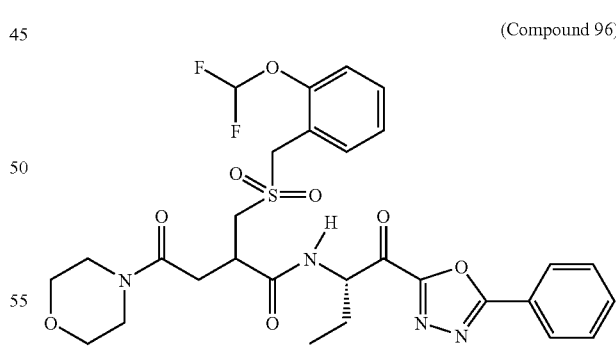

1:1 Mixture of diastereomers. ¹H NMR: (DMSO), 8.89 (d, J=5.6 Hz), 8.82 (d, J=6 Hz) 1H], 8.08–8.03 (m, 2H), 7.70–7.18 (m, 7H),, 7.11 (t, JH,F=74 Hz), 7.08 (t, JH,F=74 Hz) 1H], 5.01–4.90 (m, 1H), 4.56–4.43 (m, 2H), 3.56–3.13 (m, 10H), 2.68–2.40 (m, 3H), 2.00–1.90 (m, 1H), 1.78–1.68 (m, 1H), 0.96 (t, J=7 Hz, 3H). MS: (M+H)⁺ 635.

Example 41

2-(2-Difluoromethoxy-benzylsulfonylmethyl)-N-[1-(5-ethyl-[1,3,4]oxadiazole-2-carbonyl)-butyl]-4-morpholin-4-yl-4-oxo-butyramide

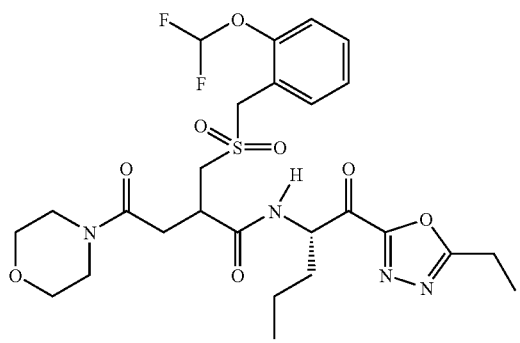

(Compound 97)

1:1 Mixture of diastereomers. $^1$H NMR: (DMSO), 8.82 (d, J=5.5 Hz), 8.77 (d, J=5 Hz) 1H], 7.51–7.42 (m, 2H), 7.30–7.19 (m, 2H),, 7.11 (t, JH,F=74 Hz), 7.10 (t, JH,F=74 Hz) 1H], 5.02–4.92 (m, 1H), 4.56–4.43 (m, 2H), 3.58–3.26 (m, 10H), 3.20–3.12 (m, 1H), 2.98–2.89 (m, 2H), 2.68–2.44 (m, 2H), 1.86–1.76 (m, 1H), 1.69–1.58 (m, 1H), 1.46–1.20 (m, 5H), 0.88 (t, J=7 Hz, 3H). MS: (M+H)$^+$ 601.

Example 42

N-[1-(Benzooxazole-2-carbonyl)-propyl]-2-(2-difluoromethoxy-benzyl-sulfonylmethyl)-4-morpholin-4-yl-4-oxo-butyramide

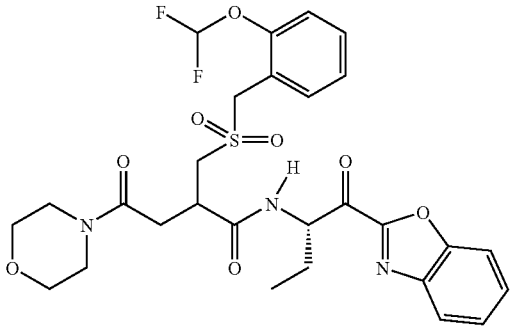

(Compound 98)

1:1 Mixture of diastereomers. $^1$H NMR: (DMSO), 8.85 (d, J=5.311z), 8.76 (d, J=5.3 Hz) 1H], 7.97 (t, J=6.5 Hz, 1H), 7.89–7.84 (m, 1H), 7.64–7.18 (m, 6H),, 7.12 (t, JH,F=74 Hz), 7.10 (t, JH,F=74 Hz) 1H], 5.22–5.11 (m, 11H), 4.56–4.42 (m, 2H), 3.58–3.12 (m, 1H), 2.67–2.42 (m, 2H), 2.02–1.92 (m, 1H), 1.78–1.66 (m, 1H), 0.96 (t, J=7 Hz, 3H). MS: (M+H)$^+$ 608.

Example 43

2-(2-Morpholin-4-yl-2-oxo-ethyl)-5-phenyl-pentanoic acid, 1-(benzooxazole-2-carbonyl)-propyl]-amide

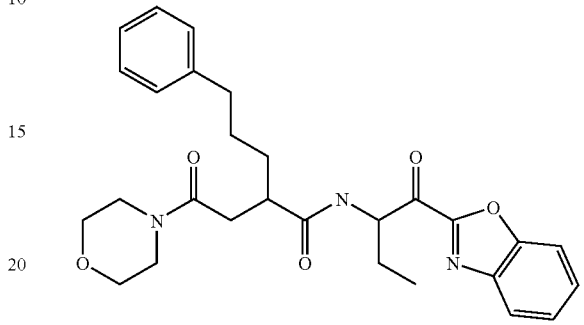

(Compound 99)

2-(2-Morpholin-4-yl-2-oxo-ethyl)-5-phenyl-pentanoic acid (83.7 mg, 0.274 mmol), prepared as in reference 25, and HOBT (62.9 mg, 0.466 mmol) were added to a suspension of PS-bound N-Cyclohexylcarbodiimide (HL 200–400 mesh cross linked with 2% DVB) from Novabiochem (322.3 mg, 0.548 mmol, 1.7 mmol/g loading) in methylene chloride (8 ml) and stirred at room temperature for 15 minutes. 2-Amino-1-benzooxazol-2-yl-butan-1-ol (56.5 mg. 0.274 mmol), prepared as in reference 20, was added and the reaction mixture stirred overnight at room temperature. Silicycle trisamine-3 (380.5 mg, 1.37 mmol, 3.6 mmol/g loading) was added and stirred for another 2 hours. The mixture was filtered and the filtrate evaporated under reduced pressure to give 2-(2-morpholin-4-yl-2-oxo-ethyl)-5-phenyl-pentanoic acid, 1-(benzooxazol-2-yl-hydroxy-methyl)-propyl]-amide as a yellow solid (128 mg).

To a solution of 2-(2-morpholin-4-yl-2-oxo-ethyl)-5-phenyl-pentanoic acid, 1-(benzooxazol-2-yl-hydroxy-methyl)-propyl]-amide (128 mg, 0.259 mmol) in methylene chloride (5 ml), Dess-Martin Periodinane (0.519 mmol, 220 mg) was added and stirred at room temperature for 90 minutes. The reaction mixture was washed with a solution of $Na_2S_2O_3$ in saturated $NaHCO_3$, dried over $MgSO_4$ and concentrated under reduced pressure. The residue was purified by chromatography, eluting with a mixture of ethyl acetate and heptane, to give 2-(2-morpholin-4-yl-2-oxo-ethyl)-5-phenyl-pentanoic acid, 1-(benzooxazole-2-carbonyl)-propyl]-amide as a mixture of diastereoisomers (77 mg); $^1$H NMR (CDCl$_3$) 7.90 (d, J=8 Hz, 1H), 7.65 (d, J=8.2 Hz, 1H), 7.55 (t, J=7.3 Hz, 1H), 7.46 (t, J=7.2 Hz, 1H), 7.4–7.1 (m, 5H),, 7.0 (d, J=7.4 Hz), 6.76 (d, J=7.1 Hz), 1H], 5.60 (m, 1H), 3.8–3.4 (m, 8H), 3.1–2.5 (m, 4H), 2.4–2.1 (m, 2H), 2.0–1.6 (m, 4H), 1.5 (m, 1H), 1.1 (m, 3H). MS: 492 (MH$^+$).

Example 44

(R)-2-Cyclohexylmethyl-4-morpholin-4-yl-4-oxo-N-[(S)-1-(5-phenyl-1,2,4-oxadiazole-3-carbonyl)-propyl]-butyramide (Compound 100)

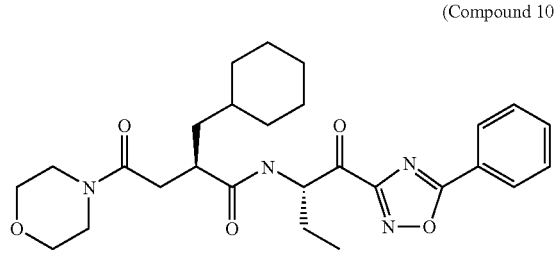

Similarly prepared according to the general procedure given for Example 43 but using (R)-2-cyclohexylmethyl-4-morpholin-4-yl-4-oxo-butyric acid, prepared as described in reference 21, and (S)-2-amino-1-(5-phenyl-[1,2,4]oxadiazol-3-yl)-butan-1-ol, prepared as in reference 26; MS: 519 (M+Na), LC-MS retention time 4.5 min; $^1$H NMR (CDCl$_3$) 8.19 (d, J=7 Hz, 2H), 7.65–7.51 (m, 3H), 6.64 (d, J=7 Hz, 1H), 5.44–5.38 (m, 1H), 3.69–3.38 (m, 8H), 3.05–2.98 (m, 1H), 2.76 (dd, J=16 Hz & 10 Hz, 1H), 2.26 (dd, J=16 Hz & 3 Hz, 1H), 2.10 (m, 1H), 1.80 (m, 1H), 1.75–1.59 (m, 6H), 1.28–1.13 (m, 5H), 1.03–0.98 (t, J=7 Hz, 3H), 0.92–0.81 (m, 2H).

Example 45

2-(2-Morpholin-4-yl-2-oxo-ethyl)-5-phenyl-pentanoic acid, (S)-1-(5-phenyl-[1,2,4]oxadiazole-3-carbonyl)-propyl-amide (Compound 101)

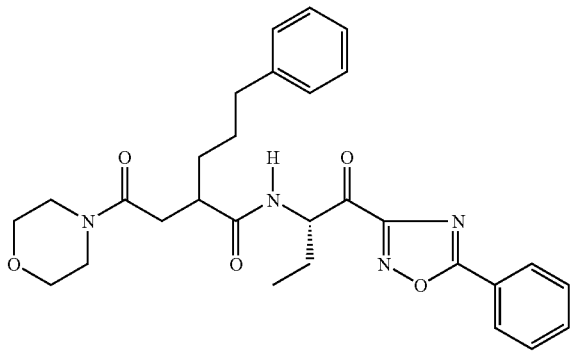

Similarly prepared according to the procedure for Example 43 but using 2-(2-morpholin-4-yl-2-oxo-ethyl)-5-phenyl-pentanoic acid and (S)-2-amino-1-(5-phenyl-[1,2,4]oxadiazol-3-yl)-butan-1-ol; MS: 541 (M+Na), LCMS retention time 4.44 and 4.53 min; $^1$H NMR (CDCl$_3$) 8.18 (d, J=7 Hz, 2H), 7.69–7.51 (m, 3H), 7.27–7.10 (m, 5H), 6.99–6.7 (d, J=7 Hz, 1H), 5.38 (m, 1H), 3.70–3.36 (m, 8H), 2.99–2.56 (m, 4H), 2.27 (m, 1H), 2.11 (m, 1H), 1.87–1.60 (m, 4H), 1.44 (m, 1H), 1.02–0.97 (dt, J=7 Hz, 3H).

Example 46

4-Morpholin-4-yl-4-oxo-2-benzylsulfonylmethyl-N-[(S)-1-(5-phenyl-1,2,4-oxadiazole-3-carbonyl)-propyl]-butyramide (Compound 102)

Similarly prepared according to the procedure for Example 43 but using 4-morpholin-4-yl-4-oxo-2-benzylsulfonylmethyl-butyric acid and (S)-2-amino-1-(5-phenyl-[1,2,4]oxadiazol-3-yl)-butan-1-ol; MS: 569 (MH$^+$), LCMS retention time 4.1 min; $^1$H NMR (CDCl$_3$) 8.18 (d, J=7.9 Hz, 2H), 7.74–7.31 (m, 9H), 5.27 (m, 1H), 4.25 (m, 2H), 3.71–3.41 (m, 8H), 2.95 (m, 1H), 2.78–2.70 (m, 2H), 2.10 (m, 1H), 1.85 (m, 1H), 1.0 (m, 3H).

Example 47

(R)-2-Cyclohexylmethyl-4-morpholin-4-yl-4-oxo-N-[(S)-1-(3-phenyl-1,2,4-oxadiazole-5-carbonyl)-propyl]-butyramide (Compound 103)

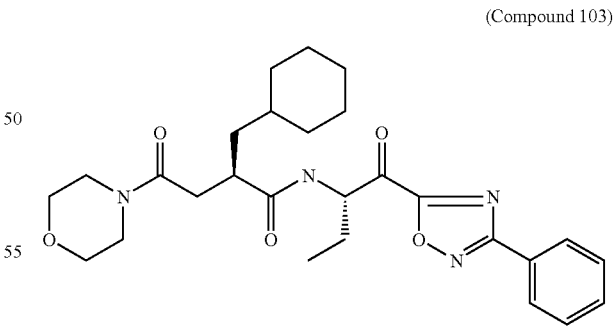

Similarly prepared according to the general procedure given for Example 43 above but using (R)-2-cyclohexylmethyl-4-morpholin-4-yl-4-oxo-butyric acid and (S)-2-amino-1 (3-phenyl-[1,2,4]oxadiazol-5-yl)-butan-1-ol; MS: 497 (MH$^+$).

Example 48

4-Morpholin-4-yl-N-[1-(oxazole-2-carbonyl)-3-phenyl-propyl]-4-oxo-2-benzylsulfonylmethyl-butyramide (Compound 104)

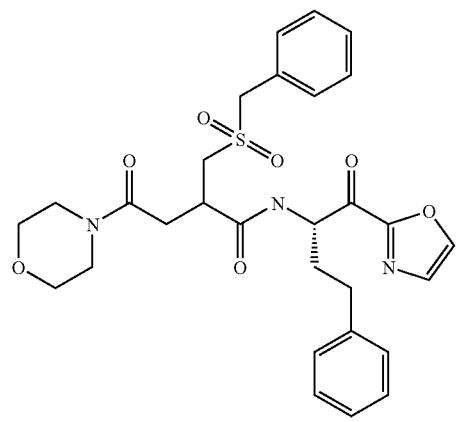

Compound 104 was synthesized according to the following reaction protocol:

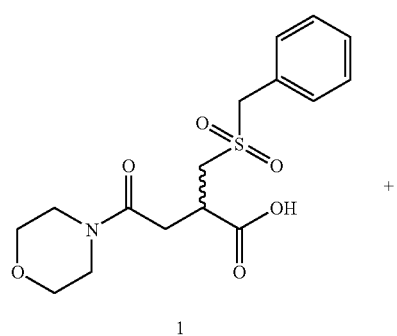

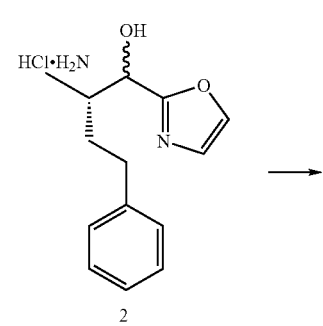

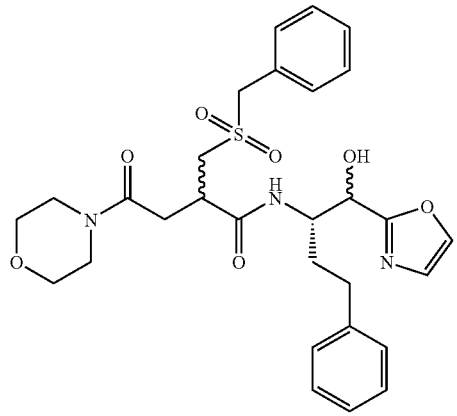

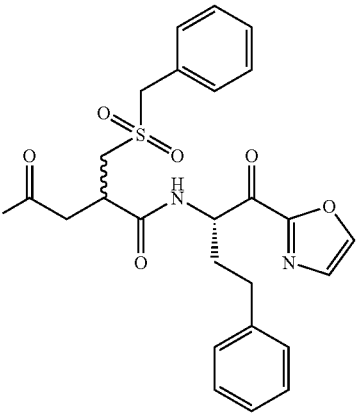

Compound 1 (0.1066 g, 0.3 mmol) and compound 2 (0.0806 g, 0.3 mmol) were mixed with EDC (0.0633 g, 0.33 mmol), HOBT (0.0446 g, 0.33 mmol) and DIEA (0.2 ml, 1.2 mmol) in 3 ml of DMF which was stirred at room temperature overnight. The reaction was diluted with ethyl acetate and washed with cold 1N HCl, saturated sodium bicarbonate and brine. The organic layer was dried over magnesium sulfate, filtered and concentrated under reduced pressure. The crude product was purified using a 10 g silica gel column eluting with 10% ethyl acetate/n-heptane to 80% ethyl acetate/n-heptane to give 79.4 mg (46%) of product 3. Compound 3 (73 mg, 0.13 mmol) was then dissolved in 1 ml of methylene chloride and Dess-Martin periodinane (15% in methylene chloride, 0.7358 g) was added and the reaction was allowed to at room temperature for 3 hours and excess Dess-Martin reagent was consumed by adding sodium thiosulfate in saturated sodium bicarbonate. The product was extracted with ethyl acetate and the organic layer was dried over magnesium sulfate, filtered and concentrated under reduced pressure. The product was purified using a 10 g silica gel column eluting with 100% n-heptane to 30% n-heptane/ethyl acetate to yield 32.2 mg (44%) of the final compound 4; LCMS retention time 3:57 minutes, M+1 (568.2).

Example 49

N-(1,1-Dimethyl-2-oxazol-2-yl-2-oxo-ethyl)-4-morpholin-4-yl-4-oxo-2-benzylsulfonylmethyl-butyramide (Compound 105)

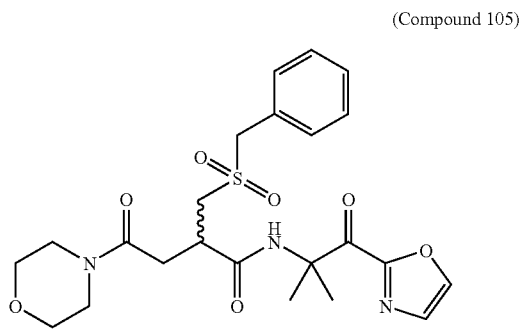

Compound 105 was synthesized according to the following reaction protocol:

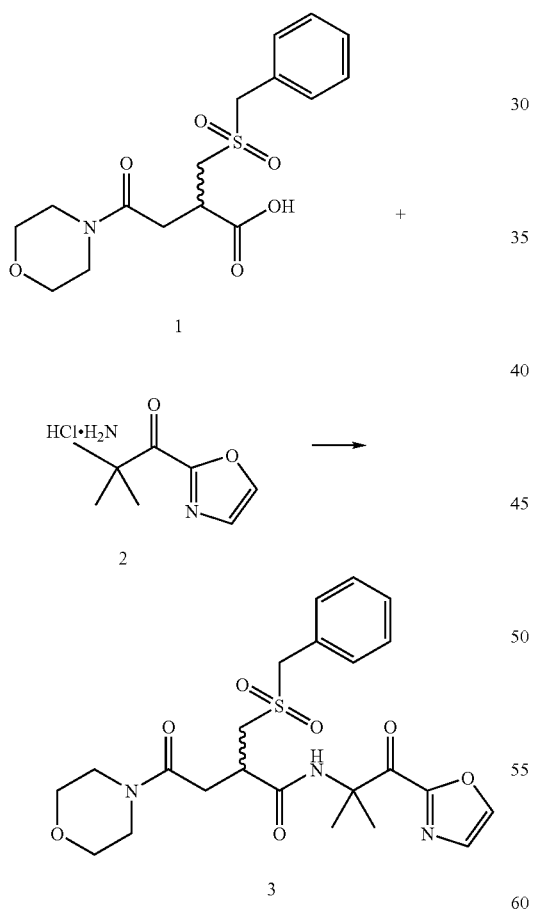

Compound 1 (0.1066 g, 0.3 mmol) and compound 2 (0.0572 g, 0.3 mmol) were mixed with EDC (0.0633 g, 0.33 mmol), HOBT (0.0446 g, 0.33 mmol) and DIEA (0.2 ml, 1.2 mmol) in 3 ml of DMF which was stirred at room temperature overnight. The reaction was diluted with ethyl acetate and washed with cold 1N HCl, saturated sodium bicarbonate and brine. The organic layer was dried over magnesium sulfate, filtered and concentrated under reduced pressure. The crude product was purified using a 10 g silica gel column eluting with 10% ethyl acetate/n-heptane to 80% ethyl acetate/n-heptane to give 15 mg (10%) of final product 3; LCMS retention time 3:10 minutes, M+1(492.2).

Example 50

N-4-Isopropyl-N-1-[1-(oxazole-2-carbonyl)-3-phenyl-propyl]-2-benzylsulfonylmethyl-succinamide (Compound 106)

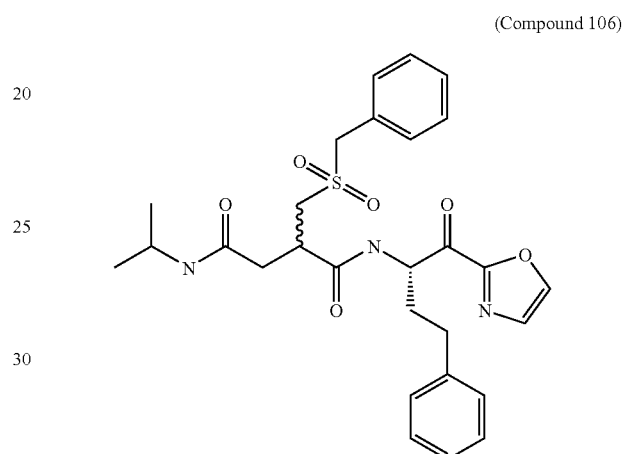

Compound 106 was synthesized according to the following reaction protocol:

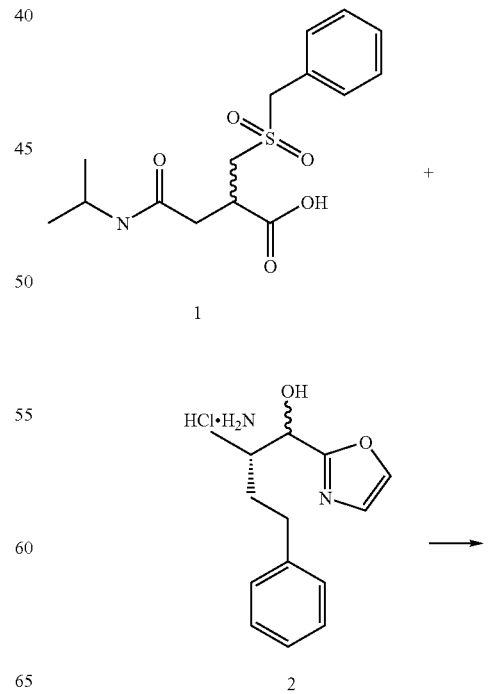

-continued

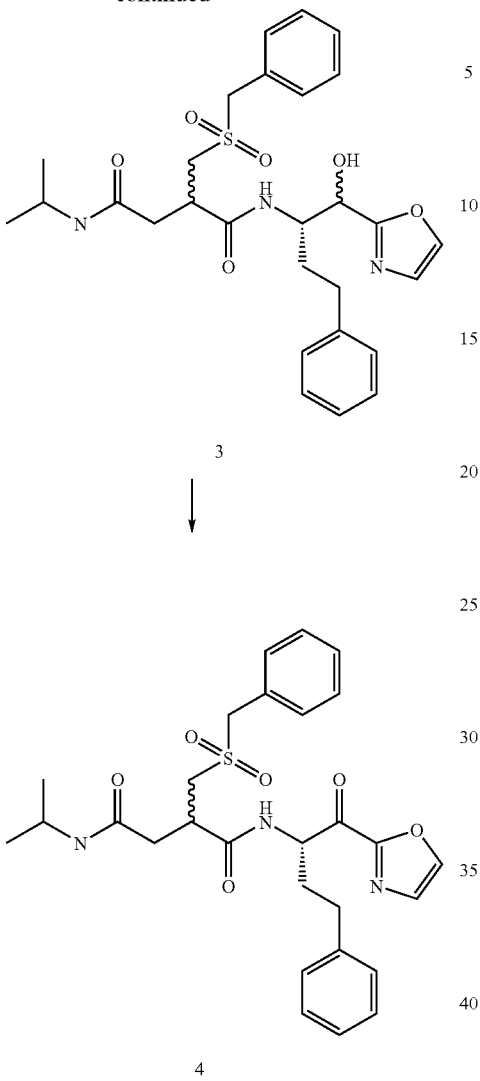

3

↓

4

To a stirring suspension of N-Cyclohexylcarbodiimide, N'-methyl polystyrene resin (1.7 mmole/gram, 0.3529 g, 0.6 mmol) in 10 ml of methylene chloride was added the acid 1 (98.2 mg, 0.3 mmol) and HOBT (69 mg, 0.51 mmol) which was allowed to stir for 15 minutes at room temperature. Compound 2 (80.6 mg, 0.3 mmol) and DIEA (0.1 ml, 0.5 mmol) were added and the reaction was allowed to stir for 5 hours at room temperature. Then silicycle triamine™ (0.42 g, 1.5 mmol) was added and the reaction was stirred overnight at room temperature. The reaction was filtered and the solvent was removed under reduced pressure. The crude product 3 was used without further purification. Crude compound 3 was dissolved in methylene chloride and Dess-Martin reagent (15% in methylene chloride, 1.13 g, 0.6 mmol) was added and the reaction was allowed to stir at room temperature for 3 hours. The excess Dess-Martin reagent was consumed by adding sodium thiosulfate in saturated sodium bicarbonate. The product was extracted with ethyl acetate and washed with brine. The organic layer was dried over magnesium sulfate, filtered and concentrated under reduced pressure. The product was purified using HPLC to yield 15 mg of final compound 4; LCMS retention time 3:07 minutes, M+1(540.2).

Example 51

2-(2-Difluoromethoxy-benzylsulfonylmethyl)-4-morpholin-4-yl-N-[1-(oxazole-2-carbonyl)-3-phenyl-propyl]-4-oxo-butyramide (Compound 107)

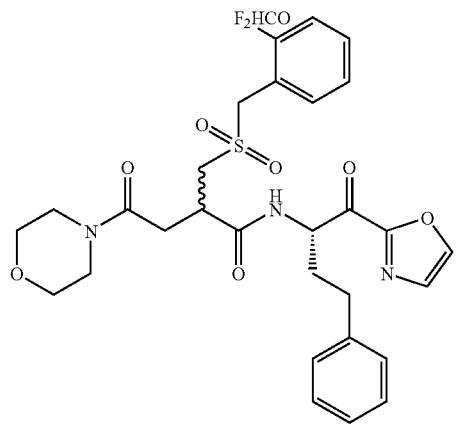

Compound 107 was synthesized according to the following reaction protocol:

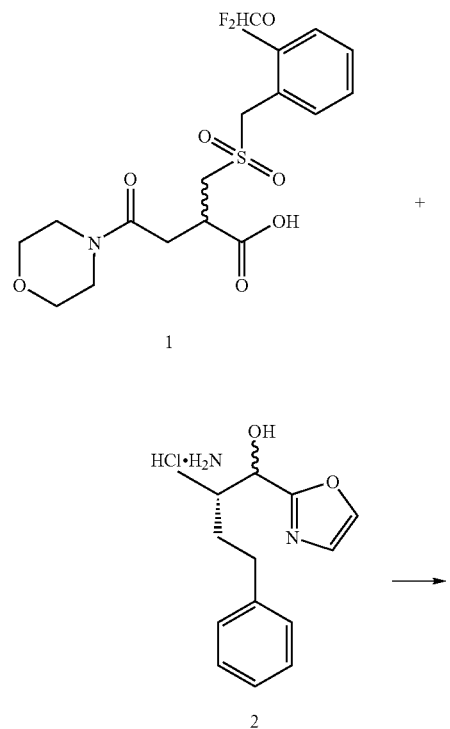

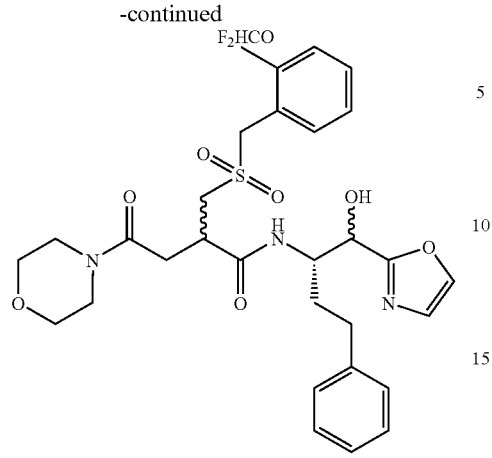

3

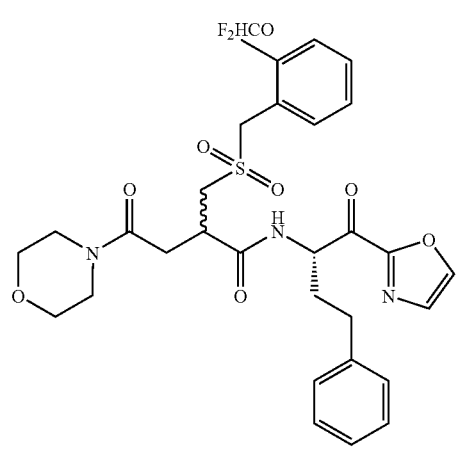

4

To a stirring suspension of N-Cyclohexylcarbodiimide, N'-methyl polystyrene resin (1.7 mmole/gram, 0.2353 g, 0.4 mmol) in 10 ml of methylene chloride was added the acid 1 (84.3 mg, 0.2 mmol) and HOBT (45.9 mg, 0.34 mmol) which was allowed to stir for 15 minutes at room temperature. Compound 2 (53.75 mg, 0.2 mmol) and DIEA (0.068 ml, 0.4 mmol) were added and the reaction was allowed to stir for 5 hours at room temperature. Then silicycle triamine™ (0.28 g, 1.0 mmol) was added and the reaction was stirred overnight at room temperature. The reaction was filtered and the solvent was removed under reduced pressure. The crude product 3 was used without further purification. Crude compound 3 was dissolved in methylene chloride and Dess-Martin reagent (15% in methylene chloride, 1.13 g, 0.6 mmol) was added and the reaction was allowed to stir at room temperature for 3 hours. The excess Dess-Martin reagent was consumed by adding sodium thiosulfate in saturated sodium bicarbonate. The product was extracted with ethyl acetate and washed with brine. The organic layer was dried over magnesium sulfate, filtered and concentrated under reduced pressure. The product was purified using HPLC to yield 6 mg of final compound 4; LCMS retention time 3:09 minutes, M+1(634.4).

Example 52

2-(2-Methyl-propane-1-sulfonylmethyl)-4-morpholin-4-yl-N-[1-(oxazole-2-carbonyl)-3-phenyl-propyl]-4-oxo-butyramide (Compound 108)

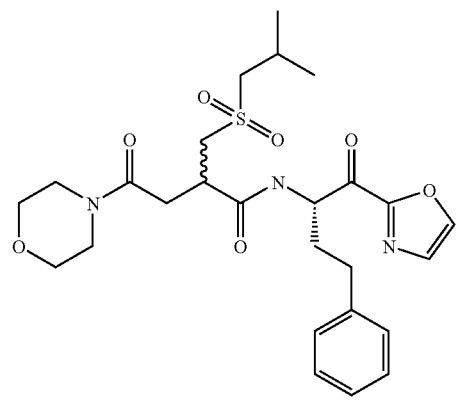

Compound 108 was synthesized according to the following reaction protocol:

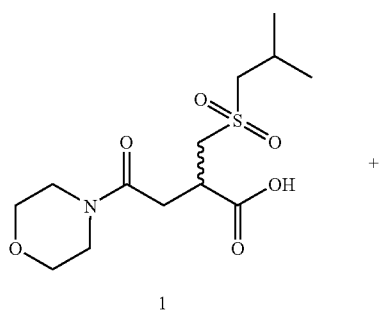

1

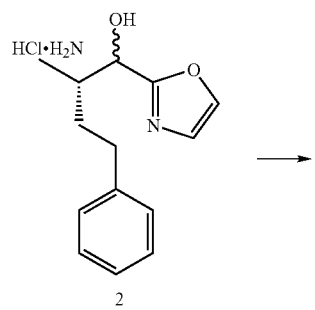

2

1481

-continued

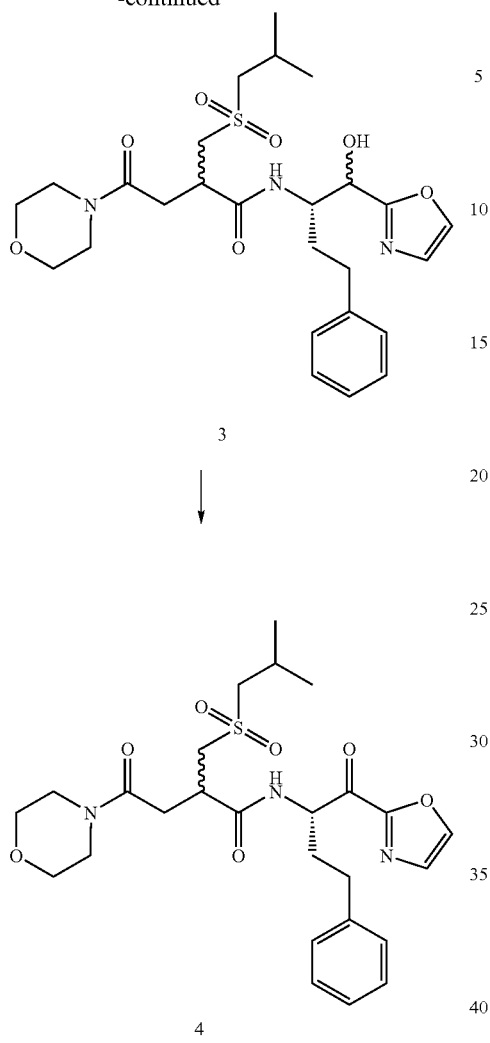

3

↓

4

To a stirring suspension of N-Cyclohexylcarbodiimide, N'-methyl polystyrene resin (1.7 mmole/gram, 0.2353 g, 0.4 mmol) in 10 ml of methylene chloride was added the acid 1 (64.3 mg, 0.2 mmol) and HOBT (45.9 mg, 0.34 mmol) which was allowed to stir for 15 minutes at room temperature. Compound 2 (53.75 mg, 0.2 mmol) and DIEA (0.068 ml, 0.4 mmol) were added and the reaction was allowed to stir for 5 hours at room temperature. Then silicycle triamine™ (0.28 g, 1.0 mmol) was added and the reaction was stirred overnight at room temperature. The reaction was filtered and the solvent was removed under reduced pressure. The crude product 3 was used without further purification. Crude compound 3 was dissolved in methylene chloride and Dess-Martin reagent (15% in methylene chloride, 1.13 g, 0.6 mmol) was added and the reaction was allowed to stir at room temperature for 3 hours. The excess Dess-Martin reagent was consumed by adding sodium thiosulfate in saturated sodium bicarbonate. The product was extracted with ethyl acetate and washed with brine. The

1482 organic layer was dried over magnesium sulfate, filtered and concentrated under reduced pressure. The product was purified using HPLC to yield 25.7 mg of final compound 4; LCMS retention time 2:89 minutes, M+1(534.4).

Example 53

2-Cyclopropylmethylsulfonylmethyl-4-morpholin-4-yl-N-[1-(oxazole-2-carbonyl)-3-phenyl-propyl]-4-oxo-butyramide (Compound 109)

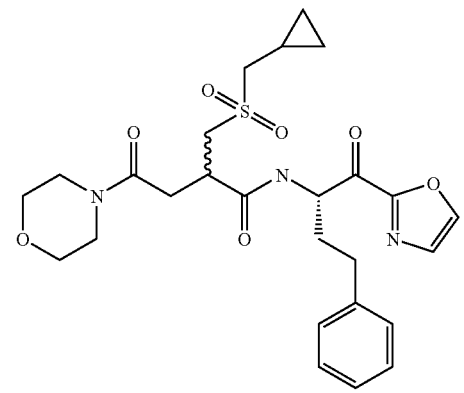

Compound 109 was synthesized according to the following reaction protocol:

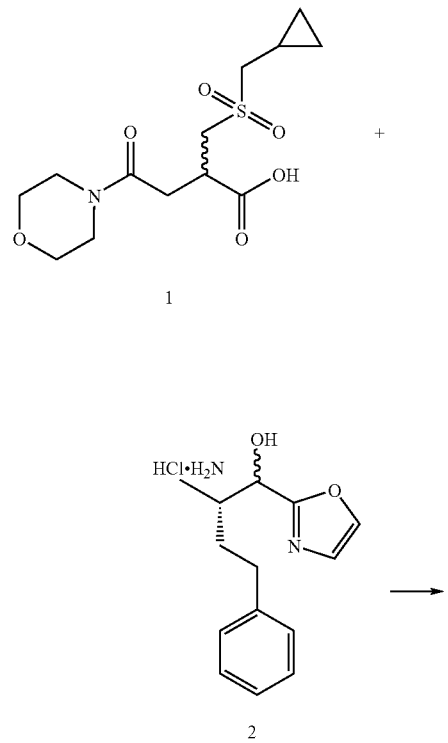

-continued

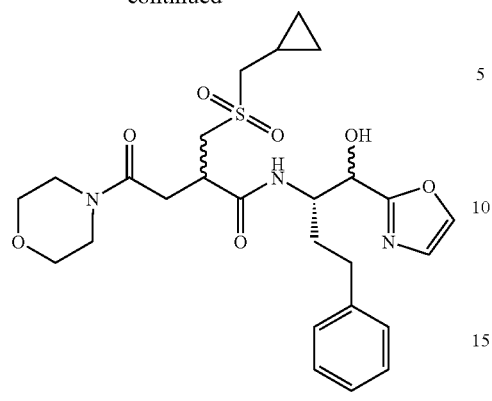

3

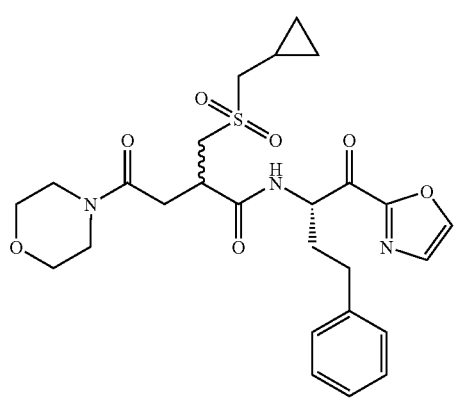

4

To a stirring suspension of N-Cyclohexylcarbodiimide, N'-methyl polystyrene resin (1.7 mmole/gram, 0.2353 g, 0.4 mmol) in 10 ml of methylene chloride was added the acid 1 (63.9 mg, 0.2 mmol) and HOBT (45.9 mg, 0.34 mmol) which was allowed to stir for 15 minutes at room temperature. Compound 2 (53.75 mg, 0.2 mmol) and DIEA (0.068 ml, 0.4 mmol) were added and the reaction was allowed to stir for 5 hours at room temperature. Then silicycle triamine™ (0.28 g, 1.0 mmol) was added and the reaction was stirred overnight at room temperature. The reaction was filtered and the solvent was removed under reduced pressure. The crude product 3 was used without further purification. Crude compound 3 was dissolved in methylene chloride and Dess-Martin reagent (15% in methylene chloride, 1.13 g, 0.6 mmol) was added and the reaction was allowed to stir at room temperature for 3 hours. The excess Dess-Martin reagent was consumed by adding sodium thiosulfate in saturated sodium bicarbonate. The product was extracted with ethyl acetate and washed with brine. The organic layer was dried over magnesium sulfate, filtered and concentrated under reduced pressure. The product was purified using HPLC to yield 11.6 mg of final compound 4; LCMS retention time 2:77 minutes, M+1 (532.4).

Example 54

N-[1-(Benzooxazole-2-carbonyl)-butyl]-2-benzylsulfonyl-3-(tetrahydro-pyran-4-yloxymethyl)-propionamide (Compound 110)

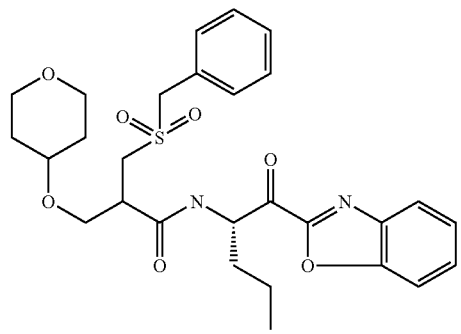

Diisopropylethylamine (0.184 ml, 1.05 mmol) was added to a mixture of 3-benzylsulfonyl-2-(tetrahydro-pyran-4-yloxymethyl)-propionic acid (362 mg, 1.05 mmol), prepared as in reference 27, and 2-amino-1-benzooxazol-2-yl-pentan-1-ol (238 mg, 1.05 mmol) and HATU (402 mg, 1.05 mmol) in DMF (10 ml) and stirred at room temperature overnight. Solvent was evaporated under reduced pressure, crude extract was taken up in ethyl acetate (30 ml) and washed with 1N HCl, saturated NaHCO₃ and brine. After drying over MgSO₄ the solvent was removed by rotary evaporation and the residue chromatographed on silica eluting with ethyl acetate/heptane mixture to give N-[(S)-1-yloxy)-propionamide (Yield: 258 mg); MS: 545 (M+1); LCMS retention time 3.71 and 3.76 minutes.

A solution of N-[(S)-1-(benzoxazol-2-yl-hydroxy-methyl)-butyl]-2-benzylsulfonylmethyl-3-(tetrahydro-pyran-4-yloxy)-propionamide (243 mg, 0.45 mmol) methylene chloride (8 ml) was treated with Dess-Martin periodinane (190 mg, 0.45 mmol) at room temperature for 2 hours. Washed with 0.26M solution of Na₂SO₃, NaHCO₃ and brine. After drying over MgSO₄ the solvent was removed by rotary evaporation and the residue chromatographed on silica eluting with ethyl acetate/heptane mixture to give N-[1-(benzooxazole-2-carbonyl)-butyl]-2-benzylsulfonyl-3-(tetrahydro-pyran-4-yloxymethyl)-propionamide as off white solid (Yield: 60 mg); MS: 543 (M+1); LCMS retention time 4.1 minutes.

Example 55

N-[1-(Benzooxazole-2-carbonyl)-butyl]-3-ethanesulfonyl-2-(tetrahydro-pyran-4-yloxymethyl)-propionamide (Compound 111)

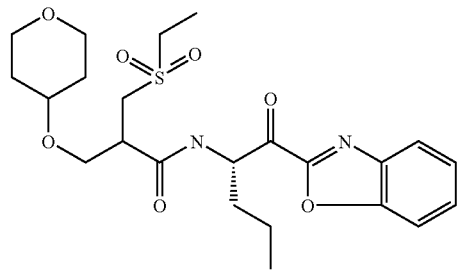

By following the method for Example 54 but substituting the required carboxylic acid with 3-ethyl sulfonyl-2-(tetrahydro-pyran-4-yloxymethyl)-propionic acid, as prepared in reference 27b, N-[1-(benzooxazole-2-carbonyl)-butyl]-3-ethanesulfonyl-2-(tetrahydro-pyran-4-yloxymethyl)-propionamide was prepared. MS: 481 (M+1); LCMS retention time 3.7 minutes.

Example 56

N-(1-Benzenesulfonyl-3-oxo-azepan-4-yl)-2-cyclopropylmethylsulfonylmethyl-4-morpholin-4-yl-4-oxo-butyramide (Compound 112)

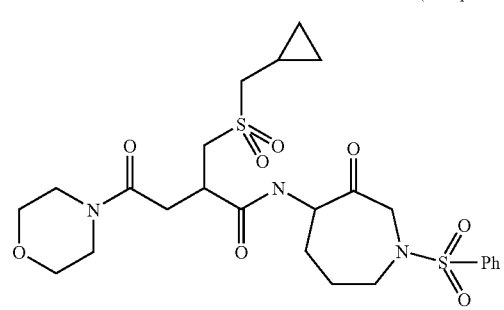

Compound 112 was prepared by the following protocol. The circle symbolizes the polystyrene backbone while the square symbolizes the silicium dioxide backbone:

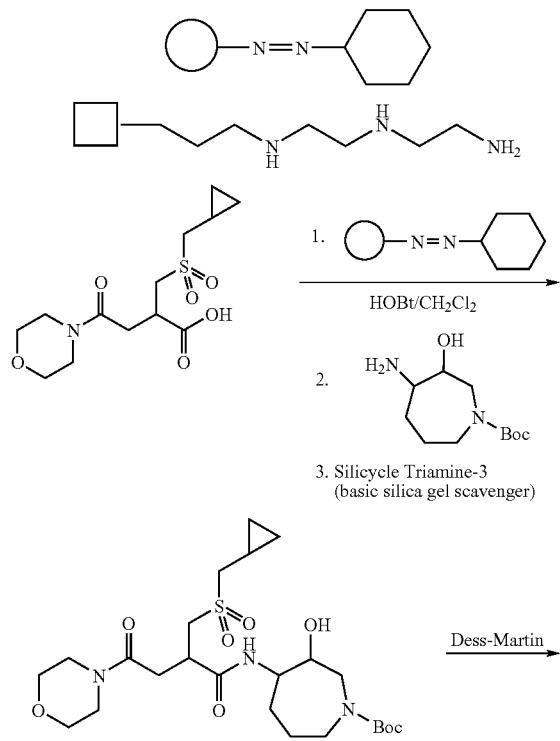

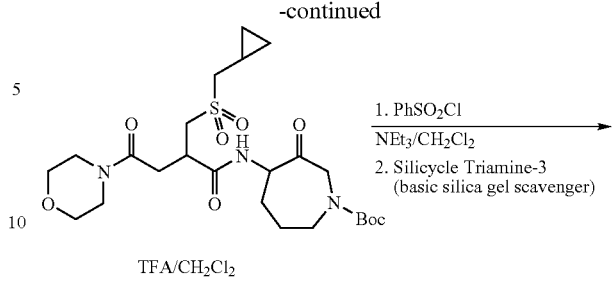

-continued

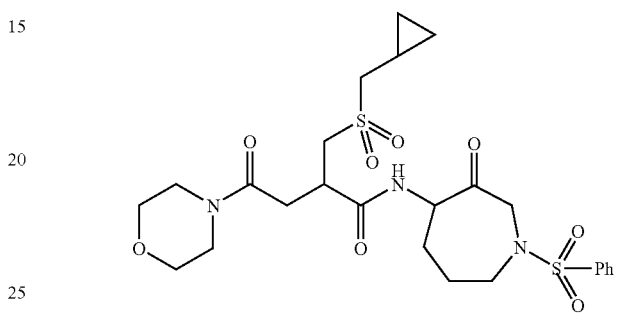

1.16 mol-equivalents of the acid were dissolved in dichloromethyl. N-Cyclohexylcarbodiimide, N'-methylpolystyrene (2 mol-equivalents) and hydroxybenzotriazole (1.72 mol-equivalents) were added and the resulting reaction mixture stirred for 10 minutes. 4-Amino-3-hydroxy-azepane-1-carboxylic acid tert-butyl ester (1 mol-equivalent) was added and stirring continued for 21 hours. Silicycle-Triamine-3™ was added and the resulting mixture stirred for six hours. The mixture was filtered under suction and the filtrate concentrated under vacuum.

The alcohol was dissolved in dichloromethyl and 2 mol-equivalents of Dess-Martin periodinane were added to the solution. The reaction mixture was stirred for one hour. Equal volumes of saturated sodium thiosulfate solution and sat sodium bicarbonate solution were added and the phases separated. The aqueous phase was extracted three times with dichloromethyl. The combined organic phases were washed with saturated sodium bicarbonate solution and saturated sodium chloride solution. The solution was dried with magnesium sulfate and the solvents evaporated.

The azepanone-1-carboxylic acid tert-butyl ester was dissolved in a dichloromethyl solution (20 vol-%) of trifluoroacetic acid. After stirring for one hour dichloromethyl was removed under reduced pressure and trifluoroacetic acid under high vacuum. The solid residue was re-dissolved in dichloromethyl and five mol-equivalent of triethylamine were added. 1.2 mol-equivalent of benzenesulfonyl chloride were added and the reaction mixture stirred for four hours. 12 mol-equivalents of Silicycle Triamine™ were added and stirring continued for two hours. The mixture was filtered under suction and the dichloromethyl evaporated under reduced pressure. The crude product was purified via preparative HPLC yielding N-(1-benzenesulfonyl-3-oxo-azepan-4-yl)-2-cyclopropylmethylsulfonylmethyl-4-morpholin-4-yl-4-oxo-butyramide as an off-white solid; LC/MS retention time 2.61 minutes, m/z=570 (M+H).

The following examples were prepared according to methods described in Example 56:

2-Cyclopropylmethylsulfonylmethyl-N-{(S)-1-[(R)-hydroxy-(3-phenyl-1,2,4-oxadiazol-5-yl)-methyl]-propyl}-4-morpholin-4-yl-4-oxo-butyramide (Compound 122)

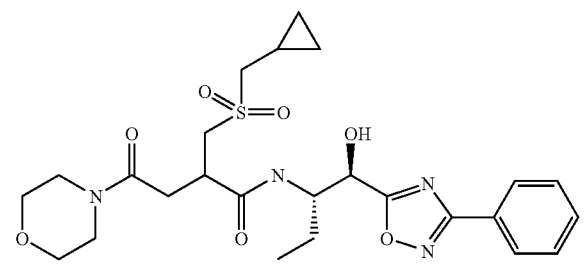

Tan solid; LC/MS retention time 3.456 minutes (TIC), m/z=557 (M+Na).

N-{(S)-1-[(R)-hydroxy-(3-phenyl-1,2,4-oxadiazol-5-yl)-methyl]-propyl}-2-(2-methyl-propane-1-sulfonylmethyl)-4-morpholin-4-yl-4-oxo-butyramide (Compound 123)

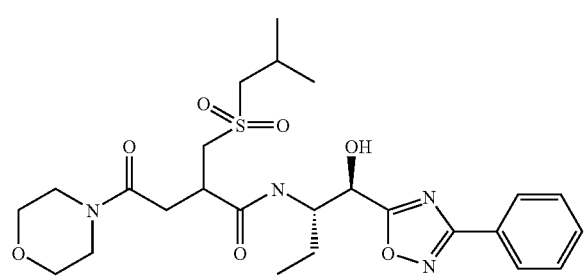

Tan solid; LC/MS retention time 3.594 minutes (TIC), m/z=559 (M+Na).

2-(2-Morpholin-4-yl-2-oxo-ethyl)-5-phenyl-pentanoic acid {(S)-1-[(R)-hydroxy-(3-phenyl-1,2,4-oxadiazol-5-yl)-methyl]-propyl}-amide (Compound 124)

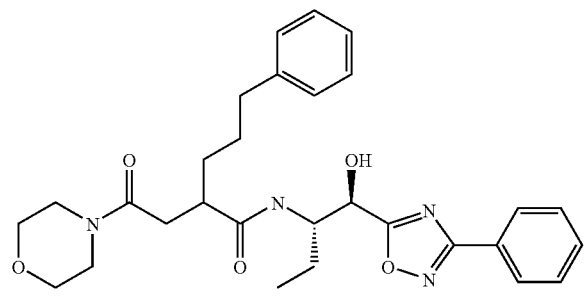

Tan solid; LC/MS retention time 3.379 minutes (TIC), m/z=521 (M+H).

2-Cyclopropylmethylsulfonylmethyl-4-morpholin-4-yl-4-oxo-N-[(S)-1-(3-phenyl-1,2,4-oxadiazole-5-carbonyl)-propyl]-butyramide (Compound 125)

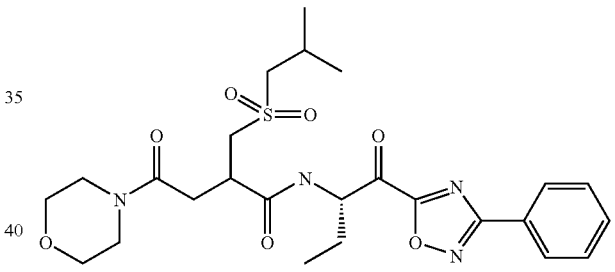

Tan solid; LC/MS retention time 2.976 minutes (TIC), m/z=533 (M+H).

2-(2-methyl-propane-1-sulfonylmethyl)-4-morpholin-4-yl-4-oxo-N-[(S)-1-(3-phenyl-1,2,4-oxadiazole-5-carbonyl)-propyl]-butyramide (Compound 126)

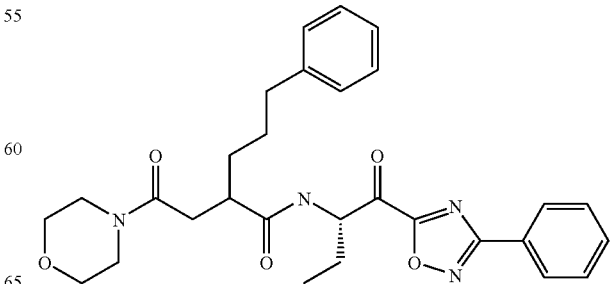

Tan solid; LC/MS retention time 3.433 minutes (TIC), m/z=535 (M+H).

2-(2-Morpholin-4-yl-2-oxo-ethyl)-5-phenyl-pentanoic acid, (S)-1-(3-phenyl-1,2,4-oxadiazole-5-carbonyl)-propyl}-amide (Compound 127)

Tan solid; LC/MS retention time 3.762 minutes (TIC), m/z=519 (M+H).

Example 57

3-Hydroxy-4-(4-morpholin-4-yl-4-oxo-2-benzylsulfonylmethyl-butyrylamino)-azepane-1-carboxylic acid tert-butyl ester (Compound 113)

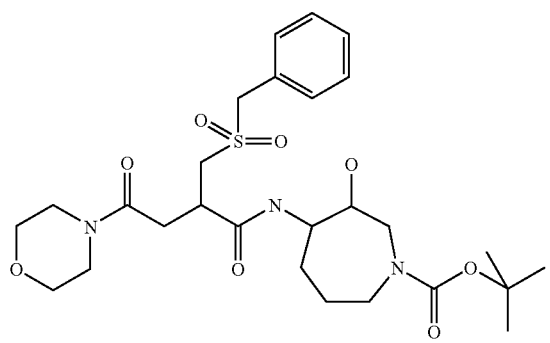

Tan solid prepared according to example 56; LC/MS retention time 2.985 minutes (TIC), m/z=568 (M+H) and 590 (M+Na).

Example 58

4-(2-Cyclopropylmethylsulfonylmethyl-4-morpholin-4-yl-4-oxo-butyrylamino)-3-hydroxy-azepane-1-carboxylic acid tert-butyl ester (Compound 114)

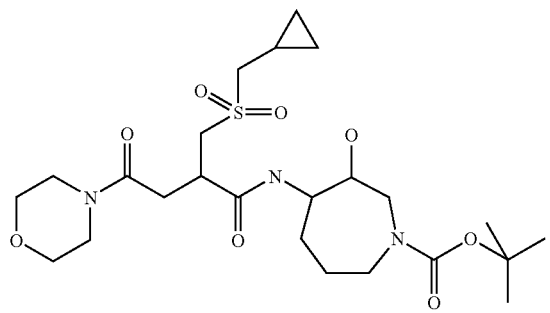

Tan solid prepared according example 56; LC/MS retention time 2.786 minutes (TIC), m/z=532 (M+H) and 554 (M+Na).

Example 59

3-Hydroxy-4-[2-(2-methyl-propane-1-sulfonylmethyl)-4-morpholin-4-yl-4-oxo-butyrylamino-azepane-1-carboxylic acid tert-butyl ester (Compound 115)

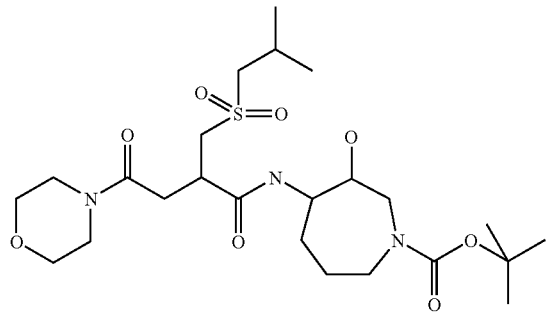

Tan solid prepared according example 56; LC/MS retention time 2.903 minutes (TIC), m/z=534 (M+H).

Example 60

4-(4-Morpholin-4-yl-4-oxo-2-benzylsulfonylmethyl-butyrylamino)-3-oxo-azepane-1-carboxylic acid tert-butyl ester (Compound 116)

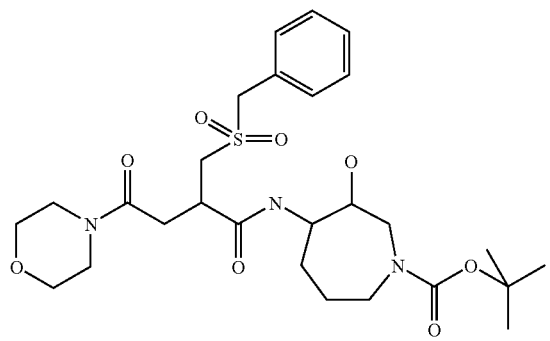

Tan solid prepared according example 56; LC/MS retention time 3.163 minutes (TIC), m/z=566 (M+H).

Example 61

4-(2-Cyclopropylmethylsulfonylmethyl-4-morpholin-4-yl-4-oxo-butyrylamino)-3-oxo-azepane-1-carboxylic acid tert-butyl ester

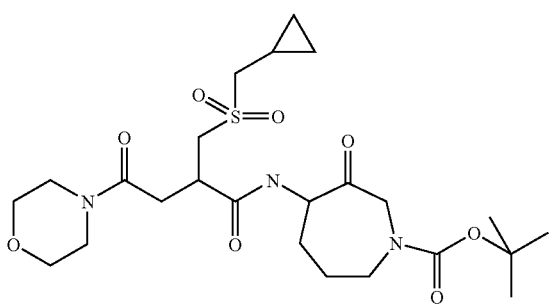

Tan solid prepared according to example 56; LC/MS retention time 2.965 minutes (TIC), m/z=530 (M+H).

Example 62

4-[2-(2-Methyl-1-propane-1-sulfonylmethyl)-4-morpholin-4-yl-4-oxo-butyrylamino]-3-oxo-azepane-1-carboxylic acid tert-butyl ester

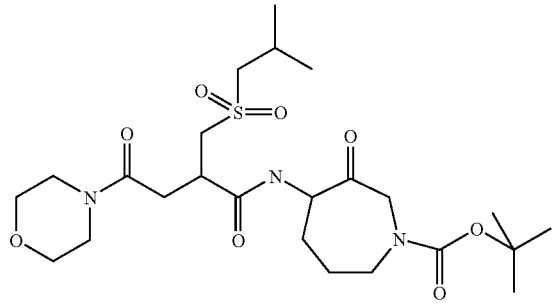

Tan solid prepared according to example 56; LC/MS retention time 3.083 minutes (TIC), m/z=532 (M+H).

Example 63

N-(1-Benzenesulfonyl-3-oxo-azepan-4-yl)-4-morpholin-4-yl-4-oxo-2-benzylsulfonylmethyl-butyramide (Compound 119)

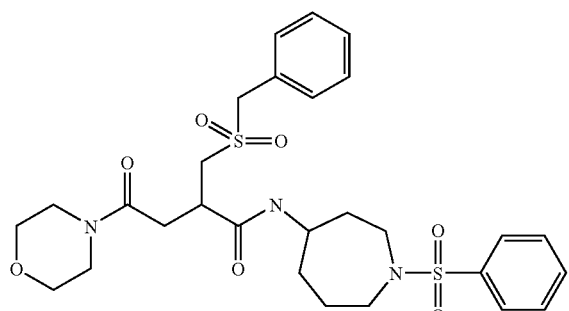

Off-white solid prepared according to example 56; LC/MS retention time 2.83 minutes TIC), m/z=606 (M+H).

Example 64

N-(1-Benzenesulfonyl-3-oxo-azepan-4-yl)-2-(2-methyl-propane-1-sulfonylmethyl)-4-morpholin-4-yl-4-oxo-butyramide (Compound 120)

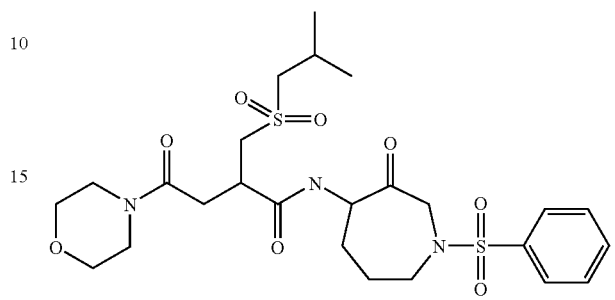

Off-white solid prepared according example 56; LC/MS retention time 2.72 minutes (TIC), m/z=572 (M+H).

Example 65

N-[(1S)-1-(Benzooxazol-2-yl-hydroxy-methyl)-3-phenyl-propyl]-2-cyclopropylmethylsulfonylmethyl-4-morpholin-4-yl-4-oxo-butyramide (Compound 121)

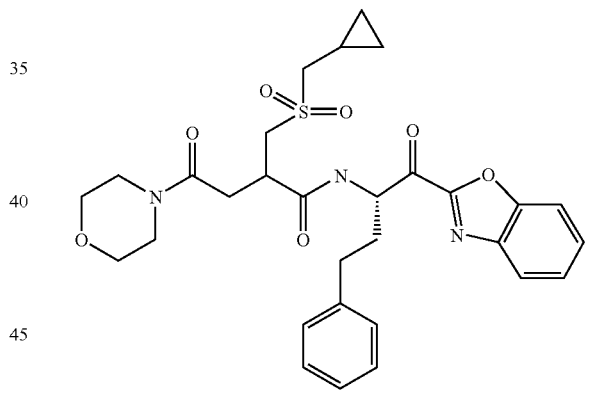

Compound 121 was prepared according to the following reaction scheme:

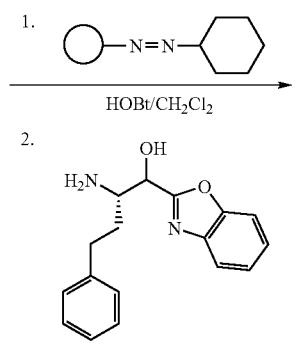

1.

HOBt/CH₂Cl₂

2.

3. Silicycle Triamine-3
(basic silica gel scavenger)

1493

-continued

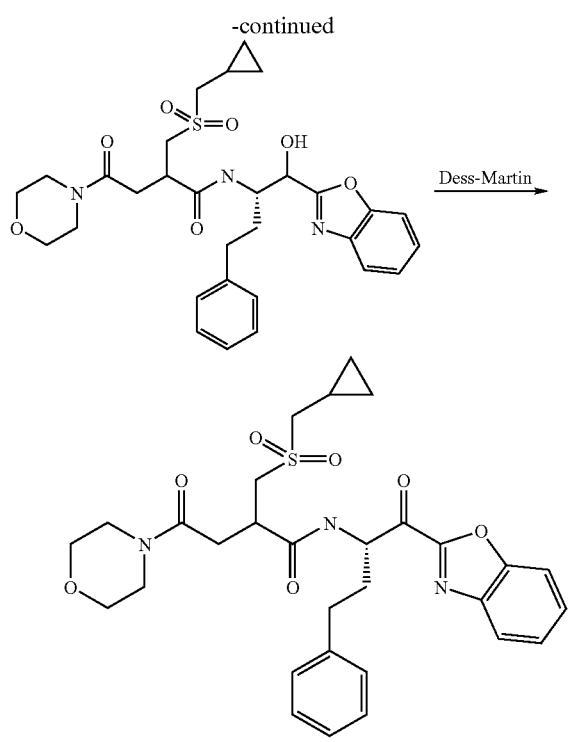

0.25 mmol (1.16 mol-equivalent) of 2-cyclopropylmethylsulfonylmethyl-4-morpholin-4-yl-4-oxo-butyric acid was dissolved in 10 ml dichloromethyl. 252 mg, 0.43 mmol N-cyclohexylcarbodiimide, N'-methylpolystyrene (2 mol-equivalents) and 50 mg, 0.37 mmol hydroxybenzotriazole (1.72 mol-equivalents) were added and the resulting reaction mixture stirred for 10 minutes. 61 mg, 0.215 mmol 2-amino-1-benzooxazol-2-yl-4-phenyl-butan-1-ol (1 mol-equivalents) was added and stirring continued for 21 hours. 510 mg, 2.15 mmol Silicycle-Triamine-3™ was added and the resulting mixture stirred for 6 hours. The mixture was filtered under suction and the filtrate concentrated under vacuum yielding 83 mg, 0.142 mmol (66%) of N-[(1S)-1-(Benzooxazol-2-yl-hydroxy-methyl)-3-phenyl-propyl]-2-cyclopropylmethylsulfonyl-0methyl-4-morpholin-4-yl-4-oxo-butyramide as a tan solid; LC/MS retention time 3.256 min (TIC), m/z=584 (M+H).

Example 66

(R)-2-((S)-1-Hydroxy-2-morpholin-4-yl-2-oxo-ethyl)-5-phenyl-pentanoic acid, 1-(benzoxazole-2-carbonyl)-propyl]-amide (Compound 128)

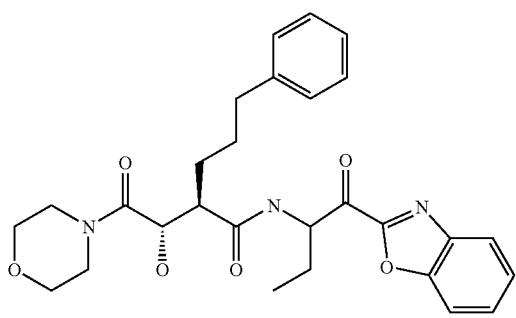

1494

PyBOP (126 mg, 0.24 mmol), DIPEA (0.096 ml, 0.55 mmol) and 2-Amino-1-benzooxazol-2-yl-butan-1-one hydrochloride (53 mg, 0.22 mmol) were added to a solution of (R)-2-((S)-1-Hydroxy-2-morpholin-4-yl-2-oxo-ethyl)-5-phenyl-pentanoic acid (70.7 mg, 0.22 mmol) in dry methylene chloride (5 ml) and the reaction mixture was stirred overnight at room temperature. The reaction was concentrated under reduced pressure, the residue dissolved in ethyl acetate and washed with water. Organic extract was dried over MgSO$_4$ and evaporated under reduced pressure. Column chromatography on silica eluting with a mixture of ethyl acetate and heptane gave the title compound as white solid (38 mg); $^1$H NMR (CDCl$_3$) δ 1.02 (t, J=7.4 Hz, 3H), 1.97–1.62 (m, 5H), 2.21–2.15 (m, 1H), 2.74–2.59 (m, 3H), 3.65–3.49 (m, 8H), 4.41 (m, 1H), 4.70 (m, 1H), 5.62 (m, 1H), 6.93 (d, J=7.1 Hz) 6.68 (d, J=7.1 Hz, 1H), 7.33–7.13 (m, 5H), 7.49 (t, J=8 Hz, 1H), 7.57 (t, J=8 Hz, 1H), 7.66 (d, J=5.9, 1H), 7.92 (d, J=8 Hz, 1H); MS: 508(MH$^+$); LC/MS retention time was 3.05 minutes.

Example 67

(R)-5-(2-Difluoromethoxy-phenyl)-2-((S)-1-hydroxy-2-morpholin-4-yl-2-oxo-ethyl)-pentanoic acid, 1-(benzoxazole-2-carbonyl)-propyl]-amide (Compound 129)

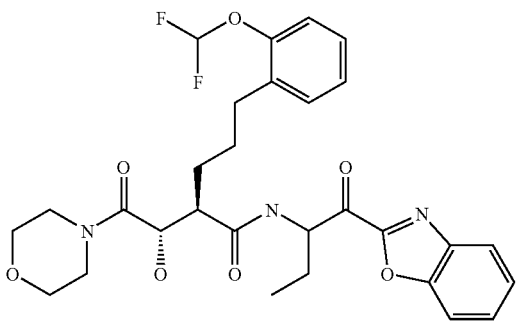

Similarly prepared according to the procedure in Example 66 but using (R)-5-(2-difluoromethoxy-phenyl)-2-((S)-1-hydroxy-2-morpholin-4-yl-2-oxo-ethyl)-pentanoic acid as the acidic component; $^1$H NMR (CDCl$_3$) δ 1.06 (t, J=7.5 Hz, 3H), 1.97–1.63 (m, 5H), 2.23–2.14 (m, 1H), 2.79–2.68 (m, 3H), 3.75–3.50 (m, 8H), 4.42 (m, 1H), 4.81–4.62 (m, 1H), 5.61 (m, 1H), 6.53 (t, J=74 Hz, 1H), 6.73 (d, J=7.1 Hz), 6.98 (d, J=7.1 Hz, 1H), 7.24–7.06 (m, 4H), 7.59–7.49 (m, 2H), 7.69–7.64 (m, 1H), 7.91 (d, J=7.9 Hz, 1H); MS: 574 (MH$^+$).

Example 68

4-Morpholin-4-yl-N-[1-(oxazole-2-carbonyl)-cyclopropyl]-4-oxo-2-benzylsulfonyl methyl-butyramide

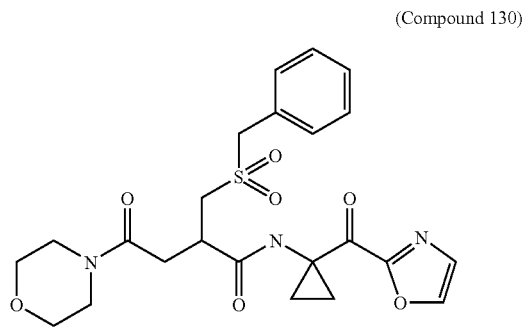

(Compound 130)

Similarly prepared according to the procedure in Example 66 but using 4-morpholin-4-yl-4-oxo-2-benzylsulfonylmethyl-butyric acid as the acidic component and (1-Aminocyclopropyl)-oxazol-2-yl-methanone hydrochloride as the basic component; MS: 490 (MH$^+$); LC/MS, retention time 2.44 minutes.

Example 69

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at ambient temperature. Z-Val-Val-Arg-AMC (9 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 70

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at ambient temperature. Z-FR-AMC (20 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 71

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (4 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 72

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (1 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested according to the above-described assays for protease inhibition and observed to exhibit selective cathepsin S inhibitory activity. For example, the compounds of the invention were found to inhibit cathepsin S protease activity at concentrations that are least 50 fold less than those concentrations required to produce an equiactive inhibition of cathepsin K protease activity. The apparent inhibition constants ($K_i$) for compounds of the invention, against Cathepsin S, were in the range from about $10^{-10}$ M to about $10^{-7}$ M.

Example 73

Representative Pharmaceutical Formulations Containing a Compound of Formula I

| ORAL FORMULATION | |
| --- | --- |
| Compound of Formula I | 10–100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
| --- | --- |
| Compound of Formula I | 0.1–10 mg |
| Dextrose Monohydrate | q.s. to make isotonic |

-continued

| INTRAVENOUS FORMULATION | |
|---|---|
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of Formula I | 1% |
| Microcrystalline Cellulose | 73% |
| Stearic Acid | 25% |
| Colloidal Silica | 1%. |

The invention claimed is:
1. A compound of Formula I:

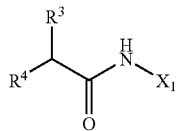

I in which:
   $X^1$ is —$C(R^1)(R^2)X^2$;
   $X^2$ is cyano, —CHO, —$C(R^7)(R^8)R^5$, —$C(R^7)(R^8)CF_3$, —$C(R^7)(R^8)CF_2CF_2R^9$, —CH=$CHS(O)_2R^5$, —$C(R^7)(R^8)CF_2C(O)NR^5R^6$, —$C(R^7)(R^8)C(R^7)(R^8)NR^5R^6$, —$C(R^7)(R^8)C(R^7)(R^8)OR^5$, —$C(R^7)(R^8)CH_2OR^5$, —$C(R^7)(R^8)CH_2N(R^6)SO_2R^5$, —$C(R^7)(R^8)C(R^7)(R^8)N(R^6)(CH_2)_2OR^6$, —$C(R^7)(R^8)C(R^7)(R^8)N(R^6)CH_2)_2NR^6$ or —$C(R^7)(R^8)C(R^7)(R^8)R^5$; wherein $R^5$ is ($C_{1-4}$)alkyl, ($C_{6-10}$)aryl($C_{0-6}$)alkyl, hetero($C_{4-10}$)aryl($C_{0-6}$)alkyl, ($C_{4-10}$)cycloalkyl($C_{0-6}$)alkyl or hetero($C_{4-10}$)cycloalkyl($C_{0-6}$)alkyl wherein hetero($C_{4-10}$)aryl or hetero($C_{4-10}$)cycloalkyl is pyran, thiopyran, pyrimidine, thiazole, isothiazole, pyridine, furan, imidazole, isoxazole, oxadiazole, oxazole or triazole; $R^6$ is hydrogen or ($C_{1-6}$)alkyl; $R^7$ is hydrogen or ($C_{1-4}$)alkyl and $R^8$ is hydroxy or $R^7$ and $R^8$ together form oxo; $R^9$ is hydrogen, halo, ($C_{1-4}$)alkyl, or ($C_{5-10}$)aryl($C_{0-6}$)alkyl;
   wherein within $X^1$ any cycloalkyl, is substituted or unsubstituted;
   $R^1$ and $R^2$ are both fluoro; or
   $R^1$ is hydrogen or ($C_{1-6}$)alkyl and $R^2$ is selected from the group consisting of hydrogen, ($C_{1-6}$)alkyl, cyano, —$X^4NR^{12}R^{12}$, —$X^4NR^{12}C(O)R^{12}$, —$X^4NR^{12}C(O)OR^{12}$, —$X^4NR^{12}C(O)NR^{12}R^{12}$, —$X^4NR^{12}C(NR^{12})NR^{12}R^{12}$, —$X^4OR^{13}$, —$X^4SR^{13}$, —$X^4C(O)OR^{12}$, —$X^4C(O)R^{13}$, —$X^4OC(O)R^{13}$, —$X^4C(O)NR^{12}R^{12}$, —$X^4S(O)_2NR^{12}R^{12}$, —$X^4NR^{12}S(O)_2R^{13}$, —$X^4P(O)(OR^{12})OR^{12}$, —$X^4OP(O)(OR^{12})OR^{12}$, —$X^4S(O)R^{14}$, —$X^4S(O)_2R^{14}$, —$R^{15}$, —$X^4OR^{15}$, —$X^4SR^{15}$, —$X^4S(O)R^{15}$, —$X^4S(O)_2R^{15}$, —$X^4C(O)R^{15}$, —$X^4C(O)OR^{15}$, —$X^4OC(O)R^{15}$, —$X^4NR^{15}R^{12}$, —$X^4NR^{12}C(O)R^{15}$, —$X^4NR^{12}C(O)OR^{15}$, —$X^4C(O)NR^{15}R^{12}$, —$X^4S(O)_2NR^{15}R^{12}$, —$X^4NR^{12}S(O)_2R^{15}$, —$X^4NR^{12}C(O)NR^{15}R^{12}$ and —$X^4NR^{12}C(NR^{12})NR^{15}R^{12}$, wherein $X^4$ is a bond or ($C_{1-6}$)alkylene, $R^{12}$ at each occurrence independently is hydrogen or ($C_{1-6}$)alkyl, $R^{13}$ is hydrogen, ($C_{1-6}$)alkyl or halo-substituted($C_{1-6}$)alkyl, $R^{14}$ is ($C_{1-6}$)alkyl or halo-substituted($C_{1-6}$)alkyl, and $R^{15}$ is ($C_{3-10}$)cycloalkyl($C_{0-6}$)alkyl, ($C_{6-10}$)aryl($C_{0-6}$)alkyl, or ($C_{9-12}$)bicycloaryl($C_{0-6}$)alkyl;
   or $R^1$ and $R^2$ taken together with the carbon atom to which both $R^1$ and $R^2$ are attached form ($C_{3-8}$)cycloalkylene; wherein $R^2$, and said cycloalkylene may be substituted further with 1 to 3 radicals independently selected from ($C_{1-6}$)alkyl, cyano, halo, halo-substituted($C_{1-4}$)alkyl, nitro, —$X^4NR^{12}R^{12}$, —$X^4NR^{12}C(O)R^{12}$, —$X^4NR^{12}C(O)OR^{12}$, —$X^4NR^{12}C(O)NR^{12}R^{12}$, —$X^4NR^{12}C(NR^{12})N^{12}R^{12}$, —$X^4OR^{13}$, —$X^4SR^{13}$, —$X^4C(O)OR^{12}$, —$C(O)R^{13}$, —$X^4OC(O)R^{13}$, —$X^4C(O)NR^{12}R^{12}$, —$X^4S(O)_2NR^{12}R^{12}$, —$X^4NR^{12}S(O)_2R^{13}$, —$X^4P(O)(OR^{12})OR^{12}$, —$X^4OP(O)(OR^{12})OR^{12}$, —$X^4S(O)R^{14}$ and —$X^4S(O)_2R^{14}$, wherein —$X^4$, $R^{12}$, $R^{13}$ and $R^{14}$ are as defined above;
   $R^3$ is —$C(R^{16})(R^{17})X^7$, wherein $R^{16}$ and $R^{17}$ are hydrogen, ($C_{1-6}$)alkyl or fluoro, or $R^{16}$ is hydrogen and $R^{17}$ is hydroxyl; and $X^7$ is selected from —$X^4NR^{12}R^{12}$, —$X^4NR^{12}C(O)R^{12}$, —$X^4NR^{12}C(O)OR^{12}$, —$X^4NR^{12}C(O)NR^{12}R^{12}$, —$X^4NR^{12}C(NR^{12})NR^{12}R^{12}$, —$X^4OR^{13}$, —$X^4SR^{13}$, —$X^4C(O)OR^{12}$, —$X^4C(O)R^{13}$, —$X^4OC(O)R^{13}$, —$X^4C(O)NR^{12}R^{12}$, —$X^4S(O)_2NR^{12}R^{12}$, —$X^4NR^{12}S(O)_2R^{13}$, —$X^4P(O)(OR^{12})OR^{12}$, —$X^4OP(O)(OR^{12})OR^{12}$, —$X^4S(O)R^{14}$, —$X^4S(O)_2R^{14}$, —$R^{15}$, —$X^4OR^{15}$, —$X^4SR^{15}$, —$X^4S(O)R^{15}$, —$X^4S(O)_2R^{15}$, —$X^4C(O)R^{15}$, —$X^4C(O)OR^{15}$, —$X^4OC(O)R^{15}$, —$X^4NR^{15}R^{12}$, —$X^4NR^{12}C(O)R^{15}$, —$X^4NR^{12}C(O)OR^{15}$, —$X^4C(O)NR^{15}R^{12}$, —$X^4S(O)_2NR^{15}R^{12}$, —$X^4NR^{12}S(O)_2R^{15}$, —$X^4NR^{12}C(O)NR^{15}R^{12}$ and —$X^4NR^{12}C(NR^{12})NR^{15}R^{12}$, wherein $X^4$, $R^{12}$, $R^{13}$, $R^{14}$ and $R^{15}$ are as defined above;
   $R^4$ is —$C(R^{16})(R^{17})X^7$, wherein $R^{16}$ and $R^{17}$ are hydrogen, ($C_{1-6}$)alkyl or fluoro, or $R^{16}$ is hydrogen and $R^{17}$ is hydroxy and $X^7$ is selected from —$R^{15}$, —$X^4OR^{15}$, —$X^4SR^{15}$, —$X^4S(O)R^{15}$, —$X^4NR^{12}C(O)OR^{15}$, —$X^4C(O)NR^{15}R^{12}$, —$X^4S(O)_2NR^{15}R^{12}$, —$X^4NR^{12}S(O)_2R^{15}$, —$X^4NR^{12}C(O)NR^{15}R^{12}$ and —$X^4NR^{12}C(NR^{12})NR^{15}R^{12}$, wherein $X^4$, $R^{12}$, $R^{13}$ and $R^{14}$ are as defined above for $R^3$ and $R^{15}$ is hetero($C_{3-10}$)cycloalkyl($C_{0-3}$) alkyl wherein said hetero($C_{3-10}$)cycloalkyl($C_{0-3}$) alkyl is morpholinyl,
   wherein within one of $R^3$ or $R^4$ any cycloalkyl or aryl is substituted or unsubstituted and provided that when $X^2$ is cyano and $X^7$ within one of $R^3$ or $R^4$ is —$X^4C(O)R^{13}$ or —$X^4C(O)R^{15}$, wherein $X^4$ is a bond, then $X^7$ within the other of $R^3$ or $R^4$ is limited to —$X^4SR^{15}$, —$X^4S(O)R^{15}$ and —$X^4S(O)_2R^{15}$, wherein $R^{15}$ is as defined above for each of $R^3$ and $R^4$, respectively;
   or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.
2. The compound of claim 1 in which:
   $X^2$ is —CHO, —$C(O)R^5$, —$C(O)CF_3$, —$C(O)CF_2CF_2R^9$ —CH=$CHS(O)_2R^5$, —$C(O)CF_2C(O)NR^5R^6$, —$C(O)C(O)NR^5R^6$, —$C(O)C(O)OR^5$, —$C(O)CH_2OR^5$, —$C(O)CH_2N(R^6)SO_2R^5$, —$C(O)C(O)N(R^6)(CH_2)OR^6$, —$C(O)C(O)N(R^6)(CH_2)_2NR^6$ or —$C(O)C(O)R^5$, wherein $R^5$ is ($C_{1-4}$)alkyl, ($C_{6-10}$)aryl($C_{0-6}$)alkyl, or ($C_{4-10}$)cycloalkyl($C_{0-6}$)alkyl, $R^6$ is hydrogen or ($C_{1-6}$)alkyl and $R^9$ is halo;
   wherein within $X^1$ any cycloalkyl, or aryl is unsubstituted or substituted with 1 radical selected from —$R^{15}$ and —$X^4C(O)R^{15}$; and wherein $X^1$ is unsubstituted or substituted further with 1 to 3 radicals independently selected from $(C_{1-6})$alkyl, halo-substituted$(C_{1-4})$alkyl, $-X^4NR^{12}R^{12}$, $-X^4OR^{13}$ and $-X^4S(O)_2R^{14}$, wherein $X^4$, $R^{12}$, $R^{13}$, $R^{14}$ and $R^{15}$ are as defined above;

$R^1$ and $R^2$ are both fluoro; or $R^1$ is hydrogen or $(C_{1-6})$alkyl and $R^2$ is selected from the group consisting of hydrogen, $(C_{1-6})$alkyl, $-X^4OR^{13}$ and $-R^{15}$; or $R^1$ and $R^2$ taken together with the carbon atom to which both $R^1$ and $R^2$ are attached form $(C_{3-8})$cycloalkylene; wherein $R^2$ may be substituted further with $(C_{1-6})$alkyl; wherein $X^4$, $R^{13}$ and $R^{15}$ are as defined above;

$R^3$ is $-C(R^{16})(R^{17})X^7$, wherein $R^{16}$ and $R^{17}$ are hydrogen, $(C_{1-6})$alkyl or fluoro, or $R^{16}$ is hydrogen and $R^{17}$ is hydroxy and $X^7$ is selected from $-X^4SR^{13}$, $-X^4C(O)R^{13}$, $-X^4C(O)NR^{12}R^{12}$, $-R^{15}$, $-X^4OR^{15}$, $-X^4SR^{15}$, $X^4S(O)_2R^{15}$, $-X^4C(O)R^{15}$ and $-X^4C(O)NR^{15}R^{12}$, wherein $X^4$, $R^{12}$, $R^{13}$ and $R^{15}$ are as defined above;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

3. A compound of claim 2 in which $R^3$ is $-CH_2X^7$, wherein $X^7$ is selected from $X^4SR^{13}$, $-X^4C(O)R^{13}$, $-X^4C(O)NR^{12}R^{12}$, $R^{15}$, $-X^4OR^{15}$, $-X^4SR^{15}$, $-X^4S(O)_2R^{15}$, $-X^4C(O)R^{15}$ and $-X^4C(O)NR^{15}R^{12}$, wherein $X^4$ is a bond or $(C_{1-6})$alkylene, $R^{12}$ at each occurrence independently is hydrogen or $(C_{1-6})$alkyl, $R^{13}$ is hydrogen, $(C_{1-6})$alkyl or halo-substituted$(C_{1-6})$alkyl, $R^{14}$ is $(C_{1-6})$alkyl or halo-substituted$(C_{1-6})$alkyl and $R^{15}$ for $R^3$ is $(C_{3-10})$cycloalkyl$(C_{0-6})$alkyl, $(C_{6-10})$aryl$(C_{0-6})$alkyl, or $(C_{9-12})$bicycloaryl$(C_{0-6})$alkyl; wherein $R^3$ may be substituted or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

4. A compound of claim 3 in which $R^3$ is selected from 3-cyclohexylpropyl, 2-cyclohexylpropyl, 2-cyclopentylpropyl, 3-phenylpropyl, 3-(2-difluoromethoxy)phenylpropyl, 2-phenylcyclopropylmethyl, 2,2-difluoro-3-phenylpropyl, 1-benzylcyclopropylmethy, 1-isobutylcyclopropylmethyl, cyclopropylmethylsulfanylmethyl, 2,2-dimethyl-3-phenylpropyl, 3-chloro-2-fluoro-benzylsulfonylmethyl, benzenesulfonylmethyl, benzylsulfonylmethyl, 2-(1,1-difluoromethoxy)-benzylsulfonylmethyl, 2-benzenesulfonyl-ethyl, 2-benzylsulfonyl-ethyl, 4-methoxy-benzylsulfonylmethyl, p-tolylmethylsulfonylmethyl, 4-chloro-benzylsulfonylmethyl, o-tolylmethylsulfonylmethyl, 3,5-dimethyl-benzylsulfonylmethyl, 4-trifluoromethyl-benzylsulfonylmethyl, 4-trifluoromethoxy-benzylsulfonylmethyl, 2-bromo-benzylsulfonylmethyl, 3-methyl-benzylsulfonylmethyl, 3-trifluoromethyl-benzylsulfonylmethyl, 3-trifluoromethoxy-benzylsulfonylmethyl, 4-fluoro-2-trifluoromethoxy-benzylsulfonylmethyl, 2-fluoro-6-trifluoromethyl-benzylsulfonylmethyl, 3-chloro-benzylsulfonylmethyl, 2-fluoro-benzylsulfonylmethyl, 2-trifluoro-benzylsulfonylmethyl, 2-cyano-benzylsulfonylmethyl, 4-tert-butyl-benzylsulfonylmethyl, 2-fluoro-3-methyl-benzylsulfonylmethyl, 3-fluoro-benzylsulfonylmethyl, 4-fluoro-benzylsulfonylmethyl, 2-chloro-benzylsulfonylmethyl, 2,5-difluoro-benzylsulfonylmethyl, 2,6-difluoro-benzylsulfonylmethyl, 2,5-dichloro-benzylsulfonylmethyl, 3,4-dichloro-benzylsulfonylmethyl, 2-(1,1-difluoro-methoxy)-benzylsulfonylmethyl, 2-cyano-benzylsulfonylmethyl, 3-cyano-benzylsulfonylmethyl, 2-trifluoromethoxy-benzylsulfonylmethyl, 2,3-difluoro-benzylsulfonylmethyl, 2,5-difluoro-benzylsulfonylmethyl, biphenyl-2-ylmethylsulfonylmethyl, cyclohexylmethyl, 3-fluoro-benzylsulfonylmethyl, 3,4-difluoro-benzylsulfonylmethyl, 2,4-difluoro-benzylsulfonylmethyl, 2,4,6-fluoro-benzylsulfonylmethyl, 2,4,5-trifluoro-benzylsulfonylmethyl, 2,3,4-trifluoro-benzylsulfonylmethyl, 2,3,5-trifluoro-benzylsulfonylmethyl, 2,5,6-trifluoro-benzylsulfonylmethyl, 2-chloro-5-trifluoromethylbenzylsulfonylmethyl, 2-methyl-propane-1-sulfonyl, 2-fluoro-3-trifluoromethylbenzylsulfonylmethyl, 2-fluoro-4-trifluoromethylbenzylsulfonylmethyl, 2-fluoro-5-trifluoromethylbenzylsulfonylmethyl, 4-fluoro-3-trifluoromethylbenzylsulfonylmethyl, 2-methoxy-benzylsulfonylmethyl, 3,5 bis-trifluoromethyl-benzylsulfonylmethyl, 4-difluoromethoxy-benzylsulfonylmethyl, 2-fluoromethoxy-benzylsulfonylmethyl, 3-difluoromethoxy-benzylsulfonylmethyl, 2,6-dichloro-benzylsulfonylmethyl, biphenyl-4-ylmethylsulfonylmethyl, 2-[4-(1,1-Difluoromethoxy)-benzenesulfonyl]-ethyl, 2-[2-(1,1-Difluoro-methoxy)-benzenesulfonyl]-ethyl, 2-[3-(1,1-Difluoro-methoxy)-benzenesulfonyl]-ethyl, 2(4-trifluoromethoxy-benzenesulfonyl)-ethyl, 2-(3-trifluoromethoxy-benzenesulfonyl)-ethyl, 2-(2-trifluoromethoxy-benzenesulfonyl)-ethyl, (cyanomethyl-methyl-carbamoyl)-methyl, biphenyl-3-ylmethyl, 2-benzenesulfonyl-ethyl, isobutylsulfanylmethyl, 2-phenylsulfanyl-ethyl, cyclohexylmethylsulfonylmethyl, 2-cyclohexyl-ethanesulfonyl, benzyl, naphthalen-2-yl, benzylsulfanylmethyl, 2-trifluoromethyl-benzylsulfanylmethyl, phenylsulfanyl-ethyl and cyclopropylmethylsulfonylmethyl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

5. A compound of claim 4 in which $R^4$ is selected from 1-hydroxy-2-morpholin-4-yl-2-oxoethyl, and 2-morpholin-4-yl-2-oxo-ethyl;

or the N-oxide derivatives, prodrug derivatives, protected derivatives, individual isomers and mixtures, of isomers thereof; or the pharmaceutically acceptable salts and solvates of such compounds or the N-oxide derivatives, prodrug derivatives, protected derivatives, individual isomers and mixtures of isomers thereof.

6. The compound of claim 5 in which $R^1$ is hydrogen or $(C_{1-6})$alkyl and $R^2$ is hydrogen, $-X^4OR^{13}$, $(C_{5-10})$aryl$(C_{0-6})$alkyl or $(C_{1-6})$alkyl; or $R^1$ and $R^2$ taken together with the carbon atom to which both $R^1$ and $R^2$ are attached form $(C_{3-8})$cycloalkylene; wherein the cycloalkylene is optionally substituted with 1 to 3 $(C_{1-6})$alkyl radicals;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

7. The compound of claim 6 in which $R^1$ is hydrogen or methyl and $R^2$ is methoxymethyl, methoxyethyl, methyl, ethyl, propyl, butyl, or phenethyl; or $R^1$ and $R^2$ taken together with the carbon atom to which both $R^1$ and $R^2$ are attached form cyclopropyl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

8. The compound of claim 7 of Formula I(a):

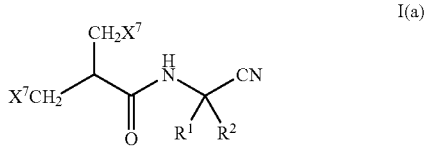

I(a)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

9. The compound of claim 7 of Formula I(b):

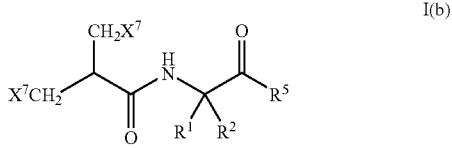

I(b)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

10. The compound of claim 9 in which $R^5$ is 1H-benzoimidazol-2-yl, benzooxazol-2-yl, oxazolo[4,5-b]pyridin-2-yl, benzothiazol-2-yl, 5-phenyl-[1,3,4]oxadiazol-2-yl, 4-(5-pyridin-4-yl-[1,3,4]oxadiazol-2-yl, 5-pyridin-3-yl-[1,3,4]oxadiazol-2-yl, pyrimidin-2-yl, 3-penyl-[1,2,4]oxadiazol-5-yl, 5-methoxymethyl-[1,3,4]oxadiazol-2-yl, phenyldicarbonyl, 5-methyl-[1,3,4]thiadiazol-2-yl, 5-trifluoromethyl-[1,3,4]oxadiazol-2-yl, 5-methyl-[1,3,4]oxadiazol-yl, 5-methyl-[1,2,4]oxadiazol-3-yl, 5-phenyl-[1,2,4]oxadiazol-3-yl, 5-trifluoromethyl-[1,2,4]oxadiazol-3-yl, or 3-methyl-[1,2,4]oxadiazol-5-yl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

11. The compound of claim 10 selected from the group consisting of N-[(S)-1-(1-benzothiazol-2-yl-methanoyl)-propyl]-4-morpholin-4-yl-4-oxo-2-benzylsulfonylmethyl-butyramide; N-[(S)-1-(1-benzooxazol-2-yl-methanoyl)-propyl]-4-morpholin-4-yl-4-oxo-2-benzylsulfonylmethyl-butyramide; N-[(S)-1-(1-Benzooxazol-2-yl-methanoyl)-pentyl]-4-morpholin-4-yl-4-oxo-2-benzylsulfonylmethyl-butyramide; 4-Morpholin-4-yl-4-oxo-2-benzylsulfonylmethyl-N-{(S)-1-[1-(3-phenyl-[1,2,4]oxadiazol-5-yl)-methanoyl]-propyl}-butyramide; N-[(S)-1-(1-Benzooxazol-2-yl-methanoyl)-butyl]-2-[2-(1,1-difluoro-methoxy)-benzylsulfonylmethyl]-3-benzylsulfonyl-propionamide; 4-Morpholin-4-yl-4-oxo-N-[1-(2-oxo-2-phenyl-acetyl)-pentyl]-2-benzylsulfonylmethyl-butyramide; N-(1,1-Dimethyl-2-oxazolo[4,5-b]pyridin-2-yl-2-oxo-ethyl)-4-morpholin-4-yl-4-oxo-2-benzylsulfonylmethyl-butyramide; N-[1-(5-Ethyl-[1,3,4]oxadiazole-2-carbonyl)-butyl]-4-morpholin-4-yl-4-oxo-2-benzylsulfonylmethyl-butyramide; N-[1-(5-Methoxymethyl-[1,3,4]oxadiazole-2-carbonyl)-propyl]-4-morpholin-4-yl-4-oxo-2-benzylsulfonylmethyl-butyramide; 4-Morpholin-4-yl-4-oxo-2-benzylsulfonylmethyl-N-[1-(5-phenyl-[1,3,4]oxadiazole-2-carbonyl)-propyl]-butyramide; 4-Morpholin-4-yl-N-[1-(oxazolo[4,5-b]pyridine-2-carbonyl)-propyl]-4-oxo-2-benzylsulfonylmethyl-butyramide; 4-Morpholin-4-yl-4-oxo-2-benzylsulfonylmethyl-N-[1-(5-pyridin-4-yl-[1,3,4]oxadiazole-2-carbonyl)-propyl]-butyramide; 4-Oxo-2-benzylsulfonylmethyl-4-piperidin-1-yl-N-[1-(5-pyridin-4-yl-[1,3,4]oxadiazole-2-carbonyl)-propyl]-butyramide; 4-Morpholinyl-4-yl-4-oxo-2-benzylsulfonylmethyl-N-[1-(5-pyridin-3-yl-[1,3,4]oxadiazole-2-carbonyl)-propyl]-butyramide; N-[1-(Benzooxazole-2-carbonyl)-propyl]-2-cyclohexylmethyl-4-morpholin-4-yl-4-oxo-butyramide; 2-Cyclohexylmethyl-4-morpholin-4-yl-N-[1-(oxazolo[4,5-b]pyridine-2-carbonyl)-propyl]-4-oxo-butyramide; 2-Cyclohexylmethyl-N-[1-(5-ethyl-[1,3,4]oxadiazole-2-carbonyl)-butyl]-4-morpholin-4-yl-4-oxo-butyramide; N-(2-Benzooxazol-2-yl-1-methoxymethyl-2-oxo-ethyl)-2-(2-difluoromethoxy-benzylsulfonylmethyl)-4-morpholin-4-yl-4-oxo-butyramide; N-[1-(Benzooxazole-2-carbonyl)-propyl]-2-(2-cyclohexyl-ethyl)-4-morpholin-4-yl-4-oxo-butyramide; 2-(2-Cyclohexyl-ethyl)-4-morpholin-4-yl-N-[1-(oxazolo[4,5-b]pyridine-2-carbonyl)-propyl]-4-oxo-butyramide; 2-(2-Cyclohexyl-ethyl)-4-morpholin-4-yl-oxo-N-[1-(5-phenyl-[1,3,4]oxadiazole-2-carbonyl)-propyl]-butyramide; 2-(2-Difluoromethoxy-benzylsulfonylmethyl)-4-morpholin-4-yl-4-oxo-N-[1-(5-phenyl-[1,3,4]oxadiazole-2-carbonyl)-propyl]-butyramide; 2-(2-Difluoromethoxy-benzylsulfonylmethyl)-N-[1-(5-ethyl-[1,3,4]oxadiazole-2-carbonyl)-butyl]-4-morpholin-4-yl-4-oxo-butyramide; N-[1-(Benzooxazole-2-carbonyl)-propyl]-2-(2-difluoromethoxy-benzyl-sulfonylmethyl)-4-morpholin-4-yl-4-oxo-butyramide;

(R)-2-Cyclohexylmethyl-4-morpholin-4-yl-4-oxo-N-[(S)-1-(5-phenyl-1,2,4-oxadiazole-3-carbonyl)-propyl]-butyramide; 4-Morpholin-4-yl-4-oxo-2-benzylsulfonylmethyl-N-[(S)-1-(5-phenyl-1,2,4-oxadiazole-3-carbonyl)-propyl]-butyramide; (R)-2-Cyclohexylmethyl-4-morpholin-4-yl-4-oxo-N-[(S)-1-(3-phenyl-1,2,4-oxadiazole-5-carbonyl)-propyl]-butyramide; 4-Morpholin-4-yl-N-[1-(oxazole-2-carbonyl)-3-phenyl-propyl]-4-oxo-2-benzylsulfonylmethyl-butyramide; N-(1,1-Dimethyl-2-oxazol-2-yl-2-oxo-ethyl)-4-morpholin-4-yl-4-oxo-2-benzylsulfonylmethyl-butyramide; 2-(2-Difluoromethoxy-benzylsulfonylmethyl)-4-morpholin-4-yl-N-[1-(oxazole-2-carbonyl)-3-phenyl-propyl]-4-oxo-butyramide; 2-(2-Methyl-propane-1-sulfonylmethyl)-4-morpholin-4-yl-N-[1-(oxazole-2-carbonyl)-3-phenyl-propyl]-4-oxo-butyramide; 2-Cyclopropylmethylsulfonylmethyl-4-morpholin-4-yl-N-[1-(oxazole-2-carbonyl)-3-phenyl-propyl]-4-oxo-butyramide; 2-Cyclopropylmethylsulfonylmethyl-N-{(S)-1-[(R)-hydroxy-(3-phenyl-1,2,4-oxadiazol-5-yl)-methyl]-propyl}-4-morpholin-4-yl-4-oxo-butyramide; N-{(S)-1-[(R)-hydroxy-(3-phenyl-1,2,4-oxadiazol-5-yl)-methyl]-propyl}-2-(2-methyl-propane-1-sulfonyl-methyl)-4-morpholin-4-yl-4-oxo-butyramide; 2-Cyclopropylmethylsulfonylmethyl-4-morpholin-4-yl-4-oxo-N-[(S)-1-(3-phenyl-1,2,4-oxadiazole-5-carbonyl)- propyl]-butyramide; 2-(2-methyl-propane-1-sulfonylmethyl)-4-morpholin-4-yl-4-oxo-N-[(S)-1-(3-phenyl-1,2,4-oxadiazole-5-carbonyl)-propyl]-butyramide; N-[(1S)-1-(Benzooxazol-2-yl-hydroxymethyl)-3-phenyl-propyl]-2-cyclopropylmethylsulfonylmethyl-4-morpholin-4-yl-4-oxo-butyramide; and 4-Morpholin-4-yl-N-[1-(oxazole-2-carbonyl)-cyclopropyl]-4-oxo-2-benzylsulfonyl methyl-butyramide;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

12. The compound of claim 7 of Formula I(c):

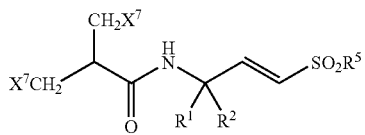

I(c)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

13. The compound of claim 12 in which $R^5$ is phenyl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

14. The compound of claim 7 of Formula I(d):

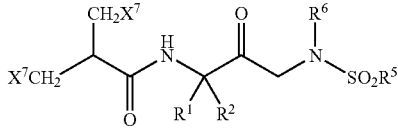

I(d)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

15. The compound of claim 14 in which $R^5$ is phenyl and $R^6$ is hydrogen;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

16. The compound of claim 15 namely N-(3-benzenesulfonylamino-2-oxo-propyl)-4-morpholin-4-yl-4-oxo-2-benzylsulfonylmethyl-butyramide;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

17. The compound of claim 7 of Formula I(e):

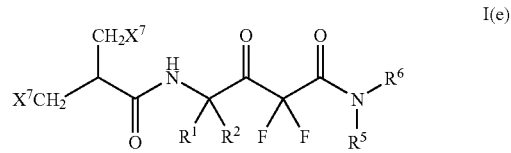

I(e)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

18. The compound of claim 17 in which $R^5$ and $R^6$ is methyl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

19. The compound of claim 7 of Formula I(f):

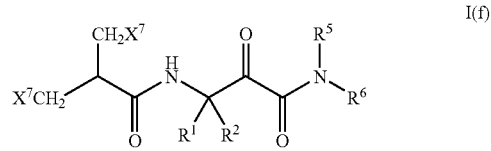

I(f)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

20. The compound of claim 19 in which $R^5$ is methyl, benzyl, phenethyl, cyclohexyl, tetrahydro-pyran-4-yl, pyridin-2-yl, pyridin-2-ylmethyl or oxazol-2-ylmethyl; or $R^6$ is hydrogen or methyl;

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

21. The compound of claim 7 of Formula I(g):

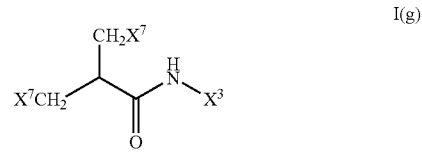

I(g)

or the N-oxide derivatives, prodrug derivatives, protected derivatives, individual isomers and mixtures of isomers thereof; or the pharmaceutically acceptable salts and solvates of such compounds or the N-oxide derivatives, prodrug derivatives, protected derivatives, individual isomers and mixtures of isomers thereof.

22. A pharmaceutical composition comprising a therapeutically effective amount of a compound of claim 1 in combination with a pharmaceutically acceptable excipient.

* * * * *